US011746120B2

(12) United States Patent
Mainolfi et al.

(10) Patent No.: US 11,746,120 B2
(45) Date of Patent: Sep. 5, 2023

(54) STAT DEGRADERS AND USES THEREOF

(71) Applicant: Kymera Therapeutics, Inc., Watertown, MA (US)

(72) Inventors: Nello Mainolfi, Belmont, MA (US); Nan Ji, Arlington, MA (US); Bin Yang, Lexington, MA (US); Yi Zhang, Belmont, MA (US)

(73) Assignee: Kymera Therapeutics, Inc., Watertown, MA (US)

( * ) Notice: Subject to any disclaimer, the term of this patent is extended or adjusted under 35 U.S.C. 154(b) by 1 day.

(21) Appl. No.: 18/045,390

(22) Filed: Oct. 10, 2022

(65) Prior Publication Data

US 2023/0120381 A1 Apr. 20, 2023

Related U.S. Application Data

(60) Continuation of application No. 17/736,669, filed on May 4, 2022, which is a division of application No. 16/841,095, filed on Apr. 6, 2020, now Pat. No. 11,485,750.

(60) Provisional application No. 62/967,921, filed on Jan. 30, 2020, provisional application No. 62/949,053, filed on Dec. 17, 2019, provisional application No. 62/947,310, filed on Dec. 12, 2019, provisional application No. 62/944,810, filed on Dec. 6, 2019, provisional application No. 62/932,957, filed on Nov. 8, 2019, provisional application No. 62/926,127, filed on Oct. 25, 2019, provisional application No. 62/887,872, filed on Aug. 16, 2019, provisional application No. 62/877,051, filed on Jul. 22, 2019, provisional application No. 62/875,362, filed on Jul. 17, 2019, provisional application No. 62/860,512, filed on Jun. 12, 2019, provisional application No. 62/855,259, filed on May 31, 2019, provisional application No. 62/833,331, filed on Apr. 12, 2019, provisional application No. 62/830,095, filed on Apr. 5, 2019.

(51) Int. Cl.

| | |
|---|---|
| *C07F 9/6561* | (2006.01) |
| *A61K 45/06* | (2006.01) |
| *C07F 9/6506* | (2006.01) |

(52) U.S. Cl.
CPC ........ *C07F 9/6561* (2013.01); *C07F 9/65068* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,650,750 | A | 3/1987 | Giese |
| 4,709,016 | A | 11/1987 | Giese |
| 5,360,811 | A | 11/1994 | Tegeler et al. |
| 5,360,819 | A | 11/1994 | Giese |
| 5,516,931 | A | 5/1996 | Giese et al. |
| 5,602,273 | A | 2/1997 | Giese et al. |
| 5,604,104 | A | 2/1997 | Giese et al. |
| 5,610,020 | A | 3/1997 | Giese et al. |
| 5,650,270 | A | 7/1997 | Giese et al. |
| 5,721,246 | A | 2/1998 | Yoshino et al. |
| 6,306,663 | B1 | 10/2001 | Kenten et al. |
| 6,552,065 | B2 | 4/2003 | Remiszewski et al. |
| 6,559,280 | B2 | 5/2003 | Kenten et al. |
| 6,627,754 | B2 | 9/2003 | Blumenkopf et al. |
| 6,949,537 | B2 | 9/2005 | Garlich et al. |
| 7,041,298 | B2 | 5/2006 | Deshaies et al. |
| 7,071,189 | B2 | 7/2006 | Kawashima et al. |
| 7,074,620 | B2 | 7/2006 | Kenten et al. |
| 7,173,015 | B2 | 2/2007 | Schreiber et al. |
| 7,208,157 | B2 | 4/2007 | Dashaies et al. |
| 7,273,920 | B2 | 9/2007 | Kenten et al. |
| 7,307,077 | B2 | 12/2007 | Kawashima et al. |
| 7,390,799 | B2 | 6/2008 | Bruncko et al. |
| 7,402,325 | B2 | 7/2008 | Addington |
| 7,449,458 | B2 | 11/2008 | Bhamidipati et al. |
| 7,501,496 | B1 | 3/2009 | Endl et al. |
| 7,514,444 | B2 | 4/2009 | Honigberg et al. |
| 7,528,143 | B2 | 5/2009 | Noronha et al. |
| 7,557,210 | B2 | 7/2009 | Singh et al. |
| 7,598,257 | B2 | 10/2009 | Rodgers et al. |
| 7,622,496 | B2 | 11/2009 | Larsen et al. |
| 7,667,039 | B2 | 2/2010 | Garcia-Echeverria et al. |
| 7,713,943 | B2 | 5/2010 | Klippel-Giese et al. |
| 7,781,433 | B2 | 8/2010 | Chuckowree et al. |
| 7,786,142 | B2 | 8/2010 | Rao et al. |
| 7,932,260 | B2 | 4/2011 | Fowler et al. |
| 7,960,434 | B2 | 6/2011 | Turkson et al. |
| 7,989,622 | B2 | 8/2011 | Bajjalieh et al. |

(Continued)

FOREIGN PATENT DOCUMENTS

| | | | |
|---|---|---|---|
| CN | 105085620 | B | 5/2018 |
| WO | WO-2001042246 | A2 | 6/2001 |

(Continued)

OTHER PUBLICATIONS

Adams, et al., "Big opportunities for small molecules in immuno-oncology," Nature Reviews: Drug Discovery, vol. 14, No. 9, 2015 (pp. 603-622).
Alas et al., "Inhibition of Constitutive STAT3 Activity Sensitizes Resistant Non-Hodgkin's Lymphoma and Multiple Myeloma to Chemotherapeutic Drug-mediated Apoptosis," Clinical Cancer Research. 2003; 9:316-326.
Andrés et al., "Studies of Jak/STAT 3 expression and signaling in psoriasis identifies STAT 3?Ser727 phosphorylation as a modulator of transcriptional activity," Experimental Dermatology. 2013;22(5):323-328.

(Continued)

*Primary Examiner* — Po-Chih Chen
(74) *Attorney, Agent, or Firm* — Dechert LLP; Andrea L. C. Reid; Todd K. Macklin

(57) ABSTRACT

The present invention provides compounds, compositions thereof, and methods of using the same.

30 Claims, 26 Drawing Sheets

(56) References Cited

U.S. PATENT DOCUMENTS 8,138,347 B2 3/2012 Knight et al.
8,143,412 B2 3/2012 Priebe et al.
8,185,616 B2 5/2012 Nagata et al.
8,217,035 B2 7/2012 Burger et al.
8,263,599 B2 9/2012 Sekiguchi et al.
8,338,439 B2 12/2012 Singh et al.
8,446,290 B2 5/2013 Affolter et al.
8,486,941 B2 7/2013 Burns et al.
8,796,320 B2 8/2014 Asai et al.
8,841,257 B2 9/2014 McMurray et al.
8,883,749 B2 11/2014 Li et al.
8,906,682 B2 12/2014 June et al.
9,500,653 B2 11/2016 Crews et al.
9,632,089 B2 4/2017 Crews et al.
9,694,084 B2 7/2017 Bradner et al.
9,750,816 B2 9/2017 Bradner et al.
9,770,512 B2 9/2017 Bradner et al.
9,821,068 B2 11/2017 Bradner et al.
9,969,710 B2 5/2018 Jorand-Lebrun et al.
10,125,114 B2 11/2018 Bradner et al.
10,336,744 B2 7/2019 Hading et al.
10,874,743 B2 12/2020 Mainolfi et al.
11,117,889 B1 9/2021 Mainolfi et al.
2001/0053782 A1 12/2001 Blumenkopf et al.
2002/0042427 A1 4/2002 Tang et al.
2002/0068063 A1 6/2002 Deshaies et al.
2002/0183360 A1 12/2002 Muller et al.
2004/0029902 A1 2/2004 Singh et al.
2004/0048859 A1 3/2004 Germann et al.
2004/0106569 A1 6/2004 Klippel-Giese et al.
2004/0116421 A1 6/2004 Kawashima et al.
2004/0138189 A1 7/2004 Sebti et al.
2004/0242631 A1 12/2004 Garlich et al.
2005/0014802 A1 1/2005 Attardo et al.
2005/0075306 A1 4/2005 Schreiber et al.
2005/0277680 A1 12/2005 Priebe et al.
2006/0211657 A1 9/2006 Singh et al.
2006/0247318 A1 11/2006 Song et al.
2007/0010428 A1 1/2007 McMurray et al.
2007/0098719 A1 5/2007 Smith et al.
2007/0135461 A1 6/2007 Rodgers et al.
2007/0191405 A1 8/2007 Noronha et al.
2008/0076768 A1 3/2008 Chuckowree et al.
2008/0108636 A1 5/2008 Honigberg et al.
2008/0139456 A1 6/2008 Burke et al.
2008/0194579 A1 8/2008 Garcia-Echeverria et al.
2008/0275067 A1 11/2008 Fowler et al.
2009/0055944 A1 2/2009 Korman et al.
2009/0136494 A1 5/2009 Ponath et al.
2009/0233903 A1 9/2009 Rodgers et al.
2010/0087440 A1 4/2010 Bajjalieh et al.
2010/0150892 A1 6/2010 Han
2010/0197671 A1 8/2010 Burns et al.
2010/0197686 A1 8/2010 Xing et al.
2010/0203056 A1 8/2010 Irving et al.
2010/0233183 A1 9/2010 Triebel et al.
2010/0249092 A1 9/2010 Singh et al.
2010/0249126 A1 9/2010 Burger et al.
2011/0008331 A1 1/2011 Triebel
2011/0053941 A1 3/2011 Mautino et al.
2011/0136796 A1 6/2011 Mautino et al.
2011/0144043 A1 6/2011 Frank
2011/0165156 A1 7/2011 Dimoudis et al.
2011/0274683 A1 11/2011 Wong et al.
2011/0319362 A1 12/2011 Wang et al.
2012/0053208 A1 3/2012 Li et al.
2012/0189639 A1 7/2012 Schebye et al.
2012/0277217 A1 11/2012 Mautino et al.
2012/0302524 A1 11/2012 Asai et al.
2012/0329997 A1 12/2012 Fertig et al.
2013/0005949 A1 1/2013 Fertig et al.
2013/0149236 A1 6/2013 Johnson et al.
2013/0190340 A1 7/2013 Hedstrom et al.
2013/0225621 A1 8/2013 Turkson et al.
2014/0066625 A1 3/2014 Mautino et al.
2014/0079699 A1 3/2014 Wong et al.
2014/0079706 A1 3/2014 Cannarile et al.
2014/0093511 A1 4/2014 Lonberg et al.
2014/0302523 A1 10/2014 Crews et al.
2014/0336363 A1 11/2014 Fertig et al.
2014/0341917 A1 11/2014 Nastri et al.
2014/0356322 A1 12/2014 Crews et al.
2015/0158894 A1 6/2015 Gunning et al.
2015/0166484 A1 6/2015 Daniels et al.
2015/0225449 A1 8/2015 Donnell et al.
2015/0232434 A1 8/2015 Li et al.
2015/0259366 A1 9/2015 Sebti et al.
2015/0274738 A1 10/2015 Gray et al.
2015/0291562 A1 10/2015 Crew et al.
2015/0374678 A1 12/2015 Chamberlain et al.
2016/0022642 A1 1/2016 Crews et al.
2016/0045607 A1 2/2016 Crew et al.
2016/0058872 A1 3/2016 Crew et al.
2016/0060239 A1 3/2016 Kwon et al.
2016/0068478 A1 3/2016 Turkson et al.
2016/0137663 A1 5/2016 Chang et al.
2016/0214972 A1 7/2016 Jin et al.
2016/0235730 A1 8/2016 Bradner et al.
2016/0235731 A1 8/2016 Bradner et al.
2016/0243247 A1 8/2016 Bradner et al.
2016/0272596 A1 9/2016 Chen et al.
2016/0272639 A1 9/2016 Crew et al.
2017/0008904 A1 1/2017 Crew et al.
2017/0037004 A1 2/2017 Crew et al.
2017/0121321 A1 5/2017 Crews et al.
2017/0281784 A1 10/2017 Wang et al.
2017/0320889 A1 11/2017 Park et al.
2017/0327469 A1 11/2017 Crew et al.
2018/0009779 A1 1/2018 Bradner et al.
2018/0028475 A1 2/2018 Reuveni et al.
2018/0085465 A1 3/2018 Bradner et al.
2018/0118733 A1 5/2018 Harling et al.
2018/0134684 A1 5/2018 Bradner et al.
2018/0147202 A1 5/2018 Crew et al.
2018/0155360 A1 6/2018 Martin et al.
2018/0228907 A1 8/2018 Crew et al.
2019/0071415 A1 3/2019 Bradner et al.
2019/0076539 A1 3/2019 Phillips et al.
2019/0076540 A1 3/2019 Phillips et al.
2019/0076541 A1 3/2019 Phillips et al.
2019/0076542 A1 3/2019 Phillips et al.
2019/0151457 A1 5/2019 Bradner et al.
2019/0192668 A1 6/2019 Mainolfi et al.
2019/0276474 A1 9/2019 Chan et al.
2020/0010468 A1 1/2020 Ji et al.
2020/0347045 A1 11/2020 Mainolfi et al.
2020/0377469 A1 12/2020 Mainolfi et al.
2021/0002296 A1 1/2021 Mainolfi et al.
2021/0228562 A1 7/2021 Weiss
2021/0238193 A1 8/2021 Mainolfi et al.
2022/0185831 A1* 6/2022 Wang .................... C07F 9/6561

FOREIGN PATENT DOCUMENTS

WO WO-2002020740 A2 3/2002
WO WO-2003063794 A2 8/2003
WO WO-2004019973 A1 3/2004
WO WO-2004089925 A1 10/2004
WO WO-2004106328 A1 12/2004
WO WO-2005007623 A2 1/2005
WO WO-2005113554 A2 12/2005
WO WO-2006029879 A2 3/2006
WO WO-2006078846 A1 7/2006
WO WO-2006105021 A2 10/2006
WO WO-2006122806 A2 11/2006
WO WO-2007001306 A1 1/2007
WO WO-2007005874 A2 1/2007
WO WO-2007016176 A2 2/2007
WO WO-2007042912 A2 4/2007
WO WO-2007044729 A2 4/2007
WO WO-2007053452 A1 5/2007
WO WO-2007070514 A1 6/2007
WO WO-2007084786 A1 7/2007
WO WO-2007129161 A2 11/2007

(56) References Cited

FOREIGN PATENT DOCUMENTS

| | | | |
|---|---|---|---|
| WO | WO-2007136858 | A2 | 11/2007 |
| WO | WO-2008039218 | A2 | 4/2008 |
| WO | WO-2008067270 | A1 | 6/2008 |
| WO | WO-2008109943 | A1 | 9/2008 |
| WO | WO-2008118802 | A1 | 10/2008 |
| WO | WO-2008132601 | A1 | 11/2008 |
| WO | WO-2008156644 | A2 | 12/2008 |
| WO | WO-2009009116 | A2 | 1/2009 |
| WO | WO-2009032338 | A1 | 3/2009 |
| WO | WO-2009044273 | A2 | 4/2009 |
| WO | WO-2009073620 | A2 | 6/2009 |
| WO | WO-2009114512 | A1 | 9/2009 |
| WO | WO-2009115665 | A1 | 9/2009 |
| WO | WO-2009132238 | A3 | 10/2009 |
| WO | WO-2010005807 | A2 | 1/2010 |
| WO | WO-2010019570 | A2 | 2/2010 |
| WO | WO-2010077589 | A2 | 7/2010 |
| WO | WO-2010077634 | A1 | 7/2010 |
| WO | WO-2010118309 | A2 | 10/2010 |
| WO | WO-2010121007 | A1 | 10/2010 |
| WO | WO-2011028683 | A1 | 3/2011 |
| WO | WO-2011056652 | A1 | 5/2011 |
| WO | WO-2011066263 | A1 | 6/2011 |
| WO | WO-2011070024 | A1 | 6/2011 |
| WO | WO-2011090760 | A1 | 7/2011 |
| WO | WO-2011107553 | A1 | 9/2011 |
| WO | WO-2011109400 | A2 | 9/2011 |
| WO | WO-2011131407 | A1 | 10/2011 |
| WO | WO-2011140249 | A2 | 11/2011 |
| WO | WO-2011163424 | A2 | 12/2011 |
| WO | WO-2012003281 | A3 | 1/2012 |
| WO | WO-2012018868 | A1 | 2/2012 |
| WO | WO-2012032433 | A1 | 3/2012 |
| WO | WO-2012078559 | A2 | 6/2012 |
| WO | WO-2012078982 | A2 | 6/2012 |
| WO | WO-2012097351 | A1 | 7/2012 |
| WO | WO-2012142237 | A1 | 10/2012 |
| WO | WO-2012142615 | A2 | 10/2012 |
| WO | WO-2012145493 | A1 | 10/2012 |
| WO | WO-2013079174 | A1 | 6/2013 |
| WO | WO-2013087699 | A1 | 6/2013 |
| WO | WO-2013106643 | A2 | 7/2013 |
| WO | WO-2013106646 | A2 | 7/2013 |
| WO | WO-2013119716 | A1 | 8/2013 |
| WO | WO-2013132044 | A1 | 9/2013 |
| WO | WO-2013169264 | A1 | 11/2013 |
| WO | WO-2013177534 | A2 | 11/2013 |
| WO | WO-2013187965 | A1 | 12/2013 |
| WO | WO-2014008218 | A1 | 1/2014 |
| WO | WO-2014028909 | A1 | 2/2014 |
| WO | WO-2014036357 | A1 | 3/2014 |
| WO | WO-2014044622 | A1 | 3/2014 |
| WO | WO-2014063061 | A1 | 4/2014 |
| WO | WO-2014070859 | A1 | 5/2014 |
| WO | WO-2014108452 | A1 | 7/2014 |
| WO | WO-2014153495 | A2 | 9/2014 |
| WO | WO-2014205416 | A1 | 12/2014 |
| WO | WO-2015071393 | A1 | 5/2015 |
| WO | WO-2015160845 | A3 | 10/2015 |
| WO | WO-2016089060 | A2 | 6/2016 |
| WO | WO-2016105518 | A1 | 6/2016 |
| WO | WO-2016115455 | A2 | 7/2016 |
| WO | WO-2016118666 | A1 | 7/2016 |
| WO | WO-2016125169 | A1 | 8/2016 |
| WO | WO-2016149668 | A1 | 9/2016 |
| WO | WO-2016169989 | A1 | 10/2016 |
| WO | WO-2016193332 | A1 | 12/2016 |
| WO | WO-2016197032 | A1 | 12/2016 |
| WO | WO-2016197114 | A1 | 12/2016 |
| WO | WO-2017007612 | A1 | 1/2017 |
| WO | WO-2017011371 | A1 | 1/2017 |
| WO | WO-2017011590 | A1 | 1/2017 |
| WO | WO-2017030814 | A1 | 2/2017 |
| WO | WO-2017079267 | A1 | 5/2017 |
| WO | WO-2017117473 | A1 | 7/2017 |
| WO | WO-2017117474 | A1 | 7/2017 |
| WO | WO-2017161119 | A1 | 9/2017 |
| WO | WO-2017176708 | A1 | 10/2017 |
| WO | WO-2017176957 | A1 | 10/2017 |
| WO | WO-2017176958 | A1 | 10/2017 |
| WO | WO-2017197036 | A1 | 11/2017 |
| WO | WO-2017197046 | A1 | 11/2017 |
| WO | WO-2017197051 | A1 | 11/2017 |
| WO | WO-2017197055 | A1 | 11/2017 |
| WO | WO-2017197056 | A1 | 11/2017 |
| WO | WO-2017201449 | A1 | 11/2017 |
| WO | WO-2017211924 | A1 | 12/2017 |
| WO | WO-2018098367 | A1 | 5/2018 |
| WO | WO-2018104295 | A1 | 6/2018 |
| WO | WO-2018136935 | A1 | 7/2018 |
| WO | WO-2018144649 | A1 | 8/2018 |
| WO | WO-2018237026 | A1 | 12/2018 |
| WO | WO-2019043214 | A1 | 3/2019 |
| WO | WO-2019060693 | A1 | 3/2019 |
| WO | WO-2019060742 | A1 | 3/2019 |
| WO | WO-2019084026 | A1 | 5/2019 |
| WO | WO-2019084030 | A1 | 5/2019 |
| WO | WO-2019099868 | A1 | 5/2019 |
| WO | WO-2019099926 | A1 | 5/2019 |
| WO | WO-2019133531 | A1 | 7/2019 |
| WO | WO-2019140380 | A1 | 7/2019 |
| WO | WO-2019140387 | A1 | 7/2019 |
| WO | WO-2019165229 | A1 | 8/2019 |
| WO | WO-2019236483 | | 12/2019 |
| WO | WO-2020010177 | A1 | 1/2020 |
| WO | WO-2020010210 | A1 | 1/2020 |
| WO | WO-2020010227 | A1 | 1/2020 |
| WO | WO-2020113233 | A1 | 6/2020 |
| WO | WO-2020206424 | A1 | 10/2020 |
| WO | WO-2020264490 | A1 | 12/2020 |
| WO | WO-2020264499 | A1 | 12/2020 |
| WO | WO-2021011631 | A1 | 1/2021 |
| WO | WO-2021011634 | A1 | 1/2021 |
| WO | WO-2021011868 | A1 | 1/2021 |
| WO | WO-2021011871 | A1 | 1/2021 |
| WO | WO-2021119159 | A1 | 6/2021 |
| WO | WO-2021127190 | A1 | 6/2021 |
| WO | WO-2021127278 | A1 | 6/2021 |
| WO | WO-2021127283 | A2 | 6/2021 |
| WO | WO-2021158634 | A1 | 8/2021 |

OTHER PUBLICATIONS

Aoki et al., “Inhibition of STAT3 Signaling Induces Apoptosis and Decreases Surviving Expression in Primary Effusion Lymphoma,” Blood. 2003;101(4):1535-1542.

Aruri et al., “Metal-free Cross-Dehydrogenative Coupling of HN-azoles with a-C(sp3)-H Amides via C—H Activation and Its Mechanistic and Application Studies,” 2016, The Journal of Organic Chemistry 82(2): 1000-1012.

Berge et al., “Pharmaceutical Salts,” Journal of Pharmaceutical Sciences, vol. 66, No. 1, 1977 (pp. 1-19).

Berndsen et al., “New Insights Into Ubiquitin E3 Ligase Mechanism,” Nature Structural and Molecular Biology. 2014; 21(4):301-307.

Boichenko et al. “A FRET-Based Assay for the Identification and Characterization of Cereblon Ligands,” Journal of Medicinal Chemistry, vol. 59, No. 2, 2016 (pp. 770-774).

Botta et al., “Identification of Lead Compounds as Inhibitors of STAT3: Design, Synthesis and Bioactivity,” Molecular Informatics. 2015; 34(10):689-697.

Bowman et al., “STATs in oncogenesis,” Oncogene. 2000; 19:2474-2488.

Bromberg et al., “Signal transducers and activators of transcription as regulators of growth, apoptosis and breast development,” Breast Cancer Research. 2000; 2:86-90.

Bromberg et al., “The Role of STATs in Transcriptional Control and Their Impact on Cellular Function,” Oncogene. 2000, 19(21):2468-73.

Bromberg et al., “Stat3 Activation Is Required for Cellular Transformation by v-src,” Molecular and Cellular Biology. 1998; 18(5):2553-2558.

(56) References Cited

OTHER PUBLICATIONS

Bromberg et al., "Stat3 as an Oncogene," Cell. 1999; 98:295-303.
Burke et al., "Inhibition of constitutively active Stat3 suppresses growth of human ovarian and breast cancer cells," Oncogene. 2001, 20:7925-7934.
Campbell, "Cytokine-mediated Inflammation, Tumorigenesis, and Disease-Associated JAK/STAT/SOCS Signaling Circuits in the CNS," Brain Research Reviews. 2005; 48(2):166-167.
Catlett-Falcone et al., "Constitutive Activation of Stat3 Signaling Confers Resistance to Apoptosis in Human U266 Myeloma Cells," Immunity. 1999; 10(1):105-15.
Catlett-Falcone et al., "STAT proteins as novel targets for cancer therapy," Currrent Opinion in Oncology. 1999; 11(6):490-496.
Chang et al., "What is the functional role of the thalidomide binding protein cereblon?", International Journal of Biochemistry and Molecular Biology, vol. 2, No. 3, 2011 (pp. 287-294).
Chen et al., "Structure-Based Design of Conformationally Constrained, Cell-Permeable STAT3 Inhibitors," Medicinal Chemistry Letters. 2010, 1:85-89.
Chun et al., "Alantolactone Selectively Suppresses STAT3 Activation and Exhibits Potent Anticancer Activity in MDA-MB-231 Cells," Cancer Letters. 2015, 357(1):393-403.
Connolly et al., "Complexities of TGF-? Targeted Cancer Therapy," International Journal of Biological Sciences, vol. 8, 2012 (pp. 964-978).
Contino-Pepin et al., "Preliminary biological evaluations of new thalidomide analogues for multiple sclerosis application," Bioorganic & Medicinal Chemistry Letters, vol. 19, No. 2, 2009 (pp. 878-881).
Crews et al., "Targeting the Undruggable Proteome: The Small Molecules of My Dreams," Chemistry & Biology, vol. 17, No. 6, 2010 (pp. 551-555).
Daka et al., "Design, Synthesis and Evaluation of XZH-5 Analogues as STAT3 Inhibitors," Bioorganic and Medicinal Chemistry. 2015, 23(6):1348-55.
Darnell et al., "Transcription Factors as Targets for Cancer Therapy," Nature Reviews. Cancer. 2002, 2(10):740-9.
Darnell et al., "Jak-STAT Pathways and Transcriptional Activation in Response to IFNs and Other Extracellular Signaling Proteins," Science. 1994, 264(5164):1415-21.
Dechow et al., "Requirement of Matrix metalloproteinase-9 for the Transformation of Human Mammary Epithelial Cells by Stat3-C," Proceedings of the National Academy of Sciences of the United States of America. USA 2004, 101(29):10602-7.
Deshaies et al., "RING domain E3 ubiquitin ligases," Annual Review of Biochemistry, vol. 78, 2009, (pp. 399-434).
Dhanik, A. et al., "Binding Modes of Peptidomimetics Designed to Inhibit STAT3," PLoS One. 2012, 7(12):e51603.
Epling-Burnette et al., "Inhibition of STAT3 Signaling Leads to Apoptosis of Leukemic Large Granular Lymphocytes and Decreased Mcl-1 Expression," Journal of Clinical Investigation. 2001, 107(3):351-62.
Feng, T. et al., "Arctigenin Inhibits STAT3 and Exhibits Anticancer Potential in Human Triple-Negative Breast Cancer Therapy," Oncotarget. 2017, 8(1):329-344.
Fischer et al., "Structure of the DDB1-CRBN E3 ubiquitin ligase in complex with thalidomide," Nature, vol. 512, No. 7512, 2014 (pp. 49-53).
Gao et al., "Design, synthesis and biological evaluation of benzyloxyphenyl-methylaminophenol derivatives as STAT3 signaling pathway inhibitors," Bioorganic and Medicinal Chemistry. 2016, 24(11):2549-2558.
Gao et al., "STAT proteins—key regulators of anti-viral responses, inflammation, and tumorigenesis in the liver," Journal of Hepatology. 2012, 57(2):430-441.
Garcia et al., "Constitutive Activation of Stat3 by the Src and JAK Tyrosine Kinases Participates in Growth Regulation of Human Breast Carcinoma Cells," Oncogene. 2001; 20:2499-2513.
Garcia et al., "Constitutive Activation of Stat3 in Fibroblasts Transformed by Diverse Oncoproteins and in Breast Carcinoma Cells," Cell Growth and Differentiation. 1997; 8: 1267-1276.
Goropevšek et al., "The Role of STAT Signaling Pathways in the Pathogenesis of Systemic Lupus Erythematosus," Clinical Reviews in Allergies and Immunology. 2017, 52(2):164-181.
Gough et al., "Mitochondrial STAT3 Supports Ras-dependent Oncogenic Transformation," Science. 2009, 324(5935):1713-6.
Grivennikov et al., "Dangerous Liaisons: STAT3 and NF-kappaB Collaboration and Crosstalk in Cancer," Cytokine & Growth Factor Reviews. 2010, 21(1):11-9.
Grote et al., "JANUS under stress—Role of JAK/STAT signaling pathway in vascular diseases," Vascular Pharmacology. 2005, 43:357-363.
Gurzov et al., "The JAK/STAT pathway in obesity and diabetes," The FEBS Journal. 2016, 283(16):3002-3015.
Hagner et al., "CC-122, a pleiotropic pathway modifier, mimics an interferon response and has antitumor activity in DLBCL," Blood, vol. 126, 2015 (pp. 779-789).
Hillgren et al., "In vitro systems for studying intestinal drug absorption," Medicinal Research Reviews. 1995, 15(2):83-109.
Hines et al., "MDM2-Recruiting PROTAC Offers Superior, Synergistic Antiproliferative Activity via Simultaneous Degradation of BRD4 and Stabilization of p53," Cancer Research, vol. 79. No. 1, 2019 (pp. 251-262) DOI: 10.1158/0008-5472.CAN-18-2918.
Hodge et al., "Constitutive activation of STAT5A and STAT5B regulates IgM secretion in Waldenstrom's macroglobulinemia," Blood. 2014, 123(7):1055-1058.
Huang et al., "First Discovery of Novel 3-hydroxy-quinazoline-2,4(1H,3H)-diones as Specific Anti-Vaccinia and Adenovirus Agents via 'Privileged Scaffold' Refining Approach," Bioorganic and Medicinal Chemistry Letters. 2016, 26:5172-5176.
Iconomou et al., "Systematic approaches to identify E3 ligase substrates," Biochemical Journal, vol. 473, 2016 (pp. 4083-4101).
Ito et al., "Identification of a primary target of thalidomide teratogenicity," Science, vol. 327, No. 5971, 2010 (pp. 1345-1350).
Jamroskovic, J. et al., "Quinazoline Ligands Induce Cancer Cell Death through Selective STAT3 Inhibition and G?Quadruplex Stabilization," Journal of American Chemical Society. 2020, 42:2876-2888.
Jatiani et al., "Jak/STAT Pathways in Cytokine Signaling and Myeloproliferative Disorders: Approaches for Targeted Therapies," Genes & Cancer. 2011, 1(10):979-993.
Ji et al., "4-Carbonyl-2,6-dibenzylidenecyclohexanone Derivatives as Small Molecule Inhibitors of STAT3 Signaling Pathway," Bioorganic & Medicinal Chemistry. 2016, 24(23):6174-6182.
Kester et al., "Optimization of Benzodiazepinones as Selective Inhibitors of the X-Linked Inhibitor of Apoptosis Protein (XIAP) Second Baculovirus IAP Repeat (BIR2) Domain," Journal of Medicinal Chemistry, vol. 56, No. 20, 2013 (pp. 7788-7803).
Kiuchi et al., "STAT3 Is Required for the gp130-mediated Full Activation of the c-myc Gene," Journal of Experimental Medicine. 1999, 189(1):63-73.
Kolosenko et al., Identification of Novel Small Molecules That Inhibit STAT3-dependent Transcription and Function, PLoS One 2017, 12(6):e0178844.
Krönke et al., "Lenalidomide causes selective degradation of IKZF1 and IKZF3 in multiple myeloma cells" Science, vol. 343, No. 6168, 2014 (pp. 301-305).
Lavecchia et al., "STAT-3 inhibitors: state of the art and new horizons for cancer treatment," Current Medicinal Chemistry. 2011, 18(16):2359-75.
Leung et al., "Discovery of a small-molecule inhibitor of STAT3 by ligand-based pharmacophore screening," Methods. 2015, 71:38-43.
Levy et al., "Stats: Transcriptional Control and Biological Impact," Nature Reviews. Molecular Cell Biology. 2002, 3(9):651-62.
Li et al., "Genome-wide and functional annotation of human E3 ubiquitin ligases identifies MULAN, a mitochondrial E3 that regulates the organelle's dynamics and signaling," PLoS One, 2008, vol. 3, No. 1: e1487, Feb. 2008 (pp. 1-14).
Lu et al., "The myeloma drug lenalidomide promotes the cereblon-dependent destruction of Ikaros proteins," Science, vol. 343, No. 6168 2014 (pp. 305-309).

(56) References Cited

OTHER PUBLICATIONS

Mora et al., "Constitutive Activation of Stat3 in Human Prostate Tumors and Cell Lines: Direct Inhibition of Stat3 Signaling Induces Apoptosis of Prostate Cancer Cells," Cancer Research. 2002, 62(22):6659-66.
Morlacchi et al., "Targeting SH2 Domains in Breast Cancer," Future Medicinal Chemisry. 2014, 6(17):1909-26.
Muller et al. "Amino-Substituted Thalidomide Analogs: Potent Inhibitors of TNF-? Production," Bioorganic & Medicinal Chemistry Letters, vol. 9, 1999 (pp. 1625-1630).
Müller et al., "A high-throughput assay for signal transducer and activator of transcription 5b based on fluorescence polarization" Analytical Biochemistry. 2008, 375(2):249-54.
Ni et al., "Inhibition of Constitutively Activated Stat3 Signaling Pathway Suppresses Growth of Prostate Cancer Cells," Cancer Research. 2000, 60:1225-1228.
Nielsen et al., "Inhibition of constitutively activated Stat3 correlates with altered Bcl-2/Bax expression and induction of apoptosis in mycosis fungoides tumor cells," Leukemia. 1999, 13:735-738.
Niu et al., "Constitutive Stat3 activity up-regulates VEGF expression and tumor angiogenesis," Oncogene. 2002, 21(13):2000-2008.
O'Shea et al., "JAKs and STATs in Immunity, Immunodeficiency, and Cancer," New England Journal of Medicine. 2013, 368(2):161-70.
Oh et al., "Investigational Therapeutics Targeting the IL-4/IL-13/STAT-6 Pathway for the Treatment of Asthma," European Respiratory Review. 2019, 19(115):46-54.
Okazaki et al., "A rheostat for immune responses: the unique properties of PD-1 and their advantages for clinical application," Nat. Immunol. 2013; 14(12): 1212-1218.
Ortiz-Muñoz et al., "Suppressors of Cytokine Signaling Modulate JAK/STAT-Mediated Cell Responses During Atherosclerosis," Arteriosclerosis, Thrombosis, and Vascular Biology 2009, 29(4):525-531.
PCT International Search Report and Written Opinion from PCT/US2018/052181, dated Feb. 26, 2019.
PCT International Search Report and Written Opinion from PCT/US2019/013491, dated Mar. 18, 2019.
PCT International Search Report and Written Opinion from PCT/US2019/040462, dated Sep. 20, 2019.
PCT International Search Report and Written Opinion from PCT/US2020/026869, dated Jul. 27, 2020.
Pei et al., "STAT3 Inhibition Enhances CDN-induced STING Signaling and Antitumor Immunity," Cancer Letters. 2019, 450:110-122.
Priyadarshini et al., "Copper catalyzed oxidative cross-coupling of aromatic amines with 2-pyrrolidinone: a facile synthesis of N-aryl-r-amino-r-lactams," 2014, Tetrahedron 70(36): 6068-6074.
Pubmed Compound Summary for CID 101524675, created Dec. 18, 2015 (5 pages).
Pubmed Compound Summary for CID 138728787, created Jul. 29, 2019 (6 pages).
Pubmed Compound Summary for CID 63661260, created Oct. 22, 2012 (6 pages).
Pubmed Compound Summary for CID 65967733, created Dec. 24, 2015 (7 pages).
Pubmed Compound Summary for CID 65968760, created Oct. 24, 2012 (6 pages).
Pubmed Compound Summary for CID 84036945, created Oct. 20, 2014 (7 pages).
Pubmed Compound Summary for CID 83543479, created Oct. 20, 2014 (6 pages).
Pubmed Compound Summary for CID 110491408, created Jan. 18, 2016 (7 pages).
Pubmed Compound Summary for CID 110491555, , created Jan. 18, 2016, (7 pages).
Pubmed Compound Summary for CID 102164987, created Dec. 24, 2015 (7 pages).
Puthier et al., "IL-6 up-regulates Mcl-1 in human myeloma cells through JAK/STAT rather than Ras / MAP kinase pathway," The European Journal of Immunology. 1999, 29(12):3945-50.
Qiu, H.Y. et al., Identification of New Shikonin Derivatives as Antitumor Agents Targeting STAT3 SH2 Domain, Scientific Reports. 2017, 7(2863): 1-13.
Rahaman et al., "Inhibition of Constitutively Active Stat3 Suppresses Proliferation and Induces Apoptosis in Glioblastoma Multiforme Cells," Oncogene. 2002, 21(55):8404-13.
Raina et al., "Chemical Inducers of Targeted Protein Degradation," Journal of Biological Chemistry, vol. 285, No. 15, 2010 (pp. 11057-11060).
Ramirez, et al., "Defining causative factors contributing in the activation of hedgehog signaling in diffuse large B-cell lymphoma" Leukemia Research, vol. 36, No. 10, 2012 (pp. 1267-1273).
Rauch et al., "The regulation of inflammation by interferons and their STATs," Jak-Stat. 2013, 2(1):e23820.
Real et al., "Resistance to Chemotherapy via Stat3-dependent Overexpression of Bcl-2 in Metastatic Breast Cancer Cells," Oncogene. 2002, 21(50):7611-8.
Rokosz et al., "Kinase inhibitors as drugs for chronic inflammatory and immunological diseases: progress and challenges," Expert Opinions on Therapeutic Targets, vol. 12, No. 7, 2008 (pp. 883-903).
Ronnebaum et al., "Synthesis of 1, 2, 3-triazole 'click' analogues of thalidomide," Tetrahedron, vol. 72, No. 40, 2016 (pp. 6136-6141).
Ross et al., "Bispecific T cell engager (BITE®) antibody constructs can mediate bystander tumor cell killing", PLoS One, vol. 12, No. 8, (e0183390), Aug. 24, 2017, https://doi.org/10.1371/journal.pone.0183390. Date Accessed: Feb. 12, 2020 (24 pages).
Rostovtsev et al., "A Stepwise Huisgen Cycloaddition Process: Copper(I)?Catalyzed Regioselective "Ligation" of Azides and Terminal Alkynes," Angewandte Chemie International Edition, vol. 41, No. 14, Jul. 2002, (pp. 2596-2599).
Sartor et al., "Role of Epidermal Growth Factor Receptor and STAT-3 Activation in Autonomous Proliferation of SUM-1O2PT Human Breast Cancer Cells," Cancer Research. 1997, 57:978-987.
Schnnekloth et al., "Chemical approaches to controlling intracellular protein degradation," Chembiochem: a European Journal of Chemical Biology, vol. 6, No. 1, 2005 (pp. 40-46).
Schust et al., "A high-throughput fluorescence polarization assay for signal transducer and activator of transcription 3," Analytical Biochemistry. 2004, 330(1):114-8.
Sgrignani et al., "Structural Biology of STAT3 and Its Implications for Anticancer Therapies Development," International Journal of Molecular Sciences. 2018, 19(6):1591.
Shanmugasundaram, K. et al. "A modular PROTAC design for target destruction using a degradation signal based on a single amino acid," Journal of Biochemical Chemistry, Sep. 11, 2019, https://www.jbc.org/content/early/2019/09/11/jbc.AC119.010790.full.pdf. Date Accessed: Feb. 11, 2020 (10 pages).
Song et al., "Stat3 upregulates MEK5 expression in human breast cancer cells," Oncogene. 2004, 23:8301-8309.
Spradin et al., "Harnessing the Anti-Cancer Natural Product Nimbolide for Targeted Protein Degradation," bioRxiv.org (doi: https://doi.org/10.1101/436998), First Posted, Oct. 15, 2018, https://www.biorxiv.org/content/biorxiv/early/2019/04/09/436998.full.pdf. Date Accessed, Oct. 3, 2019 (41 pages).
Spratt et al., "RBR E3 ubiquitin ligases: new structures, new insights, new question," Biochemical Journal, vol. 458, Pt. 3, 2014 (pp. 421-437).
Stewart et al., "Efforts toward elucidating Thalidomide's molecular target: an expedient synthesis of the first Thalidomide biotin analogue," Organic & Biomolecular Chemistry, vol. 8, No. 18, 2010, 4059-4062.
Sugimoto, "Role of STAT3 in Inflammatory Bowel Disease," World Journal of Gastroenterology. 2008, 14(33):5110.
Sun et al., "Carbohydrate and protein immobilization onto solid surfaces by sequential Diels-Alder and azide-alkyne cycloadditions," Bioconjugate Chemistry, vol. 17, No. 1, 2006 (pp. 52-57).
Szelag, M. et al., "Identification of STAT1 and STAT3 Specific Inhibitors Using Comparative Virtual Screening and Docking Validation," PLoS One. 2015, 10(2):e0116688.

(56) References Cited

OTHER PUBLICATIONS

Tamiya et al., "Suppressors of Cytokine Signaling (SOCS) Proteins and JAK/STAT Pathways: Regulation of T-cell Inflammation by SOCS1 and SOCS3," Arteriosclerosis, Thrombosis, and Vascular Biology. 2011, 31(5):980-5.
Toogood, P., "Small molecule immuno-oncology therapeutic agents," Bioorganic & Medicinal Chemistry Letters, vol. 28, No. 3, 2017 (pp. 319-329).
Toure et al., "Small-Molecule PROTACS: New Approaches to Protein Degradation," Angewandte Chemie International Edition, vol. 55, No. 6, 2016 (pp. 1966-1973).
Turkson et al., "STAT Proteins: Novel Molecular Targets for Cancer Drug Discovery," Oncogene. 2000, 19(56):6613-6626.
Turkson, "STAT proteins as novel targets for cancer drug discovery," Expert Opinion on Therapeutic Targets. 2004, 8(5):409-422.
U.S. Appl. No. 62/694,924, filed Jul. 6, 2018 (160 pages).
U.S. Appl. No. 62/820,634, filed Mar. 19, 2019 (287 pages).
U.S. Appl. No. 62/863,949, filed Jun. 19, 2019 (309 pages).
Uehara et al., "Selective degradation of splicing factor CAPER? by anticancer sulfonamides," Nature Chemical Biology, vol. 13, No. 6, 2017 (pp. 675-680).
Varfolomeev et al., "IAP antagonists induce autoubiquitination of c-IAPs, NF-kappaB activation, and TNFalpha-dependent apoptosis," Cell, vol. 131, No. 4, 2007 (pp. 669-681).
Walker et al., "The Jak-STAT Pathway in Rheumatoid Arthritis," Journal of Rheumatology. 2005, 32(9):1650-1653.
Wang et al., "Regulation of the Innate and Adaptive Immune Responses by Stat-3 Signaling in Tumor Cells," Nature Medicine. 2004, 10(1):48-54.
Wang et al., "Roles of F-box proteins in cancer," Nature Reviews. Cancer, vol. 14, No. 4, 2014 (pp. 233-247).
Ward et al., "Covalent Ligand Screening Uncovers a RNF4 E3 Ligase Recruiter for Targeted Protein Degradation Applications," bioRxiv.org (doi: https://doi.org/10.1101/439125) First Posted, Oct. 16, 2018, https://www.biorxiv.org/content/biorxiv/early/2018/11/16/439125.full.pdf. Date Accessed, Oct. 3, 2019 (24 pages).
Wei et al., "Interleukin-6 Promotes Cervical Tumor Growth by VEGF-dependent Angiogenesis via a STAT3 Pathway," Oncogene. 2003, 22(10):1517-27.
Winter et al., "Selective Target Protein Degradation via Phthalimide Conjugation," Science, vol. 348, No. 6241, 2015 (pp. 1376-1381).
Yang et al., "Exploiting synthetic lethality for the therapy of ABC diffuse large B cell lymphoma" Cancer Cell, vol. 21, No. 6, 2012 (pp. 723-737).
Yesylevskyy et al., "Selective Inhibition of STAT3 with Respect to STAT1: Insights from Molecular Dynamics and Ensemble Docking Simulations," Journal of Chemical Information and Modeling. 2016, 56(8):1588-1596.
Yu et al., "Discovery of an Orally Selective Inhibitor of Signal Transducer and Activator of Transcription 3 Using Advanced Multiple Ligand Simultaneous Docking," The Journal of Medicinal Chemistry. 2017, 60(7):2718-2731.
Yu et al., "STATs in cancer inflammation and immunity: a leading role for STAT3," Nature Reviews. Cancer. 2009, 9(11): 798-809.
Yu et al., "The STATs of Cancer—New Molecular Targets Come of Age," Nature Reviews. Cancer. 2004, 4(2):97-105.
Yu et al., "Crosstalk Between Cancer and Immune Cells: Role of STAT3 in the Tumour Microenvironment," Nature. Reviews. Immunology. 2007, 7(1):41-51.
Yu. X et al., Eriocalyxin B Inhibits STAT3 Signaling by Covalently Targeting STAT3 and Blocking Phosporylation and Activation of STAT3, PLoS One. 2015, 10(5):e0128406.
Zhang et al., "Antagonizing STAT3 Activation With Benzo[b]thiophene 1, 1-dioxide Based Small Molecules," European Journal of Medicinal Chemistry. 2017, 5;125:538-550.
Zhang et al., "Electrophilic PROTACs that degrade nuclear proteins by engaging DCAF16," bioRxiv.org (doi: https://doi.org/10.1101/443804), First Posted, Oct. 15, 2018, https://www.biorxiv.org/content/biorxiv/early/2018/10/15/443804.full.pdf. Date Accessed, Oct. 3, 2019 (38 pages).
Zheng, W. et al., "Discovery of monocarbonyl curcumin-BTP hydbrids as STAT3 inhibitors for drug-sensitive and drug-resistant breast cancer therapy," Scientific Reports. 2017, 7:46352.
Zheng, W. et al., "MMPP Attenuates Non-Small Cell Lung Cancer Growth by Inhibiting the STAT3 DNA-Binding Activity via Direct Binding to the STAT3 DNA-Binding Domain," Theranostics. 2017, 7(18):4632-4642.
Zhong et al., "Stat3: A Stat Family Member Activated by Tyrosine Phosphorylation in Response to Epidermal Growth Factor and interleukin-6," Science. 1994, 264(5155):95-8.
Zhou et al., "Small molecules inhibit STAT3 activation, autophagy, and cancer cell anchorage-independent growth," Bioorganic & Medicinal Chemistry. 2017, 25(12):2995-3005.
Zhou et al., "Targets of curcumin," Current Drug Targets, vol. 12, No. 3, 2011 (pp. 332-347).
Zou et al., "PD-L1 (B7-H1) and PD-1 Pathway Blockade for Cancer Therapy: Mechanisms, Response Biomarkers and Combinations," Science Translational Medicine, vol. 8., No. 328, Mar. 2016 (pp. 1-34).

* cited by examiner

I-1 binds both STAT3 and E3 ligase

| Binding assay | | I-1 |
|---|---|---|
| E3 binding $IC_{50}$ (μM) | -STAT3 | 0.37 |
| STAT3 binding $IC_{50}$ (μM) | -E3 | 0.39 |
| | +E3 | 0.061 |

Ternary complex formation and STAT3 ubiquitination

I-103 downregulates STAT3- dependent gene expression and inhibits cell proliferation A. RT-qPCR in SU-DHL-1 cells, 24hr B. Viability, CellTiterGlo, 4 days

| Gene | mRNA IC$_{50}$ (nM)/ Max inh% 24hr |
|---|---|
| STAT3 | 141 / 62 |
| SOCS3 | 185 / 87 |
| PDL-1 | 58 / 82 |

| Assay | MOLM-16 | SU-DHL-1 |
|---|---|---|
| CTG IC$_{50}$ (nM) at Day 4 | 16 | 167 |
| STAT3 MSD DC$_{50}$ (nM) at 24hr | 4 | 28 |

I-103 promoted regression in xenograft models of leukemia and lymphoma at tolerated doses SU-DHL-1 tumor xenograft C. Tumor STAT3 and pSTAT3 degradation I-103 promoted regression in xenograft models of leukemia and lymphoma at tolerated doses SU-DHL-1 tumor xenograft D. Efficacy in NOD/SCID mice C. I-103 treatment induces apoptosis at 48 hours that leads to cell death D. Treatment with I-103 leads to an increase in subG1 cells (PI/RNAse analysis, FACS)

A. Wash-out study demonstrates sustained degradation is required for SU-DHL-1 cells to commit to death

| I-174 | Tumor STAT3 KD* |
|---|---|
| ○ Vehicle | - |
| ○ 2.5 mpk | 89.0% |
| ○ 5 mpk | 93.3% |
| ○ 10 mpk | 95.0% |
| ○ 25 mpk | 98.6% |

HiBiT-STAT3 live cell time-course in A549 cells

STAT DEGRADERS AND USES THEREOF

CROSS-REFERENCE TO RELATED APPLICATIONS

This application is a continuation of U.S. patent application Ser. No. 17/736,669, filed May 4, 2022, which is a division of U.S. patent application Ser. No. 16/841,095, filed Apr. 6, 2020, which claims the benefit of U.S. Provisional Application No. 62/830,095, filed on Apr. 5, 2019, U.S. Provisional Application No. 62/833,331, filed Apr. 12, 2019, U.S. Provisional Application No. 62/855,259, filed May 31, 2019, U.S. Provisional Application No. 62/860,512, filed Jun. 12, 2019, U.S. Provisional Application No. 62/875,362, filed Jul. 17, 2019, U.S. Provisional Application No. 62/877,051, filed Jul. 22, 2019, U.S. Provisional Application No. 62/887,872, filed Aug. 16, 2019, U.S. Provisional Application No. 62/926,127, filed Oct. 25, 2019, U.S. Provisional Application No. 62/932,957, filed Nov. 8, 2019, U.S. Provisional Application No. 62/944,810, filed Dec. 6, 2019, U.S. Provisional Application No. 62/947,310, filed Dec. 12 2019, U.S. Provisional Application No. 62/949,053, filed Dec. 17 2019, and U.S. Provisional Application No. 62/967,921, filed Jan. 30, 2020, the content of each of which is hereby incorporated by reference.

TECHNICAL FIELD OF THE INVENTION

The present invention relates to compounds and methods useful for the modulation of one or more signal transducers and activators of transcription ("STAT") via ubiquitination and/or degradation by compounds according to the present invention. The invention also provides pharmaceutically acceptable compositions comprising compounds of the present invention and methods of using said compositions in the treatment of various disorders.

BACKGROUND OF THE INVENTION

Ubiquitin-Proteasome Pathway (UPP) is a critical pathway that regulates key regulator proteins and degrades misfolded or abnormal proteins. UPP is central to multiple cellular processes, and if defective or imbalanced, it leads to pathogenesis of a variety of diseases. The covalent attachment of ubiquitin to specific protein substrates is achieved through the action of E3 ubiquitin ligases.

There are over 600 E3 ubiquitin ligases which facilitate the ubiquitination of different proteins in vivo, which can be divided into four families: HECT-domain E3s, U-box E3s, monomeric RING E3s and multi-subunit E3s. See generally Li et al. (PLOS One, 2008, 3, 1487) titled "Genome-wide and functional annotation of human E3 ubiquitin ligases identifies MULAN, a mitochondrial E3 that regulates the organelle's dynamics and signaling."; Berndsen et al. (Nat. Struct. Mol. Biol., 2014, 21, 301-307) titled "New insights into ubiquitin E3 ligase mechanism"; Deshaies et al. (Ann. Rev. Biochem., 2009, 78, 399-434) titled "RING domain E3 ubiquitin ligases."; Spratt et al. (Biochem. 2014, 458, 421-437) titled "RBR E3 ubiquitin ligases: new structures, new insights, new questions."; and Wang et al. (Nat. Rev. Cancer., 2014, 14, 233-347) titled "Roles of F-box proteins in cancer."

UPP plays a key role in the degradation of short-lived and regulatory proteins important in a variety of basic cellular processes, including regulation of the cell cycle, modulation of cell surface receptors and ion channels, and antigen presentation. The pathway has been implicated in several forms of malignancy, in the pathogenesis of several genetic diseases (including cystic fibrosis, Angelman's syndrome, and Liddle syndrome), in immune surveillance/viral pathogenesis, and in the pathology of muscle wasting. Many diseases are associated with an abnormal UPP and negatively affect cell cycle and division, the cellular response to stress and to extracellular modulators, morphogenesis of neuronal networks, modulation of cell surface receptors, ion channels, the secretory pathway, DNA repair and biogenesis of organelles.

Aberrations in the process have recently been implicated in the pathogenesis of several diseases, both inherited and acquired. These diseases fall into two major groups: (a) those that result from loss of function with the resultant stabilization of certain proteins, and (b) those that result from gain of function, i.e. abnormal or accelerated degradation of the protein target.

The UPP is used to induce selective protein degradation, including use of fusion proteins to artificially ubiquitinate target proteins and synthetic small-molecule probes to induce proteasome-dependent degradation. Bifunctional compounds composed of a target protein-binding ligand and an E3 ubiquitin ligase ligand, induced proteasome-mediated degradation of selected proteins via their recruitment to E3 ubiquitin ligase and subsequent ubiquitination. These drug-like molecules offer the possibility of temporal control over protein expression. Such compounds are capable of inducing the inactivation of a protein of interest upon addition to cells or administration to an animal or human, and could be useful as biochemical reagents and lead to a new paradigm for the treatment of diseases by removing pathogenic or oncogenic proteins (Crews C, Chemistry & Biology, 2010, 17(6):551-555; Schnnekloth J S Jr., Chembiochem, 2005, 6(1):40-46).

An ongoing need exists in the art for effective treatments for disease, especially hyperplasia and cancer, such as breast cancer. However, non-specific effects, and the inability to target and modulate certain classes of proteins altogether, such as transcription factors, remain as obstacles to the development of effective anti-cancer agents. As such, small molecule therapeutic agents that leverage E3 ligase mediated protein degradation to target cancer-associated proteins such as signal transducers and activators of transcription ("STAT") hold promise as therapeutic agents. Accordingly, there remains a need to find compounds that are STAT degraders useful as therapeutic agents.

SUMMARY OF THE INVENTION

The present application relates novel bifunctional compounds, which function to recruit STAT proteins to E3 ubiquitin ligase for degradation, and methods of preparation and uses thereof. In particular, the present disclosure provides bifunctional compounds, which find utility as modulators of targeted ubiquitination of STAT proteins, which are then degraded and/or otherwise inhibited by the bifunctional compounds as described herein. Also provided are monovalent compounds, which find utility as inducers of targeted ubiquitination of STAT proteins, which are then degraded and/or otherwise inhibited by the monovalent compounds as described herein. An advantage of the compounds provided herein is that a broad range of pharmacological activities is possible, consistent with the degradation/inhibition of STAT proteins. In addition, the description provides methods of using an effective amount of the compounds as described herein for the treatment or amelioration of a disease condition, such as cancer, e.g., breast cancer.

The present application further relates to targeted degradation of STAT proteins through the use of bifunctional molecules, including bifunctional molecules that link a cereblon-binding moiety to a ligand that binds STAT proteins.

It has now been found that compounds of this invention, and pharmaceutically acceptable compositions thereof, are effective as degraders of STAT proteins. Such compounds have the general formula I:

I

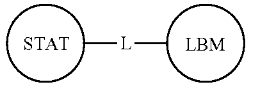

or a pharmaceutically acceptable salt thereof, wherein each variable is as defined and described herein.

It has also now been found that compounds of this invention, and pharmaceutically acceptable compositions thereof, are effective as degraders of STAT proteins. Such compounds have the general formula II:

II

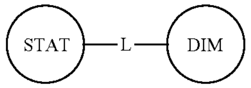

or a pharmaceutically acceptable salt thereof, wherein each variable is as defined and described herein.

Compounds of the present invention, and pharmaceutically acceptable compositions thereof, are useful for treating a variety of diseases, disorders or conditions, associated with regulation of signaling pathways implicating STAT proteins. Such diseases, disorders, or conditions include those described herein.

Compounds provided by this invention are also useful for the study of STAT proteins in biological and pathological phenomena; the study of intracellular signal transduction pathways occurring in bodily tissues; and the comparative evaluation of new STAT inhibitors or STAT degraders or other regulators of cell cycling, metastasis, angiogenesis, and immune cell evasion, in vitro or in vivo.

DETAILED DESCRIPTION OF CERTAIN EMBODIMENTS

Figures 1, 2:
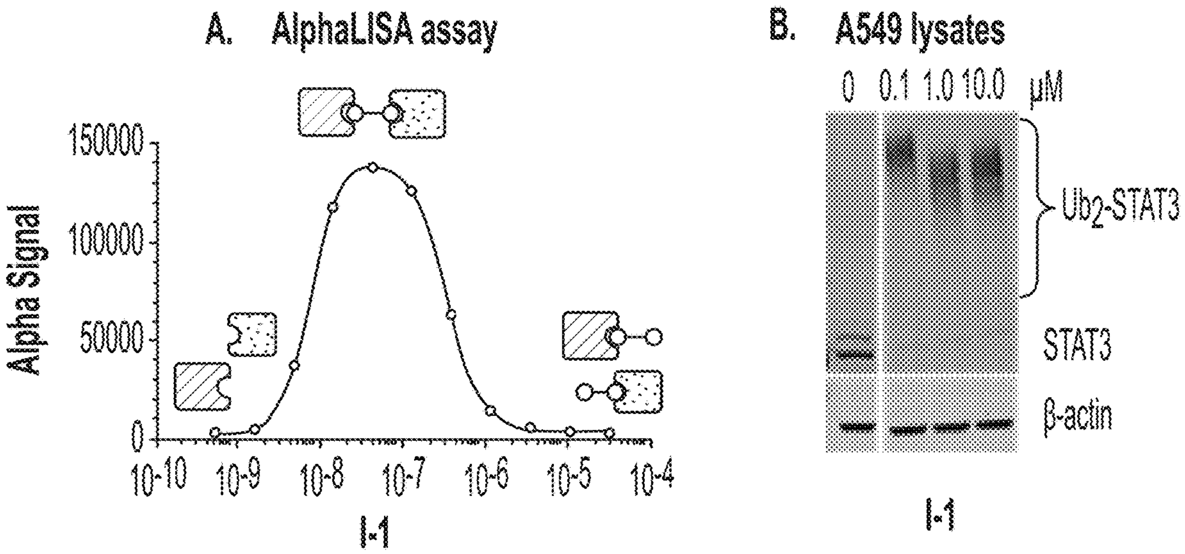
FIG. 1 shows the binding $IC_{50}$ (μM) of I-1 to both STAT3 and E3 ligase.
FIG. 2 includes images of the results of an AlphaLISA assay (A) and A549 lysates (B) of I-1 indicating efficient ternary complex formation and STAT3 ubiquitination.

1. General Description of Certain Embodiments of the Invention

Compounds of the present invention, and compositions thereof, are useful as degraders and/or inhibitors of one or more STAT proteins. In some embodiments, a provided compound degrades and/or inhibits one or more of STAT1, STAT2, STAT3, STAT4, STAT5A, STAT5B, or STAT6.

In certain embodiments, the present invention provides a compound of formula I:

I

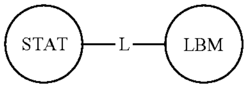

or a pharmaceutically acceptable salt thereof, wherein:
STAT is a STAT binding moiety capable of binding to one or more of STAT1, STAT2, STAT3, STAT4, STAT5A, STAT5B, or STAT6;
L is a bivalent moiety that connects STAT to LBM; and
LBM is a ligase binding moiety.

In certain embodiments, the present invention provides a compound of formula II:

II

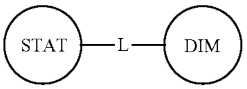

or a pharmaceutically acceptable salt thereof, wherein:
STAT is a STAT binding moiety capable of binding to one or more of STAT1, STAT2, STAT3, STAT4, STAT5A, STAT5B, or STAT6;
L is a bivalent moiety that connects STAT to DIM; and
DIM is a degradation inducing moiety.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, $75^{th}$ Ed. Additionally, general principles of organic chemistry are described in "Organic Chemistry", Thomas Sorrell, University Science Books, Sausalito: 1999, and "March's Advanced Organic Chemistry", $5^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. In some embodiments, a carbocyclic ring may be a 5-12 membered bicyclic, bridged bicyclic, or spirocyclic ring. A carbocyclic ring may include one or more oxo (=O) or thioxo (=S) substituent. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

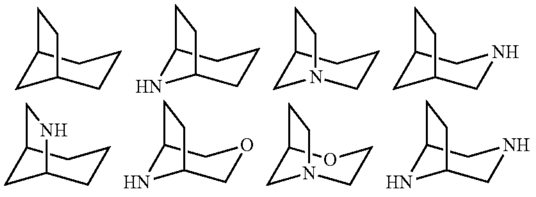

-continued

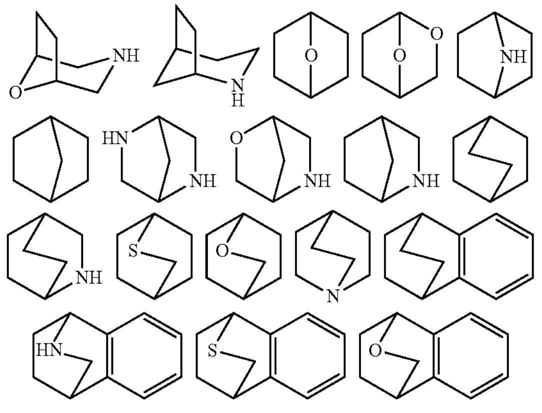

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR•(as in N-substituted pyrrolidinyl)).

The term "unsaturated," as used herein, means that a moiety has one or more units of unsaturation.

As used herein, the term "bivalent $C_{1-8}$(or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the

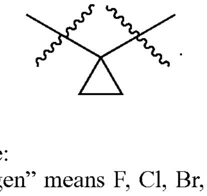

following structure:

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or *NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. In some embodiments, a heterocyclic ring may be a 5-12 membered bicyclic, bridged bicyclic, or spirocyclic ring. A heterocyclic ring may include one or more oxo (=O) or thioxo (=S) substituent. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $—(CH_2)_{0-4}R^\circ$; $—(CH_2)_{0-4}OR^\circ$; $—O(CH_2)_{0-4}R^\circ$, $—O—(CH_2)_{0-4}C(O)OR^\circ$; $—(CH_2)_{0-4}CH(OR^\circ)_2$; $—(CH_2)_{0-4}SR^\circ$; $—(CH_2)_{0-4}Ph$, which may be substituted with $R^\circ$; $—(CH_2)_{0-4}O(CH_2)_{0-1}Ph$ which may be substituted with $R^\circ$; $—CH{=}CHPh$, which may be substituted with $R^\circ$; $—(CH_2)_{0-4}O(CH_2)_{0-1}$-pyridyl which may be substituted with $R^\circ$; $—NO_2$; $—CN$; $—N_3$; $—(CH_2)_{0-4}N(R^\circ)_2$; $—(CH_2)_{0-4}N(R^\circ)C(O)R^\circ$; $—N(R^\circ)C(S)R^\circ$; $—(CH_2)_{0-4}N(R^\circ)C(O)NR^\circ_2$; $—N(R^\circ)C(S)NR^\circ_2$; $—(CH_2)_{0-4}N(R^\circ)C(O)OR^\circ$; $—N(R^\circ)N(R^\circ)C(O)R^\circ$; $—N(R^\circ)N(R^\circ)C(O)NR^\circ_2$; $—N(R^\circ)N(R^\circ)C(O)OR^\circ$; $—(CH_2)_{0-4}C(O)R^\circ$; $—C(S)R^\circ$; $—(CH_2)_{0-4}C(O)OR^\circ$; $—(CH_2)_{0-4}C(O)SR^\circ$; $—(CH_2)_{0-4}C(O)OSiR^\circ_3$; $—(CH_2)_{0-4}OC(O)R^\circ$; $—OC(O)(CH_2)_{0-4}SR—$, $SC(S)SR^\circ$; $—(CH_2)_{0-4}SC(O)R^\circ$; $—(CH_2)_{0-4}C(O)NR^\circ_2$; $—C(S)NR^\circ_2$; $—C(S)SR^\circ$; $—SC(S)SR^\circ$, $—(CH_2)_{0-4}OC(O)NR^\circ_2$; $—C(O)N(OR^\circ)R^\circ$; $—C(O)C(O)R^\circ$; $—C(O)CH_2C(O)R^\circ$; $—C(NOR^\circ)R^\circ$; $—(CH_2)_{0-4}SSR^\circ$; $—(CH_2)_{0-4}S(O)_2R^\circ$; $—(CH_2)_{0-4}S(O)_2OR^\circ$; $—(CH_2)_{0-4}OS(O)_2R^\circ$; $—S(O)_2NR^\circ_2$; $—(CH_2)_{0-4}S(O)R^\circ$; $—N(R^\circ)S(O)_2NR^\circ_2$; $—N(R^\circ)S(O)_2R^\circ$; $—N(OR^\circ)R^\circ$; $—C(NH)NR^\circ_2$; $—P(O)_2R^\circ$; $—P(O)R^\circ_2$; $—OP(O)R^\circ_2$; $—OP(O)(OR^\circ)_2$; $SiR^\circ_3$; $—(C_{1-4}$ straight or branched alkylene)$O—N(R^\circ)_2$; or $—(C_{1-4}$ straight or branched alkylene)$C(O)O—N(R^\circ)_2$, wherein each $R^\circ$ may be substituted as defined below and is independently hydrogen, $C_{1-6}$ aliphatic, $—CH_2Ph$, $—O(CH_2)_{0-1}Ph$, $—CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $—(CH_2)_{0-2}R^\bullet$, -(halo$R^\bullet$), $—(CH_2)_{0-2}OH$, $—(CH_2)_{0-2}OR^\bullet$, $—(CH_2)_{0-2}CH(OR^\bullet)_2$; $—O$(halo$R^\bullet$), $—CN$, $—N_3$, $—(CH_2)_{0-2}C(O)R^\bullet$, $—(CH_2)_{0-2}C(O)OH$, $—(CH_2)_{0-2}C(O)OR^\bullet$, $—(CH_2)_{0-2}SR^\bullet$, $—(CH_2)_{0-2}SH$, $—(CH_2)_{0-2}NH_2$, $—(CH_2)_{0-2}NHR^\bullet$, $—(CH_2)_{0-2}NR^\bullet_2$, $—NO_2$, $—SiR^\bullet_3$, $—OSiR^\bullet_3$, $—C(O)SR^\bullet$, $—(C_{1-4}$ straight or branched alkylene)$C(O)OR^\bullet$, or $—SSR^\bullet$ wherein each $R^\bullet$ is unsubstituted or where preceded by "halo" is substituted only with one or more halogens, and is independently selected from $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include $=O$ and $=S$.

Suitable divalent substituents on a saturated carbon atom of an "optionally substituted" group include the following: $=O$, $=S$, $=NNR^*_2$, $=NNHC(O)R^*$, $=NNHC(O)OR^*$, $=NNHS(O)_2R^*$, $=NR^*$, $=NOR^*$, $—O(C(R^*_2))_{2-3}O—$, or $—S(C(R^*_2))_{2-3}S—$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $—O(CR^*2)_{2-3}O—$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, $—R^\bullet$, -(halo$R^\bullet$), $—OH$, $—OR^\bullet$, $—O$(halo$R^\bullet$), $—CN$, $—C(O)OH$, $—C(O)OR^\bullet$, $—NH_2$, $—NHR^\bullet$, $—NR^\bullet_2$, or $—NO_2$, wherein each $R^\bullet$ is unsubstituted or where preceded by "halo" is substituted only with one or more halogens, and is independently $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $—R^\dagger$, $—NR^\dagger_2$, $—C(O)R^\dagger$, $—C(O)OR^\dagger$, $—C(O)C(O)R^\dagger$, $—C(O)CH_2C(O)R^\dagger$, $—S(O)_2R^\dagger$, $—S(O)_2NR^\dagger_2$, $—C(S)NR^\dagger_2$, $—C(NH)NR^\dagger_2$, or $—N(R^\dagger)S(O)_2R^\dagger$; wherein each $R^{\backslash}$ is independently hydrogen, $C_{1-6}$ aliphatic which may be substituted as defined below, unsubstituted $—OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^{\backslash}$, taken together with their intervening atom(s) form an unsubstituted 3-12-membered saturated, partially unsaturated, or aryl mono or bicyclic ring having 0-4 heteroatoms independently selected from nitrogen, oxygen, or sulfur.

Suitable substituents on the aliphatic group of $R^{\backslash}$ are independently halogen, $—R^\bullet$, -(halo$R^\bullet$), $—OH$, $—OR^\bullet$, $—O$(halo$R^\bullet$), $—CN$, $—C(O)OH$, $—C(O)OR^\bullet$, $—NH_2$, —NHR$^{\bullet}$, —NR$^{\bullet}_2$, or —$NO_2$, wherein each R$^{\bullet}$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}\text{-alkyl})_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate. In some embodiments, the provided compounds are purified in salt form for convenience and/or ease of purification, e.g., using an acidic or basic mobile phase during chromatography. Salts forms of the provided compounds formed during chromotagraphic purification are comtemplated herein (e.g., diammonium salts) and are readily apparent to those having skill in the art.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a 13C- or $^{14}C$-enriched carbon are within the scope of this invention. Such compounds are useful, for example, as analytical tools, as probes in biological assays, or as therapeutic agents in accordance with the present invention As used herein, the term "provided compound" refers to any genus, subgenus, and/or species set forth herein.

The term "prodrug" refers to a compound that is made more active in vivo. The present compounds can also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound. The term "therapeutically acceptable prodrug," refers to those prodrugs or zwitterions which are suitable for use in contact with the tissues of patients without undue toxicity, irritation, and allergic response, are commensurate with a reasonable benefit/risk ratio, and are effective for their intended use.

As used herein, the term "inhibitor" is defined as a compound that binds to and/or inhibits an STAT protein with measurable affinity. In certain embodiments, an inhibitor has an $IC_{50}$ and/or binding constant of less than about 50 μM, less than about 1 μM, less than about 500 nM, less than about 100 nM, less than about 10 nM, or less than about 1 nM.

As used herein, the term "degrader" is defined as a heterobifunctional compound that binds to and/or inhibits both an STAT protein and an E3 ligase with measurable affinity resulting in the ubiquitination and subsequent degradation of the STAT protein. In certain embodiments, a degrader has an $DC_{50}$ of less than about 50 μM, less than about 1 μM, less than about 500 nM, less than about 100 nM, less than about 10 nM, or less than about 1 nM. As used herein, the term "monovalent" refers to a degrader compound without an appended E3 ligase binding moiety.

A compound of the present invention may be tethered to a detectable moiety. It will be appreciated that such compounds are useful as imaging agents. One of ordinary skill in the art will recognize that a detectable moiety may be attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties may be directly attached to a provided compound or via a tethering group, such as a bivalent saturated or unsaturated hydrocarbon chain. In some embodiments, such moieties may be attached via click chemistry. In some embodiments, such moieties may be attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41, 2596-99 and Sun et al., Bioconjugate Chem., 2006, 17, 52-57.

As used herein, the term "detectable moiety" is used interchangeably with the term "label" and relates to any moiety capable of being detected, e.g., primary labels and secondary labels. Primary labels, such as radioisotopes (e.g., tritium, $^{32}P$, $^{33}P$, $^{35}S$, or $^{14}C$), mass-tags, and fluorescent labels are signal generating reporter groups which can be detected without further modifications. Detectable moieties also include luminescent and phosphorescent groups.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360,8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The terms "measurable affinity" and "measurably inhibit," as used herein, means a measurable change in a STAT protein activity between a sample comprising a compound of the present invention, or composition thereof, and a STAT protein, and an equivalent sample comprising a STAT protein, in the absence of said compound, or composition thereof.

3. Description of Exemplary Embodiments

As described above, in certain embodiments, the present invention provides a compound of formula I:

I

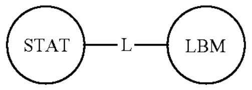

or a pharmaceutically acceptable salt thereof, wherein:

STAT is a STAT protein binding moiety capable of binding to one or more of STAT1, STAT2, STAT3, STAT4, STAT5A, STAT5B, or STAT6;

L is a bivalent moiety that connects STAT to LBM; and

LBM is a E3 ubiquitin ligase binding moiety.

In some embodiments, the present invention provides a compound of formula L:

I

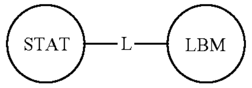

or a pharmaceutically acceptable salt thereof, wherein:

STAT is a STAT3 binding moiety;

L is a bivalent moiety that connects STAT to LBM; and

LBM is a cereblon E3 ubiquitin ligase binding moiety.

As described above, in certain embodiments, the present invention provides a compound of formula II:

II

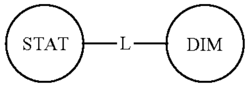

or a pharmaceutically acceptable salt thereof, wherein:

STAT is a STAT protein binding moiety capable of binding to one or more of STAT1, STAT2, STAT3, STAT4, STAT5A, STAT5B, or STAT6;

L is a bivalent moiety that connects STAT to DIM; and

DIM is a degradation inducing moiety.

In some embodiments, the present invention provides a compound of formula II:

II

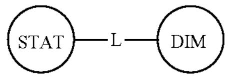

or a pharmaceutically acceptable salt thereof, wherein:

STAT is a STAT3 binding moiety;

L is a bivalent moiety that connects STAT to DIM; and

DIM is LBM, a lysine mimetic, or a hydrogen atom.

Ligase Binding Moiety (LBM)

In some embodiments, LBM is an E3 ligase ligand. Such E3 ligase ligands are well known to one of ordinary skill in the art and include those described in M. Toure, C. M. Crews, Angew. Chem. Int. Ed. 2016, 55, 1966, T. Uehara et al. *Nature Chemical Biology* 2017, 13, 675, WO 2017/176708, US 2017/0281784, WO 2017/161119, WO 2017/176957, WO 2017/176958, WO 2015/160845, US 2015/0291562, WO 2016/197032, WO 2016/105518, US 2018/0009779, WO 2017/007612, 2018/0134684, WO 2013/106643, US 2014/0356322, WO 2002/020740, US 2002/0068063, WO 2012/078559, US 2014/0302523, WO 2012/003281, US 2013/0190340, US 2016/0022642, WO 2014/063061, US 2015/0274738, WO 2016/118666, US 2016/0214972, WO 2016/149668, US 2016/0272639, WO 2016/169989, US 2018/0118733, WO 2016/197114, US 2018/0147202, WO 2017/011371, US 2017/0008904, WO 2017/011590, US 2017/0037004, WO 2017/079267, US 2017/0121321, WO 2017/117473, WO 2017/117474, WO 2013/106646, WO 2014/108452, WO 2017/197036, WO 2017/197046, WO 2017/197051, WO 2017/197055, and WO 2017/197056 each of, the entirety of each of which is herein incorporated by reference.

As defined herein and described below, wherein a formula is depicted using square brackets, e.g,

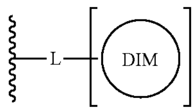

or

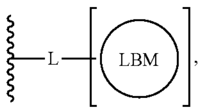

,

L is attached to a modifiable carbon, oxygen, or nitrogen atom within DIM or LBM including substitution or replacement of a defined group in DIM or LBM.

In certain embodiments, the present invention provides a compound of Formula I, wherein LBM is an E3 ubiquitin ligase (cereblon) binding moiety thereby forming a compound of formula I-a-1, I-a-2, I-a-3, I-a-4, I-a-5, I-a-6, I-a-7, I-a-8, I-a-9, or I-a-10 respectively:

I-a-1

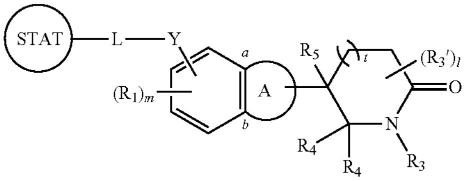

-continued

I-a-2

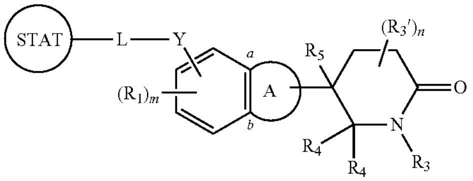

I-a-3

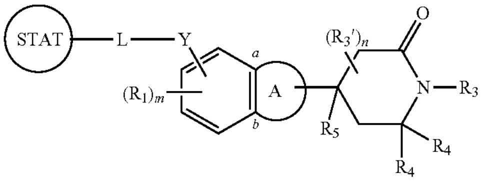

I-a-4

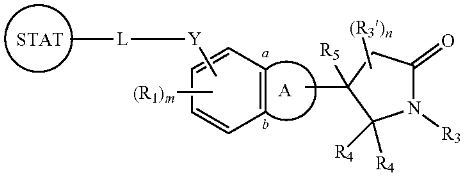

I-a-5

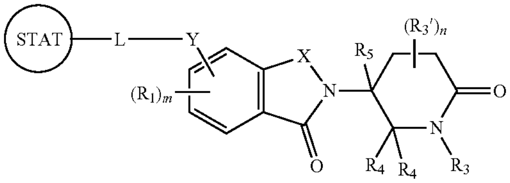

I-a-6

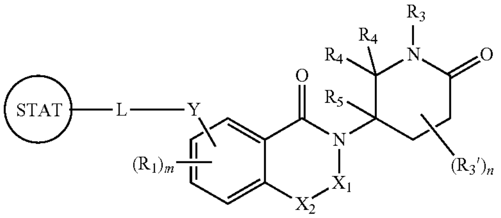

I-a-7

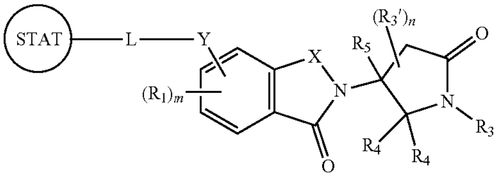

I-a-8

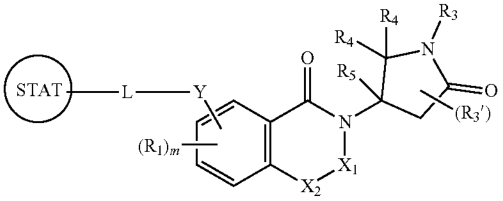

I-a-9

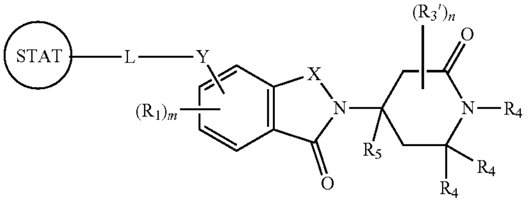

-continued
I-a-10
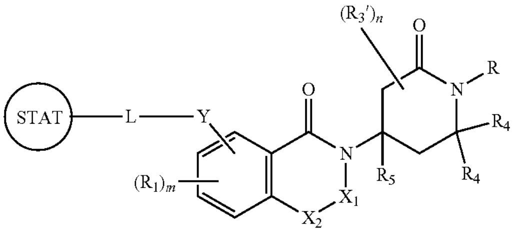
or a compound of formula I-a'-1, I-a'-2, I-a'-3, I-a'-4, I-a'-5, I-a'-6, I-a'-7, I-a'-8, I-a'-9, or I-a'-10 respectively:
I-a'-1
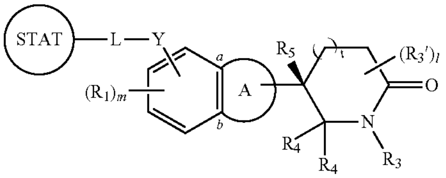
I-a'-2
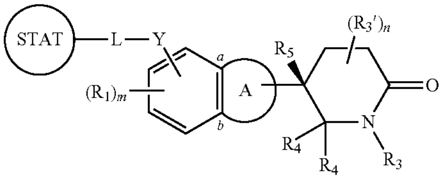
I-a'-3
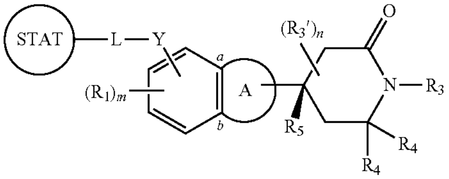
I-a'-4
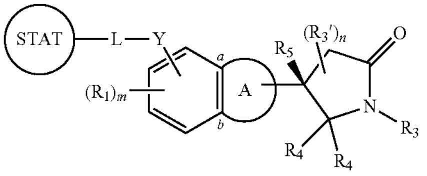
I-a'-5
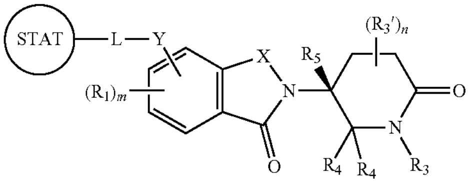
I-a'-6
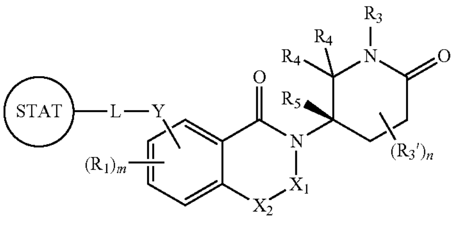
-continued
I-a'-7
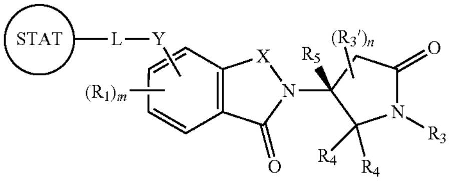
I-a'-8
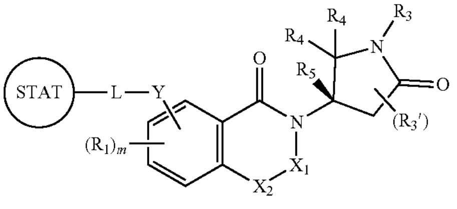
I-a'-9
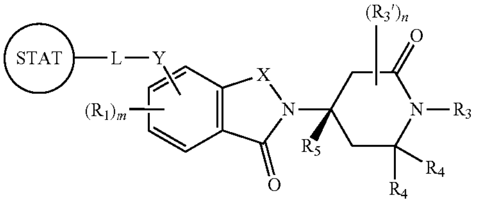
I-a'-10
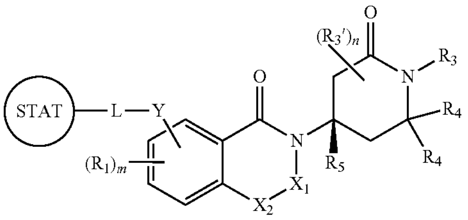
I-a'-9
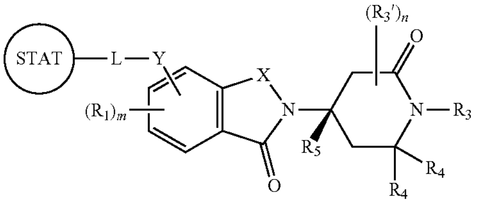
I-a'-10
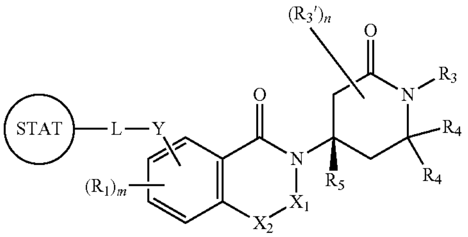
or a compound of formula I-a"-1, I-a"-2, I-a"-3, I-a"-4, I-a"-5, I-a"-6, I-a"-7, I-a"-8, I-a"-9, or I-a"-10 respectively:
I-a"-1
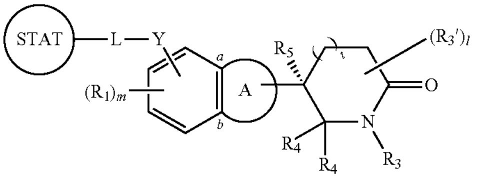

-continued

I-a''-2

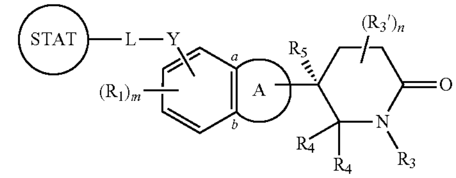

I-a''-3

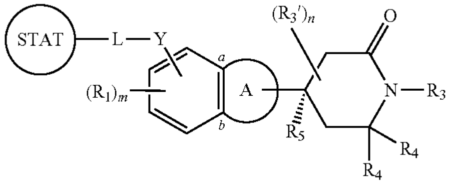

I-a''-4

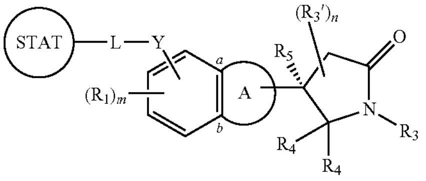

I-a''-5

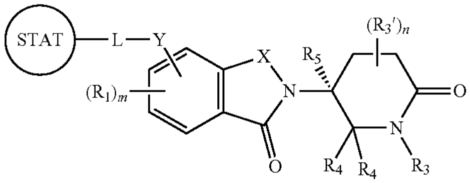

I-a''-6

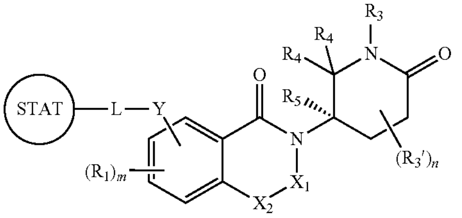

I-a''-7

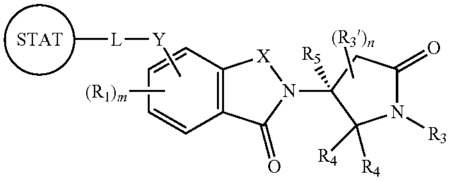

I-a''-8

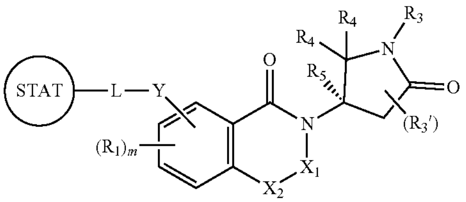

I-a''-9

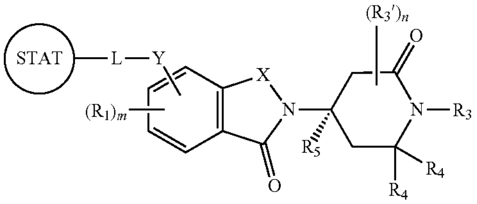

-continued

I-a''-9

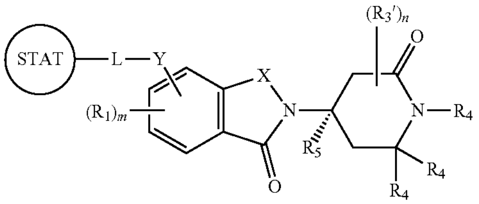

I-a''-10

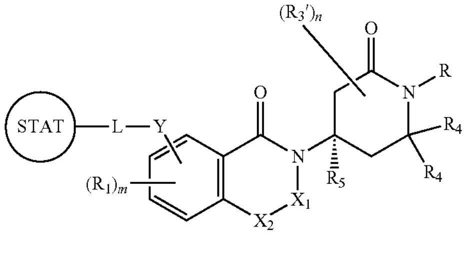

or a pharmaceutically acceptable salt thereof, wherein L and STAT are as defined above and described in embodiments herein, and wherein each of the variables

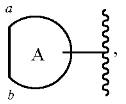

X, $X_1$, $X_2$, Y, $R_1$, $R_3$, $R^{3'}$, $R_4$, $R_5$, t, m and n is as defined and described in WO 2017/007612 and US 2018/0134684, the entirety of each of which is herein incorporated by reference.

In certain embodiments, the present invention provides a compound of Formula I, wherein LBM is an E3 ubiquitin ligase (cereblon) binding moiety thereby forming a compound of formula I-b-1, I-b-2, I-b-3, I-b-4, I-b-5, or I-b-6 respectively:

I-b-1

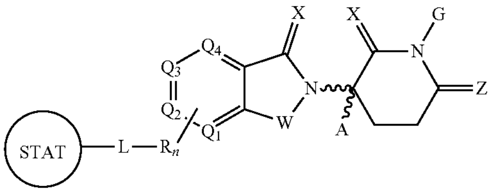

I-b-2

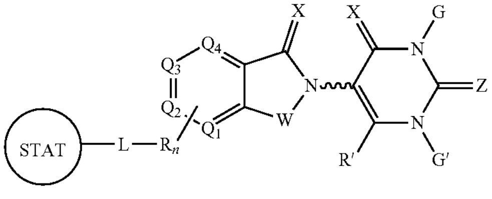

I-b-3

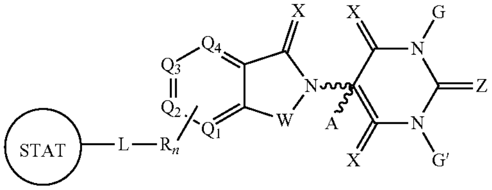

-continued

I-b-4

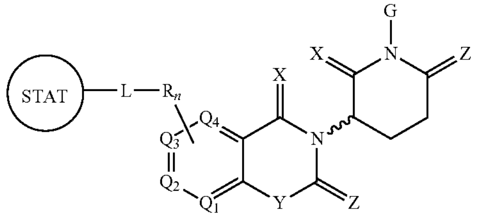

I-b-5

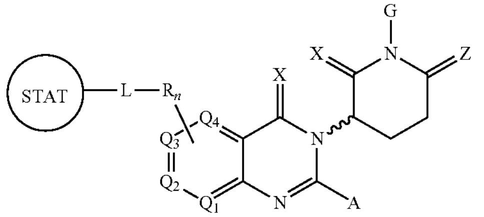

I-b-6

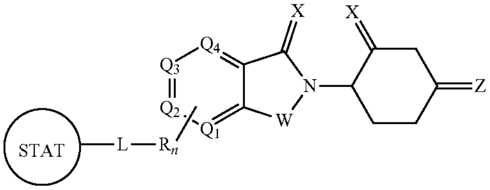

or a pharmaceutically acceptable salt thereof, wherein L and STAT are as defined above and described in embodiments herein, and wherein each of the variables A, G, G', $Q_1$, $Q_2$, $Q_3$, $Q_4$, R, R', W, X, Y, Z, ⁓, and n is as defined and described in WO 2016/197114 and US 2018/0147202, the entirety of each of which is herein incorporated by reference.

In some embodiments, LBM is

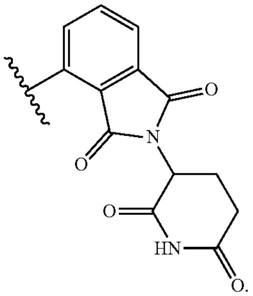 [SMILES: *c1cccc2c1C(=O)N(C1CCC(=O)NC1=O)C2=O]

In some embodiments, LBM is

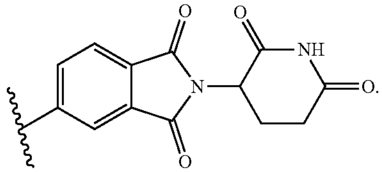 [SMILES: *c1ccc2c(c1)C(=O)N(C1CCC(=O)NC1=O)C2=O]

In some embodiments, LBM is

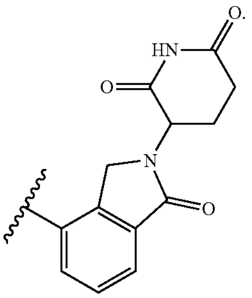

In some embodiments, LBM is

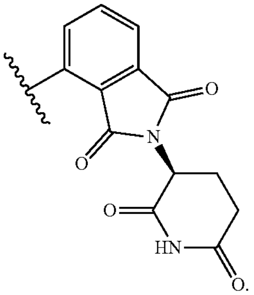 [SMILES: *c1cccc2c1C(=O)N([C@H]1CCC(=O)NC1=O)C2=O]

In some embodiments, LBM is

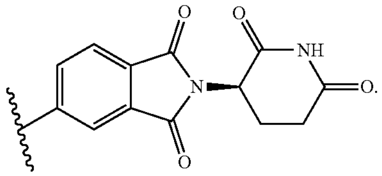 [SMILES: *c1ccc2c(c1)C(=O)N([C@@H]1CCC(=O)NC1=O)C2=O]

In some embodiments, LBM is

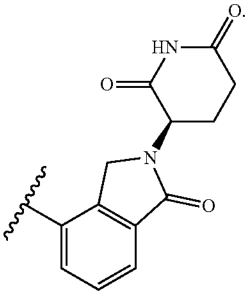 [SMILES: *c1cccc2c1CN([C@@H]1CCC(=O)NC1=O)C2=O]

In some embodiments, LBM is

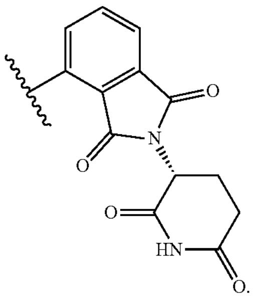 [SMILES: *c1cccc2c1C(=O)N([C@@H]1CCC(=O)NC1=O)C2=O]

In some embodiments, LBM is

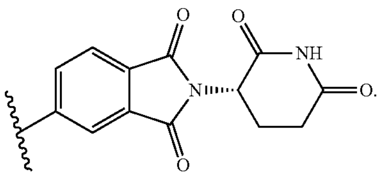 [SMILES: *c1ccc2c(c1)C(=O)N([C@H]1CCC(=O)NC1=O)C2=O]

In some embodiments, LBM is

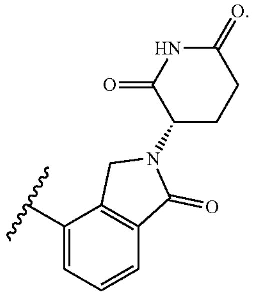 [SMILES: *c1cccc2c1CN([C@H]1CCC(=O)NC1=O)C2=O]

In certain embodiments, the present invention provides a compound of formula I, wherein LBM is an E3 ubiquitin ligase (cereblon) binding moiety thereby forming a compound of formula I-c:

I-c

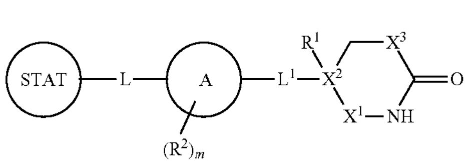

or a pharmaceutically acceptable salt thereof, wherein L and STAT are as defined above and described herein, and wherein:

$X^1$ is a bivalent moiety selected from a covalent bond, —$CH_2$—, —$CHCF_3$—, —$SO_2$—, —S(O)—, —P(O)R—, —P(O)OR—, —P(O)$NR_2$—, —C(O)—, —C(S)—, or

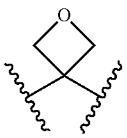

;

$X^2$ is a carbon atom or silicon atom;

$X^3$ is a bivalent moiety selected from —$CR_2$—, —NR—, —O—, —S—, or —Si($R_2$)—;

$R^1$ is hydrogen, deuterium, halogen, —CN, —OR, —SR, —S(O)R, —$S(O)_2R$, —$N(R)_2$, —P(O)$(OR)_2$, —P(O)($NR_2$)OR, —P(O)$(NR_2)_2$, —$Si(OH)_2R$, —Si(OH)$(R)_2$, —$Si(R)_3$, or an optionally substituted $C_{1-4}$ aliphatic;

each $R^2$ is independently hydrogen, deuterium, —$R^6$, halogen, —CN, —$NO_2$, —OR, —SR, —$N(R)_2$, —$Si(R)_3$, —$S(O)_2R$, —$S(O)_2N(R)_2$, —S(O)R, —C(O)R, —C(O)OR, —C(O)$N(R)_2$, —C(O)N(R)OR, —$C(R)_2$N(R)C(O)R, —$C(R)_2$N(R)C(O)$N(R)_2$, —OC(O)R, —OC(O)$N(R)_2$, —OP(O)$R_2$, —OP(O)$(OR)_2$, —OP(O)(OR)($NR_2$), —OP(O)$(NR_2)_2$—, —N(R)C(O)OR, —N(R)C(O)R, —N(R)C(O)$N(R)_2$, —N(R)$S(O)_2R$, —NP(O)$R_2$, —N(R)P(O)$(OR)_2$, —N(R)P(O)(OR)($NR_2$) —N(R)P(O)$(NR_2)_2$ or —N(R)$S(O)_2R$;

Ring A is a bi- or tricyclic ring selected from

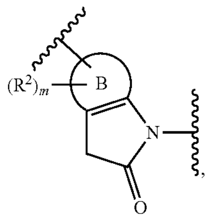

,

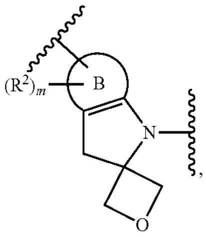

,

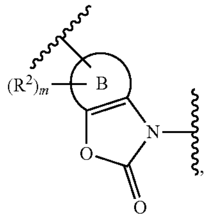

,

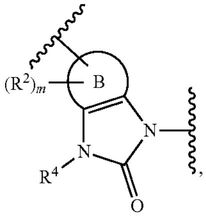

,

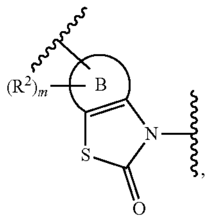

,

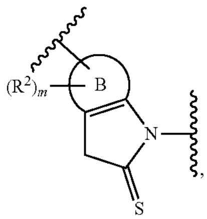

,

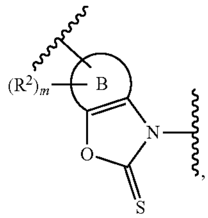

,

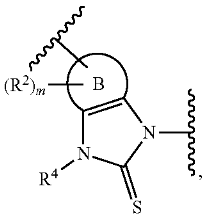

,

-continued
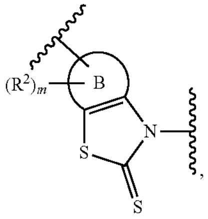
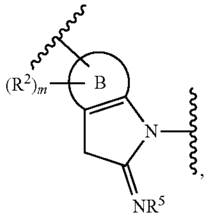
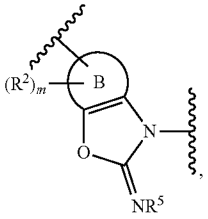
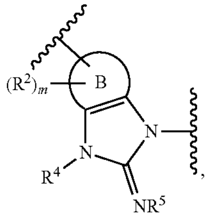
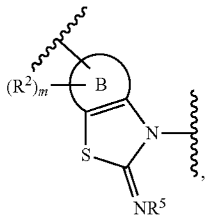
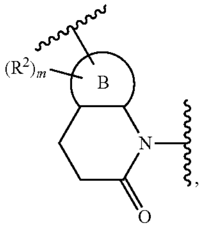
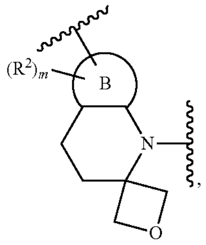
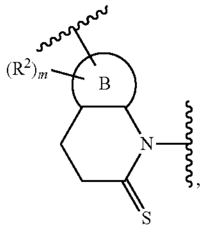
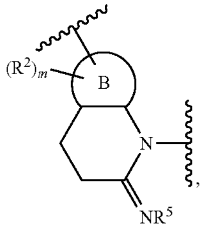
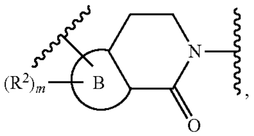
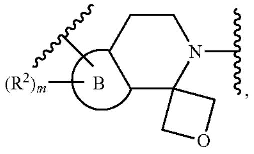
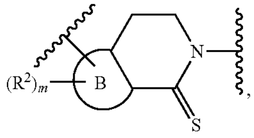
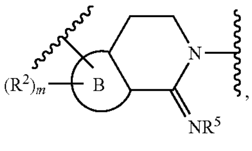
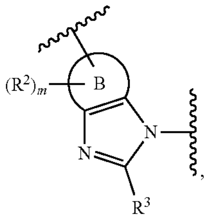
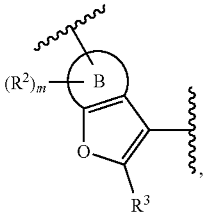
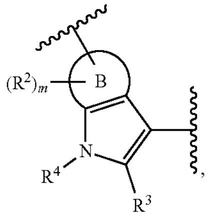
-continued
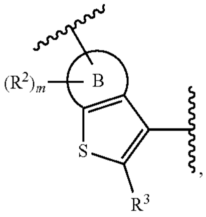
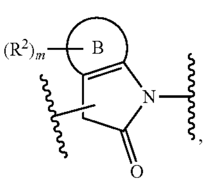
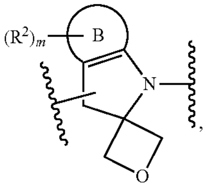
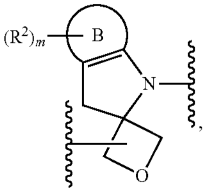
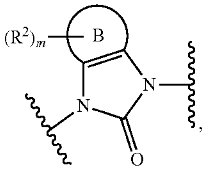
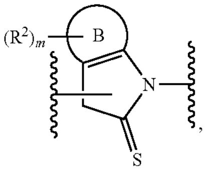
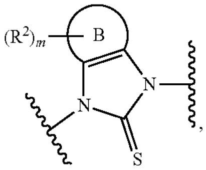
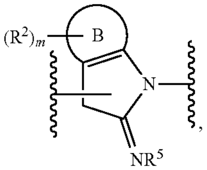
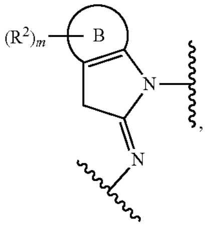
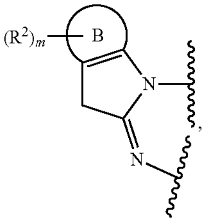
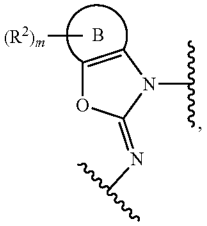
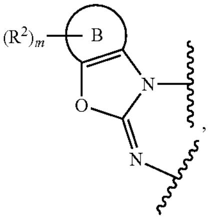
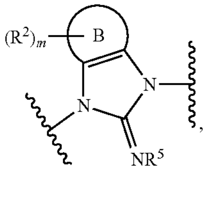
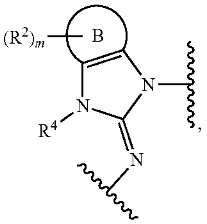
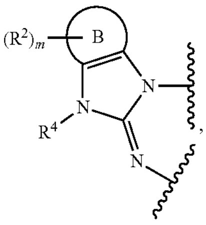
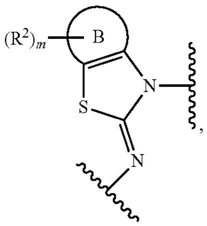

-continued

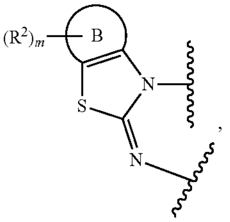,
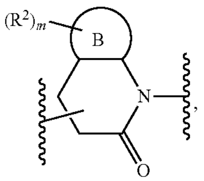,
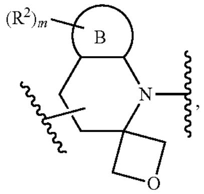,
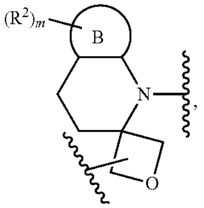,
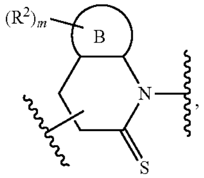,
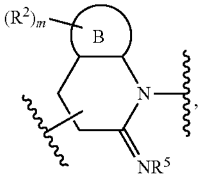,
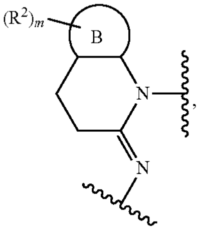,
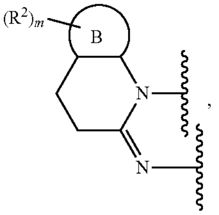,
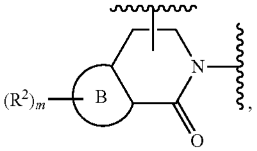,
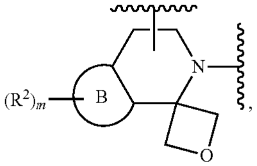,
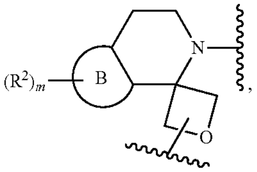,
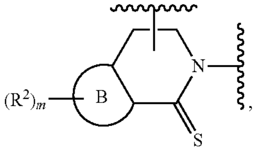,
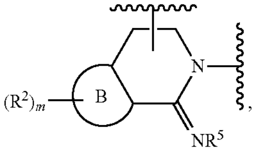,
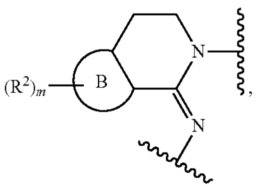,
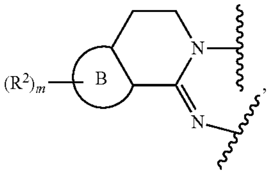,
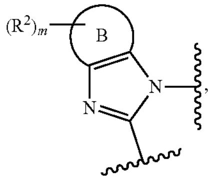

-continued

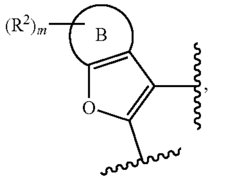,
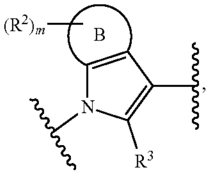,
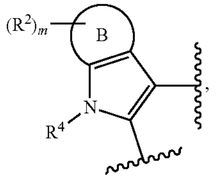, or
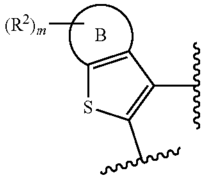

wherein

Ring B is a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;

$R^3$ is selected from hydrogen, halogen, —OR, —N(R)$_2$, or —SR;

each $R^4$ is independently hydrogen, —$R^6$, halogen, —CN, —$NO_2$, —OR, —SR, —$NR_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

$R^5$ is hydrogen, $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

$L^1$ is a covalent bond or a $C_{1-3}$ bivalent straight or branched saturated or unsaturated hydrocarbon chain wherein 1-2 methylene units of the chain are independently and optionally replaced with —O—, —C(O)—C(S)—, —C(R)$_2$—, —CH(R)—, —C(F)$_2$—, —N(R)—, —S(O)$_2$— or —(C)═CH—;

m is 0, 1, 2, 3 or 4;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

Where a point of attachment of —$(R^2)_m$ is depicted on Ring B, it is intended, and one of ordinary skill in the art would appreciate, that the point of attachment of —$(R^2)_m$ may be on Ring A and may also be at any available carbon or nitrogen atom on Ring A including the ring to which Ring B is fused. Where —$R^2$ is attached to a nitrogen atom bound to $R^4$ or R, $R^4$ or $R^5$ is absent and —$R^2$ takes the place of the $R^4$ or $R^5$ group. Where —$R^2$ is attached to a carbon atom bound to $R^3$, $R^3$ is absent and —$R^2$ takes the place of the $R^3$ group.

In some embodiments, a compound of formula I-c above is provided as a compound of formula I-c' or formula I-c'':

I-c'

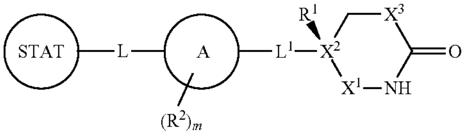

I-c''

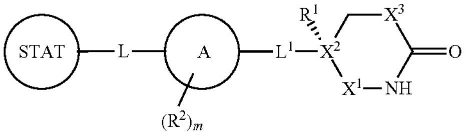

or a pharmaceutically acceptable salt thereof, wherein: each of STAT, Ring A, L, $L^1$, $R^1$, $R^2$, $X^1$, $X^2$, $X^3$, and m is as defined above.

In certain embodiments, the present invention provides a compound of Formula I, wherein LBM is an E3 ubiquitin ligase (cereblon) binding moiety thereby forming a compound of formula I-d:

I-d

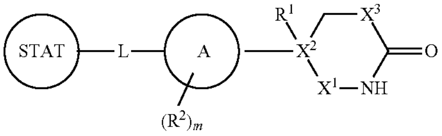

or a pharmaceutically acceptable salt thereof, wherein L and STAT are as defined above and described in embodiments herein, and wherein:

$X^1$ is a bivalent moiety selected from a covalent bond, —$CH_2$—, —$CHCF_3$—, —$SO_2$—, —S(O)—, —P(O)R—, —P(O)OR—, —P(O)$NR_2$—, —C(O)—, —C(S)—, or

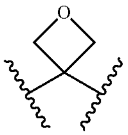

;

$X^2$ is a carbon atom or silicon atom;

$X^3$ is a bivalent moiety selected from —$CR_2$—, —NR—, —O—, —S—, or —Si($R_2$)—;

$R^1$ is hydrogen, deuterium, halogen, —CN, —OR, —SR, —S(O)R, —S(O)$_2$R, —N(R)$_2$, —P(O)(OR)$_2$, —P(O)($NR_2$)OR, —P(O)($NR_2$)$_2$, —Si(OH)$_2$R, —Si(OH)(R)$_2$, —Si(R)$_3$, or an optionally substituted $C_{1-4}$ aliphatic;

each $R^2$ is independently hydrogen, deuterium, —$R^6$, halogen, —CN, —$NO_2$, —OR, —SR, —N(R)$_2$, —Si(R)$_3$, —S(O)$_2$R, —S(O)$_2$N(R)$_2$, —S(O)R, —C(O)R, —C(O)OR, —C(O)N(R)$_2$, —C(O)N(R)OR, —C(R)$_2$N(R)C(O)R, —C(R)$_2$N(R)C(O)N(R)$_2$, —OC(O)R, —OC(O)N(R)$_2$, —OP(O)$R_2$, —OP(O)(OR)$_2$, —OP(O)(OR)($NR_2$), —OP(O)($NR_2$)$_2$—, —N(R)C(O)OR, —N(R)C(O)R, —N(R)C(O)N(R)$_2$, —N(R)S(O)$_2$R, —NP(O)$R_2$, —N(R)P(O)(OR)$_2$, —N(R)P(O)(OR)($NR_2$), —N(R)P(O)($NR_2$)$_2$, or —N(R)S(O)$_2$R;

Ring A is a bi- or tricyclic ring selected from

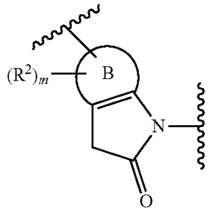

wherein Ring B is other than imidazo or benzo,

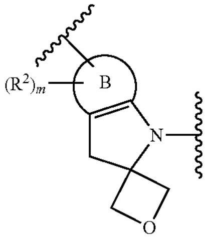

,

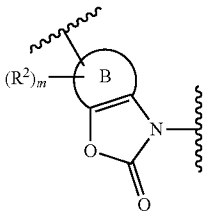

wherein Ring B is other than benzo,

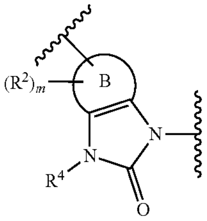

wherein Ring B is other than benzo,

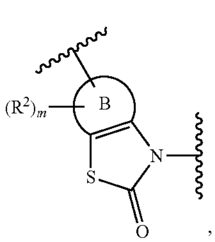

,

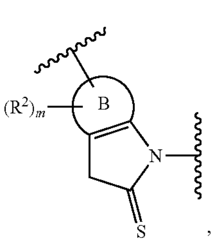

,

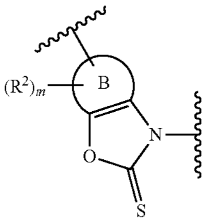

,

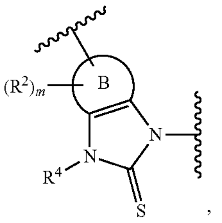

,

-continued
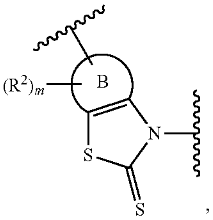,
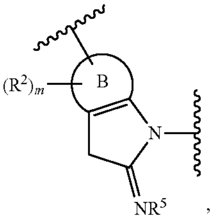,
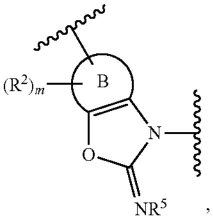,
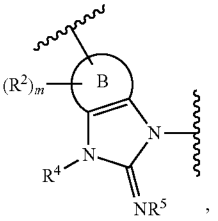,
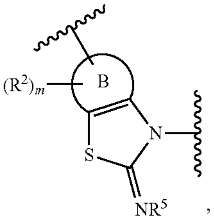,
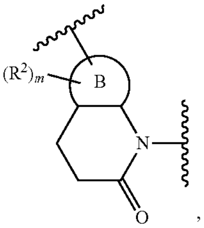,
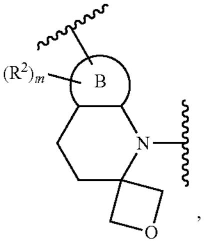,
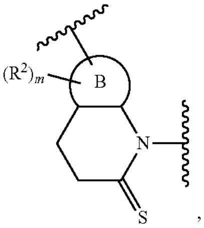,
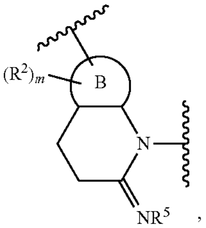,
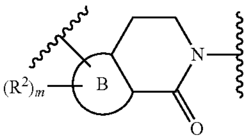
wherein Ring B is other than benzo,
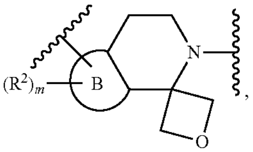,
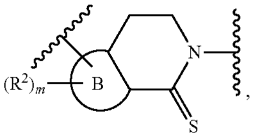,
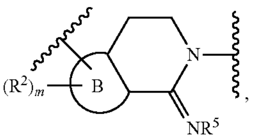,
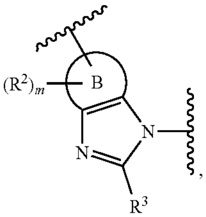,
-continued
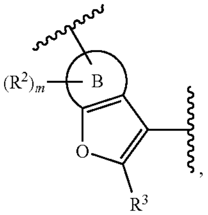,
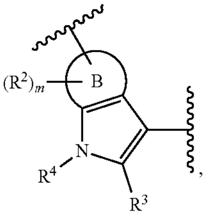,
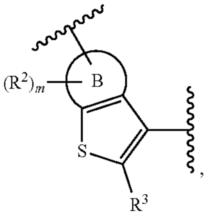,
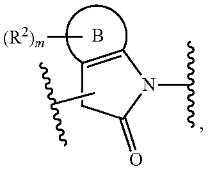,
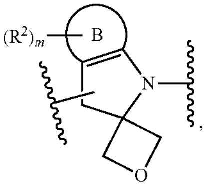,
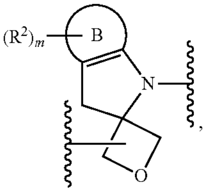,
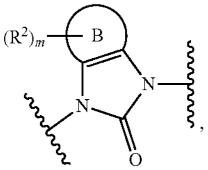,
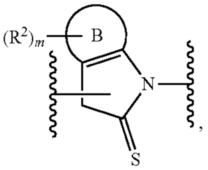,
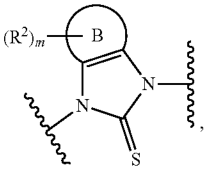,
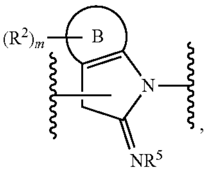,
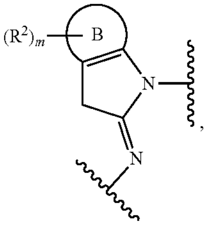,
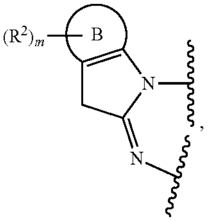,
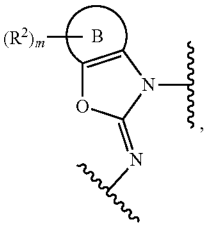,
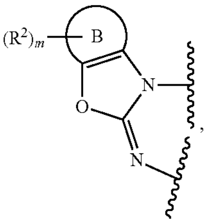,
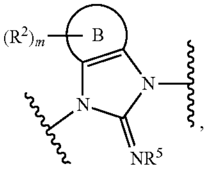,
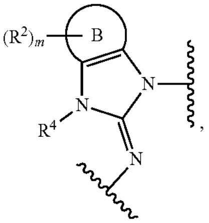, -continued

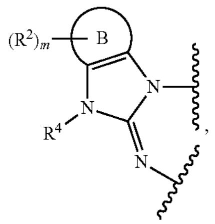
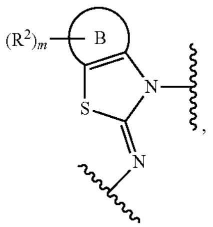
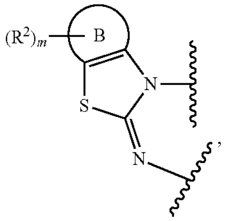
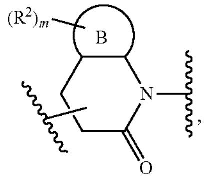
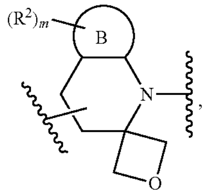
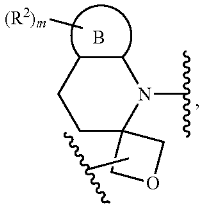
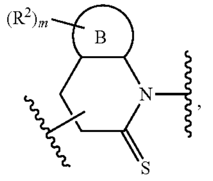
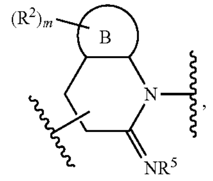
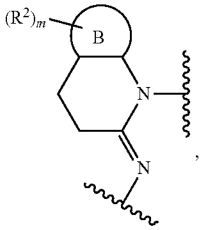
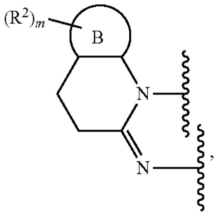
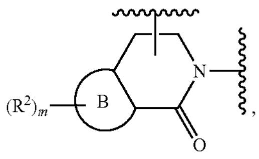
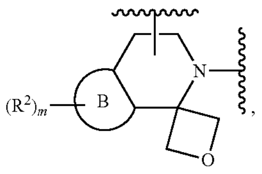
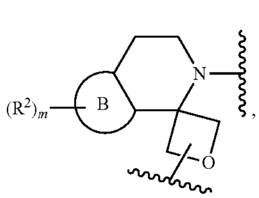
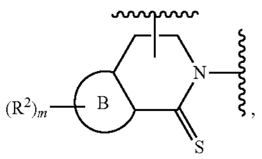
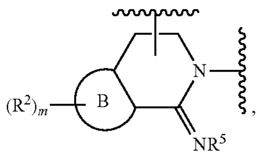
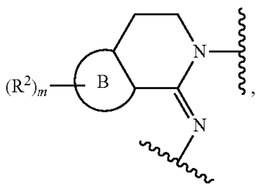

-continued

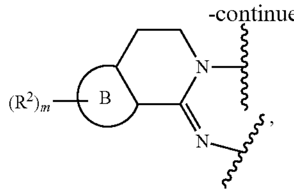
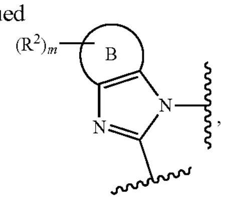
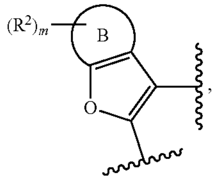
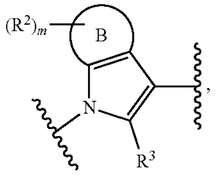
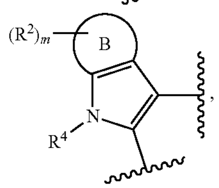
or
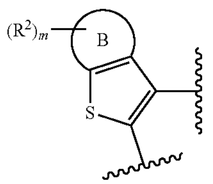

wherein

Ring B is a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;

$R^3$ is selected from hydrogen, halogen, —OR, —$N(R)_2$, or —SR;

each $R_4$ is independently hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —$C(O)NR_2$, —C(O)N(R)OR, —OC(O)R, —$OC(O)NR_2$, —N(R)C(O)OR, —N(R)C(O)R, —$N(R)C(O)NR_2$, or —$N(R)S(O)_2R$;

$R^5$ is hydrogen, $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, 2, 3 or 4; and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

Where a point of attachment of —$(R^2)_m$ is depicted on Ring B, it is intended, and one of ordinary skill in the art would appreciate, that the point of attachment of —$(R^2)_m$ may be on Ring A and may also be at any available carbon or nitrogen atom on Ring A including the ring to which Ring B is fused. Where —$R^2$ is attached to a nitrogen atom bound to $R^4$ or $R^5$, $R^4$ or $R^5$ is absent and —$R^2$ takes the place of the $R^4$ or $R^5$ group. Where —$R^2$ is attached to a carbon atom bound to $R^3$, $R^3$ is absent and —$R^2$ takes the place of the $R^3$ group.

In some embodiments, the compound of formula I-d above is provided as a compound of formula I-d' or formula I-d":

I-d'

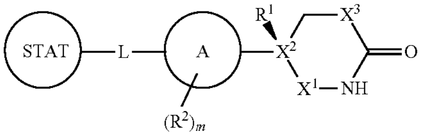

I-d"

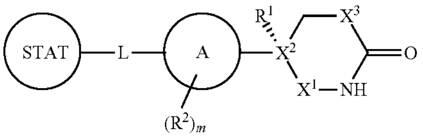

or a pharmaceutically acceptable salt thereof, wherein:

each of STAT, Ring A, L, $R^1$, $R^2$, $X^1$, $X^2$, $X^3$, and m is as defined above.

In certain embodiments, the present invention provides a compound of Formula I, wherein LBM is an E3 ubiquitin ligase (cereblon) binding moiety thereby forming a compound of formula I-e:

I-e

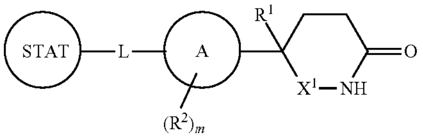

or a pharmaceutically acceptable salt thereof, wherein L and STAT are as defined above and described in embodiments herein, and wherein:

X is a bivalent moiety selected from a covalent bond, —$CH_2$—, —C(O)—, —C(S)—, or

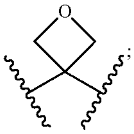 [SMILES: *C1(*)COC1]

;

$R^1$ is hydrogen, deuterium, halogen, —CN, —OR, —SR, —S(O)R, —$S(O)_2R$, —$NR_2$, or an optionally substituted $C_{1-4}$ aliphatic;

each $R^2$ is independently hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)$S(O)_2R$;

Ring A is a bi- or tricyclic ring selected from

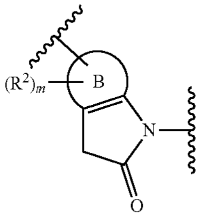,
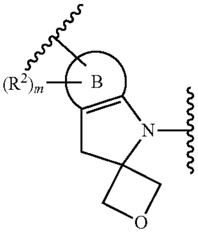,
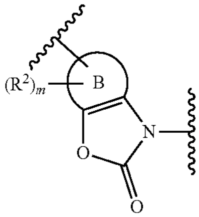,
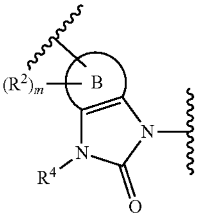,
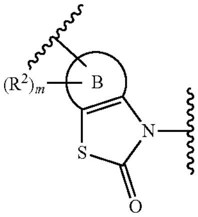,
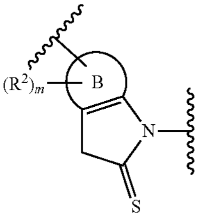,
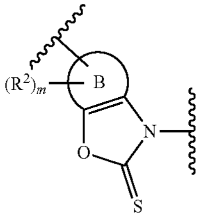,
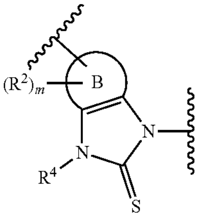,
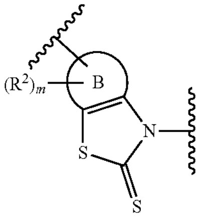,
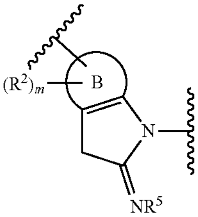,
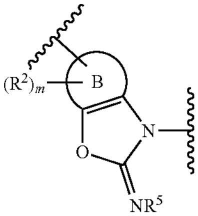,
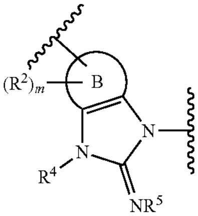,
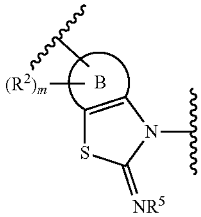,
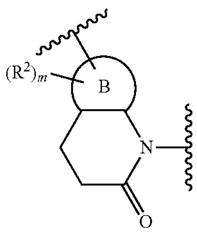, -continued
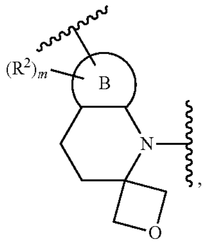
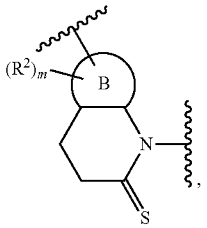
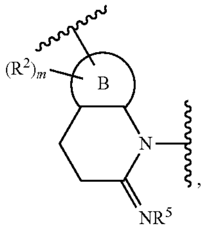
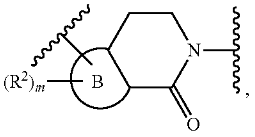
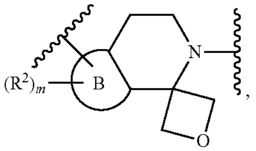
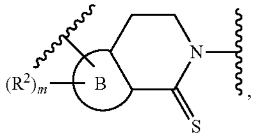
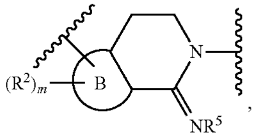
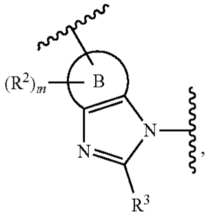
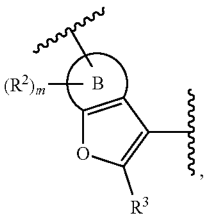
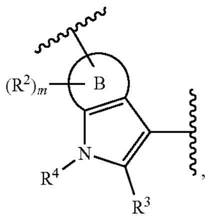
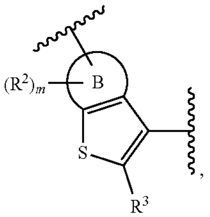
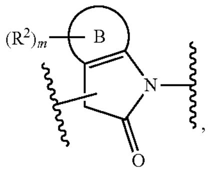
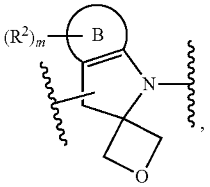
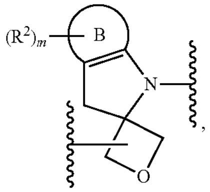
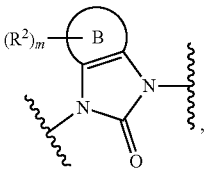
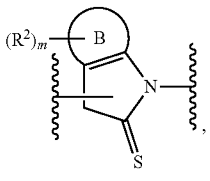
-continued
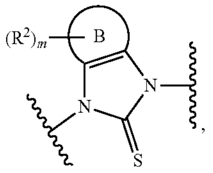
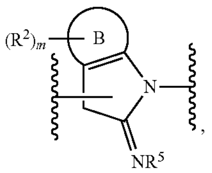
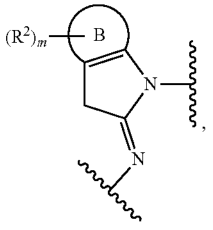
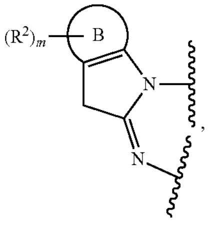
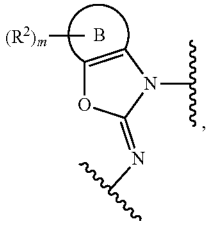
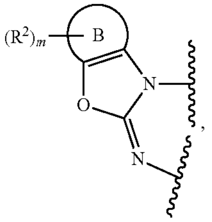
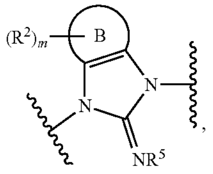
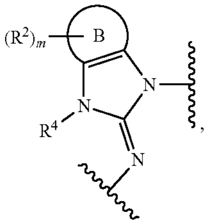
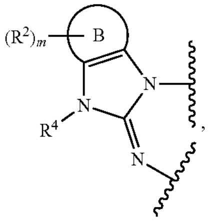
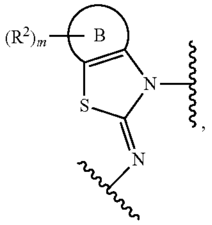
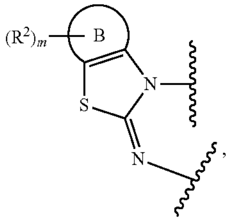
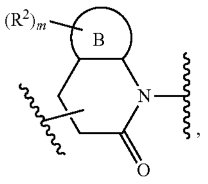
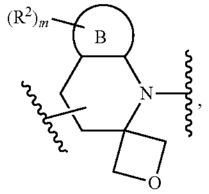
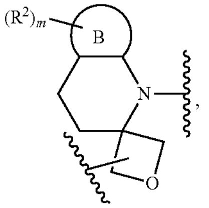
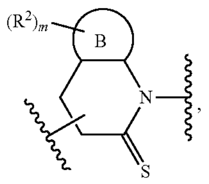
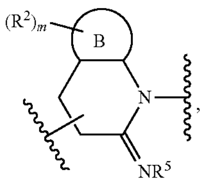

-continued

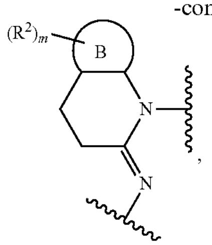,
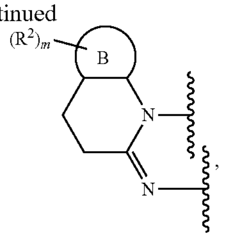,
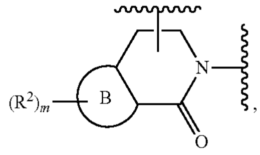,
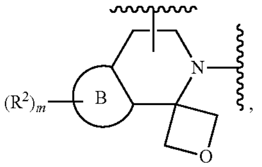,
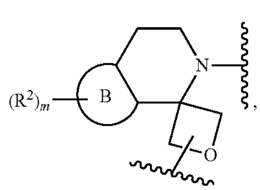,
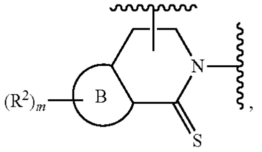,
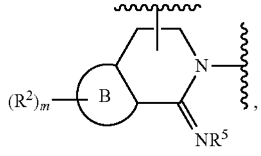,
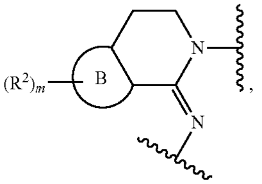,
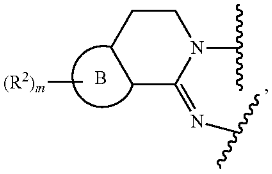,
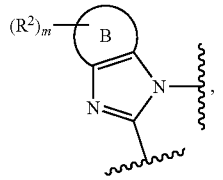,
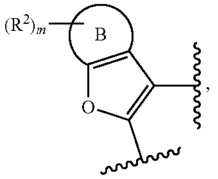,
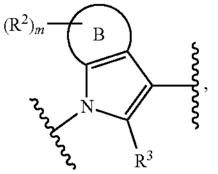,
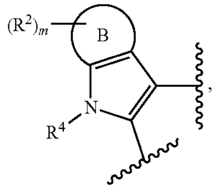, or
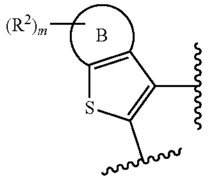

wherein

Ring B is a fused ring selected from 6-membered aryl, 6-membered heteroaryl containing 1-4 heteroatoms independently selected from nitrogen, oxygen, and sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;

$R^3$ is selected from hydrogen, halogen, —OR, —$N(R)_2$, or —SR;

each $R_4$ is independently hydrogen, —R, halogen, —CN, —$NO_2$, —OR, —SR, —$NR_2$, —$S(O)_2R$, —$S(O)_2NR_2$, —S(O)R, —C(O)R, —C(O)OR, —$C(O)NR_2$, —C(O)N(R)OR, —OC(O)R, —$OC(O)NR_2$, —N(R)C(O)OR, —N(R)C(O)R, —N(R)C(O)$NR_2$, or —N(R)$S(O)_2R$;

$R^5$ is hydrogen, $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, 2, 3 or 4; and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

Where a point of attachment of —$(R^2)_m$ is depicted on Ring B, it is intended, and one of ordinary skill in the art would appreciate, that the point of attachment of —$(R^2)_m$ may be on Ring A and may also be at any available carbon or nitrogen atom on Ring A including the ring to which Ring B is fused. Where —$R^2$ is attached to a nitrogen atom bound to $R^4$ or $R^5$, $R^4$ or $R^5$ is absent and —$R^2$ takes the place of the $R^4$ or $R^5$ group. Where —$R^2$ is attached to a carbon atom bound to $R^3$, $R^3$ is absent and —$R^2$ takes the place of the R group.

In some embodiments, the compound of formula I-e above is provided as a compound of formula I-e' or formula I-e":

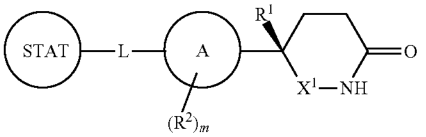

I-e'

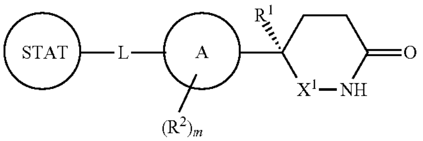

I-e"

or a pharmaceutically acceptable salt thereof, wherein:

each of STAT, Ring A, L, $R^1$, $R^2$, $X^1$, and m is as defined above.

In certain embodiments, the present invention provides a compound of formula I, wherein LBM is an E3 ubiquitin ligase (cereblon) binding moiety thereby forming a compound of formula I-f:

I-f

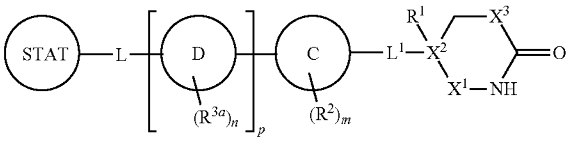

or a pharmaceutically acceptable salt thereof, wherein, L and STAT are as defined above and described in embodiments herein, and wherein:

$X^1$ is a bivalent moiety selected from a covalent bond, —$CH_2$—, —$CHCF_3$—, —$SO_2$—, —S(O)—, —P(O)R—, —P(O)OR—, —P(O)$NR_2$—, —C(O)—, —C(S)—, or

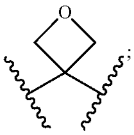 [SMILES: *C1(*)COC1];

$X^2$ is a carbon atom or silicon atom;

$X^3$ is a bivalent moiety selected from —$CR_2$—, —NR—, —O—, —S—, or —Si($R_2$)—;

$R^1$ is hydrogen, deuterium, halogen, —CN, —OR, —SR, —S(O)R, —S(O)$_2$R, —$NR_2$, —P(O)(OR)$_2$, —P(O)($NR_2$)OR, —P(O)($NR_2$)$_2$, —Si(OH)$_2$R, —Si(OH)(R)$_2$, —Si(R)$_3$, or an optionally substituted $C_{1-4}$ aliphatic;

Ring C is a mono- or bicyclic ring selected from

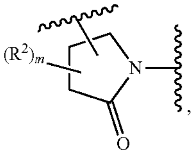, 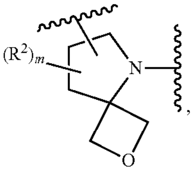,

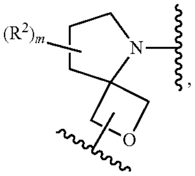, 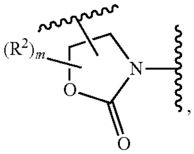,

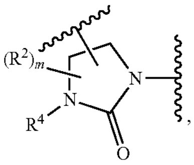, 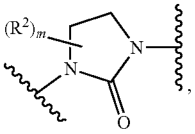,

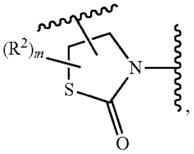, 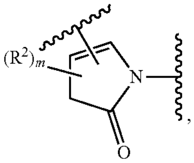,

-continued

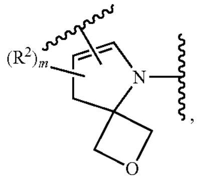, 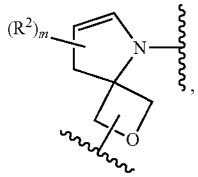,

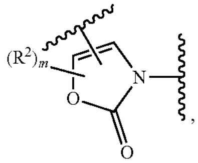, 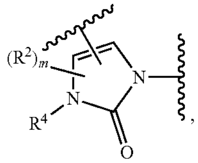,

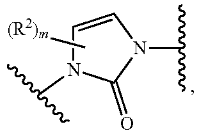, 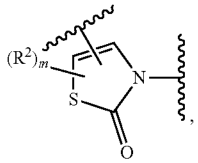,

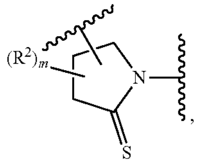, 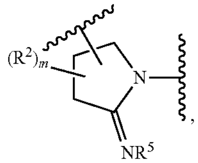,

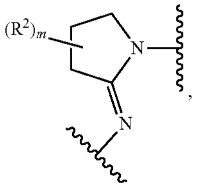, 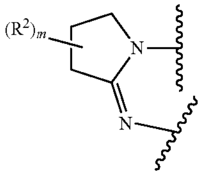,

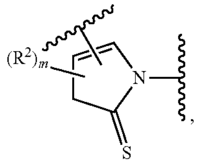, 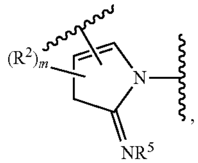,

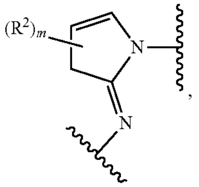, 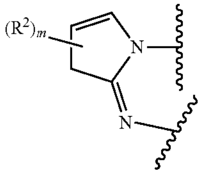,

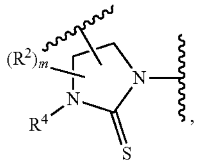, 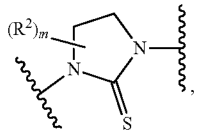,

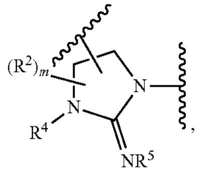, 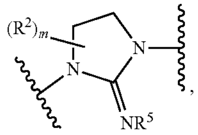,

-continued

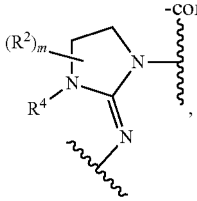, 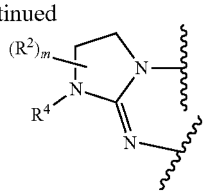,

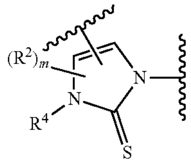, 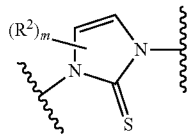,

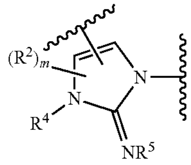, 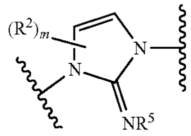,

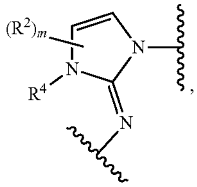, 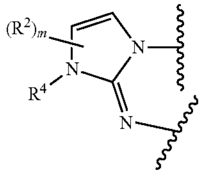,

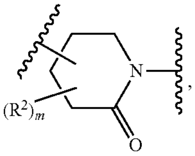, 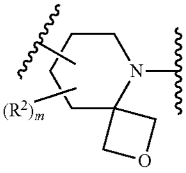,

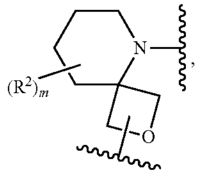, 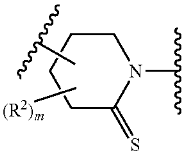,

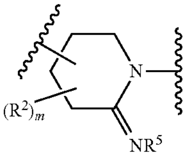, 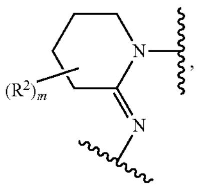, or

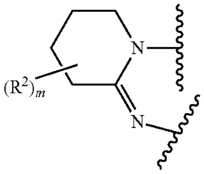;

each of $R^2$ and $R^{3a}$ is independently hydrogen, deuterium, —$R^6$, halogen, —CN, —$NO_2$, —OR, —SR, —$N(R)_2$, —$Si(R)_3$, —$S(O)_2R$, —$S(O)_2N(R)_2$, —S(O)R, —C(O)R, —C(O)OR, —$C(O)N(R)_2$, —C(O)N(R)OR, —$C(R)_2N$(R)C(O)R, —$C(R)_2N(R)C(O)N(R)_2$, —OC(O)R, —OC(O)$N(R)_2$, —$OP(O)R_2$, —$OP(O)(OR)_2$, —OP(O)(OR)($NR_2$), —$OP(O)(NR_2)_2$—, —N(R)C(O)OR, —N(R)C(O)R, —N(R)C(O)$N(R)_2$, —$N(R)S(O)_2R$, —$NP(O)R_2$, —$N(R)P(O)(OR)_2$, —N(R)P(O)(OR)($NR_2$), —N(R)P(O)$(NR_2)_2$, or —$N(R)S(O)_2R$;

Ring D is selected from a 6-membered aryl, 6-membered heteroaryl containing 1-4 heteroatoms independently selected from nitrogen, oxygen, and sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;

each $R_4$ is independently hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —$C(O)NR_2$, —C(O)N(R)OR, —OC(O)R, —OC(O)$NR_2$, —N(R)C(O)OR, —N(R)C(O)R, —N(R)C(O)$NR_2$, or —$N(R)S(O)_2R$;

$R^5$ is hydrogen, $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

$L^1$ is a covalent bond or a $C_{1-3}$ bivalent straight or branched saturated or unsaturated hydrocarbon chain wherein 1-2 methylene units of the chain are independently and optionally replaced with —O—, —C(O)—C(S)—, —$C(R)_2$—, —CH(R)—, —$C(F)_2$—, —N(R)—, —$S(O)_2$— or —(C)=CH—;

m is 0,1,2,3 or 4; n is 0, 1, 2, 3 or 4;

p is 0 or 1, wherein when p is 0, the bond connecting Ring C and Ring D is connected to

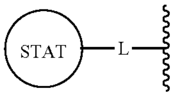

and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, a compound of formula I-f above is provided as a compound of formula I-f' or formula I-f":

I-f'

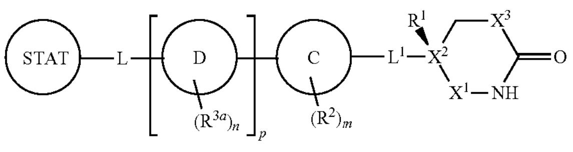

-continued

I-f''

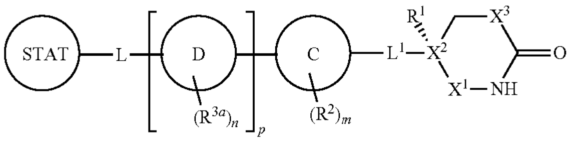

or a pharmaceutically acceptable salt thereof, wherein: each of STAT, Ring C, Ring D, L, $L^1$, $R^1$, $R^2$, $R^{3a}$, $X^1$, $X^2$, $X^3$, n, m, and p is as defined above.

In certain embodiments, the present invention provides a compound of Formula I, wherein LBM is an E3 ubiquitin ligase (cereblon) binding moiety thereby forming a compound of formula I-g:

I-g

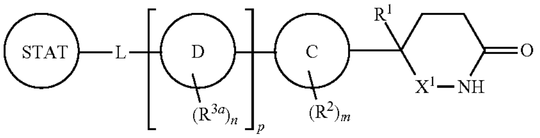

or a pharmaceutically acceptable salt thereof, wherein L and STAT are as defined above and described in embodiments herein, and wherein:

$X^1$ is a bivalent moiety selected from a covalent bond, —$CH_2$—, —C(O)—, —C(S)—, or

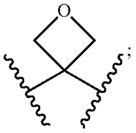 [SMILES: *C1(*)COC1]

$R^1$ is hydrogen, deuterium, halogen, —CN, —OR, —SR, —S(O)R, —$S(O)_2R$, —$NR_2$, or an optionally substituted $C_{1-4}$ aliphatic;

Ring C is a mono- or bicyclic ring selected from

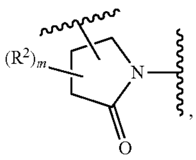 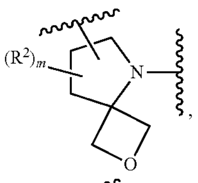

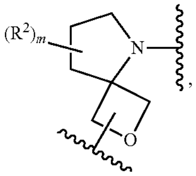 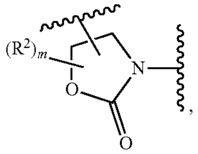

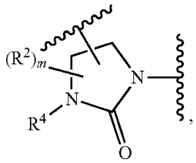 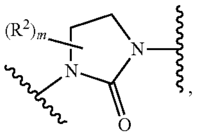

-continued

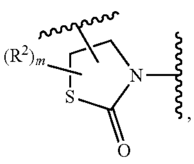 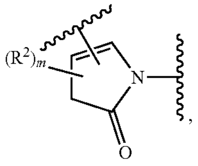

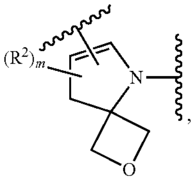 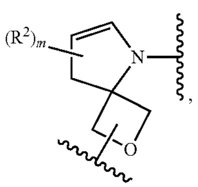

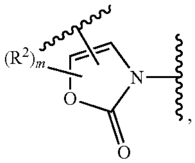 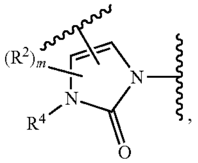

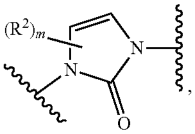 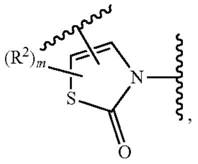

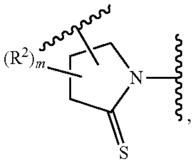 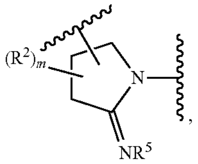

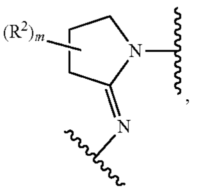 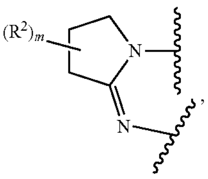

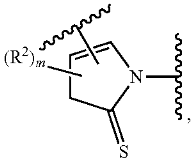 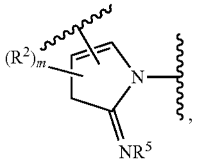

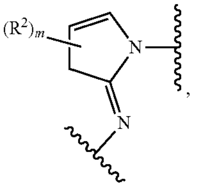 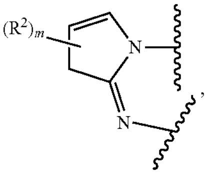

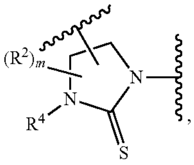 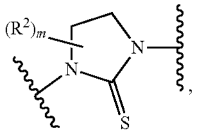

-continued

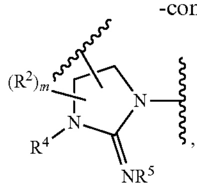,
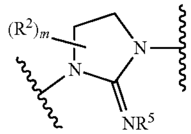,
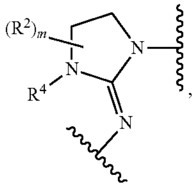,
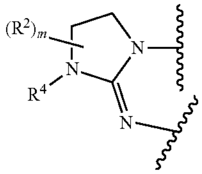,
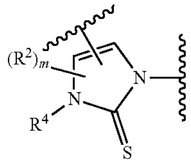,
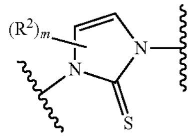,
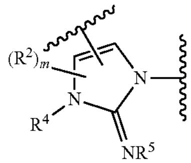,
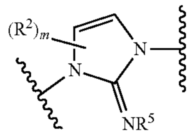,
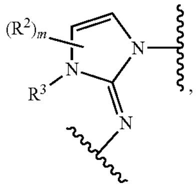,
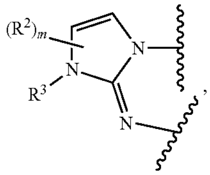,
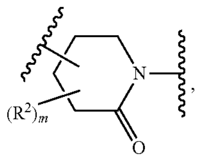,
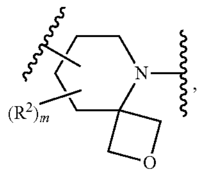,
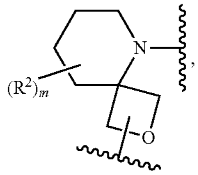,
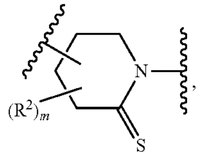,
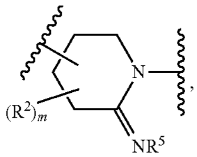,
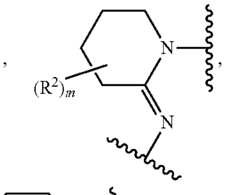, or
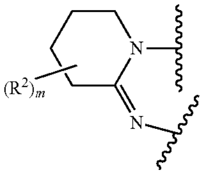;

each of $R^2$ and $R^{3a}$ is independently hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)$S(O)_2R$;

Ring D is selected from 6-membered aryl, 6-membered heteroaryl containing 1-4 heteroatoms independently selected from nitrogen, oxygen, and sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;

each $R_4$ is independently hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)$S(O)_2R$;

$R^5$ is hydrogen, $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, or 2;

n is 0, 1, 2, 3 or 4;

p is 0 or 1, wherein when p is 0, the bond connecting Ring C and Ring D is connected to

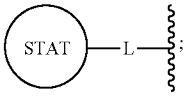;

and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, a compound of formula I-g above is provided as a compound of formula I-g' or formula I-g":

I-g'

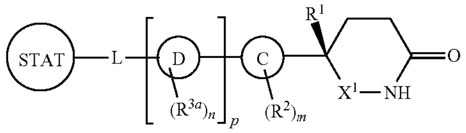

I-g"

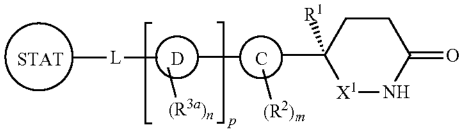

or a pharmaceutically acceptable salt thereof, wherein: each of STAT, Ring C, Ring D, L, $R^1$, $R^2$, $R^{3a}$, $X^1$, n, m, and p is as defined above.

In certain embodiments, the present invention provides a compound of formula I, wherein LBM is an E3 ubiquitin ligase (cereblon) binding moiety thereby forming a compound of formula I-h:

I-h

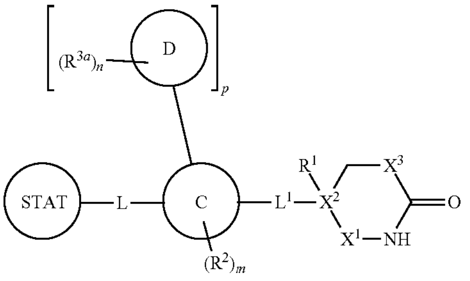

or a pharmaceutically acceptable salt thereof, wherein L and STAT are as defined above and described in embodiments herein, and wherein:

$X^1$ is a bivalent moiety selected from a covalent bond, —$CH_2$—, —$CHCF_3$—, —$SO_2$—, —S(O)—, —P(O)R—, —P(O)OR—, —P(O)$NR_2$—, —C(O)—, —C(S)—, or

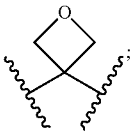 [SMILES: *C1(*)COC1]

;

$X^2$ is a carbon atom or silicon atom;

$X^3$ is a bivalent moiety selected from —$CR_2$—, —NR—, —O—, —S—, or —Si($R_2$)—;

$R^1$ is hydrogen, deuterium, halogen, —CN, —OR, —SR, —S(O)R, —S(O)$_2$R, —$NR_2$, —P(O)(OR)$_2$, —P(O)($NR_2$)OR, —P(O)($NR_2$)$_2$, —Si(OH)$_2$R, —Si(OH)(R)$_2$, —Si(R)$_3$, or an optionally substituted $C_1$0.4 aliphatic;

Ring C is a mono- or bicyclic ring selected from

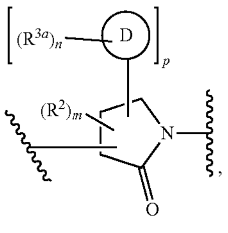

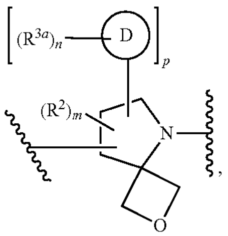

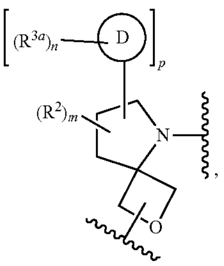

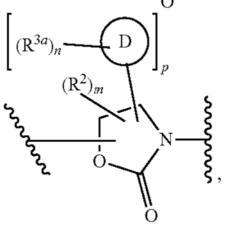

-continued

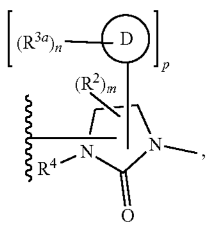

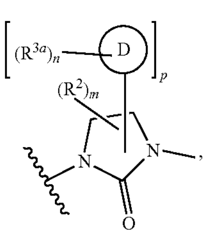

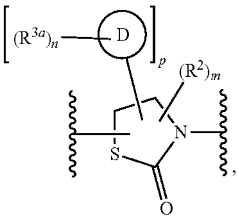

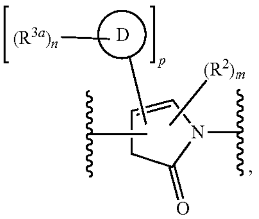

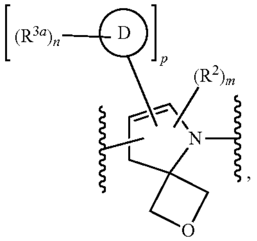

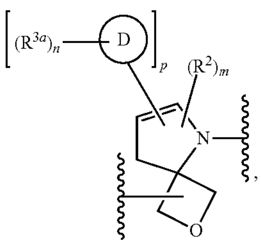

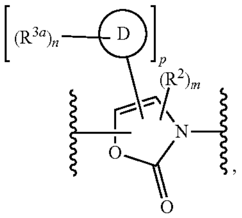

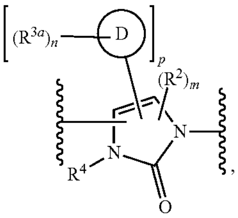

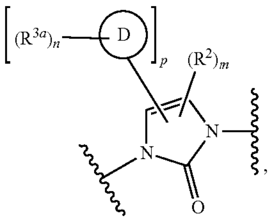

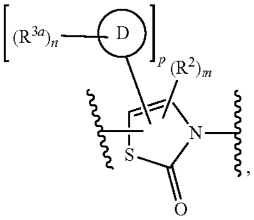

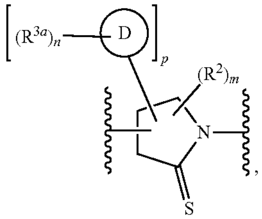

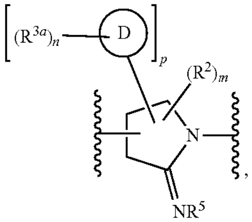

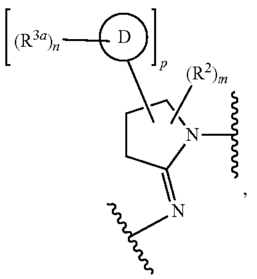

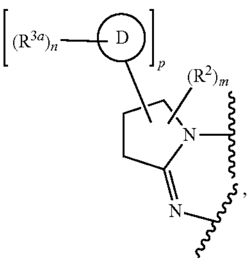

-continued

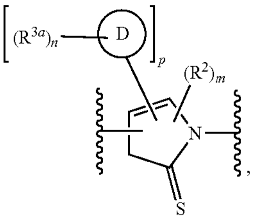,
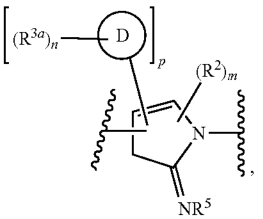,
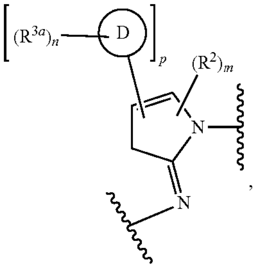,
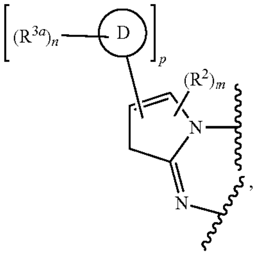,
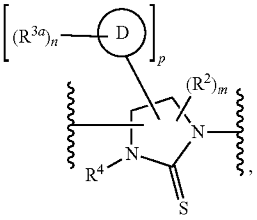,
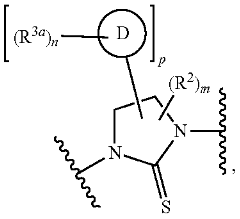,
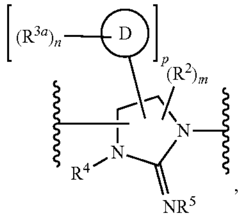,
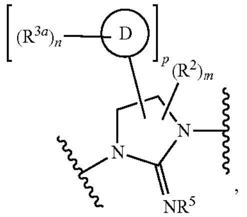,
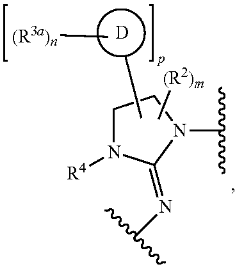,
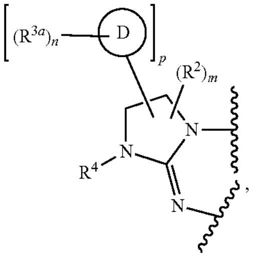,
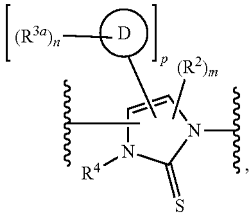,
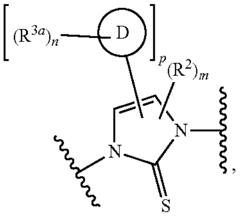,
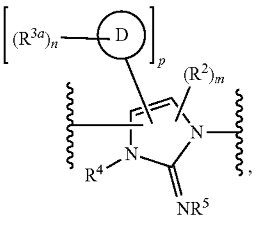,
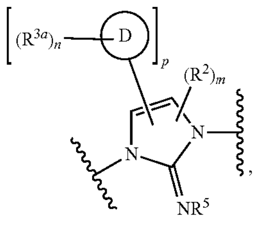, -continued

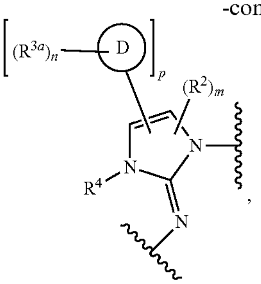,
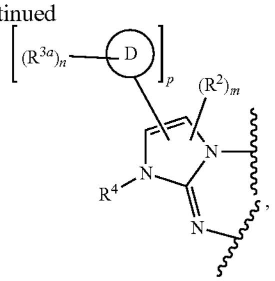,
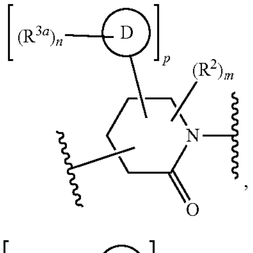,
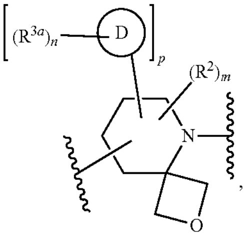,
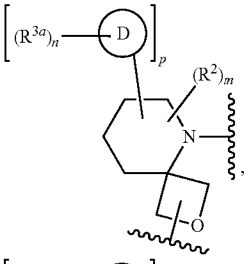,
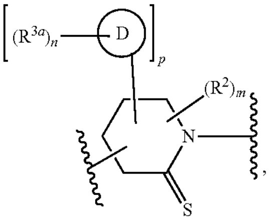,
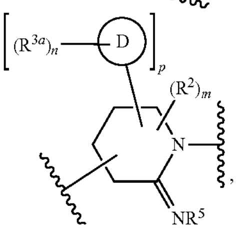,
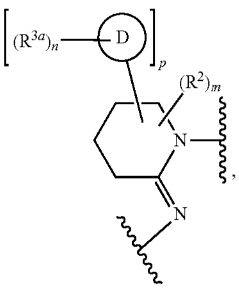, or
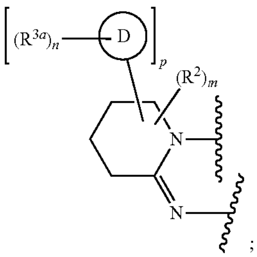;

each or $R^2$ and $R^{3a}$ is independently hydrogen, deuterium, —$R^6$, halogen, —CN, —$NO_2$, —OR, —SR, —$N(R)_2$, —$Si(R)_3$, —$S(O)_2R$, —$S(O)_2N(R)_2$, —S(O)R, —C(O)R, —C(O)OR, —$C(O)N(R)_2$, —C(O)N(R)OR, —$C(R)_2N$(R)C(O)R, —$C(R)_2N(R)C(O)N(R)_2$, —OC(O)R, —OC(O)$N(R)_2$, —$OP(O)R_2$, —$OP(O)(OR)_2$, —OP(O)(OR)($NR_2$), —$OP(O)(NR_2)_2$—, —N(R)C(O)OR, —N(R)C(O)R, —$N(R)C(O)N(R)_2$, —$N(R)S(O)_2R$, —$NP(O)R_2$, —$N(R)P(O)(OR)_2$, —N(R)P(O)(OR)($NR_2$), —N(R)P(O)$(NR_2)_2$, or —$N(R)S(O)_2R$;

Ring D is selected from 6-membered aryl, 6-membered heteroaryl containing 1-4 heteroatoms independently selected from nitrogen, oxygen, and sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;

each $R_4$ is independently hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)$S(O)_2$R;

$R^5$ is hydrogen, $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

$L^1$ is a covalent bond or a $C_{1-3}$ bivalent straight or branched saturated or unsaturated hydrocarbon chain wherein 1-2 methylene units of the chain are independently and optionally replaced with —O—, —C(O)—C(S)—, —$C(R)_2$—, —CH(R)—, —$C(F)_2$—, —N(R)—, —$S(O)_2$— or —(C)═CH—;

m is 0, 1, 2, 3 or 4;

n is 0, 1, 2, 3 or 4;

p is 0 or 1; and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, a compound of formula I-h above is provided as a compound of formula I-h' or formula I-h":

I-h'

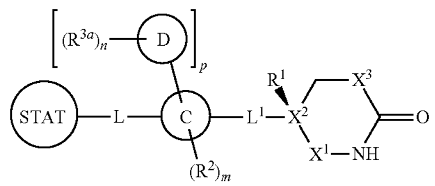

I-h"

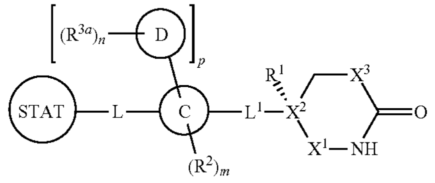

or a pharmaceutically acceptable salt thereof, wherein:

each of STAT, Ring C, Ring D, L, $L^1$, $R^1$, $R^2$, $R^{3a}$, $X^1$, $X^2$, $X^3$, m, n, and p is as defined above.

In certain embodiments, the present invention provides a compound of Formula I, wherein LBM is an E3 ubiquitin ligase (cereblon) binding moiety thereby forming a compound of formula I-i:

I-i

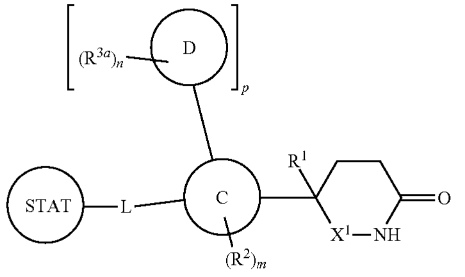

or a pharmaceutically acceptable salt thereof, wherein L and STAT are as defined above and described in embodiments herein, and wherein:

$X^1$ is a bivalent moiety selected from a covalent bond, —$CH_2$—, —C(O)—, —C(S)—, or

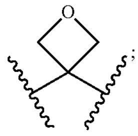 [SMILES: *C1(*)COC1]

;

$R^1$ is hydrogen, deuterium, halogen, —CN, —OR, —SR, —S(O)R, —$S(O)_2$R, —$NR_2$, or an optionally substituted $C_{1-4}$ aliphatic;

Ring C is a mono- or bicyclic ring selected from

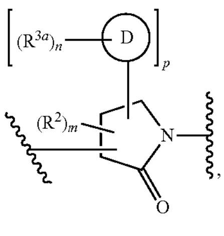

,

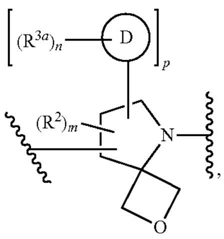

,

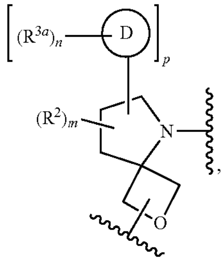

,

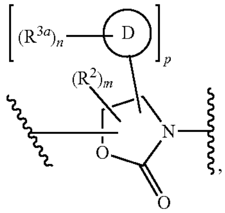

,

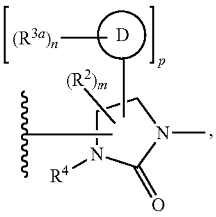

,

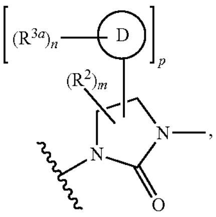

,

-continued
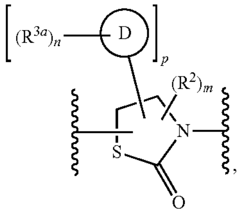,
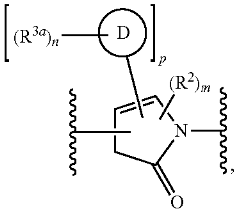,
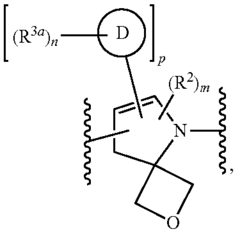,
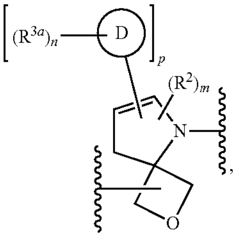,
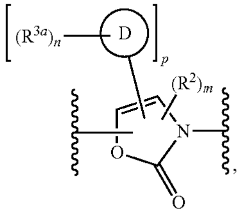,
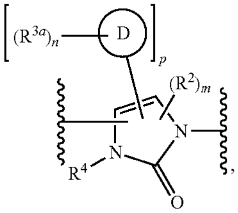,
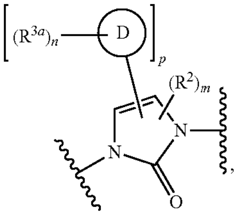,
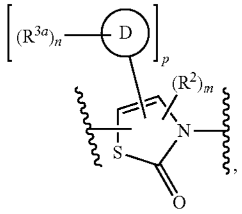,
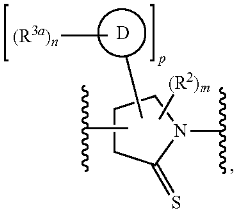,
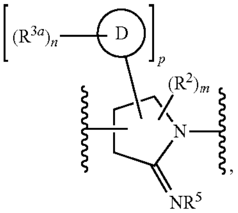,
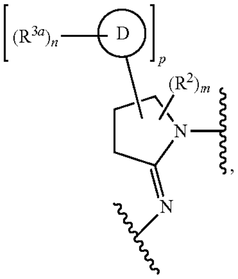,
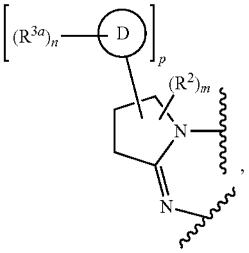,
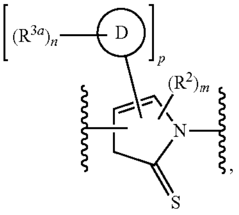,
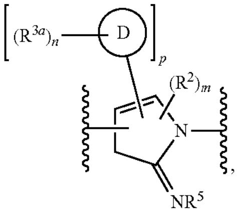,
-continued
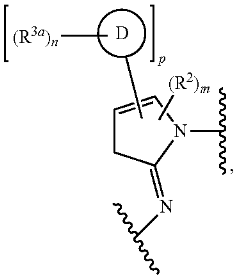,
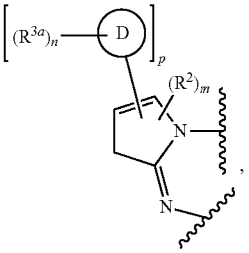,
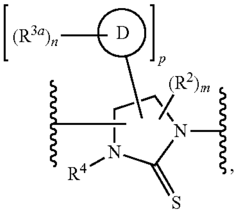,
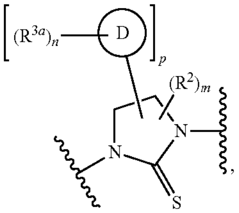,
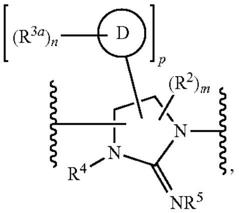,
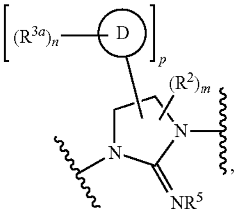,
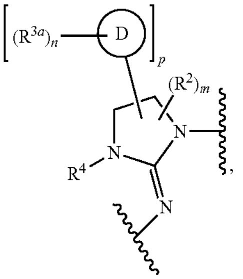,
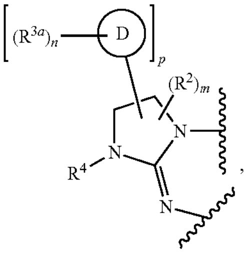,
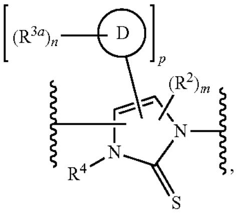,
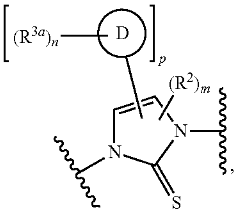,
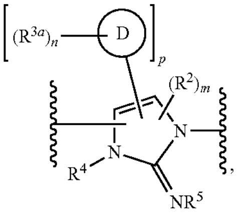,
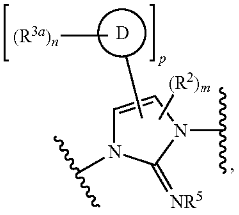,
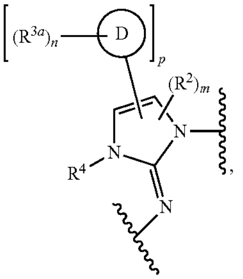,
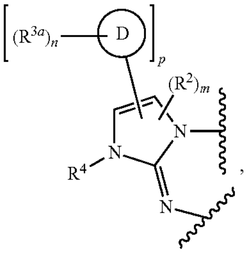, -continued

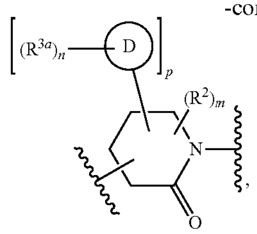

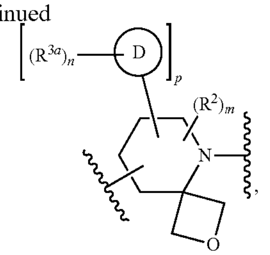

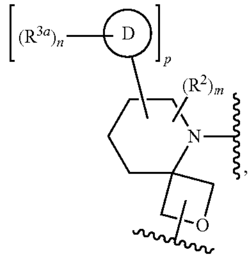

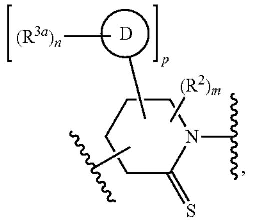

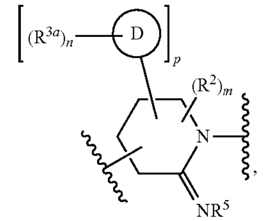

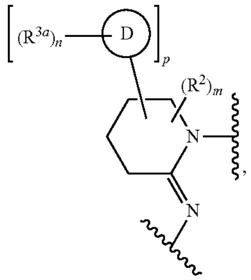

or

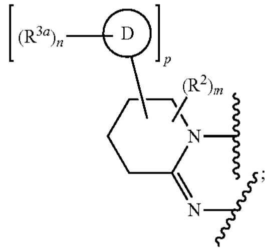

each of $R^2$, $R^{3a}$, and $R^4$ is independently hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)$S(O)_2R$;

Ring D is selected from 6-membered aryl, 6-membered heteroaryl containing 1-4 heteroatoms independently selected from nitrogen, oxygen, and sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;

$R^5$ is hydrogen, $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, or 2;

n is 0, 1, 2, 3, or 4;

p is 0 or 1; and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, a compound of formula I-i above is provided as a compound of formula I-i' or formula I-i":

I-i'

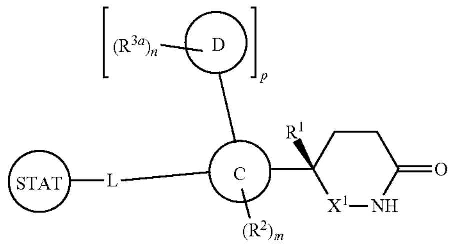

I-i"

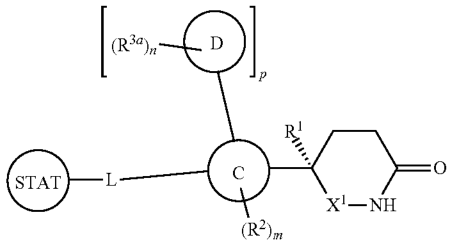

or a pharmaceutically acceptable salt thereof, wherein:

each of STAT, Ring C, Ring D, L, $R^1$, $R^2$, $R^{3a}$, $X^1$, m, n, and p is as defined above.

In certain embodiments, the present invention provides a compound of Formula I, wherein LBM is an E3 ubiquitin ligase (cereblon) binding moiety thereby forming a compound of formula I-j:

I-j

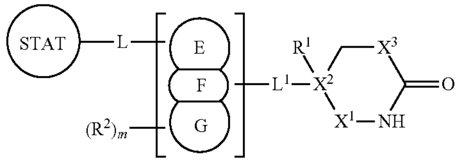

or a pharmaceutically acceptable salt thereof, wherein L and STAT are as defined above and described in embodiments herein, and wherein:

$X^1$ is a bivalent moiety selected from a covalent bond, —$CH_2$—, —$CHCF_3$—, —$SO_2$—, —S(O)—, —P(O)R—, —P(O)OR—, —P(O)$NR_2$—, —C(O)—, —C(S)—, or

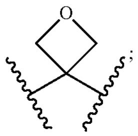 [SMILES: *C1(*)COC1]

$X^2$ is a carbon atom or silicon atom;

$X^3$ is a bivalent moiety selected from —$CR_2$—, —NR—, —O—, —S—, or —$Si(R_2)$—;

$R^1$ is hydrogen, deuterium, halogen, —CN, —OR, —SR, —S(O)R, —$S(O)_2R$, —$N(R)_2$, —$P(O)(OR)_2$, —P(O)($NR_2$)OR, —$P(O)(NR_2)_2$, —$Si(OH)_2R$, —$Si(OH)(R)_2$, —$Si(R)_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, —$R^6$, halogen, —CN, —$NO_2$, —OR, —SR, —$N(R)_2$, —$Si(R)_3$, —$S(O)_2R$, —$S(O)_2N(R)_2$, —S(O)R, —C(O)R, —C(O)OR, —$C(O)N(R)_2$, —C(O)N(R)OR, —$C(R)_2N(R)C(O)R$, —$C(R)_2N(R)C(O)N(R)_2$, —OC(O)R, —$OC(O)N(R)_2$, —$OP(O)R_2$, —$OP(O)(OR)_2$, —$OP(O)(OR)(NR_2)$, —$OP(O)(NR_2)_2$—, —N(R)C(O)OR, —N(R)C(O)R, —$N(R)C(O)N(R)_2$, —$N(R)S(O)_2R$, —$NP(O)R_2$, —$N(R)P(O)(OR)_2$, —$N(R)P(O)(OR)(NR_2)$, —$N(R)P(O)(NR_2)_2$, or —$N(R)S(O)_2R$;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each of Ring E, Ring F, and Ring G is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur, wherein each of Ring E, Ring F, and Ring G is independently and optionally further substituted with 1-2 oxo groups;

$L^1$ is a covalent bond or a $C_{1-3}$ bivalent straight or branched saturated or unsaturated hydrocarbon chain wherein 1-2 methylene units of the chain are independently and optionally replaced with —O—, —C(O)—C(S)—, —$C(R)_2$—, —CH(R)—, —$C(F)_2$—, —N(R)—, —$S(O)_2$— or —(C)=CH—; and m is 0, 1, 2, 3, 4, 5, 6, 7, 8, 9, 10, 11, 12, 13, 14, 15, or 16.

Where a point of attachment of

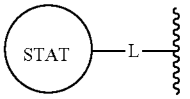

is depicted on Ring E, Ring F, or Ring G, it is intended, and one of ordinary skill in the art would appreciate, that the point of attachment of

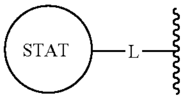

may be on any available carbon or nitrogen atom on Ring E, Ring F, or Ring G, including the ring to which Ring E or Ring G are fused to Ring F.

Where a point of attachment of —$(R^2)_m$ is depicted on Ring E, Ring F, or Ring G, it is intended, and one of ordinary skill in the art would appreciate, that the point of attachment of —$(R^2)_m$ may be at any available carbon or nitrogen atom on Ring E, Ring F, or Ring G including the carbon atom to which Ring E or Ring G are fused to Ring F.

Where a point of attachment of

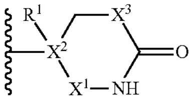

is depicted on Ring E, Ring F, or Ring G, it is intended, and one of ordinary skill in the art would appreciate, that the point of attachment of

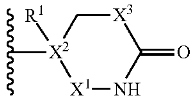

may be on any available carbon or nitrogen atom on Ring E, Ring F, or Ring G, including the carbon atom to which Ring E or Ring G are fused to Ring F.

In some embodiments, a compound of formula I-j above is provided as a compound of formula I-j' or formula I-j":

I-j'

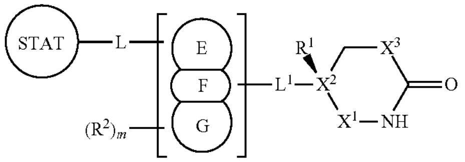

I-j"

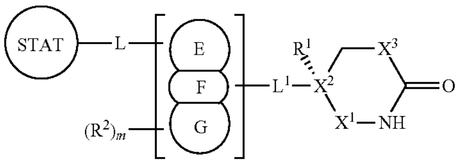

or a pharmaceutically acceptable salt thereof, wherein: each of STAT, Ring E, Ring F, Ring G, L, $L^1$, $R^1$, $R^2$, $X^1$, $X^2$, $X^3$, and m is as defined above.

In certain embodiments, the present invention provides a compound of Formula I, wherein LBM is an E3 ubiquitin ligase (cereblon) binding moiety thereby forming a compound of formula I-k:

I-k

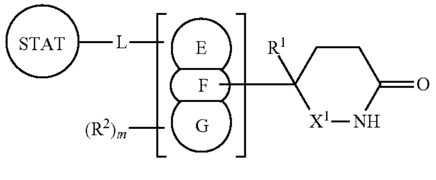

or a pharmaceutically acceptable salt thereof, wherein L and STAT are as defined above and described in embodiments herein, and wherein:

$X^1$ is a bivalent moiety selected from a covalent bond, $—CH_2—$, —C(O)—, —C(S)—, or;

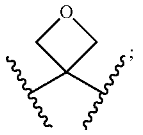 [SMILES: *C1(*)COC1]

$R^1$ is hydrogen, deuterium, halogen, —CN, —OR, —SR, —S(O)R, $—S(O)_2R$, $—N(R)_2$, $—Si(R)_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, $—R^6$, halogen, —CN, $—NO_2$, —OR, —SR, $—N(R)_2$, $—Si(R)_3$, $—S(O)_2R$, $—S(O)_2N(R)_2$, —S(O)R, —C(O)R, —C(O)OR, $—C(O)N(R)_2$, —C(O)N(R)OR, $—C(R)_2N(R)C(O)R$, $—C(R)_2N(R)C(O)N(R)_2$, —OC(O)R, $—OC(O)N(R)_2$, —N(R)C(O)OR, —N(R)C(O)R, $—N(R)C(O)N(R)_2$, or $—N(R)S(O)_2R$;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each of Ring E, Ring F, and Ring G is independently a fused ring selected from 6-membered aryl containing 0-3 nitrogens, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-3 heteroatoms independently selected from nitrogen, oxygen or sulfur, wherein each of Ring E, Ring F, and Ring G is independently and optionally further substituted with 1-2 oxo groups; and m is 0, 1, 2, 3, or 4.

Where a point of attachment of

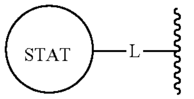

is depicted on Ring E, Ring F, or Ring G, it is intended, and one of ordinary skill in the art would appreciate, that the point of attachment of

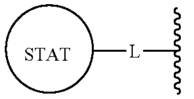

may be on any available carbon or nitrogen atom on Ring E, Ring F, or Ring G, including the ring to which Ring E or Ring G are fused to Ring F.

Where a point of attachment of $—(R^2)_m$ is depicted on Ring E, Ring F, or Ring G, it is intended, and one of ordinary skill in the art would appreciate, that the point of attachment of $—(R^2)_m$ may be at any available carbon or nitrogen atom on Ring E, Ring F, or Ring G including the carbon atom to which Ring E or Ring G are fused to Ring F.

In some embodiments, a compound of formula I-k above is provided as a compound of formula I-k' or formula I-k":

I-k'

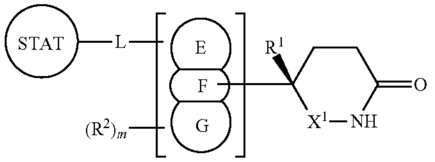

I-k"

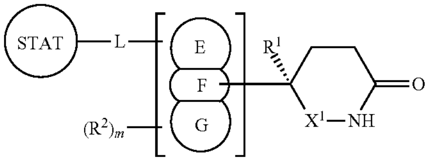

or a pharmaceutically acceptable salt thereof, wherein:

each of STAT, L, Ring E, Ring F, Ring G, L, $R^1$, $R^2$, $X^1$, and m is as defined above.

In certain embodiments, the present invention provides a compound of Formula I, wherein LBM is an E3 ubiquitin ligase (cereblon) binding moiety thereby forming a compound of formula I-1:

I-1

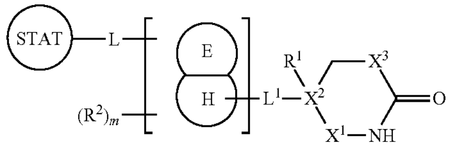

or a pharmaceutically acceptable salt thereof, wherein L and STAT are as defined above and described in embodiments herein, and wherein:

$X^1$ is a bivalent moiety selected from a covalent bond, —$CH_2$—, —$CHCF_3$—, —$SO_2$—, —S(O)—, —P(O)R—, —P(O)OR—, —P(O)$NR_2$—, —C(O)—, —C(S)—, or

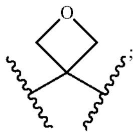 [SMILES: *C1(*)COC1]

$X^2$ is a carbon atom or silicon atom;

$X^3$ is a bivalent moiety selected from —$CR_2$—, —NR—, —O—, —S—, or —Si($R_2$)—;

$R^1$ is hydrogen, deuterium, halogen, —CN, —OR, —SR, —S(O)R, —$S(O)_2R$, —$N(R)_2$, —P(O)$(OR)_2$, —P(O)($NR_2$)OR, —P(O)$(NR_2)_2$, —Si$(OH)_2$R, —Si(OH)$(R)_2$, —$Si(R)_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, —$R^6$, halogen, —CN, —$NO_2$, —OR, —SR, —$N(R)_2$, —$Si(R)_3$, —$S(O)_2R$, —$S(O)_2N(R)_2$, —S(O)R, —C(O)R, —C(O)OR, —C(O)$N(R)_2$, —C(O)N(R)OR, —$C(R)_2$N(R)C(O)R, —$C(R)_2$N(R)C(O)$N(R)_2$, —OC(O)R, —OC(O)$N(R)_2$, —OP(O)$R_2$, —OP(O)$(OR)_2$, —OP(O)(OR)($NR_2$), —OP(O)$(NR_2)_2$—, —N(R)C(O)OR, —N(R)C(O)R, —N(R)C(O)$N(R)_2$, —N(R)$S(O)_2$R, —NP(O)$R_2$, —N(R)P(O)$(OR)_2$, —N(R)P(O)(OR)($NR_2$), —N(R)P(O)$(NR_2)_2$, or —N(R)$S(O)_2$R;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring E is a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;

Ring H is a fused ring selected from a 7-9 membered saturated or partially unsaturated carbocyclyl or heterocyclyl ring with 1-3 heteroatoms independently selected from boron, nitrogen, oxygen, silicon, or sulfur, wherein Ring E is optionally further substituted with 1-2 oxo groups;

$L^1$ is a covalent bond or a $C_{1-3}$ bivalent straight or branched saturated or unsaturated hydrocarbon chain wherein 1-2 methylene units of the chain are independently and optionally replaced with —O—, —C(O)—C(S)—, —$C(R)_2$—, —CH(R)—, —$C(F)_2$—, —N(R)—, —$S(O)_2$— or —(C)=CH—;

m is 0, 1, 2, 3, or 4.

Where a point of attachment of

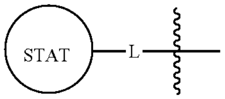

is depicted on Ring E or Ring H, it is intended, and one of ordinary skill in the art would appreciate, that the point of attachment of

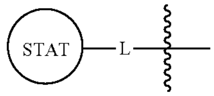

may be on any available carbon or nitrogen atom on Ring E or Ring H including the carbon atom to which Ring E and Ring H are fused.

Where a point of attachment of —$(R^2)_m$ is depicted on Ring E and Ring H, it is intended, and one of ordinary skill in the art would appreciate, that the point of attachment of —$(R^2)_m$ may be on any available carbon or nitrogen atom on Ring E or Ring H including the carbon atom to which Ring E and Ring H are fused.

Where a point of attachment of

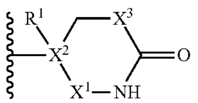

is depicted on Ring E and Ring H, it is intended, and one of ordinary skill in the art would appreciate, that the point of attachment of

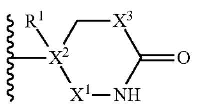

may be on any available carbon or nitrogen atom on Ring E or Ring H including the carbon atom to which Ring E and Ring H are fused.

In some embodiments, a compound of formula I-1 above is provided as a compound of formula I-1' or formula I-1'':

I-l′

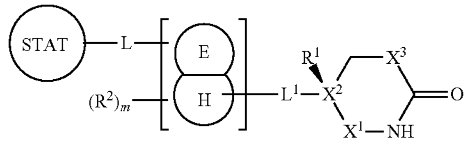

I-l″

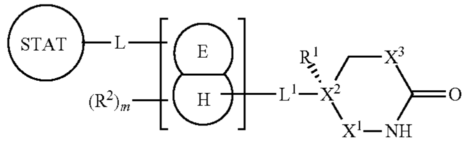

or a pharmaceutically acceptable salt thereof, wherein: each of STAT, Ring E, Ring H, L, L1, $R^1$, $R^2$, $X^1$, $X^2$, $X^3$, and m is as defined above.

In certain embodiments, the present invention provides a compound of Formula I, wherein LBM is an E3 ubiquitin ligase (cereblon) binding moiety thereby forming a compound of formula I-m:

I-m

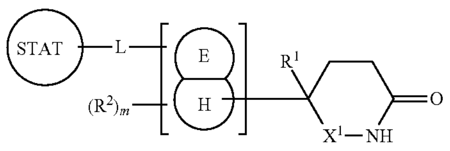

or a pharmaceutically acceptable salt thereof, wherein L and STAT are as defined above and described in embodiments herein, and wherein:

$X^1$ is a bivalent moiety selected from a covalent bond, —$CH_2$—, —C(O)—, —C(S)—, or

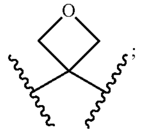 [SMILES: *C1(*)COC1]

$R^1$ is hydrogen, deuterium, halogen, —CN, —OR, —SR, —S(O)R, —$S(O)_2R$, —$N(R)_2$, —$Si(R)_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, —$R^6$, halogen, —CN, —$NO_2$, —OR, —SR, —$N(R)_2$, —$Si(R)_3$, —$S(O)_2R$, —$S(O)_2N(R)_2$, —S(O)R, —C(O)R, —C(O)OR, —$C(O)N(R)_2$, —C(O)N(R)OR, —$C(R)_2N(R)C(O)R$, —$C(R)_2N(R)C(O)N(R)_2$, —OC(O)R, —$OC(O)N(R)_2$, —N(R)C(O)OR, —N(R)C(O)R, —$N(R)C(O)N(R)_2$, or —$N(R)S(O)_2R$;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring E is a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;

Ring H is a ring selected from a 7-9 membered saturated or partially unsaturated carbocyclyl or heterocyclyl ring with 1-3 heteroatoms independently selected from boron, nitrogen, oxygen, silicon, or sulfur, wherein Ring E is optionally further substituted with 1-2 oxo groups; and m is 0, 1, 2, 3, or 4.

Where a point of attachment of

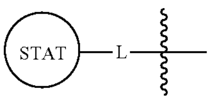

is depicted on Ring E or Ring H, it is intended, and one of ordinary skill in the art would appreciate, that the point of attachment of

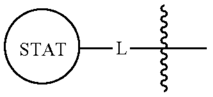

may be on any available carbon or nitrogen atom on Ring E or Ring H including the carbon atom to which Ring E and Ring H are fused.

Where a point of attachment of —$(R^2)_m$ is depicted on Ring E and Ring H, it is intended, and one of ordinary skill in the art would appreciate, that the point of attachment of —$(R^2)_m$ may be on any available carbon or nitrogen atom on Ring E or Ring H including the carbon atom to which Ring E and Ring H are fused.

Where a point of attachment of

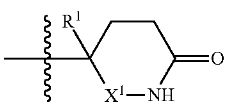

is depicted on Ring E and Ring H, it is intended, and one of ordinary skill in the art would appreciate, that the point of attachment of

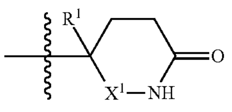

may be on any available carbon or nitrogen atom on Ring E or Ring H including the carbon atom to which Ring E and Ring H are fused.

In some embodiments, a compound of formula I-m above is provided as a compound of formula I-m' or formula I-m''.

I-m'

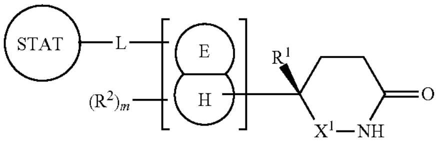

I-m''

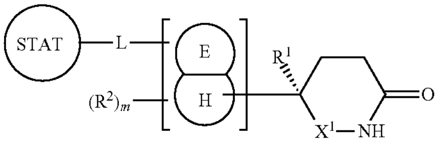

or a pharmaceutically acceptable salt thereof, wherein:

each of STAT, Ring E, Ring H, L, $R^1$, $R^2$, $X^1$, and m is as defined above.

In some embodiments, a compound of formula I-m above is provided as a compound of formula I-m-1:

I-m-1

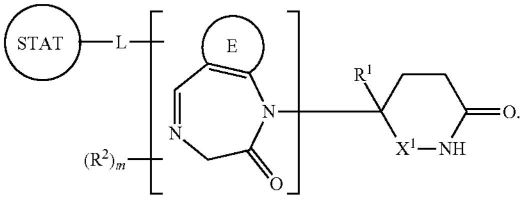

or a pharmaceutically acceptable salt thereof, wherein:

each of STAT, L, Ring E, $X^1$, $R^1$, $R^2$, and m is as defined above.

In certain embodiments, the present invention provides a compound of Formula I, wherein LBM is an E3 ubiquitin ligase (cereblon) binding moiety thereby forming a compound of formula I-n:

I-n

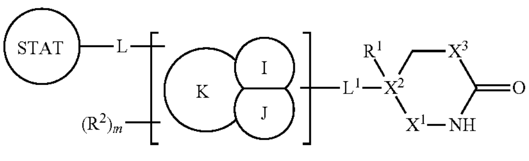

or a pharmaceutically acceptable salt thereof, wherein:

$X^1$ is a bivalent moiety selected from a covalent bond, —$CH_2$—, —$CHCF_3$—, —$SO_2$—, —S(O)—, —P(O)R—, —P(O)OR—, —P(O)$NR_2$—, —C(O)—, —C(S)—, or

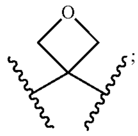 [SMILES: *C1(*)COC1]

;

$X^2$ is a carbon atom or silicon atom;

$X^3$ is a bivalent moiety selected from —$CR_2$—, —NR—, —O—, —S—, or —Si($R_2$)—;

$R^1$ is hydrogen, deuterium, halogen, —CN, —OR, —SR, —S(O)R, —$S(O)_2R$, —$NR_2$, —P(O)$(OR)_2$, —P(O)($NR_2$)OR, —P(O)$(NR_2)_2$, —Si$(OH)_2$R, —Si(OH)$(R)_2$, —Si$(R)_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, —R, halogen, —CN, —$NO_2$, —OR, —SR, —N$(R)_2$, —Si$(R)_3$, —$S(O)_2R$, —$S(O)_2N(R)_2$, —S(O)R, —C(O)R, —C(O)OR, —C(O)N$(R)_2$, —C(O)N(R)OR, —C$(R)_2$N(R)C(O)R, —C$(R)_2$N(R)C(O)N$(R)_2$, —OC(O)R, —OC(O)N$(R)_2$, —OP(O)$R_2$, —OP(O)$(OR)_2$, —OP(O)(OR)($NR_2$), —OP(O)$(NR_2)_2$—, —N(R)C(O)OR, —N(R)C(O)R, —N(R)C(O)N$(R)_2$, —N(R)$S(O)_2R$, —NP(O)$R_2$, —N(R)P(O)$(OR)_2$, —N(R)P(O)(OR)($NR_2$), —N(R)P(O)$(NR_2)_2$, or —N(R)$S(O)_2R$;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each of Ring I and J is independently a fused ring selected from 6-membered aryl, 6-membered heteroaryl containing 1-4 heteroatoms independently selected from nitrogen, oxygen, and sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;

Ring K is a fused ring selected from a 6-12 membered saturated or partially unsaturated carbocyclyl or heterocyclyl ring with 1-3 heteroatoms independently selected from boron, nitrogen, oxygen, silicon, or sulfur, wherein Ring H is optionally further substituted with 1-2 oxo groups;

$L^1$ is a covalent bond or a $C_{1-3}$ bivalent straight or branched saturated or unsaturated hydrocarbon chain wherein 1-2 methylene units of the chain are independently and optionally replaced with —O—, —C(O)—C(S)—, —C$(R)_2$—, —CH(R)—, —C$(F)_2$—, —N(R)—, —$S(O)_2$— or —(C)═CH—; and m is 0, 1, 2, 3, or 4.

Where a point of attachment of

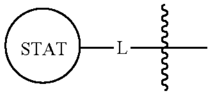

is depicted on Ring I, Ring J, and Ring K, it is intended, and one of ordinary skill in the art would appreciate, that the point of attachment of

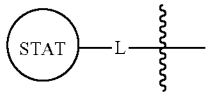

may be on any available carbon or nitrogen atom on Ring I, Ring J, or Ring K, including the carbon atom to which Ring I, Ring J, and Ring K are fused.

Where a point of attachment of $-(R^2)_m$ is depicted on Ring I, Ring J, and Ring K, it is intended, and one of ordinary skill in the art would appreciate, that the point of attachment of $-(R^2)_m$ may be on any available carbon or nitrogen atom on Ring I, Ring J, or Ring K, including the carbon atom to which Ring I, Ring J, and Ring K are fused.

Where a point of attachment of

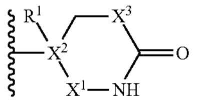

is depicted on Ring I, Ring J, and Ring K, it is intended, and one of ordinary skill in the art would appreciate, that the point of attachment of

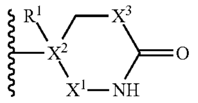

may be on any available carbon or nitrogen atom on Ring I, Ring J, or Ring K, including the carbon atom to which Ring I, Ring J, and Ring K are fused.

In some embodiments, a compound of formula I-n above is provided as a compound of formula I-n' or formula I-n'':

I-n'

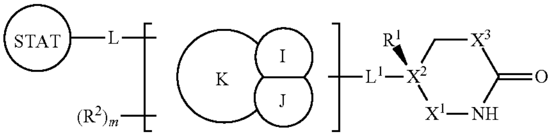

I-n''

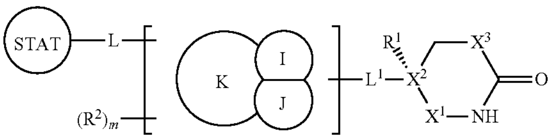

or a pharmaceutically acceptable salt thereof, wherein: each of STAT, Ring I, Ring J, Ring K, L, LI, $R^1$, $R^2$, $X^1$, $X^2$, $X^3$, and m is as defined above.

In certain embodiments, the present invention provides a compound of formula I-o:

I-o

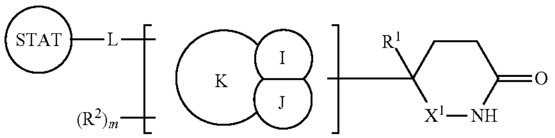

or a pharmaceutically acceptable salt thereof, wherein:

$X^1$ is a bivalent moiety selected from a covalent bond, $-CH_2-$, $-C(O)-$, $-C(S)-$, or

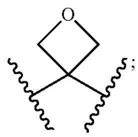 [SMILES: *C1(*)COC1]

;

$R^1$ is hydrogen, deuterium, halogen, $-CN$, $-OR$, $-SR$, $-S(O)R$, $-S(O)_2R$, $-N(R)_2$, $-Si(R)_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, $-R^6$, halogen, $-CN$, $-NO_2$, $-OR$, $-SR$, $-N(R)_2$, $-Si(R)_3$, $-S(O)_2R$, $-S(O)_2N(R)_2$, $-S(O)R$, $-C(O)R$, $-C(O)OR$, $-C(O)N(R)_2$, $-C(O)N(R)OR$, $-C(R)_2N(R)C(O)R$, $-C(R)_2N(R)C(O)N(R)_2$, $-OC(O)R$, $-OC(O)N(R)_2$, $-N(R)C(O)OR$, $-N(R)C(O)R$, $-N(R)C(O)N(R)_2$, or $-N(R)S(O)_2R$;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each of Ring I and J is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;

Ring K is a fused ring selected from a 6-12 membered saturated or partially unsaturated carbocyclyl or heterocyclyl ring with 1-3 heteroatoms independently selected from boron, nitrogen, oxygen, silicon, or sulfur, wherein Ring H is optionally further substituted with 1-2 oxo groups; and m is 0, 1, 2, 3, or 4.

Where a point of attachment of

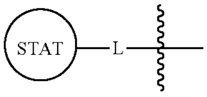

is depicted on Ring I, Ring J, and Ring K, it is intended, and one of ordinary skill in the art would appreciate, that the point of attachment of

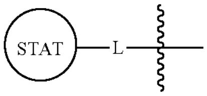

may be on any available carbon or nitrogen atom on Ring I, Ring J, or Ring K, including the carbon atom to which Ring I, Ring J, and Ring K are fused.

Where a point of attachment of —$(R^2)_m$ is depicted on Ring I, Ring J, and Ring K, it is intended, and one of ordinary skill in the art would appreciate, that the point of attachment of —$(R^2)_m$ may be on any available carbon or nitrogen atom on Ring I, Ring J, or Ring K, including the carbon atom to which Ring I, Ring J, and Ring K are fused.

Where a point of attachment of

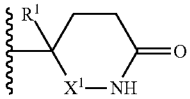

is depicted on Ring I, Ring J, and Ring K, it is intended, and one of ordinary skill in the art would appreciate, that the point of attachment of

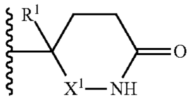

may be on any available carbon or nitrogen atom on Ring I, Ring J, or Ring K, including the carbon atom to which Ring I, Ring J, and Ring K are fused.

In some embodiments, a compound of formula I-o above is provided as a compound of formula I-o' or formula I-o":

I-o'

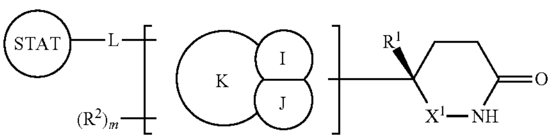

-continued

I-o"

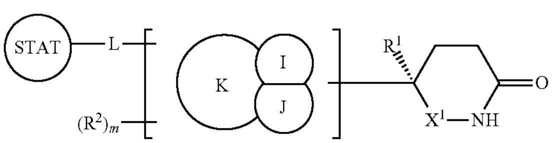

or a pharmaceutically acceptable salt thereof, wherein: each of STAT, Ring I, Ring J, Ring K, L, $R^1$, $R^2$, $X^1$, and m is as defined above.

In some embodiments, a compound of formula I-o above is provided as a compound of formula I-o-1:

I-o-1

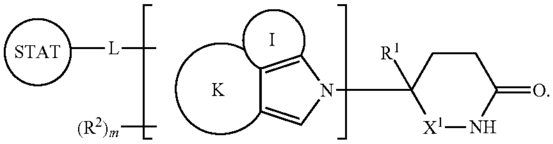

or a pharmaceutically acceptable salt thereof, wherein: each of STAT, L, Ring I, Ring K, $X^1$, $R^1$, $R^2$, and m is as defined above.

In certain embodiments, the present invention provides a compound of Formula I, wherein LBM is an E3 ubiquitin ligase (cereblon) binding moiety thereby forming a compound of formula I-o-2 or I-o-3:

I-o-2

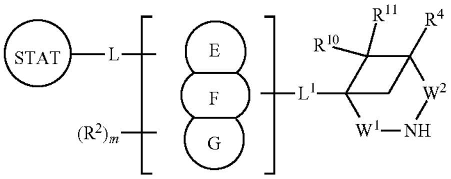

I-o-3

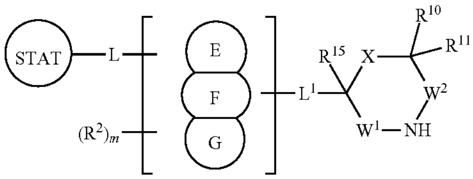

or a pharmaceutically acceptable salt thereof, wherein L and STAT are as defined above and described in embodiments herein, and wherein:

each $R^2$ is independently hydrogen, deuterium, —$R^6$, halogen, —CN, —$NO_2$, —OR, —SR, —$NR_2$, —$SiR_3$, —$S(O)_2R$, —$S(O)_2NR_2$, —S(O)R, —C(O)R, —C(O)OR, —$C(O)NR_2$, —C(O)N(R)OR, —$C(R)_2N(R)C(O)R$, —$C(R)_2N(R)C(O)N(R)_2$, —OC(O)R, —$OC(O)N(R)_2$, —$OP(O)R_2$, —$OP(O)(OR)_2$, —$OP(O)(OR)NR_2$, —$OP(O)(NR_2)_2$—, —N(R)C(O)OR, —N(R)C(O)R, —$N(R)C(O)NR_2$, —$N(R)S(O)_2R$, —$NP(O)R_2$, —$N(R)P(O)(OR)_2$, —$N(R)P(O)(OR)NR_2$, —$N(R)P(O)(NR_2)_2$, or $N(R)S(O)_2R$;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each of Ring E, Ring F, and Ring G is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur, wherein each of Ring E, Ring F, and Ring G is independently and optionally further substituted with 1-2 oxo groups;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

$L^1$ is a covalent bond or a $C_{1-3}$ bivalent straight or branched saturated or unsaturated hydrocarbon chain wherein 1-2 methylene units of the chain are independently and optionally replaced with —O—, —C(O)—C(S)—, —$C(R)_2$—, —CH(R)—, —$C(F)_2$—, —N(R)—, —S—, —$S(O)_2$— or —(C)═CH—;

m is 0, 1, 2, 3, 4, 5, 6, 7, 8, 9, 10, 11, 12, 13, 14, 15, or 16; and $R_4$, $R^{10}$, $R^{11}$, $R^{15}$, $W^1$, $W^2$, and X is as defined in WO 2019/099868, the entirety of each of which is herein incorporated by reference.

Where a point of attachment of

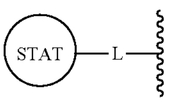

is depicted on Ring E, Ring F, or Ring G, it is intended, and one of ordinary skill in the art would appreciate, that the point of attachment of

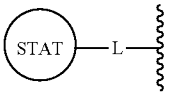

may be on any available carbon or nitrogen atom on Ring E, Ring F, or Ring G, including the ring to which Ring E or Ring G are fused to Ring F.

Where a point of attachment of —$(R^2)_m$ is depicted on Ring E, Ring F, or Ring G, it is intended, and one of ordinary skill in the art would appreciate, that the point of attachment of —$(R^2)_m$ may be at any available carbon or nitrogen atom on Ring E, Ring F, or Ring G including the carbon atom to which Ring E or Ring G are fused to Ring F.

Where a point of attachment of

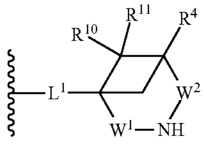

or

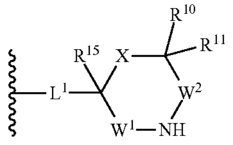

is depicted on Ring E, Ring F, or Ring G, it is intended, and one of ordinary skill in the art would appreciate, that the point of attachment of

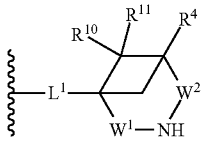

or

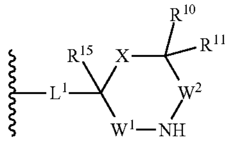

may be on any available carbon or nitrogen atom on Ring E, Ring F, or Ring G, including the carbon atom to which Ring E or Ring G are fused to Ring F.

As defined above and described herein, $X^1$ is a bivalent moiety selected from a covalent bond, —$CH_2$—, —$C(R)_2$—, —C(O)—, —C(S)—, —CH(R)—, —CH$(CF_3)$—, —P(O)(OR)—, —P(O)(R)—, —P(O)$(NR_2)$—, —S(O)—, —$S(O)_2$—, or

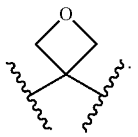 [SMILES: *C1(*)COC1]

In some embodiments, $X^1$ is a covalent bond. In some embodiments, $X^1$ is —$CH_2$—. In some embodiments, $X^1$ is —$C(R)_2$—. In some embodiments, $X^1$ is —C(O)—. In some embodiments, $X^1$ is —C(S)—. In some embodiments, $X^1$ is —CH(R)—. In some embodiments, $X^1$ is —CH$(CF_3)$—. In some embodiments, $X^1$ is —P(O)(OR)—. In some embodiments, $X^1$ is —P(O)(R)—. In some embodiments, $X^1$ is —P(O)$(NR_2)$—. In some embodiments, $X^1$ is —S(O)—. In some embodiments, $X^1$ is —$S(O)_2$—. In some embodiments, $X^1$ is

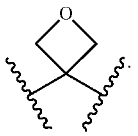 [SMILES: *C1(*)COC1]

In some embodiments, $X^1$ is selected from those depicted in Table 1, below.

As defined above and described herein, $X^2$ is a carbon atom or silicon atom.

In some embodiments, $X^2$ is a carbon atom. In some embodiments, $X^2$ is a silicon atom.

In some embodiments, $X^2$ is selected from those depicted in Table 1, below.

As defined above and described herein, $X^3$ is a bivalent moiety selected from —$CH_2$—, —$C(R)_2$—, —N(R)—, —$CF_2$—, —CHF—, —S—, —CH(R)—, —$Si(R_2)$—, or —O—.

In some embodiments, $X^3$ is —$CH_2$—. In some embodiments, $X^1$ is —$C(R)_2$—. In some embodiments, $X^3$ is —N(R)—. In some embodiments, $X^3$ is —$CF_2$—. In some embodiments, $X^3$ is —CHF—. In some embodiments, $X^3$ is —S—. In some embodiments, $X^3$ is —CH(R)—. In some embodiments, $X^3$ is —$Si(R_2)$—. In some embodiments, $X^3$ is —O—.

In some embodiments, $X^3$ is selected from those depicted in Table 1, below.

As defined above and described herein, $R^1$ is hydrogen, deuterium, halogen, —CN, —OR, —SR, —S(O)R, —$S(O)_2R$, —$NR_2$, —$P(O)(OR)_2$, —$P(O)(NR_2)OR$, —$P(O)(NR_2)_2$, —$Si(OH)_2R$, —$Si(OH)(R)_2$, —$Si(R)_3$, an optionally substituted $C_{1-4}$ aliphatic, or $R^1$ and $X^1$ or $X^4$ are taken together with their intervening atoms to form a 5-7 membered saturated, partially unsaturated, carbocyclic ring or heterocyclic ring having 1-3 heteroatoms, independently selected from nitrogen, oxygen, or sulfur.

In some embodiments, $R^1$ is hydrogen. In some embodiments, $R^1$ is deuterium. In some embodiments, $R^1$ is halogen. In some embodiments, $R^1$ is —CN. In some embodiments, $R^1$ is —OR. In some embodiments, $R^1$ is —SR. In some embodiments, $R^1$ is —S(O)R. In some embodiments, $R^1$ is —$S(O)_2R$. In some embodiments, $R^1$ is —$NR_2$. In some embodiments, $R^1$ is —$P(O)(OR)_2$. In some embodiments, $R^1$ is —$P(O)(NR_2)OR$. In some embodiments, $R^1$ is —$P(O)(NR_2)_2$. In some embodiments, $R^1$ is —$Si(OH)_2R$. In some embodiments, $R^1$ is —$Si(OH)(R)_2$. In some embodiments, $R^1$ is —$Si(R)_3$. In some embodiments, $R^1$ is an optionally substituted $C_{1-4}$ aliphatic. In some embodiments, $R^1$ and $X^1$ or $X^4$ are taken together with their intervening atoms to form a 5-7 membered saturated, partially unsaturated, carbocyclic ring or heterocyclic ring having 1-3 heteroatoms, independently selected from nitrogen, oxygen, or sulfur.

In some embodiments, $R^1$ is selected from those depicted in Table 1, below.

As defined above and described herein, each R is independently hydrogen, deuterium, or an optionally substituted group selected from $C_{1-6}$ aliphatic, phenyl, a 4-7 membered saturated or partially unsaturated heterocyclic having 1-3 heteroatoms independently selected from boron, nitrogen, oxygen, silicon, and sulfur, and a 5-6 membered heteroaryl ring having 1-4 heteroatoms independently selected from boron, nitrogen, oxygen, silicon, and sulfur, or two R groups on the same nitrogen are taken together with their intervening atoms to form a 4-7 membered saturated, partially unsaturated, or heteroaryl ring having 0-3 heteroatoms, in addition to the nitrogen, independently selected from boron, nitrogen, oxygen, silicon, and sulfur.

In some embodiments, R is hydrogen. In some embodiments, R is deuterium. In some embodiments, R is optionally substituted $C_{1-6}$ aliphatic. In some embodiments, R is optionally substituted phenyl. In some embodiments, R is optionally substituted 4-7 membered saturated or partially unsaturated heterocyclic having 1-3 heteroatoms independently selected from boron, nitrogen, oxygen, silicon, and sulfur. In some embodiments, R is optionally substituted 5-6 membered heteroaryl ring having 1-4 heteroatoms independently selected from boron, nitrogen, oxygen, silicon, and sulfur. In some embodiments, two R groups on the same nitrogen are taken together with their intervening atoms to form a 4-7 membered saturated, partially unsaturated, or heteroaryl ring having 0-3 heteroatoms, in addition to the nitrogen, independently selected from boron, nitrogen, oxygen, silicon, and sulfur.

In some embodiments, R is selected from those depicted in Table 1, below.

As defined above and described herein, each of $R^2$ and $R^{3a}$ is independently hydrogen, deuterium, —$R^6$, halogen, —CN, —$NO_2$, —OR, —$Si(OH)_2R$, —$Si(OH)R_2$, —SR, —$NR_2$, —$SiR_3$, —$S(O)_2R$, —$S(O)_2NR_2$, —S(O)R, —C(O)R, —C(O)OR, —$C(O)NR_2$, —C(O)N(R)OR, —$C(R)_2N(R)C(O)R$, —$C(R)_2N(R)C(O)NR_2$, —OC(O)R, —$OC(O)NR_2$, —$OP(O)R_2$, —$OP(O)(OR)_2$, —$OP(O)(OR)NR_2$, —$OP(O)(NR_2)_2$—, —N(R)C(O)OR, —N(R)C(O)R, —$N(R)C(O)NR_2$, —$N(R)S(O)_2R$, —$NP(O)R_2$, —$N(R)P(O)(OR)_2$, —$N(R)P(O)(OR)NR_2$, —$N(R)P(O)(NR_2)_2$, or —$N(R)S(O)_2R$.

In some embodiments, $R^2$ and $R^{3a}$ is independently hydrogen. In some embodiments, $R^2$ and $R^{3a}$ is independently deuterium. In some embodiments, $R^2$ and $R^{3a}$ is independently —R. In some embodiments, $R^2$ and $R^{3a}$ is independently halogen. In some embodiments, $R^2$ and $R^{3a}$ is independently —CN. In some embodiments, $R^2$ and $R^{3a}$ is independently —$NO_2$. In some embodiments, $R^2$ and $R^{3a}$ is independently —OR. In some embodiments, $R^2$ and $R^{3a}$ is independently —$Si(OH)_2R$. In some embodiments, $R^2$ and $R^{3a}$ is independently —$Si(OH)R_2$. In some embodiments, $R^2$ and $R^{3a}$ is independently —SR. In some embodiments, $R^2$ and $R^{3a}$ is independently —$NR_2$. In some embodiments, $R^2$ and $R^{3a}$ is independently —$SiR_3$. In some embodiments, $R^2$ and $R^{3a}$ is independently —$S(O)_2R$. In some embodiments, $R^2$ and $R^{3a}$ is independently —$S(O)_2NR_2$. In some embodiments, $R^2$ and $R^{3a}$ is independently —S(O)R. In some embodiments, $R^2$ and $R^{3a}$ is independently —C(O)R. In some embodiments, $R^2$ and $R^{3a}$ is independently —C(O)OR. In some embodiments, $R^2$ and $R^{3a}$ is independently —$C(O)NR_2$. In some embodiments, $R^2$ and $R^{3a}$ is independently —C(O)N(R)OR. In some embodiments, $R^2$ and $R^{3a}$ is independently —$C(R)_2N(R)C(O)R$. In some embodiments, $R^2$ and $R^{3a}$ is independently —$C(R)_2N(R)C(O)NR_2$. In some embodiments, $R^2$ and $R^{3a}$ is independently —OC(O)R. In some embodiments, $R^2$ and $R^{3a}$ is independently —$OC(O)NR_2$. In some embodiments, $R^2$ and $R^{3a}$ is independently —$OP(O)R_2$. In some embodiments, $R^2$ and $R^{3a}$ is independently —$OP(O)(OR)_2$. In some embodiments, $R^2$ and $R^{3a}$ is independently —$OP(O)(OR)NR_2$. In some embodiments, $R^2$ and $R^{3a}$ is independently —$OP(O)(NR_2)_2$—. In some embodiments, $R^2$ and $R^{3a}$ is independently —N(R)C(O)OR. In some embodiments, $R^2$ and $R^{3a}$ is independently —N(R)C(O)R. In some embodiments, $R^2$ and $R^{3a}$ is independently —$N(R)C(O)NR_2$. In some embodiments, $R^2$ and $R^{3a}$ is independently —$NP(O)R_2$. In some embodiments, $R^2$ and $R^{3a}$ is independently —$N(R)P(O)(OR)_2$. In some embodiments, $R^2$ and $R^{3a}$ is independently —$N(R)P(O)(OR)NR_2$. In some embodiments, $R^2$ and $R^{3a}$ is independently —$N(R)P(O)(NR_2)_2$. In some embodiments, $R^2$ and $R^{3a}$ is independently —$N(R)S(O)_2R$.

In some embodiments, $R^2$ and $R^{3a}$ is independently —OH. In some embodiments, $R^2$ and $R^{3a}$ is independently —$NH_2$. In some embodiments, $R^2$ and $R^{3a}$ is independently —$CH_2NH_2$. In some embodiments, $R^2$ and $R^{3a}$ is independently —$CH_2NHCOMe$. In some embodiments, $R^2$ and $R^{3a}$ is independently —$CH_2NHCONHMe$. In some embodiments, $R^2$ and $R^{3a}$ is independently —NHCOMe. In some embodiments, $R^2$ and $R^{3a}$ is independently—NHCONHEt. In some embodiments, $R^2$ and $R^{3a}$ is independently —$SiMe_3$. In some embodiments, $R^2$ and $R^{3a}$ is independently —$SiMe_2OH$. In some embodiments, $R^2$ and $R^{3a}$ is independently —$SiMe(OH)_2$. In some embodiments $R^2$ and $R^{3a}$ is independently

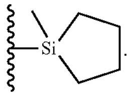 [SMILES: *[Si]1(C)CCCC1]

In some embodiments, $R^2$ and $R^{3a}$ is independently Br. In some embodiments, $R^2$ and $R^{3a}$ is independently Cl. In some embodiments, $R^2$ and $R^{3a}$ is independently F. In some embodiments, $R^2$ and $R^{3a}$ is independently Me. In some embodiments, $R^2$ and $R^{3a}$ is independently —NHMe. In some embodiments, $R^2$ and $R^{3a}$ is independently —$NMe_2$. In some embodiments, $R^2$ and $R^{3a}$ is independently —$NHCO_2Et$. In some embodiments, $R^2$ and $R^{3a}$ is independently —CN. In some embodiments, $R^2$ and $R^{3a}$ is independently —$CH_2Ph$. In some embodiments, $R^2$ and $R^{3a}$ is independently —$NHCO_2tBu$. In some embodiments, $R^2$ and $R^{3a}$ is independently —$CO_2tBu$. In some embodiments, $R^2$ and $R^{3a}$ is independently —OMe. In some embodiments, $R^2$ and $R^{3a}$ is independently —$CF_3$.

In some embodiments, $R^2$ or $R^{3a}$ is selected from those depicted in Table 1, below.

As defined above and described herein, $R_3$ is hydrogen, deuterium, halogen, —CN, —$NO_2$, —OR, —$NR_2$, —SR, —$S(O)_2R$, —$S(O)_2NR_2$, —S(O)R, —C(O)R, —C(O)OR, —$C(O)NR_2$, —C(O)NR(OR), —OC(O)R, —$OC(O)NR_2$, —$OP(O)(OR)_2$, —$OP(O)(NR_2)_2$, —$OP(O)(OR)NR_2$, —N(R)C(O)R, —N(R)C(O)OR, —$N(R)C(O)NR_2$, —$N(R)S(O)_2R$, —$N(R)S(O)_2NR_2$, —$N(R)P(O)(OR)_2$, —$N(R)P(O)(OR)NR_2$, —$P(O)(OR)_2$, —$P(O)(NR_2)OR$, —$P(O)(NR_2)_2$, —$Si(OH)_2R$, —$Si(OH)(R)_2$, or —$Si(R)_3$.

In some embodiments, $R^3$ is hydrogen. In some embodiments, $R^3$ is deuterium. In some embodiments, $R^3$ is halogen. In some embodiments, $R^3$ is —CN. In some embodiments, $R^3$ is —$NO_2$. In some embodiments, $R^3$ is —OR. In some embodiments, $R^3$ is —$NR_2$. In some embodiments, $R^3$ is —SR. In some embodiments, $R^3$ is —$S(O)_2R$. In some embodiments, $R^3$ is —$S(O)_2NR_2$. In some embodiments, $R^3$ is —S(O)R. In some embodiments, $R^3$ is —C(O)R. In some embodiments, $R^3$ is —C(O)OR. In some embodiments, $R^3$ is —$C(O)NR_2$. In some embodiments, $R^3$ is —C(O)NR(OR). In some embodiments, $R^3$ is —OC(O)R. In some embodiments, $R^3$ is —$OC(O)NR_2$. In some embodiments, $R^3$ is —$OP(O)(OR)_2$. In some embodiments, $R^3$ is —$OP(O)(NR_2)_2$. In some embodiments, $R^3$ is —$OP(O)(OR)NR_2$. In some embodiments, $R^3$ is —N(R)C(O)R. In some embodiments, $R^3$ is —N(R)C(O)OR. In some embodiments, $R^3$ is —$N(R)C(O)NR_2$. In some embodiments, $R^3$ is —$N(R)S(O)_2R$. In some embodiments, $R^3$ is —$N(R)S(O)_2NR_2$. In some embodiments, $R^3$ is —$N(R)P(O)(OR)_2$. In some embodiments, $R^3$ is —$N(R)P(O)(OR)NR_2$. In some embodiments, $R^3$ is —$P(O)(OR)_2$. In some embodiments, $R^3$ is —$P(O)(NR_2)OR$. In some embodiments, $R^3$ is —$P(O)(NR_2)_2$. In some embodiments, $R^3$ is —$Si(OH)_2R$. In some embodiments, $R^3$ is —$Si(OH)(R)_2$. In some embodiments, $R^3$ is —$Si(R)_3$.

In some embodiments, $R^3$ is methyl. In some embodiments, $R^3$ is —$OCH_3$. In some embodiments, $R^3$ is chloro.

In some embodiments, $R^3$ is selected from those depicted in Table 1, below.

As defined above and described herein, each $R^4$ is independently hydrogen, deuterium, —$R^6$, halogen, —CN, —$NO_2$, —OR, —SR, —$NR_2$, —$S(O)_2R$, —$S(O)_2NR_2$, —S(O)R, —C(O)R, —C(O)OR, —$C(O)NR_2$, —C(O)N(R)OR, —OC(O)R, —$OC(O)NR_2$, —N(R)C(O)OR, —N(R)C(O)R, —$N(R)C(O)NR_2$, —$N(R)S(O)_2R$, —$P(O)(OR)_2$, —$P(O)(NR_2)OR$, or —$P(O)(NR_2)_2$.

In some embodiments, $R^4$ is hydrogen. In some embodiments, $R^4$ is —$R^6$. In some embodiments, $R^4$ is halogen. In some embodiments, $R^4$ is —CN. In some embodiments, $R^4$ is —$NO_2$. In some embodiments, $R^4$ is —OR. In some embodiments, $R^4$ is —SR. In some embodiments, $R^4$ is —$NR_2$. In some embodiments, $R^4$ is —$S(O)_2R$. In some embodiments, $R^4$ is —$S(O)_2NR_2$. In some embodiments, $R^4$ is —S(O)R. In some embodiments, $R^4$ is —C(O)R. In some embodiments, $R^4$ is —C(O)OR. In some embodiments, $R^4$ is —$C(O)NR_2$. In some embodiments, $R^4$ is —C(O)N(R)OR. In some embodiments, $R^4$ is —OC(O)R. In some embodiments, $R^4$ is —$OC(O)NR_2$. In some embodiments, $R^4$ is —N(R)C(O)OR. In some embodiments, $R^4$ is —N(R)C(O)R. In some embodiments, $R^4$ is —$N(R)C(O)NR_2$. In some embodiments, $R^4$ is —$N(R)S(O)_2R$. In some embodiments, $R^4$ is —$P(O)(OR)_2$. In some embodiments, $R^4$ is —$P(O)(NR_2)OR$. In some embodiments, $R^4$ is —$P(O)(NR_2)_2$.

In some embodiments, $R^4$ is methyl. In some embodiments, $R^4$ is ethyl. In some embodiments, $R^4$ is cyclopropyl.

In some embodiments, $R^4$ is selected from those depicted in Table 1, below.

As defined above and described herein, $R^5$ is hydrogen, deuterium, an optionally substitute $C_{1-4}$ aliphatic, or —CN.

In some embodiments, $R^5$ is hydrogen. In some embodiments, $R^5$ is deuterium. In some embodiments, $R^5$ is an optionally substituted $C_{1-4}$ aliphatic. In some embodiments, $R^5$ is —CN.

In some embodiments, $R^5$ is selected from those depicted in Table 1, below.

As defined above and described herein, each $R^6$ is independently an optionally substituted group selected from $C_{1-6}$ aliphatic, phenyl, a 4-7 membered saturated or partially unsaturated heterocyclic ring having 1-3 heteroatoms independently selected from boron, nitrogen, oxygen, silicon, and sulfur, and a 5-6 membered heteroaryl ring having 1-4 heteroatoms independently selected from boron, nitrogen, oxygen, silicon, and sulfur.

In some embodiments, $R^6$ is an optionally substituted $C_{1-6}$ aliphatic. In some embodiments, $R^6$ is an optionally substituted phenyl. In some embodiments, $R^6$ is an optionally substituted 4-7 membered saturated or partially unsaturated heterocyclic ring having 1-3 heteroatoms independently selected from boron, nitrogen, oxygen, silicon, and sulfur. In some embodiments, $R^6$ is an optionally substituted 5-6 membered heteroaryl ring having 1-4 heteroatoms independently selected from boron, nitrogen, oxygen, silicon, and sulfur.

In some embodiments, $R^6$ is selected from those depicted in Table 1, below.

As defined above and described herein, Ring A is a bi- or tricyclic ring selected from

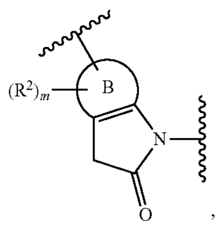
,
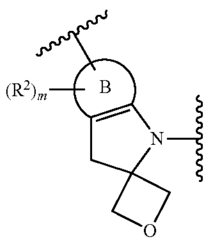
,

-continued
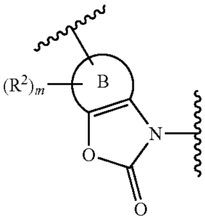,
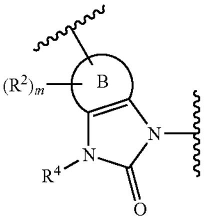,
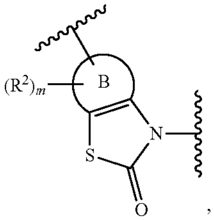,
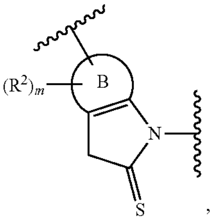,
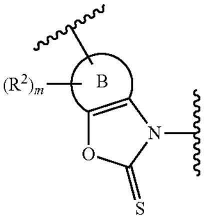,
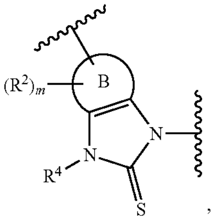,
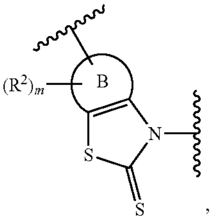,
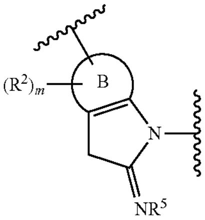,
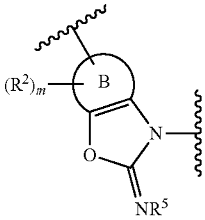,
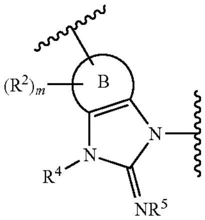,
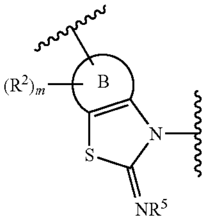,
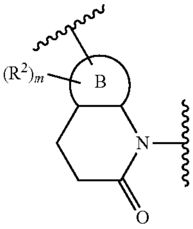,
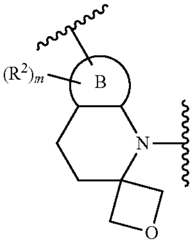,
-continued
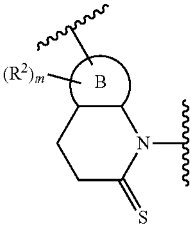,
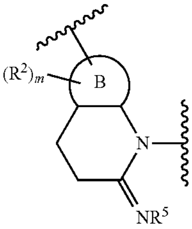,
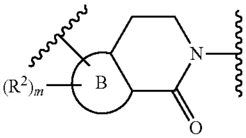,
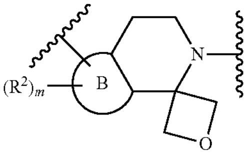,
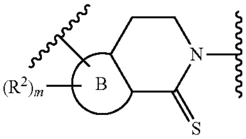,
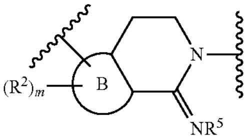,
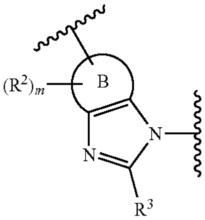,
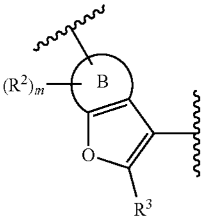,
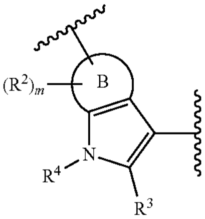, or
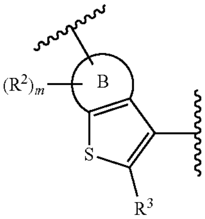.
In some embodiments, Ring A is
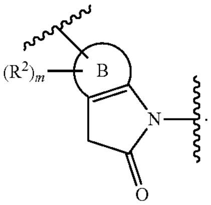.
In some embodiments, Ring A is
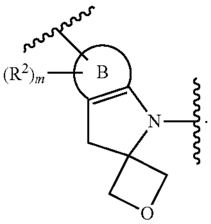.

In some embodiments, Ring A is
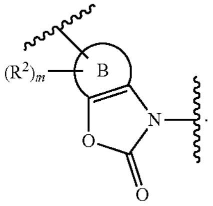
In some embodiments, Ring A is
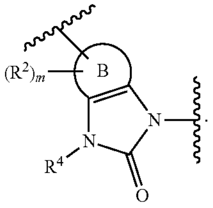
In some embodiments, Ring A is
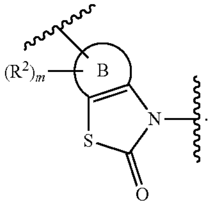
In some embodiments, Ring A is
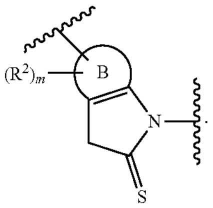
In some embodiments, Ring A is
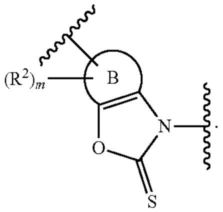
In some embodiments, Ring A is
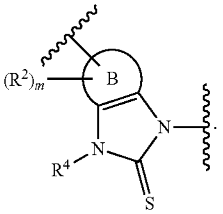
In some embodiments, Ring A is
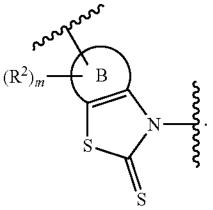
In some embodiments, Ring A is
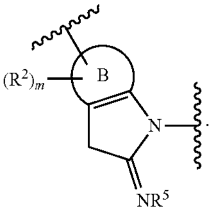
In some embodiments, Ring A is
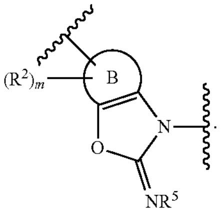
In some embodiments, Ring A is
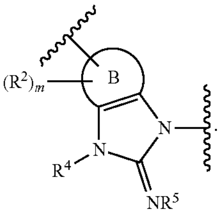

In some embodiments, Ring A is
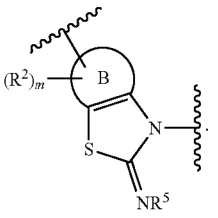
In some embodiments, Ring A is
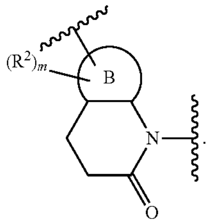
In some embodiments, Ring A is
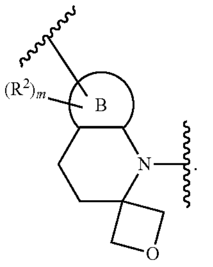
In some embodiments, Ring A is
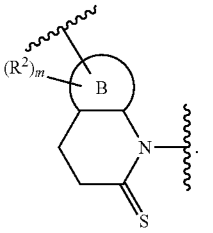
In some embodiments, Ring A is
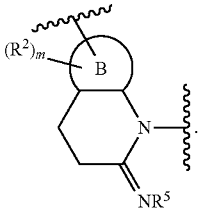
In some embodiments, Ring A is
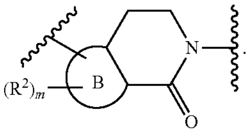
In some embodiments, Ring A is
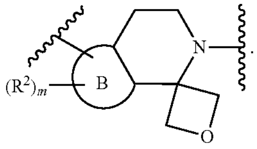
In some embodiments, Ring A is
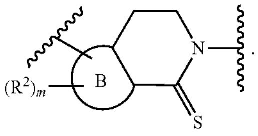
In some embodiments, Ring A is
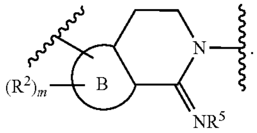
In some embodiments, Ring A is
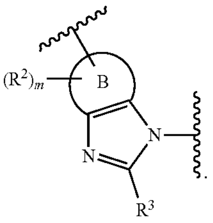
In some embodiments, Ring A is
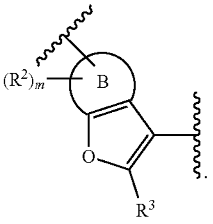

In some embodiments, Ring A is
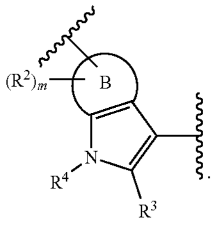
In some embodiments, Ring A is
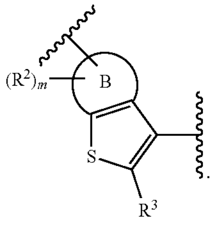
In some embodiments, Ring A is
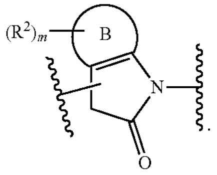
In some embodiments, Ring A is
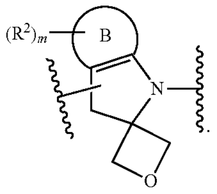
In some embodiments, Ring A is
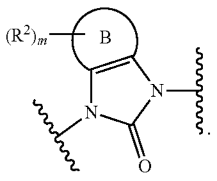
In some embodiments, Ring A is
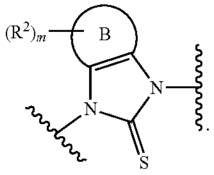
In some embodiments, Ring A is
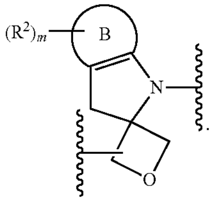
In some embodiments, Ring A is
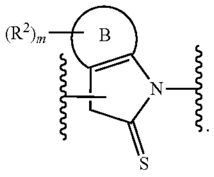
In some embodiments, Ring A is
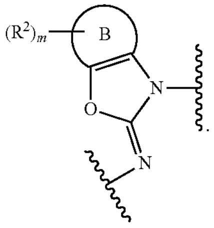
In some embodiments, Ring A is
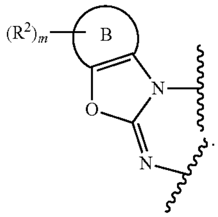

In some embodiments, Ring A is
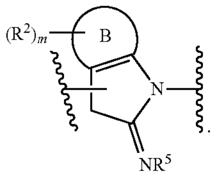
In some embodiments, Ring A is
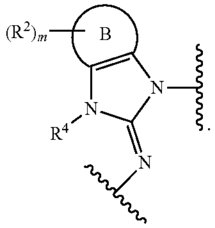
In some embodiments, Ring A is
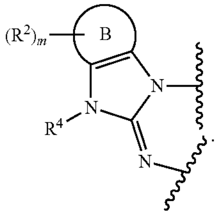
In some embodiments, Ring A is
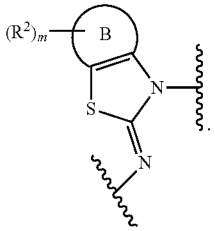
In some embodiments, Ring A is
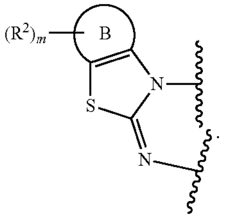
In some embodiments, Ring A is
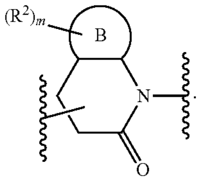
In some embodiments, Ring A is
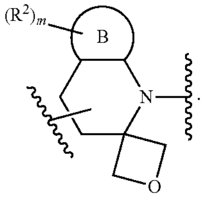
In some embodiments, Ring A is
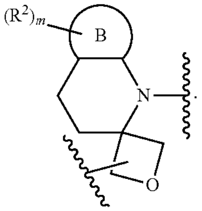
In some embodiments, Ring A is
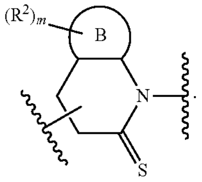
In some embodiments, Ring A is
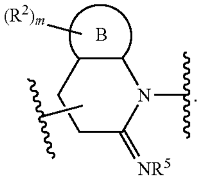

In some embodiments, Ring A is
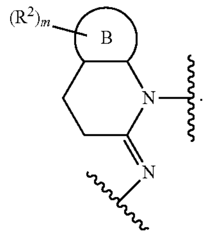
In some embodiments, Ring A is
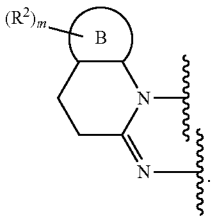
In some embodiments,
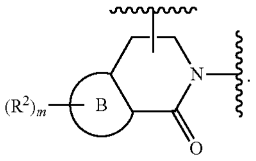
Ring A is
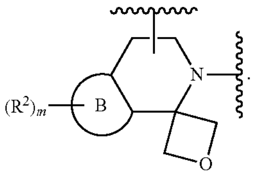
In some embodiments, Ring A is
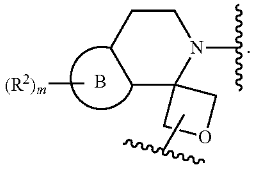
In some embodiments, Ring A is
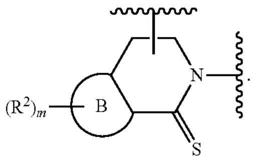
In some embodiments, Ring A is
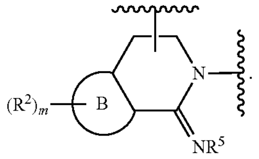
In some embodiments, Ring A is
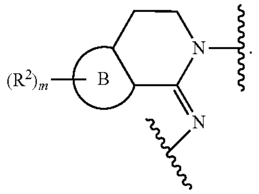
In some embodiments, Ring A is
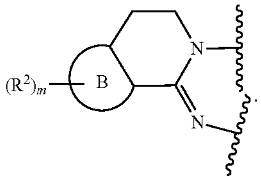
In some embodiments, Ring A is
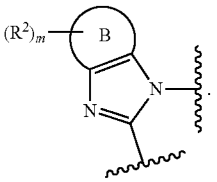
In some embodiments, Ring A is
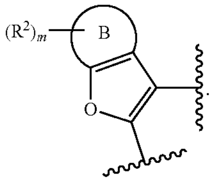
In some embodiments, Ring A is
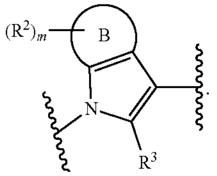

In some embodiments, Ring A is

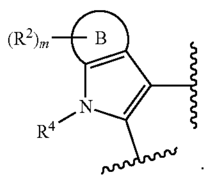

In some embodiments, Ring A is

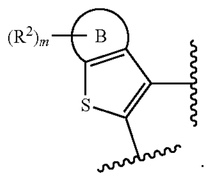

In some embodiments, Ring A is

In some embodiments, Ring A is selected from those depicted in Table 1, below.

As defined above and described herein, Ring B is a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;

In some embodiments, Ring B is a fused 6-membered aryl. In some embodiments, Ring B is a fused 6-membered heteroaryl containing 1-4 heteroatoms independently selected from nitrogen, oxygen, or sulfur. In some embodiments, Ring B is a fused 5 to 7-membered saturated or partially unsaturated carbocyclyl. In some embodiments, Ring B is fused 5 to 7-membered saturated or partially saturated heterocyclyl with 1-3 heteroatoms independently selected from boron, nitrogen, oxygen, silicon, or sulfur. In some embodiments, Ring B is fused 5-membered heteroaryl with 1-4 heteroatoms independently selected from boron, nitrogen, oxygen, silicon, or sulfur.

In some embodiments, Ring B is

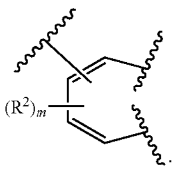

In some embodiments, Ring B is

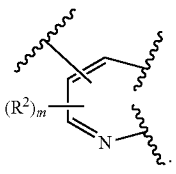

In some embodiments, Ring B is

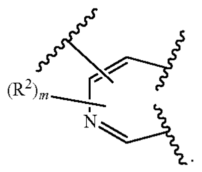

In some embodiments, Ring B is

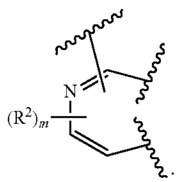

In some embodiments, Ring B is

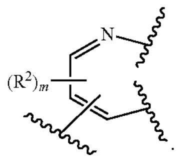

In some embodiments, Ring B is

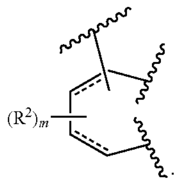

In some embodiments, Ring B is

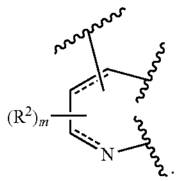

In some embodiments, Ring B is

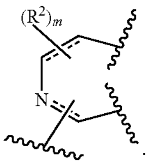

In some embodiments, Ring B is
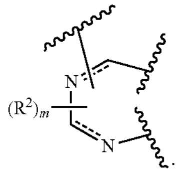
In some embodiments, Ring B is
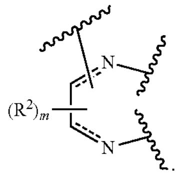
In some embodiments, Ring B is
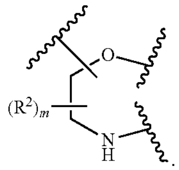
In some embodiments, Ring B is
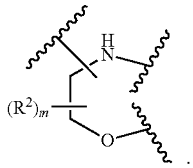
In some embodiments, Ring B is
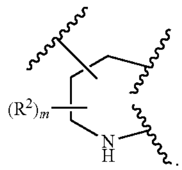
In some embodiments, Ring B is
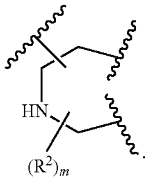
In some embodiments, Ring B is
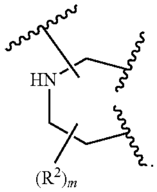
In some embodiments, Ring B is
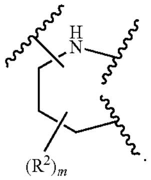
In some embodiments, Ring B is
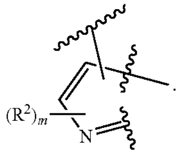
In some embodiments, Ring B is
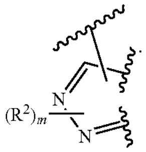
In some embodiments, Ring B is
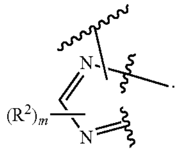
In some embodiments, Ring B is
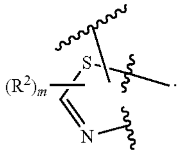

In some embodiments, Ring B is
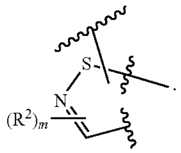
In some embodiments, Ring B is
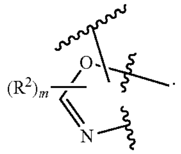
In some embodiments, Ring B is
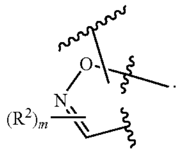
In some embodiments, Ring B is
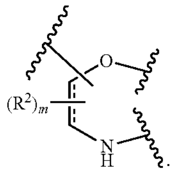
In some embodiments, Ring B is
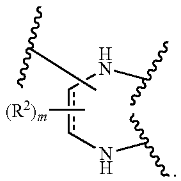
In some embodiments, Ring B is
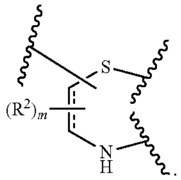
In some embodiments, Ring B is
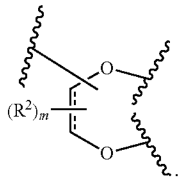
In some embodiments, Ring B is
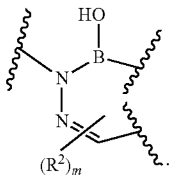
In some embodiments, Ring B is selected from
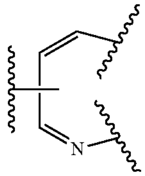,
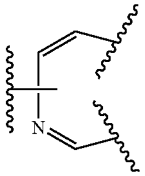,
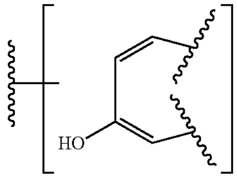,
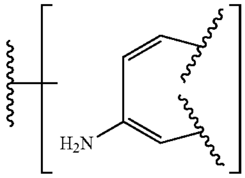,
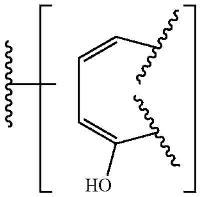,
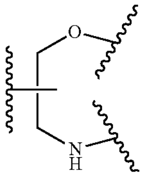,
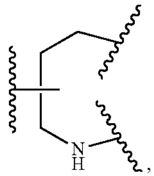,
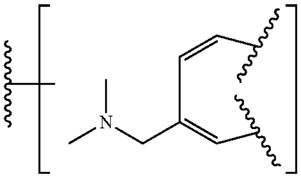,
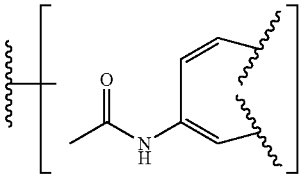,
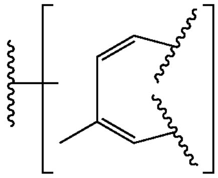,
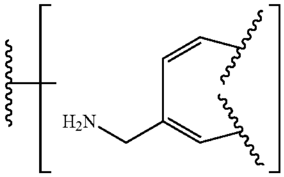,
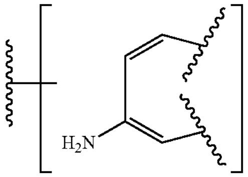, -continued
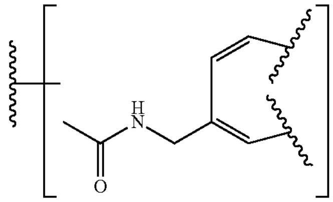,
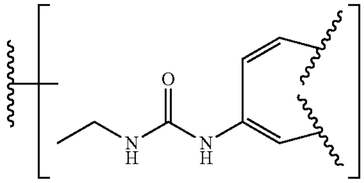,
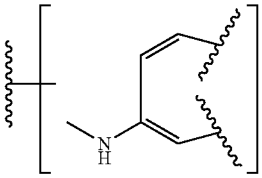, 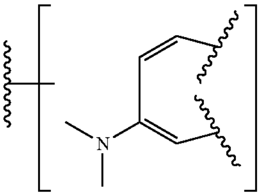,
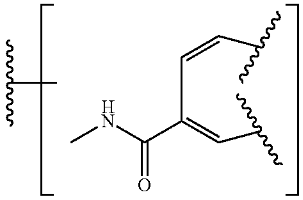,
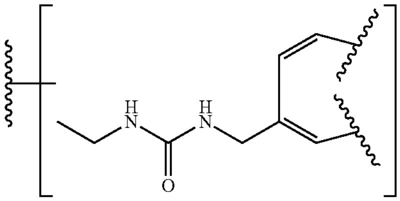,
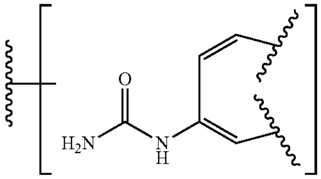, 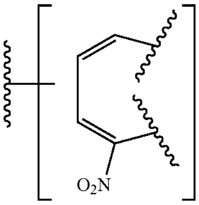,
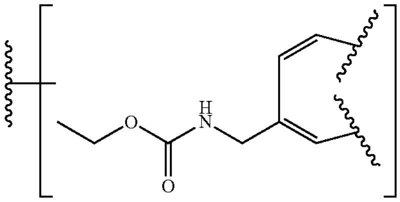,
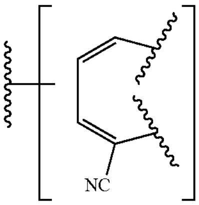, 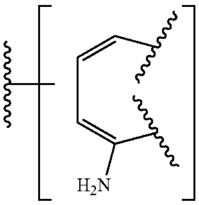,
-continued
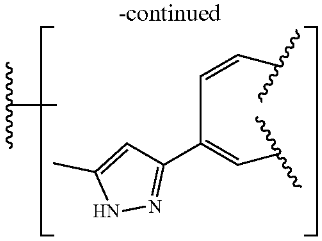,
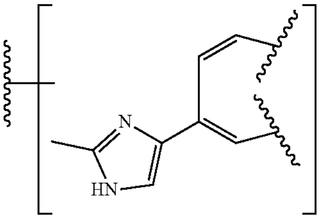, or
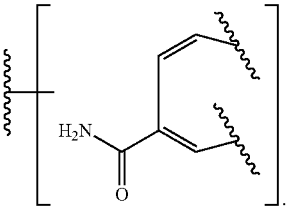.
In some embodiments, Ring B is selected from those depicted in Table 1, below.
As defined above and described herein, Ring C is a mono- or bicyclic ring selected from
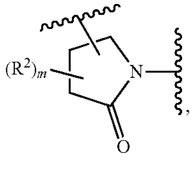, 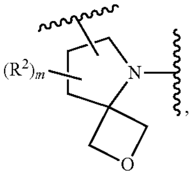,
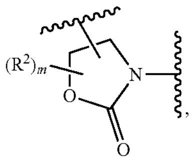, 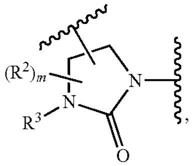,
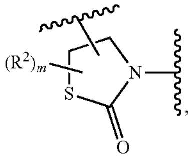, 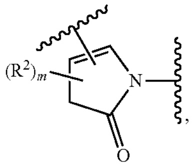,
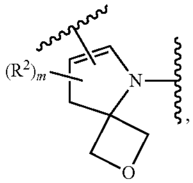, 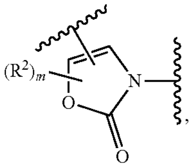,
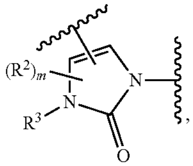, 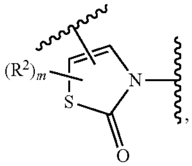, -continued
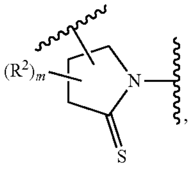,
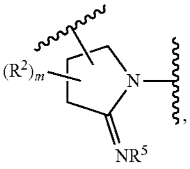,
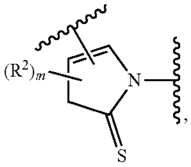,
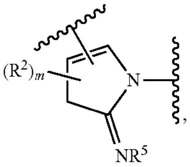,
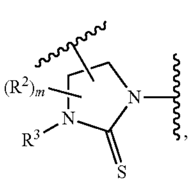,
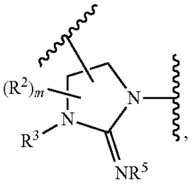,
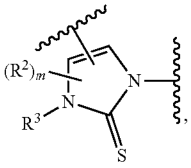,
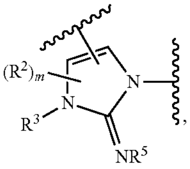,
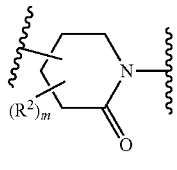,
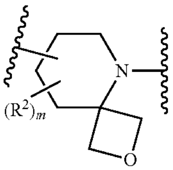,
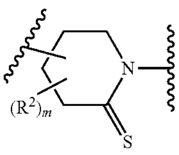
or
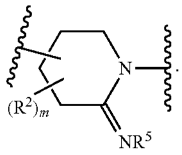.
In some embodiments, Ring C is
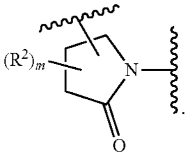.
In some embodiments, Ring C is
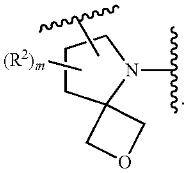.
In some embodiments, Ring C is
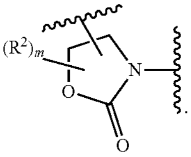.
In some embodiments, Ring C is
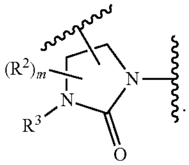.
In some embodiments, Ring C is
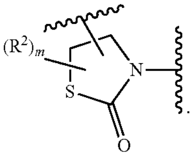.
In some embodiments, Ring C is
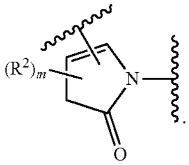.
In some embodiments, Ring C is
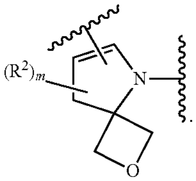.
In some embodiments, Ring C is
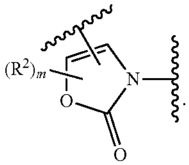.

In some embodiments, Ring C is
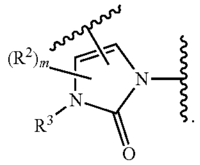
In some embodiments, Ring C is
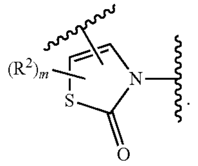
In some embodiments, Ring C is
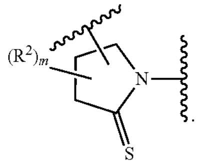
In some embodiments, Ring C is
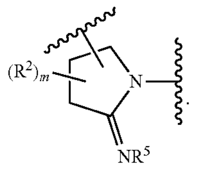
In some embodiments, Ring C is
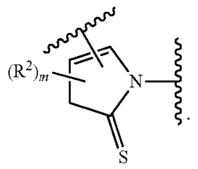
In some embodiments, Ring C is
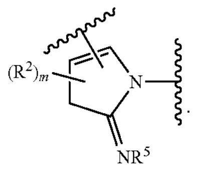
In some embodiments, Ring C is
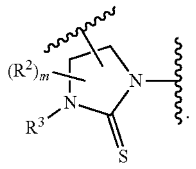
In some embodiments, Ring C is
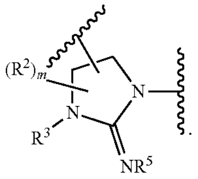
In some embodiments, Ring C is
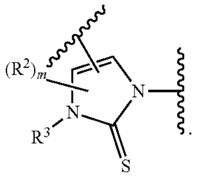
In some embodiments, Ring C is
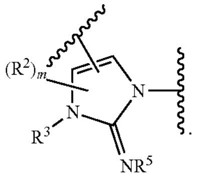
In some embodiments, Ring C is
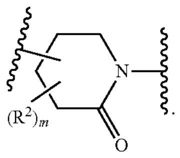
In some embodiments, Ring C is
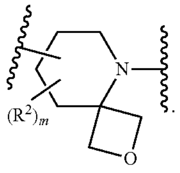

In some embodiments, Ring C is
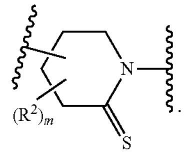
In some embodiments, Ring C is
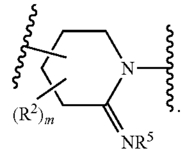
In some embodiments, Ring C is
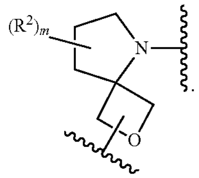
In some embodiments, Ring C is
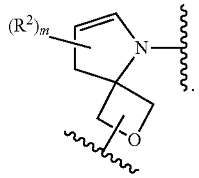
In some embodiments, Ring C is
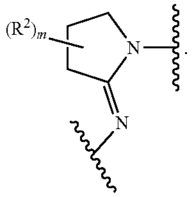
In some embodiments, Ring C is
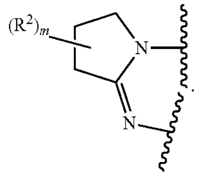
In some embodiments, Ring C is
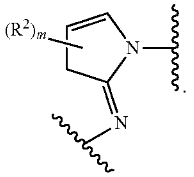
In some embodiments, Ring C is
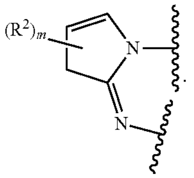
In some embodiments, Ring C is
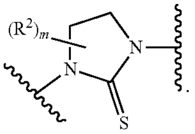
In some embodiments, Ring C is
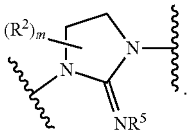
In some embodiments, Ring C is
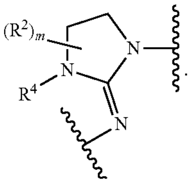
In some embodiments, Ring C is
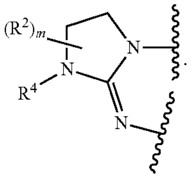

In some embodiments, Ring C is
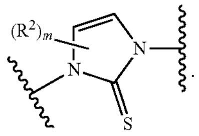
In some embodiments, Ring C is
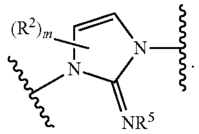
In some embodiments, Ring C is
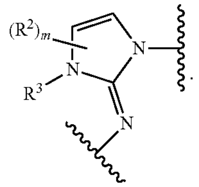
In some embodiments, Ring C is
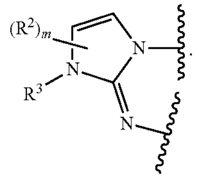
In some embodiments, Ring C is
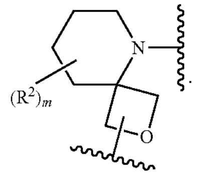
In some embodiments, Ring C is
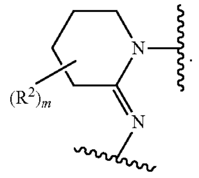
In some embodiments, Ring C is
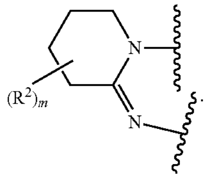
In some embodiments, Ring C is a mono- or bicyclic ring selected from
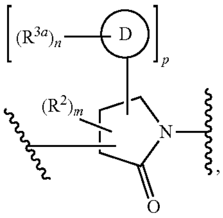,
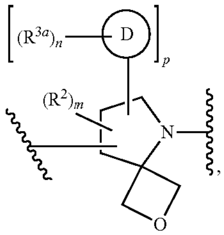,
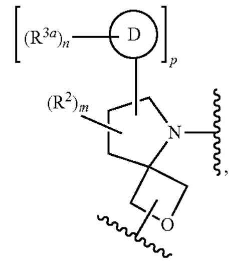,
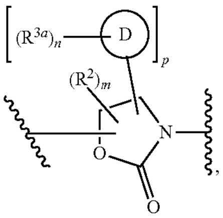,
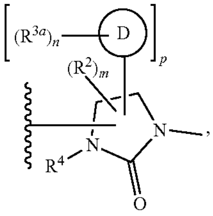,
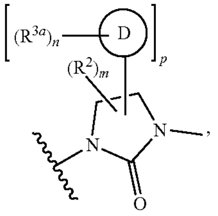,
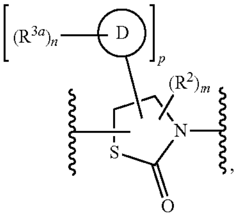,
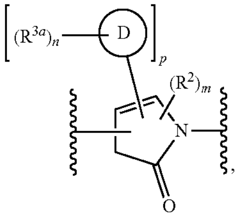,
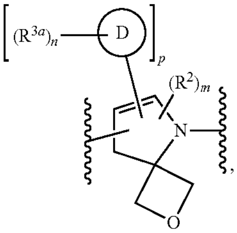,
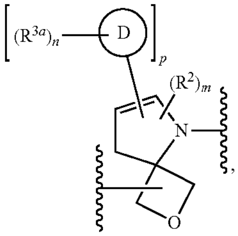,
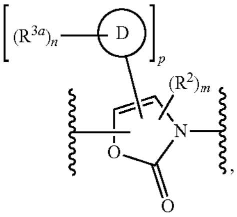,
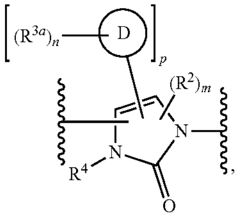, -continued
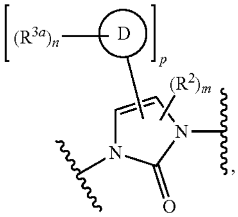,
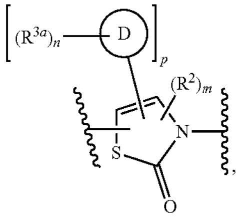,
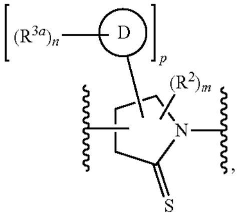,
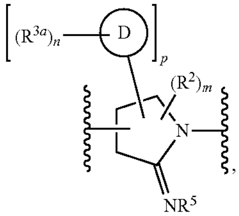,
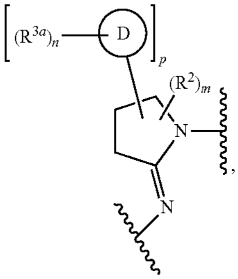,
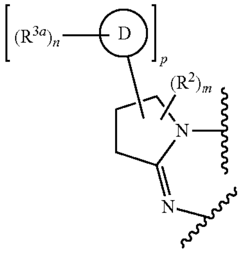,
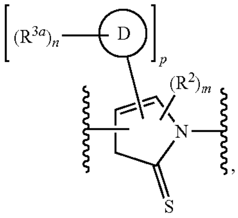,
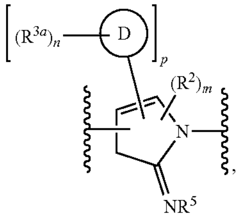,
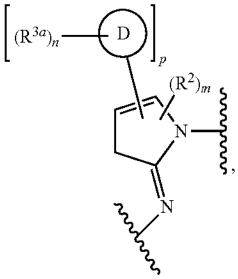,
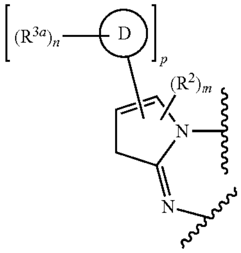,
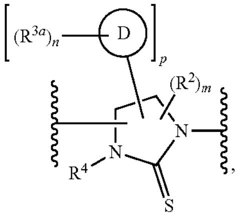,
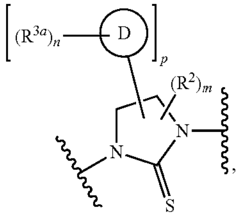,
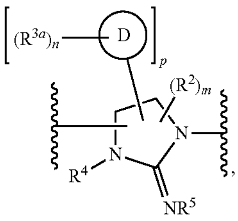,
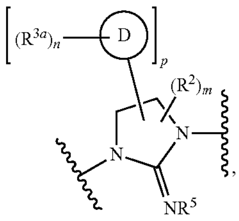,
-continued
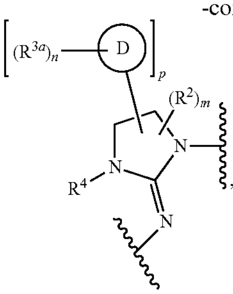,
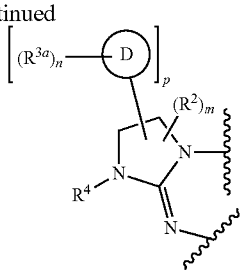,
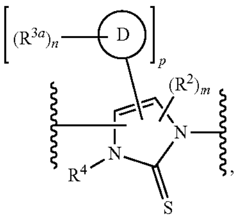,
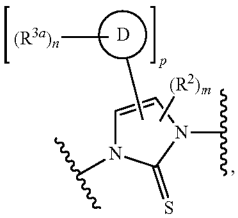,
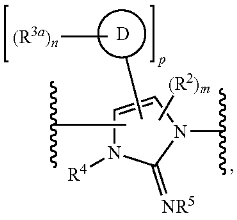,
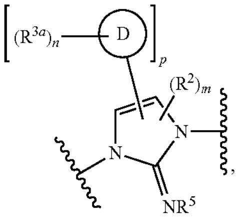,
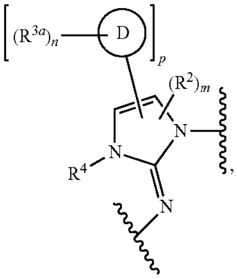,
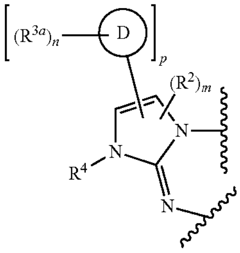,
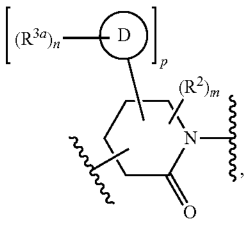,
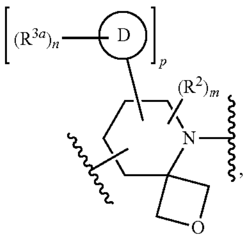,
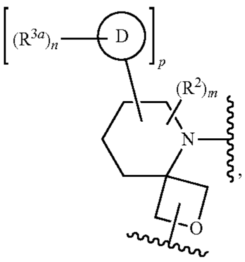,
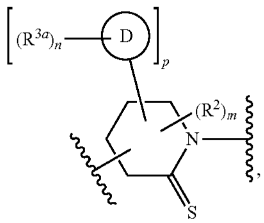, -continued

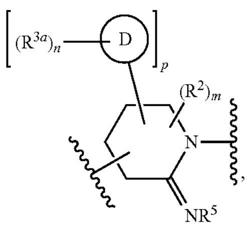

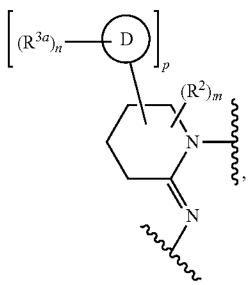

or

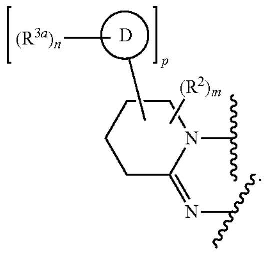

In some embodiments, Ring C is selected from

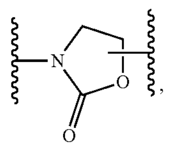

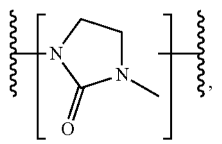

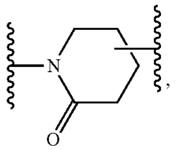

or

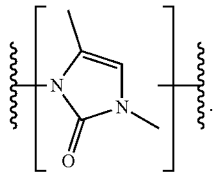

In some embodiments, Ring C is selected from

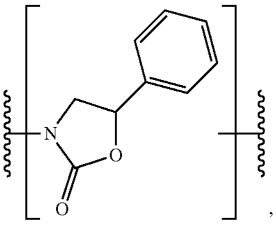

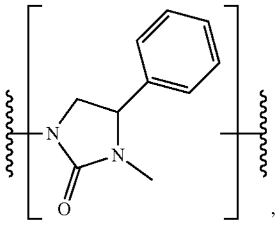

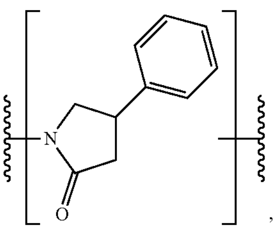

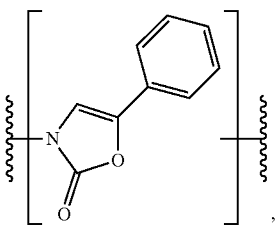

-continued

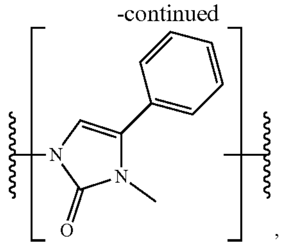

or

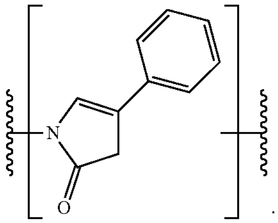

In some embodiments, Ring C is selected from those depicted in Table 1, below.

As defined above and described herein, Ring D is a ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;

In some embodiments, Ring D is a 6-membered aryl. In some embodiments, Ring D is a 6-membered heteroaryl containing 1-4 heteroatoms independently selected from nitrogen, oxygen, or sulfur. In some embodiments, Ring D is a 5 to 7-membered saturated or partially unsaturated carbocyclyl. In some embodiments, Ring D is 5 to 7-membered saturated or partially saturated heterocyclyl with 1-3 heteroatoms independently selected from boron, nitrogen, oxygen, silicon, or sulfur. In some embodiments, Ring D is 5-membered heteroaryl with 1-4 heteroatoms independently selected from boron, nitrogen, oxygen, silicon, or sulfur.

In some embodiments, Ring D is selected from those depicted in Table 1, below.

As defined above and described herein, each of Ring E, Ring F, and Ring G is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur, wherein each of Ring E, Ring F, and Ring G is independently and optionally further substituted with 1-2 oxo groups.

In some embodiments, each Ring E, Ring F, and Ring G is independently a 6-membered aryl. In some embodiments, each Ring E, Ring F, and Ring G is independently a 6-membered heteroaryl containing 1-4 heteroatoms independently selected from nitrogen, oxygen, or sulfur. In some embodiments, each Ring E, Ring F, and Ring G is independently a 5 to 7-membered saturated or partially unsaturated carbocyclyl. In some embodiments, each Ring E, Ring F, and Ring G is independently a 5 to 7-membered saturated or partially unsaturated heterocyclyl with 1-3 heteroatoms independently selected from boron, nitrogen, oxygen, silicon, or sulfur. In some embodiments, each Ring E, Ring F, and Ring G is independently a 5-membered heteroaryl with 1-4 heteroatoms independently selected from nitrogen, oxygen or sulfur. In some embodiments, each of Ring E, Ring F, and Ring G is independently and optionally further substituted with 1-2 oxo groups.

In some embodiments, Ring F is

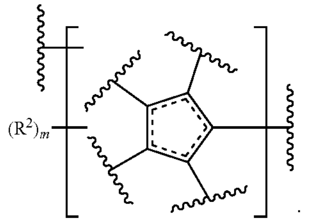

In some embodiments, Ring F is

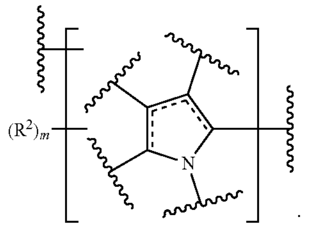

In some embodiments, Ring F is

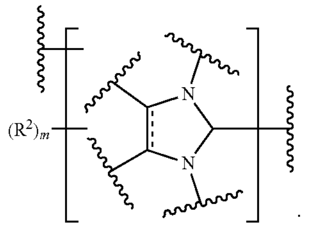

In some embodiments, Ring F is

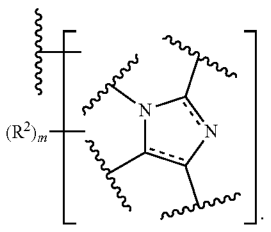

In some embodiments, Ring F is

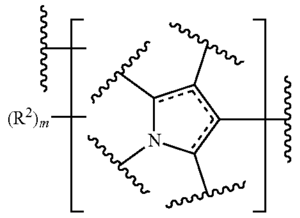

In some embodiments, Ring F is

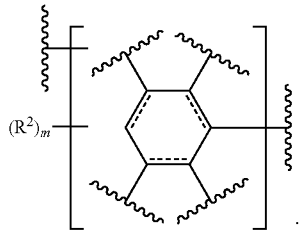

In some embodiments, Ring F is

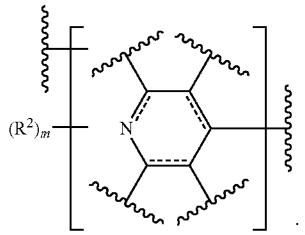

In some embodiments, Ring F is

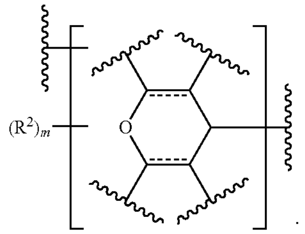

In some embodiments, Ring F is

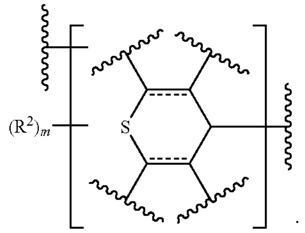

In some embodiments, Ring F is
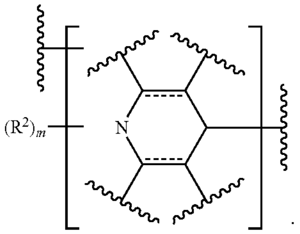
In some embodiments, Ring F is
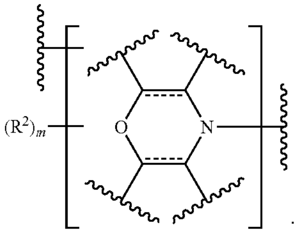
In some embodiments, Ring F is
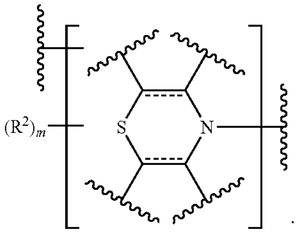
In some embodiments, Ring F is
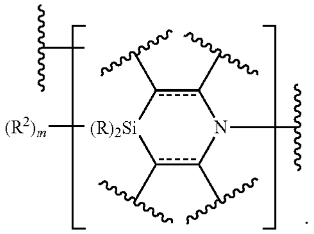
In some embodiments, Ring F is
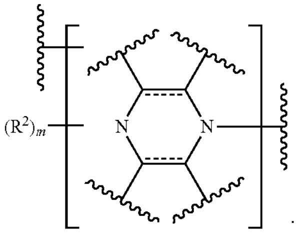
In some embodiments, Ring F is
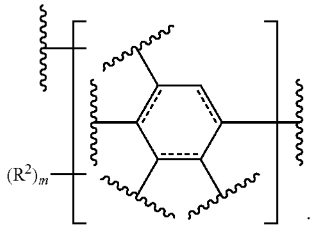
In some embodiments, Ring F is
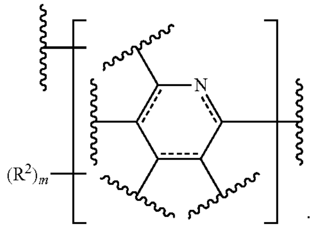
In some embodiments, Ring F is
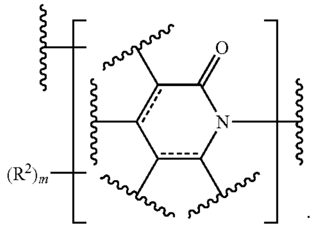
In some embodiments, Ring F is
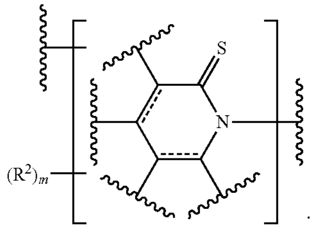
In some embodiments, Ring F is
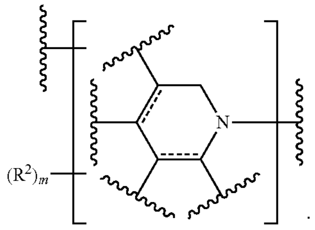

In some embodiments, Ring F is
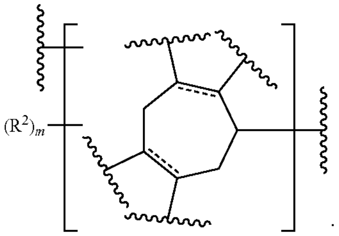
In some embodiments, Ring F is
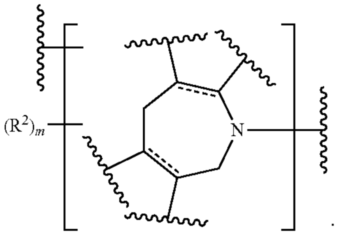
In some embodiments, Ring F is
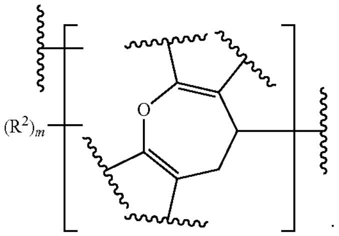
In some embodiments, Ring F is
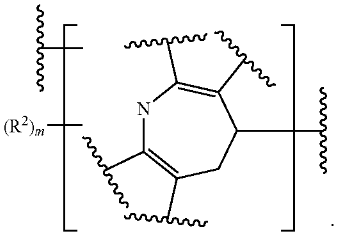
In some embodiments, Ring F is
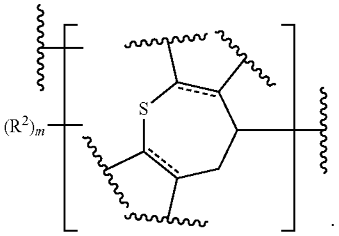
In some embodiments, Ring F is
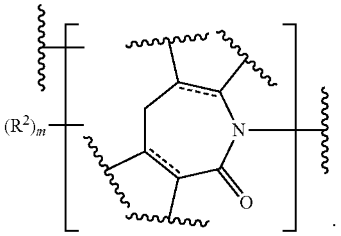
In some embodiments, Ring F is
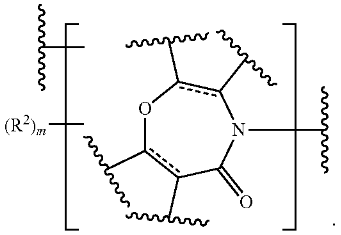
In some embodiments, Ring F is
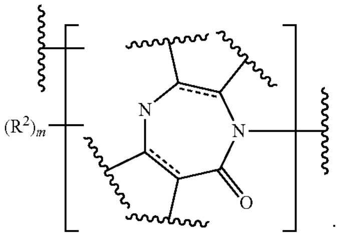
In some embodiments, Ring F is
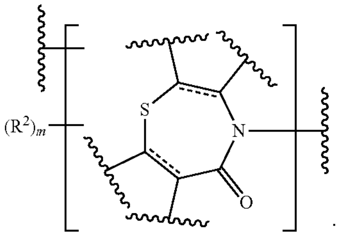
In some embodiments, Ring F is
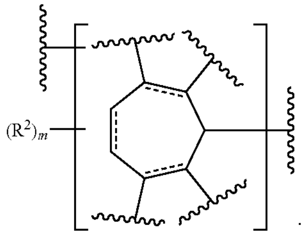

In some embodiments, Ring F is

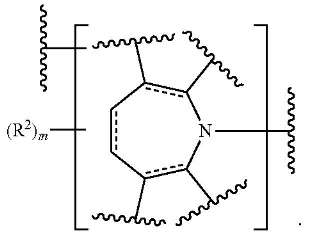

In some embodiments, Ring F is

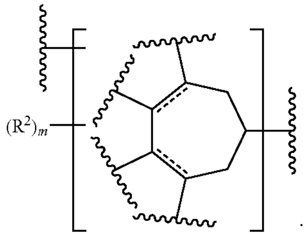

In some embodiments, Ring F is

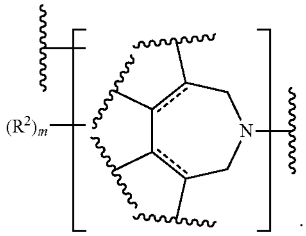

In some embodiments, Ring F is

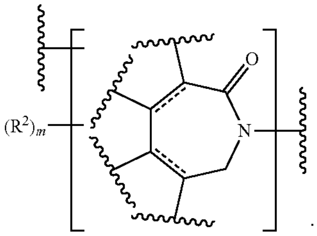

In some embodiments, Ring F is

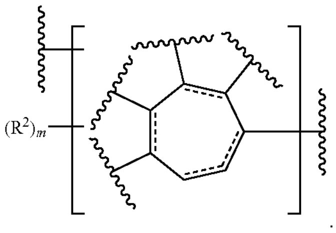

In some embodiments, Ring F is

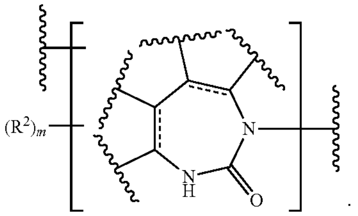

In some embodiments, Ring F is

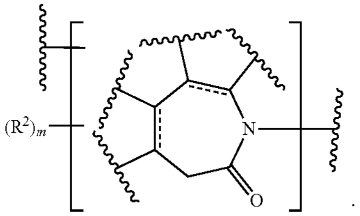

In some embodiments, each Ring E and Ring G is independently

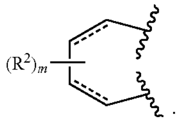

In some embodiments, each Ring E and Ring G is independently

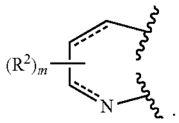

In some embodiments, each Ring E and Ring G is independently

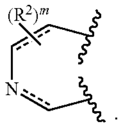

In some embodiments, each Ring E and Ring G is independently

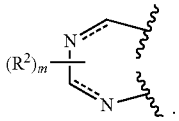

In some embodiments, Ring E and Ring G is independently

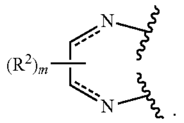

In some embodiments, Ring E and Ring G is independently is

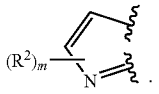

In some embodiments, Ring E and Ring G is independently

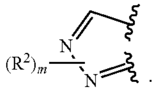

In some embodiments, Ring E and Ring G is independently

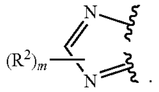

In some embodiments, Ring E and Ring G is independently

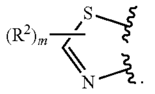

In some embodiments, Ring E and Ring G is independently
In some embodiments, Ring E and Ring G is independently

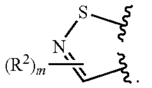

In some embodiments, Ring E and Ring G is independently

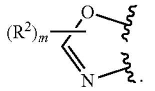

In some embodiments, Ring E and Ring G is independently

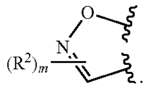

In some embodiments, Ring E and Ring G is independently

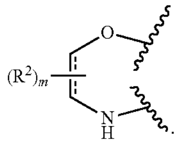

In some embodiments, Ring E and Ring G is independently

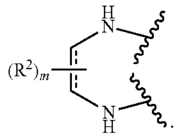

In some embodiments, Ring E and Ring G is independently

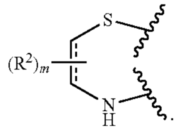

H In some embodiments, Ring E and Ring G is independently

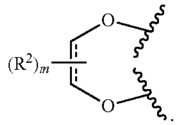

In some embodiments, Ring E and Ring G is independently

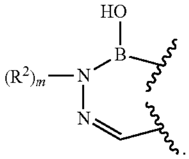

In some embodiments, Ring E, Ring F, and Ring G is

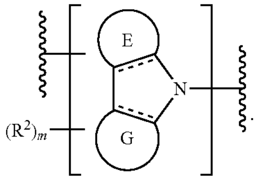

In some embodiments, Ring E, Ring F, and Ring G is

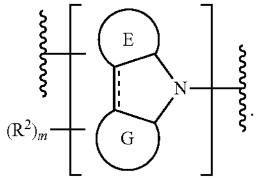

In some embodiment, Ring E, Ring F, and Ring G is

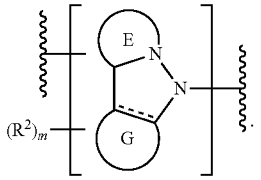

In some embodiments, Ring E, Ring F, and Ring G is

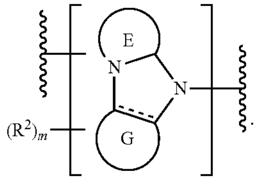

In some embodiments, Ring E, Ring F, and Ring G is

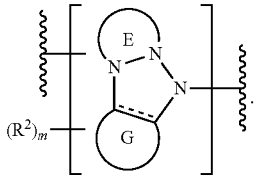

In some embodiments, Ring E, Ring F, and Ring G is

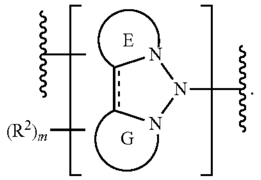

In some embodiments, Ring E, Ring F, and Ring G is

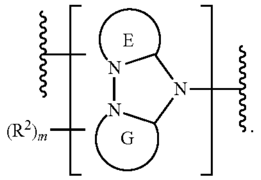

In some embodiments, Ring E, Ring F, and Ring G is

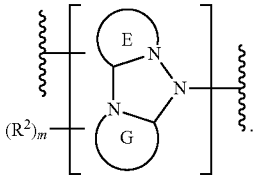

In some embodiments, Ring E, Ring F, and Ring G is

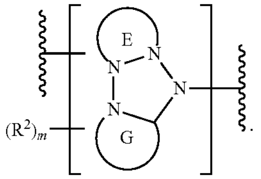

some embodiments, Ring E, Ring F, and Ring G is

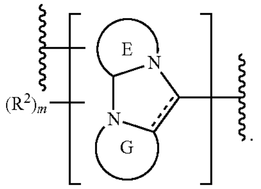

In some embodiments, Ring E, Ring F, and Ring G is

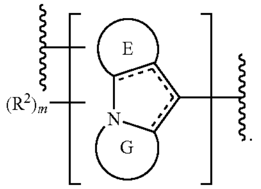

In some embodiments, Ring E, Ring F, and Ring G is

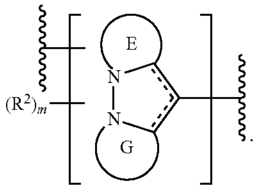

In some embodiments, Ring E, Ring F, and Ring G is

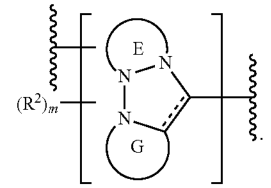

In some embodiments, Ring E, Ring F, and Ring G is

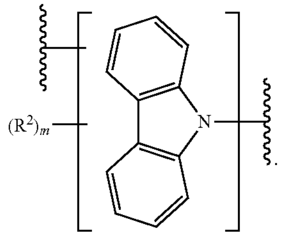

In some embodiments, Ring E, Ring F, and Ring G is

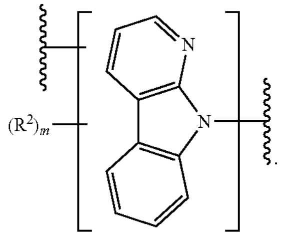

In some embodiments, Ring E, Ring F, and Ring G is

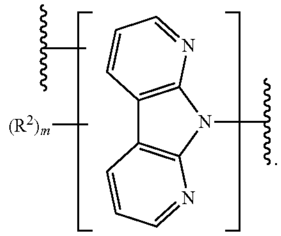

In some embodiments, Ring E, Ring F, and Ring G is

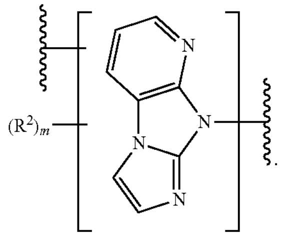

In some embodiments, Ring E, Ring F, and Ring G is

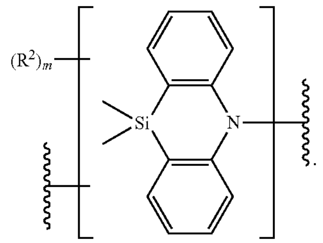

In some embodiments, Ring E, Ring F, and Ring G is

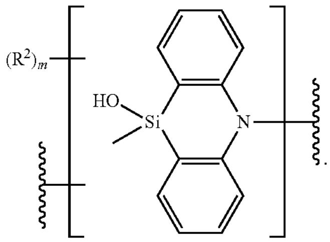

In some embodiments, Ring E, Ring F, and Ring G is

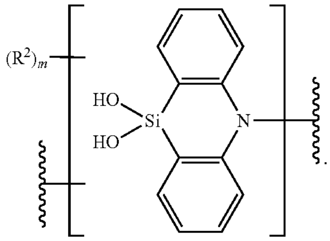

In some embodiments, Ring E, Ring F, and Ring G is

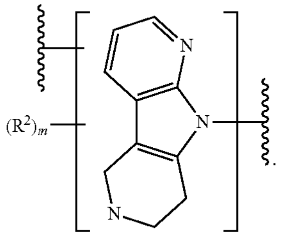

In some embodiments, Ring E, Ring F, and Ring G is
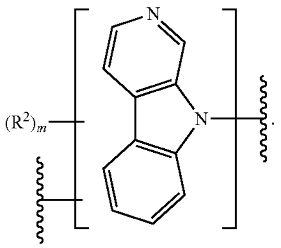
In some embodiments, Ring E, Ring F, and Ring G is
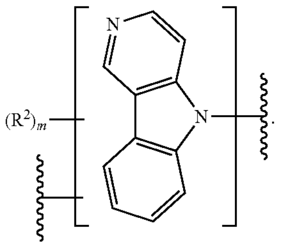
In some embodiments, Ring E, Ring F, and Ring G is
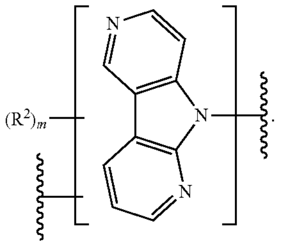
In some embodiments, Ring E, Ring F, and Ring G is
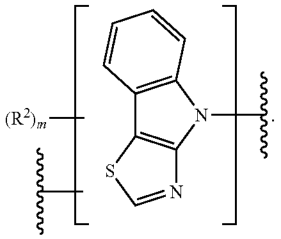
In some embodiments, Ring E, Ring F, and Ring G is
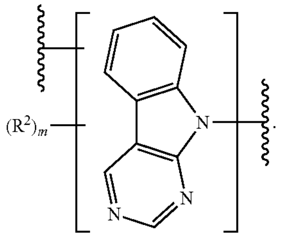
In some embodiments, Ring E, Ring F, and Ring G is
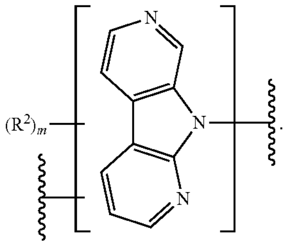
In some embodiments, Ring E, Ring F, and Ring G is
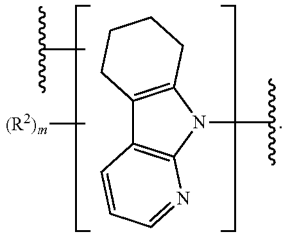
In some embodiments, Ring E, Ring F, and Ring G is
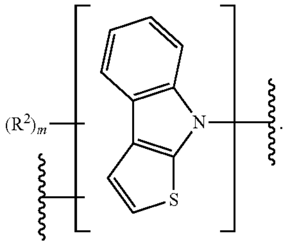

In some embodiments, Ring E, Ring F, and Ring G is

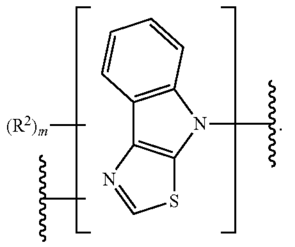

In some embodiments, Ring E, Ring F, and Ring G is

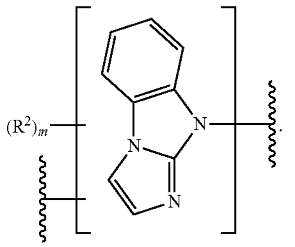

In some embodiments, Ring E, Ring F, and Ring G is

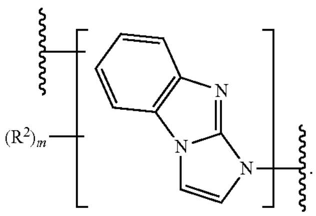

In some embodiments, Ring E, Ring F, and Ring G is

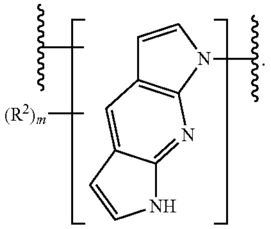

In some embodiments, Ring E, Ring F, and Ring G is

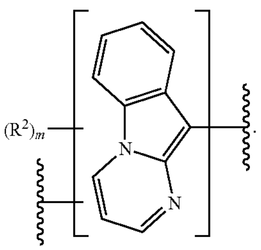

In some embodiments, Ring E, Ring F, and Ring G is

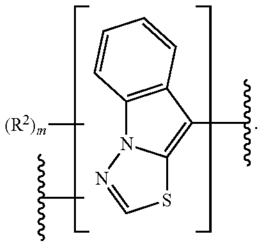

In some embodiments, Ring E, Ring F, and Ring G is selected from those depicted in Table 1, below.

As defined above and described herein, Ring H is a ring selected from a 7-9 membered saturated or partially unsaturated carbocyclyl or heterocyclyl ring with 1-3 heteroatoms independently selected from boron, nitrogen, oxygen, silicon, or sulfur, wherein Ring E is optionally further substituted with 1-2 oxo groups.

In some embodiments, Ring H is a ring selected from a 7-9 membered saturated or partially unsaturated carbocyclyl or heterocyclyl ring with 1-3 heteroatoms independently selected from boron, nitrogen, oxygen, silicon, or sulfur, wherein Ring H is optionally further substituted with 1-2 oxo groups.

In some embodiments, Ring H is

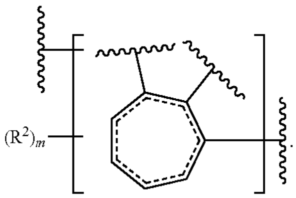

In some embodiments, Ring H is

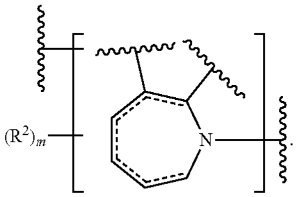

In some embodiments, Ring H is

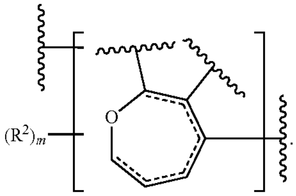

In some embodiments, Ring H is
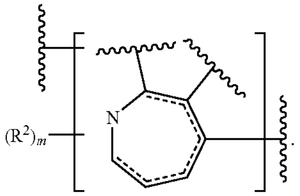
In some embodiments, Ring H is
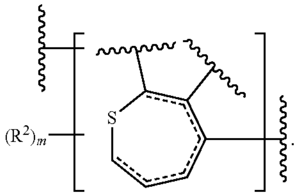
In some embodiments, Ring H is
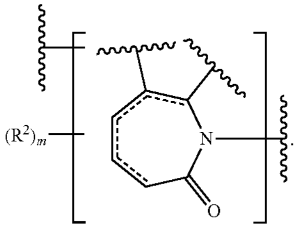
In some embodiments, Ring H is
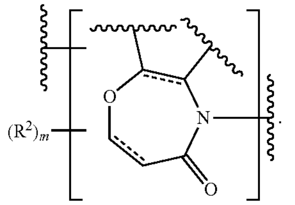
In some embodiments, Ring H is
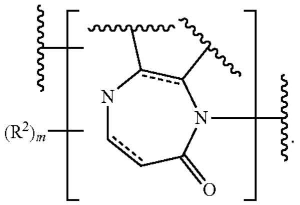
In some embodiments, Ring H is
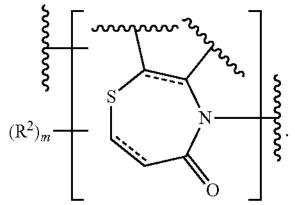
some embodiments, Ring H is
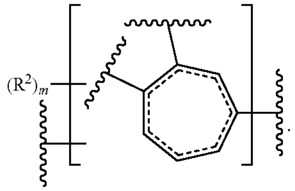
In some embodiments, Ring H is
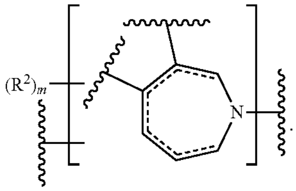
In some embodiments, Ring H is
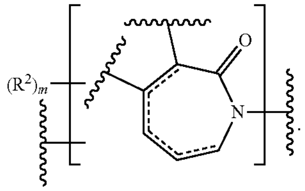
In some embodiments, Ring H is
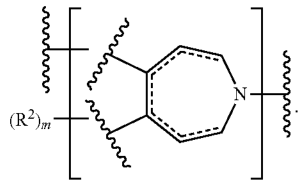

In some embodiments, Ring H is

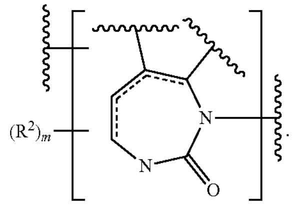

In some embodiments, Ring H is

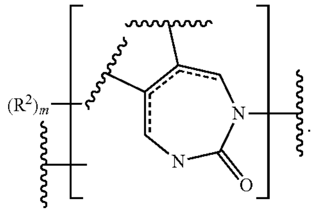

In some embodiments, Ring H is

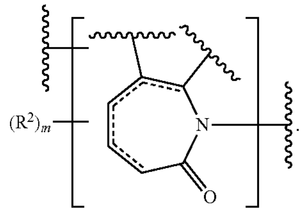

In some embodiments, Ring H is

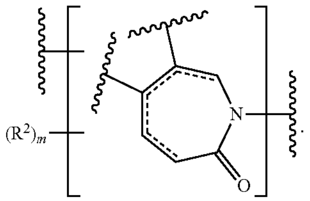

In some embodiments, Ring H is

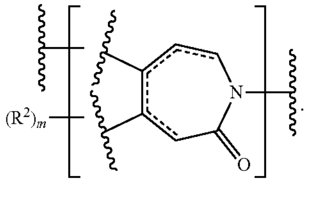

In some embodiments, Ring H is

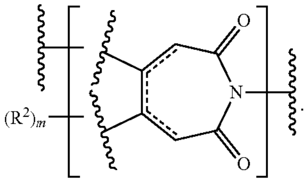

In some embodiments, Ring H is

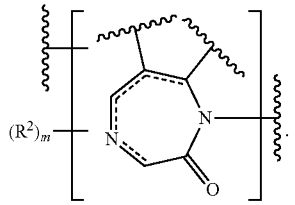

In some embodiments, Ring H is

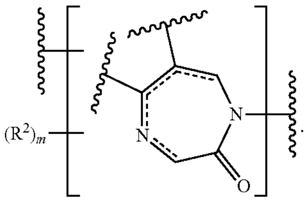

In some embodiments, Ring E and Ring H is

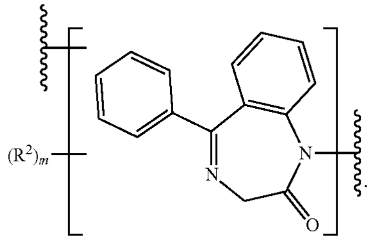

In some embodiments, Ring E and Ring H is selected from those depicted in Table 1, below.

As defined above and described herein, each of Ring I and Ring J is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur In some embodiments, each of Ring I and Ring J is independently a 6-membered aryl. In some embodiments, each of Ring I and Ring J is independently a 6-membered heteroaryl containing 1-4 heteroatoms independently selected from nitrogen, oxygen, or sulfur. In some embodiments, each of Ring I and Ring J is independently a 5 to 7-membered saturated or partially unsaturated carbocyclyl. In some embodiments, each of Ring I and Ring J is independently a 5 to 7-membered saturated or partially unsaturated heterocyclyl ring with 1-3 heteroatoms independently selected from boron, nitrogen, oxygen, silicon, or sulfur. In some embodiments, each of Ring I and Ring J is independently a 5-membered heteroaryl with 1-3 heteroatoms independently selected from nitrogen, oxygen or sulfur.

In some embodiments, each Ring I and Ring J is independently

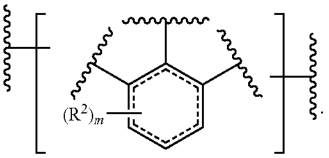

In some embodiments, each Ring I and Ring J is independently

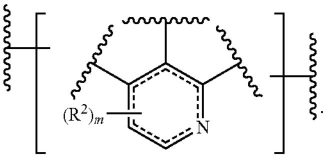

In some embodiments, each Ring I and Ring J is independently

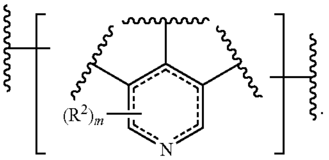

In some embodiments, each Ring I and Ring J is independently

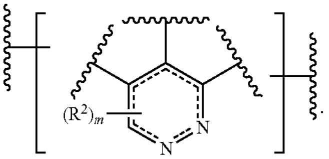

In some embodiments, Ring I and Ring J is independently

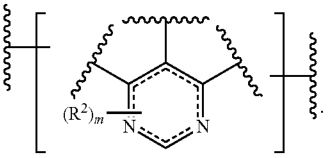

In some embodiments, Ring I and Ring J is independently is

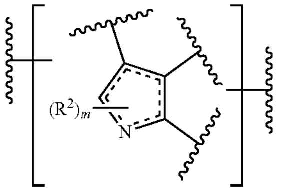

In some embodiments, Ring I and Ring J is independently

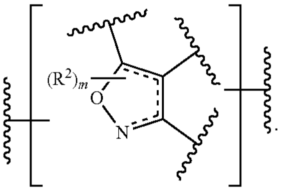

In some embodiments, Ring I and Ring J is independently

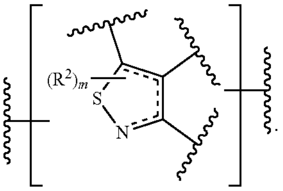

As defined above and described herein, Ring K is a fused ring selected from a 6-12 membered saturated or partially unsaturated carbocyclyl or heterocyclyl ring with 1-3 heteroatoms independently selected from boron, nitrogen, oxygen, silicon, or sulfur, wherein Ring H is optionally further substituted with 1-2 oxo groups.

In some embodiments, Ring K is a fused ring selected from a 6-12 membered saturated or partially unsaturated carbocyclyl. In some embodiments, Ring K is a 6-12 membered saturated or partially unsaturated heterocyclyl ring with 1-3 heteroatoms independently selected from boron, nitrogen, oxygen, silicon, or sulfur. In some embodiments, Ring K is optionally further substituted with 1-2 oxo groups.

In some embodiments, Ring K is

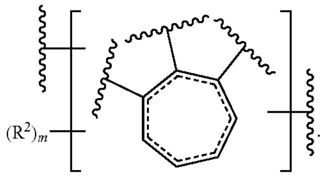

In some embodiments, Ring K is
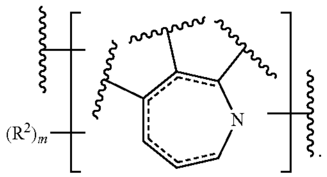
In some embodiments, Ring K is
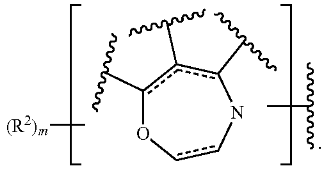
In some embodiments, Ring K is
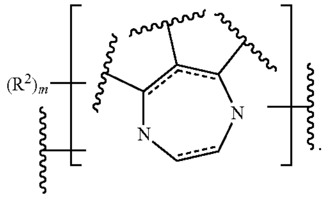
In some embodiments, Ring K is
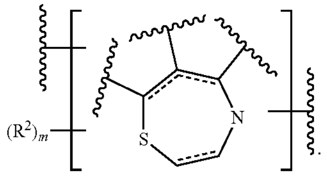
In some embodiments, Ring K is
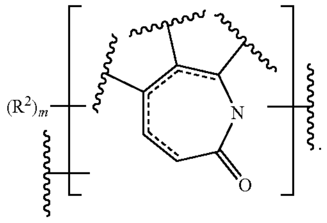
In some embodiments, Ring K is
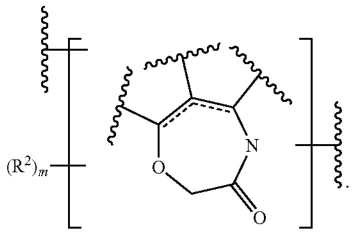
In some embodiments, Ring K is
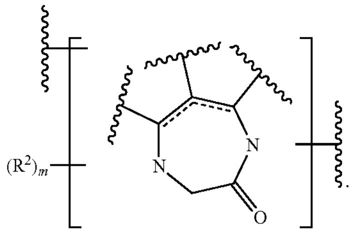
In some embodiments, Ring K is
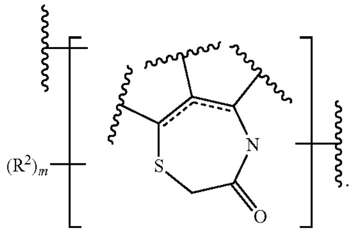
some embodiments, Ring K is
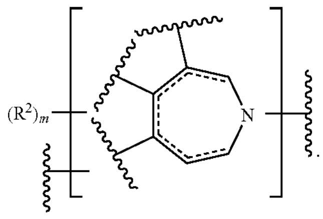
In some embodiments, Ring K is
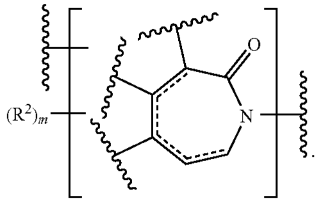

In some embodiments, Ring K is

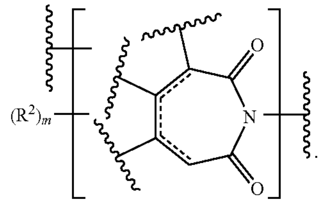

In some embodiments, Ring K is

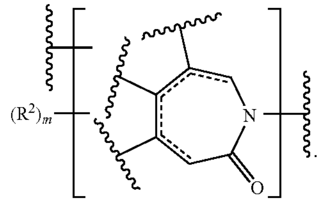

In some embodiments, Ring K is

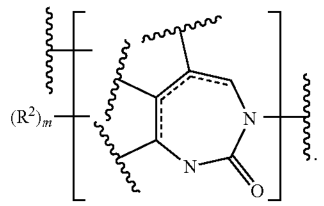

In some embodiments, Ring K is

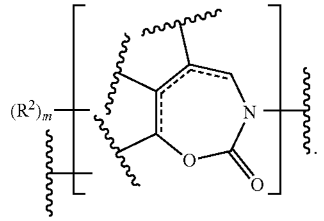

In some embodiments, Ring I, Ring J, and Ring K is

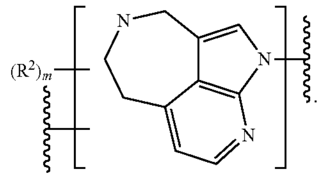

In some embodiments, Ring I, Ring J, and Ring K is selected from those depicted in Table 1, below.

As defined above and described here, $L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —$C(R)_2$—, —CH(R)—, —$C(F)_2$—, —N(R)—, —$S(O)_2$or —(C)═CH—;

In some embodiments, $L^1$ is a covalent bond. In some embodiments, $L^1$ is a $C_{1-3}$ aliphatic. In some embodiments, $L^1$ is —$CH_2$—. In some embodiments, $L^1$ is —C(D)(H)—. In some embodiments, $L^1$ is —$C(D)_2$—. In some embodiments, $L^1$ is —$CH_2CH_2$—. In some embodiments, $L^1$ is —NR—. In some embodiments, $L^1$ is —$CH_2$NR—. In some embodiments, $L^1$ is or —O—. In some embodiments, $L^1$ is —$CH_2$O—. In some embodiments, $L^1$ is —S—. In some embodiments, $L^1$ is —OC(O)—. In some embodiments, $L^1$ is —C(O)O—. In some embodiments, $L^1$ is —C(O)—. In some embodiments, $L^1$ is —S(O)—. In some embodiments, $L^1$ is —$S(O)_2$—. In some embodiments, $L^1$ is —NRS$(O)_2$—. In some embodiments, $L^1$ is —$S(O)_2$NR—. In some embodiments, $L^1$ is —NRC(O)—. In some embodiments, $L^1$ is —C(O)NR—.

In some embodiments, Ring $L^1$ is selected from those depicted in Table 1, below.

As defined above and described herein, ⎓ is a single or double bond.

In some embodiments, ⎓ is a single bond. In some embodiments, ⎓ is a double bond.

In some embodiments, ⎓ is selected from those depicted in Table 1, below.

As defined above and described herein, m is 0, 1, 2, 3, 4, 5, 6, 7, 8, 9, 10, 11, 12, 13, 14, 15, or 16.

In some embodiments, m is 0. In some embodiments, m is 1. In some embodiments, m is 2. In some embodiments, m is 3. In some embodiments, m is 4. In some embodiments, m is 5. In some embodiments, m is 6. In some embodiments, m is 7. In some embodiments, m is 8. In some embodiments, m is 9. In some embodiments, m is 10. In some embodiments, m is 11. In some embodiments, m is 12. In some embodiments, m is 13. In some embodiments, m is 14. In some embodiments, m is 15. In some embodiments, m is 16.

In some embodiments, m is selected from those depicted in Table 1, below.

As defined above and described herein, n is 0, 1, 2, 3 or 4.

In some embodiments, n is 0. In some embodiments, n is 1. In some embodiments, n is 2. In some embodiments, n is 3. In some embodiments, n is 4.

In some embodiments, n is selected from those depicted in Table 1, below.

As defined above and described herein, p is 0 or 1.

In some embodiments, p is 0. In some embodiments, p is 1.

In some embodiments, p is selected from those depicted in Table 1, below.

In some embodiments, LBM is

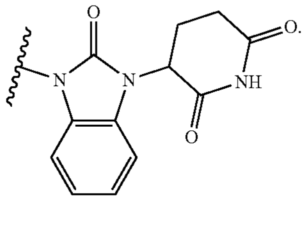 [SMILES: *n1c(=O)n(C2CCC(=O)NC2=O)c2ccccc21]

In some embodiments, LBM is
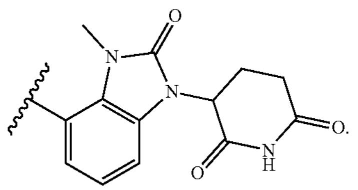 [SMILES: *c1cccc2c1n(C)c(=O)n2C1CCC(=O)NC1=O]
In some embodiments, LBM is
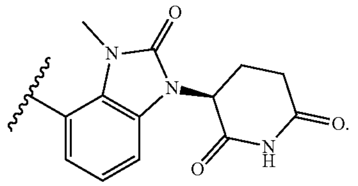 [SMILES: *c1cccc2c1n(C)c(=O)n2[C@H]1CCC(=O)NC1=O]
In some embodiments, LBM is
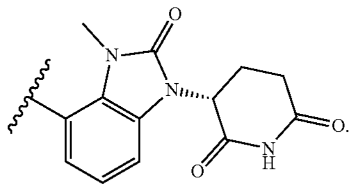 [SMILES: *c1cccc2c1n(C)c(=O)n2[C@@H]1CCC(=O)NC1=O]
In some embodiments, LBM is
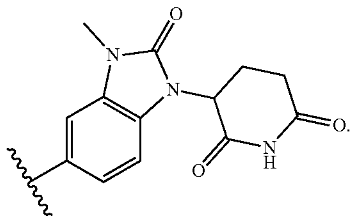 [SMILES: *c1ccc2c(c1)n(C)c(=O)n2C1CCC(=O)NC1=O]
In some embodiments, LBM is
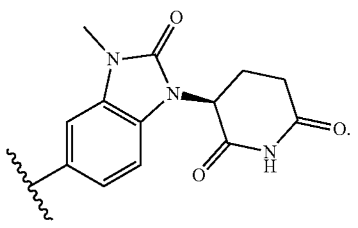 [SMILES: *c1ccc2c(c1)n(C)c(=O)n2[C@H]1CCC(=O)NC1=O]
In some embodiments, LBM is
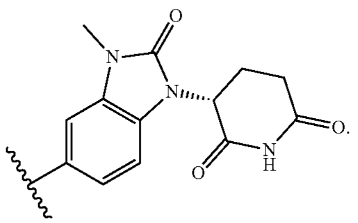 [SMILES: *c1ccc2c(c1)n(C)c(=O)n2[C@@H]1CCC(=O)NC1=O]
In some embodiments, LBM is
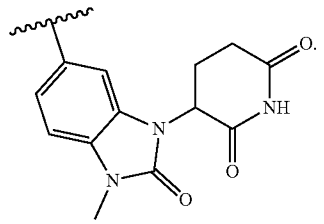 [SMILES: *c1ccc2c(c1)n(C1CCC(=O)NC1=O)c(=O)n2C]
In some embodiments, LBM is
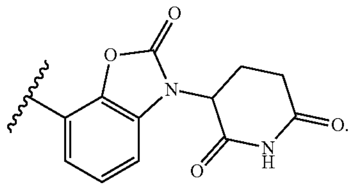 [SMILES: *c1cccc2c1oc(=O)n2C1CCC(=O)NC1=O]
In some embodiments, LBM is
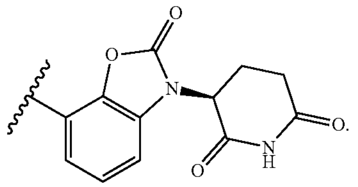 [SMILES: *c1cccc2c1oc(=O)n2[C@H]1CCC(=O)NC1=O]
In some embodiments, LBM is
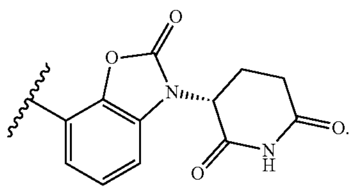 [SMILES: *c1cccc2c1oc(=O)n2[C@@H]1CCC(=O)NC1=O]

In some embodiments, LBM is
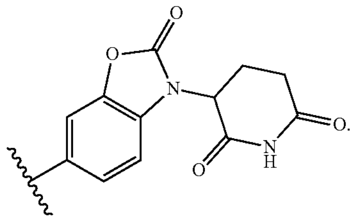 [SMILES: *c1ccc2c(c1)oc(=O)n2C1CCC(=O)NC1=O]
In some embodiments, LBM is
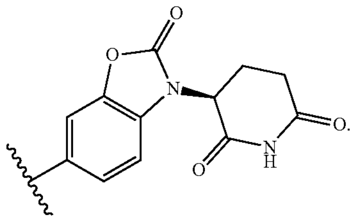 [SMILES: *c1ccc2c(c1)oc(=O)n2[C@H]1CCC(=O)NC1=O]
In some embodiments, LBM is
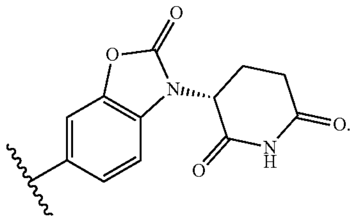 [SMILES: *c1ccc2c(c1)oc(=O)n2[C@@H]1CCC(=O)NC1=O]
In some embodiments, LBM is
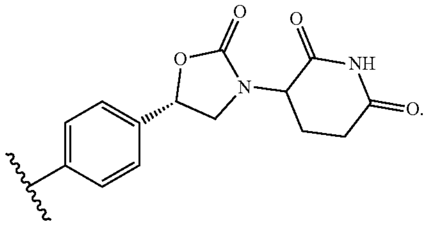 [SMILES: *c1ccc([C@H]2CN(C3CCC(=O)NC3=O)C(=O)O2)cc1]
In some embodiments, LBM is
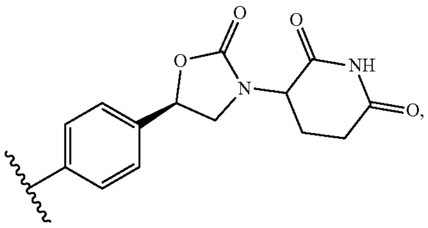
-continued
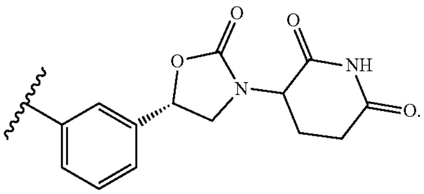
In some embodiments, LBM is
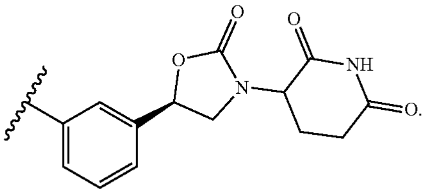 [SMILES: *c1cccc([C@@H]2CN(C3CCC(=O)NC3=O)C(=O)O2)c1]
In some embodiments, LBM is
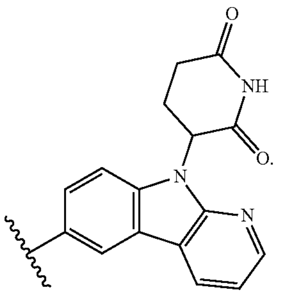 [SMILES: *c1ccc2c(c1)c1cccnc1n2C1CCC(=O)NC1=O]
In some embodiments, LBM is
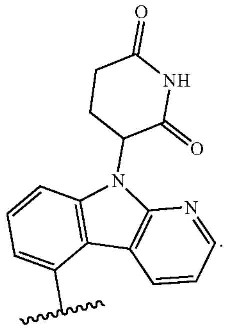 [SMILES: *c1cccc2c1c1cccnc1n2C1CCC(=O)NC1=O]

In some embodiments, LBM is

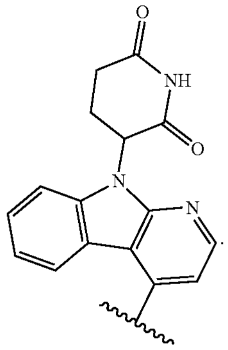 [SMILES: *c1ccnc2c1c1ccccc1n2C1CCC(=O)NC1=O]

In some embodiments, LBM is

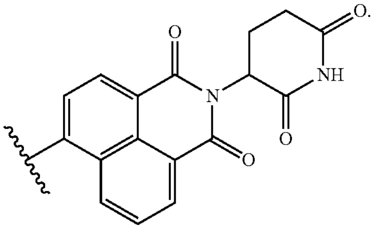 [SMILES: *c1ccc2c3c(cccc13)C(=O)N(C1CCC(=O)NC1=O)C2=O]

In some embodiments, LBM is

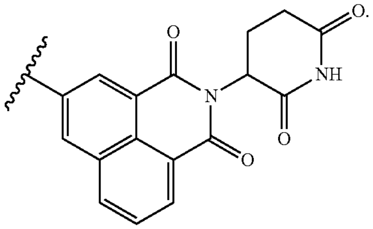 [SMILES: *c1cc2c3c(cccc3c1)C(=O)N(C1CCC(=O)NC1=O)C2=O]

In certain embodiments, the present invention provides a compound of Formula I, wherein LBM is an E3 ubiquitin ligase (cereblon) binding moiety thereby forming a compound of formula I-p-1, I-p-2, or I-p-3 respectively:

I-p-1

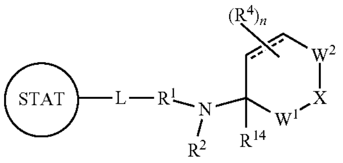

I-p-2

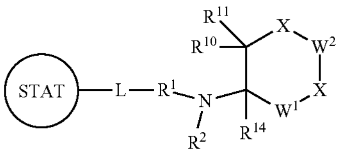

-continued

I-p-3

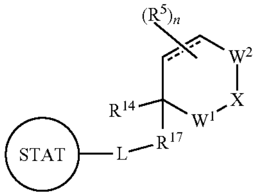

or a pharmaceutically acceptable salt thereof, wherein L and STAT are as defined above and described herein, and wherein each of the variables $R^1$, $R^2$, $R^4$, $R^5$, $R^{10}$, $R^{11}$, $R^{14}$, $R^{17}$, $W^1$, $W^2$, X, ---, and n is as defined in WO 2017/197051 which is herein incorporated by reference in its entirety and wherein

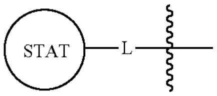

is attached to $R^1$, the ring formed by combining $R^1$ and $R^2$, or $R^{17}$ at the site of attachment of $R^{12}$ as defined in WO 2017/197051 such that

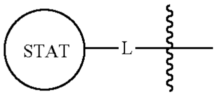

takes the place of the $R^2$ substituent.

In some embodiments, the present invention provides a compound of formula I, wherein LBM is an E3 ubiquitin ligase (cereblon) binding moiety thereby forming a compound of formula I-q-1, I-q-2, I-q-3, or I-q-4, respectively:

I-q-1

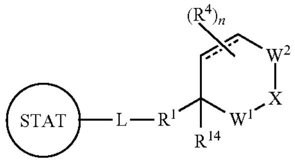

I-q-2

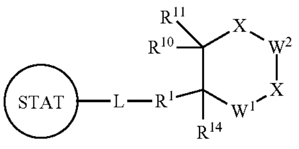

I-q-3

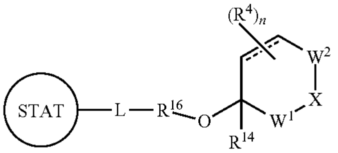

-continued

I-q-4

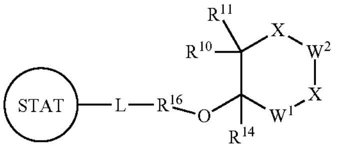

or a pharmaceutically acceptable salt thereof, wherein L and STAT are as defined above and described herein, and wherein each of the variables $R^1$, $R^4$, $R^{10}$, $R^{11}$, $R^{14}$, $R^{16}$, $W^1$, $W^2$, X, ---, and n is as defined in WO 2018/237026, the entirety of each of which is herein incorporated by reference, and wherein

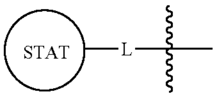

is attached to $R^1$ or $R^{16}$ at the site of attachment of $R^{12}$ as defined in WO 2018/237026, such that

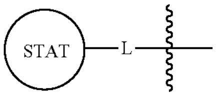

takes the place of the $R^{12}$ substituent.

In some embodiments, the present invention provides a compound of formula I, wherein LBM is an E3 ubiquitin ligase (cereblon) binding moiety thereby forming a compound of formula I-r-1 or I-r-3, respectively:

I-r-1

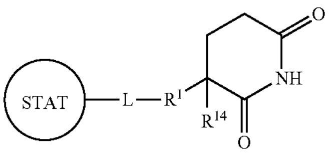

I-r-3

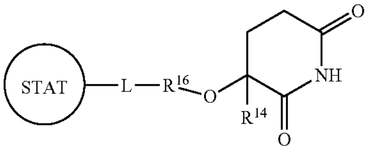

or a pharmaceutically acceptable salt thereof, wherein L and STAT are as defined above and described herein, and wherein each of the variables $R^1$, $R^{14}$, and $R^{16}$ is as defined in WO 2018/237026, the entirety of each of which is herein incorporated by reference, and wherein

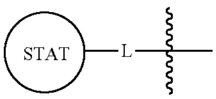

is attached to $R^1$ or $R^{16}$ at the site of attachment of $R^{12}$ as defined in WO 2018/237026, such that

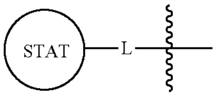

takes the place of the $R^{12}$ substituent.

In certain embodiments, the present invention provides a compound of formula I, wherein LBM is an E3 ubiquitin ligase (cereblon) binding moiety thereby forming a compound of formula I-s-1, I-s-2, I-s-3, I-s-4, I-s-5, I-s-6, I-s-7, or I-s-8:

I-s-1

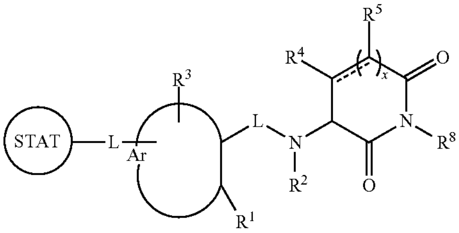

I-s-2

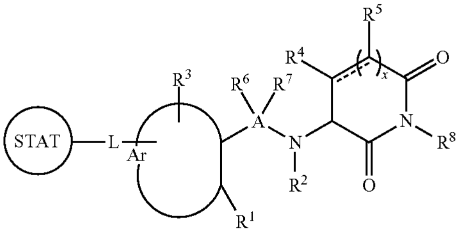

I-s-3

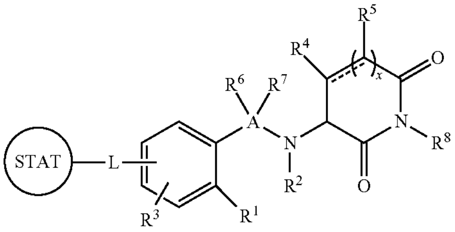

I-s-4

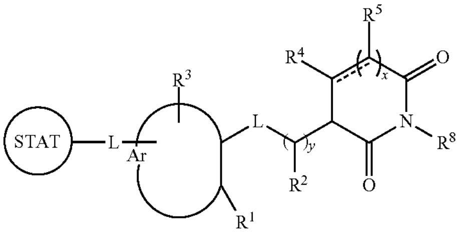

I-s-5

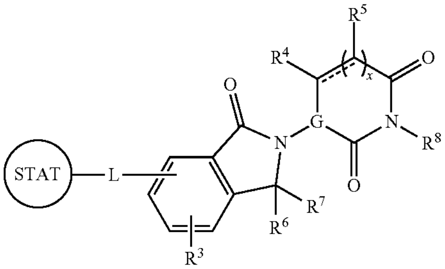

-continued

I-s-6

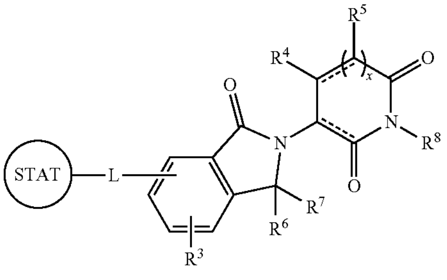

I-s-7

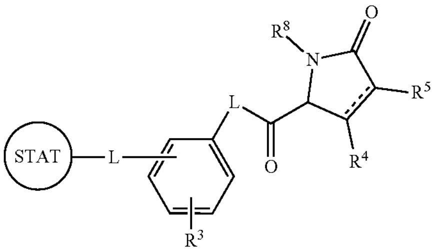

I-s-8

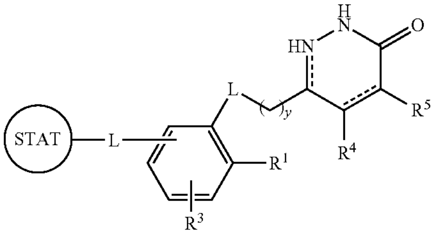

or a pharmaceutically acceptable salt thereof, wherein L and STAT are as defined above and described in embodiments herein, and wherein each of the variables Ar, $R^1$, $R^2$, $R^3$, $R^4$, $R^5$, $R^6$, $R^7$, $R^8$, A, L, x, y, and ⚋ is as described and defined in WO 2017/161119, the entirety of each of which is herein incorporated by reference.

In certain embodiments, the present invention provides a compound of formula I, wherein LBM is an E3 ubiquitin ligase (cereblon) binding moiety thereby forming a compound of formula I-t:

I-t

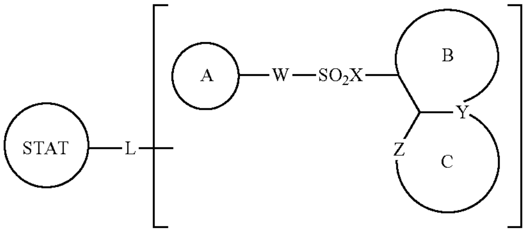

or a pharmaceutically acceptable salt thereof, wherein L and STAT are as defined above and described in embodiments herein, and wherein each of the variables A, B, C, W, X, Y, and Z is as described and defined in U.S. Pat. No. 5,721,246, the entirety of each of which is herein incorporated by reference.

In certain embodiments, the present invention provides a compound of formula I, wherein LBM is an E3 ubiquitin ligase (cereblon) binding moiety thereby forming a compound of formula I-t-1:

I-t-1

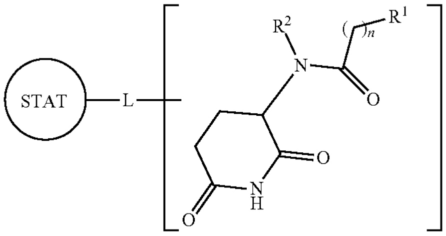

or a pharmaceutically acceptable salt thereof, wherein L and STAT are as defined above and described in embodiments herein, and wherein each of the variables $R_1$, $R_2$, and n is as described and defined in WO 2019/043214, the entirety of each of which is herein incorporated by reference.

In some embodiments, LBM is a IAP E3 Ubiquitin ligase binding moiety recited in Varfolomeev, E. et al., *IAP Antagonists Induce Autoubiquitination of c-IAPs, NF-κB activation, and TNFα-DependentApoptosis*, Cell, 2007, 131(4): 669-81, such as, for example:

MV1

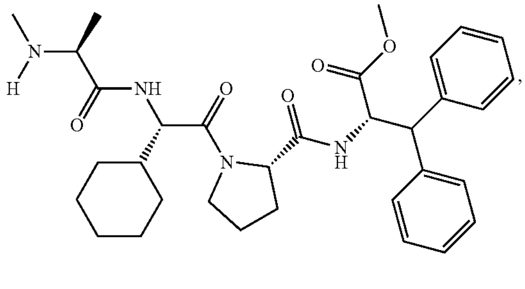

, and

-continued

BV6

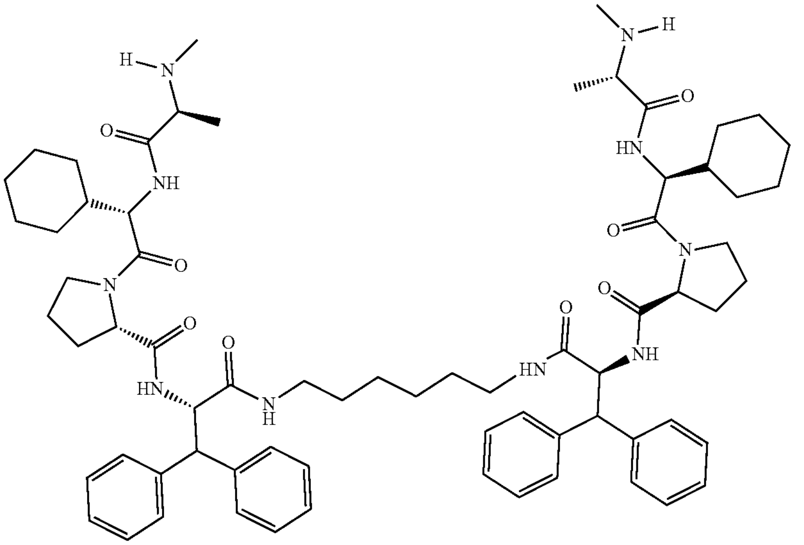

wherein

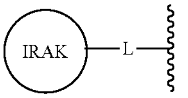

is attached to a modifiable carbon, oxygen, nitrogen or sulfur atom.

In certain embodiments, the present invention provides a compound of Formula I, wherein LBM is a VHL E3 ubiquitin ligase binding moiety thereby forming a compound of formula I-u-1, I-u-2, I-u-3, I-u-4, or I-u-5 respectively:

I-u-1

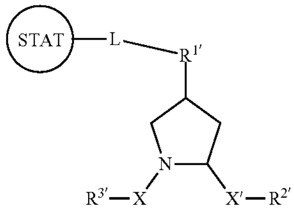

I-u-2

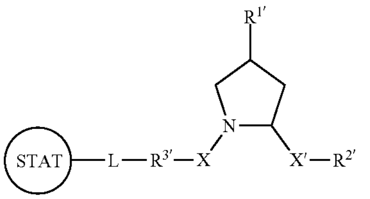

-continued

I-u-3

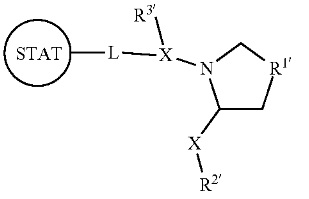

I-u-4

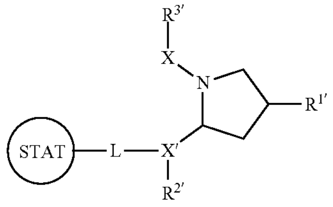

I-u-5

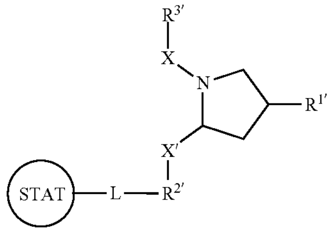

or a pharmaceutically acceptable salt thereof, wherein L and STAT are as defined above and described in embodiments herein, and wherein each of the variables $R^{1'}$, $R^{2'}$, $R^{3'}$, X, and X' is as defined and described in WO 2013/106643 and US 2014/0356322, the entirety of each of which is herein incorporated by reference.

In certain embodiments, the present invention provides a compound of Formula I, wherein LBM is a VHL E3 ubiquitin ligase binding moiety thereby forming a compound of formula I-v-1, I-v-2, I-v-3, I-v-4, I-v-5 or I-v-6 respectively:

I-v-1

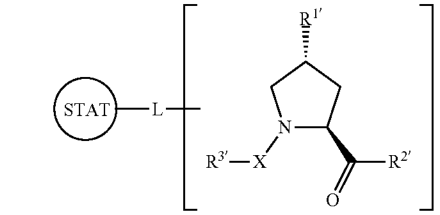

I-v-2

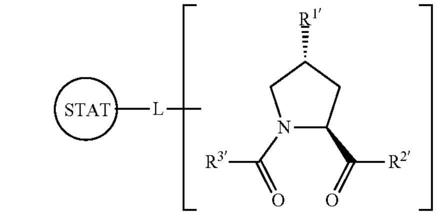

I-v-3

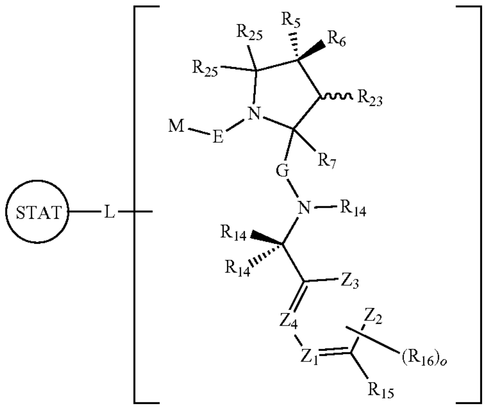

I-v-4

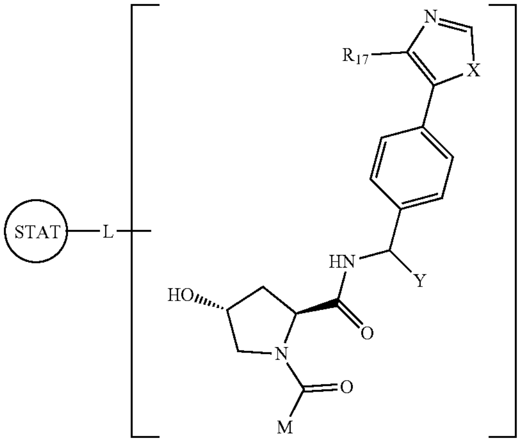

-continued

I-v-5

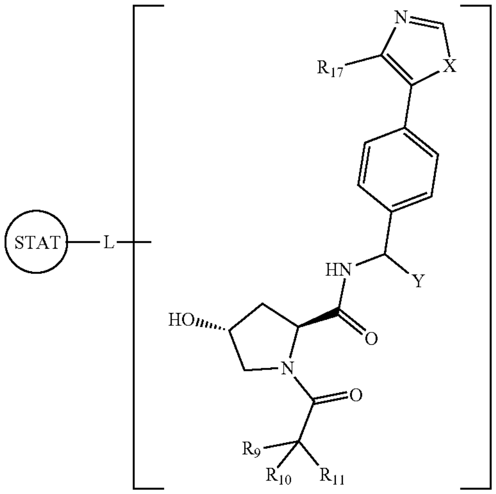

I-v-6

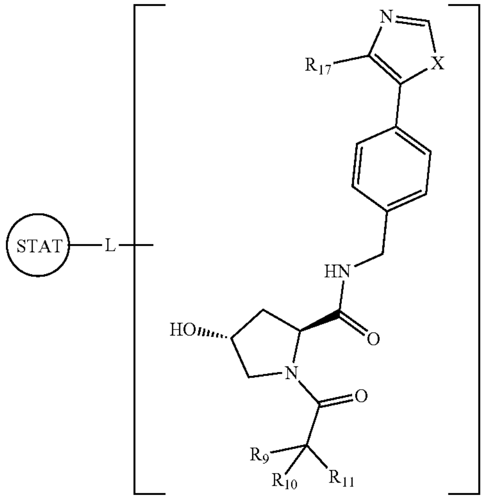

or a pharmaceutically acceptable salt thereof, wherein L and STAT are as defined above and described in embodiments herein, and wherein each of the variables $R^{1'}$, $R^{2'}$, $R^{3'}$, $R_5$, $R_6$, $R_7$, $R_9$, $R_{10}$, $R_{11}$, $R_{14}$, $R_{15}$, $R_{16}$, $R^{17}$, $R_{23}$, $R_{25}$, E, G, M, X, X', Y, $Z_1$, $Z_2$, $Z_3$, $Z_4$, and o is as defined and described in WO 2016/149668 and US 2016/0272639, the entirety of each of which is herein incorporated by reference.

As used herein, depiction of brackets around any LBM

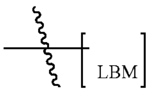

means that the

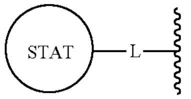

moiety is covalently attached to said LBM at any available modifiable carbon, nitrogen, oxygen, or sulfur atom. For purposes of clarity and by way of example, such available modifiable carbon, nitrogen, oxygen, or sulfur atoms in the following LBM compound structure are depicted below, wherein each wavy bond defines the point of attachment to said

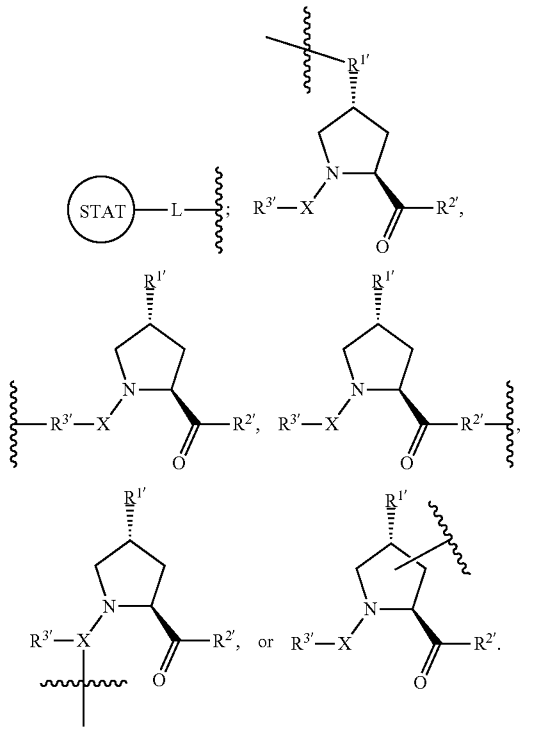

In certain embodiments, the present invention provides a compound of Formula I, wherein LBM is a VHL E3 ubiquitin ligase binding moiety thereby forming a compound of formula I-w-1, I-w-2, or I-w-3 respectively:

I-w-1

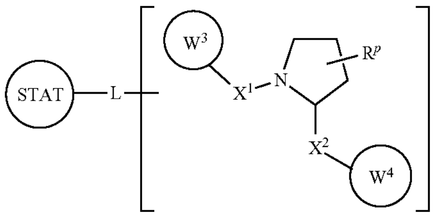

I-w-2

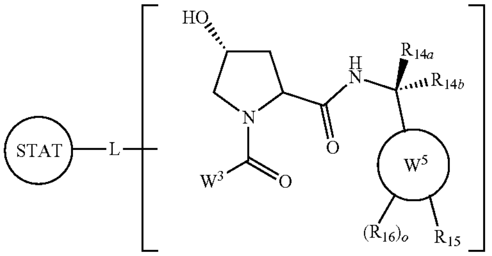

-continued

I-w-3

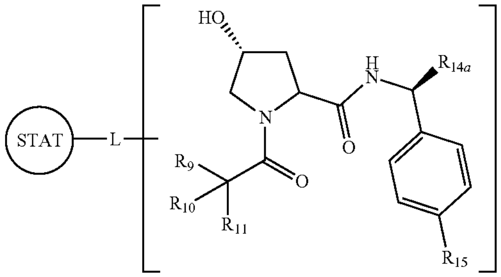

or a pharmaceutically acceptable salt thereof, wherein L and STAT are as defined above and described in embodiments herein, and wherein each of the variables $R^p$, $R_9$, $R_{10}$, $R_{11}$, $R_{14a}$, $R_{14b}$, $R_{15}$, $R_{16}$, $W^3$, $W^4$, $W^5$, $X^1$, $X^2$, and o is as defined and described in WO 2016/118666 and US 2016/0214972, the entirety of each of which is herein incorporated by reference.

In certain embodiments, the present invention provides a compound of Formula I, wherein LBM is a CRBN or VHL E3 ubiquitin ligase binding moiety thereby forming a compound of formula I-x-1, I-x-2, I-x-3, I-x-4, I-x-5, I-x-6, or I-x-7 respectively:

I-x-1

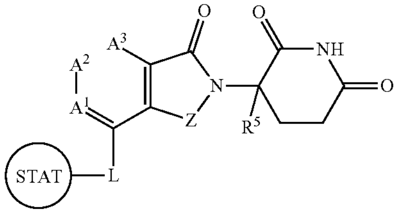

I-x-2

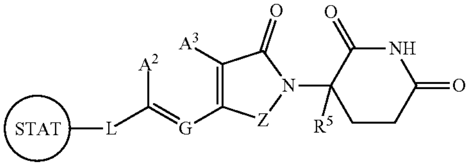

I-x-3

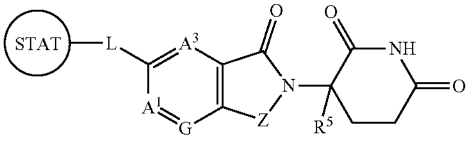

I-x-4

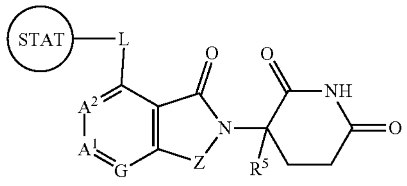

-continued

I-x-5

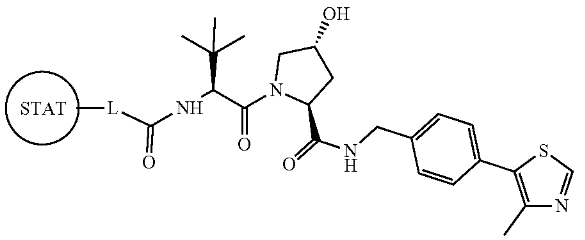

I-x-6

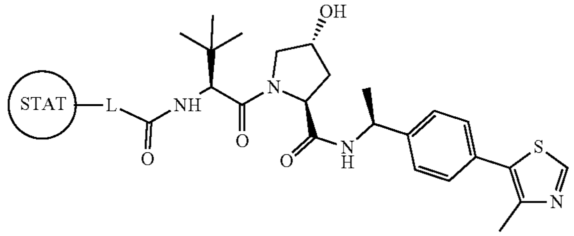

I-x-7

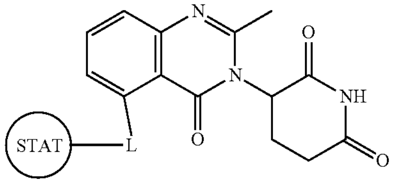

or a pharmaceutically acceptable salt thereof, wherein L and STAT are as defined above and described in embodiments herein, and wherein each of the variables $A^1$, $A^2$, $A^3$, $R^5$, G and Z is as defined and described in WO 2017/176958.

In certain embodiments, the present invention provides a compound of Formula I, wherein LBM is a CRBN E3 ubiquitin ligase binding moiety thereby forming a compound of formula I-x'-1, I-x"-1, I-x'-2, I-x"-2, I-x'-3, I-x"-3, I-x'-4, I-x"-4, I-x'-7 or I-x"-7 respectively:

I-x'-1

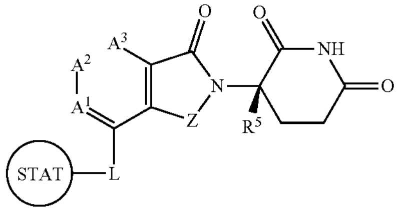

I-x"-1

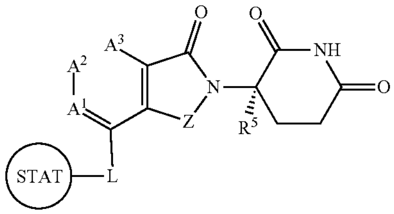

I-x'-2

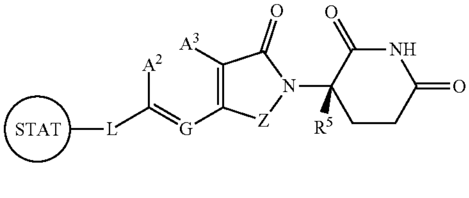

-continued

I-x"-2

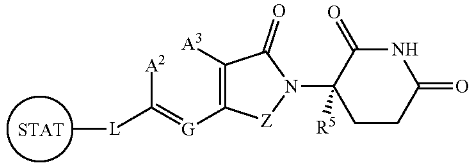

I-x'-3

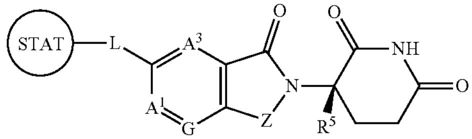

I-x"-3

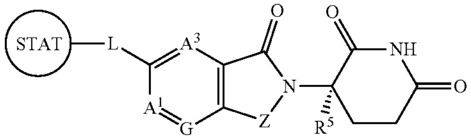

I-x'-4

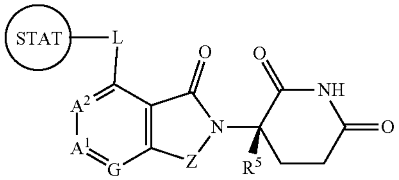

I-x"-4

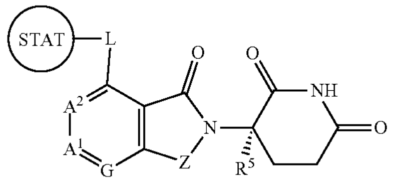

I-x'-7

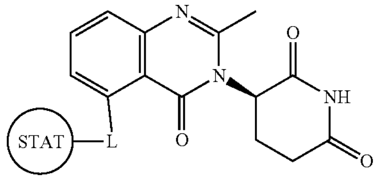

I-x"-7

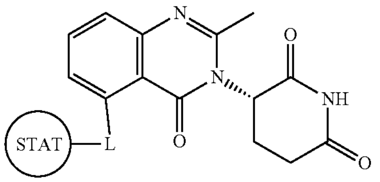

or a pharmaceutically acceptable salt thereof, wherein L and STAT are as defined above and described in embodiments herein, and wherein each of the variables $A^1$, $A^2$, $A^3$, $R^5$, G and Z is as defined and described in WO 2017/176958, the entirety of which is herein incorporated by reference.

In certain embodiments, the present invention provides a compound of Formula I, wherein LBM is a MDM2 (i.e. human double minute 2 or HDM2) E3 ligase binding moiety thereby forming a compound of formula I-y-1, I-y-2, I-y-3, I-y-4, I-y-5, I-y-6, I-y-7, I-y-8, I-y-9, I-y-10, I-y-11, I-y-12, I-y-13, I-y-14, I-y-15, I-y-16, I-y-17, or I-y-18 respectively:

I-y-1
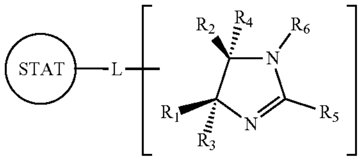
I-y-2
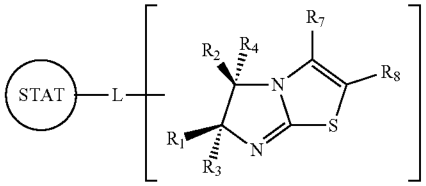
I-y-3
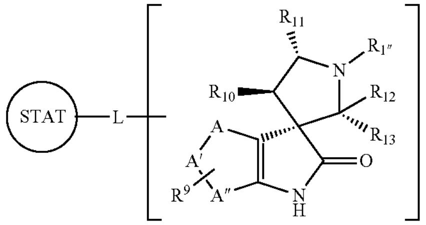
I-y-4
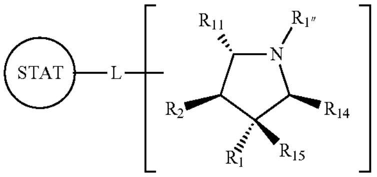
I-y-5
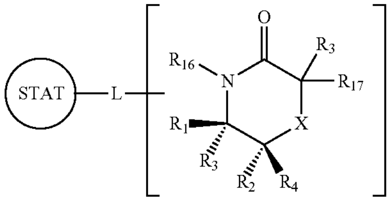
I-y-6
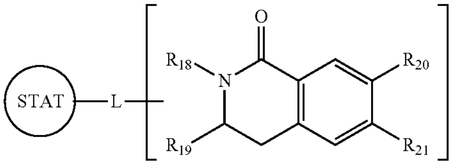
I-y-7
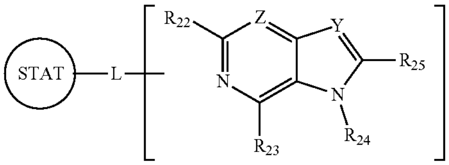
I-y-8
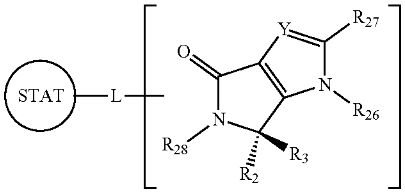
-continued
I-y-9
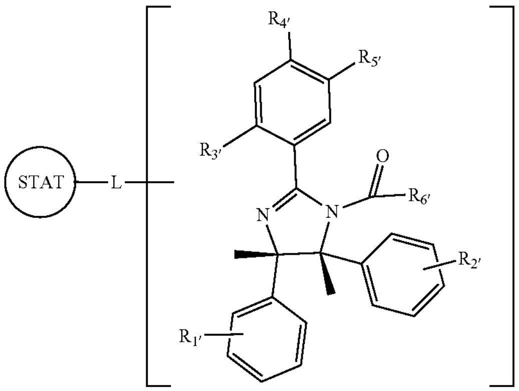
I-y-10
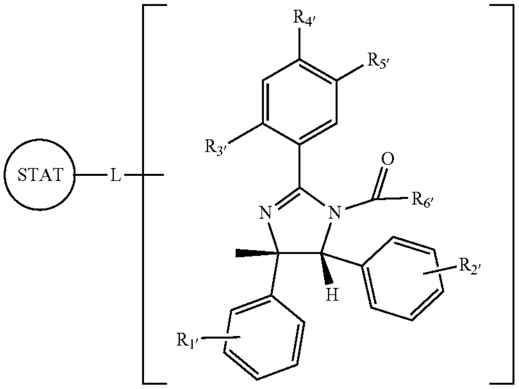
I-y-11
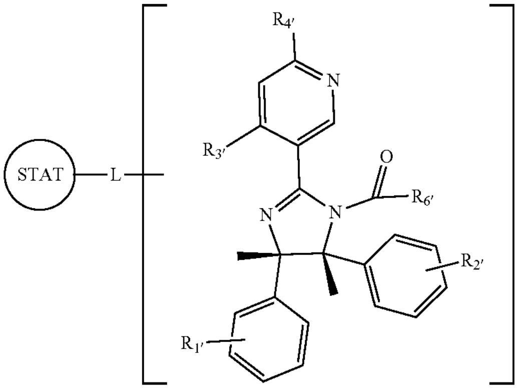
I-y-12
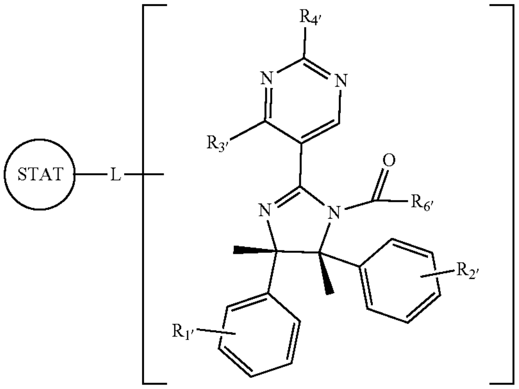

-continued

I-y-13

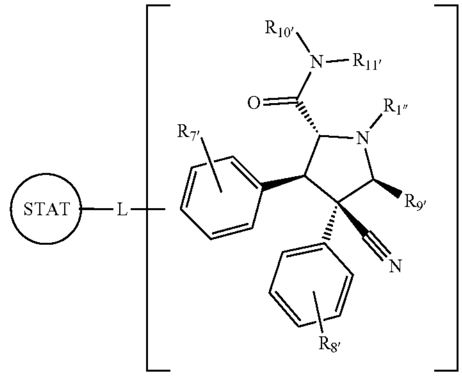

I-y-14

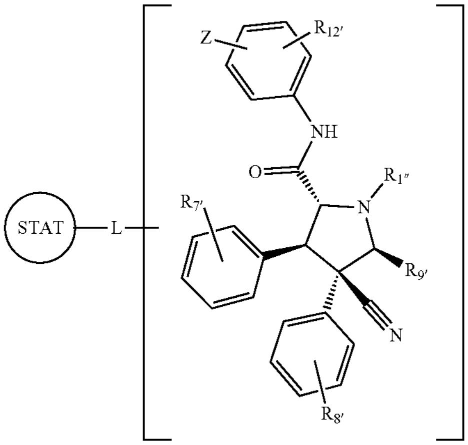

I-y-15

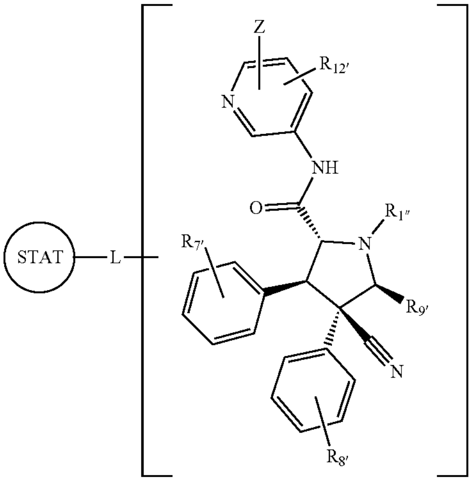

-continued

I-y-16

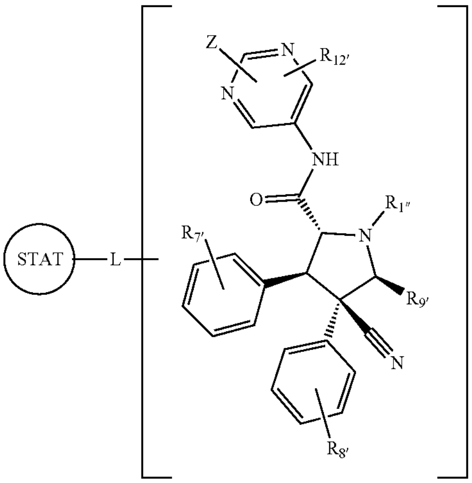

I-y-17

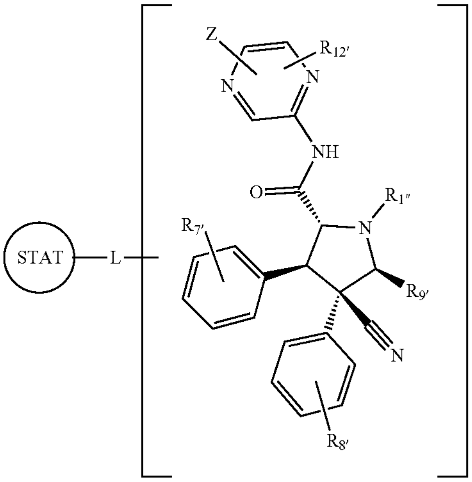

I-y-18

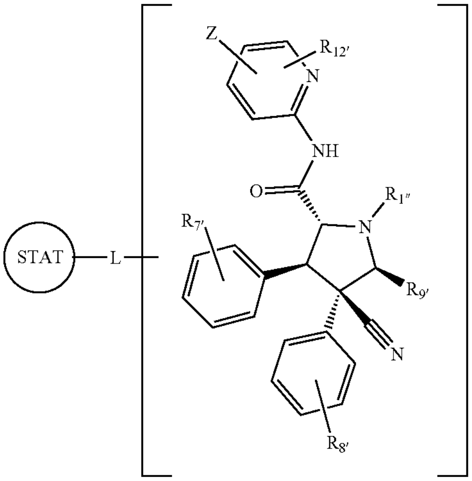

or a pharmaceutically acceptable salt thereof, wherein L and STAT are as defined above and described in embodiments herein, and wherein each of the variables $R_1$, $R_2$, $R_3$, $R_4$, $R_5$, $R_6$, $R_7$, $R_8$, $R_9$, $R_{10}$, $R_{11}$, $R_{12}$, $R_{13}$, $R^{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{1'}$, $R_{2'}$, $R^{3'}$, $R_{4'}$, $R_{5'}$, $R_{6'}$, $R_{7'}$, $R_{8'}$, $R_9$, $R^{10'}$, $R_{11'}$, $R_{12'}$, $R_{1''}$, A, A', A'', X, Y, and Z is as defined and described in WO 2017/011371 and US 2017/0008904, the entirety of each of which is herein incorporated by reference.

In certain embodiments, the present invention provides a compound of Formula I, wherein LBM is an IAP E3 ubiquitin ligase binding moiety thereby forming a compound of formula I-z-1, I-z-2, I-z-3, or I-z-4 respectively:

I-z-1

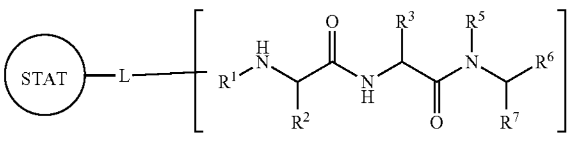

I-z-2

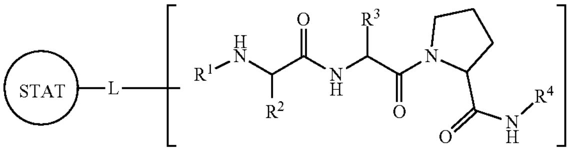

I-z-3

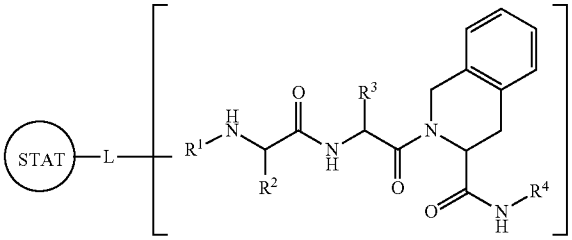

I-z-4

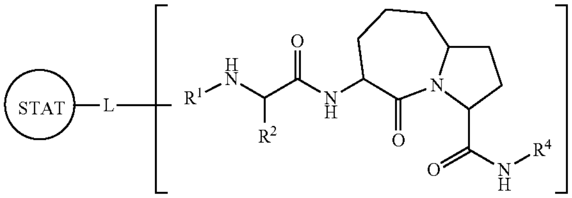

or a pharmaceutically acceptable salt thereof, wherein L and STAT are as defined above and described in embodiments herein, and wherein each of the variables $R^1$, $R^2$, $R^3$, $R^4$, $R^5$, $R^6$, and $R^7$, is as defined and described in WO 2017/011590 and US 2017/0037004, the entirety of each of which is herein incorporated by reference.

In certain embodiments, the present invention provides a compound of Formula I, wherein LBM is an E3 ubiquitin ligase (cereblon) binding moiety, a DCAF15 E3 ubiquitin ligase binding moiety, or a VHL E3 ubiquitin ligase binding moiety; thereby forming a compound of formula I-aa-1, I-aa-2, or I-aa-3:

I-aa-1

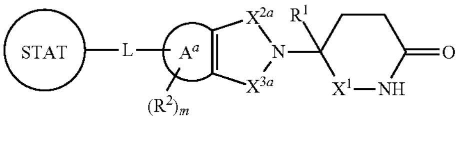

-continued

I-aa-2

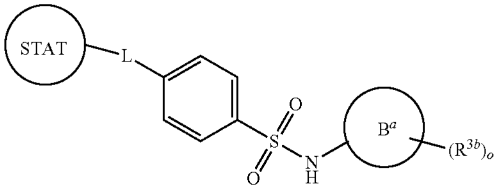

I-aa-3

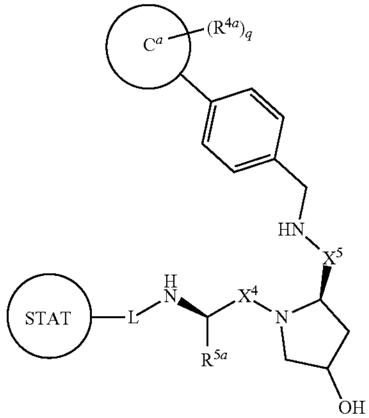

or a pharmaceutically acceptable salt thereof, wherein L and STAT is as defined above and described in embodiments herein, and wherein: each of $X^1$, $X^{2a}$, and $X^{3a}$ is independently a bivalent moiety selected from a covalent bond, —$CH_2$—, —C(O)—, —C(S)—, or

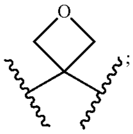 [SMILES: *C1(*)COC1]

;

each of $X^4$ and $X^5$ is independently a bivalent moiety selected from —$CH_2$—, —C(O)—, —C(S)—, or

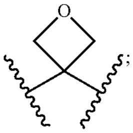 [SMILES: *C1(*)COC1]

;

$R^1$ is hydrogen, deuterium, halogen, —CN, —OR, —SR, —S(O)R, —$S(O)_2R$, —$NR_2$, or an optionally substituted $C_{1-4}$ aliphatic;

each of $R^2$, $R^{3b}$, and $R^{4a}$ is independently hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)$S(O)_2R$;

$R^{5a}$ is hydrogen or $C_{1-6}$ aliphatic;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring $A^a$ is a fused ring selected from 6-membered aryl containing 0-2 nitrogen atoms, 5 to 7-membered partially saturated carbocyclyl, 5 to 7-membered partially saturated heterocyclyl with 1-2 heteroatoms independently selected from nitrogen, oxygen or sulfur, or 5-membered heteroaryl with 1-3 heteroatoms independently selected from nitrogen, oxygen or sulfur;

Ring $B^a$ is selected from 6-membered aryl containing 0-2 nitrogen atoms or a 8-10 membered bicyclic heteroaryl having 1-5 heteroatoms independently selected from nitrogen, oxygen, or sulfur;

Ring $C^a$ is a selected from 6-membered aryl containing 0-2 nitrogen atoms or a 5-membered heteroaryl with 1-3 heteroatoms independently selected from nitrogen, oxygen or sulfur;

m is 0, 1, 2, 3 or 4;

is 0, 1, 2, 3 or 4;

q is 0, 1, 2, 3 or 4; and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In certain embodiments, the present invention provides a compound of Formula I-aa, wherein LBM is an E3 ubiquitin ligase (cereblon) binding moiety thereby forming a compound of formula I-aa'-1 or I-aa"-1:

I-aa'-1

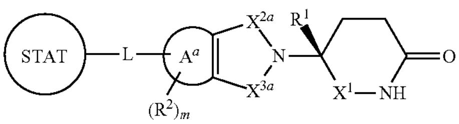

I-aa"-1

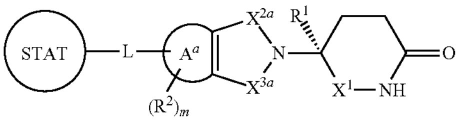

or a pharmaceutically acceptable salt thereof, wherein STAT, L, Ring $A^a$, $X^1$, $X^{2a}$, $X^{3a}$, $R^1$, $R^2$ and m are as described above.

As defined above and described herein, each of $X^1$, $X^{2a}$, and $X^{3a}$ is independently a bivalent moiety selected from a covalent bond, —$CH_2$—, —C(O)—, —C(S)—, or

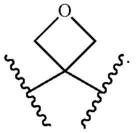 [SMILES: *C1(*)COC1]

In some embodiments, $X^1$ is a covalent bond, —$CH_2$—, —C(O)—, —C(S)—,

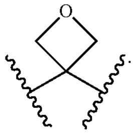 [SMILES: *C1(*)COC1]

In some embodiments, $X^1$ is selected from those depicted in Table 1, below.

In some embodiments, $X^{2a}$ is a covalent bond, —$CH_2$—, —C(O)—, —C(S)—, or

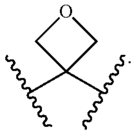 [SMILES: *C1(*)COC1]

In some embodiments, $X^{2a}$ is selected from those depicted in Table 1, below.

In some embodiments, $X^{3a}$ is a covalent bond, —$CH_2$—, —C(O)—, —C(S)—, or

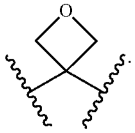 [SMILES: *C1(*)COC1]

In some embodiments, $X^{3a}$ is selected from those depicted in Table 1, below.

As defined above and described herein, each of $X^4$ and $X^5$ is independently a bivalent moiety selected from —$CH_2$—, —C(O)—, —C(S)—, or

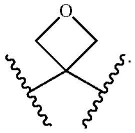 [SMILES: *C1(*)COC1]

In some embodiments, $X^{4a}$ is —$CH_2$—, —C(O)—, —C(S)—, or

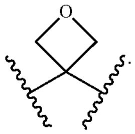 [SMILES: *C1(*)COC1]

In some embodiments, $X^{4a}$ is selected from those depicted in Table 1, below.

In some embodiments, $X^{5a}$ is —$CH_2$—, —C(O)—, —C(S)—, or

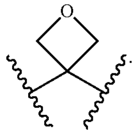 [SMILES: *C1(*)COC1]

In some embodiments, $X^{5a}$ is selected from those depicted in Table 1, below.

As defined above and described herein, $R^1$ is hydrogen, deuterium, halogen, —CN, —OR, —SR, —S(O)R, —$S(O)_2R$, —$NR_2$, or an optionally substituted $C_{1-4}$ aliphatic.

In some embodiments, $R^1$ is hydrogen, deuterium, halogen, —CN, —OR, —SR, —S(O)R, —$S(O)_2R$, —$NR_2$, or an optionally substituted $C_{1-4}$ aliphatic.

In some embodiments, $R^1$ is selected from those depicted in Table 1, below.

As defined above and described herein, each of $R^2$, $R^{3b}$, and $R^{4a}$ is independently hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)$S(O)_2R$.

In some embodiments, $R^2$ is hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)$S(O)_2R$.

In some embodiments, $R^2$ is selected from those depicted in Table 1, below.

In some embodiments, $R^{3b}$ is hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)$S(O)_2R$.

In some embodiments, $R^{3b}$ is methyl.

In some embodiments, $R^{3b}$ is selected from those depicted in Table 1, below.

In some embodiments, $R^{4a}$ is hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)$S(O)_2R$.

In some embodiments, $R^{4a}$ is methyl.

In some embodiments, $R^{4a}$ is selected from those depicted in Table 1, below.

As defined above and described herein, $R^a$ is hydrogen or $C_{1-6}$ aliphatic.

In some embodiments, $R^{5a}$ is t-butyl.

In some embodiments, $R^{5a}$ is selected from those depicted in Table 1, below.

As defined above and described herein, each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur.

In some embodiments, $R^6$ is an optionally substituted $C_{1-6}$ aliphatic group. In some embodiments, $R^6$ is an optionally substituted phenyl. In some embodiments, $R^6$ is an optionally substituted 4-7 membered saturated or partially unsaturated heterocyclic ring having 1-2 heteroatoms independently selected from nitrogen, oxygen, and sulfur. In some embodiments, $R^6$ is an optionally substituted 5-6 membered heteroaryl ring having 1-4 heteroatoms independently selected from nitrogen, oxygen, and sulfur.

In some embodiments, $R^6$ is selected from those depicted in Table 1, below.

As defined above and described herein, Ring $A^a$ is a fused ring selected from 6-membered aryl containing 0-2 nitrogen atoms, 5 to 7-membered partially saturated carbocyclyl, 5 to 7-membered partially saturated heterocyclyl with 1-2 heteroatoms independently selected from nitrogen, oxygen or sulfur, or 5-membered heteroaryl with 1-3 heteroatoms independently selected from nitrogen, oxygen or sulfur.

In some embodiments Ring $A^a$ is a fused 6-membered aryl containing 0-2 nitrogen atoms. In some embodiments Ring $A^a$ is a fused 5 to 7-membered partially saturated carbocyclyl. In some embodiments Ring $A^a$ is a fused 5 to 7-membered partially saturated heterocyclyl with 1-2 heteroatoms independently selected from nitrogen, oxygen or sulfur. In some embodiments Ring $A^a$ is a fused 5-membered heteroaryl with 1-3 heteroatoms independently selected from nitrogen, oxygen or sulfur.

In some embodiments, Ring $A^a$ is a fused phenyl.

In some embodiments, Ring $A^a$ is selected from those depicted in Table 1, below.

As defined above and described herein, Ring $B^a$ is selected from 6-membered aryl containing 0-2 nitrogen atoms or a 8-10 membered bicyclic heteroaryl having 1-5 heteroatoms independently selected from nitrogen, oxygen, or sulfur.

In some embodiments, Ring $B^a$ is a 6-membered aryl containing 0-2 nitrogen atoms. In some embodiments, Ring $B^a$ is a 8-10 membered bicyclic heteroaryl having 1-5 heteroatoms independently selected from nitrogen, oxygen, or sulfur.

In some embodiments, Ring $B^a$ is

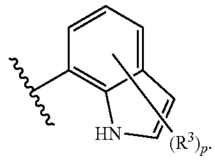

In some embodiments, Ring $B^a$ is selected from those depicted in Table 1, below.

As defined above and described herein, Ring $C^a$ is selected from 6-membered aryl containing 0-2 nitrogen atoms or a 5-membered heteroaryl with 1-3 heteroatoms independently selected from nitrogen, oxygen or sulfur.

In some embodiments, Ring $C^a$ is a 6-membered aryl containing 0-2 nitrogen atoms. In some embodiments, Ring $C^a$ is a 5-membered heteroaryl with 1-3 heteroatoms independently selected from nitrogen, oxygen or sulfur.

In some embodiments, Ring $C^a$ is

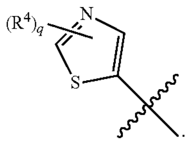

In some embodiments, Ring $C^a$ is selected from those depicted in Table 1, below.

As defined above and described herein, m is 0, 1, 2, 3 or 4.

In some embodiments, m is 0. In some embodiments, m is 1. In some embodiments, m is 2. In some embodiments, m is 3. In some embodiments, m is 4.

In some embodiments, m is selected from those depicted in Table 1, below.

In some embodiments, o is selected from those depicted in Table 1, below.

As defined above and described herein, o is 0, 1, 2, 3 or 4.

In some embodiments, o is 0. In some embodiments, o is 1. In some embodiments, o is 2. In some embodiments, o is 3. In some embodiments, o is 4.

In some embodiments, o is selected from those depicted in Table 1, below.

As defined above and described herein, q is 0, 1, 2, 3 or 4.

In some embodiments, q is 0. In some embodiments, q is 1. In some embodiments, q is 2. In some embodiments, q is 3. In some embodiments, q is 4.

In some embodiments, q is selected from those depicted in Table 1, below.

As defined above and described herein, each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or: two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, R is hydrogen. In some embodiments, R is phenyl. In some embodiments, R is a 4-7 membered saturated or partially unsaturated heterocyclic having 1-2 heteroatoms independently selected from nitrogen, oxygen, and sulfur. In some embodiments, R is a 5-6 membered heteroaryl ring having 1-4 heteroatoms independently selected from nitrogen, oxygen, and sulfur. In some embodiments, two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, R is selected from those depicted in Table 1, below.

In certain embodiments, the present invention provides a compound of formula I, wherein LBM is a VHL binding moiety thereby forming a compound of formula I-ab:

I-ab

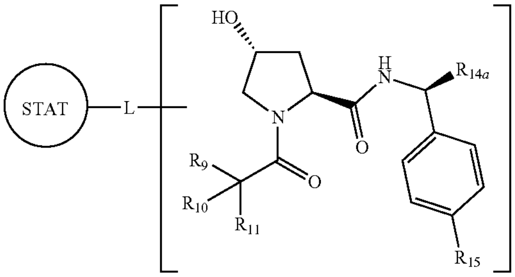

or a pharmaceutically acceptable salt thereof, wherein L and STAT are as defined above and described in embodiments herein, and wherein each of the variables $R_9$, $R_{10}$, $R_{11}$, $R_{14a}$, and $R_{15}$ is as described and defined in WO 2017/030814, WO 2016/118666, and US 2017/0327469, the entirety of each of which is herein incorporated by reference.

In certain embodiments, the present invention provides a compound of formula I, wherein LBM is a VHL binding moiety thereby forming a compound of formula I-ac-1 or I-ac-2:

I-ac-1

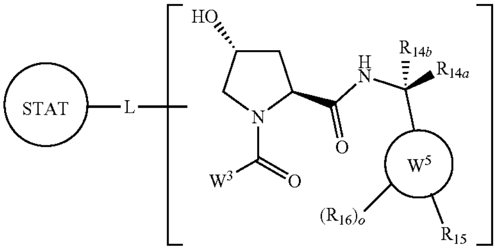

I-ac-2

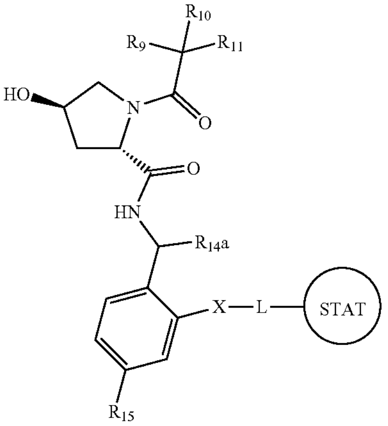

or a pharmaceutically acceptable salt thereof, wherein L and STAT are as defined above and described in embodiments herein, and wherein each of the variables X, $W^3$, $W^5$, $R_9$, $R_{10}$, $R_{11}$, $R_{14a}$, $R_{14b}$, $R_{15}$, $R_{16}$, and o is as described and defined in WO 2017/030814, WO 2016/118666, and US 2017/0327469, the entirety of each of which is herein incorporated by reference.

In certain embodiments, the present invention provides a compound of formula I, wherein LBM is an IAP binding moiety thereby forming a compound of formula I-ad:

I-ad

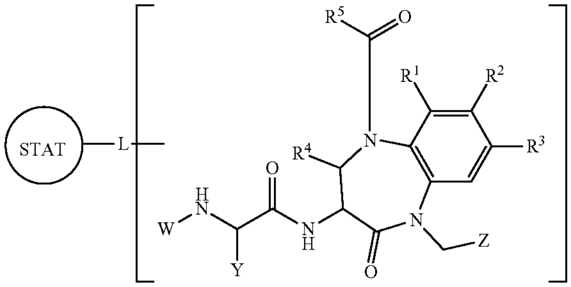

or a pharmaceutically acceptable salt thereof, wherein L and STAT are as defined above and described in embodiments herein, and wherein each of the variables W, Y, Z, $R^1$, $R^2$, $R^3$, $R^4$, and $R^5$ is as described and defined in WO 2014/044622, US 2015/0225449. WO 2015/071393, and US 2016/0272596, the entirety of each of which is herein incorporated by reference.

In certain embodiments, the present invention provides a compound of formula I, wherein LBM is a MDM2 binding moiety thereby forming a compound of formula I-ae:

I-ae

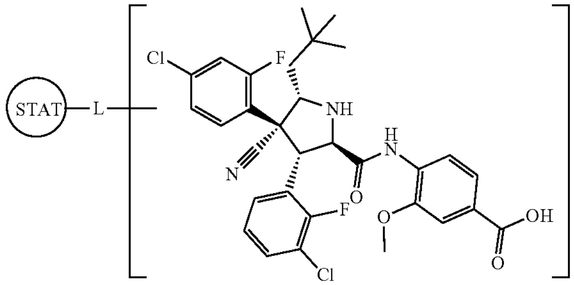

or a pharmaceutically acceptable salt thereof, as described and defined in Hines, J. et al., *Cancer Res.* (DOI: 10.1158/0008-5472.CAN-18-2918), the entirety of each of which is herein incorporated by reference.

In certain embodiments, the present invention provides a compound of formula I, wherein LBM is a DCAF16 binding moiety thereby forming a compound of formula I-af:

I-af

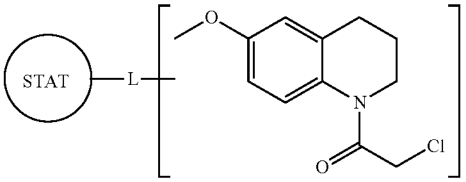

or a pharmaceutically acceptable salt thereof, as described and defined in Zhang, X. et al., bioRxiv (doi: https://doi.org/10.1101/443804), the entirety of each of which is herein incorporated by reference.

In certain embodiments, the present invention provides a compound of formula I, wherein LBM is a RNF114 binding moiety thereby forming a compound of formula I-ag:

I-ag

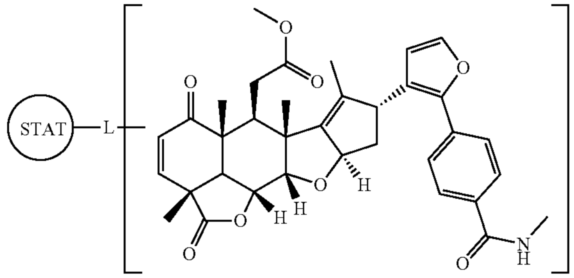

or a pharmaceutically acceptable salt thereof, as described and defined in Spradin, J. N. et al., bioRxiv (doi: https://doi.org/10.1101/436998), the entirety of each of which is herein incorporated by reference.

In certain embodiments, the present invention provides a compound of formula I, wherein LBM is a RNF4 binding moiety thereby forming a compound of formula I-ah:

I-ah

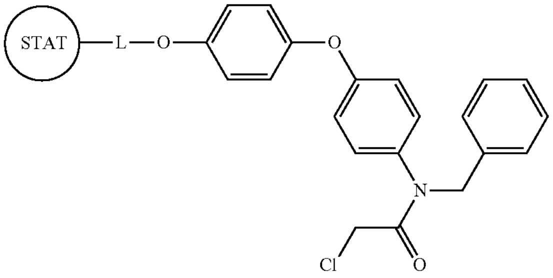

or a pharmaceutically acceptable salt thereof, as described and defined in Ward, C. C., et al., bioRxiv (doi: https://doi.org/0.111/4391.25), the entirety of each of which is herein incorporated by reference.

In certain embodiments, the present invention provides a compound of formula I, wherein LBM is a VHL binding moiety thereby forming a compound of formula I-aay-1 or I-aay-2:

I-aay-1

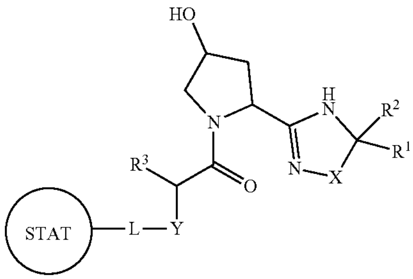

I-aay-2

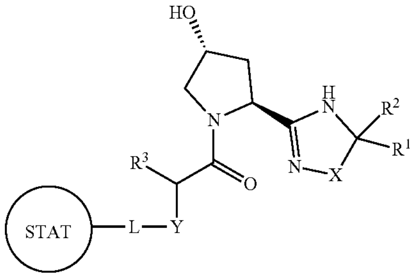

or a pharmaceutically acceptable salt thereof, wherein L and STAT are as defined above and described in embodiments herein, and wherein each of the variables $R^1$, $R^2$, $R^3$, X, and Y is as defined and described in WO 2019/084026, the entirety of each of which is herein incorporated by reference.

In certain embodiments, the present invention provides a compound of formula I, wherein LBM is a VHL binding moiety thereby forming a compound of formula I-aaz-1 or I-aaz-2:

I-aaz-1

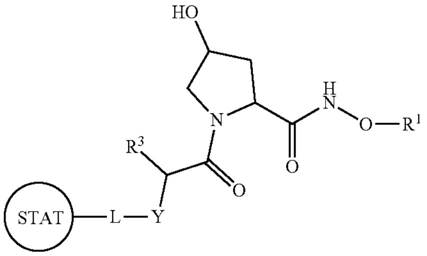

I-aaz-2

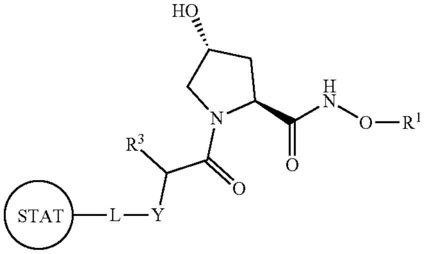

or a pharmaceutically acceptable salt thereof, wherein L and STAT are as defined above and described in embodiments herein, and wherein each of the variables $R^1$, $R^3$, and Y is as defined and described in WO 2019/084030, the entirety of each of which is herein incorporated by reference.

In certain embodiments, the present invention provides a compound of formula I, wherein LBM is a E3 ubiquitin ligase (cereblon) binding moiety thereby forming a compound of formula I-aaaa-1, I-aaaa-2, I-aaaa-3, or I-aaaa-4:

I-aaaa-1

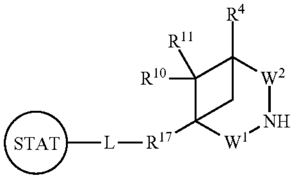

I-aaaa-2

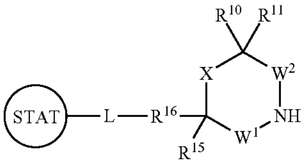

I-aaaa-3

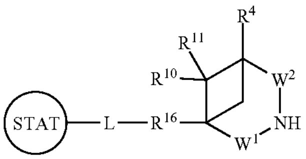

I-aaaa-4

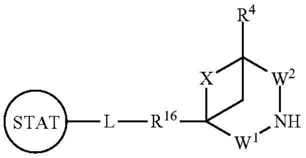

or a pharmaceutically acceptable salt thereof, wherein L and STAT are as defined above and described herein, and wherein each of the variables $R^4$, $R^{10}$, $R^{11}$, $R^{15}$, $R^{16}$, $R^{17}$, $W^1$, $W^2$, and X is as defined in WO 2019/099868 which is herein incorporated by reference in its entirety, and wherein

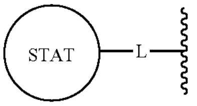

is attached to $R^{17}$ or $R^{16}$ at the site of attachment of $R^{12}$ as defined in WO 2018/237026, such that

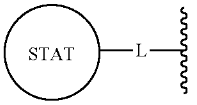

takes the place of the $R^{12}$ substituent.

In some embodiments, LBM is

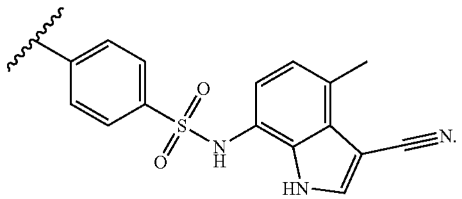 [SMILES: *c1ccc(S(=O)(=O)Nc2ccc(C)c3c(C#N)c[nH]c23)cc1]

In some embodiments, LBM is

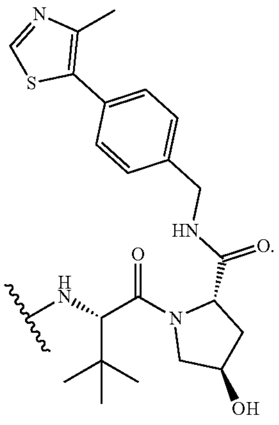 [SMILES: *N[C@H](C(=O)N1C[C@H](O)C[C@H]1C(=O)NCc1ccc(-c2scnc2C)cc1)C(C)(C)C]

In some embodiments, LBM is
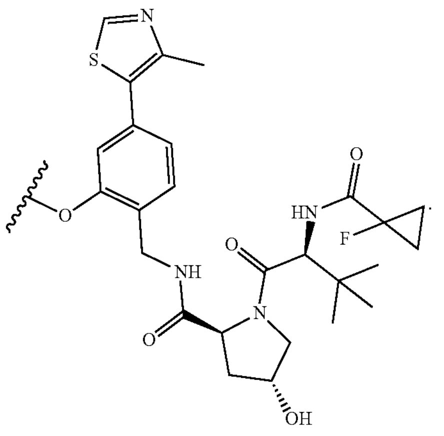 [SMILES: *Oc1cc(-c2scnc2C)ccc1CNC(=O)[C@@H]1C[C@@H](O)CN1C(=O)[C@@H](NC(=O)C1(F)CC1)C(C)(C)C]
In some embodiments, LBM is
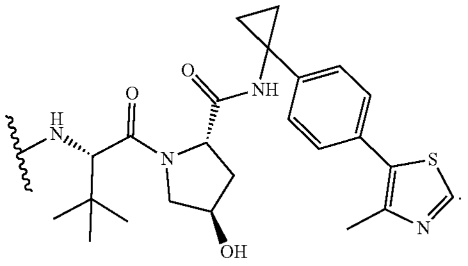 [SMILES: *N[C@H](C(=O)N1C[C@H](O)C[C@H]1C(=O)NC1(c2ccc(-c3scnc3C)cc2)CC1)C(C)(C)C]
In some embodiments, LBM is
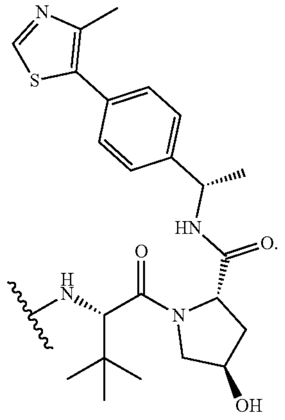 [SMILES: *N[C@H](C(=O)N1C[C@H](O)C[C@H]1C(=O)N[C@@H](C)c1ccc(-c2scnc2C)cc1)C(C)(C)C]
In some embodiments, LBM is
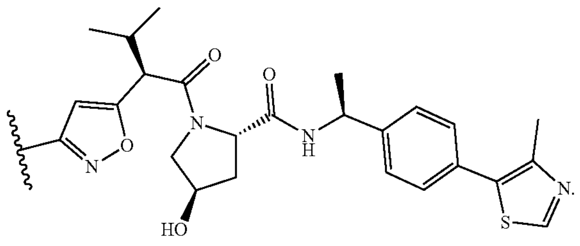 [SMILES: *c1cc([C@H](C(=O)N2C[C@H](O)C[C@H]2C(=O)N[C@@H](C)c2ccc(-c3scnc3C)cc2)C(C)C)on1]
In some embodiments, LBM is
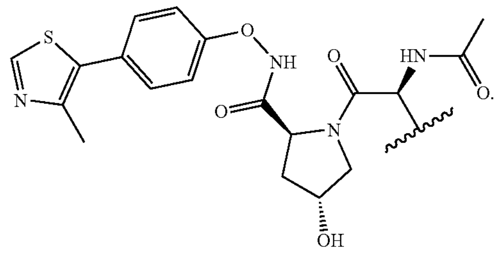 [SMILES: *[C@H](NC(C)=O)C(=O)N1C[C@H](O)C[C@H]1C(=O)NOc1ccc(-c2scnc2C)cc1]
In some embodiments, LBM is
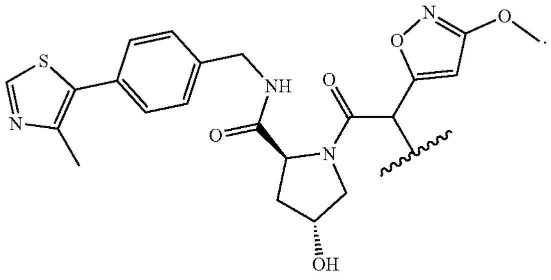 [SMILES: *C(C(=O)N1C[C@H](O)C[C@H]1C(=O)NCc1ccc(-c2scnc2C)cc1)c1cc(OC)no1]
In some embodiments, LBM is
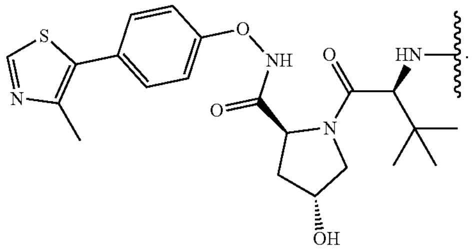 [SMILES: *N[C@H](C(=O)N1C[C@H](O)C[C@H]1C(=O)NOc1ccc(-c2scnc2C)cc1)C(C)(C)C]

In some embodiments, LBM is
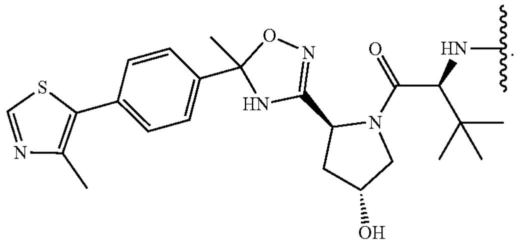 [SMILES: *N[C@H](C(=O)N1C[C@H](O)C[C@H]1C1=NOC(C)(c2ccc(-c3scnc3C)cc2)N1)C(C)(C)C]
In some embodiments, LBM is
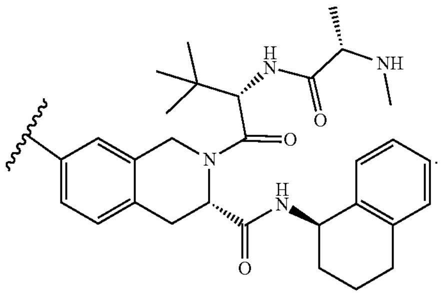 [SMILES: *c1ccc2c(c1)CN(C(=O)[C@@H](NC(=O)[C@H](C)NC)C(C)(C)C)[C@H](C(=O)N[C@@H]1CCCc3ccccc31)C2]
In some embodiments, LBM is
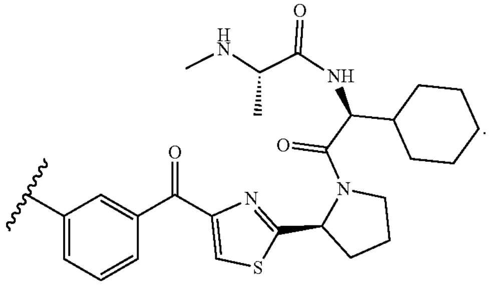 [SMILES: *c1cccc(C(=O)c2csc([C@@H]3CCCN3C(=O)[C@@H](NC(=O)[C@H](C)NC)C3CCCCC3)n2)c1]
In some embodiments, LBM is
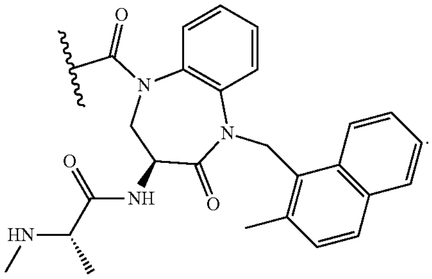 [SMILES: *C(=O)N1C[C@H](NC(=O)[C@H](C)NC)C(=O)N(Cc2c(C)ccc3ccccc23)c2ccccc21]
In some embodiments, LBM is
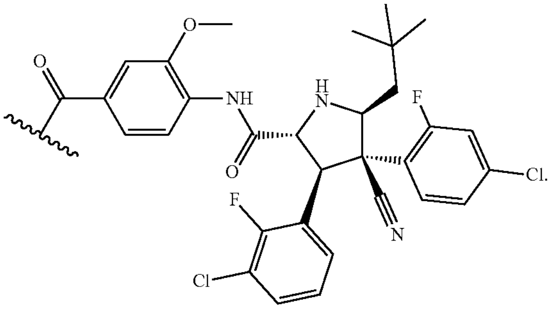 [SMILES: *C(=O)c1ccc(NC(=O)[C@@H]2N[C@@H](CC(C)(C)C)[C@](C#N)(c3ccc(Cl)cc3F)[C@H]2c2cccc(Cl)c2F)c(OC)c1]
In some embodiments, LBM is
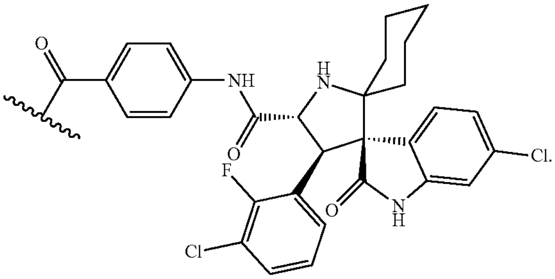 [SMILES: *C(=O)c1ccc(NC(=O)[C@@H]2NC3(CCCCC3)[C@@]3(C(=O)Nc4cc(Cl)ccc43)[C@H]2c2cccc(Cl)c2F)cc1]
In some embodiments, LBM is
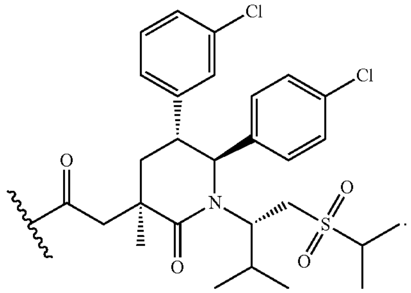 [SMILES: *C(=O)C[C@@]1(C)C[C@H](c2cccc(Cl)c2)[C@@H](c2ccc(Cl)cc2)N([C@H](CS(=O)(=O)C(C)C)C(C)C)C1=O]
In some embodiments, LBM is
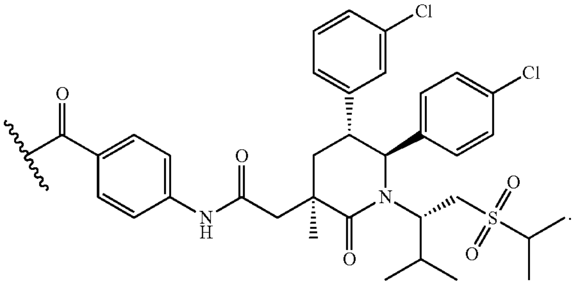 [SMILES: *C(=O)c1ccc(NC(=O)C[C@@]2(C)C[C@H](c3cccc(Cl)c3)[C@@H](c3ccc(Cl)cc3)N([C@H](CS(=O)(=O)C(C)C)C(C)C)C2=O)cc1]

In some embodiments, LBM is
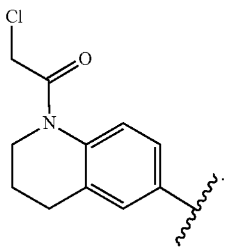 [SMILES: *c1ccc2c(c1)CCCN2C(=O)CCl]
In some embodiments, LBM is
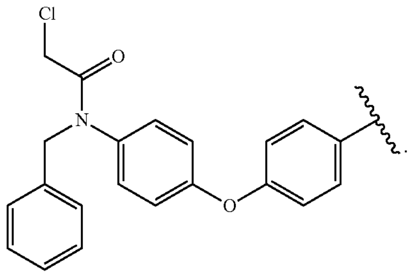 [SMILES: *c1ccc(Oc2ccc(N(Cc3ccccc3)C(=O)CCl)cc2)cc1]
In some embodiments, LBM is
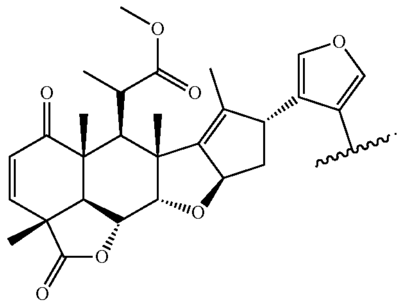 [SMILES: *c1cocc1[C@@H]1C[C@H]2O[C@@H]3[C@@H]4OC(=O)[C@]5(C)C=CC(=O)[C@](C)([C@@H](C(C)C(=O)OC)[C@]3(C)C2=C1C)[C@@H]45]
In some embodiments, LBM is
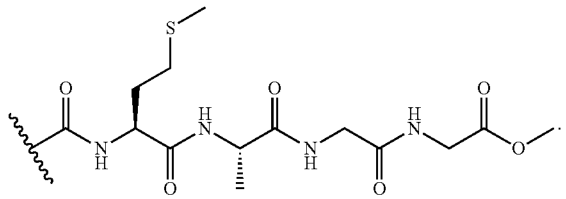 [SMILES: *C(=O)N[C@@H](CCSC)C(=O)N[C@@H](C)C(=O)NCC(=O)NCC(=O)OC]
In some embodiments, LBM is
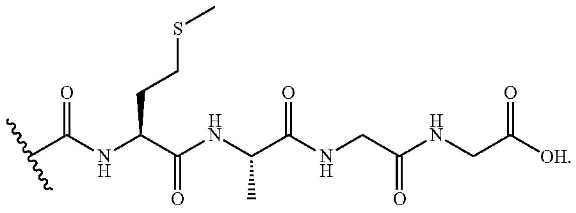 [SMILES: *C(=O)N[C@@H](CCSC)C(=O)N[C@@H](C)C(=O)NCC(=O)NCC(=O)O]
In some embodiments, LBM is
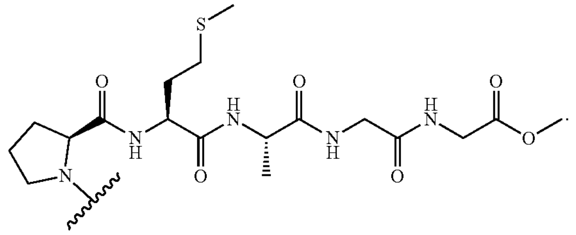 [SMILES: *N1CCC[C@H]1C(=O)N[C@@H](CCSC)C(=O)N[C@@H](C)C(=O)NCC(=O)NCC(=O)OC]
In some embodiments, LBM is
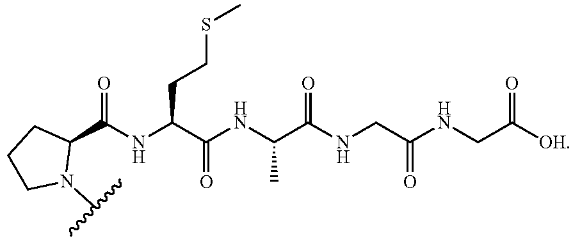 [SMILES: *N1CCC[C@H]1C(=O)N[C@@H](CCSC)C(=O)N[C@@H](C)C(=O)NCC(=O)NCC(=O)O]
In some embodiments, LBM is
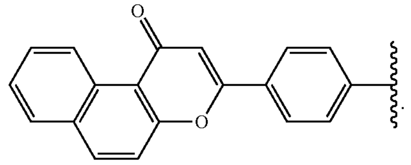 [SMILES: *c1ccc(-c2cc(=O)c3c(ccc4ccccc43)o2)cc1]
In some embodiments, LBM is
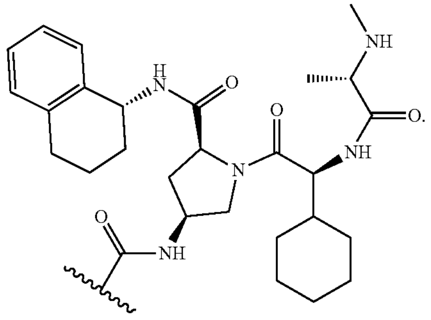 [SMILES: *C(=O)N[C@H]1C[C@@H](C(=O)N[C@@H]2CCCc3ccccc32)N(C(=O)[C@@H](NC(=O)[C@H](C)NC)C2CCCCC2)C1]

In some embodiments, LBM is

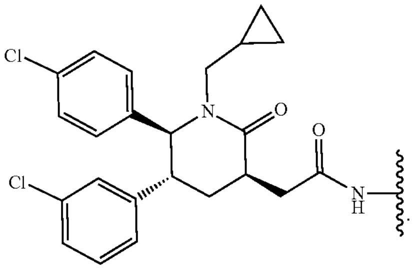 [SMILES: *NC(=O)C[C@H]1C[C@H](c2cccc(Cl)c2)[C@@H](c2ccc(Cl)cc2)N(CC2CC2)C1=O]

In some embodiments, LBM is

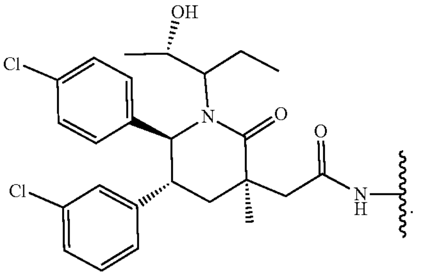 [SMILES: *NC(=O)C[C@@]1(C)C[C@H](c2cccc(Cl)c2)[C@@H](c2ccc(Cl)cc2)N(C(CC)[C@H](C)O)C1=O]

In some embodiments, LBM is

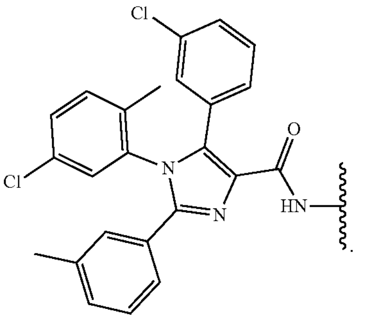 [SMILES: *NC(=O)c1nc(-c2cccc(C)c2)n(-c2cc(Cl)ccc2C)c1-c1cccc(Cl)c1]

In some embodiments, LBM is

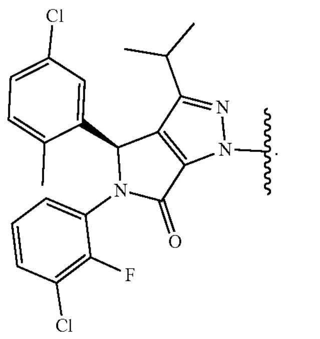 [SMILES: *n1nc(C(C)C)c2c1C(=O)N(c1cccc(Cl)c1F)[C@H]2c1cc(Cl)ccc1C]

In certain embodiments, the present invention provides a compound of formula I, wherein LBM is a E3 ubiquitin ligase (cereblon) binding moiety thereby forming a compound of formula formula I-bbbb:

I-bbbb

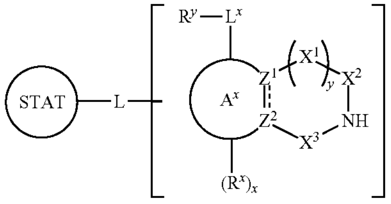

or a pharmaceutically acceptable salt thereof, wherein L and STAT are as defined above and described in embodiments herein, wherein:

each $X^1$ is independently —$CH_2$—, —O—, —NR—, —$CF_2$—,

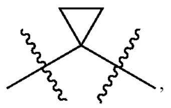

—C(O)—, —C(S)—, or

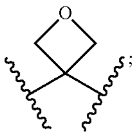 [SMILES: *C1(*)COC1]

$X^2$ and $X^3$ are independently —$CH_2$—, —C(O)—, —C(S)—, or

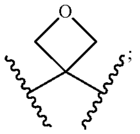 [SMILES: *C1(*)COC1]

$Z^1$ and $Z^2$ are independently a carbon atom or a nitrogen atom;

Ring $A^x$ is a fused ring selected from benzo or a 5-6 membered heteroaryl ring having 1-4 heteroatoms independently selected from nitrogen, oxygen, and sulfur;

$L^x$ is a covalent bond or a $C_{1-3}$ bivalent straight or branched saturated or unsaturated hydrocarbon chain wherein 1-2 methylene units of the chain are independently and optionally replaced with —O—, —S—, —C(O)—, —C(S)—, —$CR_2$—, —CRF—, —$CF_2$—, —NR—, or —$S(O)_2$—;

each $R^x$ is independently selected from hydrogen, deuterium, $R^z$, halogen, —CN, —$NO_2$, —OR, —SR, —$NR_2$, —$S(O)_2R$, —$S(O)_2NR_2$, —S(O)R, —$CF_2R$, —$CF_3$, —$CR_2$(OR), —$CR_2$($NR_2$), —C(O)R, —C(O)OR, —C(O)$NR_2$, —C(O)N(R)OR, —OC(O)R, —OC(O)$NR_2$, —C(S)$NR_2$, —N(R)C(O)OR, —N(R)C(O)R, —N(R)C(O)$NR_2$, —N(R)$S(O)_2R$, —OP(O)$R_2$, —OP(O)$(OR)_2$, —OP(O)(OR)$NR_2$, —OP(O)$(NR_2)_2$, —Si(OR)$R_2$, and —$SiR_3$; or two $R^x$ groups are optionally taken together to form an optionally substituted 5-8 membered partially unsaturated or aryl fused ring having 0-2 heteroatoms independently selected from nitrogen, oxygen, or sulfur;

each R is independently selected from hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same carbon or nitrogen are optionally taken together with their intervening atoms to form an optionally substituted 4-7 membered saturated, partially unsaturated, or heteroaryl ring having 0-3 heteroatoms, in addition to the carbon or nitrogen, independently selected from nitrogen, oxygen, and sulfur;

$R^y$ is selected from

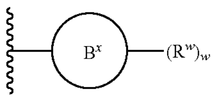

or hydrogen;

Ring $B^x$ is phenyl, a 4-10 membered saturated or partially unsaturated mono- or bicyclic carbocyclic or heterocyclic ring having 1-3 heteroatoms independently selected from nitrogen, oxygen, and sulfur, or a 5-6 membered heteroaryl ring having 1-4 heteroatoms independently selected from nitrogen, oxygen, and sulfur, wherein Ring $B^x$ is further optionally substituted with 1-2 oxo groups;

each $R^w$ is independently selected from hydrogen, deuterium, $R^z$, halogen, —CN, —$NO_2$, —OR, —SR, —$NR_2$, —$S(O)_2R$, —$S(O)_2NR_2$, —S(O)R, —$CF_2R$, —$CF_3$, —$CR_2(OR)$, —$CR_2(NR_2)$, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, —N(R)$S(O)_2R$, —OP(O)$R_2$, —OP(O)$(OR)_2$, —OP(O)(OR)$NR_2$, —OP(O)$(NR_2)_2$, and —$SiR_3$;

each $R^z$ is independently selected from an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

⎓ is a single or double bond;

x is 0, 1, 2, 3 or 4;

y is 0, 1 or 2; and w is 0, 1, 2, 3 or 4.

As defined above and described herein, each $X^1$ is independently —$CH_2$—, —O—, —NR—, —$CF_2$—,

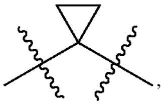 [SMILES: *C1(*)CC1]

—C(O)—, —C(S)—, or

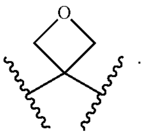 [SMILES: *C1(*)COC1]

In some embodiments, $X^1$ is a covalent bond. In some embodiments, $X^1$ is —$CH_2$—. In some embodiments, $X^1$ is —O—. In some embodiments, $X^1$ is —NR—. In some embodiments, $X^1$ is —$CF_2$—. In some embodiments, $X^1$ is

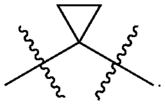 [SMILES: *C1(*)CC1]

In some embodiments, $X^1$ is —C(O)—. In some embodiments, $X^1$ is —C(S)—. In some embodiments, $X^1$ is

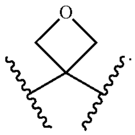 [SMILES: *C1(*)COC1]

In certain embodiments, $X^1$ is selected from those shown in the compounds of Table 1.

As defined above and described herein, $X^2$ and $X^3$ are independently —$CH_2$—, —C(O)—, —C(S)—, or

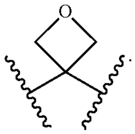

In some embodiments, $X^2$ and $X^3$ are independently —$CH_2$—. In some embodiments, $X^2$ and $X^3$ are independently —C(O)—. In some embodiments, $X^2$ and $X^3$ are independently —C(S)—. In some embodiments, $X^2$ and $X^3$ are independently

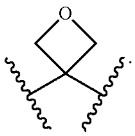

In certain embodiments, $X^2$ and $X^3$ are independently selected from those shown in the compounds of Table 1.

As define above and described herein, $Z^1$ and $Z^2$ are independently a carbon atom or a nitrogen atom.

In some embodiments, $Z^1$ and $Z^2$ are independently a carbon atom. In some embodiments, $Z^1$ and $Z^2$ are independently a carbon atom.

In certain embodiments, $Z^1$ and $Z^2$ are independently selected from those shown in the compounds of Table 1.

As defined above and described herein, Ring $A^x$ is fused ring selected from benzo or a 5-6 membered heteroaryl ring having 1-4 heteroatoms independently selected from nitrogen, oxygen, and sulfur.

In some embodiments, Ring $A^x$ is benzo. In some embodiments, Ring $A^x$ is a 5-6 membered heteroaryl ring having 1-4 heteroatoms independently selected from nitrogen, oxygen, and sulfur.

In some embodiments, Ring $A^x$ is

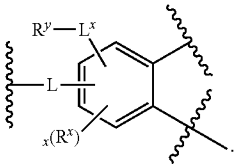

In some embodiments, Ring $A^x$ is

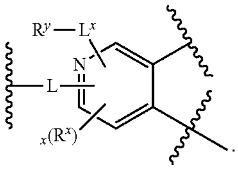

In some embodiments, Ring $A^x$ is

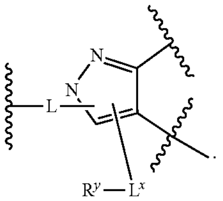

In some embodiments, Ring $A^x$ is

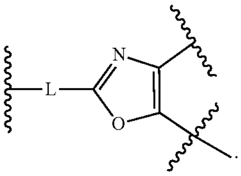

In certain embodiments, Ring AX is selected from those shown in the compounds of Table 1.

As defined above and described herein, LU is a covalent bond or a $C_{1-3}$ bivalent straight or branched saturated or unsaturated hydrocarbon chain wherein 1-2 methylene units of the chain are independently and optionally replaced with —O—, —S—, —C(O)—, —C(S)—, —$CR_2$—, —CRF—, —$CF_2$—, —NR—, or $S(O)_2$—.

In some embodiments, LU is a covalent bond. In some embodiments, LU is a $C_{1-3}$ bivalent straight or branched saturated or unsaturated hydrocarbon chain wherein 1-2 methylene units of the chain are independently and optionally replaced with —O—, —S—, —C(O)—, —C(S)—, —$CR_2$—, —CRF—, —$CF_2$—, —NR—, or —$S(O)_2$—.

In some embodiments, $L^x$ is —C(O)—.

In certain embodiments, $L^x$ is selected from those shown in the compounds of Table 1.

As defined above and described herein, each R is independently selected from hydrogen, deuterium, $R^z$, halogen, —CN, —$NO_2$, —OR, —SR, —$NR_2$, —$S(O)_2R$, —$S(O)_2NR_2$, —S(O)R, —$CF_2R$, —$CF_3$, —$CR_2(OR)$, —$CR_2(NR_2)$, —C(O)R, —C(O)OR, —$C(O)NR_2$, —C(O)N(R)OR, —OC(O)R, —$OC(O)NR_2$, —$C(S)NR_2$, —N(R)C(O)OR, —N(R)C(O)R, —N(R)C(O)$NR_2$, —N(R)$S(O)_2R$, —OP(O)$R_2$, —OP(O)$(OR)_2$, —OP(O)(OR)$NR_2$, —OP(O)$(NR_2)_2$, —Si(OR)$R_2$, and —$SiR_3$, or two $R^x$ groups are optionally taken together to form an optionally substituted 5-8 membered partially unsaturated or aryl fused ring having 0-2 heteroatoms independently selected from nitrogen, oxygen, or sulfur.

In some embodiments, $R^x$ is hydrogen. In some embodiments, $R^x$ is deuterium. In some embodiments, $R^x$ is $R^z$. In some embodiments, $R^x$ is halogen. In some embodiments, $R^x$ is —CN. In some embodiments, $R^x$ is —$NO_2$. In some embodiments, $R^x$ is —OR. In some embodiments, $R^x$ is —SR. In some embodiments, $R^x$ is —$NR_2$. In some embodiments, $R^x$ is —$S(O)_2R$. In some embodiments, Rx is —$S(O)_2NR_2$. In some embodiments, $R^x$ is —S(O)R. In some embodiments, $R^x$ is —$CF_2R$. In some embodiments, Rx is —$CF_3$. In some embodiments, $R^x$ is —$CR_2(OR)$. In some embodiments, $R^x$ is —$CR_2(NR_2)$. In some embodiments, Rx is —C(O)R. In some embodiments, $R^x$ is —C(O)OR. In some embodiments, Rx is —$C(O)NR_2$. In some embodiments, $R^x$ is —C(O)N(R)OR. In some embodiments, Rx is —OC(O)R. In some embodiments, Rx is —$OC(O)NR_2$. In some embodiments, $R^x$ is —$C(S)NR_2$. In some embodiments, $R^x$ is —N(R)C(O)OR. In some embodiments, $R^x$ is —N(R)C(O)R. In some embodiments, $R^x$ is —N(R)C(O)$NR_2$. In some embodiments, $R^x$ is —N(R)$S(O)_2R$. In some embodiments, $R^x$ is —OP(O)$R_2$. In some embodiments, $R^x$ is —OP(O)$(OR)_2$. In some embodiments, Rx is —OP(O)(OR)$NR_2$. In some embodiments, $R^x$ is —OP(O)$(NR_2)_2$. In some embodiments, $R^x$ is —Si(OR)$R_2$. In some embodiments, Rx is —$SiR_3$. In some embodiments, two $R^x$ groups are optionally taken together to form an optionally substituted 5-8 membered partially unsaturated or aryl fused ring having 0-2 heteroatoms independently selected from nitrogen, oxygen, or sulfur.

In some embodiments, Rx is fluoro. In some embodiments, Rx is bromo. In some embodiments, $R^x$ is methyl. In some embodiments, $R^x$ is —OH. In some embodiments, $R^x$ is —$NH_2$. In some embodiments, $R^x$ is —$NHCH_3$. In some embodiments, $R^x$ is —$N(CH_3)_2$. In some embodiments, $R^x$ is —$NHCH(CH_3)_2$. In some embodiments, Rx is —$NHSO_2CH_3$. In some embodiments, $R^x$ is —$CH_2OH$. In some embodiments, Rx is —$CH_2NH_2$. In some embodiments, $R^x$ is —$C(O)NH_2$. In some embodiments, $R^x$ is —$C(O)NHCH_3$. In some embodiments, $R^x$ is

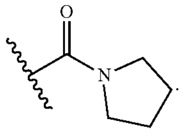 [SMILES: *C(=O)N1CCCC1]

In some embodiments, $R^x$ is

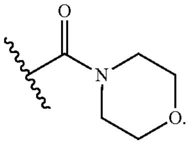 [SMILES: *C(=O)N1CCOCC1]

In some embodiments, $R^x$ is

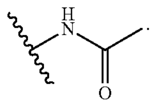 [SMILES: *NC(C)=O]

In some embodiments, $R^x$

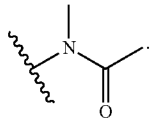 [SMILES: *N(C)C(C)=O]

In some embodiments, $R^x$

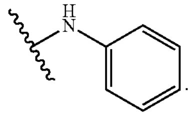 [SMILES: *Nc1ccccc1]

In some embodiments, $R^x$

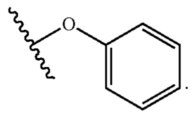 [SMILES: *Oc1ccccc1]

In some embodiments, $R^x$ is

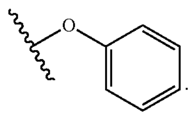

In some embodiments, $R^x$ is In

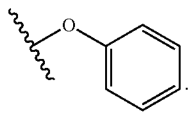 [SMILES: *Oc1ccccc1]

embodiments, $R^x$ is

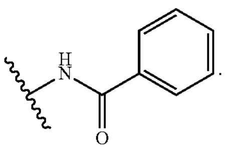 [SMILES: *NC(=O)c1ccccc1]

In some embodiments, R is

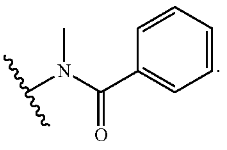 [SMILES: *N(C)C(=O)c1ccccc1]

In certain embodiments, each $R^x$ is independently selected from those shown in the compounds of Table 1.

As defined above and described here, each R is independently selected from hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or two R groups on the same carbon or nitrogen are optionally taken together with their intervening atoms to form an optionally substituted 4-7 membered saturated, partially unsaturated, or heteroaryl ring having 0-3 heteroatoms, in addition to the carbon or nitrogen, independently selected from nitrogen, oxygen, and sulfur.

In some embodiments, R is hydrogen. In some embodiments, R is an optionally substituted $C_{1-6}$ aliphatic. In some embodiments, R is an optionally substituted phenyl. In some embodiments, R is an optionally substituted 4-7 membered saturated or partially unsaturated heterocyclic having 1-2 heteroatoms independently selected from nitrogen, oxygen, and sulfur. In some embodiments, R is an optionally substituted a 5-6 membered heteroaryl ring having 1-4 heteroatoms independently selected from nitrogen, oxygen, and sulfur. In some embodiments, two R groups on the same carbon or nitrogen are optionally taken together with their intervening atoms to form an optionally substituted 4-7 membered saturated, partially unsaturated, or heteroaryl ring having 0-3 heteroatoms, in addition to the carbon or nitrogen, independently selected from nitrogen, oxygen, and sulfur.

As defined above and described herein, R is selected from

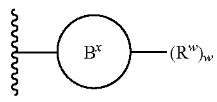

or hydrogen.

In some embodiment $R^y$ is

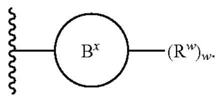

In some embodiments, R is hydrogen.

In certain embodiments, R is selected from those shown in the compounds of Table 1.

As defined above and described herein, Ring $B^x$ is phenyl, a 4-10 membered saturated or partially unsaturated mono- or bicyclic carbocyclic or heterocyclic ring having 1-3 heteroatoms independently selected from nitrogen, oxygen, and sulfur, or a 5-6 membered heteroaryl ring having 1-4 heteroatoms independently selected from nitrogen, oxygen, and sulfur, wherein Ring $B^x$ is further optionally substituted with 1-2 oxo groups.

In some embodiments, Ring $B^x$ is phenyl. In some embodiments, Ring $B^x$ is a 4-10 membered saturated or partially unsaturated mono- or bicyclic carbocyclic or heterocyclic ring having 1-3 heteroatoms independently selected from nitrogen, oxygen, and sulfur In some embodiments, Ring $B^x$ is a 5-6 membered heteroaryl ring having 1-4 heteroatoms independently selected from nitrogen, oxygen, and sulfur. In some embodiments, Ring $B^x$ is further optionally substituted with 1-2 oxo groups.

In some embodiments, Ring $B^x$ is

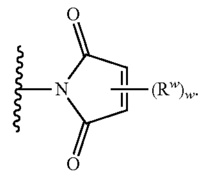

In some embodiments, Ring $B^x$ is

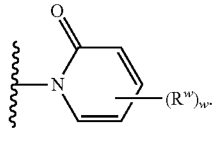

In some embodiments, Ring $B^x$ is

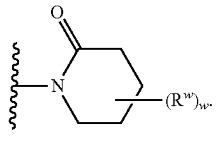

In some embodiments, Ring $B^x$ is

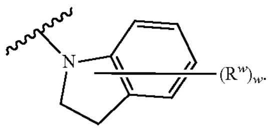

In some embodiments, Ring $B^x$ is

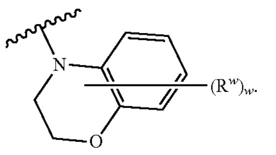

In certain embodiments, Ring $B^x$ is selected from those shown in the compounds of Table 1.

As defined above and described herein, each $R^w$ is independently selected from hydrogen, deuterium, $R^z$, halogen, —CN, —$NO_2$, —OR, —SR, —$NR_2$, —$S(O)_2R$, —$S(O)_2NR_2$, —S(O)R, —$CF_2R$, —$CF_3$, —$CR_2(OR)$, —$CR_2(NR_2)$, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, —N(R)$S(O)_2R$, —OP(O)$R_2$, —OP(O)$(OR)_2$, —OP(O)(OR)$NR_2$, —OP(O)$(NR_2)_2$, and —$SiR_3$.

In some embodiments, $R^w$ is hydrogen. In some embodiments, $R^w$ is deuterium. In some embodiments, $R^w$ is $R^z$. In some embodiments, $R^w$ is halogen. In some embodiments, $R^w$ is —CN. In some embodiments, $R^w$ is —$NO_2$. In some embodiments, $R^w$ is —OR. In some embodiments, $R^w$ is —SR. In some embodiments, $R^w$ is —$NR_2$. In some embodiments, $R^w$ is —$S(O)_2R$. In some embodiments, $R^w$ is —$S(O)_2NR_2$. In some embodiments, $R^w$ is —S(O)R. In some embodiments, $R^w$ is —$CF_2R$. In some embodiments, $R^w$ is —$CF_3$. In some embodiments, $R^w$ is —$CR_2(OR)$. In some embodiments, $R^w$ is —$CR_2(NR_2)$. In some embodiments, $R^w$ is —C(O)R. In some embodiments, $R^w$ is —C(O)OR. In some embodiments, $R^w$ is —C(O)$NR_2$. In some embodiments, $R^w$ is —C(O)N(R)OR. In some embodiments, $R^w$ is —OC(O)R. In some embodiments, $R^w$ is —OC(O)$NR_2$. In some embodiments, $R^w$ is —N(R)C(O)OR. In some embodiments, $R^w$ is —N(R)C(O)R. In some embodiments, $R^w$ is —N(R)C(O)$NR_2$. In some embodiments, $R^w$ is —N(R)$S(O)_2R$. In some embodiments, $R^w$ is —OP(O)$R_2$. In some embodiments, $R^w$ is —OP(O)$(OR)_2$. In some embodiments, $R^w$ is —OP(O)(OR)$NR_2$. In some embodiments, $R^w$ is —OP(O)$(NR_2)_2$. In some embodiments, $R^w$ is —$SiR_3$.

In certain embodiments, $R^w$ is selected from those shown in the compounds of Table 1.

As defined above and described herein, each $R^z$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur.

In some embodiments, $R^z$ is an optionally substituted $C_{1-6}$ aliphatic. In some embodiments, $R^z$ is an optionally substituted phenyl. In some embodiments, $R^z$ is an optionally substituted 4-7 membered saturated or partially unsaturated heterocyclic ring having 1-2 heteroatoms independently selected from nitrogen, oxygen, and sulfur. In some embodiments, $R^z$ is an optionally substituted 5-6 membered heteroaryl ring having 1-4 heteroatoms independently selected from nitrogen, oxygen, and sulfur.

In some embodiments, $R^z$ is

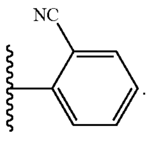 [SMILES: *c1ccccc1C#N]

In some embodiments, $R^z$ is

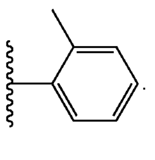

In some embodiments, $R^z$ is

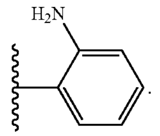 [SMILES: *c1ccccc1N]

In some embodiments, $R^z$ is

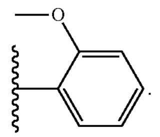 [SMILES: *c1ccccc1OC]

In some embodiments, $R^z$ is

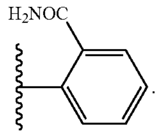 [SMILES: *c1ccccc1C(N)=O]

In some embodiments, Ring $R^z$ is

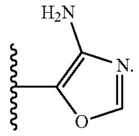

In some embodiments, Ring $R^z$ is

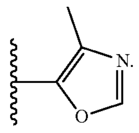

In certain embodiments, $R^z$ is selected from those shown in the compounds of Table 1.

As defined above and described herein, ~~~ is a single or double bond.

In some embodiments, ~~~ is a single bond. In some embodiments, ~~~ is a double bond.

In certain embodiments, ~~~ is selected from those shown in the compounds of Table 1.

As defined above and described herein, w is 0, 1, 2, 3 or 4.

In some embodiments, w is 0. In some embodiments, w is 1. In some embodiments, w is 2. In some embodiments, w is 3. In some embodiments, w is 4.

In certain embodiments, w is selected from those shown in the compounds of Table 1.

As defined above and described herein, x is 0, 1, 2, 3 or 4.

In some embodiments, x is 0. In some embodiments, x is 1. In some embodiments, m is 2. In some embodiments, x is 3. In some embodiments, x is 4.

In certain embodiments, x is selected from those shown in the compounds of Table 1.

As defined above and described herein, y is 0, 1 or 2.

In some embodiments, y is 0. In some embodiments, y is 1. In some embodiments, y is 2.

In certain embodiments, y is selected from those shown in the compounds of Table 1.

In some embodiments, the present invention provides a compound of formula I-bbbb, wherein Ring $A^x$ is benzo, y is 1, $X^1$ is —$CH_2$—, $X^2$ and $X^3$ are —C(O)—, and $Z^1$ and $Z^2$ are carbon atoms as shown, to provide a compound of formula I-bbbb-1:

I-bbbb-1

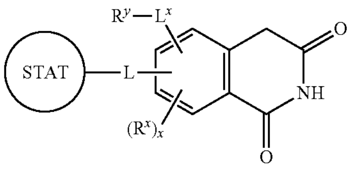

or a pharmaceutically acceptable salt thereof, wherein each of STAT, L, $L^x$, $R^x$, $R^y$, and x is as defined above and described in embodiments herein, both singly and in combination.

In some embodiments, the present invention provides a compound of formula I-bbbb, wherein Ring $A^x$ is imidazolyl, y is 1, $X^1$ is —$CH_2$—, $X^2$ and $X^3$ are —C(O)—, and $Z^1$ and $Z^2$ are carbon atoms as shown, to provide a compound of formula I-bbbb-2:

I-bbbb-2

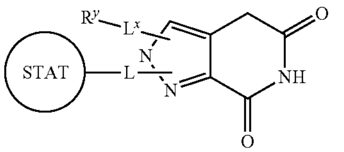

or a pharmaceutically acceptable salt thereof, wherein each of STAT, L, LU, and R is as defined above and described in embodiments herein, both singly and in combination.

In some embodiments, the present invention provides a compound of formula I-bbbb, wherein Ring $A^x$ is imidazolyl, y is 1, $X^1$ is —$CH_2$—, $X^2$ and $X^3$ are —C(O)—, and $Z^1$ and $Z^2$ are carbon atoms as shown, to provide a compound of formula I-bbbb-3:

I-bbbb-3

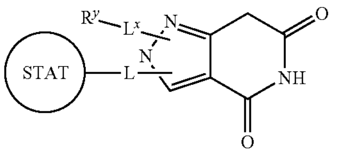

or a pharmaceutically acceptable salt thereof, wherein each of STAT, L, $L^x$, and $R^y$ is as defined above and described in embodiments herein, both singly and in combination.

In some embodiments, the present invention provides a compound of formula I-bbbb, wherein Ring $A^x$ is oxazolyl, y is 1, $X^1$ is —$CH_2$—, $X^2$ and $X^3$ are —C(O)—, and $Z^1$ and $Z^2$ are carbon atoms as shown, to provide a compound of formula I-bbbb-4:

I-bbbb-4

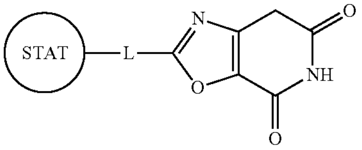

or a pharmaceutically acceptable salt thereof, wherein each of STAT and L is as defined above and described in embodiments herein, both singly and in combination.

In some embodiments, the present invention provides a compound of formula I-bbbb, wherein Ring $A^x$ is benzo, y is 0, $X^2$ and $X^3$ are —C(O)—, and $Z^1$ and $Z^2$ are carbon atoms as shown, to provide a compound of formula I-bbbb-5: STAT LNH (R)X) 0

I-bbbb-5

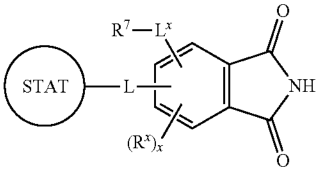

I-bbbb-5 or a pharmaceutically acceptable salt thereof, wherein each of STAT, L, $L^x$, $R^x$, $R^y$, and x is as defined above and described in embodiments herein, both singly and in combination.

In some embodiments, the present invention provides a compound of formula I-bbbb, wherein Ring $A^x$ is benzo, y is 1, $X^1$ is —O—, $X^2$ and $X^3$ are —C(O)—, and $Z^1$ and $Z^2$ are carbon atoms as shown, to provide a compound of formula I-bbbb-6:

I-bbbb-6

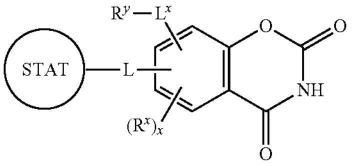

or a pharmaceutically acceptable salt thereof, wherein each of STAT, L, $L^x$, $R^x$, $R^y$, and x is as defined above and described in embodiments herein, both singly and in combination.

In some embodiments, the present invention provides a compound of formula I-bbbb, wherein Ring $A^x$ is benzo, y is 1, $X^1$ is —NR—, $X^2$ and $X^3$ are —C(O)—, and $Z^1$ and $Z^2$ are carbon atoms as shown, to provide a compound of formula I-bbbb-7:

I-bbbb-7

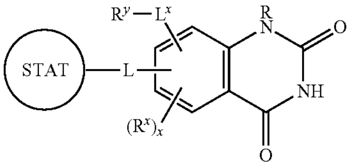

or a pharmaceutically acceptable salt thereof, wherein each of STAT, L, $L^x$, R, $R^x$, $R^y$, and x is as defined above and described in embodiments herein, both singly and in combination.

In some embodiments, the present invention provides a compound of formula I-bbbb, wherein Ring $A^x$ is benzo, y is 1, $X^1$ is —$CF_2$—, $X^2$ and $X^3$ are —C(O)—, and $Z^1$ and $Z^2$ are carbon atoms as shown, to provide a compound of formula I-bbbb-8:

I-bbbb-8

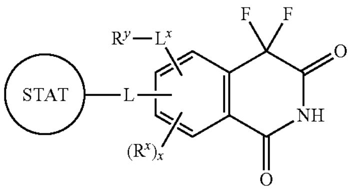

or a pharmaceutically acceptable salt thereof, wherein each of STAT, L, $L^x$, $R^x$, $R^y$, and x is as defined above and described in embodiments herein, both singly and in combination.

In some embodiments, the present invention provides a compound of formula I-bbbb, wherein Ring $A^x$ is benzo, y is 1, $X^1$ is

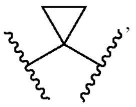 [SMILES: *C1(*)CC1]

$X^2$ and $X^3$ are —C(O)—, and $Z^1$ and $Z^2$ are carbon atoms as shown, to provide a compound of formula I-bbbb-9:

I-bbbb-9

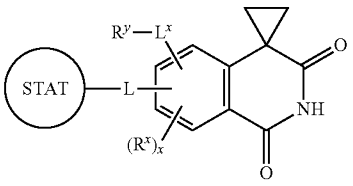

or a pharmaceutically acceptable salt thereof, wherein each of STAT, L, $L^x$, $R^x$, $R^y$, and x is as defined above and described in embodiments herein, both singly and in combination.

In some embodiments, the present invention provides a compound of formula I-bbbb, wherein Ring $A^x$ is pyridyl, y is 1, $X^1$ is —$CH_2$—, $X^2$ and $X^3$ are —C(O)—, and $Z^1$ and $Z^2$ are carbon atoms as shown, to provide a compound of formula I-bbbb-10:

I-bbbb-10

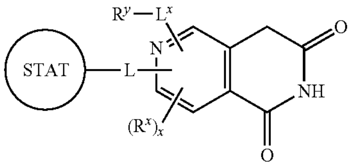

or a pharmaceutically acceptable salt thereof, wherein each of STAT, L, $L^x$, $R^x$, $R^y$, and x is as defined above and described in embodiments herein, both singly and in combination.

In some embodiments, the present invention provides a compound of formula I-bbbb, wherein Ring $A^x$ is pyridyl, y is 1, $X^1$ is —$CH_2$—, $X^2$ and $X^3$ are —C(O)—, and $Z^1$ and $Z^2$ are carbon atoms as shown, to provide a compound of formula I-bbbb-11:

I-bbbb-11

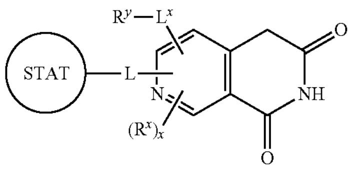

or a pharmaceutically acceptable salt thereof, wherein each of STAT, L, $L^x$, $R^x$, $R^y$, and x is as defined above and described in embodiments herein, both singly and in combination.

In some embodiments, the present invention provides a compound of formula I-bbbb, wherein Ring A is benzo, y is 1, $X^1$, $X^2$ and $X^3$ are —C(O)—, and $Z^1$ and $Z^2$ are carbon atoms as shown, to provide a compound of formula I-bbbb-12:

I-bbbb-12

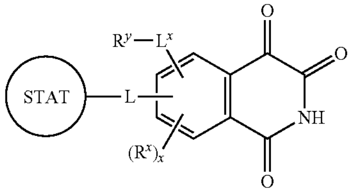

or a pharmaceutically acceptable salt thereof, wherein each of STAT, L, $L^x$, $R^x$, $R^y$, and x is as defined above and described in embodiments herein, both singly and in combination.

In some embodiments, LBM is

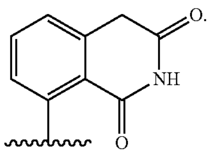 [SMILES: *c1cccc2c1C(=O)NC(=O)C2]

In some embodiments, LBM is

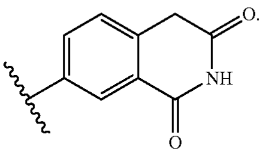 [SMILES: *c1ccc2c(c1)C(=O)NC(=O)C2]

In some embodiments, LBM is

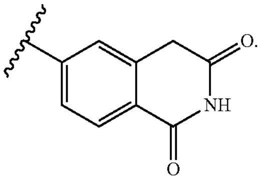 [SMILES: *c1ccc2c(c1)CC(=O)NC2=O]

In some embodiments, LBM is

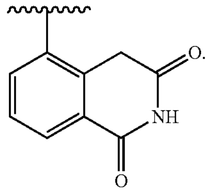 [SMILES: *c1cccc2c1CC(=O)NC2=O]

In some embodiments, LBM is

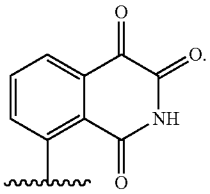 [SMILES: *c1cccc2c1C(=O)NC(=O)C2=O]

In some embodiments, LBM is

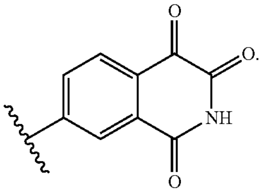 [SMILES: *c1ccc2c(c1)C(=O)NC(=O)C2=O]

In some embodiments, LBM is

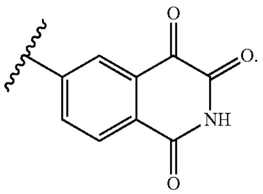 [SMILES: *c1ccc2c(c1)C(=O)C(=O)NC2=O]

In some embodiments, LBM is

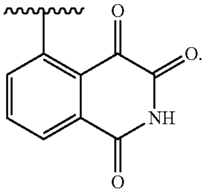 [SMILES: *c1cccc2c1C(=O)C(=O)NC2=O]

In some embodiments, LBM is selected from those in Table 1.

In certain embodiments, the present invention provides a compound of formula I, wherein LBM is a RPN13 binding moiety thereby forming a compound of formula I-cccc:

I-cccc

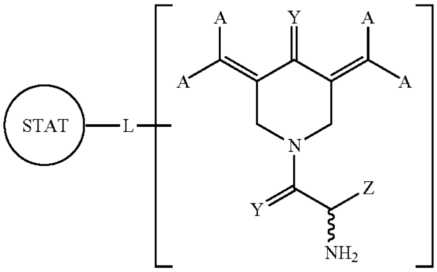

or a pharmaceutically acceptable salt thereof, wherein L and STAT are as defined above and described in embodiments herein, and wherein each of the variables A, Y, and Z is as described and defined in WO 2019/165229, the entirety of each of which is herein incorporated by reference.

In certain embodiments, the present invention provides a compound of formula I, wherein LBM is a Ubrl binding moiety as described in Shanmugasundaram, K. et al, J. Bio. Chem. 2019, doi: 10.1074/jbc.AC119.010790, the entirety of each of which is herein incorporated by reference, thereby forming a compound of formula I-dddd-1 or I-dddd-2:

I-dddd-1

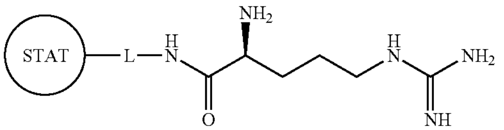

I-dddd-2

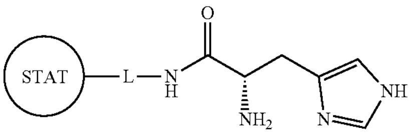

or a pharmaceutically acceptable salt thereof, wherein L and STAT are as defined above and described in embodiments herein.

In certain embodiments, the present invention provides a compound of formula I, wherein LBM is a CRBN binding moiety thereby forming a compound of formula I-eeee:

I-eeee

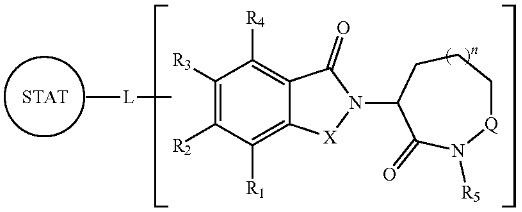

or a pharmaceutically acceptable salt thereof, wherein L and STAT are as defined above and described in embodiments herein, and wherein each of the variables $R_1$, $R_2$, $R_3$, $R_4$, $R_5$, Q, X, and n is as described and defined in US 2019/276474, the entirety of each of which is herein incorporated by reference.

In certain embodiments, the present invention provides a compound of formula I, wherein LBM is a CRBN E3 ubiquitin ligase binding moiety thereby forming a compound of formula I-ffff-1, I-ffff-2, I-ffff-3 or I-ffff-4:

I-ffff-1

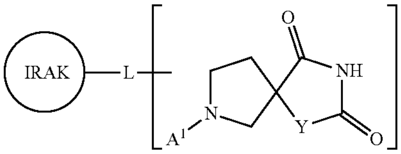

I-ffff-2

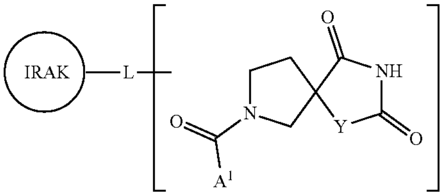

I-ffff-3

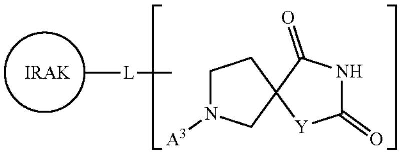

I-ffff-4

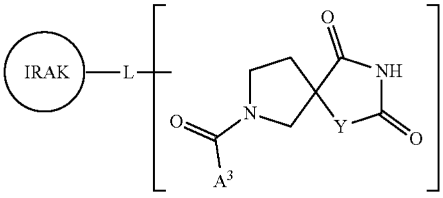

or a pharmaceutically acceptable salt thereof, wherein L and STAT are as defined above and described in embodiments herein, and wherein each of the variables Y, $A^1$, and $A^3$ is as described and defined in WO 2019/236483, the entirety of each of which is herein incorporated by reference.

Degradation Inducing Moiety (DIM)

In certain embodiments, the present invention provides a compound of formula II:

II

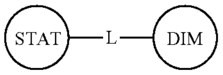

or a pharmaceutically acceptable salt thereof, wherein L and STAT are as described above and herein, and DIM is a degradation inducing moiety selected from LBM, a lysine mimetic, or a hydrogen atom.

In some embodiments, DIM is LBM as described above and herein. In some embodiments, DIM is a lysine mimetic. In some embodiments, the covalent attachment of ubiquitin to one or more members of the STAT protein family (i.e., STAT1, STAT2, STAT3, STAT4, STAT5A, STAT5B, or STAT6) is achieved through the action of a lysine mimetic. In some embodiments, upon the binding of a compound of formula II to STAT1, the moiety that mimics a lysine undergoes ubiquitination thereby marking STAT1 for degradation via the Ubiquitin-Proteasome Pathway (UPP). In some embodiments, upon the binding of a compound of formula II to STAT2, the moiety that mimics a lysine undergoes ubiquitination thereby marking STAT2 for degradation via the Ubiquitin-Proteasome Pathway (UPP). In some embodiments, upon the binding of a compound of formula II to STAT3, the moiety that mimics a lysine undergoes ubiquitination thereby marking STAT3 for degradation via the Ubiquitin-Proteasome Pathway (UPP). In some embodiments, upon the binding of a compound of formula II to STAT4, the moiety that mimics a lysine undergoes ubiquitination thereby marking STAT4 for degradation via the Ubiquitin-Proteasome Pathway (UPP). In some embodiments, upon the binding of a compound of formula II to STAT5A, the moiety that mimics a lysine undergoes ubiquitination thereby marking STAT5A for degradation via the Ubiquitin-Proteasome Pathway (UPP). In some embodiments, upon the binding of a compound of formula II to STAT5B, the moiety that mimics a lysine undergoes ubiquitination thereby marking STAT5B for degradation via the Ubiquitin-Proteasome Pathway (UPP). In some embodiments, upon the binding of a compound of formula II to STAT6, the moiety that mimics a lysine undergoes ubiquitination thereby marking STAT6 for degradation via the Ubiauitin-Proteasome Pathway (UPP).

In some embodiments, DIM is

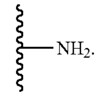

In some embodiments, DIM is

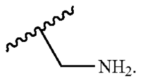

In some embodiments, DIM is

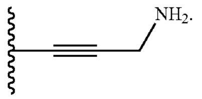

In some embodiments, DIM is selected from those depicted in Table 1A, below.

In some embodiments, the present invention provides the compound of formula I as a compound of formula II-a:

II-a

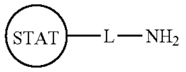

or a pharmaceutically acceptable salt thereof, wherein each of STAT and L is as defined above and described in embodiments herein, both singly and in combination.

In some embodiments, the present invention provides the compound of formula I as a compound of formula II-b:

II-b

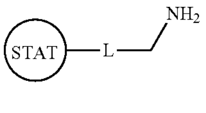

or a pharmaceutically acceptable salt thereof, wherein each of STAT and L is as defined above and described in embodiments herein, both singly and in combination.

In some embodiments, the present invention provides the compound of formula I as a compound of formula II-c:

II-c

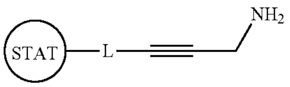

or a pharmaceutically acceptable salt thereof, wherein each of STAT and L is as defined above and described in embodiments herein, both singly and in combination.

In certain embodiments, the present invention provides a compound of Formula II, wherein DIM is a lysine mimetic

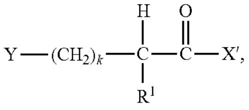

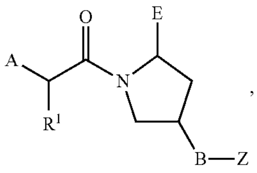

, or

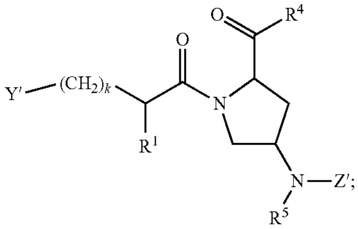

thereby forming a compound of Formulae II-d-1, II-d-2, or II-d-3, respectively:

II-d-1

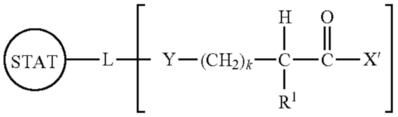

II-d-2

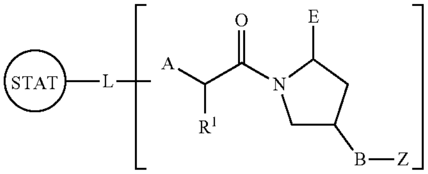

II-d-3

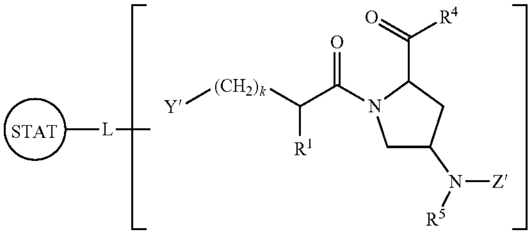

or a pharmaceutically acceptable salt thereof, wherein L and STAT are as defined above and described in embodiments herein, and wherein each of the variables $R^1$, $R^4$, $R^5$, A, B, E, Y, Y', Z, Z', and k are as defined and described in U.S. Pat. No. 7,622,496, the entirety of each of which is herein incorporated by reference.

Hydrogen Atom

In some embodiments, DIM is a hydrogen atom. In some embodiments, the covalent attachment of ubiquitin to one or more members of the STAT protein family (i.e., STAT1, STAT2, STAT3, STAT4, STAT5A, STAT5B, or STAT6) is achieved through a provided compound wherein DIM is a hydrogen atom. In some embodiments, upon the binding of a compound of formula II to STAT1, the moiety being hydrogen effectuates ubiquitination thereby marking STAT1 for degradation via the Ubiquitin-Proteasome Pathway (UPP). In some embodiments, upon the binding of a compound of formula II to STAT2, the moiety being hydrogen effectuates ubiquitination thereby marking STAT2 for degradation via the Ubiquitin-Proteasome Pathway (UPP). In some embodiments, upon the binding of a compound of formula II to STAT3, the moiety being hydrogen effectuates ubiquitination thereby marking STAT3 for degradation via the Ubiquitin-Proteasome Pathway (UPP). In some embodiments, upon the binding of a compound of formula II to STAT4, the moiety being hydrogen effectuates ubiquitination thereby marking STAT4 for degradation via the Ubiquitin-Proteasome Pathway (UPP). In some embodiments, upon the binding of a compound of formula II to STAT5A, the moiety being hydrogen effectuates ubiquitination thereby marking STAT5A for degradation via the Ubiquitin-Proteasome Pathway (UPP). In some embodiments, upon the binding of a compound of formula II to STAT5B, the moiety being hydrogen effectuates ubiquitination thereby marking STAT5B for degradation via the Ubiquitin-Proteasome Pathway (UPP). In some embodiments, upon the binding of a compound of formula II to STAT6, the moiety being hydrogen effectuates ubiquitination thereby marking STAT6 for degradation via the Ubiquitin-Proteasome Pathway (UPP).

In some embodiments, DIM is selected from those depicted in Table 1A, below.

In some embodiments, the present invention provides the compound of formula II wherein DIM is a hydrogen atom, thereby forming a compound of formula II-d-4:

II-d-4

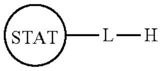

or a pharmaceutically acceptable salt thereof, wherein each of STAT and L is as defined above and described in embodiments herein, both singly and in combination.

STAT Binding Moiety (STAT)

As defined above and described herein, STAT is a STAT binding moiety capable of binding to one or more of STAT1, STAT2, STAT3, STAT4, STAT5A, STAT5B, or STAT6.

In some embodiments, STAT is a STAT binding moiety capable of binding to STAT1. In some embodiments, STAT is a STAT binding moiety capable of binding to STAT2. In some embodiments, STAT is a STAT binding moiety capable of binding to STAT3. In some embodiments, STAT is a STAT binding moiety capable of binding to STAT4. In some embodiments, STAT is a STAT binding moiety capable of binding to STAT5A. In some embodiments, STAT is a STAT binding moiety capable of binding to STAT5B. In some embodiments, STAT is a STAT binding moiety capable of binding to or STAT6.

As defined herein and described below, wherein a formula is depicted using square brackets, e.g,

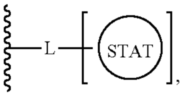

L is attached to a modifiable carbon, oxygen, or nitrogen atom within STAT including substitution or replacement of a defined group in STAT.

In certain embodiments, the present invention provides a compound of formula I or formula II, wherein STAT is a STAT3 binding moiety thereby forming a compound of formula I-ai or II-e:

I-ai

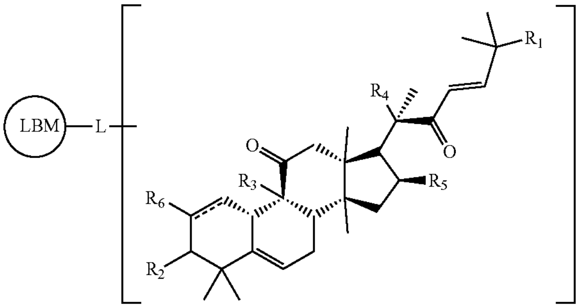

-continued

II-e

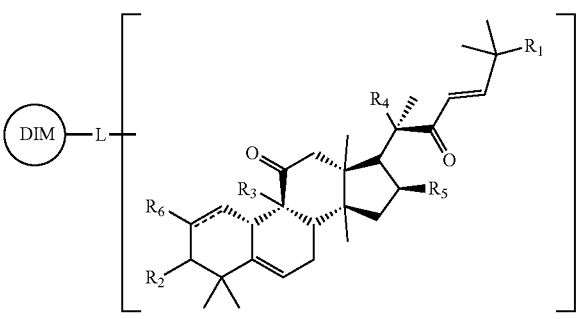

or a pharmaceutically acceptable salt thereof, wherein L and LBM or DIM are as defined above and described in embodiments herein, and wherein each of the variables $R_1$, $R_2$, $R_3$, $R_4$, $R_5$, and $R_6$ is as described and defined in US 2004/0138189, the entirety of each of which is herein incorporated by reference.

In certain embodiments, the present invention provides a compound of formula I or formula II, wherein STAT is a STAT3 binding moiety thereby forming a compound of formula I-aj or II-f:

I-aj

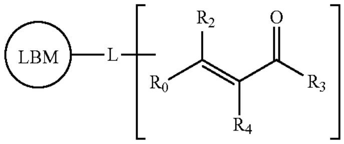

II-f

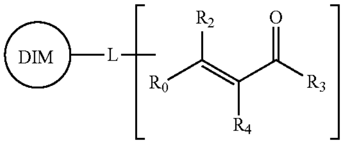

or a pharmaceutically acceptable salt thereof, wherein L and LBM or DIM are as defined above and described in embodiments herein, and wherein each of the variables Ro, $R_2$, $R_3$, and $R_4$ is as described and defined in US 2005/0277680, the entirety of each of which is herein incorporated by reference.

In certain embodiments, the present invention provides a compound of formula I or formula II, wherein STAT is a STAT3 binding moiety thereby forming a compound of formula I-ak or II-g:

I-ak

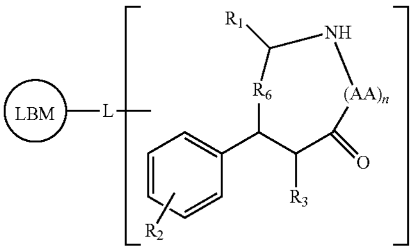

-continued

II-g

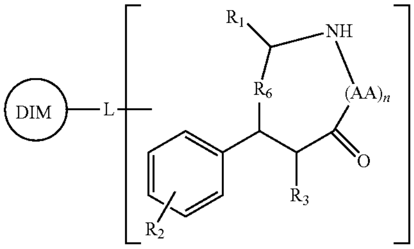

or a pharmaceutically acceptable salt thereof, wherein L and LBM or DIM are as defined above and described in embodiments herein, and wherein each of the variables $R_1$, $R_2$, $R_3$, $R_6$, AA, and n is as described and defined in US 2008/0139456, the entirety of each of which is herein incorporated by reference.

In some embodiments, the invention provides a compound of formula I or formula II, wherein STAT is a STAT3 binding moiety selected from a compound recited in US 2006/0247318 such as, for example:

I-ak-1

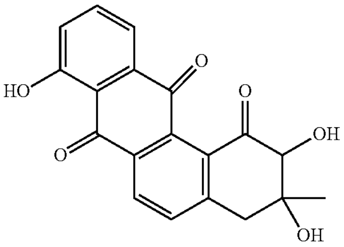

I-ak-2

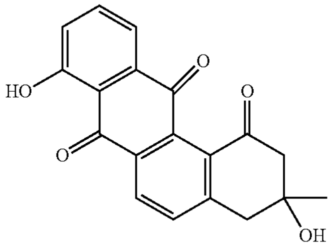

I-ak-3

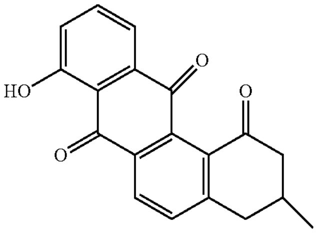

II-h-1

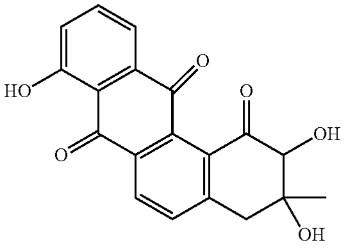

-continued

II-h-2

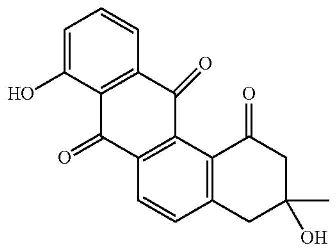

II-h-3

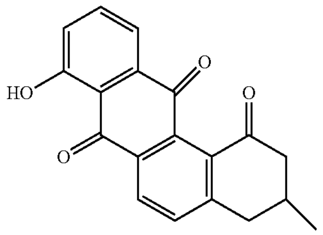

or a pharmaceutically acceptable salt thereof, wherein

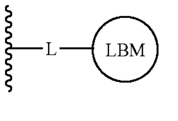

or

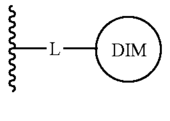

is attached to a modifiable carbon or oxygen atom.

In certain embodiments, the present invention provides a compound of formula I or formula II, wherein STAT is a STAT3 binding moiety thereby forming a compound of formula I-al or II-i:

I-al

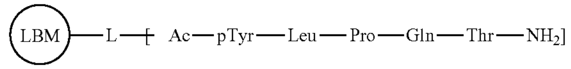

II-i

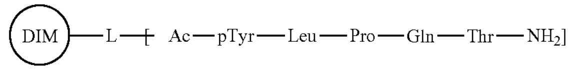

or a pharmaceutically acceptable salt thereof, wherein L and LBM or DIM are as defined above and described in embodiments herein, and wherein the one or more amino acids that have been replaced with a structural analog is as described and defined in US 2007/0010428, the entirety of each of which is herein incorporated by reference.

In certain embodiments, the present invention provides a compound of formula I or formula II, wherein STAT is a STAT3 binding moiety thereby forming a compound of formula I-am or II-j:

I-am

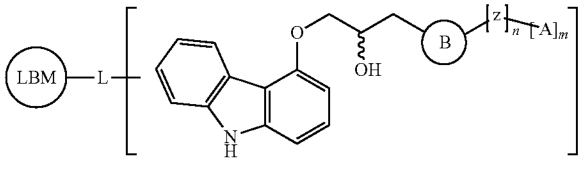

-continued

II-j

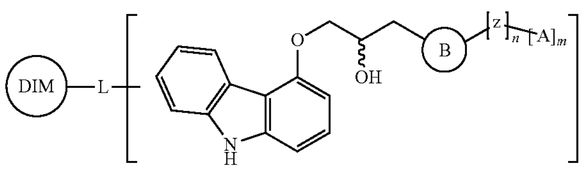

or a pharmaceutically acceptable salt thereof, wherein L and LBM or DIM are as defined above and described in embodiments herein, and wherein each of the variables A, B, Z, n, and m is as described and defined in WO 2007/042912 and U.S. Pat. No. 7,786,142, the entirety of each of which is herein incorporated by reference.

In some embodiments, the present invention provides a compound of formula I or formula II, wherein STAT is a STAT3 binding moiety selected from a compound recited in WO 2007/136858 such as, for example S31-201 (shown in FIG. 7), NSC-59263 (shown in FIG. 8), NSC-42067 (shown in FIG. 9), Formula A (shown in FIG. 10), Formula B (shown in FIG. 11), Formula C (shown in FIG. 12A), Formula D (FIG. 12B), Formula E (FIG. 12C), Formula F (FIG. 12D), NSC 75912 (shown in FIG. 50), NSC 11421 (shown in FIG. 49), NSC 91529 (shown in FIG. 51), NSC 263435 (shown in FIG. 48), HL2-006-1 (shown in FIG. 13), HL2-006-2 (shown in FIG. 14), HL2-006-3 (shown in FIG. 15), HL2-006-4 (shown in FIG. 16), HL2-006-5 (shown in FIG. 17), HL2-011-1 (shown in FIG. 18), HL2-011-2 (shown in FIG. 19), HL2-01 1-3 (shown in FIG. 20), HL2-01 1-4 (shown in FIG. 21), HL2-011-5 (shown in FIG. 22), BG2069-1 (shown in FIG. 23), HL2-011-6 (shown in FIG. 24), HL2-011-7 (shown in FIG. 25), HL2-005 (shown in FIG. 26), HL2-003 (shown in FIG. 27), BG2066 (shown in FIG. 28), BG2074 (shown in FIG. 29), BG3004 (shown in FIG. 30), BG3006A (shown in FIG. 31), BG3006B (shown in FIG. 32), BG3006D (shown in FIG. 33), BG3009 (shown in FIG. 34), RPM381 (shown in FIG. 35), RPM384 (shown in FIG. 35), RPM385 (shown in FIG. 35), RPM405 (shown in FIG. 36), RPM411 (shown in FIG. 36), RPM407 (shown in FIG. 37), RPM412 (shown in FIG. 37), RPM408 (shown in FIG. 38), RPM410 (shown in FIG. 38), RPM415 (shown in FIG. 39), RPM416 (shown in FIG. 39), RPM418 (shown in FIG. 40), RPM418-A (shown in FIG. 40), RPM427 (shown in FIG. 41), RPM431 (shown in FIG. 42), RPM432 (shown in FIG. 43), RPM444 (shown in FIG. 44) RPM448 (shown in FIG. 44), RPM445 (shown in FIG. 45), RPM447 (shown in FIG. 45), RPM452 (shown in FIG. 46) and RPM202, or a pharmaceutically acceptable salt thereof, wherein

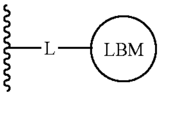

or

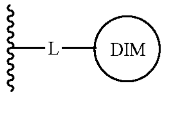

is attached to a modifiable carbon, oxygen, nitrogen or sulfur atom.

In certain embodiments, the present invention provides a compound of formula I or formula II, wherein STAT is a STAT3 or STAT5 binding moiety thereby forming a compound of formula I-an or II-k:

I-an

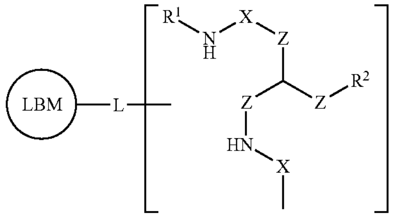

II-k

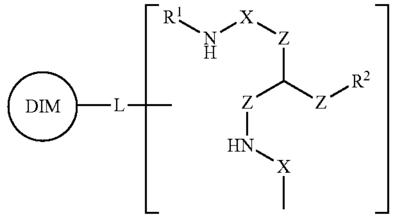

or a pharmaceutically acceptable salt thereof, wherein L and LBM or DIM are as defined above and described in embodiments herein, and wherein each of the variables $R_1$, $R_2$, X, and Z is as described and defined in U.S. Pat. No. 7,960,434, the entirety of each of which is herein incorporated by reference.

In some embodiments, the present invention provides a compound of formula I or formula II, wherein STAT is a STAT3 binding moiety selected from a compound recited in US 2006/0247318 such as, for example:

II-1

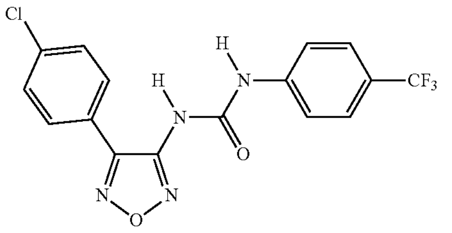

or a pharmaceutically acceptable salt thereof, wherein

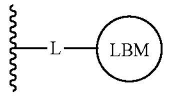

or

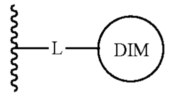

is attached to a modifiable carbon, nitrogen, or oxygen atom.

In certain embodiments, the present invention provides a compound of formula I or formula II, wherein STAT is a STAT3 or STAT5 binding moiety thereby forming a compound of formula I-ap or II-m:

I-ap

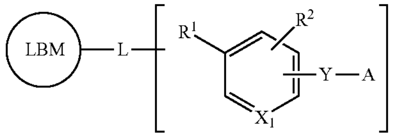

-continued

II-m

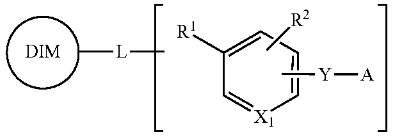

or a pharmaceutically acceptable salt thereof, wherein L and LBM or DIM are as defined above and described in embodiments herein, and wherein each of the variables $R^1$, $R^2$, A, $X_1$, and Y is as described and defined in U.S. Pat. No. 8,263,599, the entirety of each of which is herein incorporated by reference.

In certain embodiments, the present invention provides a compound of formula I or formula II, wherein STAT is a STAT3 binding moiety thereby forming a compound of formula I-aq or II-n:

I-aq

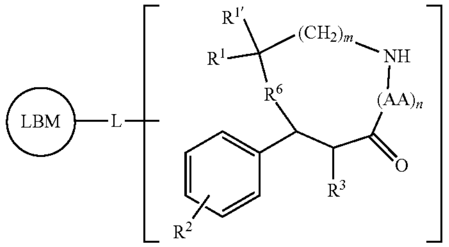

II-n

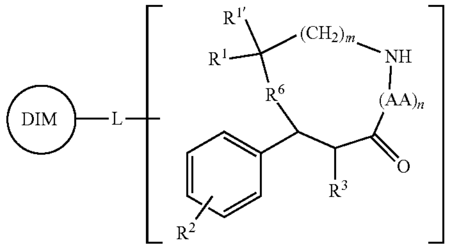

or a pharmaceutically acceptable salt thereof, wherein L and LBM or DIM are as defined above and described in embodiments herein, and wherein each of the variables $R^1$, $R^{1'}$, $R^2$, $R^3$, $R^6$, AA, and n is as described and defined in WO 2008/067270, the entirety of each of which is herein incorporated by reference.

In certain embodiments, the present invention provides a compound of formula I or formula II, wherein STAT is a STAT1, STAT3 or STAT5 binding moiety thereby forming a compound of formula I-ar-1, I-ar-2, I-ar-3, I-ar-4, II-o-1, II-o-2, II-o-3, or II-o-4:

I-ar-1

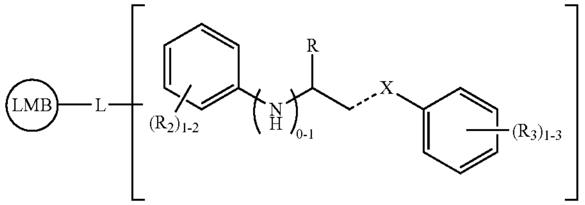

-continued

I-ar-2

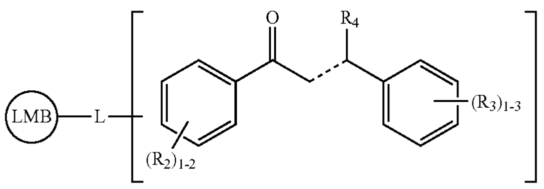

I-ar-3

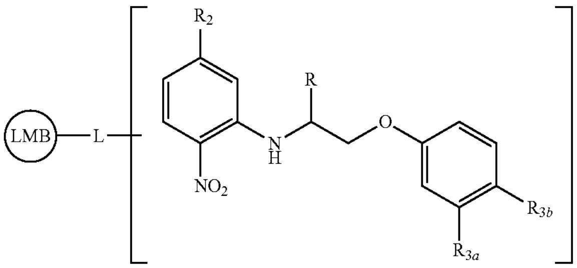

I-ar-4

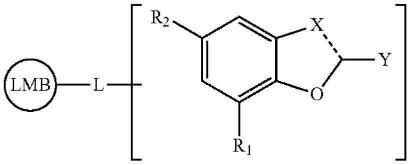

II-o-1

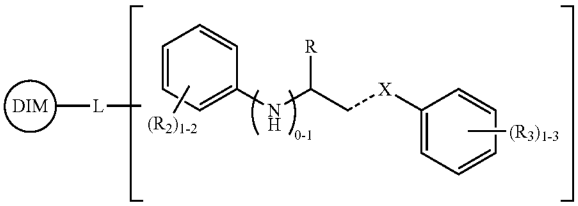

II-o-2

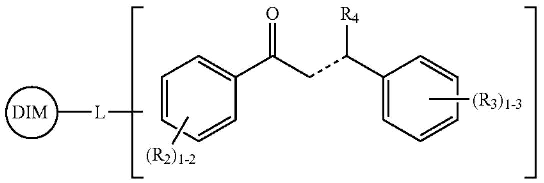

II-o-3

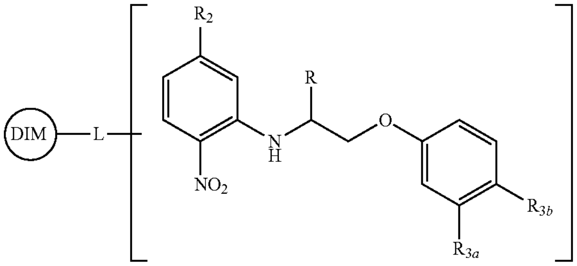

II-o-4

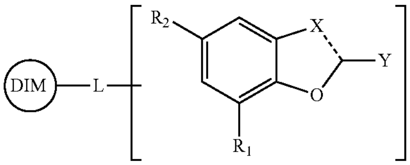

or a pharmaceutically acceptable salt thereof, wherein L and LBM or DIM are as defined above and described in embodiments herein, and wherein each of the variables R, $R^1$, $R^2$, $R^3$, $R^{3a}$, $R^{3b}$, $R^4$, x, and y is as described and defined in WO 2008/156644 and US 2011/0144043, the entirety of each of which is herein incorporated by reference.

In some embodiments, the present invention provides a compounds of formula I or formula II, wherein STAT is a STAT3 binding moiety selected from a compound recited in WO 2009/032338 such as, for example apratoxin A, apratoxin B, apratoxin C, E-dehydroapratoxin A, apratoxin D, apratoxin E, and described analogs thereof, or a pharmaceutically acceptable salt thereof, wherein

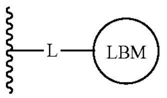 or 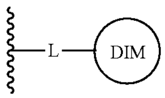

is attached to a modifiable carbon, nitrogen, or oxygen atom.

In certain embodiments, the present invention provides a compound of formula I or formula II, wherein STAT is a STAT3 binding moiety thereby forming a compound of formula I-as or II-p:

I-as

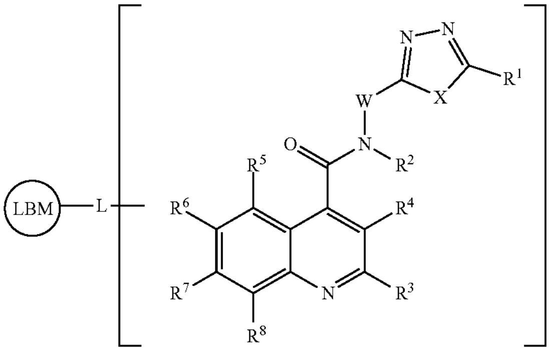

II-p

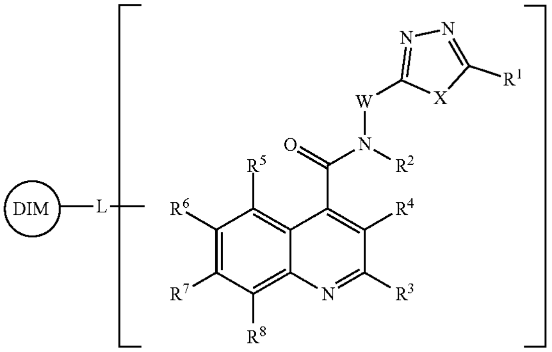

or a pharmaceutically acceptable salt thereof, wherein L and LBM or DIM are as defined above and described in embodiments herein, and wherein each of the variables $R^1$, $R^2$, R, $R_4$, R, R, $R^7$, W, and X is as described and defined in WO 2010/004761 and U.S. Pat. No. 8,446,290, the entirety of each of which is herein incorporated by reference.

In certain embodiments, the present invention provides a compound of formula I or formula II, wherein STAT is a STAT3 binding moiety thereby forming a compound of formula I-at or II-q:

I-at

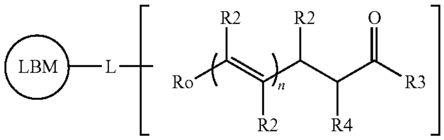

II-q

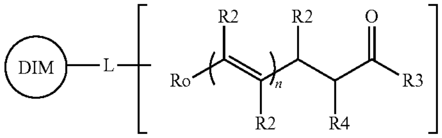

or a pharmaceutically acceptable salt thereof, wherein L and LBM or DIM are as defined above and described in embodiments herein, and wherein each of the variables Ro, $R_2$, $R_3$, $R_4$, and n is as described and defined in WO 2010/005807 and U.S. Pat. No. 8,143,412, the entirety of each of which is herein incorporated by reference.

In certain embodiments, the present invention provides a compound of formula I or formula II, wherein STAT is a STAT3 binding moiety thereby forming a compound of formula I-au or II-r:

I-au

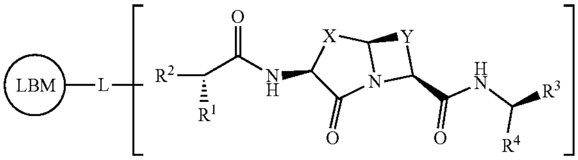

II-r

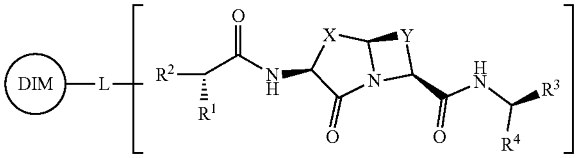

or a pharmaceutically acceptable salt thereof, wherein L and LBM or DIM are as defined above and described in embodiments herein, and wherein each of the variables $R^1$, $R^2$, $R^3$, $R^4$, X, and Y is as described and defined in WO 2010/077589 and US 2011/0319362, the entirety of each of which is herein incorporated by reference.

In certain embodiments, the present invention provides a compound of formula II, wherein STAT is a STAT3 binding moiety thereby forming a compound of formula II-r'-1, II-r'-2, II-r'-3, or II-r'-4:

II-r'-1

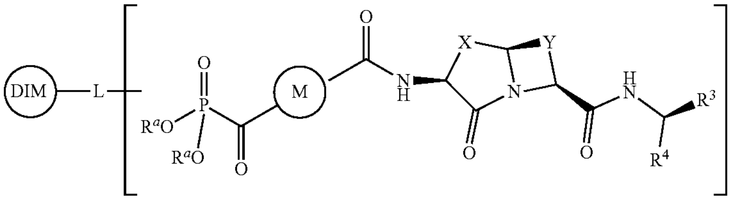

II-r'-2

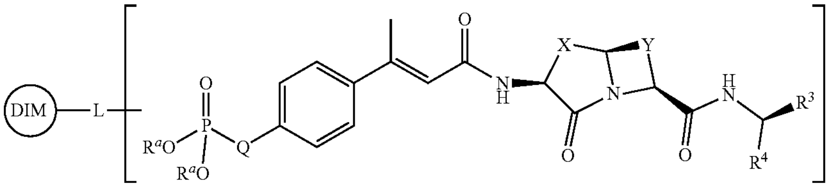

II-r'-3

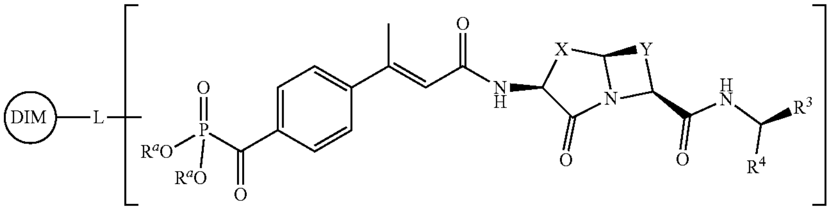

II-r'-4

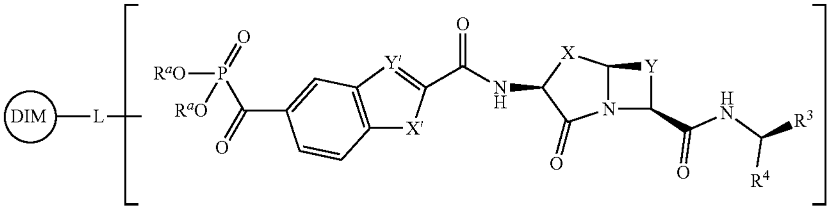

-continued

II-r'-5

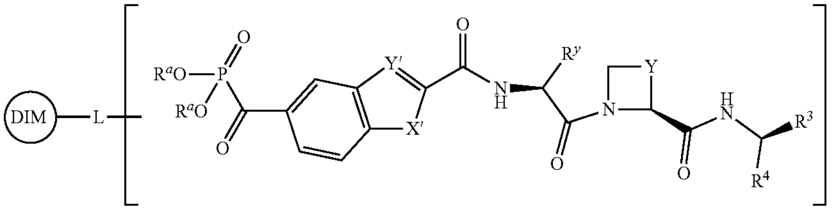

II-r'-6

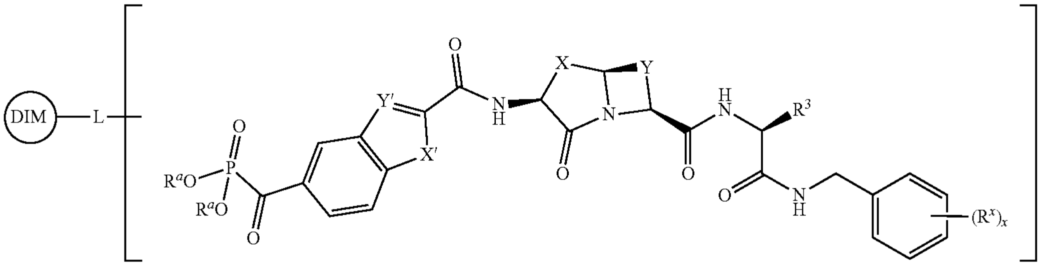

II-r'-7

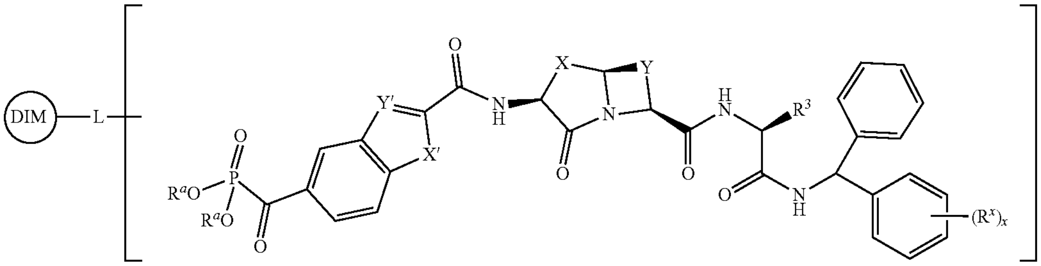

or a pharmaceutically acceptable salt thereof, wherein L and DIM are as defined above and described in embodiments herein, and wherein:

Ring M is an optionally substituted ring selected from phenyl, naphthyl, a 5 to 10-membered heteroaryl containing 1-4 heteroatoms independently selected from nitrogen, oxygen, or sulfur, a 5 to 11-membered saturated or partially unsaturated carbocyclyl, and a 5 to 11-membered saturated or partially unsaturated heterocyclyl with 1-4 heteroatoms independently selected from boron, nitrogen, oxygen, silicon, or sulfur;

each $R^x$ and $R^y$ is independently hydrogen, $R^A$, halogen, —CN, —$NO_2$, —OR, —SR, —$NR_2$, —$S(O)_2R$, —$S(O)_2NR_2$, —S(O)R, —$CFR_2$, —$CF_2R$, —$CF_3$, —$CR_2(OR)$, —$CR_2(NR_2)$, —C(O)R, —C(O)OR, —C(O)$NR_2$, —C(S)$NR_2$, —C(O)N(R)OR, —OC(O)R, —OC(O)$NR_2$, —N(R)C(O)OR, —N(R)C(O)R, —N(R)C(O)$NR_2$, —N(R)$S(O)_2R$, —$N^+(O^-)R_2$, —OP(O)$R_2$, —OP(O)$(OR)_2$, —OP(O)(OR)$NR_2$, —OP(O)$(NR_2)_2$, —P(O)$R_2$, —$SiR_3$, —$SF_5$, —Si(OR)$R_2$, or

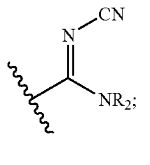

each RA is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each R is independently hydrogen, or an optionally substituted group selected from $C_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same carbon or nitrogen are optionally taken together with their intervening atoms to form a 4-7 membered saturated, partially unsaturated, or heteroaryl ring having 0-3 heteroatoms, in addition to the carbon or nitrogen, independently selected from nitrogen, oxygen, and sulfur; and each of the variables $R_3$, $R_4$, $R^a$, Q, X, X', Y, and Y' is as described and defined in WO 2010/077589 and US 2011/0319362, the entirety of each of which is herein incorporated by reference.

In some embodiments, $R^x$ is hydrogen. In some embodiments, $R^x$ is methanesulfonyl. In some embodiments, $R^x$ is isopropyl. In some embodiments, $R^x$ is isobutyl.

In certain embodiments, the present invention provides a compound of formula I or formula II, wherein STAT is a STAT3 binding moiety thereby forming a compound of formula I-av or II-s:

I-av

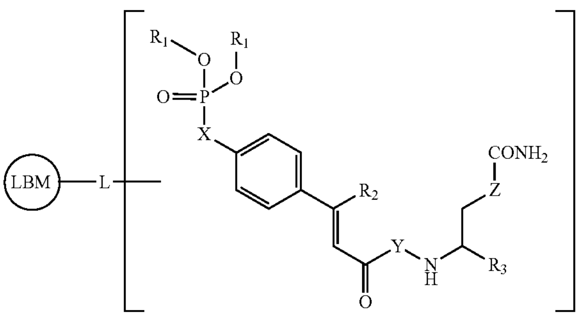

II-s

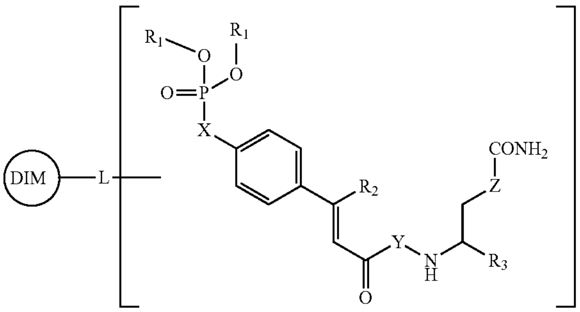

or a pharmaceutically acceptable salt thereof, wherein L and LBM or DIM are as defined above and described in embodiments herein, and wherein each of the variables $R^1$, $R^2$, $R^3$, Z, X, and Y is as described and defined in WO 2010/118309 and U.S. Pat. No. 8,841,257, the entirety of each of which is herein incorporated by reference.

In certain embodiments, the present invention provides a compound of formula II, wherein STAT is a STAT3 binding moiety thereby forming a compound of formula II-s'-1, II-s'-2, or II-s'-3:

II-s'-1

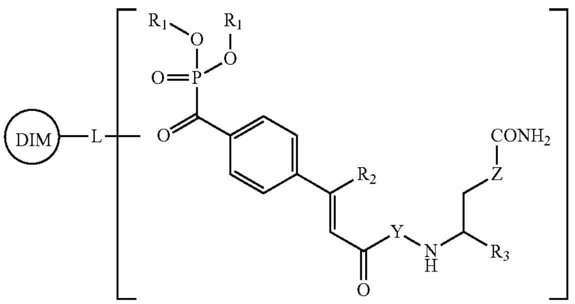

II-s'-2

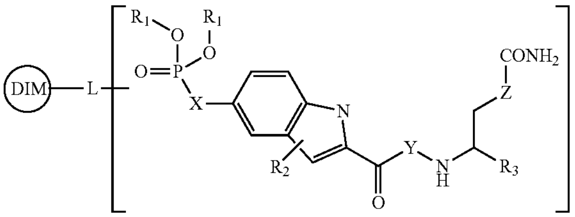

II-s'-3

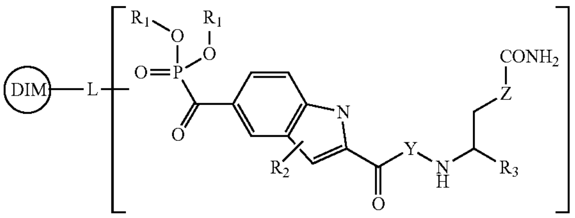

or a pharmaceutically acceptable salt thereof, wherein L and DIM are as defined above and described in embodiments herein, and wherein each of the variables $R^1$, $R^2$, $R^3$, Z, X, and Y is as described and defined in WO 2010/118309 and U.S. Pat. No. 8,841,257, the entirety of each of which is herein incorporated by reference.

In certain embodiments, the present invention provides a compound of formula II-r":

II-r"

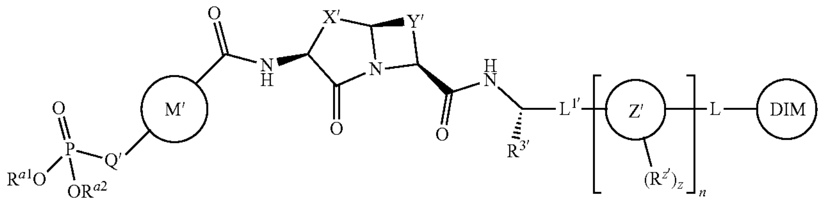

or a pharmaceutically acceptable salt thereof, wherein L and DIM are as defined above and described in embodiments herein, and wherein:

$L^{1'}$ is a covalent bond or a bivalent, saturated or partially unsaturated, straight or branched $C_{1-5}$ hydrocarbon chain, wherein 0-3 methylene units of $L^1$ are independently replaced by —O—, —NR—, —CRF—, —$CF_2$—, —C(O)—, —S—, —S(O)—, or —$S(O)_2$—;

each R is independently hydrogen, or an optionally substituted group selected from $C_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same carbon or nitrogen are optionally taken together with their intervening atoms to form an optionally substituted 4-11 membered saturated or partially unsaturated monocyclic, bicyclic, bridged bicyclic, or spirocyclic carbocyclic or heterocyclic ring having 1-3 heteroatoms, in addition to the carbon or nitrogen from which the two R groups are attached, independently selected from nitrogen, oxygen, and sulfur;

X' is an optionally substituted —$(CH_2)_x$—, wherein 1-2 methylenes of X' is optionally replaced with a bivalent group selected from —NR—, —N(COR)—, —N($CO_2$R)—, —N($SO_2$R)—, —N($CONR_2$)—, and —N($SO_2NR_2$)—, wherein:

x is 1, 2, 3, 4, or 5;

Y' is an optionally substituted —$(CH_2)_y$—, wherein: y is 1, 2, or 3;

$R^{3'}$ is hydrogen or $R^A$;

each $R^A$ is independently an optionally substituted group selected from $C_{1-6}$ aliphatic, phenyl, a 4-7 membered saturated or partially unsaturated carbocyclic or heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring M' is an optionally substituted bivalent ring selected from phenylenyl, naphthylenyl, a 5-10 membered heteroarylenyl containing 1-4 heteroatoms independently selected from nitrogen, oxygen, or sulfur, a 5-11 membered saturated or partially unsaturated carbocyclylenyl or heterocyclylenyl with 1-4 heteroatoms independently selected from nitrogen, oxygen, or sulfur;

Q' is a bivalent moiety selected from —O—, —$CR_2$—, —$CF_2$—, —CFR—, —C(O)—, —$OCR_2$—, and —C(S)—;

$R^{a1}$ and $R^{a2}$ are each independently hydrogen or $R^A$;

Ring Z' is a bivalent ring selected from phenylenyl, a 4-7 membered saturated or partially unsaturated carbocyclylenyl or heterocyclylenyl having 1-2 heteroatoms independently selected from nitrogen, oxygen, and sulfur, and a 5-6 membered heteroarylenyl having 1-4 heteroatoms independently selected from nitrogen, oxygen, and sulfur;

$R^{z'}$ is hydrogen, $R^A$, halogen, —CN, —$NO_2$, —OR, —SR, —$NR_2$, —$SiR_3$, —$S(O)_2R$, —$S(O)_2NR_2$, —S(O)R, —C(O)R, —C(O)OR, —C(O)$NR_2$, —C(O)NROR, —$CR_2$NRC(O)R, —$CR_2$NRC(O)$NR_2$, —OC(O)R, —OC(O)$NR_2$, —OP(O)$R_2$, —OP(O)$(OR)_2$, —OP(O)(OR)$NR_2$, —OP(O)$(NR_2)_2$, —NRC(O)OR, —NRC(O)R, —NRC(O)$NR_2$, —NRS$(O)_2$R, —NP(O)$R_2$, —NRP(O)$(OR)_2$, —NRP(O)(OR)$NR_2$, —NRP(O)$(NR_2)_2$, or —NRS$(O)_2$R;

z is 0, 1, 2, 3, or 4; and n is 0 or 1.

In certain embodiments, the present invention provides a compound of formula II-r"-1:

II-r"-1

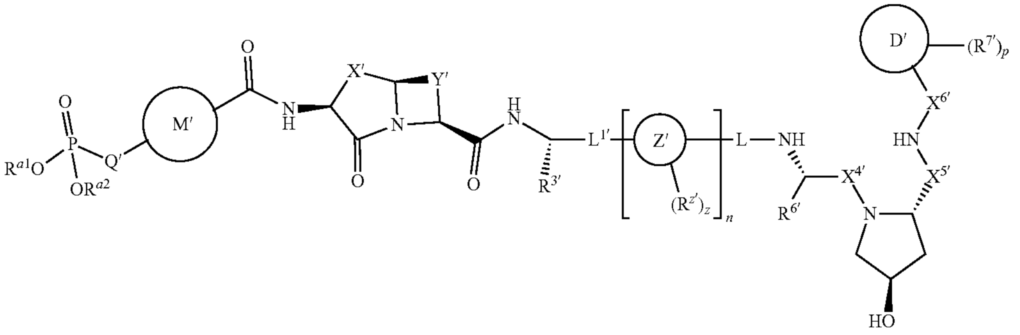

or a pharmaceutically acceptable salt thereof, wherein:

$X^{4'}$, $X^{5'}$, and $X^{6'}$ are each independently a bivalent moiety selected from a covalent bond, —$CR_2$—, —C(O)—, —C(S)—, —O—, —S(O)—, —$S(O)_2$—,

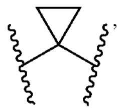, or 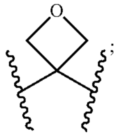;

each R is independently hydrogen, or an optionally substituted group selected from $C_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same carbon or nitrogen are optionally taken together with their intervening atoms to form an optionally substituted 4-11 membered saturated or partially unsaturated monocyclic, bicyclic, bridged bicyclic, or spirocyclic carbocyclic or heterocyclic ring having 1-3 heteroatoms, in addition to the carbon or nitrogen from which the two R groups are attached, independently selected from nitrogen, oxygen, and sulfur;

$R^{6'}$ is hydrogen or $R^A$;

each $R^A$ is independently an optionally substituted group selected from $C_{1-6}$ aliphatic, phenyl, a 4-7 membered saturated or partially unsaturated carbocyclic or heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring D' is selected from phenyl, a 4-11 membered saturated or partially unsaturated monocyclic, bicyclic, bridged bicyclic, or spirocyclic carbocyclic or heterocyclic ring having 1-3 heteroatoms independently selected from nitrogen, oxygen, and sulfur, and a 5-6 membered heteroaryl with 1-4 heteroatoms independently selected from nitrogen, oxygen or sulfur;

$R^{7'}$ is hydrogen, $R^A$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)NROR, —OC(O)R, —OC(O)$NR_2$, —NRC(O)OR, —NRC(O)R, —NRC(O)$NR_2$, or —$NRS(O)_2R$;

p is 0, 1, 2, 3, or 4;

L is a covalent bond or a bivalent, saturated or partially unsaturated, straight or branched $C_{1-20}$ hydrocarbon chain, wherein 0-6 methylene units of L are independently replaced by -Cy-, —O—, —NR—, —CRF—, —$CF_2$—, —C(O)—, —S—, —S(O)—, —$S(O)_2$—, —$SiR_2$—, —Si(OH)R—, —$Si(OH)_2$—, —P(O)OR—, —P(O)R—, or —P(O)$NR_2$—, wherein:

each -Cy- is independently an optionally substituted bivalent ring selected from phenylenyl, an 8-10 membered bicyclic arylenyl, a 4-7 membered saturated or partially unsaturated carbocyclylenyl, a 4-11 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-11 membered saturated or partially unsaturated spiro heterocyclylenyl having 1-3 heteroatoms independently selected from nitrogen, oxygen, and sulfur, an 8-10 membered bicyclic saturated or partially unsaturated heterocyclylenyl having 1-3 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;

$L^{1'}$ is a covalent bond or a bivalent, saturated or partially unsaturated, straight or branched $C_{1-5}$ hydrocarbon chain, wherein 0-3 methylene units of $L^1$ are independently replaced by —O—, —NR—, —CRF—, —$CF_2$—, —C(O)—, —S—, —S(O)—, or —$S(O)_2$—;

$X^1$ is an optionally substituted —$(CH_2)_x$—, wherein 1-2 methylenes of $X^1$ is optionally replaced with a bivalent group selected from —NR—, —N(COR)—, —$N(CO_2R)$—, —$N(SO_2R)$—, —$N(CONR_2)$—, and —$N(SO_2NR_2)$—, wherein:

x is 1, 2, 3, 4, or 5;

Y' is an optionally substituted —$(CH_2)_y$—, wherein: y is 1, 2, or 3;

$R^{u'}$ is hydrogen or $R^A$;

Ring M' is an optionally substituted bivalent ring selected from phenylenyl, naphthylenyl, a 5-10 membered heteroarylenyl containing 1-4 heteroatoms independently selected from nitrogen, oxygen, or sulfur, a 5-11 membered saturated or partially unsaturated carbocyclylenyl or heterocyclylenyl with 1-4 heteroatoms independently selected from nitrogen, oxygen, or sulfur;

Q' is a bivalent moiety selected from —O—, —$CR_2$—, —$CF_2$—, —CFR—, —C(O)—, —$OCR_2$—, and —C(S)—;

$R^{a1}$ and $R^{a2}$ are each independently hydrogen or $R^A$;

Ring Z' is a bivalent ring selected from phenylenyl, a 4-7 membered saturated or partially unsaturated carbocyclylenyl or heterocyclylenyl having 1-2 heteroatoms independently selected from nitrogen, oxygen, and sulfur, and a 5-6 membered heteroarylenyl having 1-4 heteroatoms independently selected from nitrogen, oxygen, and sulfur;

$R^{z'}$ is hydrogen, $R^A$, halogen, —CN, —$NO_2$, —OR, —SR, —$NR_2$, —$SiR_3$, —$S(O)_2R$, —$S(O)_2NR_2$, —S(O)R, —C(O)R, —C(O)OR, —C(O)$NR_2$, —C(O)NROR, —$CR_2$NRC(O)R, —$CR_2$NRC(O)$NR_2$, —OC(O)R, —OC(O)$NR_2$, —OP(O)$R_2$, —OP(O)$(OR)_2$, —OP(O)(OR)$NR_2$, —OP(O)$(NR_2)_2$, —NRC(O)OR, —NRC(O)R, —NRC(O)$NR_2$, —$NRS(O)_2R$, —NP(O)$R_2$, —NRP(O)$(OR)_2$, —NRP(O)(OR)$NR_2$, —NRP(O)$(NR_2)_2$, or —$NRS(O)_2R$;

z is 0, 1, 2, 3, or 4; and n is 0 or 1.

In some embodiments the resent invention provides a compound of formula II-r"-1, wherein Ring D' is phenyl, p is 1, $R^{7'}$ is

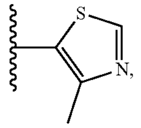

n is 1, and Q' is —C(O)— as shown, to provide a compound of formula II-r"-2:

II-r''-2

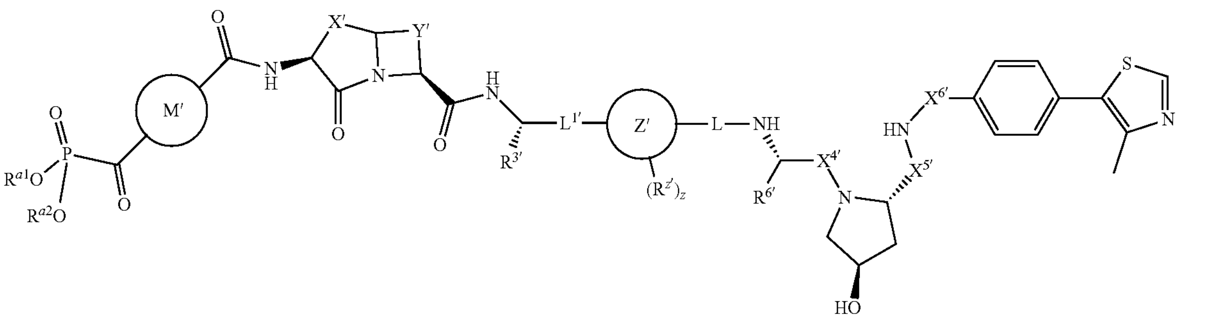

or a pharmaceutically acceptable salt thereof, wherein each of $X^{4'}$, $X^{5'}$, $X^{6'}$, $R^{3'}$, $R^{6'}$, L, $L^{1'}$, Ring M', Ring Z', X', Y', $R^{a1}$, $R^{a2}$, $R^{z'}$, and z is as defined above and described in embodiments herein, both singly and in combination.

In some embodiments, the present invention provides a compound of formula II-r''-1, wherein Ring D' is phenyl, p is 1, $R^{7'}$ is

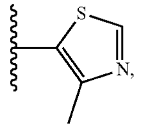 [SMILES: *c1scnc1C]

$R^{3'}$ is

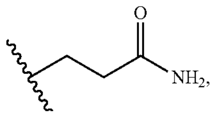 [SMILES: *CCC(N)=O]

n is 1, and $X^{4'}$, $X^{5'}$, and Q' are —C(O) as shown, to provide a compound of formula II-r''-3:

II-r''-3

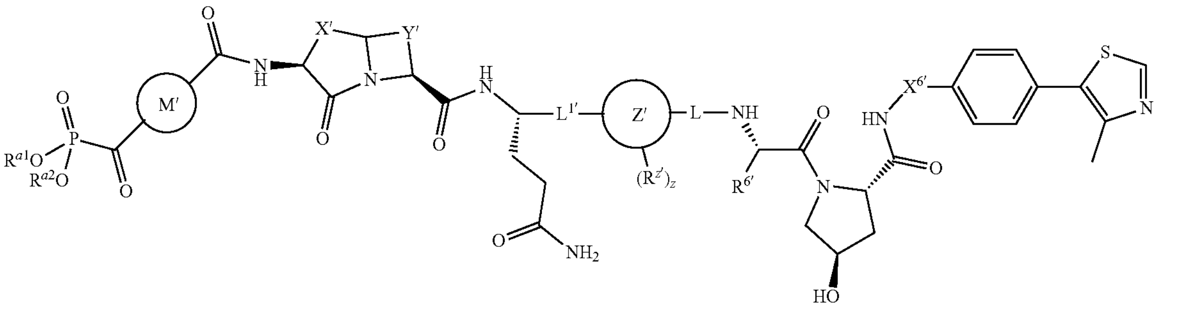

or a pharmaceutically acceptable salt thereof, wherein each of $X^{6'}$, $R^{6'}$, L, $L^{1'}$, Ring M', Ring Z', X', Y', $R^{a1}$, $R^{a2}$, $R^{z'}$, and z is as defined above and described in embodiments herein, both singly and in combination.

In some embodiments, the present invention provides a compound of formula II-r''-1, wherein Ring D' is phenyl, p is 1, $R^{7'}$

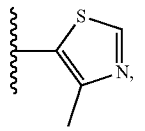 [SMILES: *c1scnc1C]

X' is

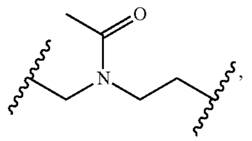 [SMILES: *CCN(C*)C(C)=O]

Y' is

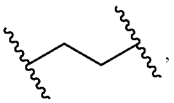 [SMILES: *CC*]

n is 1, and $X^{4'}$, $X^{5'}$, and Q' are —C(O)— as shown, to provide a compound of formula II-r"-4:

II-r''-4

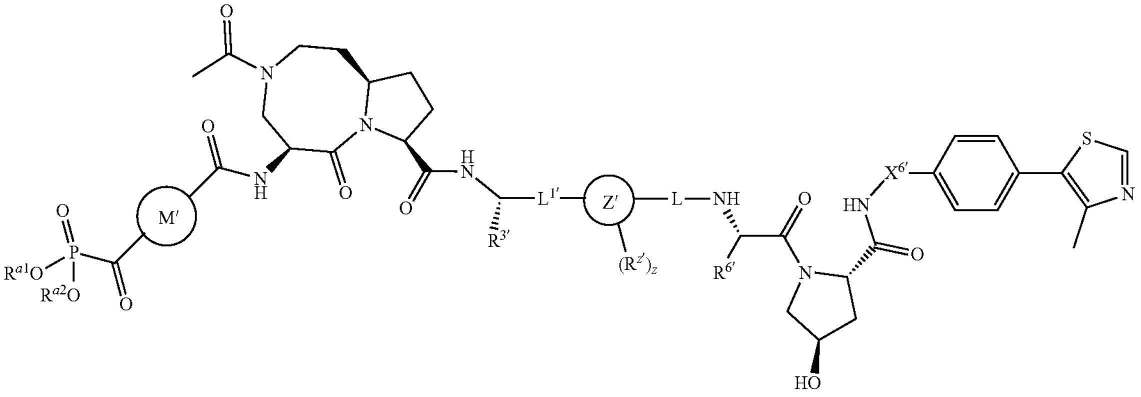

or a pharmaceutically acceptable salt thereof, wherein each of $X^{6'}$, $R^{3'}$, $R^{6'}$, L, $L^{1'}$, Ring M', Ring Z', $R^{a1}$, $R^{a2}$, $R^{z'}$, and z is as defined above and described in embodiments herein, both singly and in combination.

In some embodiments, the present invention provides a compound of formula II-r"-1, wherein Ring D' is phenyl, p is 1, $R^{7'}$ is

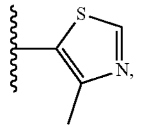

n is 1, Ring M' is

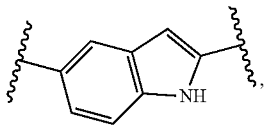 [SMILES: *c1ccc2[nH]c(*)cc2c1]

and $X^{4'}$, $X^{5'}$, and Q' are —C(O)—as shown, to provide a compound of formula II-r"-5:

II-r"-5

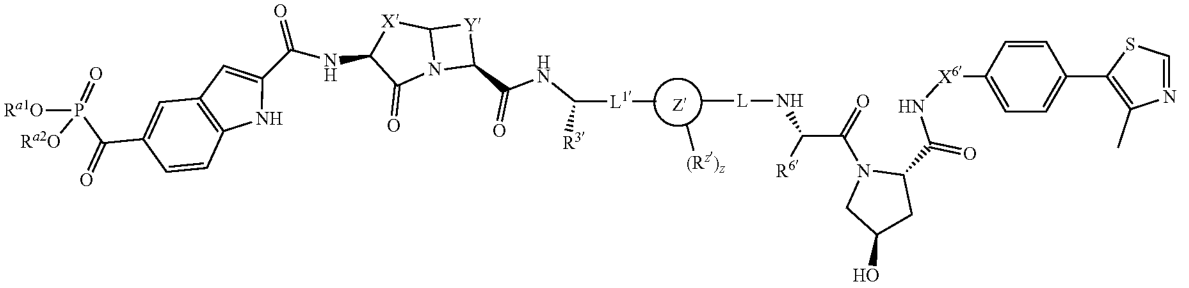

or a pharmaceutically acceptable salt thereof, wherein each of $X^{4'}$, $X^{5'}$, $X^{6'}$, $R^{3'}$, $R^{6'}$, L, $L^{1'}$, Ring Z', X', Y', $R^{a1}$, $R^{a2}$, $R^{z'}$, and z is as defined above and described in embodiments herein, both singly and in combination.

In some embodiments, the present invention provides a compound of formula II-r"-1, wherein Ring D' is phenyl, p is 1, $R^{7'}$ is

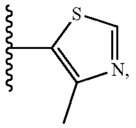

n is 1, $L^{1'}$ is

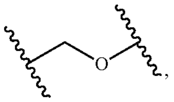 [SMILES: *CO*]

Ring Z' is phenylenyl, and $X^{4'}$, $X^{5'}$, and Q' are —C(O)— as shown, to provide a compound of formula II-r"-6:

II-r"-6

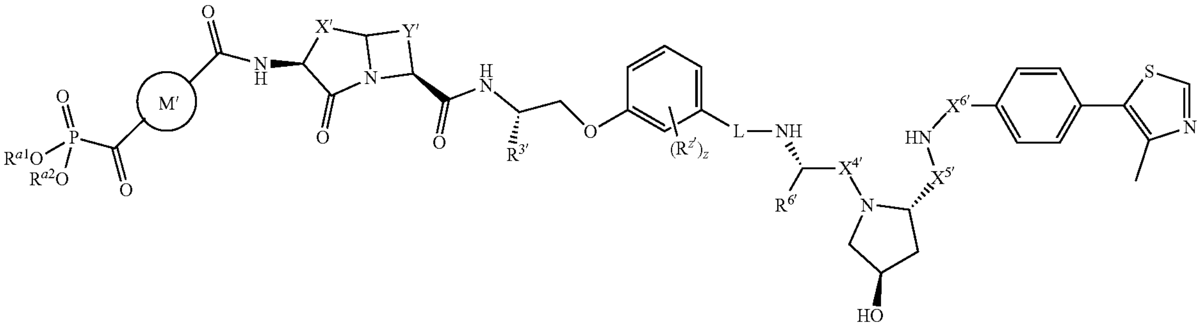

or a pharmaceutically acceptable salt thereof, wherein each of $X^{4'}$, $X^{5'}$, $X^{6'}$, $R^{3'}$, $R^{6'}$, L, Ring M', X', Y', $R^{a1}$, $R^{a2}$, $R^{z'}$, and z is as defined above and described in embodiments herein, both singly and in combination.

In certain embodiments, the present invention provides a compound of formula II-r"-7:

II-r"-7

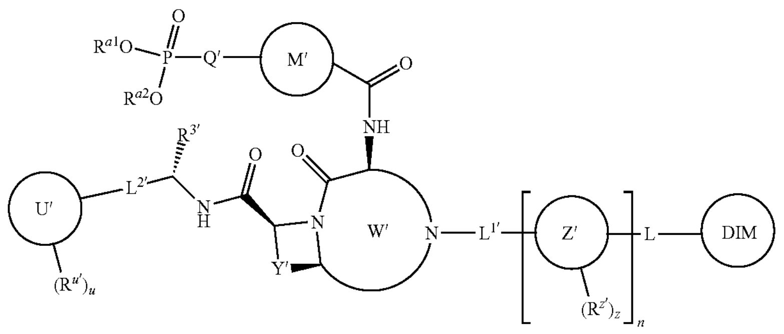

or a pharmaceutically acceptable salt thereof, wherein L and DIM are as defined above and described in embodiments herein, and wherein:

$L^{1'}$ is a covalent bond or a bivalent, saturated or partially unsaturated, straight or branched $C_{1-5}$ hydrocarbon chain, wherein 0-3 methylene units of $L^{1'}$ are independently replaced by —O—, —NR—, —CRF—, —$CF_2$—, —C(O)—, —S—, —S(O)—, or —$S(O)_2$—;

$L^{2'}$ is a covalent bond or a bivalent, saturated or partially unsaturated, straight or branched $C_{1-5}$ hydrocarbon chain, wherein 0-3 methylene units of $L^{2'}$ are independently replaced by —O—, —NR—, —CRF—, —$CF_2$—, —C(O)—, —S—, —S(O)—, or —$S(O)_2$—;

each R is independently hydrogen, or an optionally substituted group selected from $C_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same carbon or nitrogen are optionally taken together with their intervening atoms to form an optionally substituted 4-11 membered saturated or partially unsaturated monocyclic, bicyclic, bridged bicyclic, or spirocyclic carbocyclic or heterocyclic ring having 1-3 heteroatoms, in addition to the carbon or nitrogen from which the two R groups are attached, independently selected from nitrogen, oxygen, and sulfur; $R^{u'}$ is hydrogen or $R^A$;

each $R^A$ is independently an optionally substituted group selected from $C_{1-6}$ aliphatic, phenyl, a 4-7 membered saturated or partially unsaturated carbocyclic or heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring M' is an optionally substituted bivalent ring selected from phenylenyl, naphthylenyl, a 5-10 membered heteroarylenyl containing 1-4 heteroatoms independently selected from nitrogen, oxygen, or sulfur, a 5-11 membered saturated or partially unsaturated carbocyclylenyl or heterocyclylenyl with 1-4 heteroatoms independently selected from nitrogen, oxygen, or sulfur;

Q' is a bivalent moiety selected from —O—, —$CR_2$—, —$CF_2$—, —CFR—, —C(O)—, —$OCR_2$—, and —C(S)—;

$R^{a1}$ and $R^{a2}$ are each independently hydrogen or $R^A$;

Y' is an optionally substituted —$(CH_2)_y$—, wherein: y is 1, 2, or 3;

Ring W' is an optionally substituted ring selected from a 5-9 membered saturated or partially unsaturated heterocyclyl;

Ring U' is a ring selected from phenyl, a 5-6 membered heteroaryl containing 1-4 heteroatoms independently selected from nitrogen, oxygen, or sulfur, and a 5-7 membered saturated or partially unsaturated carbocyclyl or heterocyclyl with 1-3 heteroatoms independently selected from nitrogen, oxygen, or sulfur;

$R^{u'}$ is hydrogen, $R^A$, halogen, —CN, —$NO_2$, —OR, —SR, —$NR_2$, —$SiR_3$, —$S(O)_2R$, —$S(O)_2NR_2$, —S(O)R, —C(O)R, —C(O)OR, —C(O)$NR_2$, —C(O)NROR, —$CR_2$NRC(O)R, —$CR_2$NRC(O)$NR_2$, —OC(O)R, —OC(O)$NR_2$, —OP(O)$R_2$, —OP(O)$(OR)_2$, —OP(O)(OR)$NR_2$, —OP(O)$(NR_2)_2$, —NRC(O)OR, —NRC(O)R, —NRC(O)$NR_2$, —NRS$(O)_2$R, —NP(O)$R_2$, —NRP(O)$(OR)_2$, —NRP(O)(OR)$NR_2$, —NRP(O)$(NR_2)_2$, or —NRS$(O)_2$R;

u is 0, 1, 2, 3, or 4;

Ring Z' is a bivalent ring selected from phenylenyl, a 4-7 membered saturated or partially unsaturated carbocyclylenyl or heterocyclylenyl having 1-2 heteroatoms independently selected from nitrogen, oxygen, and sulfur, and a 5-6 membered heteroarylenyl having 1-4 heteroatoms independently selected from nitrogen, oxygen, and sulfur;

$R^{z'}$ is hydrogen, $R^A$, halogen, —CN, —$NO_2$, —OR, —SR, —$NR_2$, —$SiR_3$, —$S(O)_2R$, —$S(O)_2NR_2$, —S(O)R, —C(O)R, —C(O)OR, —C(O)$NR_2$, —C(O)NROR, —$CR_2$NRC(O)R, —$CR_2$NRC(O)$NR_2$, —OC(O)R, —OC(O)$NR_2$, —OP(O)$R_2$, —OP(O)$(OR)_2$, —OP(O)(OR)$NR_2$, —OP(O)$(NR_2)_2$, —NRC(O)OR, —NRC(O)R, —NRC(O)$NR_2$, —NRS$(O)_2$R, —NP(O)$R_2$, —NRP(O)$(OR)_2$, —NRP(O)(OR)$NR_2$, —NRP(O)$(NR_2)_2$, or —NRS$(O)_2$R;

z is 0, 1, 2, 3, or 4; and n is 0 or 1.

In certain embodiments, the present invention provides a compound of formula II-r"-8:

II-r''-8

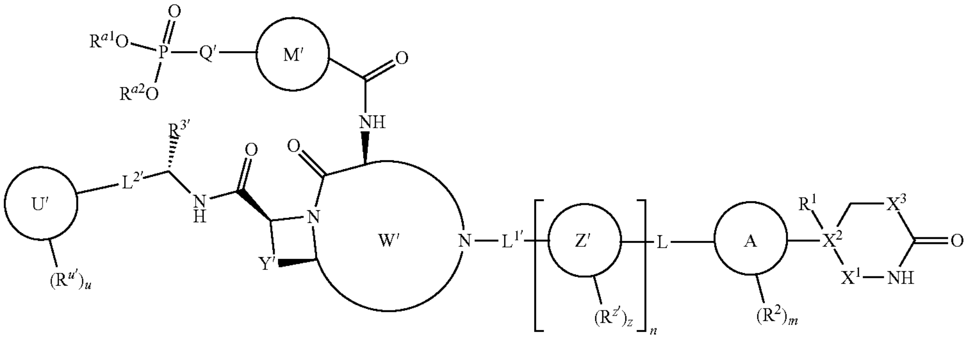

or a pharmaceutically acceptable salt thereof, wherein:

$X^1$ is a bivalent moiety selected from a covalent bond, $—CR_2—$, $—C(O)—$, $—C(S)—$, $—CR(CF_3)—$, $—P(O)OR—$, $—P(O)R—P(O)NR_2—$, $—S(O)—$, $—S(O)_2—$, or

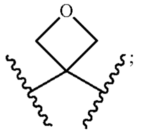 [SMILES: *C1(*)COC1]

$X^2$ is a carbon atom or silicon atom;

$X^3$ is a bivalent moiety selected from $—CR_2—$, $—NR—$, $—O—$, $—S—$, or $—SiR_2—$;

$R^1$ is hydrogen, halogen, —CN, —OR, —SR, —S(O)R, $—S(O)_2R$, $—NR_2$, $—P(O)(OR)_2$, $—P(O)NR_2OR$, $—P(O)(NR_2)_2$, $—Si(OH)_2R$, $—Si(OH)R_2$, $—SiR_3$, or an optionally substituted $C_{1-4}$ aliphatic;

each R is independently hydrogen, or an optionally substituted group selected from $C_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same carbon or nitrogen are optionally taken together with their intervening atoms to form an optionally substituted 4-11 membered saturated or partially unsaturated monocyclic, bicyclic, bridged bicyclic, or spirocyclic carbocyclic or heterocyclic ring having 1-3 heteroatoms, in addition to the carbon or nitrogen from which the two R groups are attached, independently selected from nitrogen, oxygen, and sulfur;

each $R^2$ is independently hydrogen, $R^A$, halogen, —CN, $—NO_2$, —OR, —SR, $—NR_2$, $—SiR_3$, $—S(O)_2R$, $—S(O)_2NR_2$, —S(O)R, —C(O)R, —C(O)OR, $—C(O)NR_2$, —C(O)NROR, $—CR_2NRC(O)R$, $—CR_2NRC(O)NR_2$, —OC(O)R, $—OC(O)NR_2$, $—OP(O)R_2$, $—OP(O)(OR)_2$, $—OP(O)(OR)NR_2$, $—OP(O)(NR_2)_2$, —NRC(O)OR, —NRC(O)R, $—NRC(O)NR_2$, $—NRS(O)_2R$, $—NP(O)R_2$, $—NRP(O)(OR)_2$, $—NRP(O)(OR)NR_2$, $—NRP(O)(NR_2)_2$, or $—NRS(O)_2R$;

each $R^A$ is independently an optionally substituted group selected from $C_{1-6}$ aliphatic, phenyl, a 4-7 membered saturated or partially unsaturated carbocyclic or heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a bicyclic or tricyclic ring selected from

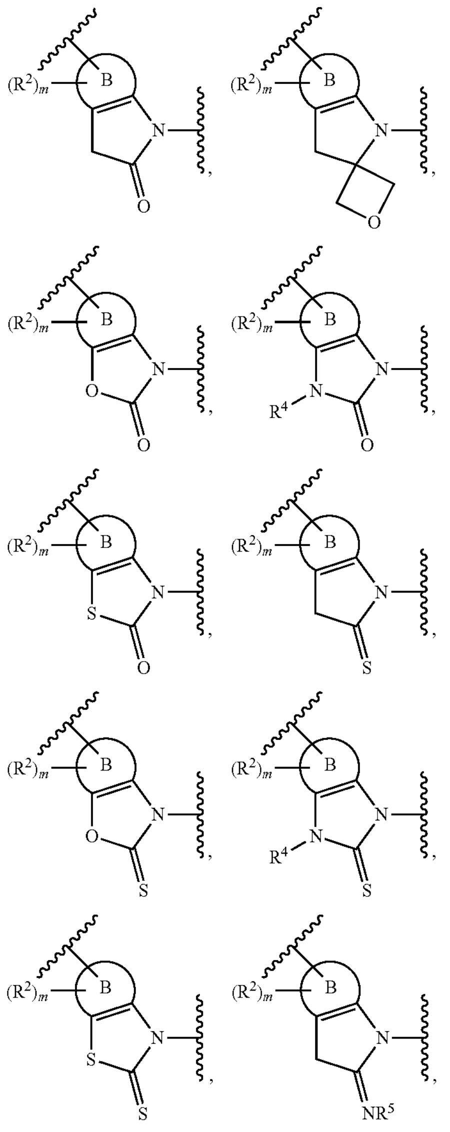

-continued
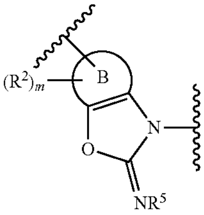,
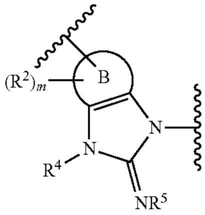,
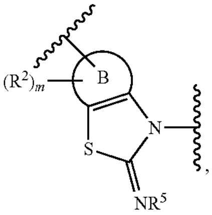,
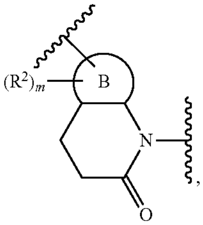,
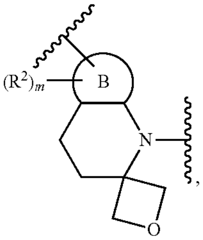,
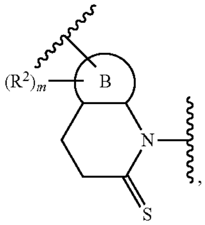,
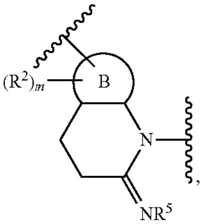,
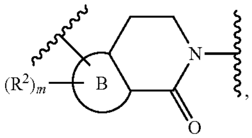,
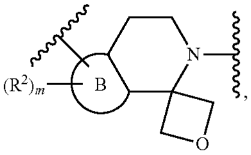,
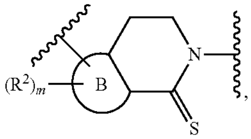,
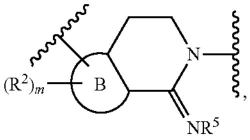,
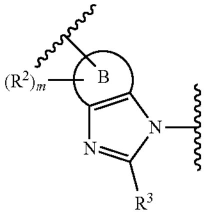,
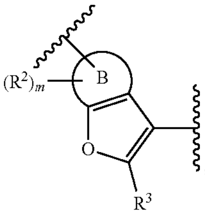,
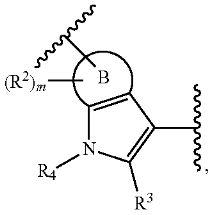,
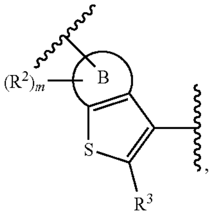,
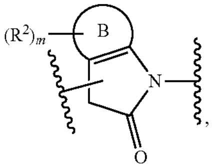,
-continued
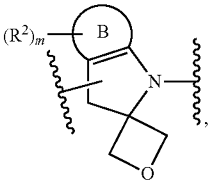,
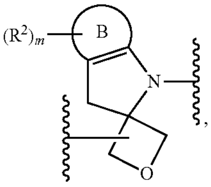,
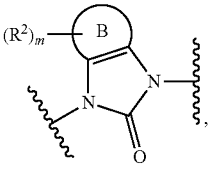,
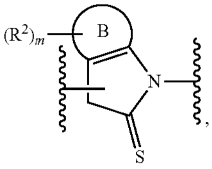,
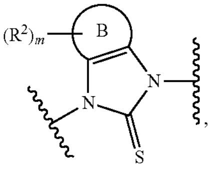,
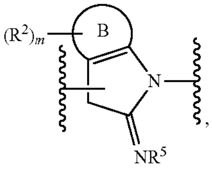,
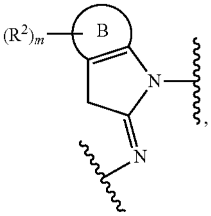,
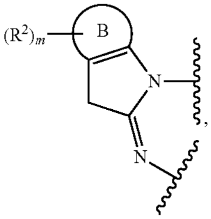,
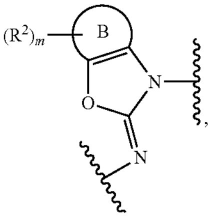,
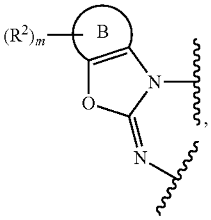,
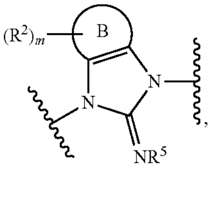,
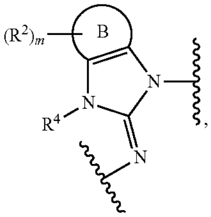,
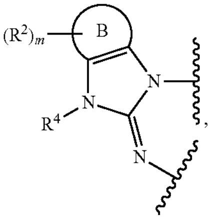,
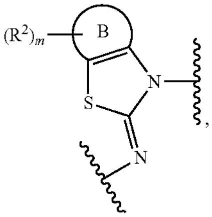,
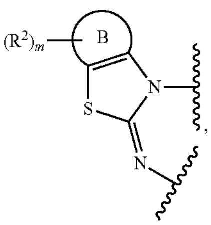,
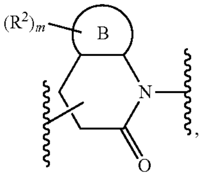, -continued

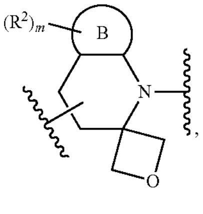
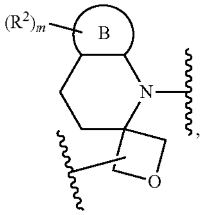
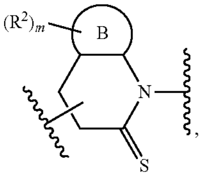
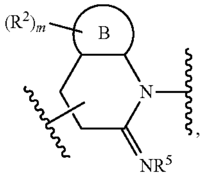
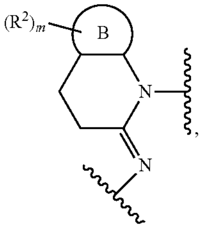
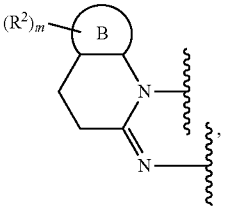
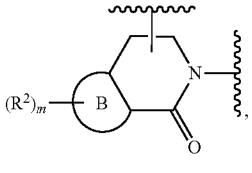
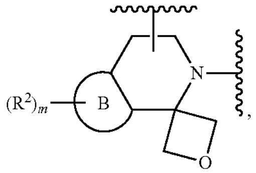
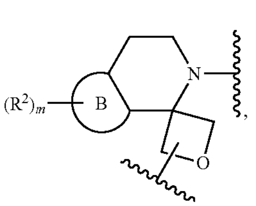
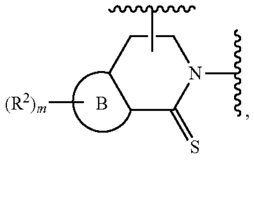
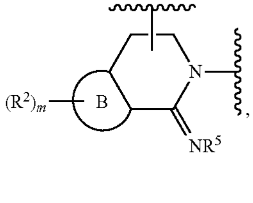
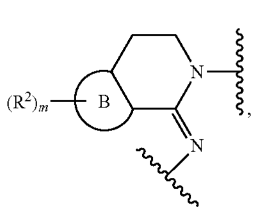
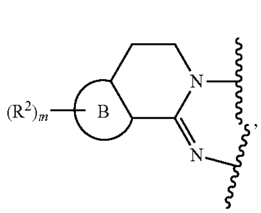
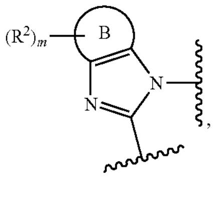
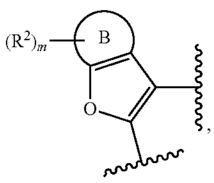

-continued

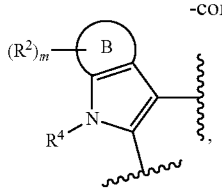
, or
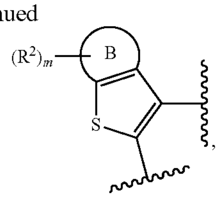

wherein:

Ring B is a fused ring selected from benzo, 5-6 membered heteroaryl containing 1-4 heteroatoms independently selected from nitrogen, oxygen, or sulfur, and a 5 to 7-membered saturated or partially unsaturated carbocyclyl or heterocyclyl with 1-3 heteroatoms independently selected from nitrogen, oxygen, or sulfur;

$R^3$ is selected from hydrogen, halogen, —OR, —$NR_2$, or —SR;

each $R^4$ is independently hydrogen, $R^A$, halogen, —CN, —$NO_2$, —OR, —SR, —$NR_2$, —$S(O)_2R$, —$S(O)_2NR_2$, —S(O)R, —C(O)R, —C(O)OR, —$C(O)NR_2$, —C(O)NROR, —OC(O)R, —$OC(O)NR_2$, —NRC(O)OR, —NRC(O)R, —$NRC(O)NR_2$, or —$NRS(O)_2R$;

$R^5$ is hydrogen, $C_{1-4}$ aliphatic, or —CN;

m is 0, 1, 2, 3 or 4;

L is a covalent bond or a bivalent, saturated or partially unsaturated, straight or branched $C_{1-20}$ hydrocarbon chain, wherein 0-6 methylene units of L are independently replaced by -Cy-, —O—, —NR—, —CRF—, —$CF_2$—, —C(O)—, —S—, —S(O)—, —$S(O)_2$—, —$SiR_2$—, —Si(OH)R—, —$Si(OH)_2$—, —P(O)OR—, —P(O)R—, or —$P(O)NR_2$—, wherein:

each -Cy- is independently an optionally substituted bivalent ring selected from phenylenyl, an 8-10 membered bicyclic arylenyl, a 4-7 membered saturated or partially unsaturated carbocyclylenyl, a 4-11 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-11 membered saturated or partially unsaturated spiro heterocyclylenyl having 1-3 heteroatoms independently selected from nitrogen, oxygen, and sulfur, an 8-10 membered bicyclic saturated or partially unsaturated heterocyclylenyl having 1-3 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;

$L^{1'}$ is a covalent bond or a bivalent, saturated or partially unsaturated, straight or branched $C_{1-5}$ hydrocarbon chain, wherein 0-3 methylene units of $L^{1'}$ are independently replaced by —O—, —NR—, —CRF—, —$CF_2$—, —C(O)—, —S—, —S(O)—, or —$S(O)_2$—;

$L^{2'}$ is a covalent bond or a bivalent, saturated or partially unsaturated, straight or branched $C_{1-5}$ hydrocarbon chain, wherein 0-3 methylene units of $L^{2'}$ are independently replaced by —O—, —NR—, —CRF—, —$CF_2$—, —C(O)—, —S—, —S(O)—, or —$S(O)_2$—;

$R^{3'}$ is hydrogen or $R^A$;

Ring M' is an optionally substituted bivalent ring selected from phenylenyl, naphthylenyl, a 5-10 membered heteroarylenyl containing 1-4 heteroatoms independently selected from nitrogen, oxygen, or sulfur, a 5-11 membered saturated or partially unsaturated carbocyclylenyl or heterocyclylenyl with 1-4 heteroatoms independently selected from nitrogen, oxygen, or sulfur;

Q' is a bivalent moiety selected from —O—, —$CR_2$—, —$CF_2$—, —CFR—, —C(O)—, —$OCR_2$—, and —C(S)—;

$R^{a1}$ and $R^{a2}$ are each independently hydrogen or $R^A$;

Y' is an optionally substituted —$(CH_2)_y$—, wherein: y is 1, 2, or 3;

Ring W' is an optionally substituted ring selected from a 5-9 membered saturated or partially unsaturated heterocyclyl;

Ring U' is a ring selected from phenyl, a 5-6 membered heteroaryl containing 1-4 heteroatoms independently selected from nitrogen, oxygen, or sulfur, and a 5-7 membered saturated or partially unsaturated carbocyclyl or heterocyclyl with 1-3 heteroatoms independently selected from nitrogen, oxygen, or sulfur;

$R^{u'}$ is hydrogen, $R^A$, halogen, —CN, —$NO_2$, —OR, —SR, —$NR_2$, —$SiR_3$, —$S(O)_2R$, —$S(O)_2NR_2$, —S(O)R, —C(O)R, —C(O)OR, —C(O)$NR_2$, —C(O)NROR, —$CR_2$NRC(O)R, —$CR_2$NRC(O)$NR_2$, —OC(O)R, —OC(O)$NR_2$, —OP(O)$R_2$, —OP(O)$(OR)_2$, —OP(O)(OR)$NR_2$, —OP(O)$(NR_2)_2$, —NRC(O)OR, —NRC(O)R, —NRC(O)$NR_2$, —NRS$(O)_2R$, —NP(O)$R_2$, —NRP(O)$(OR)_2$, —NRP(O)(OR)$NR_2$, —NRP(O)$(NR_2)_2$, or —NRS$(O)_2R$;

u is 0, 1, 2, 3, or 4;

Ring Z' is a bivalent ring selected from phenylenyl, a 4-7 membered saturated or partially unsaturated carbocyclylenyl or heterocyclylenyl having 1-2 heteroatoms independently selected from nitrogen, oxygen, and sulfur, and a 5-6 membered heteroarylenyl having 1-4 heteroatoms independently selected from nitrogen, oxygen, and sulfur;

$R^{z'}$ is hydrogen, $R^A$, halogen, —CN, —$NO_2$, —OR, —SR, —$NR_2$, —$SiR_3$, —$S(O)_2R$, —$S(O)_2NR_2$, —S(O)R, —C(O)R, —C(O)OR, —C(O)$NR_2$, —C(O)NROR, —$CR_2$NRC(O)R, —$CR_2$NRC(O)$NR_2$, —OC(O)R, —OC(O)$NR_2$, —OP(O)$R_2$, —OP(O)$(OR)_2$, —OP(O)(OR)$NR_2$, —OP(O)$(NR_2)_2$, —NRC(O)OR, —NRC(O)R, —NRC(O)$NR_2$, —NRS$(O)_2R$, —NP(O)$R_2$, —NRP(O)$(OR)_2$, —NRP(O)(OR)$NR_2$, —NRP(O)$(NR_2)_2$, or —NRS$(O)_2R$;

z is 0, 1, 2, 3, or 4; and n is 0 or 1.

In some embodiments, the present invention provides a compound of formula II-r"-8, wherein $X^1$, $X^2$, $X^3$, $R^1$, and Ring A is

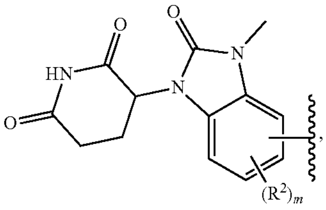

n is 1, Y' is

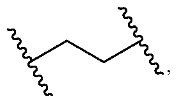 [SMILES: *CC*]

Ring W' is an 8-membered heterocyclyl, and Q' is —C(O)— as shown, to provide a compound of formula II-r"-9:

II-r"-9

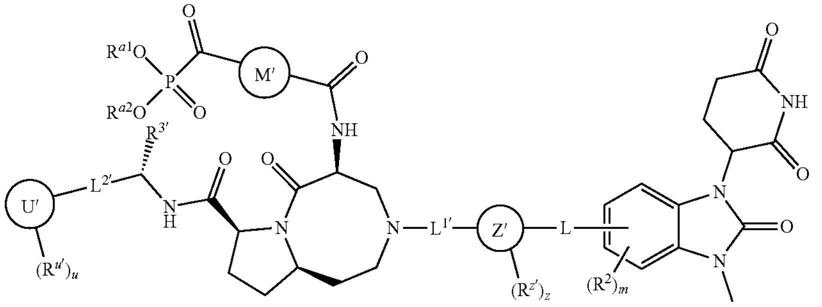

or a pharmaceutically acceptable salt thereof, wherein each of $R^2$, m, L, $L^1$, $L^{2'}$, Ring M', Ring U', Ring Z', $R^{3'}$, $R^{a1}$, $R^{a2}$, $R^{u'}$, u, $R^{z'}$, and z is as defined above and described in embodiments herein, both singly and in combination.

In some embodiments, the present invention provides a compound of formula II-r"-8, wherein $X^1$, $X^2$, $X^3$, $R^1$, and Ring A is

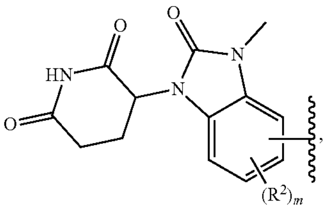

n is 1, Y' is

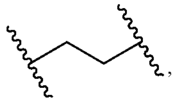 [SMILES: *CC*]

Ring W' is an 8-membered heterocyclyl, Ring M' is

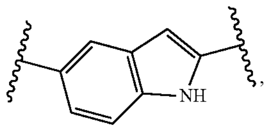 [SMILES: *c1ccc2[nH]c(*)cc2c1]

and Q' is —C(O)— as shown, to provide a compound of formula II-r"-10:

II-r"-10

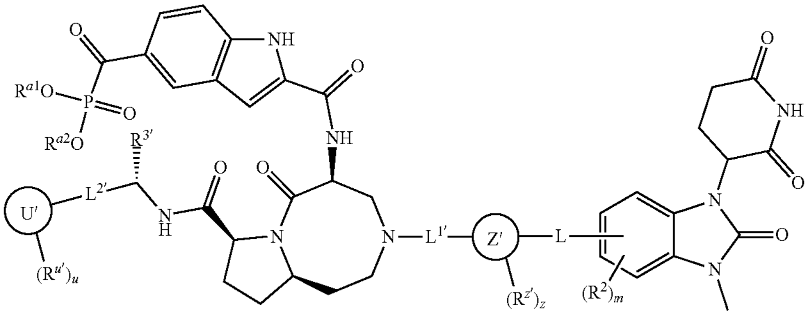

or a pharmaceutically acceptable salt thereof, wherein each of $R^2$, m, L, $L^{1'}$, $L^{2'}$, Ring U', Ring Z', $R^{3'}$, Rn, $R^{a2}$, $R^{u'}$, u, $R^{z'}$, and z is as defined above and described in embodiments herein, both singly and in combination.

In some embodiments, the present invention provides a compound of formula II-r"-8, wherein $X^1$, $X^2$, $X^3$, $R^1$, and Ring A is

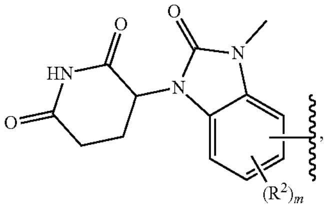

n is 1, Y' is

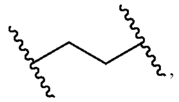

Ring W' is an 8-membered heterocyclyl, $L^{2'}$ is

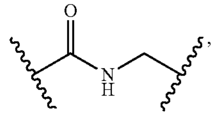 [SMILES: *CNC(*)=O]

Ring U' is phenyl, and Q' is —C(O)— as shown, to provide a compound of formula II-r"-11:

II-r"-11

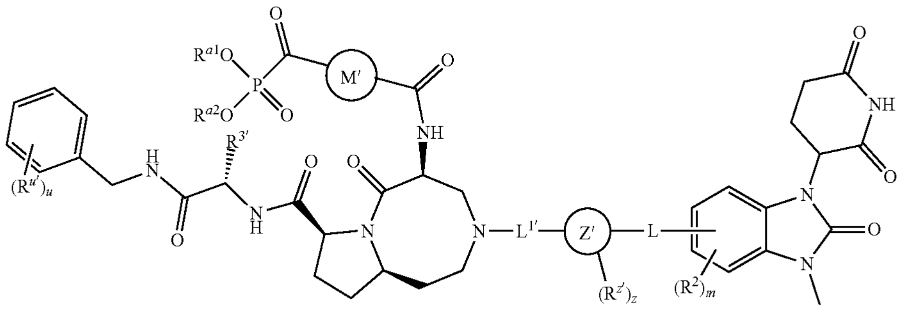

or a pharmaceutically acceptable salt thereof, wherein each of $R^2$, m, L, $L^{1'}$, Ring M', Ring Z', $R^{3'}$, $R^{a1}$, $R^{a2}$, $R^{u'}$, u, $R^{z1}$, and z is as defined above and described in embodiments herein, both singly and in combination.

In some embodiments, the present invention provides a compound of formula II-r''-8, wherein $X^1$, $X^2$, $X^3$, $R^1$, and Ring A is

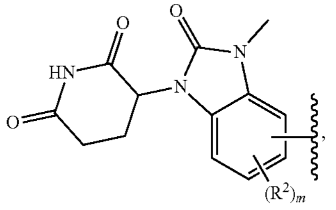

n is 1, Y' is

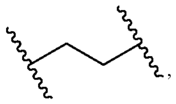 [SMILES: *CC*]

Ring W' is an 8-membered heterocyclyl, $L^{1'}$ is

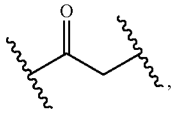 [SMILES: *CC(*)=O]

Ring Z' is cyclohexyl z is 0, and Q' is —C(O)— as shown, to provide a compound of formula II-r''-12:

II-r''-12

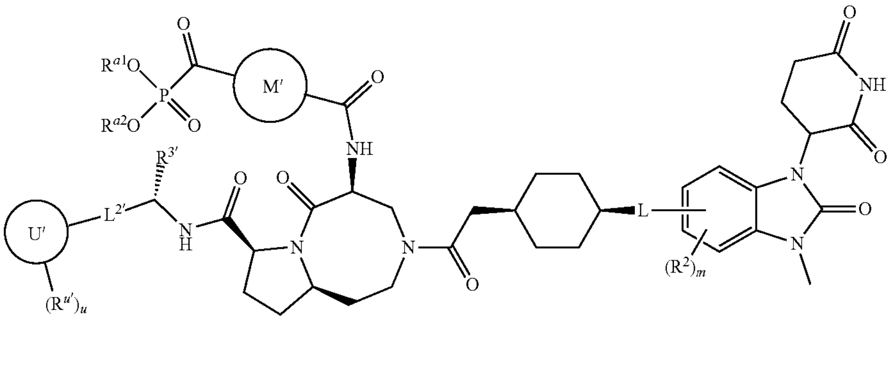

or a pharmaceutically acceptable salt thereof, wherein each of $R^2$, m, L, $L^{2'}$, Ring M', Ring U', $R^{3'}$, $R^a$, $R^{a2}$, $R^{u'}$, and u is as defined above and described in embodiments herein, both singly and in combination.

In certain embodiments, the present invention provides a compound of formula II-s'':

II-s''

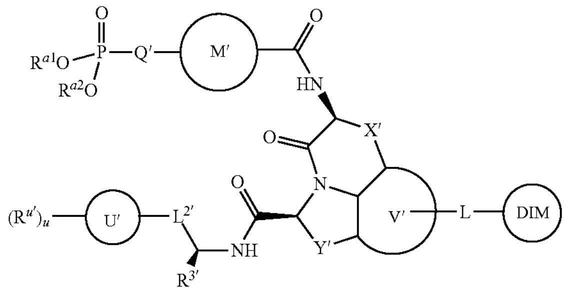

or a pharmaceutically acceptable salt thereof, wherein L and DIM are as defined above and described in embodiments herein, and wherein:

$L^{2'}$ is a covalent bond or a bivalent, saturated or partially unsaturated, straight or branched $C_{1-5}$ hydrocarbon chain, wherein 0-3 methylene units of $L^{2'}$ are independently replaced by —O—, —NR—, —CRF—, —$CF_2$—, —C(O)—, —S—, —S(O)—, or —$S(O)_2$—;

each R is independently hydrogen, or an optionally substituted group selected from $C_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same carbon or nitrogen are optionally taken together with their intervening atoms to form an optionally substituted 4-11 membered saturated or partially unsaturated monocyclic, bicyclic, bridged bicyclic, or spirocyclic carbocyclic or heterocyclic ring having 1-3 heteroatoms, in addition to the carbon or nitrogen from which the two R groups are attached, independently selected from nitrogen, oxygen, and sulfur;

$R^{u'}$ is hydrogen or $R^A$;

each $R^A$ is independently an optionally substituted group selected from $C_{1-6}$ aliphatic, phenyl, a 4-7 membered saturated or partially unsaturated carbocyclic or heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring M' is an optionally substituted bivalent ring selected from phenylenyl, naphthylenyl, a 5-10 membered heteroarylenyl containing 1-4 heteroatoms independently selected from nitrogen, oxygen, or sulfur, a 5-11 membered saturated or partially unsaturated carbocyclylenyl or heterocyclylenyl with 1-4 heteroatoms independently selected from nitrogen, oxygen, or sulfur;

Q' is a bivalent moiety selected from —O—, —$CR_2$—, —$CF_2$—, —CFR—, —C(O)—, —$OCR_2$—, and —C(S)—;

$R^{a1}$ and $R^{a2}$ are each independently hydrogen or $R^A$;

Ring V' is an optionally substituted fused ring selected from a 6-membered aryl, a 5-6 membered heteroaryl containing 1-4 heteroatoms independently selected from nitrogen, oxygen, or sulfur, and a 5-7 membered saturated or partially unsaturated carbocyclyl or heterocyclyl with 1-3 heteroatoms independently selected from nitrogen, oxygen, or sulfur;

$X^1$ is an optionally substituted —$(CH_2)_x$—, wherein:

x is 0, 1, 2, or 3;

Y' is an optionally substituted —$(CH_2)_y$—, wherein:

y is 0, 1, 2, or 3;

Ring U' is a ring selected from phenyl, a 5-6 membered heteroaryl containing 1-4 heteroatoms independently selected from nitrogen, oxygen, or sulfur, and a 5-7 membered saturated or partially unsaturated carbocyclyl or heterocyclyl with 1-3 heteroatoms independently selected from nitrogen, oxygen, or sulfur;

$R^{u'}$ is hydrogen, $R^A$, halogen, —CN, —$NO_2$, —OR, —SR, —$NR_2$, —$SiR_3$, —$S(O)_2R$, —$S(O)_2NR_2$, —S(O)R, —C(O)R, —C(O)OR, —C(O)$NR_2$, —C(O)NROR, —$CR_2$NRC(O)R, —$CR_2$NRC(O)$NR_2$, —OC(O)R, —OC(O)$NR_2$, —OP(O)$R_2$, —OP(O)$(OR)_2$, —OP(O)(OR)$NR_2$, —OP(O)$(NR_2)_2$, —NRC(O)OR, —NRC(O)R, —NRC(O)$NR_2$, —NRS$(O)_2$R, —NP(O)$R_2$, —NRP(O)$(OR)_2$, —NRP(O)(OR)$NR_2$, —NRP(O)$(NR_2)_2$, or —NRS$(O)_2$R; and u is 0, 1, 2, 3, or 4.

In certain embodiments, the present invention provides a compound of formula II-s"-1:

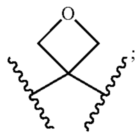 [SMILES: *C1(*)COC1]

$X^2$ is a carbon atom or silicon atom;

$X^3$ is a bivalent moiety selected from —$CR_2$—, —NR—, —O—, —S—, or —$SiR_2$—;

$R^1$ is hydrogen, halogen, —CN, —OR, —SR, —S(O)R, —$S(O)_2R$, —$NR_2$, —P(O)$(OR)_2$, —P(O)$NR_2$OR, —P(O)$(NR_2)_2$, —Si$(OH)_2$R, —Si(OH)$R_2$, —$SiR_3$, or an optionally substituted $C_{1-4}$ aliphatic;

each R is independently hydrogen, or an optionally substituted group selected from $C_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same carbon or nitrogen are optionally taken together with their intervening atoms to form an optionally substituted 4-11 membered saturated or partially unsaturated monocyclic, bicyclic, bridged bicyclic, or spirocyclic carbocyclic or heterocyclic ring having 1-3 heteroatoms, in addition to the carbon or nitrogen from which the two R groups are attached, independently selected from nitrogen, oxygen, and sulfur;

each $R^2$ is independently hydrogen, $R^A$, halogen, —CN, —$NO_2$, —OR, —SR, —$NR_2$, —$SiR_3$, —$S(O)_2R$, —$S(O)_2NR_2$, —S(O)R, —C(O)R, —C(O)OR, —C(O)$NR_2$, —C(O)NROR, —$CR_2$NRC(O)R, —$CR_2$NRC(O)$NR_2$, —OC(O)R, —OC(O)$NR_2$, —OP(O)$R_2$, —OP(O)$(OR)_2$, —OP(O)(OR)$NR_2$, —OP(O)$(NR_2)_2$, —NRC(O)OR, —NRC(O)R, —NRC(O)$NR_2$, —NRS$(O)_2$R, —NP(O)$R_2$, —NRP(O)$(OR)_2$, —NRP(O)(OR)$NR_2$, —NRP(O)$(NR_2)_2$, or —NRS$(O)_2$R;

II-s"-1

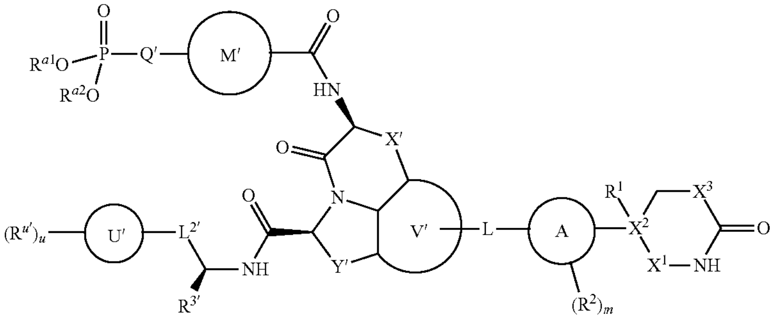

or a pharmaceutically acceptable salt thereof, wherein:

$X^1$ is a bivalent moiety selected from a covalent bond, —$CR_2$—, —C(O)—, —C(S)—, —CR$(CF_3)$—, —P(O)OR—, —P(O)R—P(O)$NR_2$—, —S(O)—, —$S(O)_2$—, or each $R^A$ is independently an optionally substituted group selected from $C_{1-6}$ aliphatic, phenyl, a 4-7 membered saturated or partially unsaturated carbocyclic or heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

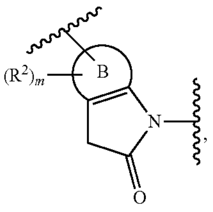
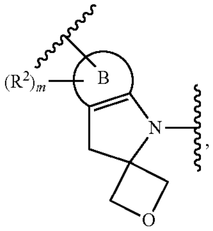
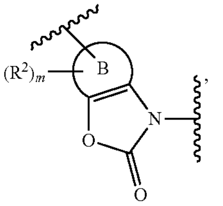
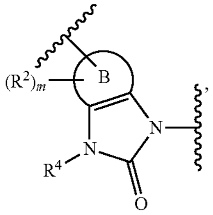
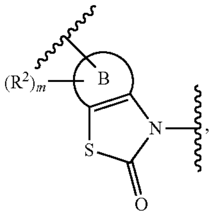
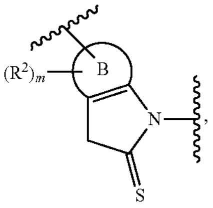
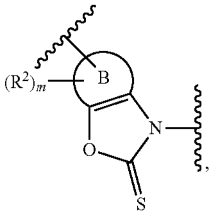
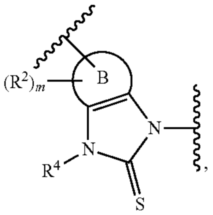
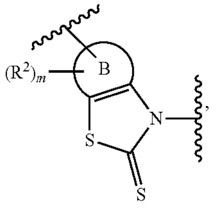
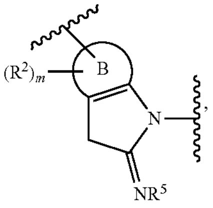
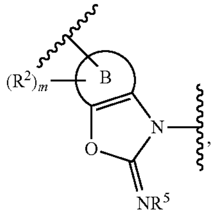
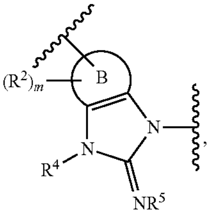
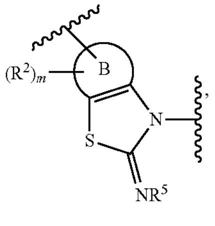
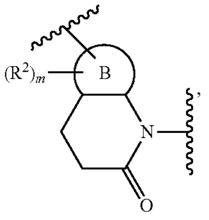
-continued
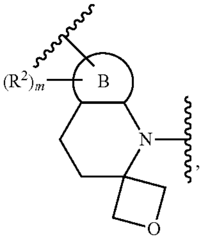
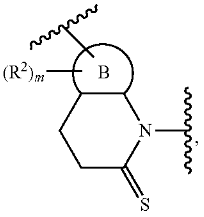
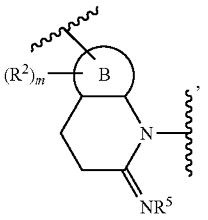
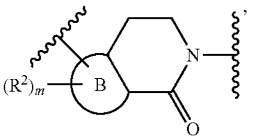
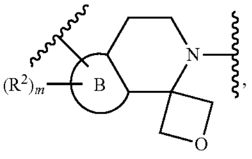
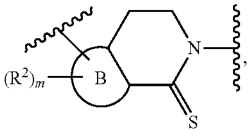
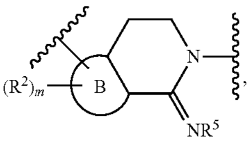
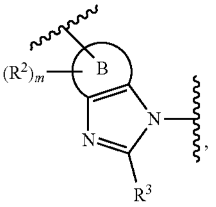
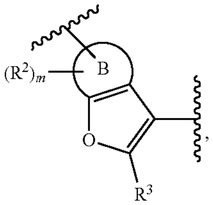
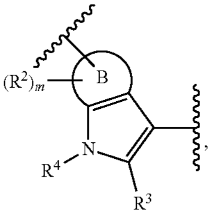
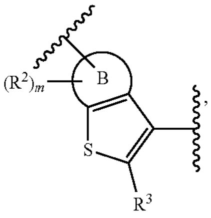
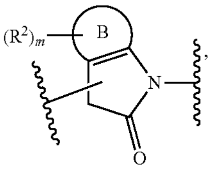
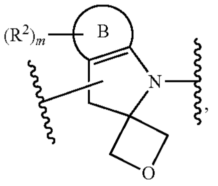
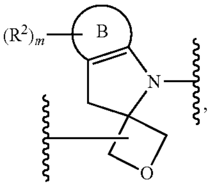
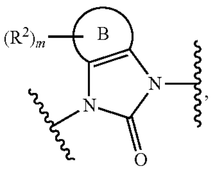
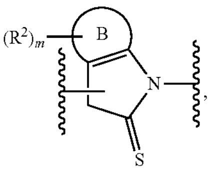

-continued

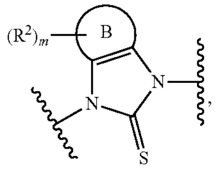
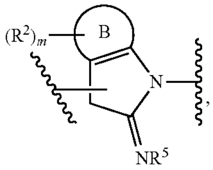
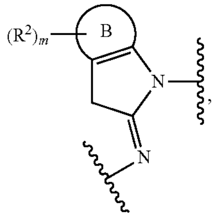
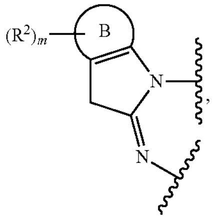
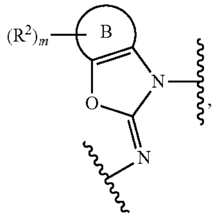
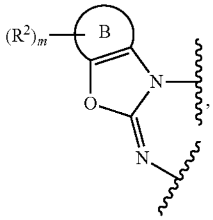
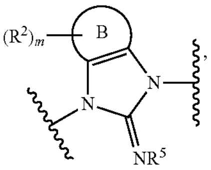
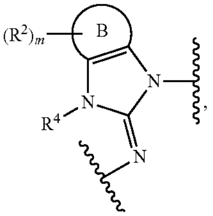
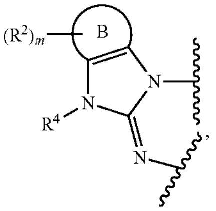
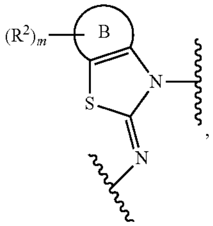
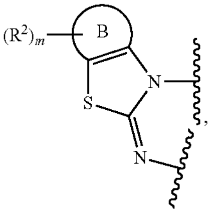
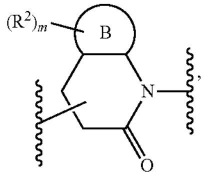
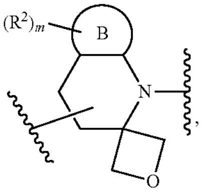
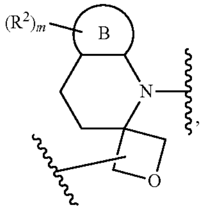
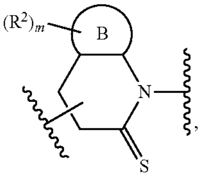
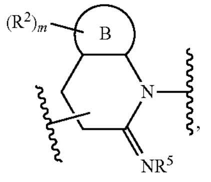

-continued

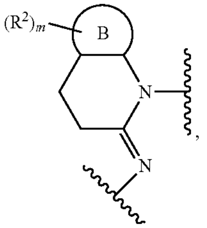
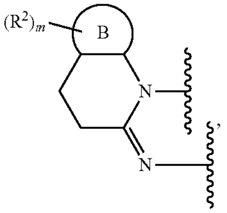
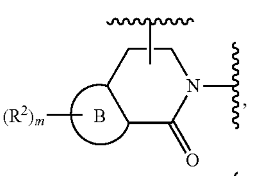
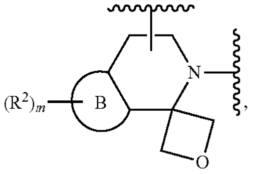
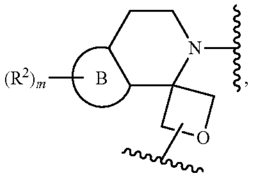
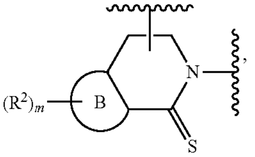
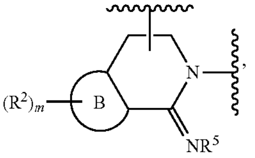
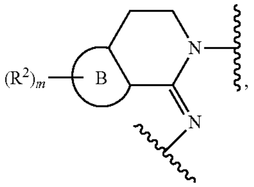
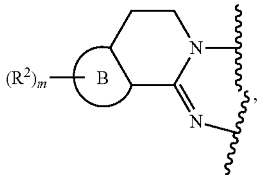
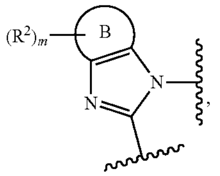
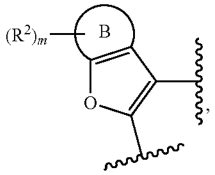
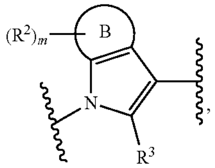
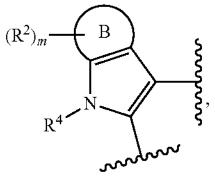
or
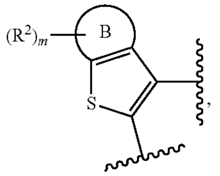

Ring A is a bicyclic or tricyclic ring selected from wherein:

Ring B is a fused ring selected from benzo, 5-6 membered heteroaryl containing 1-4 heteroatoms independently selected from nitrogen, oxygen, or sulfur, and a 5 to 7-membered saturated or partially unsaturated carbocyclyl or heterocyclyl with 1-3 heteroatoms independently selected from nitrogen, oxygen, or sulfur;

$R^3$ is selected from hydrogen, halogen, —OR, —$NR_2$, or —SR;

each $R^4$ is independently hydrogen, $R^A$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)NROR, —OC(O)R, —OC(O)$NR_2$, —NRC(O)OR, —NRC(O)R, —NRC(O)$NR_2$, or —NRS(O)$_2$R;

$R^5$ is hydrogen, $C_{1-4}$ aliphatic, or —CN;

m is 0, 1, 2, 3 or 4;

L is a covalent bond or a bivalent, saturated or partially unsaturated, straight or branched $C_{1-20}$ hydrocarbon chain, wherein 0-6 methylene units of L are independently replaced by -Cy-, —O—, —NR—, —CRF—, —$CF_2$—, —C(O)—, —S—, —S(O)—, —$S(O)_2$—, —$SiR_2$—, —Si(OH)R—, —$Si(OH)_2$—, —P(O)OR—, —P(O)R—, or —$P(O)NR_2$—, wherein:

each -Cy- is independently an optionally substituted bivalent ring selected from phenylenyl, an 8-10 membered bicyclic arylenyl, a 4-7 membered saturated or partially unsaturated carbocyclylenyl, a 4-11 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-11 membered saturated or partially unsaturated spiro heterocyclylenyl having 1-3 heteroatoms independently selected from nitrogen, oxygen, and sulfur, an 8-10 membered bicyclic saturated or partially unsaturated heterocyclylenyl having 1-3 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;

$L^{2'}$ is a covalent bond or a bivalent, saturated or partially unsaturated, straight or branched $C_{1-5}$ hydrocarbon chain, wherein 0-3 methylene units of $L^{2'}$ are independently replaced by —O—, —NR—, —CRF—, —$CF_2$—, —C(O)—, —S—, —S(O)—, or —$S(O)_2$—;

$R^{u'}$ is hydrogen or $R^A$;

Ring M' is an optionally substituted bivalent ring selected from phenylenyl, naphthylenyl, a 5-10 membered heteroarylenyl containing 1-4 heteroatoms independently selected from nitrogen, oxygen, or sulfur, a 5-11 membered saturated or partially unsaturated carbocyclylenyl or heterocyclylenyl with 1-4 heteroatoms independently selected from nitrogen, oxygen, or sulfur;

Q' is a bivalent moiety selected from —O—, —$CR_2$—, —$CF_2$—, —CFR—, —C(O)—, —$OCR_2$—, and —C(S)—;

$R^{a1}$ and $R^{a2}$ are each independently hydrogen or $R^A$;

Ring V' is an optionally substituted fused ring selected from a 6-membered aryl, a 5-6 membered heteroaryl containing 1-4 heteroatoms independently selected from nitrogen, oxygen, or sulfur, and a 5-7 membered saturated or partially unsaturated carbocyclyl or heterocyclyl with 1-3 heteroatoms independently selected from nitrogen, oxygen, or sulfur;

$X^1$ is an optionally substituted —$(CH_2)_x$—, wherein:

x is 0, 1, 2, or 3;

Y' is an optionally substituted —$(CH_2)_y$—, wherein:

y is 0, 1, 2, or 3;

Ring U' is a ring selected from phenyl, a 5-6 membered heteroaryl containing 1-4 heteroatoms independently selected from nitrogen, oxygen, or sulfur, and a 5-7 membered saturated or partially unsaturated carbocyclyl or heterocyclyl with 1-3 heteroatoms independently selected from nitrogen, oxygen, or sulfur;

$R^{u'}$ is hydrogen, $R^A$, halogen, —CN, —$NO_2$, —OR, —SR, —$NR_2$, —$SiR_3$, —$S(O)_2R$, —$S(O)_2NR_2$, —S(O)R, —C(O)R, —C(O)OR, —$C(O)NR_2$, —C(O)NROR, —$CR_2NRC(O)R$, —$CR_2NRC(O)NR_2$, —OC(O)R, —OC(O)$NR_2$, —$OP(O)R_2$, —$OP(O)(OR)_2$, —OP(O)(OR)$NR_2$, —$OP(O)(NR_2)_2$, —NRC(O)OR, —NRC(O)R, —$NRC(O)NR_2$, —$NRS(O)_2R$, —$NP(O)R_2$, —$NRP(O)(OR)_2$, —NRP(O)(OR)$NR_2$, —$NRP(O)(NR_2)_2$, or —$NRS(O)_2R$; and u is 0, 1, 2, 3, or 4;

In some embodiments, the present invention provides a compound of formula II-s"-1, wherein $X^1$, $X^2$, $X^3$, $R^1$, and Ring A

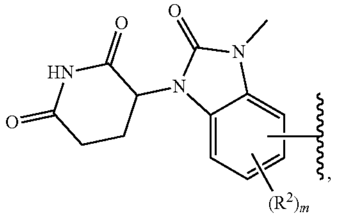

n is 1, X' is

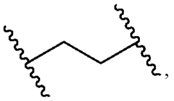 [SMILES: *CC*]

Y' is —$CH_2$—, Ring V' is a 6-member aryl, and Q' is —C(O)— as shown, to provide a compound of formula II-s"-2:

II-s"-2

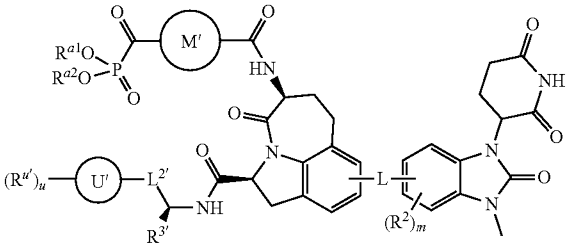

or a pharmaceutically acceptable salt thereof, wherein each of $R^2$, m, L, $L^{2'}$, Ring M', Ring U', $R^{3'}$, $R^{a1}$, $R^{a2}$, $R^{u'}$, and u is as defined above and described in embodiments herein, both singly and in combination.

In some embodiments, the present invention provides a compound of formula II-s"-1, wherein $X^1$, $X^2$, $X^3$, $R^1$, and Ring A is

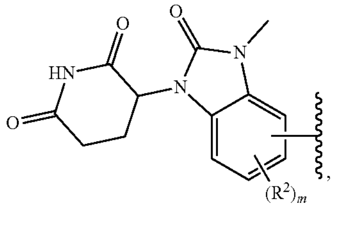

n is 1, Ring M' is

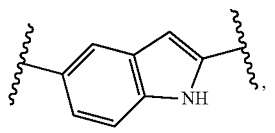 [SMILES: *c1ccc2[nH]c(*)cc2c1]

$X^1$ is

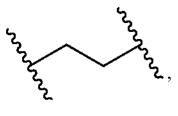 [SMILES: *CC*]

Y' is —$CH_2$—, Ring V' is a 6-member aryl, and Q' is —C(O)— as shown, to provide a compound of formula II-s"-3:

II-s"-3

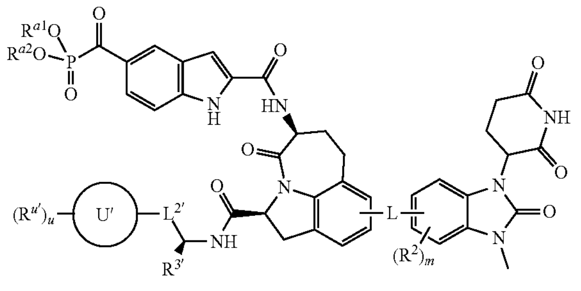

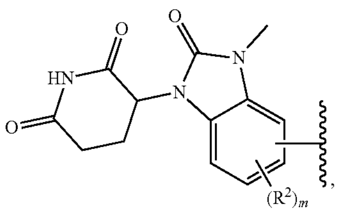

n is 1, $L^{2'}$ is

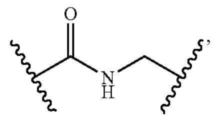 [SMILES: *CNC(*)=O]

Ring U' is phenyl, X' is

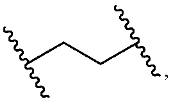 [SMILES: *CC*]

Y' is —$CH_2$—, Ring V' is a 6-member aryl, and Q' is —C(O)— as shown, to provide a compound of formula II-s"-4:

II-s"-4

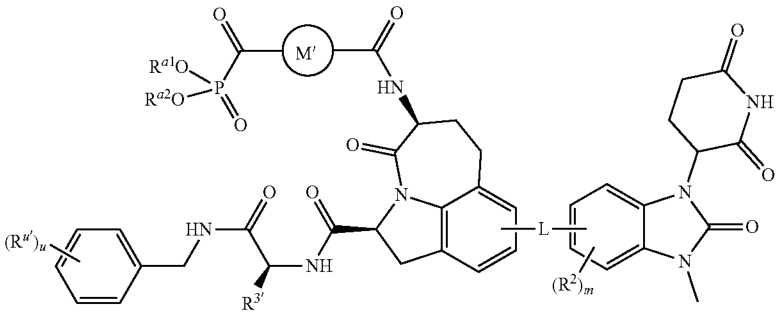

or a pharmaceutically acceptable salt thereof, wherein each of $R^2$, m, L, $L^{2'}$, Ring U', $R^{3'}$, $R^{a1}$, $R^{a2}$, $R^{u'}$, and u is as defined above and described in embodiments herein, both singly and in combination.

In some embodiments, the present invention provides a compound of formula II-s"-1, wherein $X^1$, $X^2$, $X^3$, $R^1$, and Ring A is or a pharmaceutically acceptable salt thereof, wherein each of $R^2$, m, L, Ring M', $R^{3'}$, $R^{a1}$, $R^{a2}$, $R^{u'}$, and u is as defined above and described in embodiments herein, both singly and in combination.

As defined above and described herein, $X^{4'}$, $X^{5'}$, and $X^{6'}$ are each independently a bivalent moiety selected from a covalent bond, —$CR_2$—, —C(O)—, —C(S)—, —O—, —S(O)—, —$S(O)_2$—,

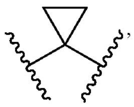, or 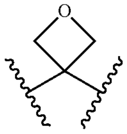

In some embodiments, $X^{4'}$ is a covalent bond. In some embodiments, $X^{4'}$ is —$CR_2$—. In some embodiments, $X^4$ is —C(O)—. In some embodiments, $X^{4'}$ is —C(S)—. In some embodiments, $X^{4'}$ is —O—. In some embodiments, $X^{4'}$ is —S(O)—. In some embodiments, $X^{4'}$ is —$S(O)_2$—. In some embodiments, $X^{4'}$ is

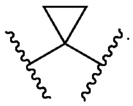 [SMILES: *C1(*)CC1]

In some embodiments, $X^{4'}$ is

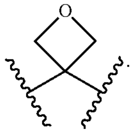 [SMILES: *C1(*)COC1]

In some embodiments, $X^{5'}$ is a covalent bond. In some embodiments, $X^{5'}$ is —$CR_2$—. In some embodiments, $X^{5'}$ is —C(O)—. In some embodiments, $X^{5'}$ is —C(S)—. In some embodiments, $X^{5'}$ is —O—. In some embodiments, $X^{5'}$ is —S(O)—. In some embodiments, $X^{5'}$ is —$S(O)_2$—

In some embodiments, $X^{5'}$ is

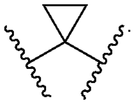

In some embodiments, $X^{5'}$ is

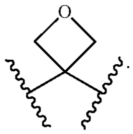 [SMILES: *C1(*)COC1]

In some embodiments, $X^{6'}$ is a covalent bond. In some embodiments, $X^{6'}$ is —$CR_2$—. In some embodiments, $X^{6'}$ is —C(O)—. In some embodiments, $X^{6'}$ is —C(S)—. In some embodiments, $X^{6'}$ is —O—. In some embodiments, $X^{6'}$ is —S(O)—. In some embodiments, $X^{6'}$ is —$S(O)_2$—. In some embodiments, $X^{6'}$ is

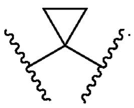

In some embodiments, $X^{6'}$ is

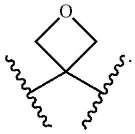 [SMILES: *C1(*)COC1]

In some embodiments, $X^{6'}$

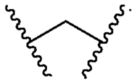

In some embodiments, $X^{6'}$ is

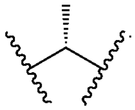

As defined above and described herein, each $R^{A}$ is independently an optionally substituted group selected from $C_{1-6}$ aliphatic, phenyl, a 4-7 membered saturated or partially unsaturated carbocyclic or heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur.

In some embodiments, $R^{A}$ is an optionally substituted $C_{1-6}$ aliphatic. In some embodiments, $R^{A}$ is an optionally substituted phenyl. In some embodiments, $R^{A}$ is an optionally substituted 4-7 membered saturated or partially unsaturated carbocyclic or heterocyclic ring having 1-2 heteroatoms independently selected from nitrogen, oxygen, and sulfur. In some embodiments, $R^{A}$ is an optionally substituted 5-6 membered heteroaryl ring having 1-4 heteroatoms independently selected from nitrogen, oxygen, and sulfur. In some embodiments, $R^{A}$ is

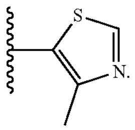

In some embodiments, $R^{A}$ is —$CH_2CO_2R$. In some embodiments, $R^{A}$ is —$CH_2OCO_2R$. In some embodiments, $R^{A}$ is —$CH_2C(O)NR_2$.

In some embodiments, $R^{A}$ is selected from those depicted in Table 1, below.

As defined above and described herein, $R^{6'}$ is hydrogen or $R^{A}$.

In some embodiments, $R^{\circ'}$ is hydrogen. In some embodiments, $R^{\circ'}$ is $R^{A}$. In some embodiments, $R^{3'}$ is ethyl. In some embodiments, $R^{3'}$ is isopropyl. In some embodiments, $R^{3'}$ is neopropyl. In some embodiments, $R^{3'}$ is tert-butyl. In some embodiments, $R^{3'}$ is cyclopropyl. In some embodiments, $R^{3'}$ is cyclobutyl. In some embodiments, $R^{3'}$ is cyclopentyl. In some embodiments, $R^{3'}$ is cyclohexyl.

In some embodiments, $R^{3'}$ is selected from those depicted in Table 1, below.

As defined above and described herein, $R^{7'}$ is hydrogen, $R^A$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)NROR, —OC(O)R, —OC(O)$NR_2$, —NRC(O)OR, —NRC(O)R, —NRC(O)$NR_2$, or —$NRS(O)_2R$.

In some embodiments, $R^{7'}$ is hydrogen. In some embodiments, $R^{7'}$ is $R^A$. In some embodiments, $R^{7'}$ is halogen. In some embodiments, $R^{7'}$ is —CN. In some embodiments, $R^{7'}$ is —$NO_2$. In some embodiments, $R^{7'}$ is —OR. In some embodiments, $R^{7'}$ is —SR. In some embodiments, $R^{7'}$ is —$NR_2$. In some embodiments, $R^{7'}$ is —$S(O)_2R$. In some embodiments, $R^{7'}$ is —$S(O)_2NR_2$. In some embodiments, $R^{7'}$ is —S(O)R. In some embodiments, $R^{7'}$ is —C(O)R. In some embodiments, $R^{7'}$ is —C(O)OR. In some embodiments, $R^{7'}$ is —C(O)$NR_2$. In some embodiments, $R^{7'}$ is —C(O)NROR. In some embodiments, $R^{7'}$ is —OC(O)R. In some embodiments, $R^{7'}$ is —OC(O)$NR_2$. In some embodiments, $R^{7'}$ is —NRC(O)OR. In some embodiments, $R^{7'}$ is —NRC(O)R. In some embodiments, $R^{7'}$ is —NRC(O)$NR_2$. In some embodiments, $R^{7'}$ is —$NRS(O)_2R$. In some embodiments, $R^{7'}$ is

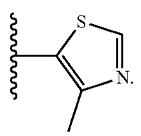 [SMILES: *c1scnc1C]

In some embodiments, $R^{7'}$ is selected from those depicted in Table 1, below.

As defined above and described herein, p is 0, 1, 2, 3, or 4.

In some embodiments, p is 0. In some embodiments, p is 1. In some embodiments, p is 2. In some embodiments, p is 3. In some embodiments, p is 4.

In some embodiments, p is selected from those depicted in Table 1, below.

As defined above and described herein, $L^{1'}$ is a covalent bond or a bivalent, saturated or partially unsaturated, straight or branched $C_{1-5}$ hydrocarbon chain, wherein 0-3 methylene units of $L^{1'}$ are independently replaced by —O—, —NR—, —CRF—, —$CF_2$—, —C(O)—, —S—, —S(O)—, or —$S(O)_2$—.

In some embodiments, $L^{1'}$ is covalent bond. In some embodiments, $L^{1'}$ is a bivalent, saturated or partially unsaturated, straight or branched $C_{1-5}$ hydrocarbon chain, wherein 0-3 methylene units of $L^{1'}$ are independently replaced by —O—, —NR—, —CRF—, —$CF_2$—, —C(O)—, —S—, —S(O)—, or —$S(O)_2$—. In some embodiments, $L^{1'}$ is

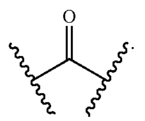 [SMILES: *C(*)=O]

In some embodiments, $L^{1'}$ is

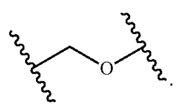 [SMILES: *CO*]

In some embodiments, $L^{1'}$ is

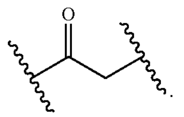 [SMILES: *CC(*)=O]

In some embodiments, $L^{1'}$ is

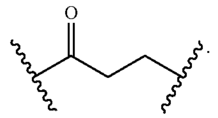 [SMILES: *CCC(*)=O]

In some embodiments, $L^{1'}$ is selected from those depicted in Table 1, below.

As defined above and described herein, $L^{2'}$ is a covalent bond or a bivalent, saturated or partially unsaturated, straight or branched $C_{1-5}$ hydrocarbon chain, wherein 0-3 methylene units of $L^{2'}$ are independently replaced by —O—, —NR—, —CRF—, —$CF_2$—, —C(O)—, —S—, —S(O)—, or —$S(O)_2$—.

In some embodiments, $L^{2'}$ is covalent bond. In some embodiments, $L^{2'}$ is a bivalent, saturated or partially unsaturated, straight or branched $C_{1-5}$ hydrocarbon chain, wherein 0-3 methylene units of $L^{2'}$ are independently replaced by —O—, —NR—, —CRF—, —$CF_2$—, —C(O)—, —S—, —S(O)—, or —$S(O)_2$—. In some embodiments, $L^{2'}$ is

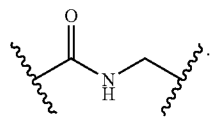 [SMILES: *CNC(*)=O]

In some embodiments, $L^{2'}$ is selected from those depicted in Table 1, below.

As defined above and described herein, Q' is a bivalent moiety selected from —O—, —$CR_2$—, —$CF_2$—, —CFR—, —C(O)—, —$OCR_2$—, and —C(S)—.

In some embodiments, Q' is —O—. In some embodiments, Q' is —$CR_2$—. In some embodiments, Q' is —$OCR_2$—. In some embodiments, Q' is —$CF_2$—. In some embodiments, Q' is —CFR—. In some embodiments, Q' is —C(O)—. In some embodiments, Q' is —C(S)—.

In some embodiments, Q' is selected from those depicted in Table 1, below.

As defined above and described herein, $X^1$ is an optionally substituted —$(CH_2)_x$—, wherein 1-2 methylenes of $X^1$ is optionally replaced with a bivalent group selected from —NR—, —N(COR)—, —N($CO_2R$)—, —N($SO_2R$)—, —N($CONR_2$)—, and —N($SO_2NR_2$)—.

In some embodiments, $X^1$ is an optionally substituted —$(CH_2)_x$—. In some embodiments, $X^1$ is an optionally substituted —$(CH_2)_x$—, wherein 1-2 methylenes of $X^1$ is replaced with a bivalent group selected from —NR—, —N(COR)—, —N($CO_2R$)—, —N($SO_2R$)—, —N($CONR_2$)—, and —N($SO_2NR_2$)—. In some embodiments, X' is

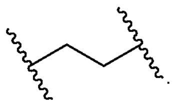 [SMILES: *CC*]

In some embodiments, X' is

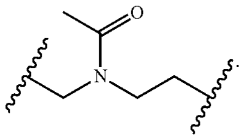 [SMILES: *CCN(C*)C(C)=O]

As defined above and described herein, x is 0, 1, 2, 3, 4, or 5.

In some embodiments, x is 0. In some embodiments, x is 1. In some embodiments, x is 2. In some embodiments, x is 3. In some embodiments, x is 4. In some embodiments, x is 5.

In some embodiments, x is selected from those depicted in Table 1, below.

As defined above and described herein, Y' is an optionally substituted $—(CH_2)_y—$.

In some embodiments, Y' is an optionally substituted $—(CH_2)_y—$. In some embodiments, Y' is $—CH_2—$. In some embodiments, Y' is

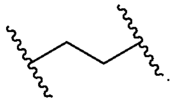 [SMILES: *CC*]

In some embodiments, Y' is selected from those depicted in Table 1, below.

As defined above and described herein, y is 0, 1, 2, or 3.

In some embodiments, y is 0. In some embodiments, y is 1. In some embodiments, y is 2. In some embodiments, y is 3.

In some embodiments, y is selected from those depicted in Table 1, below.

As defined above and described herein, $R^1$ is hydrogen or $R^A$.

In some embodiments, $R^1$ is hydrogen. In some embodiments, $R^{3'}$ is $R^A$. In some embodiments, $R^{3'}$ is

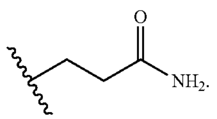 [SMILES: *CCC(N)=O]

In some embodiments, $R^{3'}$ is selected from those depicted in Table 1, below.

As defined above and described herein, $R^{a1}$ and $R^{a2}$ are each independently hydrogen, $R^A$, $—CH_2CO_2R$, or $—CH_2OCO_2R$.

In some embodiments, $R^{a1}$ is hydrogen. In some embodiments, $R^{a1}$ is $R^A$. In some embodiments, $R^{a1}$ is $—CH_2CO_2R$. In some embodiments, $R^{a1}$ is $—CH_2OCO_2R$. In some embodiments, $R^{a2}$ is hydrogen. In some embodiments, $R^{a2}$ is $R^A$. In some embodiments, $R^{a2}$ is $—CH_2CO_2R$. In some embodiments, $R^{a2}$ is $—CH_2OCO_2R$.

As defined above and described herein, Ring M' is an optionally substituted bivalent ring selected from phenylenyl, naphthylenyl, a 5-10 membered heteroarylenyl containing 1-4 heteroatoms independently selected from nitrogen, oxygen, or sulfur, a 5-11 membered saturated or partially unsaturated carbocyclylenyl or heterocyclylenyl with 1-4 heteroatoms independently selected from nitrogen, oxygen, or sulfur;

In some embodiments, Ring M' is an optionally substituted phenylenyl. In some embodiments, Ring M' is an optionally substituted naphthylenyl. In some embodiments, Ring M' is an optionally substituted 5-10 membered heteroarylenyl containing 1-4 heteroatoms independently selected from nitrogen, oxygen, or sulfur. In some embodiments, Ring M' is an optionally substituted 5-11 membered saturated or partially unsaturated carbocyclylenyl. In some embodiments, Ring M' is an optionally substituted 5-11 membered saturated or partially unsaturated heterocyclylenyl with 1-4 heteroatoms independently selected from nitrogen, oxygen, or sulfur. In some embodiments, Ring M' is

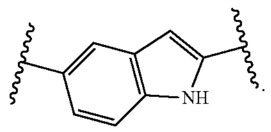 [SMILES: *c1ccc2[nH]c(*)cc2c1]

In some embodiments, Ring M' is selected from those depicted in Table 1, below.

As defined above and described herein, Ring D' is selected from phenyl, a 4-11 membered saturated or partially unsaturated monocyclic, bicyclic, bridged bicyclic, or spirocyclic carbocyclic or heterocyclic ring having 1-3 heteroatoms independently selected from nitrogen, oxygen, and sulfur, and a 5-6 membered heteroaryl with 1-4 heteroatoms independently selected from nitrogen, oxygen or sulfur.

In some embodiments, Ring D' is phenyl. In some embodiments, Ring D' is 4-11 membered saturated or partially unsaturated monocyclic, bicyclic, bridged bicyclic, or spirocyclic carbocyclic or heterocyclic ring having 1-3 heteroatoms independently selected from nitrogen, oxygen, and sulfur. In some embodiments, Ring D' is 5-6 membered heteroaryl with 1-4 heteroatoms independently selected from nitrogen, oxygen or sulfur.

In some embodiments, Ring D' is selected from those depicted in Table 1, below.

As defined above and described herein, Ring W' is an optionally substituted ring selected from a 5-9 membered saturated or partially unsaturated heterocyclyl.

In some embodiments, Ring W' is an optionally substituted ring selected from a 5-9 membered saturated or partially unsaturated heterocyclyl. In some embodiments, Ring W' is a 8-membered saturated heterocyclyl.

In some embodiments, Ring W' is selected from those depicted in Table 1, below.

As defined above and described herein, Ring U' is a ring selected from phenyl, a 5-6 membered heteroaryl containing 1-4 heteroatoms independently selected from nitrogen, oxygen, or sulfur, and a 5-7 membered saturated or partially unsaturated carbocyclyl or heterocyclyl with 1-3 heteroatoms independently selected from nitrogen, oxygen, or sulfur.

In some embodiments, Ring U' is phenyl. In some embodiments, Ring U' is a 5-6 membered heteroaryl containing 1-4 heteroatoms independently selected from nitrogen, oxygen, or sulfur. In some embodiments, Ring U' is a 5-7 membered saturated or partially unsaturated carbocyclyl or heterocyclyl with 1-3 heteroatoms independently selected from nitrogen, oxygen, or sulfur.

In some embodiments, Ring U' is selected from those depicted in Table 1, below.

As defined above and described herein, $R^{u'}$ is hydrogen, $R^A$, halogen, —CN, —$NO_2$, —OR, —SR, —$NR_2$, —$SiR_3$, —$S(O)_2R$, —$S(O)_2NR_2$, —S(O)R, —C(O)R, —C(O)OR, —$C(O)NR_2$, —C(O)NROR, —$CR_2NRC(O)R$, —$CR_2NRC(O)NR_2$, —OC(O)R, —$OC(O)NR_2$, —$OP(O)R_2$, —$OP(O)(OR)_2$, —$OP(O)(OR)NR_2$, —$OP(O)(NR_2)_2$, —NRC(O)OR, —NRC(O)R, —$NRC(O)NR_2$, —$NRS(O)_2R$, —$NP(O)R_2$, —$NRP(O)(OR)_2$, —$NRP(O)(OR)NR_2$, —$NRP(O)(NR_2)_2$, or —$NRS(O)_2R$.

In some embodiments, $R^{u'}$ is hydrogen. In some embodiments, $R^{u'}$ is $R^A$. In some embodiments, $R^{u'}$ is halogen. In some embodiments, $R^{u'}$ is —CN. In some embodiments, $R^{u'}$ is —$NO_2$. In some embodiments, $R^{3'}$ is —OR. In some embodiments, $R^{3'}$ is —SR. In some embodiments, $R^{3'}$ is —$NR_2$. In some embodiments, $R^{3'}$ is —$SiR_3$. In some embodiments, $R^{3'}$ is —$S(O)_2R$. In some embodiments, $R^{u'}$ is —$S(O)_2NR_2$. In some embodiments, $R^{3'}$ is —S(O)R. In some embodiments, $R^{3'}$ is —C(O)R. In some embodiments, $R^{3'}$ is —C(O)OR. In some embodiments, $R^{3'}$ is —$C(O)NR_2$. In some embodiments, $R^{\cdot}$ is —C(O)NROR. In some embodiments, $R^{3'}$ is —$CR_2NRC(O)R$. In some embodiments, $R^{3'}$ is —$CR_2NRC(O)NR_2$. In some embodiments, $R^{3'}$ is —OC(O)R. In some embodiments, $R^{3'}$ is —$OC(O)NR_2$. In some embodiments, $R^{3'}$ is —$OP(O)R_2$. In some embodiments, $R^{3'}$ is —$OP(O)(OR)_2$. In some embodiments, $R^{3'}$ is —$OP(O)(OR)NR_2$. In some embodiments, $R^{3'}$ is —$OP(O)(NR_2)_2$. In some embodiments, $R^{3'}$ is —NRC(O)OR. In some embodiments, $R^{3'}$ is —NRC(O)R. In some embodiments, $R^{3'}$ is —$NRC(O)NR_2$. In some embodiments, $R^{3'}$ is —$NRS(O)_2R$. In some embodiments, $R^{3'}$ is —$NP(O)R_2$. In some embodiments, $R^{u'}$ is —$NRP(O)(OR)_2$. In some embodiments, $R^{3'}$ is —$NRP(O)(OR)NR_2$. In some embodiments, $R^{3'}$ is —$NRP(O)(NR_2)_2$. In some embodiments, $R^{3'}$ is —$NRS(O)_2R$. In some embodiments, $R^{3'}$ is -iPr. In some embodiments, $R^{3'}$ is —$S(O)_2$iPr. In some embodiments, $R^{3'}$ is —$S(O)_2CH_3$.

As defined above and described herein, u is 0, 1, 2, 3, or 4.

In some embodiments, u is 0. In some embodiments, u is 1. In some embodiments, u is 2. In some embodiments, u is 3. In some embodiments, u is 4.

In some embodiments, u is selected from those depicted in Table 1, below.

As defined above and described herein, Ring V' is an optionally substituted fused ring selected from a 6-membered aryl, a 5-6 membered heteroaryl containing 1-4 heteroatoms independently selected from nitrogen, oxygen, or sulfur, and a 5-7 membered saturated or partially unsaturated carbocyclyl or heterocyclyl with 1-3 heteroatoms independently selected from nitrogen, oxygen, or sulfur.

In some embodiments, Ring V' is an optionally substituted 6-membered aryl. In some embodiments, Ring V' is an optionally substituted 5-6 membered heteroaryl containing 1-4 heteroatoms independently selected from nitrogen, oxygen, or sulfur. In some embodiments, Ring V' is an optionally substituted 5-7 membered saturated or partially unsaturated carbocyclyl or heterocyclyl with 1-3 heteroatoms independently selected from nitrogen, oxygen, or sulfur. In some embodiments, Ring V' is a 6-membered aryl.

In some embodiments, Ring V' is selected from those depicted in Table 1, below.

As defined above and described herein, Ring Z' is a bivalent ring selected from phenylenyl, a 4-7 membered saturated or partially unsaturated carbocyclylenyl or heterocyclylenyl having 1-2 heteroatoms independently selected from nitrogen, oxygen, and sulfur, and a 5-6 membered heteroarylenyl having 1-4 heteroatoms independently selected from nitrogen, oxygen, and sulfur.

In some embodiments, Ring Z' is phenylenyl. In some embodiments, Ring Z' is a 4-7 membered saturated or partially unsaturated carbocyclylenyl. In some embodiments, Ring Z' is a heterocyclylenyl having 1-2 heteroatoms independently selected from nitrogen, oxygen, and sulfur. In some embodiments, Ring Z' is a 5-6 membered heteroarylenyl having 1-4 heteroatoms independently selected from nitrogen, oxygen, and sulfur. In some embodiments, Ring Z' is

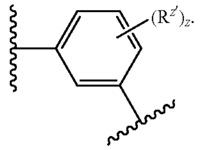

In some embodiments, Ring Z' is

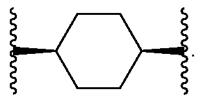 [SMILES: *[C@H]1CC[C@@H](*)CC1]

In some embodiments, Ring Z' is

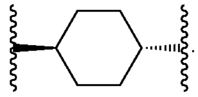 [SMILES: *[C@H]1CC[C@H](*)CC1]

In some embodiments, Ring Z' is selected from those depicted in Table 1, below.

As defined above and described herein, $R^{z'}$ is hydrogen, $R^A$, halogen, —CN, —$NO_2$, —OR, —SR, —$NR_2$, —$SiR_3$, —$S(O)_2R$, —$S(O)_2NR_2$, —S(O)R, —C(O)R, —C(O)OR, —$C(O)NR_2$, —C(O)NROR, —$CR_2NRC(O)R$, —$CR_2NRC(O)NR_2$, —OC(O)R, —$OC(O)NR_2$, —$OP(O)R_2$, —$OP(O)(OR)_2$, —$OP(O)(OR)NR_2$, —$OP(O)(NR_2)_2$, —NRC(O)OR, —NRC(O)R, —$NRC(O)NR_2$, —$NRS(O)_2R$, —$NP(O)R_2$, —$NRP(O)(OR)_2$, —$NRP(O)(OR)NR_2$, —$NRP(O)(NR_2)_2$, or —$NRS(O)_2R$.

In some embodiments, $R^{z'}$ is hydrogen. In some embodiments, $R^{z'}$ is $R^A$. In some embodiments, $R^{z'}$ is halogen. In some embodiments, $R^{z'}$ is —CN. In some embodiments, $R^{z'}$ is —$NO_2$. In some embodiments, $R^{z'}$ is —OR. In some embodiments, $R^{z'}$ is —SR. In some embodiments, $R^{z'}$ is —$NR_2$. In some embodiments, $R^{z'}$ is —$SiR_3$. In some embodiments, $R^{z'}$ is —$S(O)_2R$. In some embodiments, $R^{z'}$ is —$S(O)_2NR_2$. In some embodiments, $R^{z'}$ is —S(O)R, —C(O)R. In some embodiments, $R^{z'}$ is —C(O)OR. In some embodiments, $R^{z'}$ is —$C(O)NR_2$. In some embodiments, $R^{z'}$ is —C(O)NROR. In some embodiments, $R^{z'}$ is —$CR_2NRC(O)R$. In some embodiments, $R^{z'}$ is —$CR_2NRC(O)NR_2$. In some embodiments, $R^{z'}$ is —OC(O)R. In some embodiments, $R^{z'}$ is —$OC(O)NR_2$. In some embodiments, $R^{z'}$ is —$OP(O)R_2$. In some embodiments, $R^{z'}$ is —$OP(O)(OR)_2$. In some embodiments, $R^{z'}$ is —OP(O)(OR)$NR_2$. In some embodiments, $R^{z'}$ is —OP(O)$(NR_2)_2$. In some embodiments, $R^{z'}$ is —NRC(O)OR. In some embodiments, $R^{z'}$ is —NRC(O)R. In some embodiments, $R^{z'}$ is —NRC(O)$NR_2$. In some embodiments, $R^{z'}$ is —NRS$(O)_2$R. In some embodiments, $R^{z'}$ is —NP(O)$R_2$. In some embodiments, $R^{z'}$ is —NRP(O)$(OR)_2$. In some embodiments, $R^{z'}$ is —NRP(O)(OR)$NR_2$. In some embodiments, $R^{z'}$ is —NRP(O)$(NR_2)_2$. In some embodiments, $R^{z'}$ is —NRS$(O)_2$R. In some embodiments, $R^{z'}$ is —$CH_3$. In some embodiments, $R^{z'}$ is —Cl. In some embodiments, $R^{z'}$ is —F.

In some embodiments, $R^{z'}$ is selected from those depicted in Table 1, below.

As defined above and described herein, z is 0, 1, 2, 3 or 4.

In some embodiments, z is 0. In some embodiments, z is 1. In some embodiments, z is 2. In some embodiments, z is 3. In some embodiments, z is 4.

In some embodiments, z is selected from those depicted in Table 1, below.

As defined above and described herein, n is 0 or 1.

In some embodiments, n is 0. In some embodiments, n is 1.

In some embodiments, n is selected from those depicted in Table 1, below.

In some embodiments, the present invention provides a compound of formula II-r", wherein DIM is

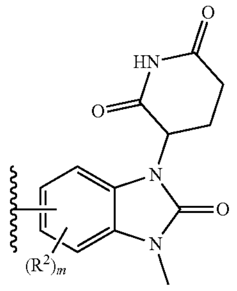

as shown, to provide a compound of formula II-r"-13:

II-r"-13

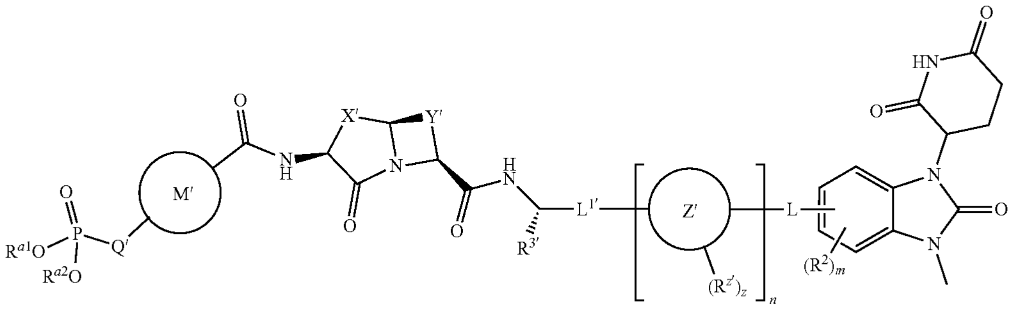

or a pharmaceutically acceptable salt thereof, wherein each of $R^2$, m, L, $L^{1'}$, Ring M', Ring Z', $R^{3'}$, Q', X', Y', $R^{a1}$, $R^{a2}$, $R^{z'}$, z, and n is as defined above and described in embodiments herein, both singly and in combination.

In some embodiments, the present invention provides a compound of formula II-r", wherein DIM is

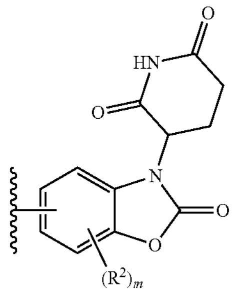

as shown, to provide a compound of formula II-r"-14:

II-r"-14

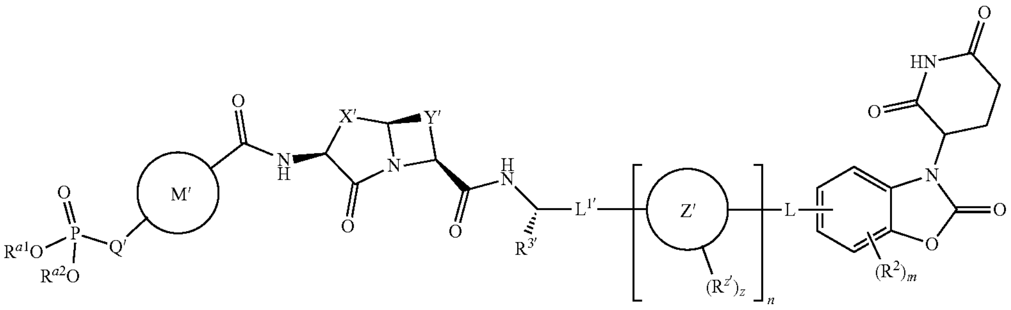

or a pharmaceutically acceptable salt thereof, wherein each of $R^2$, m, L, $L^{1'}$, Ring M', Ring Z', $R^{3'}$, Q', X', Y', $R^{a1}$, $R^{a2}$, $R^{z'}$, z, and n is as defined above and described in embodiments herein, both singly and in combination.

In some embodiments, the present invention provides a compound of formula II-r", wherein DIM is

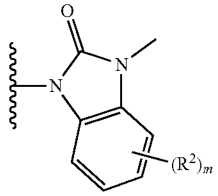

as shown, to provide a compound of formula II-r"-15:

II-r"-15

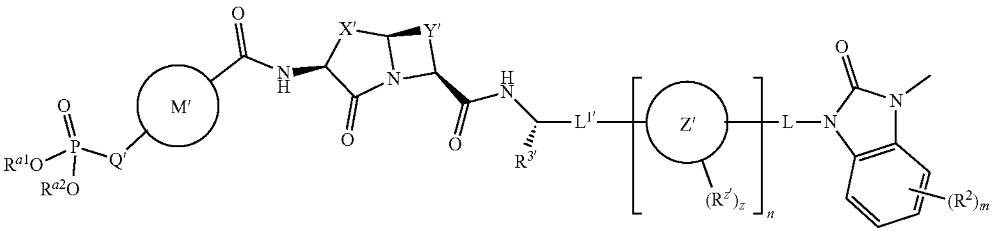

or a pharmaceutically acceptable salt thereof, wherein each of $R^2$, m, L, $L^{1'}$, Ring M', Ring Z', $R^{3'}$, Q', X', Y', $R^{a1}$, $R^{a2}$, $R^{z'}$, z, and n is as defined above and described in embodiments herein, both singly and in combination.

In some embodiments, the present invention provides a compound of formula II-r", wherein DIM is

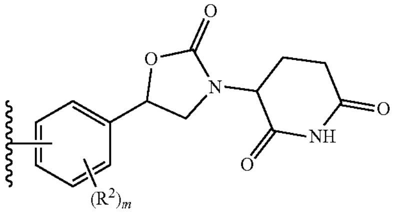

as shown, to provide a compound of formula II-r"-16:

II-r"-16

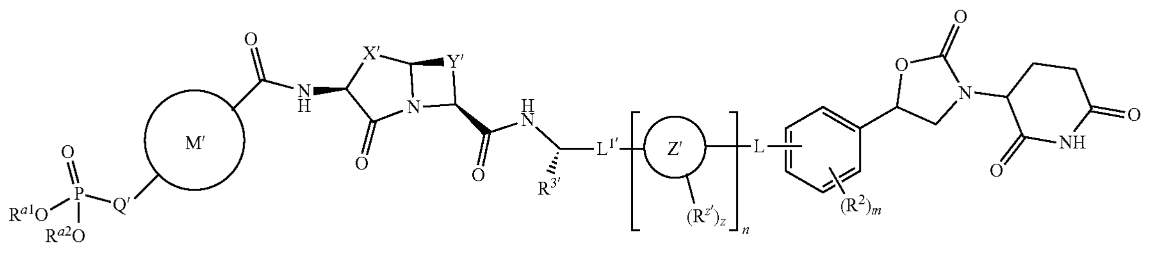

or a pharmaceutically acceptable salt thereof, wherein each of $R^2$, m, L, $L^{1'}$, Ring M', Ring Z', $R^{3'}$, Q', X', Y', $R^{a1}$, $R^2$, $R^{z'}$, z, and n is as defined above and described in embodiments herein, both singly and in combination.

In some embodiments, the present invention provides a compound of formula II-r", wherein DIM is

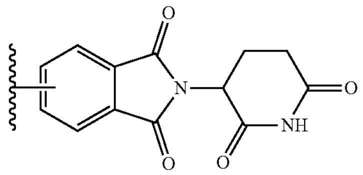

as shown, to provide a compound of formula II-r"-17:

II-r"-17

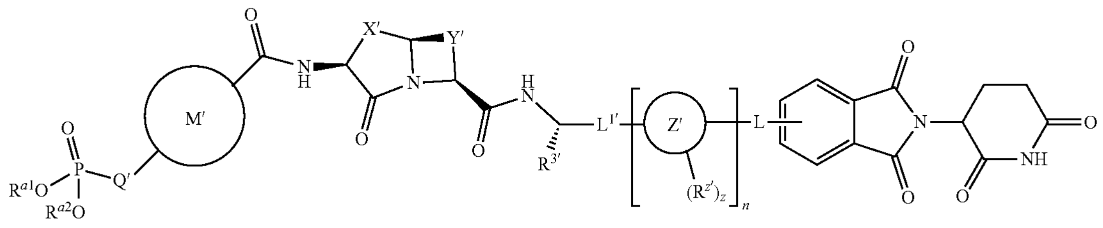

or a pharmaceutically acceptable salt thereof, wherein each of L, $L^{1'}$, Ring M', Ring Z', $R^{3'}$, Q', X', Y', $R^{a1}$, $R^{a2}$, $R^{*}$, z, and n is as defined above and described in embodiments herein, both singly and in combination.

In some embodiments, the present invention provides a compound of formula II-r", wherein DIM is

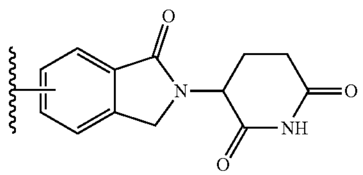

as shown, to provide a compound of formula II-r"-18:

II-r"-18

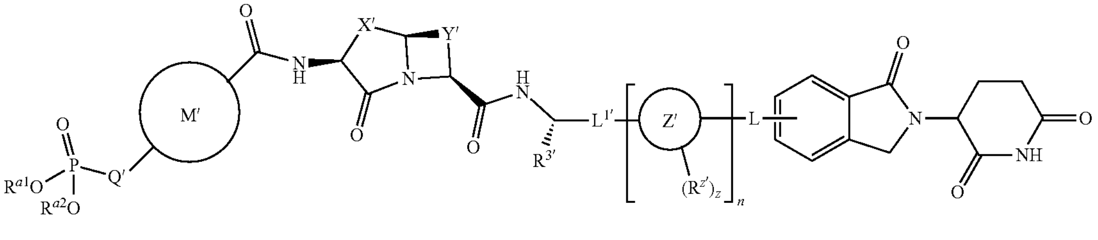

or a pharmaceutically acceptable salt thereof, wherein each of L, $L^{1'}$, Ring M', Ring Z', $R^{3'}$, Q', X', Y', $R^{a1}$, $R^{a2}$, $R^{z'}$, z, and n is as defined above and described in embodiments herein, both singly and in combination.

In some embodiments, the present invention provides a compound of formula II-r", wherein DIM is

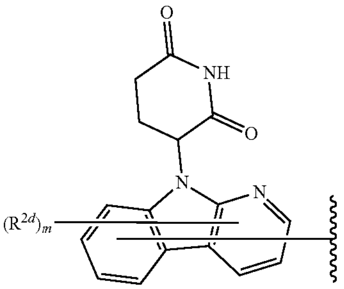

as shown, to provide a compound of formula II-r"-19:

II-r"-19

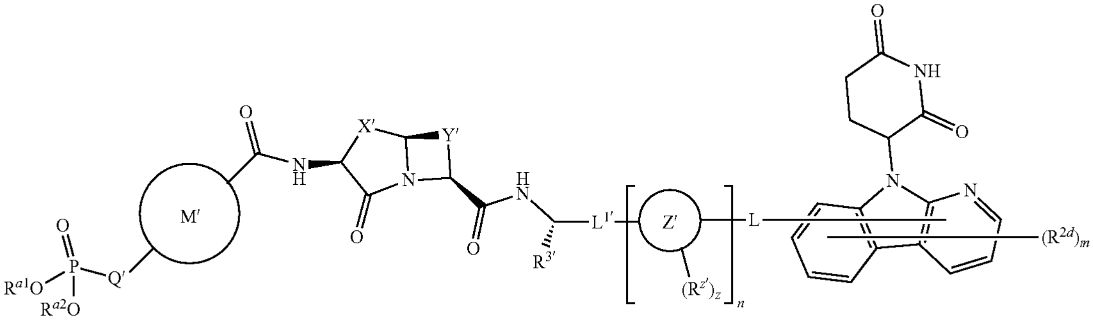

or a pharmaceutically acceptable salt thereof, wherein each of $R^{2'}$, m, L, $L^{1'}$, Ring M', Ring Z', $R^{3'}$, Q', X', Y', $R^{a1}$, $R^{a2}$, $R^{z'}$, z, and n is as defined above and described in embodiments herein, both singly and in combination.

In some embodiments herein, structures depicted as

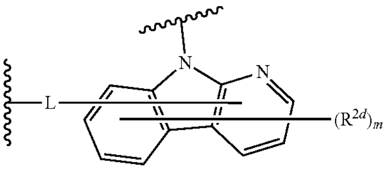

can include, for example structures

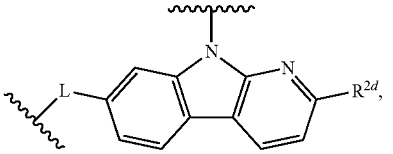

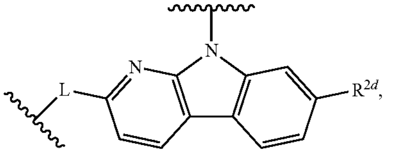

-continued

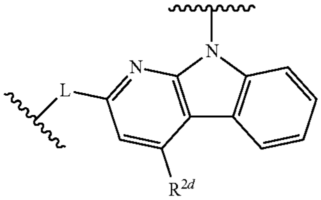

etc.

In some embodiments, the present invention provides a compound of formula II-r", wherein DIM is

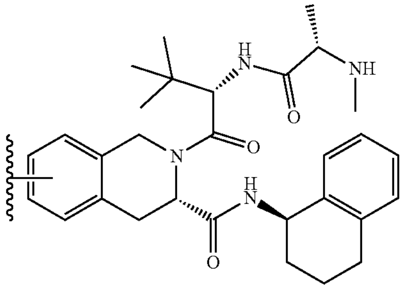

as shown, to provide a compound of formula II-r"-20:

II-r"-20

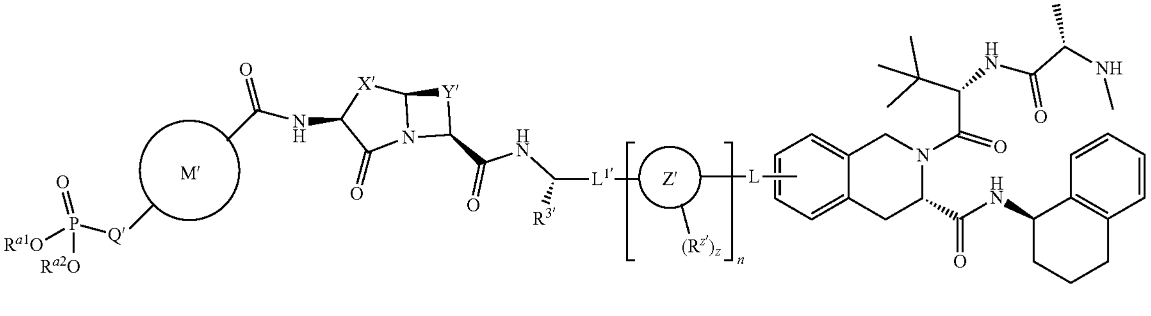

or a pharmaceutically acceptable salt thereof, wherein each of L, $L^{1'}$, Ring M', Ring Z', $R^{3'}$, Q', X', Y', $R^{a1}$, $R^{a2}$, $R^{z'}$, z, and n is as defined above and described in embodiments herein, both singly and in combination.

In some embodiments, the present invention provides a compound of formula II-r", wherein DIM is

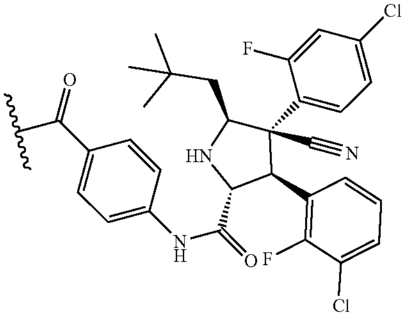 [SMILES: *C(=O)c1ccc(NC(=O)[C@@H]2N[C@@H](CC(C)(C)C)[C@](C#N)(c3ccc(Cl)cc3F)[C@H]2c2cccc(Cl)c2F)cc1]

as shown, to provide a compound of formula II-r"-21:

II-r"-21

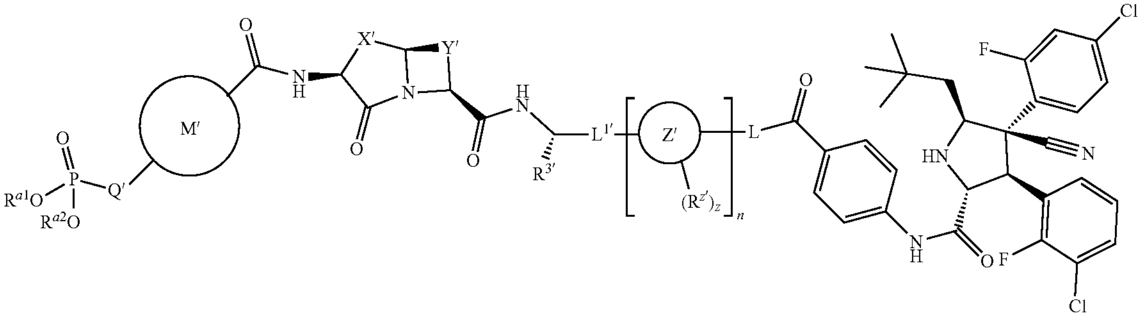

or a pharmaceutically acceptable salt thereof, wherein each of L, $L^{1'}$, Ring M', Ring Z', $R^{3'}$, Q', X', Y', $R^{a1}$, $R^{a2}$, $R^{z'}$, z, and n is as defined above and described in embodiments herein, both singly and in combination.

In some embodiments, the present invention provides a compound of formula II-r", wherein DIM is

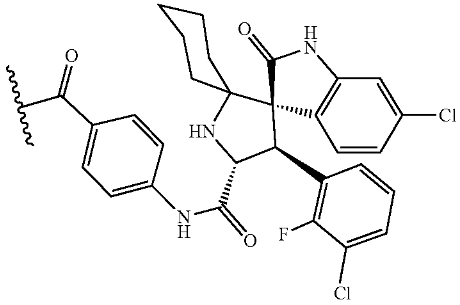 [SMILES: *C(=O)c1ccc(NC(=O)[C@@H]2NC3(CCCCC3)[C@@]3(C(=O)Nc4cc(Cl)ccc43)[C@H]2c2cccc(Cl)c2F)cc1]

as shown, to provide a compound of formula II-r"-22:

II-r"-22

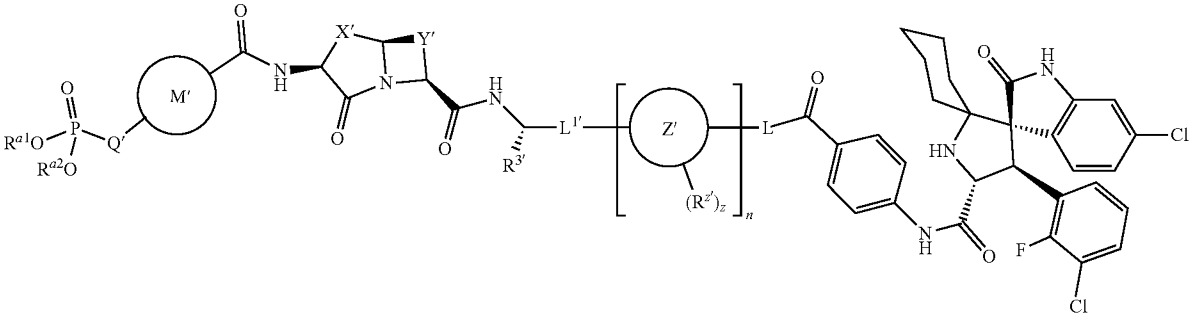

or a pharmaceutically acceptable salt thereof, wherein each of L, $L^{1'}$, Ring M', Ring Z', $R^{3'}$, Q', X', Y', $R^{a1}$, $R^{a2}$, $R^{z'}$, z, and n is as defined above and described in embodiments herein, both singly and in combination.

In some embodiments, the present invention provides a compound of formula II-r", wherein DIM is

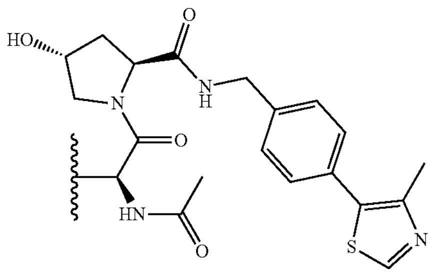 [SMILES: *[C@H](NC(C)=O)C(=O)N1C[C@H](O)C[C@H]1C(=O)NCc1ccc(-c2scnc2C)cc1]

as shown, to provide a compound of formula II-r"-23:

II-r"-23

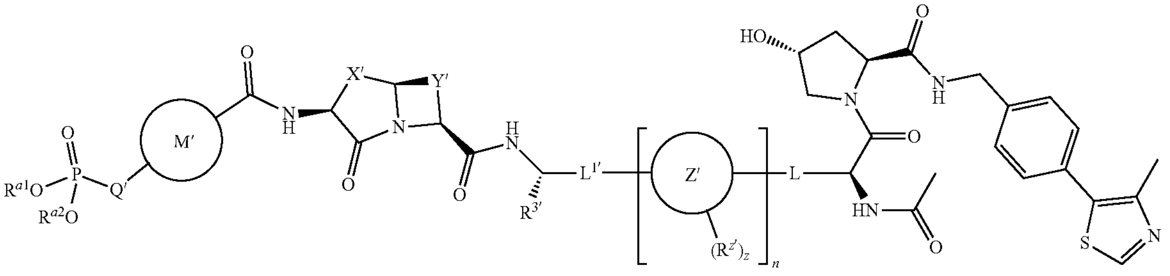

or a pharmaceutically acceptable salt thereof, wherein each of L, $L^{1'}$, Ring M', Ring Z', $R^{3'}$, Q', X', Y', $R^{a}$, $R^{a2}$, $R^{z'}$, z, and n is as defined above and described in embodiments herein, both singly and in combination.

In some embodiments, the present invention provides a compound of formula II-r", wherein DIM is

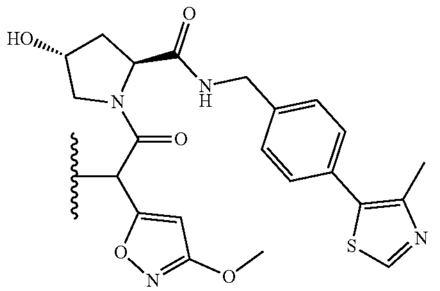 [SMILES: *C(C(=O)N1C[C@H](O)C[C@H]1C(=O)NCc1ccc(-c2scnc2C)cc1)c1cc(OC)no1]

as shown, to provide a compound of formula II-r"-24:

II-r"-24

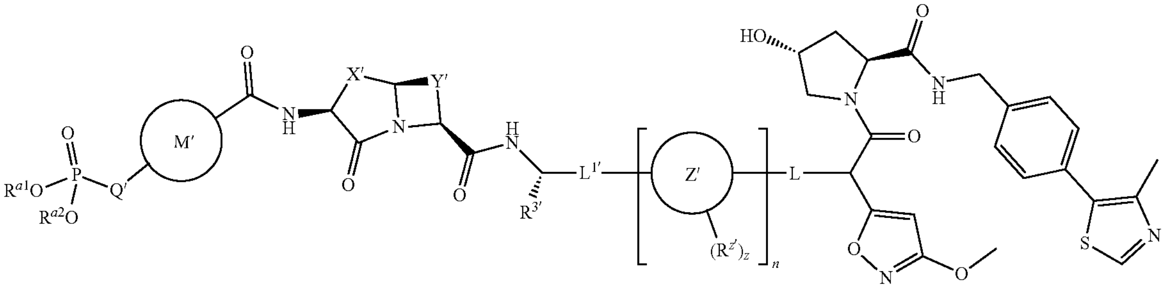

or a pharmaceutically acceptable salt thereof, wherein each of L, $L^{1'}$, Ring M', Ring Z', $R^{3'}$, Q', X', Y', $R^{a1}$, $R^{a2}$, $R^{z'}$, z, and n is as defined above and described in embodiments herein, both singly and in combination.

In some embodiments, the present invention provides a compound of formula II-r", wherein DIM is

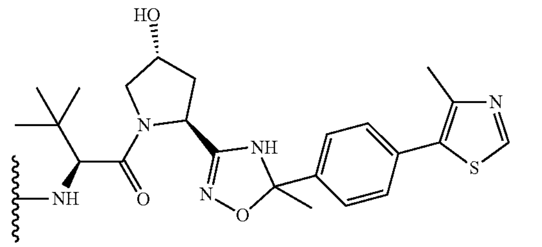 [SMILES: *N[C@H](C(=O)N1C[C@H](O)C[C@H]1C1=NOC(C)(c2ccc(-c3scnc3C)cc2)N1)C(C)(C)C]

as shown, to provide a compound of formula II-r"-25:

II-r"-25

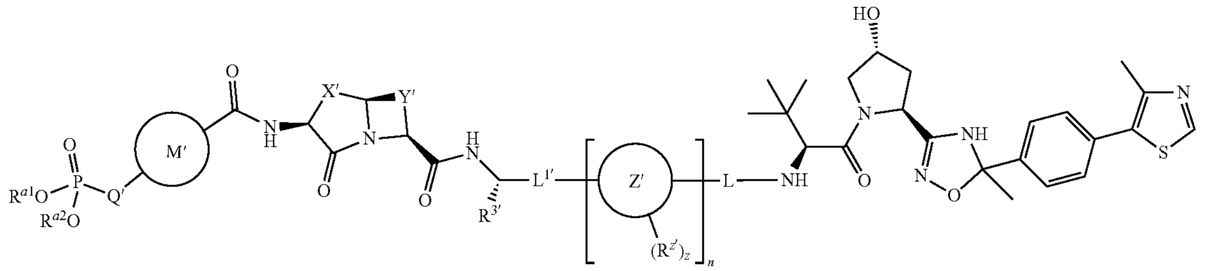

or a pharmaceutically acceptable salt thereof, wherein each of L, $L^{1'}$, Ring M', Ring Z', $R^{3'}$, Q', X', Y', $R^{a1}$, $R^{a2}$, $R^{z'}$, z, and n is as defined above and described in embodiments herein, both singly and in combination.

In some embodiments, the present invention provides a compound of formula II-r", wherein DIM is

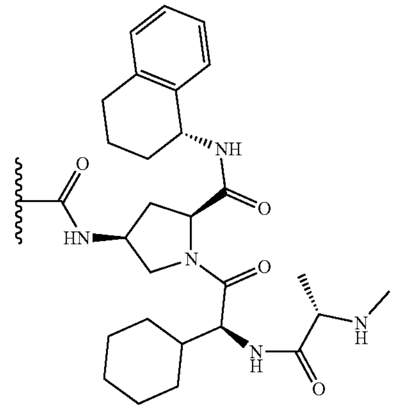 [SMILES: *C(=O)N[C@H]1C[C@@H](C(=O)N[C@@H]2CCCc3ccccc32)N(C(=O)[C@@H](NC(=O)[C@H](C)NC)C2CCCCC2)C1]

as shown, to provide a compound of formula II-r"-26:

II-r"-26

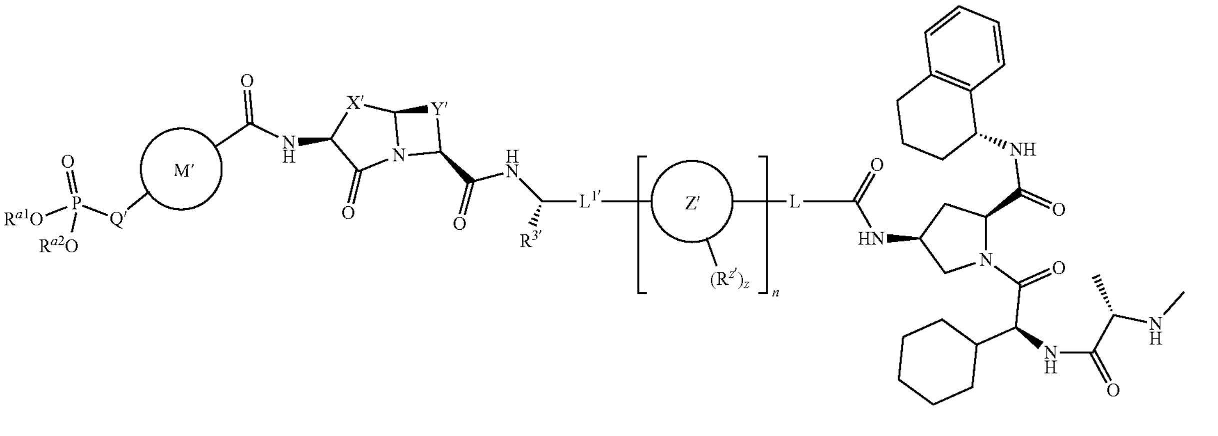

or a pharmaceutically acceptable salt thereof, wherein each of L, $L^{1'}$, Ring M', Ring Z', $R^{3'}$, Q', X', Y', $R^{a1}$, $R^{a2}$, $R^{z'}$, z, and n is as defined above and described in embodiments herein, both singly and in combination.

In some embodiments, the present invention provides a compound of formula II-r", wherein DIM is

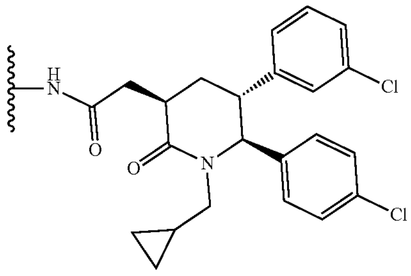 [SMILES: *NC(=O)C[C@H]1C[C@H](c2cccc(Cl)c2)[C@@H](c2ccc(Cl)cc2)N(CC2CC2)C1=O]

as shown, to provide a compound of formula II-r"-27:

II-r"-27

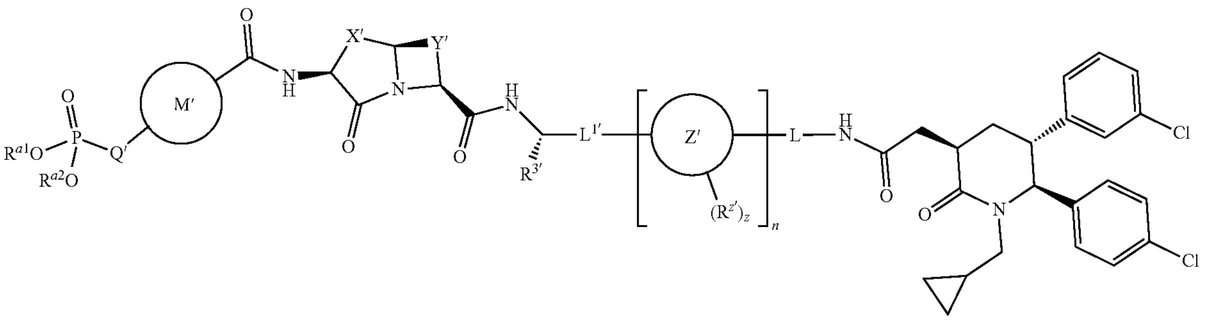

or a pharmaceutically acceptable salt thereof, wherein each of L, $L^{1'}$, Ring M', Ring Z', $R^{3'}$, Q', X', Y', $R^{a1}$, $R^{a2}$, $R^{z'}$, z, and n is as defined above and described in embodiments herein, both singly and in combination.

In some embodiments, the present invention provides a compound of formula II-r", wherein DIM is

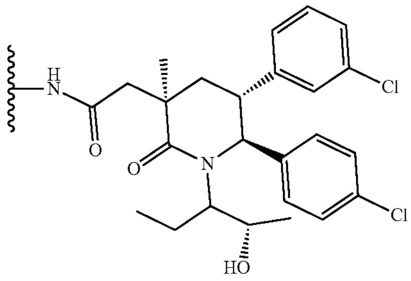 [SMILES: *NC(=O)C[C@@]1(C)C[C@H](c2cccc(Cl)c2)[C@@H](c2ccc(Cl)cc2)N(C(CC)[C@H](C)O)C1=O]

as shown, to provide a compound of formula II-r"-28:

II-r"-28

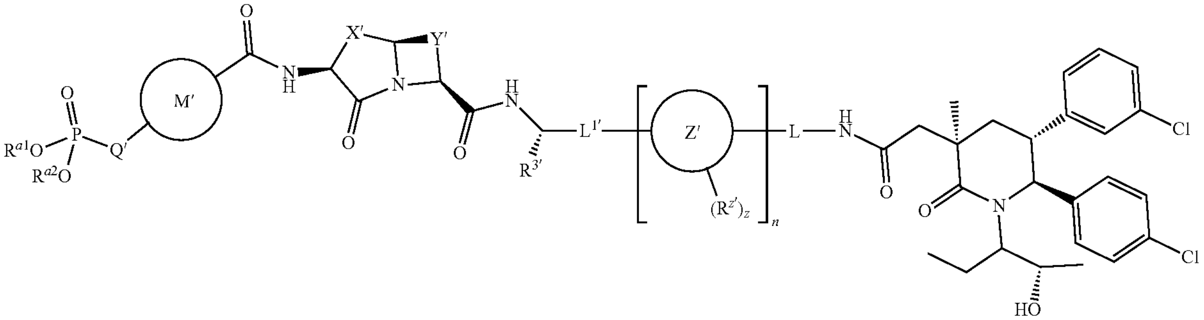

or a pharmaceutically acceptable salt thereof, wherein each of L, $L^{1'}$, Ring M', Ring Z', $R^{3'}$, Q', X', Y', $R^{a1}$, $R^{a2}$, $R^{z'}$, z, and n is as defined above and described in embodiments herein, both singly and in combination.

In some embodiments, the present invention provides a compound of formula II-r", wherein DIM is

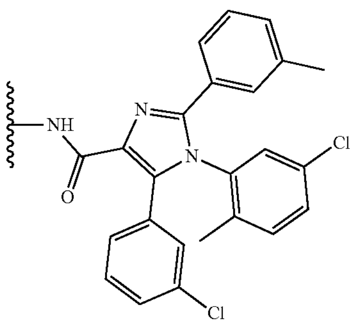 [SMILES: *NC(=O)c1nc(-c2cccc(C)c2)n(-c2cc(Cl)ccc2C)c1-c1cccc(Cl)c1]

as shown, to provide a compound of formula II-r"-20:

II-r"-29

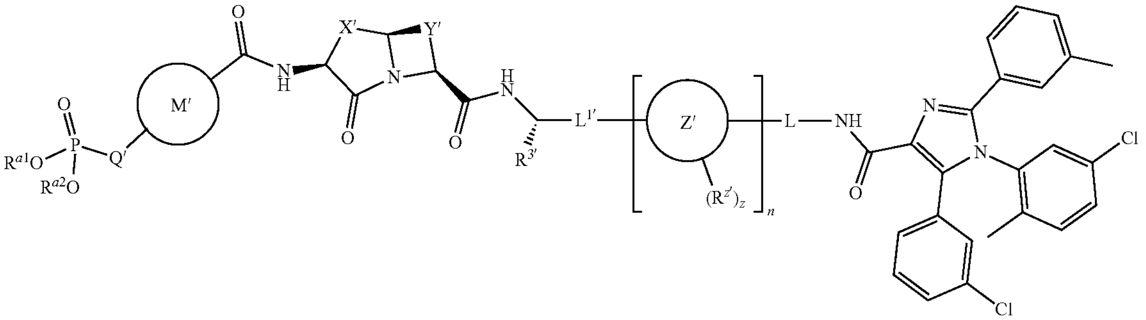

or a pharmaceutically acceptable salt thereof, wherein each of L, $L^{1'}$, Ring M', Ring Z', $R^{3'}$, Q', X', Y', $R^{a1}$, $R^{a2}$, $R^{z'}$, z, and n is as defined above and described in embodiments herein, both singly and in combination.

In some embodiments, the present invention provides a compound of formula II-r", wherein DIM is

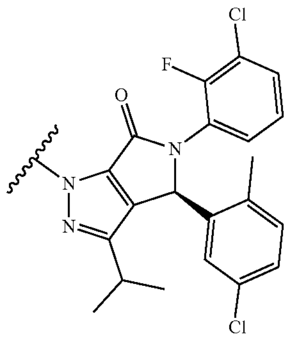 [SMILES: *n1nc(C(C)C)c2c1C(=O)N(c1cccc(Cl)c1F)[C@H]2c1cc(Cl)ccc1C]

as shown, to provide a compound of formula II-r"-30:

II-r"-30

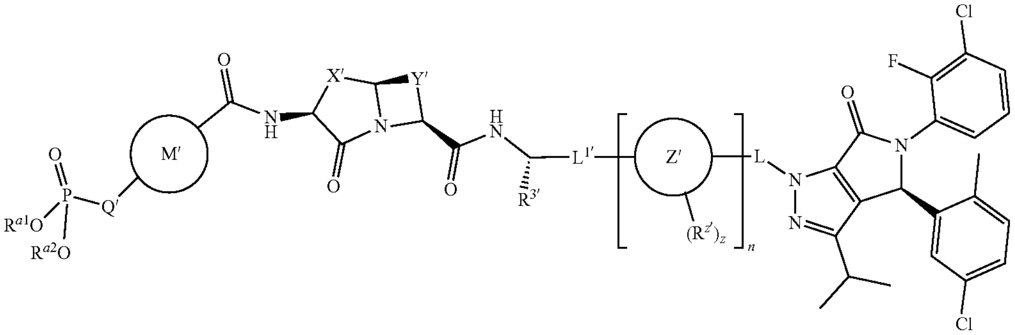

or a pharmaceutically acceptable salt thereof, wherein each of L, $L^{1'}$, Ring M', Ring Z', $R^{3'}$, Q', X', Y', $R^{a1}$, $R^{a2}$, $R^{\bullet}$, z, and n is as defined above and described in embodiments herein, both singly and in combination.

In some embodiments, the present invention provides a compound of formula II-r"-7, wherein DIM is

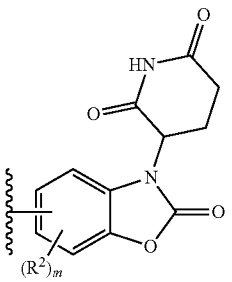

as shown, to provide a compound of formula II-r"-31:

II-r"-31

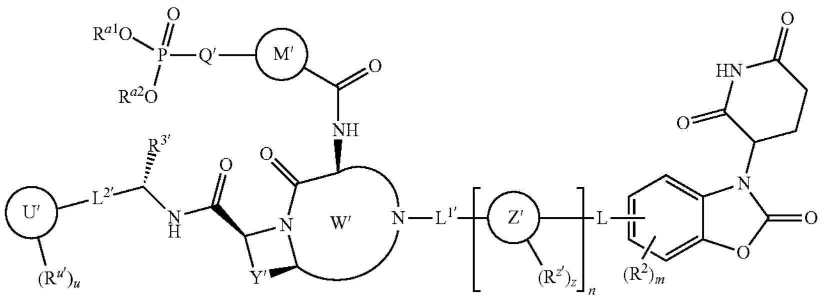

or a pharmaceutically acceptable salt thereof, wherein each of $R^2$, m, L, $L^{1'}$, $L^{2'}$, Ring M', Ring U', Ring W', Ring Z', $R^{3'}$, Y', Q', $R^{a1}$, $R^{a2}$, $R^{z'}$, z, and n is as defined above and described in embodiments herein, both singly and in combination.

In some embodiments, the present invention provides a compound of formula II-r"-7, wherein DIM is

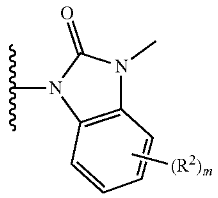

as shown, to provide a compound of formula II-r"-32:

II-r"-32

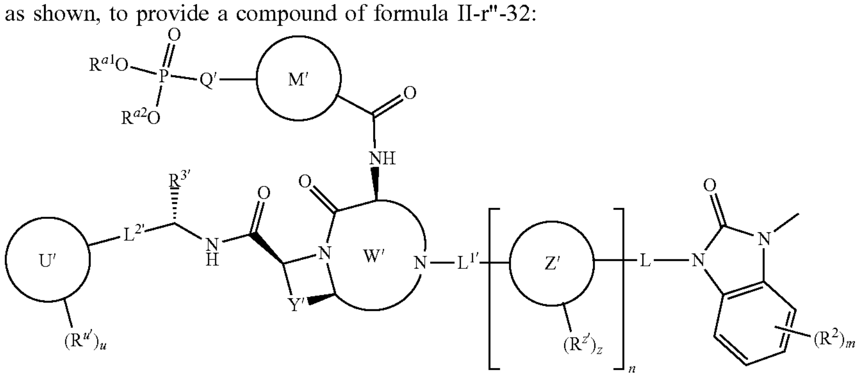

or a pharmaceutically acceptable salt thereof, wherein each of $R^2$, m, L, $L^{1'}$, $L^{2'}$, Ring M', Ring U', Ring W', Ring Z', $R^{3'}$, Y', Q', $R^{a1}$, $R^{a2}$, $R^{z'}$, z, and n is as defined above and described in embodiments herein, both singly and in combination.

In some embodiments, the present invention provides a compound of formula II-r"-7, wherein DIM is

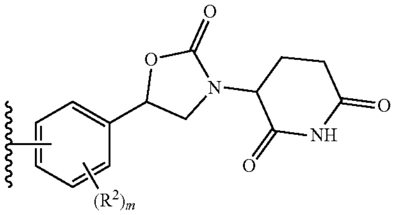

as shown, to provide a compound of formula II-r"-33:

II-r"-33

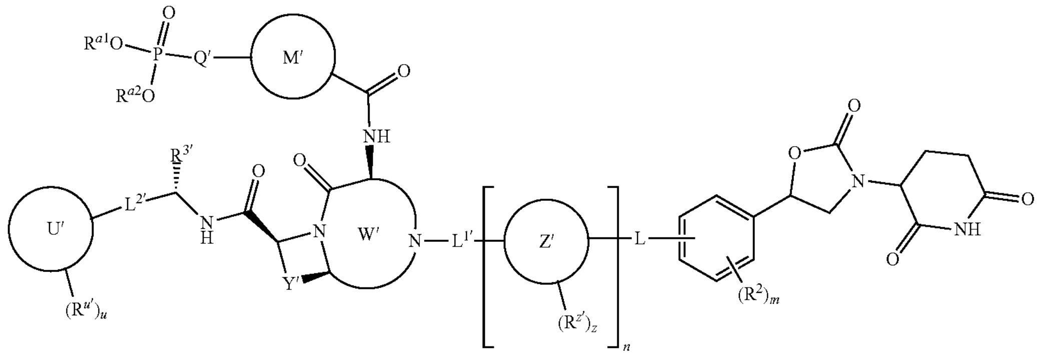

or a pharmaceutically acceptable salt thereof, wherein each of $R^2$, m, L, $L^{1'}$, $L^{2'}$, Ring M', Ring U', Ring W', Ring Z', $R^{3'}$, Y', Q', $R^{a1}$, $R^{a2}$, $R^{z'}$, z, and n is as defined above and described in embodiments herein, both singly and in combination.

In some embodiments, the present invention provides a compound of formula II-r"-7, wherein DIM is

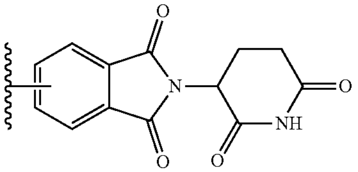

as shown, to provide a compound of formula II-r"-34:

II-r"-34

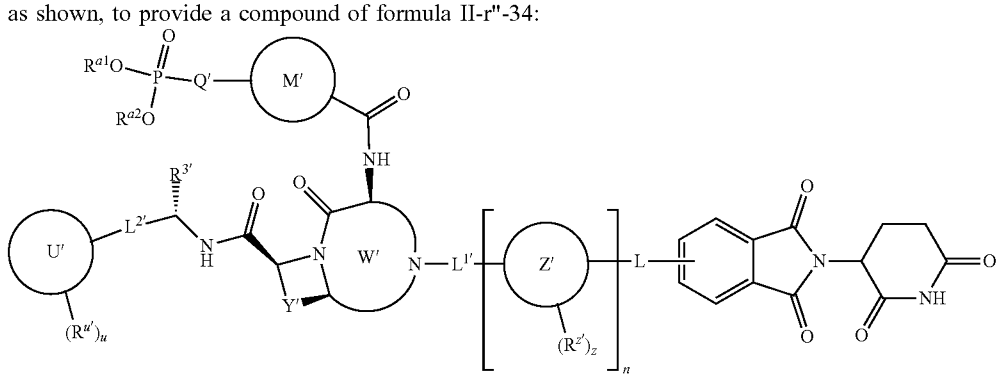

or a pharmaceutically acceptable salt thereof, wherein each of L, $L^{1'}$, $L^{2'}$, Ring M', Ring U', Ring W', Ring Z', $R^{3'}$, Y', Q', $R^{a1}$, $R^{a2}$, $R^{z'}$, z, and n is as defined above and described in embodiments herein, both singly and in combination.

In some embodiments, the present invention provides a compound of formula II-r"-7, wherein DIM is

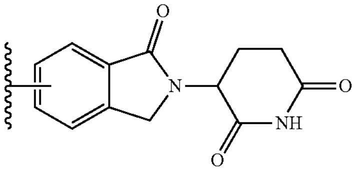

as shown, to provide a compound of formula II-r"-35:

II-r"-35

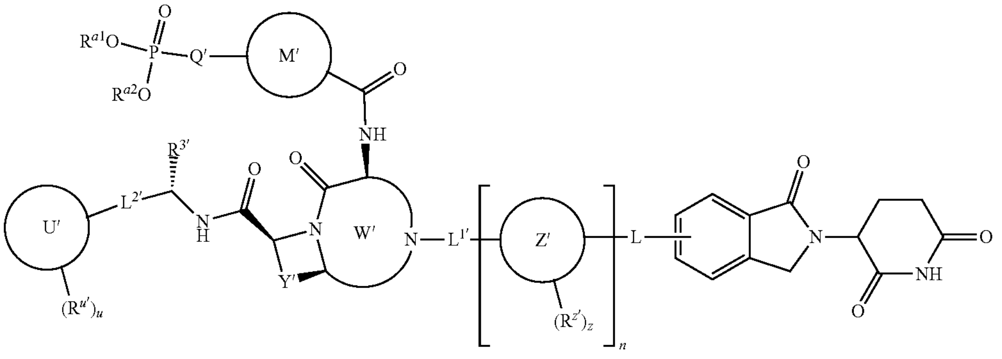

or a pharmaceutically acceptable salt thereof, wherein each of L, $L^{1'}$, $L^{2'}$, Ring M', Ring U', Ring W', Ring Z', $R^{3'}$, Y', Q', $R^{a1}$, $R^{a2}$, $R^{z'}$, z, and n is as defined above and described in embodiments herein, both singly and in combination.

In some embodiments, the present invention provides a compound of formula II-r"-7, wherein DIM is

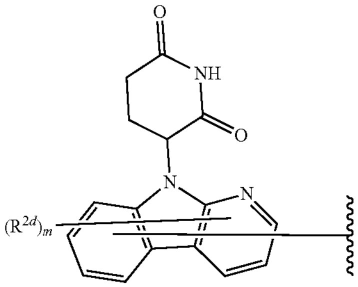

as shown, to provide a compound of formula II-r"-36:

II-r"-36

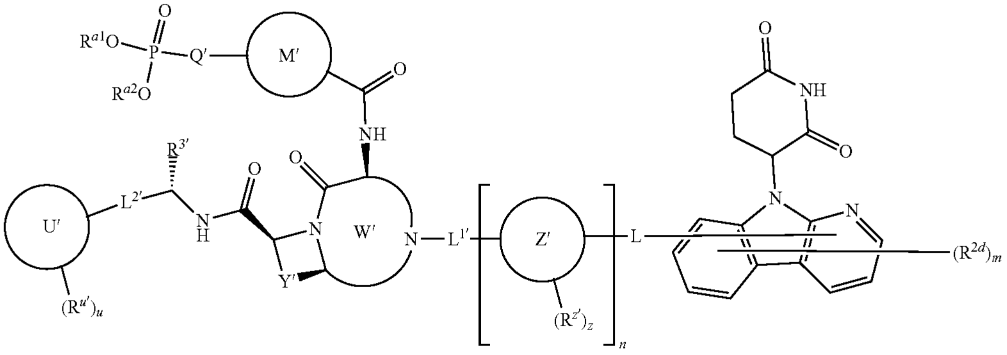

or a pharmaceutically acceptable salt thereof, wherein each of $R^{2d}$, m, L, $L^{1'}$, $L^{2'}$, Ring M', Ring U', Ring W', Ring Z', $R^{3'}$, Y', Q', $R^{a1}$, $R^{a2}$, $R^{z'}$, z, and n is as defined above and described in embodiments herein, both singly and in combination.

In some embodiments, the present invention provides a compound of formula II-r"-7, wherein DIM is

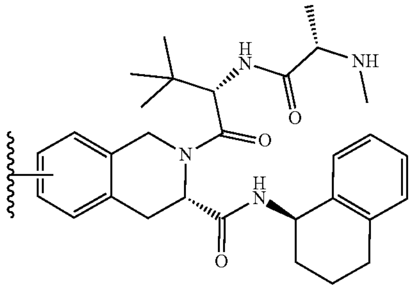

as shown, to provide a compound of formula II-r"-37:

II-r"-37

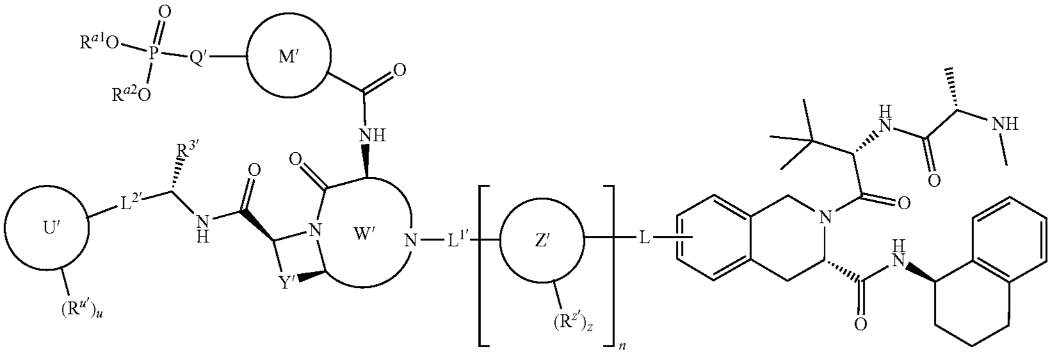

or a pharmaceutically acceptable salt thereof, wherein each of L, $L^{1'}$, $L^{2'}$, Ring M', Ring U', Ring W', Ring Z', $R^{3'}$, Y', Q', $R^{a1}$, $R^{a2}$, $R^{11}$, z, and n is as defined above and described in embodiments herein, both singly and in combination.

In some embodiments, the present invention provides a compound of formula II-r"-7, wherein DIM is

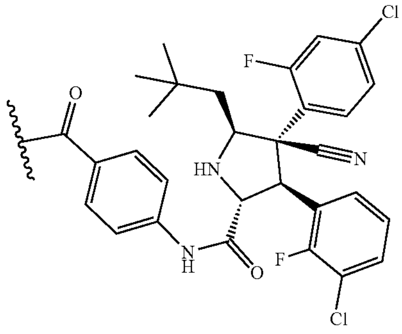 [SMILES: *C(=O)c1ccc(NC(=O)[C@@H]2N[C@@H](CC(C)(C)C)[C@](C#N)(c3ccc(Cl)cc3F)[C@H]2c2cccc(Cl)c2F)cc1]

as shown, to provide a compound of formula II-r"-38:

II-r"-38

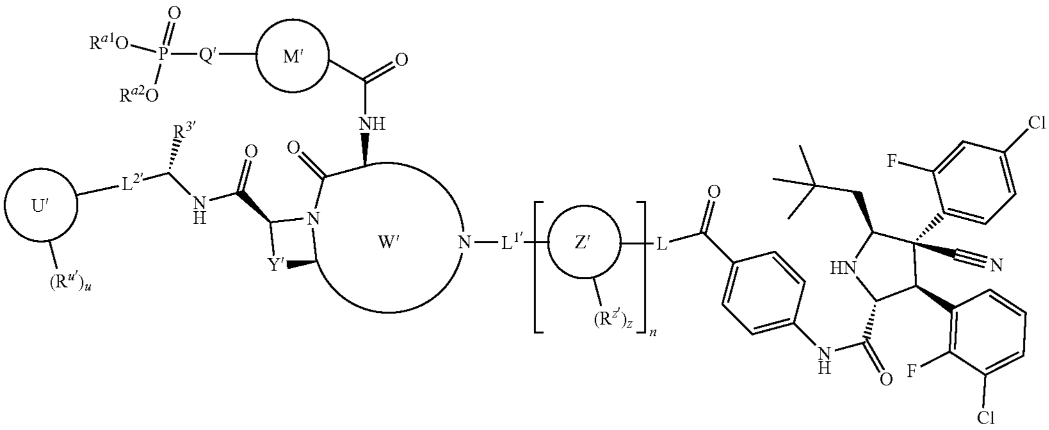

or a pharmaceutically acceptable salt thereof, wherein each of L, $L^{1'}$, $L^{2'}$, Ring M', Ring U', Ring W', Ring Z', $R^{3'}$, Y', Q', $R^{a1}$, $R^{a2}$, $R^{z'}$, z, and n is as defined above and described in embodiments herein, both singly and in combination.

In some embodiments, the present invention provides a compound of formula II-r"-7, wherein DIM is

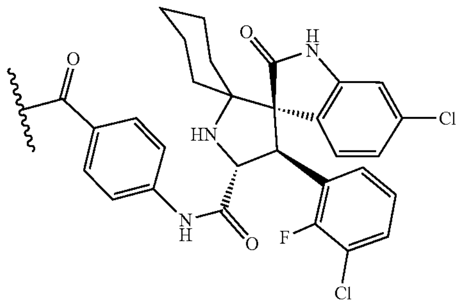 [SMILES: *C(=O)c1ccc(NC(=O)[C@@H]2NC3(CCCCC3)[C@@]3(C(=O)Nc4cc(Cl)ccc43)[C@H]2c2cccc(Cl)c2F)cc1]

as shown, to provide a compound of formula II-r"-39:

II-r"-39

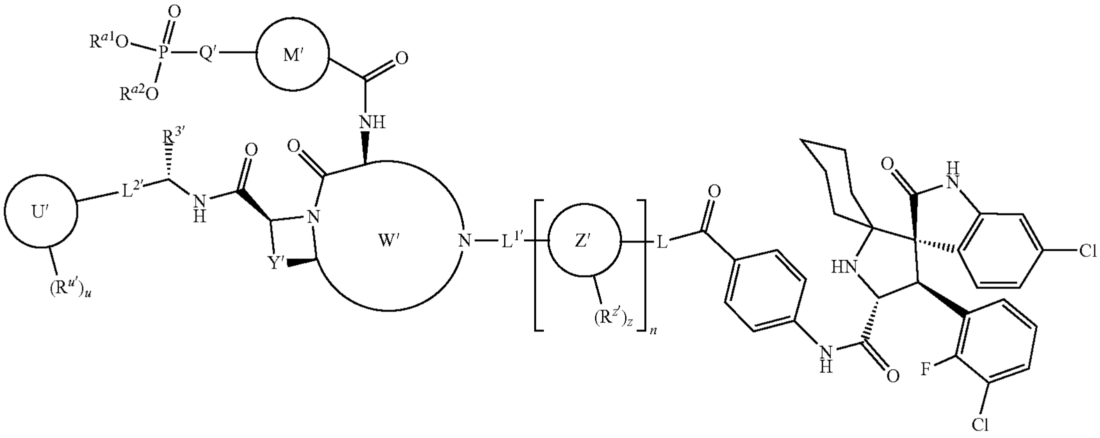

or a pharmaceutically acceptable salt thereof, wherein each of L, $L^{1'}$, $L^{2'}$, Ring M', Ring U', Ring W', Ring Z', $R^{3'}$, Y', Q', $R^{a1}$, $R^{a2}$, $R^{z'}$, z, and n is as defined above and described in embodiments herein, both singly and in combination.

In some embodiments, the present invention provides a compound of formula II-r"-7, wherein DIM is

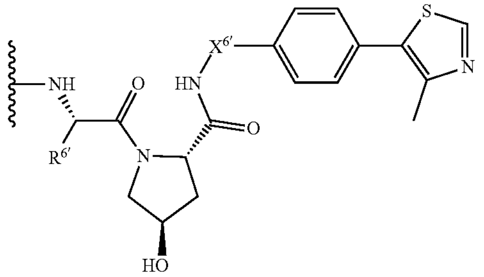

as shown, to provide a compound of formula II-r"-40:

II-r"-40

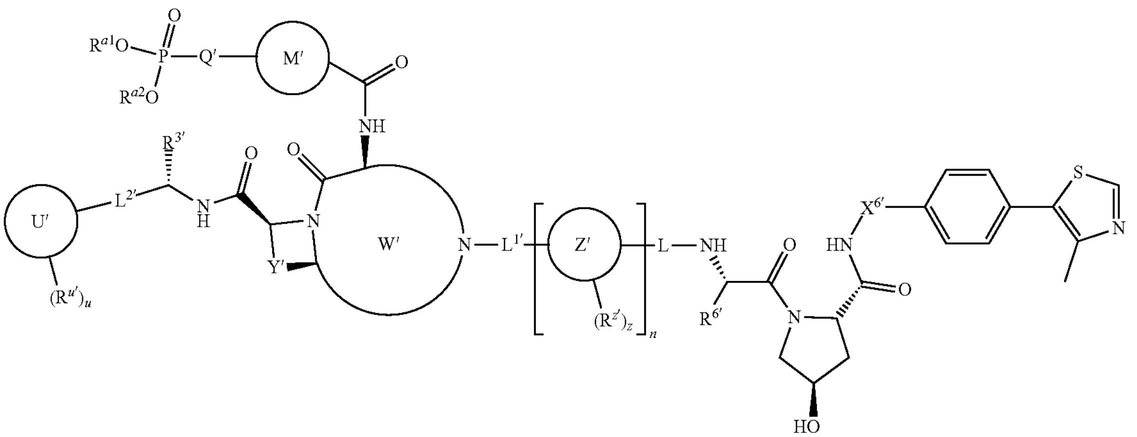

or a pharmaceutically acceptable salt thereof, wherein each of $X^{6'}$, $R^{6'}$, L, $L^{1'}$, $L^{2'}$, Ring M', Ring U', Ring W', Ring Z', $R^{3'}$, Y', Q', $R^{a1}$, $R^{a2}$, $R^{z'}$, z, and n is as defined above and described in embodiments herein, both singly and in combination.

In some embodiments, the present invention provides a compound of formula II-r"-7, wherein DIM is

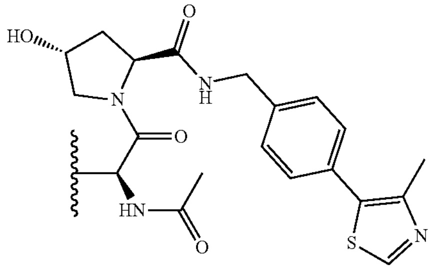 [SMILES: *[C@H](NC(C)=O)C(=O)N1C[C@H](O)C[C@H]1C(=O)NCc1ccc(-c2scnc2C)cc1]

as shown, to provide a compound of formula II-r"-41:

II-r"-41

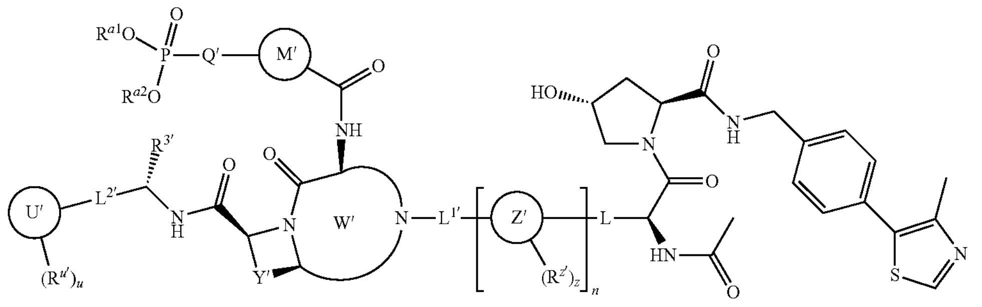

or a pharmaceutically acceptable salt thereof, wherein each of L, $L^{1'}$, $L^{2'}$, Ring M', Ring U', Ring W', Ring Z', $R^{3'}$, Y', Q', $R^{a1}$, $R^{a2}$, $R^{z'}$, z, and n is as defined above and described in embodiments herein, both singly and in combination.

In some embodiments, the present invention provides a compound of formula II-r"-7, wherein DIM is

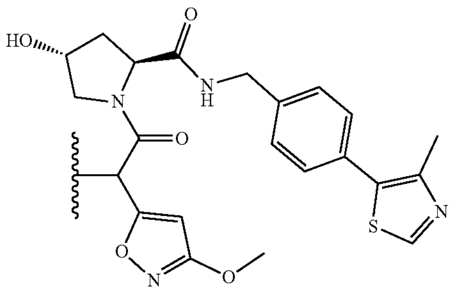 [SMILES: *C(C(=O)N1C[C@H](O)C[C@H]1C(=O)NCc1ccc(-c2scnc2C)cc1)c1cc(OC)no1]

as shown, to provide a compound of formula II-r"-42:

II-r"-42

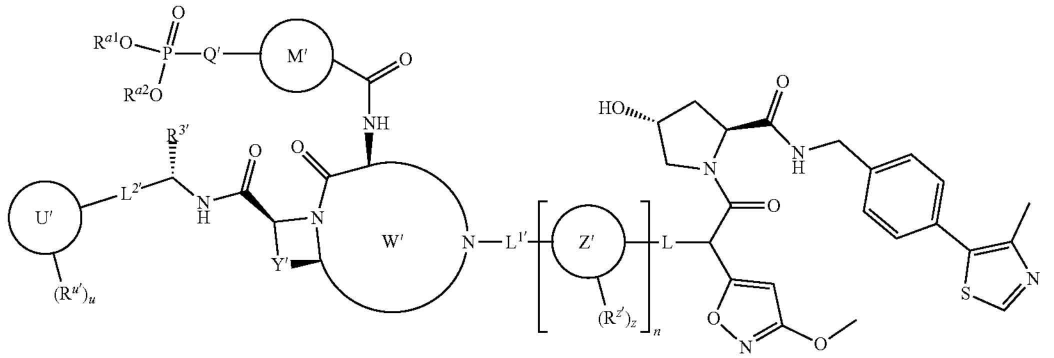

or a pharmaceutically acceptable salt thereof, wherein each of L, $L^{1'}$, $L^{2'}$, Ring M', Ring U', Ring W', Ring Z', $R^{3'}$, Y', Q', $R^{a1}$, $R^{a2}$, $R^{z'}$, z, and n is as defined above and described in embodiments herein, both singly and in combination.

In some embodiments, the present invention provides a compound of formula II-r"-7, wherein DIM is

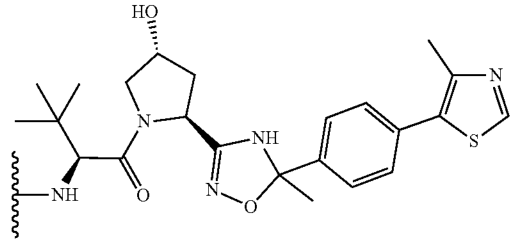 [SMILES: *N[C@H](C(=O)N1C[C@H](O)C[C@H]1C1=NOC(C)(c2ccc(-c3scnc3C)cc2)N1)C(C)(C)C]

as shown, to provide a compound of formula II-r"-43:

II-r"-43

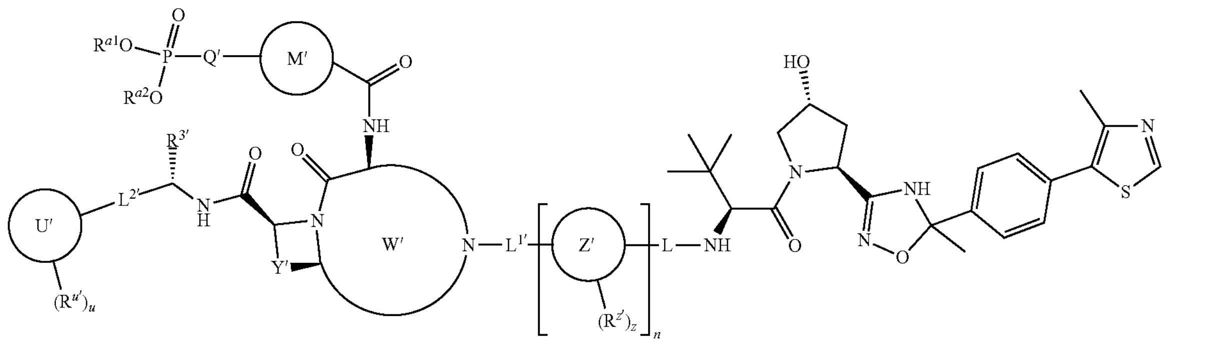

or a pharmaceutically acceptable salt thereof, wherein each of L, $L^{1'}$, $L^{2'}$, Ring M', Ring U', Ring W', Ring Z', $R^{3'}$, Y', Q', $R^{a1}$, $R^{a2}$, $R^{11}$, z, and n is as defined above and described in embodiments herein, both singly and in combination.

In some embodiments, the present invention provides a compound of formula II-r"-7, wherein DIM is

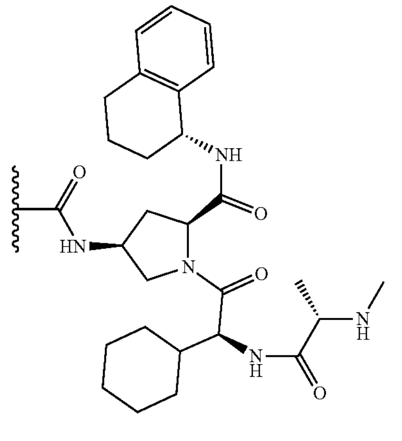 [SMILES: *C(=O)N[C@H]1C[C@@H](C(=O)N[C@@H]2CCCc3ccccc32)N(C(=O)[C@@H](NC(=O)[C@H](C)NC)C2CCCCC2)C1]

as shown, to provide a compound of formula II-r"-44:

II-r"-44

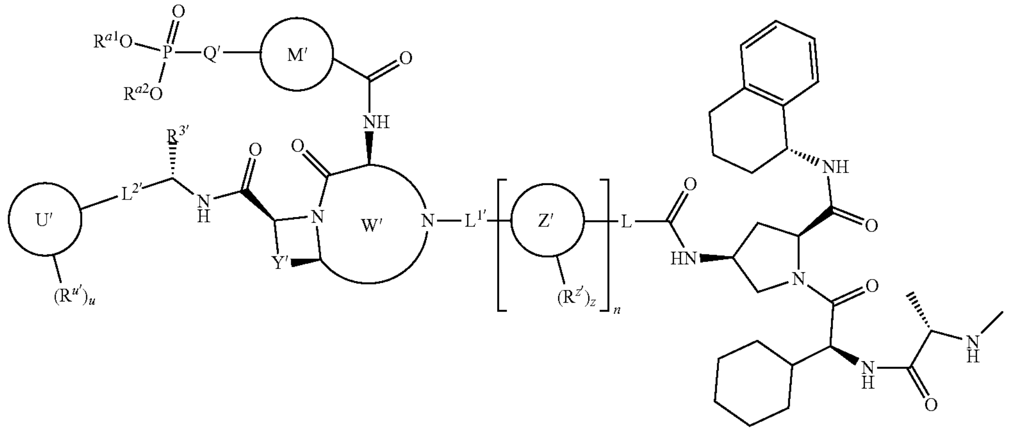

or a pharmaceutically acceptable salt thereof, wherein each of L, $L^{1'}$, $L^{2'}$, Ring M', Ring U', Ring W', Ring Z', $R^{3'}$, Y', Q', $R^{a1}$, $R^{a2}$, $R^{z'}$, z, and n is as defined above and described in embodiments herein, both singly and in combination.

In some embodiments, the present invention provides a compound of formula II-r"-7, wherein DIM is

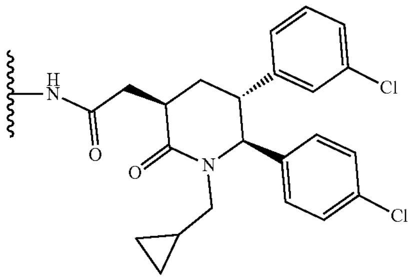 [SMILES: *NC(=O)C[C@H]1C[C@H](c2cccc(Cl)c2)[C@@H](c2ccc(Cl)cc2)N(CC2CC2)C1=O]

as shown, to provide a compound of formula II-r"-45:

II-r"-45

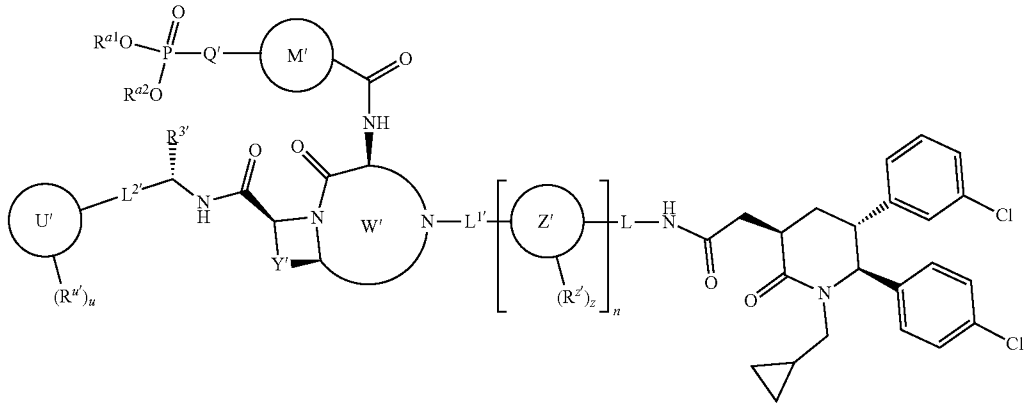

or a pharmaceutically acceptable salt thereof, wherein each of L, $L^{1'}$, $L^{2'}$, Ring M', Ring U', Ring W', Ring Z', $R^{3'}$, Y', Q', $R^{a1}$, $R^{a2}$, $R^{z'}$, z, and n is as defined above and described in embodiments herein, both singly and in combination.

In some embodiments, the present invention provides a compound of formula II-r"-7, wherein DIM is

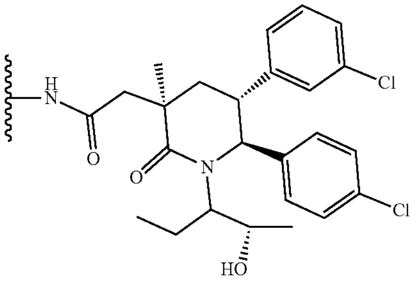 [SMILES: *NC(=O)C[C@@]1(C)C[C@H](c2cccc(Cl)c2)[C@@H](c2ccc(Cl)cc2)N(C(CC)[C@H](C)O)C1=O]

as shown, to provide a compound of formula II-r"-46:

II-r"-46

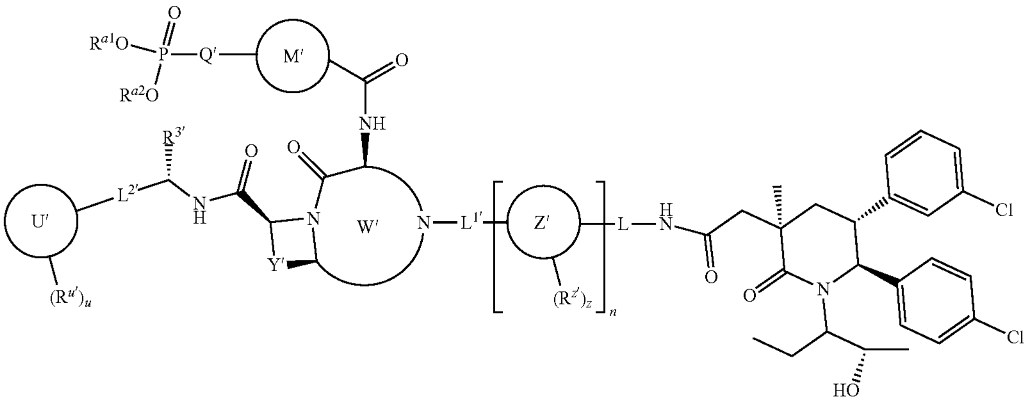

or a pharmaceutically acceptable salt thereof, wherein each of L, $L^{1'}$, $L^{2'}$, Ring M', Ring U', Ring W', Ring Z', $R^{3'}$, Y', Q', $R^{a1}$, $R^{a2}$, $R^{11}$, z, and n is as defined above and described in embodiments herein, both singly and in combination.

In some embodiments, the present invention provides a compound of formula II-r"-7, wherein DIM is

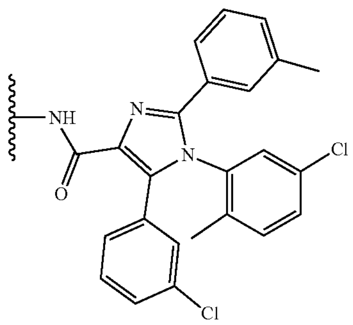 [SMILES: *NC(=O)c1nc(-c2cccc(C)c2)n(-c2cc(Cl)ccc2C)c1-c1cccc(Cl)c1]

as shown, to provide a compound of formula II-r"-47:

II-r"-47

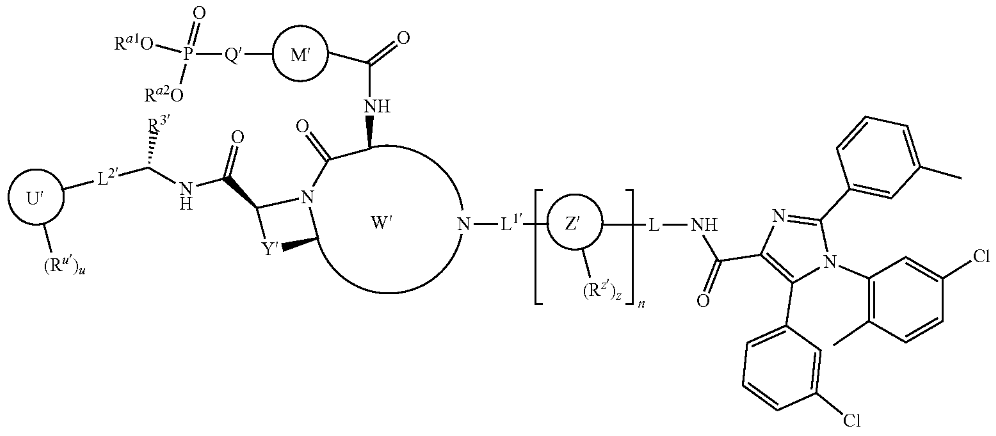

or a pharmaceutically acceptable salt thereof, wherein each of L, L$^{1'}$, L$^{2'}$, Ring M', Ring U', Ring W', Ring Z', R$^{3'}$, Y', Q', R$^{a1}$, R$^{a2}$, R$^{z'}$, z, and n is as defined above and described in embodiments herein, both singly and in combination.

In some embodiments, the present invention provides a compound of formula II-r"-7, wherein DIM is

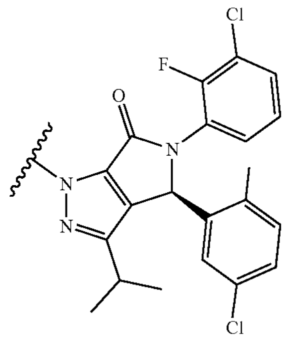 [SMILES: *n1nc(C(C)C)c2c1C(=O)N(c1cccc(Cl)c1F)[C@H]2c1cc(Cl)ccc1C]

as shown, to provide a compound of formula II-r"-48:

II-r"-48

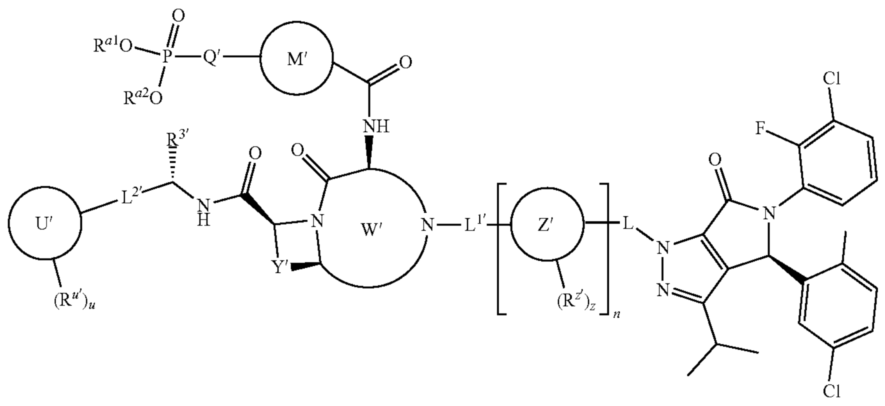

or a pharmaceutically acceptable salt thereof, wherein each of L, $L^{1'}$, $L^{2'}$, Ring M', Ring U', Ring W', Ring Z', $R^{3'}$, Y', Q', $R^{a1}$, $R^{a2}$, $R^{z'}$, z, and n is as defined above and described in embodiments herein, both singly and in combination.

In some embodiments, the present invention provides a compound of formula II-s", wherein DIM is

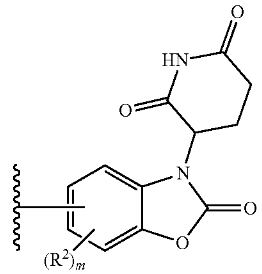

as shown, to provide a compound of formula II-s"-5:

II-s"-5

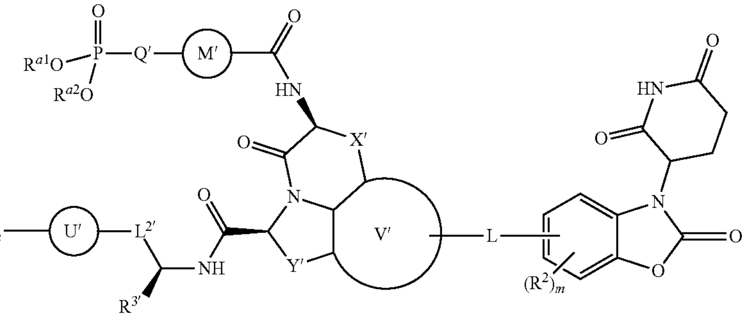

or a pharmaceutically acceptable salt thereof, wherein each of $R^2$, m, L, Ring M', Ring U', Ring V', $R^{3'}$, Q', X', Y', $R^{a1}$, and $R^{a2}$ is as defined above and described in embodiments herein, both singly and in combination.

In some embodiments, the present invention provides a compound of formula II-s", wherein DIM is

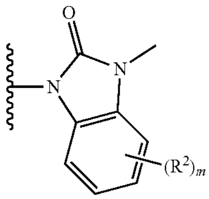

as shown, to provide a compound of formula II-s"-6:

II-s"-6

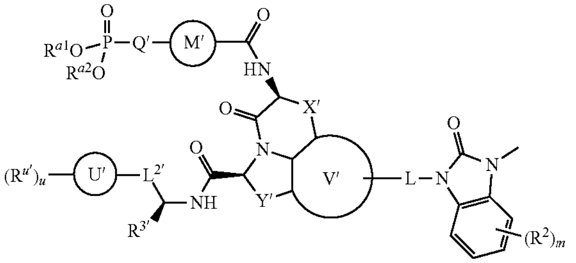

or a pharmaceutically acceptable salt thereof, wherein each of $R^2$, m, L, Ring M', Ring U', Ring V', $R^{3'}$, Q', X', Y', $R^{a1}$, and $R^{a2}$ is as defined above and described in embodiments herein, both singly and in combination.

In some embodiments, the present invention provides a compound of formula II-s", wherein DIM is

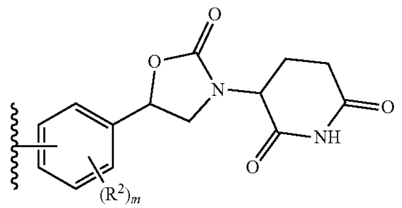

is shown, to provide a compound of formula II-s"-7:

II-s"-7

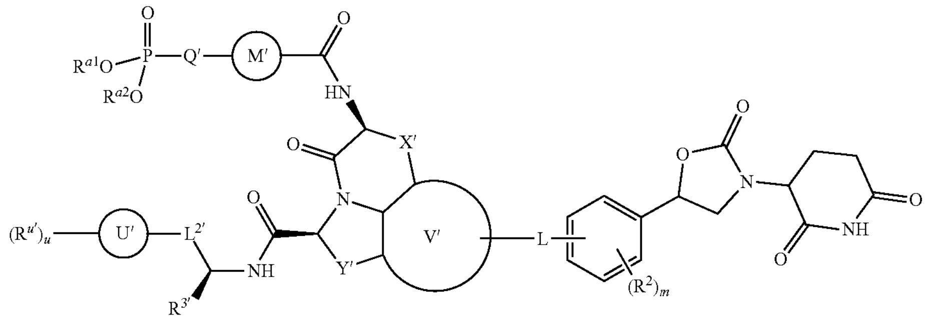

or a pharmaceutically acceptable salt thereof, wherein each of $R^2$, m, L, Ring M', Ring U', Ring V', $R^{3'}$, Q', X', Y', $R^{a1}$, and $R^{a2}$ is as defined above and described in embodiments herein, both singly and in combination.

In some embodiments, the present invention provides a compound of formula II-s", wherein DIM is

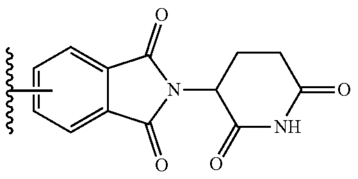

as shown, to provide a compound of formula II-s"-8:

II-s"-8

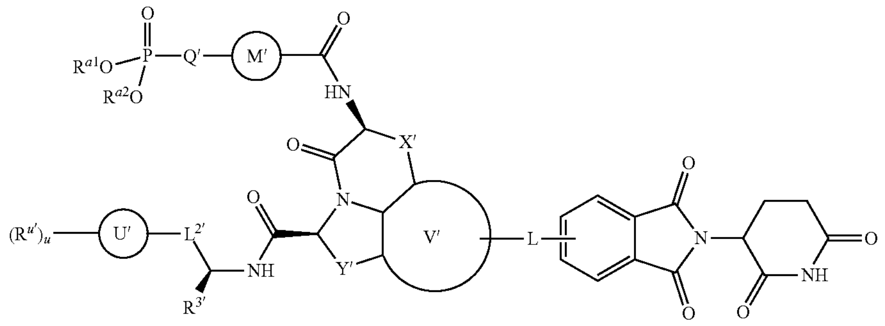

or a pharmaceutically acceptable salt thereof, wherein each of L, Ring M', Ring U', Ring V', $R^{3'}$, Q', X', Y', $R^{a1}$, and $R^2$ is as defined above and described in embodiments herein, both singly and in combination.

In some embodiments, the present invention provides a compound of formula II-s", wherein DIM is

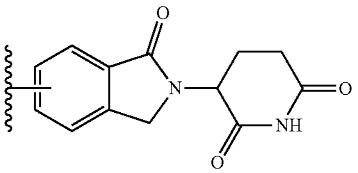

as shown, to provide a compound of formula II-s"-9:

II-s"-9

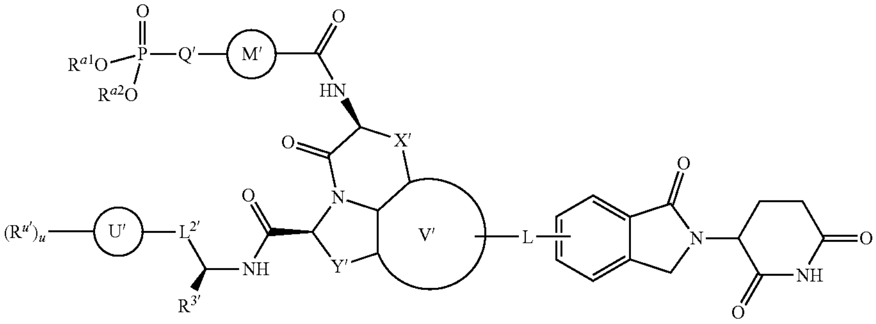

or a pharmaceutically acceptable salt thereof, wherein each of L, Ring M', Ring U', Ring V', $R^{3'}$, Q', X', Y', $R^{a1}$, and $R^2$ is as defined above and described in embodiments herein, both singly and in combination.

In some embodiments, the present invention provides a compound of formula II-s", wherein DIM is

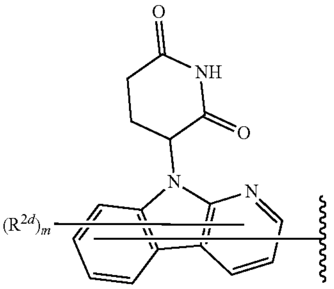

as shown, to provide a compound of formula II-s"-10:

II-s"-10

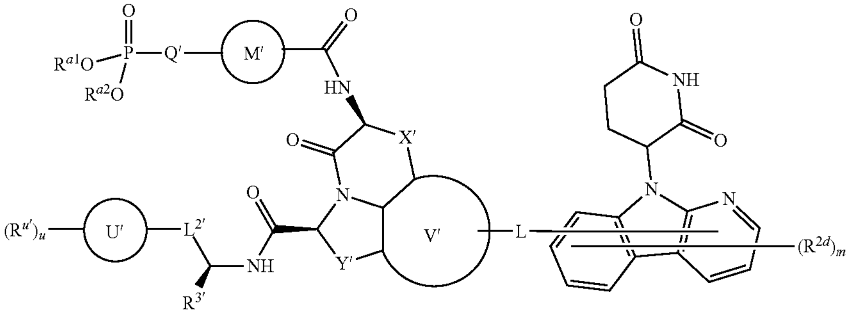

or a pharmaceutically acceptable salt thereof, wherein each of $R^2$, m, L, Ring M', Ring U', Ring V', $R^{3'}$, Q', X', Y', $R^{a1}$, and $R^{a2}$ is as defined above and described in embodiments herein, both singly and in combination.

In some embodiments, the present invention provides a compound of formula II-s", wherein DIM is

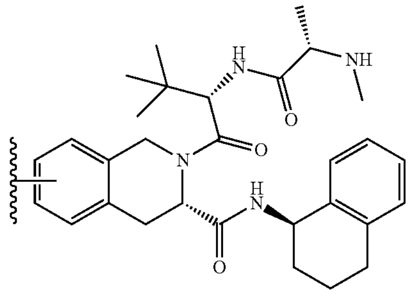

as shown, to provide a compound of formula II-s"-11:

II-s"-11

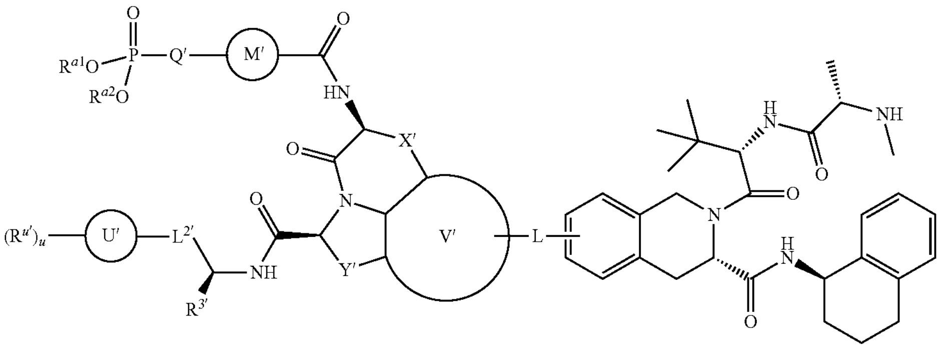

or a pharmaceutically acceptable salt thereof, wherein each of L, Ring M', Ring U', Ring V', $R^{3'}$, Q', X', Y', $R^{a1}$, and $R^{a2}$ is as defined above and described in embodiments herein, both singly and in combination.

In some embodiments, the present invention provides a compound of formula II-s", wherein DIM is

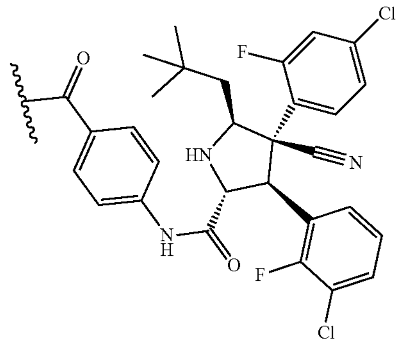 [SMILES: *C(=O)c1ccc(NC(=O)[C@@H]2N[C@@H](CC(C)(C)C)[C@](C#N)(c3ccc(Cl)cc3F)[C@H]2c2cccc(Cl)c2F)cc1]

as shown, to provide a compound of formula II-s"-12:

II-s"-12

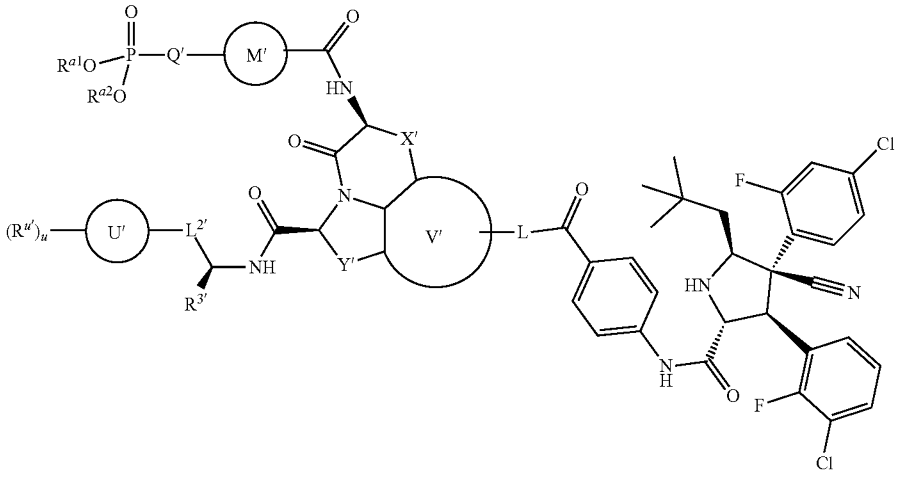

or a pharmaceutically acceptable salt thereof, wherein each of L, Ring M', Ring U', Ring V', $R^{3'}$, Q', X', Y', $R^{a1}$, and $R^2$ is as defined above and described in embodiments herein, both singly and in combination.

In some embodiments, the present invention provides a compound of formula II-s", wherein DIM is

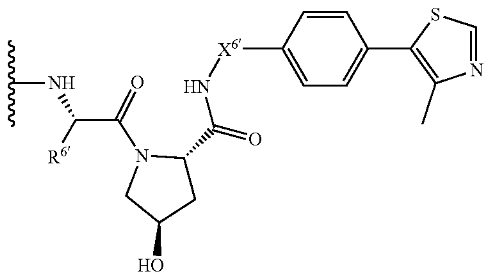

as shown, to provide a compound of formula II-s"-13:

II-s"-13

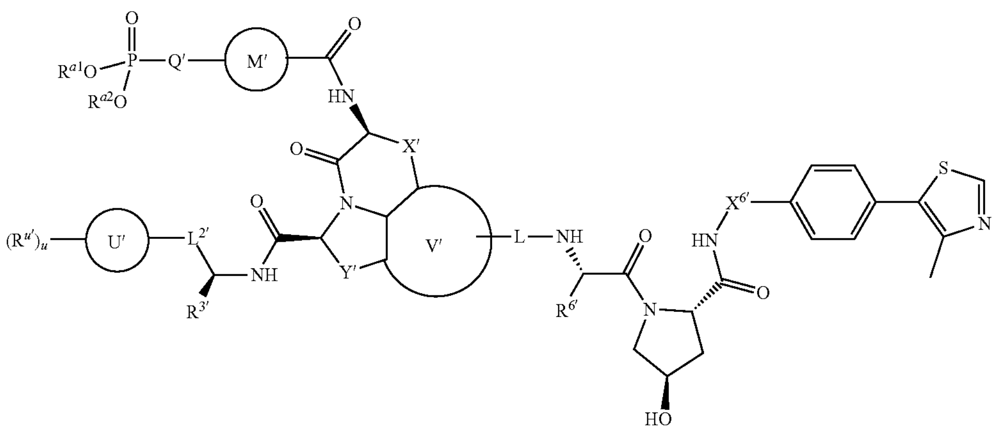

or a pharmaceutically acceptable salt thereof, wherein each of $X^{6'}$, $R^{6'}$, L, Ring M', Ring U', Ring V', $R^{3'}$, Q', X', Y', $R^{a1}$, and $R^2$ is as defined above and described in embodiments herein, both singly and in combination.

In some embodiments, the present invention provides a compound of formula II-s", wherein DIM is

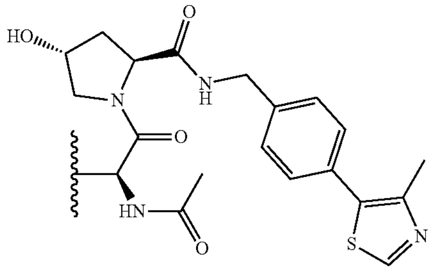 [SMILES: *[C@H](NC(C)=O)C(=O)N1C[C@H](O)C[C@H]1C(=O)NCc1ccc(-c2scnc2C)cc1]

as shown, to provide a compound of formula II-s"-14:

II-s"-14

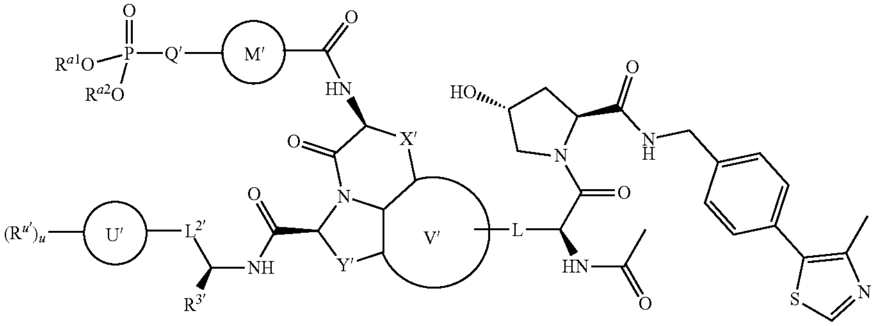

or a pharmaceutically acceptable salt thereof, wherein each of L, Ring M', Ring U', Ring V', $R^{3'}$, Q', X', Y', $R^{a1}$, and $R^{a2}$ is as defined above and described in embodiments herein, both singly and in combination.

In some embodiments, the present invention provides a compound of formula II-s", wherein DIM

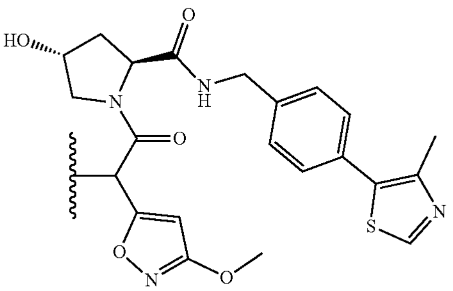 [SMILES: *C(C(=O)N1C[C@H](O)C[C@H]1C(=O)NCc1ccc(-c2scnc2C)cc1)c1cc(OC)no1]

as shown, to provide a compound of formula II-s"-15:

II-s"-15

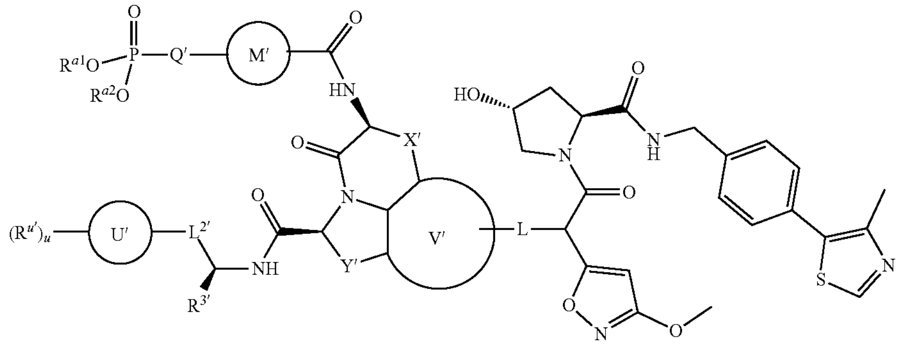

or a pharmaceutically acceptable salt thereof, wherein each of L, Ring M', Ring U', Ring V', $R^{3'}$, Q', X', Y', $R^{a1}$, and $R^{a2}$ is as defined above and described in embodiments herein, both singly and in combination.

In some embodiments, the present invention provides a compound of formula II-s", wherein DIM is

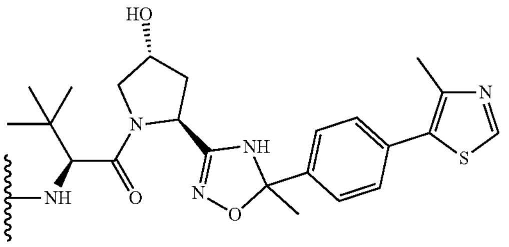 [SMILES: *N[C@H](C(=O)N1C[C@H](O)C[C@H]1C1=NOC(C)(c2ccc(-c3scnc3C)cc2)N1)C(C)(C)C]

as shown, to provide a compound of formula II-s"-16:

II-s"-16

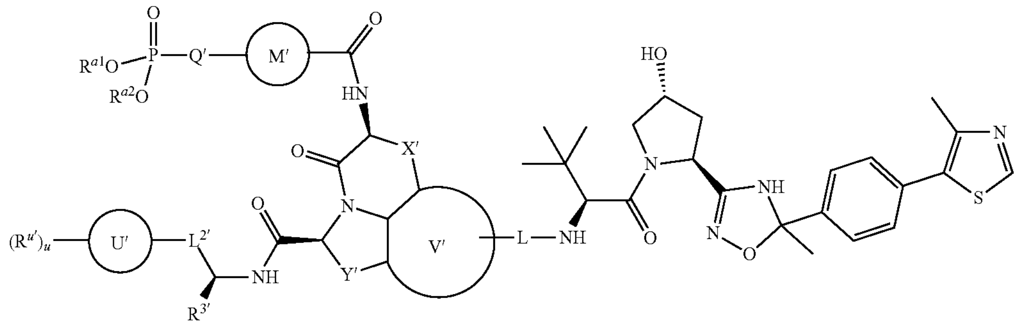

or a pharmaceutically acceptable salt thereof, wherein each of L, Ring M', Ring U', Ring V', $R^{3'}$, Q', X', Y', $R^{a1}$, and $R^{a2}$ is as defined above and described in embodiments herein, both singly and in combination.

In some embodiments, the present invention provides a compound of formula II-s", wherein DIM is

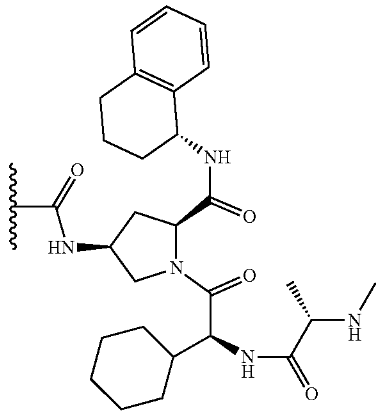 [SMILES: *C(=O)N[C@H]1C[C@@H](C(=O)N[C@@H]2CCCc3ccccc32)N(C(=O)[C@@H](NC(=O)[C@H](C)NC)C2CCCCC2)C1]
as shown, to provide a compound of formula II-s"-17:
II-s"-17
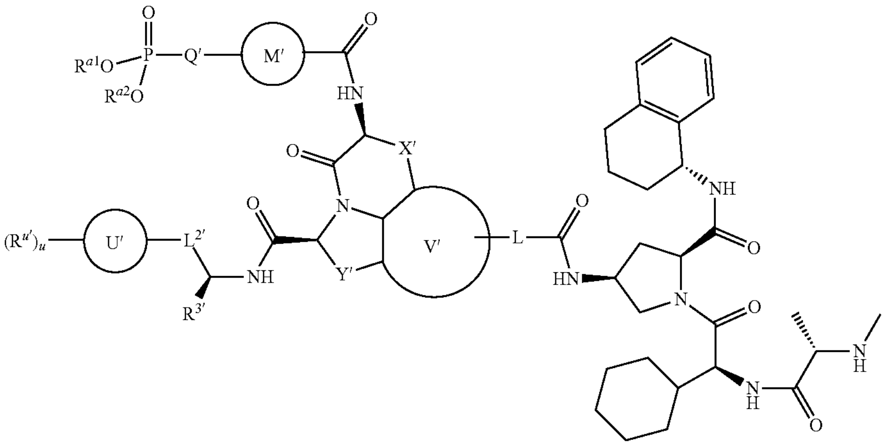
or a pharmaceutically acceptable salt thereof, wherein each of L, Ring M', Ring U', Ring V', $R^{3'}$, Q', X', Y', $R^{a1}$, and $R^2$ is as defined above and described in embodiments herein, both singly and in combination.
In some embodiments, the present invention provides a compound of formula II-s", wherein DIM is
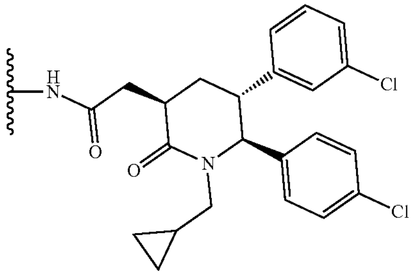 [SMILES: *NC(=O)C[C@H]1C[C@H](c2cccc(Cl)c2)[C@@H](c2ccc(Cl)cc2)N(CC2CC2)C1=O]

as shown, to provide a compound of formula II-s"-18:

II-s"-18

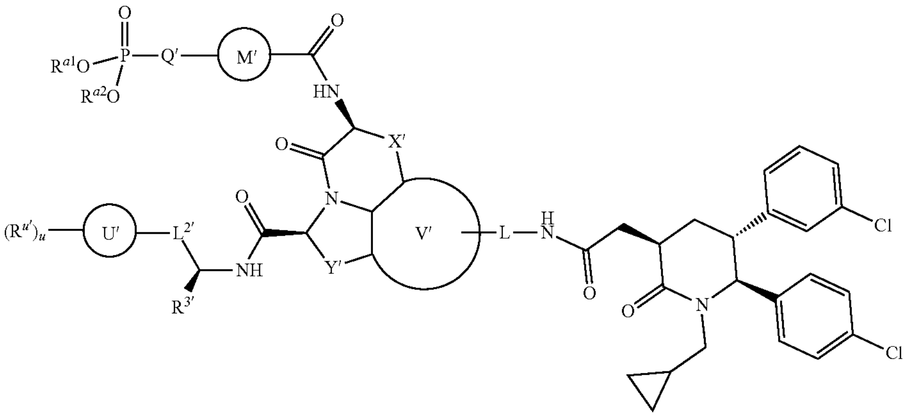

or a pharmaceutically acceptable salt thereof, wherein each of L, Ring M', Ring U', Ring V', $R^{3'}$, Q', X', Y', $R^{a1}$, and $R^2$ is as defined above and described in embodiments herein, both singly and in combination.

In some embodiments, the present invention provides a compound of formula II-s", wherein DIM is

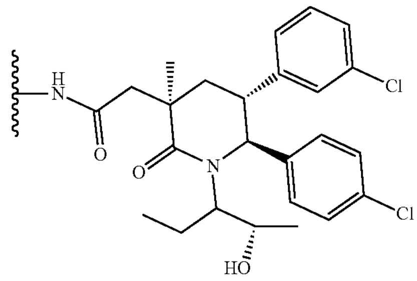 [SMILES: *NC(=O)C[C@@]1(C)C[C@H](c2cccc(Cl)c2)[C@@H](c2ccc(Cl)cc2)N(C(CC)[C@H](C)O)C1=O]

as shown, to provide a compound of formula II-s"-19:

II-s"-19

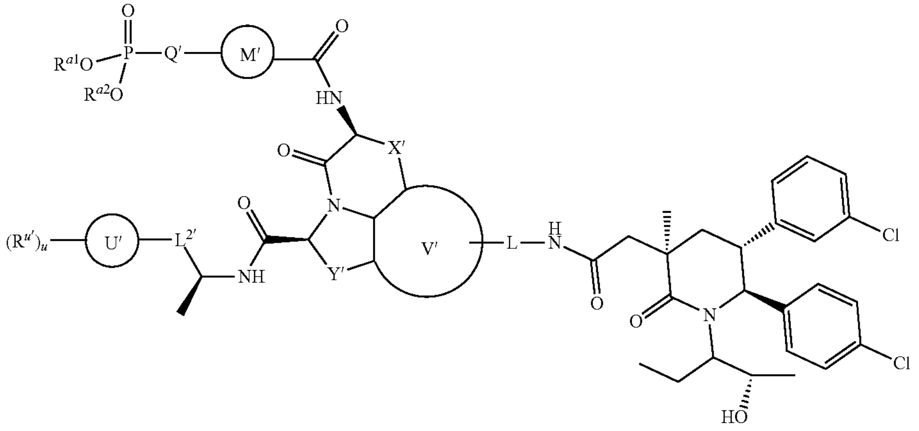

or a pharmaceutically acceptable salt thereof, wherein each of L, Ring M', Ring U', Ring V', $R^{3'}$, Q', X', Y', $R^{a1}$, and $R^{a2}$ is as defined above and described in embodiments herein, both singly and in combination.

In some embodiments, the present invention provides a compound of formula II-s", wherein DIM is

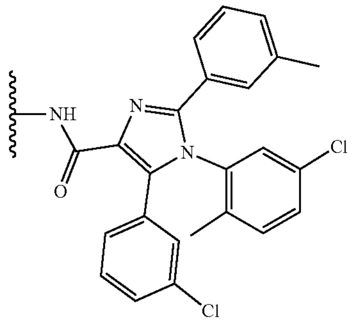 [SMILES: *NC(=O)c1nc(-c2cccc(C)c2)n(-c2cc(Cl)ccc2C)c1-c1cccc(Cl)c1]

as shown, to provide a compound of formula II-s"-20:

II-s"-20

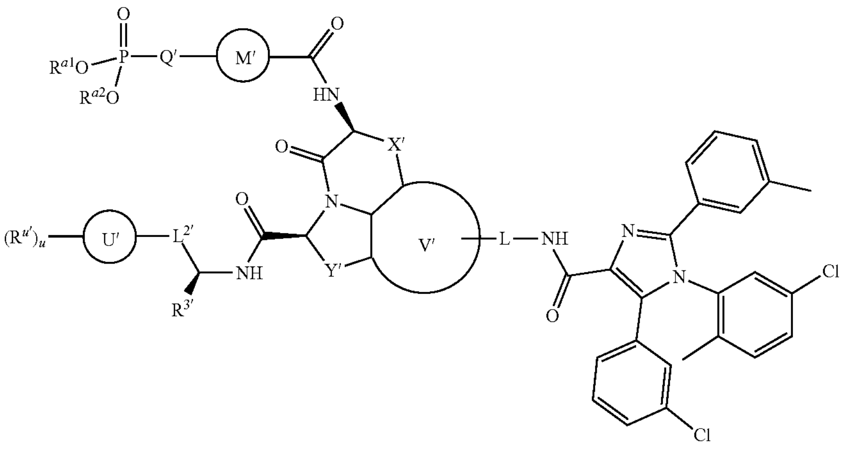

or a pharmaceutically acceptable salt thereof, wherein each of L, Ring M', Ring U', Ring V', $R^{3'}$, Q', X', Y', $R^{a1}$, and $R^2$ is as defined above and described in embodiments herein, both singly and in combination.

In some embodiments, the present invention provides a compound of formula II-s", wherein DIM is

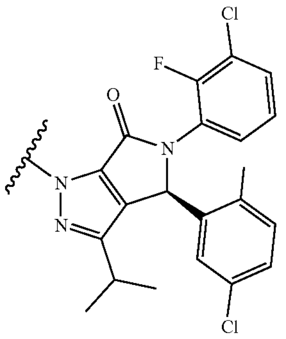 [SMILES: *n1nc(C(C)C)c2c1C(=O)N(c1cccc(Cl)c1F)[C@H]2c1cc(Cl)ccc1C]

as shown, to provide a compound of formula II-s"-21:

II-s"-21

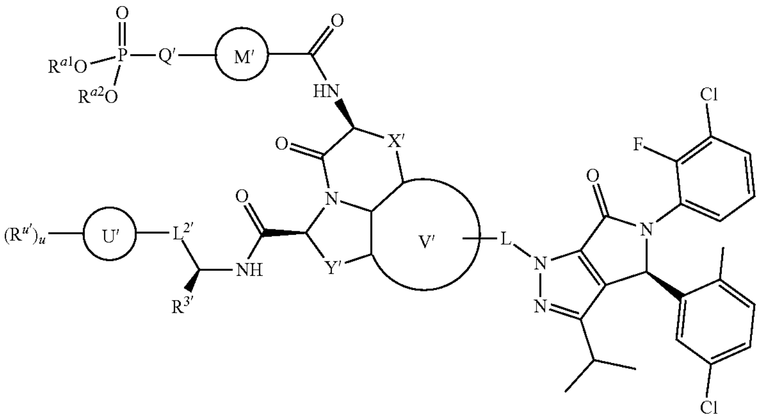

or a pharmaceutically acceptable salt thereof, wherein each of L, Ring M', Ring U', Ring V', $R^{3'}$, Q', X', Y', $R^{a1}$, and $R^{a2}$ is as defined above and described in embodiments herein, both singly and in combination.

Without being limited to any particular theory, prodrugs of compounds of formula I and formula II are included in the present invention. It is well established that a prodrug approach, wherein a compound is derivatized into a form suitable for formulation and/or administration, then released as a drug in vivo, has been successfully employed to transiently (e.g., bioreversibly) alter the physicochemical properties of the compound (see, H. Bundgaard, Ed., "Design of Prodrugs," Elsevier, Amsterdam, (1985); R. B. Silverman, "The Organic Chemistry of Drug Design and Drug Action," Academic Press, San Diego, chapter 8, (1992); K. M. Hillgren et al., *Med. Res. Rev.*, 15, 83 (1995)).

One of ordinary skill in the art will appreciate that the diflouro phosphonate moiety described above may convert in vivo to a ketone phosphonate moiety, e.g.,

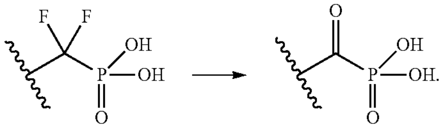 [SMILES: *C(F)(F)P(=O)(O)O ; *C(=O)P(=O)(O)O]

In certain embodiments, the present invention provides a compound of formula I or formula II, wherein STAT is a STAT3 binding moiety thereby forming a compound of formula I-aw or II-t:

I-aw

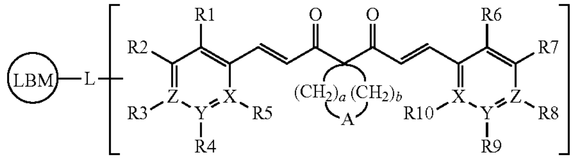

-continued

II-t

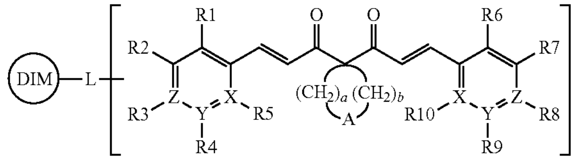

or a pharmaceutically acceptable salt thereof, wherein L and LBM or DIM are as defined above and described in embodiments herein, and wherein each of the variables $R^1$, $R^2$, $R^3$, $R^4$, $R^5$, $R^6$, $R^7$, $R^8$, $R^9$, $R^{10}$, A, Z, X, Y, a, and b is as described and defined in WO 2010/121007 and US 2012/0053208, the entirety of each of which is herein incorporated by reference.

In certain embodiments, the present invention provides a compound of formula I or formula II, wherein STAT is a STAT3 binding moiety thereby forming a compound of formula I-ax or II-u:

I-ax

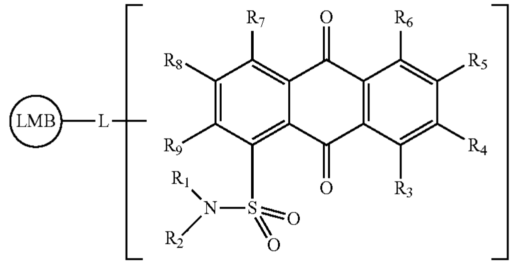

II-u

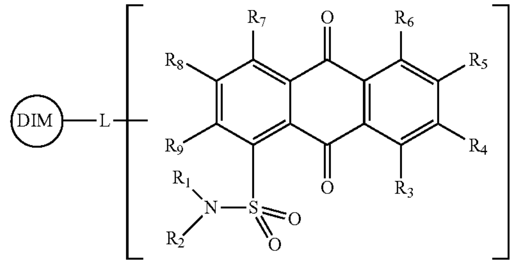

or a pharmaceutically acceptable salt thereof, wherein L and LBM or DIM are as defined above and described in embodiments herein, and wherein each of the variables $R_1$, $R_2$, $R_3$, $R_4$, $R_5$, $R_6$, $R_7$, $R_8$, and $R_9$ is as described and defined in WO 2011/066263, WO 2012/097351, and U.S. Pat. No. 8,883,749, the entirety of each of which is herein incorporated by reference.

In certain embodiments, the present invention provides a compound of formula I or formula II, wherein STAT is a STAT3 binding moiety thereby forming a compound of formula I-ay or II-v:

I-ay

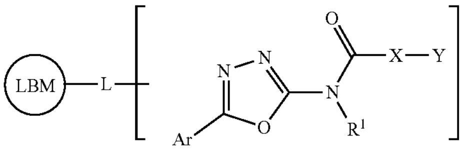

II-v

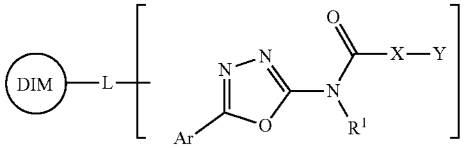

or a pharmaceutically acceptable salt thereof, wherein L and LBM or DIM are as defined above and described in embodiments herein, and wherein each of the variables $R_1$, Ar, X and Y is as described and defined in WO 2011/081205 and US 2012/302524, the entirety of each of which is herein incorporated by reference.

In certain embodiments, the present invention provides a compound of formula I or formula II, wherein STAT is a STAT3 binding moiety thereby forming a compound of formula I-az or II-w:

I-az

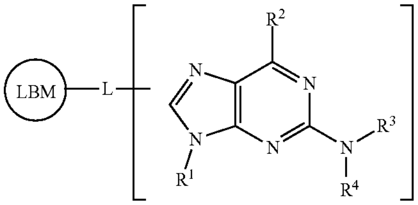

II-w

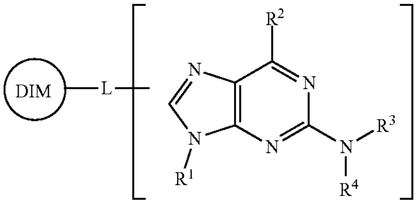

or a pharmaceutically acceptable salt thereof, wherein L and LBM or DIM are as defined above and described in embodiments herein, and wherein each of the variables $R_1$, $R_2$, $R_3$, and $R_4$ is as described and defined in WO 2011/163424 and US 2013/0172340, the entirety of each of which is herein incorporated by reference.

In certain embodiments, the present invention provides a compound of formula I or formula II, wherein STAT is a STAT3 binding moiety thereby forming a compound of formula I-aaa or II-x:

I-aaa

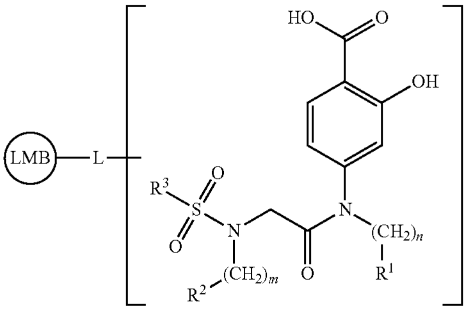

II-x

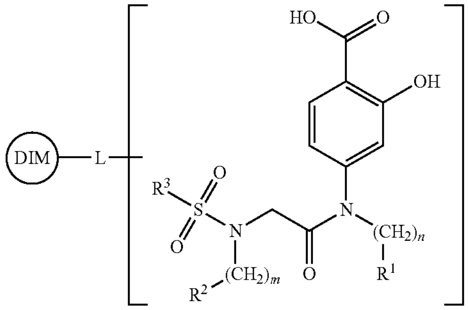

or a pharmaceutically acceptable salt thereof, wherein L and LBM or DIM are as defined above and described in embodiments herein, and wherein each of the variables $R_1$, $R_2$, $R_3$, and $R_4$ is as described and defined in WO 2012/018868 and US 2013/0225621, the entirety of each of which is herein incorporated by reference.

In certain embodiments, the present invention provides a compound of formula I or formula II, wherein STAT is a STAT3 binding moiety thereby forming a compound of formula I-aab or II-y:

I-aab

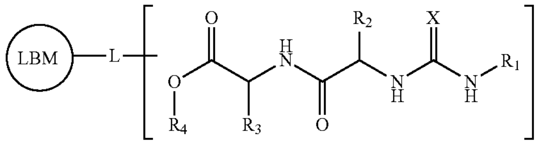

II-y

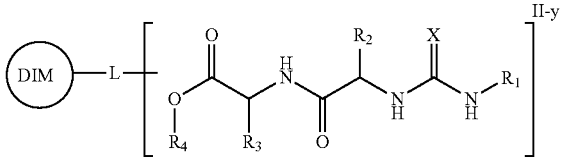

or a pharmaceutically acceptable salt thereof, wherein L and LBM or DIM are as defined above and described in embodiments herein, and wherein each of the variables $R_1$, $R_2$, $R_3$, $R_4$, and X is as described and defined in WO 2012/078982, the entirety of each of which is herein incorporated by reference.

In certain embodiments, the present invention provides a compound of formula I or formula II, wherein STAT is a STAT3 binding moiety thereby forming a compound of formula I-aac or II-z:

I-aac

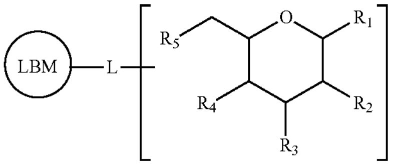

II-z

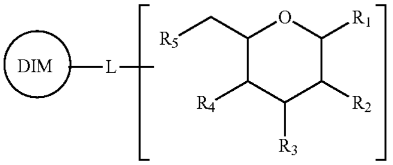

or a pharmaceutically acceptable salt thereof, wherein L and LBM or DIM are as defined above and described in embodiments herein, and wherein each of the variables $R_1$, $R_2$, $R_3$, $R_4$, and $R_5$ is as described and defined in WO 2012/142615, the entirety of each of which is herein incorporated by reference.

In certain embodiments, the present invention provides a compound of formula I or formula II, wherein STAT is a STAT3 binding moiety thereby forming a compound of formula I-aad or II-aa:

I-aad

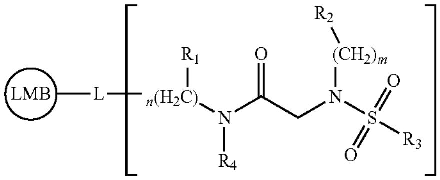

II-aa

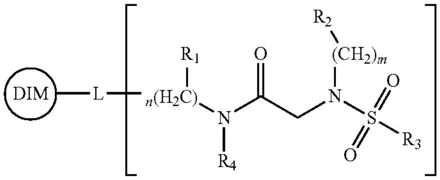

or a pharmaceutically acceptable salt thereof, wherein L and LBM or DIM are as defined above and described in embodiments herein, and wherein each of the variables $R_1$, $R_2$, $R_3$, $R_4$, m, and n is as described and defined in WO 2013/177534 and US 2015/0158894, the entirety of each of which is herein incorporated by reference.

In certain embodiments, the present invention provides a compound of formula I or formula II, wherein STAT is a STAT3 binding moiety thereby forming a compound of formula I-aae or II-bb:

I-aae

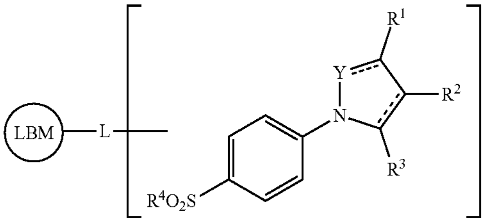

-continued

II-bb

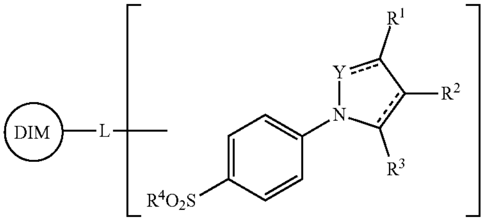

or a pharmaceutically acceptable salt thereof, wherein and or DIM are as defined above and described in embodiments herein, and wherein each of the variables $R_1$, $R_2$, $R_3$, $R_4$, Y, and ∿∿ is as described and defined in WO 2013/187965 and US 2015/0166484, the entirety of each of which is herein incorporated by reference.

In certain embodiments, the present invention provides a compound of formula I or formula II, wherein STAT is a STAT3 binding moiety thereby forming a compound of formula I-aaf or II-cc:

I-aaf

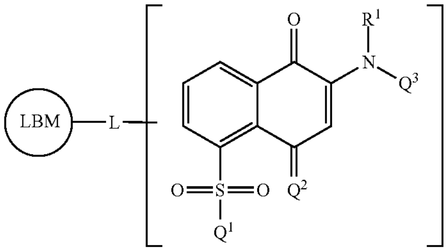

II-cc

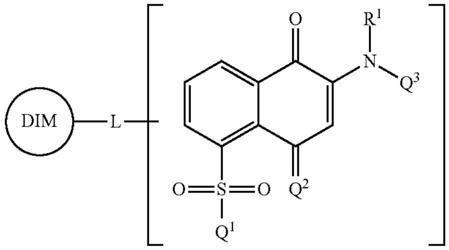

or a pharmaceutically acceptable salt thereof, wherein L and LBM or DIM are as defined above and described in embodiments herein, and wherein each of the variables $Q^1$, $Q^2$, $Q^3$, and R is as described and defined in WO 2014/028909 and US 2015/0232434, the entirety of each of which is herein incorporated by reference.

In certain embodiments, the present invention provides a compound of formula I or formula II, wherein STAT is a STAT3 binding moiety thereby forming a compound of formula I-aa or II-dd:

I-aag

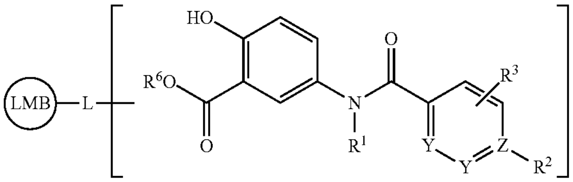

-continued

I-dd

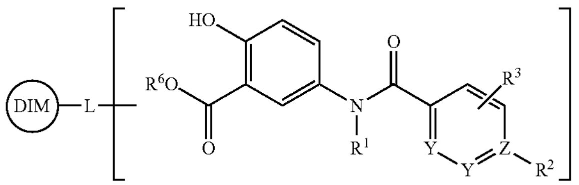

or a pharmaceutically acceptable salt thereof, wherein L and LBM or DIM are as defined above and described in embodiments herein, and wherein each of the variables $R^1$, $R^2$, $R^3$, $R^6$, Z, and Y is as described and defined in WO 2014/070859 and US 2015/0259366, the entirety of each of which is herein incorporated by reference.

In certain embodiments, the present invention provides a compound of formula I or formula II, wherein STAT is a STAT3 binding moiety thereby forming a compound of formula I-aah or II-ee:

I-aah

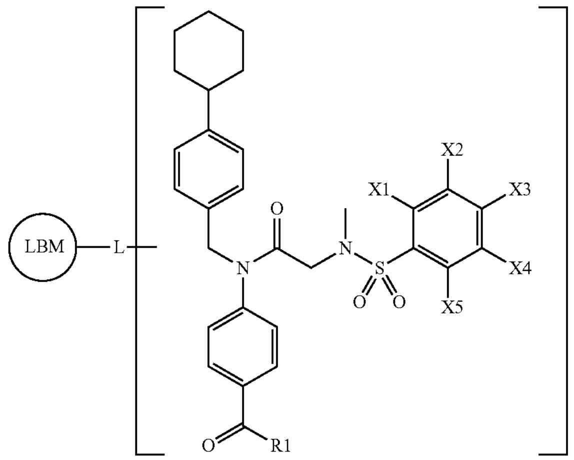

II-ee

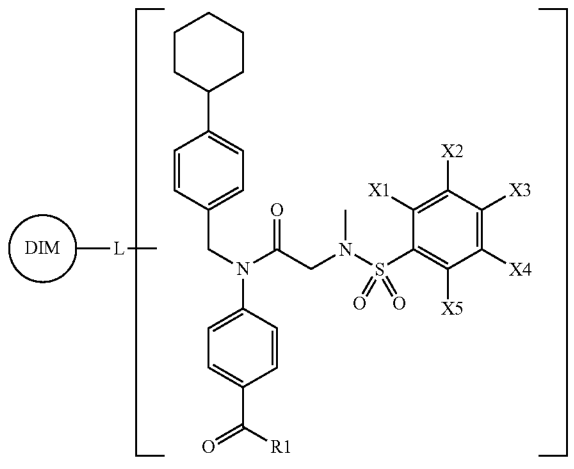

or a pharmaceutically acceptable salt thereof, wherein L and LBM or DIM are as defined above and described in embodiments herein, and wherein each of the variables RI, X1, X2, X3, X4, and X5 is as described and defined in WO 2014/153495 and US 2016/0068478, the entirety of each of which is herein incorporated by reference.

In certain embodiments, the present invention provides a compound of formula I or formula II, wherein STAT is a STAT3 binding moiety thereby forming a compound of formula I-aai or II-ff:

I-aai

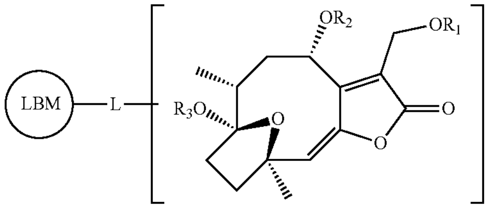

II-gg

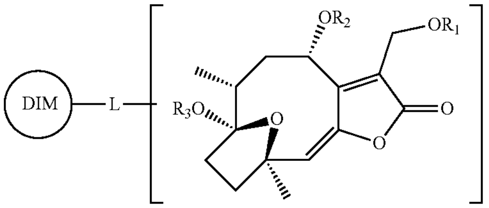

or a pharmaceutically acceptable salt thereof, wherein L and LBM or DIM are as defined above and described in embodiments herein, and wherein each of the variables $R_1$, $R_2$, and $R_3$ is as described and defined in WO 2014/205416 and US 2016/0137663, the entirety of each of which is herein incorporated by reference.

In certain embodiments, the present invention provides a compound of formula I or formula II, wherein STAT is a STAT3 binding moiety thereby forming a compound of formula I-aaj or II-hh:

I-aaj

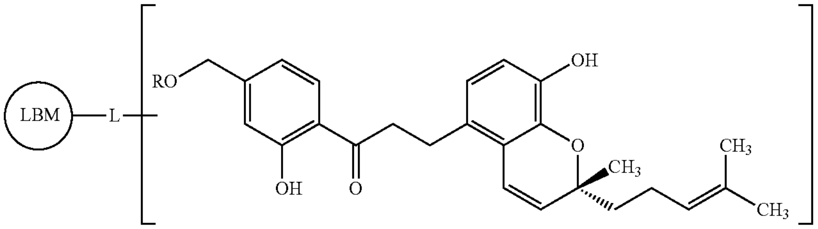

II-hh

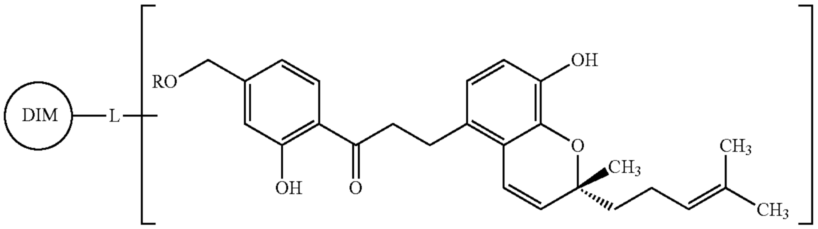

or a pharmaceutically acceptable salt thereof, wherein L and LBM or DIM are as defined above and described in embodiments herein, and wherein each of the variable R is as described and defined in US 2016/0060239, the entirety of each of which is herein incorporated by reference.

In certain embodiments, the present invention provides a compound of formula I or formula II, wherein STAT is a STAT3 binding moiety thereby forming a compound of formula I-aak or II-ii:

I-aak

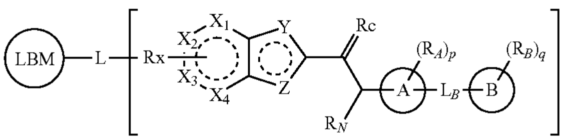

II-ii

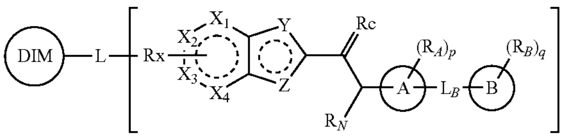

or a pharmaceutically acceptable salt thereof, wherein L and LBM or DIM are as defined above and described in embodiments herein, and wherein each of the variables Ring A, Ring B, $X_1$, $X_2$, $X_3$, $X_4$, Y, Z, $R^A$, $R_B$, $R_C$, $R_N$, $R_X$, $L_B$, p, q, and ∿∿∿ is as described and defined in WO 2016/089060 and US 2017/0320889, the entirety of each of which is herein incorporated by reference.

In certain embodiments, the present invention provides a compound of formula I or formula II, wherein STAT is a STAT3 binding moiety thereby forming a compound of formula I-aal or II-jj:

I-aal

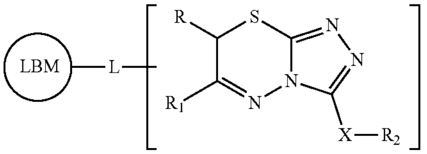

II-jj

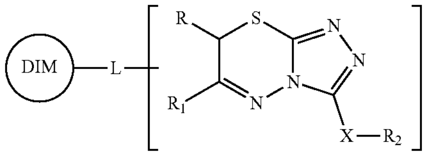

or a pharmaceutically acceptable salt thereof, wherein L and LBM or DIM are as defined above and described in embodiments herein, and wherein each of the variables $R_1$ and $R_2$ is as described and defined in WO 2016/115455, the entirety of each of which is herein incorporated by reference.

In certain embodiments, the present invention provides a compound of formula I or formula II, wherein STAT is a STAT3 binding moiety thereby forming a compound of formula I-aam or II-kk:

I-aam

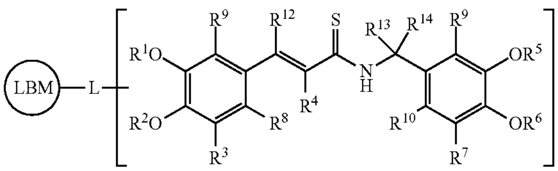

II-kk

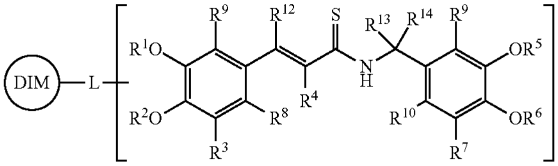

or a pharmaceutically acceptable salt thereof, wherein L and LBM or DIM are as defined above and described in embodiments herein, and wherein each of the variables $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$ is as described and defined in WO 2016/125169 and US 2018/0028475, the entirety of each of which is herein incorporated by reference.

In certain embodiments, the present invention provides a compound of formula I or formula II, wherein STAT is a STAT3 binding moiety thereby forming a compound of formula I-aan-1, I-aan-2, II-11-1, or II-11-2:

I-aan-1

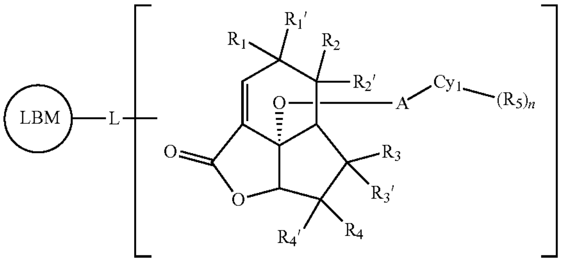

I-aan-2

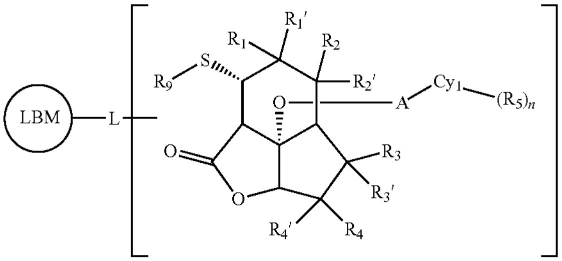

II-ll-1

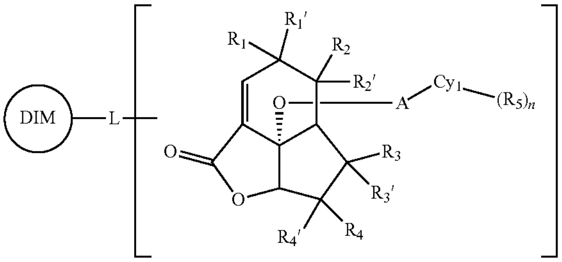

II-ll-2

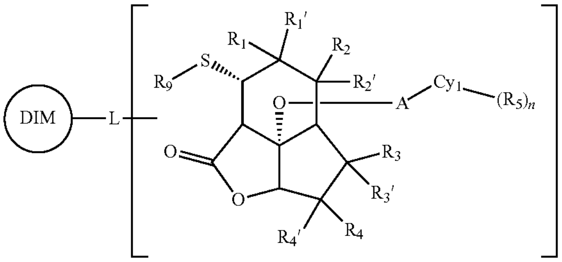

or a pharmaceutically acceptable salt thereof, wherein L and LBM or DIM are as defined above and described in embodiments herein, and wherein each of the variables $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$ is as described and defined in WO 2016/193332 and US 2018/0155360, the entirety of each of which is herein incorporated by reference.

In certain embodiments, the present invention provides a compound of formula I or formula II, wherein STAT is a STAT3 binding moiety thereby forming a compound of formula I-aao or II-mm:

I-aao

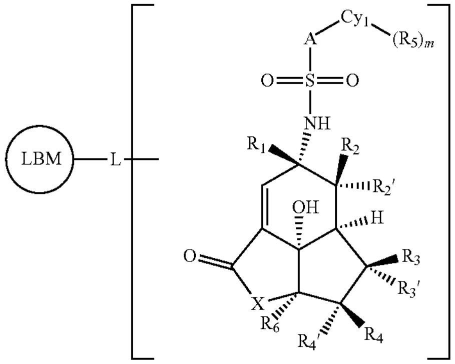

II-mm

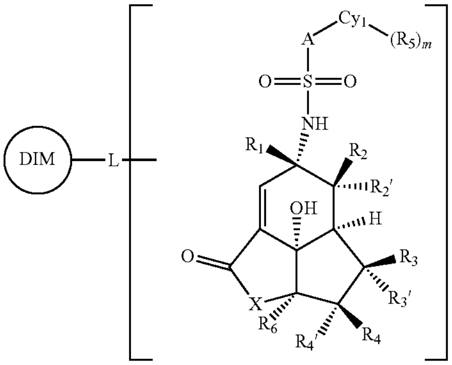

or a pharmaceutically acceptable salt thereof, wherein L and LBM or DIM are as defined above and described in embodiments herein, and wherein each of the variables $R_1$, $R_2$, $R_2'$, $R_3$, $R^{3'}$, $R_4$, $R_4'$, $R_5$, $R_6$, A, X, $Cy_1$, and m is as described and defined in WO 2018/104295, the entirety of each of which is herein incorporated by reference.

In certain embodiments, the present invention provides a compound of formula I or formula II, wherein STAT is a STAT3 binding moiety thereby forming a compound of formula I-aap or II-nn:

I-aap

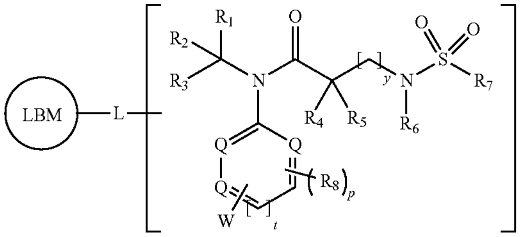

-continued

II-nn

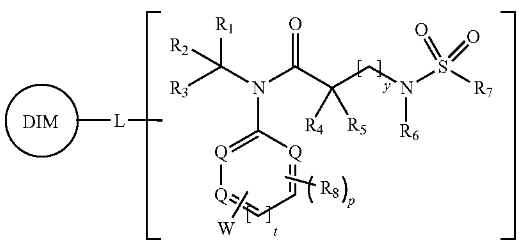

or a pharmaceutically acceptable salt thereof, wherein L and LBM or DIM are as defined above and described in embodiments herein, and wherein each of the variables $R_1$, $R_2$, $R_3$, $R_4$, $R_5$, $R_6$, $R_7$, $R_8$, Q, W, t, p, and y is as described and defined in WO 2018/136935, the entirety of each of which is herein incorporated by reference.

In some embodiments, the present invention provides a compound of formula I or formula II, wherein STAT is a STAT3 binding moiety selected from a compound recited in Dhanik, A. et al. *Binding Modes of Peptidomimetics Designed to InhibitSTAT3*, PLoS ONE 2012, 7(12):e51603 such as, for example:

I-aaq-1

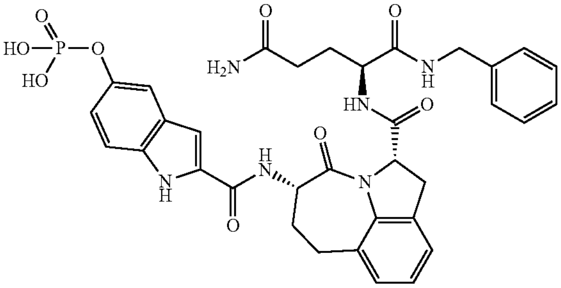

I-aaq-2

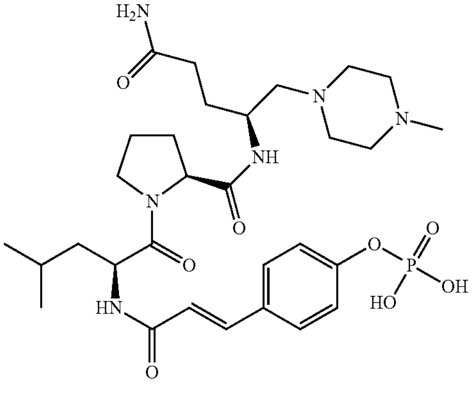

-continued

I-aaq-3

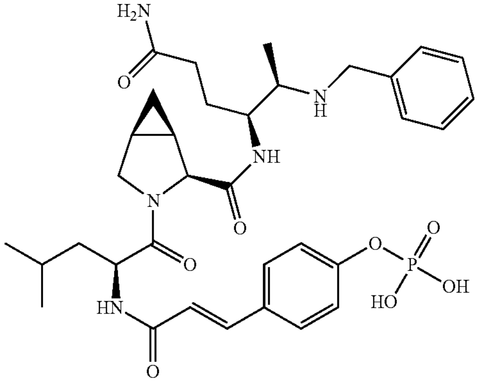

I-aaq-4

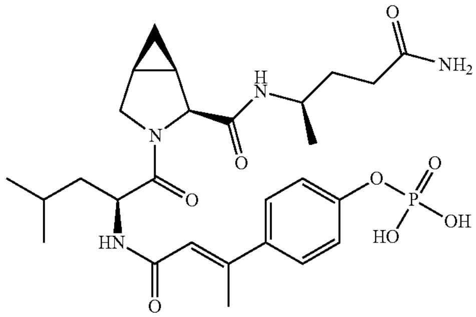

I-aaq-5

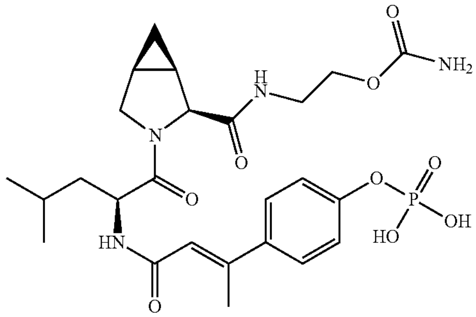

I-aaq-6

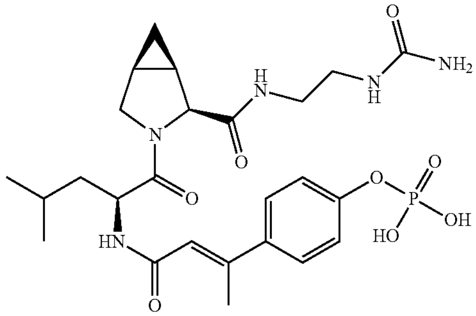

-continued
I-aaq-7
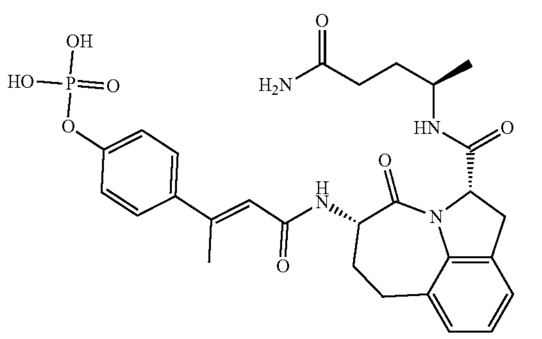
I-aaq-8
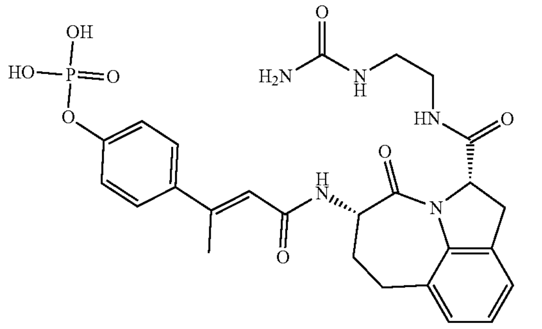
II-oo-1
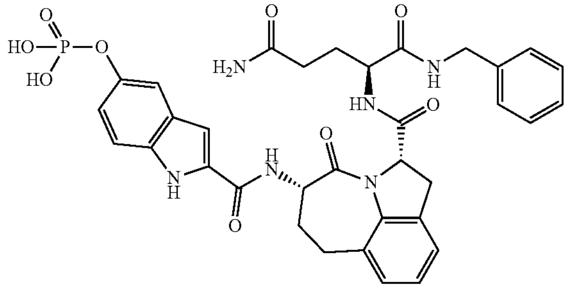
II-oo-2
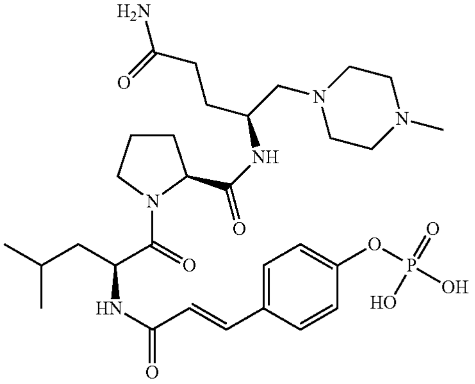
-continued
II-oo-3
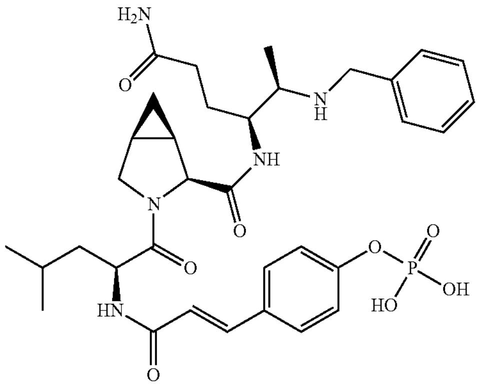
II-oo-4
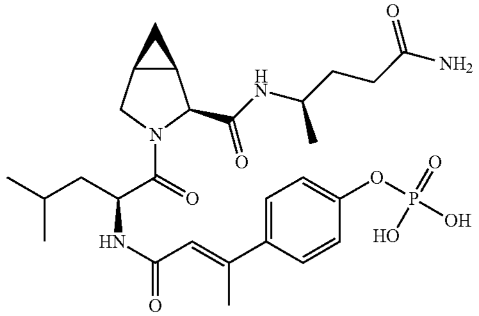
II-oo-5
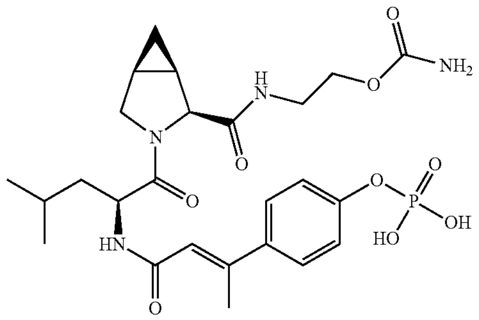
II-oo-6
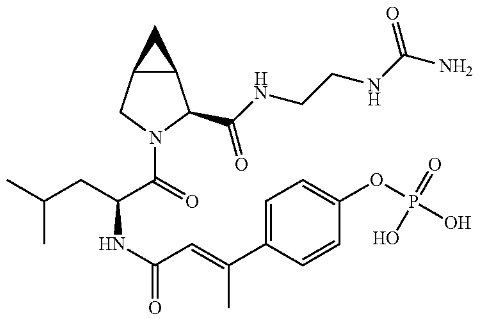

-continued

II-oo-7

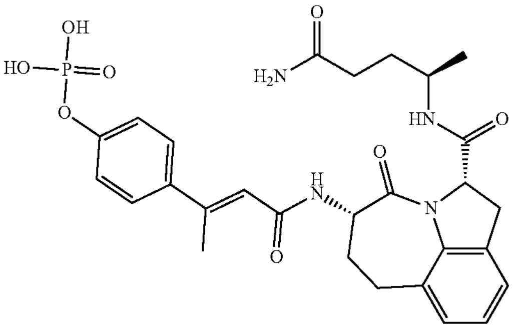

II-oo-8

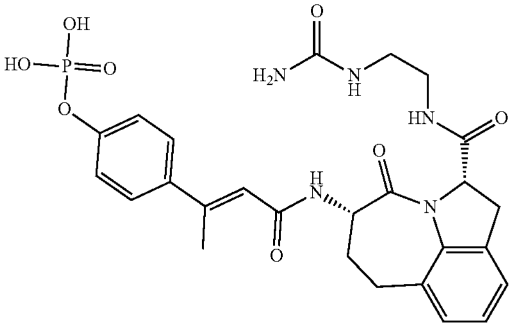

or a pharmaceutically acceptable salt thereof, wherein

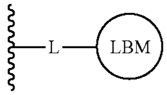

or

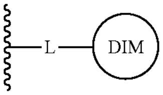

is attached to a modifiable carbon, oxygen, or nitrogen atom.

In some embodiments, the present invention provides a compound formula I or formula II, wherein STAT is a STAT3 binding moiety selected from a compound recited in Morlacchi, P. et al. *Targeting SH2 domains in breast cancer*, Future Med. Chem. 2014, 6(7):1909 such as, for example:

I-aar-1

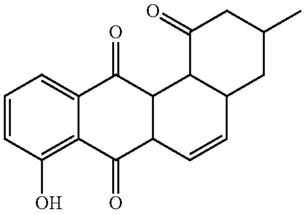

I-aar-2

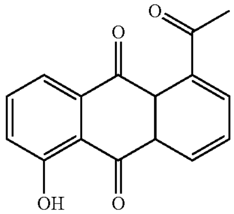

-continued

I-aar-3

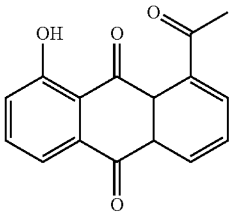

I-aar-4

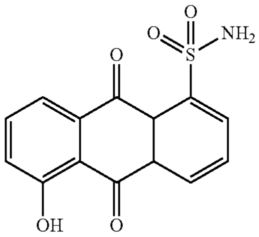

I-aar-5

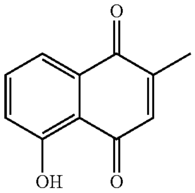

I-aar-6

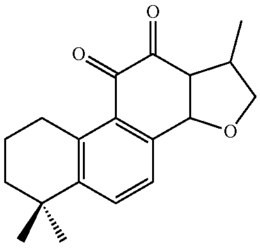

I-aar-7

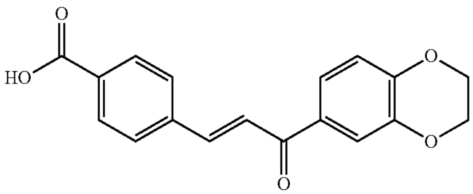

I-aar-8

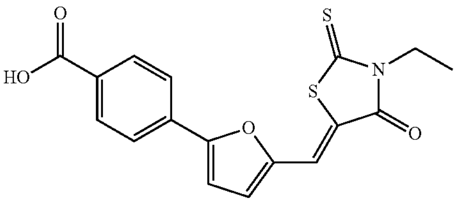

-continued
I-aar-9
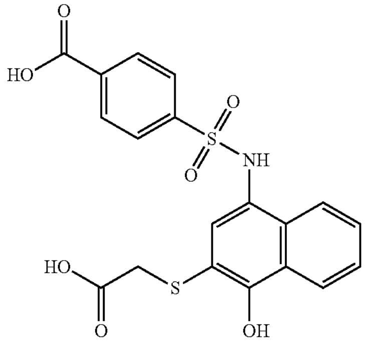
I-aar-10
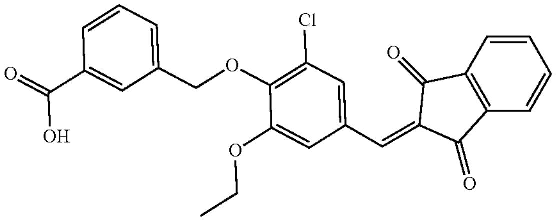
I-aar-11
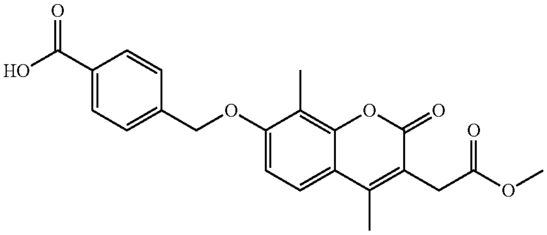
I-aar-12
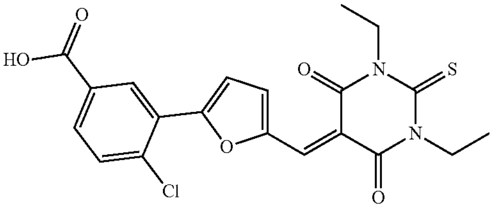
I-aar-13
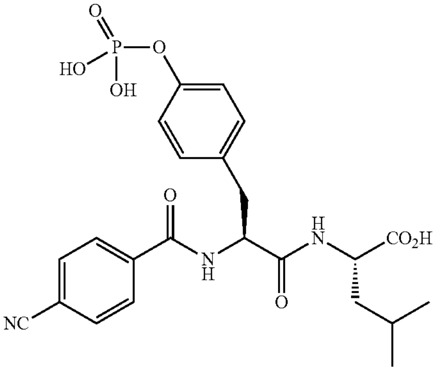
-continued
I-aar-14
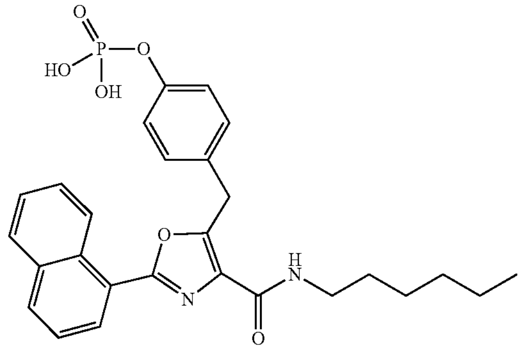
I-aar-15
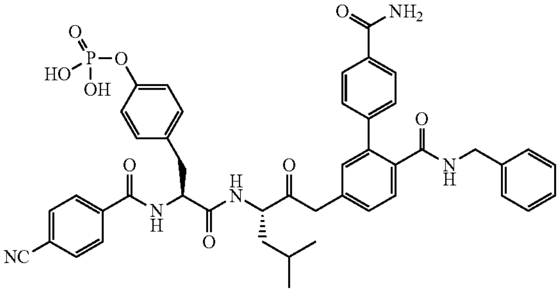
I-aar-16
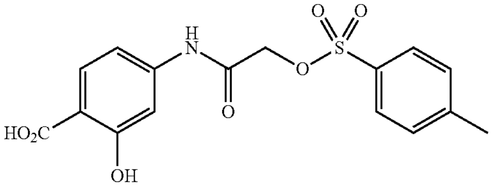
I-aar-17
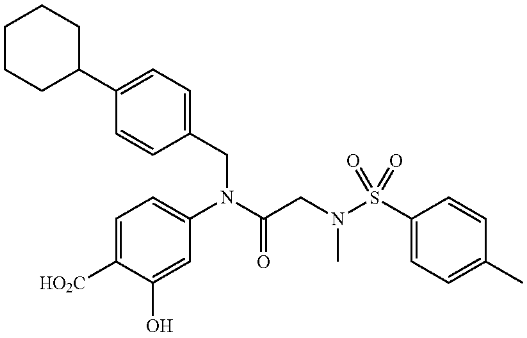
I-aar-18
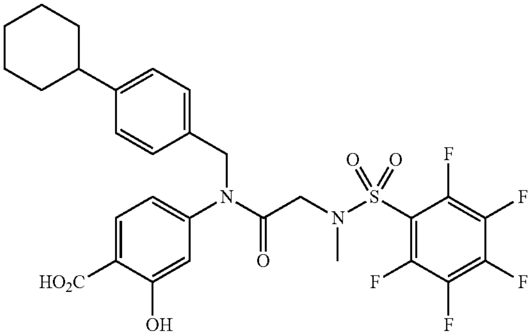

-continued
I-aar-19
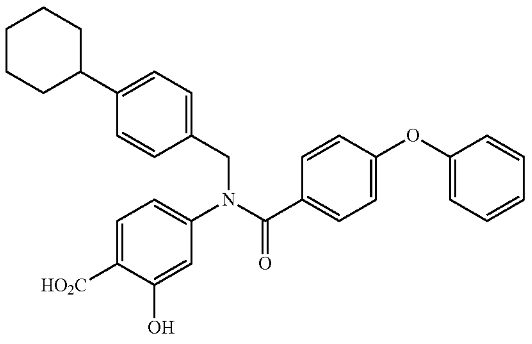
I-aar-20
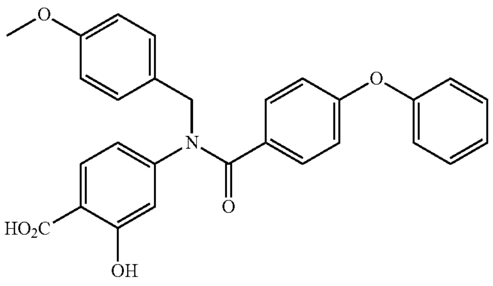
I-aar-21
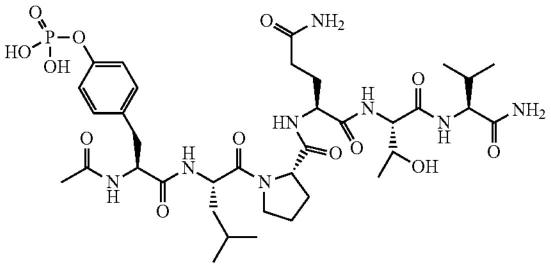
I-aar-22
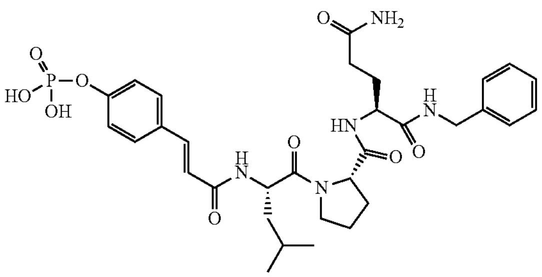
I-aar-23
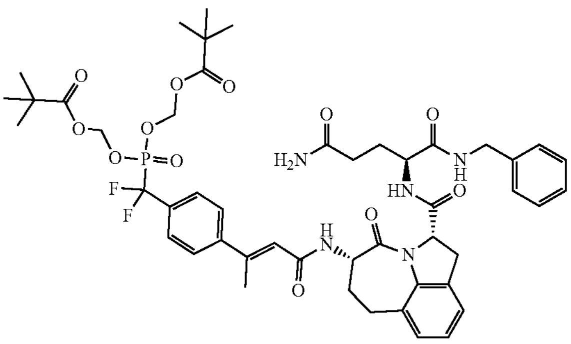
-continued
I-aar-24
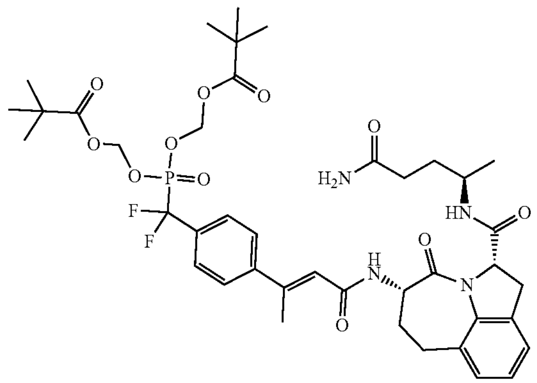
I-aar-25
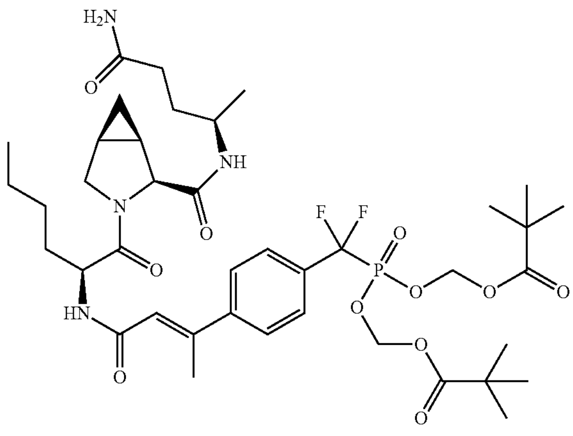
I-aar-26
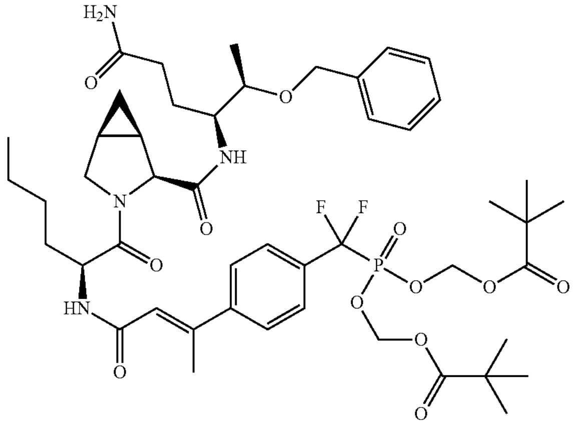
II-pp-1
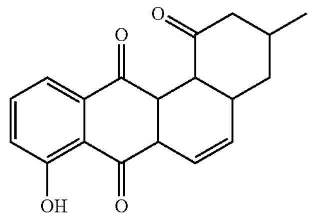

-continued
II-pp-2
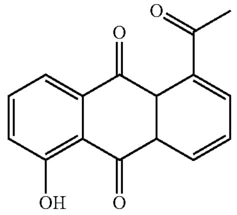
II-pp-3
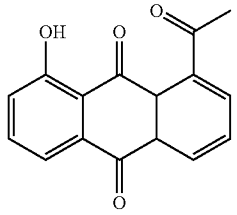
II-pp-4
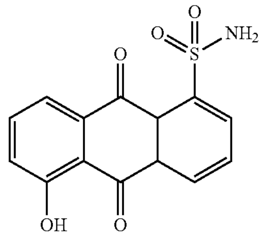
II-pp-5
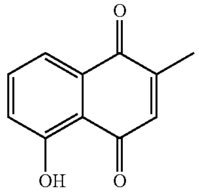
II-pp-6
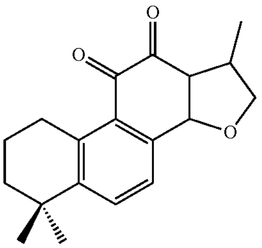
II-pp-7
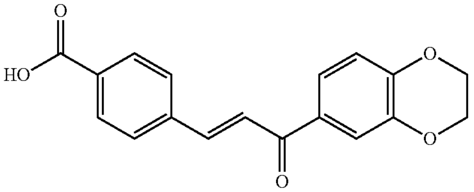
II-pp-8
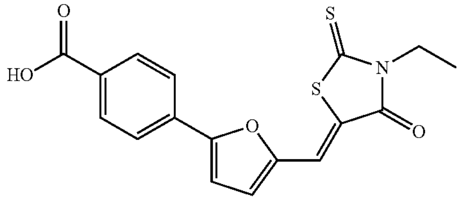
-continued
II-pp-9
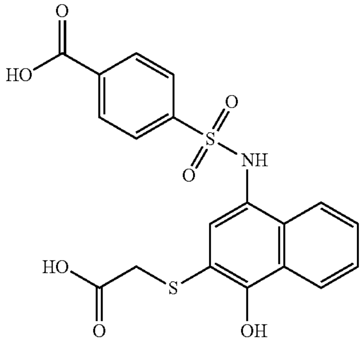
II-pp-10
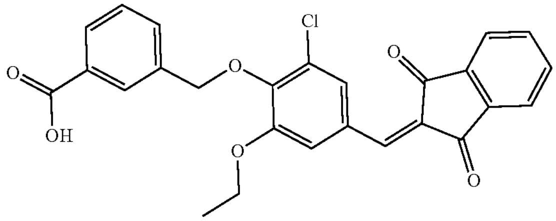
II-pp-11
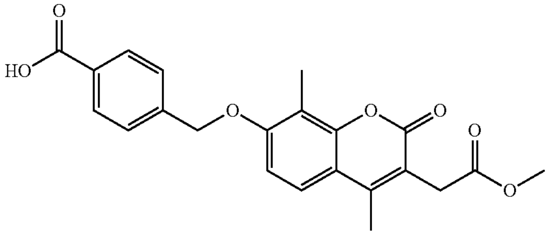
II-pp-12
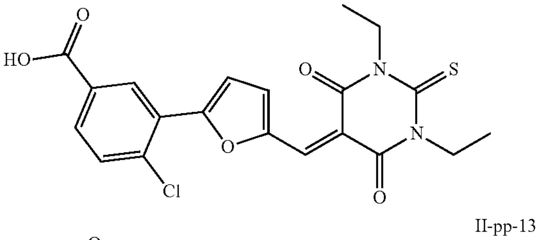
II-pp-13
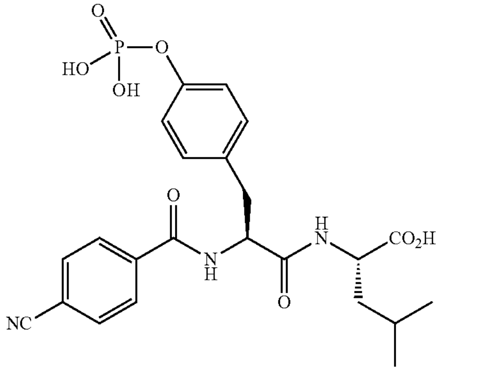

-continued
II-pp-14
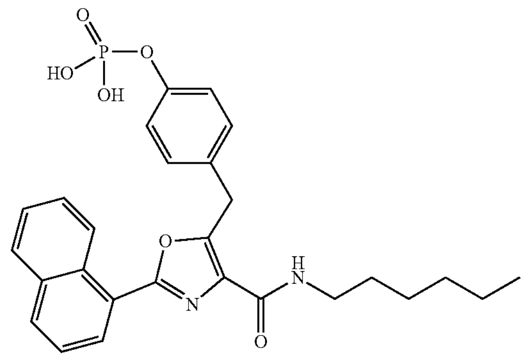
II-pp-15
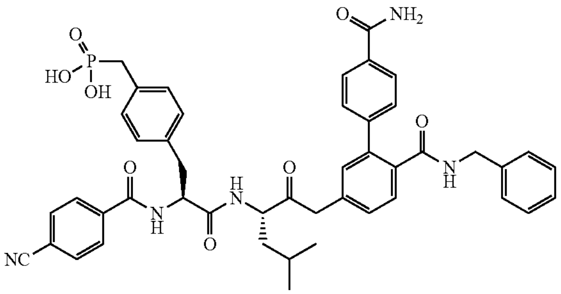
II-pp-16
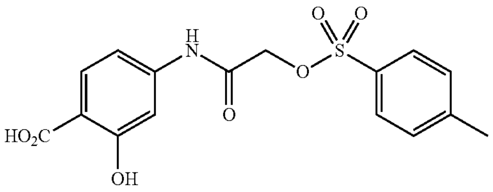
II-pp-17
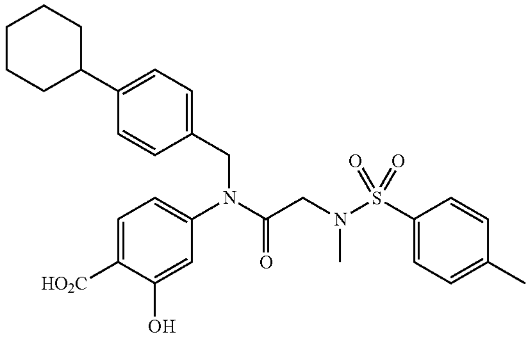
II-pp-18
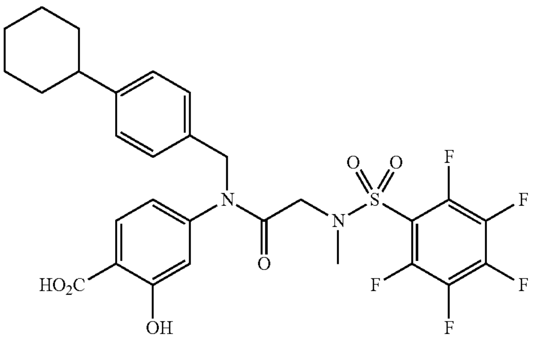
-continued
II-pp-19
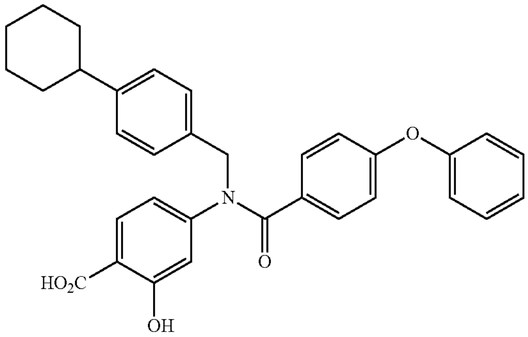
II-pp-20
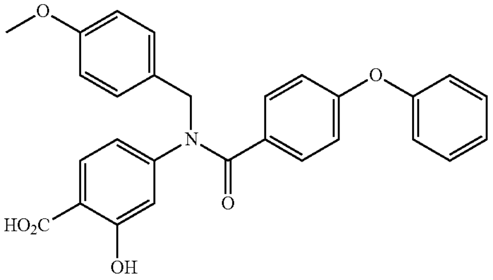
II-pp-21
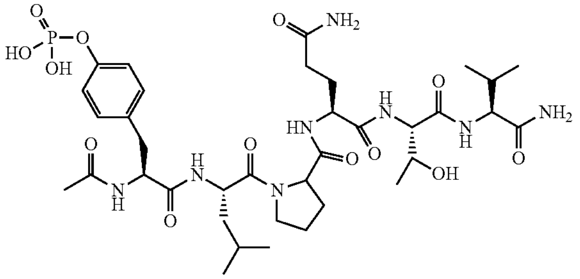
II-pp-22
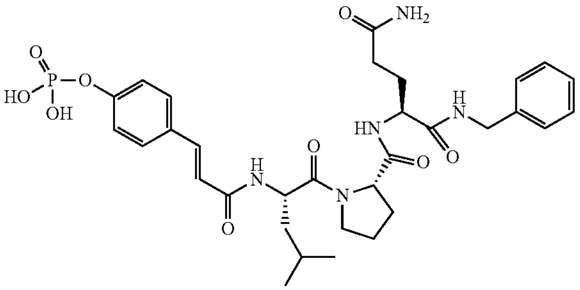
II-pp-23
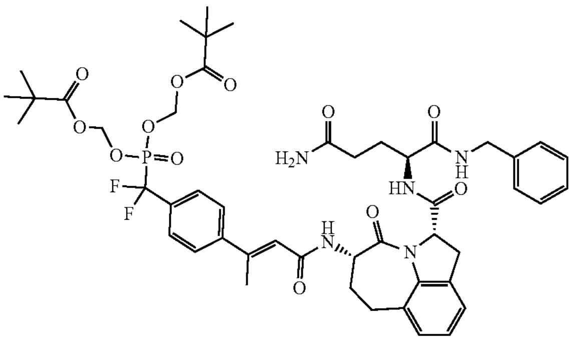

-continued

II-pp-24

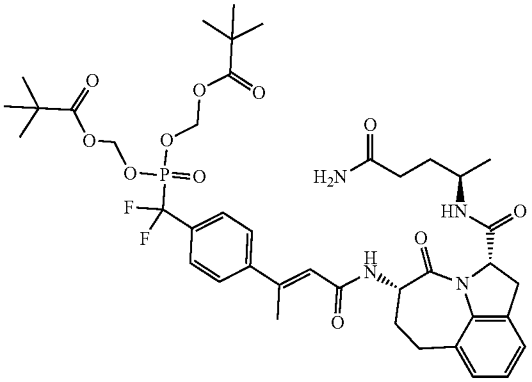

II-pp-25

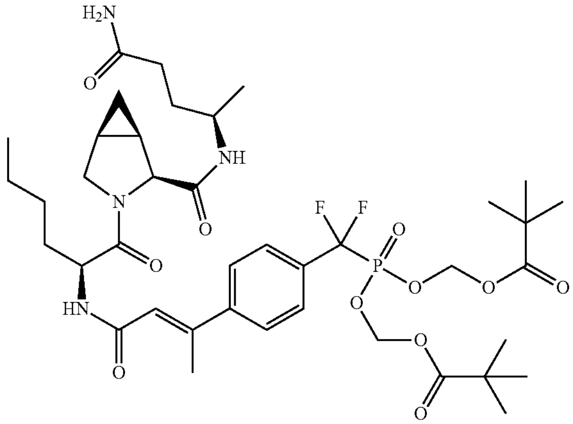

II-pp-26

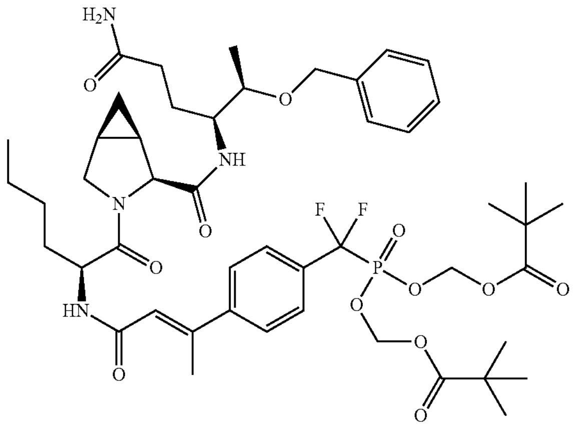

or a pharmaceutically acceptable salt thereof, wherein

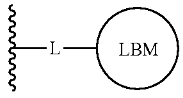
or
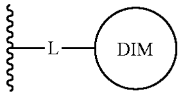

is attached to a modifiable carbon, oxygen, nitrogen or sulfur atom.

In some embodiments, the present invention provides a compound of formula I or formula II, wherein STAT is a STAT3 binding moiety selected from a compound recited in Qiu, H. Y. et al. *Identification of New Shikonin Derivatives as Antitumor Agents Targeting STAT3 SH2 Domain*, Sci. Rep. 2017, 7:2863 such as, for example:

I-aas-1

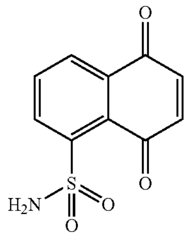

I-aas-2

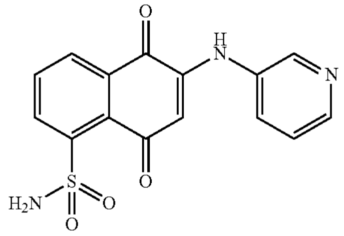

I-aas-3

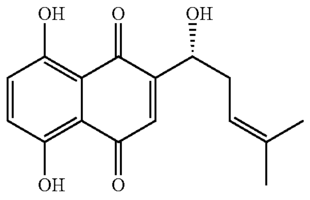

I-aas-4

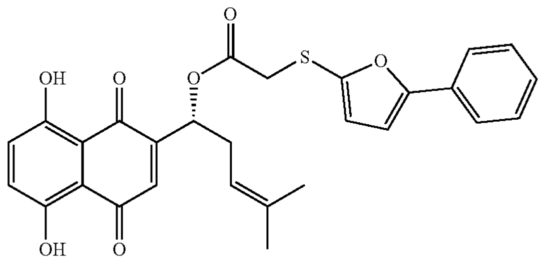

I-aas-5

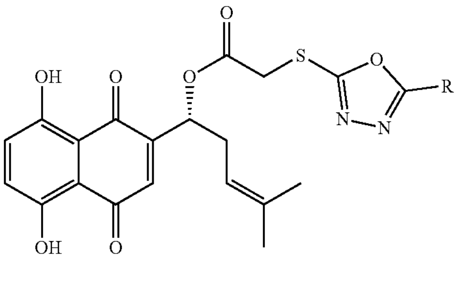

II-qq-1

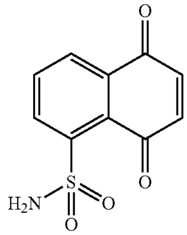

-continued

II-qq-2

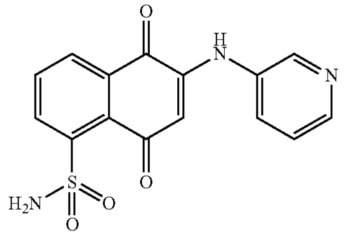

II-qq-3

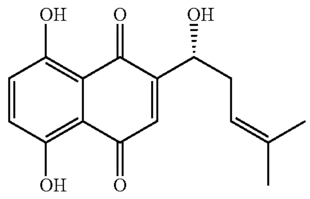

II-qq-44

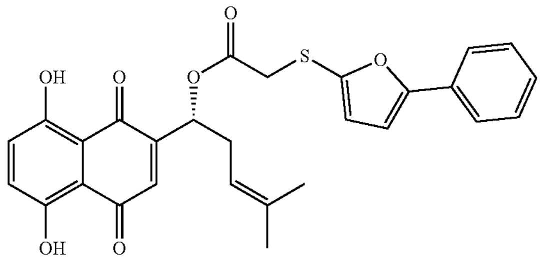

II-qq-5

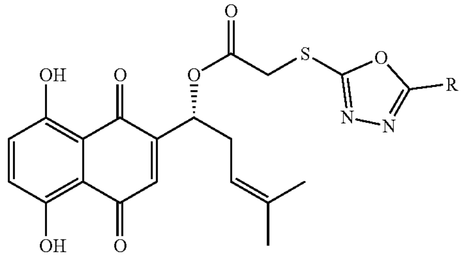

or a pharmaceutically acceptable salt thereof, wherein R is defined by compounds PMM-158 to PMM-173 and

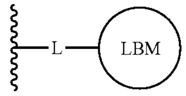

or

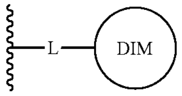

is attached to a modifiable carbon, oxygen, nitrogen or sulfur atom.

In some embodiments, the present invention provides a compound of formula I or formula II, wherein STAT is a STAT3 binding moiety selected from a compound recited in Yu. X. et al. *Eriocalyxin B Inhibits STAT3 Signaling by Covalently Targeting STAT3 and Blocking Phosporylation and Activation of STAT3*, PLoS ONE 2015, 10(5):e0128406 such as, for example:

I-aat

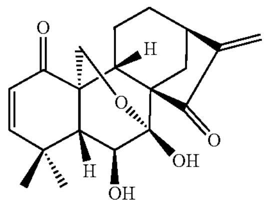

II-rr

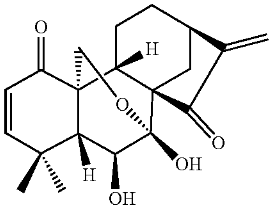

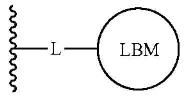

or

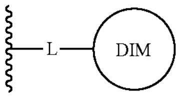

or a pharmaceutically acceptable salt thereof, wherein or is attached to a modifiable carbon or oxygen atom.

In some embodiments, the present invention provides a compound of formula I or formula II, wherein STAT is a STAT3 binding moiety selected from a compound recited in Kolosenko, I. et al. *Identification of novel small molecule that inhibit STAT3-dependent transcription and function*, PLoS ONE 2017, 12(6):e0178844 such as, for example:

I-aau-1

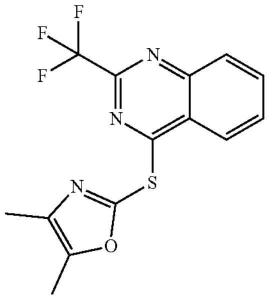

I-aau-2

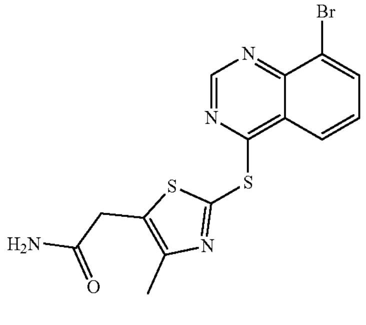

-continued

I-aau-3

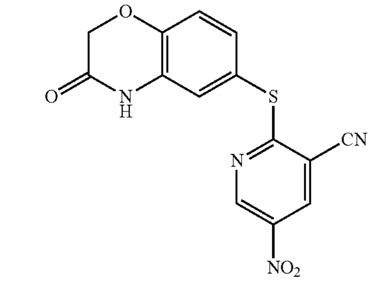

I-aau-4

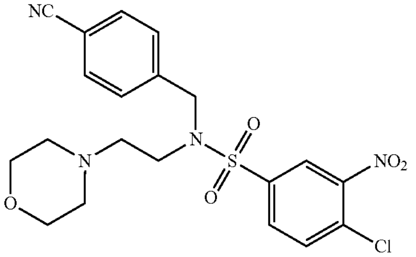

II-ss-1

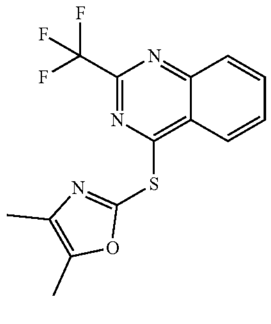

II-ss-2

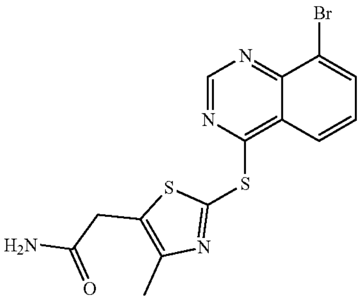

II-ss-3

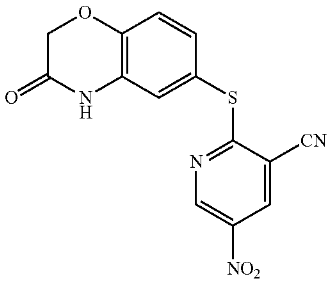

-continued

II-ss-4

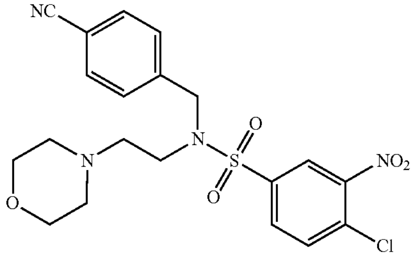

or a pharmaceutically acceptable salt thereof, wherein

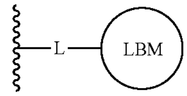

or

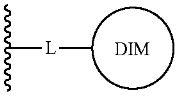

is attached to a modifiable carbon, oxygen, nitrogen or sulfur atom.

In some embodiments, the present invention provides a compound of formula I or formula II, wherein STAT is a STAT3 binding moiety selected from a compound recited in Zheng, W. et al. *Discovery of monocarbonyl curcumin-BTP hydbrids as STAT3 inhibitors for drug-sensitive and drug-resistant breast cancer therapy*, Sci. Rep. 2017, 7:46352 such as, for example:

I-aav

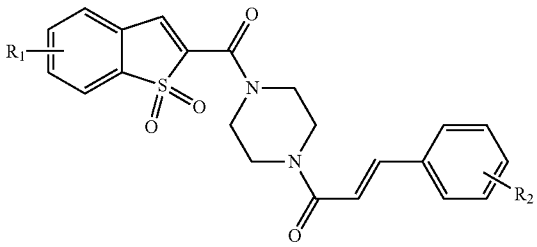

II-tt

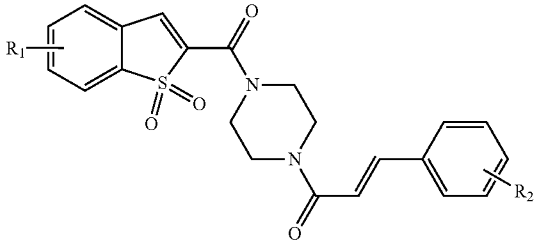

or a pharmaceutically acceptable salt thereof, wherein $R_1$ and $R_2$ are defined by compounds defined and described therein and

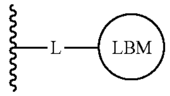

or

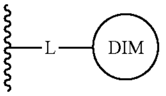

is attached to a modifiable carbon nitrogen, or oxygen atom.

In some embodiments, the present invention provides a compound of formula I or formula II, wherein STAT is a STAT3 binding moiety selected from a compound recited in Zheng, W. et al. *MMPP Attenuates Non*-Small Cell Lung Cancer Growth by Inhibiting the STAT3 DNA-Binding Activity via Direct Binding to the STAT3 *DNA-Binding Domain*, Theranostics 2017, 7(18):4632 such as, for example:
I-aaw-1
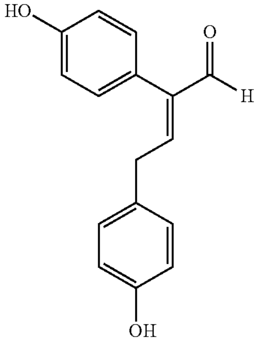
I-aaw-2
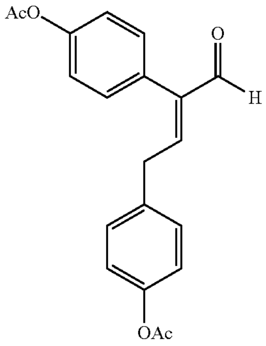
I-aaw-3
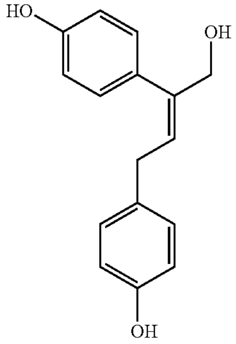
I-aaw-4
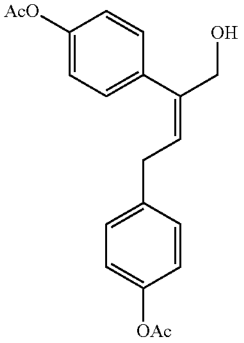
-continued
I-aaw-5
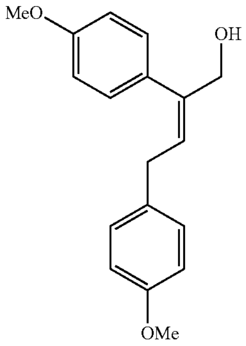
I-aaw-6
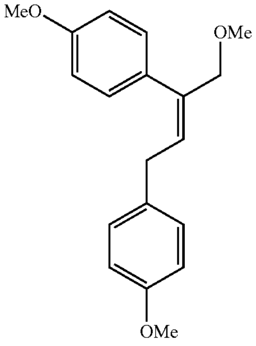
I-aaw-7
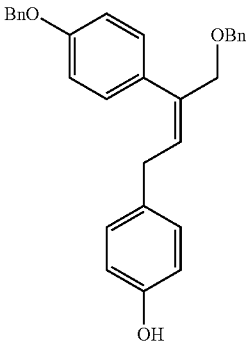
I-aaw-8
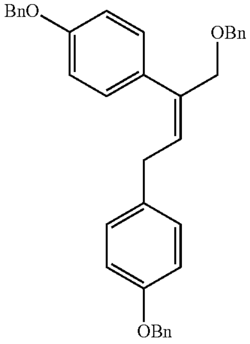

-continued
I-aaw-9
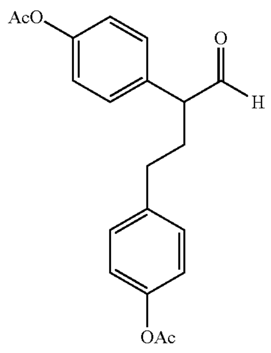
I-aaw-10
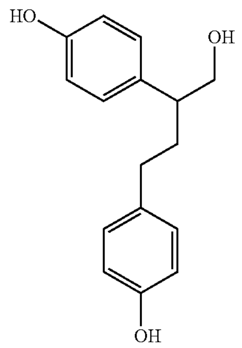
I-aaw-11
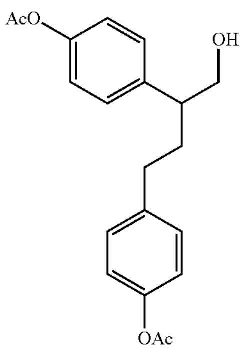
I-aaw-12
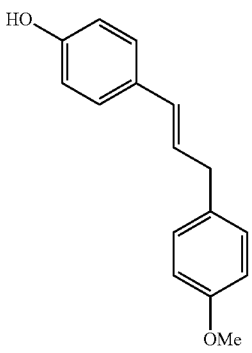
-continued
I-aaw-13
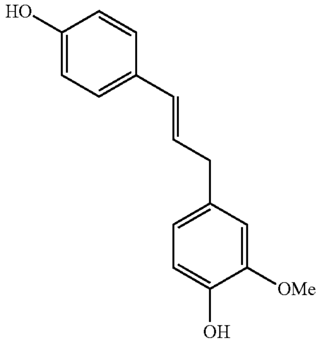
I-aaw-14
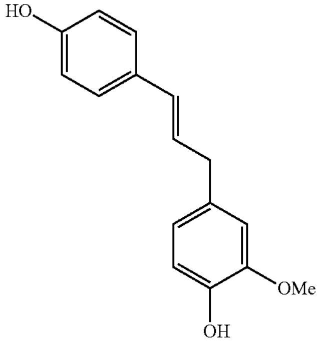
I-aaw-15
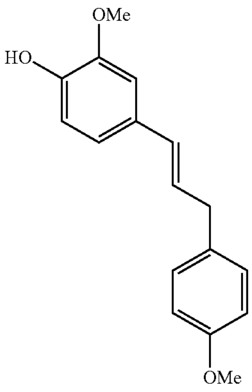
I-aaw-16
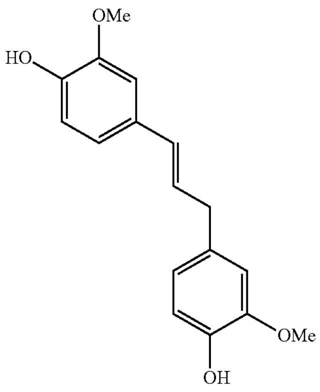

-continued
I-aaw-17
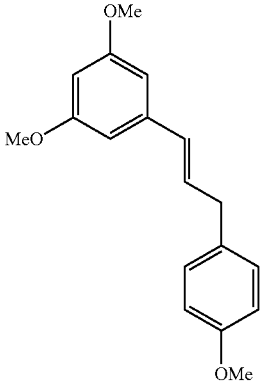
I-aaw-18
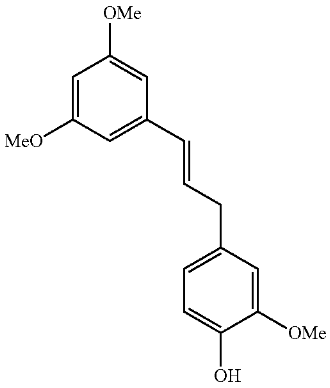
II-uu-1
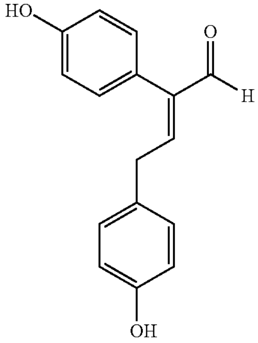
II-uu-2
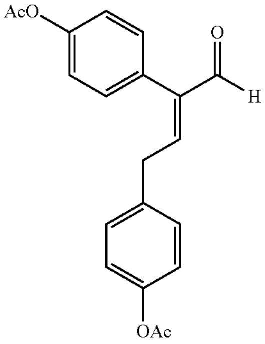
-continued
II-uu-3
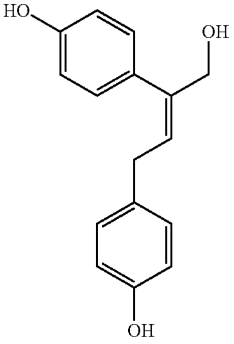
II-uu-4
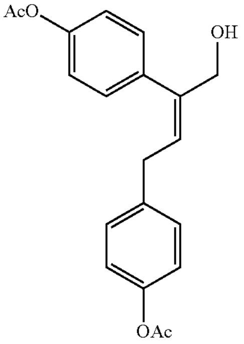
II-uu-5
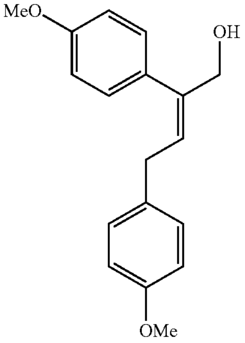
II-uu-6
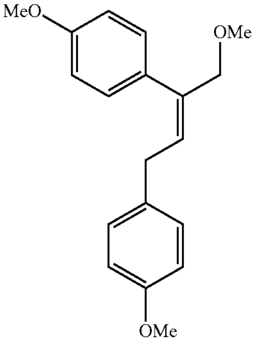

-continued
II-uu-7
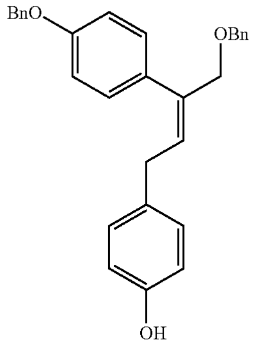
II-uu-8
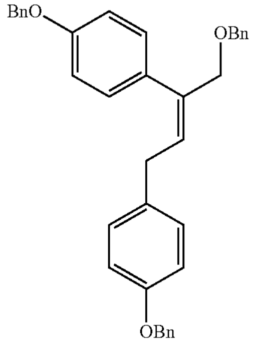
II-uu-9
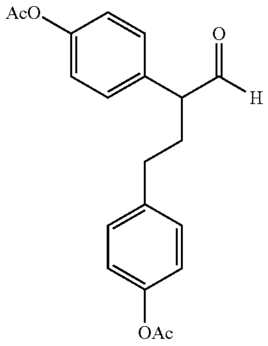
II-uu-10
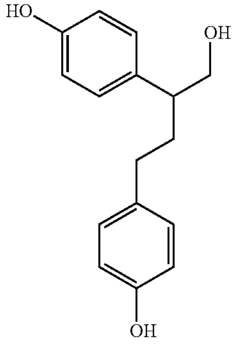
-continued
II-uu-11
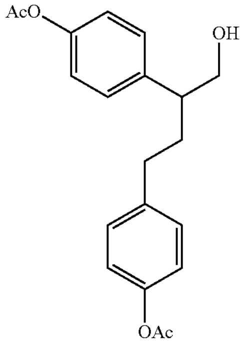
II-uu-12
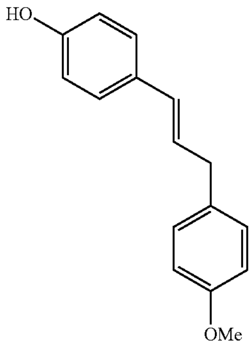
II-uu-13
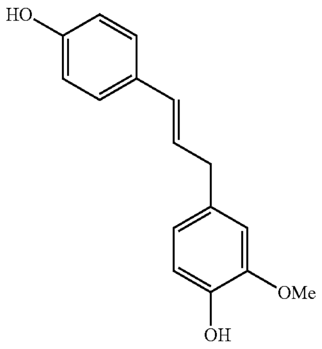
II-uu-14
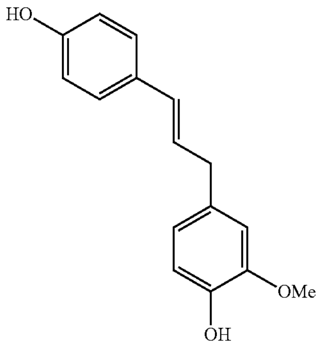

-continued

II-uu-15

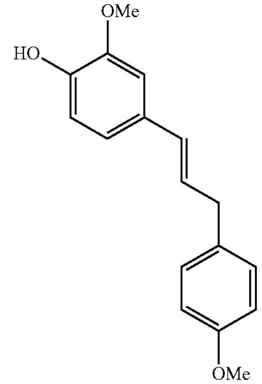

II-uu-16

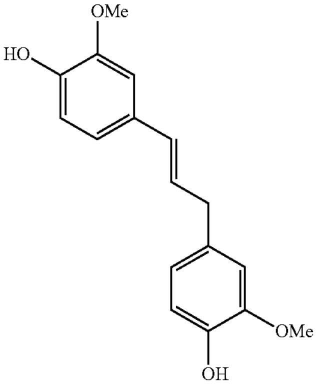

II-uu-17

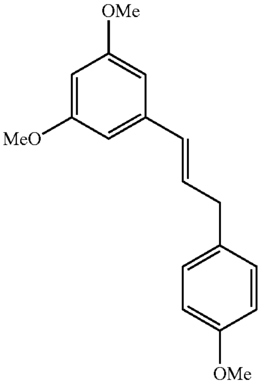

II-uu-18

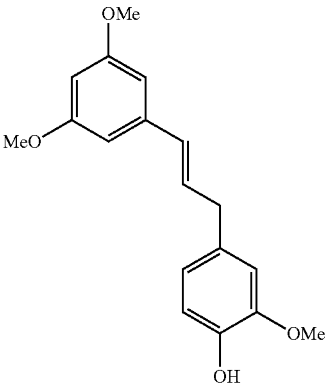

or a pharmaceutically acceptable salt thereof, wherein

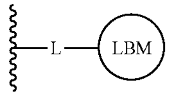 or 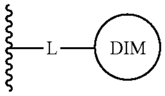

is attached to a modifiable carbon or oxygen atom.

In some embodiments, the present invention provides a compound of formula I or formula II, wherein STAT is a STAT3 binding moiety selected from a compound recited in Feng, T. et al. *Arctigenin inhibits STAT3 and exhibits anti-cancer potential in human triple-negative breast cancer therapy*, Oncotarget 2017, 8(1):329 such as, for example:

I-aax

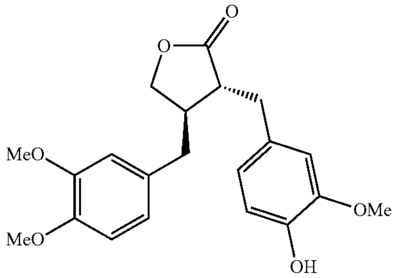

II-vv

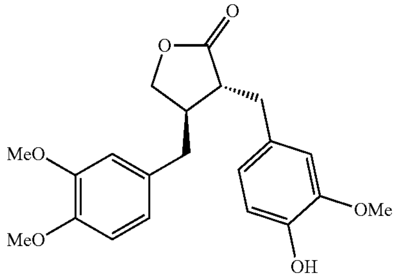

or a pharmaceutically acceptable salt thereof, wherein

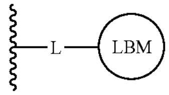 or 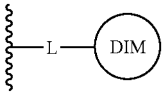

is attached to a modifiable carbon or oxygen atom.

In some embodiments, the present invention provides a compound of formula I or formula II, wherein STAT is a STAT1 or STAT3 binding moiety selected from a compound recited in Szelag, M. et al. *Identification of STAT1 and STAT3 Specific Inhibitors Using Comparative Virtual Screening and Docking Validation*, PLoS ONE 2015, 10(2): e0116688 such as, for example natural compounds (e.g., cryptotanshinone, curcumin, cucurbitacin E and cucurbitacin Q) or chemical substances of synthetic origin (e.g., LLL12, FLLL32, Cpd188, Cpd30-12, STX-0119, HJC1023, S31-201, S3I-201.1066, BP-1-102, OPB-31121, WP1066, RSVA314, and RSVA405), or a pharmaceutically acceptable salt thereof, wherein

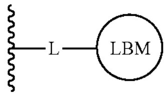

or

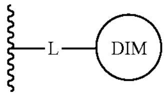

or is attached to a modifiable carbon, oxygen, nitrogen or sulfur atom.

In some embodiments, the present invention provides a compound of formula II, wherein STAT is a STAT3 binding moiety selected from a compound recited in Chen, J. et al. *Structure-Based Design of Conformationally Constrained, Cell-Permeable STAT3Inhibitors*, J. Med. Chem. Lett. 2010, 1:85 such as, for example:

II-ww-1

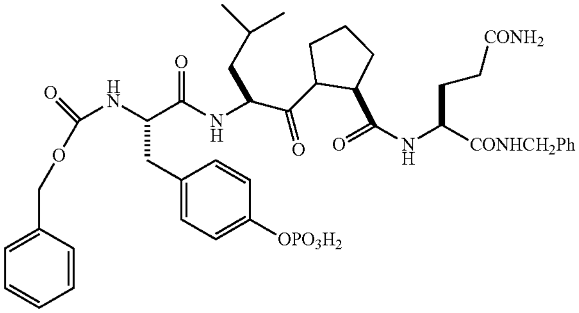

II-ww-2

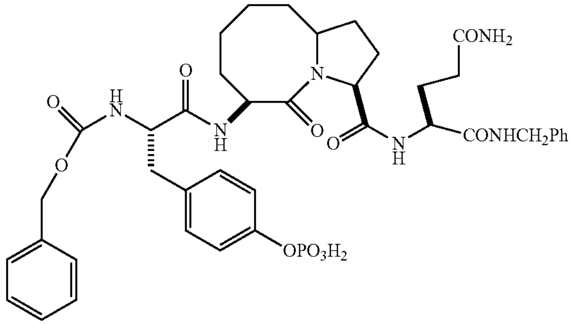

II-ww-3

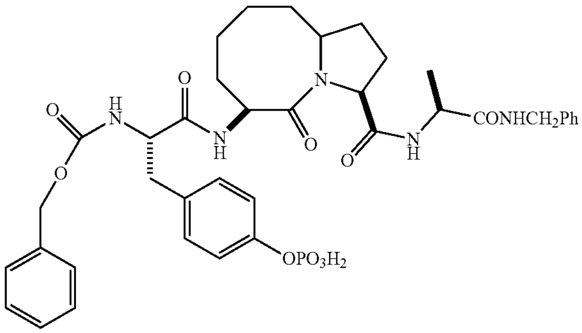

-continued

II-ww-4

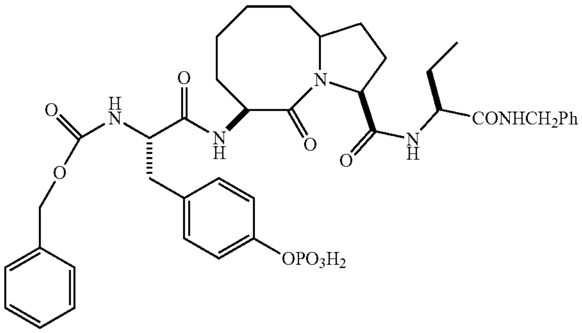

II-ww-5

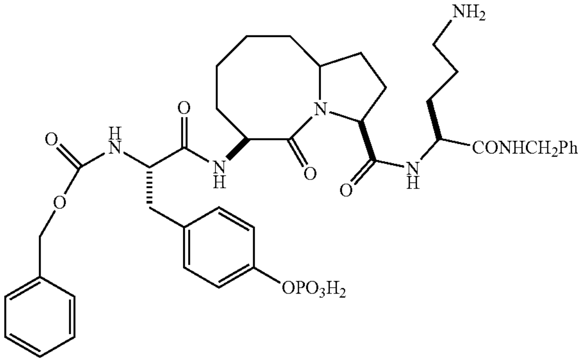

II-ww-6

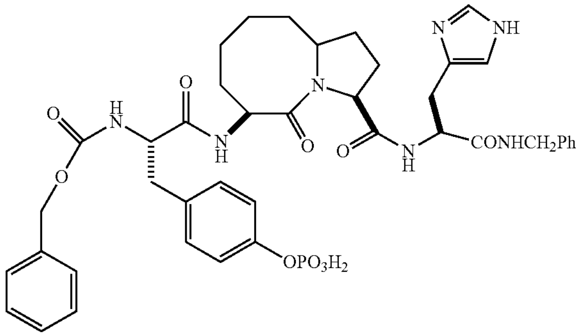

II-ww-7

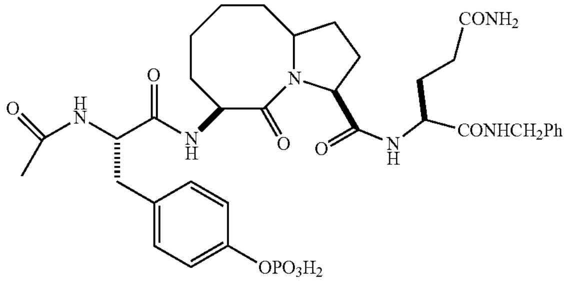

-continued
II-ww-8
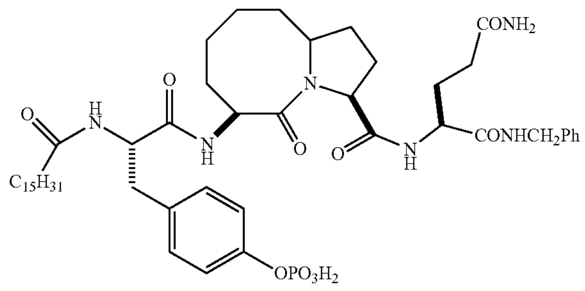
II-ww-9
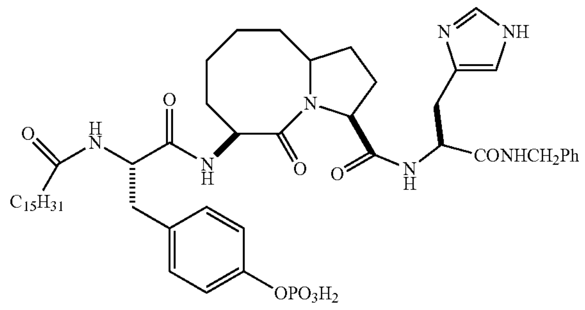
II-ww-10
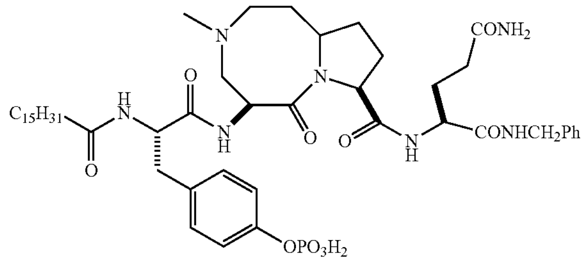
II-ww-11
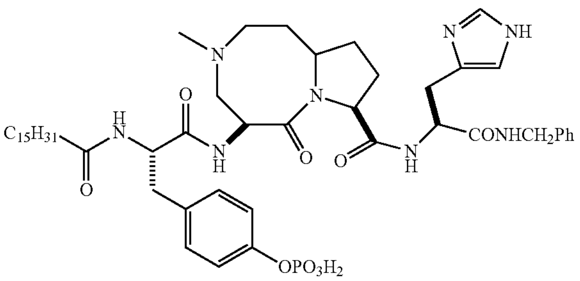
II-ww-12
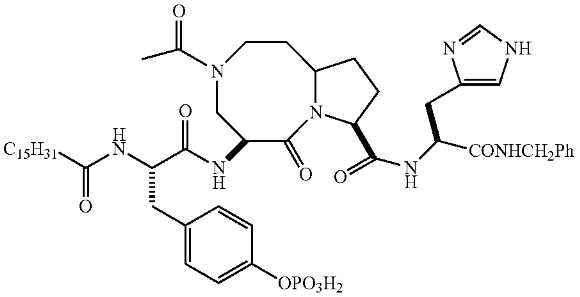
or a pharmaceutically acceptable salt thereof, wherein
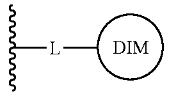
is attached to a modifiable carbon, oxygen, or nitrogen atom.
In some embodiments, the present invention provides a compound of formula II, wherein STAT is a STAT3 binding moiety selected from:
II-xx-1
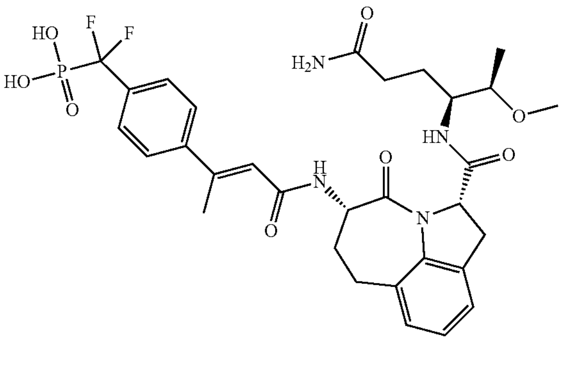
II-xx-2
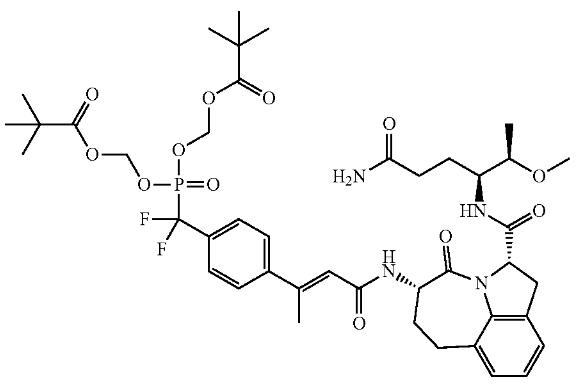

-continued
II-xx-3
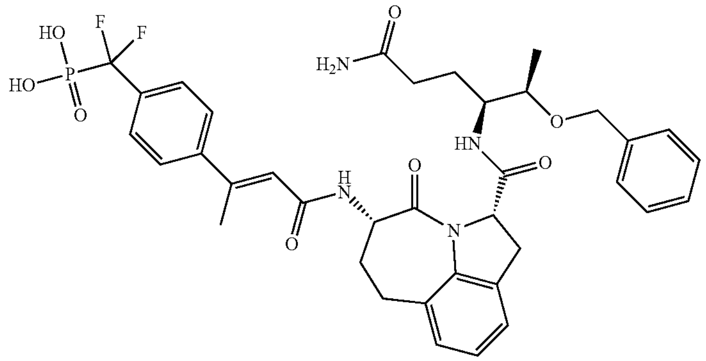
II-xx-4
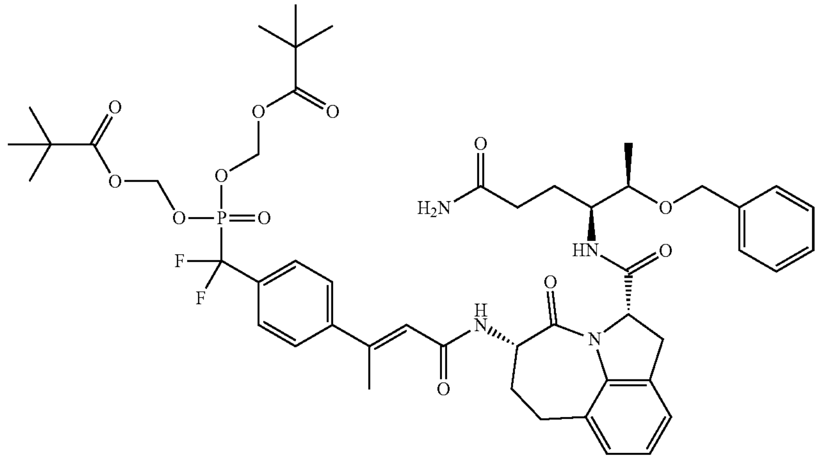
II-xx-5
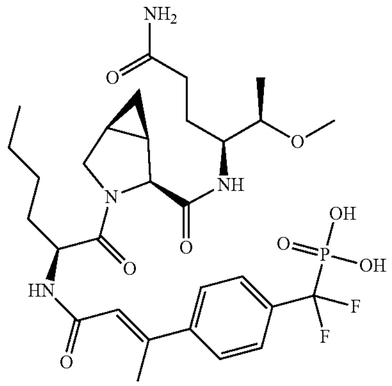
II-xx-6
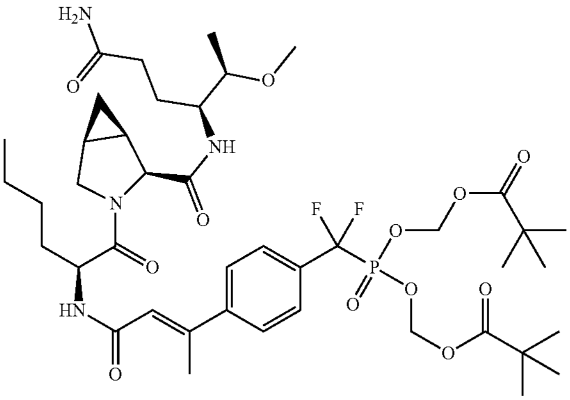
II-xx-7
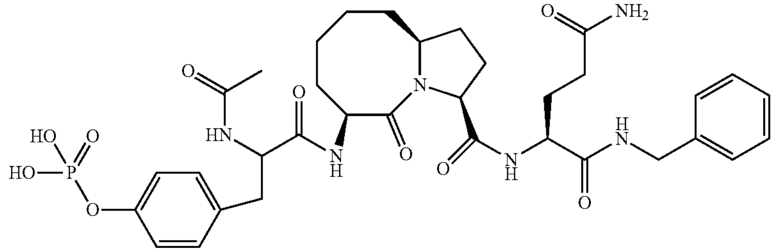

-continued
II-xx-8
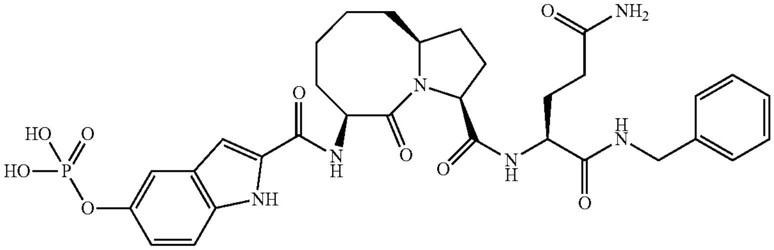
II-xx-9
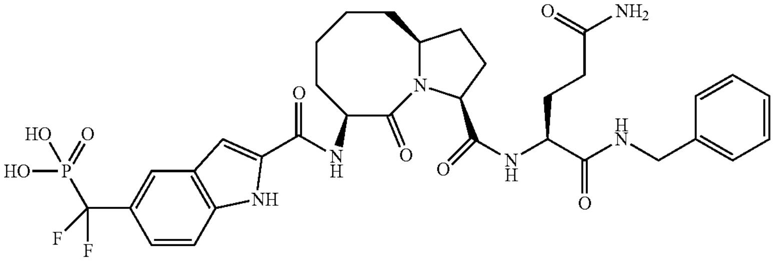
II-xx-10
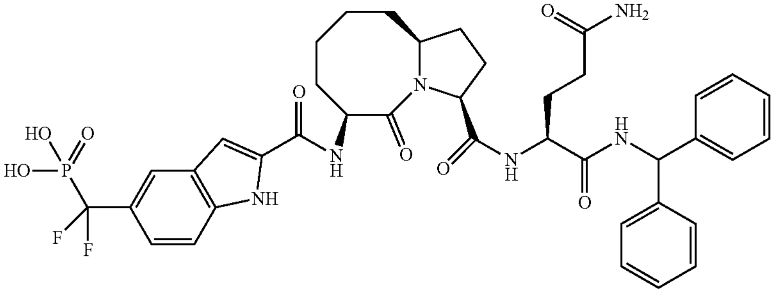
II-xx-11
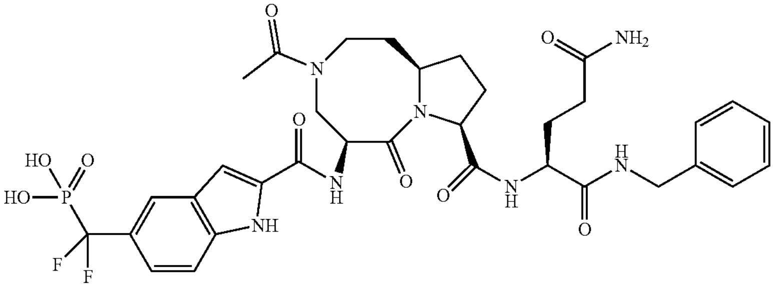
II-xx-12
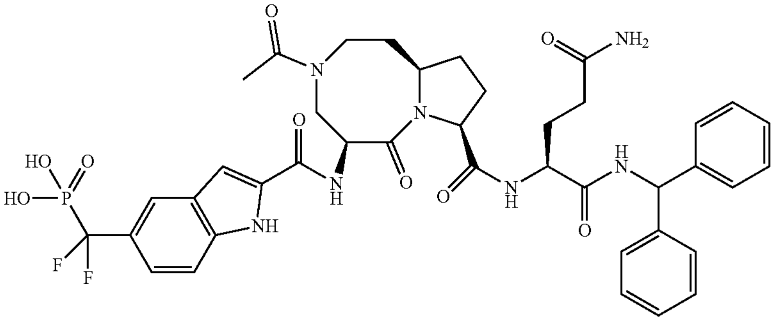

-continued
II-xx-13
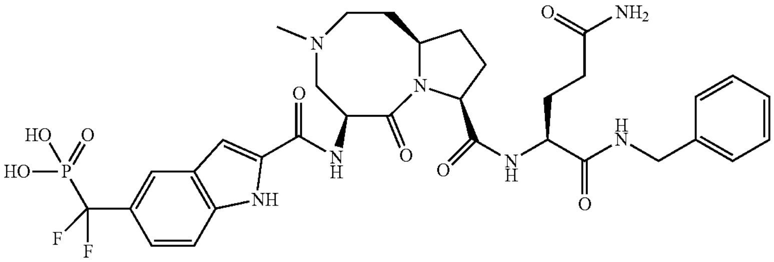
II-xx-14
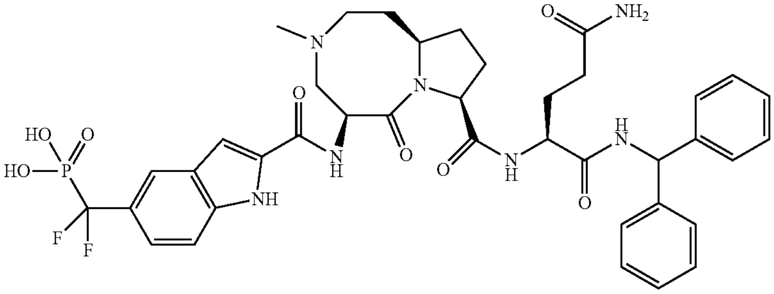
II-xx-15
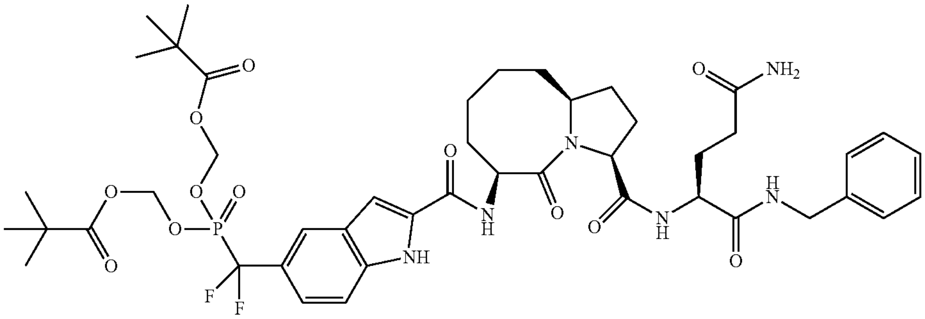
II-xx-16
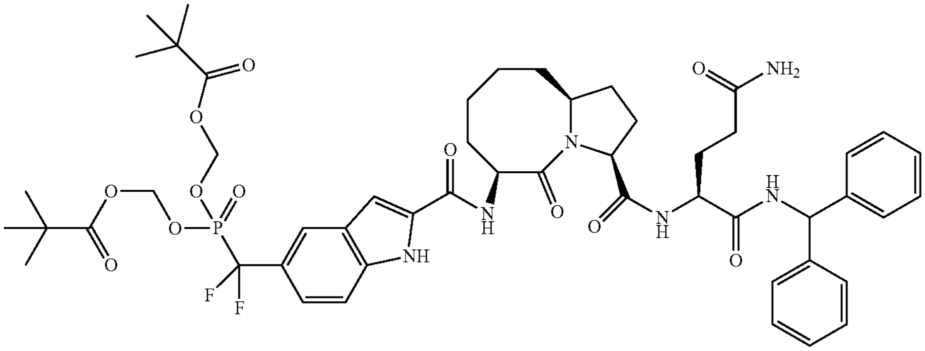
II-xx-17
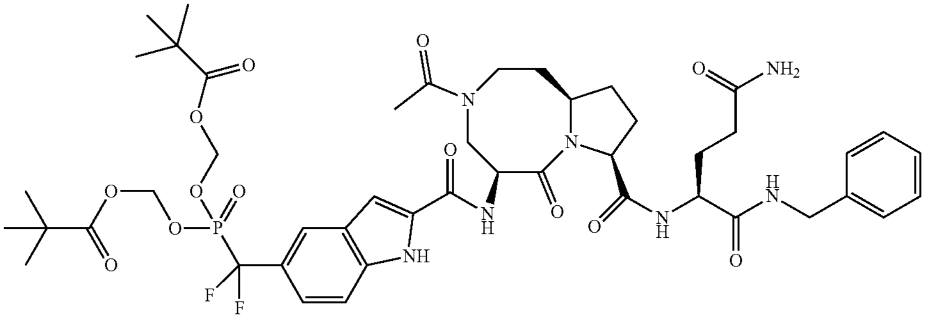

-continued
II-xx-18
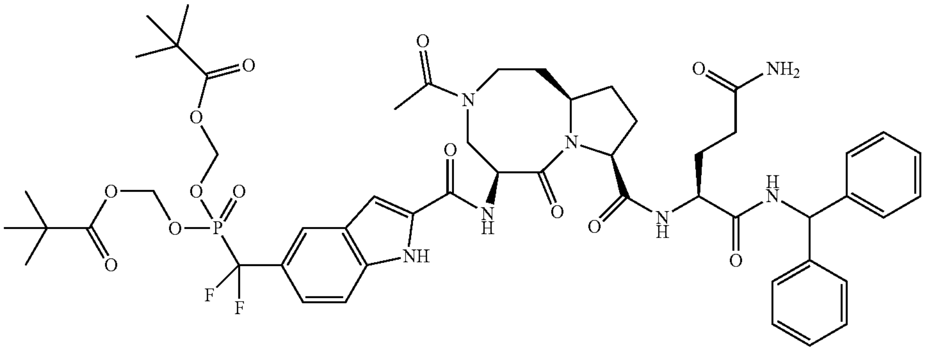
II-xx-19
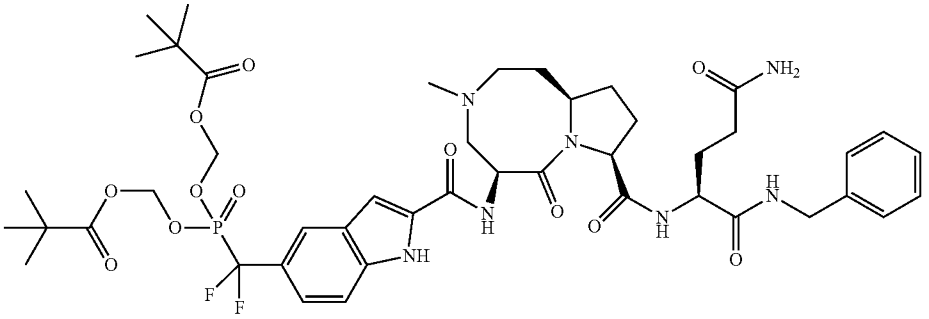
II-xx-20
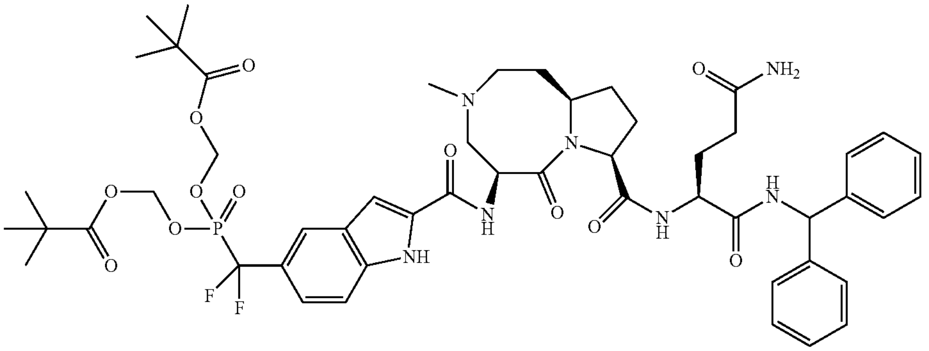
or a pharmaceutically acceptable salt thereof, wherein
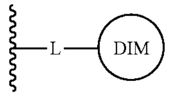
is attached to a modifiable carbon, oxygen, or nitrogen atom.
In certain embodiments, the present invention provides a compound of formula II, wherein STAT is a STAT3 binding moiety thereby forming a compound of formula II-yy-1 to II-yy-8:
II-yy-1
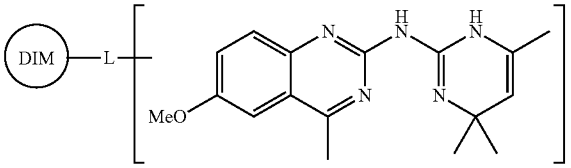
II-yy-2
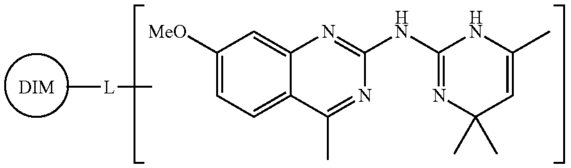

-continued

II-yy-3

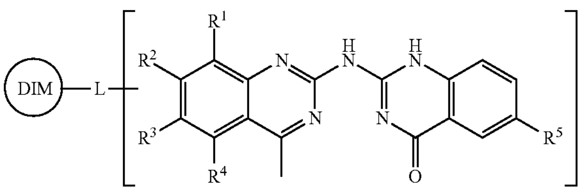

II-yy-4

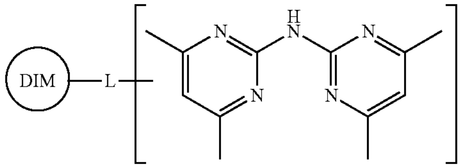

II-yy-5

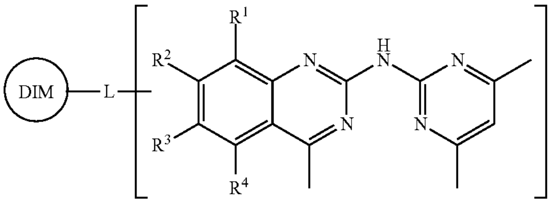

II-yy-6

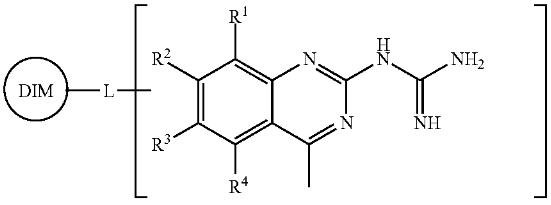

-continued

II-yy-7

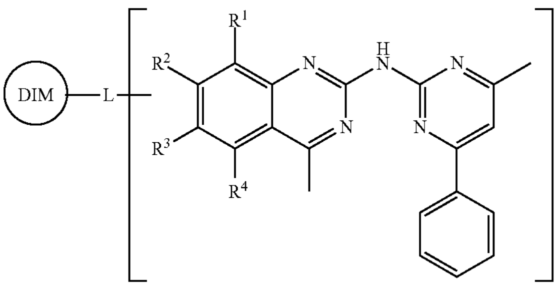

II-yy-8

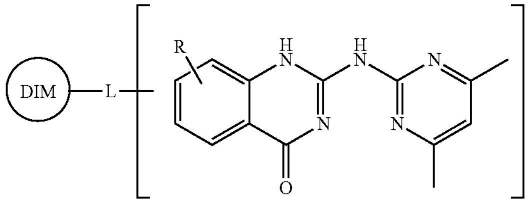

or a pharmaceutically acceptable salt thereof, wherein L and DIM are as defined above and described in embodiments herein, and wherein each of the variables R, $R^1$, $R^2$, $R^3$, $R^4$, and $R^5$ is as described and defined in Jamroskovic, J. et al., *Quinzoline Ligands Induce Cancer Call Death through Selective STAT3Inhibition and G-Quadruplex Stabilization*, J. Am. Chem. Soc., dx.doi.org/10.1021/jacs.9b11232, the entirety of each of which is herein incorporated by reference.

In some embodiments, STAT is

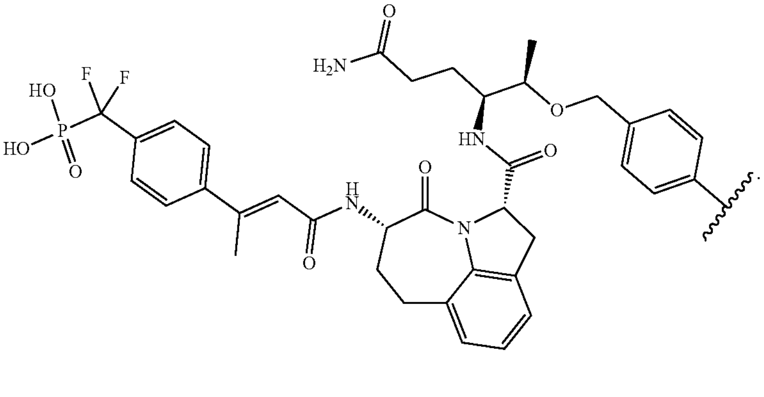 [SMILES: *c1ccc(CO[C@H](C)[C@H](CCC(N)=O)NC(=O)[C@@H]2Cc3cccc4c3N2C(=O)[C@@H](NC(=O)/C=C(\C)c2ccc(C(F)(F)P(=O)(O)O)cc2)CC4)cc1]

In some embodiments, STAT is
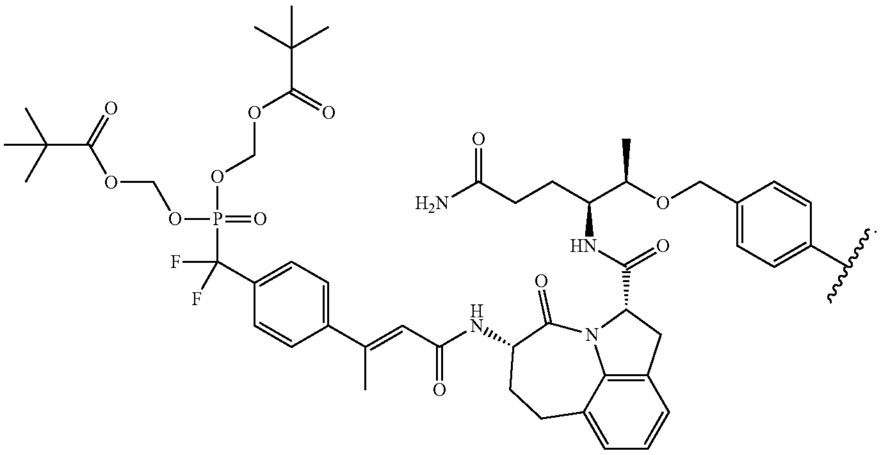 [SMILES: *c1ccc(CO[C@H](C)[C@H](CCC(N)=O)NC(=O)[C@@H]2Cc3cccc4c3N2C(=O)[C@@H](NC(=O)/C=C(\C)c2ccc(C(F)(F)P(=O)(OCOC(=O)C(C)(C)C)OCOC(=O)C(C)(C)C)cc2)CC4)cc1]
In some embodiments, STAT is
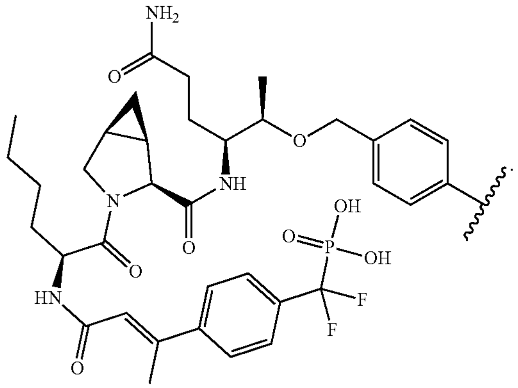 [SMILES: *c1ccc(CO[C@H](C)[C@H](CCC(N)=O)NC(=O)[C@@H]2[C@@H]3C[C@@H]3CN2C(=O)[C@H](CCCC)NC(=O)/C=C(\C)c2ccc(C(F)(F)P(=O)(O)O)cc2)cc1]
In some embodiments, STAT is
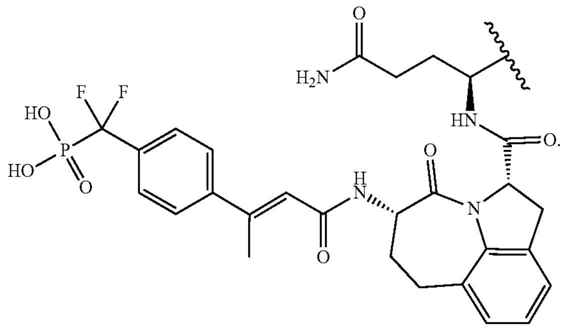
In some embodiments, STAT is
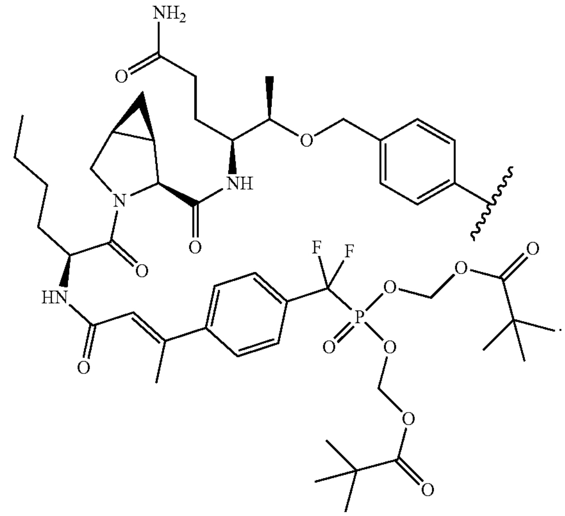 [SMILES: *c1ccc(CO[C@H](C)[C@H](CCC(N)=O)NC(=O)[C@@H]2[C@@H]3C[C@@H]3CN2C(=O)[C@H](CCCC)NC(=O)/C=C(\C)c2ccc(C(F)(F)P(=O)(OCOC(=O)C(C)(C)C)OCOC(=O)C(C)(C)C)cc2)cc1]
In some embodiments, STAT is
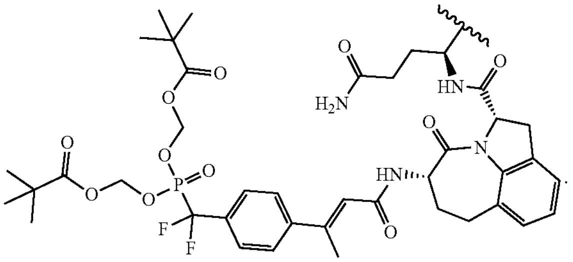 [SMILES: *[C@H](CCC(N)=O)NC(=O)[C@@H]1Cc2cccc3c2N1C(=O)[C@@H](NC(=O)/C=C(\C)c1ccc(C(F)(F)P(=O)(OCOC(=O)C(C)(C)C)OCOC(=O)C(C)(C)C)cc1)CC3]

In some embodiments, STAT is
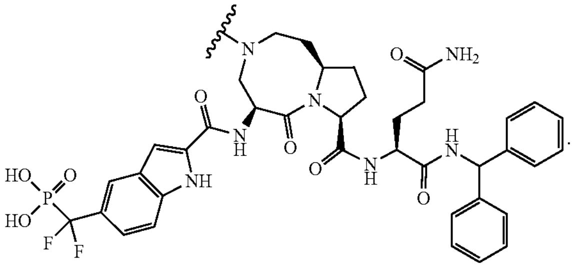 [SMILES: *N1CC[C@H]2CC[C@@H](C(=O)N[C@@H](CCC(N)=O)C(=O)NC(c3ccccc3)c3ccccc3)N2C(=O)[C@@H](NC(=O)c2cc3cc(C(F)(F)P(=O)(O)O)ccc3[nH]2)C1]
In some embodiments, STAT is
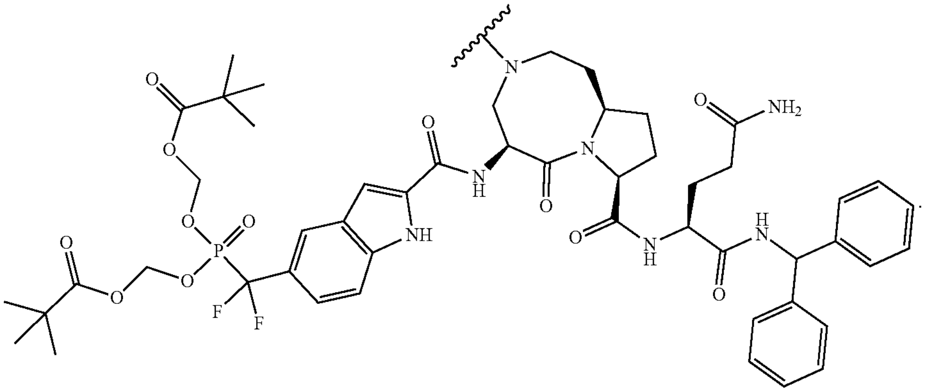 [SMILES: *N1CC[C@H]2CC[C@@H](C(=O)N[C@@H](CCC(N)=O)C(=O)NC(c3ccccc3)c3ccccc3)N2C(=O)[C@@H](NC(=O)c2cc3cc(C(F)(F)P(=O)(OCOC(=O)C(C)(C)C)OCOC(=O)C(C)(C)C)ccc3[nH]2)C1]
In some embodiments, STAT is
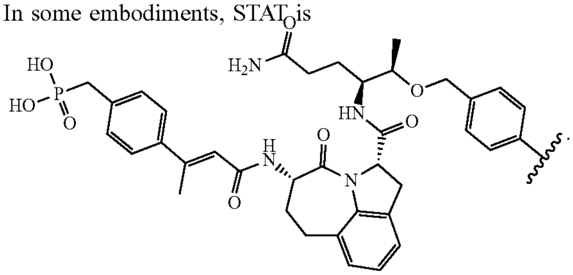
In some embodiments, STAT is
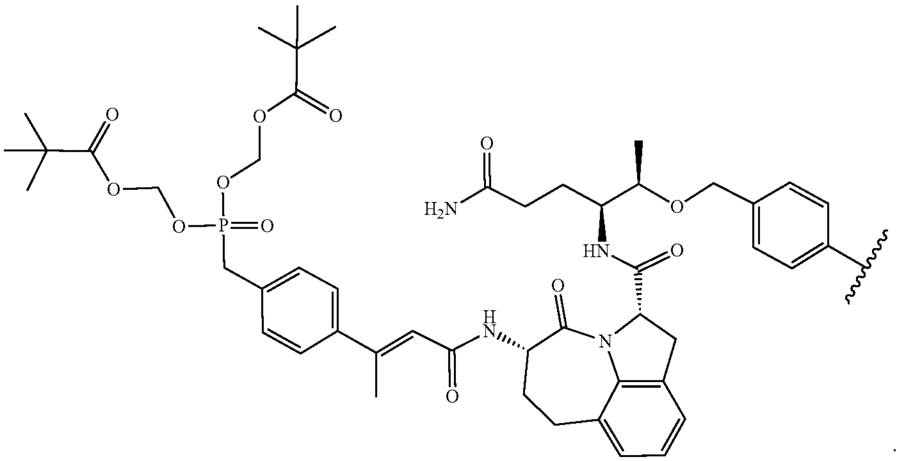 [SMILES: *c1ccc(CO[C@H](C)[C@H](CCC(N)=O)NC(=O)[C@@H]2Cc3cccc4c3N2C(=O)[C@@H](NC(=O)/C=C(\C)c2ccc(CP(=O)(OCOC(=O)C(C)(C)C)OCOC(=O)C(C)(C)C)cc2)CC4)cc1]

In some embodiments, STAT is
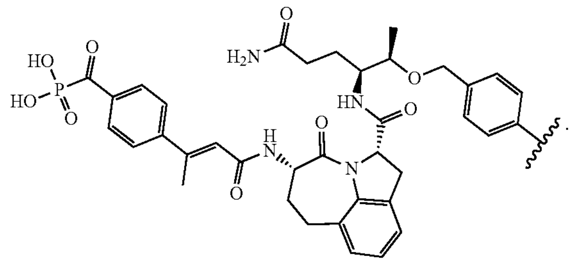 [SMILES: *c1ccc(CO[C@H](C)[C@H](CCC(N)=O)NC(=O)[C@@H]2Cc3cccc4c3N2C(=O)[C@@H](NC(=O)/C=C(\C)c2ccc(C(=O)P(=O)(O)O)cc2)CC4)cc1]
In some embodiments, STAT is
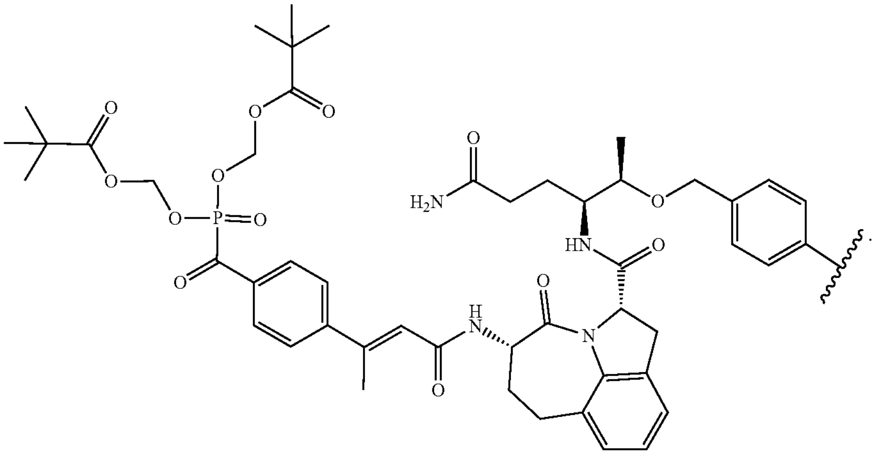 [SMILES: *c1ccc(CO[C@H](C)[C@H](CCC(N)=O)NC(=O)[C@@H]2Cc3cccc4c3N2C(=O)[C@@H](NC(=O)/C=C(\C)c2ccc(C(=O)P(=O)(OCOC(=O)C(C)(C)C)OCOC(=O)C(C)(C)C)cc2)CC4)cc1]
In some embodiments, STAT is
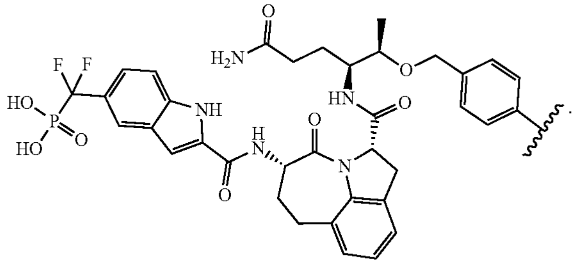 [SMILES: *c1ccc(CO[C@H](C)[C@H](CCC(N)=O)NC(=O)[C@@H]2Cc3cccc4c3N2C(=O)[C@@H](NC(=O)c2cc3cc(C(F)(F)P(=O)(O)O)ccc3[nH]2)CC4)cc1]

In some embodiments, STAT is
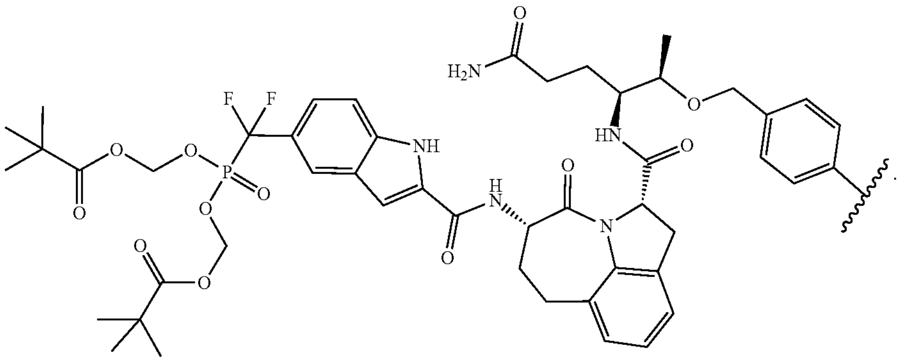 [SMILES: *c1ccc(CO[C@H](C)[C@H](CCC(N)=O)NC(=O)[C@@H]2Cc3cccc4c3N2C(=O)[C@@H](NC(=O)c2cc3cc(C(F)(F)P(=O)(OCOC(=O)C(C)(C)C)OCOC(=O)C(C)(C)C)ccc3[nH]2)CC4)cc1]
In some embodiments, STAT is
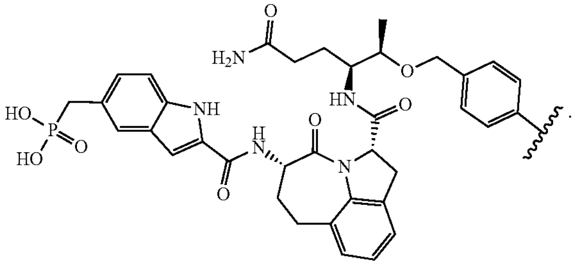 [SMILES: *c1ccc(CO[C@H](C)[C@H](CCC(N)=O)NC(=O)[C@@H]2Cc3cccc4c3N2C(=O)[C@@H](NC(=O)c2cc3cc(CP(=O)(O)O)ccc3[nH]2)CC4)cc1]
In some embodiments, STAT is
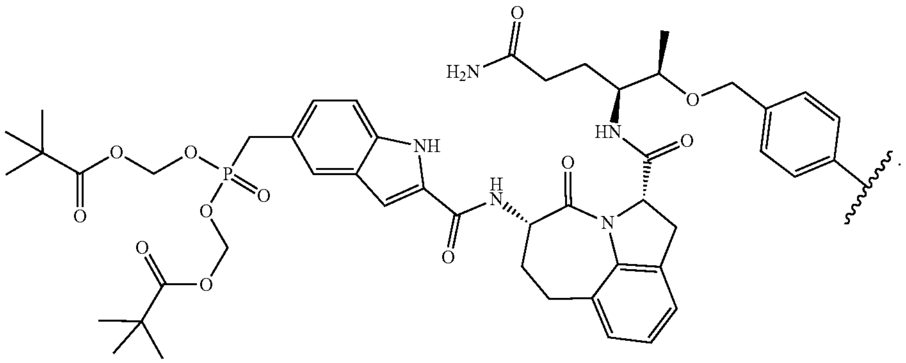 [SMILES: *c1ccc(CO[C@H](C)[C@H](CCC(N)=O)NC(=O)[C@@H]2Cc3cccc4c3N2C(=O)[C@@H](NC(=O)c2cc3cc(CP(=O)(OCOC(=O)C(C)(C)C)OCOC(=O)C(C)(C)C)ccc3[nH]2)CC4)cc1]
In some embodiments, STAT is
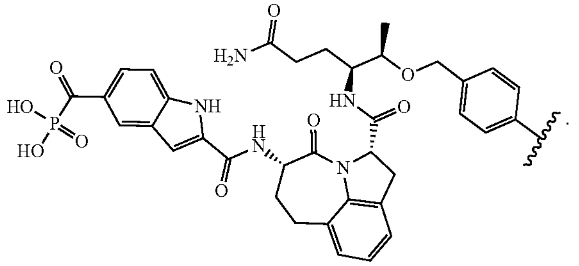 [SMILES: *c1ccc(CO[C@H](C)[C@H](CCC(N)=O)NC(=O)[C@@H]2Cc3cccc4c3N2C(=O)[C@@H](NC(=O)c2cc3cc(C(=O)P(=O)(O)O)ccc3[nH]2)CC4)cc1]

In some embodiments, STAT is
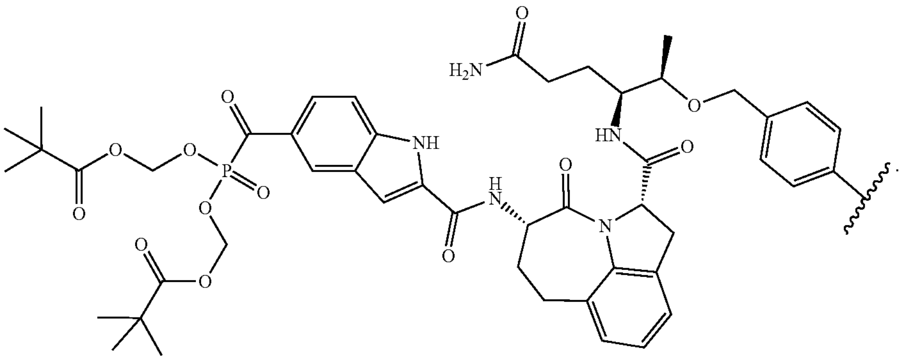 [SMILES: *c1ccc(CO[C@H](C)[C@H](CCC(N)=O)NC(=O)[C@@H]2Cc3cccc4c3N2C(=O)[C@@H](NC(=O)c2cc3cc(C(=O)P(=O)(OCOC(=O)C(C)(C)C)OCOC(=O)C(C)(C)C)ccc3[nH]2)CC4)cc1]
In some embodiments, STAT is
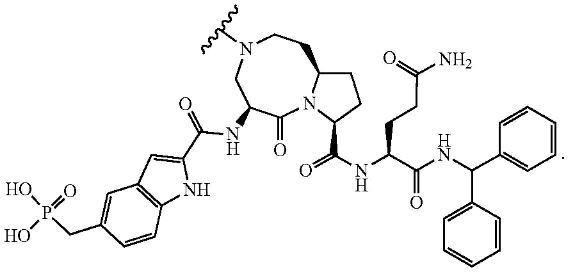 [SMILES: *N1CC[C@H]2CC[C@@H](C(=O)N[C@@H](CCC(N)=O)C(=O)NC(c3ccccc3)c3ccccc3)N2C(=O)[C@@H](NC(=O)c2cc3cc(CP(=O)(O)O)ccc3[nH]2)C1]
In some embodiments, STAT is
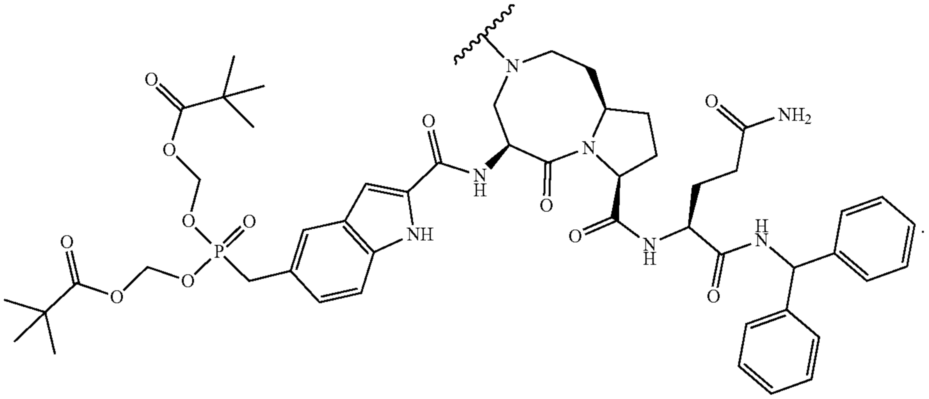 [SMILES: *N1CC[C@H]2CC[C@@H](C(=O)N[C@@H](CCC(N)=O)C(=O)NC(c3ccccc3)c3ccccc3)N2C(=O)[C@@H](NC(=O)c2cc3cc(CP(=O)(OCOC(=O)C(C)(C)C)OCOC(=O)C(C)(C)C)ccc3[nH]2)C1]
In some embodiments, STAT is
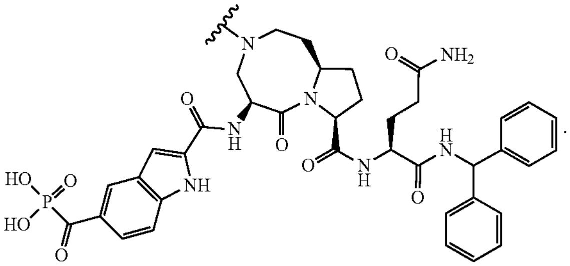 [SMILES: *N1CC[C@H]2CC[C@@H](C(=O)N[C@@H](CCC(N)=O)C(=O)NC(c3ccccc3)c3ccccc3)N2C(=O)[C@@H](NC(=O)c2cc3cc(C(=O)P(=O)(O)O)ccc3[nH]2)C1]

In some embodiments, STAT is
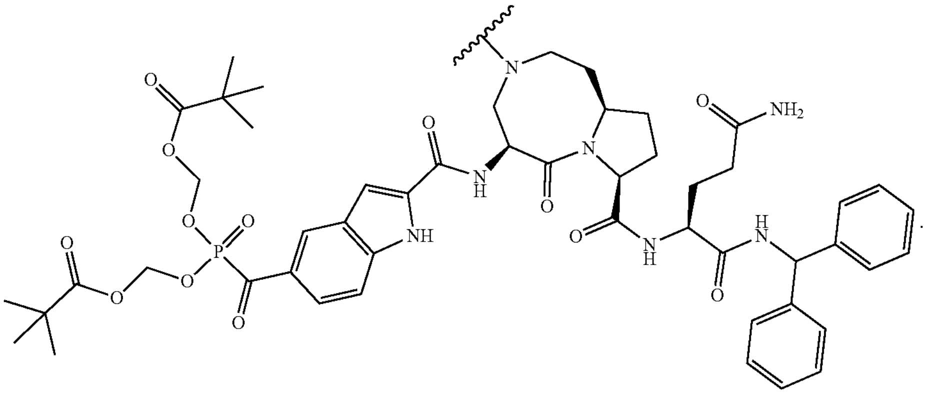 [SMILES: *N1CC[C@H]2CC[C@@H](C(=O)N[C@@H](CCC(N)=O)C(=O)NC(c3ccccc3)c3ccccc3)N2C(=O)[C@@H](NC(=O)c2cc3cc(C(=O)P(=O)(OCOC(=O)C(C)(C)C)OCOC(=O)C(C)(C)C)ccc3[nH]2)C1]
In some embodiments, STAT is
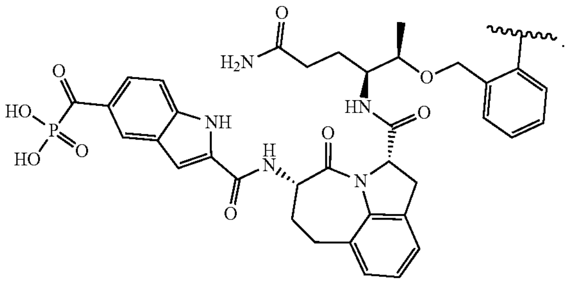 [SMILES: *c1ccccc1CO[C@H](C)[C@H](CCC(N)=O)NC(=O)[C@@H]1Cc2cccc3c2N1C(=O)[C@@H](NC(=O)c1cc2cc(C(=O)P(=O)(O)O)ccc2[nH]1)CC3]
In some embodiments, STAT is
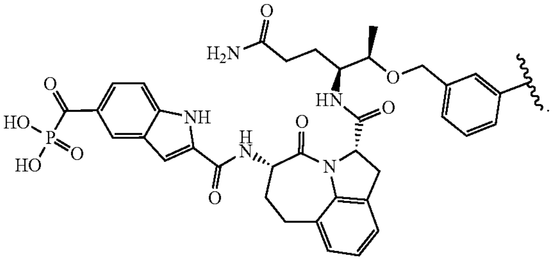 [SMILES: *c1cccc(CO[C@H](C)[C@H](CCC(N)=O)NC(=O)[C@@H]2Cc3cccc4c3N2C(=O)[C@@H](NC(=O)c2cc3cc(C(=O)P(=O)(O)O)ccc3[nH]2)CC4)c1]
In some embodiments, STAT is
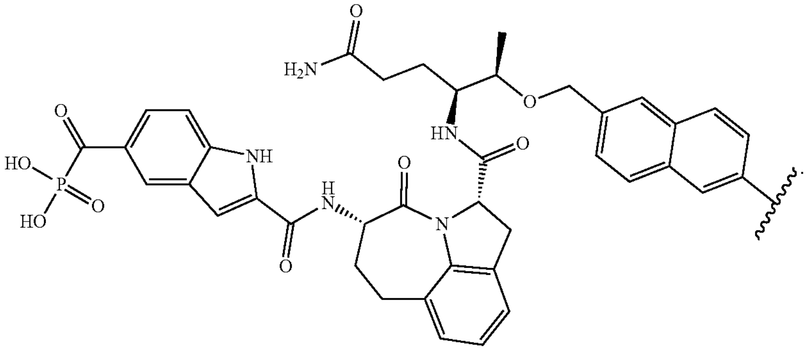 [SMILES: *c1ccc2cc(CO[C@H](C)[C@H](CCC(N)=O)NC(=O)[C@@H]3Cc4cccc5c4N3C(=O)[C@@H](NC(=O)c3cc4cc(C(=O)P(=O)(O)O)ccc4[nH]3)CC5)ccc2c1]
In some embodiments, STAT is
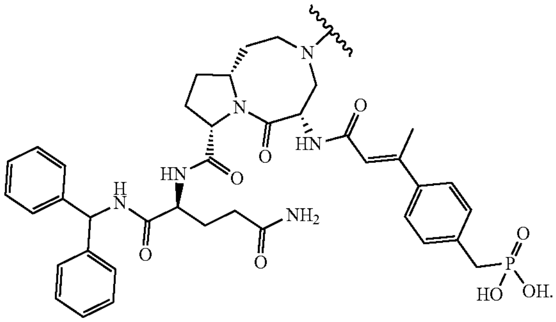 [SMILES: *N1CC[C@H]2CC[C@@H](C(=O)N[C@@H](CCC(N)=O)C(=O)NC(c3ccccc3)c3ccccc3)N2C(=O)[C@@H](NC(=O)/C=C(\C)c2ccc(CP(=O)(O)O)cc2)C1]

In some embodiments, STAT is
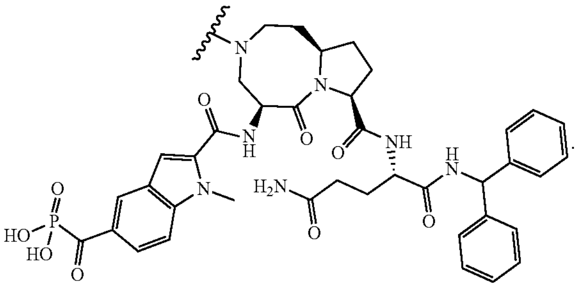 [SMILES: *N1CC[C@H]2CC[C@@H](C(=O)N[C@@H](CCC(N)=O)C(=O)NC(c3ccccc3)c3ccccc3)N2C(=O)[C@@H](NC(=O)c2cc3cc(C(=O)P(=O)(O)O)ccc3n2C)C1]
In some embodiments, STAT is
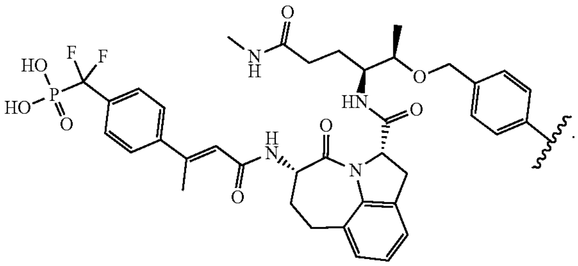 [SMILES: *c1ccc(CO[C@H](C)[C@H](CCC(=O)NC)NC(=O)[C@@H]2Cc3cccc4c3N2C(=O)[C@@H](NC(=O)/C=C(\C)c2ccc(C(F)(F)P(=O)(O)O)cc2)CC4)cc1]
In some embodiments, STAT is
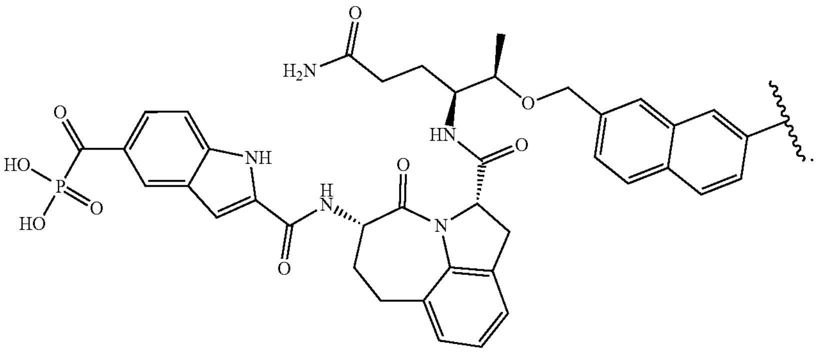 [SMILES: *c1ccc2ccc(CO[C@H](C)[C@H](CCC(N)=O)NC(=O)[C@@H]3Cc4cccc5c4N3C(=O)[C@@H](NC(=O)c3cc4cc(C(=O)P(=O)(O)O)ccc4[nH]3)CC5)cc2c1]
In some embodiments, STAT is
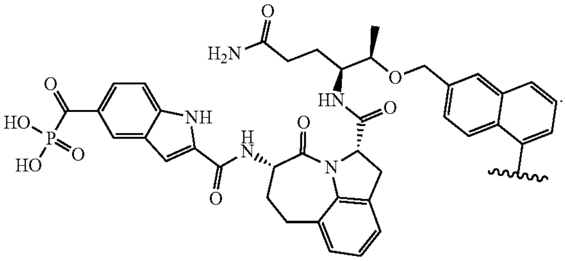 [SMILES: *c1cccc2cc(CO[C@H](C)[C@H](CCC(N)=O)NC(=O)[C@@H]3Cc4cccc5c4N3C(=O)[C@@H](NC(=O)c3cc4cc(C(=O)P(=O)(O)O)ccc4[nH]3)CC5)ccc12]
In some embodiments, STAT is
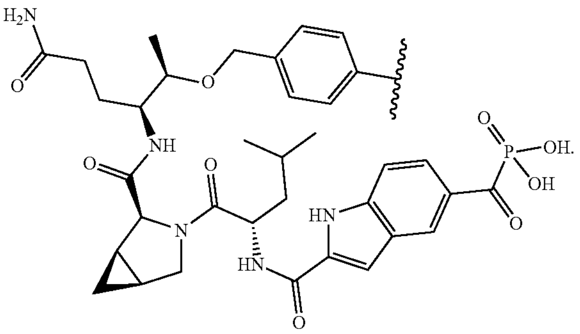 [SMILES: *c1ccc(CO[C@H](C)[C@H](CCC(N)=O)NC(=O)[C@@H]2[C@@H]3C[C@@H]3CN2C(=O)[C@H](CC(C)C)NC(=O)c2cc3cc(C(=O)P(=O)(O)O)ccc3[nH]2)cc1]
In some embodiments, STAT is
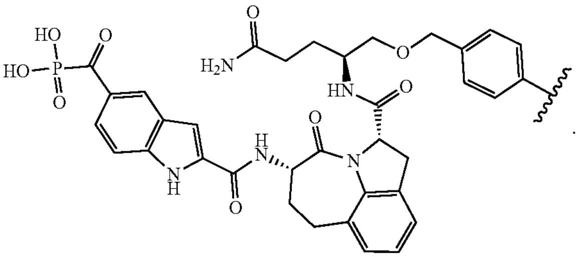 [SMILES: *c1ccc(COC[C@H](CCC(N)=O)NC(=O)[C@@H]2Cc3cccc4c3N2C(=O)[C@@H](NC(=O)c2cc3cc(C(=O)P(=O)(O)O)ccc3[nH]2)CC4)cc1]
In some embodiments, STAT is
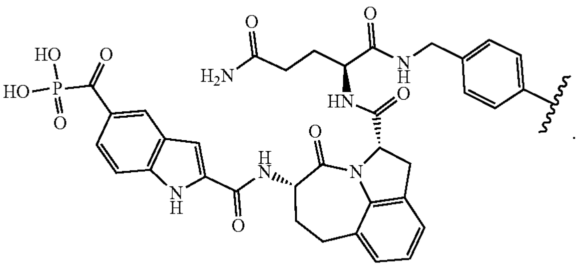 [SMILES: *c1ccc(CNC(=O)[C@H](CCC(N)=O)NC(=O)[C@@H]2Cc3cccc4c3N2C(=O)[C@@H](NC(=O)c2cc3cc(C(=O)P(=O)(O)O)ccc3[nH]2)CC4)cc1]

In some embodiments, STAT is
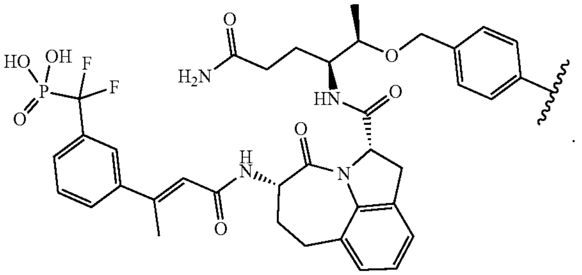 [SMILES: *c1ccc(CO[C@H](C)[C@H](CCC(N)=O)NC(=O)[C@@H]2Cc3cccc4c3N2C(=O)[C@@H](NC(=O)/C=C(\C)c2cccc(C(F)(F)P(=O)(O)O)c2)CC4)cc1]
In some embodiments, STAT is
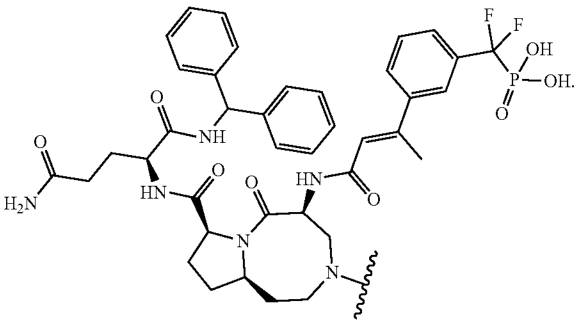 [SMILES: *N1CC[C@H]2CC[C@@H](C(=O)N[C@@H](CCC(N)=O)C(=O)NC(c3ccccc3)c3ccccc3)N2C(=O)[C@@H](NC(=O)/C=C(\C)c2cccc(C(F)(F)P(=O)(O)O)c2)C1]
In some embodiments, STAT is
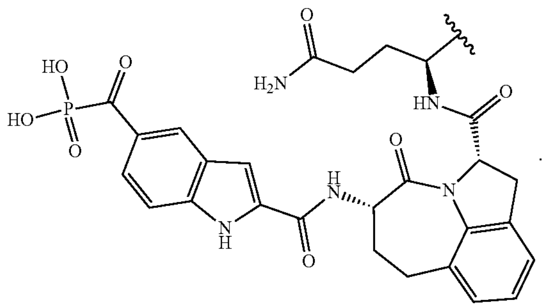 [SMILES: *[C@H](CCC(N)=O)NC(=O)[C@@H]1Cc2cccc3c2N1C(=O)[C@@H](NC(=O)c1cc2cc(C(=O)P(=O)(O)O)ccc2[nH]1)CC3]
In some embodiments, STAT is
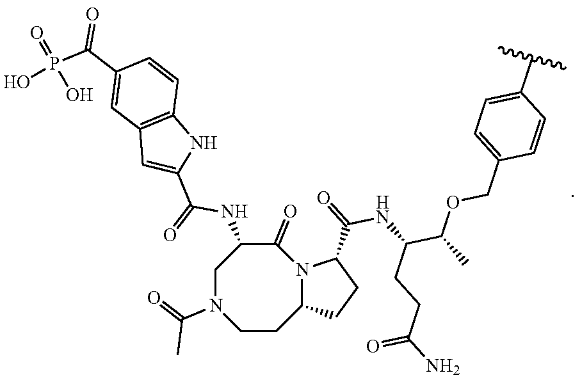 [SMILES: *c1ccc(CO[C@H](C)[C@H](CCC(N)=O)NC(=O)[C@@H]2CC[C@@H]3CCN(C(C)=O)C[C@H](NC(=O)c4cc5cc(C(=O)P(=O)(O)O)ccc5[nH]4)C(=O)N32)cc1]
In some embodiments, STAT is
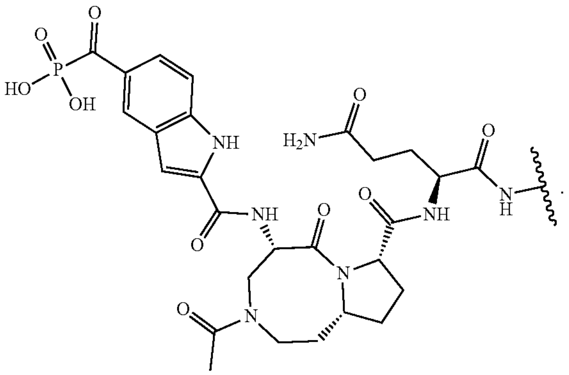 [SMILES: *NC(=O)[C@H](CCC(N)=O)NC(=O)[C@@H]1CC[C@@H]2CCN(C(C)=O)C[C@H](NC(=O)c3cc4cc(C(=O)P(=O)(O)O)ccc4[nH]3)C(=O)N21]
In some embodiments, STAT is
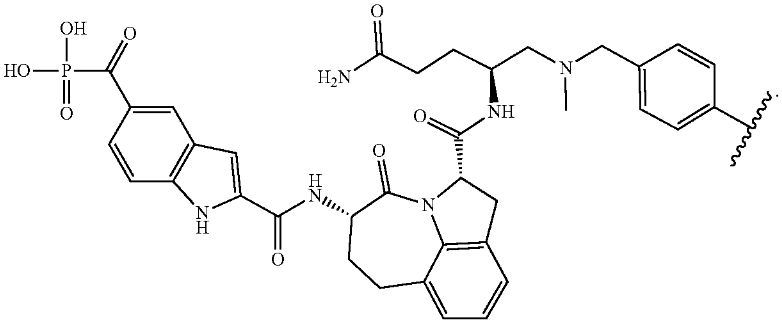 [SMILES: *c1ccc(CN(C)C[C@H](CCC(N)=O)NC(=O)[C@@H]2Cc3cccc4c3N2C(=O)[C@@H](NC(=O)c2cc3cc(C(=O)P(=O)(O)O)ccc3[nH]2)CC4)cc1]

In some embodiments, STAT is
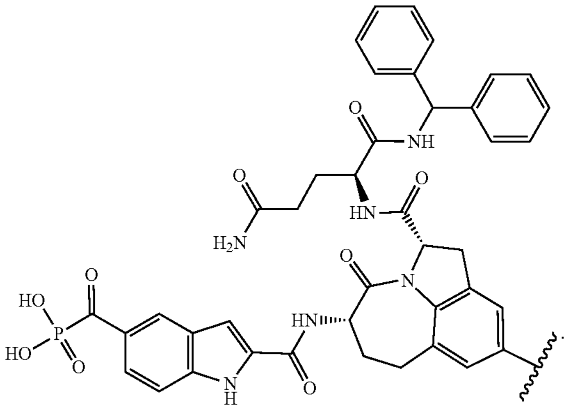 [SMILES: *c1cc2c3c(c1)C[C@@H](C(=O)N[C@@H](CCC(N)=O)C(=O)NC(c1ccccc1)c1ccccc1)N3C(=O)[C@@H](NC(=O)c1cc3cc(C(=O)P(=O)(O)O)ccc3[nH]1)CC2]
In some embodiments, STAT is
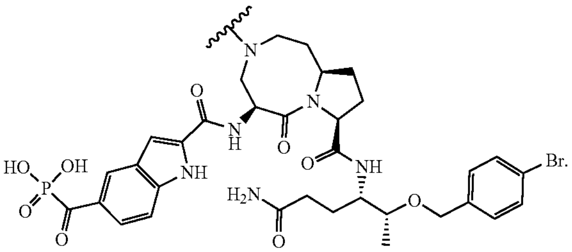 [SMILES: *N1CC[C@H]2CC[C@@H](C(=O)N[C@@H](CCC(N)=O)[C@@H](C)OCc3ccc(Br)cc3)N2C(=O)[C@@H](NC(=O)c2cc3cc(C(=O)P(=O)(O)O)ccc3[nH]2)C1]
In some embodiments, STAT is
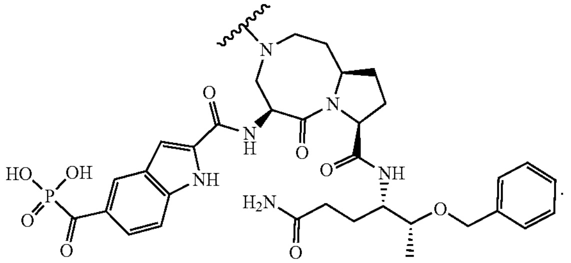 [SMILES: *N1CC[C@H]2CC[C@@H](C(=O)N[C@@H](CCC(N)=O)[C@@H](C)OCc3ccccc3)N2C(=O)[C@@H](NC(=O)c2cc3cc(C(=O)P(=O)(O)O)ccc3[nH]2)C1]
In some embodiments, STAT is
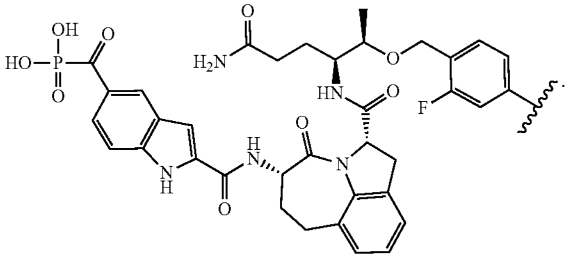 [SMILES: *c1ccc(CO[C@H](C)[C@H](CCC(N)=O)NC(=O)[C@@H]2Cc3cccc4c3N2C(=O)[C@@H](NC(=O)c2cc3cc(C(=O)P(=O)(O)O)ccc3[nH]2)CC4)c(F)c1]
In some embodiments, STAT is
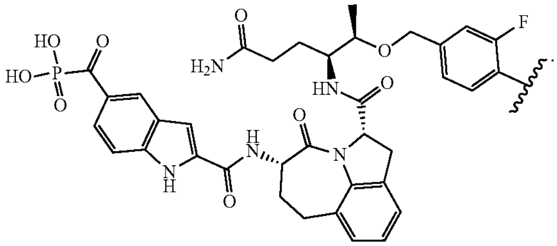 [SMILES: *c1ccc(CO[C@H](C)[C@H](CCC(N)=O)NC(=O)[C@@H]2Cc3cccc4c3N2C(=O)[C@@H](NC(=O)c2cc3cc(C(=O)P(=O)(O)O)ccc3[nH]2)CC4)cc1F]
In some embodiments, STAT is
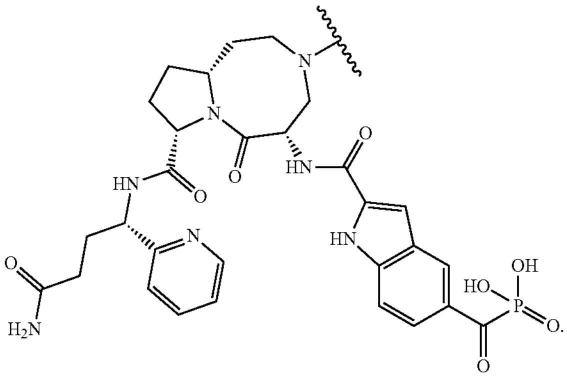 [SMILES: *N1CC[C@H]2CC[C@@H](C(=O)N[C@@H](CCC(N)=O)c3ccccn3)N2C(=O)[C@@H](NC(=O)c2cc3cc(C(=O)P(=O)(O)O)ccc3[nH]2)C1]
In some embodiments, STAT is
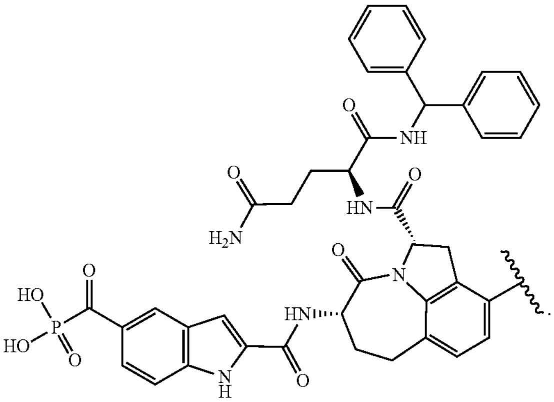

In some embodiments, STAT is
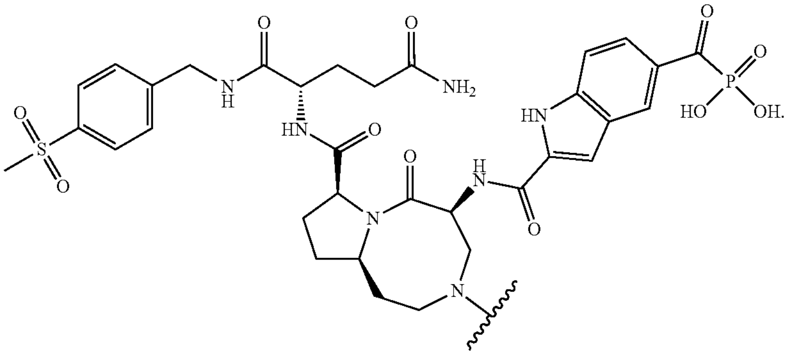 [SMILES: *N1CC[C@H]2CC[C@@H](C(=O)N[C@@H](CCC(N)=O)C(=O)NCc3ccc(S(C)(=O)=O)cc3)N2C(=O)[C@@H](NC(=O)c2cc3cc(C(=O)P(=O)(O)O)ccc3[nH]2)C1]
In some embodiments, STAT is
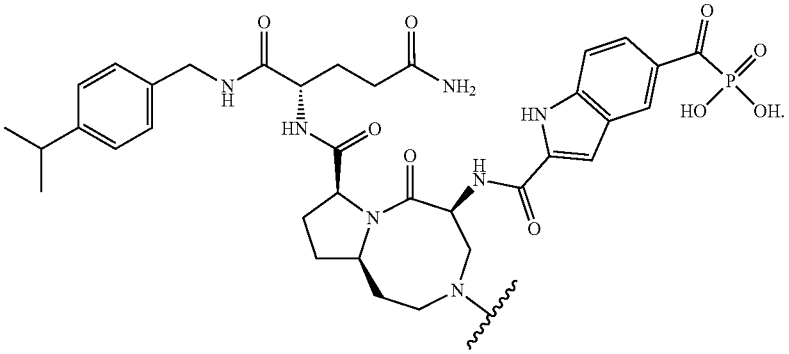 [SMILES: *N1CC[C@H]2CC[C@@H](C(=O)N[C@@H](CCC(N)=O)C(=O)NCc3ccc(C(C)C)cc3)N2C(=O)[C@@H](NC(=O)c2cc3cc(C(=O)P(=O)(O)O)ccc3[nH]2)C1]
In some embodiments, STAT is
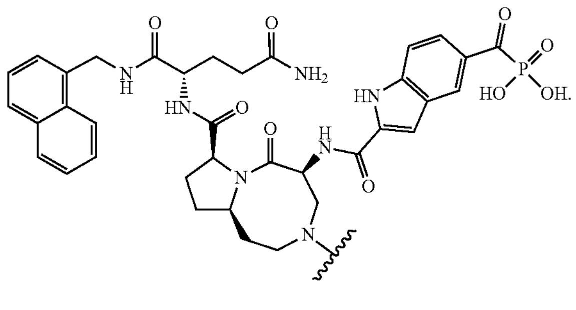 [SMILES: *N1CC[C@H]2CC[C@@H](C(=O)N[C@@H](CCC(N)=O)C(=O)NCc3cccc4ccccc34)N2C(=O)[C@@H](NC(=O)c2cc3cc(C(=O)P(=O)(O)O)ccc3[nH]2)C1]
In some embodiments, STAT is
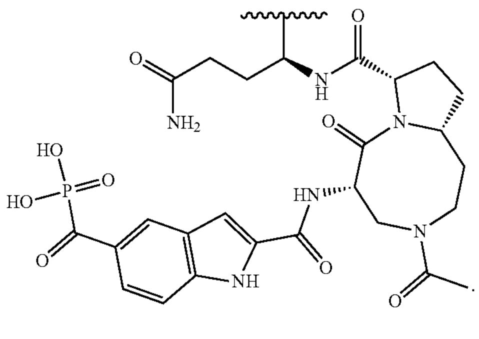 [SMILES: *[C@H](CCC(N)=O)NC(=O)[C@@H]1CC[C@@H]2CCN(C(C)=O)C[C@H](NC(=O)c3cc4cc(C(=O)P(=O)(O)O)ccc4[nH]3)C(=O)N21]

In some embodiments, STAT is

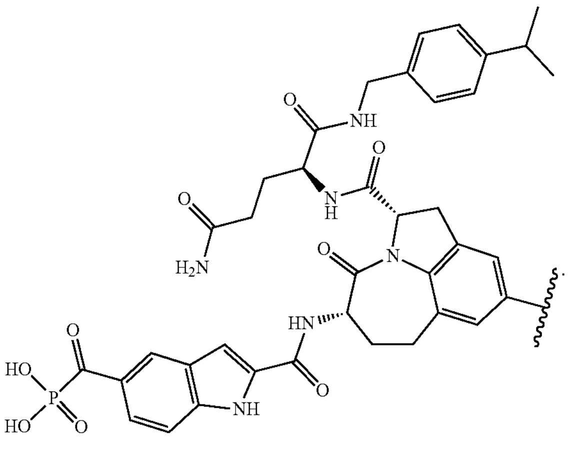 [SMILES: *c1cc2c3c(c1)C[C@@H](C(=O)N[C@@H](CCC(N)=O)C(=O)NCc1ccc(C(C)C)cc1)N3C(=O)[C@@H](NC(=O)c1cc3cc(C(=O)P(=O)(O)O)ccc3[nH]1)CC2]

In some embodiments, STAT is

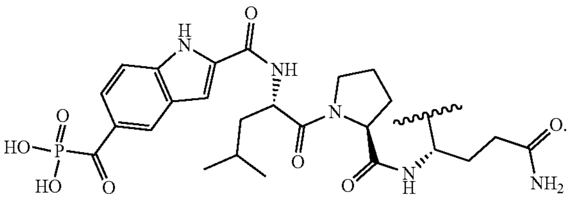 [SMILES: *[C@H](CCC(N)=O)NC(=O)[C@@H]1CCCN1C(=O)[C@H](CC(C)C)NC(=O)c1cc2cc(C(=O)P(=O)(O)O)ccc2[nH]1]

In some embodiments, STAT is

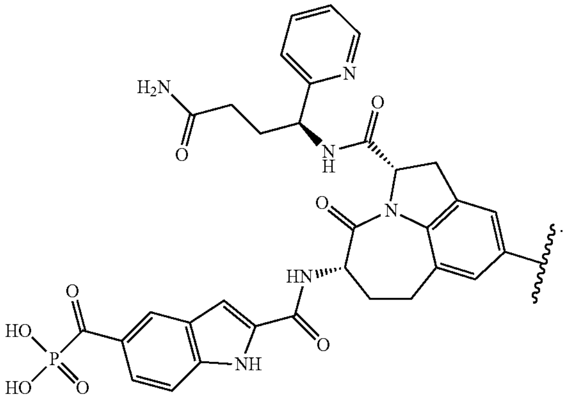 [SMILES: *c1cc2c3c(c1)C[C@@H](C(=O)N[C@@H](CCC(N)=O)c1ccccn1)N3C(=O)[C@@H](NC(=O)c1cc3cc(C(=O)P(=O)(O)O)ccc3[nH]1)CC2]

In some embodiments, STAT is

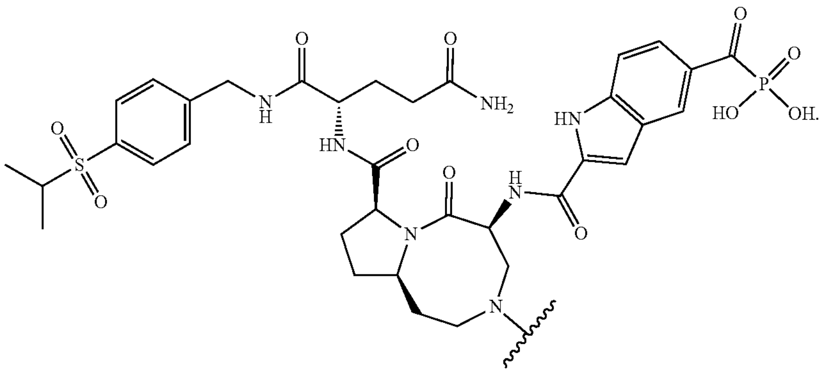 [SMILES: *N1CC[C@H]2CC[C@@H](C(=O)N[C@@H](CCC(N)=O)C(=O)NCc3ccc(S(=O)(=O)C(C)C)cc3)N2C(=O)[C@@H](NC(=O)c2cc3cc(C(=O)P(=O)(O)O)ccc3[nH]2)C1]

As defined above and described herein, L is a bivalent moiety that connects STAT to LBM or STAT to DIM.

In some embodiments, L is a bivalent moiety that connects STAT to LBM. In some embodiments, L is a bivalent moiety that connects STAT to DIM. In some embodiments, L is a bivalent moiety that connects STAT to a lysine mimetic.

In some embodiments, L is a covalent bond or a bivalent, saturated or partially unsaturated, straight or branched $C_{1-50}$ hydrocarbon chain, wherein 0-6 methylene units of L are independently replaced by —C(D)(H)—, —$C(D)_2$-, -Cy-, —O—, —N(R)—, —$Si(R)_2$—, —Si(OH)(R)—, —Si$(OH)_2$—, —P(O)(OR)—, —P(O)(R)—, —P(O)$(NR_2)$—, —S—, —OC(O)—, —C(O)O—, —C(O)—, —S(O)—, —$S(O)_2$—, —N(R)$S(O)_2$—, —$S(O)_2$N(R)—, —N(R)C(O)—, —C(O)N(R)—, —OC(O)N(R)—, —N(R)C(O)O—,

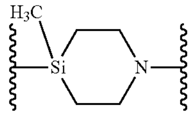,
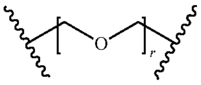,
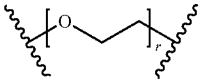,
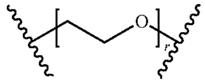,
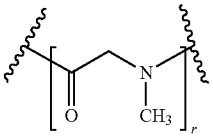, or
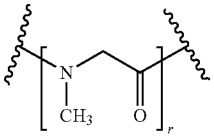, wherein each -Cy- is independently an optionally substituted bivalent ring selected from phenylenyl, an 8-10 membered bicyclic arylenyl, a 4-7 membered saturated or partially unsaturated carbocyclylenyl, a 4-11 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-11 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur, and wherein r is 0, 1, 2, 3, 4, 5, 6, 7, 8, 9, or 10.

In some embodiments, L is selected from those depicted in Table 1 or Table 1A, below.

In some embodiments, each -Cy- is independently an optionally substituted bivalent phenylenyl. In some embodiments, each -Cy- is independently an optionally substituted 8-10 membered bicyclic arylenyl. In some embodiments, each -Cy- is independently an optionally substituted 4-7 membered saturated or partially unsaturated carbocyclylenyl. In some embodiments, each -Cy- is independently an optionally substituted 4-11 membered saturated or partially unsaturated spiro carbocyclylenyl. In some embodiments, each -Cy- is independently an optionally substituted 8-10 membered bicyclic saturated or partially unsaturated carbocyclylenyl. In some embodiments, each -Cy is independently an optionally substituted 4-7 membered saturated or partially unsaturated heterocyclylenyl having 1-2 heteroatoms independently selected from nitrogen, oxygen, and sulfur. In some embodiments, each -Cy- is independently an optionally substituted 4-11 membered saturated or partially unsaturated spiro heterocyclylenyl having 1-2 heteroatoms independently selected from nitrogen, oxygen, and sulfur. In some embodiments, each -Cy- is independently an optionally substituted 8-10 membered bicyclic saturated or partially unsaturated heterocyclylenyl having 1-2 heteroatoms independently selected from nitrogen, oxygen, and sulfur. In some embodiments, each -Cy- is independently an optionally substituted 5-6 membered heteroarylenyl having 1-4 heteroatoms independently selected from nitrogen, oxygen, and sulfur. In some embodiments, each -Cy- is independently an optionally substituted 8-10 membered bicyclic heteroarylenyl having 1-5 heteroatoms independently selected from nitrogen, oxygen, or sulfur.

In some embodiments, -Cy- is

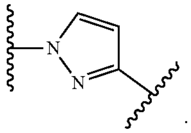 [SMILES: *c1ccn(*)n1].

In some embodiments, -Cy- is

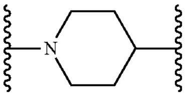.

In some embodiments, -Cy- is

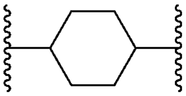.

In some embodiments, -Cy- is

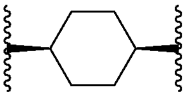.

In some embodiments, -Cy- is

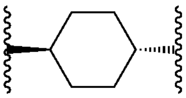.

In some embodiments, -Cy- is

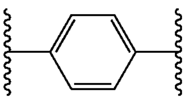.

In some embodiments, -Cy- is

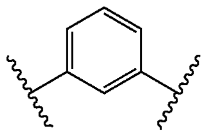.

In some embodiments, -Cy- is
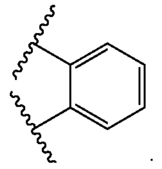 [SMILES: *c1ccccc1*]
In some embodiments, -Cy is
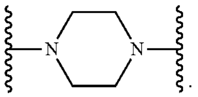
In some embodiments, -Cy- is
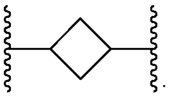 [SMILES: *C1CC(*)C1]
In some embodiments, -Cy- is
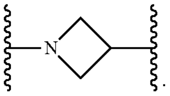 [SMILES: *C1CN(*)C1]
In some embodiments, -Cy- is
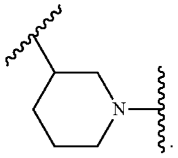 [SMILES: *C1CCCN(*)C1]
In some embodiments, -Cy- is
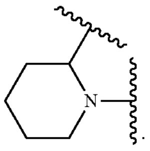 [SMILES: *C1CCCCN1*]
In some embodiments, -Cy- is
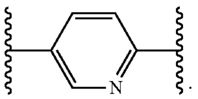 [SMILES: *c1ccc(*)nc1]
In some embodiments, -Cy- is
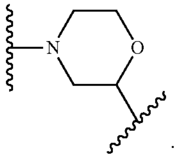 [SMILES: *C1CN(*)CCO1]
In some embodiments, -Cy- is
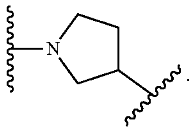 [SMILES: *C1CCN(*)C1]
In some embodiments, -Cy- is
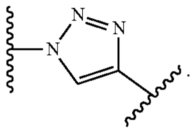 [SMILES: *c1cn(*)nn1]
In some embodiments, -Cy- is
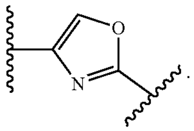 [SMILES: *c1coc(*)n1]
In some embodiments, -Cy- is
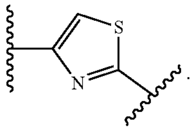
In some embodiments, -Cy- is
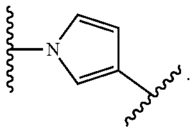 [SMILES: *c1ccn(*)c1]
In some embodiments, -Cy- is
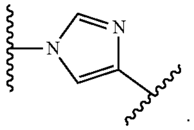 [SMILES: *c1cn(*)cn1]

In some embodiments, -Cy- is
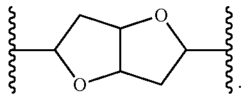 [SMILES: *C1CC2OC(*)CC2O1]
In some embodiments, -Cy- is
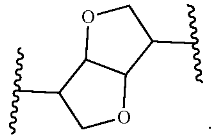 [SMILES: *C1COC2C(*)COC12]
In some embodiments, -Cy- is
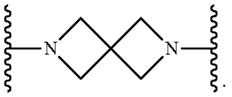 [SMILES: *N1CC2(C1)CN(*)C2]
In some embodiments, -Cy- is
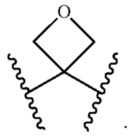 [SMILES: *C1(*)COC1]
In some embodiments, -Cy- is
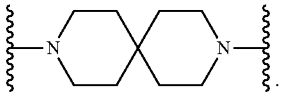
In some embodiments, -Cy- is
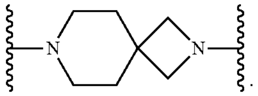 [SMILES: *N1CCC2(CC1)CN(*)C2]
In some embodiments, -Cy- is
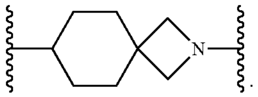 [SMILES: *C1CCC2(CC1)CN(*)C2]
In some embodiments, -Cy- is
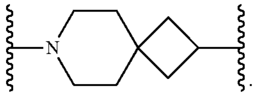
In some embodiments, -Cy- is
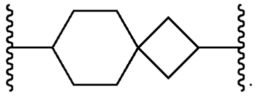
In some embodiments, -Cy- is
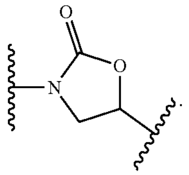 [SMILES: *C1CN(*)C(=O)O1]
In some embodiments, -Cy- is
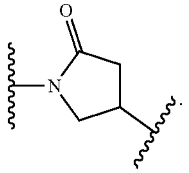 [SMILES: *C1CC(=O)N(*)C1]
In some embodiments, -Cy- is
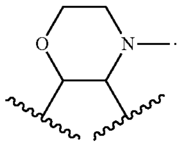 [SMILES: *C1OCCN(C)C1*]
In some embodiments, -Cy- is
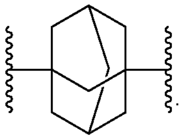 [SMILES: *C12CC3CC(C1)CC(*)(C3)C2]
In some embodiments, -Cy- is
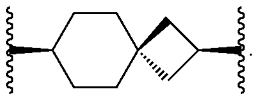

In some embodiments, -Cy- is
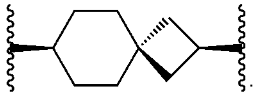
In some embodiments, -Cy- is
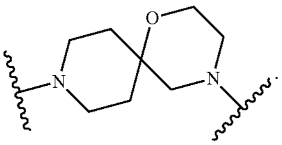 [SMILES: *N1CCC2(CC1)CN(*)CCO2]
In some embodiments, -Cy- is
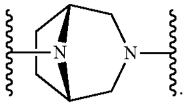 [SMILES: *N1C[C@H]2CC[C@@H](C1)N2*]
In some embodiments, -Cy- is
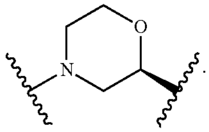 [SMILES: *[C@H]1CN(*)CCO1]
In some embodiments, -Cy- is
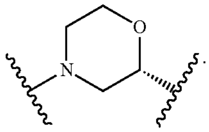 [SMILES: *[C@@H]1CN(*)CCO1]
In some embodiments, -Cy- is
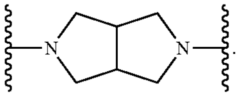 [SMILES: *N1CC2CN(*)CC2C1]
In some embodiments, -Cy- is
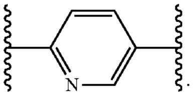 [SMILES: *c1ccc(*)nc1]
In some embodiments, -Cy- is
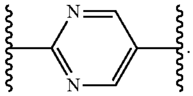 [SMILES: *c1cnc(*)nc1]
In some embodiments, -Cy- is
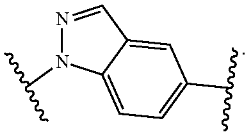 [SMILES: *c1ccc2c(cnn2*)c1]
In some embodiments, -Cy- is
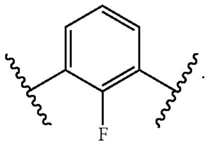 [SMILES: *c1cccc(*)c1F]
In some embodiments, -Cy- is
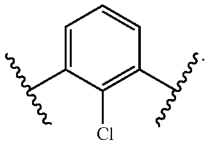
In some embodiments, -Cy- is
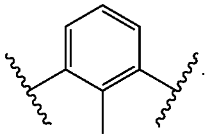 [SMILES: *c1cccc(*)c1C]
In some embodiments, -Cy- is
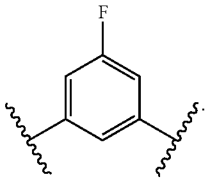 [SMILES: *c1cc(*)cc(F)c1]
In some embodiments, -Cy- is
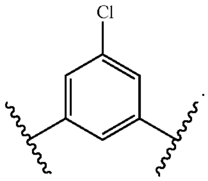

In some embodiments, -Cy- is
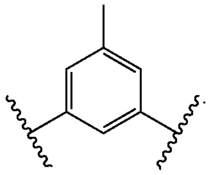 [SMILES: *c1cc(*)cc(C)c1]
In some embodiments, -Cy- is
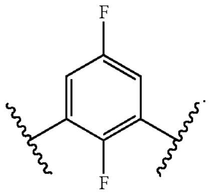 [SMILES: *c1cc(F)cc(*)c1F]
In some embodiments, -Cy- is
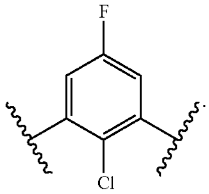 [SMILES: *c1cc(F)cc(*)c1Cl]
In some embodiments, -Cy- is
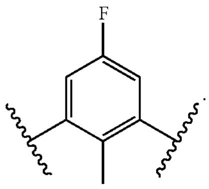 [SMILES: *c1cc(F)cc(*)c1C]
In some embodiments, -Cy- is
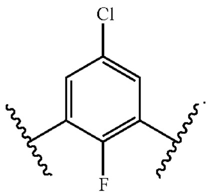 [SMILES: *c1cc(Cl)cc(*)c1F]
In some embodiments, -Cy- is
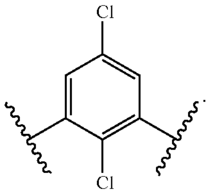 [SMILES: *c1cc(Cl)cc(*)c1Cl]
In some embodiments, -Cy- is
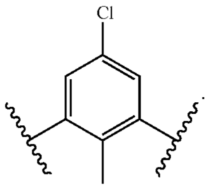
In some embodiments, -Cy- is
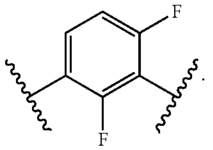 [SMILES: *c1ccc(F)c(*)c1F]
In some embodiments, -Cy- is
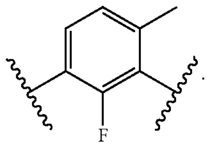 [SMILES: *c1ccc(C)c(*)c1F]
In some embodiments, -Cy- is
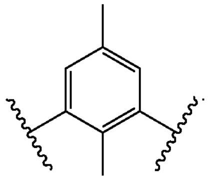 [SMILES: *c1cc(C)cc(*)c1C]
In some embodiments, -Cy- is
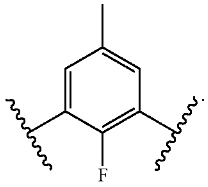 [SMILES: *c1cc(C)cc(*)c1F]

In some embodiments, -Cy- is

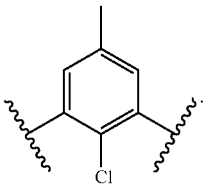 [SMILES: *c1cc(C)cc(*)c1Cl]

In some embodiments, -Cy- is selected from those depicted in Table 1 or Table 1A, below.

In some embodiments, r is 0. In some embodiments, r is 1. In some embodiments, r is 2. In some embodiments, r is 3. In some embodiments, r is 4. In some embodiments, r is 5. In some embodiments, r is 6. In some embodiments, r is 7. In some embodiments, r is 8. In some embodiments, r is 9. In some embodiments, r is 10.

In some embodiments, r is selected from those depicted in Table 1 or Table 1A, below.

In some embodiments, L is a covalent bond. In some embodiments, L is

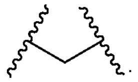 [SMILES: *C*]

In some embodiments, L is

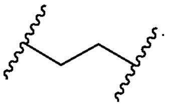 [SMILES: *CC*]

In some embodiments, L is

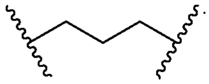 [SMILES: *CCC*]

In some embodiments, L is

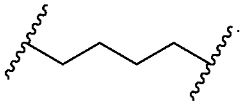 [SMILES: *CCCC*]

In some embodiments, L is

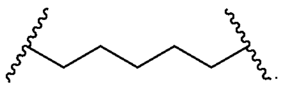 [SMILES: *CCCCC*]

In some embodiments, L is

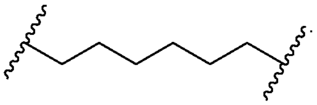 [SMILES: *CCCCCC*]

In some embodiments, L is

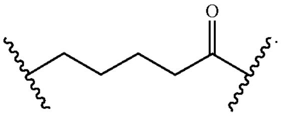 [SMILES: *CCCCC(*)=O]

In some embodiments, L is

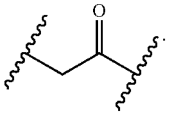 [SMILES: *CC(*)=O]

In some embodiments, L is

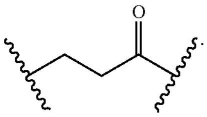 [SMILES: *CCC(*)=O]

In some embodiments, L is

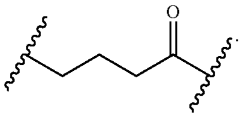 [SMILES: *CCCC(*)=O]

In some embodiments, L is

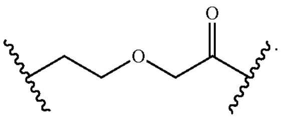

In some embodiments, L is

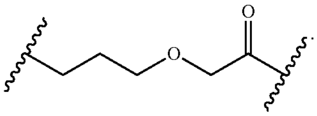 [SMILES: *CCCOCC(*)=O]

In some embodiments, L is

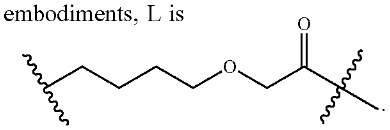

In some embodiments, L is

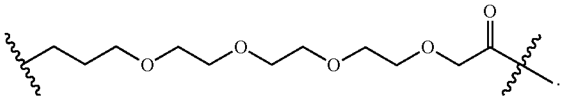 [SMILES: *CCCOCCOCCOCCOCC(*)=O]

In some embodiments, L is

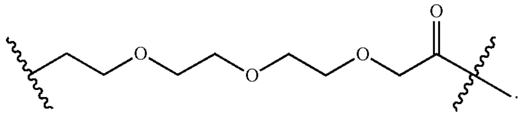 [SMILES: *CCOCCOCCOCC(*)=O]

In some embodiments, L is

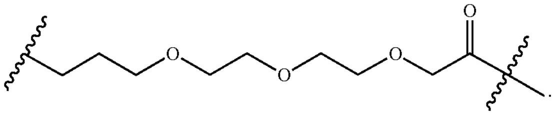 [SMILES: *CCCOCCOCCOCC(*)=O]

In some embodiments, L is

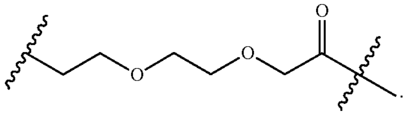 [SMILES: *CCOCCOCC(*)=O]

In some embodiments, L is

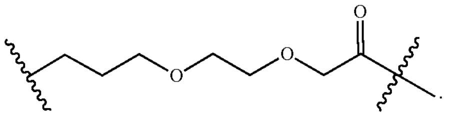 [SMILES: *CCCOCCOCC(*)=O]

In some embodiments, L is

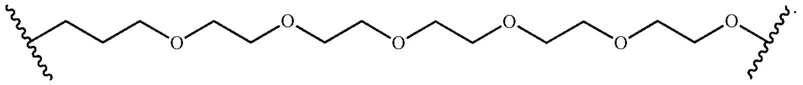 [SMILES: *CCCOCCOCCOCCOCCOCCO*]

In some embodiments, L is

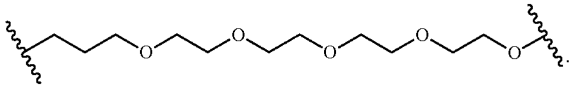 [SMILES: *CCCOCCOCCOCCOCCO*]

In some embodiments, L is

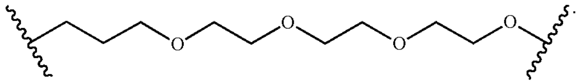 [SMILES: *CCCOCCOCCOCCO*]

In some embodiments, L is

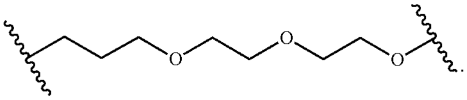 [SMILES: *CCCOCCOCCO*]

In some embodiments, L is

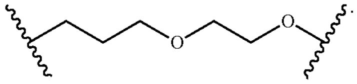 [SMILES: *CCCOCCO*]

In some embodiments, L is

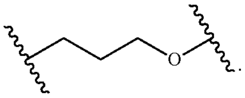 [SMILES: *CCCO*]

In some embodiments, L is

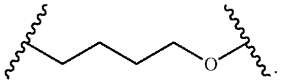 [SMILES: *CCCCO*]

In some embodiments, L is

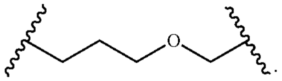 [SMILES: *CCCOC*]

In some embodiments, L is

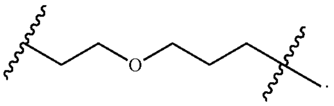 [SMILES: *CCCOCC*]

In some embodiments, L is

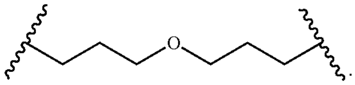 [SMILES: *CCCOCCC*]

In some embodiments, L is

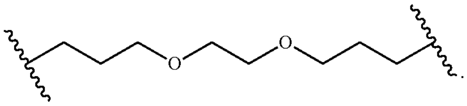 [SMILES: *CCCOCCOCCC*]

In some embodiments, L is

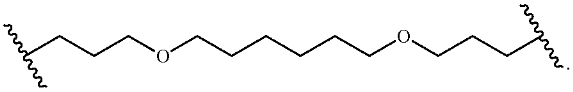 [SMILES: *CCCOCCCCCCOCCC*]

In some embodiments, L is

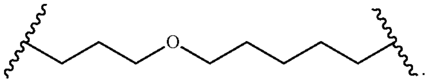 [SMILES: *CCCCCOCCC*]

In some embodiments, L is

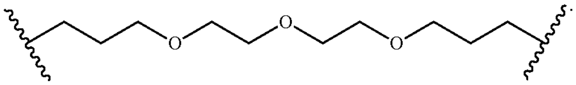 [SMILES: *CCCOCCOCCOCCC*]

In some embodiments, L is

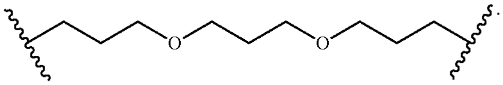 [SMILES: *CCCOCCCOCCC*]

In some embodiments, L is

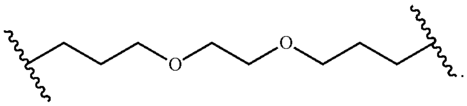 [SMILES: *CCCOCCOCCC*]

In some embodiments, L is

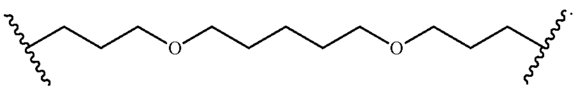 [SMILES: *CCCOCCCCCOCCC*]

In some embodiments, L is

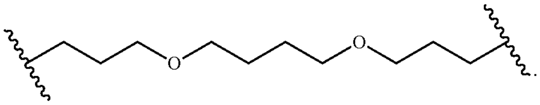 [SMILES: *CCCOCCCCOCCC*]

In some embodiments, L is

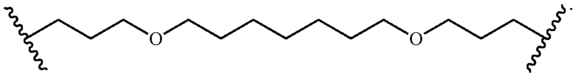 [SMILES: *CCCOCCCCCCCOCCC*]

In some embodiments, L is

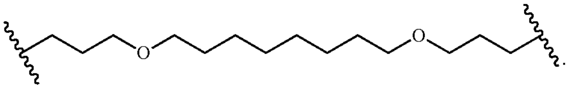 [SMILES: *CCCOCCCCCCCCOCCC*]

In some embodiments, L is

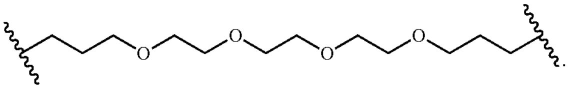 [SMILES: *CCCOCCOCCOCCOCCC*]

In some embodiments, L is

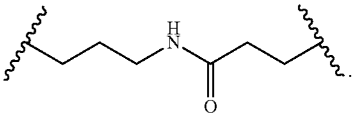 [SMILES: *CCCNC(=O)CC*]

In some embodiments, L is

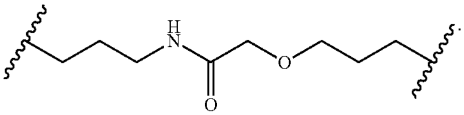 [SMILES: *CCCNC(=O)COCCC*]

In some embodiments, L is

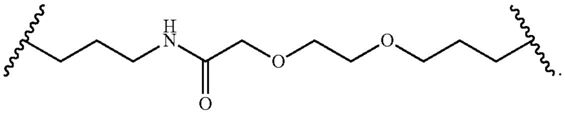 [SMILES: *CCCNC(=O)COCCOCCC*]

In some embodiments, L is

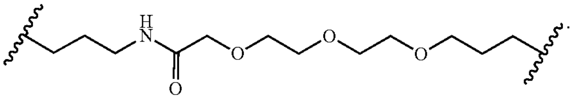 [SMILES: *CCCNC(=O)COCCOCCOCCC*]

In some embodiments, L is
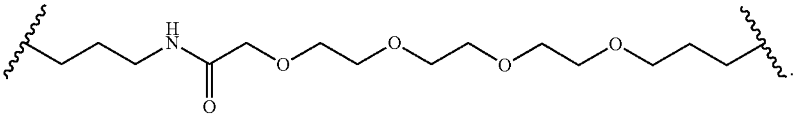 [SMILES: *CCCNC(=O)COCCOCCOCCOCCC*]
In some embodiments, L is
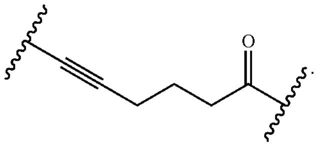 [SMILES: *C#CCCCC(*)=O]
In some embodiments, L is
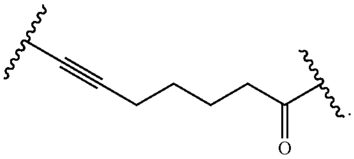 [SMILES: *C#CCCCCC(*)=O]
In some embodiments, L is
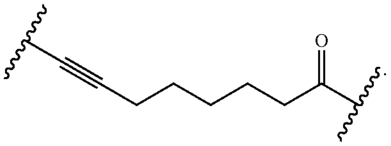 [SMILES: *C#CCCCCCC(*)=O]
In some embodiments, L is
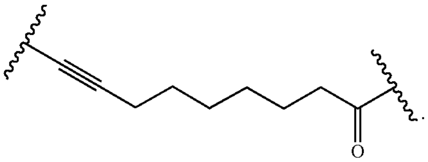 [SMILES: *C#CCCCCCCC(*)=O]
In some embodiments, L is
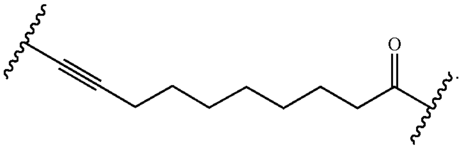 [SMILES: *C#CCCCCCCCC(*)=O]
In some embodiments, L is
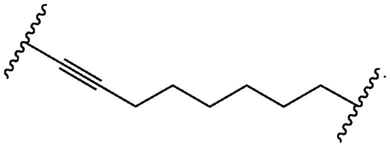 [SMILES: *C#CCCCCCC*]
In some embodiments, L is
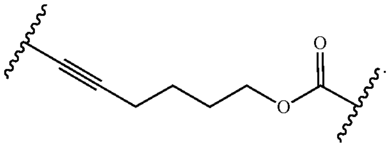 [SMILES: *C#CCCCCOC(*)=O]
In some embodiments, L is
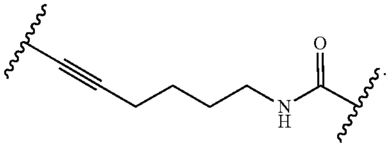 [SMILES: *C#CCCCCNC(*)=O]
In some embodiments, L is
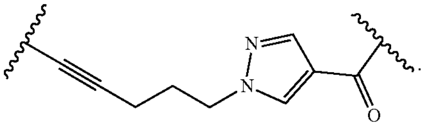 [SMILES: *C#CCCCn1cc(C(*)=O)cn1]
In some embodiments, L is
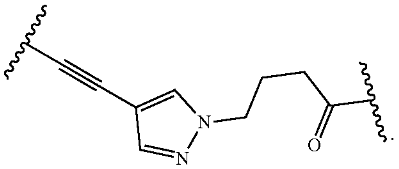 [SMILES: *C#Cc1cnn(CCCC(*)=O)c1]

In some embodiments, L is
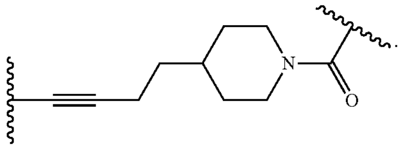 [SMILES: *C#CCCC1CCN(C(*)=O)CC1]
In some embodiments, L is
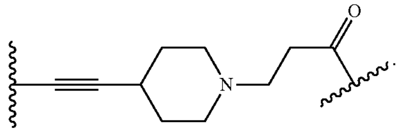 [SMILES: *C#CC1CCN(CCC(*)=O)CC1]
In some embodiments, L is
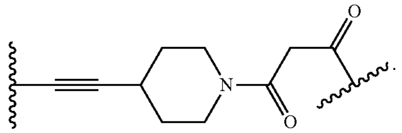 [SMILES: *C#CC1CCN(C(=O)CC(*)=O)CC1]
In some embodiments, L is
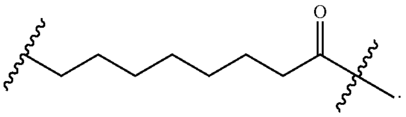 [SMILES: *CCCCCCCC(*)=O]
In some embodiments, L is
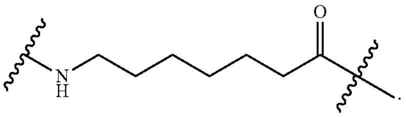 [SMILES: *NCCCCCCC(*)=O]
In some embodiments, L is
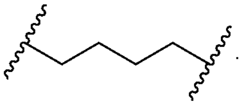 [SMILES: *CCCC*]
In some embodiments, L is
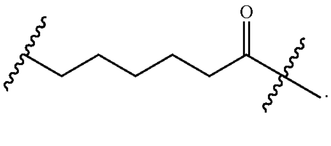 [SMILES: *CCCCCC(*)=O]
In some embodiments, L is
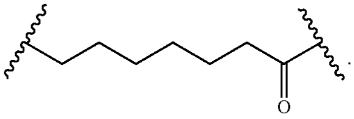 [SMILES: *CCCCCCC(*)=O]
In some embodiments, L is
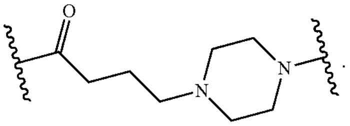 [SMILES: *C(=O)CCCN1CCN(*)CC1]
In some embodiments, L is
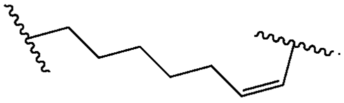 [SMILES: */C=C\CCCCC*]
In some embodiments, L is
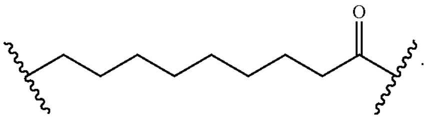 [SMILES: *CCCCCCCCC(*)=O]
In some embodiments, L is
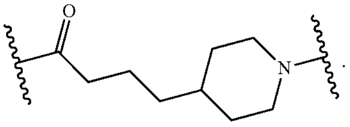 [SMILES: *C(=O)CCCC1CCN(*)CC1]
In some embodiments, L is
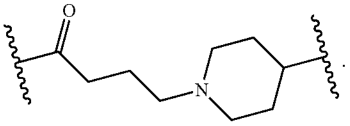 [SMILES: *C(=O)CCCN1CCC(*)CC1]
In some embodiments, L is
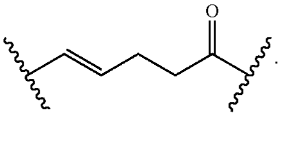 [SMILES: */C=C/CCC(*)=O]

In some embodiments, L is
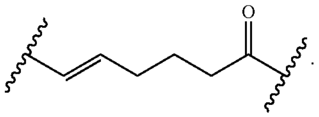 [SMILES: */C=C/CCCC(*)=O]
In some embodiments, L is
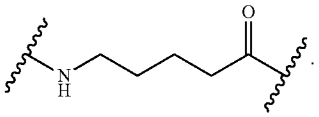 [SMILES: *NCCCCC(*)=O]
In some embodiments, L is
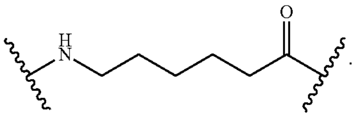 [SMILES: *NCCCCCC(*)=O]
In some embodiments, L is
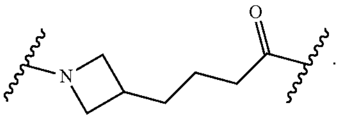 [SMILES: *C(=O)CCCC1CN(*)C1]
In some embodiments, L is
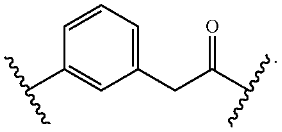 [SMILES: *C(=O)Cc1cccc(*)c1]
In some embodiments, L is
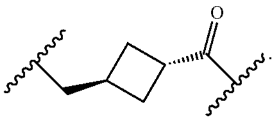 [SMILES: *C[C@H]1C[C@H](C(*)=O)C1]
In some embodiments, L is
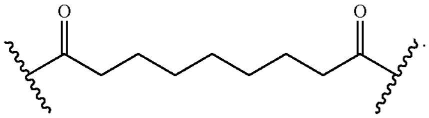 [SMILES: *C(=O)CCCCCCCC(*)=O]
In some embodiments, L is
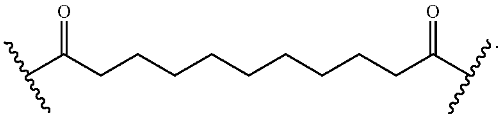 [SMILES: *C(=O)CCCCCCCCCC(*)=O]
In some embodiments, L is
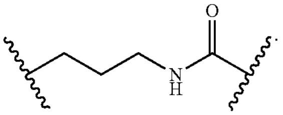 [SMILES: *CCCNC(*)=O]
In some embodiments, L is
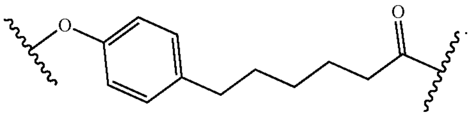 [SMILES: *Oc1ccc(CCCCCC(*)=O)cc1]
In some embodiments, L is
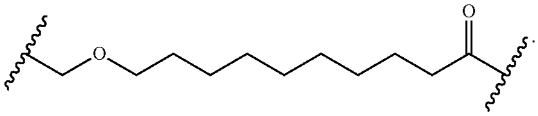 [SMILES: *COCCCCCCCCCC(*)=O]
In some embodiments, L is
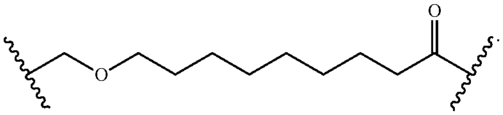 [SMILES: *COCCCCCCCCC(*)=O]
In some embodiments, L is
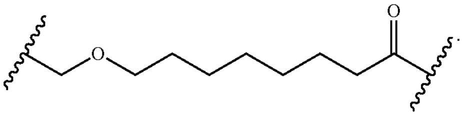 [SMILES: *COCCCCCCCC(*)=O]
In some embodiments, L is
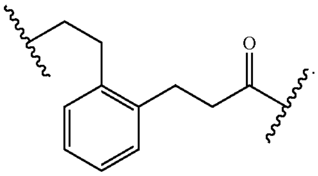 [SMILES: *CCc1ccccc1CCC(*)=O]

In some embodiments, L is
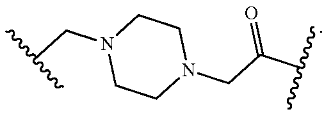 [SMILES: *CN1CCN(CC(*)=O)CC1]
In some embodiments, L is
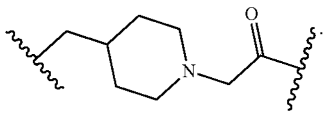 [SMILES: *CC1CCN(CC(*)=O)CC1]
In some embodiments, L is
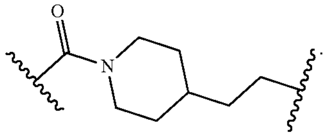 [SMILES: *CCC1CCN(C(*)=O)CC1]
In some embodiments, L is
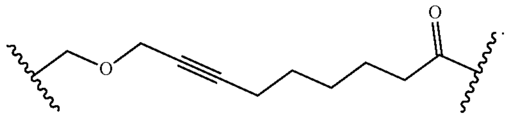 [SMILES: *COCC#CCCCCCC(*)=O]
In some embodiments, L is
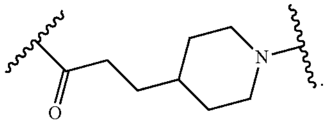 [SMILES: *C(=O)CCC1CCN(*)CC1]
In some embodiments, L is
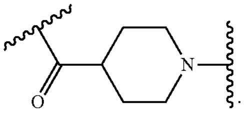
In some embodiments, L is
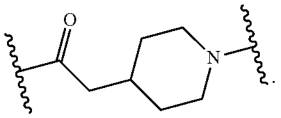 [SMILES: *C(=O)CC1CCN(*)CC1]
In some embodiments, L is
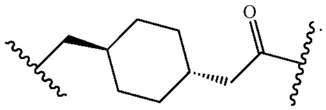 [SMILES: *C[C@H]1CC[C@H](CC(*)=O)CC1]
In some embodiments, L is
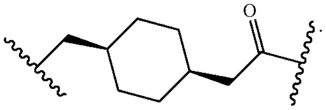 [SMILES: *C[C@H]1CC[C@@H](CC(*)=O)CC1]
In some embodiments, L is
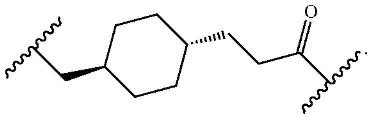 [SMILES: *C[C@H]1CC[C@H](CCC(*)=O)CC1]
In some embodiments, L is
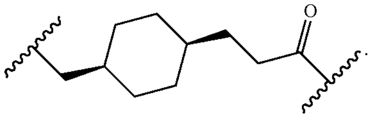 [SMILES: *C[C@H]1CC[C@@H](CCC(*)=O)CC1]
In some embodiments, L is
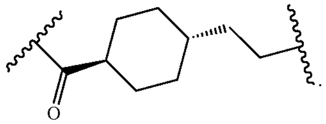 [SMILES: *CC[C@H]1CC[C@H](C(*)=O)CC1]
In some embodiments, L is
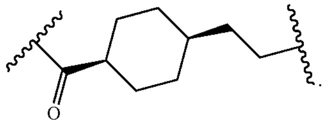 [SMILES: *CC[C@H]1CC[C@@H](C(*)=O)CC1]
In some embodiments, L is
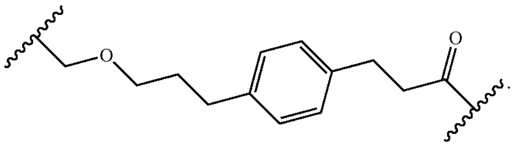 [SMILES: *COCCCc1ccc(CCC(*)=O)cc1]

In some embodiments, L is
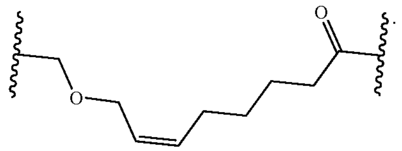 [SMILES: *COC/C=C\CCCCC(*)=O]
In some embodiments, L is
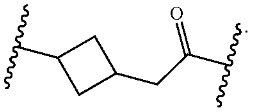 [SMILES: *C(=O)CC1CC(*)C1]
In some embodiments, L is
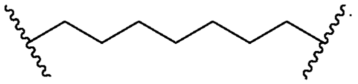 [SMILES: *CCCCCCC*]
In some embodiments, L is
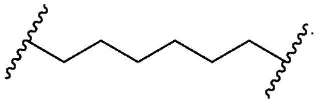 [SMILES: *CCCCCC*]
In some embodiments, L is
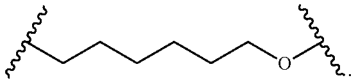 [SMILES: *CCCCCCO*]
In some embodiments, L is
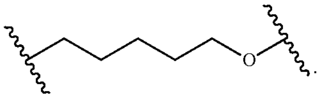 [SMILES: *CCCCCO*]
In some embodiments, L is
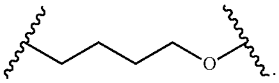 [SMILES: *CCCCO*]
In some embodiments, L is
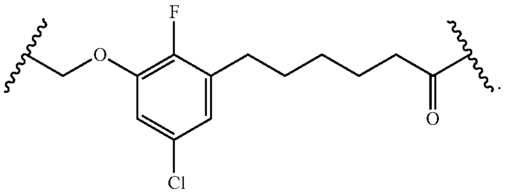 [SMILES: *COc1cc(Cl)cc(CCCCCC(*)=O)c1F]
In some embodiments, L is
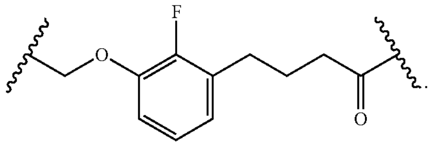 [SMILES: *COc1cccc(CCCC(*)=O)c1F]
In some embodiments, L is
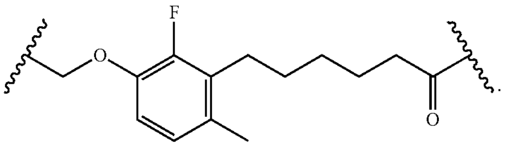 [SMILES: *COc1ccc(C)c(CCCCCC(*)=O)c1F]
In some embodiments, L is
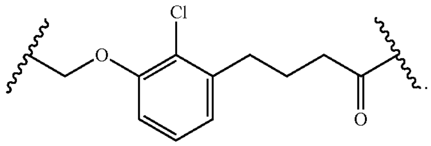 [SMILES: *COc1cccc(CCCC(*)=O)c1Cl]
In some embodiments, L is
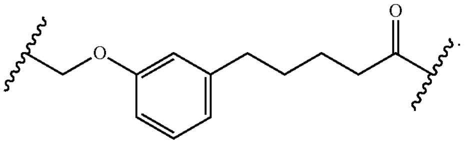 [SMILES: *COc1cccc(CCCCC(*)=O)c1]
In some embodiments, L is
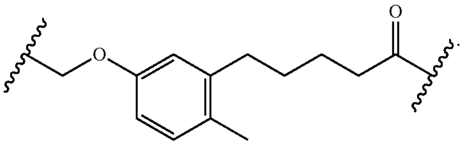 [SMILES: *COc1ccc(C)c(CCCCC(*)=O)c1]

In some embodiments, L is
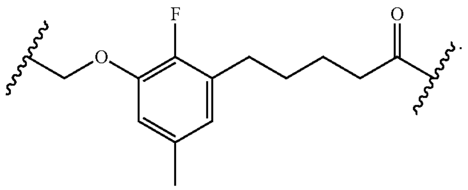 [SMILES: *COc1cc(C)cc(CCCCC(*)=O)c1F]
In some embodiments, L is
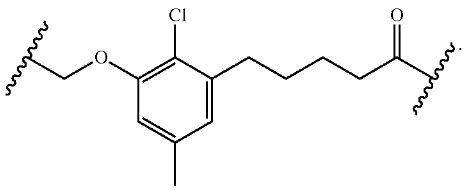
In some embodiments, L is
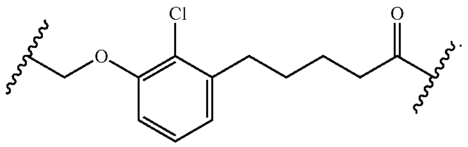
In some embodiments, L is
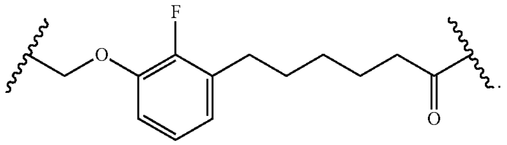 [SMILES: *COc1cccc(CCCCCC(*)=O)c1F]
In some embodiments, L is
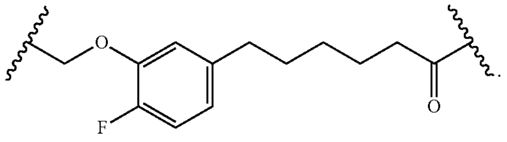 [SMILES: *COc1cc(CCCCCC(*)=O)ccc1F]
In some embodiments, L is
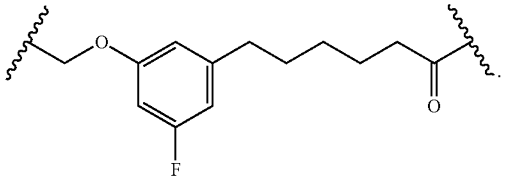 [SMILES: *COc1cc(F)cc(CCCCCC(*)=O)c1]
In some embodiments, L is
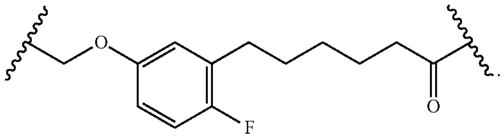
In some embodiments, L is
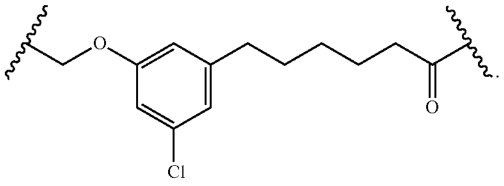 [SMILES: *COc1cc(Cl)cc(CCCCCC(*)=O)c1]
In some embodiments, L is
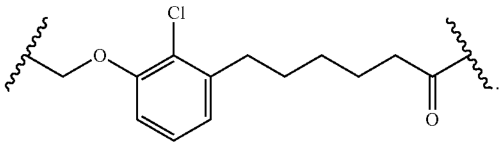 [SMILES: *COc1cccc(CCCCCC(*)=O)c1Cl]
In some embodiments, L is
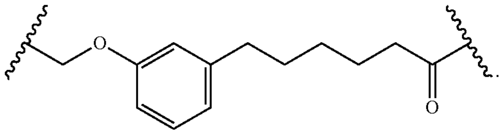 [SMILES: *COc1cccc(CCCCCC(*)=O)c1]
In some embodiments, L is
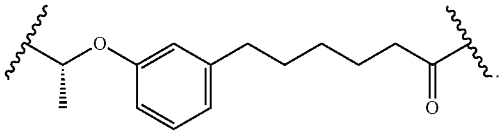 [SMILES: *C(=O)CCCCCc1cccc(O[C@@H](*)C)c1]
In some embodiments, L is
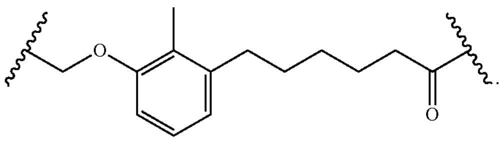 [SMILES: *COc1cccc(CCCCCC(*)=O)c1C]
In some embodiments, L is
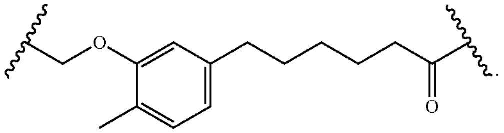 [SMILES: *COc1cc(CCCCCC(*)=O)ccc1C]

In some embodiments, L is
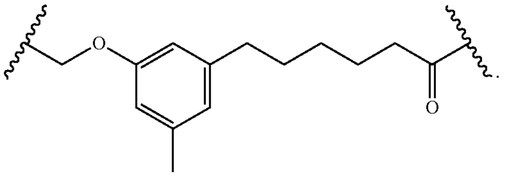 [SMILES: *COc1cc(C)cc(CCCCCC(*)=O)c1]
In some embodiments, L is
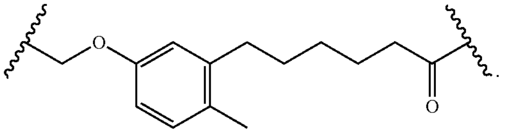 [SMILES: *COc1ccc(C)c(CCCCCC(*)=O)c1]
In some embodiments, L is
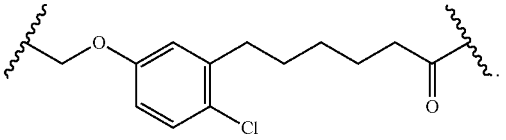 [SMILES: *COc1ccc(Cl)c(CCCCCC(*)=O)c1]
In some embodiments, L is
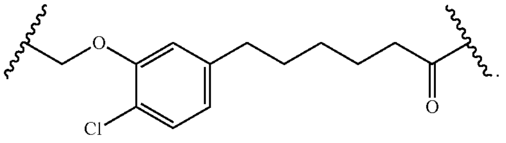 [SMILES: *COc1cc(CCCCCC(*)=O)ccc1Cl]
In some embodiments, L is
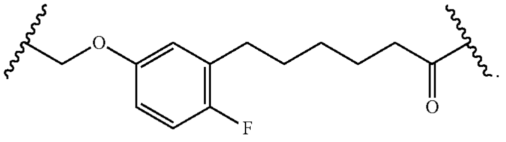 [SMILES: *COc1ccc(F)c(CCCCCC(*)=O)c1]
In some embodiments, L is
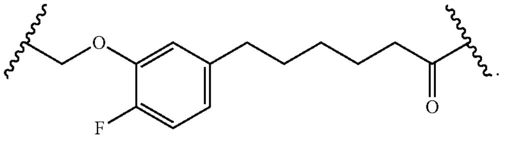 [SMILES: *COc1cc(CCCCCC(*)=O)ccc1F]
In some embodiments, L is
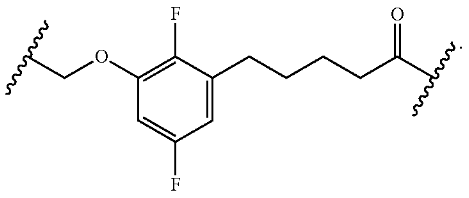 [SMILES: *COc1cc(F)cc(CCCCC(*)=O)c1F]
In some embodiments, L is
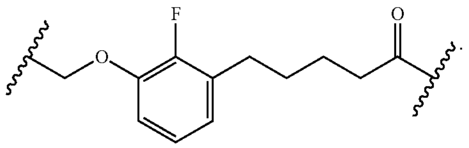 [SMILES: *COc1cccc(CCCCC(*)=O)c1F]
In some embodiments, L is
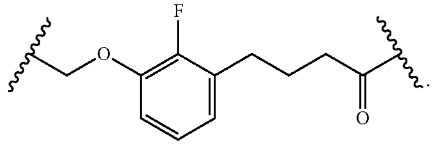 [SMILES: *COc1cccc(CCCC(*)=O)c1F]
In some embodiments, L is
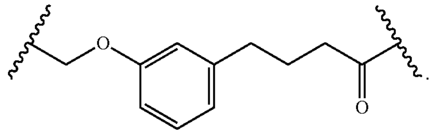 [SMILES: *COc1cccc(CCCC(*)=O)c1]
In some embodiments, L is
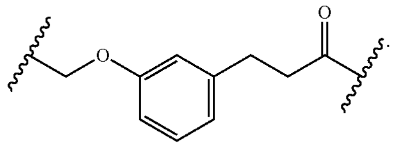 [SMILES: *COc1cccc(CCC(*)=O)c1]
In some embodiments, L is
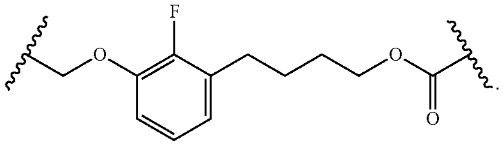 [SMILES: *COc1cccc(CCCCOC(*)=O)c1F]

In some embodiments, L is
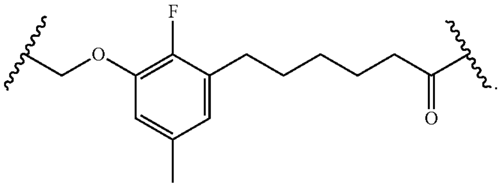 [SMILES: *COc1cc(C)cc(CCCCCC(*)=O)c1F]
In some embodiments, L is
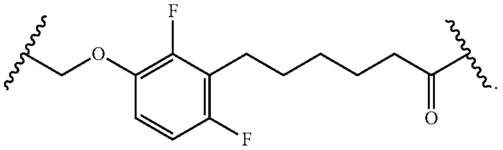 [SMILES: *COc1ccc(F)c(CCCCCC(*)=O)c1F]
In some embodiments, L is
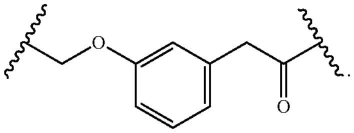 [SMILES: *COc1cccc(CC(*)=O)c1]
In some embodiments, L is
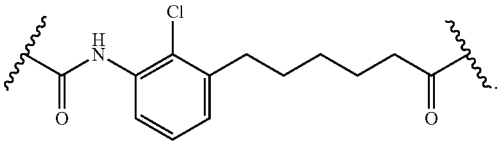
In some embodiments, L is
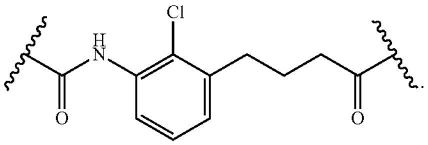 [SMILES: *C(=O)CCCc1cccc(NC(*)=O)c1Cl]
In some embodiments, L is
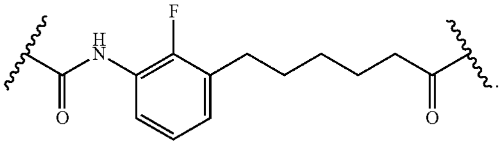 [SMILES: *C(=O)CCCCCc1cccc(NC(*)=O)c1F]
In some embodiments, L is
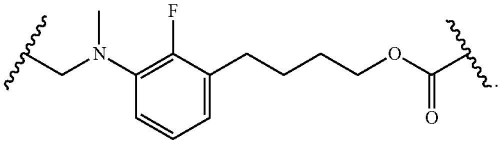 [SMILES: *CN(C)c1cccc(CCCCOC(*)=O)c1F]
In some embodiments, L is
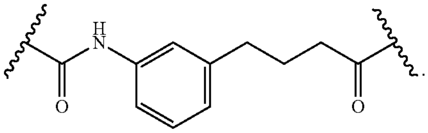 [SMILES: *C(=O)CCCc1cccc(NC(*)=O)c1]
In some embodiments, L is
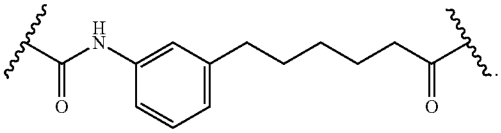 [SMILES: *C(=O)CCCCCc1cccc(NC(*)=O)c1]
In some embodiments, L is
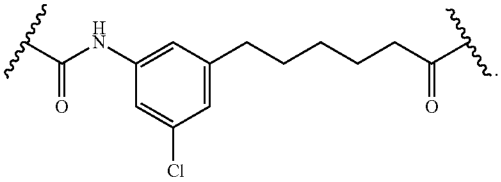 [SMILES: *C(=O)CCCCCc1cc(Cl)cc(NC(*)=O)c1]
In some embodiments, L is
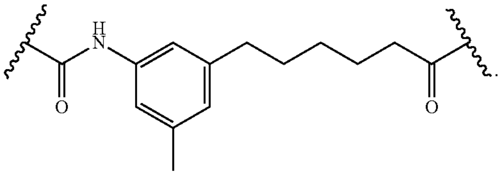 [SMILES: *C(=O)CCCCCc1cc(C)cc(NC(*)=O)c1]
In some embodiments, L is
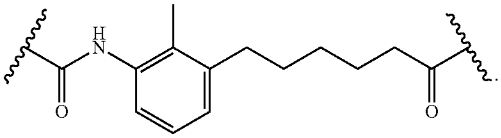 [SMILES: *C(=O)CCCCCc1cccc(NC(*)=O)c1C]

In some embodiments, L is
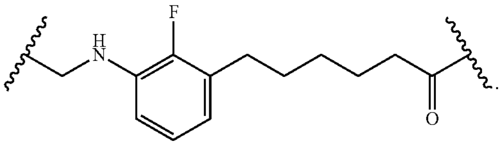
In some embodiments, L is
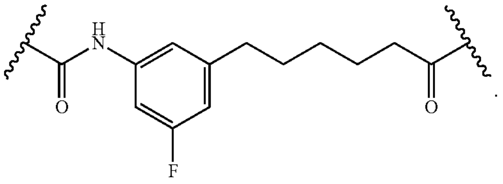 [SMILES: *C(=O)CCCCCc1cc(F)cc(NC(*)=O)c1]
In some embodiments, L is
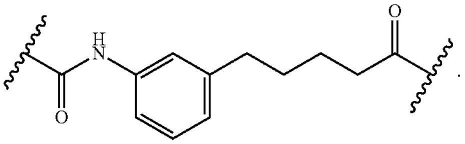 [SMILES: *C(=O)CCCCc1cccc(NC(*)=O)c1]
In some embodiments, L is
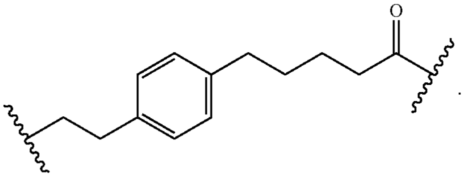 [SMILES: *CCc1ccc(CCCCC(*)=O)cc1]
In some embodiments, L is
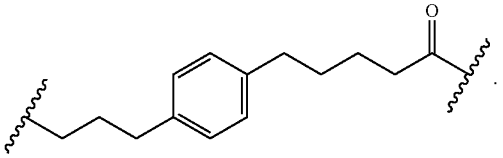 [SMILES: *CCCc1ccc(CCCCC(*)=O)cc1]
In some embodiments, L is
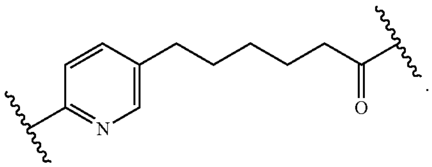 [SMILES: *C(=O)CCCCCc1ccc(*)nc1]
In some embodiments, L is
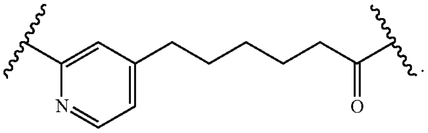 [SMILES: *C(=O)CCCCCc1ccnc(*)c1]
In some embodiments, L is
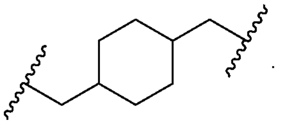 [SMILES: *CC1CCC(C*)CC1]
In some embodiments, L is
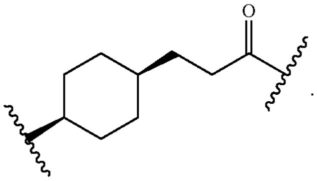 [SMILES: *C(=O)CC[C@H]1CC[C@@H](*)CC1]
In some embodiments, L is
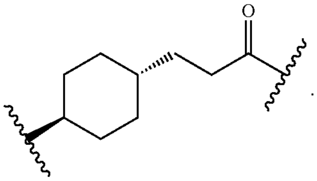 [SMILES: *C(=O)CC[C@H]1CC[C@H](*)CC1]
In some embodiments, L is
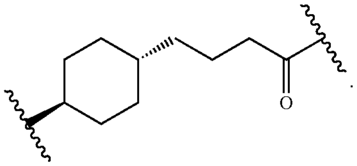 [SMILES: *C(=O)CCC[C@H]1CC[C@H](*)CC1]
In some embodiments, L is
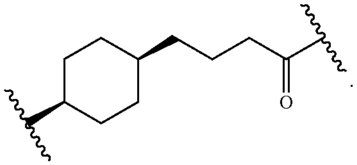 [SMILES: *C(=O)CCC[C@H]1CC[C@@H](*)CC1]

In some embodiments, L is

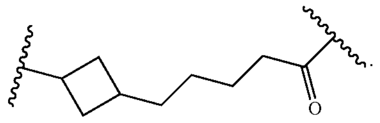 [SMILES: *C(=O)CCCCC1CC(*)C1]

In some embodiments, L is

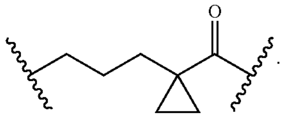 [SMILES: *CCCC1(C(*)=O)CC1]

In some embodiments, L is selected from those depicted in Table 1 or Table 1A, below.

Without limitation, the point of attachment of L to STAT and DIM can be, for example when L is

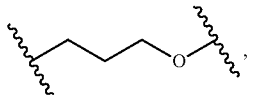 [SMILES: *CCCO*]

either

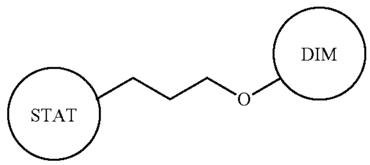

or

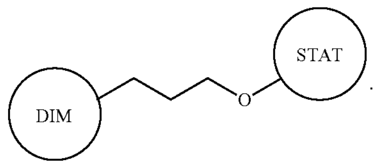

In some embodiments, a provided compound or pharmaceutically acceptable salt thereof, is selected from those wherein STAT is

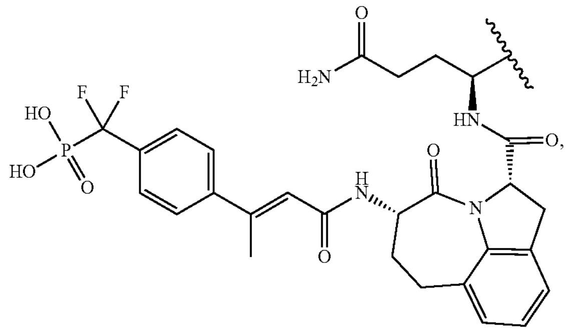 [SMILES: *[C@H](CCC(N)=O)NC(=O)[C@@H]1Cc2cccc3c2N1C(=O)[C@@H](NC(=O)/C=C(\C)c1ccc(C(F)(F)P(=O)(O)O)cc1)CC3]

LBM is selected from any of those in Table A below, and L is selected from any of those in Table B below.

In some embodiments, a provided compound or pharmaceutically acceptable salt thereof, is selected from those wherein STAT is

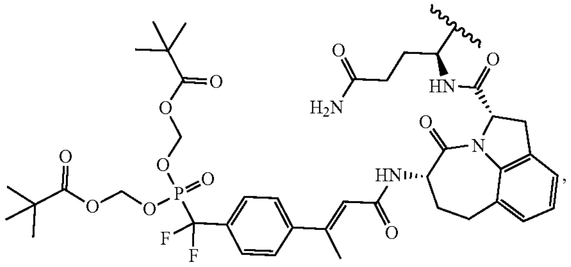 [SMILES: *[C@H](CCC(N)=O)NC(=O)[C@@H]1Cc2cccc3c2N1C(=O)[C@@H](NC(=O)/C=C(\C)c1ccc(C(F)(F)P(=O)(OCOC(=O)C(C)(C)C)OCOC(=O)C(C)(C)C)cc1)CC3]

LBM is selected from any of those in Table A below, and L is selected from any of those in Table B below.

In some embodiments, a provided compound or pharmaceutically acceptable salt thereof, is selected from those wherein STAT is

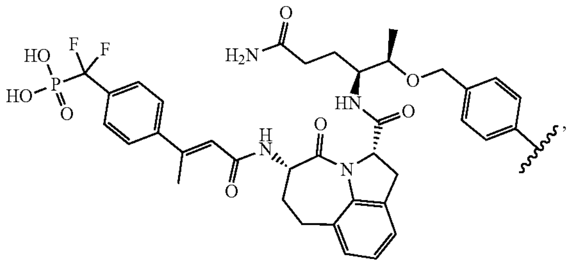 [SMILES: *c1ccc(CO[C@H](C)[C@H](CCC(N)=O)NC(=O)[C@@H]2Cc3cccc4c3N2C(=O)[C@@H](NC(=O)/C=C(\C)c2ccc(C(F)(F)P(=O)(O)O)cc2)CC4)cc1]

LBM is selected from any of those in Table A below, and L is selected from any of those in Table B below.

In some embodiments, a provided compound or pharmaceutically acceptable salt thereof, is selected from those wherein STAT is

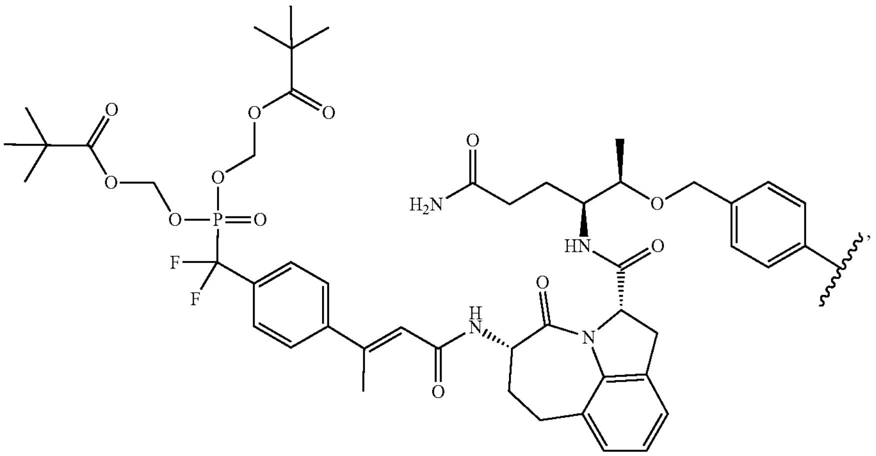 [SMILES: *c1ccc(CO[C@H](C)[C@H](CCC(N)=O)NC(=O)[C@@H]2Cc3cccc4c3N2C(=O)[C@@H](NC(=O)/C=C(\C)c2ccc(C(F)(F)P(=O)(OCOC(=O)C(C)(C)C)OCOC(=O)C(C)(C)C)cc2)CC4)cc1]

LBM is selected from any of those in Table A below, and L is selected from any of those in Table B below.

In some embodiments, a provided compound or pharmaceutically acceptable salt thereof, is selected from those wherein STAT is

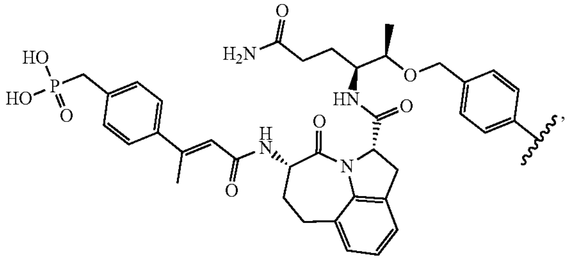 [SMILES: *c1ccc(CO[C@H](C)[C@H](CCC(N)=O)NC(=O)[C@@H]2Cc3cccc4c3N2C(=O)[C@@H](NC(=O)/C=C(\C)c2ccc(CP(=O)(O)O)cc2)CC4)cc1]

LBM is selected from any of those in Table A below, and L is selected from any of those in Table B below.

In some embodiments, a provided compound or pharmaceutically acceptable salt thereof, is selected from those wherein STAT i

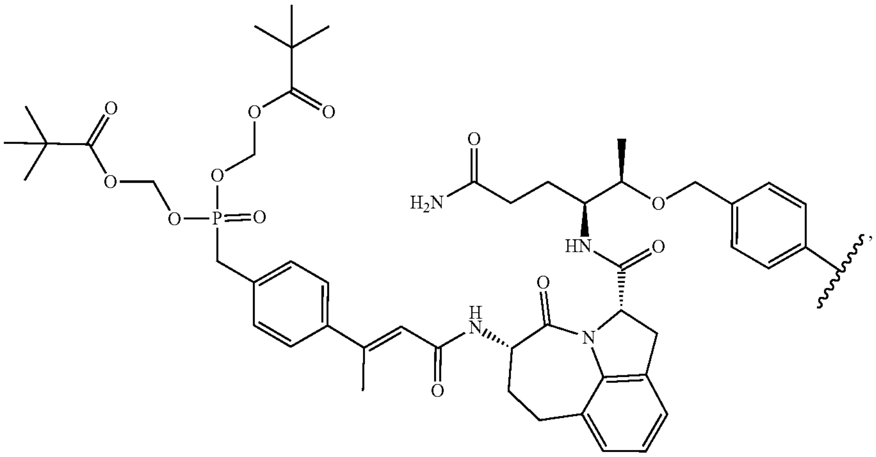 [SMILES: *c1ccc(CO[C@H](C)[C@H](CCC(N)=O)NC(=O)[C@@H]2Cc3cccc4c3N2C(=O)[C@@H](NC(=O)/C=C(\C)c2ccc(CP(=O)(OCOC(=O)C(C)(C)C)OCOC(=O)C(C)(C)C)cc2)CC4)cc1]

LBM is selected from any of those in Table A below, and L is selected from any of those in Table B below.

In some embodiments, a provided compound or pharmaceutically acceptable salt thereof, is selected from those wherein STAT is

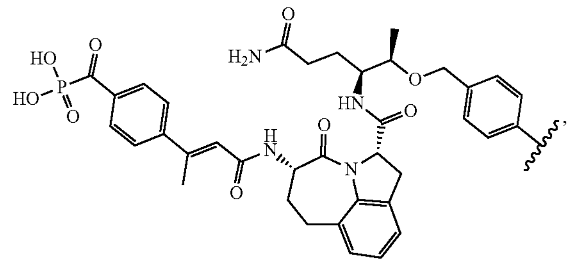 [SMILES: *c1ccc(CO[C@H](C)[C@H](CCC(N)=O)NC(=O)[C@@H]2Cc3cccc4c3N2C(=O)[C@@H](NC(=O)/C=C(\C)c2ccc(C(=O)P(=O)(O)O)cc2)CC4)cc1]

LBM is selected from any of those in Table A below, and L is selected from any of those in Table B below.

In some embodiments, a provided compound or pharmaceutically acceptable salt thereof, is selected from those wherein STAT is

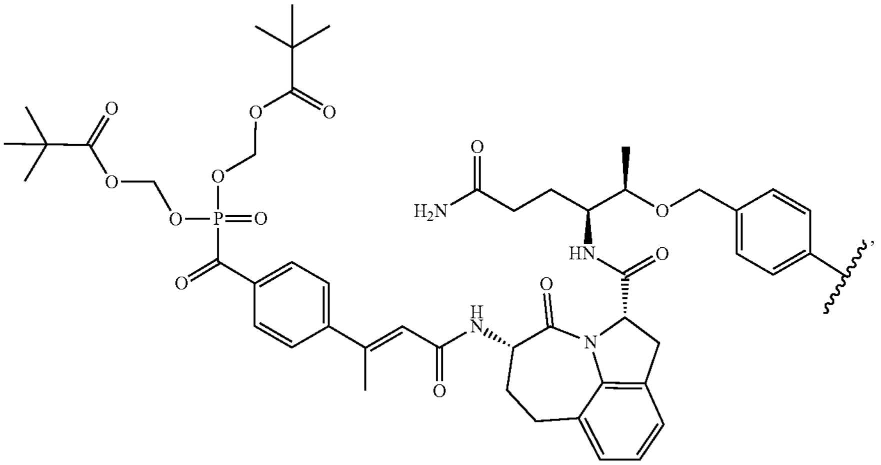 [SMILES: *c1ccc(CO[C@H](C)[C@H](CCC(N)=O)NC(=O)[C@@H]2Cc3cccc4c3N2C(=O)[C@@H](NC(=O)/C=C(\C)c2ccc(C(=O)P(=O)(OCOC(=O)C(C)(C)C)OCOC(=O)C(C)(C)C)cc2)CC4)cc1]

LBM is selected from any of those in Table A below, and L is selected from any of those in Table B below.

In some embodiments, a provided compound or pharmaceutically acceptable salt thereof, is selected from those wherein STAT is

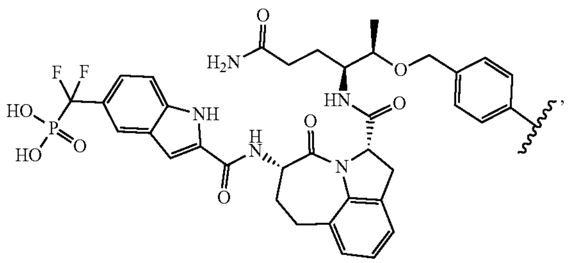 [SMILES: *c1ccc(CO[C@H](C)[C@H](CCC(N)=O)NC(=O)[C@@H]2Cc3cccc4c3N2C(=O)[C@@H](NC(=O)c2cc3cc(C(F)(F)P(=O)(O)O)ccc3[nH]2)CC4)cc1]

LBM is selected from any of those in Table A below, and L is selected from any of those in Table B below.

In some embodiments, a provided compound or pharmaceutically acceptable salt thereof, is selected from those wherein STAT is

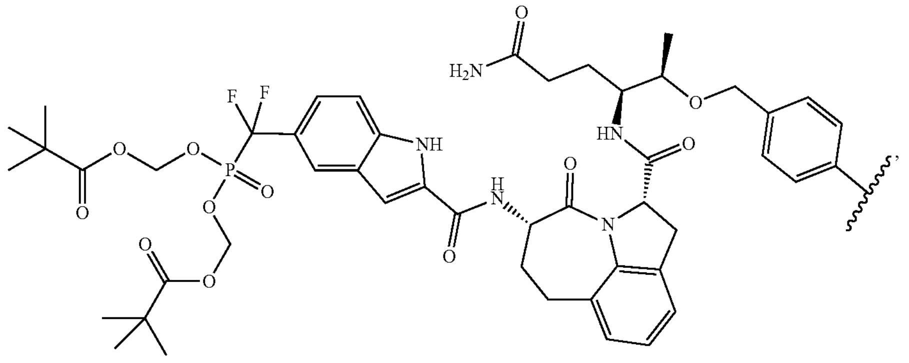 [SMILES: *c1ccc(CO[C@H](C)[C@H](CCC(N)=O)NC(=O)[C@@H]2Cc3cccc4c3N2C(=O)[C@@H](NC(=O)c2cc3cc(C(F)(F)P(=O)(OCOC(=O)C(C)(C)C)OCOC(=O)C(C)(C)C)ccc3[nH]2)CC4)cc1]

LBM is selected from any of those in Table A below, and L is selected from any of those in Table B below.

In some embodiments, a provided compound or pharmaceutically acceptable salt thereof, is selected from those wherein STAT i LBM is

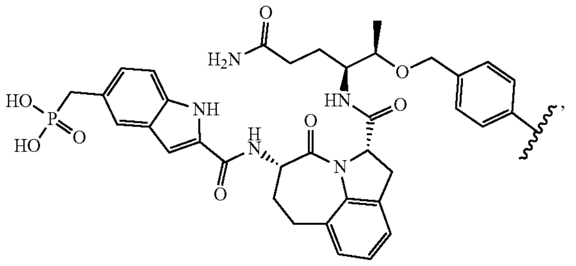 [SMILES: *c1ccc(CO[C@H](C)[C@H](CCC(N)=O)NC(=O)[C@@H]2Cc3cccc4c3N2C(=O)[C@@H](NC(=O)c2cc3cc(CP(=O)(O)O)ccc3[nH]2)CC4)cc1]

selected from any of those in Table A below, and L is selected from any of those in Table B below.

In some embodiments, a provided compound or pharmaceutically acceptable salt thereof, is selected from those wherein STAT is

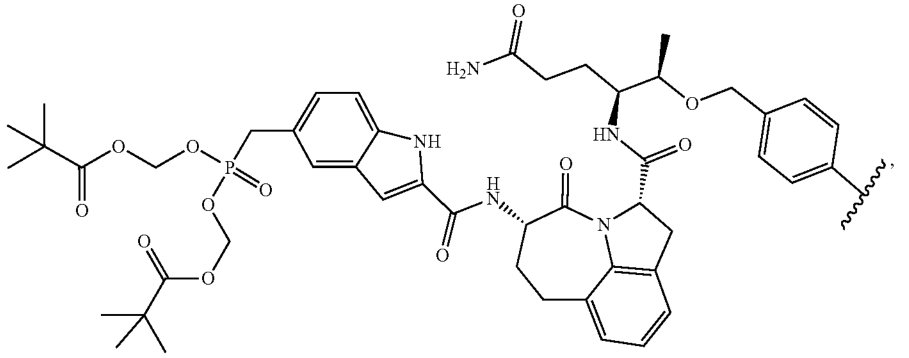 [SMILES: *c1ccc(CO[C@H](C)[C@H](CCC(N)=O)NC(=O)[C@@H]2Cc3cccc4c3N2C(=O)[C@@H](NC(=O)c2cc3cc(CP(=O)(OCOC(=O)C(C)(C)C)OCOC(=O)C(C)(C)C)ccc3[nH]2)CC4)cc1]

LBM is selected from any of those in Table A below, and L is selected from any of those in Table B below.

In some embodiments, a provided compound or pharmaceutically acceptable salt thereof, is selected from those wherein STAT is

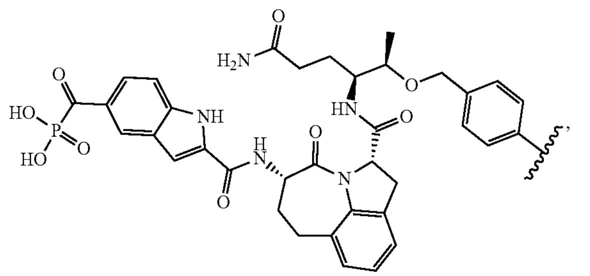 [SMILES: *c1ccc(CO[C@H](C)[C@H](CCC(N)=O)NC(=O)[C@@H]2Cc3cccc4c3N2C(=O)[C@@H](NC(=O)c2cc3cc(C(=O)P(=O)(O)O)ccc3[nH]2)CC4)cc1]

LBM is selected from any of those in Table A below, and L is selected from any of those in Table B below.

In some embodiments, a provided compound or pharmaceutically acceptable salt thereof, is selected from those wherein STAT is

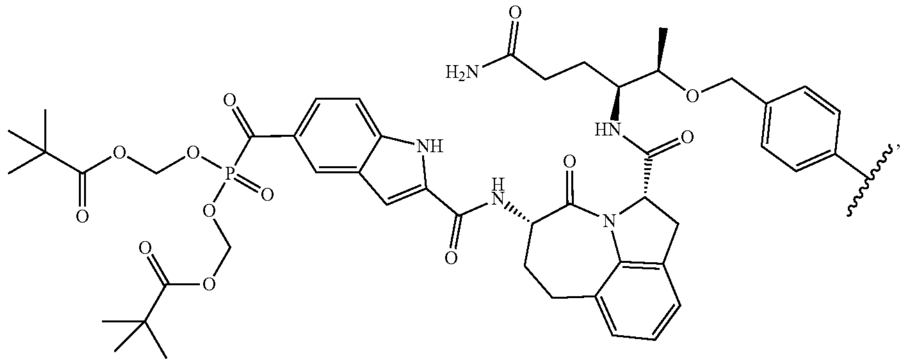 [SMILES: *c1ccc(CO[C@H](C)[C@H](CCC(N)=O)NC(=O)[C@@H]2Cc3cccc4c3N2C(=O)[C@@H](NC(=O)c2cc3cc(C(=O)P(=O)(OCOC(=O)C(C)(C)C)OCOC(=O)C(C)(C)C)ccc3[nH]2)CC4)cc1]

LBM is selected from any of those in Table A below, and L is selected from any of those in Table B below.

In some embodiments, a provided compound or pharmaceutically acceptable salt thereof, is selected from those wherein STAT is

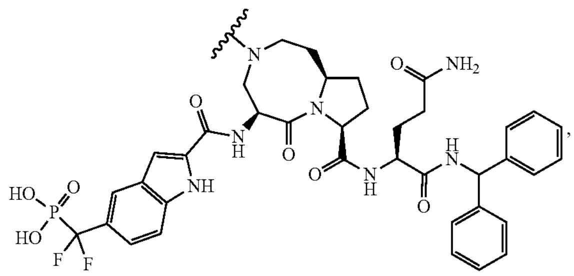 [SMILES: *N1CC[C@H]2CC[C@@H](C(=O)N[C@@H](CCC(N)=O)C(=O)NC(c3ccccc3)c3ccccc3)N2C(=O)[C@@H](NC(=O)c2cc3cc(C(F)(F)P(=O)(O)O)ccc3[nH]2)C1]

LBM is selected from any of those in Table A below, and L is selected from any of those in Table B below.

In some embodiments, a provided compound or pharmaceutically acceptable salt thereof, is selected from those wherein STAT is

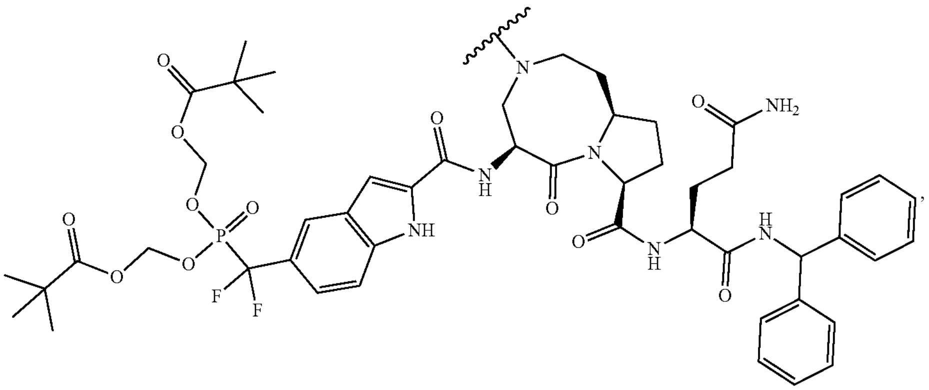 [SMILES: *N1CC[C@H]2CC[C@@H](C(=O)N[C@@H](CCC(N)=O)C(=O)NC(c3ccccc3)c3ccccc3)N2C(=O)[C@@H](NC(=O)c2cc3cc(C(F)(F)P(=O)(OCOC(=O)C(C)(C)C)OCOC(=O)C(C)(C)C)ccc3[nH]2)C1]

LBM is selected from any of those in Table A below, and L is selected from any of those in Table B below.

In some embodiments, a provided compound or pharmaceutically acceptable salt thereof, is selected from those wherein STAT is

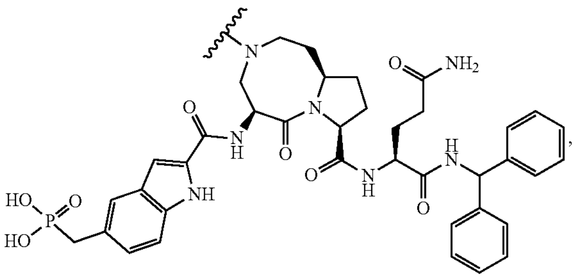 [SMILES: *N1CC[C@H]2CC[C@@H](C(=O)N[C@@H](CCC(N)=O)C(=O)NC(c3ccccc3)c3ccccc3)N2C(=O)[C@@H](NC(=O)c2cc3cc(CP(=O)(O)O)ccc3[nH]2)C1]

LBM is selected from any of those in Table A below, and L is selected from any of those in Table B below.

In some embodiments, a provided compound or pharmaceutically acceptable salt thereof, is selected from those wherein STAT is

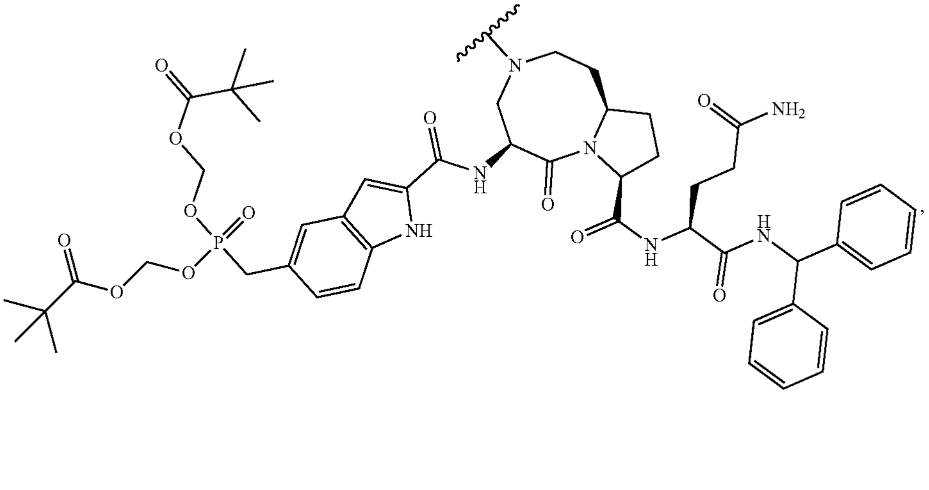 [SMILES: *N1CC[C@H]2CC[C@@H](C(=O)N[C@@H](CCC(N)=O)C(=O)NC(c3ccccc3)c3ccccc3)N2C(=O)[C@@H](NC(=O)c2cc3cc(CP(=O)(OCOC(=O)C(C)(C)C)OCOC(=O)C(C)(C)C)ccc3[nH]2)C1]

LBM is selected from any of those in Table A below, and L is selected from any of those in Table B below.

In some embodiments, a provided compound or pharmaceutically acceptable salt thereof, is selected from those wherein STAT is

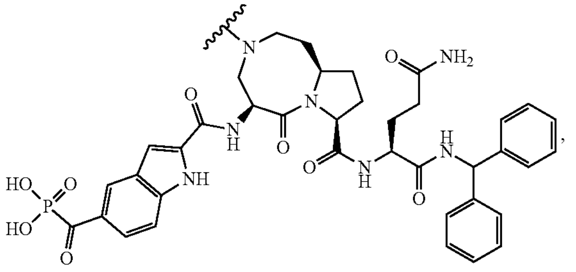 [SMILES: *N1CC[C@H]2CC[C@@H](C(=O)N[C@@H](CCC(N)=O)C(=O)NC(c3ccccc3)c3ccccc3)N2C(=O)[C@@H](NC(=O)c2cc3cc(C(=O)P(=O)(O)O)ccc3[nH]2)C1]

LBM is selected from any of those in Table A below, and L is selected from any of those in Table B below.

In some embodiments, a provided compound or pharmaceutically acceptable salt thereof, is selected from those wherein STAT is

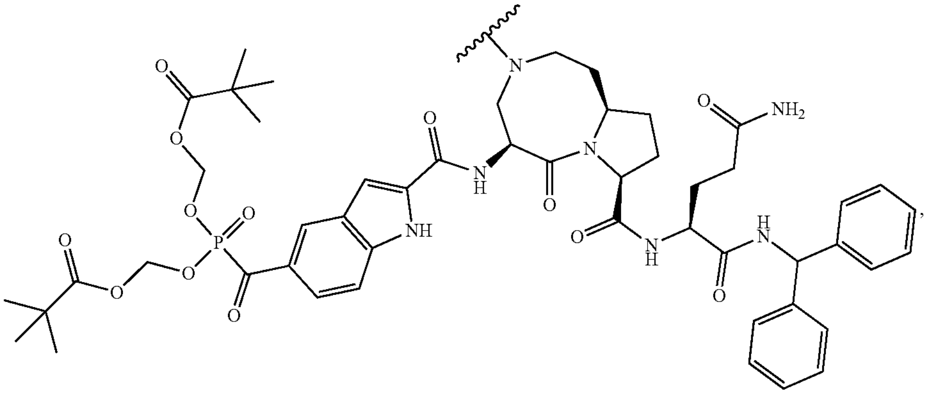 [SMILES: *N1CC[C@H]2CC[C@@H](C(=O)N[C@@H](CCC(N)=O)C(=O)NC(c3ccccc3)c3ccccc3)N2C(=O)[C@@H](NC(=O)c2cc3cc(C(=O)P(=O)(OCOC(=O)C(C)(C)C)OCOC(=O)C(C)(C)C)ccc3[nH]2)C1]

LBM is selected from any of those in Table A below, and L is selected from any of those in Table B below.

In some embodiments, a provided compound or pharmaceutically acceptable salt thereof, is selected from those wherein STAT is

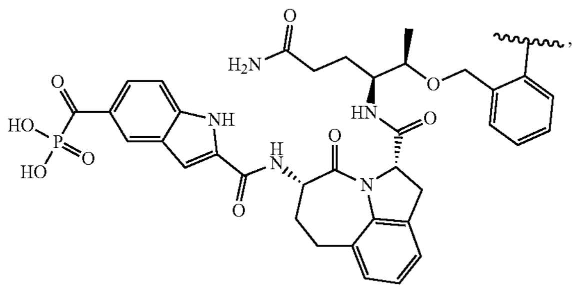 [SMILES: *c1ccccc1CO[C@H](C)[C@H](CCC(N)=O)NC(=O)[C@@H]1Cc2cccc3c2N1C(=O)[C@@H](NC(=O)c1cc2cc(C(=O)P(=O)(O)O)ccc2[nH]1)CC3]

LBM is selected from any of those in Table A below, and L is selected from any of those in Table B below.

In some embodiments, a provided compound or pharmaceutically acceptable salt thereof, is selected from those wherein STAT is

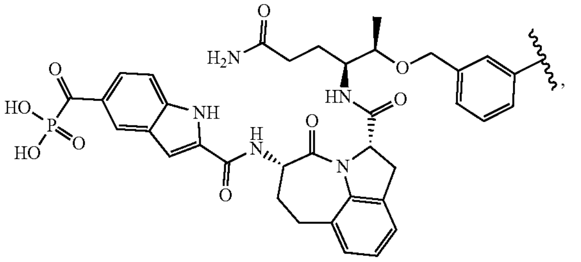 [SMILES: *c1cccc(CO[C@H](C)[C@H](CCC(N)=O)NC(=O)[C@@H]2Cc3cccc4c3N2C(=O)[C@@H](NC(=O)c2cc3cc(C(=O)P(=O)(O)O)ccc3[nH]2)CC4)c1]

LBM is selected from any of those in Table A below, and L is selected from any of those in Table B below.

In some embodiments, a provided compound or pharmaceutically acceptable salt thereof, is selected from those wherein STAT is

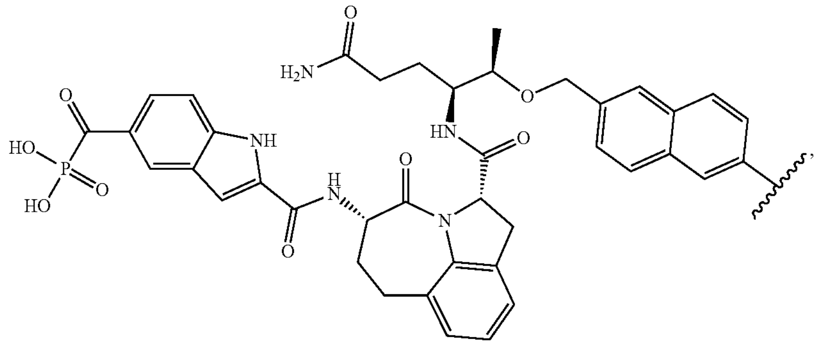 [SMILES: *c1ccc2cc(CO[C@H](C)[C@H](CCC(N)=O)NC(=O)[C@@H]3Cc4cccc5c4N3C(=O)[C@@H](NC(=O)c3cc4cc(C(=O)P(=O)(O)O)ccc4[nH]3)CC5)ccc2c1]

LBM is selected from any of those in Table A below, and L is selected from any of those in Table B below.

In some embodiments, a provided compound or pharmaceutically acceptable salt thereof, is selected from those wherein STAT is

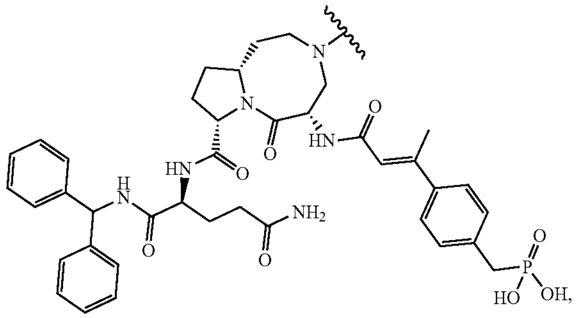 [SMILES: *N1CC[C@H]2CC[C@@H](C(=O)N[C@@H](CCC(N)=O)C(=O)NC(c3ccccc3)c3ccccc3)N2C(=O)[C@@H](NC(=O)/C=C(\C)c2ccc(CP(=O)(O)O)cc2)C1]

LBM is selected from any of those in Table A below, and L is selected from any of those in Table B below.

In some embodiments, a provided compound or pharmaceutically acceptable salt thereof, is selected from those wherein STAT is

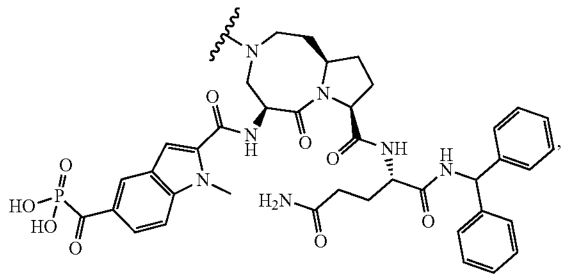 [SMILES: *N1CC[C@H]2CC[C@@H](C(=O)N[C@@H](CCC(N)=O)C(=O)NC(c3ccccc3)c3ccccc3)N2C(=O)[C@@H](NC(=O)c2cc3cc(C(=O)P(=O)(O)O)ccc3n2C)C1]

LBM is selected from any of those in Table A below, and L is selected from any of those in Table B below.

In some embodiments, a provided compound or pharmaceutically acceptable salt thereof, is selected from those wherein STAT is

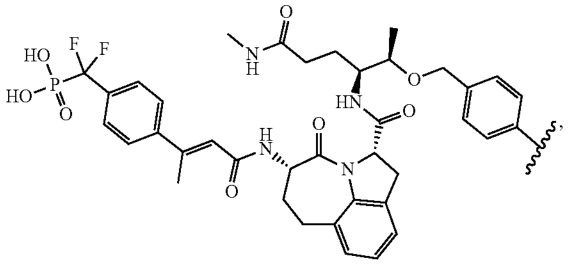 [SMILES: *c1ccc(CO[C@H](C)[C@H](CCC(=O)NC)NC(=O)[C@@H]2Cc3cccc4c3N2C(=O)[C@@H](NC(=O)/C=C(\C)c2ccc(C(F)(F)P(=O)(O)O)cc2)CC4)cc1]

LBM is selected from any of those in Table A below, and L is selected from any of those in Table B below.

In some embodiments, a provided compound or pharmaceutically acceptable salt thereof, is selected from those wherein STAT is

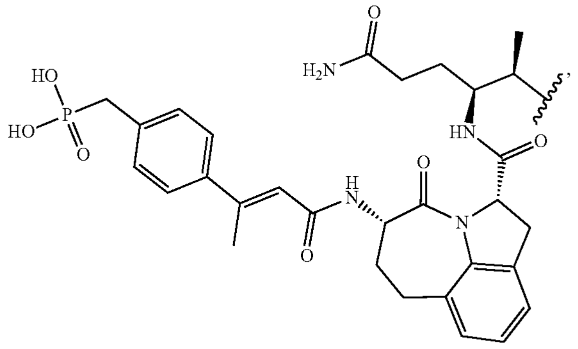 [SMILES: *[C@H](C)[C@H](CCC(N)=O)NC(=O)[C@@H]1Cc2cccc3c2N1C(=O)[C@@H](NC(=O)/C=C(\C)c1ccc(CP(=O)(O)O)cc1)CC3]

LBM is selected from any of those in Table A below, and L is selected from any of those in Table B below.

In some embodiments, a provided compound or pharmaceutically acceptable salt thereof, is selected from those wherein STAT is

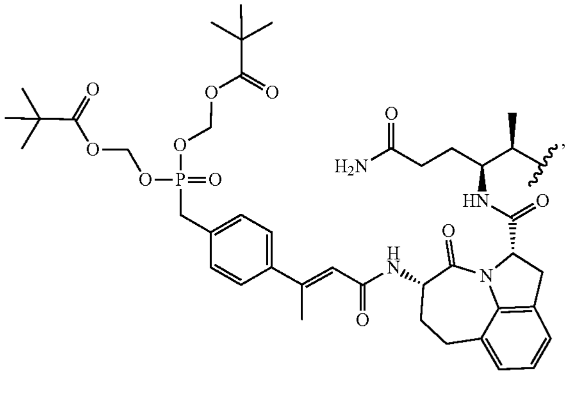 [SMILES: *[C@H](C)[C@H](CCC(N)=O)NC(=O)[C@@H]1Cc2cccc3c2N1C(=O)[C@@H](NC(=O)/C=C(\C)c1ccc(CP(=O)(OCOC(=O)C(C)(C)C)OCOC(=O)C(C)(C)C)cc1)CC3]

LBM is selected from any of those in Table A below, and L is selected from any of those in Table B below.

In some embodiments, a provided compound or pharmaceutically acceptable salt thereof, is selected from those wherein STAT is

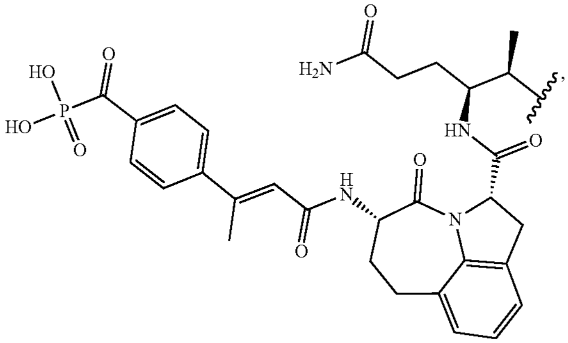 [SMILES: *[C@H](C)[C@H](CCC(N)=O)NC(=O)[C@@H]1Cc2cccc3c2N1C(=O)[C@@H](NC(=O)/C=C(\C)c1ccc(C(=O)P(=O)(O)O)cc1)CC3]

LBM is selected from any of those in Table A below, and L is selected from any of those in Table B below.

In some embodiments, a provided compound or pharmaceutically acceptable salt thereof, is selected from those wherein STAT is

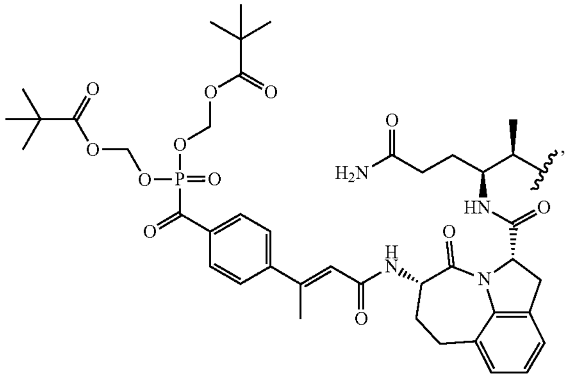 [SMILES: *[C@H](C)[C@H](CCC(N)=O)NC(=O)[C@@H]1Cc2cccc3c2N1C(=O)[C@@H](NC(=O)/C=C(\C)c1ccc(C(=O)P(=O)(OCOC(=O)C(C)(C)C)OCOC(=O)C(C)(C)C)cc1)CC3]

LBM is selected from any of those in Table A below, and L is selected from any of those in Table B below.

In some embodiments, a provided compound or pharmaceutically acceptable salt thereof, is selected from those wherein STAT

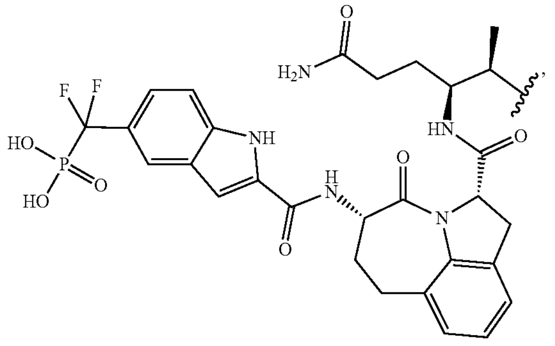 [SMILES: *[C@H](C)[C@H](CCC(N)=O)NC(=O)[C@@H]1Cc2cccc3c2N1C(=O)[C@@H](NC(=O)c1cc2cc(C(F)(F)P(=O)(O)O)ccc2[nH]1)CC3]

LBM is selected from any of those in Table A below, and L is selected from any of those in Table B below.

In some embodiments, a provided compound or pharmaceutically acceptable salt thereof, is selected from those wherein STAT is

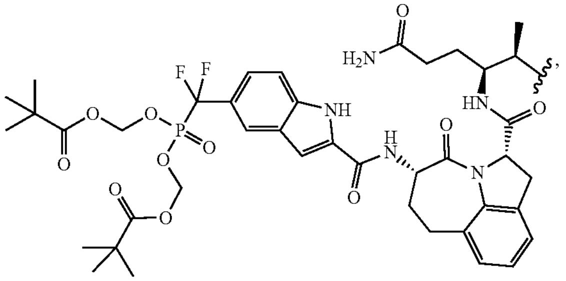 [SMILES: *[C@H](C)[C@H](CCC(N)=O)NC(=O)[C@@H]1Cc2cccc3c2N1C(=O)[C@@H](NC(=O)c1cc2cc(C(F)(F)P(=O)(OCOC(=O)C(C)(C)C)OCOC(=O)C(C)(C)C)ccc2[nH]1)CC3]

LBM is selected from any of those in Table A below, and L is selected from any of those in Table B below.

In some embodiments, a provided compound or pharmaceutically acceptable salt thereof, is selected from those wherein STAT is

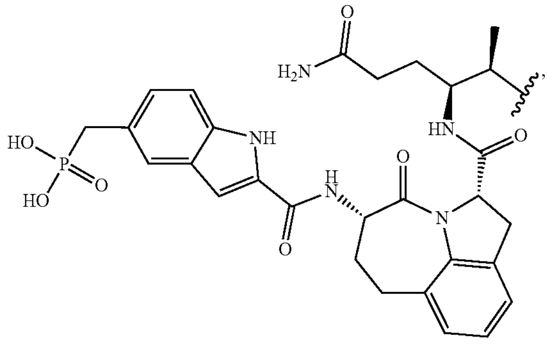 [SMILES: *[C@H](C)[C@H](CCC(N)=O)NC(=O)[C@@H]1Cc2cccc3c2N1C(=O)[C@@H](NC(=O)c1cc2cc(CP(=O)(O)O)ccc2[nH]1)CC3]

LBM is selected from any of those in Table A below, and L is selected from any of those in Table B below.

In some embodiments, a provided compound or pharmaceutically acceptable salt thereof, is selected from those wherein STAT is

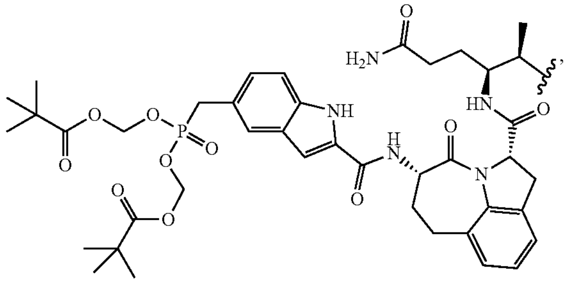 [SMILES: *[C@H](C)[C@H](CCC(N)=O)NC(=O)[C@@H]1Cc2cccc3c2N1C(=O)[C@@H](NC(=O)c1cc2cc(CP(=O)(OCOC(=O)C(C)(C)C)OCOC(=O)C(C)(C)C)ccc2[nH]1)CC3]

LBM is selected from any of those in Table A below, and L is selected from any of those in Table B below.

In some embodiments, a provided compound or pharmaceutically acceptable salt thereof, is selected from those wherein STAT is

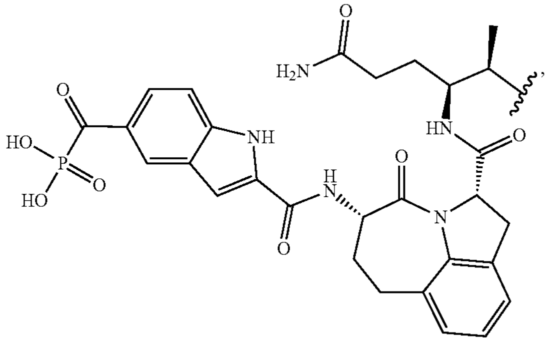 [SMILES: *[C@H](C)[C@H](CCC(N)=O)NC(=O)[C@@H]1Cc2cccc3c2N1C(=O)[C@@H](NC(=O)c1cc2cc(C(=O)P(=O)(O)O)ccc2[nH]1)CC3]

LBM is selected from any of those in Table A below, and L is selected from any of those in Table B below.

In some embodiments, a provided compound or pharmaceutically acceptable salt thereof, is selected from those wherein STAT is

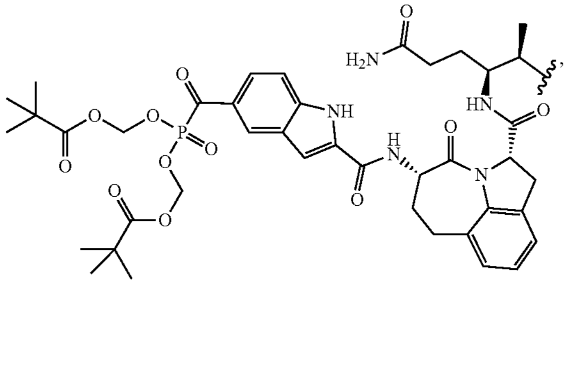 [SMILES: *[C@H](C)[C@H](CCC(N)=O)NC(=O)[C@@H]1Cc2cccc3c2N1C(=O)[C@@H](NC(=O)c1cc2cc(C(=O)P(=O)(OCOC(=O)C(C)(C)C)OCOC(=O)C(C)(C)C)ccc2[nH]1)CC3]

LBM is selected from any of those in Table A below, and L is selected from any of those in Table B below.

In some embodiments, a provided compound or pharmaceutically acceptable salt thereof, is selected from those wherein STAT is

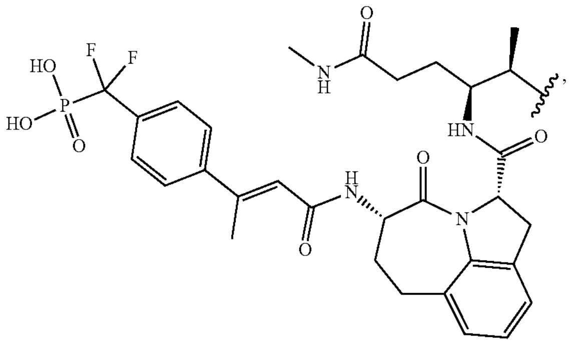 [SMILES: *[C@H](C)[C@H](CCC(=O)NC)NC(=O)[C@@H]1Cc2cccc3c2N1C(=O)[C@@H](NC(=O)/C=C(\C)c1ccc(C(F)(F)P(=O)(O)O)cc1)CC3]

LBM is selected from any of those in Table A below, and L is selected from any of those in Table B below.

In some embodiments, a provided compound or pharmaceutically acceptable salt thereof, is selected from those wherein STAT is

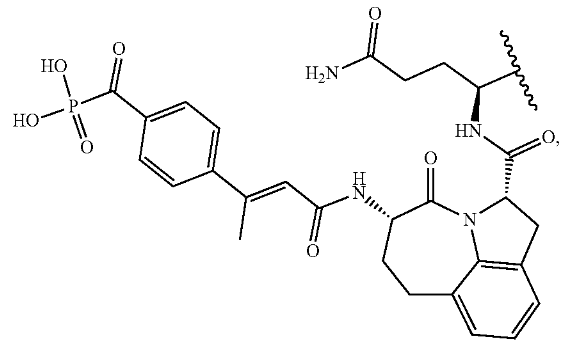 [SMILES: *[C@H](CCC(N)=O)NC(=O)[C@@H]1Cc2cccc3c2N1C(=O)[C@@H](NC(=O)/C=C(\C)c1ccc(C(=O)P(=O)(O)O)cc1)CC3]

LBM is selected from any of those in Table A below, and L is selected from any of those in Table B below.

In some embodiments, a provided compound or pharmaceutically acceptable salt thereof, is selected from those wherein STAT

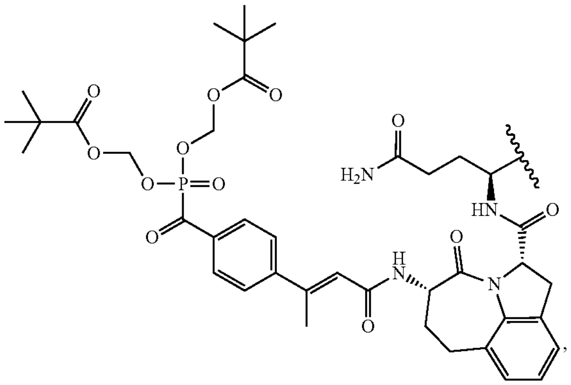 [SMILES: *[C@H](CCC(N)=O)NC(=O)[C@@H]1Cc2cccc3c2N1C(=O)[C@@H](NC(=O)/C=C(\C)c1ccc(C(=O)P(=O)(OCOC(=O)C(C)(C)C)OCOC(=O)C(C)(C)C)cc1)CC3]

LBM is selected from any of those in Table A below, and L is selected from any of those in Table B below.

In some embodiments, a provided compound or pharmaceutically acceptable salt thereof, is selected from those wherein STAT is

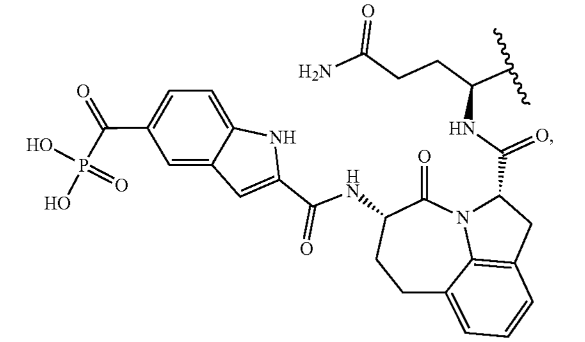 [SMILES: *[C@H](CCC(N)=O)NC(=O)[C@@H]1Cc2cccc3c2N1C(=O)[C@@H](NC(=O)c1cc2cc(C(=O)P(=O)(O)O)ccc2[nH]1)CC3]

LBM is selected from any of those in Table A below, and L is selected from any of those in Table B below.

In some embodiments, a provided compound or pharmaceutically acceptable salt thereof, is selected from those wherein STAT is

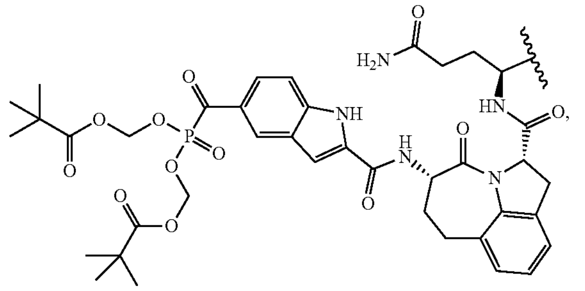 [SMILES: *[C@H](CCC(N)=O)NC(=O)[C@@H]1Cc2cccc3c2N1C(=O)[C@@H](NC(=O)c1cc2cc(C(=O)P(=O)(OCOC(=O)C(C)(C)C)OCOC(=O)C(C)(C)C)ccc2[nH]1)CC3]

LBM is selected from any of those in Table A below, and L is selected from any of those in Table B below.

In some embodiments, a provided compound or pharmaceutically acceptable salt thereof, is selected from those wherein STAT is

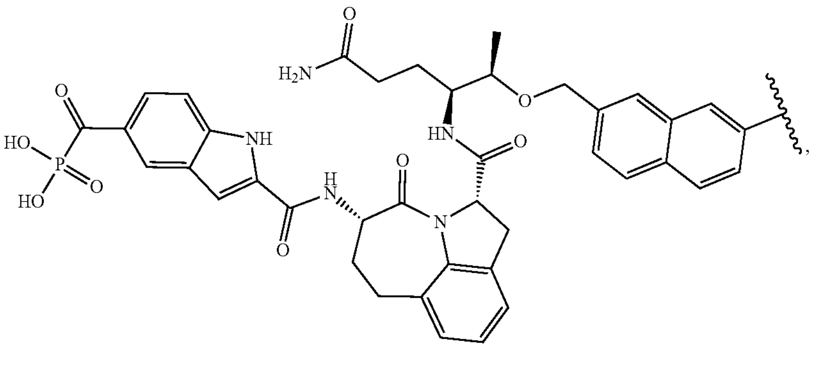 [SMILES: *c1ccc2ccc(CO[C@H](C)[C@H](CCC(N)=O)NC(=O)[C@@H]3Cc4cccc5c4N3C(=O)[C@@H](NC(=O)c3cc4cc(C(=O)P(=O)(O)O)ccc4[nH]3)CC5)cc2c1]

LBM is selected from any of those in Table A below, and L is selected from any of those in Table B below.

In some embodiments, a provided compound or pharmaceutically acceptable salt thereof, is selected from those wherein STAT is

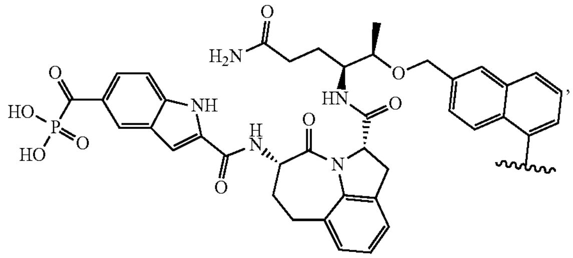 [SMILES: *c1cccc2cc(CO[C@H](C)[C@H](CCC(N)=O)NC(=O)[C@@H]3Cc4cccc5c4N3C(=O)[C@@H](NC(=O)c3cc4cc(C(=O)P(=O)(O)O)ccc4[nH]3)CC5)ccc12]

LBM is selected from any of those in Table A below, and L is selected from any of those in Table B below.

In some embodiments, a provided compound or pharmaceutically acceptable salt thereof, is selected from those wherein STAT is

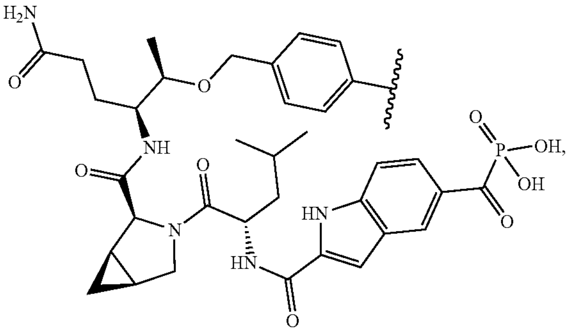 [SMILES: *c1ccc(CO[C@H](C)[C@H](CCC(N)=O)NC(=O)[C@@H]2[C@@H]3C[C@@H]3CN2C(=O)[C@H](CC(C)C)NC(=O)c2cc3cc(C(=O)P(=O)(O)O)ccc3[nH]2)cc1]

LBM is selected from any of those in Table A below, and L is selected from any of those in Table B below.

In some embodiments, a provided compound or pharmaceutically acceptable salt thereof, is selected from those wherein STAT is

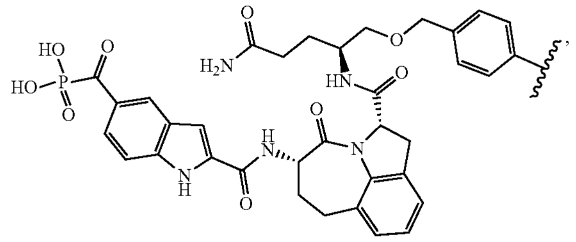 [SMILES: *c1ccc(COC[C@H](CCC(N)=O)NC(=O)[C@@H]2Cc3cccc4c3N2C(=O)[C@@H](NC(=O)c2cc3cc(C(=O)P(=O)(O)O)ccc3[nH]2)CC4)cc1]

LBM is selected from any of those in Table A below, and L is selected from any of those in Table B below.

In some embodiments, a provided compound or pharmaceutically acceptable salt thereof, is selected from those wherein STAT is

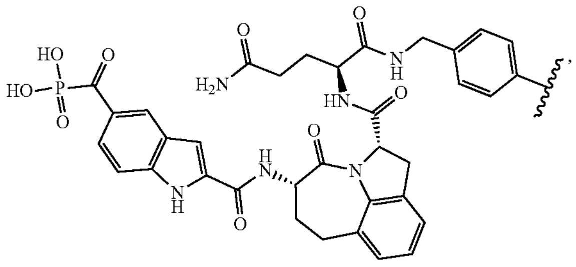 [SMILES: *c1ccc(CNC(=O)[C@H](CCC(N)=O)NC(=O)[C@@H]2Cc3cccc4c3N2C(=O)[C@@H](NC(=O)c2cc3cc(C(=O)P(=O)(O)O)ccc3[nH]2)CC4)cc1]

LBM is selected from any of those in Table A below, and L is selected from any of those in Table B below.

In some embodiments, a provided compound or pharmaceutically acceptable salt thereof, is selected from those wherein STAT is

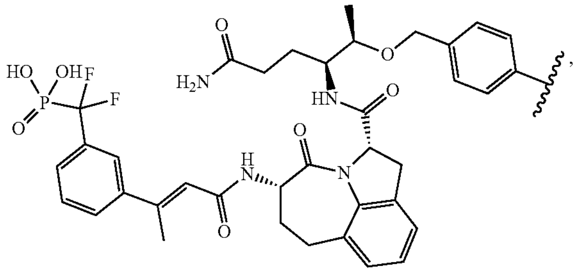 [SMILES: *c1ccc(CO[C@H](C)[C@H](CCC(N)=O)NC(=O)[C@@H]2Cc3cccc4c3N2C(=O)[C@@H](NC(=O)/C=C(\C)c2cccc(C(F)(F)P(=O)(O)O)c2)CC4)cc1]

LBM is selected from any of those in Table A below, and L is selected from any of those in Table B below.

In some embodiments, a provided compound or pharmaceutically acceptable salt thereof, is selected from those wherein STAT is

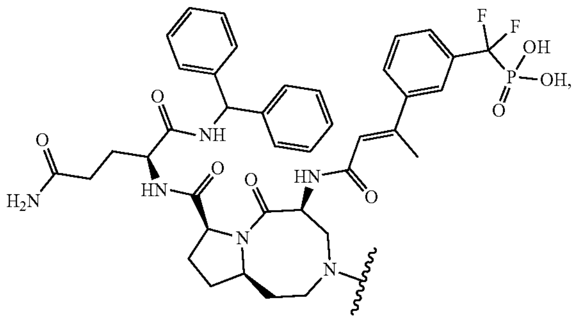 [SMILES: *N1CC[C@H]2CC[C@@H](C(=O)N[C@@H](CCC(N)=O)C(=O)NC(c3ccccc3)c3ccccc3)N2C(=O)[C@@H](NC(=O)/C=C(\C)c2cccc(C(F)(F)P(=O)(O)O)c2)C1]

LBM is from any of those in Table A below, and L is selected from any of those in Table B below.

In some embodiments, a provided compound or pharmaceutically acceptable salt thereof, is selected from those wherein STAT is

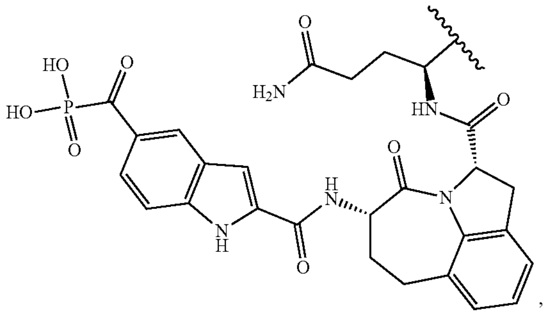 [SMILES: *[C@H](CCC(N)=O)NC(=O)[C@@H]1Cc2cccc3c2N1C(=O)[C@@H](NC(=O)c1cc2cc(C(=O)P(=O)(O)O)ccc2[nH]1)CC3]

LBM is selected from any of those in Table A below, and L is selected from any of those in Table B below.

In some embodiments, a provided compound or pharmaceutically acceptable salt thereof, is selected from those wherein STAT is

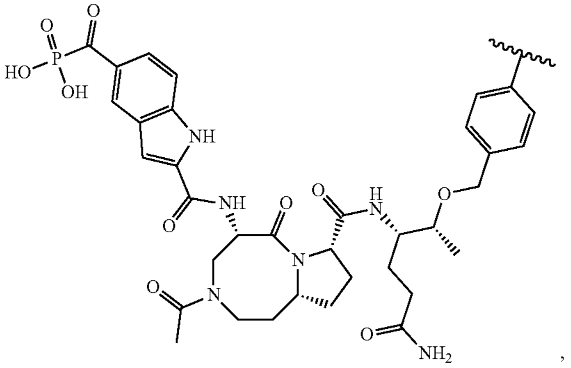 [SMILES: *c1ccc(CO[C@H](C)[C@H](CCC(N)=O)NC(=O)[C@@H]2CC[C@@H]3CCN(C(C)=O)C[C@H](NC(=O)c4cc5cc(C(=O)P(=O)(O)O)ccc5[nH]4)C(=O)N32)cc1]

LBM is selected from any of those in Table A below, and L is selected from any of those in Table B below.

In some embodiments, a provided compound or pharmaceutically acceptable salt thereof, is selected from those wherein STAT is

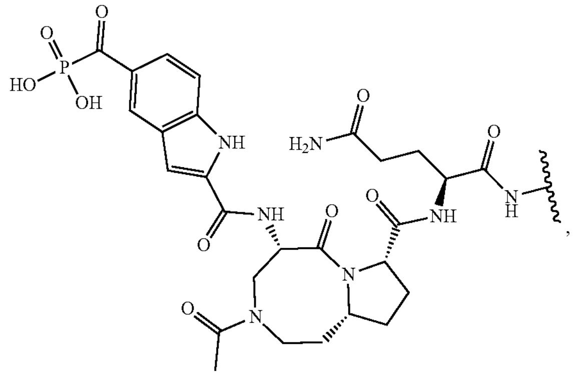 [SMILES: *NC(=O)[C@H](CCC(N)=O)NC(=O)[C@@H]1CC[C@@H]2CCN(C(C)=O)C[C@H](NC(=O)c3cc4cc(C(=O)P(=O)(O)O)ccc4[nH]3)C(=O)N21]

LBM is selected from any of those in Table A below, and L is selected from any of those in Table B below.

In some embodiments, a provided compound or pharmaceutically acceptable salt thereof, is selected from those wherein STAT is

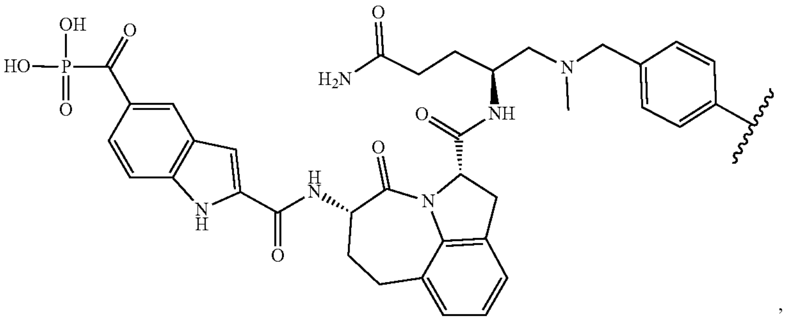 [SMILES: *c1ccc(CN(C)C[C@H](CCC(N)=O)NC(=O)[C@@H]2Cc3cccc4c3N2C(=O)[C@@H](NC(=O)c2cc3cc(C(=O)P(=O)(O)O)ccc3[nH]2)CC4)cc1]

LBM is selected from any of those in Table A below, and L is selected from any of those in Table B below.

In some embodiments, a provided compound or pharmaceutically acceptable salt thereof, is selected from those wherein STAT is

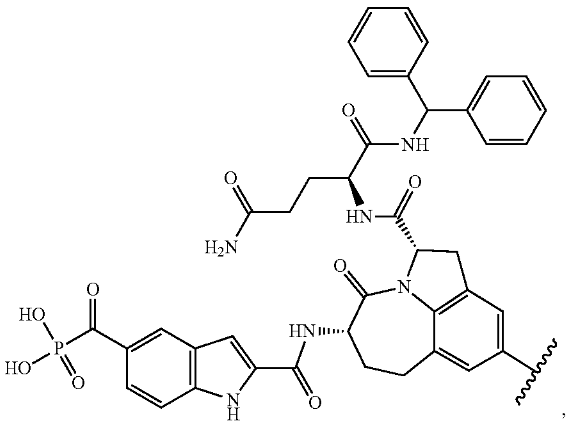 [SMILES: *c1cc2c3c(c1)C[C@@H](C(=O)N[C@@H](CCC(N)=O)C(=O)NC(c1ccccc1)c1ccccc1)N3C(=O)[C@@H](NC(=O)c1cc3cc(C(=O)P(=O)(O)O)ccc3[nH]1)CC2]

LBM is selected from any of those in Table A below, and L is selected from any of those in Table B below.

In some embodiments, a provided compound or pharmaceutically acceptable salt thereof, is selected from those wherein STAT is

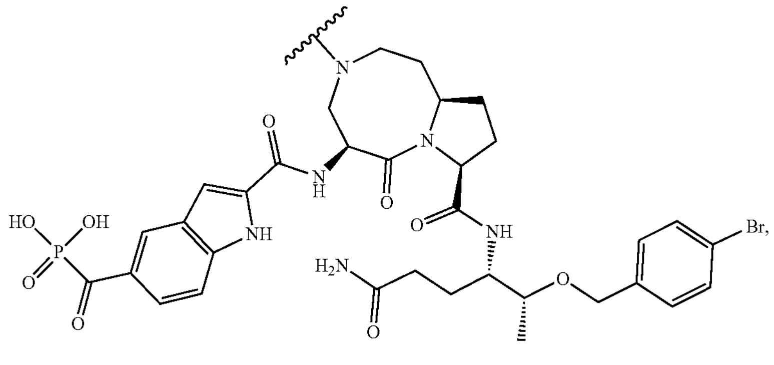 [SMILES: *N1CC[C@H]2CC[C@@H](C(=O)N[C@@H](CCC(N)=O)[C@@H](C)OCc3ccc(Br)cc3)N2C(=O)[C@@H](NC(=O)c2cc3cc(C(=O)P(=O)(O)O)ccc3[nH]2)C1]

LBM is selected from any of those in Table A below, and L is selected from any of those in Table B below.

In some embodiments, a provided compound or pharmaceutically acceptable salt thereof, is selected from those wherein STAT is

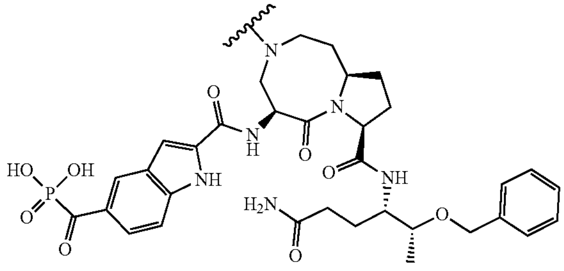
,

LBM is selected from any of those in Table A below, and L is selected from any of those in Table B below.

In some embodiments, a provided compound or pharmaceutically acceptable salt thereof, is selected from those wherein STAT is.

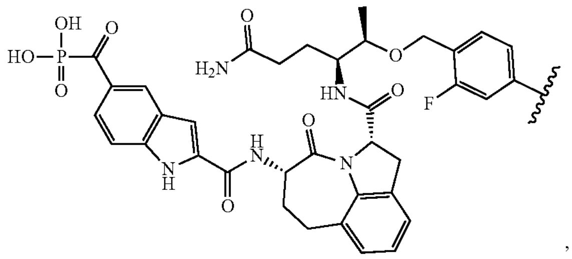 [SMILES: *c1ccc(CO[C@H](C)[C@H](CCC(N)=O)NC(=O)[C@@H]2Cc3cccc4c3N2C(=O)[C@@H](NC(=O)c2cc3cc(C(=O)P(=O)(O)O)ccc3[nH]2)CC4)c(F)c1]
,

LBM is selected from any of those in Table A below, and L is selected from any of those in Table B below.

In some embodiments, a provided compound or pharmaceutically acceptable salt thereof, is selected from those wherein STAT is

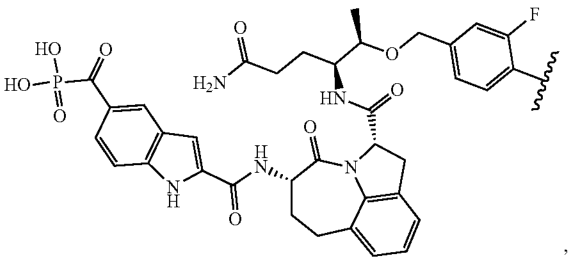 [SMILES: *c1ccc(CO[C@H](C)[C@H](CCC(N)=O)NC(=O)[C@@H]2Cc3cccc4c3N2C(=O)[C@@H](NC(=O)c2cc3cc(C(=O)P(=O)(O)O)ccc3[nH]2)CC4)cc1F]
,

LBM is selected from any of those in Table A below, and L is selected from any of those in Table B below.

In some embodiments, a provided compound or pharmaceutically acceptable salt thereof, is selected from those wherein STAT is

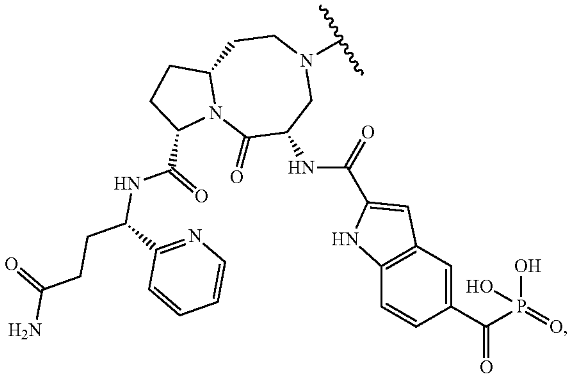 [SMILES: *N1CC[C@H]2CC[C@@H](C(=O)N[C@@H](CCC(N)=O)c3ccccn3)N2C(=O)[C@@H](NC(=O)c2cc3cc(C(=O)P(=O)(O)O)ccc3[nH]2)C1]

LBM is selected from any of those in Table A below, and L is selected from any of those in Table B below.

In some embodiments, a provided compound or pharmaceutically acceptable salt thereof, is selected from those wherein STAT is

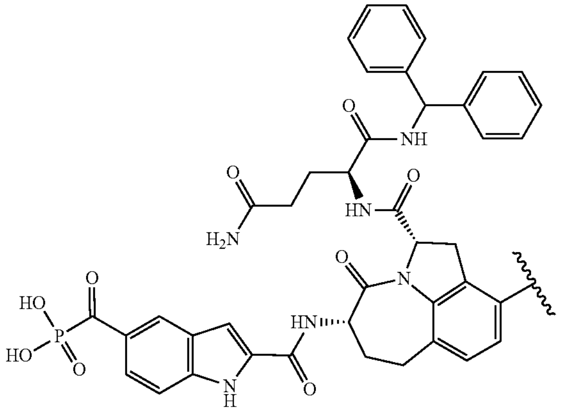

,

LBM is selected from any of those in Table A below, and L is selected from any of those in Table B below.

In some embodiments, a provided compound or pharmaceutically acceptable salt thereof, is selected from those wherein STAT is

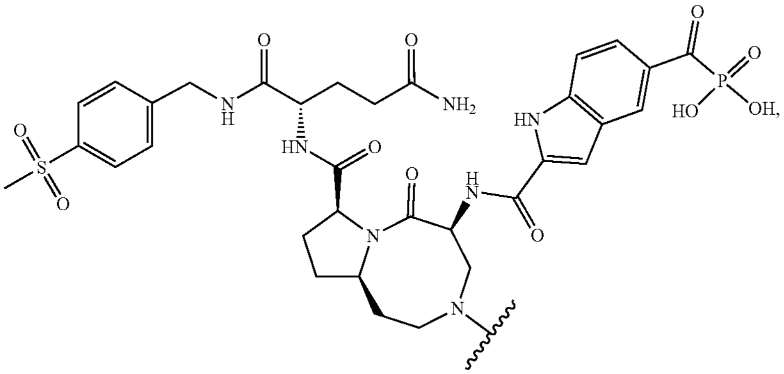 [SMILES: *N1CC[C@H]2CC[C@@H](C(=O)N[C@@H](CCC(N)=O)C(=O)NCc3ccc(S(C)(=O)=O)cc3)N2C(=O)[C@@H](NC(=O)c2cc3cc(C(=O)P(=O)(O)O)ccc3[nH]2)C1]

LBM is selected from any of those in Table A below, and L is selected from any of those in Table B below.

In some embodiments, a provided compound or pharmaceutically acceptable salt thereof, is selected from those wherein STAT is

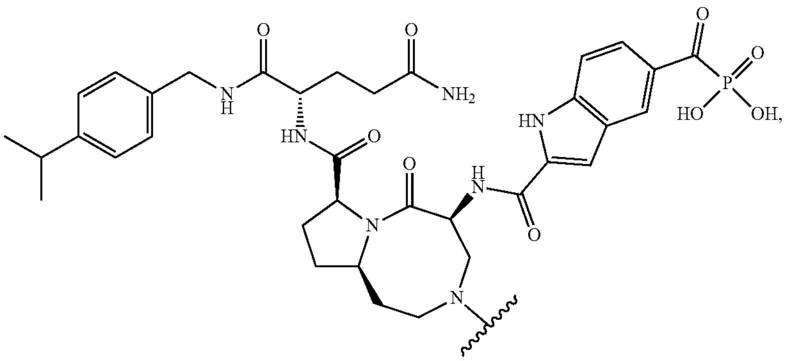 [SMILES: *N1CC[C@H]2CC[C@@H](C(=O)N[C@@H](CCC(N)=O)C(=O)NCc3ccc(C(C)C)cc3)N2C(=O)[C@@H](NC(=O)c2cc3cc(C(=O)P(=O)(O)O)ccc3[nH]2)C1]

LBM is selected from any of those in Table A below, and L is selected from any of those in Table B below.

In some embodiments, a provided compound or pharmaceutically acceptable salt thereof, is selected from those wherein STAT is

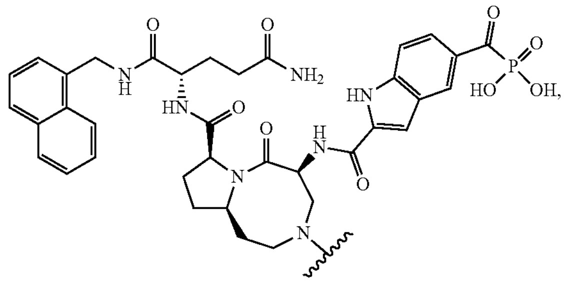 [SMILES: *N1CC[C@H]2CC[C@@H](C(=O)N[C@@H](CCC(N)=O)C(=O)NCc3cccc4ccccc34)N2C(=O)[C@@H](NC(=O)c2cc3cc(C(=O)P(=O)(O)O)ccc3[nH]2)C1]

LBM is selected from any of those in Table A below, and L is selected from any of those in Table B below.

In some embodiments, a provided compound or pharmaceutically acceptable salt thereof, is selected from those wherein STAT is

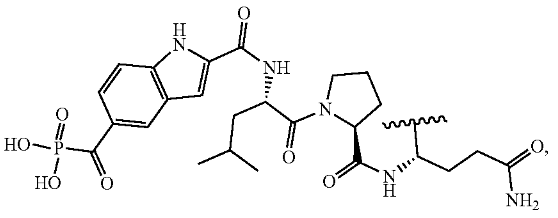

LBM is selected from any of those in Table A below, and L is selected from any of those in Table B below.

In some embodiments, a provided compound or pharmaceutically acceptable salt thereof, is selected from those wherein STAT is

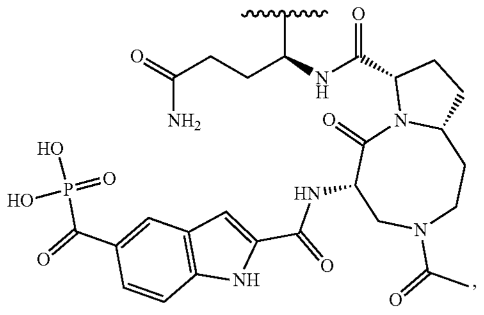 [SMILES: *[C@H](CCC(N)=O)NC(=O)[C@@H]1CC[C@@H]2CCN(C(C)=O)C[C@H](NC(=O)c3cc4cc(C(=O)P(=O)(O)O)ccc4[nH]3)C(=O)N21]

LBM is selected from any of those in Table A below, and L is selected from any of those in Table B below.

In some embodiments, a provided compound or pharmaceutically acceptable salt thereof, is selected from those wherein STAT is

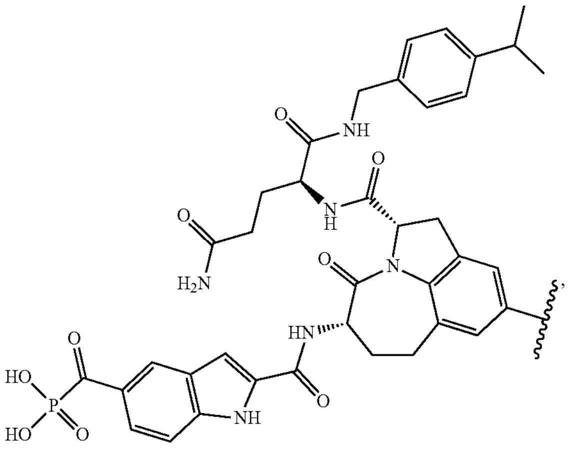 [SMILES: *c1cc2c3c(c1)C[C@@H](C(=O)N[C@@H](CCC(N)=O)C(=O)NCc1ccc(C(C)C)cc1)N3C(=O)[C@@H](NC(=O)c1cc3cc(C(=O)P(=O)(O)O)ccc3[nH]1)CC2]

LBM is selected from any of those in Table A below, and L is selected from any of those in Table B below.

In some embodiments, a provided compound or pharmaceutically acceptable salt thereof, is selected from those wherein STAT is

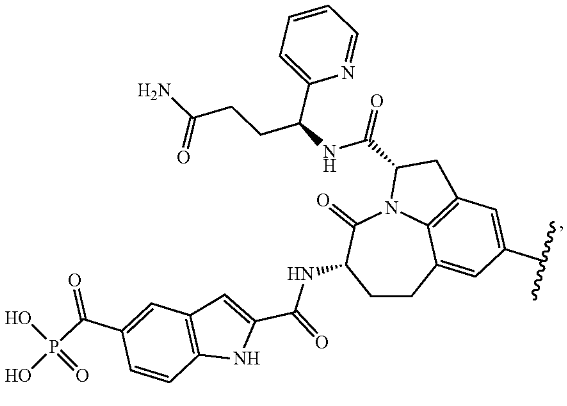 [SMILES: *c1cc2c3c(c1)C[C@@H](C(=O)N[C@@H](CCC(N)=O)c1ccccn1)N3C(=O)[C@@H](NC(=O)c1cc3cc(C(=O)P(=O)(O)O)ccc3[nH]1)CC2]

LBM is selected from any of those in Table A below, and L is selected from any of those in Table B below.

In some embodiments, a provided compound or pharmaceutically acceptable salt thereof, is selected from those wherein STAT is

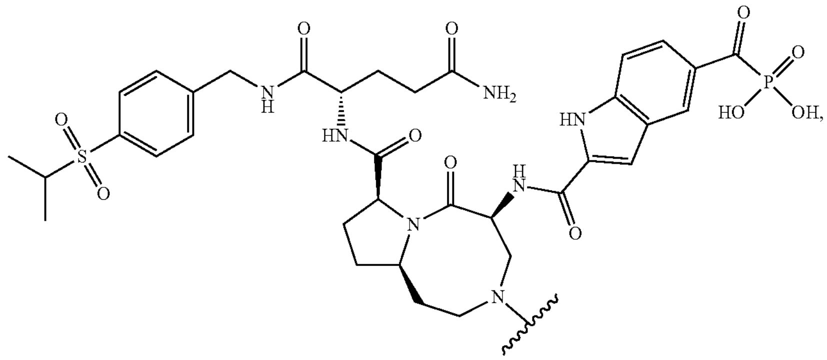 [SMILES: *N1CC[C@H]2CC[C@@H](C(=O)N[C@@H](CCC(N)=O)C(=O)NCc3ccc(S(=O)(=O)C(C)C)cc3)N2C(=O)[C@@H](NC(=O)c2cc3cc(C(=O)P(=O)(O)O)ccc3[nH]2)C1]
LBM is selected from any of those in Table A below, and L is selected from any of those in Table B below.
Table A. Exemplified E3 Ligase Binding Moiety (LBM)
(a)
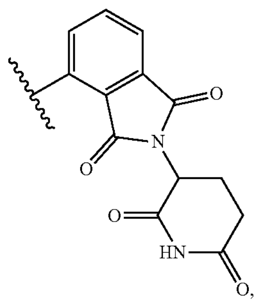
(b)
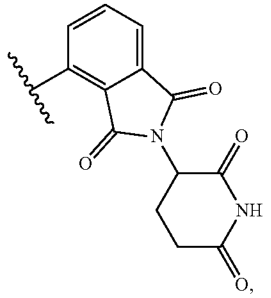
(c)
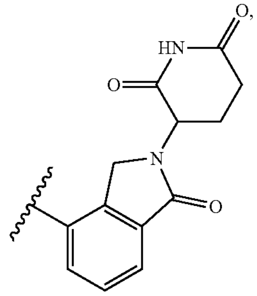
-continued
(d)
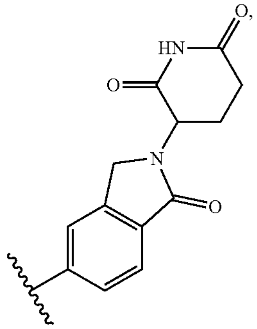
(e)
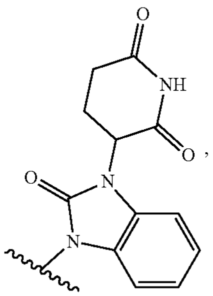
(f)
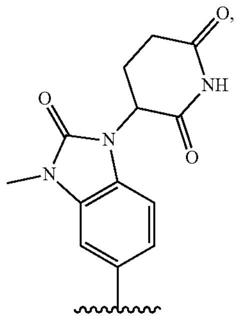

-continued
(g)
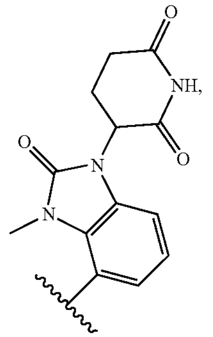
(h)
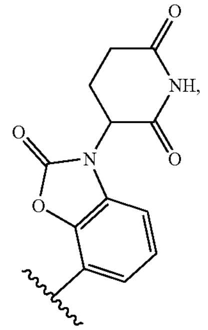
(i)
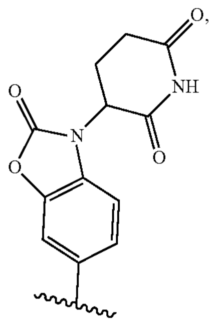
(j)
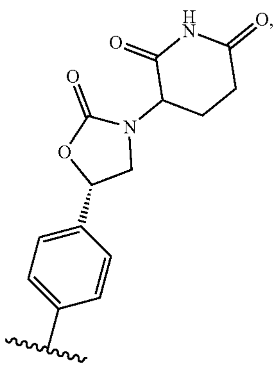
-continued
(k)
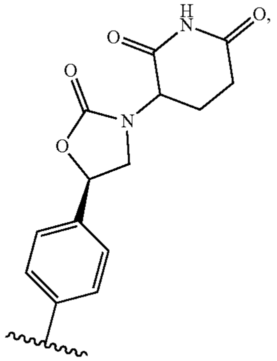
(l)
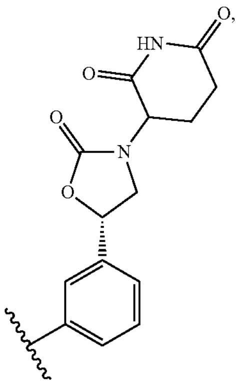
(m)
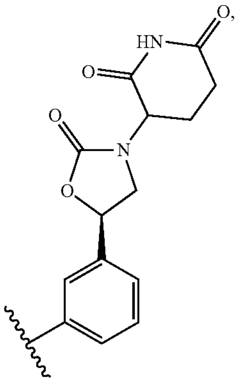
(n)
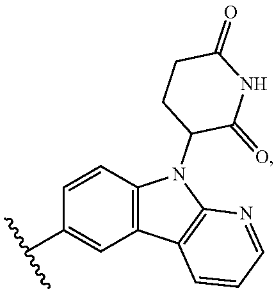

-continued
(o)
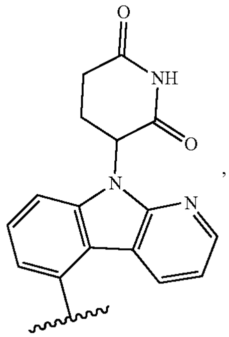
,
(p)
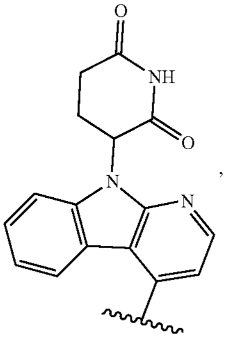
,
(q)
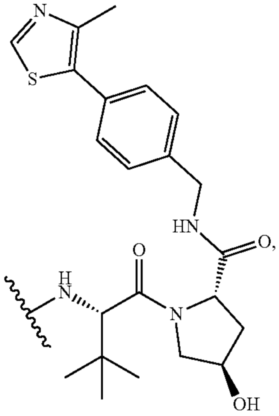
(n)
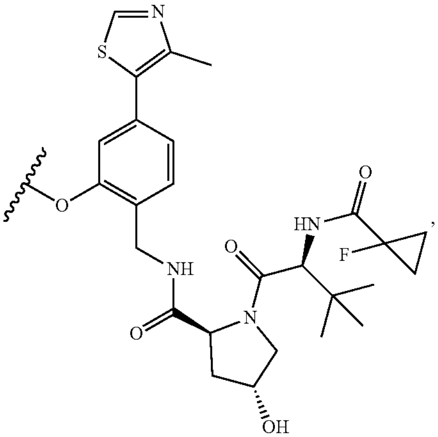
-continued
(o)
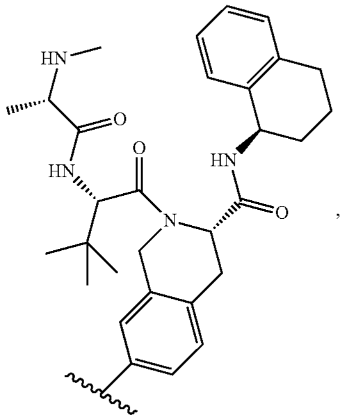
,
(p)
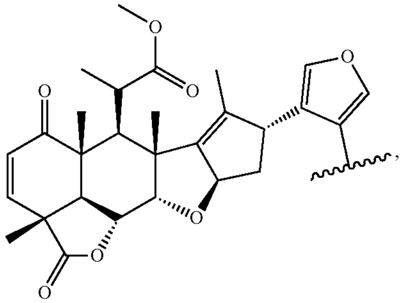
(q)
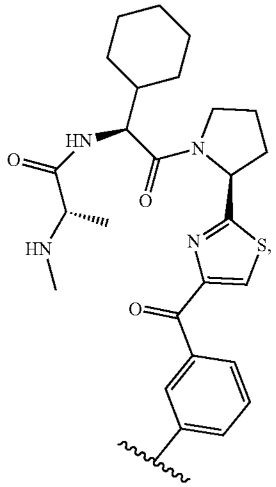
(r)
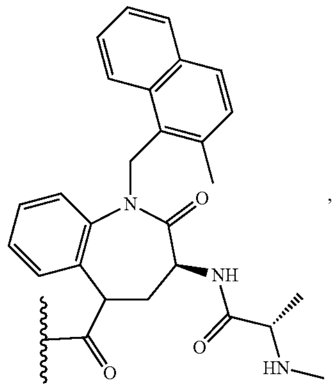
, -continued
(s)
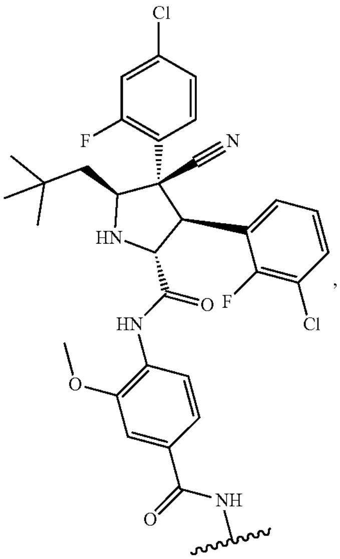
,
(t)
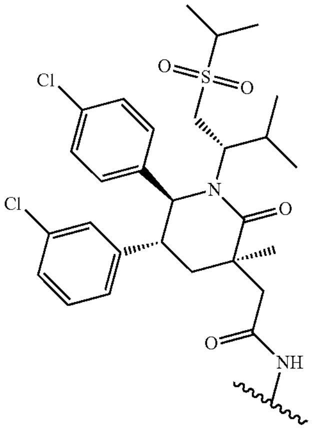
(u)
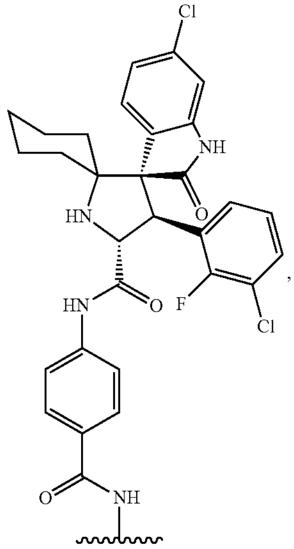
,
-continued
(v)
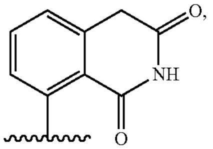
(w)
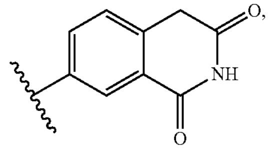
(x)
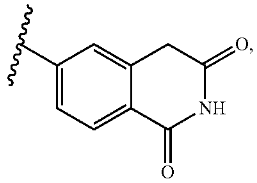
(y)
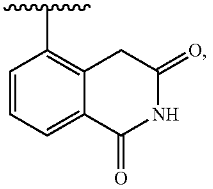
(z)
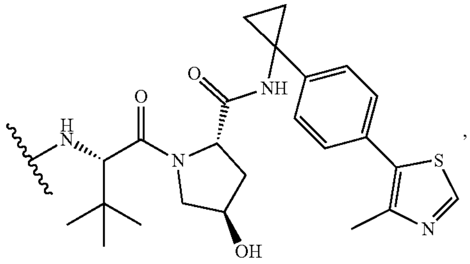
,
(aa)
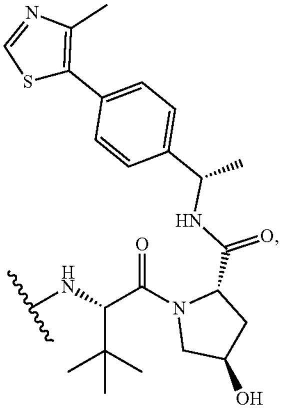
(bb)
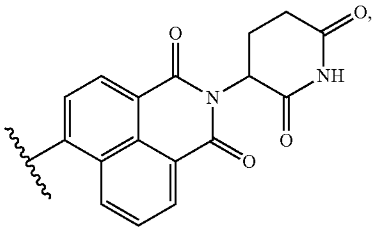

-continued
(cc)
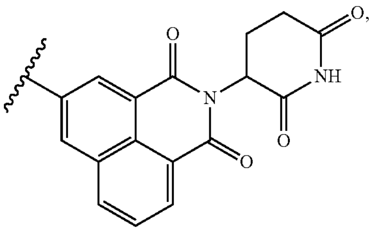
(dd)
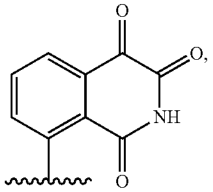
(ee)
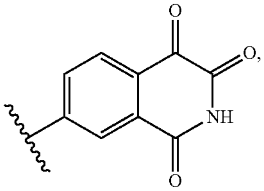
(ff)
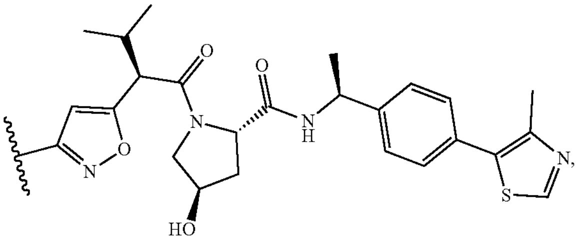
(gg)
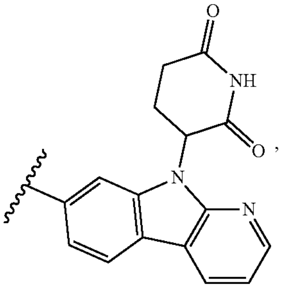
,
(hh)
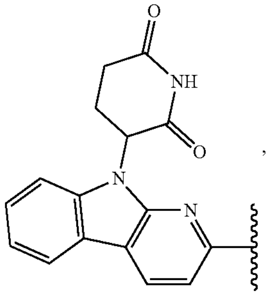
,
-continued
(ii)
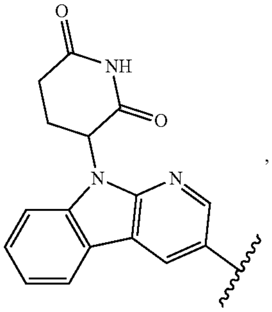
,
(jj)
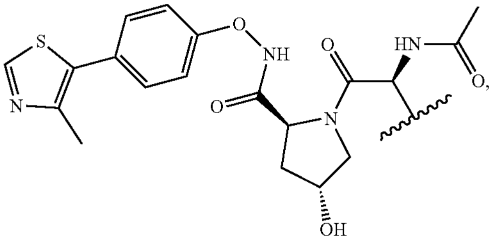
(kk)
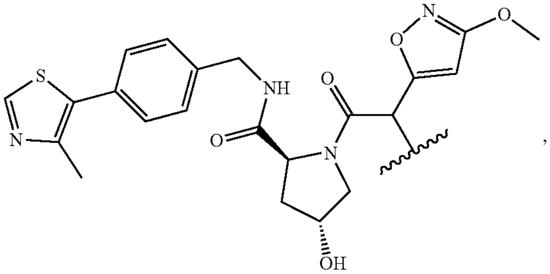
,
(ll)
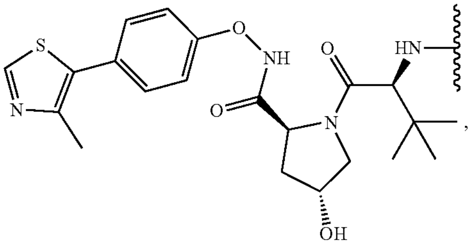
(mm)
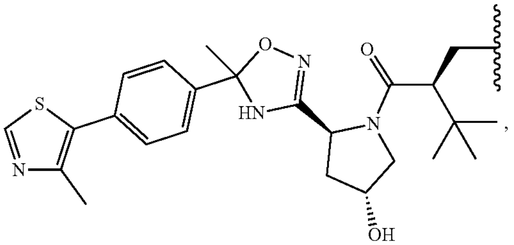

-continued
(nn)
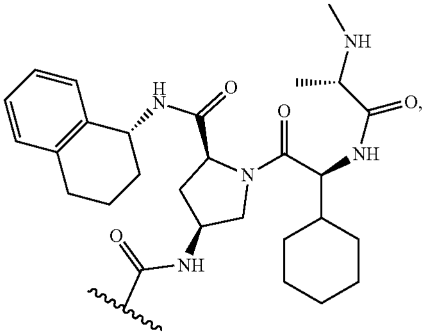
(oo)
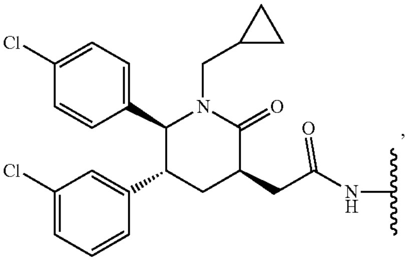
(pp)
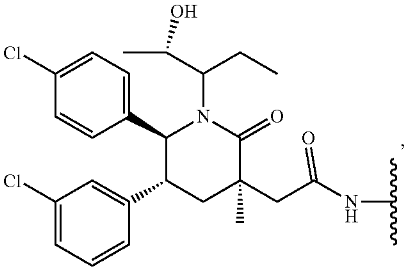
(qq)
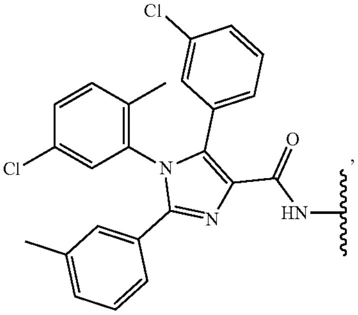
(rr)
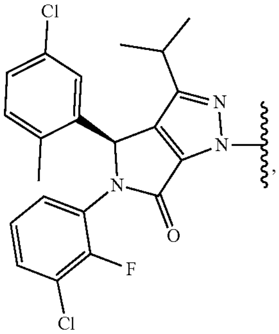
-continued
(ss)
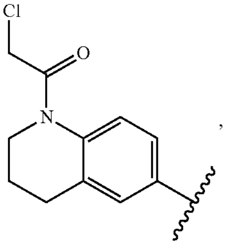
(tt)
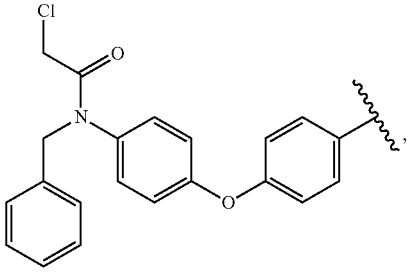
(uu)
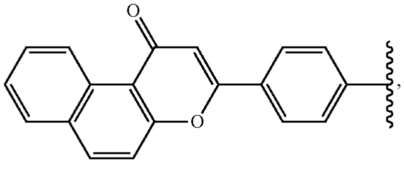
(vv)
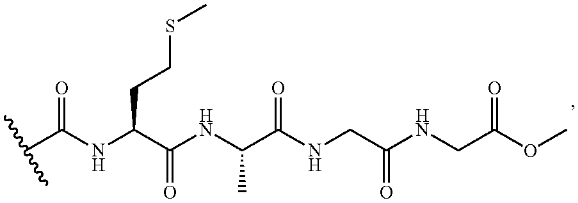
(ww)
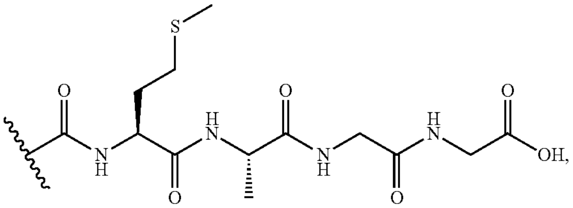
(xx)
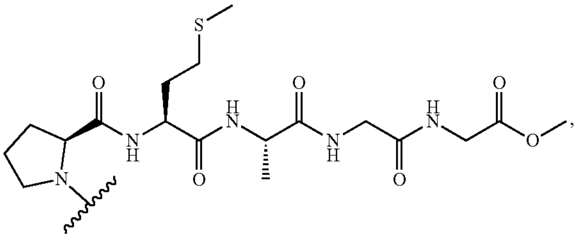

-continued
(yy)
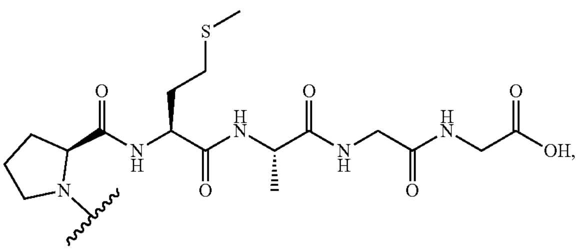
-continued
(zz)
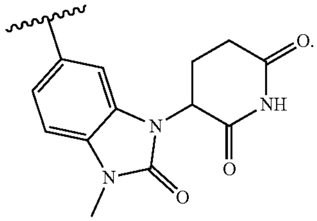
Table B. Exemplified Linkers (L)
(1)
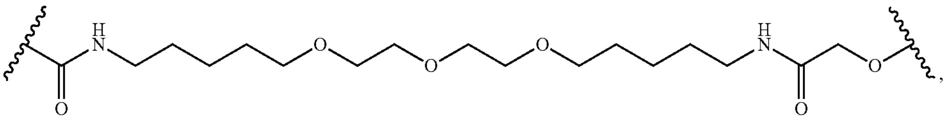
(2)
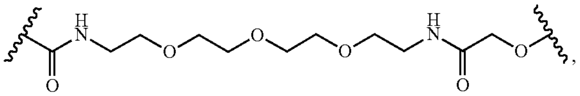
(3)
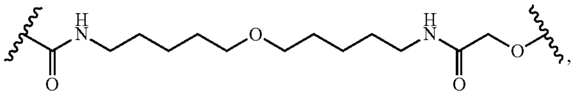
(4)
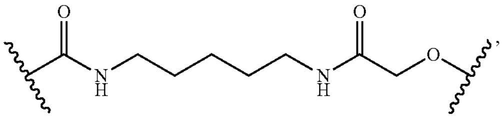
(5)
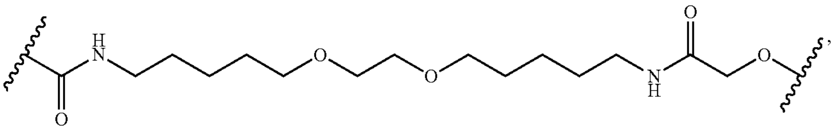
(6)
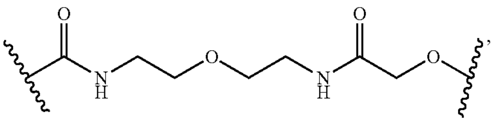
(7)
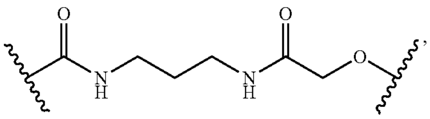
(8)
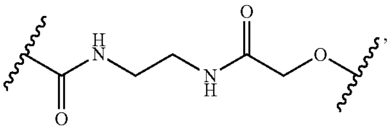
(9)
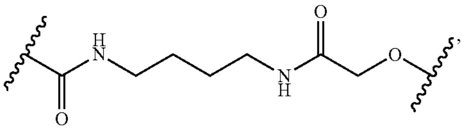
(10)
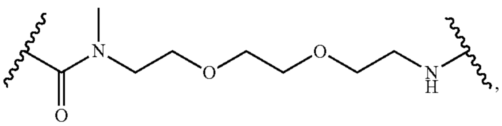
(11)
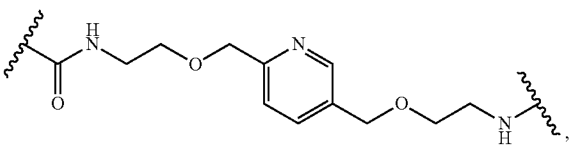
(12)
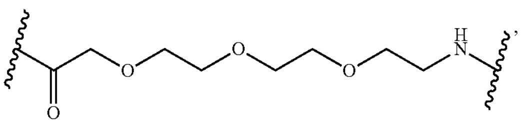
(13)
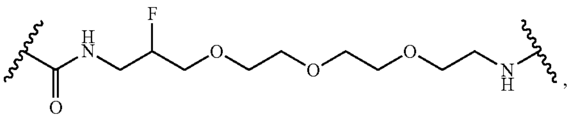

-continued
(14)
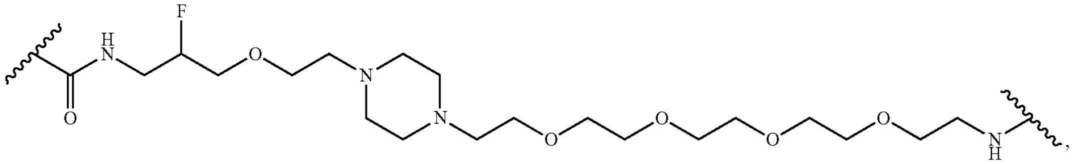
(15)
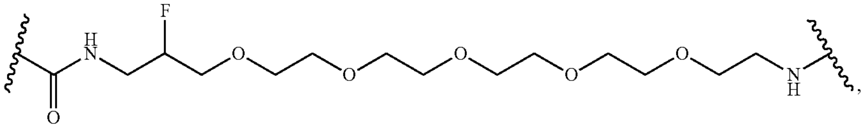
(16)
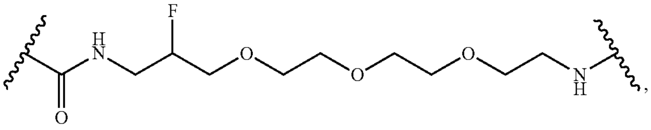
(17)
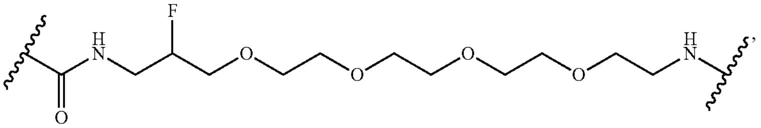
(18)
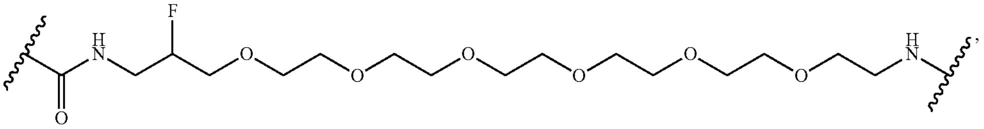
(19)
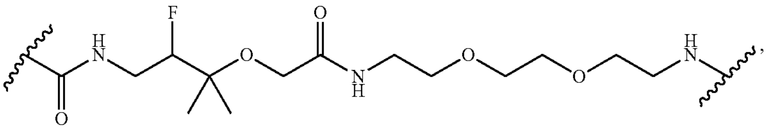
(20)
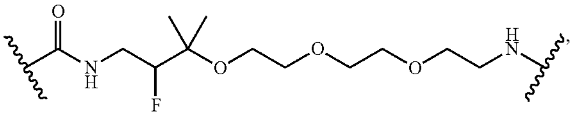
(21)
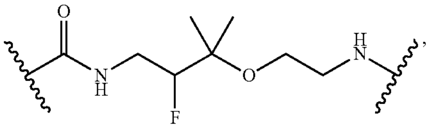
(22)
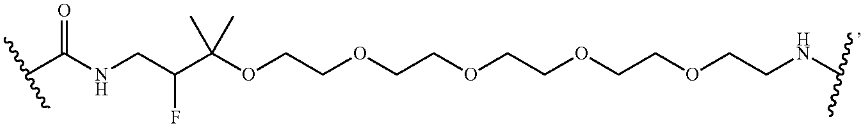
(23)
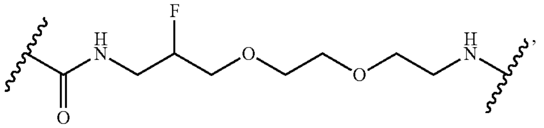
(24)
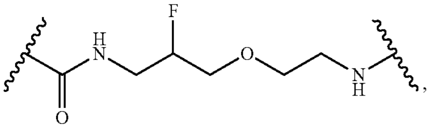
(25)
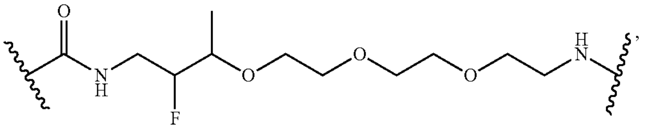
(26)
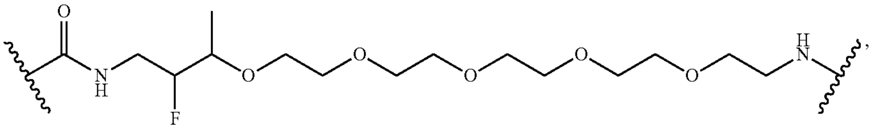

-continued
(27)
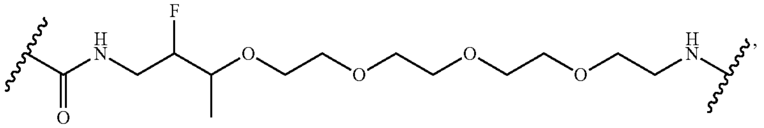
(28)
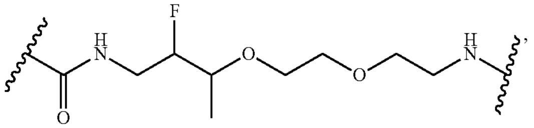
(29)
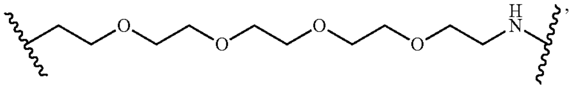
(30)
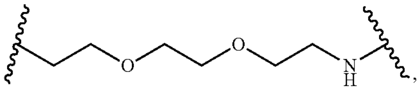
(31)
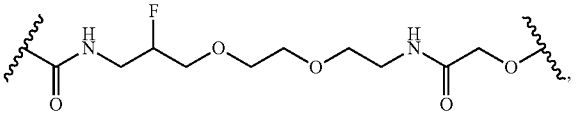
(32)
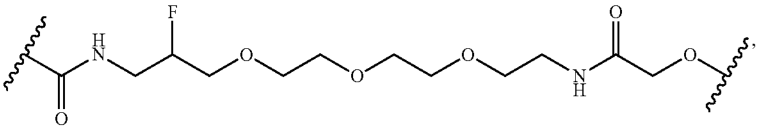
(33)
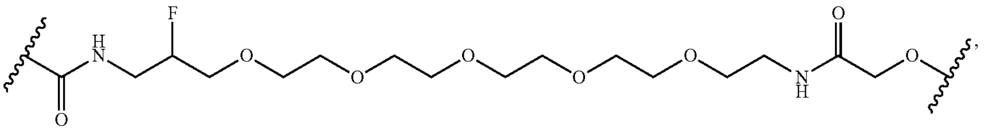
(34)
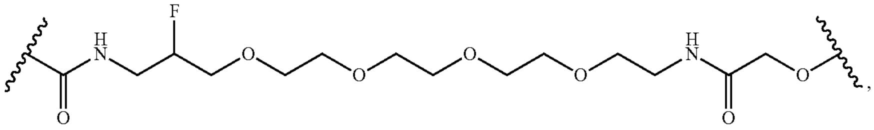
(35)
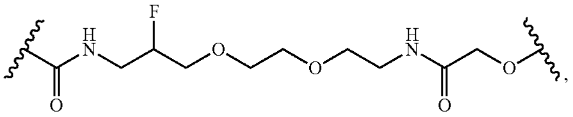
(36)
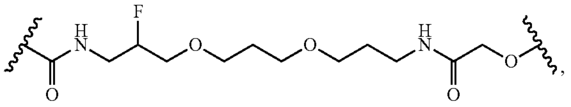
(37)
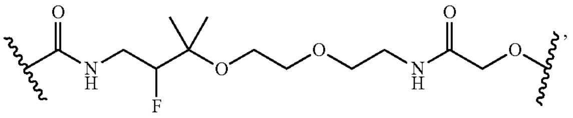
(38)
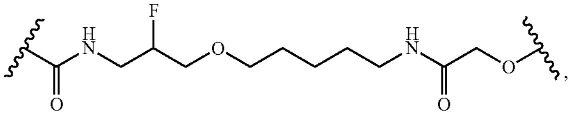
(39)
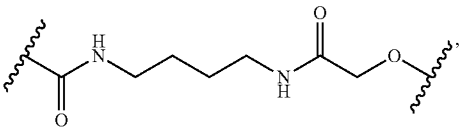
(40)
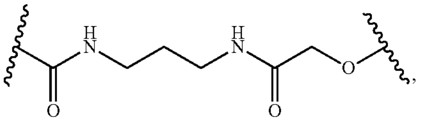
(41)
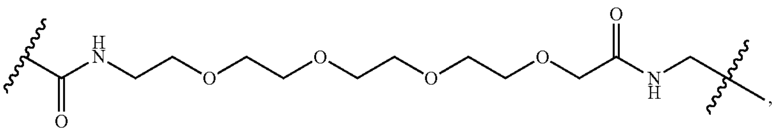
(42)
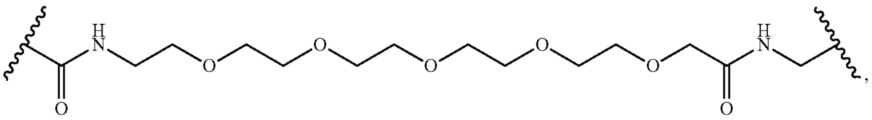

-continued
(43)
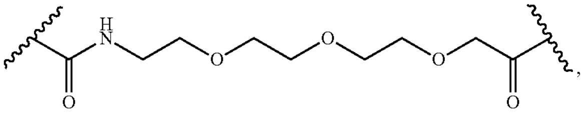
(44)
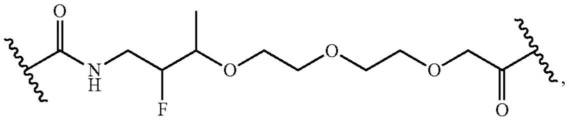
(45)
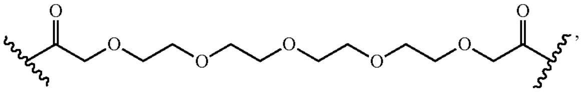
(46)
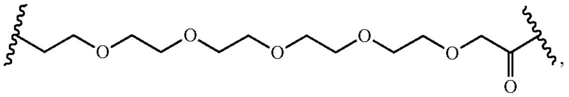
(47)
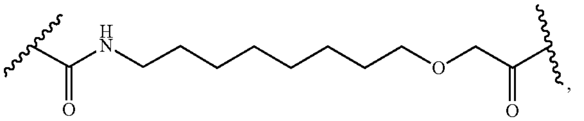
(49)
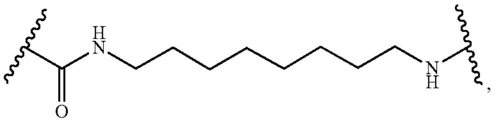
(50)
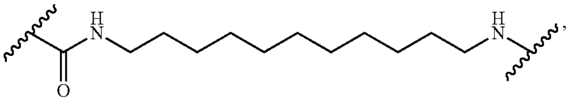
(51)
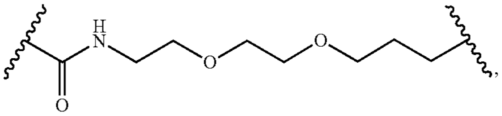
(52)
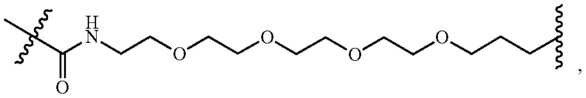
(53)
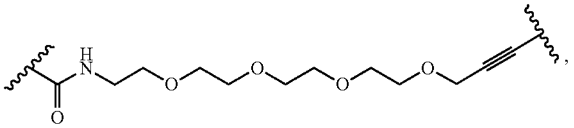
(54)
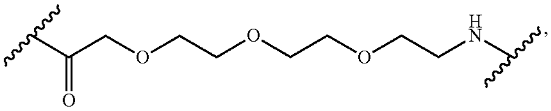
(55)
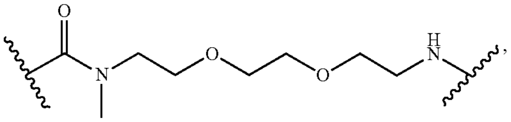
(56)
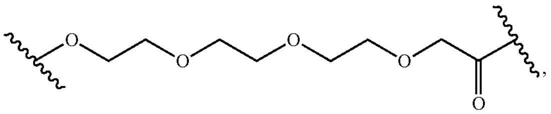
(57)
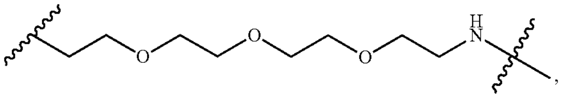
(58)
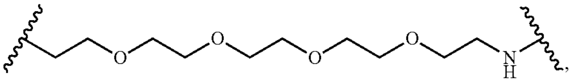
(59)
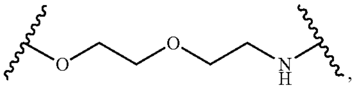
(60)
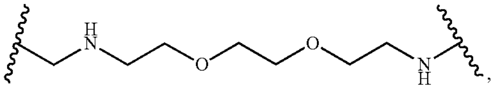
(61)
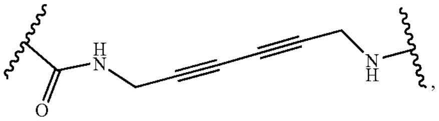
(62)
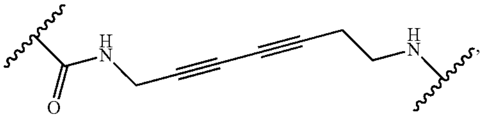
(63)
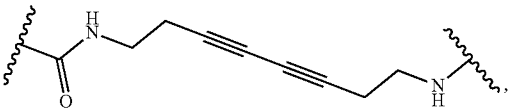
(64)
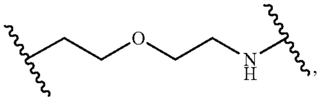
(65)
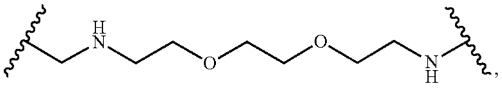

-continued
(66)
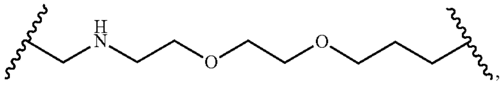
(67)
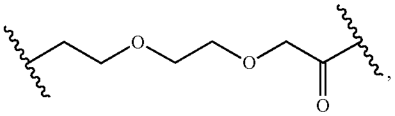
(68)
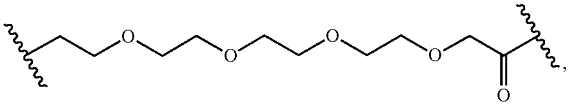
(69)
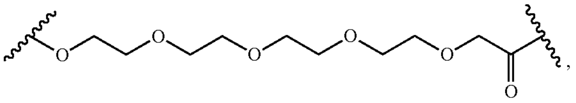
(70)
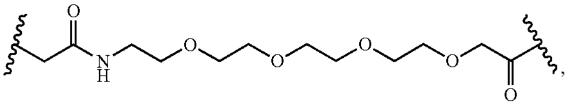
(71)
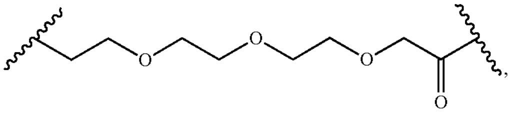
(72)
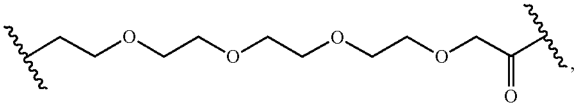
(73)
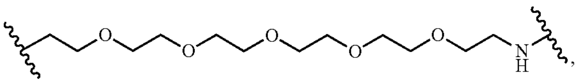
(74)
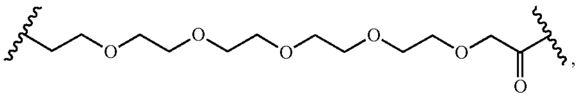
(75)
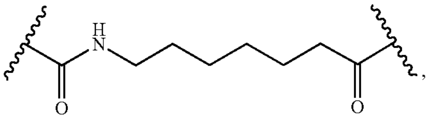
(76)
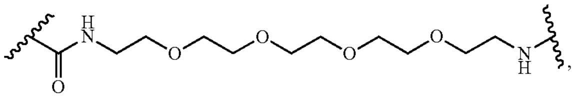
(77)
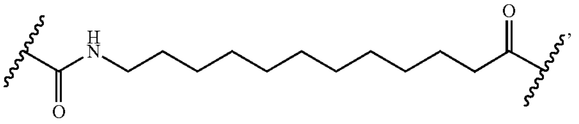
(78)
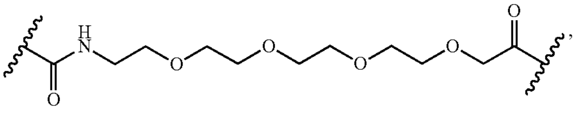
(79)
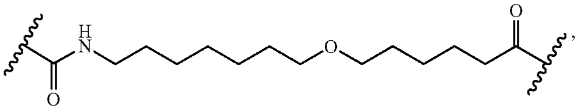
(80)
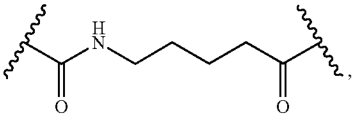
(81)
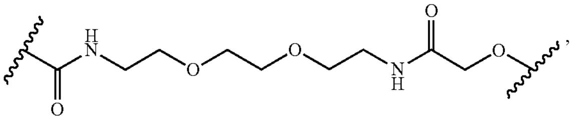
(82)
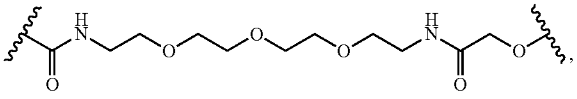
(83)
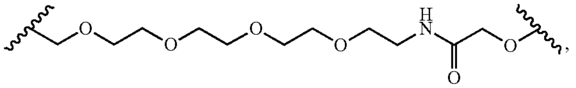
(84)
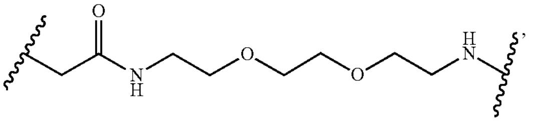
(85)
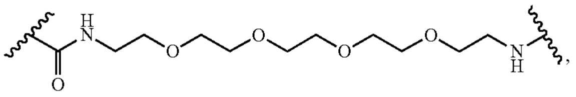
(86)
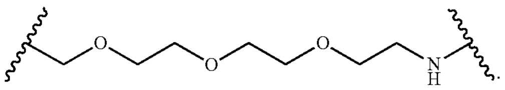
(87)
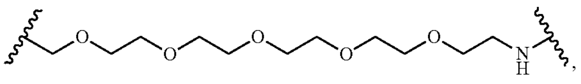

-continued
(88)
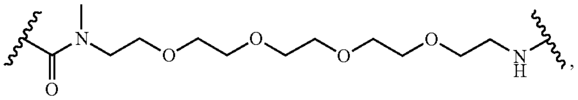
(89)
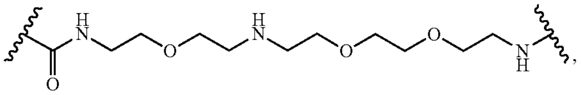
(90)
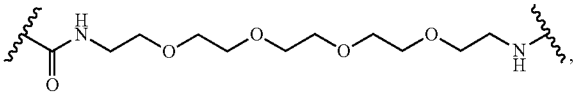
(91)
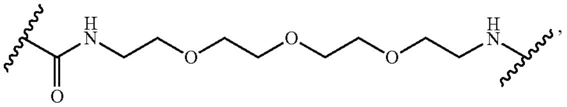
(92)
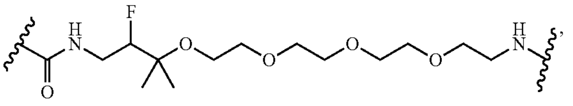
(93)
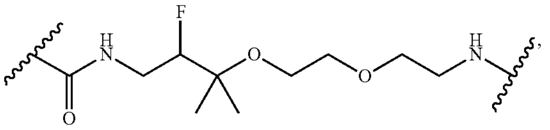
(94)
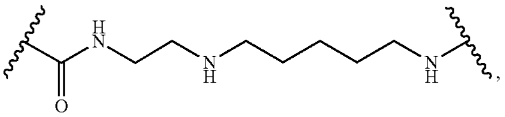
(95)
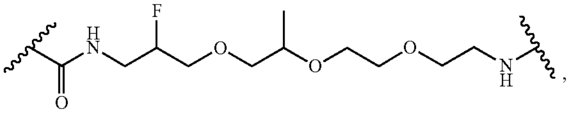
(96)
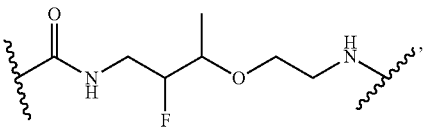
(97)
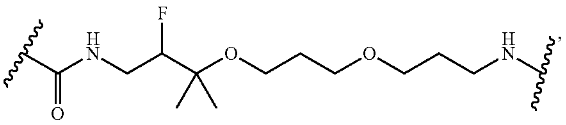
(98)
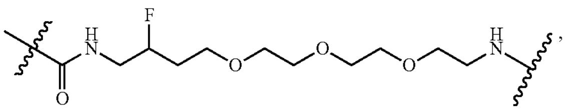
(99)
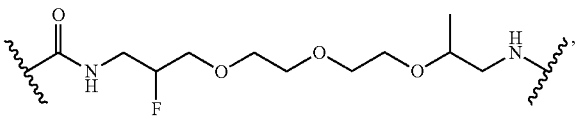
(100)
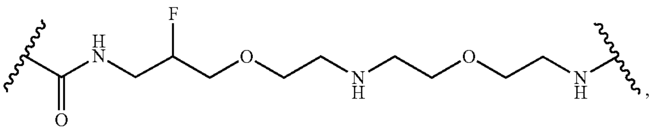
(101)
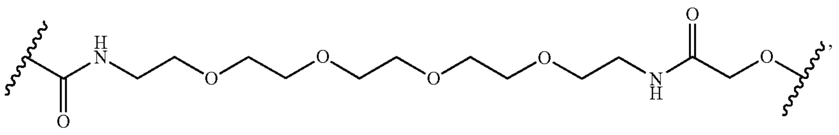
(102)
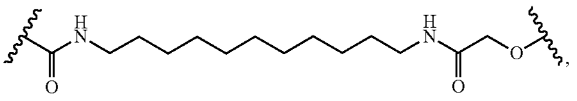
(103)
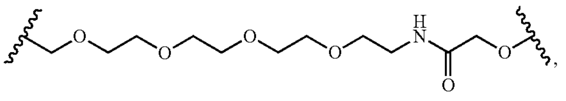
(104)
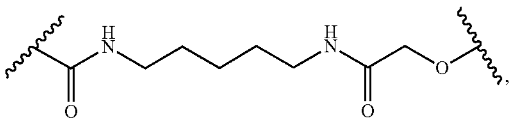
(105)
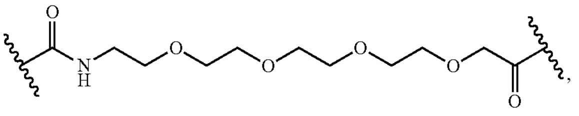
(106)
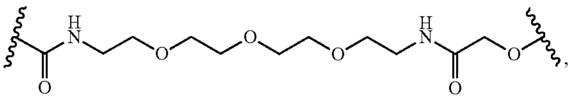
(107)
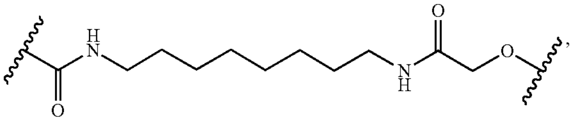

-continued
(108)
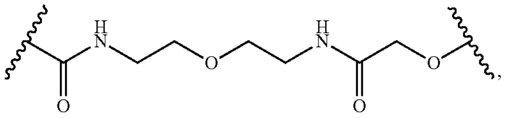
(109)
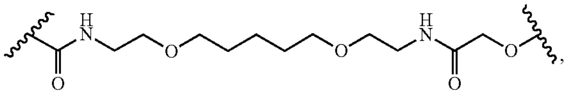
(110)
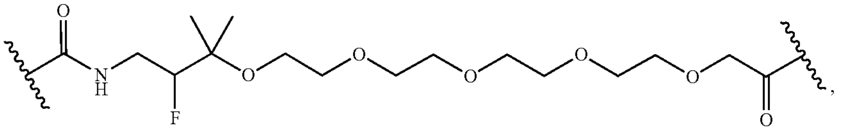
(111)
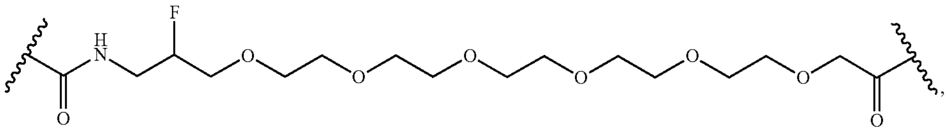
(112)
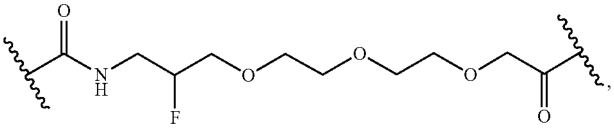
(113)
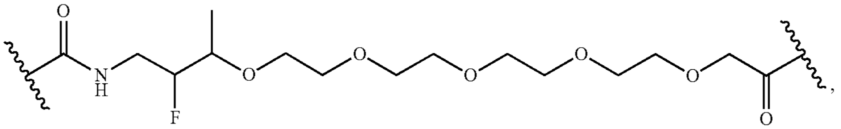
(114)
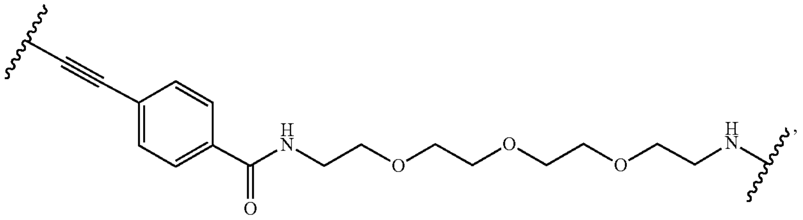
(115)
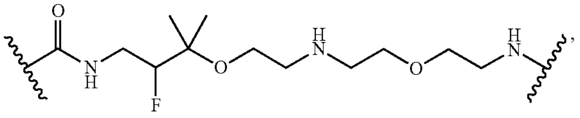
(116)
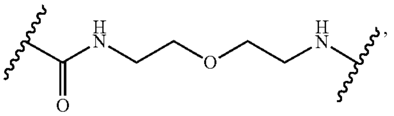
(117)
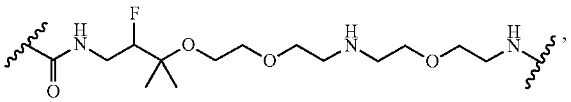
(118)
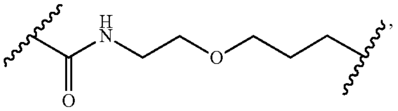
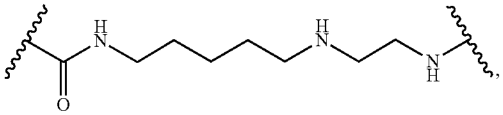
(119)
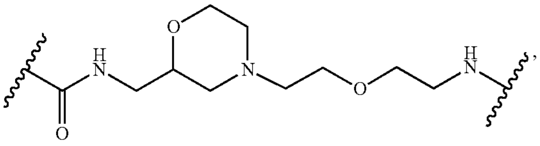
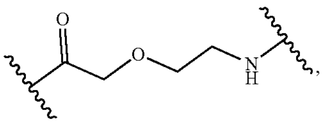
(120)
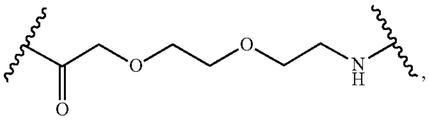

-continued
(121)
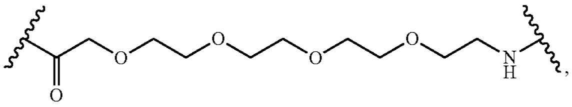
(122)
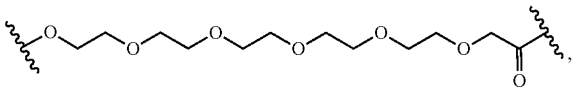
(123)
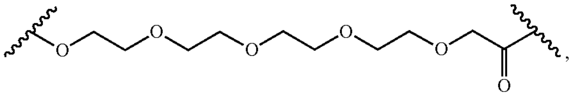
(124)
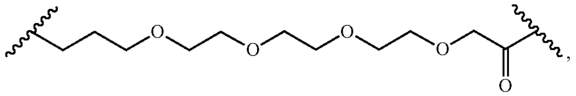
(125)
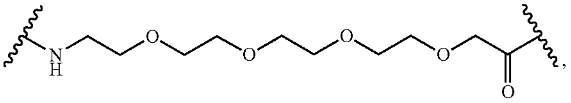
(126)
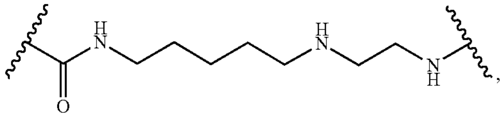
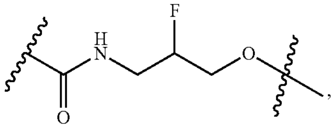
(127)
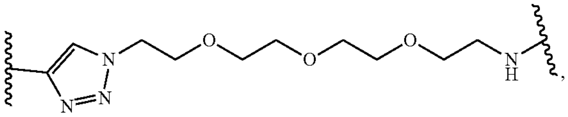
(128)
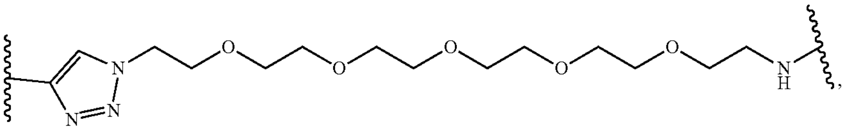
(129)
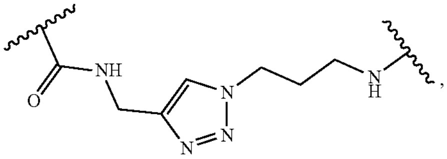
(130)
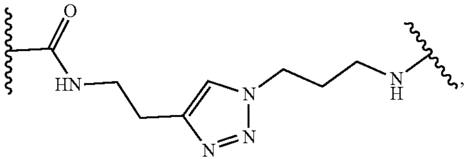
(131)
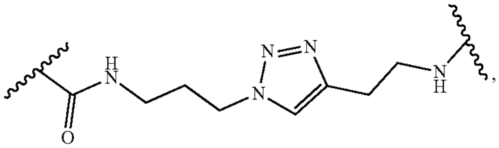
(132)
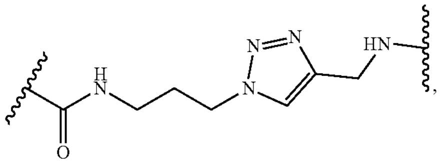
(133)
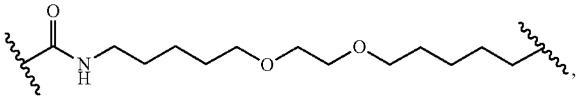
(134)
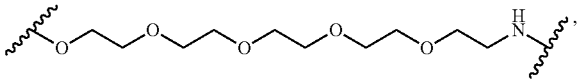
(135)
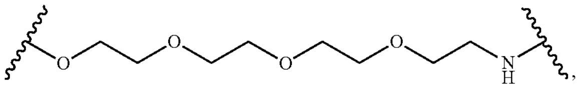
(136)
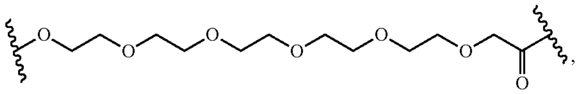
(137)
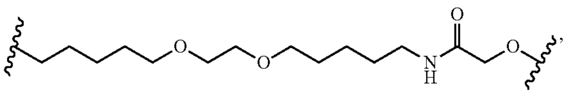
(138)
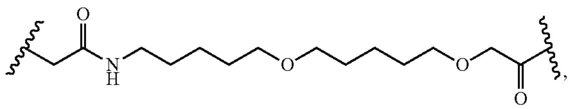
(139)
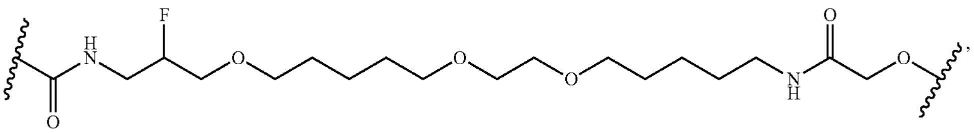

-continued
(140)
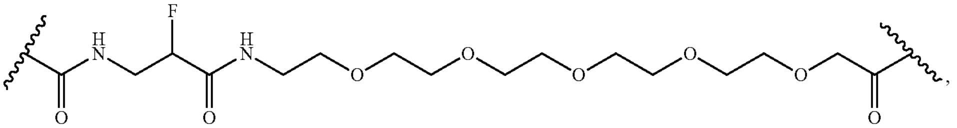
(141)
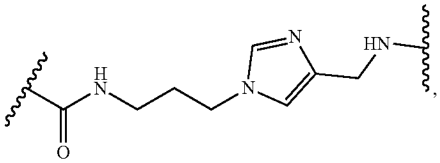
(142)
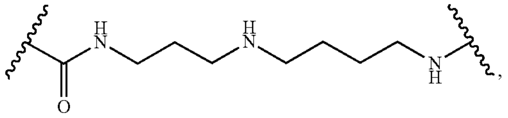
(143)
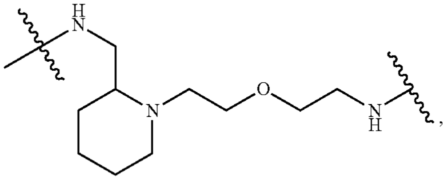
(144)
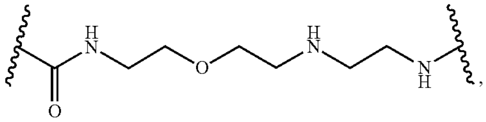
(145)
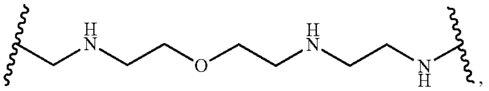
(146)
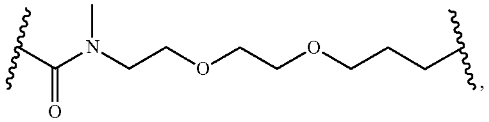
(147)
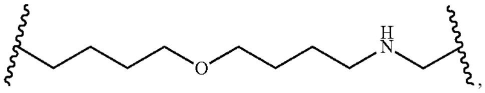
(148)
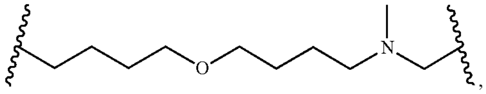
(149)
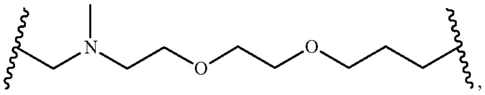
(150)
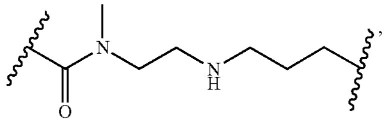
(151)
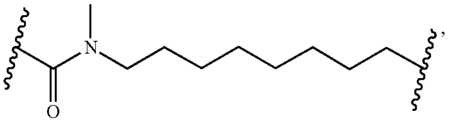
(152)
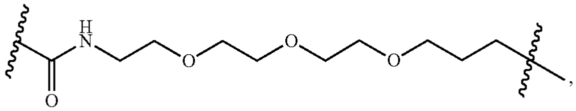
(153)
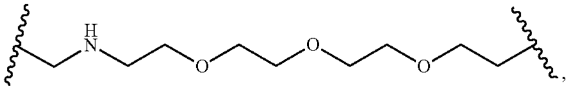
(154)
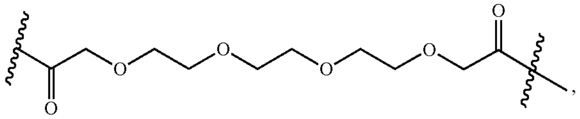
(155)
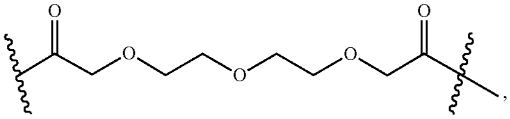
(156)
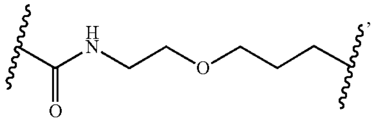
(157)
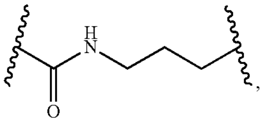
(158)
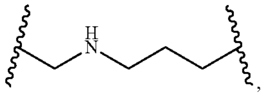
(159)
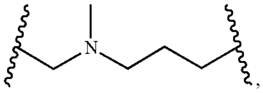
(160)
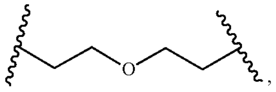

-continued
(161)
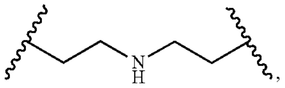
(162)
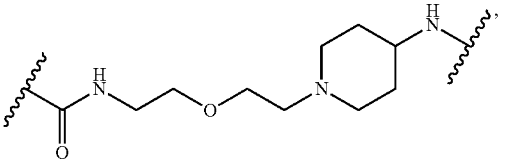
(163)
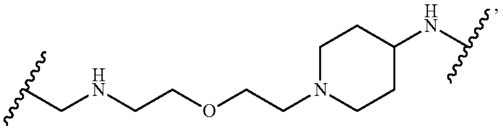
(164)
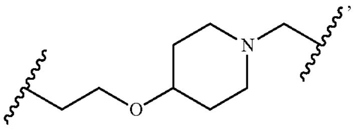
(165)
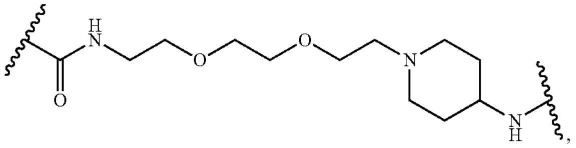
(166)
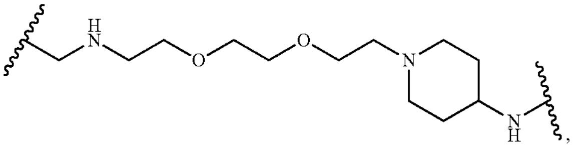
(167)
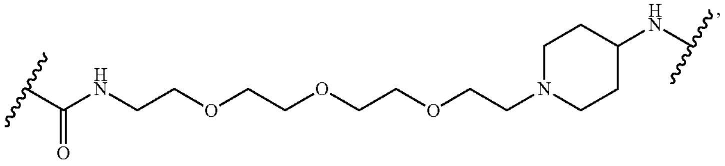
(168)
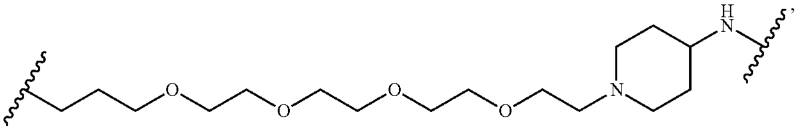
(169)
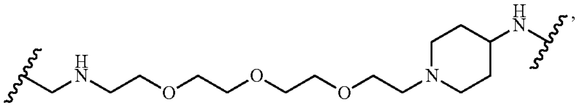
(170)
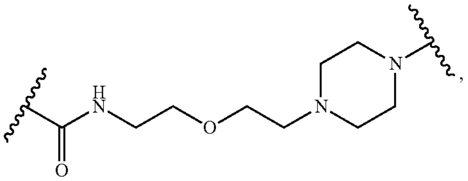
(171)
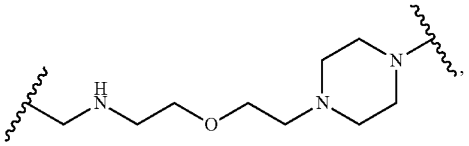
(172)
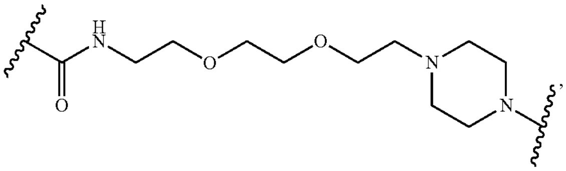
(173)
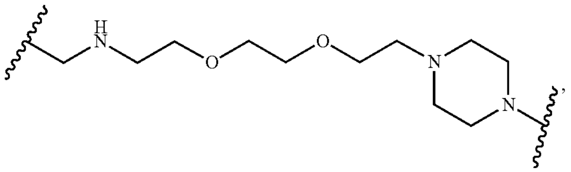
(174)
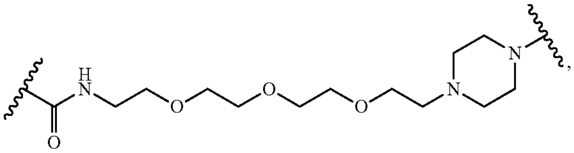
(175)
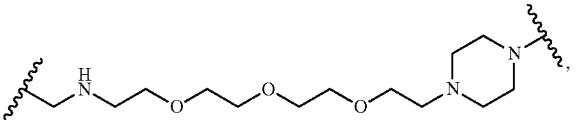
(176)
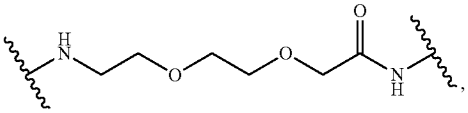

-continued
(177)
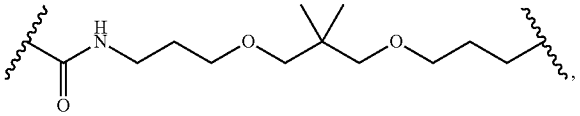
(178)
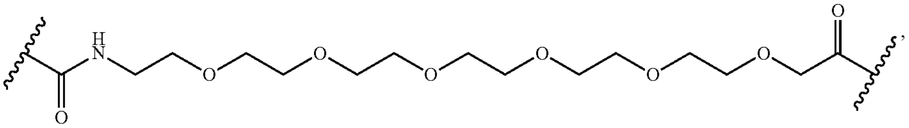
(179)
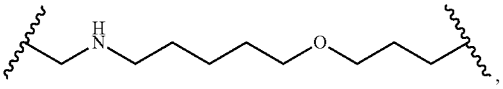
(180)
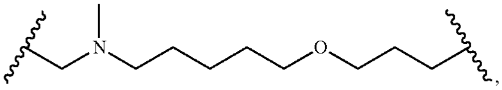
(181)
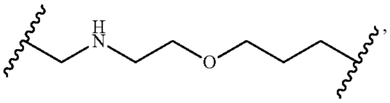
(182)
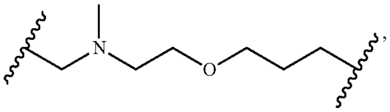
(183)
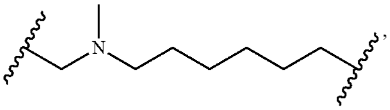
(184)
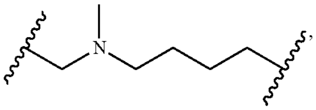
(185)
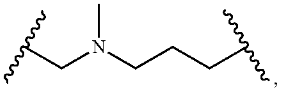
(186)
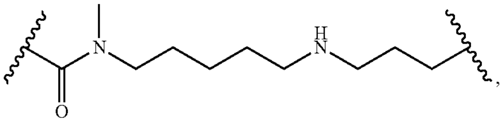
(187)
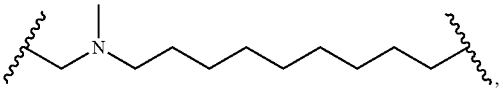
(188)
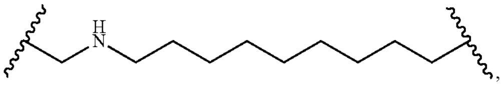
(189)
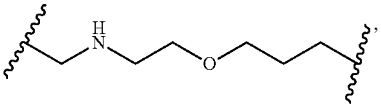
(190)
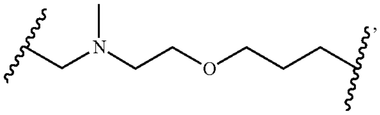
(191)
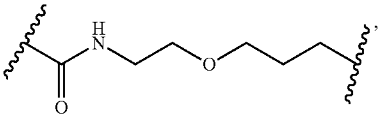
(192)
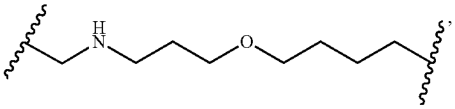
(193)
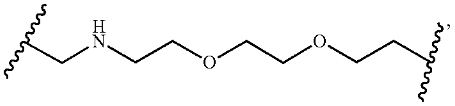
(194)
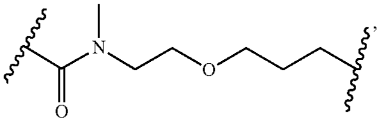
(195)
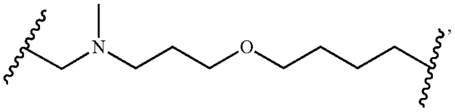
(196)
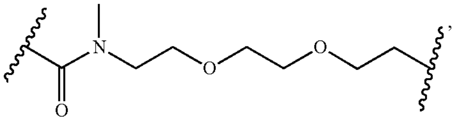
(197)
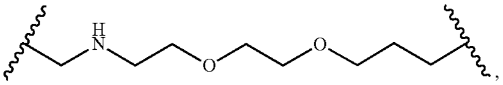
(198)
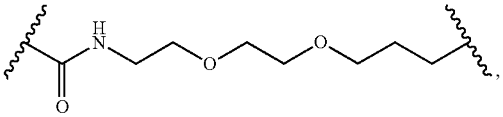

-continued
(199)
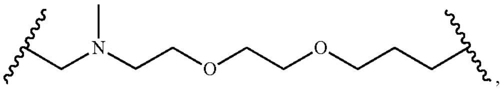
(200)
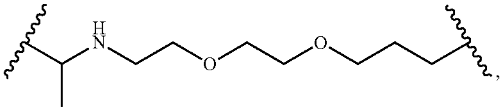
(201)
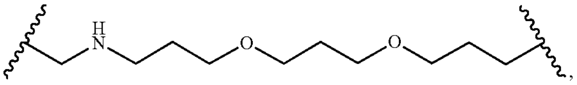
(202)
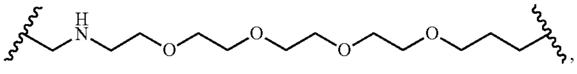
(203)
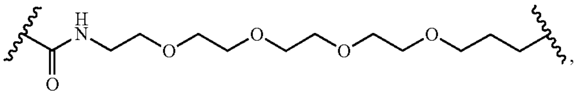
(204)
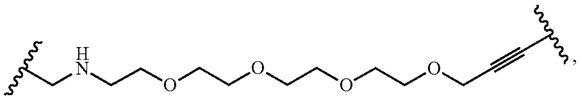
(205)
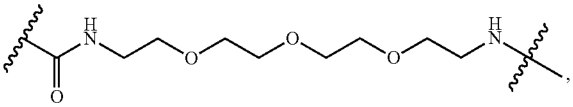
(206)
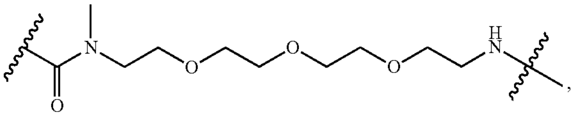
(207)
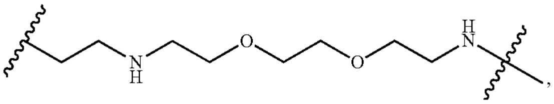
(208)
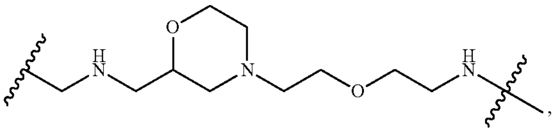
(209)
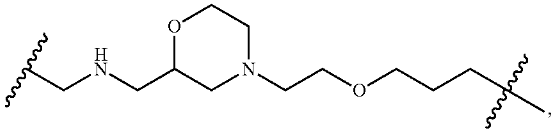
(210)
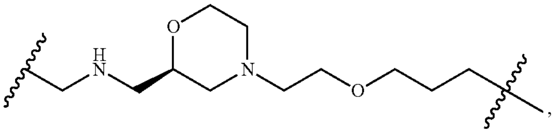
(211)
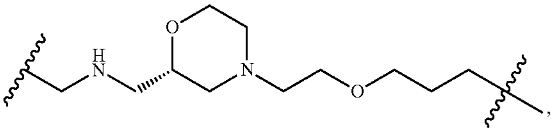
(212)
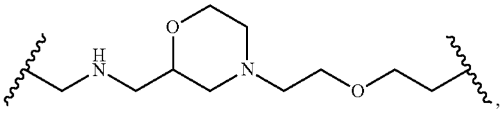
(213)
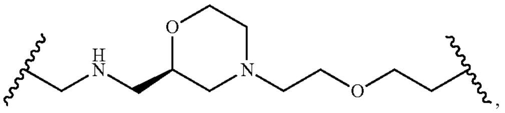
(214)
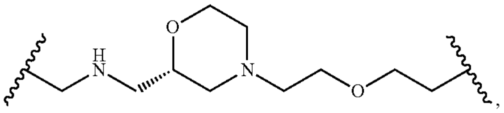
(215)
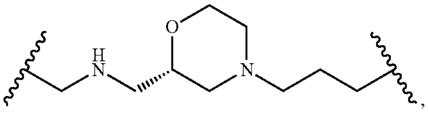
(216)
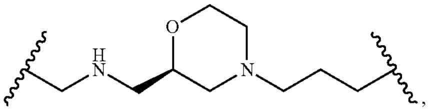
(217)
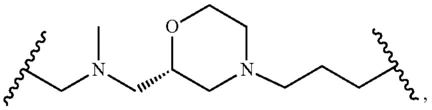
(218)
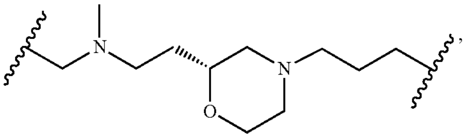
(219)
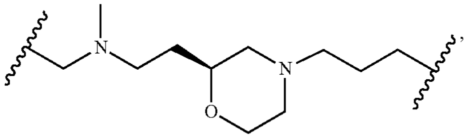
(220)
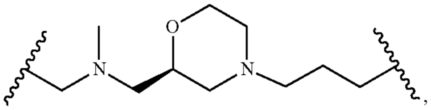

-continued
(221)
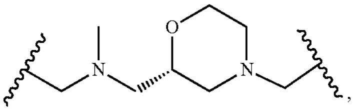
(222)
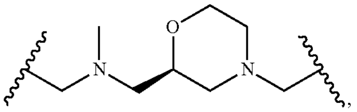
(223)
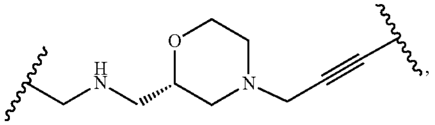
(224)
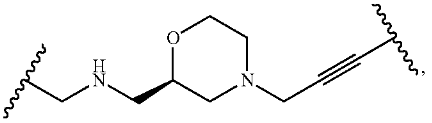
(225)
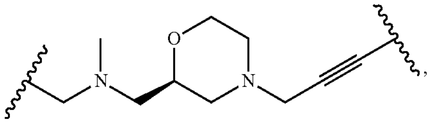
(226)
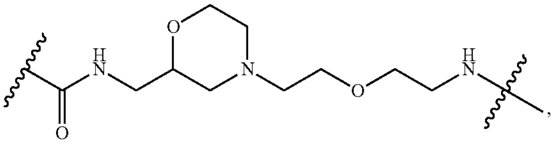
(227)
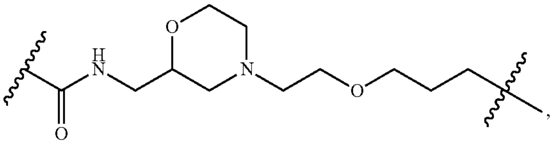
(228)
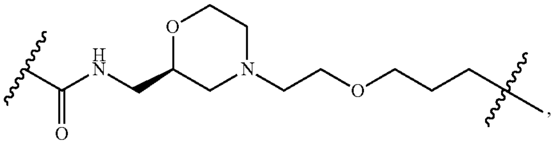
(229)
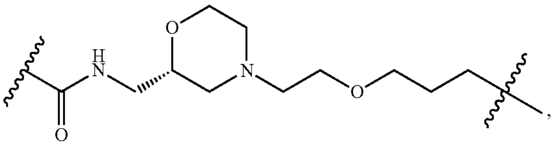
(230)
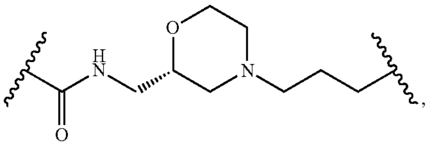
(231)
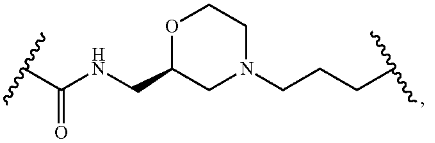
(232)
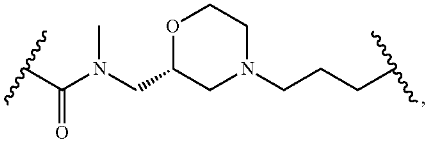
(233)
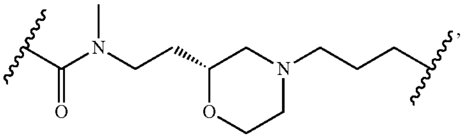
(234)
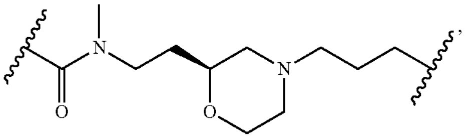
(235)
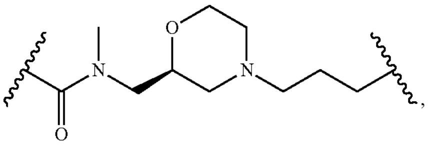
(236)
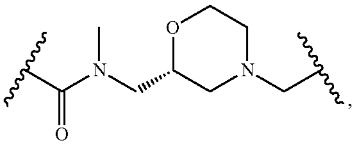
(237)
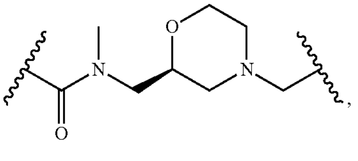
(238)
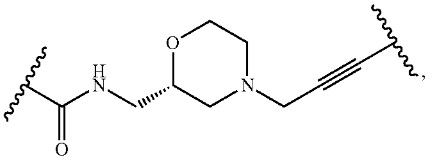
(239)
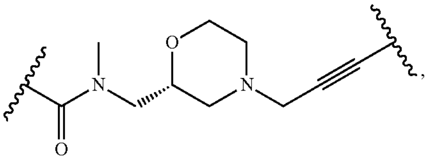
(240)
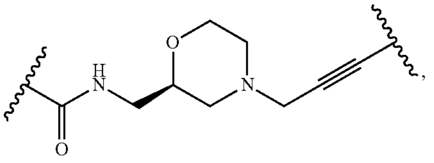

-continued
(241)
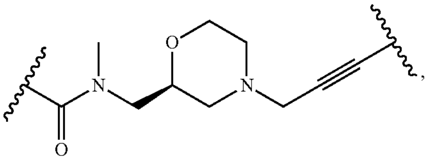
(242)
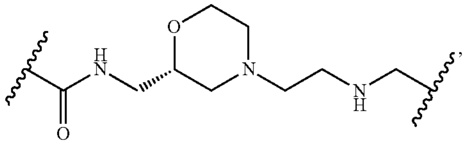
(243)
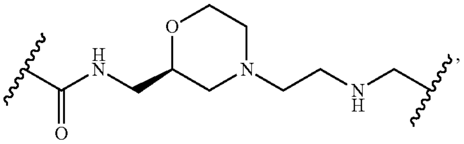
(244)
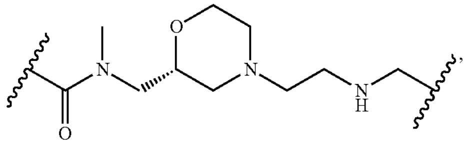
(245)
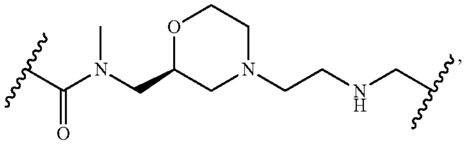
(246)
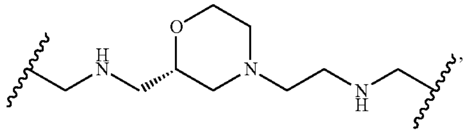
(247)
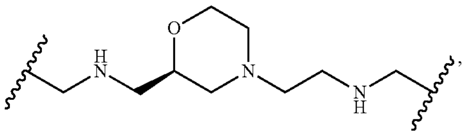
(248)
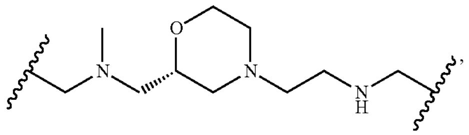
(249)
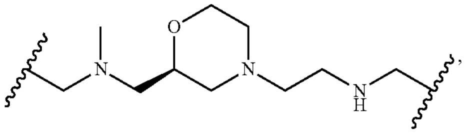
(250)
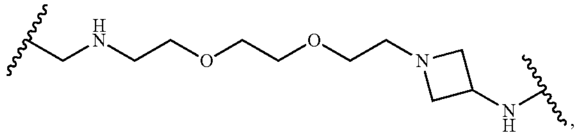
(251)
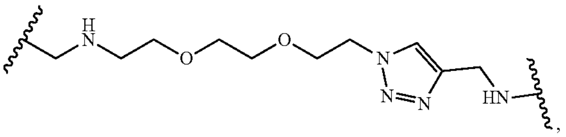
(253)
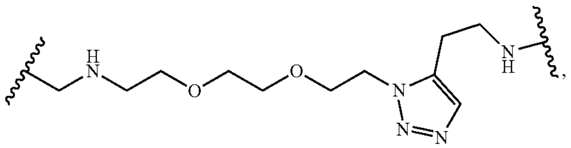
(254)
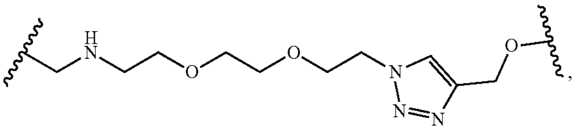
(255)
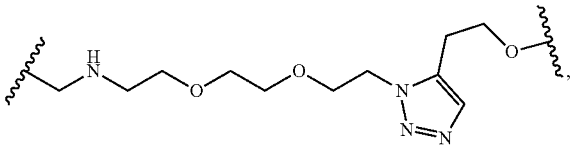
(256)
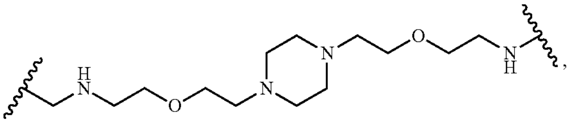
(257)
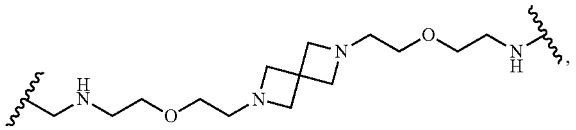
(258)
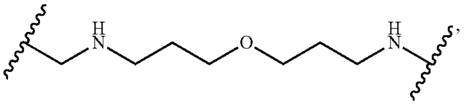
(259)
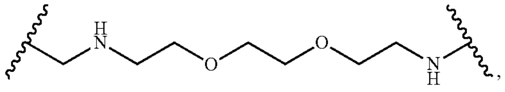
(260)
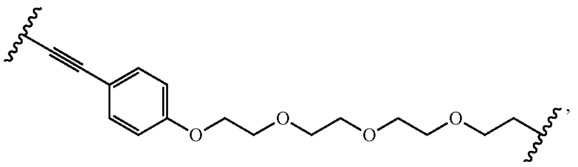
(261)
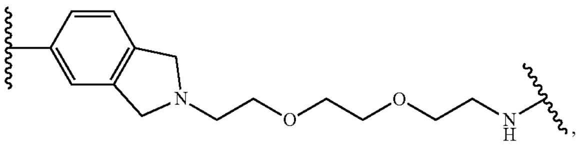

-continued
(262)
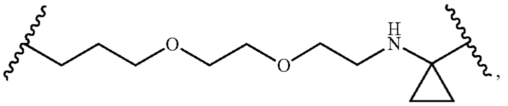
(263)
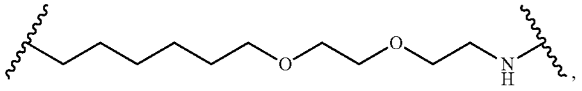
(264)
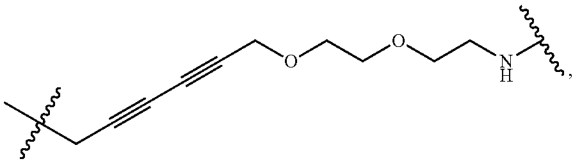
(265)
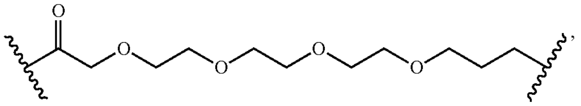
(266)
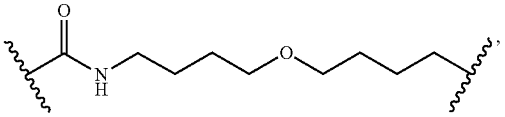
(267)
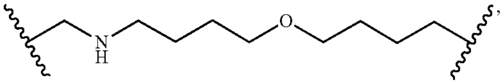
(268)
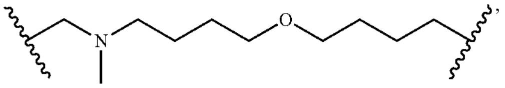
(269)
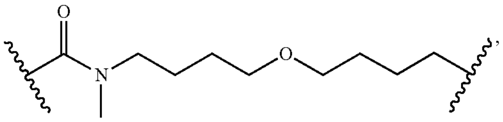
(270)
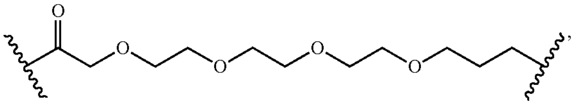
(271)
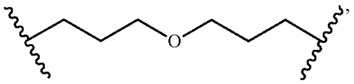
(272)
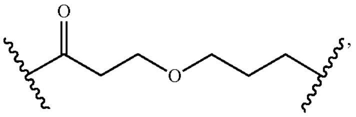
(273)
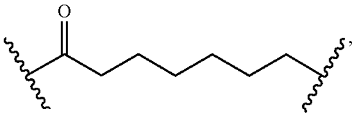
(274)
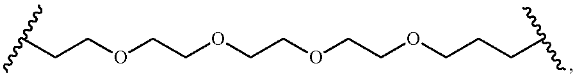
(275)
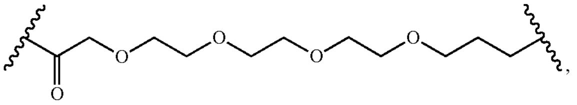
(276)
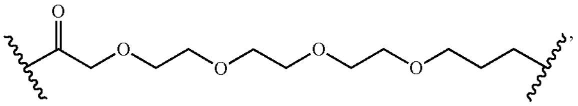
(277)
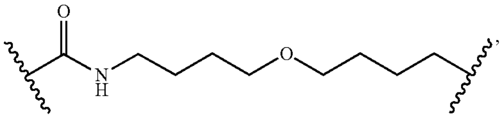
(278)
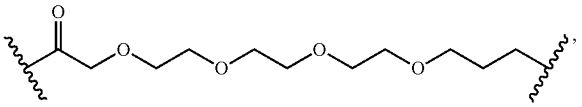
(279)
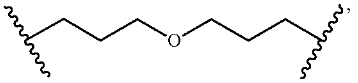
(280)
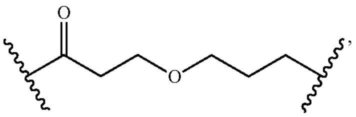
(281)
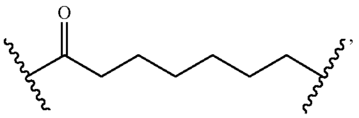
(282)
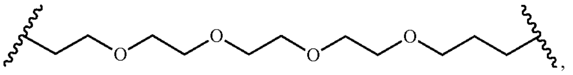
(283)
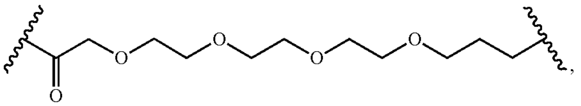

-continued
(284)
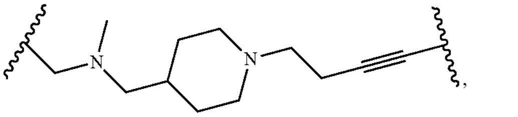
(285)
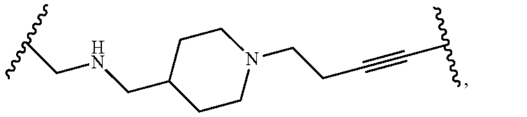
(286)
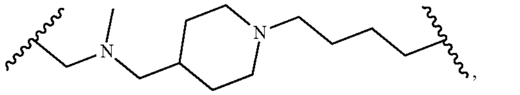
(287)
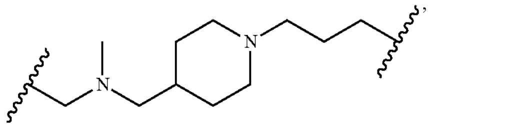
(288)
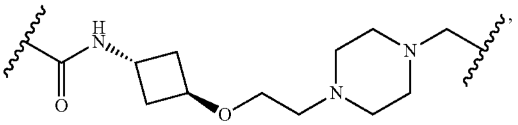
(289)
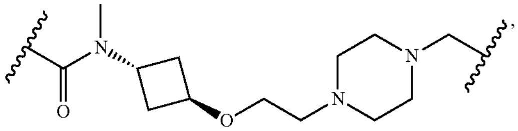
(290)
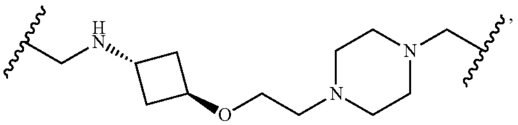
(291)
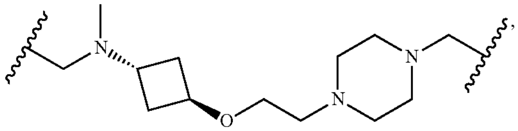
(292)
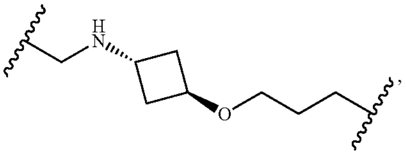
(293)
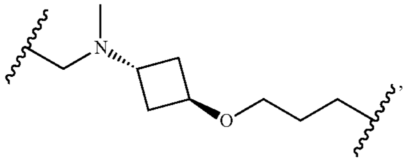
(294)
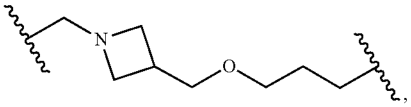
(295)
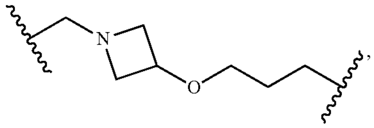
(296)
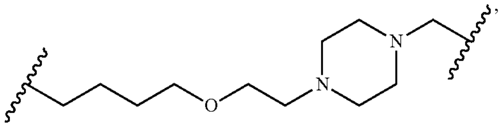
(297)
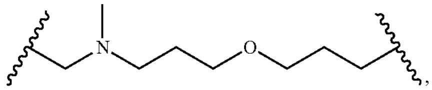
(298)
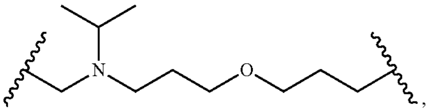
(299)
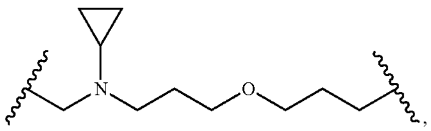
(300)
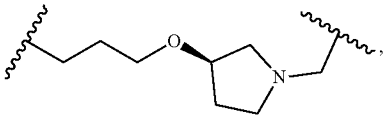
(301)
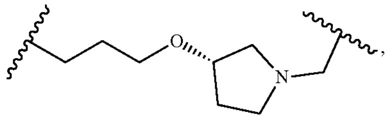
(302)
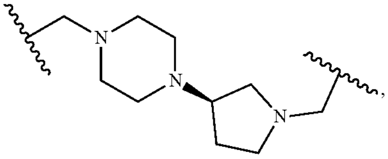
(303)
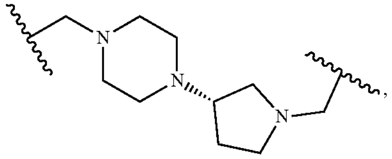
(304)
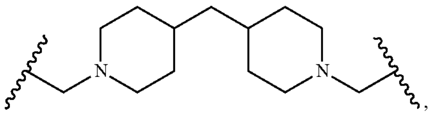
(305)
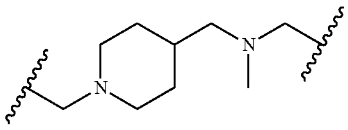

-continued
(306)
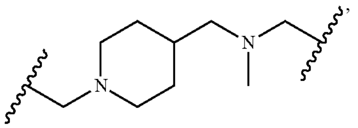
(307)
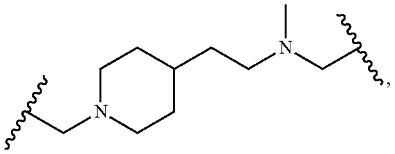
(308)
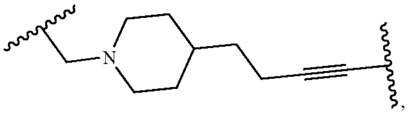
(309)
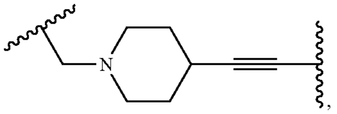
(310)
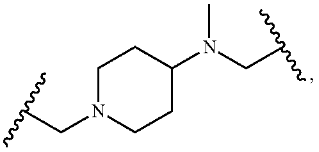
(311)
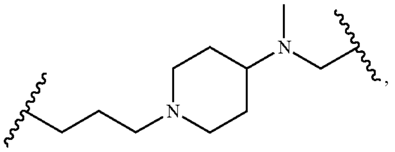
(312)
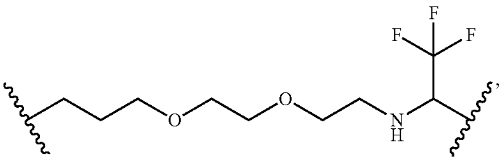
(313)
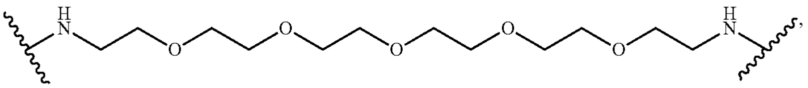
(314)
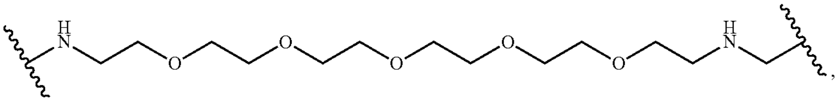
(315)
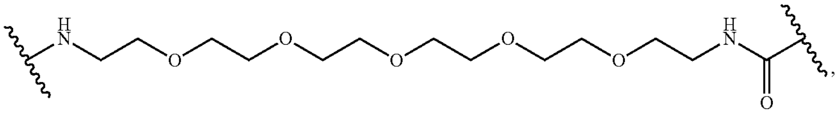
(316)
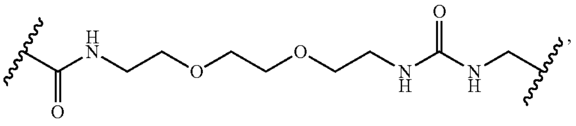
(317)
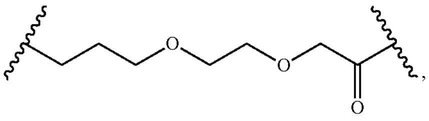
(318)
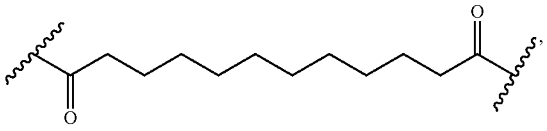
(319)
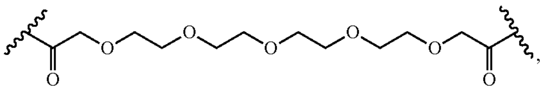
(320)
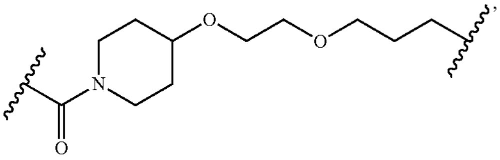
(321)
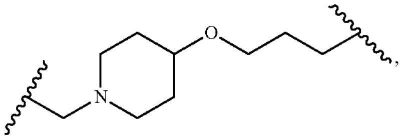

-continued
(322)
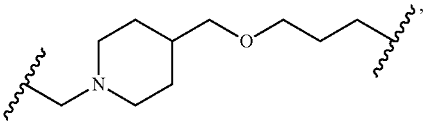
(323)
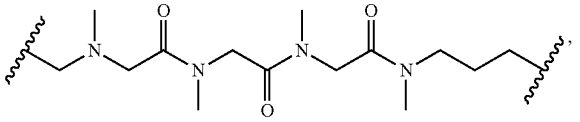
(324)
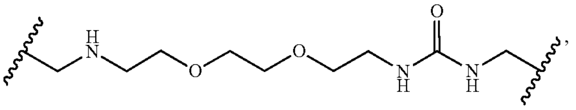
(325)
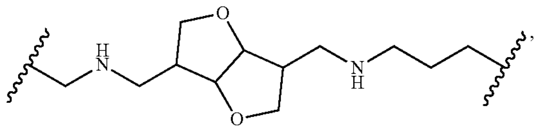
(326)
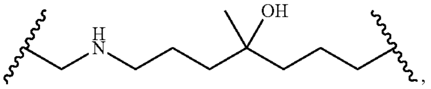
(327)
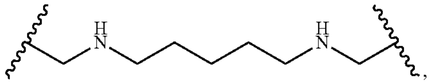
(328)
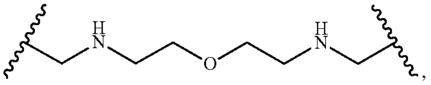
(329)
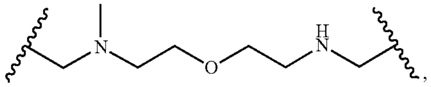
(330)
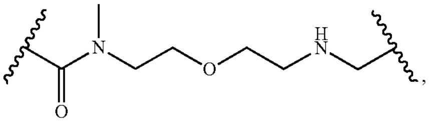
(331)
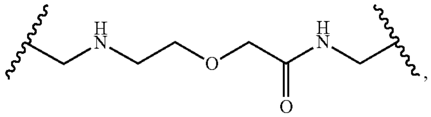
(332)
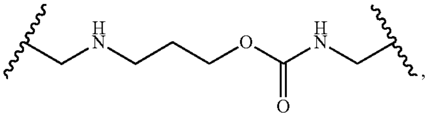
(333)
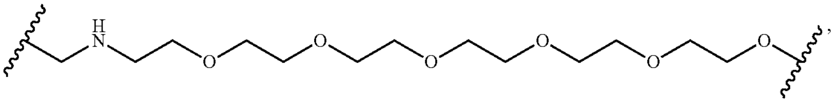
(334)
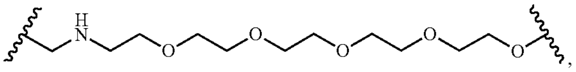
(335)
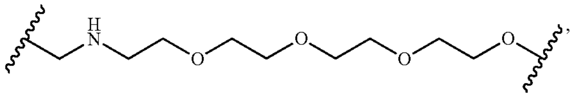
(336)
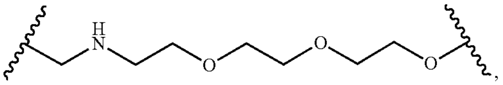
(337)
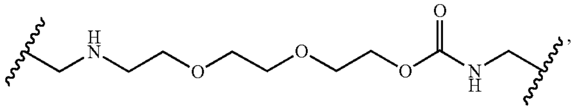
(338)
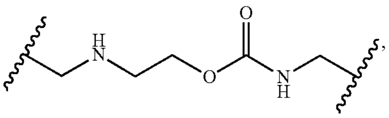
(339)
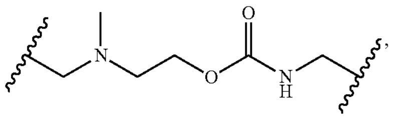
(340)
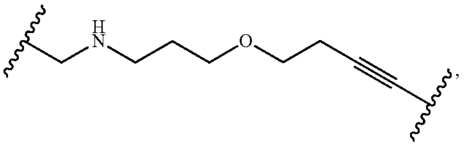
(341)
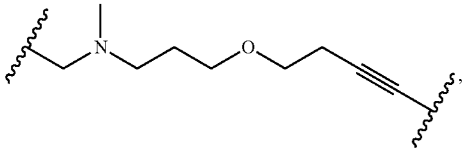
(342)
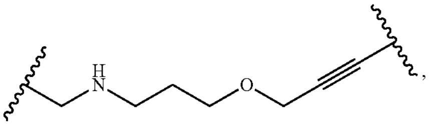
(343)
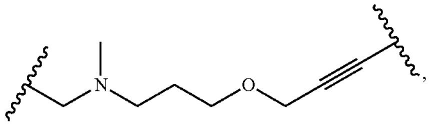

-continued
(344)
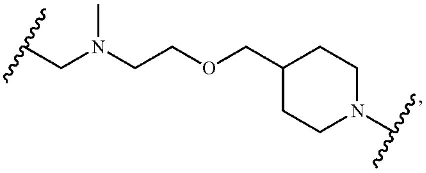
(345)
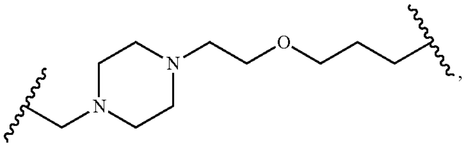
(346)
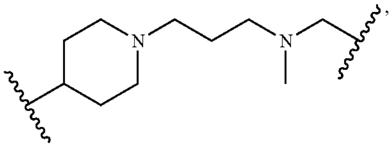
(347)
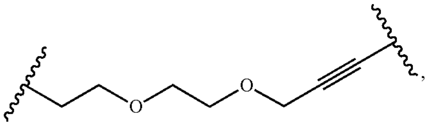
(348)
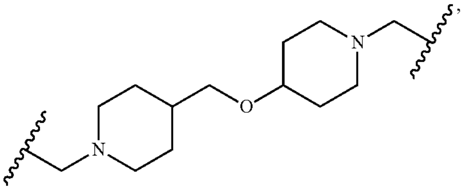
(349)
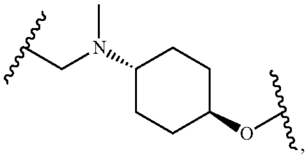
(350)
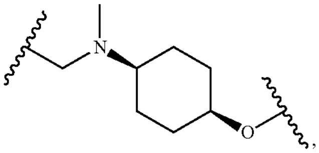
(351)
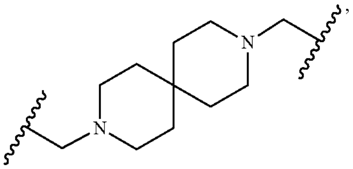
(352)
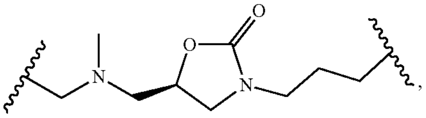
(353)
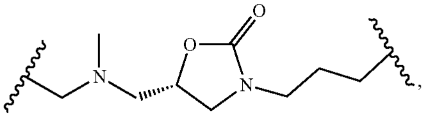
(354)
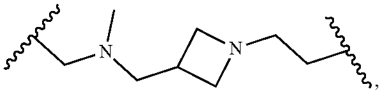
(355)
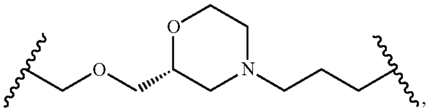
(356)
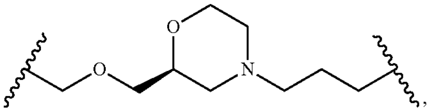
(357)
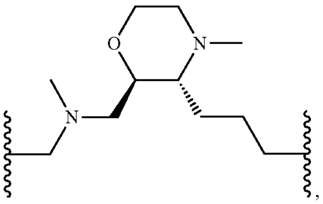
(358)
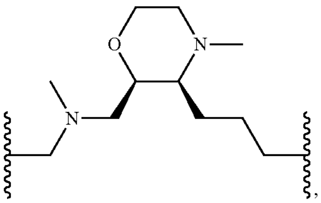
(359)
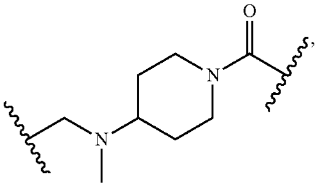
(360)
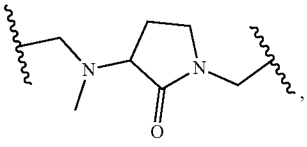
(361)
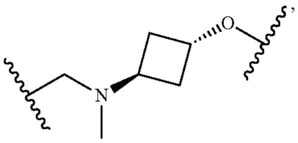

-continued
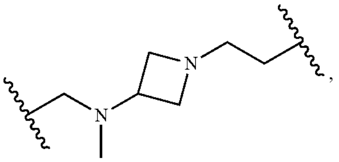
(362)
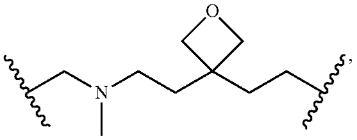
(363)
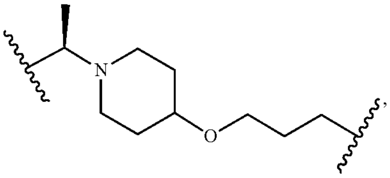
(364)
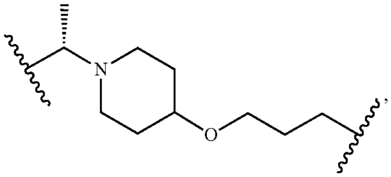
(365)
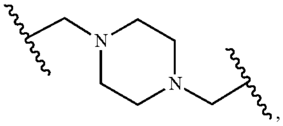
(366)
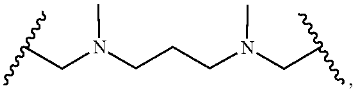
(367)
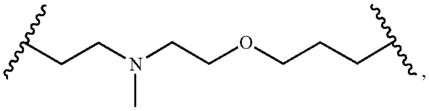
(368)
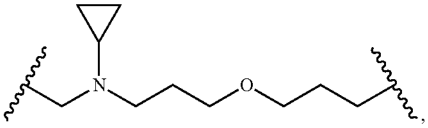
(369)
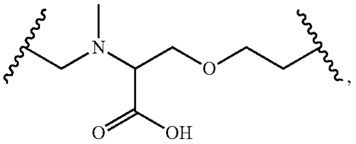
(370)
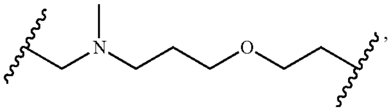
(371)
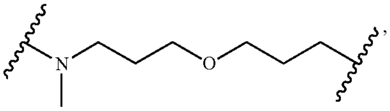
(372)
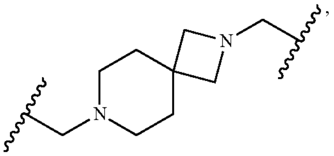
(373)
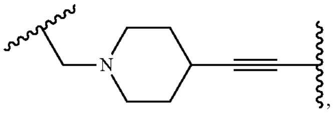
(374)
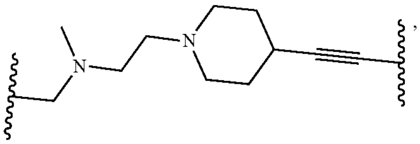
(375)
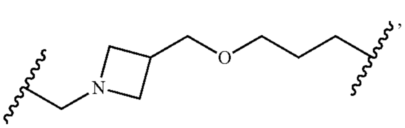
(376)
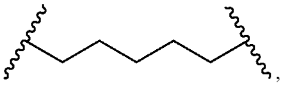
(377)
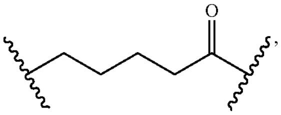
(378)
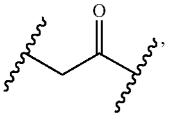
(379)
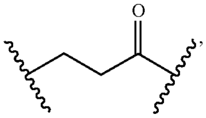
(380)
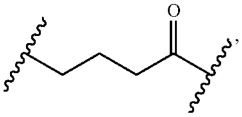
(381)

-continued
(382)
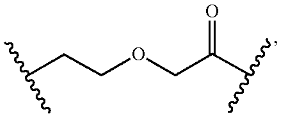
(383)
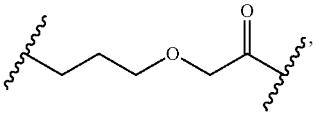
(384)
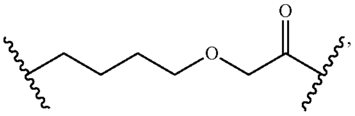
(385)
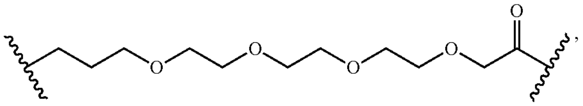
(386)
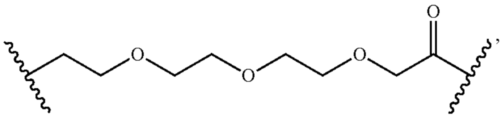
(387)
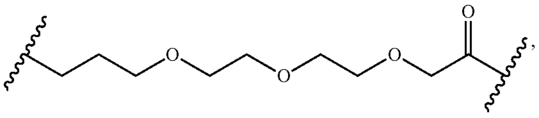
(388)
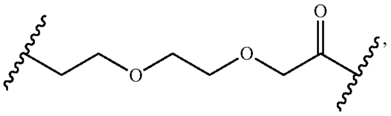
(389)
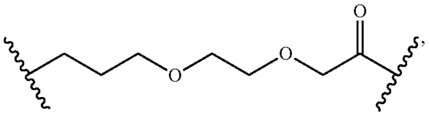
(390)
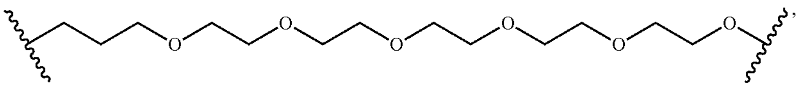
(391)
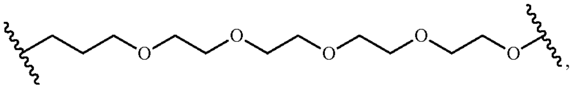
(392)
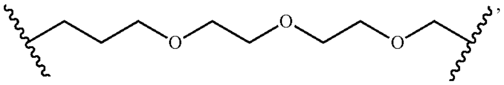
(393)
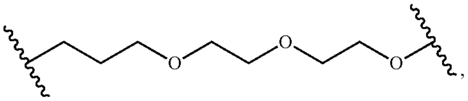
(394)
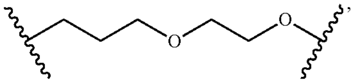
(395)
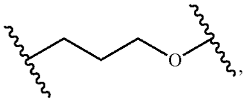
(396)
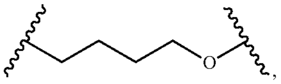
(397)
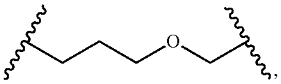
(398)
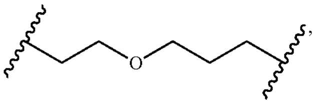
(399)
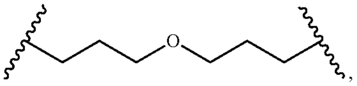
(400)
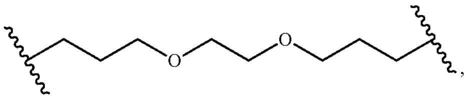
(401)
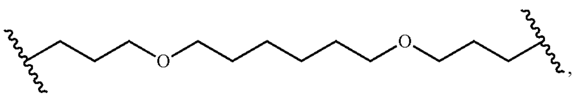
(402)
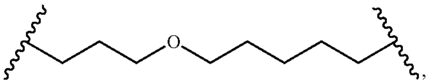
(403)
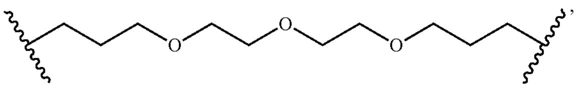
(404)
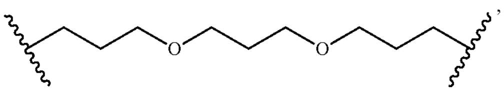

-continued
(405)
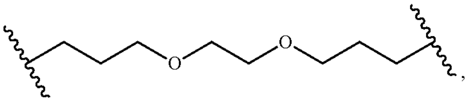
(406)
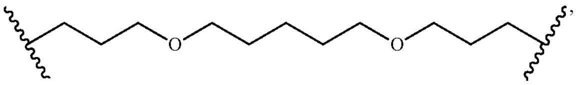
(407)
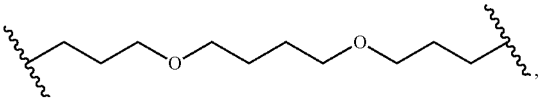
(408)
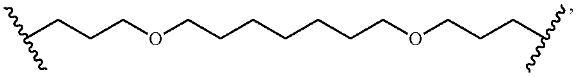
(409)
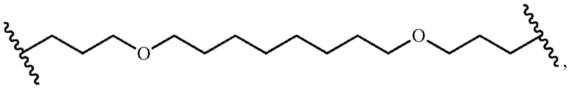
(410)
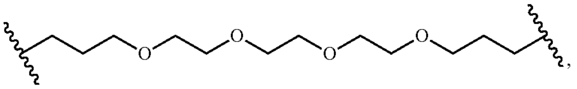
(411)
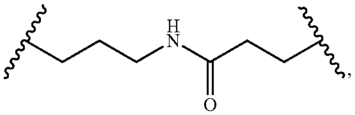
(412)
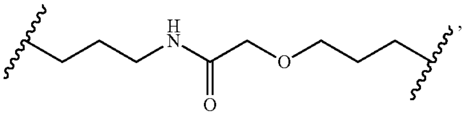
(413)
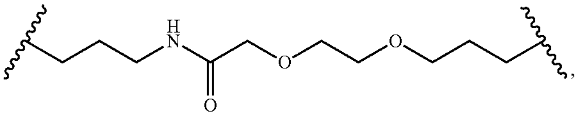
(414)
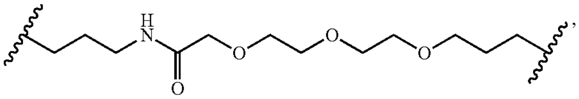
(415)
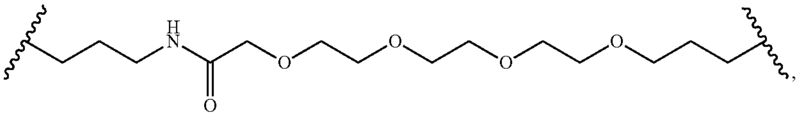
(416)
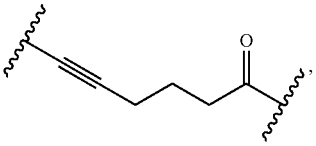
(417)
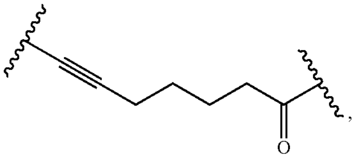
(418)
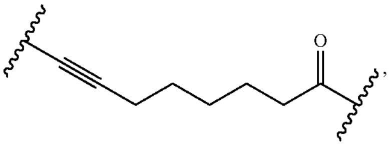
(419)
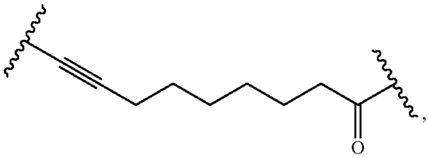
(420)
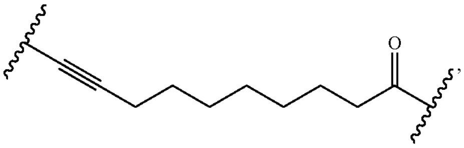
(421)
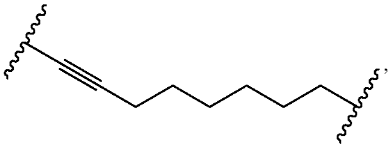
(422)
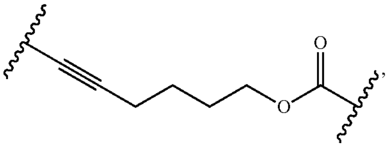
(423)
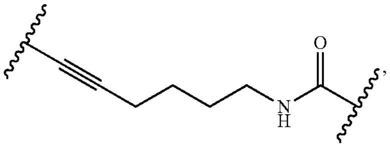

-continued
(424)
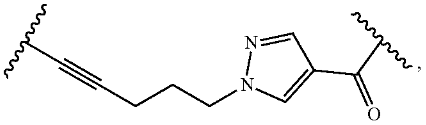
(425)
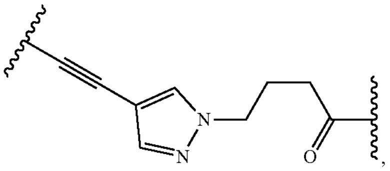
(426)
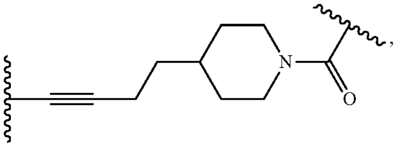
(427)
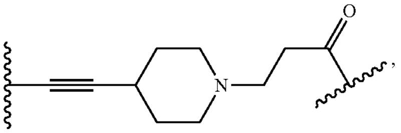
(428)
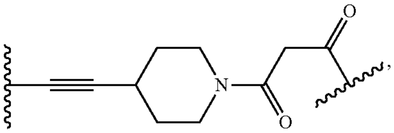
(429)
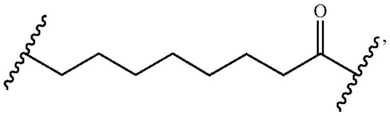
(430)
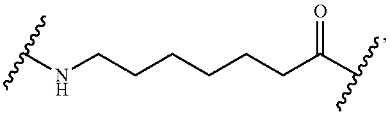
(431)
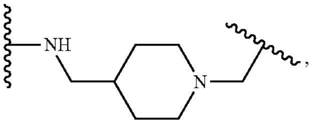
(432)
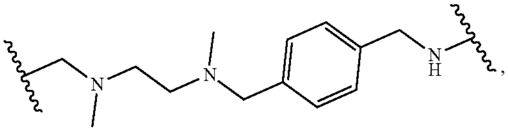
(433)
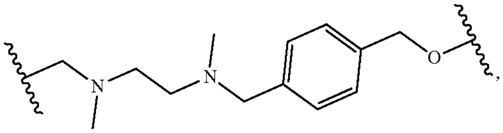
(434)
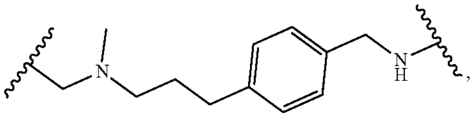
(435)
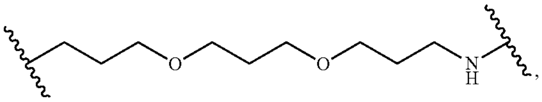
(436)
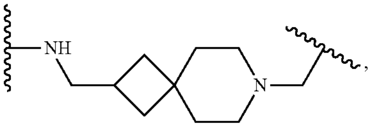
(437)
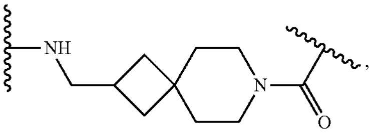
(438)
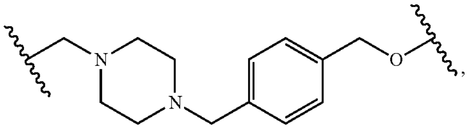
(438)
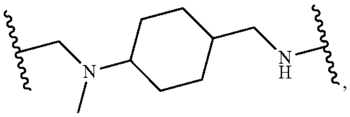
(439)
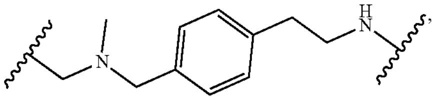
(440)
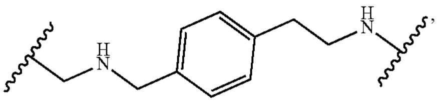
(441)
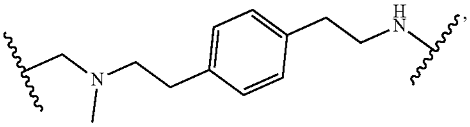
(442)
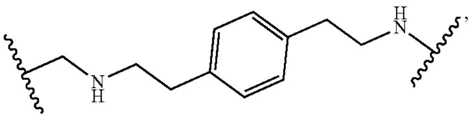
(443)
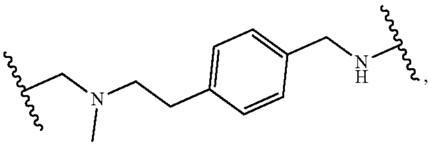
(444)
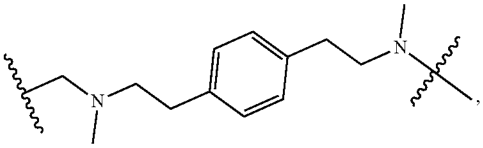

-continued
(445)
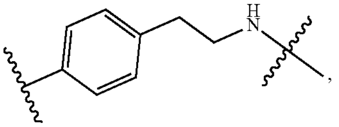
(446)
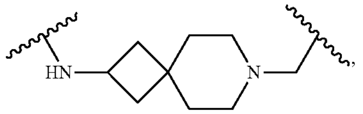
(447)
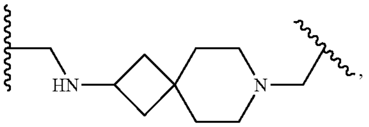
(448)
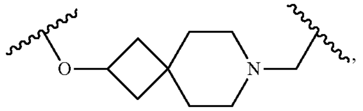
(449)
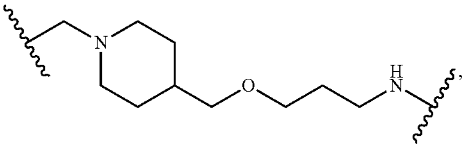
(450)
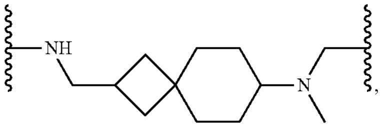
(451)
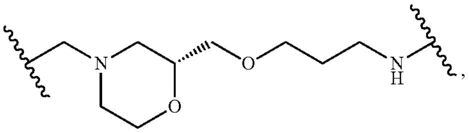
(452)
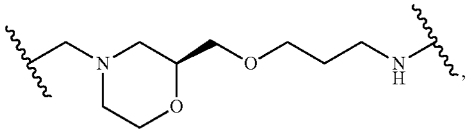
(453)
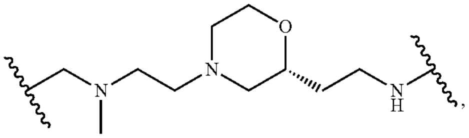
(454)
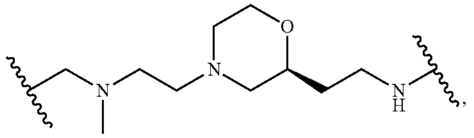
(455)
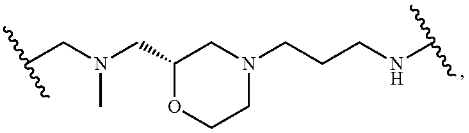
(456)
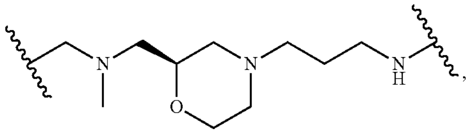
(457)
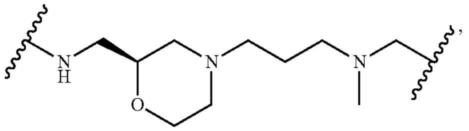
(458)
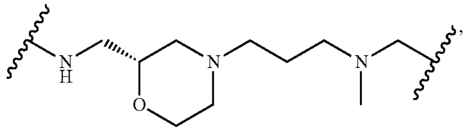
(459)
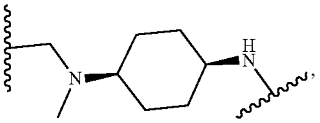
(460)
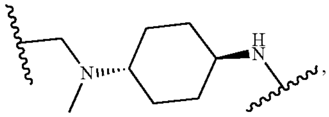
(461)
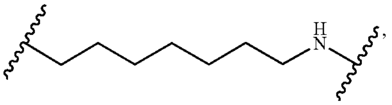
(462)
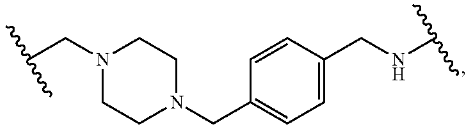
(463)
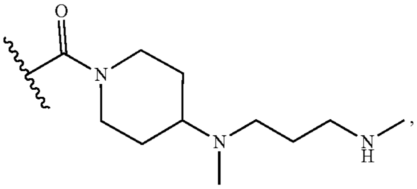
(464)
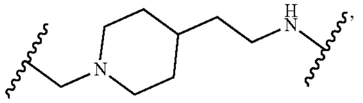
(465)
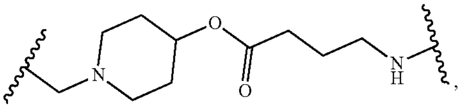
(466)
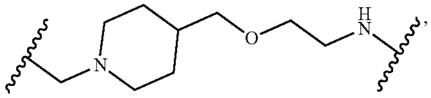

-continued
(467)
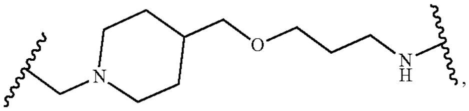
(468)
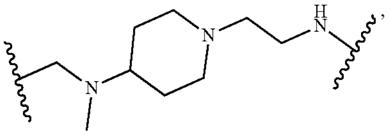
(469)
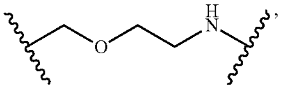
(470)
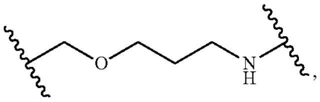
(471)
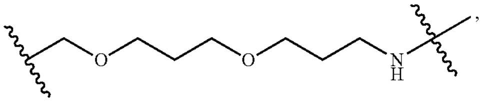
(472)
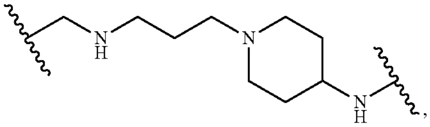
(472)
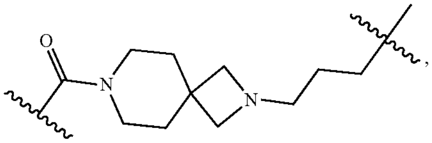
(474)
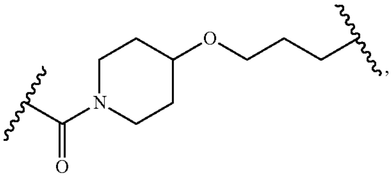
(475)
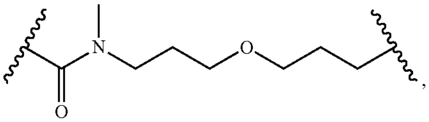
(475)
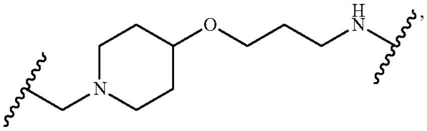
(476)
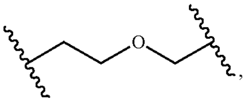
(477)
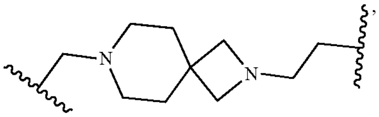
(478)
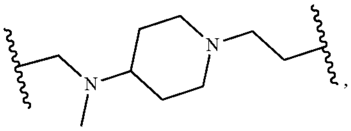
(479)
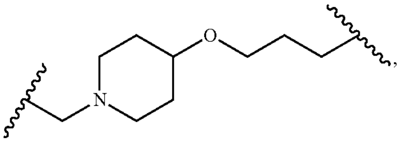
(480)
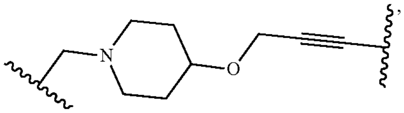
(481)
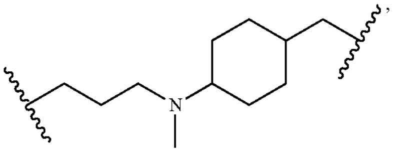
(482)
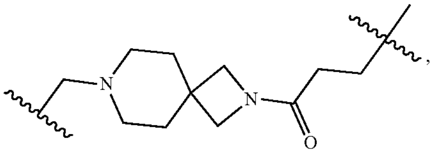
(483)
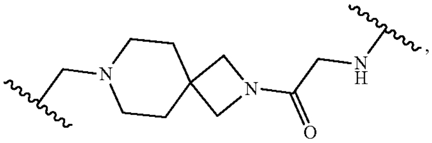
(484)
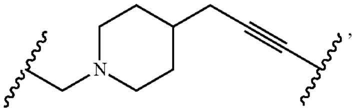
(485)
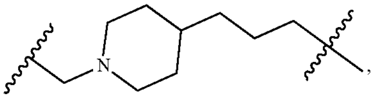

-continued
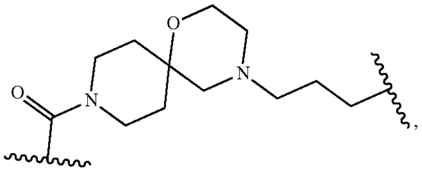
(486)
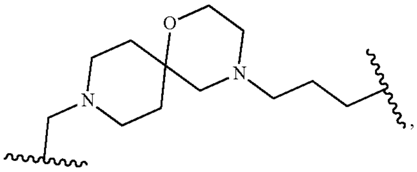
(487)
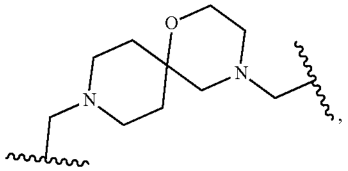
(488)
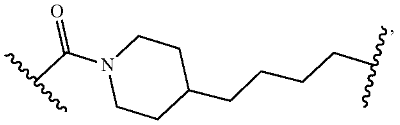
(489)
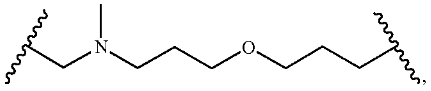
(490)
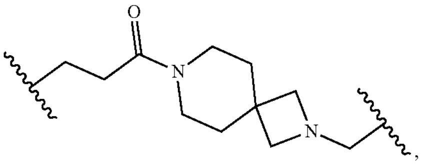
(491)
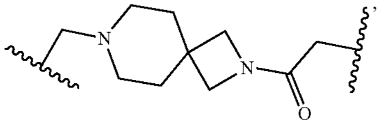
(492)
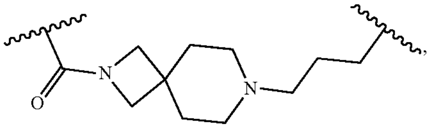
(493)
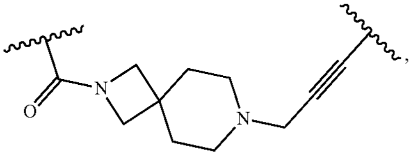
(494)
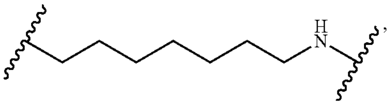
(495)
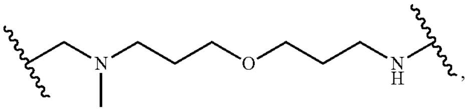
(496)
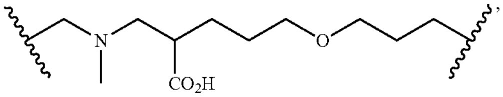
(497)
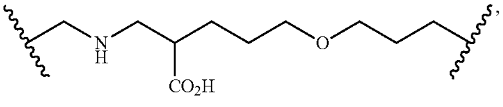
(498)
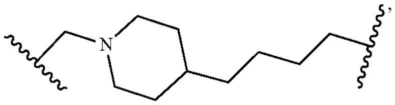
(499)
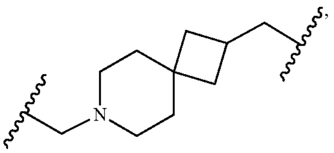
(500)
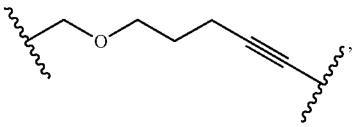
(501)
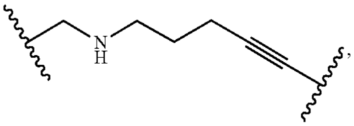
(502)
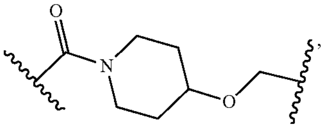
(503)
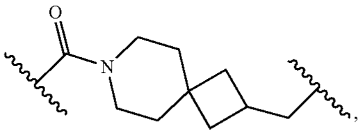
(504)
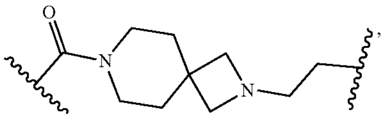
(505)

-continued
(506)
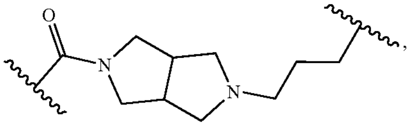
(507)
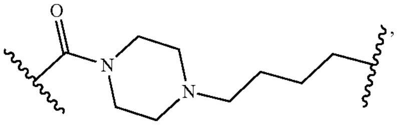
(508)
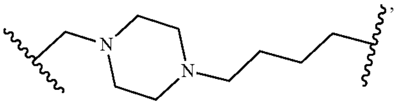
(509)
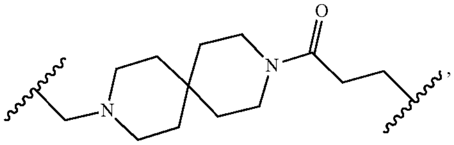
(510)
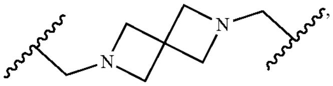
(511)
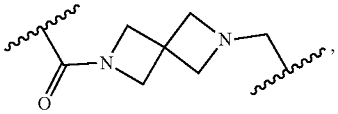
(512)
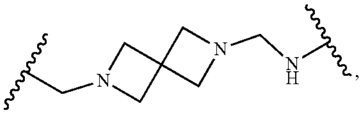
(513)
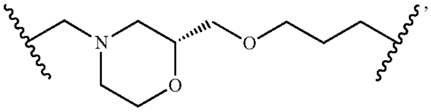
(514)
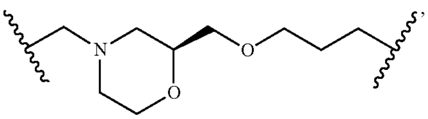
(515)
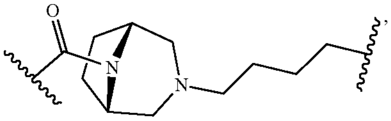
(516)
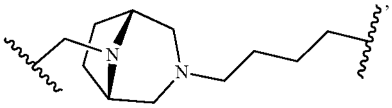
(517)
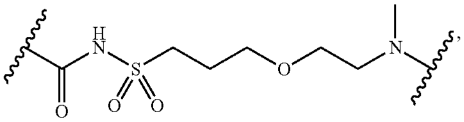
(518)
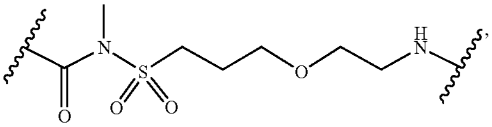
(519)
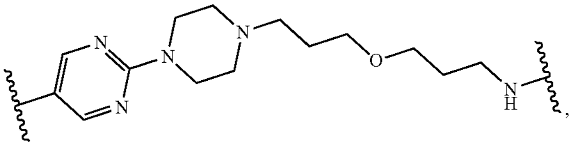
(520)
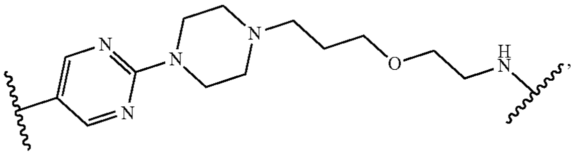
(521)
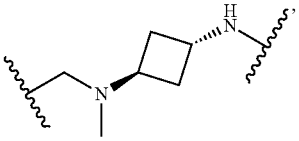
(522)
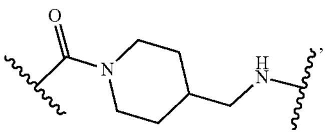
(523)
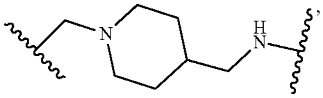
(524)
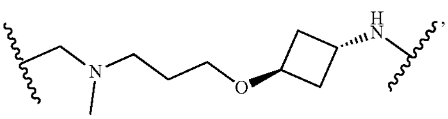
(525)
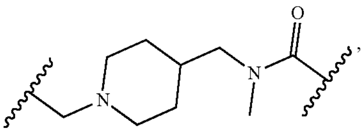

-continued
(526)
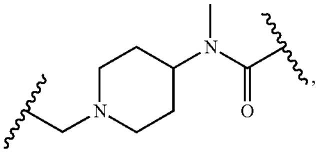
(527)
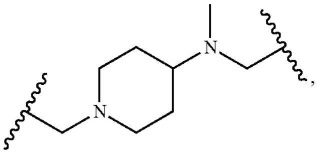
(528)
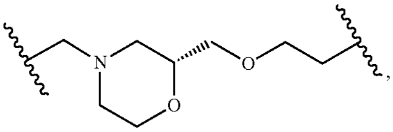
(529)
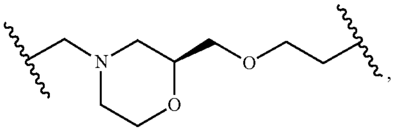
(530)
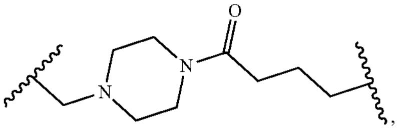
(531)
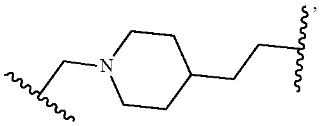
(532)
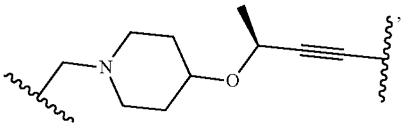
(533)
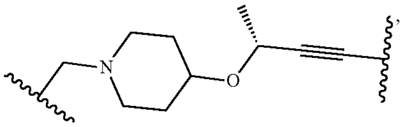
(534)
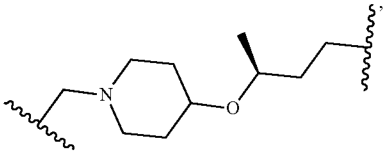
(535)
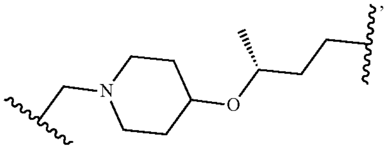
(536)
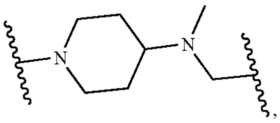
(537)
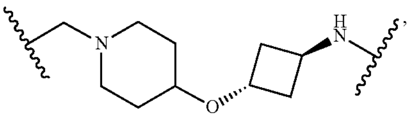
(538)
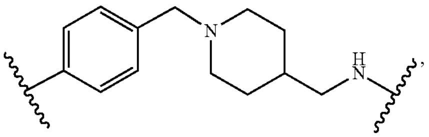
(539)
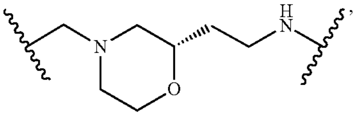
(540)
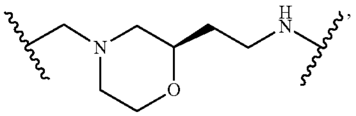
(541)
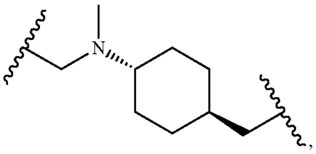
(542)
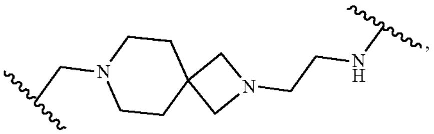
(543)
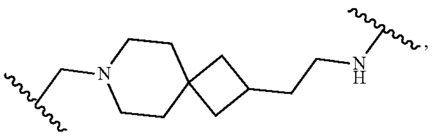
(544)
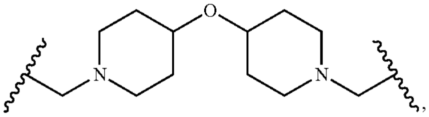

-continued
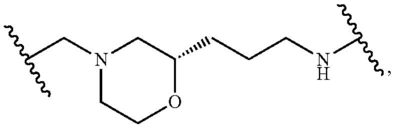
(545)
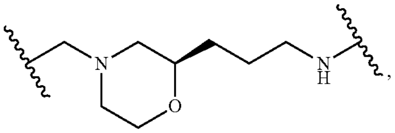
(546)
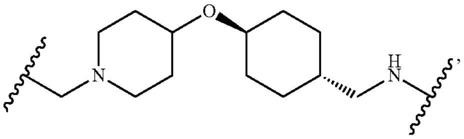
(547)
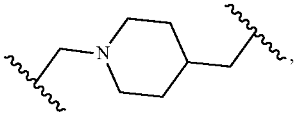
(548)
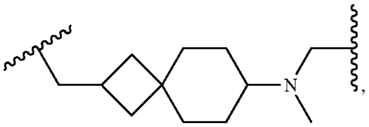
(549)
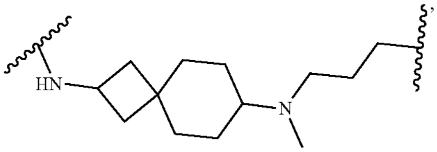
(550)
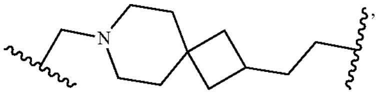
(551)
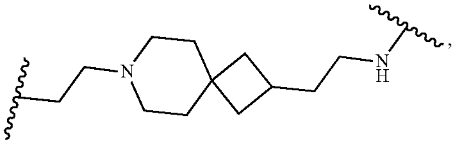
(552)
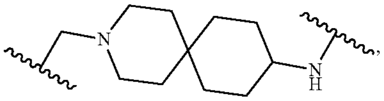
(553)
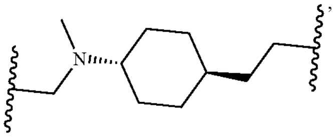
(554)
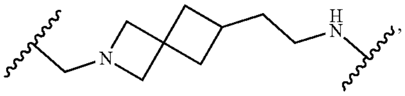
(555)
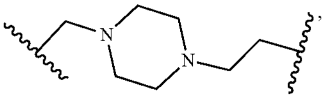
(556)
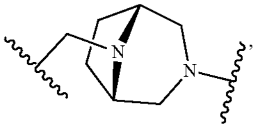
(557)
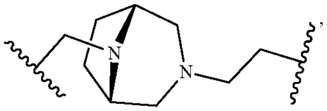
(558)
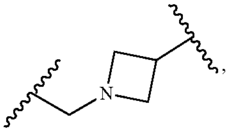
(559)
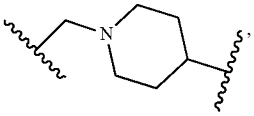
(560)
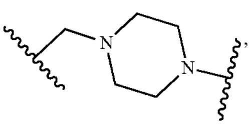
(561)
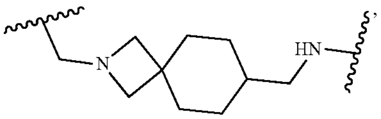
(562)
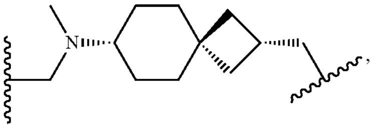
(563)
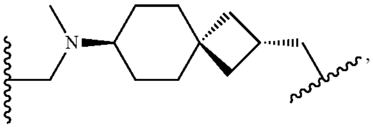
(564)
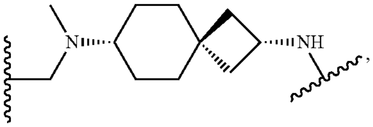
(565)
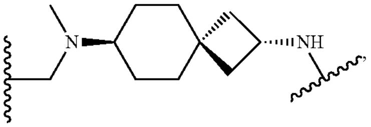
(566)

-continued
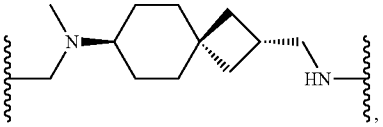
(567)
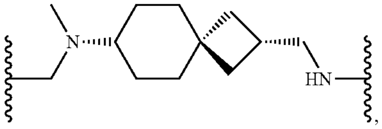
(568)
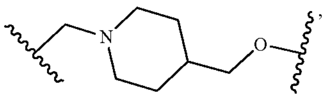
(569)
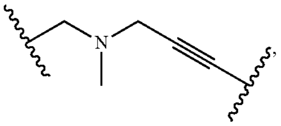
(570)
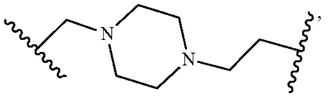
(571)
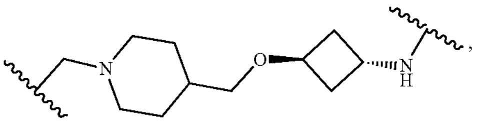
(572)
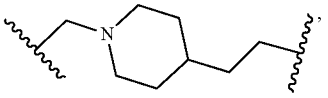
(573)
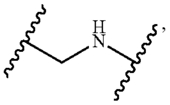
(574)
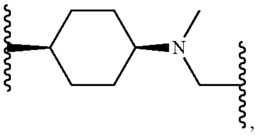
(575)
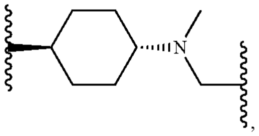
(576)
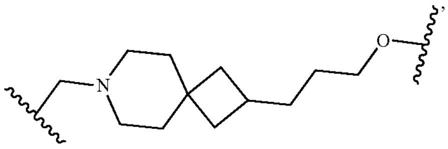
(577)
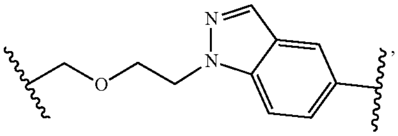
(578)
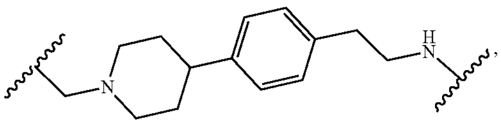
(579)
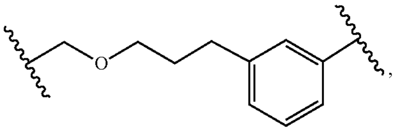
(580)
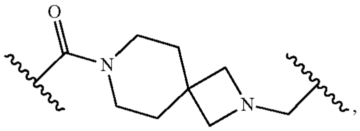
(581)
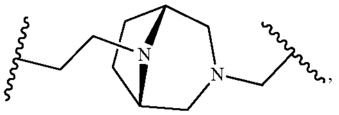
(582)
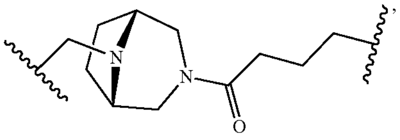
(583)
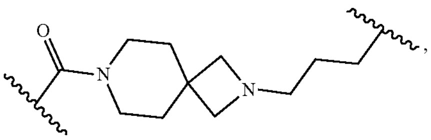
(584)
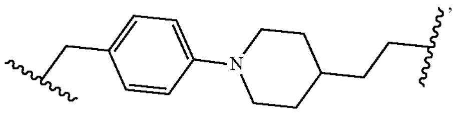
(585)
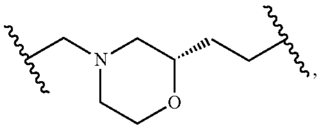
(586)
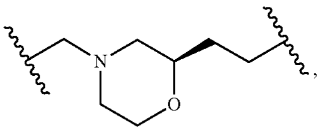
(587)
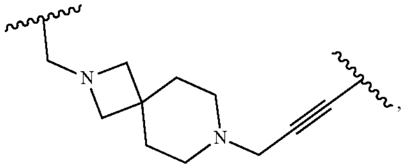
(588)

-continued
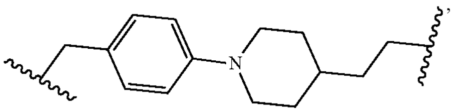
(589)
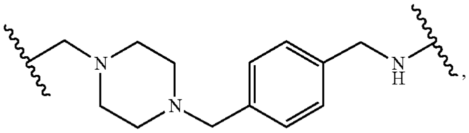
(590)
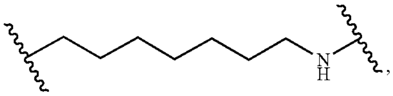
(591)
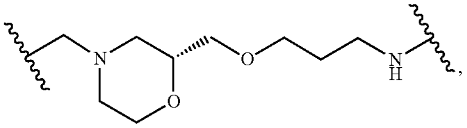
(592)
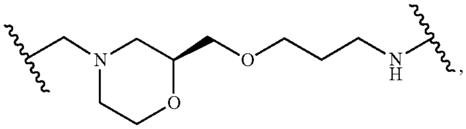
(593)
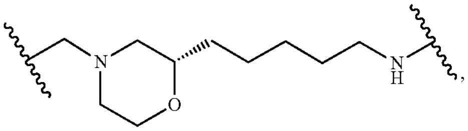
(594)
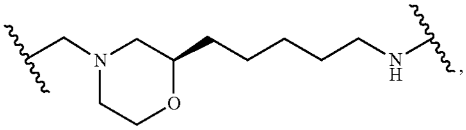
(595)
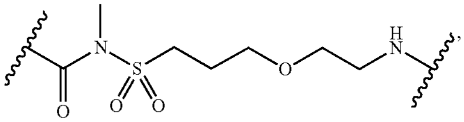
(596)
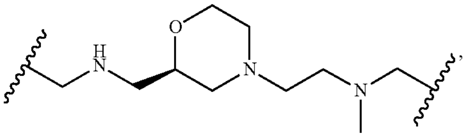
(597)
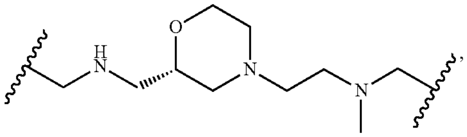
(598)
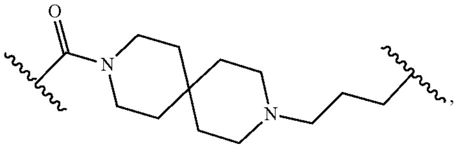
(599)
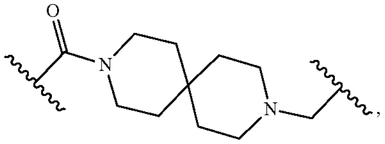
(600)
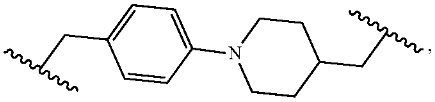
(601)
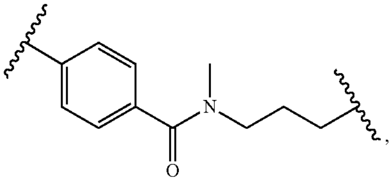
(602)
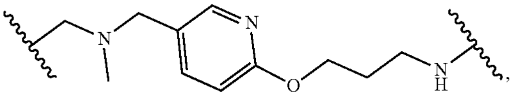
(603)
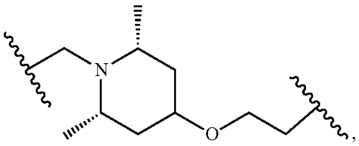
(604)
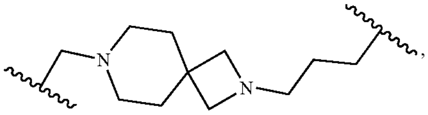
(605)
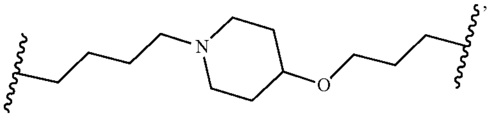
(606)
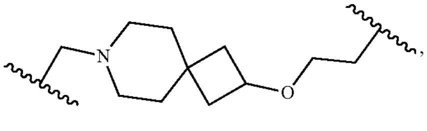
(607)
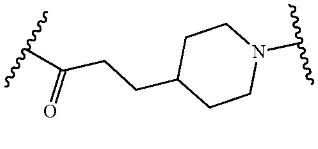
(608)

-continued
(609)
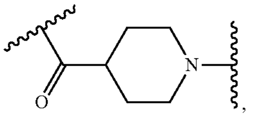
(610)
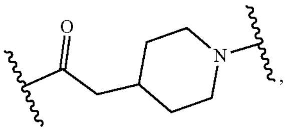
(611)
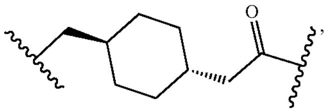
(612)
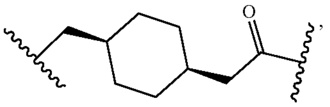
(613)
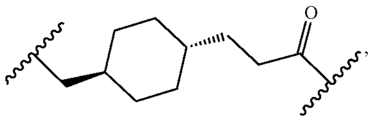
(614)
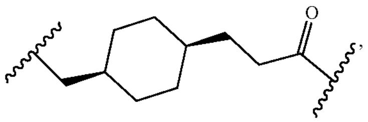
(615)
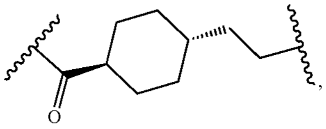
(616)
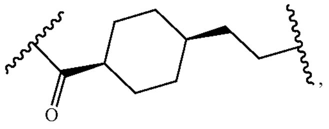
(617)
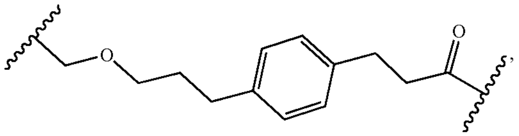
(618)
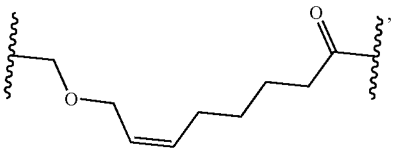
(619)
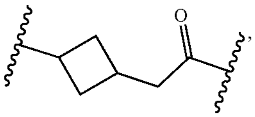
(620)
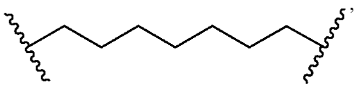
(621)
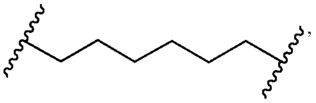
(622)
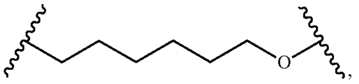
(623)
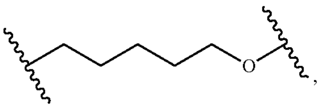
(624)
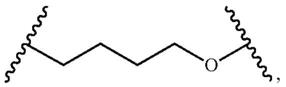
(625)
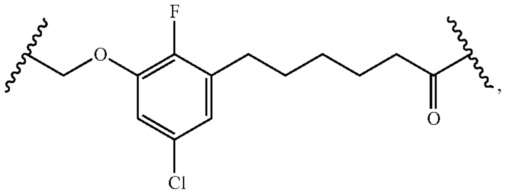
(626)
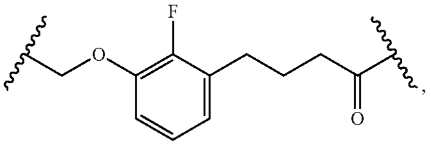
(627)
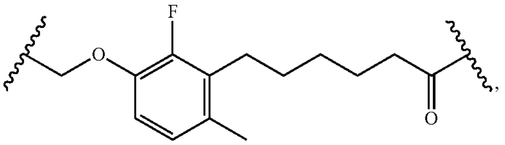
(628)
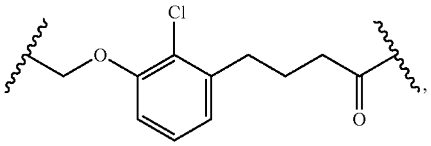
(629)
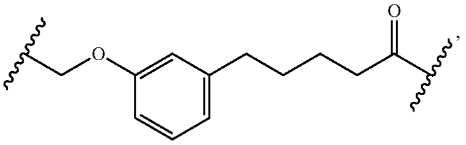
(630)
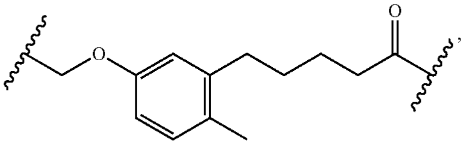

-continued
(631)
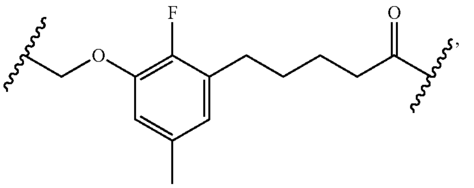
(632)
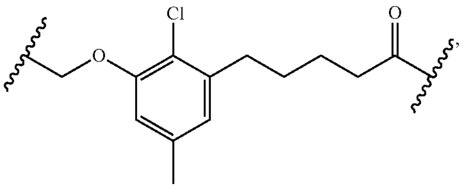
(633)
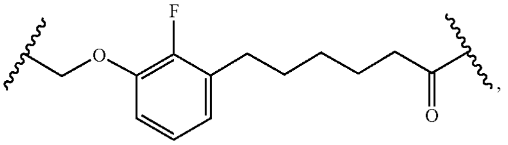
(634)
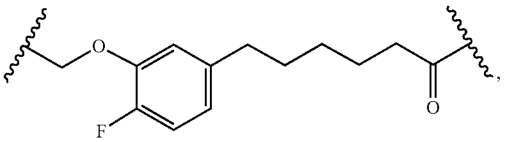
(635)
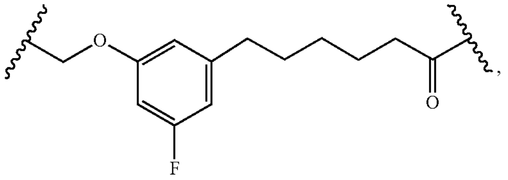
(636)
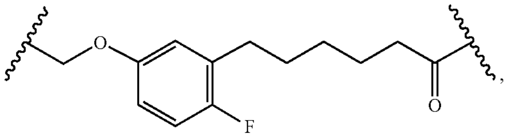
(637)
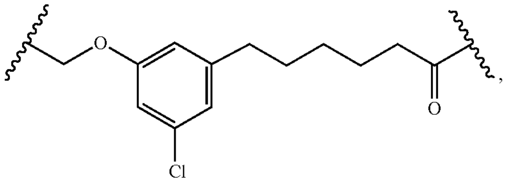
(638)
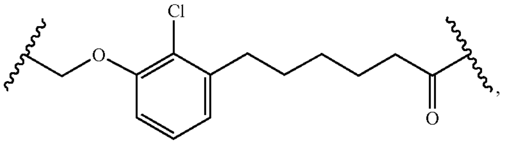
(639)
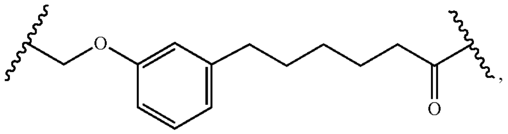
(640)
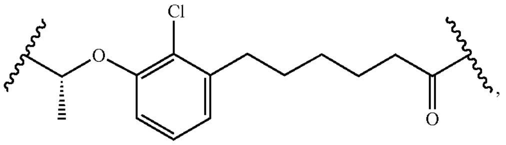
(641)
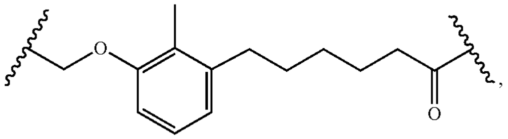
(642)
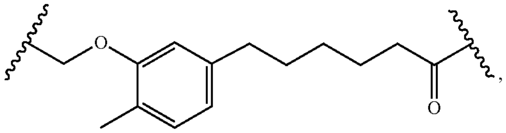
(643)
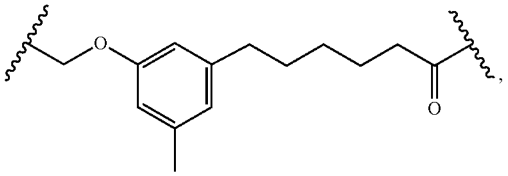
(644)
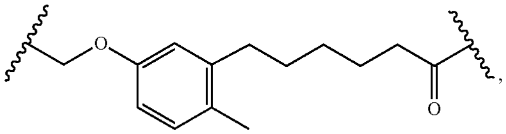
(645)
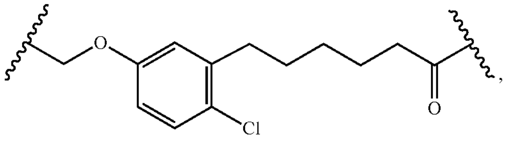
(646)
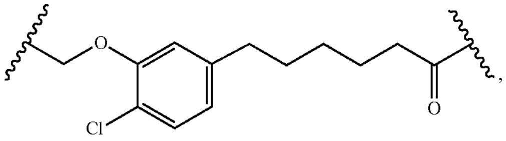
(647)
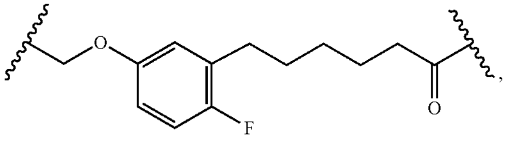
(648)
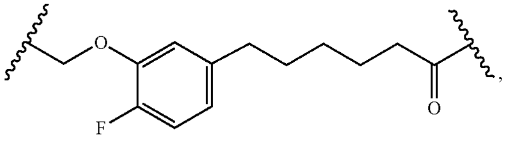

-continued
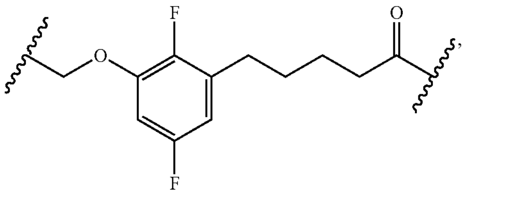
(649)
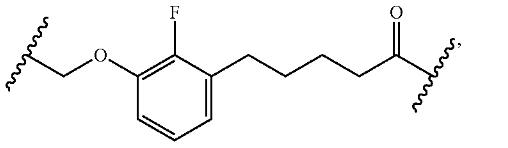
(650)
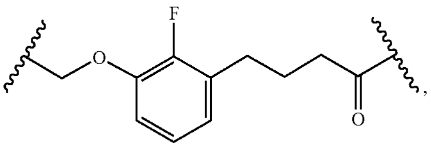
(651)
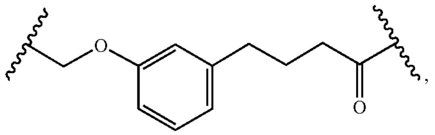
(652)
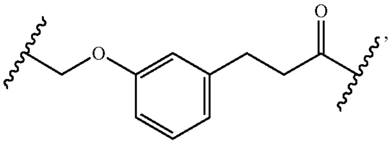
(653)
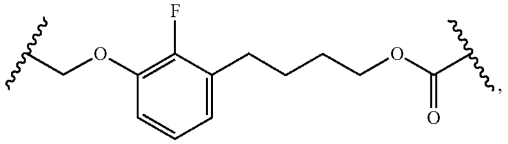
(654)
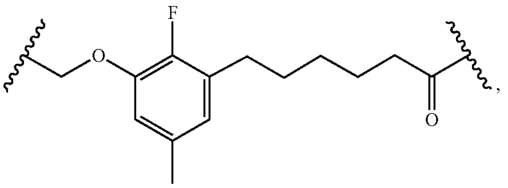
(655)
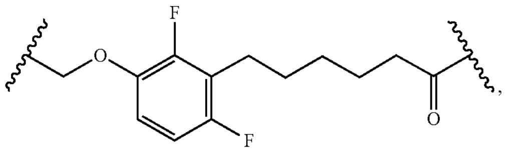
(656)
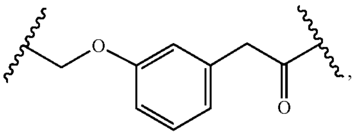
(657)
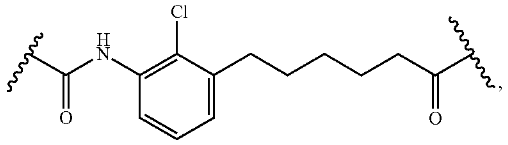
(658)
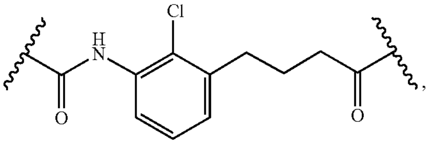
(659)
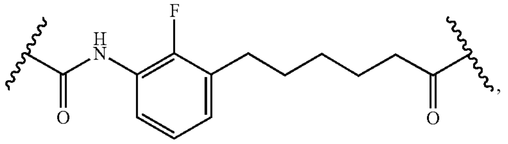
(660)
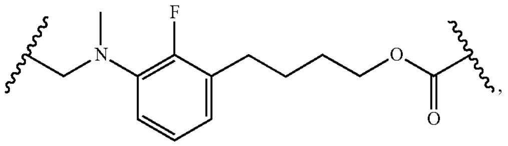
(661)
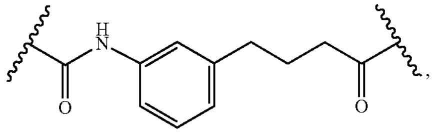
(662)
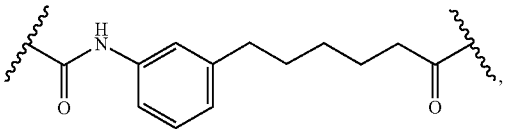
(663)
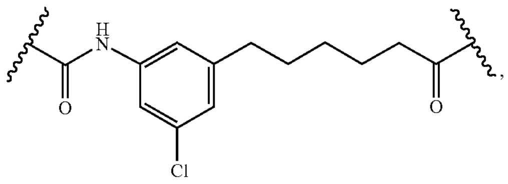
(664)
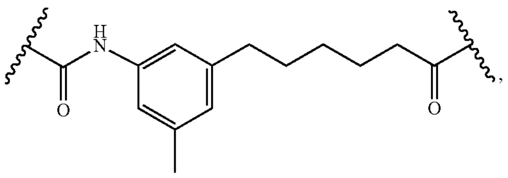
(665)
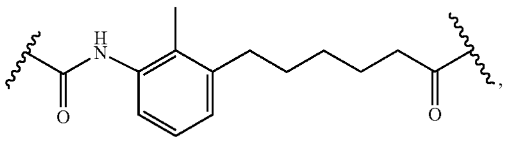
(666)

-continued
(667)
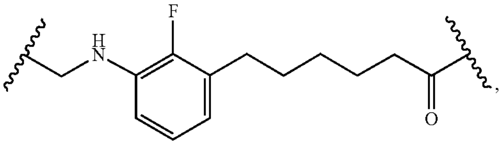
(668)
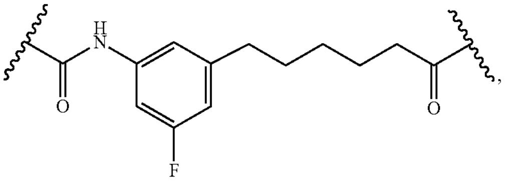
(669)
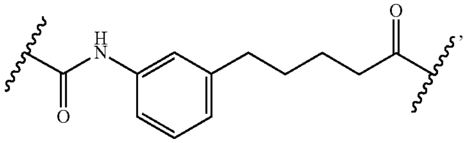
(670)
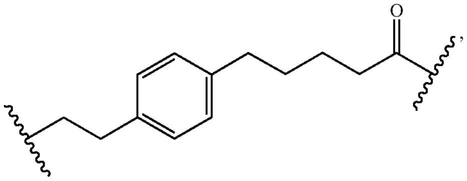
(671)
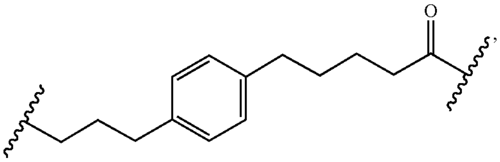
(672)
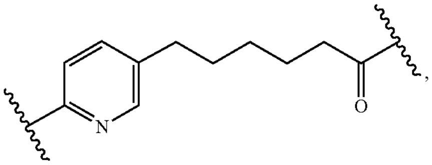
(673)
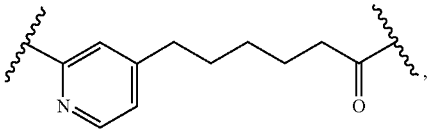
(674)
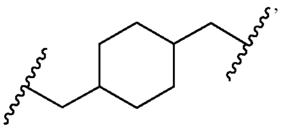
(675)
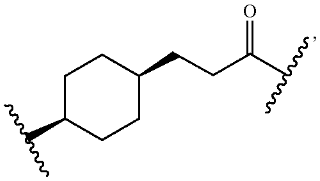
(676)
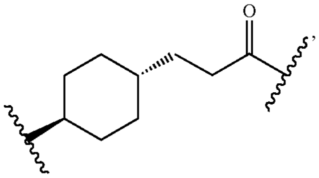
(677)
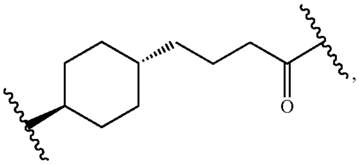
(678)
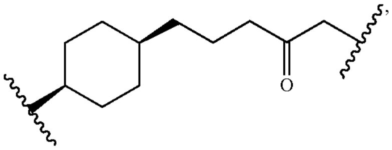
(679)
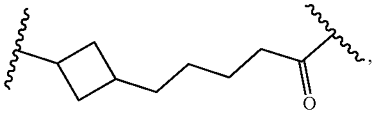
(680)
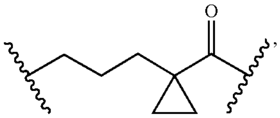
(681)
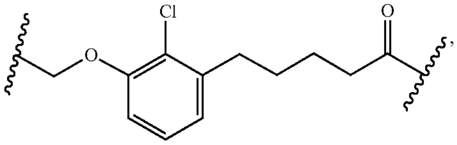
(682)
covalent bond,
(683)
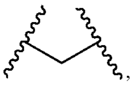
(684)
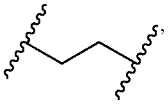
(685)
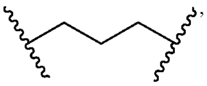
(686)
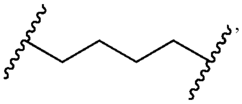

-continued
(687)
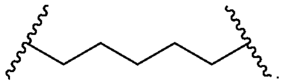
In some embodiments, the present invention provides a compound having a STAT3 binding moiety described and disclosed herein, a LBM set forth in Table A above, and a linker set forth in Table B above, or a pharmaceutically acceptable salt thereof.
Exemplary compounds of the invention are set forth in Table 1 and Table 1A, below.

TABLE 1
| Exemplary Compounds | |
|---|---|
| I-# | Structure |
| I-1 | 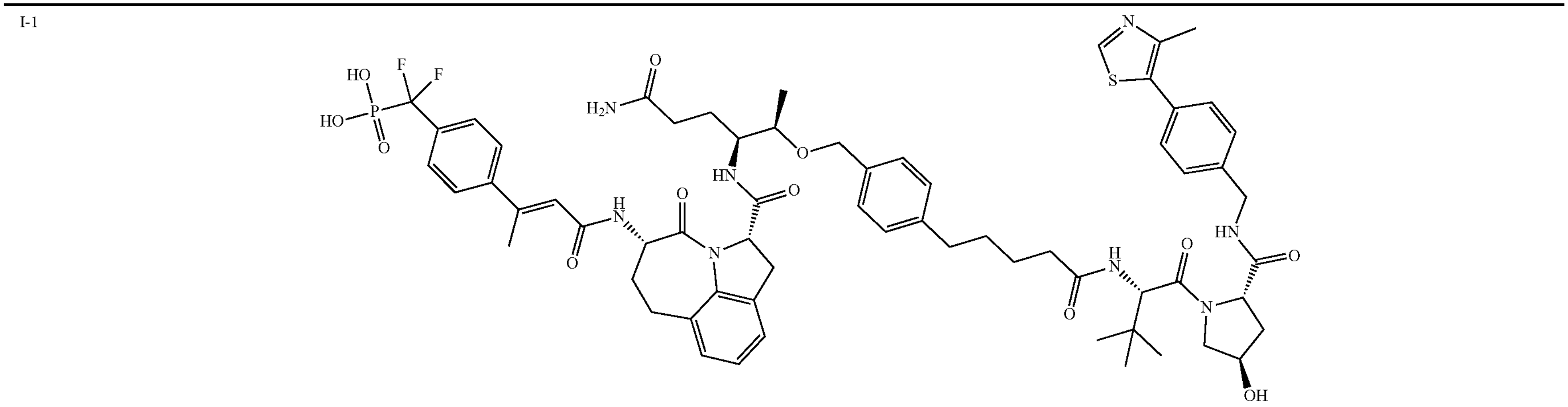 |
| I-2 | 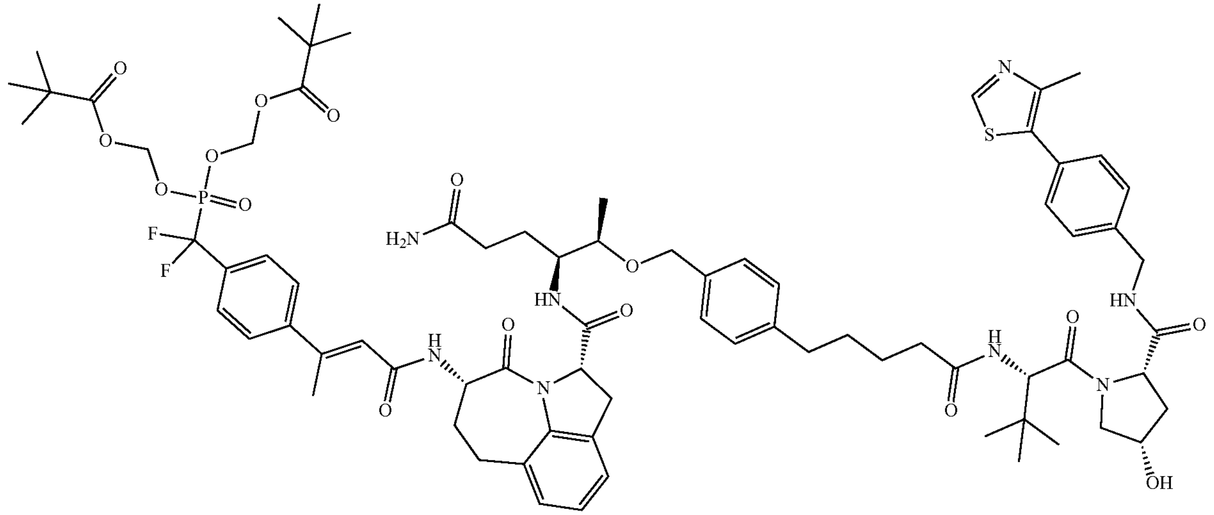 [SMILES: C/C(=C\C(=O)N[C@H]1CCc2cccc3c2N(C1=O)[C@H](C(=O)N[C@@H](CCC(N)=O)[C@@H](C)OCc1ccc(CCCCC(=O)N[C@H](C(=O)N2C[C@@H](O)C[C@H]2C(=O)NCc2ccc(-c4scnc4C)cc2)C(C)(C)C)cc1)C3)c1ccc(C(F)(F)P(=O)(OCOC(=O)C(C)(C)C)OCOC(=O)C(C)(C)C)cc1] |

TABLE 1-continued
| Exemplary Compounds | |
|---|---|
| I-# | Structure |
| I-3 | 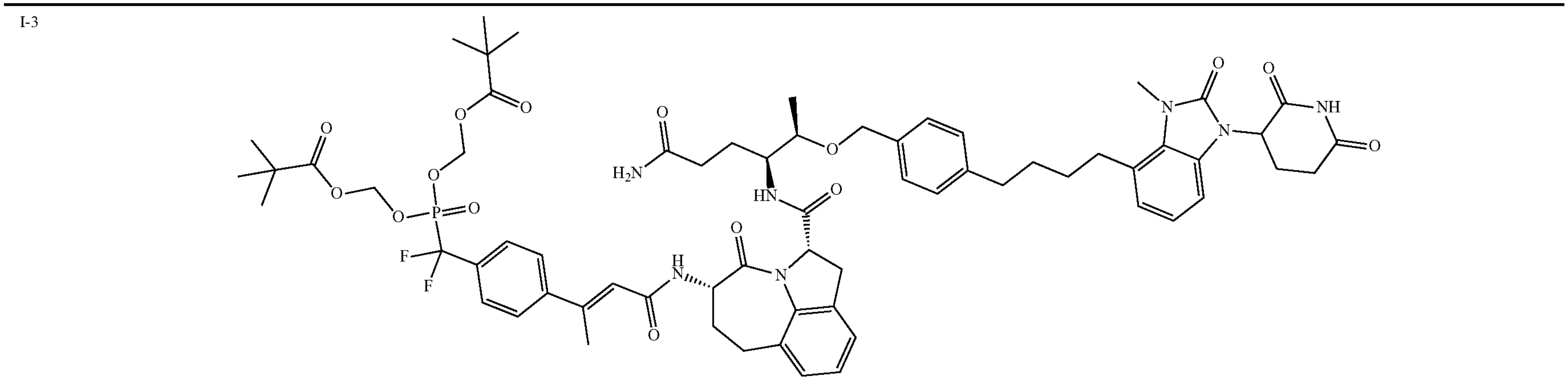 |
| I-4 | 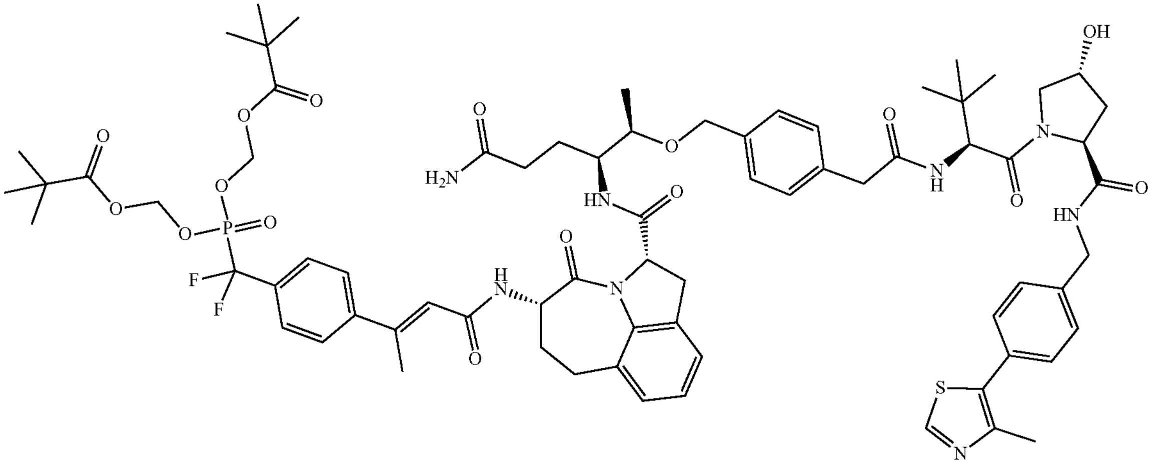 [SMILES: C/C(=C\C(=O)N[C@H]1CCc2cccc3c2N(C1=O)[C@H](C(=O)N[C@@H](CCC(N)=O)[C@@H](C)OCc1ccc(CC(=O)N[C@H](C(=O)N2C[C@H](O)C[C@H]2C(=O)NCc2ccc(-c4scnc4C)cc2)C(C)(C)C)cc1)C3)c1ccc(C(F)(F)P(=O)(OCOC(=O)C(C)(C)C)OCOC(=O)C(C)(C)C)cc1] |

TABLE 1-continued
Exemplary Compounds
| I-# | Structure |
| --- | --- |
| I-5 | 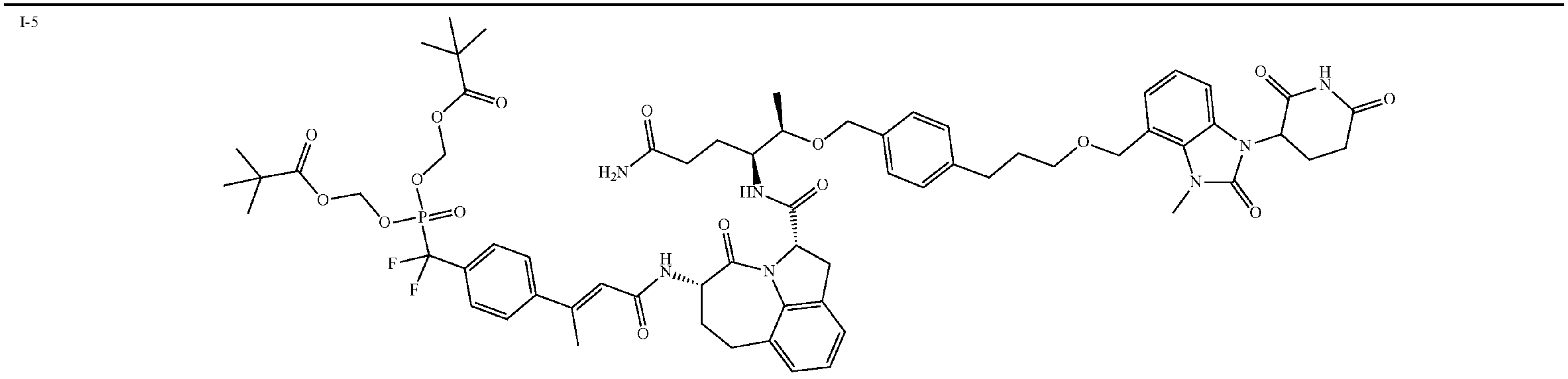 |
| I-6 | 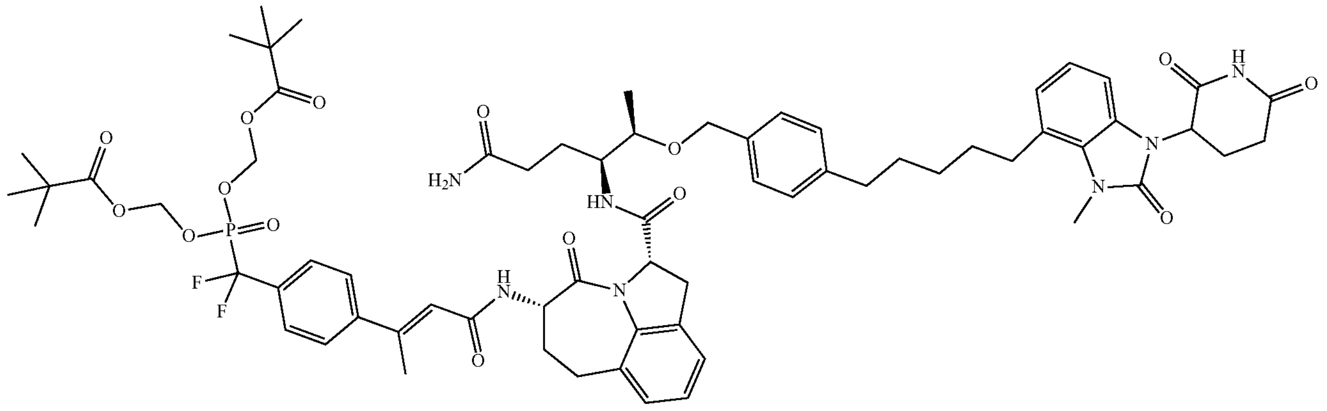 [SMILES: C/C(=C\C(=O)N[C@H]1CCc2cccc3c2N(C1=O)[C@H](C(=O)N[C@@H](CCC(N)=O)[C@@H](C)OCc1ccc(CCCCCc2cccc4c2n(C)c(=O)n4C2CCC(=O)NC2=O)cc1)C3)c1ccc(C(F)(F)P(=O)(OCOC(=O)C(C)(C)C)OCOC(=O)C(C)(C)C)cc1] |

TABLE 1-continued
| Exemplary Compounds | |
|---|---|
| I-# | Structure |
| I-7 | 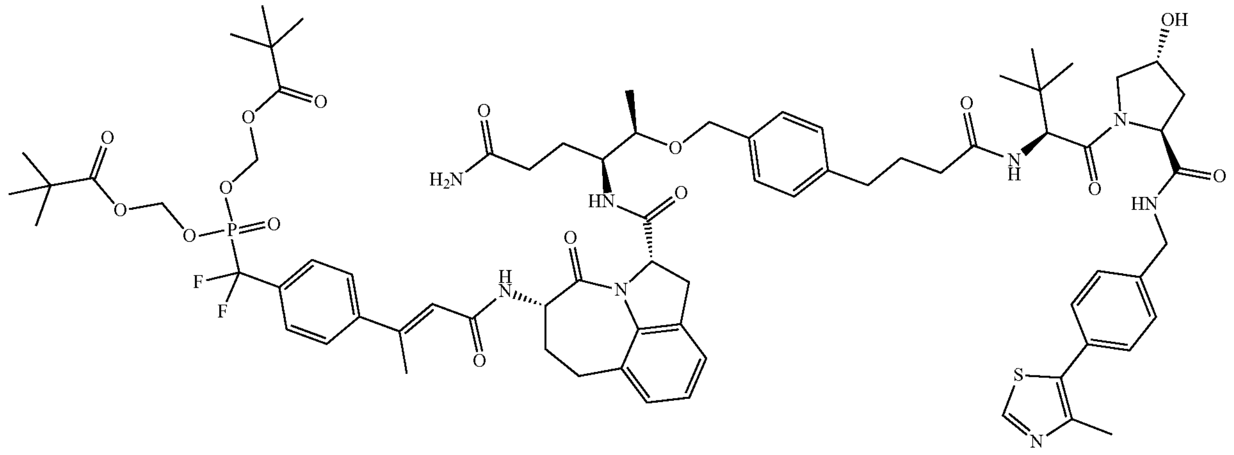 [SMILES: C/C(=C\C(=O)N[C@H]1CCc2cccc3c2N(C1=O)[C@H](C(=O)N[C@@H](CCC(N)=O)[C@@H](C)OCc1ccc(CCCC(=O)N[C@H](C(=O)N2C[C@H](O)C[C@H]2C(=O)NCc2ccc(-c4scnc4C)cc2)C(C)(C)C)cc1)C3)c1ccc(C(F)(F)P(=O)(OCOC(=O)C(C)(C)C)OCOC(=O)C(C)(C)C)cc1] |

TABLE 1-continued
| Exemplary Compounds | |
|---|---|
| I-# | Structure |
| I-8 | 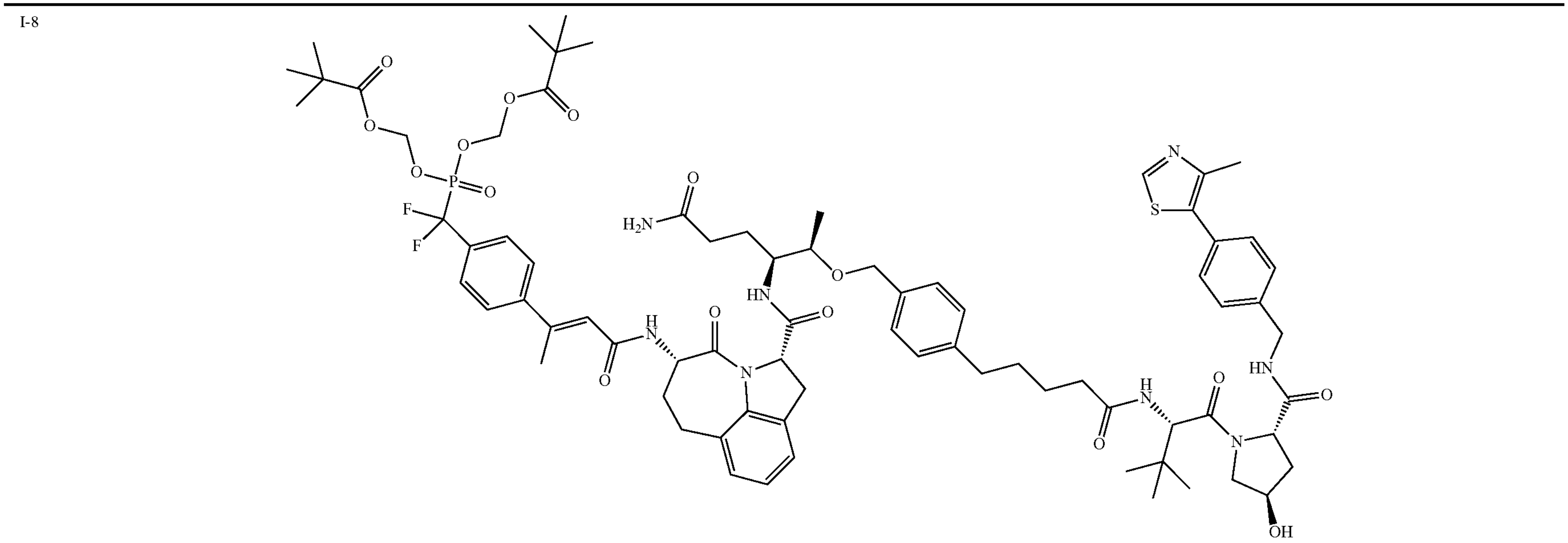 |
| I-9 | 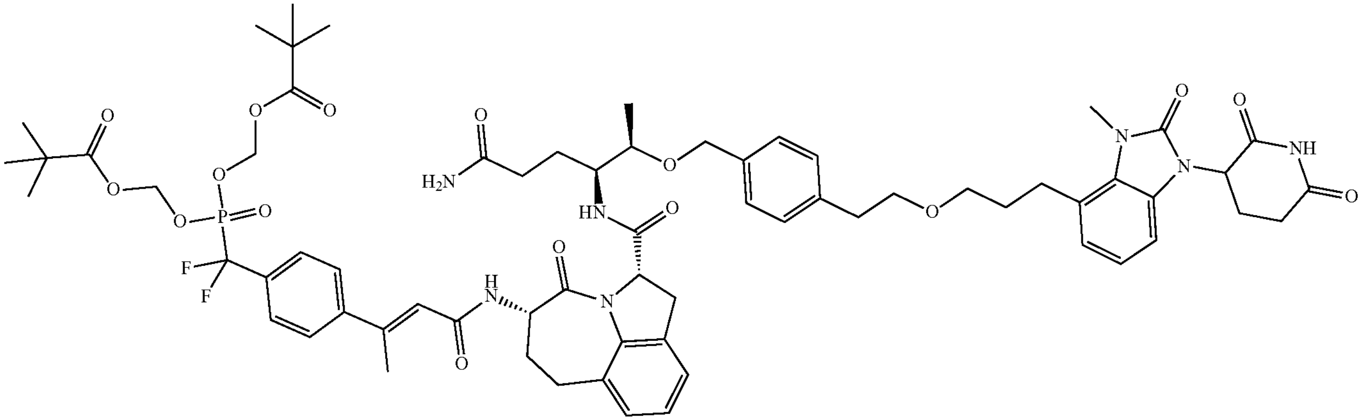 [SMILES: C/C(=C\C(=O)N[C@H]1CCc2cccc3c2N(C1=O)[C@H](C(=O)N[C@@H](CCC(N)=O)[C@@H](C)OCc1ccc(CCOCCCc2cccc4c2n(C)c(=O)n4C2CCC(=O)NC2=O)cc1)C3)c1ccc(C(F)(F)P(=O)(OCOC(=O)C(C)(C)C)OCOC(=O)C(C)(C)C)cc1] |

TABLE 1-continued
| Exemplary Compounds | |
|---|---|
| I-# | Structure |
| I-10 | 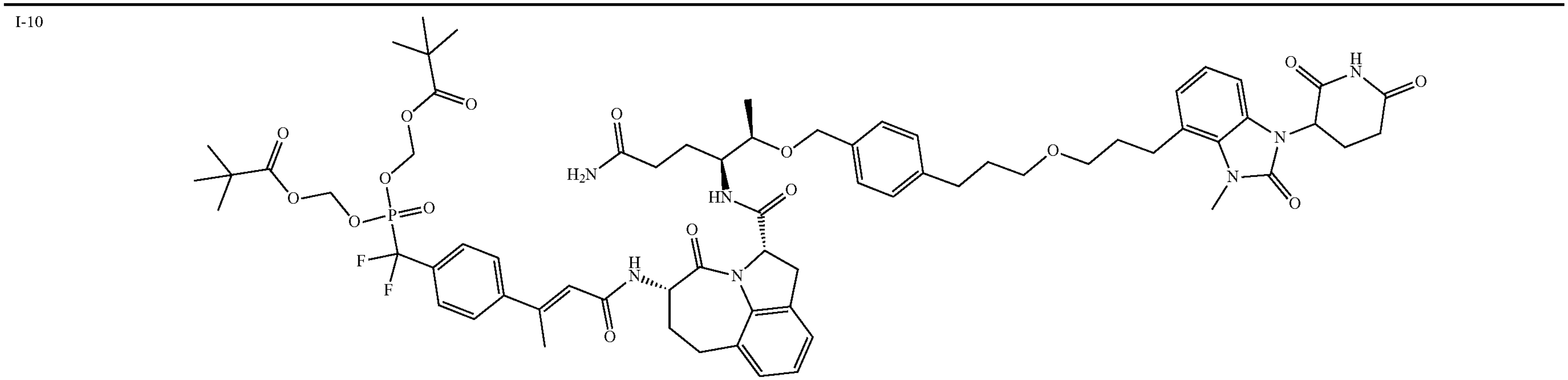 |
| I-11 | 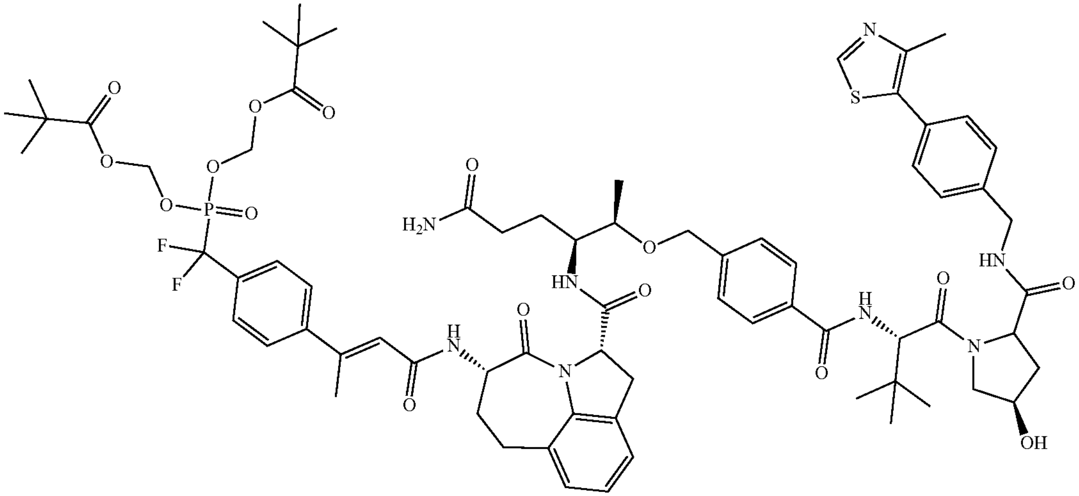 [SMILES: C/C(=C\C(=O)N[C@H]1CCc2cccc3c2N(C1=O)[C@H](C(=O)N[C@@H](CCC(N)=O)[C@@H](C)OCc1ccc(C(=O)N[C@H](C(=O)N2C[C@H](O)CC2C(=O)NCc2ccc(-c4scnc4C)cc2)C(C)(C)C)cc1)C3)c1ccc(C(F)(F)P(=O)(OCOC(=O)C(C)(C)C)OCOC(=O)C(C)(C)C)cc1] |

TABLE 1-continued
| Exemplary Compounds | |
|---|---|
| I-# | Structure |
| I-12 | 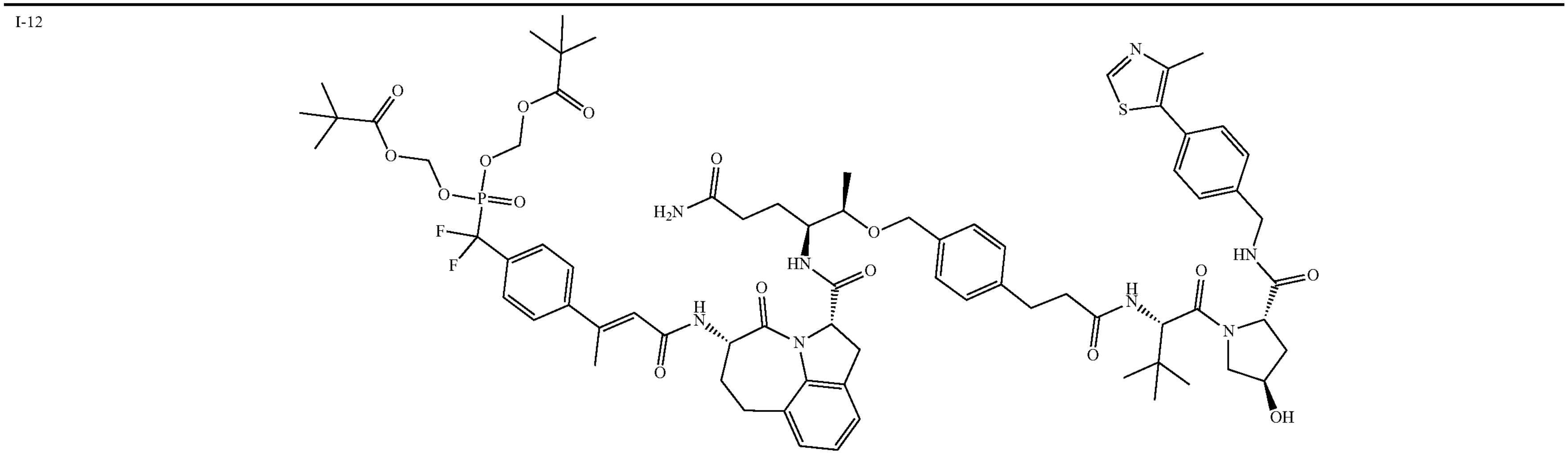 |
| I-13 | 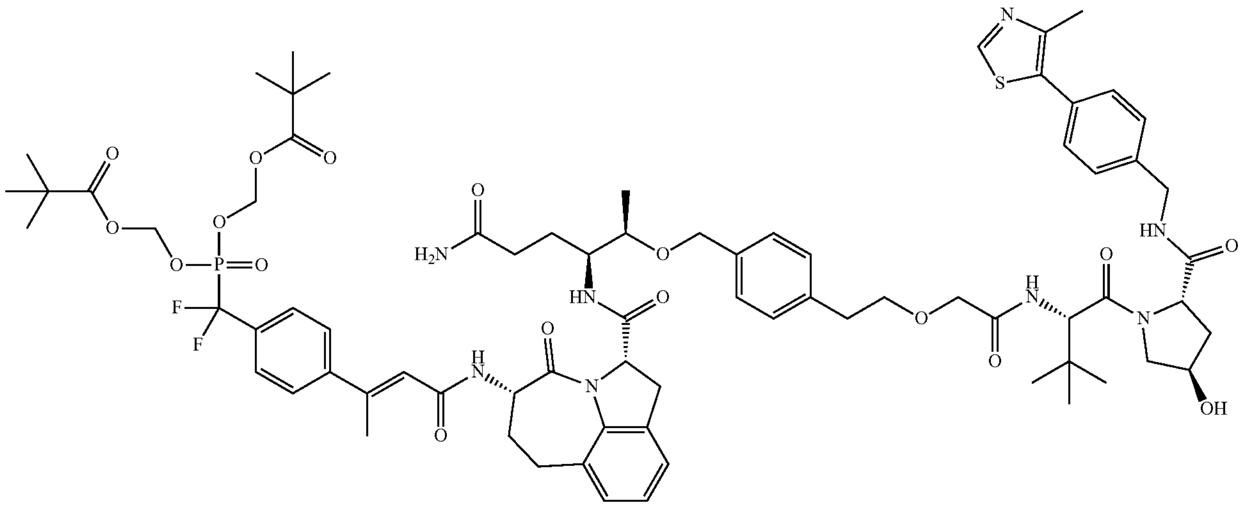 [SMILES: C/C(=C\C(=O)N[C@H]1CCc2cccc3c2N(C1=O)[C@H](C(=O)N[C@@H](CCC(N)=O)[C@@H](C)OCc1ccc(CCOCC(=O)N[C@H](C(=O)N2C[C@H](O)C[C@H]2C(=O)NCc2ccc(-c4scnc4C)cc2)C(C)(C)C)cc1)C3)c1ccc(C(F)(F)P(=O)(OCOC(=O)C(C)(C)C)OCOC(=O)C(C)(C)C)cc1] |

TABLE 1-continued
| Exemplary Compounds | |
|---|---|
| I-# | Structure |
| I-14 | 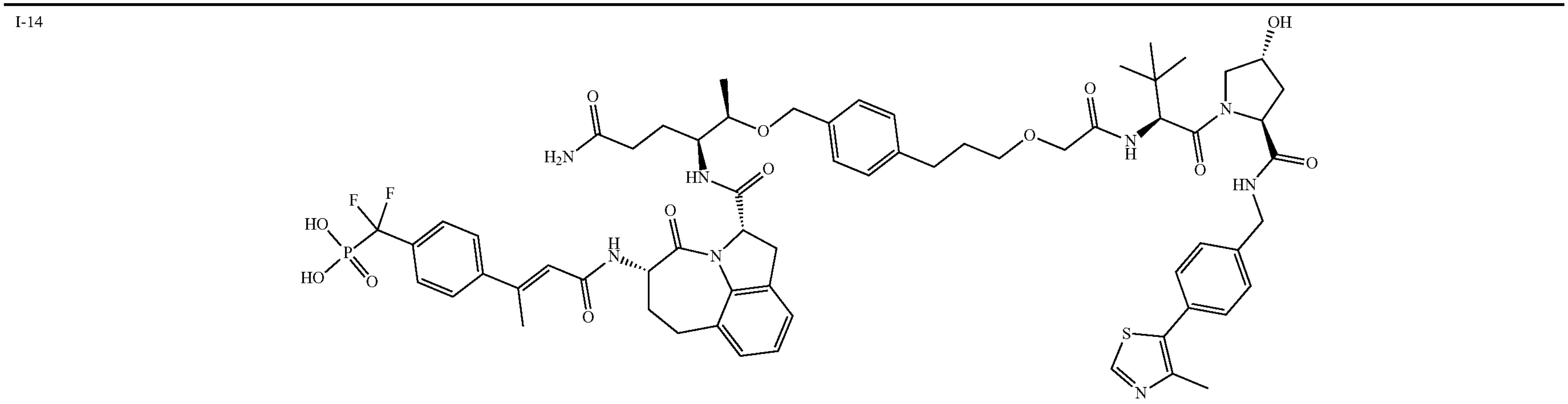 |
| I-15 | 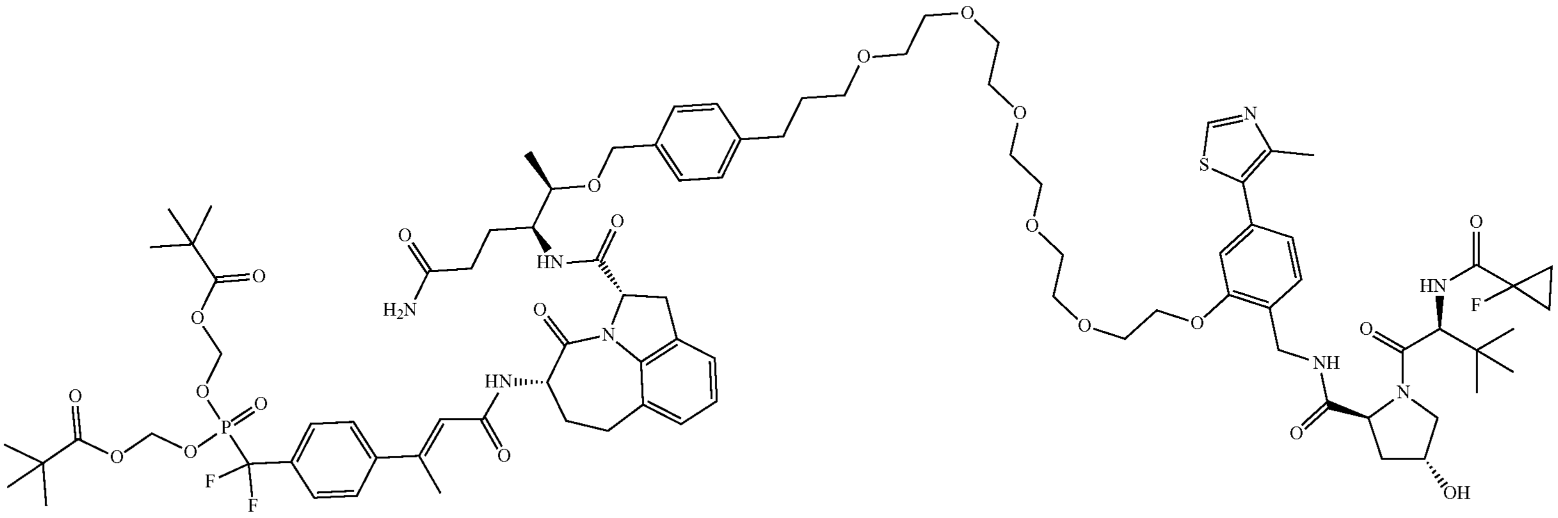 [SMILES: C/C(=C\C(=O)N[C@H]1CCc2cccc3c2N(C1=O)[C@H](C(=O)N[C@@H](CCC(N)=O)[C@@H](C)OCc1ccc(CCCOCCOCCOCCOCCOCCOc2cc(-c4scnc4C)ccc2CNC(=O)[C@@H]2C[C@@H](O)CN2C(=O)[C@@H](NC(=O)C2(F)CC2)C(C)(C)C)cc1)C3)c1ccc(C(F)(F)P(=O)(OCOC(=O)C(C)(C)C)OCOC(=O)C(C)(C)C)cc1] |

TABLE 1-continued
| Exemplary Compounds | |
|---|---|
| I-# | Structure |
| I-16 | 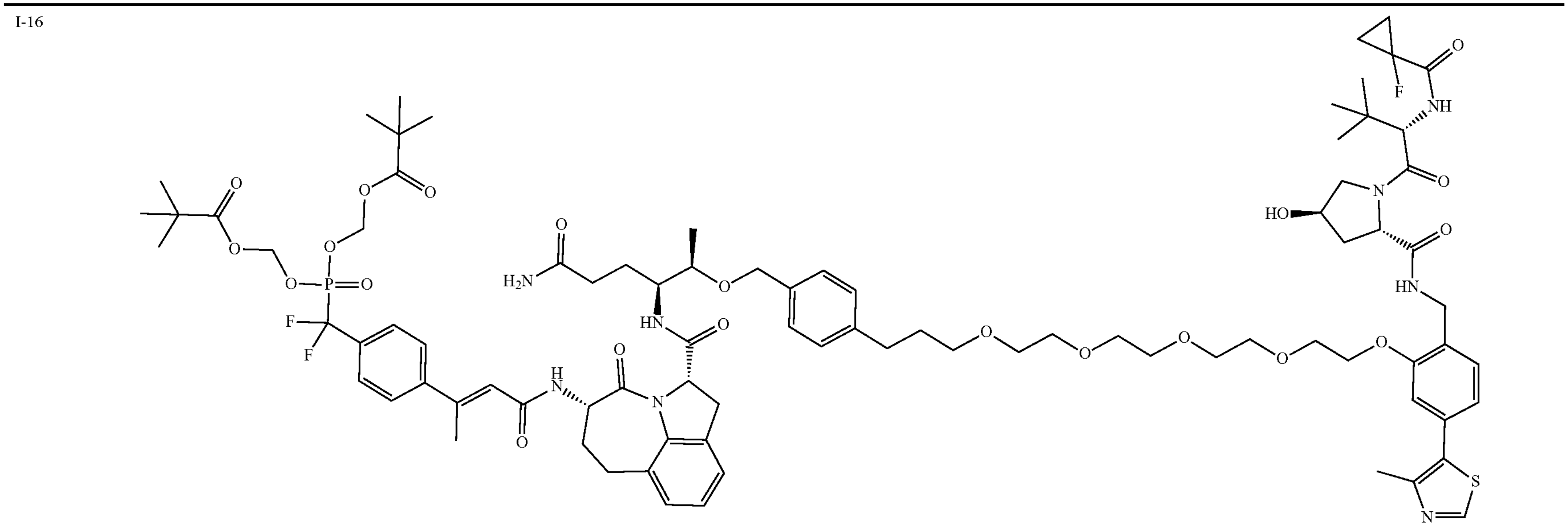 |

TABLE 1-continued
| Exemplary Compounds | |
|---|---|
| I-# | Structure |
| I-17 | 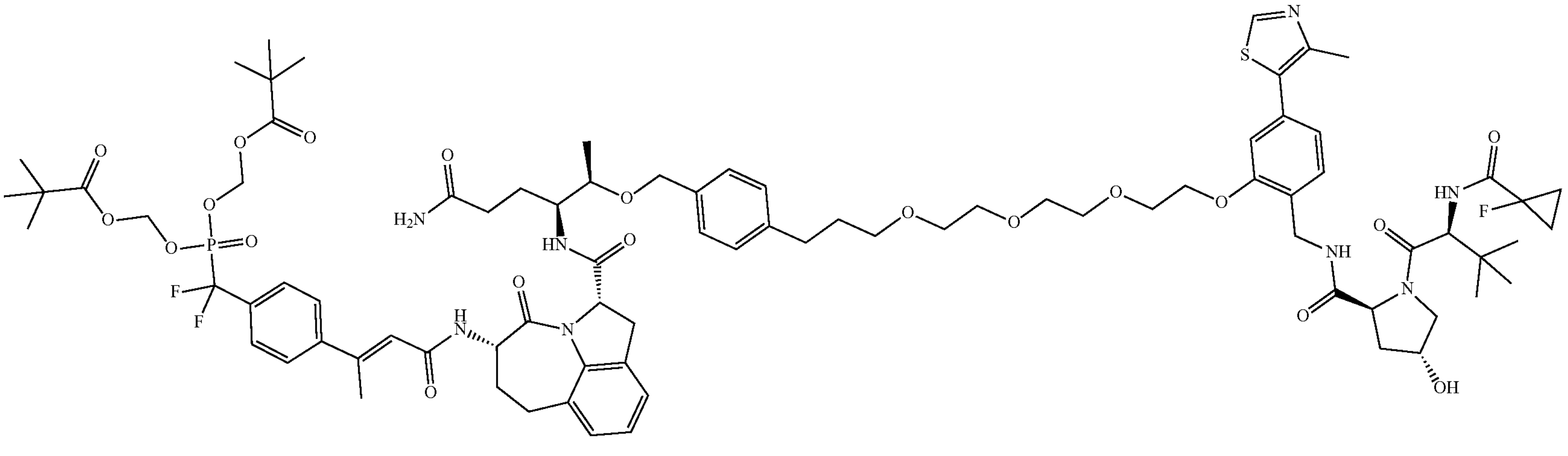 [SMILES: C/C(=C\C(=O)N[C@H]1CCc2cccc3c2N(C1=O)[C@H](C(=O)N[C@@H](CCC(N)=O)[C@@H](C)OCc1ccc(CCCOCCOCCOCCOc2cc(-c4scnc4C)ccc2CNC(=O)[C@@H]2C[C@@H](O)CN2C(=O)[C@@H](NC(=O)C2(F)CC2)C(C)(C)C)cc1)C3)c1ccc(C(F)(F)P(=O)(OCOC(=O)C(C)(C)C)OCOC(=O)C(C)(C)C)cc1] |

TABLE 1-continued
| Exemplary Compounds | |
|---|---|
| I-# | Structure |
| I-18 | 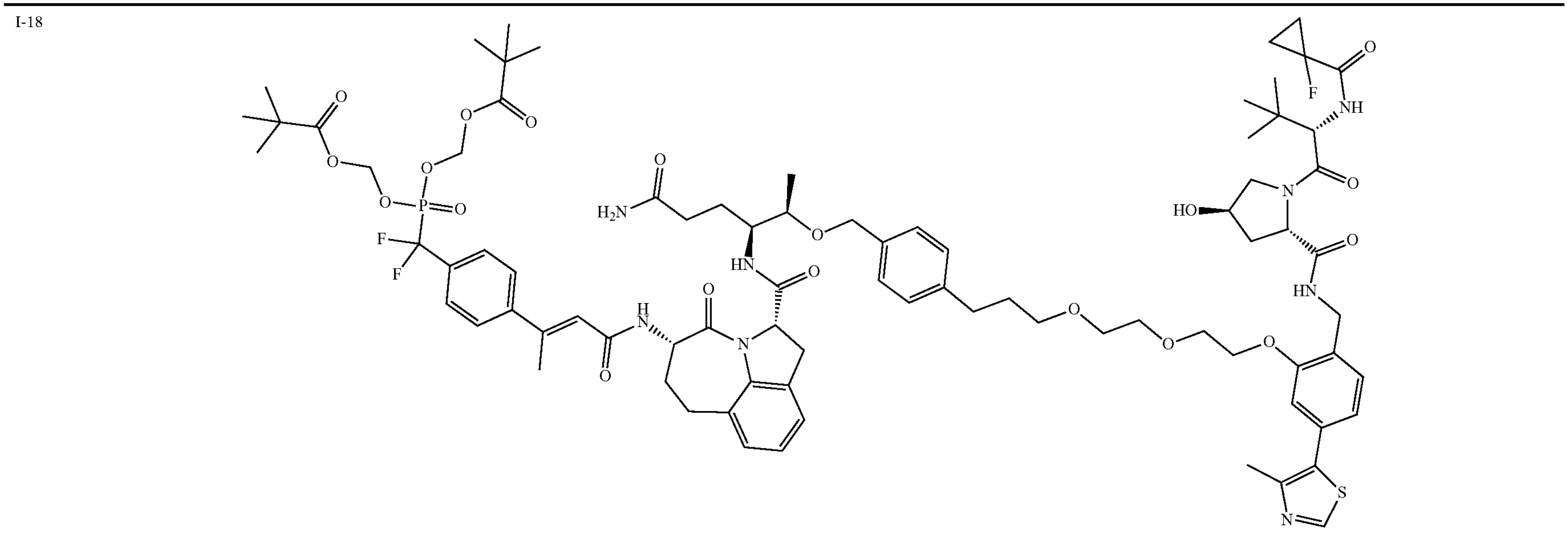 |
| I-19 | 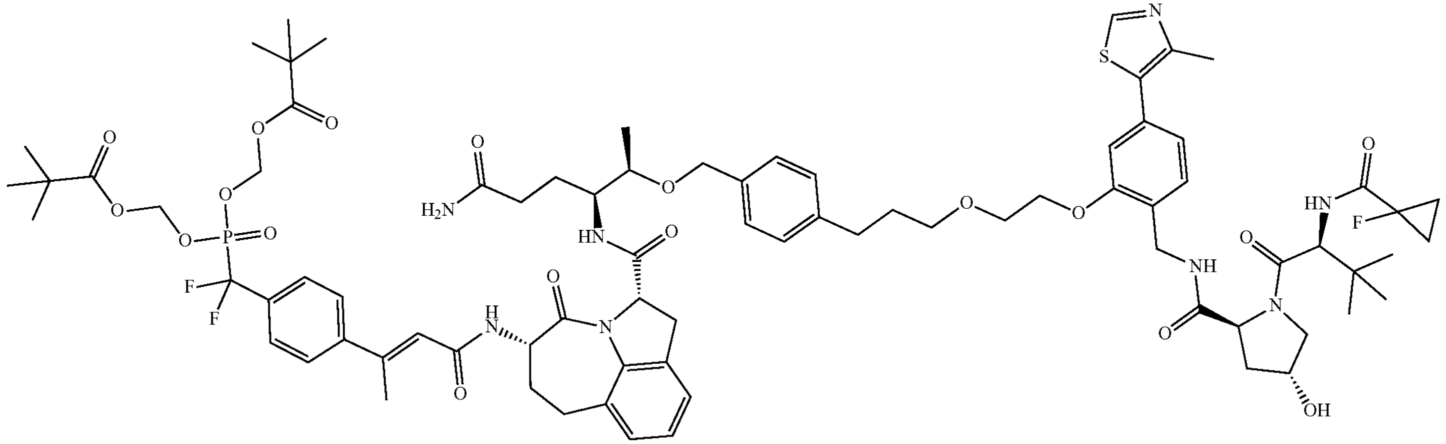 [SMILES: C/C(=C\C(=O)N[C@H]1CCc2cccc3c2N(C1=O)[C@H](C(=O)N[C@@H](CCC(N)=O)[C@@H](C)OCc1ccc(CCCOCCOc2cc(-c4scnc4C)ccc2CNC(=O)[C@@H]2C[C@@H](O)CN2C(=O)[C@@H](NC(=O)C2(F)CC2)C(C)(C)C)cc1)C3)c1ccc(C(F)(F)P(=O)(OCOC(=O)C(C)(C)C)OCOC(=O)C(C)(C)C)cc1] |

TABLE 1-continued
| Exemplary Compounds | |
|---|---|
| I-# | Structure |
| I-20 | 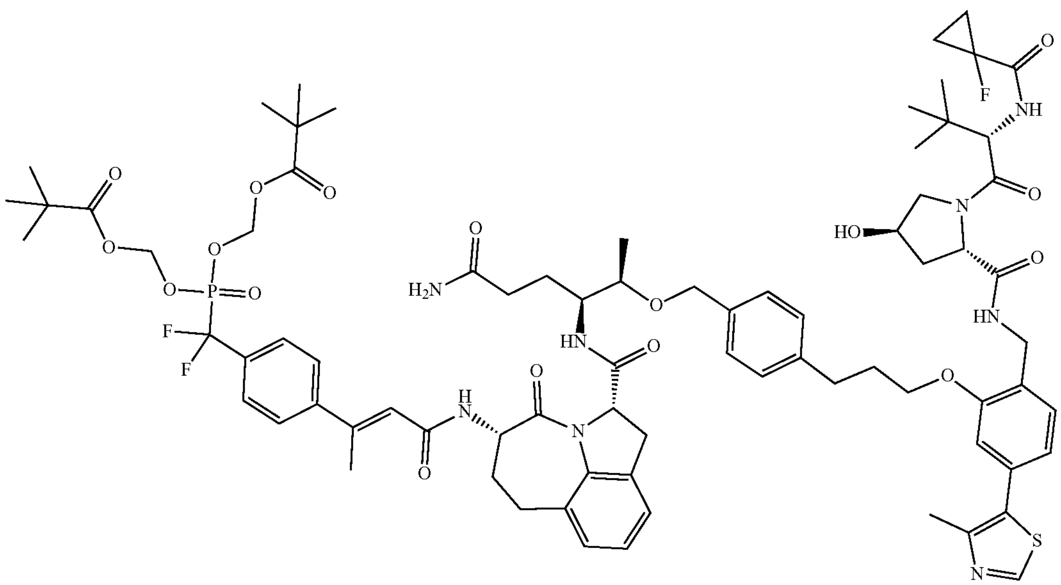 [SMILES: C/C(=C\C(=O)N[C@H]1CCc2cccc3c2N(C1=O)[C@H](C(=O)N[C@@H](CCC(N)=O)[C@@H](C)OCc1ccc(CCCOc2cc(-c4scnc4C)ccc2CNC(=O)[C@@H]2C[C@@H](O)CN2C(=O)[C@@H](NC(=O)C2(F)CC2)C(C)(C)C)cc1)C3)c1ccc(C(F)(F)P(=O)(OCOC(=O)C(C)(C)C)OCOC(=O)C(C)(C)C)cc1] |

TABLE 1-continued
| Exemplary Compounds | |
|---|---|
| I-# | Structure |
| I-21 | 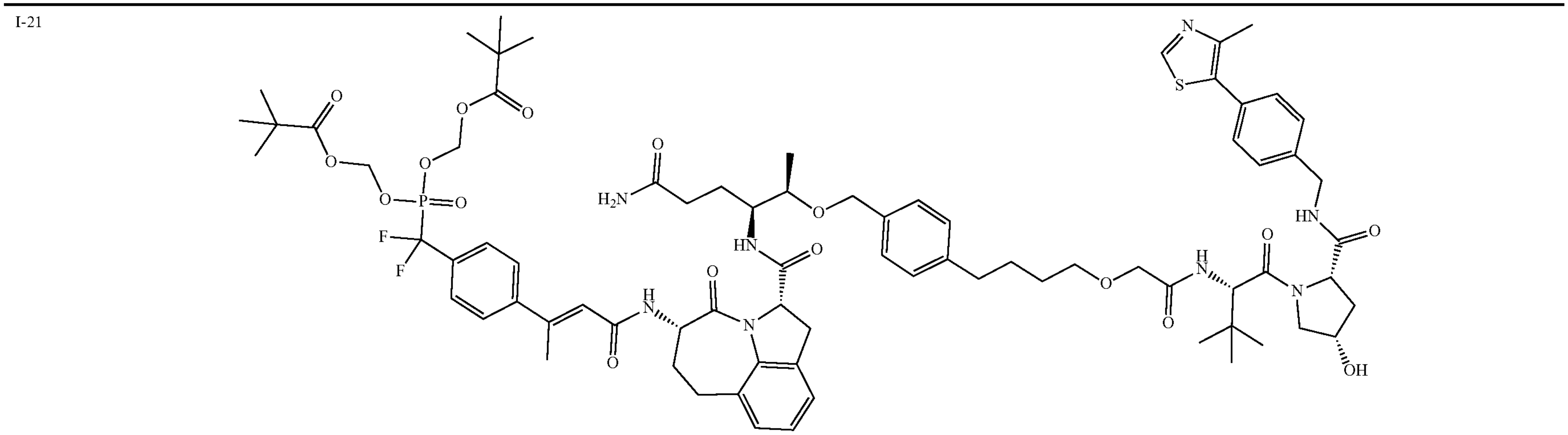 |
| I-22 | 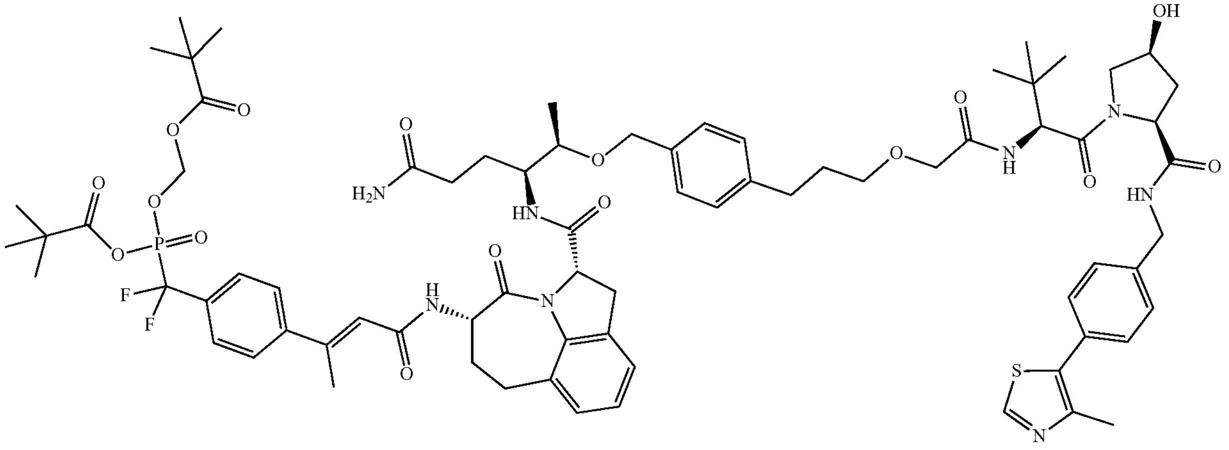 [SMILES: C/C(=C\C(=O)N[C@H]1CCc2cccc3c2N(C1=O)[C@H](C(=O)N[C@@H](CCC(N)=O)[C@@H](C)OCc1ccc(CCCOCC(=O)N[C@H](C(=O)N2C[C@@H](O)C[C@H]2C(=O)NCc2ccc(-c4scnc4C)cc2)C(C)(C)C)cc1)C3)c1ccc(C(F)(F)P(=O)(OCOC(=O)C(C)(C)C)OC(=O)C(C)(C)C)cc1] |

TABLE 1-continued
| Exemplary Compounds | |
|---|---|
| I-# | Structure |
| I-23 | 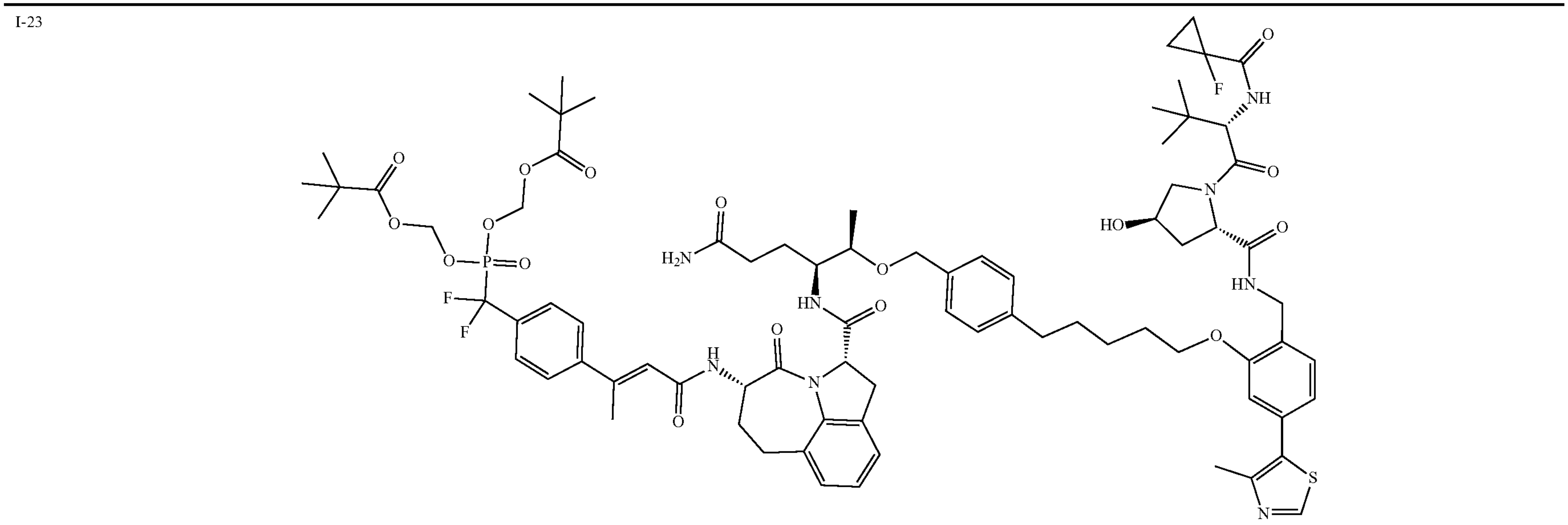 |
| I-24 | 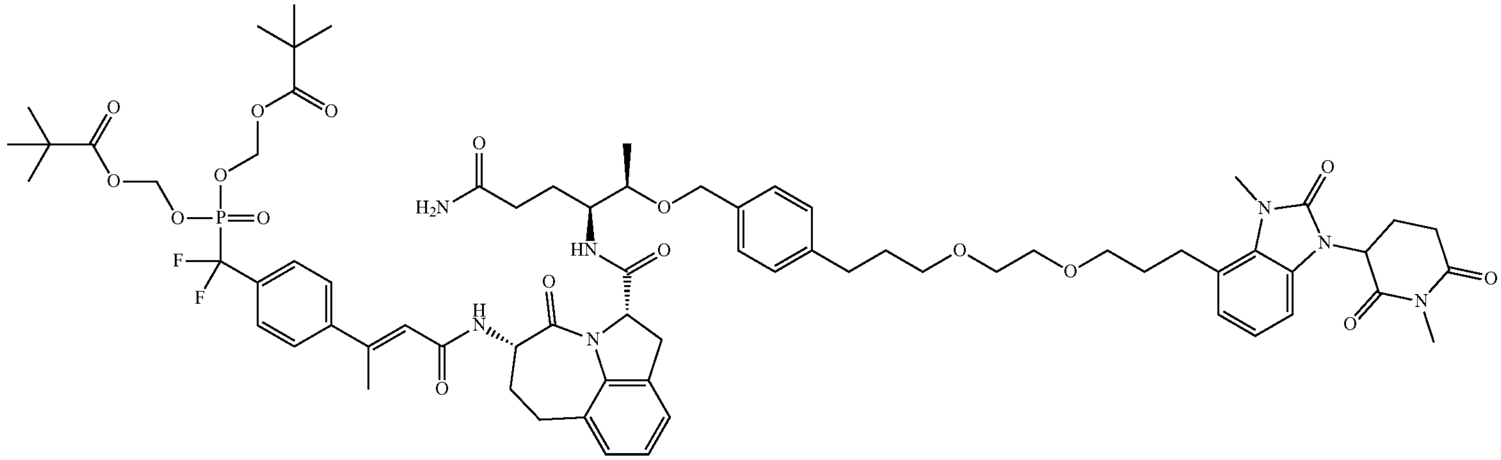 [SMILES: C/C(=C\C(=O)N[C@H]1CCc2cccc3c2N(C1=O)[C@H](C(=O)N[C@@H](CCC(N)=O)[C@@H](C)OCc1ccc(CCCOCCOCCCc2cccc4c2n(C)c(=O)n4C2CCC(=O)N(C)C2=O)cc1)C3)c1ccc(C(F)(F)P(=O)(OCOC(=O)C(C)(C)C)OCOC(=O)C(C)(C)C)cc1] |

TABLE 1-continued
| Exemplary Compounds | |
|---|---|
| I-# | Structure |
| I-25 | 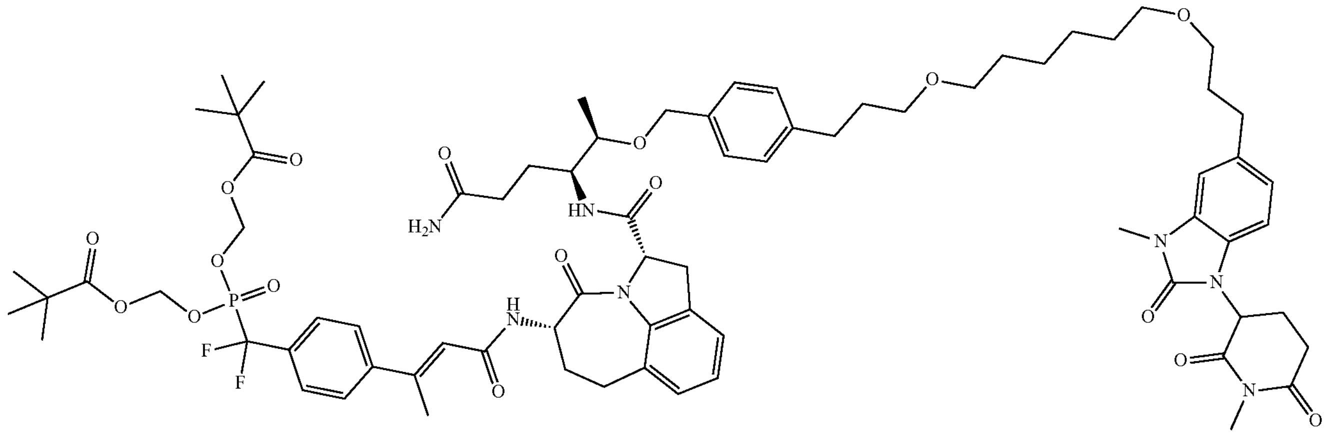 [SMILES: C/C(=C\C(=O)N[C@H]1CCc2cccc3c2N(C1=O)[C@H](C(=O)N[C@@H](CCC(N)=O)[C@@H](C)OCc1ccc(CCCOCCCCCCOCCCc2ccc4c(c2)n(C)c(=O)n4C2CCC(=O)N(C)C2=O)cc1)C3)c1ccc(C(F)(F)P(=O)(OCOC(=O)C(C)(C)C)OCOC(=O)C(C)(C)C)cc1] |
| I-26 | 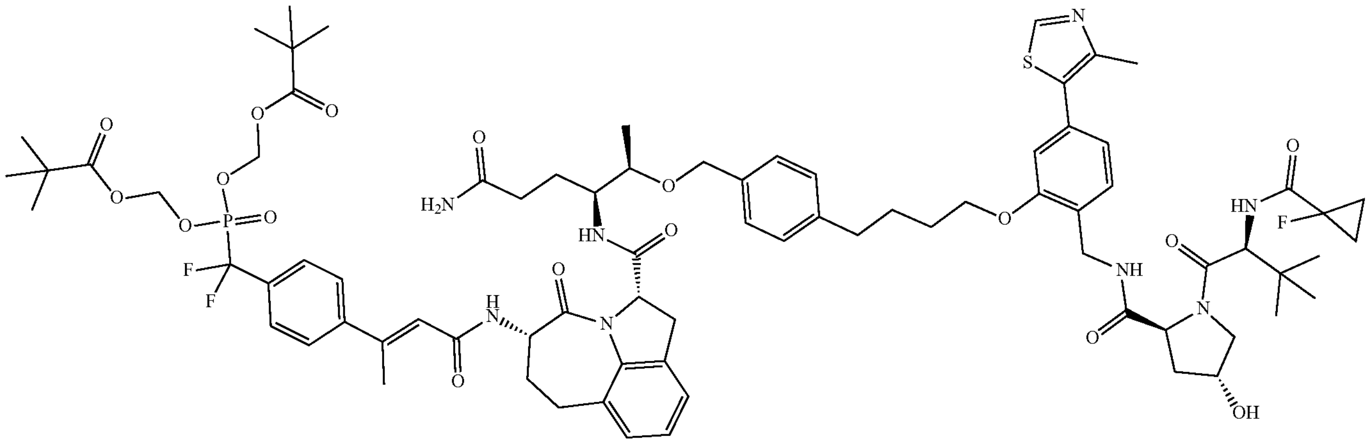 [SMILES: C/C(=C\C(=O)N[C@H]1CCc2cccc3c2N(C1=O)[C@H](C(=O)N[C@@H](CCC(N)=O)[C@@H](C)OCc1ccc(CCCCOc2cc(-c4scnc4C)ccc2CNC(=O)[C@@H]2C[C@@H](O)CN2C(=O)[C@@H](NC(=O)C2(F)CC2)C(C)(C)C)cc1)C3)c1ccc(C(F)(F)P(=O)(OCOC(=O)C(C)(C)C)OCOC(=O)C(C)(C)C)cc1] |

TABLE 1-continued
| Exemplary Compounds | |
|---|---|
| I-# | Structure |
| I-27 | 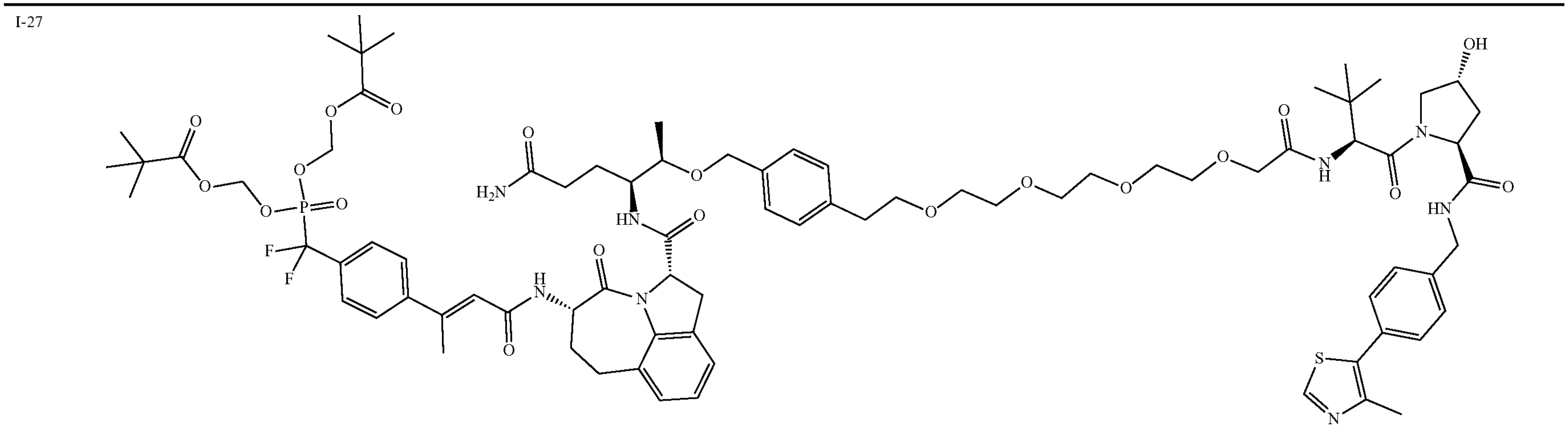 |
| I-28 | 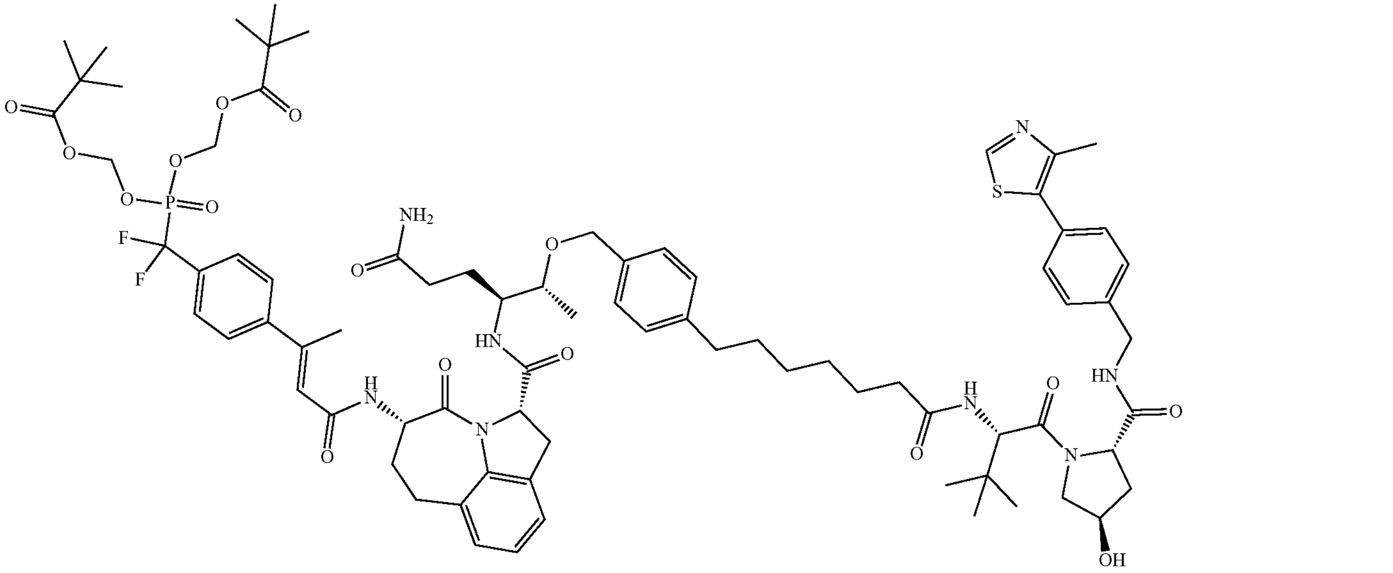 [SMILES: C/C(=C\C(=O)N[C@H]1CCc2cccc3c2N(C1=O)[C@H](C(=O)N[C@@H](CCC(N)=O)[C@@H](C)OCc1ccc(CCCCCCC(=O)N[C@H](C(=O)N2C[C@H](O)C[C@H]2C(=O)NCc2ccc(-c4scnc4C)cc2)C(C)(C)C)cc1)C3)c1ccc(C(F)(F)P(=O)(OCOC(=O)C(C)(C)C)OCOC(=O)C(C)(C)C)cc1] |

TABLE 1-continued
| Exemplary Compounds | |
|---|---|
| I-# | Structure |
| I-29 | 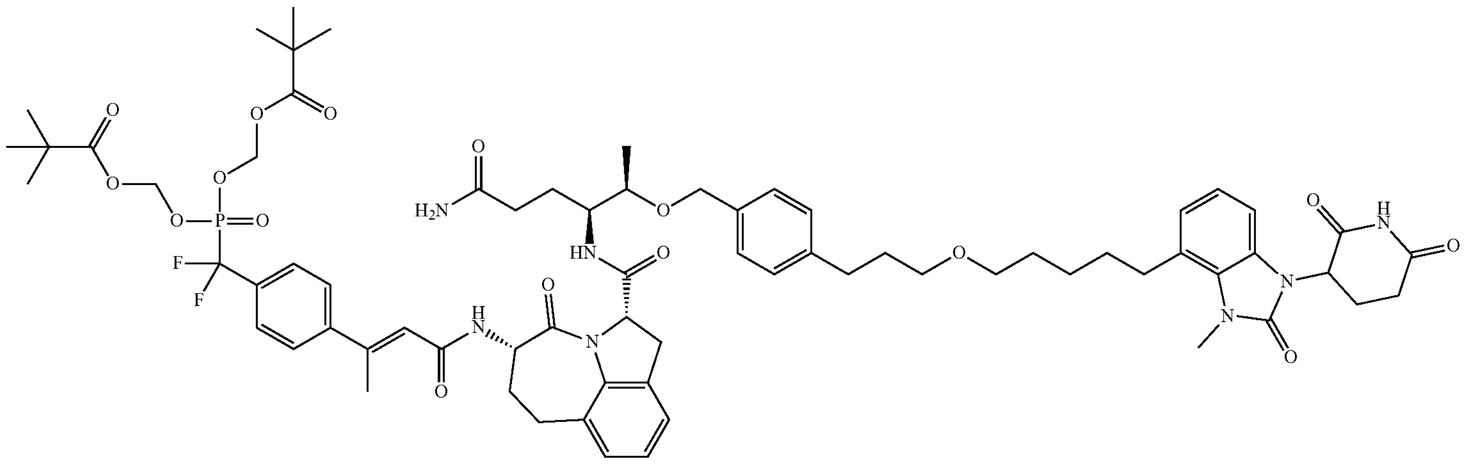 [SMILES: C/C(=C\C(=O)N[C@H]1CCc2cccc3c2N(C1=O)[C@H](C(=O)N[C@@H](CCC(N)=O)[C@@H](C)OCc1ccc(CCCOCCCCCc2cccc4c2n(C)c(=O)n4C2CCC(=O)NC2=O)cc1)C3)c1ccc(C(F)(F)P(=O)(OCOC(=O)C(C)(C)C)OCOC(=O)C(C)(C)C)cc1] |
| I-30 | 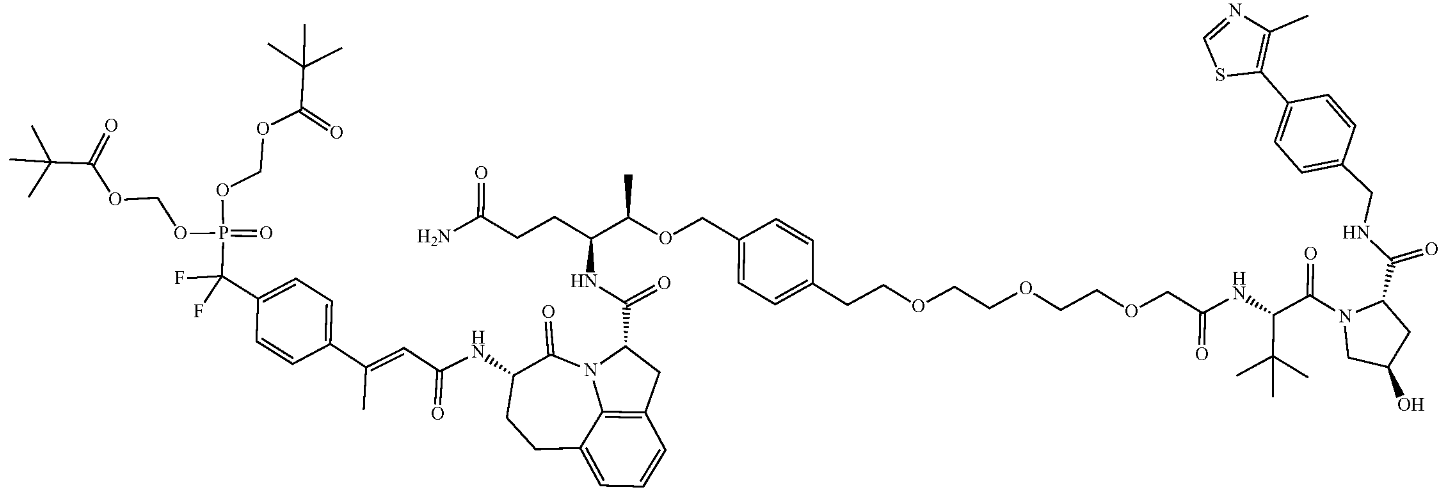 [SMILES: C/C(=C\C(=O)N[C@H]1CCc2cccc3c2N(C1=O)[C@H](C(=O)N[C@@H](CCC(N)=O)[C@@H](C)OCc1ccc(CCOCCOCCOCC(=O)N[C@H](C(=O)N2C[C@H](O)C[C@H]2C(=O)NCc2ccc(-c4scnc4C)cc2)C(C)(C)C)cc1)C3)c1ccc(C(F)(F)P(=O)(OCOC(=O)C(C)(C)C)OCOC(=O)C(C)(C)C)cc1] |

TABLE 1-continued
| Exemplary Compounds | |
|---|---|
| I-# | Structure |
| I-31 | 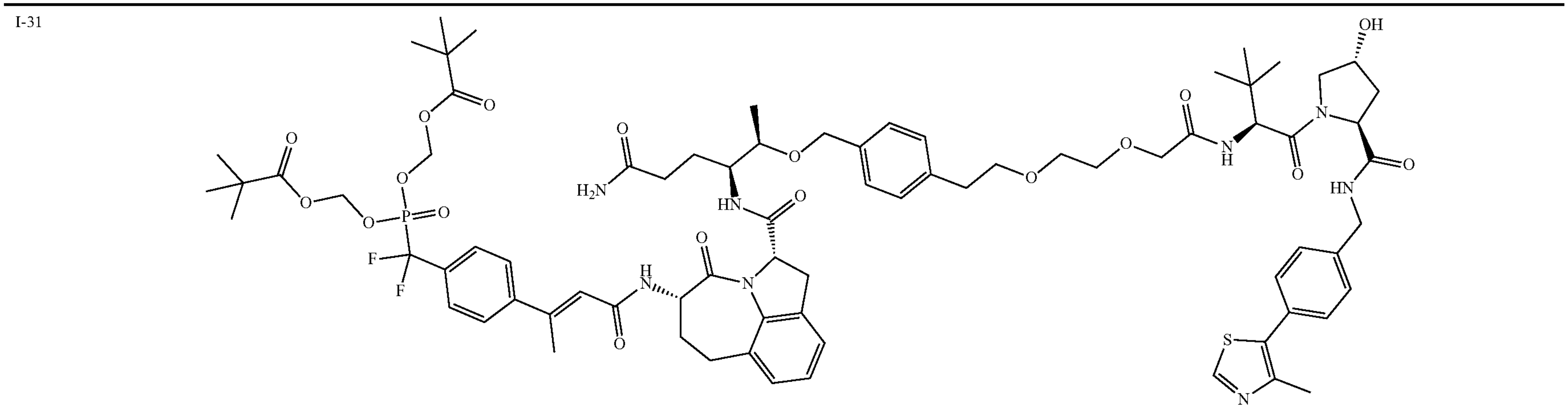 |
| I-32 | 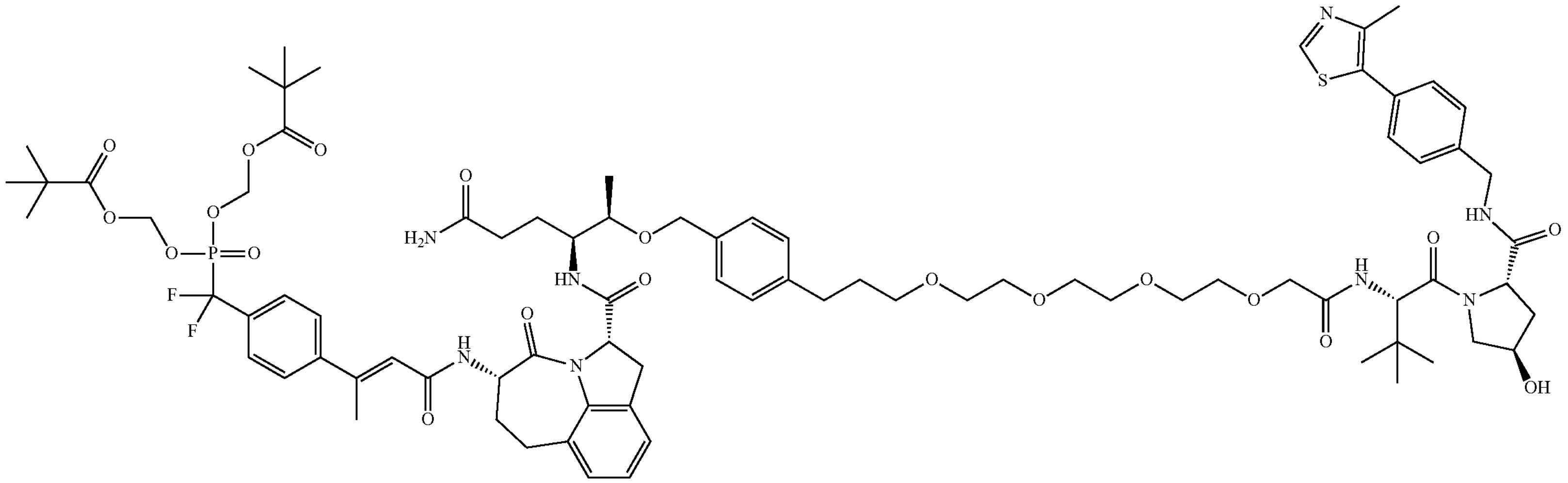 [SMILES: C/C(=C\C(=O)N[C@H]1CCc2cccc3c2N(C1=O)[C@H](C(=O)N[C@@H](CCC(N)=O)[C@@H](C)OCc1ccc(CCCOCCOCCOCCOCC(=O)N[C@H](C(=O)N2C[C@H](O)C[C@H]2C(=O)NCc2ccc(-c4scnc4C)cc2)C(C)(C)C)cc1)C3)c1ccc(C(F)(F)P(=O)(OCOC(=O)C(C)(C)C)OCOC(=O)C(C)(C)C)cc1] |

TABLE 1-continued
| Exemplary Compounds | |
|---|---|
| I-# | Structure |
| I-33 | 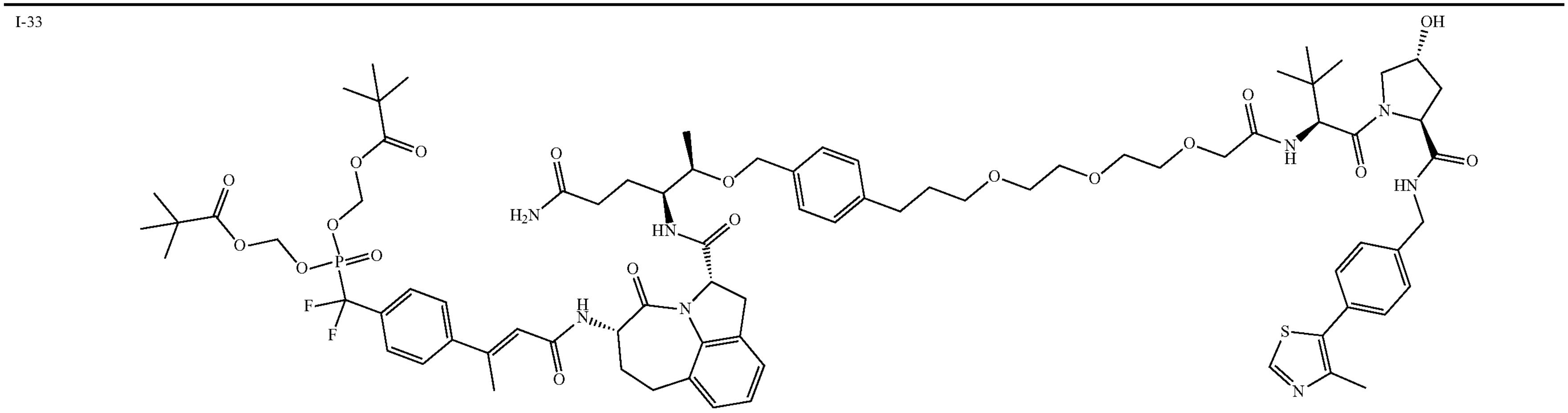 |
| I-34 | 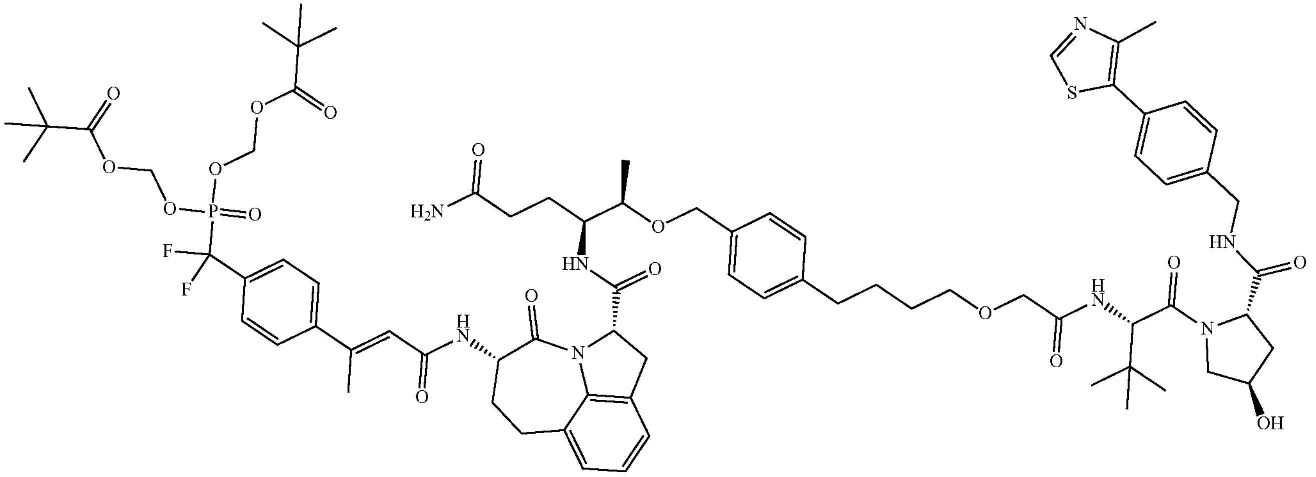 [SMILES: C/C(=C\C(=O)N[C@H]1CCc2cccc3c2N(C1=O)[C@H](C(=O)N[C@@H](CCC(N)=O)[C@@H](C)OCc1ccc(CCCCOCC(=O)N[C@H](C(=O)N2C[C@H](O)C[C@H]2C(=O)NCc2ccc(-c4scnc4C)cc2)C(C)(C)C)cc1)C3)c1ccc(C(F)(F)P(=O)(OCOC(=O)C(C)(C)C)OCOC(=O)C(C)(C)C)cc1] |

TABLE 1-continued
| Exemplary Compounds | |
|---|---|
| I-# | Structure |
| I-35 | 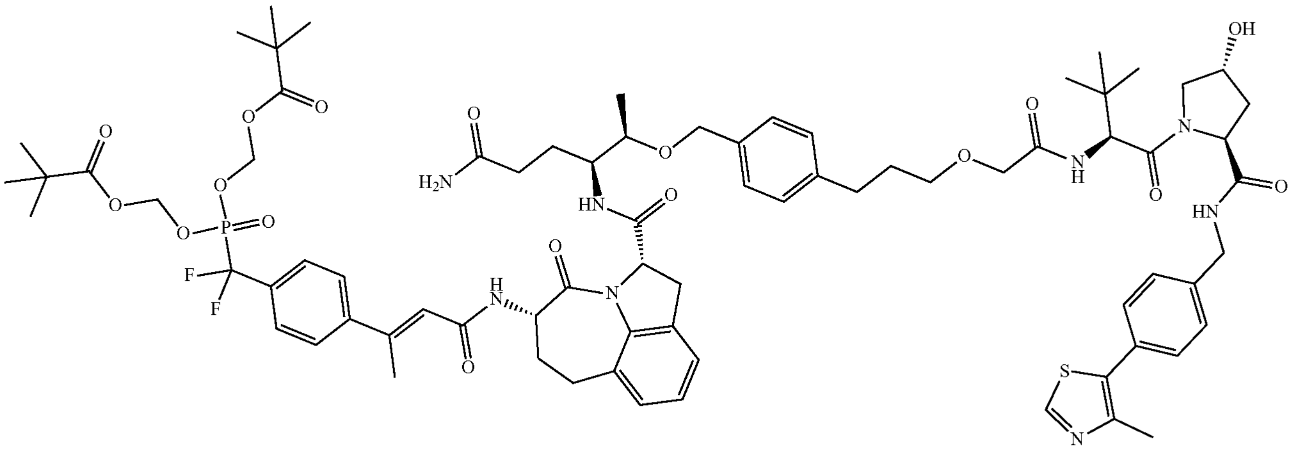 [SMILES: C/C(=C\C(=O)N[C@H]1CCc2cccc3c2N(C1=O)[C@H](C(=O)N[C@@H](CCC(N)=O)[C@@H](C)OCc1ccc(CCCOCC(=O)N[C@H](C(=O)N2C[C@H](O)C[C@H]2C(=O)NCc2ccc(-c4scnc4C)cc2)C(C)(C)C)cc1)C3)c1ccc(C(F)(F)P(=O)(OCOC(=O)C(C)(C)C)OCOC(=O)C(C)(C)C)cc1] |
| I-36 | 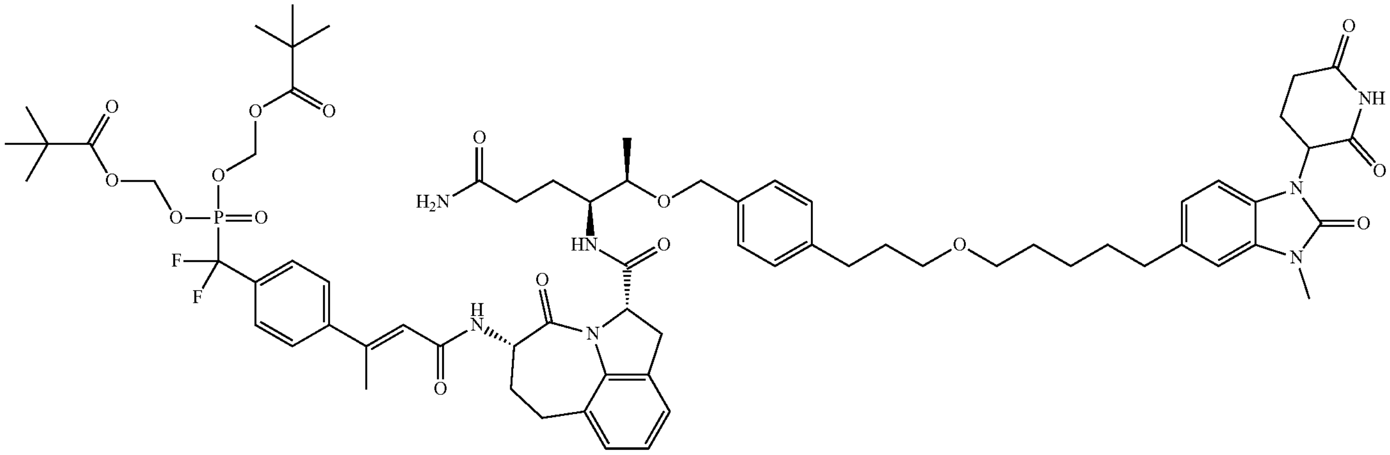 [SMILES: C/C(=C\C(=O)N[C@H]1CCc2cccc3c2N(C1=O)[C@H](C(=O)N[C@@H](CCC(N)=O)[C@@H](C)OCc1ccc(CCCOCCCCCc2ccc4c(c2)n(C)c(=O)n4C2CCC(=O)NC2=O)cc1)C3)c1ccc(C(F)(F)P(=O)(OCOC(=O)C(C)(C)C)OCOC(=O)C(C)(C)C)cc1] |

TABLE 1-continued
| Exemplary Compounds | |
|---|---|
| I-# | Structure |
| I-37 | 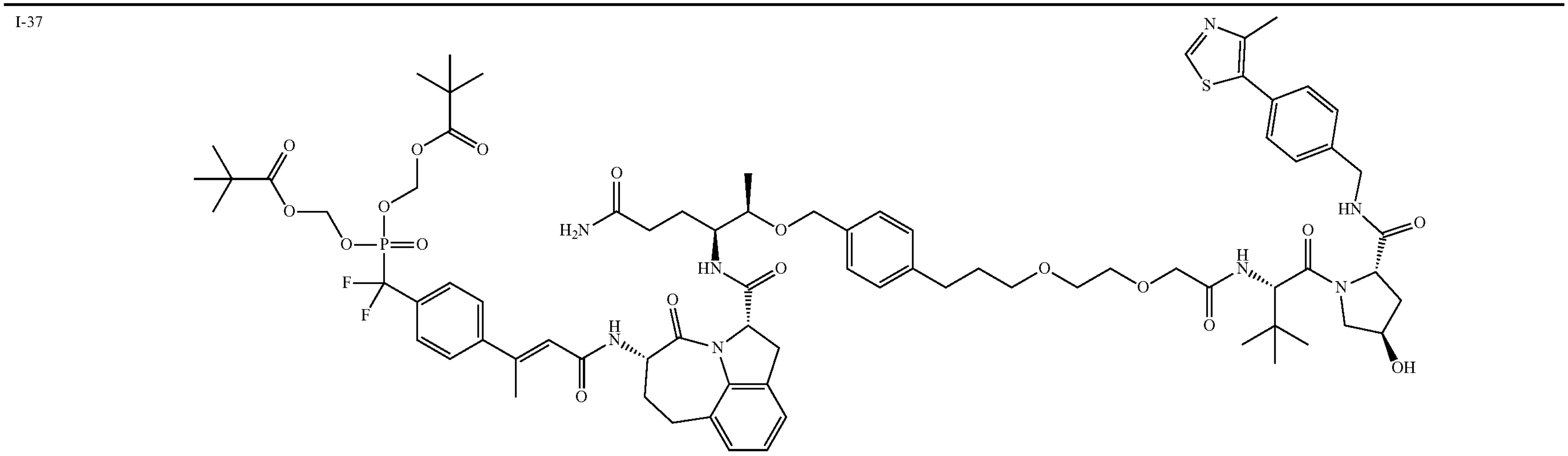 |
| I-38 | 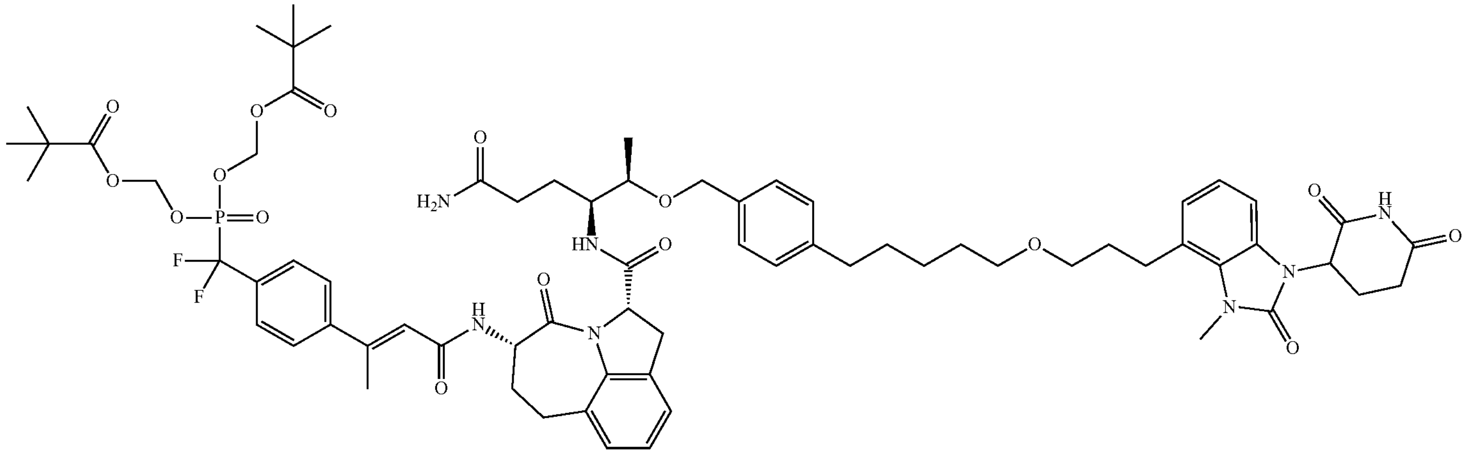 [SMILES: C/C(=C\C(=O)N[C@H]1CCc2cccc3c2N(C1=O)[C@H](C(=O)N[C@@H](CCC(N)=O)[C@@H](C)OCc1ccc(CCCCCOCCCc2cccc4c2n(C)c(=O)n4C2CCC(=O)NC2=O)cc1)C3)c1ccc(C(F)(F)P(=O)(OCOC(=O)C(C)(C)C)OCOC(=O)C(C)(C)C)cc1] |

TABLE 1-continued
| Exemplary Compounds | |
|---|---|
| I-# | Structure |
| I-39 | 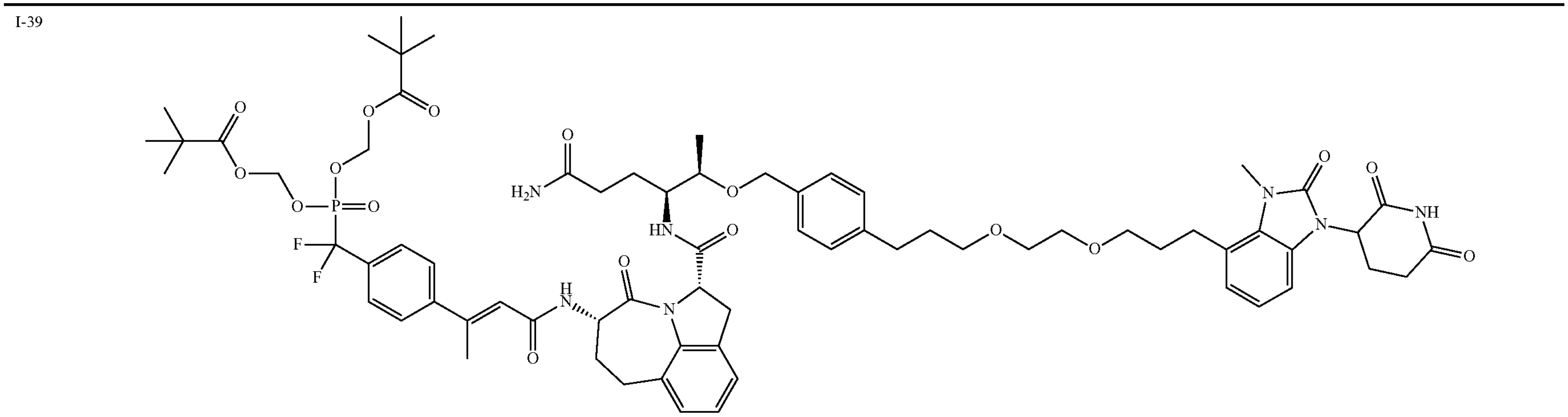 |
| I-40 | 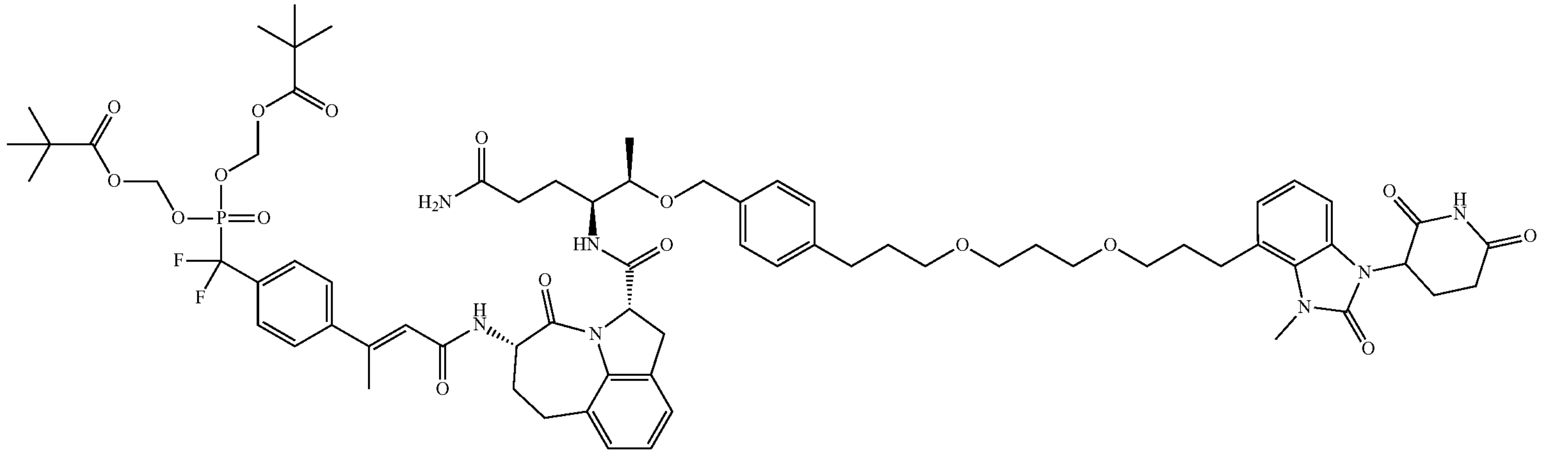 [SMILES: C/C(=C\C(=O)N[C@H]1CCc2cccc3c2N(C1=O)[C@H](C(=O)N[C@@H](CCC(N)=O)[C@@H](C)OCc1ccc(CCCOCCCOCCCc2cccc4c2n(C)c(=O)n4C2CCC(=O)NC2=O)cc1)C3)c1ccc(C(F)(F)P(=O)(OCOC(=O)C(C)(C)C)OCOC(=O)C(C)(C)C)cc1] |

TABLE 1-continued
| Exemplary Compounds | |
|---|---|
| I-# | Structure |
| I-41 | 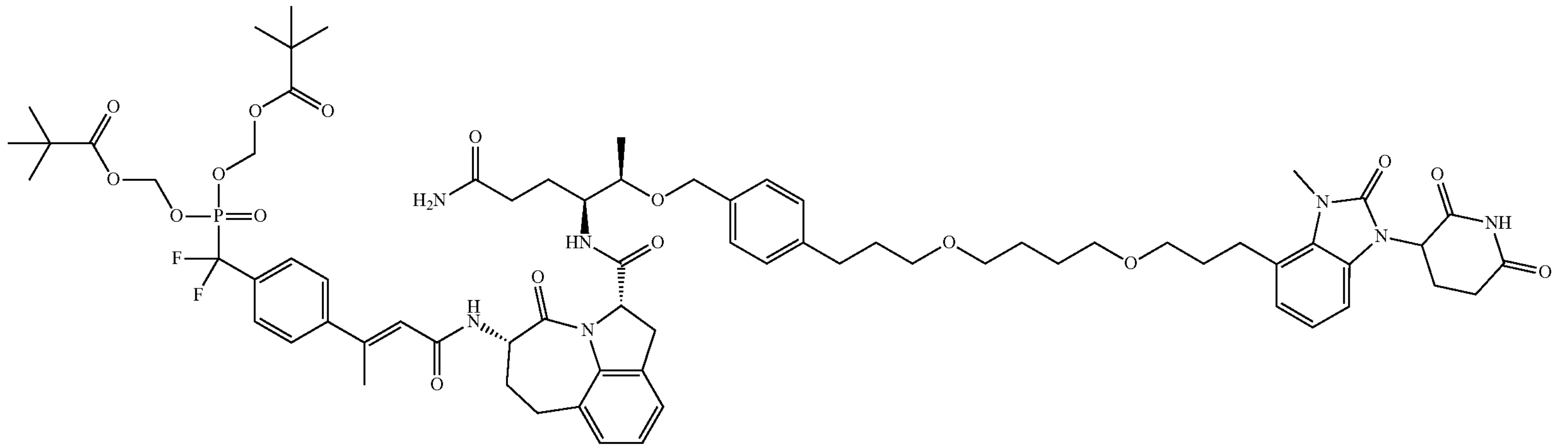 [SMILES: C/C(=C\C(=O)N[C@H]1CCc2cccc3c2N(C1=O)[C@H](C(=O)N[C@@H](CCC(N)=O)[C@@H](C)OCc1ccc(CCCOCCCCOCCCc2cccc4c2n(C)c(=O)n4C2CCC(=O)NC2=O)cc1)C3)c1ccc(C(F)(F)P(=O)(OCOC(=O)C(C)(C)C)OCOC(=O)C(C)(C)C)cc1] |
| I-42 | 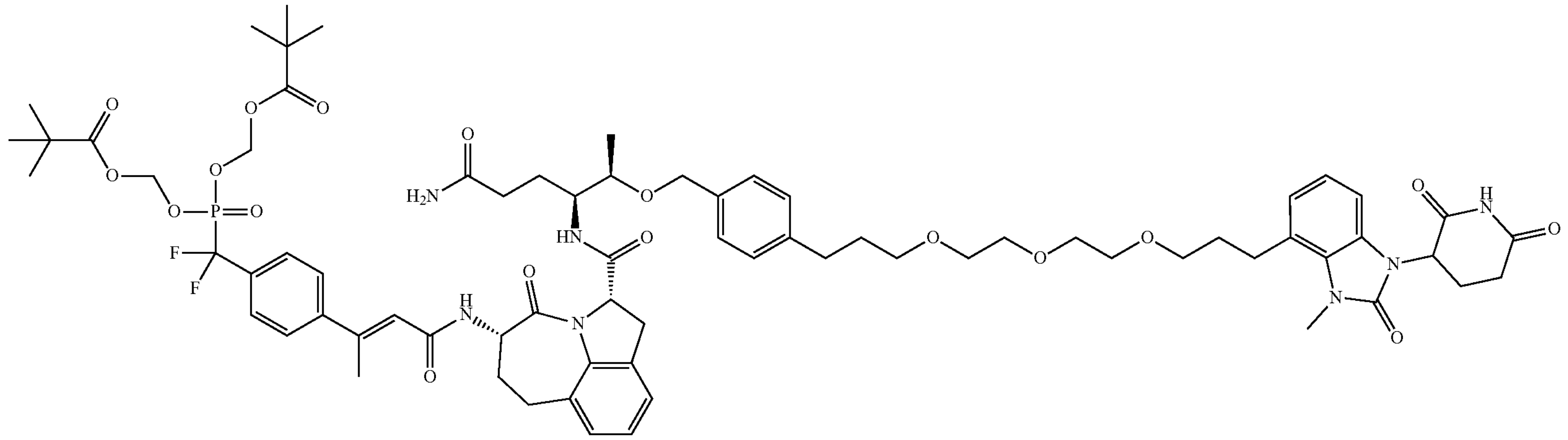 [SMILES: C/C(=C\C(=O)N[C@H]1CCc2cccc3c2N(C1=O)[C@H](C(=O)N[C@@H](CCC(N)=O)[C@@H](C)OCc1ccc(CCCOCCOCCOCCCc2cccc4c2n(C)c(=O)n4C2CCC(=O)NC2=O)cc1)C3)c1ccc(C(F)(F)P(=O)(OCOC(=O)C(C)(C)C)OCOC(=O)C(C)(C)C)cc1] |

TABLE 1-continued
| Exemplary Compounds | |
|---|---|
| I-# | Structure |
| I-43 | 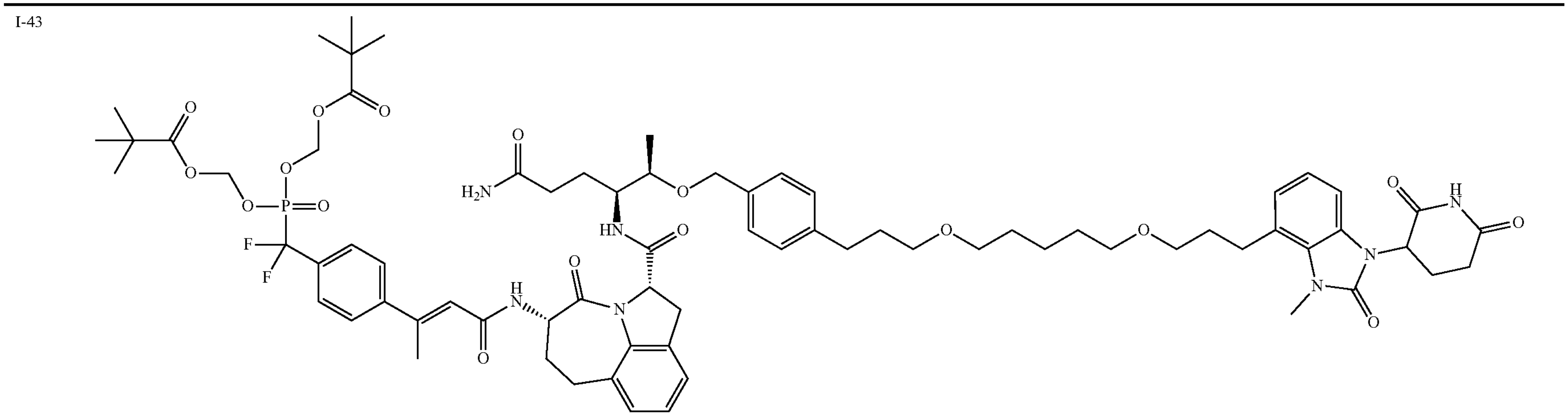 |
| I-44 | 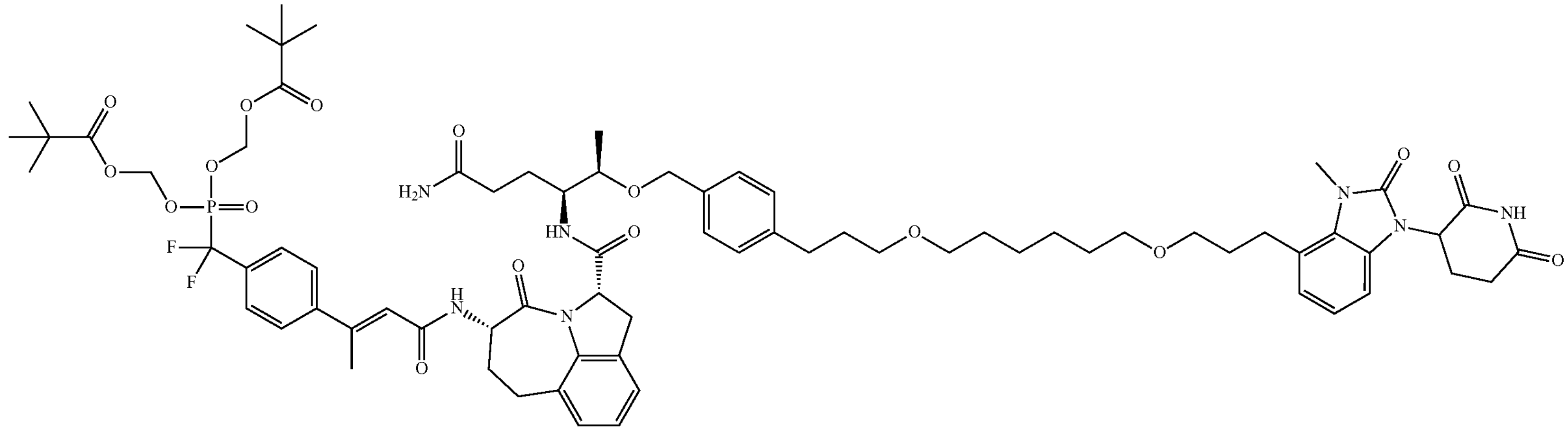 [SMILES: C/C(=C\C(=O)N[C@H]1CCc2cccc3c2N(C1=O)[C@H](C(=O)N[C@@H](CCC(N)=O)[C@@H](C)OCc1ccc(CCCOCCCCCCOCCCc2cccc4c2n(C)c(=O)n4C2CCC(=O)NC2=O)cc1)C3)c1ccc(C(F)(F)P(=O)(OCOC(=O)C(C)(C)C)OCOC(=O)C(C)(C)C)cc1] |

TABLE 1-continued
| Exemplary Compounds | |
|---|---|
| I-# | Structure |
| I-45 | 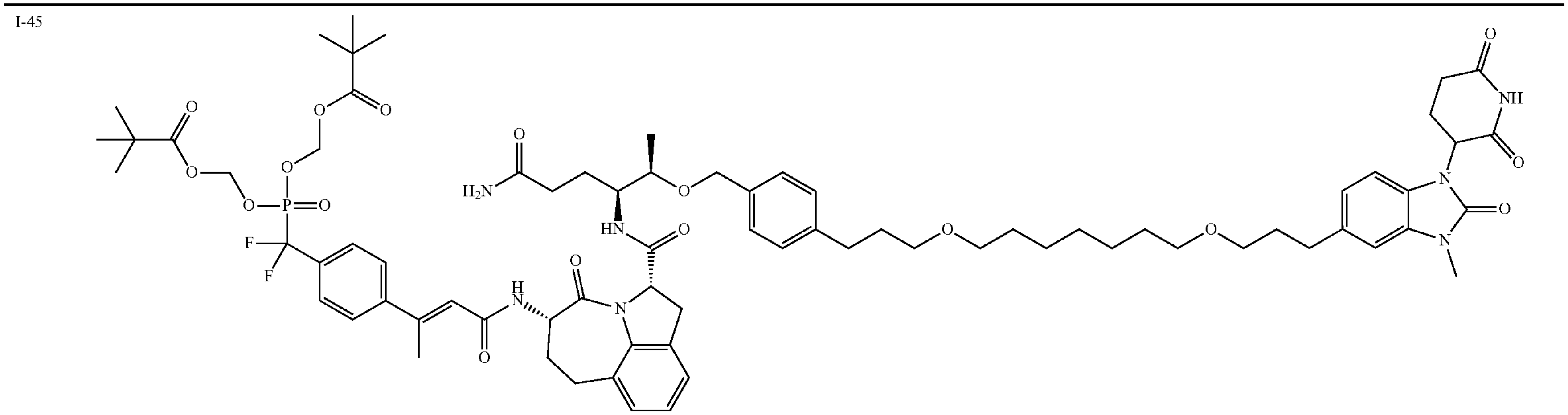 |
| I-46 | 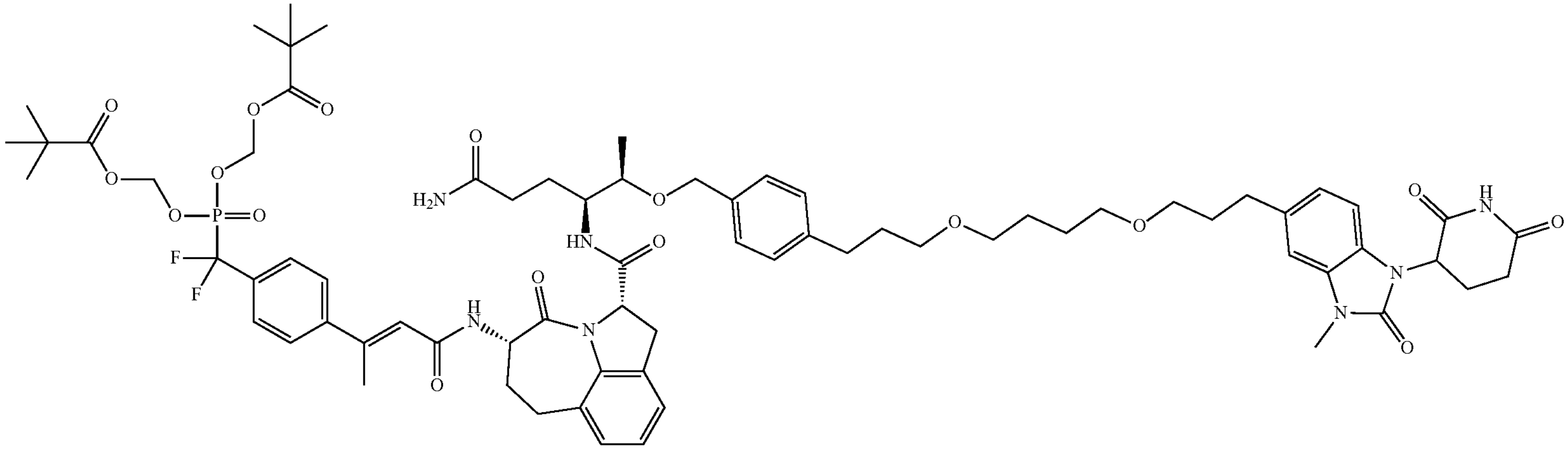 [SMILES: C/C(=C\C(=O)N[C@H]1CCc2cccc3c2N(C1=O)[C@H](C(=O)N[C@@H](CCC(N)=O)[C@@H](C)OCc1ccc(CCCOCCCCOCCCc2ccc4c(c2)n(C)c(=O)n4C2CCC(=O)NC2=O)cc1)C3)c1ccc(C(F)(F)P(=O)(OCOC(=O)C(C)(C)C)OCOC(=O)C(C)(C)C)cc1] |

TABLE 1-continued
| Exemplary Compounds | |
|---|---|
| I-# | Structure |
| I-47 | 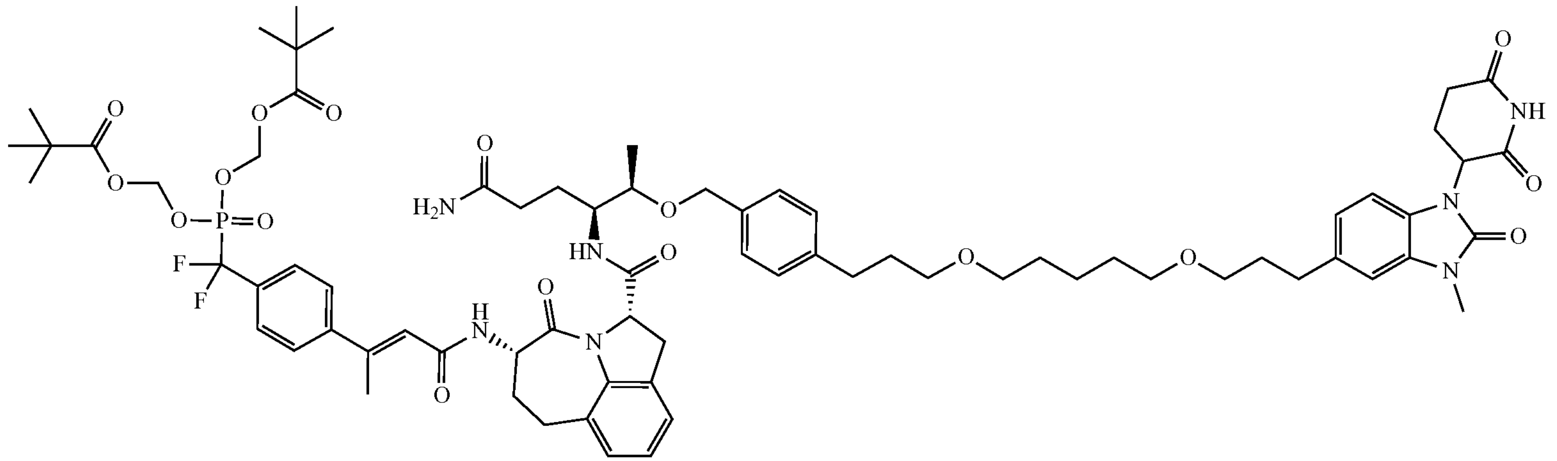 [SMILES: C/C(=C\C(=O)N[C@H]1CCc2cccc3c2N(C1=O)[C@H](C(=O)N[C@@H](CCC(N)=O)[C@@H](C)OCc1ccc(CCCOCCCCCOCCCc2ccc4c(c2)n(C)c(=O)n4C2CCC(=O)NC2=O)cc1)C3)c1ccc(C(F)(F)P(=O)(OCOC(=O)C(C)(C)C)OCOC(=O)C(C)(C)C)cc1] |
| I-48 | 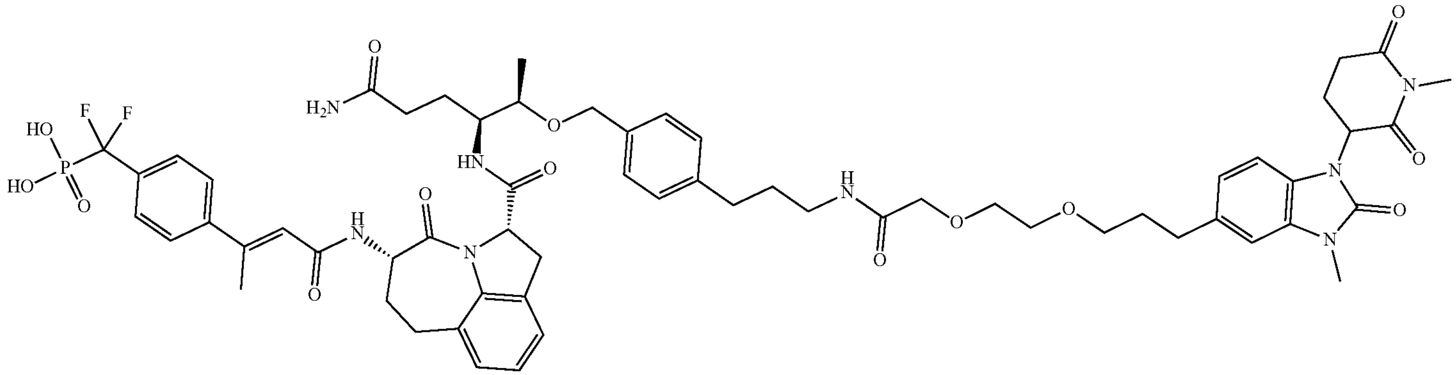 [SMILES: C/C(=C\C(=O)N[C@H]1CCc2cccc3c2N(C1=O)[C@H](C(=O)N[C@@H](CCC(N)=O)[C@@H](C)OCc1ccc(CCCNC(=O)COCCOCCCc2ccc4c(c2)n(C)c(=O)n4C2CCC(=O)N(C)C2=O)cc1)C3)c1ccc(C(F)(F)P(=O)(O)O)cc1] |

TABLE 1-continued
| Exemplary Compounds | |
|---|---|
| I-# | Structure |
| I-49 | 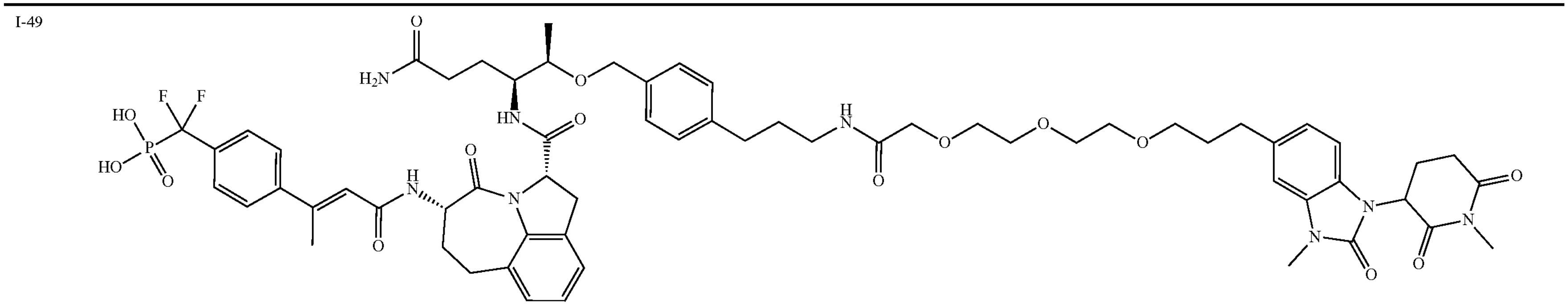 |
| I-50 | 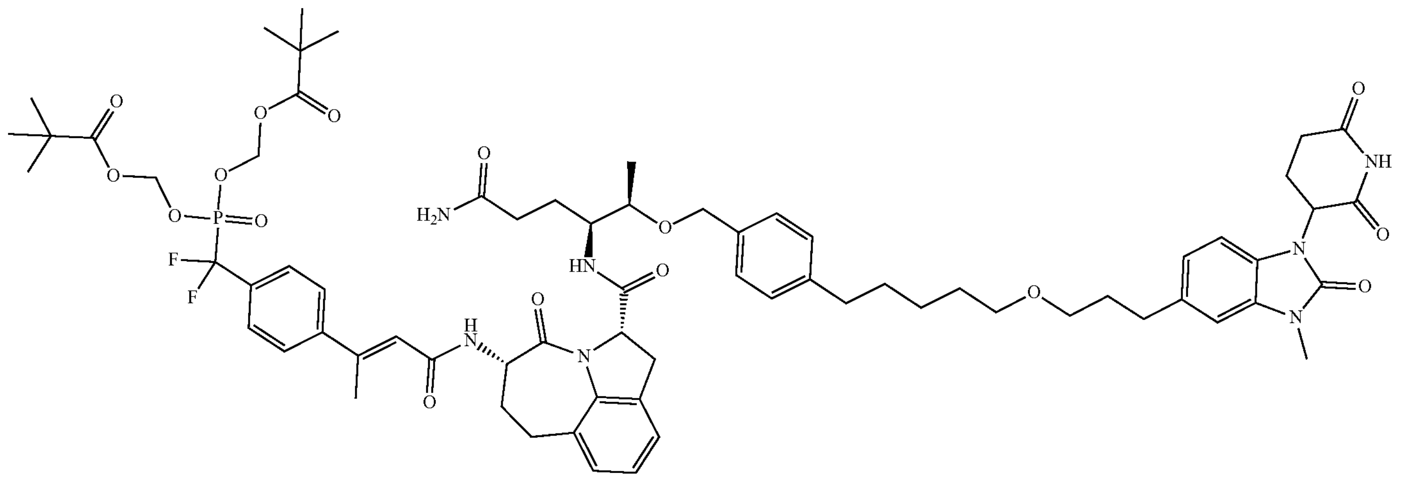 [SMILES: C/C(=C\C(=O)N[C@H]1CCc2cccc3c2N(C1=O)[C@H](C(=O)N[C@@H](CCC(N)=O)[C@@H](C)OCc1ccc(CCCCCOCCCc2ccc4c(c2)n(C)c(=O)n4C2CCC(=O)NC2=O)cc1)C3)c1ccc(C(F)(F)P(=O)(OCOC(=O)C(C)(C)C)OCOC(=O)C(C)(C)C)cc1] |

TABLE 1-continued
| Exemplary Compounds | |
|---|---|
| I-# | Structure |
| I-51 | 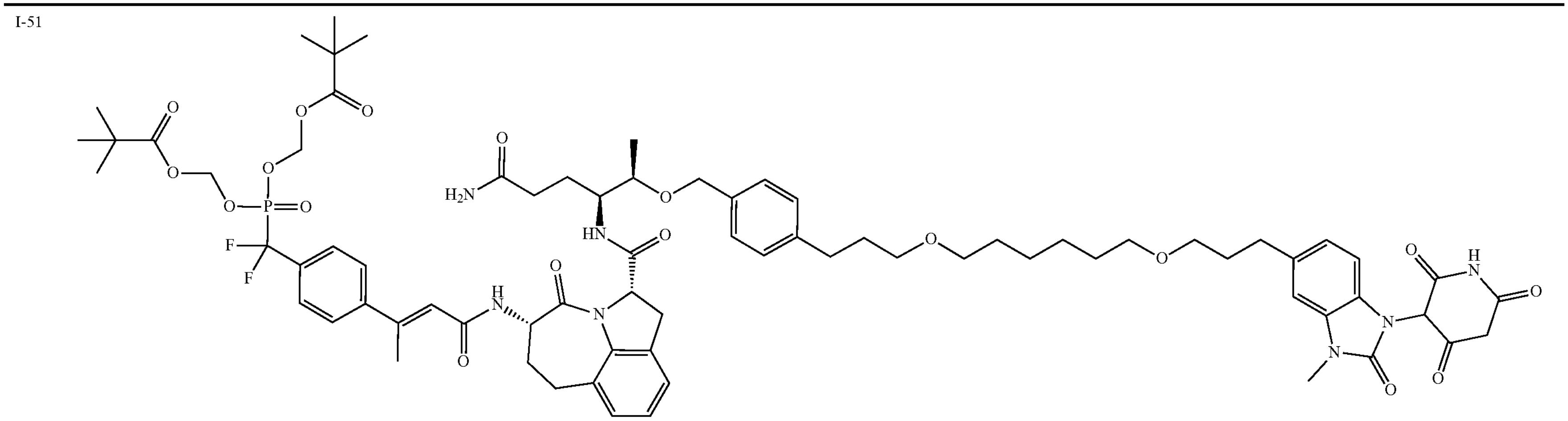 |
| I-52 | 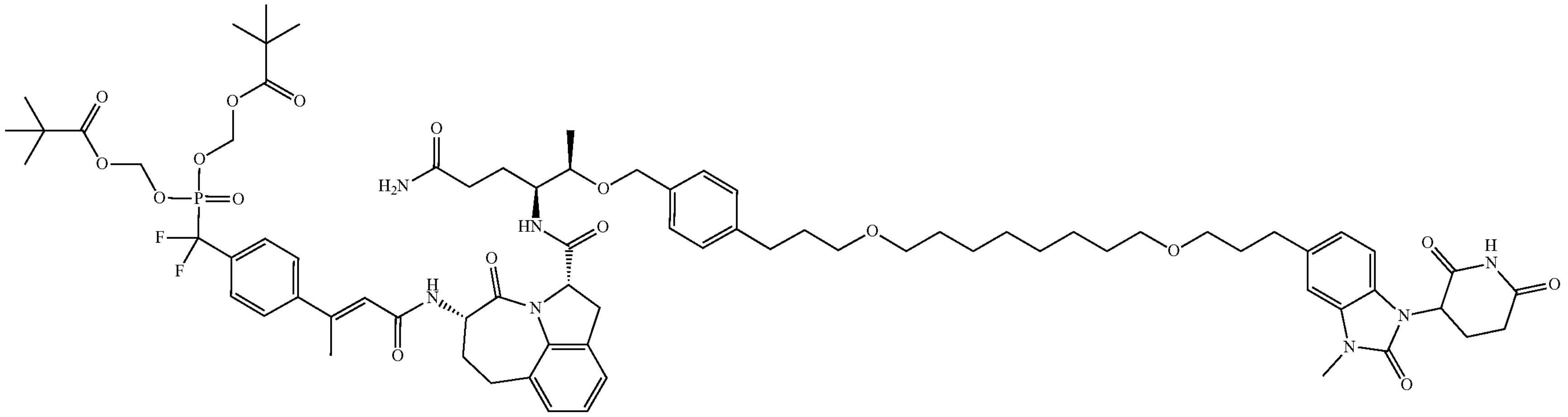 |

TABLE 1-continued
| Exemplary Compounds | |
|---|---|
| I-# | Structure |
| I-53 | 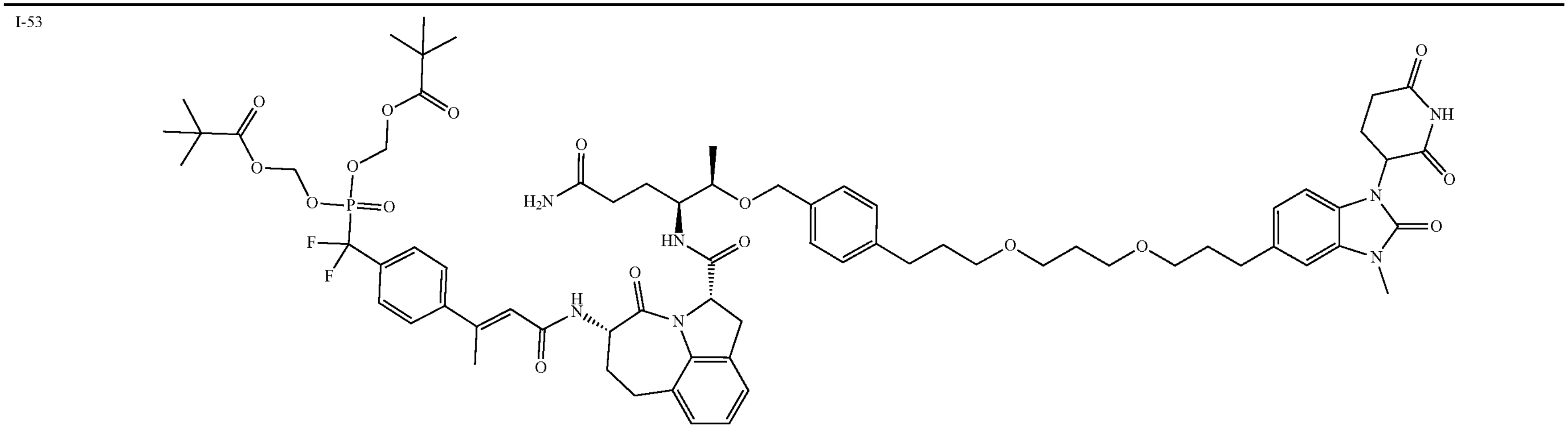 |
| I-54 | 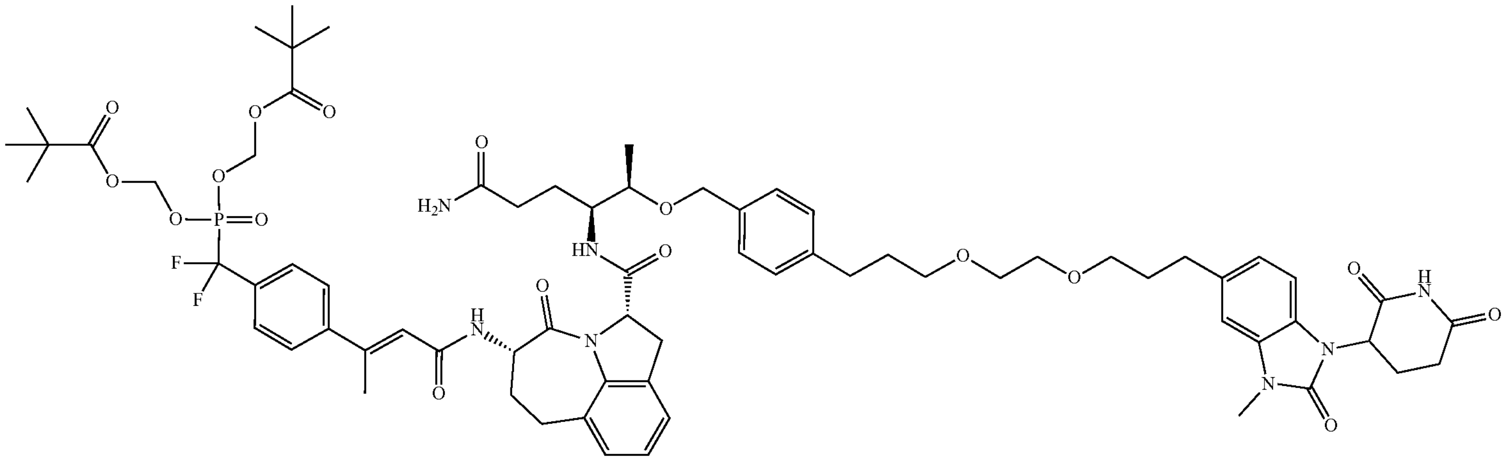 [SMILES: C/C(=C\C(=O)N[C@H]1CCc2cccc3c2N(C1=O)[C@H](C(=O)N[C@@H](CCC(N)=O)[C@@H](C)OCc1ccc(CCCOCCOCCCc2ccc4c(c2)n(C)c(=O)n4C2CCC(=O)NC2=O)cc1)C3)c1ccc(C(F)(F)P(=O)(OCOC(=O)C(C)(C)C)OCOC(=O)C(C)(C)C)cc1] |

TABLE 1-continued
| Exemplary Compounds | |
|---|---|
| I-# | Structure |
| I-55 | 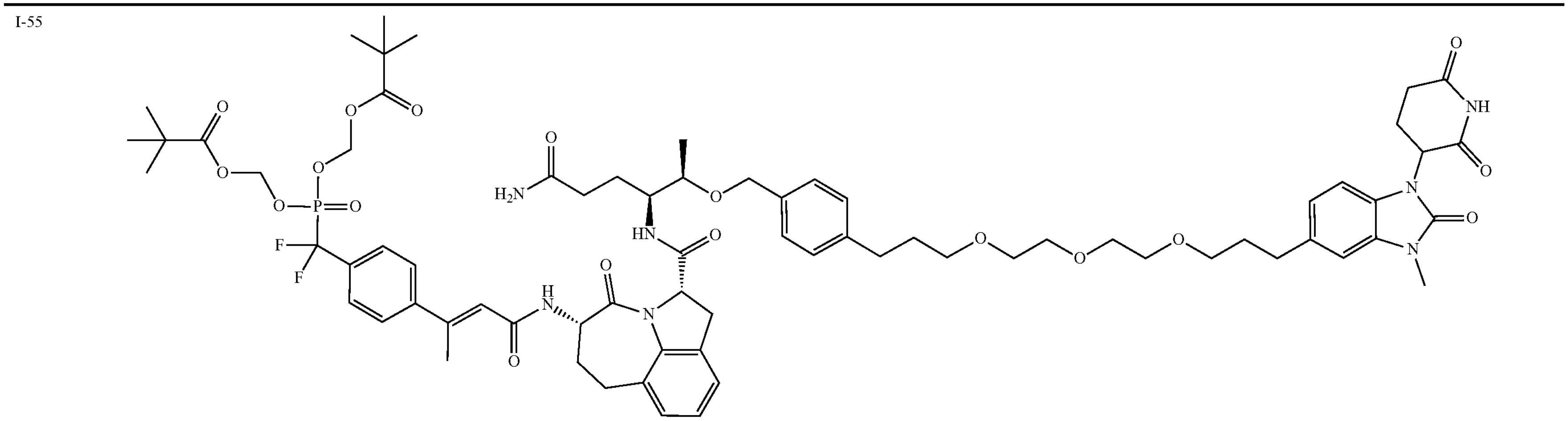 |
| I-56 | 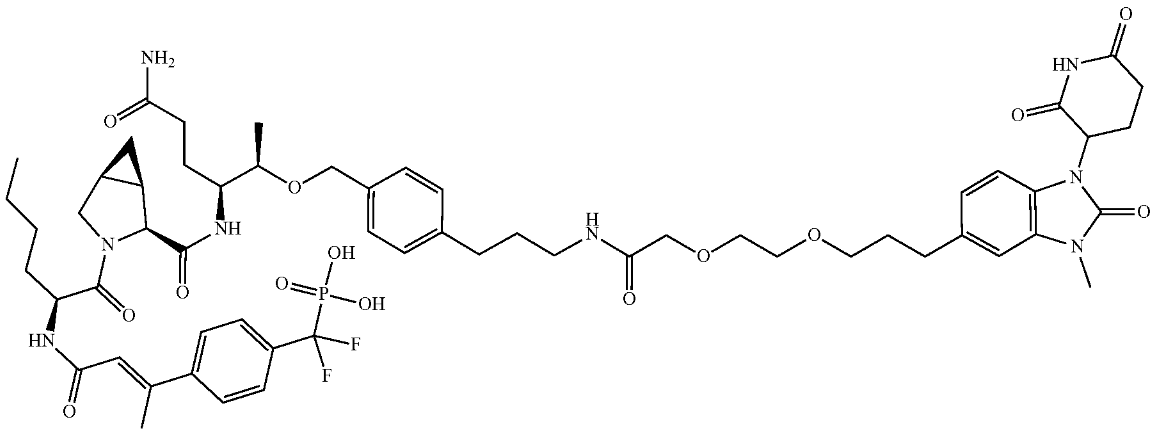 [SMILES: CCCC[C@H](NC(=O)/C=C(\C)c1ccc(C(F)(F)P(=O)(O)O)cc1)C(=O)N1C[C@H]2C[C@H]2[C@H]1C(=O)N[C@@H](CCC(N)=O)[C@@H](C)OCc1ccc(CCCNC(=O)COCCOCCCc2ccc3c(c2)n(C)c(=O)n3C2CCC(=O)NC2=O)cc1] |

TABLE 1-continued
| Exemplary Compounds | |
|---|---|
| I-# | Structure |
| I-57 | 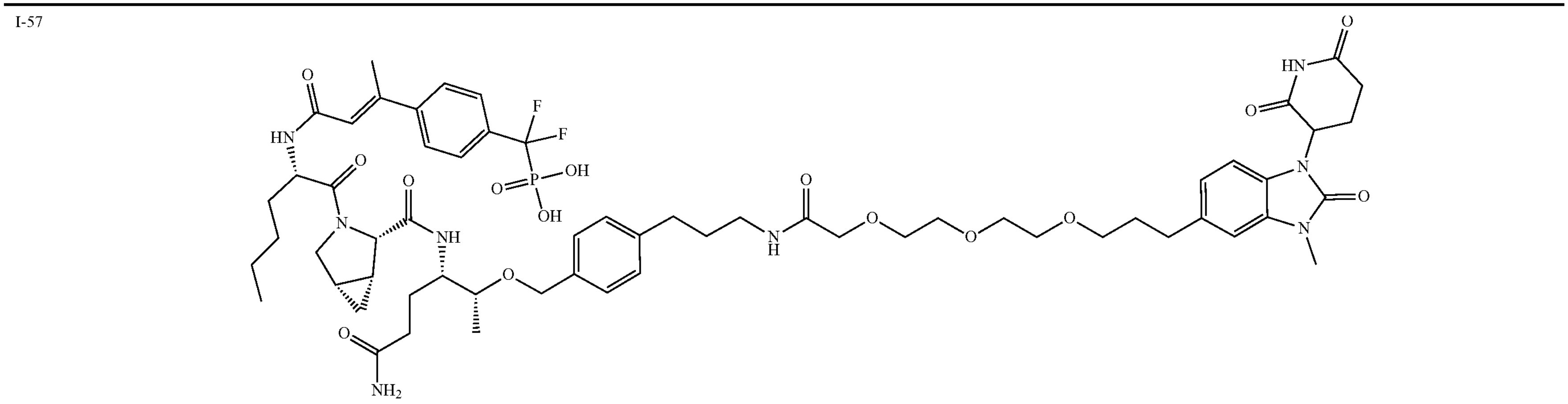 |
| I-58 | 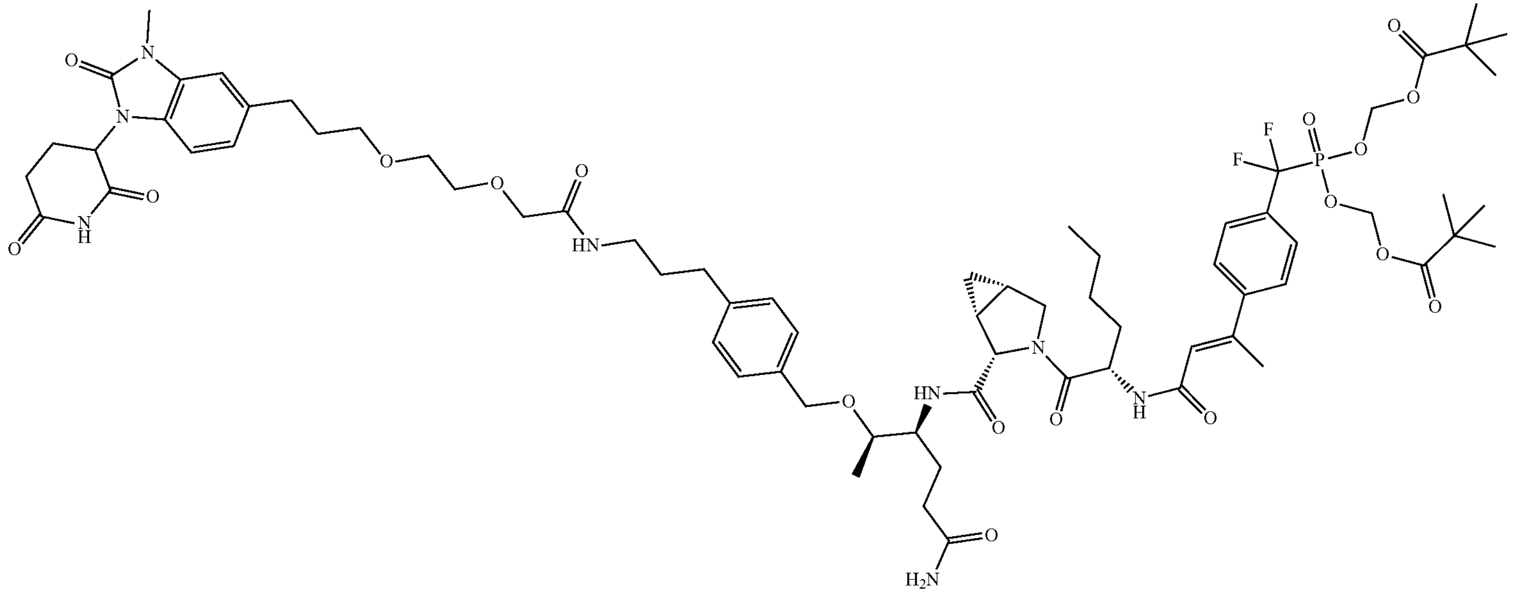 [SMILES: CCCC[C@H](NC(=O)/C=C(\C)c1ccc(C(F)(F)P(=O)(OCOC(=O)C(C)(C)C)OCOC(=O)C(C)(C)C)cc1)C(=O)N1C[C@H]2C[C@H]2[C@H]1C(=O)N[C@@H](CCC(N)=O)[C@@H](C)OCc1ccc(CCCNC(=O)COCCOCCCc2ccc3c(c2)n(C)c(=O)n3C2CCC(=O)NC2=O)cc1] |

TABLE 1-continued
| Exemplary Compounds | |
|---|---|
| I-# | Structure |
| I-59 | 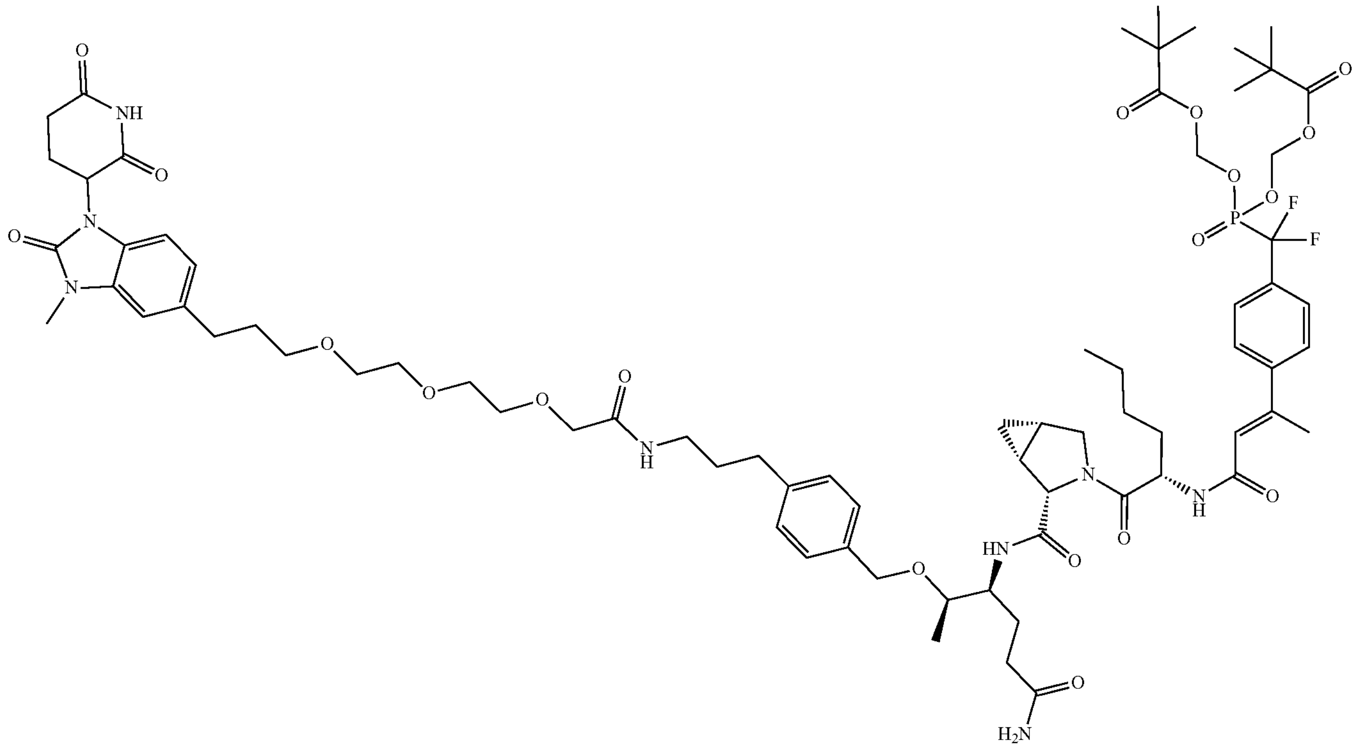 [SMILES: CCCC[C@H](NC(=O)/C=C(\C)c1ccc(C(F)(F)P(=O)(OCOC(=O)C(C)(C)C)OCOC(=O)C(C)(C)C)cc1)C(=O)N1C[C@H]2C[C@H]2[C@H]1C(=O)N[C@@H](CCC(N)=O)[C@@H](C)OCc1ccc(CCCNC(=O)COCCOCCOCCCc2ccc3c(c2)n(C)c(=O)n3C2CCC(=O)NC2=O)cc1] |

TABLE 1-continued
| Exemplary Compounds | |
|---|---|
| I-# | Structure |
| I-60 | 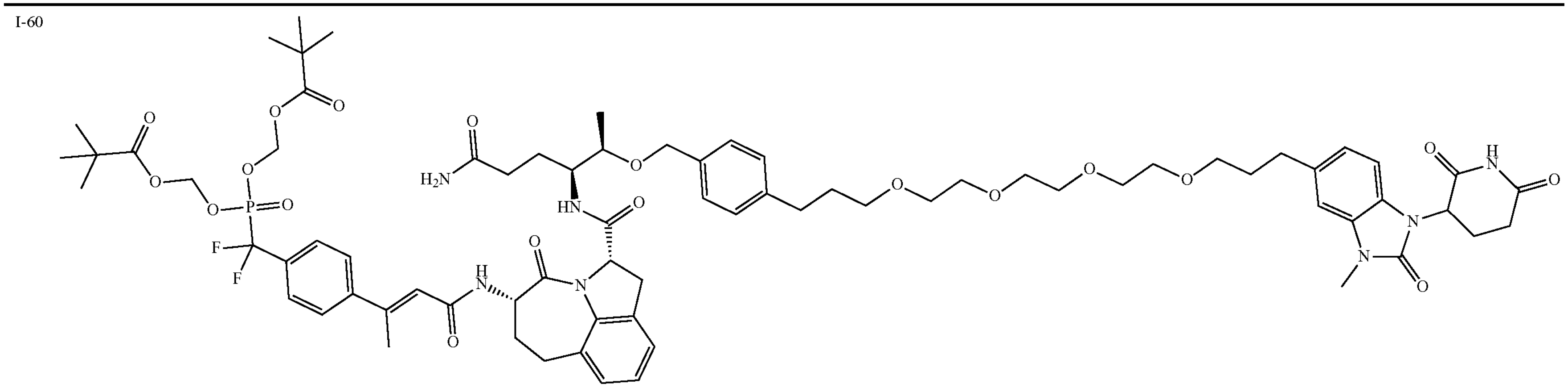 |
| I-61 | 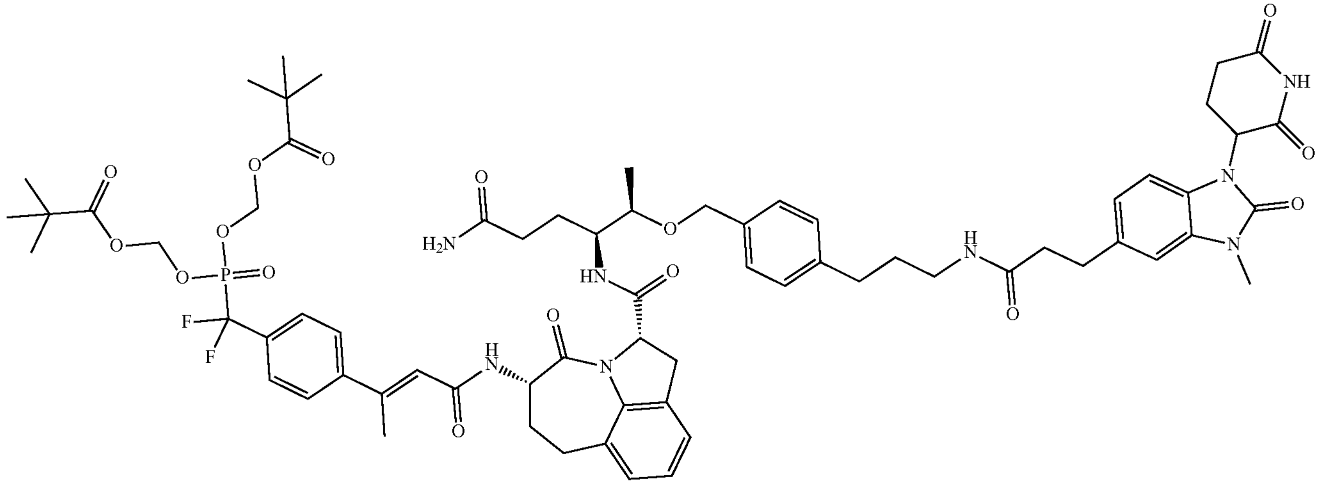 [SMILES: C/C(=C\C(=O)N[C@H]1CCc2cccc3c2N(C1=O)[C@H](C(=O)N[C@@H](CCC(N)=O)[C@@H](C)OCc1ccc(CCCNC(=O)CCc2ccc4c(c2)n(C)c(=O)n4C2CCC(=O)NC2=O)cc1)C3)c1ccc(C(F)(F)P(=O)(OCOC(=O)C(C)(C)C)OCOC(=O)C(C)(C)C)cc1] |

TABLE 1-continued
| Exemplary Compounds | |
|---|---|
| I-# | Structure |
| I-62 | 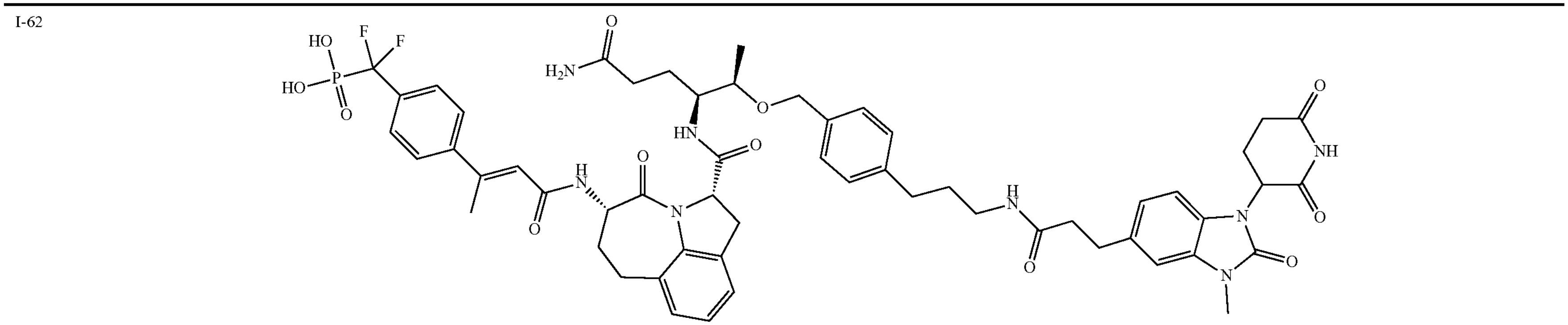 |
| I-63 | 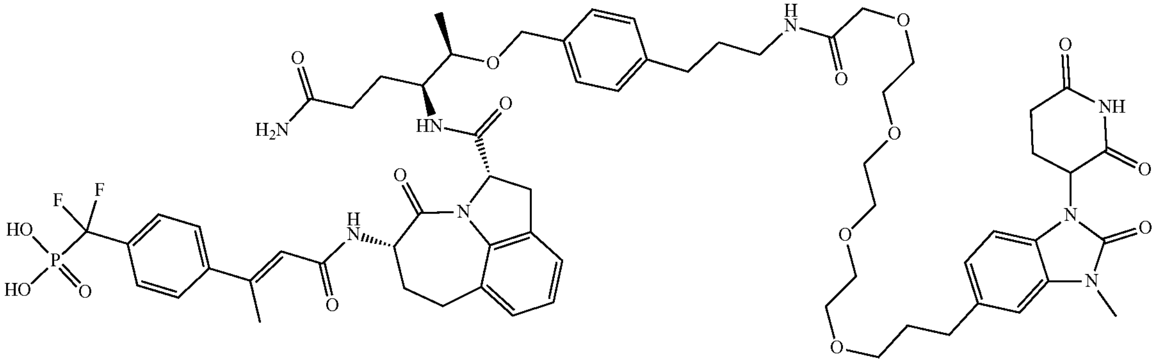 [SMILES: C/C(=C\C(=O)N[C@H]1CCc2cccc3c2N(C1=O)[C@H](C(=O)N[C@@H](CCC(N)=O)[C@@H](C)OCc1ccc(CCCNC(=O)COCCOCCOCCOCCCc2ccc4c(c2)n(C)c(=O)n4C2CCC(=O)NC2=O)cc1)C3)c1ccc(C(F)(F)P(=O)(O)O)cc1] |

TABLE 1-continued
| Exemplary Compounds | |
|---|---|
| I-# | Structure |
| I-64 | 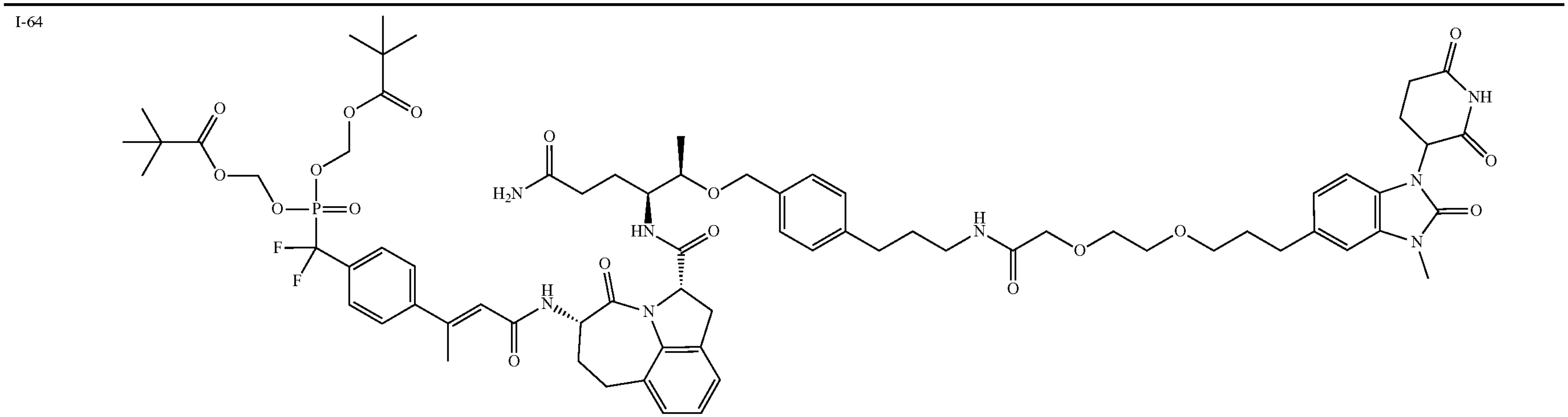 |
| I-65 | 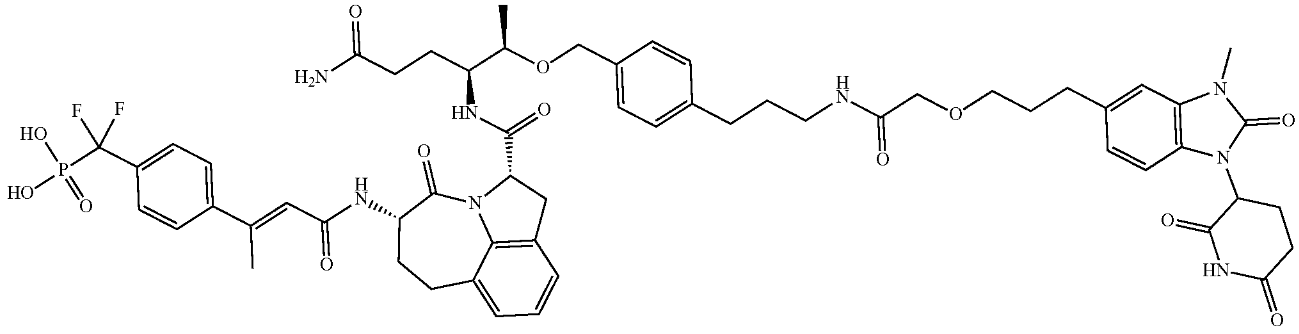 [SMILES: C/C(=C\C(=O)N[C@H]1CCc2cccc3c2N(C1=O)[C@H](C(=O)N[C@@H](CCC(N)=O)[C@@H](C)OCc1ccc(CCCNC(=O)COCCCc2ccc4c(c2)n(C)c(=O)n4C2CCC(=O)NC2=O)cc1)C3)c1ccc(C(F)(F)P(=O)(O)O)cc1] |

TABLE 1-continued
| Exemplary Compounds | |
|---|---|
| I-# | Structure |
| I-66 | 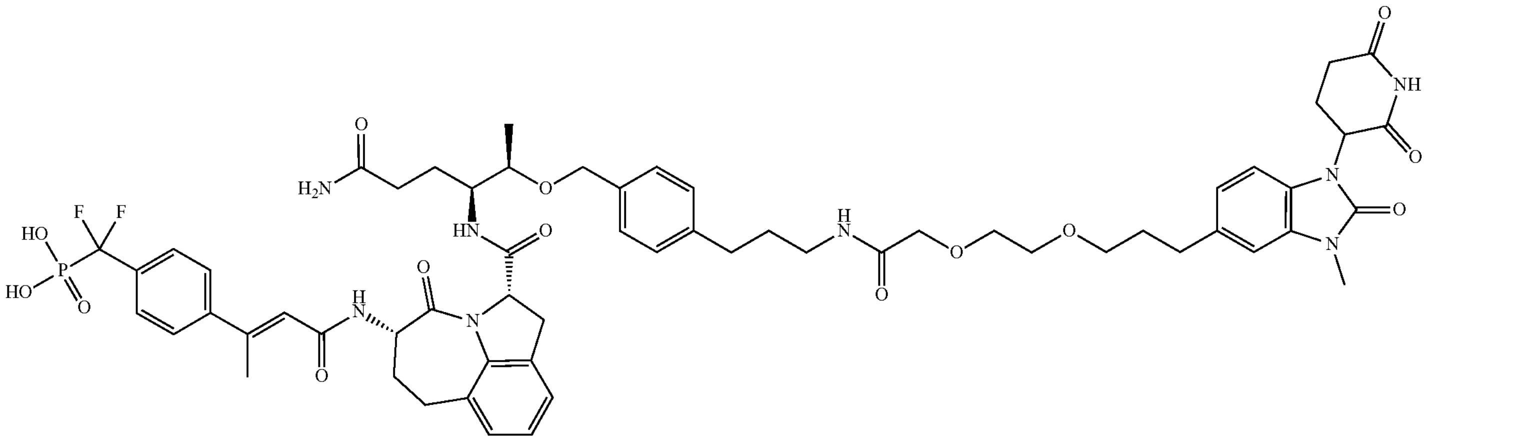 [SMILES: C/C(=C\C(=O)N[C@H]1CCc2cccc3c2N(C1=O)[C@H](C(=O)N[C@@H](CCC(N)=O)[C@@H](C)OCc1ccc(CCCNC(=O)COCCOCCCc2ccc4c(c2)n(C)c(=O)n4C2CCC(=O)NC2=O)cc1)C3)c1ccc(C(F)(F)P(=O)(O)O)cc1] |
| I-67 | 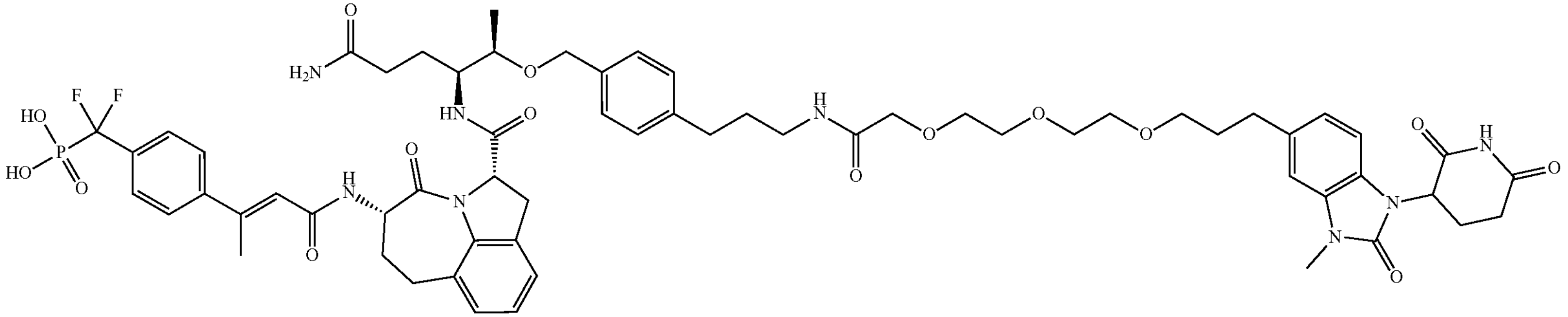 [SMILES: C/C(=C\C(=O)N[C@H]1CCc2cccc3c2N(C1=O)[C@H](C(=O)N[C@@H](CCC(N)=O)[C@@H](C)OCc1ccc(CCCNC(=O)COCCOCCOCCCc2ccc4c(c2)n(C)c(=O)n4C2CCC(=O)NC2=O)cc1)C3)c1ccc(C(F)(F)P(=O)(O)O)cc1] |

TABLE 1-continued
| Exemplary Compounds | |
|---|---|
| I-# | Structure |
| I-68 | 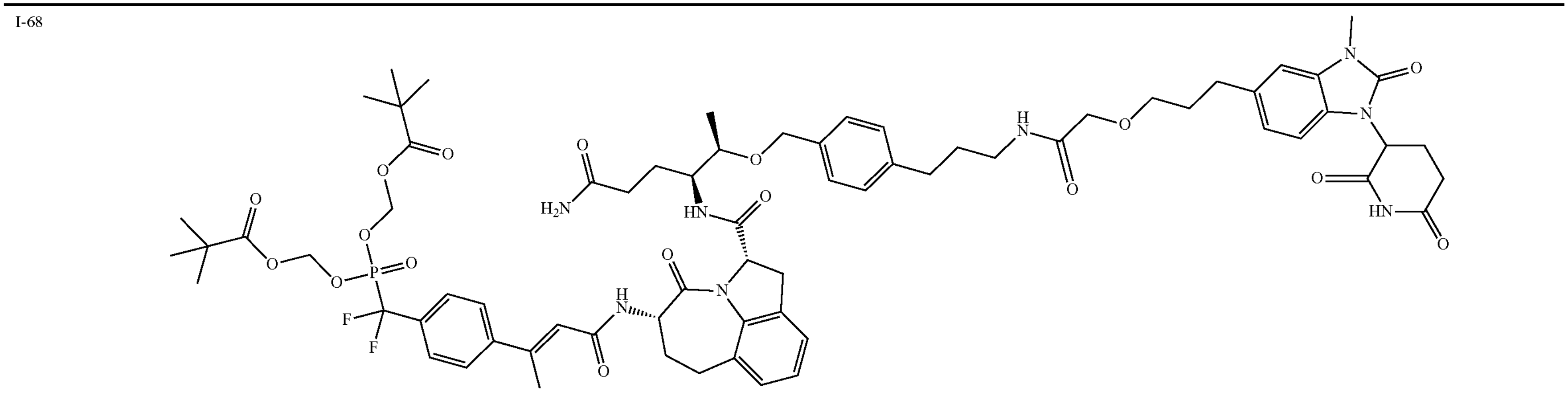 |
| I-69 | 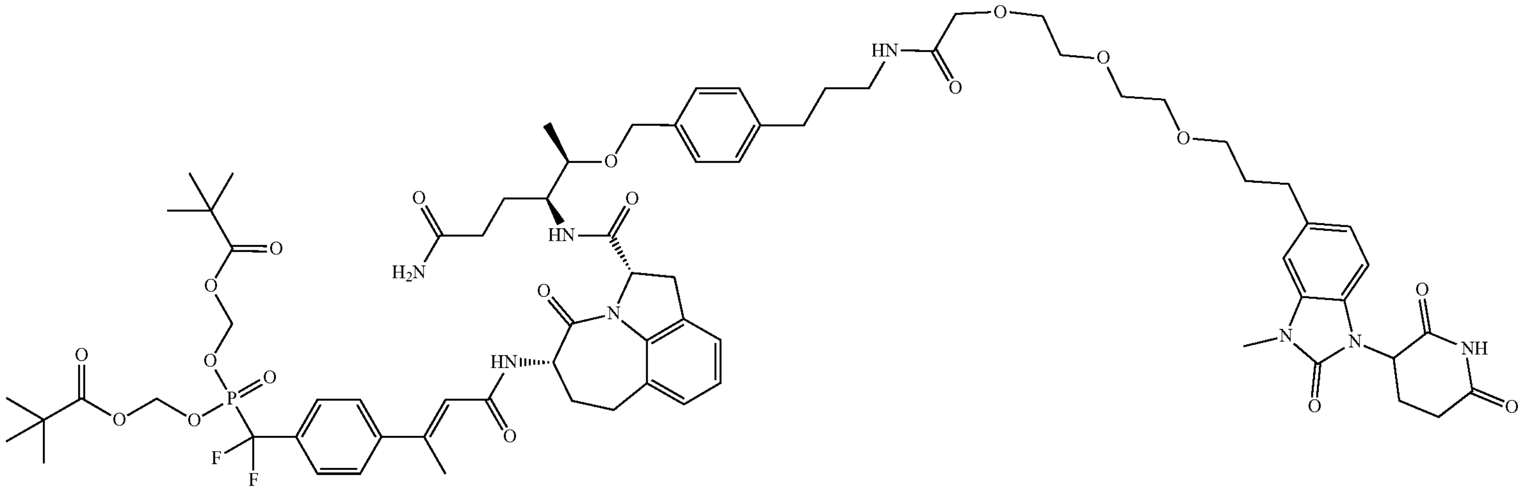 [SMILES: C/C(=C\C(=O)N[C@H]1CCc2cccc3c2N(C1=O)[C@H](C(=O)N[C@@H](CCC(N)=O)[C@@H](C)OCc1ccc(CCCNC(=O)COCCOCCOCCCc2ccc4c(c2)n(C)c(=O)n4C2CCC(=O)NC2=O)cc1)C3)c1ccc(C(F)(F)P(=O)(OCOC(=O)C(C)(C)C)OCOC(=O)C(C)(C)C)cc1] |

TABLE 1-continued
| Exemplary Compounds | |
|---|---|
| I-# | Structure |
| I-70 | 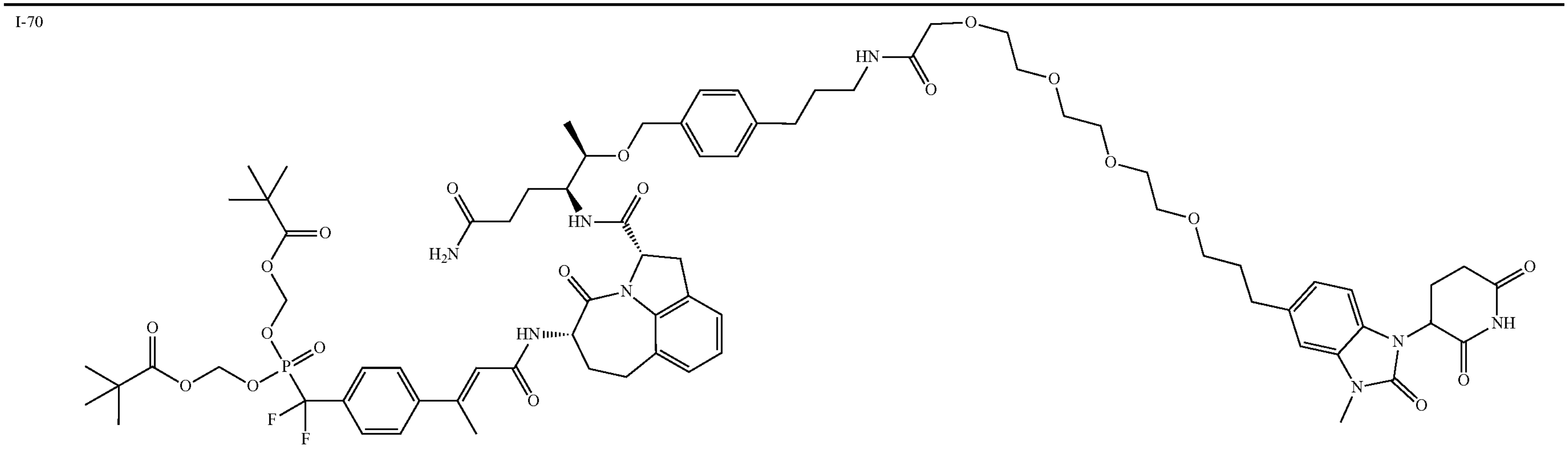 |
| I-71 | 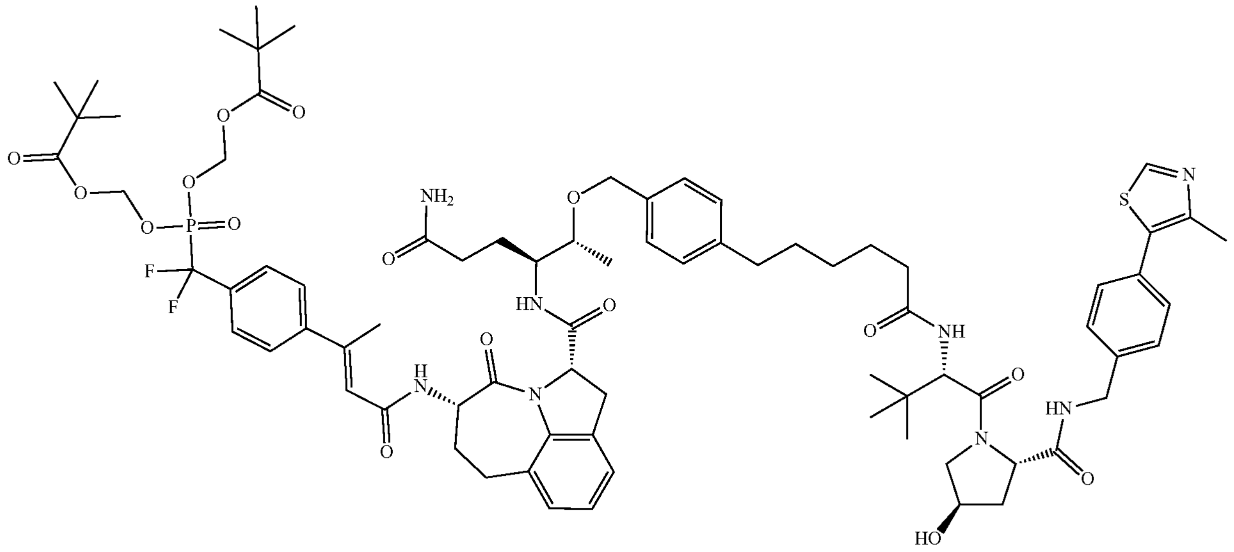 [SMILES: C/C(=C\C(=O)N[C@H]1CCc2cccc3c2N(C1=O)[C@H](C(=O)N[C@@H](CCC(N)=O)[C@@H](C)OCc1ccc(CCCCCC(=O)N[C@H](C(=O)N2C[C@H](O)C[C@H]2C(=O)NCc2ccc(-c4scnc4C)cc2)C(C)(C)C)cc1)C3)c1ccc(C(F)(F)P(=O)(OCOC(=O)C(C)(C)C)OCOC(=O)C(C)(C)C)cc1] |

TABLE 1-continued
| Exemplary Compounds | |
|---|---|
| I-# | Structure |
| I-80 | 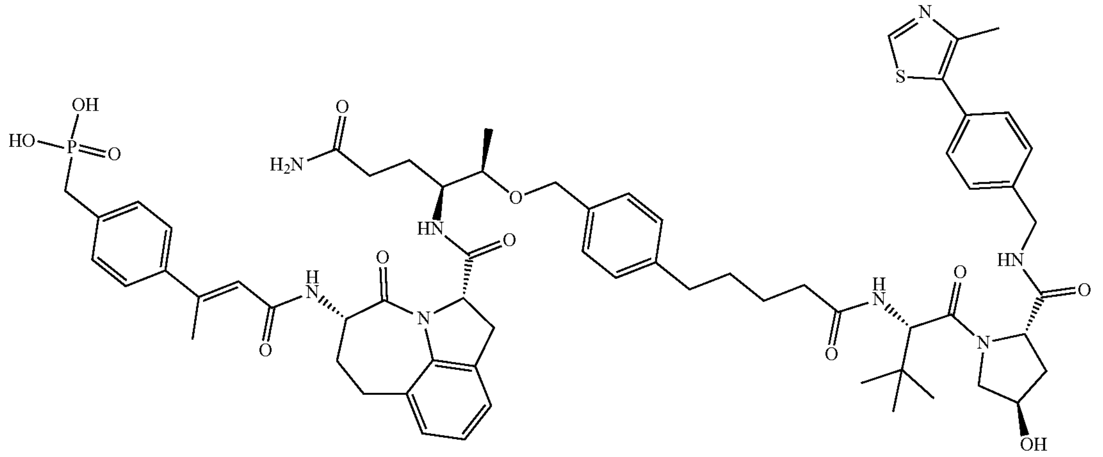 [SMILES: C/C(=C\C(=O)N[C@H]1CCc2cccc3c2N(C1=O)[C@H](C(=O)N[C@@H](CCC(N)=O)[C@@H](C)OCc1ccc(CCCCC(=O)N[C@H](C(=O)N2C[C@H](O)C[C@H]2C(=O)NCc2ccc(-c4scnc4C)cc2)C(C)(C)C)cc1)C3)c1ccc(CP(=O)(O)O)cc1] |
| I-81 | 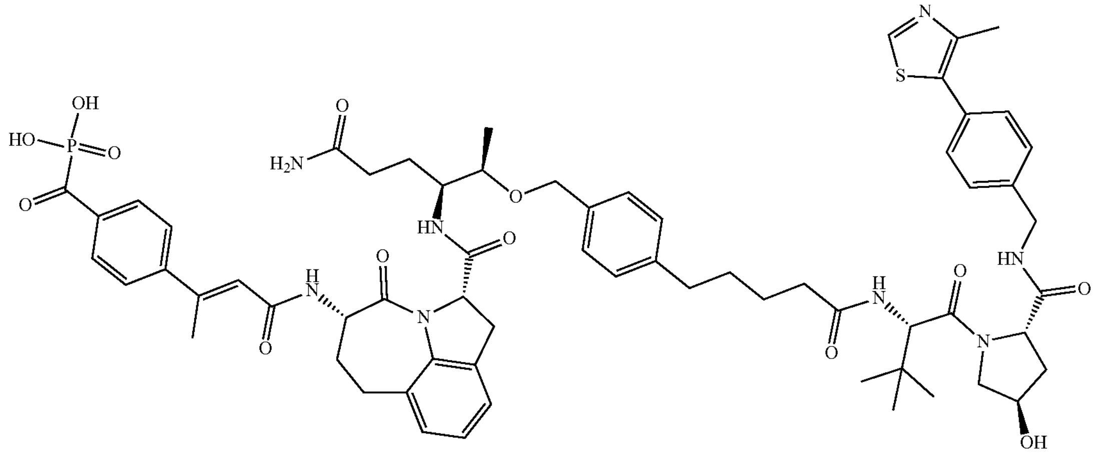 [SMILES: C/C(=C\C(=O)N[C@H]1CCc2cccc3c2N(C1=O)[C@H](C(=O)N[C@@H](CCC(N)=O)[C@@H](C)OCc1ccc(CCCCC(=O)N[C@H](C(=O)N2C[C@H](O)C[C@H]2C(=O)NCc2ccc(-c4scnc4C)cc2)C(C)(C)C)cc1)C3)c1ccc(C(=O)P(=O)(O)O)cc1] |

TABLE 1-continued
| Exemplary Compounds | |
|---|---|
| I-# | Structure |
| I-82 | 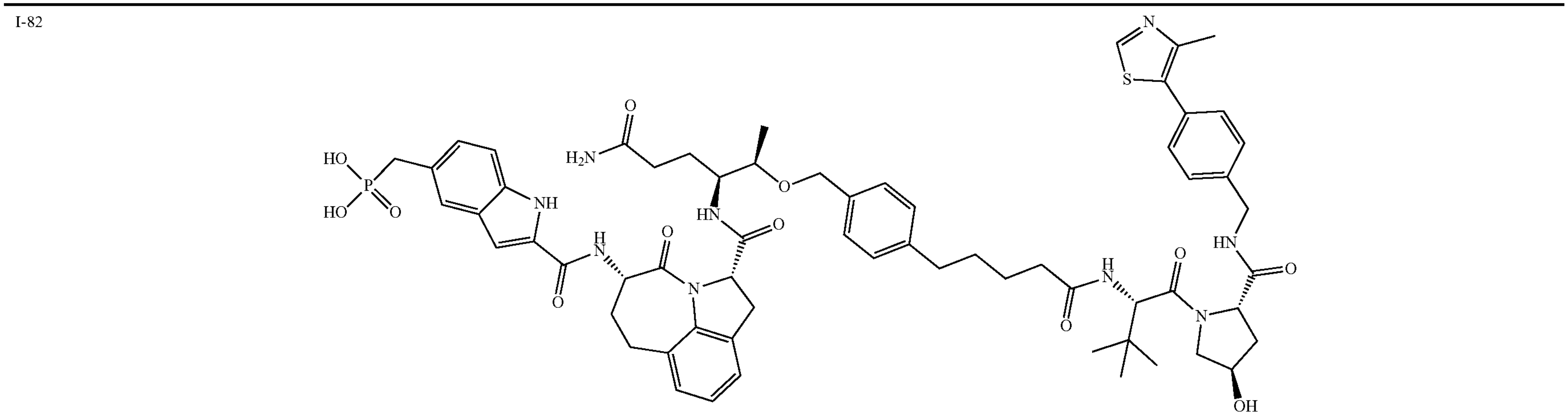 |
| I-83 | 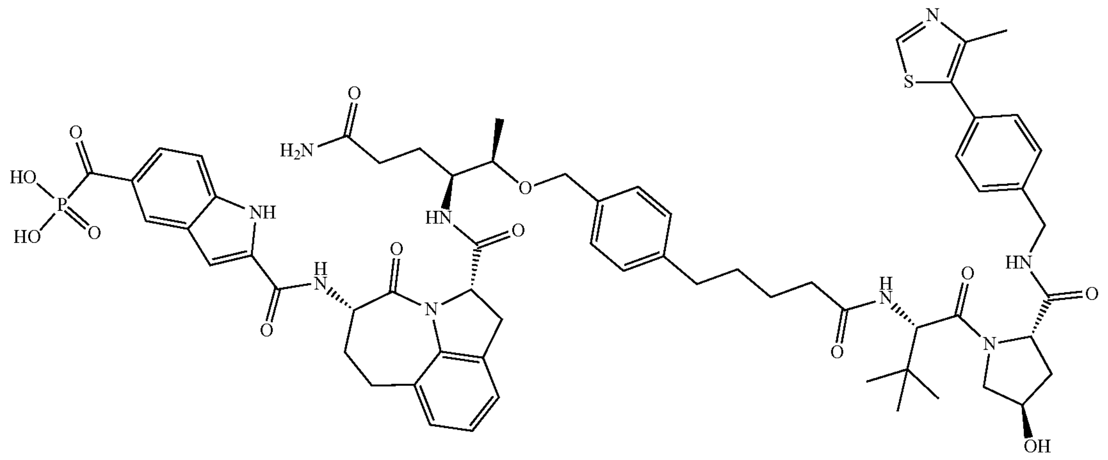 [SMILES: Cc1ncsc1-c1ccc(CNC(=O)[C@@H]2C[C@@H](O)CN2C(=O)[C@@H](NC(=O)CCCCc2ccc(CO[C@H](C)[C@H](CCC(N)=O)NC(=O)[C@@H]3Cc4cccc5c4N3C(=O)[C@@H](NC(=O)c3cc4cc(C(=O)P(=O)(O)O)ccc4[nH]3)CC5)cc2)C(C)(C)C)cc1] |

TABLE 1-continued
| Exemplary Compounds | |
|---|---|
| I-# | Structure |
| I-84 | 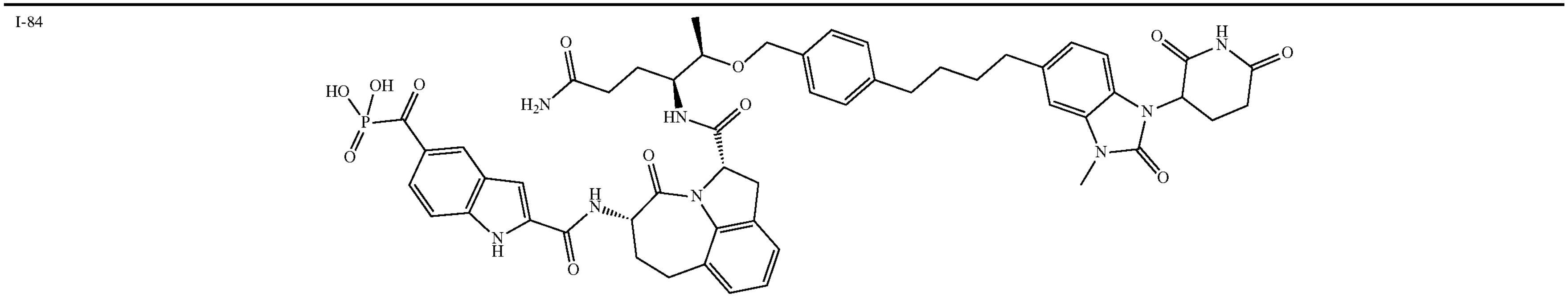 |
| I-85 | 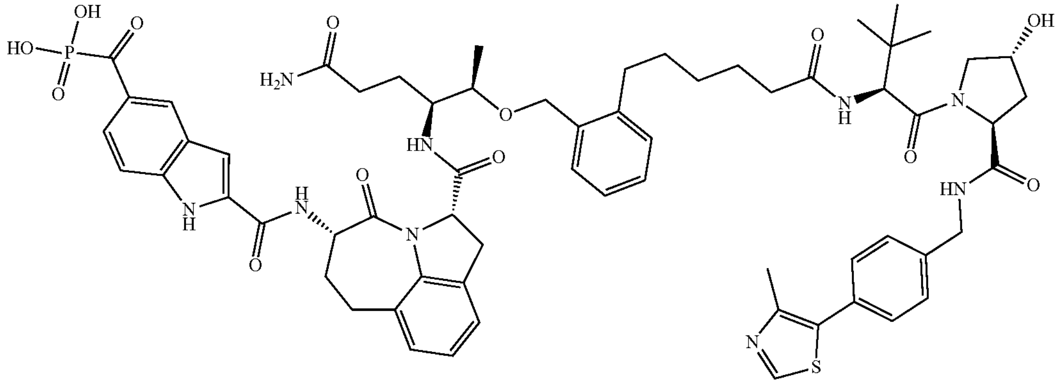 [SMILES: Cc1ncsc1-c1ccc(CNC(=O)[C@@H]2C[C@@H](O)CN2C(=O)[C@@H](NC(=O)CCCCCc2ccccc2CO[C@H](C)[C@H](CCC(N)=O)NC(=O)[C@@H]2Cc3cccc4c3N2C(=O)[C@@H](NC(=O)c2cc3cc(C(=O)P(=O)(O)O)ccc3[nH]2)CC4)C(C)(C)C)cc1] |

TABLE 1-continued
| Exemplary Compounds | |
|---|---|
| I-# | Structure |
| I-86 | 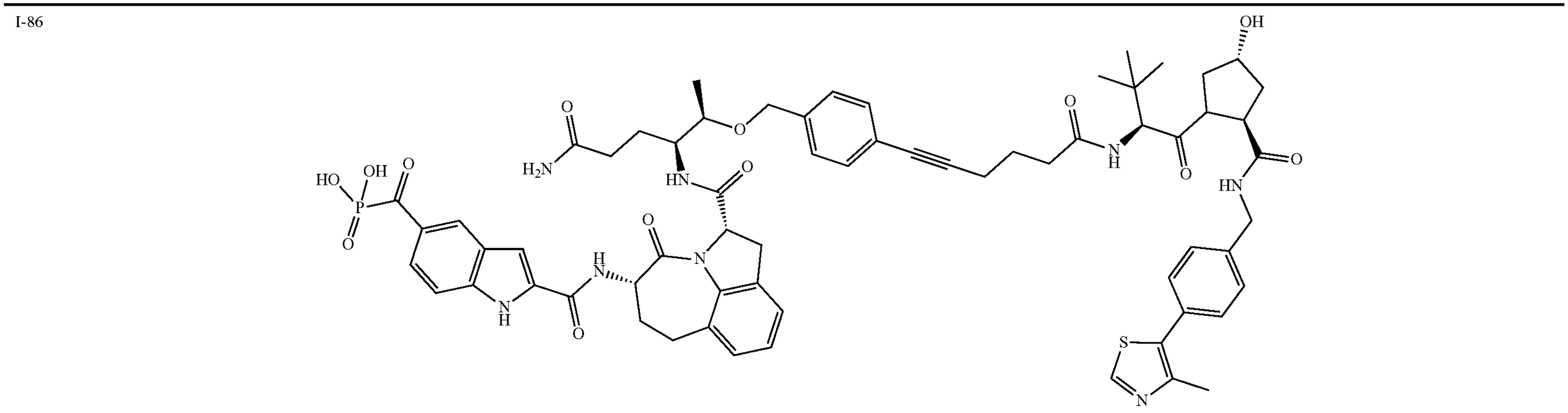 |
| I-87 | 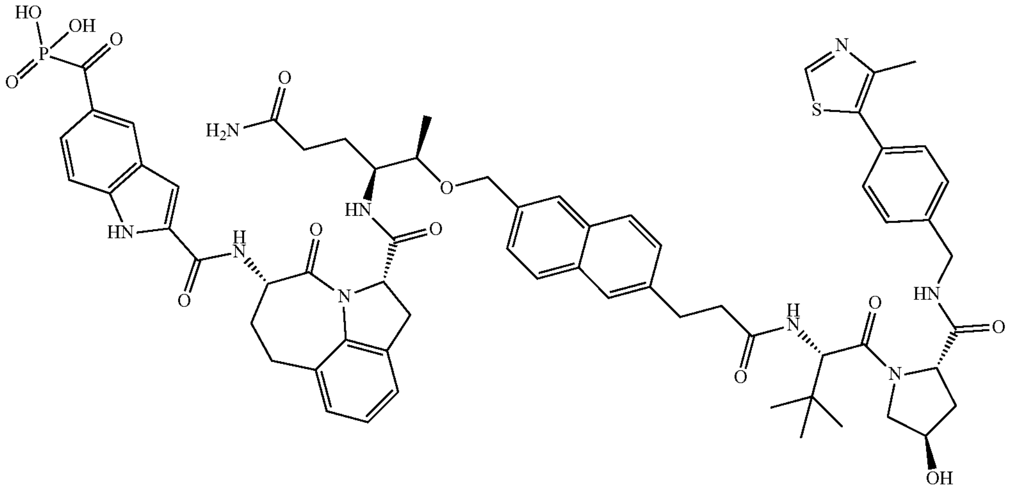 [SMILES: Cc1ncsc1-c1ccc(CNC(=O)[C@@H]2C[C@@H](O)CN2C(=O)[C@@H](NC(=O)CCc2ccc3cc(CO[C@H](C)[C@H](CCC(N)=O)NC(=O)[C@@H]4Cc5cccc6c5N4C(=O)[C@@H](NC(=O)c4cc5cc(C(=O)P(=O)(O)O)ccc5[nH]4)CC6)ccc3c2)C(C)(C)C)cc1] |

TABLE 1-continued
| Exemplary Compounds | |
|---|---|
| I-# | Structure |
| I-88 | 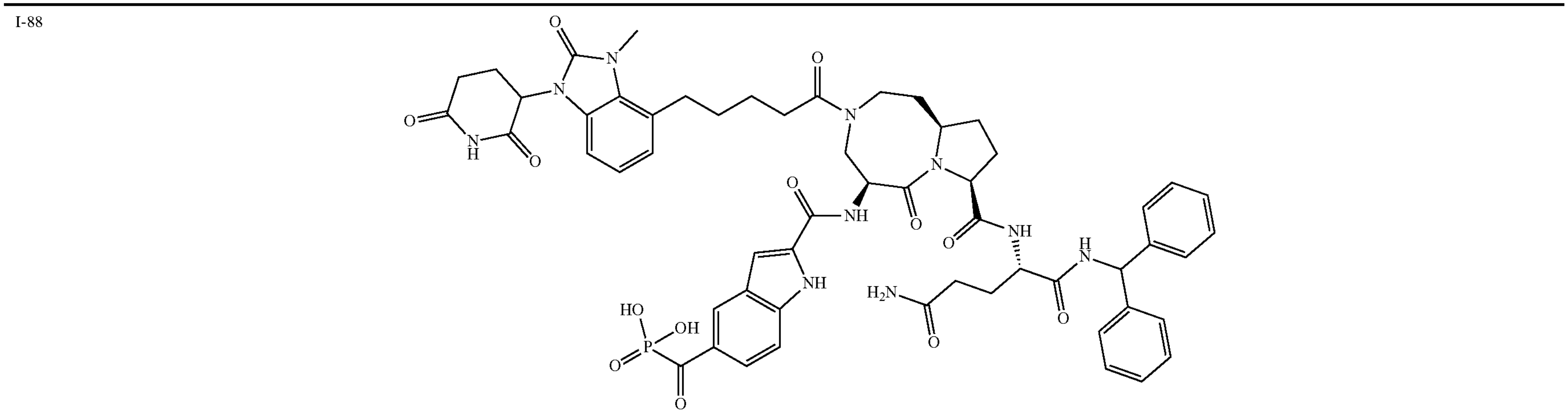 |
| I-89 | 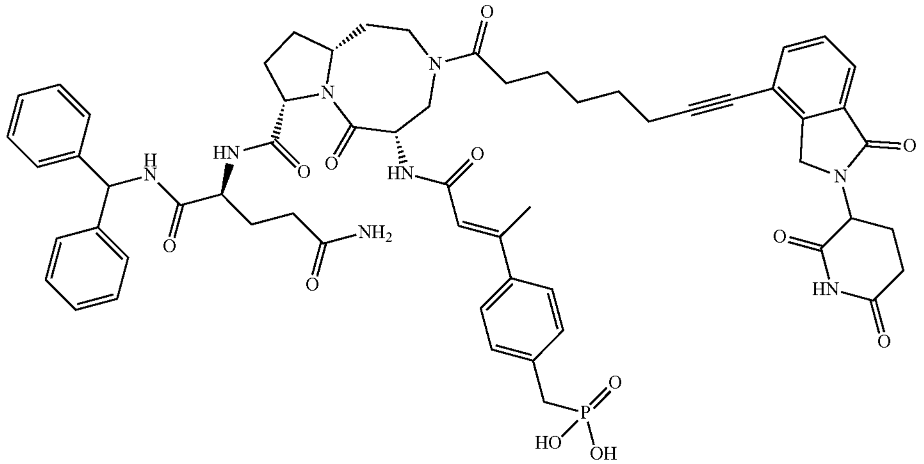 [SMILES: C/C(=C\C(=O)N[C@H]1CN(C(=O)CCCCCC#Cc2cccc3c2CN(C2CCC(=O)NC2=O)C3=O)CC[C@H]2CC[C@@H](C(=O)N[C@@H](CCC(N)=O)C(=O)NC(c3ccccc3)c3ccccc3)N2C1=O)c1ccc(CP(=O)(O)O)cc1] |

TABLE 1-continued
| Exemplary Compounds | |
|---|---|
| I-# | Structure |
| I-90 | 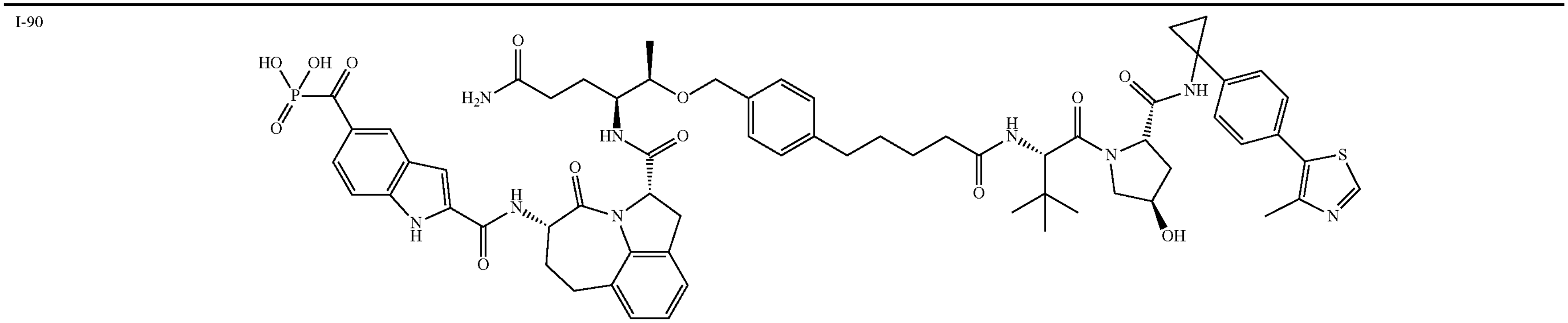 |
| I-91 | 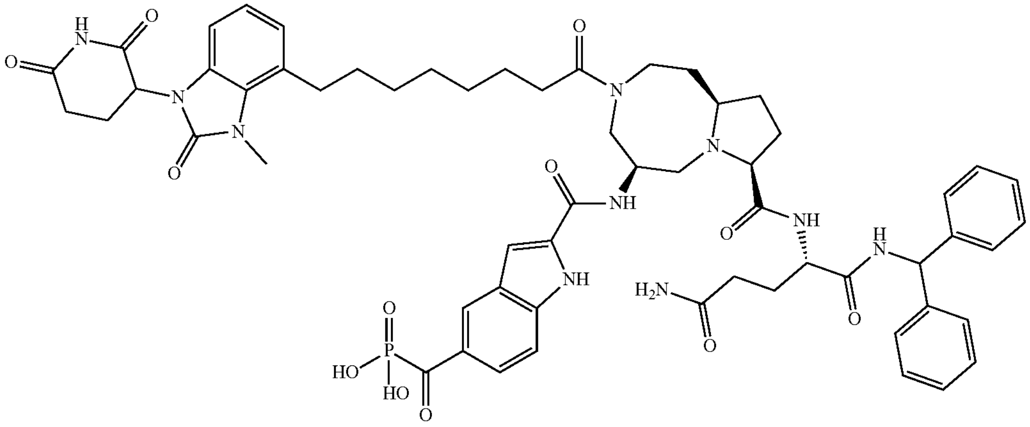 [SMILES: Cn1c(=O)n(C2CCC(=O)NC2=O)c2cccc(CCCCCCCC(=O)N3CC[C@H]4CC[C@@H](C(=O)N[C@@H](CCC(N)=O)C(=O)NC(c5ccccc5)c5ccccc5)N4C[C@@H](NC(=O)c4cc5cc(C(=O)P(=O)(O)O)ccc5[nH]4)C3)c21] |

TABLE 1-continued
| Exemplary Compounds | |
|---|---|
| I-# | Structure |
| I-92 | 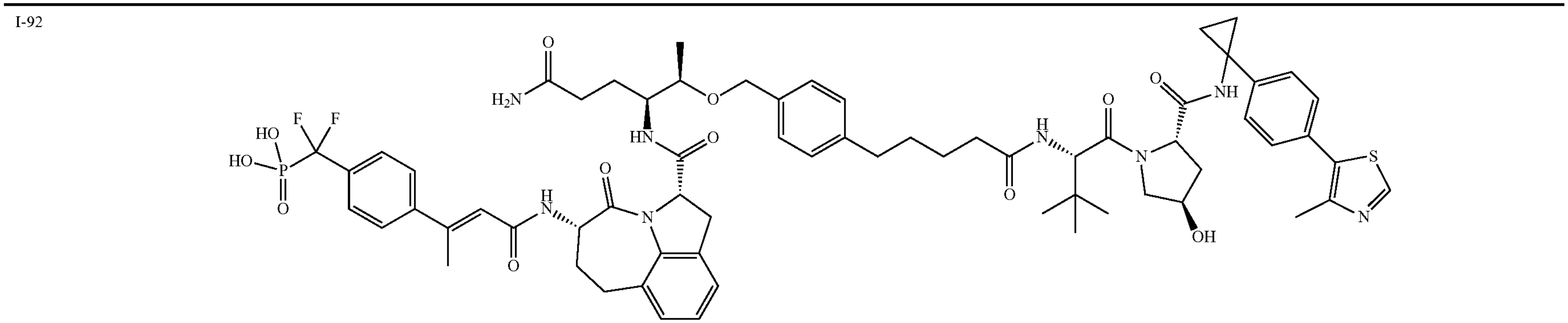 |
| I-93 | 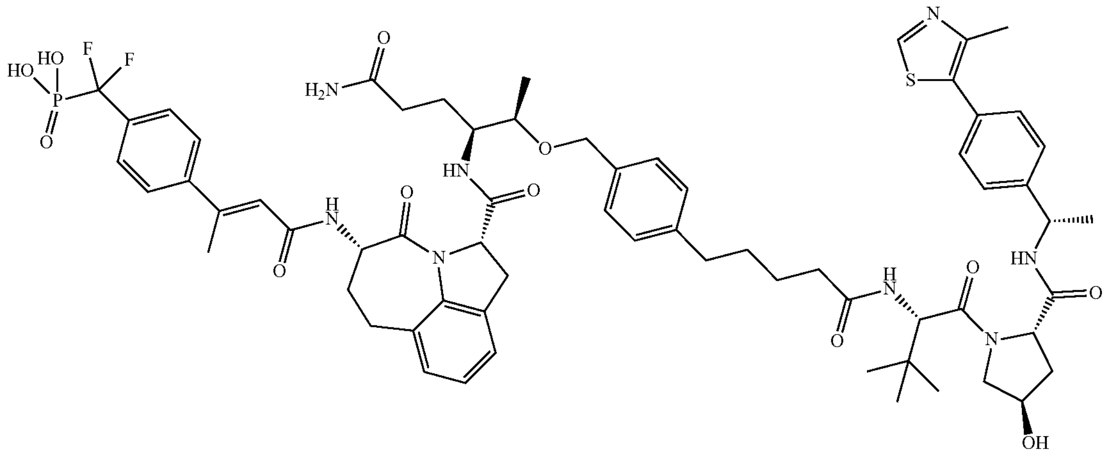 [SMILES: C/C(=C\C(=O)N[C@H]1CCc2cccc3c2N(C1=O)[C@H](C(=O)N[C@@H](CCC(N)=O)[C@@H](C)OCc1ccc(CCCCC(=O)N[C@H](C(=O)N2C[C@H](O)C[C@H]2C(=O)N[C@@H](C)c2ccc(-c4scnc4C)cc2)C(C)(C)C)cc1)C3)c1ccc(C(F)(F)P(=O)(O)O)cc1] |

TABLE 1-continued
| Exemplary Compounds | |
|---|---|
| I-# | Structure |
| I-94 | 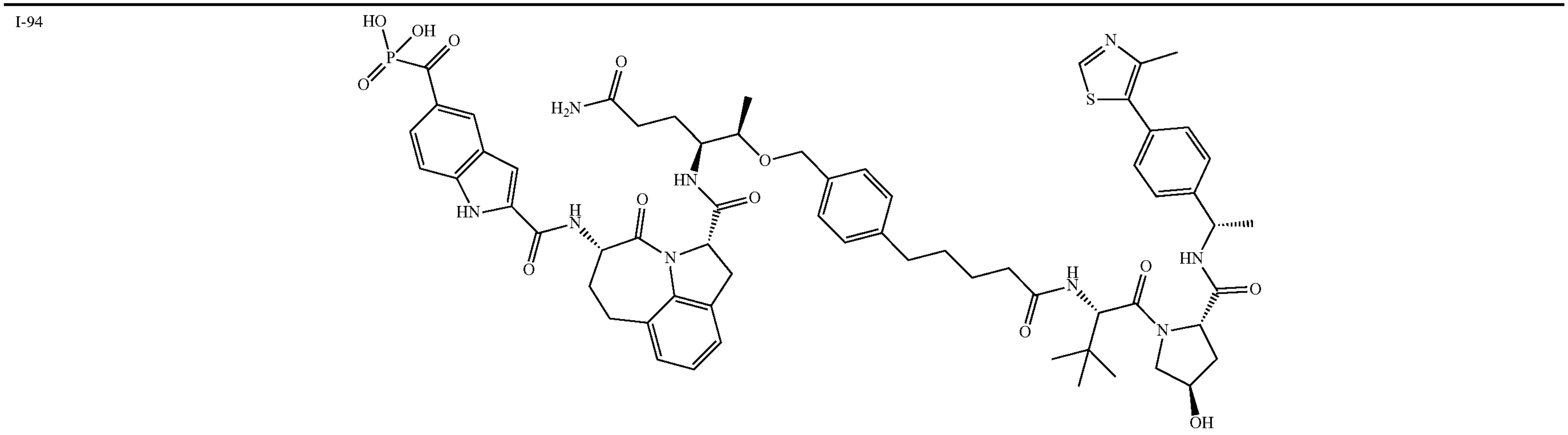 |
| I-95 | 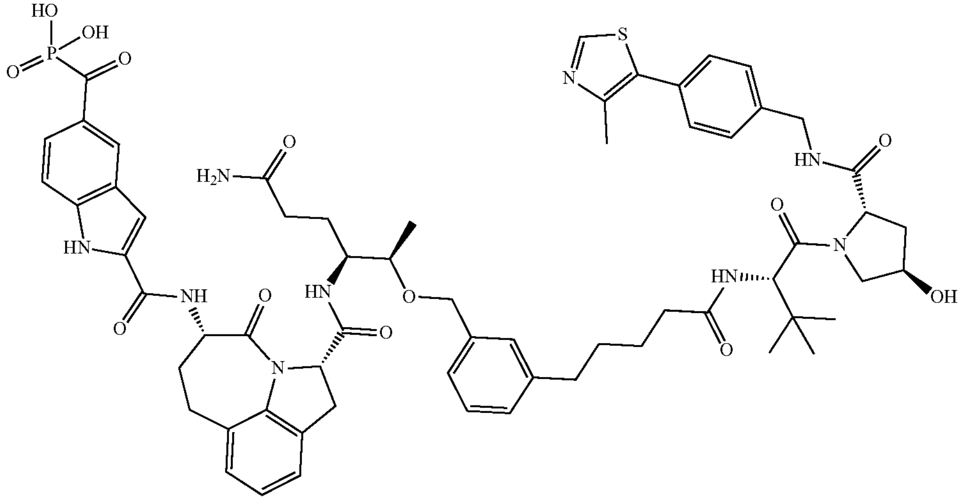 [SMILES: Cc1ncsc1-c1ccc(CNC(=O)[C@@H]2C[C@@H](O)CN2C(=O)[C@@H](NC(=O)CCCCc2cccc(CO[C@H](C)[C@H](CCC(N)=O)NC(=O)[C@@H]3Cc4cccc5c4N3C(=O)[C@@H](NC(=O)c3cc4cc(C(=O)P(=O)(O)O)ccc4[nH]3)CC5)c2)C(C)(C)C)cc1] |

TABLE 1-continued
| Exemplary Compounds | |
|---|---|
| I-# | Structure |
| I-96 | 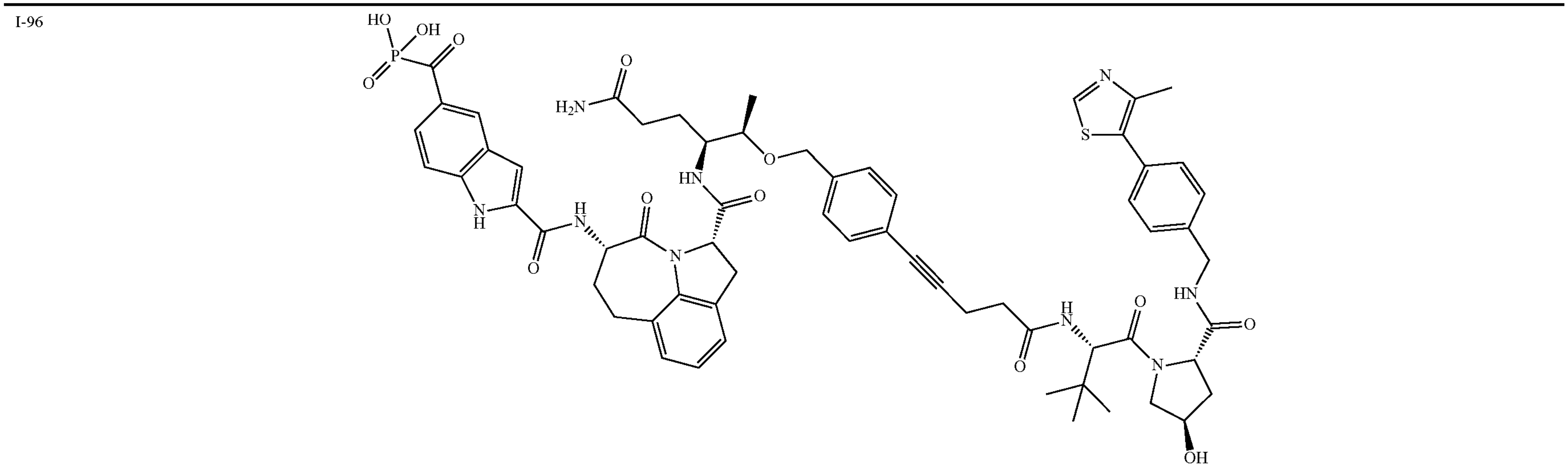 |
| I-97 | 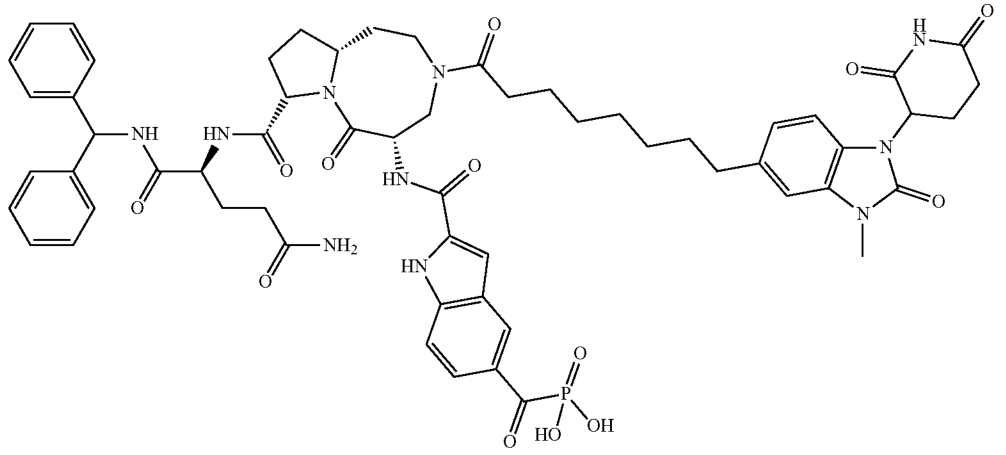 |

TABLE 1-continued
| Exemplary Compounds | |
|---|---|
| I-# | Structure |
| I-98 | 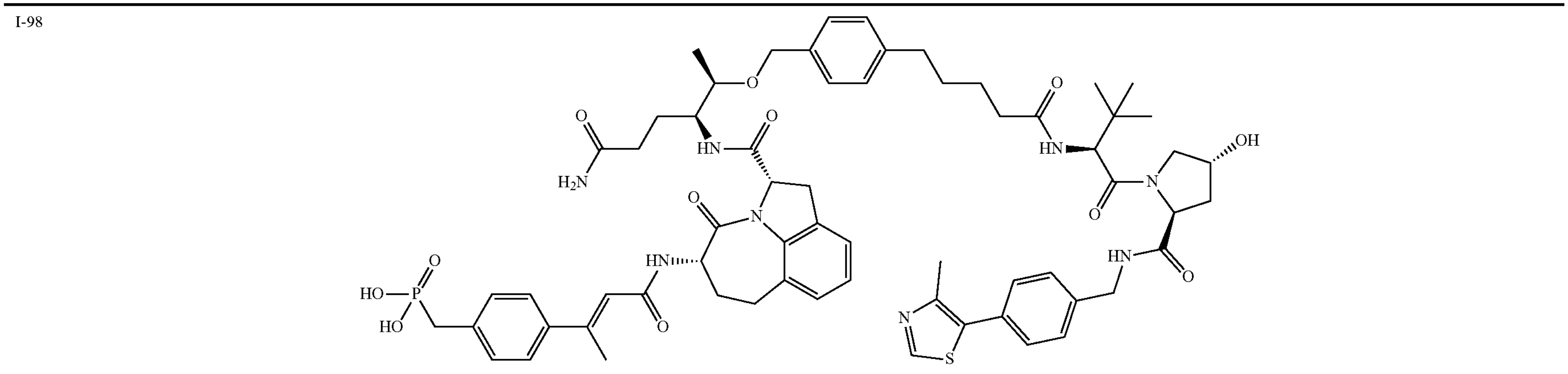 |
| I-99 | 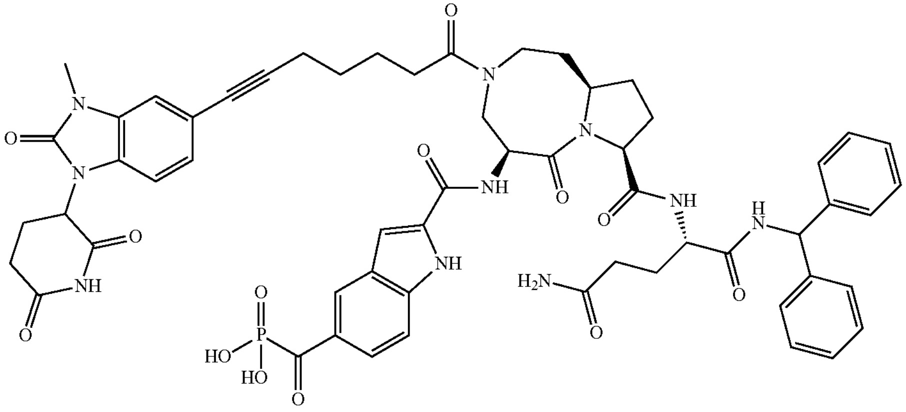 [SMILES: Cn1c(=O)n(C2CCC(=O)NC2=O)c2ccc(C#CCCCCC(=O)N3CC[C@H]4CC[C@@H](C(=O)N[C@@H](CCC(N)=O)C(=O)NC(c5ccccc5)c5ccccc5)N4C(=O)[C@@H](NC(=O)c4cc5cc(C(=O)P(=O)(O)O)ccc5[nH]4)C3)cc21] |

TABLE 1-continued
| Exemplary Compounds | |
|---|---|
| I-# | Structure |
| I-100 | 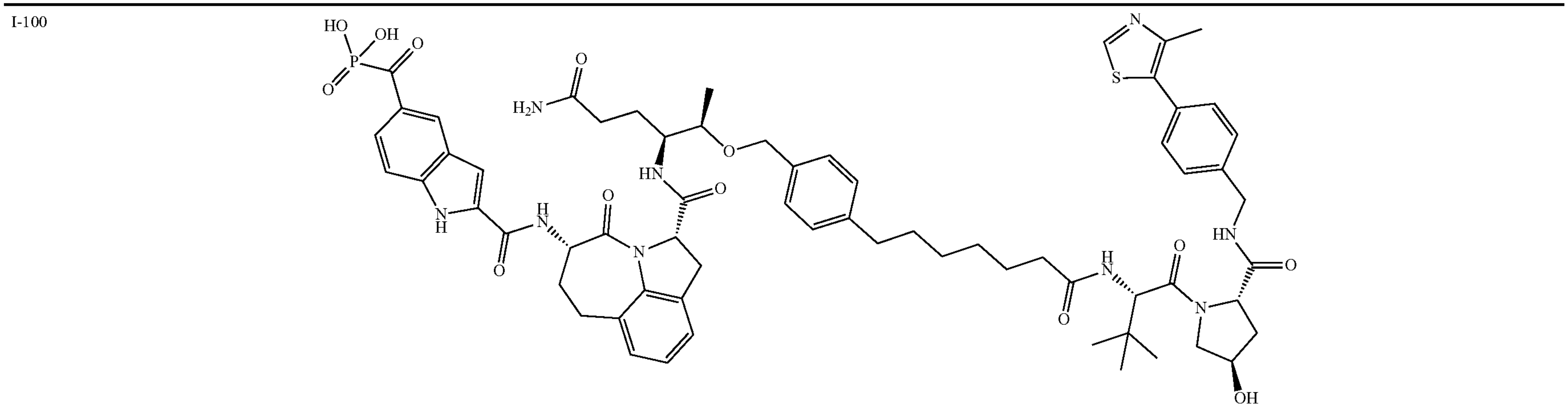 |
| I-101 | 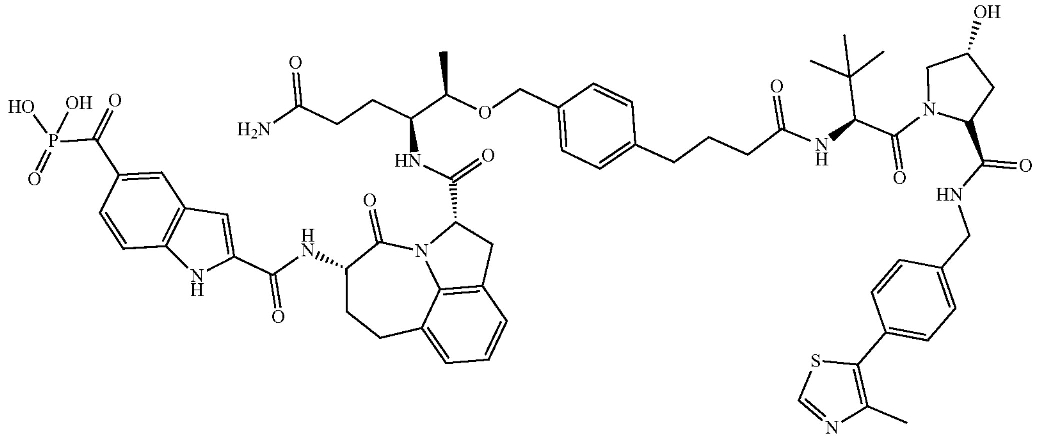 |

TABLE 1-continued
| Exemplary Compounds | |
|---|---|
| I-# | Structure |
| I-102 | 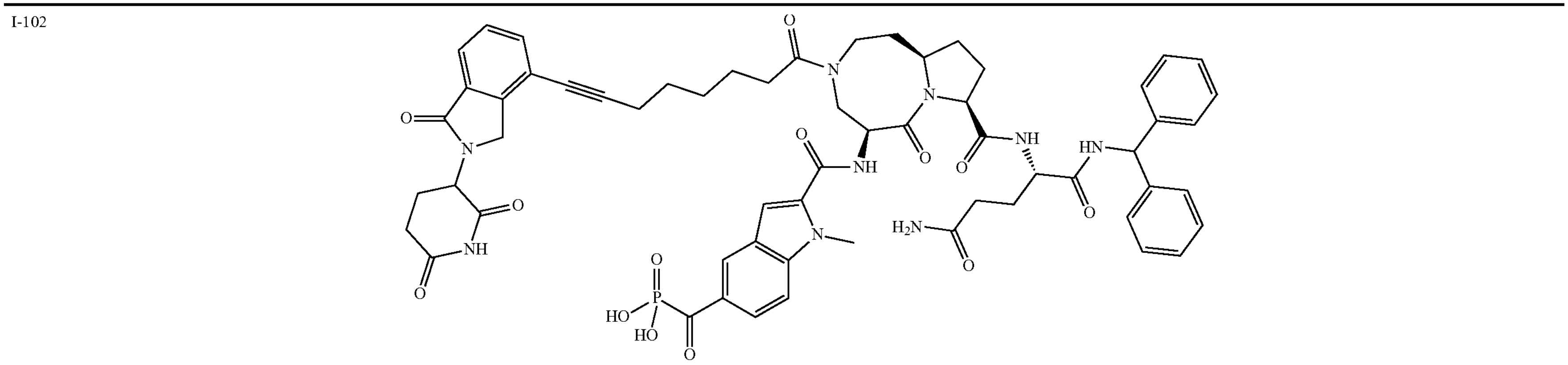 |
| I-103 | 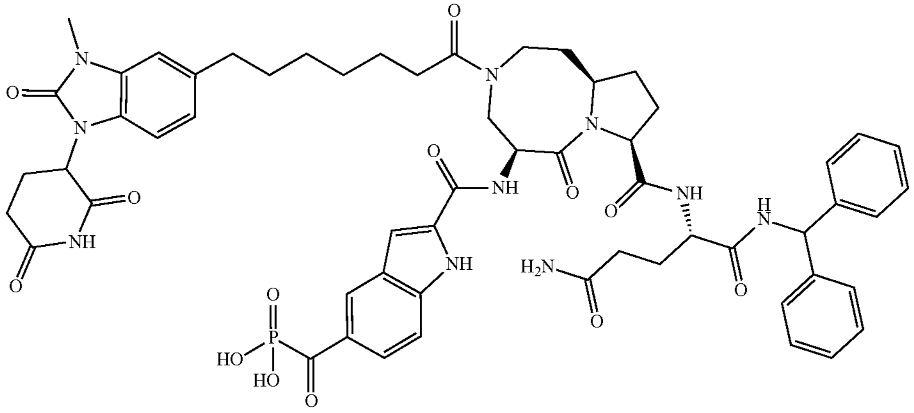 [SMILES: Cn1c(=O)n(C2CCC(=O)NC2=O)c2ccc(CCCCCCC(=O)N3CC[C@H]4CC[C@@H](C(=O)N[C@@H](CCC(N)=O)C(=O)NC(c5ccccc5)c5ccccc5)N4C(=O)[C@@H](NC(=O)c4cc5cc(C(=O)P(=O)(O)O)ccc5[nH]4)C3)cc21] |

TABLE 1-continued
| Exemplary Compounds | |
|---|---|
| I-# | Structure |
| I-104 | 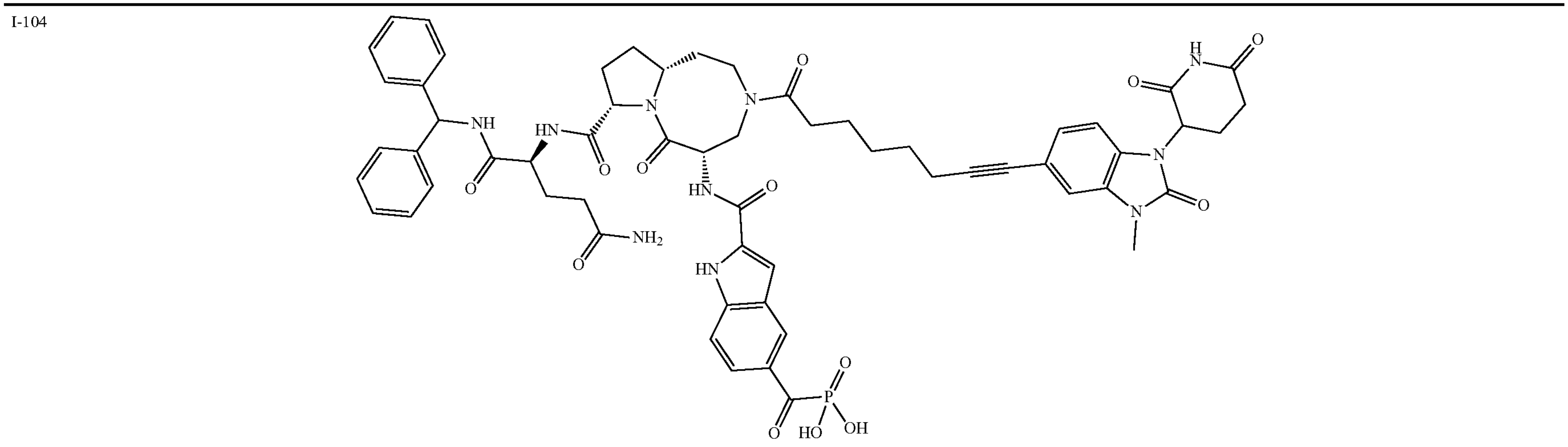 |
| I-105 | 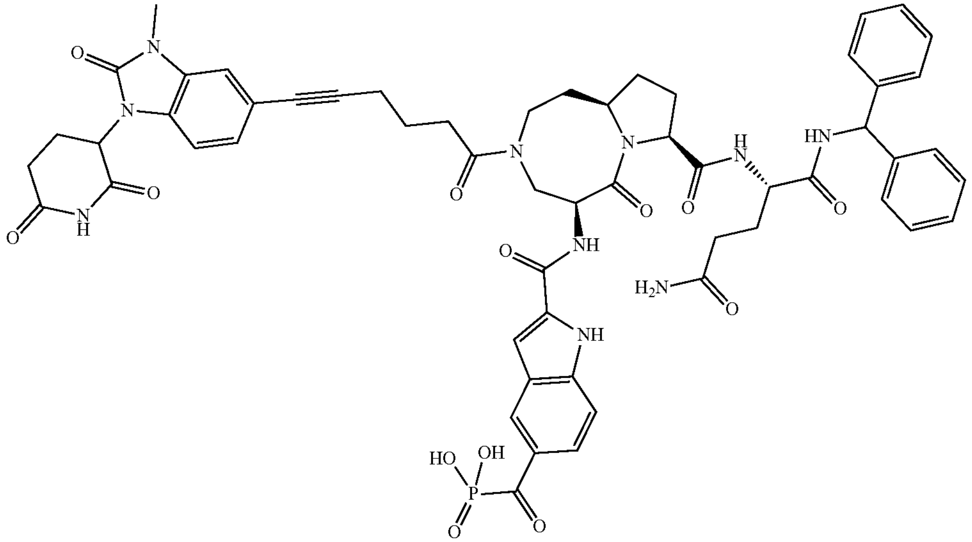 [SMILES: Cn1c(=O)n(C2CCC(=O)NC2=O)c2ccc(C#CCCCC(=O)N3CC[C@H]4CC[C@@H](C(=O)N[C@@H](CCC(N)=O)C(=O)NC(c5ccccc5)c5ccccc5)N4C(=O)[C@@H](NC(=O)c4cc5cc(C(=O)P(=O)(O)O)ccc5[nH]4)C3)cc21] |

TABLE 1-continued
| Exemplary Compounds | |
|---|---|
| I-# | Structure |
| I-106 | 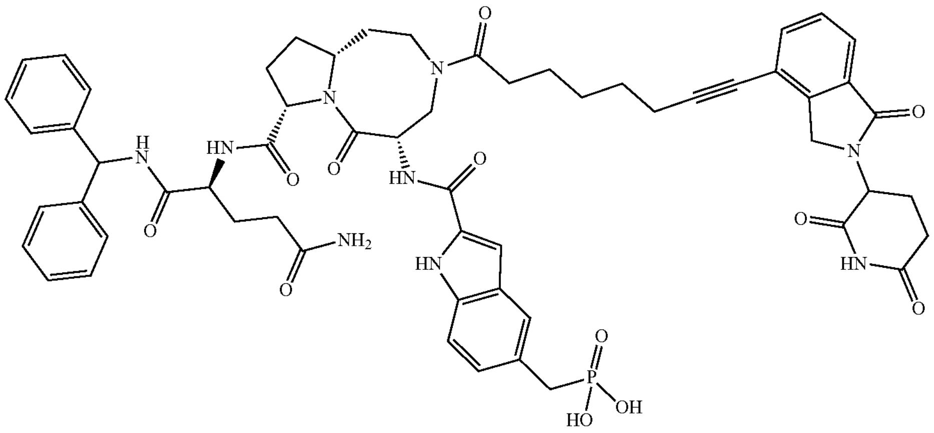 |

TABLE 1-continued
| Exemplary Compounds | |
|---|---|
| I-# | Structure |
| I-107 | 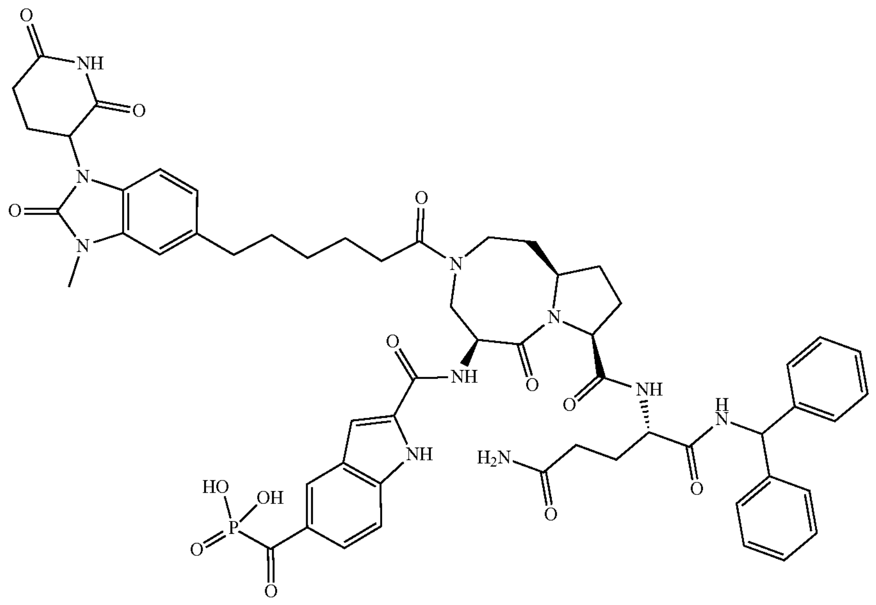 [SMILES: Cn1c(=O)n(C2CCC(=O)NC2=O)c2ccc(CCCCCC(=O)N3CC[C@H]4CC[C@@H](C(=O)N[C@@H](CCC(N)=O)C(=O)NC(c5ccccc5)c5ccccc5)N4C(=O)[C@@H](NC(=O)c4cc5cc(C(=O)P(=O)(O)O)ccc5[nH]4)C3)cc21] |
| I-108 | 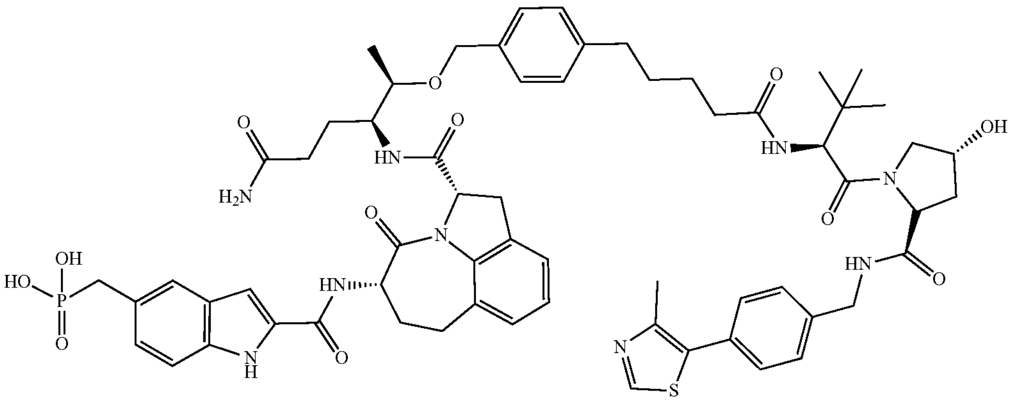 |

TABLE 1-continued
| Exemplary Compounds | |
|---|---|
| I-# | Structure |
| I-109 | 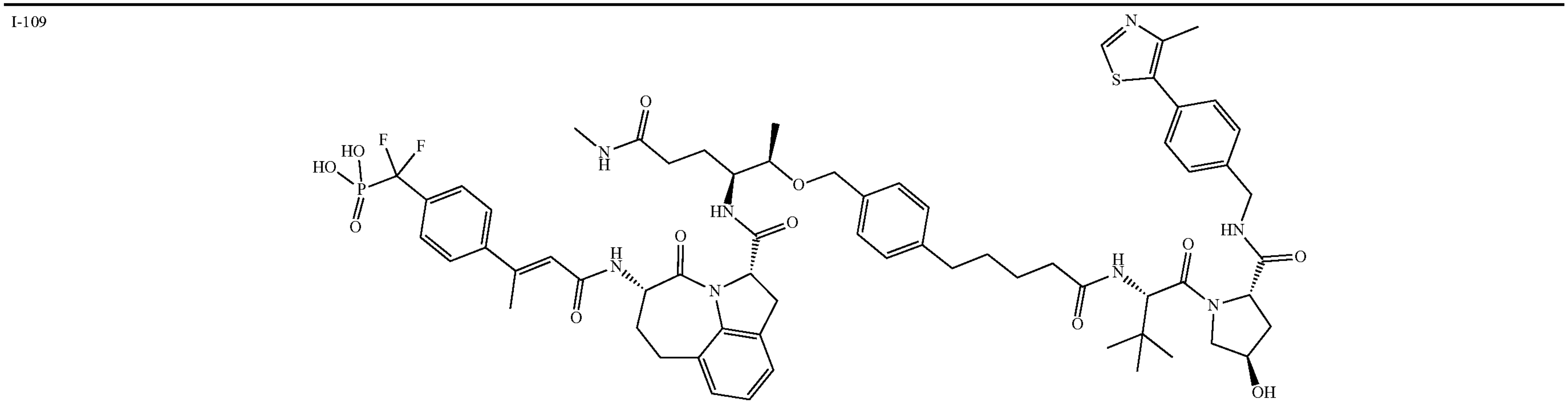 |
| I-110 | 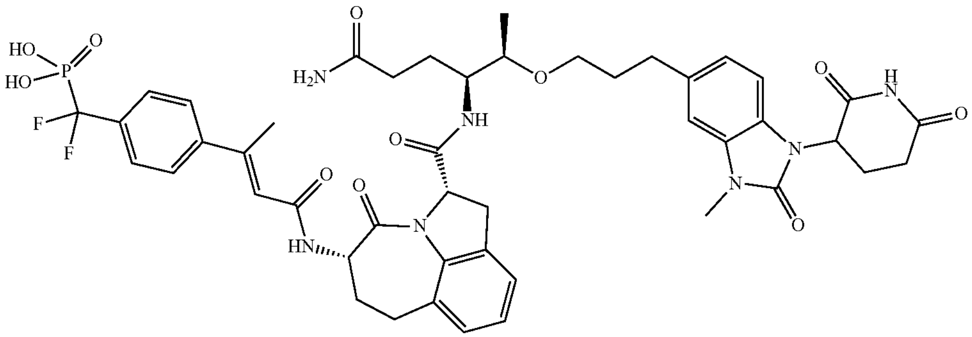 [SMILES: C/C(=C\C(=O)N[C@H]1CCc2cccc3c2N(C1=O)[C@H](C(=O)N[C@@H](CCC(N)=O)[C@@H](C)OCCCc1ccc2c(c1)n(C)c(=O)n2C1CCC(=O)NC1=O)C3)c1ccc(C(F)(F)P(=O)(O)O)cc1] |

TABLE 1-continued
| Exemplary Compounds | |
|---|---|
| I-# | Structure |
| I-111 | 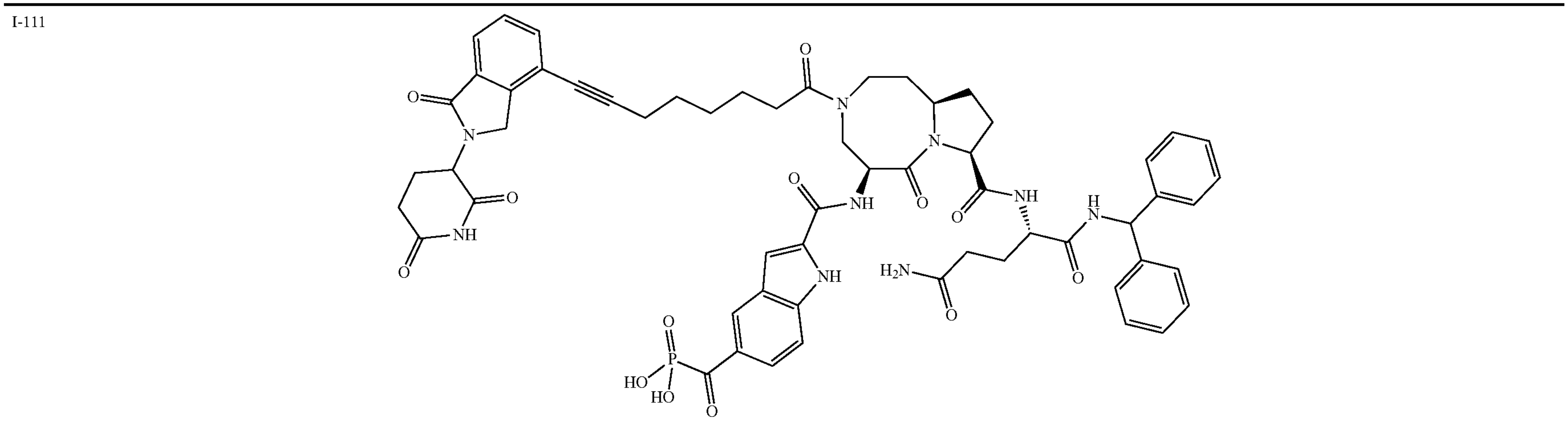 |
| I-112 | 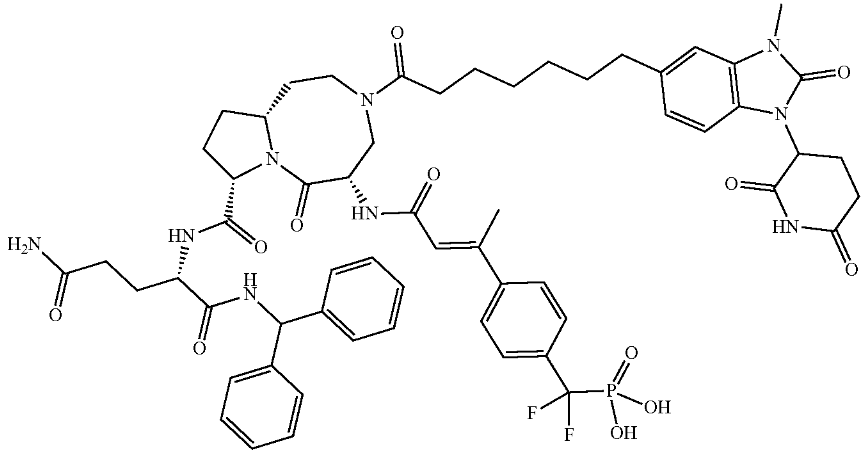 [SMILES: C/C(=C\C(=O)N[C@H]1CN(C(=O)CCCCCCc2ccc3c(c2)n(C)c(=O)n3C2CCC(=O)NC2=O)CC[C@H]2CC[C@@H](C(=O)N[C@@H](CCC(N)=O)C(=O)NC(c3ccccc3)c3ccccc3)N2C1=O)c1ccc(C(F)(F)P(=O)(O)O)cc1] |

TABLE 1-continued
| Exemplary Compounds | |
|---|---|
| I-# | Structure |
| I-113 | 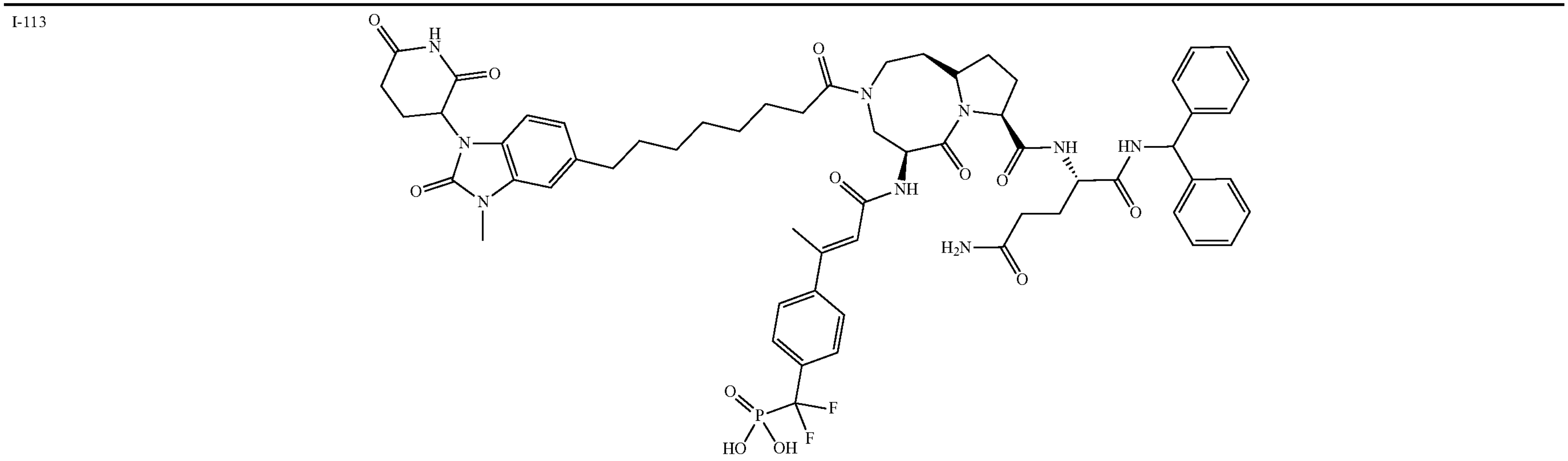 |
| I-114 | 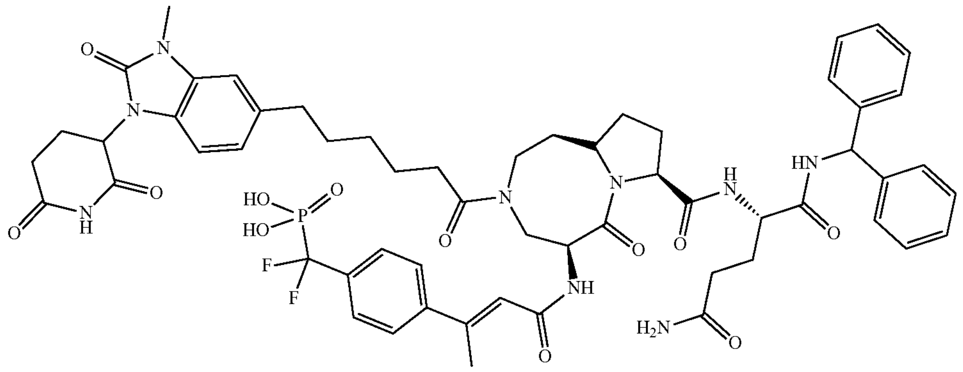 |

TABLE 1-continued
| Exemplary Compounds | |
|---|---|
| I-# | Structure |
| I-115 | 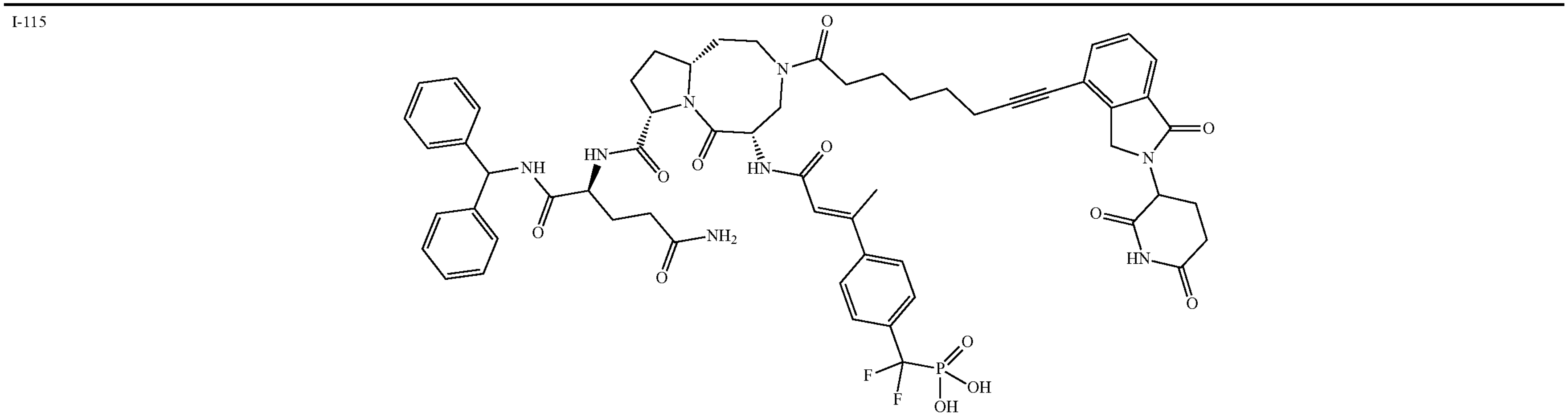 |
| I-117 | 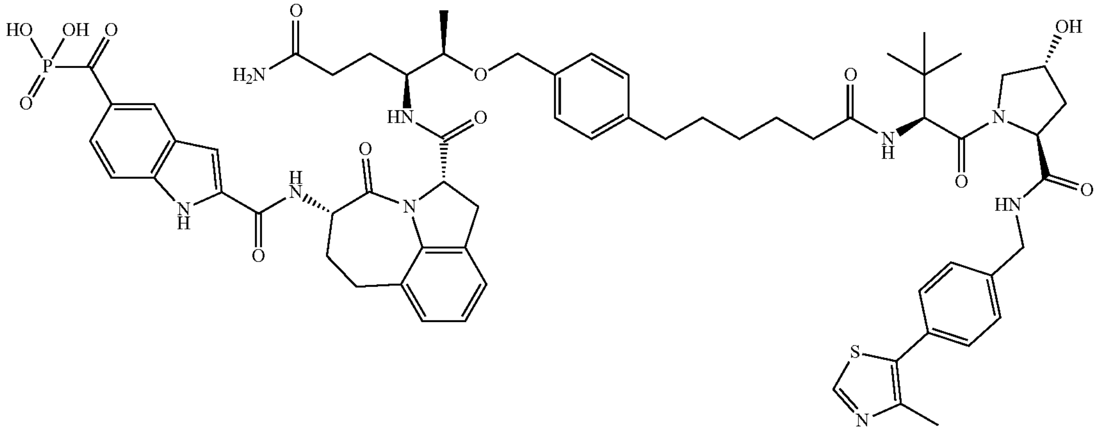 [SMILES: Cc1ncsc1-c1ccc(CNC(=O)[C@@H]2C[C@@H](O)CN2C(=O)[C@@H](NC(=O)CCCCCc2ccc(CO[C@H](C)[C@H](CCC(N)=O)NC(=O)[C@@H]3Cc4cccc5c4N3C(=O)[C@@H](NC(=O)c3cc4cc(C(=O)P(=O)(O)O)ccc4[nH]3)CC5)cc2)C(C)(C)C)cc1] |

TABLE 1-continued
| Exemplary Compounds | |
|---|---|
| I-# | Structure |
| I-118 | 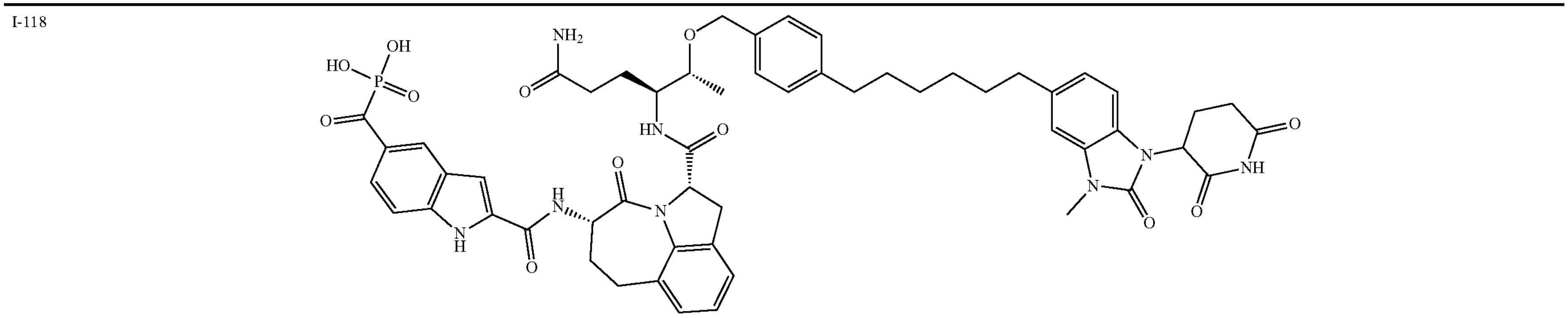 |
| I-119 | 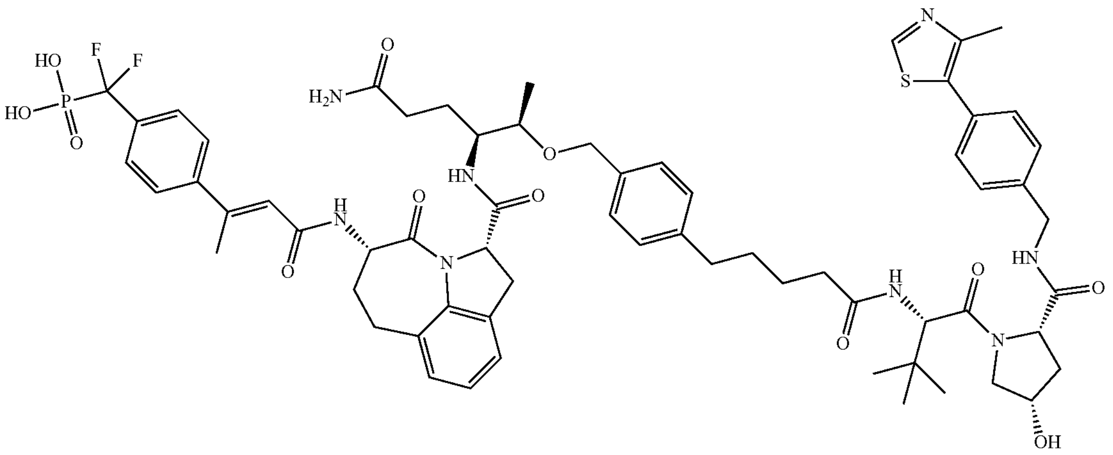 [SMILES: C/C(=C\C(=O)N[C@H]1CCc2cccc3c2N(C1=O)[C@H](C(=O)N[C@@H](CCC(N)=O)[C@@H](C)OCc1ccc(CCCCC(=O)N[C@H](C(=O)N2C[C@@H](O)C[C@H]2C(=O)NCc2ccc(-c4scnc4C)cc2)C(C)(C)C)cc1)C3)c1ccc(C(F)(F)P(=O)(O)O)cc1] |

TABLE 1-continued
| Exemplary Compounds | |
|---|---|
| I-# | Structure |
| I-120 | 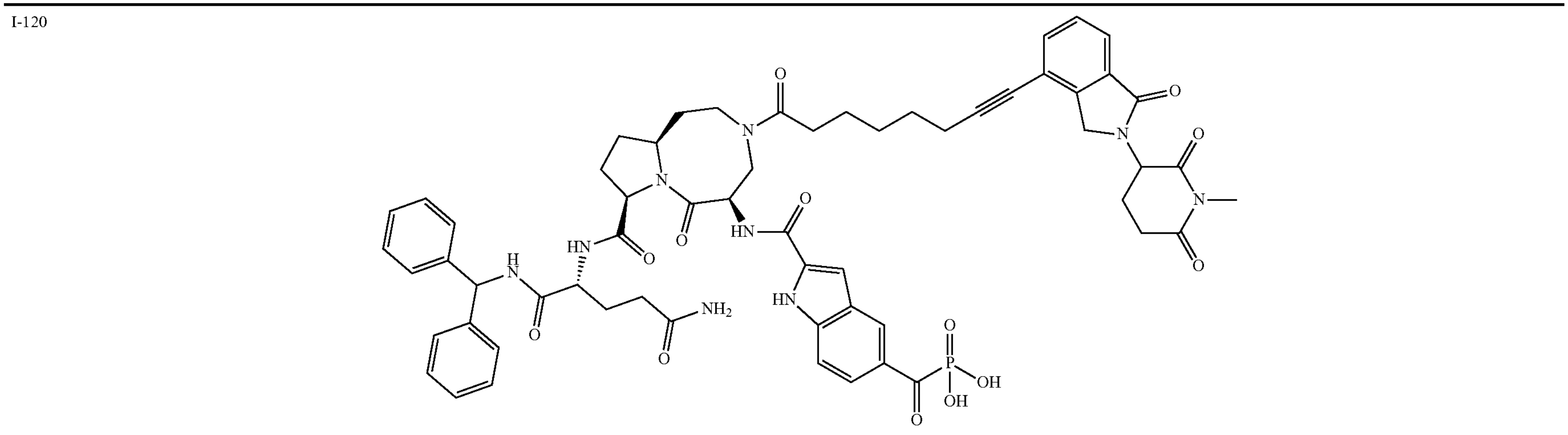 |
| I-121 | 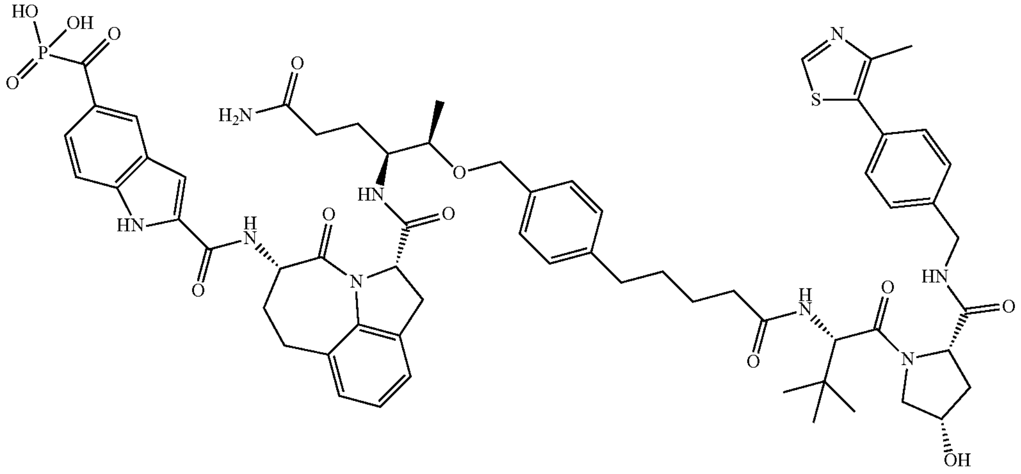 [SMILES: Cc1ncsc1-c1ccc(CNC(=O)[C@@H]2C[C@H](O)CN2C(=O)[C@@H](NC(=O)CCCCc2ccc(CO[C@H](C)[C@H](CCC(N)=O)NC(=O)[C@@H]3Cc4cccc5c4N3C(=O)[C@@H](NC(=O)c3cc4cc(C(=O)P(=O)(O)O)ccc4[nH]3)CC5)cc2)C(C)(C)C)cc1] |

TABLE 1-continued
| Exemplary Compounds | |
|---|---|
| I-# | Structure |
| I-122 | 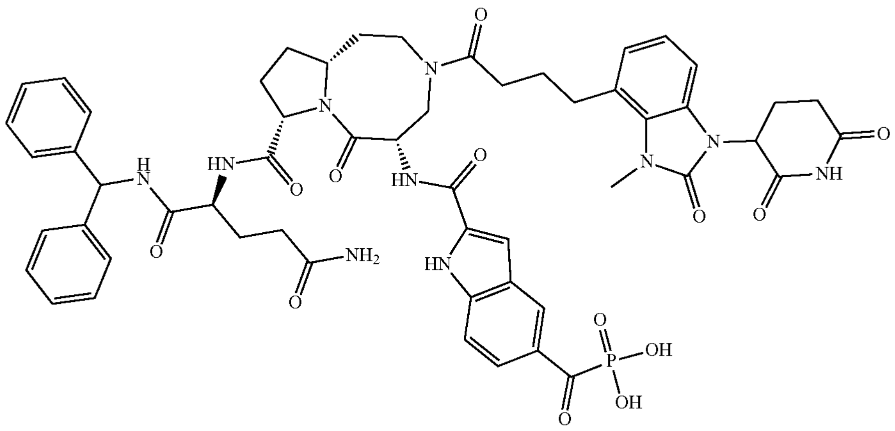 [SMILES: Cn1c(=O)n(C2CCC(=O)NC2=O)c2cccc(CCCC(=O)N3CC[C@H]4CC[C@@H](C(=O)N[C@@H](CCC(N)=O)C(=O)NC(c5ccccc5)c5ccccc5)N4C(=O)[C@@H](NC(=O)c4cc5cc(C(=O)P(=O)(O)O)ccc5[nH]4)C3)c21] |
| I-123 | 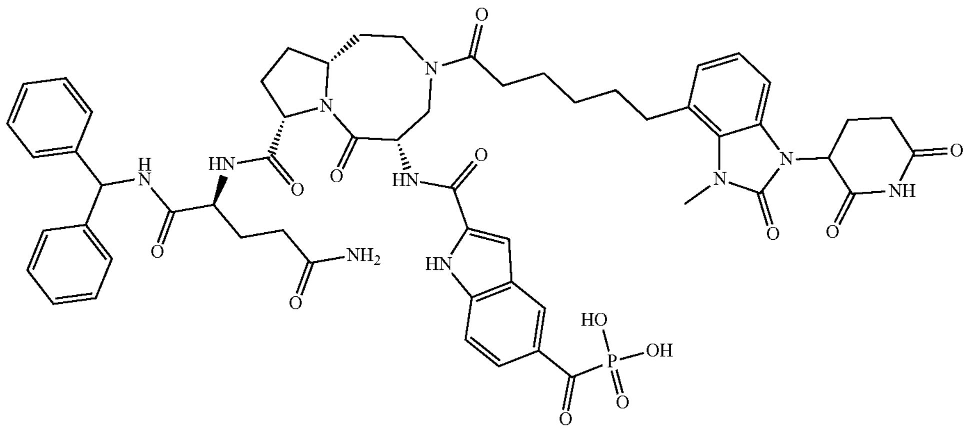 [SMILES: Cn1c(=O)n(C2CCC(=O)NC2=O)c2cccc(CCCCCC(=O)N3CC[C@H]4CC[C@@H](C(=O)N[C@@H](CCC(N)=O)C(=O)NC(c5ccccc5)c5ccccc5)N4C(=O)[C@@H](NC(=O)c4cc5cc(C(=O)P(=O)(O)O)ccc5[nH]4)C3)c21] |

TABLE 1-continued
| Exemplary Compounds | |
|---|---|
| I-# | Structure |
| I-124 | 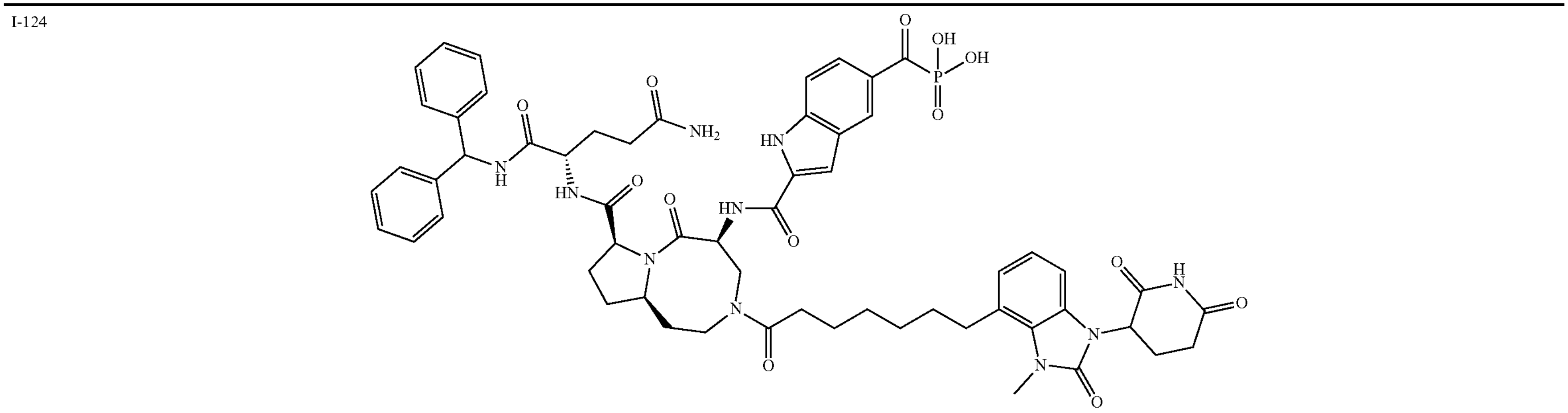 |
| I-125 | 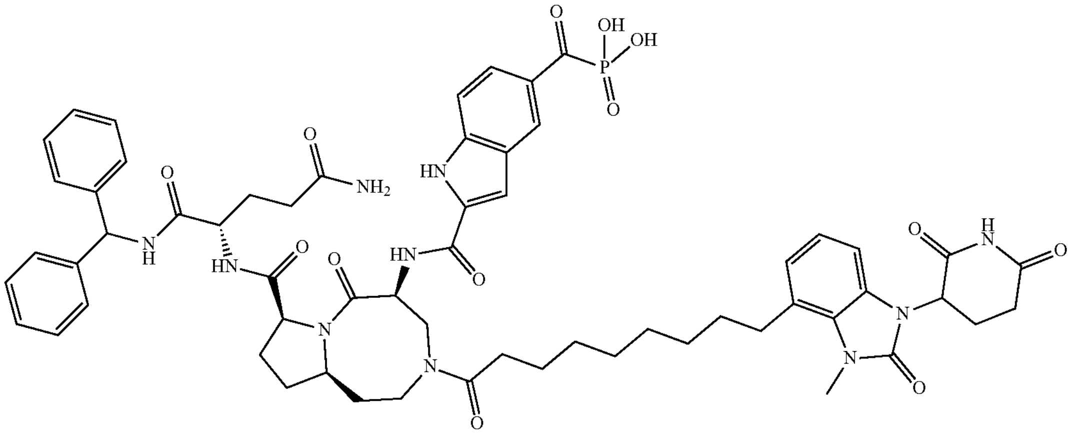 [SMILES: Cn1c(=O)n(C2CCC(=O)NC2=O)c2cccc(CCCCCCCCC(=O)N3CC[C@H]4CC[C@@H](C(=O)N[C@@H](CCC(N)=O)C(=O)NC(c5ccccc5)c5ccccc5)N4C(=O)[C@@H](NC(=O)c4cc5cc(C(=O)P(=O)(O)O)ccc5[nH]4)C3)c21] |

TABLE 1-continued
| Exemplary Compounds | |
|---|---|
| I-# | Structure |
| I-126 | 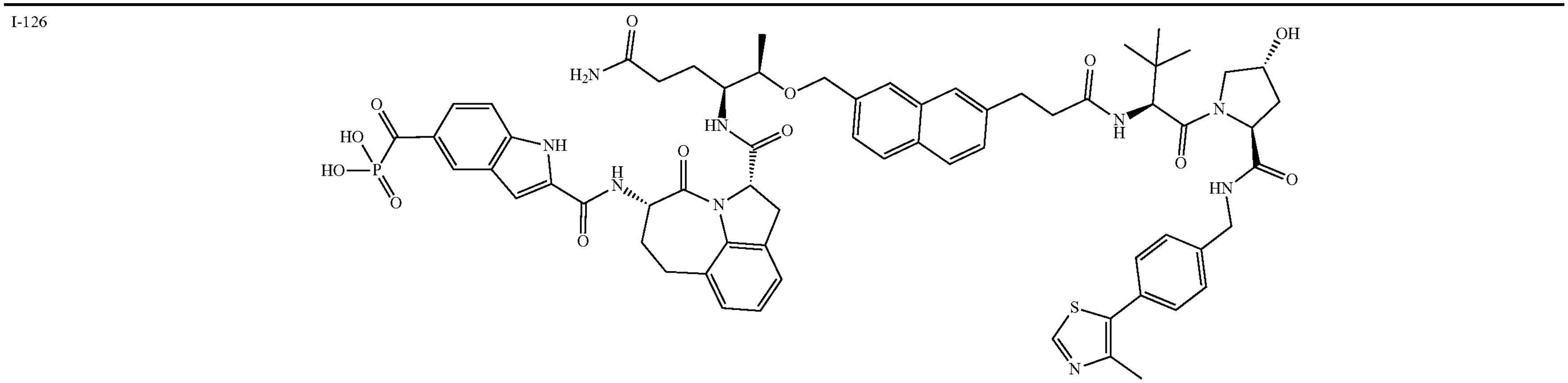 |
| I-127 | 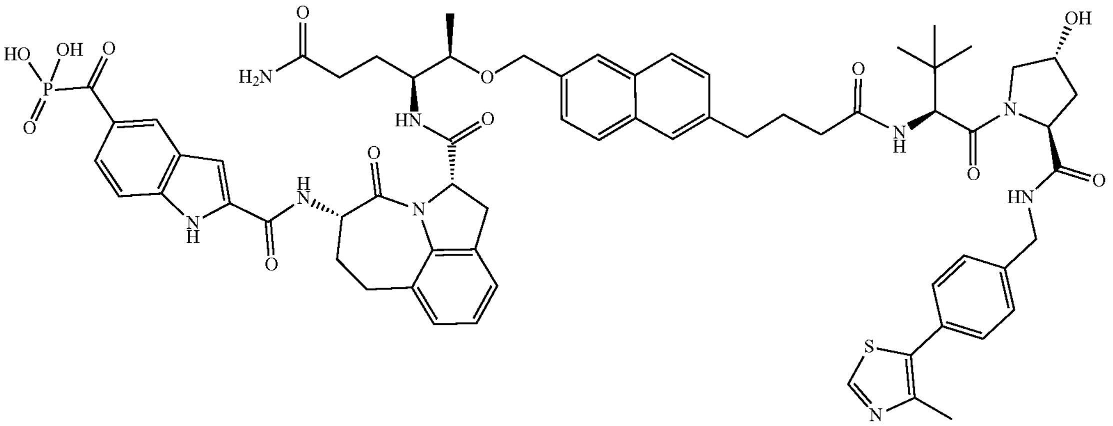 [SMILES: Cc1ncsc1-c1ccc(CNC(=O)[C@@H]2C[C@@H](O)CN2C(=O)[C@@H](NC(=O)CCCc2ccc3cc(CO[C@H](C)[C@H](CCC(N)=O)NC(=O)[C@@H]4Cc5cccc6c5N4C(=O)[C@@H](NC(=O)c4cc5cc(C(=O)P(=O)(O)O)ccc5[nH]4)CC6)ccc3c2)C(C)(C)C)cc1] |

TABLE 1-continued
| Exemplary Compounds | |
|---|---|
| I-# | Structure |
| I-128 | 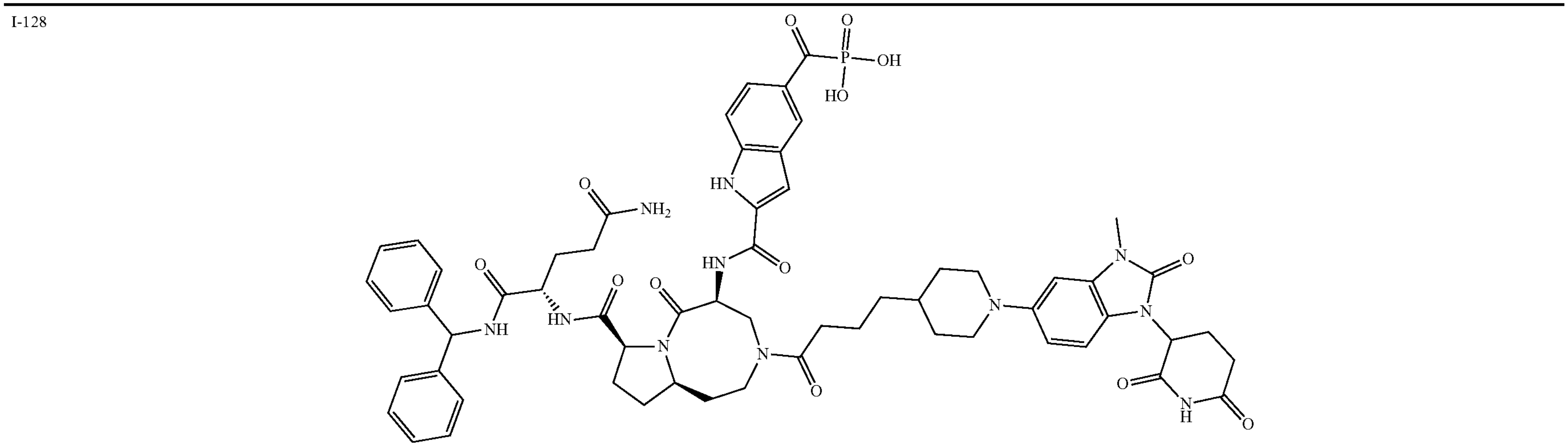 |
| I-129 | 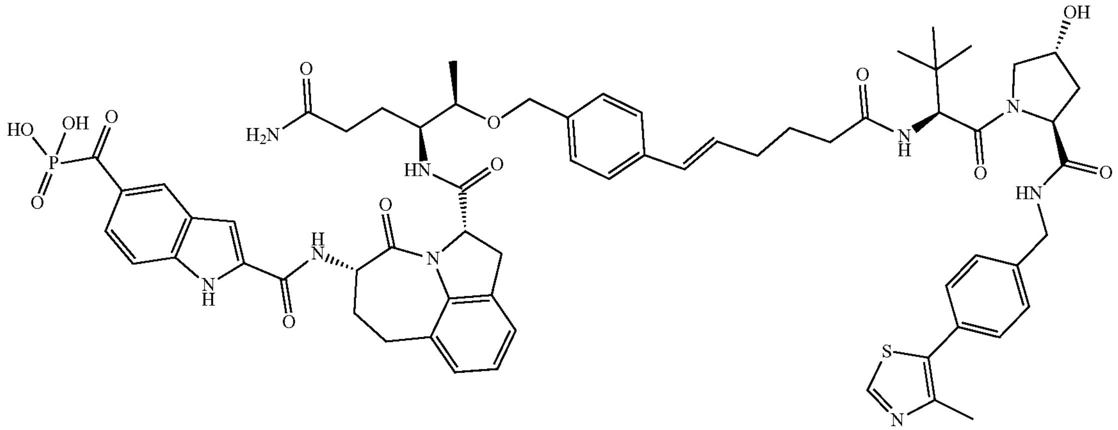 [SMILES: Cc1ncsc1-c1ccc(CNC(=O)[C@@H]2C[C@@H](O)CN2C(=O)[C@@H](NC(=O)CCC/C=C/c2ccc(CO[C@H](C)[C@H](CCC(N)=O)NC(=O)[C@@H]3Cc4cccc5c4N3C(=O)[C@@H](NC(=O)c3cc4cc(C(=O)P(=O)(O)O)ccc4[nH]3)CC5)cc2)C(C)(C)C)cc1] |

TABLE 1-continued
| Exemplary Compounds | |
|---|---|
| I-# | Structure |
| I-130 | 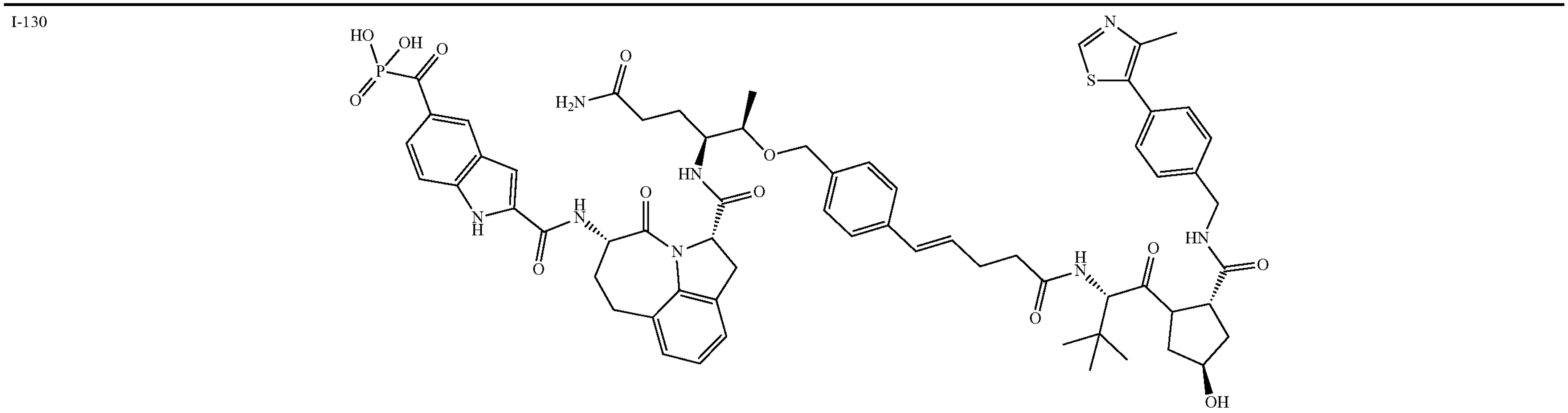 |
| I-131 | 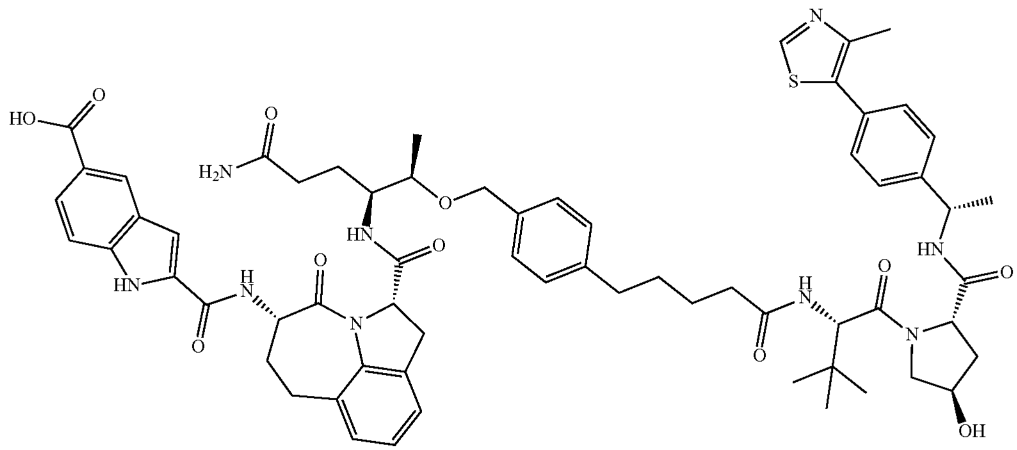 [SMILES: Cc1ncsc1-c1ccc([C@H](C)NC(=O)[C@@H]2C[C@@H](O)CN2C(=O)[C@@H](NC(=O)CCCCc2ccc(CO[C@H](C)[C@H](CCC(N)=O)NC(=O)[C@@H]3Cc4cccc5c4N3C(=O)[C@@H](NC(=O)c3cc4cc(C(=O)O)ccc4[nH]3)CC5)cc2)C(C)(C)C)cc1] |

TABLE 1-continued
| Exemplary Compounds | |
|---|---|
| I-# | Structure |
| I-132 | 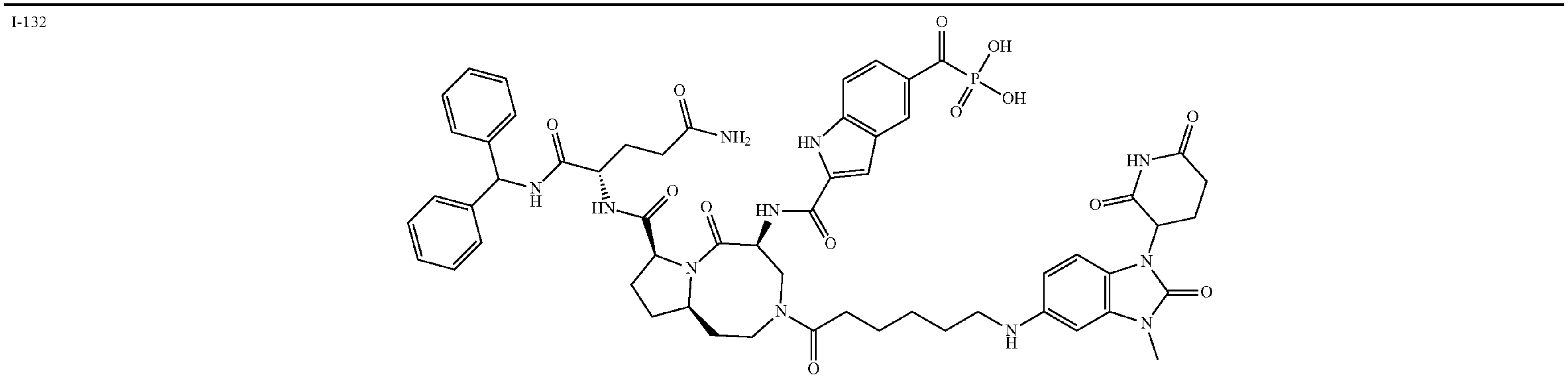 |
| I-133 | 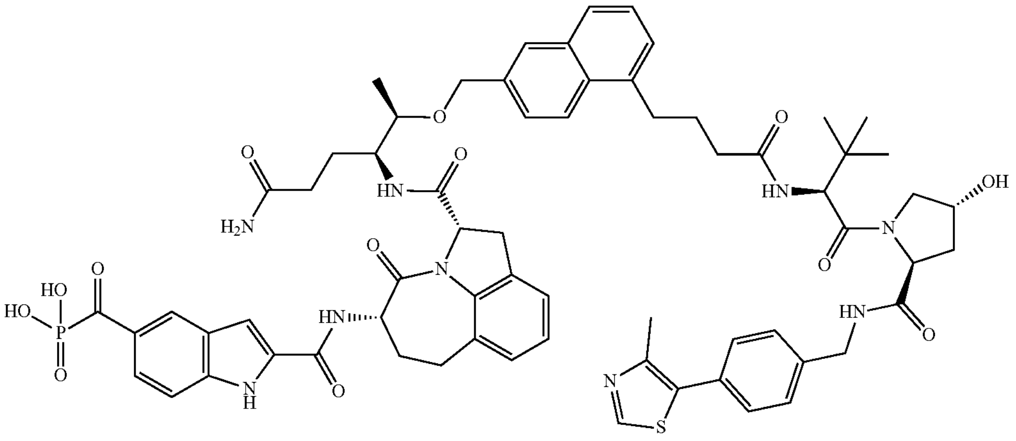 [SMILES: Cc1ncsc1-c1ccc(CNC(=O)[C@@H]2C[C@@H](O)CN2C(=O)[C@@H](NC(=O)CCCc2cccc3cc(CO[C@H](C)[C@H](CCC(N)=O)NC(=O)[C@@H]4Cc5cccc6c5N4C(=O)[C@@H](NC(=O)c4cc5cc(C(=O)P(=O)(O)O)ccc5[nH]4)CC6)ccc23)C(C)(C)C)cc1] |

TABLE 1-continued
| Exemplary Compounds | |
|---|---|
| I-# | Structure |
| I-134 | 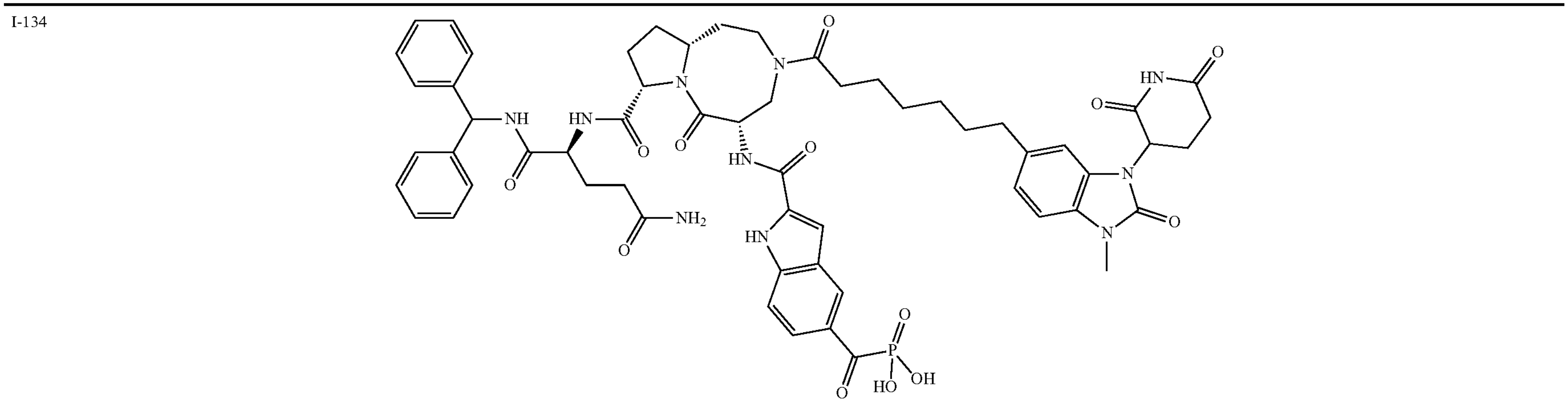 |
| I-135 | 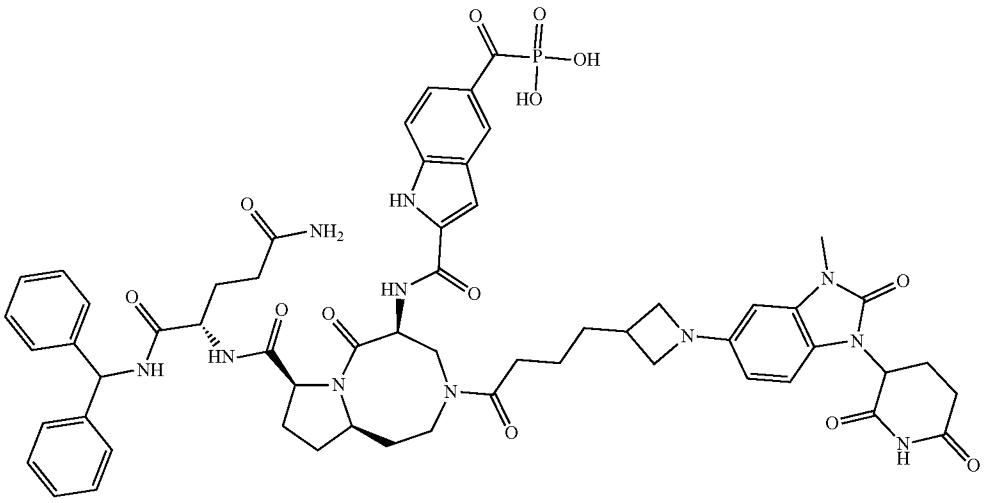 [SMILES: Cn1c(=O)n(C2CCC(=O)NC2=O)c2ccc(N3CC(CCCC(=O)N4CC[C@H]5CC[C@@H](C(=O)N[C@@H](CCC(N)=O)C(=O)NC(c6ccccc6)c6ccccc6)N5C(=O)[C@@H](NC(=O)c5cc6cc(C(=O)P(=O)(O)O)ccc6[nH]5)C4)C3)cc21] |

TABLE 1-continued
| Exemplary Compounds | |
|---|---|
| I-# | Structure |
| I-136 | 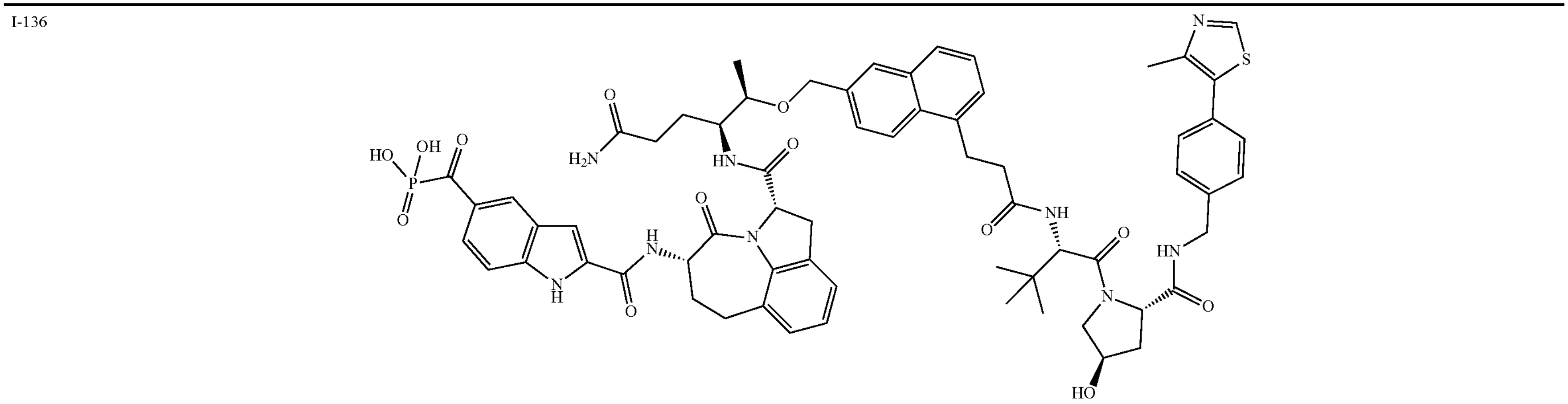 |
| I-137 | 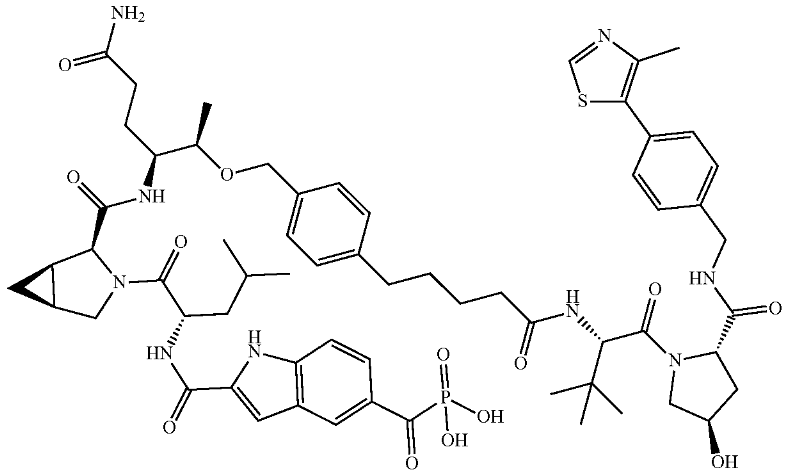 [SMILES: Cc1ncsc1-c1ccc(CNC(=O)[C@@H]2C[C@@H](O)CN2C(=O)[C@@H](NC(=O)CCCCc2ccc(CO[C@H](C)[C@H](CCC(N)=O)NC(=O)[C@@H]3[C@@H]4C[C@@H]4CN3C(=O)[C@H](CC(C)C)NC(=O)c3cc4cc(C(=O)P(=O)(O)O)ccc4[nH]3)cc2)C(C)(C)C)cc1] |

TABLE 1-continued
| Exemplary Compounds | |
|---|---|
| I-# | Structure |
| I-138 | 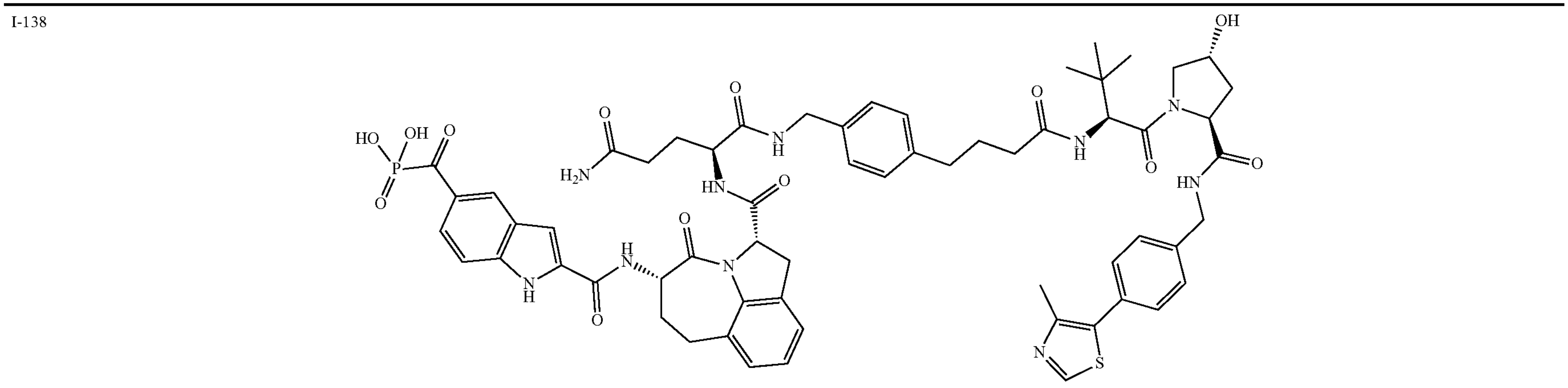 |
| I-139 | 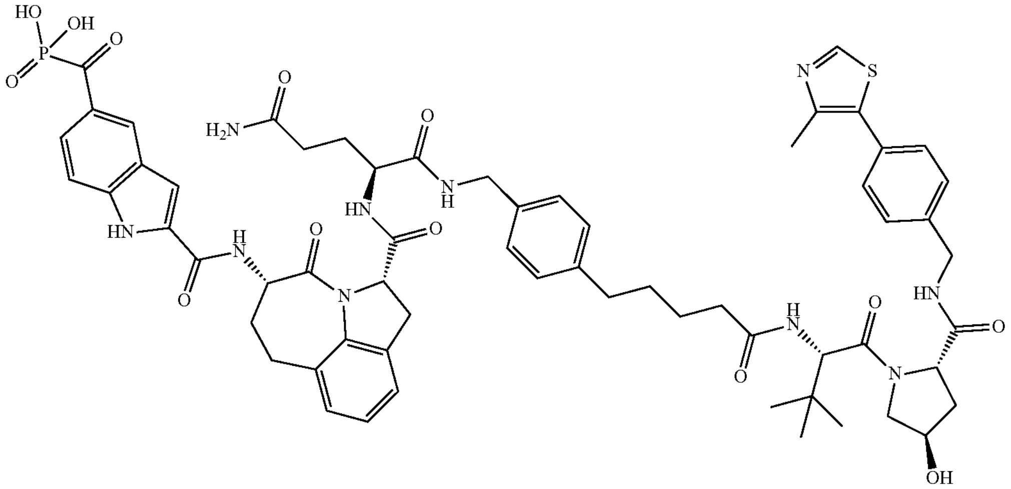 [SMILES: Cc1ncsc1-c1ccc(CNC(=O)[C@@H]2C[C@@H](O)CN2C(=O)[C@@H](NC(=O)CCCCc2ccc(CNC(=O)[C@H](CCC(N)=O)NC(=O)[C@@H]3Cc4cccc5c4N3C(=O)[C@@H](NC(=O)c3cc4cc(C(=O)P(=O)(O)O)ccc4[nH]3)CC5)cc2)C(C)(C)C)cc1] |

TABLE 1-continued
| Exemplary Compounds | |
|---|---|
| I-# | Structure |
| I-140 | 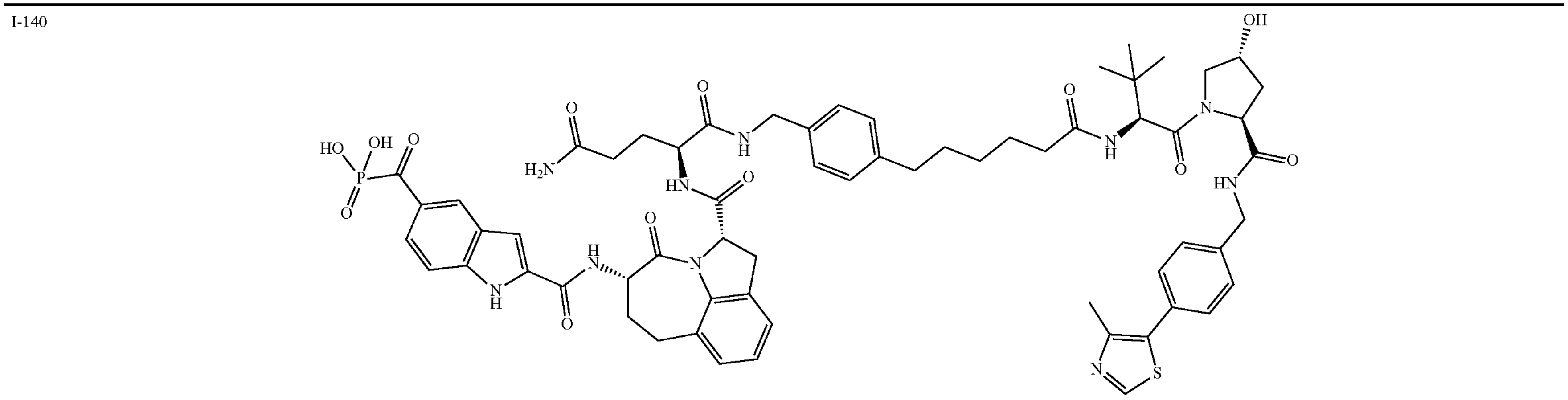 |
| I-141 | 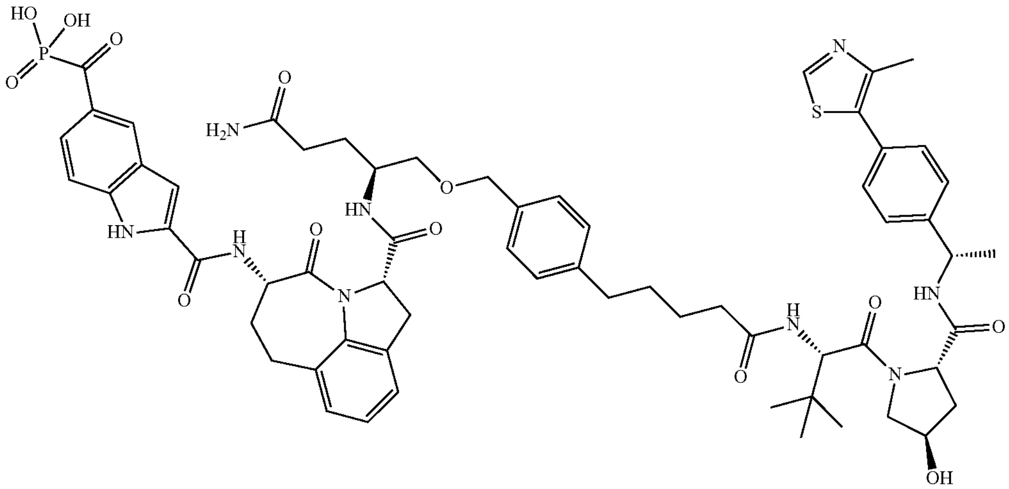 [SMILES: Cc1ncsc1-c1ccc([C@H](C)NC(=O)[C@@H]2C[C@@H](O)CN2C(=O)[C@@H](NC(=O)CCCCc2ccc(COC[C@H](CCC(N)=O)NC(=O)[C@@H]3Cc4cccc5c4N3C(=O)[C@@H](NC(=O)c3cc4cc(C(=O)P(=O)(O)O)ccc4[nH]3)CC5)cc2)C(C)(C)C)cc1] |

TABLE 1-continued
| Exemplary Compounds | |
|---|---|
| I-# | Structure |
| I-142 | 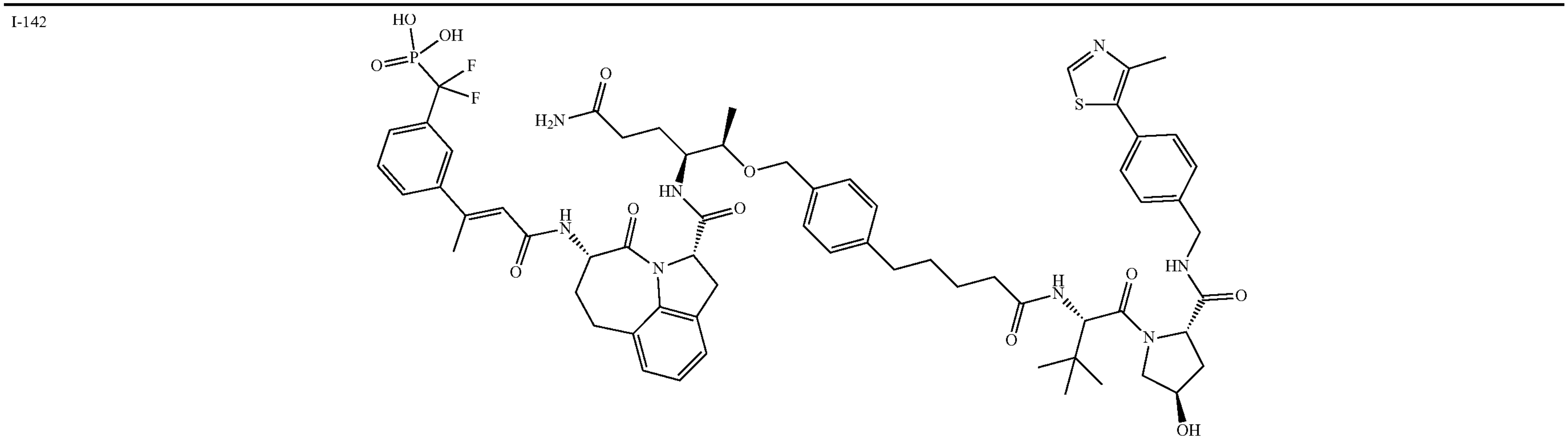 |
| I-143 | 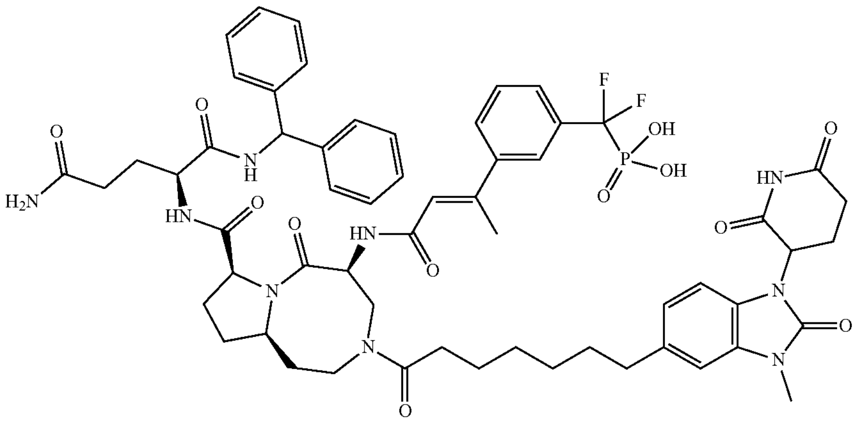 [SMILES: C/C(=C\C(=O)N[C@H]1CN(C(=O)CCCCCCc2ccc3c(c2)n(C)c(=O)n3C2CCC(=O)NC2=O)CC[C@H]2CC[C@@H](C(=O)N[C@@H](CCC(N)=O)C(=O)NC(c3ccccc3)c3ccccc3)N2C1=O)c1cccc(C(F)(F)P(=O)(O)O)c1] |

TABLE 1-continued
| Exemplary Compounds | |
|---|---|
| I-# | Structure |
| I-144 | 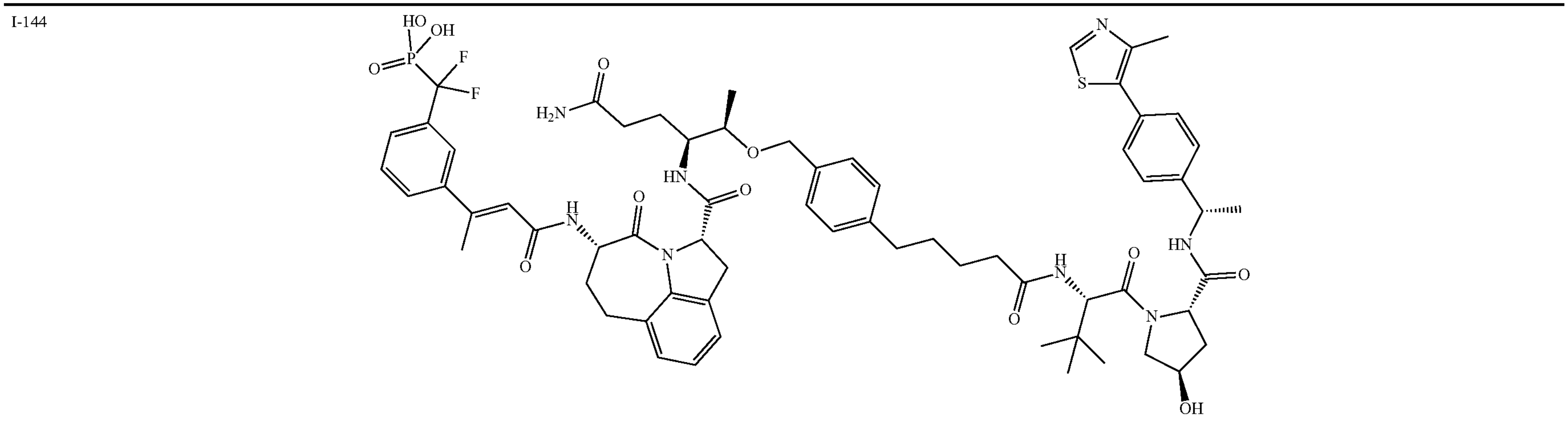 |
| I-145 | 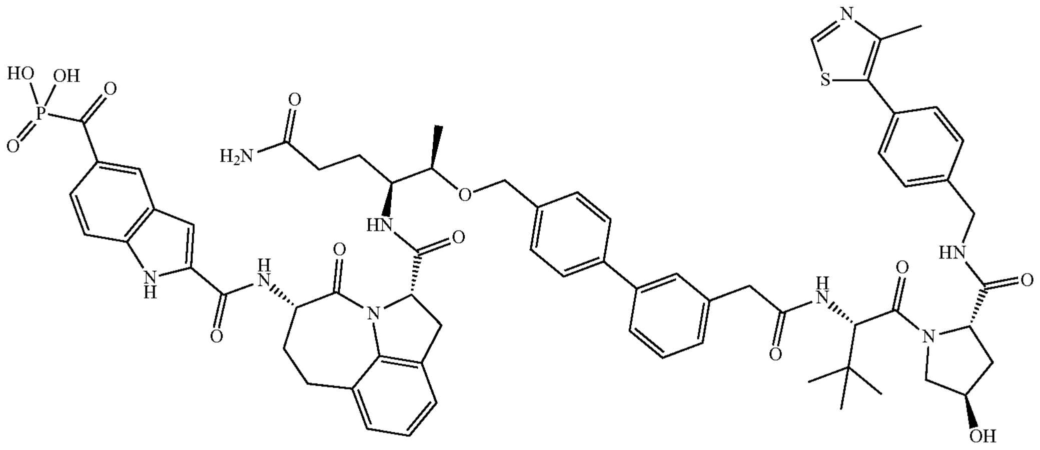 [SMILES: Cc1ncsc1-c1ccc(CNC(=O)[C@@H]2C[C@@H](O)CN2C(=O)[C@@H](NC(=O)Cc2cccc(-c3ccc(CO[C@H](C)[C@H](CCC(N)=O)NC(=O)[C@@H]4Cc5cccc6c5N4C(=O)[C@@H](NC(=O)c4cc5cc(C(=O)P(=O)(O)O)ccc5[nH]4)CC6)cc3)c2)C(C)(C)C)cc1] |

TABLE 1-continued
| Exemplary Compounds | |
|---|---|
| I-# | Structure |
| I-146 | 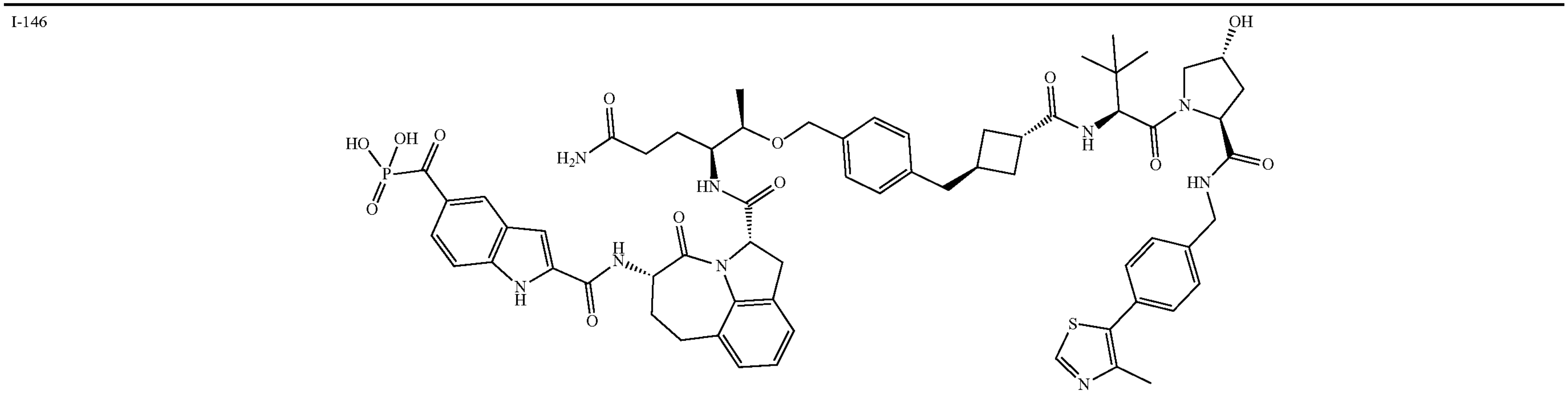 |
| I-147 | 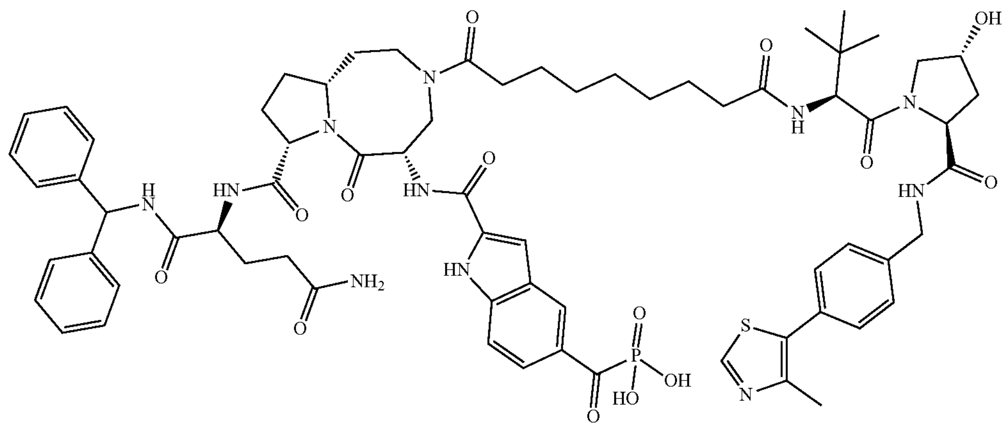 [SMILES: Cc1ncsc1-c1ccc(CNC(=O)[C@@H]2C[C@@H](O)CN2C(=O)[C@@H](NC(=O)CCCCCCCC(=O)N2CC[C@H]3CC[C@@H](C(=O)N[C@@H](CCC(N)=O)C(=O)NC(c4ccccc4)c4ccccc4)N3C(=O)[C@@H](NC(=O)c3cc4cc(C(=O)P(=O)(O)O)ccc4[nH]3)C2)C(C)(C)C)cc1] |

TABLE 1-continued
Exemplary Compounds
| I-# | Structure |
| --- | --- |
| I-148 | 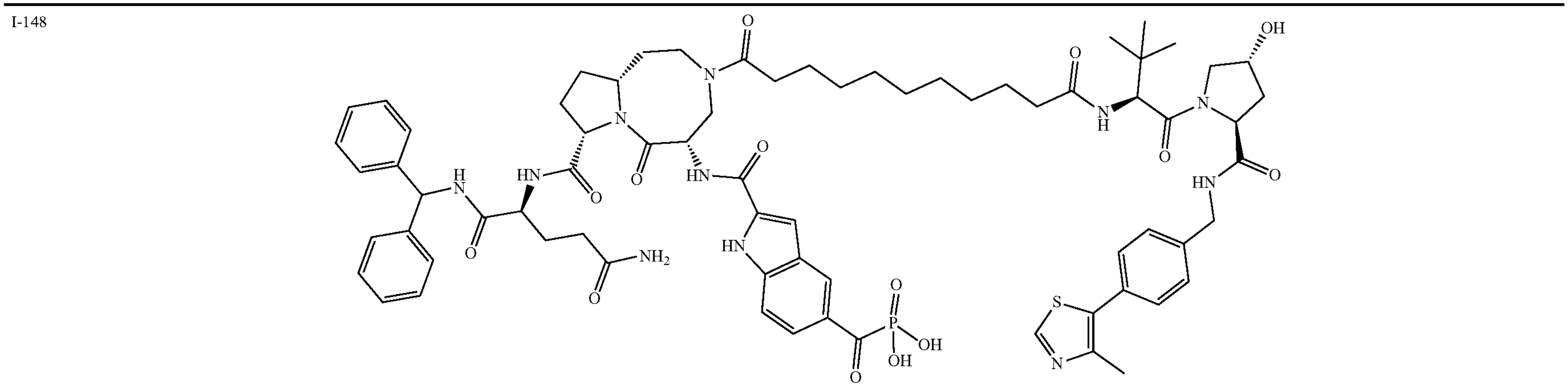 |
| I-149 | 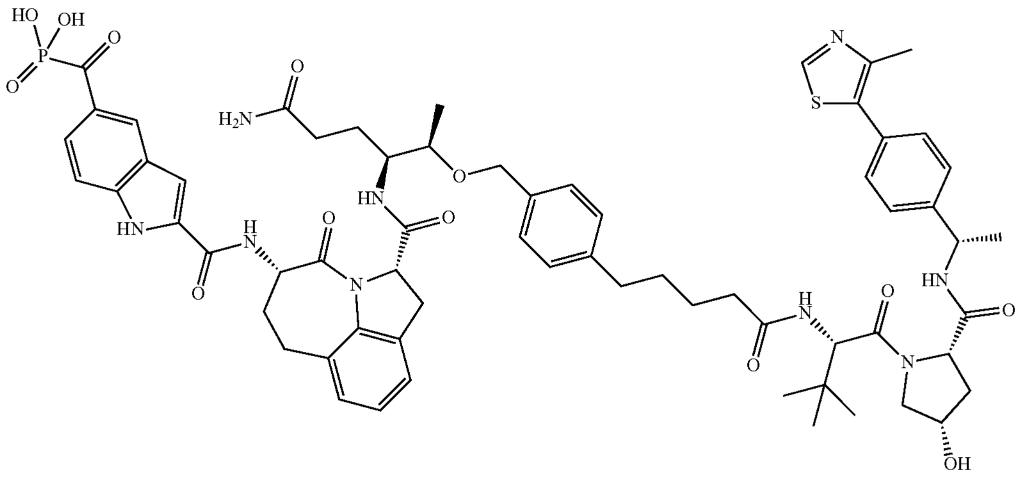 [SMILES: Cc1ncsc1-c1ccc([C@H](C)NC(=O)[C@@H]2C[C@H](O)CN2C(=O)[C@@H](NC(=O)CCCCc2ccc(CO[C@H](C)[C@H](CCC(N)=O)NC(=O)[C@@H]3Cc4cccc5c4N3C(=O)[C@@H](NC(=O)c3cc4cc(C(=O)P(=O)(O)O)ccc4[nH]3)CC5)cc2)C(C)(C)C)cc1] |

TABLE 1-continued
| Exemplary Compounds | |
|---|---|
| I-# | Structure |
| I-150 | 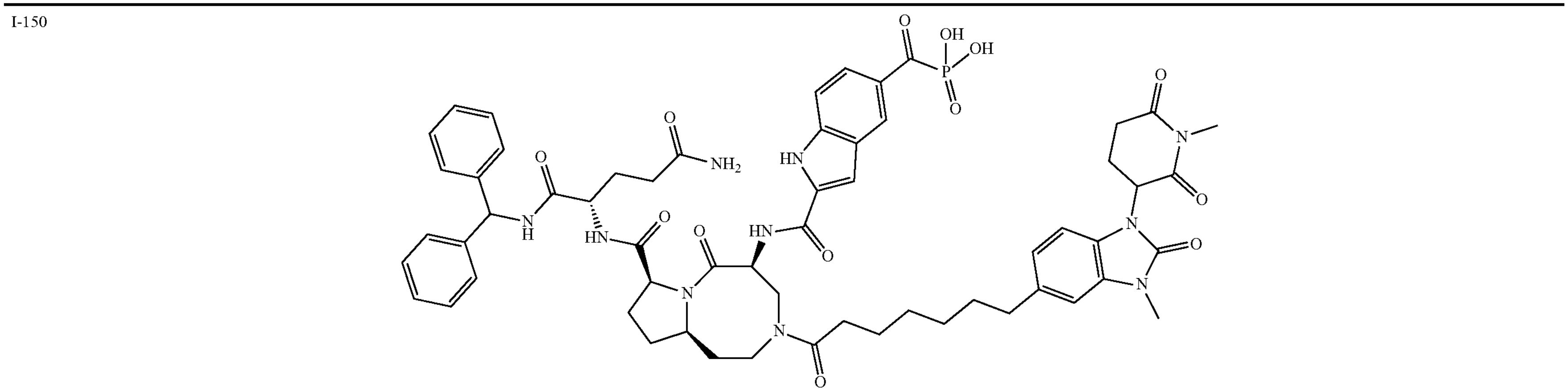 |
| I-151 | 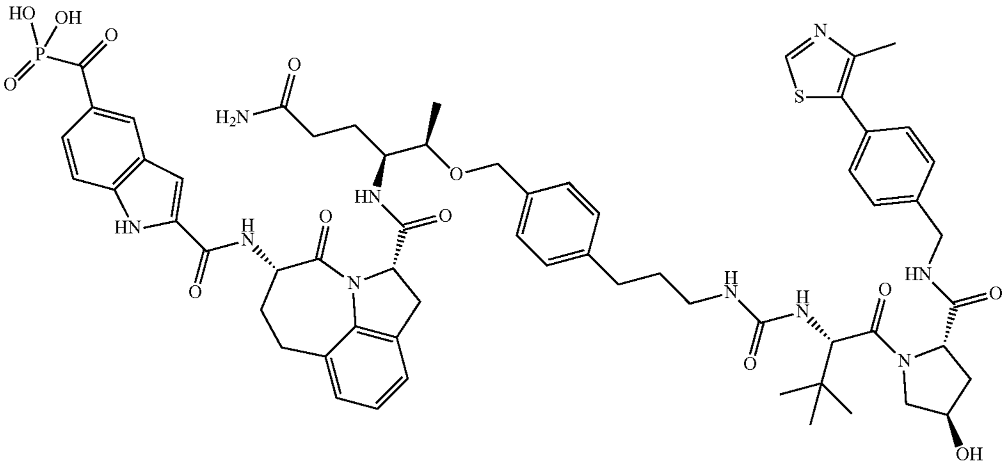 [SMILES: Cc1ncsc1-c1ccc(CNC(=O)[C@@H]2C[C@@H](O)CN2C(=O)[C@@H](NC(=O)NCCCc2ccc(CO[C@H](C)[C@H](CCC(N)=O)NC(=O)[C@@H]3Cc4cccc5c4N3C(=O)[C@@H](NC(=O)c3cc4cc(C(=O)P(=O)(O)O)ccc4[nH]3)CC5)cc2)C(C)(C)C)cc1] |

TABLE 1-continued
| Exemplary Compounds | |
|---|---|
| I-# | Structure |
| I-152 | 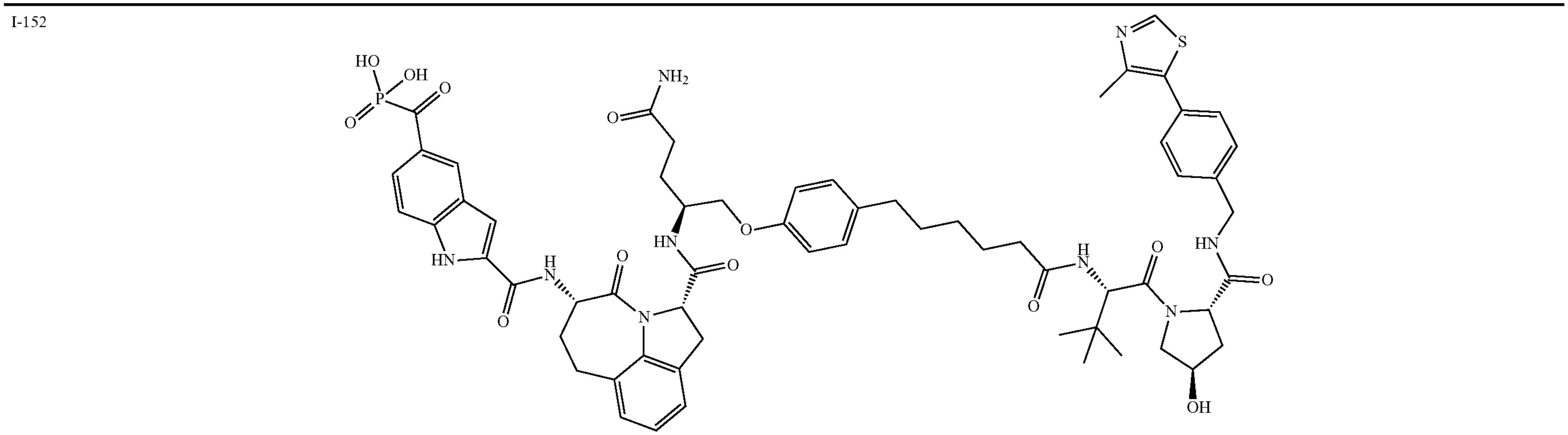 |
| I-153 | 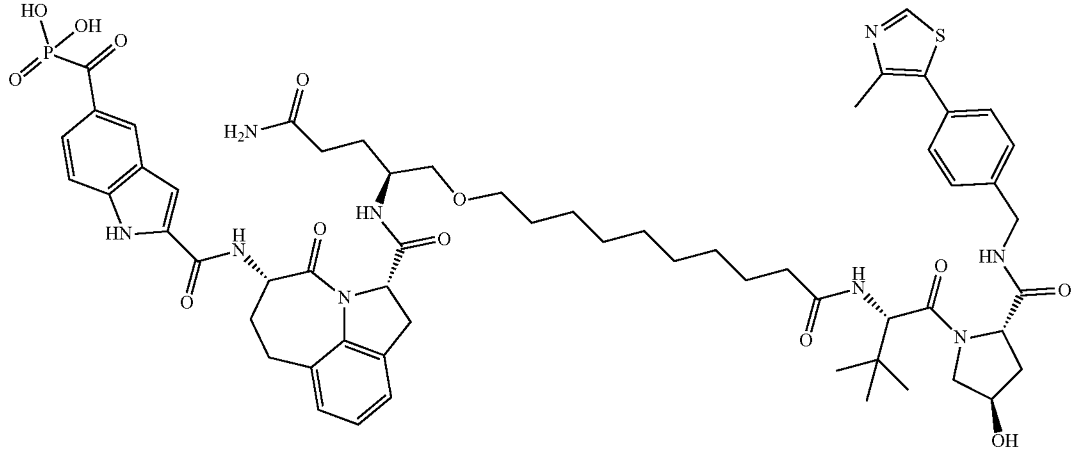 [SMILES: Cc1ncsc1-c1ccc(CNC(=O)[C@@H]2C[C@@H](O)CN2C(=O)[C@@H](NC(=O)CCCCCCCCCOC[C@H](CCC(N)=O)NC(=O)[C@@H]2Cc3cccc4c3N2C(=O)[C@@H](NC(=O)c2cc3cc(C(=O)P(=O)(O)O)ccc3[nH]2)CC4)C(C)(C)C)cc1] |

TABLE 1-continued
| Exemplary Compounds | |
|---|---|
| I-# | Structure |
| I-154 | 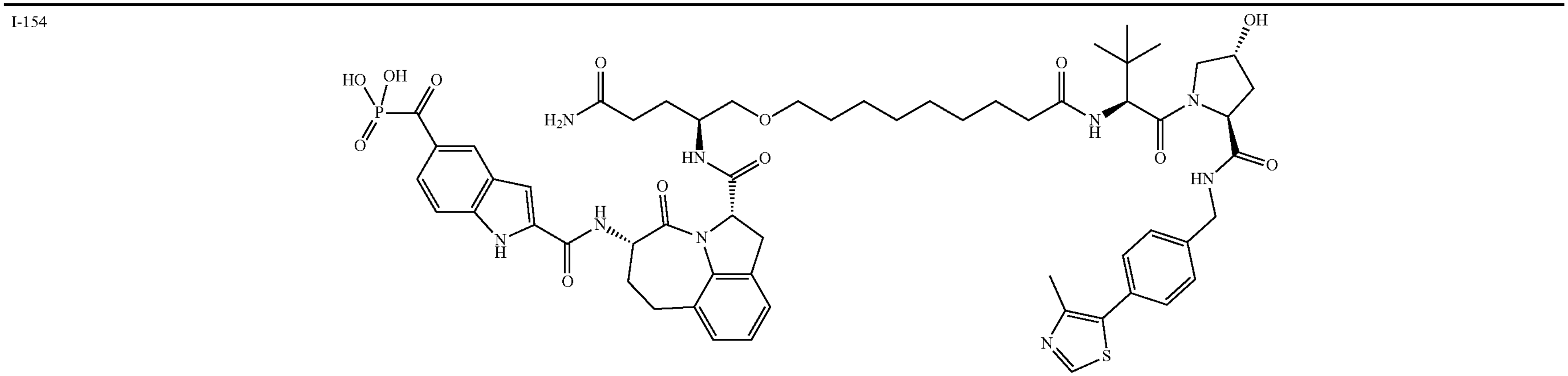 |
| I-155 | 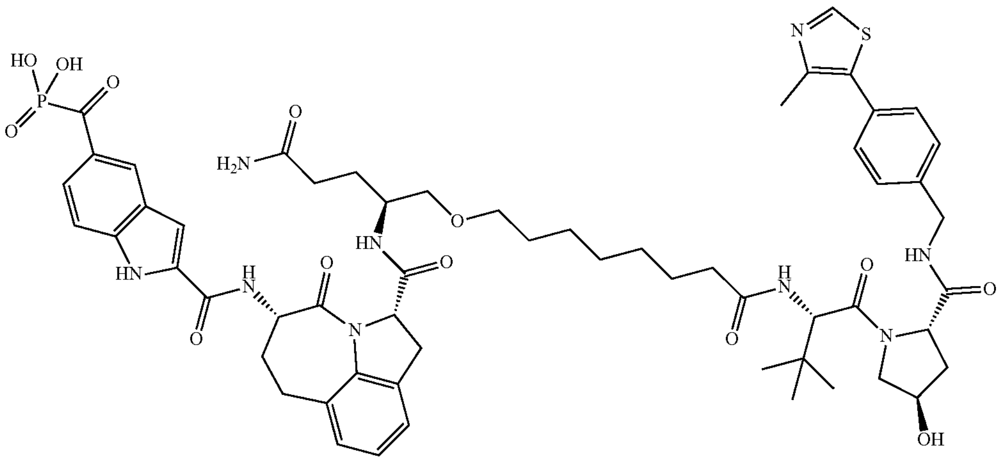 [SMILES: Cc1ncsc1-c1ccc(CNC(=O)[C@@H]2C[C@@H](O)CN2C(=O)[C@@H](NC(=O)CCCCCCCOC[C@H](CCC(N)=O)NC(=O)[C@@H]2Cc3cccc4c3N2C(=O)[C@@H](NC(=O)c2cc3cc(C(=O)P(=O)(O)O)ccc3[nH]2)CC4)C(C)(C)C)cc1] |

TABLE 1-continued
| Exemplary Compounds | |
|---|---|
| I-# | Structure |
| I-156 | 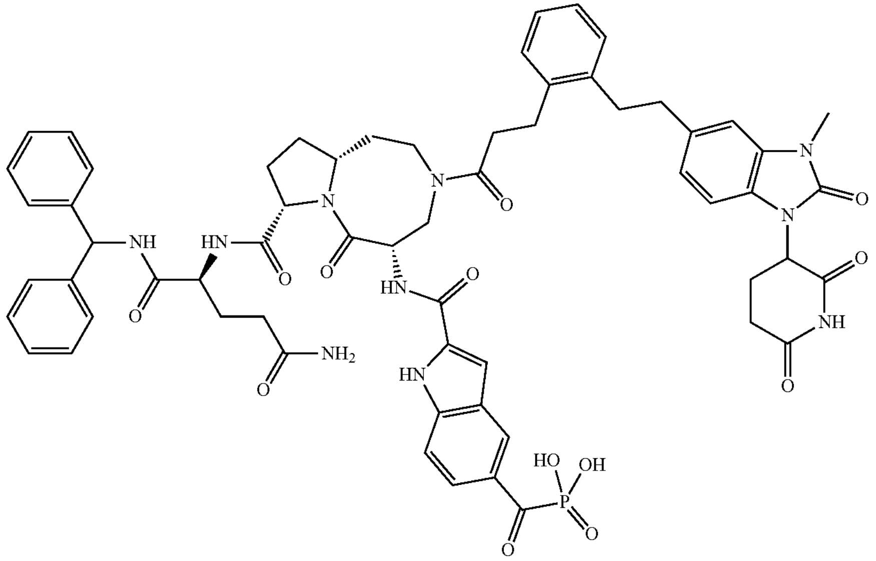 [SMILES: Cn1c(=O)n(C2CCC(=O)NC2=O)c2ccc(CCc3ccccc3CCC(=O)N3CC[C@H]4CC[C@@H](C(=O)N[C@@H](CCC(N)=O)C(=O)NC(c5ccccc5)c5ccccc5)N4C(=O)[C@@H](NC(=O)c4cc5cc(C(=O)P(=O)(O)O)ccc5[nH]4)C3)cc21] |
| I-157 | 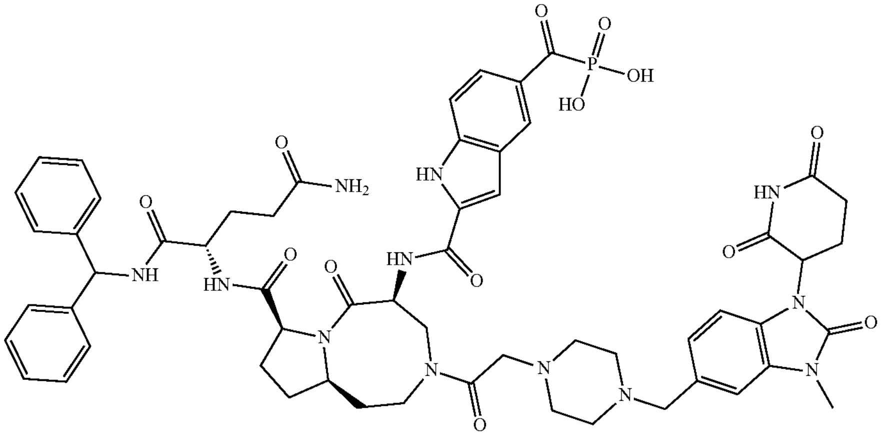 |

TABLE 1-continued
| Exemplary Compounds | |
|---|---|
| I-# | Structure |
| I-158 | 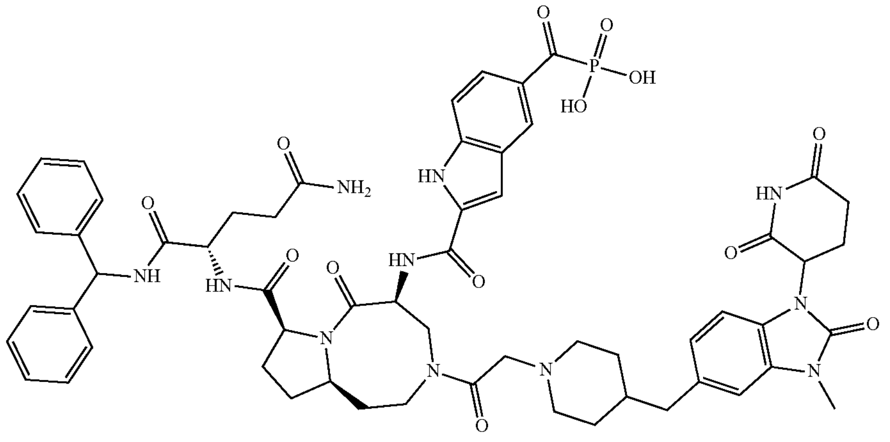 [SMILES: Cn1c(=O)n(C2CCC(=O)NC2=O)c2ccc(CN3CCN(CC(=O)N4CC[C@H]5CC[C@@H](C(=O)N[C@@H](CCC(N)=O)C(=O)NC(c6ccccc6)c6ccccc6)N5C(=O)[C@@H](NC(=O)c5cc6cc(C(=O)P(=O)(O)O)ccc6[nH]5)C4)CC3)cc21] |
| I-159 | 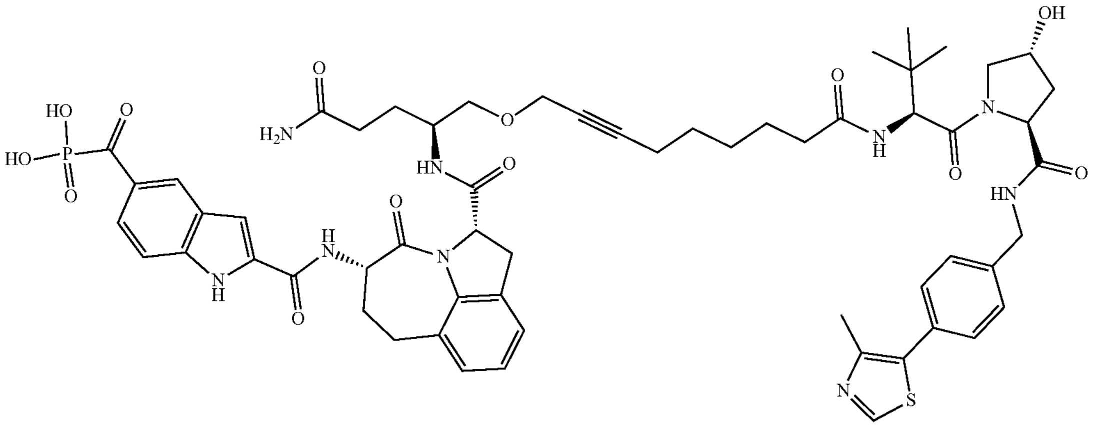 [SMILES: Cc1ncsc1-c1ccc(CNC(=O)[C@@H]2C[C@@H](O)CN2C(=O)[C@@H](NC(=O)CCCCCC#CCOC[C@H](CCC(N)=O)NC(=O)[C@@H]2Cc3cccc4c3N2C(=O)[C@@H](NC(=O)c2cc3cc(C(=O)P(=O)(O)O)ccc3[nH]2)CC4)C(C)(C)C)cc1] |

TABLE 1-continued
| Exemplary Compounds | |
| --- | --- |
| I-# | Structure |
| I-160 | 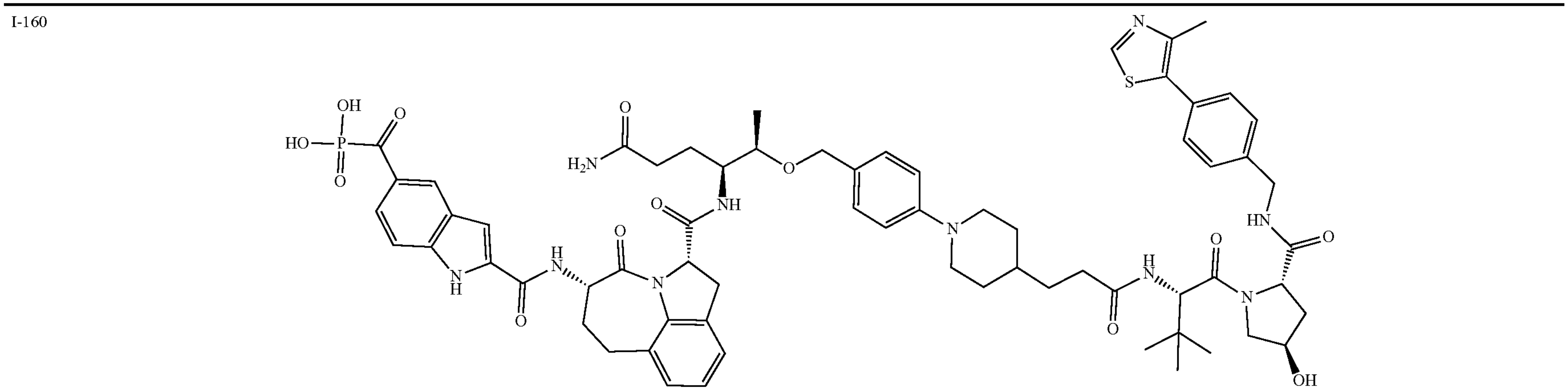 |
| I-161 | 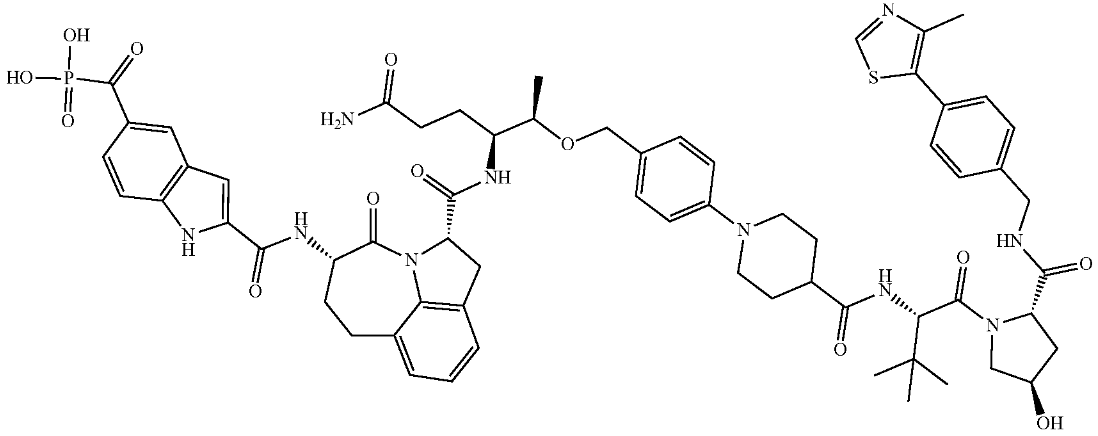 [SMILES: Cc1ncsc1-c1ccc(CNC(=O)[C@@H]2C[C@@H](O)CN2C(=O)[C@@H](NC(=O)C2CCN(c3ccc(CO[C@H](C)[C@H](CCC(N)=O)NC(=O)[C@@H]4Cc5cccc6c5N4C(=O)[C@@H](NC(=O)c4cc5cc(C(=O)P(=O)(O)O)ccc5[nH]4)CC6)cc3)CC2)C(C)(C)C)cc1] |

TABLE 1-continued
| Exemplary Compounds | |
|---|---|
| I-# | Structure |
| I-162 | 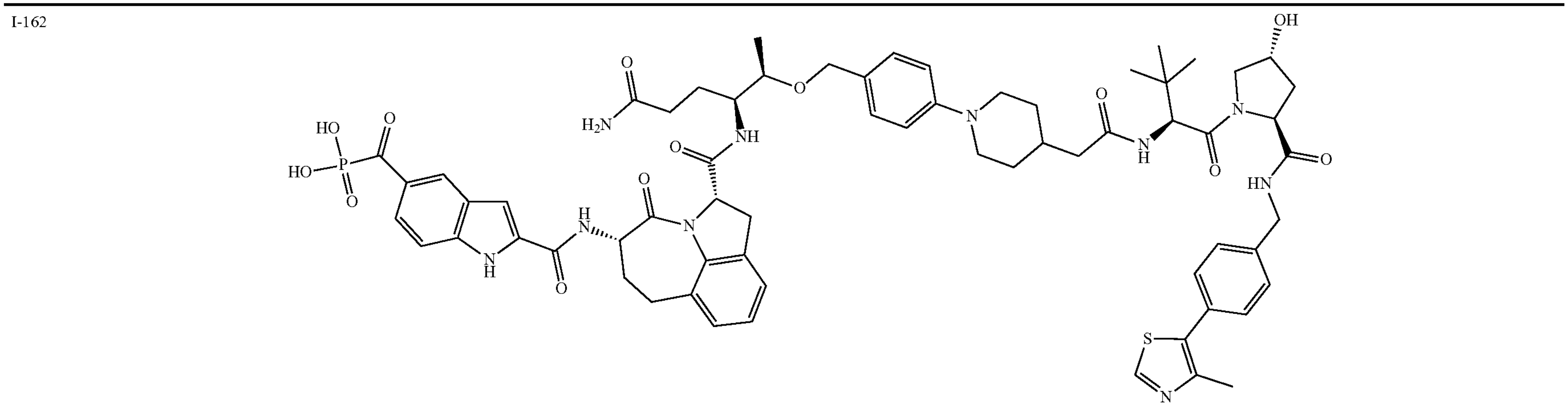 |
| I-163 | 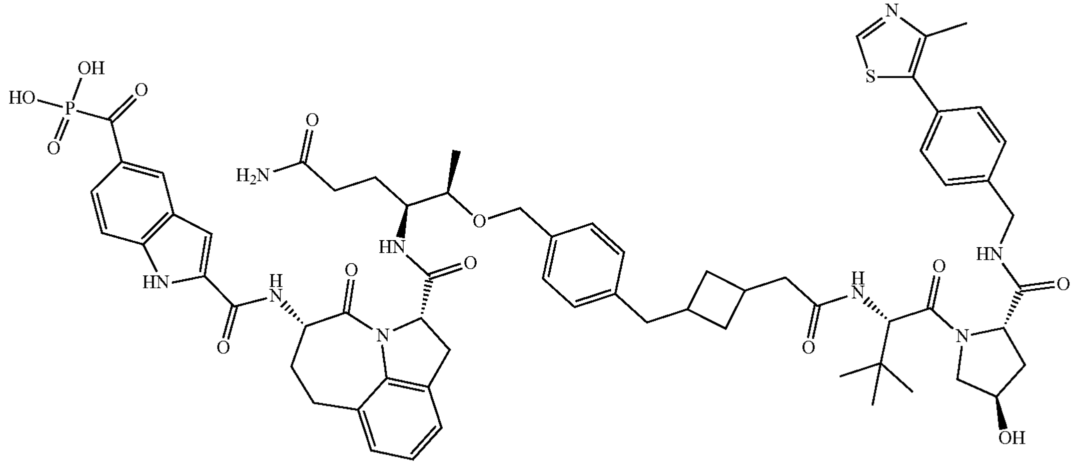 [SMILES: Cc1ncsc1-c1ccc(CNC(=O)[C@@H]2C[C@@H](O)CN2C(=O)[C@@H](NC(=O)CC2CC(Cc3ccc(CO[C@H](C)[C@H](CCC(N)=O)NC(=O)[C@@H]4Cc5cccc6c5N4C(=O)[C@@H](NC(=O)c4cc5cc(C(=O)P(=O)(O)O)ccc5[nH]4)CC6)cc3)C2)C(C)(C)C)cc1] |

TABLE 1-continued
| Exemplary Compounds | |
|---|---|
| I-# | Structure |
| I-164 | 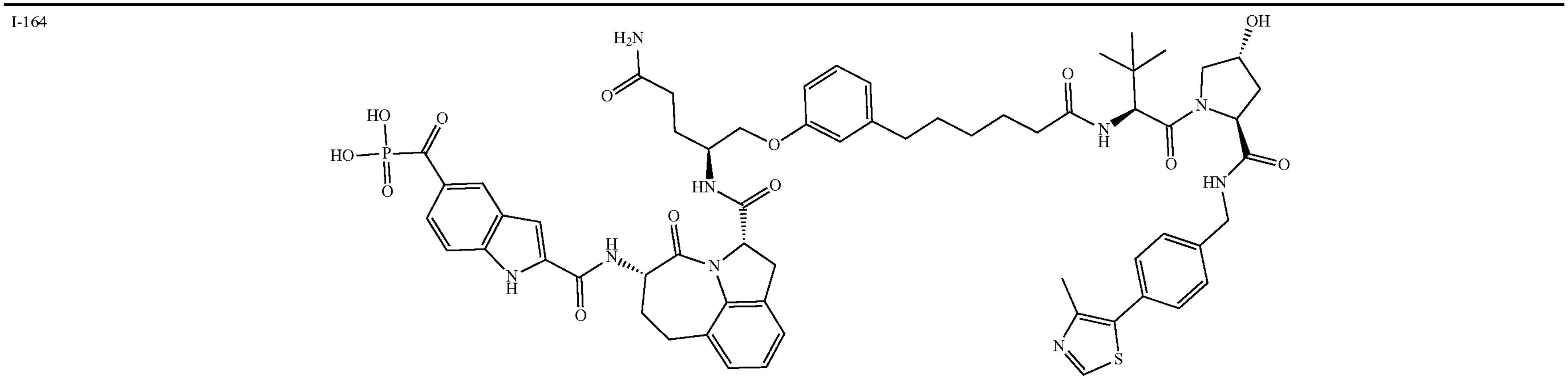 |
| I-165 | 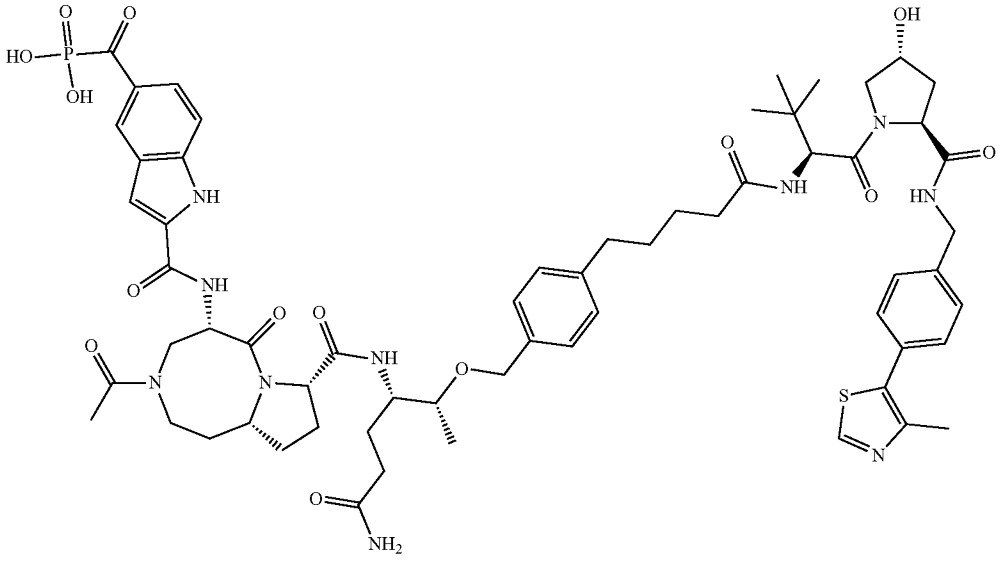 [SMILES: CC(=O)N1CC[C@H]2CC[C@@H](C(=O)N[C@@H](CCC(N)=O)[C@@H](C)OCc3ccc(CCCCC(=O)N[C@H](C(=O)N4C[C@H](O)C[C@H]4C(=O)NCc4ccc(-c5scnc5C)cc4)C(C)(C)C)cc3)N2C(=O)[C@@H](NC(=O)c2cc3cc(C(=O)P(=O)(O)O)ccc3[nH]2)C1] |

TABLE 1-continued
| Exemplary Compounds | |
|---|---|
| I-# | Structure |
| I-166 | 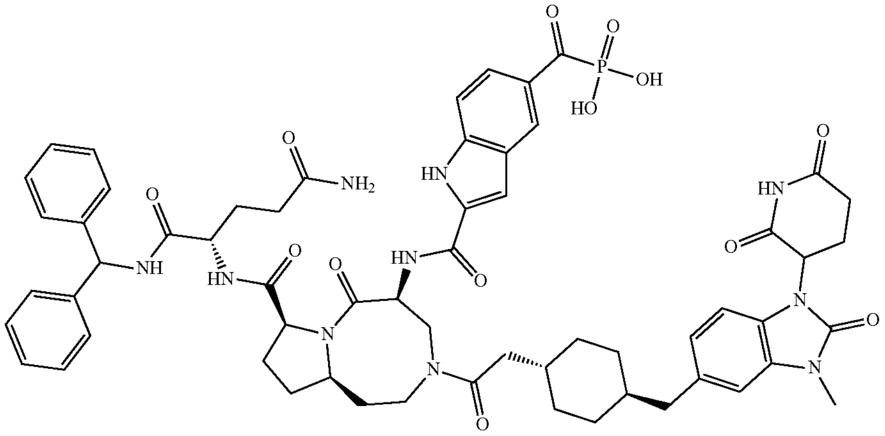 [SMILES: Cn1c(=O)n(C2CCC(=O)NC2=O)c2ccc(C[C@H]3CC[C@H](CC(=O)N4CC[C@H]5CC[C@@H](C(=O)N[C@@H](CCC(N)=O)C(=O)NC(c6ccccc6)c6ccccc6)N5C(=O)[C@@H](NC(=O)c5cc6cc(C(=O)P(=O)(O)O)ccc6[nH]5)C4)CC3)cc21] |
| I-167 | 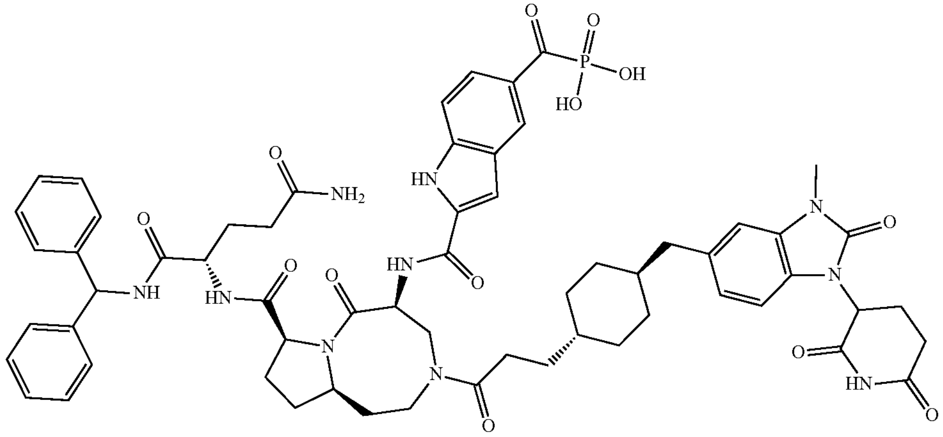 [SMILES: Cn1c(=O)n(C2CCC(=O)NC2=O)c2ccc(C[C@H]3CC[C@H](CCC(=O)N4CC[C@H]5CC[C@@H](C(=O)N[C@@H](CCC(N)=O)C(=O)NC(c6ccccc6)c6ccccc6)N5C(=O)[C@@H](NC(=O)c5cc6cc(C(=O)P(=O)(O)O)ccc6[nH]5)C4)CC3)cc21] |

TABLE 1-continued
| Exemplary Compounds | |
|---|---|
| I-# | Structure |
| I-168 | 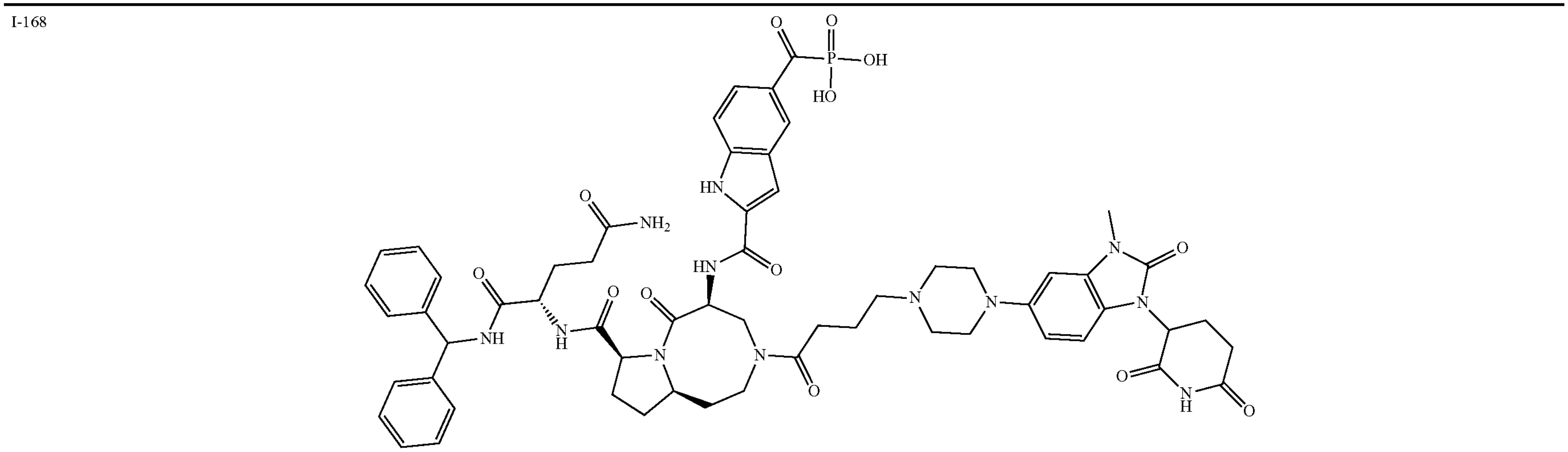 |
| I-169 | 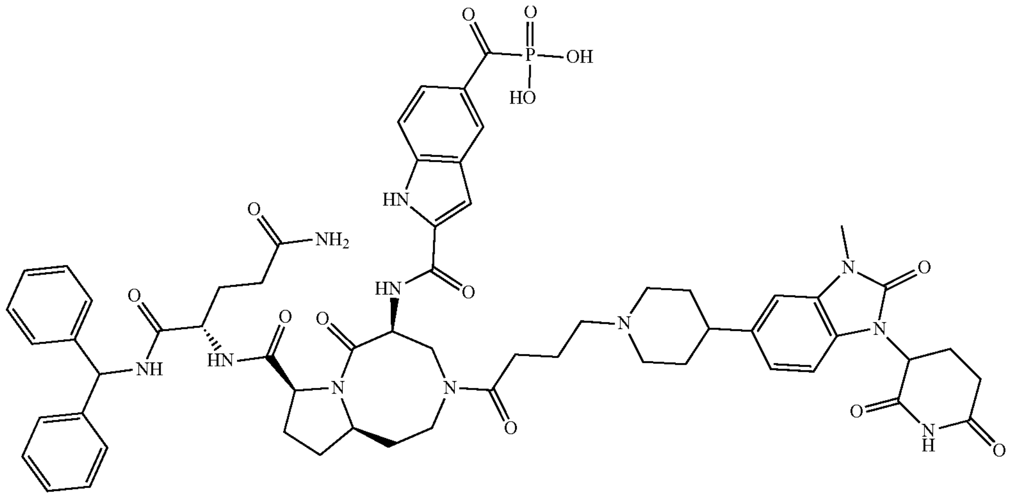 [SMILES: Cn1c(=O)n(C2CCC(=O)NC2=O)c2ccc(C3CCN(CCCC(=O)N4CC[C@H]5CC[C@@H](C(=O)N[C@@H](CCC(N)=O)C(=O)NC(c6ccccc6)c6ccccc6)N5C(=O)[C@@H](NC(=O)c5cc6cc(C(=O)P(=O)(O)O)ccc6[nH]5)C4)CC3)cc21] |

TABLE 1-continued
| Exemplary Compounds | |
|---|---|
| I-# | Structure |
| I-170 | 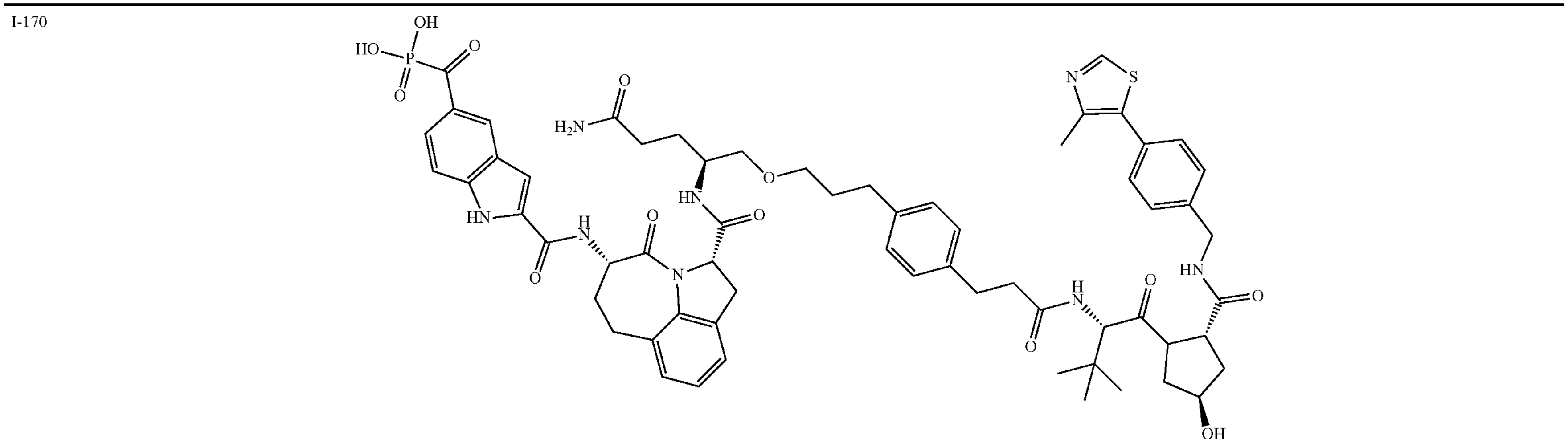 |
| I-171 | 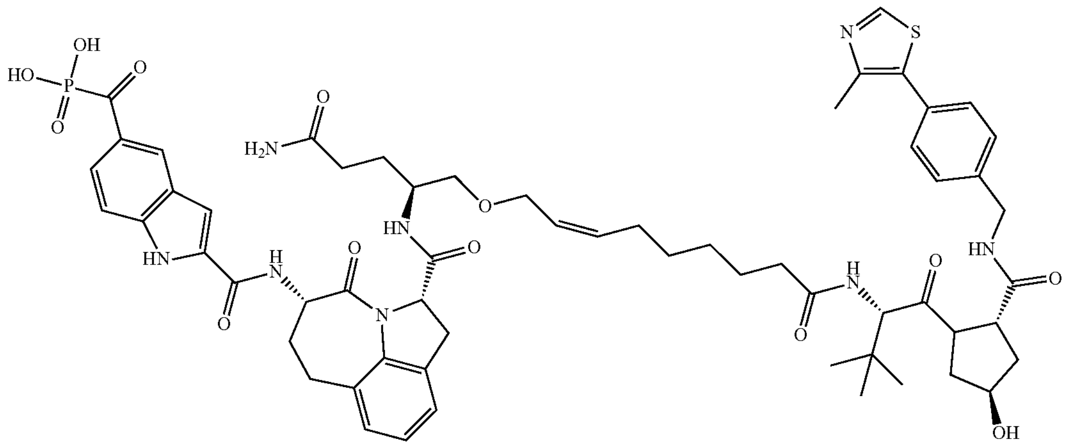 [SMILES: Cc1ncsc1-c1ccc(CNC(=O)[C@@H]2C[C@@H](O)CC2C(=O)[C@@H](NC(=O)CCCCC/C=C\COC[C@H](CCC(N)=O)NC(=O)[C@@H]2Cc3cccc4c3N2C(=O)[C@@H](NC(=O)c2cc3cc(C(=O)P(=O)(O)O)ccc3[nH]2)CC4)C(C)(C)C)cc1] |

TABLE 1-continued
| Exemplary Compounds | |
|---|---|
| I-# | Structure |
| I-172 | 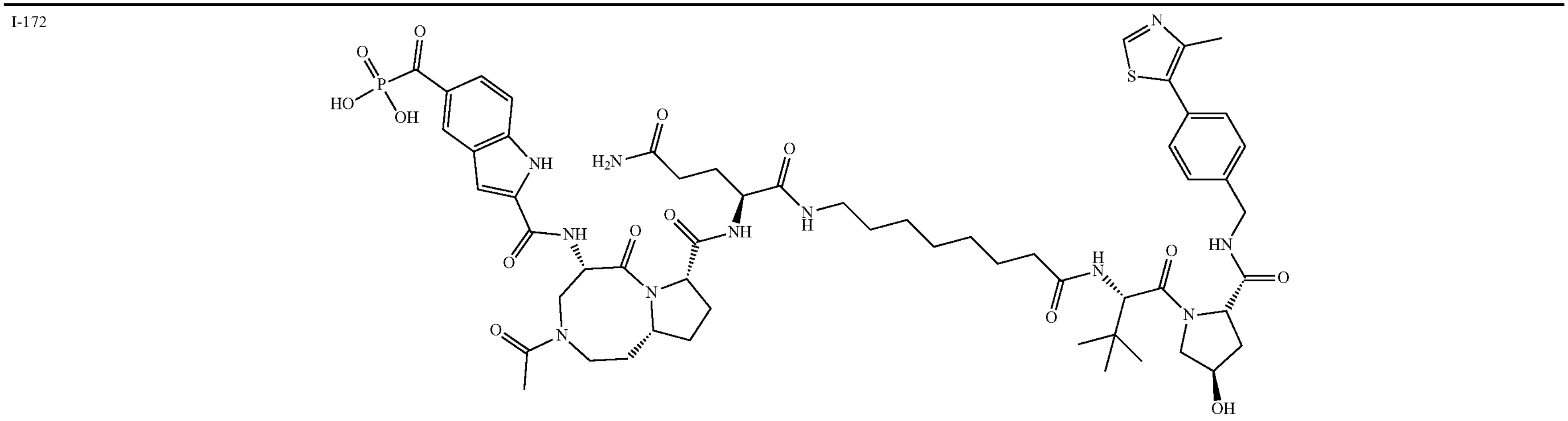 |
| I-173 | 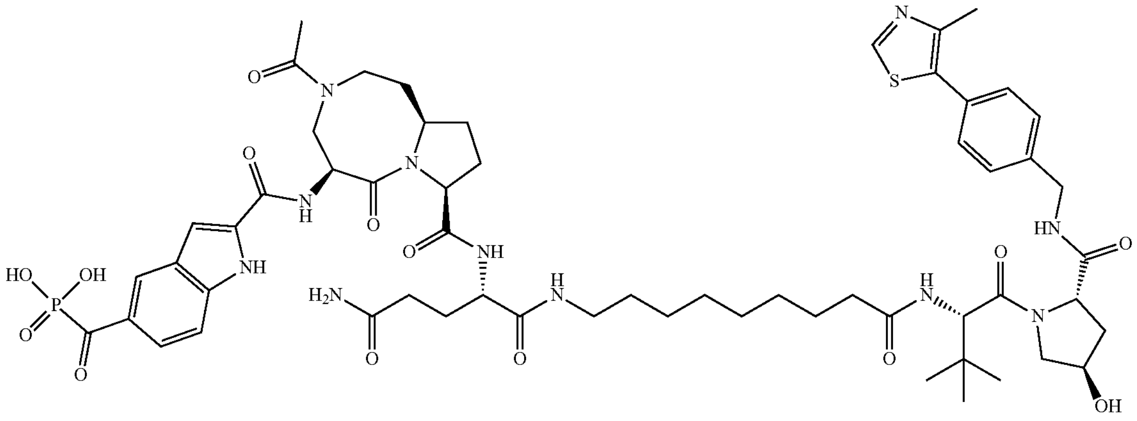 [SMILES: CC(=O)N1CC[C@H]2CC[C@@H](C(=O)N[C@@H](CCC(N)=O)C(=O)NCCCCCCCCC(=O)N[C@H](C(=O)N3C[C@H](O)C[C@H]3C(=O)NCc3ccc(-c4scnc4C)cc3)C(C)(C)C)N2C(=O)[C@@H](NC(=O)c2cc3cc(C(=O)P(=O)(O)O)ccc3[nH]2)C1] |

TABLE 1-continued
| Exemplary Compounds | |
|---|---|
| I-# | Structure |
| I-174 | 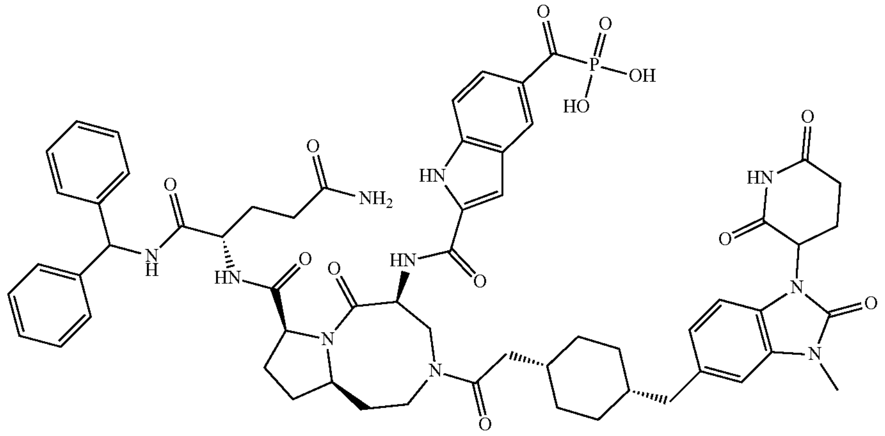 [SMILES: Cn1c(=O)n(C2CCC(=O)NC2=O)c2ccc(C[C@H]3CC[C@@H](CC(=O)N4CC[C@H]5CC[C@@H](C(=O)N[C@@H](CCC(N)=O)C(=O)NC(c6ccccc6)c6ccccc6)N5C(=O)[C@@H](NC(=O)c5cc6cc(C(=O)P(=O)(O)O)ccc6[nH]5)C4)CC3)cc21] |
| I-175 | 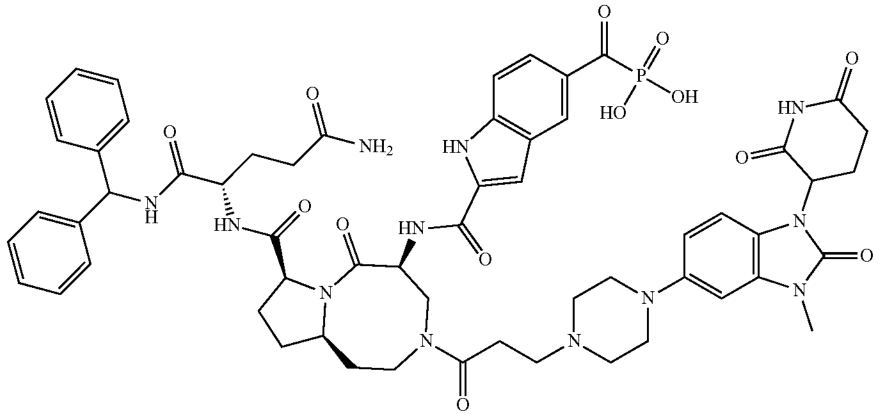 [SMILES: Cn1c(=O)n(C2CCC(=O)NC2=O)c2ccc(N3CCN(CCC(=O)N4CC[C@H]5CC[C@@H](C(=O)N[C@@H](CCC(N)=O)C(=O)NC(c6ccccc6)c6ccccc6)N5C(=O)[C@@H](NC(=O)c5cc6cc(C(=O)P(=O)(O)O)ccc6[nH]5)C4)CC3)cc21] |

TABLE 1-continued
| Exemplary Compounds | |
|---|---|
| I-# | Structure |
| I-176 | 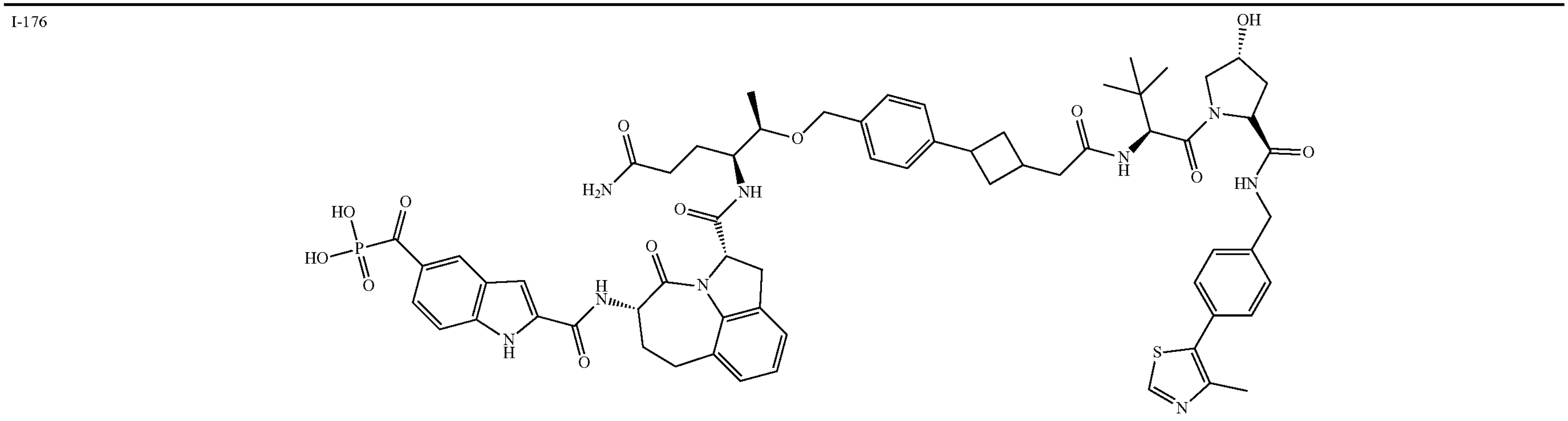 |
| I-177 | 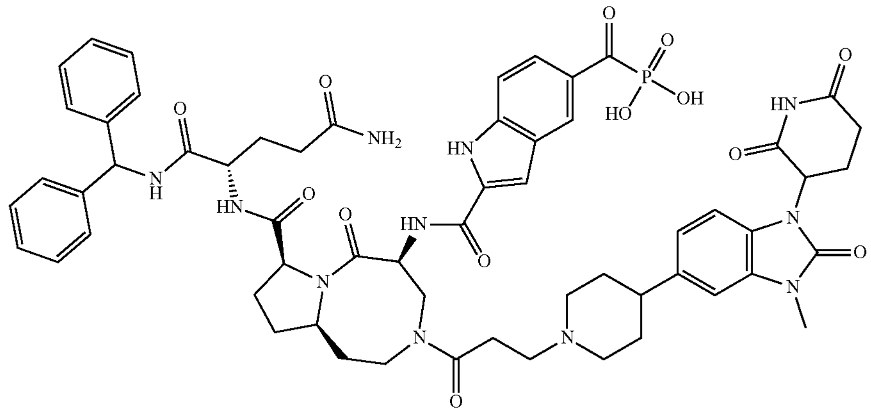 [SMILES: Cn1c(=O)n(C2CCC(=O)NC2=O)c2ccc(C3CCN(CCC(=O)N4CC[C@H]5CC[C@@H](C(=O)N[C@@H](CCC(N)=O)C(=O)NC(c6ccccc6)c6ccccc6)N5C(=O)[C@@H](NC(=O)c5cc6cc(C(=O)P(=O)(O)O)ccc6[nH]5)C4)CC3)cc21] |

TABLE 1-continued
| Exemplary Compounds | |
|---|---|
| I-# | Structure |
| I-178 | 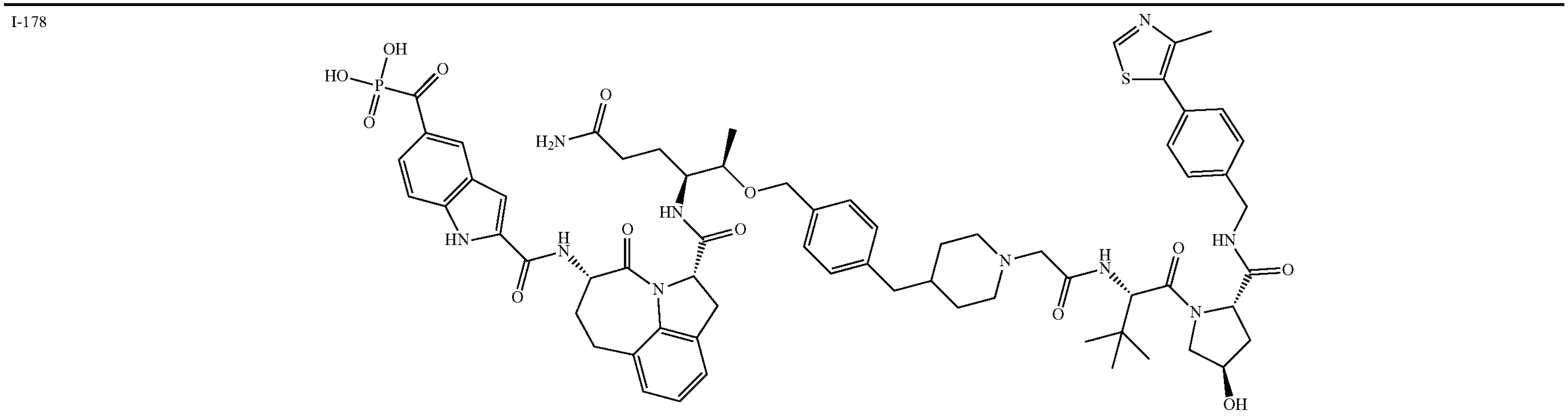 |
| I-179 | 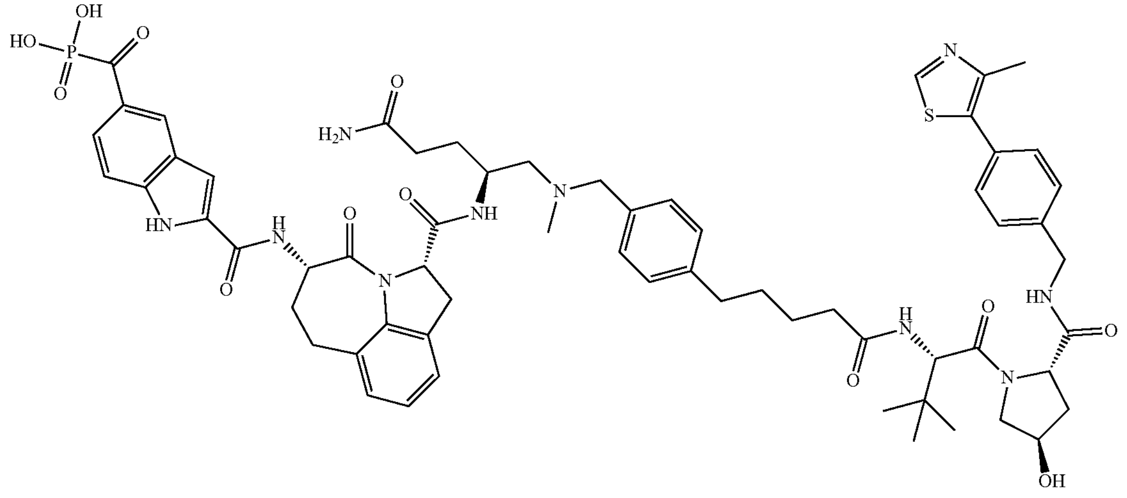 [SMILES: Cc1ncsc1-c1ccc(CNC(=O)[C@@H]2C[C@@H](O)CN2C(=O)[C@@H](NC(=O)CCCCc2ccc(CN(C)C[C@H](CCC(N)=O)NC(=O)[C@@H]3Cc4cccc5c4N3C(=O)[C@@H](NC(=O)c3cc4cc(C(=O)P(=O)(O)O)ccc4[nH]3)CC5)cc2)C(C)(C)C)cc1] |

TABLE 1-continued
| Exemplary Compounds | |
|---|---|
| I-# | Structure |
| I-180 | 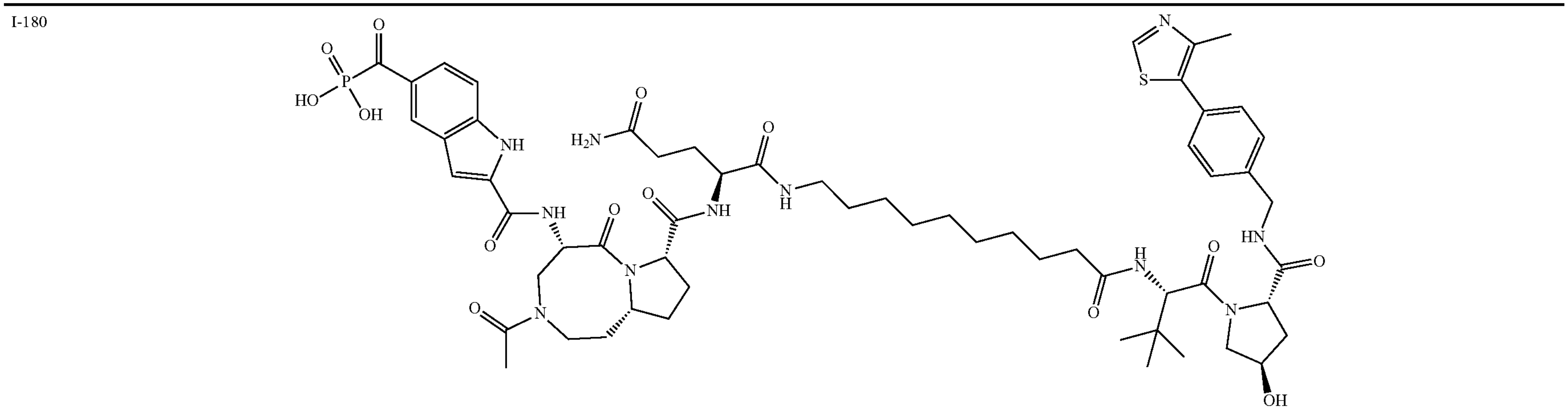 |
| I-181 | 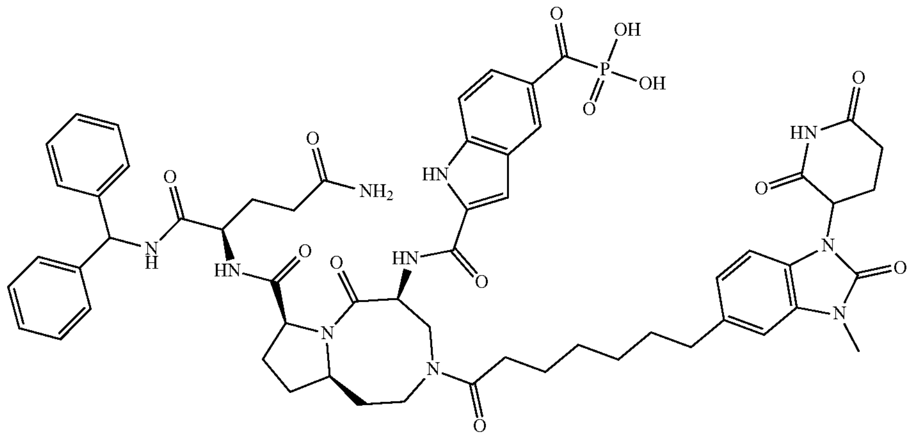 [SMILES: Cn1c(=O)n(C2CCC(=O)NC2=O)c2ccc(CCCCCCC(=O)N3CC[C@H]4CC[C@@H](C(=O)N[C@H](CCC(N)=O)C(=O)NC(c5ccccc5)c5ccccc5)N4C(=O)[C@@H](NC(=O)c4cc5cc(C(=O)P(=O)(O)O)ccc5[nH]4)C3)cc21] |

TABLE 1-continued
Exemplary Compounds
| I-# | Structure |
| --- | --- |
| I-182 | 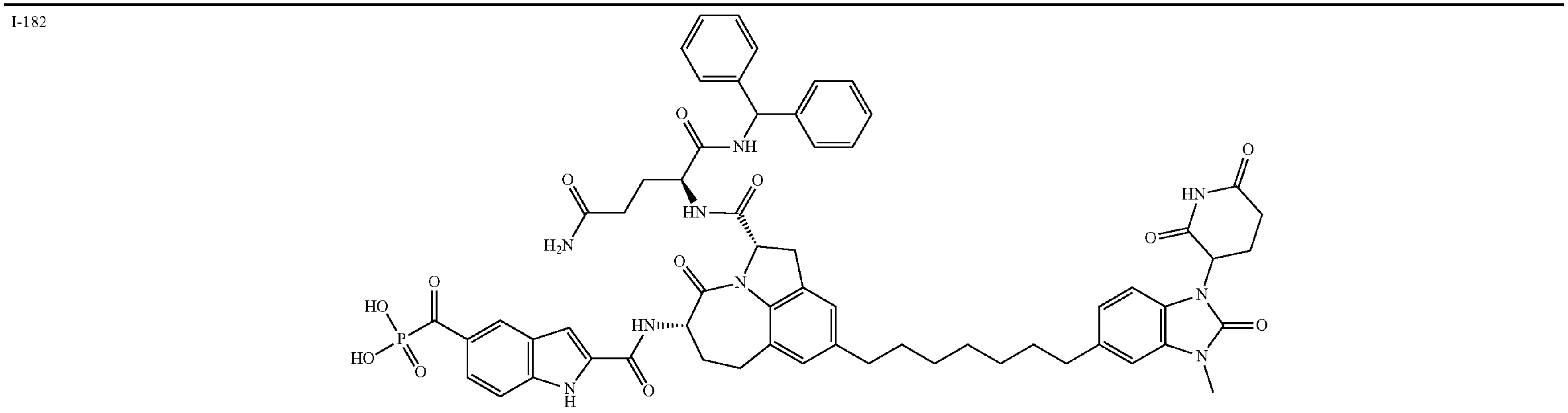 |
| I-183 | 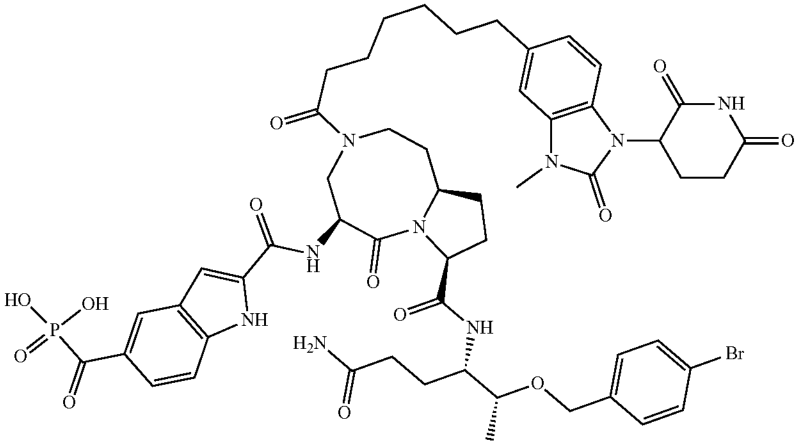 [SMILES: C[C@@H](OCc1ccc(Br)cc1)[C@H](CCC(N)=O)NC(=O)[C@@H]1CC[C@@H]2CCN(C(=O)CCCCCCc3ccc4c(c3)n(C)c(=O)n4C3CCC(=O)NC3=O)C[C@H](NC(=O)c3cc4cc(C(=O)P(=O)(O)O)ccc4[nH]3)C(=O)N21] |

TABLE 1-continued
| Exemplary Compounds | |
|---|---|
| I-# | Structure |
| I-184 | 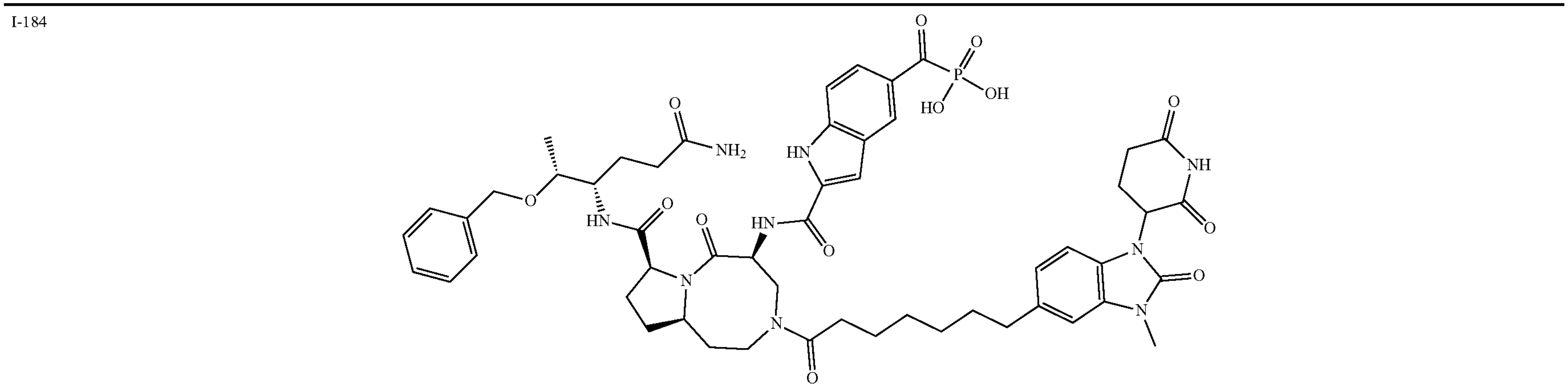 |
| I-185 | 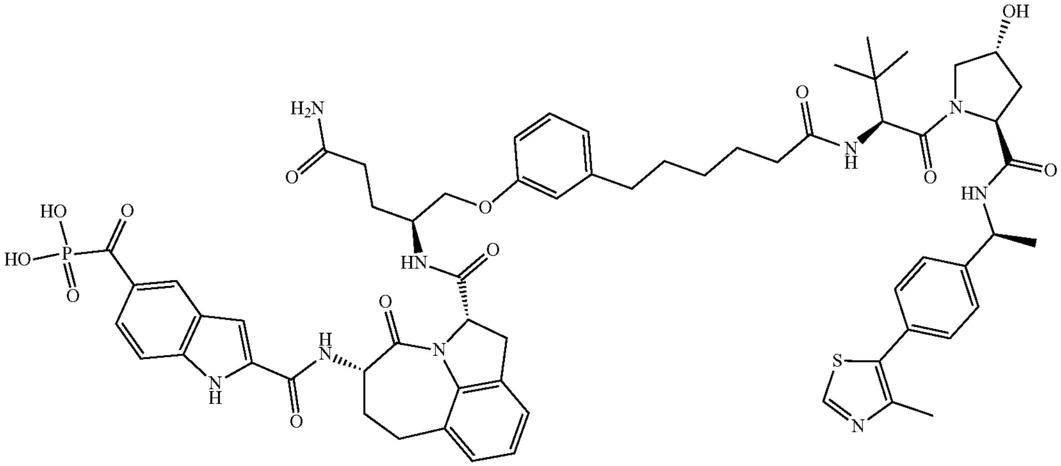 [SMILES: Cc1ncsc1-c1ccc([C@H](C)NC(=O)[C@@H]2C[C@@H](O)CN2C(=O)[C@@H](NC(=O)CCCCCc2cccc(OC[C@H](CCC(N)=O)NC(=O)[C@@H]3Cc4cccc5c4N3C(=O)[C@@H](NC(=O)c3cc4cc(C(=O)P(=O)(O)O)ccc4[nH]3)CC5)c2)C(C)(C)C)cc1] |

TABLE 1-continued
| Exemplary Compounds | |
|---|---|
| I-# | Structure |
| I-186 | 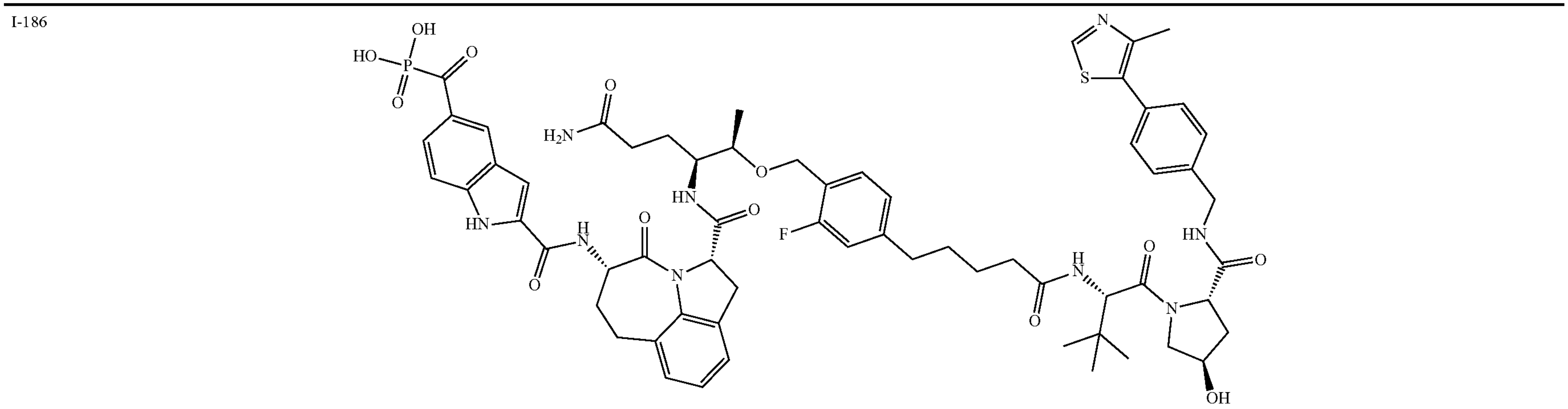 |
| I-187 | 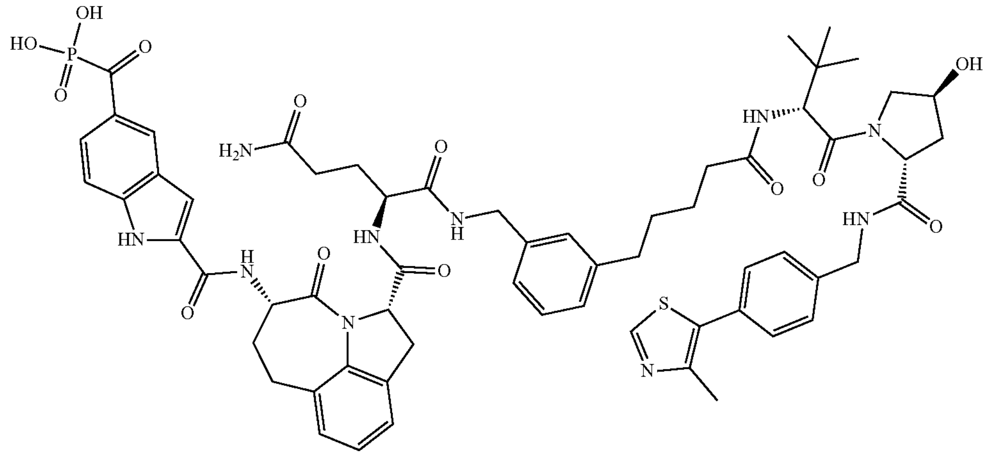 [SMILES: Cc1ncsc1-c1ccc(CNC(=O)[C@H]2C[C@H](O)CN2C(=O)[C@H](NC(=O)CCCCc2cccc(CNC(=O)[C@H](CCC(N)=O)NC(=O)[C@@H]3Cc4cccc5c4N3C(=O)[C@@H](NC(=O)c3cc4cc(C(=O)P(=O)(O)O)ccc4[nH]3)CC5)c2)C(C)(C)C)cc1] |

TABLE 1-continued
| Exemplary Compounds | |
|---|---|
| I-# | Structure |
| I-188 | 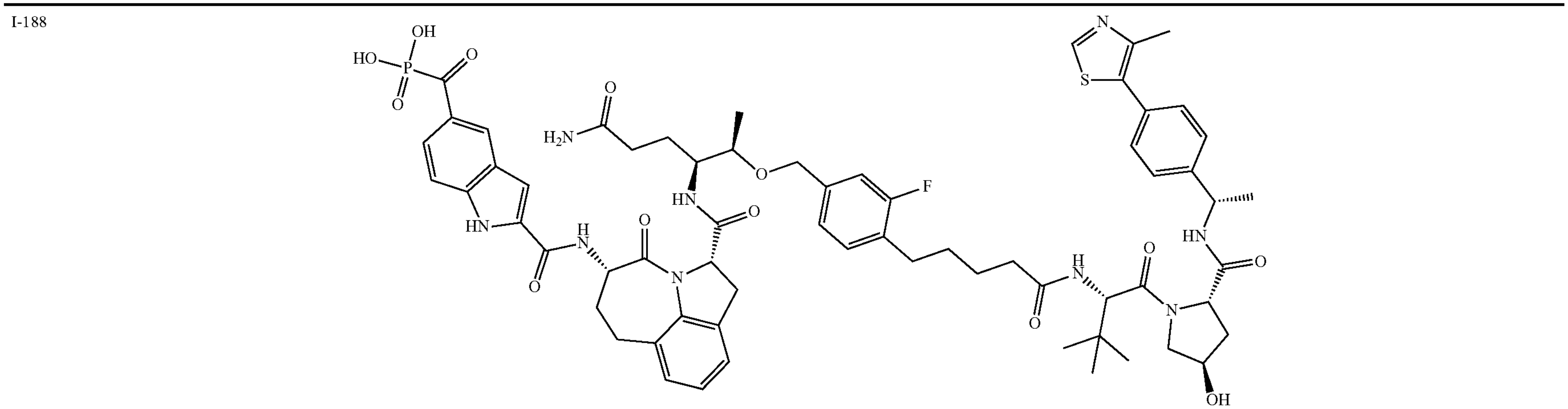 |
| I-189 | 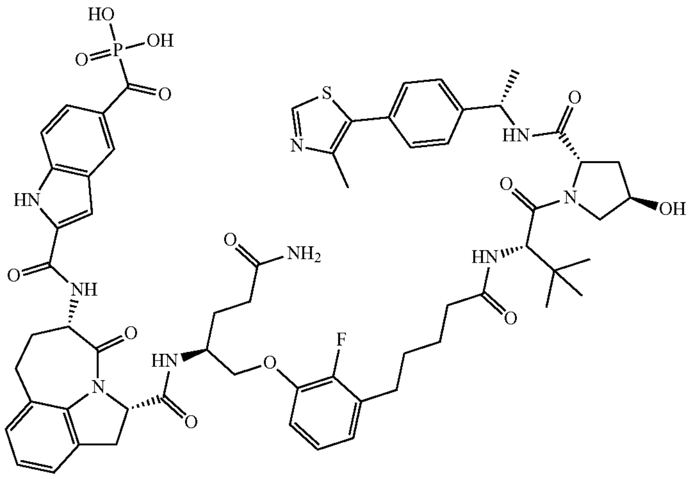 [SMILES: Cc1ncsc1-c1ccc([C@H](C)NC(=O)[C@@H]2C[C@@H](O)CN2C(=O)[C@@H](NC(=O)CCCCc2cccc(OC[C@H](CCC(N)=O)NC(=O)[C@@H]3Cc4cccc5c4N3C(=O)[C@@H](NC(=O)c3cc4cc(C(=O)P(=O)(O)O)ccc4[nH]3)CC5)c2F)C(C)(C)C)cc1] |

TABLE 1-continued
Exemplary Compounds
| I-# | Structure |
| --- | --- |
| I-190 | 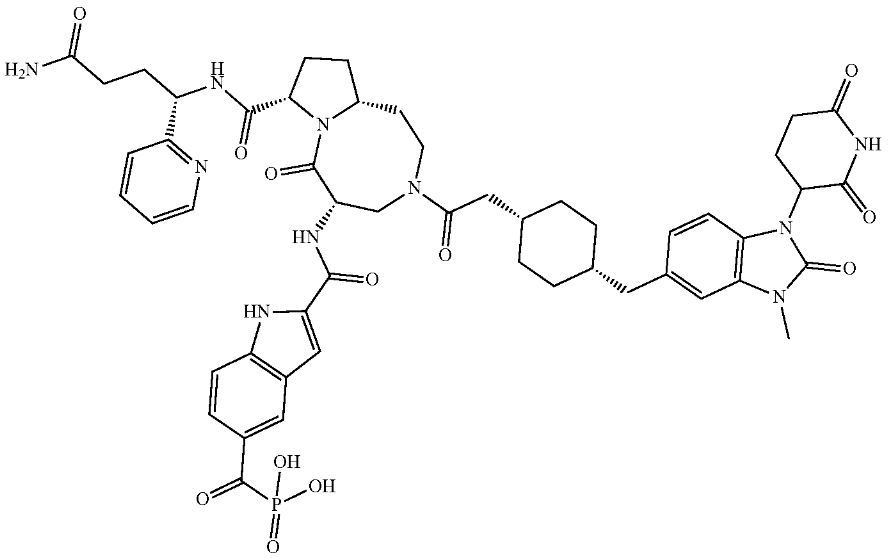 [SMILES: Cn1c(=O)n(C2CCC(=O)NC2=O)c2ccc(C[C@H]3CC[C@@H](CC(=O)N4CC[C@H]5CC[C@@H](C(=O)N[C@@H](CCC(N)=O)c6ccccn6)N5C(=O)[C@@H](NC(=O)c5cc6cc(C(=O)P(=O)(O)O)ccc6[nH]5)C4)CC3)cc21] |
| I-191 | 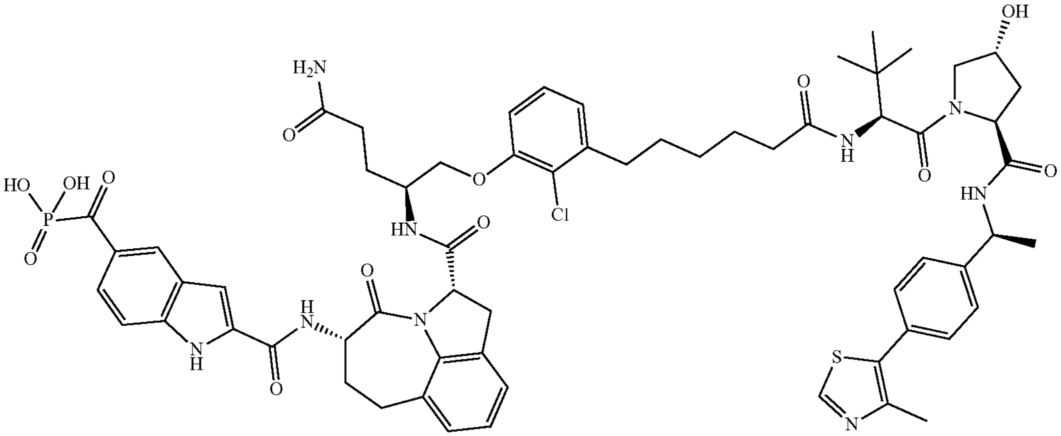 |

TABLE 1-continued
| Exemplary Compounds | |
|---|---|
| I-# | Structure |
| I-192 | 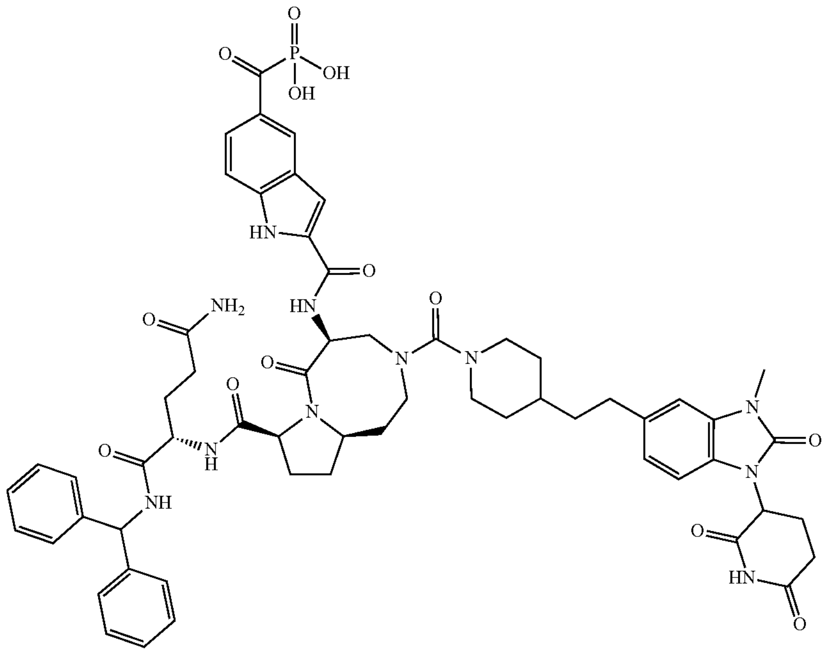 [SMILES: Cn1c(=O)n(C2CCC(=O)NC2=O)c2ccc(CCC3CCN(C(=O)N4CC[C@H]5CC[C@@H](C(=O)N[C@@H](CCC(N)=O)C(=O)NC(c6ccccc6)c6ccccc6)N5C(=O)[C@@H](NC(=O)c5cc6cc(C(=O)P(=O)(O)O)ccc6[nH]5)C4)CC3)cc21] |

TABLE 1-continued
| Exemplary Compounds | |
|---|---|
| I-# | Structure |
| I-193 | 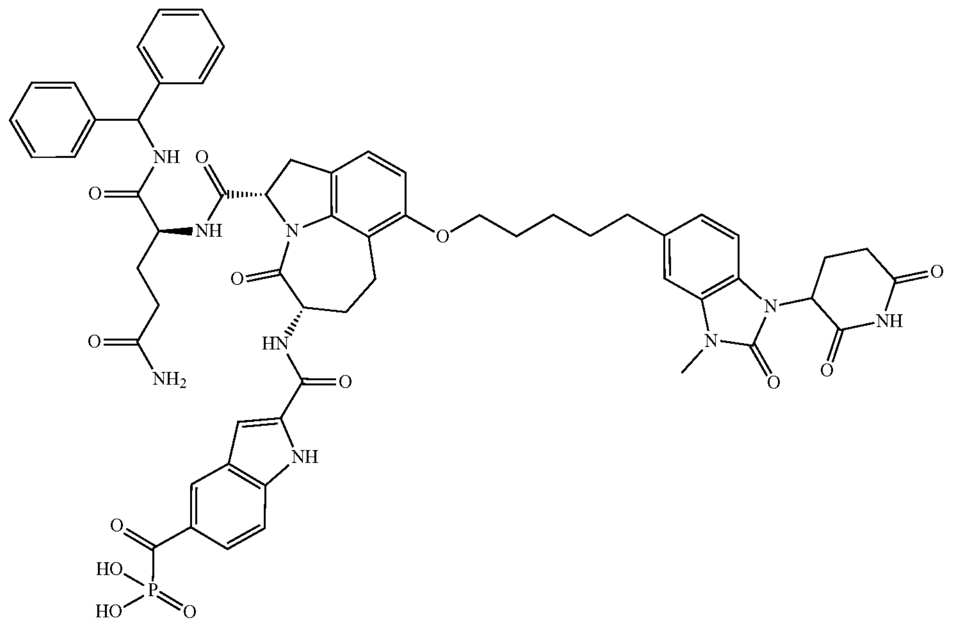 [SMILES: Cn1c(=O)n(C2CCC(=O)NC2=O)c2ccc(CCCCCOc3ccc4c5c3CC[C@H](NC(=O)c3cc6cc(C(=O)P(=O)(O)O)ccc6[nH]3)C(=O)N5[C@H](C(=O)N[C@@H](CCC(N)=O)C(=O)NC(c3ccccc3)c3ccccc3)C4)cc21] |

TABLE 1-continued
| Exemplary Compounds | |
| --- | --- |
| I-# | Structure |
| I-194 | 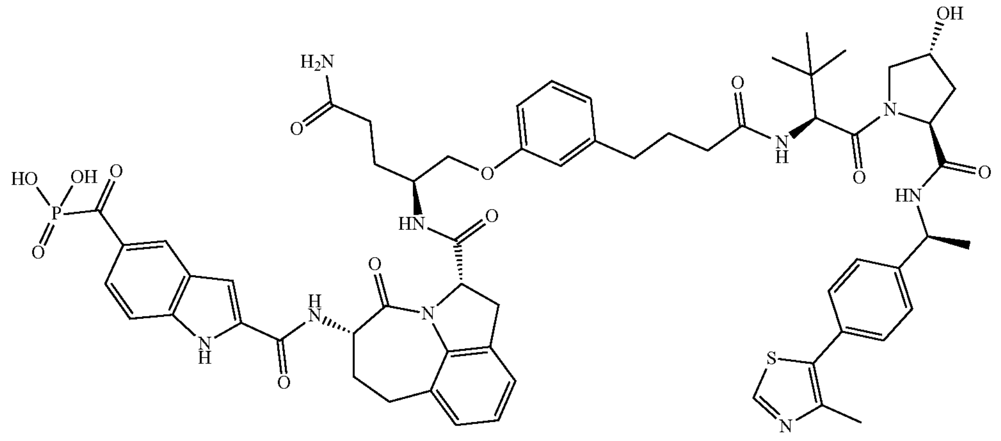 [SMILES: Cc1ncsc1-c1ccc([C@H](C)NC(=O)[C@@H]2C[C@@H](O)CN2C(=O)[C@@H](NC(=O)CCCc2cccc(OC[C@H](CCC(N)=O)NC(=O)[C@@H]3Cc4cccc5c4N3C(=O)[C@@H](NC(=O)c3cc4cc(C(=O)P(=O)(O)O)ccc4[nH]3)CC5)c2)C(C)(C)C)cc1] |

TABLE 1-continued
| Exemplary Compounds | |
|---|---|
| I-# | Structure |
| I-195 | 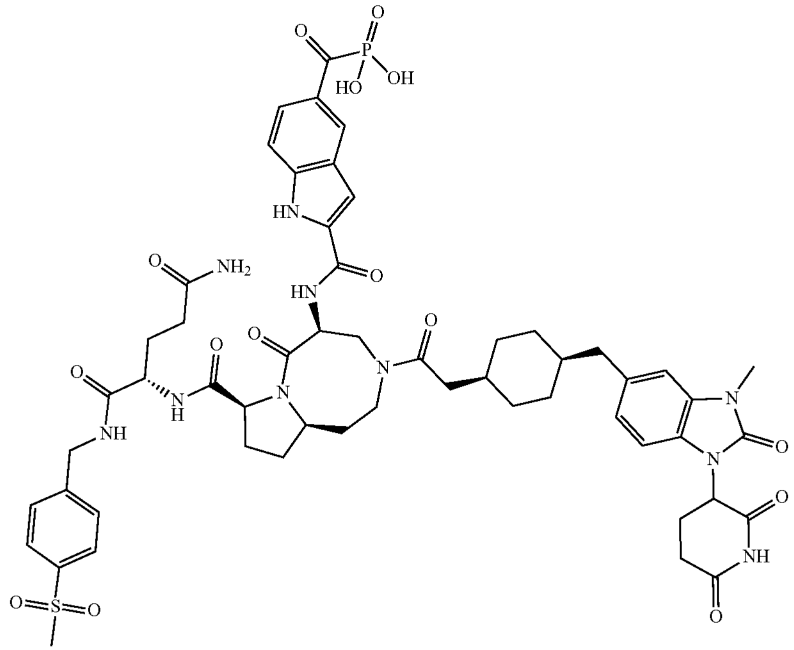 [SMILES: Cn1c(=O)n(C2CCC(=O)NC2=O)c2ccc(C[C@H]3CC[C@@H](CC(=O)N4CC[C@H]5CC[C@@H](C(=O)N[C@@H](CCC(N)=O)C(=O)NCc6ccc(S(C)(=O)=O)cc6)N5C(=O)[C@@H](NC(=O)c5cc6cc(C(=O)P(=O)(O)O)ccc6[nH]5)C4)CC3)cc21] |

TABLE 1-continued
| Exemplary Compounds | |
|---|---|
| I-# | Structure |
| I-196 | 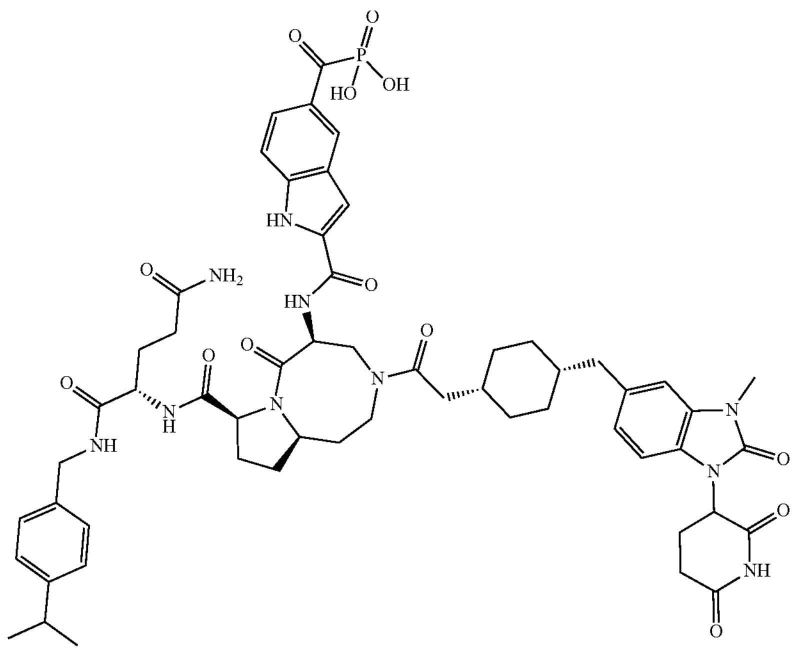 [SMILES: CC(C)c1ccc(CNC(=O)[C@H](CCC(N)=O)NC(=O)[C@@H]2CC[C@@H]3CCN(C(=O)C[C@H]4CC[C@@H](Cc5ccc6c(c5)n(C)c(=O)n6C5CCC(=O)NC5=O)CC4)C[C@H](NC(=O)c4cc5cc(C(=O)P(=O)(O)O)ccc5[nH]4)C(=O)N32)cc1] |

TABLE 1-continued
| Exemplary Compounds | |
|---|---|
| I-# | Structure |
| I-197 | 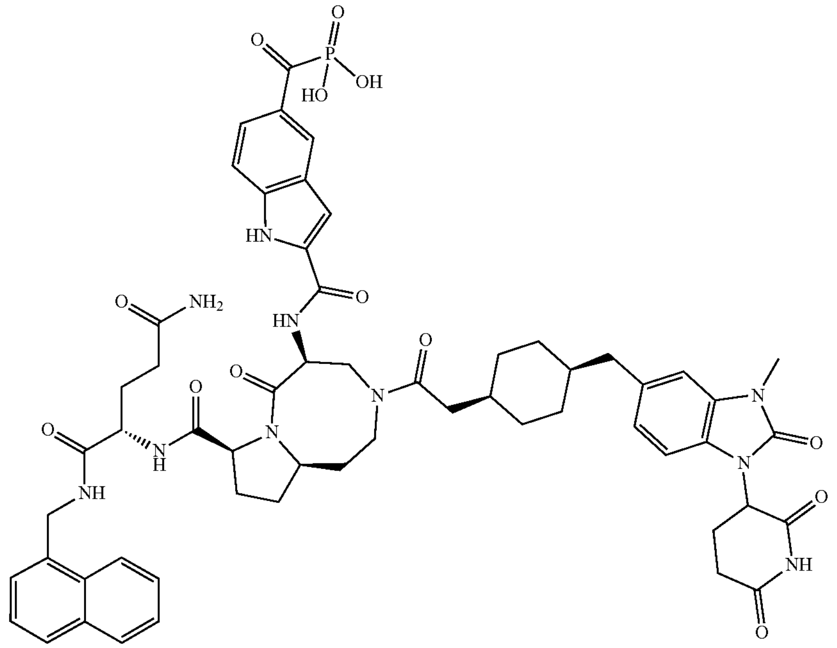 [SMILES: Cn1c(=O)n(C2CCC(=O)NC2=O)c2ccc(C[C@H]3CC[C@@H](CC(=O)N4CC[C@H]5CC[C@@H](C(=O)N[C@@H](CCC(N)=O)C(=O)NCc6cccc7ccccc67)N5C(=O)[C@@H](NC(=O)c5cc6cc(C(=O)P(=O)(O)O)ccc6[nH]5)C4)CC3)cc21] |

TABLE 1-continued
| Exemplary Compounds | |
|---|---|
| I-# | Structure |
| I-198 | 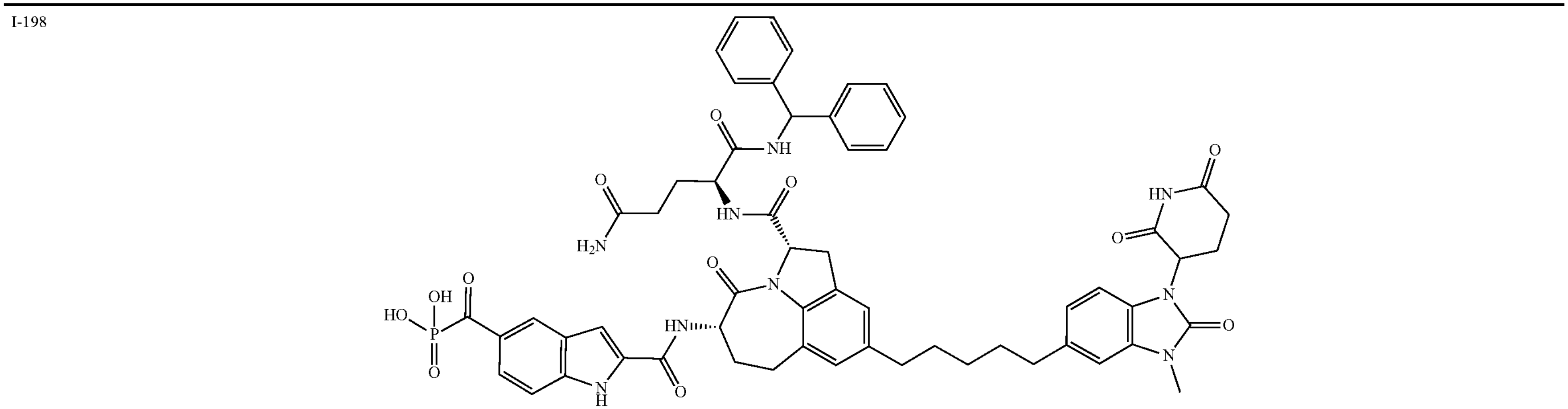 |
| I-199 | 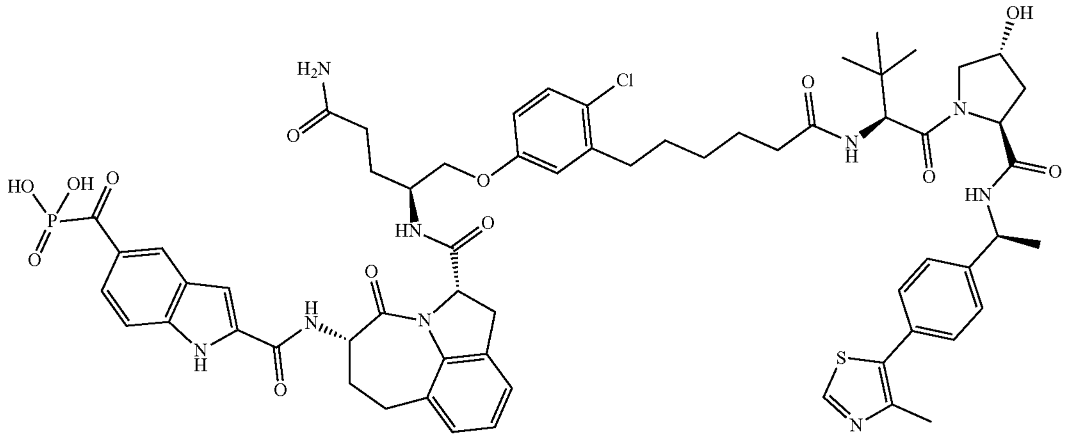 [SMILES: Cc1ncsc1-c1ccc([C@H](C)NC(=O)[C@@H]2C[C@@H](O)CN2C(=O)[C@@H](NC(=O)CCCCCc2cc(OC[C@H](CCC(N)=O)NC(=O)[C@@H]3Cc4cccc5c4N3C(=O)[C@@H](NC(=O)c3cc4cc(C(=O)P(=O)(O)O)ccc4[nH]3)CC5)ccc2Cl)C(C)(C)C)cc1] |

TABLE 1-continued
Exemplary Compounds
| I-# | Structure |
| --- | --- |
| I-200 | 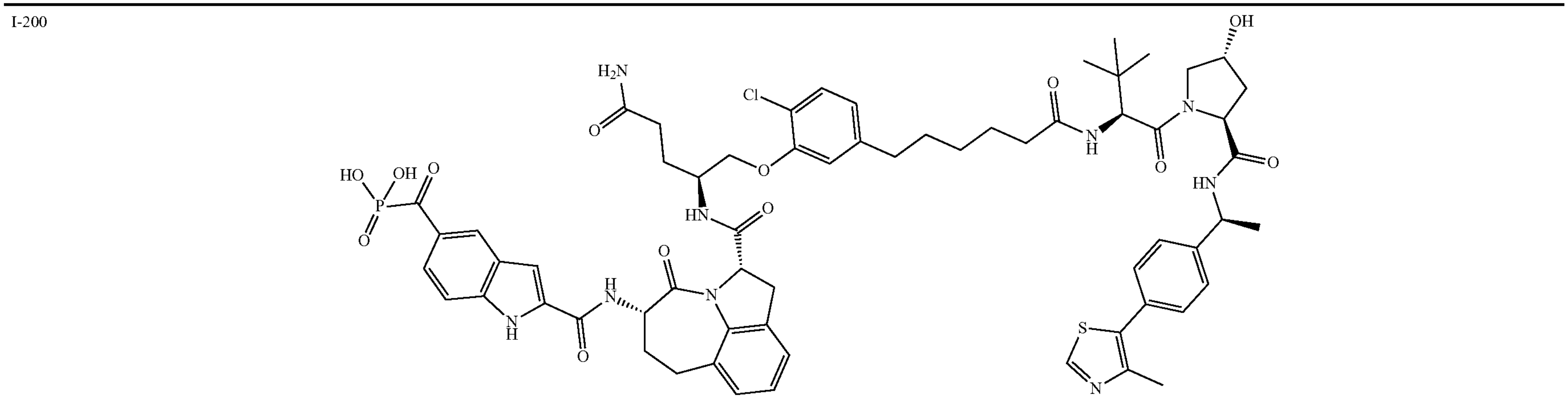 |
| I-201 | 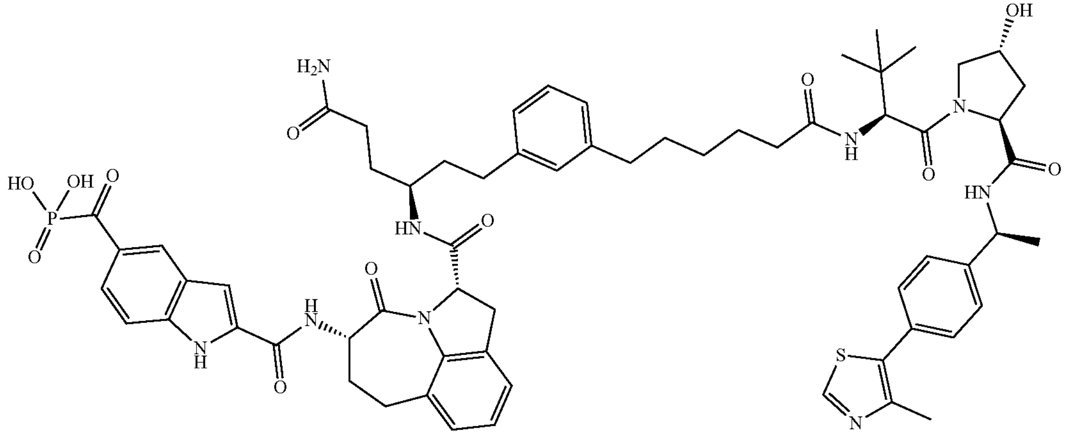 [SMILES: Cc1ncsc1-c1ccc([C@H](C)NC(=O)[C@@H]2C[C@@H](O)CN2C(=O)[C@@H](NC(=O)CCCCCc2cccc(CC[C@H](CCC(N)=O)NC(=O)[C@@H]3Cc4cccc5c4N3C(=O)[C@@H](NC(=O)c3cc4cc(C(=O)P(=O)(O)O)ccc4[nH]3)CC5)c2)C(C)(C)C)cc1] |

TABLE 1-continued
| Exemplary Compounds | |
|---|---|
| I-# | Structure |
| I-202 | 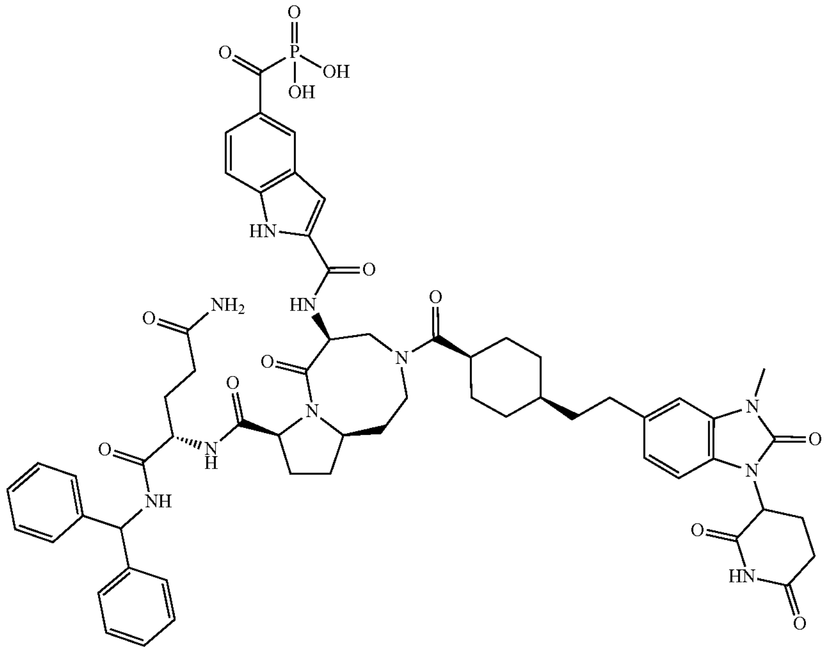 [SMILES: Cn1c(=O)n(C2CCC(=O)NC2=O)c2ccc(CC[C@H]3CC[C@@H](C(=O)N4CC[C@H]5CC[C@@H](C(=O)N[C@@H](CCC(N)=O)C(=O)NC(c6ccccc6)c6ccccc6)N5C(=O)[C@@H](NC(=O)c5cc6cc(C(=O)P(=O)(O)O)ccc6[nH]5)C4)CC3)cc21] |

TABLE 1-continued
| Exemplary Compounds | |
|---|---|
| I-# | Structure |
| I-203 | 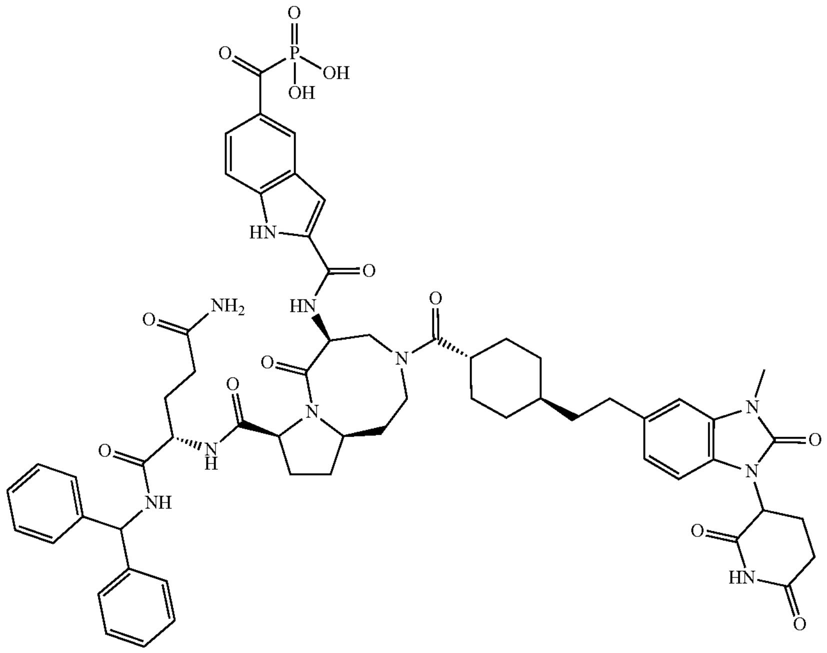 [SMILES: Cn1c(=O)n(C2CCC(=O)NC2=O)c2ccc(CC[C@H]3CC[C@H](C(=O)N4CC[C@H]5CC[C@@H](C(=O)N[C@@H](CCC(N)=O)C(=O)NC(c6ccccc6)c6ccccc6)N5C(=O)[C@@H](NC(=O)c5cc6cc(C(=O)P(=O)(O)O)ccc6[nH]5)C4)CC3)cc21] |

TABLE 1-continued
| Exemplary Compounds | |
|---|---|
| I-# | Structure |
| I-204 | 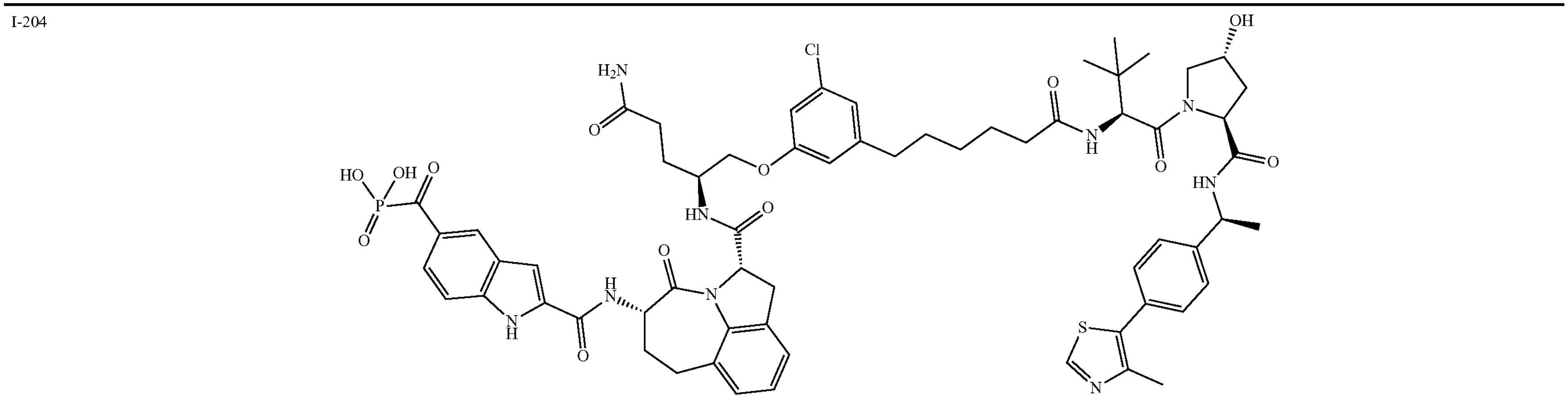 |
| I-205 | 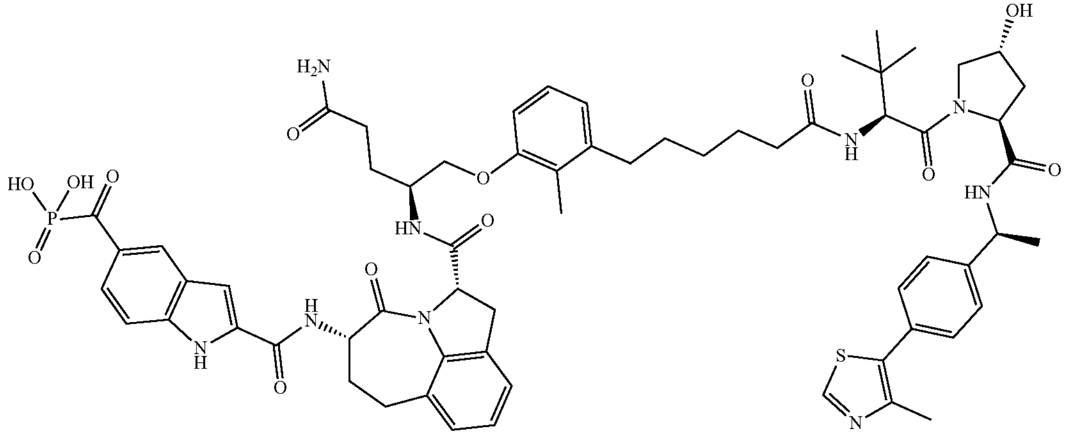 [SMILES: Cc1ncsc1-c1ccc([C@H](C)NC(=O)[C@@H]2C[C@@H](O)CN2C(=O)[C@@H](NC(=O)CCCCCc2cccc(OC[C@H](CCC(N)=O)NC(=O)[C@@H]3Cc4cccc5c4N3C(=O)[C@@H](NC(=O)c3cc4cc(C(=O)P(=O)(O)O)ccc4[nH]3)CC5)c2C)C(C)(C)C)cc1] |

TABLE 1-continued
| Exemplary Compounds | |
|---|---|
| I-# | Structure |
| I-206 | 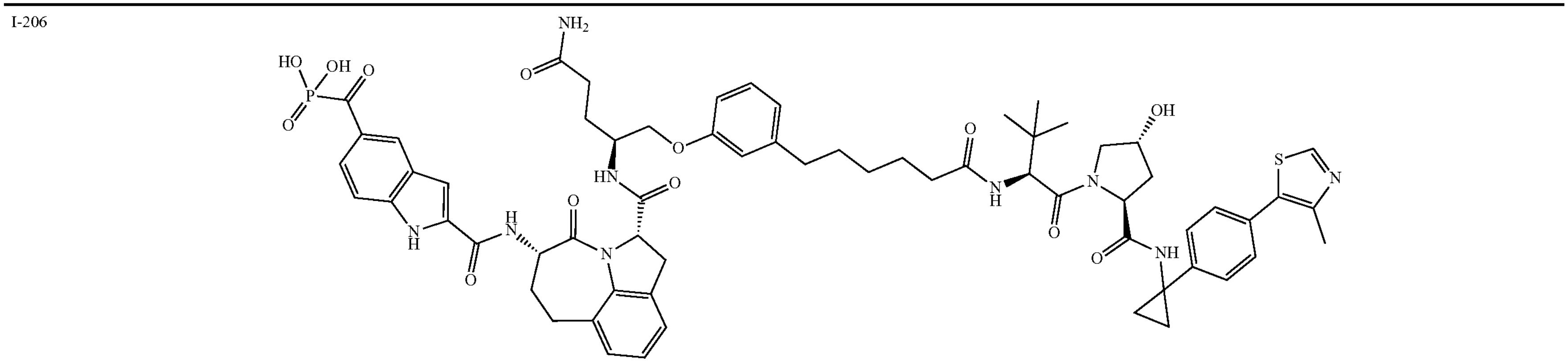 |
| I-207 | 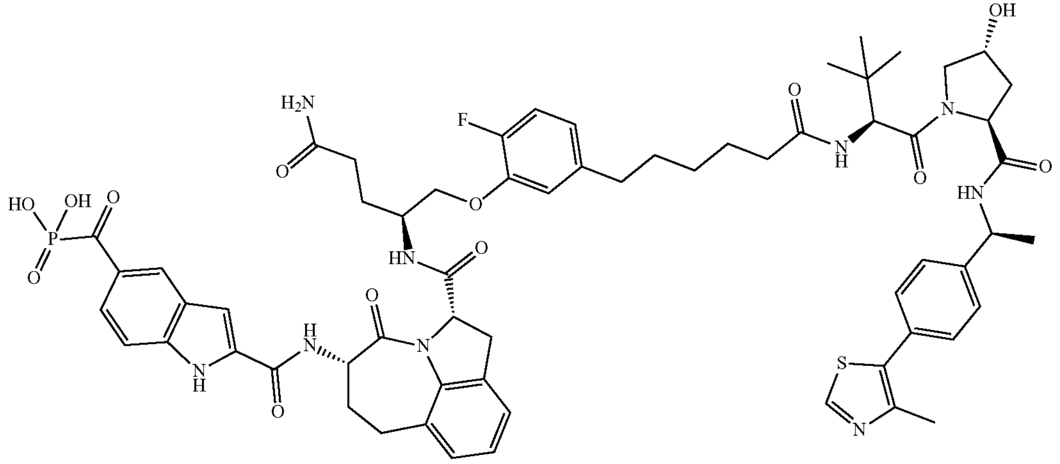 [SMILES: Cc1ncsc1-c1ccc([C@H](C)NC(=O)[C@@H]2C[C@@H](O)CN2C(=O)[C@@H](NC(=O)CCCCCc2ccc(F)c(OC[C@H](CCC(N)=O)NC(=O)[C@@H]3Cc4cccc5c4N3C(=O)[C@@H](NC(=O)c3cc4cc(C(=O)P(=O)(O)O)ccc4[nH]3)CC5)c2)C(C)(C)C)cc1] |

TABLE 1-continued
| Exemplary Compounds | |
|---|---|
| I-# | Structure |
| I-208 | 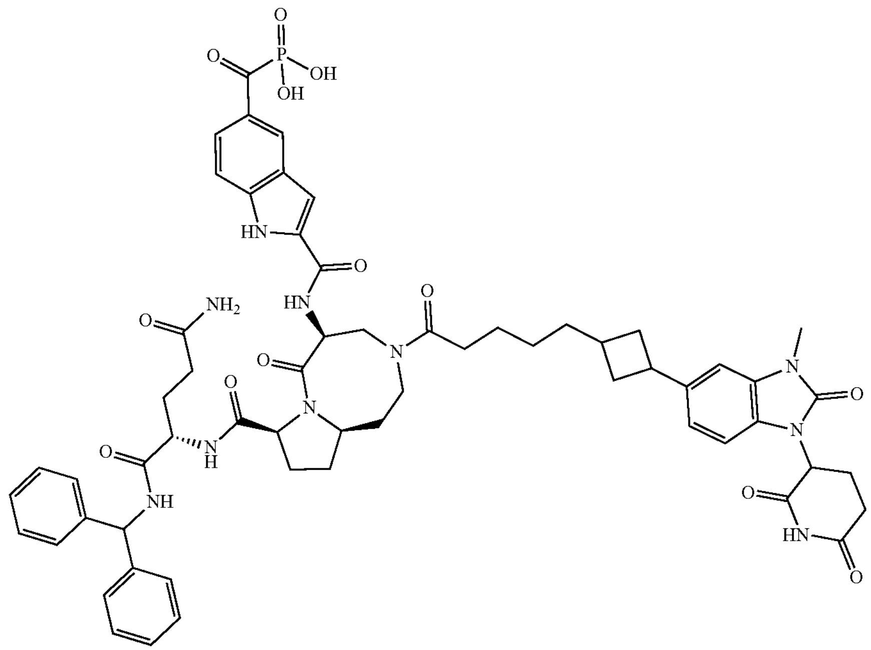 [SMILES: Cn1c(=O)n(C2CCC(=O)NC2=O)c2ccc(C3CC(CCCCC(=O)N4CC[C@H]5CC[C@@H](C(=O)N[C@@H](CCC(N)=O)C(=O)NC(c6ccccc6)c6ccccc6)N5C(=O)[C@@H](NC(=O)c5cc6cc(C(=O)P(=O)(O)O)ccc6[nH]5)C4)C3)cc21] |

TABLE 1-continued
| Exemplary Compounds | |
|---|---|
| I-# | Structure |
| I-209 | 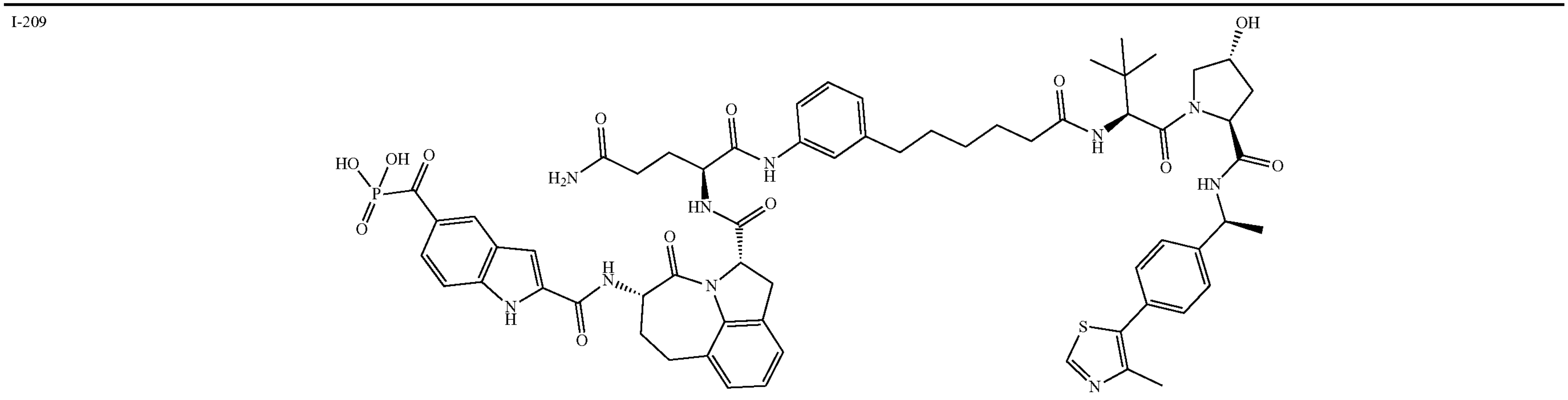 |
| I-210 | 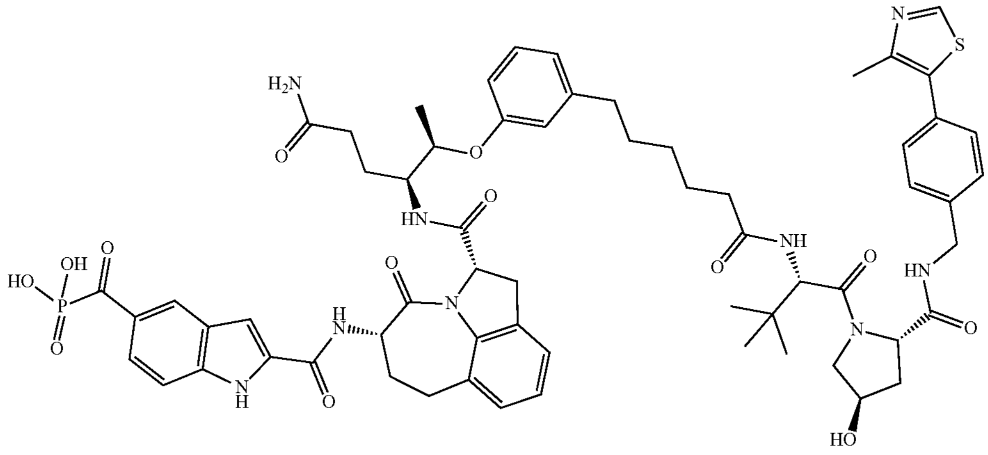 [SMILES: Cc1ncsc1-c1ccc(CNC(=O)[C@@H]2C[C@@H](O)CN2C(=O)[C@@H](NC(=O)CCCCCc2cccc(O[C@H](C)[C@H](CCC(N)=O)NC(=O)[C@@H]3Cc4cccc5c4N3C(=O)[C@@H](NC(=O)c3cc4cc(C(=O)P(=O)(O)O)ccc4[nH]3)CC5)c2)C(C)(C)C)cc1] |

TABLE 1-continued
| Exemplary Compounds | |
|---|---|
| I-# | Structure |
| I-211 | 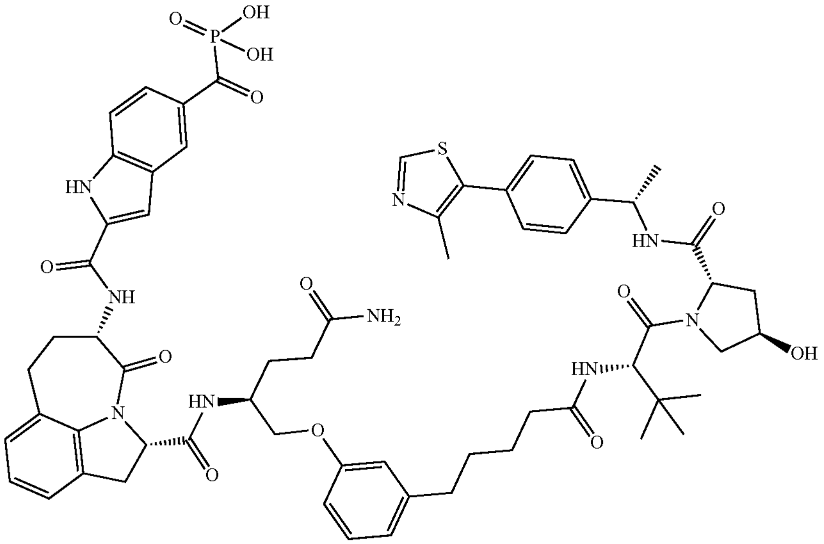 [SMILES: Cc1ncsc1-c1ccc([C@H](C)NC(=O)[C@@H]2C[C@@H](O)CN2C(=O)[C@@H](NC(=O)CCCCc2cccc(OC[C@H](CCC(N)=O)NC(=O)[C@@H]3Cc4cccc5c4N3C(=O)[C@@H](NC(=O)c3cc4cc(C(=O)P(=O)(O)O)ccc4[nH]3)CC5)c2)C(C)(C)C)cc1] |
| I-212 | 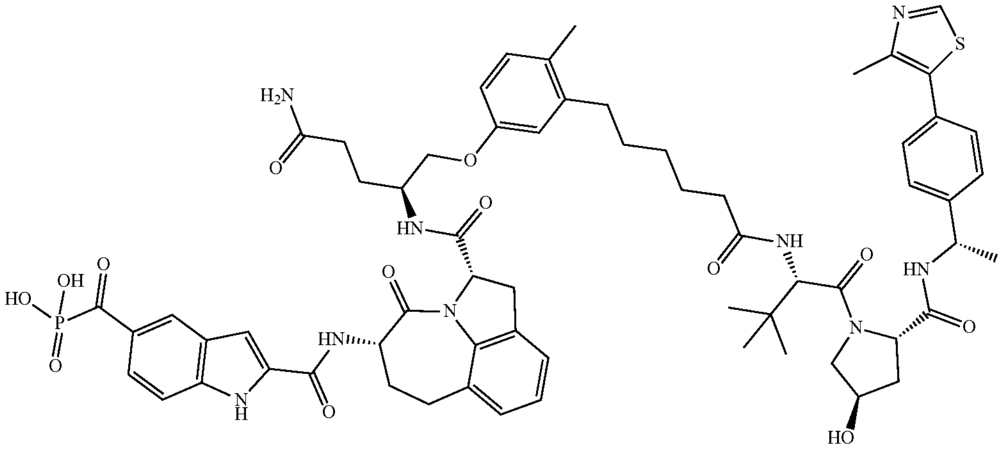 [SMILES: Cc1ccc(OC[C@H](CCC(N)=O)NC(=O)[C@@H]2Cc3cccc4c3N2C(=O)[C@@H](NC(=O)c2cc3cc(C(=O)P(=O)(O)O)ccc3[nH]2)CC4)cc1CCCCCC(=O)N[C@H](C(=O)N1C[C@H](O)C[C@H]1C(=O)N[C@@H](C)c1ccc(-c2scnc2C)cc1)C(C)(C)C] |

TABLE 1-continued
| Exemplary Compounds | |
|---|---|
| I-# | Structure |
| I-213 | 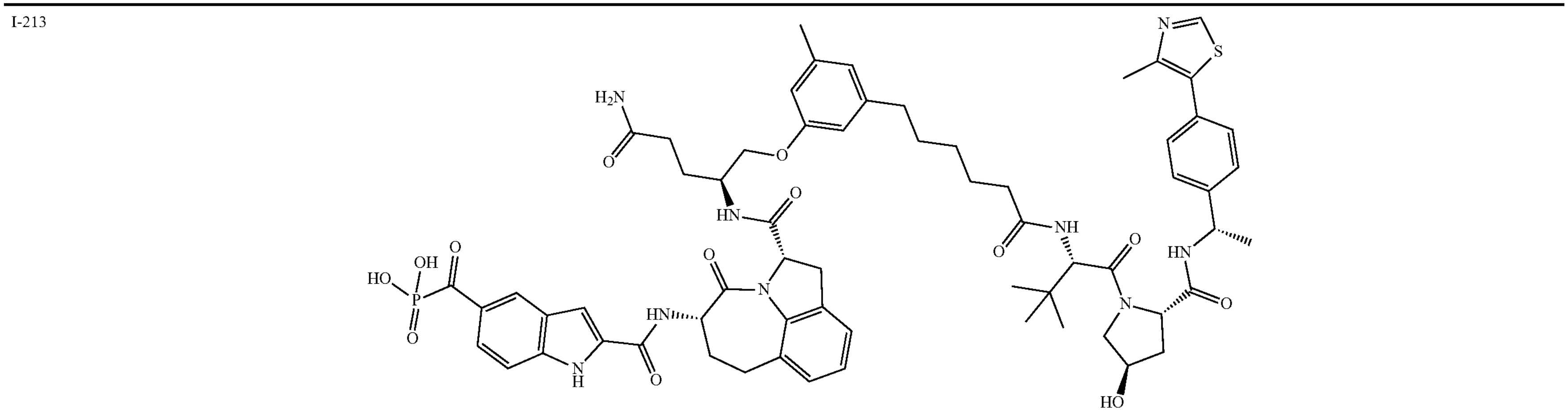 |
| I-214 | 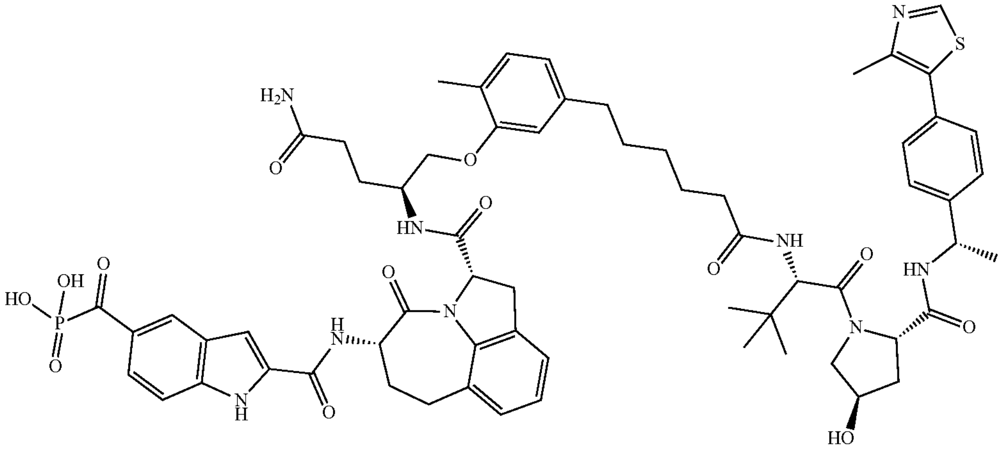 [SMILES: Cc1ccc(CCCCCC(=O)N[C@H](C(=O)N2C[C@H](O)C[C@H]2C(=O)N[C@@H](C)c2ccc(-c3scnc3C)cc2)C(C)(C)C)cc1OC[C@H](CCC(N)=O)NC(=O)[C@@H]1Cc2cccc3c2N1C(=O)[C@@H](NC(=O)c1cc2cc(C(=O)P(=O)(O)O)ccc2[nH]1)CC3] |

TABLE 1-continued
| Exemplary Compounds | |
|---|---|
| I-# | Structure |
| I-215 | 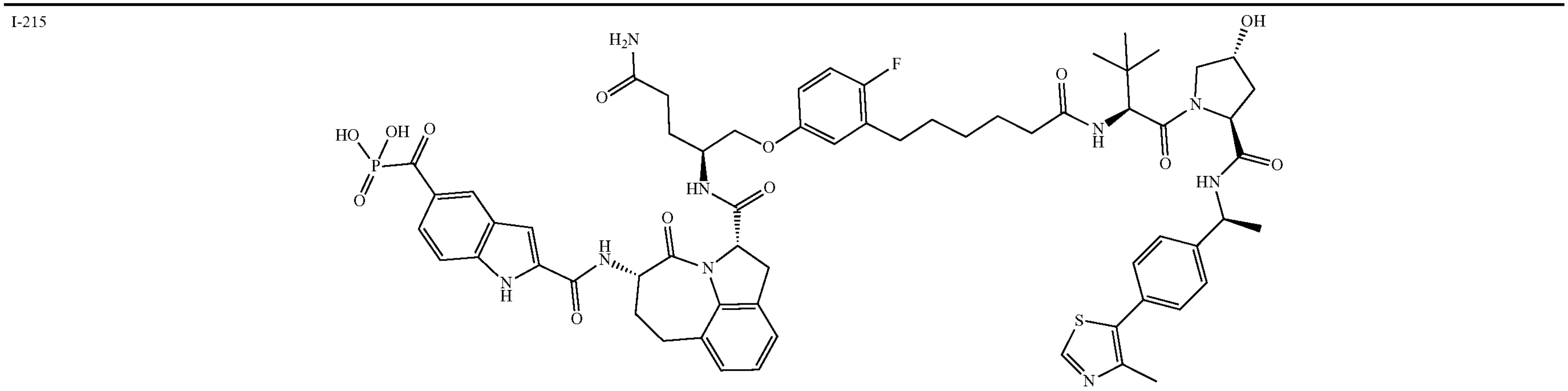 |
| I-216 | 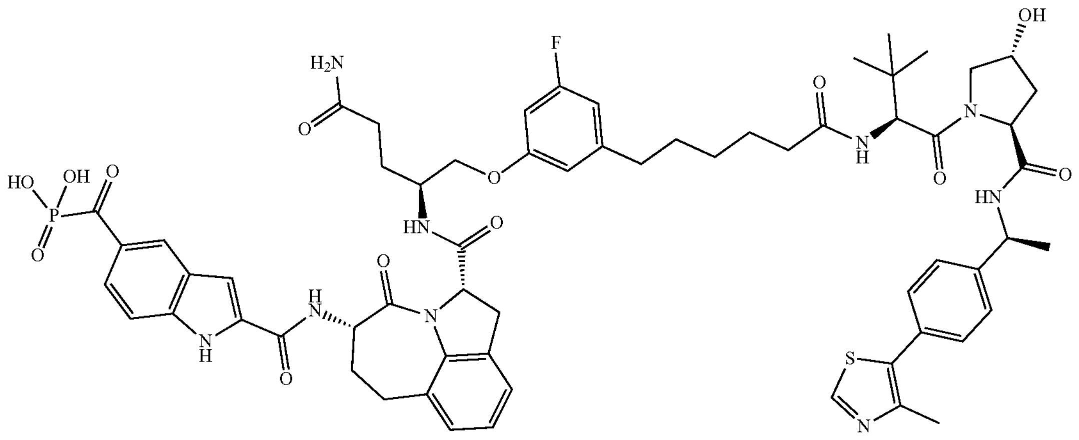 [SMILES: Cc1ncsc1-c1ccc([C@H](C)NC(=O)[C@@H]2C[C@@H](O)CN2C(=O)[C@@H](NC(=O)CCCCCc2cc(F)cc(OC[C@H](CCC(N)=O)NC(=O)[C@@H]3Cc4cccc5c4N3C(=O)[C@@H](NC(=O)c3cc4cc(C(=O)P(=O)(O)O)ccc4[nH]3)CC5)c2)C(C)(C)C)cc1] |

TABLE 1-continued
| Exemplary Compounds | |
|---|---|
| I-# | Structure |
| I-217 | 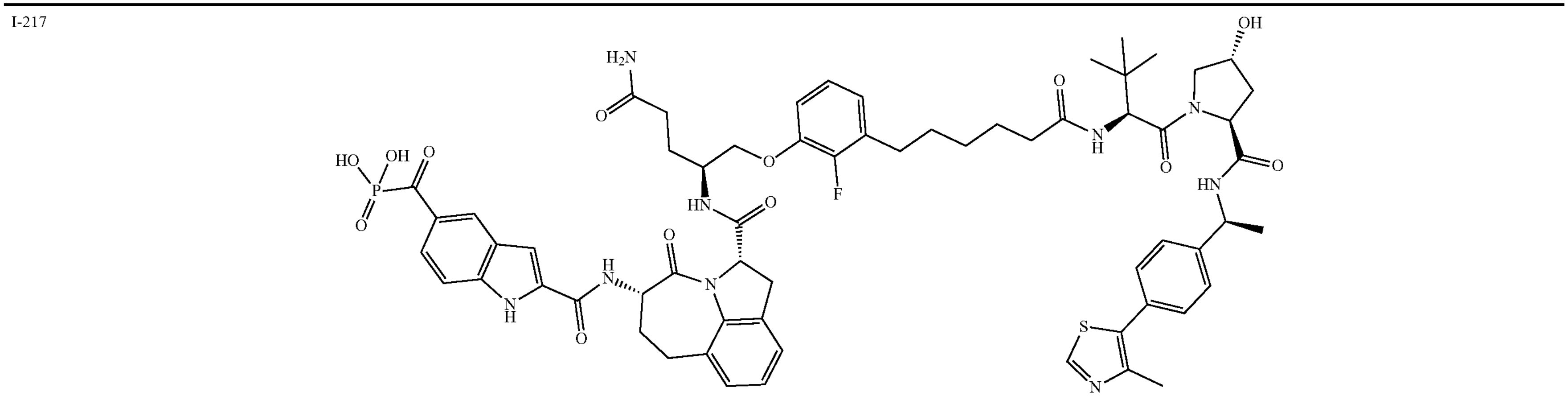 |
| I-218 | 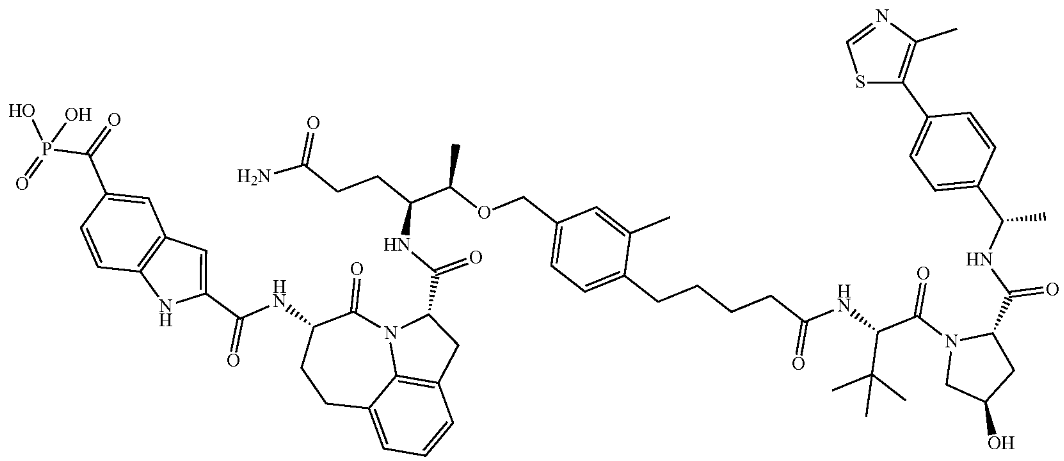 [SMILES: Cc1cc(CO[C@H](C)[C@H](CCC(N)=O)NC(=O)[C@@H]2Cc3cccc4c3N2C(=O)[C@@H](NC(=O)c2cc3cc(C(=O)P(=O)(O)O)ccc3[nH]2)CC4)ccc1CCCCC(=O)N[C@H](C(=O)N1C[C@H](O)C[C@H]1C(=O)N[C@@H](C)c1ccc(-c2scnc2C)cc1)C(C)(C)C] |

TABLE 1-continued
| Exemplary Compounds | |
|---|---|
| I-# | Structure |
| I-219 | 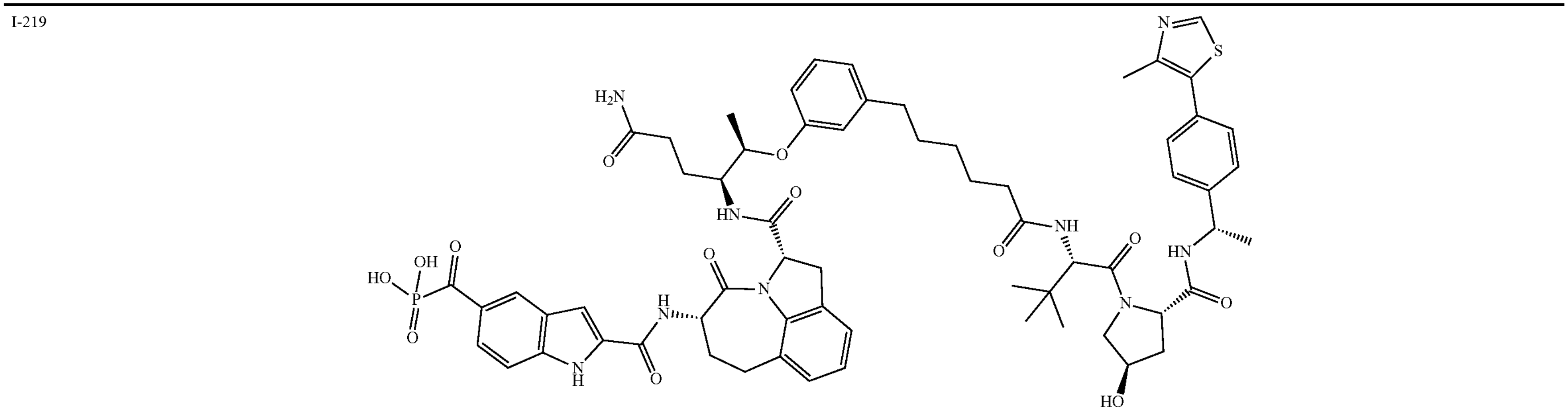 |
| I-220 | 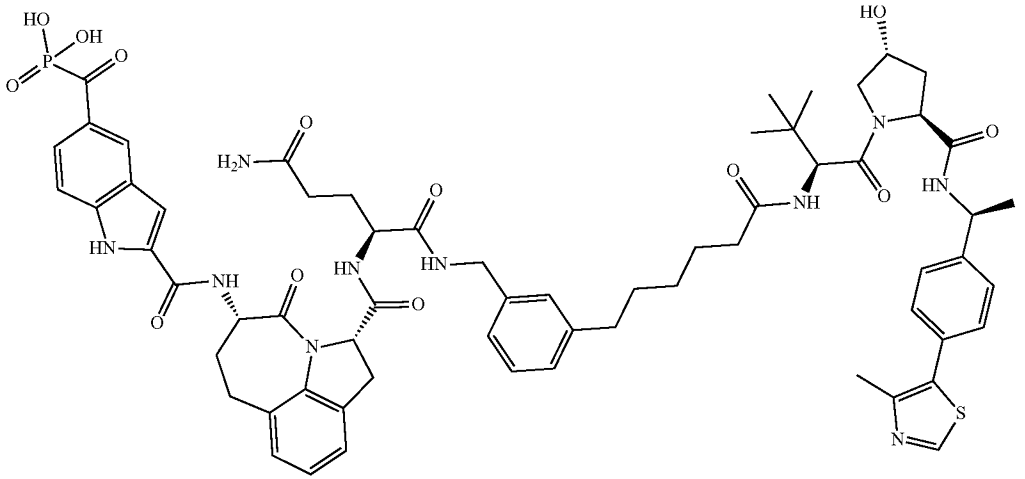 [SMILES: Cc1ncsc1-c1ccc([C@H](C)NC(=O)[C@@H]2C[C@@H](O)CN2C(=O)[C@@H](NC(=O)CCCCCc2cccc(CNC(=O)[C@H](CCC(N)=O)NC(=O)[C@@H]3Cc4cccc5c4N3C(=O)[C@@H](NC(=O)c3cc4cc(C(=O)P(=O)(O)O)ccc4[nH]3)CC5)c2)C(C)(C)C)cc1] |

TABLE 1-continued
| Exemplary Compounds | |
|---|---|
| I-# | Structure |
| I-221 | 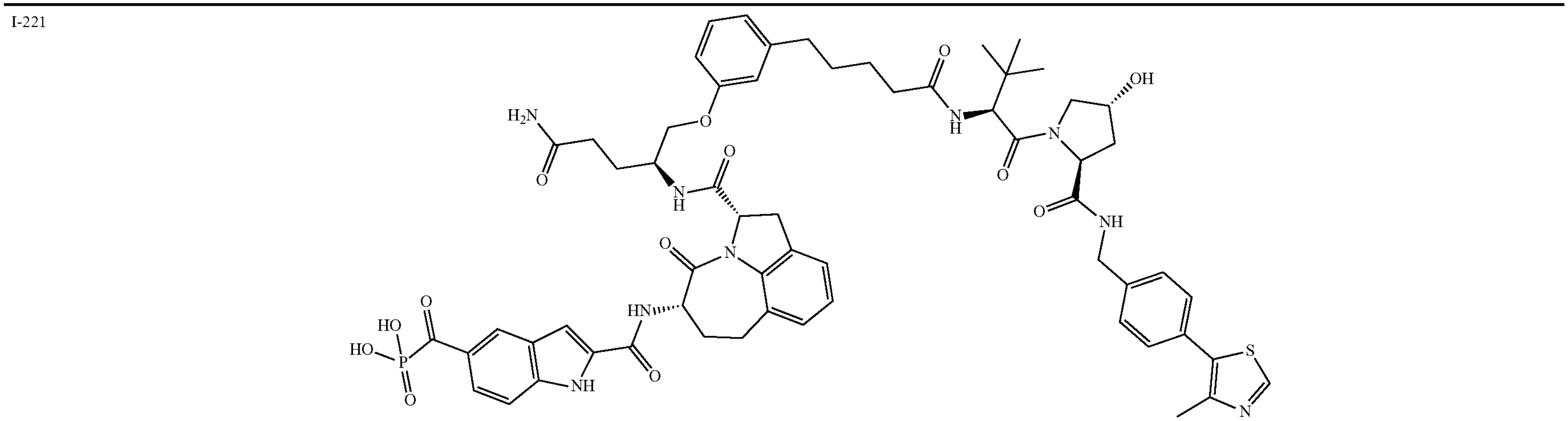 |
| I-222 | 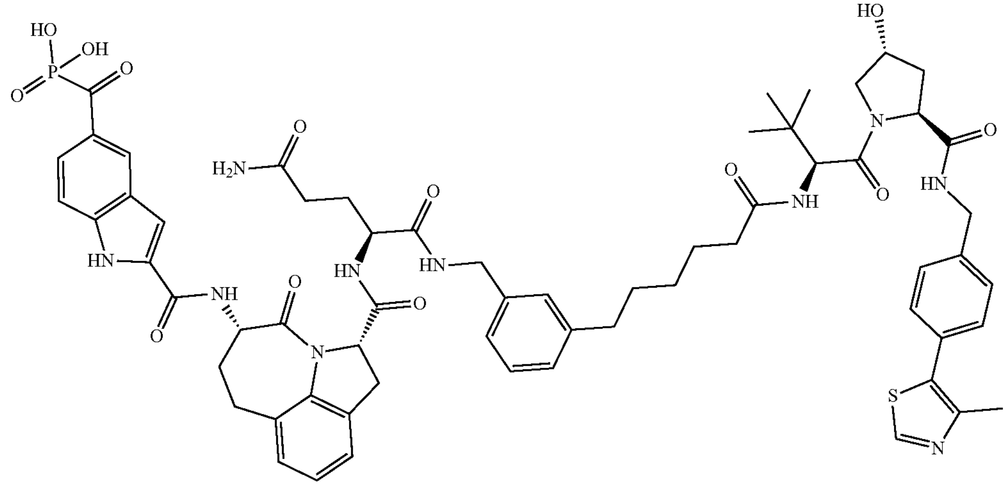 [SMILES: Cc1ncsc1-c1ccc(CNC(=O)[C@@H]2C[C@@H](O)CN2C(=O)[C@@H](NC(=O)CCCCCc2cccc(CNC(=O)[C@H](CCC(N)=O)NC(=O)[C@@H]3Cc4cccc5c4N3C(=O)[C@@H](NC(=O)c3cc4cc(C(=O)P(=O)(O)O)ccc4[nH]3)CC5)c2)C(C)(C)C)cc1] |

TABLE 1-continued
| Exemplary Compounds | |
|---|---|
| I-# | Structure |
| I-223 | 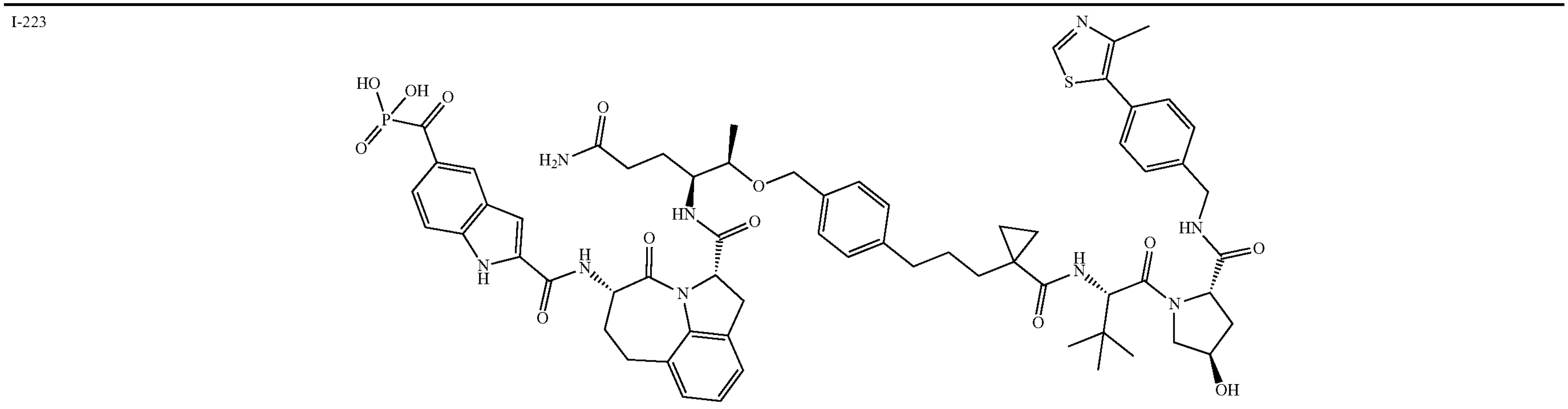 |
| I-224 | 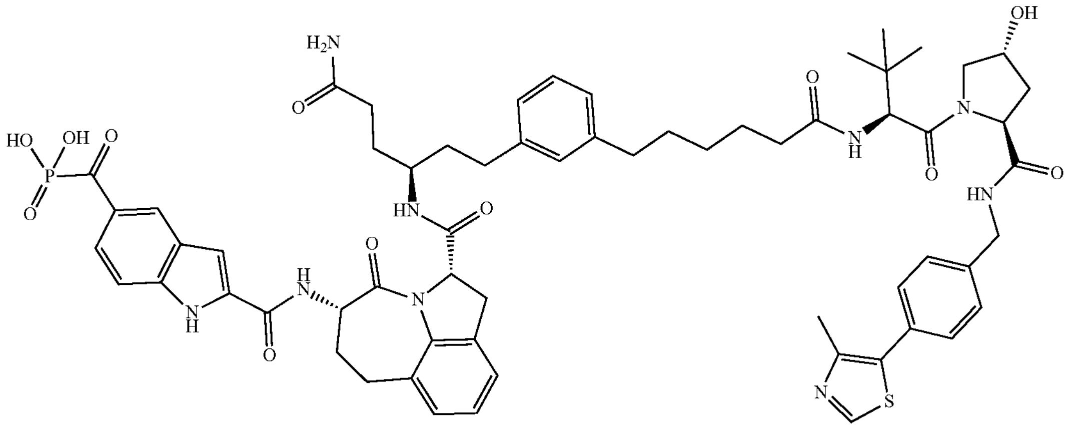 [SMILES: Cc1ncsc1-c1ccc(CNC(=O)[C@@H]2C[C@@H](O)CN2C(=O)[C@@H](NC(=O)CCCCCc2cccc(CC[C@H](CCC(N)=O)NC(=O)[C@@H]3Cc4cccc5c4N3C(=O)[C@@H](NC(=O)c3cc4cc(C(=O)P(=O)(O)O)ccc4[nH]3)CC5)c2)C(C)(C)C)cc1] |

TABLE 1-continued
| Exemplary Compounds | |
|---|---|
| I-# | Structure |
| I-225 | 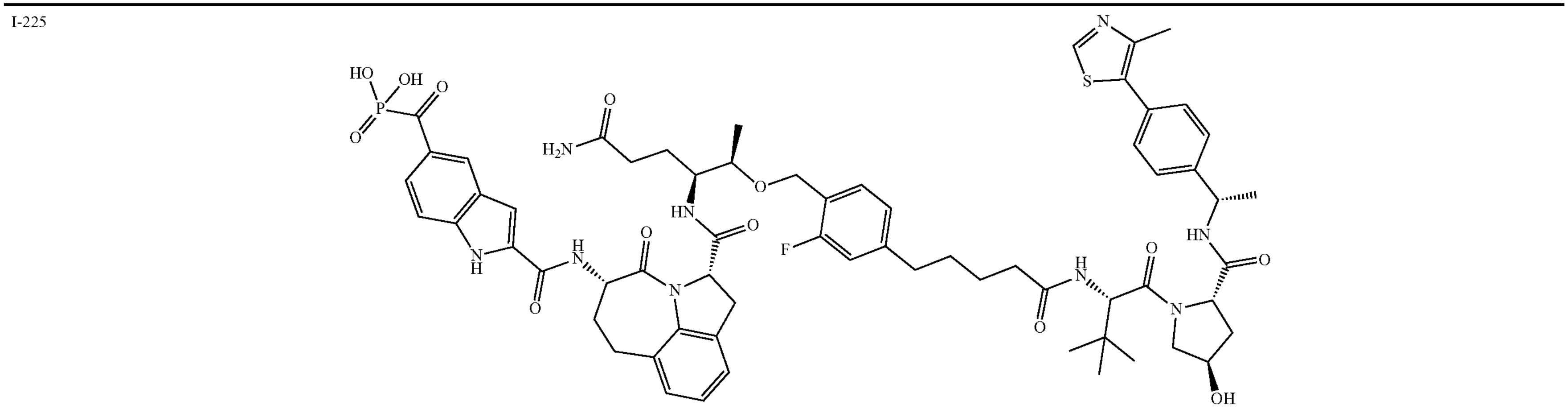 |
| I-226 | 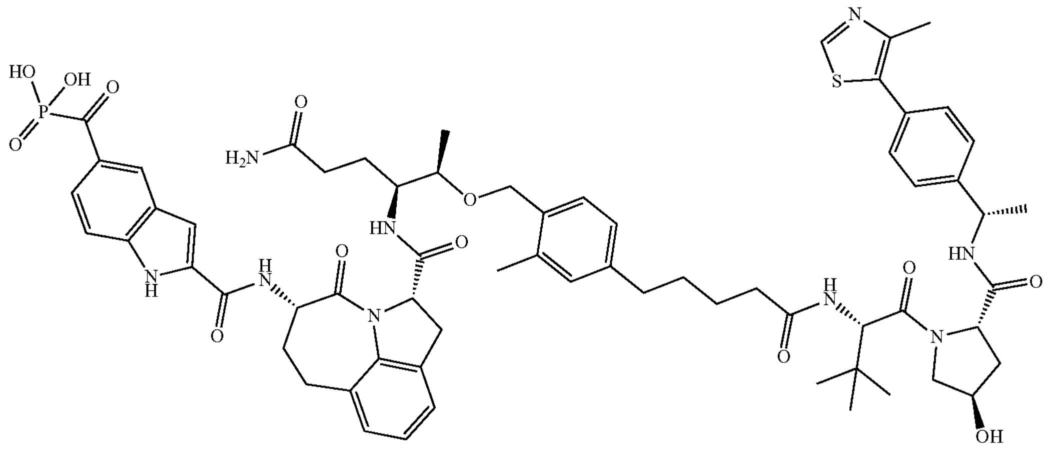 [SMILES: Cc1cc(CCCCC(=O)N[C@H](C(=O)N2C[C@H](O)C[C@H]2C(=O)N[C@@H](C)c2ccc(-c3scnc3C)cc2)C(C)(C)C)ccc1CO[C@H](C)[C@H](CCC(N)=O)NC(=O)[C@@H]1Cc2cccc3c2N1C(=O)[C@@H](NC(=O)c1cc2cc(C(=O)P(=O)(O)O)ccc2[nH]1)CC3] |

TABLE 1-continued
| Exemplary Compounds | |
|---|---|
| I-# | Structure |
| I-227 | 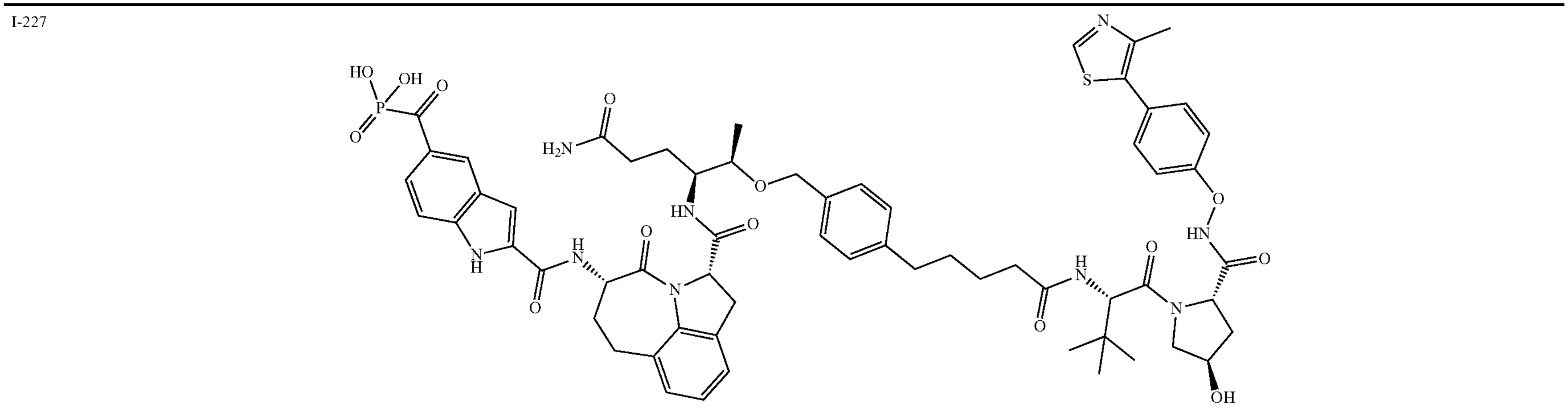 |
| I-228 | 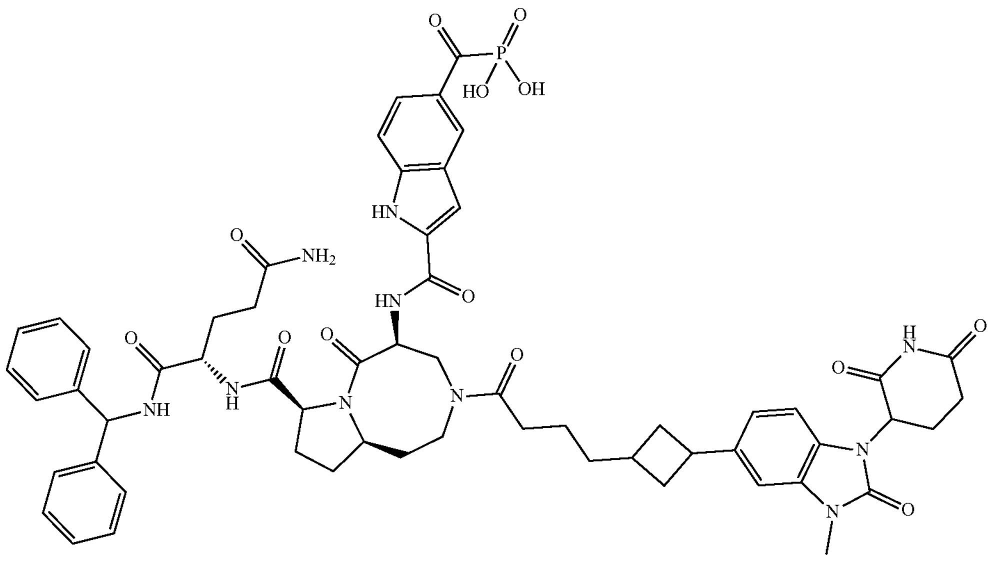 [SMILES: Cn1c(=O)n(C2CCC(=O)NC2=O)c2ccc(C3CC(CCCC(=O)N4CC[C@H]5CC[C@@H](C(=O)N[C@@H](CCC(N)=O)C(=O)NC(c6ccccc6)c6ccccc6)N5C(=O)[C@@H](NC(=O)c5cc6cc(C(=O)P(=O)(O)O)ccc6[nH]5)C4)C3)cc21] |

TABLE 1-continued
| Exemplary Compounds | |
|---|---|
| I-# | Structure |
| I-229 | 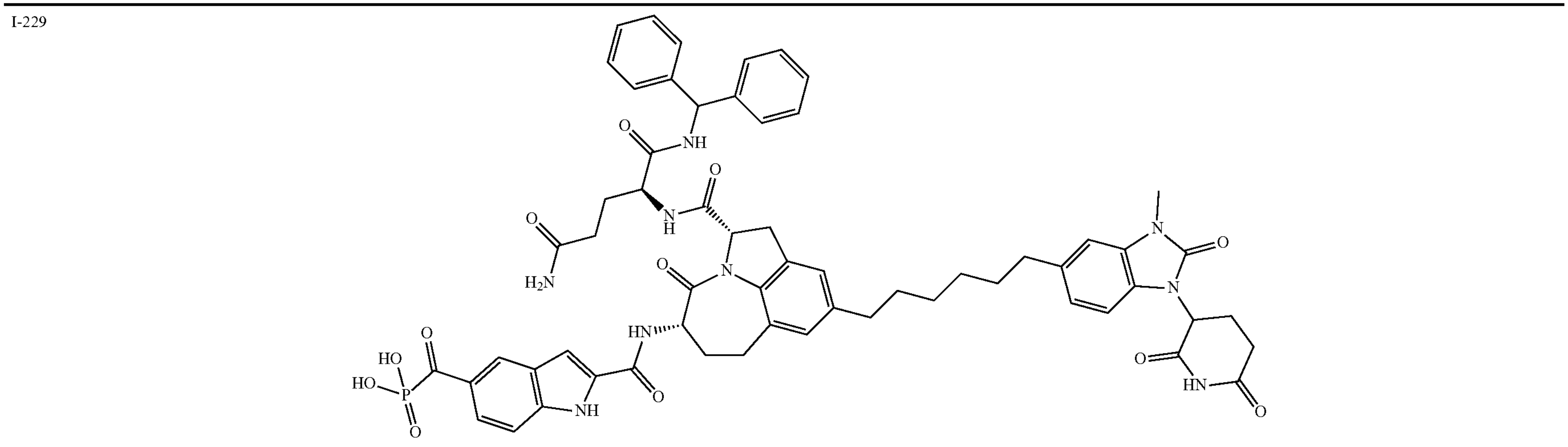 |
| I-230 | 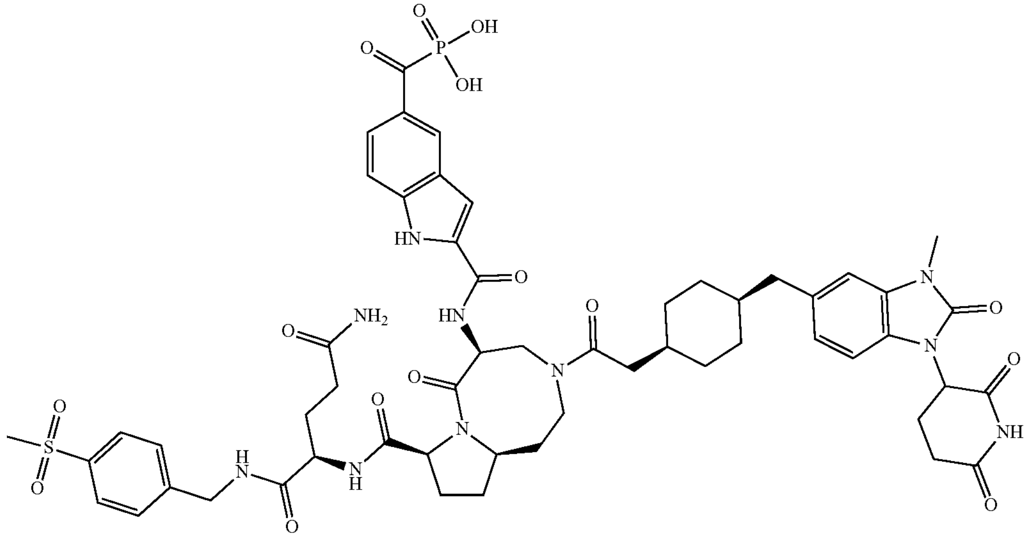 [SMILES: Cn1c(=O)n(C2CCC(=O)NC2=O)c2ccc(C[C@H]3CC[C@@H](CC(=O)N4CC[C@H]5CC[C@@H](C(=O)N[C@H](CCC(N)=O)C(=O)NCc6ccc(S(C)(=O)=O)cc6)N5C(=O)[C@@H](NC(=O)c5cc6cc(C(=O)P(=O)(O)O)ccc6[nH]5)C4)CC3)cc21] |

TABLE 1-continued
| Exemplary Compounds | |
|---|---|
| I-# | Structure |
| I-231 | 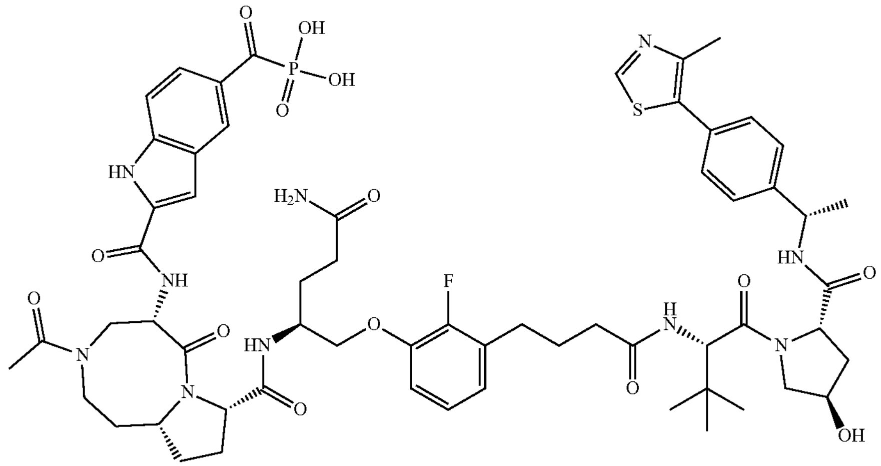 [SMILES: CC(=O)N1CC[C@H]2CC[C@@H](C(=O)N[C@@H](CCC(N)=O)COc3cccc(CCCC(=O)N[C@H](C(=O)N4C[C@H](O)C[C@H]4C(=O)N[C@@H](C)c4ccc(-c5scnc5C)cc4)C(C)(C)C)c3F)N2C(=O)[C@@H](NC(=O)c2cc3cc(C(=O)P(=O)(O)O)ccc3[nH]2)C1] |
| I-232 | 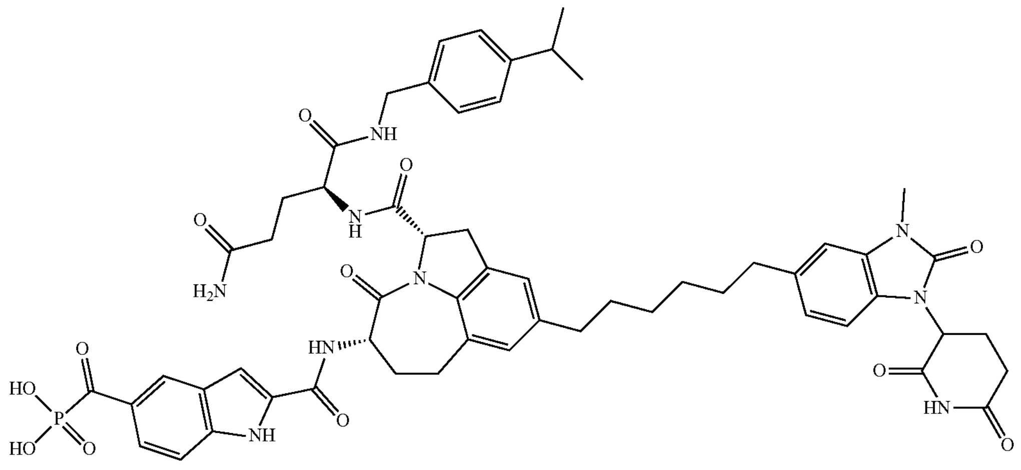 [SMILES: CC(C)c1ccc(CNC(=O)[C@H](CCC(N)=O)NC(=O)[C@@H]2Cc3cc(CCCCCCc4ccc5c(c4)n(C)c(=O)n5C4CCC(=O)NC4=O)cc4c3N2C(=O)[C@@H](NC(=O)c2cc3cc(C(=O)P(=O)(O)O)ccc3[nH]2)CC4)cc1] |

TABLE 1-continued
| Exemplary Compounds | |
|---|---|
| I-# | Structure |
| I-233 | 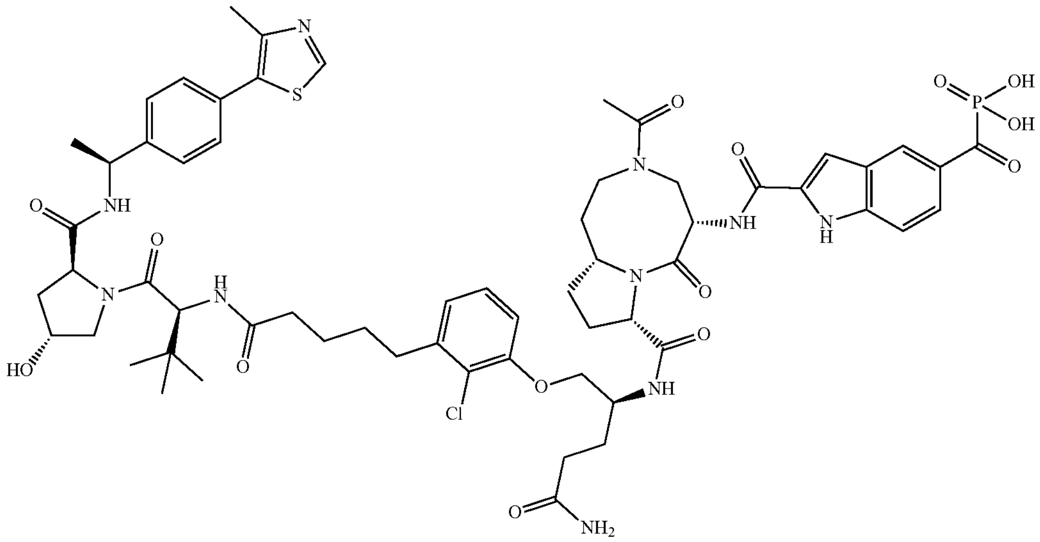 [SMILES: CC(=O)N1CC[C@H]2CC[C@@H](C(=O)N[C@@H](CCC(N)=O)COc3cccc(CCCCC(=O)N[C@H](C(=O)N4C[C@H](O)C[C@H]4C(=O)N[C@@H](C)c4ccc(-c5scnc5C)cc4)C(C)(C)C)c3Cl)N2C(=O)[C@@H](NC(=O)c2cc3cc(C(=O)P(=O)(O)O)ccc3[nH]2)C1] |

TABLE 1-continued
| Exemplary Compounds | |
|---|---|
| I-# | Structure |
| I-234 | 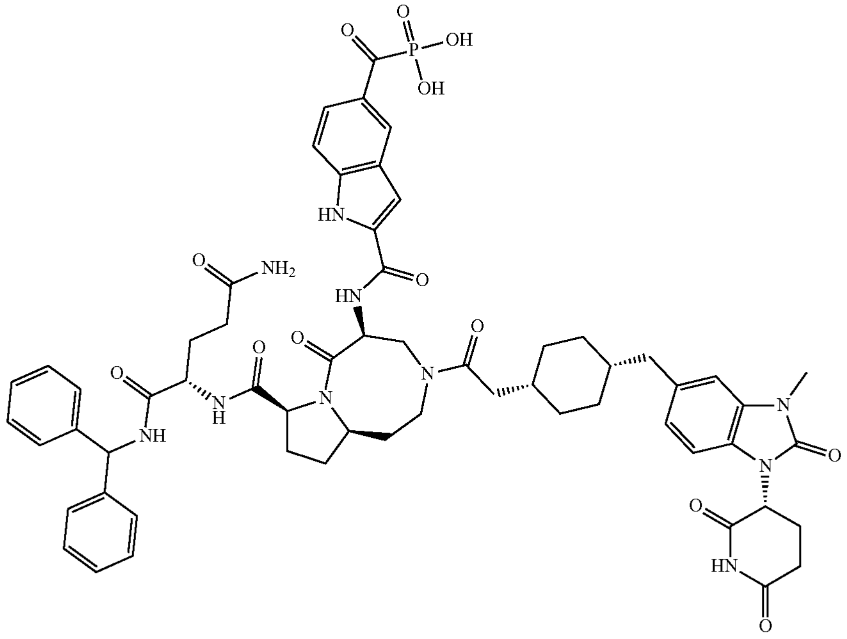 [SMILES: Cn1c(=O)n([C@@H]2CCC(=O)NC2=O)c2ccc(C[C@H]3CC[C@@H](CC(=O)N4CC[C@H]5CC[C@@H](C(=O)N[C@@H](CCC(N)=O)C(=O)NC(c6ccccc6)c6ccccc6)N5C(=O)[C@@H](NC(=O)c5cc6cc(C(=O)P(=O)(O)O)ccc6[nH]5)C4)CC3)cc21] |

TABLE 1-continued
| Exemplary Compounds | |
|---|---|
| I-# | Structure |
| I-235 | 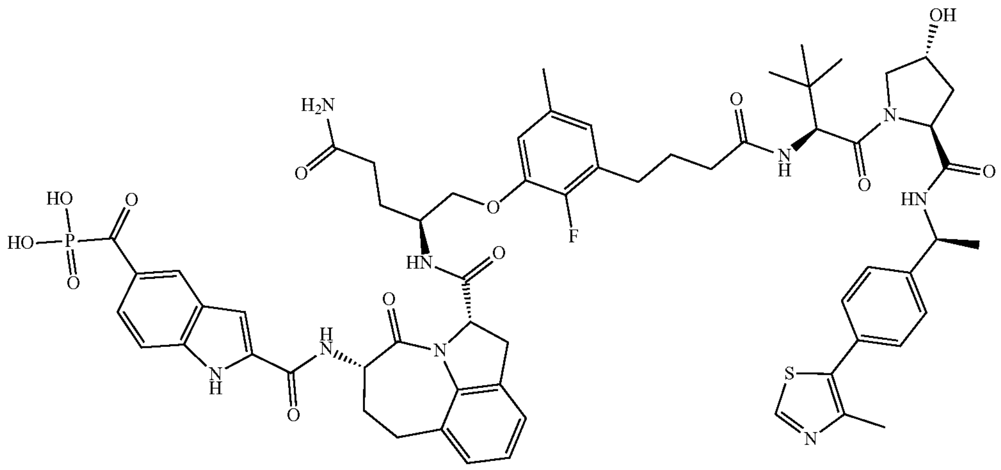 [SMILES: Cc1cc(CCCC(=O)N[C@H](C(=O)N2C[C@H](O)C[C@H]2C(=O)N[C@@H](C)c2ccc(-c3scnc3C)cc2)C(C)(C)C)c(F)c(OC[C@H](CCC(N)=O)NC(=O)[C@@H]2Cc3cccc4c3N2C(=O)[C@@H](NC(=O)c2cc3cc(C(=O)P(=O)(O)O)ccc3[nH]2)CC4)c1] |

TABLE 1-continued
| Exemplary Compounds | |
|---|---|
| I-# | Structure |
| I-236 | 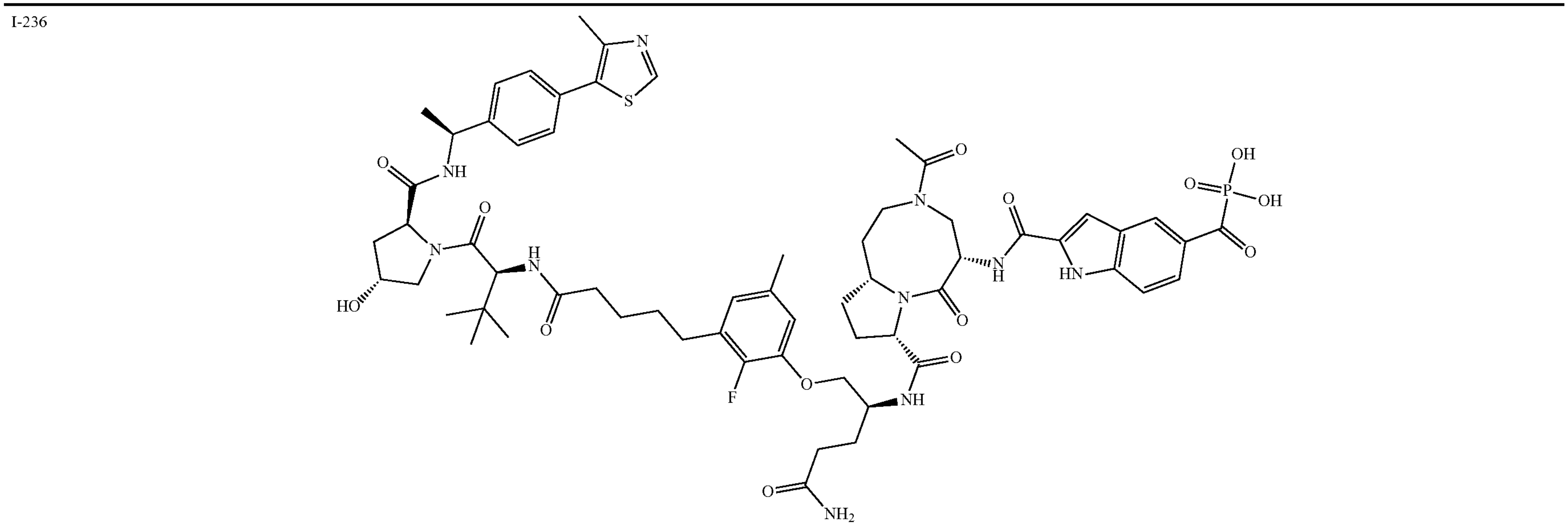 |
| I-237 | 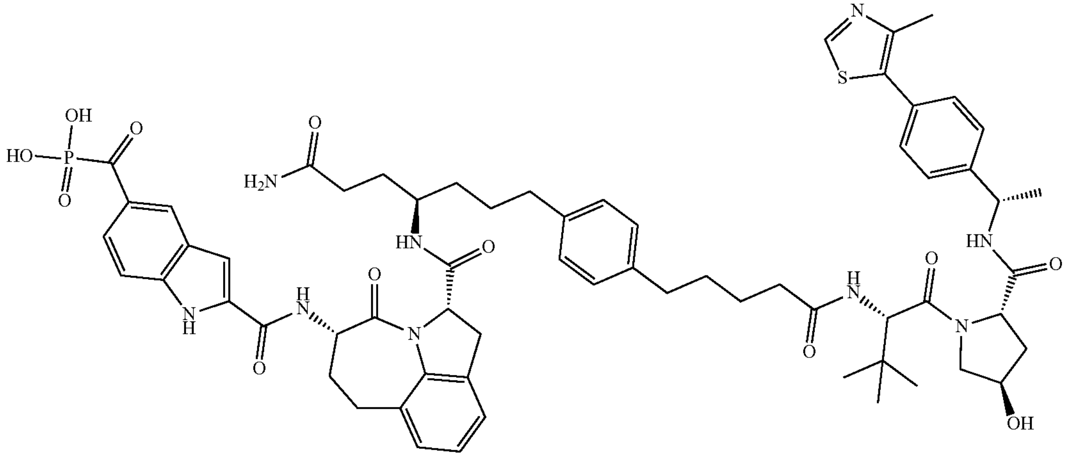 [SMILES: Cc1ncsc1-c1ccc([C@H](C)NC(=O)[C@@H]2C[C@@H](O)CN2C(=O)[C@@H](NC(=O)CCCCc2ccc(CCC[C@H](CCC(N)=O)NC(=O)[C@@H]3Cc4cccc5c4N3C(=O)[C@@H](NC(=O)c3cc4cc(C(=O)P(=O)(O)O)ccc4[nH]3)CC5)cc2)C(C)(C)C)cc1] |

TABLE 1-continued
| Exemplary Compounds | |
|---|---|
| I-# | Structure |
| I-238 | 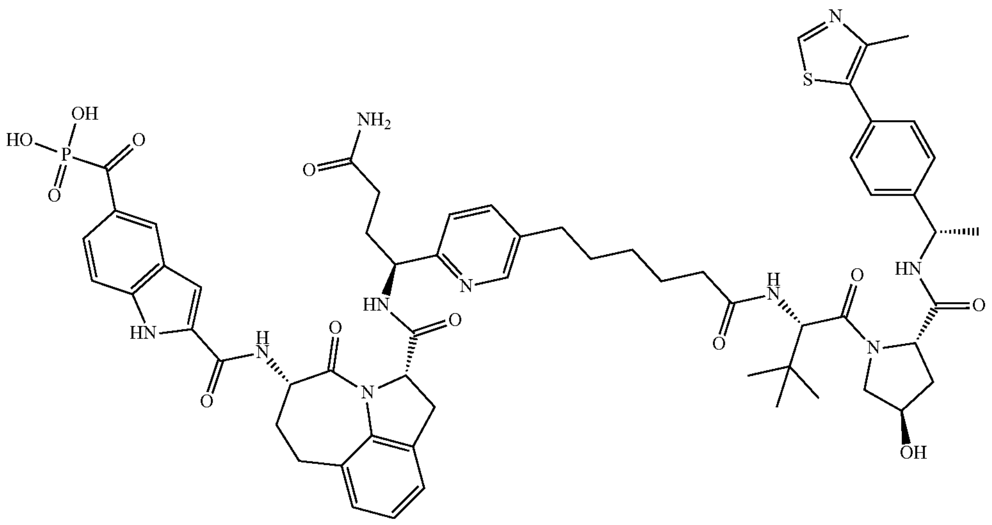 [SMILES: Cc1ncsc1-c1ccc([C@H](C)NC(=O)[C@@H]2C[C@@H](O)CN2C(=O)[C@@H](NC(=O)CCCCCc2ccc([C@H](CCC(N)=O)NC(=O)[C@@H]3Cc4cccc5c4N3C(=O)[C@@H](NC(=O)c3cc4cc(C(=O)P(=O)(O)O)ccc4[nH]3)CC5)nc2)C(C)(C)C)cc1] |

TABLE 1-continued
| Exemplary Compounds | |
|---|---|
| I-# | Structure |
| I-239 | 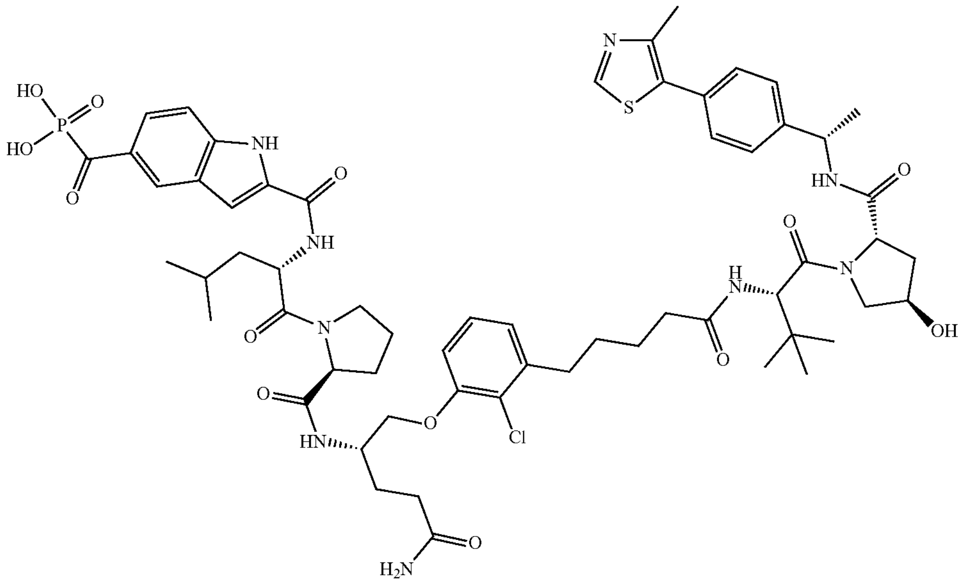 [SMILES: Cc1ncsc1-c1ccc([C@H](C)NC(=O)[C@@H]2C[C@@H](O)CN2C(=O)[C@@H](NC(=O)CCCCc2cccc(OC[C@H](CCC(N)=O)NC(=O)[C@@H]3CCCN3C(=O)[C@H](CC(C)C)NC(=O)c3cc4cc(C(=O)P(=O)(O)O)ccc4[nH]3)c2Cl)C(C)(C)C)cc1] |

TABLE 1-continued
| Exemplary Compounds | |
|---|---|
| I-# | Structure |
| I-240 | 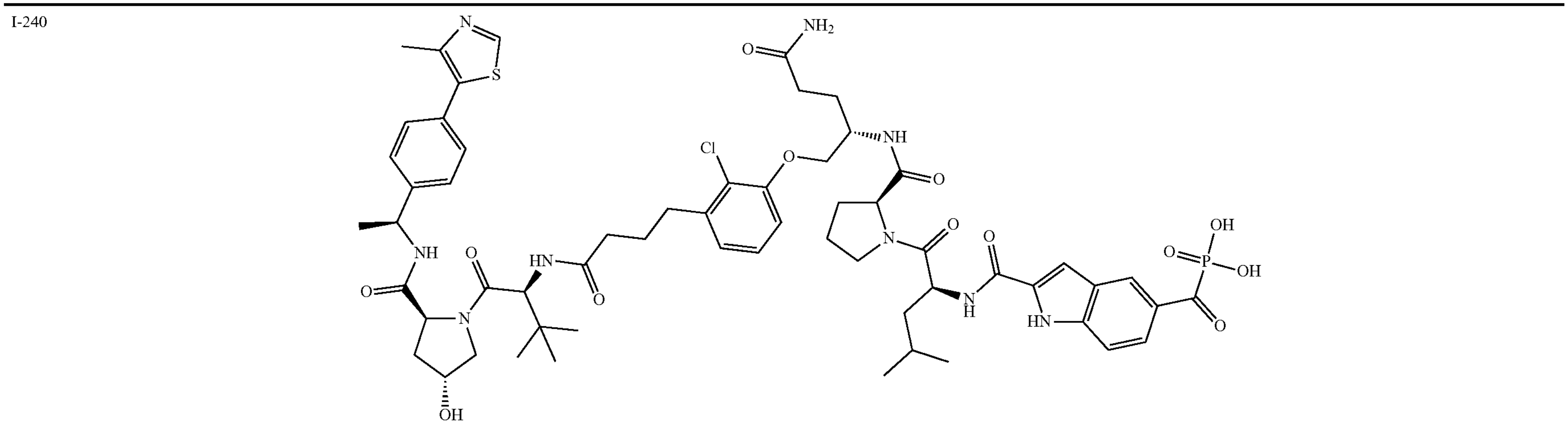 |
| I-241 | 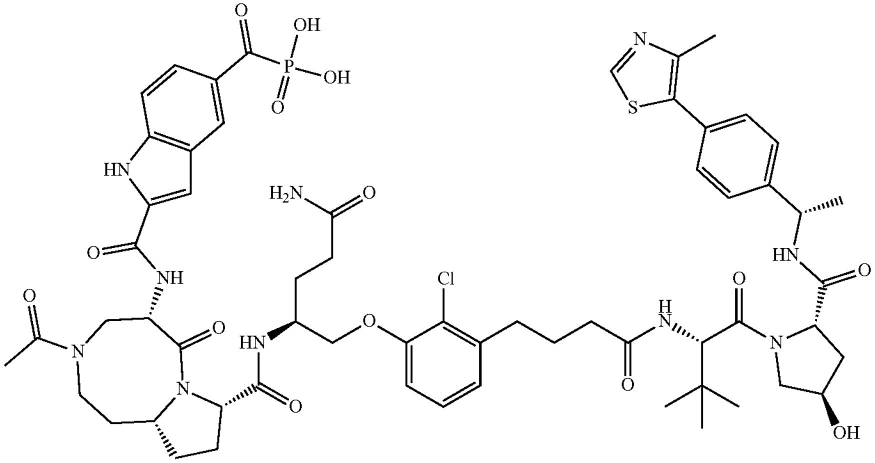 [SMILES: CC(=O)N1CC[C@H]2CC[C@@H](C(=O)N[C@@H](CCC(N)=O)COc3cccc(CCCC(=O)N[C@H](C(=O)N4C[C@H](O)C[C@H]4C(=O)N[C@@H](C)c4ccc(-c5scnc5C)cc4)C(C)(C)C)c3Cl)N2C(=O)[C@@H](NC(=O)c2cc3cc(C(=O)P(=O)(O)O)ccc3[nH]2)C1] |

TABLE 1-continued
| Exemplary Compounds | |
|---|---|
| I-# | Structure |
| I-242 | 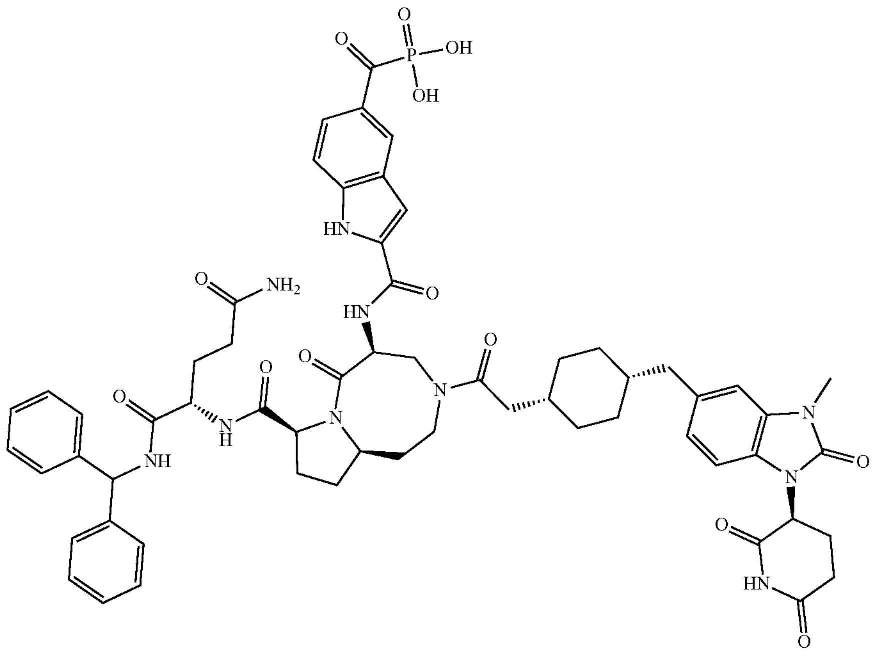 [SMILES: Cn1c(=O)n([C@H]2CCC(=O)NC2=O)c2ccc(C[C@H]3CC[C@@H](CC(=O)N4CC[C@H]5CC[C@@H](C(=O)N[C@@H](CCC(N)=O)C(=O)NC(c6ccccc6)c6ccccc6)N5C(=O)[C@@H](NC(=O)c5cc6cc(C(=O)P(=O)(O)O)ccc6[nH]5)C4)CC3)cc21] |

TABLE 1-continued
| Exemplary Compounds | |
|---|---|
| I-# | Structure |
| I-243 | 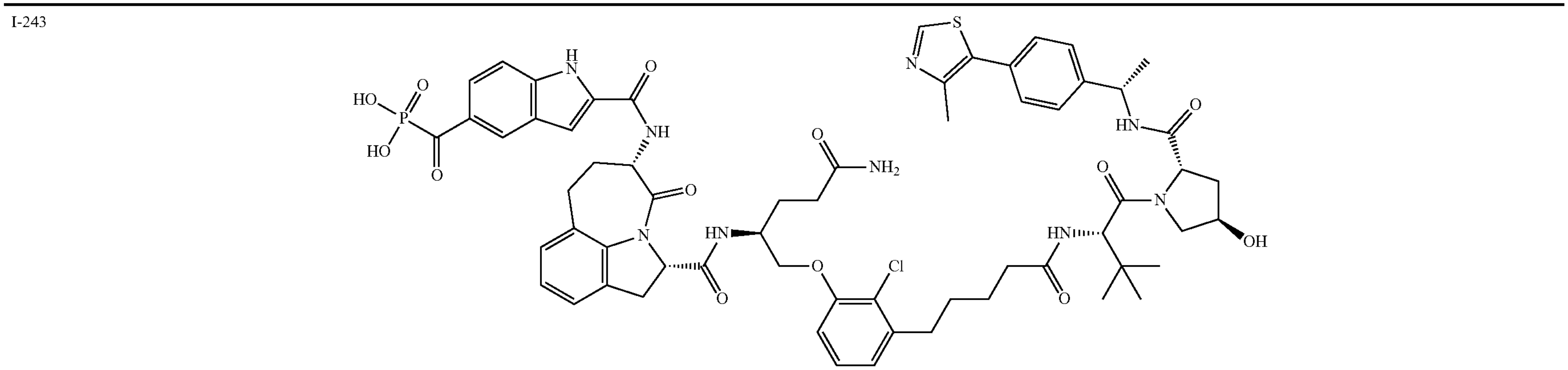 |
| I-244 | 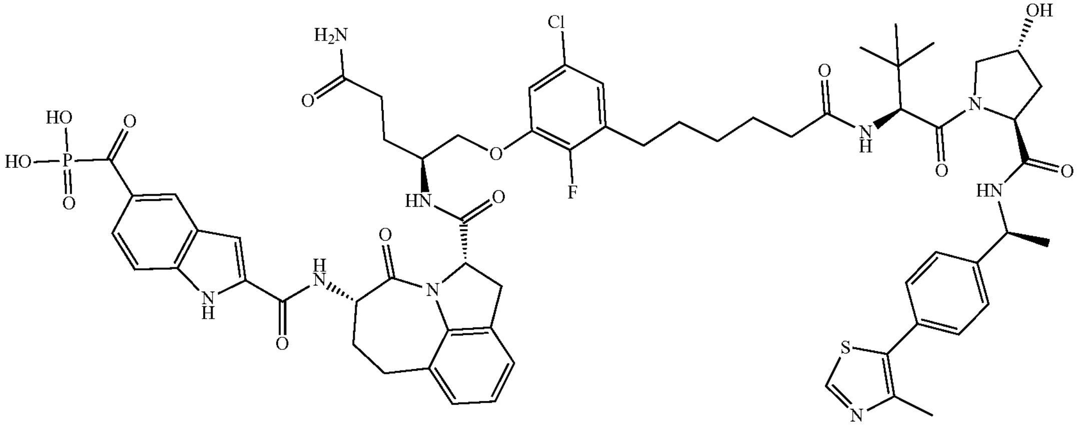 [SMILES: Cc1ncsc1-c1ccc([C@H](C)NC(=O)[C@@H]2C[C@@H](O)CN2C(=O)[C@@H](NC(=O)CCCCCc2cc(Cl)cc(OC[C@H](CCC(N)=O)NC(=O)[C@@H]3Cc4cccc5c4N3C(=O)[C@@H](NC(=O)c3cc4cc(C(=O)P(=O)(O)O)ccc4[nH]3)CC5)c2F)C(C)(C)C)cc1] |

TABLE 1-continued
| Exemplary Compounds | |
|---|---|
| I-# | Structure |
| I-245 | 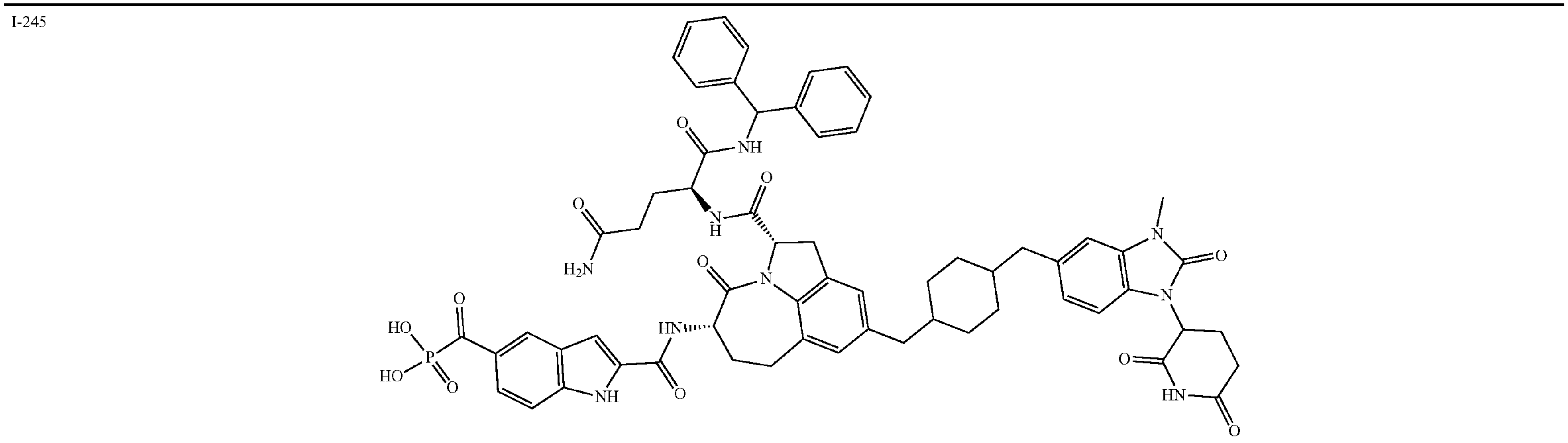 |
| I-246 | 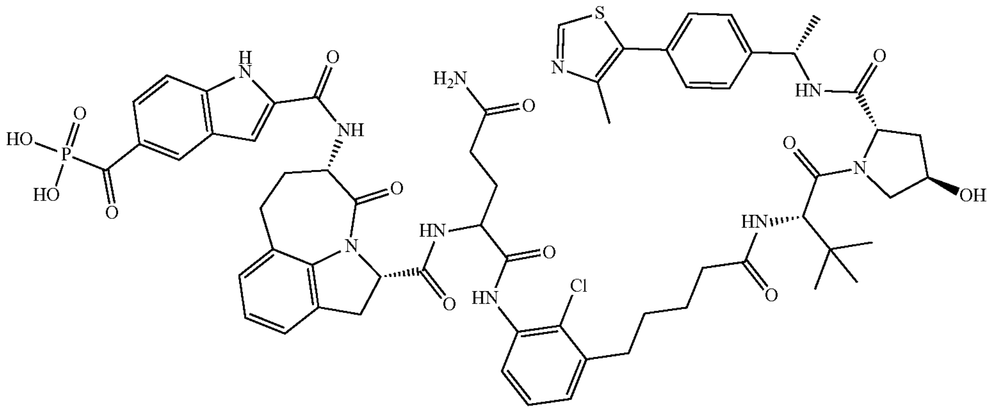 [SMILES: Cc1ncsc1-c1ccc([C@H](C)NC(=O)[C@@H]2C[C@@H](O)CN2C(=O)[C@@H](NC(=O)CCCCc2cccc(NC(=O)C(CCC(N)=O)NC(=O)[C@@H]3Cc4cccc5c4N3C(=O)[C@@H](NC(=O)c3cc4cc(C(=O)P(=O)(O)O)ccc4[nH]3)CC5)c2Cl)C(C)(C)C)cc1] |

TABLE 1-continued
| Exemplary Compounds | |
|---|---|
| I-# | Structure |
| I-247 | 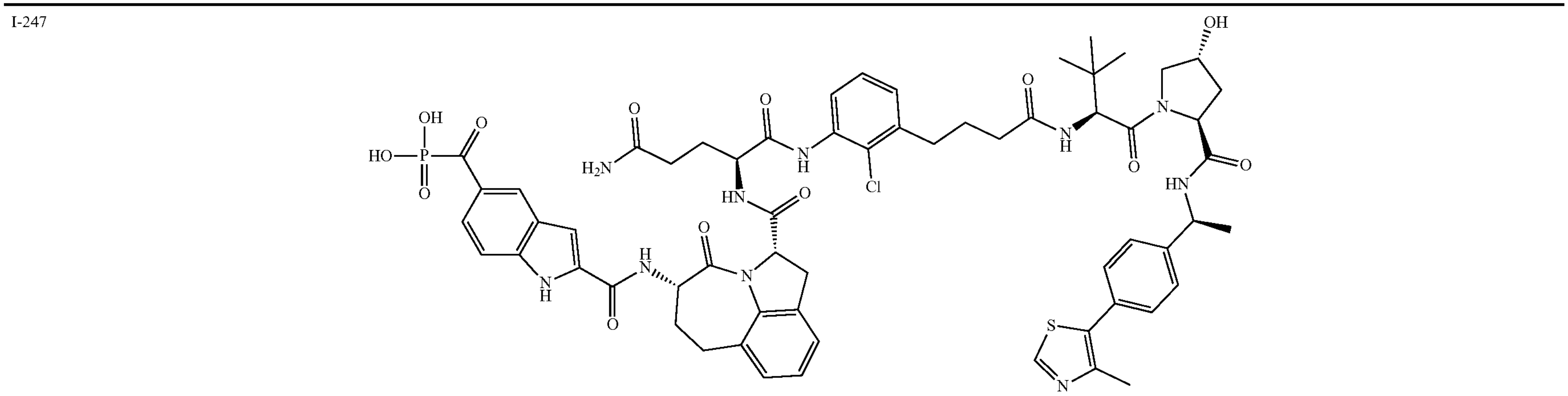 |
| I-248 | 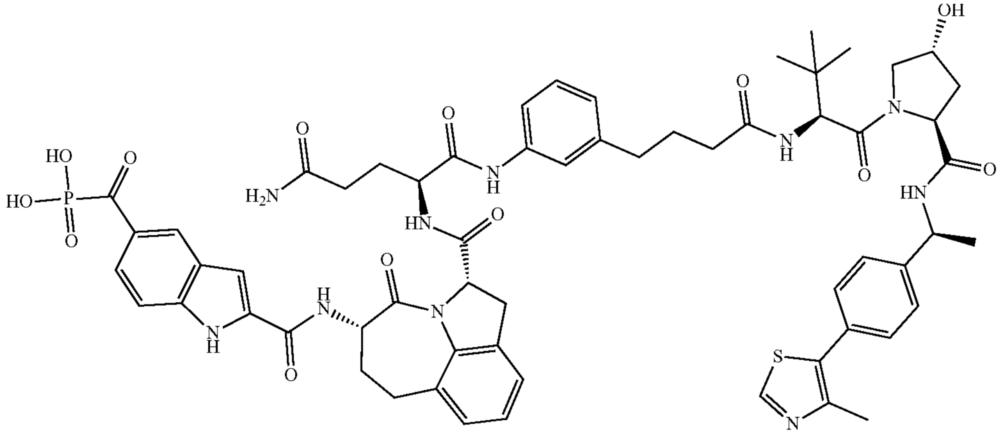 [SMILES: Cc1ncsc1-c1ccc([C@H](C)NC(=O)[C@@H]2C[C@@H](O)CN2C(=O)[C@@H](NC(=O)CCCc2cccc(NC(=O)[C@H](CCC(N)=O)NC(=O)[C@@H]3Cc4cccc5c4N3C(=O)[C@@H](NC(=O)c3cc4cc(C(=O)P(=O)(O)O)ccc4[nH]3)CC5)c2)C(C)(C)C)cc1] |

TABLE 1-continued
| Exemplary Compounds | |
|---|---|
| I-# | Structure |
| I-249 | 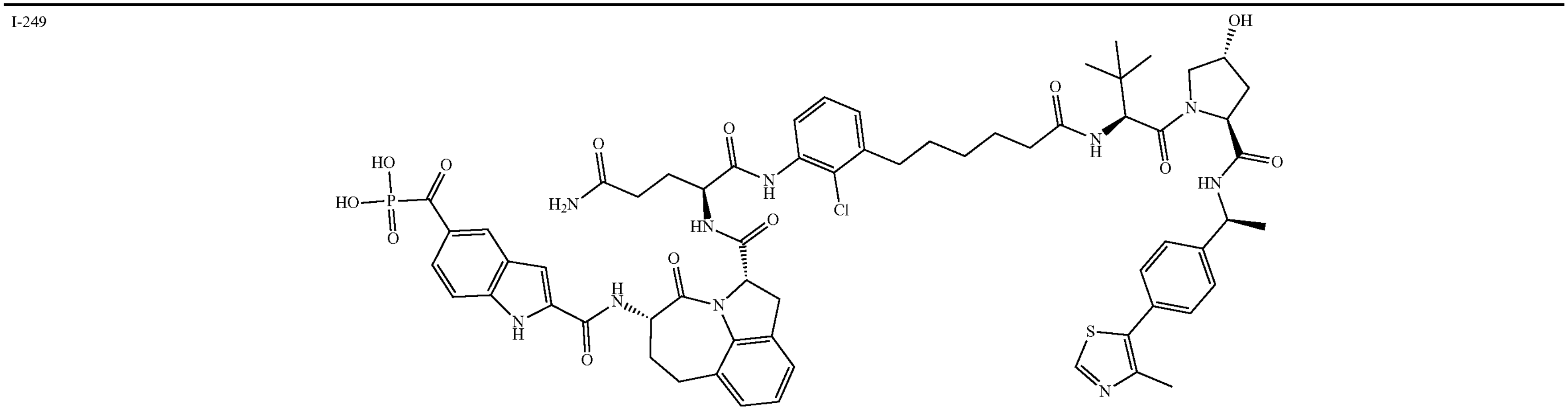 |
| I-250 | 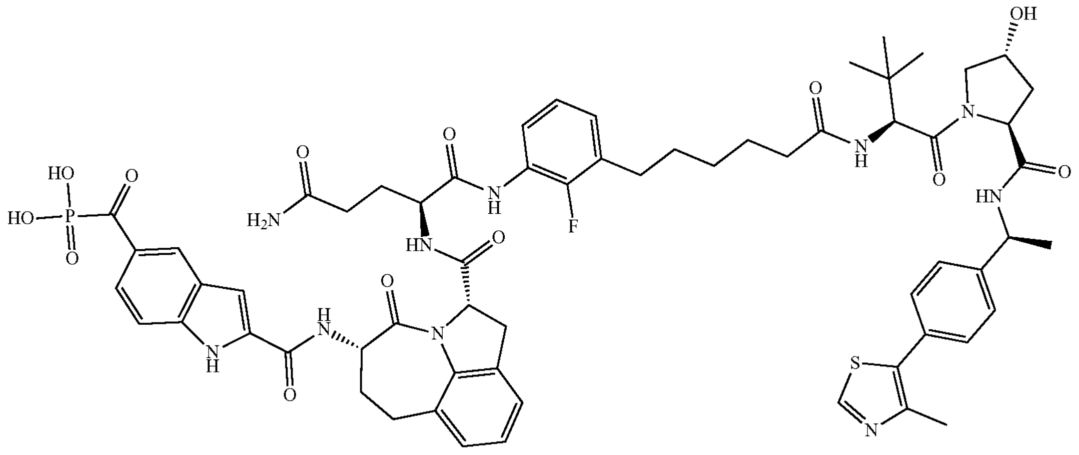 [SMILES: Cc1ncsc1-c1ccc([C@H](C)NC(=O)[C@@H]2C[C@@H](O)CN2C(=O)[C@@H](NC(=O)CCCCCc2cccc(NC(=O)[C@H](CCC(N)=O)NC(=O)[C@@H]3Cc4cccc5c4N3C(=O)[C@@H](NC(=O)c3cc4cc(C(=O)P(=O)(O)O)ccc4[nH]3)CC5)c2F)C(C)(C)C)cc1] |

TABLE 1-continued
| Exemplary Compounds | |
|---|---|
| I-# | Structure |
| I-251 | 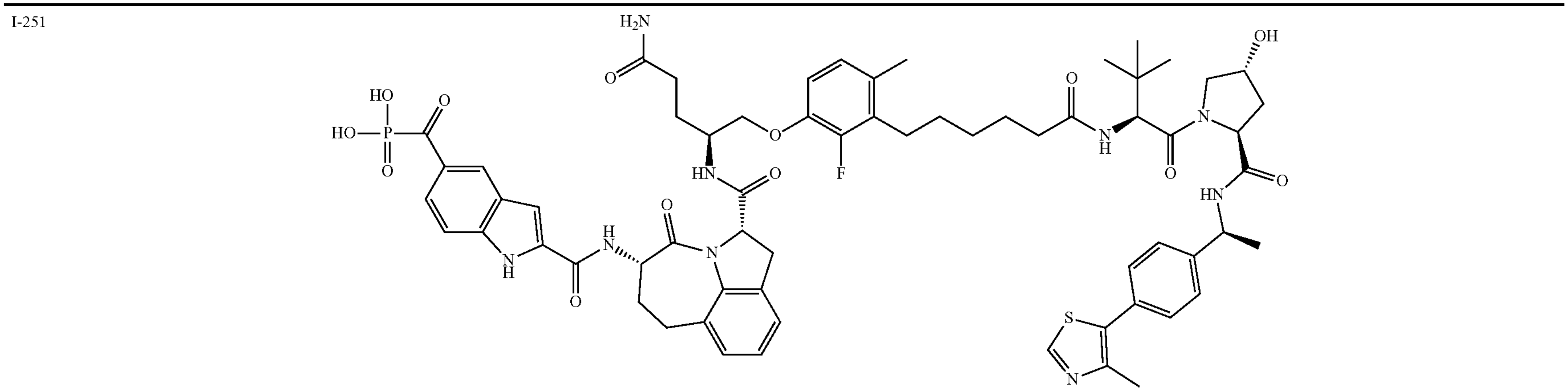 |
| I-252 | 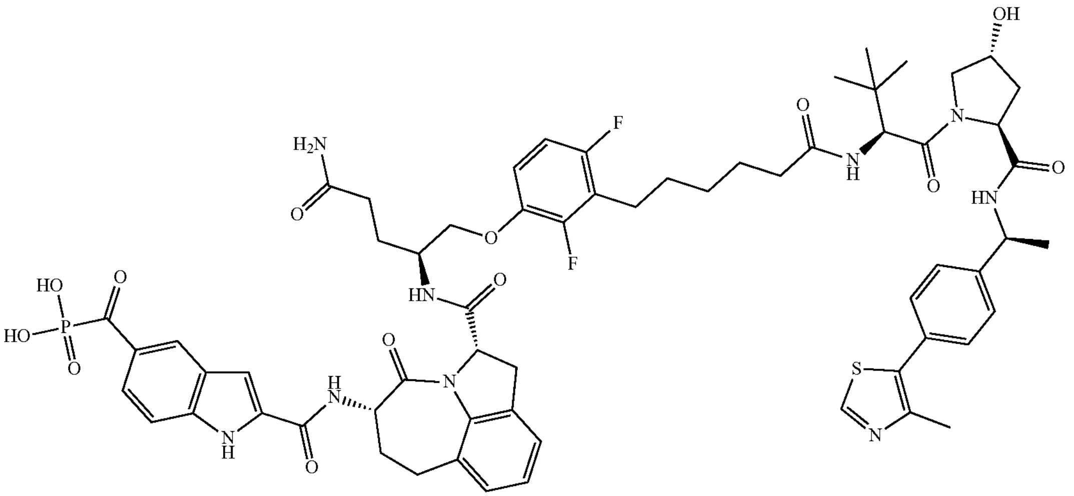 [SMILES: Cc1ncsc1-c1ccc([C@H](C)NC(=O)[C@@H]2C[C@@H](O)CN2C(=O)[C@@H](NC(=O)CCCCCc2c(F)ccc(OC[C@H](CCC(N)=O)NC(=O)[C@@H]3Cc4cccc5c4N3C(=O)[C@@H](NC(=O)c3cc4cc(C(=O)P(=O)(O)O)ccc4[nH]3)CC5)c2F)C(C)(C)C)cc1] |

TABLE 1-continued
| Exemplary Compounds | |
|---|---|
| I-# | Structure |
| I-253 | 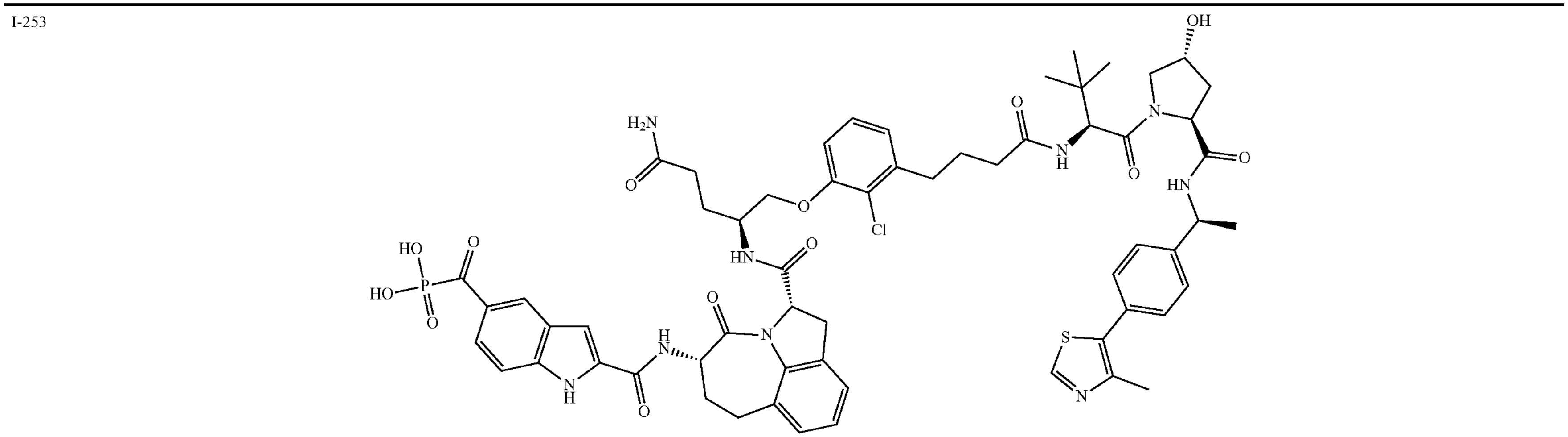 |
| I-254 | 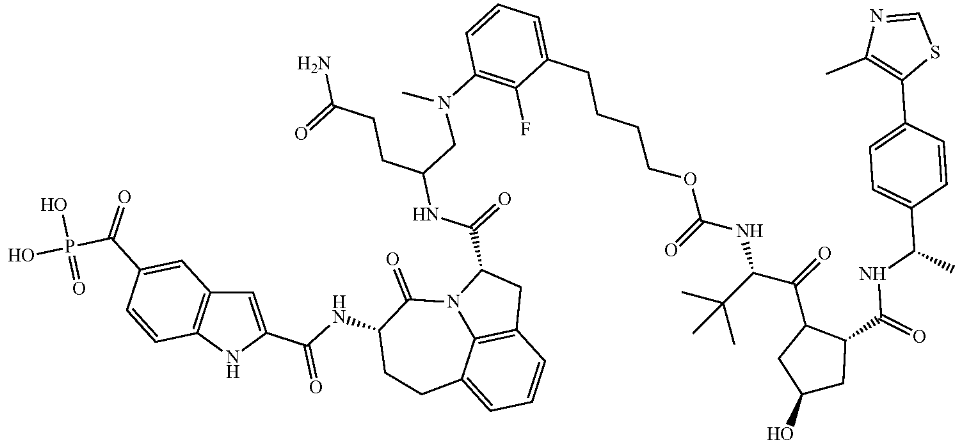 [SMILES: Cc1ncsc1-c1ccc([C@H](C)NC(=O)[C@@H]2C[C@@H](O)CC2C(=O)[C@@H](NC(=O)OCCCCc2cccc(N(C)CC(CCC(N)=O)NC(=O)[C@@H]3Cc4cccc5c4N3C(=O)[C@@H](NC(=O)c3cc4cc(C(=O)P(=O)(O)O)ccc4[nH]3)CC5)c2F)C(C)(C)C)cc1] |

TABLE 1-continued
| Exemplary Compounds | |
|---|---|
| I-# | Structure |
| I-255 | 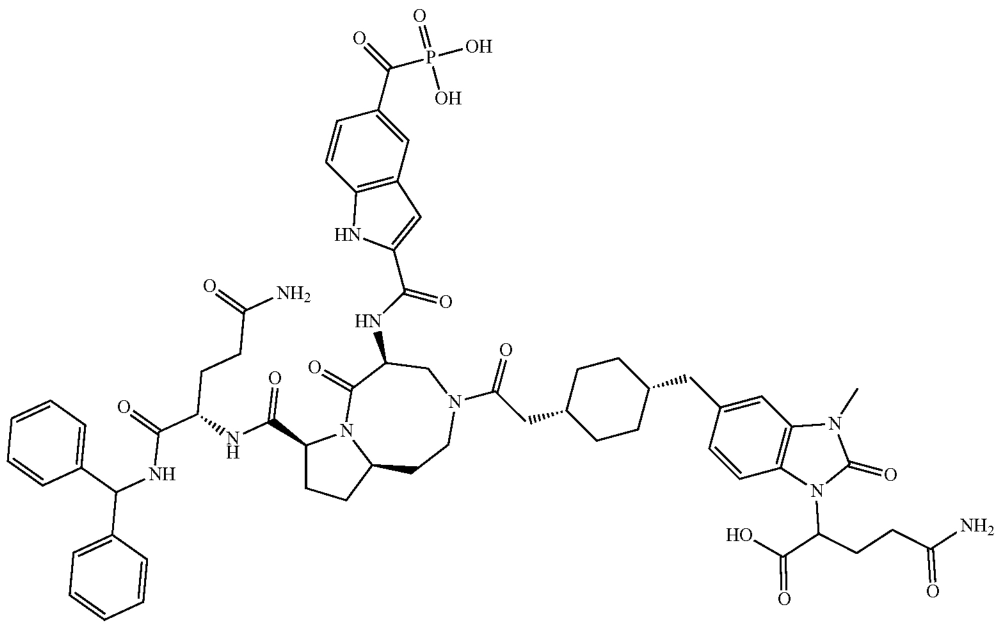 [SMILES: Cn1c(=O)n(C(CCC(N)=O)C(=O)O)c2ccc(C[C@H]3CC[C@@H](CC(=O)N4CC[C@H]5CC[C@@H](C(=O)N[C@@H](CCC(N)=O)C(=O)NC(c6ccccc6)c6ccccc6)N5C(=O)[C@@H](NC(=O)c5cc6cc(C(=O)P(=O)(O)O)ccc6[nH]5)C4)CC3)cc21] |

TABLE 1-continued
| Exemplary Compounds | |
|---|---|
| I-# | Structure |
| I-256 | 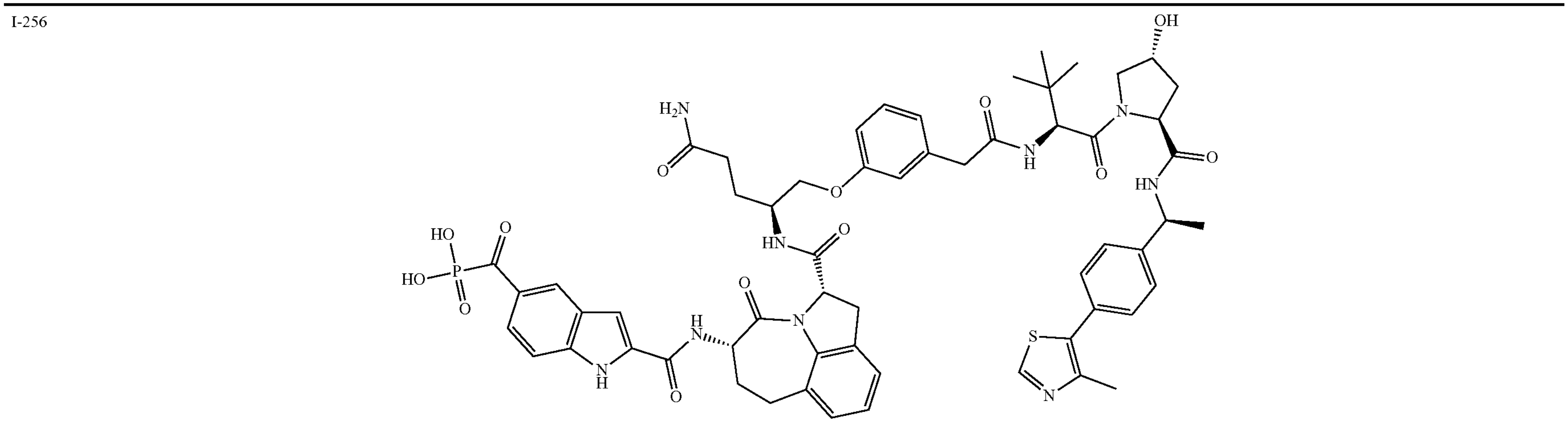 |
| I-257 | 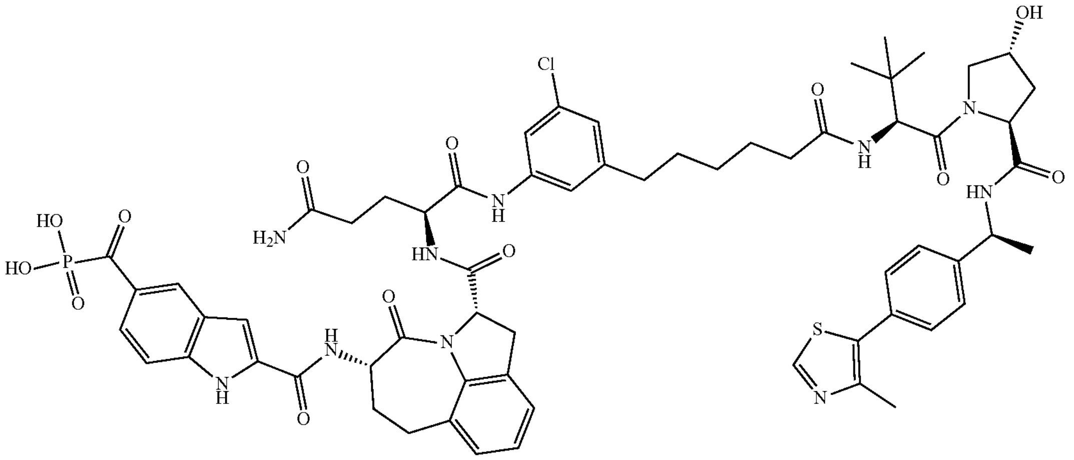 [SMILES: Cc1ncsc1-c1ccc([C@H](C)NC(=O)[C@@H]2C[C@@H](O)CN2C(=O)[C@@H](NC(=O)CCCCCc2cc(Cl)cc(NC(=O)[C@H](CCC(N)=O)NC(=O)[C@@H]3Cc4cccc5c4N3C(=O)[C@@H](NC(=O)c3cc4cc(C(=O)P(=O)(O)O)ccc4[nH]3)CC5)c2)C(C)(C)C)cc1] |

TABLE 1-continued
| Exemplary Compounds | |
|---|---|
| I-# | Structure |
| I-258 | 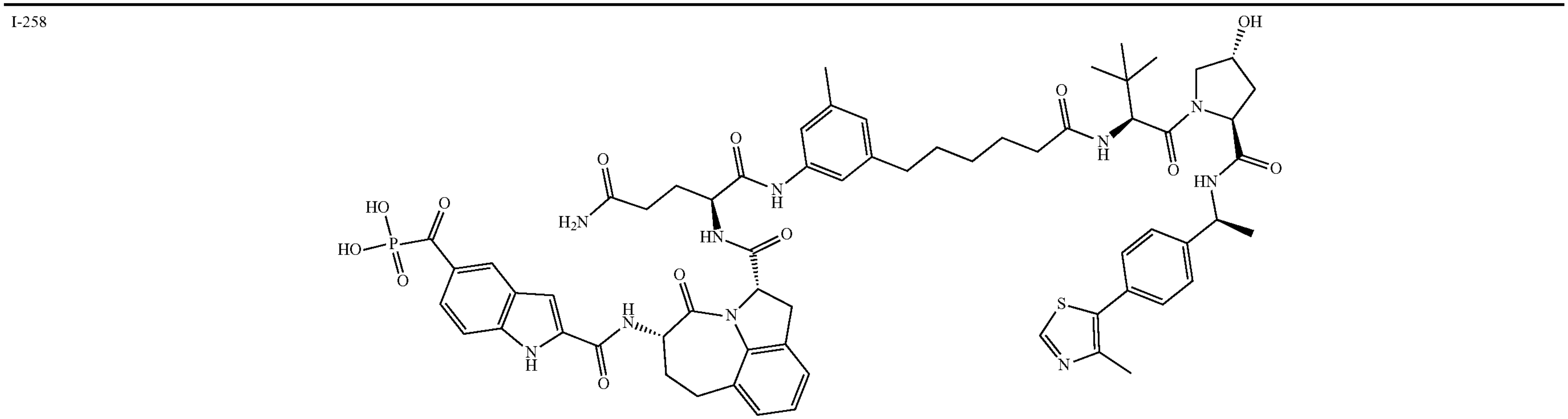 |
| I-259 | 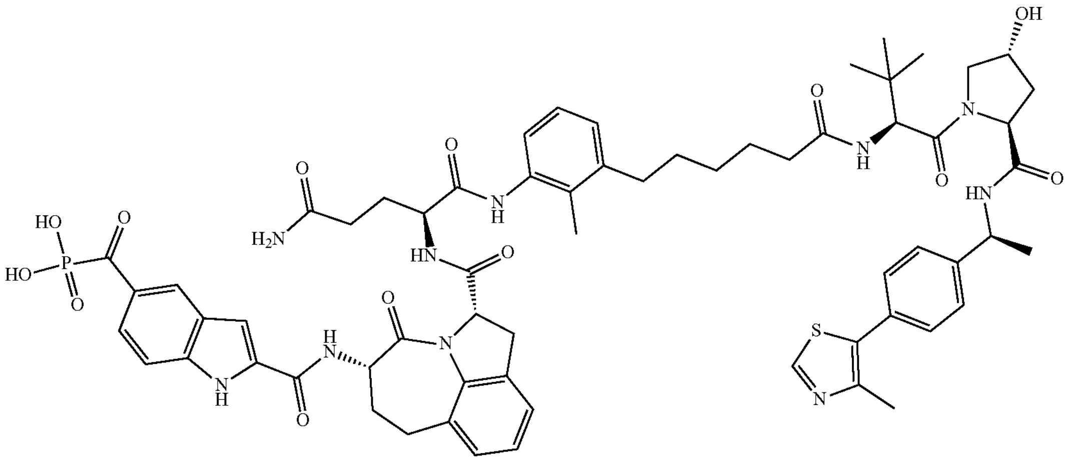 [SMILES: Cc1ncsc1-c1ccc([C@H](C)NC(=O)[C@@H]2C[C@@H](O)CN2C(=O)[C@@H](NC(=O)CCCCCc2cccc(NC(=O)[C@H](CCC(N)=O)NC(=O)[C@@H]3Cc4cccc5c4N3C(=O)[C@@H](NC(=O)c3cc4cc(C(=O)P(=O)(O)O)ccc4[nH]3)CC5)c2C)C(C)(C)C)cc1] |

TABLE 1-continued
| Exemplary Compounds | |
|---|---|
| I-# | Structure |
| I-260 | 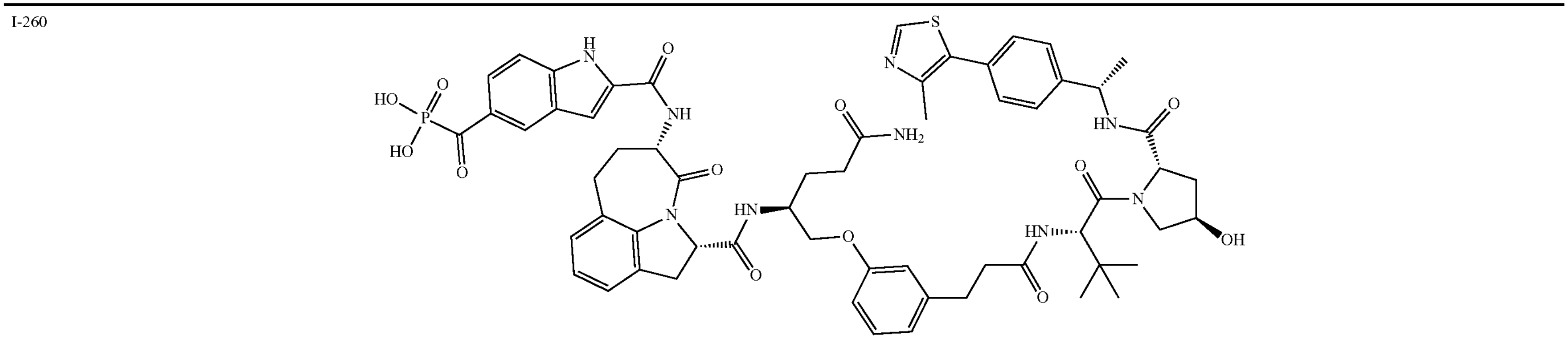 |
| I-261 | 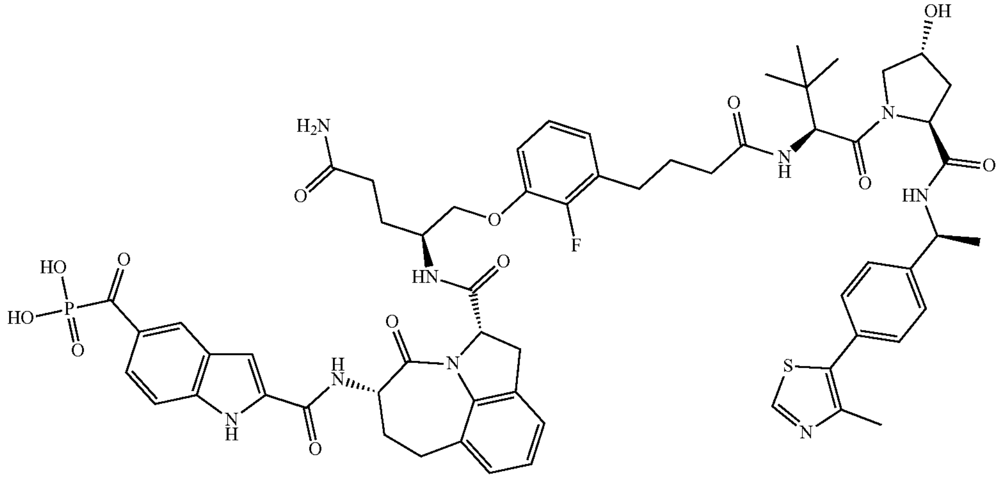 [SMILES: Cc1ncsc1-c1ccc([C@H](C)NC(=O)[C@@H]2C[C@@H](O)CN2C(=O)[C@@H](NC(=O)CCCc2cccc(OC[C@H](CCC(N)=O)NC(=O)[C@@H]3Cc4cccc5c4N3C(=O)[C@@H](NC(=O)c3cc4cc(C(=O)P(=O)(O)O)ccc4[nH]3)CC5)c2F)C(C)(C)C)cc1] |

TABLE 1-continued
| Exemplary Compounds | |
|---|---|
| I-# | Structure |
| I-262 | 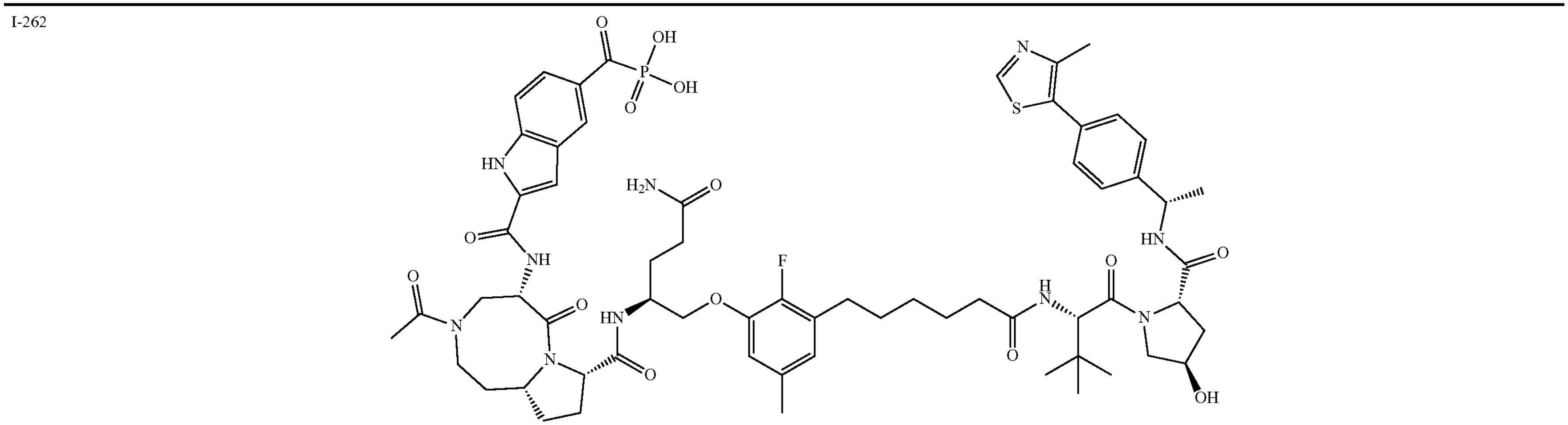 |
| I-263 | 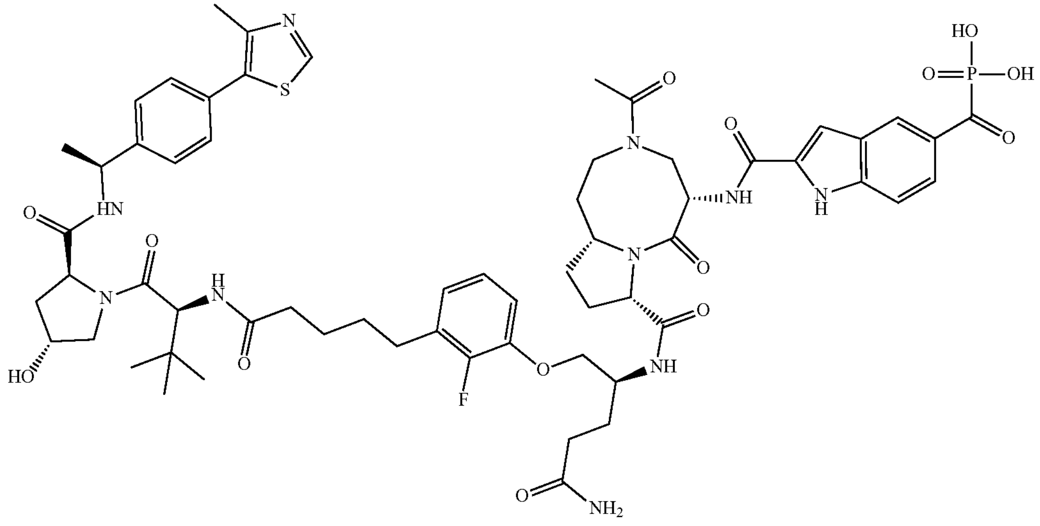 [SMILES: CC(=O)N1CC[C@H]2CC[C@@H](C(=O)N[C@@H](CCC(N)=O)COc3cccc(CCCCC(=O)N[C@H](C(=O)N4C[C@H](O)C[C@H]4C(=O)N[C@@H](C)c4ccc(-c5scnc5C)cc4)C(C)(C)C)c3F)N2C(=O)[C@@H](NC(=O)c2cc3cc(C(=O)P(=O)(O)O)ccc3[nH]2)C1] |

TABLE 1-continued
| Exemplary Compounds | |
|---|---|
| I-# | Structure |
| I-264 | 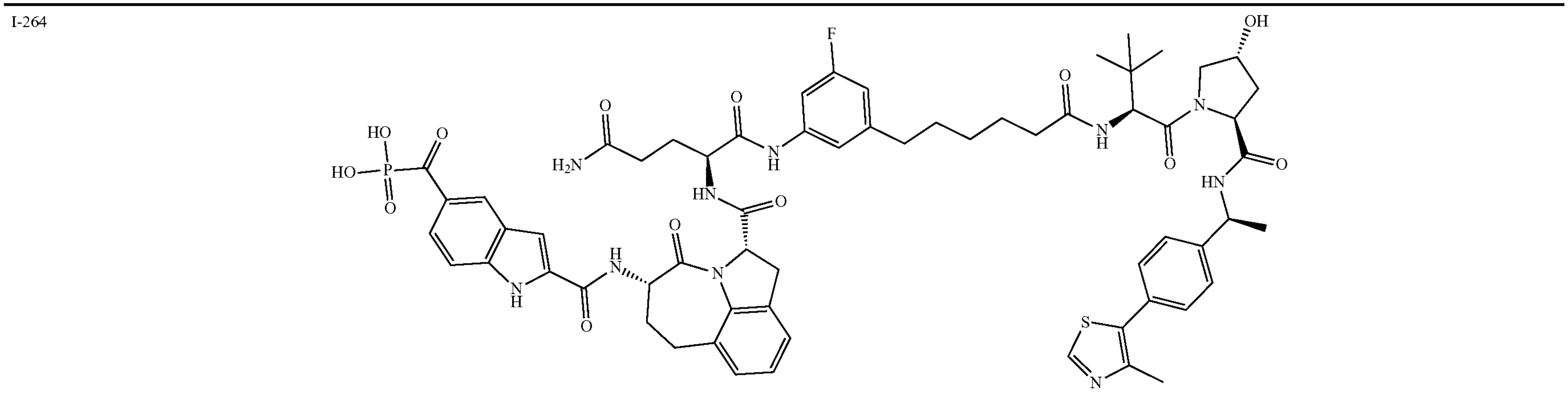 |
| I-265 | 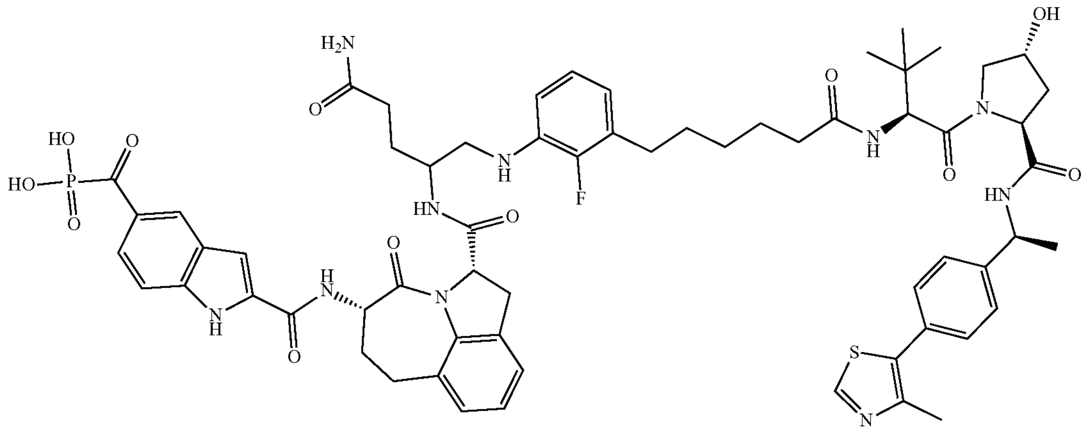 [SMILES: Cc1ncsc1-c1ccc([C@H](C)NC(=O)[C@@H]2C[C@@H](O)CN2C(=O)[C@@H](NC(=O)CCCCCc2cccc(NCC(CCC(N)=O)NC(=O)[C@@H]3Cc4cccc5c4N3C(=O)[C@@H](NC(=O)c3cc4cc(C(=O)P(=O)(O)O)ccc4[nH]3)CC5)c2F)C(C)(C)C)cc1] |

TABLE 1-continued
| Exemplary Compounds | |
|---|---|
| I-# | Structure |
| I-266 | 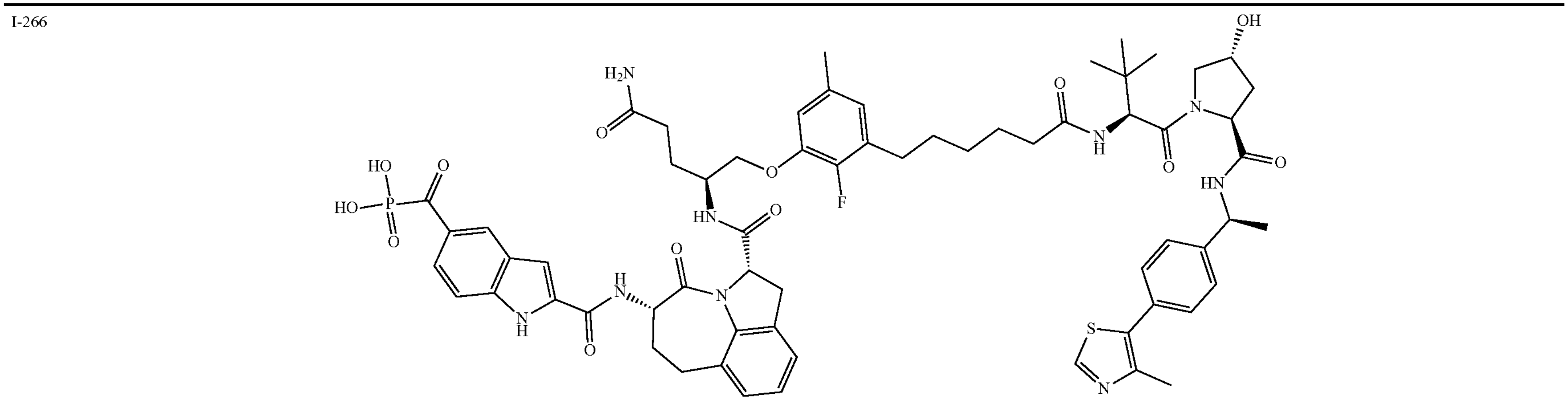 |
| I-267 | 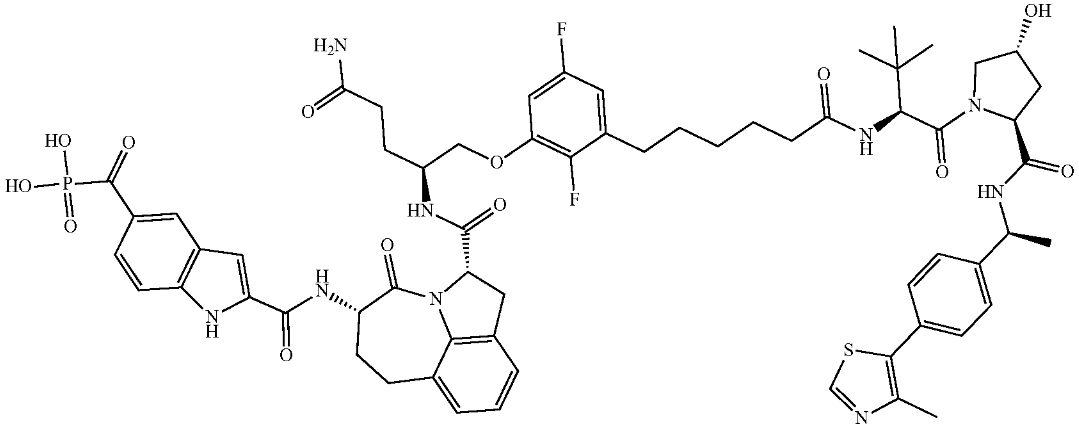 [SMILES: Cc1ncsc1-c1ccc([C@H](C)NC(=O)[C@@H]2C[C@@H](O)CN2C(=O)[C@@H](NC(=O)CCCCCc2cc(F)cc(OC[C@H](CCC(N)=O)NC(=O)[C@@H]3Cc4cccc5c4N3C(=O)[C@@H](NC(=O)c3cc4cc(C(=O)P(=O)(O)O)ccc4[nH]3)CC5)c2F)C(C)(C)C)cc1] |

TABLE 1-continued
| Exemplary Compounds | |
|---|---|
| I-# | Structure |
| I-268 | 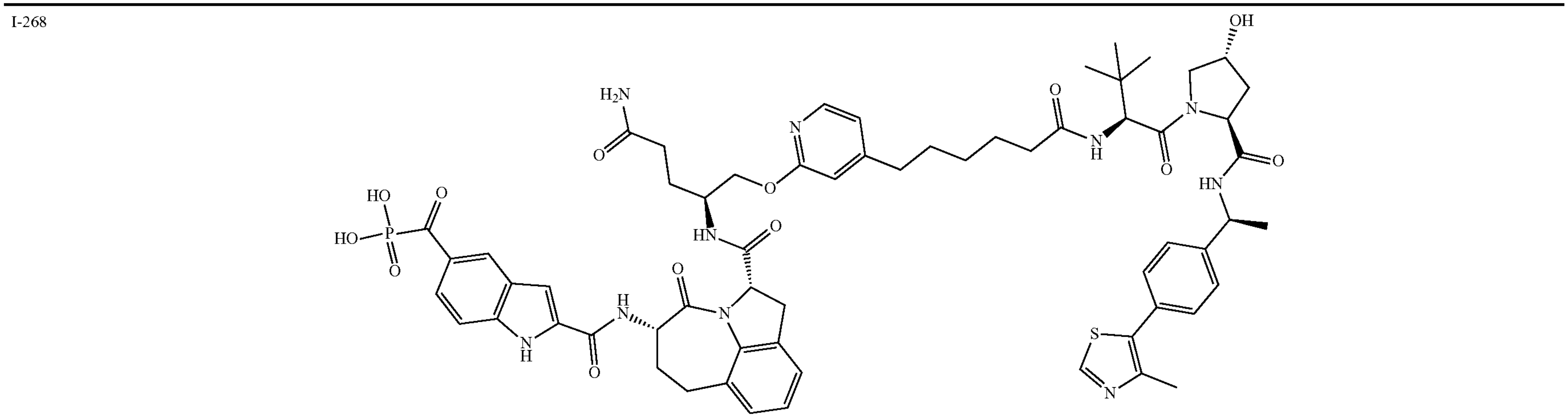 |
| I-269 | 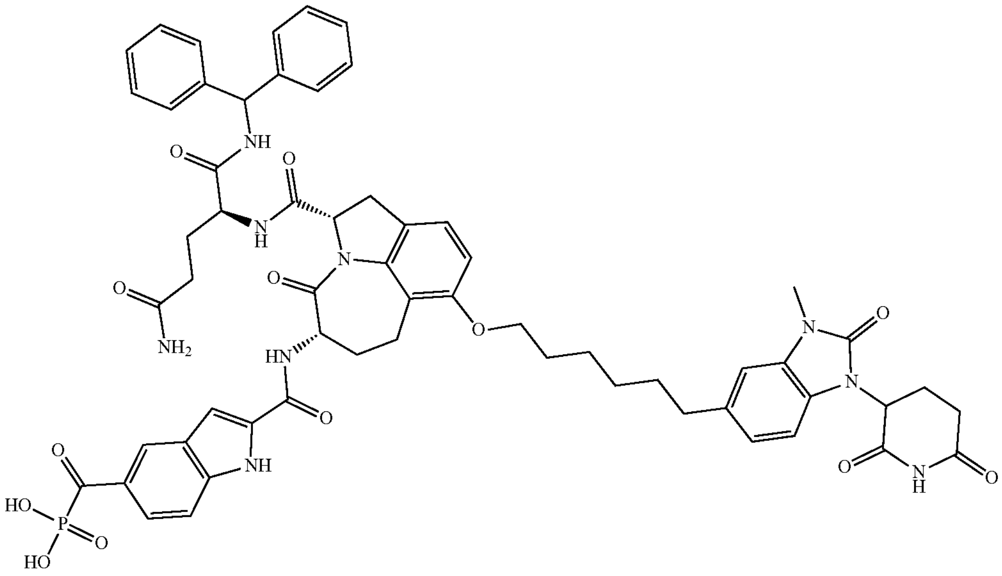 [SMILES: Cn1c(=O)n(C2CCC(=O)NC2=O)c2ccc(CCCCCCOc3ccc4c5c3CC[C@H](NC(=O)c3cc6cc(C(=O)P(=O)(O)O)ccc6[nH]3)C(=O)N5[C@H](C(=O)N[C@@H](CCC(N)=O)C(=O)NC(c3ccccc3)c3ccccc3)C4)cc21] |

TABLE 1-continued
| Exemplary Compounds | |
|---|---|
| I-# | Structure |
| I-270 | 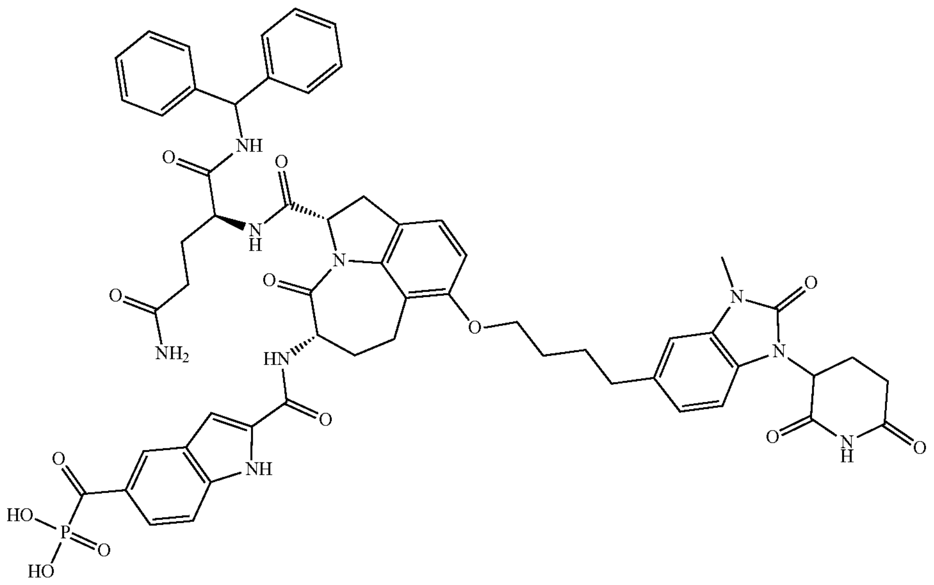 [SMILES: Cn1c(=O)n(C2CCC(=O)NC2=O)c2ccc(CCCCOc3ccc4c5c3CC[C@H](NC(=O)c3cc6cc(C(=O)P(=O)(O)O)ccc6[nH]3)C(=O)N5[C@H](C(=O)N[C@@H](CCC(N)=O)C(=O)NC(c3ccccc3)c3ccccc3)C4)cc21] |

TABLE 1-continued
| Exemplary Compounds | |
|---|---|
| I-# | Structure |
| I-271 | 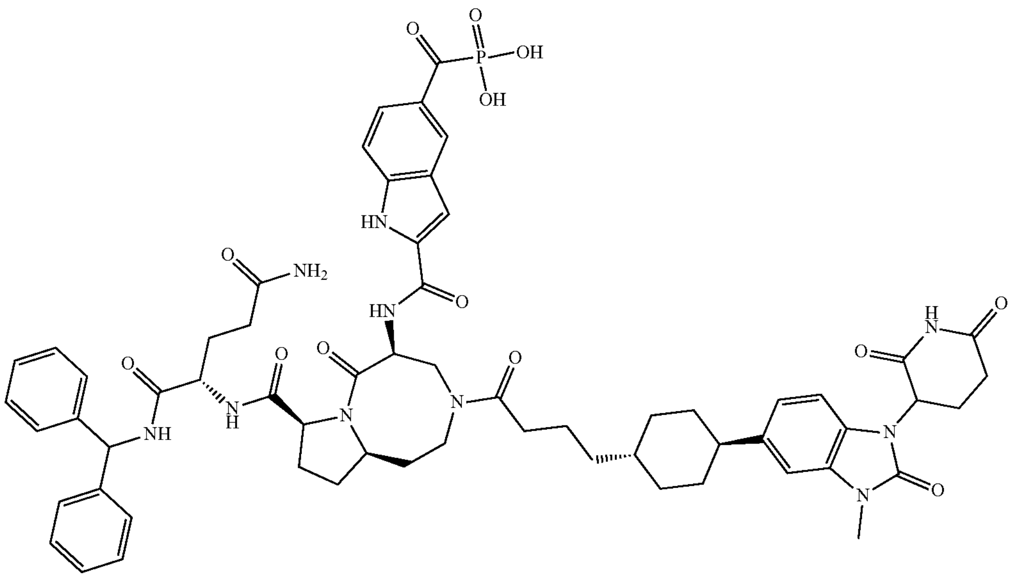 [SMILES: Cn1c(=O)n(C2CCC(=O)NC2=O)c2ccc([C@H]3CC[C@H](CCCC(=O)N4CC[C@H]5CC[C@@H](C(=O)N[C@@H](CCC(N)=O)C(=O)NC(c6ccccc6)c6ccccc6)N5C(=O)[C@@H](NC(=O)c5cc6cc(C(=O)P(=O)(O)O)ccc6[nH]5)C4)CC3)cc21] |

TABLE 1-continued
| Exemplary Compounds | |
|---|---|
| I-# | Structure |
| I-272 | 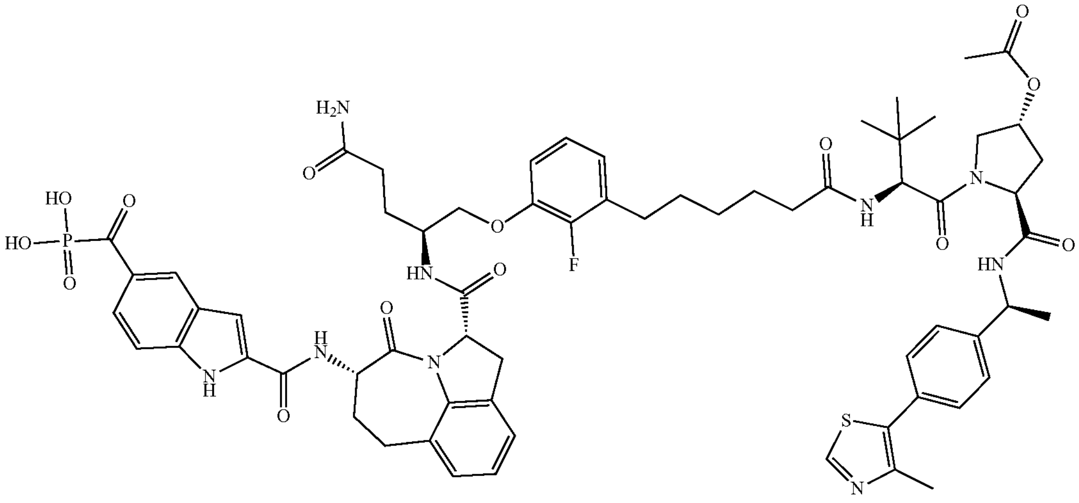 [SMILES: CC(=O)O[C@@H]1C[C@@H](C(=O)N[C@@H](C)c2ccc(-c3scnc3C)cc2)N(C(=O)[C@@H](NC(=O)CCCCCc2cccc(OC[C@H](CCC(N)=O)NC(=O)[C@@H]3Cc4cccc5c4N3C(=O)[C@@H](NC(=O)c3cc4cc(C(=O)P(=O)(O)O)ccc4[nH]3)CC5)c2F)C(C)(C)C)C1] |

TABLE 1-continued
| Exemplary Compounds | |
|---|---|
| I-# | Structure |
| I-273 | 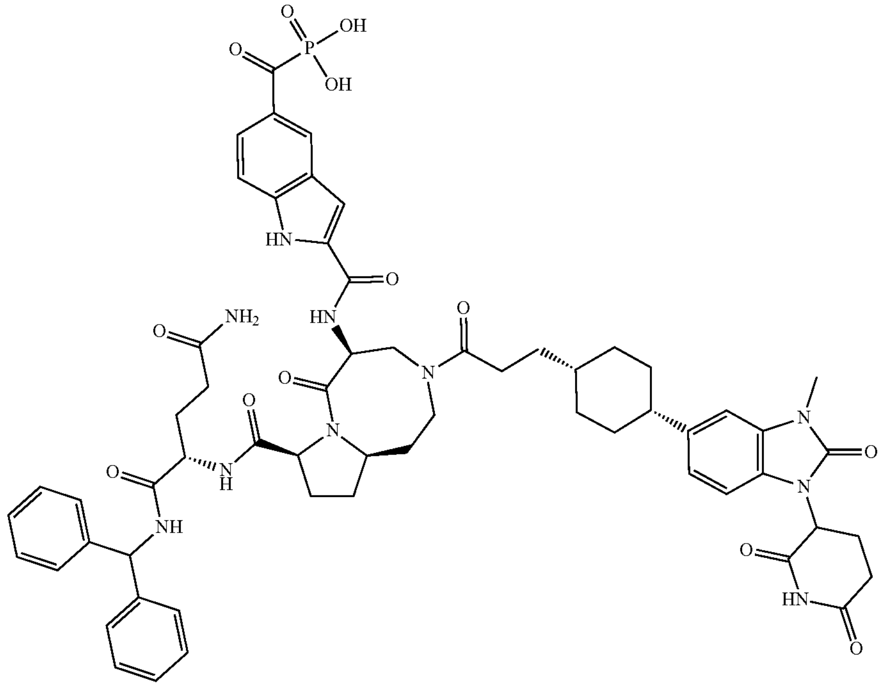 [SMILES: Cn1c(=O)n(C2CCC(=O)NC2=O)c2ccc([C@H]3CC[C@@H](CCC(=O)N4CC[C@H]5CC[C@@H](C(=O)N[C@@H](CCC(N)=O)C(=O)NC(c6ccccc6)c6ccccc6)N5C(=O)[C@@H](NC(=O)c5cc6cc(C(=O)P(=O)(O)O)ccc6[nH]5)C4)CC3)cc21] |

TABLE 1-continued
| Exemplary Compounds | |
|---|---|
| I-# | Structure |
| I-274 | 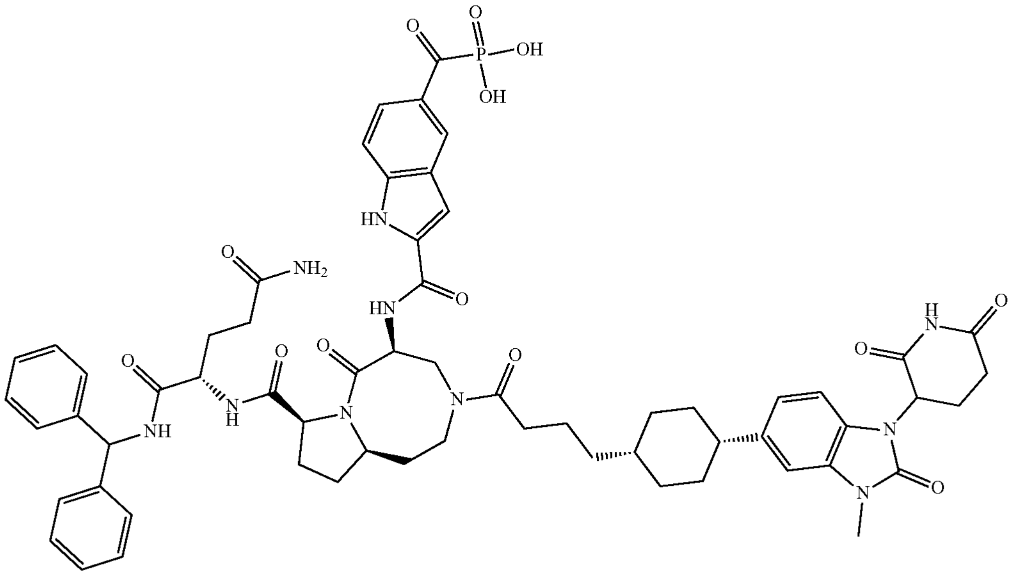 [SMILES: Cn1c(=O)n(C2CCC(=O)NC2=O)c2ccc([C@H]3CC[C@@H](CCCC(=O)N4CC[C@H]5CC[C@@H](C(=O)N[C@@H](CCC(N)=O)C(=O)NC(c6ccccc6)c6ccccc6)N5C(=O)[C@@H](NC(=O)c5cc6cc(C(=O)P(=O)(O)O)ccc6[nH]5)C4)CC3)cc21] |

TABLE 1-continued
| Exemplary Compounds | |
|---|---|
| I-# | Structure |
| I-275 | 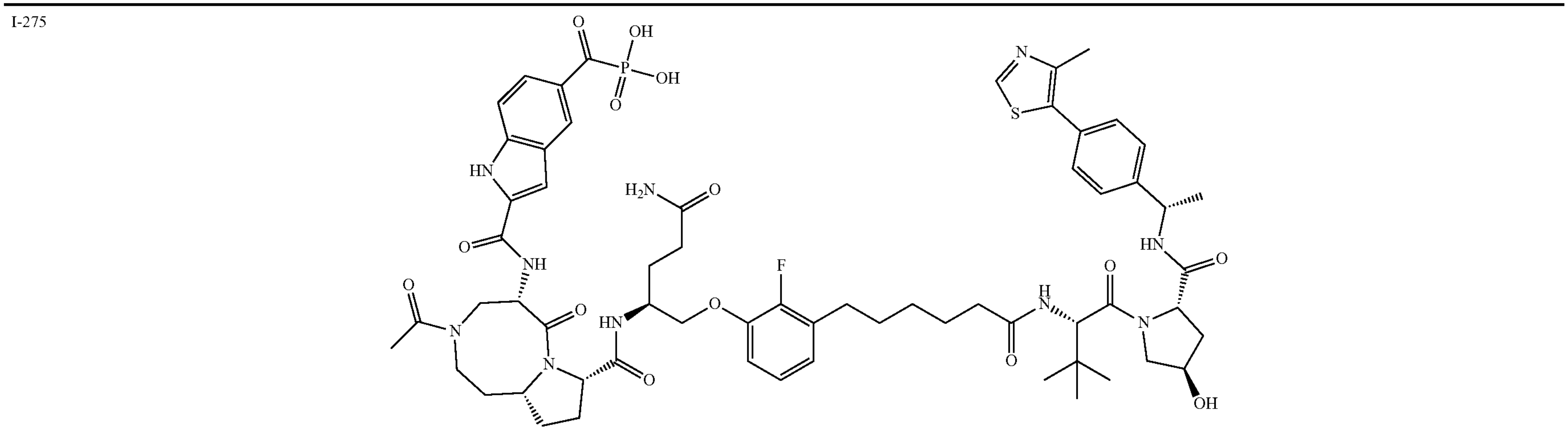 |
| I-276 | 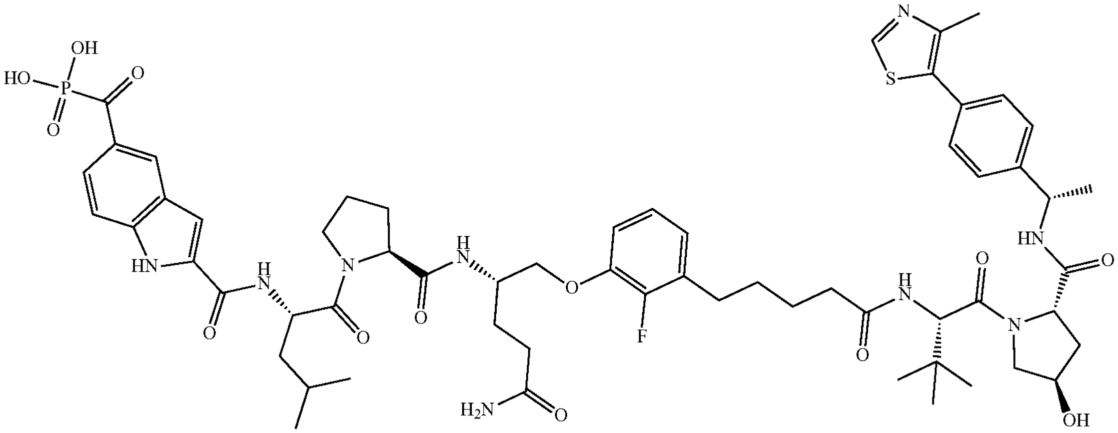 [SMILES: Cc1ncsc1-c1ccc([C@H](C)NC(=O)[C@@H]2C[C@@H](O)CN2C(=O)[C@@H](NC(=O)CCCCc2cccc(OC[C@H](CCC(N)=O)NC(=O)[C@@H]3CCCN3C(=O)[C@H](CC(C)C)NC(=O)c3cc4cc(C(=O)P(=O)(O)O)ccc4[nH]3)c2F)C(C)(C)C)cc1] |

TABLE 1-continued
| Exemplary Compounds | |
|---|---|
| I-# | Structure |
| I-277 | 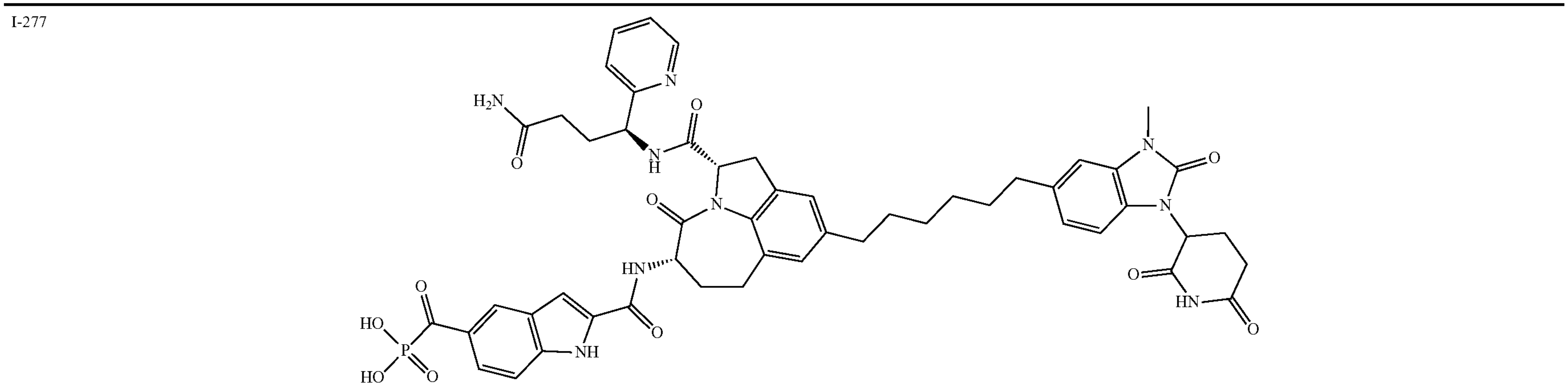 |
| I-278 | 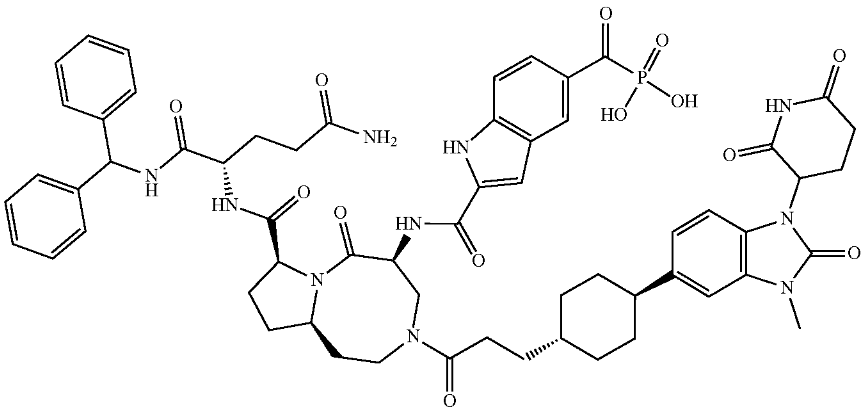 [SMILES: Cn1c(=O)n(C2CCC(=O)NC2=O)c2ccc([C@H]3CC[C@H](CCC(=O)N4CC[C@H]5CC[C@@H](C(=O)N[C@@H](CCC(N)=O)C(=O)NC(c6ccccc6)c6ccccc6)N5C(=O)[C@@H](NC(=O)c5cc6cc(C(=O)P(=O)(O)O)ccc6[nH]5)C4)CC3)cc21] |

TABLE 1-continued
Exemplary Compounds
| I-# | Structure |
|---|---|
| I-279 | 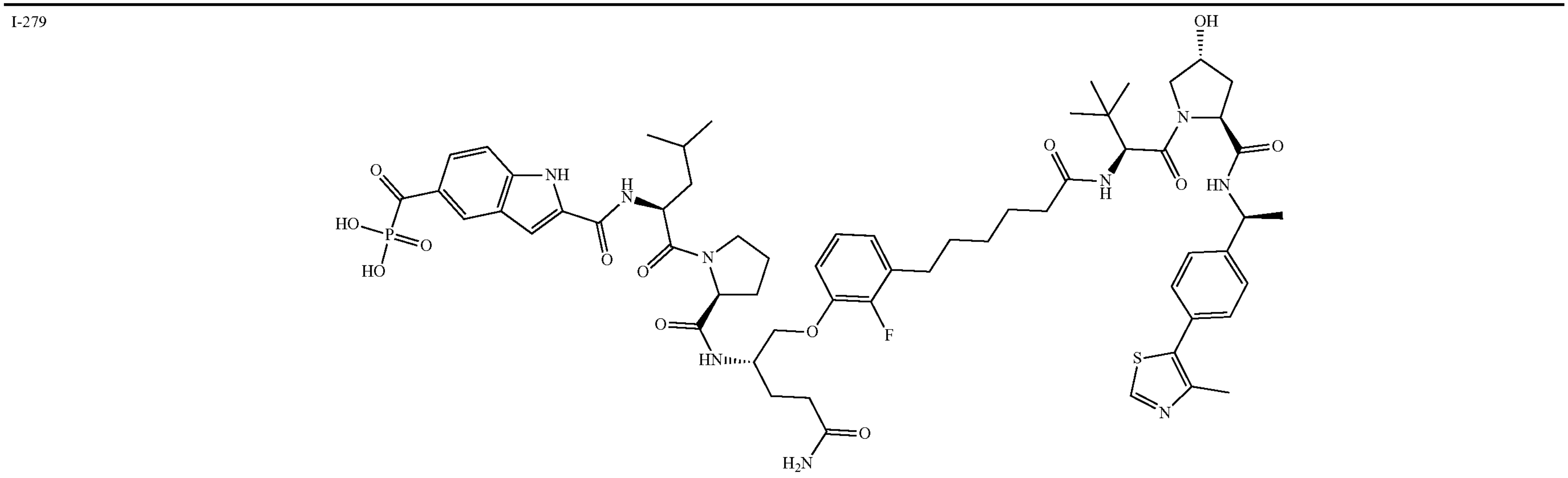 |
| I-280 | 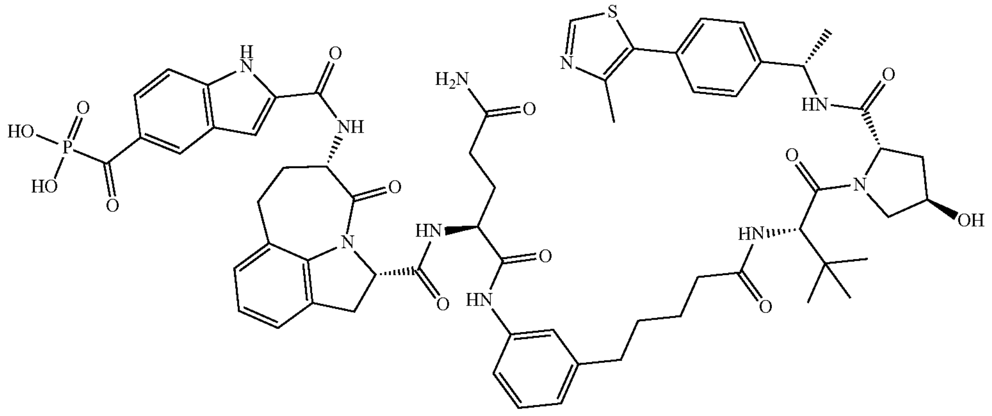 [SMILES: Cc1ncsc1-c1ccc([C@H](C)NC(=O)[C@@H]2C[C@@H](O)CN2C(=O)[C@@H](NC(=O)CCCCc2cccc(NC(=O)[C@H](CCC(N)=O)NC(=O)[C@@H]3Cc4cccc5c4N3C(=O)[C@@H](NC(=O)c3cc4cc(C(=O)P(=O)(O)O)ccc4[nH]3)CC5)c2)C(C)(C)C)cc1] |

TABLE 1-continued
| Exemplary Compounds | |
|---|---|
| I-# | Structure |
| I-281 | 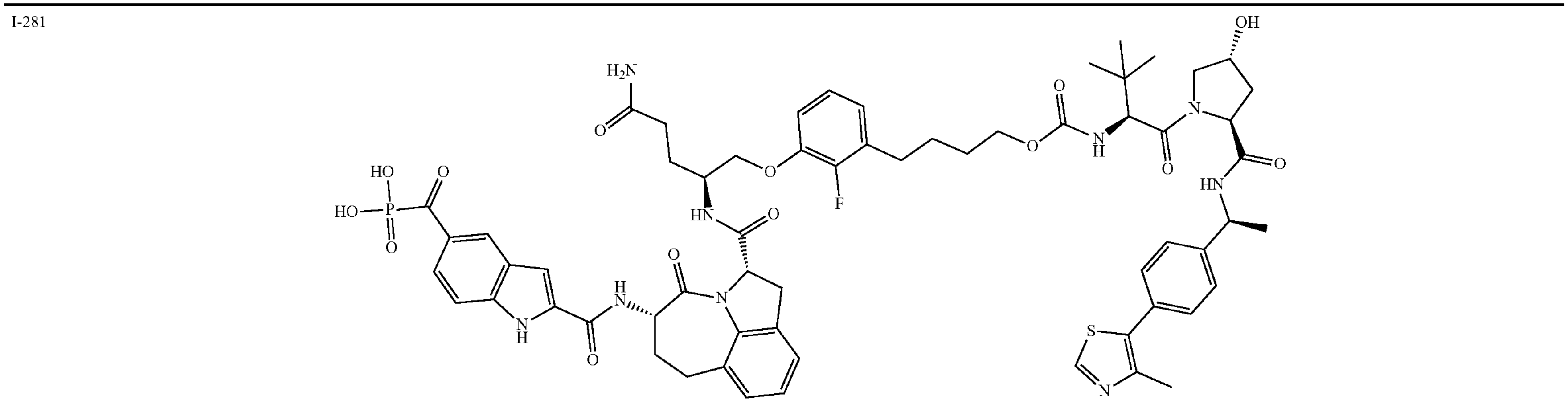 |
| I-282 | 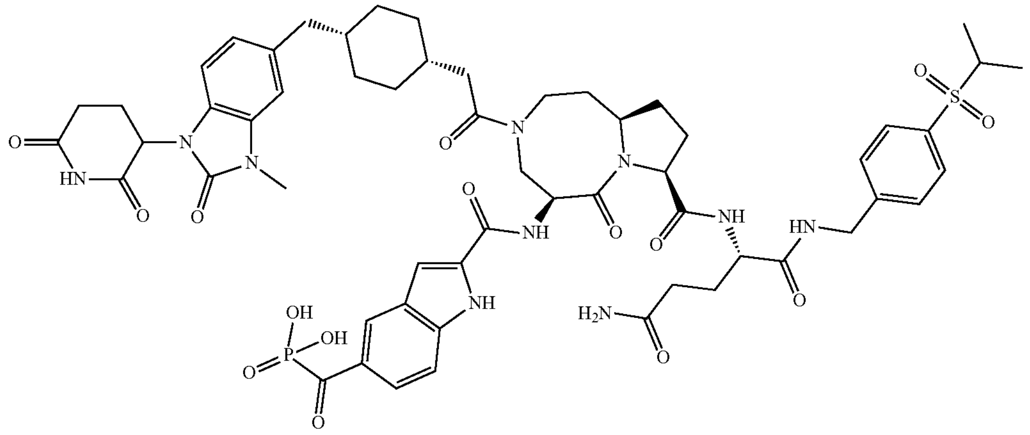 [SMILES: CC(C)S(=O)(=O)c1ccc(CNC(=O)[C@H](CCC(N)=O)NC(=O)[C@@H]2CC[C@@H]3CCN(C(=O)C[C@H]4CC[C@@H](Cc5ccc6c(c5)n(C)c(=O)n6C5CCC(=O)NC5=O)CC4)C[C@H](NC(=O)c4cc5cc(C(=O)P(=O)(O)O)ccc5[nH]4)C(=O)N32)cc1] |

TABLE 1-continued
| Exemplary Compounds | |
|---|---|
| I-# | Structure |
| I-283 | 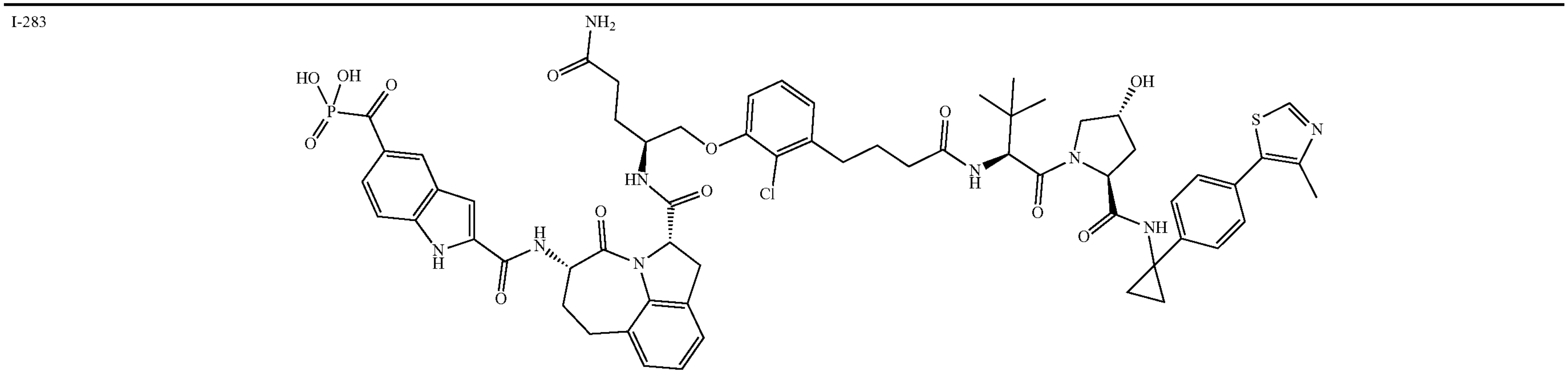 |
| I-284 | 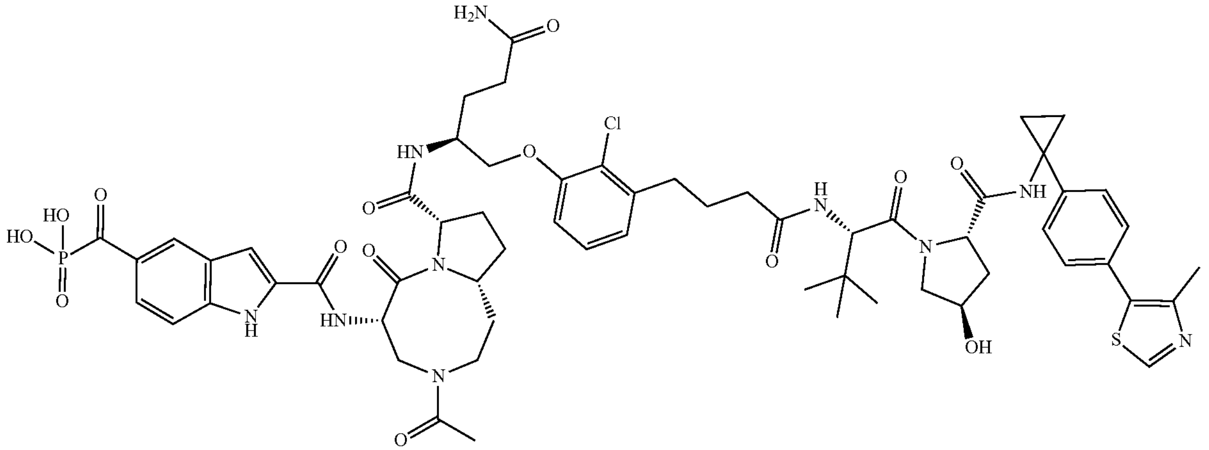 |

TABLE 1-continued
| Exemplary Compounds | |
|---|---|
| I-# | Structure |
| I-285 | 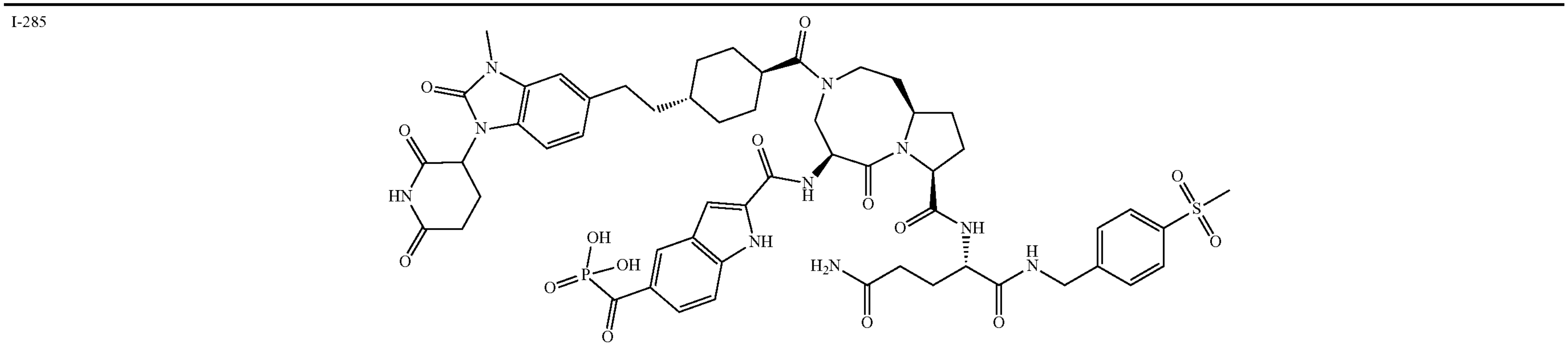 |
| I-286 | 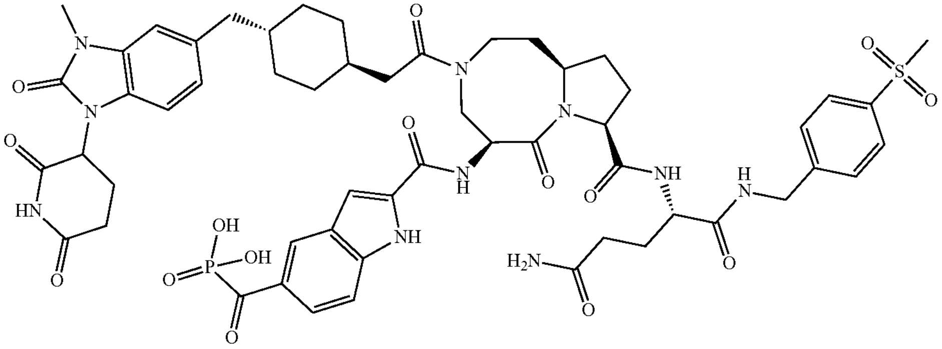 |

TABLE 1-continued
| Exemplary Compounds | |
|---|---|
| I-# | Structure |
| I-287 | 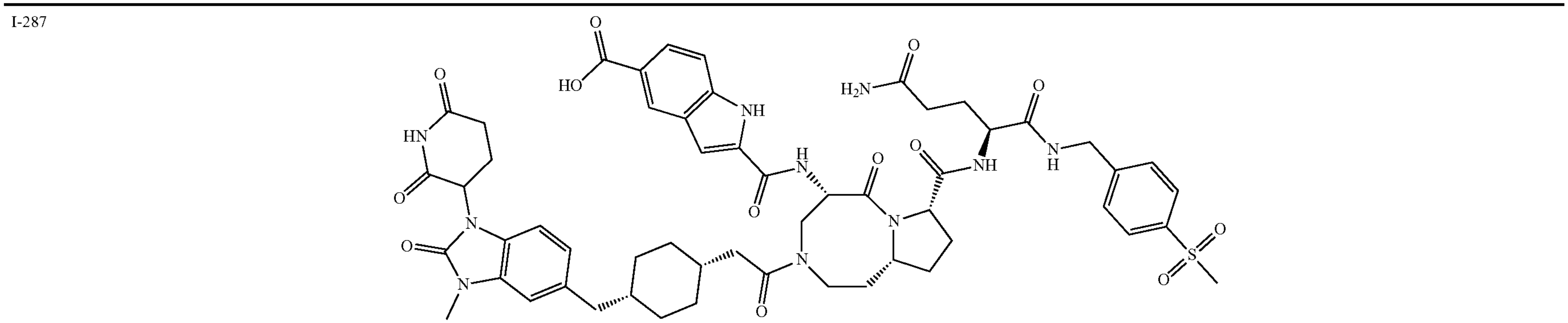 |
| I-288 | 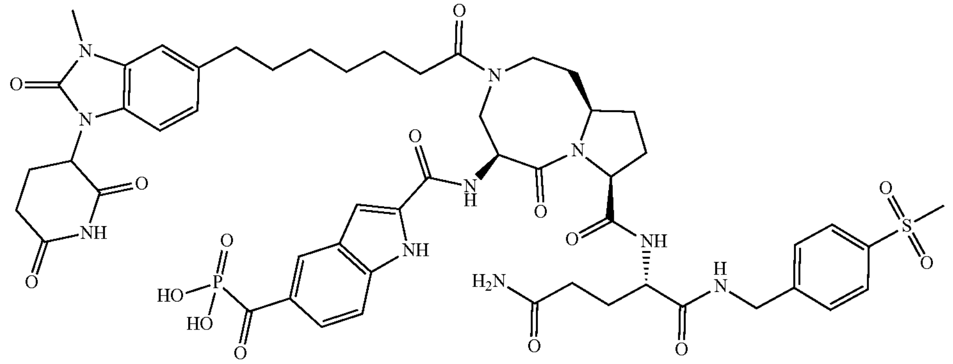 |

TABLE 1-continued
| Exemplary Compounds | |
|---|---|
| I-# | Structure |
| I-289 | 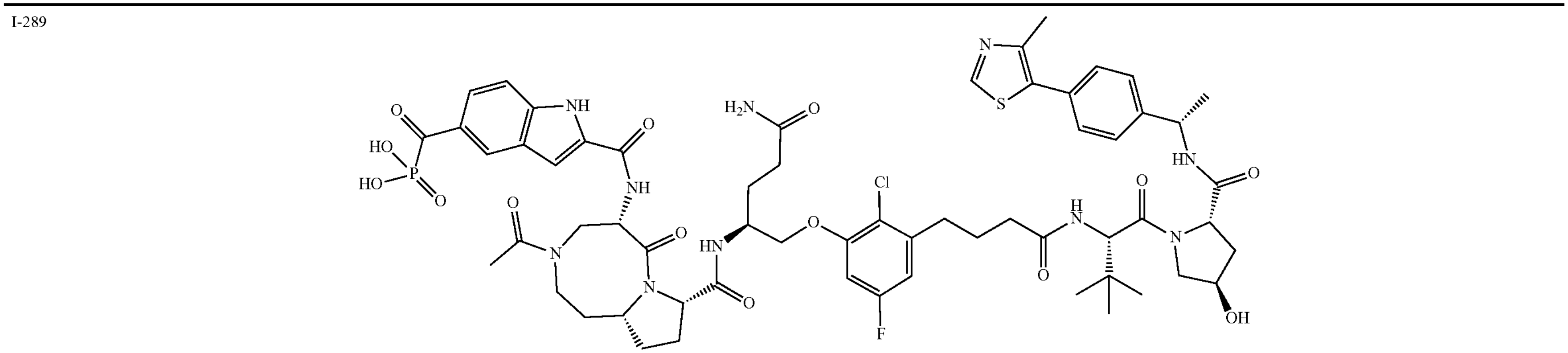 |
| I-290 | 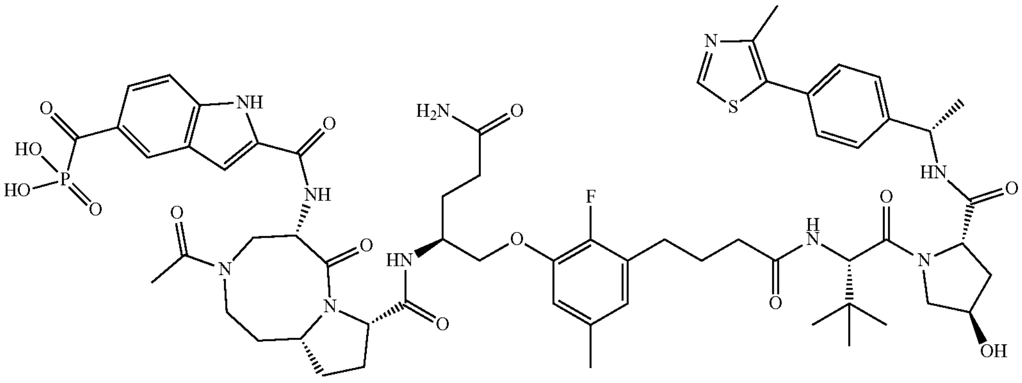 [SMILES: CC(=O)N1CC[C@H]2CC[C@@H](C(=O)N[C@@H](CCC(N)=O)COc3cc(C)cc(CCCC(=O)N[C@H](C(=O)N4C[C@H](O)C[C@H]4C(=O)N[C@@H](C)c4ccc(-c5scnc5C)cc4)C(C)(C)C)c3F)N2C(=O)[C@@H](NC(=O)c2cc3cc(C(=O)P(=O)(O)O)ccc3[nH]2)C1] |

TABLE 1-continued
| Exemplary Compounds | |
|---|---|
| I-# | Structure |
| I-291 | 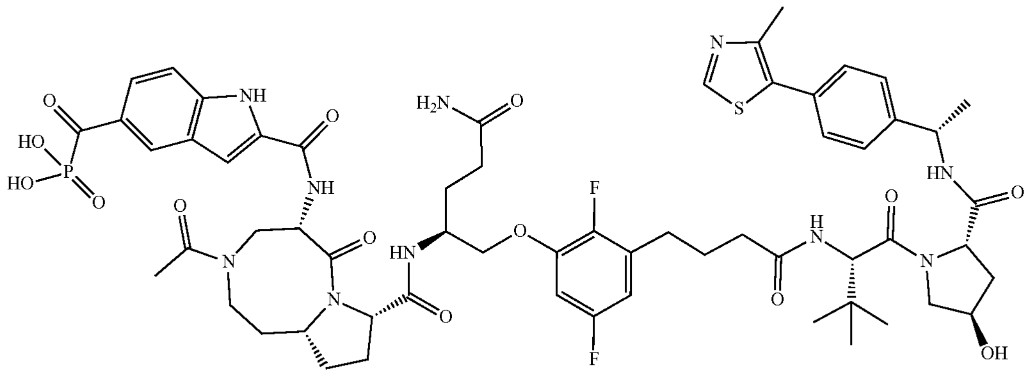 |
| I-292 | 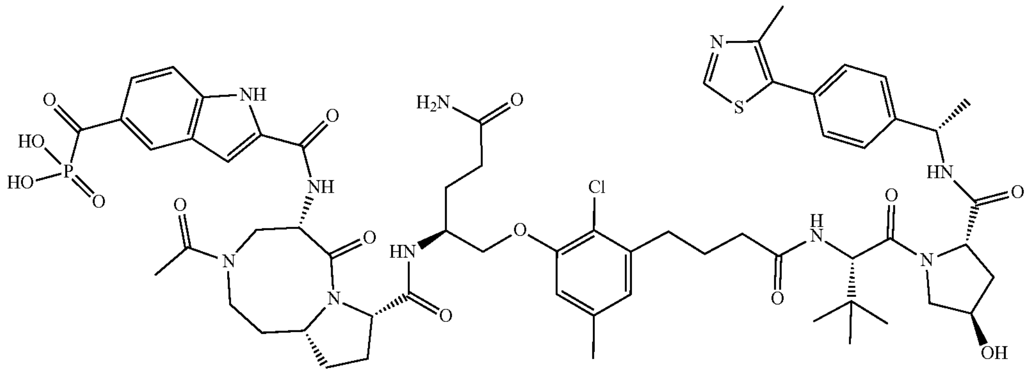 [SMILES: CC(=O)N1CC[C@H]2CC[C@@H](C(=O)N[C@@H](CCC(N)=O)COc3cc(F)cc(CCCC(=O)N[C@H](C(=O)N4C[C@H](O)C[C@H]4C(=O)N[C@@H](C)c4ccc(-c5scnc5C)cc4)C(C)(C)C)c3F)N2C(=O)[C@@H](NC(=O)c2cc3cc(C(=O)P(=O)(O)O)ccc3[nH]2)C1] |

TABLE 1-continued
| Exemplary Compounds | |
|---|---|
| I-# | Structure |
| I-293 | 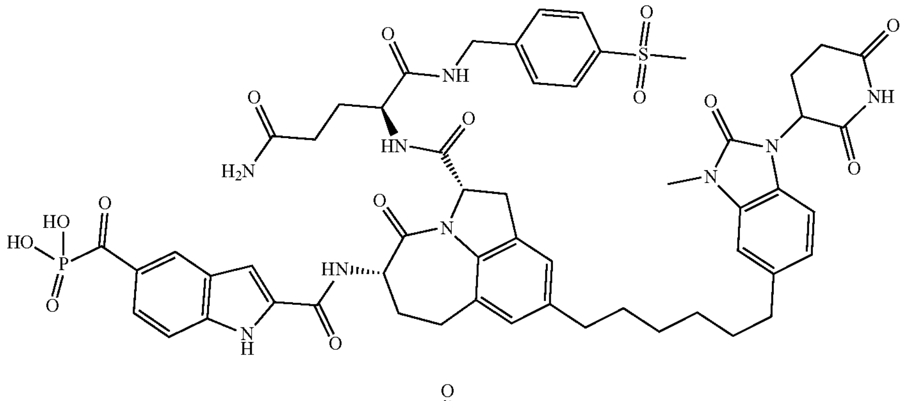 |
| I-294 | 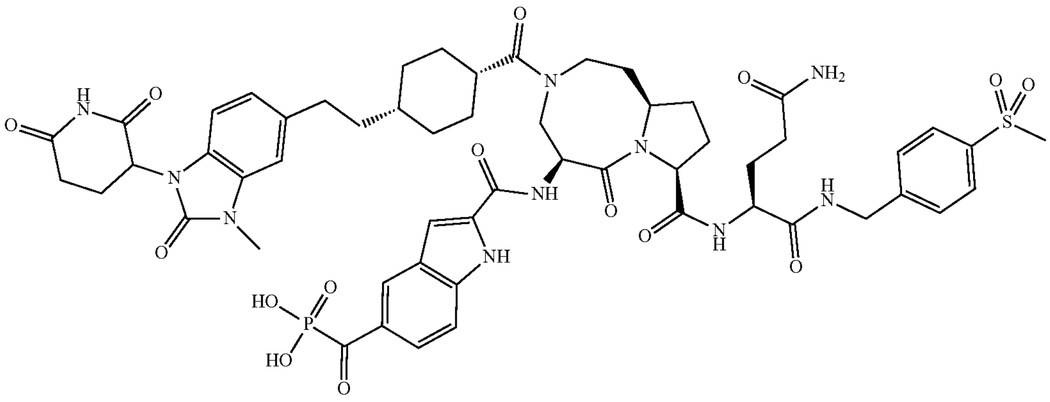 [SMILES: Cn1c(=O)n(C2CCC(=O)NC2=O)c2ccc(CC[C@H]3CC[C@@H](C(=O)N4CC[C@H]5CC[C@@H](C(=O)N[C@@H](CCC(N)=O)C(=O)NCc6ccc(S(C)(=O)=O)cc6)N5C(=O)[C@@H](NC(=O)c5cc6cc(C(=O)P(=O)(O)O)ccc6[nH]5)C4)CC3)cc21] |

TABLE 1-continued
| Exemplary Compounds | |
|---|---|
| I-# | Structure |
| I-295 | 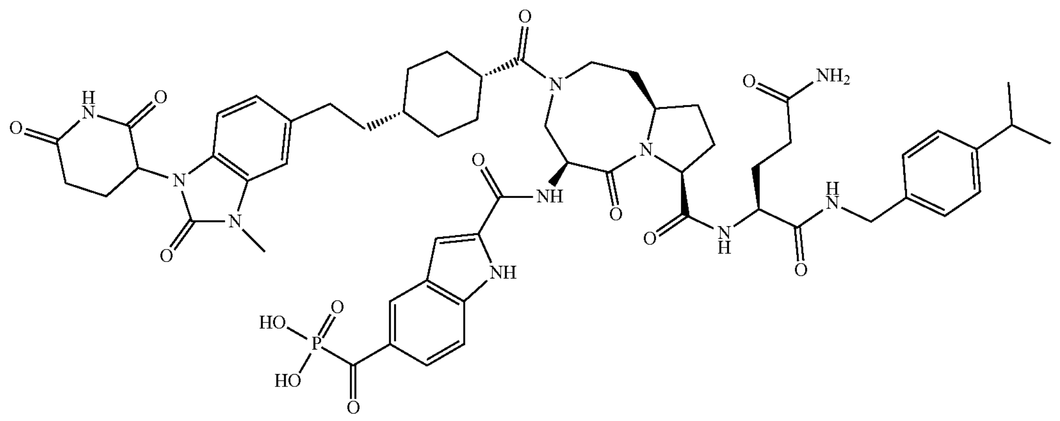 [SMILES: CC(C)c1ccc(CNC(=O)[C@H](CCC(N)=O)NC(=O)[C@@H]2CC[C@@H]3CCN(C(=O)[C@H]4CC[C@@H](CCc5ccc6c(c5)n(C)c(=O)n6C5CCC(=O)NC5=O)CC4)C[C@H](NC(=O)c4cc5cc(C(=O)P(=O)(O)O)ccc5[nH]4)C(=O)N32)cc1] |

In some embodiments, the present invention provides a compound set forth in Table 1, above, or a pharmaceutically acceptable salt thereof. In some embodiments, the present invention provides a compound set forth in Table 1 as a diammonium salt.
Further exemplary compounds of the invention are set forth in Table IA, below.
TABLE 1A
| Exemplary Compounds | |
|---|---|
| I-# | Structure |
| I-72 | 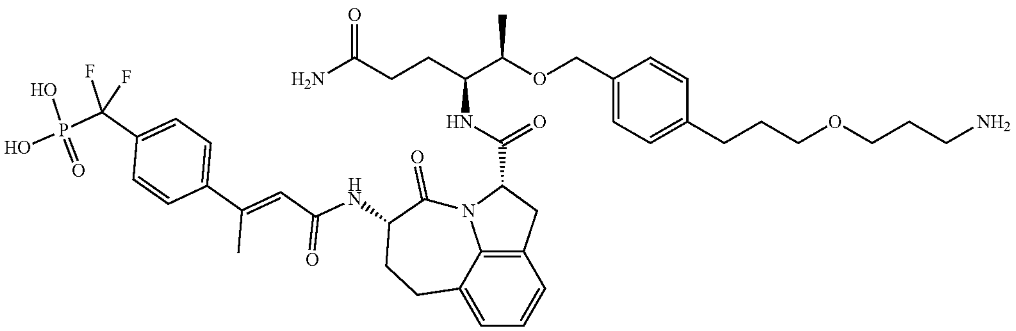 [SMILES: C/C(=C\C(=O)N[C@H]1CCc2cccc3c2N(C1=O)[C@H](C(=O)N[C@@H](CCC(N)=O)[C@@H](C)OCc1ccc(CCCOCCCN)cc1)C3)c1ccc(C(F)(F)P(=O)(O)O)cc1] |
| I-73 | 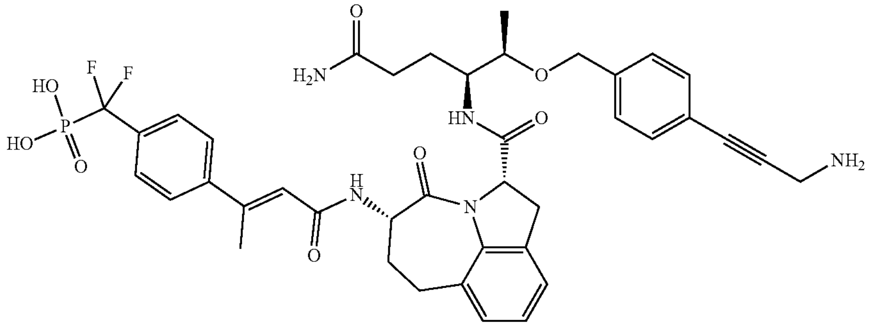 [SMILES: C/C(=C\C(=O)N[C@H]1CCc2cccc3c2N(C1=O)[C@H](C(=O)N[C@@H](CCC(N)=O)[C@@H](C)OCc1ccc(C#CCN)cc1)C3)c1ccc(C(F)(F)P(=O)(O)O)cc1] |
| I-74 | 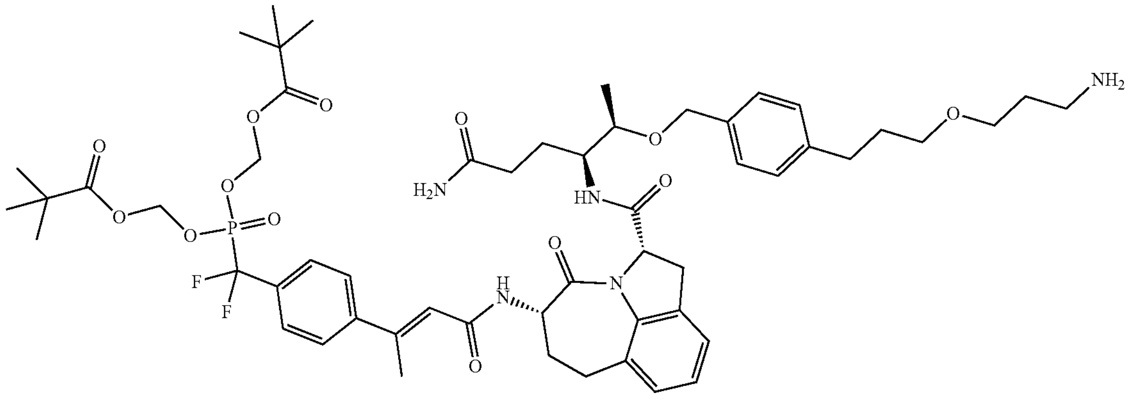 [SMILES: C/C(=C\C(=O)N[C@H]1CCc2cccc3c2N(C1=O)[C@H](C(=O)N[C@@H](CCC(N)=O)[C@@H](C)OCc1ccc(CCCOCCCN)cc1)C3)c1ccc(C(F)(F)P(=O)(OCOC(=O)C(C)(C)C)OCOC(=O)C(C)(C)C)cc1] |

TABLE 1A-continued
| Exemplary Compounds | |
|---|---|
| I-# | Structure |
| I-75 | 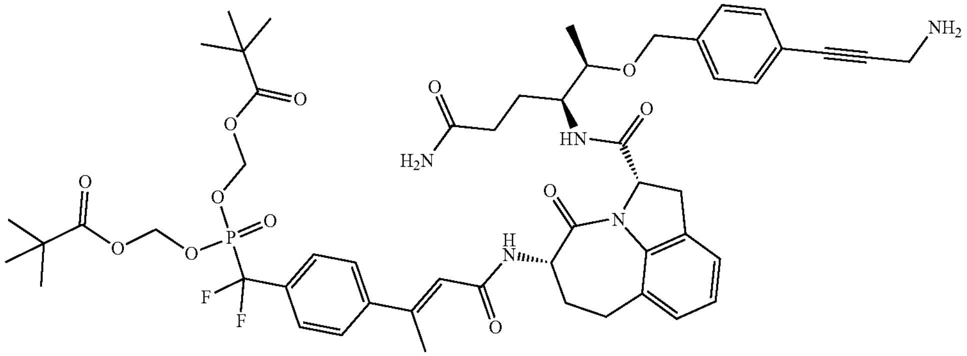 [SMILES: C/C(=C\C(=O)N[C@H]1CCc2cccc3c2N(C1=O)[C@H](C(=O)N[C@@H](CCC(N)=O)[C@@H](C)OCc1ccc(C#CCN)cc1)C3)c1ccc(C(F)(F)P(=O)(OCOC(=O)C(C)(C)C)OCOC(=O)C(C)(C)C)cc1] |
| I-76 | 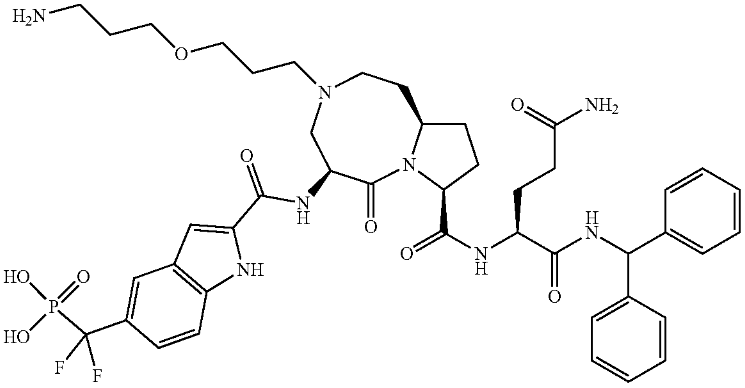 [SMILES: NCCCOCCCN1CC[C@H]2CC[C@@H](C(=O)N[C@@H](CCC(N)=O)C(=O)NC(c3ccccc3)c3ccccc3)N2C(=O)[C@@H](NC(=O)c2cc3cc(C(F)(F)P(=O)(O)O)ccc3[nH]2)C1] |
| I-77 | 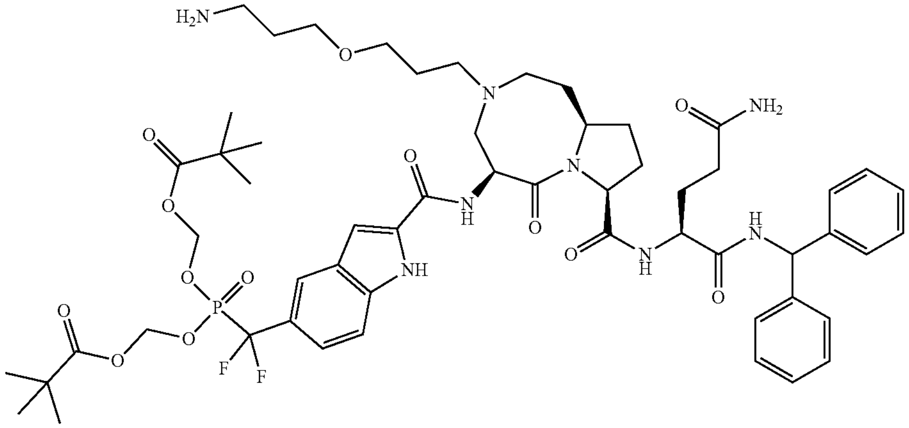 [SMILES: CC(C)(C)C(=O)OCOP(=O)(OCOC(=O)C(C)(C)C)C(F)(F)c1ccc2[nH]c(C(=O)N[C@H]3CN(CCCOCCCN)CC[C@H]4CC[C@@H](C(=O)N[C@@H](CCC(N)=O)C(=O)NC(c5ccccc5)c5ccccc5)N4C3=O)cc2c1] |
| I-78 | 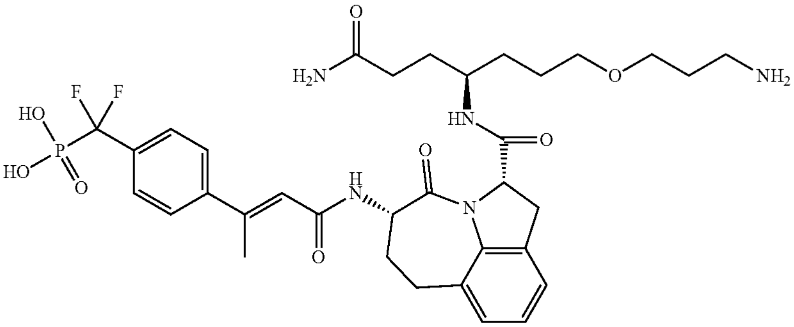 [SMILES: C/C(=C\C(=O)N[C@H]1CCc2cccc3c2N(C1=O)[C@H](C(=O)N[C@H](CCCOCCCN)CCC(N)=O)C3)c1ccc(C(F)(F)P(=O)(O)O)cc1] |

TABLE 1A-continued

| Exemplary Compounds | |
|---|---|
| I-# | Structure |
| I-79 | 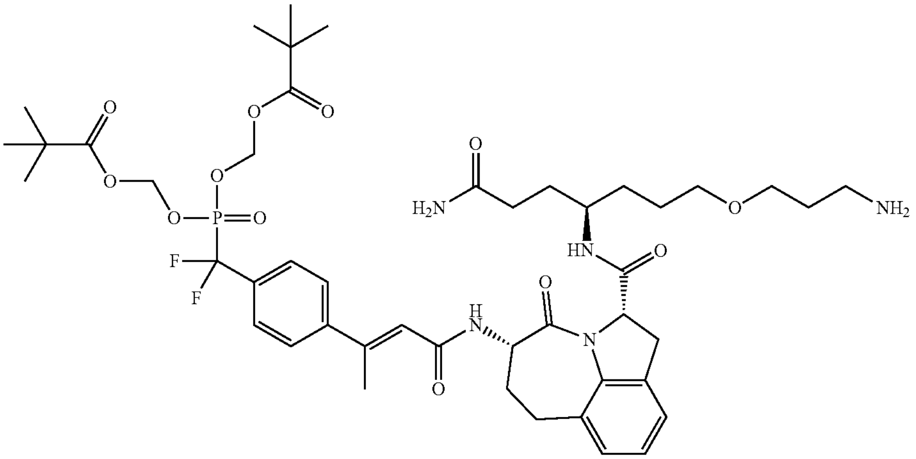 [SMILES: C/C(=C\C(=O)N[C@H]1CCc2cccc3c2N(C1=O)[C@H](C(=O)N[C@H](CCCOCCCN)CCC(N)=O)C3)c1ccc(C(F)(F)P(=O)(OCOC(=O)C(C)(C)C)OCOC(=O)C(C)(C)C)cc1] |

In some embodiments, the present invention provides a compound set forth in Table IA, above, or a pharmaceutically acceptable salt thereof.

4. General Methods of Providing the Present Compounds

The compounds of this invention may be prepared or isolated in general by synthetic and/or semi-synthetic methods known to those skilled in the art for analogous compounds and by methods described in detail in the Examples, herein.

In the Schemes below, where a particular protecting group, leaving group, or transformation condition is depicted, one of ordinary skill in the art will appreciate that other protecting groups, leaving groups, and transformation conditions are also suitable and are contemplated. Such groups and transformations are described in detail in March's Advanced Organic Chemistry: Reactions, Mechanisms, and Structure, M. B. Smith and J. March, 5th Edition, John Wiley & Sons, 2001, *Comprehensive Organic Transformations*, R. C. Larock, 2nd Edition, John Wiley & Sons, 1999, and *Protecting Groups in Organic Synthesis*, T. W. Greene and P. G. M. Wuts, 3rd edition, John Wiley & Sons, 1999, the entirety of each of which is hereby incorporated herein by reference.

As used herein, the phrase "oxygen protecting group" includes, for example, carbonyl protecting groups, hydroxyl protecting groups, etc. Hydroxyl protecting groups are well known in the art and include those described in detail in *Protecting Groups in Organic Synthesis*, T. W. Greene and P. G. M. Wuts, 3rd edition, John Wiley & Sons, 1999, the entirety of each of which is herein incorporated by reference. Examples of suitable hydroxyl protecting groups include, but are not limited to, esters, allyl ethers, ethers, silyl ethers, alkyl ethers, arylalkyl ethers, and alkoxyalkyl ethers. Examples of such esters include formates, acetates, carbonates, and sulfonates. Specific examples include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate (trimethylacetyl), crotonate, 4-methoxy-crotonate, benzoate, p-benylbenzoate, 2,4,6-trimethylbenzoate, carbonates such as methyl, 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl. Examples of such silyl ethers include trimethylsilyl, triethylsilyl, t-butyldimethylsilyl, t-butyldiphenylsilyl, triisopropylsilyl, and other trialkylsilyl ethers. Alkyl ethers include methyl, benzyl, p-methoxybenzyl, 3,4-dimethoxybenzyl, trityl, t-butyl, allyl, and allyloxycarbonyl ethers or derivatives. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyranyl ethers. Examples of arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, and 2- and 4-picolyl.

Amino protecting groups are well known in the art and include those described in detail in *Protecting Groups in Organic Synthesis*, T. W. Greene and P. G. M. Wuts, 3rd edition, John Wiley & Sons, 1999, the entirety of each of which is herein incorporated by reference. Suitable amino protecting groups include, but are not limited to, aralkylamines, carbamates, cyclic imides, allyl amines, amides, and the like. Examples of such groups include t-butyloxycarbonyl (BOC), ethyloxycarbonyl, methyloxycarbonyl, trichloroethyloxycarbonyl, allyloxycarbonyl (Alloc), benzyloxocarbonyl (CBZ), allyl, phthalimide, benzyl (Bn), fluorenylmethylcarbonyl (Fmoc), formyl, acetyl, chloroacetyl, dichloroacetyl, trichloroacetyl, phenylacetyl, trifluoroacetyl, benzoyl, and the like.

In the schemes below, where a final degrader is formed having a free amine DIM moiety, it is not shown but it is generally appreciated and well known by those having ordinary skill in the art that the reactivity of said free amine may be masked by employing a suitable amino protecting group that can thereafter be removed in situ or during a separate synthetic step to form the final degrader product.

In certain embodiments, compounds of the present invention are generally prepared according to Scheme 1 set forth below:

Scheme 1: Synthesis of Compounds of the Invention

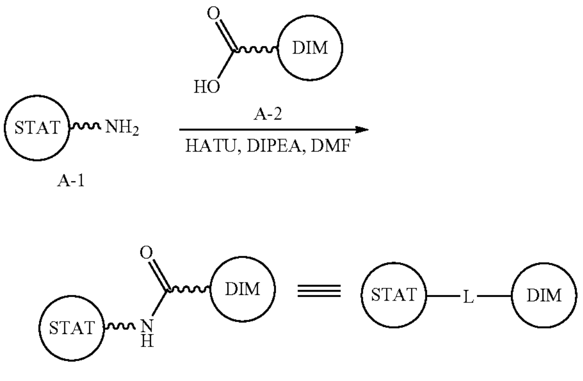

As depicted in Scheme 1, above, amine A-1 is coupled to acid A-2 using the coupling agent HATU in the presence of the base DIPEA in DMF to form a compound of the invention with a linker comprising an amide bond. The squiggly bond, ~~~, represents the portion of the linker between STAT and the terminal amino group of A-1 or the portion of the linker between DIM and the terminal carboxyl group of A-2, respectively. Additionally, an amide bond can be formed using coupling reagents known in the art such as, but not limited to DCC, DIC, EDC, HBTU, HCTU, PyAOP, PyBrOP, BOP, BOP-Cl, DEPBT, T3P, TATU, TBTU, TNTU, TOTU, TPTU, TSTU, or TDBTU.

In certain embodiments, compounds of the present invention are generally prepared according to Scheme 2 set forth below:

Scheme 2: Synthesis of Compounds of the Invention

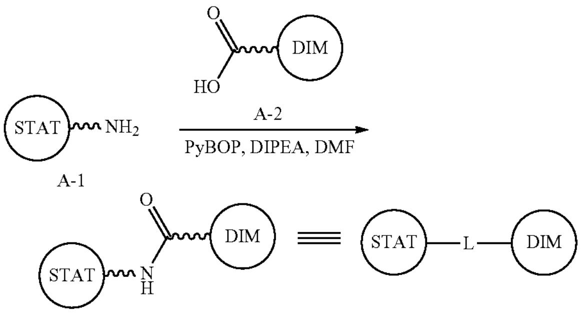

As depicted in Scheme 2, above, amine A-1 is coupled to acid A-2 using the coupling agent PyBOP in the presence of the base DIPEA in DMF to form a compound of the invention with a linker comprising an amide bond. The squiggly bond, ~~~, represents the portion of the linker between STAT and the terminal amino group of A-1 or the portion of the linker between DIM and the terminal carboxyl group of A-2, respectively. Additionally, an amide bond can be formed using coupling reagents known in the art such as, but not limited to DCC, DIC, EDC, HBTU, HCTU, PyAOP, PyBrOP, BOP, BOP-Cl, DEPBT, T3P, TATU, TBTU, TNTU, TOTU, TPTU, TSTU, or TDBTU.

In certain embodiments, compounds of the present invention are generally prepared according to Scheme 3 set forth below:

Scheme 3: Synthesis of Compounds of the Invention

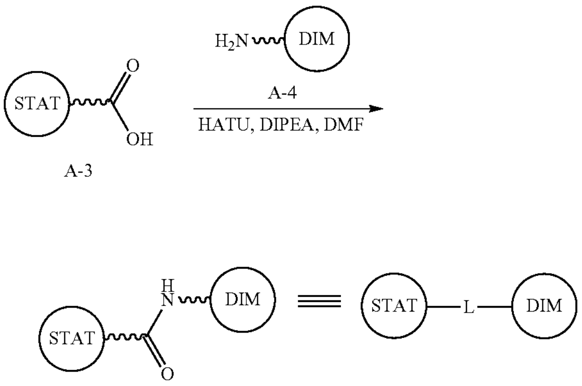

As depicted in Scheme 3, above, acid A-3 is coupled to amine A-4 using the coupling agent PyBOP in the presence of the base DIPEA in DMF to form a compound of the invention with a linker comprising an amide bond. The squiggly bond, ~~~, represents the portion of the linker between STAT and the terminal carboxyl group of A-3 or the portion of the linker between DIM and the terminal amino group of A-4, respectively. Additionally, an amide bond can be formed using coupling reagents known in the art such as, but not limited to DCC, DIC, EDC, HBTU, HCTU, PyAOP, PyBrOP, BOP, BOP-Cl, DEPBT, T3P, TATU, TBTU, TNTU, TOTU, TPTU, TSTU, or TDBTU.

In certain embodiments, compounds of the present invention are generally prepared according to Scheme 4 set forth below:

Scheme 4: Synthesis of Compounds of the Invention

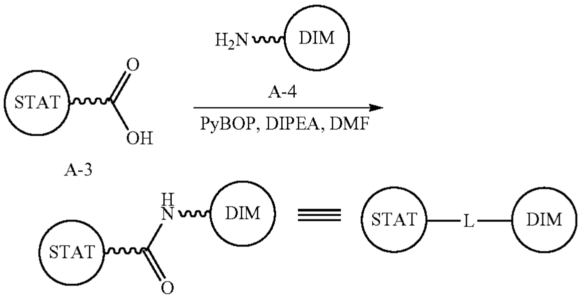

As depicted in Scheme 4, above, acid A-3 is coupled to amine A-4 using the coupling agent PyBOP in the presence of the base DIPEA in DMF to form a compound of the invention with a linker comprising an amide bond. The squiggly bond, ~~~, represents the portion of the linker between STAT and the terminal carboxyl group of A-3 or the portion of the linker between DIM and the terminal amino group of A-4, respectively. Additionally, an amide bond can be formed using coupling reagents known in the art such as, but not limited to DCC, DIC, EDC, HBTU, HCTU, PyAOP, PyBrOP, BOP, BOP-Cl, DEPBT, T3P, TATU, TBTU, TNTU, TOTU, TPTU, TSTU, or TDBTU.

In certain embodiments, compounds of the present invention are generally prepared according to Scheme 5 set forth below:

Scheme 5: Synthesis of Compounds of the Invention

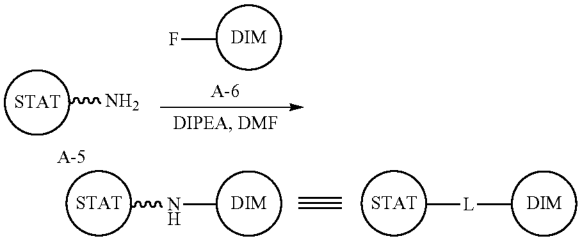

As depicted in Scheme 5, above, an $S_NAr$ displacement of fluoride A-6 by amine A-5 is effected in the presence of the base DIPEA in DMF to form a compound of the invention with a linker comprising a secondary amine. The squiggly bond, ~~~, represents the portion of the linker between STAT and the terminal amino group of A-5.

In certain embodiments, compounds of the present invention are generally prepared according to Scheme 6 set forth below:

Scheme 6: Synthesis of Compounds of the Invention

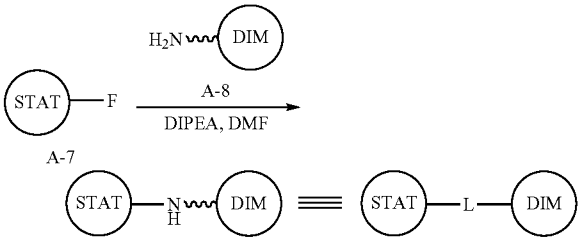

As depicted in Scheme 6, above, an $S_NAr$ displacement of fluoride A-7 by amine A-8 is effected in the presence of the base DIPEA in DMF to form a compound of the invention with a linker comprising a secondary amine. The squiggly bond, ~~~, represents the portion of the linker between DIM and the terminal amino group of A-8.

In certain embodiments, compounds of the present invention are generally prepared according to Scheme 7 set forth below:

Scheme 7: Synthesis of Compound of the Invention

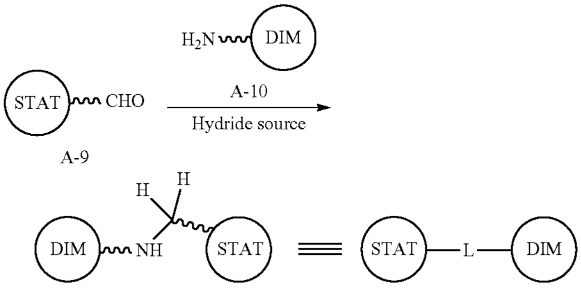

As depicted in Scheme 7, above, reductive alkylation of aldehyde A-9 by amine A-10 is effected in the presence of a mild hydride source (e.g., sodium cyanoborohydride or sodium triacetoxyborohydride) to form a provided compound with a linker comprising a secondary amine. The squiggly bond, ~~~, represents the portion of the linker between DIM and the terminal amino group of A-10.

In certain embodiments, compounds of the present invention are generally prepared according to Scheme 8 set forth below:

Scheme 8: Synthesis of Compound of the Invention

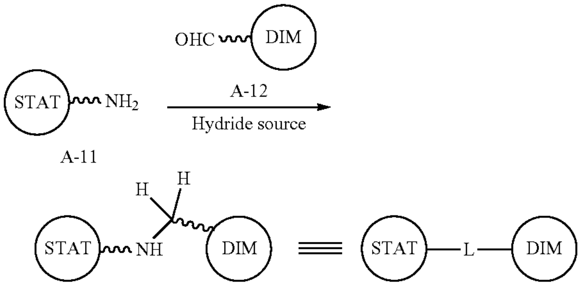

As depicted in Scheme 8, above, reductive alkylation of aldehyde A-12 by amine A-11 is effected in the presence of a mild hydride source (e.g., sodium cyanoborohydride or sodium triacetoxyborohydride) to form a provided compound with a linker comprising a secondary amine. The squiggly bond, ~~~, represents the portion of the linker between STAT and the terminal amino group of A-11.

One of skill in the art will appreciate that various functional groups present in compounds of the invention such as aliphatic groups, alcohols, carboxylic acids, esters, amides, aldehydes, halogens and nitriles can be interconverted by techniques well known in the art including, but not limited to reduction, oxidation, esterification, hydrolysis, partial oxidation, partial reduction, halogenation, dehydration, partial hydration, and hydration. See for example, "March's Advanced Organic Chemistry", $5^{th}$ Ed., Ed.: Smith, M. B. and March, J., John Wiley & Sons, New York: 2001, the entirety of each of which is herein incorporated by reference. Such interconversions may require one or more of the aforementioned techniques, and certain methods for synthesizing compounds of the invention are described below in the Exemplification.

5. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably degrade and/or inhibit a STAT protein, or a mutant thereof, in a biological sample or in a patient. In certain embodiments, the amount of compound in compositions of this invention is such that is effective to measurably degrade and/or inhibit an STAT protein, or a mutant thereof, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily or degratorily active metabolite or residue thereof.

As used herein, the term "inhibitorily active metabolite or residue thereof" means that a metabolite or residue thereof is also an inhibitor of a STAT protein, or a mutant thereof.

As used herein, the term "degratorily active metabolite or residue thereof" means that a metabolite or residue thereof is also a degrader of an STAT protein, or a mutant thereof.

In certain embodiments, a provided compound is administered as a prodrug.

The term "prodrug" refers to a compound that is made more active in vivo. A provided compound can also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the provided compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as a phosphonate ester (the "prodrug"), but then is metabolically hydrolyzed to the phosphonic acid or a conjugate base thereof, the active entity. Additional examples include peptidyl derivatives of a compound. The term "therapeutically acceptable prodrug," refers to those prodrugs or zwitterions which are suitable for use in contact with the tissues of patients without undue toxicity, irritation, and allergic response, are commensurate with a reasonable benefit/risk ratio, and are effective for their intended use.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the compound can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the degradation and/or inhibition of STAT protein activity.

Examples of STAT protein that are degraded and/or inhibited by the compounds and compositions described herein and against which the methods described herein are useful include those of the signal transducer and activators of transcription (STAT) family of proteins, the members of which include STAT1, STAT2, STAT3, STAT4, STAT5A, STAT5B, or STAT6, or a mutant thereof. Yu et al., "Crosstalk between cancer and immune cells: Role of STAT3 in the tumour microenvironment" Nat. Rev. Immunol. 2007, 7, 41-51., Levy et al., "STATs: Transcriptional controland biological impact" Nat. Rev. Mol. Cell Biol. 2002, 3, 651-662, the entirety of each of which is herein incorporated by reference.

The activity of a compound utilized in this invention as a degrader and/or inhibitor of STAT1, STAT2, STAT3, STAT4, STAT5A, STAT5B, or STAT6, or a mutant thereof, may be assayed in vitro, in vivo or in a cell line. In vitro assays include assays that determine inhibition of either the activity and/or the subsequent functional consequences of activated STAT protein, or a mutant thereof. Alternate in vitro assays quantitate the ability of the inhibitor to bind to a STAT protein. Inhibitor binding may be measured by radiolabeling the inhibitor prior to binding, isolating the inhibitor/STAT complex and determining the amount of radiolabel bound. Alternatively, inhibitor binding may be determined by running a competition experiment where new inhibitors are incubated with a STAT protein bound to known radioligands. Representative in vitro and in vivo assays useful in assaying a STAT inhibitor include those described and disclosed in, e.g., Schust et al., "A high-throughput fluorescence polarization assay for signal transducer and activator of transcription 3" *Anal. Biochem.* 2004, 333(1):114; Müller et al., "A high-throughput assay for signal transducer and activator of transcription 5b based on fluorescence polarization" Anal. Biochem. 2008, 375(2):249. Detailed conditions for assaying a compound utilized in this invention as a degrader and/or inhibitor of STAT proteins, or a mutant thereof, are set forth in the Examples below.

The STAT family of proteins are cytoplasmic transcription factors with important roles in mediating responses to cytokines and growth factors, including promoting cell growth and differentiation, and inflammation and immune responses (Bromberg et al., *Breast Cancer Res.* 2000, 2:86-90; Darnell et al., *Nat. Rev. Cancer* 2002, 2:740-749). STAT proteins are classically activated by tyrosine (Tyr) kinases, such as Janus kinases (JAKs) and Src family kinases, in response to the binding of cytokine and growth factors to their cognate receptors (Darnell et al., *Science* 1994, 264:1415). The Tyr phosphorylation (pTyr) promotes dimerization between two activated STAT:STAT monomers through a reciprocal pTyr-Src homology SH2 domain interactions. Active STAT:STAT dimers translocate to the nucleus to induce gene transcription by binding to specific DNA-response elements in the promoters of target genes to regulate gene expression. By contrast, aberrantly-active STAT3, one of the STAT family members, has been implicated in many human tumors and represents an attractive target for drug discovery. Persistently activated STAT3 and, to some extent, STAT5 increase tumour cell proliferation, survival and invasion while suppressing anti-tumour immunity. The persistent activation of STAT3 also mediates tumour-promoting inflammation. This aberrant activation of STAT3 occurs in glioma, breast, prostate, ovarian, and many other human cancers, whereby it promotes malignant progression (Yu & Jove, *Nat. Rev. Cancer* 2004, 4:97-105). JAKs, Src, and epidermal growth factor receptor (EGFR) are STAT3 upstream regulators (Bromberg et al., *Mol. Cell. Biol.* 1998, 18:2553; Sartor et al., *Cancer Res.* 1997, 57:978; Garcia et al., *Oncogene* 2001, 20:2499). Mechanisms by which constitutively-active STAT3 mediates tumorigenesis include dysregulation of gene expression that leads to uncontrolled growth and survival of tumor cells, enhanced tumor angiogenesis, and metastasis and the suppression of tumor immune surveillance (Yu & Jove 2004; Bromberg & Darnell, Oncogene 2000, 19:2468-2473; Bowman et al., *Oncogene* 2000, 19:2474-2488; Turkson & Jove, Oncogene 2000, 19:6613-6626; Turkson, *Expert Opin. Ther Targets* 2004, 8:409-422; Wang et al., *Nat. Med.* 2004, 10:48-54).

The main domains of STAT3 protein include the tetramerization and leucine zipper at the N-terminus, the DNA binding domain, and the SH2 transactivation domain at the carboxy-terminal end. The SH2 region is responsible for the binding of STAT3 to the tyrosine-phosphorylated receptors and for the dimerization which is necessary for DNA binding and gene expression (Zhong et al., *Science* 1994, 264:95). STAT3 is activated by phosphorylation at Y-705, which leads to dimer formation, nuclear translocation, recognition of STAT3-specific DNA binding elements, and activation of target gene transcription (Damell 1994; Zhong 1994).

The constitutive activation of STAT3 is frequently detected in breast carcinoma cell lines but not in normal breast epithelial cells (Garcia et al., *Cell. Growth. Differ.* 1997, 8:1267; Bowman 2000). It has been reported that approximately 60 percent of breast tumors contain persistently activated STAT3 (Dechow et al., *Proc. Natl. Acad. Sci. USA* 2004, 101:10602). STAT3 has been classified as a proto-oncogene because activated STAT3 can mediate oncogenic transformation in cultured cells and tumor formation in nude mice (Bromberg et al., *Cell* 1999, 98:295). STAT3 may participate in oncogenesis by stimulating cell proliferation, promoting angiogenesis, and conferring resistance to apoptosis induced by conventional therapies (Catlett-Falcone et al., *Curr. Opin. Oncol.* 1999, 11:1; Catlett-Falcone et al., *Immunity* 1999, 10:105; Alas et al., *Clin. Cancer Res.* 2003, 9:316; Wei et al., *Oncogene* 2003, 22:1517). Possible downstream targets through which STAT3 promotes oncogenesis include up-regulation of anti-apoptotic factors (Bcl-2, survivin, Mcl-1, and Bcl-$X_L$), cell-cycle regulators (cyclin D1, MEK5, and c-myc), and inducer of tumor angiogenesis (VEGF) (Bromberg et al., *Cell* 1999, 98:295; Wei et al., *Oncogene* 2003, 22:1517; Real et al., *Oncogene* 2002, 21:7611; Puthier et al., *Eur. J. Immunol.* 1999, 29:3945; Niu et al., *Oncogene* 2002, 21:2000; Kiuchi et al., *J Exp. Med.* 1999, 189:63; Song et al., *Oncogene* 2004, 23:8301). Activated STAT3 signaling directly contributes to malignant progression of cancer. STAT3 oncogenic function acts through the pro-survival proteins such as survivin, Mcl-1, Bcl-2, and Bcl-$X_L$ and results in the prevention of apoptosis (Real et al., *Oncogene* 2002, 21:7611; Aoki et al., *Blood* 2003, 101:1535; Epling-Burnette et al., *J. Clin. Invest.* 2001, 107:351; Nielsen et al., *Leukemia* 1999, 13:735). Blockade of STAT3 signaling inhibits cancer cell growth, demonstrating that STAT3 is essential to the survival or growth of tumor cells (Alas et al., *Clin. Cancer Res.* 2003, 9:316; Aoki et al., *Blood* 2003, 101:1535; Epling-Bumette et al., *J. Clin. Invest.* 2001, 107:351; Burke et al., *Oncogene* 2001, 20:7925; Mora et al., *Cancer Res.* 2002, 62:6659; Ni et al., *Cancer Res.* 2000, 60:1225; Rahaman et al., *Oncogene* 2002, 21:8404).

Recent evidence also reveals the role of STAT3 in modulating mitochondrial functions and STAT3 crosstalk with other proteins, such as NF-κB, that promotes the malignant phenotype. Many human tumors harbor aberrantly-active STAT3 signaling, and studies in experimental models indicate tumor cells and tumors harboring constitutively-active STAT3 are responsive to STAT3 signaling modulators (Gough et al., *Science* 2009, 324:1713; Yu et al., *Nat. Rev. Cancer* 2009, 9:798; Grivennikov & Karin, *Cytokine & Growth Factor Rev.* 2010, 21:11).

Representative STAT inhibitors include those described and disclosed in e.g., Morlacchi et al. *Future Med. Chem.* 2014, 6(7):1909; Sgrignani et al. *Int. J. Mol. Sci.* 2018, 19:1591, Botta et al. *Mol. Inf* 2015, 34:689; Leung et al. *Methods* 2015, 71:38; Lavecchia et al. *Cur. Med. Chem.* 2011, 18:1; Chun et al. *Can. Lett.* 2015, 357:393; Zhang et al. *Eur J. Med. Chem.* 2017, 125:538; Yesylevskyy et al. *J. Chem. Inf Model.* 2016, 56:1588; Huang et al. *Bioorg. Med. Chem. Lett.* 2016, 26:5172; Gao et al. *Bioorg. Med. Chem.* 2016, 24:2549; Daka et al. *Bioorg. Med. Chem.* 2015, 23:1348; Ji et al. *Bioorg. Med. Chem.* 2016, 24:6174; Zhou et al. *Bioorg. Med. Chem.* 2017, 25:2995; and Yu et al. *J. Med. Chem.* 2017, 60:2718; Chen et al. *Med. Chem. Lett.* 2010, 1:85; the entirety of each of which is herein incorporated by reference.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are degraders and/or inhibitors of one of more STAT protein and are therefore useful for treating one or more disorders associated with activity of one or more of STAT protein. Thus, in certain embodiments, the present invention provides a method for treating a STAT1-mediated, STAT2-mediated, STAT3-mediated, STAT4-mediated, STAT5A-mediated, STAT5B-mediated, or STAT6-mediated disorder comprising the step of administering to a patient in need thereof a compound of the present invention, or pharmaceutically acceptable composition thereof.

As used herein, the terms "STAT1-mediated", "STAT2-mediated", "STAT3-mediated", "STAT4-mediated", "STAT5A-mediated", "STAT5B-mediated", and/or "STAT6-mediated" disorders, diseases, and/or conditions as used herein means any disease or other deleterious condition in which one or more STAT1, STAT2, STAT3, STAT4, STAT5A, STAT5B, or STAT6, or a mutant thereof, are known to play a role. Accordingly, another embodiment of the present invention relates to treating or lessening the severity of one or more diseases in which one or more STAT1, STAT2, STAT3, STAT4, STAT5A, STAT5B, or STAT6, or a mutant thereof, are known to play a role.

In some embodiments, the present invention provides a method for treating one or more disorders, diseases, and/or conditions wherein the disorder, disease, or condition is a cancer, a neurodegenative disorder, a viral disease, an autoimmune disease, an inflammatory disorder, a hereditary disorder, a hormone-related disease, a metabolic disorder, conditions associated with organ transplantation, immunodeficiency disorders, a destructive bone disorder, a proliferative disorder, an infectious disease, a condition associated with cell death, thrombin-induced platelet aggregation, liver disease, pathologic immune conditions involving T cell activation, a cardiovascular disorder, or a CNS disorder.

Diseases and conditions treatable according to the methods of this invention include, but are not limited to, cancer (see, e.g., Turkson & Jove, *Oncogene* 2000, 19:6613-6626), diabetes (see, e.g., Gurzov et al., *FEBS* 2016, 283:3002), cardiovascular disease (see, e.g., Grote et al., *Vasc. Pharmacol.* 2005, 43:2005), viral disease (see, e.g., Gao et al., *J. Hepatol.* 2012, 57(2):430), autoimmune diseases such as lupus (see, e.g., Goropevšek et al., *Clin. Rev. Alleg. & Immun.* 2017, 52(2):164), and rheumatoid arthritis (see, e.g., Walker & Smith, *J. Rheumat.* 2005, 32(9):1650), autoinflammatory syndromes (see, e.g., Rauch et al., *Jak-Stat*

2013, 2(1):e23820), atherosclerosis (see, e.g., Ortiz-Munoz et al., *Arterio., Thrombo., Vasc. Bio.* 2009, 29:525), psoriasis (see, e.g., Andrés et al., *Exp. Derm.* 2013, 22(5):323), allergic disorders (see, e.g., Oh et al., *Eur. Respir. Rev.* 2019, 19(115):46), inflammatory bowel disease (see, e.g., Sugimoto, *World J. Gastroenterol.* 2008, 14(33):5110), inflammation (see, e.g., Tamiya et al., *Arterio., Thrombo., Vasc. Bio.* 2011, 31:980), acute and chronic gout and gouty arthritis, neurological disorders (see, e.g.,Campbell, *Brain Res.* Rev. 2005, 48(2):166), metabolic syndrome, immunodeficiency disorders such as AIDS and HIV (see, e.g., O'Shea et al., *N. Engl. J Med.* 2013, 368:161), destructive bone disorders (see, e.g.,Jatiani et al., *Genes & Can.* 2011, 1(10):979), osteoarthritis, proliferative disorders, Waldenström's Macroglobulinemia (see, e.g., Hodge et al., *Blood* 2014, 123(7):1055) infectious diseases, conditions associated with cell death, pathologic immune conditions involving T cell activation, and CNS disorders in a patient. In one embodiment, a human patient is treated with a compound of the current invention and a pharmaceutically acceptable carrier, adjuvant, or vehicle, wherein said compound is present in an amount to measurably degrade and/or inhibit one or more STAT1, STAT2, STAT3, STAT4, STAT5A, STAT5B, or STAT6, or a mutant thereof Compounds of the current invention are useful in the treatment of a proliferative disease selected from a benign or malignant tumor, solid tumor, liquid tumor, carcinoma of the brain, kidney, liver, adrenal gland, bladder, breast, stomach, gastric tumors, ovaries, colon, rectum, prostate, pancreas, lung, vagina, cervix, testis, genitourinary tract, esophagus, larynx, skin, bone or thyroid, sarcoma, glioblastomas, neuroblastomas, multiple myeloma, gastrointestinal cancer, especially colon carcinoma or colorectal adenoma, a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, Hodgkins and Non-Hodgkins, a mammary carcinoma, follicular carcinoma, undifferentiated carcinoma, papillary carcinoma, seminoma, melanoma, an IL-1 driven disorder, an MyD88 driven disorder, Smoldering of indolent multiple myeloma, or hematological malignancies (including leukemia, diffuse large B-cell lymphoma (DLBCL), ABC DLBCL, chronic lymphocytic leukemia (CLL), chronic lymphocytic lymphoma, primary effusion lymphoma, Burkitt lymphoma/leukemia, acute lymphocytic leukemia, B-cell prolymphocytic leukemia, lymphoplasmacytic lymphoma, Waldenstrom's macroglobulinemia (WM), splenic marginal zone lymphoma, multiple myeloma, plasmacytoma, intravascular large B-cell lymphoma).

In some embodiments, the aberrant activation of STAT3 which can be treated according to the methods of this invention is a human cancer. In some embodiments, the human cancer which can be treated according to the methods of this invention is selected from glioma, breast cancer, prostate cancer, head and neck squamous cell carcinoma, skin melanomas, and ovarian cancer. In some embodiments, abnormal STAT3 activation also correlates with the progression of diverse hematopoietic malignancies, such as various leukemias and lymphomas, and STAT3 is frequently activated in both multiple myeloma cell lines and tumor cell lines derived from patient bone marrows.

In some embodiments, the present invention provides a method of treating a cancer selected from glioma, breast cancer, prostate cancer, head and neck squamous cell carcinoma, skin melanomas, ovarian cancer, malignant peripheral nerve shealth tumors (MPNST), pancreatic cancer, non-small cell lung cancer, urothelial cancer, liver cancer, bile duct cancer, kidney cancer, colon cancer, esophageal cancer, gastric cancer, gastrointestinal stromal tumors, and hematological malignancies include lymphomas, leukemias, myelomas, myeloproliferative neoplasms and myelodysplastic syndromes.

In some embodiments, the present invention provides a method of treating a JAK-associated disease. In some embodiments, the JAK-associated disease is cancer including those characterized by solid tumors (e.g., prostate cancer, renal cancer, hepatic cancer, pancreatic cancer, gastric cancer, breast cancer, lung cancer, cancers of the head and neck, thyroid cancer, glioblastoma, Kaposi's sarcoma, Castleman's disease, uterine leiomyosarcoma, melanoma etc.), hematological cancers (e.g., lymphoma, leukemia Such as acute lymphoblastic leukemia (ALL), acute myelogenous leukemia (AML) or multiple myeloma), and skin cancer such as cutaneous T-cell lymphoma (CTCL) and cutaneous B-cell lymphoma. Example CTCLs include Sezary syndrome and mycosis fungoides.

In some embodiments, the present invention provides a method oftreating triple negative breast cancer in a patient in need thereof, comprising administering a compound of the present invention, or a pharmaceutically acceptable salt thereof.

In some embodiments, the present invention provides a method of treating malignant peripheral nerve sheath tumors (MPNST) in a patient in need thereof, comprising administering a compound of the present invention, or a pharmaceutically acceptable salt thereof.

In some embodiments, the present invention provides a method of treating lung cancer, in a patient in need thereof, comprising administering a compound of the present invention, or a pharmaceutically acceptable salt thereof.

In some embodiments, the present invention provides a method of treating colorectal cancer, in a patient in need thereof, comprising administering a compound of the present invention, or a pharmaceutically acceptable salt thereof.

In some embodiments, the present invention provides a method of treating peripheral T-cell lymphoma, in a patient in need thereof, comprising administering a compound of the present invention, or a pharmaceutically acceptable salt thereof.

In some embodiments, the present invention provides a method of treating pancreatic cancer in a patient in need thereof, comprising administering a compound of the present invention, or a pharmaceutically acceptable salt thereof.

Compounds according to the invention are useful in the treatment of inflammatory or obstructive airways diseases, resulting, for example, in reduction of tissue damage, airways inflammation, bronchial hyperreactivity, remodeling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics.

Compounds according to the invention are useful in the treatment of heteroimmune diseases. Examples of such heteroimmune diseases include, but are not limited to, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, such as therapy for or intended to restrict or abort symptomatic attack when it occurs, for example antiinflammatory or bronchodilatory. Prophylactic benefit in asthma may in particular be apparent in subjects prone to “morning dipping”. “Morning dipping” is a recognized asthmatic syndrome, common to a substantial percentage of asthmatics and characterized by asthma attack, e.g. between the hours of about 4 to 6 am, i.e. at a time normally substantially distant form any previously administered symptomatic asthma therapy.

Compounds of the current invention can be used for other inflammatory or obstructive airways diseases and conditions to which the present invention is applicable and include acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, but not limited to, acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

With regard to their anti-inflammatory activity, in particular in relation to inhibition of eosinophil activation, compounds of the invention are also useful in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil- related disorders of the airways consequential or concomitant to Loffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

Compounds of the invention are also useful in the treatment of inflammatory or allergic conditions of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, systemic lupus erythematosus, pemphigus vulgaris, pemphigus *foliaceus*, paraneoplastic pemphigus, epidermolysis bullosa acquisita, acne vulgaris, and other inflammatory or allergic conditions of the skin.

Compounds of the invention may also be used for the treatment of other diseases or conditions, such as diseases or conditions having an inflammatory component, for example, treatment of diseases and conditions of the eye such as ocular allergy, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), irritable bowel syndrome, celiac disease, periodontitis, hyaline membrane disease, kidney disease, glomerular disease, alcoholic liver disease, multiple sclerosis, endocrine opthalmopathy, Grave's disease, sarcoidosis, alveolitis, chronic hypersensitivity pneumonitis, multiple sclerosis, primary biliary cirrhosis, uveitis (anterior and posterior), Sjogren's syndrome, keratoconjunctivitis sicca and vernal keratoconjunctivitis, interstitial lung fibrosis, psoriatic arthritis, systemic juvenile idiopathic arthritis, cryopyrin-associated periodic syndrome, nephritis, vasculitis, diverticulitis, interstitial cystitis, glomerulonephritis (with and without nephrotic syndrome, e.g. including idiopathic nephrotic syndrome or minal change nephropathy), chronic granulomatous disease, endometriosis, leptospiriosis renal disease, glaucoma, retinal disease, ageing, headache, pain, complex regional pain syndrome, cardiac hypertrophy, musclewasting, catabolic disorders, obesity, fetal growth retardation, hyperchlolesterolemia, heart disease, chronic heart failure, mesothelioma, anhidrotic ecodermal dysplasia, Behcet's disease, incontinentia pigmenti, Paget's disease, pancreatitis, hereditary periodic fever syndrome, asthma (allergic and non-allergic, mild, moderate, severe, bronchitic, and exercise-induced), acute lung injury, acute respiratory distress syndrome, eosinophilia, hypersensitivities, anaphylaxis, nasal sinusitis, ocular allergy, silica induced diseases, COPD (reduction of damage, airways inflammation, bronchial hyperreactivity, remodeling or disease progression), pulmonary disease, cystic fibrosis, acid-induced lung injury, pulmonary hypertension, polyneuropathy, cataracts, muscle inflammation in conjunction with systemic sclerosis, inclusion body myositis, myasthenia gravis, thyroiditis, Addison's disease, lichen planus, Type 1 diabetes, or Type 2 diabetes, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis.

In some embodiments, the present invention provides a method of treating an autoimmune disease selected from systemic sclerosis, idiopathic pulmonary fibrosis, inflammatory bowel disease, atopic dermatitis, rheumatoid arthritis, graft versus host disease (acute and chronic), and other tissue fibrosis diseases.

In some embodiments, the present invention provides a method of treating a hematologic malignancy selected from LGL leukemia (T and NK cell), cutaneous T cell lymphoma (CTCL), peripheral T cell lymphomas (PTCL, all subtypes including ALCL), diffuse large B cell lymphoma (DLBCL), acute myelogenous leukemia, multiple myeloma, and myelofibrosis In some embodiments, the present invention provides a method of treating tissue fibrosis or chronic tissue disease, including liver and kidney fibrosis, in a patient in need thereof, comprising administering a compound of the present invention, or a pharmaceutically acceptable salt thereof.

In some embodiments, the present invention provides a method of treating idiopathic interstitial pneumonia(s) (IIPs), including any type of lung fibrosis, either interstitial lung disease associated with rheumatoid disease (including SSc) or IPF itself, in a patient in need thereof, comprising administering a compound of the present invention, or a pharmaceutically acceptable salt thereof.

In some embodiments the inflammatory disease which can be treated according to the methods of this invention is an disease of the skin. In some embodiments, the inflammatory disease of the skin is selected from contact dermatitis, atopic dermatitis, alopecia areata, erythema multiforma, dermatitis herpetiformis, scleroderma, vitiligo, hypersensitivity angiitis, urticaria, bullous pemphigoid, pemphigus vulgaris, pemphigus *foliaceus*, paraneoplastic pemphigus, epidermolysis bullosa acquisita, and other inflammatory or allergic conditions of the skin.

In some embodiments the inflammatory disease which can be treated according to the methods of this invention is selected from acute and chronic gout, chronic gouty arthritis, psoriasis, psoriatic arthritis, rheumatoid arthritis, Juvenile rheumatoid arthritis, Systemic juvenile idiopathic arthritis (SJIA), Cryopyrin Associated Periodic Syndrome (CAPS), and osteoarthritis.

In some embodiments the inflammatory disease which can be treated according to the methods of this invention is a TH17 mediated disease. In some embodiments the TH17 mediated disease is selected from Systemic lupus erythematosus, Multiple sclerosis, and inflammatory bowel disease (including Crohn's disease or ulcerative colitis).

In some embodiments the inflammatory disease which can be treated according to the methods of this invention is selected from Sjogren's syndrome, allergic disorders, osteoarthritis, conditions of the eye such as ocular allergy, conjunctivitis, keratoconjunctivitis sicca and vernal conjunctivitis, and diseases affecting the nose such as allergic rhinitis.

Cardiovascular diseases which can be treated according to the methods of this invention include, but are not limited to, restenosis, cardiomegaly, atherosclerosis, myocardial infarction, ischemic stroke, congestive heart failure, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, and deep venous thrombosis.

In some embodiments, the neurodegenerative disease which can be treated according to the methods of this invention include, but are not limited to, Alzheimer's disease, Parkinson's disease, amyotrophic lateral sclerosis, Huntington's disease, cerebral ischemia, and neurodegenerative disease caused by traumatic injury, glutamate neurotoxicity, hypoxia, epilepsy, treatment of diabetes, metabolic syndrome, obesity, organ transplantation and graft versus host disease.

In some embodiments the invention provides a method of treating, preventing or lessening the severity of Alzheimer's disease comprising administering to a patient in need thereof a provided compound or a pharmaceutically acceptable salt or composition thereof.

In some embodiments the invention provides a method of treating a disease or condition commonly occurring in connection with transplantation. In some embodiments, the disease or condition commonly occurring in connection with transplantation is selected from organ transplantation, organ transplant rejection, and graft versus host disease.

In some embodiments the invention provides a method of treating a metabolic disease. In some embodiments the metabolic disease is selected from Type 1 diabetes, Type 2 diabetes, metabolic syndrome, and obesity.

In some embodiments the invention provides a method of treating a viral disease. In some embodiments, the viral infection is HIV infection.

Furthermore, the invention provides the use of a compound according to the definitions herein, or a pharmaceutically acceptable salt, or a hydrate or solvate thereof for the preparation of a medicament for the treatment of a proliferative disease, an inflammatory disease, an obstructive respiratory disease, a cardiovascular disease, a metabolic disease, a neurological disease, a neurodegenerative disease, a viral disease, or a disorder commonly occurring in connection with transplantation.

Combination Therapies

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated."

In certain embodiments, a provided combination, or composition thereof, is administered in combination with another therapeutic agent.

In some embodiments, the present invention provides a method of treating a disclosed disease or condition comprising administering to a patient in need thereof an effective amount of a compound disclosed herein or a pharmaceutically acceptable salt thereof and co-administering simultaneously or sequentially an effective amount of one or more additional therapeutic agents, such as those described herein. In some embodiments, the method includes co-administering one additional therapeutic agent. In some embodiments, the method includes co-administering two additional therapeutic agents. In some embodiments, the combination of the disclosed compound and the additional therapeutic agent or agents acts synergistically.

Examples of agents the combinations of this invention may also be combined with include, without limitation: treatments for Alzheimer's Disease such as Aricept® and Excelon®; treatments for HIV such as ritonavir; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif*), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 $R^A$, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-ylral agents; agents for treating blood disorders such as corticosteroids, anti-leukemic agents, and growth factors; agents that prolong or improve pharmacokinetics such as cytochrome P450 inhibitors (i.e., inhibitors of metabolic breakdown) and CYP3A4 inhibitors (e.g., ketokenozole and ritonavir), and agents for treating immunodeficiency disorders such as gamma globulin.

In certain embodiments, combination therapies of the present invention, or a pharmaceutically acceptable composition thereof, are administered in combination with a monoclonal antibody or an siRNA therapeutic.

Those additional agents may be administered separately from a provided combination therapy, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a combination of the present invention may be administered with another therapeutic agent simultaneously or sequentially in separate unit dosage forms or together in a single unit dosage form.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

One or more other therapeutic agent may be administered separately from a compound or composition of the invention, as part of a multiple dosage regimen. Alternatively, one or more other therapeutic agents may be part of a single dosage form, mixed together with a compound of this invention in a single composition. If administered as a multiple dosage regime, one or more other therapeutic agent and a compound or composition of the invention may be administered simultaneously, sequentially or within a period of time from one another, for example within 1, 2, 3, 4, 5, 6, 7, 8, 9, 10, 11, 12, 13, 14, 15, 16, 17, 18, 18, 20, 21, 22, 23, or 24 hours from one another. In some embodiments, one or more other therapeutic agent and a compound or composition of the invention are administered as a multiple dosage regimen within greater than 24 hours apart.

In one embodiment, the present invention provides a composition comprising a provided compound and one or more additional therapeutic agents. The therapeutic agent may be administered together with a provided compound, or may be administered prior to or following administration of a provided compound. Suitable therapeutic agents are described in further detail below. In certain embodiments, a provided compound may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a provided compound may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In another embodiment, the present invention provides a method of treating an inflammatory disease, disorder or condition by administering to a patient in need thereof a provided compound and one or more additional therapeutic agents. Such additional therapeutic agents may be small molecules or recombinant biologic agents and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), canakinumab (Ilaris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmocort®), and flunisolide (Aerobid®), Afviar®, Symbicort®, Dulera®, cromolyn sodium (Intal®), methylxanthines such as theophyl]ine (Theo-Dur®, Theolair®, Slo-bid®, Uniphyl®, Theo-24®) and aminophyl]ine, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Revlimid®), or any combination(s) thereof.

In another embodiment, the present invention provides a method of treating gout comprising administering to a patient in need thereof a provided compound and one or more additional therapeutic agents selected from non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol and febuxostat (Uloric®).

In another embodiment, the present invention provides a method of treating rheumatoid arthritis comprising administering to a patient in need thereof a provided compound and one or more additional therapeutic agents selected from non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-I" agents such as anakinra (Kineret®) and rilonacept (Arcalyst®), antibodies such as rituximab (Rituxan®), "anti-T-cell" agents such as abatacept (Orencia®) and "anti-IL-6" agents such as tocilizumab (Actemra®).

In some embodiments, the present invention provides a method of treating osteoarthritis comprising administering to a patient in need thereof a provided compound and one or more additional therapeutic agents selected from acetaminophen, non-steroidal anti-inflammatory drugs (NSAIDS) such as aspirin, ibuprofen, naproxen, etodolac (Lodine®) and celecoxib, diclofenac, cortisone, hyaluronic acid (Synvisc® or Hyalgan®) and monoclonal antibodies such as tanezumab.

In some embodiments, the present invention provides a method of treating lupus comprising administering to a patient in need thereof a provided compound and one or more additional therapeutic agents selected from acetaminophen, non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, antimalarials such as hydroxychloroquine (Plaquenil®) and chloroquine (Aralen®), cyclophosphamide (Cytoxan®), methotrexate (Rheumatrex®), azathioprine (Imuran®) and anticoagulants such as heparin (Calcinparine® or Liquaemin®) and warfarin (Coumadin®).

In some embodiments, the present invention provides a method of treating inflammatory bowel disease comprising administering to a patient in need thereof a provided compound and one or more additional therapeutic agents selected from mesalamine (Asacol®) sulfasalazine (Azulfidine®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot® and anticholinergics or antispasmodics such as dicyclomine (Bentyl®), anti-TNF therapies, steroids, and antibiotics such as Flagyl or ciprofloxacin.

In some embodiments, the present invention provides a method of treating asthma comprising administering to a patient in need thereof a provided compound and one or more additional therapeutic agents selected from Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, cromolyn sodium (Intal®), methylxanthines such as theophyl]ine (Theo-Dur®, Theolair®, Slo-bid®, Uniphyl®, Theo-24®) and aminophyl]ine, and IgE antibodies such as omalizumab (Xolair®).

In some embodiments, the present invention provides a method of treating COPD comprising administering to a patient in need thereof a provided compound and one or more additional therapeutic agents selected from beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), methylxanthines such as theophyl]ine (Theo-Dur®, Theolair®, Slo-bid®, Uniphyl®, Theo-24®) and aminophyl]ine, inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, In some embodiments, the present invention provides a method of treating HIV comprising administering to a patient in need thereof a provided compound and one or more additional therapeutic agents selected from nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), and combinations thereof.

In another embodiment, the present invention provides a method of treating a hematological malignancy comprising administering to a patient in need thereof a provided compound and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a TYK2 inhibitor, a P13K inhibitor, a SYK inhibitor, and combinations thereof.

In another embodiment, the present invention provides a method of treating a solid tumor comprising administering to a patient in need thereof a provided compound and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a TYK2 inhibitor, a P13K inhibitor, a SYK inhibitor, and combinations thereof.

In another embodiment, the present invention provides a method of treating a hematological malignancy comprising administering to a patient in need thereof a provided compound and a Hedgehog (Hh) signaling pathway inhibitor. In some embodiments, the hematological malignancy is DLBCL (Ramirez et al "Defining causative factors contributing in the activation of hedgehog signaling in diffuse large B-cell lymphoma" Leuk. Res. (2012), published online July 17, and incorporated herein by reference in its entirety).

In another embodiment, the present invention provides a method of treating diffuse large B-cell lymphoma (DLBCL) comprising administering to a patient in need thereof a provided compound and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, and combinations thereof.

In another embodiment, the present invention provides a method of treating multiple myeloma comprising administering to a patient in need thereof a provided compound and one or more additional therapeutic agents selected from bortezomib (Velcade®), and dexamethasone (Decadron®), a hedgehog signaling inhibitor, a BTK inhibitor, a JAK/pan-JAK inhibitor, a TYK2 inhibitor, a PI3K inhibitor, a SYK inhibitor in combination with lenalidomide (Revlimid®).

In another embodiment, the present invention provides a method of treating Waldenstrom's macroglobulinemia comprising administering to a patient in need thereof a provided compound and one or more additional therapeutic agents selected from chlorambucil (Leukeran®), cyclophosphamide (Cytoxan®, Neosar®), fludarabine (Fludara®), cladribine (Leustatin®), rituximab (Rituxan®), a hedgehog signaling inhibitor, a BTK inhibitor, a JAK/pan-JAK inhibitor, a TYK2 inhibitor, a PI3K inhibitor, and a SYK inhibitor.

In some embodiments, one or more other therapeutic agent is an antagonist of the hedgehog pathway. Approved hedgehog pathway inhibitors which may be used in the present invention include sonidegib (Odomzo®, Sun Pharmaceuticals); and vismodegib (Erivedge®, Genentech), both for treatment of basal cell carcinoma.

In some embodiments, one or more other therapeutic agent is a Poly ADP ribose polymerase (PARP) inhibitor. In some embodiments, a PARP inhibitor is selected from olaparib (Lynparza®, AstraZeneca); rucaparib (Rubraca®, Clovis Oncology); niraparib (Zejula®, Tesaro); talazoparib (MDV3800/BMN 673/LT00673, Medivation/Pfizer/Biomarin); veliparib (ABT-888, AbbVie); and BGB-290 (BeiGene, Inc.).

In some embodiments, one or more other therapeutic agent is a histone deacetylase (HDAC) inhibitor. In some embodiments, an HDAC inhibitor is selected from vorinostat (Zolinza®, Merck); romidepsin (Istodax®, Celgene); panobinostat (Farydak®, Novartis); belinostat (Beleodaq®, Spectrum Pharmaceuticals); entinostat (SNDX-275, Syndax Pharmaceuticals) (NCT00866333); and chidamide (Epidaza®, HBI-8000, Chipscreen Biosciences, China).

In some embodiments, one or more other therapeutic agent is a CDK inhibitor, such as a CDK4/CDK6 inhibitor. In some embodiments, a CDK 4/6 inhibitor is selected from palbociclib (Ibrance®, Pfizer); ribociclib (Kisqali®, Novartis); abemaciclib (Ly2835219, Eli Lilly); and trilaciclib (G1T28, G1 Therapeutics).

In some embodiments, one or more other therapeutic agent is a folic acid inhibitor. Approved folic acid inhibitors useful in the present invention include pemetrexed (Alimta®, Eli Lilly).

In some embodiments, one or more other therapeutic agent is a CC chemokine receptor 4 (CCR4) inhibitor. CCR4 inhibitors being studied that may be useful in the present invention include mogamulizumab (Poteligeo®, Kyowa Hakko Kirin, Japan).

In some embodiments, one or more other therapeutic agent is an isocitrate dehydrogenase (IDH) inhibitor. IDH inhibitors being studied which may be used in the present invention include AG120 (Celgene; NCT02677922); AG221 (Celgene, NCT02677922; NCT02577406); BAY1436032 (Bayer, NCT02746081); IDH305 (Novartis, NCT02987010).

In some embodiments, one or more other therapeutic agent is an arginase inhibitor. Arginase inhibitors being studied which may be used in the present invention include AEB1102 (pegylated recombinant arginase, Aeglea Biotherapeutics), which is being studied in Phase 1 clinical trials for acute myeloid leukemia and myelodysplastic syndrome (NCT02732184) and solid tumors (NCT02561234); and CB-1158 (Calithera Biosciences).

In some embodiments, one or more other therapeutic agent is a glutaminase inhibitor. Glutaminase inhibitors being studied which may be used in the present invention include CB-839 (Calithera Biosciences).

In some embodiments, one or more other therapeutic agent is an antibody that binds to tumor antigens, that is, proteins expressed on the cell surface of tumor cells. Approved antibodies that bind to tumor antigens which may be used in the present invention include rituximab (Rituxan®, Genentech/BiogenIdec); ofatumumab (anti-CD20, Arzerra®, GlaxoSmithKline); obinutuzumab (anti-CD20, Gazyva®, Genentech), ibritumomab (anti-CD20 and Yttrium-90, Zevalin®, Spectrum Pharmaceuticals); daratumumab (anti-CD38, Darzalex®, Janssen Biotech), dinutuximab (anti-glycolipid GD2, Unituxin®, United Therapeutics); trastuzumab (anti-HER2, Herceptin®, Genentech); ado-trastuzumab emtansine (anti-HER2, fused to emtansine, Kadcyla®, Genentech); and pertuzumab (anti-HER2, Perjeta®, Genentech); and brentuximab vedotin (anti-CD30-drug conjugate, Adcetris®, Seattle Genetics).

In some embodiments, one or more other therapeutic agent is a topoisomerase inhibitor. Approved topoisomerase inhibitors useful in the present invention include irinotecan (Onivyde®, Merrimack Pharmaceuticals); topotecan (Hycamtin®, GlaxoSmithKline). Topoisomerase inhibitors being studied which may be used in the present invention include pixantrone (Pixuvri®, CTI Biopharma).

In some embodiments, one or more other therapeutic agent is an inhibitor of anti-apoptotic proteins, such as BCL-2. Approved anti-apoptotics which may be used in the present invention include venetoclax (Venclexta®, AbbVie/Genentech); and blinatumomab (Blincyto®, Amgen). Other therapeutic agents targeting apoptotic proteins which have undergone clinical testing and may be used in the present invention include navitoclax (ABT-263, Abbott), a BCL-2 inhibitor (NCT02079740).

In some embodiments, one or more other therapeutic agent is an androgen receptor inhibitor. Approved androgen receptor inhibitors useful in the present invention include enzalutamide (Xtandi®, Astellas/Medivation); approved inhibitors of androgen synthesis include abiraterone (Zytiga®, Centocor/Ortho); approved antagonist of gonadotropin-releasing hormone (GnRH) receptor (degaralix, Firmagon®, Ferring Pharmaceuticals).

In some embodiments, one or more other therapeutic agent is a selective estrogen receptor modulator (SERM), which interferes with the synthesis or activity of estrogens. Approved SERMs useful in the present invention include raloxifene (Evista®, Eli Lilly).

In some embodiments, one or more other therapeutic agent is an inhibitor of bone resorption. An approved therapeutic which inhibits bone resorption is Denosumab (Xgeva®, Amgen), an antibody that binds to RANKL, prevents binding to its receptor RANK, found on the surface of osteoclasts, their precursors, and osteoclast-like giant cells, which mediates bone pathology in solid tumors with osseous metastases. Other approved therapeutics that inhibit bone resorption include bisphosphonates, such as zoledronic acid (Zometa®, Novartis).

In some embodiments, one or more other therapeutic agent is an inhibitor of interaction between the two primary p53 suppressor proteins, MDMX and MDM2. Inhibitors of p53 suppression proteins being studied which may be used in the present invention include ALRN-6924 (Aileron), a stapled peptide that equipotently binds to and disrupts the interaction of MDMX and MDM2 with p53. ALRN-6924 is currently being evaluated in clinical trials for the treatment of AML, advanced myelodysplastic syndrome (MDS) and peripheral T-cell lymphoma (PTCL) (NCT02909972; NCT02264613).

In some embodiments, one or more other therapeutic agent is an inhibitor of transforming growth factor-beta (TGF-beta or TGFβ). Inhibitors of TGF-beta proteins being studied which may be used in the present invention include NIS793 (Novartis), an anti-TGF-beta antibody being tested in the clinic for treatment of various cancers, including breast, lung, hepatocellular, colorectal, pancreatic, prostate and renal cancer (NCT 02947165). In some embodiments, the inhibitor of TGF-beta proteins is fresolimumab (GC1008; Sanofi-Genzyme), which is being studied for melanoma (NCT00923169); renal cell carcinoma (NCT00356460); and non-small cell lung cancer (NCT02581787). Additionally, in some embodiments, the additional therapeutic agent is a TGF-beta trap, such as described in Connolly et al. (2012) Int'l J. Biological Sciences 8:964-978. One therapeutic compound currently in clinical trials for treatment of solid tumors is M7824 (Merck KgaA—formerly MSB0011459X), which is a bispecific, anti-PD-L1/TGFβ trap compound (NCT02699515); and (NCT02517398). M7824 is comprised of a fully human IgG1 antibody against PD-L1 fused to the extracellular domain of human TGF-beta receptor II, which functions as a TGFβ "trap."

In some embodiments, one or more other therapeutic agent is selected from glembatumumab vedotin-monomethyl auristatin E (MMAE) (Celldex), an anti-glycoprotein NMB (gpNMB) antibody (CR011) linked to the cytotoxic MMAE. gpNMB is a protein overexpressed by multiple tumor types associated with cancer cells' ability to metastasize.

In some embodiments, one or more other therapeutic agent is an antiproliferative compound. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, $AZd_6244$ from AstraZeneca, PD181461 from Pfizer and leucovorin.

In some embodiments, the present invention provides a method of treating Alzheimer's disease comprising administering to a patient in need thereof a provided compound and one or more additional therapeutic agents selected from donepezil (Aricept®), rivastigmine (Excelon®), galantamine (Razadyne®), tacrine (Cognex®), and memantine (Namenda®).

In some embodiments, one or more other therapeutic agent is a taxane compound, which causes disruption of microtubules, which are essential for cell division. In some embodiments, a taxane compound is selected from paclitaxel (Taxol®, Bristol-Myers Squibb), docetaxel (Taxotere®, Sanofi-Aventis; Docefrez®, Sun Pharmaceutical), albumin-bound paclitaxel (Abraxane®; Abraxis/Celgene), cabazitaxel (Jevtana®, Sanofi-Aventis), and SID530 (SK Chemicals, Co.) (NCT00931008).

In some embodiments, one or more other therapeutic agent is a nucleoside inhibitor, or a therapeutic agent that interferes with normal DNA synthesis, protein synthesis, cell replication, or will otherwise inhibit rapidly proliferating cells.

In some embodiments, a nucleoside inhibitor is selected from trabectedin (guanidine alkylating agent, Yondelis®, Janssen Oncology), mechlorethamine (alkylating agent, Valchlor®, Aktelion Pharmaceuticals); vincristine (Oncovin®, Eli Lilly; Vincasar®, Teva Pharmaceuticals; Marqibo®, Talon Therapeutics); temozolomide (prodrug to alkylating agent 5-(3-methyltriazen-1-yl)-imidazole-4-carboxamide (MTIC) Temodar®, Merck); cytarabine injection (ara-C, antimetabolic cytidine analog, Pfizer); lomustine (alkylating agent, CeeNU®, Bristol-Myers Squibb; Gleostine®, NextSource Biotechnology); azacitidine (pyrimidine nucleoside analog of cytidine, Vidaza®, Celgene); omacetaxine mepesuccinate (cephalotaxine ester) (protein synthesis inhibitor, Synribo®; Teva Pharmaceuticals); asparaginase *Erwinia chrysanthemi* (enzyme for depletion of asparagine, Elspar®, Lundbeck; Erwinaze®, EUSA Pharma); eribulin mesylate (microtubule inhibitor, tubulin-based antimitotic, Halaven®, Eisai); cabazitaxel (microtubule inhibitor, tubulin-based antimitotic, Jevtana®, Sanofi-Aventis); capacetrine (thymidylate synthase inhibitor, Xeloda®, Genentech); bendamustine (bifunctional mechlorethamine derivative, believed to form interstrand DNA cross-links, Treanda®, Cephalon/Teva); ixabepilone (semi-synthetic analog of epothilone B, microtubule inhibitor, tubulin-based antimitotic, Ixempra®, Bristol-Myers Squibb); nelarabine (prodrug of deoxyguanosine analog, nucleoside metabolic inhibitor, Arranon®, Novartis); clorafabine (prodrug of ribonucleotide reductase inhibitor, competitive inhibitor of deoxycytidine, Clolar®, Sanofi-Aventis); and trifluridine and tipiracil (thymidine-based nucleoside analog and thymidine phosphorylase inhibitor, Lonsurf®, Taiho Oncology).

In some embodiments, one or more other therapeutic agent is a kinase inhibitor or VEGF-R antagonist. Approved VEGF inhibitors and kinase inhibitors useful in the present invention include: bevacizumab (Avastin®, Genentech/Roche) an anti-VEGF monoclonal antibody; ramucirumab (Cyramza®, Eli Lilly), an anti-VEGFR-2 antibody and ziv-aflibercept, also known as VEGF Trap (Zaltrap®; Regeneron/Sanofi). VEGFR inhibitors, such as regorafenib (Stivarga®, Bayer); vandetanib (Caprelsa®, AstraZeneca); axitinib (Inlyta®, Pfizer); and lenvatinib (Lenvima®, Eisai); Raf inhibitors, such as sorafenib (Nexavar®, Bayer A G and Onyx); dabrafenib (Tafinlar®, Novartis); and vemurafenib (Zelboraf®, Genentech/Roche); MEK inhibitors, such as cobimetanib (Cotellic®, Exelexis/Genentech/Roche); trametinib (Mekinist®, Novartis); Bcr-Abl tyrosine kinase inhibitors, such as imatinib (Gleevec®, Novartis); nilotinib (Tasigna®, Novartis); dasatinib (Sprycel®, BristolMyersSquibb); bosutinib (Bosulif®, Pfizer); and ponatinib (Inclusig®, Ariad Pharmaceuticals); Her2 and EGFR inhibitors, such as gefitinib (Iressa®, AstraZeneca); erlotinib (Tarceeva®, Genentech/Roche/Astellas); lapatinib (Tykerb®, Novartis); afatinib (Gilotrif®, Boehringer Ingelheim); osimertinib (targeting activated EGFR, Tagrisso®, AstraZeneca); and brigatinib (Alunbrig®, Ariad Pharmaceuticals); c-Met and VEGFR2 inhibitors, such as cabozanitib (Cometriq®, Exelexis); and multikinase inhibitors, such as sunitinib (Sutent®, Pfizer); pazopanib (Votrient®, Novartis); ALK inhibitors, such as crizotinib (Xalkori®, Pfizer); ceritinib (Zykadia®, Novartis); and alectinib (Alecenza®, Genentech/Roche); Bruton's tyrosine kinase inhibitors, such as ibrutinib (Imbruvica®, Pharmacyclics/Janssen); and Flt3 receptor inhibitors, such as midostaurin (Rydapt®, Novartis).

Other kinase inhibitors and VEGF-R antagonists that are in development and may be used in the present invention include tivozanib (Aveo Pharmaceuticals); vatalanib (Bayer/Novartis); lucitanib (Clovis Oncology); dovitinib (TK1258, Novartis); Chiauanib (Chipscreen Biosciences); CEP-11981 (Cephalon); linifanib (Abbott Laboratories); neratinib (HKI-272, Puma Biotechnology); radotinib (Supect®, IY5511, Il-Yang Pharmaceuticals, S. Korea); ruxolitinib (Jakafi®, Incyte Corporation); PTC299 (PTC Therapeutics); CP-547,632 (Pfizer); foretinib (Exelexis, GlaxoSmithKline); quizartinib (Daiichi Sankyo) and motesanib (Amgen/Takeda).

In another embodiment, the present invention provides a method of treating organ transplant rejection or graft vs. host disease comprising administering to a patient in need thereof a provided compound and one or more additional therapeutic agents selected from a steroid, cyclosporin, FK506, rapamycin, a hedgehog signaling inhibitor, a BTK inhibitor, a JAK/pan-JAK inhibitor, a TYK2 inhibitor, a PI3K inhibitor, and a SYK inhibitor.

In another embodiment, the present invention provides a method of treating or lessening the severity of a disease comprising administering to a patient in need thereof a provided compound and a BTK inhibitor, wherein the disease is selected from inflammatory bowel disease, arthritis, systemic lupus erythematosus (SLE), vasculitis, idiopathic thrombocytopenic purpura (ITP), rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, autoimmune thyroiditis, Sjogren's syndrome, multiple sclerosis, systemic sclerosis, Lyme neuroborreliosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, autoimmune gastritis, pernicious anemia, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, membranous glomerulonephropathy, endometriosis, interstitial cystitis, pemphigus vulgaris, bullous pemphigoid, neuromyotonia, scleroderma, vulvodynia, a hyperproliferative disease, rejection of transplanted organs or tissues, Acquired Immunodeficiency Syndrome (AIDS, also known as HIV), type 1 diabetes, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis, asthma, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis, B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis, breast cancer, prostate cancer, or cancer of the mast cells (e.g., mastocytoma, mast cell leukemia, mast cell sarcoma, systemic mastocytosis), bone cancer, colorectal cancer, pancreatic cancer, diseases of the bone and joints including, without limitation, rheumatoid arthritis, seronegative spondyloarthropathies (including ankylosing spondylitis, psoriatic arthritis and Reiter's disease), Behcet's disease, Sjogren's syndrome, systemic sclerosis, osteoporosis, bone cancer, bone metastasis, a thromboembolic disorder, (e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, deep venous thrombosis), inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleraderma, mycosis fungoides, acute inflammatory responses (such as acute respiratory distress syndrome and ischemia/reperfusion injury), and Graves' disease.

In another embodiment, the present invention provides a method of treating or lessening the severity of a disease comprising administering to a patient in need thereof a provided compound and a PI3K inhibitor, wherein the disease is selected from a cancer, a neurodegenative disorder, an angiogenic disorder, a viral disease, an autoimmune disease, an inflammatory disorder, a hormone-related disease, conditions associated with organ transplantation, immunodeficiency disorders, a destructive bone disorder, a proliferative disorder, an infectious disease, a condition associated with cell death, thrombin-induced platelet aggregation, chronic myelogenous leukemia (CML), chronic lymphocytic leukemia (CLL), liver disease, pathologic immune conditions involving T cell activation, a cardiovascular disorder, and a CNS disorder.

In another embodiment, the present invention provides a method of treating or lessening the severity of a disease comprising administering to a patient in need thereof a provided compound and a PI3K inhibitor, wherein the disease is selected from benign or malignant tumor, carcinoma or solid tumor of the brain, kidney (e.g., renal cell carcinoma (RCC)), liver, adrenal gland, bladder, breast, stomach, gastric tumors, ovaries, colon, rectum, prostate, pancreas, lung, vagina, endometrium, cervix, testis, genitourinary tract, esophagus, larynx, skin, bone or thyroid, sarcoma, glioblastomas, neuroblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, (including, for example, non-Hodgkin's Lymphoma (NHL) and Hodgkin's lymphoma (also termed Hodgkin's or Hodgkin's disease)), a mammary carcinoma, follicular carcinoma, undifferentiated carcinoma, papillary carcinoma, seminoma, melanoma, or a leukemia, diseases include Cowden syndrome, Lhermitte-Dudos disease and Bannayan-Zonana syndrome, or diseases in which the PI3K/PKB pathway is aberrantly activated, asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection, acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy, bronchitis of whatever type or genesis including, but not limited to, acute, arachidic, catarrhal, croupus, chronic or phthinoid bronchitis, pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis, Loffler's syndrome, eosinophilic, pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction, psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy, restenosis, cardiomegaly, atherosclerosis, myocardial infarction, ischemic stroke and congestive heart failure, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

In some embodiments, one or more other therapeutic agent is a phosphatidylinositol 3 kinase (P13K) inhibitor. In some embodiments, a P13K inhibitor is selected from idelalisib (Zydelig®, Gilead), alpelisib (BYL719, Novartis), taselisib (GDC-0032, Genentech/Roche); pictilisib (GDC-0941, Genentech/Roche); copanlisib (BAY806946, Bayer); duvelisib (formerly IPI-145, Infinity Pharmaceuticals); PQR309 (Piqur Therapeutics, Switzerland); and TGR1202 (formerly RP5230, TG Therapeutics).

The compounds and compositions, according to the method of the present invention, may be administered using any amount and any route of administration effective for treating or lessening the severity of a cancer, an autoimmune disorder, a proliferative disorder, an inflammatory disorder, a neurodegenerative or neurological disorder, schizophrenia, a bone-related disorder, liver disease, or a cardiac disorder. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms fortopical ortransdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting protein kinase activity or degading a protein kinase in a biological sample comprising the step of contacting said biological sample with a compound of this invention, or a composition comprising said compound.

According to another embodiment, the invention relates to a method of inhibiting or degrading STAT1, STAT2, STAT3, STAT4, STAT5A, STAT5B, or STAT6, or a mutant thereof, activity in a biological sample comprising the step of contacting said biological sample with a compound of this invention, or a composition comprising said compound.

The term "biological sample", as used herein, includes, without limitation, cell cultures or extracts thereof, biopsied material obtained from a mammal or extracts thereof, and blood, saliva, urine, feces, semen, tears, or other body fluids or extracts thereof.

Inhibition and/or degradation of a STAT protein, or a protein selected from STAT1, STAT2, STAT3, STAT4, STAT5A, STAT5B, or STAT6, or a mutant thereof, activity in a biological sample is useful for a variety of purposes that are known to one of skill in the art. Examples of such purposes include, but are not limited to, blood transfusion, organ-transplantation, biological specimen storage, and biological assays.

Another embodiment of the present invention relates to a method of degrading a protein kinase and/or inhibiting protein kinase activity in a patient comprising the step of administering to said patient a compound of the present invention, or a composition comprising said compound.

According to another embodiment, the invention relates to a method of degrading and/or inhibiting one or more of STAT1, STAT2, STAT3, STAT4, STAT5A, STAT5B, or STAT6, or a mutant thereof, activity in a patient comprising the step of administering to said patient a compound of the present invention, or a composition comprising said compound. In other embodiments, the present invention provides a method for treating a disorder mediated by one or more of STAT1, STAT2, STAT3, STAT4, STAT5A, STAT5B, or STAT6, or a mutant thereof, in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

A compound of the current invention may also be used to advantage in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3;

Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin.

The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™. Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

In some embodiments, one or more other therapeutic agent is an mTOR inhibitor, which inhibits cell proliferation, angiogenesis and glucose uptake. In some embodiments, an mTOR inhibitor is everolimus (Afinitor®, Novartis); temsirolimus (Torisel®, Pfizer); and sirolimus (Rapamune®, Pfizer).

In some embodiments, one or more other therapeutic agent is an aromatase inhibitor. In some embodiments, an aromatase inhibitor is selected from exemestane (Aromasin®, Pfizer); anastazole (Arimidex®, AstraZeneca) and letrozole (Femara®, Novartis).

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™ Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™) The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™), daunorubicin, epirubicin, idarubicin and nemorubicin, the anthraquinones mitoxantrone and losoxantrone, and the podophillotoxines etoposide and teniposide. Etoposide is marketed under the trade name Etopophos™ Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; *vinca* alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™. Docetaxel is marketed under the trade name Taxotere™. Vinblastine sulfate is marketed under the trade name Vinblastin R.P™. Vincristine sulfate is marketed under the trade name Farmistin™

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof, see WO2008118802), navitoclax (and analogs thereof, see U.S. Pat. No. 7,390,799), NH-1 (Shenayng Pharmaceutical University), obatoclax (and analogs thereof, see WO2004106328), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, TYK2, BTK and TEC family, and/or members of the cyclin-dependent kinase family (CDK) including staurosporne derivatives, such as midostaurin; examples of further compounds include UCN-01, safingol, BAY 43-9006, Bryostatin 1, Perifosine; llmofosine; RO 318220 and RO 320432; GO 6976; 1sis 3521; LY333531/LY379196; isochinoline compounds; FTIs; PD184352 or QAN697 (a P13K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin A G 213; Tyrphostin A G 1748; Tyrphostin A G 490; Tyrphostin B44; Tyrphostin B44 (+) enantiomer; Tyrphostin A G 555; AG 494; Tyrphostin A G 556, AG957 and adaphostin (4-{[(2,5-dihydroxyphenyl)methyl]amino}-benzoic acid adamantyl ester; NSC 680410, adaphostin); 1) compounds targeting, decreasing or inhibiting the activity of the epidermal growth factor family of receptor tyrosine kinases ($EGFR_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, C1-1033, EKB-569, GW-2016, ELI, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

Compounds which target, decrease or inhibit the activity of a protein or lipid phosphatase are e.g. inhibitors of phosphatase 1, phosphatase 2A, or CDC25, such as okadaic acid or a derivative thereof.

In some embodiments, one or more other therapeutic agent is a growth factor antagonist, such as an antagonist of platelet-derived growth factor (PDGF), or epidermal growth factor (EGF) or its receptor (EGFR). Approved PDGF antagonists which may be used in the present invention include olaratumab (Lartruvo®; Eli Lilly). Approved EGFR antagonists which may be used in the present invention include cetuximab (Erbitux®, Eli Lilly); necitumumab (Portrazza®, Eli Lilly), panitumumab (Vectibix®, Amgen); and osimertinib (targeting activated EGFR, Tagrisso®, AstraZeneca).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3β-C2β, PI3β-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PI3K inhibitory compounds, and conditions treatable by such compounds in combination with compounds of this invention can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2- arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or $R_{115777}$ (Zamestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™), ); carfilzomib (Kyprolis®, Amgen); and ixazomib (Ninlaro®, Takeda), and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-O-D-arabinofuransylcytosine (ara-c) and bisulfan; and ALK inhibitors, which are compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino, 17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin$^{T}$M), rituximab (Rituxan©), PR064553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]- amino]methyl] phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term “ionizing radiation” referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., $4^{th}$ Edition, Vol. 1, pp. 248-275 (1993).

Also included are EDG binders and ribonucleotide reductase inhibitors. The term “EDG binders” as used herein refers to a class of immunosuppressants that modulates lymphocyte recirculation, such as FTY720. The term “ribonucleotide reductase inhibitors” refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1 ,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgG1 antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-a-epihydrocotisol, cortexolone, 17a-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The compounds of the invention are also useful as co-therapeutic compounds for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. A compound of the invention may be mixed with the other drug substance in a fixed pharmaceutical composition or it may be administered separately, before, simultaneously with or after the other drug substance. Accordingly the invention includes a combination of a compound of the invention as hereinbefore described with an anti-inflammatory, bronchodilatory, antihistamine or anti-tussive drug substance, said compound of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate; non-steroidal glucocorticoid receptor agonists; LTB4 antagonists such LY293111, CGS025019C, CP-195543, SC-53228, BIIL 284, ONO 4057, SB 209247; LTD4 antagonists such as montelukast and zafirlukast; PDE4 inhibitors such cilomilast (Ariflo® GlaxoSmithKline), Roflumilast (Byk Gulden),V-11294A (Napp), BAY19-8004 (Bayer), SCH-351591 (Schering- Plough), Arofyl]ine (Almirall Prodesfarma), PD189659/PD168787 (Parke-Davis), AWD-12- 281 (Asta Medica), CDC-801 (Celgene), SeICID(TM)CC-10004 (Celgene), VM554/UM565 (Vemalis), T-440 (Tanabe), KW-4490 (Kyowa Hakko Kogyo); A2a agonists; A2b antagonists; and beta-2 adrenoceptor agonists such as albuterol (salbutamol), metaproterenol, terbutaline, salmeterol fenoterol, procaterol, and especially, formoterol and pharmaceutically acceptable salts thereof. Suitable bronchodilatory drugs include anticholinergic or antimuscarinic compounds, in particular ipratropium bromide, oxitropium bromide, tiotropium salts and CHF 4226 (Chiesi), and glycopyrrolate.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine.

Other useful combinations of compounds of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH- 55700 and SCH-D, and Takeda antagonists such as N-[[4-[[[6,7-dihydro-2-(4-methylphenyl)-5H-benzo-cyclohepten-8-yl]carbonyl]amino]phenyl]-methyl] tetrahydro-N,N-dimethyl-2H-pyran-4-aminium chloride (TAK-770).

The structure of the active compounds identified by code numbers, generic or trade names may be taken from the actual edition of the standard compendium “The Merck Index” or from databases, e.g. Patents International (e.g. IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 μg/kg body weight/day of the additional therapeutic agent can be administered.

The amount of one or more other therapeutic agent present in the compositions of this invention may be no more than the amount that would normally be administered in a composition comprising that therapeutic agent as the only active agent. Preferably the amount of one or more other therapeutic agent in the presently disclosed compositions will range from about 50% to 100% of the amount normally present in a composition comprising that agent as the only therapeutically active agent. In some embodiments, one or more other therapeutic agent is administered at a dosage of about 50%, about 55%, about 60%, about 65%, about 70%, about 75%, about 80%, about 85%, about 90%, or about 95% of the amount normally administered for that agent. As used herein, the phrase "normally administered" means the amount an FDA approved therapeutic agent is provided for dosing per the FDA label insert.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

Exemplary Immuno-Oncology Agents

In some embodiments, one or more other therapeutic agent is an immuno-oncology agent. As used herein, the term "an immuno-oncology agent" refers to an agent which is effective to enhance, stimulate, and/or up-regulate immune responses in a subject. In some embodiments, the administration of an immuno-oncology agent with a compound of the invention has a synergic effect in treating a cancer.

An immuno-oncology agent can be, for example, a small molecule drug, an antibody, or a biologic or small molecule. Examples of biologic immuno-oncology agents include, but are not limited to, cancer vaccines, antibodies, and cytokines. In some embodiments, an antibody is a monoclonal antibody. In some embodiments, a monoclonal antibody is humanized or human.

In some embodiments, an immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses.

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α1β2, FAS, FASL, RELT, DR6, TROY, NGFR.

In some embodiments, an immuno-oncology agent is a cytokine that inhibits T cell activation (e.g., IL-6, IL-10, TGF-0, VEGF, and other immunosuppressive cytokines) or a cytokine that stimulates T cell activation, for stimulating an immune response.

In some embodiments, a combination of a compound of the invention and an immuno-oncology agent can stimulate T cell responses. In some embodiments, an immuno-oncology agent is: (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIRI, TIM-1, and TIM-4; or (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

In some embodiments, an immuno-oncology agent is an antagonist of inhibitory receptors on NK cells or an agonists of activating receptors on NK cells. In some embodiments, an immuno-oncology agent is an antagonists of KIR, such as lirilumab.

In some embodiments, an immuno-oncology agent is an agent that inhibits or depletes macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In some embodiments, an immuno-oncology agent is selected from agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell energy or exhaustion) and agents that trigger innate immune activation and/or inflammation at tumor sites.

In some embodiments, an immuno-oncology agent is a CTLA-4 antagonist. In some embodiments, a CTLA-4 antagonist is an antagonistic CTLA-4 antibody. In some embodiments, an antagonistic CTLA-4 antibody is YERVOY (ipilimumab) or tremelimumab.

In some embodiments, an immuno-oncology agent is a PD-1 antagonist. In some embodiments, a PD-1 antagonist is administered by infusion. In some embodiments, an immuno-oncology agent is an antibody or an antigen-binding portion thereof that binds specifically to a Programmed Death-1 (PD-1) receptor and inhibits PD-1 activity. In some embodiments, a PD-1 antagonist is an antagonistic PD-1 antibody. In some embodiments, an antagonistic PD-1 antibody is OPDIVO (nivolumab), KEYTRUDA (pembrolizumab), or MEDI-0680 (AMP-514; WO2012/145493). In some embodiments, an immuno-oncology agent may be pidilizumab (CT-011). In some embodiments, an immuno-oncology agent is a recombinant protein composed of the extracellular domain of PD-L2 (B7-DC) fused to the Fc portion of IgG1, called AMP-224.

In some embodiments, an immuno-oncology agent is a PD-L1 antagonist. In some embodiments, a PD-L1 antagonist is an antagonistic PD-L1 antibody. In some embodiments, a PD-L1 antibody is MPDL3280A (RG7446; WO2010/077634), durvalumab (MED14736), BMS-936559 (WO2007/005874), and MSB0010718C (WO2013/79174).

In some embodiments, an immuno-oncology agent is a LAG-3 antagonist. In some embodiments, a LAG-3 antagonist is an antagonistic LAG-3 antibody. In some embodiments, a LAG3 antibody is BMS-986016 (WO10/19570, WO14/08218), or IMP-731 or IMP-321 (WO08/132601, W0009/44273).

In some embodiments, an immuno-oncology agent is a CD137 (4-1BB) agonist. In some embodiments, a CD137 (4-1BB) agonist is an agonistic CD137 antibody. In some embodiments, a CD137 antibody is urelumab or PF-05082566 (WO12/32433).

In some embodiments, an immuno-oncology agent is a GITR agonist. In some embodiments, a GITR agonist is an agonistic GITR antibody. In some embodiments, a GITR antibody is BMS-986153, BMS-986156, TRX-518 (WO006/105021, WO009/009116), or MK-4166 (WO11/028683).

In some embodiments, an immuno-oncology agent is an indoleamine (2,3)-dioxygenase (IDO) antagonist. In some embodiments, an IDO antagonist is selected from epacadostat (INCB024360, Incyte); indoximod (NLG-8189, NewLink Genetics Corporation); capmanitib (INC280, Novartis); GDC-0919 (Genentech/Roche); PF-06840003 (Pfizer); BMS.F001287 (Bristol-Myers Squibb); Phy906/KD108 (Phytoceutica); an enzyme that breaks down kynurenine (Kynase, Kyn Therapeutics); and NLG-919 (WO09/73620, WO009/1156652, WO11/56652, WO12/142237).

In some embodiments, an immuno-oncology agent is an OX40 agonist. In some embodiments, an OX40 agonist is an agonistic OX40 antibody. In some embodiments, an OX40 antibody is MEDI-6383 or MEDI-6469.

In some embodiments, an immuno-oncology agent is an OX40L antagonist. In some embodiments, an OX40L antagonist is an antagonistic OX40 antibody. In some embodiments, an OX40L antagonist is RG-7888 (WO06/029879).

In some embodiments, an immuno-oncology agent is a CD40 agonist. In some embodiments, a CD40 agonist is an agonistic CD40 antibody. In some embodiments, an immuno-oncology agent is a CD40 antagonist. In some embodiments, a CD40 antagonist is an antagonistic CD40 antibody. In some embodiments, a CD40 antibody is lucatumumab or dacetuzumab.

In some embodiments, an immuno-oncology agent is a CD27 agonist. In some embodiments, a CD27 agonist is an agonistic CD27 antibody. In some embodiments, a CD27 antibody is varlilumab.

In some embodiments, an immuno-oncology agent is MGA271 (to B7H3) (WO11/109400).

In some embodiments, an immuno-oncology agent is abagovomab, adecatumumab, afutuzumab, alemtuzumab, anatumomab mafenatox, apolizumab, atezolimab, avelumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, or tremelimumab.

In some embodiments, an immuno-oncology agent is an immunostimulatory agent. For example, antibodies blocking the PD-1 and PD-L1 inhibitory axis can unleash activated tumor-reactive T cells and have been shown in clinical trials to induce durable anti-tumor responses in increasing numbers of tumor histologies, including some tumor types that conventionally have not been considered immunotherapy sensitive. See, e.g., Okazaki, T. et al. (2013) Nat. Immunol. 14, 1212-1218; Zou et al. (2016) Sci. Transl. Med. 8. The anti-PD-1 antibody nivolumab (Opdivo®, Bristol-Myers Squibb, also known as ONO-4538, MDX1106 and BMS- 936558), has shown potential to improve the overall survival in patients with RCC who had experienced disease progression during or after prior anti-angiogenic therapy.

In some embodiments, the immunomodulatory therapeutic specifically induces apoptosis of tumor cells. Approved immunomodulatory therapeutics which may be used in the present invention include pomalidomide (Pomalyst®, Celgene); lenalidomide (Revlimid®, Celgene); ingenol mebutate (Picato®, LEO Pharma).

In some embodiments, an immuno-oncology agent is a cancer vaccine. In some embodiments, the cancer vaccine is selected from sipuleucel-T (Provenge®, Dendreon/Valeant Pharmaceuticals), which has been approved for treatment of asymptomatic, or minimally symptomatic metastatic castrate-resistant (hormone-refractory) prostate cancer; and talimogene laherparepvec (Imlygic®, BioVex/Amgen, previously known as T-VEC), a genetically modified oncolytic viral therapy approved for treatment of unresectable cutaneous, subcutaneous and nodal lesions in melanoma. In some embodiments, an immuno-oncology agent is selected from an oncolytic viral therapy such as pexastimogene devacirepvec (PexaVec/JX-594, SillaJen/formerly Jennerex Biotherapeutics), a thymidine kinase- (TK-) deficient vaccinia virus engineered to express GM-CSF, for hepatocellular carcinoma (NCT02562755) and melanoma (NCT00429312); pelareorep (Reolysin®, Oncolytics Biotech), a variant of respiratory enteric orphan virus (reovirus) which does not replicate in cells that are not RAS-activated, in numerous cancers, including colorectal cancer (NCT01622543); prostate cancer (NCT01619813); head and neck squamous cell cancer (NCT01166542); pancreatic adenocarcinoma (NCT00998322); and non-small cell lung cancer (NSCLC) (NCT 00861627); enadenotucirev (NG-348, PsiOxus, formerly known as ColoAdl), an adenovirus engineered to express a full length CD80 and an antibody fragment specific for the T-cell receptor CD3 protein, in ovarian cancer (NCT02028117); metastatic or advanced epithelial tumors such as in colorectal cancer, bladder cancer, head and neck squamous cell carcinoma and salivary gland cancer (NCT02636036); ONCOS-102 (Targovax/formerly Oncos), an adenovirus engineered to express GM-CSF, in melanoma (NCT03003676); and peritoneal disease, colorectal cancer or ovarian cancer (NCT02963831); GL-ONC1 (GLV-1h68/GLV-1hl53, Genelux GmbH), vaccinia viruses engineered to express beta-galactosidase (beta-gal)/beta-glucoronidase or beta-gal/human sodium iodide symporter (hNIS), respectively, were studied in peritoneal carcinomatosis (NCT01443260); fallopian tube cancer, ovarian cancer (NCT 02759588); or CG0070 (Cold Genesys), an adenovirus engineered to express GM-CSF, in bladder cancer (NCT02365818).

In some embodiments, an immuno-oncology agent is selected from JX-929 (SillaJen/formerly Jennerex Biotherapeutics), a TK- and vaccinia growth factor-deficient vaccinia virus engineered to express cytosine deaminase, which is able to convert the prodrug 5-fluorocytosine to the cytotoxic drug 5-fluorouracil; TG01 and TG02 (Targovax/formerly Oncos), peptide-based immunotherapy agents targeted for difficult-to-treat RAS mutations; and TILT-123 (TILT Biotherapeutics), an engineered adenovirus designated: Ad5/3-E2F-delta24-hTNFα-IRES-hIL20; and VSV-GP (ViraTherapeutics) a vesicular stomatitis virus (VSV) engineered to express the glycoprotein (GP) of lymphocytic choriomeningitis virus (LCMV), which can be further engineered to express antigens designed to raise an antigen-specific CD8+ T cell response.

In some embodiments, an immuno-oncology agent is a T-cell engineered to express a chimeric antigen receptor, or CAR. The T-cells engineered to express such chimeric antigen receptor are referred to as a CAR-T cells.

CARs have been constructed that consist of binding domains, which may be derived from natural ligands, single chain variable fragments (scFv) derived from monoclonal antibodies specific for cell-surface antigens, fused to endodomains that are the functional end of the T-cell receptor (TCR), such as the CD3-zeta signaling domain from TCRs, which is capable of generating an activation signal in T lymphocytes. Upon antigen binding, such CARs link to endogenous signaling pathways in the effector cell and generate activating signals similar to those initiated by the TCR complex.

For example, in some embodiments the CAR-T cell is one of those described in U.S. Pat. No. 8,906,682 (June; hereby incorporated by reference in its entirety), which discloses CAR-T cells engineered to comprise an extracellular domain having an antigen binding domain (such as a domain that binds to CD19), fused to an intracellular signaling domain of the T cell antigen receptor complex zeta chain (such as CD3 zeta). When expressed in the T cell, the CAR is able to redirect antigen recognition based on the antigen binding specificity. In the case of CD19, the antigen is expressed on malignant B cells. Over 200 clinical trials are currently in progress employing CAR-T in a wide range of indications. [https://clinicaltrials.gov/ct2/results?term=chimeric+antigen+receptors&pg=1].

In some embodiments, an immunostimulatory agent is an activator of retinoic acid receptor-related orphan receptor γ (RORγt). RORγt is a transcription factor with key roles in the differentiation and maintenance of Type 17 effector subsets of CD4+(Th17) and CD8+(Tc17) T cells, as well as the differentiation of IL-17 expressing innate immune cell subpopulations such as NK cells. In some embodiments, an activator of RORγt is LYC-55716 (Lycera), which is currently being evaluated in clinical trials for the treatment of solid tumors (NCT02929862).

In some embodiments, an immunostimulatory agent is an agonist or activator of a toll-like receptor (TLR). Suitable activators of TLRs include an agonist or activator of TLR9 such as SD-101 (Dynavax). SD-101 is an immunostimulatory CpG which is being studied for B-cell, follicular and other lymphomas (NCT02254772). Agonists or activators of TLR8 which may be used in the present invention include motolimod (VTX-2337, VentiRx Pharmaceuticals) which is being studied for squamous cell cancer of the head and neck (NCT02124850) and ovarian cancer (NCT02431559).

Other immuno-oncology agents that may be used in the present invention include urelumab (BMS-663513, Bristol-Myers Squibb), an anti-CD137 monoclonal antibody; varlilumab (CDX-1127, Celldex Therapeutics), an anti-CD27 monoclonal antibody; BMS-986178 (Bristol-Myers Squibb), an anti-OX40 monoclonal antibody; lirilumab (IPH2102/BMS-986015, Innate Pharma, Bristol-Myers Squibb), an anti-KIR monoclonal antibody; monalizumab (IPH2201, Innate Pharma, AstraZeneca) an anti-NKG2A monoclonal antibody; andecaliximab (GS-5745, Gilead Sciences), an anti-MMP9 antibody; MK-4166 (Merck & Co.), an anti-GITR monoclonal antibody.

In some embodiments, an immunostimulatory agent is selected from elotuzumab, mifamurtide, an agonist or activator of a toll-like receptor, and an activator of RORγt.

In some embodiments, an immunostimulatory therapeutic is recombinant human interleukin 15 (rhIL-15). rhIL-15 has been tested in the clinic as a therapy for melanoma and renal cell carcinoma (NCT01021059 and NCT01369888) and leukemias (NCT02689453). In some embodiments, an immunostimulatory agent is recombinant human interleukin 12 (rhIL-12). In some embodiments, an IL-15 based immunotherapeutic is heterodimeric IL-15 (hetIL-15, Novartis/Admune), a fusion complex composed of a synthetic form of endogenous IL-15 complexed to the soluble IL-15 binding protein IL-15 receptor alpha chain (IL15:sIL-15RA), which has been tested in Phase 1 clinical trials for melanoma, renal cell carcinoma, non-small cell lung cancer and head and neck squamous cell carcinoma (NCT02452268). In some embodiments, a recombinant human interleukin 12 (rhIL-12) is NM-IL-12 (Neumedicines, Inc.), NCT02544724, or NCT02542124.

In some embodiments, an immuno-oncology agent is selected from those descripted in Jerry L. Adams et al., "Big opportunities for small molecules in immuno-oncology," Cancer Therapy 2015, Vol. 14, pages 603-622, the content of which is incorporated herein by reference in its entirety. In some embodiments, an immuno-oncology agent is selected from the examples described in Table 1 of Jerry L. Adams et al. In some embodiments, an immuno-oncology agent is a small molecule targeting an immuno-oncology target selected from those listed in Table 2 of Jerry L. Adams E T. AL. In some embodiments, an immuno-oncology agent is a small molecule agent selected from those listed in Table 2 of Jerry L. Adams et al.

In some embodiments, an immuno-oncology agent is selected from the small molecule immuno-oncology agents described in Peter L. Toogood, "Small molecule immuno-oncology therapeutic agents," Bioorganic & Medicinal Chemistry Letters 2018, Vol. 28, pages 319-329, the content of which is incorporated herein by reference in its entirety. In some embodiments, an immuno-oncology agent is an agent targeting the pathways as described in Peter L. Toogood.

In some embodiments, an immuno-oncology agent is selected from those described in Sandra L. Ross et al., "Bispecific T cell engager (BiTE®) antibody constructs can mediate bystander tumor cell killing", PLoS ONE 12(8): e0183390, the contents of which is incorporated herein by reference in its entirety. In some embodiments, an immuno-oncology agent is a bispecific T cell engager (BiTE®) antibody construct. In some embodiments, a bispecific T cell engager (BiTE®) antibody construct is a CD19/CD3 bispecific antibody construct. In some embodiments, a bispecific T cell engager (BiTE®) antibody construct is an EGFR/CD3 bispecific antibody construct. In some embodiments, a bispecific T cell engager (BiTE®) antibody construct activates T cells. In some embodiments, a bispecific T cell engager (BiTE®) antibody construct activates T cells, which release cytokines inducing upregulation of intercellular adhesion molecule 1 (ICAM-1) and FAS on bystander cells. In some embodiments, a bispecific T cell engager (BiTE®) antibody construct activates T cells which result in induced bystander cell lysis. In some embodiments, the bystander cells are in solid tumors. In some embodiments, the bystander cells being lysed are in proximity to the BiTE®-activated T cells. In some embodiment, the bystander cells comprises tumor-associated antigen (TAA) negative cancer cells. In some embodiment, the bystander cells comprise EGFR-negative cancer cells. In some embodiments, an immuno-oncology agent is an antibody which blocks the PD-L1/PD1 axis and/or CTLA4. In some embodiments, an immuno-oncology agent is an ex-vivo expanded tumor-infiltrating T cell. In some embodiments, an immuno-oncology agent is a bispecific antibody construct or chimeric antigen receptors (CARs) that directly connect T cells with tumor-associated surface antigens (TAAs).

Exemplary Immune Checkpoint Inhibitors

In some embodiments, an immuno-oncology agent is an immune checkpoint inhibitor as described herein.

The term "checkpoint inhibitor" as used herein relates to agents useful in preventing cancer cells from avoiding the immune system of the patient. One of the major mechanisms of anti-tumor immunity subversion is known as "T-cell exhaustion," which results from chronic exposure to antigens that has led to up-regulation of inhibitory receptors. These inhibitory receptors serve as immune checkpoints in order to prevent uncontrolled immune reactions.

PD-1 and co-inhibitory receptors such as cytotoxic T-lymphocyte antigen 4 (CTLA-4, B and T Lymphocyte Attenuator (BTLA; CD272), T cell Immunoglobulin and Mucin domain-3 (Tim-3), Lymphocyte Activation Gene-3 (Lag-3; CD223), and others are often referred to as a checkpoint regulators. They act as molecular "gatekeepers" that allow extracellular information to dictate whether cell cycle progression and other intracellular signaling processes should proceed.

In some embodiments, an immune checkpoint inhibitor is an antibody to PD-1. PD-1 binds to the programmed cell death 1 receptor (PD-1) to prevent the receptor from binding to the inhibitory ligand PDL-1, thus overriding the ability of tumors to suppress the host anti-tumor immune response.

In one aspect, the checkpoint inhibitor is a biologic therapeutic or a small molecule. In another aspect, the checkpoint inhibitor is a monoclonal antibody, a humanized antibody, a fully human antibody, a fusion protein or a combination thereof. In a further aspect, the checkpoint inhibitor inhibits a checkpoint protein selected from CTLA-4, PDL1, PDL2, PDl, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an additional aspect, the checkpoint inhibitor interacts with a ligand of a checkpoint protein selected from CTLA-4, PDL1, PDL2, PDl, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an aspect, the checkpoint inhibitor is an immunostimulatory agent, a T cell growth factor, an interleukin, an antibody, a vaccine or a combination thereof. In a further aspect, the interleukin is IL-7 or IL-15. In a specific aspect, the interleukin is glycosylated IL-7. In an additional aspect, the vaccine is a dendritic cell (DC) vaccine.

Checkpoint inhibitors include any agent that blocks or inhibits in a statistically significant manner, the inhibitory pathways of the immune system. Such inhibitors may include small molecule inhibitors or may include antibodies, or antigen binding fragments thereof, that bind to and block or inhibit immune checkpoint receptors or antibodies that bind to and block or inhibit immune checkpoint receptor ligands. Illustrative checkpoint molecules that may be targeted for blocking or inhibition include, but are not limited to, CTLA-4, PDL1, PDL2, PD1, B7-H3, B7-H4, BTLA, HVEM, GAL9, LAG3, TIM3, VISTA, KIR, 2B4 (belongs to the CD2 family of molecules and is expressed on all NK, γδ, and memory CD8+(ap) T cells), CD160 (also referred to as BY55), CGEN-15049, CHK 1 and CHK2 kinases, A2aR, and various B-7 family ligands. B7 family ligands include, but are not limited to, B7- 1, B7-2, B7-DC, B7-H1, B7-H2, B7-H3, B7-H4, B7-H5, B7-H6 and B7-H7. Checkpoint inhibitors include antibodies, or antigen binding fragments thereof, other binding proteins, biologic therapeutics, or small molecules, that bind to and block or inhibit the activity of one or more of CTLA-4, PDL1, PDL2, PD1, BTLA, HVEM, TIM3, GAL9, LAG3, VISTA, KIR, 2B4, CD 160 and CGEN-15049. Illustrative immune checkpoint inhibitors include Tremelimumab (CTLA-4 blocking antibody), anti-OX40, PD-L1 monoclonal Antibody (Anti-B7-H1; MED14736), MK-3475 (PD-1 blocker), Nivolumab (anti-PDI antibody), CT-011 (anti-PDI antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody), and ipilimumab (anti-CTLA-4 checkpoint inhibitor). Checkpoint protein ligands include, but are not limited to PD-L1, PD-L2, B7-H3, B7-H4, CD28, CD86 and TIM-3.

In certain embodiments, the immune checkpoint inhibitor is selected from a PD-1 antagonist, a PD-L1 antagonist, and a CTLA-4 antagonist. In some embodiments, the checkpoint inhibitor is selected from the group consisting of nivolumab (Opdivo®), ipilimumab (Yervoy®), and pembrolizumab (Keytruda®). In some embodiments, the checkpoint inhibitor is selected from nivolumab (anti-PD-1 antibody, Opdivo®, Bristol-Myers Squibb); pembrolizumab (anti-PD-1 antibody, Keytruda®, Merck); ipilimumab (anti-CTLA-4 antibody, Yervoy®, Bristol-Myers Squibb); durvalumab (anti-PD-L1 antibody, Imfinzi®, AstraZeneca); and atezolizumab (anti-PD-L1 antibody, Tecentriq®, Genentech).

In some embodiments, the checkpoint inhibitor is selected from the group consisting of lambrolizumab (MK-3475), nivolumab (BMS-936558), pidilizumab (CT-011), AMP-224, MDX-1105, MED14736, MPDL3280A, BMS-936559, ipilimumab, lirlumab, IPH2101, pembrolizumab (Keytruda®), and tremelimumab.

In some embodiments, an immune checkpoint inhibitor is REGN2810 (Regeneron), an anti-PD-1 antibody tested in patients with basal cell carcinoma (NCT03132636); NSCLC (NCT03088540); cutaneous squamous cell carcinoma (NCT02760498); lymphoma (NCT02651662); and melanoma (NCT03002376); pidilizumab (CureTech), also known as CT-011, an antibody that binds to PD-1, in clinical trials for diffuse large B-cell lymphoma and multiple myeloma; avelumab (Bavencio®, Pfizer/Merck K GaA), also known as MSB0010718C), a fully human IgG1 anti-PD-L1 antibody, in clinical trials for non-small cell lung cancer, Merkel cell carcinoma, mesothelioma, solid tumors, renal cancer, ovarian cancer, bladder cancer, head and neck cancer, and gastric cancer; or PDR001 (Novartis), an inhibitory antibody that binds to PD-1, in clinical trials for non-small cell lung cancer, melanoma, triple negative breast cancer and advanced or metastatic solid tumors. Tremelimumab (CP-675,206; Astrazeneca) is a fully human monoclonal antibody against CTLA-4 that has been in studied in clinical trials for a number of indications, including: mesothelioma, colorectal cancer, kidney cancer, breast cancer, lung cancer and non-small cell lung cancer, pancreatic ductal adenocarcinoma, pancreatic cancer, germ cell cancer, squamous cell cancer of the head and neck, hepatocellular carcinoma, prostate cancer, endometrial cancer, metastatic cancer in the liver, liver cancer, large B-cell lymphoma, ovarian cancer, cervical cancer, metastatic anaplastic thyroid cancer, urothelial cancer, fallopian tube cancer, multiple myeloma, bladder cancer, soft tissue sarcoma, and melanoma. AGEN-1884 (Agenus) is an anti-CTLA4 antibody that is being studied in Phase 1 clinical trials for advanced solid tumors (NCT02694822).

In some embodiments, a checkpoint inhibitor is an inhibitor of T-cell immunoglobulin mucin containing protein-3 (TIM-3). TIM-3 inhibitors that may be used in the present invention include TSR-022, LY3321367 and MBG453. TSR-022 (Tesaro) is an anti-TIM-3 antibody which is being studied in solid tumors (NCT02817633). LY3321367 (Eli Lilly) is an anti-TIM-3 antibody which is being studied in solid tumors (NCT03099109). MBG453 (Novartis) is an anti-TIM-3 antibody which is being studied in advanced malignancies (NCT02608268).

In some embodiments, a checkpoint inhibitor is an inhibitor of T cell immunoreceptor with Ig and ITIM domains, or TIGIT, an immune receptor on certain T cells and NK cells. TIGIT inhibitors that may be used in the present invention include BMS-986207 (Bristol-Myers Squibb), an anti-TIGIT monoclonal antibody (NCT02913313); OMP-313M32 (Oncomed); and anti-TIGIT monoclonal antibody (NCT03119428).

In some embodiments, a checkpoint inhibitor is an inhibitor of Lymphocyte Activation Gene-3 (LAG-3). LAG-3 inhibitors that may be used in the present invention include BMS-986016 and REGN3767 and IMP321. BMS-986016 (Bristol-Myers Squibb), an anti-LAG-3 antibody, is being studied in glioblastoma and gliosarcoma (NCT02658981). REGN3767 (Regeneron), is also an anti-LAG-3 antibody, and is being studied in malignancies (NCT03005782). IMP321 (Immutep S.A.) is an LAG-3-Ig fusion protein, being studied in melanoma (NCT02676869); adenocarcinoma (NCT02614833); and metastatic breast cancer (NCT00349934).

Checkpoint inhibitors that may be used in the present invention include OX40 agonists. OX40 agonists that are being studied in clinical trials include PF-04518600/PF-8600 (Pfizer), an agonistic anti-OX40 antibody, in metastatic kidney cancer (NCT03092856) and advanced cancers and neoplasms (NCT02554812; NCT05082566); GSK3174998 (Merck), an agonistic anti-OX40 antibody, in Phase 1 cancer trials (NCT02528357); MEDI0562 (Medimmune/AstraZeneca), an agonistic anti-OX40 antibody, in advanced solid tumors (NCT02318394 and NCT02705482); MEDI6469, an agonistic anti-OX40 antibody (Medimmune/AstraZeneca), in patients with colorectal cancer (NCT02559024), breast cancer (NCT01862900), head and neck cancer (NCT02274155) and metastatic prostate cancer (NCT01303705); and BMS-986178 (Bristol-Myers Squibb) an agonistic anti-OX40 antibody, in advanced cancers (NCT02737475).

Checkpoint inhibitors that may be used in the present invention include CD137 (also called 4-1BB) agonists. CD137 agonists that are being studied in clinical trials include utomilumab (PF-05082566, Pfizer) an agonistic anti-CD137 antibody, in diffuse large B-cell lymphoma (NCT02951156) and in advanced cancers and neoplasms (NCT02554812 and NCT05082566); urelumab (BMS-663513, Bristol-Myers Squibb), an agonistic anti-CD137 antibody, in melanoma and skin cancer (NCT02652455) and glioblastoma and gliosarcoma (NCT02658981).

Checkpoint inhibitors that may be used in the present invention include CD27 agonists. CD27 agonists that are being studied in clinical trials include varlilumab (CDX-1127, Celldex Therapeutics) an agonistic anti-CD27 antibody, in squamous cell head and neck cancer, ovarian carcinoma, colorectal cancer, renal cell cancer, and glioblastoma (NCT02335918); lymphomas (NCT01460134); and glioma and astrocytoma (NCT02924038).

Checkpoint inhibitors that may be used in the present invention include glucocorticoid-induced tumor necrosis factor receptor (GITR) agonists. GITR agonists that are being studied in clinical trials include TRX518 (Leap Therapeutics), an agonistic anti-GITR antibody, in malignant melanoma and other malignant solid tumors (NCT01239134 and NCT02628574); GWN323 (Novartis), an agonistic anti-GITR antibody, in solid tumors and lymphoma (NCT 02740270); INCAGN01876 (Incyte/Agenus), an agonistic anti-GITR antibody, in advanced cancers (NCT02697591 and NCT03126110); MK-4166 (Merck), an agonistic anti-GITR antibody, in solid tumors (NCT02132754) and MED11873 (Medimmune/AstraZeneca), an agonistic hexameric GITR-ligand molecule with a human IgG1 Fc domain, in advanced solid tumors (NCT02583165).

Checkpoint inhibitors that may be used in the present invention include inducible T-cell co-stimulator (ICOS, also known as CD278) agonists. ICOS agonists that are being studied in clinical trials include MEDI-570 (Medimmune), an agonistic anti-ICOS antibody, in lymphomas (NCT02520791); GSK3359609 (Merck), an agonistic anti-ICOS antibody, in Phase 1 (NCT02723955); JTX-2011 (Jounce Therapeutics), an agonistic anti-ICOS antibody, in Phase 1 (NCT02904226).

Checkpoint inhibitors that may be used in the present invention include killer IgG-like receptor (KIR) inhibitors. KIR inhibitors that are being studied in clinical trials include lirilumab (IPH2102/BMS-986015, Innate Pharma/Bristol-Myers Squibb), an anti-KIR antibody, in leukemias (NCT01687387, NCT02399917, NCT02481297, NCT02599649), multiple myeloma (NCT02252263), and lymphoma (NCT01592370); IPH2101 (1-7F9, Innate Pharma) in myeloma (NCT01222286 and NCT01217203); and IPH4102 (Innate Pharma), an anti-KIR antibody that binds to three domains of the long cytoplasmic tail (KIR3DL2), in lymphoma (NCT02593045).

Checkpoint inhibitors that may be used in the present invention include CD47 inhibitors of interaction between CD47 and signal regulatory protein alpha (SIRPa). CD47/SIRPa inhibitors that are being studied in clinical trials include ALX-148 (Alexo Therapeutics), an antagonistic variant of (SIRPa) that binds to CD47 and prevents CD47/SIRPa-mediated signaling, in phase 1 (NCT03013218); TTI-621 (SIRPa-Fc, Trillium Therapeutics), a soluble recombinant fusion protein created by linking the N-terminal CD47-binding domain of SIRPa with the Fc domain of human IgG1, acts by binding human CD47, and preventing it from delivering its "do not eat" signal to macrophages, is in clinical trials in Phase 1 (NCT02890368 and NCT02663518); CC-90002 (Celgene), an anti-CD47 antibody, in leukemias (NCT02641002); and Hu5F9-G4 (Forty Seven, Inc.), in colorectal neoplasms and solid tumors (NCT02953782), acute myeloid leukemia (NCT02678338) and lymphoma (NCT02953509).

Checkpoint inhibitors that may be used in the present invention include CD73 inhibitors. CD73 inhibitors that are being studied in clinical trials include MEDI9447 (Medimmune), an anti-CD73 antibody, in solidtumors (NCT02503774); and BMS-986179 (Bristol-Myers Squibb), an anti-CD73 antibody, in solid tumors (NCT02754141).

Checkpoint inhibitors that may be used in the present invention include agonists of stimulator of interferon genes protein (STING, also known as transmembrane protein 173, or TMEM173). Agonists of STING that are being studied in clinical trials include MK-1454 (Merck), an agonistic synthetic cyclic dinucleotide, in lymphoma (NCT03010176); and ADU-S100 (MIW815, Aduro Biotech/Novartis), an agonistic synthetic cyclic dinucleotide, in Phase 1 (NCT02675439 and NCT03172936).

In some embodiments, STAT3 inhibition/degradation can significantly enhance CDN-induced STING signaling and antitumor immunity (Pei et al., *Can. Lett.* 2019, 450:110).

Checkpoint inhibitors that may be used in the present invention include CSF1R inhibitors. CSF1R inhibitors that are being studied in clinical trials include pexidartinib (PLX3397, Plexxikon), a CSF1R small molecule inhibitor, in colorectal cancer, pancreatic cancer, metastatic and advanced cancers (NCT02777710) and melanoma, non-small cell lung cancer, squamous cell head and neck cancer, gastrointestinal stromal tumor (GIST) and ovarian cancer (NCT02452424); and IMC-CS4 (LY3022855, Lilly), an anti-CSF-1R antibody, in pancreatic cancer (NCT03153410), melanoma (NCT03101254), and solid tumors (NCT02718911); and BLZ945 (4-[2((1R,2R)-2-hydroxycyclohexylamino)-benzothiazol-6-yloxyl]-pyridine-2-carboxylic acid methylamide, Novartis), an orally available inhibitor of CSF1R, in advanced solid tumors (NCT02829723).

Checkpoint inhibitors that may be used in the present invention include NKG2A receptor inhibitors. NKG2A receptor inhibitors that are being studied in clinical trials include monalizumab (IPH2201, Innate Pharma), an anti-NKG2A antibody, in head and neck neoplasms (NCT02643550) and chronic lymphocytic leukemia (NCT02557516).

In some embodiments, the immune checkpoint inhibitor is selected from nivolumab, pembrolizumab, ipilimumab, avelumab, durvalumab, atezolizumab, or pidilizumab.

EXEMPLIFICATION

Abbreviations

Ac: acetyl
AcOH: acetic acid
ACN: acetonitrile
Ad: adamantly
AIBN: 2,2'-azo bisisobutyronitrile
Anhyd: anhydrous
Aq: aqueous
$B_2Pin_2$: bis (pinacolato)diboron -4,4,4',4',5,5,5',5'-octamethyl-2,2'-bi(1,3,2-dioxaborolane)
BINAP: 2,2'-bis(diphenylphosphino)-1,1'-binaphthyl
$BH_3$: Borane
Bn: benzyl
Boc: tert-butoxycarbonyl
$Boc_20$: di-tert-butyl dicarbonate
BPO: benzoyl peroxide
$^nBuOH$: n-butanol
CDI: carbonyldiimidazole
COD: cyclooctadiene
d: days
DABCO: 1,4-diazobicyclo[2.2.2]octane
DAST: diethylaminosulfur trifluoride
dba: dibenzylideneacetone
DBU: 1,8-diazobicyclo[5.4.0]undec-7-ene
DCE: 1,2-dichloroethane
DCM: dichloromethane
DEA: diethylamine
DHP: dihydropyran
DIBAL-H: diisobutylaluminum hydride
DIPA: diisopropylamine
DIPEA or DIEA: N,N-diisopropylethylamine
DMA: N,N-dimethylacetamide
DME: 1,2-dimethoxyethane
DMAP: 4-dimethylaminopyridine
DMF: N,N-dimethylformamide DMP: Dess-Martin periodinane
DMSO-dimethyl sulfoxide
DPPA: diphenylphosphoryl azide
dppf: 1,1'-bis(diphenylphosphino)ferrocene
EDC or EDCI: 1-(3-dimethylaminopropyl)-3-ethylcarbodiimide hydrochloride
ee: enantiomeric excess
ESI: electrospray ionization
EA: ethyl acetate
EtOAc: ethyl acetate
EtOH: ethanol
FA: formic acid
h or hrs: hours
HATU: N,N,N',N'-tetramethyl-O-(7-azabenzotriazol-1-yl)uronium hexafluorophosphate
HCl: hydrochloric acid
HPLC: high performance liquid chromatography
HOAc: acetic acid
IBX: 2-iodoxybenzoic acid
IPA: isopropyl alcohol
KHMDS: potassium hexamethyldisilazide
$K_2CO_3$: potassium carbonate
LAH: lithium aluminum hydride
LDA: lithium diisopropylamide
m-CPBA: meta-chloroperbenzoic acid
M: molar
MeCN: acetonitrile
MeOH: methanol
$Me_2S$: dimethyl sulfide
MeONa: sodium methylate
Mel: iodomethane
min: minutes
mL: milliliters
mM: millimolar
mmol: millimoles
MPa: mega pascal
MOMCl: methyl chloromethyl ether
MsCl: methanesulfonyl chloride
MTBE: methyl tert-butyl ether
nBuLi: n-butyl]ithium
$NaNO_2$: sodium nitrite
NaOH: sodium hydroxide
$Na_2SO_4$: sodium sulfate
NBS: N-bromosuccinimide
NCS: N-chlorosuccinimide
NFSI: N-Fluorobenzenesulfonimide
NMO: N:-methylno&rpholine N-oxide
NMP: N-methylpyrrolidine
NMR: Nuclear Magnetic Resonance
° C.: degrees Celsius
Pd/C: Palladium on Carbon
$Pd(OAc)_2$: Palladium Acetate
PBS: phosphate buffered saline
PE: petroleum ether
$POCl_3$: phosphorus oxychloride
$PPh_3$: triphenylphosphine
PyBOP: (Benzotriazol-1-yloxy)tripyrrolidinophosphonium hexafluorophosphate
Rel: relative
R.T. or rt: room temperature
sat: saturated
SEMCl: chloromethyl-2-trimethylsilylethyl ether
SFC: supercritical fluid chromatography
$SOCl_2$: sulfur dichloride
tBuOK: potassium tert-butoxide
TBAB: tetrabutylammonium bromide
TBAI: tetrabutylammonium iodide
TEA: triethylamine
Tf: trifluoromethanesulfonate
TfAA, TFMSA or $Tf_2O$: trifluoromethanesulfonic anhydride
TFA: trifluoracetic acid
TIPS: triisopropylsilyl
THF: tetrahydrofuran
THP: tetrahydropyran
TLC: thin layer chromatography
TMEDA: tetramethylethylenediamine
pTSA: para-toluenesulfonic acid
wt: weight
Xantphos: 4,5-bis(diphenylphosphino)-9,9-dimethylxanthene General Synthetic Methods The following examples are intended to illustrate the invention and are not to be construed as being limitations thereon. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

All reactions are carried out under nitrogen or argon unless otherwise stated.

Proton NMR ($^1H$ NMR) is conducted in deuterated solvent. In certain compounds disclosed herein, one or more $^1H$ shifts overlap with residual proteo solvent signals; these signals have not been reported in the experimental provided hereinafter.

TABLE 2

| Analytical instruments | |
|---|---|
| LCMS | Shimadzu UFLC MS: LCMS-2020 Agilent Technologies 1200 series MS: Agilent Technologies 6110 Agilent Technologies 1200 series MS: LC/MSD VL |
| NMR | BRUKER AVANCE III/400; Frequency (MHz) 400.13; Nucleus: 1H; Number of Transients: 8 |
| Prep-HPLC | Gilson GX-281 systems: instruments GX-A, GX-B, GX-C, GX-D, GX-E, GX-F, GX-G and GX-H |
| GCMS | SHIMADZU GCMS-QP2010 Ultra |
| Analytical cSFC | Agilent Technologies 1290 Infinity |
| Prep-cSFC | Waters SFC Prep 80 |

For acidic LCMS data: LCMS was recorded on an Agilent 1200 Series LC/MSD or Shimadzu LCMS2020 equipped with electro-spray ionization and quadruple MS detector [ES+ve to give $MH^+$] and equipped with Chromolith Flash RP-18e 25*2.0 mm, eluting with 0.0375 vol % TFA in water (solvent A) and 0.01875 vol % TFA in acetonitrile (solvent B). Other LCMS was recorded on an Agilent 1290 Infinity RRLC attached with Agilent 6120 Mass detector. The column used was BEH C18 50*2.1 mm, 1.7 micron. Column flow was 0.55 ml/min and mobile phase were used (A) 2 mM Ammonium Acetate in 0.1% Formic Acid in Water and (B) 0.1% Formic Acid in Acetonitrile.

For basic LCMS data: LCMS was recorded on an Agilent 1200 Series LC/MSD or Shimadzu LCMS 2020 equipped with electro-spray ionization and quadruple MS detector [ES+ve to give $MH^+$] and equipped with Xbridge C18, $2.1x^{50}$ mm columns packed with 5 mm C18-coated silica or Kinetex EVO C18 $2.1X^{30}$ mm columns packed with 5 mm C18-coated silica, eluting with 0.05 vol % $NH_3$ $H_2O$ in water (solvent A) and acetonitrile (solvent B).

HPLC Analytical Method: HPLC was carried out on X Bridge C18 150*4.6 mm, 5 micron. Column flow was 1.0 ml/min and mobile phase were used (A) 0.1% Ammonia in water and (B) 0.1% Ammonia in Acetonitrile.

Prep HPLC Analytical Method: The compound was purified on Shimadzu LC-20AP and UV detector. The column used was X-BRIDGE C18 (250*19)mm, 5. Column flow was 16.0 ml/min. Mobile phase were used (A) 0.1% Formic Acid in Water and (B) Acetonitrile Basic method used (A) 5 mM ammonium bicarbonate and 0.1% NH3 in Water and (B) Acetonitrile or (A) 0.1% Ammonium Hydroxide in Water and (B) Acetonitrile. The UV spectra were recorded at 202 nm & 254 nm.

NMR Method: The 1H NMR spectra were recorded on a Bruker Ultra Shield Advance 400 MHz/5 mm Probe (BBFO). The chemical shifts are reported in part-per-million.

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Intermediates

Tert-butyl N-[(3S,4R)-4- [(4-bromophenyl) methoxy]-1-carbamoylpentan-3-yl]carbamate (Intermediate A)

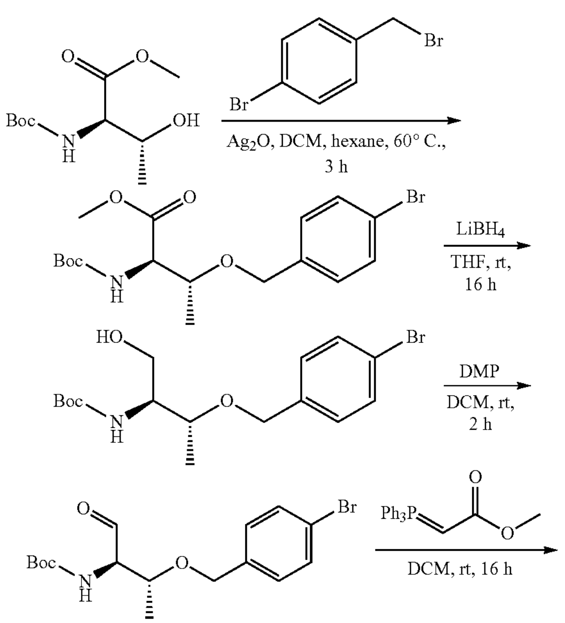

-continued

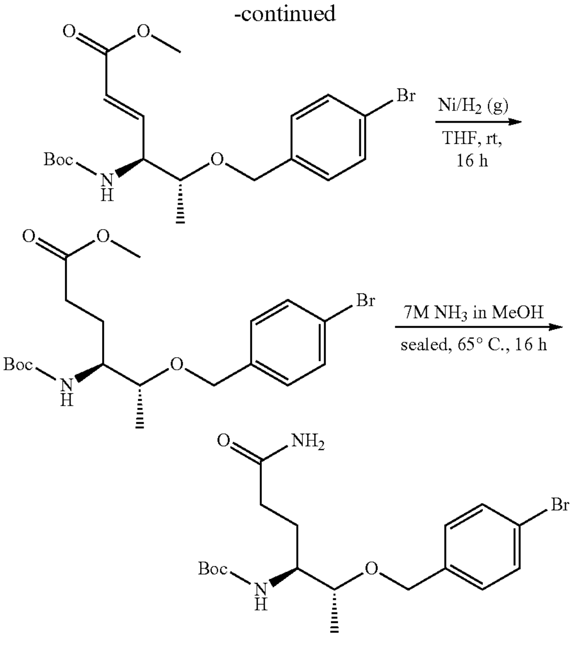

Intermediate A

Step 1. Methyl (2R,3R)-3-[(4-bromophenyl)methoxy]-2-[[(tert-butoxy)carbonyl]amino]butanoate. To a solution of methyl (2R,3R)-2-[[(tert-butoxy)carbonyl]amino]-3-hydroxybutanoate (11.7 g, 50.2 mmol) and 1-bromo-4-(bromomethyl)benzene (15.1 g, 60.2 mmol) in DCM (80 mL) were added silver oxide (17.4 g, 75.2 mmol) and n-hexane (10 mL) at room temperature under nitrogen atmosphere. The resulting mixture was stirred for 3 hours at 60° C. under nitrogen atmosphere. The reaction mixture was cooled down to room temperature and filtered. The filtered cake was washed with DCM (3×80 mL). The combined filtrates was concentrated under reduced pressure. The residue was purified by silica gel column chromatography, eluted with 10% ethyl acetate in petroleum ether to afford the title compound as a light yellow oil (7.30 g, 35%): $^1H$ NMR (400 MHz, $CDCl_3$) δ 7.48-7.41 (m, 2H), 7.19 (d, J=8.1 Hz, 2H), 5.28 (d, J=8.9 Hz, 1H), 4.55 (dd, J=9.0, 3.9 Hz, 1H), 4.51 (s, 2H), 3.83 (td, J=6.4, 4.0 Hz, 1H), 3.75 (s, 3H), 1.44 (s, 9H), 1.22 (d, J=6.4 Hz, 3H); MS (ESI, m/z): [(M+1)]+=402.15, 404.15.

Step 2. Tert-butyl N-[(2S,3R)-3-[(4-bromophenyl) methoxy]-1-hydroxybutan-2-yl]carbamate. To a solution of methyl (2R,3R)-3-[(4-bromophenyl)methoxy]-2-[[(tert-butoxy)carbonyl]amino]butanoate (7.00 g, 17.4 mmol) in THF (20 mL) was added $LiBH_4$ (2 M solution in THF, 17.5 mL, 538 mmol) at room temperature under nitrogen atmosphere. The resulting solution was stirred for 16 hours at room temperature under nitrogen atmosphere. The resulting mixture was diluted with water (200 mL) and extracted with ethyl acetate (3×60 mL). The combined organic layers was washed with brine (100 mL) and dried over anhydrous $Na_2SO_4$. After filtration, the filtrate was concentrated under reduced pressure. The residue was purified by silica gel column chromatography, eluted with 30% ethyl acetate in petroleum ether to afford the title compound as a light yellow oil (6.50 g, 95%): $^1H$ NMR (400 MHz, $CDCl_3$) δ 7.50-7.45 (m, 2H), 7.22-7.17 (m, 2H), 5.37-5.26 (m, 1H), 4.58 (d, J=11.9 Hz, 1H), 4.37 (d, J=11.9 Hz, 1H), 3.97 (dd, J=11.5, 3.5 Hz, 1H), 3.85-3.76 (m, 1H), 3.64 (dd, J=11.5, 3.7 Hz, 1H), 3.60-3.52 (m, 1H), 2.81 (s, 1H), 1.44 (s, 9H), 1.26 (dd, J=6.8, 2.2 Hz, 3H); MS (ESI, m/z): [(M+23)]+=396.20, 398.20.

The following intermediates in Table 3 were prepared according to Step 2 of the procedure to prepare Intermediate A.

TABLE 3

| Characterization data for intermediates prepared according to above. | | | | |
|---|---|---|---|---|
| Intermediate | Structure | Chemical Name | MS: $[(M+1)]^+$ | $^1$H-NMR |
| A-2-1 | 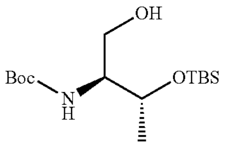 [SMILES: C[C@@H](O[Si](C)(C)C(C)(C)C)[C@H](CO)NC(=O)OC(C)(C)C] | tert-butyl N-(2S, 3R)-3-[(tert-butyldimethylsilyl) oxy]-1-hydroxybutan-2-yl]carbamate | 320.15 | (400 MHz, $CDCl_3$) δ 5.40 (d, J = 8.1 Hz, 1H), 4.24-4.15 (m, 1H), 4.17-4.09 (m, 1H), 3.63 (dd, J = 11.6, 3.4 Hz, 1H), 3.45-3.38 (m, 1H), 1.47 (s, 9H), 1.26 (d, J = 6.4 Hz, 3H), 0.91 (s, 9H), 0.11 (s, 6H) |
| A-2-2 | 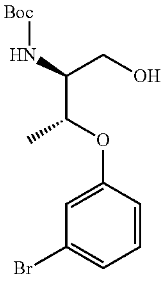 [SMILES: C[C@@H](Oc1cccc(Br)c1)[C@H](CO)NC(=O)OC(C)(C)C] | tert-butyl N-[(2S,3R)-3-(3-bromophenoxy)-1-hydroxybutan-2-yl]carbamate | 360.00, 362.00 | (400 MHz, DMSO-$d_6$) δ 7.23 (t, J = 8.0 Hz, 1H), 7.13-7.07 (m, 2H), 6.95-6.89 (m, 1H), 6.64 (d, J = 9.2 Hz, 1H), 4.71 (t, J = 5.4 Hz, 1H), 4.53-4.47 (m, 1H), 3.73-3.67 (m, 1H), 3.49-3.42 (m, 2H), 1.39 (s, 9H), 1.20 (d, J = 6.3 Hz, 3H) |
| A-2-3 | 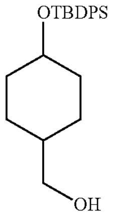 | [4-[(tert-butyldiphenylsilyl) oxy]cyclohexyl] methanol | N/A | (400 MHz, $CDCl_3$) δ 7.75-7.65 (m, 4H), 7.46-7.37 (m, 6H), 3.62-3.55 (m, 1H), 3.39 (d, J = 6.4 Hz, 2H), 1.89 (dd, J = 13.4, 3.8 Hz, 2H), 1.72 (d, J = 13.4 Hz, 2H), 1.46-1.39 (m, 4H), 1.08 (s, 9H), 0.89-0.78 (m, 2H) |

Step 3. Tert-butyl N-[(2R,3R)-3-[(4-bromophenyl) methoxy]-1-oxobutan-2-yl]carbamate. To a mixture of tert-butyl N-[(2S,3R)-3- [(4-bromophenyl)methoxy]-1-hydroxybutan-2-yl]carbamate (6.50 g, 17.4 mmol) in DCM (200 mL) was added DMP (9.58 g, 22.6 mmol) in portions at room temperature under nitrogen atmosphere. After stirring for additional 2 hours, the resulting mixture was filtered. The filtered cake was washed with DCM (2×10 mL). The combined filtrates was concentrated under reduced pressure. The residue was purified by silica gel column chromatography, eluted with 1000 ethyl acetate in petroleum ether to afford the title compound as a light yellow oil (5.30 g, 740%): $^1$H NMR (400 MHz, $CDCl_3$) δ 9.77 (s, 1H), 7.52-7.41 (m, 2H), 7.22-7.09 (m, 2H), 5.39 (d, J=7.3 Hz, 1H), 4.55 (d, J=11.9 Hz, 1H), 4.42 (d, J=12.0 Hz, 1H), 4.33 (dd, J=7.2, 3.9 Hz, 1H), 3.92 (qd, J=6.6, 4.4, 2.6 Hz, 1H), 1.45 (s, 9H), 1.40 (d, J=6.6 Hz, 3H); MS (ESI, m/z): [(M−1)]+=371.00, 373.00.

The intermediates in Table 4 were prepared according to Step 3 of the procedure to prepare Intermediate A.

TABLE 4

| Characterization data for intermediates prepared according to above. | | | | |
|---|---|---|---|---|
| Intermediate | Structure | Chemical Name | MS: $[(M+1)]^+$ | $^1$H-NMR |
| A-3-1 | 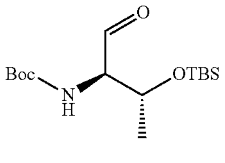 [SMILES: C[C@@H](O[Si](C)(C)C(C)(C)C)[C@H](C=O)NC(=O)OC(C)(C)C] | tert-butyl N-[(2R, 3R)-3-R[(tert-butyldimethylsilyl) oxy]-1-oxobutan-2-yl]carbamate | 318.20 | (400 MHz, $CDCl_3$) δ 9.81 (s, 1H), 5.43 (s, 1H), 4.21 (s, 2H), 1.48 (s, 9H), 0.94 (d, J = 2.6 Hz, 3H), 0.91 (t, J = 4.0 Hz, 1H), 0.87 (s, 9H), 0.09 (s, 6H) |
| A-3-2 | 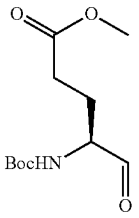 [SMILES: COC(=O)CC[C@@H](C=O)NC(=O)OC(C)(C)C] | methyl (S)-4-((tert-butoxycarbonyl) amino)-5-oxopentanoate | 246.13 | (400 MHz, $CDCl_3$) δ 9.63 (s, 1H), 5.25-5.22 (m, 1H), 4.33-4.30 (m, 1H), 3.73 (s, 3H), 2.57-2.39 (m, 2H), 2.34-2.30 (m, 1H), 1.98-1.88 (m, 1H), 1.49 (s, 9H). |

TABLE 4-continued

Characterization data for intermediates prepared according to above.

| Intermediate | Structure | Chemical Name | MS: [(M + 1)]$^+$ | $^1$H-NMR |
|---|---|---|---|---|
| A-3-3 | 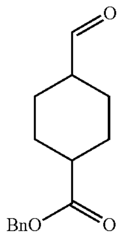 | benzyl 4-formylcyclohexane-1-carboxylate | 247.13 | (400 MHz, Chloroform-d) δ 9.68 (s, 1H), 7.43-7.30 (m, 5H), 5.14 (d, J = 4.6 Hz, 2H), 2.52 (p, J = 6.1 Hz, 1H), 2.38 (tt, J = 6.5, 4.9 Hz, 1H), 1.99 (dq, J = 12.1, 5.6 Hz, 2H), 1.86-1.68 (m, 4H), 1.68-1.51 (m, 2H) |
| A-3-4 | 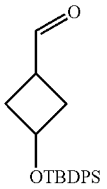 | 3-[(tert-butyldiphenylsilyl)oxy]cyclobutane-1-carbaldehyde | N/A | (400 MHz, Methanol-$d_4$) δ 7.71-7.62 (m, 4H), 7.50-7.34 (m, 6H), 4.40 (d, J = 6.0 Hz, 1H), 4.14-4.02 (m, 1H), 2.47-2.30 (m, 1H), 2.32-2.09 (m, 2H), 2.05-1.72 (m, 2H), 1.04 (s, 9H) |
| A-3-5 | 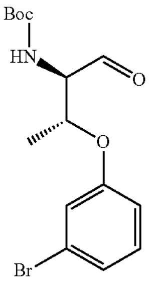 [SMILES: C[C@@H](Oc1cccc(Br)c1)[C@H](C=O)NC(=O)OC(C)(C)C] | tert-butyl N-[(2R,3R)-3-(3-bromophenoxy)-1-oxobutan-2-yl]carbamate | [(M − 1)]$^-$ = 356.05, 358.05 | (400 MHz, DMSO-$d_6$) δ 9.59 (s, 1H), 7.51 (d, J = 7.6 Hz, 1H), 7.25 (t, J = 8.2 Hz, 1H), 7.19-7.06 (m, 2H), 6.96 (d, J = 8.5 Hz, 1H), 4.90-4.83 (m, 1H), 4.29-4.13 (m, 1H), 1.41 (s, 9H), 1.27 (d, J = 6.4 Hz, 3H) |
| A-3-6 | 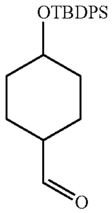 | 4-[(tert-butyldiphenylsilyl)oxy]cyclohexane-1-carbaldehyde | N/A | (400 MHz, DMSO-$d_6$) δ 9.50 (s, 1H), 7.64-7.52 (m, 4H), 7.52-7.35 (m, 6H), 3.64-3.58 (m, 1H), 2.26-2.18 (m, 1H), 1.91-1.67 (m, 4H), 1.45-1.30 (m, 2H), 1.23-1.06 (m, 2H), 1.01 (s, 9H) |

Step 4. Methyl (2E44SS5R)-5-(4-bromophenyl)methoxy]-4-(tert-butoxy)carbonyl]amino]hex-2-enoate. To a solution of tert-butyl N-[(2R,3R)-3-[(4-bromophenyl)methoxy]-1-oxobutan-2-yl]carbamate (20.3 g, 54.5 mmol) in DCM (350 mL) was added methyl 2-(triphenyl-lambda5-phosphanylidene)acetate (20.1 g, 60.0 mmol) at room temperature under nitrogen atmosphere. After stirring for 16 hours at room temperature, the resulting mixture was concentrated under reduced pressure. The residue was purified by silica gel column chromatography, eluted with 5%0 ethyl acetate in petroleum ether. Desired fractions were collected and concentrated under reduced pressure to afford the title compound as a white solid (20.5 g, 854): HH NMR (400 MHz, $CDCl_3$) δ 8.73 (s, 1H), 7.24 (d, J 7.8 Hz, 2H), 7.17 (d, J 7.7 Hz, 2H), 6.94-6.86 (m, 2H), 6.73 (d, J=8.0 Hz, 1H), 4.81-4.78 (m, 1H), 4.45-4.42 (m, 1H), 4.33 (t, J=4.7 Hz, 2H), 4.26-4.21 (m, 1H), 3.92-3.88 (m, 4H), 3.81 (s, 5H), 3.58-3.53 (m, 4H), 3.47-3.41 (, 3H), 2.80-2.54 (9, 7H), 1.88 (s, 5H), 1.27 (s, 3H); MS (ESI, m/z): [(M+23)]I=450.20, 452.20.

The intermediates in Table 5 were prepared according to Step 4 of the procedure to prepare Intermediate A.

TABLE 5

Characterization data for intermediates prepared according to above.

| Intermediate | Structure | Chemical Name | MS: [(M + 1)]+ | $^1$H-NMR |
|---|---|---|---|---|
| A-4-1 | 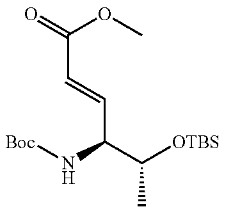 [SMILES: COC(=O)/C=C/[C@H](NC(=O)OC(C)(C)C)[C@@H](C)O[Si](C)(C)C(C)(C)C] | methyl (2E,4S,5R)-4-[(tert-butoxycarbonyl)amino]-5-[(tert-butyldimethylsilyl)oxy]hex-2-enoate | 374.25 | (400 MHz, $CDCl_3$) δ 6.94 (dd, J = 15.7, 6.6 Hz, 1H), 5.99 (d, J = 15.7 Hz, 1H), 4.84 (d, J = 8.9 Hz, 1H), 4.18 (d, J = 7.5 Hz, 1H), 3.97 (s, 1H), 3.76 (s, 3H), 1.46 (s, 9H), 1.15 (d, J = 6.3 Hz, 3H), 0.91 (s, 9H), 0.12 (s, 6H) |
| A-4-2 | 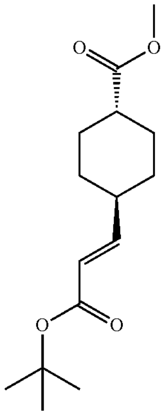 [SMILES: COC(=O)[C@H]1CC[C@H](/C=C/C(=O)OC(C)(C)C)CC1] | methyl (1r,4r)-4-((E)-3-(tert-butoxy)-3-oxoprop-1-en-1-yl)cyclohexane-1-carboxylate | N/A | (400 MHz, DMSO-$d_6$) δ 6.73 (dd, J = 15.7, 6.7 Hz, 1H), 5.69 (dd, J = 15.7, 1.4 Hz, 1H), 3.59 (s, 3H), 2.29-2.25 (m, 1H), 2.14-2.10 (m, 1H),1.98-1.88 (m, 2H), 1.81-1.74 (m, 2H), 1.43 (s, 9H), 1.38-1.34 (m, 2H), 1.18-1.14 (m, 2H). |
| A-4-3 | 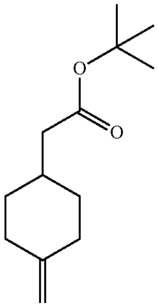 | tert-butyl 2-(4-methylenecyclohexyl) acetate | N/A | (300 MHz, CDCl3) δ 4.63 (s, 2H), 2.33-2.30 (m, 2H), 2.14 (d, J = 7.0 Hz, 2H), 2.7-2.04 (m, 2H), 2.00-1.77 (m, 3H), 1.47 (s, 9H), 1.18-1.01 (m, 2H). |
| A-4-4 | 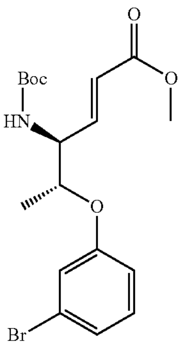 | methyl (2E,4S,5R)-5-(3-bromophenoxy)-4-[(tert-butoxycarbonyl)amino]hex-2-enoate | 414.05, 416.05 | (300 MHz, DMSO-d6) δ 7.37-7.20 (m, 2H), 7.17-7.12 (m, 2H), 7.01-6.88 (m, 2H), 6.03 (dd, J = 15.7, 1.6 Hz, 1H), 4.61-4.40 (m, 2H), 3.68 (s, 3H), 1.40 (s, 9H), 1.20 (d, J = 6.2 Hz, 3H) |

TABLE 5-continued

| Characterization data for intermediates prepared according to above. | | | | |
|---|---|---|---|---|
| Intermediate | Structure | Chemical Name | MS: [(M + 1)]+ | $^1$H-NMR |
| A-4-5 | 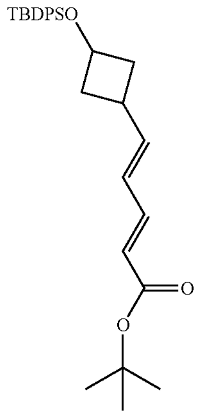 | tert-butyl (2E,4E)-5-[3-[(tert-butyldiphenylsilyl)oxy]cyclobutyl]penta-2,4-dienoate | N/A | (400 MHz, Methanol-d4) δ 7.69-7.65 (m, 4H), 7.48-7.36 (m, 6H), 7.20-7.11 (m, 1H), 6.16-6.11 (m, 1H), 5.75 (d, J = 15.3 Hz, 1H), 4.21-4.13 (m, 1H), 2.39-2.33 (m, 3H), 1.99-1.86 (m, 1H), 1.49 (s, 9H), 1.04 (s, 9H), 0.95-0.85 (m, 2H) |
| A-4-6 | 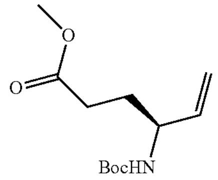 [SMILES: C=C[C@H](CCC(=O)OC)NC(=O)OC(C)(C)C] | methyl (4S)-4-[(tert-butoxycarbonyl)amino]hex-5-enoate | 244.20 | (400 MHz, Chloroform-d) δ 5.76 (ddd, J = 17.2, 10.4, 5.6 Hz, 1H), 5.26-5.10 (m, 2H), 4.56-4.53 (m, 1H), 4.21-4.04 (m, 1H), 3.69 (s, 3H), 2.40 (t, J = 7.6 Hz, 2H), 2.00-1.85 (m, 1H), 1.82-1.78 (m, 1H), 1.45 (s, 9H). |
| A-4-7 | 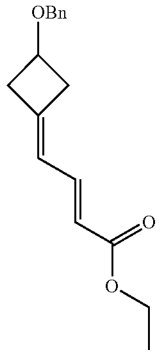 [SMILES: CCOC(=O)/C=C/C=C1CC(OCc2ccccc2)C1] | ethyl (2E)-4-[3-(benzyloxy)cyclobutylidene]but-2-enoate | [(M + Na)]+ = 294.20 | (400 MHz, DMSO-d6) δ 7.40-7.27 (m, 5H), 7.13 (dd, J = 15.3, 11.4 Hz, 1H), 6.20-6.12 (m, 1H), 5.84 (d, J = 15.3 Hz, 1H), 4.43 (s, 2H), 4.12 (q, J = 7.1 Hz, 2H), 3.26-3.11 (m, 1H), 3.07-2.94 (m, 1H), 2.79-2.74 (m, 2H), 1.21 (t, J = 7.1 Hz, 3H). |
| A-4-8 | 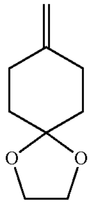 | 8-methylidene-1,4-dioxaspiro[4.5]decane | N/A | (400 MHz, CDCl3) 4.71-4.67 (m, 2H), 4.02-3.97 (m, 4H), 2.33-2.28 (m, 4H), 1.76-1.70 (m, 4H) |
| A-4-9 | 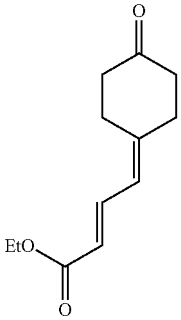 [SMILES: CCOC(=O)/C=C/C=C1CCC(=O)CC1] | ethyl (2E)-4-(4-oxocyclohexylidene)but-2-enoate | N/A | (300 MHz, DMSO-$d_6$) δ 7.56-7.47 (m, 1H), 6.25 (d, J = 11.7 Hz, 1H), 5.97 (d, J = 15.1 Hz, 1H), 4.22-4.08 (m, 2H), 2.79-2.74 (m, 2H), 2.64-2.62 (m 2H), 2.45-2.38 (m, 4H), 1.27-1.20 (m, 3H) |

TABLE 5-continued

| Characterization data for intermediates prepared according to above. | | | | |
|---|---|---|---|---|
| Intermediate | Structure | Chemical Name | MS: $[(M + 1)]^+$ | $^1$H-NMR |
| A-4-10 | 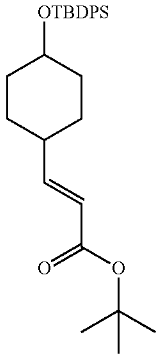 | tert-butyl (2E)-3-4-[(tert-butyldiphenylsilyl)oxy]cyclohexyl]prop-2-enoate | N/A | (400 MHz, DMSO-$d_6$) δ 7.66-7.58 (m, 4H), 7.52-7.40 (m, 6H), 6.65 (dd, J = 15.7, 6.9 Hz, 1H), 5.64 (dd, J = 15.8, 1.4 Hz, 1H), 3.62-3.57 (m, 1H), 2.14-2.03 (m, 1H), 1.80 (d, J = 12.4 Hz, 2H), 1.65 (d, J = 13.2 Hz, 2H), 1.40 (s, 9H), 1.05-0.98 (m, 12H), 0.89-0.83 (m, 1H) |

Step 5. Methyl (4S 5R)-5-[(4-bromophenyl)methoxy-4-[[(tert-butoxyl)carbonyl]amino]hexanoate. To a solution of methyl (2E,4S,5R)-5-[(4-bromophenyl)methoxy]-4-[[(tert-butoxy)carbonyl]amino]hex-2-enoate (20.0 g, 46.7 mmol) in THF (350 mL) was added aluminum nickel alloy (4.00 g, 4.70 mmol, 10% w/w) at room temperature under nitrogen atmosphere. The mixture was purged with hydrogen for 3 times and stirred for 16 hours under hydrogenation atmosphere (2 atm.) at room temperature. The resulting mixture was filtered. The filtered cake was washed with THF (3×100 mL). The combined filtrates was concentrated under reduced pressure to afford the title compound as a light yellow oil (19.0 g, 85t): $^1$H NMR (400 MHz, $CDCl_3$) 1 7.53-7.39 (m, 2H), 7.19 (d, J=8.3 Hz, 2H), 4.70 (d, J=10.1 Hz, 1H), 4.56-4.49 (m, 1H), 4.38 (dd, J 11.5, 6.3 Hz, 1H), 3.73 (s, 1H), 3.66 (s, 3H), 2.41-2.32 (m, 2H), 1.95 (dtd, J=15.4, 7.9, 7.4, 3.1 Hz, 1H), 1.67 (tdd, J=14.4, 11.9, 9.7, 7.0 Hz, 1H), 1.42 (d, JA 4.1 Hz, 9H), 1.18 (dd, J 6.2, 3.9 Hz, 3H); MS (ESI, m/z): $[(M+23)]^+$=452.20, 454.20.

The intermediates in Table 6 were prepared according to Step 5 of the procedure to prepare Intermediate A.

TABLE 6

| Characterization data for intermediates prepared according to above. | | | | |
|---|---|---|---|---|
| Intermediate | Structure | Chemical Name | MS: $[(M + 1)]^+$ | $^1$H-NMR |
| A-5-1 | 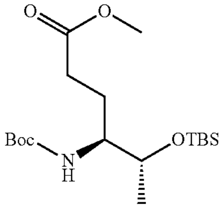 [SMILES: COC(=O)CC[C@H](NC(=O)OC(C)(C)C)[C@@H](C)O[Si](C)(C)C(C)(C)C] | methyl (4S,5R)-4-((tert-butoxycarbonyl)amino)-5-((tert-butyldimethylsilyl)oxy)hexanoate | 376.20 | (400 MHz, $CDCl_3$) δ 4.58 (d, J = 9.9 Hz, 1H), 3.95-3.88 (m, 1H), 3.70 (s, 3H), 3.47 (s, 1H), 2.50-2.32 (m, 2H), 1.95 (p, J = 7.2 Hz, 1H), 1.70-1.60 (m, 1H), 1.45 (s, 9H), 1.15 (d, J = 6.4 Hz, 3H), 0.91 (s, 9H), 0.07 (s, 6H) |
| A-5-2 | 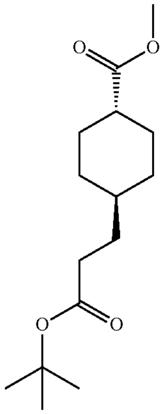 [SMILES: COC(=O)[C@H]1CC[C@H](CCC(=O)OC(C)(C)C)CC1] | methyl (1r,4r)-4-(3-(tert-butoxy)-3-oxopropyl)cyclohexane-1-carboxylate | N/A | (400 MHz, DMSO-$d_6$) δ 3.58 (s, 3H), 2.26-2.15 (m, 3H), 1.92-1.84 (m, 2H), 1.76-1.68 (m, 2H), 1.41-1.39 (m, 11H), 1.37-1.24 (m, 2H), 1.19-1.15 (m, 1H), 0.97-0.90 (m, 2H). |

TABLE 6-continued

| Characterization data for intermediates prepared according to above. | | | | |
|---|---|---|---|---|
| Intermediate | Structure | Chemical Name | MS: $[(M + 1)]^+$ | $^1$H-NMR |
| A-5-3 | 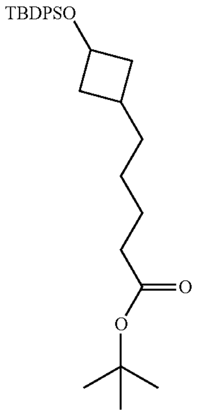 | tert-butyl 5-[3-[(tert-butyldiphenylsilyl) oxy]cyclobutyl] pentanoate | N/A | (400 MHz, DMSO-$d_6$) δ 7.61-7.59 (m, 4H), 7.46-7.40 (m, 6H), 4.09-4.02 (m, 1H), 2.29-2.19 (m, 1H), 2.16-2.11 (m, 2H), 1.60-1.48 (m, 3H), 1.47-1.40 (m, 2H), 1.38 (s, 9H), 1.37-1.19 (m, 3H), 1.18-1.08 (m, 2H), 0.97 (s, 9H) |
| A-5-4 | 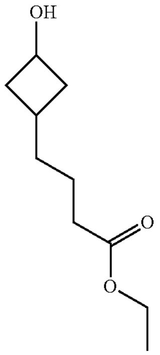 | ethyl 4-(3-hydroxycyclobutyl) butanoate | N/A | (400 MHz, DMSO-$d_6$) δ 4.90 (br, 1H), 4.16 (p, J = 6.7 Hz, 0.4 H), 4.05 (q, J = 7.1 Hz, 2H), 3.90-3.81 (m, 0.6H), 2.34-2.21 (m, 3H), 2.18-1.96 (m, 1H), 1.94-1.79 (m, 2H), 1.60-1.56 (m, 1H), 1.48- 1.27 (m, 4H), 1.18 (t, J = 7.1 Hz, 3H). |
| A-5-5 | 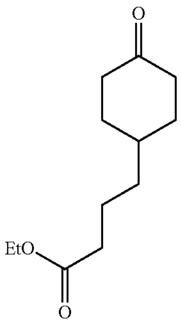 [SMILES: CCOC(=O)CCCC1CCC(=O)CC1] | ethyl 4-(4-oxocyclohexyl) butanoate | N/A | (400 MHz, DMSO-$d_6$) δ 4.09-4.04 (m, 2H), 2.50-2.27 (m, 4H), 2.27-2.14 (m, 2H), 2.02-1.90 (m, 2H), 1.79-1.65 (m, 1H), 1.65-1.52 (m, 2H), 1.40-1.23 (m, 4H), 1.21-1.17(m, 3H) |
| A-5-6 | 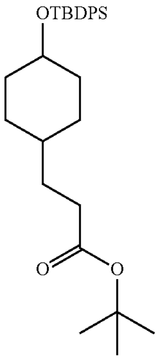 | tert-butyl 3-[4-[(tert-butyldiphenylsilyl) oxylcyclohexyl] propanoate | N/A | (400 MHz, DMSO-$d_6$) δ 7.65-7.58 (m, 4H), 7.50-7.39 (m, 6H), 3.60-3.52 (m, 1H), 2.12 (t, J = 7.7 Hz, 2H), 1.76 (d, J = 12.2 Hz, 2H), 1.60 (d, J = 13.1 Hz, 2H), 1.38 (s, 9H), 1.35-1.22 (m, 4H), 1.19-1.07 (m, 1H), 1.00 (s, 9H), 0.79-0.65 (m, 2H) |

Step 6. Tert-butyl N-[(3S,4R)-4-[(4-bromophenyl) methoxy]-1-carbamoylpentan-3-yl]carbamate (Intermediate A'). Methyl (4S,5R)-5-[(4-bromophenyl)methoxy]-4-[[I (tert-butoxy)carbonyl]amino]hexanoate (13.8 g, 32.1 minol) was added to a solution of 7 M $NH_3$ (g) in MeOH (120 mL) at room temperature. The reaction mixture was sealed and stirred for 16 hours at 90 TC. The resulting mixture was cooled down to room temperature and concentrated under reduced pressure. The residue was purified by reversed phase flash chromatography with the following conditions: Column: WelFlash™ C18-I, 20~40 µm, 330 g; Eluent A: water (plus 10 mmol/$LNH_4HCO_3$); Eluent B: ACN; Gradient: 35% - 55% B in 25 min; Flow rate: 80 mL/min; Detector: UV 220/254 nm; desired fractions were collected at 48% B and concentrated under reduced pressure to afford the title compound as a white solid (8.30 g, 63%): $^1$H NMR (400 MHz, DMSO-$d_6$) δ 7.52 (d, J=8.1 Hz, 2H), 7.30 (d, J=8.2 Hz, 2H), 7.23 (s, 1H), 6.75-6.62 (m, 2H), 4.51-4.41 (m, 2H), 3.41 (tt, J=11.9, 6.7 Hz, 2H), 2.04 (qdd, J=15.1, 9.7, 5.9 Hz, 2H), 1.77 (dt, J=6.9, 3.7 Hz, 1H), 1.48 (ddd, J=14.2, 9.9, 5.4 Hz, 1H), 1.38 (s, 9H), 1.06 (d, J=6.1 Hz, 3H); MS (ESI, m/z): $[(M1+1)]^+$=415.15, 417.15.

The intermediates in Table 7 were prepared according to Step 6 of the procedure to prepare Intermediate A.

TABLE 7

Characterization data for intermediates prepared according to above.

| Intermediate | Structure | Chemical Name | MS: $[(M + 1)]^+$ | $^1$H-NMR |
|---|---|---|---|---|
| A1 | 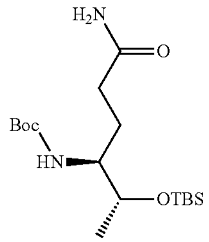 [SMILES: C[C@@H](O[Si](C)(C)C(C)(C)C)[C@H](CCC(N)=O)NC(=O)OC(C)(C)C] | tert-butyl N-(3S,4R)-4-[tert-butyldimethylsilyl)oxyl-1-carbamoylpentan-3-yl]carbamate | 361.35 | (400 MHz, $CDCl_3$) δ 6.36 (s, 1H), 5.52 (s, 1H), 4.75 (d, J = 9.7 Hz, 1H), 3.90 (qd, J = 6.3, 3.4 Hz, 1H), 3.57-3.45 (m, 1H), 2.37-2.17 (m, 2H), 2.00-1.87 (m, 1H), 1.64 (ddt, J = 14.3, 12.2, 6.4 Hz, 1H), 1.45 (s, 9H), 1.14 (d, J = 6.3 Hz, 3H), 0.90 (s, 9H), 0.07 (s, 6H) |
| A2 | 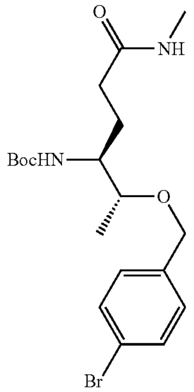 [SMILES: CNC(=O)CC[C@H](NC(=O)OC(C)(C)C)[C@@H](C)OCc1ccc(Br)cc1] | tert-butyl N-[(3S,4R)-4-[(4-bromophenyl)methoxy]-1-(methylcarbamoyl)pentan-3-yl]carbamate | 429.13, 431.13 | (400 MHz, $CDCl_3$) δ 7.48 (d, J = 8.4 Hz, 2H), 7.21 (d, J = 8.4 Hz, 2H), 6.25 (s, 1H), 4.81 (d, J = 9.6 Hz, 1H), 4.55 (d, J = 11.8 Hz, 1H), 4.38 (d, J = 11.8 Hz, 1H), 3.69-3.51 (m, 2H), 2.82 (d, J = 4.7 Hz, 3H), 2.33-2.14 2H), 2.05-1.90 (m, 1H), 1.77-1.59 (m, 1H), 1.45 (s, 9H), 1.20 (d, J = 6.3 Hz, 3H) |
| A51 | 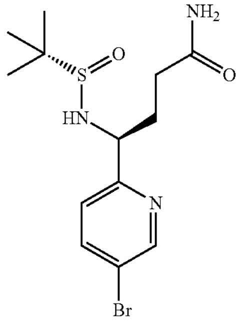 | (4S)-4-(5-bromopyridin-2-yl)-4[(2-methylpropane-2-sulfinyl)amino]butanamide | 362.10, 364.10 | (400 MHz, DMSO-$d_6$) δ 8.34-8.32 (d, J = 2.4 Hz, 1H), 7.73-7.71 (m, 1H), 7.65-7.63 (d, J = 8.2 Hz, 1H), 7.29 (s, 1H), 6.80 (s, 1H), 5.79-5.77 (d, J = 5.4 Hz, 1H), 4.34-4.29 (m, 1H), 2.22-1.98 (m, 3H), 1.95-1.70 (m, 1H), 1.08 (s, 9H) |
| A52 | 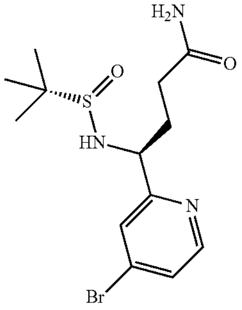 | (4S)-4-(4-bromopyridin-2-yl)-4-[(2-methylpropane-2-sulfinyl)amino]butanamide | 362.00, 364.00 | (400 MHz, DMSO-$d_6$) δ 8.35 (d, J = 5.1 Hz, 1H), 7.62 (s, 1H), 7.41 (dd, J = 5.1, 1.4 Hz, 1H), 7.31 (s, 1H), 6.85 (s, 1H), 5.86 (d, J = 6.0 Hz, 1H), 4.32 (q, J = 6.5 Hz, 1H), 2.22-1.97 (m, 3H), 1.91-1.82 (m, 1H), 1.10 (s, 9H) |

Tert-butyl N-[(3S,4R)-4- [(3-bromophenyl) methoxy]-1-carbamoylpentan-3-yl]carbamate (Intermediate A3)

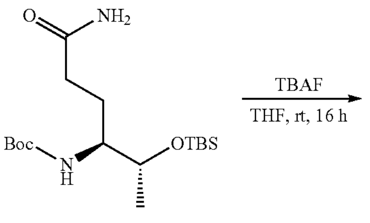

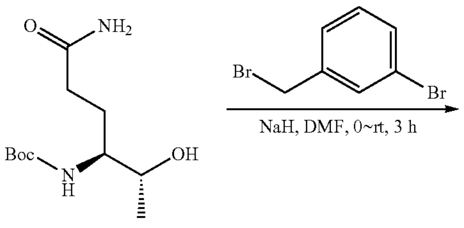

-continued

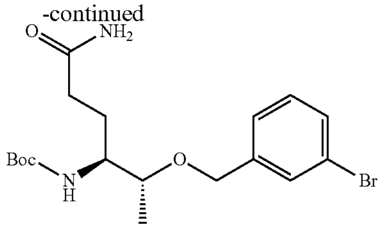

Intermediate A3

Step 1: Tert-butyl N-[(3S,4R)-1-carbamoyl-4-hydroxy-pentan-3-yl]carbamate. To a solution of tert-butyl N-[(3S, 4R)-4-[(tert-butyldimethylsilyl)oxy]-1-carbamoylpentan-3-yl]carbamate (36.0 g, 99.8 mmol) in THF (720 mL) was added TBAF (31.3 g, 120 mmol) at room temperature. After stirring for additional 16 h, the resulting mixture was concentrated under reduced pressure. The residue was purified by silica gel column chromatography, eluted with $CH_2Cl_2$/MeOH (50:1 to 10:1) to afford the title compound as a colorless solid (22.0 g, 900%): $^1$HNMR (400 MHz, $CD_3OD$) δ 6.45 (d, J=9.5 Hz, 1H), 3.64 (p, J=6.3 Hz, 1H), 3.45-3.33 (m, 1H), 2.36-2.17 (m, 2H), 2.03 (dtd, J=13.3, 6.6, 3.4 Hz, 1H), 1.66-1.52 (m, 1H), 1.46 (s, 9H), 1.17 (d, J=6.4 Hz, 3H); LC/MS (ESI, m/z): $[(M+H)]^+$=247.25.

The intermediates in Table 8 were prepared according to step 1 of the procedure to prepare Intermediate A3.

TABLE 8

Characterization data for intermediates prepared according to above.

| Intermediate | Structure | Chemical Name | MS: $[(M + 1)]^+$ | $^1$H-NMR |
|---|---|---|---|---|
| A3-1-1 | 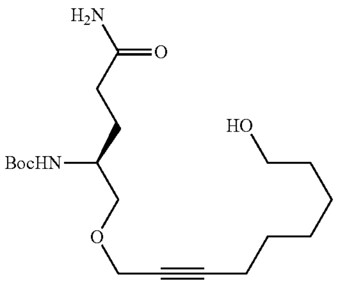 [SMILES: CC(C)(C)OC(=O)N[C@@H](CCC(N)=O)COCC#CCCCCCCO] | tert-butyl (S)-(5-amino-1-((9-hydroxynon-2-yn-1-yl)oxy)-5-oxopentan-2-yl)carbamate | 371.20 | (400 MHz, DMSO-$d_6$) δ 7.22 (s, 1H), 6.69 (s, 1H), 6.63 (d, J = 8.6 Hz, 1H), 4.33 (t, J = 5.2 Hz, 1H), 4.09 (t, J = 2.1 Hz, 2H), 3.49 (d, J = 4.9 Hz, 1H), 3.38 (td, J = 6.5, 5.2 Hz, 2H), 3.31-3.26 (m, 2H), 2.23-2.18 (m, 2H), 2.07-2.03 (m, 2H), 1.75-1.61 (m, 2H), 1.43 (dd, J = 14.0, 7.0 Hz, 4H), 1.38(s, 9H), 1.36 -1.21 (m, 4H). |
| A3-1-2 | 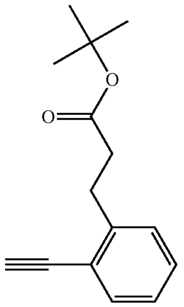 [SMILES: C#Cc1ccccc1CCC(=O)OC(C)(C)C] | tert-butyl 3-(2-ethynylphenyl) propanoate | N/A | (400 MHz, DMSO-$d_6$) δ 7.47-7.43 (m, 1H), 7.37-7.28 (m, 2H), 7.23 (td, J = 7.3, 1.8 Hz, 1H), 4.39 (s, 1H), 2.97 (t, J = 7.6 Hz, 2H), 2.54 (t, J = 7.6 Hz, 2H), 1.37 (s, 9H). |

TABLE 8-continued

| Characterization data for intermediates prepared according to above. | | | | |
|---|---|---|---|---|
| Intermediate | Structure | Chemical Name | MS: [(M + 1)]$^+$ | $^1$H-NMR |
| A3-1-3 | 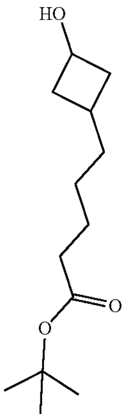 [SMILES: CC(C)(C)OC(=O)CCCCC1CC(O)C1] | tert-butyl 5-(3-hydroxycyclobutyl) pentanoate | N/A | (400 MHz, Methanol-$d_4$) δ 4.07-3.96 (m, 1H), 2.44-2.37 (m, 2H), 2.24-2.20 (m, 2H), 2.09-1.93 (m, 1H), 1.76-1.63 (m, 1H), 1.63-1.52 (m, 2H), 1.49-1.40 (m, 12H), 1.34-1.19 (m, 2H) |
| A3-1-4 | 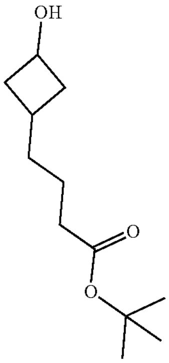 | tert-butyl 4-(3-hydroxycyclobutyl) butanoate | N/A | (400 MHz, DMSO-$d_6$) δ 4.87 (dd, J = 6.4, 1.6 Hz, 1H), 4.17-4.13 (m, 0.4H), 3.91-3.79 (m, 0.6H), 2.36-2.20 (m, 1H), 2.18-2.13 (m, 2H), 2.06-1.80 (m, 2H), 1.70-1.49 (m, 1H), 1.46-1.26 (m, 13H), 1.00-0.82 (m, 1H) |
| A3-1-5 | 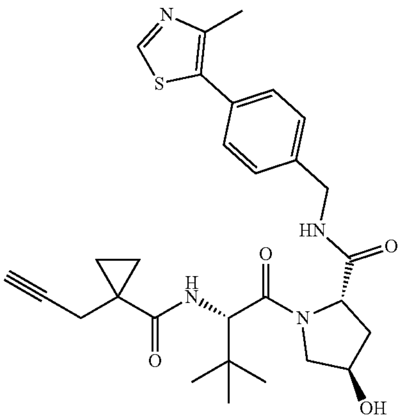 [SMILES: C#CCC1(C(=O)N[C@H](C(=O)N2C[C@H](O)C[C@H]2C(=O)NCc2ccc(-c3scnc3C)cc2)C(C)(C)C)CC1] | (2S,4R)-1-[(2S)-3,3-dimethyl-2-[[1-(prop-2-yn-1-yl)cyclopropyl] formamido]butanoyl]-4-hydroxy-N-[[4-(4-methyl-1,3-thiazol-5-yl)phenyl]methyl] pyrrolidine-2-carboxamide | 537.25 | (400 MHz, Methanol-$d_4$) δ 8.89 (s, 1H), 7.52-7.41 (m, 4H), 4.73 (s, 1H), 4.63-4.57 (m, 2H), 4.55-4.50 (m, 1H), 4.38 (d, J = 15.4 Hz, 1H), 3.89 (d, J = 11.1 Hz, 1H), 3.82 (dd, J = 11.0, 3.8 Hz, 1H), 2.87-2.81 (m, 1H), 2.57-2.48 (m, 1H), 2.50 (s, 3H), 2.39 (dd, J = 17.9, 2.7 Hz, 1H), 2.30-2.16 (m, 1H), 2.16-2.05 (m, 1H), 1.26-1.18 (m, 1H), 1.18-1.07 (m, 1H), 1.08 (s, 9H), 0.90-0.77 (m, 2H) |

TABLE 8-continued

| Characterization data for intermediates prepared according to above. | | | | |
|---|---|---|---|---|
| Intermediate | Structure | Chemical Name | MS: $[(M + 1)]^+$ | $^1$H-NMR |
| A3-1-6 | 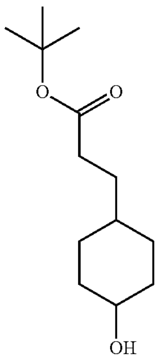 [SMILES: CC(C)(C)OC(=O)CCC1CCC(O)CC1] | tert-butyl 3-(4-hydroxycyclohexyl) propanoate | N/A | (400 MHz, DMSO-$d_6$) δ 4.44 (d, J = 4.5 Hz, 1H), 3.31-3.26 (m, 1H), 2.18 (t, J = 8.5 Hz, 2H), 1.84-1.75 (m, 2H), 1.66 (d, J = 13.0 Hz, 2H), 1.40 (s, 9H), 1.37-1.35 (m, 1H), 1.15-1.02 (m, 3H), 0.93-0.83 (m, 3H) |

Step 2: Tert-butyl N-[(3S,4R)-4-[(3-bromophenyl) methoxy]-1-carbamoylpentan-3-yl]carbamate (Intermediate A3). To a solution of tert-butyl N-[(3S,4R)-1-carbamoyl-4-hydroxypentan-3-yl]carbamate (2.00 g, 8.12 minol) in DMF (30.0 mL) was added NaH (60% dispersion in mineral oil, 0.34 g, 8.53 minol) at 0 TC. The reaction mixture was stirred at 0 TC for 1 h. To the above solution was added dropwise a solution of 1-bromo-3-(bromomethyl) benzene (2.23 g, 8.93 mmol) in DMF (20.0 mL) at 0 TC. The mixture was warmed slowly to room temperature and was stirred for additional 2 h. The resulting solution was quenched with water (100 mL), extracted with EtOAc (3x50.0 mL). The combined organic layers were washed with brine (3x30.0 mL) and dried over anhydrous $Na_2SO_4$. After filtration, the filtrate was concentrated under reduced pressure. The residue was purified by Prep-HPLC with the following conditions (Column: XBridge Shield RP18 OBD Column, 30x150 mm, 5 m; Mobile Phase A: water (plus 10 mmol/ $LNH_4HCO_3$), Mobile Phase B: ACN; Flow rate: 60 mL/min; Gradient: (B%) 5%~35% in 7 min; Detector: UV 220 nm). The fractions containing desired product were collected at 6.3 min and concentrated under reduced pressure to afford the title compound as a colorless solid (1.20 g, 350%): $^1$H NMR (400 MHz, DMSO-4) [7.53 (s, 1H), 7.46 (dt, J=7.6, 1.8 Hz, 1H), 7.35-7.26 (, 2H), 7.24 (s, 1H), 6.73-6.63 (m, 2H), 4.48 (s, 2H), 3.50 (p, J=7.4, 6.0 Hz, 1H), 3.42 (p, J=5.9 Hz, 1H), 2.06 (qdd, J=15.1, 9.7, 6.0 Hz, 2H), 1.76 (dtd, J=13.7, 7.0, 6.6, 3.4 Hz, 1H), 1.52-1.44 (m, 1H), 1.39 (s, 9H), 1.07 (d, J=6.2 Hz, 3H); LC/MS (ESI, m -z): $[(M+H)]^+$=415.05, 417.05.

The intermediates in Table 9 were prepared according to Step 2 of the procedure to prepare Intermediate A3.

TABLE 9

| Characterization for intermediates prepared according to above. | | | | |
|---|---|---|---|---|
| Intermediate | Structure | Chemical Name | MS: $[(M + 1)]^+$ | $^1$H-NMR |
| A4 | 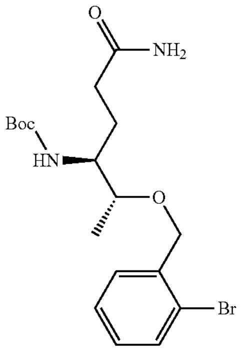 [SMILES: C[C@@H](OCc1ccccc1Br)[C@H](CCC(N)=O)NC(=O)OC(C)(C)C] | tert-butyl N-[(3S,4R)-4-[(2-bromophenyl) methoxy]-1-carbamoylpentan-3-yl]carbamate | 415.10, 417.10 | (400 MHz, $CD_3OD$) δ 7.56 (td, J = 8.2, 1.5 Hz, 2H), 7.35 (td, J = 7.5, 1.2 Hz, 1H), 7.20 (td, J = 7.7, 1.8 Hz, 1H), 4.67 (d, J = 12.4 Hz, 1H), 4.58 (d, J = 12.4 Hz, 1H), 3.65-3.53 (m, 2H), 2.39-2.17 (m, 2H), 2.09-1.90 (m, 1H), 1.64 (td, J = 9.8, 5.0 Hz, 1H), 1.45 (s, 9H), 1.23 (d, J = 5.9 Hz, 3H). |

TABLE 9-continued

Characterization for intermediates prepared according to above.

| Intermediate | Structure | Chemical Name | MS: $[(M + 1)]^+$ | $^1$H-NMR |
|---|---|---|---|---|
| A5 | 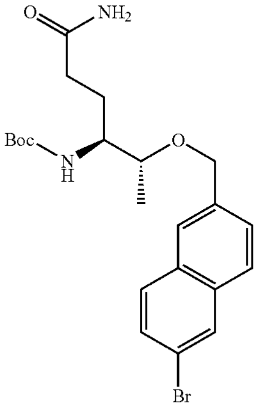 [SMILES: C[C@@H](OCc1ccc2cc(Br)ccc2c1)[C@H](CCC(N)=O)NC(=O)OC(C)(C)C] | tert-butyl N-[(3S,4R)-4-[(6-bromonaphthalen-2-yl)methoxyl-1-carbamoylpentan-3-yl]carbamate | 465.10, 467.10 | (400 MHz, DMSO-$d_6$) δ 8.19 (d, J = 2.0 Hz, 1H), 7.92-7.83 (m, 3H), 7.63 (dd, J = 8.7, 2.0 Hz, 1H), 7.54 (dd, J = 8.6, 1.5 Hz, 1H), 7.24 (s, 1H), 6.73-6.63 (m, 2H), 4.70-4.58 (m, 2H), 3.49 (s, 1H), 3.54-3.41 (m, 1H), 2.07 (qdd, J = 15.0, 9.8, 5.9 Hz, 2H), 1.88-1.75 (m, 1H), 1.57-1.43 (m, 1H), 1.37 (s, 9H), 1.11 (d, J = 5.9 Hz, 3H). |
| A6 | 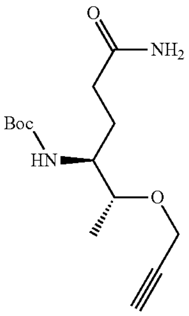 [SMILES: C#CCO[C@H](C)[C@H](CCC(N)=O)NC(=O)OC(C)(C)C] | tert-butyl N-[(3S,4R)-1-carbamoyl-4-(prop-2-yn-1-yloxy)pentan-3-yl]carbamate | 285.35 | (400 MHz, DMSO-$d_6$) δ 7.22 (s, 1H), 6.68 (s, 1H), 6.62 (d, J = 9.3 Hz, 1H), 4.21-4.07 (m, 2H), 3.48 (p, J = 6.2 Hz, 1H), 3.37 (t, J = 2.4 Hz, 1H), 2.13-1.92 (m, 2H), 1.76 (dddd, J = 13.4, 9.8, 6.2, 3.1 Hz, 1H), 1.48-1.40 (m, 1H), 1.39 (s, 9H), 1.03 (d, J = 6.2 Hz, 3H). |
| A7 | 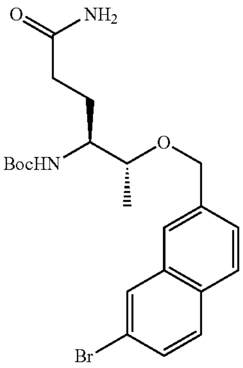 [SMILES: C[C@@H](OCc1ccc2ccc(Br)cc2c1)[C@H](CCC(N)=O)NC(=O)OC(C)(C)C] | tert-butyl ((2R,3S)-6-amino-2-((7-bromonaphthalen-2-yl)methoxy)-6-oxohexan-3-yl)carbamate | 465.07, 467.05 | (400 MHz, DMSO-$d_6$) δ 8.16 (d, J = 2.0 Hz, 1H), 7.94-7.84 (m, 3H), 7.61 (dd, J = 8.7, 2.0 Hz, 1H), 7.52 (dd, J = 8.4, 1.6 Hz, 1H), 7.25 (s, 1H), 6.77-6.64 (m, 2H), 4.75-4.57 (m, 2H), 3.51-3.45 (m, 2H), 2.10-2.03 (m, 2H), 1.84-1.80 (m, 1H), 1.54-1.50 (m, 1H), 1.36 (s, 9H), 1.11 (d, J = 5.9 Hz, 3H). |
| A8 | 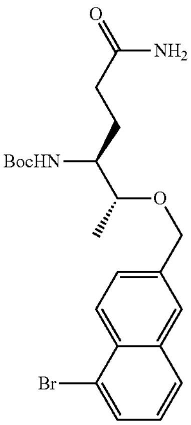 [SMILES: C[C@@H](OCc1ccc2c(Br)cccc2c1)[C@H](CCC(N)=O)NC(=O)OC(C)(C)C] | tert-butyl ((2R,3S)-6-amino-2-((5-bromonaphthalen-2-yl)methoxy)-6-oxohexan-3-yl)carbamate | 465.07, 467.05 | (400 MHz, DMSO-$d_6$) δ 8.09 (d, J = 8.7 Hz, 1H), 7.98-7.92 (m, 2H), 7.85 (dd, J = 7.4, 1.0 Hz, 1H), 7.66 (dd, J = 8.8, 1.7 Hz, 1H), 7.48-7.41 (m, 1H), 7.24 (s, 1H), 6.75-6.63 (m, 2H), 4.74-4.64 (m, 2H), 3.52-3.47 (m, 2H), 2.09-2.05 (m, 2H), 1.83-1.81 (m, 1H), 1.53-1.50 (m, 1H), 1.35 (s, 9H), 1.11 (d, J = 5.9 Hz, 3H). |

TABLE 9-continued

Characterization for intermediates prepared according to above.

| Intermediate | Structure | Chemical Name | MS: [(M + 1)]$^+$ | $^1$H-NMR |
|---|---|---|---|---|
| A9 | 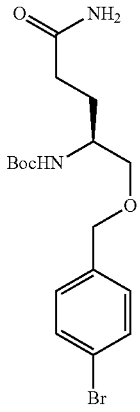 | tert-butyl (S)-(5-amino-1-((4-bromobenzyl)oxy)-5-oxopentan-2-yl)carbamate | 401.00, 403.00 | (400 MHz, DMSO-$d_6$) δ 7.56-7.51 (m, 2H), 7.32-7.26 (m, 2H), 7.23 (s, 1H), 6.74-6.63 (m, 2H), 4.44 (s, 2H), 3.59-3.54 (m, 1H), 3.33-3.29 (m, 2H), 2.08-2.04 (m, 2H), 1.72-1.68 1H), 1.52-1.49 (m 1H), 1.38 (s, 9H). |
| A10 | 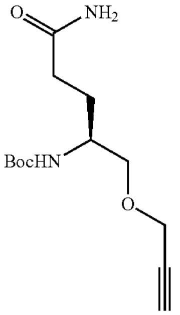 [SMILES: C#CCOC[C@H](CCC(N)=O)NC(=O)OC(C)(C)C] | tert-butyl (S)-(5-amino-5-oxo-1-(prop-2-yn-1-yloxy)pentan-2-yl)carbamate | 271.10 | (400 MHz, $CDCl_3$) δ 6.50 (s, 1H), 5.41 (s, 1H), 4.96 (d, J = 8.9 Hz, 1H), 4.24 (s, 2H), 3.83-3.81 (m, 1H), 3.62-3.52 (m, 2H), 2.46 (t, J = 2.4 Hz, 1H), 2.37-2.27 (m, 2H), 1.92-1.88 (m, 1H), 1.71-1.68 (m, 1H), 1.47 (s, 9H). |
| A11 | 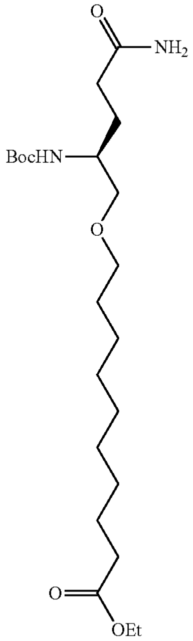 [SMILES: CCOC(=O)CCCCCCCCCOC[C@H](CCC(N)=O)NC(=O)OC(C)(C)C] | ethyl (S)-10-((5-amino-2-((tert-butoxycarbonyl) amino)-5-oxopentyl)oxy) decanoate | 431.30 | (400 MHz, $CDCl_3$) δ 6.73 (s, 1 H), 5.45 (s, 1H), 5.02-4.99 (m, 1H), 4.15 (q, J = 7.1 Hz, 2H), 3.79-3.76 (m, 1H), 3.46-3.37 (m, 3H), 2.37-2.28 (m, 4H), 1.89-1.85 (m, 2H), 1.78-1.74 (m, 2H), 1.65-1.61 (m, 2H), 1.58-1.54 (m, 1H), 1.47 (s, 9 H), 1.34-1.30 (m, 10H), 1.28 (t, J = 7.1 Hz, 3H). |

TABLE 9-continued

| Characterization for intermediates prepared according to above. | | | | |
|---|---|---|---|---|
| Intermediate | Structure | Chemical Name | MS: [(M + 1)]+ | 1H-NMR |
| A12 | 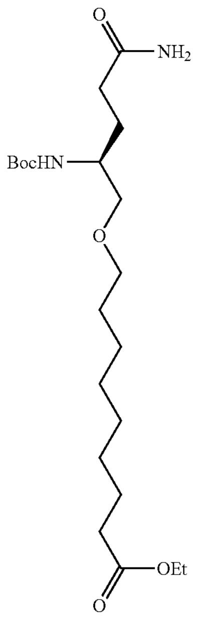 | ethyl (S)-9-((5-amino-2-((tert-butoxycarbonyl) amino)-5-oxopentyl)oxy) nonanoate | 417.30 | (400 MHz, $CDCl_3$) δ 6.67 (s, 1 H), 5.67 (s, 1H), 4.97-4.95 (m, 1H), 4.15 (q, J = 7.1 Hz, 2H), 3.79-3.76 (m, 1H), 3.58-3.45 (m, 2H), 3.27-3.23 (m, 1H), 2.26 (t, J = 7.3 Hz, 2H), 2.15-1.97 (m, 1H), 1.84-1.61 (m, 2H), 1.59-1.43 (m, 6H), 1.38 (s, 9 H), 1.27-1.24 (m, 8H), 1.28 (t, J = 7.1 Hz, 3H). |
| A13 | 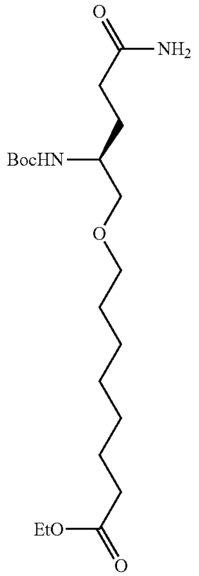 [SMILES: CCOC(=O)CCCCCCCOC[C@H](CCC(N)=O)NC(=O)OC(C)(C)C] | ethyl (S)-8-((5-amino-2-((tert-butoxycarbonyl) amino)-5-oxopentyl)oxy) octanoate | 403.30 | (400 MHz, $CDCl_3$) δ 4.15 (q, J = 7.1 Hz, 2H), 3.47-3.38 (m, 3H), 2.39-2.21 (m, 5H), 2.10-2.04 (m, 1H), 1.89 (q, J = 7.2 Hz, 2H), 1.84-1.54 (m, 4H), 1.51 (d, J = 2.6 Hz, 1H), 1.47 (s, 9H), 1.41-1.31 (m, 5H), 1.30-1.25 (t, J = 7.1 Hz, 3H) |
| A14 | 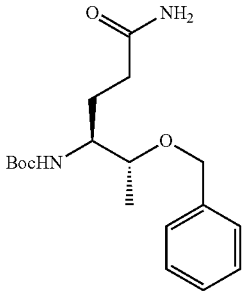 [SMILES: C[C@@H](OCc1ccccc1)[C@H](CCC(N)=O)NC(=O)OC(C)(C)C] | tert-butyl N-[(3S,4R)-4-(benzyloxy)-1-carbamoylpentan-3-yl]carbamate | 337.20 | (400 MHz, DMSO-$d_6$) δ 7.44-7.15 (m, 6H), 6.75-6.51 (m, 2H), 4.52-4.42 (m, 2H), 3.49-3.41 (m, 2H), 2.17-1.93 (m, 2H), 1.86-1.74 (m, 1H), 1.56-1.43 (m, 1H), 1.39 (s, 9H), 1.07 (d, J = 6.0 Hz, 3H) |

TABLE 9-continued

| Characterization for intermediates prepared according to above. | | | | |
|---|---|---|---|---|
| Intermediate | Structure | Chemical Name | MS: $[(M + 1)]^+$ | $^1$H-NMR |
| A15 | 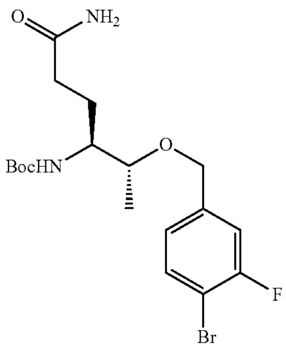 [SMILES: C[C@@H](OCc1ccc(Br)c(F)c1)[C@H](CCC(N)=O)NC(=O)OC(C)(C)C] | tert-butyl N-[(3S,4R)-4-[(4-bromo-3-fluorophenyl) methoxy]-1-carbamoylpentan-3-yl]carbamate | 433.32, 435.32 | (400 MHz, DMSO-$d_6$) δ 7.65 (t, J = 7.7 Hz, 1H), 7.35 (dd, J = 10.0, 1.9 Hz, 1H), 7.22 (s, 1H), 7.13 (dd, J = 8.2, 1.9 Hz, 1H), 6.73-6.64 (m, 2H), 4.58-4.37 (m, 2H), 3.52-3.38 (m, 2H), 2.15-1.96 (m, 2H), 1.84-1.69 (m, 1H), 1.54-1.44 (m, 1H), 1.49 (s, 9H), 1.07 (d, J = 6.1 Hz, 3H) |
| A16 | 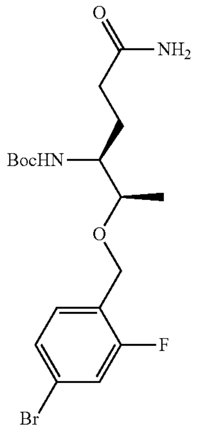 [SMILES: C[C@@H](OCc1ccc(Br)cc1F)[C@H](CCC(N)=O)NC(=O)OC(C)(C)C] | tert-butyl N-[(3S,4R)-4-[(4-bromo-2-fluorophenyl) methoxy]-1-carbamoylpentan-3-yl]carbamate | 433.10 435.10 | (400 MHz, DMSO-$d_6$) δ 7.52 (d, J = 9.6 Hz, 1H), 7.47-7.38 (m, 2H), 7.21 (s, 1H), 6.68-6.64 (m, 2H), 4.50 (q, J = 12.3 Hz, 2H), 3.45-3.43 (m, 2H), 2.36-1.90 (m, 2H), 1.77-1.75 (m, 1H), 1.49-1.46 (m, 1H), 1.37 (s, 9H), 1.07 (d, J = 5.5 Hz, 3H). |
| A17 | 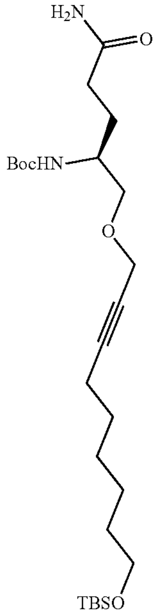 | tert-butyl N-[(2S)-1-([9-[(tert-butyldimethylsilyl) oxy]non-2-yn-1-yl]oxy)-4-carbamoylbutan-2-yl]carbamate | 485.35 | (400 MHz, DMSO-$d_6$) δ 7.22 (s, 1H), 6.69 (s, 1H), 6.62 (d, J = 8.5 Hz, 1H), 4.23 (t, J = 6.6 Hz, 1H), 4.09 (t, J = 2.1 Hz, 2H), 3.57 (t, J = 6.3 Hz, 2H), 3.35-3.28 (m, 4H), 2.22-2.18 (m, 2H), 2.08-2.02 (m, 2H), 1.67-1.64 (m, 1H), 1.55-1.35 (s, 16H), 0.86 (s, 9H), 0.03 (s, 6H). |

TABLE 9-continued

| Characterization for intermediates prepared according to above. | | | | |
|---|---|---|---|---|
| Intermediate | Structure | Chemical Name | MS: $[(M + 1)]^+$ | $^1$H-NMR |
| A21 | 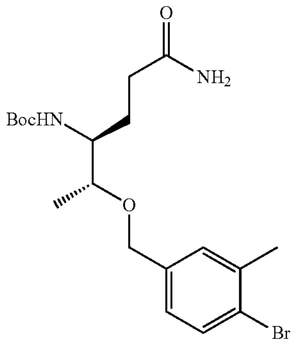 [SMILES: Cc1cc(CO[C@H](C)[C@H](CCC(N)=O)NC(=O)OC(C)(C)C)ccc1Br] | tert-butyl N-[(3S,4R)-4-[(4-bromo-3-methylphenyl) methoxy]-1-carbamoylpentan-3-yl]carbamate | 429.10, 431.10 | (400 MHz, DMSO-$d_6$) δ 7.52 (d, J = 8.1 Hz, 1H), 7.32 (d, J = 2.1 Hz, 1H), 7.23-7.19 (m, 1H), 7.09 (dd, J = 8.1, 2.2 Hz, 1H), 6.68 (s, 1H), 6.61 (d, J = 9.2 Hz, 1H), 4.48-4.36 (m, 2H), 3.47-3.38 (m, 2H), 2.34 (s, 3H), 2.05 (s, 1H), 2.15-1.95 (m, 1H), 1.78-1.76 (m, 1H), 1.49-1.46 (m, 1H), 1.38 (s, 9H), 1.06 (d, J = 6.1 Hz, 3H) |
| A22 | 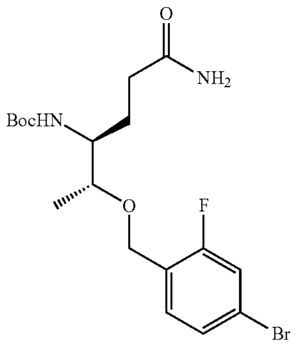 [SMILES: C[C@@H](OCc1ccc(Br)cc1F)[C@H](CCC(N)=O)NC(=O)OC(C)(C)C] | tert-butyl N-[(3S,4R)-4-[(4-bromo-2-fluorophenyl) methoxy]-1-carbamoylpentan-3-yl]carbamate | 433.10 435.10 | (400 MHz, DMSO-$d_6$) δ 7.52 (d, J = 9.6 Hz, 1H), 7.47-7.37 (m, 2H), 7.21 (s, 1H), 6.68 (s 1H) 6.61 (d, J = 8.7 Hz, 1H), 4.50 (q, J = 12.3 Hz, 2H), 3.43 (d, J = 6.3 Hz, 2H), 2.11-1.93 (m, 2H), 1.79-1.71 (m, 1H), 1.48-1.43 (m, 1H), 1.37 (s, 9H), 1.35 (s, 1H), 1.07 (d, J = 5.5 Hz, 3H) |
| A23 | 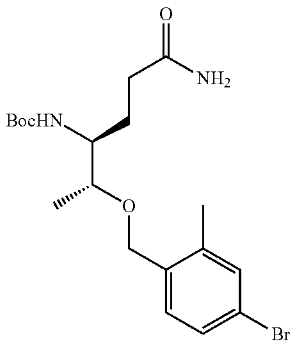 [SMILES: Cc1cc(Br)ccc1CO[C@H](C)[C@H](CCC(N)=O)NC(=O)OC(C)(C)C] | tert-butyl N-[(3S,4R)-4-[(4-bromo-2-methylphenyl) methoxy]-1-carbamoylpentan-3-yl]carbamate | 431.10, 433.10 | (400 MHz, Methanol-$d_4$) δ 7.35 (s, 1H), 7.28 (q, J = 8.2 Hz, 2H), 4.60-4.43 (m, 2H), 3.61-3.51 (m, 2H), 2.34 (s, 3H), 2.31-2.16 (m, 2H), 2.02-1.84 (m, 1H), 1.69-1.53 (m, 1H), 1.45 (s, 9H), 1.20 (d, J = 6.1 Hz, 3H) |

Tert-butyl N-[(2S)-1-(4-bromophenoxy)-4-carbamoylbutan-2-yl]carbamate (Intermediate A18)

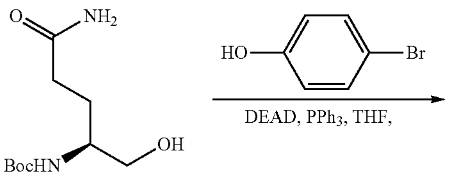

-continued

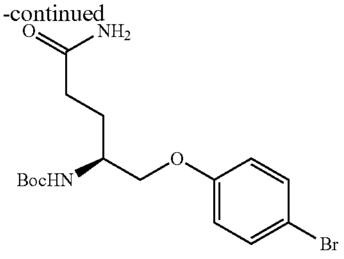

Intermediate A18

To a stirred solution of 4-bromophenol (968 mg, 5.59 minol) in THF (45.0 mL) were added $PPh_3$ (1.69 g, 6.44 minol) and DEAD (1.12 g, 6.43 minol) dropwise at 0 TC under nitrogen atmosphere. To the above mixture was added tert-butyl N-[(25)-4-carbamoyl-1-hydroxybutan-2-yl]carbamate (1.00 g, 4.31 mmol) at room temperature. The resulting mixture was stirred for additional 6 h at room temperature. The resulting mixture was concentrated under reduced pressure. The residue was purified by reverse phase flash chromatography with the following conditions: Column: WelFlash™ C18-I, 20~40 um, 80 g; Eluent A: water (plus 10 mmol/LFA); Eluent B: ACN; Gradient: 35]- 60% B in 25 mi; Flow rate: 80 mL/min; Detector: UV 220/254 nm; desired fractions were collected at 5100 B and concentrated under reduced pressure to afford the title compound as a light yellow solid (350 mg, 21%): $^1$H NMR (400 MHz, DMSO-) 7.47-7.41 (m, 2H), 7.26 (s, 1H), 6.93-6.88 (m, 2H), 6.84 (d, J=8.5 Hz, 1H), 6.73 (s, 1H), 3.94-3.77 (m, 2H), 3.77-3.65 (m, 1H), 2.18-2.04 (m, 2H), 1.87-1.74 (m, 1H), 1.64-1.50 (m, 1H), 1.39 (s, 9H); LC/MS (ESI, mcz): [(M+1)]$^+$=386.95, 388.95

The intermediates in Table 10 were prepared according to the above procedure to prepare intermediate A18.

TABLE 10

Characterization data for intermediates prepared according to above.

| Intermediate | Structure | Chemical Name | MS: [(M + 1)]$^+$ | $^1$H-NMR |
|---|---|---|---|---|
| A19 | 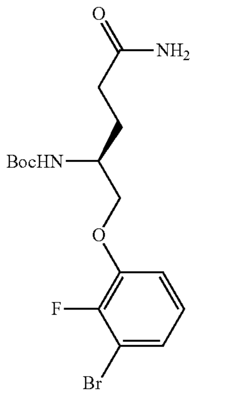 [SMILES: CC(C)(C)OC(=O)N[C@@H](CCC(N)=O)COc1cccc(Br)c1F] | tert-butyl N-[(2S)-1-(3-bromo-2-fluorophenoxy)-4-carbamoylbutan-2-yl]carbamate | 405.26 | (400 MHz, DMSO-$d_6$) δ 7.27 (s, 1H), 7.26-7.17 (m, 2H), 7.09 (td, J = 8.2, 1.7 Hz, 1H), 6.85 (d, J = 8.5 Hz, 1H), 6.74 (s, 1H), 3.41-3.97 (m, 2H), 3.77-3.73 (m, 1H), 2.21-2.04 (m, 2H), 1.87-1.72 (m, 1H), 1.69-1.52 (m, 1H), 1.38 (s, 9H) |
| A20 | 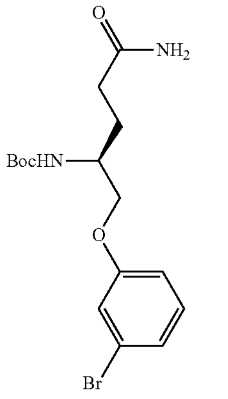 [SMILES: CC(C)(C)OC(=O)N[C@@H](CCC(N)=O)COc1cccc(Br)c1] | tert-butyl N-[(2S)-1-(3-bromophenoxy)-4-carbamoylbutan-2-yl]carbamate (800 mg, 23.99%) as a light yellow oil | 387.00, 388.95 | (400 MHz, DMSO-$d_6$) δ 7.24 (t, J = 8.0 Hz, 2H), 7.15-7.11 (m, 2H), 6.97-6.93 (m, 1H), 6.83 (d, J = 8.5 Hz, 1H), 6.73 (s, 1H), 4.23 (t, J = 6.6 Hz, 1H), 3.92-3.87 (m, 2H), 3.70 (d, J = 11.8 Hz, 1H), 2.12 (q, J = 6.7 Hz, 2H), 1.80 (d, J = 14.8 Hz, 1H), 1.39 (s, 9H) |
| A24 | 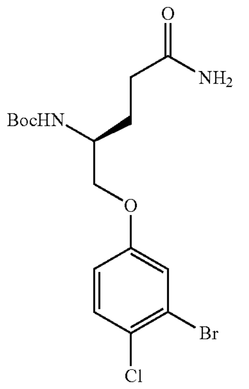 [SMILES: CC(C)(C)OC(=O)N[C@@H](CCC(N)=O)COc1ccc(Cl)c(Br)c1] | tert-butyl N-[(2S)-4-carbamoyl-1-(4-chloro-3-iodophenoxy) butan-2-yl]carbamate | [(M − 1)]$^-$ = 467.10 | (300 MHz, DMSO-$d_6$) δ 7.67-7.51 (m, 1H), 7.44 (d, J = 10.7 Hz, 1H), 7.23 (d, 1H), 6.99 (d, J = 8.9 Hz, 1H), 6.80 (d, J = 8.4 Hz, 1H), 6.70 (d, 1H), 3.87 (m, J = 5.9 Hz, 2H), 3.30 (m, 1H), 2.52-2.49 (m, J = 1.9 Hz, 8H), 1.75-1.71 (m, 1H), 1.61-1.57 (m, 1H), 1.26-1.22 (m, 1H), 0.96-0.78 (m, 2H) |

TABLE 10-continued

| Characterization data for intermediates prepared according to above. | | | | |
|---|---|---|---|---|
| Intermediate | Structure | Chemical Name | MS: [(M + 1)]$^+$ | $^1$H-NMR |
| A25 | 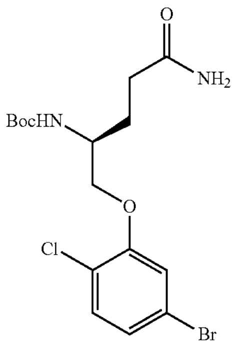 [SMILES: CC(C)(C)OC(=O)N[C@@H](CCC(N)=O)COc1cc(Br)ccc1Cl] | tert-butyl N-[(2S)-1-(5-bromo-2-chlorophenoxy)-4-carbamoylbutan-2-yl]carbamate | 421.15, 423.15 | (400 MHz, DMSO-$d_6$) δ 7.55-7.52 (m, 1H), 7.38 (d, J = 2.5 Hz, 1H), 7.26 (s, 1H), 7.15 (dd, J = 8.4, 2.1 Hz, 1H), 6.81 (d, J = 8.5 Hz, 1H), 6.75-6.73 (m, 1H), 4.37-4.17 (m, 1H), 4.01-3.97 (m, 2H), 3.89-3.74 (m, 2H), 2.66-2.60 (m, 3H), 2.16-1.98 (m, 2H), 1.89-1.67 (m, 2H), 1.64-1.46 (m, 1H), 1.36-1.29 (m, 1H), 1.26-1.03 (m, 1H), 0.90-0.80 (m, 1H) |
| A26 | 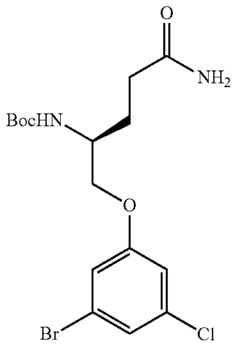 [SMILES: CC(C)(C)OC(=O)N[C@@H](CCC(N)=O)COc1cc(Cl)cc(Br)c1] | tert-butyl N-[(2S)-1-(3-bromo-5-chlorophenoxy)-4-carbamoylbutan-2-yl]carbamate | 421.05, 423.05 | (400 MHz, DMSO-$d_6$) δ 7.86 (s, 1H), 7.29-7.23 (m, 2H), 7.15 (t, J = 2.0 Hz, 1H), 7.07 (t, J = 2.0 Hz, 1H), 6.84 (d, J = 8.5 Hz, 1H), 4.39 (t, J = 8.6 Hz, 1H), 3.88-3.78 (m, 1H), 3.75-3.65 (m, 1H), 2.19-2.07 (m, 2H), 1.69-1.52 (m, 2H), 1.38 (s, 9H) |
| A27 | 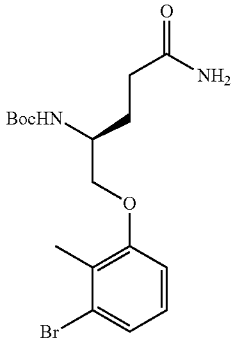 [SMILES: Cc1c(Br)cccc1OC[C@H](CCC(N)=O)NC(=O)OC(C)(C)C] | tert-butyl N-[(2S)-1-(3-bromo-2-methylphenoxy)-4-carbamoylbutan-2-yl]carbamate | 400.90, 402.95 | (400 MHz, DMSO-$d_6$) δ 7.26 (s, 1H), 7.16 (dd, J = 8.1, 1.1 Hz, 1H), 7.09 (t, J = 8.1 Hz, 1H), 7.02-6.91 (m, 1H), 6.84 (d, J = 8.4 Hz, 1H), 6.77-6.67 (m, 1H), 3.95-3.92 (m, 1H), 3.89-3.73 (m, 2H), 2.24 (s, 3H), 2.19-2.06 (m, 2H), 1.85-1.77 (m, 1H), 1.71-1.51 (m, 1H), 1.39 (s, 9H) |
| A28 | 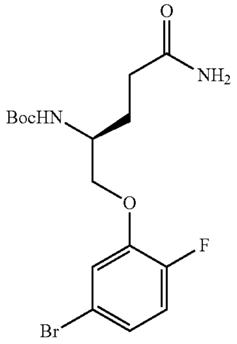 [SMILES: CC(C)(C)OC(=O)N[C@@H](CCC(N)=O)COc1cc(Br)ccc1F] | tert-butyl N-[(2S)-1-(4-bromo-2-fluorophenoxy)-4-carbamoylbutan-2-yl]carbamate | 405.05, 407.05 | (400 MHz, DMSO-$d_6$) δ 7.75-7.53 (m, 2H), 7.40 (d, J = 7.7, 2.3 Hz, 1H), 7.27 (s, 1H), 7.24-7.08 (m, 1H), 6.73 (s, 1H), 4.39 (d, J = 8.5 Hz,1H), 4.09-3.91 (m, 4H), 3.88-3.66 (m, 2H), 2.66-2.51 (m, 1H), 2.21-2.04 (m, 2H), 1.88-1.66 (m, 2H), 1.64-1.60 (m, 1H), 1.33 (s, 1H), 1.29-1.14 (m, 2H) |

TABLE 10-continued

| Intermediate | Structure | Chemical Name | MS: [(M + 1)]$^+$ | $^1$H-NMR |
|---|---|---|---|---|
| Characterization data for intermediates prepared according to above. | | | | |
| A29 | 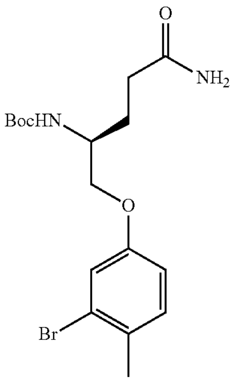 [SMILES: Cc1ccc(OC[C@H](CCC(N)=O)NC(=O)OC(C)(C)C)cc1Br] | tert-butyl N-[(2S)-1-(3-bromo-4-methylphenoxy)-4-carbamoylbutan-2-yl]carbamate | 401.30, 403.30 | (400 MHz, DMSO-$d_6$) δ 7.27-7.24 (m, 1H), 7.15 (d, J = 2.6 Hz, 1H), 6.88 (s, 1H), 6.82 (s, 1H), 6.75 (d, J = 13.5 Hz, 2H), 3.86-3.84 (m, 2H), 3.70-3.68 (m, 1H), 2.27 (s, 3H), 2.11-2.09 (m, 2H), 1.79-1.77 (m, 1H), 1.60-1.56 (m, 1H), 1.38 (s, 9H) |
| A30 | 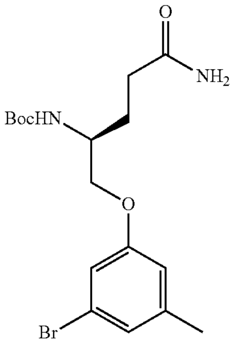 [SMILES: Cc1cc(Br)cc(OC[C@H](CCC(N)=O)NC(=O)OC(C)(C)C)c1] | tert-butyl N-[(2S)-1-(3-bromo-5-methylphenoxy)-4-carbamoylbutan-2-yl]carbamate | 401.00, 403.00 | (400 MHz, DMSO-$d_6$) δ 7.26 (s, 1H), 6.97 (d, J = 1.4, 1.0 Hz, 1H), 6.93 (d, J = 2.2 Hz, 1H), 6.83 (d, J = 8.5 Hz, 1H), 6.78 (s, 1H), 6.74 (s, 1H), 3.89-3.85 (m, 2H), 3.71-3.67 (m, 1H), 2.26 (s, 3H), 2.13-2.09 (m, 2H), 1.87-1.71 (m, 1H), 1.66-1.50 (m, 1H), 1.39 (s, 9H) |
| A31 | 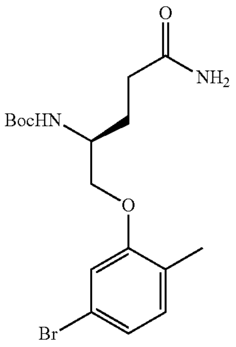 [SMILES: Cc1ccc(Br)cc1OC[C@H](CCC(N)=O)NC(=O)OC(C)(C)C] | tert-butyl N-[(2S)-1-(5-bromo-2-methylphenoxy)-4-carbamoylbutan-2-yl]carbamate | 401.05, 403.05 | (400 MHz, DMSO-$d_6$) δ 7.27 (s, 1H), 7.09 (d, J = 7.4, 1.4 Hz, 2H), 7.02 (d, J = 7.9, 1.8 Hz, 1H), 6.82 (d, J = 8.5 Hz, 1H), 6.73 (s, 1H), 3.96-3.92 (m, 1H), 3.84-3.80 (m, 2H), 2.20-2.06 (m, 5H), 1.82-1.78 (m, 1H), 1.69-1.57 (m, 1H), 1.39 (s, 9H) |
| A32 | 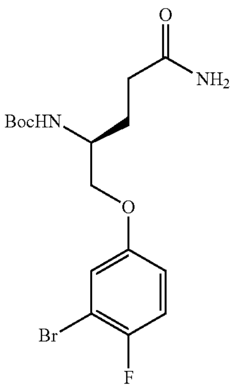 [SMILES: CC(C)(C)OC(=O)N[C@@H](CCC(N)=O)COc1ccc(F)c(Br)c1] | tert-butyl N-[(2S)-1-(3-bromo-4-fluorophenoxy)-4-carbamoylbutan 2-yl]carbamate | 404.95, 406.95 | (400 MHz, DMSO-$d_6$) δ 7.34-7.23 (m, 3H), 7.00-6.96 (m, 1H), 6.83 (d, J = 8.5 Hz, 1H), 6.73 (s, 1H), 3.90-3.86 (m, 2H), 3.71-3.67 (m, 1H), 2.20-2.03 (m, 2H), 1.85-1.72 (m, 1H), 1.64-1.56 (m, 1H), 1.39 (s, 9H) |

TABLE 10-continued

Characterization data for intermediates prepared according to above.

| Intermediate | Structure | Chemical Name | MS: $[(M + 1)]^+$ | $^1$H-NMR |
|---|---|---|---|---|
| A33 | 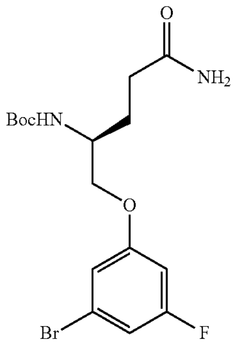 [SMILES: CC(C)(C)OC(=O)N[C@@H](CCC(N)=O)COc1cc(F)cc(Br)c1] | tert-butyl N-[(2S)-1-(3-bromo-5-fluorophenoxy)-4-carbamoylbutan-2-yl]carbamate | 405.00, 407.00 | (400 MHz, DMSO-$d_6$) δ 7.26 (s, 1H), 7.09 (dt, J = 8.3, 2.0 Hz, 1H), 7.02 (d, J = 2.2 Hz, 1H), 6.93-6.81 (m, 2H), 6.73 (s, 1H), 4.03-3.90 (m, 2H), 3.73-3.69 (m, 1H), 2.17-2.13 (m, 1H), 2.14-2.03 (m, 1H), 1.87-1.74 (m, 1H), 1.62-1.58 (m, 1H), 1.38 (s, 9H) |
| A34 | 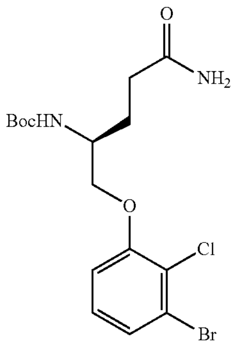 [SMILES: CC(C)(C)OC(=O)N[C@@H](CCC(N)=O)COc1cccc(Br)c1Cl] | tert-butyl N-[(2S)-1-(3-bromo-2-chlorophenoxy)-4-carbamoylbutan-2-yl]carbamate | 421.00, 423.00 | (300 MHz, DMSO-$d_6$) δ 7.66-7.57 (m, 1H), 7.32 (dd, J = 7.8, 1.7 Hz, 1H), 7.23 (dd, J = 10.4, 5.6 Hz, 2H), 6.80 (d, J = 8.4 Hz, 1H), 6.72 (s, 1H), 4.06-3.89 (m, 2H), 3.78-3.74 (m, 1H), 2.24-2.10 (m, 1H), 2.15-2.01 (m, 1H), 1.91-1.73 (m, 1H), 1.63-1.59 (m, 1H), 1.37 (s, 9H) |
| A35 | 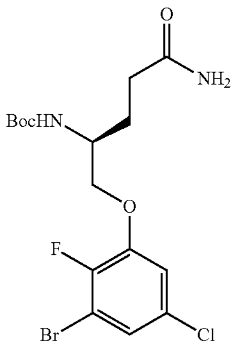 [SMILES: CC(C)(C)OC(=O)N[C@@H](CCC(N)=O)COc1cc(Cl)cc(Br)c1F] | tert-butyl N-[(2S)-1-(3-bromo-5-chloro-2-fluorophenoxy)-4-carbamoylbutan-2-yl]carbamate | 438.95, 440.95 | (400 MHz, DMSO-$d_6$) 6 7.42-7.36 (m, 2H), 7.30-7.25 (m, 1H), 6.86 (t, J = 8.7 Hz, 1H), 6.75 (s, 1H), 3.76-3.73 (m, 1H), 2.13 (m, 2H), 1.76 (m, 1H), 1.68-1.60 (m, 3H), 1.37 (s, 9H) |
| A36 | 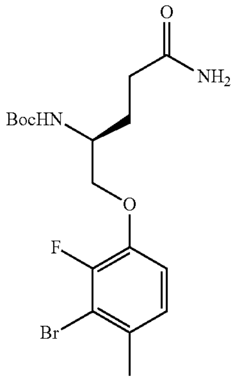 [SMILES: Cc1ccc(OC[C@H](CCC(N)=O)NC(=O)OC(C)(C)C)c(F)c1Br] | tert-butyl N-bromo-2-fluoro-4-methylphenoxy)-4-carbamoylbutan-2-yl]carbamate | 419.05, 421.05 | (400 MHz, DMSO-$d_6$) δ 7.27 (s, 1H), 7.17-7.08 (m, 2H), 6.84 (d, J = 8.5 Hz, 1H), 6.74 (s, 1H), 4.02-3.89 (m, 2H), 3.72 (d, J = 4.7 Hz, 1H), 2.31 (s, 3H), 2.21-2.03 (m, 2H), 1.86-1.73 (m, 1H), 1.66-1.53 (m, 1H), 1.38 (s, 9H) |

TABLE 10-continued

| Characterization data for intermediates prepared according to above. | | | | |
|---|---|---|---|---|
| Intermediate | Structure | Chemical Name | MS: $[(M + 1)]^+$ | $^1$H-NMR |
| A37 | 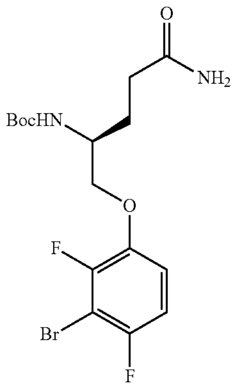 [SMILES: CC(C)(C)OC(=O)N[C@@H](CCC(N)=O)COc1ccc(F)c(Br)c1F] | tert-butyl N-[(2S)-1-(3-bromo-2,4-difluorophenoxy)-4-carbamoylbutan-2-yl]carbamate | 423.00, 425.00 | (400 MHz, DMSO-$d_6$) δ 7.33-7.16 (m, 3H), 6.84 (d, J = 8.5 Hz, 1H), 6.73 (s, 1H), 4.23 (t, J = 6.5 Hz, 1H), 4.06-3.91 (m, 2H), 2.13-2.09 (m, 2H), 1.84-1.74 (m, 1H), 1.71-1.61 (m, 1H), 1.38 (s, 9H) |
| A38 | 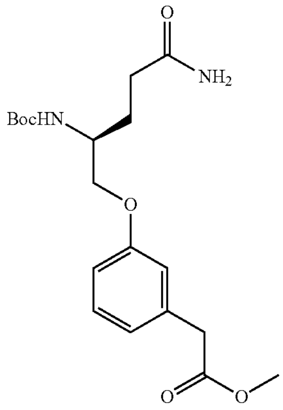 [SMILES: COC(=O)Cc1cccc(OC[C@H](CCC(N)=O)NC(=O)OC(C)(C)C)c1] | methyl 2-[3-[(2S)-2-[(tert-butoxycarbonyl) amino]-4-carbamoylbutoxy] phenyl]acetate | $[(M - 1)]^-$ = 379.20 | N/A |
| A39 | 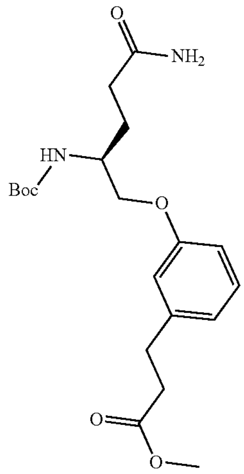 [SMILES: COC(=O)CCc1cccc(OC[C@H](CCC(N)=O)NC(=O)OC(C)(C)C)c1] | methyl 3-[3-[(2S)-2-[(tert-butoxycarbonyl) amino]-4-carbamoylbutoxy] phenyl]propanoate | 395.11 | (400 MHz, DMSO-$d_6$) δ 7.56 (s, 1H), 7.42-7.10 (m, 1H), 6.78 (ddt, J = 23.2, 14.9, 8.0 Hz, 4H), 5.86-5.72 (m, 1H), 4.13-3.68 (m, 3H), 3.67-3.51 (m, 2H), 3.35-3.32 (m, 1H), 2.72-2.55 (m, 3H), 2.26-1.76 (m, 4H), 1.60-1.55(m, 1H), 1.39 (s, 9H) |

TABLE 10-continued

| Characterization data for intermediates prepared according to above. | | | | |
|---|---|---|---|---|
| Intermediate | Structure | Chemical Name | MS: $[(M + 1)]^+$ | $^1$H-NMR |
| A40 | 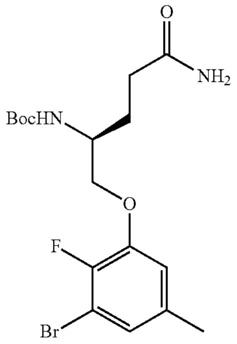 [SMILES: Cc1cc(Br)c(F)c(OC[C@H](CCC(N)=O)NC(=O)OC(C)(C)C)c1] | tert-butyl N-[(2S)-1-(3-bromo-2-fluoro-5-methylphenoxy)-4-carbamoylbutan-2-yl]carbamate | 419.10, 421.10 | (400 MHz, DMSO-$d_6$) δ 7.27 (s, 1H), 7.04 (d, J = 6.4 Hz, 2H), 6.85 (d, J = 8.4 Hz, 1H), 6.75 (s, 1H), 4.01-3.90 (m, 2H), 3.78-3.69 (m, 1H), 2.27 (s, 3H), 2.22-2.06 (m, 2H), 1.87-1.72 (m, 2H), 1.38 (s, 9H) |
| A41 | 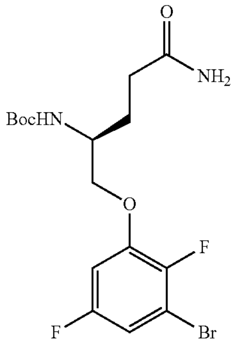 [SMILES: CC(C)(C)OC(=O)N[C@@H](CCC(N)=O)COc1cc(F)cc(Br)c1F] | tert-butyl N-[(2S)-1-(3-bromo-2,5-difluorophenoxy)-4-carbamoylbutan-2-yl]carbamate | 423.05, 425.05 | (400 MHz, $CDCl_3$) δ 6.96-6.90 (m, 1H), 6.75-6.68 (m, 1H), 6.19 (s, 1H), 5.52 (s, 1H), 5.10 (d, J = 8.1 Hz, 1H), 4.10-3.98 (m, 3H), 2.40 (t, J = 7.0 Hz, 2H), 2.11-1.99 (m, 2H), 1.49 (s, 9H) |
| A53 | 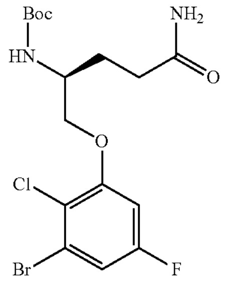 [SMILES: CC(C)(C)OC(=O)N[C@@H](CCC(N)=O)COc1cc(F)cc(Br)c1Cl] | tert-butyl N-[(2S)-1-(3-bromo-2-chloro-5-fluorophenoxy)-4-carbamoylbutan-2-yl]carbamate | 439.00, 441.00 | (300 MHz, DMSO-$d_6$) δ 7.34 (dd, J = 7.6, 2.7 Hz, 1H), 7.29-7.23 (m, 2H), 6.85 (d, J = 8.4 Hz, 1H), 6.76 (s, 1H), 4.12-3.94 (m, 2H), 3.80-3.78 (m, 1H), 2.17-2.13 (m, 2H), 1.84-1.80 (m, 1H), 1.64-1.60 (m, 1H), 1.40 (s, 9H) |

Tert-butyl N-[(1S)-1-[(3-bromophenyl)carbamoyl]-3-carbamoylpropyl]carbamate (Intermediate A42)

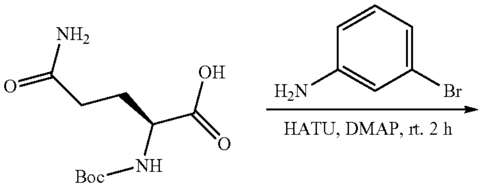

-continued

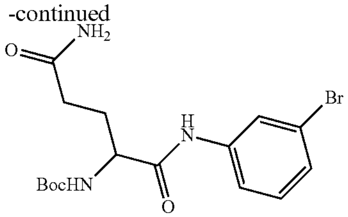

A42

Tert-butyl N-[(1S)-1-[(3-bromophenyl)carbamoyl]-3-carbamoylpropyl]carbamate. To a stirred solution of (2S)-2-[(tert-butoxycarbonyl)amino]-4-carbamoylbutanoic acid (900 mg, 3.66 mmol) and 3-bromoaniline (629 mg, 3.66 mmol) in THF (20 mL) were added DMAP (45 mg, 0.37 mmol) and DCC (1.13 g, 5.49 mmol) in portions at 0° C. under nitrogen atmosphere. The resulting mixture was stirred for 2 h at ambient temperature under nitrogen atmosphere. The resulting mixture was concentrated under reduced pressure. The residue was purified by reverse phase flash chromatography with the following conditions: Spherical C18 Column, 20~40 um, 330 g; Mobile Phase A: Water (plus 10 mmol/LFA), Mobile Phase B: ACN; Gradient: 15% to 44% B in 30 min; Detector: UV 254/220 nm. Desired fractions were collected at 40% B, concentrated under reduced pressure and lyophilized to afford title compound (700 mg, 43%) as a white solid: $^1$H NMR (400 MHz, DMSO-$d_6$) δ 10.16 (s, 1H), 7.98 (t, J=1.9 Hz, 1H), 7.51 (dt, J=7.8, 1.8 Hz, 1H), 7.32-7.21 (m, 4H), 6.80-6.77 (m, 1H), 4.02 (td, J=8.3, 7.6, 4.9 Hz, 1H), 2.15-2.11 (m, 2H), 1.97-1.72 (m, 2H), 1.39 (s, 9H); LC/MS (ESI, m/z): [(M+1)]+=400.10, 402.10

The intermediates in Table 11 were prepared according to the procedure to prepare Intermediate A42.

TABLE 11

Characterization data for intermediates prepared according to above.

| Intermediate | Structure | Chemical Name | MS: $[(M + 1)]^+$ | $^1$H-NMR |
|---|---|---|---|---|
| A43 | 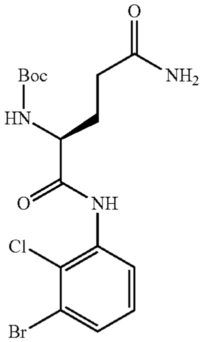 [SMILES: CC(C)(C)OC(=O)N[C@@H](CCC(N)=O)C(=O)Nc1cccc(Br)c1Cl] | tert-butyl N-R15)-1-[(3-bromo-2-chlorophenyl) carbamoyl]-3-carbamoylpropyl] carbamate | 433.95, 435.95 | (400 MHz, DMSO-$d_6$) δ 7.84 (d, J = 8.1 Hz, 1H), 7.59 (dd, J = 8.0, 1.5 Hz, 1H), 7.36-7.21 (m, 4H), 6.82 (s, 1H), 4.16-4.12 (m, 1H), 2.25-2.13 (m, 2H), 2.02-1.95 (m, 1H), 1.86-1.78 (m, 1H), 1.41 (s, 9H) |
| A44 | 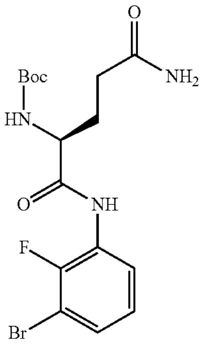 | tert-butyl N-[(1S)-1-[(3-bromo-2-fluorophenyl) carbamoyl]-3-carbamoylpropyl] carbamate | 418.05, 420.05 | (300 MHz, DMSO-$d_6$) δ 9.87 (s, 1H), 7.87 (t, J = 7.7 Hz, 1H), 7.48-7.43 (m, 1H), 7.33 (s, 1H), 7.24-7.04 (m, 2H), 6.82 (s, 1H), 4.19 (q, J = 7.4 Hz, 1H), 2.34-2.08 (m, 2H), 1.98-1.68 (m, 2H), 1.40 (s, 9H) |
| A45 | 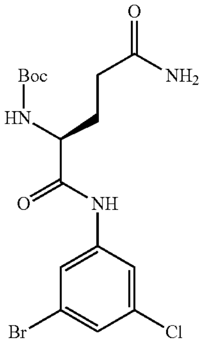 [SMILES: CC(C)(C)OC(=O)N[C@@H](CCC(N)=O)C(=O)Nc1cc(Cl)cc(Br)c1] | tert-butyl N-[(1S)-1-[(3-bromophenyl) carbamoyl]-3-carbamoylpropyl] carbamate | $[(M - 1)]^-$ = 432.00, 434.00 | N/A |
| A46 | 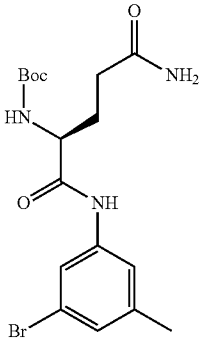 [SMILES: Cc1cc(Br)cc(NC(=O)[C@H](CCC(N)=O)NC(=O)OC(C)(C)C)c1] | Tert-butyl N-[(1S)-1-[(3-bromo-5-methylphenyl) carbamoyl]-3-carbamoylpropyl] carbamate | 414.15, 416.15 | (300 MHz, DMSO-$d_6$) δ 10.06 (s, 1H), 7.76 (s, 1H), 7.36-7.28 (m 2H), 7.14-7.06 (m, 2H), 6.79 (s, 1H), 4.01 (q, J = 7.4 Hz, 1H), 2.29 (s, 3H), 2.15 (q, J = 7.8 Hz, 2H), 1.95-1.73 (m, 2H), 1.40 (s, 9H) |

TABLE 11-continued

| Characterization data for intermediates prepared according to above. | | | | |
|---|---|---|---|---|
| Intermediate | Structure | Chemical Name | MS: $[(M + 1)]^+$ | $^1$H-NMR |
| A47 | 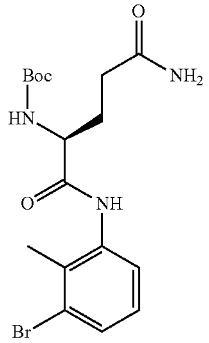 [SMILES: Cc1c(Br)cccc1NC(=O)[C@H](CCC(N)=O)NC(=O)OC(C)(C)C] | tert-butyl N-[(1S)-1-[(3-bromo-2-methylphenyl) carbamoyl]-3-carbamoylpropyl] carbamate | 414.10, 416.10 | (300 MHz, DMSO-$d_6$) δ 9.59 (s, 1H), 7.47 (dd, J = 8.0, 1.3 Hz, 1H), 7.39-7.27 (m, 2H), 7.21-7.01 (m, 2H), 6.81 (s, 1H), 4.06 (t, J = 7.2 Hz, 1H), 2.26 (s, 3H), 2.25-2.09 (m, 2H), 2.08-1.71 (m, 2H), 1.41 (s, 9H) |
| A48 | 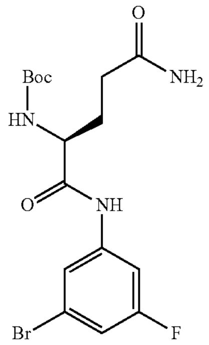 [SMILES: CC(C)(C)OC(=O)N[C@@H](CCC(N)=O)C(=O)Nc1cc(F)cc(Br)c1] | tert-butyl N-[(1S)-1-[(3-bromo-5-fluorophenyl) carbamoyl]-3-carbamoylpropyl] carbamate | 418.10, 420.10 | (300 MHz, DMSO-$d_6$) δ 10.33 (s, 1H), 7.71 (d, J = 2.0 Hz, 1H), 7.53 (d, J = 11.2 Hz, 1H), 7.39-7.06 (m, 3H), 6.80 (s, 1H), 4.01 (s, 1H), 2.17 (q, J = 7.6 Hz, 2H), 1.90-1.74 (m, 2H), 1.40 (s, 9H) |

Tert-butyl (S)-(5-amino-1-((3-bromo-2-fluorophenyl)amino)-5-oxopentan-2-yl)carbamate (Intermediate A49)

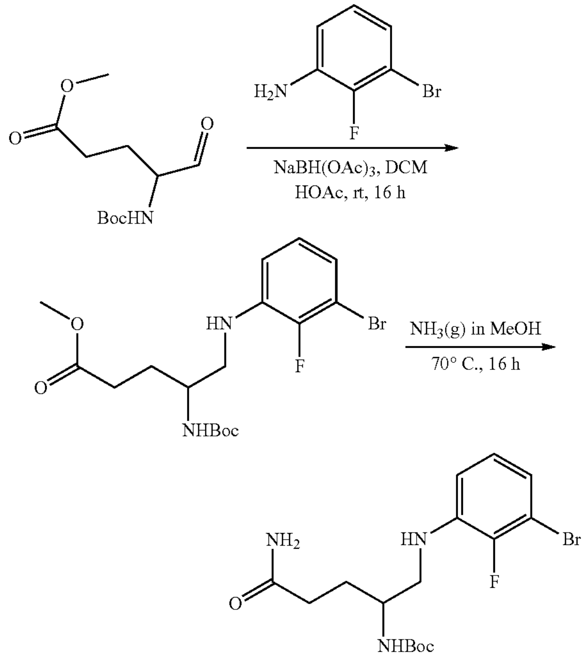

A49

Step 1: methyl (4S)-5-[(3-bromo-2-fluorophenyl)amino]-4-[(tert-butoxycarbonyl)amino]pentanoate. To a stirred solution of methyl (4S)-4-[(tert-butoxycarbonyl)amino]-5-oxopentanoate (3.01 g, 12.25 mmol) and 3-bromo-2-fluoroaniline (1.94 g, 10.2 mmol) in $CH_2Cl_2$ (40 mL) were added $NaBH(OAc)_3$ (4.33 g, 20.4 mmol) and HOAc (0.67 g, 11.2 mmol) in portions at room temperature under nitrogen atmosphere. The resulting mixture was stirred for 16 h at room temperature under nitrogen atmosphere followed by concentration under reduced pressure. The residue was purified by reverse phase flash chromatography with the following conditions: Spherical C18 Column, 20~40 um, 330 g; Mobile Phase A: Water (plus 10 mmol/L$NH_4HCO_3$), Mobile Phase B: ACN; Gradient: 30% to 50% B in 10 min; Detector: UV 254/220 nm. Desired fractions were collected at 43% B, concentrated under reduced pressure and lyophilized to afford title compound (2.1 g, 49%) as a white solid: $^1$H NMR (400 MHz, DMSO-$d_6$) δ 6.91 (t, J=8.0 Hz, 1H), 6.83-6.75 (m, 2H), 6.75 (dd, J=7.8, 1.6 Hz, 1H), 5.75 (s, 1H), 3.62 (s, 1H), 3.56 (s, 3H), 3.08 (t, J=6.2 Hz, 2H), 2.42-2.23 (m, 2H), 1.61-1.57 (m, 1H), 1.39-1.35 (m, 8H), 1.29-1.25 (m, 2H); LC/MS (ESI, m/z): $[(M+1)]^+$=419.15, 421.15.

The intermediates in Table 12 were prepared according to step 1 of the procedure to prepare Intermediate A49.

TABLE 12

| Characterization data for intermediates prepared according to above. | | | | |
|---|---|---|---|---|
| Intermediate | Structure | Chemical Name | MS: $[(M+1)]^+$ | $^1$H-NMR |
| A49-1-1 | 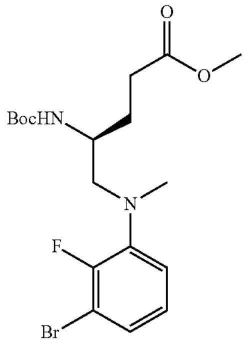 [SMILES: COC(=O)CC[C@@H](CN(C)c1cccc(Br)c1F)NC(=O)OC(C)(C)C] | methyl (4S)-5-[(3-bromo-2-fluorophenyl)(methyl) amino]-4-[(tert-butoxycarbonyl) amino]pentanoate | 433.20, 435.20 | (400 MHz, DMSO-$d_6$) δ 7.09-7.06 (m, 1H), 7.01-6.86 (m, 2H), 6.60 (d, J = 9.2 Hz, 1H), 3.69-3.67 (m, 1H), 3.57 (s, 3H), 3.19-3.08 (m, 2H), 2.89 (s, 3H), 2.29 (dd, J = 8.6, 6.5 Hz, 2H), 1.74 (dtd, J= 16.0, 7.9, 3.8 Hz, 1H), 1.48 (ddt, J = 13.9, 9.6, 7.1 Hz, 1H), 1.33 (s, 9H). |

Step 2: Tert-butyl (S)-(5-amino-1-((3-bromo-2-fluorophenyl)amino)-5-oxopentan-2-yl)carbamate. To a mixture of methyl (4S)-5-[(3-bromo-2-fluorophenyl)amino]-4-[(tert-butoxycarbonyl)amino]pentanoate (1.02 g, 2.43 mmol) and $NH_3$ (g) in MeOH (5.00 mL, 7M) in a sealed tube was stirred for 16 h at 70° C. After cooling down to ambient temperature, the resulting mixture was concentrated under reduced pressure to afford Tert-butyl (S)-(5-amino-1-((3-bromo-2-fluorophenyl)amino)-5-oxopentan-2-yl)carbamate (691 mg, 70%) as a yellow solid: $^1$H NMR (400 MHz, DMSO-$d_6$) δ 7.24 (s, 1H), 6.91 (t, J=8.0 Hz, 1H), 6.85-6.72 (m, 3H), 6.73-6.69 (m, 2H), 3.58 (s, 1H), 3.08 (s, 2H), 2.19-1.98 (m, 2H), 1.81-1.71 (m, 1H), 1.57-1.53 (m, 1H), 1.38 (s, 9H); LC/MS (ESI, m/z): $[(M+1)]^+$=404.20, 406.20.

The intermediates in Table 13 were prepared according to step 2 of the procedure to prepare Intermediate A49.

TABLE 13

| Characterization data for intermediates prepared according to above. | | | | |
|---|---|---|---|---|
| Intermediate | Structure | Chemical Name | MS: $[(M+1)]^+$ | $^1$H-NMR |
| A50 | 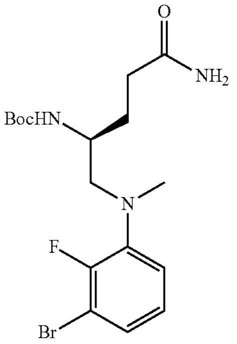 [SMILES: CN(C[C@H](CCC(N)=O)NC(=O)OC(C)(C)C)c1cccc(Br)c1F] | tert-butyl (S)-(5-amino-1-((3-bromo-2-fluorophenyl) (methyl)amino)-5-oxopentan-2-yl)carbamate | 418.20, 420.20 | (400 MHz, DMSO-$d_6$) δ 7.22 (s, 1H), 7.06 (ddd, J = 7.8, 5.8, 1.7 Hz, 1H), 7.01-6.86 (m, 2H), 6.69 (s, 1H), 6.57 (d, J = 9.2 Hz, 1H), 3.67-3.64 (m, 1H), 3.22 (m, 3H), 2.86 (s, 3H), 2.09-1.96 (m, 2H), 1.70-1.66 (m, 1H), 1.33 (s, 9H) |

Tert-butyl N-[(3S,4R)-1-Carbamoyl-4-([4-[3-(2-[3-[1-(2,6-dioxopiperidin-3-yl)-3-methyl-2-oxo-1,3-benzodiazol-5-yl]propoxy]ethoxy)propyl]phenyl] methoxy)pentan-3-yl]carbamate (Intermediate B)

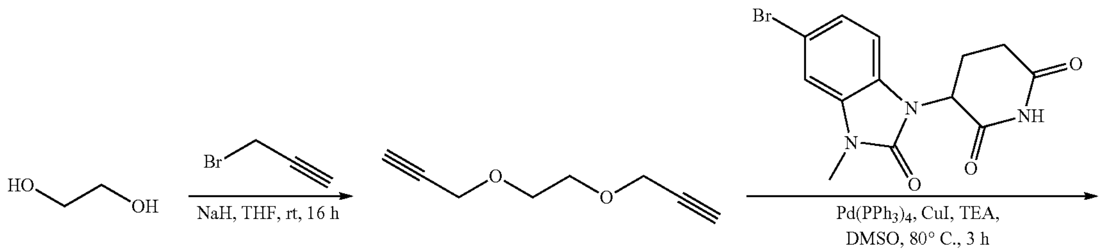

-continued

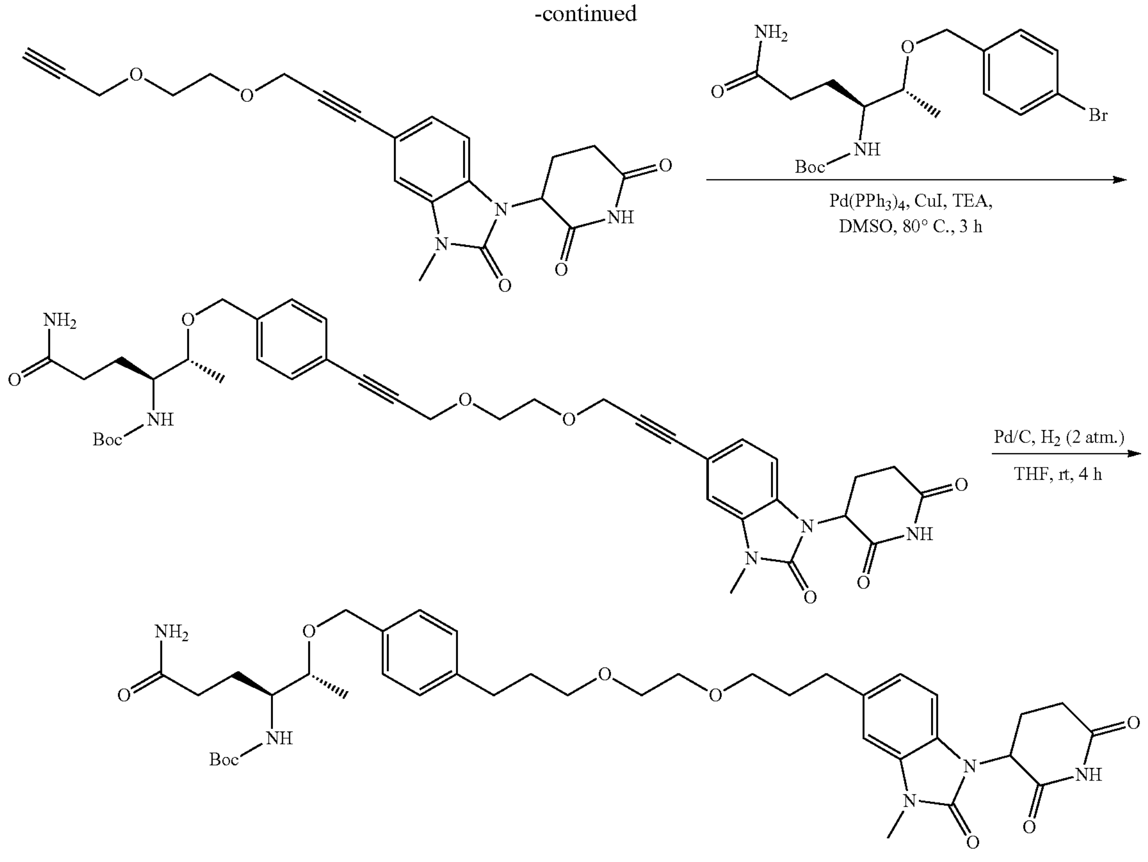

Intermediate B

Step 1. 3-[2-(Prop-2-yn-1-yloxy)ethoxy]prop-1-yn. To a solution of ethylene glycol (10.0 g, 161 mmol) in THF (250 mL) was added NaH (16.1 g, 402 mmol, 60% dispersed in mineral oil) in portions at 0° C. under nitrogen atmosphere. The resulting mixture was stirred for 30 min at 0° C. under nitrogen atmosphere. To the above mixture was added a solution of propargyl bromide (47.9 g, 402 mmol) in THF (50.0 mL) at 0° C. over 10 min. The resulting mixture was stirred for 16 hours at room temperature under nitrogen atmosphere. The resulting mixture was quenched with saturated aqueous ammonium chloride (200 mL) at 0° C. The resulting mixture was extracted with ethyl acetate (2×300 mL). The combined organic layer was washed with brine (300 mL) and dried over anhydrous $Na_2SO_4$. After filtration, the filtrate was concentrated under reduced pressure. The residue was purified by silica gel column chromatography, eluted with 1% ethyl acetate in petroleum ether to afford the title compound as a brown oil (8.20 g, 37%): $^1$H NMR (400 MHz, $CDCl_3$) δ 4.22 (dd, J=2.4, 0.9 Hz, 4H), 3.73 (d, J=1.0 Hz, 4H), 2.44 (td, J=2.4, 0.8 Hz, 2H); MS (ESI, m/z): $[(M+18)]^+$=156.20.

The intermediates in Table 14 were prepared according to Step 1 of the procedure to prepare Intermediate B.

TABLE 14

Characterization data for intermediates prepared according to above.

| Intermediate | Structure | Chemical Name | $^1$H-NMR |
|---|---|---|---|
| B-1-1 | 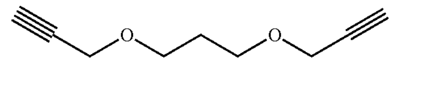 | 3-[3-(Prop-2-yn-1-yloxy)propoxy]prop-1-yne | $^1$H NMR (400 MHz, $CDCl_3$) δ 4.10-4.08 (m, 4H), 3.55 (t, J = 6.3 Hz, 4H), 2.41 (d, J = 4.8 Hz, 2H), 1.83 (p, J = 6.3 Hz, 2H). |
| B-1-2 | 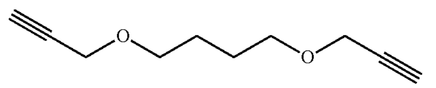 | 1,4-bis(prop-2-yn-1-yloxy)butane | $^1$H NMR (400 MHz, $CDCl_3$) δ 4.17-4.15 (m, 4H), 3.60-3.53 (m, 4H), 2.43 (t, J = 2.4 Hz, 2H), 1.74-1.68 (m, 4H). |
| B-1-3 | 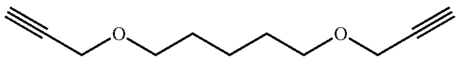 | 1,5-bis(prop-2-yn-1-yloxy)pentane | $^1$H NMR (400 MHz, $CDCl_3$) δ 4.17-4.15 (m, 4H), 3.55 (t, J = 6.5 Hz, 4H), 2.44 (t, J = 2.4 Hz, 2H), 1.71-1.60 (m, 4H), 1.53-1.40 (m, 2H). |

TABLE 14-continued

| Characterization data for intermediates prepared according to above. | | | |
|---|---|---|---|
| Intermediate | Structure | Chemical Name | $^1$H-NMR |
| B-1-4 | 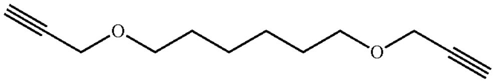 | 1,6-bis(prop-2-yn-1-yloxy)hexane | $^1$H NMR (400 MHz, $CDCl_3$) δ 4.17-4.15 (m, 4H), 3.54 (td, J = 6.6, 2.7 Hz, 4H), 2.44 (q, J = 2.3 Hz, 2H), 1.69-1.59 (m, 4H), 1.41 (h, J = 3.2 Hz, 4H). |
| B-1-5 | 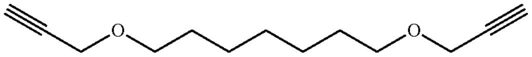 | 1,7-bis(prop-2-yn-1-yloxy)heptane | $^1$H NMR (400 MHz, $CDCl_3$) δ 4.17-4.15 (m, 4H), 3.53 (t, J = 6.6 Hz, 4H), 2.44 (d, J = 2.5 Hz, 2H), 1.62 (d, J = 13.8 Hz, 4H), 1.44-1.34 (m, 6H). |
| B-1-6 | 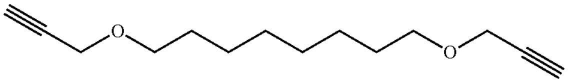 [SMILES: C#CCOCCCCCCCCOCC#C] | 1,8-bis(prop-2-yn-1-yloxy)octane | $^1$H NMR (400 MHz, $CDCl_3$) δ 4.17-4.15 (m, 4H), 3.52 (t, J = 6.6 Hz, 4H), 2.43 (t, J = 2.4 Hz, 2H), 1.67-1.53 (m, 4H), 1.43-1.28 (m, 8H). |
| B-1-7[a] | 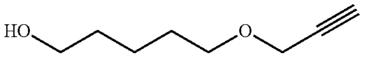 | 5-(prop-2-yn-1-yloxy)pentan-l-ol | $^1$H NMR (400 MHz, $CDCl_3$) δ 4.16 (d, J = 2.3 Hz, 2H), 3.68 (td, J = 6.5, 2.0 Hz, 2H), 3.55 (td, J = 6.5, 1.5 Hz, 2H), 2.44 (q, J = 2.6 Hz, 1H), 1.70-1.59 (m, 4H), 1.51-1.43 (m, 3H). |

[a]Propargyl bromide (1 eq.) and NaH (1.1 eq.) used.

Step 2. 3-(3-Methyl-2-oxo-5-[3-[2-(prop-2-yn-1-yloxy) ethoxy]prop-1-yn-1-v]-1,3-benzodiazol-1-yl)piperidine-2,6-dione. To a solution of 3-(5-bromo-3-methyl-2-oxo-1,3-benzodiazol-1-yl)piperidine-2,6-dione (1.00 g, 2.96 mmol), $Pd(PPh_3)_4$(342 mg, 0.30 mmol) and CuI (56.3 mg, 0.30 mmol) in DMSO (20 mL) were added TEA (10 mL) and 3-[2-(prop-2-yn-1-yloxy)ethoxy]prop-1-yne (3.27 g, 23.7 mmol). The mixture was purged with nitrogen for three times and stirred for 3 hours at 80° C. under nitrogen atmosphere. The resulting mixture was cooled down to room temperature and concentrated under reduced pressure. The residue was acidified to pH 5 with acetic acid and purified by reversed phase flash chromatography with the following conditions: Column: WelFlash™ C18-I, 20~40 um, 330 g; Eluent A: water (plus 10 mmol/L AcOH); Eluent B: ACN; Gradient: 20% - 40% B in 20 min; Flow rate: 80 mL/min; Detector: UV 220/254 nm; desired fractions were collected at 37% B and concentrated under reduced pressure. The crude product was re-purified by silica gel column chromatography, eluted with 50% ethyl acetate in petroleum ether to afford the title compound as a light brown solid (450 mg, 39%): $^1$H NMR (400 MHz, DMSO-$d_6$) δ 11.12 (s, 1H), 7.38-7.32 (m, 1H), 7.21-7.10 (m, 2H), 5.39 (dd, J=12.6, 5.4 Hz, 1H), 4.39 (d, J=2.4 Hz, 2H), 4.16 (t, J=2.4 Hz, 2H), 3.68-3.61 (m, 4H), 3.44 (dd, J=3.4, 2.3 Hz, 1H), 3.34 (d, J=2.3 Hz, 3H), 2.88 (t, J=15.6 Hz, 1H), 2.76-2.57 (m, 2H), 2.08-1.98 (m, 1H); MS (ESI, m/z): $[(M+1)]^+$=396.15.

Step 3. tert-Butyl ((2R,3S)-6-amino-2-((4-(3-(2-((3-(1-(2,6-dioxopiperidin-3-yl)-3-methyl-2-oxo-2,3-dihydro-1H-benzo[d]imidazol-5-yl)prop-2-yn-1-yl)oxy)ethoxy)prop-1-yn-1-yl)benzyl)oxy)-6-oxohexan-3-yl)carbamate. The title compound was prepare according to Step 2 above: $^1$H NMR (400 MHz, DMSO-$d_6$) δ 11.12 (s, 1H), 7.69 (d, J=13.2 Hz, 1H), 7.54-7.27 (m, 4H), 7.20 (d, J=12.8 Hz, 1H), 7.14 (t, J=7.9 Hz, 1H), 6.73-6.59 (m, 1H), 5.39 (dd, J=12.7, 5.4 Hz, 1H), 4.48 (s, 1H), 4.41 (s, 3H), 4.22 (t, J=6.6 Hz, 1H), 3.70 (s, 2H), 3.41 (d, J=6.0 Hz, 1H), 3.35 (s, 2H), 3.33 (s, 3H), 2.94-2.83 (m, 1H), 2.76-2.58 (m, 2H), 2.54 (s, 1H), 2.13-1.97 (m, 2H), 1.76 (s, 1H), 1.67-1.60 (m, 1H), 1.37 (s, 9H), 1.26 (d, J=19.3 Hz, 1H), 1.06 (d, J=6.1 Hz, 2H), 0.89 (dt, J=13.4, 6.8 Hz, 2H); MS (ESI, m/z): $[(M+1)]^+$=728.3.

The intermediates in Table 15 were prepared according to Step 2 and 3 of the procedure to prepare Intermediate B.

TABLE 15

Characterization data for intermediates prepared according to above.

| Intermediate | Structure | Chemical Name | MS: $[(M + 1)]^+$ | $^1$H-NMR |
|---|---|---|---|---|
| B-2-1 | 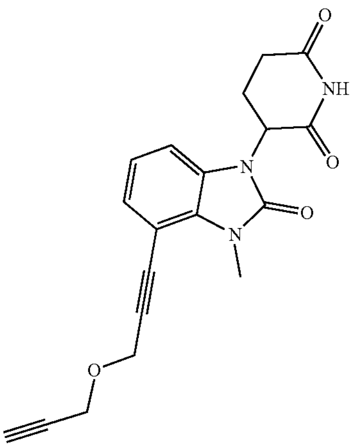 [SMILES: C#CCOCC#Cc1cccc2c1n(C)c(=O)n2C1CCC(=O)NC1=O] | 3-[3-methyl-2-oxo-4-[3-(prop-2-yn-1-yloxy)prop-1-yn-1-yl]-1,3-benzodiazol-1-yl]piperidine-2,6-dione | 352.1 | (400 MHz, $CD_3OD$) δ 7.19 (d, J = 1.2 Hz, 1H) 7.13 (d, J = 1.3 Hz, 1H), 7.06 (s, 1H), 5.37 (t, J = 4.1 Hz, 1H), 4.56 (s, 2H), 3.76 (d, J = 1.7 Hz, 3H), 2.96-2.93 (m, 2H), 2.82-2.76 (m, 2H), 2.18-2.13 (m, 1H) |
| B-2-2 | 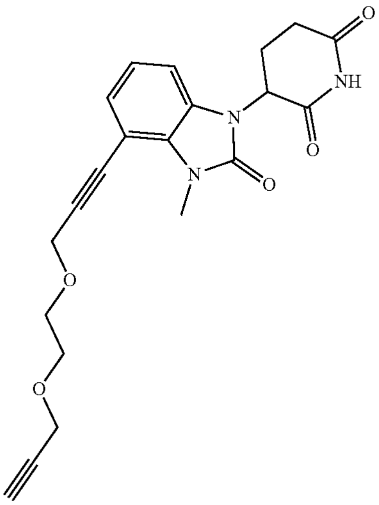 [SMILES: C#CCOCCOCC#Cc1cccc2c1n(C)c(=O)n2C1CCC(=O)NC1=O] | 3-[3-methyl-2-oxo-4-[3-[2-(prop-2-yn-1-yloxy)ethyoxy]prop-1-yn-1-yl]-1,3-benzodiazol-1-yl]piperidine-2,6-dione | 396.2 | (400 MHz, $CD_3OD$) δ 7.24-7.08 (m, 3H), 5.38 (s, 1H), 4.51 (s, 2H), 4.26-4.20 (m, 2H), 3.81-3.78 (m, 3H), 3.53 (s, 2H), 3.20 (s, 2H), 2.86 (s, 4H), 2.21 (s, 1H). |
| B-2-3 | 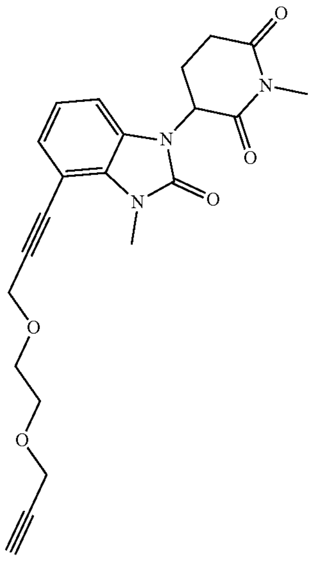 [SMILES: C#CCOCCOCC#Cc1cccc2c1n(C)c(=O)n2C1CCC(=O)N(C)C1=O] | 1-methyl-3-(3-methyl-2-oxo-5-[3-[2-(prop-2-yn-1-yloxy)ethyoxy]prop-1-yn-1-yl]-1,3-benzodiazol-1-yl]piperidine-2,6-dione | 410.3 | (400 MHz, DMSO-$d_6$) δ 7.39 (d, J = 7.5 Hz, 1H), 7.12 (d, J = 7.7 Hz, 1H), 7.01 (q, J = 7.6 Hz, 1H), 5.51-5.39 (m, 1H), 4.48 (d, J = 7.2 Hz, 3H), 3.71 (s, 4H), 3.64 (d, J = 6.8 Hz, 3H), 3.03 (d, J = 6.3 Hz, 3H), 2.83-2.66 (m, 2H), 2.03 (s, 4H). |

TABLE 15-continued

| Characterization data for intermediates prepared according to above. | | | | |
|---|---|---|---|---|
| Inter-mediate | Structure | Chemical Name | MS: $[(M + 1)]^+$ | $^1$H-NMR |
| B-2-4 | 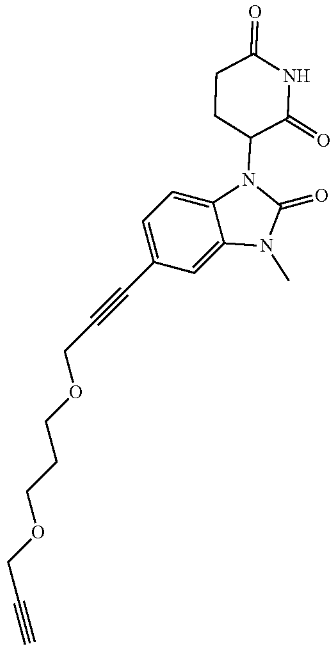 [SMILES: C#CCOCCCOCC#Cc1ccc2c(c1)n(C)c(=O)n2C1CCC(=O)NC1=O] | 3-[3-methyl-2-oxo-5-[3-[2-(prop-2-yn-1-yloxy)propoxy]prop-1-yn-1-yl]-2,3-dihydro-1H-1,3-benzodiazol-1-yl]piperidine-2,6-dione | 408.2 | (400 MHz, $CDCl_3$) δ 8.36 (s, 1H), 7.22 (dd, J = 8.2, 1.5 Hz, 1H), 7.14 (d, J = 1.5 Hz, 1H), 6.77 (d, J = 8.2 Hz, 1H), 5.22 (dd, J = 12.7, 5.3 Hz, 1H), 3.70-3.66 (m, 4H), 3.44 (s, 3H), 3.04-2.61 (m, 4H), 2.44 (t, J = 2.4 Hz, 1H), 1.51-1.27 (m, 6H). |
| B-2-5 | 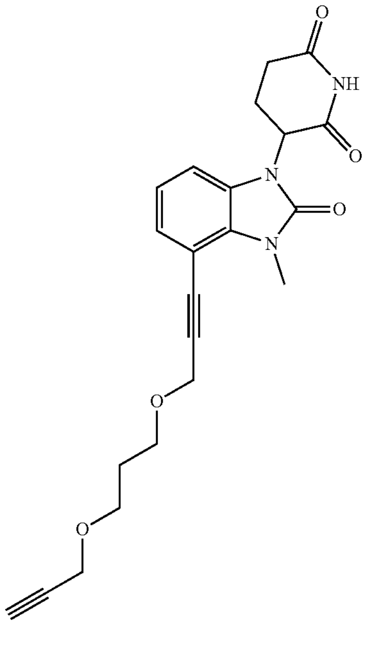 [SMILES: C#CCOCCCOCC#Cc1cccc2c1n(C)c(=O)n2C1CCC(=O)NC1=O] | 3-[3-methyl-2-oxo-4-[3-[2-(prop-2-yn-1-yloxy)propoxy]prop-1-yn-1-yl]-1,3-benzodiazol-1-yl]piperidine-2,6-dione | 410.2 | (400 MHz, DMSO-$d_6$) δ 11.11 (d, J = 8.1 Hz, 1H), 7.21-7.08 (m, 2H), 7.04 (t, J = 7.9 Hz, 1H), 5.41 (dd, J = 12.5, 5.4 Hz, 1H), 4.43 (d, J = 10.2 Hz, 2H), 4.17-4.05 (m, 2H), 3.73-3.55 (m, 5H), 3.55-3.47 (m, 2H), 3.40 (d, J = 4.8 Hz, 1H), 2.98-2.82 (m, 1H), 2.77-2.56 (m, 2H), 2.04 (d, J = 12.4 Hz, 1H), 1.87-1.72 (m, 2H). |

TABLE 15-continued

| Characterization data for intermediates prepared according to above. | | | | |
|---|---|---|---|---|
| Inter-mediate | Structure | Chemical Name | MS: $[(M + 1)]^+$ | $^1$H-NMR |
| B-2-6 | 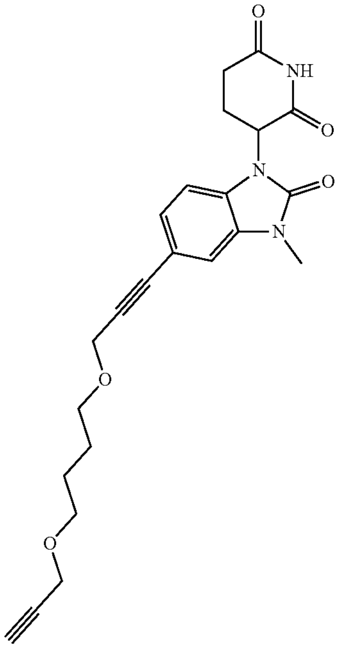 [SMILES: C#CCOCCCCOCC#Cc1ccc2c(c1)n(C)c(=O)n2C1CCC(=O)NC1=O] | 3-[3-methyl-2-oxo-5-[3-[2-(prop-2-yn-1-yloxy)butoxy]prop-1-yn-1-yl]-1,3-benzodiazol-1-yl]piperidine-2,6-dione | 422.2 | (400 MHz, DMSO-$d_6$) δ 11.12 (s, 1H), 7.34 (d, J = 1.3 Hz, 1H), 7.20-7.10 (m, 2H), 5.40 (dd, J = 12.7, 5.3 Hz, 1H), 4.36 (s, 2H), 4.11 (d, J = 2.4 Hz, 2H), 3.56-3.50 (m, 2H), 3.46 (q, J = 4.6, 3.2 Hz, 2H), 3.40 (d, J = 4.9 Hz, 1H), 2.97-2.83 (m, 1H), 2.78-2.58 (m, 2H), 2.03 (ddd, J = 16.2, 7.4, 4.6 Hz, 1H), 1.60-1.58 (m, 5H), 1.24 (s, 1H), 1.21-1.06 (m, 1H). |
| B-2-7 | 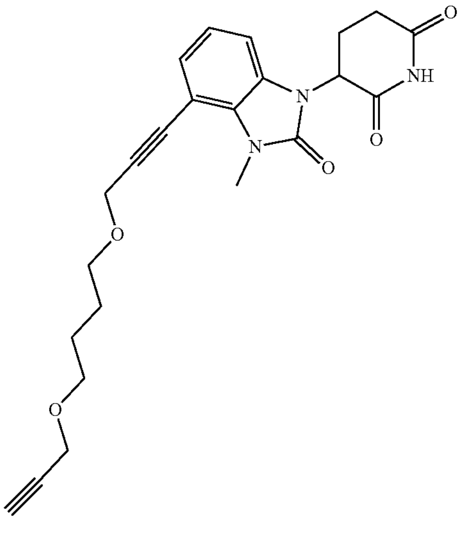 [SMILES: C#CCOCCCCOCC#Cc1cccc2c1n(C)c(=O)n2C1CCC(=O)NC1=O] | 3-[3-methyl-2-oxo-4-[3-[4-(prop-2-yn-1-yloxy)butoxy]prop-1-yn-1-yl]-1,3-benzo diazol-1-yl]piperidine-2,6-dione | 424.2 | (400 MHz, DMSO-$d_6$) δ 11.12 (s, 1H), 7.16 (dd, J = 19.4, 7.8 Hz, 2H), 7.04 (t, J = 7.8 Hz, 1H), 5.41 (dd, J = 12.7, 5.4 Hz, 1H), 4.43 (s, 2H), 4.10 (d, J = 2.4 Hz, 2H), 3.65 (s, 3H), 3.55 (d, J = 11.7 Hz, 2H), 3.46 (d, J = 11.6 Hz, 2H), 3.38 (t, J = 2.4 Hz, 1H), 2.94-2.86 (m, 1H), 2.73-2.58 (m, 2H), 2.03 (dd, J = 11.6, 5.9 Hz, 1H), 1.60 (m, 4H). |

TABLE 15-continued

| Characterization data for intermediates prepared according to above. | | | | |
|---|---|---|---|---|
| Inter-mediate | Structure | Chemical Name | MS: $[(M + 1)]^+$ | $^1$H-NMR |
| B-2-8 | 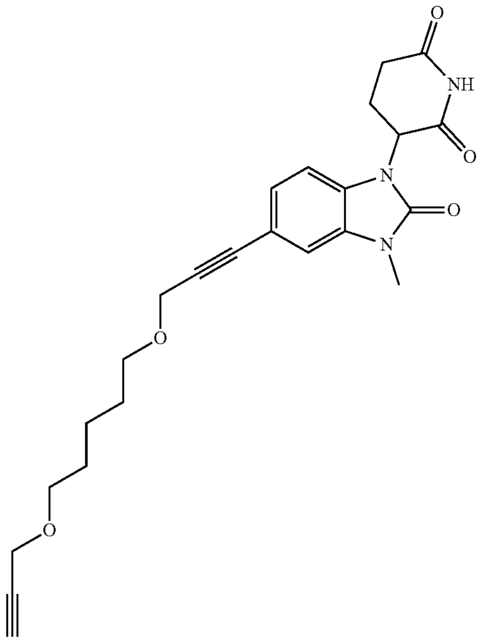 [SMILES: C#CCOCCCCCOCC#Cc1ccc2c(c1)n(C)c(=O)n2C1CCC(=O)NC1=O] | 3-[3-methyl-2-oxo-5-(3-[[5-(prop-2-yn-1-yloxy)pentyl]oxy]prop-1-yn-1-yl)-1,3-benzodiazol-1-yl]piperidine-2,6-dione | 436.3 | (400 MHz, $CDCl_3$) δ 8.12 (s, 1H), 7.22 (dd, J = 8.1, 1.5 Hz, 1H), 7.14 (d, J = 1.6 Hz, 1H), 6.77 (d, J = 8.2 Hz, 1H), 5.21 (dd, J = 12.6, 5.3 Hz, 1H), 4.38 (s, 2H), 4.15 (d, J = 2.4 Hz, 2H), 3.61 (t, J = 6.6 Hz, 2H), 3.55 (t, J = 6.5 Hz, 2H), 3.45 (s, 3H), 3.03-2.93 (m, 1H), 2.79 (dqd, J = 39.2, 13.3, 4.9 Hz, 2H), 2.43 (t, J = 2.4 Hz, 1H), 2.32-2.21 (m, 1H), 1.75-1.61 (m, 4H), 1.56-1.43 (m, 2H). |
| B-2-9 | 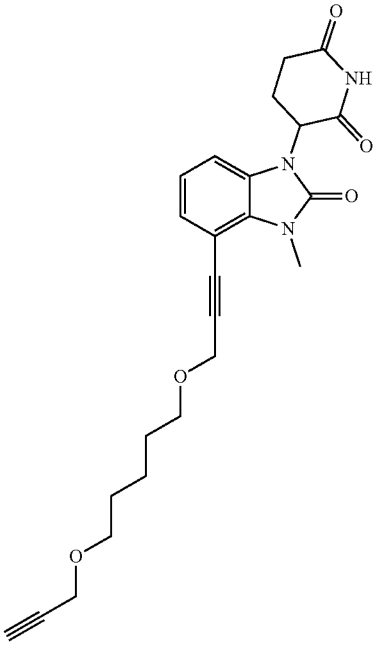 [SMILES: C#CCOCCCCCOCC#Cc1cccc2c1n(C)c(=O)n2C1CCC(=O)NC1=O] | 3-[3-methyl-2-oxo-4-(3-[[5-(prop-2-yn-1-yloxy)pentyl]oxy]prop-1-yn-1-yl)-1,3-benzodiazol-1-yl]piperidine-2,6-dione | 438.3 | (400 MHz, DMSO-$d_6$) δ 11.12 (s, 1H), 7.18 (dd, J = 7.9, 1.2 Hz, 1H), 7.13 (dd, J = 7.9, 1.1 Hz, 1H), 7.04 (t, J = 7.8 Hz, 1H), 5.40 (dd, J = 12.6, 5.3 Hz, 1H), 4.43 (s, 2H), 4.10 (d, J = 2.4 Hz, 2H), 3.54 (t, J = 6.4 Hz, 2H), 3.43 (t, J = 6.4 Hz, 2H), 3.38 (t, J = 2.4 Hz, 1H), 3.31 (s, 2H), 2.95-2.83 (m, 1H), 2.75 (dd, J = 12.8, 4.3 Hz, 1H), 2.73-2.64 (m, 1H), 2.09-1.99 (m, 1H), 2.02 (s, 1H), 1.71-1.48 (m, 4H), 1.43-1.31 (m, 2H). |

TABLE 15-continued

| Characterization data for intermediates prepared according to above. | | | | |
|---|---|---|---|---|
| Intermediate | Structure | Chemical Name | MS: $[(M + 1)]^+$ | $^1H$-NMR |
| B-2-10 | 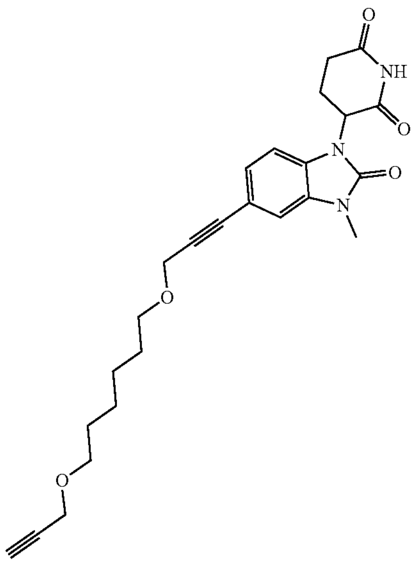 [SMILES: C#CCOCCCCCCOCC#Cc1ccc2c(c1)n(C)c(=O)n2C1CCC(=O)NC1=O] | 3-[3-methyl-2-oxo-5-(3-[[6-(prop-2-yn-1-yloxy)hexyl]oxy]prop-1-yn-1-yl)-2,3-dihydro-1H-1,3-benzodiazol-1-yl]piperidine-2,6-dione | 452.2 | (400 MHz, DMSO-$d_6$) δ 11.12 (d, J = 4.2 Hz, 1H), 7.33 (d, J = 5.9 Hz, 1H), 7.19-7.11 (m, 2H), 5.39 (dt, J = 10.3, 5.0 Hz, 1H), 4.35 (d, J = 5.6 Hz, 2H), 4.08 (dd, J = 5.6, 2.4 Hz, 2H), 3.50 (q, J = 6.2 Hz, 2H), 3.45-3.37 (m, 3H), 2.89 (dd, J = 17.0, 12.9 Hz, 1H), 2.78-2.58 (m, 2H), 2.02 (dt, J = 15.8, 6.0 Hz, 2H), 1.53-1.50 (m, 4H), 1.42-1.21 (m, 5H), 1.20-1.14 (m, 1H). |
| B-2-11 | 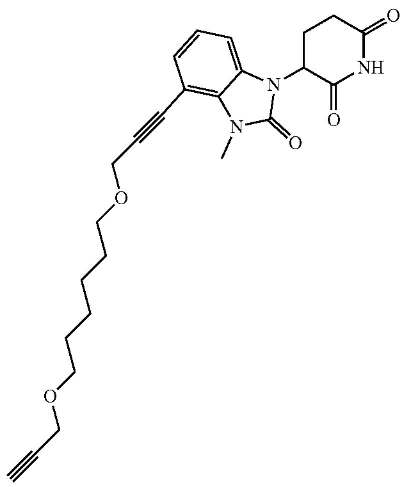 [SMILES: C#CCOCCCCCCOCC#Cc1cccc2c1n(C)c(=O)n2C1CCC(=O)NC1=O] | 3-[3-methyl-2-oxo-4-(3-[[6-(prop-2-yn-1-yloxy)hexyl]oxy]prop-1-yn-1-yl)-1,3-benzodiazol-1-yl]piperidine-2,6-dione | 452.2 | (400 MHz, DMSO-$d_6$) δ 11.13 (s, 1H), 7.18 (d, J = 7.8 Hz, 1H), 7.13 (d, J = 7.8 Hz, 1H), 7.04 (t, J = 7.9 Hz, 1H), 5.41 (dd, J = 12.6, 5.4 Hz, 1H), 4.42 (s, 2H), 4.09 (d, J = 2.4 Hz, 2H), 3.65 (s, 3H), 3.53 (t, J = 6.5 Hz, 2H), 3.45-3.34 (m, 3H), 2.90 (ddd, J = 17.1, 12.8, 5.1 Hz, 1H), 2.78-2.59 (m, 2H), 2.10-1.95 (m, 1H), 1.53 (dp, J = 19.6, 7.1, 6.4 Hz, 4H), 1.35-1.32 (m, 4H). |

TABLE 15-continued

Characterization data for intermediates prepared according to above.

| Inter-mediate | Structure | Chemical Name | MS: $[(M + 1)]^+$ | $^1$H-NMR |
|---|---|---|---|---|
| B-2-12 | 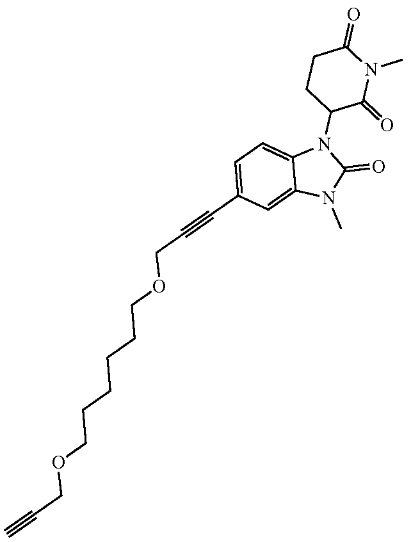 [SMILES: C#CCOCCCCCCOCC#Cc1ccc2c(c1)n(C)c(=O)n2C1CCC(=O)N(C)C1=O] | 1-methyl-3-[3-methyl-2-oxo-5-(3-[[6-(prop-2-yn-1-yloxy)hexyl]oxy]prop-1-yn-1-yl)-1,3-benzodiazol-1-yl]piperidine-2,6-dione | N/A | (400 MHz, DMSO-$d_6$) δ 7.34 (s, 1H), 7.15 (d, J = 1.0 Hz, 2H), 5.76 (s, 1H), 5.46 (dd, J = 13.0, 5.3 Hz, 1H), 4.36 (s, 2H), 4.11-3.99 (m, 2H), 3.51 (t, J = 6.5 Hz, 2H), 3.46-3.36 (m, 3H), 3.32 (s, 1H), 3.04 (s, 3H), 3.03-2.91 (m, 1H), 2.83-2.75 (m, 1H), 2.70 (td, J = 13.1, 4.5 Hz, 1H), 2.09-1.97 (m, 1H), 1.55-1.52 (m, 4H), 1.43-1.30 (m, 5H). |
| B-2-13 | 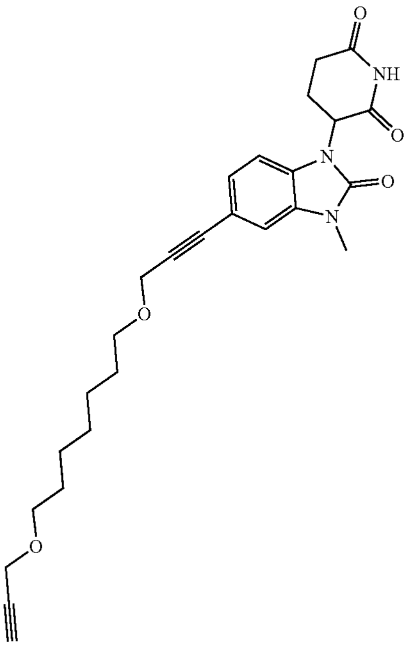 [SMILES: C#CCOCCCCCCCOCC#Cc1ccc2c(c1)n(C)c(=O)n2C1CCC(=O)NC1=O] | 3-[3-methyl-2-oxo-5-(3-[[7-(prop-2-yn-1-yloxy)heptyl]oxy]prop-1-yn-1-yl)-1,3-benzodiazol-1-yl]piperidine-2,6-dione | 488.2 | (400 MHz, DMSO-$d_6$) δ 11.12 (s, 1H), 7.33 (d, J = 1.4 Hz, 1H), 7.19-7.10 (m, 2H), 5.39 (dd, J = 12.7, 5.3 Hz, 1H), 4.35 (s, 2H), 4.09 (d, J = 2.3 Hz, 2H), 3.51 (t, J = 6.5 Hz, 2H), 3.44-3.37 (m, 3H), 3.32 (s, 1H), 2.96-2.84 (m, 1H), 2.77-2.59 (m, 2H), 2.09-1.97 (m, 1H), 1.54-1.51 (m, 4H), 1.31 (s, 7H). |

TABLE 15-continued

| Characterization data for intermediates prepared according to above. | | | | |
|---|---|---|---|---|
| Inter-mediate | Structure | Chemical Name | MS: $[(M + 1)]^+$ | $^1$H-NMR |
| B-2-14 | 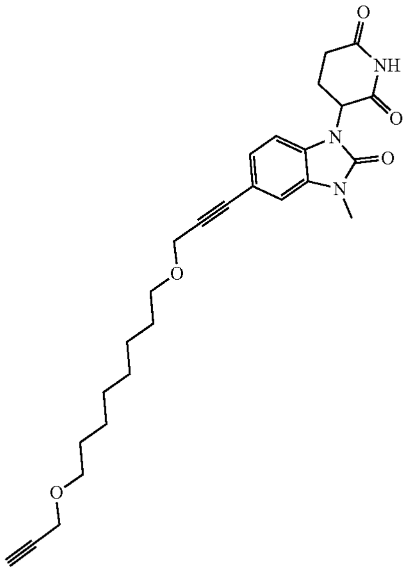 [SMILES: C#CCOCCCCCCCCOCC#Cc1ccc2c(c1)n(C)c(=O)n2C1CCC(=O)NC1=O] | 3-[3-methyl-2-oxo-5-(3-[[8-(prop-2-yn-1-yloxy) oxtyl]oxy]prop-1-yn-1-yl)-1,3-benzodiazol-1-yl]piperidine-2,6-dione | 502.3 | (400 MHz, $CDCl_3$) δ 8.16 (s, 1H), 7.22 (dd, J = 8.1, 1.5 Hz, 1H), 7.14 (d, J = 1.5 Hz, 1H), 6.77 (d, J = 8.2 Hz, 1H), 5.22 (dd, J = 12.7, 5.3 Hz, 1H), 4.38 (s, 2H), 4.15 (d, J = 2.4 Hz, 2H), 3.59 (t, J = 6.7 Hz, 2H), 3.52 (t, J = 6.6 Hz, 2H), 3.44 (s, 3H), 3.03-2.67 (m, 3H), 2.44 (t, J = 2.4 Hz, 1H),1.78-1.55 (m, 6H), 1.47-1.26 (m, 7H). |
| B-2-15 | 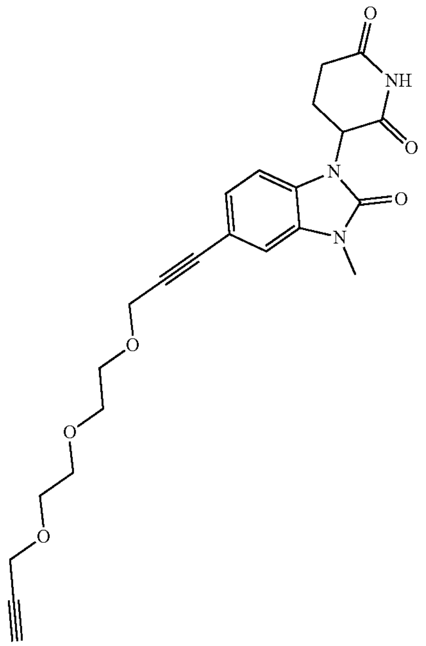 [SMILES: C#CCOCCOCCOCC#Cc1ccc2c(c1)n(C)c(=O)n2C1CCC(=O)NC1=O] | 3-[3-methyl-2-oxo-5-(3-[2-[2-(prop-2-yn-1-yloxy)ethoxy] ethoxy]prop-1-yn-1-yl)-2,3-dihydro-1H-1,3-benzodiazol-1-yl]piperidine-2,6-dione | 462.3 | (400 MHz, DMSO-$d_6$) δ 11.12 (d, J = 6.8 Hz, 1H), 7.34 (d, J = 8.9 Hz, 1H), 7.19-7.09 (m, 2H), 5.39 (dt, J = 12.7, 6.8 Hz, 1H), 4.43-4.36 (m, 2H), 4.17-4.11 (m, 2H), 3.66-3.60 (m, 2H), 3.59-3.49 (m, 6H), 3.45-3.40 (m, 1H), 3.35 (s, 1H), 3.32 (d, J = 0.9 Hz, 1H), 2.95-2.81 (m, 1H), 2.75-2.55 (m, 2H), 2.08-1.95 (m, 1H), 1.31-1.12 (m, 1H). |

TABLE 15-continued

Characterization data for intermediates prepared according to above.

| Inter-mediate | Structure | Chemical Name | MS: $[(M+1)]^+$ | $^1$H-NMR |
|---|---|---|---|---|
| B-2-16 | 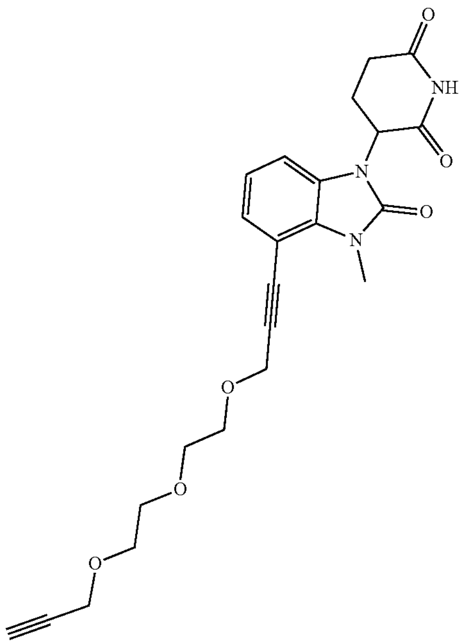 [SMILES: C#CCOCCOCCOCC#Cc1cccc2c1n(C)c(=O)n2C1CCC(=O)NC1=O] | 3-[3-methyl-2-oxo-4-(3-[2-[2-(prop-2-yn-1-yloxy)ethoxy]ethoxy]prop-1-yn-1-yl)-1,3-benzodiazol-1-yl]piperidine-2,6-dione | 440.2 | (400 MHz, $CDCl_3$) δ 8.20 (s, 1H), 7.19 (dd, J = 8.0, 1.0 Hz, 1H), 7.00 (d, J = 7.9 Hz, 1H), 6.78 (dd, J = 7.9 Hz, 1.1 Hz, 1H), 5.22 (dd, J = 12.5, 5.3 Hz, 1H), 4.49 (s, 2H), 4.23 (d, J = 2.4 Hz, 2H), 3.84-3.78 (m, 1H), 3.80 (s, 3H), 3.81-3.69 (m, 6H), 3.01-2.92 (m, 1H), 2.91-2.67 (m, 2H), 2.45 (t, J = 2.4 Hz, 1H), 2.30-2.19 (m, 1H), 1.02-0.87 (m, 1H). |
| B-2-17 | 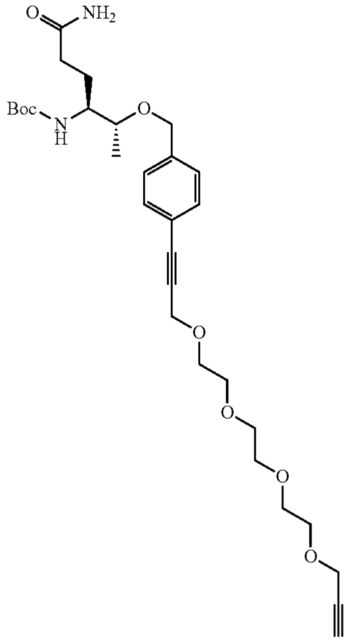 [SMILES: C#CCOCCOCCOCCOCC#Cc1ccc(CO[C@H](C)[C@H](CCC(N)=O)NC(=O)OC(C)(C)C)cc1] | tert-butyl N-[(3S,4R)-1-carbamoyl-4-[[4-(4,7,10,13-tetraxahexadeca-1,15-diyn-1-yl)phenyl]methoxy]pentan-3-yl]carbamate | 561.3 | (400 MHz, $CDCl_3$) δ 7.46-7.40 (m, 2H), 7.29 (s, 2H), 6.47 (s, 1H), 5.44 (s, 1H), 4.45 (s, 2H), 4.22 (d, J = 2.4 Hz, 3H), 3.82-3.77 (m, 2H), 3.75-3.70 (m, 10H), 3.62 (dd, J = 6.4, 3.6 Hz, 1H), 2.45 (t, J = 2.4 Hz, 1H), 2.33-2.26 (m, 2H), 2.02-1.96 (m, 1H), 1.73 (ddt, J = 18.9, 12.0, 6.4 Hz, 2H), 1.45 (s, 9H), 1.21 (d, J = 6.3 Hz, 3H). |
| B-2-18 | 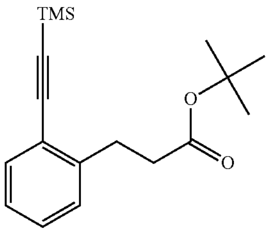 [SMILES: CC(C)(C)OC(=O)CCc1ccccc1C#C[Si](C)(C)C] | tert-butyl 3-[2-[2-(trimethylsilyl)ethynyl]phenyl]propanoate | N/A | (400 MHz, DMSO-$d_6$) δ 7.41 (dd, J = 7.4, 1.3 Hz, 1H), 7.35-7.28 (m, 2H), 7.23-7.21 (m, 1H), 2.99-2.92 (m, 2H), 2.55-2.53 (m, 2H), 1.38 (s, 9H), 0.24 (s, 9H). |

TABLE 15-continued

| Characterization data for intermediates prepared according to above. | | | | |
|---|---|---|---|---|
| Inter-mediate | Structure | Chemical Name | MS: $[(M + 1)]^+$ | $^1$H-NMR |
| B-3-1 | 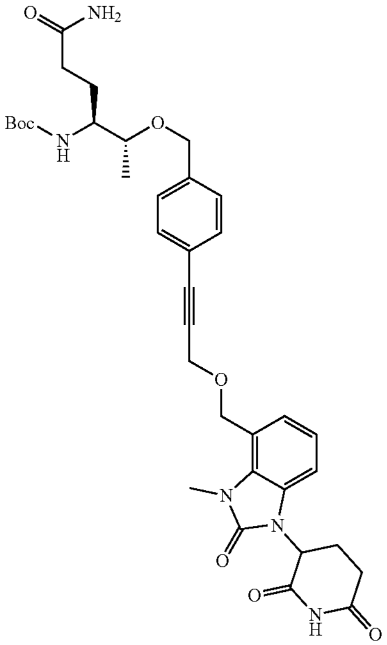 [SMILES: C[C@@H](OCc1ccc(C#CCOCc2cccc3c2n(C)c(=O)n3C2CCC(=O)NC2=O)cc1)[C@H](CCC(N)=O)NC(=O)OC(C)(C)C] | tert-butyl N-[(3S,4R)-1-carbamoyl-4-[[4-(3-[[1-(2,6-dioxopiperidin-3-yl)-3-methyl-2-oxo,1,3-benzodiazol-4-yl]methoxy]prop-1-yn-1-yl)phenyl]methoxy]pentan-3-yl]carbamate | 662.4 | (400 MHz, DMSO-$d_6$) δ 11.10 (s, 1H), 7.43 (d, J = 7.9, Hz, 2H), 7.35 (d, J = 8.0 Hz, 2H), 7.21 (s, 1H), 7.15 (d, J = 7.5 Hz, 1H), 7.10-6.98 (m, 1H), 6.68 (s, 1H), 6.63 (d, J = 9.0 Hz, 1H), 5.76 (s, 1H), 5.40 (dd, J = 12.5, 5.3 Hz, 1H), 4.85 (s, 2H), 4.56-4.45 (m, 3H), 4.33 (d, J = 4.2 Hz, 1H), 3.31 (s, 4H), 2.95-2.83 (m, 1H), 2.75-2.58 (m, 2H), 2.01 (s, 3H), 1.78 (s, 1H), 1.47 (s, 1H), 1.38 (s, 7H), 1.07 (d, J = 6.0 Hz, 2H), 1.04 (d, J = 6.1 Hz, 3H). |
| B-3-2 | 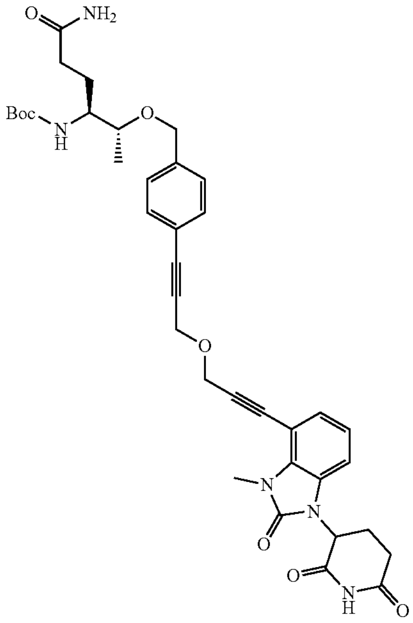 [SMILES: C[C@@H](OCc1ccc(C#CCOCC#Cc2cccc3c2n(C)c(=O)n3C2CCC(=O)NC2=O)cc1)[C@H](CCC(N)=O)NC(=O)OC(C)(C)C] | tert-butyl N-[(3S,4R)-1-carbamoyl-4-([4-[3-([3-[1-(2,6-dioxopiperidin-3-yl)-3-methyl-2-oxo,1,3-benzodiazol-4-yl]prop-2-yn-1-yl]oxy)prop-1-yn-1-yl]phenyl]methoxy)pentan-3-yl]carbamate | 686.5 | (400 MHz, DMSO-$d_6$) δ 11.12 (d, J = 6.2 Hz, 1H), 7.42 (t, J = 7.9 Hz, 2H), 7.38-7.25 (m, 2H), 7.17 (dt, J = 15.2, 8.2 Hz, 3H), 7.03 (q, J = 7.9 Hz, 1H), 6.64 (dd, J = 19.5, 10.8 Hz, 2H), 5.40 (dt, J = 12.3, 5.8 Hz, 1H), 4.59 (d, J = 7.3 Hz, 2H), 4.57-4.43 (m, 4H), 4.27-4.17 (m, 1H), 3.66-3.63 (m, 3H), 3.43 (dq, J = 18.0, 6.0 Hz, 1H), 2.76-2.59 (m, 1H), 2.49 (s, 1H), 2.07-1.99 (m, 3H), 1.38-1.36 (m, 9H), 1.11-1.00 (m, 6H). |

TABLE 15-continued

| Characterization data for intermediates prepared according to above. | | | | |
|---|---|---|---|---|
| Intermediate | Structure | Chemical Name | MS: $[(M+1)]^+$ | $^1$H-NMR |
| B-3-3 | 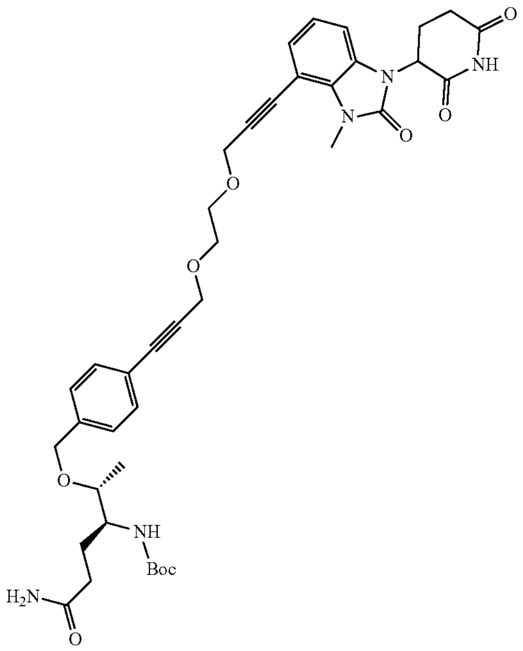 [SMILES: C[C@@H](OCc1ccc(C#CCOCCOCC#Cc2cccc3c2n(C)c(=O)n3C2CCC(=O)NC2=O)cc1)[C@H](CCC(N)=O)NC(=O)OC(C)(C)C] | tert-butyl N-[(3S,4R)-1-carbamoyl-4-[(4-[3-[2-([3-[1-(2,6-dioxopiperidin-3-yl)-3-methyl-2-oxo,1,3-benzodiazol-4-yl]prop-2-yn-1-yl]oxy)ethoxy]prop-1-yn-1-yl]phenyl)methoxy]pentan-3-yl]carbamate | 730.4 | (400 MHz, $CD_3OD$) δ 7.75-7.62 (m, 1H), 7.53-7.30 (m, 3H), 7.28-6.92 (m, 3H), 5.51 (s, 1H), 5.36 (s, 1H), 4.69-4.23 (m, 6H), 3.84-3.77 (m, 6H), 6.58-3.51 (m, 2H), 3.04-2.68 (m, 3H), 2.20 (s, 3H), 1.98 (s, 1H), 1.51-1.41 (m, 7H), 1.32 (s, 2H), 1.18 (d, J = 6.6 Hz, 2H), 1.00-0.92 (m, 2H). |
| B-3-4 | 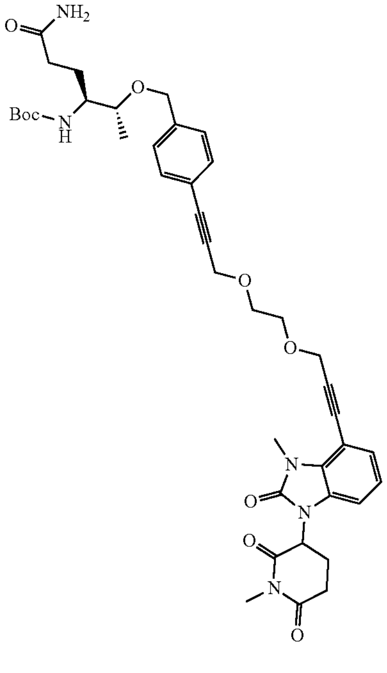 [SMILES: C[C@@H](OCc1ccc(C#CCOCCOCC#Cc2cccc3c2n(C)c(=O)n3C2CCC(=O)N(C)C2=O)cc1)[C@H](CCC(N)=O)NC(=O)OC(C)(C)C] | tert-butyl N-[(3S,4R)-1-carbamoyl-4-[(4-[3-[2-([3-[3-methyl-1-(1-methyl-2,6-dioxopiperidin-3-yl)-3-oxo,1,3-benzodiazol-4-yl]prop-2-yn-1-yl]oxy)ethoxy]prop-1-yn-1-yl]phenyl)methoxy]pentan-3-yl]carbamate | 744.5 | (400 MHz, DMSO-$d_6$) δ 7.51-7.49 (m, 1H), 7.39 (d, J = 7.5 Hz, 2H), 7.35-7.34 (m, 3H), 7.24-7.07 (m, 3H), 7.01 (q, J = 7.6 Hz, 1H), 6.71-6.56 (m, 2H), 5.76-5.74 (m, 1H), 5.50-5.41 (m, 1H), 4.47-4.41 (m, 7H), 3.78-3.56 (m, 7H), 3.46-3.38 (m, 2H), 3.12-2.87 (m, 4H), 2.83-2.66 (m, 2H), 2.03 (s, 4H), 1.76 (s, 1H), 1.46 (s, 2H), 1.23 (d, J = 9.3 Hz, 1H), 1.08-1.06 (m, 4H). |

TABLE 15-continued

| Characterization data for intermediates prepared according to above. | | | | |
|---|---|---|---|---|
| Inter-mediate | Structure | Chemical Name | MS: [(M + 1)]$^+$ | $^1$H-NMR |
| B-3-5 | 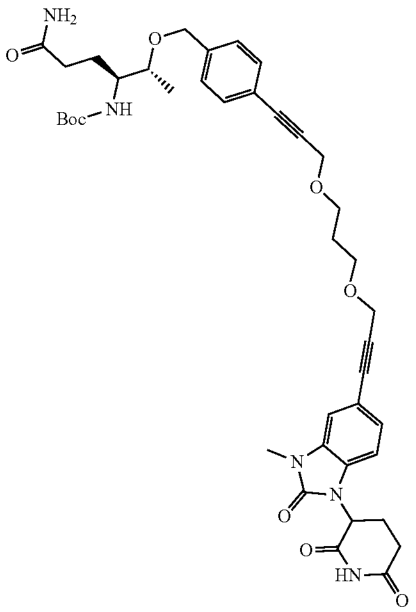 [SMILES: C[C@@H](OCc1ccc(C#CCOCCCOCC#Cc2ccc3c(c2)n(C)c(=O)n3C2CCC(=O)NC2=O)cc1)[C@H](CCC(N)=O)NC(=O)OC(C)(C)C] | tert-butyl N-[(3S,4R)-1-carbamoyl-4-[(4-[3-[3-([3-[1-(2,6-dioxopiperidin-3-yl)-3-methyl-2-oxo-2,3-dihydro-1H-1,3-benzodiazol-5-yl]prop-2-yn-1-yl]oxy)propoxy]prop-1-yn-1-yl]phenyl)methoxy]pentan-3-yl]carbamate | 744.3 | (400 MHz, $CDCl_3$) δ 9.30 (s, 1H), 7.40 (dd, J = 8.1, 3.1 Hz, 2H), 7.25-7.22 (m, J 3H), 7.12 (s, 1H), 6.76 (d, J = 8.0 Hz, 1H), 5.22 (dd, J = 12.9, 5.2 Hz, 1H), 4.92 (d, J = 9.8 Hz, 1H), 4.57 (d, J = 11.9 Hz, 1H), 4.38 (s, 4H), 3.74 (d, J = 2.2 Hz, 1H), 3.59 (s, 1H), 3.40 (d, J = 2.6 Hz, 3H), 2.98-2.78 (m, 3H), 2.37-2.17 (m, 5H), 1.99-1.96 (m, 3H), 1.44 (s, 9H), 1.19 (dd, J = 6.4, 1.6 Hz, 3H), 0.93-0.88 (m, 3H). |
| B-3-6 | 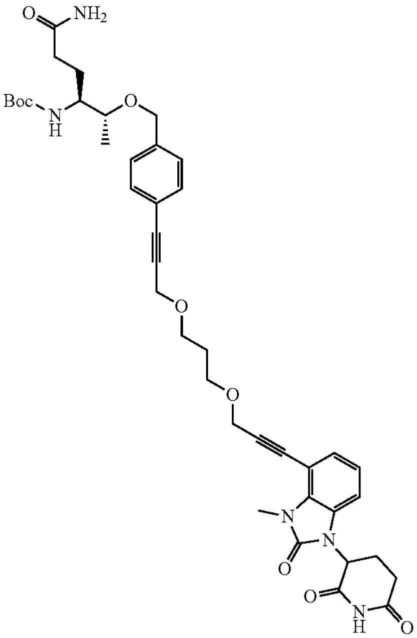 [SMILES: C[C@@H](OCc1ccc(C#CCOCCCOCC#Cc2cccc3c2n(C)c(=O)n3C2CCC(=O)NC2=O)cc1)[C@H](CCC(N)=O)NC(=O)OC(C)(C)C] | tert-butyl N-[(3S,4R)-1-carbamoyl-4-[(4-[3-[3-([3-[1-(2,6-dioxopiperidin-3-yl)-3-methyl-2-oxo-1,3-benzodiazol-4-yl]prop-2-yn-1-yl]oxy)propoxy]prop-1-yn-1-yl]phenyl)methoxy]pentan-3-yl]carbamate | 744.5 | (400 MHz, $CD_3OD$) δ 7.71-6.80 (m, 7H), 5.35 (s, 1H), 4.64-4.17 (m, 6H), 3.75 (s, 6H), 3.51 (s, 3H), 2.88-2.84 (m, 3H), 2.25 (s, 3H), 1.95 (s, 3H), 1.40-1.36 (m, 9H), 1.18 (s, 4H). |

TABLE 15-continued

| Characterization data for intermediates prepared according to above. | | | | |
|---|---|---|---|---|
| Inter-mediate | Structure | Chemical Name | MS: $[(M + 1)]^+$ | $^1$H-NMR |
| B-3-7 | 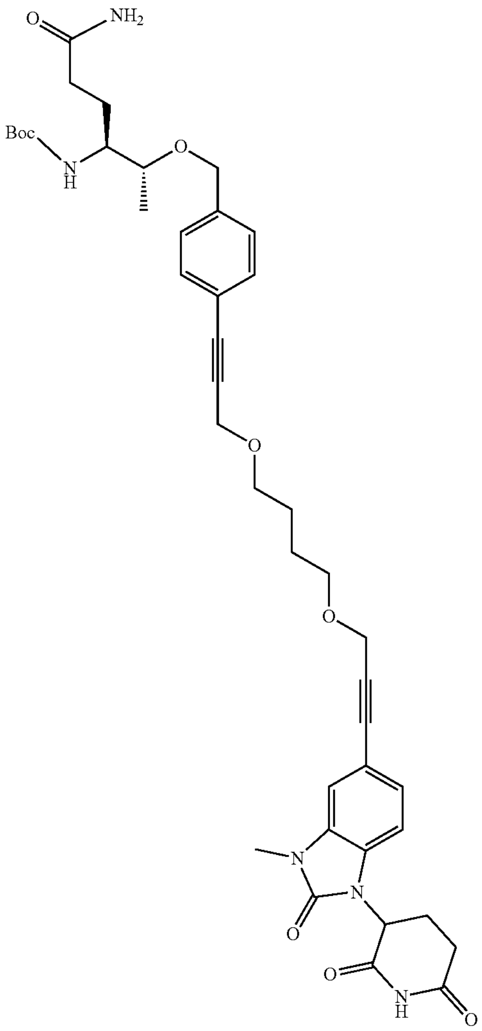 [SMILES: C[C@@H](OCc1ccc(C#CCOCCCCOCC#Cc2ccc3c(c2)n(C)c(=O)n3C2CCC(=O)NC2=O)cc1)[C@H](CCC(N)=O)NC(=O)OC(C)(C)C] | tert-butyl N-[(3S,4R)-1-carbamoyl-4-[(4-[3-[4-([3-[1-(2,6-dioxopiperidin-3-yl)-3-methyl-2-oxo-1,3-benzodiazol-5-yl]prop-2-yn-1-yl]oxy)butoxy]prop-1-yn-1-yl]phenyl)methoxy]pentan-3-yl]carbamate | 758.5 | (400 MHz, DMSO-d6) δ 11.12 (s, 1H), 7.40 (d, J = 8.1 Hz, 2H), 7.34-7.32 (m, 3H), 7.23-7.11 (m, 3H), 6.72-6.59 (m, 2H), 5.76 (s, 1H), 5.39 (dd, J = 12.8, 5.3 Hz, 1H), 4.56-4.44 (m, 2H), 4.37-4.35 (m, 4H), 3.56-3.53 (m, 4H), 3.42 (q, J = 5.6 Hz, 1H), 3.34 (s, 3H), 2.92-2.84 (m, 1H), 2.77-2.59 (m, 2H), 2.15-1.96 (m, 3H), 1.78 (dt, J = 6.9, 3.8 Hz, 1H), 1.64-1.61 (m, 4H), 1.48 (dt, J = 9.2, 4.9 Hz, 1H), 1.38 (s, 9H), 1.07 (d, J = 6.0 Hz, 3H). |

TABLE 15-continued

Characterization data for intermediates prepared according to above.

| Inter-mediate | Structure | Chemical Name | MS: $[(M + 1)]^+$ | $^1$H-NMR |
|---|---|---|---|---|
| B-3-8 | 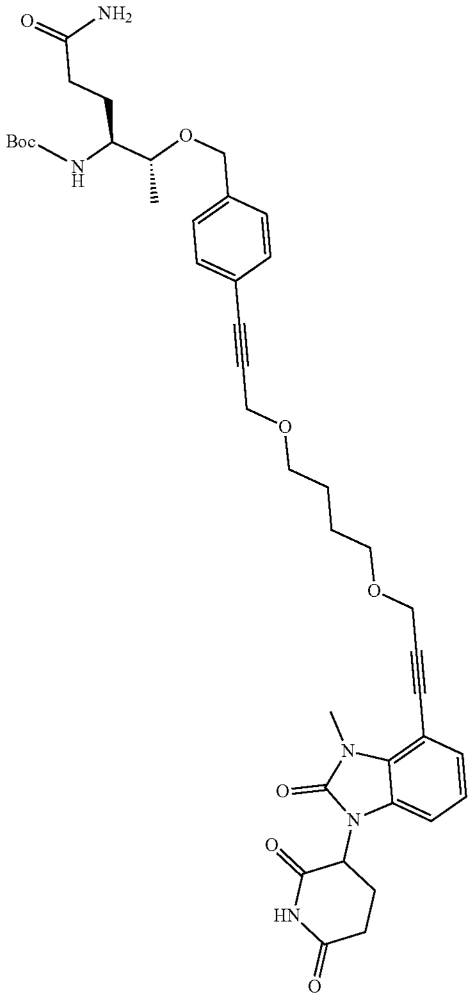 [SMILES: C[C@@H](OCc1ccc(C#CCOCCCCOCC#Cc2cccc3c2n(C)c(=O)n3C2CCC(=O)NC2=O)cc1)[C@H](CCC(N)=O)NC(=O)OC(C)(C)C] | tert-butyl N-[(3S,4R)-1-carbamoyl-4-[(4-[3-[4-([3-[1-(2,6-dioxopiperidin-3-yl)-3-methyl-2-oxo-1,3-benzodiazol-4-yl]prop-2-yn-1-yl]oxy)butoxy]prop-1-yn-1-yl]phenyl)methoxy]pentan-3-yl]carbamate | 758.5 | (400 MHz, DMSO-$d_6$) δ 11.13 (s, 1H), 7.40 (d, J = 7.9 Hz, 2H), 7.33 (d, J = 8.0 Hz, 2H), 7.26-7.15 (m, 2H), 7.12 (d, J = 7.8 Hz, 1H), 7.03 (t, J = 7.9 Hz, 1H), 6.74-6.56 (m, 2H), 5.40 (dd, J = 12.6, 5.4 Hz, 1H), 4.55-4.38 (m, 4H), 4.36 (s, 2H), 3.60-3.50 (m, 4H), 3.43 (dq, J = 17.5 5.9 Hz, 2H), 2.95-2.83 (m, 2H), 2.78-2.58 (m, 2H), 2.15-1.96 (m, 3H), 1.76 (q, J = 9.9, 9.0 Hz, 1H), 1.68-1.55 (m, 5H), 1.55-1.42 (m, 1H), 1.38 (s, 10H), 1.07 (d, J = 6.0 Hz, 3H). |

TABLE 15-continued

| Characterization data for intermediates prepared according to above. | | | | |
|---|---|---|---|---|
| Intermediate | Structure | Chemical Name | MS: $[(M + 1)]^+$ | $^1$H-NMR |
| B-3-9 | 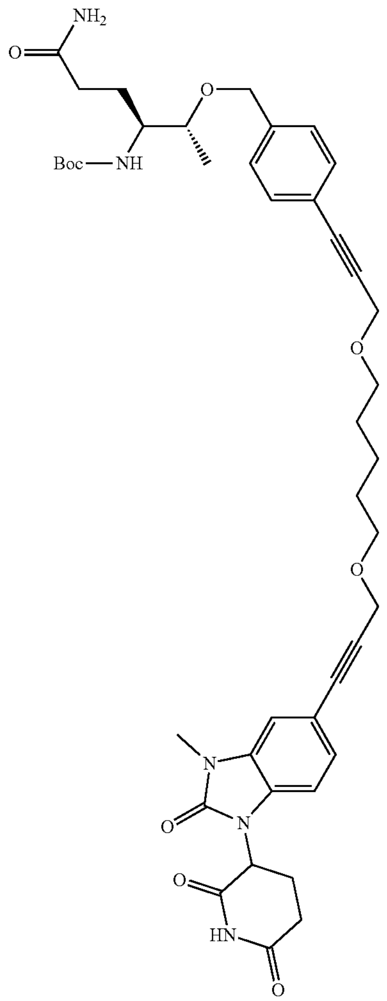 [SMILES: C[C@@H](OCc1ccc(C#CCOCCCCCOCC#Cc2ccc3c(c2)n(C)c(=O)n3C2CCC(=O)NC2=O)cc1)[C@H](CCC(N)=O)NC(=O)OC(C)(C)C] | tert-butyl N-[(3S,4R)-1-carbamoyl-4-[(4-[3-[[5-([3-[1-(2,6-dioxopiperidin-3-yl)-3-methyl-2-oxo-1,3-benzodiazol-5-yl]prop-2-yn-1-yl]oxy)pentyl]oxy]prop-1-yn-1-yl)phenyl]methoxy]pentan-3-yl]carbamate | 772.4 | (400 MHz, $CD_3OD$) δ 7.72-7.53 (m, 1H), 7.52-7.45 (m, 1H), 7.43-7.19 (m, 6H), 7.10 (d, J = 8.2 Hz, 1H), 5.35 (dd, J = 12.5, 5.4 Hz, 1H), 4.62-4.45 (m, 3H), 4.39-4.34 (m, 4H), 3.68-3.53 (m, 5H), 3.52 (dd, J = 6.2, 2.6 Hz, 1H), 3.44 (d, J = 4.0 Hz, 1H), 3.42 (s, 3H), 2.9 (ddd, J = 18.9, 14.3, 5.1 Hz, 1H), 2.87-2.77 (m, 2H), 2.68 (s, 2H), 2.32-2.15 (m, 2H), 2.05 (s, 2H), 2.03-1.92 (m, 1H), 1.59-1.50 (m, 1H), 1.45 (s, 9H), 1.18 (dd, J = 6.2, 2.7 Hz, 3H). |

TABLE 15-continued

| Characterization data for intermediates prepared according to above. | | | | |
|---|---|---|---|---|
| Intermediate | Structure | Chemical Name | MS: $[(M + 1)]^+$ | $^1$H-NMR |
| B-3-10 | 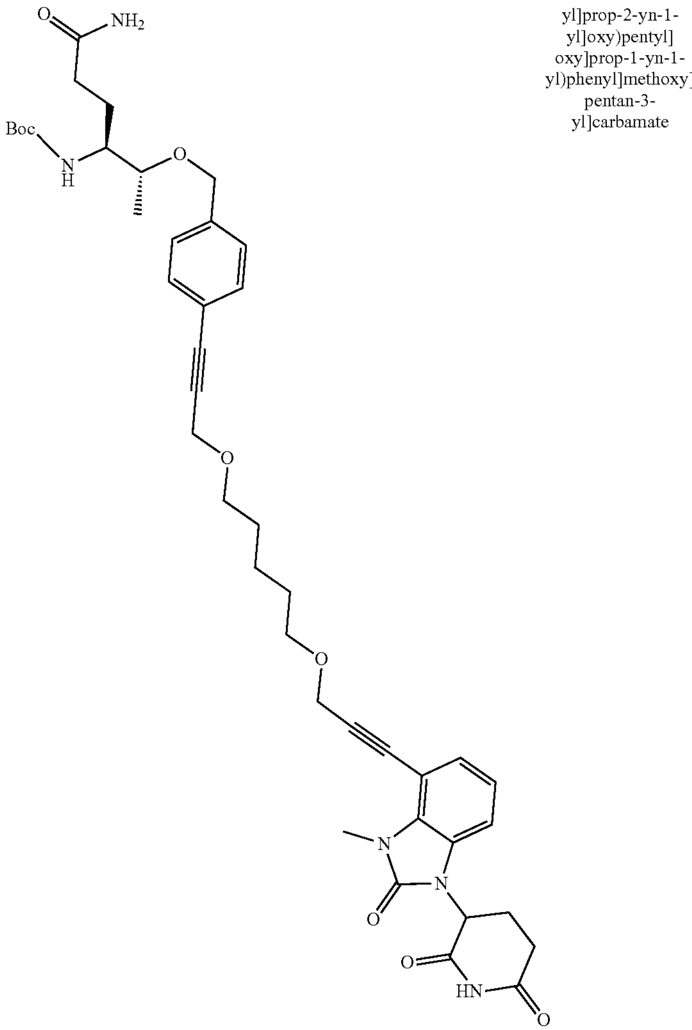 | tert-butyl N-[(3S,4R)-1-carbamoyl-4-[(4-[3-[[5-([3-[1-(2,6-dioxopiperidin-3-yl)-3-methyl-2-oxo-1,3-benzodiazol-4-yl]prop-2-yn-1-yl]oxy)pentyl]oxy]prop-1-yn-1-yl)phenyl]methoxy]pentan-3-yl]carbamate | 772.5 | (400 MHz, $CD_3OD$) δ 7.39 (d, J = 7.9 Hz, 2H), 7.33 (d, J = 8.0 Hz, 2H), 7.19 (dd, J = 7.7, 1.3 Hz, 1H) 7.13 (d, J = 7.8 Hz, 1H), 7.07 (t, J = 7.8 Hz, 1H), 6.41 (d, J = 9.7 Hz, 1H), 5.35 (dd, J = 12.2, 5.4 Hz, 1H), 4.57 (d, J = 12.0 Hz, 1H), 4.49 (d, J = 12.1 Hz, 1H), 4.44 (s, 2H), 4.36 (s, 2H), 3.76 (s, 2H), 3.66-3.62 (m, 3H), 3.58 (s, 2H), 3.54-3.47 (m, 2H), 2.97-2.77 (m, 2H), 2.32-2.14 (m, 2H), 1.97 (s, 1H), 1.70-1.68 (m, 5H), 1.59-1.49 (m, 3H), 1.44 (s, 9H), 1.18 (d, J = 6.3 Hz, 3H). |

TABLE 15-continued
| Characterization data for intermediates prepared according to above. | | | | |
|---|---|---|---|---|
| Inter-mediate | Structure | Chemical Name | MS: [(M + 1)]+ | 1H-NMR |
| B-3-11 | 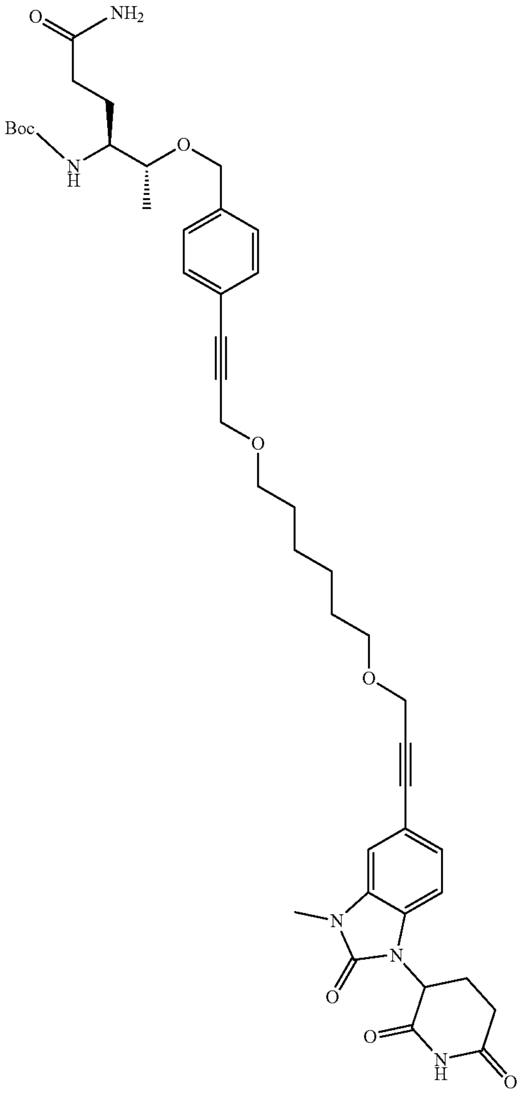 [SMILES: C[C@@H](OCc1ccc(C#CCOCCCCCCOCC#Cc2ccc3c(c2)n(C)c(=O)n3C2CCC(=O)NC2=O)cc1)[C@H](CCC(N)=O)NC(=O)OC(C)(C)C] | tert-butyl N-[(3S,4R)-1-carbamoyl-4-[(4-[3-[[6-([3-[1-(2,6-dioxopiperidin-3-yl)-3-methyl-2-oxo-2,3-dihydro-1H-1,3-benzodiazol-5-yl]prop-2-yn-1-yl]oxy)hexyl]oxy]prop-1-yn-1-yl)phenyl]methoxy]pentan-3-yl]carbamate | 786.5 | (400 MHz, DMSO-$d_6$) δ 11.12 (s, 1H), 7.40 (d, J = 8.0 Hz, 2H), 7.34-7.30 (m, 5H), 7.22 (s, 1H), 7.19-7.12 (m, 2H), 5.39 (dd, J = 12.7, 5.3 Hz, 1H), 4.53-4.40 (m, 3H), 4.35 (d, J = 3.4 Hz, 4H), 3.52-3.54 (m, 4H), 2.95-2.83 (m, 1H), 2.76-2.59 (m, 2H), 2.07-2.01 (m, 4H), 1.92 (s, 1H), 1.77 (s, 1H), 1.60-1.44 (m, 6H), 1.38 (s, 12H), 1.09-1.06 (m, 5H). |

TABLE 15-continued

| Characterization data for intermediates prepared according to above. | | | | |
|---|---|---|---|---|
| Intermediate | Structure | Chemical Name | MS: $[(M + 1)]^+$ | $^1$H-NMR |
| B-3-12 | 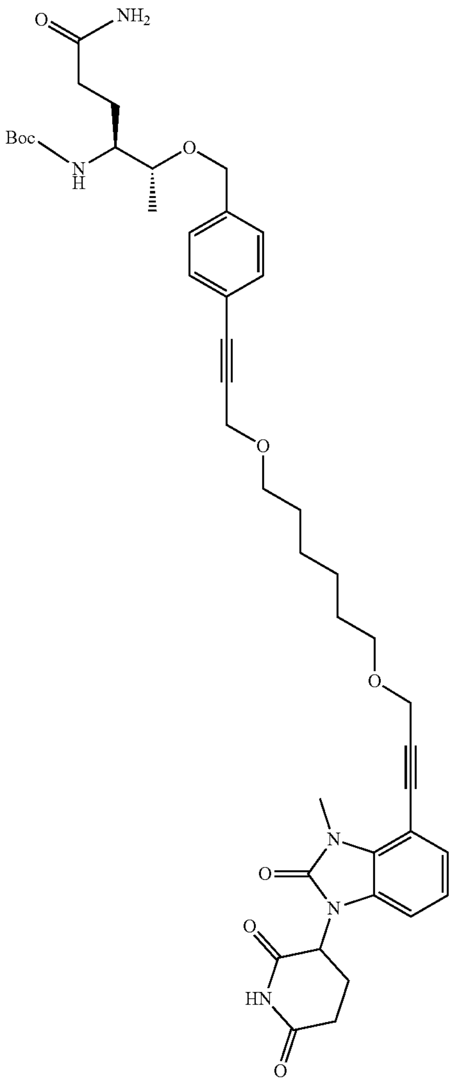 [SMILES: C[C@@H](OCc1ccc(C#CCOCCCCCCOCC#Cc2cccc3c2n(C)c(=O)n3C2CCC(=O)NC2=O)cc1)[C@H](CCC(N)=O)NC(=O)OC(C)(C)C] | tert-butyl N-[(3S,4R)-1-carbamoyl-4-[(4-[3-[[6-([3-[1-(2,6-dioxopiperidin-3-yl)-3-methyl-2-oxo-1,3-benzodiazol-4-yl]prop-2-yn-1-yl]oxy)hexyl]oxy]prop-1-yn-1-yl)phenyl]methoxy]pentan-3-yl]carbamate | 786.5 | (400 MHz, DMSO-$d_6$) δ 11.13 (s, 1H), 7.40 (d, J = 7.9 Hz, 2H), 7.33 (d, J = 8.0 Hz, 2H), 7.22 (s, 1H), 7.18 (d, J = 7.8 Hz, 1H), 7.12 (d, J = 7.8 Hz, 1H), 7.03 (t, J = 7.8 Hz, 1H), 6.69 (s, 1H), 6.63 (d, J = 9.1 Hz, 1H), 5.41 (dd, J = 12.6, 5.4 Hz, 1H), 4.54-4.44 (m, 2H), 4.42 (s, 2H), 4.34 (s, 2H), 3.56-3.37 (m, 7H), 2.90 (ddd, J = 16.9, 12.6, 5.0 Hz, 1H), 2.77-2.57 (m, 2H), 2.13-1.98 (m, 3H), 1.83-1.72 (m, 1H), 1.61-1.42 (m, 6H), 1.38-1.35 (m, 14H), 1.07 (d, J = 6.0 Hz, 3H). |

TABLE 15-continued

| Characterization data for intermediates prepared according to above. | | | | |
|---|---|---|---|---|
| Inter-mediate | Structure | Chemical Name | MS: $[(M+1)]^+$ | $^1H$-NMR |
| B-3-13 | 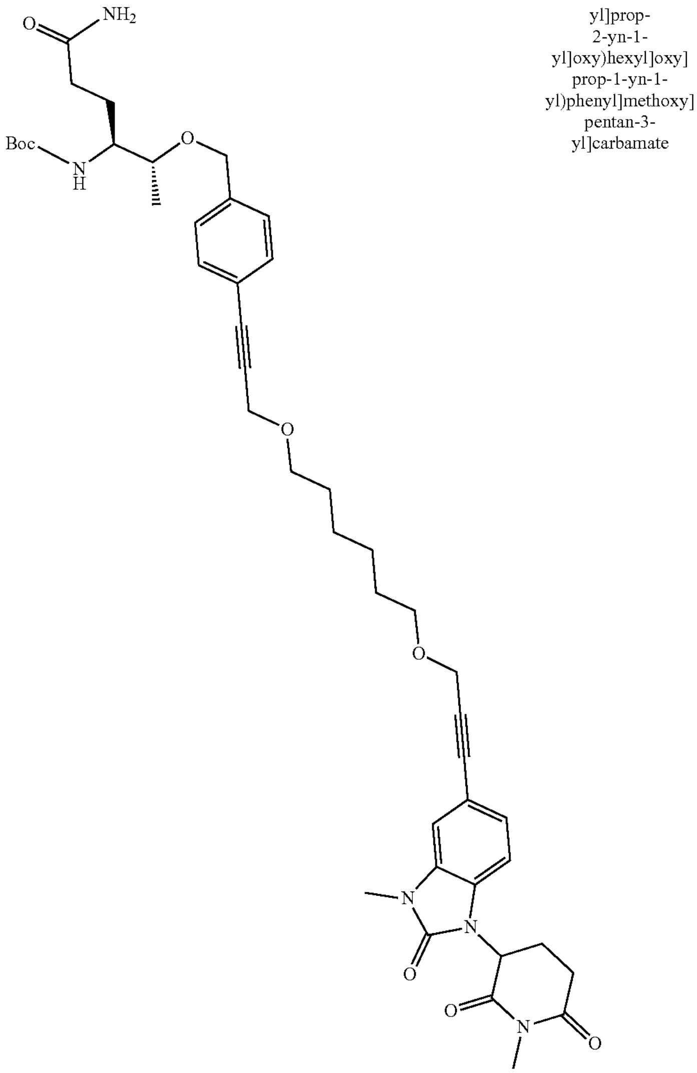 | tert-butyl N-[(3S,4R)-1-carbamoyl-4-[(4-[3-[[6-([3-[3-methyl-1-(1-methyl-2,6-dioxopiperidin-3-yl)-2-oxo-1,3-benzodiazol-5-yl]prop-2-yn-1-yl]oxy)hexyl]oxy]prop-1-yn-1-yl)phenyl]methoxy]pentan-3-yl]carbamate | 800.6 | (400 MHz, DMSO-$d_6$) δ 7.40 (d, J = 8.0 Hz, 2H), 7.36-7.32 (m, 3H), 7.21 (s, 1H), 7.15 (d, J = 1.1 Hz, 2H), 6.67 (s, 1H), 6.66-6.59 (m, 1H), 5.46 (dd, J = 12.9, 5.3 Hz, 1H), 4.55-4.43 (m, 2H), 4.37-4.34 (m, 4H), 3.52-3.48 (m, 4H), 3.41 (dt, J = 12.1, 5.9 Hz, 1H), 3.04 (s, 3H), 3.02-2.91 (m, 1H), 2.81 (s, 1H), 2.79-2.67 (m, 2H), 2.10-1.99 (m, 1H), 1.92 (s, 1H), 1.78 (s, 1H), 1.55 (d, J = 6.7 Hz, 2H), 1.40-1.32 (m, 14H), 1.07 (d, J = 6.0 Hz, 3H). |

TABLE 15-continued

| Characterization data for intermediates prepared according to above. | | | | |
|---|---|---|---|---|
| Intermediate | Structure | Chemical Name | MS: $[(M + 1)]^+$ | $^1$H-NMR |
| B-3-14 | 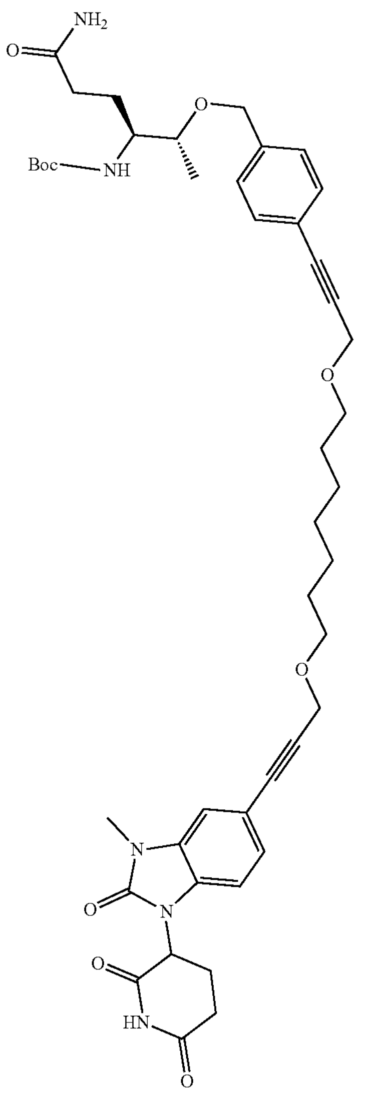 [SMILES: C[C@@H](OCc1ccc(C#CCOCCCCCCCOCC#Cc2ccc3c(c2)n(C)c(=O)n3C2CCC(=O)NC2=O)cc1)[C@H](CCC(N)=O)NC(=O)OC(C)(C)C] | tert-butyl N-[(3S,4R)-1-carbamoyl-4-[(4-[3-[[7-([3-[1-(2,6-dioxopiperidin-3-yl)-3-methyl-2-oxo-1,3-benzodiazol-5-yl]prop-2-yn-1-yl]oxy)hexyl]oxy]prop-1-yn-1-yl)phenyl]methoxy]pentan-3-yl]carbamate | 800.4 | (400 MHz, DMSO-$d_6$) δ 11.12 (s, 1H), 7.40 (d, J = 7.9 Hz, 2H), 7.34 (d, J = 8.3 Hz, 3H), 7.22 (s, 1H), 7.19-7.10 (m, 2H), 6.68 (s, 1H), 6.63 (d, J = 9.2 Hz, 1H), 5.39 (dd, J = 12.6, 5.4 Hz, 1H), 4.55-4.43 (m, 2H), 4.34 (d, J = 3.7 Hz, 4H), 3.52-3.48 (m, 4H), 3.42 (q, J = 5.7 Hz, 1H), 2.96-2.84 (m, 1H), 2.77-2.60 (m, 2H), 2.05-2.01 (m, 7H), 1.77 (s, 1H), 1.55-1.52 (m, 5H), 1.36-3.30 (m, 15H, 1.07 (d, J = 6.1 Hz, 3H). |

TABLE 15-continued

| Characterization data for intermediates prepared according to above. | | | | |
|---|---|---|---|---|
| Inter-mediate | Structure | Chemical Name | MS: $[(M+1)]^+$ | $^1$H-NMR |
| B-3-15 | 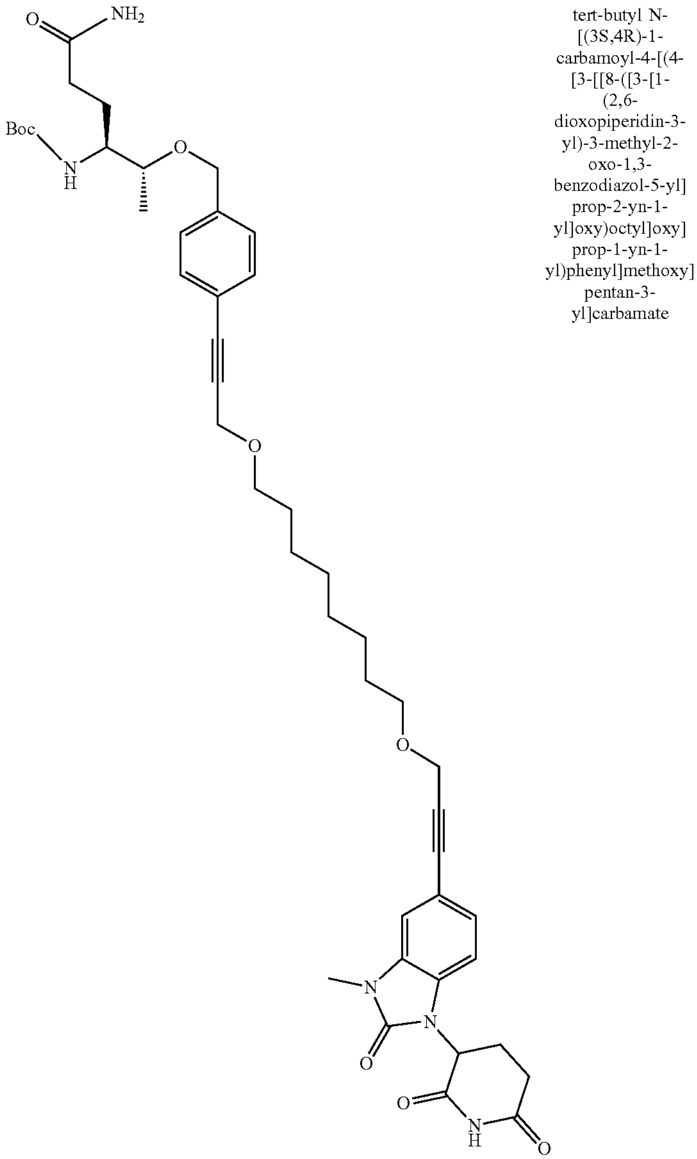 | tert-butyl N-[(3S,4R)-1-carbamoyl-4-[(4-[3-[[8-([3-[1-(2,6-dioxopiperidin-3-yl)-3-methyl-2-oxo-1,3-benzodiazol-5-yl]prop-2-yn-1-yl]oxy)octyl]oxy]prop-1-yn-1-yl)phenyl]methoxy]pentan-3-yl]carbamate | 814.5 | (400 MHz, $CDCl_3$) δ 8.46 (s, 1H), 7.44 (d, J = 7.9 Hz, 2H), 7.27 (s, 2H), 7.24-7.19 (m, 1H), 7.13 (d, J = 1.4 Hz, 1H), 6.77 (d, J = 8.2 Hz, 1H), 5.21 (dd, J = 12.6, 5.3 Hz, 1H), 4.87 (d, J = 9.5 Hz, 1H), 4.60 (d, J = 12.0 Hz, 1H), 4.42 (d, J = 12.0 Hz, 1H), 4.37 (s, 4H), 4.35-4.32 (m, 6H), 3.68 (s, 1H), 3.61-3.56 (m, 4H), 3.44 (s, 3H), 2.96 (d, J = 16.6 Hz, 1H), 2.89-2.73 (m, 2H), 2.37-2.22 (m, 4H), 1.75-1.71 (m, 5H), 1.66-1.61 (m, 5H), 1.45 (s, 9H), 1.37 (s, 3H). |

TABLE 15-continued
| Characterization data for intermediates prepared according to above. | | | | |
|---|---|---|---|---|
| Intermediate | Structure | Chemical Name | MS: $[(M + 1)]^+$ | $^1$H-NMR |
| B-3-16 | 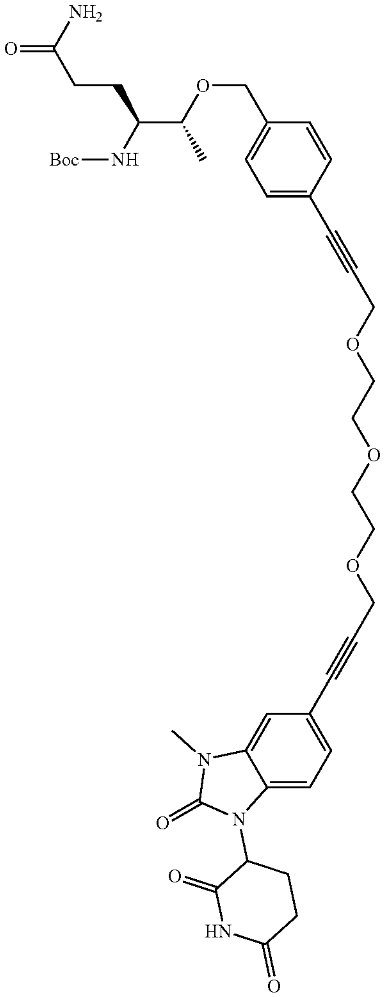 [SMILES: C[C@@H](OCc1ccc(C#CCOCCOCCOCC#Cc2ccc3c(c2)n(C)c(=O)n3C2CCC(=O)NC2=O)cc1)[C@H](CCC(N)=O)NC(=O)OC(C)(C)C] | tert-butyl N-[(3S,4R)-1-carbamoyl-4-[(4-[3-[2-[2-([3-[1-(2,6-dioxopiperidin-3-yl)-3-methyl-2-oxo-2,3-dihydro-1H-1,3-benzodiazol-5-yl]prop-2-yn-1-yl]oxy)ethoxy]ethoxy]prop-1-yn-1-yl)phenyl]methoxy]pentan-3-yl]carbamate | 774.5 | (400 MHz, DMSO-$d_6$) δ 11.14 (s, 1H), 7.55-7.49 (m, 2H), 7.41 (d, J = 8.1 Hz, 2H), 7.36-7.28 (m, 4H), 7.24 (s, 1H), 7.20-7.11 (m, 2H), 6.73-6.62 (m, 3H), 5.40 (dd, J = 12.8, 5.3 Hz, 1H), 3.70-3.52 (m, 8H), 3.34 (s, 6H), 2.96-2.84 (m, 1H), 2.78-2.58 (m, 2H), 1.38 (s, 13H), 1.08-1.06 (m, 5H). |

TABLE 15-continued

| Characterization data for intermediates prepared according to above. | | | | |
|---|---|---|---|---|
| Intermediate | Structure | Chemical Name | MS: [(M + 1)]+ | $^1$H-NMR |
| B-3-17 | 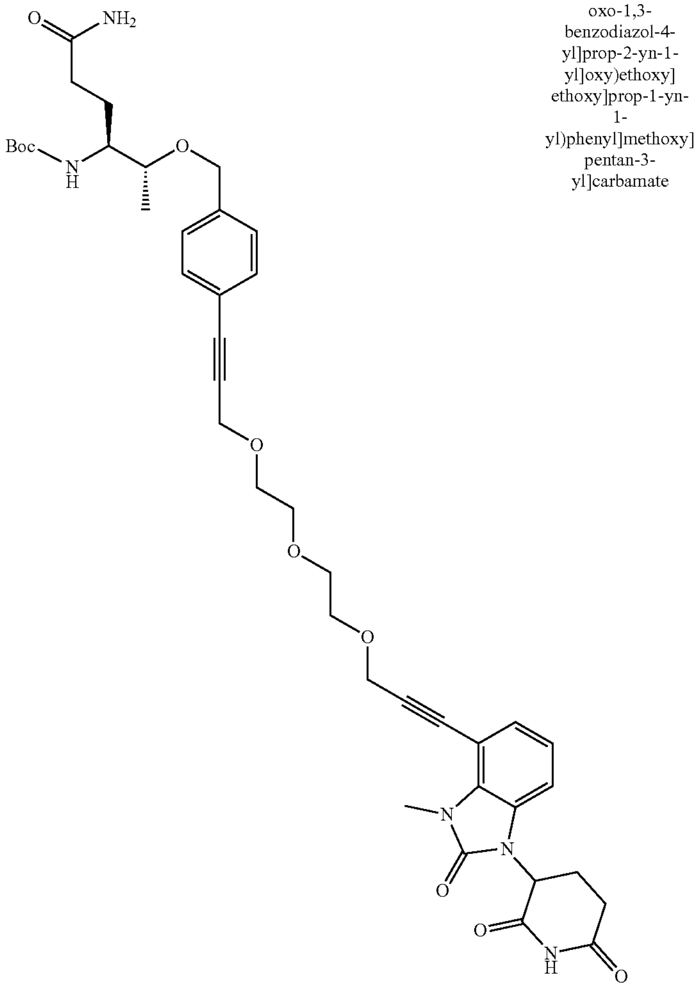 | tert-butyl N-[(3S,4R)-1-carbamoyl-4-[(4-[3-[2-[2-([3-[1-(2,6-dioxopiperidin-3-yl)-3-methyl-2-oxo-1,3-benzodiazol-4-yl]prop-2-yn-1-yl]oxy)ethoxy]ethoxy]prop-1-yn-1-yl)phenyl]methoxy]pentan-3-yl]carbamate | 774.5 | (400 MHz, DMSO-$d_6$) δ 11.12 (s, 1H), 7.41 (d, J = 8.0 Hz, 2H), 7.33 (d, J = 8.0 Hz, 2H), 7.24-7.11 (m, 3H), 7.03 (t, J = 7.9 Hz, 1H), 6.74-6.57 (m, 2H), 5.76 (s, 1H), 5.40 (dd, J = 12.7, 5.3 Hz, 1H), 4.50-4.46 (m, 4H), 4.40 (s, 2H), 3.71-3.34 (m, 13H), 2.96-2.83 (m, 1H), 2.78-2.60 (m, 2H), 2.13-1.96 (m, 3H), 1.77 (s, 1H), 1.38 (s, 9H), 1.07 (d, J = 6.0 Hz, 3H). |

TABLE 15-continued

Characterization data for intermediates prepared according to above.

| Inter-mediate | Structure | Chemical Name | MS: $[(M+1)]^+$ | $^1$H-NMR |
|---|---|---|---|---|
| B-3-18 | 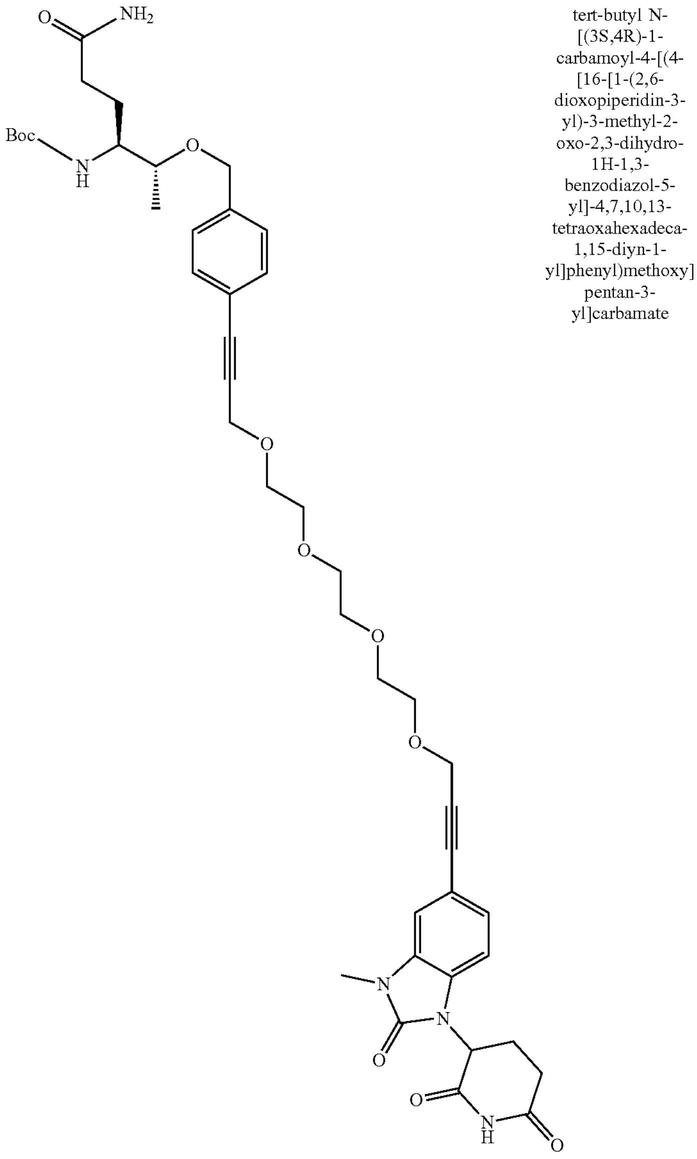 | tert-butyl N-[(3S,4R)-1-carbamoyl-4-[(4-[16-[1-(2,6-dioxopiperidin-3-yl)-3-methyl-2-oxo-2,3-dihydro-1H-1,3-benzodiazol-5-yl]-4,7,10,13-tetraoxahexadeca-1,15-diyn-1-yl]phenyl)methoxy]pentan-3-yl]carbamate | 818.5 | (400 MHz, DMSO-$d_6$) δ 11.13 (s, 1H), 7.66-7.52 (m, 2H), 7.41 (d, J = 7.9 Hz, 2H), 7.37-7.28 (m, 3H), 7.27-7.10 (m, 3H), 6.77-6.58 (m, 2H), 5.40 (dd, J = 12.7, 5.3 Hz, 1H), 4.54-4.45 (m, 2H), 4.42-4.38 (m, 4H), 3.65-3.61 (m, 4H), 3.59-3.57 (m, 4H), 3.47-3.38 (m, 2H), 3.34 (s, 3H), 2.95-2.82 (m, 1H), 2.75-2.58 (m, 2H), 2.08-1.97 (m, 3H), 1.77 (s, 1H), 1.56-1.44 (m, 1H), 1.38 (s, 9H), 1.06 (d, J = 6.0 Hz, 3H). |

TABLE 15-continued

Characterization data for intermediates prepared according to above.

| Inter-mediate | Structure | Chemical Name | MS: $[(M + 1)]^+$ | $^1$H-NMR |
|---|---|---|---|---|
| B-3-19 | 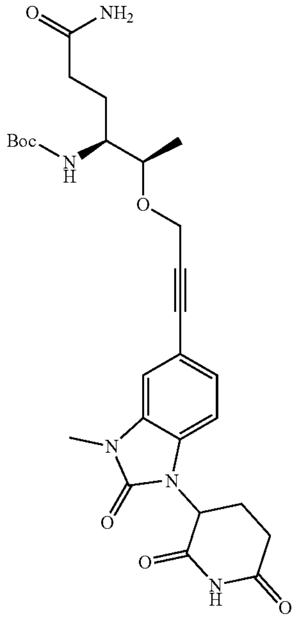 [SMILES: C[C@@H](OCC#Cc1ccc2c(c1)n(C)c(=O)n2C1CCC(=O)NC1=O)[C@H](CCC(N)=O)NC(=O)OC(C)(C)C] | tert-butyl N-[(3S,4R)-1-carbamoyl-4-[(3-[1-(2,6-dioxopiperidin-3-yl)-3-methyl-2-oxo-1,3-benzodiazol-5-yl]prop-2-yn-1-yl]oxy)pentan-3-yl]carbamate | 542.3 | (400 MHz, $CD_3OD$) δ 7.39 (d, J = 1.8 Hz, 1H), 7.32.-721 (m, 1H), 7.08 (d, J = 8.3 Hz, 1H), 5.34 (d, J = 9.8 Hz, 1H), 4.54-4.38 (m, 1H), 4.31 (d, J = 5.6 Hz, 1H), 3.74 (q, J = 6.2 Hz, 1H), 3.62 (p, J = 6.3 Hz, 1H), 3.43 (s, 3H), 3.02-2.75 (m, 4H), 2.37-2.13 (m, 2H), 2.12-1.85 (m, 1H), 1.71-1.53 (m, 1H), 1.45 (s, 9H), 1.19 (d, J = 6.3 Hz, 3H). |
| B-4-1 | 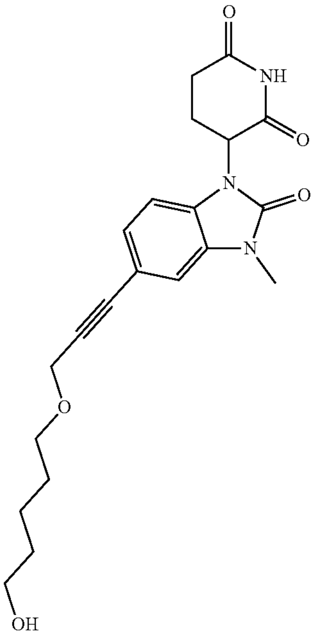 [SMILES: Cn1c(=O)n(C2CCC(=O)NC2=O)c2ccc(C#CCOCCCCCO)cc21] | 3-(5-[3-[(5-hydroxypentyl)oxy]prop-1-yn-1-yl]-3-methyl-2-oxo-1,3-benzodiazol-1-yl)piperidine-2,6-dione | 400.3 | (400 MHz, DMSO-$d_6$) δ 11.12 (s, 1H), 7.33 (d, J = 1.4 Hz, 1H), 7.21-7.09 (m, 2H), 5.39 (dd, J = 12.6, 5.4 Hz, 1H), 4.35 (d, J = 3.0 Hz, 3H), 3.51 (t, J = 6.5 Hz, 2H), 3.40 (q, J = 6.1 Hz, 2H), 3.32 (s, 1H), 2.98-2.82 (m, 1H), 2.78-2.60 (m, 2H), 2.09-2.00 (m, 2H), 1.55 (p, J = 6.8 Hz, 2H), 1.48-1.41 (m, 2H), 1.36 (qd, J = 8.8, 7.3, 2.9 Hz, 2H). |

TABLE 15-continued

Characterization data for intermediates prepared according to above.

| Inter-mediate | Structure | Chemical Name | MS: $[(M + 1)]^+$ | $^1$H-NMR |
|---|---|---|---|---|
| B-4-2 | 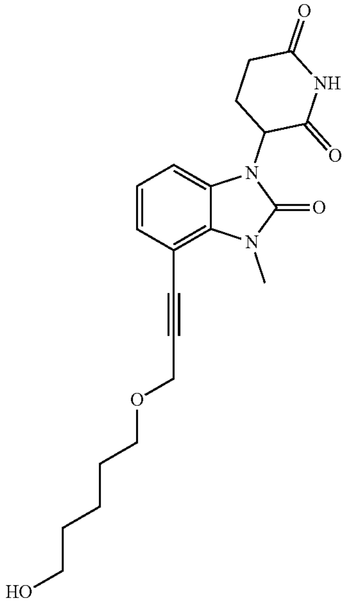 [SMILES: Cn1c(=O)n(C2CCC(=O)NC2=O)c2cccc(C#CCOCCCCCO)c21] | 3-(4-[3-[(5-hydroxypentyl)oxy]prop-1-yn-1-yl]-3-methyl-2-oxo-1,3-benzodiazol-1-yl)piperidine-2,6-dione | 400.2 | (400 MHz, DMSO-$d_6$) δ 11.13 (s, 1H), 7.19-7.13 (m, 2H), 7.04 (t, J = 7.9 Hz, 1H), 5.41 (dd, J = 12.6, 5.3 Hz, 1H), 4.42 (s, 2H), 4.35 (t, J = 5.1 Hz, 1H), 3.65 (s, 3H), 3.53 (t, J = 6.5 Hz, 2H), 3.39 (q, J = 5.9 Hz, 2H), 2.90 (ddd, J = 17.0, 12.8, 5.2 Hz, 1H), 2.78-2.58 (m, 2H), 2.09-1.98 (m, 1H), 1.56 (p, J = 6.8 Hz, 2H), 1.47-1.39 (m, 2H), 1.36 (td, J = 9.0, 5.2 Hz, 2H). |
| B-4-3 | 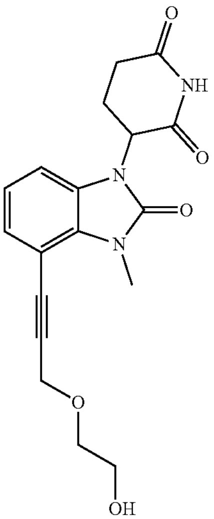 [SMILES: Cn1c(=O)n(C2CCC(=O)NC2=O)c2cccc(C#CCOCCO)c21] | 3-(4-[3-[(5-hydroxyethoxy)prop-1-yn-1-yl]-3-yl]-3-methyl-2-methyl-2-oxo-1,3-benzodiazol-1-yl)piperidine-2,6-dione | 358.2 | (400 MHz, DMSO-$d_6$) δ 11.11 (s, 1H), 7.20-7.16 (m, 1H), 7.15-7.11 (m, 1H), 7.03 (td, J = 7.9, 2.9 Hz, 1H), 5.44-5.36 (m, 1H), 4.67 (p, J = 2.7 Hz, 1H), 4.46 (d, J = 2.8 Hz, 2H), 3.58-3.54 (m, 4H), 3.31 (s, 2H), 2.89 (t, J = 15.2 Hz, 1H), 2.79-2.58 (m, 3H), 2.03 (t, J = 7.4 Hz, 1H). |

TABLE 15-continued

| Inter-mediate | Structure | Chemical Name | MS: [(M + 1)]+ | $^1$H-NMR |
|---|---|---|---|---|
| Characterization data for intermediates prepared according to above. | | | | |
| B-4-4 | 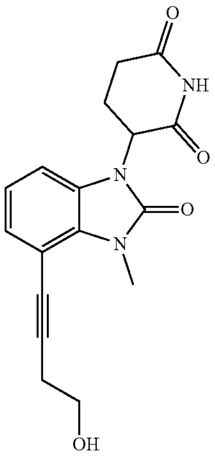 [SMILES: Cn1c(=O)n(C2CCC(=O)NC2=O)c2cccc(C#CCCO)c21] | 3-[4-(4-hydroxybut-1-yn-)1-yl)-3-methyl-2-oxo-1,3-benzodiazol-1-yl]piperidine-2,6-dione | 328.3 | (400 MHz, DMSO-$d_6$) δ 11.12 (s, 1H), 7.12 (dd, J = 7.9, 1.2 Hz, 1H), 7.06 (dd, J = 7.8 Hz, 1H), 1H), 6.99 (t, J = 7.8z, 1H), 5.39 (dd, J = 12.6, 5.4 Hz, 1H), 4.93 (t, J = 5.5 Hz, 1H), 3.65 (s, 3H), 3.63 (t, J = 5.9 Hz, 2H), 2.95-2.84 m, 1H), 2.72 (td, J = 12.9, 4.4 Hz, 1H) 2.63 (q, J = 6.7, 6.2 Hz, 3H), 2.06-1.98 (m, 1H). |
| B-4-5 | 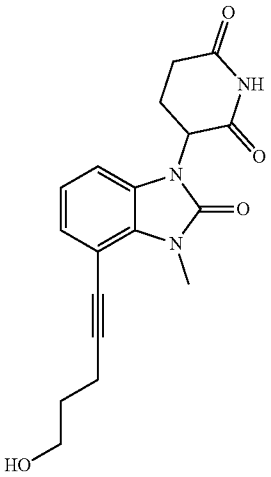 [SMILES: Cn1c(=O)n(C2CCC(=O)NC2=O)c2cccc(C#CCCCO)c21] | 3-[4-(5-hydroxypent-1-yn-1-yl)-3-methyl-2-oxo-1,3-benzodiazol-1-yl]piperidine-2,6-dione | 342.3 | (400 MHz, DMSO-$d_6$) δ 11.12 (s, 1H), 7.12 (dd, J = 7.7, 1.2 Hz, 1H), 7.08-7.04 (m, 1H), 6.99 (t, J = 7.8 Hz, 1H), 5.39 (dd, J = 12.7, 5.3 Hz, 1H), 4.56 (t, J = 5.1 Hz, 1H), 3.64 (s, 3H), 3.53 (q, J = 6.1 Hz, 2H), 3.43 (tt, J = 11.6, 5.5 Hz, 1H), 2.96-2.83 (m, 1H), 2.77-2.59 (m, 2H), 2.03 (ddt, J = 10.9, 5.7m 2.7 Hz, 1H), 1.79-1.69 (m, 2H) 1.66-1.44 (m, 1H). |
| B-4-6 | 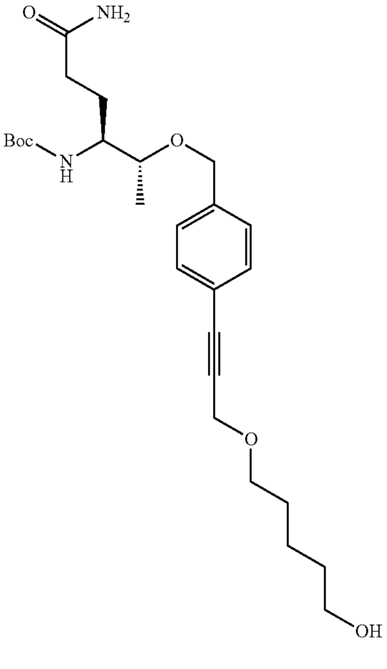 [SMILES: C[C@@H](OCc1ccc(C#CCOCCCCCO)cc1)[C@H](CCC(N)=O)NC(=O)OC(C)(C)C] | tert-butyl N-[(3S,4R)-1-carbamoyl-4-[(4-[3-[(5-hydroxypentyl)oxy[prop-1-yn-1-yl]phenyl)methoxy]pentan-3-yl]carbamate | 477.4 | (400 MHz, DMSO-$d_6$) δ 7.41 (d, J = 7.9 Hz, 2H), 7.34 (d, J = 8.0 Hz, 2H), 7.22 (s, 1H), 6.68 (s, 1H), 6.63 (d, J = 9.1 Hz, 1H), 4.55-4.44 (m, 2H), 4.35 (s, 2H), 4.35 (d, J = 10.3 Hz, 1H), 3.50 (t, J = 6.5 Hz, 2H), 3.46-3.36 (m, 3H), 2.04 (ddd, J = 22.3, 11.6, 6.3 Hz, 1H), 1.78 (s, 1H), 1.54 (h, J = 7.8, 7.3 Hz, 2H), 1.48 (s, 2H), 1.47-1.40 (m, 2H), 1.38 (s, 7H), 1.39-1.30 (m, 5H), 1.07 (d, J = 6.0 Hz, 3H). |

TABLE 15-continued

| Characterization data for intermediates prepared according to above. | | | | |
|---|---|---|---|---|
| Inter-mediate | Structure | Chemical Name | MS: [(M + 1)]+ | $^1$H-NMR |
| B-4-7 | 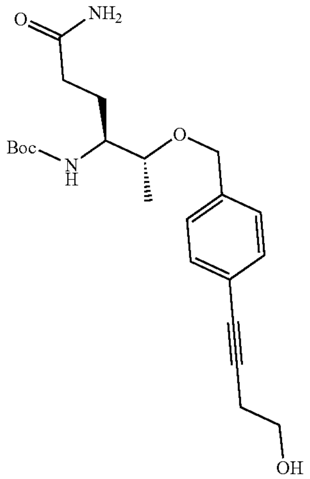 [SMILES: C[C@@H](OCc1ccc(C#CCCO)cc1)[C@H](CCC(N)=O)NC(=O)OC(C)(C)C] | tert-butyl N-[(3S,4R)-1-carbamoyl-4-[[4-(4-hydroxybut)-1-yn-1-yl]phenyl]methoxy]pentan-3-yl]carbamate | 405.3 | (400 MHz, DMSO-$d_6$) δ 7.35-7.30 (m, 4H), 7.22 (s, 1H), 6.68 (s, 1H), 6.62 (d, J = 9.2 Hz, 1H), 4.88 (t, J = 5.6 Hz, 1H), 4.53-4.42 (m, 2H), 3.58 (q, J = 6.7 Hz, 2H), 3.47-3.43 (m, 1H), 3.40 (d, J = 5.9 Hz, 1H), 3.32 (s, 1H), 2.55 (t, J = 6.9z, 2H), 2.12-1.95 (m, 2H), 1.82-1.71 (m, 1H), 1.52-1.43 (m, 1H), 1.38 (s, 8H), 1.06 (d, J = 6.1 Hz, 3H). |
| B-4-8 | 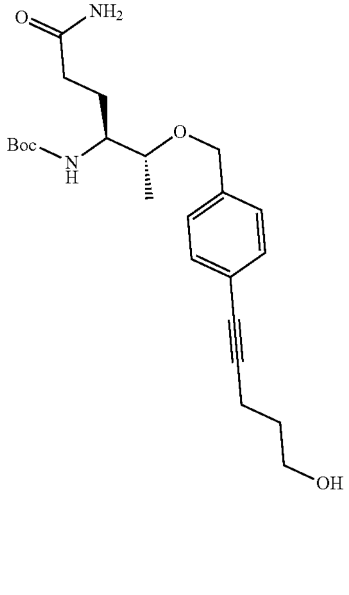 [SMILES: C[C@@H](OCc1ccc(C#CCCCO)cc1)[C@H](CCC(N)=O)NC(=O)OC(C)(C)C] | tert-butyl N-[(3S,4R)-1-carbamoyl-4-[[4-(5-hydroxypent-1-yn-1-yl]phenyl)methoxy]pentan-3-yl]carbamate | 419.3 | (400 MHz, DMSO-$d_6$) δ 7.38 (d, J = 7.9 Hz, 2H), 7.25 (d, J = 7.9 Hz, 2H), 6.58 (s, 1H), 5.59 (s, 1H) 4.86 (d, J = 9.7 Hz, 1H) 4.59 (d, J = 12.0 Hz, 1H), 4.40 (d, J = 11.9 Hz, 1H), 3.84 (t, J = 6.1 Hz, 2H), 3.73-3.57 (m, 2H), 2.56 (t, J = 7.0 Hz, 2H), 2.36-2.22 (m, 3H), 1.98 (t, J = 7.6 Hz, 1H), 1.88 (p, J = 6.6 Hz, 2H), 1.76-1.64 (m, 1H), 1.45 (s, 9H), 1.21 (d, J = 6.3 Hz, 3H). |

TABLE 15-continued

Characterization data for intermediates prepared according to above.

| Inter-mediate | Structure | Chemical Name | MS: $[(M + 1)]^+$ | $^1$H-NMR |
|---|---|---|---|---|
| B-4-9 | 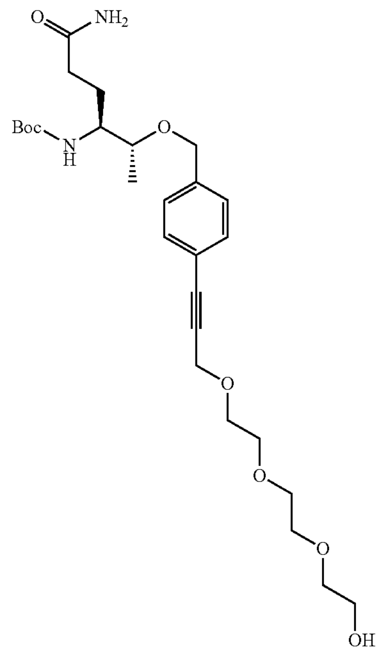 [SMILES: C[C@@H](OCc1ccc(C#CCOCCOCCOCCO)cc1)[C@H](CCC(N)=O)NC(=O)OC(C)(C)C] | tert-butyl N-[(3S,4R)-1-carbamoyl-4-[[4-(3-[2-[2-[(2-hydroxyethoxy)ethoxy]ethoxy]prop-1-yn-1-yl]phenyl]methoxy]pentan-3-yl]carbamate | 523.4 | (400 MHz, $CDCl_3$) δ 7.46-7.42 (m, 2H), 7.29 (s, 1H), 7.27 (s, 1H), 6.43 (s, 1H), 5.47 (s, 1H), 4.86 (d, J = 9.7 Hz, 1H), 4.60 (d, J = 12.0 Hz, 1H), 4.46-4.43 (m, 3H), 3.83-3.78 (m, 2H), 3.77-3.74 (m, 4H), 3.71 (s, 5H), 3.66-3.60 (m, 3H), 2.38-2.22 (m, 3H), 2.04-1.94 (m, 1H), 1.72-1.69 (m, 1H), 1.45 (s, 9H), 1.21 (d, J = 6.3 Hz, 3H). |
| B-4-10 | 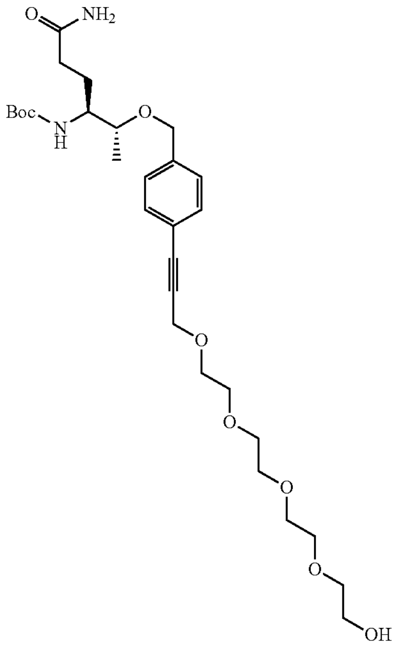 [SMILES: C[C@@H](OCc1ccc(C#CCOCCOCCOCCOCCO)cc1)[C@H](CCC(N)=O)NC(=O)OC(C)(C)C] | tert-butyl N-[(3S,4R)-1-carbamoyl-4-[[4-(1-hydroxy-3,6,9,12-tetraoxapentadec-14-yn-15-yl)phenyl]methoxy]pentan-3-yl]carbamate | 567.4 | (400 MHz, $CDCl_3$) δ 7.46-7.41 (m, 2H), 7.29 (s, 1H), 7.27 (s, 1H), 6.56 (s, 1H), 5.64 (s, 1H), 4.87 (d, J = 9.7 Hz, 1H), 4.61 (d, J = 12.0 Hz, 1H), 4.44 (d, J = 5.3 Hz, 3H), 3.82-3.77 (m, 2H), 3.77-3.72 (m, 4H), 3.72-3.66 (m, 9H), 3.65-3.61 (m, 3H), 2.41-2.21 (m, 2H), 2.03 (s, 2H), 1.76-1.65 (m, 1H), 1.45 (s, 9H), 1.22 (d, J = 6.3 Hz, 3H). |

TABLE 15-continued

Characterization data for intermediates prepared according to above.

| Intermediate | Structure | Chemical Name | MS: [(M + 1)]$^+$ | $^1$H-NMR |
|---|---|---|---|---|
| B-4-11 | 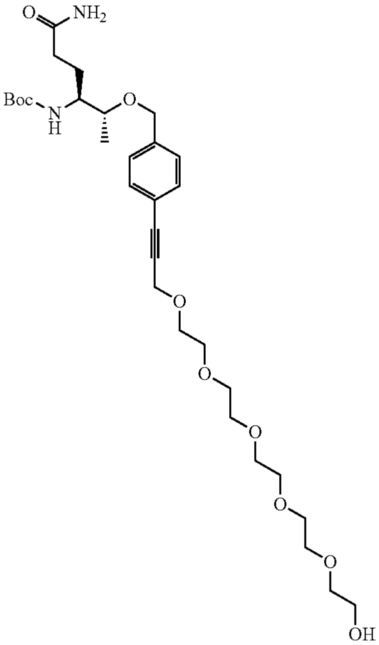 [SMILES: C[C@@H](OCc1ccc(C#CCOCCOCCOCCOCCOCCO)cc1)[C@H](CCC(N)=O)NC(=O)OC(C)(C)C] | tert-butyl N-[(3S,4R)-1-carbamoyl-4-[[4-(1-hydroxy-3,6,9,12,15-pentaoxaoctadec-17-yn-18-yl)phenyl]methoxy]pentan-3-yl]carbamate | 611.3 | (400 MHz, $CDCl_3$) δ 7.45-7.41 (m, 2H), 7.29 (s, 1H), 7.27 (s, 1H), 6.40 (s, 1H), 5.50 (s, 1H), 4.86 (d, J = 9.7 Hz, 1H), 4.60 (d, J = 12.0 Hz, 1H), 4.44 (d, J = 3.5 Hz, 2H), 3.81-3.77 (m, 2H), 3.76-3.73 (m, 4H), 3.71-3.68 (m, 14H), 3.63 (t, J = 4.5 Hz, 3H), 2.30 (q, J = 6.1, 5.0 Hz, 3H), 2.02-1.98 (m, 1H), 1.71 (dt, J = 13.8, 6.2 Hz, 1H), 1.46 (s, 9H), 1.22 (d, J = 6.3 Hz, 3H). |
| B-4-12 | 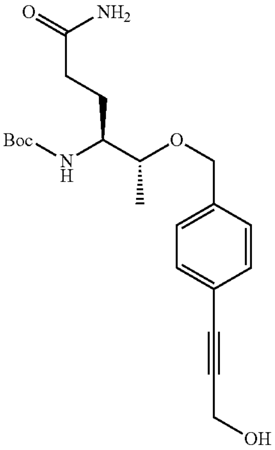 [SMILES: C[C@@H](OCc1ccc(C#CCO)cc1)[C@H](CCC(N)=O)NC(=O)OC(C)(C)C] | tert-butyl N-[(3S,4R)-1-carbamoyl-4-[[4-(3-hydroxyprop-1-yn-1-yl)phenyl]methoxy]pentan-3-yl]carbamate | [(M + Na)]$^+$ = 413.3 | (400 MHz, DMSO-$d_6$) δ 7.40-7.31 (m, 4H), 7.22 (s, 1H), 6.71-6.61 (m, 2H), 5.32 (t, J = 6.0 Hz, 1H), 4.55-4.44 (m, 2H), 4.30 (d, J = 6.0 Hz, 2H), 3.42 (dd, J = 14.0, 7.9 Hz, 2H), 2.03 (tq, J = 14.8, 8.2, 6.7 Hz, 2H), 1.83-1.43 (m, 2H), 1.38 (s, 9H), 1.07 (d, J = 6.0 Hz, 3H). |

TABLE 15-continued

| Characterization data for intermediates prepared according to above. | | | | |
|---|---|---|---|---|
| Inter-mediate | Structure | Chemical Name | MS: $[(M+1)]^+$ | $^1$H-NMR |
| B-4-13 | 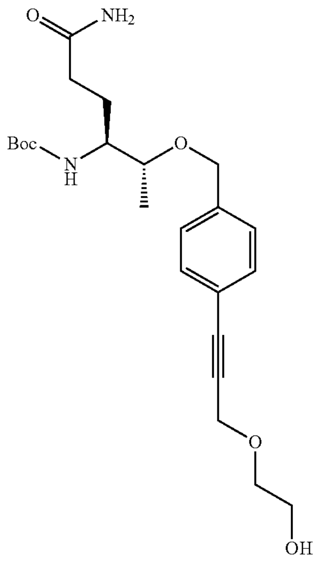 [SMILES: C[C@@H](OCc1ccc(C#CCOCCO)cc1)[C@H](CCC(N)=O)NC(=O)OC(C)(C)C] | tert-butyl N-[(3S,4R)-1-carbamoyl-4-([4-[3-(2-hydroxyethoxy)prop-1-yn-1-yl]phenyl]methoxy)pentan-3-yl]carbamate | 435.4 | (400 MHz, $CDCl_3$) δ 7.44 (d, J = 7.9 Hz, 2H), 7.29 (s, 2H), 6.36 (s, 1H), 5.46 (s, 1H), 4.85 (d, J = 9.7 Hz, 1H), 4.60 (d, J = 12.0 Hz, 1H), 4.45 (d, J = 4.1 Hz, 2H), 3.82 (d, J = 5.5 Hz, 2H), 3.74 (dd, J = 5.1, 3.8 Hz, 2H), 3.70-3.58 (m, 2H), 2.30 (s, 2H), 1.99 (d, J = 6.7 Hz, 2H), 1.45 (s, 9H, 1.21 (d, J = 6.3 Hz, 3H). |
| B-4-14 | 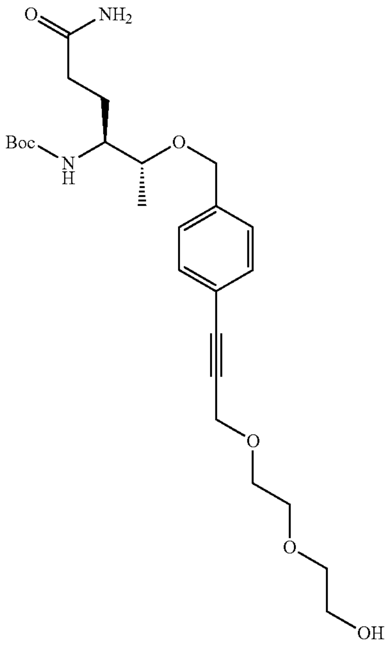 [SMILES: C[C@@H](OCc1ccc(C#CCOCCOCCO)cc1)[C@H](CCC(N)=O)NC(=O)OC(C)(C)C] | tert-butyl N-[(3S,4R)-1-carbamoyl-4-[(4-[3-[2-(2-hydroxyethoxy)ethoxy]prop-1-yn-1-yl]phenyl)methoxy]pentan-3-yl]carbamate | 479.3 | (400 MHz, DMSO-$d_6$) δ 7.41 (d, J = 8.1 Hz, 2H), 7.34 (d, J = 8.0 Hz, 2H), 7.21 (s, 1H), 6.68 (s, 1H), 6.63 (d, J = 9.0 Hz, 1H), 4.58 (t, J = 5.5 Hz, 1H), 4.55-4.44 (m, 2H), 4.40 (s, 2H), 3.64 (dd, J = 5.9, 3.5 Hz, 2H), 3.58 (dd, J = 6.2, 3.5 Hz, 2H), 3.54-3.38 (m, 5H), 3.31 (s, 1H), 2.08 (s, 2H), 1.50 (dd, J = 14.2, 9.2 Hz, 1H), 1.38 (s, 9H), 1.07 (d, J = 6.1 Hz, 3H). |

TABLE 15-continued

| Characterization data for intermediates prepared according to above. | | | | |
|---|---|---|---|---|
| Inter-mediate | Structure | Chemical Name | MS: [(M + 1)]+ | $^1$H-NMR |
| B-4-15 | 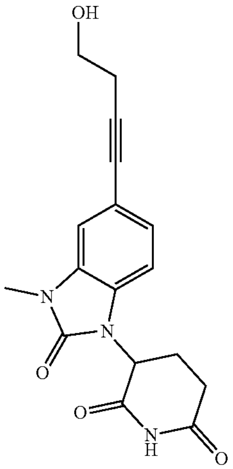 [SMILES: Cn1c(=O)n(C2CCC(=O)NC2=O)c2ccc(C#CCCO)cc21] | 3-[5-(4-hydroxypentbut-1-yn-1-yl)-3-methyl-2-oxo-1,3-benzodiazol-1-yl]piperidine-2,6-dione | 328.2 | (400 MHz, DMSO-$d_6$) δ 11.11 (s, 1H), 7.25 (d, J = 1.3 Hz, 1H), 7.10 (d, J = 1.1 Hz, 2H), 5.38 (dd, J = 12.8, 5.3 Hz, 1H), 4.88 (s, 1H), 3.60 (d, J = 7.7 Hz, 2H), 3.34 (s, 3H), 2.95-2.83 (m, 1H), 2.75-2.59 (m, 2H), 2.55 (t, J = 3.5 Hz, 2H), 2.03 (ddd, J = 10.2, 5.9, 3.7 Hz, 1H). |
| B-4-16 | 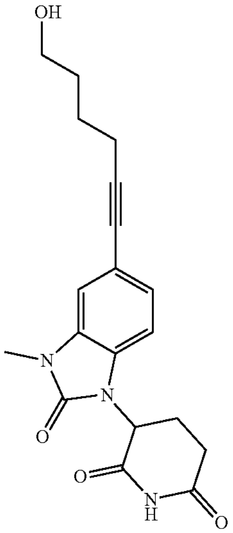 [SMILES: Cn1c(=O)n(C2CCC(=O)NC2=O)c2ccc(C#CCCCCO)cc21] | 3-[5-(6-hydroxyhex-1-yn-1-yl)-3-methyl-2-oxo-1,3-benzodiazol-1-yl]piperidine-2,6-dione | 356.2 | (400 MHz, DMSO-$d_6$) δ 11.11 (s, 1H), 7.24 (s, 1H), 7.09 (s, 2H), 5.38 (dd, J = 12.8, 5.4 Hz, 1H), 4.43 (s, 1H), 3.46 (d, J = 5.5 Hz, 2H), 3.34 (s, 3H), 2.97-2.83 (m, 1H), 2.77-2.58 (m, 2H), 2.47-2.39 (m, 2H), 2.07-1.97 (m, 1H), 1.64-1.54 (m, 4H). |

TABLE 15-continued

| Characterization data for intermediates prepared according to above. | | | | |
|---|---|---|---|---|
| Inter-mediate | Structure | Chemical Name | MS: $[(M + 1)]^+$ | $^1H$-NMR |
| B-4-17 | 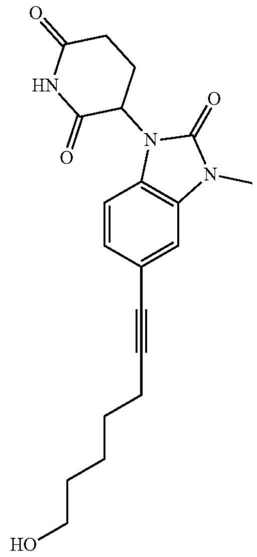 [SMILES: Cn1c(=O)n(C2CCC(=O)NC2=O)c2ccc(C#CCCCCCO)cc21] | 3-[5-(7-hydroxyhept-1-yn-1-yl)-3-methyl-2-oxo-1,3-benzodiazol-1-yl]piperidine-2,6-dione | 370.30 | (400 MHz, $CDCl_3$) δ 8.31 (s, 1H), 7.15 (dd, J = 8.1, 1.5 Hz, 1H), 7.08 (d, J = 1.4 Hz, 1H), 6.73 (d, J = 8.1 Hz, 1H), 5.20 (dd, J = 12.7, 5.4 Hz, 1H), 3.70 (t, J = 6.5 Hz, 2H), 3.43 (s, 3H), 3.02-2.90 (m, 1H), 2.85-2.73 (m, 2H), 2.45 (t, J = 7.0 Hz, 2H), 2.3-2.19 (m, 1H), 1.79-1.49 (m, 6H). |

Step 4. Tert-butyl N-r(3S,4R)-1-Carbamoyl-4-([4-[3-(2-[3-[1-(2,6-dioxopiperidin-3-yl)-3-methyl-2-oxo-1.3-benzodiazol-5-yl]propoxy]ethoxy)propyl]phenyl]methoxy)pentan-3-yl]carbamate (Intermediate B). To a solution of tert-butyl N-[(3S,4R)-1-carbamoyl-4-[(4-[3-[2-(113-Ill-(2,6-dioxopiperidin-3-yl)-3-methyl-2-oxo-1,3-benzodiazol-5-yl] prop-2-yn-11-yl]oxy)ethoxy]prop-1-yn-1-yl]phenyl) methoxy]pentan-3-yl]carbamate (490 mg, 0.67 minol) in THF (20 mL) was added palladium on charcoal (400 mg, 1000 w/w) at room temperature under nitrogen atmosphere. The resulting mixture was purged with hydrogen for 3 times and stirred for 4 hours at room temperature under hydrogen atmosphere (2 atm.). The reaction mixture was filtered through a celite pad. The filtrate was concentrated under reduced pressure to afford the title compound as a dark brown solid (410 mg, 83%): $^1H$ NMR (400 MHz, DMSO-$d_6$) δ 11.07 (d, J=10.8 Hz, 1H), 7.76-7.61 (in, 1H), 7.37-7.26 (in, 1H), 7.19-7.14 (m, 4H), 7.06-6.93 (m, 2H), 6.86 (d, J=12.5 Hz, 2H), 6.72-6.56 (in, 2H), 5.34 (dd, J=12.7, 5.4 Hz, 1H), 4.53-4.33 (m, 2H), 4.21 (dt, J=13.6, 6.7 Hz, 1H), 3.66-3.33 (m, 12H), 2.89 (d, J=12.6 Hz, 1H), 2.73-2.54 (m, 5H), 2.47 (s, 1H), 2.17 (d, J=13.3 Hz, 1H), 2.02-1.97 (m, 3H), 1.88-1.69 (m, 9H), 1.64 (dd, J=14.5, 7.0 Hz, 1H), 1.05 (dt, J=11.3, 6.4 Hz, 3H), 0.91-0.82 (in, 2H).; MS (ESI, m/z): $[1(M-1)]^+$=736.40.

The intermediates in Table 16 below were prepared according to Step 4 of the procedure to prepare Intermediate B.

TABLE 16

Characterization data for intermediates prepared according to above.

| Intermediate | Structure | Chemical Name | MS: [(M + 1)]+ | 1H-NMR |
|---|---|---|---|---|
| B1 | 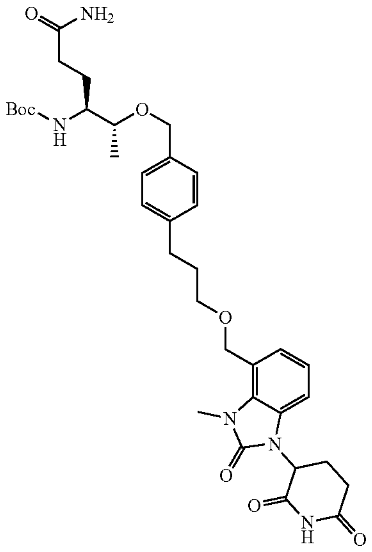 [SMILES: C[C@@H](OCc1ccc(CCCOCc2cccc3c2n(C)c(=O)n3C2CCC(=O)NC2=O)cc1)[C@H](CCC(N)=O)NC(=O)OC(C)(C)C] | tert-butyl N-[(3S,4R)-1-carbamoyl-4-[[4-(3-[[1-(2,6-dioxopiperidin-3-yl)-3-methyl-2-oxo-1,3-benzodiazol-4-yl]methoxy]propyl)phenyl]methoxy]pentan-3-yl]carbamate | 666.4 | (400 MHz, DMSO-$d_6$) δ 11.04 (s, 1H), 7.18-6.94 (m, 7H), 6.61-6.54 (m, 2H), 5.34 (s, 1H), 4.63 (s, 2H), 4.36 (s, 2H), 3.38-3.35 (m, 3H), 3.53 (s, 3H), 3.26 (s, 2H), 2.84 (s, 1H), 2.74-2.66 (m, 5H), 2.02-1.95 (m, 3H), 1.77 (s, 3H), 1.39-1.28 (m, 9H), 1.00 (s, 3H). |
| B2 | 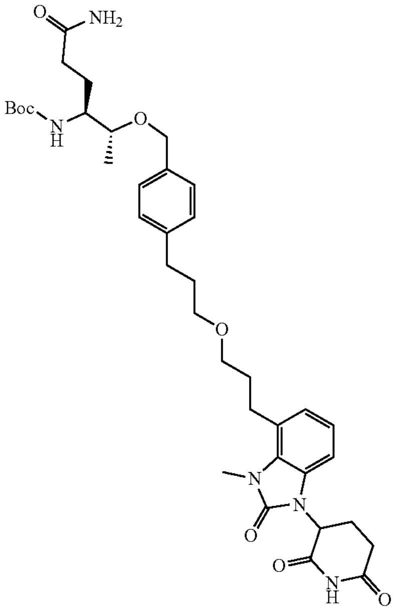 [SMILES: C[C@@H](OCc1ccc(CCCOCCCc2cccc3c2n(C)c(=O)n3C2CCC(=O)NC2=O)cc1)[C@H](CCC(N)=O)NC(=O)OC(C)(C)C] | tert-butyl N-[(3S,4R)-1-carbamoyl-4-[[4-(3-[3-[1-(2,6-dioxopiperidin-3-yl)-3-methyl-2-oxo-1,3-benzodiazol-4-yl]propoxy]propyl)phenyl]methoxy]pentan-3-yl]carbamate | 694.5 | (400 MHz, DMSO-$d_6$) δ 11.08 (s, 1H), 7.24 (d, J = 7.9 Hz, 2H), 7.20 (s, 1H), 7.15 (d, J = 7.7 Hz, 2H), 6.96 (dd, J = 5.1, 3.3 Hz, 2H), 6.87 (dd, J = 5.3, 3.7 Hz, 1H), 6.69-6.64 (m, 1H), 6.60 (d, J = 9.0 Hz, 1H), 5.36 (dd, J = 12.6, 5.3 Hz, 1H), 4.49-4.37 (m, 2H), 3.59-3.56 (m, 3H), 3.44-3.37 (m, 4H), 3.01-2.93 (m, 2H), 2.92-2.82 (m, 1H), 2.77-2.58 (m, 4H), 2.09-2.06 (m, 3H), 1.98 (d, J = 14.4 Hz, 1H), 1.92-1.75 (m, 5H), 1.45 (s, 2H), 1.41-1.35 (m, 9H), 1.06 (d, J = 5.8 Hz, 3H). |

TABLE 16-continued

| Characterization data for intermediates prepared according to above. | | | | |
|---|---|---|---|---|
| Intermediate | Structure | Chemical Name | MS: $[(M + 1)]^+$ | $^1$H-NMR |
| B3 | 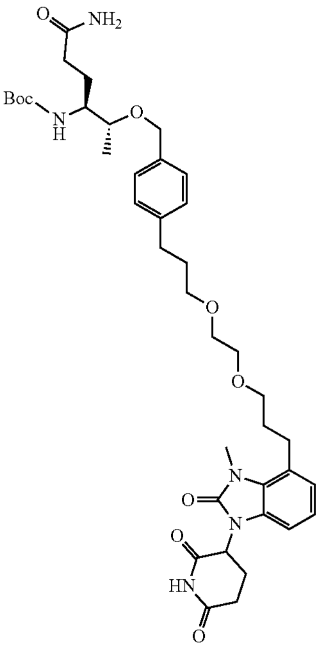 [SMILES: C[C@@H](OCc1ccc(CCCOCCOCCCc2cccc3c2n(C)c(=O)n3C2CCC(=O)NC2=O)cc1)[C@H](CCC(N)=O)NC(=O)OC(C)(C)C] | tert-butyl N-[(3S,4R)-1-carbamoyl-4-([4-[3-(2-[3-[1-(2,6-dioxopiperidin-3-yl)-3-methyl-2-oxo-1,3-benzodiazol-4-yl]propoxy]ethoxy)propyl]phenyl]methoxy)pentan-3-yl]carbamate | 738.5 | (400 MHz, $CD_3OD$) δ 7.26 (d, J = 7.8 Hz, 2H), 7.18 (d, J = 7.8 Hz, 2H), 7.03 (q, J = 7.5, 6.9 Hz, 1H), 6.98 (d, J = 7.3 Hz, 2H), 6.40 (d, J = 9.5 Hz, 1H), 5.33 (dd, J = 12.2, 5.6 Hz, 1H), 4.53 (d, J = 11.4 Hz, 1H), 4.45 (d, J = 11.5 Hz, 1H), 3.67 (s, 3H), 3.59 (s, 1H), 3.63-3.45 (m, 10H), 3.07 (q, J = 8.0 Hz, 2H), 2.97-2.84 (m, 1H), 2.87-2.77 (m, 2H), 2.70 (t, J = 7.6 Hz, 2H), 2.30-2.20 (m, 1H), 2.15 (dt, J = 10.8, 6.4 Hz, 1H), 1.96 (t, J = 6.4 Hz, 1H), 1.92-1.84 (4H), 1.60 (s, 1H), 1.45 (s, 8H), 1.17 (d, J = 6.2 Hz, 3H). |
| B4 | 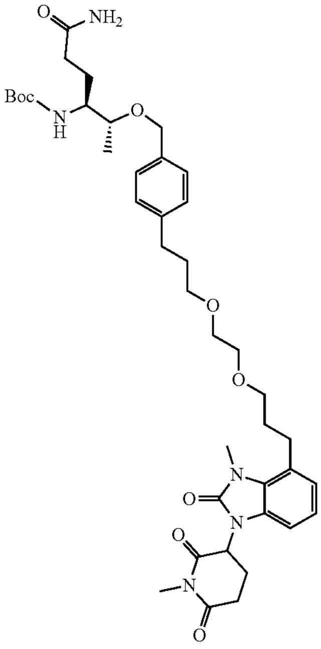 | tert-butyl N-[(3S,4R)-1-carbamoyl-4-([4-[3-(2-[3-[3-methyl-1-(1-methyl-2,6-dioxopiperidin-3-yl)-2-oxo-1,3-benzodiazol-4-yl]propoxy]ethoxy)propyl]phenyl]methoxy)pentan-3-yl]carbamate | 752.6 | (400 MHz, DMSO-$d_6$) 7.31 (q, J = 7.0, 5.7 Hz, 1H), 7.22-7.14 (m, 4H), 6.99-6.85 (m, 3H), 6.66 (s, 1H), 6.63-6.54 (m, 1H), 5.46-5.38 (m, 1H), 4.41 (s, 2H), 3.59-3.49 (m, 3H), 3.52-3.36 (m, 6H), 3.32 (s, 1H), 3.03 (d, J = 7.4 Hz, 2H), 2.99-2.91 (m, 3H), 2.74 (s, 1H), 2.60 (q, J = 7.9 Hz, 1H), 2.18 (d, J = 8.3 Hz, 1H), 2.01 (s, 3H), 1.83 (d, J = 7.1 Hz, 1H), 1.80 (s, 3H), 1.77 (t, J = 7.3 Hz, 2H), 1.46 (s, 1H), 1.39-1.32 (m, 13H), 1.04 (t, J = 6.5 Hz, 3H). |

TABLE 16-continued

Characterization data for intermediates prepared according to above.

| Intermediate | Structure | Chemical Name | MS: $[(M + 1)]^+$ | $^1$H-NMR |
|---|---|---|---|---|
| B5 | 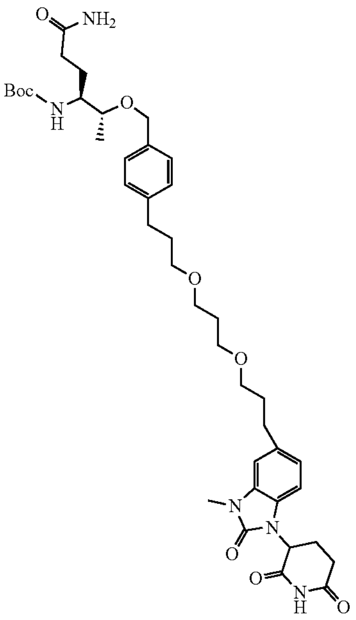 [SMILES: C[C@@H](OCc1ccc(CCCOCCCOCCCc2ccc3c(c2)n(C)c(=O)n3C2CCC(=O)NC2=O)cc1)[C@H](CCC(N)=O)NC(=O)OC(C)(C)C] | tert-butyl N-[(3S,4R)-1-carbamoyl-4-([4-[3-(3-[3-[1-(2,6-dioxopiperidin-3-yl)-3-methyl-2-oxo-1,3-benzodiazol-5-yl]propoxy]propoxy)propyl]phenyl]methoxy)pentan-3-yl]carbamate | 752.5 | (400 MHz, $CDCl_3$) δ 8.73 (s, 1H), 7.24 (d, J = 7.8 Hz, 2H), 7.17 (d, J = 7.7 Hz, 2H), 6.94-6.86 (m, 2H), 6.73 (d, J = 8.0 Hz, 1H), 5.23 (dd, J = 12.7, 5.3 Hz, 1H), 4.92 (d, J = 9.7 Hz, 1H), 4.58 (d, J = 11.5 Hz, 1H), 4.39 (dd, J = 11.4, 2.0 Hz, 1H), 3.68 (s, 1H), 3.64-3.58 (m, 1H), 3.56-3.51 (m, 5H), 3.48-3.37 (m, 7H), 2.92 (s, 1H), 2.86 (dd, J = 13.1, 5.1 Hz, 1H), 2.74-2.62 (m, 5H), 2.32-2.21 (m, 3H), 1.95-1.87 (m, 6H), 1.76-1.65 (m, 1H), 1.45 (s, 9H), 1.28 (s, 1H), 1.21 (dd, J = 6.3, 1.4 Hz, 3H). |
| B6 | 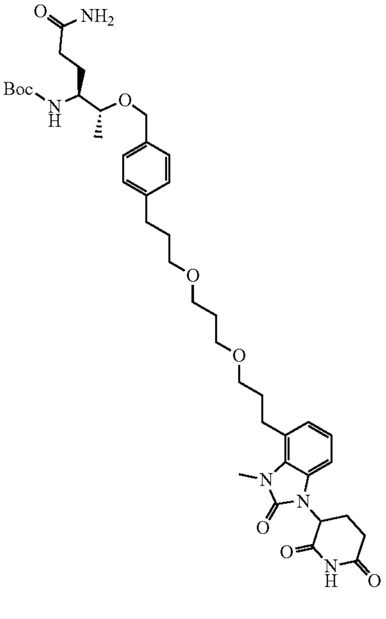 [SMILES: C[C@@H](OCc1ccc(CCCOCCCOCCCc2cccc3c2n(C)c(=O)n3C2CCC(=O)NC2=O)cc1)[C@H](CCC(N)=O)NC(=O)OC(C)(C)C] | tert-butyl N-[(3S,4R)-1-carbamoyl-4-([4-[3-(3 -[3-[1 -(2,6-dioxopiperidin-3-yl)-3-methyl-2-oxo-1,3-benzodiazol-4-yl]propoxy]propoxy)propyl]phenyl]methoxy)pentan-3-yl]carbamate | 752.5 | (400 MHz, $CD_3OD$) δ 7.7.24-7.13 (m, 4H), 6.97 (s, 3H), 5.33 (s, 1H), 4.53-4.48 (m, 2H), 3.67 (s, 3H), 3.52 (s, 6H), 3.44 (s, 3H), 3.07 (s, 3H), 2.82 (s, 2H), 2.68 (s, 2H), 2.24 (s, 3H), 1.87 (s, 8H), 1.60 (s, 1H), 1.44 (s, 9H), 1.16 (s, 3H). |

TABLE 16-continued

| Characterization data for intermediates prepared according to above. | | | | |
|---|---|---|---|---|
| Intermediate | Structure | Chemical Name | MS: [(M + 1)]+ | $^1$H-NMR |
| B7 | 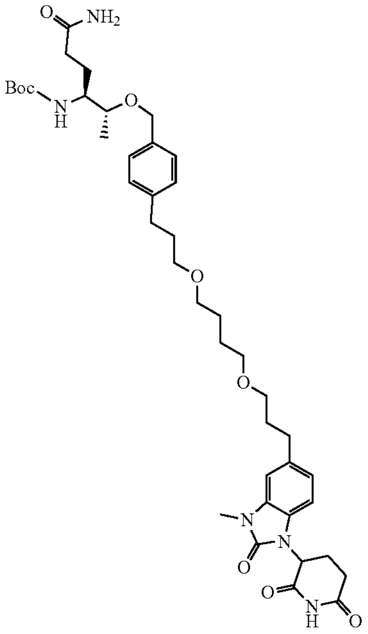 [SMILES: C[C@@H](OCc1ccc(CCCOCCCCOCCCc2ccc3c(c2)n(C)c(=O)n3C2CCC(=O)NC2=O)cc1)[C@H](CCC(N)=O)NC(=O)OC(C)(C)C] | tert-butyl N-[(3S,4R)-1-carbamoyl-4-([4-[3-(4-[3-[1-(2,6-dioxopiperidin-3-yl)-3-methyl-2-oxo-1,3-benzodiazol-5-yl]propoxy]butoxy)propyl]phenyl]methoxy)pentan-3-yl]carbamate | 766.5 | (400 MHz, DMSO-$d_6$) δ 11.08 (s, 1H), 7.25-7.19 (m, 2H), 7.14 (d, J = 7.8 Hz, 1H), 7.08-6.98 (m, 2H), 6.87 (dd, J = 8.0, 1.5 Hz, 1H), 6.71-6.56 (m, 1H), 5.34 (dd, J = 12.7, 5.3 Hz, 1H), 4.47-4.39 (m, 1H), 3.63-3.59 (m, 6H), 3.38-3.35 (m, 6H), 2.97-2.84 (m, 1H), 2.77-2.55 (m, 5H), 2.14-1.94 (m, 3H), 1.87-1.72 (m, 12H), 1.63-1.50 (m, 4H), 1.39-1.35 (m, 9H), 1.03 (dd, J = 18.7, 6.2 Hz, 3H). |
| B8 | 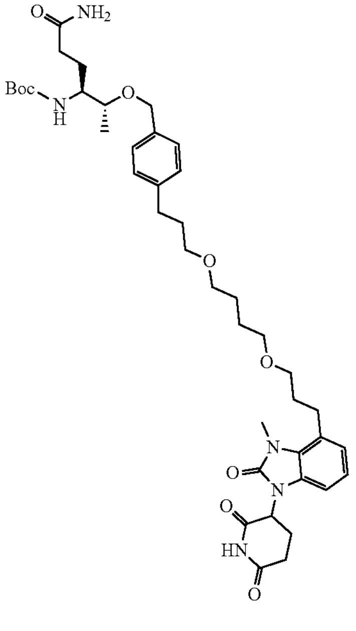 [SMILES: C[C@@H](OCc1ccc(CCCOCCCCOCCCc2cccc3c2n(C)c(=O)n3C2CCC(=O)NC2=O)cc1)[C@H](CCC(N)=O)NC(=O)OC(C)(C)C] | tert-butyl N-[(3S,4R)-1-carbamoyl-4-([4-[3-(4-[3-[1-(2,6-dioxopiperidin-3-yl)-3-methyl-2-oxo-1,3-benzodiazol-4-yl]propoxy]butoxy)propyl]phenyl]methoxy)pentan-3-yl]carbamate | 766.5 | (400 MHz, DMSO-$d_6$) δ 11.09 (s, 1H), 7.25-7.21 (m, 3H), 7.14 (d, J = 7.8 Hz, 2H), 6.99-6.92 (m, 2H), 6.90-6.83 (m, 1H), 6.68 (s, 1H), 6.66-6.57 (m, 1H), 5.37 (dd, J = 12.5, 5.4 Hz, 1H), 4.48-4.37 (m, 2H), 3.47-3.30 (m, 10H), 3.00-2.92 (m, 2H), 2.92-2.83 (m, 1H), 2.72 (td, J = 12.8, 4.3 Hz, 1H), 2.63 (d, J = 10.4 Hz, 1H), 2.59 (d, J = 7.7 Hz, 2H), 2.19 (s, 1H), 2.02 (tdd, J = 15.7 , 10.0, 5.4 Hz, 2H), 1.82-1.74 (m, 6H), 1.59-1.52 (m, 4H), 1.40-1.33 (m, 12H), 1.05 (d, J = 6.1 Hz, 3H). |

TABLE 16-continued

| Intermediate | Structure | Chemical Name | MS: [(M + 1)]+ | $^1$H-NMR |
|---|---|---|---|---|
| Characterization data for intermediates prepared according to above. | | | | |
| B9 | 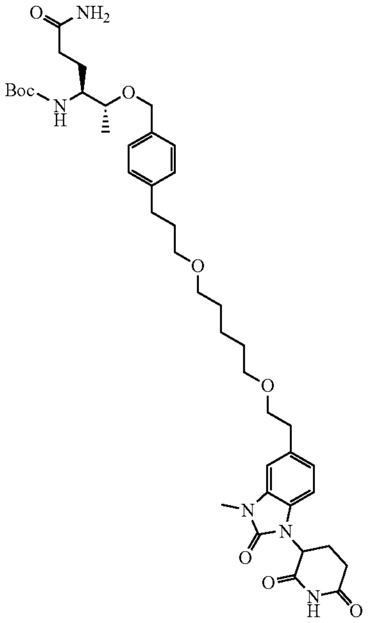 [SMILES: C[C@@H](OCc1ccc(CCCOCCCCCOCCc2ccc3c(c2)n(C)c(=O)n3C2CCC(=O)NC2=O)cc1)[C@H](CCC(N)=O)NC(=O)OC(C)(C)C] | tert-butyl N-[(3S,4R)-1-carbamoyl-4-[(4-[3-[(5-[3-[1-(2,6-dioxopiperidin-3-yl)-3-methyl-2-oxo-1,3-benzodiazol-5-yl]propoxy]pentyl)oxy]propyl]phenyl)methoxy]pentan-3-yl]carbamate | 780.7 | (400 MHz, $CD_3OD$) δ 7.26 (d, J = 7.7 Hz, 2H), 7.15 (d, J = 7.7 Hz, 2H), 7.06-6.93 (m, 3H), 5.31 (dd, J = 12.4, 5.3 Hz, 1H), 4.54 (d, J = 11.4 Hz, 1H), 4.47 (d, J = 11.6 Hz, 1H), 3.58 (s, 1H), 3.49-3.39 (m, 11H), 2.96-2.86 (m, 1H), 2.81-2.76 (m, 4H), 2.67 (t, J = 7.7 Hz, 2H), 2.25 (q, J = 9.2 Hz, 1H), 2.17 (s, 1H), 1.92-1.85 (m, 4H), 1.64-1.61 (m, 6H), 1.50 (d, J = 6.8 Hz, 1H), 1.45 (s, 11H), 1.31 (s, 1H), 1.16 (d, J = 6.2 Hz, 3H). |
| B10 | 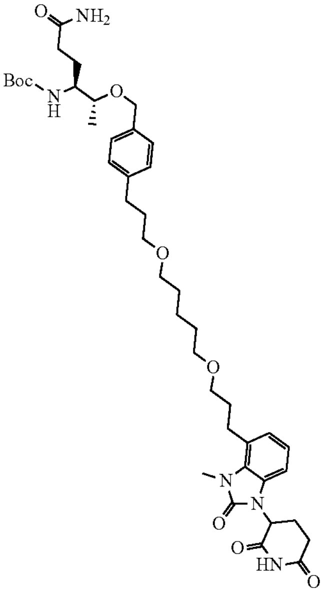 [SMILES: C[C@@H](OCc1ccc(CCCOCCCCCOCCCc2cccc3c2n(C)c(=O)n3C2CCC(=O)NC2=O)cc1)[C@H](CCC(N)=O)NC(=O)OC(C)(C)C] | tert-butyl N-[(3S,4R)-1-carbamoyl-4-[(4-[3-[(5-[3-[1-(2,6-dioxopiperidin-3-yl)-3-methyl-2-oxo-1,3-benzodiazol-4-yl]propoxy]pentyl)oxy]propyl]phenyl)methoxy]pentan-3-yl]carbamate | 780.7 | (400 MHz, $CD_3OD$) δ 7.25 (d, J = 7.9 Hz, 2H), 7.15 (d, J = 7.8 Hz, 2H), 7.08-7.00 (m, 1H), 6.97 (t, J = 7.2 Hz, 2H), 6.40 (d, J = 9.4 Hz, 1H), 5.33 (dd, J = 12.2, 5.5 Hz, 1H), 4.53 (d, J = 11.4 Hz, 1H), 4.46 (d, J = 11.5 Hz, 1H), 3.70-3.66 (m, 3H), 3.58 (s, 1H), 3.55-3.39 (m, 8H), 3.08 (dd, J = 8.9, 6.7 Hz, 2H), 3.01-2.87 (m, 1H), 2.85-2.77 (m, 2H), 2.68 (dd, J = 8.4, 6.8 Hz, 2H), 2.31-2.10 (m, 2H), 1.93 (s, 3H), 1.99-1.81 (m, 2H), 1.63 (s, 6H), 1.51 (d, J = 6.8 Hz, 1H), 1.45 (s, 9H), 1.17 (d, J = 6.2 Hz, 3H). |

TABLE 16-continued

| Characterization data for intermediates prepared according to above. | | | | |
|---|---|---|---|---|
| Intermediate | Structure | Chemical Name | MS: $[(M + 1)]^+$ | $^1$H-NMR |
| B11 | 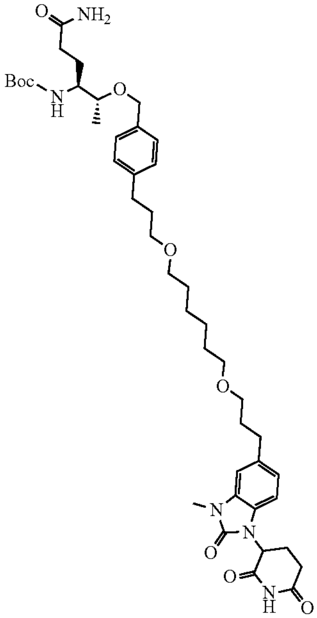 [SMILES: C[C@@H](OCc1ccc(CCCOCCCCCCOCCCc2ccc3c(c2)n(C)c(=O)n3C2CCC(=O)NC2=O)cc1)[C@H](CCC(N)=O)NC(=O)OC(C)(C)C] | tert-butyl N-[(3S,4R)-1-carbamoyl-4-[(4-[3-[(6-[3-[1-[2,6-dioxopiperidin-3-yl)-3-methyl-2-oxo-1,3-benzodiazol-5-yl]propoxy]hex-yl)oxy]pro-pyl]phenyl)meth-oxy]pentan-3-yl]carbamate | 794.5 | (400 MHz, $CDCl_3$) δ 8.43 (s, 1H), 7.27-7.24 (m, 3H), 7.18 (d, J = 7.8 Hz, 2H), 6.94-6.86 (m, 3H), 6.73 (d, J = 8.0 Hz, 1H), 5.93 (s, 1H), 5.23 (dd, J = 12.5, 5.2 Hz, 1H), 4.93 (d, J = 9.4 Hz, 1H), 4.59 (d, J = 11.4 Hz, 1H), 4.39 (d, J = 11.4 Hz, 1H), 3.63 (s, 2H), 3.45-3.42 (m, 8H), 2.94 (s, 1H), 2.76-2.67 (m, 6H), 2.36-2.21 (m, 4H), 1.92-1.86 (m, 7H), 1.46 (m, 17H), 1.22 (d, J = 6.1 Hz, 3H). |
| B12 | 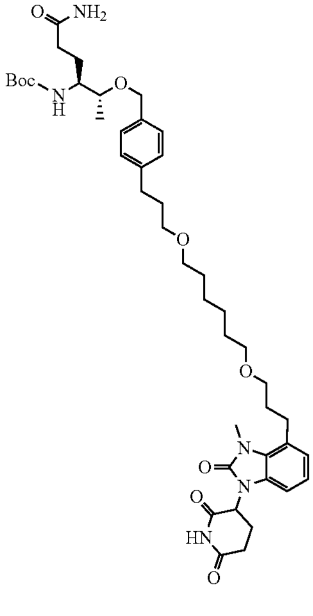 [SMILES: C[C@@H](OCc1ccc(CCCOCCCCCCOCCCc2cccc3c2n(C)c(=O)n3C2CCC(=O)NC2=O)cc1)[C@H](CCC(N)=O)NC(=O)OC(C)(C)C] | tert-butyl N-[(3S,4R)-1-carbamoyl-4-[(4-[3-[(6-[3-[1-[2,6-dioxopiperidin-3-yl)-3-methyl-2-oxo-1,3-benzodiazol-4-yl]propoxy]hex-yl)oxy]propyl]phen-yl)methoxy]pentan-3-yl]carbamate | 794.7 | (400 MHz, DMSO-$d_6$) δ 11.09 (s, 1H), 7.25-7.19 (m, 3H), 7.13 (d, J = 7.8 Hz, 2H), 7.00-6.93 (m, 2H), 6.88 (s, 1H), 6.63 (dd, J = 23.7, 11.5 Hz, 2H), 5.37 (dd, J = 12.6, 5.4 Hz, 1H), 4.48-4.37 (m, 2H), 3.64-3.57 (m, 4H), 3.44-3.36 (m, 7H), 3.00-2.84 (m, 3H), 2.77-2.57 (m, 4H), 2.11-1.96 (m, 3H), 1.83-1.76 (m, 6H), 1.53-1.49 (m, 5H), 1.39-1.34 (m, 14H), 1.06 (d, J = 6.0 Hz, 3H). |

TABLE 16-continued

| Characterization data for intermediates prepared according to above. | | | | |
|---|---|---|---|---|
| Intermediate | Structure | Chemical Name | MS: [(M + 1)]$^+$ | $^1$H-NMR |
| B13 | 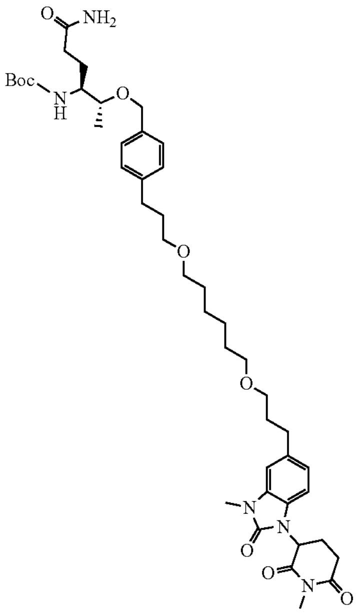 [SMILES: C[C@@H](OCc1ccc(CCCOCCCCCCOCCCc2ccc3c(c2)n(C)c(=O)n3C2CCC(=O)N(C)C2=O)cc1)[C@H](CCC(N)=O)NC(=O)OC(C)(C)C] | tert-butyl N-[(3S,4R)-1-carbamoyl-4-[(4-[3-[(6-[3-[3-methyl-1-(1-methyl-2,6-dioxopiperidin-3-yl)-2-oxo-1,3-benzodiazol-5-yl]propoxy]hexyl)oxy]propyl]phenyl)methoxy]pentan-3-yl]carbamate | 808.6 | (400 MHz, DMSO-$d_6$) δ 7.23 (d, J = 7.9 Hz, 2H), 7.14 (d, J = 7.8 Hz, 2H), 7.06-6.98 (m, 2H), 6.90-6.82 (m, 2H), 6.67 (s, 1H), 6.65-6.56 (m, 1H), 5.40 (dd, J = 13.0, 5.3 Hz, 1H), 4.48-4.37 (m, 2H), 3.43-3.29 (m, 12H), 3.04 (s, 3H), 2.96 (dd, J = 13.2, 5.0 Hz, 1H), 2.80 (s, 1H), 2.78-2.69 (m, 1H), 2.72-2.63 (m, 2H), 2.62-2.57 (m, 3H), 2.19 (s, 1H), 2.11-1.99 (m, 1H), 1.83-1.76 (m, 5H), 1.53 (d, J = 4.9 Hz, 1H), 1.50 (s, 4H), 1.40-1.36 (m, 14H), 1.34 (s, 3H), 1.06 (d, J = 6.0 Hz, 3H). |
| B14 | 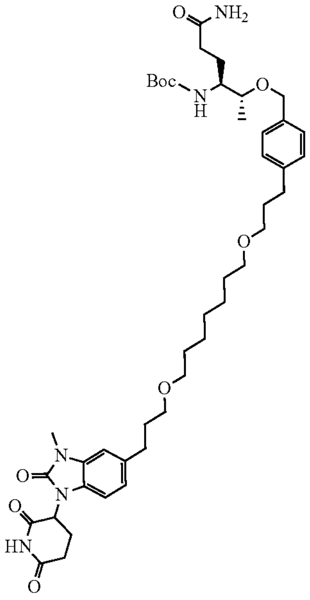 [SMILES: C[C@@H](OCc1ccc(CCCOCCCCCCCOCCCc2ccc3c(c2)n(C)c(=O)n3C2CCC(=O)NC2=O)cc1)[C@H](CCC(N)=O)NC(=O)OC(C)(C)C] | tert-butyl N-[(3S,4R)-1-carbamoyl-4-[(4-[3-[(7-[3-[1-(2,6-dioxopiperidin-3-yl)-3-methyl-2-oxo-1,3-benzodiazol-5-yl]propoxy]heptyl)oxy]propyl]phenyl)methoxy]pentan-3-yl]carbamate | 808.6 | (400 MHz, DMSO-$d_6$) δ 11.08 (s, 1H), 7.25-7.21 (m, 3H), 7.13 (d, J = 7.8 Hz, 2H), 7.05-6.97 (m, 2H), 6.89-6.84 (m, 1H), 6.68 (s, 1H), 6.60 (d, J = 9.2 Hz, 1H), 5.34 (dd, J = 12.6, 5.4 Hz, 1H), 4.48-4.38 (m, 2H), 3.49-3.33 (m, 8H), 2.96-2.85 (m, 1H), 2.76-2.56 (m, 6H), 2.07-1.98 (m, 3H), 1.87-1.72 (m, 6H), 1.57-1.42 (m, 6H), 1.41-1.26 (m, 18H), 1.06 (d, J = 6.0 Hz, 3H). |

TABLE 16-continued

| Intermediate | Structure | Chemical Name | MS: $[(M + 1)]^+$ | $^1$H-NMR |
|---|---|---|---|---|
| Characterization data for intermediates prepared according to above. | | | | |
| B15 | 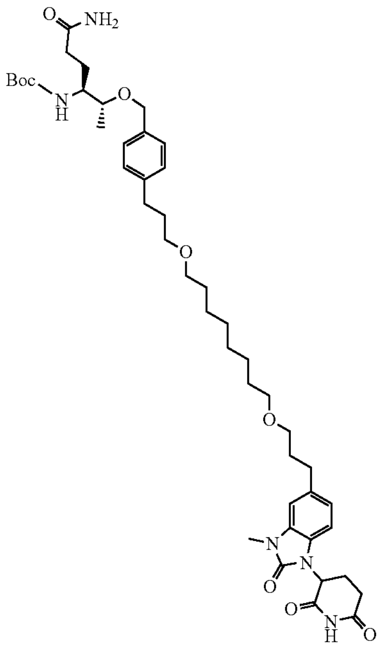 | tert-butyl N-[(3S,4R)-1-carbamoyl-4-[(4-[3-[(8-[3-[1-(2,6-dioxopiperidin-3-yl)-3-methyl-2-oxo-1,3-benzodiazol-5-yl]propoxy]octyl)oxy]propyl]phenyl)methoxy]pentan-3-yl]carbamate | 822.6 | (400 MHz, $CDCl_3$) δ 8.46 (d, J = 7.7 Hz, 1H), 7.25 (d, J = 7.9 Hz, 2H), 7.18 (d, J = 7.8 Hz, 1H), 7.00 (s, 1H), 6.95-6.87 (m, 1H), 6.73 (d, J = 8.0 Hz, 1H), 5.23 (dd, J = 12.6, 5.4 Hz, 1H), 4.92 (d, J = 9.6 Hz, 1H), 4.59 (d, J = 11.4 Hz, 1H), 4.39 (d, J = 11.4 Hz, 1H), 4.36-4.31 (m, 5H), 3.79-3.75 (m, 1H), 3.70-3.59 (m, 2H), 3.46-3.40 (m, 8H), 2.95 (d, J = 16.9 Hz, 1H), 2.89-2.79 (m, 1H), 2.75-2.70 (m, 4H), 2.33 (d, J = 15.8 Hz, 1H), 2.26 (dd, J = 7.9, 5.0 Hz, 1H), 1.93-1.87 (m, 4H), 1.81-1.69 (m, 10H), 1.62-1.57 (m, 4H), 1.46 (s, 10H), 1.36 (s, 3H). |
| B16 | 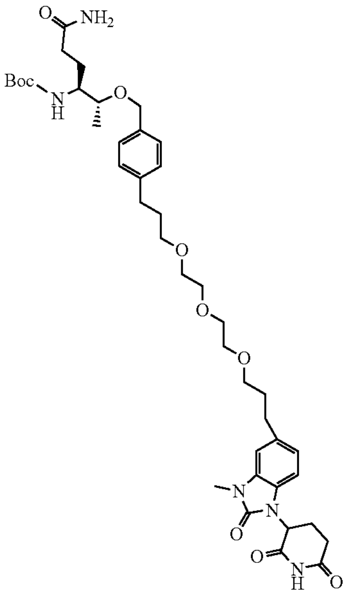 [SMILES: C[C@@H](OCc1ccc(CCCOCCOCCOCCCc2ccc3c(c2)n(C)c(=O)n3C2CCC(=O)NC2=O)cc1)[C@H](CCC(N)=O)NC(=O)OC(C)(C)C] | tert-butyl N-[(3S,4R)-1-carbamoyl-4-[(4-[3-[2-(2-[3-[1-(2,6-dioxopiperidin-3-yl)-3-methyl-2-oxo-2,3-dihydro-1H-1,3-benzodiazol-5-yl]propoxy]ethoxy)ethoxy]propyl]phenyl)methoxy]pentan-3-yl]carbamate | 782.5 | (400 MHz, DMSO-$d_6$) δ 11.08 (s, 1H), 7.22 (d, J = 7.7 Hz, 3H), 7.13 (d, J = 7.8 Hz, 2H), 7.04 (d, J = 1.4 Hz, 1H), 7.00 (d, J = 8.0 Hz, 1H), 6.87 (d, J = 8.3 Hz, 1H), 6.68 (s, 1H), 6.61 (d, J = 9.3 Hz, 1H), 5.34 (dd, J = 12.7, 5.4 Hz, 1H), 4.47-4.35 (m, 2H), 3.58-3.46 (m, 9H), 3.43-3.34 (m, 6H), 2.88 (d, J = 16.5 Hz, 1H), 2.70-2.62 (m, 3H), 2.59 (t, J = 7.6 Hz, 2H), 2.09-2.01 (m, 4H), 1.82-1.75 (m, 5H), 1.38 (s, 12H), 1.05 (d, J = 6.0 Hz, 3H). |

TABLE 16-continued

| Characterization data for intermediates prepared according to above. | | | | |
|---|---|---|---|---|
| Intermediate | Structure | Chemical Name | MS: $[(M + 1)]^+$ | $^1$H-NMR |
| B17 | 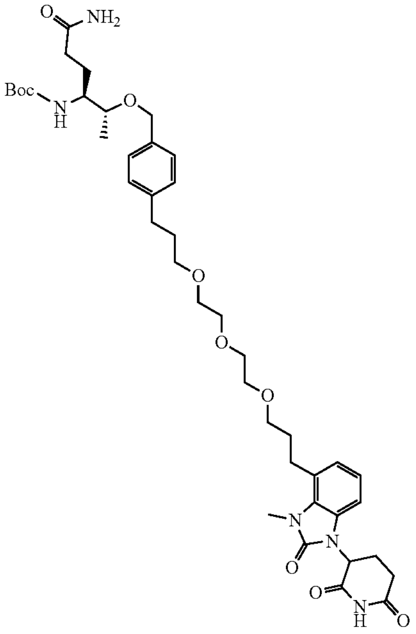 [SMILES: C[C@@H](OCc1ccc(CCCOCCOCCOCCCc2cccc3c2n(C)c(=O)n3C2CCC(=O)NC2=O)cc1)[C@H](CCC(N)=O)NC(=O)OC(C)(C)C] | tert-butyl N-[(3S,4R)-1-carbamoyl-4-[(4-[3-[2-[2-[3-[1-(2,6-dioxopiperidin-3-yl)-3-methyl-2-oxo-1,3-benzodiazol-4-yl]propoxy]ethoxy)ethoxy]propyl]phenyl)methoxy]pentan-3-yl]carbamate | 782.5 | (400 MHz, DMSO-$d_6$) δ 11.09 (s, 1H), 7.25-7.20 (m, 3H), 7.13 (d, J = 7.8 Hz, 2H), 7.00-6.92 (m, 2H), 6.87 (dd, J = 5.8, 3.0 Hz, 1H), 6.72-6.56 (m, 2H), 5.37 (dd, J = 12.5, 5.4 Hz, 1H), 4.50-4.36 (m, 2H), 3.58-3.42 (m, 14H), 3.39-3.36 (m, 3H), 3.02-2.83 (m, 3H), 2.78-2.54 (m, 4H), 2.08-2.01 (m, 3H), 1.88-1.72 (m, 5H), 1.39-1.35 (m, 10H), 1.05 (d, J = 6.0 Hz, 3H). |
| B18 | 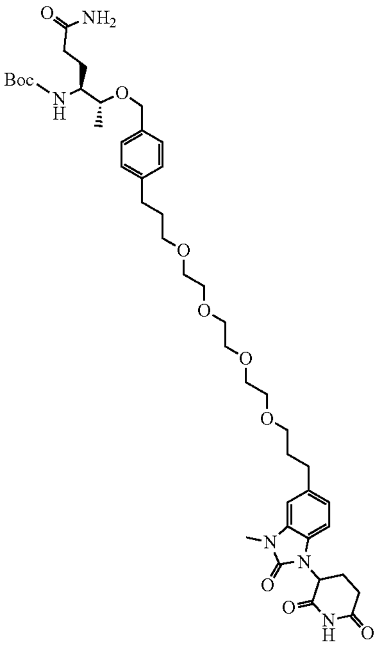 [SMILES: C[C@@H](OCc1ccc(CCCOCCOCCOCCOCCCc2ccc3c(c2)n(C)c(=O)n3C2CCC(=O)NC2=O)cc1)[C@H](CCC(N)=O)NC(=O)OC(C)(C)C] | tert-butyl N-[(3S,4R)-1-carbamoyl-4-[(4-[16-[1-(2,6-dioxopiperidin-3-yl)-3-methyl-2-oxo-2,3-dihydro-1H-1,3-benzodiazol-5-yl]-4,7,10,13-tetraoxahexadecan-1-yl]phenyl)methoxy]pentan-3-yl]carbamate | 826.6 | (400 MHz, $CDCl_3$) δ 8.47-8.45 (m, 1H), 7.72-7.67 (m, 1H), 7.53 (d, J = 33.8 Hz, 1H), 7.24 (d, J = 7.7 Hz, 2H), 7.17 (d, J = 7.7 Hz, 2H), 6.95-6.86 (m, 2H), 6.73 (d, J = 8.0 Hz, 1H), 5.79 (s, 1H), 5.27-5.17 (m, 1H), 4.94-4.92 (m, 1H), 4.58 (d, J = 11.4 Hz, 1H), 4.38 (d, J = 11.5 Hz, 1H), 3.81-3.54 (m, 15H), 3.51-5.47 (m, 4H), 3.44 (s, 3H), 2.96 (d, J = 16.9 Hz, 1H), 2.86 (d, J = 14.4 Hz, 1H), 2.75-2.71 (m, 5H), 2.30-2.26 (m, 3H), 2.09-1.59 (m, 11H), 1.21 (d, J = 6.0 Hz, 3H). |

TABLE 16-continued

Characterization data for intermediates prepared according to above.

| Intermediate | Structure | Chemical Name | MS: $[(M + 1)]^+$ | $^1$H-NMR |
|---|---|---|---|---|
| B19 | 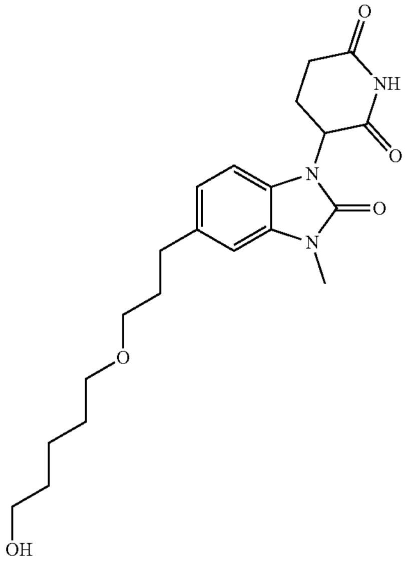 [SMILES: Cn1c(=O)n(C2CCC(=O)NC2=O)c2ccc(CCCOCCCCCO)cc21] | 3-(5-[3-[(5-hydroxy-pentyl)oxy]pro-pyl]-3-methyl-2-oxo-1,3-benzodiazol-1-yl)piperidine-2,6-dione | 404.2 | (400 MHz, DMSO-$d_6$) δ 11.09 (s, 1H), 7.07-6.97 (m, 2H), 6.87 (dd, J = 8.1, 1.6 Hz, 1H), 5.34 (dd, J = 12.7, 5.4 Hz, 1H), 4.35-4.33 (m, 1H), 3.43-3.34 (m, 9H), 2.90 (ddd, J = 17.0, 12.9, 5.2 Hz, 1H), 2.79-2.58 (m, 4H), 2.06-1.95 (m, 1H), 1.87-1.77 (m, 2H), 1.51 (dt, J = 14.0, 6.8 Hz, 2H), 1.46-1.39 (m, 2H), 1.38-1.30 (m, 2H). |
| B20 | 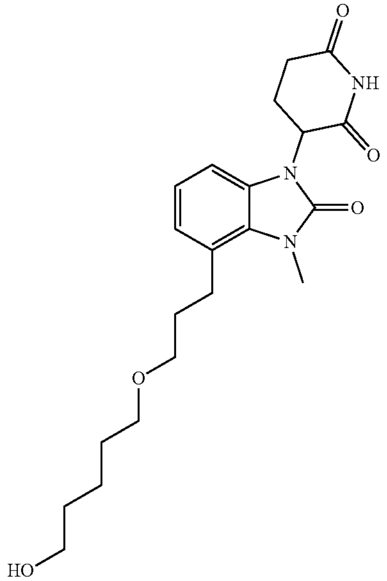 [SMILES: Cn1c(=O)n(C2CCC(=O)NC2=O)c2cccc(CCCOCCCCCO)c21] | 3-(4-[3-[(5-hydroxy-pentyl)oxy]pro-pyl]-3-methyl-2-oxo-1,3-benzodiazol-1-yl)piperidine-2,6-dione | 404.3 | (400 MHz, DMSO-$d_6$) δ 11.09 (s, 1H), 6.97 (d, J = 4.6 Hz, 2H), 6.88 (q, J = 4.4 Hz, 1H), 5.37 (dd, J = 12.5, 5.4 Hz, 1H), 4.34 (t, J = 5.2 Hz, 1H), 3.62-3.54 (m, 4H), 3.43-3.38 (m, 4H), 3.01-2.83 (m, 3H), 2.77-2.58 (m, 2H), 2.05-1.95 (m, 1H), 1.86-1.74 (m, 3H), 1.52 (p, J = 6.8 Hz, 2H), 1.43 (q, J = 6.8, 6.1 Hz, 2H), 1.38-1.32 (m, 2H). |
| B20 | 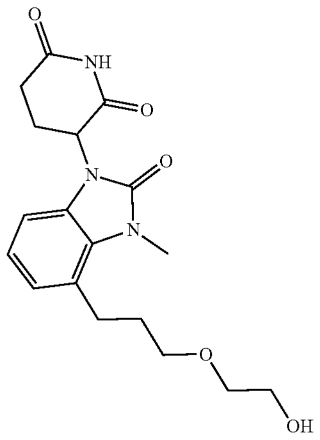 [SMILES: Cn1c(=O)n(C2CCC(=O)NC2=O)c2cccc(CCCOCCO)c21] | 3-[4-[3-(2-hydroxyethoxy)pro-pyl]-3-methyl-2-oxo-1,3-benzodiazol-l-yl]piperidine-2,6-dione | 362.2 | (400 MHz, DMSO-$d_6$) δ 11.08 (s, 1H), 6.97 (d, J = 4.4 Hz, 2H), 6.89 (d, J = 4.7 Hz, 1H), 5.36 (dd, J = 12.6, 5.4 Hz, 1H), 4.57 (dd, J = 6.1, 4.8 Hz, 1H), 3.63-3.39 (m, 9H), 3.00-2.84 (m, 3H), 2.76-2.58 (m, 2H), 2.05-1.96 (m, 1H), 1.89-1.74 (m, 2H). |

TABLE 16-continued

| Characterization data for intermediates prepared according to above. | | | | |
|---|---|---|---|---|
| Intermediate | Structure | Chemical Name | MS: $[(M + 1)]^+$ | $^1$H-NMR |
| B21 | 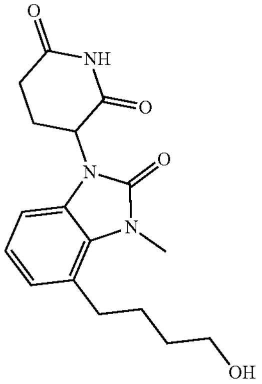 [SMILES: Cn1c(=O)n(C2CCC(=O)NC2=O)c2cccc(CCCCO)c21] | 3-[4-(4-hydroxybutyl)-3-methyl-2-oxo-1,3-benzodiazol-l-yl]piperidine-2,6-dione | 332.2 | (400 MHz, DMSO-$d_6$) δ 11.09 (s, 1H), 7.00-6.94 (m, 2H), 6.87 (dd, J = 5.2, 3.7 Hz, 1H), 5.37 (dd, J = 12.5, 5.4 Hz, 1H), 4.40 (t, J = 5.2 Hz, 1H), 3.56 (s, 3H), 3.48-3.42 (m, 2H), 2.90 (dd, J = 9.5, 6.0 Hz, 2H), 2.77-2.59 (m, 2H), 2.04-1.97 (m, 1H), 1.79-1.74 (m, 1H), 1.63 (tt, J = 8.2, 5.8 Hz, 2H), 1.58-1.50 (m, 2H). |
| B22 | 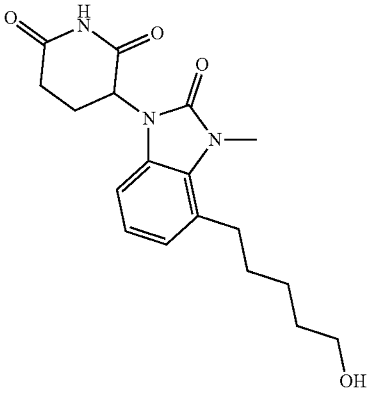 [SMILES: Cn1c(=O)n(C2CCC(=O)NC2=O)c2cccc(CCCCCO)c21] | 3-[4-(5-hydroxypentyl)-3-methyl-2-oxo-1,3-benzodiazol-1-yl]piperidine-2,6-dione | 346.3 | (400 MHz, DMSO-$d_6$) δ 11.09 (s, 1H), 6.99-6.93 (m, 2H), 6.87 (q, J = 4.3 Hz, 1H), 5.36 (dd, J = 12.5, 5.4 Hz, 1H), 4.35 (t, J = 5.1 Hz, 1H), 3.56 (s, 3H), 3.43-3.37 (m, 2H), 2.89 (t, J = 7.8 Hz, 2H), 2.72 (td, J = 12.8, 4.3 Hz, 1H), 2.66-2.58 (m, 1H), 2.05-1.95 (m, 1H), 1.61 (p, J = 7.6 Hz, 2H), 1.47 (q, J = 7.2 Hz, 2H), 1.41 (t, J = 7.8 Hz, 2H), 1.25 (s, 1H). |
| B23 | 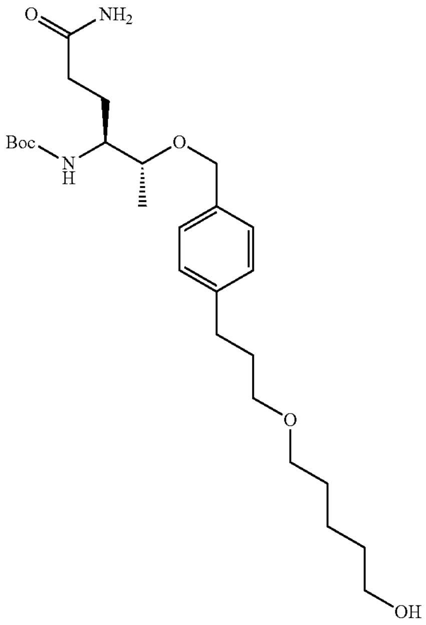 | tert-butyl N-[(3S,4R)-1-carbamoyl-4-[(4-[3-[(5-hydroxy-pentyl)oxy]pro-pyl]phenyl)meth-oxy]pentan-3-yl]carbamate | 481.4 | (400 MHz, DMSO-$d_6$) δ 7.24-7.22 (m, 3H), 7.14 (d, J = 7.7 Hz, 2H), 6.68 (s, 1H), 6.66-6.57 (m, 1H), 4.49-4.38 (m, 2H), 4.34 (t, J = 5.2 Hz, 1H), 3.61 (s, 1H), 3.46-3.29 (m, 9H), 2.60 (t, J = 7.6 Hz, 2H), 2.07-2.02 (m, 1H), 1.80-1.75 (m, 4H), 1.50 (p, J = 6.7 Hz, 2H), 1.44 (d, J = 7.3 Hz, 1H), 1.40-1.36 (m, 15H), 1.06 (d, J = 6.0 Hz, 3H). |

TABLE 16-continued

| Characterization data for intermediates prepared according to above. | | | | |
|---|---|---|---|---|
| Intermediate | Structure | Chemical Name | MS: [(M + 1)]+ | $^1$H-NMR |
| B24 | 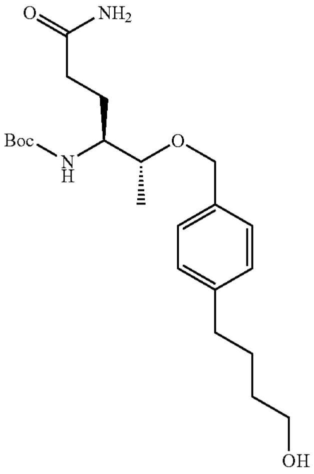 [SMILES: C[C@@H](OCc1ccc(CCCCO)cc1)[C@H](CCC(N)=O)NC(=O)OC(C)(C)C] | tert-butyl N-[(3S,4R)-1-carbamoyl-4-[[4-(4-hydroxy-butyl)phenyl]meth-oxy]pentan-3-yl]carbamate | 409.2 | (400 MHz, DMSO-$d_6$) δ 7.22 (t, J = 7.4 Hz, 3H), 7.17-7.02 (m, 3H), 6.67 (s, 1H), 6.60 (t, J = 8.5 Hz, 1H), 4.49-4.35 (m, 2H), 4.35 (t, J = 5.1 Hz, 1H), 3.42-3.39 (m, 3H), 3.17 (t, J = 5.6 Hz, 1H), 2.60-2.52 (m, 2H), 2.51-2.46 (m, 1H), 2.03 (tq, J = 14.9, 8.5, 6.9 Hz, 1H), 1.64-1.51 (m, 2H), 1.50-1.32 (m, 11H), 1.05 (t, J = 6.2 Hz, 3H). |
| B25 | 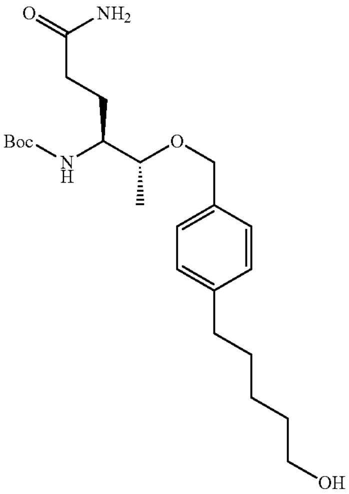 [SMILES: C[C@@H](OCc1ccc(CCCCCO)cc1)[C@H](CCC(N)=O)NC(=O)OC(C)(C)C] | tert-butyl N-[(3S,4R)-1-carbamoyl-4-[[4-(5-hydroxy-pentyl)phenyl]meth-oxy]pentan-3-yl]carbamate | 423.3 | (400 MHz, $CDCl_3$) δ 7.25 (d, J = 7.8 Hz, 2H), 7.17 (d, J = 7.9 Hz, 2H), 6.55 (s, 1H), 5.53 (s, 1H), 4.91 (d, J = 9.6 Hz, 1H), 4.59 (d, J = 11.5 Hz, 1H), 4.38 (d, J = 11.5 Hz, 1H), 3.67-3.34 (m, 3H), 2.64 (t, J = 7.6 Hz, 2H), 2.32-2.25 (m, 2H), 1.99 (dq, J = 15.7, 8.7, 8.2 Hz, 2H), 1.71-1.58 (m, 5H), 1.45 (s, 12H), 1.21 (d, J = 6.2 Hz, 3H). |

TABLE 16-continued

Characterization data for intermediates prepared according to above.

| Intermediate | Structure | Chemical Name | MS: [(M + 1)]$^+$ | $^1$H-NMR |
|---|---|---|---|---|
| B26 | 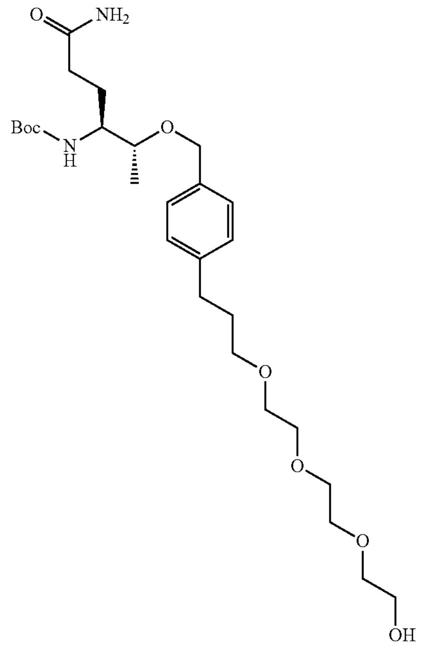 [SMILES: C[C@@H](OCc1ccc(CCCOCCOCCOCCO)cc1)[C@H](CCC(N)=O)NC(=O)OC(C)(C)C] | tert-butyl N-[(3S,4R)-1-carbamoyl-4-[[4-(3-[2-[2-(2-hydroxyethoxy)ethoxy]ethoxy]propyl)phenyl]methoxy]pentan-3-yl]carbamate | 527.4 | (400 MHz, $CDCl_3$) δ 7.25 (d, J = 7.9 Hz, 2H), 7.19 (d, J = 7.9 Hz, 2H), 6.53 (s, 1H), 5.46 (s, 1H), 4.91 (d, J = 9.7 Hz, 1H), 4.60 (d, J = 11.5 Hz, 1H), 4.39 (d, J = 11.5 Hz, 1H), 3.75 (dd, J = 5.4, 3.6 Hz, 2H), 3.71-3.68 (m, 6H), 3.66-3.31 (m, 5H), 3.49 (t, J = 6.5 Hz, 2H), 2.71 (t, J = 7.6 Hz, 2H), 2.29 (q, J = 6.3, 5.8 Hz, 2H), 2.09 (s, 2H), 2.05-1.87 (m, 3H), 1.72 (d, J = 12.8 Hz, 1H), 1.46 (s, 9H), 1.22 (d, J = 6.3 Hz, 3H). |
| B27 | 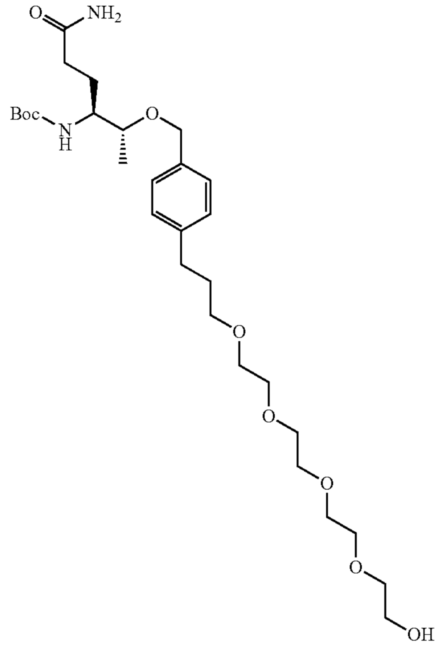 [SMILES: C[C@@H](OCc1ccc(CCCOCCOCCOCCOCCO)cc1)[C@H](CCC(N)=O)NC(=O)OC(C)(C)C] | tert-butyl N-[(3S,4R)-1-carbamoyl-4-[[4-(1-hydroxy-3,6,9,12-tetraoxapentadecan-15-yl)phenyl]methoxy]pentan-3-yl]carbamate | 571.4 | (400 MHz, $CDCl_3$) δ 7.25 (d, J = 7.8 Hz, 2H), 7.19 (d, J = 7.9 Hz, 2H), 6.52 (s, 1H), 5.48 (s, 1H), 4.91 (d, J = 9.6 Hz, 1H), 4.59 (d, J = 11.5 Hz, 1H), 4.39 (d, J = 11.5 Hz, 1H), 3.74 (t, J = 4.4 Hz, 2H), 3.69 (s, 10H), 3.65-3.59 (m, 5H), 3.49 (t, J = 6.5 Hz, 2H), 2.70 (t, J = 7.6 Hz, 2H), 2.35-2.21 (m, 3H), 2.05-1.87 (m, 3H), 1.75 (d, J = 5.6 Hz, 1H), 1.46 (s, 9H), 1.22 (d, J = 6.2 Hz, 3H). |

TABLE 16-continued

| Characterization data for intermediates prepared according to above. | | | | |
|---|---|---|---|---|
| Intermediate | Structure | Chemical Name | MS: $[(M + 1)]^+$ | $^1$H-NMR |
| B28 | 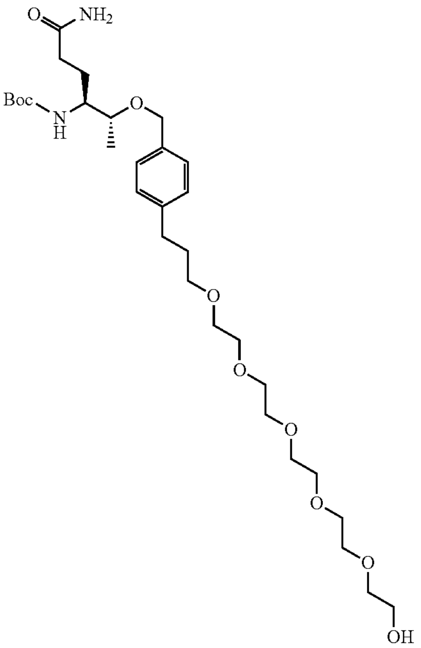 [SMILES: C[C@@H](OCc1ccc(CCCOCCOCCOCCOCCOCCO)cc1)[C@H](CCC(N)=O)NC(=O)OC(C)(C)C] | tert-butyl N-[(3S,4R)-1-carbamoyl-4-[[4-(1-hydroxy-3,6,9,12,15-pentaoxa-octadecan-18-yl)phenyl]meth-oxy]pentan-3-yl]carbamate | 615.6 | (400 MHz, $CDCl_3$) δ 7.25 (d, J = 7.9 Hz, 2H), 7.18 (d, J = 7.8 Hz, 2H), 6.49 (s, 1H), 5.49 (s, 1H), 4.91 (d, J = 9.7 Hz, 1H), 4.59 (d, J = 11.5 Hz, 1H), 4.38 (d, J = 11.5 Hz, 1H), 3.79-3.56 (m, 22H), 3.48 (t, J = 6.5 Hz, 2H), 2.69 (t, J = 7.7 Hz, 2H), 2.36-2.23 (m, 2H), 2.02 (s, 2H), 1.91 (dq, J = 8.8, 6.6 Hz, 2H), 1.77-1.64 (m, 1H), 1.45 (s, 9H), 1.21 (d, J = 6.2 Hz, 3H). |
| B29 | 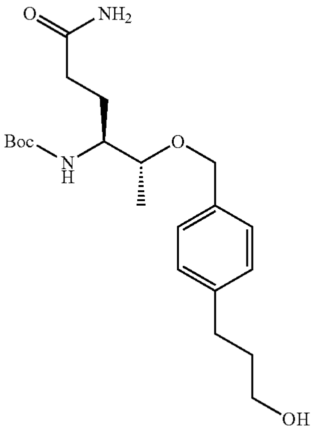 [SMILES: C[C@@H](OCc1ccc(CCCO)cc1)[C@H](CCC(N)=O)NC(=O)OC(C)(C)C] | tert-butyl N-[(3S,4R)-1-carbamoyl-4-[[4-(3-hydroxy-propyl)phenyl]meth-oxy]pentan-3-yl]carbamate | 395.3 | (400 MHz, DMSO-$d_6$) δ 7.25-7.21 (m, 3H), 7.15 (d, J = 7.8 Hz, 2H), 6.68 (s, 1H), 6.60 (d, J = 9.0 Hz, 1H), 4.47-4.39 (m, 3H), 3.64-3.59 (m, 1H), 3.43-3.40 (m, 3H), 2.59 (t, J = 7.8 Hz, 2H), 2.10-1.98 (m, 2H), 1.84-1.65 (m, 4H), 1.38 (s, 9H), 1.06 (d, J = 5.9 Hz, 3H). |

TABLE 16-continued

| Characterization data for intermediates prepared according to above. | | | | |
|---|---|---|---|---|
| Intermediate | Structure | Chemical Name | MS: $[(M + 1)]^+$ | $^1H$-NMR |
| B30 | 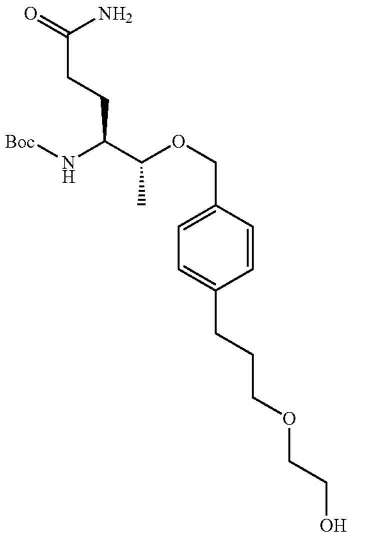 [SMILES: C[C@@H](OCc1ccc(CCCOCCO)cc1)[C@H](CCC(N)=O)NC(=O)OC(C)(C)C] | tert-butyl N-[(3S,4R)-1-carbamoyl-4-([4-[3-(2-hydroxyethoxy)propyl]phenyl]methoxy)pentan-3-yl]carbamate | 439.3 | (400 MHz, $CDCl_3$) δ 7.26 (s, 2H), 7.18 (d, J = 7.8 Hz, 2H), 4.91 (d, J = 9.7 Hz, 1H),4.59 (d, J = 11.4 Hz, 1H), 4.39 (d, J = 11.5 Hz, 1H), 3.75-3.58 (m, 4H), 3.56-3.49 (m, 3H), 2.71 (t, J = 7.6 Hz, 2H), 2.28 (q, J = 5.5, 4.5 Hz, 2H), 1.96-1.90 (m, 2H), 1.89-1.85 (m, 4H), 1.71 (td, J = 12.2, 6.1 Hz, 1H), 1.45 (s, 9H), 1.21 (d, J = 6.3 Hz, 3H). |
| B31 | 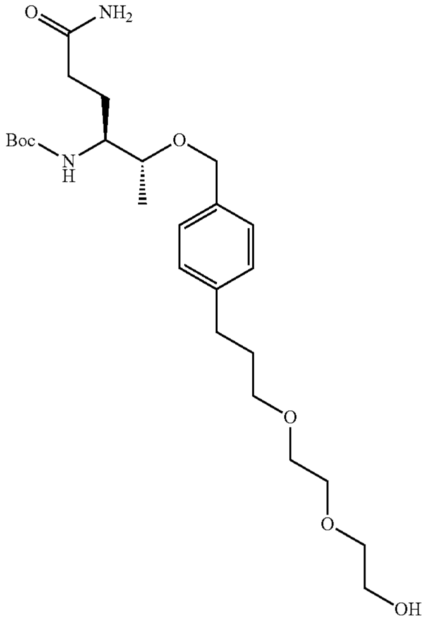 [SMILES: C[C@@H](OCc1ccc(CCCOCCOCCO)cc1)[C@H](CCC(N)=O)NC(=O)OC(C)(C)C] | tert-butyl N-[(3S,4R)-1-carbamoyl-4-[(4-[3-[2-(2-hydroxyethoxy)ethoxy]propyl]phenyl)methoxy]pentan-3-yl]carbamate | 483.3 | (400 MHz, DMSO-$d_6$) δ 7.21 (d, J = 7.0 Hz, 2H), 7.15 (d, J = 7.8 Hz, 2H), 6.67 (s, 1H), 6.64-6.56 (m, 1H), 4.56 (td, J = 5.4, 1.5 Hz, 1H), 4.51-4.38 (m, 2H), 3.68-3.57 (m, 1H), 3.53 (dd, J = 5.6, 3.3 Hz, 2H), 3.51-3.45 (m, 4H), 3.43 (dd, J = 6.2, 4.8 Hz, 3H), 3.39 (d, J = 6.4 Hz, 2H), 2.60 (t, J = 7.7 Hz, 2H), 2.14-.94 (m, 2H), 1.81-1.74 (m, 3H), 1.50 (d, J = 17.4 Hz, 2H), 1.37 (d, J = 9.6 Hz, 9H), 1.06 (d, J = 6.0 Hz, 3H). |

TABLE 16-continued

Characterization data for intermediates prepared according to above.

| Intermediate | Structure | Chemical Name | MS: $[(M + 1)]^+$ | $^1$H-NMR |
|---|---|---|---|---|
| B33 | 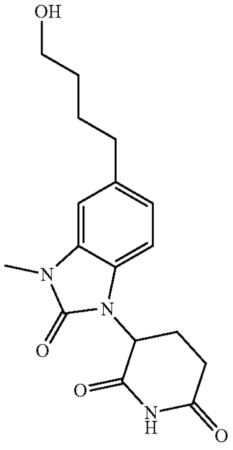 [SMILES: Cn1c(=O)n(C2CCC(=O)NC2=O)c2ccc(CCCCO)cc21] | 3-[5-(4-hydroxybutyl)-3-methyl-2-oxo-1,3-benzodiazol-1-yl]piperidine-2,6-dione | 332.2 | (400 MHz, DMSO-$d_6$) δ 11.09 (s, 1H), 7.03 (d, J = 1.5 Hz, 1H), 7.00 (d, J = 8.0 Hz, 1H), 6.87 (dd, J = 8.1, 1.6 Hz, 1H), 5.34 (dd, J = 12.7, 5.4 Hz, 1H), 4.37 (t, J = 5.2 Hz, 1H), 3.41 (q, J = 6.2 Hz, 2H), 3.34 (s, 1H), 2.98-2.82 (m, 1H), 2.72 (td, J = 12.9, 4.3 Hz, 1H), 2.67-2.58 (m, 3H), 2.00 (ddd, J = 11.2, 6.1, 3.9 Hz, 1H), 1.62 (p, J = 7.6 Hz, 2H), 1.45 (p, J = 6.7 Hz, 2H). |
| B34 | 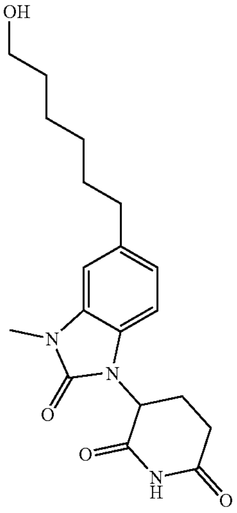 [SMILES: Cn1c(=O)n(C2CCC(=O)NC2=O)c2ccc(CCCCCCO)cc21] | 3-[5-(6-hydroxyhexyl)-3-methyl-2-oxo-1,3-benzodiazol-1-yl]piperidine-2,6-dione | 360.3 | (400 MHz, DMSO-$d_6$) δ 11.08 (s, 1H), 7.03 (d, J = 1.5 Hz, 1H), 7.00 (d, J = 8.0 Hz, 1H), 6.86 (dd, J = 8.1, 1.6 Hz, 1H), 5.34 (dd, J = 12.7, 5.4 Hz, 1H), 4.32 (s, 1H), 3.38 (q, J = 5.8 Hz, 2H), 3.33 (s, 3H), 2.99-2.84 (m, 1H), 2.72 (td, J = 12.9, 4.4 Hz, 1H), 2.66-2.57 (m, 3H), 2.00 (ddd, J = 10.9, 5.8, 3.7 Hz, 1H), 1.59 (p, J = 7.7 Hz, 2H), 1.41 (q, J = 6.5 Hz, 2H), 1.36-1.25 (m, 4H). |
| B35 | 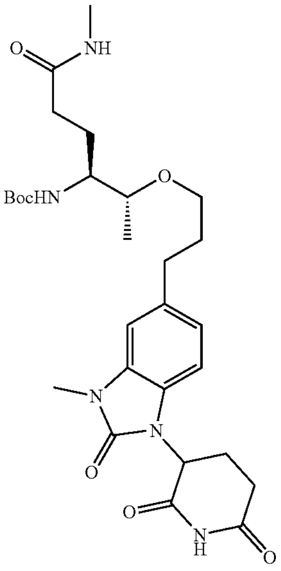 [SMILES: CNC(=O)CC[C@H](NC(=O)OC(C)(C)C)[C@@H](C)OCCCc1ccc2c(c1)n(C)c(=O)n2C1CCC(=O)NC1=O] | tert-butyl N-[(3S,4R)-1-carbamoyl-4-[3-[1-(2,6-dioxopiperidin-3-yl)-3-methyl-2-oxo-1,3-benzodiazol-5-yl]propoxy]pentan-3-yl]carbamate | 546.3 | (400 MHz, $CD_3OD$) δ 7.40 (d, J = 1.9 Hz, 1H), 7.26 (dd, J = 8.4, 1.9 Hz, 1H), 7.03-6.99 (m, 1H), 5.38-5.29 (m, 2H), 3.59-3.48 (m, 1H), 3.48-3.45 (m, 1H), 3.43 (s, 3H), 2.97-2.89 (m, 1H), 2.87-2.75 (m, 5H), 2.33-2.12 (m, 1H), 2.00 (s, 4H), 1.91 (q, J = 6.9 Hz, 1H), 1.61 (s, 1H), 1.45 (s, 9H), 1.17-1.09 (m, 3H). |

TABLE 16-continued

| Characterization data for intermediates prepared according to above. | | | | |
|---|---|---|---|---|
| Intermediate | Structure | Chemical Name | MS: $[(M + 1)]^+$ | $^1$H-NMR |
| B36 | 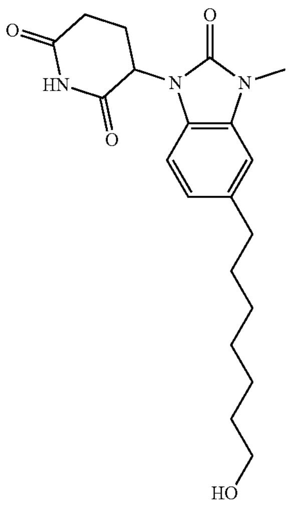 [SMILES: Cn1c(=O)n(C2CCC(=O)NC2=O)c2ccc(CCCCCCCO)cc21] | 3-[5-(7-hydroxyheptyl)-3-methyl-2-oxo-1,3-benzodiazol-1-yl]piperidine-2,6-dione | 374.20 | (400 MHz, DMSO-$d_6$) δ 11.08 (s, 1H), 7.02 (d, J = 1.5 Hz, 1H), 7.00 (d, J = 8.0 Hz, 1H), 6.86 (dd, J = 8.1, 1.6 Hz, 1H), 5.34 (dd, J = 12.7, 5.3 Hz, 1H), 4.31 (t, J = 5.2 Hz, 1H), 3.38 (q, J = 6.3 Hz, 2H), 3.33 (s, 3H), 2.98-2.83 (m, 1H), 2.75-2.69 (m, 1H), 2.6-2.55 (m, 3H), 2.05-1.94 (m, 1H), 1.60-1.58 (m, 2H), 1.42-1.39 (m, 2H), 1.31-1.27 (m, 6H). |

3-1[3-Methyl-2-oxo-4-I[(prop-2-yn-1-yloxy)methyl]-1,3-benzodiazol-1-yl]piperidine-2,6-dione (Intermediate B32)

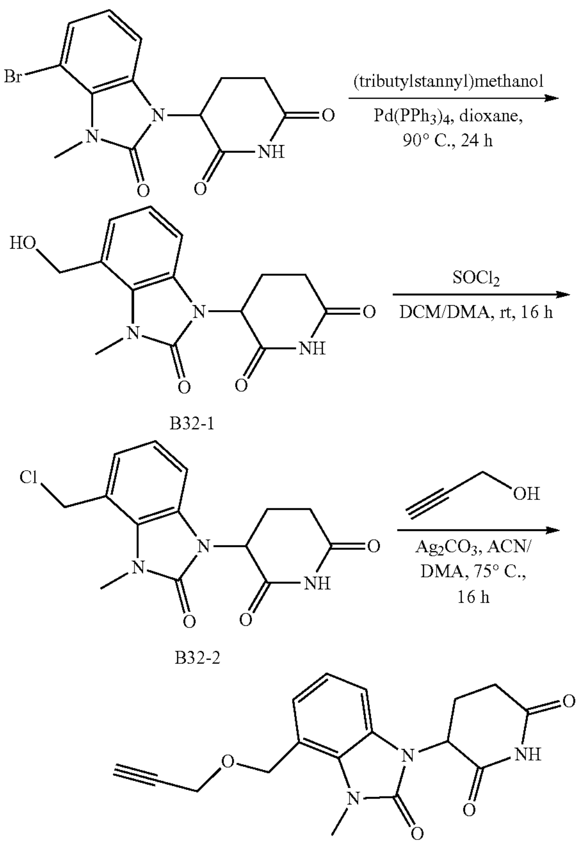

B32-1

B32-2

B32

Step 1. 3-[4-(Hydroxymethyl)-3-methyl-2-oxo-1,3-benzodiazol-1-yl]piperidine-2,6-dione. To a solution of 3-(4-bromo-3-methyl-2-oxo-1,3-benzodiazol-1-yl)piperidine-2,6-dione (500 mg, 1.48 mmol) in dioxane (10.0 mL) were added $Pd(PPh_3)_4$(171 mg, 0.15 mmol) and (tributylstannyl)methanol (950 mg, 2.96 mmol) at room temperature under nitrogen atmosphere. The resulting mixture was stirred for 24 hours at 90° C. After cooling down to room temperature, the reaction was quenched with saturated aqueous KF solution (20.0 mL) and extracted with ethyl acetate (3×20.0 mL). The combined organic layers were dried over anhydrous $Na_2SO_4$. After filtration, the filtrate was concentrated under reduced pressure. The residue was purified by reversed phase flash chromatography with the following conditions: Column: Wel Flash™ C18-I, 20~40 um, 330 g; EluentA: water (plus 10 mmol/LFA); Eluent B: ACN; Gradient: 20% - 40% B in 20 min; Flow rate: 80 mL/min; Detector: UV 220/254 nm; desired fractions were collected at 30% B and concentrated under reduced pressure to afford the title compound as white solid (200 mg, 47%): $^1$H NMR (400 MHz, DMSO-$d_6$) δ 11.10 (s, 1H), 7.07 (dd, J=7.2, 1.9 Hz, 1H), 7.05-7.01 (m, 1H), 7.01-6.95 (m, 1H), 5.39 (dd, J=12.7, 5.4 Hz, 1H), 4.75 (s, 2H), 3.62 (s, 3H), 2.91 (m, 1H), 2.74 (m, 1H), 2.69-2.59 (m, 1H), 2.06-1.96 (m, 1H); MS (ESI, m/z): $[(M+1)]^+$=290.25.

Step 2. 3-[4-(Chloromethyl)-3-methyl-2-oxo-1,3-benzodiazol-1-yl]piperidine-2,6-dione. To a solution of 3-[4-(hydroxymethyl)-3-methyl-2-oxo-1,3-benzodiazol-1-yl]piperidine-2,6-dione (1.00 g, 3.46 mmol) in DCM (10.0 mL) were added DMF (5 mL) and $SOCl_2$ (0.50 mL, 4.22 mmol) at 0° C. under nitrogen atmosphere. After stirring for 2 hours at room temperature, the reaction was quenched by the addition of water (20.0 mL) at 0° C. and extracted with DCM (3×30.0 mL). The combined organic layers were dried over anhydrous $Na_2SO_4$. After filtration, the filtrate was concentrated under reduced pressure. The residue was concentrated under reduced pressure to afford the title compound as a white solid (1.00 g, 94%): $^1$H NMR (400 MHz, DMSO-$d_6$) δ 11.10 (s, 1H), 7.15-6.88 (m, 3H), 5.39 (dd, J=12.7, 5.4 Hz, 1H), 4.74 (s, 2H), 3.62 (s, 3H), 2.91 (ddd, J=16.6, 13.4, 5.2 Hz, 1H), 2.80-2.58 (m, 2H), 2.07-1.91 (m, 1H); MS (ESI, m/z): $[(M+1)]^+$=308.07.

Step 3. 3-[3-Methyl-2-oxo-4-[(prop-2-yn-1-yloxy)methyl]-1,3-benzodiazol-1-yl]piperidine-2,6-dione (Intermediate B32). To a mixture of 3-[4-(chloromethyl)-3-methyl-2-oxo-1,3-benzodiazol-1-yl]piperidine-2,6-dione (1.50 g, 4.87 mmol) and $Ag_2CO_3$ (4.03 g, 14.6 mmol) in ACN (15.0 mL)/DMA (5.00 mL) was added propargyl alcohol (1.37 g, 24.4 mmol) at room temperature under nitrogen atmosphere. The resulting mixture was stirred for 16 hours at 75° C. After cooling down to room temperature, the mixture was filtered. The filtered cake was washed with DCM (3x10.0 mL). The combined filtrates were concentrated under reduced pressure. The residue was purified by reversed phase flash chromatography with the following conditions: Column: WelFlash™ C18-I, 20~40 um, 330 g; Eluent A: water (plus 10 mmol/L$NH_4HCO_3$); Eluent B: ACN; Gradient: 25% - 45% B in 20 min; Flow rate: 80 mL/min; Detector: UV 220/254 nm; desired fractions were collected at 38% B and concentrated under reduced pressure to afford the title compound as a light yellow solid (450 mg, 29%): $^1H$ NMR (400 MHz, DMSO-$d_6$) δ 10.54 (s, 1H), 7.15 (p, J=4.0 Hz, 1H), 7.02 (d, J=4.5 Hz, 2H), 5.40 (dd, J=12.7, 5.4 Hz, 1H), 4.77 (s, 2H), 4.22 (d, J=2.4 Hz, 2H), 3.58 (s, 3H), 3.53 (t, J=2.4 Hz, 1H), 2.90 (m, 1H), 2.78-2.59 (m, 2H), 2.03 (m, 1H); MS (ESI, m/z): $[(M+1)]^+$=328.10.

Tert-butyl N-[3-[4-([[(2R,3S)-3-amino-5-carbamoylpentan-2-yl]oxy]methyl)phenyl]propyl]carbamate (Intermediate C)

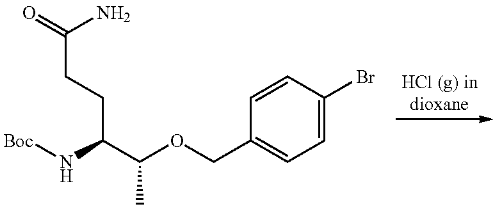

Intermediate A

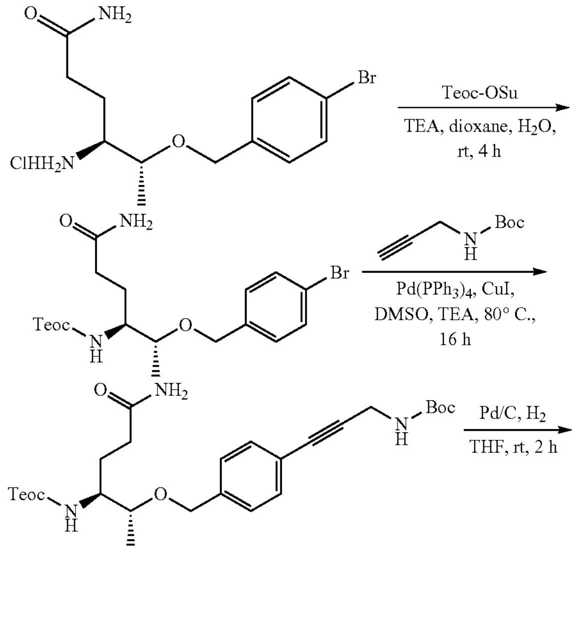

-continued

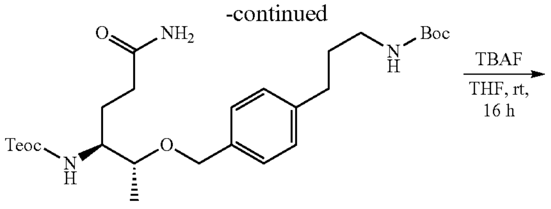

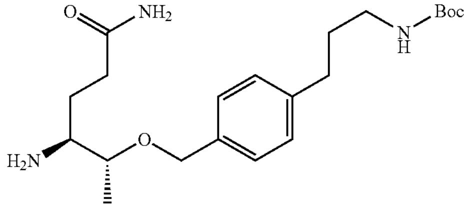

Intermediate C

Step 1. (4S,5R)-4-Amino-5-[(4-bromophenyl)methoxy]hexanamide hydrochloride. To a solution of tert-butyl N-[(3S,4R)-4-[(4-bromophenyl)methoxy]-1-carbamoylpentan-3-yl]carbamate (4.50 g, 10.8 mmol) in 1,4-dioxane (50.0 mL) was added a HCl solution (4 M in 1,4-dioxane, 16.0 mL) at 0° C. under nitrogen atmosphere. The resulting mixture was stirred for 1 hour at room temperature. The resulting mixture was concentrated under reduced pressure to afford the title compound as a white solid (2.60 g, 65%): $^1H$ NMR (400 MHz, D20) δ 7.54-7.46 (m, 2H), 7.22 (d, J=8.2 Hz, 2H), 4.52 (d, J=11.9 Hz, 1H), 4.43 (d, J=11.9 Hz, 1H), 3.77 (dd, J=6.5, 3.6 Hz, 1H), 3.37-3.30 (m, 1H), 2.29 (t, J=7.6 Hz, 2H), 1.81 (dh, J=22.4, 7.2 Hz, 2H), 1.12 (d, J=6.6 Hz, 3H); MS (ESI, m/z): $[(M+1)]^+$=315.10, 317.10.

Step 2. 2-(Trimethylsilyl)ethyl N-[(3S,4R)-4-[(4-bromophenyl)methoxy]-1-carbamoylpentan-3-yl]carbamate. To a stirred solution of (4S,5R)-4-amino-5-[(4-bromophenyl)methoxy]hexanamide hydrochloride (3.40 g, 9.67 mmol) in water (35.0 mL) was added a solution of TEA (2.93 g, 29.0 mmol) in 1,4-dioxane (35.0 mL) followed by the addition of 2,5-dioxopyrrolidin-1-yl2-(trimethylsilyl)ethyl carbonate (2.76 g, 10.7 mmol) at room temperature. The resulting mixture was stirred for 16 hours at room temperature under nitrogen atmosphere. The resulting mixture was concentrated under reduced pressure. The residue was purified by reversed phase flash chromatography with the following conditions: column, C18 silica gel; 20~40 μm, 330 g; Eluent A: water (plus 10 mmol/L AcOH); Eluent B: ACN; Gradient: 60%-80% B in 20 min; Flow rate: 80 mL/min; Detector: UV 220/254 nm; desired fractions were collected at 65% and concentrated under reduced pressure to afford the title compound as a colorless solid (3.50 g, 79%): $^1H$ NMR (400 MHz, DMSO-d4) δ 7.56-7.47 (m, 2H), 7.36-7.16 (m, 3H), 6.87 (d, J=9.3 Hz, 1H), 6.70 (s, 1H), 4.53-4.41 (m, 2H), 4.11-3.94 (m, 2H), 3.57-3.39 (m, 2H), 2.18-1.96 (m, 2H), 1.85-1.72 (m, 1H), 1.58-1.40 (m, 1H), 1.07 (d, J=6.1 Hz, 3H), 0.92 (t, J=8.4 Hz, 2H), 0.02 (s, 9H); MS (ESI, m/z): $[(M+1)]^+$=459.10, 461.10.

Step 3. Tert-butyl N-[3-[4-([[(2R,3S)-5-carbamoyl-3-([[2-(trimethylsilyl)ethoxy]carbonyl]amino)pentan-2-yl]oxy]methyl)phenyl]prop-2-yn-1-yl]carbamate. To a solution of 2-(trimethylsilyl)ethyl N-[(3S,4R)-4-[(4-bromophenyl)methoxy]-1-carbamoylpentan-3-yl]carbamate (2.18 g, 4.75 mmol) in DMSO (30 mL) were added tert-butyl N-(prop-2-yn-1-yl)carbamate (3.68 g, 23.7 mmol), TEA (15 mL), CuI (90.4 mg, 0.48 mmol) and $Pd(PPh_3)_4$(548 mg, 0.48 mmol) at room temperature under nitrogen atmosphere. The reaction mixture was purged with nitrogen for 3 times and was stirred for 16 hours at 90° C. under nitrogen atmosphere. The resulting mixture cooled down to room temperature and concentrated under reduced pressure. The residue was purified by reversed phase flash chromatography with the following conditions: column, C18 silica gel; 20~40 m, 330 g; Eluent A: water (plus 10 mmol/L TEA); Eluent B: ACN; Gradient: 55% - 75% B in 20 min; Flow rate: 80 mL/min; Detector: UV 220/254 nm; desired fractions were collected at 65% and concentrated under reduced pressure to afford the title compound as a brown solid (2.30 g, 91%): $^1$H NMR (400 MHz, DMSO-$d_6$) δ 7.37-7.31 (m, 4H), 7.21 (s, 1H), 6.87 (d, J=9.2 Hz, 1H), 6.69 (s, 1H), 4.49 (d, J=2.1 Hz, 2H), 4.12-3.88 (m, 4H), 3.56-3.38 (m, 2H), 2.15-1.97 (m, 2H), 1.78 (dd, J=10.0, 3.7 Hz, 1H), 1.47 (s, 1H), 1.40 (s, 1OH), 1.07 (d, J=6.2 Hz, 3H), 0.92 (t, J=8.4 Hz, 2H), 0.00 (s, 9H).; MS (ESI, m/z): $[(M+1)]^+$=534.30.

The intermediates in Table 17 were prepared according to step 3 of the procedure to prepare Intermediate C.

Step 4. Tert-butyl N-[3-[4-([[(2R,3S)-5-carbamoyl-3-([[2-(trimethylsilyl)ethoxy]carbonyl]amino)pentan-2-yl]oxy]methyl)phenyl]propyl]carbamate. To a solution of tert-butyl N-[3-[4-([[(2R,3S)-5-carbamoyl-3-([[2-(trimethylsilyl)ethoxy]carbonyl]amino)pentan-2-yl]oxy]methyl)phenyl]prop-2-yn-1-yl]carbamate (330 mg, 0.62 mmol) in THF (20.0 mL) was added Pd—C (100 mg, 10% palladium on activated carbon) at room temperature under nitrogen atmosphere. The resulting mixture was purged with $H_2$ for 3 times and stirred for 2 hours at room temperature under hydrogen atmosphere. The reaction mixture was filtered through a Celite pad. The filtrate was concentrated under reduced pressure to afford the title compound as a brown solid (300 mg, 90%): $^1$H NMR (400 MHz, DMSO-d) 8 7.24-7.22 (m, 3H), 7.14 (d, J=7.8 Hz, 2H), 6.84 (d, J=8.7 Hz, 1H), 6.66 (d, J=14.7 Hz, 1H), 4.50-4.38 (m, 2H), 4.11-3.95 (m, 2H), 3.49 (d, J=8.7 Hz, 1H), 3.41 (t, J=6.0 Hz, 1H), 2.92 (q, J=6.6 Hz, 2H), 2.55 (d, J=7.7 Hz, 2H), 2.13-1.97 (m, 2H), 1.79 (dt, J=11.8, 4.4 Hz, 1H), 1.65 (p, J=7.3 Hz, 2H), 1.57-1.41 (m, 2H), 1.38 (s, 9H), 1.06 (d, J=6.1 Hz, 3H), 0.92 (t, J=8.4 Hz, 2H), 0.00 (s, 9H); MS (ESI, m/z): $[(M+1)]^+$=538.45.

The intermediates in Table 18 were prepared according to step 4 of the procedure to prepare Intermediate C.

TABLE 17

Characterization data for intermediates prepared according to above.

| Intermediate | Structure | Chemical Name | MS: $[(M + 1)]^+$ | $^1$H-NMR |
|---|---|---|---|---|
| C-3-1 | 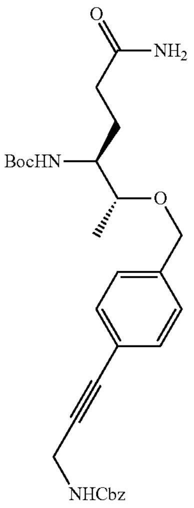 [SMILES: C[C@@H](OCc1ccc(C#CCNC(=O)OCc2ccccc2)cc1)[C@H](CCC(N)=O)NC(=O)OC(C)(C)C] | tert-butyl ((2R,3S)-6-amino-2-((4-(3-(((benzyloxy)carbonyl)amino)prop-1-yn-1-yl)benzyl)oxy)-6-oxohexan-3-yl)carbamate | 524.30 | (400 MHz, DMSO-$d_6$) δ 7.44-7.29 (m, 10H), 7.23 (s, br, 1H), 6.69 (s, 1H), 6.65-6.30 (m, 1H), 5.07 (s, 2H), 4.57-4.38 (m, 2H), 4.07 (d, J = 5.6 Hz, 1H), 3.47-3.41 (m, 3H), 2.09-2.05 (m, 2H), 1.79-1.75 (m, 1H), 1.52-1.48 (m, 1H), 1.39 (s, 9H), 1.07 (d, J = 6.0 Hz, 3H). |

TABLE 18

Characterization data for intermediates prepared according to above.

| Intermediate | Structure | Chemical Name | MS: $[(M+1)]^+$ | $^1$H-NMR |
|---|---|---|---|---|
| C-4-1 | 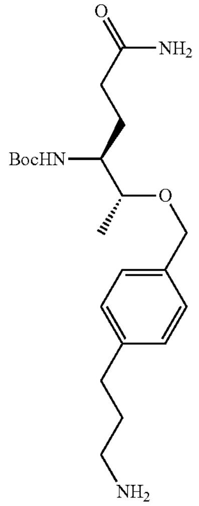 [SMILES: C[C@@H](OCc1ccc(CCCN)cc1)[C@H](CCC(N)=O)NC(=O)OC(C)(C)C] | tert-butyl N-[(3S,4R)-4-[[4-(3-amino-propyl)phenyl]meth-oxy]-1-carbamoyl-pentan-3-yl]carbamate | 394.30 | $^1$H NMR (400 MHz, DMSO-$d_6$) δ 7.26-7.19 (m, 3H), 7.14 (d, J = 7.8 Hz, 2H), 6.68 (s, 1H), 6.61 (d, J = 9.1 Hz, 1H), 4.49-4.37 (m, 2H), 3.53-3.38 (m, 2H), 3.18 (s, 2H), 2.62-2.51 (m, 4H), 2.12-1.95 (m, 2H), 1.88-1.74 (m, 1H), 1.64-1.60 (m, 2H), 1.53-1.43 (m, 1H), 1.39 (s, 9H), 1.06 (s, 3H) |
| C-4-2 | 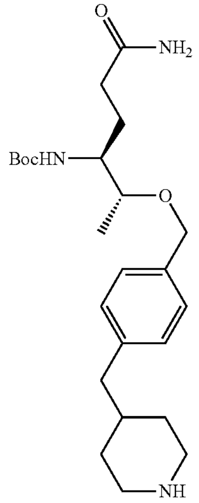 [SMILES: C[C@@H](OCc1ccc(CC2CCNCC2)cc1)[C@H](CCC(N)=O)NC(=O)OC(C)(C)C] | tert-butyl N-[(3S,4R)-1-carbamoyl-4-[[4-(piperidin-4-yl-methyl)phenyl]meth-oxy]pentan-3-yl]carbamate | 434.30 | $^1$H NMR (400 MHz, DMSO-$d_6$) δ 7.27-7.17 (m, 3H), 7.10 (d, J = 7.8 Hz, 2H), 6.69 (s, 1H), 6.62 (d, J = 9.1 Hz, 1H), 4.53-4.36 (m, 2H), 3.52-3.19 (m, 4H), 2.95-2.79 (m, 2H), 2.45 (d, J = 6.9 Hz, 2H), 2.40-2.31 (m, 2H), 2.08-2.01 (m, 2H), 1.81-1.77 (m, 1H), 1.58-1.40 (m, 3H), 1.39 (s, 9H), 1.09-0.95 (m, 5H). |

Step 5. Tert-butyl N-[3-[4-([[(2R,3S)-3-amino-5-carbamoylpentan-2-yl]oxy]methyl)phenyl]propyl]carbamate (Intermediate C). A solution of tert-butyl N-[13-[14-([[(2R,3S)-5-carbamoyl-3-([[2-(trimethylsilyl) ethoxy]carbonyl] amino)pentan-2-yl]oxy]methyl)phenyl]propyl]carbamate (200 mg, 0.37 minol) and TBAF (292 mg, 1.12 minol) in THF (10.0 mL) was stirred for 16 hours at room temperature under nitrogen atmosphere. The resulting mixture was concentrated under reduced pressure. The residue was purified by reversed phase flash chromatography with the following conditions: column, C18 silica gel; 20~40 μm, 40 g; Mobile phase A: water (plus 10 mmol/L AcOH); Mobile phase B: CAN. Gradient: 15% to 35% B in 20 min; Detector: UV 254/220 nm; desired fractions were collected at 2700 B and concentrated under reduced pressure to afford the title compound as a white solid (130 mg, 89%): $^1$H NMR (400 MHz, DMSO-$d_6$) δ 7.23 (d, J=7.9 Hz, 2H), 7.16 (d, J=7.9 Hz, 2H), 4.47 (d, J=11.7 Hz, 1H), 4.38 (d, J=11.7 Hz, 1H), 3.32 (dd, J=6.4, 4.7 Hz, 1H), 2.92 (q, J=6.7 Hz, 2H), 2.71-2.61 (m, 1H), 2.55 (d, J=7.6 Hz, 2H), 2.26-2.00 (m, 2H), 1.65 (s, 8H), 1.38 (s, 9H), 1.08 (dd, J=9.8, 6.1 Hz, 3H); MS (ESI, m/z): $[(M+1)]^+$=394.30.

(9H-fluoren-9-yl)methyl N-1(2S)-1-1(1R,2S,5S)-2-11(3S,4R)-4-14-(3-aminopropyl)phenyl]methoxy]-1-carbamoylpentan-3-yl]carbamoyl]-3-azabicyclo [3.1.0]hexan-3-yl]-1-oxohexan-2-yl]carbamate hydrochloride (Intermediate D)

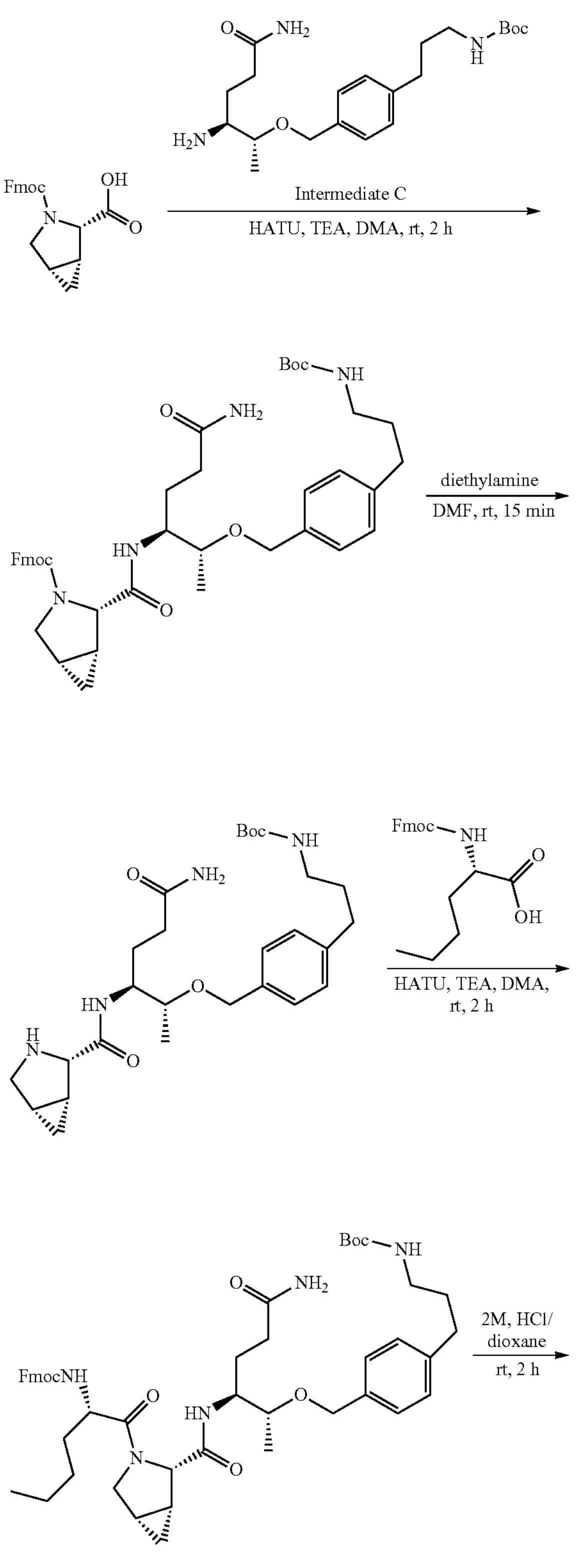

-continued

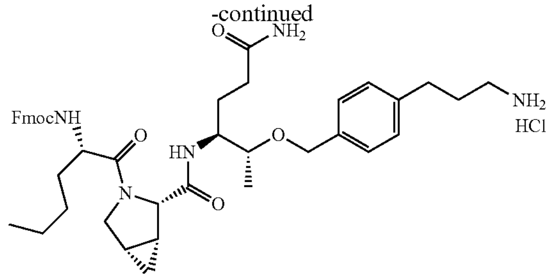

Intermediate D

Step 1. 9H-fluoren-9-ylmethyl (1R,2S,5S)-2-[[(3S,4R)-4-[(4-[3-[(tert-butoxycarbonyl)amino]propyl]phenyl) methoxy]-1-carbamoylpentan-3-yl]carbamoyl]-3-azabicyclo[3.1.01hexane-3-carboxylate. To a solution of (1R,2S,5S)-3-[(9H-fluoren-9-ylmethoxy)carbonyl]-3-azabicyclo [3.1.0]hexane-2-carboxylic acid (390 mg, 1.12 mmol) and tert-butyl N-[3-[4-([[(2R,3S)-3-amino-5-carbamoylpentan-2-yl]oxy]methyl)phenyl]propyl]carbamate (439 mg, 1.12 mmol) in DMA (10 mL) was added TEA (339 mg, 3.35 mmol). The mixture was stirred at room temperature for 5 min then HATU (552 mg, 1.45 mmol) was added. The mixture was stirred at room temperature for 1 hour. The resulting mixture was purified by reversed phase flash chromatography with the following conditions: Column: WelFlash™ C18-I, 20~40 um, 330 g; EluentA: water (plus 10 mmol/L HOAc); Eluent B: ACN; Gradient: 40% - 60% B in 20 min; Flow rate: 80 mL/min; Detector: UV 220/254 nm; desired fractions were collected at 58% B and concentrated under reduced pressure to afford the title compound (610 mg, 76%) as a white solid: $^{1}H$ NMR (400 MHz, DMSO-$d_6$) δ 7.91 (d, J=8.0 Hz, 2H), 7.64 (q, J=7.0, 6.6 Hz, 2H), 7.43 (t, J=7.4 Hz, 2H), 7.39-7.28 (m, 2H), 7.26-7.04 (m, 5H), 6.86 (s, 1H), 6.73-6.58 (m, 1H), 4.50-4.38 (m, 2H), 4.33-4.08 (m, 3H), 3.78 (d, J=39.1 Hz, 1H), 3.40 (t, J=6.0 Hz, 2H), 2.94-2.86 (m, 2H), 2.55 (d, J=8.0 Hz, 2H), 2.09-1.93 (m, 2H), 1.82 (s, 2H), 1.66-1.62 (m, 4H), 1.38 (s, 1OH), 1.13-1.06 (m, 3H), 0.69 (s, 1H), 0.55 (s, 1H); MS (ESI, m/z): $[(M+1)]^+$=725.35.

Step 2. Tert-butyl N-[3-[4-([[(2R,3S)-3-[[(1R,2S,5S)-3-azabicyclo[3.1.0]hexan-2-yl]formamido]-5-carbamoylpentan-2-yl]oxy]methyl)phenyl]propyl]carbamate. To a solution of (9H-fluoren-9-yl)methyl (1R,2S,5S)-2-[[(3S,4R)-4-[[4-(3-[[(tert-butoxy)carbonyl]amino]propyl)phenyl] methoxy]-1-carbamoylpentan-3-yl]carbamoyl]-3-azabicyclo[3.1.0]hexane-3-carboxylate (610 mg, 0.84 mmol) in DMF (10 mL) was added diethylamine (2 mL) at room temperature. The mixture was stirred at room temperature for 20 min. The resulting mixture was acidified to pH=6 with HOAc (4 mL) at 0° C. and purified by reversed phase flash chromatography with the following conditions: Column: WelFlash™ C18-I, 20~40 um, 120 g; Eluent A: water (plus 10 mmol/L HOAc); Eluent B: ACN; Gradient: 15% - 35% B in 20 min; Flow rate: 80 mL/min; Detector: UV 220/254 nm; desired fractions were collected at 26% B and concentrated under reduced pressure to afford the title compound as a white solid (400 mg, 95%): $^{1}H$ NMR (400 MHz, DMSO-$d_6$) δ 7.70 (d, J=9.4 Hz, 1H), 7.28-7.20 (m, 3H), 7.18-7.13 (m, 2H), 6.85 (d, J=6.2 Hz, 1H), 6.69 (s, 1H), 4.50-4.38 (m, 2H), 3.83-3.73 (m, 1H), 3.56 (d, J=3.9 Hz, 1H), 3.44 (p, J=6.1 Hz, 1H), 2.94-2.90 (m, 3H), 2.81 (dd, J=10.7, 3.6 Hz, 1H), 2.55 (d, J=7.6 Hz, 2H), 2.08-1.97 (m, 2H), 1.87 (dtd, J=17.2, 7.1, 3.8 Hz, 1H), 1.66 (q, J=7.3 Hz, 2H), 1.61-1.49 (m, 2H), 1.38 (s, 11H), 1.09 (d, J=6.3 Hz, 3H), 0.32 (q, J=4.3 Hz, 1H), 0.25 (td, J=7.7, 4.7 Hz, 1H); MS (ESI, m/z): $[(M+1)]^+$=503.40.

Step 3. (9H-fluoren-9-yl)methyl N-[(2S)-1-[(1R,2S,5S)-2-[[(3S,4R)-4-[[4-(3-[[(tert-butoxy)carbonyl]amino]propyl)phenyl]methoxy]-1-carbamoylpentan-3-yl]carbamoyl]-3-azabicyclo[3.1.0]hexan-3-yl]-1-oxohexan-2-yl]carbamate. To a solution of tert-butyl N-[3-[4-([[(2R,3S)-3-[[(1R,2S,5S)-3-azabicyclo[3.1.0]hexan-2-yl]formamido]-5-carbamoylpentan-2-yl]oxy]methyl)phenyl]propyl]carbamate (400 mg, 0.80 mmol) and (2S)-2-([[(9H-fluoren-9-yl)methoxy]carbonyl]amino)hexanoic acid (281 mg, 0.80 mmol) in DMA (8 mL) was added TEA (242 mg, 2.39 mmol). The mixture was stirred at room temperature for 5 min then HATU (393 mg, 1.04 mmol) was added. The mixture was stirred at room temperature for 1 hour. The resulting mixture was purified by reversed phase flash chromatography with the following conditions: Column: WelFlash™ C18-I, 20~40 um, 330 g; Eluent A: water (plus 10 mmol/L HOAc); Eluent B: ACN; Gradient: 40% - 60% B in 20 min; Flow rate: 80 mL/min; Detector: UV 220/254 nm; desired fractions were collected at 58% B and concentrated under reduced pressure to afford the title compound as a white solid (600 mg, 90%): $^1$H NMR (400 MHz, DMSO-d4) δ 7.90 (d, J=7.5 Hz, 2H), 7.74 (dd, J=7.5, 3.9 Hz, 2H), 7.60 (dd, J=12.4, 8.3 Hz, 2H), 7.43 (t, J=7.5 Hz, 2H), 7.34 (t, J=7.4 Hz, 2H), 7.25 (d, J=7.8 Hz, 2H), 7.16 (d, J=7.8 Hz, 2H), 7.06 (s, 1H), 6.86 (s, 1H), 6.68 (s, 1H), 4.53-4.32 (m, 3H), 4.29-4.19 (m, 3H), 4.11 (d, J=6.3 Hz, 1H), 3.88 (d, J=9.9 Hz, 1H), 3.72 (s, 1H), 3.60 (d, J=9.7 Hz, 1H), 3.38 (t, J=6.2 Hz, 1H), 2.94-2.88 (m, 2H), 2.70 (s, 1H), 2.55 (d, J=7.8 Hz, 2H), 2.11 (d, J=9.2 Hz, 2H), 1.81 (s, 1H), 1.69 (s, 1H), 1.65 (t, J=7.4 Hz, 2H), 1.55-1.52 (m, 3H), 1.39 (s, 9H), 1.31-1.26 (m, 3H), 1.10-1.07 (m, 3H), 0.89-0.86 (m, 3H), 0.71 (d, J=4.5 Hz, 1H), 0.57 (s, 1H); MS (ESI, m/z): $[(M+1)]^+$=838.35.

Step 4. (9H-fluoren-9-yl)methyl N-[(2S)-1-[(1R,2S,5S)-2-[[(3S,4R)-4-[[4-(3-aminopropyl)phenyl]methoxy]-1-carbamoylpentan-3-yl]carbamoyl]-3-azabicyclo[3.1.0]hexan-3-yl]-1-oxohexan-2-yl]carbamate hydrochloride (Intermediate D). To a solution of (9H-fluoren-9-yl)methyl N-[(2S)-1-[(1R,2S,5S)-2-[[(3S,4R)-4-[[4-(3-[[(tert-butoxy)carbonyl]amino]propyl)phenyl]methoxy]-1-carbamoylpentan-3-yl]carbamoyl]-3-azabicyclo[3.1.0]hexan-3-yl]-1-oxohexan-2-yl]carbamate (600 mg, 0.72 mmol) in dioxane (6 mL) was added 4 M HCl (gas) in 1,4-dioxane (6 mL) at room temperature. The reaction mixture was stirred at room temperature for 1 hour. The resulting mixture was concentrated under reduced pressure to give the title compound as a white solid (550 mg, 99%): $^1$H NMR (400 MHz, DMSO-$d_6$) δ 7.91-7.89 (m, 4H), 7.73 (dd, J=7.3, 3.9 Hz, 2H), 7.61 (d, J=8.4 Hz, 2H), 7.42 (t, J=7.5 Hz, 2H), 7.33 (t, J=7.3 Hz, 2H), 7.28 (d, J=7.8 Hz, 2H), 7.18 (d, J=7.9 Hz, 2H), 7.08 (s, 1H), 6.69 (s, 1H), 4.50-4.36 (m, 3H), 4.28-4.18 (m, 3H), 4.14-4.05 (m, 1H), 3.91-3.83 (m, 1H), 3.71 (s, 1H), 2.79 (s, 5H), 2.64 (t, J=7.7 Hz, 2H), 2.11 (d, J=8.2 Hz, 2H), 1.85-1.80 (m, 3H), 1.71 (s, 1H), 1.52-1.47 (m, 3H), 1.36-1.19 (m, 5H), 1.09 (d, J=6.2 Hz, 3H), 0.88-0.85 (m, 3H), 0.72-0.70 (m, 1H), 0.60-0.53 (m, 1H); MS (ESI, m/z): $[(M+1)]^+$=738.35.

(9H-fluoren-9-yl)methyl N-[(2S,11S)-2-[[(3S,4R)-4-[[4-(3-aminopropyl)phenyl]methoxy]-1-carbamoylpentan-3-yl]carbamoyl]-12-oxo-1-azatricyclo[6.4.1.0[4,13]]trideca-4(13), 5,7-trien-11-yl]carbamate (Intermediate E)

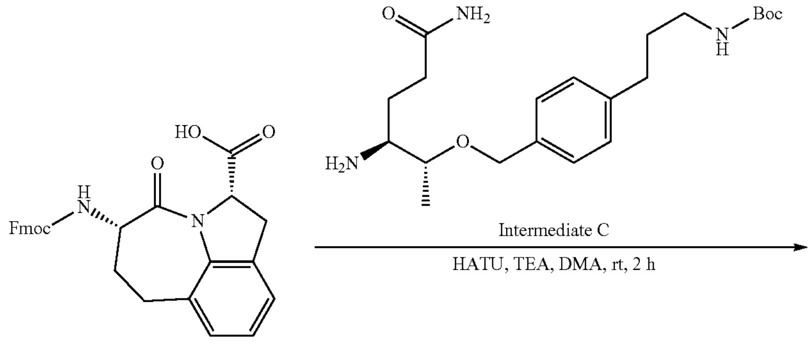

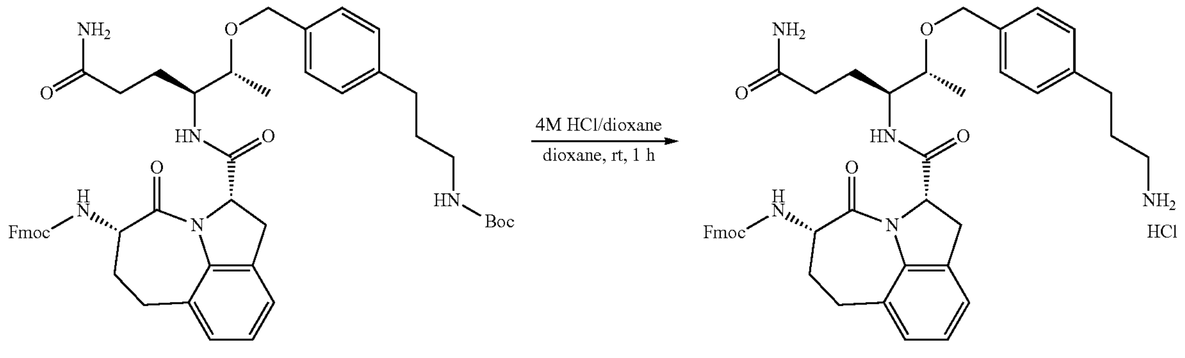

Intermediate E

Step 1. (9H-fluoren-9-yl)methyl N-[(2S,11S)-2-[[(3S,4R)-4-[[4-(3-[[(tert-butoxy)carbonyl]amino]propyl)phenyl]methoxy]-1-carbamoylpentan-3-yl]carbamoyl]-12-oxo-1-azatricyclo[6.4.1.0[4,13]]trideca-4(13), 5,7-trien-11-yl]carbamate. To a solution of (2S,11S)-11-([[(9H-fluoren-9-yl)methoxy]carbonyl]amino)-12-oxo-1-azatricyclo[6.4.1.0[4,13]]trideca-4(13), 5,7-triene-2-carboxylic acid (850 mg, 1.81 mmol) in DMA (15 mL) were added TEA (551 mg, 5.44 mmol) and HATU (897 mg, 2.36 mmol) at room temperature. The mixture was stirred at room temperature for 10 min. Then tert-butyl N-[3-[4-([[(2R,3S)-3-amino-5-carbamoylpentan-2-yl]oxy]methyl)phenyl]propyl]carbamate (714 mg, 1.81 mmol) was added. The mixture was stirred at room temperature for 1 hour. The resulting mixture was diluted with water (50 mL). The precipitated solids were collected by filtration and washed with water (3×30 mL), dried under vacuum to give the title compound as a white solid (1.40 g, 91%): $^1$H NMR (400 MHz, DMSO-$d_6$) δ 7.90 (d, J=7.5 Hz, 2H), 7.84 (d, J=9.2 Hz, 1H), 7.75 (q, J=8.3, 7.6 Hz, 3H), 7.43 (t, J=7.6 Hz, 2H), 7.34 (t, J=7.5 Hz, 2H), 7.17 (d, J=7.8 Hz, 3H), 7.11 (d, J=7.8 Hz, 2H), 7.06 (d, J=7.6 Hz, 2H), 6.97 (t, J=7.4 Hz, 1H), 6.85 (s, 1H), 6.69 (s, 1H), 5.06 (d, J=10.2 Hz, 1H), 4.40 (s, 2H), 4.34-4.21 (m, 3H), 4.13 (s, 1H), 3.79 (s, 1H), 3.46-3.40 (m, 2H), 3.17 (d, J=16.8 Hz, 1H), 3.08 (d, J=14.4 Hz, 1H), 2.96-2.91 (m, 2H), 2.85 (d, J=16.7 Hz, 1H), 2.55 (d, J=7.6 Hz, 2H), 2.11-2.02 (m, 3H), 1.78 (s, 1H), 1.67 (q, J=7.3 Hz, 2H), 1.57 (s, 1H), 1.39 (s, 9H), 1.08 (d, J=6.2 Hz, 3H), 0.94 (t, J=7.3 Hz, 1H); MS (ESI, m/z): [(M+1)]$^+$=844.50.

The intermediates in Table 19 were prepared according to step 1 of the procedure to prepare Intermediate E.

TABLE 19

Characterization data for intermediates prepared according to above.

| Intermediate | Structure | Chemical Name | MS: [(M + 1)]$^+$ | $^1$H-NMR |
|---|---|---|---|---|
| E-1-1 | 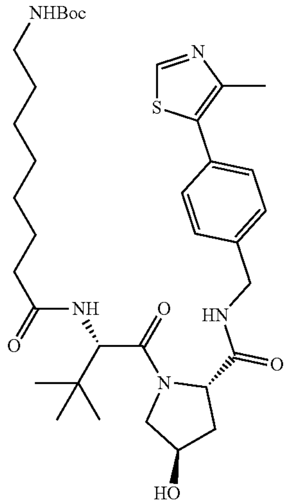 [SMILES: Cc1ncsc1-c1ccc(CNC(=O)[C@@H]2C[C@@H](O)CN2C(=O)[C@@H](NC(=O)CCCCCCCNC(=O)OC(C)(C)C)C(C)(C)C)cc1] | tert-butyl N-(7-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]heptyl)carbamate | 672.45 | (400 MHz, DMSO-$d_6$) δ 8.99 (s, 1H), 8.56 (t, J = 6.1 Hz, 1H), 7.84 (d, J = 9.3 Hz, 1H), 7.41 (q, J = 8.5 Hz, 4H), 6.74 (d, J = 6.1 Hz, 1H), 4.55 (d, J = 9.4 Hz, 1H), 4.44 (q, J = 7.7 Hz, 2H), 4.36 (s, 1H), 4.24-4.20 (m, 1H), 3.65 (t, J = 8.7 Hz, 1H), 3.31 (s, 2H), 2.88 (q, J = 6.7 Hz, 2H), 2.45 (s, 3H), 2.28-2.24 (m, 1H), 2.16-2.05 (m, 1H), 2.04-2.00 (m, 1H), 1.93-1.89 (m, 1H), 1.55-1.42 (m, 2H), 1.37 (s, 9H), 1.25-1.20 (m, 8H), 0.94 (s, 9H) |
| E-1-2 | 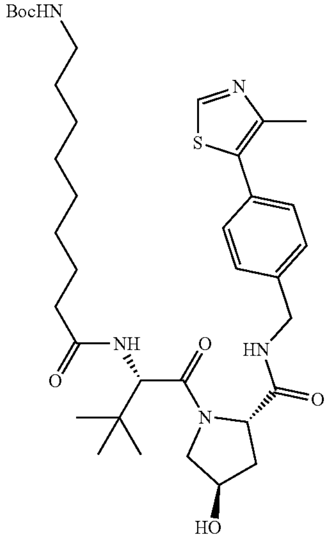 [SMILES: Cc1ncsc1-c1ccc(CNC(=O)[C@@H]2C[C@@H](O)CN2C(=O)[C@@H](NC(=O)CCCCCCCCNC(=O)OC(C)(C)C)C(C)(C)C)cc1] | tert-butyl N-(8-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]octyl)carbamate | 686.30 | (400 MHz, DMSO-$d_6$) δ 8.99 (s, 1H), 8.56 (t, J = 6.1 Hz, 1H), 7.84 (d, J = 9.3 Hz, 1H), 7.41 (q, J = 8.4 Hz, 4H), 6.75 (t, J = 5.5 Hz, 1H), 5.13 (s, 1H), 4.55 (d, J = 9.4 Hz, 1H), 4.51-4.39 (m, 2H), 4.36 (s, 1H), 4.22 (dd, J = 15.9, 5.5 Hz, 1H), 3.72-3.60 (m, 2H), 2.88 (q, J = 6.6 Hz, 2H), 2.45 (s, 3H), 2.29-2.23 (m, 1H), 2.17-2.04 (m, 1H), 2.05-2.01 (m, 1H), 1.94-1.89 (m, 1H), 1.49-1.45 (m, 2H), 1.37 (s, 9H), 1.37-1.33 (m, 2H), 1.25-1.18 (m, 8H), 0.94 (s, 9H) |

TABLE 19-continued

Characterization data for intermediates prepared according to above.

| Inter-mediate | Structure | Chemical Name | MS: $[(M + 1)]^+$ | $^1$H-NMR |
|---|---|---|---|---|
| E-1-3 | 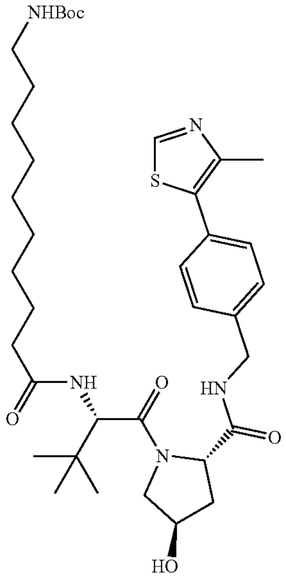 [SMILES: Cc1ncsc1-c1ccc(CNC(=O)[C@@H]2C[C@@H](O)CN2C(=O)[C@@H](NC(=O)CCCCCCCCCNC(=O)OC(C)(C)C)C(C)(C)C)cc1] | tert-butyl N-(9-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]nonyl)carbamate | 700.60 | (400 MHz, DMSO-$d_6$) δ 8.99 (s, 1H), 8.57 (t, J = 6.1 Hz, 1H), 7.84 (d, J = 9.3 Hz, 1H), 7.41 (q, J = 8.3 Hz, 4H), 6.75 (t, J = 5.8 Hz, 1H), 5.13 (s, 1H), 4.55 (d J = 9.4 Hz, 1H), 4.51-4.39 (m, 2H), 4.36 (s, 1H), 4.24-4.20 (m, 1H), 3.72-3.61 (m, 2H), 3.18 (s, 1H), 2.97-2.84 (m, 2H), 2.45 (s, 3H), 2.32-2.20 (m, 1H), 2.15 -1.99 (m, 2H), 1.93-1.89 (m, 1H), 1.52-1.48 (m, 1H), 1.37 (s, 9H), 1.25-1.21 (m, 12H), 0.94 (s, 9H) |
| E-1-4 | 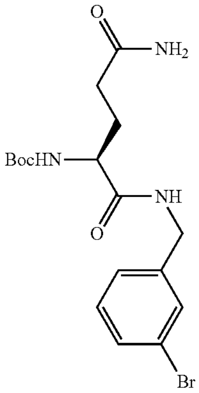 [SMILES: CC(C)(C)OC(=O)N[C@@H](CCC(N)=O)C(=O)NCc1cccc(Br)c1] | tert-butyl N-[(1S)-1-[[(3-bromophenyl)methyl]carbamoyl]-3-carbamoylpropyl]carbamate | 413.95, 415.95 | (400 MHz, $CDCl_3$) δ 7.46-.40 (m, 2H), 7.24-7.21 (m, 2H), 7.12 (s, 1H), 6.06 (s, 1H), 5.71 (s, 1H), 5.49 (s, 1H), 4.44 (d, J = 5.6 Hz, 2H), 4.20 (s, 1H), 2.53-2.42 (m, 1H), 2.40-2.31 (m, 1H), 2.21-2.08 (m, 1H), 2.06-1.96 (m, 1H), 1.45 (s, 9H) |

Step 2. (9H-fluoren-9-yl)methyl N-[(2S,11S)-2-[[(3SAR)-4-[[4-(3-aminopropyl)phenyl]methoxy]-1-carbamoylpentan-3-yl]carbamoyl]-12-oxo-1-azatricyclo[6.4.1.0^[4.13]]trideca-4(13), 5,7-trien-11-yl]carbamate (Intermediate E). To a solution of (9H-fluoren-9-yl)methyl N-[(2S,11S)-2-[[(3S,4R)-4-[[4-(3-[[(tert-butoxy) carbonyl]amino]propyl)phenyl]methoxy]-1-carbamoylpentan-3-yl]carbamoyl]-12-oxo-1-azatricyclo[6.4.1.0^[4, 13]]trideca-4(13), 5,7-trien-11-yl]carbamate (1.40 g, 1.66 minol) in dioxane (15 mL) was added a solution of 4 M HCl (gas) in 1,4-dioxane (1S mL) at room temperature. The mixture was stirred at room temperature for 1 hour. The resulting mixture was concentrated under reduced pressure to give the title compound as a white solid (1.20 g, 97R): 1H NMR (400 MHz, DMSO-)) 9 7.94-7.83 (s, 3H), 7.76 (t, J 7.1 Hz, 2H), 7.43 (t, J 7.5 Hz, 2H), 7.38-7.31 (8, 2H), 7.25-7.09 (d, 5H), 7.09-6.94 (i, 3H), 6.71 (s, 1H), 5.06 (d, J=10.8 Hz, 1H), 4.41 (s, 2H), 4.33-4.22 (m, 2H), 4.13 (s, 1H), 3.78 (s, 1H), 3.45 (dd, J=11.6, 6.0 Hz, 2H), 3.35-3.30 (m, 3H), 3.20-3.13 (m, 2H), 3.05 (s, 1H), 2.85 (d, J=16.7 Hz, 1H), 2.72 (d, J=7.4 Hz, 1H), 2.60 (d, J 7.7 Hz, 1H), 2.09-2.06 (m, 3H), 1.87-1.71 (m, 3H), 1.57 (s, 2H), 1.31 (p, J=7.1 Hz, 2H), 1.08 (d, J=6.2 Hz, 3H); MS (ESI, m/z): 5M+1))=744.35.

The intermediates in Table 20 were prepared according to step 2 of the procedure to prepare Intermediate E.

TABLE 20

| Characterization data for intermediates prepared according to above. | | | | |
|---|---|---|---|---|
| Intermediate | Structure | Chemical Name | MS :[(M + 1)]$^+$ | $^1$H-NMR |
| E1 | 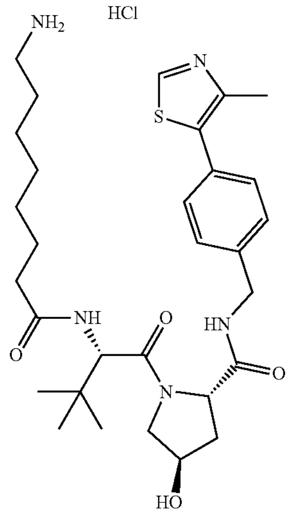 [SMILES: Cl ; Cc1ncsc1-c1ccc(CNC(=O)[C@@H]2C[C@@H](O)CN2C(=O)[C@@H](NC(=O)CCCCCCCN)C(C)(C)C)cc1] | (2S,4R)-1-[(2S)-2-(8-amino-octanamido)-3,3-dimethylbutanoyl]-4-hydroxy-N-[[4-(4-methyl-1,3-thiazol-5-yl)phenyl]methyl]pyrrolidine-2-carboxamide hydrochloride | 572.50 | (400 MHz, DMSO-d$_6$) δ 9.13 (s, 1H), 8.61 (d, J = 6.4 Hz, 1H), 7.85 (d, J = 9.3 Hz, 1H), 7.42 (q, J = 8.3 Hz, 4H), 5.76 (s, 1H), 4.55 (d, J = 9.4 Hz, 1H), 4.48-4.39 (m, 2H), 4.35 (s, 1H), 4.23 (dd, J = 15.9, 5.2 Hz, 1H), 3.71--3.63 (m, 2H), 2.74 (d, J = 8.0 Hz, 2H), 2.46 (s, 3H), 2.28-2.24 (m, 1H), 2.19-2.00 (m, 2H), 1.92-1.89 (m, 1H), 1.82-1.70 (m, 2H), 1.60-1.42 (m, 2H), 1.28-1.24 (m, 8H), 0.94 (s, 9H) |
| E2 | 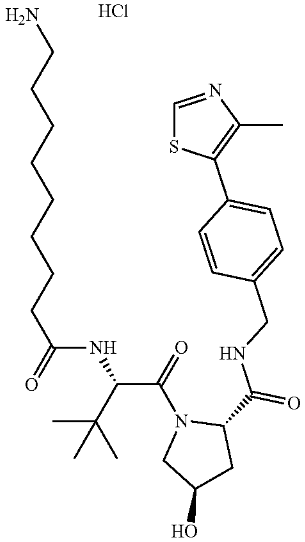 [SMILES: Cl ; Cc1ncsc1-c1ccc(CNC(=O)[C@@H]2C[C@@H](O)CN2C(=O)[C@@H](NC(=O)CCCCCCCCN)C(C)(C)C)cc1] | (2S,4R)-1-[(2S)-2-(9-aminononanamido)-3,3-dimethylbutanoyl]-4-hydroxy-N-[[4-(4-methyl-1,3-thiazol-5-yl)phenyl]methyl]pyrrolidine-2-carboxamide hydrochloride | 586.50 | (400 MHz, DMSO-d$_6$) δ 9.30-9.09 (m, 1H), 8.63 (t, J = 5.7 Hz, 1H), 7.85 (d, J = 9.4 Hz, 1H), 7.44-7.40 (m, 4H), 5.26 (d, J = 13.9 Hz, 1H), 4.54 (d, J = 9.4 Hz, 1H), 4.48-4.38 (m, 2H), 4.35 (d, J = 4.1 Hz, 1H), 4.25-4.21 (m, 1H), 3.71-3.63 (m, 2H), 2.73 (q, J = 7.5, 7.0 Hz, 2H), 2.47 (s, 3H), 2.30-2.24 (m, 1H), 2.18-2.00 (m, 2H), 1.93-1.88 (m, 1H), 1.61-1.57 (m, 4H), 1.20-1.16 (m, 10H), 0.94 (s, 9H) |

TABLE 20-continued

Characterization data for intermediates prepared according to above.

| Intermediate | Structure | Chemical Name | MS :[(M + 1)]$^+$ | $^1$H-NMR |
|---|---|---|---|---|
| E3 | 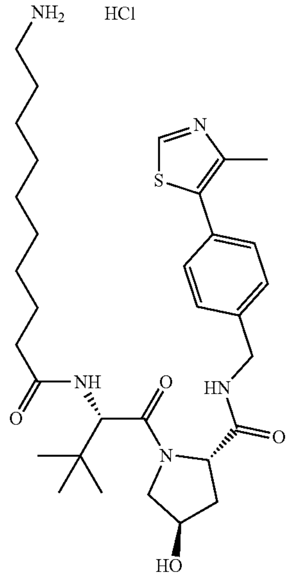 [SMILES: Cc1ncsc1-c1ccc(CNC(=O)[C@@H]2C[C@@H](O)CN2C(=O)[C@@H](NC(=O)CCCCCCCCCN)C(C)(C)C)cc1 ; Cl] | (2S,4R)-1-[(2S)-2-(10-aminodecan-amido)-3,3-dimethylbutanoyl]-4-hydroxy-N-[[4-(4-methyl-1,3-thiazol-5-yl)phenyl]methyl]pyr-rolidine-2-carboxamide hydrochloride | 600.50 | (400 MHz, DMSO-$d_6$) δ 9.07 (s, 1H), 8.59 (t, J = 6.1 Hz, 1H), 7.93 (s, 1H), 7.84 (d, J = 9.3 Hz, 1H), 7.46-7.36 (m, 4H), 4.55 (d, J = 9.3 Hz, 1H), 4.49-4.39 (m, 2H), 4.36 (s, 1H), 4.24-4.20 (m, 1H), 3.71-3.63 (m, 2H), 2.76-2.72 (m, 2H), 2.46 (d, J = 3.7 Hz, 3H), 2.27-2.23 (m, 1H), 2.17-2.01 (m, 2H), 1.93-1.88 (m, 1H), 1.55-1.48 (m, 4H), 1.27-1.23 (m, 12H), 0.94 (s, 9H) |
| E4 | 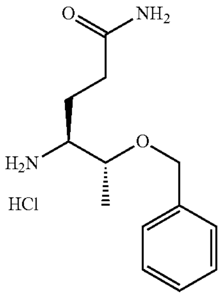 [SMILES: Cl ; C[C@@H](OCc1ccccc1)[C@@H](N)CCC(N)=O] | (4S,5R)-4-Amino-5-(benzyloxy)hex-anamide hydrochloride | 237.25 | (400 MHz, DMSO-$d_6$) δ 8.29-8.10 (m, 2H), 7.50 (s, 1H), 7.42-7.25 (m, 6H), 6.92 (s, 1H), 4.47 (s, 2H), 3.86-3.75 (m, 1H), 3.33-3.12 (m, 1H), 2.27 (t, J = 8.0 Hz, 2H), 1.77 (p, J = 7.5 Hz, 2H), 1.16 (d, J = 6.4 Hz, 3H) |
| E5 | 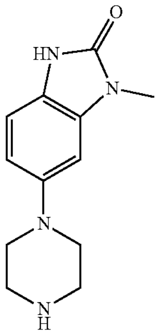 [SMILES: Cn1c(=O)[nH]c2ccc(N3CCNCC3)cc21] | 1-Methyl-6-(piperazin-1-yl)-3H-1,3-benzodiazol-2-one | 233.10 | (400 MHz, DMSO-$d_6$) δ 10.54 (s, 1H), 6.82 (d, J = 8.4 Hz, 1H), 6.73 (s, 1H), 6.57 (d, J = 8.5 Hz, 1H), 3.24 (s, 3H), 3.04-2.97 (m, 4H), 2.94-2.86 (m, 4H), 1.42-1.37 (m, 1H) |

TABLE 20-continued

Characterization data for intermediates prepared according to above.

| Intermediate | Structure | Chemical Name | MS :[(M + 1)]+ | $^1$H-NMR |
|---|---|---|---|---|
| E6 | 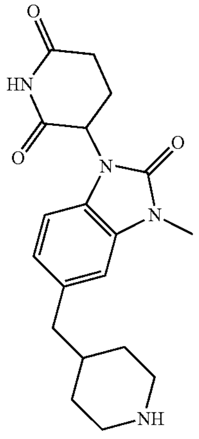 TFA | 3-[3-Methyl-2-oxo-5-(piperidin-4-ylmethyl)-1,3-benzodiazol-1-yl]piperidine-2,6-dione trifluoroacetate | 357.15 | (400 MHz, DMSO-$d_6$) δ 11.09 (s, 1H), 8.61 (d, J = 11.3 Hz, 1H), 7.04 (d, J = 7.4 Hz, 2H), 6.86 (d, J = 8.0 Hz, 1H), 5.35 (dd, J = 12.7, 5.4 Hz, 1H), 3.47-3.42 (s, 1H), 3.33 (s, 3H), 3.25 (d, J = 12.5 Hz, 2H), 2.99-2.54 (m, 6H), 2.04-1.96 (m, 1H), 1.84-1.67 (m, 3H), 1.42-1.26 (m, 2H) |
| E7 | 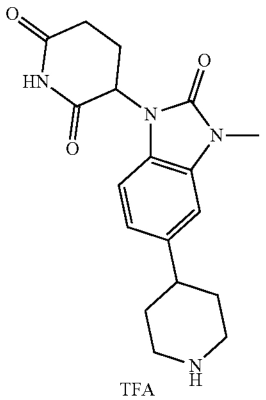 TFA | 3-[3-Methyl-2-oxo-5-(piperidin-4-yl)-1,3-benzodiazol-1-yl]piperidine-2,6-dione trifluoroacetate | 343.15 | (400 MHz, DMSO-$d_6$) δ 11.10 (s, 1H), 8.75 (d, J = 11.5 Hz, 1H), 8.46 (d, J = 11.7 Hz, 1H), 7.13-7.02 (m, 2H), 6.91 (dd, J = 8.2, 1.6 Hz, 1H), 5.36 (dd, J = 12.7, 5.4 Hz, 1H), 3.35 (s, 3H), 3.11-2.84 (m, 4H), 2.78-2.58 (m, 2H), 2.09-1.75 (m, 5H) |
| E8 | 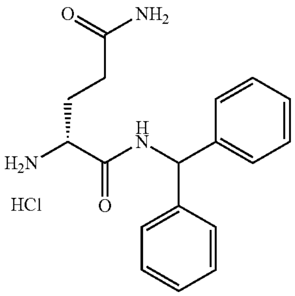 HCl | (2R)-2-amino-N-(diphenyl-methyl)pentane-diamide hydrochloride | 312.10 | (400 MHz, DMSO-$d_6$) δ 9.62 (d, J = 8.9 Hz, 1H), 8.40 (s, 3H), 7.52 (s, 1H), 7.41-7.28 (m, 8H), 7.31-7.22 (m, 2H), 6.96 (s, 1H), 6.15 (d, J = 8.4 Hz, 1H), 4.02 (d, J = 9.5 Hz, 1H), 2.21 (dd, J = 9.2, 6.4 Hz, 2H), 2.04-1.94 (m, 2H) |
| E9 | HCl 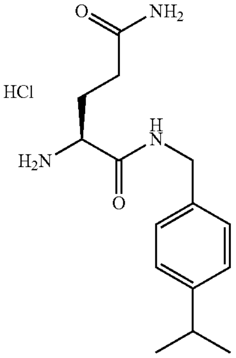 | (2S)-2-amino-N-[(4-isopropyl-phenyl)meth-yl]pentanedi-amide hydrochloride | 278.20 | (400 MHz, DMSO-$d_6$) δ 8.99 (d, J = 5.3 Hz, 1H), 8.35-8.27 (s, 2H), 7.49 (s, 1H), 7.24-7.20 (m, 4H), 6.95 (s, 1H), 4.30 (t, J = 5.8 Hz, 2H), 3.81 (d, J = 5.9 Hz, 1H), 2.92-2.84 (m, 1H), 2.20 (m, 2H), 1.98-1.94 (m, 2H), 1.19 (d, J = 6.9 Hz, 6H) |

TABLE 20-continued

| Characterization data for intermediates prepared according to above. | | | | |
|---|---|---|---|---|
| Intermediate | Structure | Chemical Name | MS :[(M + 1)]+ | $^1$H-NMR |
| E10 | 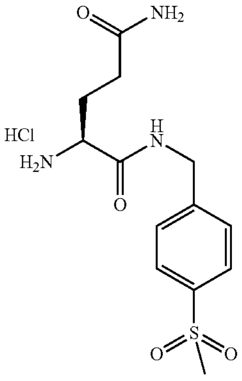 [SMILES: Cl ; CS(=O)(=O)c1ccc(CNC(=O)[C@@H](N)CCC(N)=O)cc1] | (2S)-2-amino-N-[(4-methanesulfonyl-phenyl)meth-yl]pentanediamide hydrochloride | 314.05 | (300 MHz, DMSO-d$_6$) δ 9.40 (t, J = 5.8 Hz, 1H), 8.48 (br, 3H), 7.96-7.83 (m, 2H), 7.74-7.53 (m, 2H), 7.13 (d, J = 100.0 Hz, 3H), 4.56-4.27 (m, 2H), 4.02-3.81 (m, 1H), 3.22 (s, 3H), 2.24 (t, J = 8.0 Hz, 2H), 2.02 (q, J = 8.3, 7.7 Hz, 2H) |

Tert-butyl N-[(3S,4R)-1-carbamoyl-4-[[4-(5-13-[1-(2,6-dioxopiperidin-3-yl)-3-methyl-2-oxo-1,3-benzodiazol-5-yl]propoxy]pentyl)phenyl]methoxy]pentan-3-yl]carbamate (Intermediate F)

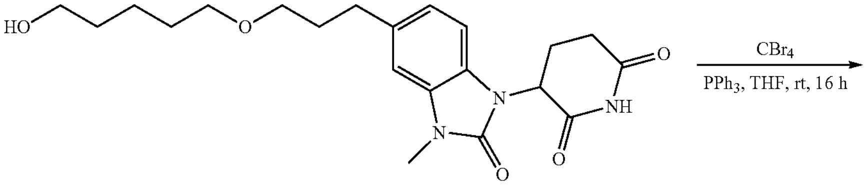

F-1

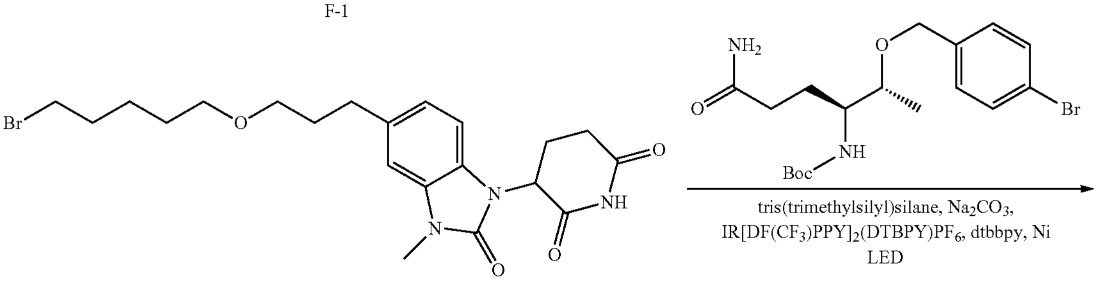

F-2

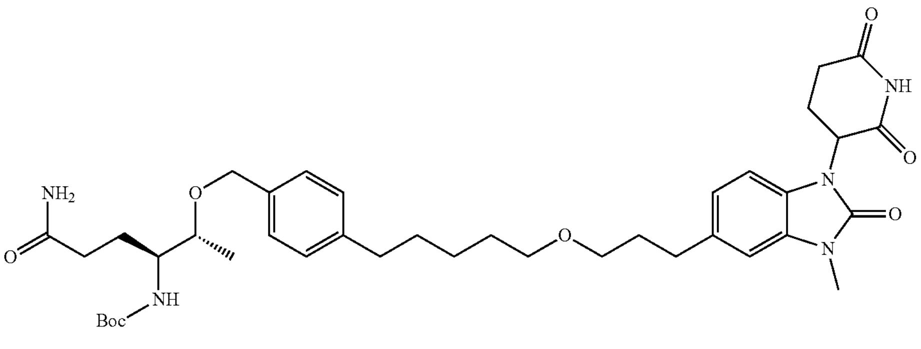

Intermediate F

Step 1. 3-(5-[3-[(5-Bromopentyl)oxy]propyl]-3-methyl-2-oxo-1,3-benzodiazol-1-yl)piperidine-2,6-dione. To a solution of 3-(5-[3-[(5-hydroxypentyl)oxy]propyl]-3-methyl-2-oxo-1,3-benzodiazol-1-yl)piperidine-2,6-dione (760 mg, 1.88 mmol) in THF (20.0 mL) were added $PPh_3$ (988 mg, 3.77 mmol) and $CBr_4$ (1.25 g, 3.77 mmol) at 0° C. The mixture was stirred at 25° C. for 16 hours. The mixture was purified by reverse phase flash chromatography with the following conditions: Column: WelFlash™ C18-I, 20~40 um, 330 g; Eluent A: water (plus 10 mmol/L HOAc); Eluent B: ACN; Gradient: 40% - 60% B in 20 min; Flow rate: 50 mL/min; Detector: UV 220/254 nm; desired fractions were collected at 53% B and concentrated under reduced pressure to afford the title compound as a green oil (780 mg, 89%): $^1$H NMR (400 MHz, DMSO-$d_6$) δ 11.08 (s, 1H), 7.08-6.96 (m, 2H), 6.87 (dd, J=8.1, 1.6 Hz, 1H), 5.34 (dd, J=12.7, 5.4 Hz, 1H), 3.55 (t, J=6.7 Hz, 2H), 3.42-3.33 (m, 7H), 2.90 (ddd, J=16.5, 13.0, 5.2 Hz, 1H), 2.79-2.58 (m, 4H), 2.05-1.95 (m, 1H), 1.83-1.80 (m, 4H), 1.60-1.40 (m, 4H); MS (ESI, m/z): $[(M+1)]^+$=466.15, 468.15.

The intermediates in Table 21 below were prepared according Step 1 of the procedure to prepare Intermediate F.

TABLE 21

Characterization data for intermediates prepared according to above.

| Intermediate | Structure | Chemical Name | MS: $[(M + 1)]^+$ | $^1$H-NMR |
|---|---|---|---|---|
| F-2-1 | 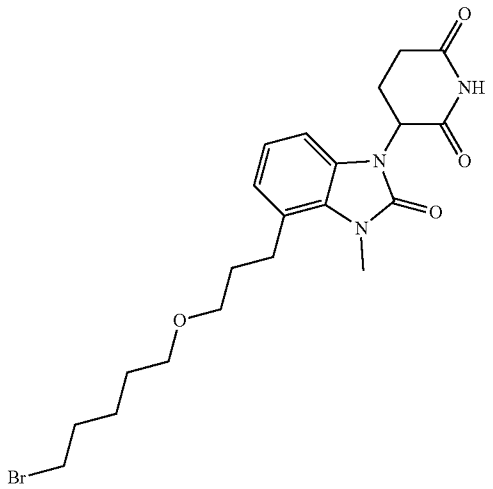 [SMILES: Cn1c(=O)n(C2CCC(=O)NC2=O)c2cccc(CCCOCCCCCBr)c21] | 3-(4-[3-[(5-bromopentyl)oxy]propyl]-3-methyl-2-oxo-1,3-benzodiazol-1-yl)piperidine-2,6-dione | 466.2 468.2 | (400 MHz, DMSO-$d_6$) δ 11.09 (s, 1H), 6.97 (d, J = 4.6 Hz, 2H), 6.88 (q, J = 4.3 Hz, 1H), 5.37 (dd, J = 12.6, 5.4 Hz, 1H), 3.55 (t, J = 6.8 Hz, 3H), 3.41 (dt, J = 15.7, 6.2 Hz, 4H), 3.00-2.92 (m, 2H), 2.95-2.83 (m, 1H), 2.78-2.61 (m, 2H), 2.51 (p, J = 1.9 Hz, 2H), 2.05-1.95 (m, 1H), 1.85-1.81 (m, 4H), 1.55 (p, J = 6.4 Hz, 2H), 1.50-1.39 (m, 2H). |
| F-2-2 | 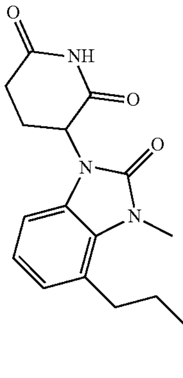 | 3-(4-[3-[(2-bromoethoxy)propyl]-3-methyl-2-oxo-1,3-benzodiazol-1-yl]piperidine-2,6-dione | 424.2 446.2 | (400 MHz, DMSO-$d_6$) δ 11.10 (s, 1H), 6.97 (d, J = 4.8 Hz, 2H), 6.97-6.86 (m, 1H), 5.37 (dd, J = 12.6, 5.4 Hz, 1H), 3.74 (t, J = 5.6 Hz, 2H), 3.63 (t, J = 5.6 Hz, 2H), 3.52 (t, J = 6.1 Hz, 2H), 3.33 (s, 1H), 3.03-2.95 (m, 2H), 2.90 (ddd, J = 17.2, 12.9, 5.2 Hz, 1H), 2.72 (td, J = 12.8, 4.3 Hz, 1H), 2.63 (d, J = 18.4 Hz, 1H), 2.05-1.96 (m, 1H), 1.85 (dq, J = 12.5, 6.3 Hz, 2H), 0.88 (ddd, J = 24.3, 12.0, 6.7 Hz, 1H). |
| F-2-3 | 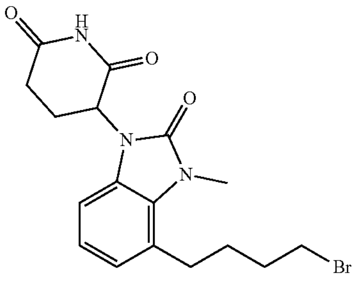 [SMILES: Cn1c(=O)n(C2CCC(=O)NC2=O)c2cccc(CCCCBr)c21] | 3-[4-(4-bromobutyl)-3-methyl-2-oxo-1,3-benzodiazol-yl]piperidine-2,6-dione | 394.2 396.2 | (400 MHz, DMSO-$d_6$) δ 11.09 (s, 1H), 7.02-6.94 (m, 2H), 6.87 (dd, J = 5.8, 3.1 Hz, 1H), 5.37 (dd, J = 12.6, 5.4 Hz, 1H), 3.60 (t, J = 6.7 Hz, 2H), 3.56 (s, 3H), 2.99-2.83 (m, 3H), 2.77-2.58 (m, 2H), 2.06-1.97 (m, 1H), 1.92 (p, J = 6.8 Hz, 2H), 1.78-1.66 (m, 2H). |

TABLE 21-continued

Characterization data for intermediates prepared according to above.

| Inter-mediate | Structure | Chemical Name | MS: [(M + 1)] + | $^1$H-NMR |
|---|---|---|---|---|
| F-2-4 | 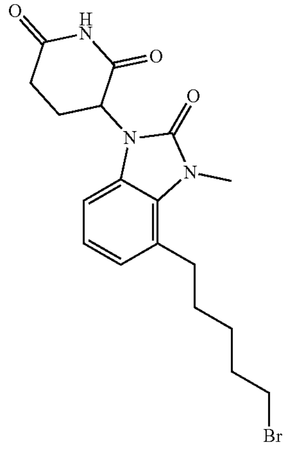 [SMILES: Cn1c(=O)n(C2CCC(=O)NC2=O)c2cccc(CCCCCBr)c21] | 3-[4-(5-bromo-pentyl)-3-methyl-2-oxo-1,3-benzo-diazol-1-yl] piperidine-2,6-dione | 408.1 410.1 | (400 MHz, DMSO-$d_6$) δ 11.09 (s, 1H), 7.01-6.93 (m, 2H), 6.88 (dd, J = 5.4, 3.5 Hz, 1H), 5.37 (dd, J = 12.6, 5.4 Hz, 1H), 3.58-3.54 (m, 4H), 2.89 (dt, J = 13.9, 6.7 Hz, 3H), 2.78-2.59 (m, 2H), 2.08 (s, 1H), 2.04-1.96 (m, 1H), 1.88 (p, J = 6.9 Hz, 2H), 1.68-1.59 (m, 2H), 1.56-1.47 (m, 2H). |
| F-2-5 | 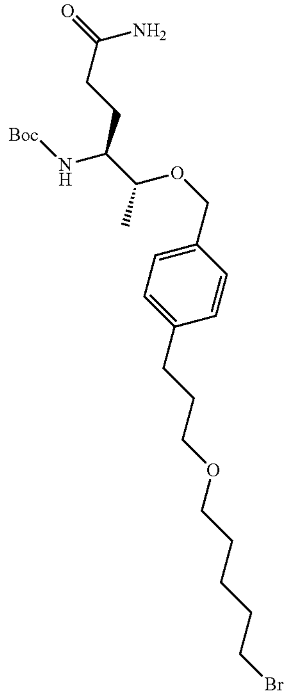 [SMILES: C[C@@H](OCc1ccc(CCCOCCCCCBr)cc1)[C@H](CCC(N)=O)NC(=O)OC(C)(C)C] | tert-butyl N-[(3S,4R)-4-[(4-[3-[(5-bromo-pentyl) oxylpropyl] phenyl) methoxy]-1-carbamoyl pentan-3-yl] carbamate | 565.5 567.5 | (400 MHz, DMSO-$d_6$) δ 7.23 (d, J = 7.9 Hz, 3H), 7.15 (d, J = 7.8 Hz, 2H), 6.68 (s, 1H), 6.61 (d, J = 9.1 Hz, 1H), 4.49-4.38 (m, 2H), 3.54 (t, J = 6.7 Hz, 2H), 3.43-3.28 (m, 6H), 2.60 (t, J = 7.6 Hz, 2H), 2.04 (ddd, J = 15.2, 9.5, 5.6 Hz, 1H), 1.88-1.72 (m, 6H), 1.58-1.40 (m, 4H), 1.39 (s, 9H), 1.36 (s, 1H), 1.06 (d, J = 6.0 Hz, 3H). |

TABLE 21-continued

Characterization data for intermediates prepared according to above.

| Intermediate | Structure | Chemical Name | MS: [(M + 1)]$^+$ | $^1$H-NMR |
|---|---|---|---|---|
| F-2-6 | 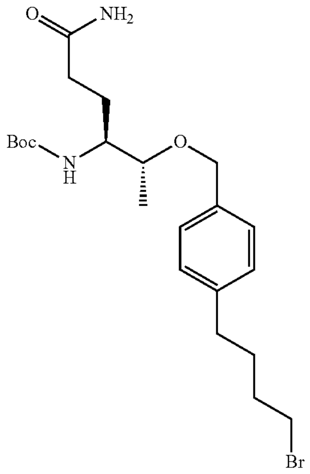 [SMILES: C[C@@H](OCc1ccc(CCCCBr)cc1)[C@H](CCC(N)=O)NC(=O)OC(C)(C)C] | tert-butyl N-[(3S,4R)-4-[[4-(4-bromo-butyl) phenyl] methoxy]-1-carbamoyl pentan-3-yl] carbamate | 471.2 473.2 | (400 MHz, DMSO-$d_6$) δ 7.31-7.02 (m, 5H), 6.67 (s, 1H), 6.60 (d, J = 9.1 Hz, 1H), 4.47 (s, 1H), 4.44 (d, J = 4.3 Hz, 2H), 3.55 (t, J = 6.6 Hz, 2H), 3.40 (t, J = 6.7 Hz, 2H), 2.59 (q, J = 7.0, 6.4 Hz, 2H), 2.13-1.96 (m, 2H), 1.81 (t, J = 7.5 Hz, 2H), 1.68 (p, J = 7.4 Hz, 2H), 1.48-1.45 (m, 1H), 1.39 (s, 9H), 1.06 (d, J = 6.0 Hz, 3H). |
| F-2-7 | 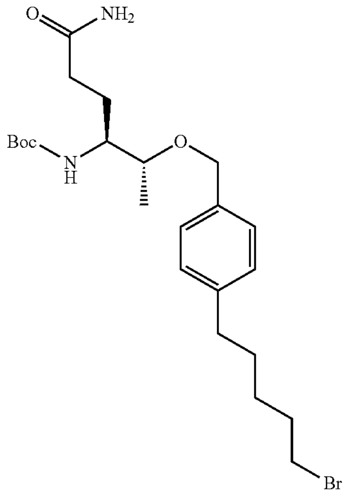 [SMILES: C[C@@H](OCc1ccc(CCCCCBr)cc1)[C@H](CCC(N)=O)NC(=O)OC(C)(C)C] | tert-butyl N-[(3S,4R)-4-[[4-(5-bromo-pentyl) phenyl] methoxy]-1-carbamoyl pentan-3-yl] carbamate | 485.3 487.3 | (400 MHz, $CDCl_3$) δ 7.26 (d, J = 7.9 Hz, 2H), 7.17 (d, J = 7.8 Hz, 2H), 6.47 (s, 1H), 5.36 (s, 1H), 4.90 (d, J = 9.6 Hz, 1H), 4.60 (d, J = 11.5 Hz, 1H), 4.40 (d, J = 11.5 Hz, 1H), 3.73-3.59 (m, 2H), 3.43 (t, J = 6.8 Hz, 2H), 2.64 (t, J = 7.7 Hz, 2H), 2.30 (ddd, J = 8.5, 6.2, 2.9 Hz, 2H), 2.01 (dd, J = 14.8, 7.2 Hz, 1H), 1.96-1.88 (m, 2H), 1.72 (dd, J = 10.0, 4.9 Hz, 1H), 1.66 (td, J = 9.0, 8.4, 5.1 Hz, 2H), 1.50 (t, J = 7.6 Hz, 2H), 1.46 (s, 9H), 1.22 (d, J = 6.2 Hz, 3H). |

TABLE 21-continued

Characterization data for intermediates prepared according to above.

| Inter-mediate | Structure | Chemical Name | MS: [(M + 1)] + | $^1$H-NMR |
|---|---|---|---|---|
| F-2-8 | 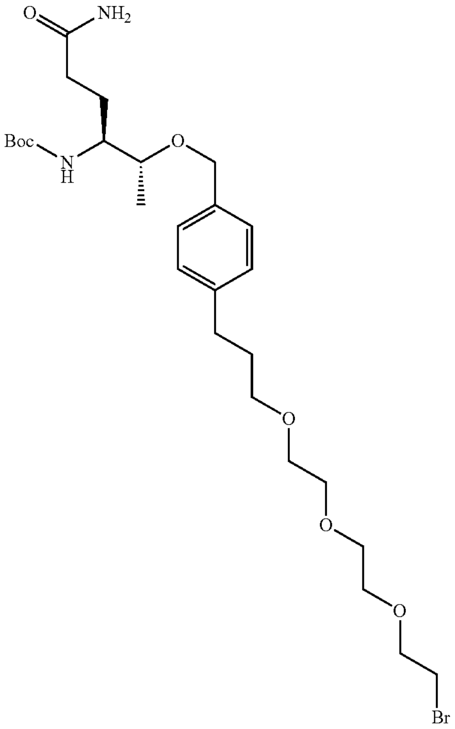 [SMILES: C[C@@H](OCc1ccc(CCCOCCOCCOCCBr)cc1)[C@H](CCC(N)=O)NC(=O)OC(C)(C)C] | tert-butyl N-[(3S,4R)-4-[[4-(3-[2-[2-(2-bromo-ethoxy) ethoxy] ethoxy] propyl) phenyl] methoxy]-1-carbamoyl pentan-3-yl] carbamate | 589.4 571.4 | (400 MHz, $CDCl_3$) δ 7.25 (d, J = 7.8 Hz, 2H), 7.19 (d, J = 8.0 Hz, 2H), 6.48 (s, 1H), 5.37 (s, 1H), 4.90 (d, J = 9.7 Hz, 1H), 4.59 (d, J = 11.5 Hz, 1H), 4.39 (d, J = 11.4 Hz, 1H), 3.84 (t, J = 6.3 Hz, 2H), 3.76-3.57 (m, 9H), 3.49 (td, J = 6.4, 2.1 Hz, 4H), 2.73-2.64 (m, 2H), 2.36-2.20 (m, 2H), 2.15-1.61 (m, 5H), 1.46 (s, 9H), 1.22 (d, J = 6.3 Hz, 3H). |
| F-2-9 | 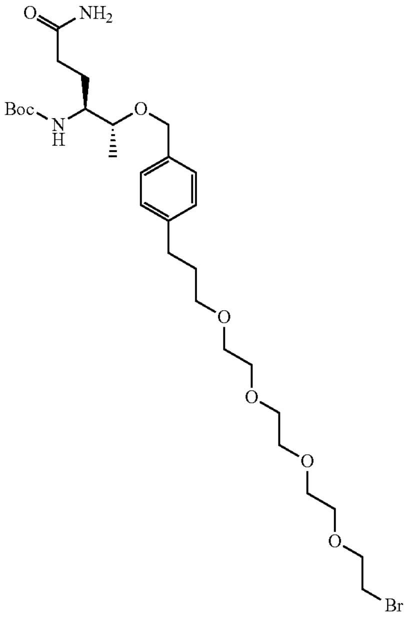 [SMILES: C[C@@H](OCc1ccc(CCCOCCOCCOCCOCCBr)cc1)[C@H](CCC(N)=O)NC(=O)OC(C)(C)C] | tert-butyl N-[(3S,4R)-4-[[4-(1-bromo-3,6,9,12-tetraoxa-penta-decan-15-yl)phenyl] methoxy]-1-carbamoyl pentan-3-yl] carbamate | 633.4 635.4 | (400 MHz, $CDCl_3$) δ 7.25 (d, J = 7.9 Hz, 2H), 7.19 (d, J = 7.9 Hz, 2H), 6.72 (s, 1H), 5.60 (s, 1H), 4.92 (d, J = 9.5 Hz, 1H), 4.59 (d, J = 11.5 Hz, 1H), 4.39 (d, J = 11.5 Hz, 1H), 3.83 (t, J = 6.3 Hz, 2H), 3.73-3.65 (m, 11H), 3.58-3.54 (m, 3H), 3.51-3.46 (m, 4H), 2.74-2.66 (m, 2H), 2.30 (h, J = 8.0 Hz, 2H), 2.04-1.86 (m, 3H), 1.72 (s, 1H), 1.46 (s, 9H), 1.22 (d, J = 6.2 Hz, 3H). |

TABLE 21-continued

| Characterization data for intermediates prepared according to above. | | | | |
|---|---|---|---|---|
| Inter-mediate | Structure | Chemical Name | MS: [(M + 1)]$^+$ | $^1$H-NMR |
| F-2-10 | 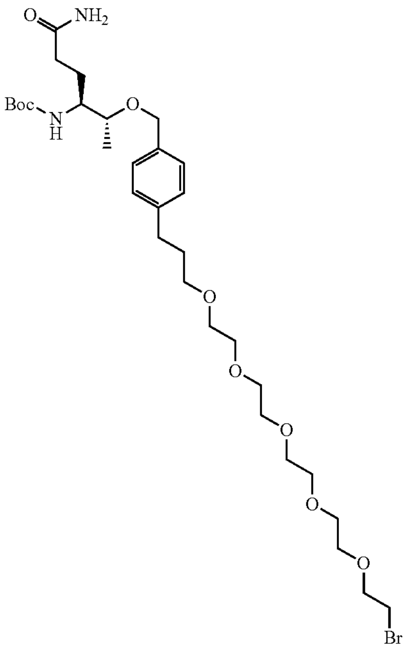 [SMILES: C[C@@H](OCc1ccc(CCCOCCOCCOCCOCCOCCBr)cc1)[C@H](CCC(N)=O)NC(=O)OC(C)(C)C] | tert-butyl N-[(3S,4R)-4-[[4-(1-bromo-3,6,9,12,15-penta-oxaocta-decan-18-yl)phenyl] methoxy]-1-carbamoyl-pentan-3-yl] carbamate | 677.3 679.3 | (400 MHz, $CDCl_3$) δ 7.25 (d, J = 7.7 Hz, 2H), 7.19 (d, J = 7.8 Hz, 2H), 6.55 (s, 1H), 5.43 (s, 1H), 4.91 (d, J = 9.9 Hz, 1H), 4.59 (d, J = 11.5 Hz, 1H), 4.39 (d, J = 11.5 Hz, 1H), 3.83 (t, J = 6.3 Hz, 2H), 3.70-3.68 (m, 14H), 3.62-3.60 (m, 3H), 3.51-3.49 (m, 4H), 2.70 (t, J = 7.7 Hz, 2H), 2.34-2.25 (m, 2H), 2.05-1.97 (m, 1H), 1.96-1.86 (m, 3H), 1.76-1.67 (m, 1H), 1.46 (s, 9H), 1.22 (d, J = 6.3 Hz, 3H). |
| F-2-11 | 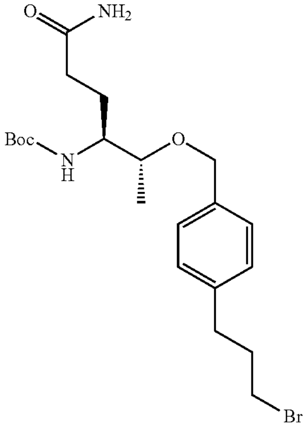 [SMILES: C[C@@H](OCc1ccc(CCCBr)cc1)[C@H](CCC(N)=O)NC(=O)OC(C)(C)C] | tert-butyl N-[(3S,4R)-4-[[4-(3-bromo-propyl) phenyl] methoxy]-1-carbamoyl-pentan-3-yl] carbamate | 457.1 459.1 | (400 MHz, DMSO-$d_6$) δ 7.30-7.13 (m, 5H), 6.73-6.55 (m, 2H), 4.43 (t, J = 8.2 Hz, 2H), 3.50-3.35 (m, 4H), 2.70 (t, J = 7.5 Hz, 2H), 2.14-1.96 (m, 4H), 1.79 (dtd, J = 13.2, 9.7, 8.6, 4.8 Hz, 1H), 1.49 (dd, J = 14.0, 8.8 Hz, 1H), 1.39 (s, 9H), 1.06 (d, J = 6.0 Hz, 3H). |

TABLE 21-continued

| Characterization data for intermediates prepared according to above. | | | | |
|---|---|---|---|---|
| Inter-mediate | Structure | Chemical Name | MS: [(M + 1)]$^+$ | $^1$H-NMR |
| F-2-12 | 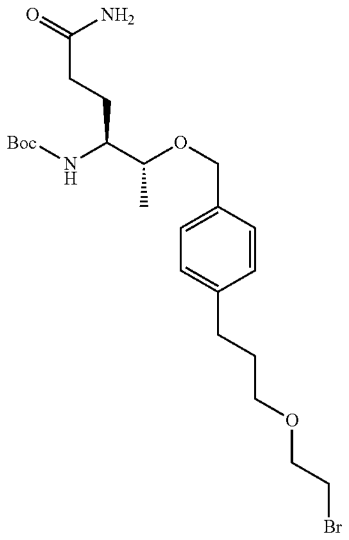 [SMILES: C[C@@H](OCc1ccc(CCCOCCBr)cc1)[C@H](CCC(N)=O)NC(=O)OC(C)(C)C] | tert-butyl N-[(3S,4R)-4-([4-[3-(2-bromo-ethoxy) propyl] phenyl] methoxy)-1-carbamoyl-pentan-3-yl] carbamate | 501.2 503.2 | (400 MHz, $CDCl_3$) δ 7.26 (d, J = 8.1 Hz, 2H), 7.20 (d, J = 7.9 Hz, 2H), 6.48 (s, 1H), 5.34 (d, J = 11.4 Hz, 1H), 4.90 (d, J = 9.7 Hz, 1H), 4.59 (d, J = 11.5 Hz, 1H), 4.39 (d, J = 11.4 Hz, 1H), 3.77 (t, J = 6.2 Hz, 2H), 3.73 (s, 1H), 3.52-3.41 (m, 4H), 2.73 (t, J = 7.6 Hz, 2H), 2.32-2.26 (m, 2H), 2.01 (dd, J = 14.0, 7.1 Hz, 1H), 1.96-1.89 (m, 2H), 1.70 (dd, J = 13.9, 5.8 Hz, 1H), 1.46 (s, 9H), 1.22 (d, J = 6.3 Hz, 3H). |
| F-2-13 | 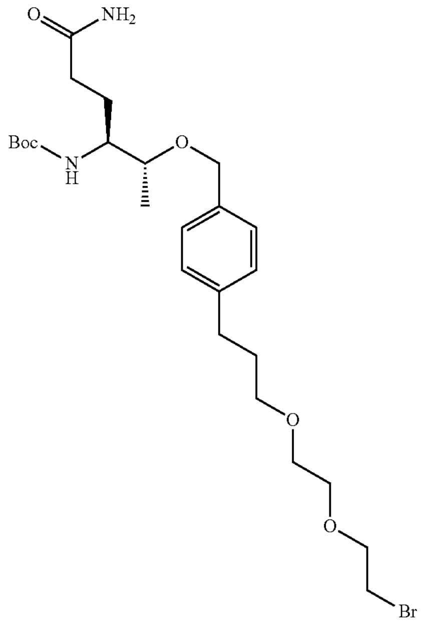 [SMILES: C[C@@H](OCc1ccc(CCCOCCOCCBr)cc1)[C@H](CCC(N)=O)NC(=O)OC(C)(C)C] | tert-butyl N-[(3S,4R)-4-[(4-[3-[2-(2-bromo-ethoxy) ethoxy] propyl] phenyl) methoxy]-1-carbamoyl-pentan-3-yl] carbamate | [(M + 23)]$^+$ = 567.3 569.3 | (400 MHz, DMSO-$d_6$) δ 7.25-7.20 (m, 3H), 7.15 (d, J = 7.8 Hz, 2H), 6.67 (s, 1H), 6.60 (d, J = 9.0 Hz, 1H), 4.49-4.39 (m, 2H), 3.75 (td, J = 5.8, 1.9 Hz, 2H), 3.61-3.55 (m, 4H), 3.50 (dd, J = 6.0, 3.5 Hz, 2H), 3.41-3.37 (m, 4H), 2.60 (t, J = 7.8 Hz, 2H), 2.04 (dt, J= 15.0, 9.3 Hz, 2H), 1.81-1.76 (m, 3H), 1.47 (s, 1H), 1.38 (s, 9H), 1.06 (d, J = 6.0 Hz, 3H) |

TABLE 21-continued

Characterization data for intermediates prepared according to above.

| Inter-mediate | Structure | Chemical Name | MS: $[(M + 1)]^+$ | $^1$H-NMR |
|---|---|---|---|---|
| F-2-14 | 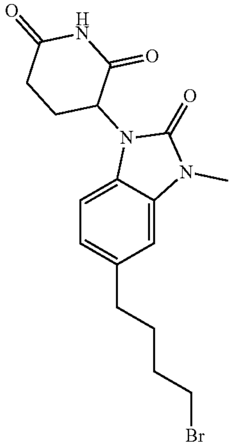 [SMILES: Cn1c(=O)n(C2CCC(=O)NC2=O)c2ccc(CCCCBr)cc21] | 3-[5-(4-bromo-butyl)-3-methyl-2-oxo-1,3-benzo-diazol-1-yl] piperidine-2,6-dione | 394.1, 396.1 | (400 MHz, DMSO-$d_6$) δ 11.10 (s, 1H), 7.06-6.99 (m, 2H), 6.88 (dd, J = 8.1, 1.6 Hz, 1H), 5.35 (dd, J = 12.7, 5.3 Hz, 1H), 3.56 (t, J = 6.6 Hz, 2H), 3.33 (s, 3H), 2.97-2.84 (m, 1H), 2.78-2.57 (m, 4H), 2.01 (tq, J = 8.9, 3.5, 2.9 Hz, 1H), 1.88-1.77 (m, 2H), 1.72 (p, J = 7.0, 6.4 Hz, 2H). |
| F-2-15 | 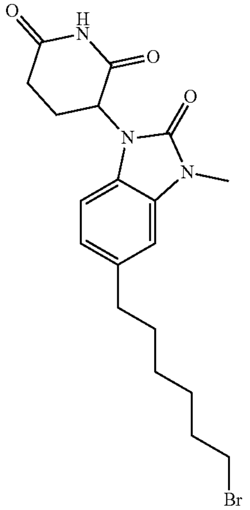 [SMILES: Cn1c(=O)n(C2CCC(=O)NC2=O)c2ccc(CCCCCCBr)cc21] | 3-[5-(6-bromo-hexyl)-3-methyl-2-oxo-1,3-benzo-diazol-1-yl] piperidine-2,6-dione | 422.2, 424.2 | (400 MHz, DMSO-$d_6$) δ 11.09 (s, 1H), 7.11-6.96 (m, 2H), 6.87 (d, J = 7.7 Hz, 1H), 5.34 (dd, J = 12.7, 5.3 Hz, 1H), 3.53 (t, J = 6.7 Hz, 2H), 3.33 (s, 3H), 2.98-2.84 (m, 1H), 2.72 (td, J = 12.9, 4.3 Hz, 1H), 2.67-2.58 (m, 3H), 2.07-1.98 (m, 1H), 1.81 (p, J = 6.9 Hz, 2H), 1.61 (p, J = 7.5 Hz, 2H), 1.43 (t, J = 7.8 Hz, 2H), 1.34 (q, J = 7.1 Hz, 2H). |
| F-2-16 | 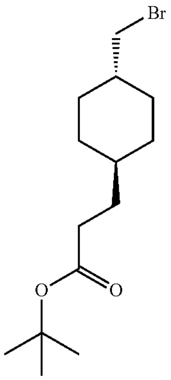 [SMILES: CC(C)(C)OC(=O)CC[C@H]1CC[C@H](CBr)CC1] | tert-butyl 3-[(1r,4r)-4-(bromo-methyl) cyclo-hexyl] propanoate | N/A | (400 MHz, DMSO-$d_6$) δ 3.41 (d, J = 6.2 Hz, 2H), 3.25 (t, J = 6.5 Hz, 1H), 2.19 (t, J = 7.7 Hz, 2H), 1.86-1.78 (m, 2H), 1.77-1.68 (m, 2H), 1.59-1.47 (m, 1H), 1.47-1.41 (m, 1H), 1.39 (s, 9H), 1.20-1.13 (m, 1H), 1.04-0.84 (m, 4H) |

TABLE 21-continued

Characterization data for intermediates prepared according to above.

| Inter-mediate | Structure | Chemical Name | MS: [(M + 1)] + | $^1$H-NMR |
|---|---|---|---|---|
| F-2-17 | 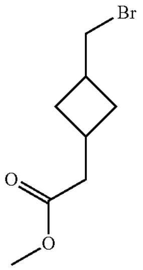 | methyl 2-[3-(bromo-methyl) cyclobutyl] acetate | N/A | (400 MHz, $CD_3OD$) δ 3.68-3.64 (m, 3H), 3.55-3.42 (m, 2H), 2.77-2.39 (m, 4H), 2.32-2.28 (m, 1H), 2.08-1.85 (m, 2H), 1.49-1.45 (m, 1H) |
| F-2-18 | 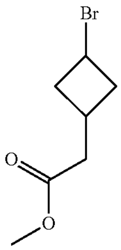 | Methyl 2-(3-bromo-cyclobutyl) acetate | N/A | (400 MHz, $CD_3OD$) δ 4.40-3.87 (m, 1H), 3.52 (d, J = 1.8 Hz, 3H), 2.66-2.41 (m, 1H), 2.42, (dd, J = 7.2, 2.2 Hz, 2H), 2.07-2.01 (m, 2H), 1.65-1.48 (m, 2H) |
| F-2-19 | 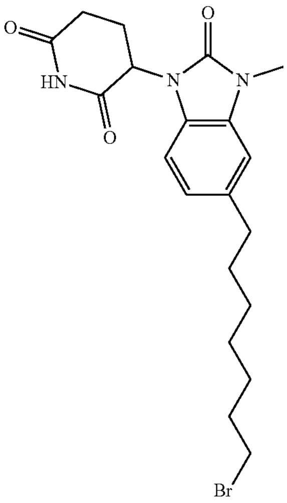 [SMILES: Cn1c(=O)n(C2CCC(=O)NC2=O)c2ccc(CCCCCCCBr)cc21] | 3-[5-(7-bromo-heptyl)-3-methyl-2-oxo-1,3-benzo-diazol-1-yl] piperidine-2,6-dione | 436.1, 438.1 | (400 MHz, DMSO-$d_6$) δ 11.08 (s, 1H), 7.10-6.94 (m, 2H), 6.87 (dd, J = 8.1, 1.6 Hz, 1H), 5.34 (dd, J = 12.7, 5.4 Hz, 1H), 3.53 (t, J = 6.7 Hz, 2H), 3.33 (s, 3H), 3.00-2.90 (m, 1H), 2.72 (td, J = 12.9, 4.3 Hz, 1H), 2.66-2.56 (m, 3H), 2.01 (ddd, J = 10.9, 5.8, 3.6 Hz, 1H), 1.79 (p, J = 6.8 Hz, 2H), 1.60 (p, J = 7.0 Hz, 2H), 1.41-1.27 (m, 6H) |
| F-2-20 | 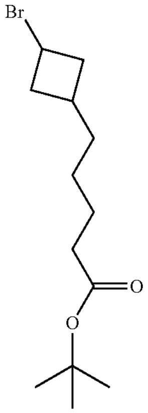 [SMILES: CC(C)(C)OC(=O)CCCCC1CC(Br)C1] | tert-butyl 5-(3-bromo-cyclobutyl) pentanoate | N/A | (400 MHz, Chloroform-d) δ 4.60-4.51 (m, 1H), 2.64-2.50 (m, 3H), 2.40-2.29 (m, 2H), 2.22 (t, J = 7.4 Hz, 2H), 1.62-1.54 (m, 3H), 1.50-1.48 (m, 1H), 1.46 (s, 9H), 1.31-1.19 (m, 2H) |

TABLE 21-continued

| Characterization data for intermediates prepared according to above. | | | | |
|---|---|---|---|---|
| Intermediate | Structure | Chemical Name | MS: $[(M + 1)]^+$ | $^1$H-NMR |
| F-2-21 | 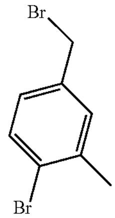 | (4-bromo-3-methyl-phenyl) methanol | 201.0, 203.0 | (400 MHz, DMSO-$d_6$) δ 7.51 (d, J = 8.2 Hz, 1H), 7.29 (dd, J = 2.1, 1.0 Hz, 1H), 7.08 (dd, J = 8.2, 2.1 Hz, 1H), 5.24 (s, 1H), 4.44 (s,2H), 2.34 (s, 3H) |
| F-2-22 | 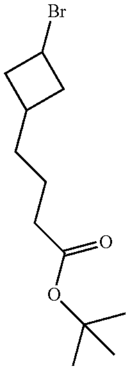 | tert-butyl 4-(3-bromo-cyclobutyl) butanoate | N/A | (400 MHz, DMSO-$d_6$) δ 4.72-4.68 (m, 0.7H), 4.51-4.47 (m, 0.3H), 2.87-2.65 (m, 0.3H), 2.49-2.43 (m, 0.7H), 2.40-2.27 (m, 1H), 2.25-2.12 (m, 2H), 2.10-1.97 (m, 1H), 1.66-1.51 (m, 1H), 1.46-1.26 (m, 13H), 1.33-1.20 (m, 1H). |
| F-2-23 | 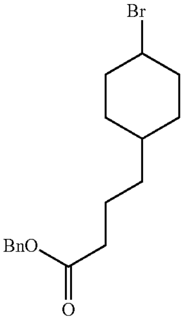 [SMILES: O=C(CCCC1CCC(Br)CC1)OCc1ccccc1] | benzyl 4-(4-bromo-cyclohexyl) butanoate | N/A | (300 MHz, $CD_3OD$) δ 7.37-7.31 (m, 5H), 4.85-4.84 (m, 2H) 4.63 (d, J = 5.2 Hz, 1H), 2.39-2.28 (m, 2H), 2.05-1.99 (m, 2H), 1.88-1.83 (m, 2H), 1.69-1.48 (m, 6H), 1.30-1.25 (m, 3H) |
| F-2-24 | 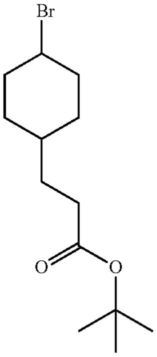 [SMILES: CC(C)(C)OC(=O)CCC1CCC(Br)CC1] | tert-butyl 3-(4-bromo-cyclohexyl) propanoate | N/A | (400 MHz, $CDCl_3$) δ 4.73-4.60 (m, 2H), 2.53-2.41 (m, 1H), 2.33-2.23 (m, 2H), 2.26-2.05, (m, 2H), 2.03-1.92 (m 3H) 1.90-1.86 (m, 1H), 1.65-1.50 (m, 3H), 1.47 (s, 9H). |

Step 2. Tert-butyl N-[(3S4R')-1-carbamoyl-4-[[4-(5-[3-[1-(2,6-dioxopiperidin-3-yl)-3-methyl-2-oxo-1.3-benzodiazol-5-yl]propoxy]pentyl)phenyl]methoxy]pentan-3-yl]carbamate (Intermediate F'). To a mixture of 3-(5-[3-[(5-bromopentyl)oxy]propyl]-3-methyl-2-oxo-1,3-benzodiazol-1-yl)piperidine -2,6-dione (420 mg, 0.90 minol), tert-butyl N-[(3S,4R)-4-[(4-bromophenyl)methoxy]-1-carbamoylpentan-3-yl]carbamate (449 mg, 1.08 mmol), tris(trimethylsilyl) silane (224 mg, 0.90 mmol), $Na_2CO_3$ (286 mg, 2.70 mmol) and $IR[DF(CF_3)PPY]_2(DTBPY)PF_6$ (10 mg, 0.01 mmol) in DME (6.00 mL) was added dtbbpy (2.40 mg, 0.01 mmol) and 1,2-dimethoxyethane dihydrochloride nickel (2.00 mg, 0.01 mmol) in DME (6.00 mL) at room temperature under nitrogen atmosphere. The mixture was stirred for 4 hours under 34W blue LED at room temperature. The resulting mixture was filtered. The filter cake was washed with DCM (3×15.0 mL). The filtrate was concentrated under reduced pressure. The residue was purified by reversed phase Flash chromatography with the following conditions: Column: WelFlash™ C18-I, 20~40 um, 330 g; Eluent A: water (plus 10 mmol/L HOAc); Eluent B: ACN; Gradient: 50% - 75% B in 25 min; Flow rate: 80 mL/min; Detector: UV 220/254 nm; desired fractions were collected at 70% B and concentrated under reduced pressure to afford the title compound as a yellow solid (290 mg, 45%): $^1$H NMR (400 MHz, DMSO-$d_6$) δ 11.08 (s, 1H), 7.24-7.21 (m, 3H), 7.14 (d, J=7.9 Hz, 2H), 7.06-7.00 (m, 2H), 6.86 (dd, J=8.1, 1.6 Hz, 1H), 6.68 (s, 1H), 6.60 (d, J=9.1 Hz, 1H), 5.34 (dd, J=12.7, 5.4 Hz, 1H), 4.47-4.37 (m, 2H), 3.49-3.32 (m, 9H), 2.90 (ddd, J=16.9, 12.8, 5.1 Hz, 1H), 2.77-2.53 (m, 7H), 2.04-1.94 (m, 2H), 1.82-1.77 (m, 3H), 1.60-1.50 (m, 5H), 1.38 (s, 11H), 1.05 (d, J=6.0 Hz, 3H); MS (ESI, m/z): $[(M+1)]^+$=722.40.

The following intermediates in Table 22 were prepared according to Step 2 of the procedure to prepare Intermediate F.

TABLE 22

Characterization data for intermediates prepared according to above.

| Intermediate | Structure | Chemical Name | MS: $[(M + 1)]^+$ | $^1$H-NMR |
|---|---|---|---|---|
| F1 | 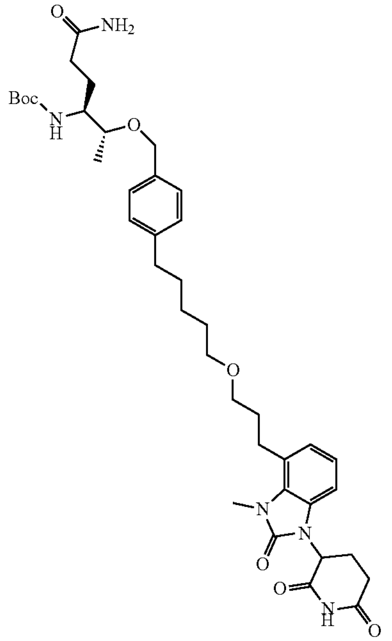 | tert-butyl N-[(3S,4R)-1-carbamoyl-4-[[4-(5-[3-[1-(2,6-dioxopiperidin-3-yl)-3-methyl-2-oxo-1,3-benzodiazol-4-yl]propoxyl pentyl)phenyl] methoxy] pentan-3-yl] carbamate | 722.6 | $^1$H NMR (400 MHz, DMSO-$d_6$) δ 11.09 (s, 1H), 7.24-7.20 (m, 3H), 7.14 (d, J = 7.8 Hz, 2H), 6.99-6.92 (m, 2H), 6.86 (dd, J = 5.6, 3.4 Hz, 1H), 6.68 (s, 1H), 6.60 (d, J = 9.1 Hz, 1H), 5.37 (dd, J = 12.7, 5.5 Hz, 1H), 4.47-4.36 (m, 2H), 3.45-3.30 (m, 7H), 2.98-2.83 (m, 3H), 2.72 (td, J = 12.9, 4.4 Hz, 1H), 2.67-2.52 (m, 3H), 2.10-2.00 (m, 1H), 2.01 (s, 3H), 1.86-1.76 (m, 3H), 1.64-1.54 (m, 2H), 1.56-1.45 (m, 2H), 1.38 (s, 13H), 1.05 (dd, J = 6.1, 2.0 Hz, 3H). |
| F2 | 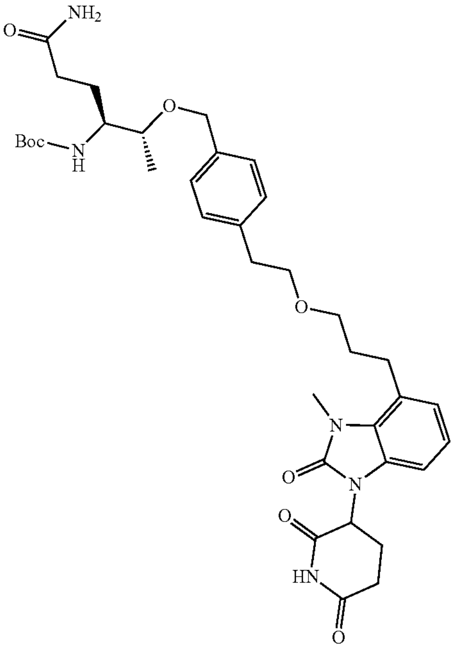 [SMILES: C[C@@H](OCc1ccc(CCOCCCc2cccc3c2n(C)c(=O)n3C2CCC(=O)NC2=O)cc1)[C@H](CCC(N)=O)NC(=O)OC(C)(C)C] | tert-butyl N-[(3S,4R)-1-carbamoyl-4-[[4-(2-[3-[1-(2,6-dioxopiperidin-3-yl)-3-methyl-2-oxo-1,3-benzodiazol-4-yl]propoxy] ethyl)phenyl] methoxy] pentan-3-yl]carbamate | 680.4 | $^1$H NMR (400 MHz, DMSO-$d_6$) δ 11.09 (s, 1H), 7.26-7.22 (m, 5H), 6.98-6.90 (m, 2H), 6.81 (dd, J = 6.4, 2.5 Hz, 1H), 6.70-6.65 (m, 1H), 6.60 (d, J = 9.1 Hz, 1H), 5.36 (dd, J = 12.6, 5.3 Hz, 1H), 4.49-4.38 (m, 2H), 3.59 (t, J = 6.8 Hz, 2H), 3.45-3.36 (m, 4H), 3.32 (s, 1H), 2.96-2.88 (m, 4H), 2.83 (dt, J = 13.6, 6.1 Hz, 2H), 2.78-2.62 (m, 2H), 2.08 (s, 2H), 1.87-1.77 (m, 1H), 1.81 (s, 3H), 1.38 (s, 10H), 1.05 (d, J = 6.0 Hz, 3H). |

TABLE 22-continued

| Intermediate | Structure | Chemical Name | MS: $[(M + 1)]^+$ | $^1$H-NMR |
|---|---|---|---|---|
| | Characterization data for intermediates prepared according to above. | | | |
| F3 | 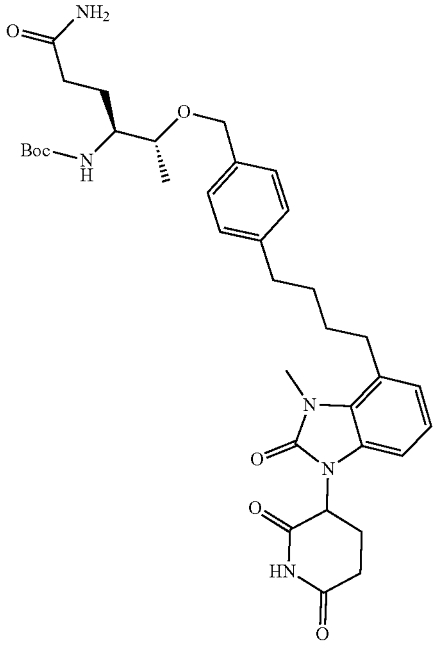 [SMILES: C[C@@H](OCc1ccc(CCCCc2cccc3c2n(C)c(=O)n3C2CCC(=O)NC2=O)cc1)[C@H](CCC(N)=O)NC(=O)OC(C)(C)C] | tert-butyl N-[(3S,4R)-1-carbamoyl-4-[(4-[4-[1-(2,6-dioxo-piperidin-3-yl)-3-methyl-2-oxo-1,3-benzodiazol-4-yl]butyl]phenyl)methoxy]pentan-3-yl]carbamate | 650.5 | $^1$H NMR (400 MHz, DMSO-$d_6$) δ 11.09 (s, 1H), 7.28-7.09 (m, 5H), 6.99-6.91 (m, 2H), 6.85 (dd, J = 6.4, 2.5 Hz, 1H), 6.69 (s, 1H), 6.61 (d, J = 9.2 Hz, 1H), 5.36 (dd, J = 12.6, 5.4 Hz, 1H), 4.48-4.39 (m, 2H), 3.48-3.36 (m, 2H), 2.99-2.82 (m, 3H), 2.72 (td, J = 12.9, 4.4 Hz, 1H), 2.67-2.57 (m, 3H), 2.07-1.96 (m, 2H), 1.79 (tdt, J = 9.4, 5.6, 2.7 Hz, 1H), 1.74-1.57 (m, 4H), 1.54-1.44 (m, 2H), 1.38 (s, 11H), 1.06 (d, J = 5.9 Hz, 3H). |
| F4 | 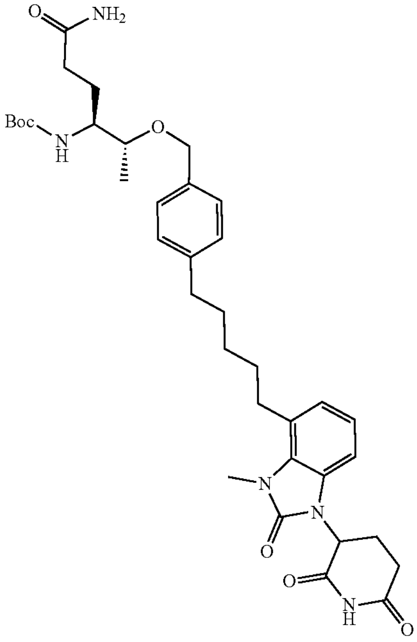 | tert-butyl N-[(3S,4R)-1-carbamoyl-4-[(4-[5-[1-(2,6-dioxo-piperidin-3-yl)-3-methyl-2-oxo-1,3-benzodiazol-4-yl]pentyl]phenyl)methoxy]pentan-3-yl]carbamate | 664.5 | $^1$HNMR (400 MHz, DMSO-$d_6$) δ 11.09 (s, 1H), 7.23 (d, J = 7.8 Hz, 3H), 7.14 (d, J = 7.8 Hz, 2H), 7.00-6.91 (m, 2H), 6.85 (dd, J = 5.9, 3.0 Hz, 1H), 6.68 (s, 1H), 6.61 (d, J = 9.1 Hz, 1H), 5.37 (dd, J = 12.5, 5.4 Hz, 1H), 4.49-4.38 (m, 2H), 3.54 (s, 3H), 3.49-3.35 (m, 2H), 2.92-2.88 (m, 3H), 2.77-2.55 (m, 4H), 2.14-1.96 (m, 3H), 1.85-1.75 (m, 1H), 1.67-1.59 (m, 4H), 1.39 (s, 12H), 1.06 (d, J = 6.1 Hz, 3H). |

TABLE 22-continued

| Characterization data for intermediates prepared according to above. | | | | |
|---|---|---|---|---|
| Inter-me-diate | Structure | Chemical Name | MS: [(M + 1)]+ | $^1$H-NMR |
| F5 | 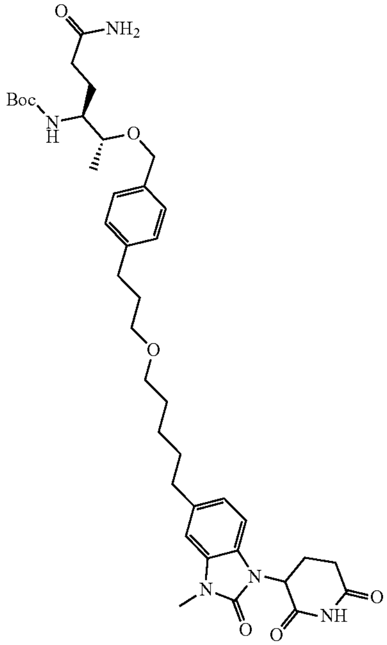 [SMILES: C[C@@H](OCc1ccc(CCCOCCCCCc2ccc3c(c2)n(C)c(=O)n3C2CCC(=O)NC2=O)cc1)[C@H](CCC(N)=O)NC(=O)OC(C)(C)C] | tert-butyl N-[(3S,4R)-1-carbamoyl-4-([4-[3-([5-[1-(2,6-dioxo-piperidin-3-yl)-3-methyl-2-oxo-1,3-benzodiazol-5-yl] pentyl]oxy) propyl] phenyl] methoxy) pentan-3-yl] carbamate | 722.6 | $^1$H NMR (400 MHz, DMSO-$d_6$) δ 11.07 (s, 1H), 7.24-7.22 (m, 3H), 7.13 (d, J = 7.8 Hz, 2H), 7.05-6.97 (m, 2H), 6.87 (d, J = 8.0 Hz, 1H), 6.67 (s, 1H), 6.60 (d, J = 9.2 Hz, 1H), 5.33 (dd, J = 12.8, 5.4 Hz, 1H), 4.47-4.38 (m, 2H), 3.37 (dd, J = 26.7, 6.4 Hz, 9H), 2.88 (d, J = 16.7 Hz, 1H), 2.76-2.55 (m, 6H), 2.10-1.96 (m, 3H), 1.78-1.73 (m, 3H), 1.64-1.60 (m, 2H), 1.55-1.52 (m, 2H), 1.38 (s, 12H), 1.06 (d, J = 6.0 Hz, 3H). |
| F6 | 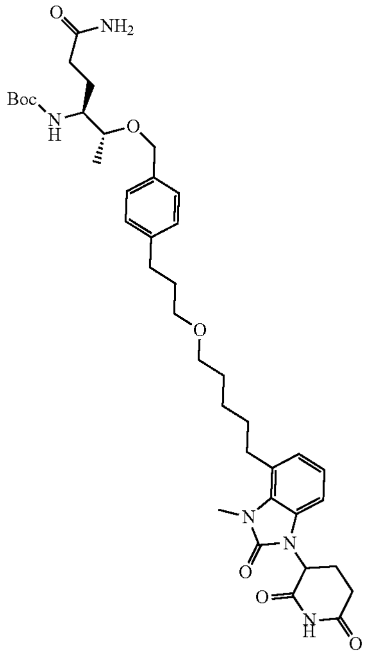 | tert-butyl N-[(3S,4R)-1-carbamoyl-4-([4-[3-([5-[1-(2,6-dioxo-piperidin-3-yl)-3-methyl-2-oxo-1,3-benzodiazol-4-yl] pentyl] oxy) propyl] phenyl] methoxy) pentan-3-yl] carbamate | 722.5 | $^1$H NMR (400 MHz, DMSO-$d_6$) δ 11.09 (s, 1H), 7.25-7.22 (m, 3H), 7.14 (d, J = 7.8 Hz, 2H), 6.99-6.92 (m, 2H), 6.88 (q, J = 4.8 Hz, 1H), 6.68 (s, 1H), 6.60 (d, J = 9.0 Hz, 1H), 5.36 (dd, J = 12.4, 5.3 Hz, 1H), 4.48-4.39 (m, 2H), 3.56 (s, 3H), 3.48-3.32 (m, 6H), 2.96-2.82 (m, 3H), 2.76-2.56 (m, 4H), 2.09-1.95 (m, 3H), 1.80-1.76 (m, 3H), 1.61-1.57 (m, 4H), 1.46-1.44 (m, 3H), 1.39 (s, 9H), 1.06 (d, J = 6.0 Hz, 3H). |

TABLE 22-continued

| Characterization data for intermediates prepared according to above. | | | | |
|---|---|---|---|---|
| Inter-me-diate | Structure | Chemical Name | MS: [(M + 1)]$^+$ | $^1$H-NMR |
| F15 | 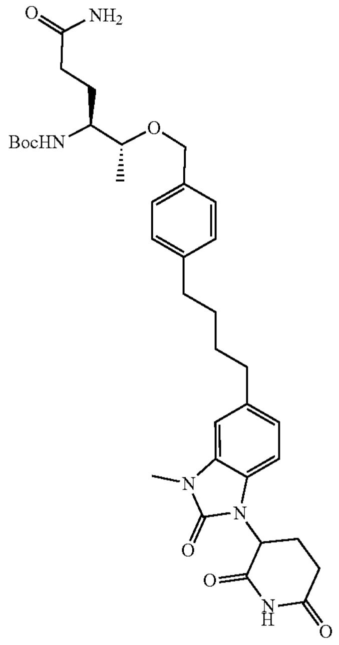 | tert-butyl N-[(3S,4R)-1-carbamoyl-4-[(4-[4-[1-(2,6-dioxo-piperidin-3-yl)-3-methyl-2-oxo-1,3-benzodiazol-5-yl]butyl]phenyl)methoxy]pentan-3-yl]carbamate | 650.2 | Used in the next step without further purification |
| F16 | 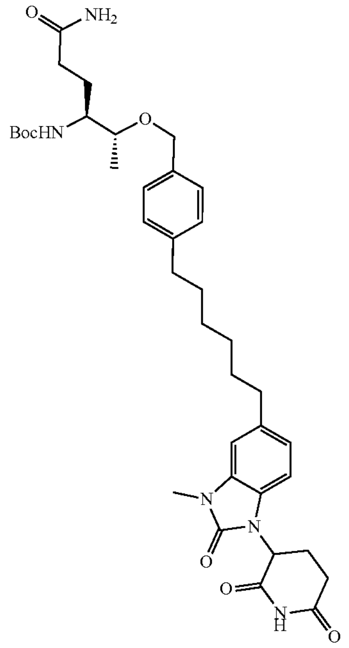 | tert-butyl N-[(3S,4R)-1-carbamoyl-4-[(4-[6-[1-(2,6-dioxo-piperidin-3-yl)-3-methyl-2-oxo-1,3-benzodiazol-5-yl]hexyl]phenyl)methoxy]pentan-3-yl]carbamate | 678.5 | $^1$H NMR (400 MHz, DMSO-$d_6$) δ 11.07 (s, 1H), 7.21 (m, 3H), 7.12 (d, J = 7.9 Hz, 2H), 7.03-6.96 (m, 2H), 6.85 (dd, J = 8.1, 1.6 Hz, 1H), 6.67 (s, 1H), 6.60 (d, J = 9.1 Hz, 1H), 5.33 (dd, J = 12.7, 5.4 Hz, 1H), 4.47-4.37 (m, 2H), 3.41 (dq, J = 15.9, 6.2 Hz, 1H), 3.31 (s, 3H), 2.98-2.84 (m, 1H), 2.77-2.50 (m, 7H), 2.12-1.94 (m, 2H), 1.78 (dddd, J = 13.1, 9.4, 5.9, 2.9 Hz, 1H), 1.63-1.51 (m, 4H), 1.50-1.40 (m, 1H), 1.38 (s, 9H), 1.34-1.27 (m, 5H), 1.05 (d, J = 6.0 Hz, 3H). |

TABLE 22-continued

Characterization data for intermediates prepared according to above.

| Inter-me-diate | Structure | Chemical Name | MS: $[(M + 1)]^+$ | $^1$H-NMR |
|---|---|---|---|---|
| F17 | 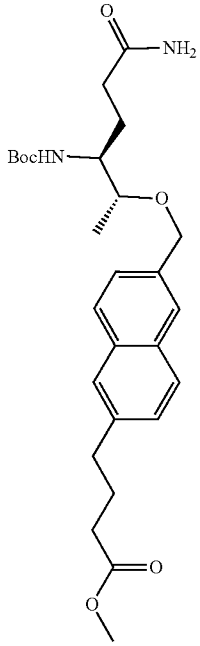 [SMILES: COC(=O)CCCc1ccc2cc(CO[C@H](C)[C@H](CCC(N)=O)NC(=O)OC(C)(C)C)ccc2c1] | methyl 4-[6-([[(2R,3S)-3-[tert-butoxy-carbonyl)amino]-5-carbamoyl-pentan-2-yl]oxy]methyl)naphthalen-2-yl]butanoate | 487.20 | (400 MHz, $CD_3OD$) δ 7.83-7.75 (m, 3H), 7.64 (d, J = 1.5 Hz, 1H), 7.49 (dd, J = 8.4, 1.7 Hz, 1H), 7.36 (dd, J = 8.4, 1.8 Hz, 1H), 4.75 (d, J = 11.8 Hz, 1H), 4.66 (d, J = 11.8 Hz, 1H), 3.66 (s, 3H), 3.69-3.52 (m, 2H), 2.82 (t, J = 7.6 Hz, 2H), 2.39 (t, J = 7.3 Hz, 2H), 2.35-2.18 (m, 2H), 2.09-1.95 (m, 3H), 1.65 (dtd, J = 15.1, 9.9, 5.9 Hz, 1H), 1.41 (s, 9H), 1.22 (d, J = 6.0 Hz, 3H) |
| F18 | 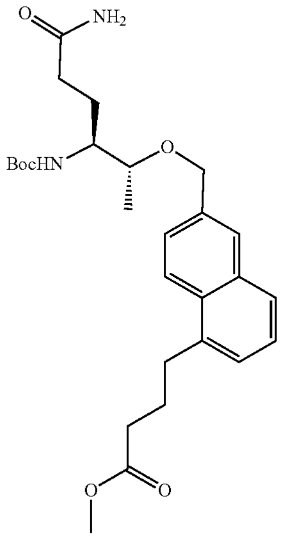 [SMILES: COC(=O)CCCc1cccc2cc(CO[C@H](C)[C@H](CCC(N)=O)NC(=O)OC(C)(C)C)ccc12] | methyl 4-[6-([[(2R,3S)-3-(tert-butoxy-carbonyl)amino]-5-carbamoyl-pentan-2-yl]oxy]methyl)naphthalen-1-yl]butanoate | 487.20 | (400 MHz, DMSO-$d_6$) δ 8.07 (d, J = 8.7 Hz, 1H), 7.85 (d, J = 1.7 Hz, 1H), 7.77-7.65 (m, 1H), 7.52 (dd, J = 8.7, 1.8 Hz, 1H), 7.42 (dd,J = 8.2, 7.0 Hz, 1H), 7.32 (dd, J = 7.0, 1.3 Hz, 1H), 7.24 (s, 1H), 6.72-6.63 (m, 2H), 4.72-4.60 (m, 2H), 4.23 (t, J = 6.5 Hz, 2H), 3.60 (s, 3H), 3.54-3.46 (m, 2H), 3.09-3.03 (m, 2H), 2.09-2.05 (m, 2H), 1.66-1.64 (m, 2H), 1.37 (s, 9H), 1.25-1.23 (m, 1H), 1.18-1.15 (m, 1H), 1.11 (d, J = 5.8 Hz, 3H). |
| F19 | 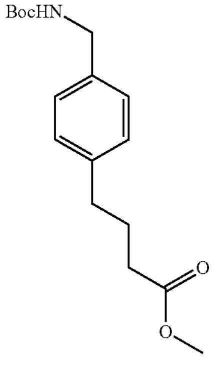 [SMILES: COC(=O)CCCc1ccc(CNC(=O)OC(C)(C)C)cc1] | methyl 4-(4-[[(tert-butoxy-carbonyl)amino]methyl]phenyl)butanoate | $[(M + NH_4)]^+$ = 325.20 | (400 MHz, DMSO-$d_6$) δ 7.33 (t, J = 6.5 Hz, 1H), 7.17-7.09 (m, 4H), 4.08 (d, J = 6.1 Hz, 2H), 3.57 (s, 3H), 2.58-2.51 (m, 2H), 2.29 (t, J = 7.4 Hz, 2H), 1.88-1.75 (m, 2H), 1.39 (s, 9H) |

TABLE 22-continued

| Characterization data for intermediates prepared according to above. | | | | |
|---|---|---|---|---|
| Inter-me-diate | Structure | Chemical Name | MS: $[(M + 1)]^+$ | $^1$H-NMR |
| F20 | 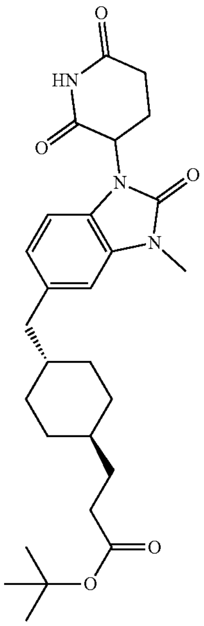 [SMILES: Cn1c(=O)n(C2CCC(=O)NC2=O)c2ccc(C[C@H]3CC[C@H](CCC(=O)OC(C)(C)C)CC3)cc21] | tert-butyl 3-[(1r,4r)-4-[[1-(2,6-dioxo-piperidin-3-yl)-3-methyl-2-oxo-1,3-benzodiazol-5-yl]methyl]cyclohexyl]propanoate | $[(M - H)]^-$ = 485.05 | (400 MHz, DMSO-$d_6$) δ 11.08 (s, 1H), 6.99 (d, J = 8.0 Hz, 2H), 6.82 (dd, J = 8.0, 1.6 Hz, 1H), 5.36-5.32 (m, 1H), 3.31 (s, 3H), 2.97-2.85 (m, 1H), 2.78-2.59 (m, 2H), 2.48 (s, 1H), 2.17 (t, J = 7.6 Hz, 2H), 2.06-1.94 (m, 1H), 1.70-1.64 (m, 4H), 1.47-1.41 (m, 1H), 1.39 (s, 9H), 1.36 (d, J = 7.6 Hz, 2H), 1.24 (d, J = 6.7 Hz, 1H), 1.20-1.13 (m, 1H), 1.00-0.75 (m, 4H) |
| F21 | 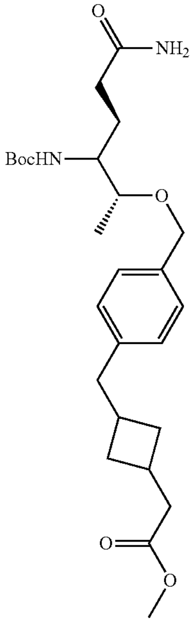 | methyl 2-(3-[[4-([[(2R,3S)-3-[(tert-butoxy-carbonyl)amino]-5-carbamoyl-pentan-2-yl]xy]methyl)phenyl]methyl]cyclobutyl)acetate | 477.30 | (400 MHz, $CD_3OD$) δ 7.27 (dd, J = 8.1, 2.1 Hz, 2H), 7.13 (t, J = 8.7 Hz, 2H), 4.62-4.44 (m, 2H), 3.64 s, 3H), 3.63-3.56 (m, 1H), 3.52-3.49 (m, 1H), 2.81-2.62 (m, 2H), 2.62-2.54 (m, 1H), 2.53-2.35 (m, 3H), 2.35-2.15 (m, 4H), 2.06-1.89 (m, 2H), 1.87-1.76 (m, 1H), 1.69-1.57 (m, 1H), 1.46 (s, 9H), 1.17 (s, 3H) |

TABLE 22-continued

| Characterization data for intermediates prepared according to above. | | | | |
|---|---|---|---|---|
| Inter-me-diate | Structure | Chemical Name | MS: $[(M + 1)]^+$ | $^1$H-NMR |
| F22 | 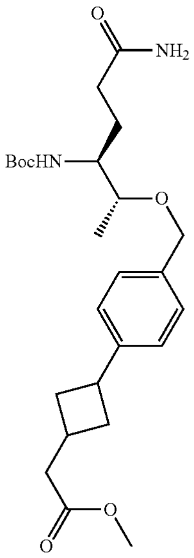 [SMILES: COC(=O)CC1CC(c2ccc(CO[C@H](C)[C@H](CCC(N)=O)NC(=O)OC(C)(C)C)cc2)C1] | Methyl 2-[3-[4-([[(2R,3S)-3-[(tert-butoxy-carbonyl)amino]-5-carbamoyl-pentan-2-yl]oxy]methyl)phenyl]cyclobutyl]acetate | 463.45 | (400 MHz, $CD_3OD$) δ 7.35-7.28 (m, 2H), 7.26-7.12 (m, 2H), 4.68-4.38 (m, 2H), 3.67 s, 3H), 3.67-3.56 (m, 1H), 3.57-3.46 (m, 1H), 3.46-3.34 (m, 1H), 2.75-2.42 (m, 4H), 2.36-2.32 (m, 1H), 2.25-2.13 (m, 1H), 2.05 (s, 2H), 2.04-1.93 (m, 1H), 1.88-1.76 (m, 1H), 1.69-1.59 (m, 1H), 1.45 (s, 9H), 1.20 (s, 3H) |
| F23 | 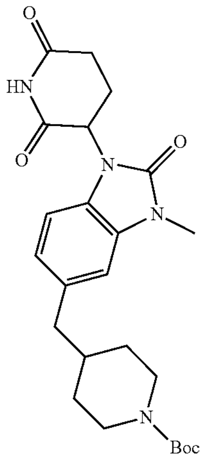 [SMILES: Cn1c(=O)n(C2CCC(=O)NC2=O)c2ccc(CC3CCN(C(=O)OC(C)(C)C)CC3)cc21] | tert-butyl 4-[[1-(2,6-dioxo-piperidin-3-yl)-3-methyl-2-oxo-1,3-benzodiazol-5-yl]methyl]piperidine-1-carboxylate | 456.95 | (400 MHz, DMSO-d6) δ 11.08 (s, 1H), 7.03-6.94 (m, 2H), 6.84 (dd, J = 8.0, 1.5 Hz, 1H), 5.34 (dd, J = 12.7, 5.4 Hz, 1H), 3.92 (d, J = 13.0 Hz, 2H), 2.90 (m, 1H), 2.77-2.57 (m, 4H), 2.54 (m, 4H), 2.05-1.95 (m, 2H), 1.77-1.60 (m, 1H), 1.61-1.52 (m, 2H), 1.39 (s, 9H), 1.10-0.96 (m, 2H) |
| F24 | 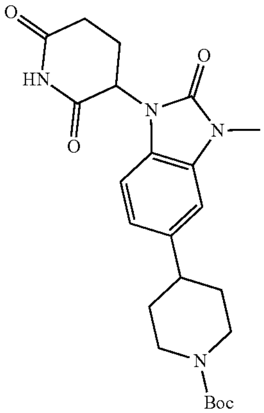 [SMILES: Cn1c(=O)n(C2CCC(=O)NC2=O)c2ccc(C3CCN(C(=O)OC(C)(C)C)CC3)cc21] | tert-butyl 4-[1-(2,6-dioxo-piperidin-3-yl)-3-methyl-2-oxo-1,3-benzodiazol-5-yl]piperidine-1-carboxylate | 443.20 | (400 MHz, DMSO-$d_6$) δ 11.09 (s, 1H), 7.12 (d, J = 1.7 Hz, 1H), 7.02 (d, J = 8.1 Hz, 1H), 6.92 (dd, J = 8.1, 1.6 Hz, 1H), 5.34 (dd, J = 12.7, 5.4 Hz, 1H), 4.10 (d, J = 12.9 Hz, 2H), 3.34 (s, 3H), 2.99-2.57 (m, 6H), 2.05-1.98 (m, 1H), 1.80-1.71 (m, 2H), 1.56 (tt, J = 12.7, 6.4 Hz, 2H), 1.43 (s, 9H) |

TABLE 22-continued

Characterization data for intermediates prepared according to above.

| Inter-me-diate | Structure | Chemical Name | MS: $[(M + 1)]^+$ | $^1$H-NMR |
|---|---|---|---|---|
| F25 | 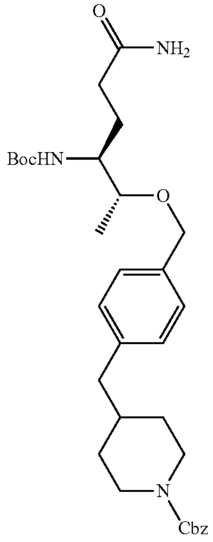 [SMILES: C[C@@H](OCc1ccc(CC2CCN(C(=O)OCc3ccccc3)CC2)cc1)[C@H](CCC(N)=O)NC(=O)OC(C)(C)C] | benzyl 4-[[4-([[2R,3S)-3-(tert-butoxy-carbonyl)amino]-5-carbamoyl-pentan-2-yl]oxy]methyl)phenyl]methyl]piperidine-1-carboxylate | 568.30 | (400 MHz, DMSO-$d_6$) δ 7.43-7.28 (m, 6H), 7.24 (d, J = 8.0 Hz, 2H), 7.12 (d, J = 8.0 Hz, 2H), 6.68 (s, 1H), 6.61 (d, J = 9.1 Hz, 1H), 5.06 (d, J = 2.5 Hz, 2H), 4.49-4.34 (m, 1H), 4.02-3.96 (m, 4H), 3.55-3.37 (m, 1H), 2.72 (d, J = 31.2 Hz, 4H), 2.06-2.02 (m, 1H), 1.83-1.68 (m, 1H), 1.65-1.42 (m, 4H), 1.39 (s, 9H), 1.11-0.93 (m, 6H) |
| F26 | 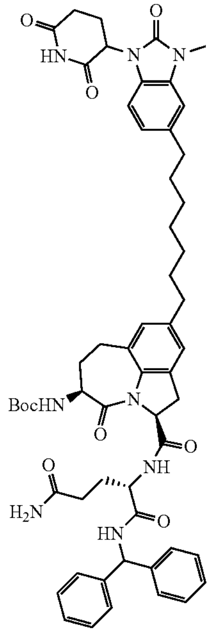 [SMILES: Cn1c(=O)n(C2CCC(=O)NC2=O)c2ccc(CCCCCCCc3cc4c5c(c3)C[C@@H](C(=O)N[C@@H](CCC(N)=O)C(=O)NC(c3ccccc3)c3ccccc3)N5C(=O)[C@@H](NC(=O)OC(C)(C)C)CC4)cc21] | tert-butyl N-[(2S,11S)-2-[[(1S)-3-carbamoyl-1-(diphenyl-methyl-carbamoyl)propyl]carbamoyl]-6-[7-[1-(2,6-dioxo-piperidin-3-yl)-3-methyl-2-oxo-1,3-benzodiazol-5-yl]heptyl]-12-oxo-1-azatricyclo-[6.4.1.0^[4,13]]trideca-4(13),5,7-trien-11-yl]carbamate | 995.40 | (400 MHz, DMSO-$d_6$) δ 11.08 (s, 1H), 8.78 (d, J = 8.5 Hz, 1H), 8.20-8.14 (m, 3H), 7.36-7.19 (m, 9H), 7.04-6.97 (m, 2H), 6.91-6.81 (m, 3H), 6.75-6.73 (m, 1H), 6.66 (s, 1H), 6.03-5.98 (m, 1H), 5.36-5.32 (m, 3H), 5.12 (m, 1H), 4.33-4.31 (m, 1H), 4.05-3.98 (m, 1H), 3.32 (s, 3H), 3.04-3.01 (m, 2H), 2.87 (d, J = 18.0 Hz, 2H), 2.72-2.65 (m, 4H), 2.22-1.89 (m, 7H), 1.58-1.45 (m, 4H), 1.39 (s, 9H), 1.33-1.25 (m, 7H) |

TABLE 22-continued

| Characterization data for intermediates prepared according to above. | | | | |
|---|---|---|---|---|
| Inter-me-diate | Structure | Chemical Name | MS: $[(M + 1)]^+$ | $^1$H-NMR |
| F27 | 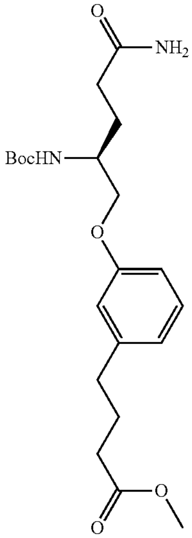 [SMILES: COC(=O)CCCc1cccc(OC[C@H](CCC(N)=O)NC(=O)OC(C)(C)C)c1] | methyl 4-[3-[(2S)-2-(tert-butoxy-carbonyl) amino]-4-carbamoyl-butoxy] phenyl] butanoate | 409.30 | (400 MHz, DMSO-$d_6$) δ 7.26 (s, 1H), 7.23-7.14 (m, 1H), 6.81 (d, J = 8.5 Hz, 1H), 6.75 (dt, J = 5.3, 2.7 Hz, 3H), 6.72 (s, 1H), 3.87-3.83 (m, 2H), 3.71 (dd, J = 12.0, 5.1 Hz, 1H), 3.59 (s, 3H), 2.56 (t, J = 7.6 Hz, 2H), 2.30 (t, J = 7.4 Hz, 2H), 2.21-2.04 (m, 2H), 1.88-1.75 (m, 3H), 1.62-1.58 (m, 1H), 1.40 (s, 9H) |
| F28 | 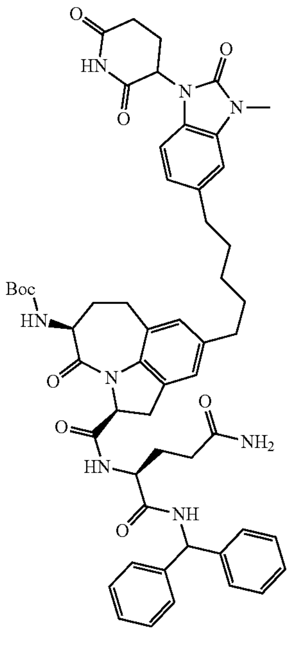 [SMILES: Cn1c(=O)n(C2CCC(=O)NC2=O)c2ccc(CCCCCc3cc4c5c(c3)C[C@@H](C(=O)N[C@@H](CCC(N)=O)C(=O)NC(c3ccccc3)c3ccccc3)N5C(=O)[C@@H](NC(=O)OC(C)(C)C)CC4)cc21] | tert-butyl N-(2S,11S)-2-[[(1S)-3-carbamoyl-1-(diphenyl-methyl-carbamoyl) propyl] carbamoyl]-6-[5-[1-(2,6-dioxo-piperidin-3-yl)-3-methyl-2-oxo-1,3-benzodiazol-5-yl]pentyl]-12-oxo-1-azatricyclo [6.4.1.0^ [4, 13]] trideca-4(13),5,7-trien-11-yl] carbamate | 967.60 | (300 MHz, Chloroform-d) δ 9.07-8.70 (m, 1H), 7.92-7.78 (m, 2H), 7.35-7.30 (m, 2H), 7.26-7.11 (m, 4H), 6.91-6.69 (m, 4H), 6.26 (d, J = 8.3 Hz, 1H), 5.92-5.84 (m, 2H), 5.28-5.17 (m, 1H), 5.12 (dd, J = 11.0, 3.4 Hz, 1H), 4.58-4.51 (m, 2H), 4.27 (s, 1H), 3.41 (s, 3H), 3.37-3.25 (m, 1H), 3.20-3.05 (m, 2H), 2.95-2.59 (m, 4H), 2.53 (t, J = 7.4 Hz, 1H), 2.29-2.18 (m, 6H), 2.10-2.00 (m, 2H), 1.71-1.57 (m, 4H), 1.49-1.47 (m, 13H), 1.38-1.29 (m, 5H) |

TABLE 22-continued

| Characterization data for intermediates prepared according to above. | | | | |
|---|---|---|---|---|
| Inter-me-diate | Structure | Chemical Name | MS: $[(M + 1)]^+$ | $^1$H-NMR |
| F29 | 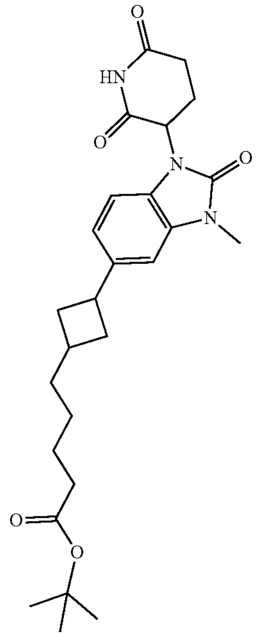 [SMILES: Cn1c(=O)n(C2CCC(=O)NC2=O)c2ccc(C3CC(CCCCC(=O)OC(C)(C)C)C3)cc21] | tert-butyl 5-[3-[1-(2,6-dioxo-piperidin-3-yl)-3-methyl-2-oxo-1,3-benzodiazol-5-yl] cyclobutyl] pentanoate | 470.20 | (400 MHz, Chloroform-d) δ 8.37 (s, 1H), 6.99-6.83 (m, 2H), 6.74 (dd, J = 8.1, 6.3 Hz, 1H), 5.27-5.22 (m, 1H), 3.67-3.59 (m, 1H), 3.46 (d, J = 1.4 Hz, 3H), 3.42-3.33 (m, 1H), 3.00-2.65 (m, 3H), 2.56-2.48 (m, 1H), 2.32-2.18 (m, 3H), 2.16-2.07 (m, 1H), 1.74-1.54 (m, 4H), 1.47 (d, J = 2.3 Hz, 9H), 1.45-1.39 (m, 2H), 1.39-1.23 (m, 2H) |
| F30 | 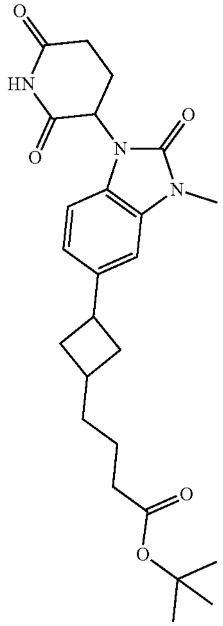 [SMILES: Cn1c(=O)n(C2CCC(=O)NC2=O)c2ccc(C3CC(CCCC(=O)OC(C)(C)C)C3)cc21] | tert-butyl 4-[3-[1-(2,6-dioxo-piperidin-3-yl)-3-methyl-2-oxo-1,3-benzodiazol-5-yl] cyclobutyl] butanoate | 456.20 | (400 MHz, Methanol-$d_4$) δ 7.13-6.93 (m, 3H), 5.37-5.27 (m, 1H), 4.59 (s, 2H), 3.73-3.55 (m, 1H), 3.46-3.44 (m, 3H), 3.01-2.87 (m, 1H), 2.87-2.74 (m, 2H), 2.55 (dt, J = 10.4, 7.8 Hz, 1H), 2.36-2.04 (m, 5H), 1.75-1.73 (m, 1H), 1.68-1.52 (m, 2H), 1.49-1.46 (m, 12H). |

TABLE 22-continued

| Characterization data for intermediates prepared according to above. | | | | |
|---|---|---|---|---|
| Inter-me-diate | Structure | Chemical Name | MS: $[(M+1)]^+$ | $^1$H-NMR |
| F31 | 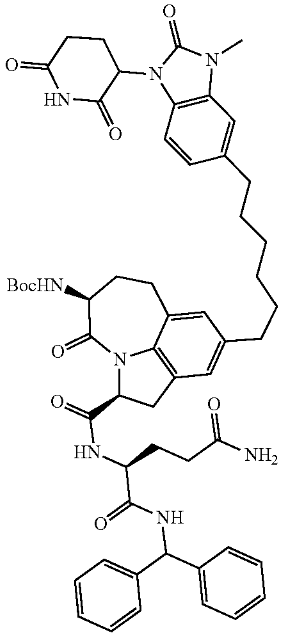 [SMILES: Cn1c(=O)n(C2CCC(=O)NC2=O)c2ccc(CCCCCCc3cc4c5c(c3)C[C@@H](C(=O)N[C@@H](CCC(N)=O)C(=O)NC(c3ccccc3)c3ccccc3)N5C(=O)[C@@H](NC(=O)OC(C)(C)C)CC4)cc21] | tert-butyl N-[(2S,11S)-2-[[(1S)-3-carbamoyl-1-(diphenyl-methyl-carbamoyl) propyl] carbamoyl]-6-[6-[1-(2,6-dioxo-piperidin-3-yl)-3-methyl-2-oxo-1,3-benzodiazol-5-yl]hexyl]-12-oxo-l-azatricyclo [6.4.1.0^[4,13]] trideca-4(13),5,7-trien-11-yl] carbamate | 981.65 | (400 MHz, DMSO-$d_6$) δ 11.08 (s, 1H), 8.79 (d, J = 8.5 Hz, 1H), 8.19 (d, J = 8.0 Hz, 1H), 7.38-7.16 (m, 13H), 7.05-6.96 m, 3H), 6.91-6.83 (m, 3H), 6.75 (s, 1H), 6.08 (d, J = 8.3 Hz, 1H), 5.34 (dd, J = 12.8, 5.3 Hz, 1H), 5.08 (dd, J = 11.0, 2.9 Hz, 1H), 4.36-4.30 (m, 1H), 4.04-4.00 (m, 1H), 3.32 (s, 3H), 3.04-2.86 (m, 2H), 2.76-2.58 (m, 3H), 2.17-1.95 (m, 6H), 1.91-1.76 (m, 1H), 1.63-1.52 (m, 3H), 1.39 (s, 9H), 1.35-1.24 (m, 9H) |
| F32 | 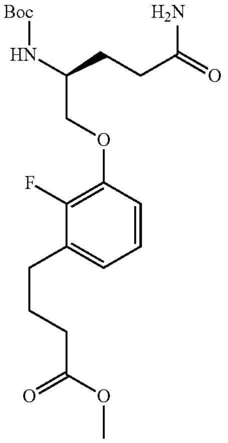 [SMILES: COC(=O)CCCc1cccc(OC[C@H](CCC(N)=O)NC(=O)OC(C)(C)C)c1F] | methyl 4-[3-[(2S)-2-(tert-butoxy-carbonyl) amino]-4-carbamoyl-butoxy]-2-fluoro-phenyl] butanoate | 427.20 | (300 MHz, DMSO-$d_6$) δ 7.29-7.27 (m, 1H), 7.03 (d, J = 5.8 Hz, 2H), 6.83 (d, J = 9.6 Hz, 2H), 6.77-6.74 (m, 1H), 3.93 (d, J = 6.0 Hz, 2H), 3.75-3.73 (m, 1H), 3.34 (d, J = 1.2 Hz, 1H), 2.64-2.59 (m, 2H), 2.33-2.31 (m, 3H), 2.15-2.12 (m, 2H), 1.84-1.81 (m, 3H), 1.62 (d, J = 10.3 Hz, 1H), 1.54-1.51 (m, 1H), 1.40 (s, 9H) |

TABLE 22-continued

| Characterization data for intermediates prepared according to above. | | | | |
|---|---|---|---|---|
| Inter-me-diate | Structure | Chemical Name | MS: [(M + 1)]+ | $^1$H-NMR |
| F33 | 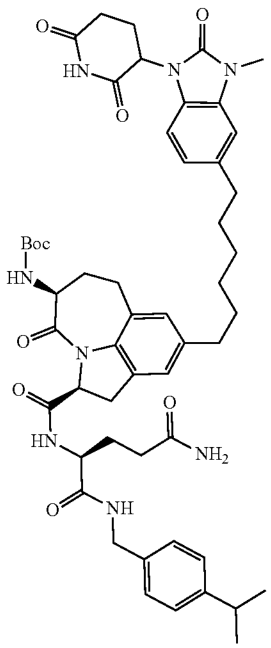 [SMILES: CC(C)c1ccc(CNC(=O)[C@H](CCC(N)=O)NC(=O)[C@@H]2Cc3cc(CCCCCCc4ccc5c(c4)n(C)c(=O)n5C4CCC(=O)NC4=O)cc4c3N2C(=O)[C@@H](NC(=O)OC(C)(C)C)CC4)cc1] | tert-butyl N-[(2S,11S)-2-[[(1S)-3-carbamoyl-1-[[(4-isopropyl-phenyl) methyl] carbamoyl] propyl] carbamoyl]-6-[6-[1-(2,6-dioxo-piperidin-3-yl)-3-methyl-2-oxo-1,3-benzodiazol-5-yl]hexyl]-12-oxo-1-azatricyclo [6.4.1.0^ [4,13] trideca-4(13),5,7-trien-11-yl] carbamate | 947.25 | (400 MHz, DMSO-$d_6$) δ 11.09 (s, 1H), 8.34 (t, J = 5.9 Hz, 1H), 8.19 (d, J = 7.9 Hz, 1H), 7.29-7.23 (m, 1H), 7.18-7.10 (m, 4H), 7.06 (d, J = 8.1 Hz, 1H), 7.03 (d, J = 1.5 Hz, 1H), 6.99 (d, J = 8.0 Hz, 1H), 6.90 (s, 1H), 6.88- 6.83 (m, 2H), 6.79-6.74 (m, 1H), 5.35-5.32 (m, 1H), 5.10-5.07 (m, 1H), 4.22-4.18 (m, 3H), 4.05-3.99 (m, 1H), 3.32 (s, 3H), 3.12-2.97 (m, 2H), 2.96-2.88 (m, 2H), 2.87-2.81 (m, 1H), 2.77-2.56 (m, 5H), 2.49-2.46 (m, 1H), 2.12-1.95 (m, 5H), 1.94-1.71 (m, 3H), 1.64-1.48 (m, 4H), 1.39 (s, 9H), 1.35-1.32 (m, 4H), 1.17 (d, J = 6.9 Hz, 6H) |
| F34 | 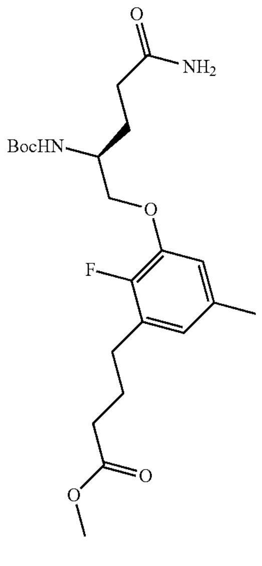 [SMILES: COC(=O)CCCc1cc(C)cc(OC[C@H](CCC(N)=O)NC(=O)OC(C)(C)C)c1F] | methyl 4-[3-[(2S)-2-[(tert-butoxy-carbonyl) amino]-4-carbamoyl-butoxy]-2-fluoro-5-methyl-phenyl] butanoate | 441.25 | (300 MHz, DMSO-$d_6$) δ 7.25 (s, 1H), 6.80 (d, J = 8.1 Hz, 2H), 6.71 (s, 1H), 6.64-6.56 (m, 1H), 3.88 (d, J = 6.0 Hz, 2H), 3.77-3.65 (m, 1H), 3.57 (s, 3H), 2.59-2.52 (m, 2H), 2.22 (s, 3H), 2.17-2.08 (m, 2H), 1.81-1.74 (m, 2H), 1.49 (q, J = 7.0 Hz, 4H), 1.37 (s, 9H) |

TABLE 22-continued

| Characterization data for intermediates prepared according to above. | | | | |
|---|---|---|---|---|
| Inter-me-diate | Structure | Chemical Name | MS: $[(M+1)]^+$ | $^1$H-NMR |
| F35 | 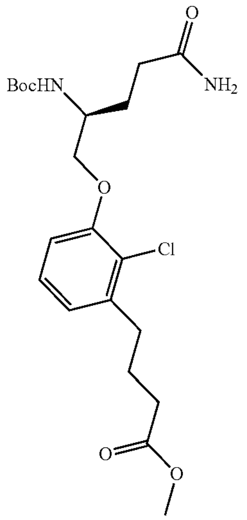 [SMILES: COC(=O)CCCc1cccc(OC[C@H](CCC(N)=O)NC(=O)OC(C)(C)C)c1Cl] | methyl 4-[3-[(2S)-2-[(tert-butoxy-carbonyl) amino]-4-carbamoyl-butoxy]-2-chloro-phenyl] butanoate | 443.15 | (400 MHz, DMSO-$d_6$) δ 7.27 (s, 1H), 7.21 (t, J = 7.9 Hz, 1H), 7.00 (dd, J = 8.3, 1.4 Hz, 1H), 6.90 (dd, J = 7.7, 1.3 Hz, 1H), 6.81 (d, J = 8.5 Hz, 1H), 6.74 (s, 1H), 3.93 (d, J = 6.3 Hz, 2H), 3.77 (q, J = 7.2, 4.4 Hz, 1H), 3.59 (s, 3H), 2.71 (dd, J = 8.7, 6.6 Hz, 2H), 2.34 (t, J = 7.4 Hz, 2H), 2.13 (tt, J = 14.7, 7.3 Hz, 2H), 1.91-1.76 (m, 3H), 1.39 (s, 9H), |
| F36 | 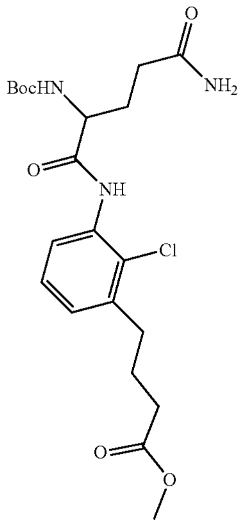 [SMILES: COC(=O)CCCc1cccc(NC(=O)C(CCC(N)=O)NC(=O)OC(C)(C)C)c1Cl] | methyl 4-[3-[(2S)-2-[(tert-butoxy-carbonyl) amino]-4-carbamoyl-butanamido]-2-chloro-phenyl] butanoate | 456.20 | (400 MHz, DMSO-$d_6$) δ 9.33 (s, 1H), 7.75 (d, J = 8.0 Hz, 1H), 7.28 (td, J = 8.6, 7.8, 5.8 Hz, 3H), 7.13 (dd, J = 7.6, 1.6 Hz, 1H), 6.84-6.79 (m, 1H), 4.15-4.09 (m, 1H), 3.59 (s, 3H), 2.76-2.72 (m, 2H), 2.36 (t, J = 7.3 Hz, 2H), 2.20 (s, 3H), 2.02-1.97 (m, 1H), 1.89-1.73 (m, 2H), 1.41 (s, 9H) |

TABLE 22-continued

| Characterization data for intermediates prepared according to above. | | | | |
|---|---|---|---|---|
| Inter-me-diate | Structure | Chemical Name | MS: [(M + 1)]+ | $^1$H-NMR |
| F37 | 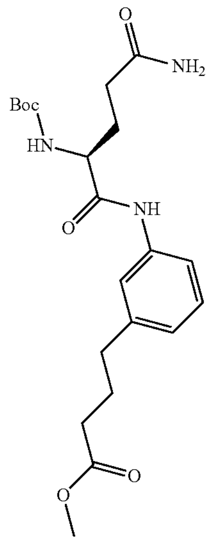 [SMILES: COC(=O)CCCc1cccc(NC(=O)[C@H](CCC(N)=O)NC(=O)OC(C)(C)C)c1] | methyl 4-[3-[(2S)-2-[(tert-butoxy-carbonyl) amino]-4-carbamoyl-butanamido]-phenyl] butanoate | 422.25 | (400 MHz, DMSO-d$_6$) δ 9.89 (s, 1H), 7.47-7.41 (m, 2H), 7.29 (s, 1H), 7.22 (dd, J = 8.6, 7.6 Hz, 1H), 7.03 (d, J = 7.7 Hz, 1H), 6.88 (d, J = 7.5 Hz, 1H), 6.78 (s, 1H), 5.76 (s, 1H), 4.08-3.98 (m, 1H), 3.59 (s, 3H), 2.56 (dd, J = 8.6, 6.7 Hz, 2H), 2.33 (t, J = 7.4 Hz, 2H), 2.15-2.09 (m, 2H), 1.96-1.71 (m, 3H), 1.39 (s, 9H) |
| F38 | 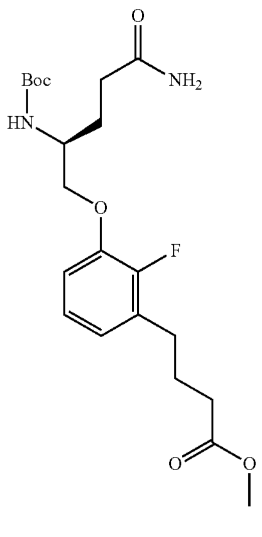 [SMILES: COC(=O)CCCc1cccc(OC[C@H](CCC(N)=O)NC(=O)OC(C)(C)C)c1F] | methyl 4-[3-[(2S)-2-[(tert-butoxy-carbonyl) amino]-4-carbamoyl-butoxy]-2-fluoro-phenyl] butanoate | 427.20 | (400 MHz, DMSO-d$_6$) δ 7.27 (s, 1H), 7.07-6.97 (m, 2H), 6.84-6.79 (m, 2H), 6.74 (s, 1H), 3.92 (d, J = 6.0 Hz, 2H), 3.76-3.72 (m, 1H), 3.58 (s, 3H), 2.61 (t, J = 7.6 Hz, 2H), 2.32 (t, J = 7.4 Hz, 2H), 2.18-2.05 (m, 2H), 1.82-1.78 (m, 3H), 1.64-1.52 (m, 1H), 1.39 (s, 9H) |

TABLE 22-continued

| Characterization data for intermediates prepared according to above. | | | | |
|---|---|---|---|---|
| Intermediate | Structure | Chemical Name | MS: $[(M+1)]^+$ | $^1$H-NMR |
| F39 | 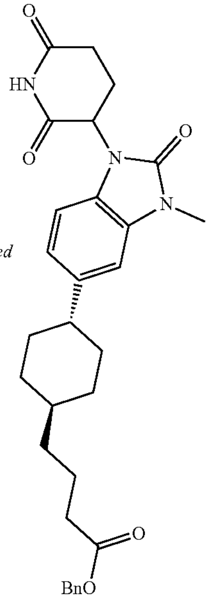 assumed | benzyl 4-[(1r,4s)-4-[1-(2,6-dioxo-piperidin-3-yl)-3-methyl-2-oxo-1,3-benzodiazol-5-yl] cyclohexyl] butanoate | 518.30 | (300 MHz, CDCl3) δ 8.03 (s, 1H), 7.36 (d, J = 10.7 Hz, 4H), 6.94 (d, J = 8.2 Hz, 1H), 6.89-6.86 (m, 1H), 6.73 (d, J = 8.0 Hz, 1H), 5.22-5.19 (m, 1H), 5.16-5.14 (m, 2H), 3.44 (s, 3H), 3.00-2.68 (m, 3H), 2.62-2.60 (m, 1H), 2.43-2.39 (m, 2H), 2.26-2.24 (m, 1H), 1.95-1.89 (m, 5H), 1.32-1.26 (m, 5H), 0.93-0.84 (m, 4H) |
| F40 | 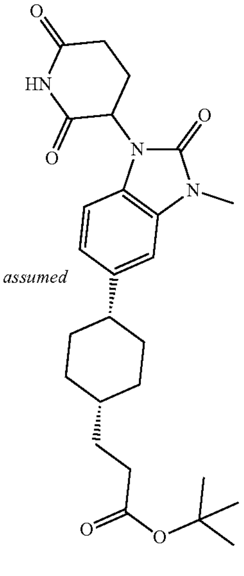 [SMILES: Cn1c(=O)n(C2CCC(=O)NC2=O)c2ccc([C@H]3CC[C@@H](CCC(=O)OC(C)(C)C)CC3)cc21] assumed | tert-butyl 3-((1s,4s)-4-(1-(2,6-dioxo-piperidin-3-yl)-3-methyl-2-oxo-2,3-dihydro-1H-benzo[d] imidazol-5-yl) cyclohexyl) propanoate | 470.30 | (300 MHz, CDCl3) δ 8.39 (s, 1H), 6.98-6.86 (m, 2H), 6.74 (d, J = 8.0 Hz, 1H), 5.35-5.18 (m, 1H), 3.45 (s, 3H), 3.00-2.88 (m, 1H), 2.92-2.62 (m, 2H), 2.56-2.52 (m, 1H), 2.35-2.18 (m, 3H), 1.95-1.89 (m, 4H), 1.73-1.70 (m, 1H), 1.60-1.56 (m, 2H), 1.48 (s, 9H), 1.45-1.33 (m, 4H), 1.25-1.02 (m, 2H). |

TABLE 22-continued

| Characterization data for intermediates prepared according to above. | | | | |
|---|---|---|---|---|
| Inter-me-diate | Structure | Chemical Name | MS: $[(M + 1)]^+$ | $^1$H-NMR |
| F41 | 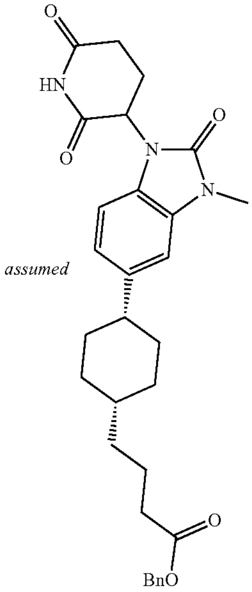 [SMILES: Cn1c(=O)n(C2CCC(=O)NC2=O)c2ccc([C@H]3CC[C@@H](CCCC(=O)OCc4ccccc4)CC3)cc21] | benzyl 4-[(1s,4r)-4-[1-(2,6-dioxo-piperidin-3-yl)-3-methyl-2-oxo-1,3-benzodiazol-5-yl] cyclohexyl] butanoate | 518.30 | (300 MHz, CDCl3) δ 8.10 (s, 1H), 7.41-7.36 (m, 4H), 7.34 (s, 1H), 6.97-6.85 (m, 2H), 6.73 (d, J = 8.0 Hz, 1H), 5.21 (dd, J = 12.4, 5.2 Hz, 1H), 5.14 (s, 2H), 3.44 (s, 3H), 3.00-2.64 (m, 3H), 2.51 (t, J = 12.4 Hz, 1H), 2.38 (t, J = 7.5 Hz, 2H), 2.29-2.17 (m, 1H), 1.93-1.85 (m, 4H), 1.75-1.71 (m, 3H), 1.51-1.45 (m, 1H), 1.32-1.26 (m, 3H), 1.18-1.06 (m, 2H). |
| F42 | 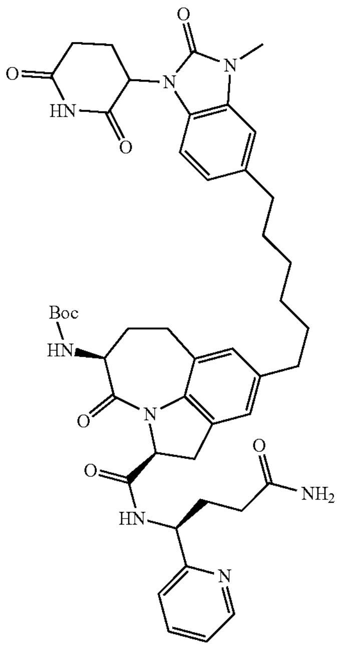 [SMILES: Cn1c(=O)n(C2CCC(=O)NC2=O)c2ccc(CCCCCCc3cc4c5c(c3)C[C@@H](C(=O)N[C@@H](CCC(N)=O)c3ccccn3)N5C(=O)[C@@H](NC(=O)OC(C)(C)C)CC4)cc21] | tert-butyl N-[(2S,11S)-2-[[(1S)-3-carbamoyl-1-(pyridin-2-yl) propyl] carbamoyl]-6-[6-[1-(2,6-dioxo-piperidin-3-yl)-3-methyl-2-oxo-1,3-benzodiazol-5-yl]hexyl]-12-oxo-1-azatricyclo [6.4.1.0^[4,13]] trideca-4(13),5,7-trien-11-yl] carbamate | 849.35 | (400 MHz, DMSO-$d_6$) δ 11.08 (s, 1H), 8.52 (d, J = 4.8 Hz, 1H), 8.47 (d, J = 8.0 Hz, 1H), 7.78-7.72 (m, 1H), 7.31 (d, J = 7.8 Hz, 1H), 7.26 (dd, J = 7.6, 4.8 Hz, 1H), 7.19 (s, 1H), 7.09 (d, J = 7.9 Hz, 1H), 7.05-6.96 (m, 2H), 6.91-6.81 (m, 3H), 6.70 (s, 1H), 5.34 (dd, J = 12.6, 5.4 Hz, 1H), 5.11 (dd, J = 10.5, 2.7 Hz, 1H), 4.83-4.75 (m, 1H), 4.07-3.99 (m, 1H), 3.51-3.34 (m, 2H), 3.32 (s, 3H), 3.06-2.78 (m, 4H), 2.74-2.56 (m, 4H), 2.46 (t, J = 7.8 Hz, 2H), 2.07-1.94 (m, 6H), 1.63-1.55 (m, 2H), 1.54-1.47 (m, 2H), 1.40 (s, 9H), 1.34-1.28 (m, 4H) |

TABLE 22-continued

Characterization data for intermediates prepared according to above.

| Intermediate | Structure | Chemical Name | MS: $[(M + 1)]^+$ | $^1H$-NMR |
|---|---|---|---|---|
| F43 | 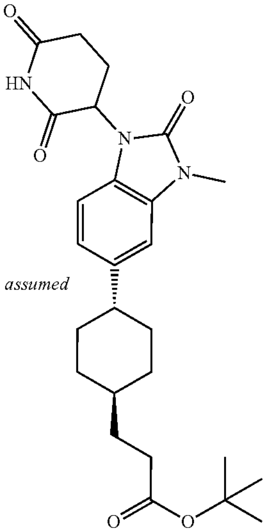 [SMILES: Cn1c(=O)n(C2CCC(=O)NC2=O)c2ccc([C@H]3CC[C@H](CCC(=O)OC(C)(C)C)CC3)cc21] | tert-butyl 3-[(1r,4r)-4-[1-(2,6-dioxo-piperidin-3-yl)-3-methyl-2-oxo-1,3-benzodiazol-5-yl]cyclohexyl]propanoate | 470.25 | (300 MHz, CDCl3) δ 8.03 (s, 1H), 7.01-6.88 (m, 2H), 6.74 (d, J = 8.0 Hz, 1H), 5.23 (dd, J = 12.5, 5.4 Hz, 1H), 3.47 (s, 3H), 2.97 (d, J = 16.1 Hz, 1H), 2.93-2.66 (m, 2H), 2.62 (s, 1H), 2.28 (t, J = 7.5 Hz, 3H), 1.90-1.88 (m, 1H), 1.84-1.71 (m, 3H), 1.68-1.61 (m, 6H), 1.49 (s, 9H), 1.30-1.21 (m, 1H) |
| F44 | 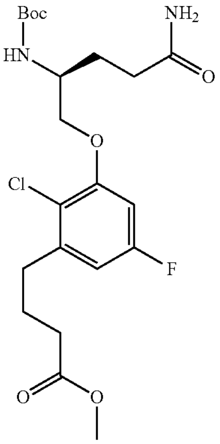 [SMILES: COC(=O)CCCc1cc(F)cc(OC[C@H](CCC(N)=O)NC(=O)OC(C)(C)C)c1Cl] | methyl 4-[3-[(2S)-2-[(tert-butoxy-carbonyl)amino]-4-carbamoyl-butoxy]-2-chloro-5-fluoro phenyl]butanoate | 461.25 | (300 MHz, DMSO-$d_6$) δ 7.28 (s, 1H), 6.99 (dd, J = 10.6, 2.9 Hz, 1H), 6.89-6.71 (m, 3H), 4.06-3.89 (m, 2H), 3.78 (d, J = 5.2 Hz, 1H), 2.83-2.67 (m, 2H), 2.36-2.30 (m, 2H), 2.16-2.11 (m, 2H), 1.85-1.80 (m, 3H), 1.69-1.45 (m, 2H), 1.39 (s, 9H), 1.40-1.26 (m, 2H) |
| F45 | 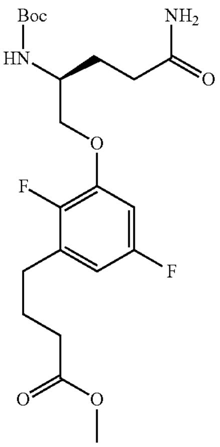 [SMILES: COC(=O)CCCc1cc(F)cc(OC[C@H](CCC(N)=O)NC(=O)OC(C)(C)C)c1F] | methyl 4-[3-[(2S)-2-[(tert-butoxy-carbonyl)amino]-4-carbamoyl-butoxy]-2,5-difluoro phenyl]butanoate | 445.15 | (300 MHz, DMSO-$d_6$) δ 7.27 (s, 1H), 7.03-6.93 (m, 1H), 6.85 (d, J = 8.4 Hz, 1H), 6.78-6.65 (m, 2H), 3.95 (t, J = 6.0 Hz, 2H), 3.76-3.74 (m, 1H), 3.59 (s, 3H), 2.61-2.55 (m, 2H), 2.32-2.27 (m, 2H), 2.11-2.08 (m, 2H), 1.81-1.75 (m, 3H), 1.52-1.47 (m, 1H), 1.39 (s, 9H) |

TABLE 22-continued

Characterization data for intermediates prepared according to above.

| Intermediate | Structure | Chemical Name | MS: [(M + 1)]+ | 1H-NMR |
|---|---|---|---|---|
| F46 | 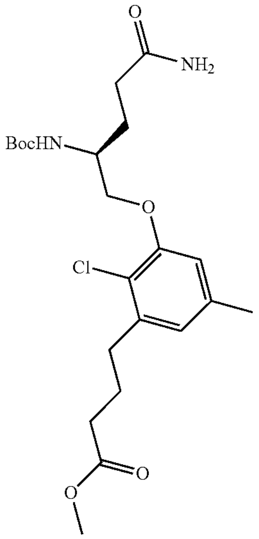 [SMILES: COC(=O)CCCc1cc(C)cc(OC[C@H](CCC(N)=O)NC(=O)OC(C)(C)C)c1Cl] | methyl 4-[3-[(2S)-2-[(tert-butoxy-carbonyl)amino]-4-carbamoyl-butoxy]-2-chloro-5-methyl-phenyl]butanoate | 457.20 | 1H NMR (300 MHz, Chloroform-d) δ 6.68 (s, 1H), 6.59 (s, 1H), 6.39 (s, 1H), 5.41 (s, 1H), 5.16 (d, J = 8.5 Hz, 1H), 4.06-4.03 (m, 3H), 3.69 (s, 3H), 2.74 (t, J = 8.7 Hz, 2H), 2.37 (t, J = 7.3 Hz, 4H), 2.30 (s, 3H), 2.14-2.02 (m, 2H), 2.00-1.91 (m, 2H), 1.47 (s, 9H) |
| F47 | 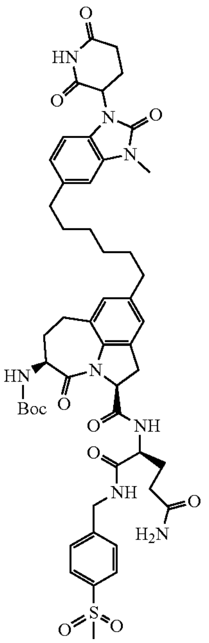 [SMILES: Cn1c(=O)n(C2CCC(=O)NC2=O)c2ccc(CCCCCCc3cc4c5c(c3)C[C@@H](C(=O)N[C@@H](CCC(N)=O)C(=O)NCc3ccc(S(C)(=O)=O)cc3)N5C(=O)[C@@H](NC(=O)OC(C)(C)C)CC4)cc21] | tert-butyl N-[(2S,11S)-2-[[(1S)-3-carbamoyl-1-[[(4-methane-sulfonyl-phenyl)methyl]carbamoyl]propyl]carbamoyl]-6-[6-[1-(2,6-dioxo-piperidin-3-yl)-3-methyl-2-oxo-1,3-benzodiazol-5-yl]hexyl]-12-oxo-1-azatricyclo[6.4.1.0^[4,13]]trideca-4(13),5,7-trien-11-yl]carbamate | 983.20 | (300 MHz, DMSO-$d_6$) δ 11.06 (s, 1H), 8.22 (d, J = 9.1 Hz, 1H), 7.84 (t, J = 8.0 Hz, 2H), 7.53-7.41 (m, 2H), 7.26-7.24 (m, 1H), 7.03-6.98 (m, 3H), 6.94-6.80 (m, 4H), 6.75 (s, 1H), 5.36-5.26 (m, 4H), 5.07-5.05 (m, 1H), 4.39-4.34 (m, 2H), 4.22-4.18 (m, 1H), 4.02-3.98 (m, 1H), 3.17-2.96 (m, 4H), 2.70-2.60 (m, 5H), 2.10-1.70 (m, 7H), 1.58-1.46 (m, 5H), 1.39 (s, 9H), 1.38-1.32 (m, 8H) |

Tert-butyl N-[(3S,4R)-1-carbamoyl-4-[(4-[4-[2-([[(2S,4R)-1-[(2S)-2-[(1-fluorocyclopropyl)formamido]-3,3-dimethylbutanoyl]-4-hydroxypyrrolidin-2-yl]formamido]methyl)-5-(4-methyl-1,3-thiazol-5-yl)phenoxy]butyl]phenyl)methoxy]pentan-3-yl]carbamate. (Intermediate F7)

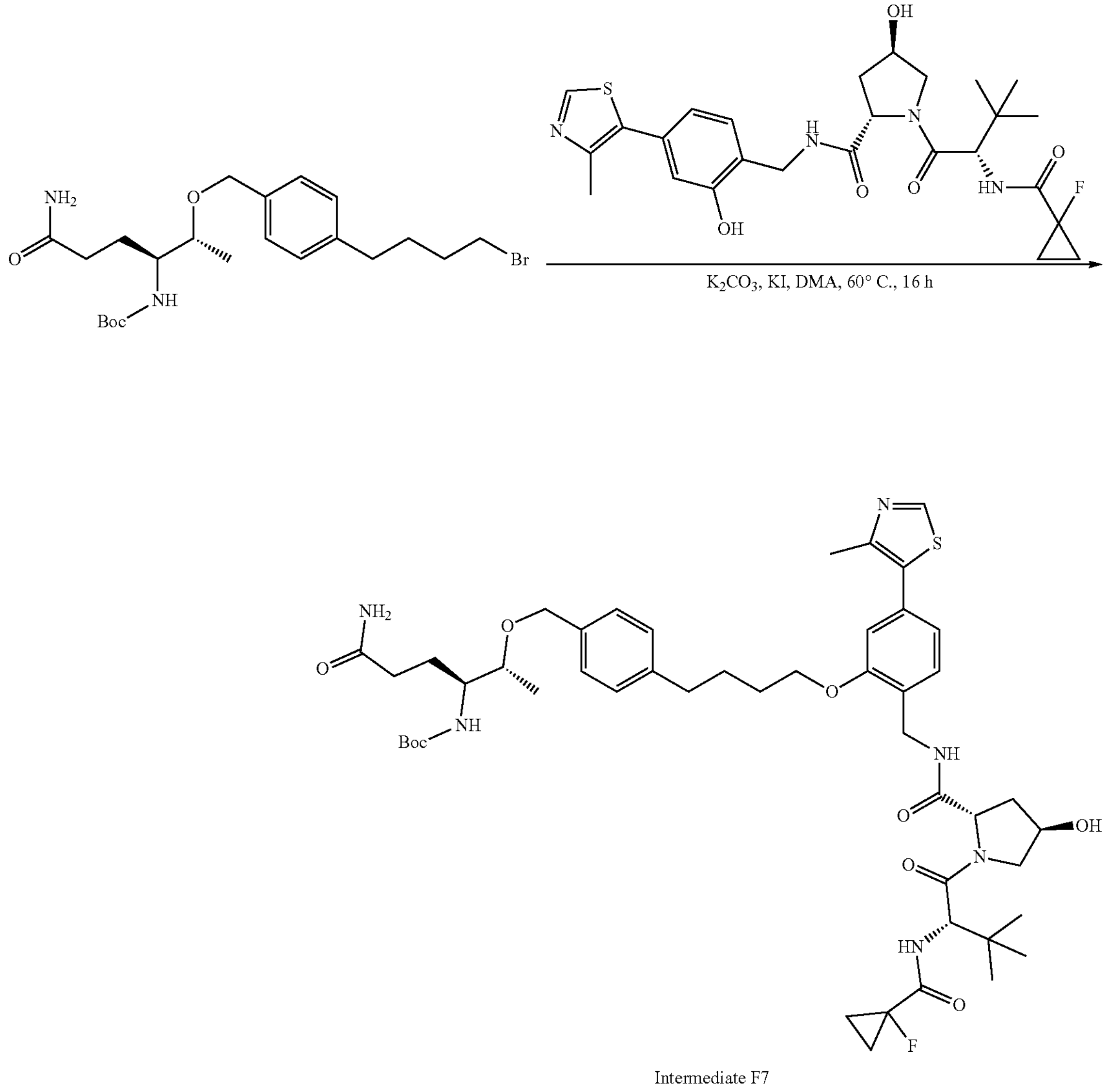

Intermediate F7

A mixture of tert-butyl N-[(3S,4R)-4-[[4-(4-bromobutyl)phenyl]methoxy]-1-carbamoylpentan-3-yl]carbamate (18.0 mg, 0.038 mmol), (2S,4R)-1-[(2S)-2-[(1-fluorocyclopropyl)formamido]-3,3-dimethylbutanoyl]-4-hydroxy-N-[[2-hydroxy-4-(4-methyl-1,3-thiazol-5-yl)phenyl]methyl]pyrrolidine-2-carboxamide (20.3 mg, 0.038 mmol), $K_2CO_3$ (10.6 mg, 0.076 mmol) and KI (1.00 mg, 0.006 mmol) in DMA (1.00 mL) was stirred for 16 hours at 60° C. under nitrogen atmosphere. The mixture was cooled down to room temperature. The mixture was purified by reversed phase flash chromatography with the following conditions: Column: WelFlash™ C18-I, 20~40 um, 120 g; EluentA: water (plus 10 mmol/LAcOH); Eluent B: ACN; Gradient: 40% - 60% B in 20 min; Flow rate: 50 mL/min; Detector: UV 220/200 nm; desired fractions were collected at 56% B to afford the title compound as a white solid (10.0 mg, 28%): $^1$H NMR (400 MHz, DMSO-$d_6$) δ 8.98 (s, 1H), 8.50 (t, J=6.0 Hz, 1H), 7.41 (d, J=7.8 Hz, 1H), 7.27-7.22 (m, 6H), 7.05-6.90 (m, 2H), 6.69 (s, 1H), 6.61 (d, J=9.1 Hz, 1H), 5.17 (s, 1H), 4.61 (d, J=9.2 Hz, 1H), 4.52 (t, J=8.3 Hz, 1H), 4.45 (d, J=12.7 Hz, 2H), 4.39-4.15 (m, 3H), 4.07 (s, 2H), 3.64 (q, J=11.0 Hz, 2H), 3.52-3.38 (m, 2H), 2.65 (d, J=6.3 Hz, 2H), 2.46 (s, 3H), 2.09-2.04 (m, 4H), 1.94 (d, J=11.4 Hz, 1H), 1.77 (s, 5H), 1.38 (s, 11H), 1.23 (d, J=8.1 Hz, 2H), 1.09-1.05 (m, 3H), 0.97 (s, 9H); MS (ESI, m/z): $[(M+1)]^+$=923.65.

The following intermediates in Table 23 were prepared according to the above procedure to prepare Intermediate F7.

TABLE 23

Characterization data for intermediates prepared according to above.

| Intermediate | Structure | Chemical Name | MS: $[(M + 1)]^+$ | $^1$H-NMR |
|---|---|---|---|---|
| F8 | 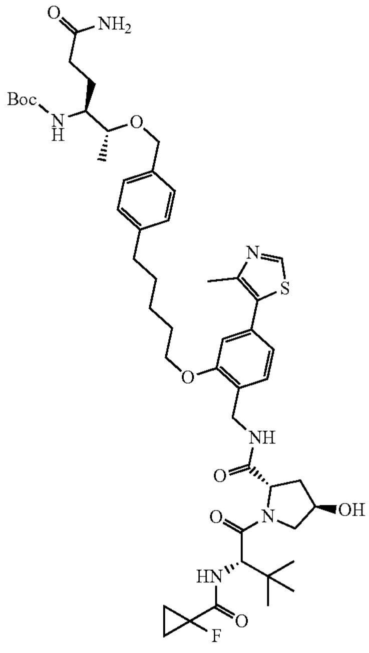 [SMILES: Cc1ncsc1-c1ccc(CNC(=O)[C@@H]2C[C@@H](O)CN2C(=O)[C@@H](NC(=O)C2(F)CC2)C(C)(C)C)c(OCCCCCc2ccc(CO[C@H](C)[C@H](CCC(N)=O)NC(=O)OC(C)(C)C)cc2)c1] | tert-butyl N-(3S,4R)-1-carbamoyl-4-[(4-[5-[2-([[(2S,4R)-1-[(2S)-2-[(1-fluorocyclo-propyl) formamido]-3,3-dimethyl-butanoyl]-4-hydroxy pyrrolidin-2-yl] formamido] methyl)-5-(4-methyl-1,3-thiazol-5-yl)phenoxy] pentyl]phenyl) methoxy] pentan-3-yl] carbamate | 937.6 | $^1$H NMR (400 MHz, DMSO-$d_6$) δ 8.98 (s, 1H), 8.49 (t, J = 5.9 Hz, 1H), 7.41 (d, J = 7.8 Hz, 1H), 7.32-7.26 (m, 1H), 7.24-7.20 (m, 3H), 7.16 (d, J = 7.9 Hz, 2H), 7.00 (d, J = 1.7 Hz, 1H), 6.95 (dd, J = 7.8, 1.6 Hz, 1H), 6.67 (s, 1H),6.59 (d, J = 9.1Hz, 1H), 5.17 (s, 1H), 4.61 (d, J = 9.1 Hz, 1H), 4.53 (t, J = 8.2 Hz, 1H), 4.43 (d, J = 4.6 Hz, 2H), 4.38 (d, J = 10.6 Hz, 1H), 4.29 (dd, J = 16.4, 6.0 Hz, 1H), 4.19 (dd, J = 16.6, 5.6 Hz, 1H), 4.05 (t, J = 6.3 Hz, 2H), 3.70-3.59 (m, 2H), 3.49-3.38 (m, 2H), 2.60 (t, J = 7.6 Hz, 2H), 2.46 (s, 3H), 2.15-2.01 (m, 3H), 1.96-1.90 (m, 1H), 1.80-1.77 (m, 3H), 1.68-1.64 (m, 2H), 1.52-1.47 (m, 3H), 1.38 (s, 11H), 1.27-1.19 (m, 2H), 1.06 (d, J = 6.0 Hz, 3H), 0.97 (s, 9H). |
| F9 | 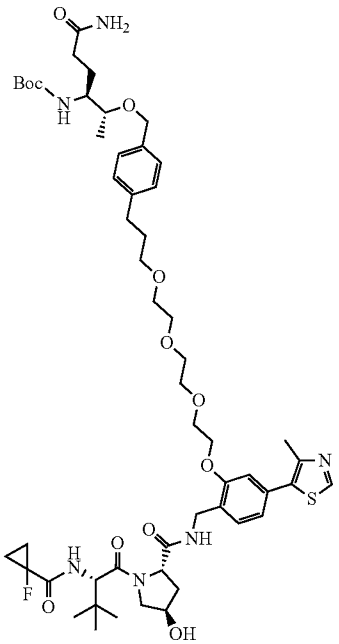 [SMILES: Cc1ncsc1-c1ccc(CNC(=O)[C@@H]2C[C@@H](O)CN2C(=O)[C@@H](NC(=O)C2(F)CC2)C(C)(C)C)c(OCCOCCOCCOCCCc2ccc(CO[C@H](C)[C@H](CCC(N)=O)NC(=O)OC(C)(C)C)cc2)c1] | tert-butyl N-[(3S,4R)-1-carbamoyl-4-[(4-[3-[2-(2-[2-[2-([[(2S,4R)-1-[(2S)-2-[(1-fluorocyclo-propyl) formamido]-3,3-dimethyl-butanoyl]-4-hydroxy-pyrrolidin-2-yl] formamido] methyl)-5-(4-methyl-1,3-thiazol-5-yl)phenoxy] ethoxy] ethoxy) ethoxy] propyl] phenyl) methoxy] pentan-3-yl]carbamate | 543.6 | $^1$H NMR (400 MHz DMSO-$d_6$) δ 8.98 (s, 1H), 8.47 (t, J = 6.0 Hz, 1H), 7.41 (d, J = 7.8 Hz, 1H), 7.29 (dd, J = 9.3, 2.7 Hz, 1H), 7.23-7.20 (m, 3H), 7.13 (d, J = 7.8 Hz, 2H), 7.04 (d, J = 1.6 Hz, 1H), 6.97 (dd, J = 7.8, 1.6 Hz, 1H), 6.67 (s, 1H), 6.59 (d, J = 9.1 Hz, 1H), 5.16 (d, J = 3.6 Hz, 1H), 4.60 (d, J = 9.2 Hz, 1H), 4.52 (t, J = 8.2 Hz, 1H), 4.42 (d, J = 3.3 Hz, 2H), 4.36 (s, 1H), 4.34-4.27 (m, 1H), 4.26-4.15 (m, 3H), 3.80 (dd, J = 5.7, 3.6 Hz, 2H), 3.72-3.60 (m, 3H), 3.60-3.38 (m, 6H), 3.41-3.29 (m, 6H), 2.58 (t, J = 7.7 Hz, 2H), 2.46 (s, 3H), 2.14-1.98 (m, 2H), 1.98-1.88 (m, 1H), 1.82-1.70 (m, 3H), 1.48 (s, 1H), 1.38 (s, 9H), 1.37-1.34 (m, 2H), 1.24-1.20 (m, 2H), 1.08-0.99 (m, 3H), 0.96 (s, 9H). |

TABLE 23-continued

| Characterization data for intermediates prepared according to above. | | | | |
|---|---|---|---|---|
| Intermediate | Structure | Chemical Name | MS: $[(M + 1)]^+$ | $^1$H-NMR |
| F10 | 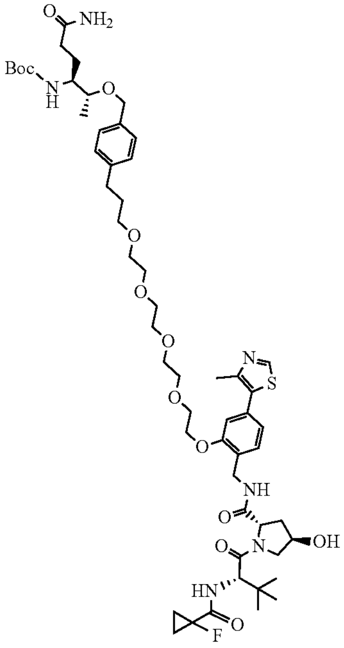 [SMILES: Cc1ncsc1-c1ccc(CNC(=O)[C@@H]2C[C@@H](O)CN2C(=O)[C@@H](NC(=O)C2(F)CC2)C(C)(C)C)c(OCCOCCOCCOCCOCCCc2ccc(CO[C@H](C)[C@H](CCC(N)=O)NC(=O)OC(C)(C)C)cc2)c1] | tert-butyl N-[(3S,4R)-1-carbamoyl-4-[(4-[1-[2-([[(2S,4R)-1-[(2S)-2-[(1-fluorocyclopropyl) formamido]-3,3-dimethylbutanoyl]-4-hydroxypyrrolidin-2-yl] formamido] methyl)-5-(4-methyl-1,3-thiazol-5-yl)phenoxy]-3,6,9,12-tetraoxapentadecan-15-yl]phenyl) methoxy] pentan-3-yl] carbamate | 1086.3 | $^1$H NMR (400 MHz, DMSO-$d_6$) δ 8.98 (s, 1H), 8.47 (t, J = 5.9 Hz, 1H), 7.41 (d, J = 7.8 Hz, 1H), 7.32-7.25 (m, 1H), 7.24-7.19 (m, 3H), 7.13 (d, J = 7.8 Hz, 2H), 7.04 (d, J = 1.7 Hz, 1H), 6.97 (dd, J = 7.8, 1.6 Hz, 1H), 6.67 (s, 1H), 6.59 (d, J = 9.1 Hz, 1H), 5.16 (d, J = 3.6 Hz, 1H), 4.60 (d, J = 9.2 Hz, 1H), 4.52 (t, J = 8.2 Hz, 1H), 4.42 (d, J = 3.4 Hz, 2H), 4.36 (s, 1H), 4.33-4.26 (m, 1H), 4.26-4.15 (m, 3H), 3.79 (t, J = 4.7 Hz, 2H), 3.66-3.60 (m, 3H), 3.58-3.33 (m, 15H), 2.58 (t, J = 7.7 Hz, 2H), 2.46 (s, 3H), 2.13-1.98 (m, 3H), 1.98-1.89 (m, 1H), 1.83-1.72 (m, 3H), 1.48 (t, J = 7.1 Hz, 1H), 1.38 (s, 11H), 1.26-1.18 (m, 2H), 1.05 (d, J = 6.0 Hz, 3H), 0.96 (s, 9H). |
| F11 | 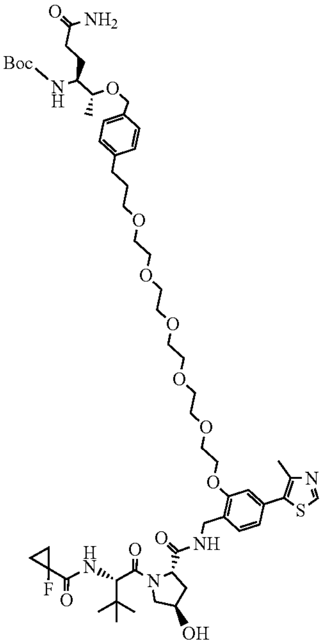 [SMILES: Cc1ncsc1-c1ccc(CNC(=O)[C@@H]2C[C@@H](O)CN2C(=O)[C@@H](NC(=O)C2(F)CC2)C(C)(C)C)c(OCCOCCOCCOCCOCCOCCCc2ccc(CO[C@H](C)[C@H](CCC(N)=O)NC(=O)OC(C)(C)C)cc2)c1] | tert-butyl N-[(3S,4R)-1-carbamoyl-4-[(4-[1-[2-([[(2S,4R)-1-[(2S)-2-[(1-fluorocyclopropyl) formamido]-3,3-dimethylbutanoyl]-4-hydroxypyrrolidin-2-yl] formamido] methyl)-5-(4-methyl-1,3-thiazol-5-yl)phenoxy]-3,6,9,12,15-n pentaoxaoctadecan-18-yl] phenyl) methoxy] pentan-3-yl] carbamate | 1129.8 | $^1$H NMR (400 MHz, DMSO-$d_6$) δ 8.98 (s, 1H), 8.48 (t, J = 6.0 Hz, 1H), 7.67-7.54 (m, 1H), 7.41 (d, J = 7.8 Hz, 1H), 7.29 (d, J = 9.0 Hz, 1H), 7.25-7.21 (m, 3H), 7.14 (d, J = 7.8 Hz, 2H), 7.04 (d, J = 1.7 Hz, 1H), 6.97 (dd, J = 7.8, 1.6 Hz, 1H), 6.67 (s, 1H), 6.59 (d, J = 9.0 Hz, 1H), 5.16 (d, J = 3.7 Hz, 1H), 4.60 (d, J = 9.2 Hz, 1H), 4.56-4.44 (m, 1H), 4.42 (d, J = 3.3 Hz, 2H), 4.36 (s, 2H), 4.34-4.26 (m, 1H), 4.26-4.15 (m, 3H), 3.79 (dd, J = 5.7, 3.5 Hz, 2H), 3.68-3.44 (m, 8H), 3.43-3.36 (m, 1H), 3.34 (d, J = 18.8 Hz, 6H), 2.58 (t, J =7.6 Hz, 3H), 2.46 (s, 4H), 2.14-1.88 (m, 2H), 1.80-1.72 (m, 4H), 1.48 (s, 1H), 1.38 (s, 10H), 1.35 (d, J = 8.3 Hz, 2H), 1.26-1.19 (m, 3H), 1.08-0.99 (m, 5H), 0.96 (s, 9H). |

TABLE 23-continued

Characterization data for intermediates prepared according to above.

| Inter-mediate | Structure | Chemical Name | MS: [(M + 1)]+ | 1H-NMR |
|---|---|---|---|---|
| F12 | 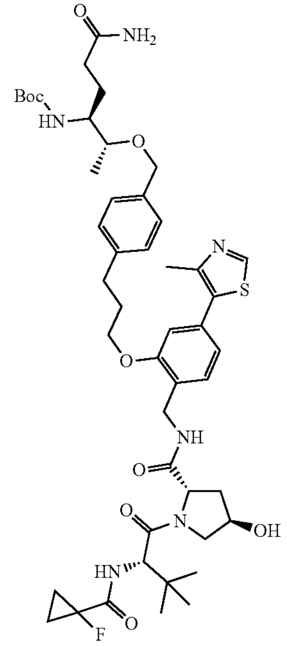 [SMILES: Cc1ncsc1-c1ccc(CNC(=O)[C@@H]2C[C@@H](O)CN2C(=O)[C@@H](NC(=O)C2(F)CC2)C(C)(C)C)c(OCCCc2ccc(CO[C@H](C)[C@H](CCC(N)=O)NC(=O)OC(C)(C)C)cc2)c1] | tert-butyl N-[(3S,4R)-1-carbamoyl-4-[(4-[3-[2-([[(2S,4R)-1-[(2S)-2-[(1-fluorocyclo-propyl) formamidol-3,3-dimethyl-butanoyl]-4-hydroxy-pyrrolidin-2-yl] formamidol] methyl)-5-(4-methyl-1,3-thiazol-5-yl)phenoxy] propyl] phenyl) methoxy] pentan-3-yl] carbamate | 909.6 | $^1$H NMR (400 MHz, DMSO-$d_6$) δ 8.98 (s, 1H), 8.51 (t, J = 6.0 Hz, 1H), 7.42 (d, J = 7.7 Hz, 1H), 7.33-7.17 (m, 6H), 6.97 (s, 2H), 7.01-6.93 (m, 1H), 6.68 (s, 1H), 6.60 (d, J = 9.1 Hz, 1H), 5.17 (d, J = 3.6 Hz, 1H), 4.61 (d, J = 9.2 Hz, 1H), 4.53 (t, J = 8.2 Hz, 1H), 4.49-4.38 (m, 2H), 4.36 (s, 1H), 4.37-4.21 (m, 2H), 4.05 (t, J = 6.0 Hz, 2H), 3.70-3.57 (m, 2H), 3.43-3.36 (m, 1H), 3.33 (s, 1H), 2.82-2.74 (m, 2H), 2.45 (s, 3H), 2.14-2.01 (m, 5H), 2.03-1.88 (m, 1H), 1.51- 1.39 (m, 1H), 1.37 (s, 8H), 1.36-1.32 (m, 2H), 1.23 (dd, J = 8.5, 3.3 Hz, 2H), 1.08-0.99 (m, 4H), 0.97 (s, 9H). |
| F13 | 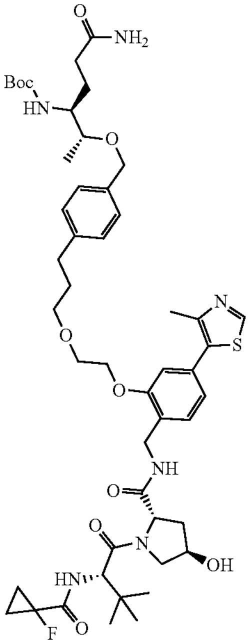 [SMILES: Cc1ncsc1-c1ccc(CNC(=O)[C@@H]2C[C@@H](O)CN2C(=O)[C@@H](NC(=O)C2(F)CC2)C(C)(C)C)c(OCCOCCCc2ccc(CO[C@H](C)[C@H](CCC(N)=O)NC(=O)OC(C)(C)C)cc2)c1] | tert-butyl N-[(3S,4R)-1-carbamoyl-4-[[4-(3-[2-[2-([[(2S,4R)-1-[(2S)-2-[(1-flourocyclo-propyl) formamido]-3,3-dimethyl-butanoyl]-4-hydroxy-pyrrolidin-2-yl]formamido] methyl)-5-(4-methyl-1,3-thiazol-5-yl)phenoxy] ethoxy] propyl) phenyl] methoxy] pentan-3-yl] carbamate | 953.5 | $^1$H NMR (400 MHz, $CDCl_3$) δ 8.71 (s, 1H), 7.36 (d, J = 7.6 Hz, 1H), 7.32 (d, J = 5.8 Hz, 1H), 7.22 (d, J = 7.8 Hz, 2H), 7.16 (d, J = 7.8 Hz, 2H), 7.07 (dd, J = 9.0, 3.4 Hz, 1H), 6.99 (dd, J =7.7, 1.5 Hz, 1H), 6.94 (d, J = 1.6 Hz, 1H), 6.39 (s, 1H), 5.51 (s, 1H), 4.95 (d, J = 9.7 Hz, 1H), 4.67 (t, J = 7.8 Hz, 1H), 4.61-4.54 (m, 2H), 4.51 (q, J = 6.2, 5.6 Hz, 2H), 4.47-4.35 (m, 2H), 4.22 (q, J = 5.2 Hz, 2H), 3.95 (d, J = 11.0 Hz, 1H), 3.90-3.82 (m, 2H), 3.66 (dd, J = 11.1,3.9 Hz, 2H), 3.60-3.54 (m, 4H), 2.71 (t, J = 7.5 Hz, 2H), 2.55 (s, 3H), 2.42 (dt, J = 13.0, 6.9 Hz, 1H), 2.27 (d, J = 9.5 Hz, 2H), 1.99-1.91 (m, 4H), 1.75-1.67 (m, 1H), 1.45 (s, 9H), 1.36-1.22 (m, 4H), 1.22 (d, J = 6.2 Hz, 3H), 0.96 (s, 9H). |

TABLE 23-continued

| Characterization data for intermediates prepared according to above. | | | | |
|---|---|---|---|---|
| Intermediate | Structure | Chemical Name | MS: $[(M + 1)]^+$ | $^1$H-NMR |
| F14 | 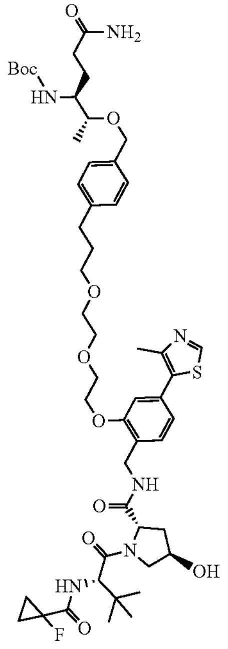 [SMILES: Cc1ncsc1-c1ccc(CNC(=O)[C@@H]2C[C@@H](O)CN2C(=O)[C@@H](NC(=O)C2(F)CC2)C(C)(C)C)c(OCCOCCOCCCc2ccc(CO[C@H](C)[C@H](CCC(N)=O)NC(=O)OC(C)(C)C)cc2)c1] | tert-butyl N-[(3S,4R)-1-carbamoyl-4-[[4-[3-[2-[2-[2-([[(2S,4R)-1-[(2S)-2-[(1-fluorocyclopropyl)formamido]-3,3-dimethylbutanoyl]-4-hydroxy-pyrrolidin-2-yl]formamido]methyl)-5-(4-methyl-1,3-thiazol-5-yl)phenoxy]ethoxy]ethoxy)propyl]phenyl]methoxy)pentan-3-yl]carbamate | 997.7 | $^1$H NMR (400 MHz, $CDCl_3$) δ 8.71 (s, 1H), 7.36 (d, J = 7.6 Hz, 1H), 7.32 (d, J = 5.8 Hz, 1H), 7.22 (d, J = 7.8 Hz, 2H), 7.16 (d, J = 7.8 Hz, 2H), 7.07 (dd, J = 9.0, 3.4 Hz, 1H), 6.99 (dd, J =7.7 , 1.5 Hz, 1H), 6.94 (d, J = 1.6 Hz, 1H), 6.39 (s, 1H), 5.51 (s, 1H), 4.95 (d, J = 9.7 Hz, 1H), 4.67 (t, J = 7.8 Hz, 1H), 4.61-4.54 (m, 2H), 4.51 (q, J = 6.2, 5.6 Hz, 2H), 4.47-4.35 (m, 2H), 4.22 (q, J = 5.2 Hz, 2H), 3.95 (d, J = 11.0 Hz, 1H), 3.90-3.82 (m, 2H), 3.66 (dd, J = 11.1, 3.9 Hz, 2H), 3.60-3.54 (m, 8H), 2.71 (t, J = 7.5 Hz, 2H), 2.55 (s, 3H), 2.42 (dt, J = 13.0, 6.9 Hz, 1H), 2.27 (d, J = 9.5 Hz, 2H), 1.99-1.91 (m, 4H), 1.75-1.67 (m, 1H), 1.45 (s, 9H), 1.36-1.22 (m, 4H), 1.22 (d, J = 6.2 Hz, 3H), 0.96 (s, 9H). |

(9H-fluoren-9-yl)methyl ((3S,6S)-6-(((2R,3S)-6-amino-2-((4-(16-(1-(2,6-dioxopiperidin-3-yl)-3-methyl-2-oxo-2,3-dihydro-1H-benzo[d]imidazol-5-yl)-5-oxo-7,10,13-trioxa-4-azahexadecyl)benzyl)oxy)-6-oxohexan-3-yl)carbamoyl)-4-oxo-1,2,3,4,6,7-hexahydroazepino[3,2,1-hi]indol-3-yl)carbamate (Intermediate G)

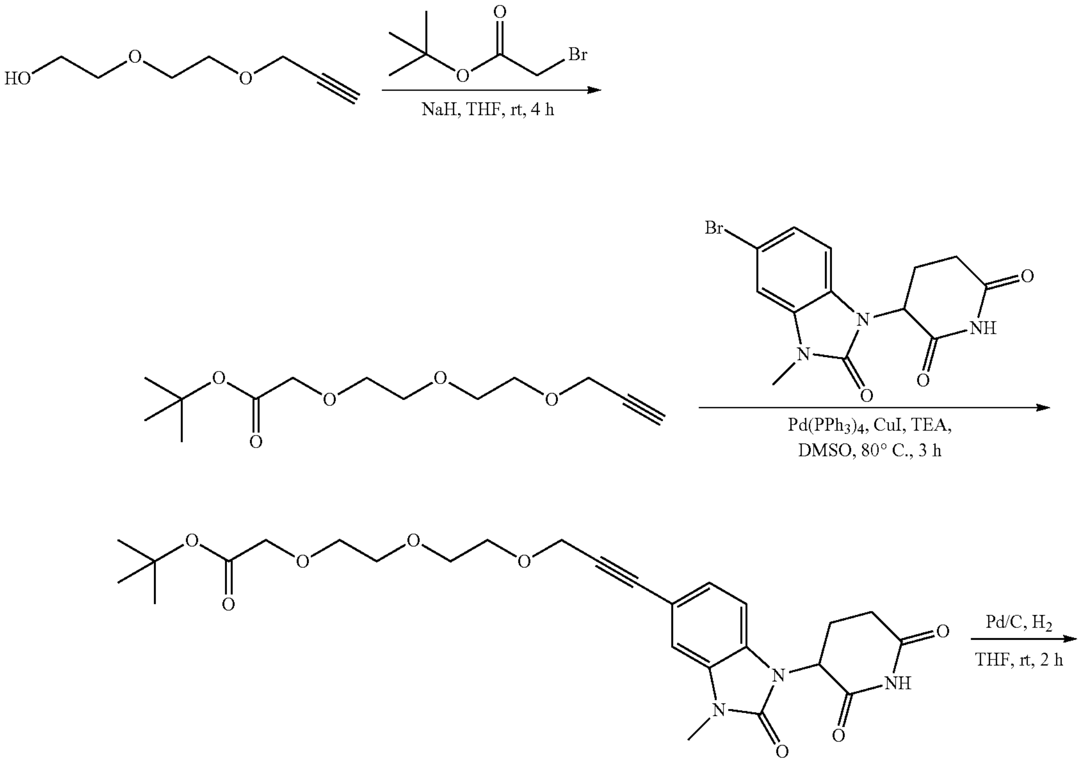

-continued

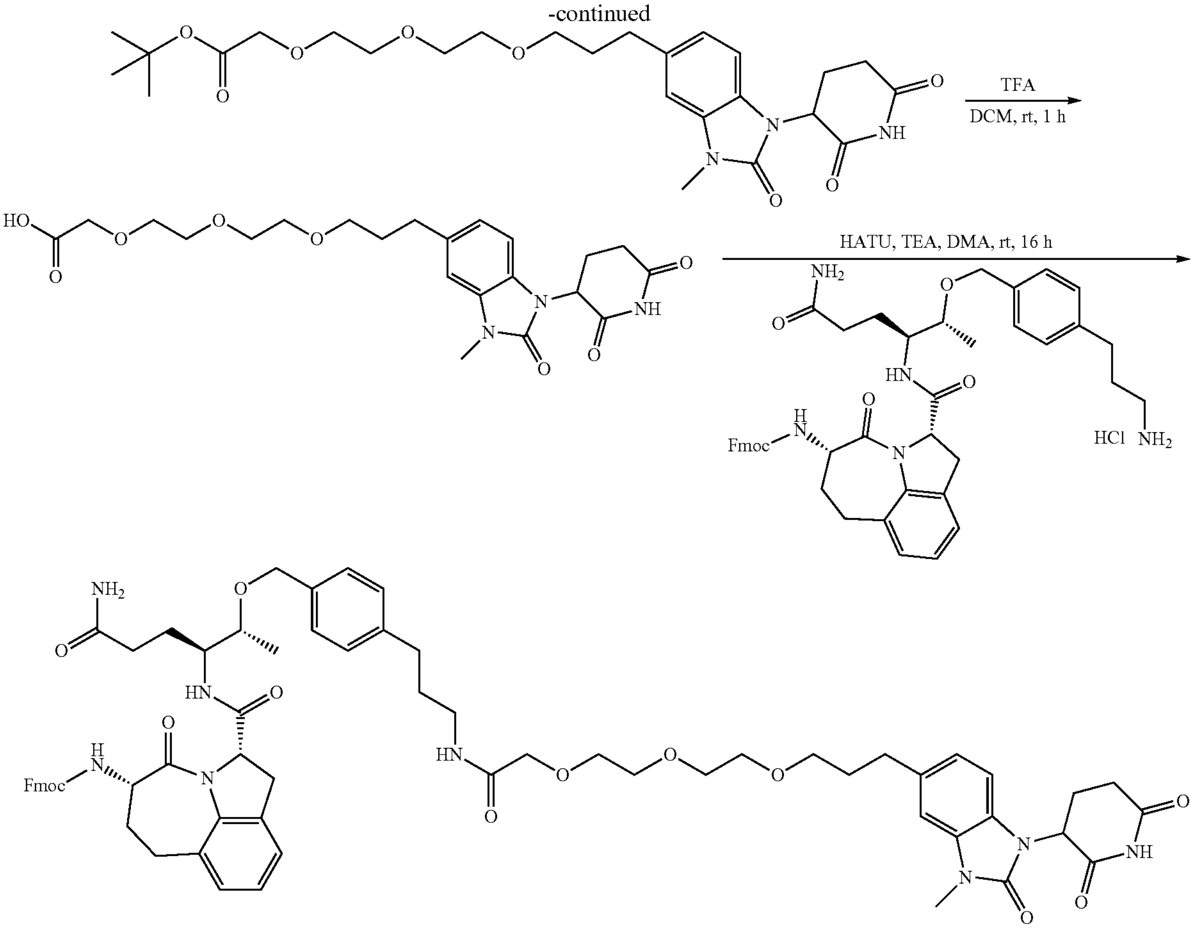

Intermediate G

Step 1. Tert-butyl 2-(2-(2-(prop-2-yn-1-yloxy)ethoxy)ethoxy)acetate. A solution of 2-[2-(prop-2-yn-1-yloxy)ethoxy]ethan-1-ol (7.50 g, 52.0 mmol) in THF (100 mL) was treated with NaH (2.70 g, 67.6 mmol, 60% dispersion in mineral oil) at 0° C. for 1 hour under nitrogen atmosphere. Followed by the addition of a solution of tert-butyl 2-bromoacetate (12.2 g, 62.4 mmol) in THF (50.0 mL) dropwise at 0° C. The resulting mixture was stirred for 16 hours at room temperature under nitrogen atmosphere and quenched with saturated aqueous $NH_4Cl$ solution (200 mL) at 0° C. The resulting mixture was extracted with ethyl acetate (2×200 mL). The combined organic layers was washed with brine (300 mL) and dried over anhydrous $Na_2SO_4$. After filtration, the filtrate was concentrated under reduced pressure. The residue was purified by silica gel column chromatography, eluted with 10% ethyl acetate in petroleum ether to afford the title compound as a light yellow oil (2.70 g, 20%): $^1H$ NMR (400 MHz, $CDCl_3$) δ 4.21 (d, J=2.4 Hz, 2H), 4.03 (s, 2H), 3.74-3.62 (m, 8H), 2.43 (t, J=2.4 Hz, 1H), 1.48 (s, 9H).

The following intermediates in Table 24 were prepared according to Step 1 to prepare Intermediate G.

TABLE 24

Characterization data for intermediates prepared according to procedure above.

| Intermediate | Structure | Chemical Name | $^1H$-NMR |
|---|---|---|---|
| G-1-1 | 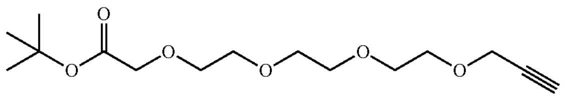 [SMILES: C#CCOCCOCCOCCOCC(=O)OC(C)(C)C] | tert-butyl 3,6,9,12-tetraoxa-pentadec-14-yn-1-oate | $^1H$ NMR (400 MHz, $CDCl_3$) 4.21 (d, J = 2.4 Hz, 2H), 4.03 (s, 2H), 3.75-3.61 (m, 8H), 2.43 (t, J = 2.4 Hz, 1H), 1.48 (s, 9H). |

TABLE 24-continued

| Characterization data for intermediates prepared according to procedure above. | | | |
|---|---|---|---|
| Intermediate | Structure | Chemical Name | $^1$H-NMR |
| G-1-2 | 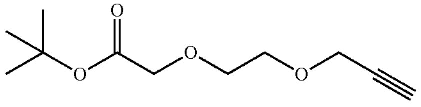 | tert-butyl 2-[2-(prop-2-yn-1-yloxy) ethoxy] acetate | $^1$H NMR (400 MHz, $CDCl_3$) δ 4.23 (d, J = 2.3 Hz, 2H), 4.03 (d, J = 1.3 Hz, 2H), 3.75 (s, 4H), 2.43 (t, J = 2.4 Hz, 1H), 1.48 (s, 9H). |
| G-1-3 | 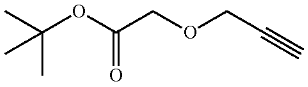 | tert-butyl 2-(prop-2-yn-1-yloxy) acetate | $^1$H NMR (400 MHz, $CDCl_3$) δ 4.32 (d, J = 2.4 Hz, 2H), 4.09 (s, 2H), 2.48 (t, J = 2.4 Hz, 1H), 1.50 (s, 9H). |

Step 2. tert-Butyl 2-(2-(2-((3-(1-(2,6-dioxopiperidin-3-yl)-3-methyl-2-oxo-2,3-dihydro-1H-benzo[d]imidazol-5-yl)prop-2-yn-1-yl)oxy)ethoxy)ethoxy)acetate. The titled compound was prepared according to Step 2 and 3 to prepare Intermediate B. $^1$H NMR (400 MHz, DMSO-$d_6$) δ 11.13 (s, 1H), 7.35 (d, J=1.5 Hz, 1H), 7.24-7.09 (m, 2H), 5.40 (dd, J=12.7, 5.3 Hz, 1H), 4.40 (d, J=3.3 Hz, 2H), 4.15 (d, J=2.4 Hz, 1H), 4.01-3.97 (m, 3H), 3.64 (tt, J=3.6, 1.8 Hz, 2H), 3.35 (s, 2H), 3.01-2.81 (m, 1H), 2.79-2.57 (m, 2H), 2.11-2.00 (m, 2H), 1.43 (s, 4H), 1.42 (s, 9H); MS (ESI, m/z): $[(M+1)]^+$=514.3.

The following intermediates in Table 25 below were prepared according Step 2 to prepare Intermediate G above using the different bromides (1 equiv.) and terminal alkynes (4-5 equiv.).

TABLE 25

| Characterization data for intermediates prepared according to procedure above. | | | | |
|---|---|---|---|---|
| Intermediate | Structure | Chemical Name | MS: $[(M + 1)]^+$ | $^1$H-NMR |
| G-2-2 | 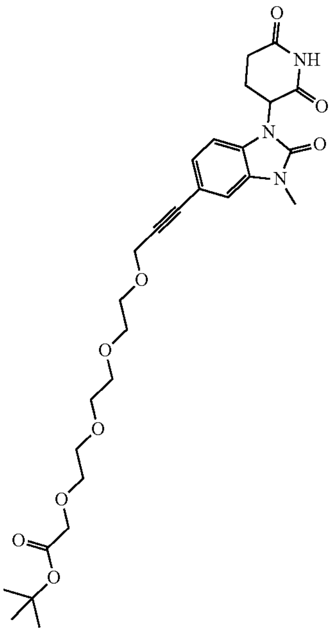 [SMILES: Cn1c(=O)n(C2CCC(=O)NC2=O)c2ccc(C#CCOCCOCCOCCOCC(=O)OC(C)(C)C)cc21] | tert-butyl 15-[1-(2,6-dioxopiperidin-3-yl)-3-methyl-2-oxo-2,3-dihydro-1H-1,3-benzodiazol-5-yl]-3,6,9,12-tetraoxapentadec-14-ynoate | $[(M + 18)]^+$ = 577.4 | (400 MHz, DMSO-$d_6$) δ 11.13 (s, 1H), 7.35 (d, J = 1.4 Hz, 1H), 7.21-7.12 (m, 2H), 5.40 (dd, J = 12.6, 5.4 Hz, 1H), 4.40 (s, 2H), 3.99 (d, J = 1.3 Hz, 3H), 3.71-3.56 (m, 12H), 3.55 (s, 2H), 1.79-1.74 (m, 4H), 1.42 (s, 9H). |

TABLE 25-continued

| Intermediate | Structure | Chemical Name | MS: $[(M+1)]^+$ | $^1$H-NMR |
|---|---|---|---|---|
| Characterization data for intermediates prepared according to procedure above. | | | | |
| G-2-3 | 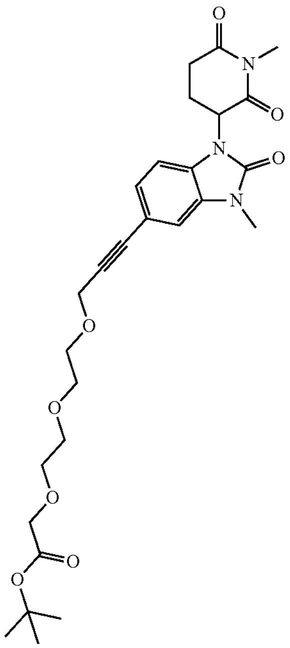 [SMILES: CN1C(=O)CCC(n2c(=O)n(C)c3cc(C#CCOCCOCCOCC(=O)OC(C)(C)C)ccc32)C1=O] | tert-butyl 2-[2-[2-([3-[3-methyl-1-(1-methyl-2,6-dioxopiperidin-3-yl)-2-oxo-1,3-benzodiazol-5-yl]prop-2-yn-1-yl]oxy)ethoxy]ethoxy]acetate | $[(M+23)]^+$ = 552.3 | (400 MHz, DMSO-$d_6$) δ 7.35 (d, J = 3.1 Hz, 1H), 7.16 (d, J = 2.7 Hz, 2H), 5.46 (dd, J = 12.7, 4.3 Hz, 1H ), 4.40 (d, J = 2.8 Hz, 2H), 3.99 (d, J = 2.8 Hz, 2H), 3.68-3.51 (m, 8H), 3.35 (d, J = 2.8 Hz, 3H), 3.04 (d, J = 2.6 Hz, 3H), 2.96 (d, J = 15.2 Hz, 1H), 2.78 (d, J = 17.7 Hz, 1H), 2.71 (d, J = 13.4 Hz, 1H), 2.08 (t, J = 2.2 Hz, 1H), 1.42 (d, J = 3.0 Hz, 9H). |
| G-2-4 | 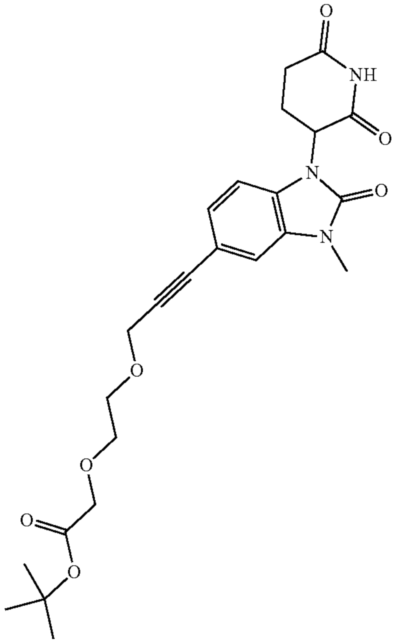 [SMILES: Cn1c(=O)n(C2CCC(=O)NC2=O)c2ccc(C#CCOCCOCC(=O)OC(C)(C)C)cc21] | tert-butyl 2-[2-([3-[1-(2,6-dioxopiperidin-3-yl)-3-methyl-2-oxo-2,3-dihydro-1H-1,3-benzodiazol-5-yl]prop-2-yn-1-yl]oxy)ethoxy]acetate | 470.2 | (400 MHz, DMSO-$d_6$) δ 11.13 (s, 1H), 7.35 (d, J = 1.5 Hz, 1H), 7.25-7.10 (m, 2H), 5.40 (dd, J = 12.7, 5.4 Hz, 1H), 4.41 (d, J = 2.1 Hz, 2H), 4.00 (d, J = 10.4 Hz, 2H), 3.68-3.63 (m, 4H), 3.35 (s, 3H), 3.00-2.81 (m, 1H), 2.81-2.59 (m, 2H), 2.07-1.98 (m, 1H), 1.43 (d, J = 2.2 Hz, 9H). |

TABLE 25-continued

| Characterization data for intermediates prepared according to procedure above. | | | | |
|---|---|---|---|---|
| Intermediate | Structure | Chemical Name | MS: $[(M+1)]^+$ | $^1$H-NMR |
| G-2-5 | 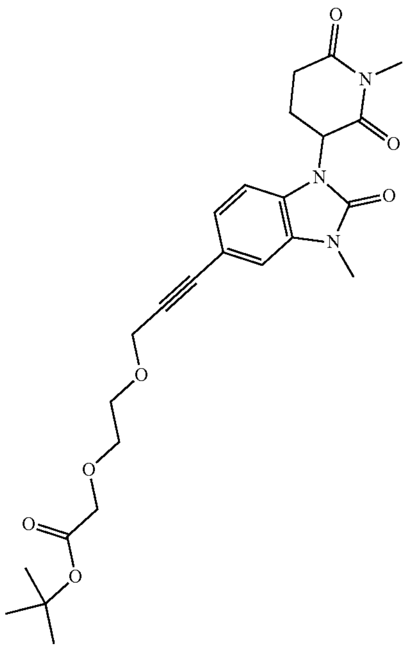 [SMILES: CN1C(=O)CCC(n2c(=O)n(C)c3cc(C#CCOCCOCC(=O)OC(C)(C)C)ccc32)C1=O] | tert-butyl 2-[2-([3-[3-methyl-1-(1-methyl-2,6-dioxopiperidin-3-yl)-2-oxo-1,3-benzodiazol-5-yl]prop-2-yn-1-yl]oxy)ethoxy]acetate | $[(M+18)]^+$ = 503.3 | (400 MHz, DMSO-$d_6$) δ 7.35 (s, 1H), 7.16 (s, 2H), 5.46 (dd, J = 13.1, 5.3 Hz, 1H), 4.41 (s, 2H), 4.01 (s, 2H), 3.66-3.64 (m, 4H), 3.36 (s, 3 H), 3.04 (s, 3H), 3.01-2.92 (m, 1H), 2.83-2.65 (m, 2H), 2.15-1.90 (m, 1 H), 1.43 (s, 9H). |
| G-2-6 | 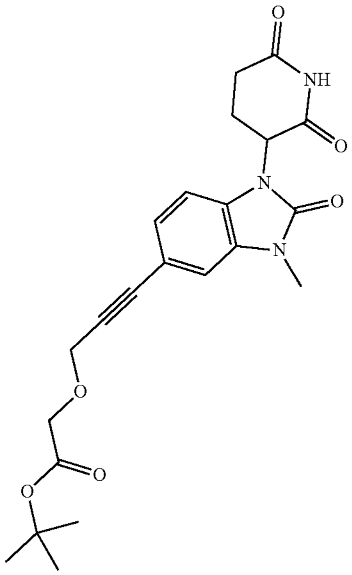 [SMILES: Cn1c(=O)n(C2CCC(=O)NC2=O)c2ccc(C#CCOCC(=O)OC(C)(C)C)cc21] | tert-butyl 2-([3-[1-(2,6-dioxopiperidin-3-yl)-3-methyl-2-oxo-2,3-dihydro-1H-1,3-benzodiazol-5-yl]prop-2-yn-1-yl]oxy)acetate | 428.2 | (400 MHz, DMSO-$d_6$) δ 11.14 (s, 1H), 7.36 (d, J = 1.4 Hz, 1H), 7.22-7.12 (m, 2H), 5.40 (dd,J = 12.7, 5.4 Hz, 1H), 4.47 (s, 2H), 4.11 (s, 2H), 3.35 (s, 3H), 2.96-2.83 (m, 1H), 2.78-2.60 (m, 2H), 2.07-2.00 (m, 1H), 1.44 (s, 9H). |

TABLE 25-continued

| Characterization data for intermediates prepared according to procedure above. | | | | |
|---|---|---|---|---|
| Intermediate | Structure | Chemical Name | MS: $[(M + 1)]^+$ | $^1$H-NMR |
| G-2-7 | 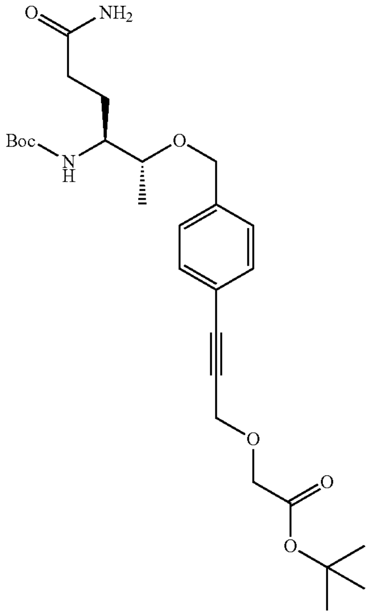 [SMILES: C[C@@H](OCc1ccc(C#CCOCC(=O)OC(C)(C)C)cc1)[C@H](CCC(N)=O)NC(=O)OC(C)(C)C] | tert-butyl 2-([3-[4-([[(2R,3S)-3-[(tert-butoxycarbonyl) amino]-5-carbamoylpentan-2-yl]oxy] methyl)phenyl] prop-2-yn-1-yl] oxy)acetate | 505.4 | (400 MHz, DMSO-$d_6$) δ 7.42 (d, J = 7.9 Hz, 2H), 7.35 (d, J = 7.9 Hz, 2H), 7.22 (s, 1H), 6.71-6.59 (m, 2H), 5.76 (d, J = 1.3 Hz, 1H), 4.54-4.44 (m, 4H), 4.09 (s, 2H), 3.52-3.36 (m, 2H), 2.14-1.96 (m, 2H), 1.78 (d, J = 9.8 Hz, 1H), 1.43 (d, J =1.2 Hz, 9H), 1.38 (s, 9H), 1.07 (d, J = 6.0 Hz, 3H). |
| G-2-8 | 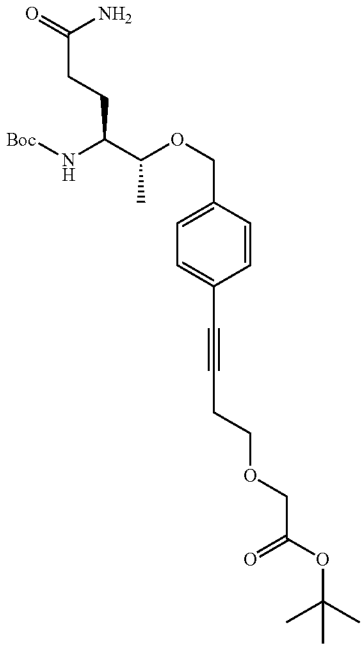 [SMILES: C[C@@H](OCc1ccc(C#CCCOCC(=O)OC(C)(C)C)cc1)[C@H](CCC(N)=O)NC(=O)OC(C)(C)C] | tert-butyl 2-([4-[4-([[(2R,3S)-3-[4(tert-butoxycarbonyl) amino]-5-carbamoylpentan-2-yl]oxy]methyl) phenyl]but-3-yn-1-yl]oxy) acetate | 519.4 | (400 MHz, DMSO-$d_6$) δ 7.36-7.28 (m, 4H), 7.22 (s, 1H), 6.71-6.59 (m, 2H), 4.47 (t, J = 2.8 Hz, 2H), 4.04 (d, J = 3.0 Hz, 2H), 3.64 (td, J = 6.8, 2.6 Hz, 2H), 3.40 (d, J = 6.1 Hz, 2H), 2.68 (td, J = 6.8, 2.7 Hz, 2H), 2.14-1.96 (m, 2H), 1.78 (s, 1H), 1.48 (s, 1H), 1.43 (d, J = 2.9 Hz, 9H), 1.38 (d, J = 2.7 Hz, 9H), 1.06 (dd, J = 6.1, 2.6 Hz, 3H). |

TABLE 25-continued

| Intermediate | Structure | Chemical Name | MS: $[(M + 1)]^+$ | $^1$H-NMR |
|---|---|---|---|---|
| | Characterization data for intermediates prepared according to procedure above. | | | |
| G-2-9 | 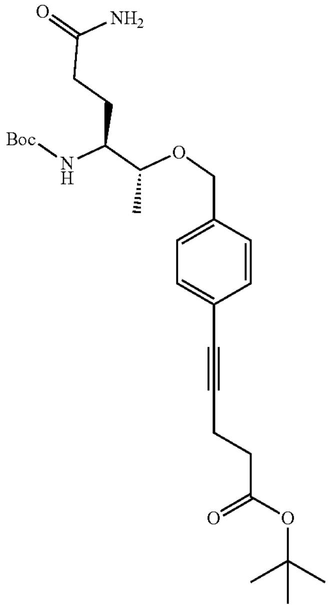 [SMILES: C[C@@H](OCc1ccc(C#CCCC(=O)OC(C)(C)C)cc1)[C@H](CCC(N)=O)NC(=O)OC(C)(C)C] | tert-butyl 5-[4-([[(2R,3S)-3-[(tert-butoxycarbonyl)amino]-5-carbamoyl pentan-2-yl]oxy]methyl)phenyl] pent-4-ynoate | 489.3 | (400 MHz, $CD_3OD$) δ 7.32 (d, J = 1.5 Hz, 4H), 4.62-4.46 (m, 2H), 3.63-3.46 (m, 2H), 2.67 (t, J = 7.3 Hz, 2H), 2.56-2.48 (m, 2H), 2.35-2.17 (m, 2H), 1.98 (ddt, J = 13.5, 10.0, 4.8 Hz, 1H), 1.70-1.57 (m, 1H), 1.49 (s, 9H), 1.45 (s, 9H), 1.18 (d, J = 6.2 Hz, 3H). |
| G-2-10 | 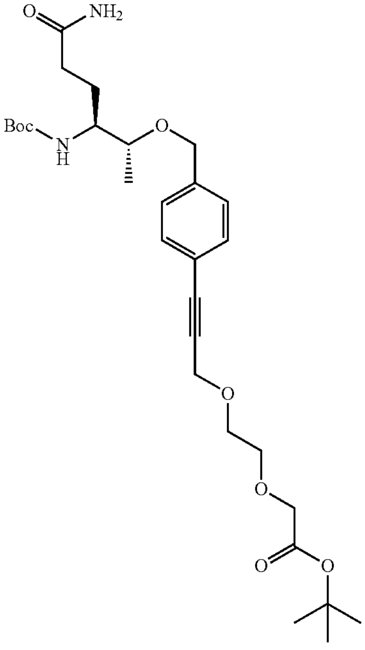 [SMILES: C[C@@H](OCc1ccc(C#CCOCCOCC(=O)OC(C)(C)C)cc1)[C@H](CCC(N)=O)NC(=O)OC(C)(C)C] | tert-butyl 2-[2-([3-[4-([[(2R,3S)-3-[(tert-butoxycarbonyl)amino]-5-carbamoylpentan-2-yl]oxy]methyl)phenyl]prop-2-yn-1-yl]oxy)ethoxy] acetate | 549.4 | (400 MHz, DMSO-$d_6$) 7.41 (d, J = 8.0 Hz, 2H), 7.34 (d, J = 8.0 Hz, 2H), 7.21 (s, 1H), 6.72-6.58 (m, 2H), 4.56-4.45 (m, 2H), 4.40 (s, 2H), 4.01 (s, 2H), 3.62-3.55 (m, 1H), 3.44 (dt, J = 11.7, 7.2 Hz, 2H), 2.08-1.96 (m, 2H), 1.85-1.71 (m, 1H), 1.43 (s, 9H), 1.38 (s, 9H), 1.07 (d, J = 6.0 Hz, 3H). |

TABLE 25-continued

| Characterization data for intermediates prepared according to procedure above. | | | | |
|---|---|---|---|---|
| Intermediate | Structure | Chemical Name | MS: $[(M + 1)]^+$ | $^1$H-NMR |
| G-2-11 | 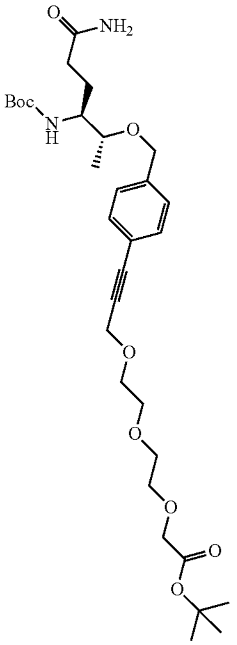 [SMILES: C[C@@H](OCc1ccc(C#CCOCCOCCOCC(=O)OC(C)(C)C)cc1)[C@H](CCC(N)=O)NC(=O)OC(C)(C)C] | tert-butyl 2-[2-[2-([3-4-([[(2R,3S)-3-[(tert-butoxycarbonyl) amino]-5-carbamoylpentan-2-yl]oxy] methyl)phenyl] prop-2-yn-1-yl]oxy)ethoxy] ethoxy]acetate | 593.4 | (400 MHz, DMSO-$d_6$) δ 7.41 (d, J = 8.0 Hz, 2H), 7.34 (d, J = 8.0 Hz, 2H), 7.21 (s, 1H), 6.71-6.59 (m, 2H), 4.55-4.44 (m, 2H), 4.40 (s, 2H), 3.99 (s, 2H), 3.64 (dd, J = 6.3, 3.6 Hz, 2H), 3.63-3.54 (m, 4H), 3.55 (t, J = 5.2 Hz, 3H), 3.49-3.37 (m, 2H), 2.07-1.93 (m, 1H), 1.84-1.73 (m, 1H), 1.43 (d, J = 2.5 Hz, 9H), 1.38 (s, 9H), 1.07 (d, J = 6.0 Hz, 3H). |
| G-2-12 | 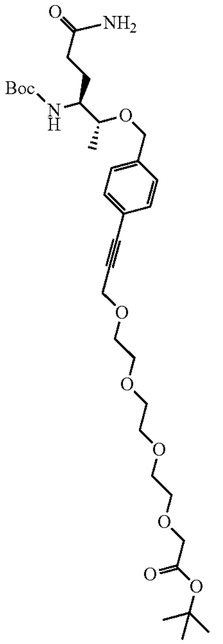 [SMILES: C[C@@H](OCc1ccc(C#CCOCCOCCOCCOCC(=O)OC(C)(C)C)cc1)[C@H](CCC(N)=O)NC(=O)OC(C)(C)C] | tert-butyl 15-[4-([[(2R,3S)-3-[(tert-butoxycarbonyl) amino]-5-carbamoylpentan-2-yl]oxy] methyl)phenyl]-3,6,9,12-tetraoxa-pentadec-14-ynoate | 637.4 | (400 MHz, DMSO-$d_6$) δ 7.41 (d, J = 8.0 Hz, 2H), 7.37-7.27 (m, 2H), 7.21 (s, 1H), 6.68 (s, 1H), 6.63 (d, J = 9.0 Hz, 1H), 4.55-4.43 (m, 2H), 4.39 (d, J = 3.4 Hz, 2H), 3.98 (d, J = 3.4 Hz, 2H), 3.67-3.56 (m, 3H), 3.60-3.35 (m, 9H), 2.16-1.95 (m, 3H), 1.78 (s, 1H), 1.49 (s, 1H), 1.45-1.35 (m, 18H), 1.10-1.04 (m, 3H). |

TABLE 25-continued

| Characterization data for intermediates prepared according to procedure above. | | | | |
|---|---|---|---|---|
| Intermediate | Structure | Chemical Name | MS: $[(M + 1)]^+$ | $^1$H-NMR |
| G-2-16 | 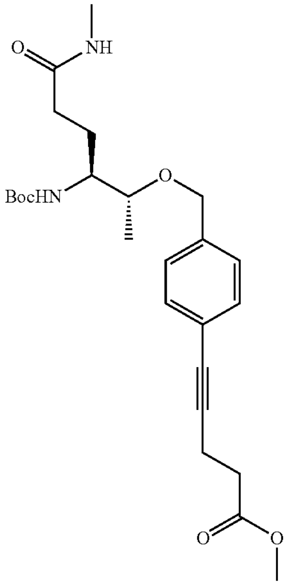 [SMILES: CNC(=O)CC[C@H](NC(=O)OC(C)(C)C)[C@@H](C)OCc1ccc(C#CCCC(=O)OC)cc1] | methyl 5-[4-([[(2R,3S)-3-[(tert-butoxycarbonyl)amino]-5-(methylcarbamoyl)pentan-2-yl]oxy]methyl)phenyl]pent-4-ynoate | 461.3 | (400 MHz, DMSO-$d_6$) δ 7.67 (d, J = 5.0 Hz, 1H), 7.35-7.26 (m, 4H), 6.61 (d, J = 9.1 Hz, 1H), 4.53-4.41 (m, 2H), 3.64 (s, 3H), 3.62 (s, 3H), 3.49-3.35 (m, 1H), 2.72-2.57 (m, 4H), 2.55-2.51 (m, 2H), 2.12-1.98 (m, 1H), 1.78 (dtd, J = 13.2, 9.1, 5.5 Hz, 1H), 1.49 (dt, J = 14.0, 4.7 Hz, 1H), 1.38 (s, 9H), 1.06 (d, J = 6.0 Hz, 3H). |
| G-2-17 | 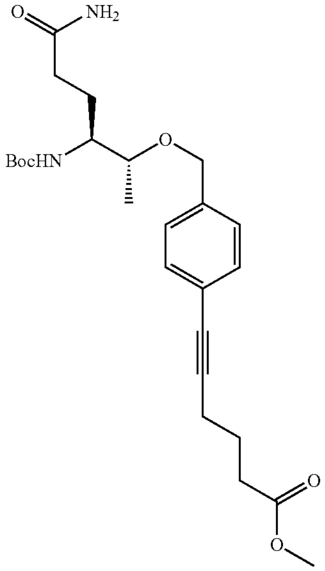 [SMILES: COC(=O)CCCC#Cc1ccc(CO[C@H](C)[C@H](CCC(N)=O)NC(=O)OC(C)(C)C)cc1] | methyl 6-[4-([[(2R,3S)-3-[(tert-butoxycarbonyl)amino]-5-carbamoylpentan-2-yl]oxy]methyl)phenyl]hex-5-ynoate | 461.2 | (400 MHz, DMSO-$d_6$) δ 7.36-7.30 (m, 4H), 7.23 (s, 1H), 6.69 (s, 1H), 6.63 (d, J = 9.1 Hz, 1H), 4.49 (t, J = 8.0 Hz, 2H), 3.61 (s, 3H), 3.48-3.37 (m, 1H), 2.50-2.40 (m, 2H), 2.37 (dt, J = 18.0, 7.1 Hz, 2H), 2.04 (td, J = 14.8, 8.4 Hz, 2H), 1.85-1.70 (m, 4H), 1.50-1.40 (m, 1H), 1.38 (s, 9H), 1.07 (d, J = 6.1 Hz, 3H). |

TABLE 25-continued

Characterization data for intermediates prepared according to procedure above.

| Intermediate | Structure | Chemical Name | MS: $[(M + 1)]^+$ | $^1$H-NMR |
|---|---|---|---|---|
| G-2-18 | 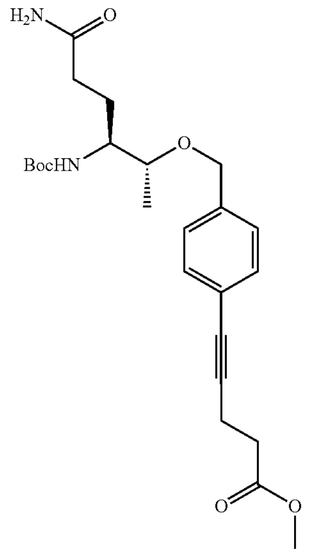 [SMILES: COC(=O)CCC#Cc1ccc(CO[C@H](C)[C@H](CCC(N)=O)NC(=O)OC(C)(C)C)cc1] | methyl 5-[4-([[(2R,3S)-3-[(tert-butoxycarbonyl) amino]-5-carbamoylpentan-2-yl]oxy] methyl)phenyl] pent-4-ynoate | 447.4 | (400 MHz, $CDCl_3$) δ 7.42-7.35 (m, 2H), 7.27-7.22 (m, 2H), 6.49 (s, 1H), 6.05 (s, 1H), 4.85 (d, J = 9.7 Hz, 1H), 4.59 (d, J = 12.0 Hz, 1H), 4.40 (d, J = 12.0 Hz, 1H), 3.74 (s, 3H), 3.72-3.55 (m, 2H), 2.75 (ddd, J = 8.3, 6.7, 1.5 Hz, 2H), 2.66 (ddd, J = 8.2, 6.8, 1.5 Hz, 2H), 2.37-2.22 (m, 2H), 1.97 (td, J = 12.8, 11.2, 5.6 Hz, 1H), 1.70 (ddd, J = 20.3, 12.1, 6.0 Hz, 1H), 1.45 (s, 9H), 1.20 (d, J = 6.3 Hz, 3H). |
| G-2-19 | 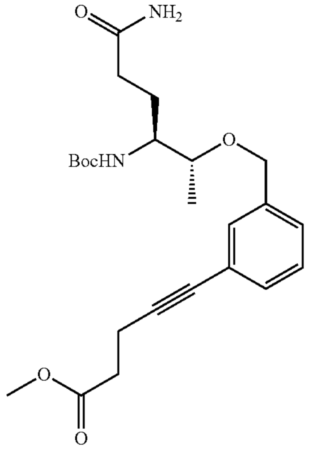 [SMILES: COC(=O)CCC#Cc1cccc(CO[C@H](C)[C@H](CCC(N)=O)NC(=O)OC(C)(C)C)c1] | methyl 5-[3-([[(2R,3S)-3-[(tert-butoxycarbonyl) amino]-5-carbamoylpentan-2-yl]oxy] methyl)phenyl] pent-4-ynoate | 447.3 | (400 MHz, $CD_3OD$) δ 7.38 (d, J = 1.7 Hz, 1H), 7.35-7.25 (m, 3H), 4.55 (d, J = 11.7 Hz, 1H), 4.50 (d, J = 11.7 Hz, 1H), 3.72 (s, 3H), 3.61 (ddd, J = 10.8, 5.2, 3.2 Hz, 1H), 3.57-3.49 (m, 1H), 2.76-2.69 (m, 2H), 2.69-2.60 (m, 2H), 2.36-2.17 (m, 2H), 1.97 (dddd, J = 12.9, 9.6, 6.7, 3.2 Hz, 1H), 1.70-1.55 (m, 1H), 1.46 (s, 9H), 1.18 (d, J = 6.2 Hz, 3H). |
| G-2-20 | 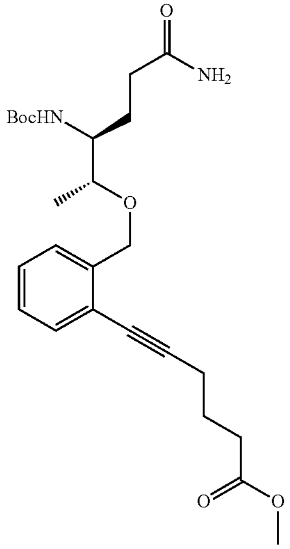 [SMILES: COC(=O)CCCC#Cc1ccccc1CO[C@H](C)[C@H](CCC(N)=O)NC(=O)OC(C)(C)C] | methyl 6-[2-([[(2R,3S)-3-[(tert-butoxycarbonyl) amino]-5-carbamoylpentan-2-yl]oxy] methyl)phenyl] hex-5-ynoate | 461.2 | (400 MHz, DMSO-$d_6$) δ 7.66-7.18 (m, 5H), 6.73-6.59 (m, 2H), 4.69-4.49 (m, 2H), 3.61 (s, 3H), 3.55-3.40 (m, 2H), 2.43-2.30 (m, 6H), 2.05 (ddt, J = 15.0, 10.0, 5.2 Hz, 1H), 1.83 (p, J = 7.2 Hz, 1H), 1.72 (p, J = 7.1 Hz, 2H), 1.39 (s, 9H), 1.11 (t, J = 5.3 Hz, 3H). |

TABLE 25-continued

Characterization data for intermediates prepared according to procedure above.

| Intermediate | Structure | Chemical Name | MS: [(M + 1)]+ | 1H-NMR |
|---|---|---|---|---|
| G-2-21 | 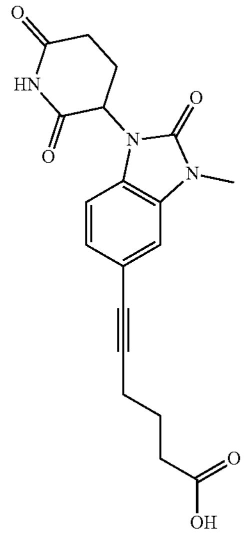 [SMILES: Cn1c(=O)n(C2CCC(=O)NC2=O)c2ccc(C#CCCCC(=O)O)cc21] | 6-[1-(2,6-dioxopiperidin-3-yl)-3-methyl-2-oxo-1,3-benzodiazol-5-yl]hex-5-ynoic acid | 370.1 | (400 MHz, DMSO-$d_6$) δ 12.11 (br, 1H), 11.12 (s, 1H), 7.26 (d, J = 1.1 Hz, 1H), 7.10 (m, 2H), 5.38 (dd, J = 12.7, 5.4 Hz, 1H), 3.34 (s, 3H), 2.98-2.83 (m, 1H), 2.78-2.58 (m, 2H), 2.46 (t, J = 7.1 Hz, 2H), 2.39 (q, J = 5.9, 4.5 Hz, 1H), 2.36-2.14 (m, 1H), 2.08-1.98 (m, 1H), 1.78 (p, J = 7.2 Hz, 2H). |
| G-2-22 | 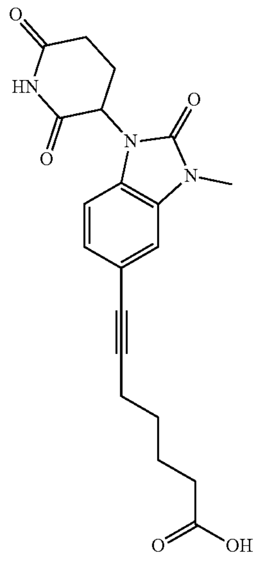 [SMILES: Cn1c(=O)n(C2CCC(=O)NC2=O)c2ccc(C#CCCCCC(=O)O)cc21] | 7-[1-(2,6-dioxopiperidin-3-yl)-3-methyl-2-oxo-1,3-benzodiazol-5-yl]hept-6-ynoic acid | 384.1 | (400 MHz, DMSO-$d_6$) δ 12.09 (br, 1H), 11.11 (s, 1H), 7.24 (d, J = 1.4 Hz, 1H), 7.18-6.97 (m, 2H), 5.43 (dd, J = 12.7, 5.3 Hz, 1H), 3.37 (s, 3H), 3.03-2.83 (m, 1H), 2.79-2.56 (m, 2H), 2.43 (t, J = 6.9 Hz, 2H), 2.28 (t, J = 7.2 Hz, 2H), 2.07-1.98 (m, 1H), 1.65 (ddd, J = 11.8, 8.7, 5.7 Hz, 2H), 1.56 (dq, J = 8.2, 6.4, 5.9 Hz, 2H). |

TABLE 25-continued

| Characterization data for intermediates prepared according to procedure above. | | | | |
|---|---|---|---|---|
| Intermediate | Structure | Chemical Name | MS: [(M + 1)]$^+$ | $^1$H-NMR |
| G-2-23 | 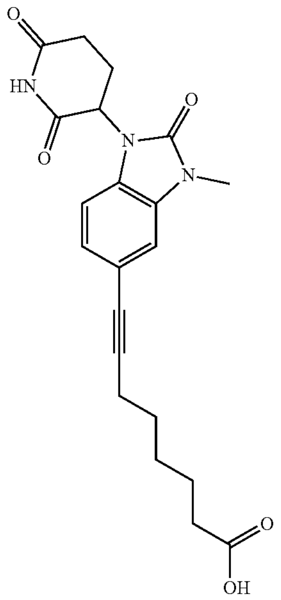 [SMILES: Cn1c(=O)n(C2CCC(=O)NC2=O)c2ccc(C#CCCCCCC(=O)O)cc21] | 8-[1-(2,6-dioxopiperidin-3-yl)-3-methyl-2-oxo-1,3-benzodiazol-5-yl]oct-7-ynoic acid | 398.2 | (400 MHz, DMSO-$d_6$) δ 12.00 (br, 1H), 11.13 (s, 1H), 7.24 (s, 1H), 7.09 (s, 2H), 5.38 (dd, J = 12.9, 5.2 Hz, 1H), 3.33 (s, 3H), 2.89 (t, J = 16.8 Hz, 1H), 2.67 (m, 2H), 2.42 (t, J = 7.0 Hz, 2H), 2.23 (t, J = 7.3 Hz, 2H), 2.10-2.00 (m, 1H), 1.55 (m, 4H), 1.43 (q, J = 7.6 Hz, 2H). |
| G-2-24 | 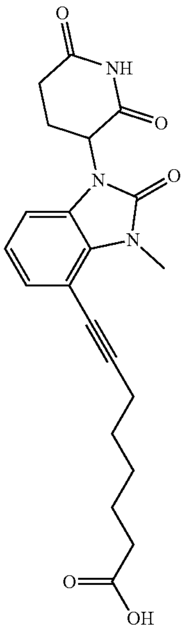 [SMILES: Cn1c(=O)n(C2CCC(=O)NC2=O)c2cccc(C#CCCCCCC(=O)O)c21] | 8-[1-(2,6-dioxopiperidin-3-yl)-3-methyl-2-oxo-1,3-benzodiazol-4-yl]oct-7-ynoic acid | 398.2 | (400 MHz, DMSO-$d_6$) δ 12.02 (br, 1H), 11.13 (s, 1H), 7.12 (dd, J = 7.7, 1.3 Hz, 1H), 7.06 (dd, J = 7.9, 1.2 Hz, 1H), 6.99 (t, J = 7.8 Hz, 1H), 5.39 (dd, J = 12.7, 5.4 Hz, 1H), 3.64 (s, 3H), 2.98-2.82 (m, 1H), 2.79-2.56 (m, 2H), 2.24 (t, J = 7.1 Hz, 2H), 2.18 (dd, J = 9.4, 7.3 Hz, 1H), 2.02 (ddd, J = 10.8, 5.8, 3.6 Hz, 1H), 1.63-1.37 (m, 6H), 1.37-1.19 (m, 1H). |

TABLE 25-continued

| Characterization data for intermediates prepared according to procedure above. | | | | |
|---|---|---|---|---|
| Intermediate | Structure | Chemical Name | MS: [(M + 1)]+ | $^1$H-NMR |
| G-2-25 | 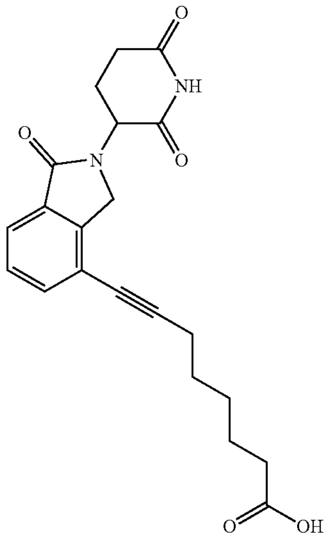 [SMILES: O=C(O)CCCCCC#Cc1cccc2c1CN(C1CCC(=O)NC1=O)C2=O] | 8-[2-(2,6-dioxopiperidin-3-yl)-1-oxo-3H-isoindol-4-yl]oct-7-ynoic acid | 383.2 | (400 MHz, DMSO-$d_6$) δ 11.99 (br, 1H), 10.99 (s, 1H), 7.71 (dd, J = 7.6, 1.1 Hz, 1H), 7.64 (dd, J = 7.7, 1.1 Hz, 1H), 7.57-7.48 (m, 1H), 5.14 (dd, J = 13.3, 5.1 Hz, 1H), 4.45 (d, J = 17.7 Hz, 1H), 4.31 (d, J = 17.7 Hz, 1H), 2.91 (ddd, J = 17.9, 13.6, 5.5 Hz, 1H), 2.60 (d, J = 17.4 Hz, 2H), 2.48 (d, J = 6.9 Hz, 2H), 2.23 (t, J = 7.2 Hz, 2H), 2.09-1.97 (m, 1H), 1.57 (m, 4H), 1.45 (td, J = 8.3, 4.3 Hz, 2H). |
| G-2-26 | 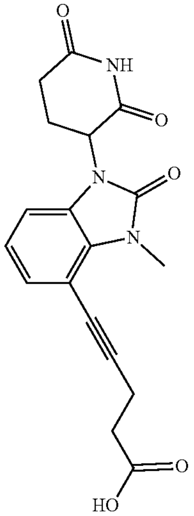 [SMILES: Cn1c(=O)n(C2CCC(=O)NC2=O)c2cccc(C#CCCC(=O)O)c21] | 5-[1-(2,6-dioxopiperidin-3-yl)-3-methyl-2-oxo-1,3-benzodiazol-4-yl]pent-4-ynoic acid | 356.1 | (400 MHz, DMSO-$d_6$) δ 12.14 (br, 1H), 11.11 (s, 1H), 7.08-7.00 (m, 2H), 6.95 (dd, J = 6.9, 2.1 Hz, 1H), 5.38 (dd, J = 12.6, 5.4 Hz, 1H), 3.52 (s, 3H), 2.98 (ddd, J = 8.5, 7.0, 2.2 Hz, 2H), 2.90 (ddd, J = 16.6, 13.2, 5.3 Hz, 1H), 2.78-2.53 (m, 4H), 2.02 (ddt, J = 11.1, 8.8, 2.3 Hz, 1H). |
| G-2-27 | 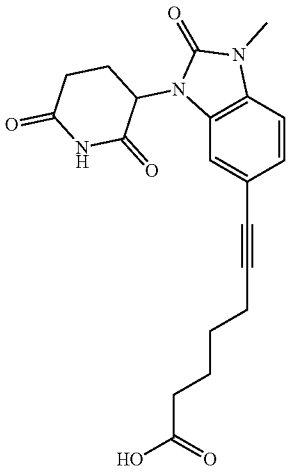 [SMILES: Cn1c(=O)n(C2CCC(=O)NC2=O)c2cc(C#CCCCCC(=O)O)ccc21] | 7-[3-(2,6-dioxopiperidin-3-yl)-1-methyl-2-oxo-1,3-benzodiazol-5-yl]hept-6-ynoic acid | 384.05 | (400 MHz, DMSO-$d_6$) δ 12.09 (s, 1H), 11.10 (s, 1H), 7.22 (s, 1H), 7.20-7.10 (m, 2H), 5.39 (dd, J = 12.7, 5.3 Hz, 1H), 3.34 (s, 3H), 2.94-2.81 (m, 1H), 2.79-2.69 (m, 1H), 2.67-2.58 (m, 1H), 2.42 (t, J = 6.9 Hz, 2H), 2.35-2.20 (m, 1H), 2.05-1.97 (m, 1H), 1.69-1.61 (m, 2H), 1.57-1.53 (m, 2H) |

TABLE 25-continued

Characterization data for intermediates prepared according to procedure above.

| Intermediate | Structure | Chemical Name | MS: $[(M + 1)]^+$ | $^1$H-NMR |
|---|---|---|---|---|
| G-2-28 | 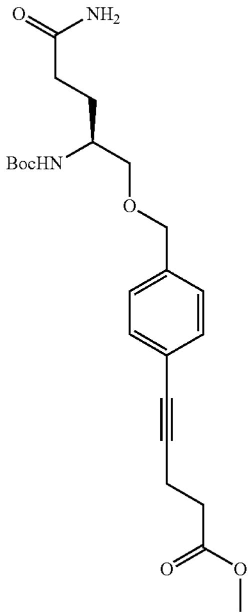 [SMILES: COC(=O)CCC#Cc1ccc(COC[C@H](CCC(N)=O)NC(=O)OC(C)(C)C)cc1] | methyl 5-(4-[[(2S)-2-[(tert-butoxycarbonyl)amino]-4-carbamoylbutoxy]methyl]phenyl)pent-4-ynoate | 433.20 | (400 MHz, DMSO-$d_6$) δ 7.38-7.35 (m, 2H), 7.32-7.28 (m, 2H), 6.84-6.82 (d, J = 8.6 Hz, 1H), 6.73-6.68 (m, 2H), 4.46 (s, 2H), 3.95-3.93 (m, 1H), 3.64 (s, 3H), 3.61-3.52 (m, 2H), 3.32 (s, 2H), 2.74-2.57 (m, 6H), 2.08-2.04 (m, 2H), 1.37 (s, 9H) |
| G-2-29 | 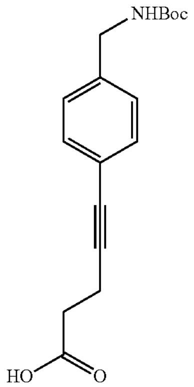 [SMILES: CC(C)(C)OC(=O)NCc1ccc(C#CCCC(=O)O)cc1] | 5-(4-[[(tert-butoxycarbonyl)amino]methyl]phenyl)pent-4-ynoic acid | 304.15 | (400 MHz, DMSO-$d_6$) δ 7.23 (q, J = 8.1 Hz, 4H), 6.25 (t, J = 2.3 Hz, 1H), 4.11 (d, J = 6.1 Hz, 2H), 3.19-3.10 (m, 2H), 2.83-2.72 (m, 2H), 1.40 (s, 9H) |
| G-2-30 | 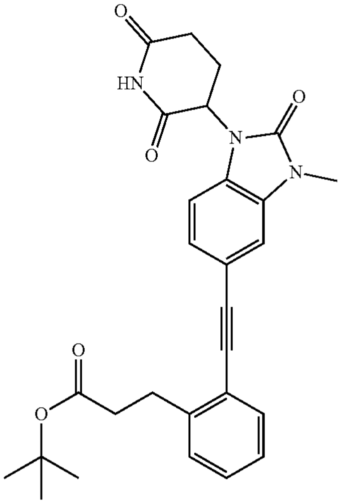 [SMILES: Cn1c(=O)n(C2CCC(=O)NC2=O)c2ccc(C#Cc3ccccc3CCC(=O)OC(C)(C)C)cc21] | tert-butyl 3-(2[2-[1-(2,6-dioxopiperidin-3-yl)-3-methyl-2-oxo-1,3-benzodiazol-5-yl]ethynyl]phenyl)propanoate | 488.15 | (400 MHz, DMSO-$d_6$) δ 11.14 (s, 1H), 7.51 (dd, J = 7.3, 1.3 Hz, 1H), 7.41 (d, J = 1.5 Hz, 1H), 7.36-7.32 (m, 2H), 7.30-7.25 (m, 2H), 7.21 (d, J = 8.2 Hz, 1H), 5.45-5.41 (m, 1H), 3.38 (s, 3H), 3.08 (t, J = 7.7 Hz, 2H), 2.96-2.85 (m, 1H), 2.77-2.73 (m, 1H), 2.68-2.66 (m, 1H), 2.64-2.61 (m, 2H), 2.10-2.01 (m, 1H), 1.60-1.44 (m, 2H), 1.38 (s, 9H) |

TABLE 25-continued

Characterization data for intermediates prepared according to procedure above.

| Intermediate | Structure | Chemical Name | MS: $[(M+1)]^+$ | $^1$H-NMR |
|---|---|---|---|---|
| G-2-31 | 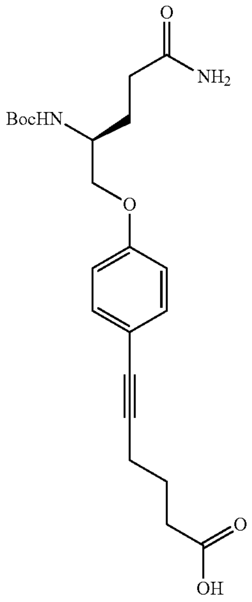 [SMILES: CC(C)(C)OC(=O)N[C@@H](CCC(N)=O)COc1ccc(C#CCCCC(=O)O)cc1] | 6-[4-[(2S)-2-[(tert-butoxycarbonyl) amino]-4-carbamoyl-butoxy]phenyl] hex-5-ynoic acid | 419.15 | (400 MHz, DMSO-$d_6$) δ 12.07 (s, 1H), 7.34-7.28 (m, 2H), 7.26 (s, 1H), 6.93-6.87 (m, 2H), 6.84 (d, J = 8.5 Hz, 1H), 6.73 (s, 1H), 3.90-3.81 (m, 2H), 3.71 (dq, J = 9.1, 4.7 Hz, 1H), 2.46-2.42 (m, 4H), 2.21-2.05 (m, 3H), 1.76 (h, J = 7.2, 6.7 Hz, 2H), 1.64-1.61 (m, 1H), 1.39 (s, 9H) |
| G-2-32 | 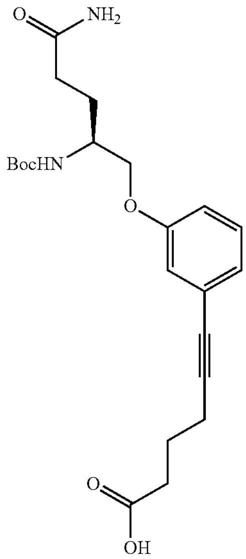 [SMILES: CC(C)(C)OC(=O)N[C@@H](CCC(N)=O)COc1cccc(C#CCCCC(=O)O)c1] | 6-[3-[(2S)-2-[(tert-butoxycarbonyl) amino]-4-carbamoyl-butoxy]phenyl] hex-5-ynoic acid | $[(M-1)]^-$ = 417.23 | 400 MHz, DMSO-$d_6$) δ 7.25 (t, J = 7.6 Hz, 2H), 6.97 (d, J = 7.6 Hz, 1H), 6.92 (d, J = 7.5 Hz, 2H), 6.82 (d, J = 8.5 Hz, 1H), 6.73 (s, 1H), 3.92-3.86 (m, 3H), 3.75- 3.67 (m, 1H), 3.38 (s, 1H), 2.46 (s, 2H), 2.18-2.04 (m, 3H), 1.84-1.75 (m, 3H), 1.64-1.58 (m, 1H), 1.40 (s, 9H) |

TABLE 25-continued

| Characterization data for intermediates prepared according to procedure above. | | | | |
|---|---|---|---|---|
| Intermediate | Structure | Chemical Name | MS: $[(M + 1)]^+$ | $^1$H-NMR |
| G-2-33 | 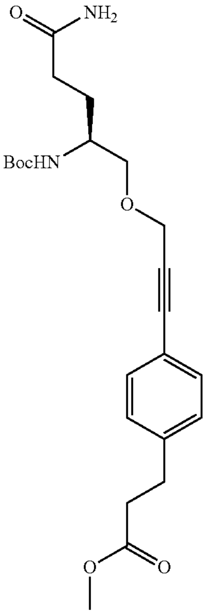 [SMILES: COC(=O)CCc1ccc(C#CCOC[C@H](CCC(N)=O)NC(=O)OC(C)(C)C)cc1] | methyl 3-(4-[3-[(2S)-2-[(tert-butoxycarbonyl) amino]-4-carbamoylbutoxy] prop-1-yn-1-yl]phenyl) propanoate | 432.52 | (400 MHz, $CDCl_3$) 7.38 (d, J = 8.0 Hz, 2H), 7.17 (d, J = 8.0 Hz, 2H), 6.52 (s, 1H), 5.49 (s, 1H), 5.02 (d, J = 9.0 Hz, 1H), 4.38 (s, 2H), 3.91-3.77 (m, 1H), 3.68 (s, 3H), 3.66-3.60 (m, 2H), 2.96 (t, J = 8.7, 2H), 2.64 (t, J = 8.2 Hz, 2H), 2.35-2.29 (m, 2H), 1.96-1.87 (m, 2H), 1.45 (s, 9H) |
| G-2-34 | 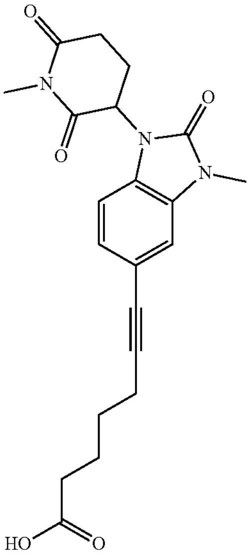 | 7-[3-methyl-1-(1-methyl-2,6-dioxopiperidin-3-yl)-2-oxo-1,3-benzodiazol-5-yl]hept-6-ynoic acid | 398.05 | (400 MHz, $CDCl_3$) δ 7.18-7.13 (m, 1H), 7.09 (d, J = 1.5 Hz, 1H), 6.71 12.6, 4.9 Hz, 1H), 3.44 (s, 3H), 3.26 (s, 3H), 3.11-3.00 (m, 1H), 2.94-2.80 (m, 1H), 2.79-2.64 (m, 1H), 2.47 (q, J = 6.8 Hz, 4H), 2.40 (dd, J = 13.0, 6.7 Hz, 1H), 2.27-2.09 (m, 1H), 1.90-1.78 (m, 2H), 1.74-1.70 (m, 2H) |

TABLE 25-continued

Characterization data for intermediates prepared according to procedure above.

| Intermediate | Structure | Chemical Name | MS: $[(M + 1)]^+$ | $^1$H-NMR |
|---|---|---|---|---|
| G-2-35 | 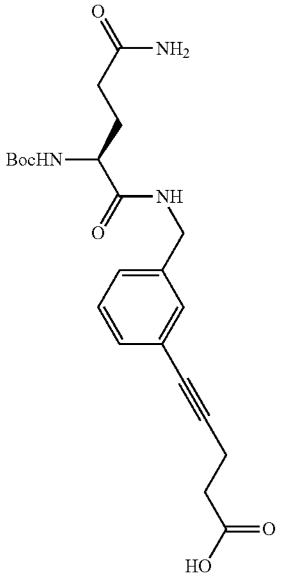 [SMILES: CC(C)(C)OC(=O)N[C@@H](CCC(N)=O)C(=O)NCc1cccc(C#CCCC(=O)O)c1] | 5-(3-[[(2S)-2-[(tert-butoxycarbonyl) amino]-4-carbamoyl-butanamido] methyl] phenyl)pent-4-ynoic acid | 432.20 | (400 MHz, DMSO-$d_6$) δ 8.32 (t, J = 6.1 Hz, 1H), 7.33-.22 (m, 2H), 7.16 (d, J = 9.4 Hz, 2H), 7.13-7.05 (m, 2H), 6.94-6.90 (m, 1H), 6.76 (s, 1H), 6.24 (t, J = 2.3 Hz, 1H), 4.29-4.26 (m, 2H), 3.96-.86 (m, 1H), 3.18-3.13 (m, 2H), 2.84 -2.75 (m, 1H), 2.19 -2.03 (m, 2H), 1.95-1.79 (m, 1H), 1.76-1.69 (m, 1H), 1.39 (s, 9H) |
| G-2-36 | 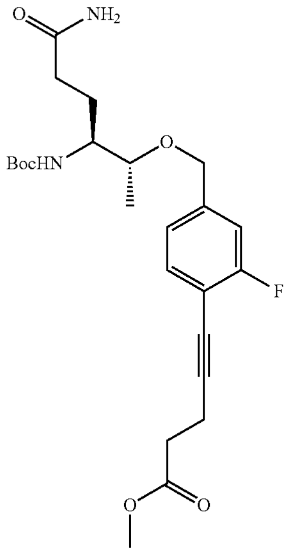 [SMILES: COC(=O)CCC#Cc1ccc(CO[C@H](C)[C@H](CCC(N)=O)NC(=O)OC(C)(C)C)cc1F] | methyl 5-[4-([[(2R,3S)-3-[(tert-butoxycarbonyl) amino]-5-carbamoyl-pentan-2-yl]oxy] methyl)-2-fluorophenyl] pent-4-ynoate | 464.534 | (400 MHz, DMSO-$d_6$) δ 7.38 (t, J = 7.7 Hz, 1H), 7.23 (d, J = 9.8 Hz, 2H), 7.13 (dd, J = 7.9, 1.5 Hz, 1H), 6.71-6.62 (m, 2H), 4.55-4.43 (m, 2H), 3.64 (s, 3H), 3.49 (d, J = 12.4 Hz, 1H), 3.44-3.40 (m, 1H), 2.72 (dd, J = 7.6, 5.7 Hz, 2H), 2.65-2.61 (m, 2H), 2.15-1.95 (m, 2H), 1.78-1.74 (m, 1H), 1.54-1.43 (m, 1H), 1.38 (s, 9H), 1.07 (d, J = 6.1 Hz, 3H) |

TABLE 25-continued

Characterization data for intermediates prepared according to procedure above.

| Intermediate | Structure | Chemical Name | MS: $[(M + 1)]^+$ | $^1$H-NMR |
|---|---|---|---|---|
| G-2-37 | 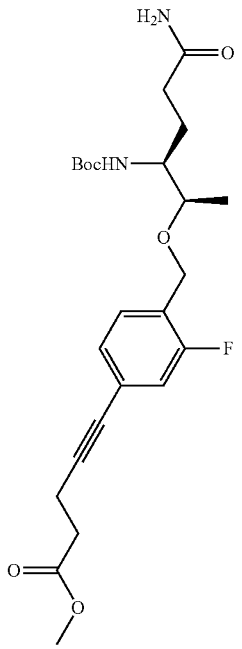 [SMILES: COC(=O)CCC#Cc1ccc(CO[C@H](C)[C@H](CCC(N)=O)NC(=O)OC(C)(C)C)c(F)c1] | methyl 5-[4-([[(2R,3S)-3-[(tert-butoxycarbonyl)amino]-5-carbamoyl-pentan-2-yl]oxylmethyl)-3-fluorophenyl]pent-4-ynoate | 465.20 | (400 MHz, DMSO-$d_6$) δ 7.43 (t, J = 7.8 Hz, 1H), 7.19 (t, J = 8.2 Hz, 3H), 6.68 (s, 1H), 6.61 (d, J = 8.9 Hz, 1H), 4.52 (q, J = 12.4 Hz, 2H), 3.64 (s, 3H), 3.46-3.41 (m, 2H), 2.72-2.59 (m, 4H), 2.13-1.97 (m, 2H), 1.82-1.69 (m, 1H), 1.51-1.42 (m, 1H), 1.38 (s, 9H), 1.07 (d, J = 5.7 Hz, 3H). |
| G-2-38 | 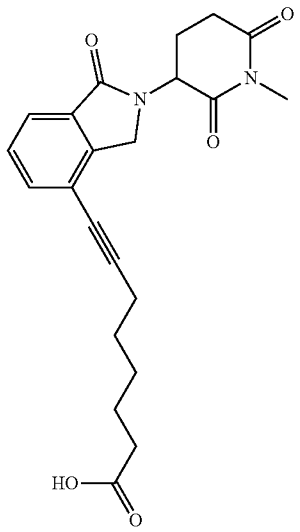 [SMILES: CN1C(=O)CCC(N2Cc3c(C#CCCCCCC(=O)O)cccc3C2=O)C1=O] | 8-[2-(1-methyl-2,6-dioxopiperidin-3-yl)-1-oxo-3H-isoindol-4-yl]oct-7-ynoic acid | 397.20 | (400 MHz, DMSO-$d_6$) δ 11.99 (s, 1H), 7.72 (d, J = 7.5 Hz, 1H), 7.64 (d, J = 7.5 Hz, 1H), 7.53 (t, J = 7.6 Hz, 1H), 5.22 (dd, J = 13.5, 5.1 Hz, 1H), 4.51-4.27 (m, 2H), 3.07-2.94 (m, 4H), 2.78-2.75 (m, 1H), 2.50-2.40 (m, 3H), 2.23 (t, J = 7.2 Hz, 2H), 2.06-2.20 (m, 1H), 1.58-1.54 (m, 4H), 1.46-1.43 (m, 2H). |

TABLE 25-continued

Characterization data for intermediates prepared according to procedure above.

| Intermediate | Structure | Chemical Name | MS: [(M + 1)]+ | $^1$H-NMR |
|---|---|---|---|---|
| G-2-39 | 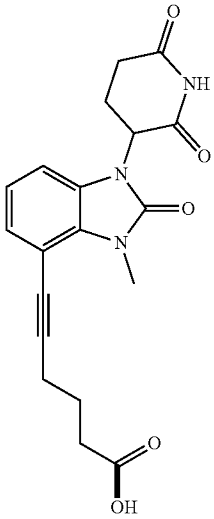 | 6-[1-[2,6-dioxopiperidin-3-yl)-3-methyl-2-oxo-1,3-benzodiazol-4-yl]hex-5-ynoic acid | 370.00 | (400 MHz, DMSO-$d_6$) δ 12.09 (s, 1H), 11.11 (s, 1H), 7.16-7.10 (m, 1H), 7.07 (d, J = 7.9 Hz, 1H), 6.99 (d, J = 7.9 Hz, 1H), 5.39 (dd, J = 12.6, 5.3 Hz, 1H), 3.64 (s, 3H), 2.40 (t, J = 7.2 Hz, 2H), 2.36-2.28 (m, 4H), 2.24-2.14 (m, 2H), 1.86-1.78 (m, 2H) |
| G-2-40 | 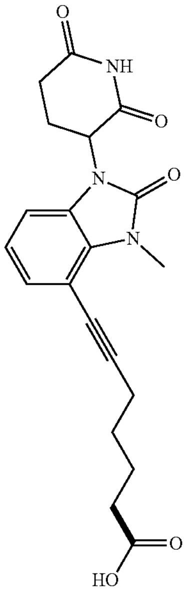 | 7-[1-(2,6-dioxopiperidin-3-yl)-3-methyl-2-oxo-1,3-benzodiazol-4-yl]hept-6-ynoic acid | 384.15 | (400 MHz, DMSO-$d_6$) δ 12.03 (s, 1H), 11.13 (d, J = 8.0 Hz, 1H), 7.12 (d, J = 7.7, 1H), 7.06 (d, J = 7.9, 1H), 6.99 (dd, J = 7.9, 7.7 Hz, 1H), 5.40 (dd, J = 12.5, 5.4 Hz, 1H), 3.64 (s, 3H), 2.96-2.83 (m, 1H), 2.79-2.59 (m, 3H), 2.54-2.52 (m, 2H), 2.38-2.24 (m, 2H), 1.67 (d, J = 7.3 Hz, 1H), 1.62 (d, J = 6.8 Hz, 1H), 1.60-1.56 (m, 1H), 1.47 (d, J = 7.9 Hz, 1H) |

TABLE 25-continued

Characterization data for intermediates prepared according to procedure above.

| Intermediate | Structure | Chemical Name | MS: $[(M + 1)]^+$ | $^1$H-NMR |
|---|---|---|---|---|
| G-2-41 | 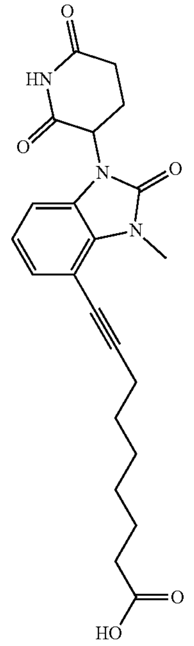 [SMILES: Cn1c(=O)n(C2CCC(=O)NC2=O)c2cccc(C#CCCCCCCC(=O)O)c21] | 9-[1-(2,6-dioxopiperidin-3-yl)-3-methyl-2-oxo-1,3-benzodiazol-4-yl]non-8-ynoic acid | 412.25 | (400 MHz, DMSO-$d_6$) δ 11.99 (s, 1H), 11.13 (s, 1H), 7.12 (dd, J = 7.8, 1.3 Hz, 1H), 7.06 (dd, J = 7.8, 1.2 Hz, 1H), 6.99 (t, J = 7.8 Hz, 1H), 5.39 (dd, J = 12.6, 5.4 Hz, 1H), 3.64 (s, 3H), 2.76-2.67 (m, 1H), 2.64-2.58 (m, 1H), 2.26-2.18 (m, 2H), 1.67-1.47 (m, 6H), 1.45-1.21 (m, 6H) |
| G-2-42 | 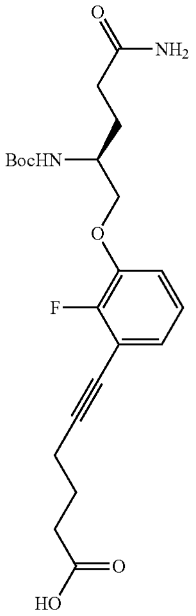 [SMILES: CC(C)(C)OC(=O)N[C@@H](CCC(N)=O)COc1cccc(C#CCCCC(=O)O)c1F] | 6-[3-R2S)-2-[(tert-butoxycarbonyl) amino]-4-carbamoylbutoxy]-2-fluorophenyl] hex-5-ynoic acid | 436 48 | (400 MHz, DMSO-$d_6$) δ 7.80 (s, 1H), 7.27 (s, 1H), 7.17 (t, J = 8.1 Hz, 1H), 7.07 (t, J = 7.9 Hz, 1H), 6.99 (t, J = 6.7 Hz, 1H), 6.73 (s, 1H), 3.97-3.93 (m, 2H), 2.77 -2.72 (m, 1H), 2.48 (s, 2H), 2.17-2.03 (m, 2H), 1.83-1.79 (m, 4H), 1.62-1.58 (m, 1H), 1.38 (s, 9H), 1.33-1.31 (m, 2H) |

TABLE 25-continued

| Intermediate | Structure | Chemical Name | MS: $[(M + 1)]^+$ | $^1$H-NMR |
|---|---|---|---|---|
| Characterization data for intermediates prepared according to procedure above. | | | | |
| G-2-49 | 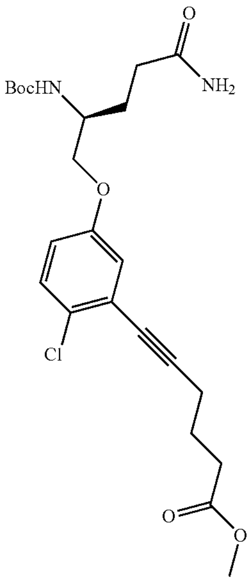 [SMILES: COC(=O)CCCC#Cc1cc(OC[C@H](CCC(N)=O)NC(=O)OC(C)(C)C)ccc1Cl] | methyl 6-[5-[(2S)-2-[(tert-butoxycarbonyl)amino]-4-carbamoyl-butoxy]-2-chlorophenyl]hex-5-ynoate | $[(M - 1)]^-$ = 465.20 | (400 MHz, DMSO-$d_6$) 6 7.39 (d, J = 8.9 Hz, 1H), 7.25 (d, 1H), 7.06 (d, J = 3.0 Hz, 1H), 6.94 (d, J = 8.9, 3.1 Hz, 1H), 6.82 (d, J = 8.5 Hz, 1H), 6.72 (d, 1H), 3.86-3.88 (m, J = 5.9 Hz, 2H), 3.71-3.68 (m, 2H), 2.52 (d, J = 14.9 Hz, 1H), 2.43-2.30 (m, 5H), 2.09-2.01 (m, 2H), 1.88-1.62 (m, 3H), 1.60-1.56 (m, 1H), 1.39 (s, 9H) |
| G-2-50 | 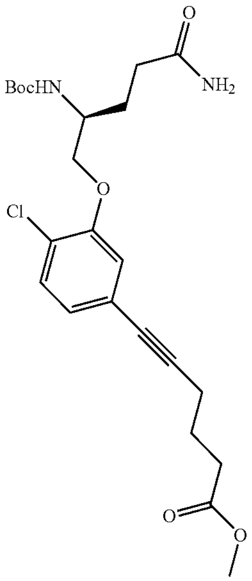 [SMILES: COC(=O)CCCC#Cc1ccc(Cl)c(OC[C@H](CCC(N)=O)NC(=O)OC(C)(C)C)c1] | methyl 6-[3-[(2S)-2-[(tert-butoxycarbonyl)amino]-4-carbamoylbutoxy]-4-chlorophenyl]hex-5-ynoate | 467.20 | (400 MHz, DMSO-$d_6$) δ 7.38 (d, J = 8.1 Hz, 1H), 7.26 (s, 1H), 7.15 (d, J = 1.8 Hz, 1H), 6.98 (dd, J = 8.1, 1.8 Hz, 1H), 6.79 (d, J = 8.5 Hz, 1H), 6.73 (m, 1H), 3.97-3.79 (m, 2H), 3.76-3.53 (m, 1H), 3.32-3.08 (m, 1H), 2.48-2.26 ( m, 4H), 2.45-2.26 (m, 7H), 2.21-2.05 (m, 2H), 1.82-1.70 (m, 5H), 1.69-1.57 (m, 1H), 1.44-1.40 (m, 1H), 1.36-1.24 (m, 1H) |

TABLE 25-continued

| Characterization data for intermediates prepared according to procedure above. | | | | |
|---|---|---|---|---|
| Intermediate | Structure | Chemical Name | MS: $[(M + 1)]^+$ | $^1$H-NMR |
| G-2-51 | 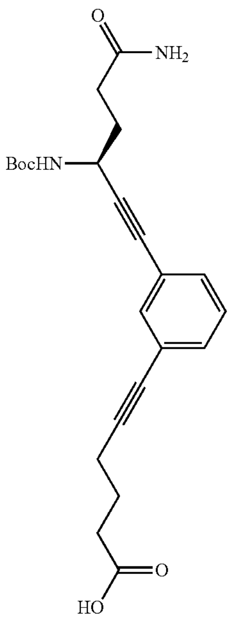 [SMILES: CC(C)(C)OC(=O)N[C@H](C#Cc1cccc(C#CCCCC(=O)O)c1)CCC(N)=O] | 6-[3-[(3S)-3-[(tert-butoxycarbonyl)amino]-5-carbamoylpent-1-yn-1-yl]phenyl]hex-5-ynoic acid | 413.10 | (300 MHz, DMSO-$d_6$) δ 12.08 (s, 1H), 7.73-7.13 (m, 6H), 6.76 (s, 1H), 4.45 (d, J = 7.9 Hz, 1H), 2.44 (d, J = 7.0 Hz, 2H), 2.38 (t, J = 7.4 Hz, 2H), 2.22 (td, J = 7.3, 2.5 Hz, 2H),1.84 (q, J = 7.3 Hz, 2H), 1.75 (q, J = 7.2 Hz, 2H), 1.40 (s, 9H) |
| G-2-52 | 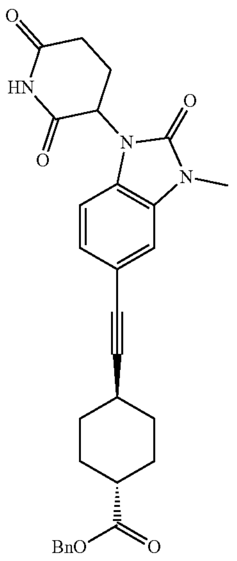 [SMILES: Cn1c(=O)n(C2CCC(=O)NC2=O)c2ccc(C#C[C@H]3CC[C@H](C(=O)OCc4ccccc4)CC3)cc21] | benzyl(1r,4r)-4-[2-[1-(2,6-dioxopiperidin-3-yl)-3-methyl-2-oxo-1,3-benzodiazol-5-yl]ethynyl]cyclohexane-1-carboxylate | 500.10 | (400 MHz, Chloroform-d) δ 8.15 (s, 1H), 7.44-7.31 (m, 5H), 7.15 (dd, J = 8.1, 1.5 Hz, 1H), 7.07 (d, J = 1.5 Hz, 1H), 6.73 (d, J = 8.2 Hz, 1H), 5.20 (dd, J = 12.3, 5.1 Hz, 1H), 5.15 (s, 2H), 3.43 (s, 3H), 3.01-2.92 (m, 1H), 2.91-2.66 (m, 2H), 2.50 (s, 1H), 2.54-2.35 (m, 1H), 2.31-2.22 m, 1H), 2.18-1.98 (m, 4H), 1.60-1.43 (m, 4H) |

TABLE 25-continued

| Intermediate | Structure | Chemical Name | MS: $[(M + 1)]^+$ | $^1$H-NMR |
|---|---|---|---|---|
| Characterization data for intermediates prepared according to procedure above. | | | | |
| G-2-53 | 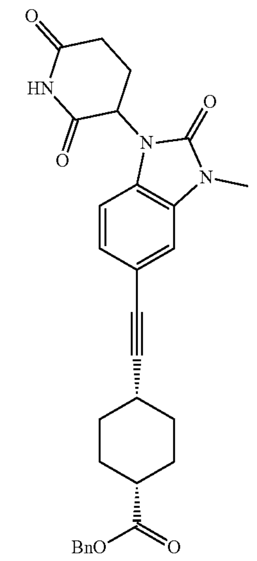 [SMILES: Cn1c(=O)n(C2CCC(=O)NC2=O)c2ccc(C#C[C@H]3CC[C@@H](C(=O)OCc4ccccc4)CC3)cc21] | (1s,4s)-4-((1-(2,6-dioxopiperidin-3-yl)-3-methyl-2-oxo-2,3-dihydro-1H-benzo[d] imidazol-5-yl)ethynyl) cyclohexane-1-carboxylate | 500.10 | (400 MHz, Chloroform-d) δ 8.30 (s, 1H), 7.38 (d, J = 4.6 Hz, 5H), 7.16 (dd, J = 8.1, 1.5 Hz, 1H), 7.09 (d, J = 1.5 Hz, 1H), 6.74 (d, J = 8.1 Hz, 1H), 5.21 (dd, J = 12.6, 5.4 Hz, 1H), 5.16 (s, 2H), 3.44 (s, 3H), 2.96 (dt, J = 19.6, 4.2 Hz, 2H), 2.79 (dtt, J = 38.0, 13.0, 6.7 Hz, 2H), 2.45 (tt, J = 10.3, 3.6 Hz, 1H), 2.26 (dq, J = 13.0, 3.1, 2.3 Hz, 1H), 2.14-1.93 (m, 3H), 1.90 (dtd, J = 17.5, 8.9, 4.2 Hz, 3H), 1.73-1.61 (m, 2H) |
| G-2-54 | 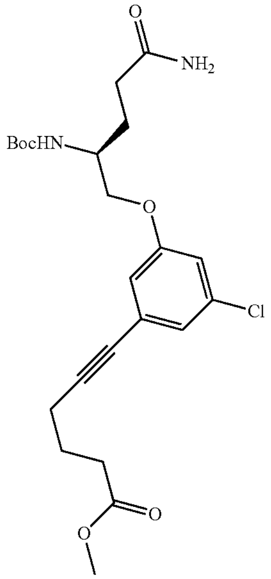 [SMILES: COC(=O)CCCC#Cc1cc(Cl)cc(OC[C@H](CCC(N)=O)NC(=O)OC(C)(C)C)c1] | methyl 6-[3-[(2S)-2-[(tert-butoxycarbonyl) amino]-4-carbamoylbutoxy]-5-chlorophenyl] hex-5-ynoate | 467.05 | (400 MHz, DMSO-$d_6$) δ 7.26 (s, 1H), 7.04-6.99 (m, 2H), 6.92 (t, J = 1.8 Hz, 1H), 6.83 (d, J = 8.5 Hz, 1H), 6.73 (s, 1H), 4.48-4.34 (m, 1H), 3.91 (d, J = 5.8 Hz, 2H), 3.60 (s, 3H), 2.15-2.09 (m, 2H), 1.79 (d, J = 7.3 Hz, 2H), 1.76-1.69 (m, 2H), 1.62 (d, J = 14.1 Hz, 2H), 1.58-1.46 (m, 2H), 1.38 (s, 9H) |

TABLE 25-continued

Characterization data for intermediates prepared according to procedure above.

| Intermediate | Structure | Chemical Name | MS: $[(M+1)]^+$ | $^1$H-NMR |
|---|---|---|---|---|
| G-2-55 | 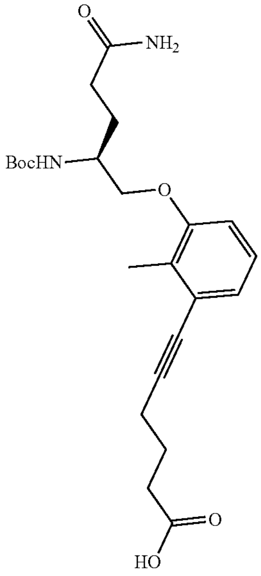 [SMILES: Cc1c(C#CCCCC(=O)O)cccc1OC[C@H](CCC(N)=O)NC(=O)OC(C)(C)C] | 6-[3-(2S)-2-[(tert-butoxycarbonyl)amino]-4-carbamoylbutoxy]-2-methylphenyl]hex-5-ynoic acid | $[(M-1)]^- =$ 431.05 | (400 MHz, DMSO-$d_6$) δ 12.12 (s, 1H), 7.69-7.52 (m, 2H), 7.27 (s, 1H), 7.10 (t, J = 7.9 Hz, 1H), 6.93 (dd, J = 12.1, 7.9 Hz, 2H), 6.83 (d, J = 8.3 Hz, 1H), 6.73 (s, 1H), 3.92-3.88 (m, 1H), 3.86-3.70 (m, 2H), 2.40 (t, J = 6.9 Hz, 2H), 2.23 (s, 3H), 2.15-2.09 (m, 2H), 1.86-1.73 (m, 3H), 1.68-1.52 (m, 1H), 1.39 (s, 9H) |
| G-2-56 | 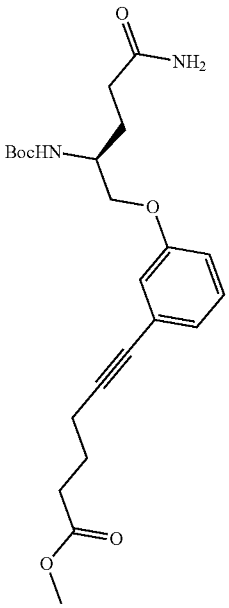 [SMILES: COC(=O)CCCC#Cc1cccc(OC[C@H](CCC(N)=O)NC(=O)OC(C)(C)C)c1] | 6-[3-[(2S)-2-[(tert-butoxycarbonyl)amino]-4-carbamoylbutoxy]phenyl]hex-5-ynoate | 433.30 | (400 MHz, DMSO-$d_6$) δ 7.56 (td, J = 7.4, 2.5 Hz, 1H), 7.28-7.21 (m, 1H), 6.96 (dt, J = 7.6, 1.2 Hz, 1H), 6.91 (dd, J = 7.0, 1.1 Hz, 2H), 6.82 (d, J = 8.5 Hz, 1H), 6.72 (s, 1H), 3.90-3.86 (m, 2H), 3.72-3.68 (m, 1H), 3.61 (s, 3H), 2.47 (s, 3H), 2.20-2.03 (m, 2H), 1.82-1.78 (m, 4H), 1.61 (s, 1H), 1.39 (s, 9H) |

TABLE 25-continued

| Characterization data for intermediates prepared according to procedure above. | | | | |
|---|---|---|---|---|
| Intermediate | Structure | Chemical Name | MS: $[(M + 1)]^+$ | $^1$H-NMR |
| G-2-57 | 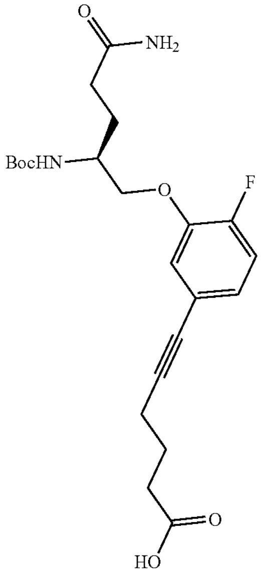 [SMILES: CC(C)(C)OC(=O)N[C@@H](CCC(N)=O)COc1cc(C#CCCCC(=O)O)ccc1F] | 6-[4-[(2S)-2-[(tert-butoxycarbonyl) amino]-4-carbamoylbutoxy]-3-fluorophenyl] hex-5-ynoic acid | $[(M - 1)]^- =$ 435.05 | (400 MHz, DMSO-$d_6$) δ 12.08 (s, 1H), 7.62 (d, J =10.4 Hz, 1H), 7.60-7.51 (m, 1H), 7.27 (s, 1H), 7.22-7.13 (m, 1H), 6.83 (d, J = 8.5 Hz, 1H),6.74 (s, 1H), 3.98-3.94 (m, 2H), 3.74-3.70 (m, 1H), 2.48-2.33 (m, 2H), 2.21-2.04 (m, 2H), 1.79 (s, 1H), 1.78-1.76 (m, 2H), 1.38-1.35 (m, 9H), 1.34-1.31 (m, 1H), 1.30-1.20 (m, 1H), 0.90-0.82 (m, 1H) |
| G-2-58 | 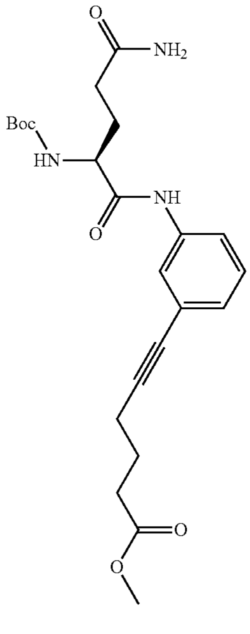 [SMILES: COC(=O)CCCC#Cc1cccc(NC(=O)[C@H](CCC(N)=O)NC(=O)OC(C)(C)C)c1] | methyl 6-[3-[(2S)-2-[(tert-butoxycarbonyl) amino]-4-carbamoyl-butanamido] phenyl]hex-5-ynoate | 446.15 | (300 MHz, DMSO-$d_6$) δ 10.02 (s, 1H), 7.71 (t, J = 1.8 Hz, 1H), 7.50 (d, J = 8.5 Hz, 1H), 7.27 (t, J = 7.9 Hz, 2H), 7.08-7.04 (m, 2H), 6.76 (s, 1H), 4.00 (q, J = 7.5 Hz, 1H), 3.60 (s, 3H), 2.47-2.44 (m, 4H), 2.14 (q, J = 7.7 Hz, 2H), 1.87-1.75 (m, 4H), 1.38 (s, 9H) |

TABLE 25-continued

| Characterization data for intermediates prepared according to procedure above. | | | | |
|---|---|---|---|---|
| Intermediate | Structure | Chemical Name | MS: $[(M + 1)]^+$ | $^1$H-NMR |
| G-2-59 | 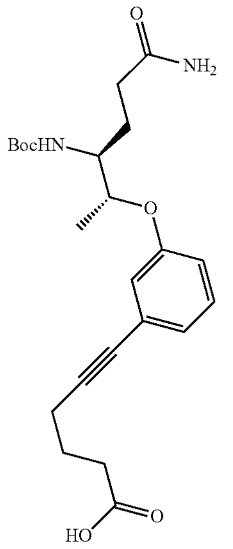 [SMILES: C[C@@H](Oc1cccc(C#CCCCC(=O)O)c1)[C@H](CCC(N)=O)NC(=O)OC(C)(C)C] | 6-(3-[[(2R,3S)-3-[(tert-butoxycarbonyl) amino]-5-carbamoylpentan-2-yl]oxy] phenyl)hex-5-ynoic acid | 433.15 | (400 MHz, DMSO-$d_6$) δ 7.79 (s, 1H), 7.26-7.21 (m, 2H), 6.94 (d, J = 7.5 Hz, 1H), 6.88-6.86 (m, 2H), 6.81-6.66 (m, 2H), 4.36-4.31 (m, 1H), 3.56-3.44 (m, 1H), 3.17 (s, 1H), 2.46-2.39 (m, 3H), 2.14-2.00 (m, 2H), 1.87-1.76 (m, 3H), 1.58-1.45 (m, 1H), 1.38 (s, 9H), 1.17 (d, J = 5.9 Hz, 3H) |
| G-2-60 | 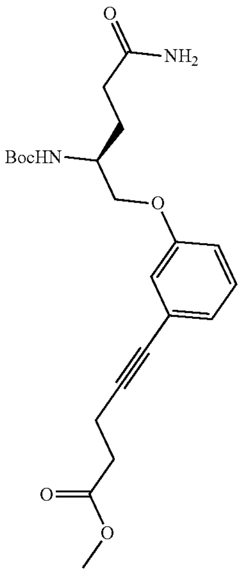 [SMILES: COC(=O)CCC#Cc1cccc(OC[C@H](CCC(N)=O)NC(=O)OC(C)(C)C)c1] | methyl 5-[3-[(2S)-2-[(tert-butoxycarbonyl) amino]-4-carbamoylbutoxy] phenyl]pent-4-ynoate | 419.05 | (400 MHz, DMSO-$d_6$) δ 7.26 (s, 1H), 7.25 (t, J = 7.9 Hz, 1H), 6.99-6.86 (m, 3H), 6.81 (d, J = 8.5 Hz, 1H), 6.72 (s, 1H), 3.90-3.86 (m, 2H), 3.73-3.69 (m, 1H), 3.64 (s, 3H), 2.71-2.56 (m, 4H), 2.21-2.03 (m, 2H), 1.86-1.73 (m, 1H), 1.67-1.53 (m, 1H), 1.39 (s, 9H) |

TABLE 25-continued

| Characterization data for intermediates prepared according to procedure above. | | | | |
|---|---|---|---|---|
| Intermediate | Structure | Chemical Name | MS: $[(M + 1)]^+$ | $^1$H-NMR |
| G-2-61 | 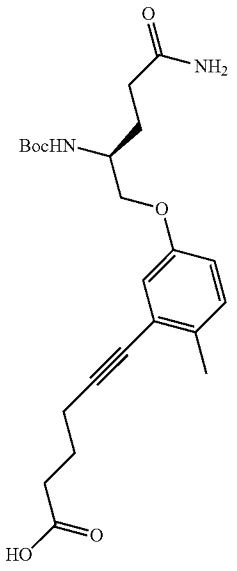 [SMILES: Cc1ccc(OC[C@H](CCC(N)=O)NC(=O)OC(C)(C)C)cc1C#CCCCC(=O)O] | 6-[5-[(2S)-2-[(tert-butoxycarbonyl)amino]-4-carbamoylbutoxy]-2-methylphenyl]hex-5-ynoic acid | 433.05 | (400 MHz, DMSO-$d_6$) δ 12.06 (s, 1H), 7.25 (s, 1H), 7.14 (d, J = 8.5 Hz, 1H), 6.88 (d, J = 2.7 Hz, 1H), 6.85-6.77 (m, 2H), 6.75 (s, 1H), 3.89-3.78 (m, 2H), 3.70-3.68 (m, 2H), 2.41-2.39 (m, 2H), 2.27-2.25 (m, 3H), 2.11-2.09 (m, 2H), 1.78 (s, 3H), 1.60-1.58 (m, 2H), 1.39 (s, 9H) |
| G-2-62 | 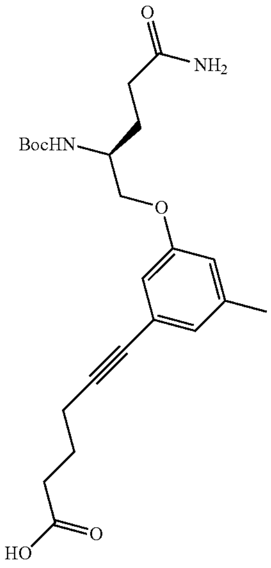 [SMILES: Cc1cc(C#CCCCC(=O)O)cc(OC[C@H](CCC(N)=O)NC(=O)OC(C)(C)C)c1] | 6-[3-[(2S)-2-[(tert-butoxycarbonyl)amino]-4-carbamoylbutoxy]-5-methylphenyl]hex-5-ynoic acid | $[(M - 1)]^-$ = 431.05 | (400 MHz, DMSO-$d_6$) δ 12.09 (s, 1H), 7.25 (s, 1H), 6.80 (d, J = 4.7 Hz, 2H), 6.75-6.71 (m, 3H), 3.91-3.80 (m, 2H), 3.71-3.67 (m, 1H), 2.41 (d, J = 24.6, 7.2 Hz, 3H), 2.24-2.20 (m, 3H), 2.18-2.06 (m, 3H), 1.78-1.74 (m, 2H), 1.62-1.58 (m, 1H), 1.39 (s, 9H), 1.28 -1.24 (m, 1H) |

TABLE 25-continued

| Characterization data for intermediates prepared according to procedure above. | | | | |
|---|---|---|---|---|
| Intermediate | Structure | Chemical Name | MS: $[(M + 1)]^+$ | $^1$H-NMR |
| G-2-63 | 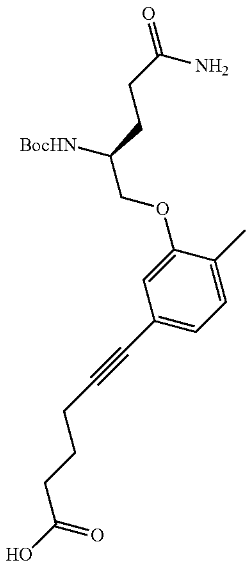 [SMILES: Cc1ccc(C#CCCCC(=O)O)cc1OC[C@H](CCC(N)=O)NC(=O)OC(C)(C)C] | 6-[3-[(2S)-2-[(tert-butoxycarbonyl) amino]4-carbamoylbutoxy]-4-methylphenyl] hex-5-ynoic acid | 433.20 | (400 MHz, DMSO-$d_6$) δ 12.13 (s, 1H), 7.27 (s, 1H), 7.09 (d, J = 7.5 Hz, 1H), 6.88 (d, J = 9.3, 1.8 Hz, 2H), 6.80 (d, J = 8.4 Hz, 1H), 6.73 (s, 1H), 3.94-3.90 (m, 1H), 3.86-3.71 (m, 2H), 2.44-2.40 (m, 2H), 2.40-2.36 (m, 2H), 2.15-2.11 (m, 5H), 1.75-.72 (m, 2H), 1.68-1.54 (m, 2H), 1.39 (s, 9H) |
| G-2-64 | 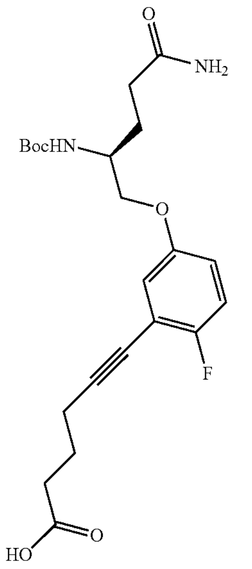 | 6-[5-[(2S)-2-[(tert-butoxycarbonyl) amino]-4-carbamoylbutoxy]-2-fluorophenyl] hex-5-ynoic acid | 437.05 | (400 MHz, DMSO-$d_6$) δ 12.09 (s, 1H), 7.25 (s, 1H), 7.16 (t, J = 9.1 Hz, 1H), 6.98 (dd, J = 5.8, 3.1 Hz, 1H), 6.95-6.91 (m, 1H), 6.81 (d, J = 8.5 Hz, 1H), 6.72 (s, 1H), 3.91-3.80 (m, 2H), 3.69 (s, 1H), 2.50-2.48 (m, 2H), 2.39 (t, J = 7.4 Hz, 2H), 2.13-2.09 (m, 2H), 1.79-1.75 (m, 3H), 1.62-1.58 (m, 1H), 1.39 (s, 9H) |

TABLE 25-continued

Characterization data for intermediates prepared according to procedure above.

| Intermediate | Structure | Chemical Name | MS: [(M + 1)]+ | $^1$H-NMR |
|---|---|---|---|---|
| G-2-65 | 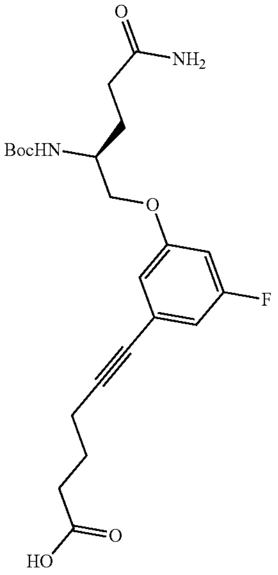 [SMILES: CC(C)(C)OC(=O)N[C@@H](CCC(N)=O)COc1cc(F)cc(C#CCCCC(=O)O)c1] | 6-[3-[(2S)-2-[(tert-butoxycarbonyl) amino]-4-carbamoylbutoxy]-5-fluorophenyl] hex-5-ynoic acid | 437.05 | (400 MHz, DMSO-$d_6$) δ 12.09 (s, 1H), 7.56-7.53 (m, 2H), 7.26 (s, 1H), 6.876.77 (m, 3H), 3.91 (d, J = 5.9 Hz, 2H), 3.73-3.69 (m, 1H), 2.46 (t, J = 7.0 Hz, 2H), 2.38 (t, J = 7.7 Hz, 2H), 2.20-2.05 (m, 2H), 1.85-1.69 (m, 3H), 1.61-1.57 (m, 1H), 1.39 (s, 9H) |
| G-2-66 | 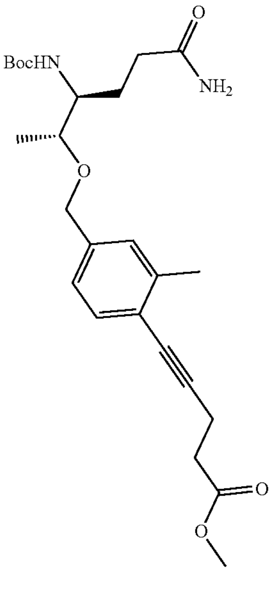 [SMILES: COC(=O)CCC#Cc1ccc(CO[C@H](C)[C@H](CCC(N)=O)NC(=O)OC(C)(C)C)cc1C] | methy 5-[4-([[(2R,3S)-3-[(tert-butoxycarbonyl) amino]-5-carbamoylpentan-2-yl]oxy]methyl)-2-methylphenyl] pent-4-ynoate | 461.25 | (400 MHz, Methanol-$d_4$) δ 7.28 (d, J = 7.9 Hz, 1H), 7.21 (s, 1H), 7.12 (d, J = 7.9 Hz, 1H), 4.60-4.42 (m, 2H), 3.72 (s, 3H), 3.70-3.68 (m, 3H), 3.62-3.55 (m, 1H), 3.53-3.47 (m, 1H), 2.76 (t, J = 7.0 Hz, 2H), 2.65 (t, J = 7.1 Hz, 2H), 2.38 (s, 3H), 2.33-2.19 (m, 2H), 2.02-1.94 (m, 1H), 1.68-1.58 (m, 1H), 1.45 (s, 9H), 1.18 (d, J = 6.2 Hz, 3H) |

TABLE 25-continued

Characterization data for intermediates prepared according to procedure above.

| Intermediate | Structure | Chemical Name | MS: $[(M+1)]^+$ | $^1$H-NMR |
|---|---|---|---|---|
| G-2-67 | 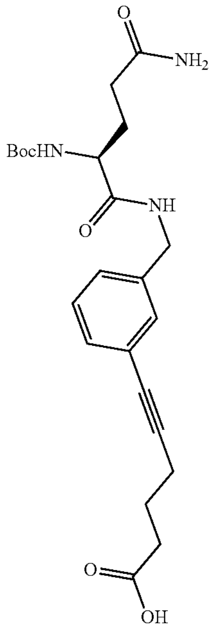 [SMILES: CC(C)(C)OC(=O)N[C@@H](CCC(N)=O)C(=O)NCc1cccc(C#CCCCC(=O)O)c1] | 6-(3-[[2S)-2-[(tert-butoxycarbonyl) amino]-4-carbamoyl-butanamido] methyl]phenyl) hex-5-ynoic acid | 446.20 | (400 MHz, DMSO-$d_6$) δ 12.11 (s, 1H), 8.40-8.27 (m, 1H), 7.29-7.25 (m, 3H), 7.22-7.20 (m, 1H), 6.95 (d, J = 7.8 Hz, 1H), 6.76 (s, br, 1H), 4.35-4.17 (m, 2H), 3.89 (q, J = 7.7 Hz, 1H), 2.45 (t, J = 7.0 Hz, 2H), 2.41-2.29 (m, 3H), 2.26-2.19 (m, 1H), 2.13-2.11 (m, 1H), 1.87-1.83 (m, 1H), 1.74-1.70 (m, 3H), 1.39 (s, 9H) |
| G-2-68 | 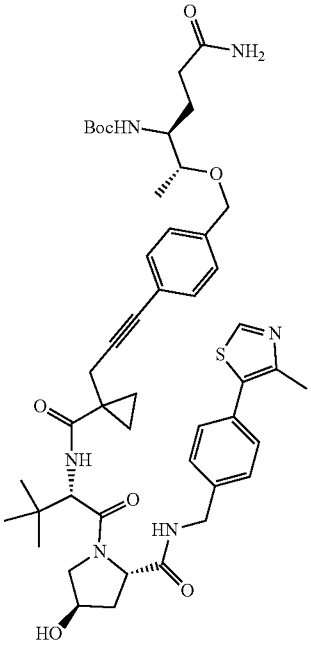 [SMILES: Cc1ncsc1-c1ccc(CNC(=O)[C@@H]2C[C@@H](O)CN2C(=O)[C@@H](NC(=O)C2(CC#Cc3ccc(CO[C@H](C)[C@H](CCC(N)=O)NC(=O)OC(C)(C)C)cc3)CC2)C(C)(C)C)cc1] | tert-butyl N-[(3S,4R)-1-carbamoyl-4-([4-[3-(1-[[(2S)-1-[(2S,4R)-4-hydroxy-2-([[4-(4-methyl-1,3-thiazol-5-yl)phenyl]methyl] carbamoyl) pyrrolidin-1-yl]-3,3-dimethyl-1-oxobutan-2-yl] carbamoyl] cyclopropyl)prop-1-yn-1-yl]phenyl] methoxy)pentan-3-yl]carbamate | 871.40 | (400 MHz, Methanol-$d_4$) δ 8.90 (s, 1H), 7.66 (dd, J = 12.7, 7.4 Hz, 1H), 7.58 (td, J = 8.2, 7.8, 3.0 Hz, 1H), 7.50 (d, J = 8.0 Hz, 2H), 7.46-7.39 (m, 1H), 7.35 (d, J = 11.7 Hz, 1H), 7.27 (d, J = 7.9 Hz, 2H), 4.75 (d, J = 13.4 Hz, 1H), 4.65-4.42 (m, 5H), 4.35 (d, J = 15.5 Hz, 1H), 3.93-3.78 (m, 2H), 3.60 (dd, J = 10.1, 6.2 Hz, 1H), 3.58-3.44 (m, 1H), 3.03 (d, J = 18.1Hz, 1H), 2.67 (d, J = 9.1 Hz, 1H), 2.47 (d, J = 12.3 Hz, 3H), 2.27 (dt, J = 19.9, 9.8 Hz, 3H), 2.11-1.98 (m, 1H), 1.97 (d, J = 11.7 Hz, 1H), 1.62 (d, J = 15.1 Hz, 1H), 1.45 (d, J = 5.0 Hz, 9H), 1.33-1.23 (m, 1H), 1.17 (dd, J = 10.4, 6.3 Hz, 4H), 1.06 (d, J = 9.9 Hz, 9H), 1.02 (d, J = 8.0 Hz, 1H), 0.88 (q, J = 3.8, 3.3 Hz, 1H) |

TABLE 25-continued

Characterization data for intermediates prepared according to procedure above.

| Intermediate | Structure | Chemical Name | MS: [(M + 1)]+ | $^1$H-NMR |
|---|---|---|---|---|
| G-2-69 | 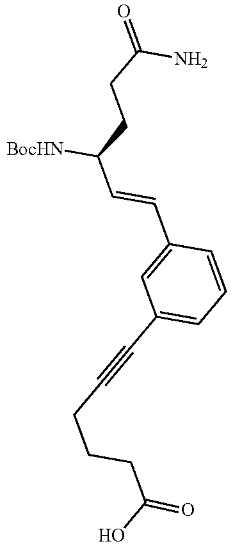 [SMILES: CC(C)(C)OC(=O)N[C@H](/C=C/c1cccc(C#CCCCC(=O)O)c1)CCC(N)=O] | 6-[3-[(1E,3S)-3-[(tert-butoxycarbonyl) amino]-5-carbamoylpent-1-en-1-yl]phenyl] hex-5-ynoic acid | 415.10 | (400 MHz, DMSO-$d_6$) δ 12.13 (s, (s, 1H), 6.40 (d, J = 15.9 Hz, 1H), 6.21 (dd, J = 16.0, 6.6 Hz, 1H), 4.08-4.02 (m, 1H), 2.47 (t, J = 6.9 Hz, 2H), 2.44-2.36 (m, 2H), 2.13-2.10 (m, 2H), 1.82-1.69 (m, 4H), 1.40 (s, 9H) |
| G-2-70 | 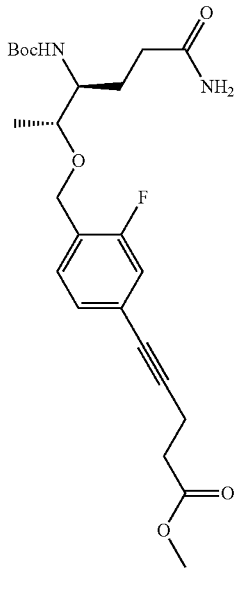 | methyl 5-[4-([[(2R,3S)-3-[(tert-butoxycarbonyl)-amino]5-carbamoylpentan-2-yl]oxy]methyl)-3-fluorophenyl] pent-4-ynoate | 465.20 | (400 MHz, DMSO-$d_6$) δ 7.43 (t, J = 7.7 Hz, 1H), 7.21-7.17 (m, 3H), 6.68 (s, 1H), 6.61 (d, J = 8.8 Hz, 1H), 4.52 (q, J = 12.4 Hz, 2H), 3.64 (s, 3H), 3.46-3.40 (m, 2H), 2.70-2.61 (m, 4H), 2.11-1.97 (m, 2H), 1.80-1.72 (m, 1H), 1.37 (s, 9H), 1.34 (s, 1H), 1.07 (d, J = 5.6 Hz, 3H) |

TABLE 25-continued

| Characterization data for intermediates prepared according to procedure above. | | | | |
|---|---|---|---|---|
| Intermediate | Structure | Chemical Name | MS: $[(M+1)]^+$ | $^1$H-NMR |
| G-2-71 | 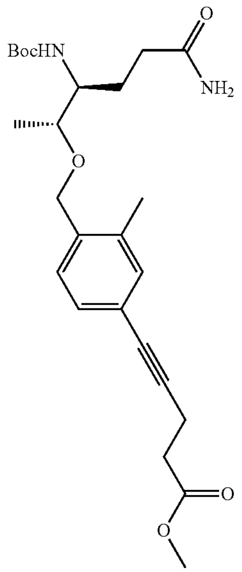 [SMILES: COC(=O)CCC#Cc1ccc(CO[C@H](C)[C@H](CCC(N)=O)NC(=O)OC(C)(C)C)c(C)c1] | methyl 5-[4-([[(2R,3S)-3-[(tert-butoxycarbonyl)amino]-5-carbamoylpentan-2-yl]oxy]methyl)-3-methylphenyl]pent-4-ynoate | 461.24 | (400 MHz, DMSO-$d_6$) δ 7.67-7.52 (m, 1H), 7.29 (d, J = 7.7 Hz, 1H), 7.22 (s, 1H), 7.18-7.12 (m, 2H), 6.68 (s, 1H), 6.60 (d, J = 8.7 Hz, 1H), 4.45 (q, J = 12.1 Hz, 2H), 3.61 (d, J = 10.2 Hz, 1H), 3.43 (h, J = 6.8, 5.8 Hz, 2H), 3.32 (d, J = 9.6 Hz, 1H), 2.64 (dq, J = 12.2, 6.2 Hz, 4H), 2.55 (d, J = 5.3 Hz, 1H), 2.23 (s, 3H), 2.12-1.97 (m, 2H), 1.81-1.73 (m, 1H), 1.38 (s, 9H), 1.08 (d, J = 5.6 Hz, 3H) |
| G-2-72 | 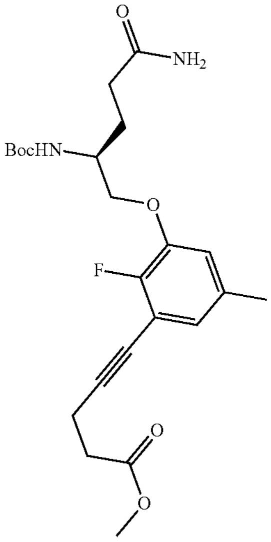 [SMILES: COC(=O)CCC#Cc1cc(C)cc(OC[C@H](CCC(N)=O)NC(=O)OC(C)(C)C)c1F] | methyl 5-[3-[(2S)-2-[(tert-butoxycarbonyl)amino]-4-carbamoylbutoxy]-2-fluoro-5-methylphenyl]pent-4-ynoate | 451.20 | (400 MHz, DMSO-$d_6$) δ 7.26 (s, 1H), 7.00 (d, J = 7.7 Hz, 1H), 6.84 (d, J = 8.4 Hz, 1H), 6.80-6.71 (m, 2H), 3.95-3.90 (m, 2H), 3.76-3.68 (m, 1H), 3.64 (s, 3H), 2.70 (dd, J = 7.6, 5.6 Hz, 2H), 2.64-2.58 (m, 2H), 2.23 (s, 3H), 2.16-2.07 (m, 2H), 1.85-1.73 (m, 1H), 1.66-1.52 (m, 1H), 1.39 (s, 9H) |

TABLE 25-continued

| Characterization data for intermediates prepared according to procedure above. | | | | |
|---|---|---|---|---|
| Intermediate | Structure | Chemical Name | MS: $[(M+1)]^+$ | $^1$H-NMR |
| G-2-73 | 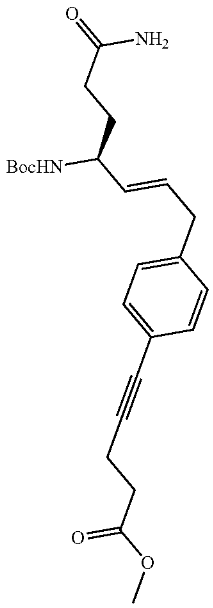 [SMILES: COC(=O)CCC#Cc1ccc(C/C=C/[C@H](CCC(N)=O)NC(=O)OC(C)(C)C)cc1] | methyl 5-[4-[(2E,4S)-4-[(tert-butoxycarbonyl)amino]-6-carbamoylhex-2-en-1-yl]phenyl]pent-4-ynoate | 429.25 | (400 MHz, DMSO-$d_6$) δ 7.29 (d, J =7.9 Hz, 2H), 7.23 (s, 1H), 7.16 (d, J = 8.0 Hz, 2H), 6.87 (d, J = 8.8 Hz, 1H), 6.71 (s, 1H), 5.67-5.51 (m, 1H), 5.46-5.31 (m, 1H), 3.87-3.85 (m, 1H), 3.65 (s, 3H), 3.35-3.31 (m, 2H), 2.74-2.56 (m, 4H), 2.04 (t, J = 7.7 Hz, 2H), 1.68-1.57 (m, 2H), 1.38 (s, 9H) |
| G-2-74 | 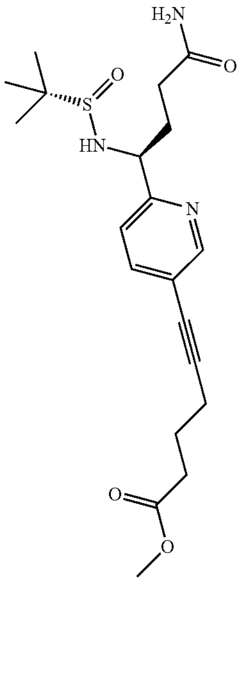 | methyl 6-[6-[(1S)-3-carbamoyl-1-[(2-methylpropane-2-sulfinyl)amino]propyl]pyridin-3-yl]hex-5-ynoate | 408.15 | (400 MHz, DMSO-$d_6$) δ 8.45 (s, 1H), 7.72-7.71 (m, 1H), 7.45-7.43 (d, J = 8.0 Hz, 1H), 7.28 (s, 1H), 6.78 (s, 1H), 5.75-5.74 (d, J = 5.3 Hz, 1H), 4.33-4.28 (m, 1H), 3.61 (s, 3H), 2.48 (s, 2H), 2.47 (s, 1H), 2.19-1.99 (m, 4H), 1.86-1.78 (m, 3H), 1.08 (s, 9H) |

TABLE 25-continued

| Characterization data for intermediates prepared according to procedure above. | | | | |
|---|---|---|---|---|
| Intermediate | Structure | Chemical Name | MS: $[(M + 1)]^+$ | $^1$H-NMR |
| G-2-75 | 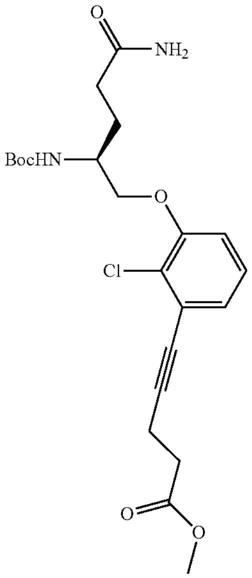 [SMILES: COC(=O)CCC#Cc1cccc(OC[C@H](CCC(N)=O)NC(=O)OC(C)(C)C)c1Cl] | methyl 5-[3-[(2S)-2-[(tert-butoxycarbonyl) amino]-4-carbamoylbutoxy]-2-chlorophenyl] pent-4-ynoate | 453.10 | (300 MHz, DMSO-$d_6$) δ 7.31-7.20 (m, 2H), 7.15 (d, J = 8.2 Hz, 1H), 7.11-7.03 (m, 1H), 6.83 (d, J = 8.4 Hz, 1H), 6.75 (s, 1H), 3.96 (dd, J = 6.2, 3.0 Hz, 2H), 3.78 (s, 1H), 3.65 (s, 3H), 2.80-2.59 (m, 4H), 2.16-2.12 (m, 2H), 1.85-1.81 (s, 1H), 1.63-1.59 (m, 1H), 1.40 (s, 9H) |
| G-2-76 | 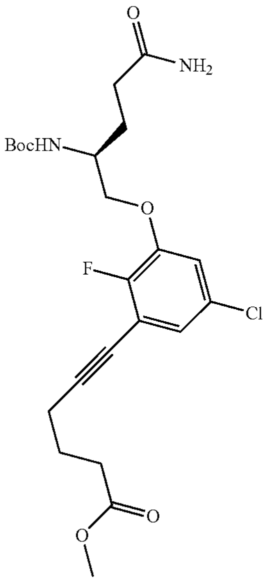 [SMILES: COC(=O)CCCC#Cc1cc(Cl)cc(OC[C@H](CCC(N)=O)NC(=O)OC(C)(C)C)c1F] | methyl 6-[3-[(2S)-2-[(tert-butoxycarbonyl) amino]-4-carbamoylbutoxy]-5-chloro-2-fluorophenyl]hex-5-ynoate | 485.20 | (300 MHz, DMSO-$d_6$) δ 7.37-7.33 (m, 1H), 7.27 (s, 1H), 7.10-7.08 (m, 1H) , 6.85 (d, J = 8.4 Hz, 1H), 6.74 (s, 1H), 4.03-3.98 (m, 3H), 3.74-3.72 (m, 1H), 3.61 (s, 3H), 2.15-2.12 (m, 2H), 1.87-1.69 (m, 6H), 1.62-1.58 (m, 1H), 1.39 (s, 9H) |

TABLE 25-continued

| Characterization data for intermediates prepared according to procedure above. | | | | |
|---|---|---|---|---|
| Intermediate | Structure | Chemical Name | MS: $[(M+1)]^+$ | $^1$H-NMR |
| G-2-77 | 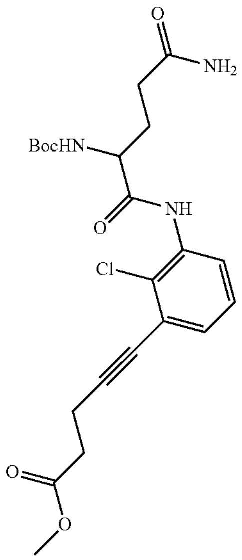 [SMILES: COC(=O)CCC#Cc1cccc(NC(=O)C(CCC(N)=O)NC(=O)OC(C)(C)C)c1Cl] | methyl 5-(3-[2-[(tert-butoxycarbonyl) amino]-4-carbamoylbutanamido]-2-chlorophenyl) pent-4-ynoate | 466.20 | (400 MHz, DMSO-$d_6$) δ 9.45 (s, 1H), 7.87-7.79 (m, 1H), 7.63 (td, J = 6.2, 5.1, 3.4 Hz, 1H), 7.63-7.52 (m, 1H), 7.29 (d, J = 4.8 Hz, 2H), 6.81 (s, 1H), 4.13 (s, 1H), 3.64 (s, 3H), 2.75 (dd, J = 7.4, 5.8 Hz, 2H), 2.65 (dd, J = 7.4, 5.8 Hz, 2H), 2.20 (d, J = 8.1 Hz, 2H), 2.00 (s, 1H), 1.83-1.79 (m, 1H), 1.41 (s, 9H) |
| G-2-78 | 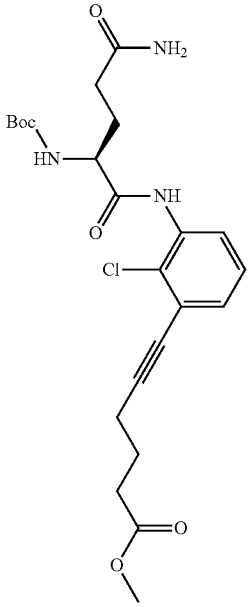 [SMILES: COC(=O)CCCC#Cc1cccc(NC(=O)[C@H](CCC(N)=O)NC(=O)OC(C)(C)C)c1Cl] | methyl 6-[3-[(2S)-2-[(tert-butoxycarbonyl) amino]-4-carbamoylbutanamido]-2-chlorophenyl] hex-5-ynoate | 480.20 | (300 MHz, DMSO-$d_6$) δ 9.76 (s, 1H), 7.87-7.81 (m, 1H), 7.72-7.50 (m, 4H), 7.32 (s, 1H), 7.23 (t, J = 6.9 Hz, 1H), 7.15 (t, J = 7.8 Hz, 2H), 6.81 (s, 1H), 4.20-4.14 (m, 1H), 3.62 (s, 3H), 2.23-2.16 (m, 2H), 2.01-1.72 (m, 4H), 1.41 (s, 9H) |

TABLE 25-continued

| Characterization data for intermediates prepared according to procedure above. | | | | |
|---|---|---|---|---|
| Intermediate | Structure | Chemical Name | MS: $[(M + 1)]^+$ | $^1$H-NMR |
| G-2-79 | 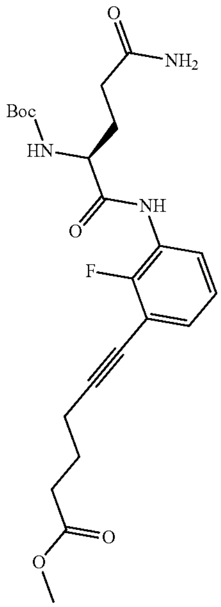 [SMILES: COC(=O)CCCC#Cc1cccc(NC(=O)[C@H](CCC(N)=O)NC(=O)OC(C)(C)C)c1F] | methyl 6-[3-[(2S)-2-[(tert-butoxycarbonyl)amino]-4-carbamoylbutanamido]-2-fluorophenyl]hex-5-ynoate | 464.15 | (300 MHz, DMSO-$d_6$) δ 9.45 (s, 1H), 7.84 (d, J = 4.9 Hz, 1H), 7.41-7.19 (m, 4H), 6.82 (s, 1H), 4.17-4.12 (m, 1H), 3.34 (s, 3H), 2.59-2.54 (m, 4H), 2.23-2.19 (m, 2H), 2.04-1.97 (m, 1H), 1.90-1.80 (m, 3H), 1.42 (s, 9H) |
| G-2-80 | 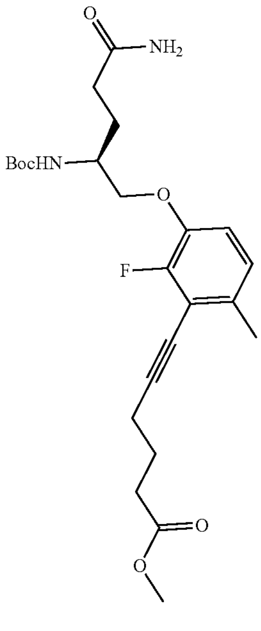 [SMILES: COC(=O)CCCC#Cc1c(C)ccc(OC[C@H](CCC(N)=O)NC(=O)OC(C)(C)C)c1F] | methyl 6-[3-[(2S)-2-[(tert-butoxycarbonyl)amino]-4-carbamoylbutoxy]-2-fluoro-6-methylphenyl]hex-5-ynoate | 465.15 | (400 MHz, DMSO-$d_6$) δ 7.26 (s, 1H), 7.17-6.95 (m, 2H), 6.84 (dd, J = 8.5, 5.4 Hz, 1H), 6.74 (s, 1H), 4.00-3.88 (m, 2H), 3.72 (s, 1H), 3.61 (s, 3H), 2.60-2.52 (m, 2H), 2.30 (s, 3H), 2.20-2.03 (m, 2H), 1.88-1.73 (m, 2H), 1.66-1.57 (m, 2H), 1.58-1.43 (m, 2H), 1.38 (s, 9H) |

TABLE 25-continued

Characterization data for intermediates prepared according to procedure above.

| Intermediate | Structure | Chemical Name | MS: $[(M + 1)]^+$ | $^1$H-NMR |
|---|---|---|---|---|
| G-2-81 | 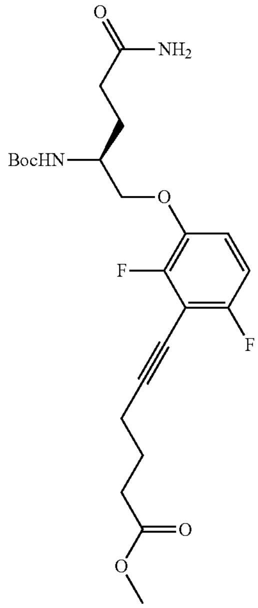 [SMILES: COC(=O)CCCC#Cc1c(F)ccc(OC[C@H](CCC(N)=O)NC(=O)OC(C)(C)C)c1F] | 6-[3-[(2S)-2-[(tert-butoxycarbonyl) amino]-4-carbamoylbutoxyl-2,6-difluorophenyl] hex-5-ynoate | 469.15 | (400 MHz, DMSO-$d_6$) δ 7.22 (dd, J = 15.2, 9.7 Hz, 2H), 7.10-7.06 (m, 1H), 6.83 (d, J = 8.4 Hz, 1H), 6.73 (s, 1H), 3.97-3.93 (m, 2H), 3.74-3.69 (m, 1H), 3.61 (s, 3H), 2.59-2.55 (m, 2H), 2.51-2.38 (m, 2H), 2.19-2.03 (m, 1H), 1.88-1.72 (m, 4H), 1.61-1.56 (m, 1H), 1.38 (s, 9H) |
| G-2-82 | 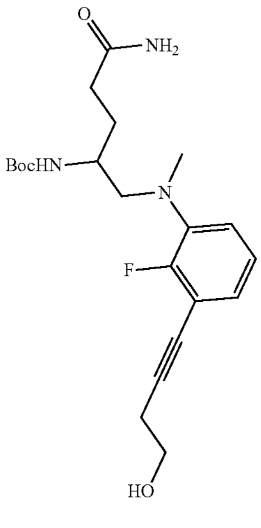 [SMILES: CN(CC(CCC(N)=O)NC(=O)OC(C)(C)C)c1cccc(C#CCCO)c1F] | tert-butyl N-(4-carbamoyl-1-[[2-fluoro-3-(4-hydroxybut-1-yn-1-yl)phenyl] (methyl)amino] butan-2-yl)carbamate | 408.15 | (400 MHz, DMSO-$d_6$) δ 7.22 (s, 1H), 6.98 (t, J = 7.8 Hz, 1H), 6.94-6.82 (m, 2H), 6.69 (s, 1H), 6.57 (d, J = 9.1 Hz, 1H), 4.90 (t, J = 5.5 Hz, 1H), 3.61-3.57 (m, 2H), 3.32 (d, J = 9.5 Hz, 2H), 3.17-3.07 (m, 2H), 2.81 (s, 3H), 2.59 (t, J = 6.9 Hz, 2H), 2.07-2.03 (m, 2H), 2.09-1.99 (m, 1H), 1.34 (s, 9H) |

TABLE 25-continued

Characterization data for intermediates prepared according to procedure above.

| Intermediate | Structure | Chemical Name | MS: $[(M + 1)]^+$ | $^1$H-NMR |
|---|---|---|---|---|
| G-2-83 | 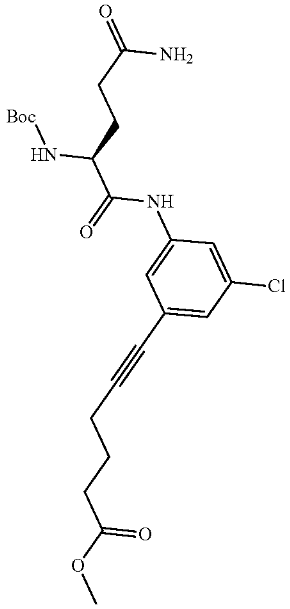 [SMILES: COC(=O)CCCC#Cc1cc(Cl)cc(NC(=O)[C@H](CCC(N)=O)NC(=O)OC(C)(C)C)c1] | methyl 6-[3-[(2S)-2-[(tert-butoxycarbonyl)amino]-4-carbamoylbutanamido]-5-chlorophenyl]hex-5-ynoate | 480.20 | (400 MHz, $CDCl_3$) δ 9.75 (s, 1H), 7.69 (s, 1H), 7.49 (s, 1H), 7.12 (t, J = 1.6 Hz, 1H), 6.22 (d, J = 38.6 Hz, 2H), 5.82 (s, 1H), 4.43 (s, 1H), 3.72 (s, 3H), 2.59-2.43 (m, 6H), 2.33-2.22 (m, 1H), 2.12-1.94 (m, 3H), 1.48 (s, 9H) |
| G-2-84 | 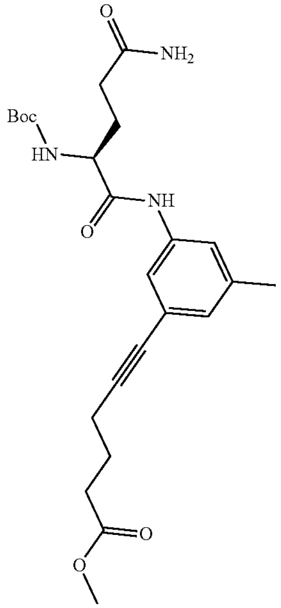 [SMILES: COC(=O)CCCC#Cc1cc(C)cc(NC(=O)[C@H](CCC(N)=O)NC(=O)OC(C)(C)C)c1] | Methyl 6-[3-[(2S)-2-[(tert-butoxycarbonyl)amino]-4-carbamoylbutanamido]-5-methylphenyl]hex-5-ynoate | 460.20 | (300 MHz, DMSO-$d_6$) δ 9.94 (s, 1H), 7.52 (s, 1H), 7.36 (s, 1H), 7.30 (s, 1H), 7.06 (d, J = 7.5 Hz, 1H), 6.92 (s, 1H), 6.79 (s, 1H), 4.02 (q, J = 7.4 Hz, 1H), 3.62 (s, 3H), 2.53-2.44 (m, 3H), 2.26 (s, 3H), 2.23-2.03 (m, 3H), 1.87-1.78 (m, 4H), 1.40 (s, 9H) |

TABLE 25-continued

| Characterization data for intermediates prepared according to procedure above. | | | | |
|---|---|---|---|---|
| Intermediate | Structure | Chemical Name | MS: $[(M + 1)]^+$ | $^1$H-NMR |
| G-2-85 | 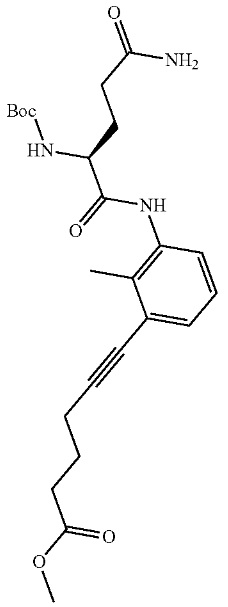 [SMILES: COC(=O)CCCC#Cc1cccc(NC(=O)[C@H](CCC(N)=O)NC(=O)OC(C)(C)C)c1C] | methyl 6-[3-[(2S)-2-[(tert-butoxycarbonyl)amino]-4-carbamoylbutanamido]-2-methylphenyl]hex-5-ynoate | 460.25 | (400 MHz, DMSO-$d_6$) δ 9.40 (s, 1H), 7.35-7.29 (m, 2H), 7.22 (dd, J =7.7, 1.5 Hz, 1H), 7.15 (d, J = 7.8 Hz, 1H), 7.08 (d, J = 7.5 Hz, 1H), 6.81 (s, 1H), 4.10-4.01 (m, 1H), 3.61 (s, 3H), 2.26 (s, 3H), 2.25-2.11 (m, 4H), 1.98-1.92 (m, 2H), 1.86-1.81 (m, 4H), 1.41 (s, 9H) |
| G-2-86 | 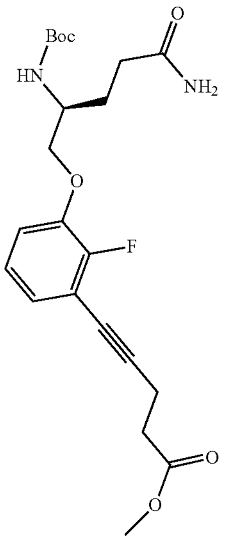 [SMILES: COC(=O)CCC#Cc1cccc(OC[C@H](CCC(N)=O)NC(=O)OC(C)(C)C)c1F] | methyl 5-[3-[(2S)-2-[(tert-butoxycarbonyl)amino]-4-carbamoylbutoxy]-2-fluorophenyl]pent-4-ynoate | 437.15 | (400 MHz, DMSO-$d_6$) δ 7.27 (s, 1H), 7.18 (t, J = 8.2, 1.6 Hz, 1H), 7.07 (t, J = 8.1, 1.2 Hz, 1H), 6.97 (m, 1H), 6.85 (d, J = 8.5 Hz, 1H), 6.74 (s, 1H), 3.97-3.93 (m, 2H), 3.75-3.71 (m, 1H), 3.64 (s, 3H), 2.72 (t, J = 5.7 Hz, 2H), 2.64-2.62 (m, 2H), 2.17-2.05 (m, 2H), 1.84-1.74 (m, 1H), 1.61-1.57 (m, 1H), 1.38 (s, 9H) |

TABLE 25-continued

| Characterization data for intermediates prepared according to procedure above. | | | | |
|---|---|---|---|---|
| Intermediate | Structure | Chemical Name | MS: $[(M+1)]^+$ | $^1$H-NMR |
| G-2-87 | 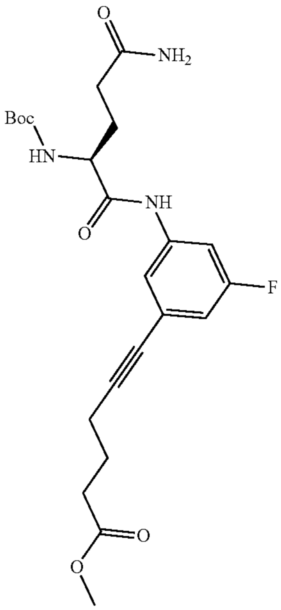 [SMILES: COC(=O)CCCC#Cc1cc(F)cc(NC(=O)[C@H](CCC(N)=O)NC(=O)OC(C)(C)C)c1] | methyl 6-[3-[(2S)-2-[(tert-butoxycarbonyl) amino]-4-carbamoylbutanamido]-5-fluorophenyl] hex-5-ynoate | 464.25 | (300 MHz, DMSO-$d_6$) δ 10.23 (s, 1H), 7.59-7.50 (m, 1H), 7.48 (s, 1H), 7.30 (s, 1H), 7.13 (d, J = 7.3 Hz, 1H), 6.99-6.87 (m, 1H), 6.80 (s, 1H), 4.12-3.93 (m, 1H), 3.62 (s, 3H), 2.50-2.44 (m, 4H), 2.26-2.08 (m, 2H), 1.98-1.74 (m, 4H), 1.40 (s, 9H) |
| G-2-88 | 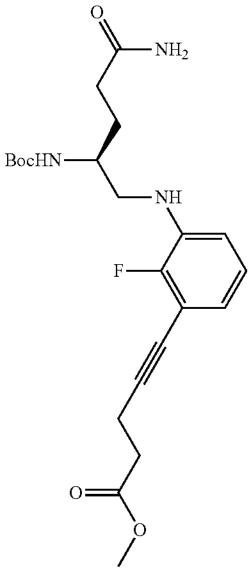 [SMILES: COC(=O)CCC#Cc1cccc(NC[C@H](CCC(N)=O)NC(=O)OC(C)(C)C)c1F] | methyl 6-[3-([2-[(tert-butoxycarbonyl) amino]-4-carbamoylbutyl] amino)-2-fluorophenyl] hex-5-ynoate | 450.30 | (400 MHz, DMSO-$d_6$) δ 7.25 (s, 1H), 6.90-6.76 (m, 1H), 6.72 (s, 1H), 6.60 (t, J = 8.2 Hz, 1H), 6.41 (t, J = 7.1 Hz, 2H), 5.23 (s, 1H), 3.60-3.56 (m, 4H), 3.18 (s, 1H), 3.09-3.05 (m, 1H), 2.52 (d, J = 15.5 Hz, 1H), 2.31-2.27 (m, 2H), 2.16-1.98 (m, 1H), 1.91-1.87 (m, 1H), 1.79-1.75 (m, 1H), 1.62-1.47 (m, 4H), 1.29 (s, 9H) |

TABLE 25-continued

Characterization data for intermediates prepared according to procedure above.

| Intermediate | Structure | Chemical Name | MS: $[(M+1)]^+$ | $^1$H-NMR |
|---|---|---|---|---|
| G-2-89 | 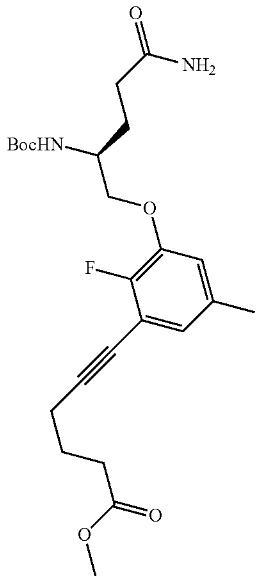 [SMILES: COC(=O)CCCC#Cc1cc(C)cc(OC[C@H](CCC(N)=O)NC(=O)OC(C)(C)C)c1F] | methyl 6-[3-[(2S)-2-[(tert-butoxycarbonyl) amino]-4-carbamoylbutoxy]-2-fluoro-5-methylphenyl] hex-5-ynoate | 465.25 | (400 MHz, DMSO-$d_6$) δ 7.26 (s, 1H), 7.03-6.96 (m, 1H), 6.87-6.77 (m, 2H), 6.74 (s, 1H), 3.99-3.87 (m, 2H), 3.78-3.66 (m, 1H), 3.61 (s, 3H), 2.49-2.44 (m, 2H), 2.24 (s, 3H), 2.18-2.05 (m, 4H), 1.85-1.74 (m, 3H), 1.65-1.52 (m, 1H), 1.39 (s, 9H) |
| G-2-90 | 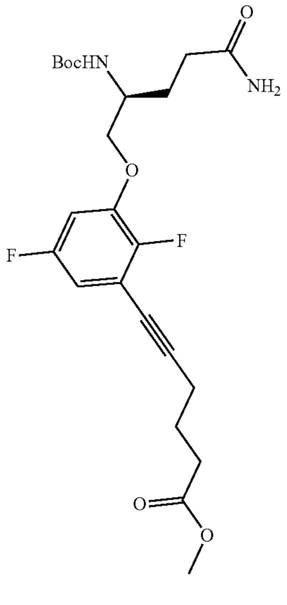 [SMILES: COC(=O)CCCC#Cc1cc(F)cc(OC[C@H](CCC(N)=O)NC(=O)OC(C)(C)C)c1F] | methyl 6-[3-[(2S)-2-[(tert-butoxycarbonyl) amino]-4-carbamoylbutoxy]-2,5-difluorophenyl] hex-5-ynoate | 469.05 | (400 MHz, $CDCl_3$) δ 6.74-6.62 (m, 2H), 6.20 (s, 1H), 5.45 (s, 1H), 5.06 (s, 1H), 4.04 (br, 3H), 3.72 (s, 3H), 2.55 (td, J = 7.1, 4.7 Hz, 4H), 2.38 (t, J = 6.9 Hz, 2H), 2.13-1.98 (m, 4H), 1.48 (s, 9H) |

TABLE 25-continued

| Characterization data for intermediates prepared according to procedure above. | | | | |
|---|---|---|---|---|
| Intermediate | Structure | Chemical Name | MS: $[(M+1)]^+$ | $^1H$-NMR |
| G-2-91 | 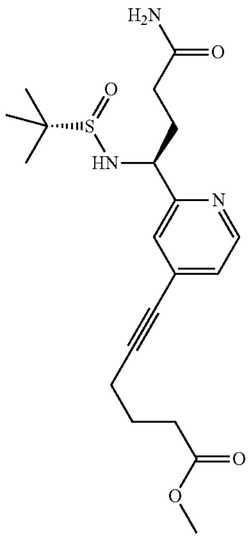 | methyl 6-[2-[(1S)-3-carbamoyl-1-[(2-methylpropane-2-sulfinyl)amino]propyl]pyridin-4-yl]hex-5-ynoate | 408.15 | (400 MHz, DMSO-$d_6$) δ 8.58-8.37 (m, 1H), 7.43 (s, 1H), 7.31-7.29 (d, J = 4.7 Hz, 2H), 6.80 (s, 1H), 5.81-5.79 (d, J = 5.8 Hz, 1H), 4.29-4.25 (m, 1H), 3.61 (s, 3H), 2.49-2.47 (d, J = 9.3 Hz, 3H), 2.18-2.01 (m, 3H), 1.89-1.78 (m, 3H), 1.09 (s, 9H) |
| G-2-92 | 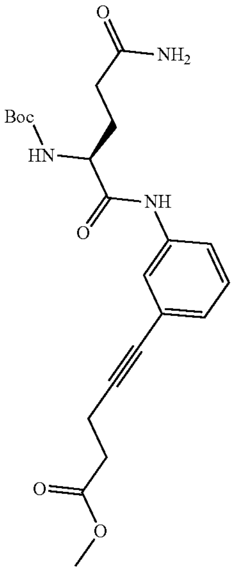 [SMILES: COC(=O)CCC#Cc1cccc(NC(=O)[C@H](CCC(N)=O)NC(=O)OC(C)(C)C)c1] | methyl 5-[3-[(2S)-2-[(tert-butoxycarbonyl)amino]-4-carbamoylbutanamido]phenyl]pent-4-ynoate | 432.20 | (300 MHz, DMSO-$d_6$) δ 10.02 (s, 1H), 7.73 (d, J = 2.1 Hz, 1H), 7.53-7.50 (m, 1H), 7.35-7.20 (m, 2H), 7.06 (d, J = 7.6 Hz, 1H), 6.78 (s, 1H), 4.06-4.01 (m, 1H), 3.66 (s, 3H), 2.71-2.60 (m, 5H), 2.20-2.12 (m, 2H), 1.99-1.70 (m, 2H), 1.40 (s, 9H) |

TABLE 25-continued

| Characterization data for intermediates prepared according to procedure above. | | | | |
|---|---|---|---|---|
| Intermediate | Structure | Chemical Name | MS: $[(M + 1)]^+$ | $^1$H-NMR |
| G-2-93 | 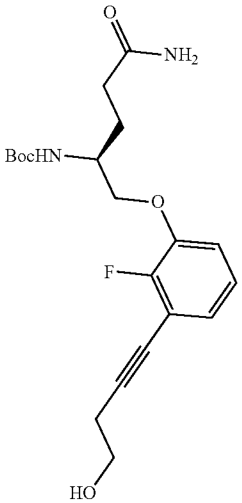 [SMILES: CC(C)(C)OC(=O)N[C@@H](CCC(N)=O)COc1cccc(C#CCCO)c1F] | tert-butyl N-[(2S)-4-carbamoyl-1-[2-fluoro-3-(4-hydroxybut-1-yn-1-yl)phenoxy]butan-2-yl]carbamate | 395.25 | (400 MHz, DMSO-$d_6$) δ 7.27 (s, 1H), 7.17 (td, J = 8.1, 1.7 Hz, 1H), 7.07 (t, J = 8.0 Hz, 1H), 7.01-6.99 (m, 1H), 6.85 (d, J = 8.4 Hz, 1H), 6.74 (s, 1H), 4.92 (s, 1H), 3.95 (d, J = 6.1 Hz, 2H), 3.75-3.70 (m, 1H), 3.59 (t, J = 6.8 Hz, 2H), 2.60 (t, J = 6.8 Hz, 2H), 2.21-2.03 (m, 2H), 1.79 (s, 1H), 1.59 (s, 1H), 1.39 (s, 9H) |
| G-2-96 | 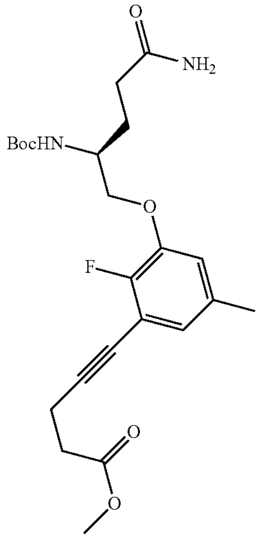 [SMILES: COC(=O)CCC#Cc1cc(C)cc(OC[C@H](CCC(N)=O)NC(=O)OC(C)(C)C)c1F] | methyl 5-[3-[(2S)-2-[(tert-butoxycarbonyl) amino]-4-carbamoylbutoxy]-2-fluoro-5-methylphenyl] pent-4-ynoate | 451.20 | (400 MHz, DMSO-$d_6$) δ 7.26 (s, 1H), 7.00 (d, J = 7.7 Hz, 1H), 6.84 (d, J = 8.4 Hz, 1H), 6.80-6.71 (m, 2H), 3.95-3.90 (m, 2H), 3.76-3.68 (m, 1H), 3.64 (s, 3H), 2.70 (dd, J = 7.6, 5.6 Hz, 2H), 2.64-2.58 (m, 2H), 2.23 (s, 3H), 2.16-2.07 (m, 2H), 1.85-1.73 (m, 1H), 1.66-1.52 (m, 1H), 1.39 (s, 9H) |

Tert-butyl (2E)-3-[1-(2,6-dioxopiperidin-3-yl)-3-methyl-2-oxo-2,3-dihydro-1H-1,3-benzodiazol-5-

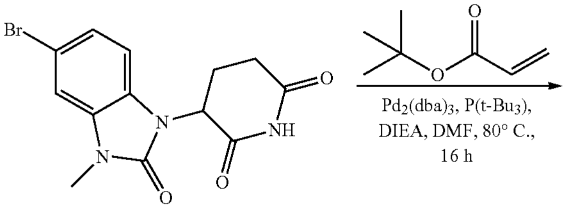

-continued

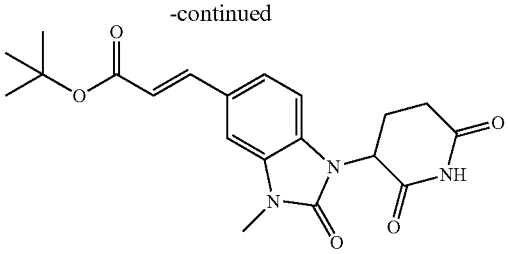

Intermediate G-2-13

To a mixture of 3-(5-bromo-3-methyl-2-oxo-2,3-dihydro-1H-1,3-benzodiazol-1-yl)piperidine-2,6-dione (1.00 g, 3.00 mmol), tert-butyl-prop-2-enoate (3.79 g, 29.6 mmol), DIEA (0.76 g, 5.90 mmol) and $Pd_2(dba)_3$ (0.27 g, 0.30 mmol) in DMA (30.0 mL) was added $P(t\text{-}Bu)_3$ (10% in hexane, 1.20 g, 0.59 mmol) at room temperature under nitrogen atmosphere. The mixture was purged with nitrogen for 3 times and stirred for 16 hours at 80° C. under nitrogen atmosphere. The mixture was cooled down to room temperature and concentrated under reduced pressure. The residue was purified by reversed phase flash chromatography with the following conditions: Column: WelFlash™ C18-I, 20~40 m, 330 g; Eluent A: water (plus 10 mmol/L HOAc); Eluent B: ACN; Gradient: 30% - 50% B in 25 min; Flow rate: 80 mL/min; Detector: UV 220/254 nm; desired fractions were collected at 39% B and concentrated under reduced pressure to afford the title compound as a brown solid (0.91 g, 80%): $^1$H NMR (400 MHz, $CDCl_3$) δ 7.62 (d, J=15.9 Hz, 1H), 7.27-7.18 (m, 2H), 6.82 (d, J=8.1 Hz, 1H), 6.35 (d, J=15.9 Hz, 1H), 5.24 (dd, J=12.7, 5.3 Hz, 1H), 3.48 (d, J=1.2 Hz, 3H), 2.98 (d, J=17.0 Hz, 1H), 2.92-2.74 (m, 2H), 2.27 (dd, J=10.2, 5.3 Hz, 1H), 1.56 (s, 9H); MS (ESI, m/z): $[(M+1)]^+$=386.25.

The following intermediate in Table 26 below was prepared according to the above procedure to prepare Intermediate G-2-13.

TABLE 26

Characterization data for intermediate prepared according to procedure above.

| Intermediate | Structure | Chemical Name | MS: $[(M + 1)]^+$ | $^1$H-NMR |
|---|---|---|---|---|
| G-2-14 | 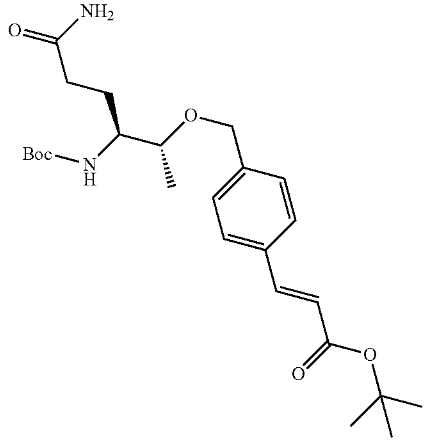 [SMILES: C[C@@H](OCc1ccc(/C=C/C(=O)OC(C)(C)C)cc1)[C@H](CCC(N)=O)NC(=O)OC(C)(C)C] | (2E)-3-[4-([[(2R,3S)-3-[(tert-butoxycarbonyl)amino]-5-carbamoyl pentan-2-yl]oxy]methyl)phenyl]prop-2-enoate | 463.4 | (400 MHz, $CDCl_3$) δ 7.60 (d, J = 16.0 Hz, 1H), 7.51 (d, J = 8.1 Hz, 2H), 7.34 (d, J = 8.0 Hz, 2H), 6.38 (d, J = 15.9 Hz, 2H), 5.42 (s, 1H), 4.87 (d, J = 9.6 Hz, 1H), 4.62 (d, J = 12.1 Hz, 1H), 4.45 (d, J = 12.1 Hz, 1H), 3.77-3.61 (m, 2H), 2.34-2.27 (m, 2H), 2.00 (d, J = 7.8 Hz, 1H), 1.78-1.66 (m, 1H), 1.51 (s, 9H), 1.45 (s, 9H), 1.23 (d, J = 6.4 Hz, 3H). |
| G-2-15 | 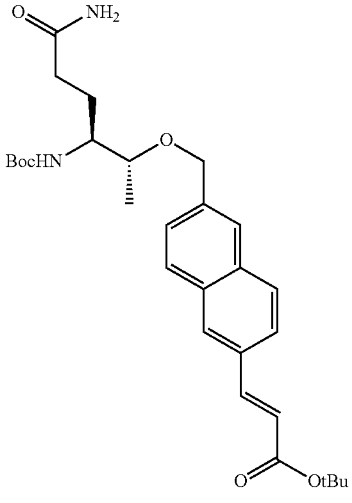 [SMILES: C[C@@H](OCc1ccc2cc(/C=C/C(=O)OC(C)(C)C)ccc2c1)[C@H](CCC(N)=O)NC(=O)OC(C)(C)C] | tert-butyl (2E)-3-[6-([[(2R,3S)-3-[(tert-butoxycarbonyl)amino]-5-carbamoyl pentan-2-yl]oxy]methyl)naphthalen-2-yl]prop-2-enoate | 513.3 | (400 MHz, $CD_3OD$) δ 8.01 (s, 1H), 7.93-7.72 (m, 2H), 7.56 (d, J = 8.3 Hz, 1H), 7.46 (dd, J = 5.0, 1.9 Hz, 2H), 7.29 (dd, J = 16.0, 1.3 Hz, 1H), 6.56 (d, J = 15.9 Hz, 1H), 4.77 (d, J = 12.0 Hz, 1H), 4.69 (d, J = 12.1 Hz, 1H), 3.68-3.53 (m, 2H), 2.35-2.19 (m, 2H), 2.11-1.96 (m, 1H), 1.72-1.63 (m, 1H), 1.57 (s, 9H), 1.42 (s, 9H), 1.23 (d, J = 6.1 Hz, 3H). |

TABLE 26-continued

| Characterization data for intermediate prepared according to procedure above. | | | | |
|---|---|---|---|---|
| Inter-mediate | Structure | Chemical Name | MS: $[(M + 1)]^+$ | $^1$H-NMR |
| G-2-43 | 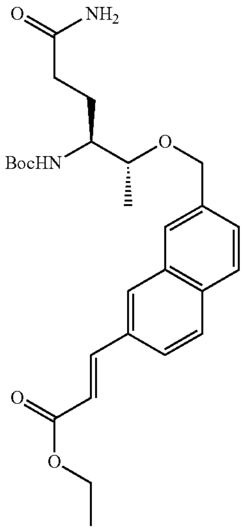 [SMILES: CCOC(=O)/C=C/c1ccc2ccc(CO[C@H](C)[C@H](CCC(N)=O)NC(=O)OC(C)(C)C)cc2c1] | ethyl (2E)-3-[7-([[(2R,3S)-3-[(tert-butoxycarbonyl)amino]-5-carbamoyl pentan-2-yl]oxy]methyl) naphthalen-2-yl]prop-2-enoate | 485.25 | (400 MHz, DMSO-$d_6$) δ 8.18 (s, 1H), 7.95-7.86 (m, 4H), 7.80 (d, J = 16.0 Hz, 1H), 7.54 (dd, J = 8.4, 1.6 Hz, 1H), 7.25 (s, 1H), 6.80-6.65 (m, 3H), 4.70-4.61 (m, 2H), 4.22 (q, J = 7.1 Hz, 2H), 4.04-4.02 (m, 1H), 3.52-3.47 (m, 2H), 2.12-2.08 (m, 2H), 1.88-1.80 (m, 1H), 1.59-1.45 (m, 1H), 1.37 (s, 9H), 1.30-1.26 (m, 2H), 1.11 (d, J = 5.9 Hz, 3H) |
| G-2-44 | 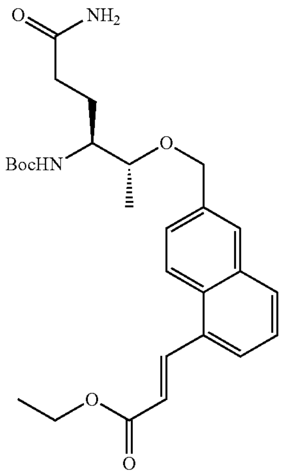 [SMILES: CCOC(=O)/C=C/c1cccc2cc(CO[C@H](C)[C@H](CCC(N)=O)NC(=O)OC(C)(C)C)ccc12] | ethyl (2E)-3-[6-([[2R,3S)-3-[(tert-butoxycarbonyl)amino]-5-carbamoyl pentan-2-yl]oxy]methyl) naphthalen-1-yl]prop-2-enoate | 485.15 | (400 MHz, DMSO-$d_6$) δ 8.43 (d, J = 15.8 Hz, 1H), 8.17 (d, J = 8.8 Hz, 1H), 8.02-7.91 (m, 3H), 7.63-7.52 (m, 2H), 7.24 (s, 1H), 6.69 (dd, J = 8.4 Hz, 3H), 4.74-4.62 (m, 2H), 4.26-4.23 (m, 2H), 3.49-3.45 (m, 2H), 2.08-2.04 (m, 2H), 1.90-1.78 (m, 1H), 1.53-1.49 (m, 1H), 1.36 (s, 9H), 1.30 (t, J = 7.1 Hz, 3H), 1.12 (t, J = 5.5 Hz, 3H) |
| G-2-45 | 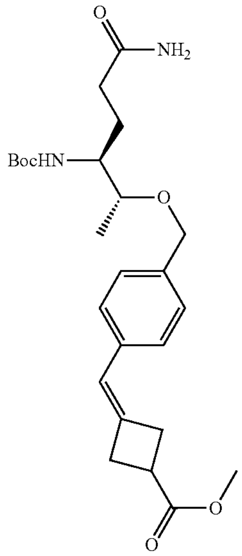 [SMILES: COC(=O)C1CC(=Cc2ccc(CO[C@H](C)[C@H](CCC(N)=O)NC(=O)OC(C)(C)C)cc2)C1] | methyl 3-[[4-([[2R,3S)-3-[(tert-butoxycarbonyl)amino]-5-cabamoyl pentan-2-yl]oxy]methyl) phenyl] methylidene] cyclobutane-1-carboxylate | 461.25 | (400 MHz, $CDCl_3$) δ 7.51-7.47 (m, 1H), 7.38-7.32 (m, 1H), 7.24-7.15 (m, 2H), 5.41 (s, 1H), 4.86 (dd, J = 18.0, 9.3 Hz, 1H), 4.56 (d, J = 11.8 Hz, 1H), 4.42-4.37 (m, 1H), 3.75 (s, 3H), 3.72-3.59 (m, 2H), 3.42-2.93 (m, 2H), 2.29 (td, J = 8.3, 7.6, 3.3 Hz, 2H), 2.05-1.60 (m, 4H), 1.45 (s, 9H), 1.23-1.18 (m, 3H) |

TABLE 26-continued

Characterization data for intermediate prepared according to procedure above.

| Inter-mediate | Structure | Chemical Name | MS: $[(M + 1)]^+$ | $^1$H-NMR |
|---|---|---|---|---|
| G-2-46 | 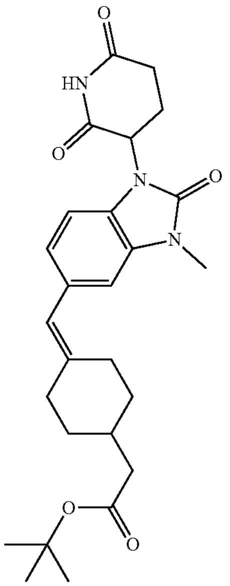 [SMILES: Cn1c(=O)n(C2CCC(=O)NC2=O)c2ccc(C=C3CCC(CC(=O)OC(C)(C)C)CC3)cc21] | tert-butyl 2-(4-((1-(2,6-dioxopiperidin-3-yl)-3-methyl-2-oxo-2,3-dihydro-1H-benzo[d]imidazol-5-yl)methylene)cyclohexyl)acetate | 468.25 | (300 MHz, $CDCl_3$) δ 8.26 (s, 1H), 6.96-6.88 (m, 1H), 6.86 (s, 1H), 6.76 (d, J = 8.1 Hz, 1H), 6.30 (s, 1H), 5.26-5.23 (m, 1H), 3.44 (s, 3H), 3.02-2.66 (m, 4H), 2.45-2.19 (m, 3H), 2.17 J = 6.9 Hz, 2H), 2.05-1.78 (m, 2H), 1.62-1.60 (m, 1H), 1.48 (s, 11H), 1.25-1.02 (m, 1H) |
| G-2-94 | 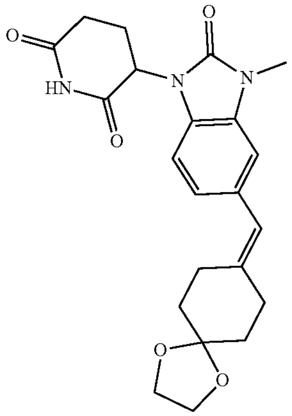 [SMILES: Cn1c(=O)n(C2CCC(=O)NC2=O)c2ccc(C=C3CCC4(CC3)OCCO4)cc21] | 3-(5-[1,4-dioxaspiro[4.5]decan-8-ylidenemethyl]-3-methyl-2-oxo-1,3-benzodiazol-1-yl)piperidine-2,6-dione | 412.20 | (400 MHz, DMSO-$d_6$) δ 11.10 (s, 1H), 7.07 (d, J = 8.1 Hz, 1H), 7.02 (d, J = 1.4 Hz, 1H), 6.91-6.88 (m, 1H), 6.37-6.35 (m, 1H), 5.38-5.35 (m, 1H), 3.93-3.84 (m, 4H), 3.37-3.35 (m, 1H), 3.31 (d, J = 16.7 Hz, 1H), 2.96-2.94 (m, 1H), 2.93-2.86 (m, 1H), 2.80-2.78 (m, 1H), 2.74-2.59 (m, 2H), 2.48-2.46 (m, 1H), 2.38-2.36 (m, 1H), 2.05-1.99 (m, 1H), 1.98-1.96 (m, 1H), 1.72-1.69 (m, 2H), 1.63-1.60 (m, 2H) |

Methyl (5E)-6-1[4-([[(2R,3S)-3- [(tert-butoxycarbonyl)amino]-5-carbamoylpentan-2-yl]oxy]methyl) phenyl]hex-5-enoate (Intermediate G-2-47)

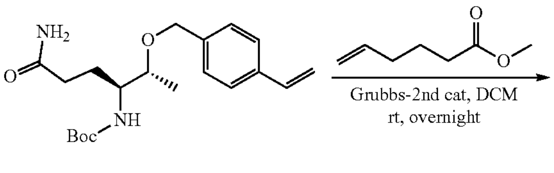

-continued

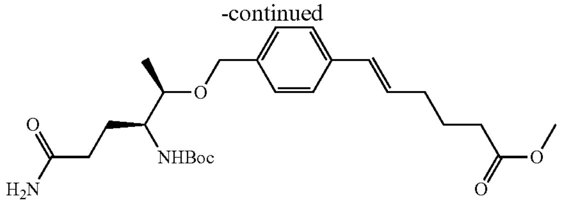

G-2-47

To a stirred solution of tert-butyl N-[(3S,4R)-1-carbamoyl-4-[(4-ethenylphenyl)methoxy]pentan-3-yl]carbamate (480 mg, 1.33 mmol) and methyl hex-5-enoate (509 mg, 3.97 mmol) in DCM (5.00 mL) was added Grubbs 2nd (112 mg, 0.13 mmol) in portions at room temperature under nitrogen atmosphere. The resulting mixture was stirred for 16 h at room temperature under nitrogen atmosphere. The resulting mixture was concentrated under reduced pressure. The crude product was purified by reverse phase flash chromatography with the following conditions: Column: Spherical C1[8] Column, 20~40 um, 120 g; Mobile Phase A: water (plus 0.1% FA), Mobile Phase B: ACN; Flow rate: 60 mL/min; Gradient: 20% B to 40% B in 25 min, Detector: UV 220/254 nm. The fractions containing the desired product were collected at 35% B and concentrated under reduced pressure to afford the title compound as a white solid (390 mg, 64%): $^1$H NMR (400 MHz, $CDCl_3$) δ 7.33 (d, J=7.9 Hz, 2H), 7.30-7.24 (m, 2H), 6.41 (d, J=15.9 Hz, 1H), 6.23-6.19 (m, 1H), 5.41-5.38 (m, 2H), 4.87 (d, J=9.6 Hz, 1H), 4.60 (d, J=12.0 Hz, 1H), 4.39 (d, J=11.8 Hz, 1H), 3.69-3.60 (m, 1H), 2.39 (t, J=7.5 Hz, 2H), 2.34-2.25 (m, 4H), 2.11-1.94 (m, 2H), 1.88-1.80 (m, 2H), 1.75-1.67 (m, 4H), 1.45 (s, 9H), 1.21 (d, J=6.5 Hz, 3H); LC/MS (ESI, m/z): $[(M+Na)]^+$=485.20

The intermediates in Table 27 were prepared according to the above procedure to prepare Intermediate G-2-47.

Step 3. tert-butyl 2-[2-(2-[3-[1-(2,6-dioxopiperidin-3-yl)-3-methyl-2-oxo-2,3-dihydro-1H-1,3-benzodiazol-5-yl]propoxy]ethoxy)ethoxy]acetate. The titled compound was prepare according to the procedure of Step 4 of the procedure to prepare Intermediate B. $^1$H NMR (400 MHz, DMSO-d4) δ 11.09 (s, 1H), 7.08-6.97 (m, 2H), 6.90-6.85 (m, 1H), 5.34 (dd, J=12.7, 5.4 Hz, 1H), 3.99 (d, J=1.0 Hz, 3H), 3.51-3.44 (m, 4H), 3.39 (t, J=6.5 Hz, 2H), 3.33 (s, 4H), 3.01-2.84 (m, 1H), 2.78-2.57 (m, 4H), 2.08-1.95 (m, 1H), 1.80 (dq, J=14.2, 6.8 Hz, 2H), 1.41 (s, 9H), 1.35 (s, 2H); MS (ESI, m/z): $[(M+23)]^+$=542.3.

The following intermediates in Table 28 were prepared according to the procedure of Step 3 of the procedure to prepare Intermediate G.

TABLE 27

Characterization data for intermediates prepared according to above.

| Intermediate | Structure | Chemical Name | MS: $[(M + 1)]^+$ | $^1$H-NMR |
|---|---|---|---|---|
| G-2-48 | 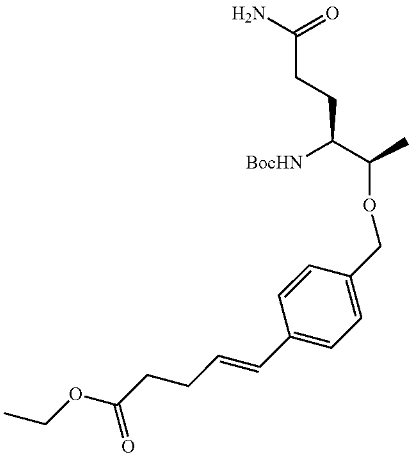 [SMILES: CCOC(=O)CC/C=C/c1ccc(CO[C@H](C)[C@H](CCC(N)=O)NC(=O)OC(C)(C)C)cc1] | ethyl (4E)-5-[4-([[(2R,3S)-3-[(tert-butoxycarbonyl)amino]-5-carbamoylpentan-2-yl]oxy]methyl)phenyl]pent-4-enoate | $[(M + Na)]^+$ = 485.20 | Used in the next step without further purification |
| G-2-95 | 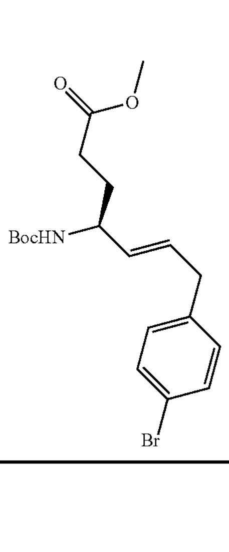 | methyl (4S,5E)-7-(4-bromophenyl)-4-[(tert-butoxycarbonyl)amino]hept-5-enoate | 412.10, 414.10 | (400 MHz, DMSO-$d_6$) δ 7.47 (d, J = 8.0 Hz, 2H), 7.15 (d, J = 8.0 Hz, 2H), 6.80 (s, 1H), 5.61 (dt, J = 14.2, 6.7 Hz, 1H), 5.40 (dd, J = 15.3, 6.7 Hz, 1H), 3.90 (s, 1H), 3.57 (s, 3H), 3.30 (d, J = 6.7 Hz, 2H), 2.27 (t, J = 7.7 Hz, 2H), 1.65 (dq, J = 13.1, 6.5 Hz, 2H), 1.37 (s, 9H) |

TABLE 28

| Intermediates prepare according to Step 3 above. | | | | |
|---|---|---|---|---|
| Inter-mediate | Structure | Chemical Name | MS: [(M + 1)]+ | $^1$H-NMR |
| G-3-2 | 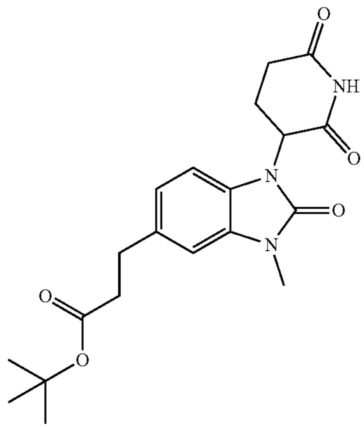 [SMILES: Cn1c(=O)n(C2CCC(=O)NC2=O)c2ccc(CCC(=O)OC(C)(C)C)cc21] | tert-butyl 3-[1-(2,6-dioxopiperidin-3-yl)-3-methyl-2-oxo-2,3-dihydro-1H-1,3-benzodiazol-5-yl]propanoate | 388.3 | (400 MHz, DMSO-$d_6$) δ 11.09 (s, 1H), 7.08 (d, J = 1.6 Hz, 1H), 7.01 (d, J = 8.0 Hz, 1H), 6.92-6.86 (m, 1H), 5.34 (dd, J = 12.8, 5.4 Hz, 1H), 3.34 (s, 1H), 2.95- 2.76 (m, 4H), 2.76-2.53 (m, 4H), 2.00 (ddd, J = 11.3, 6.0, 3.9 Hz, 1H), 1.39 (s, 9H). |
| G-3-3 | 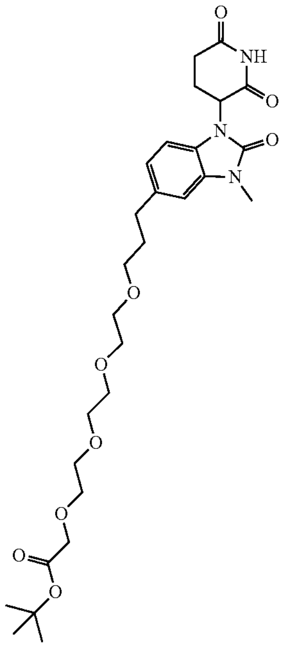 [SMILES: Cn1c(=O)n(C2CCC(=O)NC2=O)c2ccc(CCCOCCOCCOCCOCC(=O)OC(C)(C)C)cc21] | tert-butyl 15-[1-(2,6-dioxopiperidin-3-yl)-3-methyl-2-oxo-2,3-dihydro-1H-1,3-benzodiazol-5-y]-3,6,9,12-tetraoxapentadecanoate | [(M + 18)]+ = 581.4 | (400 MHz, DMSO-$d_6$) δ 11.09 (s, 1H), 7.08-6.97 (m, 2H), 6.88 (t, J = 4.0 Hz, 1H), 5.34 (dd, J = 12.5, 5.4 Hz, 1H), 4.00-3.97 (m, 8H), 3.49-3.46 (m, 7H), 2.99-2.84 (m, 1H), 2.78-2.58 (m, 4H), 2.18 (d, J = 5.6 Hz, 1H), 2.06-1.95 (m, 1H), 1.81 (h, J = 6.9 Hz, 2H), 1.43 (s, 9H), 1.36 (s, 3H). |

TABLE 28-continued

| Intermediates prepare according to Step 3 above. | | | | |
|---|---|---|---|---|
| Inter-mediate | Structure | Chemical Name | MS: $[(M + 1)]^+$ | $^1$H-NMR |
| G-3-4 | 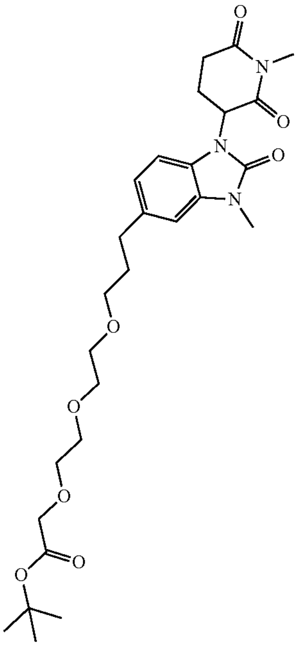 [SMILES: CN1C(=O)CCC(n2c(=O)n(C)c3cc(CCCOCCOCCOCC(=O)OC(C)(C)C)ccc32)C1=O] | tert-butyl 2-[2-(2-[3-[3-methyl-1-(1-methyl-2,6-dioxopiperidin-3-yl)-2-oxo-1,3-benzodiazol-5-yl]propoxy]ethoxy)ethoxy]acetate | 534.4 | (400 MHz, DMSO-$d_6$) δ 6.98 (dd, J = 14.5, 6.0 Hz, 2H), 6.82 (s, 1H), 5.36 (d, J = 11.4 Hz, 1H), 4.02-3.90 (m, 2H), 3.54-3.52 (m, 4H), 3.50-3.38 (m, 2H), 3.37-3.24 (m, 5H), 2.99 (s, 3H), 2.91 (d, J = 15.3 Hz, 1H), 2.77-2.65 (m, 1H), 2.60 (s, 3H), 2.45 (s, 1H), 1.96 (s, 1H), 1.77 (s, 2H), 1.41 (s, 1H), 1.39-1.27 (m, 9H). |
| G-3-5 | 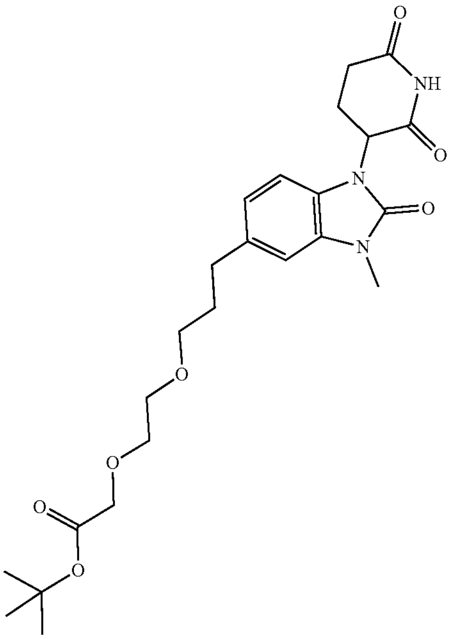 [SMILES: Cn1c(=O)n(C2CCC(=O)NC2=O)c2ccc(CCCOCCOCC(=O)OC(C)(C)C)cc21] | tert-butyl 2-(2-[3-[1-(2,6-dioxopiperidin-3-yl)-3-methyl-2-oxo-2,3-dihydro-1H-1,3-benzodiazol-5-yl]propoxy]ethoxy)acetate | $[(M + 23)]^+$ = 498.2 | (400 MHz, DMSO-$d_6$) δ 11.08 (d, J = 8.4 Hz, 1H), 7.11-6.93 (m, 2H), 6.91-6.82 (m, 1H), 5.34 (dd, J = 12.7, 5.5 Hz, 1H), 4.00 (d, J = 8.9 Hz, 2H), 3.59 (dd, J = 5.9, 3.6 Hz, 2H), 3.53-3.45 (m, 2H), 3.39 (s, 5H), 3.00-2.81 (m, 1H), 2.67 (dd, J = 19.5, 11.1 Hz, 3H), 2.00 (d, J = 12.2 Hz, 1H), 1.88-1.72 (m, 2H), 1.45-1.35 (m, 9H). |

TABLE 28-continued

| Intermediates prepare according to Step 3 above. | | | | |
|---|---|---|---|---|
| Inter-mediate | Structure | Chemical Name | MS: $[(M + 1)]^+$ | $^1$H-NMR |
| G-3-6 | 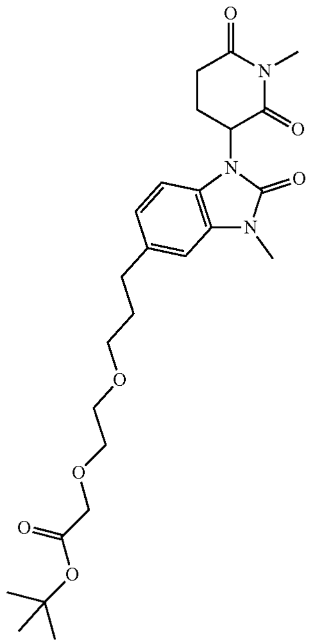 [SMILES: CN1C(=O)CCC(n2c(=O)n(C)c3cc(CCCOCCOCC(=O)OC(C)(C)C)ccc32)C1=O] | tert-butyl 2-[2-(3-[3-methyl-1-(1-methyl-2,6-dioxopiperidin-3-yl)-2-oxo-1,3-benzodiazol-5-yl]propoxy]ethoxy) acetate | $[(M + 23)]^+$ = 512.3 | (400 MHz, DMSO-$d_6$) δ 6.97 (s, 2H), 6.81 (s, 1H), 5.41 (m, 1H), 4.01 (s, 1H), 3.95 (s, 1H), 3.60 (dd, J = 5.9, 3.6 Hz, 1H), 3.54 (s, 2H), 3.55-3.49 (m, 1H), 3.52-3.37 (m, 3H), 3.04 (s, 1H), 2.98 (s, 3H), 2.67 (q, J = 7.6 Hz, 1H), 2.60 (s, 1H), 2.45 (s, 1H), 1.96 (s, 1H), 1.77 (s, 2H), 1.70 (s, 1H), 1.43 (s, 2H), 1.37 (s, 9H). |
| G-3-7 | 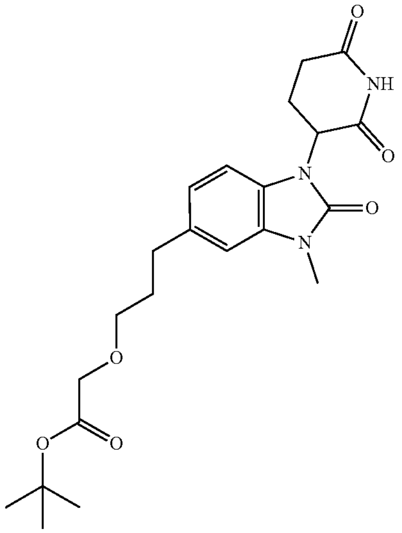 [SMILES: Cn1c(=O)n(C2CCC(=O)NC2=O)c2ccc(CCCOCC(=O)OC(C)(C)C)cc21] | tert-butyl 2-[3-[1-(2,6-dioxpiperidin-3-yl)-3-methyl-2-oxo-2,3-dihydro-1H-1,3-benzodiazol-5-yl]propoxy]acetate | $[(M + 18)]^+$ = 449.3 | (400 MHz, $CDCl_3$) δ 8.40 (s, 1H), 6.97-6.87 (m, 2H), 6.73 (d, J = 7.9 Hz, 1H), 5.24 (dd, J = 12.6, 5.3 Hz, 1H), 3.98 (s, 2H), 3.56 (t, J = 6.3 Hz, 2H), 3.44 (s, 3H), 2.99-2.67 (m, 5H), 2.27-2.19 (m, 1H), 2.00-1.91 (m, 2H), 1.48 (s, 9H). |

TABLE 28-continued

| Intermediates prepare according to Step 3 above. | | | | |
|---|---|---|---|---|
| Inter-mediate | Structure | Chemical Name | MS: $[(M + 1)]^+$ | $^1$H-NMR |
| G-3-8 | 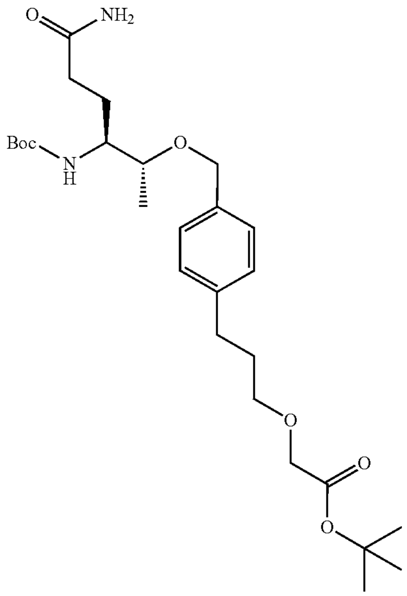 [SMILES: C[C@@H](OCc1ccc(CCCOCC(=O)OC(C)(C)C)cc1)[C@H](CCC(N)=O)NC(=O)OC(C)(C)C] | tert-butyl 2-[3-[4-([[(2R,3S)-3-[(tert-butoxycarbonyl) amino]-5-carbamoylpentan-2-yl]oxy]methyl)phenyl] propoxy]acetate | 509.4 | (400 MHz, DMSO-$d_6$) δ 7.24-7.19 (m, 3H), 7.16 (d, J = 7.8 Hz, 2H), 6.65 (d, J = 13.6 Hz, 1H), 6.60 (d, J = 9.0 Hz, 1H), 4.57-4.37 (m, 2H), 3.95 (s, 2H), 3.50-3.35 (m, 4H), 3.31 (s, 1H), 2.61 (q, J = 7.3 Hz, 2H), 2.03 (tdd, J = 14.8, 9.3, 5.4 Hz, 2H), 1.85-1.72 (m, 3H), 1.42 (s, 9H), 1.38 (s, 9H), 1.06 (d, J = 6.0 Hz, 3H). |
| G-3-9 | 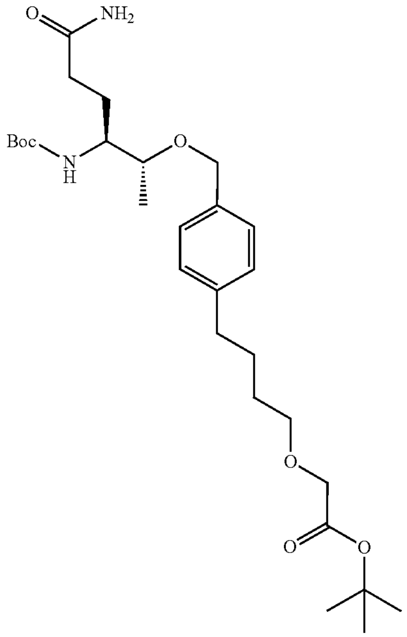 [SMILES: C[C@@H](OCc1ccc(CCCCOCC(=O)OC(C)(C)C)cc1)[C@H](CCC(N)=O)NC(=O)OC(C)(C)C] | tert-butyl 2-([4-[4-([[(2R,3S)-3-[(tert-butoxycarbonyl) amino]-5-carbamoylpentan-2-yl]oxy]methyl)phenyl] but-3-yn-1-yl]oxy)acetate | 523.4 | (400 MHz, DMSO-$d_6$) δ 7.38-7.01 (m, 5H), 6.63-6.60 (m, 2H), 4.50-4.35 (m, 2H), 3.96-3.86 (m, 2H), 3.44-3.39 (m, 4H), 2.57 (q, J = 7.3 Hz, 2H), 2.26-1.95 (m, 2H), 1.90-1.69 (m, 2H), 1.60 (q, J = 7.2 Hz, 2H), 1.51 (t, J = 7.3 Hz, 2H), 1.44-1.31 (m, 18H), 1.04 (d, J = 6.0 Hz, 3H). |

TABLE 28-continued

| Intermediates prepare according to Step 3 above. | | | | |
|---|---|---|---|---|
| Intermediate | Structure | Chemical Name | MS: $[(M+1)]^+$ | $^1$H-NMR |
| G-3-10 | 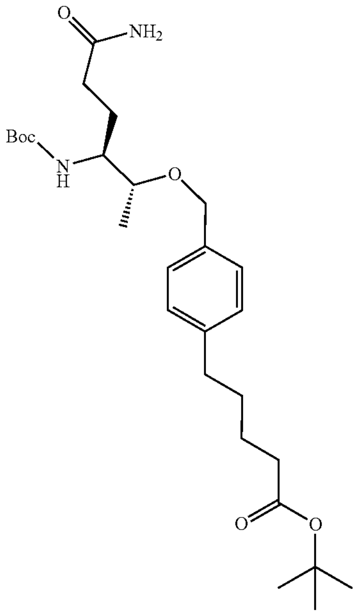 [SMILES: C[C@@H](OCc1ccc(CCCCC(=O)OC(C)(C)C)cc1)[C@H](CCC(N)=O)NC(=O)OC(C)(C)C] | tert-butyl 5-[4-([[(2R,3S)-3-[(tert-butoxycarbonyl) amino]-5-carbamoylpentan-2-yl]oxy]methyl)phenyl] pent-4-ynoate | 493.4 | (400 MHz, DMSO-$d_6$) δ 7.23 (d, J = 8.0 Hz, 2H), 7.20 (s, 1H), 7.13 (d, J = 8.0 Hz, 2H), 6.67 (s, 1H), 6.59 (d, J = 9.1 Hz, 1H), 4.49-4.37 (m, 2H), 3.43-3.36 (m, 1H), 3.31 (s, 3H), 2.56 (t, J = 7.2 Hz, 2H), 2.20 (t, J = 7.0 Hz, 2H), 2.04 (ddd, J = 15.2, 9.6, 5.6 Hz, 1H), 1.60-1.45 (m, 6H), 1.42-1.38 (m, 17H), 1.06 (d, J = 6.0 Hz, 3H). |
| G-3-11 | 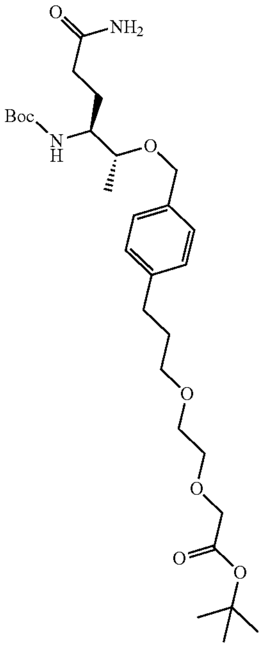 [SMILES: C[C@@H](OCc1ccc(CCCOCCOCC(=O)OC(C)(C)C)cc1)[C@H](CCC(N)=O)NC(=O)OC(C)(C)C] | tert-butyl 2-(2-[3-[4-([[(2R,3S)-3-[(tert-butoxycarbonyl) amino]-5-carbamoylpentan-2-yl]oxy]methyl)phenyl] propoxy]ethoxy) acetate | 553.4 | (400 MHz, DMSO-$d_6$) δ 7.23 (d, J = 7.9 2H), 7.15 (d, J = 7.7 Hz, 2H), 6.73-6.56 (m, 2H), 4.50-4.38 (m, 2H), 4.00 (s, 2H), 3.64-3.55 (m, 3H), 3.50 (dd, J = 5.9, 3.5 Hz, 2H), 3.40-3.38 (m, 3H), 2.60 (t, J = 7.7 Hz, 2H), 2.12-1.97 (m, 2H), 1.83-1.72 (m, 4H), 1.43 (s, 9H), 1.37 (d, J = 9.5 Hz, 9H), 1.06 (d, J = 6.0 Hz, 3H). |

TABLE 28-continued

| Intermediates prepare according to Step 3 above. | | | | |
|---|---|---|---|---|
| Intermediate | Structure | Chemical Name | MS: $[(M+1)]^+$ | $^1$H-NMR |
| G-3-12 | 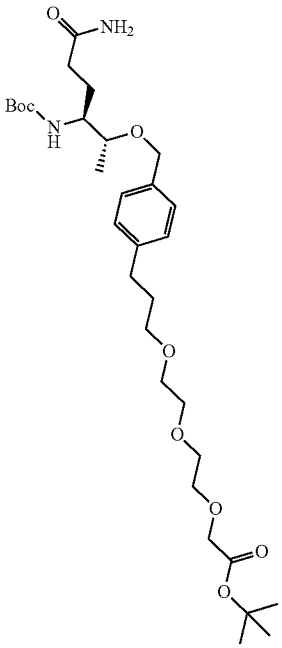 [SMILES: C[C@@H](OCc1ccc(CCCOCCOCCOCC(=O)OC(C)(C)C)cc1)[C@H](CCC(N)=O)NC(=O)OC(C)(C)C] | tert-butyl 2-[2-(2-[3-[4-([[(2R,3S)-3-[(tert-butoxycarbonyl) amino]-5-carbamoylpentan-2-yl]oxy]methyl)phenyl] yl]propoxy]ethoxy) ethoxy]acetate | 597.5 | (400 MHz, DMSO-$d_6$) δ 7.23 (d, J = 7.9 Hz, 2H), 7.15 (d, J = 7.8 Hz, 2H), 6.71-6.57 (m, 2H), 4.49-4.39 (m, 2H), 3.99 (s, 2H), 3.63-3.57 (m, 4H), 3.56-3.52 (m, 4H), 3.48 (dd, J = 5.9, 3.3 Hz, 2H), 3.38 (t, J = 6.4 Hz, 2H), 2.60 (t, J = 7.7 Hz, 2H), 2.15-1.96 (m, 2H), 1.79-1.76 (, 4H), 1.42 (s, 9H), 1.38 (d, J = 9.5 Hz, Hz, 9H), 1.06 (d, J = 6.0 Hz, 3H). |
| G-3-13 | 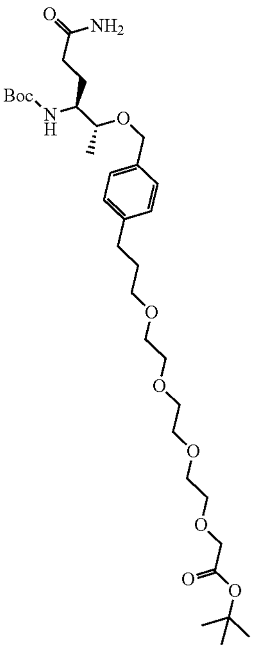 [SMILES: C[C@@H](OCc1ccc(CCCOCCOCCOCCOCC(=O)OC(C)(C)C)cc1)[C@H](CCC(N)=O)NC(=O)OC(C)(C)C] | tert-butyl 15-[4-([[(2R,3S)-3-[(tert-butoxycarbonyl) amino]-5-carbamoylpentan-2-yl]oxy]methyl)phenyl]-3,6,9,12-tetraoxapentadecanoate | 641.5 | (400 MHz, DMSO-$d_6$) δ 7.23 (d, J = 7.9 Hz, 2H), 7.15 (d, J = 7.8 Hz, 2H), 6.65-6.62 (m, 2H), 4.51-4.38 (m, 2H), 3.98 (d, J = 2.8 Hz, 2H), 3.63-3.45 (m, 7H), 3.43-3.29 (m, 4H), 2.60 (t, J = 7.6 Hz, 2H), 1.82-1.74 (m, 3H), 1.45-1.34 (m, 24H), 1.06 (d, J = 5.9 Hz, 3H). |

TABLE 28-continued

| Intermediates prepare according to Step 3 above. | | | | |
|---|---|---|---|---|
| Inter-mediate | Structure | Chemical Name | MS: $[(M + 1)]^+$ | $^1$H-NMR |
| G-3-14 | 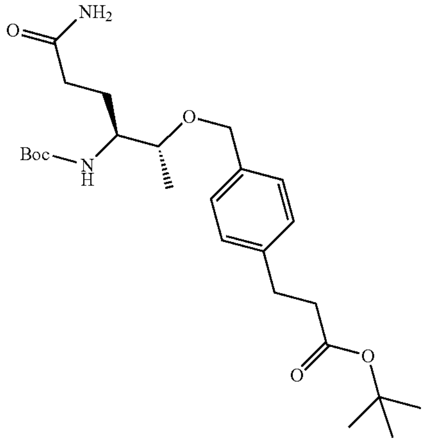 [SMILES: C[C@@H](OCc1ccc(CCC(=O)OC(C)(C)C)cc1)[C@H](CCC(N)=O)NC(=O)OC(C)(C)C] | tert-butyl 3-[4-([[(2R,3S)-3-[(tert-butoxycarbonyl) amino]-5-carbamoylpentan-2-yl]oxy]methyl)phenyl] propanoate | 465.5 | (400 MHz, $CDCl_3$) δ 7.25 (d, J = 8.1 Hz, 2H), 7.19 (d, J = 7.9 Hz, 2H), 6.52 (s, 1H), 5.60-5.45 (m, 1H), 4.90 (d, J = 9.7 Hz, 1H), 4.58 (d, J = 11.5 Hz, 1H), 4.39 (d, J = 11.5 Hz, 1H), 3.73-3.55 (m, 2H), 2.92 (t, J = 7.8 Hz, 2H), 2.54 (dd, J = 8.5, 7.2 Hz, 2H), 2.28 (q, J = 6.0, 5.0 Hz, 2H), 2.05-1.94 (m, 1H), 1.76-1.64 (m, 1H), 1.46-1.45 (m, 18H), 1.20 (d, J = 6.3 Hz, 3H). |
| G-3-15 | 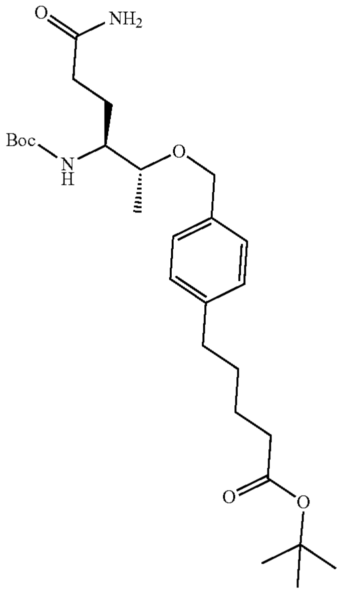 [SMILES: C[C@@H](OCc1ccc(CCCCC(=O)OC(C)(C)C)cc1)[C@H](CCC(N)=O)NC(=O)OC(C)(C)C] | tert-butyl 5-[4-([[(2R,3S)-3-[(tert-butoxycarbonyl) amino]-5-carbamoylpentan-2-yl]oxy]methyl)phenyl] pentanoate | 943.4 | (400 MHz, DMSO-$d_6$) δ 7.27-7.17 (m, 3H), 7.13 (d, J = 8.0 Hz, 2H), 6.67 (s, 1H), 6.59 (d, J = 9.1 Hz, 1H), 4.52-4.33 (m, 2H), 3.51-3.35 (m, 2H), 2.56 (t, J = 7.2 Hz, 2H), 2.20 (t, J = 7.0 Hz, 2H), 2.13-1.95 (m, 2H), 1.85-1.72 (m, 1H), 1.61-1.45 (m, 5H), 1.40-1.39 (m, 18H), 1.06 (d, J = 6.0 Hz, 3H). |

TABLE 28-continued

| Intermediates prepare according to Step 3 above. | | | | |
|---|---|---|---|---|
| Intermediate | Structure | Chemical Name | MS: $[(M + 1)]^+$ | $^1$H-NMR |
| G-3-16 | 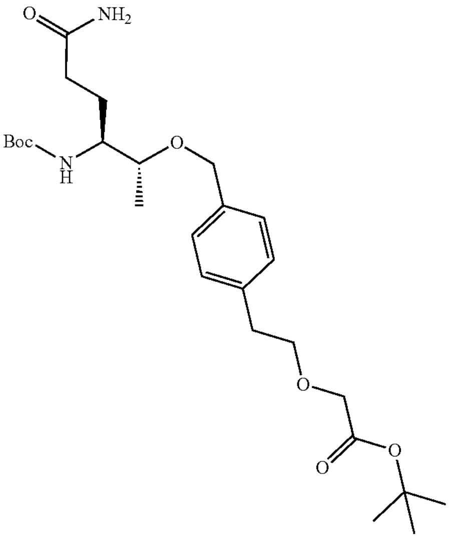 [SMILES: C[C@@H](OCc1ccc(CCOCC(=O)OC(C)(C)C)cc1)[C@H](CCC(N)=O)NC(=O)OC(C)(C)C] | tert-butyl 2-[2-[4-([[(2R,3S)-3-[(tert-butoxycarbonyl)amino]-5-carbamoylpentan-2-yl]oxy]methyl)phenyl]ethoxy]acetate | 495.4 | (400 MHz, DMSO-$d_6$) δ 7.24-7.20 (m, 5H), 6.68 (s, 1H), 6.61 (d, J = 9.0 Hz, 1H), 4.49-4.38 (m, 2H), 3.96 (s, 2H), 3.65 (t, J = 6.9 Hz, 2H), 3.43 (s, 2H), 3.42-3.36 (m, 1H), 2.81 (t, J = 6.9 Hz, 2H), 2.10-1.98 (m, 1H), 1.79 (s, 1H), 1.43-1.38 (m, 18H), 1.06 (d, J = 6.0 Hz, 3H). |
| G-3-17 | 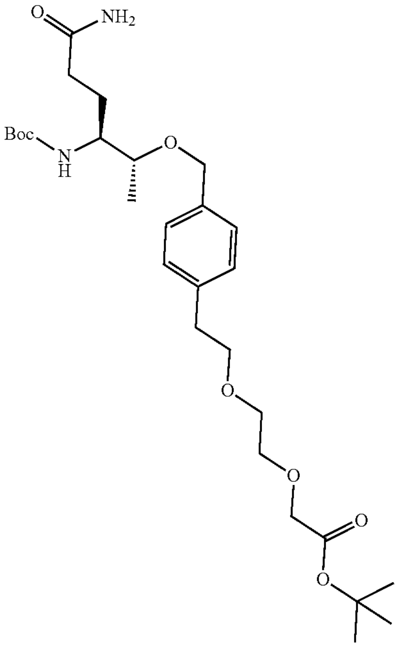 [SMILES: C[C@@H](OCc1ccc(CCOCCOCC(=O)OC(C)(C)C)cc1)[C@H](CCC(N)=O)NC(=O)OC(C)(C)C] | tert-butyl 2-(2-[2-[4-([[(2R,3S)-3-[(tert-butoxycarbonyl)amino]-5-carbamoylpentan-2-yl]oxy]methyl)phenyl]ethoxy]ethoxy)acetate | 539.4 | (400 MHz, DMSO-$d_6$) δ 7.25-7.17 (m, 5H), 6.77-6.53 (m, 2H), 4.50-4.36 (m, 2H), 3.97 (s, 2H), 3.63-3.50 (m, 6H), 3.49-3.36 (m, 2H), 2.79 (t, J = 7.0 Hz, 2H), 2.13-1.98 (m, 2H), 1.79 (dt, J = 6.7, 3.7 Hz, 1H), 1.45-1.36 (m, 18H), 1.06 (d, J = 6.0 Hz, 3H). |

TABLE 28-continued

| Intermediates prepare according to Step 3 above. | | | | |
|---|---|---|---|---|
| Intermediate | Structure | Chemical Name | MS: $[(M + 1)]^+$ | $^1$H-NMR |
| G-3-18 | 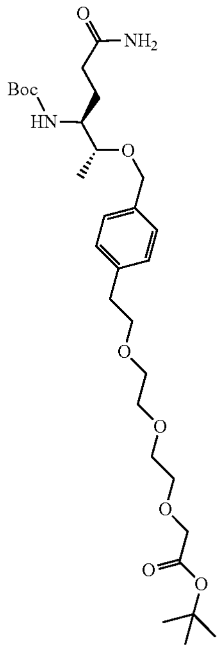 [SMILES: C[C@@H](OCc1ccc(CCOCCOCCOCC(=O)OC(C)(C)C)cc1)[C@H](CCC(N)=O)NC(=O)OC(C)(C)C] | tert-butyl 2-[2-(2-[2-[4-([[(2R,3S)-3-[(tert-butoxycarbonyl) amino]-5-carbamoylpentan-2-yl]oxy]methyl)phenyl] ethoxy]ethoxy)ethoxy] acetate | 583.3 | (400 MHz, DMSO-$d_6$) δ 7.26-7.19 (m 3H), 7.19-7.15 (m, 1H), 6.67 (s, 1H), 6.60 (t, J = 8.1 Hz, 1H), 4.51-4.35 (m, 2H), 3.98 (d, J = 6.0 Hz, 2H), 3.62-3.53 (m, 4H), 5.53-3.48 (m, 5H), 2.78 (q, J = 6.6 Hz, 2H), 2.05 (ddp, J = 14.6, 10.5, 4.9 Hz, 2H), 1.78 (s, 1H), 1.63-1.42 (m, 1H), 1.45-1.38 (m, 18H), 1.06-1.05 (m, 3H). |
| G-3-19 | 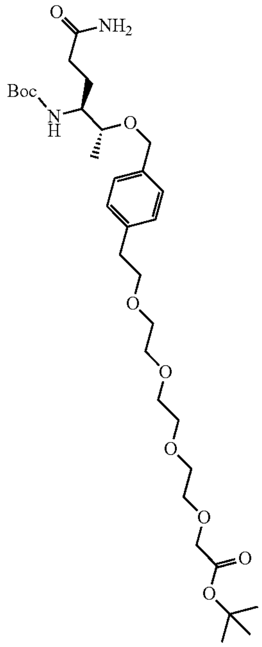 [SMILES: C[C@@H](OCc1ccc(CCOCCOCCOCCOCC(=O)OC(C)(C)C)cc1)[C@H](CCC(N)=O)NC(=O)OC(C)(C)C] | tert-butyl 14-[4-([[(2R,3S)-3-[(tert-butoxycarbonyl) amino]-5-carbamoylpentan-2-yl]oxy]methyl)phenyl]-3,6,9,12-tetraoxapentadecanoate | 627.5 | (400 MHz, DMSO-$d_6$) δ 7.23 (d, J = 8.0 Hz, 2H), 7.18 (d, J = 8.1 Hz, 2H), 6.71-6.62 (m, 1H), 6.59 (d, J = 9.1 Hz, 1H), 4.52-4.37 (m, 2H), 3.98 (d, J = 2.0 Hz, 2H), 3.63-3.55 (m, 4H), 3.55-3.47 (m, 10H), 3.45-3.35 (m, 2H), 2.78 (t, J = 7.0 Hz, 2H), 2.17-1.94 (m, 3H), 1.86-1.73 (m, 1H), 1.42-1.38 (m, 18H), 1.05 (d, J = 6.0 Hz, 3H). |

TABLE 28-continued

| Intermediates prepare according to Step 3 above. | | | | |
|---|---|---|---|---|
| Inter-mediate | Structure | Chemical Name | MS: $[(M + 1)]^+$ | $^1$H-NMR |
| G-3-20 | 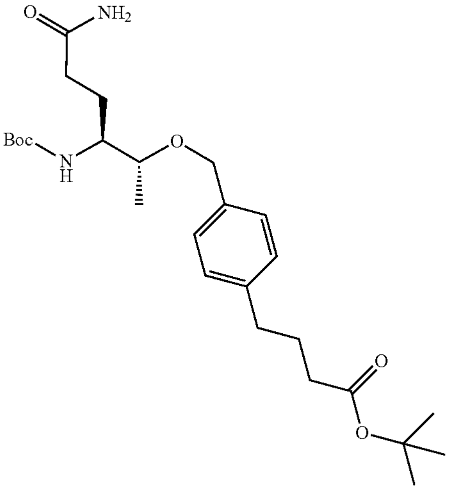 [SMILES: C[C@@H](OCc1ccc(CCCC(=O)OC(C)(C)C)cc1)[C@H](CCC(N)=O)NC(=O)OC(C)(C)C] | tert-butyl 4-[4-([[(2R,3S)-3-[(tert-butoxycarbonyl) amino]-5-carbamoylpentan-2-yl]oxy]methyl)phenyl] butanoate | 479.3 | (400 MHz, $CDCl_3$) δ 7.26 (d, J = 7.9 Hz, 2H), 7.18 (d, J = 7.8 Hz, 2H), 6.72 (s, 1H), 5.62 (s, 1H), 4.92 (d, J = 9.5 Hz, 1H), 4.60 (d, J = 11.4 Hz, 1H), 4.39 (d, J = 11.4 Hz, 1H), 3.67 (s, 1H), 3.51 (s, 2H), 2.65 (t, J = 7.6 Hz, 2H), 2.30-2.25 (m, 4H), 1.92 (p, J = 7.6 Hz, 2H), 1.46 (d, J = 5.4 Hz, 18H), 1.39 (s, 1H), 1.22 (d, J = 6.2 Hz, 3H). |
| G-3-21 | 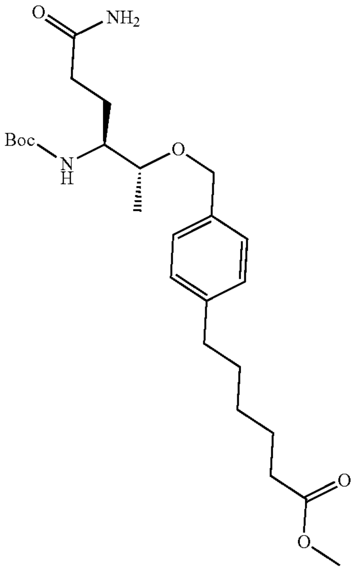 [SMILES: COC(=O)CCCCCc1ccc(CO[C@H](C)[C@H](CCC(N)=O)NC(=O)OC(C)(C)C)cc1] | methyl 6-[4-([[(2R,3S)-3-[(tert-butoxycarbonyl) amino]-5-carbamoylpentan-2-yl]oxy]methyl)phenyl] hexanoate | 465.4 | (400 MHz, $CDCl_3$) δ 7.24 (d, J = 7.7 Hz, 2H), 7.16 (d, J = 7.7 Hz, 2H), 6.45 (s, 1H), 5.43 (s, 1H), 4.91 (d, J = 9.7 Hz, 1H), 4.58 (d, J = 11.5 Hz, 1H), 4.38 (d, J = 11.4 Hz, 1H), 3.68 (s, 3H), 3.62 (q, J = 7.0, 6.1 Hz, 1H), 2.62 (t, J = 7.7 Hz, 2H), 2.33-2.29 (m 4H), 1.99 (d, J = 11.6 Hz, 1H), 1.69-1.65 (m, 5H), 1.45 (s, 9H), 1.38 (s, 3H), 1.21 (d, J = 6.2 Hz, 3H). |

TABLE 28-continued

Intermediates prepare according to Step 3 above.

| Inter-mediate | Structure | Chemical Name | MS: $[(M + 1)]^+$ | $^1$H-NMR |
|---|---|---|---|---|
| G-3-22 | 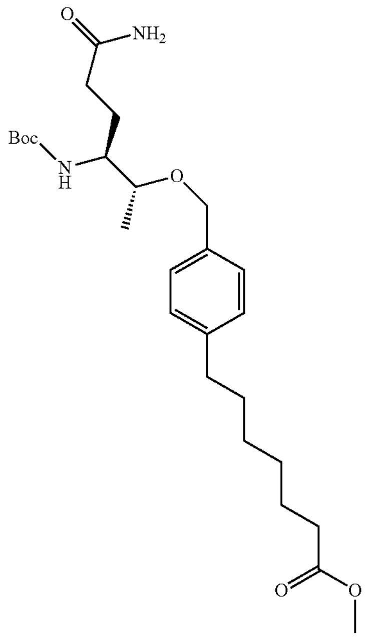 [SMILES: COC(=O)CCCCCCc1ccc(CO[C@H](C)[C@H](CCC(N)=O)NC(=O)OC(C)(C)C)cc1] | methyl 7-[4-([[(2R,3S)-3-[(tert-butoxycarbonyl) amino]-5-carbamoylpentan-2-yl]oxy]methyl)phenyl] heptanoate | $[(M + 23)]^+$ = 501.3 | (400 MHz, $CD_3OD$) δ 7.28 (d, J = 7.8 Hz, 2H), 7.16 (d, J = 7.8 Hz, 2H), 4.59-4.44 (m, 2H), 3.66 (s, 3H), 3.57 (dt, J = 7.6, 4.4 Hz, 1H), 3.53 (d, J = 6.0 Hz, 1H), 2.62 (t, J = 7.6 Hz, 2H), 2.39-2.21 (m, 4H), 2.06-1.92 (m, 1H), 1.65-1.59 (m, 5H), 1.56-1.41 (m, 9H), 1.38-1.34 (m, 4H), 1.18 (d, J = 6.1 Hz, 3H). |
| G-3-25 | 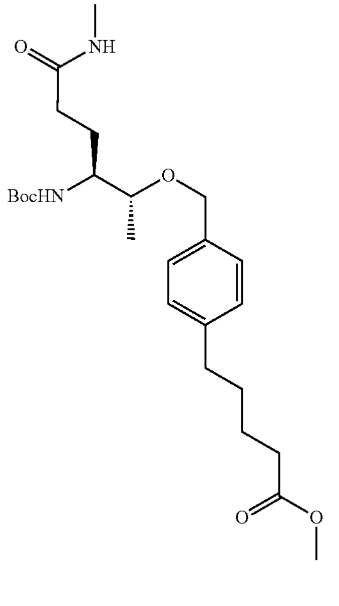 [SMILES: CNC(=O)CC[C@H](NC(=O)OC(C)(C)C)[C@@H](C)OCc1ccc(CCCCC(=O)OC)cc1] | Methyl 5-[4-([[(2R,3S)-3-[(tert-butoxycarbonyl) amino]-5-(methylcarbamoyl) pentan-2-yl]oxy]methyl)phenyl] pentanoate | 464.5 | (400 MHz, $CD_3OD$) δ 7.10-7.03 (m, 4H), 3.66 (s, 3H), 3.64 (t, J = 6.3 Hz, 1H), 3.36 (ddd, J = 7.4, 3.7, 2.6 Hz, 1H), 2.72 (s, 3H), 2.62-2.54 (m, 2H), 2.38-2.29 (m, 5H), 2.23 (ddd, J = 13.9, 9.1, 6.0 Hz, 1H), 2.01 (dddd, J = 13.8, 9.6, 6.6, 3.2 Hz, 1H), 1.69-1.55 (m, 7H), 1.46 (s, 9H), 1.17 (d, J = 6.3 Hz, 3H). |

TABLE 28-continued

| Intermediates prepare according to Step 3 above. | | | | |
|---|---|---|---|---|
| Inter-mediate | Structure | Chemical Name | MS: $[(M + 1)]^+$ | $^1$H-NMR |
| G-3-26 | 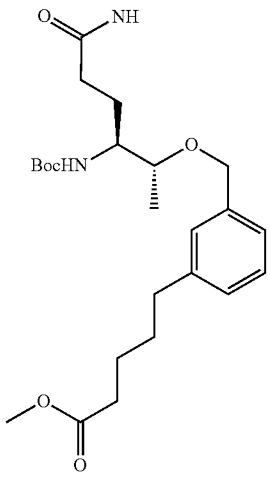 [SMILES: COC(=O)CCCCc1cccc(CO[C@H](C)[C@H](CCC(N)=O)NC(=O)OC(C)(C)C)c1] | Methyl 5-[3-([[(2R,3S)-3-[(tert-butoxycarbonyl)amino]-5-carbamoylpentan-2-yl]oxy]methyl)phenyl]pentanoate | 451.3 | (400 MHz, $CD_3OD$) δ 7.25 (t, J = 7.5 Hz, 1H), 7.22-7.15 (m, 2H), 7.11 (dt, J = 7.4, 1.6 Hz, 1H), 4.57 (d, J = 11.5 Hz, 1H), 4.51 (d, J = 11.5 Hz, 1H), 3.66 (s, 3H), 3.64-3.56 (m, 1H), 3.52 (p, J = 6.0 Hz, 1H), 2.69-2.61 (m, 2H), 2.41-2.32 (m, 2H), 2.35-2.17 (m, 2H), 1.99 (dddd, J = 13.0, 9.7, 6.7, 3.2 Hz, 1H), 1.72-1.57 (m, 5H), 1.46 (s, 9H), 1.18 (d, J = 6.2 Hz, 3H). |
| G-3-27 | 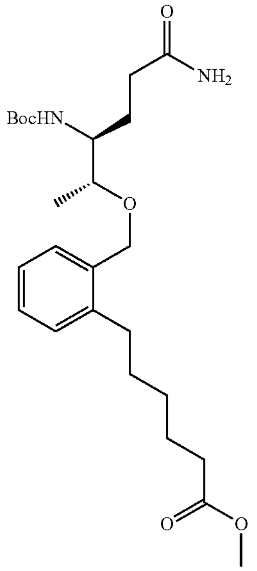 [SMILES: COC(=O)CCCCCc1ccccc1CO[C@H](C)[C@H](CCC(N)=O)NC(=O)OC(C)(C)C] | Methyl 6-[2-([[(2R,3S)-3-[(tert-butoxycarbonyl)amino]-5-carbamoylpentan-2-yl]oxy]methyl)phenyl]hexanoate | 465.3 | (400 MHz, DMSO-$d_6$) δ 7.36-7.29 (m, 1H), 7.24-7.11 (m, 4H), 6.71-6.56 (m, 2H), 4.54-4.41 (m, 2H), 3.58 (s, 3H), 3.46 (dd, J = 9.3, 6.2 Hz, 2H), 2.63-2.56 (m, 2H), 2.31 (t, J = 7.4 Hz, 2H), 2.13-1.96 (m, 2H), 1.78 (qt, J = 8.0, 4.3 Hz, 1H), 1.55 (m, 5H), 1.39 (s, 9H), 1.35-1.23 (m, 2H), 1.08 (d, J = 5.7 Hz, 3H). |

TABLE 28-continued

| Intermediates prepare according to Step 3 above. | | | | |
|---|---|---|---|---|
| Inter-mediate | Structure | Chemical Name | MS: $[(M + 1)]^+$ | $^1$H-NMR |
| G-3-28 | 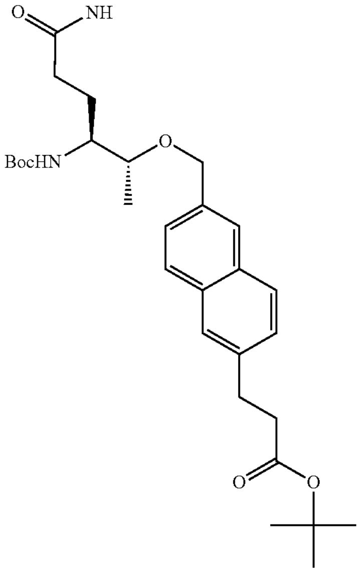 [SMILES: C[C@@H](OCc1ccc2cc(CCC(=O)OC(C)(C)C)ccc2c1)[C@H](CCC(N)=O)NC(=O)OC(C)(C)C] | tert-Butyl 3-[6-([[(2R,3S)-3-[(tert-butoxycarbonyl) amino]-5-carbamoylpentan-2-yl]oxy]methyl) naphthalen-2-yl]propanoate | 515.3 | (400 MHz, $CD_3OD$) δ 7.78 (d, J = 5.8 Hz, 1H), 7.66 (d, J = 1.5 Hz, 1H), 7.49 (dd, J = 8.5, 1.7 Hz, 1H), 7.38 (dd, J = 8.5, 1.8 Hz, 1H), 7.26-7.22 (m, 1H), 7.16 (dt, J = 6.3, 1.8 Hz, 1H), 4.79-4.58 (m, 2H), 3.60 (tq,J = 11.6, 6.0, 5.5 Hz, 2H), 3.06 (t, J = 7.5 Hz, 2H), 2.89-2.79 (m, 1H), 2.75 (td, J = 7.3, 1.6 Hz, 1H), 2.65 (t, J = 7.5 Hz, 2H), 2.38-2.18 (m, 1H), 2.02 (dt, J = 10.3, 2.8 Hz, 1H), 1.42 (s, 9H), 1.40 (s, 9H), 1.22 (d, J = 6.0 Hz, 3H). |
| G-3-29 | 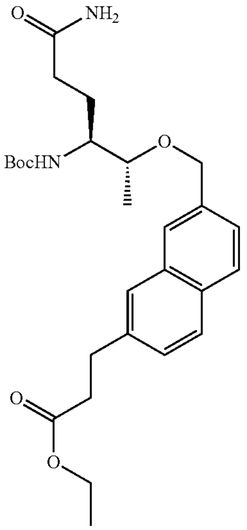 [SMILES: CCOC(=O)CCc1ccc2ccc(CO[C@H](C)[C@H](CCC(N)=O)NC(=O)OC(C)(C)C)cc2c1] | ethyl 3-[7-([[(2R,3S)-3-[(tert-butoxycarbonyl) amino]-5-carbamoylpentan-2-yl]oxy]methyl) naphthalen-2-yl]propanoate | 487.30 | (400 MHz, DMSO-$d_6$) δ 7.83-7.81 (m, 2H), 7.76 (s, 1H), 7.68 (s, 1H), 7.46-7.38 (m, 2H), 7.23 (s, 1H), 6.72-6.60 (m, 2H), 4.67-4.59 (m, 2H), 4.05 (q, J = 7.1 Hz, 2H), 3.48-3.44 (m, 2H), 3.03-2.98 (m, 2H), 2.73-2.69 (m, 2H), 2.12-2.05 (m, 2H), 1.90-1.82(m, 1H), 1.58-1.45 (m, 1H), 1.38 (s, 9H), 1.16-1.14 (m, 3H), 1.10 (d, J = 5.8 Hz, 3H) |

TABLE 28-continued

| Intermediates prepare according to Step 3 above. | | | | |
|---|---|---|---|---|
| Inter-mediate | Structure | Chemical Name | MS: $[(M + 1)]^+$ | $^1H$-NMR |
| G-3-30 | 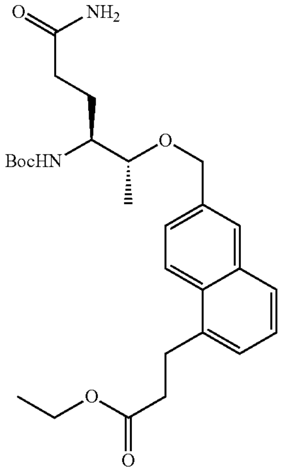 [SMILES: CCOC(=O)CCc1cccc2cc(CO[C@H](C)[C@H](CCC(N)=O)NC(=O)OC(C)(C)C)ccc12] | ethyl 3-[6-([[(2R,3S)-3-[(tert-butoxycarbonyl)amino]-5-carbamoylpentan-2-yl]oxy]methyl)naphthalen-1-yl]propanoate | 487.20 | Used in the next step without further purification |
| G-3-31 | 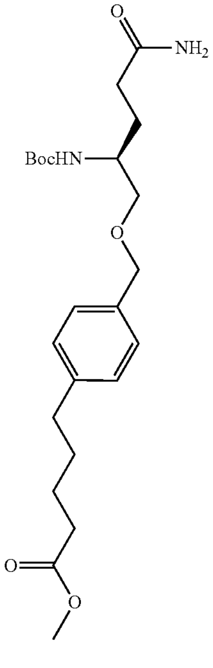 [SMILES: COC(=O)CCCCc1ccc(COC[C@H](CCC(N)=O)NC(=O)OC(C)(C)C)cc1] | methyl 5-(4-[[(2S)-2-[(tert-butoxycarbonyl)amino]-4-carbamoylbutoxy]methyl]phenyl)pentanoate | 437.25 | (400 MHz, DMSO-$d_6$) δ 7.26-7.20 (m, 3H), 7.15 (d, J = 7.9 Hz, 2H), 6.73-6.63 (m, 2H), 4.41 (s, 2H), 3.37-3.22 (m, 4H), 2.60-2.55 (m, 2H), 2.32 (t, J = 6.8 Hz, 2H), 2.12-2.01 (m, 2H), 1.80-1.68 (m, 1H), 1.62-1.44 (m, 8H), 1.37 (s, 9H) |

TABLE 28-continued

| Intermediates prepare according to Step 3 above. | | | | |
|---|---|---|---|---|
| Inter-mediate | Structure | Chemical Name | MS: $[(M + 1)]^+$ | $^1$H-NMR |
| G-3-32 | 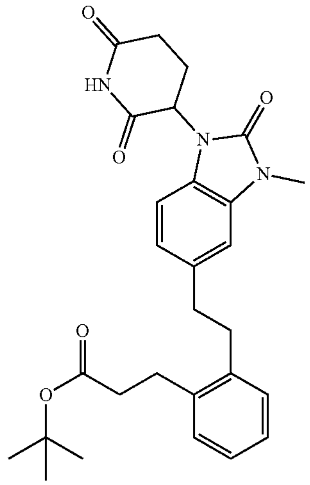 [SMILES: Cn1c(=O)n(C2CCC(=O)NC2=O)c2ccc(CCc3ccccc3CCC(=O)OC(C)(C)C)cc21] | tert-butyl 3-(2-(2-(1-(2,6-dioxopiperidin-3-yl)-3-methyl-2-oxo-2,3-dihydro-1H-benzo[d]imidazol-5-yl)ethyl)phenyl) propanoate | $[(M-1)]^-$ = 490.05 | (400 MHz, DMSO-$d_6$) δ 11.09 (s, 1H), 7.27-7.20 (m, 1H), 7.19-7.10 (m, 4H), 7.03 (d, J = 8.0 Hz, 1H), 6.92 (dd, J = 8.0, 1.6 Hz, 1H), 5.35 (dd, J = 12.7, 5.4 Hz, 1H), 3.34 (s, 3H), 3.00-2.80 (m, 8H), 2.79-2.58 (m, 2H), 2.47-2.44 (m, 2H), 2.11-1.92 (m, 1H), 1.37 (s, 9H). |
| G-3-33 | 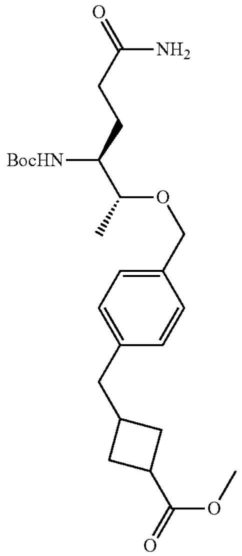 [SMILES: COC(=O)C1CC(Cc2ccc(CO[C@H](C)[C@H](CCC(N)=O)NC(=O)OC(C)(C)C)cc2)C1] | methyl 3-[[4-([[(2R,3S)-3-[(tert-butoxycarbonyl) amino]-5-carbamoylpentan-2-yl]oxy]methyl)phenyl] methyl]cyclobutane-1-carboxylate | 463.27 | (400 MHz, $CDCl_3$) δ 7.52-7.46 (m, 1H), 7.23 (t, J = 8.2 Hz, 2H), 7.13 (dd, J = 8.1, 3.9 Hz, 1H), 6.43 (d, J = 41.5 Hz, 1H), 5.38 (s, 1H), 4.87 (dd, J = 27.7, 9.8 Hz, 1H), 4.57 (dd, J = 11.7, 7.9 Hz, 1H), 4.38 (d, J = 11.7 Hz, 1H), 3.74-3.56 (m, 2H), 3.51 (s, 3H), 3.04-2.66 (m, 1H), 2.55-2.22 (m, 3H), 2.12-1.96 (m, 1H), 1.79-1.50 (m, 4H), 1.46 (s, 10H), 1.21 (d, J = 6.3 Hz, 3H) |

TABLE 28-continued

Intermediates prepare according to Step 3 above.

| Intermediate | Structure | Chemical Name | MS: $[(M + 1)]^+$ | $^1$H-NMR |
|---|---|---|---|---|
| G-3-34 | 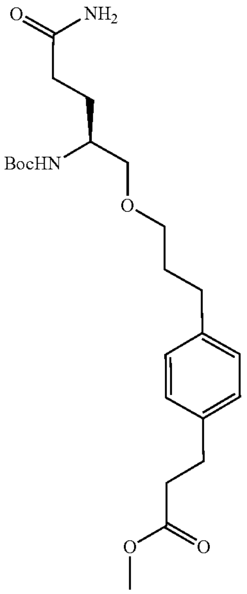 [SMILES: COC(=O)CCc1ccc(CCCOC[C@H](CCC(N)=O)NC(=O)OC(C)(C)C)cc1] | methyl 3-(4-[3-[(2S)-2-[(tert-butoxycarbonyl)amino]-4-carbamoylbutoxy]propyl]phenyl)propanoate | 436.55 | (400 MHz, $CDCl_3$) δ 7.20-7.19 (m, 1H), 7.16-7.08 (m, 3H), 6.65-6.51 (m, 1H), 5.56 (s, 1H), 5.01-4.98 (m, 1H), 4.25 (d, J = 6.3 Hz, 1H), 3.78 (s, 1H), 3.69 (s, 3H), 3.53-3.36 (m, 4H), 2.99-2.92 (m, 2H), 2.64 (q, J = 7.3 Hz, 3H), 2.37-2.24 (m, 2H), 1.98-1.81 (m, 4H), 1.46 (s, 9H) |
| G-3-35 | 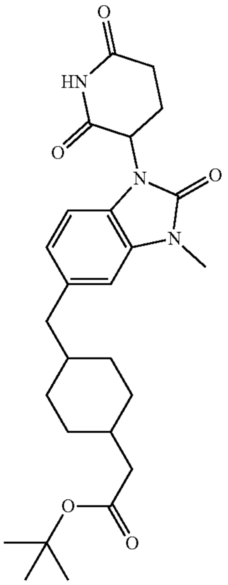 | tert-butyl 2-(4-[[1-(2,6-dioxopiperidin-3-yl)-3-methyl-2-oxo-1,3-benzodiazol-5-yl]methyl]cyclohexyl)acetate | $[(M - H)]^- =$ 468.20 | 300 MHz, $CDCl_3$) δ 8.30 (s, 1H), 6.91-6.78 (m, 2H), 6.71 (d, J = 8.0 Hz, 1H), 5.22 (dd, J = 12.4, 5.3 Hz, 1H), 3.43 (s, 3H), 3.01-2.68 (m, 4H), 2.61 (d, J = 7.5 Hz, 1.6 H, cis), 2.53 (d, J = 7.0 Hz, 0.5H, trans), 2.28-2.18 (m, 2H), 2.05-2.01 (m, 1H), 1.76-1.73 (m, 2H), 1.57-1.43 (m, 16H) |

TABLE 28-continued

| Intermediates prepare according to Step 3 above. | | | | |
|---|---|---|---|---|
| Inter-mediate | Structure | Chemical Name | MS: $[(M + 1)]^+$ | $^1$H-NMR |
| G-3-36 | 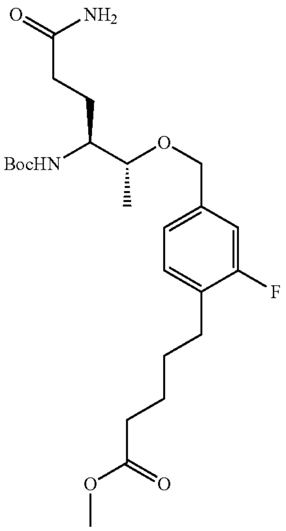 [SMILES: COC(=O)CCCCc1ccc(CO[C@H](C)[C@H](CCC(N)=O)NC(=O)OC(C)(C)C)cc1F] | methyl 5-[4-([[2R,3S)-3-[(tert-butoxycarbonyl)amino]-5-carbamoylpentan-2-yl]oxy]methyl)-2-fluorophenyl]pentanoate | 469.25 | (400 MHz, DMSO-$d_6$) δ 7.26-7.18 (m, 2H), 7.14-7.03 (m, 2H), 6.70-6.60 (m, 2H), 4.51-4.39 (m, 2H), 3.58 (s, 3H), 3.49-3.45 (m, 1H), 3.43-3.39 (m, 1H), 2.59 (s, 2H), 2.33 (td, J = 6.9, 5.7, 3.1 Hz, 2H), 2.13-1.95 (m, 2H), 1.82-1.70 (m, 1H), 1.60-1.45 (m, 5H), 1.38 (s, 9H), 1.06 (d, J = 6.1 Hz, 3H) |
| G-3-37 | 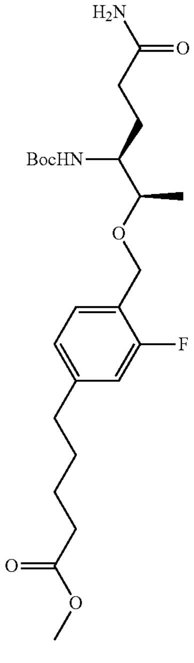 [SMILES: COC(=O)CCCCc1ccc(CO[C@H](C)[C@H](CCC(N)=O)NC(=O)OC(C)(C)C)c(F)c1] | methyl 5-[4-([[2R,3S)-3-[(tert-butoxycarbonyl)amino]-5-carbamoylpentan-2-yl]oxy]methyl)-3-fluorophenyl]pentanoate | 469.30 | (400 MHz, DMSO-$d_6$) δ 7.34 (t, J = 8.0 Hz, 1H), 7.21 (s, 1H), 7.05-6.96 (m, 2H), 6.67 (s, 1H), 6.59 (d, J = 8.7 Hz, 1H), 4.49 (q, J = 8.0 Hz, 2H) 3.58 (s, 3H), 3.47-3.39 (m, 2H), 3.18 (d, J = 5.2 Hz, 1H), 2.59 (t, J = 7.1 Hz, 2H), 2.33 (t, J = 7.0 Hz, 2H), 2.10-1.97 (m, 2H), 1.84-1.71 (m, 1H), 1.64-1.48 (m, 4H), 1.38 (s, 9H), 1.07 (d, J = 5.7 Hz, 3H) |

TABLE 28-continued

| Intermediates prepare according to Step 3 above. | | | | |
|---|---|---|---|---|
| Inter-mediate | Structure | Chemical Name | MS: $[(M + 1)]^+$ | $^1$H-NMR |
| G-3-55 | 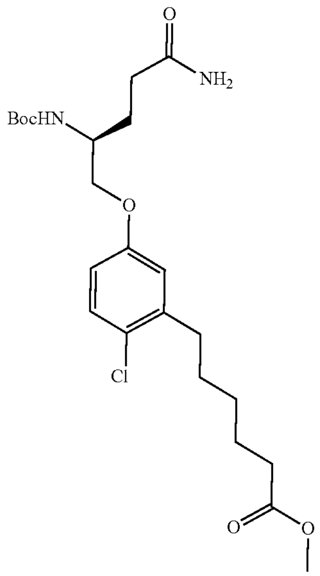 [SMILES: COC(=O)CCCCCc1cc(OC[C@H](CCC(N)=O)NC(=O)OC(C)(C)C)ccc1Cl] | methyl 6-[5-[(2S)-2-[(tert-butoxycarbonyl) amino]-4-carbamoylbutoxy]-2-chlorophenyl] hexanoate | 471.30 | (400 MHz, DMSO-$d_6$) δ 7.31-7.24 (m, 2H), 6.93-6.88 (m, 1H), 6.86-6.75 (m, 2H), 6.79-6.70 (m, 1H), 3.84-3.86 (m, 2H), 3.73-3.69 (m, 1H), 3.59-3.56 (m, 3H), 2.67-2.58 (m, 2H), 2.35-2.25 (m, 4H), 2.17-2.07 (m, 2H), 1.63-1.53 (m, 5H), 1.55-1.51 (m, 1H), 1.25 (s, 9H |
| G-3-56 | 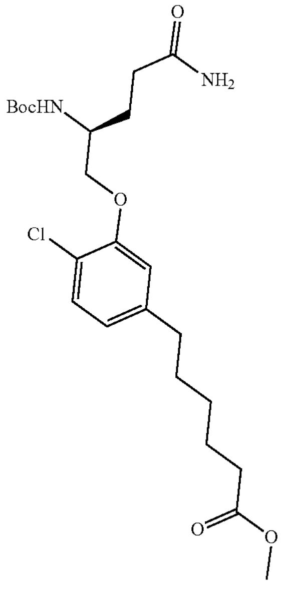 [SMILES: COC(=O)CCCCCc1ccc(Cl)c(OC[C@H](CCC(N)=O)NC(=O)OC(C)(C)C)c1] | methyl 6-[3-[(2S)-2-[(tert-butoxycarbonyl) amino]-4-carbamoylbutoxy]-4-chlorophenyl] hexanoate | 471.25 | (400 MHz, DMSO-$d_6$) δ 7.28 (d, J = 8.0 Hz, 1H), 7.26-7.24 (m, 1H), 7.00-6.98 (m, 1H), 6.8-6.70 (m, 3H), 3.94 (d, J = 6.1 Hz, 2H), 3.77 (s, 1H), 3.58-3.35 (m, 3H), 3.32 (s, 1H), 2.34-2.25 (m, 5H), 2.13-1.90 (m, 2H), 1.84-1.61 (m, 1H), 1.67-1.54 (m, 3H), 1.39 (s, 9H), 1.19-1.10 (m, 2H) |

TABLE 28-continued

| Intermediate | Structure | Chemical Name | MS: $[(M + 1)]^+$ | $^1$H-NMR |
|---|---|---|---|---|
| Intermediates prepare according to Step 3 above. | | | | |
| G-3-57 | 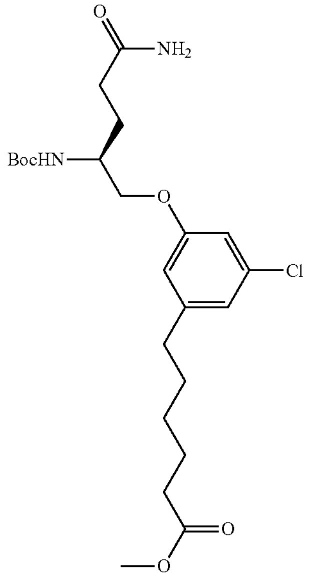 [SMILES: COC(=O)CCCCCc1cc(Cl)cc(OC[C@H](CCC(N)=O)NC(=O)OC(C)(C)C)c1] | methyl 6-[3-[(2S)-2-[(tert-butoxycarbonyl)amino]-4-carbamoylbutoxy]-5-chlorophenyl]hexanoate | 471.10 | $^1$H NMR (400 MHz, DMSO-$d_6$) δ 7.25 (s, 1H), 6.90-6.79 (m, 3H), 6.79-6.70 (m, 2H), 4.48-4.34 (m, 1H), 3.90-3.84 (m, 2H), 3.76-3.65 (m, 1H), 3.64-3.59 (m, 1H), 3.58 (s, 3H), 2.31-2.28 (m, 2H), 2.15-2.08 (m, 2H), 1.80-1.73 (m, 2H), 1.57-1.53 (m, 4H), 1.38 (s, 9H), 1.30-1.26 (m, 2H) |
| G-3-58 | 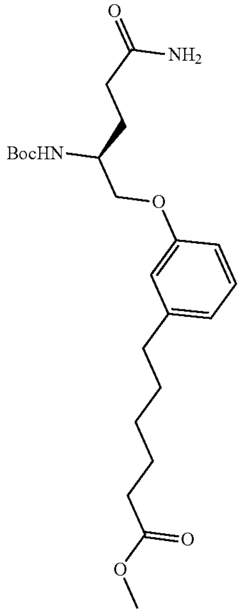 [SMILES: COC(=O)CCCCCc1cccc(OC[C@H](CCC(N)=O)NC(=O)OC(C)(C)C)c1] | 6-[3-[(2S)-2-[(tert-butoxycarbonyl)amino]-4-carbamoylbutoxy]-phenyl]hexanoate | 437.35 | $^1$H NMR (400 MHz, DMSO-$d_6$) δ 7.27 (s, 1H), 7.17 (t, J = 8.0 Hz, 1H), 6.82 (d, J = 8.5 Hz, 1H), 6.74 (dd, J = 12.2, 6.3 Hz, 4H), 3.86-3.82 (m, 2H), 3.70 (t, J = 7.0 Hz, 1H), 3.58 (s, 3H), 2.57-2.51 (m, 2H), 2.30 (t, J = 7.4 Hz, 2H), 2.12-2.08 (m, 2H), 1.81 (s, 2H), 1.58-1.54 (m, 4H), 1.40 (s, 9H), 1.32-1.22 (m, 2H) |

TABLE 28-continued

| Intermediates prepare according to Step 3 above. | | | | |
|---|---|---|---|---|
| Intermediate | Structure | Chemical Name | MS: $[(M + 1)]^+$ | $^1$H-NMR |
| G-3-59 | 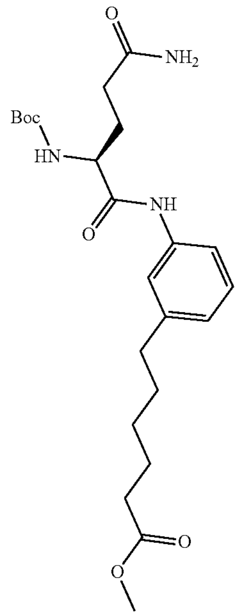 | methyl 6-[3-[(2S)-2-[(tert-butoxycarbonyl) amino]-4-carbamoylbutanamido] phenyl]hexanoate | 450.25 | $^1$H NMR (300 MHz, DMSO-$d_6$) δ 9.84 (s, 1H), 7.42 (t, J = 1.8 Hz, 2H), 7.18 (d, J = 8.6 Hz, 1H), 7.06 (t, J = 7.9 Hz, 2H), 7.04-6.98 (m, 1H), 6.75 (s, 1H), 4.00 (q, J = 7.5 Hz, 1H), 3.57 (s, 3H), 3.17 (d, J = 5.3 Hz, 2H), 2.74-2.71 (m, 1H), 2.34-2.24 (m, 2H), 2.18-2.10 (m, 1H), 1.60-1.50 (m, 4H), 1.38 (s, 9H), 1.33-1.24 (m, 4H) |
| G-3-60 | 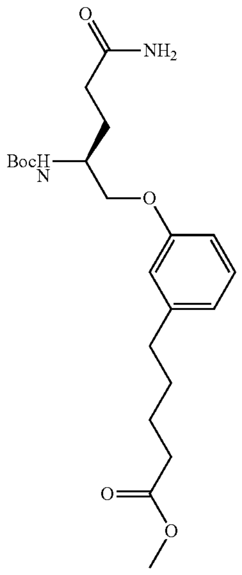 [SMILES: COC(=O)CCCCc1cccc(OC[C@H](CCC(N)=O)NC(=O)OC(C)(C)C)c1] | methyl 5-[3-[(2S)-2-[(tert-butoxycarbonyl) amino]-4-carbamoylbutoxy]-phenyl]pentanoate | 423.10 | $^1$H NMR (400 MHz, DMSO-$d_6$) δ 7.26 (s, 1H), 7.17 (t, J = 8.0 Hz, 1H), 6.81 (d, J = 8.4 Hz, 1H), 6.78-6.69 (m, 4H), 3.86-3.82 (m, 2H), 3.74-3.70 (m, 1H), 3.58 (s, 3H), 2.56-2.54 (m, 2H), 2.38-2.24 (m, 4H), 2.19-2.05 (m, 1H), 1.85-1.80 (m, 1H), 1.59-1.49 (m, 4H), 1.39 (s, 9H) |

TABLE 28-continued

| Intermediates prepare according to Step 3 above. | | | | |
|---|---|---|---|---|
| Intermediate | Structure | Chemical Name | MS: $[(M+1)]^+$ | $^1$H-NMR |
| G-3-61 | 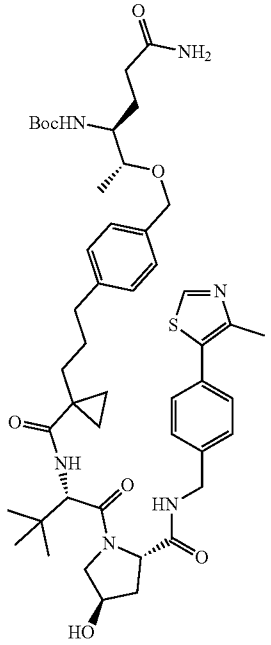 [SMILES: Cc1ncsc1-c1ccc(CNC(=O)[C@@H]2C[C@@H](O)CN2C(=O)[C@@H](NC(=O)C2(CCCc3ccc(CO[C@H](C)[C@H](CCC(N)=O)NC(=O)OC(C)(C)C)cc3)CC2)C(C)(C)C)cc1] | tert-butyl N-[(3S,4R)-1-carbamoyl-4-([4-[3-(1-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]cyclopropyl)propyl]phenyl]methoxy)pentan-3-yl]carbamate | 875.55 | $^1$H NMR (400 MHz, Methanol-$d_4$) δ 8.89 (s, 1H), 7.60-7.42 (m, 4H), 7.30-7.22 (m, 2H), 7.18 (d, J = 8.1 Hz, 2H), 4.75-4.68 (m, 1H), 4.65-4.58 (m, 1H), 4.60-4.53 (m, 1H), 4.51 (s, 2H), 4.46 (d, J = 11.4 Hz, 1H), 4.36 (d, J = 15.5 Hz, 1H), 3.87 (d, J = 11.2 Hz, 1H), 3.85-3.72 (m, 1H), 3.57 (s, 1H), 3.62-3.44 (m, 1H), 2.70-2.61 (m, 2H), 2.30-2.22 (m, 1H), 2.25 (s, 1H), 2.26-2.16 (m, 1H), 2.18-2.05 (m, 1H), 1.96 (s, 1H), 1.94 (s, 3H), 1.85-1.76 (m, 3H), 1.62 (s, 1H), 1.45 (s, 9H), 1.38-1.26 (m, 2H), 1.20-1.09 (m, 4H), 1.03 (s, 9H), 0.70-0.59 (m, 2H) |
| G-3-62 | 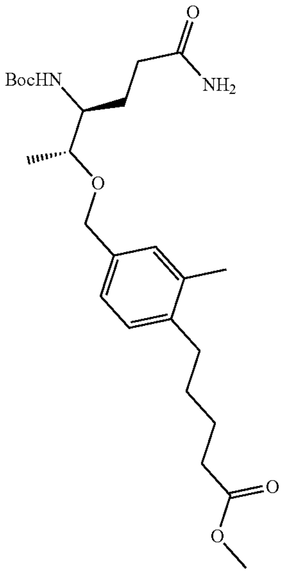 [SMILES: COC(=O)CCCCc1ccc(CO[C@H](C)[C@H](CCC(N)=O)NC(=O)OC(C)(C)C)cc1C] | methyl 5-[4-([[(2R,3S)-3-[(tert-butoxycarbonyl)amino]-5-carbamoylpentan-2-yl]oxy]methyl)-2-methylphenyl]pentanoate | 465.30 | $^1$H NMR (400 MHz, DMSO-$d_6$) δ 7.21 (s, 1H), 7.11-7.03 (m, 3H), 6.67 (s, 1H), 6.59 (d, J = 9.2 Hz, 1H), 4.43-4.35 (m, 2H), 3.59 (s, 3H), 3.48-3.37 (m, 1H), 2.56-2.54 (m, 3H), 2.35 (t, J = 7.2 Hz, 2H), 2.24 (s, 3H), 2.12-1.97 (m, 2H), 1.83-1.76 (m, 1H), 1.63-1.42 (m, 5H), 1.39 (s, 9H), 1.05 (d, J = 6.0 Hz, 3H) |

TABLE 28-continued

| Intermediates prepare according to Step 3 above. | | | | |
|---|---|---|---|---|
| Inter-mediate | Structure | Chemical Name | MS: $[(M + 1)]^+$ | $^1$H-NMR |
| G-3-63 | 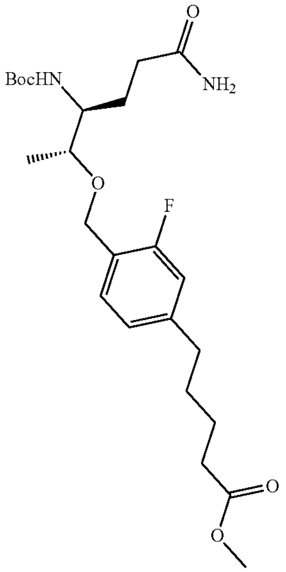 [SMILES: COC(=O)CCCCc1ccc(CO[C@H](C)[C@H](CCC(N)=O)NC(=O)OC(C)(C)C)c(F)c1] | methyl 5-[4-([[2R,3S)-3-[(tert-butoxycarbonyl) amino]-5-carbamoylpentan-2-yl]oxy]methyl)-3-fluorophenyl] pentanoate | 469.30 | $^1$H NMR (400 MHz, DMSO-$d_6$) δ 7.34 (t, J = 7.8 Hz, 1H), 7.21 (s, 1H), 7.04-6.96 (m, 2H), 6.68 (s, 1H), 6.60 (d, J = 8.6 Hz, 1H), 4.57-4.37 (m, 2H), 3.58 (s, 3H), 3.45-3.38 (m, 2H), 2.58 (t, J = 7.1 Hz, 2H), 2.33 (t, J = 7.0 Hz, 2H), 2.12-1.92 (m, 2H), 1.81-1.74 (m, 1H), 1.63-1.47 (m, 4H), 1.38 (s, 9H), 1.35 (s, 1H), 1.06 (d, J = 5.4 Hz, 3H) |
| G-3-64 | 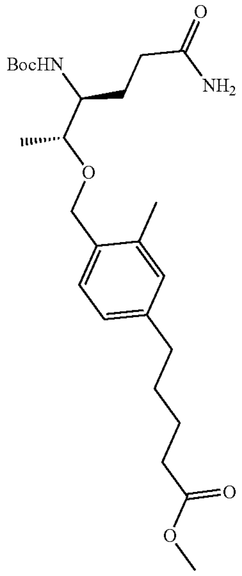 [SMILES: COC(=O)CCCCc1ccc(CO[C@H](C)[C@H](CCC(N)=O)NC(=O)OC(C)(C)C)c(C)c1] | methyl 5-[4-([[2R,3S)-3-[(tert-butoxycarbonyl) amino]-5-carbamoylpentan-2-yl]oxy]methyl)-3-methylphenyl] pentanoate | 465.40 | $^1$H NMR (400 MHz, Methanol-$d_4$) δ 7.22 (d, J = 7.6 Hz, 1H), 7.03-6.95 (m, 2H), 4.61-4.45 (m, 2H), 3.66 (d, J = 3.1 Hz, 4H), 3.61-3.50 (m, 2H), 2.61-2.56 (m, 2H), 2.37-2.31 (m, 5H), 2.28-2.17 (m, 2H), 2.01-1.92 (m, 1H), 1.65-1.61 (m, 4H), 1.45 (s, 9H), 1.19 (d, J = 6.0 Hz, 3H) |

TABLE 28-continued

| Intermediates prepare according to Step 3 above. | | | | |
|---|---|---|---|---|
| Intermediate | Structure | Chemical Name | MS: $[(M + 1)]^+$ | $^1$H-NMR |
| G-3-65 | 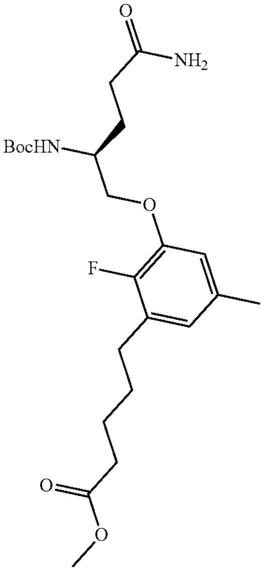 [SMILES: COC(=O)CCCCc1cc(C)cc(OC[C@H](CCC(N)=O)NC(=O)OC(C)(C)C)c1F] | methyl 5-[3-[(2S)-2-[(tert-butoxycarbonyl)amino]-4-carbamoylbutoxy]-2-fluoro-5-methylphenyl]pentanoate | 455.25 | (300 MHz, DMSO-$d_6$) δ 7.24 (s, 1H), 6.85-6.74 (m, 2H), 6.71 (s, 1H), 6.64-6.55 (m, 1H), 3.88 (d, J = 6.0 Hz, 2H), 3.77-3.67 (m, 1H), 3.57 (s, 3H), 2.61-2.51 (m, 2H), 2.22 (s, 3H), 2.16-2.06 (m, 2H), 1.60-1.44 (m, 8H), 1.37 (s, 9H) |
| G-3-66 | 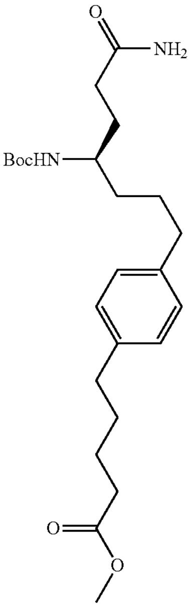 [SMILES: COC(=O)CCCCc1ccc(CCC[C@H](CCC(N)=O)NC(=O)OC(C)(C)C)cc1] | methyl 5-[4-[(4R)-4-[(tert-butoxycarbonyl)amino]-6-carbamoylhexyl]phenyl]pentanoate | 435.30 | (400 MHz, DMSO-$d_6$) δ 7.21 (s, 1H), 7.10-7.06 (m, 4H), 6.68 (s, 1H), 6.59 (d, J = 9.0 Hz, 1H), 3.58 (s, 3H), 3.41-3.34 (m, 1H), 2.61-2.56 (m, 2H), 2.50-2.47 (m, 1H), 2.32-2.32 (m, 2H), 2.02 (t, J = 7.9 Hz, 2H), 1.64-1.48 (m, 11H), 1.38 (s, 9H) |

TABLE 28-continued

| Intermediates prepare according to Step 3 above. | | | | |
|---|---|---|---|---|
| Inter-mediate | Structure | Chemical Name | MS: $[(M + 1)]^+$ | $^1H$-NMR |
| G-3-67 | 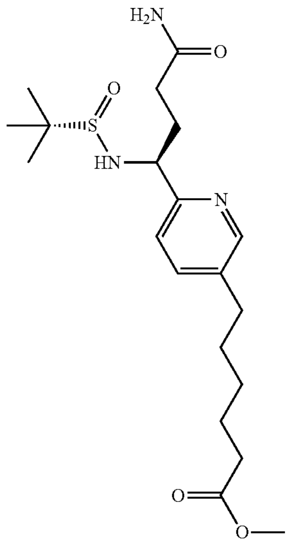 | methyl 6-[6-[(1S)-3-carbamoyl-1-[(2-methylpropane-2-sulfinyl)amino] propyl]pyridin-3-yl]hexanoate | 412.30 | (400 MHz, DMSO-$d_6$) δ 8.39-8.37 (d, J = 2.3 Hz, 1H), 7.63-7.61 (dd, J = 8.0, 2.3 Hz, 1H), 7.33-7.17 (m, 2H), 6.78 (s, 1H), 5.57-5.66 (d, J = 5.2 Hz, 1H), 4.27-4.22 (m, 1H), 3.57 (s, 3H), 2.71-2.67 (t, J = 7.7 Hz, 2H), 2.31-2.28 (t, J = 7.4 Hz, 2H), 2.17-2.10 (m, 1H), 2.08-1.97 (m, 2H), 1.93-1.80 (m, 1H), 1.70-1.62 (m, 2H), 1.60-1.52 (m, 2H), 1.38-1.21 (m, 2H), 1.08 (s, 9H) |
| G-3-68 | 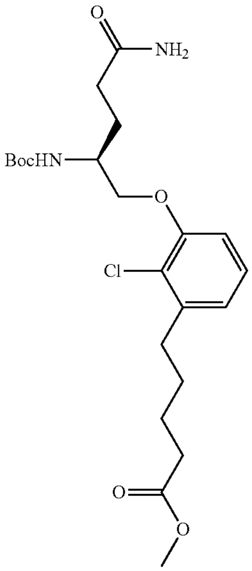 [SMILES: COC(=O)CCCCc1cccc(OC[C@H](CCC(N)=O)NC(=O)OC(C)(C)C)c1Cl] | methyl 5-[3-[(2S)-2-[(tert-butoxycarbonyl) amino]-4-carbamoylbutoxy]-2-chlorophenyl] pentanoate | 457.15 | (400 MHz, DMSO-$d_6$) δ 7.27 (s, 1H), 7.20 (t, J = 7.9 Hz, 1H), 6.98 (dd, J = 8.4, 1.4 Hz, 1H), 6.90 (dd, J = 7.7, 1.3 Hz, 1H) 6.81 (d, J = 8.5 Hz, 1H), 6.77-6.72 (m, 1H), 3.92 (d, J = 6.1 Hz, 2H), 3.82-3.72 (m, 1H), 3.58 (s, 3H), 2.69 (s, 2H), 2.38-2.29 (m, 2H), 2.23-2.05 (m, 2H), 1.91-1.78 (m, 1H), 1.69-1.59 (m, 1H), 1.59-1.51 (m, 4H), 1.39 (s, 9H) |

TABLE 28-continued

| Intermediates prepare according to Step 3 above. | | | | |
|---|---|---|---|---|
| Inter-mediate | Structure | Chemical Name | MS: $[(M + 1)]^+$ | $^1$H-NMR |
| G-3-69 | 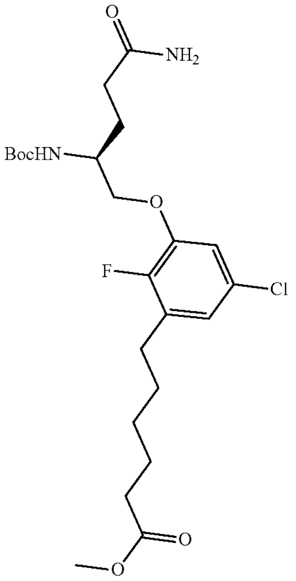 [SMILES: COC(=O)CCCCCc1cc(Cl)cc(OC[C@H](CCC(N)=O)NC(=O)OC(C)(C)C)c1F] | methyl 6-[3-[(2S)-2-[(tert-butoxycarbonyl)amino]-4-carbamoylbutoxy]-5-chloro-2-fluorophenyl]hexanoate | 489.20 | (300 MHz, DMSO-$d_6$) δ 7.28 (s, 1H), 7.13-7.11 (m, 1H), 6.93-6.91 (m, 1H), 6.84 (d, J = 8.4 Hz, 1H), 6.75 (s, 1H), 4.02-3.86 (m, 2H), 3.75-3.73 (m, 1H), 3.59 (s, 3H), 2.58 (d, J = 7.5 Hz, 2H), 2.16-2.14 (m, 2H), 1.83-1.71 (m, 1H), 1.58-1.51 (m, 9H), 1.39 (s, 9H) |
| G-3-70 | 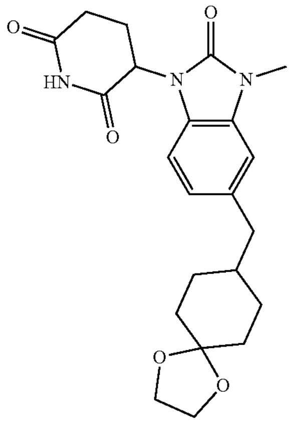 [SMILES: Cn1c(=O)n(C2CCC(=O)NC2=O)c2ccc(CC3CCC4(CC3)OCCO4)cc21] | 3-(5-[1,4-dioxaspiro[4.5]decan-8-ylmethyl]-3-methyl-2-oxo-1,3-benzodiazol-1-yl)piperidine-2,6-dione | 414.20 | (300 MHz, DMSO-$d_6$) δ 7.04-7.00 (m, 2H), 6.85-6.82 (m, 1H), 5.38-5.34 (m, 1H), 3.85-3.83 (m, 4H), 3.21-3.17 (m, 2H), 2.92-2.90 (m, 1H), 2.79-2.57 (m, 3H), 2.06-1.97 (m, 1H), 1.65-1.60 (m, 6H), 1.42-1.39 (m, 2H), 1.21 (s, 3H) |

TABLE 28-continued

| Intermediates prepare according to Step 3 above. | | | | |
|---|---|---|---|---|
| Intermediate | Structure | Chemical Name | MS: [(M + 1)]+ | $^1$H-NMR |
| G-3-71 | 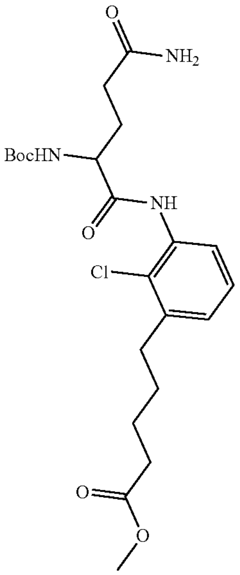 [SMILES: COC(=O)CCCCc1cccc(NC(=O)C(CCC(N)=O)NC(=O)OC(C)(C)C)c1Cl] | methyl 5-(3-[2-[(tert-butoxycarbonyl)amino]-4-carbamoylbutanamido]-2-chlorophenyl)pentanoate | 470.15 | (400 MHz, DMSO-d6) δ 9.32 (s, 1H), 7.74 (d, J = 8.0 Hz, 1H), 7.68-7.61 (m, 1H), 7.65-7.55 (m, 1H), 7.33-7.22 (m, 1H), 7.13 (dd, J = 7.6, 1.6 Hz, 1H), 6.81 (s, 1H), 4.15-4.09 (m, 1H), 3.58 (s, 3H), 2.72 (d, J = 13.7 Hz, 1H),2.39-2.31 (m, 2H), 2.19 (s, 3H), 1.88 (s, 3H), 1.58 (d, J = 3.6 Hz, 3H), 1.41 (s, 9H) |
| G-3-72 | 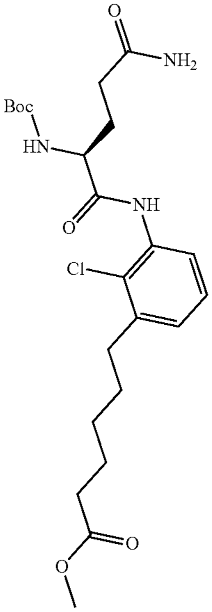 [SMILES: COC(=O)CCCCCc1cccc(NC(=O)[C@H](CCC(N)=O)NC(=O)OC(C)(C)C)c1Cl] | methyl 6-[3-[(2S)-2-[(tert-butoxycarbonyl)amino]-4-carbamoylbutanamido]-2-chlorophenyl]hexanoate | 484.25 | (300 MHz, DMSO-$d_6$) δ 9.32 (s, 1H), 7.74 (d, J = 7.7 Hz, 1H), 7.31-7.24 (m, 1H), 7.14 (d, J = 7.5 Hz, 1H), 6.81 (s, 1H), 4.11 (q, J = 5.2 Hz, 1H), 3.59 (s, 3H), 3.18 (d, J = 5.3 Hz, 2H), 2.77-2.66 (m, 2H), 2.32 (t, J = 7.3 Hz, 2H), 2.23-2.18 (m, 2H), 2.11-1.71 (m, 2H), 1.63-1.55 (m, 5H), 1.42 (s, 9H), 1.37-1.25 (m, 1H) |

TABLE 28-continued

Intermediates prepare according to Step 3 above.

| Inter-mediate | Structure | Chemical Name | MS: $[(M + 1)]^+$ | $^1H$-NMR |
|---|---|---|---|---|
| G-3-73 | 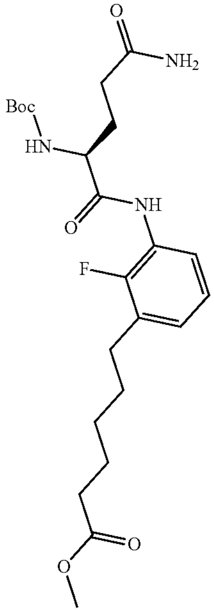 [SMILES: COC(=O)CCCCCc1cccc(NC(=O)[C@H](CCC(N)=O)NC(=O)OC(C)(C)C)c1F] | methyl 6-[3-[(2S)-2-[(tert-butoxycarbonyl) amino]-4-carbamoylbutanamido]-2-fluorophenyl] hexanoate | $[(M - 1)]^-$ = 466.20 | (300 MHz, DMSO-$d_6$) δ 9.58 (s, 1H), 7.77-7.73 (m, 1H), 7.69-7.51 (m, 4H), 7.30 (s, 1H), 7.14-7.01 (m, 3H), 6.80 (s, 1H), 4.18-4.14 (m, 1H), 3.18 (d, J = 5.2 Hz, 1H), 2.61 (t, J = 7.6 Hz, 2H), 2.31 (t, J = 7.3 Hz, 2H), 2.22-2.14 (m, 1H), 2.04-1.67 (m, 1H), 1.62-1.52 (m, 4H), 1.40 (s, 9H), 1.37-1.22 (m, 2H) |
| G-3-74 | 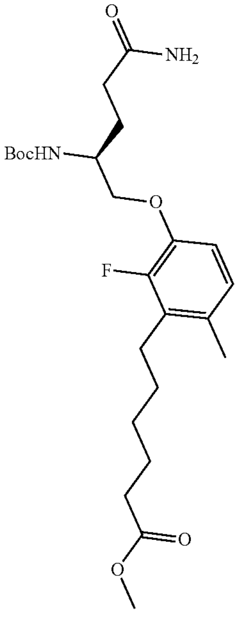 [SMILES: COC(=O)CCCCCc1c(C)ccc(OC[C@H](CCC(N)=O)NC(=O)OC(C)(C)C)c1F] | methyl 6-[3-[(2S)-2-[(tert-butoxycarbonyl) amino]-4-carbamoylbutoxy]-2-fluoro-6-methylphenyl] hexanoate | 469.15 | (400 MHz, DMSO-$d_6$) δ 7.26 (s, 1H), 6.92-6.84 (m, 2H), 6.82 (d, J = 8.4 Hz, 1H), 6.73 (s, 1H), 3.91-3.84 (m, 2H), 3.79-3.62 (m, 1H), 3.58 (s, 3H), 2.56 (s, 2H), 2.30 (t, J = 7.4 Hz, 2H), 2.21 (s, 3H), 2.18-2.04 (m, 2H), 1.87-1.74 (m, 1H), 1.65-1.51 (m, 3H), 1.48-1.44 (m, 2H), 1.39 (s, 9H), 1.37-1.26 (m, 2H) |

TABLE 28-continued

Intermediates prepare according to Step 3 above.

| Inter-mediate | Structure | Chemical Name | MS: $[(M + 1)]^+$ | $^1$H-NMR |
|---|---|---|---|---|
| G-3-75 | 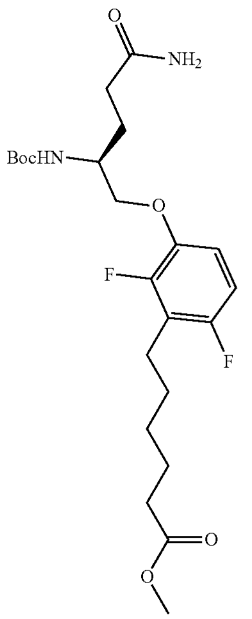 [SMILES: COC(=O)CCCCCc1c(F)ccc(OC[C@H](CCC(N)=O)NC(=O)OC(C)(C)C)c1F] | methyl 6-[3-[(2S)-2-[(tert-butoxycarbonyl) amino]-4-carbamoylbutoxy]-2,6-difluorophenyl] hexanoate | 473.10 | (400 MHz, DMSO-$d_6$) δ 7.26 (s, 1H), 7.06-7.02 (m, 1H), 6.98-6.94 (m, 1H), 6.83 (d, J = 8.4 Hz, 1H), 6.74 (s, 1H), 3.93-3.89 (m, 2H), 3.78-3.65 (m, 1H), 3.57 (s, 3H), 2.62-2.58 (m, 2H), 2.31-2.27 (m, 2H), 2.21-2.05 (m, 2H), 1.84-1.80 (m, 1H), 1.63-1.46 (m, 5H), 1.38 (s, 9H), 1.33-1.20 (m, 2H) |
| G-3-76 | 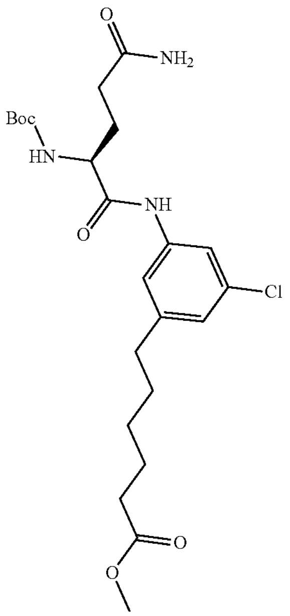 [SMILES: COC(=O)CCCCCc1cc(Cl)cc(NC(=O)[C@H](CCC(N)=O)NC(=O)OC(C)(C)C)c1] | methyl 6-[3-[(2S)-2-[(tert-butoxycarbonyl) amino]-4-carbamoylbutanamido]-5-chlorophenyl] hexanoate | 484.15 | (300 MHz, DMSO-$d_6$) δ 10.08 (s, 1H), 7.63 (d, J = 2.0 Hz, 1H), 7.28 (s, 2H), 7.06 (d, J = 7.5 Hz, 1H), 6.95 (d, J = 1.7 Hz, 1H), 6.76 (s, 1H), 4.03-3.95 (m, 1H), 3.56 (s, 3H), 2.54 (d, J = 7.6 Hz, 2H), 2.29 (t, J = 7.3 Hz, 2H), 2.22-2.06 (m, 2H), 1.91-1.68 (m, 2H), 1.37 (s, 9H), 1.35-1.26 (m, 6H) |

TABLE 28-continued

| Intermediates prepare according to Step 3 above. | | | | |
|---|---|---|---|---|
| Inter-mediate | Structure | Chemical Name | MS: $[(M+1)]^+$ | $^1H$-NMR |
| G-3-77 | 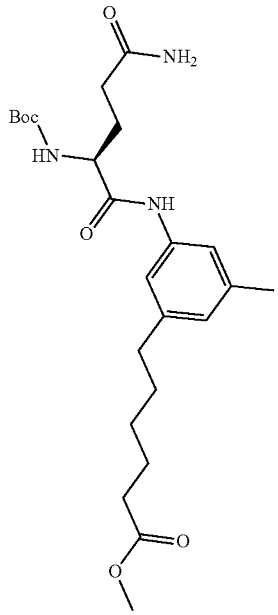 [SMILES: COC(=O)CCCCCc1cc(C)cc(NC(=O)[C@H](CCC(N)=O)NC(=O)OC(C)(C)C)c1] | Methyl 6-[3-[(2S)-2-[(tert-butoxycarbonyl) amino]-4-carbamoylbutanamido]-5-methylphenyl] hexanoate | 464.20 | (300 MHz, DMSO-$d_6$) δ 9.78 (s, 1H), 7.32-7.26 (m, 2H), 7.22 (s, 1H), 7.00 (d, J = 7.7 Hz, 1H), 6.78 (s, 1H), 6.71 (s, 1H), 4.02 (d, J = 6.8 Hz, 1H), 3.59 (s, 3H), 2.31 (t, J = 7.4 Hz, 2H), 2.25 (s, 3H), 2.20-2.08 (m, 2H), 1.97-1.69 (m, 3H), 1.56 (pd, J = 7.4, 3.3 Hz, 5H), 1.40 (s, 9H), 1.37-1.23 (m, 2H) |
| G-3-78 | 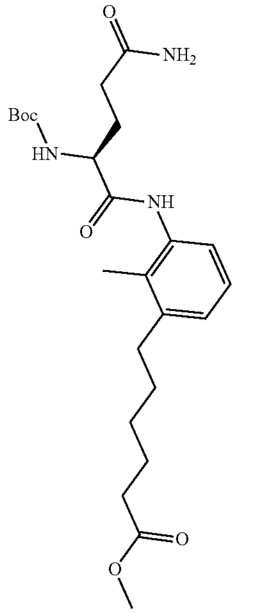 [SMILES: COC(=O)CCCCCc1cccc(NC(=O)[C@H](CCC(N)=O)NC(=O)OC(C)(C)C)c1C] | methyl 6-[3-[(2S)-2-[(tert-butoxycarbonyl) amino]-4-carbamoylbutanamido]-2-methylphenyl] hexanoate | 464.25 | (300 MHz, DMSO-$d_6$) δ 9.27 (d, J = 5.3 Hz, 1H), 7.32 (s, 1H), 7.18 (d, J = 7.6 Hz, 1H), 7.09-6.99 (m, 3H), 6.80 (s, 1H), 4.13-4.04 (m, 1H), 3.60 (s, 3H), 2.60 (t, J = 7.7 Hz, 2H), 2.32 (t, J = 7.4 Hz, 2H), 2.20 (d, J = 5.3 Hz, 2H), 2.12 (s, 3H), 2.06-1.74 (m, 2H), 1.64-1.47 (m, 3H), 1.42 (s, 9H), 1.38-1.31 (m, 3H) |

TABLE 28-continued

| Intermediates prepare according to Step 3 above. | | | | |
|---|---|---|---|---|
| Intermediate | Structure | Chemical Name | MS: $[(M + 1)]^+$ | $^1$H-NMR |
| G-3-79 | 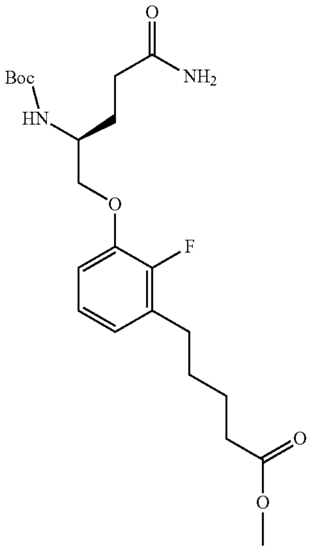 [SMILES: COC(=O)CCCCc1cccc(OC[C@H](CCC(N)=O)NC(=O)OC(C)(C)C)c1F] | methyl 5-[3-[(2S)-2-[(tert-butoxycarbonyl)amino]-4-carbamoylbutoxy]-2-fluorophenyl]pentanoate | 441.20 | (400 MHz, DMSO-$d_6$) δ 7.27 (s, 1H), 7.04-6.97 (m, 2H), 6.85-6.81 (m, 2H), 6.74 (s, 1H), 4.11 (q, J = 5.3 Hz, 1H), 3.91 (d, J = 6.1 Hz, 2H), 3.76-3.72 (m, 1H), 3.58 (s, 3H), 2.58 (t, J = 7.1 Hz, 2H), 2.36-2.30 (m, 2H), 2.18-2.07 (m, 2H), 1.87-1.77 (m, 1H), 1.57-1.51 (m, 4H), 1.39 (s, 9H) |
| G-3-80 | 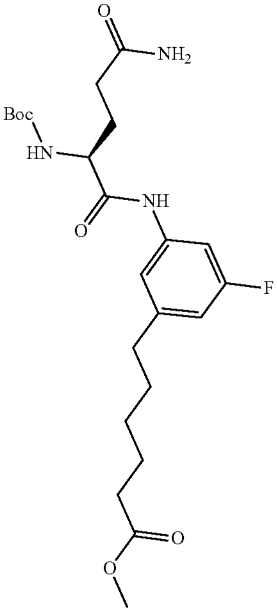 [SMILES: COC(=O)CCCCCc1cc(F)cc(NC(=O)[C@H](CCC(N)=O)NC(=O)OC(C)(C)C)c1] | methyl 6-[3-[(2S)-2-[(tert-butoxycarbonyl)amino]-4-carbamoylbutanamido]-5-fluorophenyl]hexanoate | 468.20 | (400 MHz, DMSO-$d_6$) δ 10.13 (s, 1H), 7.45-7.31 (m, 1H), 7.31 (s, 1H), 7.16 (t, J = 1.6 Hz, 1H), 7.09 (d, J = 7.6 Hz, 1H), 6.80 (s, 1H), 6.73 (dt, J = 9.8, 1.9 Hz, 1H), 4.04-4.02 (m, 1H), 3.58 (s, 3H), 2.56-2.54 (m, 2H), 2.30 (t, J = 7.4 Hz, 2H), 2.24-2.06 (m, 2H), 1.97-1.73 (m, 2H), 1.60-1.52 (m, 4H), 1.39 (s, 9H), 1.32-1.26 (m, 2H) |

TABLE 28-continued

| Intermediates prepare according to Step 3 above. | | | | |
|---|---|---|---|---|
| Inter-mediate | Structure | Chemical Name | MS: $[(M + 1)]^+$ | $^1$H-NMR |
| G-3-81 | 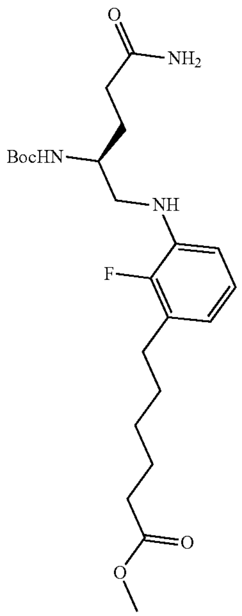 [SMILES: COC(=O)CCCCCc1cccc(NC[C@H](CCC(N)=O)NC(=O)OC(C)(C)C)c1F] | methyl 6-[3-([2-[(tert-butoxycarbonyl)amino]-4-carbamoylbutyl]amino)-2-fluorophenyl]hexanoate | 454.20 | (400 MHz, DMSO-$d_6$) δ 7.25 (s, 1H), 6.90-6.76 (m, 2H), 6.72 (s, 1H), 6.60 (t, J = 8.2 Hz, 1H), 6.41 (t, J = 7.1 Hz, 1H), 5.23 (s, 1H), 3.60-3.56 (m, 4H), 3.18 (s, 1H), 3.07-3.03 (m, 3H), 2.52 (d, J = 15.5 Hz, 1H), 2.29 (t, J = 7.4 Hz, 2H), 2.16-1.98 (m, 2H), 1.91-1.87 (m, 1H), 1.79-1.75 (m, 1H), 1.68-1.64 (m, 1H), 1.63-1.47 (m, 4H), 1.27 (s, 9H) |
| G-3-82 | 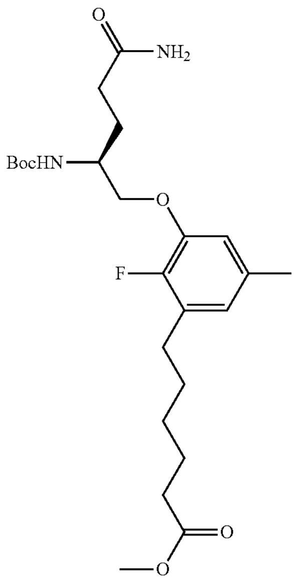 [SMILES: COC(=O)CCCCCc1cc(C)cc(OC[C@H](CCC(N)=O)NC(=O)OC(C)(C)C)c1F] | methyl 6-[3-[(2S)-2-[(tert-butoxycarbonyl)amino]-4-carbamoylbutoxy]-2-fluoro-5-methylphenyl]hexanoate | 469.30 | (400 MHz, DMSO-$d_6$) δ 7.27 (s, 1H), 6.86-6.76 (m, 2H), 6.74 (s, 1H), 6.61 (d, J = 6.0 Hz, 1H), 3.93-3.84 (m, 2H), 3.75-3.69 (m, 1H), 2.61-2.52 (m, 2H), 2.29 (t, J = 7.4 Hz, 2H), 2.23 (s, 3H), 2.17-2.05 (m, 2H), 1.88-1.75 (m, 1H), 1.65-1.47 (m, 6H), 1.39 (s, 9H), 1.34-1.22 (m, 4H) |

TABLE 28-continued

| Intermediates prepare according to Step 3 above. | | | | |
|---|---|---|---|---|
| Inter-mediate | Structure | Chemical Name | MS: $[(M + 1)]^+$ | $^1$H-NMR |
| G-3-83 | 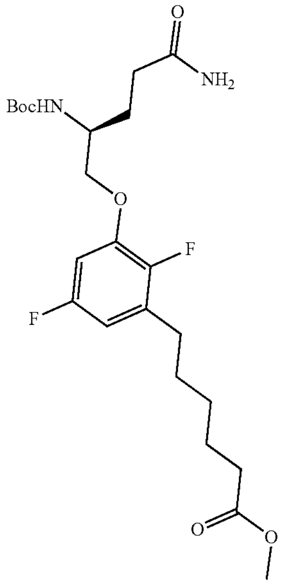 [SMILES: COC(=O)CCCCCc1cc(F)cc(OC[C@H](CCC(N)=O)NC(=O)OC(C)(C)C)c1F] | methyl 6-[3-[(2S)-2-[(tert-butoxycarbonyl) amino]-4-carbamoylbutoxy]-2,5-difluorophenyl] hexanoate | 473.20 | (400 MHz, CD3OD) δ 6.78-6.72 (m, 1H), 6.58-6.51 (m, 1H), 3.98 (d, J = 5.5 Hz, 2H), 3.88 (s, 1H), 3.64 (s, 3H), 2.62 (t, J = 7.6 Hz, 2H), 2.37-2.27 (m, 4H), 2.03-1.94 (m, 3H), 1.84-1.77 (m, 1H), 1.71-1.55 (m, 4H), 1.44 (s, 9H) |
| G-3-84 | 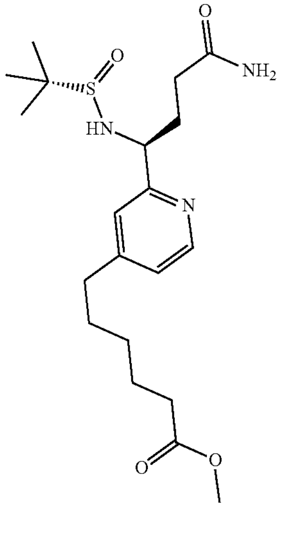 | methyl 6-[2-[(1S)-3-carbamoyl-1-[(2-methylpropane-2-sulfinyl)amino] propyl]pyridin-4-yl]hexanoate | 412.20 | (400 MHz, DMSO-$d_6$) δ 8.40 (d, J = 5.1 Hz, 1H), 7.29 (s, 1H), 7.21-7.09 (m, 2H), 6.80 (s, 1H), 5.74 (d, J = 5.5 Hz, 1H), 4.25-4.20 (m, 1H), 3.58 (s, 3H), 2.71-2.67 (m, 2H), 2.30-2.27 (t, J = 7.4 Hz, 2H), 2.16-2.01 (m, 3H), 1.93-1.78 (m, 1H), 1.69-1.62 (m, 2H), 1.59-1.51 (p, J = 7.5 Hz, 2H), 1.34-1.23 (m, 2H), 1.09 (s, 9H) |

TABLE 28-continued

Intermediates prepare according to Step 3 above.

| Intermediate | Structure | Chemical Name | MS: $[(M+1)]^+$ | $^1$H-NMR |
|---|---|---|---|---|
| G-3-85 | 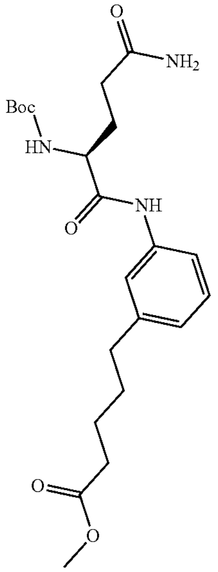 [SMILES: COC(=O)CCCCc1cccc(NC(=O)[C@H](CCC(N)=O)NC(=O)OC(C)(C)C)c1] | methyl 5-[3-[(2S)-2-[(tert-butoxycarbonyl)amino]-4-carbamoylbutanamido]phenyl]pentanoate | 436.25 | (300 MHz, DMSO-$d_6$) δ 9.88 (s, 1H), 7.68-7.64 (m, 2H), 7.44 (s, 2H), 7.20 (d, J = 8.2 Hz, 1H), 6.89 (d, J = 7.5 Hz, 1H), 3.59 (s, 3H), 3.19 (d, J = 5.3 Hz, 2H), 2.36-2.32 (m, 2H), 1.61-1.55 (m, 5H), 1.40 (s, 9H), 1.28-1.26 (m, 5H) |

Tert-butyl 2- [4-([[(2R,3S)-3- [(tert-butoxycarbonyl)amino]-5-carbamoylpentan-2-yl]oxy]methyl)phenyl] acetate (Intermediate G-3-23)

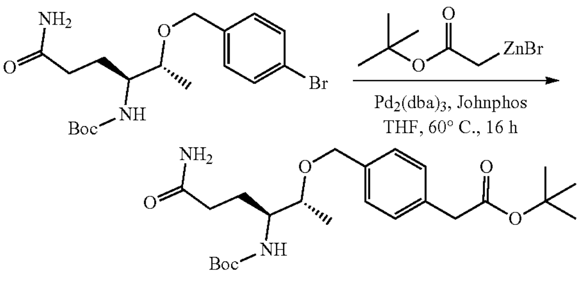

Intermediate G-3-23

To a stirred solution of tert-butyl N-[(3S,4R)-4-[(4-bromophenyl)methoxy]-1-carbamoylpentan-3-yl]carbamate (800 mg, 1.90 minol) and tert-butyl 3-bromopropanoate (806 mg, 3.90 minol) in THF (40.0 mL) were added $Pd_2(dba)_3.CHCl_3$ (399 mg, 0.39 minol) and X-Phos (368 mg, 0.77 minol) at room temperature under nitrogen atmosphere. The resulting mixture was stirred for 16 hours at 65° C. under nitrogen atmosphere. The resulting mixture was cooled down to room temperature and concentrated under reduced pressure. The residue was purified by reversed phase flash chromatography with the following conditions (Column: Spherical C18, 20~40 um, 330 g; Mobile Phase A: water (plus 0.0500 AcOH), Mobile Phase B: ACN; Flow rate: 45 mL/min; Gradient (B%): 5%~45%, 4 min; 45%~75%, 30 min; Detector: UV 254 nm. The fractions containing the desired product were collected at 70% B and concentrated under reduced pressure to afford the title compound as a brown oil (270 mg, 31%): $^1$H NMR (400 MHz, $CDCl_3$) δ 7.37-7.20 (m, 4H), 6.50 (s, 1H), 4.92 (d, J=9.6 Hz, 1H), 4.59 (d, J=11.6 Hz, 1H), 4.40 (d, J=11.6 Hz, 1H), 3.64 (ddd, J=16.5, 9.7, 3.2 Hz, 2H), 3.53 (s, 2H), 2.36-2.21 (m, 2H), 2.13-1.95 (m, 1H), 1.46-1.45 (m, 18H), 1.21 (d, J=6.3 Hz, 3H); MS (ESI, m/z): $[(M+1)]^+$=451.35.

Tert-butyl 2-[2-(2-[2-[4-([[(2R,3S)-3-[(tert-butoxycarbonyl)amino]-5-carbamoylpentan-2-yl]oxy]methyl)phenyl]ethoxy]ethoxy)ethoxy]acetate (Intermediate G-3-24)

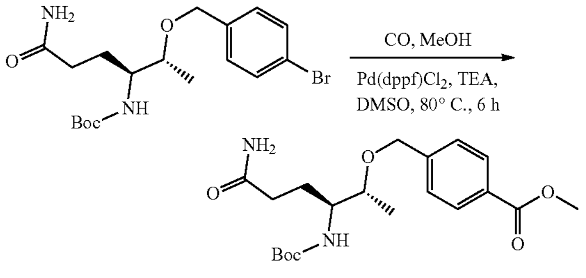

Intermediate G-3-24

To a stirred mixture of tert-butyl N-[(3S,4R)-4-[(4-bromophenyl)methoxy]-1-carbamoylpentan-3-yl]carbamate (400 mg, 0.96 mmol) in DMSO (4.00 mL) were added MeOH (13.0 mL), $Pd(dppf)Cl_2$ (70.5 mg, 0.096 mmol) and TEA (13.0 mL) at 25° C. under CO (1.5 atm.) atmosphere. The resulting mixture was purged with CO for three times and stirred for additional 16 hours at 80° C. The resulting mixture was cooled down to room temperature and concentrated under reduced pressure. The residue was purified by reversed phase flash chromatography with the following conditions: Column: WelFlash™ C18-I, 20~40 um, 40 g;

Eluent A: water (plus 10 mmol/L AcOH); Eluent B: ACN; Gradient: 35% - 55% B in 20 min; Flow rate: 30 mL/min; Detector: UV 220/200 nm; desired fractions were collected at 55% B and concentrated under reduced pressure to afford the title compound as a yellow solid (215 mg, 57%): $^{1}H$ NMR (400 MHz, DMSO-$d_6$) δ 7.96-7.89 (m, 2H), 7.48 (d, J=8.2 Hz, 2H), 7.22 (s, 1H), 6.71-6.62 (m, 2H), 4.63-4.52 (m, 2H), 3.85 (s, 3H), 3.45 (dd, J=14.4, 8.3 Hz, 2H), 2.12-2.00 (m, 1H), 1.93-1.70 (m, 1H), 1.54-1.45 (m, 1H), 1.38 (s, 9H), 1.09 (d, J=6.0 Hz, 3H); MS (ESI, m/z): $[(M+1)]^+$=395.30.

Tert-butyl 1-[4-([[(2R,3S)-3-[(tert-butoxycarbonyl) amino]-5-carbamoylpentan-2-yl]oxy]methyl)phenyl] piperidine-4-carboxylate (Intermediate G-3-38)

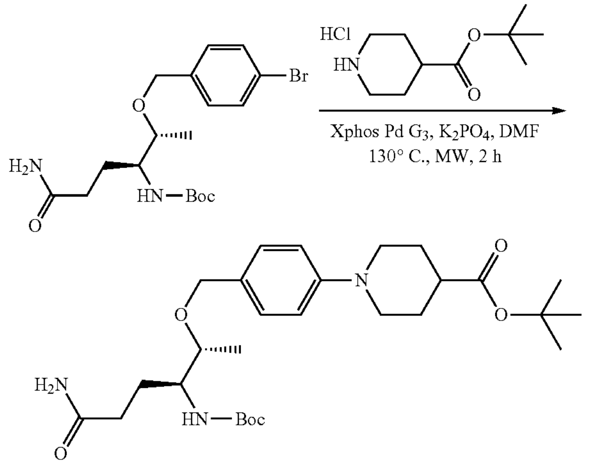

Intermediate G-3-38

To a stirred solution of tert-butyl N-[(3S,4R)-4-[(4-bromophenyl)methoxy]-1-carbamoylpentan-3-yl]carbamate (500 mg, 1.21 mmol) and tert-butyl piperidine-4-carboxylate hydrochloride (320 mg, 1.45 mmol) in DMF (10.0 mL) was added XPhos Pd $G_3$ (153 mg, 0.18 mmol) and $K_3PO_4$ (1022 mg, 4.82 mmol) at 25° C. under nitrogen atmosphere. The final reaction mixture was irradiated with microwave radiation for 2 h at 130° C. The mixture was allowed to cool down to room temperature. The reaction was purified by reverse phase flash chromatography with the following conditions: Column: Spherical C1[8] Column, 20~40 um, 120 g; Mobile Phase A: water (plus 0.05% $NH4HCO_3$), Mobile Phase B: ACN; Flow rate: 60 mL/min; Gradient: 30% B to 50% B in 25 min; Detector: UV 254/220 nm. The fractions containing the desired product were collected at 40% B to afford the title compound as a white solid (160 mg, 26%): $^{1}H$ NMR (400 MHz, $CD_3OD$) δ 7.27-7.23 (m, 2H), 6.99-6.94 (m, 2H), 4.53-4.40 (m, 2H), 3.63 (dt, J=12.5, 3.8 Hz, 2H), 3.56-3.54 (m, 1H), 3.50 (t, J=5.9 Hz, 1H), 2.82-2.74 (m, 2H), 2.40-2.38 (m, 1H), 2.27-2.25 (m, 2H), 2.02-1.93 (m, 3H), 1.80-1.76 (m, 2H), 1.62-1.60 (m, 1H), 1.48-1.46 (m, 18H), 1.16 (d, J=6.2 Hz, 3H); LC/MS (ESI, m/z): $[(M+Na)]^+$=542.30.

The intermediates in Table 29 were prepared according to the above procedure to prepare Intermediate G-3-38.

TABLE 29

Characterization data for intermediates prepared according to above.

| Intermediate | Structure | Chemical Name | MS: $[(M + 1)]^+$ | $^{1}H$-NMR |
|---|---|---|---|---|
| G-3-39 | 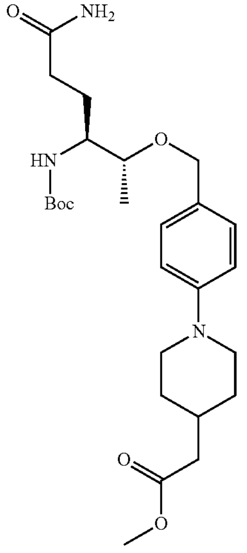 [SMILES: COC(=O)CC1CCN(c2ccc(CO[C@H](C)[C@H](CCC(N)=O)NC(=O)OC(C)(C)C)cc2)CC1] | methyl 2-[1-[4-([[(2R,3S)-3-[(tert-butoxycarbonyl) amino]-5-carbamoylpentan-2-yl]oxy]methyl) phenyl]piperidin-4-yl]acetate | 492.45 | (400 MHz, $CD_3OD$) δ 7.27-7.22 (m, 2H), 6.99-6.94 (m, 2H), 4.52-4.40 (m, 2H), 3.69 (s, 3H), 3.66 (d, J = 3.2 Hz, 1H), 3.59-3.53 (m, 1H), 3.51-3.46 (m, 1H), 2.75-2.68 (m, 2H), 2.33 (d, J = 7.0 Hz, 2H), 2.29-2.20 (m, 2H), 2.01-1.90 (m, 2H), 1.86-1.81 (m, 2H), 1.63-1.58 (m, 1H), 1.45 (s, 9H), 1.44-1.36 (m, 3H), 1.19-1.12 (m, J = 6.2 Hz, 3H) |

TABLE 29-continued

Characterization data for intermediates prepared according to above.

| Intermediate | Structure | Chemical Name | MS: $[(M + 1)]^+$ | $^1$H-NMR |
|---|---|---|---|---|
| G-3-40 | 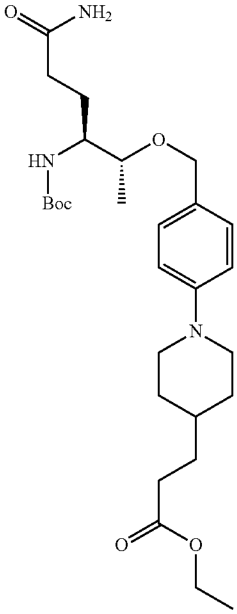 [SMILES: CCOC(=O)CCC1CCN(c2ccc(CO[C@H](C)[C@H](CCC(N)=O)NC(=O)OC(C)(C)C)cc2)CC1] | ethyl 3-[1-[4-([[(2R,3S)-3-[(tert-butoxycarbonyl)amino]-5-carbamoylpentan-2-yl]oxy]methyl)phenyl]piperidin-4-yl]propanoate | 520.05 | Used in the next step without further purification |
| G-3-41 | 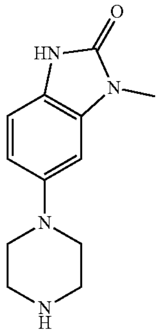 [SMILES: Cn1c(=O)[nH]c2ccc(N3CCNCC3)cc21] | 1-methyl-6-(piperazin-1-yl)-3H-1,3-benzodiazol-2-one | 233.10 | (400 MHz, DMSO-$d_6$) δ 10.54 (s, 1H), 6.82 (d, J = 8.4 Hz, 1H), 6.73 (s, 1H), 6.57 (d, J = 8.5 Hz, 1H), 3.24 (s, 3H), 3.04-2.97 (m, 4H), 2.94-2.86 (m, 4H), 1.42-1.37 (m, 1H) |

Ethyl 2-[4'-([[(2R,3S)-3-[(tert-butoxycarbonyl)amino]-5-carbamoylpentan-2-yl]oxy]methyl)-[1,1'-biphenyl]-3-yl]acetate (Intermediate G-3-42)

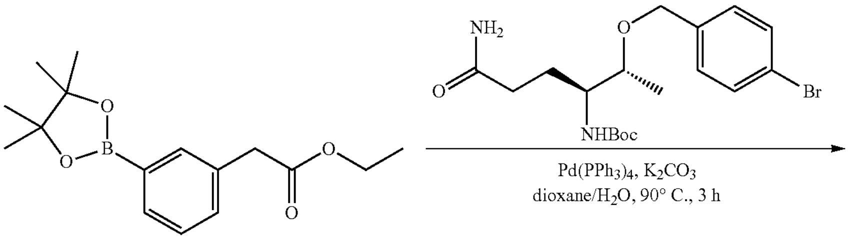

-continued

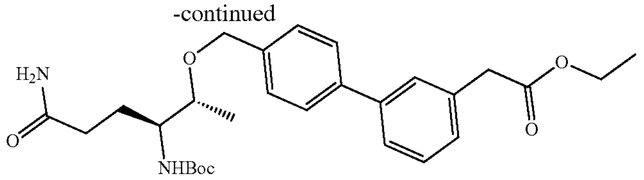

Intermediate G-3-42

To a stirred solution of ethyl 2-[3-(4,4,5,5-tetramethyl-1,3,2-dioxaborolan-2-yl)phenyl]acetate (0.70 g, 2.41 mmol) and tert-butyl N-[(3S,4R)-4-[(4-bromophenyl)methoxy]-1-carbamoylpentan-3-yl]carbamate (1.00 g, 2.41 mmol) in dioxane (10.0 mL) and $H_2O$ (1.00 mL) were added $K_2CO_3$ (0.67 g, 4.85 mmol) and $Pd(PPh_3)_4$(0.22 g, 0.19 mmol, 0.08 equiv) at 25° C. The resulting mixture was stirred for additional 3 h at 90° C. under nitrogen atmosphere. The resulting solution was cooled down to room temperature and was purified by reverse phase flash chromatography with the following conditions: Column: Spherical $C^{18}$ Column, 20~40 um, 120 g; Mobile Phase A: water (plus 0.1% HOAc), Mobile Phase B: ACN; Flow rate: 60 mL/min; Gradient: 50% B to 70% B in 25 min; Detector: UV 254/220 nm. The fractions containing the desired product were collected at 60% B and concentrated under reduced pressure to afford the title compound as a black solid (390 mg, 32%): $^1$H NMR (400 MHz, DMSO-$d_6$) δ 7.62 (d, J=8.2 Hz, 2H), 7.56 (dd, J=7.0, 1.4 Hz, 2H), 7.42 (t, J=8.3 Hz, 3H), 7.29-7.20 (m, 2H), 6.72-6.61 (m, 2H), 4.58-4.49 (m, 2H), 4.11 (q, J=7.1 Hz, 2H), 3.75 (s, 2H), 3.47 (m, J=11.7, 6.1 Hz, 2H), 2.12-2.03 (m, 2H), 1.85-1.81 (m, 1H), 1.56-1.45 (m, 1H), 1.40 (s, 9H), 1.21 (t, J=7.1 Hz, 3H), 1.10 (d, J=5.9 Hz, 3H); LC/MS (ESI, m/z): $[(M+1)]^+$=499.30.

The intermediates in Table 30 were prepared according to the above procedure to prepare Intermediate G-3-42.

TABLE 30

Characterization data for intermediates prepared according to above.

| Intermediate | Structure | Chemical Name | MS: $[(M + 1)]^+$ | $^1$H-NMR |
|---|---|---|---|---|
| G-3-43 | 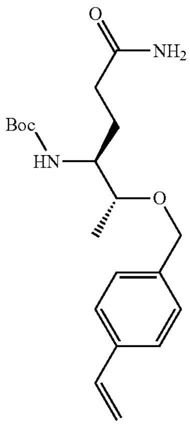 [SMILES: C=Cc1ccc(CO[C@H](C)[C@H](CCC(N)=O)NC(=O)OC(C)(C)C)cc1] | tert-butyl N-[(3S,4R)-1-carbamoyl-4-[(4-ethenylphenyl) methoxy]pentan-3-yl]carbamate | 263.10 | (400 MHz, DMSO-$d_6$) δ 7.43 (d, J = 8.1 Hz, 2H), 7.31 (d, J = 8.1 Hz, 2H), 7.27-7.19 (m, 1H), 6.76-6.61 (m, 3H), 5.82 (dd, J = 17.7, 1.1 Hz, 1H), 5.24 (dd, J = 11.0, 1.0 Hz, 1H), 4.54-4.39 (m, 2H), 3.48-3.37 (m, 2H), 2.12-1.97 (m, 2H), 1.83-1.77 (m, 1H), 1.52-1.44 (m, 1H), 1.38 (s, 9H), 1.07 (d, J = 6.0 Hz, 3H) |

Tert-butyl 2-(4-[[1-(2,6-dioxopiperidin-3-yl)-3-methyl-2-oxo-1,3-benzodiazol-5-yl]methyl]piperidin-1-yl)acetate (Intermediate G-3-44)

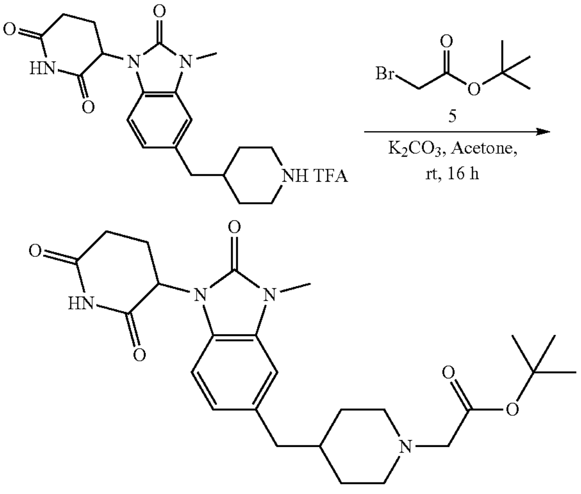

Intermediate G-3-44

To a stirred mixture of 3-[3-methyl-2-oxo-5-(piperidin-4-ylmethyl)-1,3-benzodiazol-1-yl]piperidine-2,6-dione trifluoroacetate (1.30 g, 0.003 mmol) and tert-butyl 2-bromoacetate (0.67 g, 3.44 mmol) in acetone (30.0 mL) was added $K_2CO_3$ (0.99 g, 7.16 mmol) at room temperature under nitrogen atmosphere. The resulting mixture was stirred for 16 h at room temperature under nitrogen atmosphere. The resulting mixture was filtered. The filtered cake was washed with DCM (3×5.00 mL). The combined filtrates was concentrated under reduced pressure. The residue was purified by reverse phase flash chromatography with the following conditions: Column: WelFlash™ C18-I, 20~40 um, 330 g; Eluent A: water (plus 10 mmol/LFA); Eluent B: ACN; Gradient: 25% - 50% B in 25 min; Flow rate: 80 mL/min; Detector: UV 220/254 nm; desired fractions were collected at 45% B and concentrated under reduced pressure to afford the title compound as a light yellow solid (1.0 g, 70%): $^1$H NMR (400 MHz, $CDCl_3$) δ 8.65 (s, 1H), 6.87-6.79 (m, 2H), 6.74 (d, J=8.0 Hz, 1H), 5.23 (dd, J=12.7, 5.4 Hz, 1H), 3.44 (s, 3H), 3.29 (d, J=10.8 Hz, 2H), 2.99-2.59 (m, 8H), 2.26-2.18 (m, 2H), 1.78-1.54 (m, 5H), 1.47 (s, 9H); LC/MS (ESI, m/z): $[(M+1)]^+$=471.15.

The intermediates in Table 31 were prepared according to the above procedure to prepare Intermediate G-3-44.

TABLE 31

| Intermediate | Structure | Chemical Name | MS: $[(M + 1)]^+$ | $^1$H-NMR |
|---|---|---|---|---|
| Characterization data for intermediates prepared according to above. | | | | |
| G-3-45 | 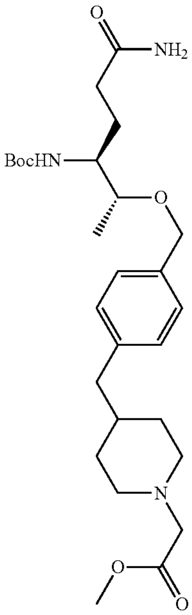 [SMILES: COC(=O)CN1CCC(Cc2ccc(CO[C@H](C)[C@H](CCC(N)=O)NC(=O)OC(C)(C)C)cc2)CC1] | methyl 2-(4-[[4-([[(2R,3S)-3-[(tert-butoxycarbonyl)amino]-5-carbamoylpentan-2-yl]oxy]methyl)phenyl]methyl]piperidin-1-yl)acetate | 506.35 | (400 MHz, DMSO-$d_6$) δ 7.28-7.19 (m, 3H), 7.11 (d, J = 7.8 Hz, 2H), 6.68 (s, 1H), 6.61 (d, J = 9.0 Hz, 1H), 4.52-4.38 (m, 2H), 3.59 (s, 3H), 3.44-3.40 (m, 2H), 3.17 (s, 2H), 2.78 (dt, J = 11.3, 3.4 Hz, 2H), 2.48 (d, J = 6.8 Hz, 2H), 2.19-1.94 (m, 4H), 1.81-1.78 (m, 1H), 1.52-1.48 (m, 3H), 1.40 (s, 9H), 1.22-1.14 (m, 2H), 1.06 (d, J = 6.0 Hz, 3H) |

Tert-butyl 2-(4-[[1-(2,6-dioxopiperidin-3-yl)-3-methyl-2-oxo-1,3-benzodiazol-5-yl]methyl]piperazin-

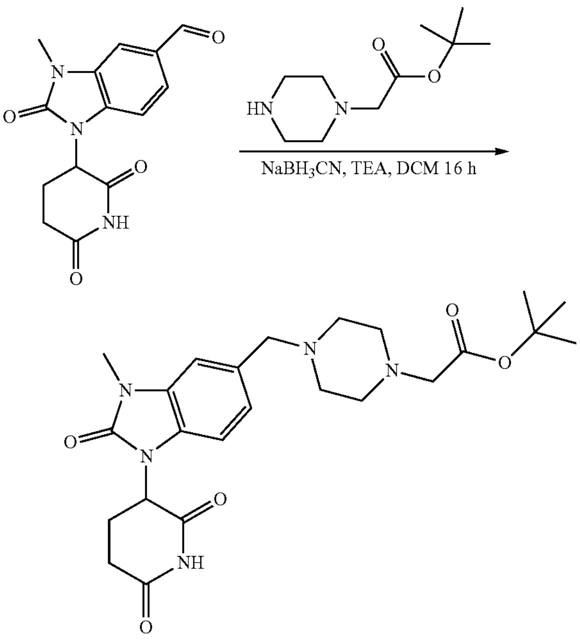

Intermediate G-3-46

To a stirred mixture of 1-(2,6-dioxopiperidin-3-yl)-3-methyl-2-oxo-1,3-benzodiazole-5-carbaldehyde (500 mg, 1.74 mmol) and tert-butyl 2-(piperazin-1-yl)acetate (697.18 mg, 3.481 mmol) in DCM (10.00 mL) was added TEA (352.24 mg, 3.481 mmol) at room temperature under nitrogen atmosphere. To the above mixture were added $NaBH_3CN$ (218.75 mg, 3.481 mmol) and AcOH (0.50 mL) at room temperature. The resulting mixture was stirred for overnight at room temperature. The resulting mixture was concentrated under reduced pressure. The residue product was purified by reverse phase flash chromatography with the following conditions: Column: Spherical C18, 20~40 um, 330 g; Mobile Phase A: water (plus 0.05% TFA), Mobile Phase B: ACN; Flow rate: 80 mL/min; Gradient B1: 30 4-65, 30 min; Detector: UV 254/220 nm; Rt: 35 min to afford the title compound as a light yellow solid (200 mg, 240%): $^1$H NMR (400 MHz, $CDCl_3$) 8.65 (s, 1H), 6.87-6.79 (m, 2H), 6.74 (d, J=8.0 Hz, 1H), 5.23 (dd, J=12.7, 5.4 Hz, 1H), 4.07 (s, 2H), 3.44 (s, 3H), 3.30-3.26 (m, 2H), 2.99-2.59 (m, 11H), 2.26-2.18 (m, 1H), 1.47 (s, 9H); LC/MS (ESI, m/z): [(M+1)$^+$=472.15

The intermediates in Table 32 were prepared according to the above procedure to prepare Intermediate G-3-46.

TABLE 32

Characterization data for intermediates prepared according to above.

| Intermediate | Structure | Chemical Name | MS: $[(M + 1)]^+$ | $^1$H-NMR |
|---|---|---|---|---|
| G-3-47 | 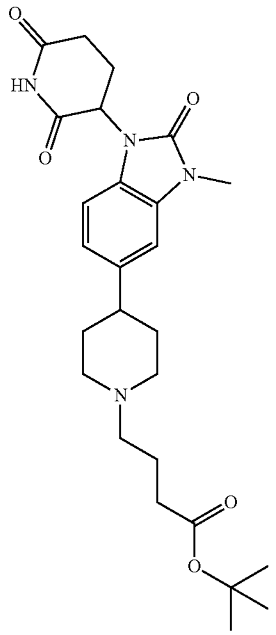 [SMILES: Cn1c(=O)n(C2CCC(=O)NC2=O)c2ccc(C3CCN(CCCC(=O)OC(C)(C)C)CC3)cc21] | tert-butyl 4-[4-[1-(2,6-dioxopiperidin-3-yl)-3-methyl-2-oxo-1,3-benzodiazol-5-yl]piperidin-1-yl]butanoate | 485.20 | (400 MHz, DMSO-$d_6$) δ 11.10 (s, 1H), 7.14-6.99 (m, 2H), 6.92 (d, J = 8.1 Hz, 1H), 5.36 (dd, J = 12.7, 5.5 Hz, 1H), 3.56-3.48 (m, 2H), 3.35 (s, 3H), 3.14-2.78 (m, 4H), 2.76-2.56 (m, 3H), 2.33 (dd, J = 7.5, 3.0 Hz, 2H), 2.22 (t, J = 7.5 Hz, 2H), 2.07-1.84 (m, 6H), 1.43 (s, 9H) |
| G-3-48 | 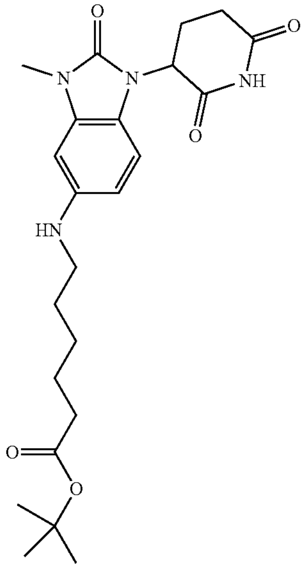 [SMILES: Cn1c(=O)n(C2CCC(=O)NC2=O)c2ccc(NCCCCCC(=O)OC(C)(C)C)cc21] | tert-butyl 6-[[1-(2,6-dioxopiperidin-3-yl)-3-methyl-2-oxo-1,3-benzodiazol-5-yl]amino]hexanoate | 445.25 | (400 MHz, $CDCl_3$) δ 8.11 (s, 1H), 6.62 (d, J = 8.4 Hz, 1H), 6.39-6.30 (m, 2H), 5.18 (dd, J = 12.7, 5.4 Hz, 1H), 3.40 (s, 3H), 3.14 (t, J = 7.1 Hz, 2H), 2.99-2.90 (m, 1H), 2.89-2.77 (m, 1H), 2.72-2.68 (m, 1H), 2.30-2.18 (m, 3H), 2.03 (s, 3H), 1.7-1.62 (m, 1H), 1.69-1.65 (m, 3H), 1.47 (s, 9H) |

TABLE 32-continued

| Characterization data for intermediates prepared according to above. | | | | |
|---|---|---|---|---|
| Intermediate | Structure | Chemical Name | MS: $[(M + 1)]^+$ | $^1$H-NMR |
| G-3-49 | 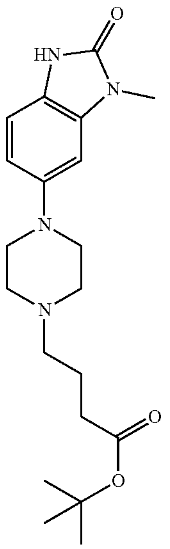 [SMILES: Cn1c(=O)[nH]c2ccc(N3CCN(CCCC(=O)OC(C)(C)C)CC3)cc21] | tert-butyl 4-[4-(3-methyl-2-oxo-1H-1,3-benzodiazol-5-yl)piperazin-1-yl]butanoate | 375.20 | (400 MHz, DMSO-$d_6$) δ 10.52 (s, 1H), 6.83 (d, J = 8.4 Hz, 1H), 6.75 (s, 1H), 6.59 (d, J = 8.5 Hz, 1H), 3.24 (s, 3H), 3.16-3.08 (m, 4H), 2.75-2.68 (m, 4H), 2.26 (t, J = 7.2 Hz, 2H), 1.96-1.89 (m, 2H), 1.78-1.69 (m, 2H), 1.41 (s, 9H) |

Tert-butyl 3-[4-[1-(2,6-dioxopiperidin-3-yl)-3-methyl-2-oxo-1,3-benzodiazol-5-yl]piperidin-1-yl]propanoate (Intermediate G-3-50)

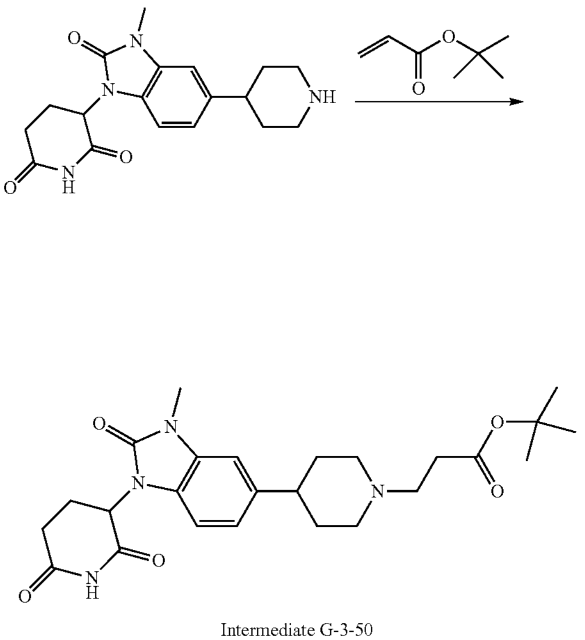

Intermediate G-3-50

To a stirred solution of 3-[3-methyl-2-oxo-5-(piperidin-4-yl)-1,3-benzodiazol-1-yl]piperidine-2,6-dione; trifluoroacetic acid (600 mg, 1.32 mmol) and tert-butyl prop-2-enoate (350.83 mg, 2.737 mmol) in EtOH (15.00 mL) was added TEA (415.46 mg, 4.106 mmol) at room temperature under nitrogen atmosphere. The resulting mixture was stirred for 2 h at 80° C. under nitrogen atmosphere. The resulting mixture was concentrated under reduced pressure to afford the title compound as a yellow oil (600 mg, 79%): $^1$H NMR (400 MHz, DMSO-d4) δ 11.09 (s, 1H), 7.13-6.99 (m, 2H), 6.98-6.84 (m, 1H), 5.35 (dd, J=12.7, 5.4 Hz, 1H), 3.45 (q, J=7.1 Hz, 1H), 3.34 (s, 3H), 2.98-2.86 (m, 3H), 2.80-2.53 (m, 5H), 2.07-1.69 (m, 8H), 1.43 (s, 9H); LC/MS (ESI, m/z): $[(M+1)]^+$=471.15.

The intermediates in Table 33 were prepared according to the above procedure to prepare Intermediate G-3-50.

TABLE 33

| Characterization data for intermediates prepared according to above. | | | | |
|---|---|---|---|---|
| Intermediate | Structure | Chemical Name | MS: $[(M + 1)]^+$ | $^1$H-NMR |
| G-3-51 | 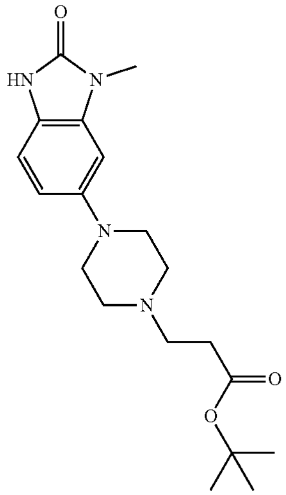 [SMILES: Cn1c(=O)[nH]c2ccc(N3CCN(CCC(=O)OC(C)(C)C)CC3)cc21] | tert-butyl 3-[4-(3-methyl-2-oxo-1H-1,3-benzodiazol-5-yl)piperazin-1-yl]propanoate | 361.15 | (400 MHz, DMSO-$d_6$) δ 10.50 (s, 1H), 6.81 (d, J = 8.4 Hz, 1H), 6.74 (s, 1H), 6.57 (d, J = 8.5 Hz, 1H), 3.24 (s, 3H), 3.08-3.02 (m, 4H), 2.59 (t, J = 7.1 Hz, 2H), 2.60-2.54 (m, 2H), 2.52-2.46 (m, 2H), 2.39 (t, J = 7.1 Hz, 2H), 1.40 (s, 9H) |

Tert-butyl 2-[(1s, 4s)-4-[[1-(2,6-dioxopiperidin-3-yl)-3-methyl-2-oxo-1,3-benzodiazol-5-yl]methyl]cyclohexyl]acetate (Intermediate G-3-52) and tert-butyl 2-[(1r, 4r)-4-[[1-(2,6-dioxopiperidin-3-yl)-3-methyl-2-oxo-1,3-benzodiazol-5-yl]methyl]cyclohexyl]acetate (Intermediate G-3-53)

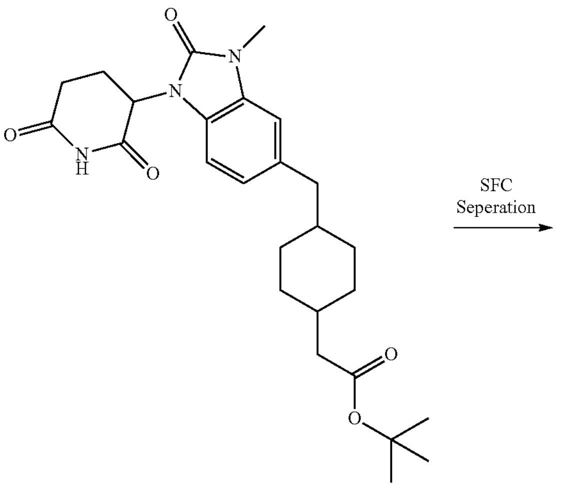

Intermediate G-3-36

-continued

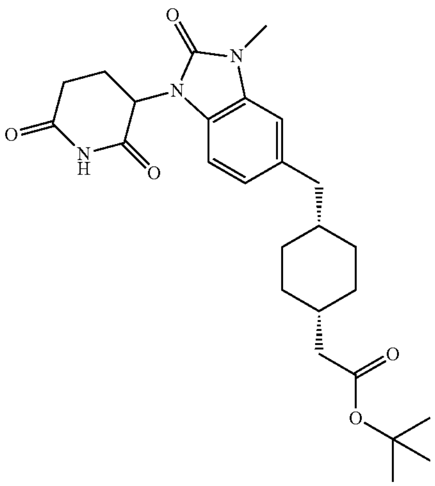

Intermediate G-3-52

-continued

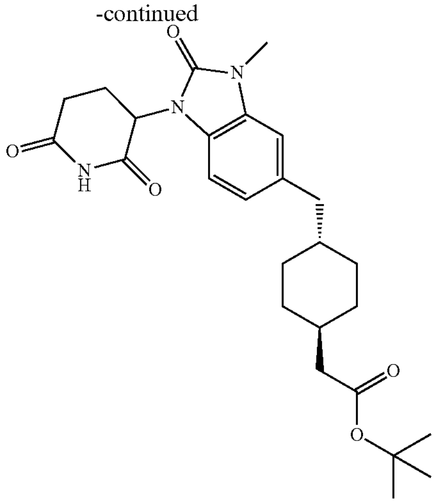

Intermediate G-3-53

A mixture of tert-butyl 2-(4-[[1-(2,6-dioxopiperidin-3-yl)-3-methyl-2-oxo-1,3-benzodiazol-5-yl]methyl]cyclohexyl)acetate (13.00 g) was separated by SFC with the following conditions: Column: CHIRAL ART Amylose-SC, 5×25 cm (5 um); Mobile Phase A: $CO_2$, Mobile Phase B: IPA:MeCN=1:1; Flow rate: 200 mL/min; Gradient: 50% B; Detector: UV 220/254 nm; RTL: 5.28 min; RT2: 10.29 min; The first peak fractions (RT1: 5.28 min) were collected and concentrated in vacuum to give compound 1 (S configuration, assumed) 5.3 g. The second peak fractions (RT2: 10.29 min) were collected and concentrated in vacuum to give compound 2 (R configuration, assumed) 5.6 g. Compound 1 was further separated by SFC with the following conditions: Column: Phenomenex Lux 5u Cellulose-3, 5×25 cm, 5 um; Mobile Phase A: $CO_2$, Mobile Phase B: MeOH; Flow rate: 150 mL/min; Gradient: 40% B; Detector: UV 220/254 nm; RT11: 4.84 min; RT12: 6.2 min; The compound 2 was further separated by SFC with the following conditions: Column: Phenomenex Lux 5u Cellulose-3, 5×25 cm, 5 um; Mobile Phase A: $CO_2$, Mobile Phase B: MeOH; Flow rate: 200 mL/min; Gradient: 50% B; Detector: UV 220/254 nm; RT21: 2.98 min; RT22: 4.58 min.

The two first peak fractions (RT11: 4.84 min and RT21: 2.98 min) were mixed and concentrated in vacuum to give the title cis-intermediate G-3-52 as an off-white solid (6 g, 44%): $^1$H NMR (400 MHz, $CDCl_3$) δ 8.32 (s, 1H), 6.87 (dd, J 8.0, 1.5 Hz, 1H), 6.83 (d, J 1.5 Hz, 1H), 6.73 (d, J 8.0 Hz, 1H), 5.24 (dd, J 12.6, 5.3 Hz, 1H), 3.45 (s, 3H), 3.01-2.95 (m, 1H), 2.88-2.68 (m, 2H), 2.63 (d, J 7.5 Hz, 2H), 2.28-2.23 (m, 3H), 2.03-2.01 (m, 1H), 1.81-1.68 (m, 1H), 1.50-1.45 (m, 15H), 1.40-1.26 (m, 2H); LC/MS (ESI, m/z): $[(M+1-56)]^+$=414.15.

The two second peak fractions (RT12: 6.2 min and RT22: 4.58 min) were mixed and concentrated in vacuum to give the title trans-intermediate G-3-53 as an off-white solid. (2 g, 14%): $^1$H NMR (400 MHz, $CDCl_3$) δ N—H (not shown), 6.86 (dd, J 8.0, 1.5 Hz, 1H), 6.82 (d, J 1.5 Hz, 1H), 6.72 (d, J 8.0 Hz, 1H), 5.27 (dd, J 12.6, 5.3 Hz, 1H), 3.45 (s, 3H), 2.98-2.87 (m, 2H), 2.82-2.62 (m, 1H), 2.54 (d, J 7.1 Hz, 2H), 2.26-2.23 (m, 1H), 2.08-2.05 (m, 2H), 1.76-1.72 (m, 4H), 1.56-1.38 (m, 11H), 1.02-0.95 (m, 4H); LC/MS (ESI, m/z): $[(M+1-56)]^+$=414.15.

Benzyl 4-[1-[1-(2,6-dioxopiperidin-3-yl)-3-methyl-2-oxo-1,3-benzodiazol-5-yl]azetidin-3-yl]butanoate (Intermediate G-3-54)

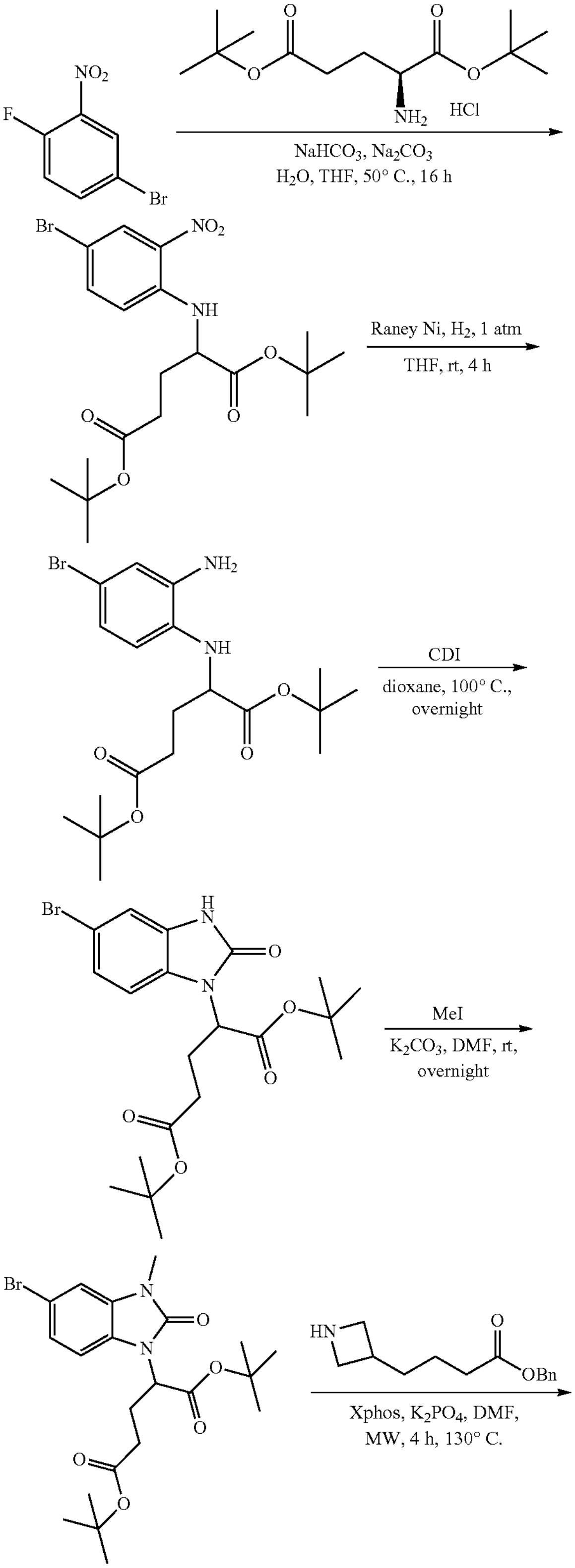

-continued

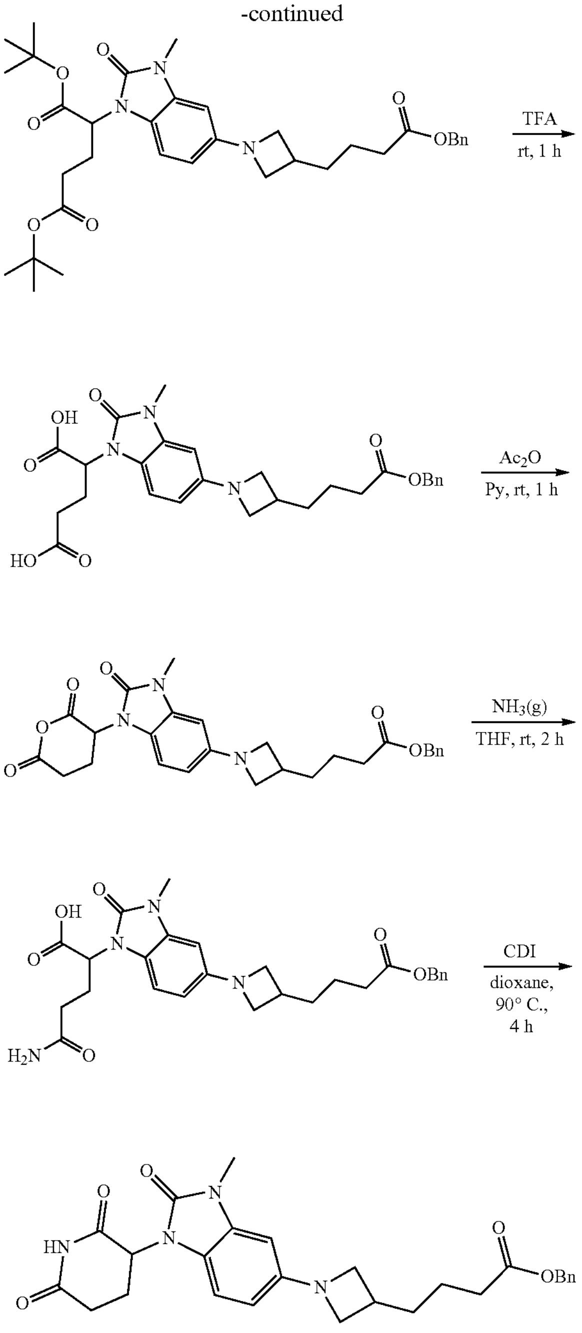

Intermediate G-3-54

Step 1. 1,5-Di-tert-butyl 2-(4-bromo-2-nitrophenyl) amino]pentanedioate. A solution of 4-bromo-1-fluoro-2-nitrobenzene (498.9 g, 2.26 mol), 1,5-di-tert-butyl (2S)-2-aminopentanedioate hydrochloride (806.74 g, 2.73 mol) and $Na_2CO_3$ (963.54 g, 9.09 mol) in THF (3.00 L)/$H_2O$ (3.00 L) was stirred for 24 h at 60° C. under nitrogen atmosphere. The resulting solution was cooled down to room temperature and was diluted with water (2 L). The mixture was extracted with petroleum ether (2×3 L). The combined organic phase was acidified to pH 5 with aqueous HCl (0.5 M, 2 L). The combined organic phase was washed with water (2×3 L), brine (2 L), dried with $Na_2SO_4$ and filtered. The filtrate was concentrated under reduced pressure to afford the title compound as a yellow oil (1000 g, 96%): $^1$H NMR (400 MHz, DMSO-d4) δ 8.27 (d, J=7.6 Hz, 1H), 8.20 (d, J=2.4 Hz, 1H), 7.70 (dd, J=9.2, 2.4 Hz, 1H), 7.03 (d, J=9.3 Hz, 1H), 4.55-4.46 (m, 1H), 2.40-2.28 (m, 2H), 2.17-1.99 (m, 2H), 1.44 (s, 9H), 1.35 (s, 9H); LC/MS (ESI, m/z): [(M+1)]$^+$=459.05, 461.05.

Step 2. 1,5-Di-tert-butyl 2-[(2-amino-4-bromophenyl) amino]pentanedioate. The title compound was prepared according to the procedure of step 5 to prepare Intermediate A. $^1$H NMR (400 MHz, DMSO-$d_6$) δ 6.69 (d, J=2.4 Hz, 1H), 6.65-6.52 (m, 1H), 6.18 (d, J=8.4 Hz, 1H), 4.98 (s, 2H), 4.76 (d, J=9.2 Hz, 1H), 3.82-3.76 (m, 1H), 2.40 (t, J=7.4 Hz, 2H), 1.99-1.85 (m, 2H), 1.40 (d, J=6.2 Hz, 18H); LC/MS (ESI, m/z): [(M+1)]$^+$=429.20, 431.20.

Step 3. 1,5-Di-tert-butyl 2-(5-bromo-2-oxo-3H-1,3-benzodiazol-1-yl)pentanedioate. A solution of 1,5-di-tert-butyl 2-[(2-amino-4-bromophenyl)amino]pentanedioate (950.00 g, 2.21 mol) and CDI (717.55 g, 4.43 mol) in dioxane (12.00 L) was stirred for overnight at 90° C. under nitrogen atmosphere. The mixture was allowed to cool down to room temperature. The resulting mixture was concentrated under reduced pressure. The residue was purified by trituration with water (10 L)/petroleum ether (10 L). The resulting mixture was filtered. The filter cake was washed with water (2×5 L) and dried under reduced pressure to afford the title compound as a light pink solid (760 g, 75%): $^1$H NMR (400 MHz, $CD_3OD$) δ 7.27-7.18 (m, 2H), 7.08 (d, J=1.0 Hz, 1H), 6.98 (d, J=8.3 Hz, 1H), 5.04 (dd, J=10.7, 5.1 Hz, 1H), 2.56-2.32 (m, 2H), 2.24 (dd, J=7.6, 6.4 Hz, 2H), 1.40 (d, J=11.9 Hz, 18H); LC/MS (ESI, m/z): [(M+1)]$^+$=455.05, 457.05.

Step 4. 1,5-Di-tert-butyl (2-(5-bromo-3-methyl-2-oxo-1,3-benzodiazol-1-yl)pentanedioate. To a stirred solution of 1,5-di-tert-butyl 2-(5-bromo-2-oxo-3H-1,3-benzodiazol-1-yl)pentanedioate (760.00 g, 1.67 mol) and $K_2CO_3$ (922.69 g, 6.68 mol) in DMF (3.50 L) was added $CH_3I$ (592.26 g, 4.17 mol) at room temperature under nitrogen atmosphere. The resulting mixture was stirred for overnight at room temperature under nitrogen atmosphere. The resulting solution was diluted with water (30 L) and triturated for 2 h. After filtration, the filter cake was triturated with petroleum ether (10 L) for 2 h again. The resulting mixture was filtered. The filter cake was washed with petroleum ether (1 L) and dried under reduced pressure to afford the title compound as a white solid (675 g, 86%): $^1$H NMR (400 MHz, $CD_3OD$) δ 7.39 (d, J=1.8 Hz, 1H), 7.26 (dd, J=8.4, 1.9 Hz, 1H), 7.02 (d, J=8.4 Hz, 1H), 5.07 (dd, J=10.7, 5.1 Hz, 1H), 3.43 (s, 3H), 2.56-2.34 (m, 2H), 2.23 (dd, J=7.6, 6.4 Hz, 2H), 1.40 (d, J=14.9 Hz, 18H); LC/MS (ESI, m/z): [(M+1)]$^+$=469.30, 471.30.

Step 5. 1,5-Dibutyl 2-(5-[3-[4-(benzyloxy)-4-oxobutyl] azetidin-1-yl]-3-methyl-2-oxo-1,3-benzodiazol-1-yl)pentanedioate. The title compound was prepared according to the procedure to prepare Intermediate G-3-39. $^1$H NMR (400 MHz, DMSO-$d_6$) δ 7.42-7.23 (m, 5H), 6.85 (d, J=8.4 Hz, 1H), 6.26 (d, J=2.1 Hz, 1H), 6.08 (dd, J=8.4, 2.2 Hz, 1H), 5.10 (s, 2H), 4.91 (dd, J=10.3, 5.1 Hz, 1H), 3.89 (t, J=7.3 Hz, 2H), 3.36-3.34 (m, 3H), 3.27 (s, 3H), 2.72-2.59 (m, 1H), 2.46-2.36 (m, 2H), 2.36-2.19 (m, 2H), 2.19-2.03 (m, 2H), 1.56 (q, J=7.2, 5.3 Hz, 3H), 1.34 (d, J=7.6 Hz, 18H); LC/MS (ESI, m/z): [(M+1)]+=622.50.

The intermediates in Table 34 were prepared according to step 5 of the procedure to prepare Intermediate G-3-54.

TABLE 34

Characterization data for intermediates prepared according to above.

| Intermediate | Structure | Chemical Name | MS: [(M + 1)]$^+$ | $^1$H-NMR |
|---|---|---|---|---|
| G-5-1 | 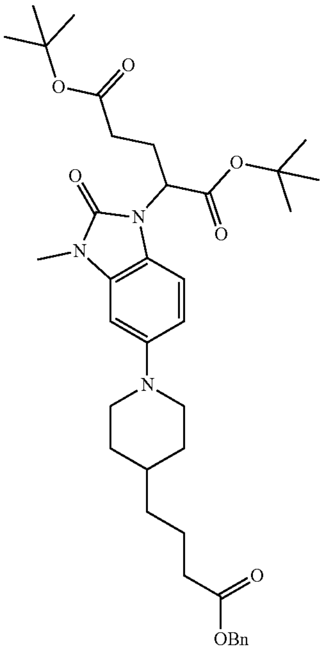 [SMILES: Cn1c(=O)n(C(CCC(=O)OC(C)(C)C)C(=O)OC(C)(C)C)c2ccc(N3CCC(CCCC(=O)OCc4ccccc4)CC3)cc21] | 1,5-dibutyl 2-(5-[4-[4-(benzyloxy)-4-oxobutyl]piperidin-1-yl]-3-methyl-2-oxo-1,3-benzodiazol-1-yl)pentanedioate | 650.50 | (400 MHz, DMSO-$d_6$) δ 7.41-7.29 (m, 5H), 6.88 (d, J = 8.6 Hz, 1H), 6.80 (d, J = 2.2 Hz, 1H), 6.62 (dd, J = 8.6, 2.3 Hz, 1H), 5.09 (d, J = 4.2 Hz, 2H), 4.92 (dd, J = 10.3, 5.1 Hz, 1H), 3.57 (d, J = 11.8 Hz, 2H), 3.29 (s, 3H), 2.58 (t, J = 11.6 Hz, 2H), 2.37 (t, J = 7.3 Hz, 2H), 2.32-2.20 (m, 2H), 2.20-2.06 (m, 2H), 1.73 (d, J = 12.2 Hz, 2H), 1.64-1.57 (m, 3H), 1.34 (d, J = 10.5 Hz, 18H), 1.28-1.21 (m, 4H) |

Step 6. 2-(5-[3-[4-(Benzyloxy)-4-oxobutyl]azetidin-1-yl]-3-methyl-2-oxo-1,3-benzodiazol-1-yl)pentanedioic acid. A mixture of 1,5-dibutyl 2-(5-[3-[4-(benzyloxy)-4-oxobutyl]azetidin-1-yl]-3-methyl-2-oxo-1,3-benzodiazol-1-yl)pentanedioate (1.80 g, 2.895 mmol) in TFA (25.00 mL) was stirred for 1 h at room temperature under nitrogen atmosphere. The resulting mixture was concentrated under reduced pressure to give the crude title compound (2.6 g), which was used in the next step directly without further purification: LC/MS (ESI, m/z): [(M+1)]$^+$=510.20.

The intermediates in Table 35 were prepared according to step 6 of the procedure to prepare Intermediate G-3-54.

TABLE 35

| Characterization data for intermediates prepared according to above. | | | | |
|---|---|---|---|---|
| Intermediate | Structure | Chemical Name | MS: $[(M + 1)]^+$ | $^1$H-NMR |
| G-6-1 | 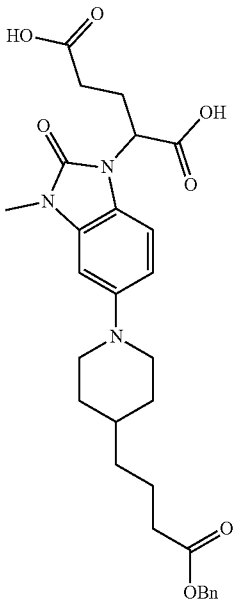 [SMILES: Cn1c(=O)n(C(CCC(=O)O)C(=O)O)c2ccc(N3CCC(CCCC(=O)OCc4ccccc4)CC3)cc21] | 2-(5-[4-[4-(benzyloxy)-4-oxobutyl]piperidin-1-yl]-3-methyl-2-oxo-1,3-benzodiazol-1-yl)pentanedioic acid | 538.20 | Used in the next step without further purification |

Step 7. Benzyl 4-b-(2.6-dioxooxan-3-yl)-3-methyl-2-oxo-1.3-benzodiazol-5-yl]azetidin-3-1 butanoate. A mixture of 2-(5-[3-[4-(benzyloxy)-4-oxobutyl]azetidin-1-yl]-3-methyl-2-oxo-1,3-benzodiazol-1-yl)pentanedioic acid (2.60 g, 5.102 mmol) and $Ac_2O$ (7.00 mL) in pyridine (20.00 mL) was stirred for 1 h at room temperature under nitrogen atmosphere. The resulting mixture was concentrated under reduced pressure to give the crude title compound (4.7 g), which was used in the next step directly without further purification: LC/MS (ESI m/z): $[(M+1)]^+$=492.35.

The intermediates in Table 36 were prepared according to step 7 of the procedure to prepare Intermediate G-3-54.

TABLE 36

| Characterization data for intermediates prepared according to above. | | | | |
|---|---|---|---|---|
| Intermediate | Structure | Chemical Name | MS: $[(M + 1)]^+$ | $^1$H-NMR |
| G-7-1 | 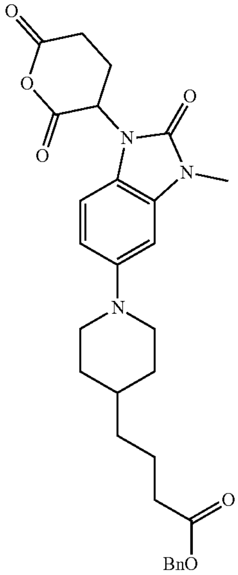 [SMILES: Cn1c(=O)n(C2CCC(=O)OC2=O)c2ccc(N3CCC(CCCC(=O)OCc4ccccc4)CC3)cc21] | benzyl 4-[1-[1-(2,6-dioxooxan-3-yl)-3-methyl-2-oxo-1,3-benzodiazol-5-yl]piperidin-4-yl]butanoate | 520.20 | Used in the next step without further purification |

Step 8. 2-(5-[3-[4-(Benzyloxy)-4-oxobutyl]azetidin-1-yl]-3-methyl-2-oxo-1.3-benzodiazol-1-yl)-4-carbamoylbutanoic acid. $NH_3$ (g) was bubbled in a stirred mixture of benzyl 4-[1-[1-(2,6-dioxooxan-3-yl)-3-methyl-2-oxo-1,3-benzodiazol-5-yl]azetidin-3-yl]butanoate (4.50 g, 9.155 mmol) in THF (30.00 mL) at room temperature for 30 min. The resulting mixture was stirred for 2 h at room temperature under nitrogen atmosphere. The resulting mixture was concentrated under reduced pressure. The residue was purified by reverse phase flash chromatography with the following conditions: Column: WelFlash™ C18-I, 20~40 um, 330 g; Eluent A: water (plus 10 mmol/L TFA); Eluent B: ACN; Gradient: 15% - 45% B in 25 min; Flow rate: 80 mL/min; Detector: UV 220/254 nm; desired fractions were collected at 35% B and concentrated under reduced pressure to afford the title compound as a yellow solid (1.5 g, 32%): $^1$H NMR (400 MHz, DMSO-d4) δ 7.38-7.32 (m, 6H), 7.23-7.20 (m, 1H), 6.95 (d, J=16.0 Hz, 1H), 6.73 (s, 1H), 6.56 (s, 1H), 6.34-6.32 (m, 1H), 5.10 (s, 3H), 4.95 (dd, J=10.8, 4.8 Hz, 1H), 4.06 (t, J=7.4 Hz, 2H), 3.64-3.54 (m, 3H), 2.77-2.68 (m, 1H), 2.40 (t, J=7.0 Hz, 3H), 2.06-1.95 (m, 1H), 1.94-1.86 (m, 1H), 1.65-1.52 (m, 6H); LC/MS (ESI, m/z): $[(M+1)]^+$=509.40.

The intermediates in Table 37 were prepared according to step 8 of the procedure to prepare Intermediate G-3-54.

Step 9. Benzyl 4-[1-[1-(2,6-dioxopiperidin-3-yl)-3-methyl-2-oxo-1,3-benzodiazol-5-yl]azetidin-3-yl]butanoate. The title compound was prepared according to the procedure of step 3 to prepare Intermediate G-3-54. $^1$H NMR (400 MHz, DMSO-$d_6$) δ 11.07 (s, 1H), 7.47-7.25 (m, 5H), 6.98 (d, J=8.4 Hz, 1H), 6.54 (s, 1H), 6.30 (d, J=8.5 Hz, 1H), 5.31 (dd, J=12.8, 5.3 Hz, 1H), 5.10 (s, 2H), 4.04 (t, J=7.6 Hz, 2H), 3.55 (d, J=6.9 Hz, 2H), 3.31 (s, 3H), 2.92-2.86 (m, 1H), 2.80-2.57 (m, 3H), 2.40 (t, J=6.9 Hz, 2H), 2.06-1.91 (m, 1H), 1.70-1.43 (m, 4H); LC/MS (ESI, m/z): $[(M+1)]^+$=491.15.

The intermediates in Table 38 were prepared according to step 9 of the procedure to prepare Intermediate G-3-54.

TABLE 37

Characterization data for intermediates prepared according to above.

| Intermediate | Structure | Chemical Name | MS: $[(M + 1)]^+$ | $^1$H NMR |
|---|---|---|---|---|
| G-8-1 | 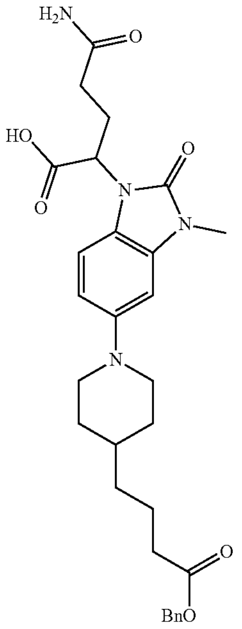 [SMILES: Cn1c(=O)n(C(CCC(N)=O)C(=O)O)c2ccc(N3CCC(CCCC(=O)OCc4ccccc4)CC3)cc21] | 2-(5-[4-[4-(benzyloxy)-4-oxobutyl]piperidin-1-yl]-3-methyl-2-oxo-1,3-benzodiazol-1-yl)-4-carbamoylbutanoic acid | 537.45 | $^1$H NMR (400 MHz, DMSO-$d_6$) δ 7.70-7.43 (m, 1H), 7.46-7.30 (m, 5H), 7.21 (s, 2H), 6.74 (s, 1H), 5.11 (s, 2H), 5.05 (dd, J = 10.8, 4.9 Hz, 1H), 3.61-3.58 (m, 4H), 3.37 (s, 3H), 2.41 (t, J = 7.3 Hz, 3H), 2.36-2.22 (m, 1H), 2.08-1.98 (m, 2H), 1.98-1.85 (m, 3H), 1.70-1.41 (m, 6H), 1.35-1.29 (m, 2H) |

TABLE 38

| Characterization data for intermediates prepared according to above. | | | | |
|---|---|---|---|---|
| Intermediate | Structure | Chemical Name | MS: $[(M + 1)]^+$ | $^1$H-NMR |
| G-3-55 | 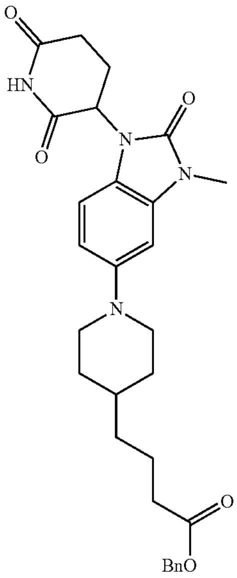 [SMILES: Cn1c(=O)n(C2CCC(=O)NC2=O)c2ccc(N3CCC(CCCC(=O)OCc4ccccc4)CC3)cc21] | benzyl 4-[1-[1-(2,6-dioxopiperidin-3-yl)-3-methyl-2-oxo-1,3-benzodiazol-5-yl]piperidin-4-yl]butanoate | 519.20 | (400 MHz, DMSO-$d_6$) δ 11.14 (s, 1H), 7.52 (s, 1H), 7.43-7.30 (m, 5H), 7.24 (s, 2H), 5.41 (dd, J = 12.7, 5.4 Hz, 1H), 5.11 (s, 2H), 3.66-3.52 (m, 3H), 3.38 (s, 3H), 2.95-2.87 (m, 1H), 2.81-2.57 (m, 2H), 2.41 (t, J = 7.3 Hz, 2H), 2.06-1.98 (m, 1H), 1.97-1.90 (m, 2H), 1.75-1.40 (m, 6H), 1.34-1.29 (m, 2H) |

Step 4. 2-[2-(2-[3-[1-(2,6-Dioxopiperidin-3-yl)-3-methyl-2-oxo-2,3-dihydro-1H-1,3-benzodiazol-5-yl]propoxy]ethoxy)ethoxy]acetic acid. A solution of tert-butyl 2-[2-(2-[3-[1-(2,6-dioxopiperidin-3-yl)-3-methyl-2-oxo-2,3-dihydro-1H-1,3-benzodiazol-5-yl]propoxy]ethoxy)ethoxy]acetate (700 mg, 1.35 mmol) in DCM (10.0 mL) and TFA (10.0 mL) was stirred for 30 min at room temperature under nitrogen atmosphere. The resulting mixture was concentrated under reduced pressure. The residue was purified by reversed phase flash chromatography with the following conditions: Column: WelFlash™ C18-I, 20~40 um, 330 g; EluentA: water (plus 10 mmol/LFA); Eluent B: ACN; Gradient: 20% - 40% B in 20 min; Flow rate: 80 mL/min; Detector: UV 220/254 nm; desired fractions were collected at 31% B and concentrated under reduced pressure to afford the title compound as a light yellow solid (520 mg, 83%): $^1$H NMR (400 MHz, DMSO-$d_6$) δ 12.58 (s, 1H), 11.09 (s, 1H), 7.09-6.97 (m, 2H), 6.88 (dd, J=8.1, 1.6 Hz, 1H), 5.34 (dd, J=12.7, 5.4 Hz, 1H), 4.03 (s, 2H), 3.62-3.48 (m, 8H), 3.40 (t, J=6.5 Hz, 2H), 3.33 (s, 3H), 2.97-2.85 (m, 1H), 2.77-2.58 (m, 4H), 2.06-1.96 (m, 1H), 1.88-1.77 (m, 2H); MS (ESI, m/z): $[(M+1)]^+$=464.30.

The following intermediates in Table 39 were prepared according Step 4 of the procedure to prepare Intermediate G.

TABLE 39

| Characterization data for intermediates prepared according to procedure above. | | | | |
|---|---|---|---|---|
| Intermediate | Structure | Chemical Name | MS: $[(M + 1)]^+$ | $^1$H-NMR |
| G-4-1 | 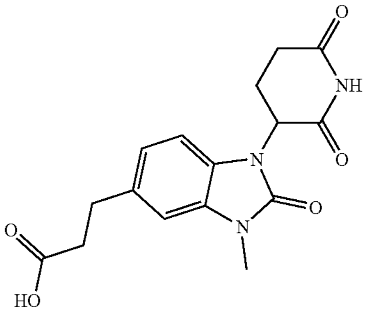 [SMILES: Cn1c(=O)n(C2CCC(=O)NC2=O)c2ccc(CCC(=O)O)cc21] | 3-[1-(2,6-dioxopiperidin-3-yl)-3-methyl-2-oxo-2,3-dihydro-1H-1,3-benzodiazol-5-yl]propanoic acid | 332.2 | (400 MHz, DMSO-$d_6$) δ 12.13 (s, 1H), 11.10 (s, 1H), 7.09 (d, J = 1.6 Hz, 1H), 7.01 (d, J = 8.0 Hz, 1H), 6.91 (dd, J = 8.1, 1.6 Hz, 1H), 5.34 (dd, J = 12.7, 5.4 Hz, 1H), 3.32 (s, 3H), 2.97-2.78 (m, 3H), 2.78-2.53 (m, 4H), 2.00 (s, 1H). |

TABLE 39-continued

| Characterization data for intermediates prepared according to procedure above. | | | | |
|---|---|---|---|---|
| Intermediate | Structure | Chemical Name | MS: $[(M + 1)]^+$ | $^1$H-NMR |
| G-4-2 | 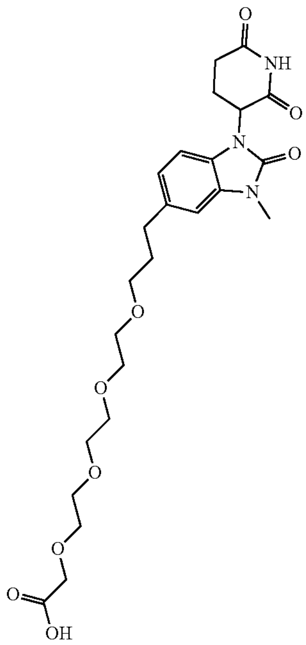 [SMILES: Cn1c(=O)n(C2CCC(=O)NC2=O)c2ccc(CCCOCCOCCOCCOCC(=O)O)cc21] | 15-[1-(2,6-dioxopiperidin-3-yl)-3-methyl-2-oxo-2,3-dihydro-1H-1,3-benzodiazol-5-yl]-3,6,9,12-tetraoxapentadecanoic acid | 508.3 | (400 MHz, DMSO-$d_6$) 12.58 (s, 1H), 11.09 (s, 1H), 7.08-6.97 (m, 2H), 6.88 (dd, J = 8.0, 1.6 Hz, 1H), 5.34 (dd, J = 12.7, 5.4 Hz, 1H), 4.02 (d, J = 2.0 Hz, 2H), 3.58 (dd, J = 6.4, 3.5 Hz, 2H), 3.54 (s, 5H), 3.51-3.44 (m, 3H), 3.43-3.35 (m, 4H), 2.90 (ddd, J = 17.3, 13.0, 5.2 Hz, 1H), 2.77-2.59 (m, 4H), 2.08 (s, 3H), 2.00 (dd, J = 11.1, 5.4 Hz, 1H), 1.88-1.76 (m, 2H). |
| G-4-3 | 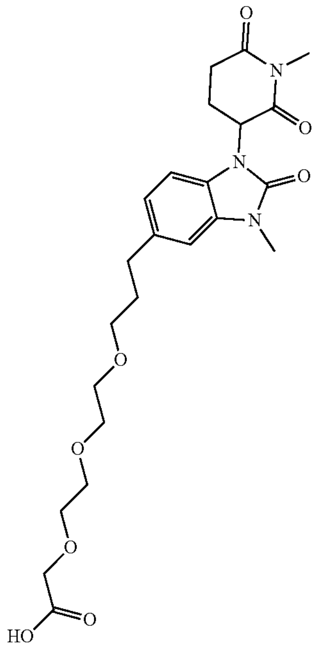 [SMILES: CN1C(=O)CCC(n2c(=O)n(C)c3cc(CCCOCCOCCOCC(=O)O)ccc32)C1=O] | [2-(2-[3-[3-methyl-1-(1-methyl-2,6-dioxopiperidin-3-yl)-2-oxo-1,3-benzodiazol-5-yl]propoxy]ethoxy)ethoxy]acetic acid | 578.3 | (400 MHz, DMSO-$d_6$) δ 12.57 (s, 1H), 7.08-6.96 (m, 2H), 6.86 (t, J = 7.8 Hz, 1H), 5.40 (dt, J = 12.8, 6.2 Hz, 1H), 4.02 (d, J = 6.4 Hz, 2H), 3.62-3.49 (m, 5H), 3.49 (t, J = 3.7 Hz, 2H), 3.43-3.35 (m, 2H), 3.03 (d, J = 6.9 Hz, 3H), 2.82-2.60 (m, 4H), 2.49 (s, 2H), 2.10-1.96 (m, 2H), 1.81 (q, J = 7.3 Hz, 3H). |

TABLE 39-continued

| Characterization data for intermediates prepared according to procedure above. | | | | |
|---|---|---|---|---|
| Intermediate | Structure | Chemical Name | MS: $[(M + 1)]^+$ | $^1H$-NMR |
| G-4-4 | 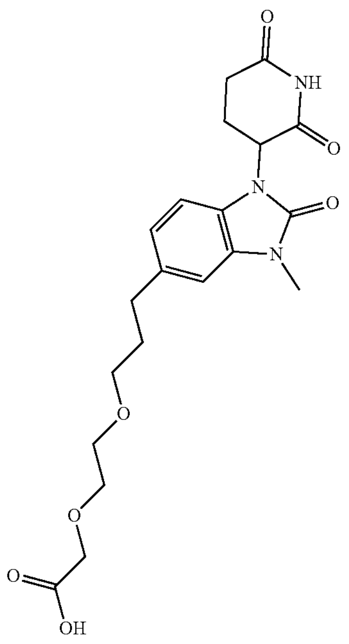 [SMILES: Cn1c(=O)n(C2CCC(=O)NC2=O)c2ccc(CCCOCCOCC(=O)O)cc21] | 2-(2-[3-[1-(2,6-dioxopiperidin-3-yl)-3-methyl-2-oxo-2,3-dihydro-1H-1,3-benzodiazol-5-yl]propoxy]ethoxy) acetic acid | 420.3 | (400 MHz, DMSO-$d_6$) δ 12.59 (s, 1H), 11.09 (s, 1H), 7.04 (d, J = 13.4 Hz, 2H), 6.88 (d, J = 8.2 Hz, 1H), 5.34 (dd, J = 12.8, 5.4 Hz, 1H), 4.05 (s, 2H), 3.61 (dd, J = 5.9, 3.5 Hz, 2H), 3.51 (dd, J = 5.9, 3.6 Hz, 2H), 3.40 (t, J = 6.4 Hz, 2H), 3.33 (s, 3H), 2.88 (d, J = 17.8 Hz, 1H), 2.77-2.58 (m, 4H), 2.05-1.97 (m, 1H), 1.81 (q, J = 7.4, 7.0 Hz, 2H). |
| G-4-5 | 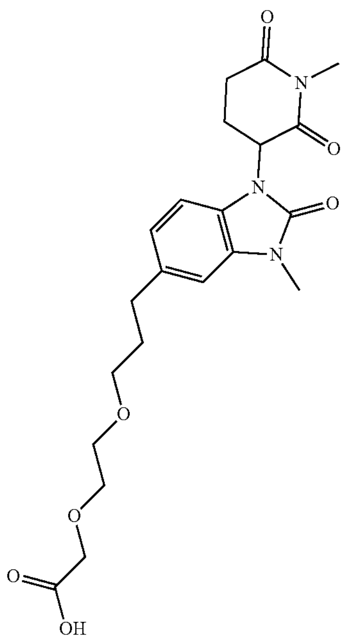 [SMILES: CN1C(=O)CCC(n2c(=O)n(C)c3cc(CCCOCCOCC(=O)O)ccc32)C1=O] | (2-[3-[3-methyl-1-(1-methyl-2,6-dioxopiperidin-3-yl)-2-oxo-1,3-benzodiazol-5-yl]propoxy]ethoxy) acetic acid | 432.2 | (400 MHz, DMSO-$d_6$) δ 7.08-6.98 (m, 2H), 6.87 (d, J = 8.1 Hz, 1H), 5.41 (dd, J = 13.2, 5.3 Hz, 1H), 4.04 (s, 2H), 3.61 (dd, J = 5.9, 3.7 Hz, 2H), 3.52 (dd, J = 5.9, 3.6 Hz, 2H), 3.41 (t, J = 6.4 Hz, 2H), 3.33 (s, 2H), 3.04 (s, 3H), 3.02-2.91 (m, 1H), 2.82-2.62 (m, 4H), 2.02 (d, J = 12.0 Hz, 1H), 1.82 (p, J = 6.7 Hz, 3H). |

TABLE 39-continued

| Characterization data for intermediates prepared according to procedure above. | | | | |
|---|---|---|---|---|
| Intermediate | Structure | Chemical Name | MS: [(M + 1)]$^+$ | $^1$H-NMR |
| G-4-6 | 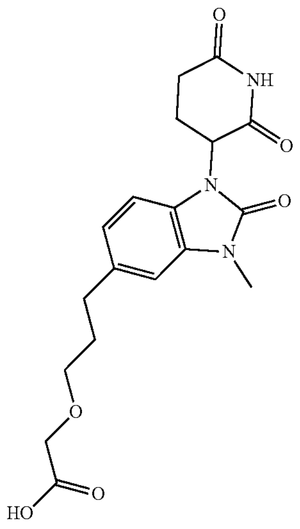 [SMILES: Cn1c(=O)n(C2CCC(=O)NC2=O)c2ccc(CCCOCC(=O)O)cc21] | 2-[3-[1-(2,6-dioxopiperidin-3-yl)-3-methyl-2-oxo-2,3-dihydro-1H-1,3-benzodiazol-5-yl]propoxy]acetic acid | 376.1 | (400 MHz, DMSO-$d_6$) δ 12.59 (s, 1H), 11.10 (s, 1H), 7.07 (d, J = 1.5 Hz, 1H), 7.01 (d, J = 8.0 Hz, 1H), 6.89 (dd, J = 8.1, 1.6 Hz, 1H), 5.34 (dd, J = 12.7, 5.4 Hz, 1H), 4.01 (s, 2H), 3.47 (t, J = 6.4 Hz, 2H), 3.33 (s, 3H), 2.90 (ddd, J = 17.1, 13.1, 5.3 Hz, 1H), 2.77-2.58 (m, 4H), 2.06-1.96 (m, 1H), 1.83 (dq, J = 8.7, 6.6 Hz, 2H) |
| G-4-34 | 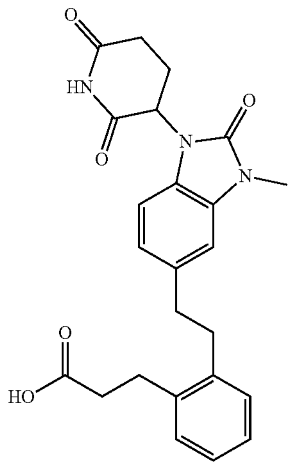 [SMILES: Cn1c(=O)n(C2CCC(=O)NC2=O)c2ccc(CCc3ccccc3CCC(=O)O)cc21] | 3-(2-[2-[1-(2,6-dioxopiperidin-3-yl)-3-methyl-2-oxo-1,3-benzodiazol-5-yl]ethyl]phenyl) propanoic acid | 436.10 | (400 MHz, DMSO-$d_6$) δ 11.08 (s, 1H), 7.26-7.23 (m, 1H), 7.20-7.17 (m, 1H), 7.18-7.09 (m, 3H), 7.02 (d, J = 8.0 Hz, 1H), 6.93 (dd, J = 8.1, 1.6 Hz, 1H), 5.35 (dd, J = 12.6, 5.4 Hz, 1H), 3.34 (s, 3H), 2.94-2.83 (m, 9H), 2.78-2.58 (m, 2H), 2.04-1.96 (m, 1H) |

TABLE 39-continued

| Characterization data for intermediates prepared according to procedure above. | | | | |
|---|---|---|---|---|
| Intermediate | Structure | Chemical Name | MS: $[(M+1)]^+$ | $^1H$-NMR |
| G-4-35 | 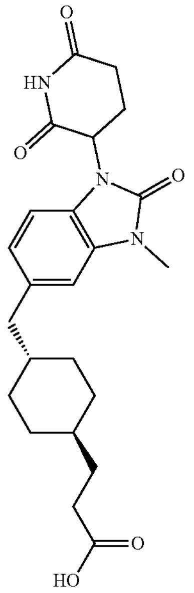 [SMILES: Cn1c(=O)n(C2CCC(=O)NC2=O)c2ccc(C[C@H]3CC[C@H](CCC(=O)O)CC3)cc21] | [(1r,4r)-4-[[1-(2,6-dioxopiperidin-3-yl)-3-methyl-2-oxo-1,3-benzodiazol-5-yl]methyl]cyclohexyl]acetic acid | 428.15 | (400 MHz, DMSO-$d_6$) δ 11.91 (s, 1H), 11.08 (s, 1H), 6.99 (d, J = 8.1 Hz, 2H), 6.81 (dd, J = 8.0, 1.6 Hz, 1H), 5.36 (dd, J = 12.7, 5.4 Hz, 1H), 2.96-2.85 (m, 1H), 2.77-2.58 (m, 3H), 2.48 (s, 2H), 2.21-2.17 (m, 2H), 2.08-1.97 (m, 1H), 1.70-1.64 (m, 5H), 1.42-1.36 (m, 2H), 1.22-1.10 (m, 2H), 0.98-0.78 (m, 5H) |
| G-4-36 | 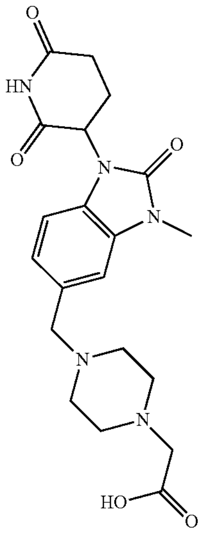 [SMILES: Cn1c(=O)n(C2CCC(=O)NC2=O)c2ccc(CN3CCN(CC(=O)O)CC3)cc21] | (4-[[1-(2,6-dioxopiperidin-3-yl)-3-methyl-2-oxo-1,3-benzodiazol-5-yl]methyl]piperazin-1-yl)acetic acid | 416.12 | Used in the next step without further purification |

TABLE 39-continued

| Characterization data for intermediates prepared according to procedure above. | | | | |
|---|---|---|---|---|
| Intermediate | Structure | Chemical Name | MS: $[(M+1)]^+$ | $^1$H-NMR |
| G-4-37 | 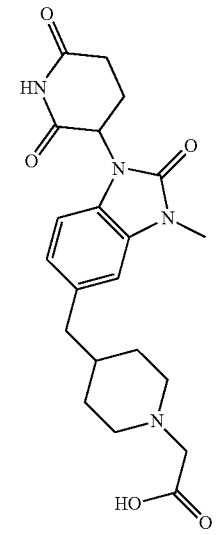 | (4-[[1-(2,6-Dioxopiperidin-3-yl)-3-methyl-2-oxo-1,3-benzodiazol-5-yl]methyl]piperidin-1-yl)acetic acid | 415.10 | (400 MHz, DMSO-$d_6$) δ 11.09 (s, 1H), 9.75-9.58 (s, 1H), 7.12-6.99 (m, 2H), 6.87 (dd, J = 8.1, 1.5 Hz, 1H), 5.35 (dd, J = 12.8, 5.3 Hz, 1H), 4.13-4.05 (m, 2H), 3.49 (d, J = 11.9 Hz, 2H), 3.33 (s, 3H), 3.02-2.84 (m, 2H), 2.77-2.55 (m, 4H), 1.96-1.89 (m, 1H), 1.78 (d, J = 13.1 Hz, 3H), 1.58-1.44 (m, 3H) |
| G-4-38 | 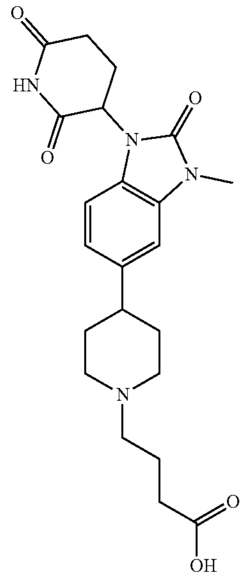 [SMILES: Cn1c(=O)n(C2CCC(=O)NC2=O)c2ccc(C3CCN(CCCC(=O)O)CC3)cc21] | 4-[4-[1-(2,6-Dioxopiperidin-3-yl)-3-methyl-2-oxo-1,3-benzodiazol-5-yl]piperidin-1-yl]butanoic acid | 429.20 | (400 MHz, DMSO-$d_6$) δ 11.09 (s, 1H), 7.12-7.00 (m, 2H), 6.92 (dd, J = 8.2, 1.6 Hz, 1H), 5.35 (dd, J = 12.8, 5.3 Hz, 1H), 3.81-3.78 (m, 1H), 3.35 (s, 3H), 2.97-2.85 (m, 1H), 2.84-2.66 (m, 4H), 2.66-2.56 (m, 3H), 2.33 (t, J = 7.0 Hz, 2H), 2.06-1.70 (m, 8H) |

TABLE 39-continued

| Characterization data for intermediates prepared according to procedure above. | | | | |
|---|---|---|---|---|
| Intermediate | Structure | Chemical Name | MS: $[(M + 1)]^+$ | $^1$H-NMR |
| G-4-39 | 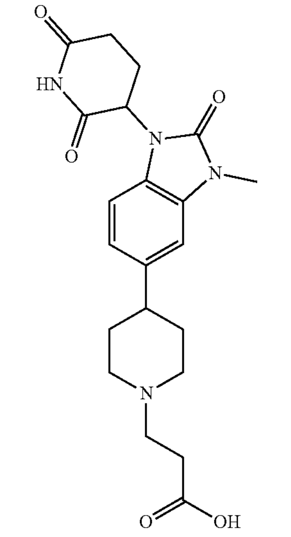 [SMILES: Cn1c(=O)n(C2CCC(=O)NC2=O)c2ccc(C3CCN(CCC(=O)O)CC3)cc21] | 3-[4-[1-(2,6-Dioxopiperidin-3-yl)-3-methyl-2-oxo-1,3-benzodiazol-5-yl]piperidin-1-yl]propanoic acid | 415.15 | (400 MHz, DMSO-$d_6$) δ 11.09 (s, 1H), 7.10 (d, J = 1.6 Hz, 1H), 7.03 (d, J = 8.1 Hz, 1H), 6.92 (dd, J = 8.2, 1.6 Hz, 1H), 5.35 (dd, J = 12.7, 5.3 Hz, 1H), 3.34 (s, 3H), 3.16 (d, J = 11.7 Hz, 2H), 3.00-2.56 (m, 5H), 2.47 (d, J = 7.2 Hz, 2H), 2.40-2.29 (m, 2H), 2.08-1.95 (m, 1H), 1.89-1.67 (m, 5H) |
| G-4-40 | 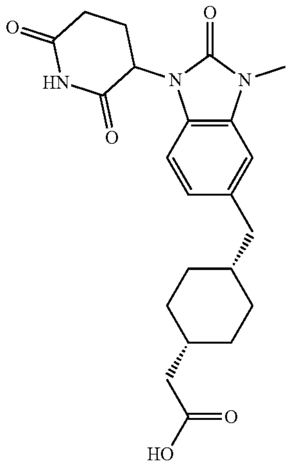 [SMILES: Cn1c(=O)n(C2CCC(=O)NC2=O)c2ccc(C[C@H]3CC[C@@H](CC(=O)O)CC3)cc21] | [(1s,4s)-4-[[1-(2,6-dioxopiperidin-3-yl)-3-methyl-2-oxo-1,3-benzodiazol-5-yl]methyl]cyclohexyl] acetic acid | 414.15 | (300 MHz, DMSO-$d_6$) δ 12.50 (br, 1H), 11.06 (s, 1H), 6.70-6.96 (m, 2H), 6.82 (dd, J = 8.1, 1.5 Hz, 1H), 5.32 (dd, J = 12.7, 5.4 Hz, 1H), 3.31 (s, 3H), 3.00-2.79 (m, 1H), 2.78-2.53 (m, 4H), 2.21 (d, J = 7.3 Hz, 2H), 2.04-2.00 (m, 1H), 1.91-1.86 (m, 1H), 1.70-1.67 (m, 1H), 1.55-1.48 (m, 6 H) 1.35-1.28 (m, 2H). |
| G-4-41 | 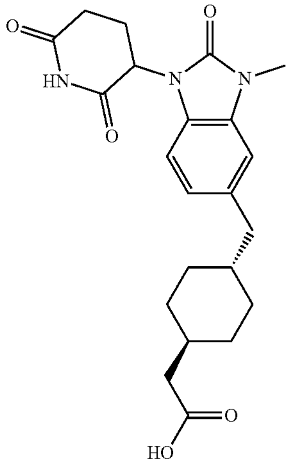 [SMILES: Cn1c(=O)n(C2CCC(=O)NC2=O)c2ccc(C[C@H]3CC[C@H](CC(=O)O)CC3)cc21] | [(1r,4r)-4-[[1-(2,6-dioxopiperidin-3-yl)-3-methyl-2-oxo-1,3-benzodiazol-5-yl]methyl]cyclohexyl] acetic acid | 414.15 | (400 MHz, DMSO-$d_6$) δ 11.96 (s, 1H), 11.09 (s, 1H), 7.02-6.96 (m, 2H), 6.83-6.81 (m, 1H), 5.36-5.32 (m, 1H), 3.32 (s, 4H), 2.96-2.85 (m, 1H), 2.77-2.58 (m, 2H), 2.48 (s, 2H), 2.09-2.05 (m, 3H), 2.04-1.97 (m, 1H), 1.67 (t, J = 13.2 Hz, 4H), 1.01-0.85 (m, 4H) |

TABLE 39-continued

| Characterization data for intermediates prepared according to procedure above. | | | | |
|---|---|---|---|---|
| Intermediate | Structure | Chemical Name | MS: [(M + 1)]$^+$ | $^1$H-NMR |
| G-4-42 | 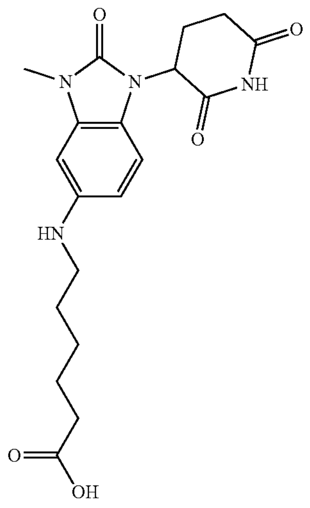 [SMILES: Cn1c(=O)n(C2CCC(=O)NC2=O)c2ccc(NCCCCCC(=O)O)cc21] | 6-[[1-(2,6-dioxopiperidin-3-yl)-3-methyl-2-oxo-1,3-benzodiazol-5-yl]amino]hexanoic acid | 389.20 | (400 MHz, $CD_3OD$) δ 7.39 (d, J = 2.0 Hz, 1H), 7.31 (d, J = 8.5 Hz, 1H), 7.28-7.19 (m, 1H), 5.41 (dd, J = 12.5, 5.4 Hz, 1H), 3.47-3.45 (m, 4H), 3.50-3.41 (m, 1H), 3.02-2.75 (m, 3H), 2.35-2.32 (m, 2H), 2.23-2.19 (m, 1H), 1.85-1.77 (m, 1H), 1.77 (t, J = 6.4 Hz, 1H), 1.67 (p, J = 7.3 Hz, 2H), 1.51-1.47 (m, 2H). |
| G-4-85 | 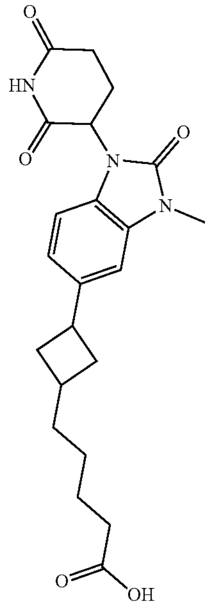 [SMILES: Cn1c(=O)n(C2CCC(=O)NC2=O)c2ccc(C3CC(CCCCC(=O)O)C3)cc21] | 5-[3-[1-(2,6-dioxopiperidin-3-yl)-3-methyl-2-oxo-1,3-benzodiazol-5-yl]cyclobutyl] pentanoic acid | 414.20 | (300 MHz, Chloroform-d) δ 8.74 (s, 1H), 7.06-6.94 (m, 2H), 6.89-6.73 (m, 1H), 5.51-5.36 (m, 1H), 3.69-3.62 (m, 1H), 3.52 (s, 3H), 3.48-3.31 (m, 1H), 3.07-2.84 (m, 2H), 2.81-2.68 (m, 1H), 2.61-2.36 (m, 2H), 2.34-2.25 (m, 3H), 2.18-2.12 (m, 1H), 1.83-1.52 (m, 4H), 1.52-1.15 (m, 4H) |

TABLE 39-continued

| Characterization data for intermediates prepared according to procedure above. | | | | |
|---|---|---|---|---|
| Intermediate | Structure | Chemical Name | MS: [(M + 1)]$^+$ | $^1$H-NMR |
| G-4-86 | 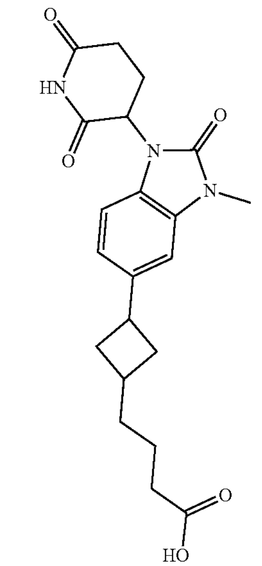 [SMILES: Cn1c(=O)n(C2CCC(=O)NC2=O)c2ccc(C3CC(CCCC(=O)O)C3)cc21] | 4-[3-[1-(2,6-dioxopiperidin-3-yl)-3-methyl-2-oxo-1,3-benzodiazol-5-yl]cyclobutyl]butanoic acid | 400.10 | (400 MHz, Methanol-$d_4$) δ 7.14-6.93 (m, 3H), 5.32 (ddd, J = 12.3, 5.5, 2.3 Hz, 1H), 3.67 (p, J = 7.6, 6.8 Hz, 1H), 3.51-3.39 (m, 3H), 2.97-2.93 (m, 1H), 2.82-2.78 (m, 2H), 2.56-2.53 (m, 1H), 2.34-2.30 (m, 4H), 2.19-2.15 (m, 2H), 1.80-1.43 (m, 5H), 1.43-1.12 (m, 1H). |
| G-4-109 | 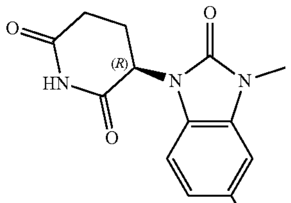 R assumed | [(1s,4s)-4-[[1-(2,6-dioxopiperidin-3-yl)-3-methyl-2-oxo-1,3-benzodiazol-5-yl]methyl]cyclohexyl] acetic acid | 414.15 | (400 MHz, DMSO-$d_6$) δ 11.81 (s, 1H), 11.09 (s, 1H), 7.01-6.99 (m, 2H), 6.83 (dd, J = 8.0, 1.5 Hz, 1H), 5.34 (dd, J = 12.7, 5.4 Hz, 1H), 3.32 (s, 3H), 2.97-2.83 (m, 1H), 2.77-2.62 (m, 2H), 2.59 (d, J = 6.3 Hz, 2H), 2.22 (d, J = 7.3 Hz, 2H), 2.04-1.98 (m, 1H), 1.93-1.87 (m, 1H), 1.78-1.64 (m, 1H), 1.48-1.38 (m, 6H), 1.33-1.26 (m, 2H) |
| G-4-110 | 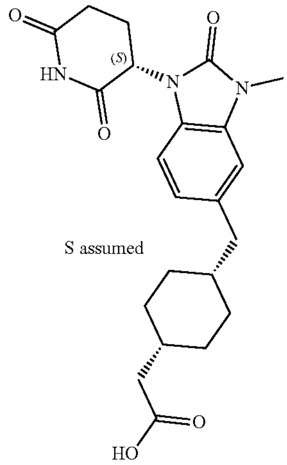 S assumed | [(1s,4s)-4-[[1-(2,6-dioxopiperidin-3-yl)-3-methyl-2-oxo-1,3-benzodiazol-5-yl]methyl]cyclohexyl] acetic acid | 414.15 | (400 MHz, DMSO-$d_6$) δ 11.81 (s, 1H), 11.09 (s, 1H), 7.01-6.99 (m, 2H), 6.83 (dd, J = 8.0, 1.5 Hz, 1H), 5.34 (dd, J = 12.7, 5.4 Hz, 1H), 3.32 (s, 3H), 2.97-2.83 (m, 1H), 2.77-2.62 (m, 2H), 2.59 (d, J = 6.3 Hz, 2H), 2.22 (d, J = 7.3 Hz, 2H), 2.04-1.98 (m, 1H), 1.93-1.87 (m, 1H), 1.78-1.64 (m, 1H), 1.48-1.38 (m, 6H), 1.33-1.26 (m, 2H) |

TABLE 39-continued

| Characterization data for intermediates prepared according to procedure above. | | | | |
|---|---|---|---|---|
| Intermediate | Structure | Chemical Name | MS: $[(M+1)]^+$ | $^1H$-NMR |
| G-4-111 | 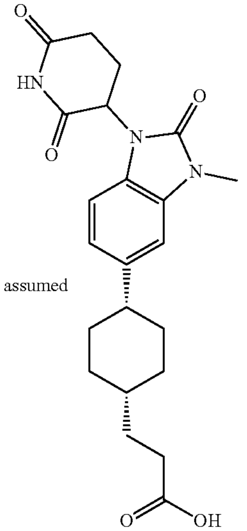 [SMILES: Cn1c(=O)n(C2CCC(=O)NC2=O)c2ccc([C@H]3CC[C@@H](CCC(=O)O)CC3)cc21] | 3-[(1s,4s)-4-[1-(2,6-dioxopiperidin-3-yl)-3-methyl-2-oxo-1,3-benzodiazol-5-yl]cyclohexyl] propanoic acid | 414.15 | (300 MHz, DMSO-$d_6$) δ 11.08 (s, 1H), 7.07 (d, J = 1.5 Hz, 1H), 7.00 (d, J = 8.1 Hz, 1H), 6.90 (dd, J = 8.1, 1.6 Hz, 1H), 5.34 (dd, J = 12.7, 5.4 Hz, 1H), 3.34 (s, 3H), 2.99-2.83 (m, 1H), 2.81-2.57 (m, 2H), 2.27 (t, J = 7.6 Hz, 2H), 2.01 (d, J = 11.6 Hz, 1H), 1.83-1.80 (m, 4H), 1.48-1.44 (m, 4H), 1.32-1.29 (m, 1H), 1.16-0.97 (m, 2H) |
| G-4-112 | 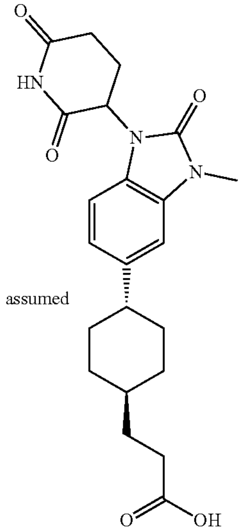 [SMILES: Cn1c(=O)n(C2CCC(=O)NC2=O)c2ccc([C@H]3CC[C@H](CCC(=O)O)CC3)cc21] | 3-[(1r,4r)-4-[1-(2,6-dioxopiperidin-3-yl)-3-methyl-2-oxo-1,3-benzodiazol-5-yl]cyclohexyl] propanoic acid | 414.15 | (300 MHz, DMSO-$d_6$) δ 12.00 (s, 1H), 11.08 (s, 1H), 7.10 (d, J = 1.5 Hz, 1H), 7.01 (d, J = 8.1 Hz, 1H), 6.92 (dd, J = 8.1, 1.5 Hz, 1H), 5.34 (dd, J = 12.7, 5.4 Hz, 1H), 3.33-3.31 (m, 4H), 2.99-2.81 (m, 1H), 2.69-2.61 (m, 2H), 2.25-2.21 (m, 2H), 2.07-1.95 (m, 1H), 1.65-1.61 (m, 11H) |

[4-([[(2R,3S)-3-[(tert-butoxycarbonyl)amino-5-carbamoylpentan-2-yl]oxy]methyl)phenyl]acetic acid. (Intermediate G-4-7)

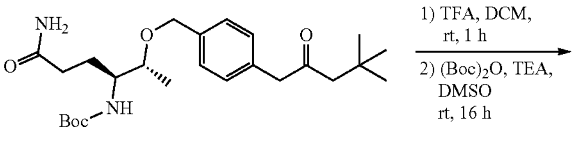

-continued

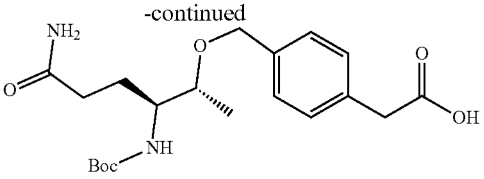

Intermediate G-4-7

A solution of tert-butyl 2-[4-([[(2R,3S)-3-[(tert-butoxycarbonyl)amino]-5-carbamoylpentan-2-yl]oxy]methyl)phenyl]acetate (270 mg, 0.60 minol) in DCM (3.00 mL) was treated with TFA (3.00 mL) for 20 min at 25° C. under nitrogen atmosphere. The resulting mixture was concentrated under reduced pressure. The residue was dissolved in DMSO (5.00 mL) and TEA (1.00 mL). To the solution was added $Boc_2O$ (196 mg, 0.90 minol) at 25° C. under nitrogen atmosphere. The resulting mixture was stirred for 30 min at 25° C. under nitrogen atmosphere. The resulting mixture was purified by reversed phase flash chromatography with the following conditions: Column: WelFlash™ C18-I, 20~40 um, 330 g; Eluent A: water (plus 10 mmol/L AcOH); Eluent B: ACN; Gradient: 30% - 50% B in 20 min; Flow rate: 80 mL/min; Detector: UV 220/254 nm; desired fractions were collected at 45% B and concentrated under reduced pressure to afford the title compound as a light yellow oil (150 mg, 63): $^1$H NMR (400 MHz, DMSO-$d_6$) 12.26 (s, 1H), 7.27 (d, J=8.1 Hz, 2H), 7.22-7.20 (m, 3H), 6.67 (s, 1H), 6.61 (d, J=9.1 Hz, 1H), 4.51-4.40 (m, 2H), 3.55 (s, 2H), 3.49-3.38 (m, 2H), 2.14-1.95 (m, 2H, 1.79 (dddd, J=13.4, 9.8, 6.1, 3.0 Hz, 1H), 1.50 (td, J=9.3, 8.9, 5.0 Hz, 1H), 1.39 (s, 9H), 1.06 (d, J=6.0 Hz, 3H); MS (ESI, m/z): [(M+1)+=395.30.

The following intermediates in Table 40 were prepared according to the above procedure for Intermediate G-4-7.

TABLE 40

Characterization data for intermediates prepared according to procedure above.

| Intermediate | Structure | Chemical Name | MS: [(M + 1)]$^+$ | $^1$H-NMR |
|---|---|---|---|---|
| G-4-8 | 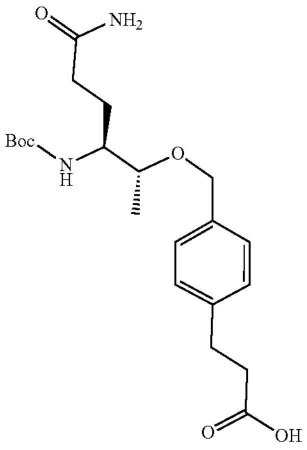 [SMILES: C[C@@H](OCc1ccc(CCC(=O)O)cc1)[C@H](CCC(N)=O)NC(=O)OC(C)(C)C] | 3-[4-([[(2R,3S)-3-[(tert-butoxycarbonyl)amino]-5-carbamoylpentan-2-yl]oxy]methyl)phenyl]propanoic acid | 409.2 | (400 MHz, $CDCl_3$) δ 7.26 (d, J = 7.8 Hz, 2H), 7.21 (d, J = 7.7 Hz, 2H), 6.62 (s, 1H), 6.36 (s, 1H), 4.89 (d, J = 9.6 Hz, 1H), 4.60 (d, J = 11.6 Hz, 1H), 4.37 (d, J = 11.6 Hz, 1H), 3.68-3.53 (m, 2H), 2.96 (t, J = 7.6 Hz, 2H), 2.66 (t, J = 7.7 Hz, 2H), 2.27 (td, J = 8.0, 4.7 Hz, 2H), 1.97-1.88 (m, 1H), 1.74-1.59 (m, 1H), 1.45 (s, 9H), 1.20 (d, J = 6.3 Hz, 3H). |
| G-4-9 | 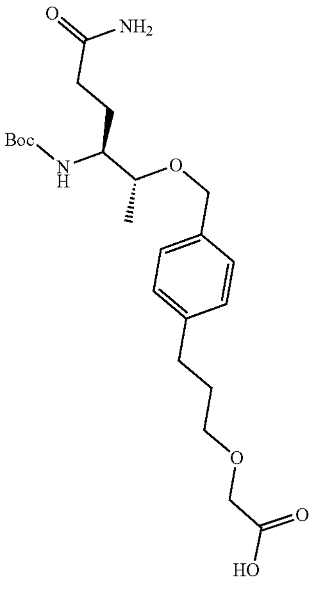 [SMILES: C[C@@H](OCc1ccc(CCCOCC(=O)O)cc1)[C@H](CCC(N)=O)NC(=O)OC(C)(C)C] | [3-[4-([[(2R,3S)-3-[(tert-butoxycarbonyl)amino]-5-carbamoylpentan-2-yl]oxy]methyl)phenyl]propoxy]acetic acid | 453.3 | (400 MHz, DMSO-$d_6$) δ 12.45 (s, 1H), 7.23 (dd, J = 7.9, 5.6 Hz, 3H), 7.16 (dd, J = 8.0, 5.9 Hz, 2H), 6.72-6.55 (m, 2H), 4.50-4.37 (m, 2H), 3.98 (s, 2H), 3.52-3.36 (m, 4H), 2.62 (td, J = 8.0, 5.6 Hz, 2H), 2.09-2.07 (m, 3H), 1.91 (d, J = 5.7 Hz, 1H), 1.83-1.77 (m, 2H), 1.39 (s, 9H), 1.06 (t, J = 5.5 Hz, 3H). |

TABLE 40-continued

Characterization data for intermediates prepared according to procedure above.

| Inter-mediate | Structure | Chemical Name | MS: $[(M+1)]^+$ | $^1$H-NMR |
| --- | --- | --- | --- | --- |
| G-4-10 | 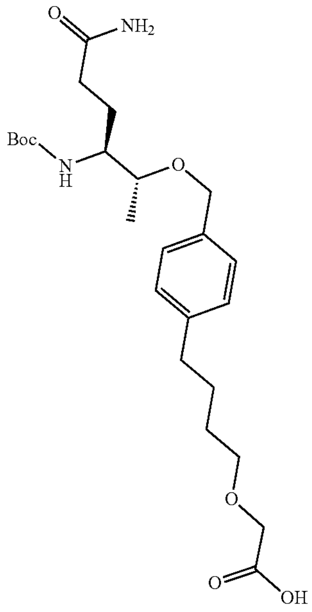 [SMILES: C[C@@H](OCc1ccc(CCCCOCC(=O)O)cc1)[C@H](CCC(N)=O)NC(=O)OC(C)(C)C] | [3-[4-([[(2R,3S)-3-[(tert-butoxycarbonyl)amino]-5-carbamoylpentan-2-yl]oxy]methyl)phenyl]propoxy]acetic acid | 467.2 | (400 MHz, DMSO-$d_6$) δ 12.48 (s, 1H), 7.34-7.08 (m, 5H), 6.69-6.59 (m, 2H), 4.43 (t, J = 4.4 Hz, 2H), 3.94 (d, J = 5.1 Hz, 2H), 3.49-3.35 (m, 4H), 2.57 (q, J = 6.0, 3.5 Hz, 2H), 2.13-1.96 (m, 3H), 1.84-1.72 (m, 1H), 1.60 (s, 2H), 1.52 (d, J = 8.7 Hz, 2H), 1.46-1.32 (m, 9H), 1.06 (d, J = 6.0, 3H). |
| G-4-11 | 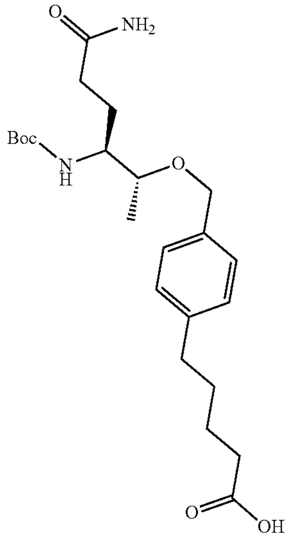 [SMILES: C[C@@H](OCc1ccc(CCCCC(=O)O)cc1)[C@H](CCC(N)=O)NC(=O)OC(C)(C)C] | 5-[4-([[(2R,3S)-3-[(tert-butoxycarbonyl)amino]-5-carbamoylpentan-2-yl]oxy]methyl)phenyl]pentanoic acid | 437.3 | (400 MHz, DMSO-$d_6$) δ 11.96 (s, 1H), 7.27-7.17 (m, 3H), 7.14 (d, J = 7.9 Hz, 2H), 6.67 (s, 1H), 6.59 (d, J = 9.0 Hz, 1H), 4.51-4.37 (m, 2H), 3.41 (h, J = 7.4, 6.0 Hz, 2H), 2.56 (t, J = 7.2 Hz, 2H), 2.22 (t, J = 7.1 Hz, 2H), 2.13-1.95 (m, 2H), 1.85-1.73 (m, 1H), 1.68-1.35 (m, 5H), 1.39 (s, 9H), 1.06 (d, J = 6.0 Hz, 3H). |

TABLE 40-continued

Characterization data for intermediates prepared according to procedure above.

| Inter-mediate | Structure | Chemical Name | MS: $[(M+1)]^+$ | $^1$H-NMR |
|---|---|---|---|---|
| G-4-12 | 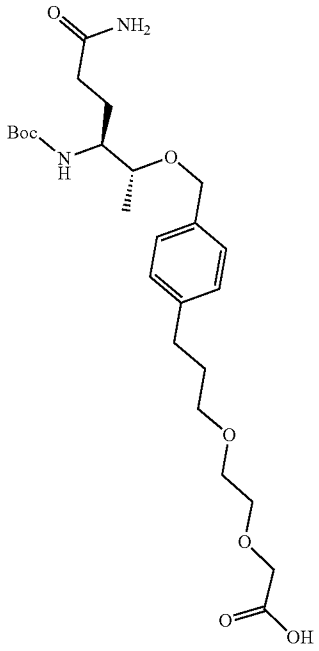 [SMILES: C[C@@H](OCc1ccc(CCCOCCOCC(=O)O)cc1)[C@H](CCC(N)=O)NC(=O)OC(C)(C)C] | (2-[3-[4-([[(2R,3S)-3-[(tert-butoxycarbonyl)amino]-5-carbamoylpentan-2-yl]oxy]methyl)phenyl]propoxy]ethoxy)acetic acid | 497.3 | (400 MHz, DMSO-$d_6$) δ 7.23 (d, J = 8.0 Hz, 2H), 7.15 (d, J = 7.7 Hz, 2H), 6.73-6.57 (m, 2H), 4.50-4.37 (m, 2H), 4.03 (s, 2H), 3.60 (dd, J = 5.9, 3.7 Hz, 2H), 3.50 (dd, J = 5.9, 3.6 Hz, 2H), 3.39-3.37 (m, 5H), 2.60 (t, J = 7.7 Hz, 2H), 2.07-1.96 (m, 2H), 1.84-1.73 (m, 3H), 1.39 (s, 9H), 1.06 (d, J = 6.0 Hz, 3H). |
| G-4-13 | 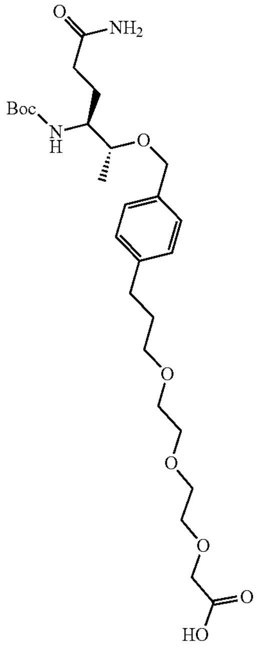 [SMILES: C[C@@H](OCc1ccc(CCCOCCOCCOCC(=O)O)cc1)[C@H](CCC(N)=O)NC(=O)OC(C)(C)C] | [2-(2-[3-[4-([[(2R,3S)-3-[(tert-butoxycarbonyl)amino]-5-carbamoylpentan-2-yl]oxy]methyl)phenyl]propoxy]ethoxy)ethoxy]acetic acid | 541.4 | (400 MHz, $CDCl_3$) δ 7.26 (d, J = 7.7 Hz, 2H), 7.20 (d, J = 7.8 Hz, 2H), 6.52 (s, 1H), 6.26 (s, 1H), 4.86 (d, J = 9.7 Hz, 1H), 4.61 (d, J = 11.6 Hz, 1H), 4.38 (d, J = 11.5 Hz, 1H), 4.19 (s, 2H), 3.79 (dd, J = 6.3, 3.1 Hz, 2H), 3.76-3.66 (m, 5H), 3.63-3.54 (m, 3H), 3.48 (t, J = 6.4 Hz, 2H), 2.72 (t, J = 7.5 Hz, 2H), 2.28 (t, J = 6.9 Hz, 2H), 1.92 (p, J = 6.9 Hz, 2H), 1.76-1.64 (m, 1H), 1.45 (s, 9H), 1.21 (d, J = 6.3 Hz, 3H). |

TABLE 40-continued

Characterization data for intermediates prepared according to procedure above.

| Inter-mediate | Structure | Chemical Name | MS: $[(M + 1)]^+$ | $^1$H-NMR |
|---|---|---|---|---|
| G-4-14 | 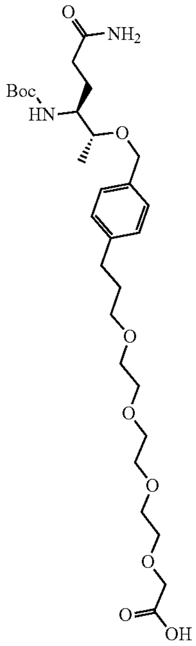 [SMILES: C[C@@H](OCc1ccc(CCCOCCOCCOCCOCC(=O)O)cc1)[C@H](CCC(N)=O)NC(=O)OC(C)(C)C] | 15-[4-([[(2R,3S)-3-[(tert-butoxycarbonyl) amino]-5-carbamoylpentan-2-yl]oxy]methyl) phenyl]-3,6,9,12-tetraoxapentadecanoic acid | 585.4 | (400 MHz, DMSO-$d_6$) δ 12.55 (s, 1H), 7.23 (d, J = 7.9 Hz, 2H), 7.15 (d, J = 7.8 Hz, 2H), 6.67 (s, 1H), 6.60 (d, J = 9.1 Hz, 1H), 4.49-4.38 (m, 2H), 4.01 (s, 2H), 3.62-3.44 (m, 12H), 3.41-3.36 (m, 3H), 2.60 (t, J = 7.6 Hz, 2H), 2.10-1.96 (m, 3H), 1.82-1.75 (m, 3H), 1.48 (s, 1H), 1.39 (s, 9H), 1.06 (d, J = 6.0 Hz, 3H). |
| G-4-15 | 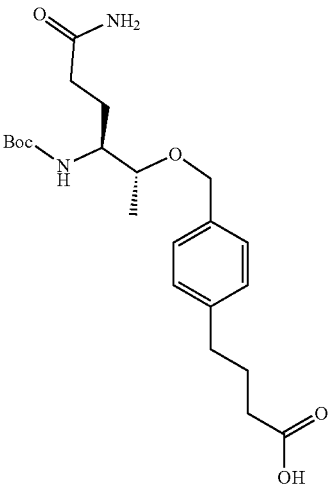 [SMILES: C[C@@H](OCc1ccc(CCCC(=O)O)cc1)[C@H](CCC(N)=O)NC(=O)OC(C)(C)C] | 4-[4-([[(2R,3S)-3-[(tert-butoxycarbonyl) amino]-5-carbamoylpentan-2-yl]oxy]methyl) phenyl]butanoic acid | 423.2 | (400 MHz, $CDCl_3$) δ 7.26-7.12 (m, 4H), 6.50 (s, 1H), 5.72 (s, 1H), 4.88 (d, J = 9.5 Hz, 1H), 4.71-4.50 (m, 1H), 4.38 (d, J = 11.4 Hz, 1H), 3.71-3.55 (m, 2H), 3.51 (s, 3H), 2.74-2.62 (m, 3H), 2.39-2.25 (m, 5H), 2.10-1.96 (, 3H), 1.46 (d, J = 6.0 Hz, 9H). |

TABLE 40-continued

| Characterization data for intermediates prepared according to procedure above. | | | | |
|---|---|---|---|---|
| Inter-mediate | Structure | Chemical Name | MS: [(M + 1)]$^+$ | $^1$H-NMR |
| G-4-16 | 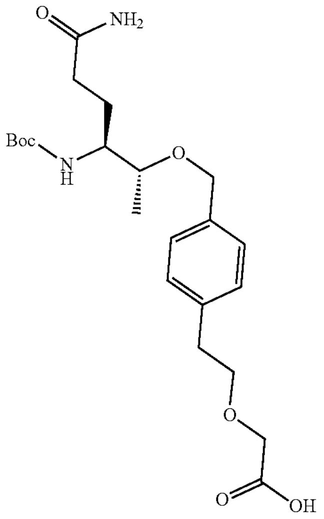 [SMILES: C[C@@H](OCc1ccc(CCOCC(=O)O)cc1)[C@H](CCC(N)=O)NC(=O)OC(C)(C)C] | [2-[4-([[(2R,3S)-3-[(tert-butoxycarbonyl) amino]-5-carbamoylpentan-2-yl]oxy]methyl) phenyl]ethoxy]acetic acid | 439.4 | (400 MHz, DMSO-$d_6$) δ 12.55 (s, 1H), 7.33-7.12 (m, 4H), 6.68 (s, 1H), 6.61 (d, J = 9.1 Hz, 1H), 4.49-4.38 (m, 2H), 4.00 (s, 2H), 3.66 (d, J = 14.0 Hz, 1H), 3.48-3.36 (m, 3H), 2.82 (t, J = 7.0 Hz, 2H), 2.21-1.89 (m, 3H), 1.39 (s, 9H), 1.06 (d, J = 5.9 Hz, 3H). |
| G-4-17 | 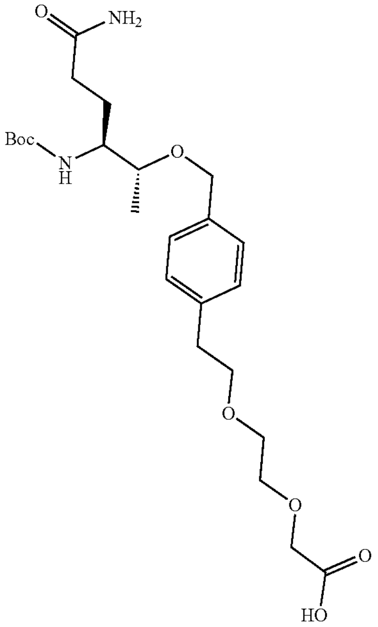 [SMILES: C[C@@H](OCc1ccc(CCOCCOCC(=O)O)cc1)[C@H](CCC(N)=O)NC(=O)OC(C)(C)C] | (2-[2-[4-([[(2R,3S)-3-[(tert-butoxycarbonyl) amino]-5-carbamoylpentan-2-yl]oxy]methyl) phenyl]ethoxy]ethoxy) acetic acid | 483.4 | (400 MHz, DMSO-$d_6$) δ 7.30-7.13 (m, 4H), 6.75-6.53 (m, 2H), 4.52-4.35 (m, 2H), 4.01 (s, 2H), 3.63-3.49 (m, 6H), 3.48-3.34 (m, 2H), 2.80 (t, J = 7.1 Hz, 2H), 2.03 (dd, J = 12.8, 7.0 Hz, 2H), 1.78 (d, J = 9.0 Hz, 1H), 1.56-1.43 (m, 1H), 1.39 (s, 9H), 1.06 (d, J = 6.0 Hz, 3H). |

TABLE 40-continued

| Characterization data for intermediates prepared according to procedure above. | | | | |
|---|---|---|---|---|
| Inter-mediate | Structure | Chemical Name | MS: $[(M + 1)]^+$ | $^1$H-NMR |
| G-4-18 | 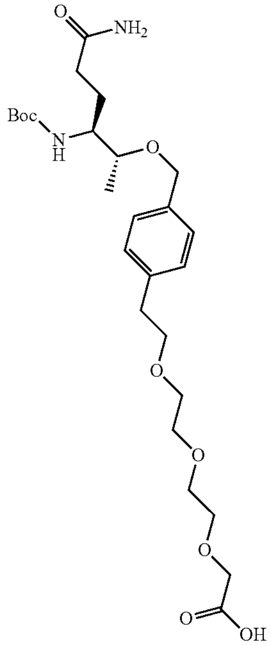 [SMILES: C[C@@H](OCc1ccc(CCOCCOCCOCC(=O)O)cc1)[C@H](CCC(N)=O)NC(=O)OC(C)(C)C] | [2-(2-[2-[4-([[(2R,3S)-3-[(tert-butoxycarbonyl)amino]-5-carbamoylpentan-2-yl]oxy]methyl)phenyl]ethoxy]ethoxy)ethoxy]acetic acid | 527.3 | (400 MHz, DMSO-$d_6$) δ 12.54 (s, 1H), 7.25-7.20 (m, 4H), 6.66-6.61 (m, 2H), 4.42 (s, 1H), 4.19-3.88 (m, 2H), 3.79-3.47 (m, 8H), 2.84 (s, 2H), 2.81-2.78 (m, 4H), 2.06 (s, 3H), 1.79 (s, 2H), 1.42 (s, 6H), 1.38 (s, 3H), 1.06 (s, 3H). |
| G-4-19 | 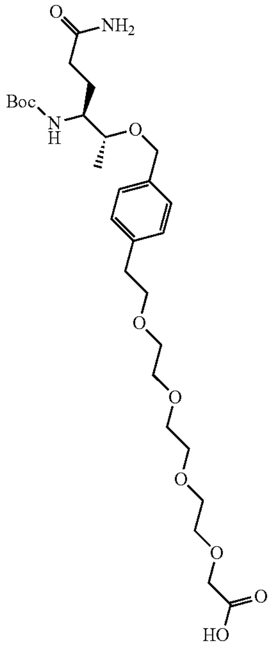 [SMILES: C[C@@H](OCc1ccc(CCOCCOCCOCCOCC(=O)O)cc1)[C@H](CCC(N)=O)NC(=O)OC(C)(C)C] | 14-[4-([[(2R,3S)-3-[(tert-butoxycarbonyl)amino]-5-carbamoylpentan-2-yl]oxy]methyl)phenyl]-3,6,9,12-tetraoxatetradecanoic acid | 571.4 | (400 MHz, DMSO-$d_6$) δ 12.53 (s, 1H), 7.30-7.15 (m, 4H), 6.73-6.55 (m, 2H), 4.50-4.39 (m, 2H), 4.02 (s, 2H), 3.65-3.53 (m, 4H), 3.53 (dd, J = 5.8, 3.2 Hz, 10H), 3.47-3.36 (m, 2H), 2.79 (t, J = 7.0 Hz, 2H), 2.12-1.99 (m, 2H), 1.79 (dt, J = 6.7, 3.6 Hz, 1H), 1.55-1.43 (m, 1H), 1.39 (s, 9H), 1.06 (d, J = 6.0 Hz, 3H). |

TABLE 40-continued

Characterization data for intermediates prepared according to procedure above.

| Inter-mediate | Structure | Chemical Name | MS: $[(M + 1)]^+$ | $^1$H-NMR |
|---|---|---|---|---|
| G-4-28 | 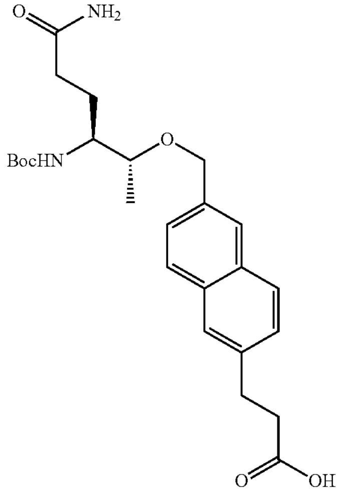 [SMILES: C[C@@H](OCc1ccc2cc(CCC(=O)O)ccc2c1)[C@H](CCC(N)=O)NC(=O)OC(C)(C)C] | 3-[6-([[(2R,3S)-3-[(tert-butoxycarbonyl)amino]-5-carbamoylpentan-2-yl]oxy]methyl)naphthalen-2-yl]propanoic acid | 459.2 | (400 MHz, $CD_3OD$) δ 7.79 (m, 3H), 7.67 (d, J = 17.6 Hz, 1H), 7.49 (d, J = 8.3 Hz, 1H), 7.38 (d, J = 7.8 Hz, 1H), 4.75 (d, J = 11.8 Hz, 1H), 4.66 (d, J = 11.8 Hz, 1H), 3.65-3.54 (m, 2H), 3.09 (q, J = 5.7, 3.7 Hz, 2 H), 2.72 (s, 2H), 2.27 (td, J = 9.5, 6.0 Hz, 2H), 1.70-1.61 (m, 2H), 1.41 (s, 9H), 1.22 (d, J = 5.9 Hz, 3H). |
| G-4-43 | 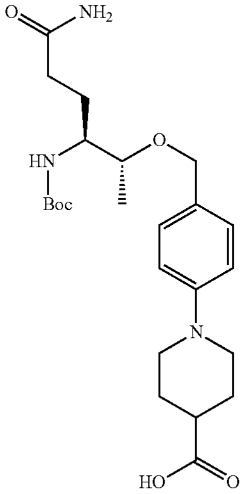 [SMILES: C[C@@H](OCc1ccc(N2CCC(C(=O)O)CC2)cc1)[C@H](CCC(N)=O)NC(=O)OC(C)(C)C] | 1-[4-([[(2R,3S)-3-[(tert-butoxycarbonyl)amino]-5-carbamoylpentan-2-yl]oxy]methyl)phenyl]piperidine-4-carboxylic acid | 464.58 | (400 MHz, DMSO-$d_6$) δ 7.15 (d, J = 8.5 Hz, 2H), 6.88 (d, J = 8.4 Hz, 2H), 4.41-4.29 (m, 2H), 3.61 (d, J = 12.5 Hz, 3H), 2.73 (t, J = 10.9 Hz, 2H), 2.63-2.55 (m, 4H), 1.89 (d, J = 12.5 Hz, 2H), 1.71-1.56 (m, 2H), 1.46 (s, 1H), 1.39 (s, 9H), 1.28-1.23 (m, 4 H), 1.04 (d, J = 6.0 Hz, 3H), 0.90-0.82 (m, 1H) |

4-([[(2R,3S)-3-[(Tert-butoxycarbonyl)amino]-5-carbamoylpentan-2-yl]oxy]methyl)benzoic acid (Intermediate G-4-20)

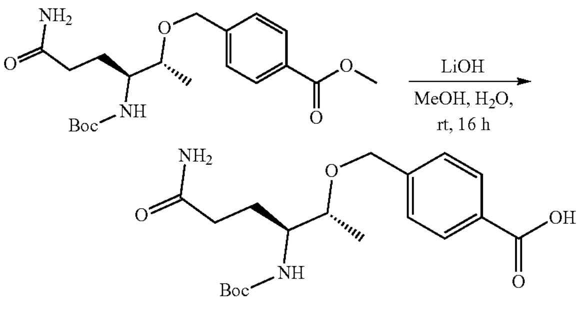

Intermediate G-4-20

To a stirred solution of methyl 4-([[(2R,3S)-3-[(tert-butoxycarbonyl)amino]-5-carbamoylpentan-2-yl]oxy]methyl)benzoate (215 mg, 0.55 mmol) in MeOH (9.00 mL) was added a solution of LiOH (131 mg, 5.45 mmol) in $H_2O$ (3.00 mL) at room temperature. The resulting mixture was stirred for 16 hours at room temperature. The mixture was acidified to pH=6 with AcOH at 0° C. and purified by reversed phase flash chromatography with the following conditions: Column: WelFlash™ C18-I, 20~40 um, 120 g; Eluent A: water (plus 10 mmol/L AcOH); Eluent B: ACN; Gradient: 20% - 40% B in 20 min; Flow rate: 50 mL/min; Detector: UV 220/200 nm; desired fractions were collected at 32% B and concentrated under reduced pressure to afford the title compound as a white solid (190 mg, 92%): $^1$H NMR (400 MHz, DMSO-$d_6$) b 12.88 (s, 1H), 7.90 (d, J=7.8 Hz, 2H), 7.45 (d, J=8.0 Hz, 2H), 7.21 (s, 1H), 6.70-6.61 (m, 2H), 4.56 (d, J=4.3 Hz, 2H), 3.65-3.37 (m, 1H), 2.08-2.00 (m, 1H), 1.78 (s, 1H), 1.50 (s, 1H), 1.37 (s, 9H), 1.09 (d, J=5.8 Hz, 3H); MS (ESI, m/z): $[(M+23)]^+$=403.20.

The following intermediates in Table 41 were prepared according to the above procedure to prepare Intermediate G-4-20.

TABLE 41

| Characterization data for intermediates prepared according to above. | | | | |
|---|---|---|---|---|
| Intermediate | Structure | Chemical Name | MS: $[(M + 1)]^+$ | $^1$H-NMR |
| G-4-21 | 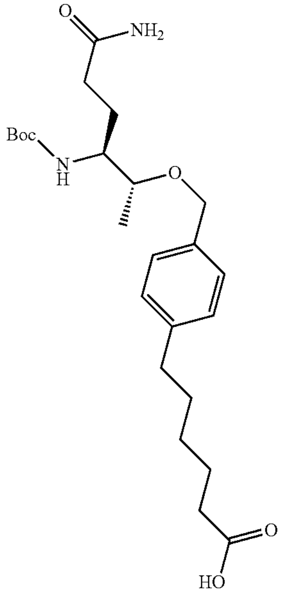 [SMILES: C[C@@H](OCc1ccc(CCCCCC(=O)O)cc1)[C@H](CCC(N)=O)NC(=O)OC(C)(C)C] | 6-[4-([[(2R,3S)-3-[(tert-butoxycarbonyl) amino]-5-carbamoylpentan-2-yl]oxy]methyl) phenyl]hexanoic acid | 451.3 | (400 MHz, $CDCl_3$) δ 7.25 (d, J = 7.8 Hz, 2H), 7.17 (d, J = 7.8 Hz, 2H), 6.70 (s, 1H), 6.41 (s, 1H), 4.80 (d, J = 9.6 Hz, 1H), 4.64 (d, J = 11.7 Hz, 1H), 4.35 (d, J = 11.8 Hz, 1H), 3.66 (s, 1H), 3.52 (d, J = 6.4 Hz, 1H), 2.65 (t, J = 6.9 Hz, 2H), 2.39-2.22 (m, 4H), 1.91 (s, 1H), 1.66 (t, J = 7.4 Hz, 5H), 1.46 (s, 9H), 1.38-1.28 (m, 2H), 1.21 (d, J = 6.2 Hz, 3H). |
| G-4-22 | 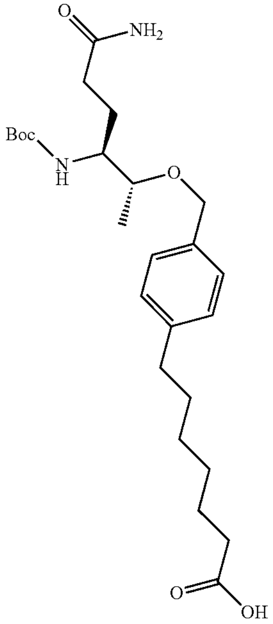 [SMILES: C[C@@H](OCc1ccc(CCCCCCC(=O)O)cc1)[C@H](CCC(N)=O)NC(=O)OC(C)(C)C] | 7-[4-([[(2R,3S)-3-[(tert-butoxycarbonyl) amino]-5-carbamoylpentan-2-yl]oxy]methyl) phenyl]heptanoic acid | 465.3 | (400 MHz, $CD_3OD$) δ 7.28 (d, J = 7.8 Hz, 2H), 7.16 (d, J = 7.8 Hz, 2H), 4.56 (d, J = 11.4 Hz, 1H), 4.49 (d, J = 11.5 Hz, 1H), 3.61-3.50 (m, 2H), 2.62 (t, J = 7.6 Hz, 2H), 2.32-2.20 (m, 4H), 2.00 (s, 1H), 1.62 (q, J = 8.6, 7.1 Hz, 6H), 1.46 (s, 9H), 1.42-1.27 (m, 4H), 1.18 (d, J = 6.1 Hz, 3H). |

TABLE 41-continued

| Characterization data for intermediates prepared according to above. | | | | |
|---|---|---|---|---|
| Intermediate | Structure | Chemical Name | MS: [(M + 1)]$^+$ | $^1$H-NMR |
| G-4-23 | 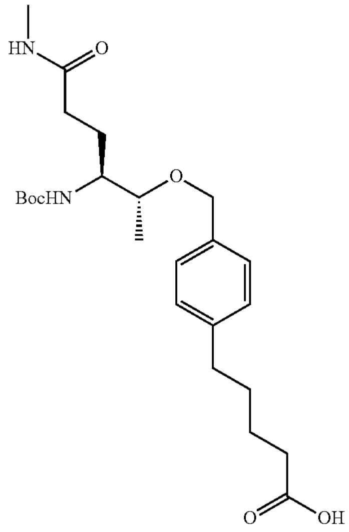 [SMILES: CNC(=O)CC[C@H](NC(=O)OC(C)(C)C)[C@@H](C)OCc1ccc(CCCCC(=O)O)cc1] | 5-[4-([[(2R,3S)-3-[(tert-butoxycarbonyl) amino]-5-(methylcarbamoyl) pentan-2-yl]oxy]methyl) phenyl]pentanoic acid | 451.3 | (400 MHz, $CDCl_3$) δ 7.25 (d, J = 8.0 Hz, 2H), 7.17 (d, J = 8.0 Hz, 2H), 6.42 (s, 1H), 4.87 (d, J = 9.6 Hz, 1H), 4.68-4.29 (m, 2H), 3.65-3.60 (m, 1H), 3.55 (q, J = 5.1, 4.6 Hz, 1H), 2.82 (s, 3H), 2.65 (q, J = 5.4, 4.1 Hz, 2H), 2.36 (d, J = 6.8 Hz, 2H), 2.33-2.14 (m, 2H), 1.97 (q, J = 7.9, 7.2 Hz, 1H), 1.75-1.60 (m, 5H), 1.45 (s, 9H), 1.19 (d, J = 6.2 Hz, 3H). |
| G-4-24 | 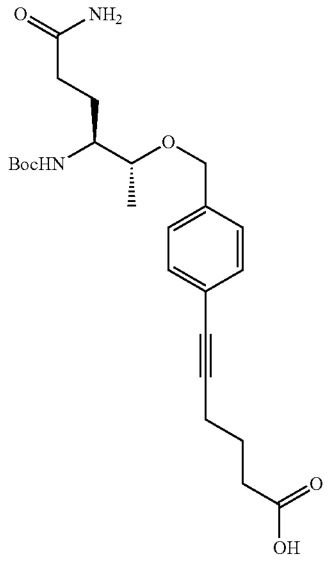 [SMILES: C[C@@H](OCc1ccc(C#CCCCC(=O)O)cc1)[C@H](CCC(N)=O)NC(=O)OC(C)(C)C] | 6-[4-([[(2R,3S)-3-[(tert-butoxycarbonyl) amino]-5-carbamoylpentan-2-yl]oxy]methyl) phenyl]hex-5-ynoic acid | 447.2 | (400 MHz, DMSO-$d_6$) δ 12.14 (br, 1H), 7.38-7.27 (m, 4H), 7.23 (s, 1H), 6.69 (s, 1H), 6.63 (d, J = 9.1 Hz, 1H), 4.54-4.42 (m, 2H), 3.41 (dd, J = 14.9, 8.7 Hz, 2H), 2.50-2.30 (m, 4H), 2.07-2.03 (m, 2H), 1.77 (m, 3H), 1.50-1.40 (m, 1H), 1.38 (s, 9H), 1.07 (d, J = 6.0 Hz, 3H). |

TABLE 41-continued

| Characterization data for intermediates prepared according to above. | | | | |
|---|---|---|---|---|
| Intermediate | Structure | Chemical Name | MS: [(M + 1)]$^+$ | $^1$H-NMR |
| G-4-25 | 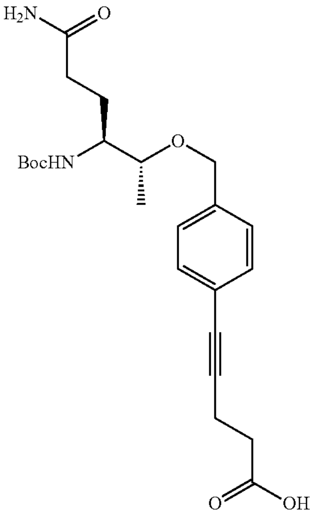 [SMILES: C[C@@H](OCc1ccc(C#CCCC(=O)O)cc1)[C@H](CCC(N)=O)NC(=O)OC(C)(C)C] | 5-[4-([[(2R,3S)-3-[(tert-butoxycarbonyl) amino]-5-carbamoylpentan-2-yl]oxy]methyl) phenyl]pent-4-ynoic acid | 433.2 | (400 MHz, $CD_3OD$) δ 7.38-7.28 (m, 4H), 4.58 (d, J = 12.0 Hz, 1H), 4.50 (d, J = 11.9 Hz, 1H), 3.58 (ddd, J = 10.8, 5.2, 3.2 Hz, 1H), 3.56-3.46 (m, 1H), 2.70 (td, J = 7.0, 1.4 Hz, 2H), 2.60 (td, J = 6.9, 1.3 Hz, 2H), 2.25 (tdd, J = 14.8, 11.8, 7.8 Hz, 2H), 2.08-1.92 (m, 1H), 1.65-1.60 (m, 1H), 1.45 (s, 9H), 1.18 (d, J = 6.2 Hz, 3H). |
| G-4-26 | 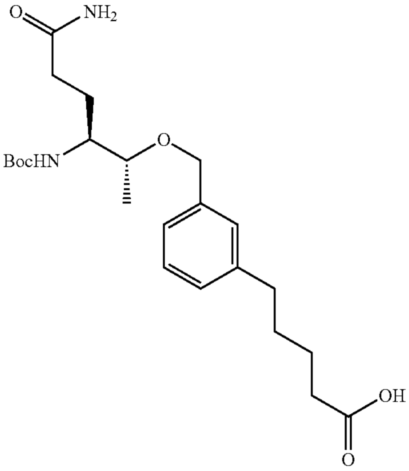 [SMILES: C[C@@H](OCc1cccc(CCCCC(=O)O)c1)[C@H](CCC(N)=O)NC(=O)OC(C)(C)C] | 5-[3-([[(2R,3S)-3-[(tert-butoxycarbonyl) amino]-5-carbamoylpentan-2-yl]oxy]methyl) phenyl]pentanoic acid | 437.3 | (400 MHz, $CD_3OD$) δ 7.30-7.06 (m, 4H), 4.63-4.41 (m, 2H), 3.75-3.44 (m, 2H), 2.65 (s, 2H), 2.43-2.15 (m, 4H), 1.98 (ddd, J = 16.5, 8.8, 3.0 Hz, 1H), 1.76-1.54 (m, 5H), 1.46 (s, 9H), 1.18 (d, J = 6.3 Hz, 3H). |
| G-4-27 | 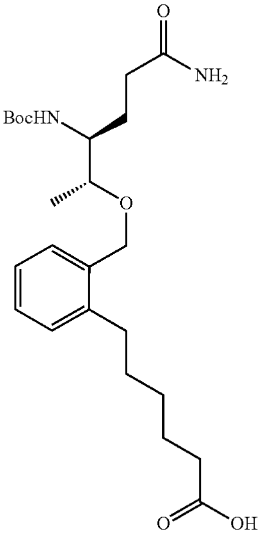 [SMILES: C[C@@H](OCc1ccccc1CCCCCC(=O)O)[C@H](CCC(N)=O)NC(=O)OC(C)(C)C] | 6-[2-([[(2R,3S)-3-[(tert-butoxycarbonyl) amino]-5-carbamoylpentan-2-yl]oxy]methyl) phenyl]hexanoic acid | 451.2 | (400 MHz, DMSO-$d_6$) δ 12.00 (br, 1H), 7.32 (d, J = 7.4 Hz, 1H), 7.20-7.05 (m, 4H), 6.71-6.57 (m, 2H), 4.55-4.40 (m, 2H), 3.45 (d, J = 6.9 Hz, 2H), 3.35-3.30 (m, 2H), 2.59 (t, J = 7.9 Hz, 2H), 2.21 (t, J = 7.3 Hz, 2H), 2.04 (tt, J = 16.3, 6.9 Hz, 2H), 1.85-1.75 (m, 1H), 1.55-1.40 (m, 5H), 1.39 (s, 9H), 1.08 (d, J = 5.5 Hz, 3H). |

TABLE 41-continued

| Characterization data for intermediates prepared according to above. | | | | |
|---|---|---|---|---|
| Intermediate | Structure | Chemical Name | MS: [(M + 1)]+ | $^1$H-NMR |
| G-4-44 | 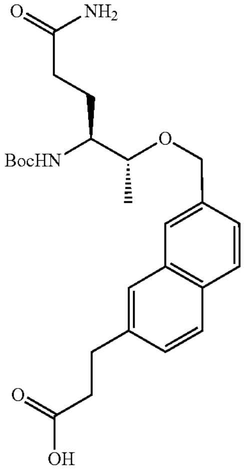 [SMILES: C[C@@H](OCc1ccc2ccc(CCC(=O)O)cc2c1)[C@H](CCC(N)=O)NC(=O)OC(C)(C)C] | 3-[7-([[(2R,3S)-3-[(tert-butoxycarbonyl) amino]-5-carbamoylpentan-2-yl]oxy]methyl) naphthalen-2-yl]propanoic acid | 459.30 | (400 MHz, DMSO-$d_6$) δ 12.09 (s, 1H), 7.84-7.80 (m, 2H), 7.76 (s, 1H), 7.68 (s, 1H), 7.48-7.36 (m, 2H), 7.24 (s, 1H), 6.73-6.61 (m, 2H), 4.67-4.59 (m, 2H), 3.48-3.44 (m, 2H), 3.01-2.97 (m, J = 7.6 Hz, 2H), 2.63 (m, J = 7.6 Hz, 2H), 2.12-2.05 (m, 2H), 1.88-1.77 (m, 1H), 1.64-1.52 (m, 1H), 1.38 (s, 9H), 1.10 (d, J = 5.9 Hz, 3H) |
| G-4-45 | 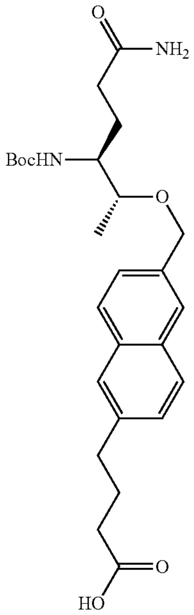 [SMILES: C[C@@H](OCc1ccc2cc(CCCC(=O)O)ccc2c1)[C@H](CCC(N)=O)NC(=O)OC(C)(C)C] | 4-[6-([[(2R,3S)-3-[(tert-butoxycarbonyl) amino]-5-carbamoylpentan-2-yl]oxy]methyl) naphthalen-2-yl]butanoic acid | 473.15 | (400 MHz, $CD_3OD$) δ 7.83-7.75 (m, 3H), 7.65 (s, 1H), 7.49 (dd, J = 8.5, 1.6 Hz, 1H), 7.38 (dd, J = 8.4, 1.7 Hz, 1H), 4.75 (d, J = 11.8 Hz, 1H), 4.66 (d, J = 11.8 Hz, 1H), 3.65-3.52 (m, 2H), 2.83 (t, J = 7.6 Hz, 2H), 2.40-2.18 (m, 4H), 2.08-1.95 (m, 3H), 1.65 (dtd, J = 14.9, 9.6, 5.8 Hz, 1H), 1.40 (s, 9H), 1.22 (d, J = 5.9 Hz, 3H) |
| G-4-46 | 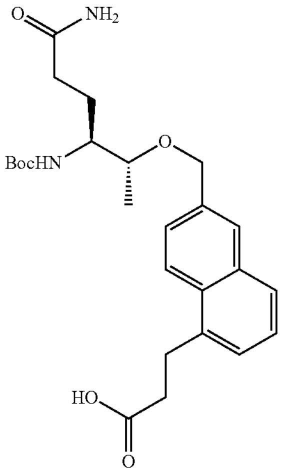 [SMILES: C[C@@H](OCc1ccc2c(CCC(=O)O)cccc2c1)[C@H](CCC(N)=O)NC(=O)OC(C)(C)C] | 3-[6-([[(2R,3S)-3-[(tert-butoxycarbonyl) amino]-5-carbamoylpentan-2-yl]oxy]methyl) naphthalen-1-yl]propanoic acid | 459.20 | (400 MHz, DMSO-$d_6$) δ 12.12 (s, 1H), 8.03 (d, J = 8.7 Hz, 1H), 7.86 (d, J = 1.7 Hz, 1H), 7.76 (d, J = 8.0 Hz, 1H), 7.53 (dd, J = 8.8, 1.8 Hz, 1H), 7.42 (t, J = 7.6 Hz, 1H), 7.36 (d, J = 6.9 Hz, 1H), 7.24 (s, 1H), 6.72-6.63 (m, 2H), 4.71-4.60 (m, 2H), 3.51-3.47 (m, 2H), 3.34-3.25 (m, 2H), 2.64 (t, J = 7.7 Hz, 2H), 2.08-2.04 (m, 2H), 1.85-1.81 (m, 1H), 1.54-1.51 (m, 1H), 1.37 (s, 9H), 1.11 (d, J = 5.8 Hz, 3H) |

TABLE 41-continued

| Characterization data for intermediates prepared according to above. | | | | |
|---|---|---|---|---|
| Intermediate | Structure | Chemical Name | MS: [(M + 1)]+ | $^1$H-NMR |
| G-4-47 | 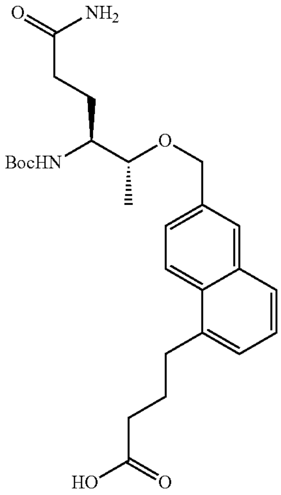 [SMILES: C[C@@H](OCc1ccc2c(CCCC(=O)O)cccc2c1)[C@H](CCC(N)=O)NC(=O)OC(C)(C)C] | 4-[6-([[(2R,3S)-3-[(tert-butoxycarbonyl)amino]-5-carbamoylpentan-2-yl]oxy]methyl)naphthalen-1-yl]butanoic acid | 473.15 | (400 MHz, DMSO-$d_6$) δ 12.11 (s, 1H), 8.08 (d, J = 8.7 Hz, 1H), 7.84 (d, J = 1.7 Hz, 1H), 7.74 (d, J = 8.1 Hz, 1H), 7.51 (dd, J = 8.8, 1.8 Hz, 1H), 7.42 (dd, J = 8.2, 7.0 Hz, 1H), 7.32 (dd, J = 7.1, 1.2 Hz, 1H), 7.23 (s, 1H), 6.72-6.61 (m, 2H), 4.71-4.59 (m, 2H), 3.47 (dq, J = 11.8, 6.6, 6.0 Hz, 2H), 3.05 (dd, J = 9.0, 6.7 Hz, 2H), 2.32 (t, J = 7.2 Hz, 2H), 2.09-2.06 (m, 2H), 1.95-1.80 (m, 3H), 1.58-1.46 (m, 1H), 1.37 (s, 9H), 1.11 (d, J = 5.8 Hz, 3H). |
| G-4-48 | 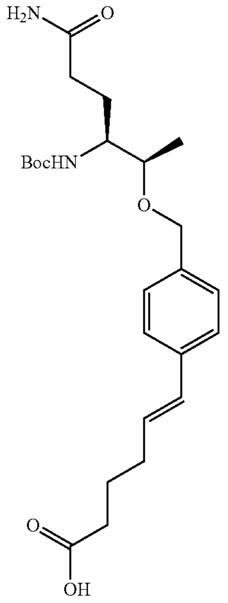 [SMILES: C[C@@H](OCc1ccc(/C=C/CCCC(=O)O)cc1)[C@H](CCC(N)=O)NC(=O)OC(C)(C)C] | (5E)-6-[4-([[(2R,3S)-3-[(tert-butoxycarbonyl)amino]-5-carbamoylpentan-2-yl]oxy]methyl)phenyl]hex-5-enoic acid | [M + Na)]+ = 472.15 | Used in the next step without further purification |

TABLE 41-continued

| Inter-mediate | Structure | Chemical Name | MS: [(M + 1)]+ | $^1$H-NMR |
|---|---|---|---|---|
| Characterization data for intermediates prepared according to above. | | | | |
| G-4-49 | 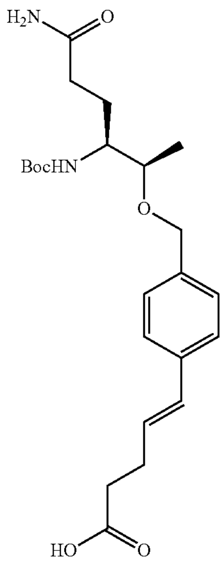 [SMILES: C[C@@H](OCc1ccc(/C=C/CCC(=O)O)cc1)[C@H](CCC(N)=O)NC(=O)OC(C)(C)C] | (4E)-5-[4-([[(2R,3S)-3-[(tert-butoxycarbonyl)amino]-5-carbamoylpentan-2-yl]oxy]methyl)phenyl]pent-4-enoic acid | 435.20 | (400 MHz, DMSO-$d_6$) δ 12.07 (s, 1H), 7.33 (d, J = 8.0 Hz, 2H), 7.26 (d, J = 8.1 Hz, 2H), 7.23 (s, 1H), 6.69 (s, 1H), 6.62 (d, J = 9.1 Hz, 1H), 6.42 (d, J = 16.0 Hz, 1H), 6.32-6.22 (m, 1H), 4.50-4.39 (m, 2H), 3.31 (s, 3H), 2.42-2.38 (m, 3H), 2.14-1.97 (m, 1H), 1.81-1.77 (s, 1H), 1.38 (s, 9H), 1.22-1.20 (m, 2H), 1.06 (d, J = 6.1 Hz, 3H) |
| G-4-50 | 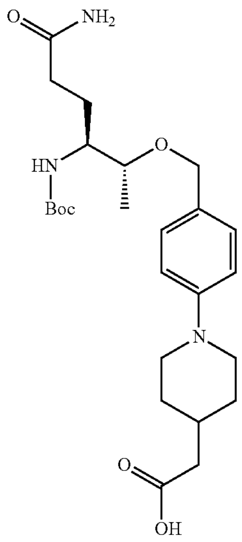 [SMILES: C[C@@H](OCc1ccc(N2CCC(CC(=O)O)CC2)cc1)[C@H](CCC(N)=O)NC(=O)OC(C)(C)C] | [1-[4-([[(2R,3S)-3-[(tert-butoxycarbonyl)amino]-5-carbamoylpentan-2-yl]oxy]methyl)phenyl]piperidin-4-yl]acetic acid | 478.30 | (400 MHz, $CD_3OD$) δ 7.29-7.20 (m, 2H), 7.02-6.93 (m, 2H), 4.50 (d, J = 11.2 Hz, 1H), 4.43 (d, J = 11.3 Hz, 1H), 3.68 (d, J = 12.2 Hz, 2H), 3.56 (s, 1H), 3.60-3.45 (m, 1H), 2.75-2.68 (m, 2H), 2.33-2.17 (m, 4H), 2.09-1.95 (m, 2H), 1.99-1.83 (m, 3H), 1.63-1.56 (m, 1H), 1.45 (s, 9H), 1.40 (dd, J = 12.1, 3.6 Hz, 1H), 1.16 (d, J = 6.2 Hz, 3H) |

TABLE 41-continued

| Characterization data for intermediates prepared according to above. | | | | |
|---|---|---|---|---|
| Intermediate | Structure | Chemical Name | MS: $[(M + 1)]^+$ | $^1$H-NMR |
| G-4-51 | 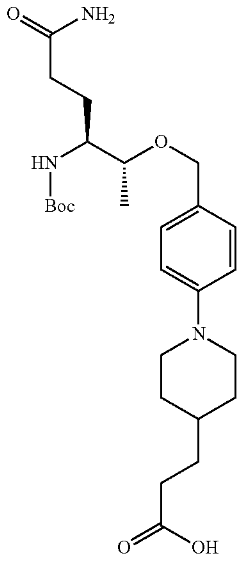 [SMILES: C[C@@H](OCc1ccc(N2CCC(CCC(=O)O)CC2)cc1)[C@H](CCC(N)=O)NC(=O)OC(C)(C)C] | 3-[1-[4-([[(2R,3S)-3-[(tert-butoxycarbonyl)amino]-5-carbamoylpentan-2-yl]oxy]methyl)phenyl]piperidin-4-yl]propanoic acid | $[(M - 1]^-$ = 490.30 | (400 MHz, $CD_3OD$) δ 7.29-7.19 (d, J = 8.6 Hz, 2H), 6.97 (d, J = 8.6 Hz, 2H), 4.46 (dd, J = 16.0, 32 Hz, 2H) 3.73-3.63 (m, 2H), 3.58-3.48 (m, 2H), 2.68 (t, J = 12.0, 2H), 2.37 (t, J = 7.6 Hz, 2H), 2.32-2.16 (m, 2H), 2.05-1.90 (m, 1H), 1.90-1.79 (m, 2H), 1.62 (q, J = 7.3 Hz, 3H), 1.45 (s, 9H), 1.41-1.31 (m, 2H), 1.16 (d, J = 6.2 Hz, 3H) |
| G-4-52 | 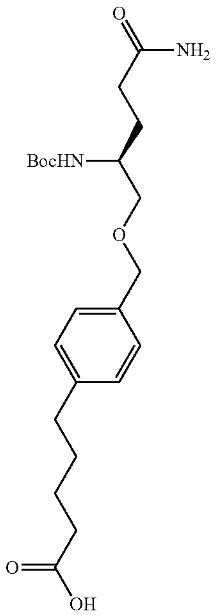 [SMILES: CC(C)(C)OC(=O)N[C@@H](CCC(N)=O)COCc1ccc(CCCCC(=O)O)cc1] | 5-(4-[[(2S)-2-[(Tert-butoxycarbonyl)amino]-4-carbamoylbutoxy]methyl]phenyl)pentanoic acid | 423.15 | (400 MHz, DMSO-$d_6$) δ 11.95 (s, 1H), 7.22 (d, J = 7.9 Hz, 3H), 7.15 (d, J = 8.0 Hz, 2H), 6.70 (s, 1H), 6.66 (d, J = 8.7 Hz, 1H), 4.42 (s, 2H), 3.56 (dq, J = 9.5, 4.5 Hz, 1H), 3.38-3.35 (m, 2H), 3.34-3.23 (m, 2H), 2.57 (t, J = 7.2 Hz, 2H), 2.23 (t, J = 7.1 Hz, 2H), 2.12-2.01 (m, 2H), 1.80-1.67 (m, 1H), 1.62-1.43 (m, 3H), 1.38 (s, 9H) |
| G-4-53 | 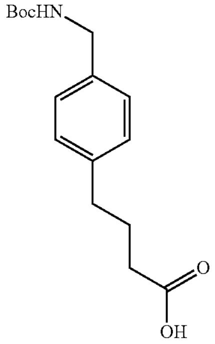 [SMILES: CC(C)(C)OC(=O)NCc1ccc(CCCC(=O)O)cc1] | 4-(4-[[(tert-butoxycarbonyl)amino]methyl]phenyl)butanoic acid | $[(M - 1)]^-$ = 292.20 | (400 MHz, DMSO-$d_6$) δ 12.05 (s, 1H), 7.36 (t, J = 6.2 Hz, 1H), 7.15-7.12 (m, 4H), 4.09 (d, J = 6.1 Hz, 2H), 2.55 (t, J = 7.6 Hz, 2H), 2.20 (t, J = 7.4 Hz, 2H), 1.77 (p, J = 7.5 Hz, 2H), 1.39 (s, 9H). |

TABLE 41-continued

| Characterization data for intermediates prepared according to above. | | | | |
|---|---|---|---|---|
| Intermediate | Structure | Chemical Name | MS: $[(M + 1)]^+$ | $^1$H-NMR |
| G-4-54 | 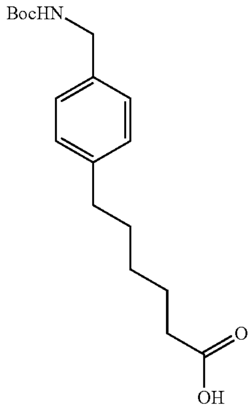 [SMILES: CC(C)(C)OC(=O)NCc1ccc(CCCCCC(=O)O)cc1] | 6-(4-[[(tert-butoxycarbonyl) amino]methyl] phenyl)hexanoic acid | 322.20 | (400 MHz, DMSO-$d_6$) δ 11.96 (s, 1H), 7.33 (t, J = 6.3 Hz, 1H), 7.13 (s, 4H), 4.08 (d, J = 6.0 Hz, 2H), 2.57-2.51 (m, 2H), 2.19 (t, J = 7.3 Hz, 2H), 1.80-1.46 (m, 4H), 1.40 (s, 9H), 1.30-1.25 (m, 2H). |
| G-4-55 | 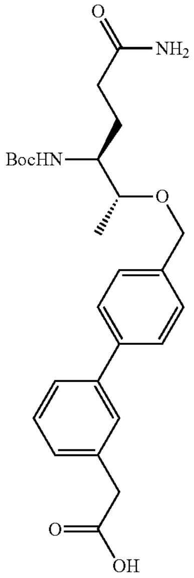 [SMILES: C[C@@H](OCc1ccc(-c2cccc(CC(=O)O)c2)cc1)[C@H](CCC(N)=O)NC(=O)OC(C)(C)C] | [4'-([[(2R,3S)-3-[(tert-butoxycarbonyl) amino]-5-carbamoylpentan-2-yl]oxy]methyl)-[1,1'-biphenyl]-3-yl]acetic acid | 471.20 | (400 MHz, DMSO-$d_6$) δ 7.61 (d, J = 8.2 Hz, 2H), 7.58-7.51 (m, 2H), 7.45-7.37 (m, 3H), 7.25 (dt, J = 9.2, 2.3 Hz, 2H), 6.73-6.61 (m, 2H), 4.60-4.48 (m, 2H), 3.64 (s, 2H), 3.49-3.42 (m, 3H), 2.06-2.04 (m, 2H), 1.83-1.81 (m, 1H), 1.56-1.45 (m, 1H), 1.39 (s, 9H), 1.09 (d, J = 5.9 Hz, 3H) |
| G-4-56 | 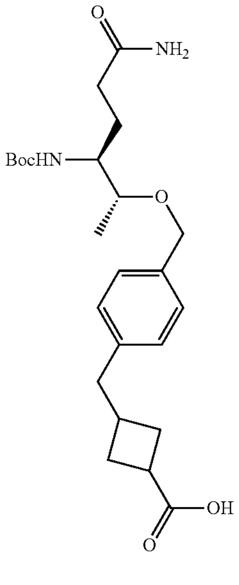 [SMILES: C[C@@H](OCc1ccc(CC2CC(C(=O)O)C2)cc1)[C@H](CCC(N)=O)NC(=O)OC(C)(C)C] | 3-[[4-([[(2R,3S)-3-[(tert-butoxycarbonyl) amino]-5-carbamoylpentan-2-yl]oxy]methyl) phenyl]methyl] cyclobutane-1-carboxylic acid | 449.25 | (400 MHz, $CDCl_3$) δ 7.25 (d, J = 7.8 Hz, 2H), 7.16-7.10 (m, 2H), 6.58 (s, 1H), 6.01 (s, 1H), 4.90 (d, J = 9.7 Hz, 1H), 4.67-4.55 (m, 1H), 4.46-4.34 (m, 1H), 3.73-3.48 (m, 2H), 3.00 (p, J = 9.1 Hz, 1H), 2.84-2.66 (m, 2H), 2.61-2.20 (m, 5H), 2.14-1.89 (m, 3H), 1.67 (dd, J = 28.1, 13.7 Hz, 1H), 1.46 (s, 9H), 1.21 (d, J = 6.1 Hz, 3H) |

TABLE 41-continued

| Characterization data for intermediates prepared according to above. | | | | |
|---|---|---|---|---|
| Inter-mediate | Structure | Chemical Name | MS: [(M + 1)]+ | $^1$H-NMR |
| G-4-57 | 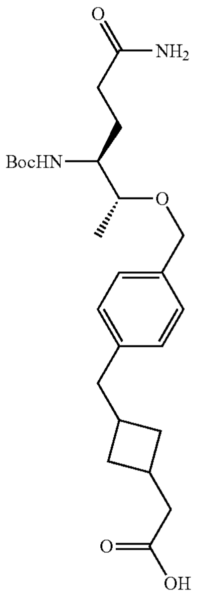 [SMILES: C[C@@H](OCc1ccc(CC2CC(CC(=O)O)C2)cc1)[C@H](CCC(N)=O)NC(=O)OC(C)(C)C] | (3-[[4-([[(2R,3S)-3-[(tert-butoxycarbonyl)amino]-5-carbamoylpentan-2-yl]oxy]methyl)phenyl]methyl]cyclobutyl)acetic acid | 463.40 | (400 MHz, DMSO-$d_6$) δ 7.21 (dd, J = 8.1, 2.5 Hz, 3H), 7.10 (dd, J = 10.7, 7.9 Hz, 2H), 6.68 (s, 1H), 6.61 (d, J = 9.1 Hz, 1H), 4.48-4.39 (m, 2H), 3.54-3.48 (m, 1H), 3.48-3.35 (m, 1H), 2.69 (d, J = 7.8 Hz, 1H), 2.64-2.51 (m, 2H), 2.40-2.24 (m, 4H), 2.18-2.04 (m, 3H), 2.04-1.95 (m, 1H), 1.90-1.66 (m, 2H), 1.56-1.42 (m, 1H), 1.39 (s, 9H), 1.05 (s, 3H) |
| G-4-58 | 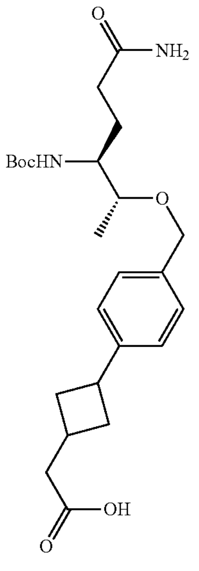 [SMILES: C[C@@H](OCc1ccc(C2CC(CC(=O)O)C2)cc1)[C@H](CCC(N)=O)NC(=O)OC(C)(C)C] | [3-[4-([[(2R,3S)-3-[(tert-butoxycarbonyl)amino]-5-carbamoylpentan-2-yl]oxy]methyl)phenyl]cyclobutyl]acetic acid | 419.15 | (400 MHz, $CD_3OD$) δ 7.30 (t, J = 8.0 Hz, 2H), 7.27-7.17 (m, 2H), 4.61-4.44 (m, 2H), 3.67-3.57 (m, 1H), 3.57-3.47 (m, 1H), 3.48-3.35 (m, 1H), 2.77-2.51 (m, 3H), 2.43 (d, J = 7.2 Hz, 1H), 2.39-2.14 (m, 4H), 2.07-1.93 (m, 1H), 1.90-1.77 (m, 1H), 1.68-1.56 (m, 1H), 1.45 (s, 9H), 1.18 (s, 3H) |

TABLE 41-continued

| Characterization data for intermediates prepared according to above. | | | | |
|---|---|---|---|---|
| Intermediate | Structure | Chemical Name | MS: [(M + 1)]+ | $^1$H-NMR |
| G-4-59 | 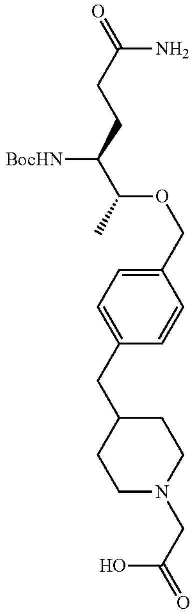 [SMILES: C[C@@H](OCc1ccc(CC2CCN(CC(=O)O)CC2)cc1)[C@H](CCC(N)=O)NC(=O)OC(C)(C)C] | (4-[[4-([[(2R,3S)-3-[(tert-butoxycarbonyl)amino]-5-carbamoylpentan-2-yl]oxy]methyl)phenyl]methyl]piperidin-1-yl)acetic acid | 492.25 | (400 MHz, DMSO-$d_6$) δ 7.25-7.23 (m, 3H), 7.12 (d, J = 7.8 Hz, 2H), 6.71 (s, 1H), 6.62 (d, J = 9.1 Hz, 1H), 4.48-4.38 (m, 2H), 4.08 (d, J = 20.1 Hz, 1H), 3.45-3.38 (m, 2H), 3.1-3.19 (m, 3H), 2.66-2.52 (m, 2H), 2.07-2.01 (m, 2H), 1.80-1.76 (m, 1H), 1.69-1.56 (m, 4H), 1.52-1.41 (m, 2H), 1.40 (s, 9H), 1.06 (d, J = 6.0 Hz, 3H) |
| G-4-60 | 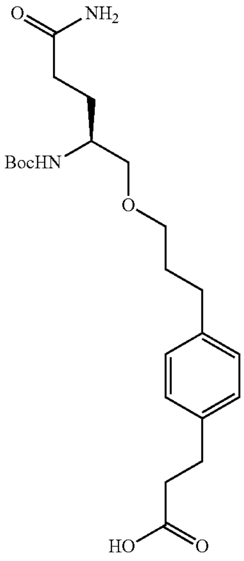 [SMILES: CC(C)(C)OC(=O)N[C@@H](CCC(N)=O)COCCCc1ccc(CCC(=O)O)cc1] | 3-(4-[3-[(2S)-2-[(tert-butoxycarbonyl)amino]-4-carbamoylbutoxy]propyl]phenyl)propanoic acid | 422.522 | (400 MHz, $CD_3OD$) δ 7.25-7.22 (m, 1H), 7.22-7.10 (m, 4H), 4.27 (dd, J = 6.3, 1.7 Hz, 1H), 3.71-3.65 (m, 1H), 3.51-3.35 (m, 4H), 2.95-2.87 (m, 3H), 2.71-2.56 (m, 4H), 2.31-2.26 (m, 3H), 1.96-1.81 (m, 3H), 1.73-1.63 (m, 1H), 1.46 (s, 9H) |

TABLE 41-continued

| Characterization data for intermediates prepared according to above. | | | | |
|---|---|---|---|---|
| Intermediate | Structure | Chemical Name | MS: $[(M + 1)]^+$ | $^1$H-NMR |
| G-4-61 | 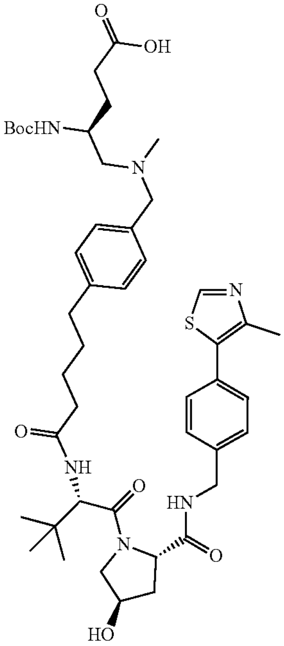 [SMILES: Cc1ncsc1-c1ccc(CNC(=O)[C@@H]2C[C@@H](O)CN2C(=O)[C@@H](NC(=O)CCCCc2ccc(CN(C)C[C@H](CCC(=O)O)NC(=O)OC(C)(C)C)cc2)C(C)(C)C)cc1] | (4S)-4-[(tert-butoxycarbonyl)amino]-5-([[4-(4-[[(2S)-1-[(2S,4R)-4-hydroxy-2-(([4-(4-methyl-1,3-thiazol-5-yl)phenyl]methyl]carbamoyl)pyrrolidin-1-yl]-3,3-dimethyl-1-oxobutan-2-yl]carbamoyl]butyl)phenyl]methyl](methyl)amino)pentanoic acid | 849.30 | (400 MHz, $CD_3OD$) δ 8.89 (s, 1H), 7.48 (d, J = 8.2 Hz, 2H), 7.45-7.41 (m, 2H), 7.37 (d, J = 7.8 Hz, 2H), 7.26 (d, J = 7.8 Hz, 2H), 4.65 (s, 1H), 4.57 (d, J = 7.6 Hz, 1H), 4.52 (s, 1H), 4.38 (d, J = 15.6 Hz, 1H), 4.14 (d, J = 12.4 Hz, 1H), 3.94 (d, J = 8.7 Hz, 2H), 3.82 (dd, J = 11.0, 3.9 Hz, 1H), 2.90 (s, 2H), 2.67 (s, 2H), 2.62 (s, 3H), 2.49 (s, 3H), 2.32-2.29 (m, 3H), 2.14-2.01 (m, 2H), 1.99 (s, 2H), 1.85 (dd, J = 14.0, 6.3 Hz, 1H), 1.70-1.58 (m, 5H), 1.48 (s, 9H), 1.05 (s, 9H) |
| G-4-62 | 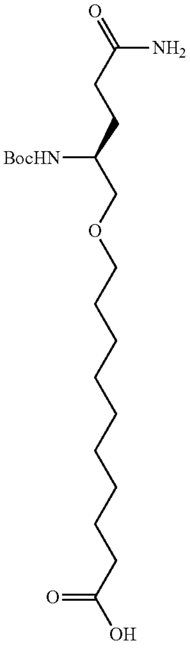 [SMILES: CC(C)(C)OC(=O)N[C@@H](CCC(N)=O)COCCCCCCCCCC(=O)O] | 10-[(2S)-2-[(tert-butoxycarbonyl)amino]-4-carbamoylbutoxy]decanoic acid | $[(M - H)]^-$ = 401.10 | (400 MHz, DMSO-$d_6$) δ 11.94 (s, 1H), 7.22 (s, 1H), 6.78-6.52 (m, 1H), 3.53 (t, J = 6.7 Hz, 1H), 3.43-3.36 (m, 1H), 3.29-3.13 (m, 1H), 2.21-2.17 (m, 2H), 2.09-1.99 (m, 1H), 1.85-1.56 (m, 1H), 1.48 (q, J = 7.2 Hz, 5H), 1.38 (s, 8H), 1.31-1.21 (m, 15H). |

TABLE 41-continued

| Characterization data for intermediates prepared according to above. | | | | |
|---|---|---|---|---|
| Intermediate | Structure | Chemical Name | MS: $[(M + 1)]^+$ | $^1$H-NMR |
| G-4-63 | 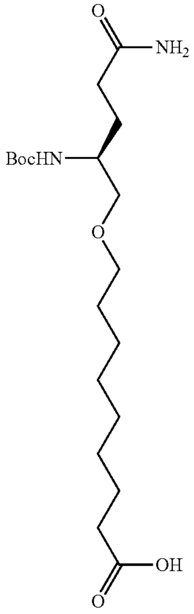 [SMILES: CC(C)(C)OC(=O)N[C@@H](CCC(N)=O)COCCCCCCCCC(=O)O] | 9-[(2S)-2-[(tert-butoxycarbonyl) amino]-4-carbamoylbutoxy] nonanoic acid | 389.35 | (400 MHz, DMSO-$d_6$) δ 11.95 (s, 1H), 7.21 (s, 1H), 6.68 (s, 1H), 6.56 (d, J = 8.9 Hz, 1H), 3.52 (t, J = 6.7 Hz, 1H), 3.51-3.48 (m, 1H), 3.40-3.35 (m, 1H), 3.28-3.14 (m, 2H), 2.21-2.15 (m, 6H), 2.11-2.00 (m, 2H), 1.79 (dt, J = 14.2, 6.8 Hz, 2H), 1.73-1.60 (m, 1H), 1.56-1.43 (m, 7H), 1.37 (s, 9H). |
| G-4-64 | 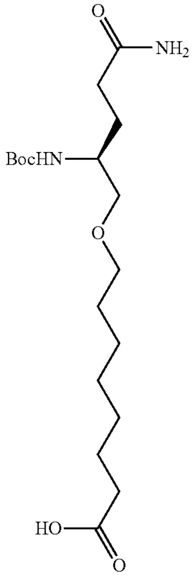 [SMILES: CC(C)(C)OC(=O)N[C@@H](CCC(N)=O)COCCCCCCCC(=O)O] | (S)-8-((5-amino-2-((tert-butoxycarbonyl) amino)-5-oxopentyl)oxy) octanoic acid | 376.20 | (400 MHz, DMSO-$d_6$) δ 7.23 (s, 1H), 6.69 (s, 1H) 6.63-6.48 (m, 1H), 3.53 (t, J = 6.7 Hz, 1H), 3.45-3.13 (m, 4H), 2.27-1.98 (m, 4H), 1.73-1.65 (m, 1H), 1.52-1.42 (m, 3H), 1.38 (s, 9H), 1.32-1.21 (m, 8H) |

TABLE 41-continued

Characterization data for intermediates prepared according to above.

| Inter-mediate | Structure | Chemical Name | MS: $[(M + 1)]^+$ | $^1$H-NMR |
|---|---|---|---|---|
| G-4-65 | 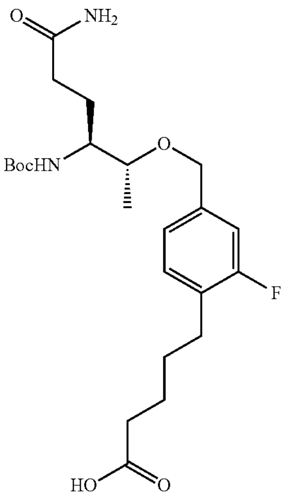 [SMILES: C[C@@H](OCc1ccc(CCCCC(=O)O)c(F)c1)[C@H](CCC(N)=O)NC(=O)OC(C)(C)C] | 5-[4-([[(2R,3S)-3-[(tert-butoxycarbonyl) amino]-5-carbamoylpentan-2-yl]oxy]methyl)-2-fluorophenyl] pentanoic acid | 455.20 | (400 MHz, DMSO-$d_6$) δ 11.87 (s, 1H), 7.26-7.18 (m, 2H), 7.08 (t, J = 11.0 Hz, 2H), 6.71-6.61 (m, 2H), 4.51-4.39 (m, 2H), 3.47 (s, 1H), 3.41 (d, J = 11.7 Hz, 1H), 2.59 (t, J = 7.1 Hz, 2H), 2.23 (t, J = 6.8 Hz, 2H), 2.11-1.99 (m, 1H), 1.84-1.68 (m, 1H), 1.55-1.45 (m, 6H), 1.38 (s, 9H), 1.06 (d, J = 6.1 Hz, 3H) |
| G-4-66 | 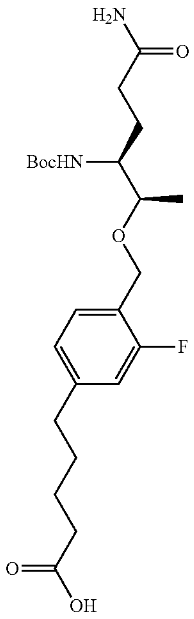 [SMILES: C[C@@H](OCc1ccc(CCCCC(=O)O)cc1F)[C@H](CCC(N)=O)NC(=O)OC(C)(C)C] | 5-[4-([[(2R,3S)-3-[(tert-butoxycarbonyl) amino]-5-carbamoylpentan-2-yl]oxy]methyl)-3-fluorophenyl] pentanoic acid | 455.15 | (400 MHz, DMSO-$d_6$) δ 7.34 (t, J = 7.9 Hz, 1H), 7.20 (s, 1H), 7.05-6.96 (m, 2H), 6.67 (s, 1H), 6.59 (d, J = 8.7 Hz, 1H), 4.48 (q, J = 8.0 Hz, 2H), 3.51-3.40 (m, 3H), 2.58 (t, J = 7.3 Hz, 2H), 2.22 (t, J = 7.2 Hz, 2H), 2.14-1.92 (m, 3H), 1.85-1.70 (m, 1H), 1.63-1.43 (m, 4H), 1.38 (s, 9H), 1.06 (d, J = 5.5 Hz, 3H) |

TABLE 41-continued

Characterization data for intermediates prepared according to above.

| Inter-mediate | Structure | Chemical Name | MS: [(M + 1)]+ | $^1$H-NMR |
|---|---|---|---|---|
| G-4-67 | 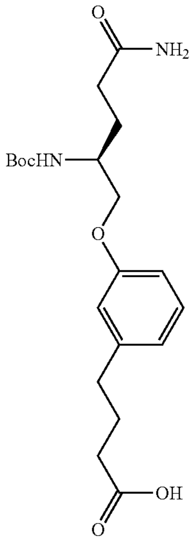 [SMILES: CC(C)(C)OC(=O)N[C@@H](CCC(N)=O)COc1cccc(CCCC(=O)O)c1] | 4-[3-[(2S)-2-[(tert-butoxycarbonyl) amino]-4-carbamoylbutoxy] phenyl]butanoic acid | 395.30 | (400 MHz, DMSO-$d_6$) δ 12.04 (s, 1H), 7.26 (s, 1H), 7.19 (dd, J = 9.0, 7.2 Hz, 1H), 6.81 (d, J = 8.5 Hz, 1H), 6.79-6.70 (m, 4H), 3.87-3.83 (m, 2H), 3.66-3.57 (m, 1H), 2.58-2.54 (m, 2H), 2.21 (t, J = 7.4 Hz, 2H), 2.15-2.11 (m, 2H), 1.87-1.73 (m, 3H), 1.65-1.61 (m, 1H), 1.40 (s, 9H) |
| G-4-87 | 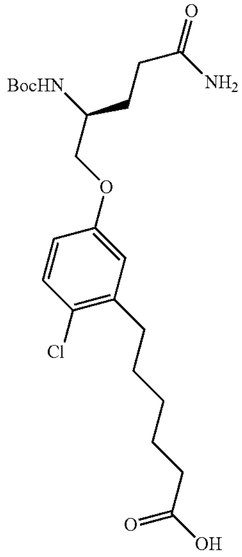 [SMILES: CC(C)(C)OC(=O)N[C@@H](CCC(N)=O)COc1ccc(Cl)c(CCCCCC(=O)O)c1] | 6-[5-[(2S)-2-[(tert-butoxycarbonyl) amino]-4-carbamoylbutoxy]-2-chlorophenyl] hexanoic acid | 457.30 | (400 MHz, DMSO-$d_6$) δ 11.94 (m, 2H), 7.28 (d, J = 8.7 Hz, 1H), 6.91 (d, J = 3.0 Hz, 1H), 6.85-6.69 (m, 2H), 3.85-3.83 (m, 2H), 3.73-3.69 (m, 1H), 2.64-2.62 (m, 2H), 2.19-2.17 (m, 4H), 2.11-2.09 (m, J = 7.8 Hz, 2H), 1.63-1.52 (m, 5H), 1.50-1.46 (m, 2H), 1.25 (s, 9H) |

TABLE 41-continued

| Characterization data for intermediates prepared according to above. | | | | |
|---|---|---|---|---|
| Intermediate | Structure | Chemical Name | MS: $[(M + 1)]^+$ | $^1$H-NMR |
| G-4-88 | 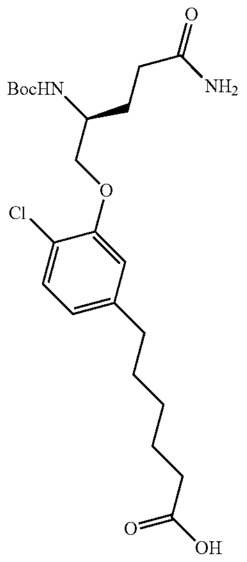 [SMILES: CC(C)(C)OC(=O)N[C@@H](CCC(N)=O)COc1cc(CCCCCC(=O)O)ccc1Cl] | 6-[3-[(2S)-2-[(tert-butoxycarbonyl) amino]-4-carbamoylbutoxy]-4-chlorophenyl] hexanoic acid | 457.30 | (300 MHz, DMSO-$d_6$) δ 11.97 (s, 1H), 7.29 (d, J = 8.1 Hz, 2H), 7.01-6.98 (m, 1H), 6.83-6.72 (m, 1H), 6.73-6.53 (m, 1H), 3.94-.91 (m, 2H), 2.57-2.35 (m, 2H), 2.22-2.19 (m, 8H), 2.14-1.96 (m, 2H), 1.64-1.44 (m, 2H), 1.52 (s, 9H), 0.92-0.80 (m, 2H) |
| G-4-89 | 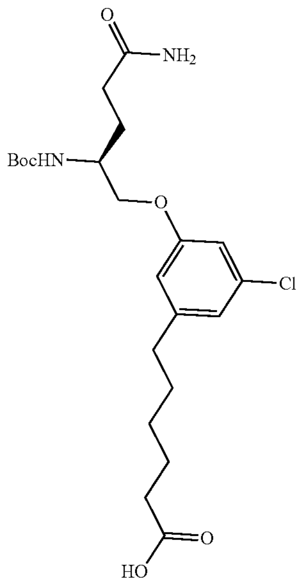 [SMILES: CC(C)(C)OC(=O)N[C@@H](CCC(N)=O)COc1cc(Cl)cc(CCCCCC(=O)O)c1] | 6-[3-[(2S)-2-[(tert-butoxycarbonyl) amino]-4-carbamoylbutoxy]-5-chlorophenyl] hexanoic acid | 457.10 | (400 MHz, DMSO-$d_6$) δ 12.01 (s, 1H), 7.27 (s, 1H), 6.88-6.79 (m, 3H), 6.77-6.72 (m, 2H), 4.48-4.34 (m, 1H), 3.90-3.84 (m, 2H), 3.76-3.65 (m, 1H), 2.19 (d, J = 7.3 Hz, 2H), 2.15-2.06 (m, 2H), 1.85-1.72 (m, 1H), 1.62-1.46 (m, 6H), 1.39 (s, 9H), 1.30-1.24 (m, 2H) |

TABLE 41-continued

| Characterization data for intermediates prepared according to above. | | | | |
|---|---|---|---|---|
| Inter-mediate | Structure | Chemical Name | MS: [(M + 1)]$^+$ | $^1$H-NMR |
| G-4-90 | 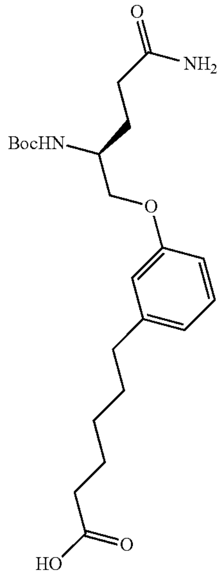 [SMILES: CC(C)(C)OC(=O)N[C@@H](CCC(N)=O)COc1cccc(CCCCCC(=O)O)c1] | 6-[3-[(2S)-2-[(tert-butoxycarbonyl)amino]-4-carbamoylbutoxy]phenyl]hexanoic acid | 423.30 | (400 MHz, DMSO-$d_6$) δ 11.94 (s, 1H), 7.26 (s, 1H), 7.17 (t, J = 8.0 Hz, 1H), 6.81 (d, J = 8.5 Hz, 1H), 6.76-6.72 (m, 4H), 3.86-3.82 (m, 2H), 3.73-3.69 (m, 1H), 2.54 (d, J = 7.6 Hz, 2H), 2.20 (t, J = 7.4 Hz, 2H), 2.14-2.10 (m, 2H), 1.88-1.75 (m, 1H), 1.56-1.52 (m, 5H), 1.40 (s, 9H), 1.32-1.22 (m, 2H) |
| G-4-91 | 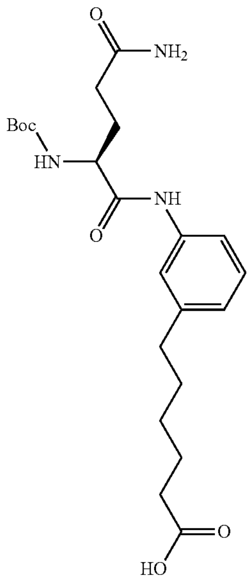 [SMILES: CC(C)(C)OC(=O)N[C@@H](CCC(N)=O)C(=O)Nc1cccc(CCCCCC(=O)O)c1] | 6-[3-[(2S)-2-[(tert-butoxycarbonyl)amino]-4-carbamoylbutanamido]phenyl]hexanoic acid | 436.30 | (300 MHz, DMSO-$d_6$) δ 11.88 (s, 1H), 9.84 (s, 1H), 7.43-7.41 (m, 2H), 7.31-7.13 (m, 2H), 6.99 (d, J = 7.6 Hz, 1H), 6.87 (d, J = 7.5 Hz, 1H), 6.75 (s, 1H), 4.05-4.01 (m, 1H), 2.22-2.05 (m, 4H), 1.97-1.67 (m, 2H), 1.60-1.47 (m, 5H), 1.38 (s, 9H), 1.35-1.20 (m, 3H) |

TABLE 41-continued

| Characterization data for intermediates prepared according to above. | | | | |
|---|---|---|---|---|
| Intermediate | Structure | Chemical Name | MS: $[(M + 1)]^+$ | $^1$H-NMR |
| G-4-92 | 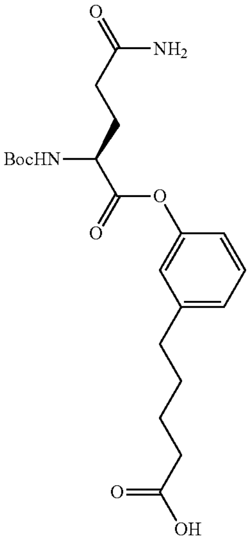 [SMILES: CC(C)(C)OC(=O)N[C@@H](CCC(N)=O)C(=O)Oc1cccc(CCCCC(=O)O)c1] | 5-[3-[(2S)-2-[(tert-butoxycarbonyl) amino]-4-carbamoylbutoxy] phenyl]pentanoic acid | 409.15 | (400 MHz, DMSO-$d_6$) δ 11.97 (s, 1H), 7.27 (s, 1H), 7.17 (t, J = 8.0 Hz, 1H), 6.82 (d, J = 8.4 Hz, 1H), 6.76-6.72 (m, 4H), 3.86-3.82 (m, 2H), 3.72-3.68 (m, 1H), 2.55 (d, J = 7.0 Hz, 2H), 2.28-2.07 (m, 4H), 1.67-1.43 (m, 6H), 1.39 (s, 9H) |
| G-4-93 | 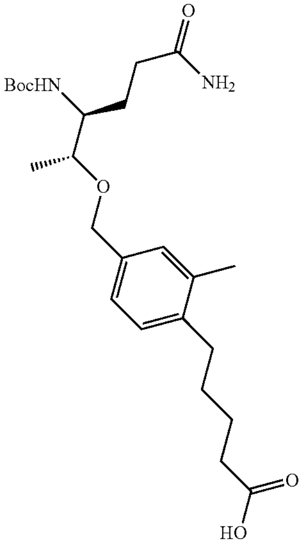 [SMILES: Cc1cc(CO[C@H](C)[C@H](CCC(N)=O)NC(=O)OC(C)(C)C)ccc1CCCCC(=O)O] | 5-[4-([[(2R,3S)-3-[(tert-butoxycarbonyl) amino]-5-carbamoylpentan-2-yl]oxy]methyl)-2-methylphenyl] pentanoic acid | 451.25 | (400 MHz, DMSO-$d_6$) δ 11.97 (s, 1H), 7.22 (s, 1H), 7.09-7.06 (m, 3H), 6.69 (s, 1H), 6.60 (d, J = 9.2 Hz, 1H), 4.44-4.34 (m, 2H), 3.50-3.35 (m, 2H), 2.56-2.54 (m, 3H), 2.27-2.23 (m, 6H), 2.12-1.97 (m, 2H), 1.83-1.75 (m, 1H), 1.60-1.43 (m, 3H), 1.39 (s, 9H), 1.05 (d, J = 6.1 Hz, 3H) |

TABLE 41-continued

| Characterization data for intermediates prepared according to above. | | | | |
|---|---|---|---|---|
| Intermediate | Structure | Chemical Name | MS: $[(M + 1)]^+$ | $^1$H-NMR |
| G-4-94 | 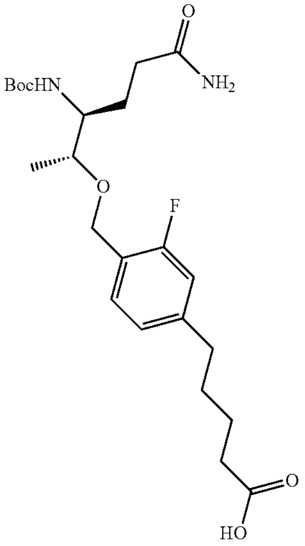 | 5-[4-([[(2R,3S)-3-[(tert-butoxycarbonyl)amino]-5-carbamoylpentan-2-yl]oxy]methyl)-3-fluorophenyl]pentanoic acid | 455.10 | (400 MHz, DMSO-$d_6$) δ 11.91 (s, 1H), 7.34 (t, J = 7.9 Hz, 1H), 7.20 (s, 1H), 7.04-6.96 (m, 2H), 6.66 (s, 1H), 6.58 (d, J = 8.8 Hz, 1H), 4.59-4.38 (m, 2H), 3.44-3.39 (m, 2H), 2.59 (t, J = 7.4 Hz, 2H), 2.23 (t, J = 7.1 Hz, 2H), 2.13-1.93 (m, 2H), 1.82-1.74 (m, 1H), 1.63-1.43 (m, 4H), 1.38 (s, 9H), 1.35 (s, 1H), 1.07 (d, J = 5.6 Hz, 3H) |
| G-4-95 | 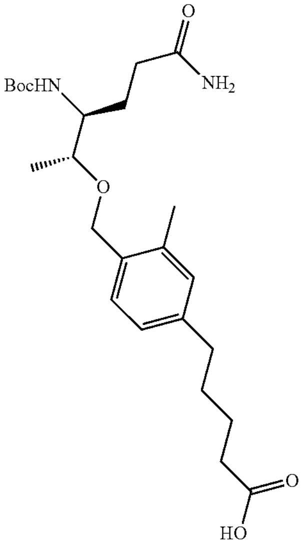 [SMILES: Cc1cc(CCCCC(=O)O)ccc1CO[C@H](C)[C@H](CCC(N)=O)NC(=O)OC(C)(C)C] | 5-[4-([[(2R,3S)-3-[(tert-butoxycarbonyl)amino]-5-carbamoylpentan-2-yl]oxy]methyl)-3-methylphenyl]pentanoic acid | 451.15 | (400 MHz, Methanol-$d_4$) δ 7.22 (d, J = 7.6 Hz, 1H), 7.02-6.96 (m, 2H), 4.61-4.44 (m, 2H), 3.60-3.53 (m, 2H), 2.64-2.56 (m, 2H), 2.37-2.17 (m, 7H), 2.03-1.90 (m, 1H), 1.67-1.61 (m, 5H), 1.45 (s, 9H), 1.19 (d, J = 6.0 Hz, 3H) |
| G-4-113 | 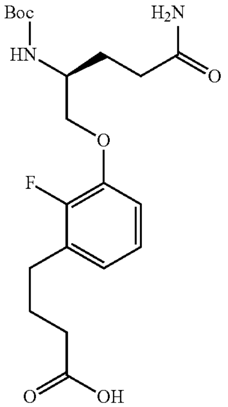 [SMILES: CC(C)(C)OC(=O)N[C@@H](CCC(N)=O)COc1cccc(CCCC(=O)O)c1F] | 4-[3-[(2S)-4-[(tert-butoxycarbonyl)amino]-4-carbamoylbutoxy]-2-fluorophenyl]butanoic acid | 413.30 | (300 MHz, DMSO-$d_6$) δ 11.99 (s, 1H), 7.29-7.27 (m, 1H), 7.06-6.97 (m, 2H), 6.88-6.79 (m, 2H), 6.76-6.74 (m, 1H), 3.93 (d, J = 6.0 Hz, 2H), 3.75-3.70 (m, 1H), 2.64-2.59 (m, 2H), 2.26-2.21 (m, 2H), 2.18-2.09 (m, 2H), 1.80-1.75 (m, 3H), 1.64-1.57 (m, 1H), 1.39 (s, 9H) |

TABLE 41-continued

Characterization data for intermediates prepared according to above.

| Inter-mediate | Structure | Chemical Name | MS: [(M + 1)]$^+$ | $^1$H-NMR |
|---|---|---|---|---|
| G-4-114 | 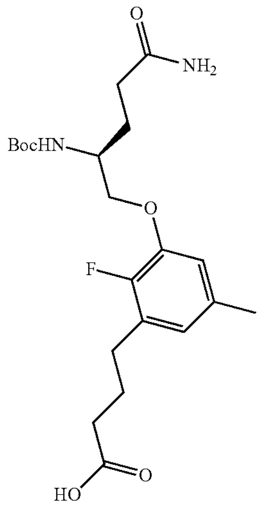 | 4-[3-[(2S)-4-[(tert-butoxycarbonyl)amino]-4-carbamoylbutoxy]2-fluoro-5-methylphenyl]butanoic acid | 427.10 | (300 MHz, DMSO-$d_6$) δ 11.97 (s, 1H), 7.24 (s, 1H), 6.80 (d, J = 8.1 Hz, 2H), 6.71 (s, 1H), 6.62-6.57 (m, 1H), 3.88 (d, J = 6.0 Hz, 2H), 3.77-3.65 (m, 1H), 2.59-2.52 (m, 2H), 2.23 (s, 3H), 2.14-2.06 (m, 2H), 1.80-1.72 (m, 2H), 1.47 (t, J = 7.1 Hz, 2H), 1.37 (s, 9H), 1.25 (p, J = 3.6 Hz, 2H) |
| G-4-115 | 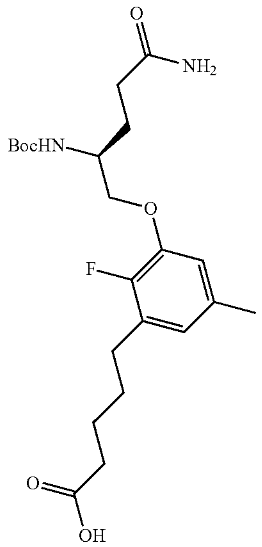 [SMILES: Cc1cc(CCCCC(=O)O)c(F)c(OC[C@H](CCC(N)=O)NC(=O)OC(C)(C)C)c1] | 5-[3-[(2S)-4-[(tert-butoxycarbonyl)amino]-4-carbamoylbutoxy]-2-fluoro-5-methylphenyl]pentanoic acid | 441.20 | (400 MHz, DMSO-$d_6$) δ 11.97 (s, 1H), 7.27 (s, 1H), 6.87-6.77 (m, 2H), 6.74 (s, 1H), 6.61 (dd, J = 6.1, 2.0 Hz, 1H), 3.89 (d, J = 6.0 Hz, 2H), 3.77-3.68 (m, 1H), 2.58-2.52 (m, 2H), 2.23 (s, 3H), 2.16-2.07 (m, 2H), 1.56-1.44 (m, 8H), 1.39 (s, 9H) |

TABLE 41-continued

| Characterization data for intermediates prepared according to above. | | | | |
|---|---|---|---|---|
| Inter-mediate | Structure | Chemical Name | MS: $[(M + 1)]^+$ | $^1$H-NMR |
| G-4-116 | 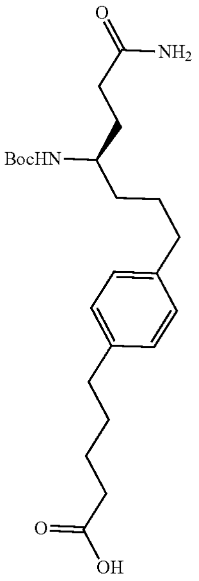 [SMILES: CC(C)(C)OC(=O)N[C@H](CCCc1ccc(CCCCC(=O)O)cc1)CCC(N)=O] | 5-[4-[(4R)-4-[(tert-butoxycarbonyl)amino]-6-carbamoylhexyl]phenyl]pentanoic acid | 421.30 | (300 MHz, DMSO-$d_6$) δ 12.01 (s, 1H), 7.23 (s, 1H), 7.09 (s, 4H), 6.69 (s, 1H), 6.60 (d, J = 9.0 Hz, 1H), 3.46-3.48 (m, 1 H), 2.64-2.55 (m, 3 H), 2.23 (s, 2H), 2.03 (t, J = 7.9 Hz, 2H), 1.53 (s, 11H), 1.39 (s, 9H) |
| G-4-117 | 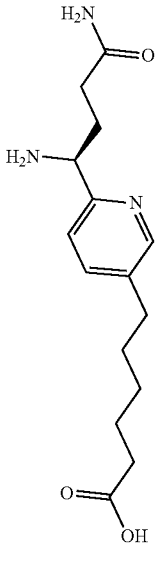 [SMILES: NC(=O)CC[C@H](N)c1ccc(CCCCCC(=O)O)cn1] | 6-[6-[(1S)-1-amino-3-carbamoylpropyl]pyridin-3-yl]hexanoic acid | 294.15 | (300 MHz, DMSO-$d_6$) δ 8.40-8.39 (d, J = 2.3 Hz, 1H), 7.67-7.64 (dd, J = 8.0, 2.3 Hz, 1H), 7.28-7.16 (m, 2H), 6.70 (s, 1H), 3.81-3.77 (m, 1H), 2.72-2.67 (t, J = 7.6 Hz, 2H), 2.21-2.17 (t, J = 7.3 Hz, 2H), 2.13-1.90 (m, 2H), 1.87-1.75 (m, 2H), 1.68-1.63 (m, 2H), 1.56-1.49 (m, 2H), 1.36-1.28 (m, 2H) |

TABLE 41-continued

| Characterization data for intermediates prepared according to above. | | | | |
|---|---|---|---|---|
| Inter-mediate | Structure | Chemical Name | MS: $[(M + 1)]^+$ | $^1$H-NMR |
| G-4-118 | 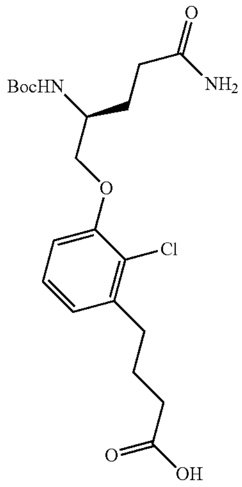 [SMILES: CC(C)(C)OC(=O)N[C@@H](CCC(N)=O)COc1cccc(CCCC(=O)O)c1Cl] | 4-[3-[(2S)-2-[(tert-butoxycarbonyl)amino]-4-carbamoylbutoxy]-2-chlorophenyl]butanoic acid | 429.05 | (400 MHz, DMSO-$d_6$) δ 12.00 (s, 1H), 7.26 (s, 1H), 7.21 (t, J = 7.9 Hz, 1H), 7.03-6.96 (m, 1H), 6.93-6.87 (m, 1H), 6.80 (d, J = 8.5 Hz, 1H), 6.73 (s, 1H), 3.93 (d, J = 6.2 Hz, 2H), 3.77 (s, 1H), 2.29-2.08 (m, 5H), 1.85-1.73 (m, 3H), 1.64-1.60 (m, 1H), 1.50-1.46 (m, 1H), 1.39 (s, 9H) |
| G-4-119 | 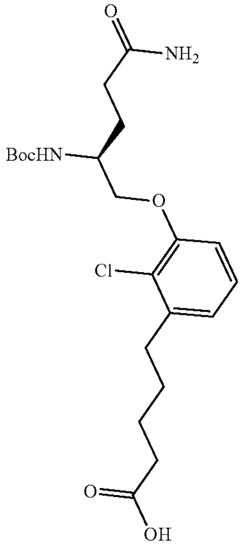 [SMILES: CC(C)(C)OC(=O)N[C@@H](CCC(N)=O)COc1cccc(CCCCC(=O)O)c1Cl] | 5-[3-[(2S)-2-[(tert-butoxycarbonyl)amino]-4-carbamoylbutoxy]-2-chlorophenyl]pentanoic acid | 443.10 | (400 MHz, DMSO-$d_6$) δ 12.00 (s, 1H), 7.30-7.25 (m, 1H), 7.20 (t, J = 7.9 Hz, 1H), 6.98 (dd, J = 8.3, 1.4 Hz, 1H), 6.91 (dd, J = 7.6, 1.3 Hz, 1H), 6.81 (d, J = 8.4 Hz, 1H), 6.75 (s, 1H), 3.92 (d, J = 6.1 Hz, 2H), 3.82-3.72 (m, 1H), 2.69 (t, J = 6.9 Hz, 2H), 2.28-2.21 (m, 2H), 2.19-2.05 (m, 2H), 1.90-1.72 (m, 2H), 1.68-1.49 (m, 4H), 1.39 (s, 9H) |

TABLE 41-continued

| Characterization data for intermediates prepared according to above. | | | | |
|---|---|---|---|---|
| Intermediate | Structure | Chemical Name | MS: [(M + 1)]$^+$ | $^1$H-NMR |
| G-4-120 | 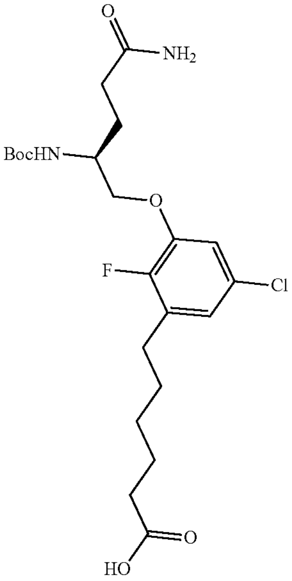 [SMILES: CC(C)(C)OC(=O)N[C@@H](CCC(N)=O)COc1cc(Cl)cc(CCCCCC(=O)O)c1F] | -[3-[(2S)-2-[(tert-butoxycarbonyl) amino]-4-carbamoylbutoxy]-5-chloro-2-fluorophenyl] hexanoic acid | 475.15 | (300 MHz, DMSO-$d_6$) δ 11.98 (s, 1H), 7.28 (s, 1H), 7.13-7.11 (m, 1H), 6.95-6.92 (m, 1H), 6.84 (d, J = 8.4 Hz, 1H), 6.75 (s, 1H), 4.01-3.86 (m, 2H), 3.74-3.71 (m, 1H), 2.57 (t, J = 7.4 Hz, 2H), 2.13-2.09 (m, 2H), 1.81-1.77 (m, 1H), 1.53-1.50 (m, 9H), 1.39 (s, 9H) |
| G-4-121 | 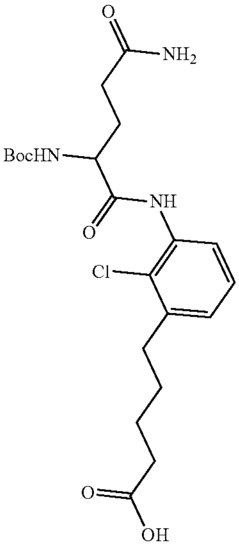 [SMILES: CC(C)(C)OC(=O)NC(CCC(N)=O)C(=O)Nc1cccc(CCCCC(=O)O)c1Cl] | 5-(3-[2-[(tert-butoxycarbonyl) amino]-4-carbamoylbutan-amido]-2-chlorophenyl) pentanoic acid | 456.10 | (400 MHz, DMSO-d6) δ 12.00 (s, 1H), 9.32 (s, 1H), 7.74 (d, J = 8.1 Hz, 1H), 7.68-7.51 (m, 1H), 7.25 (d, J = 8.0 Hz, 1H), 7.14 (dd, J = 7.6, 1.6 Hz, 1H), 6.83-6.78 (m, 1H), 4.12 (s, 1H), 3.45 (s, 1H), 2.72 (t, J = 6.8 Hz, 2H), 2.25 (t, J = 6.6 Hz, 2H), 2.20 (s, 2H), 1.87-1.73 (m, 1H), 1.58-1.54 (m, 5H), 1.41 (s, 9H) |

TABLE 41-continued

| Characterization data for intermediates prepared according to above. | | | | |
|---|---|---|---|---|
| Inter-mediate | Structure | Chemical Name | MS: [(M + 1)]$^+$ | $^1$H-NMR |
| G-4-122 | 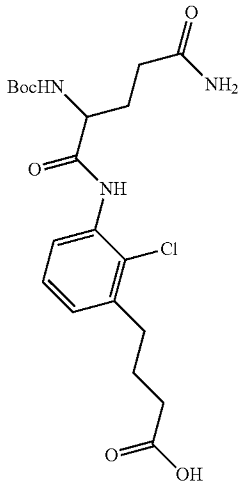 [SMILES: CC(C)(C)OC(=O)NC(CCC(N)=O)C(=O)Nc1cccc(CCCC(=O)O)c1Cl] | 4-[3-[(2S)-2-[(tert-butoxycarbonyl)amino]-4-carbamoylbutan-amido]-2-chlorophenyl]butanoic acid | 442.10 | (400 MHz, DMSO-$d_6$) δ 12.08 (s, 1H), 9.33 (s, 1H), 7.75 (d, J = 8.1 Hz, 1H), 7.33-7.23 (m, 2H), 7.13 (dd, J = 7.7, 1.6 Hz, 1H), 6.80 (s, 1H), 4.12 (s, 1H), 2.78-2.70 (m, 2H), 2.27 (t, J = 7.4 Hz, 2H), 2.19 (d, J = 9.2 Hz, 3H), 2.01-1.97 (m, 1H), 1.86-1.73 (m, 3H), 1.41 (s, 9H) |
| G-4-123 | 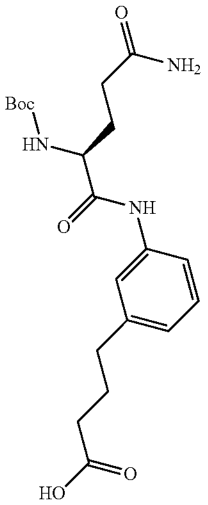 [SMILES: CC(C)(C)OC(=O)N[C@@H](CCC(N)=O)C(=O)Nc1cccc(CCCC(=O)O)c1] | 4-[3-[(2S)-2-[(tert-butoxycarbonyl)amino]-4-carbamoylbutanamido]phenyl]butanoic acid | 408.20 | (400 MHz, DMSO-$d_6$) δ 11.98 (s, 1H), 9.89 (s, 1H), 7.45 (dd, J = 8.3, 1.8 Hz, 2H), 7.29 (s, 1H), 7.25-7.18 (m, 1H), 7.01 (d, J = 7.7 Hz, 1H), 6.91-6.86 (m, 1H), 6.77 (s, 1H), 4.03 (q, J = 8.6, 8.1 Hz, 1H), 2.56-2.52 (m, 2H), 2.23-2.21 (m, 2H), 2.19-2.05 (m, 2H), 1.96-1.84 (m, 1H), 1.79-1.71 (m, 3H), 1.39 (s, 9H) |
| G-4-124 | 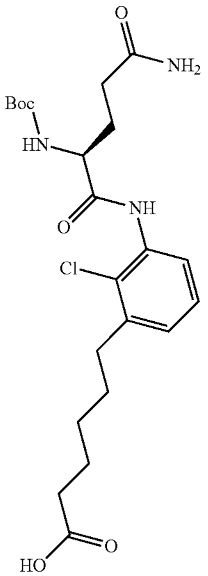 [SMILES: CC(C)(C)OC(=O)N[C@@H](CCC(N)=O)C(=O)Nc1cccc(CCCCCC(=O)O)c1Cl] | 6-[3-[(2S)-2-[(tert-butoxycarbonyl)amino]-4-carbamoylbutan-amido]-2-chlorophenyl]hexanoic acid | 470.20 | (300 MHz, DMSO-$d_6$) δ 11.96 (s, 1H), 9.59 (s, 1H), 7.78-7.70 (m, 1H), 7.31 (s, 1H), 7.18-6.95 (m, 3H), 6.81 (s, 1H), 4.19-4.12 (m, 1H), 2.62 (t, J = 7.5 Hz, 2H), 2.24-2.15 (m, 3H), 1.98-1.90 (m, 1H), 1.85-1.75 (m, 1H), 1.59-1.49 (m, 4H), 1.40-1.29 (m, 12H) |

TABLE 41-continued

| Characterization data for intermediates prepared according to above. | | | | |
|---|---|---|---|---|
| Intermediate | Structure | Chemical Name | MS: $[(M+1)]^+$ | $^1$H-NMR |
| G-4-125 | 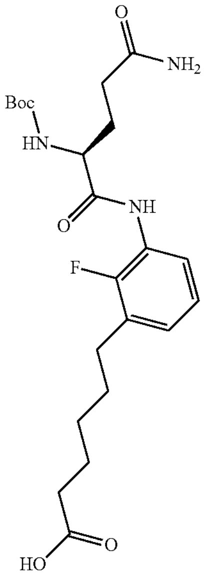 [SMILES: CC(C)(C)OC(=O)N[C@@H](CCC(N)=O)C(=O)Nc1cccc(CCCCCC(=O)O)c1F] | 6-[3-[(2S)-2-[(tert-butoxycarbonyl)amino]-4-carbamoylbutanamido]-2-fluorophenyl]hexanoic acid | 454.20 | (300 MHz, DMSO-$d_6$) δ 12.01 (s, 1H), 9.33 (s, 1H), 7.75 (d, J = 8.1 Hz, 1H), 7.32-7.24 (m, 3H), 7.16-7.13 (m, 1H), 6.82 (s, 1H), 4.16-4.10 (m, 1H), 2.72 (t, J = 7.6 Hz, 2H), 2.29-2.11 (m, 5H), 2.05-1.96 (m, 1H), 1.90-1.73 (m, 1H), 1.63-1.51 (m, 5H), 1.42 (s, 9H) |
| G-4-126 | 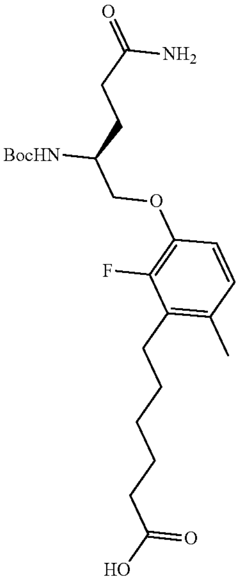 [SMILES: Cc1ccc(OC[C@H](CCC(N)=O)NC(=O)OC(C)(C)C)c(F)c1CCCCCC(=O)O] | 6-[3-[(2S)-2-[(tert-butoxycarbonyl)amino]-4-carbamoylbutoxy]-2-fluoro-6-methylphenyl]hexanoic acid | 455.35 | (400 MHz, DMSO-$d_6$) δ 11.98 (s, 1H), 7.29-7.24 (m, 1H), 6.92-6.84 (m, 2H), 6.83 (d, J = 8.5 Hz, 1H), 6.74 (s, 1H), 3.87 (d, J = 6.1 Hz, 2H), 3.74-3.70 (m, 1H), 2.59-2.55 (m, 2H), 2.21 (s, 3H), 2.17-2.05 (m, 2H), 1.87-1.73 (m, 2H), 1.65-1.43 (m, 6H), 1.39 (s, 9H), 1.35-1.31 (m, 2H) |

TABLE 41-continued

| Characterization data for intermediates prepared according to above. | | | | |
|---|---|---|---|---|
| Intermediate | Structure | Chemical Name | MS: $[(M + 1)]^+$ | $^1H$-NMR |
| G-4-127 | 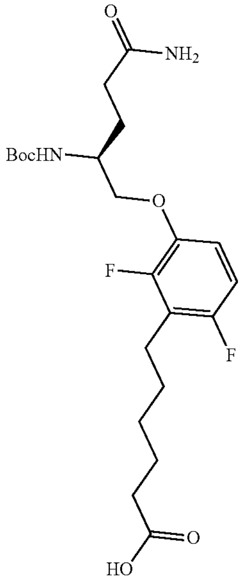 [SMILES: CC(C)(C)OC(=O)N[C@@H](CCC(N)=O)COc1ccc(F)c(CCCCCC(=O)O)c1F] | 6-[3-[(2S)-2-[(tert-butoxycarbonyl)amino]-4-carbamoylbutoxy]-2,6-difluorophenyl]hexanoic acid | 459.15 | (400 MHz, DMSO-$d_6$) δ 11.97 (s, 1H), 7.27 (s, 1H), 7.06-7.02 (m, 1H), 6.98-6.94 (m, 1H), 6.83 (d, J = 8.5 Hz, 1H), 6.74 (s, 1H), 3.98-3.87 (m, 2H), 3.73-3.69 (m, 1H), 2.60 (t, J = 7.6 Hz, 2H), 2.19 (t, J = 7.3 Hz, 2H), 2.17-2.05 (m, 2H), 1.82-1.77 (m, 1H), 1.61-1.55 (m, 1H), 1.56-1.46 (m, 4H), 1.38 (s, 9H), 1.32-1.28 (m, 2H) |
| G-4-128 | 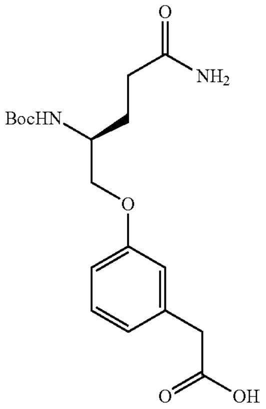 [SMILES: CC(C)(C)OC(=O)N[C@@H](CCC(N)=O)COc1cccc(CC(=O)O)c1] | [3-[(2S)-2-[(tert-butoxycarbonyl)amino]-4-carbamoylbutoxy]phenyl]acetic acid | 367.10 | (400 MHz, DMSO-$d_6$) δ 12.30 (s, 1H), 7.35-7.10 (m, 2H), 6.92-6.68 (m, 5H), 3.90-3.77 (m, 2H), 3.70-3.68 (m, 1H), 3.53 (s, 2H), 2.21-2.05 (m, 2H), 1.89-1.74 (m, 1H), 1.66-1.55 (m, 1H), 1.40 (s, 9H) |
| G-4-129 | 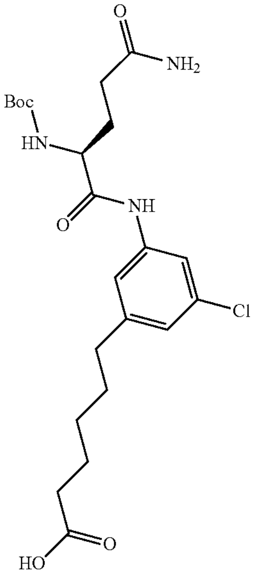 [SMILES: CC(C)(C)OC(=O)N[C@@H](CCC(N)=O)C(=O)Nc1cc(Cl)cc(CCCCCC(=O)O)c1] | 6-[3-[(2S)-2-[(tert-butoxycarbonyl)amino]-4-carbamoylbutanamido]-5-chlorophenyl]hexanoic acid | $[(M - 1)]^-$ = 468.25 | (300 MHz, DMSO-$d_6$) δ 10.70 (s, 1H), 7.73 (d, J = 2.1 Hz, 1H), 7.41 (d, J = 9.2 Hz, 2H), 7.31 (t, J = 1.7 Hz, 1H), 6.89 (t, J = 1.7 Hz, 1H), 6.77 (s, 1H), 4.01 (d, J = 6.7 Hz, 1H), 2.23-2.13 (m, 2H), 2.01-1.88 (m, 4H), 1.62-1.42 (m, 5H), 1.36 (s, 9H), 1.33-1.19 (m, 4H) |

TABLE 41-continued

| Characterization data for intermediates prepared according to above. | | | | |
|---|---|---|---|---|
| Intermediate | Structure | Chemical Name | MS: $[(M + 1)]^+$ | $^1$H-NMR |
| G-4-130 | 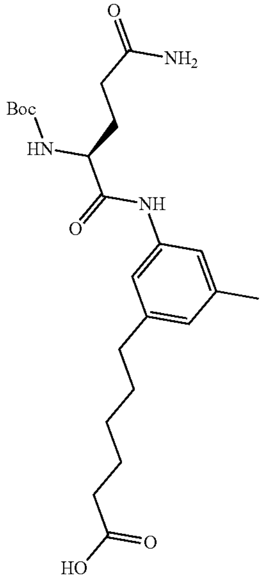 [SMILES: Cc1cc(CCCCCC(=O)O)cc(NC(=O)[C@H](CCC(N)=O)NC(=O)OC(C)(C)C)c1] | 6-[3-[(2S)-2-[(Tert-butoxycarbonyl)amino]-4-carbamoylbutan-amido]-5-methylphenyl]hexanoic acid | 450.20 | (300 MHz, DMSO-$d_6$) δ 11.99 (s, 1H), 9.79 (s, 1H), 7.32-7.22 (m, 3H), 7.00 (s, 1H), 6.84-6.72 (m, 2H), 4.03 (q, J = 7.5, 7.0 Hz, 1H), 2.25 (s, 3H), 2.24-2.06 (m, 4H), 1.96-1.82 (m, 2H), 1.62-1.48 (m, 6H), 1.40 (s, 9H), 1.38-1.29 (m, 2H) |
| G-4-131 | 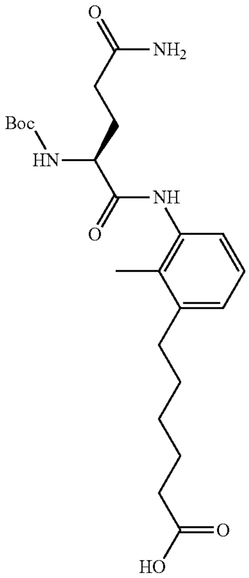 [SMILES: Cc1c(CCCCCC(=O)O)cccc1NC(=O)[C@H](CCC(N)=O)NC(=O)OC(C)(C)C] | 6-[3-[(2S)-2-[(tert-butoxycarbonyl)amino]-4-carbamoylbutan-amido]-2-methylphenyl]hexanoic acid | 450.25 | (400 MHz, DMSO-$d_6$) δ 11.98 (s, 1H), 9.27 (s, 1H), 7.32 (s, 1H), 7.22-7.12 (m, 1H), 7.12-6.94 (m, 3H), 6.89-6.74 (m, 1H), 4.07 (q, J = 7.6, 7.2 Hz, 1H), 2.65-2.55 (m, 2H), 2.20 (q, J = 6.9, 6.5 Hz, 4H), 2.10 (s, 3H), 1.99-1.95 (m, 1H), 1.85-1.81 (m, 1H), 1.62-1.44 (m, 5H), 1.41 (s, 9H), 1.37-1.29 (m, 1H) |

TABLE 41-continued

| Characterization data for intermediates prepared according to above. | | | | |
|---|---|---|---|---|
| Intermediate | Structure | Chemical Name | MS: [(M + 1)]$^+$ | $^1$H-NMR |
| G-4-132 | 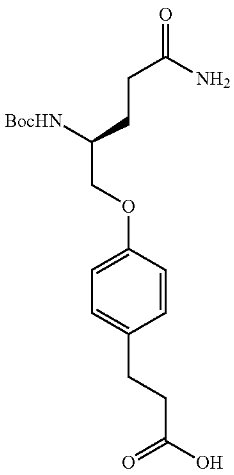 [SMILES: CC(C)(C)OC(=O)N[C@@H](CCC(N)=O)COc1ccc(CCC(=O)O)cc1] | 3-[3-[(2S)-2-[(tert-butoxycarbonyl) amino]-4-carbamoylbutoxy] phenyl]propanoic acid | 381.15 | (400 MHz, DMSO-$d_6$) δ 12.11 (s, 1H), 7.27 (s, 1H), 7.18 (t, J = 8.1 Hz, 1H), 6.83 (d, J = 8.3 Hz, 1H), 6.82-6.78 (m, 2H), 6.75 (dd, J = 8.4, 2.5 Hz, 2H), 3.84 (qd, J = 9.6, 5.9 Hz, 2H), 3.72 (tt, J = 9.2, 5.0 Hz, 1H), 2.79 (t, J = 7.6 Hz, 2H), 2.56-2.52 (m, 2H), 2.18-2.04 (m, 2H), 1.88-1.75 (m, 1H), 1.66-1.54 (m, 1H), 1.40 (s, 9H) |
| G-4-133 | 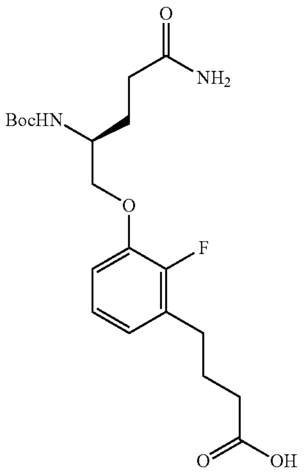 [SMILES: CC(C)(C)OC(=O)N[C@@H](CCC(N)=O)COc1cccc(CCCC(=O)O)c1F] | 4-[3-[(2S)-2-[(tert-butoxycarbonyl) amino]-4-carbamoylbutoxy]-2-fluorophenyl] butanoic acid | 413.20 | (400 MHz, DMSO-$d_6$) δ 12.05 (s, 1H), 7.27 (s, 1H), 7.05-6.98 (m, 2H), 6.85-6.78 (m, 2H), 6.74 (s, 1H), 3.92 (d, J = 6.0 Hz, 2H), 3.74-3.72 (m, 1H), 2.61 (t, J = 7.6 Hz, 2H), 2.23 (t, J = 7.3 Hz, 2H), 2.14-2.08 (m, 2H), 1.85-1.72 (m, 3H), 1.64-1.53 (m, 1H), 1.39 (s, 9H) |
| G-4-134 | 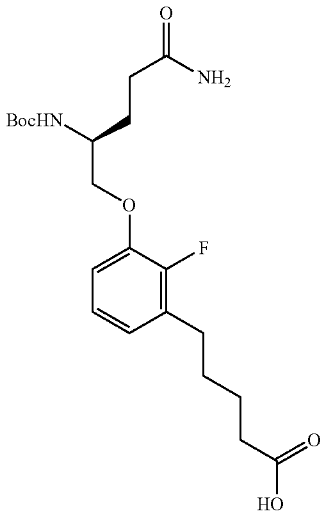 [SMILES: CC(C)(C)OC(=O)N[C@@H](CCC(N)=O)COc1cccc(CCCCC(=O)O)c1F] | 5-[3-[(2S)-2-[(tert-butoxycarbonyl) amino]-4-carbamoylbutoxy]-2-fluorophenyl] pentanoic acid | 427.15 | (400 MHz, DMSO-$d_6$) δ 11.99 (s, 1H), 7.28 (s, 1H), 7.01-6.98 (m, 2H), 6.84-6.82 (m, 2H), 6.74 (s, 1H), 3.92 (d, J = 6.0 Hz, 2H), 3.75-3.71 (m, 1H), 2.59 (t, J = 6.9 Hz, 2H), 2.23 (t, J = 6.9 Hz, 2H), 2.15-2.11 (m, 2H), 1.87-1.78 (m, 1H), 1.60-1.47 (m, 5H), 1.39 (s, 9H) |

TABLE 41-continued

| Characterization data for intermediates prepared according to above. | | | | |
|---|---|---|---|---|
| Intermediate | Structure | Chemical Name | MS: [(M + 1)]+ | 1H-NMR |
| G-4-135 | 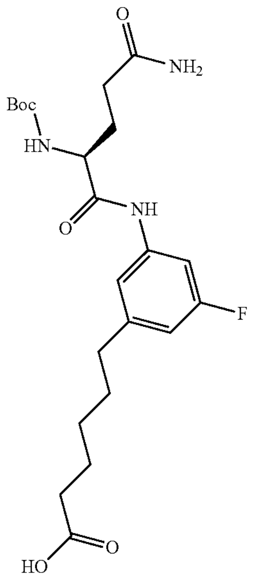 [SMILES: CC(C)(C)OC(=O)N[C@@H](CCC(N)=O)C(=O)Nc1cc(F)cc(CCCCCC(=O)O)c1] | 6-[3-[(2S)-2-[(tert-butoxycarbonyl) amino]-4-carbamoylbutan-amido]-5-fluorophenyl] hexanoic acid | 454.25 | (300 MHz, DMSO-$d_6$) δ 10.25 (s, 1H), 7.46 (dt, J = 11.5, 2.2 Hz, 1H), 7.34 (s, 1H), 7.24-7.08 (m, 2H), 6.92-6.58 (m, 2H), 4.03 (q, J = 7.5 Hz, 1H), 2.57-2.55 (m, 2H), 2.20-2.08 (m, 4H), 1.90-1.78 (m, 2H), 1.61-1.49 (m, 4H), 1.39 (s, 9H), 1.35-1.12 (m, 3H) |
| G-4-136 | 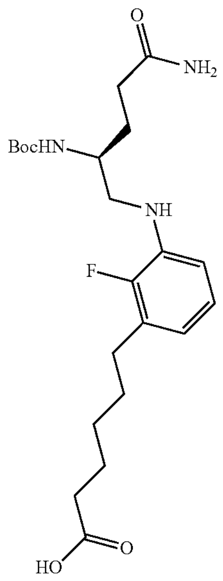 [SMILES: CC(C)(C)OC(=O)N[C@@H](CCC(N)=O)CNc1cccc(CCCCCC(=O)O)c1F] | 6-[3-([2-[(tert-butoxycarbonyl) amino]-4-carbamoylbutyl] amino)-2-fluorophenyl] hexanoic acid | 441.20 | (400 MHz, DMSO-$d_6$) δ 11.94 (s, 1H), 7.25 (s, 1H), 6.86 (t, J = 7.8 Hz, 1H), 6.79 (d, J = 8.4 Hz, 1H), 6.71 (s, 1H), 6.60 (t, J = 8.2 Hz, 1H), 6.41 (t, J = 7.2 Hz, 1H), 5.23 (s, 1H), 3.60 (s, 1H), 3.13-2.99 (m, 1H), 3.06-3.02 m, 2H), 2.55-2.51 (m, 1H), 2.21-2.17 (m, 2H), 2.09-2.05 (m, 1H), 1.78-1.74 (m, 1H), 1.54-1.50 (m, 5H), 1.39 (s, 9H), 1.33-1.29 (m, 3H) |

TABLE 41-continued

| Characterization data for intermediates prepared according to above. | | | | |
|---|---|---|---|---|
| Intermediate | Structure | Chemical Name | MS: $[(M+1)]^+$ | $^1$H-NMR |
| G-4-137 | 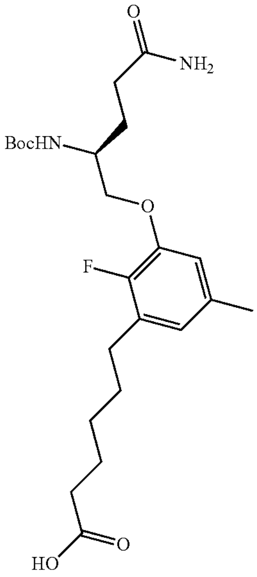 [SMILES: Cc1cc(CCCCCC(=O)O)c(F)c(OC[C@H](CCC(N)=O)NC(=O)OC(C)(C)C)c1] | 6-[3-[(2S)-2-[(tert-butoxycarbonyl)amino]-4-carbamoylbutoxy]-2-fluoro-5-methylphenyl]hexanoic acid | 455.25 | (400 MHz, DMSO-$d_6$) δ 11.96 (s, 1H), 7.27 (s, 1H), 6.81 (dd, J = 12.3, 8.1 Hz, 2H), 6.74 (s, 1H), 6.62 (dd, J = 6.0, 2.0 Hz, 1H), 3.89 (d, J = 6.0 Hz, 2H), 3.77-3.67 (m, 1H), 2.56-2.52 (m, 2H), 2.23 (s, 3H), 2.20 (t, J = 7.3 Hz, 2H), 1.86-1.74 (m, 1H), 1.66-1.58 (m, 1H), 1.55-1.49 (m, 4H), 1.39 (s, 9H), 1.36-1.22 (m, 4H) |
| G-4-138 | 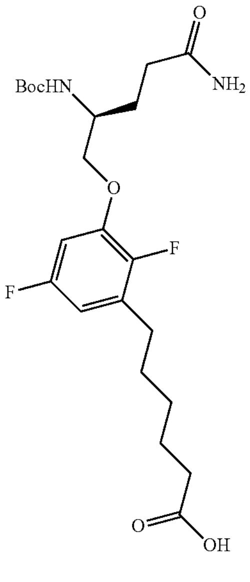 [SMILES: CC(C)(C)OC(=O)N[C@@H](CCC(N)=O)COc1cc(F)cc(CCCCCC(=O)O)c1F] | 6-[3-[(2S)-2-[(tert-butoxycarbonyl)amino]-4-carbamoylbutoxy]-2,5-difluorophenyl]hexanoic acid | 459.20 | (400 MHz, CD3OD) δ 6.80-6.73 (m, 1H), 6.61-6.53 (m, 1H), 4.00 (d, J = 5.5 Hz, 2H), 3.94-3.86 (m, 1H), 2.69-2.54 (m, 2H), 2.43-2.26 (m, 4H), 2.05-1.95 (m, 1H), 1.87-1.72 (m, 1H), 1.70-1.59 (m, 4H), 1.46 (s, 9H), 1.46-1.34 (m, 2H) |

TABLE 41-continued

Characterization data for intermediates prepared according to above.

| Inter-mediate | Structure | Chemical Name | MS: $[(M + 1)]^+$ | $^1$H-NMR |
|---|---|---|---|---|
| G-4-139 | 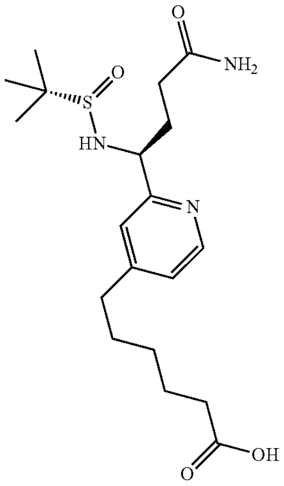 | 6-[2-[(1S)-3-carbamoyl-1-[(2-methylpropane-2-sulfinyl)amino]propyl]pyridin-4-yl]hexanoic acid | 398.20 | (300 MHz, DMSO-$d_6$) δ 8.42-8.40 (d, J = 5.0 Hz, 1H), 7.30 (s, 1H), 7.22-7.10 (m, 2H), 6.8 (s, 1H), 5.76-5.73 (d, J = 5.4 Hz, 1H), 4.27-4.21 (q, J = 6.4 Hz, 1H), 2.73-2.68 (t, J = 7.6 Hz, 2H), 2.25-1.98 (m, 5H), 1.95-1.78 (m, 1H), 1.66 (p, J = 7.6 Hz, 2H), 1.54 (p, J = 7.4 Hz, 2H), 1.49-1.27 (m, 3H), 1.10 (s, 9H) |
| G-4-140 | 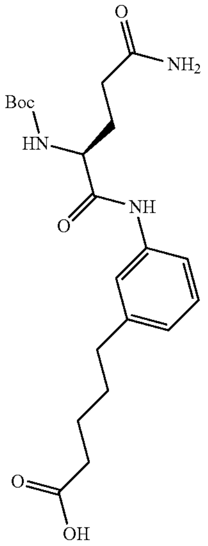 [SMILES: CC(C)(C)OC(=O)N[C@@H](CCC(N)=O)C(=O)Nc1cccc(CCCCC(=O)O)c1] | 5-[3-[(2S)-2-[(tert-butoxycarbonyl)amino]-4-carbamoylbutanamido]phenyl]pentanoic acid | 422.25 | (300 MHz, DMSO-$d_6$) δ 9.88 (s, 1H), 7.46-7.43 (m, 2H), 7.30 (s, 1H), 7.22 (t, J = 8.1 Hz, 1H), 7.03-7.01 (m, 1H), 6.90 (d, J = 7.9 Hz, 1H), 6.79 (s, 1H), 4.05-4.01 (m, 1H), 2.30-2.05 (m, 6H), 1.98-1.74 (m, 3H), 1.62-1.52 (m, 4H), 1.41 (s, 9H) |
| G-4-145 | 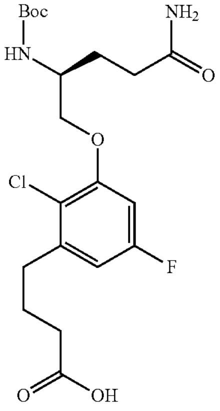 [SMILES: CC(C)(C)OC(=O)N[C@@H](CCC(N)=O)COc1cc(F)cc(CCCC(=O)O)c1Cl] | 4-[3-[(2S)-2-[(tert-butoxycarbonyl)amino]-4-carbamoylbutoxy]-2-chloro-5-fluorophenyl]butanoic acid | 447.10 | (300 MHz, DMSO-$d_6$) δ 12.10 (s, 1H), 7.28 (s, 1H), 6.99 (dd, J = 10.8, 2.7 Hz, 1H), 6.87-6.72 (m, 3H), 3.97-3.93 (m, 2H), 3.78 (d, J = 5.2 Hz, 1H), 2.72 (t, J = 7.9 Hz, 2H), 2.26 (t, J = 7.5 Hz, 2H), 2.15 (d, J = 6.9 Hz, 2H), 1.81 (q, J = 7.4 Hz, 3H), 1.63 (d, J = 13.1 Hz, 1H), 1.40 (s, 9H) |

TABLE 41-continued

| Characterization data for intermediates prepared according to above. | | | | |
|---|---|---|---|---|
| Intermediate | Structure | Chemical Name | MS: $[(M + 1)]^+$ | $^1$H-NMR |
| G-4-146 | 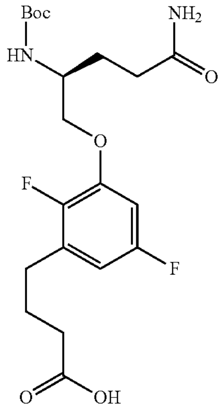 [SMILES: CC(C)(C)OC(=O)N[C@@H](CCC(N)=O)COc1cc(F)cc(CCCC(=O)O)c1F] | 4-[3-[(2S)-2-[(tert-butoxycarbonyl)amino]-4-carbamoylbutoxy]-2,5-difluorophenyl]butanoic acid | 431.20 | (400 MHz, DMSO-$d_6$) δ 7.27 (s, 1H), 6.97 (t, J = 6.9 Hz, 1H), 6.85 (d, J = 8.5 Hz, 1H), 6.74 (s, 1H), 6.71-6.65 (m, 1H), 3.94 (p, J = 9.7 Hz, 2H), 2.60-2.57 (m, 2H), 2.22-2.17 (m, 2H), 2.12-2.08 (m, 2H), 1.77-1.69 (m, 3H), 1.53-1.50 (m, 1H), 1.38 (s, 9H) |
| G-4-147 | 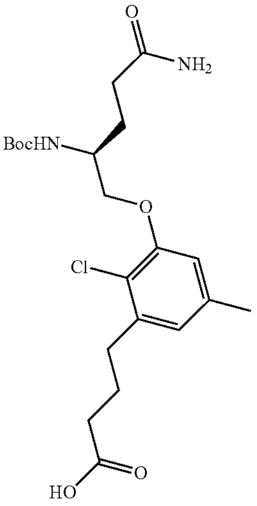 [SMILES: Cc1cc(CCCC(=O)O)c(Cl)c(OC[C@H](CCC(N)=O)NC(=O)OC(C)(C)C)c1] | 4-[3-[(2S)-2-[(tert-butoxycarbonyl)amino]-4-carbamoylbutoxy]-2-chloro-5-methylphenyl]butanoic acid | 443.05 | (300 MHz, DMSO-$d_6$) δ 11.99 (s, 1H), 7.28 (s, 1H), 6.90-6.65 (m, 3H), 3.91 (d, J = 6.1 Hz, 2H), 3.85-3.65 (m, 1H), 2.66 (dd, J = 8.7, 6.6 Hz, 2H), 2.28 (s, 3H), 2.24 (d, J = 7.3 Hz, 2H), 2.18-2.10 (m, 2H), 1.92-1.70 (m, 4H), 1.69-1.56 (m, 1H), 1.40 (s, 9H) |

The following intermediates in Table 42 were prepared according to Step 4 to prepare Intermediate B.

TABLE 42

| Characterization data for intermediates prepared according to above. | | | | |
|---|---|---|---|---|
| Inter-mediate | Structure | Chemical Name | MS: $[(M + 1)]^+$ | $^1H$ NMR |
| G-4-29 | 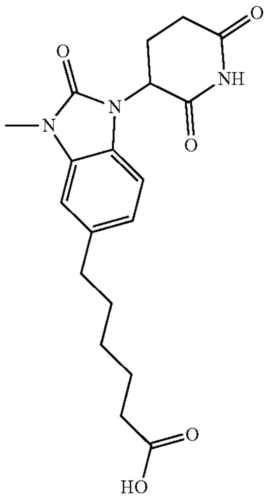 [SMILES: Cn1c(=O)n(C2CCC(=O)NC2=O)c2ccc(CCCCCC(=O)O)cc21] | 6-[1-(2,6-Dioxopiperidin-3-yl)-3-methyl-2-oxo-1,3-benzodiazol-5-yl]hexanoic acid | 374.2 | (400 MHz, DMSO-$d_6$) δ 11.98 (br, 1H), 11.09 (s, 1H), 7.07-6.96 (m, 2H), 6.86 (dd, J = 8.1, 1.6 Hz, 1H), 5.34 (dd, J = 12.7, 5.4 Hz, 1H), 3.33 (s, 3H), 2.90 (ddd, J = 15.0, 12.3, 6.9 Hz, 1H), 2.77-2.57 (m, 4H), 2.21 (t, J = 7.3 Hz, 2H), 2.05-1.97 (m, 1H), 1.60-1.50 (m, 4H), 1.36-1.23 (m, 2H) |
| G-4-30 | 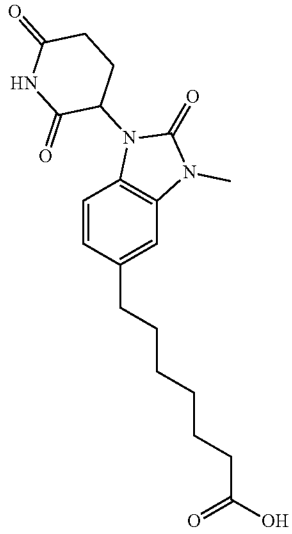 [SMILES: Cn1c(=O)n(C2CCC(=O)NC2=O)c2ccc(CCCCCCC(=O)O)cc21] | 7-[1-(2,6-dioxopiperidin-3-yl)-3-methyl-2-oxo-1,3-benzodiazol-5-yl]heptanoic acid | 388.1 | (400 MHz, DMSO-$d_6$) δ 11.95 (br, 1H), 11.09 (s, 1H), 7.07-6.96 (m, 2H), 6.86 (dd, J = 8.1, 1.6 Hz, 1H), 5.34 (dd, J = 12.8, 5.3 Hz, 1H), 3.33 (s, 3H), 2.90 (ddd, J = 16.5, 13.0, 5.2 Hz, 1H), 2.77-2.56 (m, 4H), 2.20 (t, J = 7.3 Hz, 2H), 2.07-1.93 (m, 1H), 1.58 (t, J = 6.4 Hz, 2H), 1.55-1.44 (m, 2H), 1.39-1.22 (m, 4H). |

TABLE 42-continued

| Characterization data for intermediates prepared according to above. | | | | |
|---|---|---|---|---|
| Inter-mediate | Structure | Chemical Name | MS: $[(M + 1)]^+$ | $^1H$ NMR |
| G-4-31 | 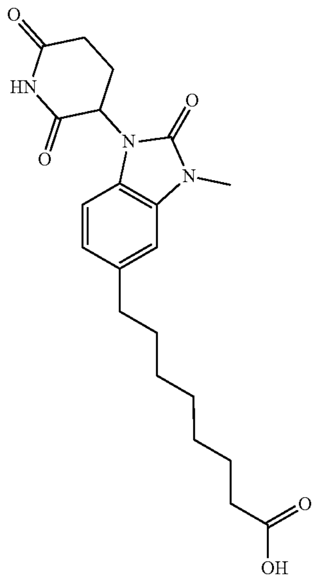 [SMILES: Cn1c(=O)n(C2CCC(=O)NC2=O)c2ccc(CCCCCCCC(=O)O)cc21] | 8-[1-(2,6-dioxopiperidin-3-yl)-3-methyl-2-oxo-1,3-benzodiazol-5-yl]octanoic acid | 402.3 | (400 MHz, DMSO-$d_6$) δ 11.98 (br, 1H), 11.10 (s, 1H), 7.06-6.97 (m, 2H), 6.86 (dd, J = 8.0, 1.6 Hz, 1H), 5.34 (dd, J = 12.8, 5.3 Hz, 1H), 3.33 (s, 3H), 2.91 (ddd, J = 17.0, 12.9, 5.2 Hz, 1H), 2.72 (td, J = 13.0, 4.4 Hz, 1H), 2.67-2.53 (m, 4H), 2.06-1.96 (m, 1H), 1.60 (d, J = 8.3 Hz, 2H), 1.49 (p, J = 7.3 Hz, 2H), 1.35-1.15 (m, 7H). |
| G-4-32 | 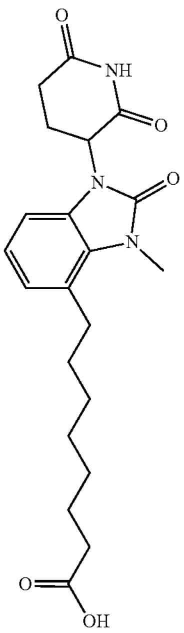 [SMILES: Cn1c(=O)n(C2CCC(=O)NC2=O)c2cccc(CCCCCCCC(=O)O)c21] | 8-[1-(2,6-dioxopiperidin-3-yl)-3-methyl-2-oxo-1,3-benzodiazol-4-yl]octanoic acid | 402.2 | (400 MHz, DMSO-$d_6$) δ 12.00 (br, 1H), 11.10 (s, 1H), 6.99-6.91 (m, 2H), 6.91-6.83 (m, 1H), 5.37 (dd, J = 12.5, 5.4 Hz, 1H), 3.55 (s, 3H), 2.97-2.80 (m, 2H), 2.78-2.58 (m, 2H), 2.20 (t, J = 7.3 Hz, 2H), 2.04-1.95 (m, 1H), 1.58 (q, J = 7.6 Hz, 2H), 1.50 (p, J = 7.3 Hz, 2H), 1.41-1.33 (m, 7H). |

TABLE 42-continued

| Characterization data for intermediates prepared according to above. | | | | |
|---|---|---|---|---|
| Intermediate | Structure | Chemical Name | MS: $[(M + 1)]^+$ | $^1H$ NMR |
| G-4-33 | 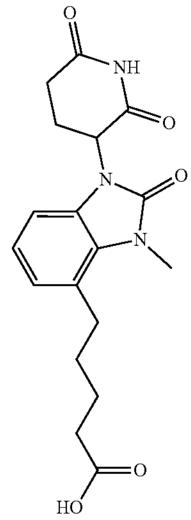 [SMILES: Cn1c(=O)n(C2CCC(=O)NC2=O)c2cccc(CCCCC(=O)O)c21] | 5-[1-(2,6-dioxopiperidin-3-yl)-3-methyl-2-oxo-1,3-benzodiazol-4-yl]pentanoic acid | 360.1 | (400 MHz, DMSO-$d_6$) δ 11.93 (br, 1H), 11.09 (s, 1H), 7.00-6.95 (m, 2H), 6.87 (dd, J = 5.8, 3.1 Hz, 1H), 5.37 (dd, J = 12.4, 5.4 Hz, 1H), 3.56 (s, 3H), 2.98-2.85 (m, 3H), 2.79-2.57 (m, 2H), 2.27 (d, J = 6.9 Hz, 2H), 2.04-1.95 (m, 1H), 1.62 (s, 4H). |
| G-4-68 | 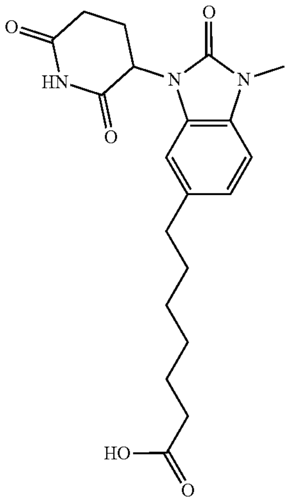 [SMILES: Cn1c(=O)n(C2CCC(=O)NC2=O)c2cc(CCCCCCC(=O)O)ccc21] | 7-3-(2,6-dioxopiperidin-3-yl)-1-methyl-2-oxo-1,3-benzodiazol-5-yl]heptanoic acid | 388.10 | (400 MHz, DMSO-$d_6$) δ 11.92 (s, 1H), 11.06 (s, 1H), 7.06 (d, J = 8.0 Hz, 1H), 6.99 (s, 1H), 6.90 (dd, J = 8.0, 1.5 Hz, 1H), 5.34 (dd, J = 12.8, 5.3 Hz, 1H), 3.31 (s, 3H), 2.97-2.83 ( m, 1H), 2.80-2.70 (m, 1H), 2.60-2.53 (m, 2H), 2.18 (t, J = 7.3 Hz, 2H), 2.04-1.95 (m, 1H), 1.54 (t, J = 7.5 Hz, 2H), 1.47 (q, J = 7.4 Hz, 2H), 1.38-1.21 (m, 5H) |
| G-4-69 | 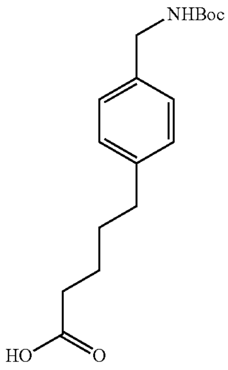 [SMILES: CC(C)(C)OC(=O)NCc1ccc(CCCCC(=O)O)cc1] | 5-(4-[[(tert-butoxycarbonyl) amino]methyl] phenyl)pentanoic acid | 308.18 | (400 MHz, DMSO-$d_6$) δ 7.35 (t, J = 6.3 Hz, 1H), 7.13 (s, 4H), 4.08 (d, J = 6.2 Hz, 2H), 2.58-2.52 (m, 2H), 2.21 (t, J = 7.0 Hz, 2H), 1.61-1.45 (m, 4H), 1.39 (s, 9H) |

TABLE 42-continued

| Characterization data for intermediates prepared according to above. | | | | |
|---|---|---|---|---|
| Inter-mediate | Structure | Chemical Name | MS: $[(M+1)]^+$ | $^1H$ NMR |
| G-4-70 | 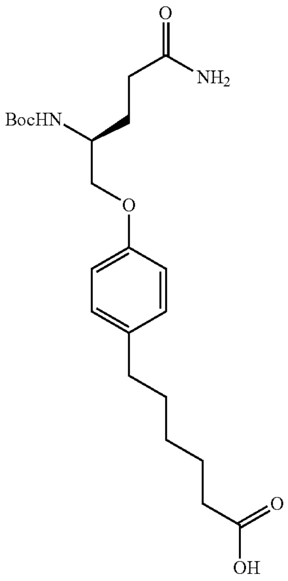 [SMILES: CC(C)(C)OC(=O)N[C@@H](CCC(N)=O)COc1ccc(CCCCCC(=O)O)cc1] | 6-[4-[(2S)-2-[(tert-butoxycarbonyl)amino]-4-carbamoylbutoxy]phenyl]hexanoic acid | 423.15 | (400 MHz, DMSO-$d_6$) δ 11.95 (s, 1H), 7.26 (s, 1H), 7.09 (d, J = 8.0 Hz, 2H), 6.82 (d, J = 8.2 Hz, 3H), 6.73 (s, 1H), 3.82 (qd, J = 9.6, 5.8 Hz, 2H), 3.70 (dp, J = 9.5, 5.1 Hz, 1H), 2.26-2.02 (m, 6H), 1.86-1.81 (m, 1H), 1.68-1.45 (m, 5H), 1.39 (s, 9H), 1.27 (p, J = 7.7, 7.2 Hz, 2H) |
| G-4-71 | 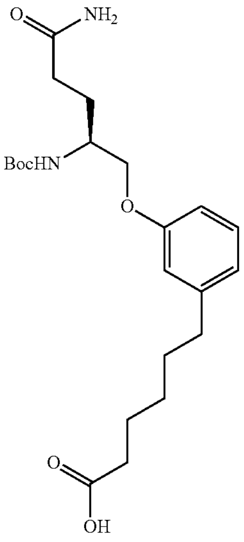 [SMILES: CC(C)(C)OC(=O)N[C@@H](CCC(N)=O)COc1cccc(CCCCCC(=O)O)c1] | 6-[3-[(2S)-2-[(tert-butoxycarbonyl)amino]-4-carbamoylbutoxy]phenyl]hexanoic acid | 423.22 | (400 MHz, DMSO-$d_6$) δ 7.27 (s, 1H), 7.16 (t, J = 8.0 Hz, 1H), 6.82 (d, J = 8.5 Hz, 1H), 6.78-6.69 (m, 4H), 3.90-3.80 (m, 2H), 3.76-3.67 (m, 1H), 2.17 (t, J = 7.4 Hz, 2H), 2.12 (dd, J = 7.4, 2.0 Hz, 1H), 2.09-2.05 (m, 3H), 1.88-1.75 (m, 1H), 1.60-1.50 (m, 5H), 1.39 (s, 9H), 1.32-1.25 (m, 3H) |

TABLE 42-continued

| Characterization data for intermediates prepared according to above. | | | | |
|---|---|---|---|---|
| Inter-mediate | Structure | Chemical Name | MS: [(M + 1)]+ | $^1$H NMR |
| G-4-72 | 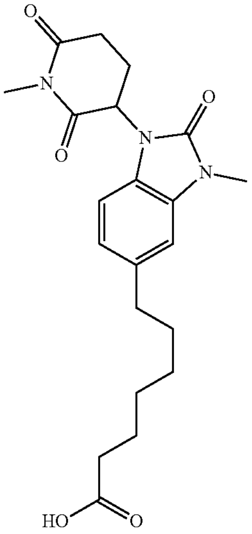 | 7-(3-methyl-1-(1-methyl-2,6-dioxopiperidin-3-yl)-2-oxo-2,3-dihydro-1H-benzo[d]imidazol-5-yl)heptanoic acid | 402.10 | (400 MHz, $CDCl_3$) δ 6.92-6.83 (m, 2H), 6.70 (d, J = 8.0 Hz, 1H), 5.21 (dd, J = 12.9, 5.3 Hz, 1H), 3.45 (s, 3H), 3.27 (s, 3H), 3.10-3.00 (m, 1H), 2.92-2.83 (m, 1H), 2.67 (t, J = 7.6 Hz, 2H), 2.36 (t, J = 7.4 Hz, 4H), 2.25-2.19 (m, 1H), 2.09-1.95 (m, 1H), 1.72-1.65 (m, 7H), 1.40-1.37 (m, 2H) |
| G-4-73 | 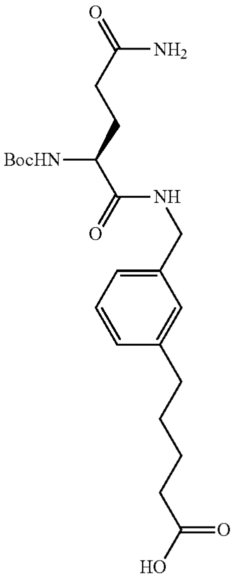 [SMILES: CC(C)(C)OC(=O)N[C@@H](CCC(N)=O)C(=O)NCc1cccc(CCCCC(=O)O)c1] | 5-(3-[(2S)-2-[(tert-butoxycarbonyl)amino]-4-carbamoylbutanamido]methyl]-phenyl)pentanoic acid | 436.32 | (400 MHz, DMSO-$d_6$) δ 8.28 (t, J = 6.0 Hz, 1H), 7.28 (s, 1H), 7.20 (t, J = 7.5 Hz, 1H), 7.11-7.01 (m, 3H), 6.94 (d, J = 7.9 Hz, 1H), 6.76 (s, 1H), 4.26 (d, J = 5.6 Hz, 2H), 3.94-3.88 (m, 1H), 3.17 (s, 2H), 2.20 (t, J = 7.0 Hz, 2H), 2.13-2.07 (m, 2H), 1.90-1.83 (m, 1H), 1.76-1.69 (m, 1H), 1.61-1.44 (m, 3H), 1.39 (s, 9H), 1.33-1.13 (m, 2H) |

TABLE 42-continued
| Characterization data for intermediates prepared according to above. | | | | |
|---|---|---|---|---|
| Inter-mediate | Structure | Chemical Name | MS: [(M + 1)]+ | 1H NMR |
| G-4-74 | 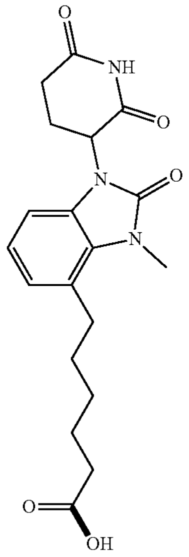 | 6-[1-(2,6-dioxopiperidin-3-yl)-3-methyl-2-oxo-1,3-benzodiazol-4-yl]hexanoic acid | 374.20 | (400 MHz, DMSO-$d_6$) δ 11.99 (s, 1H), 11.09 (s, 1H), 6.99-6.91 (m, 2H), 6.91-6.84 (m, 1H), 5.37 (dd, J = 12.5, 5.4 Hz, 1H), 3.55 (s, 3H), 2.92-2.86 (m, 3H), 2.76-2.67 (m, 1H), 2.66-2.58 (m, 1H), 2.23 (t, J = 7.3 Hz, 2H), 1.66-1.51 (m, 4H), 1.44-1.38 (m, 2H) |
| G-4-75 | 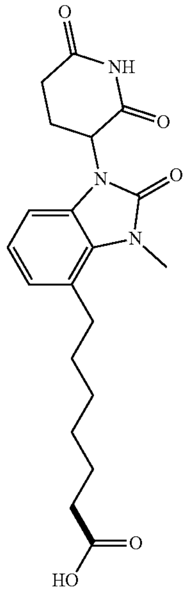 | 7-1-(2,6-dioxopiperidin-3-yl)-3-methyl-2-oxo-1,3-benzodiazol-4-yl]heptanoic acid | 388.10 | (400 MHz, DMSO-$d_6$) δ 11.10 (s, 1H), 6.99-6.91 (m, 2H), 6.91-6.83 (m, 1H), 5.37 (dd, J = 12.5, 5.4 Hz, 1H), 3.55 (s, 3H), 2.95-2.85 (m, 4H), 2.77-2.57 (m, 2H), 2.26-2.18 (m, 2H), 1.64-1.45 (m, 4H), 1.43-1.30 (m, 4H) |

TABLE 42-continued

| Characterization data for intermediates prepared according to above. | | | | |
|---|---|---|---|---|
| Intermediate | Structure | Chemical Name | MS: $[(M + 1)]^+$ | $^1H$ NMR |
| G-4-76 | 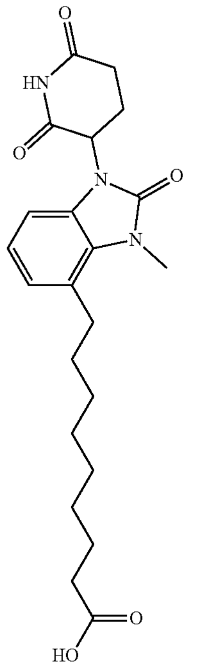 [SMILES: Cn1c(=O)n(C2CCC(=O)NC2=O)c2cccc(CCCCCCCCC(=O)O)c21] | 9-[1-(2,6-dioxopiperidin-3-yl)-3-methyl-2-oxo-1,3-benzodiazol-4-yl]nonanoic acid | 416.15 | (400 MHz, DMSO-$d_6$) δ 11.99 (s, 1H), 11.10 (s, 1H), 6.99-6.91 (m, 2H), 6.86 (dd, J = 5.2, 3.8 Hz, 1H), 5.37 (dd, J = 12.6, 5.4 Hz, 1H), 3.55 (s, 3H), 2.93-2.84 (m, 3H), 2.83-2.55 (m, 3H), 2.19 (t, J = 7.3 Hz, 2H), 1.62-1.56 (m, 2H), 1.49 (t, J = 7.2 Hz, 2H), 1.42-1.30 (m, 4H), 1.30-1.25 (m, 4H) |
| G-4-77 | 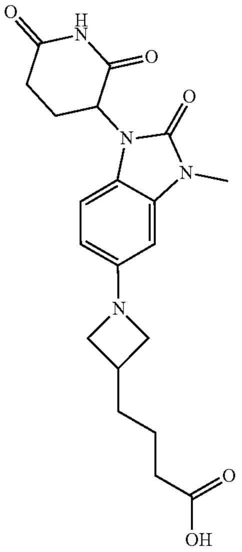 [SMILES: Cn1c(=O)n(C2CCC(=O)NC2=O)c2ccc(N3CC(CCCC(=O)O)C3)cc21] | 4-[1-[1-(2,6-dioxopiperidin-3-yl)-3-methyl-2-oxo-1,3-benzodiazol-5-yl]azetidin-3-yl]btanoic acid | 401.20 | (400 MHz, DMSO-$d_6$) δ 11.08 (s, 1H), 6.98 (d, J = 8.4 Hz, 1H), 6.58 (s, 1H), 6.34 (d, J = 8.4 Hz, 1H), 5.31 (dd, J = 12.9, 5.3 Hz, 1H), 4.07 (t, J = 7.7 Hz, 2H), 3.56 (dd, J = 15.8, 8.8 Hz, 2H), 3.31 (s, 3H), 2.93-2.88 (m, 1H), 2.81-2.56 (m, 4H), 2.24 (t, J = 7.2 Hz, 2H), 2.07-1.90 (m, 1H), 1.65-1.46 (m, 4H). |

TABLE 42-continued

Characterization data for intermediates prepared according to above.

| Intermediate | Structure | Chemical Name | MS: [(M + 1)]+ | $^1$H NMR |
|---|---|---|---|---|
| G-4-78 | 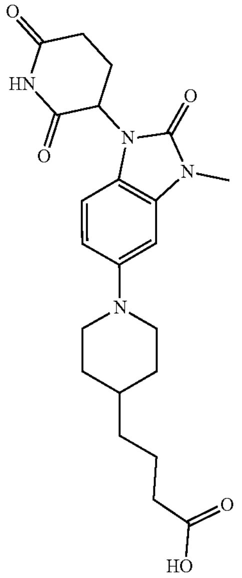 [SMILES: Cn1c(=O)n(C2CCC(=O)NC2=O)c2ccc(N3CCC(CCCC(=O)O)CC3)cc21] | 4-[1-[1-(2,6-dioxopiperidin-3-yl)-3-methyl-2-oxo-1,3-benzodiazol-5-yl]piperidin-4-yl]butanoic acid | 429.35 | (400 MHz, DMSO-$d_6$) δ 12.03 (s, 1H), 11.12 (s, 1H), 7.77-6.54 (m, 3H), 5.38 (d, J = 12.0 Hz, 1H), 3.59 (d, J = 11.4 Hz, 2H), 3.36 (s, 3H), 3.00-2.80 (m, 1H), 2.79-2.57 (m, 2H), 2.24 (t, J = 7.3 Hz, 2H), 2.01 (dd, J = 9.6, 4.2 Hz, 1H), 1.97-1.75 (m, 3H), 1.71-1.37 (m, 6H), 1.34-1.27 (m, 2H) |
| G-4-79 | 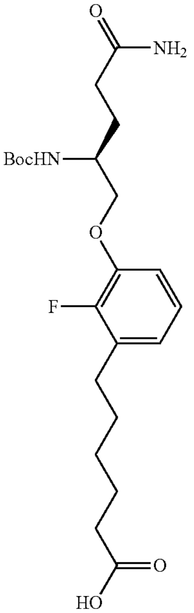 [SMILES: CC(C)(C)OC(=O)N[C@@H](CCC(N)=O)COc1cccc(CCCCCC(=O)O)c1F] | 6-[3-[(2S)-2-[(tert-butoxycarbonyl) amino]-4-carbamoylbutoxy]-2-fluorophenyl] hexanoic acid | 441.51 | (400 MHz, DMSO-$d_6$) δ 7.26 (s, 1H), 7.05-6.93 (m, 2H), 6.86-6.77 (m, 2H), 6.73 (s, 1H), 3.91 (d, J = 6.0 Hz, 2H), 3.17 (s, 1H), 2.59-2.55 (m, 2H), 2.55 (s, 3H), 2.18 (d, J = 7.3 Hz, 2H), 2.14 (d, J = 7.3 Hz, 2H), 1.90-1.86 (m, 1H), 1.53-1.49 (m, 2H), 1.39 (s, 9H), 1.35-1.20 (m, 3H) |

TABLE 42-continued

| Characterization data for intermediates prepared according to above. | | | | |
|---|---|---|---|---|
| Intermediate | Structure | Chemical Name | MS: $[(M + 1)]^+$ | $^1$H NMR |
| G-4-96 | 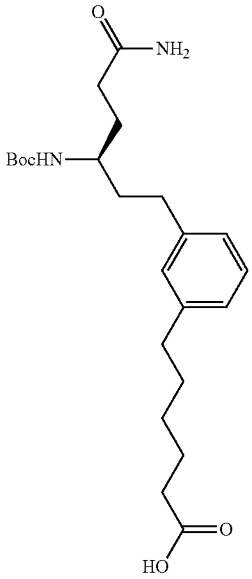 [SMILES: CC(C)(C)OC(=O)N[C@@H](CCC(N)=O)CCc1cccc(CCCCCC(=O)O)c1] | 6-[3-[(3R)-3-[(tert-butoxycarbonyl)amino]-5-carbamoylpentyl]phenyl]hexanoic acid | 421.35 | (300 MHz, DMSO-$d_6$) δ 11.92 (s, 1H), 7.17 (dt, J = 14.7, 4.6 Hz, 2H), 6.97 (d, J = 7.9 Hz, 3H), 6.67 (d, J = 8.8 Hz, 2H), 3.38 (d, J = 7.5 Hz, 1H), 2.58-2.52 (m, 2H), 2.19 (t, J = 7.3 Hz,2H), 2.02 (t, J = 7.9 Hz, 2H), 1.62-1.54 (m, 8H), 1.40 (s, 9H), 1.34-1.20 (m, 4H) |
| G-4-97 | 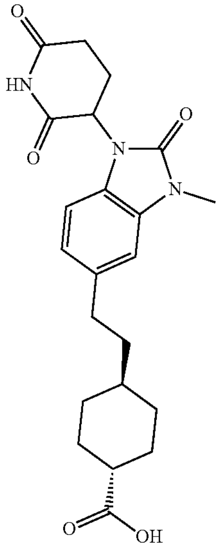 [SMILES: Cn1c(=O)n(C2CCC(=O)NC2=O)c2ccc(CC[C@H]3CC[C@H](C(=O)O)CC3)cc21] | (1r,4r)-4-[2-[1-(2,6-dioxopiperidin-3-yl)-3-methyl-2-oxo-1,3-benzodiazol-5-yl]ethyl]cyclohexane-1-carboxylic acid | 414.10 | (400 MHz, DMSO-$d_6$) δ 11.96 (s, 1H), 11.08 (s, 1H), 7.05-6.97 (m, 2H), 6.90-6.83 (m, 1H), 5.34 (dd, J = 12.7, 5.4 Hz, 1H), 3.33 (s, 3H), 2.97-2.84 (m, 1H), 2.78-2.70 (m, 1H), 2.66-2.57 (m, 3H), 2.22-2.07 (m, 1H), 2.03-1.97 (m, 1H), 1.94-1.79 (m, 4H), 1.79-1.73 (m, 1H), 1.54-1.44 (m, 2H), 1.36-1.27 (m, 1H), 1.28-1.14 (m, 3H) |

TABLE 42-continued

Characterization data for intermediates prepared according to above.

| Inter-mediate | Structure | Chemical Name | MS: $[(M + 1)]^+$ | $^1H$ NMR |
|---|---|---|---|---|
| G-4-98 | 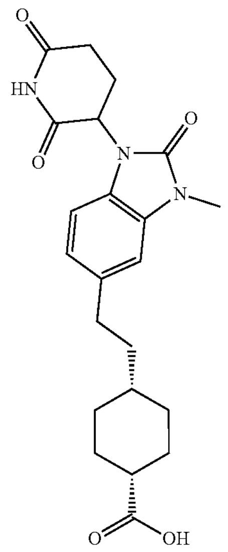 [SMILES: Cn1c(=O)n(C2CCC(=O)NC2=O)c2ccc(CC[C@H]3CC[C@@H](C(=O)O)CC3)cc21] | (1s,4s)-4-[2-[1-(2,6-dioxopiperidin-3-yl)-3-methyl-2-oxo-1,3-benzodiazol-5-yl]ethyl]cyclohexane-1-carboxylic acid | 414.20 | (400 MHz, Chloroform-d) δ 8.28 (s, 1H), 6.88 (dd, J = 8.0, 1.6 Hz, 1H), 6.83 (d, J = 1.5 Hz, 1H), 6.70 (d, J = 8.0 Hz, 1H), 5.21 (dd, J = 12.6, 5.4 Hz, 1H), 3.43 (s, 3H), 2.84-2.59 (m, 4H), 2.26-2.17 (m, 1H), 2.09-1.97 (m, 2H), 1.90-1.82 (m, 4H), 1.70-1.51 (m, 5H), 1.29-1.25 (m, 2H) |
| G-4-99 | 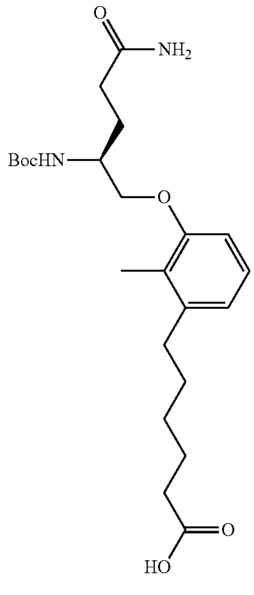 [SMILES: Cc1c(CCCCCC(=O)O)cccc1OC[C@H](CCC(N)=O)NC(=O)OC(C)(C)C] | 6-[3-[(2S)-2-[(tert-butoxycarbonyl)amino]-4-carbamoylbutoxyl-2-methylphenyl]-hexanoic acid | $[(M - 1)]^-$ = 435.05 | (400 MHz, DMSO-$d_6$) δ 7.67-7.52 (m, 2H), 7.28 (s, 1H), 7.03 (t, J = 7.9 Hz, 1H), 6.82 (d, J = 7.9 Hz, 1H), 6.73 (dd, J = 1.1, 3.7 Hz, 3H), 3.87-3.76 (m, 3H), 2.56-2.53 (m, 2H), 2.19-2.12 (m, 3H), 2.09 (s, 3H), 1.89-1.75 (m, 2H), 1.66-1.59 (m, 1H), 1.55-1.46 (m, 3H), 1.40 (s, 9H), 1.36-1.22 (m, 2H) |

TABLE 42-continued

| Characterization data for intermediates prepared according to above. | | | | |
|---|---|---|---|---|
| Intermediate | Structure | Chemical Name | MS: $[(M+1)]^+$ | $^1H$ NMR |
| G-4-100 | 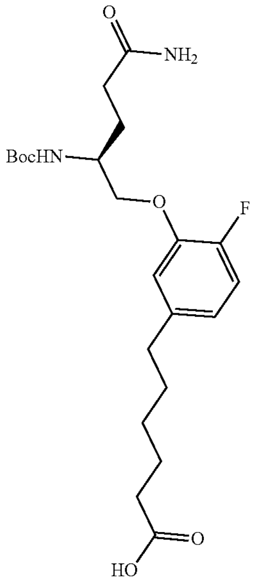 [SMILES: CC(C)(C)OC(=O)N[C@@H](CCC(N)=O)COc1cc(CCCCCC(=O)O)ccc1F] | 6-[4-[(2S)-2-[(tert-butoxycarbonyl)amino]-4-carbamoylbutoxy]-3-fluorophenyl]hexanoic acid | $[(M-1)]^- =$ 439.10 | (400 MHz, DMSO-$d_6$) δ 7.67-7.53 (m, 3H), 7.29 (s, 1H), 7.11-6.98 (m, 3H), 6.88-6.69 (m, 3H), 3.93 (d, J = 6.1 Hz, 2H), 3.76-3.72 (m, 1H), 2.55-2.51 (m, 1H), 2.15-2.11 (m, 3H), 1.91-1.74 (m, 2H), 1.57-1.52 (m, 5H), 1.39 (s, 9H) |
| G-4-101 | 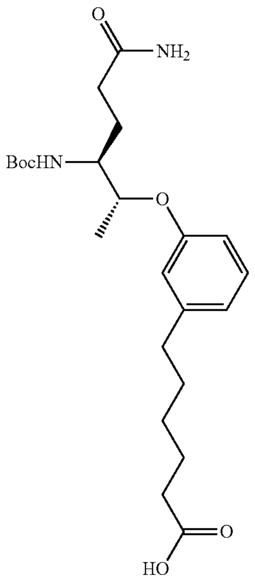 [SMILES: C[C@@H](Oc1cccc(CCCCCC(=O)O)c1)[C@H](CCC(N)=O)NC(=O)OC(C)(C)C] | 6-(3-[[(2R,3S)-3-[(tert-butoxycarbonyl)amino]-5-carbamoylpentan-2-yl]oxy]phenyl)hexanoic acid | 437.20 | (400 MHz, DMSO-$d_6$) δ 7.31-7.22 (m, 1H), 7.15 (t, J = 7.7 Hz, 1H), 6.80-6.65 (m, 5H), 4.33-4.27 (m, 1H), 3.54-3.45 (m, 1H), 3.17 (s, 1H), 2.55-2.53 (m, 1H), 2.19-1.97 (m, 4H), 1.91-1.82 (m, 1H), 1.58-1.47 (m, 5H), 1.39 (s, 9H), 1.34-1.21 (m, 3H), 1.16 (d, J = 6.1 Hz, 3H) |

TABLE 42-continued

Characterization data for intermediates prepared according to above.

| Inter-mediate | Structure | Chemical Name | MS: $[(M + 1)]^+$ | $^1H$ NMR |
|---|---|---|---|---|
| G-4-102 | 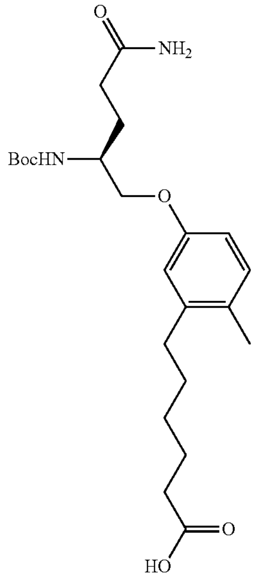 [SMILES: Cc1ccc(OC[C@H](CCC(N)=O)NC(=O)OC(C)(C)C)cc1CCCCCC(=O)O] | 6-[5-[(2S)-2-[(tert-butoxycarbonyl)amino]-4-carbamoylbutoxy]-2-methylphenyl]hexanoic acid | 437.10 | (400 MHz, DMSO-$d_6$) δ 7.27 (s, 1H), 7.01 (d, J = 8.3 Hz, 1H), 6.81 (d, J = 8.5 Hz, 1H), 6.73 (s, 1H), 6.69 (d, J = 2.7 Hz, 1H), 6.64-6.62 (m, 1H), 3.80-3.78 (m, 2H), 3.69-3.67 (m, 3H), 2.27-2.03 (m, 8H), 1.86-1.75 (m, 3H), 1.54-1.52 (m, 5H), 1.39 (s, 9H) |
| G-4-103 | 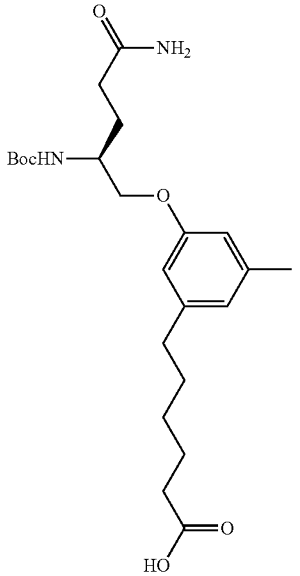 [SMILES: Cc1cc(CCCCCC(=O)O)cc(OC[C@H](CCC(N)=O)NC(=O)OC(C)(C)C)c1] | 6-[3-[(2S)-2-[(tert-butoxycarbonyl)amino]-4-carbamoylbutoxy]-5-methylphenyl]hexanoic acid | $[(M - 1)]^-$ = 435.05 | (400 MHz, DMSO-$d_6$) δ 7.39-7.16 (m, 1H), 6.81 (d, J = 8.5 Hz, 1H), 6.73 (s, 1H), 6.56-6.50 (m, 3H), 3.83-3.79 (m, 2H), 3.72-3.68 (m, 1H), 2.49-2.45 (m, 2H), 2.23 (s, 3H), 2.21-2.06 (m, 3H), 1.87-1.74 (m, 1H), 1.57-1.50 (m, 5H), 1.39 (s, 9H), 1.32-1.21 (m, 4H) |

TABLE 42-continued

| Characterization data for intermediates prepared according to above. | | | | |
|---|---|---|---|---|
| Intermediate | Structure | Chemical Name | MS: $[(M + 1)]^+$ | $^1H$ NMR |
| G-4-104 | 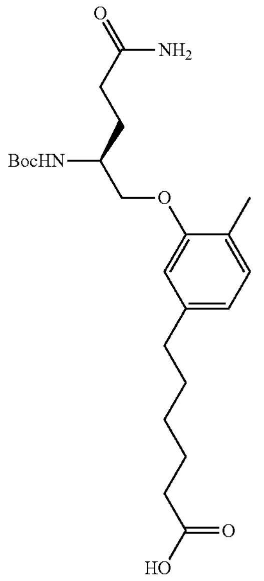 [SMILES: Cc1ccc(CCCCCC(=O)O)cc1OC[C@H](CCC(N)=O)NC(=O)OC(C)(C)C] | 6-[3-[(2S)-2-[(tert-butoxycarbonyl)amino]-4-carbamoylbutoxy]-4-methylphenyl]hexanoic acid | $[(M - 1)]^- =$ 435.15 | (400 MHz, DMSO-$d_6$) δ 12.05 (s, 1H), 7.32-7.23 (m, 1H), 6.99 (d, J = 7.5 Hz, 1H), 6.80 (d, J = 8.3 Hz, 1H), 6.75-6.72 (m, 2H), 6.64 (d, J = 7.5, 1.5 Hz, 1H), 4.03-3.69 (m, 3H), 2.29-2.00 (m, 7H), 1.95-1.66 (m, 2H), 1.65-1.48 (m, 6H), 1.39 (s, 9H), 1.30-1.26 (m, 2H) |
| G-4-105 | 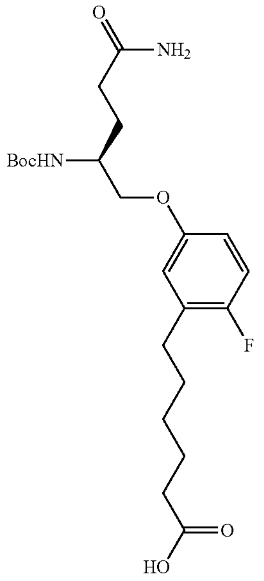 [SMILES: CC(C)(C)OC(=O)N[C@@H](CCC(N)=O)COc1ccc(F)c(CCCCCC(=O)O)c1] | 6-[5-[(2S)-2-[(tert-butoxycarbonyl)amino]-4-carbamoylbutoxy]-2-fluorophenyl]hexanoic acid | 441.10 | (400 MHz, DMSO-$d_6$) δ 7.27 (s, 1H), 7.03 (t, J = 9.3 Hz, 1H), 6.86-6.79 (m, 2H), 6.77-6.73 (m, 2H), 3.84-3.80 (m, 2H), 3.71-3.67 (m, 1H), 2.55 (t, J = 7.6 Hz, 2H), 2.18 (t, J = 7.3 Hz, 2H), 2.13-2.09 (m, 2H), 1.87-1.74 (m, 1H), 1.64-1.56 (m, 1H), 1.54-1.50 (m, 4H), 1.39 (s, 9H), 1.33-1.20 (m, 2H) |

TABLE 42-continued

| Characterization data for intermediates prepared according to above. | | | | |
|---|---|---|---|---|
| Inter-mediate | Structure | Chemical Name | MS: $[(M+1)]^+$ | $^1H$ NMR |
| G-4-106 | 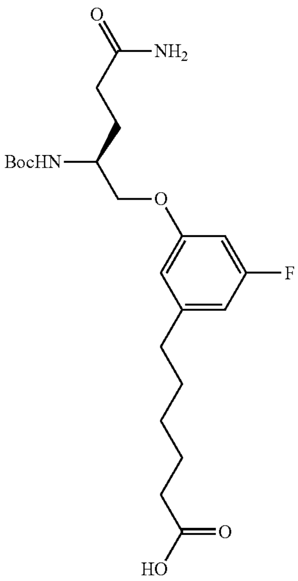 [SMILES: CC(C)(C)OC(=O)N[C@@H](CCC(N)=O)COc1cc(F)cc(CCCCCC(=O)O)c1] | -[3-[(2S)-2-[(tert-butoxycarbonyl) amino]-4-carbamoylbutoxy]-5-fluorophenyl] hexanoic acid | 441.10 | (400 MHz, DMSO-$d_6$) δ 12.00 (s, 1H), 7.26 (s, 1H), 6.82 (d, J = 8.4 Hz, 1H), 6.74 (d, J = 7.9 Hz, 1H), 6.64-6.54 (m, 3H), 3.92-3.80 (m, 2H), 3.73-3.69 (m, 1H), 2.54 (d, J = 7.6 Hz, 2H), 2.24-2.03 (m, 4H), 1.86-1.73 (m, 1H), 1.56-1.52 (m, 4H), 1.39 (s, 9H), 1.34-1.21 (m, 3H) |
| G-4-107 | 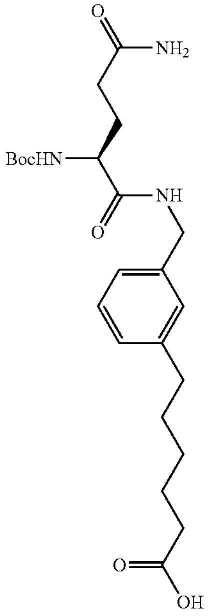 [SMILES: CC(C)(C)OC(=O)N[C@@H](CCC(N)=O)C(=O)NCc1cccc(CCCCCC(=O)O)c1] | 6-(3-[(2S)-2-[tert-butoxycarbonyl) amino]-4-carbamoylbutan-amido]methyl] phenyl)hexanoic acid | 450.25 | (400 MHz, Methanol-$d_4$) δ 7.22 (t, J = 7.5 Hz, 1H), 7.15 (s, 1H), 7.11-7.08 (m, 2H), 4.46-4.31 (m, 2H), 4.11-4.04 (m, 1H), 2.69-2.54 (m, 2H), 2.32-2.28 (m, 4H), 2.15-2.04 (m,1H), 1.91-1.89 (m, 1H), 1.72-1.56 (m, 4H), 1.46 (s, 9H), 1.41-1.32 (m, 2H). |

TABLE 42-continued

Characterization data for intermediates prepared according to above.

| Inter-mediate | Structure | Chemical Name | MS: [(M + 1)]+ | $^1$H NMR |
|---|---|---|---|---|
| G-4-108 | 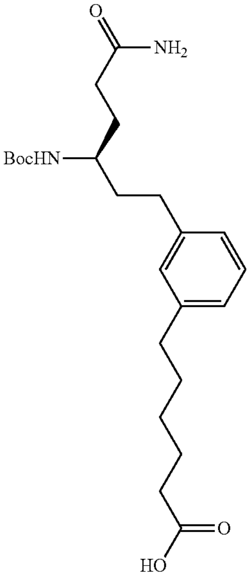 [SMILES: CC(C)(C)OC(=O)N[C@@H](CCC(N)=O)CCc1cccc(CCCCCC(=O)O)c1] | 6-[3-[(3R)-3-[(tert-butoxycarbonyl) amino]-5-carbamoylpentyl] phenyl]hexanoic acid | 421.15 | (400 MHz, DMSO-$d_6$) δ 11.91 (s, 1H), 7.21 (s, 1H), 7.16 (t, J = 7.4 Hz, 1H), 6.98 (d, J = 7.9 Hz, 3H), 6.69 (d, J = 10.2 Hz, 2H), 3.44-3.34 (m, 1H), 2.56-2.53 (m, 2H), 2.20 (t, J = 7.3 Hz, 2H), 2.03 (t, J = 7.9 Hz, 2H), 1.69-1.47 (m, 10H), 1.41 (s, 9H), 1.35-1.27 (m, 2H) |
| G-4-141 | 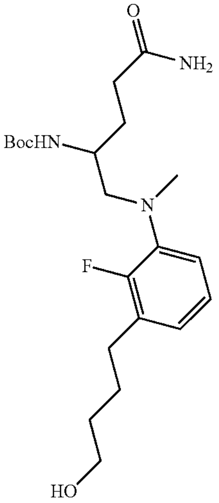 [SMILES: CN(CC(CCC(N)=O)NC(=O)OC(C)(C)C)c1cccc(CCCCO)c1F] | tert-butyl N-(4-carbamoyl-1-[[2-fluoro-3-(4-hydroxybutyl) phenyl](methyl) amino]butan-2-yl)carbamate | 412.15 | (400 MHz, DMSO-$d_6$) δ 7.22 (s, 1H), 6.94 (t, J = 7.8 Hz, 1H), 6.79 (t, J = 8.2 Hz, 1H), 6.71 (dd, J = 15.4, 8.4 Hz, 2H), 6.56 (d, J = 9.0 Hz, 1H), 4.38 (s, 1H), 3.64 (s, 1H), 3.41 (t, J = 6.4 Hz, 2H), 3.04 (d, J = 7.0 Hz, 2H), 2.78 (s, 3H), 2.56 (t, J = 7.5 Hz, 2H), 2.17-1.96 (m, 2H), 1.91 (s, 1H), 1.75-1.71 (m, 1H), 1.60-1.56 (m, 2H), 1.55 (s, 2H), 1.53 (s, 9H) |

TABLE 42-continued

| Characterization data for intermediates prepared according to above. | | | | |
|---|---|---|---|---|
| Inter-mediate | Structure | Chemical Name | MS: [(M + 1)]$^+$ | $^1$H NMR |
| G-4-142 | 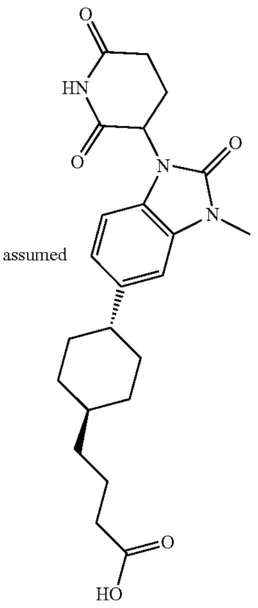 [SMILES: Cn1c(=O)n(C2CCC(=O)NC2=O)c2ccc([C@H]3CC[C@H](CCCC(=O)O)CC3)cc21] assumed | 4-[(1r,4s)-4-[1-(2,6-dioxopiperidin-3-yl)-3-methyl-2-oxo-1,3-benzodiazol-5-yl]cyclohexyl] butanoic acid | 428.20 | Used next step directly without purification |
| G-4-143 | 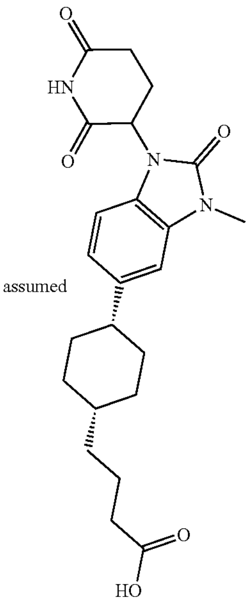 [SMILES: Cn1c(=O)n(C2CCC(=O)NC2=O)c2ccc([C@H]3CC[C@@H](CCCC(=O)O)CC3)cc21] assumed | 4-[(1s,4r)-4-[1-(2,6-dioxopiperidin-3-yl)-3-methyl-2-oxo-1,3-benzodiazol-5-yl]cyclohexyl] butanoic acid | 428.25 | (300 MHz, CD3OD) δ 7.06 (s, 1H), 7.03-7.00 (m, 2H), 5.34-5.31 (m, 1H), 3.46-3.42 (m, 3H), 2.97-2.75 (m, 3H), 2.59-2.55 (m, 1H), 2.29-2.26 (m, 2H), 2.22-2.13 (m, 1H), 1.96-1.91 (m, 4H), 1.72-1.68 (m, 2H), 1.56-1.52 (m, 2H), 1.40-1.27 (m, 3H), 1.16-1.32 (m, 2H) |

TABLE 42-continued

Characterization data for intermediates prepared according to above.

| Inter-mediate | Structure | Chemical Name | MS: $[(M + 1)]^+$ | $^1H$ NMR |
|---|---|---|---|---|
| G-4-144 | 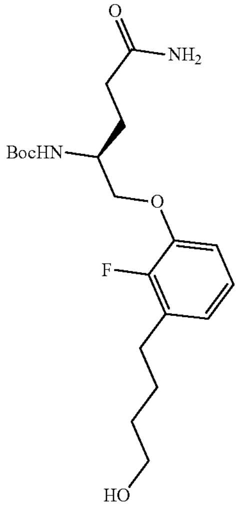 [SMILES: CC(C)(C)OC(=O)N[C@@H](CCC(N)=O)COc1cccc(CCCCO)c1F] | tert-butyl N-[(2S)-4-carbamoyl-1-[2-fluoro-3-(4-hydroxybutyl) phenoxy]butan-2-yl]carbamate | 399.30 | (400 MHz, DMSO-$d_6$) δ 7.27 (s, 1H), 7.06-6.93 (m, 2H), 6.85-6.81 (m, 2H), 6.74 (s, 1H), 4.37 (s, 1H), 3.91 (d, J = 6.1 Hz, 2H), 3.76-3.72 (m, 1H), 3.40 (t, J = 6.4 Hz, 2H), 2.59 (t, J = 7.6 Hz, 2H), 2.21-2.03 (m, 2H), 1.88-1.75 (m, 2H), 1.67-1.51 (m, 3H), 1.46-1.42 (m, 1H), 1.39 (s, 9H) |

(7Z)-9-[(2S)-2-[(tert-butoxycarbonyl)amino]-4-carbamoylbutoxy]non-7-enoic acid (Intermediate G-4-80)

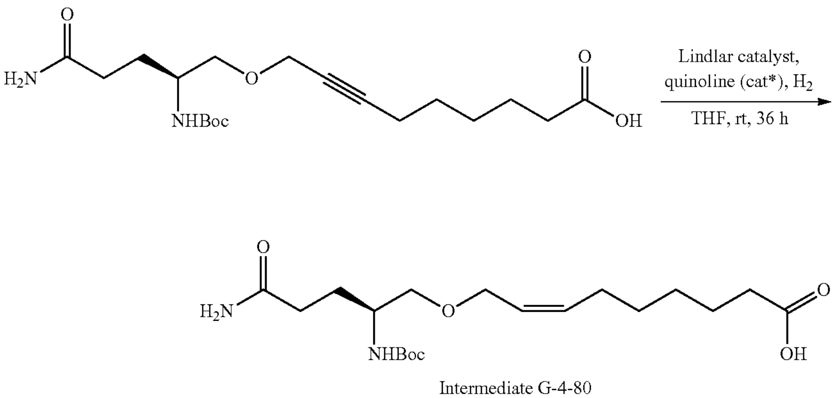

Intermediate G-4-80

To a solution of 9-[(2S)-2-[(tert-butoxycarbonyl)amino]-4-carbamoylbutoxy]non-7-ynoic acid (400.00 mg, 1.040 mmol) in THF (10.00 mL) was added Lindlar catalyst (429.70 mg, 0.104 mmol) and quinazoline (27.08 mg, 0.208 mmol) under nitrogen atmosphere. The mixture was hydrogenated at room temperature for 36 h under hydrogen atmosphere using a hydrogen balloon. It was filtered through a Celite pad. The filtrate was concentrated under reduced pressure to give the title compound as an off-white solid (340 mg, 80%): $^1H$ NMR (400 MHz, DMSO-d4) δ 11.96 (s, 1H), 7.22 (s, 1H), 6.76-6.67 (m, 1H), 6.60 (d, J 8.8 Hz, 1H), 5.55-5.41 (m, 2H), 4.00-3.94 (m, 2H), 3.28-3.03 (m, 2H), 2.28-2.13 (m, 3H), 2.08-1.99 (m, 4H), 1.77-1.64 (m, 1H), 1.54-1.44 (m, 2H), 1.43-1.40 (m, 1H), 1.38 (s, 9H), 1.37-1.23 (m, 4H). LC/MS (ESI, m/z): $[(M+1)]^+$=387.20.

4-[1-(2,6-Dioxopiperidin-3-yl)-3-methyl-2-oxo-1,3-benzodiazol-4-yl]butanoic acid (Intermediate G-4-81)

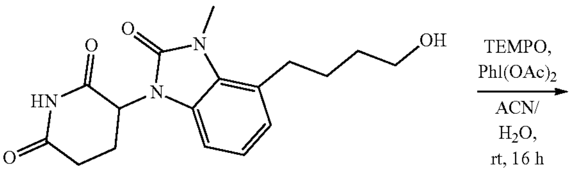

Intermediate B37

-continued

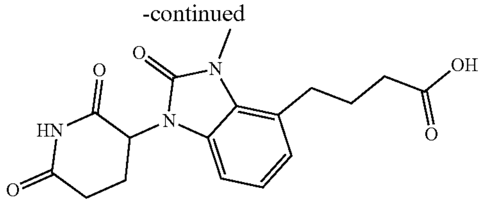

Intermediate G-4-81

To a stirred solution of 3-[4-(4-hydroxybutyl)-3-methyl-2-oxo-1,3-benzodiazol-1-yl]piperidine-2,6-dione (1.09 g, 3.289 mmol) in $CH_3CN$ (10.00 mL) and $H_2O$ (10.00 mL)

were added (acetyloxy)(phenyl)-lambda3-iodanyl acetate (2.33 g, 7.234 mmol) and TEMPO (0.13 g, 0.822 mmol) at room temperature under nitrogen atmosphere. The resulting mixture was stirred for overnight at room temperature under nitrogen atmosphere. The resulting mixture was concentrated under reduced pressure. The residue was purified by reverse phase flash chromatography with the following conditions: Column: WelFlash™ C18-I, 20~40 um, 330 g; Eluent A: water (plus 10 mmol/LFA); Eluent B: ACN; Gradient: 15% - 35% B in 20 min; Flow rate: 80 mL/min; Detector: UV 220/254 nm; desired fractions were collected at 28% B and concentrated under reduced pressure to afford the title compound as a white solid (900 mg, 79%): 1H NMR (400 MHz, DMSO-$d_6$) δ 12.11 (s, 1H), 11.09 (s, 1H), 6.98 (d, J=4.5 Hz, 2H), 6.91-6.84 (m, 1H), 5.37 (dd, J=12.5, 5.4 Hz, 1H), 3.56 (s, 3H), 2.96-2.83 (m, 3H), 2.78-2.66 (m, 1H), 2.64 (d, J=5.2 Hz, 1H), 2.34 (t, J=7.1 Hz, 2H), 2.04-1.97 (m, 1H), 1.89-1.78 (m, 2H); LC/MS (ESI, m/z): [(M+1)]+=346.05.

The intermediates in Table 43 were prepared according to the above procedure to prepare Intermediate G-4-81.

TABLE 43

Characterization data for intermediates prepared according to above.

| Intermediate | Structure | Chemical Name | MS: $[(M + 1)]^+$ | $^1$H-NMR |
|---|---|---|---|---|
| G-4-82 | 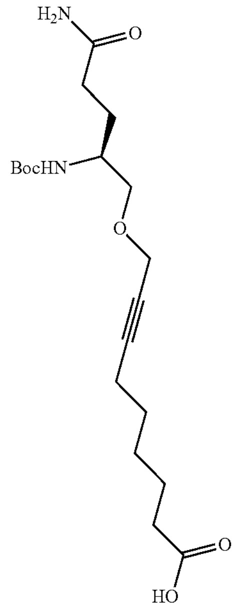 [SMILES: CC(C)(C)OC(=O)N[C@@H](CCC(N)=O)COCC#CCCCCCC(=O)O] | 9-[(2S)-2-[(tert-butoxycarbonyl) amino]-4-carbamoylbutoxy] non-7-ynoic acid | 385.15 | (400 MHz, DMSO-$d_6$) δ 11.98 (s, 1H), 7.23 (s, 1H), 6.72 (s, 1H), 6.63 (d, J = 8.7 Hz, 1H), 4.09 (t, J = 2.2 Hz, 2H), 3.50-3.48 (m, 1H), 3.35-3.28 (m, J = 8.4 Hz, 5H), 2.25-2.18 (m, J = 7.1, 3.4 Hz, 4H), 2.06-2.02 (m, 2H), 1.80-1.62 (m, 1H), 1.48-1.39 (m, 4H), 1.38 (s, 9H) |

4-[4-[1-(2,6-Dioxopiperidin-3-yl)-3-methyl-2-oxo-1,3-benzodiazol-5-yl]piperazin-1-yl]butanoic acid (Intermediate G-4-83)

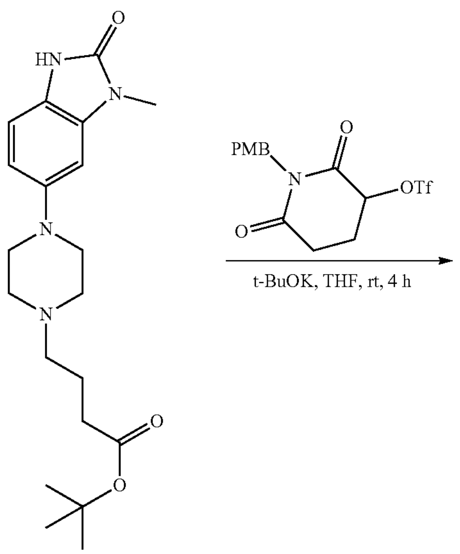

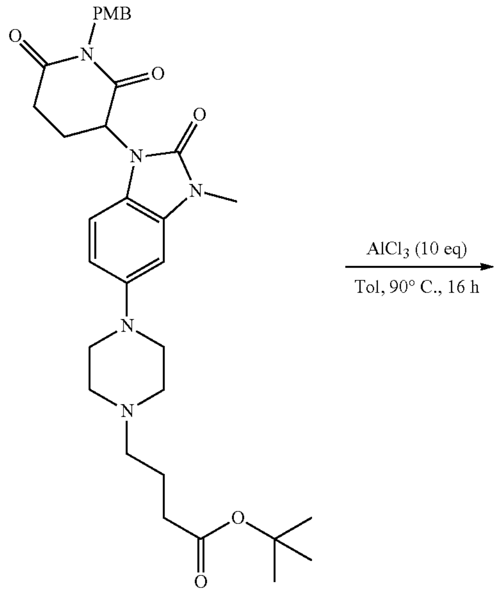

-continued

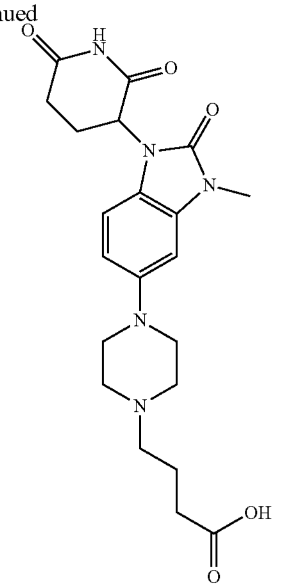

Intermediate G-4-83

Step 1. Tert-butyl 4-[4-(i-[i-[(4-methoxyphenyl)methyl]-2,6-dioxopiperidin-3-yl]-3-methyl-2-oxo-1,3-benzodiazol-5-yl)piperazin-1-yl]butanoate. To a stirred solution of tert-butyl 4-[4-(3-methyl-2-oxo-1H-1,3-benzodiazol-5-yl) piperazin-1-yl]butanoate (3.40 g, 9.079 mmol) in THF (70.00 mL) was added t-BuOK (1.53 g, 13.619 mmol) at 0° C. under nitrogen atmosphere. The resulting mixture was stirred for 1 h at 0° C. under nitrogen atmosphere. To the above mixture was added a solution of 1-[(4-methoxyphenyl)methyl]-2,6-dioxopiperidin-3-yltrifluoromethanesulfonate (4.50 g, 11.803 mmol) in THF (30.00 mL) at 0° C. under nitrogen atmosphere. The resulting mixture was stirred for 4 h at room temperature under nitrogen atmosphere. The reaction was quenched with sat. $NH_4Cl$ (100 mL) at 0° C. The resulting mixture was extracted with EtOAc (3×100 mL). The combined organic layers were washed with brine (100 mL) and dried over anhydrous $Na_2SO_4$. After filtration, the filtrate was concentrated under reduced pressure. The residue was purified by silica gel column chromatography, eluted with EtOAc to afford the title compound as a dark blue solid (2.2 g, 40%): $^1H$ NMR (400 MHz, DMSO-$d_6$) δ 7.25-7.14 (m, 2H), 6.90-6.79 (m, 4H), 6.60-6.55 (m, 1H), 5.44 (dd, J=13.1, 5.4 Hz, 1H), 4.74 (s, 2H), 3.73 (s, 3H), 3.31 (s, 3H), 3.15-3.02 (m, 6H), 2.85-2.78 (m, 1H), 2.75-2.65 (m, 1H), 2.56-2.51 (m, 2H), 2.39-2.28 (m, 2H), 2.27-2.22 (m, 2H), 2.07-1.99 (m, 2H), 1.73-1.64 (m, 2H), 1.41 (s 9H); LC/MS (ESI, m/z): $[(M+1)]^+$=606.35.

The intermediates in Table 44 were prepared according to step 1 of the procedure to prepare Intermediate G-4-83.

TABLE 44

| Characterization data for intermediates prepared according to above. | | | | |
|---|---|---|---|---|
| Intermediate | Structure | Chemical Name | MS: $[(M + 1)]^+$ | $^1$H-NMR |
| G-10-1 | 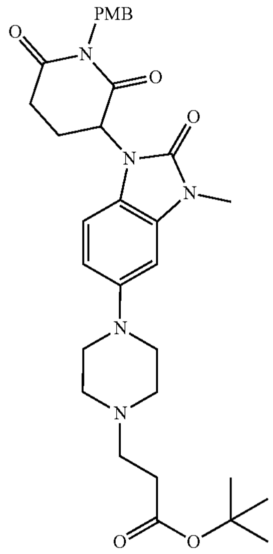 | tert-butyl 3-[4-(1-[1-[(4-methoxyphenyl) methyl]-2,6-dioxopiperidin-3-yl]-3-methyl-2-oxo-1,3-benzodiazol-5-yl)piperazin-1-yl]propanoate | 592.40 | (400 MHz, DMSO-$d_6$) δ 7.25-7.17 (m, 2H), 6.90-6.79 (m, 4H), 6.60-6.54 (m, 1H), 5.44 (dd, J = 13.1, 5.4 Hz, 1H), 4.76 (s, 2H), 3.73 (s, 3H), 3.31 (s, 3H), 3.11-3.04 (m, 4H), 2.87-2.67 (m, 4H), 2.60-2.54 (m, 4H), 2.41 (t, J = 7.0 Hz, 2H), 2.10-1.96 (m, 2H), 1.42 (s, 9H) |

Step 2. 4-[4-[1-(2,6-Dioxopiperidin-3-yl)-3-methyl-2-oxo-1,3-benzodiazol-5-yl]piperazin-1-yl]butanoic acid. To a stirred solution of tert-butyl 4-[4-(1-[1-[(4-methoxyphenyl) methyl]-2,6-dioxopiperidin-3-yl]-3-methyl-2-oxo-1,3-benzodiazol-5-yl)piperazin-1-yl]butanoate (500.00 mg, 0.825 mmol) in toluene (50.00 mL) was added $AlCl_3$ (1100.65 mg, 8.254 mmol) at room temperature under nitrogen atmosphere. The resulting mixture was stirred for overnight at 90° C. under nitrogen atmosphere. The reaction was cooled down to room temperature and quenched with water (50 mL) at 0° C. The aqueous layer was extracted with EtOAc (3×50 mL). The aqueous layer was purified by reverse phase flash chromatography with the following conditions: Column: WelFlash™ C18-I, 20~40 um, 330 g; Eluent A: water (plus 10 mmol/LFA); Eluent B: ACN; Gradient: 10% - 30% B in 15 min; Flow rate: 80 mL/min; Detector: UV 220/254 nm; desired fractions were collected at 17% B and concentrated under reduced pressure to afford the title compound as a light yellow oil (210 mg, 59%): $^1$H NMR (400 MHz, DMSO-$d_6$) δ 11.07 (s, 1H), 6.97 (d, J=8.6 Hz, 1H), 6.88 (s, 1H), 6.66 (d, J=8.7 Hz, 1H), 5.30 (dd, J=12.9, 5.4 Hz, 1H), 3.32 (s, 3H), 3.24-3.18 (m, 4H), 2.93-2.83 (m, 4H), 2.76-2.57 (m, 4H), 2.31 (t, J=7.2 Hz, 2H), 2.11-1.87 (m, 2H), 1.86-1.72 (m, 2H); LC/MS (ESI, m/z): $[(M+1)]^+$=430.10

The intermediates in Table 45 were prepared according to step 2 of the procedure to prepare Intermediate G-4-83.

TABLE 45

| Characterization data for intermediates prepared according to above. | | | | |
|---|---|---|---|---|
| Intermediate | Structure | Chemical Name | MS: $[(M + 1)]^+$ | $^1$H-NMR |
| G-4-84 | 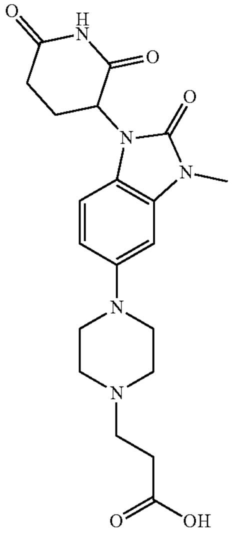 [SMILES: Cn1c(=O)n(C2CCC(=O)NC2=O)c2ccc(N3CCN(CCC(=O)O)CC3)cc21] | 3-[4-[1-(2,6-dioxopiperidin-3-yl)-3-methyl-2-oxo-1,3-benzodiazol-5-yl]piperazin-1-yl]propanoic acid | 416.10 | (400 MHz, DMSO-$d_6$) δ 11.06 (s, 1H), 6.95 (d, J = 8.6 Hz, 1H), 6.85 (s, 1H), 6.63 (d, J = 8.6 Hz, 1H), 5.30 (dd, J = 12.9, 5.4 Hz, 1H), 3.34 (s, 3H), 3.12-3.06 (m, 4H), 2.97-2.83 (m, 2H), 2.76-2.58 (m, 8H), 2.45 (t, J = 7.1 Hz, 2H) |

Step 5. (9H-fluoren-9-yl)methyl ((3S,6S)-6-(((2R,3S)-6-amino-2-((4-(16-(1-(2,6-dioxopiperidin-3-yl)-3-methyl-2-oxo-2,3-dihydro-1H-benzo[d]imidazol-5-yl)-5-oxo-7,10,13-trioxa-4-azahexadecyl)benzyl)oxy)-6-oxohexan-3-yl)carbamoyl)-4-oxo-1,2,3,4,6,7-hexahydroazepino[3,2,1-hi]indol-3-yl)carbamate (Intermediate G). To a solution of (9H-fluoren-9-yl)methyl ((3S,6S)-6-(((2R,3S)-6-amino-2-((4-(3-aminopropyl)benzyl)oxy)-6-oxohexan-3-yl)carbamoyl)-4-oxo-1,2,3,4,6,7-hexahydroazepino[3,2,1-hi]indol-3-yl)carbamate hydrochloride (300 mg, 0.39 mmol) in DMA (10.0 mL) were added 2-(2-(2-(3-(1-(2,6-dioxopiperidin-3-yl)-3-methyl-2-oxo-2,3-dihydro-1H-benzo[d]imidazol-5-yl)propoxy)ethoxy)ethoxy)acetic acid (179 mg, 0.39 mmol), TEA (118 mg, 1.17 mmol) and HATU (190 mg, 0.50 mmol) at 0° C. under nitrogen atmosphere. The resulting mixture was stirred for 16 hours at room temperature under nitrogen atmosphere. The mixture was concentrated under reduced pressure. The residue was purified by reversed phase flash chromatography with the following conditions: column, C18 silica gel; Mobile phase A: water (plus 10 mmol/L AcOH); Mobile phase B: CAN. Gradient (B%): 40% to 60% in 20 min; Detector: UV 254/220 nm; desired fractions were collected at 58% B and concentrated under reduced pressure to afford the title compound as a white solid (229 mg, 50%): $^1$H NMR (400 MHz, DMSO-$d_6$) δ 11.09 (s, 1H), 7.92-7.85 (m, 3H), 782-7.74 (m, 3H), 7.43 (t, J=7.4 Hz, 2H), 7.34 (t, J=7.4 Hz, 2H), 7.23-7.14 (m, 3H), 7.13-7.04 (m, 3H), 7.06-6.93 (m, 4H), 6.85 (d, J=8.0 Hz, 1H), 6.70 (s, 1H), 5.76 (s, 1H), 5.33 (dd, J=12.6, 5.4 Hz, 1H), 5.05 (d, J=10.5 Hz, 1H), 4.39 (s, 2H), 4.25 (d, J=7.0 Hz, 2H), 3.88 (s, 2H), 3.58 (s, 3H), 3.56-3.47 (m, 3H), 3.42 (d, J=5.5 Hz, 2H), 3.40-3.34 (m, 12H), 3.31 (s, 2H), 3.10 (s, 2H), 2.86 (s, 2H), 2.68-2.52 (m, 4H), 2.08 (s, 6H), 1.69 (s, 4H), 1.06 (d, J=6.2 Hz, 3H); MS (ESI, m/z): [(M+1)]$^+$=1189.70.

The following intermediates in Table 46 were prepared according to Step 5 above to prepare Intermediate G.

TABLE 46

Characterization data for intermediates prepared according to above.

| Inter-mediate | Structure | Chemical Name | MS: [(M + 1)]$^+$ | $^1$H NMR |
|---|---|---|---|---|
| G1 | 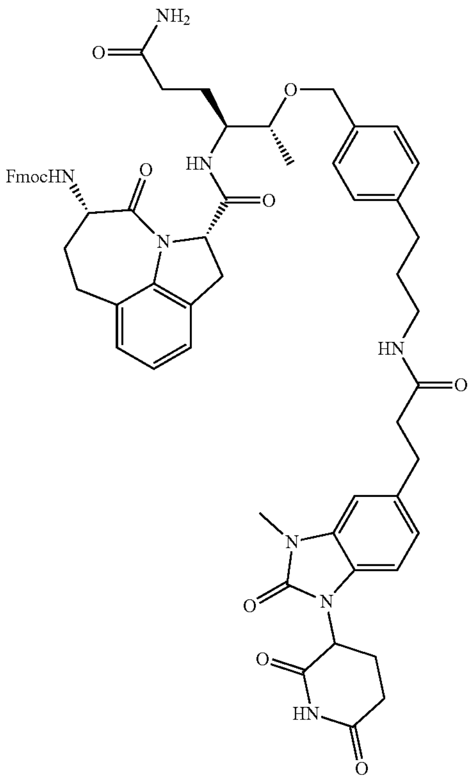 | (9H-fluoren-9-yl)methyl N-[(2S,11S)-2-[[(3S,4R)-1-carbamoyl-4-[[4-(3-[3-[1-(2,6-dioxopiperidin-3-yl)-3-methyl-2-oxo-2,3-dihydro-1H-1,3-benzodiazol-5-yl]propanamido]propyl)phenyl]methoxy]pentan-3-yl]carbamoyl]-12-oxo-1-azatricyclo[6.4.1.0^[4,13]]trideca-4(13),5,7-trien-11-yl]carbamate | 1057.6 | (400 MHz, DMSO-$d_6$) δ 7.91 (d, J = 7.5 Hz, 2H), 7.87 (d, J = 6.0 Hz, 2H), 7.76 (t, J = 7.1 Hz, 2H), 7.43 (t, J = 7.4 Hz, 2H), 7.35 (t, J = 7.5 Hz, 2H), 7.33-7.14 (m, 3H), 7.10-7.03 (m, 4H), 7.00 (d, J = 8.2 Hz, 1H), 5.33 (dd, J = 13.0, 5.4 Hz, 1H), 5.06 (d, J = 10.9 Hz, 1H), 4.41 (s, 2H), 4.27 (t, J = 6.3 Hz, 2H), 4.13 (s, 1H), 3.44 (d, J = 5.9 Hz, 2H), 3.10-2.98 (m, 3H), 2.90-2.80 (m, 3H), 2.70-2.56 (m, 2H), 2.41 (t, J = 7.7 Hz, 2H), 2.1-2.00 (m, 4H), 1.78 (s, 1H), 1.64 (q, J = 7.4 Hz, 2H), 1.08 (d, J = 6.2 Hz, 3H). |

TABLE 46-continued

Characterization data for intermediates prepared according to above.

| Inter-mediate | Structure | Chemical Name | MS: [(M + 1)]+ | 1H NMR |
|---|---|---|---|---|
| G2 | 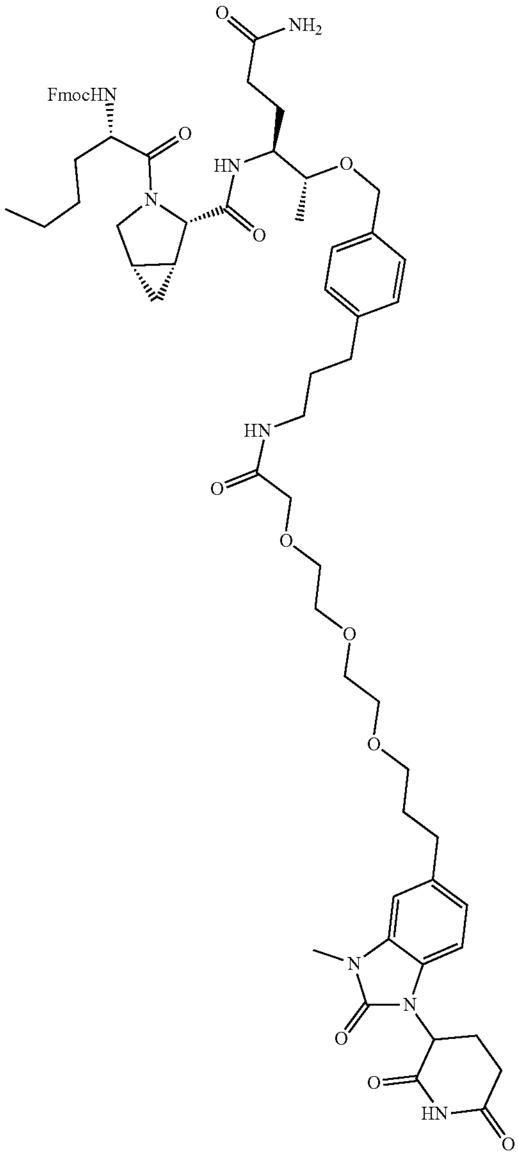 | (9H-fluoren-9-yl)methyl N-[(2S)-1-[(1R,2S,5S)-2-[[(3S,4R)-1-carbamoyl-4-[[4-(3-[2-[2-(2-[3-[1-(2,6-dioxopiperidin-3-yl)-3-methyl-2-oxo-2,3-dihydro-1H-1,3-benzodiazol-5-yl]propoxy]ethoxy)ethoxy]acetamido]propyl)phenyl]methoxy]pentan-3-yl]carbamoyl]-3-azabicyclo[3.1.0]hexan-3-yl]-1-oxohexan-2-yl]carbamate | 1183.8 | (400 MHz, DMSO-$d_6$) δ 11.09 (s, 1H), 7.90 (d, J = 7.5 Hz, 2H), 7.80-7.65 (m, 3H), 7.59 (dd, J = 12.1, 8.3 Hz, 2H), 7.42 (t, J = 7.5 Hz, 2H), 7.33 (t, J = 7.1 Hz, 2H), 7.30-7.20 (m, 3H), 7.14 (d, J = 7.8 Hz, 2H), 7.08-6.97 (m, 3H), 6.86 (d, J = 7.8 Hz, 1H), 4.50-4.33 (m, 3H), 4.29-4.19 (m, 2H), 3.88 (s, 3H), 3.60-3.46 (m, 5H), 3.42-3.35 (m, 3H), 3.35-3.29 (m, 6H), 3.11 (q, J = 6.7 Hz, 2H), 2.76-2.58 (m, 5H), 2.54 (s, 2H), 2.10-2.04 (m, 9H), 1.87-1.67 (m, 6H), 1.52 (s, 3H), 1.33-1.22 (m, 4H), 1.08 (d, J = 6.1 Hz, 3H), 0.86 (t, J = 7.0 Hz, 3H), 0.56 (s, 2H). |

TABLE 46-continued

| Characterization data for intermediates prepared according to above. | | | | |
|---|---|---|---|---|
| Intermediate | Structure | Chemical Name | MS: [(M + 1)]+ | $^1$H NMR |
| G3 | 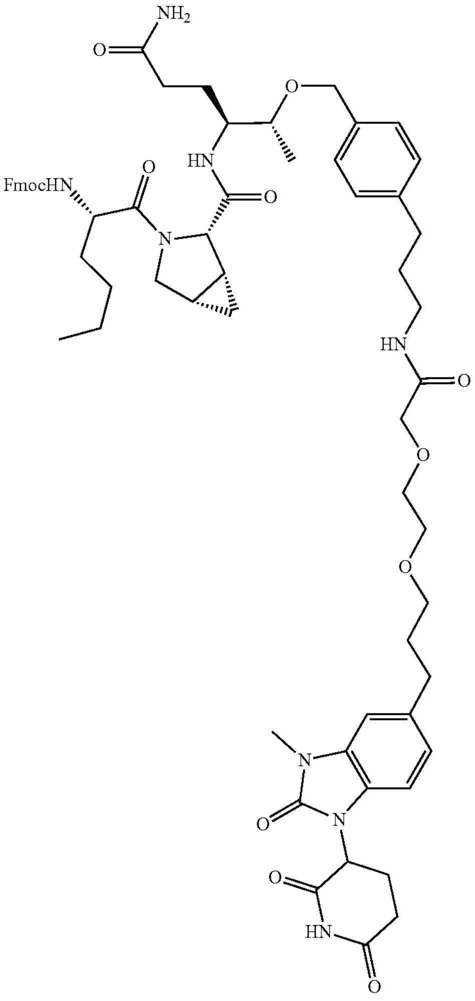 | (9H-fluoren-9-yl)methyl N-[(2S)]-1-[(1R,2S,5S)-2-[[(3S,4R)-1-carbamoyl-4-[(4-[3-[2-(2-[3-[1-(2,6-dioxopiperidin-3-yl)-3-methyl-2-oxo-2,3-dihydro-1H-1,3-benzodiazol-5-yl]propoxy]ethoxy)acetamido]propyl]phenyl)methoxy]pentan-3-yl]carbamoyl]-3-azabicyclo[3.1.0]hexan-3-yl]-1-oxohexan-2-yl]carbamate | 1139.8 | (400 MHz, DMSO-$d_6$) δ 11.09 (s, 1H), 7.90 (d, J = 7.6 Hz, 2H), 7.75-7.70 (d, J = 6.2 Hz, 2H), 7.60 (d, J = 8.6 Hz, 1H), 7.42 (t, J = 7.5 Hz, 2H), 7.34 (d, J = 7.4 Hz, 2H), 7.32-7.20 (m, 3H), 7.16-7.10 (m, 3H), 7.08-6.97 (m, 3H), 6.87 (d, J = 8.5 Hz, 1H), 6.67 (s, 1H), 5.34 (dd, J = 12.6, 5.3 Hz, 1H), 4.47 (d, J = 11.7 Hz, 1H), 4.41 (d, J = 11.3 Hz, 1H), 4.36 (d, J = 5.5 Hz, 1H), 4.26 (d, J = 11.4 Hz, 1H), 4.22 (d, J = 6.5 Hz, 2H), 4.10 (d, J = 6.7 Hz, 1H), 3.90 (s, 2H), 3.87 (s, 1H), 3.71 (s, 1H), 3.62-3.53 (m, 6H), 3.44-3.35 (m, 3H), 3.12 (q, J = 6.8 Hz, 2H), 2.90 (t, J = 14.9 Hz, 1H), 2.77-2.59 (m, 3H), 2.54 (d, J = 1.9 Hz, 9H), 2.11 (d, J = 8.1 Hz, 2H), 2.08 (s, 2H), 1.87-1.79 (m, 2H), 1.77-1.67 (m, 3H), 1.52 (s, 3H), 1.33-1.22 (m, 4H), 1.08 (d, J = 6.2 Hz, 3H), 0.87 (d, J = 7.2 Hz, 2H). |

TABLE 46-continued

| Characterization data for intermediates prepared according to above. | | | | |
|---|---|---|---|---|
| Inter-mediate | Structure | Chemical Name | MS: [(M + 1)]$^+$ | $^1$H NMR |
| G4 | 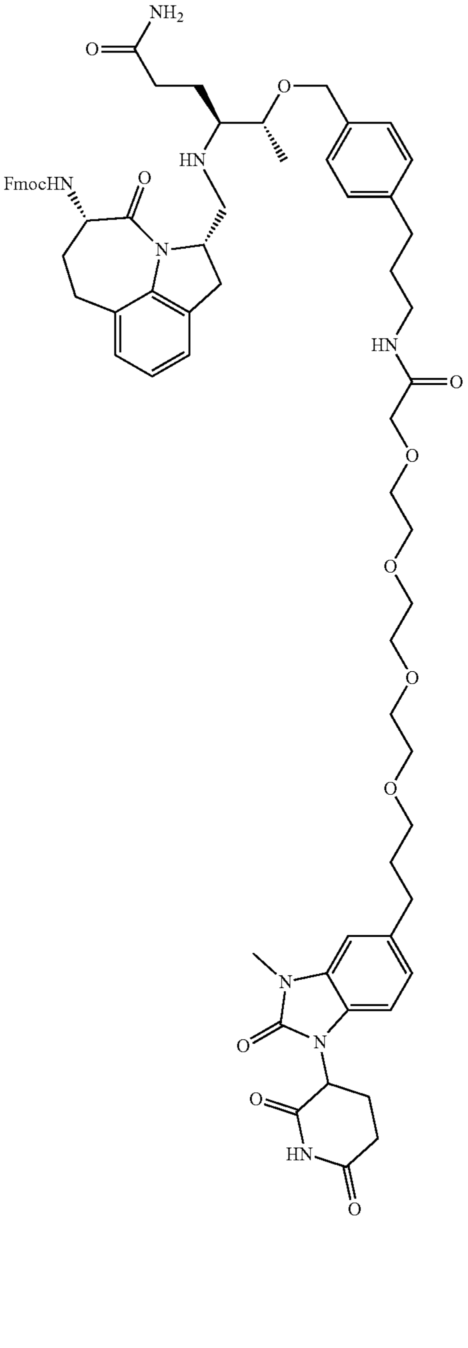 | (9H-fluoren-9-yl)methyl N-[(2S,11S)-2-[[(3S,4R)-1-carbamoyl-4-[[4-(3-[15-[1-(2,6-dioxopiperidin-3-yl)-3-methyl-2-oxo-2,3-dihydro-1H-1,3-benzodiazol-5-yl]-3,6,9,12-tetraoxapenta-decanamido]propyl) phenyl]methoxy] pentan-3-yl]carbamoyl]-12-oxo-1-azatricyclo[6.4.1.0]^[4,13]trideca-4(13),5,7-trien-11-yl]carbamate | 1233.7 | (400 MHz, DMSO-$d_6$) δ 11.09 (s, 1H), 7.95-7.81 (m, 3H), 7.81-7.69 (m, 4H), 7.43 (t, J = 7.5 Hz, 2H), 7.34 (t, J = 7.5 Hz, 2H), 7.20-6.92 (m, 10H), 6.86 (d, J = 7.9 Hz, 1H), 6.70 (s, 1H), 5.34 (dd, J = 12.7, 5.4 Hz, 1H), 5.06 (d, J = 10.4 Hz, 1H), 4.40 (s, 2H), 4.32-4.23 (m, 2H), 4.13 (s, 1H), 3.87 (s, 2H), 3.81-3.75 (m, 1H), 3.68-3.53 (m, 9H), 3.54-3.41 (m, 6H), 3.44-3.35 (m, 1H), 3.32 (s, 3H), 3.21-3.08 (m, 3H), 3.05 (s, 1H), 2.86 (t, J = 14.4 Hz, 2H), 2.76-2.52 (m, 8H), 2.11-2.06 (m, 3H), 2.01 (s, 2H), 1.88-1.73 (m, 4H), 1.56 (s, 1H), 1.07 (d, J = 6.3 Hz, 3H). |

TABLE 46-continued

| Characterization data for intermediates prepared according to above. | | | | |
|---|---|---|---|---|
| Inter-mediate | Structure | Chemical Name | MS: [(M + 1)]$^+$ | $^1$H NMR |
| G5 | 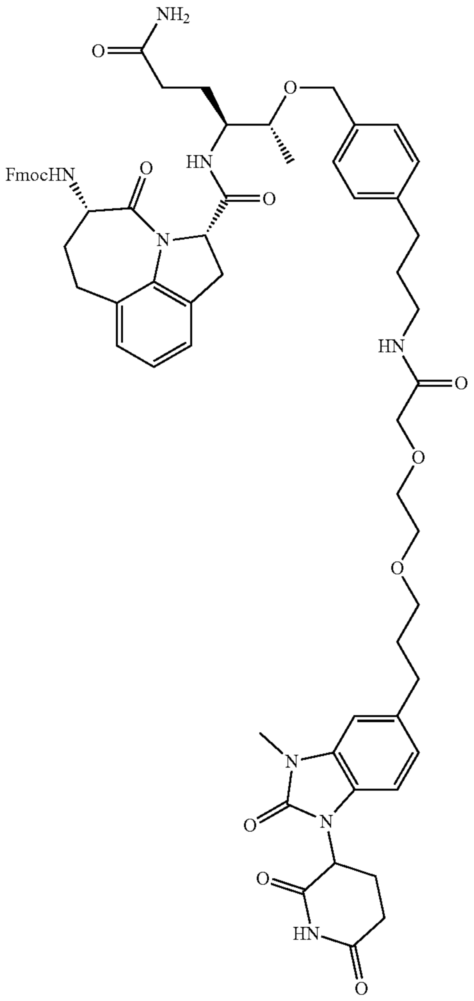 | (9H-fluoren-9-yl)methyl N-[(2S,11S)-2-[[(3S,4R)-1-carbamoyl-4-[(4-[3-[2-(2-[3-[1-(2,6-dioxopiperidin-3-yl)-3-methyl-2-oxo-2,3-dihydro-1H-1,3-benzodiazol-5-yl]propoxy]ethoxy)acetamido]propyl]phenyl)methoxy]pentan-3-yl]carbamoyl]-12-oxo-1-azatricyclo-[6.4.1.0^[4,13]]trideca-4(13),5,7-trien-11-yl]carbamate | 1145.8 | (400 MHz, DMSO-$d_6$) δ 11.08 (s, 1H), 7.94-7.81 (m, 3H), 7.80-7.65 (m, 3H), 7.46-7.31 (m, 4H), 7.25-7.12 (m, 3H), 7.09 (dd, J = 8.0, 3.5 Hz, 2H), 7.06-6.97 (m, 4H), 6.93 (dd, J = 15.1, 7.7 Hz, 1H), 6.85 (dd, J = 8.2, 1.5 Hz, 1H), 6.70 (s, 1H), 6.28 (s, 1H), 5.33 (dd, J = 12.7, 5.3 Hz, 1H), 5.09-5.02 (m, 1H), 4.39 (s, 2H), 4.29 (s, 2H), 4.12 (s, 1H), 3.89 (s, 2H), 3.77 (s, 1H), 3.70-3.57 (m, 4H), 3.50-3.38 (m, 5H), 3.37-3.25 (m, 3H), 3.12 (q, J = 6.7 Hz, 2H), 3.07-2.99 (m, 1H), 2.95-2.80 (m, 2H), 2.74-2.60 (m, 4H), 2.54 (d, J = 7.5 Hz, 2H), 2.15-1.99 (m, 6H), 1.92-1.65 (m, 5H), 1.53 (s, 1H), 1.07 (dd, J = 6.1, 1.8 Hz, 3H). |

TABLE 46-continued

| Characterization data for intermediates prepared according to above. | | | | |
|---|---|---|---|---|
| Intermediate | Structure | Chemical Name | MS: [(M + 1)]+ | ¹H NMR |
| G6 | 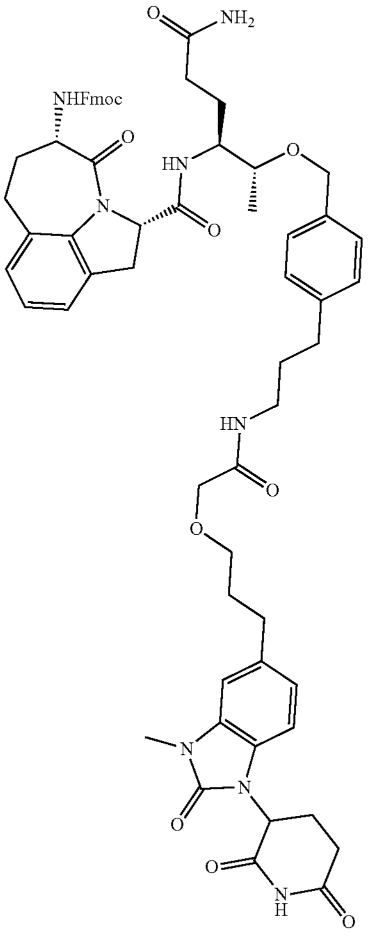 | (9H-fluoren-9-yl)methyl N-[(2S,11S)-2-[[(3S,4R)-1-carbamoyl-4-([4-[3-(2-[3-[1-(2,6-dioxopiperidin-3-yl)-3-methyl-2-oxo-2,3-dihydro-1H-1,3-benzodiazol-5-yl]propoxy]acetamido)propyl]phenyl]methoxy)pentan-3-yl]carbamoyl]-12-oxo-1-azatricyclo[6.4.1.0^[4,13]]trideca-4(13),5,7-trien-11-yl]carbamate | 1101.7 | (400 MHz, DMSO-d6) δ 11.09 (s, 1H), 7.90 (d, J = 7.5 Hz, 2H), 7.88 (dd, J = 19.4, 8.4 Hz, 2H), 7.39 (dt, J = 34.0, 7.4 Hz, 3H), 7.22-7.07 (m, 5H), 7.07-6.93 (m, 4H), 6.93-6.85 (m, 1H), 6.71 (s, 1H), 5.34 (dd, J = 12.6, 5.3 Hz, 1H), 5.05 (d, J = 10.7 Hz, 1H), 4.40 (s, 2H), 4.31-4.20 (m, 2H), 3.96-3.82 (m, 3H), 3.52-3.41 (m, 3H), 3.22-3.07 (m, 3H), 2.86 (t, J = 15.2 Hz, 2H), 2.76-2.61 (m, 3H), 2.61-2.51 (m, 9H), 2.14-2.04 (m, 7H), 1.94-1.83 (m, 2H), 1.72 (q, J = 7.4 Hz, 3H), 1.55 (s, 1H), 1.08 (d, J = 6.2 Hz, 3H). |

TABLE 46-continued

Characterization data for intermediates prepared according to above.

| Inter-mediate | Structure | Chemical Name | MS: [(M + 1)]+ | 1H NMR |
|---|---|---|---|---|
| G7 | 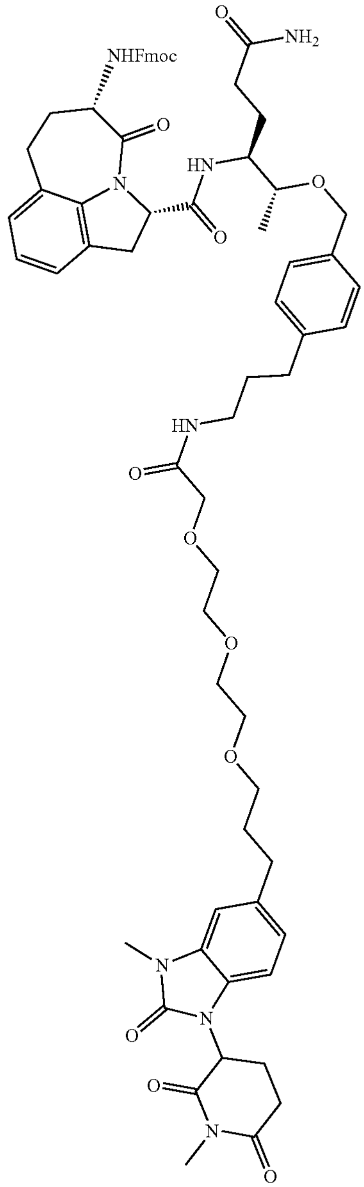 | 9H-fluoren-9-ylmethyl N-[(2S,11S)-2-[[(3S,4R)-1-carbamoyl-4-[[4-(3-[2-[2-(2-[3-[3-methyl-1-(1-methyl-2,6-dioxopiperidin-3-yl)-2-oxo-1,3-benzodiazol-5-yl]propoxy]ethoxy)ethoxy]acetamido]propyl)phenyl]methoxy]pentan-3-yl]carbamoyl]-12-oxo-1-azatricyclo[6.4.1.0]^[4,13]]trideca-4(13),5,7-trien-11-yl]carbamate | 1203.9 | (400 MHz, DMSO-$d_6$) δ 7.90 (d, J = 7.6 Hz, 2H), 7.84 (d, J = 9.2 Hz, 1H), 7.74 (dt, J = 15.1, 6.9 Hz, 4H), 7.43 (t, J = 7.5 Hz, 2H), 7.34 (t, J = 7.4 Hz, 2H), 7.16 (d, J = 6.9 Hz, 3H), 7.13-6.92 (m, 7H), 6.85 (dd, J = 8.2, 1.5 Hz, 1H), 6.69 (s, 1H), 5.40 (dd, J = 13.0, 5.3 Hz, 1H), 5.06 (d, J = 11.0 Hz, 1H), 4.40 (s, 2H), 4.27 (t, J = 6.3 Hz, 2H), 4.13 (s, 1H), 3.88 (s, 2H), 3.78 (s, 1H), 3.61-3.49 (m, 6H), 3.53-3.43 (m, 2H), 3.46-3.35 (m, 3H), 3.32 (s, 5H), 3.12 (q, J = 6.7 Hz, 2H), 3.03 (s, 3H), 3.02-2.91 (m, 1H), 2.85 (d, J = 16.7 Hz, 1H), 2.77-2.60 (m, 4H), 2.55 (d, J = 8.0 Hz, 3H), 2.08 (s, 6H), 2.12-1.96 (m, 1H), 1.76 (dp, J = 39.7, 6.9 Hz, 4H), 1.55 (s, 1H), 1.07 (d, J = 6.2 Hz, 3H). |

TABLE 46-continued

| Characterization data for intermediates prepared according to above. | | | | |
|---|---|---|---|---|
| Inter-mediate | Structure | Chemical Name | MS: [(M + 1)]+ | $^1$H NMR |
| G8 | 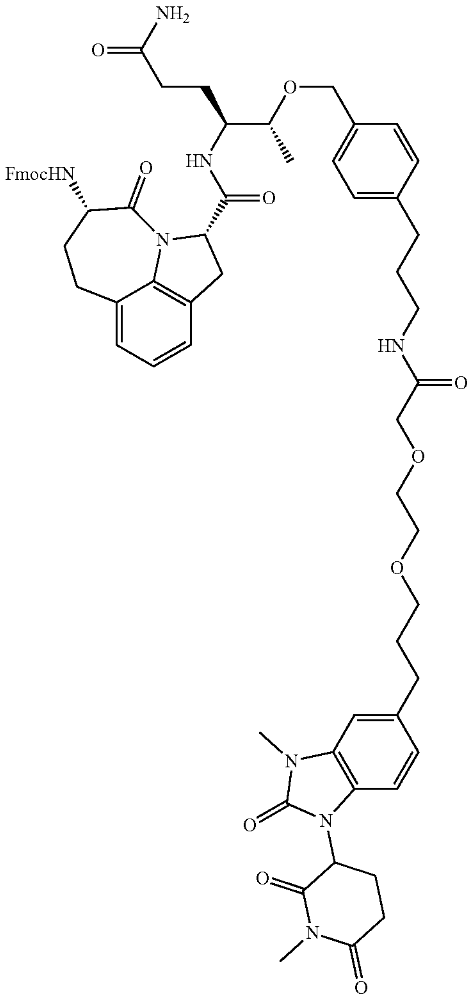 | 9H-fluoren-9-ylmethyl N-[(2S,11S)-2-[[(3S,4R)-1-carbamoyl-4-[(4-[3-[2-(2-[3-[3-methyl-1-(1-methyl-2,6-dioxopiperidin-3-yl)-2-oxo-1,3-benzodiazol-5-yl]propoxy]ethoxy)acetamido]propyl]phenyl)methoxy]pentan-3-yl]carbamoyl]-12-oxo-1-azatricyclo[6.4.1.0^[4,13]]trideca-4(13),5,7-trien-11-yl]carbamate | 1159.9 | (400 MHz, DMSO-$d_6$) δ 7.90 (d, J = 7.5 Hz, 2H), 7.84 (d, J = 9.2 Hz, 1H), 7.75 (dd, J = 12.7, 6.7 Hz, 4H), 7.43 (t, J = 7.3 Hz, 2H), 7.34 (t, J = 7.4 Hz, 2H), 7.16 (d, J = 7.4 Hz, 3H), 7.10 (d, J = 7.8 Hz, 2H), 7.07-7.01 (m, 3H), 6.99 (dd, J = 14.3, 7.7 Hz, 2H), 6.85 (dd, J = 8.0, 1.6 Hz, 1H), 6.69 (s, 1H), 5.76 (s, 4H), 5.40 (dd, J = 13.0, 5.3 Hz, 1H), 5.06 (d, J = 10.3 Hz, 1H), 4.39 (s, 2H), 4.27 (t, J = 6.4 Hz, 3H), 4.13(s, 1H), 3.90 (s, 2H), 3.78 (s, 2H), 3.64-3.51 (m, 5H), 3.43 (q, J = 6.0 Hz, 4H), 3.13 (q, J = 6.6 Hz, 3H), 3.03 (s, 4H), 3.01-2.91 (m, 1H), 2.89-2.77 (m, 2H), 2.77-2.61 (m, 4H), 2.55 (d, J = 7.9 Hz, 2H), 2.11-1.96 (m, 1H), 1.83 (p, J = 6.6 Hz, 2H), 1.71 (p, J = 7.4 Hz, 2H), 1.55 (d, J = 11.2 Hz, 1H), 1.07 (d, J = 6.2 Hz, 3H). |

TABLE 46-continued

| Characterization data for intermediates prepared according to above. | | | | |
|---|---|---|---|---|
| Inter-mediate | Structure | Chemical Name | MS: [(M + 1)]+ | $^1$H NMR |
| G9 | 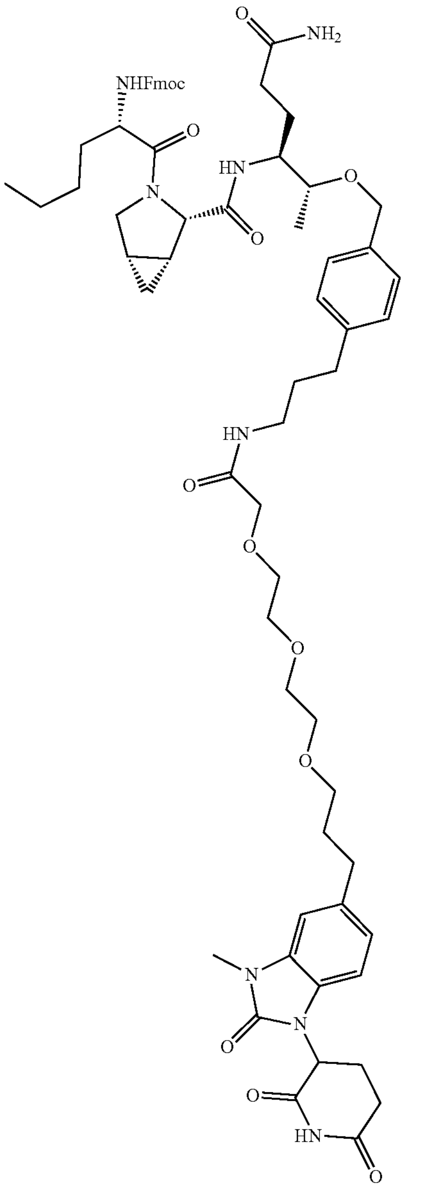 | 9H-fluoren-9-ylmethyl N-[(2S,11S)-2-[[(3S,4R)-1-carbamoyl-4-[[4-(3-[3-[1-(2,6-dioxopiperidin-3-yl)-3-methyl-2-oxo-1,3-benzodiazol-4-yl]propoxy]propyl)phenyl]methoxy]pentan-3-yl]carbamoyl]-12-oxo-1-azatricyclo-[6.4.1.0^[4,13]]trideca-4(13),5,7-trien-11-yl]carbamate | 1183.8 | (400 MHz, DMSO-$d_6$) δ 11.08 (s, 1H), 7.90 (d, J = 7.6 Hz, 2H), 7.83 (d, J = 9.1 Hz, 1H), 7.74 (q, J = 8.0, 7.5 Hz, 3H), 7.42 (t, J = 7.4 Hz, 2H), 7.34 (t, J = 7.4 Hz, 2H), 7.14 (d, J = 7.9 Hz, 2H), 7.04 (d, J = 7.8 Hz, 2H), 6.99-6.91 (m, 3H), 6.90-6.84 (m, 1H), 6.68 (s, 1H), 5.36 (dd, J = 12.6, 5.4 Hz, 1H), 5.06 (d, J = 10.5 Hz, 1H), 4.41 (s, 2H), 4.27 (dd, J = 12.6, 6.9 Hz, 2H), 4.12 (s, 1H), 3.78 (s, 3H), 3.57 (d, J = 9.7 Hz, 7H), 3.40 (dt, J = 19.8, 6.2 Hz, 5H), 3.06 (d, J = 14.5 Hz, 1H), 2.97 (t, J = 7.8 Hz, 2H), 2.86 (d, J = 16.6 Hz, 2H), 2.77-2.66 (m, 2H), 2.66-2.58 (m, 3H), 2.18-2.08 (m, 10 H), 2.01 (s, 3H), 1.82 (dt, J = 15.2, 7.6 Hz, 6H), 1.55 (s, 2H), 1.35-1.23 (m, 4H), 1.08 (d, J = 6.2 Hz, 3H). |

Tert-butyl N-[(3S,4R)-1-carbamoyl-4-[[4-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methyl)phenyl]methoxy]pentan-3-yl]carbamate (Intermediate G10)

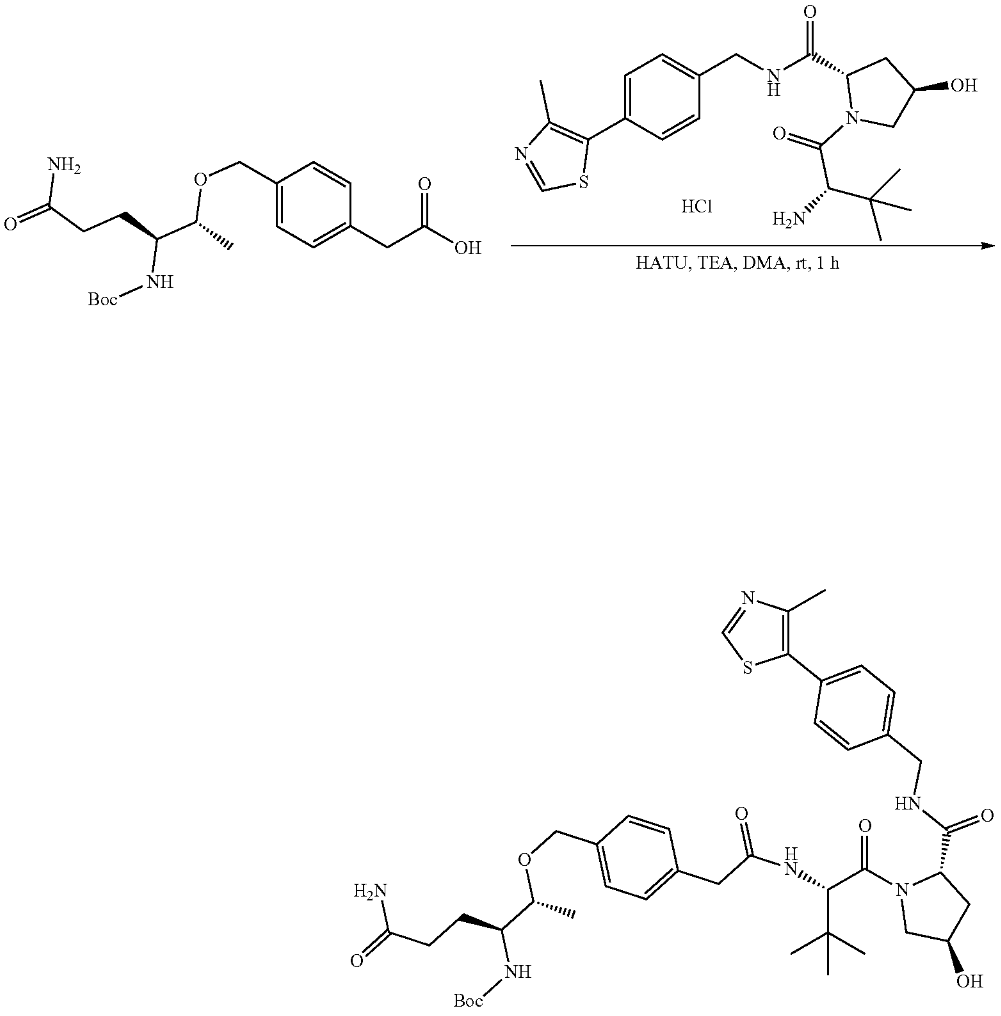

Intermediate G10

To a solution of (2S,4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide hydrochloride (302 mg, 0.65 mmol) in DMA (3.00 mL) were added [4-([[(2R,3S)-3-[(tert-butoxycarbonyl)amino]-5-carbamoylpentan-2-yl]oxy]methyl)phenyl]acetic acid (150 mg, 0.38 mmol), TEA (154 mg, 1.52 mmol) and HATU (188 mg, 0.49 mmol) at 25° C. under nitrogen atmosphere. After stirring for additional 1 hour, the resulting mixture was purified by reversed phase flash chromatography with the following conditions: Column: WelFlash™ C18-I, 20~40 um, 330 g; Eluent A: water (plus 10 mmol/L AcOH); Eluent B: ACN; Gradient: 35% - 55% B in 25 min; Flow rate: 80 mL/min; Detector: UV 254/220 nm; desired fractions were collected at 46% B and concentrated under reduced pressure to afford the title compound as a white foam (200 mg, 65%): $^{1}$H NMR (400 MHz, $CDCl_3$) δ 8.79 (s, 1H), 7.66 (s, 1H), 7.41-7.25 (m, 6H), 7.21 (d, J=7.4 Hz, 2H), 6.43-6.11 (m, 2H), 5.82 (s, 1H), 4.83 (d, J=9.2 Hz, 1H), 4.69 (s, 1H), 4.65-4.44 (m, 4H), 4.44-4.27 (m, 2H), 4.02 (d, J=11.0 Hz, 1H), 3.74-3.52 (m, 4H), 2.52 (s, 3H), 2.44 (s, 1H), 2.23 (s, 2H), 2.14 (d, J=9.3 Hz, 1H), 2.01 (s, 3H), 1.66 (s, 1H), 1.43 (s, 9H), 1.18 (d, J=5.7 Hz, 3H), 0.87 (s, 9H); MS (ESI, m/z): $[(M+1)]^+$=807.35.

The following intermediates in Table 47 were prepared according to the above procedure to prepare Intermediate G10.

TABLE 47

Characterization data for intermediates prepare according to the procedure above.

| Inter-me-diate | Structure | Chemical Name | MS: [(M + 1)]$^+$ | $^1$H-NMR |
|---|---|---|---|---|
| G11 | 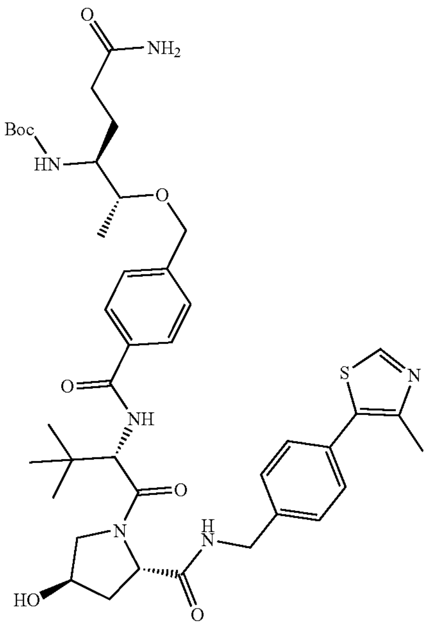 [SMILES: Cc1ncsc1-c1ccc(CNC(=O)[C@@H]2C[C@@H](O)CN2C(=O)[C@@H](NC(=O)c2ccc(CO[C@H](C)[C@H](CCC(N)=O)NC(=O)OC(C)(C)C)cc2)C(C)(C)C)cc1] | tert-butyl N-[(3S,4R)-1-carbamoyl-4-[(4-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]phenyl)methoxy]pentan-3-yl]carbamate | 793.5 | (400 MHz, DMSO-$d_6$) δ 8.99 (d, J = 3.9 Hz, 1H), 8.59 (s, 1H), 7.93 (d, J = 9.0 Hz, 1H), 7.85 (d, J = 7.5 Hz, 2H), 7.44-7.41 (m, 6H), 7.22 (s, 1H), 6.71-6.61 (m, 2H), 5.15 (s, 1H), 4.78 (dd, J = 9.1, 3.0 Hz, 1H), 4.55 (d, J = 3.4 Hz, 2H), 4.47 (t, J = 6.3 Hz, 1H), 4.43 (dd, J = 14.0, 4.5 Hz, 1H), 4.38 (s, 2H), 4.25 (dd, J = 15.3, 5.6 Hz, 1H), 3.74 (s, 2H), 3.33 (s, 1H), 2.46-2.42 (m, 3H), 2.06 (s, 4H), 1.91 (d, J = 2.9 Hz, 3H), 1.79 (s, 1H), 1.49 (s, 1H), 1.38 (s, 9H), 1.11-0.98 (m, 12H). |
| G12 | 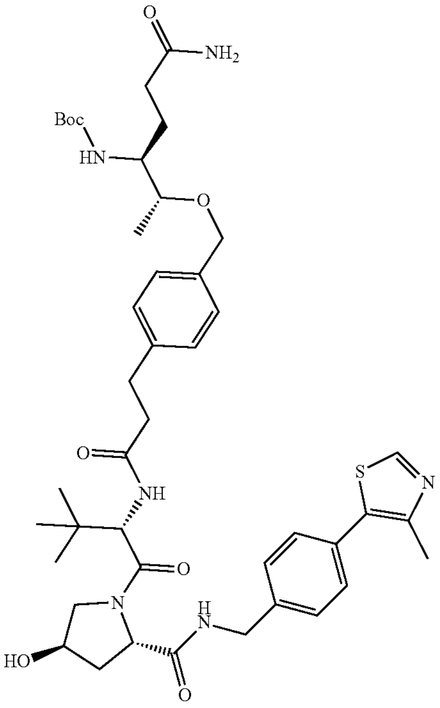 [SMILES: Cc1ncsc1-c1ccc(CNC(=O)[C@@H]2C[C@@H](O)CN2C(=O)[C@@H](NC(=O)CCc2ccc(CO[C@H](C)[C@H](CCC(N)=O)NC(=O)OC(C)(C)C)cc2)C(C)(C)C)cc1] | tert-butyl N-[(3S,4R)-1-carbamoyl-4-[[4-(2-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]ethyl)phenyl]methoxy]pentan-3-yl]carbamate | 821.6 | (400 MHz, $CDCl_3$) δ 8.71 (s, 1H), 7.42-7.32 (m, 5H), 7.22 (d, J = 7.9 Hz, 2H), 7.14 (d, J = 7.8 Hz, 2H), 6.36 (d, J = 9.1 Hz, 1H), 5.73 (s, 1H), 4.95 (d, J = 9.7 Hz, 1H), 4.70 (t, J = 7.9 Hz, 1H), 4.61-4.52 (m, 4H), 4.41-4.33 (m, 2H), 4.06 (d, J = 11.4 Hz, 1H), 3.70-3.51 (m, 3H), 3.02-2.86 (m, 2H), 2.53-2.52 (m, 5H), 2.24 (t, J = 7.0 Hz, 2H), 2.17 (t, J = 10.6 Hz, 1H), 2.00-1.90 (m, 1H), 1.72-1.58 (m, 1H), 1.44 (s, 9H), 1.19 (d, J = 6.3 Hz, 3H), 0.90 (s, 9H). |

TABLE 47-continued

| Characterization data for intermediates prepare according to the procedure above. | | | | |
|---|---|---|---|---|
| Inter-me-diate | Structure | Chemical Name | MS: [(M + 1)]+ | 1H-NMR |
| G13 | 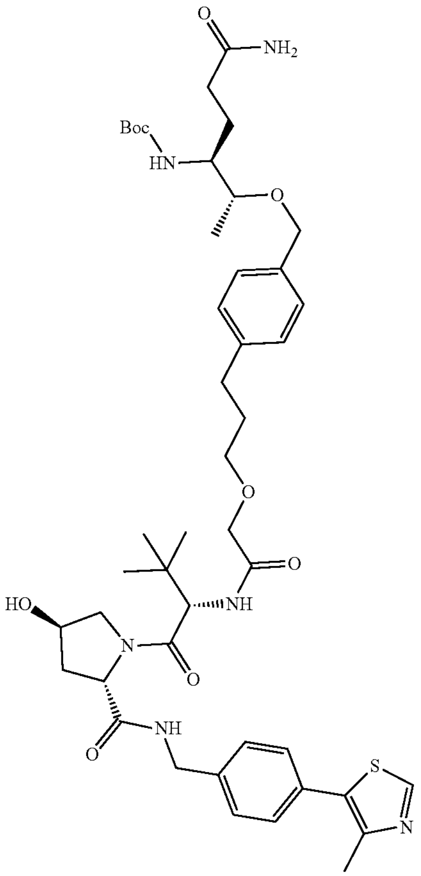 [SMILES: Cc1ncsc1-c1ccc(CNC(=O)[C@@H]2C[C@@H](O)CN2C(=O)[C@@H](NC(=O)COCCCc2ccc(CO[C@H](C)[C@H](CCC(N)=O)NC(=O)OC(C)(C)C)cc2)C(C)(C)C)cc1] | tert-butyl N-[(3S,4R)-1-carbamoyl-4-([4-[3-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methoxy)propyl]phenyl]methoxy)pentan-3-yl]carbamate | 865.6 | (400 MHz, DMSO-$d_6$) δ 8.98 (s, 1H), 8.61 (t, J = 6.0 Hz, 1H), 7.45-7.36 (m, 5H), 7.23-7.13 (m, 5H), 6.67 (s, 1H), 6.59 (d, J = 9.0 Hz, 1H), 5.16 (d, J = 3.5 Hz, 1H), 4.57 (d, J = 9.5 Hz, 1H), 4.49-4.34 (m, 5H), 4.26 (dd, J = 15.9, 5.6 Hz, 1H), 3.93 (s, 2H), 3.70-3.59 (m, 2H), 3.50-3.37 (m, 4H), 2.65 (t, J = 7.8 Hz, 2H), 2.43 (s, 3H), 2.12-1.74 (m, 8H), 1.38 (s, 9H), 1.05 (d, J = 6.0 Hz, 3H), 0.95 (s, 9H). |

TABLE 47-continued

| Characterization data for intermediates prepare according to the procedure above. | | | | |
|---|---|---|---|---|
| Inter-me-diate | Structure | Chemical Name | MS: [(M + 1)]$^+$ | $^1$H-NMR |
| G14 | 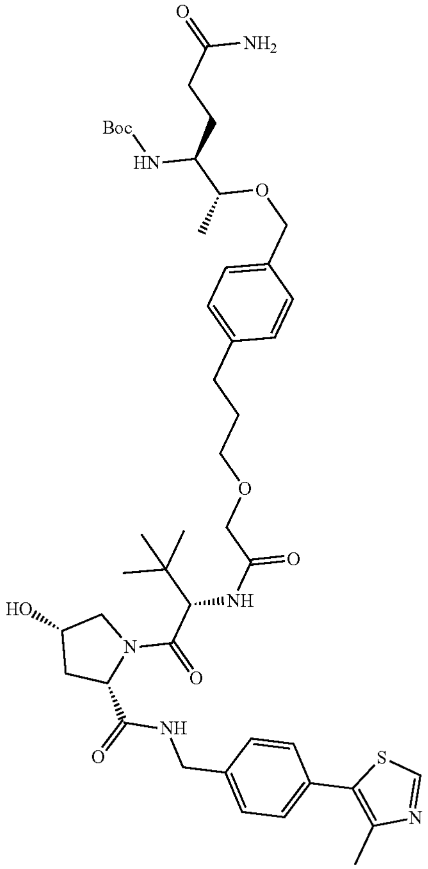 [SMILES: Cc1ncsc1-c1ccc(CNC(=O)[C@@H]2C[C@H](O)CN2C(=O)[C@@H](NC(=O)COCCCc2ccc(CO[C@H](C)[C@H](CCC(N)=O)NC(=O)OC(C)(C)C)cc2)C(C)(C)C)cc1] | tert-butyl N-[(3S,4R)-1-carbamoyl-4-([4-[3-([[(2S)-1-[(2S,4S)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methoxy)propyl]phenyl]methoxy)pentan-3-yl]carbamate | 865.6 | (400 MHz, DMSO-$d_6$) δ 8.98 (s, 1H), 8.68 (t, J = 6.1 Hz, 1H), 7.45-7.35 (m, 5H), 7.27-7.15 (m, 4H), 7.15 (d, J = 7.8 Hz, 2H), 6.67 (s, 1H), 6.59 (d, J = 9.1 Hz, 1H), 5.45 (d, J = 7.3 Hz, 1H), 4.53 (d, J = 9.3 Hz, 1H), 4.41 (s, 2H), 4.48-4.35 (m, 1H), 4.33-4.20 (m, 2H), 3.99-3.85 (m, 3H), 3.65 (s, 1H), 3.51-3.43 (m, 4H), 2.63 (q, J = 8.9, 8.3 Hz, 2H), 2.43 (s, 3H), 2.35 (ddd, J = 13.9, 8.5, 5.7 Hz, 1H), 2.10-1.99 (m, 2H), 1.85-1.73 (m, 4H), 1.48 (s, 1H), 1.38 (d, J = 2.3 Hz, 9H), 1.06 (dd, J = 6.2, 3H), 0.96 (s, 9H). |

TABLE 47-continued

| Characterization data for intermediates prepare according to the procedure above. | | | | |
|---|---|---|---|---|
| Intermediate | Structure | Chemical Name | MS: [(M + 1)]+ | 1H-NMR |
| G15 | 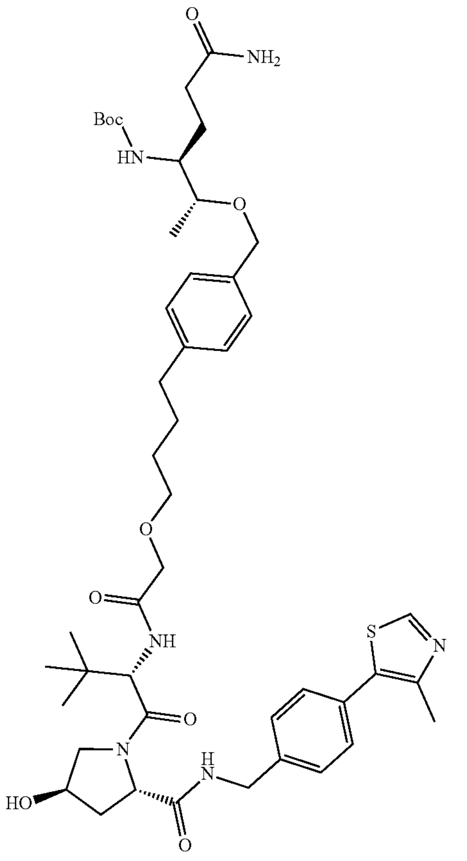 [SMILES: Cc1ncsc1-c1ccc(CNC(=O)[C@@H]2C[C@@H](O)CN2C(=O)[C@@H](NC(=O)COCCCCc2ccc(CO[C@H](C)[C@H](CCC(N)=O)NC(=O)OC(C)(C)C)cc2)C(C)(C)C)cc1] | tert-butyl N-[(3S,4R)-1-carbamoyl-4-([4-[4-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methoxy)butyl]phenyl]methoxy)pentan-3-yl]carbamate | 879.6 | (400 MHz, DMSO-$d_6$) δ 8.98 (s, 1H), 8.60 (s, 1H), 7.46-7.34 (m, 5H), 7.25-7.10 (m, 5H), 6.71-6.56 (m, 2H), 5.15 (s, 1H), 4.56 (d, J = 9.5 Hz, 1H), 4.49-4.34 (m, 5H), 4.31-4.21 (m, 1H), 3.91 (s, 2H), 3.66 (s, 1H), 3.62 (s, 1H), 3.58 (s, 2H), 3.53-3.38 (m, 4H), 2.59 (s, 2H), 2.44 (s, 3H), 2.05 (s, 3H), 1.91 (s, 1H), 1.63 (d, J = 7.7 Hz, 2H), 1.56 (s, 2H), 1.38 (s, 9H), 1.05 (d, J = 6.1 Hz, 3H), 0.94 (s, 9H). |

TABLE 47-continued

| Characterization data for intermediates prepare according to the procedure above. | | | | |
|---|---|---|---|---|
| Intermediate | Structure | Chemical Name | MS: [(M + 1)]+ | 1H-NMR |
| G16 | 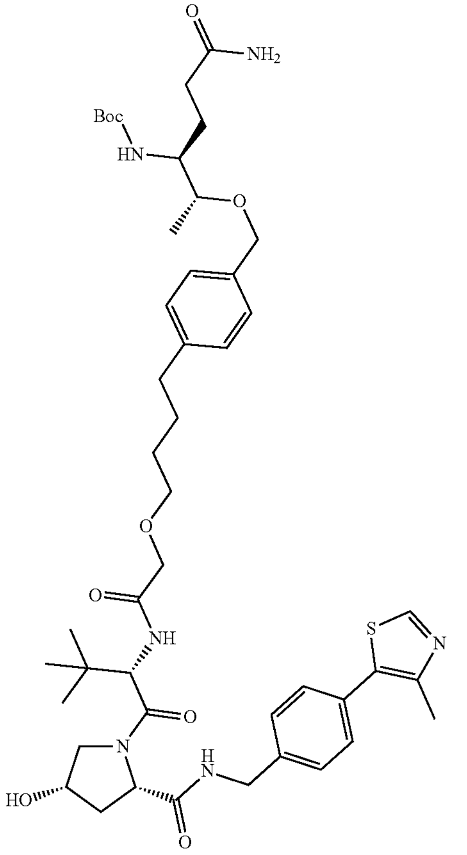 [SMILES: Cc1ncsc1-c1ccc(CNC(=O)[C@@H]2C[C@H](O)CN2C(=O)[C@@H](NC(=O)COCCCCc2ccc(CO[C@H](C)[C@H](CCC(N)=O)NC(=O)OC(C)(C)C)cc2)C(C)(C)C)cc1] | tert-butyl N-[(3S,4R)-1-carbamoyl-4-([4-[4-([[(2S)-1-[(2S,4S)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methoxy)butyl]phenyl]methoxy)pentan-3-yl]carbamate | 879.7 | (400 MHz, DMSO-$d_6$) δ 8.98 (d, J = 4.4 Hz, 1H), 8.67 (s, 1H), 7.41 (d, J = 11.4 Hz, 1H), 7.40 (s, 3H), 7.35 (d, J = 9.2 Hz, 1H), 7.24-7.19 (m, 3H), 7.17-7.11 (m, 3H), 6.67 (s, 1H), 6.59 (d, J = 8.9 Hz, 1H), 5.44 (d, J = 7.2 Hz, 1H), 4.51 (d, J = 9.3 Hz, 1H), 4.42-4.40 (m, 4H), 4.31 (d, J = 5.4 Hz, 1H), 4.25 (d, J = 14.6 Hz, 2H), 3.93-3.84 (m, 3H), 3.31 (s, 2H), 2.58 (s, 2H), 2.44 (d, J = 9.7 Hz, 1H), 2.44 (s, 2H), 2.34 (s, 1H), 1.76 (d, J = 6.8 Hz, 2H), 1.62 (d, J = 7.5 Hz, 2H), 1.55 (s, 2H), 1.46 (s, 1H), 1.38 (d, J = 3.6 Hz, 9H), 1.05 (d, J = 5.8 Hz, 3H), 0.95 (s, 9H). |

TABLE 47-continued

Characterization data for intermediates prepare according to the procedure above.

| Intermediate | Structure | Chemical Name | MS: [(M + 1)]$^+$ | $^1$H-NMR |
|---|---|---|---|---|
| G17 | 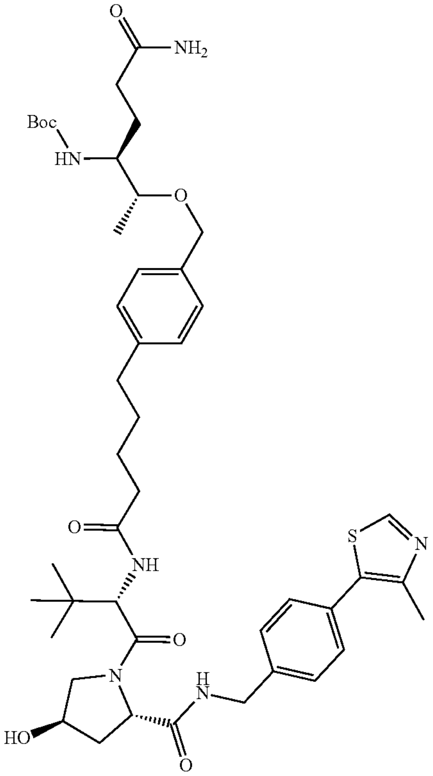 [SMILES: Cc1ncsc1-c1ccc(CNC(=O)[C@@H]2C[C@@H](O)CN2C(=O)[C@@H](NC(=O)CCCCc2ccc(CO[C@H](C)[C@H](CCC(N)=O)NC(=O)OC(C)(C)C)cc2)C(C)(C)C)cc1] | tert-butyl N-[(3S,4R)-1-carbamoyl-4-[[4-(4-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]butyl) phenyl]methoxy]pentan-3-yl]carbamate | 849.6 | (400 MHz, $CD_3OD$) δ 8.89 (s, 1H), 7.83 (d, J = 9.0 Hz, 1H), 7.48 (d, J = 8.3 Hz, 2H), 7.45-7.41 (m, 2H), 7.27 (d, J = 8.0 Hz, 2H), 7.16 (d, J = 7.8 Hz, 2H), 6.42 (d, J = 9.5 Hz, 1H), 4.68-4.34 (m, 8H), 3.92 (d, J = 11.0 Hz, 1H), 3.82 (dd, J = 11.0, 3.9 Hz, 1H), 3.68-3.46 (m, 3H), 2.63 (s, 2H), 2.49 (s, 3H), 2.37-2.21 (m, 6H), 2.10 (ddd, J = 13.2, 9.0, 4.5 Hz, 1H), 1.98 (d, J = 15.7 Hz, 2H), 1.66-1.65 (m, 5H), 1.45 (s, 9H), 1.21-1.13 (m, 3H), 1.05 (s, 9H). |
| G18 | 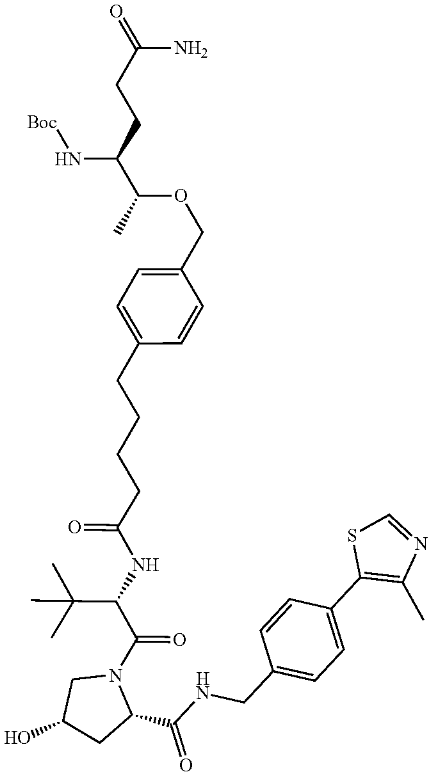 [SMILES: Cc1ncsc1-c1ccc(CNC(=O)[C@@H]2C[C@H](O)CN2C(=O)[C@@H](NC(=O)CCCCc2ccc(CO[C@H](C)[C@H](CCC(N)=O)NC(=O)OC(C)(C)C)cc2)C(C)(C)C)cc1] | tert-butyl N-[(3S,4R)-1-carbamoyl-4-[[4-(4-[[(2S)-1-[(2S,4S)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]butyl) phenyl]methoxy]pentan-3-yl]carbamate | 849.6 | (400 MHz, DMSO-$d_6$) δ 8.99 (s, 1H), 8.62 (t, J = 6.1 Hz, 1H), 7.86 (d, J = 8.8 Hz, 1H), 7.45-7.35 (m, 4H), 7.22 (d, J = 7.9 Hz, 3H), 7.12 (d, J = 7.7 Hz, 2H), 6.67 (s, 1H), 6.59 (d, J = 9.0 Hz, 1H), 5.42 (d, J = 7.2 Hz, 1H), 4.45 (dd, J = 92, 6.7 Hz, 2H), 4.42 (d, J = 2.9 Hz, 2H), 4.36 (dd, J = 8.6, 6.1 Hz, 1H), 4.31-4.16 (m, 2H), 3.93 (dd, J = 10.0, 5.7 Hz, 1H), 3.42 (ddd, J = 15.9, 11.0, 5.8 Hz, 2H), 2.54 (d, J = 7.1 Hz, 2H), 2.45 (s, 3H), 2.37-2.24 (m, 1H), 2.10-1.98 (m, 2H), 1.74 (dt, J = 12.4, 6.0 Hz, 1H), 1.51 (s, 4H), 1.49 (d, J = 6.9 Hz, 1H), 1.38 (s, 9H), 1.05 (d, J = 6.0 Hz, 3H), 0.95 (s, 9H). |

TABLE 47-continued

Characterization data for intermediates prepare according to the procedure above.

| Inter-me-diate | Structure | Chemical Name | MS: [(M + 1)]+ | 1H-NMR |
|---|---|---|---|---|
| G19 | 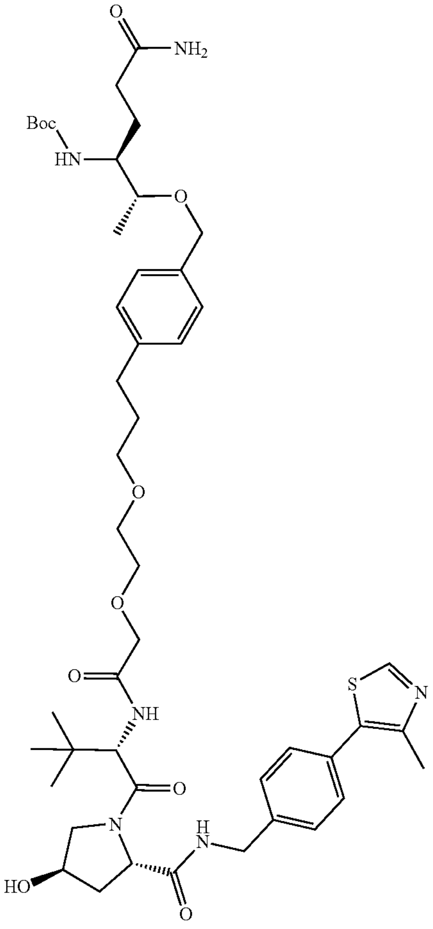 [SMILES: Cc1ncsc1-c1ccc(CNC(=O)[C@@H]2C[C@@H](O)CN2C(=O)[C@@H](NC(=O)COCCOCCCc2ccc(CO[C@H](C)[C@H](CCC(N)=O)NC(=O)OC(C)(C)C)cc2)C(C)(C)C)cc1] | tert-butyl N-[(3S,4R)-1-carbamoyl-4-[(4-[3-[2-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methoxy)ethoxy]propyl]phenyl)methoxy]pentan-3-yl]carbamate | 909.7 | (400 MHz, DMSO-$d_6$) δ 8.98 (s, 1H), 8.59 (t, J = 6.0 Hz, 1H), 7.41-7.38 (m, 4H), 7.21 (d, J = 7.8 Hz, 2H), 7.12 (d, J = 7.8 Hz, 2H), 6.73-6.57 (m, 2H), 5.15 (d, J = 3.5 Hz, 1H), 4.58 (d, J = 9.6 Hz, 1H), 4.50-4.34 (m, 5H), 4.26 (dd, J = 15.7, 5.6 Hz, 1H), 3.99 (s, 2H), 3.73-3.59 (m, 4H), 3.54 (t, J = 4.2 Hz, 2H), 3.45-3.36 (m, 4H), 2.59 (t, J = 7.7 Hz, 2H), 2.45-2.43 (m, 3H), 2.09-1.97 (m, 2H), 1.92 (s, 2H), 1.86-1.74 (m, 3H), 1.39 (s, 9H), 1.06 (d, J = 5.9 Hz, 3H), 0.96 (s, 9H). |

TABLE 47-continued

Characterization data for intermediates prepare according to the procedure above.

| Intermediate | Structure | Chemical Name | MS: [(M + 1)]+ | 1H-NMR |
| --- | --- | --- | --- | --- |
| G20 | 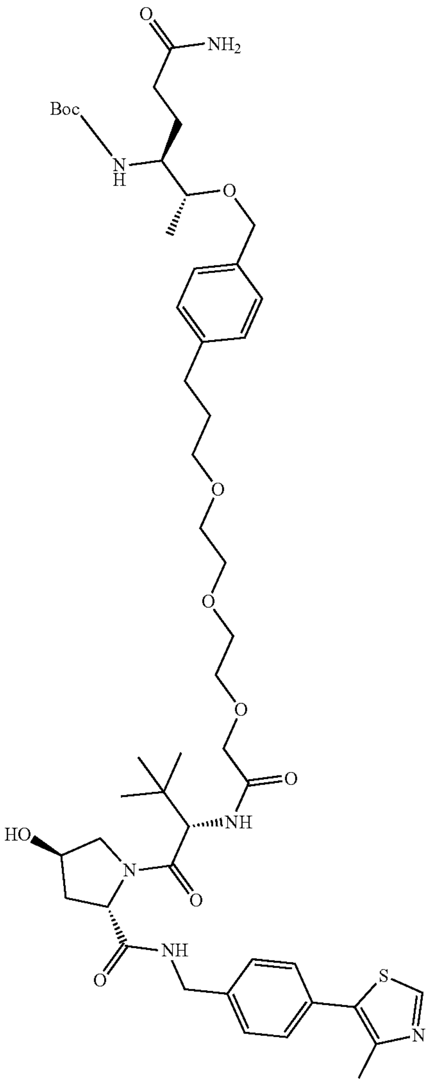 [SMILES: Cc1ncsc1-c1ccc(CNC(=O)[C@@H]2C[C@@H](O)CN2C(=O)[C@@H](NC(=O)COCCOCCOCCCc2ccc(CO[C@H](C)[C@H](CCC(N)=O)NC(=O)OC(C)(C)C)cc2)C(C)(C)C)cc1] | tert-butyl N-[(3S,4R)-1-carbamoyl-4-[[4-(3-[2-[2-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methoxy)ethoxy]ethoxy]propyl)phenyl]methoxy]pentan-3-yl]carbamate | 953.7 | (400 MHz, DMSO-$d_6$) δ 8.98 (s, 1H), 8.60 (t, J = 6.1 Hz, 1H), 7.46-7.37 (m, 4H), 7.26-7.19 (m, 3H), 7.14 (t, J = 9.4 Hz, 2H), 6.71-6.55 (m, 2H), 5.15 (d, J = 3.5 Hz, 1H), 4.57 (d, J = 9.6 Hz, 1H), 4.48-4.34 (m, 5H), 4.25 (dd, J = 15.9, 5.6 Hz, 1H), 3.98 (s, 2H), 3.68 (dd, J = 10.9, 3.9 Hz, 1H), 3.65-3.52 (m, 8H), 3.49 (t, J = 4.8 Hz, 3H), 3.42-3.31 (m, 4H), 2.58 (dt, J = 15.3, 7.5 Hz, 2H), 2.44 (s, 3H), 2.04 (td, J = 10.0, 9.6, 5.4 Hz, 2H), 1.82-1.71 (m, 3H), 1.47 (d, J = 9.7 Hz, 1H), 1.38 (s, 9H), 1.06 (d, J = 6.0 Hz, 3H), 0.95 (s, 9H). |

TABLE 47-continued

| Characterization data for intermediates prepare according to the procedure above. | | | | |
|---|---|---|---|---|
| Intermediate | Structure | Chemical Name | MS: $[(M+1)]^+$ | $^1$H-NMR |
| G21 | 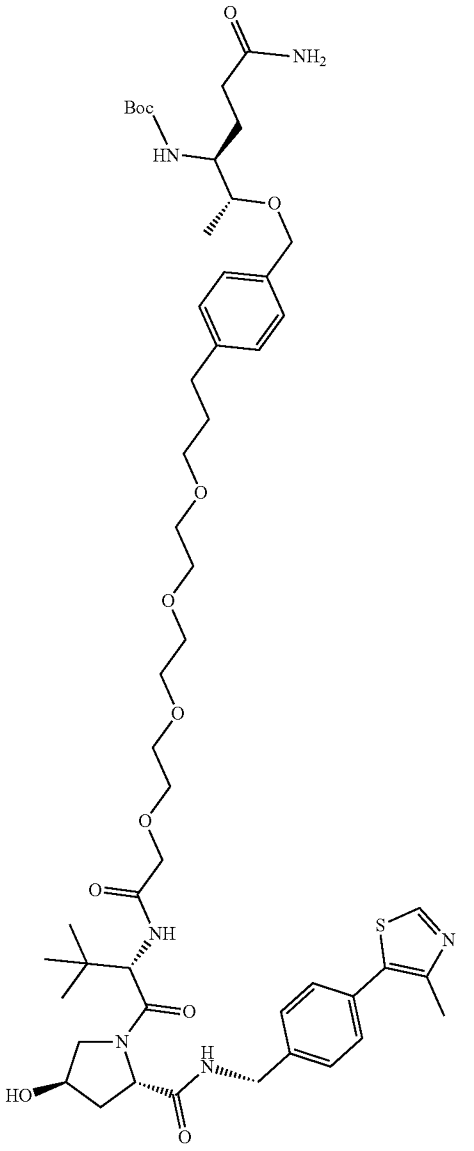 | tert-butyl N-[(3S,4R)-1-carbamoyl-4-[[4-(1-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]-2,5,8,11-tetraoxatetradecan-14-yl)phenyl]methoxy]pentan-3-yl]carbamate | 997.7 | (400 MHz, DMSO-$d_6$) δ 8.98 (d, J = 3.4 Hz, 1H), 8.60 (s, 1H), 7.40 (d, J = 3.2 Hz, 5H), 7.25-7.18 (m, 3H), 7.14 (d, J = 7.7 Hz, 2H), 6.67 (s, 1H), 6.60 (d, J = 9.1 Hz, 1H), 5.15 (d, J = 3.5 Hz, 1H), 4.57 (d, J = 9.4 Hz, 1H), 4.49-4.32 (m, 5H), 4.30-4.20 (m, 1H), 3.96 (d, J = 2.9 Hz, 2H), 3.71-3.41 (m, 9H), 3.41-3.33 (m, 2H), 2.58 (t, J = 7.9 Hz, 3H), 2.44 (d, J = 3.2 Hz, 3H), 2.06-2.04 (m, 4H), 1.91 (s, 2H), 1.78-7.74 (m, 4H), 1.48 (s, 1H), 1.38 (d, J = 3.1 Hz, 9H), 1.06 (d, J = 5.8 Hz, 3H), 0.95 (d, J = 2.9 Hz, 9H). |

TABLE 47-continued

Characterization data for intermediates prepare according to the procedure above.

| Inter-me-diate | Structure | Chemical Name | MS: [(M + 1)]+ | $^1$H-NMR |
|---|---|---|---|---|
| G22 | 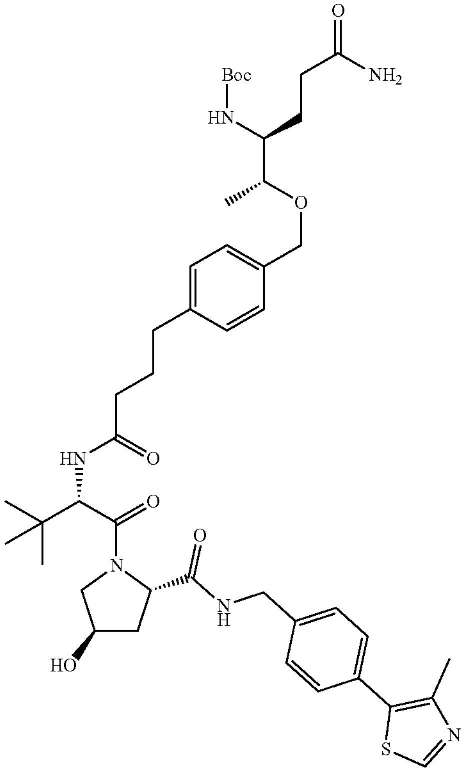 [SMILES: Cc1ncsc1-c1ccc(CNC(=O)[C@@H]2C[C@@H](O)CN2C(=O)[C@@H](NC(=O)CCCc2ccc(CO[C@H](C)[C@H](CCC(N)=O)NC(=O)OC(C)(C)C)cc2)C(C)(C)C)cc1] | tert-butyl N-[(3S,4R)-1-carbamoyl-4-[[4-(3-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]propyl)phenyl]methoxy]pentan-3-yl]carbamate | 835.4 | (400 MHz,$CDCl_3$) δ 8.93 (s, 1H), 7.42-7.35 (m, 5H), 7.25-7.21 (m, 3H), 7.13 (d, J = 7.7 Hz, 2H), 6.30-6.23 (m, 1H), 5.77-5.46 (m, 1H), 4.73 (q, J = 10.0, 7.9 Hz, 2H), 4.64-4.56 (m, 2H), 4.56-4.47 (m, 2H), 4.34 (d, J = 11.5 Hz, 2H), 4.15 (d, J = 11.5 Hz, 1H), 3.65-3.52 (m, 3H), 3.50-3.49 (m, 3H), 2.59-2.58 (m, 6H), 2.27-2.11 (m, 4H), 1.93 (s, 2H), 1.60 (d, J = 5.3 Hz, 2H), 1.43 (s, 9H), 1.19 (d, J = 6.2 Hz, 3H), 0.94 (s, 9H). |
| G23 | 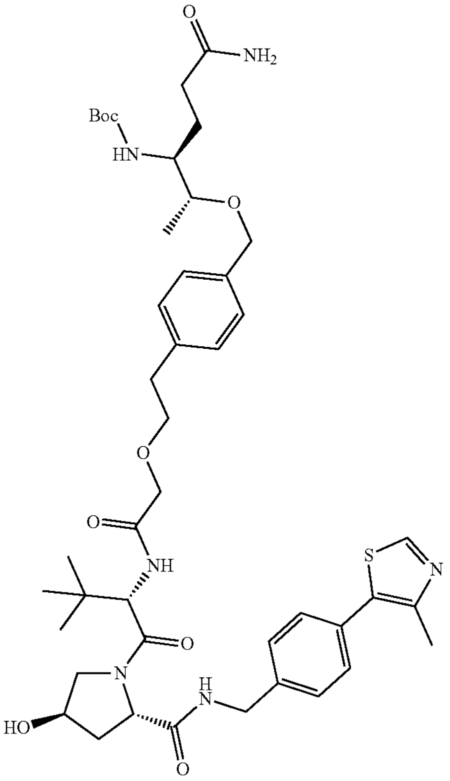 [SMILES: Cc1ncsc1-c1ccc(CNC(=O)[C@@H]2C[C@@H](O)CN2C(=O)[C@@H](NC(=O)COCCc2ccc(CO[C@H](C)[C@H](CCC(N)=O)NC(=O)OC(C)(C)C)cc2)C(C)(C)C)cc1] | tert-butyl N-[(3S,4R)-1-carbamoyl-4-([4-[2-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methoxy)ethyl]phenyl]methoxy)pentan-3-yl]carbamate | 851.6 | (400 MHz, DMSO-$d_6$) δ 8.98 (s, 1H), 8.61 (t, J = 6.0 Hz, 1H), 7.46-7.36 (m, 4H), 7.35 (d, J = 9.5 Hz, 1H), 7.23-7.22 (m, 4H), 6.68 (s, 1H), 6.60 (d, J = 9.1 Hz, 1H), 5.16 (d, J = 3.5 Hz, 1H), 4.55 (d, J = 9.6 Hz, 1H), 4.50-4.34 (m, 5H), 4.26 (dd, J = 15.9, 5.6 Hz, 1H), 3.97-3.88 (m, 2H), 3.75-3.64 (m, 3H), 3.61 (d, J = 10.7 Hz, 1H), 3.45-3.34 (m, 1H), 3.32 (s, 2H), 2.85 (t, J = 6.9 Hz, 2H), 2.45-2.43 (m, 3H), 2.08 (s, 1H), 2.08 (d, J = 11.6 Hz, 2H), 2.06-1.98 (m, 1H), 1.91 (tt, J = 8.7, 4.4 Hz, 1H), 1.38 (s, 9H), 1.04 (d, J = 6.1 Hz, 3H), 0.93 (s, 9H). |

TABLE 47-continued

| Characterization data for intermediates prepare according to the procedure above. | | | | |
|---|---|---|---|---|
| Intermediate | Structure | Chemical Name | MS: [(M + 1)]+ | 1H-NMR |
| G24 | 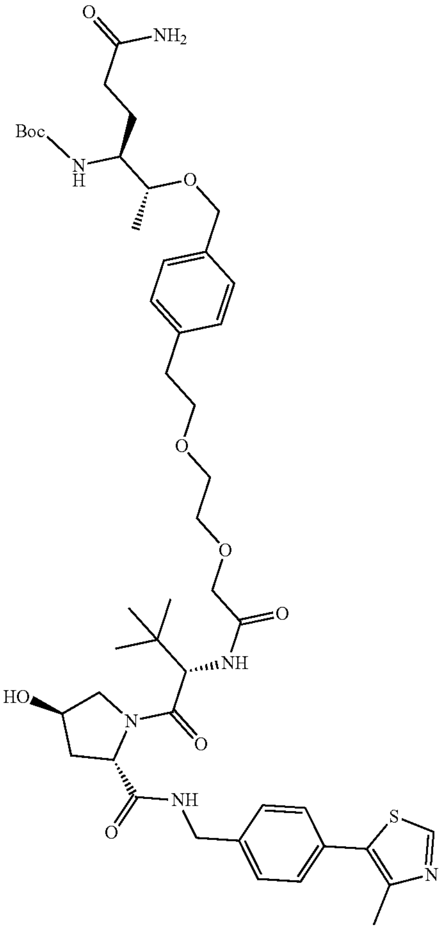 [SMILES: Cc1ncsc1-c1ccc(CNC(=O)[C@@H]2C[C@@H](O)CN2C(=O)[C@@H](NC(=O)COCCOCCc2ccc(CO[C@H](C)[C@H](CCC(N)=O)NC(=O)OC(C)(C)C)cc2)C(C)(C)C)cc1] | tert-butyl N-[(3S,4R)-1-carbamoyl-4-[(4-[2-[2-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methoxy)ethoxy]ethyl]phenyl)methoxy]pentan-3-yl]carbamate | 895.7 | (400 MHz, DMSO-$d_6$) δ 8.98 (s, 1H), 8.59 (t, J = 6.0 Hz, 1H), 7.49-7.39 (m, 4H), 7.26-7.12 (m, 5H), 6.67 (s, 1H), 6.60 (d, J = 9.1 Hz, 1H), 5.15 (d, J = 3.6 Hz, 1H), 4.59 (d, J = 9.6 Hz, 1H), 4.51-4.35 (m, 5H), 4.26 (dd, J = 15.7, 5.6 Hz, 1H), 3.97 (s, 2H), 3.70-3.54 (m, 8H), 3.32 (s, 1H), 2.82 (t, J = 7.1 Hz, 2H), 2.44 (s, 3H), 2.09 (s, 1H), 2.06 (s, 3H), 1.79 (s, 1H), 1.48 (d, J = 11.5 Hz, 1H), 1.39 (s, 9H), 1.06 (d, J = 6.0 Hz, 3H), 0.96 (s, 9H). |

TABLE 47-continued

| Characterization data for intermediates prepare according to the procedure above. | | | | |
|---|---|---|---|---|
| Intermediate | Structure | Chemical Name | MS: [(M + 1)]+ | 1H-NMR |
| G25 | 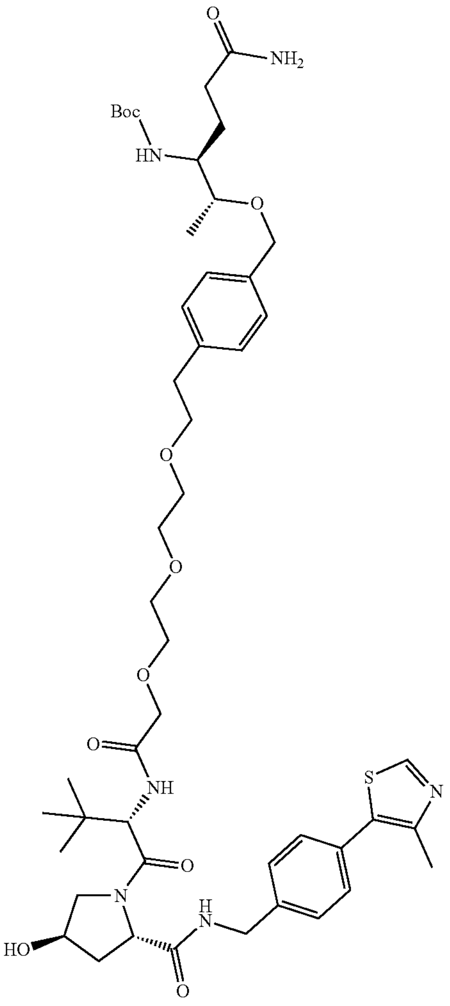 [SMILES: Cc1ncsc1-c1ccc(CNC(=O)[C@@H]2C[C@@H](O)CN2C(=O)[C@@H](NC(=O)COCCOCCOCCc2ccc(CO[C@H](C)[C@H](CCC(N)=O)NC(=O)OC(C)(C)C)cc2)C(C)(C)C)cc1] | tert-butyl N-[(3S,4R)-1-carbamoyl-4-[[4-(2-[2-[2-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methoxy)ethoxy]ethoxy]ethyl)phenyl]methoxy]pentan-3-yl]carbamate | 939.7 | (400 MHz, DMSO-$d_6$) δ 8.98 (s, 1H), 8.60 (s, 1H), 7.47-7.38 (m, 5H), 7.25-7.13 (m, 5H), 6.68 (s, 1H), 6.60 (d, J = 9.0 Hz, 1H), 5.15 (d, J = 3.5 Hz, 1H), 4.57 (d, J = 9.5 Hz, 1H), 4.49-4.34 (m, 5H), 4.24 (dd, J = 16.0, 5.7 Hz, 1H), 3.97 (s, 2H), 3.72-3.50 (m, 8H), 3.18 (d, J = 5.4 Hz, 2H), 2.76 (t, J = 7.1 Hz, 2H), 2.44 (d, J = 1.7 Hz, 3H), 2.04 (s, 3H), 1.91 (s, 3H), 1.79 (s, 1H), 1.46 (s, 1H), 1.38 (s, 9H), 1.05 (d, J = 6.1 Hz, 3H), 0.95 (s, 9H). |

TABLE 47-continued

| Characterization data for intermediates prepare according to the procedure above. | | | | |
|---|---|---|---|---|
| Inter-me-diate | Structure | Chemical Name | MS: [(M + 1)]$^+$ | $^1$H-NMR |
| G26 | 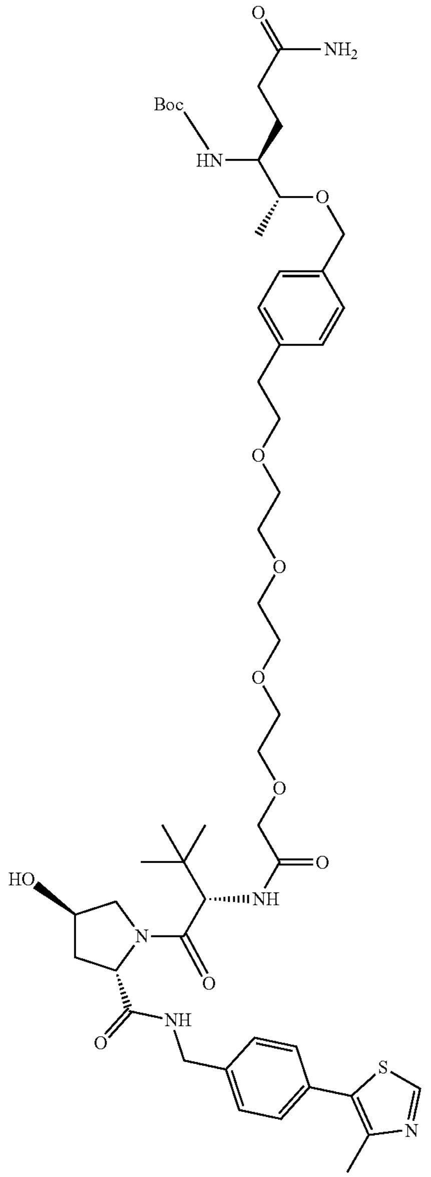 [SMILES: Cc1ncsc1-c1ccc(CNC(=O)[C@@H]2C[C@@H](O)CN2C(=O)[C@@H](NC(=O)COCCOCCOCCOCCc2ccc(CO[C@H](C)[C@H](CCC(N)=O)NC(=O)OC(C)(C)C)cc2)C(C)(C)C)cc1] | tert-butyl N-[(3S,4R)-1-carbamoyl-4-[[4-(1-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]-2,5,8,11-tetraoxatridecan-13-yl)phenyl]methoxy]pentan-3-yl]carbamate | 983.7 | (400 MHz, DMSO-$d_6$) δ 8.98 (s, 1H), 8.59 (t, J = 6.0 Hz, 1H), 7.46-7.39 (m, 5H), 7.31-7.16 (m, 5H), 6.72-6.55 (m, 2H), 5.15 (d, J = 3.5 Hz, 1H), 4.58 (d, J = 9.5 Hz, 1H), 4.46 (d, J = 8.1 Hz, 1H), 4.43 (d, J = 3.5 Hz, 2H), 4.37 (dd, J = 10.8, 4.6 Hz, 2H), 4.25 (dd, J = 15.7, 5.6 Hz, 1H), 3.97 (s, 2H), 3.68 (dd, J = 10.7, 4.0 Hz, 1H), 3.64-3.50 (m, 14H), 3.46-3.36 (m, 2H), 2.78 (q, J = 6.8 Hz, 2H), 2.45 (s, 3H), 2.12-2.01 (m, 3H), 1.79 (dtd, J = 13.7, 7.1, 6.5, 3.4 Hz, 1H), 1.50 (dt, J = 14.1, 8.6 Hz, 1H), 1.39 (s, 9H), 1.06 (d, J = 6.0 Hz, 3H), 0.95 (s, 9H). |

TABLE 47-continued

Characterization data for intermediates prepare according to the procedure above.

| Intermediate | Structure | Chemical Name | MS: [(M + 1)]+ | $^1$H-NMR |
|---|---|---|---|---|
| G27 | 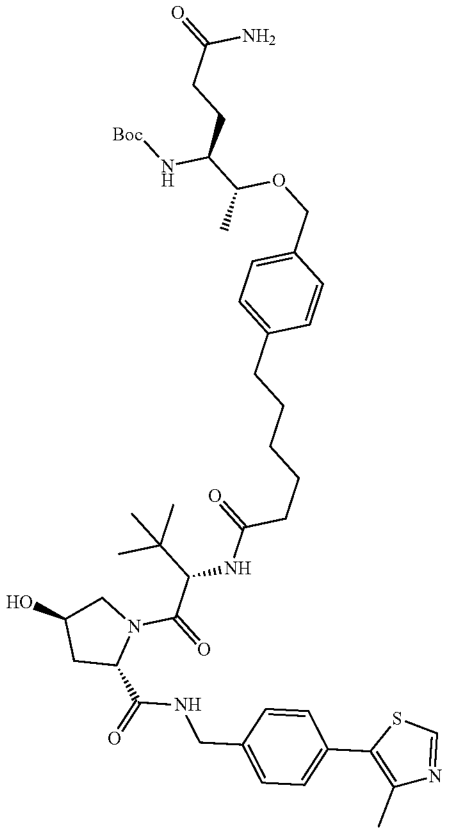 [SMILES: Cc1ncsc1-c1ccc(CNC(=O)[C@@H]2C[C@@H](O)CN2C(=O)[C@@H](NC(=O)CCCCCc2ccc(CO[C@H](C)[C@H](CCC(N)=O)NC(=O)OC(C)(C)C)cc2)C(C)(C)C)cc1] | tert-butyl N-[(3S,4R)-1-carbamoyl-4-[[4-(5-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]pentyl)phenyl]methoxy]pentan-3-yl]carbamate | 863.5 | (400 MHz, $CDCl_3$) δ 8.73 (s, 1H), 7.43-7.31 (m, 5H), 7.23 (d, J = 7.8 Hz, 2H), 7.14 (d, J = 7.7 Hz, 2H), 6.37 (s, 1H), 6.25 (d, J = 8.7 Hz, 1H), 5.56 (s, 1H), 4.88 (d, J = 9.6 Hz, 1H), 4.73 (t, J = 7.9 Hz, 1H), 4.64-4.48 (m, 4H), 4.42-4.30 (m, 2H), 4.13 (d, J = 11.3 Hz, 1H), 3.69-3.58 (m, 3H), 2.60 (t, J = 7.5 Hz, 2H), 2.54 (s, 3H), 2.27 (t, J = 6.9 Hz, 2H), 2.20 (t, J = 7.5 Hz, 2H), 2.16-2.10 (m, 1H), 2.02-1.93 (m, 1H), 1.72-1.57 (m, 5H), 1.45 (s, 9H), 1.35-1.20 (m, 2H), 1.21 (d, J = 6.2 Hz, 3H), 0.94 (s, 9H). |

TABLE 47-continued

| Characterization data for intermediates prepare according to the procedure above. | | | | |
|---|---|---|---|---|
| Intermediate | Structure | Chemical Name | MS: [(M + 1)]+ | $^1$H-NMR |
| G28 | 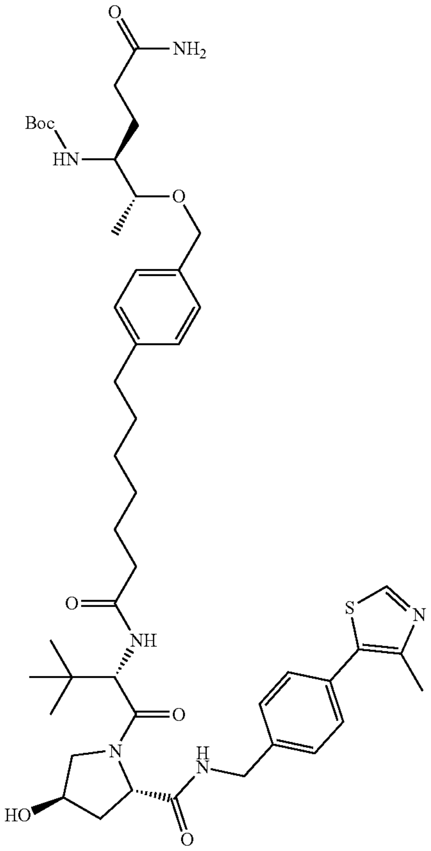 [SMILES: Cc1ncsc1-c1ccc(CNC(=O)[C@@H]2C[C@@H](O)CN2C(=O)[C@@H](NC(=O)CCCCCCc2ccc(CO[C@H](C)[C@H](CCC(N)=O)NC(=O)OC(C)(C)C)cc2)C(C)(C)C)cc1] | tert-butyl N-[(3S,4R)-1-carbamoyl-4-[[4-(6-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]hexyl)phenyl]methoxy]pentan-3-yl]carbamate | 877.6 | (400 MHz, $CD_3OD$) δ 8.87 (s, 1H), 7.46 (d, J = 8.1 Hz, 2H), 7.41 (d, J = 8.3 Hz, 2H), 7.24 (d, J = 7.8 Hz, 2H), 7.13 (d, J = 7.9 Hz, 2H), 4.63 (s, 2H), 4.60-4.42 (m, 5H), 4.35 (d, J = 15.5 Hz, 2H), 3.90 (d, J = 11.0 Hz, 1H), 3.80 (dd, J = 11.0, 3.9 Hz, 1H), 3.63-3.46 (m, 2H), 2.59 (t, J = 7.6 Hz, 2H), 2.47 (s, 3H), 2.32-2.22 (m, 1H), 2.32-2.11 (m, 4H), 2.08 (td, J = 8.9, 4.5 Hz, 1H), 1.95 (d, J = 8.1 Hz, 1H), 1.59 (s, 5H), 1.43 (s, 9H), 1.37-1.32 (m, 6H), 1.17 (dd, J = 13.8, 6.6 Hz, 3H), 1.03 (s, 9H). |

TABLE 47-continued

| Characterization data for intermediates prepare according to the procedure above. | | | | |
|---|---|---|---|---|
| Intermediate | Structure | Chemical Name | MS: [(M + 1)]$^+$ | $^1$H-NMR |
| G29 | 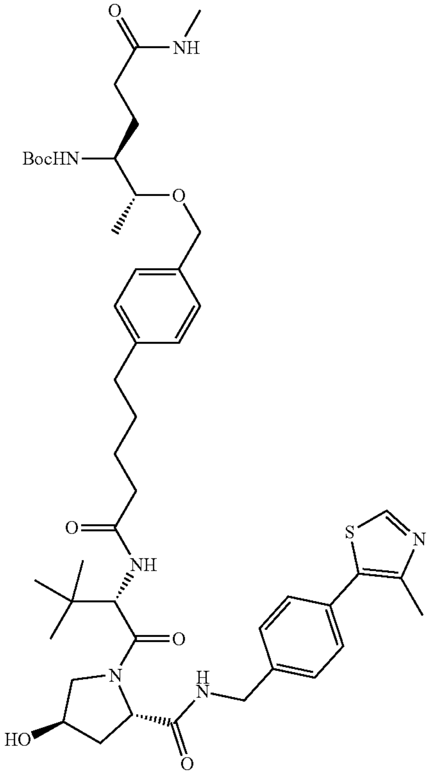 [SMILES: CNC(=O)CC[C@H](NC(=O)OC(C)(C)C)[C@@H](C)OCc1ccc(CCCCC(=O)N[C@H](C(=O)N2C[C@H](O)C[C@H]2C(=O)NCc2ccc(-c3scnc3C)cc2)C(C)(C)C)cc1] | tert-butyl N-[(3S,4R)-4-[[4-(4-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]butyl)phenyl]methoxy]-1-(methylcarbamoyl)-pentan-3-yl]carbamate | 863.7 | (400 MHz, $CDCl_3$) δ 8.72 (s, 1H), 7.42-7.30 (m, 5H), 7.23 (d, J = 7.8 Hz, 2H), 7.14 (d, J = 7.8 Hz, 2H), 6.35 (s, 1H), 6.16 (d, J = 8.0 Hz, 1H), 4.90 (d, J = 9.5 Hz, 1H), 4.71 (t, J = 7.9 Hz, 1H), 4.63-4.55 (m, 1H), 4.58-4.49 (m, 3H), 4.40-4.31 (m, 2H), 4.09 (d, J = 11.3 Hz, 1H), 3.60 (m, 3H), 2.79 (d, J = 4.6 Hz, 3H), 2.62 (d, J = 6.7 Hz, 2H), 2.53 (s, 3H), 2.28-2.12 (m, 5H), 2.00-1.92 (m, 1H), 1.66-1.60 (m, 5H), 1.44 (s, 9H), 1.19 (d, J = 6.1 Hz, 3H), 0.94 (s, 9H). |
| G30 | 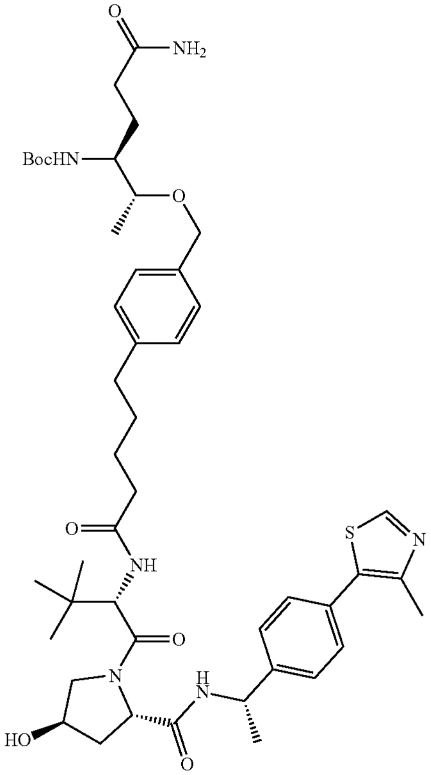 [SMILES: Cc1ncsc1-c1ccc([C@H](C)NC(=O)[C@@H]2C[C@@H](O)CN2C(=O)[C@@H](NC(=O)CCCCc2ccc(CO[C@H](C)[C@H](CCC(N)=O)NC(=O)OC(C)(C)C)cc2)C(C)(C)C)cc1] | tert-butyl N-[(3S,4R)-1-carbamoyl-4-[[4-(4-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]butyl)phenyl]methoxy]pentan-3-yl]carbamate | 863.4 | (400 MHz, $CD_3OD$) δ 8.89 (s, 1H), 7.52-7.40 (m, 4H), 7.28 (d, J = 8.0 Hz, 2H), 7.17 (d, J = 7.9 Hz, 2H), 5.10-4.97 (m, 1H), 4.66-4.62 (m, 1H), 4.62-4.52 (m, 2H), 4.52-4.42 (m, 2H), 3.90 (d, J = 11.1 Hz, 1H), 3.77 (dd, J = 11.0, 4.0 Hz, 1H), 3.64-3.46 (m, 2H), 2.65 (d, J = 7.0 Hz, 2H), 2.50 (s, 3H), 2.42-2.13 (m, 2H), 1.98 (dtd, J = 13.1, 8.5, 3.6 Hz, 2H), 1.70-1.6 1 (m, 6H), 1.53 (d, J = 7.0 Hz, 3H), 1.45 (s, 9H), 1.44-1.42 (m, 2H), 1.18 (d, J = 6.2 Hz, 3H), 1.05 (s, 9H). |

TABLE 47-continued

| Characterization data for intermediates prepare according to the procedure above. | | | | |
|---|---|---|---|---|
| Inter-me-diate | Structure | Chemical Name | MS: [(M + 1)]+ | $^1$H-NMR |
| G31 | 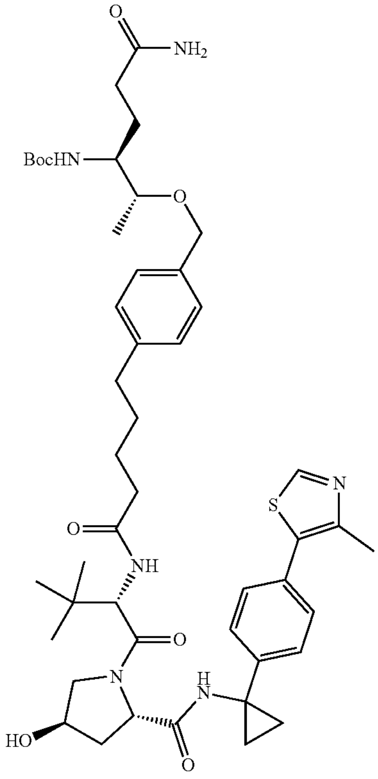 [SMILES: Cc1ncsc1-c1ccc(C2(NC(=O)[C@@H]3C[C@@H](O)CN3C(=O)[C@@H](NC(=O)CCCCc3ccc(CO[C@H](C)[C@H](CCC(N)=O)NC(=O)OC(C)(C)C)cc3)C(C)(C)C)CC2)cc1] | tert-butyl N-[(3S,4R)-1-carbamoyl-4-[[4-(4-[[(2S)-1-[(2S,4R)-4-hydroxy-2-([1-[4-(4-methyl-1,3-thiazol-5-yl)phenyl]cyclopropyl]carbamoyl)pyrrolidin-1-yl]-3,3-dimethyl-1-oxobutan-2-yl]carbamoyl]butyl)phenyl]methoxy]pentan-3-yl]carbamate | 875.4 | (400 MHz, DMSO-$d_6$) δ 8.98 (s, 1H), 8.82 (s, 1H), 7.96 (d, J = 9.2 Hz, 1H), 7.37-7.27 (m, 4H), 7.26-7.20 (m, 3H), 7.14 (d, J = 7.9 Hz, 2H), 6.70 (s, 1H), 6.62 (d, J = 9.1 Hz, 1H), 5.14 (d, J = 3.5 Hz, 1H), 4.56 (d, J = 9.4 Hz, 1H), 4.43 (d, J = 2.3 Hz, 2H), 4.39 (dd, J = 17.1, 9.1 Hz, 2H), 3.65 (s, 2H), 3.47-3.36 (m, 2H), 2.56 (d, J = 7.2 Hz, 2H), 2.45 (s, 3H), 2.33 (dt, J = 13.9, 6.9 Hz, 1H), 2.15 (dd, J = 14.0, 7.5 Hz, 1H), 2.11-2.01 (m, 1H), 2.03-1.95 (m, 1H), 1.94-1.83 (m, 1H), 1.79 (s, 1H), 1.60-1.40 (m, 7H), 1.39 (s, 9H), 1.29-1.20 (m, 1H), 1.23-1.10 (m, 2H), 1.06 (d, J = 6.0 Hz, 3H), 0.94 (s, 9H). |

TABLE 47-continued

| Characterization data for intermediates prepare according to the procedure above. | | | | |
|---|---|---|---|---|
| Inter-me-diate | Structure | Chemical Name | MS: [(M + 1)]+ | 1H-NMR |
| G32 | 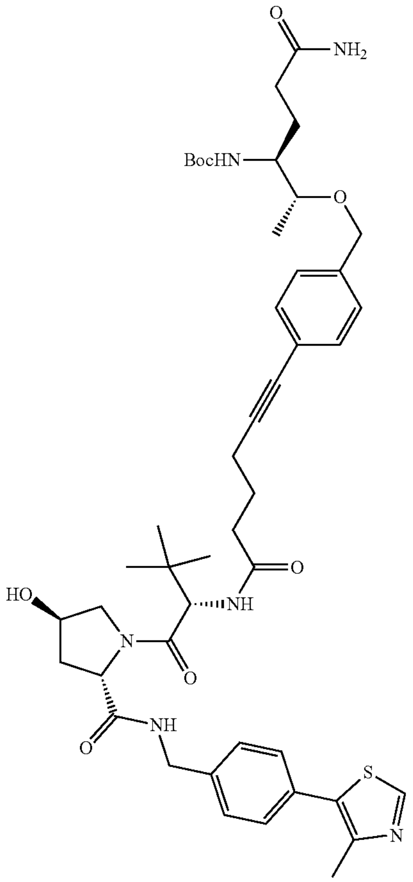 [SMILES: Cc1ncsc1-c1ccc(CNC(=O)[C@@H]2C[C@@H](O)CN2C(=O)[C@@H](NC(=O)CCCC#Cc2ccc(CO[C@H](C)[C@H](CCC(N)=O)NC(=O)OC(C)(C)C)cc2)C(C)(C)C)cc1] | tert-butyl N-[(3S,4R)-1-carbamoyl-4-[[4-(5-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]pent-1-yn-1-yl)phenyl]methoxy]pentan-3-yl]carbamate | 859.3 | Used directly in next step without further purification |

TABLE 47-continued

Characterization data for intermediates prepare according to the procedure above.

| Inter-me-diate | Structure | Chemical Name | MS: [(M + 1)]$^+$ | $^1$H-NMR |
|---|---|---|---|---|
| G33 | 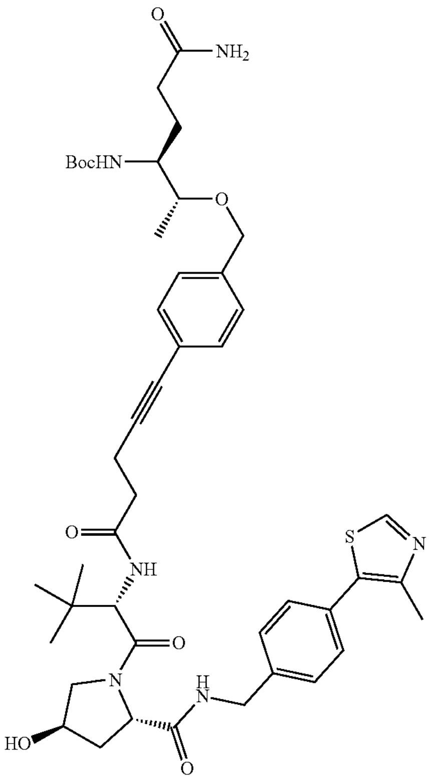 [SMILES: Cc1ncsc1-c1ccc(CNC(=O)[C@@H]2C[C@@H](O)CN2C(=O)[C@@H](NC(=O)CCC#Cc2ccc(CO[C@H](C)[C@H](CCC(N)=O)NC(=O)OC(C)(C)C)cc2)C(C)(C)C)cc1] | tert-butyl N-[(3S,4R)-1-carbamoyl-4-[[4-(4-[[(2S)-1-[(2S,4R)-4-hydroxy-2-([[4-(4-methyl-1,3-thiazol-5-yl)phenyl]methyl] carbamoyl)pyrrolidin-1-yl]-3,3-dimethyl-1-oxobutan-2-yl]carbamoyl]but-1-yn-1-yl)phenyl]methoxy] pentan-3-yl]carbamate | 845.4 | (400 MHz, $CD_3OD$) δ 8.90 (s, 1H), 7.51-7.40 (m, 4H), 7.37-7.26 (m, 4H), 4.73-4.68 (m, 1H), 4.60-4.47 (m, 5H), 4.41-4.33 (m, 1H), 3.92 (d, J = 11.0 Hz, 1H), 3.83 (dd, J = 11.0, 3.9 Hz, 1H), 3.65-3.55 (m, 1H), 3.51 (p, J = 6.1 Hz, 1H), 2.80-2.69 (m, 2H), 2.68-2.47 (m, 5H), 2.34-2.18 (m, 3H), 2.13-1.92 (m, 2H), 1.67-1.56 (m, 1H), 1.45 (s, 9H), 1.17 (d, J = 6.2 Hz, 3H), 1.05 (s, 9H). |
| G34 | 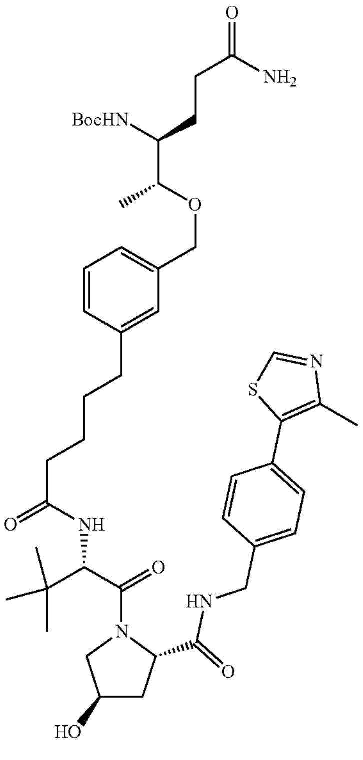 [SMILES: Cc1ncsc1-c1ccc(CNC(=O)[C@@H]2C[C@@H](O)CN2C(=O)[C@@H](NC(=O)CCCCc2cccc(CO[C@H](C)[C@H](CCC(N)=O)NC(=O)OC(C)(C)C)c2)C(C)(C)C)cc1] | tert-butyl N-[(3S,4R)-1-carbamoyl-4-[[3-(4-[[(2S)-1-[(2S,4R)-4-hydroxy-2-([[4-(4-methyl-1,3-thiazol-5-yl)phenyl]methyl] carbamoyl)pyrrolidin-1-yl]-3,3-dimethyl-1-oxobutan-2-yl]carbamoyl]butyl) phenyl]methoxy]pentan-3-yl]carbamate | 849.3 | (400 MHz, $CD_3OD$) δ 8.90 (s, 1H), 7.49 (d, J = 8.3 Hz, 2H), 7.48-7.40 (m, 2H), 7.28-7.19 (m, 2H), 7.16 (d, J = 7.6 Hz, 1H), 7.17-7.08 (m, 1H), 4.69-4.44 (m, 7H), 4.37 (d, J = 15.6 Hz, 1H), 3.93 (d, J = 11.0 Hz, 1H), 3.82 (dd, J = 11.0, 3.9 Hz, 1H), 3.59 (s, 1H), 3.50 (p, J = 6.3 Hz, 1H), 2.65 (s, 2H), 2.49 (s, 3H), 2.38-2.25 (m, 1H), 2.29-2.16 (m, 2H), 2.15-1.97 (m, 1H), 2.01 (s, 1H), 1.70-1.60 (m, 6H), 1.45 (s, 9H), 1.18 (d, J = 6.3 Hz, 3H), 1.05 (s, 9H). |

TABLE 47-continued

| Characterization data for intermediates prepare according to the procedure above. | | | | |
|---|---|---|---|---|
| Inter-me-diate | Structure | Chemical Name | MS: [(M + 1)]+ | 1H-NMR |
| G35 | 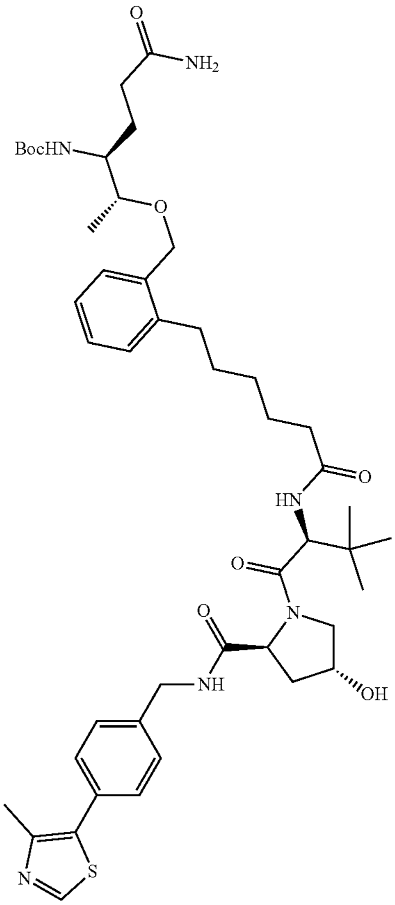 [SMILES: Cc1ncsc1-c1ccc(CNC(=O)[C@@H]2C[C@@H](O)CN2C(=O)[C@@H](NC(=O)CCCCCc2ccccc2CO[C@H](C)[C@H](CCC(N)=O)NC(=O)OC(C)(C)C)C(C)(C)C)cc1] | tert-butyl N-[(3S,4R)-1-carbamoyl-4-[[2-(5-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]pentyl)phenyl]methoxy]pentan-3-yl]carbamate | 863.6 | (400 MHz, DMSO-$d_6$) δ 8.99 (s, 1H), 8.57 (t, J = 6.1 Hz, 1H), 7.88 (d, J = 9.3 Hz, 1H), 7.43 (d, J = 8.5 Hz, 2H), 7.39 (d, J = 8.4 Hz, 2H), 7.32 (dd, J = 7.5, 1.5 Hz, 1H), 7.25-7.11 (m, 4H), 6.71 (s, 1H), 6.60 (d, J = 8.8 Hz, 1H), 4.57-4.49 (m, 2H), 4.46-4.40 (m, 3H), 4.36 (s, 1H), 4.22 (dd, J = 15.9, 5.5 Hz, 1H), 3.67 (d, J = 4.6 Hz, 2H), 3.40-3.34 (m, 2H), 2.58 (t, J = 7.8 Hz, 2H), 2.45 (s, 3H), 2.29 (dt, J = 14.8, 7.6 Hz, 2H), 2.15-1.99 (m, 5H), 1.91 (d, J = 4.2 Hz, 1H), 1.82-1.73 (m, 1H), 1.60-1.43 (m, 4H), 1.39 (s, 9H), 1.34-1.28 (m, 2H), 1.08 (d, J = 5.7 Hz, 3H), 0.94 (s, 9H). |

TABLE 47-continued

Characterization data for intermediates prepare according to the procedure above.

| Intermediate | Structure | Chemical Name | MS: [(M + 1)]⁺ | ¹H-NMR |
|---|---|---|---|---|
| G36 | 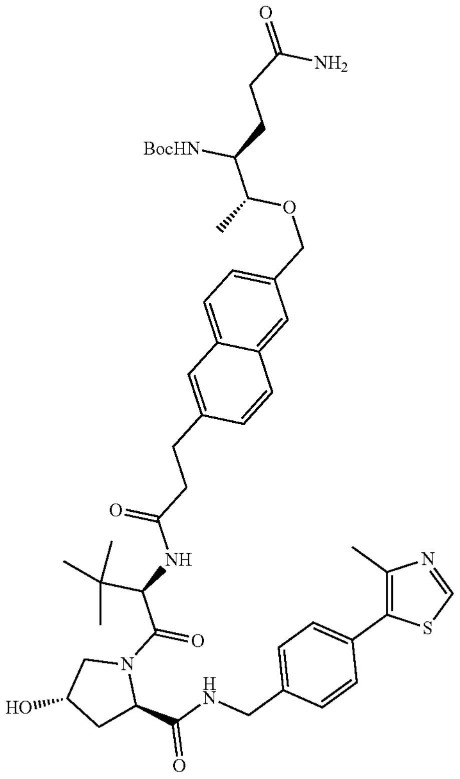 [SMILES: Cc1ncsc1-c1ccc(CNC(=O)[C@H]2C[C@H](O)CN2C(=O)[C@H](NC(=O)CCc2ccc3cc(CO[C@H](C)[C@H](CCC(N)=O)NC(=O)OC(C)(C)C)ccc3c2)C(C)(C)C)cc1] | tert-butyl N-[(3S,4R)-1-carbamoyl-4-[[6-(2-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]ethyl)naphthalen-2-yl]methoxy]pentan-3-yl]carbamate | 871.6 | (400 MHz, $CD_3OD$) δ 8.89 (s, 1H), 7.82-7.74 (m, 3H), 7.68 (s, 1H), 7.48 (m, 3H), 7.47-7.36 (m, 3H), 4.73 (d, J = 11.7 Hz, 1H), 4.67 (d, J = 11.8 Hz, 1H), 4.64-4.50 (m, 3H), 4.49 (s, 1H), 4.36 (d, J = 15.5 Hz, 1H), 3.90 (d, J = 11.0 Hz, 1H), 3.77 (dd, J = 10.9, 4.0 Hz, 1H), 3.64-3.52 (m, 1H), 3.10 (t, J = 7.6 Hz, 2H), 2.81-2.61 (m, 2H), 2.49 (s, 3H), 2.36-2.17 (m, 2H), 2.13-1.97 (m, 1H), 1.75-1.58 (m, 2H), 1.42 (s, 9H), 1.21 (d, J = 6.1 Hz, 3H), 1.16-1.01 (m, 2H), 0.92 (s, 9H). |

TABLE 47-continued

| Characterization data for intermediates prepare according to the procedure above. | | | | |
|---|---|---|---|---|
| Inter-me-diate | Structure | Chemical Name | MS: [(M + 1)]$^+$ | $^1$H-NMR |
| G37 | 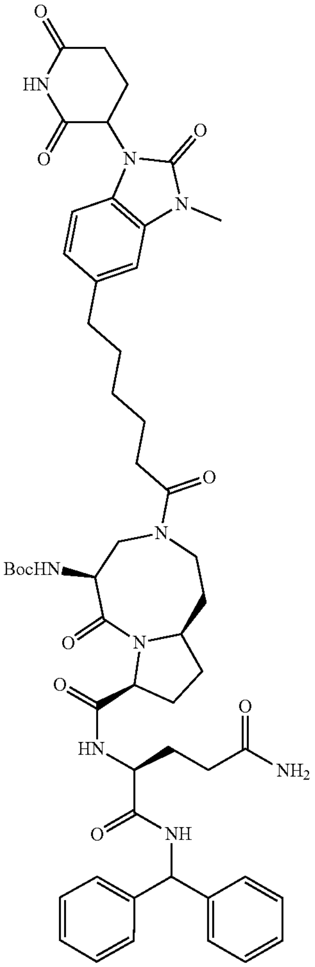 [SMILES: Cn1c(=O)n(C2CCC(=O)NC2=O)c2ccc(CCCCCC(=O)N3CC[C@H]4CC[C@@H](C(=O)N[C@@H](CCC(N)=O)C(=O)NC(c5ccccc5)c5ccccc5)N4C(=O)[C@@H](NC(=O)OC(C)(C)C)C3)cc21] | tert-butyl N-[(5S,8S,10aR)-8-[[(1S)-3-carbamoyl-1-(diphenylmethylcarbamoyl)propyl]carbamoyl]-3-[6-[1-(2,6-dioxopiperidin-3-yl)-3-methyl-2-oxo-1,3-benzodiazol-5-yl]hexanoyl]-6-oxo-octahydropyrrolo[1,2-a][1,5]diazocin-5-yl]carbamate | 976.2 | (400 MHz, $CDCl_3$) δ 9.68 (s, 1H), 9.25 (s, 1H), 8.03-7.79 (m, 1H), 7.51 (d, J = 7.0 Hz, 1H), 7.36-7.17 (m, 14H), 6.90-6.78 (m, 2H), 6.78-6.60 (m, 1H), 6.53-6.42 (m, 1H), 6.20 (dd, J = 8.2, 3.5 Hz, 1H), 5.89-5.73 (m, 2H), 5.31-5.10 (m, 1H), 4.56 (m, 1H), 4.46-4.28 (m, 2H), 4.10-3.79 (m, 2H), 3.42 (s, 3H), 3.41-3.27 (m, 1H), 3.26-3.09 (m, 1H), 3.07-2.95 (m, 1H), 2.93-2.78 (m, 1H), 2.78-2.56 (m, 3H), 2.56-2.35 (m, 1H), 2.34-2.08 (m, 4H), 2.06-1.78 (m, 2H), 1.78-1.53 (m, 5H), 1.51-1.40 (m, 9H), 1.40-1.22 (m, 2H). |

TABLE 47-continued

| Characterization data for intermediates prepare according to the procedure above. | | | | |
|---|---|---|---|---|
| Inter-me-diate | Structure | Chemical Name | MS: [(M + 1)]$^+$ | $^1$H-NMR |
| G38 | 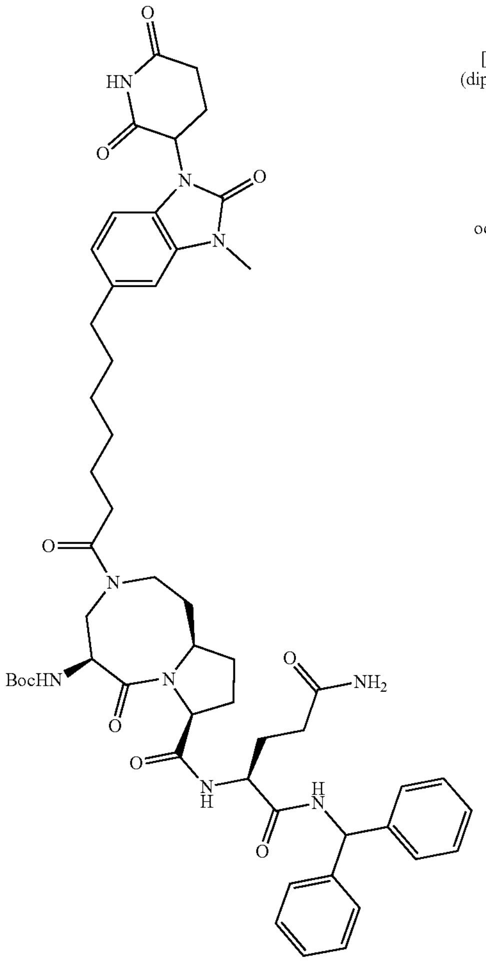 | tert-butyl N-[(5S,8S,10aR)-8-[[(1S)-3-carbamoyl-1-(diphenylmethylcarbamoyl)propyl]carbamoyl]-3-[7-[1-(2,6-dioxopiperidin-3-yl)-3-methyl-2-oxo-1,3-benzodiazol-5-yl]heptanoyl]-6-oxo-octahydropyrrolo[1,2-a][1,5]diazocin-5-yl]carbamate | 990.5 | (400 MHz, DMSO-$d_6$) δ 11.09 (s, 1H), 8.80-8.65 (m, 1H), 8.18 (t, J = 1.3 Hz, 1H), 7.40-7.14 (m, 10H), 7.04-6.91 (m, 2H), 6.86 (dt, J = 8.1, 1.8 Hz, 1H), 6.73 (d, J = 17.2 Hz, 1H), 6.49 (d, J = 6.8 Hz, 1H), 6.10 (d, J = 8.4 Hz, 1H), 5.34 (dd, J = 12.7, 5.4 Hz, 1H), 4.38 (m, 2H), 4.19-4.05 (m, 1H), 3.71 (d, J = 14.2 Hz, 1H), 3.54-3.34 (m, 1H), 3.33 (s, 3H), 3.28-2.98 (m, 2H), 2.90 (ddd, J = 16.8, 12.6, 5.1 Hz, 1H), 2.80-2.55 (m, 6H), 2.48-2.23 (m, 2H), 2.20-2.09 (m, 6H), 2.06-1.69 (m, 2H), 1.69-1.46 (m, 5H), 1.43-1.25 (m, 15H). |

TABLE 47-continued

| Characterization data for intermediates prepare according to the procedure above. | | | | |
|---|---|---|---|---|
| Inter-me-diate | Structure | Chemical Name | MS: [(M + 1)]+ | $^1$H-NMR |
| G39 | 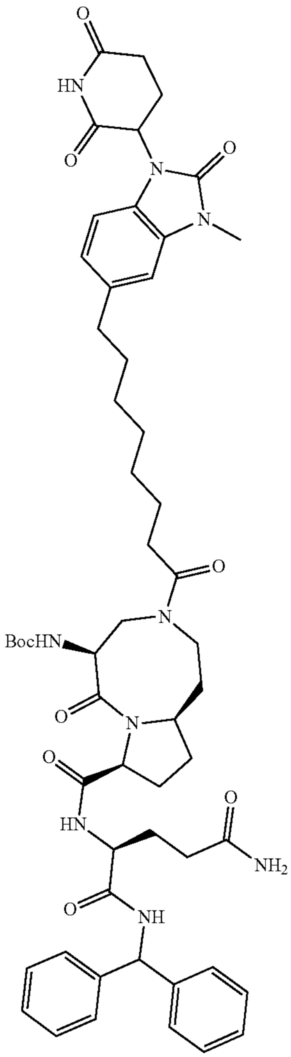 [SMILES: Cn1c(=O)n(C2CCC(=O)NC2=O)c2ccc(CCCCCCCC(=O)N3CC[C@H]4CC[C@@H](C(=O)N[C@@H](CCC(N)=O)C(=O)NC(c5ccccc5)c5ccccc5)N4C(=O)[C@@H](NC(=O)OC(C)(C)C)C3)cc21] | tert-butyl N-[(5S,8S,10aR)-8-[[(1S)-3-carbamoyl-1-(diphenylmethylcarbamoyl)propyl]carbamoyl]-3-[8-[1-(2,6-dioxopiperidin-3-yl)-3-methyl-2-oxo-1,3-benzodiazol-5-yl]octanoyl]-6-oxo-octahydropyrrolo[1,2-a][1,5]diazocin-5-yl]carbamate | 1004.6 | (400 MHz, DMSO-$d_6$) δ 11.09 (s, 1H), 8.74 (d, J = 8.5 Hz, 1H), 8.19 (t, J = 7.3 Hz, 1H), 7.38-7.19 (m, 11H), 7.05-6.91 (m, 2H), 6.85 (dt, J = 8.0, 1.8 Hz, 1H), 6.73 (d, J = 16.8 Hz, 1H), 6.48 (d, J = 6.9 Hz, 1H), 6.09 (d, J = 8.3 Hz, 1H), 5.34 (dd, J = 12.7, 5.3 Hz, 1H), 4.48-4.30 (m, 2H), 4.20-4.05 (m, 1H), 3.80-3.70 (m, 2H), 3.32 (s, 3H), 3.25-3.30 (m, 2H), 2.90-2.80 (m, 1H), 2.75-2.56 (m, 4H), 2.47-2.25 (m, 2H), 2.19-1.65 (m, 10H), 1.65-1.45 (m, 8H), 1.37 (s, 9H), 1.36-1.25 (m, 4H). |

TABLE 47-continued

| Characterization data for intermediates prepare according to the procedure above. | | | | |
|---|---|---|---|---|
| Inter-me-diate | Structure | Chemical Name | MS: [(M + 1)]$^+$ | $^1$H-NMR |
| G40 | 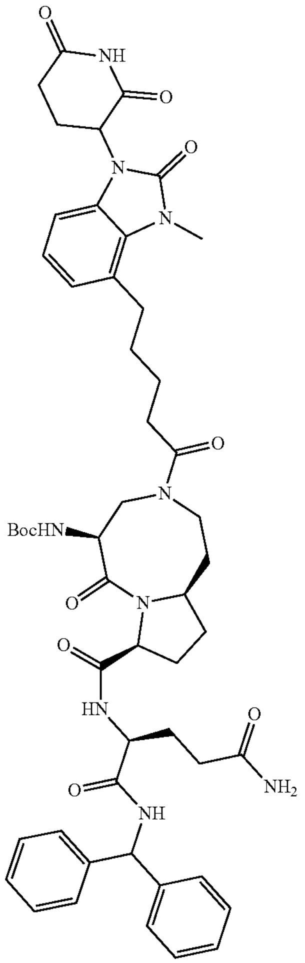 [SMILES: Cn1c(=O)n(C2CCC(=O)NC2=O)c2cccc(CCCCC(=O)N3CC[C@H]4CC[C@@H](C(=O)N[C@@H](CCC(N)=O)C(=O)NC(c5ccccc5)c5ccccc5)N4C(=O)[C@@H](NC(=O)OC(C)(C)C)C3)c21] | tert-butyl N-[(5S,8S,10aR)-8-[[(1S)-3-carbamoyl-1-(diphenylmethylcarbamoyl)propyl]carbamoyl]-3-[5-[1-(2,6-dioxopiperidin-3-yl)-3-methyl-2-oxo-1,3-benzodiazol-4-yl]pentanoyl]-6-oxo-octahydropyrrolo[1,2-a][1,5]diazocin-5-yl]carbamate | 962.4 | (400 MHz, DMSO-$d_6$) δ 11.10 (s, 1H), 8.73 (d, J = 8.5 Hz, 1H), 8.18 (dd, J = 18.3, 8.4 Hz, 1H), 7.35-4.10 (m, 12H), 7.03-6.92 (m, 2H), 6.89 (d, J = 6.3 Hz, 1H), 6.76-6.70 (m, 1H), 6.46 (d, J = 6.7 Hz, 1H), 6.11 (d, J = 8.3 Hz, 1H), 5.37 (dd, J = 12.4, 5.3 Hz, 1H), 4.45-4.36 (m, 3H), 4.13 (s, 1H), 3.76 (d, J = 14.7 Hz, 1H), 3.57 (d, J = 3.9 Hz, 3H), 3.21 (s, 1H), 3.10 (d, J = 12.7 Hz, 1H), 3.00-2.90 (m, 3H), 2.78-2.50 (m, 4H), 2.12 (d, J = 6.6 Hz, 2H), 2.09-2.00 (m, 5H), 2.00-1.86 (s, 1H), 1.84-1.75 (m, 2H), 1.70-1.50 (s, 5H), 1.38 (s, 9H). |

TABLE 47-continued

| Characterization data for intermediates prepare according to the procedure above. | | | | |
|---|---|---|---|---|
| Inter-me-diate | Structure | Chemical Name | MS: [(M + 1)]$^+$ | $^1$H-NMR |
| G41 | 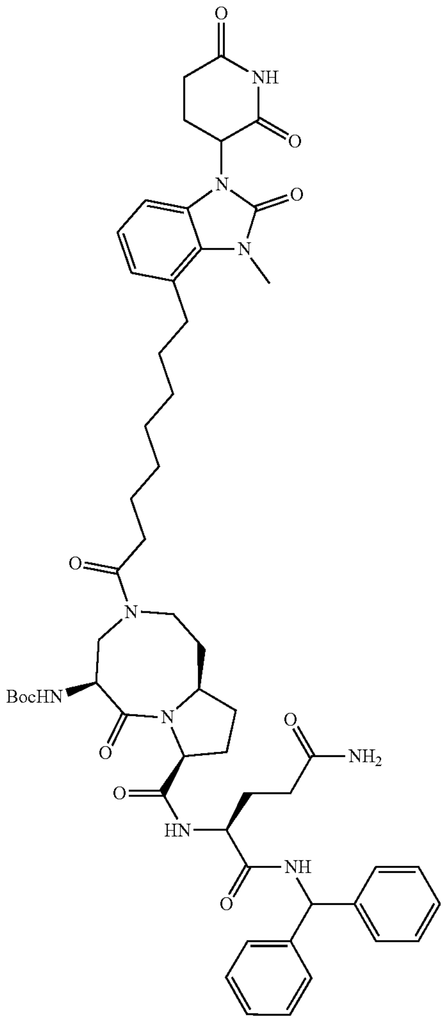 [SMILES: Cn1c(=O)n(C2CCC(=O)NC2=O)c2cccc(CCCCCCCC(=O)N3CC[C@H]4CC[C@@H](C(=O)N[C@@H](CCC(N)=O)C(=O)NC(c5ccccc5)c5ccccc5)N4C(=O)[C@@H](NC(=O)OC(C)(C)C)C3)c21] | tert-butyl N-[(5S,8S,10aR)-8-[[(1S)-3-carbamoyl-1-(diphenylmethylcarbamoyl)propyl]carbamoyl]-3-[8-[1-(2,6-dioxopiperidin-3-yl)-3-methyl-2-oxo-1,3-benzodiazol-4-yl]octanoyl]-6-oxo-octahydropyrrolo[1,2-a][1,5]diazocin-5-yl]carbamate | 1004.6 | (400 MHz, DMSO-$d_6$) δ 11.10 (s, 1H), 8.74 (d, J = 8.7 Hz, 1H), 8.18 (d, J = 9.4 Hz, 1H), 7.38-7.20 (m, 11H), 6.99-6.91 (m, 2H), 6.86 (dt, J = 5.9, 2.9 Hz, 1H), 6.80-6.70 (m, 1H), 6.47 (d, J = 6.8 Hz, 1H), 6.10 (d, J = 8.4 Hz, 1H), 5.37 (dd, J = 12.6, 5.4 Hz, 1H), 4.45-4.30 (m, 3H), 4.19-4.01 (m, 1H), 3.71 (d, J = 13.8 Hz, 2H), 3.55 (s, 3H), 3.21 (s, 1H), 3.08 (t, J = 12.6 Hz, 1H), 2.97-2.90 (m, 3H), 2.72 (td, J = 13.0, 4.5 Hz, 1H), 2.66-2.58 (m, 1H), 2.44 (q, J = 7.6 Hz, 2H), 2.30-2.20 (m, 1H), 2.15-2.00 (m, 6H), 1.98 (dd, J = 12.2, 5.9 Hz, 2H), 1.94-1.90 (m, 1H), 1.85-1.18 (m, 3H), 1.66-1.47 (m, 6H), 1.37 (s, 9H), 1.36-1.25 (m, 2H). |

TABLE 47-continued

| Characterization data for intermediates prepare according to the procedure above. | | | | |
|---|---|---|---|---|
| Inter-me-diate | Structure | Chemical Name | MS: [(M + 1)]+ | $^1$H-NMR |
| G42 | 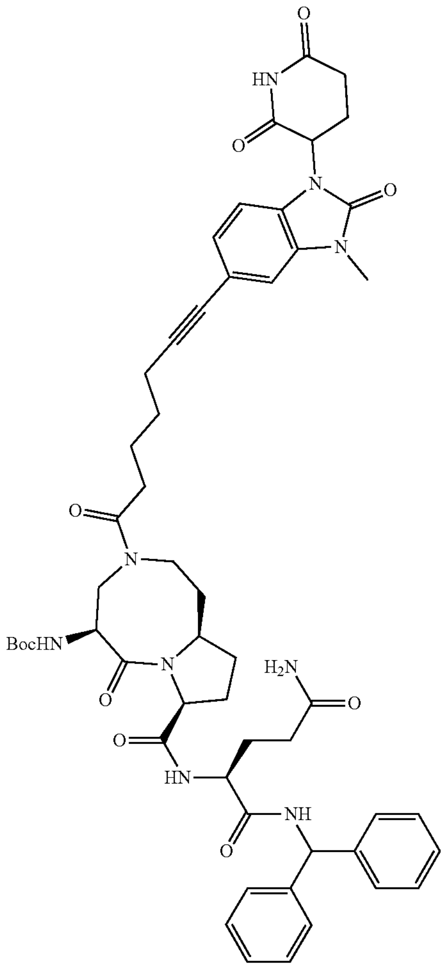 [SMILES: Cn1c(=O)n(C2CCC(=O)NC2=O)c2ccc(C#CCCCCC(=O)N3CC[C@H]4CC[C@@H](C(=O)N[C@@H](CCC(N)=O)C(=O)NC(c5ccccc5)c5ccccc5)N4C(=O)[C@@H](NC(=O)OC(C)(C)C)C3)cc21] | tert-butyl N-[(5S,8S,10aR)-8-[[(1S)-3-carbamoyl-1-(diphenylmethylcarbamoyl)propyl]carbamoyl]-3-[7-[1-(2,6-dioxopiperidin-3-yl)-3-methyl-2-oxo-1,3-benzodiazol-5-yl]hept-6-ynoyl]-6-oxo-octahydropyrrolo[1,2-a][1,5]diazocin-5-yl]carbamate | 986.8 | (400 MHz, DMSO-$d_6$) δ 11.12 (s, 1H), 8.73 (d, J = 8.5 Hz, 1H), 8.18 (dd, J = 7.9, 4.9 Hz, 1H), 7.40-7.17 (m, 14H), 7.09 (s, 2H), 6.76-6.70 (m, 1H), 6.50 (d, J = 6.6 Hz, 1H), 6.10 (d, J = 8.4 Hz, 1H), 5.38 (dd, J = 12.8, 5.3 Hz, 1H), 4.50-4.30 (m, 3H), 4.14 (s, 2H), 3.72 (t, J = 12.2 Hz, 2H), 3.34 (s, 3H), 3.23 (d, J = 12.1 Hz, 1H), 3.12 (t, J = 12.2 Hz, 1H), 2.96-2.81 (m, 1H), 2.77-2.57 (m, 3H), 2.48-2.39 (m, 3H), 2.22-1.98 (m, 4H), 1.92 (s, 2H), 1.86-1.51 (m, 6H), 1.39 (s, 9H). |

TABLE 47-continued

| Characterization data for intermediates prepare according to the procedure above. | | | | |
|---|---|---|---|---|
| Inter-me-diate | Structure | Chemical Name | MS: [(M + 1)]$^+$ | $^1$H-NMR |
| G43 | 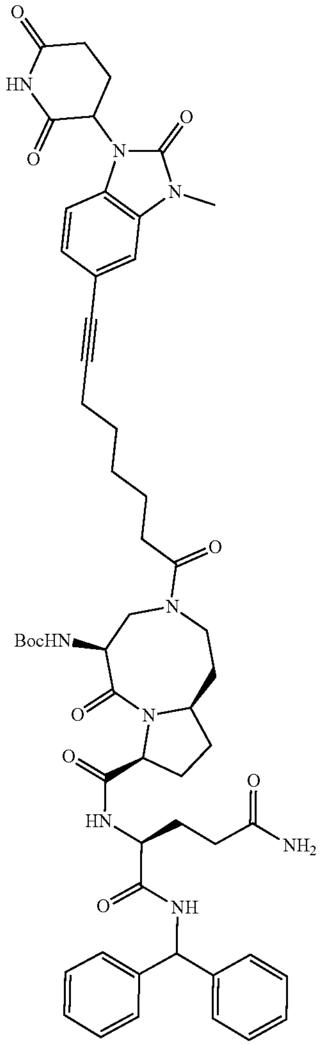 [SMILES: Cn1c(=O)n(C2CCC(=O)NC2=O)c2ccc(C#CCCCCCC(=O)N3CC[C@H]4CC[C@@H](C(=O)N[C@@H](CCC(N)=O)C(=O)NC(c5ccccc5)c5ccccc5)N4C(=O)[C@@H](NC(=O)OC(C)(C)C)C3)cc21] | tert-butyl N-[(5S,8S,10aR)-8-[[(1S)-3-carbamoyl-1-(diphenylmethylcarbamoyl)propyl]carbamoyl]-3-[8-[1-(2,6-dioxopiperidin-3-yl)-3-methyl-2-oxo-1,3-benzodiazol-5-yl]oct-7-ynoyl]-6-oxo-octahydropyrrolo[1,2-a][1,5]diazocin-5-yl]carbamate | 1000.2 | (400 MHz, $CDCl_3$) δ 10.03 (s, 1H), 9.46 (s, 1H), 7.88 (t, J = 7.3 Hz, 1H), 7.71-7.47 (m, 1H), 7.34-7.18 (m, 15H), 7.15-6.97 (m, 3H), 6.72 (dd, J = 13.0, 8.1 Hz, 1H), 6.55-6.45 (m, 1H), 6.19 (dd, J = 8.2, 2.5 Hz, 1H), 5.91-5.71 (m, 2H), 5.21 (d, J = 5.3 Hz, 1H), 4.66-4.36 (m, 2H), 4.25-4.13 (m, 1H), 4.09-3.70 (m, 2H), 3.34 (s, 3H), 3.20-2.93 (m, 2H), 2.90-2.60 (m, 3H), 2.59-2.33 (m, 4H), 2.33-1.91 (m, 6H), 1.91-1.37 (m, 14H). |

TABLE 47-continued

| Characterization data for intermediates prepare according to the procedure above. | | | | |
|---|---|---|---|---|
| Inter-me-diate | Structure | Chemical Name | MS: [(M + 1)]$^+$ | $^1$H-NMR |
| G44 | 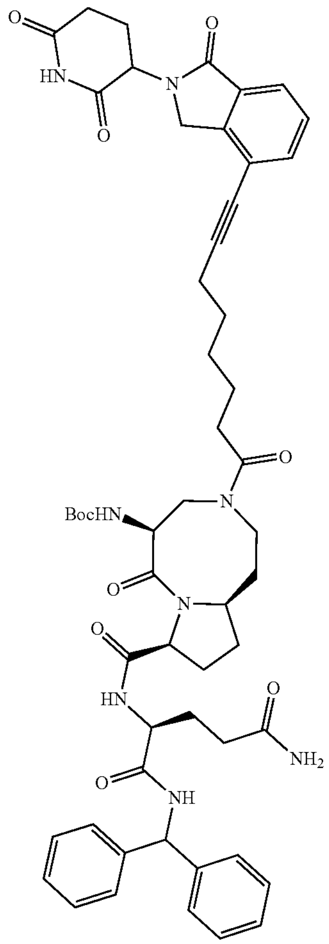 [SMILES: CC(C)(C)OC(=O)N[C@H]1CN(C(=O)CCCCCC#Cc2cccc3c2CN(C2CCC(=O)NC2=O)C3=O)CC[C@H]2CC[C@@H](C(=O)N[C@@H](CCC(N)=O)C(=O)NC(c3ccccc3)c3ccccc3)N2C1=O] | tert-butyl N-[(5S,8S,10aR)-8-[[(1S)-3-carbamoyl-1-(diphenylmethylcarbamoyl)propyl]carbamoyl]-3-[8-[2-(2,6-dioxopiperidin-3-yl)-1-oxo-3H-isoindol-4-yl]oct-7-ynoyl]-6-oxo-octahydropyrrolo[1,2-a][1,5]diazocin-5-yl]carbamate | 985.7 | (400 MHz, $CDCl_3$) δ 7.92-7.71 (m, 2H), 7.61-7.50 (m, 1H), 7.46 (dt, J = 8.8, 7.4 Hz, 1H), 7.39-7.16 (m, 15H), 6.29-6.18 (m, 1H), 5.82-5.67 (m, 1H), 5.59 (s, 1H), 5.38-5.15 (m, 1H), 4.90-4.80 (m, 1H), 4.77-4.20 (m, 4H), 4.11 (s, 1H), 3.90-3.75 (m, 1H), 3.72-3.03 (m, 2H), 2.94-2.72 (m, 1H), 2.60-2.40 (m, 4H), 2.38-1.87 (m, 6H), 1.70-1.47 (m, 12H), 1.45 (s, 9H). . |

TABLE 47-continued

| Characterization data for intermediates prepare according to the procedure above. | | | | |
|---|---|---|---|---|
| Inter-me-diate | Structure | Chemical Name | MS: [(M + 1)]$^+$ | $^1$H-NMR |
| G45 | 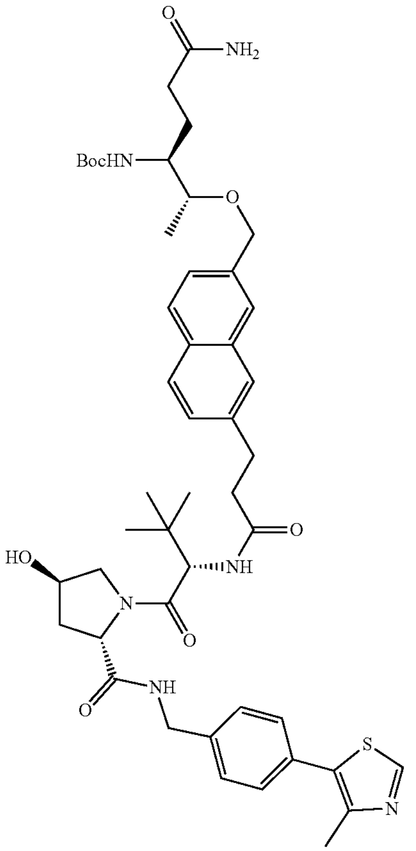 [SMILES: Cc1ncsc1-c1ccc(CNC(=O)[C@@H]2C[C@@H](O)CN2C(=O)[C@@H](NC(=O)CCc2ccc3ccc(CO[C@H](C)[C@H](CCC(N)=O)NC(=O)OC(C)(C)C)cc3c2)C(C)(C)C)cc1] | tert-butyl N-[(3S,4R)-1-carbamoyl-4-[[7-(2-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]ethyl)naphthalen-2-yl]methoxy]pentan-3-yl]carbamate | 871.55 | (400 MHz, DMSO-$d_6$) δ 8.99 (s, 1H), 8.58-8.55 (m, 1H), 8.00 (d, J = 9.4 Hz, 1H), 7.83-7.79 (m, 2H), 7.74 (s, 1H), 7.68 (s, 1H), 7.41 (m, J = 8.3 Hz, 6H), 7.24 (s, 1H), 6.73-6.61 (m, 2H), 5.16 (d, J = 3.5 Hz, 1H), 4.69-4.53 (m, 3H), 4.50-4.34 (m, 3H), 4.23-4.21 (m, 1H), 3.71-3.64 (m, 2H), 3.53-3.41 (m, 2H), 3.20-3.07 (m, 1H), 3.02-2.93 (m, 2H), 2.72-2.69 (m, 1H), 2.45 (s, 3H) 2.04-1.98 (m, 4H), 1.87-1.65 (m, 1H), 1.41-1.39 (m, 1H), 1.38 (s, 9H), 1.10 (d, J = 5.9 Hz, 3H), 0.89 (s, 9H) |

TABLE 47-continued

| Characterization data for intermediates prepare according to the procedure above. | | | | |
|---|---|---|---|---|
| Inter-me-diate | Structure | Chemical Name | MS: [(M + 1)]$^+$ | $^1$H-NMR |
| G46 | 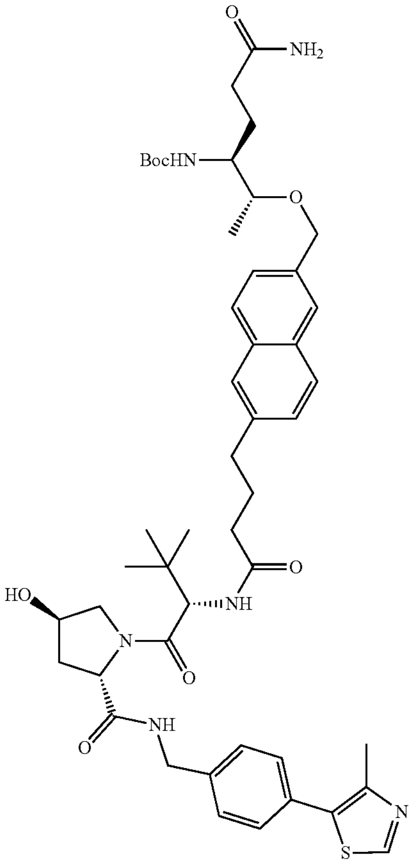 [SMILES: Cc1ncsc1-c1ccc(CNC(=O)[C@@H]2C[C@@H](O)CN2C(=O)[C@@H](NC(=O)CCCc2ccc3cc(CO[C@H](C)[C@H](CCC(N)=O)NC(=O)OC(C)(C)C)ccc3c2)C(C)(C)C)cc1] | tert-butyl N-[(3S,4R)-1-carbamoyl-4-[[6-(3-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]propyl)naphthalen-2-yl]methoxy]pentan-3-yl]carbamate | 885.40 | (400 MHz, $CD_3OD$) δ 8.89 (s, 1H), 7.90-7.73 (m, 4H), 7.66 (s, 1H), 7.52-7.34 (m, 5H), 4.78-4.50 (m, 5H), 4.37 (d, J = 15.5 Hz, 1H), 3.95 (d, J = 11.0 Hz, 1H), 3.83 (dd, J = 11.0, 3.9 Hz, 1H), 3.68-3.47 (m, 3H), 2.90-2.77 (m, 2H), 2.49 (s, 3H), 2.42-2.19 (m, 4H), 2.16-1.98 (m, 4H), 1.66 (s, 1H), 1.41 (s, 7H), 1.40 (d, J = 1.7 Hz, 2H), 1.22 (dd, J = 6.1, 3.1 Hz, 4H), 1.06 (s, 9H) |

TABLE 47-continued

| Characterization data for intermediates prepare according to the procedure above. | | | | |
|---|---|---|---|---|
| Intermediate | Structure | Chemical Name | MS: [(M + 1)]+ | $^1$H-NMR |
| G47 | 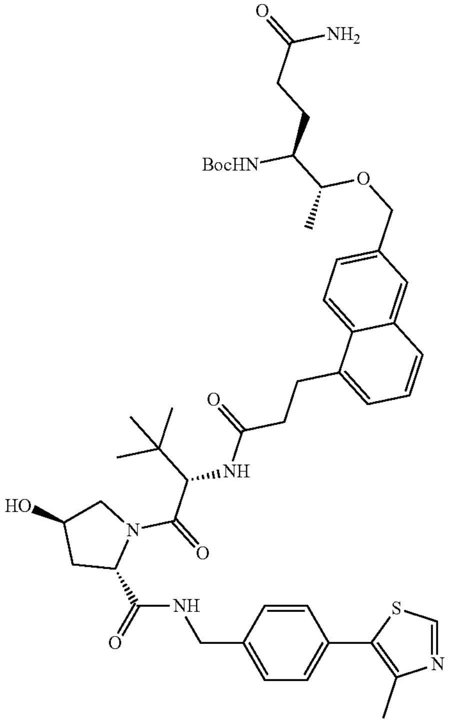 [SMILES: Cc1ncsc1-c1ccc(CNC(=O)[C@@H]2C[C@@H](O)CN2C(=O)[C@@H](NC(=O)CCc2cccc3cc(CO[C@H](C)[C@H](CCC(N)=O)NC(=O)OC(C)(C)C)ccc23)C(C)(C)C)cc1] | tert-butyl N-[(3S,4R)-1-carbamoyl-4-[[5-(2-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]ethyl)naphthalen-2-yl]methoxy]pentan-3-yl]carbamate | 871.35 | (400 MHz, DMSO-$d_6$) δ 8.99 (s, 1H), 8.58 (t, J = 6.0 Hz, 1H), 8.06 (d, J = 9.1 Hz, 2H), 7.87-7.82 (m, 1H), 7.74 (d, J = 8.1 Hz, 1H), 7.56-7.49 (m, 1H), 7.43-7.38 (m, 6H), 7.24 (s, 1H), 6.71 (s, 1H), 6.66 (d, J = 8.9 Hz, 1H), 5.17 (d, J = 3.5 Hz, 1H), 4.67 (d, J = 12.0 Hz, 1H), 4.67-4.56 (m, 2H), 4.49-4.35 (m, 3H), 4.22 (dd, J = 15.7, 5.3 Hz, 1H), 3.71-3.67 (m, 2H), 3.50-3.44 (m, 3H), 3.28-3.24 (m, 1H), 2.61-2.53 (m, 1H), 2.45 (s, 3H), 2.05 (t, J = 10.6 Hz, 3H), 1.90-1.80 (m, 4H), 1.50 (s, 1H), 1.37 (s, 9H), 1.11 (d, J = 5.8 Hz, 3H), 0.93 (s, 9H). |
| G48 | 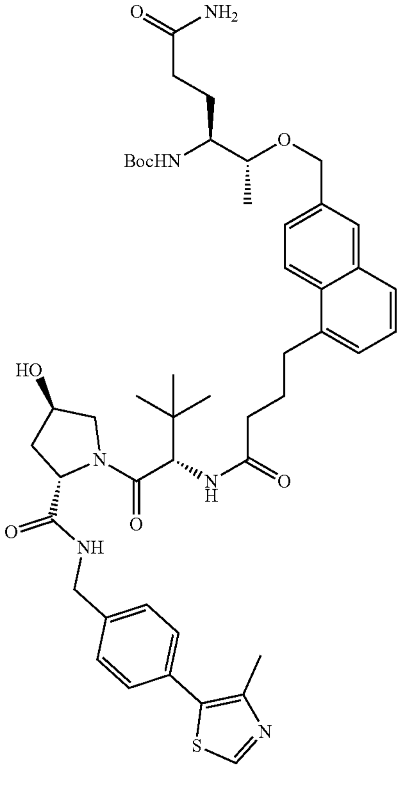 [SMILES: Cc1ncsc1-c1ccc(CNC(=O)[C@@H]2C[C@@H](O)CN2C(=O)[C@@H](NC(=O)CCCc2cccc3cc(CO[C@H](C)[C@H](CCC(N)=O)NC(=O)OC(C)(C)C)ccc23)C(C)(C)C)cc1] | tert-butyl N-[(3S,4R)-1-carbamoyl-4-[[5-(3-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]propyl)naphthalen-2-yl]methoxy]pentan-3-yl]carbamate | 885.40 | (400 MHz, DMSO-$d_6$) δ 8.99 (s, 1H), 8.56 (t, J = 6.0 Hz, 1H), 8.06 (d, J = 8.8 Hz, 1H), 7.97 (d, J = 9.3 Hz, 1H), 7.84 (s, 1H), 7.73 (d, J = 8.1 Hz, 1H), 7.51 (dd, J = 8.8, 1.7 Hz, 1H), 7.44-.40 (m, 3H), 7.40-7.37 (m, 2H), 7.32 (d, J = 7.0 Hz, 1H), 7.23 (s, 1H), 6.72-6.61 (m, 2H), 5.13 (d, J = 3.6 Hz, 1H), 4.68-4.58 (m, 3H), 4.45-4.42 (m, 2H), 4.37 (s, 1H), 4.24-4.20 (m, 1H), 3.69 (s, 2H), 3.53-3.42 (m, 2H), 3.02-2.97 (m, 2H), 2.45 (s, 3H), 2.39 (q, J = 7.2 Hz, 1H), 2.28-2.25 (m, 1H), 2.10-2.01 (m, 3H), 1.95-1.80 (m, 4H), 1.56-1.46 (m, 1H), 1.37 (s, 9H), 1.11 (d, J = 5.9 Hz, 3H), 0.96 (s, 9H). |

TABLE 47-continued

| Characterization data for intermediates prepare according to the procedure above. | | | | |
|---|---|---|---|---|
| Inter-me-diate | Structure | Chemical Name | MS: [(M + 1)]$^+$ | $^1$H-NMR |
| G49 | 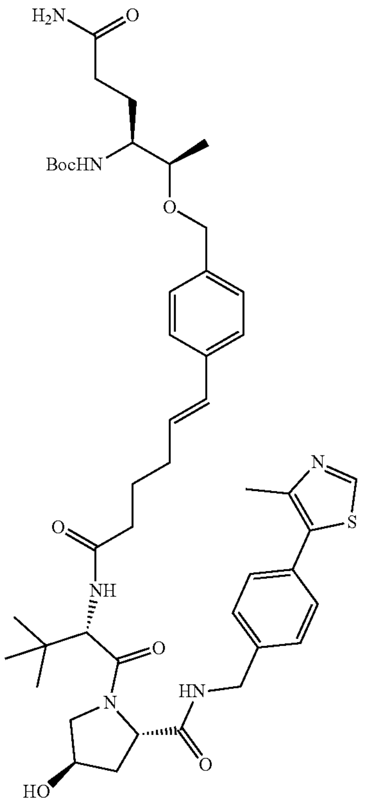 [SMILES: Cc1ncsc1-c1ccc(CNC(=O)[C@@H]2C[C@@H](O)CN2C(=O)[C@@H](NC(=O)CCC/C=C/c2ccc(CO[C@H](C)[C@H](CCC(N)=O)NC(=O)OC(C)(C)C)cc2)C(C)(C)C)cc1] | tert-butyl N-[(3.S,4R)-1-carbamoyl-4-([4-[(1E)-5-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]pent-1-en-1-yl]phenyl]methoxy)pentan-3-yl]carbamate | 861.40 | (400 MHz, DMSO-d$_6$) δ 8.99 (s, 1H), 8.57 (t, J = 6.1 Hz, 2H), 7.92 (d, J = 9.3 Hz, 1H), 7.44-7.34 (m, 9H), 7.28-7.20 (m, 3H), 6.69 (s, 1H), 6.61 (d, J = 9.1 Hz, 1H), 6.38 (d, J = 15.9 Hz, 1H), 6.33-6.22 (m, 1H), 5.76 (s, 2H), 5.13 (t, J = 3.6 Hz, 1H), 4.62-4.51 (m, 2H), 4.47-4.41 (m, 4H), 4.36 (s, 1H), 4.25-4.19 (m, 2H), 3.48-3.36 (m, 1H), 2.45 (s, 3H), 2.38-2.26 (m, 1H), 2.23-2.13 (m, 2H), 2.08-2.02 (m, 2H), 1.97-1.85 (m, 1H), 1.71-1.61 (m, 1H), 1.38 (s, 9H), 1.08-1.04 (d, J = 6.0 Hz, 3H), 0.95 (s, 9H) |
| G50 | 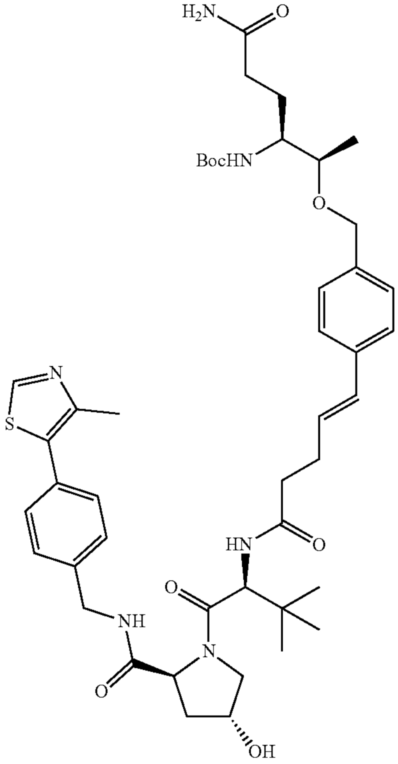 [SMILES: Cc1ncsc1-c1ccc(CNC(=O)[C@@H]2C[C@@H](O)CN2C(=O)[C@@H](NC(=O)CC/C=C/c2ccc(CO[C@H](C)[C@H](CCC(N)=O)NC(=O)OC(C)(C)C)cc2)C(C)(C)C)cc1] | tert-butyl N-[(3S,4R)-1-carbamoyl-4-([4-[(1E)-4-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]but-1-en-1-yl]phenyl]methoxy)pentan-3-yl]carbamate | 847.35 | (400 MHz, CDCl$_3$) δ 8.68 (s, 1H), 7.38-7.34 (m, 5H), 7.30 (d, J = 8.1 Hz, 2H), 7.22 (d, J = 8.1 Hz, 2H), 6.41 (d, J = 15.5 Hz, 1H), 6.34 (s, 1H), 6.21-6.10 (m, 2H), 5.39-5.33 (m, 1H), 5.30 (s, 1H), 4.84 (d, J = 9.6 Hz, 1H), 4.71-4.45 (m, 6H), 4.38-4.28 (m, 2H), 4.08 (d, J = 11.4 Hz, 1H), 3.68-3.52 (m, 3H), 2.54-2.52 (m, 3H), 2.38 (t, J = 7.6 Hz, 2H), 2.23 (t, J = 7.0 Hz, 2H), 2.12-2.03 (m, 1H), 2.00-1.90 (m, 1H), 1.63-1.58 (m, 2H) 1.42 (s, 9H), 1.25 (s, 1H), 1.18 (d, J = 6.2 Hz, 3H), 0.91 (s, 9H) |

TABLE 47-continued

| Characterization data for intermediates prepare according to the procedure above. | | | | |
|---|---|---|---|---|
| Intermediate | Structure | Chemical Name | MS: [(M + 1)]$^+$ | $^1$H-NMR |
| G51 | 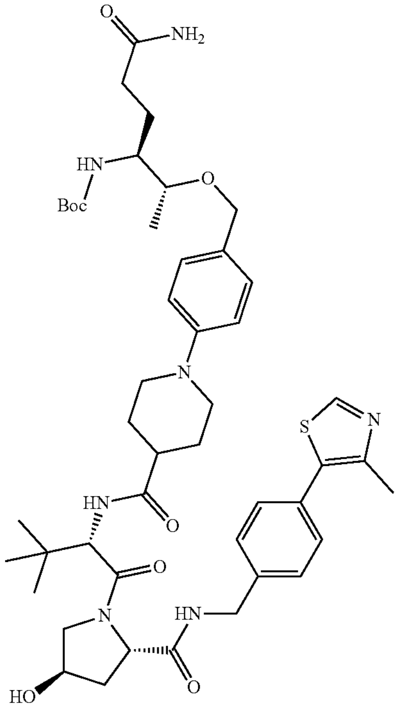 [SMILES: Cc1ncsc1-c1ccc(CNC(=O)[C@@H]2C[C@@H](O)CN2C(=O)[C@@H](NC(=O)C2CCN(c3ccc(CO[C@H](C)[C@H](CCC(N)=O)NC(=O)OC(C)(C)C)cc3)CC2)C(C)(C)C)cc1] | tert-butyl N-[(3S,4R)-1-carbamoyl-4-[[4-(4-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]piperidin-1-yl)phenyl]methoxy]pentan-3-yl]carbamate | 877.13 | (400 MHz, DMSO-$d_6$) δ 8.99 (s, 1H), 8.58 (t, J = 6.1 Hz, 1H), 7.87 (d, J = 9.2 Hz, 1H), 7.48-7.37 (m, 4H), 7.21 (s, 1H), 7.15 (d, J = 8.5 Hz, 2H), 6.88 (d, J = 8.4 Hz, 2H), 6.67 (s, 1H), 6.57 (d, J = 9.0 Hz, 1H), 5.14 (s, 1H), 4.54 (d, J = 9.3 Hz, 1H), 4.50-4.40 (m, 1H), 4.40-4.30 (m, 3H), 4.23 (dd, J = 15.8, 5.5 Hz, 1H), 3.73-3.63 (m, 5H), 2.71-2.59 (m, 2H), 2.45 (s, 3H), 2.11-1.95 (m, 4H), 1.95-1.86 (m, 1H), 1.86-1.73 (m, 2H), 1.73-1.57 (m, 3H), 1.39 (s, 9H), 1.29-1.22 (m, 3H), 1.04 (d, J = 5.9 Hz, 3H), 0.95 (s, 9H) |

TABLE 47-continued

| Characterization data for intermediates prepare according to the procedure above. | | | | |
|---|---|---|---|---|
| Inter-me-diate | Structure | Chemical Name | MS: [(M + 1)]$^+$ | $^1$H-NMR |
| G52 | 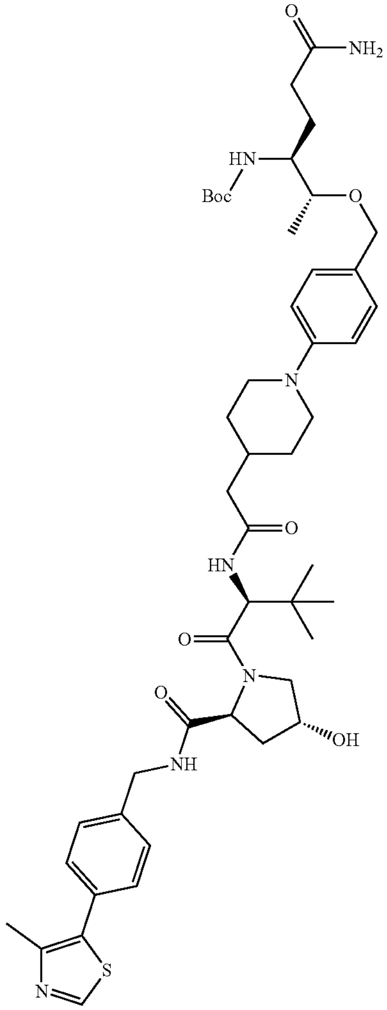 [SMILES: Cc1ncsc1-c1ccc(CNC(=O)[C@@H]2C[C@@H](O)CN2C(=O)[C@@H](NC(=O)CC2CCN(c3ccc(CO[C@H](C)[C@H](CCC(N)=O)NC(=O)OC(C)(C)C)cc3)CC2)C(C)(C)C)cc1] | tert-butyl N-[(3S,4R)-1-carbamoyl-4-([4-[4-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methyl)piperidin-1-yl]phenyl]methoxy)pentan-3-yl]carbamate | 890.51 | (400 MHz, $CD_3OD$) δ 8.89 (s, 1H), 7.49 (d, J = 8.3 Hz, 2H), 7.46-7.41 (m, 2H), 7.26-7.21 (m, 2H), 6.98-6.92 (m, 2H), 4.69-4.65 (m, 1H), 4.61-4.56 (m, 2H), 4.54-4.50 (m, 2H), 4.49-4.35 (m, 3H), 3.95 (d, J = 11.0 Hz, 1H), 3.83 (dd, J = 11.0, 3.9 Hz, 1H), 3.67 (dd, J = 12.1, 3.4 Hz, 2H), 3.60-3.47 (m, 2H), 2.74-2.65 (m, 2H), 2.29-2.21 (m, 5H), 2.14-2.08 (m, 1H), 2.01-1.88 (m, 2H), 1.84-1.77 (m, 2H), 1.62-1.54 (m, 1H), 1.50-1.42 (m, 13H), 1.16 (d, J = 6.1 Hz, 3H), 1.07 (s, 9H) |

TABLE 47-continued

| Characterization data for intermediates prepare according to the procedure above. | | | | |
|---|---|---|---|---|
| Inter-me-diate | Structure | Chemical Name | MS: [(M + 1)]$^+$ | $^1$H-NMR |
| G53 | 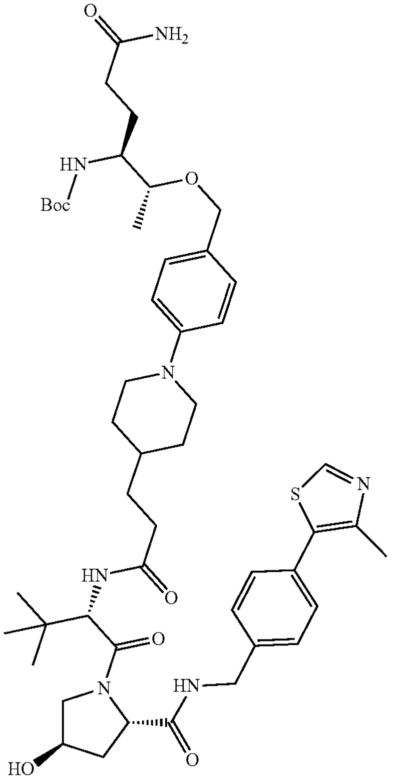 [SMILES: Cc1ncsc1-c1ccc(CNC(=O)[C@@H]2C[C@@H](O)CN2C(=O)[C@@H](NC(=O)CCC2CCN(c3ccc(CO[C@H](C)[C@H](CCC(N)=O)NC(=O)OC(C)(C)C)cc3)CC2)C(C)(C)C)cc1] | tert-butyl N-[(3S,4R)-1-carbamoyl-4-([4-[4-(2-[[(2S)-1-[(2S,4R)-4-hydroxy-2-([[4-(4-methyl-1,3-thiazol-5-yl)phenyl]methyl] carbamoyl)pyrrolidin-1-yl]-3,3-dimethyl-1-oxobutan-2-yl]carbamoyl]ethyl) piperidin-1-yl]phenyl]methoxy) pentan-3-yl]carbamate | 904.65 | (400 MHz, $CD_3OD$) δ 8.90 (s, 1H), 7.89 (d, J = 9.0 Hz, 1H), 7.53-7.40 (m, 5H), 7.24 (d, J = 8.0 Hz, 2H), 6.96 (d, J = 8.0 Hz, 2H), 6.39 (d, J = 9.6 Hz, 1H), 4.71-4.64 (m, 1H), 4.58 (t, J = 8.3 Hz, 2H), 4.56-4.47 (m, 3H), 4.47-4.34 (m, 3H), 3.93 (d, J = 11.0 Hz, 1H), 3.83 (dd, J = 11.0, 3.9 Hz, 1H), 3.67 (d, J = 12.8 Hz, 2H), 3.61-3.44 (m, 3H), 2.66 (t, J = 10.6, 2H), 2.50 (s, 3H), 2.46-2.31 (m, 2H), 2.29-2.17 (m, 3H), 2.13-2.06 (m, 1H), 2.05-1.92 (m, 1H), 1.84 (d, J = 11.8 Hz, 2H), 1.67-1.53 (m, 3H), 1.45 (s, 9H), 1.42-1.26 (m, 3H), 1.16 (d, J = 6.2 Hz, 3H), 1.06 (s, 9H) |
| G54 | 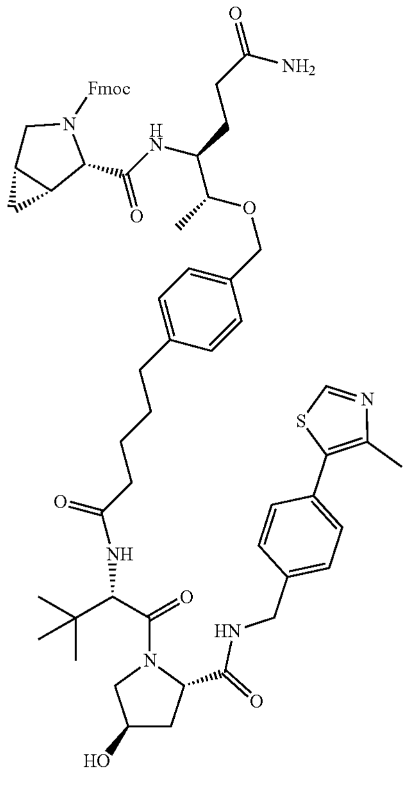 | 9H-fluoren-9-ylmethyl(1R,2S,5S)-2-[[(3S,4R)-1-carbamoyl-4-[[4-[4-(4-[[(2S)-1-[(2S,4R)-4-hydroxy-2-([[4-(4-methyl-1,3-thiazol-5-yl)phenyl]methyl] carbamoyl)pyrrolidin-1-yl]-3,3-dimethyl-1-oxobutan-2-yl]carbamoyl]butyl) phenyl]methoxy]pentan-3-yl]carbamoyl]-3-azabicyclo[3.1.0] hexane-3-carboxylate | 1080.20 | (400 MHz, DMSO-$d_6$) δ 8.99 (s, 1H), 8.57 (t, J = 6.1 Hz, 1H), 7.90 (t, J = 7.4 Hz, 4H), 7.65 (t, J = 7.3 Hz, 3H), 7.49-7.27 (m, 8H), 7.22 (d, J = 6.3 Hz, 2H), 7.12 (d, J = 7.4 Hz, 2H), 6.64 (d, J = 21.2 Hz, 1H), 5.15-5.13 (m, 1H), 4.55 (d, J = 9.4 Hz, 1H), 4.51-4.41 (m, 3H), 4.40-4.34 (m, 1H), 4.27-4.21 (m, 2H), 4.16-4.12 (m, 2H), 3.70-3.65 (m, 2H), 3.49-3.43 (m, 2H), 3.36-3.28 (m, 3H), 3.25-3.18 (m, 6H), 2.45 (s, 3H), 2.36-2.25 (m, 1H), 2.19-1.96 (m, 2H), 1.91-1.79 (m, 2H), 1.62-1.49 (m,5H), 1.20-1.09 (m, 4H), 0.94 (s, 9H), 0.70-0.69 (m, 1H), 0.57-0.52 (m, 1H) |

TABLE 47-continued

| Characterization data for intermediates prepare according to the procedure above. | | | | |
|---|---|---|---|---|
| Intermediate | Structure | Chemical Name | MS: [(M + 1)]+ | 1H-NMR |
| G55 | 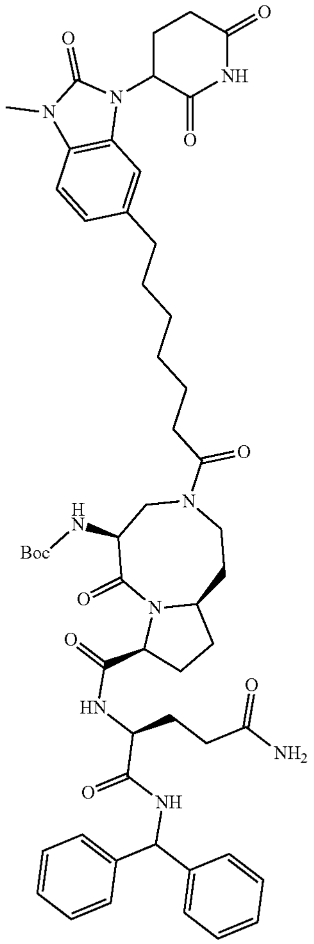 [SMILES: Cn1c(=O)n(C2CCC(=O)NC2=O)c2cc(CCCCCCC(=O)N3CC[C@H]4CC[C@@H](C(=O)N[C@@H](CCC(N)=O)C(=O)NC(c5ccccc5)c5ccccc5)N4C(=O)[C@@H](NC(=O)OC(C)(C)C)C3)ccc21] | tert-butyl N-[(5S,8S,10aR)-8-[[(1S)-3-carbamoyl-1-(diphenylmethylcarbamoyl)propyl]carbamoyl]-3-[7-[3-(2,6-dioxopiperidin-3-yl)-1-methyl-2-oxo-1,3-benzodiazol-5-yl]heptanoyl]-6-oxo-octahydropyrrolo[1,2-a][1,5]diazocin-5-yl]carbamate | 990.40 | (400 MHz, DMSO-$d_6$) δ 11.09 (s, 1H), 8.75 (dd, J = 8.3, 2.6 Hz, 1H), 8.20-8.14 (m, 1H), 7.41-7.20 (m, 11H), 7.06 (d, J = 7.9 Hz, 1H), 7.02-6.87 (m, 2H), 6.78-6.72 (m, 1H), 6.50 (d, J = 6.8 Hz, 1H), 6.10 (d, J = 8.4 Hz, 1H), 5.36 (dd, J = 12.8, 5.4 Hz, 1H), 4.46-4.25 (m, 3H), 4.19-4.05 (m, 1H), 3.75-3.70 (m, 1H), 3.60-3.42 (m, 2H), 3.30-3.19 (m, 1H), 3.09 (t, J = 12.7 Hz, 1H), 2.97-2.84 (m, 1H), 2.80-2.73 (m, 1H), 2.71-2.62 (m, 1H), 2.62-2.53 (m, 3H), 2.48-2.26 (m, 2H), 2.21-2.06 (m, 3H), 2.05-1.86 (m, 4H), 1.85-1.68 (m, 3H), 1.64-1.57 (m, 6H), 1.38 (s, 9H), 1.36-1.30 (m, 4H) |

TABLE 47-continued

| Characterization data for intermediates prepare according to the procedure above. | | | | |
|---|---|---|---|---|
| Intermediate | Structure | Chemical Name | MS: [(M + 1)]+ | $^1$H-NMR |
| G56 | 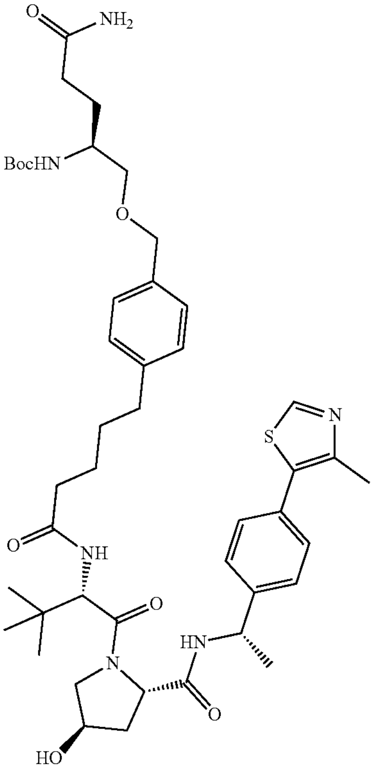 [SMILES: Cc1ncsc1-c1ccc([C@H](C)NC(=O)[C@@H]2C[C@@H](O)CN2C(=O)[C@@H](NC(=O)CCCCc2ccc(COC[C@H](CCC(N)=O)NC(=O)OC(C)(C)C)cc2)C(C)(C)C)cc1] | tert-butyl N-[(2S)-4-carbamoyl-1-[[4-(4-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]butyl)phenyl]methoxy]butan-2-yl]carbamate | 849.35 | (400 MHz, DMSO-$d_6$) δ 8.99 (s, 1H), 8.38 (d, J = 7.8 Hz, 1H), 7.83 (d, J = 9.3 Hz, 1H), 7.47-7.42 (m, 2H), 7.38 (d, J = 8.4 Hz, 2H), 7.26-7.22 (d, J = 8.0 Hz, 4H), 7.15 (d, J = 8.1 Hz, 3H), 5.11 (d, J = 3.5 Hz, 1H), 4.92 (p, J = 7.4 Hz, 1H), 4.52 (d, J = 9.3 Hz, 1H), 4.42 (d, J = 3.4 Hz, 4H), 4.28 (s, 1H), 3.68-3.51 (m, 2H), 3.32-3.28 (m, 4H), 2.56 (d, J = 7.0 Hz, 1H), 2.46 (s, 4H), 2.36-2.24 (m, 2H), 2.18-2.10 (m, 1H), 2.08-1.96 (m, 2H), 1.85-1.67 (m, 1H), 1.59-1.43 (m, 7H), 1.38 (s, 9H), 0.94 (s, 9H) |
| G57 | 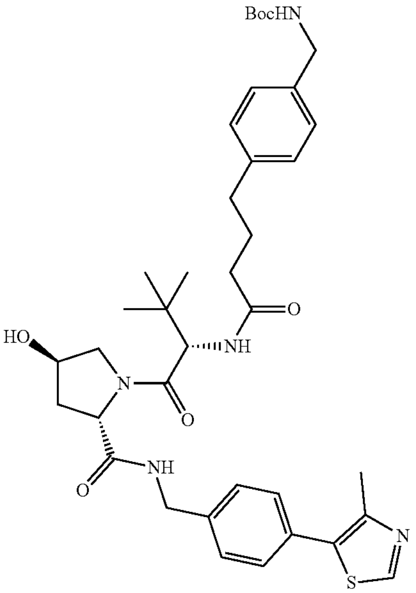 [SMILES: Cc1ncsc1-c1ccc(CNC(=O)[C@@H]2C[C@@H](O)CN2C(=O)[C@@H](NC(=O)CCCc2ccc(CNC(=O)OC(C)(C)C)cc2)C(C)(C)C)cc1] | tert-butyl N-[[4-(3-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]propyl)phenyl]methyl]carbamate | 706.40 | (400 MHz, DMSO-$d_6$) δ 8.99 (s, 1H), 8.57 (t, J = 6.0 Hz, 1H), 7.91 (d, J = 9.2 Hz, 1H), 7.46-7.30 (m, 5H), 7.15-7.12 (m, 4H), 5.15-5.13 (m, 1H), 4.56 (d, J = 9.3 Hz, 1H), 4.45-4.43 (m, 2H), 4.35 (d, J = 4.2 Hz, 1H), 4.22 (dd, J = 15.9, 5.4 Hz, 1H), 4.08 (d, J = 6.2 Hz, 2H), 3.67 (d, J = 3.5 Hz, 2H), 3.32-3.30 (m, 2H), 2.45 (s, 3H), 2.27 (dt, J = 14.8, 7.6 Hz, 1H), 2.18-2.14 (m, 1H), 2.05-2.03 (m, 1H), 1.92-1.90 (m, 1H), 1.79-1.75 (m, 2H), 1.39 (s, 9H), 0.95 (s, 9H) |

TABLE 47-continued

| Characterization data for intermediates prepare according to the procedure above. | | | | |
|---|---|---|---|---|
| Inter-me-diate | Structure | Chemical Name | MS: [(M + 1)]$^+$ | $^1$H-NMR |
| G58 | 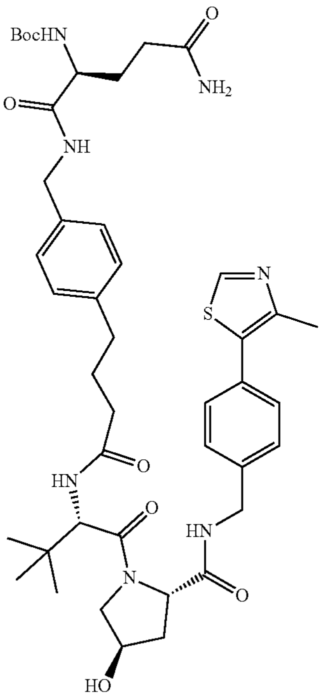 [SMILES: Cc1ncsc1-c1ccc(CNC(=O)[C@@H]2C[C@@H](O)CN2C(=O)[C@@H](NC(=O)CCCc2ccc(CNC(=O)[C@H](CCC(N)=O)NC(=O)OC(C)(C)C)cc2)C(C)(C)C)cc1] | tert-butyl N-[(1S)-3-carbamoyl-1-([[4-(3-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]propyl)phenyl]methyl]carbamoyl)propyl]carbamate | 834.30 | (400 MHz, DMSO-$d_6$) δ 8.99 (s, 1H), 8.57 (t, J = 6.1 Hz, 1H), 8.23 (t, J = 5.9 Hz, 1H), 7.91 (d, J = 9.3 Hz, 1H), 7.40 (d, J = 8.4 Hz, 4H), 7.26 (s, 1H), 7.17-7.08 (m, 4H), 6.90 (d, J = 7.9 Hz, 1H), 6.76 (s, 1H), 5.12 (d, J = 3.5 Hz, 1H), 4.56 (d, J = 9.4 Hz, 1H), 4.47-4.40 (m, 2H), 4.35 (d, J = 4.2 Hz, 1H), 4.26-4.22 (m, 2H), 3.88 (t, J = 7.0 Hz, 1H), 3.67-3.65 (m, 2H), 2.45 (s, 3H), 2.35-2.20 (m, 1H), 2.19-1.99 (m, 4H), 1.94-1.67 (m, 5H), 1.38 (s, 9H), 1.04 (d, J = 6.1 Hz, 3H), 0.94 (s, 9H) |
| G59 | 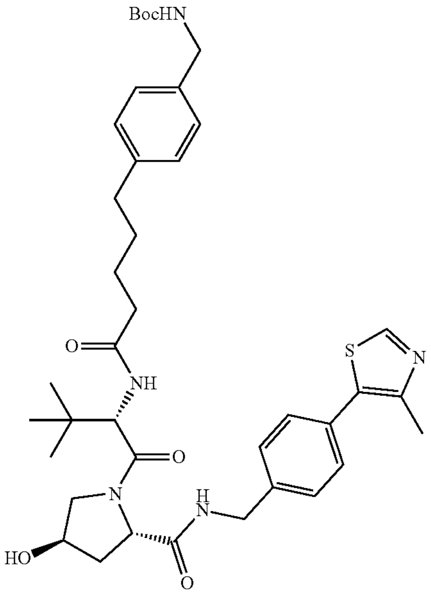 [SMILES: Cc1ncsc1-c1ccc(CNC(=O)[C@@H]2C[C@@H](O)CN2C(=O)[C@@H](NC(=O)CCCCc2ccc(CNC(=O)OC(C)(C)C)cc2)C(C)(C)C)cc1] | tert-butyl N-[[4-(4-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]butyl)phenyl]methyl]carbamate | 720.30 | (400 MHz, DMSO-$d_6$) 8.99 (s, 1H), 8.57 (t, J = 6.1 Hz, 1H), 7.88 (d, J = 9.3 Hz, 1H), 7.41 (q, J = 8.3 Hz, 4H), 7.33 (t, J = 6.2 Hz, 1H), 7.12 (s, 4H), 5.13 (d, J = 3.6 Hz, 1H), 4.55 (d, J = 9.3 Hz, 1H), 4.49-4.38 (m, 2H), 4.35 (s, 1H), 4.22 (dd, J = 15.9, 5.4 Hz, 1H), 4.08 (d, J = 6.2 Hz, 2H), 3.72-3.60 (m, 2H), 2.54 (s, 2H), 2.45 (s, 3H), 2.30 (q, J = 6.8 Hz, 1H), 2.18-2.10 (m, 1H), 2.03 (t, J = 10.2 Hz, 1H), 1.90-1.80 (m, 1H), 1.52-1.48 (m, 4H), 1.39 (s, 9H), 0.94 (s, 9H) |

TABLE 47-continued

Characterization data for intermediates prepare according to the procedure above.

| Inter-me-diate | Structure | Chemical Name | MS: [(M + 1)]+ | $^1$H-NMR |
|---|---|---|---|---|
| G60 | 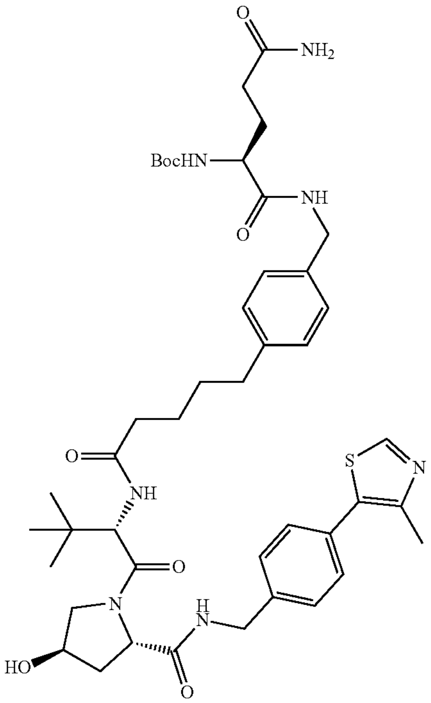 [SMILES: Cc1ncsc1-c1ccc(CNC(=O)[C@@H]2C[C@@H](O)CN2C(=O)[C@@H](NC(=O)CCCCc2ccc(CNC(=O)[C@H](CCC(N)=O)NC(=O)OC(C)(C)C)cc2)C(C)(C)C)cc1] | tert-butyl N-[(1S)-3-carbamoyl-1-([[4-(4-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]butyl)phenyl]methyl]carbamoyl)propyl]carbamate | 848.30 | (400 MHz, $CD_3OD$) δ 8.90 (s, 1H), 7.51-7.42 (m, 4H), 7.21 (d, J = 7.7 Hz, 2H), 7.16 (s, 2H), 4.67-4.49 (m, 6H), 4.42-4.34 (m, 2H), 4.07 (s, 1H), 3.92 (d, J = 11.0 Hz, 1H), 3.82 (dd, J = 11.0, 3.9 Hz, 1H), 3.56-3.47 (m, 1H), 3.50 (d, J = 1.6 Hz, 1H), 3.17-3.13 (m, 1H), 2.65-2.58 (m, 3H), 2.49 (s, 3H), 2.36-2.21 (m, 4H), 2.14-1.98 (m, 2H), 1.94-1.81 (m, 2H), 1.45 (s, 9H), 1.05 (s, 9H) |
| G61 | 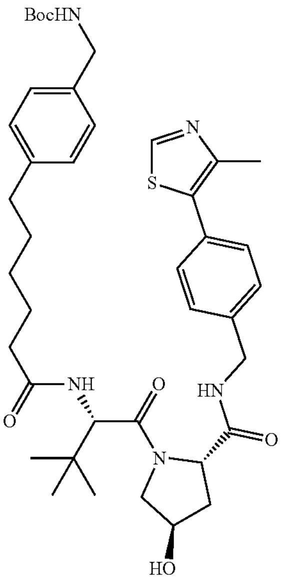 [SMILES: Cc1ncsc1-c1ccc(CNC(=O)[C@@H]2C[C@@H](O)CN2C(=O)[C@@H](NC(=O)CCCCCc2ccc(CNC(=O)OC(C)(C)C)cc2)C(C)(C)C)cc1] | tert-butyl N-[[4-(5-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]pentyl)phenyl]methyl]carbamate | 734.45 | (400 MHz, DMSO-$d_6$) δ 8.99 (s, 1H), 8.57 (t, J = 6.0 Hz, 1H), 7.85 (d, J = 9.3 Hz, 1H), 7.41 (q, J = 8.2 Hz, 4H), 7.32 (d, J = 6.3 Hz, 1H), 7.12 (s, 4H), 5.13 (d, J = 3.5 Hz, 1H), 4.54 (d, J = 9.4 Hz, 1H), 4.47-4.37 (m, 2H), 4.22 (dd, J = 15.9, 5.5 Hz, 1H), 4.08 (d, J = 6.2 Hz, 2H), 3.73-3.60 (m, 2H), 3.52-3.40 (m, 1H), 2.45 (s, 3H), 2.26 (dt, J = 14.8, 7.5 Hz, 1H), 2.08 (ddd, J = 32.5, 17.3, 7.8 Hz, 2H), 1.97-1.83 (m, 1H), 1.63-1.44 (m, 4H), 1.39 (s, 9H), 1.28-1.24 (m, 2H), 0.93 (s, 9H) |

TABLE 47-continued

| Characterization data for intermediates prepare according to the procedure above. | | | | |
|---|---|---|---|---|
| Inter-me-diate | Structure | Chemical Name | MS: [(M + 1)]$^+$ | $^1$H-NMR |
| G62 | 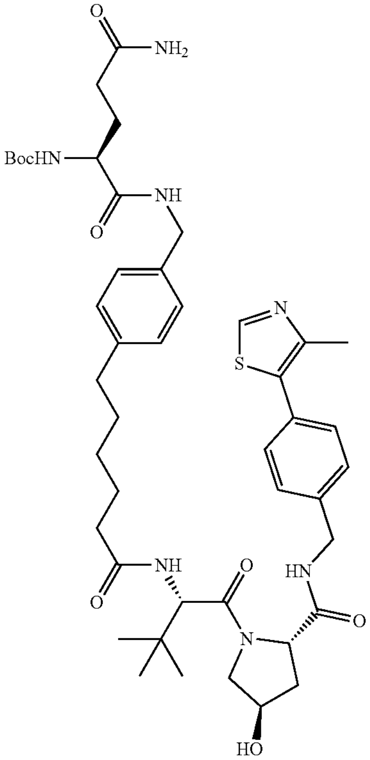 [SMILES: Cc1ncsc1-c1ccc(CNC(=O)[C@@H]2C[C@@H](O)CN2C(=O)[C@@H](NC(=O)CCCCCc2ccc(CNC(=O)[C@H](CCC(N)=O)NC(=O)OC(C)(C)C)cc2)C(C)(C)C)cc1] | tert-butyl N-[(1S)-3-carbamoyl-1-([[4-(5-[[(2S)-1-[(2S,4R)-4-hydroxy-2-([[4-(4-methyl-1,3-thiazol-5-yl)phenyl]methyl] carbamoyl)pyrrolidin-1-yl]-3,3-dimethyl-1-oxobutan-2-yl]carbamoyl]pentyl) phenyl]methyl] carbamoyl)propyl] carbamate | 862.40 | (400 MHz, DMSO-$d_6$) δ 8.99 (s, 1H), 8.57 (t, J = 6.0 Hz, 1H), 8.23 (t, J = 5.8 Hz, 1H), 7.86 (d, J = 9.3 Hz, 1H), 7.40 (q, J = 8.2 Hz, 4H), 7.26 (s, 1H), 7.15-7.08 (m, 4H), 6.90 (d, J = 8.0 Hz, 1H), 6.76 (s, 1H), 5.13 (d, J = 3.5 Hz, 1H), 4.54 (d, J = 9.3 Hz, 1H), 4.43 (q, J = 7.4 Hz, 2H), 4.35 (d, J = 4.1 Hz, 2H), 4.22 (dt, J = 11.0, 5.4 Hz, 3H), 3.90-3.87 (m, 1H), 3.82-3.73 (m, 1H), 3.68-3.64 (m, 2H), 2.45 (s, 3H), 2.26-2.22 (m, 1H), 2.15-1.98 (m, 4H), 1.94-1.78 (m, 2H), 1.73-1.69 (m, 1H), 1.52-1.47 (m, 4H), 1.38 (s, 9H), 1.32-1.21 (m, 3H), 0.93 (s, 9H). |

TABLE 47-continued

| Characterization data for intermediates prepare according to the procedure above. | | | | |
|---|---|---|---|---|
| Inter-me-diate | Structure | Chemical Name | MS: [(M + 1)]$^+$ | $^1$H-NMR |
| G63 | 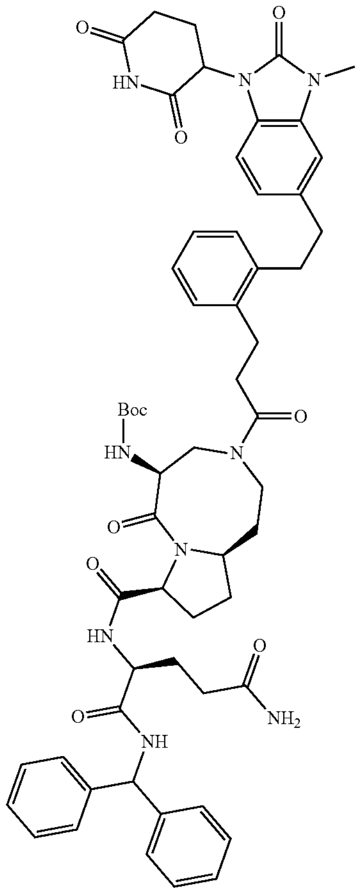 [SMILES: Cn1c(=O)n(C2CCC(=O)NC2=O)c2ccc(CCc3ccccc3CCC(=O)N3CC[C@H]4CC[C@@H](C(=O)N[C@@H](CCC(N)=O)C(=O)NC(c5ccccc5)c5ccccc5)N4C(=O)[C@@H](NC(=O)OC(C)(C)C)C3)cc21] | tert-butyl N-[(5S,8S,10aR)-8-[[(1S)-3-carbamoyl-1-(diphenylmethylcarbamoyl) propyl]carbamoyl]-3-[3-(2-[2-[1-(2,6-dioxopiperidin-3-yl)-3-methyl-2-oxo-1,3-benzodiazol-5-yl]ethyl]phenyl) propanoyl]-6-oxo-octahydropyrrolo[1,2-a][1,5]diazocin-5-yl]carbamate | 1038.40 | (400 MHz, DMSO-$d_6$) δ 11.08 (s, 1H), 8.70 (d, J = 8.3 Hz, 1H), 8.21-8.12 (m, 1H), 7.30-7.2.5 (m, 14H), 7.12-7.10 (m, 3H), 7.01 (t, J = 7.8 Hz, 1H), 6.95-6.91 (m, 1H), 6.74 (t, J = 22.0 Hz, 1H), 6.09 (d, J = 8.2 Hz, 1H), 5.39-5.29 (m, 1H), 4.37-4.34 (m, 3H), 3.95-3.92 (m, 1H), 3.74-3.71 (m, 1H), 3.35-3.31 (m, 5H), 3.14-3.05 (m, 1H), 3.01-2.58 (m, 11H), 2.16-1.52 (m, 11H), 1.37 (s, 9H). |

TABLE 47-continued

| Characterization data for intermediates prepare according to the procedure above. | | | | |
|---|---|---|---|---|
| Intermediate | Structure | Chemical Name | MS: [(M + 1)]+ | $^1$H-NMR |
| G64 | 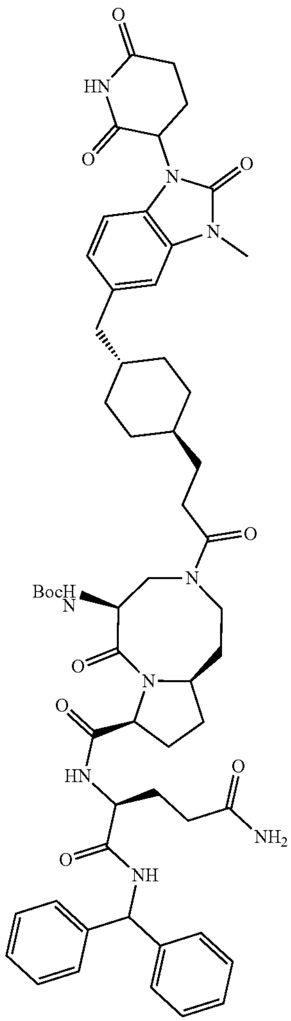 [SMILES: Cn1c(=O)n(C2CCC(=O)NC2=O)c2ccc(C[C@H]3CC[C@H](CCC(=O)N4CC[C@H]5CC[C@@H](C(=O)N[C@@H](CCC(N)=O)C(=O)NC(c6ccccc6)c6ccccc6)N5C(=O)[C@@H](NC(=O)OC(C)(C)C)C4)CC3)cc21] | tert-butyl N-[(5S,8S,10aR)-8-[[(1S)-3-carbamoyl-1-(diphenylmethylcarbamoyl)propyl]carbamoyl]-6-oxo-3-[3-[(1r,4r)-4-[[1-(2,6-dioxopiperidin-3-yl)-3-methyl-2-oxo-1,3-benzodiazol-5-yl]methyl]cyclohexyl]propanoyl]-octahydropyrrolo[1,2-a][1,5]diazocin-5-yl]carbamate | 1030.45 | (400 MHz, DMSO-$d_6$) δ 11.08 (s, 1H), 8.73 (d, J = 8.4 Hz, 1H), 8.17 (t, J = 8.8 Hz, 1H), 7.39-7.18 (m, 11H), 7.02-6.96 (m, 2H), 6.81 (dd, J = 8.1, 1.7 Hz, 1H), 6.72 (d, J = 19.1 Hz, 1H), 6.47 (d, J = 6.9 Hz, 1H), 6.09 (d, J = 8.3 Hz, 1H), 5.76 (s, 2H), 5.34 (dd, J = 12.6, 5.4 Hz, 1H), 4.43-4.27 (m, 2H), 4.09-4.01 (m, 1H), 3.70-3.66 (m, 2H), 3.32-3.30 (m, 11H), 3.24-3.04 (m, 1H), 2.98-2.84 (m, 1H), 2.75-2.60 (m, 2H), 2.47-2.44 (m, 1H), 2.17-2.04 (m, 3H), 2.09-1.90 (m, 2H), 1.83-1.56 (m, 6H), 1.43-1.34 (m, 11H), 1.18 (t, J = 7.1 Hz, 1H), 0.98-0.79 (m, 4H) |

TABLE 47-continued

Characterization data for intermediates prepare according to the procedure above.

| Inter-me-diate | Structure | Chemical Name | MS: [(M + 1)]+ | 1H-NMR |
|---|---|---|---|---|
| G65 | 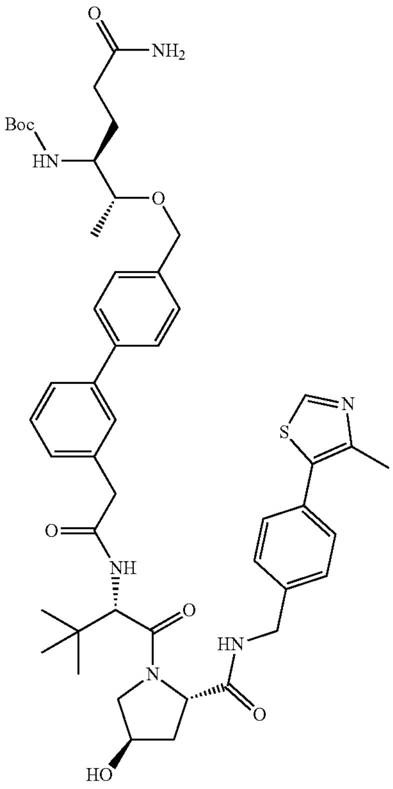 [SMILES: Cc1ncsc1-c1ccc(CNC(=O)[C@@H]2C[C@@H](O)CN2C(=O)[C@@H](NC(=O)Cc2cccc(-c3ccc(CO[C@H](C)[C@H](CCC(N)=O)NC(=O)OC(C)(C)C)cc3)c2)C(C)(C)C)cc1] | tert-butyl N-[(3S,4R)-1-carbamoyl-4-[[3'-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methyl)-[1,1'-biphenyl]-4-yl]methoxy]pentan-3-yl]carbamate | 883.43 | (400 MHz, DMSO-$d_6$) δ 8.99 (s, 1H), 8.58 (t, J = 6.0 Hz, 1H), 8.18 (d, J = 9.3 Hz, 1H), 7.62-7.57 (m, 3H), 7.50 (dd, J = 7.9, 1.6 Hz, 1H), 7.40-7.33 (m, J = 9.7, 6.5 Hz, 7H), 7.29-7.21 (m, 2H), 6.72-6.61 (m, 2H), 5.76 (s, 2H), 5.12 (d, J = 3.5 Hz, 1H), 4.58-4.50 (m, 3H), 4.48-4.41 (m, 2H), 4.35 (s, 1H), 4.23 (dd, J = 15.8, 5.4 Hz, 1H), 3.75 (d, J = 13.8 Hz, 1H), 3.70-3.61 (m, 2H), 3.52 (d, J = 13.7 Hz, 1H), 3.47-3.42 (m, 1H), 2.45 (s, 3H), 2.07 (q, J = 9.3, 8.8 Hz, 2H), 1.91 (ddd, J = 12.9, 8.5, 4.5 Hz, 1H), 1.81 (d, J = 9.9 Hz, 1H), 1.54-1.50 (m, 1H), 1.39 (s, 9H), 1.09 (d, J = 6.0 Hz, 3H), 0.93 (s, 9H) |

TABLE 47-continued

| Characterization data for intermediates prepare according to the procedure above. | | | | |
|---|---|---|---|---|
| Inter-me-diate | Structure | Chemical Name | MS: [(M + 1)]+ | 1H-NMR |
| G66 | 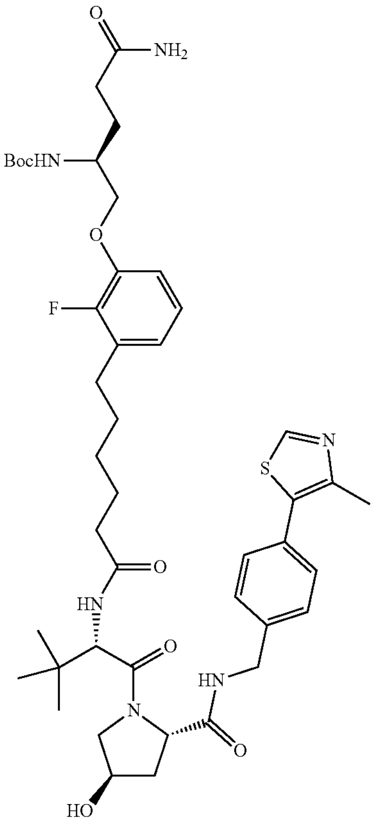 [SMILES: Cc1ncsc1-c1ccc(CNC(=O)[C@@H]2C[C@@H](O)CN2C(=O)[C@@H](NC(=O)CCCCCc2cccc(OC[C@H](CCC(N)=O)NC(=O)OC(C)(C)C)c2F)C(C)(C)C)cc1] | tert-butyl N-[(2S)-4-carbamoyl-1-[2-fluoro-3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenoxy]butan-2-yl]carbamate | 867.09 | (400 MHz, DMSO-$d_6$) δ 8.99 (s, 1H), 8.38 (d, J = 7.8 Hz, 1H), 7.80 (d, J = 9.3 Hz, 1H), 7.50-7.41 (m, 2H), 7.38 (d, J = 8.3 Hz, 2H), 7.27 (s, 1H), 7.05-6.93 (m, 2H), 6.87-6.77 (m, 2H), 6.74 (s, 1H), 5.10 (d, J = 3.5 Hz, 1H), 4.98-4.86 (m, 2H), 4.51 (d, J = 9.3 Hz, 1H), 4.45-4.41 (m, 1H), 4.28 (s, 1H), 3.91 (d, J = 6.1 Hz, 2H), 3.77-3.70 (m, 1H), 3.61 (d, J = 3.8 Hz, 2H), 2.58-2.54 (m, 2H), 2.46 (s, 3H), 2.27-2.23 (m, 1H), 2.12 (s, 1H), 2.11-2.09 (m, 3H), 2.06-1.96 (m, 1H), 1.81-1.77 (m, 1H), 1.55-1.52 (m, 4H), 1.51-1.47 (m, 1H), 1.39 (s, 9H), 1.39-1.35 (m, 2H), 1.32-1.28 (m, 2H), 1.27-1.23 (m, 1H), 0.93 (s, 9H) |

TABLE 47-continued

| Characterization data for intermediates prepare according to the procedure above. | | | | |
|---|---|---|---|---|
| Inter-me-diate | Structure | Chemical Name | MS: [(M + 1)]+ | ¹H-NMR |
| G67 | 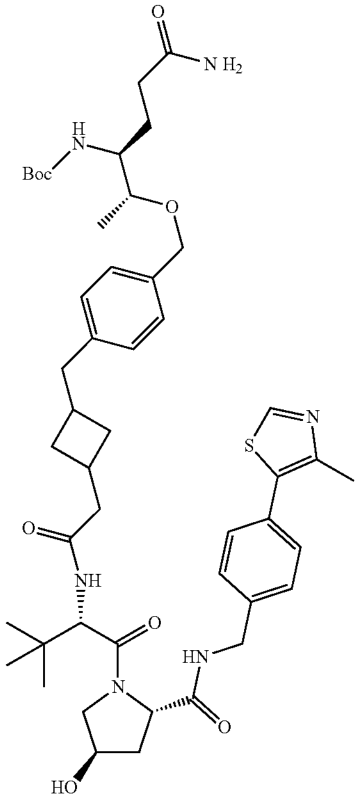 | tert-butyl N-[(3S,4R)-1-carbamoyl-4-[(4-[[3-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methyl)cyclobutyl]methyl]phenyl)methoxy]pentan-3-yl]carbamate | 875.30 | (400 MHz, $CD_3OD$) δ 8.89 (s, 1H), 8.65 (t, J = 6.0 Hz, 1H), 7.74 (dd, J = 18.4, 9.1 Hz, 1H), 7.51-7.40 (m, 4H), 7.31-7.08 (m, 4H), 6.41 (d, J = 9.5 Hz, 1H), 4.64 (d, J = 9.1 Hz, 1H), 4.62-4.42 (m, 7H), 4.43-4.33 (m, 1H), 3.90 (d, J = 11.1 Hz, 1H), 3.85-3.77 (m, 1H), 3.66-3.56 (m, 2H), 3.50 (q, J = 6.1 Hz, 1H), 2.75 (d, J = 7.7 Hz, 1H), 2.69-2.56 (m, 2H), 2.49 (d, J = 1.1 Hz, 3H), 2.49-2.32 (m, 2H), 2.31-2.16 (m, 4H), 2.15-2.03 (m, 1H), 2.03-1.81 (m, 2H), 1.66-1.58 (m, 1H), 1.54-1.47 (m, 1H), 1.45 (s, 9H), 1.17 (s, 3H), 1.04 (s, 9H) |
| G68 | 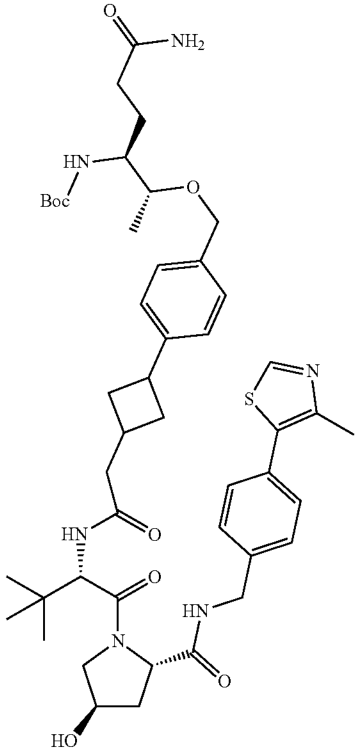 [SMILES: Cc1ncsc1-c1ccc(CNC(=O)[C@@H]2C[C@@H](O)CN2C(=O)[C@@H](NC(=O)CC2CC(c3ccc(CO[C@H](C)[C@H](CCC(N)=O)NC(=O)OC(C)(C)C)cc3)C2)C(C)(C)C)cc1] | tert-butyl N-[(3S,4R)-1-carbamoyl-4-([4-[3-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methyl)cyclobutyl]phenyl]methoxy)pentan-3-yl]carbamate | 861.70 | (400 MHz, $CD_3OD$) δ 8.89 (s, 1H), 7.48 (dd, J = 8.3, 2.0 Hz, 2H), 7.43 (dd, J = 8.2, 1.6 Hz, 2H), 7.29 (dd, J = 8.1, 6.1 Hz, 2H), 7.23-7.19 (m, 2H), 4.66 (d, J = 4.2 Hz, 1H), 4.64-4.44 (m, 7H), 4.38 (dd, J = 15.5, 1.8 Hz, 1H), 3.92 (dd, J = 11.3, 1.9 Hz, 1H), 3.82 (dd, J = 11.0, 3.9 Hz, 1H), 3.71-3.47 (m, 2H), 3.42-3.35 (m, 1H), 2.79-2.50 (m, 2H), 2.49 (d, J = 1.0 Hz, 3H), 2.48-2.36 (m, 1H), 2.39-2.15 (m, 3H), 2.15-2.04 (m, 1H), 2.04-1.93 (m, 1H), 1.88-1.84 (m, 1H), 1.66-1.59 (m, 1H), 1.57 (s, 1H), 1.45 (s, 9H), 1.17 (s, 3H), 1.06 (s, 9H). |

TABLE 47-continued

| Characterization data for intermediates prepare according to the procedure above. | | | | |
|---|---|---|---|---|
| Inter-me-diate | Structure | Chemical Name | MS: [(M + 1)]+ | 1H-NMR |
| G69 | 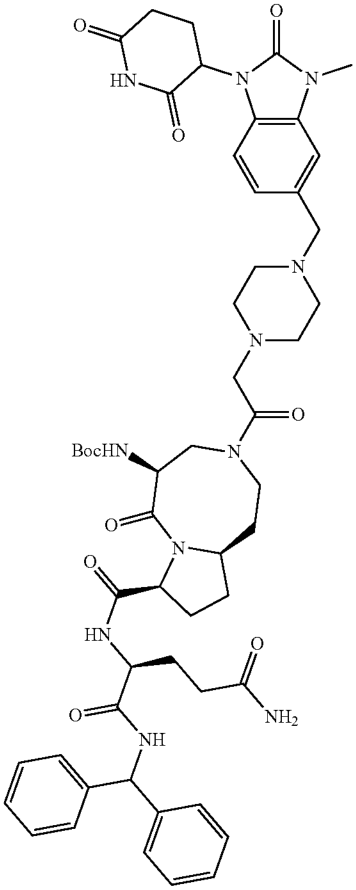 [SMILES: Cn1c(=O)n(C2CCC(=O)NC2=O)c2ccc(CN3CCN(CC(=O)N4CC[C@H]5CC[C@@H](C(=O)N[C@@H](CCC(N)=O)C(=O)NC(c6ccccc6)c6ccccc6)N5C(=O)[C@@H](NC(=O)OC(C)(C)C)C4)CC3)cc21] | tert-butyl N-[(5S,8S,10aR)-8-[[(1S)-3-carbamoyl-1-(diphenylmethylcarbamoyl)propyl]carbamoyl]-3-[2-(4-[[1-(2,6-dioxopiperidin-3-yl)-3-methyl-2-oxo-1,3-benzodiazol-5-yl]methyl]piperazin-1-yl)acetyl]-6-oxo-octahydropyrrolo[1,2-a][1,5]diazocin-5-yl]carbamate | 1018.43 | (400 MHz, DMSO-$d_6$) δ 12.70 (s, 1H), 11.12 (s, 1H), 9.53-9.38 (m, 1H), 8.81 (dd, J = 11.2, 8.2 Hz, 1H), 8.71-8.59 (m, 1H), 8.28-8.21 (m, 1H), 7.43-7.19 (m, 10H), 7.19-6.90 (m, 2H), 6.79 (d, J = 12.3 Hz, 1H), 6.12-6.07 (m, 1H), 5.39 (s, 1H), 4.42-4.27 (m, 3H), 3.09-2.97 (m, 32H), 2.20-2.06 (m, 2H), 1.40 (s, 9H) |

TABLE 47-continued

| Characterization data for intermediates prepare according to the procedure above. | | | | |
|---|---|---|---|---|
| Inter-me-diate | Structure | Chemical Name | MS: [(M + 1)]+ | 1H-NMR |
| G70 | 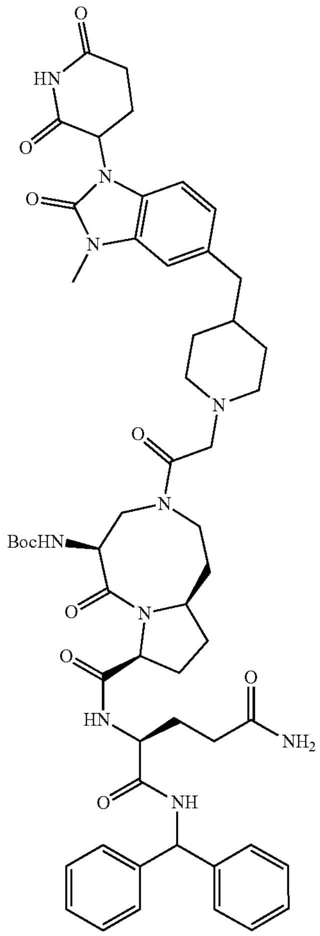 [SMILES: Cn1c(=O)n(C2CCC(=O)NC2=O)c2ccc(CC3CCN(CC(=O)N4CC[C@H]5CC[C@@H](C(=O)N[C@@H](CCC(N)=O)C(=O)NC(c6ccccc6)c6ccccc6)N5C(=O)[C@@H](NC(=O)OC(C)(C)C)C4)CC3)cc21] | Tert-butyl N-[(5S,8S,10aR)-8-[[(1S)-3-carbamoyl-1-(diphenylmethylcarbamoyl)propyl]carbamoyl]-3-[2-(4-[[1-(2,6-dioxopiperidin-3-yl)-3-methyl-2-oxo-1,3-benzodiazol-5-yl]methyl]piperidin-1-yl)acetyl]-6-oxo-octahydropyrrolo[1,2-a][1,5]diazocin-5-yl]carbamate | 1017.45 | (400 MHz, DMSO-$d_6$) δ 11.09 (s, 1H), 8.62-8.55 (m, 1H), 8.31-8.20 (m, 1H), 7.44-7.16 (m, 11H), 7.10-6.97 (m, 2H), 6.91-6.53 (m, 3H), 6.09 (d, J = 8.2 Hz, 1H), 5.35 (dd, J = 12.8, 5.4 Hz, 1H), 4.62 (d, J = 51.5 Hz, 2H), 4.47-4.11 (m, 7H), 3.95-3.54 (m, 4H), 3.31 (s, 3H), 2.96-2.86 (m, 2H), 2.76-2.57 (m, 4H), 2.38-2.32 (m, 2H), 2.21-2.01 (m, 4H), 2.06-1.83 (m, 3H), 1.69-1.50 (m, 2H), 1.48-1.44 (m, 4H), 1.38 (s, 9H), 1.28-1.22 (m, 1H) |

TABLE 47-continued

Characterization data for intermediates prepare according to the procedure above.

| Inter-me-diate | Structure | Chemical Name | MS: [(M + 1)]+ | 1H-NMR |
|---|---|---|---|---|
| G71 | 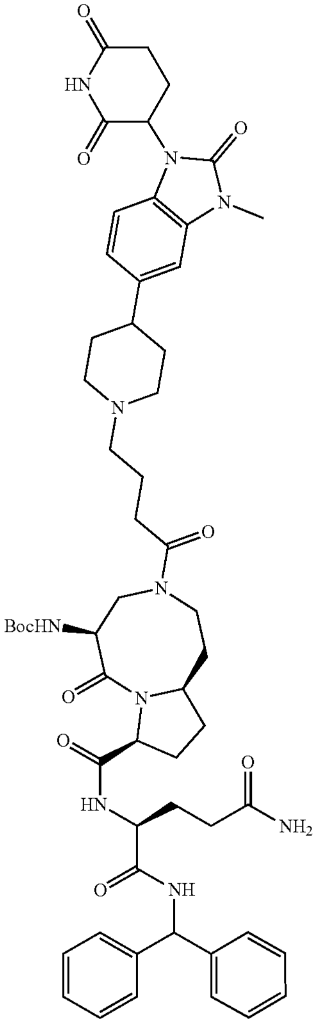 [SMILES: Cn1c(=O)n(C2CCC(=O)NC2=O)c2ccc(C3CCN(CCCC(=O)N4CC[C@H]5CC[C@@H](C(=O)N[C@@H](CCC(N)=O)C(=O)NC(c6ccccc6)c6ccccc6)N5C(=O)[C@@H](NC(=O)OC(C)(C)C)C4)CC3)cc21] | Tert-butyl N-[(5S,8S,10aR)-8-[[(1S)-3-carbamoyl-1-(diphenylmethylcarbamoyl)propyl]carbamoyl]-3-(4-[4-[1-(2,6-dioxopiperidin-3-yl)-3-methyl-2-oxo-1,3-benzodiazol-5-yl]piperidin-1-yl]butanoyl)-6-oxo-octahydropyrrolo[1,2-a][1,5]diazocin-5-yl]carbamate | 1031.45 | $^1$H NMR (400 MHz, DMSO-$d_6$) δ 11.09 (s, 1H), 8.72 (d, J = 8.5 Hz, 1H), 8.20 (d, J = 8.1 Hz, 1H), 7.38-7.19 (m, 11H), 7.11-6.86 (m, 3H), 6.81-6.66 (m, 1H), 6.58 (d, J = 6.8 Hz, 1H), 6.09 (dd, J = 8.4, 2.4 Hz, 1H), 5.34 (dd, J = 12.8, 5.4 Hz, 1H), 4.60-4.08 (m, 6H), 3.78 (dt, J = 12.1, 6.1 Hz, 2H), 3.33 (s, 3H), 3.24-2.85 (m, 4H), 2.79-2.54 (m, 2H), 2.49-2.30 (m, 2H), 2.22-1.84 (m, 6H), 1.84-1.58 (m, 11H), 1.38 (s, 9H), 1.28-1.20 (m, 3H), 0.92-0.82 (m, 1H) |

TABLE 47-continued

Characterization data for intermediates prepare according to the procedure above.

| Inter-me-diate | Structure | Chemical Name | MS: [(M + 1)]+ | 1H-NMR |
|---|---|---|---|---|
| G72 | 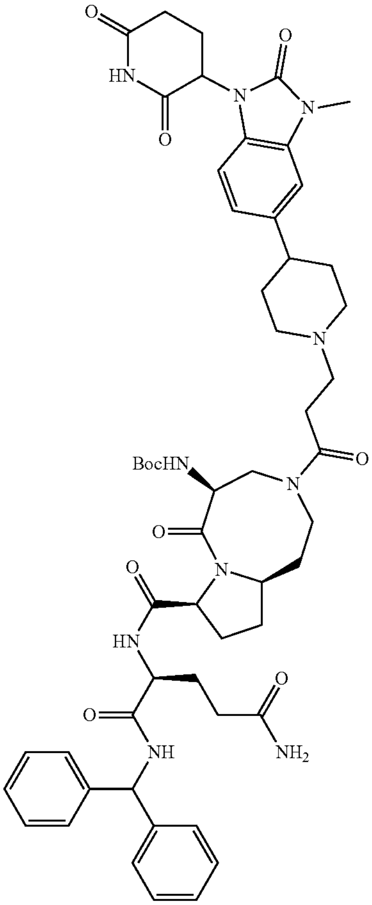 [SMILES: Cn1c(=O)n(C2CCC(=O)NC2=O)c2ccc(C3CCN(CCC(=O)N4CC[C@H]5CC[C@@H](C(=O)N[C@@H](CCC(N)=O)C(=O)NC(c6ccccc6)c6ccccc6)N5C(=O)[C@@H](NC(=O)OC(C)(C)C)C4)CC3)cc21] | Tert-butyl N-[(5S,8S,10aR)-8-[[(1S)-3-carbamoyl-1-(diphenylmethylcarbamoyl)propyl]carbamoyl]-3-(3-[4-[1-(2,6-dioxopiperidin-3-yl)-3-methyl-2-oxo-1,3-benzodiazol-5-yl]piperidin-1-yl]propanoyl)-6-oxo-octahydropyrrolo[1,2-a][1,5]diazocin-5-yl]carbamate | 1017.45 | (400 MHz, DMSO-$d_6$) δ 11.12 (s, 1H), 8.66 (d, J = 8.4 Hz, 1H), 8.36-8.19 (m, 1H), 7.39-7.20 (m, 11H), 7.14-7.00 (m, 2H), 6.92 (d, J = 7.9 Hz, 1H), 6.82 (s, 1H), 6.71 (d, J = 21.6 Hz, 1H), 6.16-6.04 (m, 1H), 5.36 (dt, J = 13.0, 6.4 Hz, 1H), 4.70-4.25 (m, 2H), 3.75-3.50 (m, 8H), 3.35 (s, 3H), 3.26-3.14 (m, 1H), 2.95-2.81 (m, 2H), 2.81-2.55 (m, 2H), 2.15 (t, J = 8.2 Hz, 4H), 2.07-1.87 (m, 8H), 1.48-1.42 (m, 8H), 1.38 (s, 9H) |

TABLE 47-continued

| Characterization data for intermediates prepare according to the procedure above. | | | | |
|---|---|---|---|---|
| Inter-me-diate | Structure | Chemical Name | MS: [(M + 1)]+ | 1H-NMR |
| G73 | 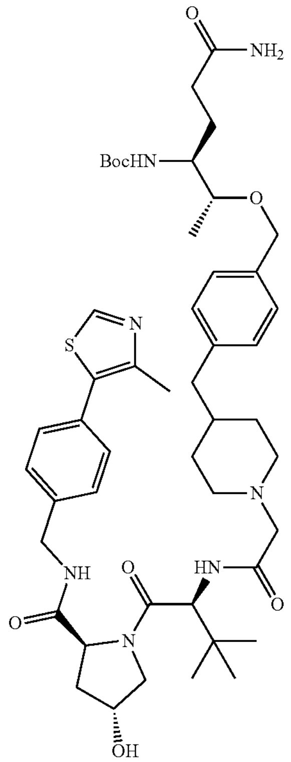 [SMILES: Cc1ncsc1-c1ccc(CNC(=O)[C@@H]2C[C@@H](O)CN2C(=O)[C@@H](NC(=O)CN2CCC(Cc3ccc(CO[C@H](C)[C@H](CCC(N)=O)NC(=O)OC(C)(C)C)cc3)CC2)C(C)(C)C)cc1] | tert-butyl N-[(3S,4R)-1-carbamoyl-4-[(4-[[1-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methyl)piperidin-4-yl]methyl]phenyl)methoxy]pentan-3-yl]carbamate | 904.75 | (400 MHz, $CDCl_3$) δ 8.70 (s, 1H), 7.93 (d, J = 8.4 Hz, 1H), 7.56 (s, 1H), 7.49 (t, J = 6.0 Hz, 1H), 7.43-7.34 (m, 4H), 7.24 (d, J = 7.8 Hz, 2H), 7.12 (d, J = 7.9 Hz, 2H), 6.40 (s, 1H), 5.32 (m, 1H), 4.90 (d, J = 9.7 Hz, 1H), 4.77 (t, J = 8.0 Hz, 1H), 4.66-4.49 (m, 3H), 4.45-4.30 (m, 3H), 4.22-4.13 (m, 1H), 3.72-3.58 (m, 3H), 3.04-2.88 (m, 2H), 2.87-2.74 (m, 2H), 2.54 (s, 3H), 2.33-2.23 (m, 2H), 2.22-2.04 (m, 4H), 2.03-1.87 (m, 2H), 1.7-1.62 (m, 4H), 1.54 (td, J = 7.3, 3.7 Hz, 1H), 1.45 (s, 9H), 1.39-1.25 (m, 3H), 1.21 (d, J = 6.3 Hz, 3H), 0.98 (s, 9H) |
| G74 | 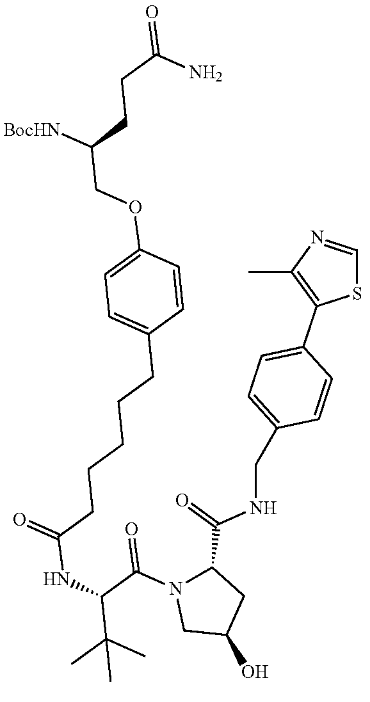 [SMILES: Cc1ncsc1-c1ccc(CNC(=O)[C@@H]2C[C@@H](O)CN2C(=O)[C@@H](NC(=O)CCCCCc2ccc(OC[C@H](CCC(N)=O)NC(=O)OC(C)(C)C)cc2)C(C)(C)C)cc1] | Tert-butyl N-[(2S)-4-carbamoyl-1-[4-(5-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]pentyl)phenoxy]butan-2-yl]carbamate | 835.35 | (400 MHz, DMSO-$d_6$) δ 8.99 (s, 1H), 8.56 (t, J = 6.1 Hz, 1H), 7.84 (d, J = 9.3 Hz, 1H), 7.41 (q, J = 8.2 Hz, 4H), 7.26 (s, 1H), 7.11-7.05 (m, 2H), 6.86-6.77 (m, 3H), 6.72 (s, 1H), 5.1 (d, J = 3.6 Hz, 1H), 4.59-4.32 (m, 4H), 4.25-4.18 (m, 1H), 3.88-3.75 (m, 2H), 3.75-3.62 (m, 2H), 3.32-3.28 (m, 2H), 2.47 (d, J = 6.8 Hz, 3H), 2.45 (s, 3H), 2.32-2.00 (m, 4H), 1.96-1.76 (m, 2H), 1.54 (m, 4H), 1.39 (s, 9H), 1.24 (p, J = 7.6 Hz, 2H), 0.93 (s, 9H) |

TABLE 47-continued

Characterization data for intermediates prepare according to the procedure above.

| Inter-me-diate | Structure | Chemical Name | MS: [(M + 1)]$^+$ | $^1$H-NMR |
|---|---|---|---|---|
| G75 | 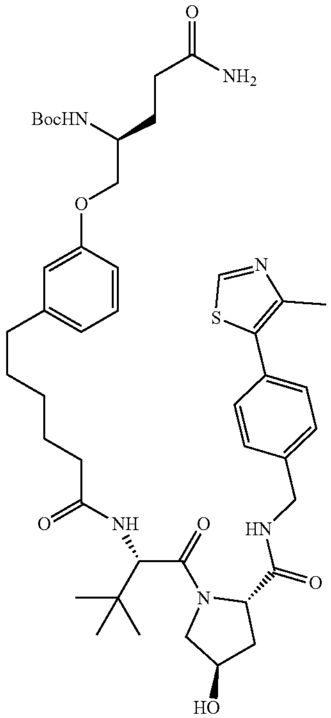 [SMILES: Cc1ncsc1-c1ccc(CNC(=O)[C@@H]2C[C@@H](O)CN2C(=O)[C@@H](NC(=O)CCCCCc2cccc(OC[C@H](CCC(N)=O)NC(=O)OC(C)(C)C)c2)C(C)(C)C)cc1] | tert-butyl N-[(2S)-4-carbamoyl-1-[3-(5-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]pentyl)phenoxy]butan-2-yl]carbamate | 835.44 | (400 MHz, DMSO-$d_6$) δ 8.99 (s, 1H), 8.55 (t, J = 6.0 Hz, 1H), 7.84 (d, J = 9.3 Hz, 1H), 7.46-7.35 (m, 4H), 7.25 (s, 1H), 7.16 (t, J = 7.9 Hz, 1H), 6.81 (d, J = 8.5 Hz, 1H), 6.77-6.73 (m, 3H), 4.54 (d, J = 9.4 Hz, 1H), 4.49-4.39 (m, 2H), 4.36 (s, 1H), 4.22 (dd, J = 15.9, 5.5 Hz, 1H), 3.90-3.77 (m, 1H), 3.72-3.61 (m, 2H), 3.05-3.00 (m, 5H), 2.45 (s, 3H), 2.31-2.23 (m, 1H), 2.17-2.09 (m, 2H), 2.02 (d, J = 9.5 Hz, 1H), 1.94-1.87 (m, 1H), 1.76-1.72 (m, 4H), 1.59-1.44 (m, 4H), 1.39 (s, 9H), 1.30-1.23 (m, 2H), 0.93 (s, 9H) |
| G76 | 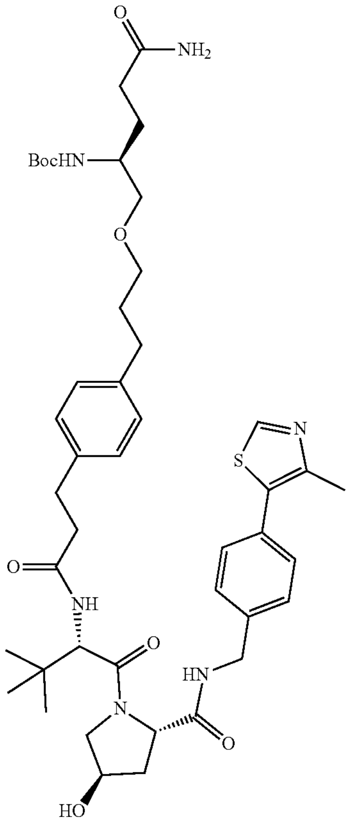 [SMILES: Cc1ncsc1-c1ccc(CNC(=O)[C@@H]2C[C@@H](O)CN2C(=O)[C@@H](NC(=O)CCc2ccc(CCCOC[C@H](CCC(N)=O)NC(=O)OC(C)(C)C)cc2)C(C)(C)C)cc1] | tert-butyl N-[(2S)-4-carbamoyl-1-[3-[4-(2-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]ethyl)phenyl]propoxy]butan-2-yl]carbamate | 835.07 | (400 MHz, DMSO-$d_6$) δ 8.99 (s, 1H), 8.55 (t, J = 6.1 Hz, 1H), 7.96-7.87 (m, 1H), 7.41 (q, J = 8.3 Hz, 5H), 7.22 (d, J = 7.6 Hz, 2H), 7.15-7.05 (m, 4H), 6.69 (s, 1H), 6.62-6.51 (m, 1H), 5.74 (d, J = 14.1 Hz, 1H), 5.13 (s, 1H), 4.60-4.34 (m, 5H), 3.67 (s, 2H), 2.84-2.74 (m, 3H), 2.57 (d, J = 7.3 Hz, 2H), 2.45 (s, 3H), 2.06 (d, J = 8.7 Hz, 4H), 1.94-1.87 (m, 2H), 1.77-1.68 (m, 3H), 1.37 (s, 9H), 1.32-1.28 (m, 2H), 0.90 (s, 9H) |

TABLE 47-continued

| Characterization data for intermediates prepare according to the procedure above. | | | | |
|---|---|---|---|---|
| Intermediate | Structure | Chemical Name | MS: [(M + 1)]+ | $^1$H-NMR |
| G77 | 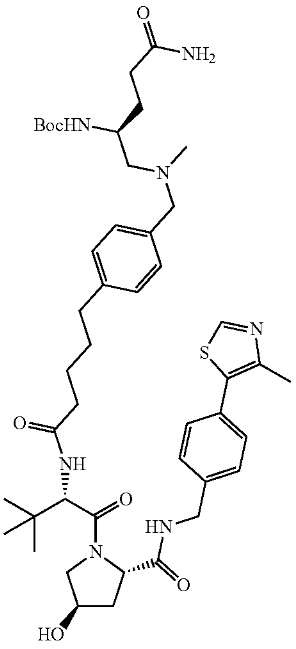 [SMILES: Cc1ncsc1-c1ccc(CNC(=O)[C@@H]2C[C@@H](O)CN2C(=O)[C@@H](NC(=O)CCCCc2ccc(CN(C)C[C@H](CCC(N)=O)NC(=O)OC(C)(C)C)cc2)C(C)(C)C)cc1] | tert-butyl N-[(2S)-4-carbamoyl-1-([[4-(4-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]butyl)phenyl]methyl](methyl)amino)butan-2-yl]carbamate | 848.60 | (400 MHz, $CD_3OD$) δ 8.89 (s, 1H), 7.51-7.41 (m, 4H), 7.24 (d, J = 7.9 Hz, 2H), 7.14 (d, J = 7.9 Hz, 2H), 4.65 (s, 1H), 4.62-4.55 (m, 2H), 4.54-4.50 (m, 2H), 4.37 (d, J = 15.6 Hz, 1H), 3.92 (d, J = 11.0 Hz, 1H), 3.82 (dd, J = 10.9, 3.9 Hz, 1H), 3.74 (s, 1H), 3.55-3.47 (m, 2H), 2.63 (t, J = 8.0 Hz, 2H), 2.49 (s, 3H), 2.45-2.16 (m, 10H), 2.13-2.07 (m, 1H), 1.99-1.87 (m, 1H), 1.70-1.63 (m, 4H), 1.47 (s, 9H), 1.05 (s, 9H) |
| G78 | 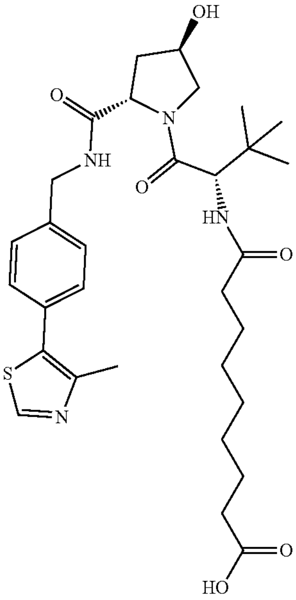 [SMILES: Cc1ncsc1-c1ccc(CNC(=O)[C@@H]2C[C@@H](O)CN2C(=O)[C@@H](NC(=O)CCCCCCCC(=O)O)C(C)(C)C)cc1] | 9-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-9-oxononanoic acid | 601.45 | (400 MHz, DMSO-$d_6$) δ 11.88 (s, 1H), 8.99 (s, 1H), 8.56 (t, J = 5.9 Hz, 1H), 7.84 (d, J = 9.3 Hz, 1H), 7.41 (q, J = 8.4 Hz, 4H), 5.12 (d, J = 3.6 Hz, 1H), 4.55 (d, J = 9.3 Hz, 1H), 4.46-4.42 (m, 2H), 4.35 (s, 1H), 4.22 (dd, J = 16.0, 5.5 Hz, 1H), 3.66 (s, 1H), 2.45 (s, 3H), 2.32-2.05 (m, 4H), 2.05-2.01 (m, 1H), 1.96-1.85 (m, 1H), 1.50-1.46 (m, 1H), 1.27-1.23 (m, 8H), 0.94 (s, 9H) |

TABLE 47-continued

| Characterization data for intermediates prepare according to the procedure above. | | | | |
|---|---|---|---|---|
| Inter-me-diate | Structure | Chemical Name | MS: [(M + 1)]$^+$ | $^1$H-NMR |
| G79 | 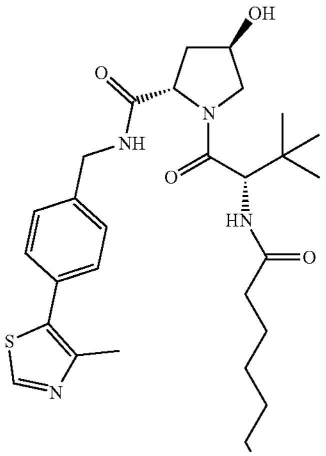 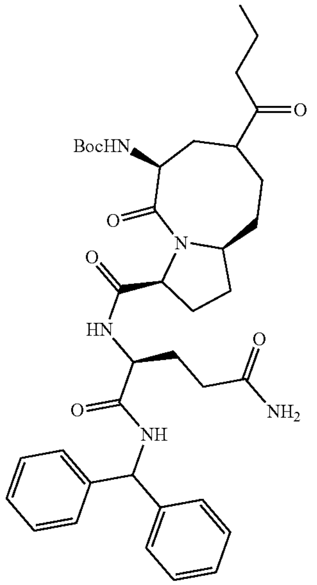 | tert-butyl N-[(5S,8S,10aR)-8-[[(1S)-3-carbamoyl-1-(diphenylmethyl-carbamoyl)propyl]carbamoyl]-3-(8-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]octanoyl)-6-oxo-octahydropyrrolo[1,2-a][1,5]diazocin-5-yl]carbamate | 1203.51 | (400 MHz, DMSO-$d_6$) δ 8.99 (s, 1H), 8.72 (d, J = 8.6 Hz, 1H), 8.56 (t, J = 6.2 Hz, 1H), 8.18 (t, J = 7.4 Hz, 1 H), 7.83 (d, J = 9.5 Hz, 1H), 7.41 (q, J = 8.2 Hz, 4H), 7.35-7.24 (m, 10H), 7.22 (s, 1H), 6.72 (d, J = 17.5 Hz, 1H), 6.47 (d, J = 7.0 Hz, 1H), 6.10 (d, J = 8.4 Hz, 1H), 5.12 (d, J = 3.6 Hz, 1H), 4.55 (d, J = 9.4 Hz, 1H), 4.49-4.28 (m, 5H), 4.22 (dd, J = 15.9, 5.5 Hz, 1H), 4.11 (s, 1H), 3.74-3.64 (m, 3H), 3.46 (s, 1H), 3.26-3.16 (m, 1H), 3.08 (s, 1H), 2.45 (s, 3H), 2.28-2.24 (m, 1H), 2.13-2.09 (m, 4H), 2.08 (s, 2H), 1.96-1.85 (m, 1H), 1.76 (s, 3H), 1.61 (s, 1H), 1.53-1.49 (m, 5H), 1.38 (s, 9H), 1.32-1.20 (m, 10H), 0.94 (s, 9H) |

TABLE 47-continued

Characterization data for intermediates prepare according to the procedure above.

| Intermediate | Structure | Chemical Name | MS: [(M + 1)]+ | 1H-NMR |
|---|---|---|---|---|
| G80 | 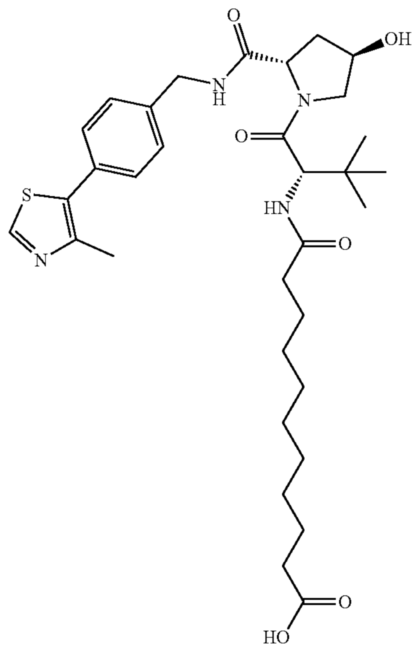 [SMILES: Cc1ncsc1-c1ccc(CNC(=O)[C@@H]2C[C@@H](O)CN2C(=O)[C@@H](NC(=O)CCCCCCCCCC(=O)O)C(C)(C)C)cc1] | 10-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]-decanoic acid | 629.35 | (400 MHz, DMSO-$d_6$) δ 8.99 (s, 1H), 8.56 (t, J = 6.1 Hz, 1H), 7.84 (d, J = 9.3 Hz, 1H), 7.43-7.39 (m, 4H), 5.12 (s, 1H), 4.55 (d, J = 9.4 Hz, 1H), 4.51-4.38 (m, 2H), 4.35 (s, 1H), 4.22 (dd, J = 15.8, 5.5 Hz, 1H), 3.72-3.61 (m, 1H), 2.45 (s, 3H), 2.25-2.07 (m, 3H), 1.93-1.91 (m, 1H), 1.50-1.46 (m, 5H), 1.30-1.24 (m, 13H), 0.94 (s, 9H) |
| G81 | 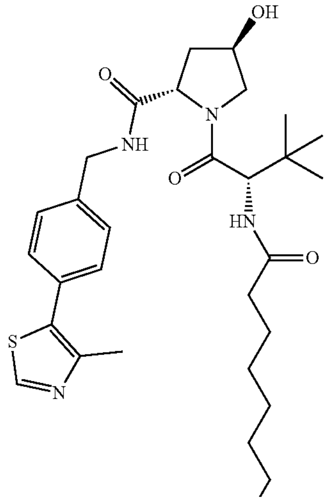 | tert-butyl N-[(5S,8S,10aR)-8-[[(1S)-3-carbamoyl-1-(diphenylmethylcarbamoyl)propyl]carbamoyl]-3-(10-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]decanoyl)-6-oxo-octahydropyrrolo[1,2-a][1,5]diazocin-5-yl]carbamate | 1231.85 | (400 MHz, DMSO-$d_6$) δ 8.99 (s, 1H), 8.72 (d, J = 8.4 Hz, 1H), 8.56 (t, J = 6.1 Hz, 1H), 7.84 (d, J = 9.3 Hz, 1H), 7.41 (q, J = 8.2 Hz, 4H), 7.39-7.30 (m, 11H), 6.72 (d, J = 17.5 Hz, 1H), 6.46 (d, J = 7.1 Hz, 1H), 6.09 (d, J = 8.4 Hz, 1H), 5.14-5.10 (m, 1H), 4.57-4.53 (m, 1H), 4.44-4.34 (m, 4H), 4.22 (dd, J = 15.9, 5.3 Hz, 1H), 4.11 (s, 1H), 3.75-3.60 (m, 3H), 3.33-3.27 (m, 10H), 3.09-3.05 (m, 1H), 2.45 (s, 3H), 2.10-2.06 (m, 1H), 1.52-1.48 (m, 4H), 1.41-1.35 (m, 17H), 1.32-1.24 (m, 12H), 0.94 (s, 9H) |

TABLE 47-continued

Characterization data for intermediates prepare according to the procedure above.

| Inter-me-diate | Structure | Chemical Name | MS: [(M + 1)]+ | $^1$H-NMR |
|---|---|---|---|---|
| | 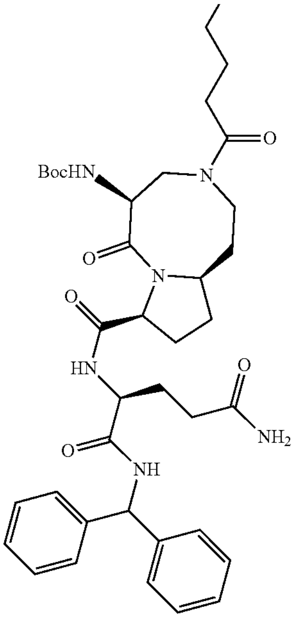 | | | |
| G82 | 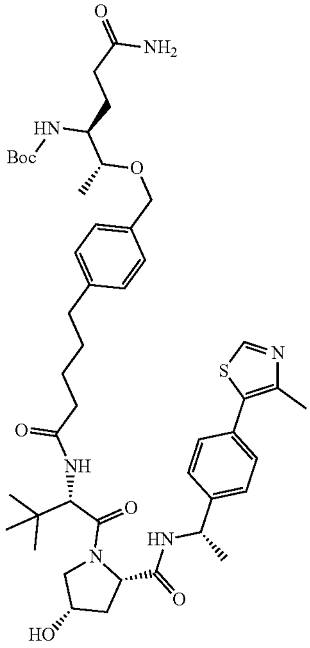 [SMILES: Cc1ncsc1-c1ccc([C@H](C)NC(=O)[C@@H]2C[C@H](O)CN2C(=O)[C@@H](NC(=O)CCCCc2ccc(CO[C@H](C)[C@H](CCC(N)=O)NC(=O)OC(C)(C)C)cc2)C(C)(C)C)cc1] | tert-butyl N-[(3S,4R)-1-carbamoyl-4-[[4-(4-[[(2S)-1-[(2S,4S)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]butyl)phenyl]methoxy]pentan-3-yl]carbamate | 864.45 | (400 MHz, $CDCl_3$) δ 8.78 (s, 1H), 8.07 (s, 1H), 7.64 (d, J = 8.0 Hz, 1H), 7.48-7.37 (m, 4H), 7.25 (d, J = 7.8 Hz, 2H), 7.16 (d, J = 7.9 Hz, 2H), 5.11 (q, J = 7.1 Hz, 1H), 4.89 (d, J = 9.8 Hz, 1H), 4.74 (d, J = 9.0 Hz, 1H), 4.59 (dd, J = 10.2, 6.1 Hz, 2H), 4.48 (s, 1H), 4.38 (d, J = 11.5 Hz, 1H), 3.96 (dd, J = 11.0, 4.2 Hz, 1H), 3.86 (d, J = 11.0 Hz, 1H), 3.69-3.65 (m, 1H), 3.63-3.59 (m, 1H), 2.67-2.63 (m, 2H), 2.57 (s, 3H), 2.37-2.33 (m, 1H), 2.29-2.25 (m, 4H), 2.18-2.14 (m, 1H), 2.00-1.96 (m, 1H), 1.73-1.65 (m, 4H), 1.52 (s, 3H), 1.45 (s, 9H), 1.22 (s, 3H), 1.07 (s, 9H) |

TABLE 47-continued

Characterization data for intermediates prepare according to the procedure above.

| Inter-me-diate | Structure | Chemical Name | MS: [(M + 1)]+ | $^1$H-NMR |
|---|---|---|---|---|
| G83 | 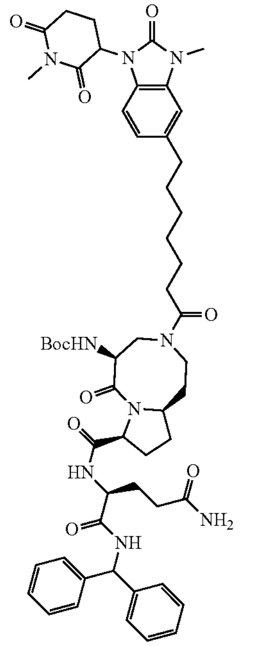 [SMILES: CN1C(=O)CCC(n2c(=O)n(C)c3cc(CCCCCCC(=O)N4CC[C@H]5CC[C@@H](C(=O)N[C@@H](CCC(N)=O)C(=O)NC(c6ccccc6)c6ccccc6)N5C(=O)[C@@H](NC(=O)OC(C)(C)C)C4)ccc32)C1=O] | tert-butyl N-[(5S,8S,10aR)-8-[[(1S)-3-carbamoyl-1-(diphenylmethylcarbamoyl)propyl]carbamoyl]-3-[7-[3-methyl-1-(1-methyl-2,6-dioxopiperidin-3-yl)-2-oxo-1,3-benzodiazol-5-yl]heptanoyl]-6-oxo-octahydropyrrolo[1,2-a][1,5]diazocin-5-yl]carbamate | 1004.75 | (400 MHz, $CDCl_3$) δ 7.40-7.17 (m, 10H), 6.93-6.83 (m, 2H), 6.70 (d, J = 7.2 Hz, 1H), 6.23 (t, J = 8.4 Hz, 1H), 5.73 (d, J = 6.3 Hz, 1H), 5.51 (s, 1H), 5.18 (dd, J = 12.8, 5.2 Hz, 1H), 4.61-4.02 (m, 4H), 3.89 (d, J = 13.8 Hz, 1H), 3.44 (s, 3H), 3.27 (s, 3H), 3.12-3.02 (m, 1H), 2.92-2.79 (m, 1H), 2.79-2.61 (m, 3H), 2.6-2.42 (m, 1H), 2.40-2.12 (m, 3H), 2.11-1.98 (m, 12H), 1.97-1.71 (m, 1H), 1.68-1.55 (m, 5H), 1.46 (s, 9H), 1.40-1.35 (m, 5H) |
| G84 | 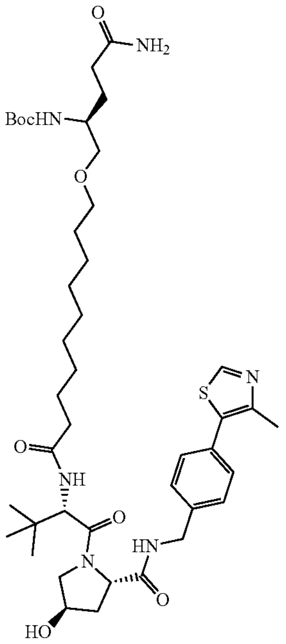 [SMILES: Cc1ncsc1-c1ccc(CNC(=O)[C@@H]2C[C@@H](O)CN2C(=O)[C@@H](NC(=O)CCCCCCCCCOC[C@H](CCC(N)=O)NC(=O)OC(C)(C)C)C(C)(C)C)cc1] | tert-butyl N-[(2S)-4-carbamoyl-1-[(9-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]nonyl)oxy]butan-2-yl]carbamate | 815.45 | (400 MHz, DMSO-$d_6$) δ 8.99 (s, 1H), 8.56 (t, J = 6.1 Hz, 1H), 7.85 (d, J = 9.3 Hz, 1H), 7.41 (q, J = 8.4 Hz, 4H), 7.23 (s, 1H), 6.70 (s, 1H), 6.57 (d, J = 8.7 Hz, 1H), 5.13 (d, J = 3.6 Hz, 1H), 4.55 (d, J = 9.4 Hz, 1H), 4.49-4.39 (m, 2H), 4.36 (s, 1H), 4.23 (dd, J = 15.9, 5.5 Hz, 1H), 3.72-3.61 (m, 2H), 3.29-3.16 (m, 2H), 2.46 (s, 3H), 2.31-2.21 (m, 1H), 2.15-2.10 (m, 2H), 2.08 (s, 3H), 2.07-2.01 (m, 2H), 1.96-1.88 (m, 1H), 1.74-1.64 (m, 1H), 1.55-1.43 (m, 1H), 1.38 (s, 9H), 1.30-1.21 (m, 14H), 0.94 (s, 9H) |

TABLE 47-continued

| Characterization data for intermediates prepare according to the procedure above. | | | | |
|---|---|---|---|---|
| Inter-me-diate | Structure | Chemical Name | MS: [(M + 1)]+ | $^1$H-NMR |
| G85 | 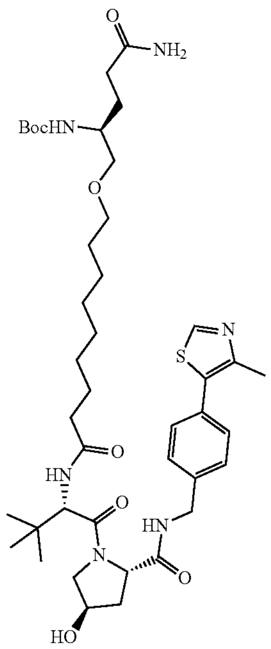 [SMILES: Cc1ncsc1-c1ccc(CNC(=O)[C@@H]2C[C@@H](O)CN2C(=O)[C@@H](NC(=O)CCCCCCCCOC[C@H](CCC(N)=O)NC(=O)OC(C)(C)C)C(C)(C)C)cc1] | tert-butyl N-[(2S)-4-carbamoyl-1-[(8-[[(2S)-1-[(2S,4R)-4-hydroxy-2-([[4-(4-methyl-1,3-thiazol-5-yl)phenyl]methyl] carbamoyl)pyrrolidin-1-yl]-3,3-dimethyl-1-oxobutan-2-yl]carbamoyl]octyl) oxy]butan-2-yl]carbamate | 801.55 | (400 MHz, DMSO-$d_6$) δ 8.99 (s, 1H), 8.57 (t, J = 6.1 Hz, 1H), 7.85 (d, J = 9.3 Hz, 1H), 7.41 (q, J = 8.4 Hz, 4H), 7.23 (s, 1H), 6.70 (s, 1H), 6.57 (d, J = 8.7 Hz, 1H), 5.15-5.13 (m, 1H), 4.55 (d, J = 9.3 Hz, 1H), 4.48-4.38 (m, 2H), 4.37-4.35 (m, 1H), 4.22 (dd, J = 15.8, 5.4 Hz, 1H), 3.65 (t, J = 8.7 Hz, 2H), 3.49-3.45 (m, 1H), 3.40-3.35 (m, 2H), 3.33-3.12 (m, 2H), 2.45 (s, 3H), 2.28-2.24 (m, 1H), 2.10-2.04 (m, 3H), 1.92-1.88 (m, 1H), 1.73-1.71 (m, 1H), 1.48-1.44 (m, 6H), 1.38 (s, 9H), 1.28-1.23 (m, 8H), 0.94 (s, 9H) |
| G86 | 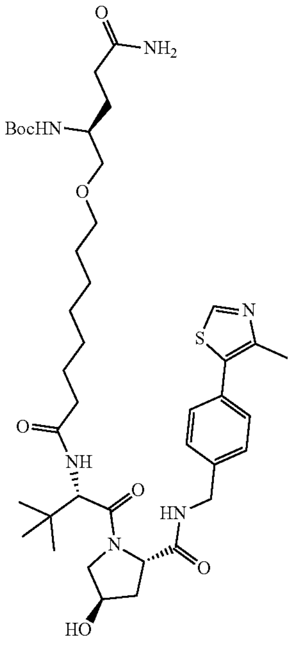 [SMILES: Cc1ncsc1-c1ccc(CNC(=O)[C@@H]2C[C@@H](O)CN2C(=O)[C@@H](NC(=O)CCCCCCCOC[C@H](CCC(N)=O)NC(=O)OC(C)(C)C)C(C)(C)C)cc1] | tert-butyl ((S)-5-amino-1-((8-(((S)-1-((2S,4R)-4-hydroxy-2-((4-(4-methylthiazol-5-yl)benzyl)carbamoyl) pyrrolidin-1-yl)-3,3-dimethyl-1-oxobutan-2-yl)amino)-8-oxooctyl)oxy)-5-oxopentan-2-yl)carbamate | 787.60 | (400 MHz, DMSO-$d_6$) δ 9.00 (s, 1H), 8.57 (t, J = 6.0 Hz, 1H), 7.85 (d, J = 9.4 Hz, 1H), 7.46-7.40 (m, 4H), 7.23 (s, 1H), 6.77-6.50 (m, 2H), 5.13 (s, 1H), 4.61-4.17 (m, 4H) 3.66 (t, J = 8.8 Hz, 2H), 3.06-2.99 (m, 2H), 2.46 (s, 3H), 2.33-1.86 (m, 6H), 1.74-1.68 (m, 1H), 1.52-1.44 (m, 4H), 1.38 (s, 9H), 1.29-1.24 (m, 6H), 1.20-1.14 (m, 3H), 0.94 (s, 9H) |

TABLE 47-continued

Characterization data for intermediates prepare according to the procedure above.

| Intermediate | Structure | Chemical Name | MS: [(M + 1)]+ | $^1$H-NMR |
|---|---|---|---|---|
| G87 | 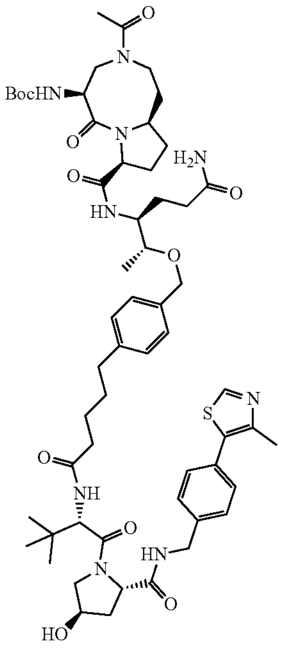 [SMILES: CC(=O)N1CC[C@H]2CC[C@@H](C(=O)N[C@@H](CCC(N)=O)[C@@H](C)OCc3ccc(CCCCC(=O)N[C@H](C(=O)N4C[C@H](O)C[C@H]4C(=O)NCc4ccc(-c5scnc5C)cc4)C(C)(C)C)cc3)N2C(=O)[C@@H](NC(=O)OC(C)(C)C)C1] | tert-butyl N-[(5S,8S,10aR)-3-acetyl-8-[[(3S,4R)-1-carbamoyl-4-[[4-(4-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]butyl)phenyl]methoxy]pentan-3-yl]carbamoyl]-6-oxo-octahydropyrrolo[1,2-a][1,5]diazocin-5-yl]carbamate | 1100.35 | (400 MHz, DMSO-d$_6$) δ 8.99 (s, 1H), 8.56 (t, J = 6.1 Hz, 1H), 7.88 (d, J = 9.4 Hz, 1H), 7.82-7.75 (m, 1H), 7.41 (q, J = 8.4 Hz, 4H), 7.23 (d, J = 8.0 Hz, 2H), 7.14 (d, J = 7.9 Hz, 2H), 7.08 (s, 1H), 6.68 (s, 1H), 6.57 (d, J = 7.2 Hz, 1H), 5.13 (d, J = 3.6 Hz, 1H), 4.55 (d, J = 9.4 Hz, 1H), 4.49-4.28 (m, 6H), 4.24 (d, J = 5.5 Hz, 1H), 4.23-4.12 (m, 1H), 3.80-3.72 (m, 2H), 3.66 (q, J = 12.9, 9.7 Hz, 4H), 3.45-3.35 (m, 2H), 3.20-3.09 (m, 1H), 2.57 (d, J = 6.2 Hz, 3H), 2.45 (s, 3H), 2.29 (t, J = 7.0 Hz, 1H), 2.20-2.09 (m, 3H), 2.11-1.97 (m, 5H), 1.98-1.80 (m, 1H), 1.79-1.59 (m, 1H), 1.59-1.45 (m, 9H), 1.38 (s, 9H), 1.06 (dd, J = 6.3, 2.2 Hz, 3H), 0.94 (s, 9H). |
| G88 | 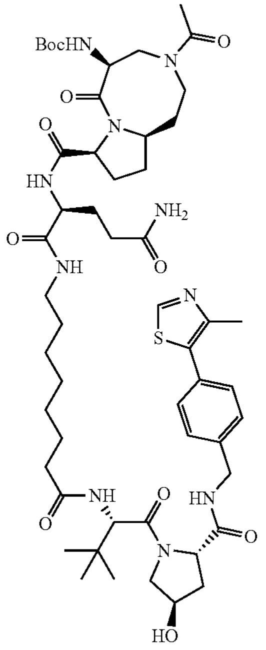 [SMILES: CC(=O)N1CC[C@H]2CC[C@@H](C(=O)N[C@@H](CCC(N)=O)C(=O)NCCCCCCCC(=O)N[C@H](C(=O)N3C[C@H](O)C[C@H]3C(=O)NCc3ccc(-c4scnc4C)cc3)C(C)(C)C)N2C(=O)[C@@H](NC(=O)OC(C)(C)C)C1] | tert-butyl N-[(5S,8S,10aR)-3-acetyl-8-[[(1S)-3-carbamoyl-1-[(7-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]heptyl)carbamoyl]propyl]carbamoyl]-6-oxo-octahydropyrrolo[1,2-a][1,5]diazocin-5-yl]carbamate | 1051.85 | (400 MHz, DMSO-d$_6$) δ 8.99 (s, 1H), 8.57 (t, J = 6.1 Hz, 1H), 8.07 (d, J = 8.1 Hz, 1H), 7.84 (dd, J = 10.5, 7.4 Hz, 2H), 7.41 (q, J = 8.4 Hz, 4H), 7.20 (s, 1H), 6.74 (s, 1H), 6.58 (d, J = 7.0 Hz, 1H), 5.76 (s, 1H), 5.13 (d, J = 3.5 Hz, 1H), 4.55 (d, J = 9.4 Hz, 1H), 4.49-4.43 (m, 2H), 4.36 (s, 2H), 4.27-4.11 (m, 2H), 3.69-3.65 (m, 3H), 3.10-3.02 (m, 1H), 3.00 (dd, J = 13.1, 6.3 Hz, 1H), 2.45 (s, 3H), 2.31-2.20 (m, 2H), 2.18-1.96 (m, 13H), 1.96-1.78 (m, 3H), 1.80-1.59 (m, 3H), 1.50-1.46 (m, 2H), 1.38 (s, 9H), 1.26-1.22 (m, 8H), 0.94 (s, 9H) |

TABLE 47-continued

| Characterization data for intermediates prepare according to the procedure above. | | | | |
|---|---|---|---|---|
| Inter-me-diate | Structure | Chemical Name | MS: [(M + 1)]$^+$ | $^1$H-NMR |
| G89 | 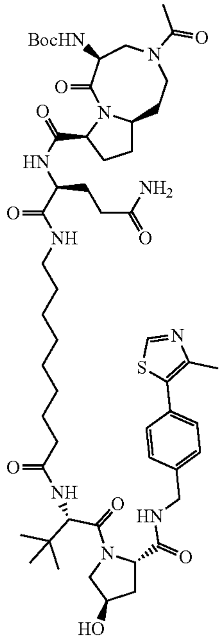 [SMILES: CC(=O)N1CC[C@H]2CC[C@@H](C(=O)N[C@@H](CCC(N)=O)C(=O)NCCCCCCCCC(=O)N[C@H](C(=O)N3C[C@H](O)C[C@H]3C(=O)NCc3ccc(-c4scnc4C)cc3)C(C)(C)C)N2C(=O)[C@@H](NC(=O)OC(C)(C)C)C1] | tert-butyl N-[(5S,8S,10aR)-3-acetyl-8-[[(1S)-3-carbamoyl-1-[(8-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]octyl)carbamoyl]propyl]carbamoyl]-6-oxo-octahydropyrrolo[1,2-a][1,5]diazocin-5-yl]carbamate | 1065.85 | (400 MHz, DMSO-$d_6$) δ 8.99 (s, 1H), 8.57 (t, J = 6.1 Hz, 1H), 8.07 (d, J = 7.8 Hz, 1H), 7.90-7.79 (m, 2H), 7.41 (q, J = 8.4 Hz, 4H), 7.21 (s, 1H), 6.75 (s, 1H), 6.58 (d, J = 7.0 Hz, 1H), 5.13 (d, J = 3.5 Hz, 1H), 4.55 (d, J = 9.4 Hz, 1H), 4.51-4.37 (m, 3H), 4.36 (s, 2H), 4.27-4.13 (m, 1H), 4.16 (s, 2H), 3.72-3.65 (m, 2H), 3.63 (s, 2H), 3.32 (s, 1H), 3.09-2.97 (m, 2H), 2.45 (s, 3H), 2.29-2.24 (m, 2H), 2.12 (s, 3H), 2.09-2.05 (m, 5H), 2.01 (s, 1H), 1.93-1.89 (m, 1H), 1.84 (s, 2H), 1.80-1.66 (m, 1H), 1.65-1.61 (m, 1H), 1.49-1.45 (m, 2H), 1.40-1.36 (m, 11H), 1.26-1.21 (m, 10H), 0.94 (s, 9H) |
| G90 | 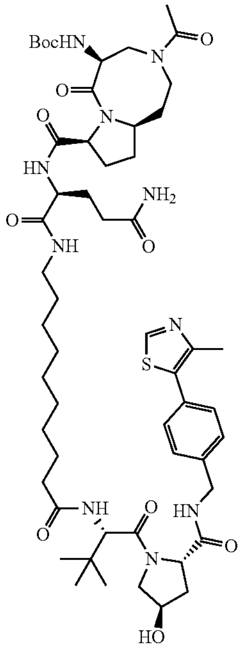 [SMILES: CC(=O)N1CC[C@H]2CC[C@@H](C(=O)N[C@@H](CCC(N)=O)C(=O)NCCCCCCCCCC(=O)N[C@H](C(=O)N3C[C@H](O)C[C@H]3C(=O)NCc3ccc(-c4scnc4C)cc3)C(C)(C)C)N2C(=O)[C@@H](NC(=O)OC(C)(C)C)C1] | tert-butyl N-[(5S,8S,10aR)-3-acetyl-8-[[(1S)-3-carbamoyl-1-[(9-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]nonyl)carbamoyl]propyl]carbamoyl]-6-oxo-octahydropyrrolo[1,2-a][1,5]diazocin-5-yl]carbamate | 1079.90 | (400 MHz, DMSO-$d_6$) δ 8.99 (s, 1H), 8.55 (t, J = 6.1 Hz, 1H), 8.06 (d, J = 7.8 Hz, 1H), 7.82 (dd, J = 12.6, 7.3 Hz, 2H), 7.41 (q, J = 8.4 Hz, 4H), 7.19 (s, 1H), 6.73 (s, 1H), 6.65-6.53 (m, 1H), 5.12 (d, J = 3.5 Hz, 1H), 4.55 (d, J = 9.4 Hz, 1H), 4.51-4.39 (m, 2H), 4.36 (s, 2H), 4.28-4.13 (m, 1H), 4.16 (s, 2H), 3.77-3.51 (m, 7H), 3.06-2.97 (m, 3H), 2.45 (s, 3H), 2.30-2.24 (m, 1H), 2.18-1.99 (m, 10H), 1.96-1.86 (m, 1H), 1.87-1.81 (m, 2H), 1.74-1.68 (m, 1H), 1.57-1.41 (m, 1H), 1.40-1.36 (m, 11H), 1.25-1.22 (m, 12H), 0.94 (s, 9H) |

TABLE 47-continued

Characterization data for intermediates prepare according to the procedure above.

| Inter-me-diate | Structure | Chemical Name | MS: [(M + 1)]+ | ¹H-NMR |
|---|---|---|---|---|
| G91 | 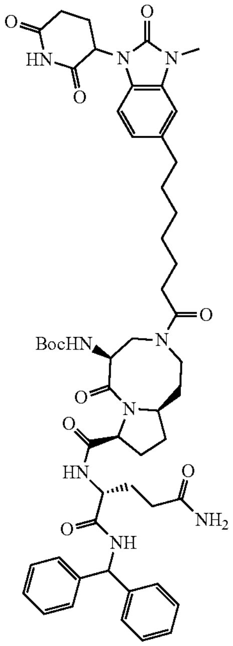 [SMILES: Cn1c(=O)n(C2CCC(=O)NC2=O)c2ccc(CCCCCCC(=O)N3CC[C@H]4CC[C@@H](C(=O)N[C@H](CCC(N)=O)C(=O)NC(c5ccccc5)c5ccccc5)N4C(=O)[C@@H](NC(=O)OC(C)(C)C)C3)cc21] | tert-butyl N-[(5S,8S,10aR)-8-[[(1R)-3-carbamoyl-1-(diphenylmethylcarbamoyl) propyl]carbamoyl]-3-[7-[1-(2,6-dioxopiperidin-3-yl)-3-methyl-2-oxo-1,3-benzodiazol-5-yl]heptanoyl]-6-oxo-octahydropyrrolo[1,2-a] [1,5]diazocin-5-yl]carbamate | 990.60 | (400 MHz, $CD_3OD$) δ 7.44-7.34 (m, 4H), 7.30 (t, J = 7.1 Hz, 3H), 7.27-7.19 (m, 3H), 7.03 (s, 1H), 7.01-6.93 (m, 2H), 6.31-6.25 (m, 1H), 5.39-5.24 (m, 1H), 4.49-4.31 (m, 3H), 4.20-4.07 (m, 1H), 3.83 (d, J = 14.1 Hz, 1H), 3.75-3.64 (m, 1H), 3.43 (d, J = 2.0 Hz, 1H), 3.41 (s, 3H), 3.24-3.11 (m, 1H), 2.98-2.87 (m, 1H), 2.86-2.65 (m, 6H), 2.48 (s, 2H), 2.38-2.20 (m, 5H), 2.20-2.01 (m, 4H), 1.99-1.80 (m, 3H), 1.66 (d, J = 18.3 Hz, 5H), 1.46 (s, 9H) |
| G92 | 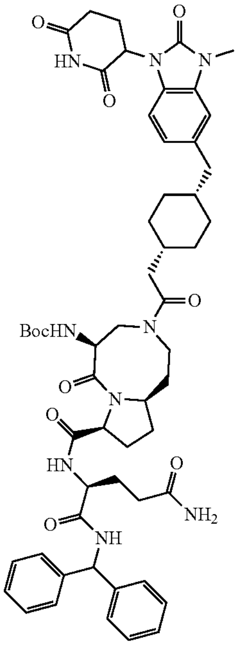 [SMILES: Cn1c(=O)n(C2CCC(=O)NC2=O)c2ccc(C[C@H]3CC[C@@H](CC(=O)N4CC[C@H]5CC[C@@H](C(=O)N[C@@H](CCC(N)=O)C(=O)NC(c6ccccc6)c6ccccc6)N5C(=O)[C@@H](NC(=O)OC(C)(C)C)C4)CC3)cc21] | N-[(5S,8S,10aR)-8-[[(1S)-3-carbamoyl-1-(diphenylmethylcarbamoyl) propyl]carbamoyl]-6-oxo-3-[2-[(1s,4s)-4-[[1-(2,6-dioxopiperidin-3-yl)-3-methyl-2-oxo-1,3-benzodiazol-5-yl]methyl]cyclohexyl] acetyl]-octahydropyrrolo[1,2-a] [1,5]diazocin-5-yl]carbamate | 1016.80 | (400 MHz, DMSO-$d_6$) δ 11.09 (s, 1H), 8.74 (d, J = 8.3 Hz, 1H), 8.21 (dd, J = 17.3, 7.9 Hz, 1H), 7.42-7.17 (m, 11H), 7.05-6.91 (m, 2H), 6.85-6.82 (m, 1H), 6.76-6.72 (m, 1H), 6.47 (d, J = 6.7 Hz, 1H), 6.11 (d, J = 8.4 Hz, 1H), 5.34 (dd, J = 12.8, 5.4 Hz, 1H), 4.54-4.19 (m, 3H), 4.10-3.95 (m, 1H), 3.84-3.80 (m, 2H), 3.33 (s, 3H), 3.23-3.02 (m, 1H), 2.98-2.81 (m, 1H), 2.77-2.56 (m, 5H), 2.46-2.22 (m, 1H), 2.10-2.06 (m, 4H), 2.03-1.88 (m, 6H), 1.86-1.55 (m, 5H), 1.45-1.39 (m, 16H) |

TABLE 47-continued

Characterization data for intermediates prepare according to the procedure above.

| Inter-me-diate | Structure | Chemical Name | MS: [(M + 1)]$^+$ | $^1$H-NMR |
|---|---|---|---|---|
| G93 | 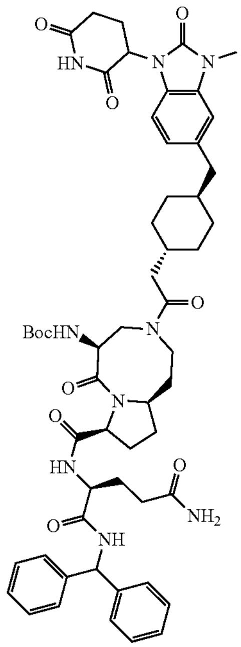 [SMILES: Cn1c(=O)n(C2CCC(=O)NC2=O)c2ccc(C[C@H]3CC[C@H](CC(=O)N4CC[C@H]5CC[C@@H](C(=O)N[C@@H](CCC(N)=O)C(=O)NC(c6ccccc6)c6ccccc6)N5C(=O)[C@@H](NC(=O)OC(C)(C)C)C4)CC3)cc21] | tert-butyl N-[(5S,8S,10aR)-8-[[(1S)-3-carbamoyl-1-(diphenylmethylcarbamoyl) propyl]carbamoyl]-6-oxo-3-[2-[(1r,4r)-4-[[1-(2,6-dioxopiperidin-3-yl)-3-methyl-2-oxo-1,3-benzodiazol-5-yl]methyl]cyclohexyl] acetyl]-octahydropyrrolo[1,2-a] [1,5]diazocin-5-yl]carbamate | 1016.50 | (300 MHz, $CDCl_3$) δ 9.50 (d, J = 10.0 Hz, 1H), 8.11 (d, J = 8.2 Hz, 1H), 7.74 (d, J = 9.6 Hz, 2H), 7.24 (td, J = 11.8, 9.9, 5.9 Hz, 16H), 6.80 (dq, J = 14.6, 8.1 Hz, 4H), 6.52 (d, J = 7.0 Hz, 1H), 6.23-6.14 (m, 1H), 6.02-5.81 (m, 2H), 5.28-5.11 (m, 2H), 4.65 (s, 2H), 4.36 (dd, J = 19.8, 11.7 Hz, 2H), 4.00 (d, J = 13.5 Hz, 3H), 3.07 (s, 1H), 2.92-2.34 (m, 8H), 2.19 (d, J = 12.8 Hz, 6H), 2.00-1.60 (m, 1H), 1.46 (d, J = 15.4 Hz, 16H) |
| G94 | 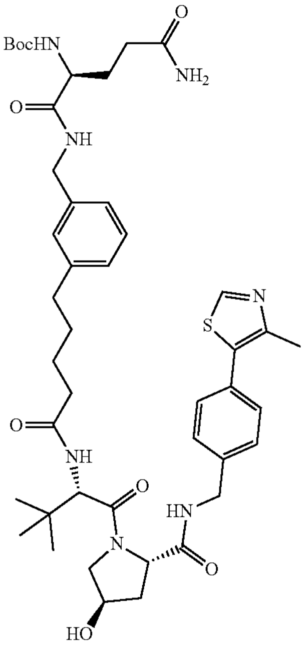 [SMILES: Cc1ncsc1-c1ccc(CNC(=O)[C@@H]2C[C@@H](O)CN2C(=O)[C@@H](NC(=O)CCCCc2cccc(CNC(=O)[C@H](CCC(N)=O)NC(=O)OC(C)(C)C)c2)C(C)(C)C)cc1] | tert-butyl N-[(1S)-3-carbamoyl-1-([[3-(4-[[(2S)-1-[(2S,4R)-4-hydroxy-2-([[4-(4-methyl-1,3-thiazol-5-yl)phenyl]methyl] carbamoyl)pyrrolidin-1-yl]-3,3-dimethyl-1-oxobutan-2-yl]carbamoyl]butyl) phenyl]methyl] carbamoyl)propyl] carbamate | 848.42 | (300 MHz, DMSO-$d_6$) δ 8.98 (s, 1H), 8.55 (t, J = 6.1 Hz, 1H), 8.26 (t, J = 5.9 Hz, 1H), 7.89 (d, J = 9.3 Hz, 1H), 7.45-7.35 (m, 5H), 7.27 (s, 1H), 7.19 (t, J = 7.5 Hz, 1H), 7.11-6.99 (m, 3H), 6.89 (d, J = 7.8 Hz, 1H), 6.77 (s, 1H), 5.11 (s, 1H), 4.54 (d, J = 9.3 Hz, 1H), 4.50-4.30 (m, 3H), 4.25 (d, J = 5.8 Hz, 3H), 3.94-3.87 (m, 1H), 3.69-3.62 (m, 2H), 2.57-2.53 (m, 3H), 2.44 (s, 3H), 2.34-2.23 (m, 1H), 2.20-2.00 (m, 3H), 1.94-1.82 (m, 1H), 1.76-1.67 (m, 1H), 1.60-1.43 (m, 4H), 1.38 (s, 9H), 0.93 (s, 9H) |

TABLE 47-continued

Characterization data for intermediates prepare according to the procedure above.

| Intermediate | Structure | Chemical Name | MS: [(M + 1)]$^+$ | $^1$H-NMR |
|---|---|---|---|---|
| G95 | 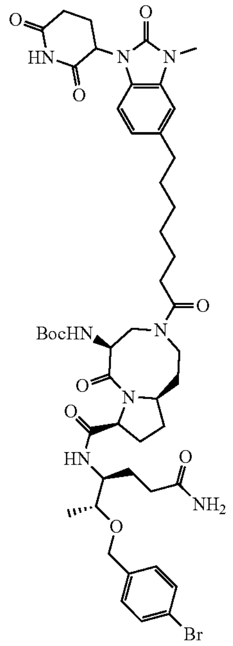 [SMILES: C[C@@H](OCc1ccc(Br)cc1)[C@H](CCC(N)=O)NC(=O)[C@@H]1CC[C@@H]2CCN(C(=O)CCCCCCc3ccc4c(c3)n(C)c(=O)n4C3CCC(=O)NC3=O)C[C@H](NC(=O)OC(C)(C)C)C(=O)N21] | tert-butyl N-[(5S,8S,10aR)-8-[[(3S,4R)-4-[(4-bromophenyl)methoxy]-1-carbamoylpentan-3-yl]carbamoyl]-3-[7-[1-(2,6-dioxopiperidin-3-yl)-3-methyl-2-oxo-1,3-benzodiazol-5-yl]heptanoyl]-6-oxo-octahydropyrrolo[1,2-a][1,5]diazocin-5-yl]carbamate | 993.20, 995.20 | (400 MHz, DMSO-$d_6$) δ 11.09 (s, 1H), 7.82 (t, J = 8.7 Hz, 1H), 7.55-7.49 (m, 2H), 7.29 (dd, J = 8.4, 3.4 Hz, 2H), 7.12-6.98 (m, 3H), 6.84 (d, J = 1.6 Hz, 1H), 6.69 (s, 1H), 6.62-6.53 (m, 1H), 5.34 (dd, J = 12.7, 5.4 Hz, 1H), 4.56-4.28 (m, 5H), 4.21-4.04 (m, 1H), 3.87-3.46 (m, 4H), 3.41 (p, J = 6.2 Hz, 1H), 3.34 (s, 3H), 3.30-3.09 (m, 1H), 2.98-2.84 (m, 1H), 2.77-2.55 (m, 5H), 2.47-2.37 (m, 1H), 2.34-1.91 (m, 4H), 1.91-1.43 (m, 8H), 1.43-1.27 (m, 15H), 1.06 (d, J = 6.3 Hz, 3H) |
| G96 | 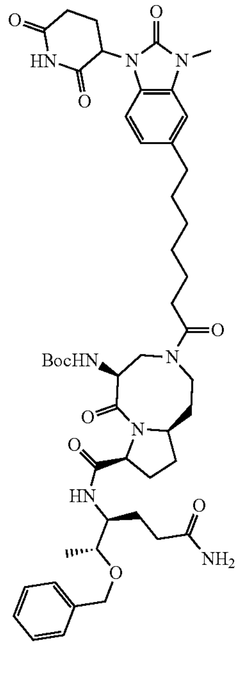 [SMILES: C[C@@H](OCc1ccccc1)[C@H](CCC(N)=O)NC(=O)[C@@H]1CC[C@@H]2CCN(C(=O)CCCCCCc3ccc4c(c3)n(C)c(=O)n4C3CCC(=O)NC3=O)C[C@H](NC(=O)OC(C)(C)C)C(=O)N21] | tert-butyl N-[(5S,8S,10aR)-8-[[(3S,4R)-4-(benzyloxy)-1-carbamoylpentan-3-yl]carbamoyl]-3-[7-[1-(2,6-dioxopiperidin-3-yl)-3-methyl-2-oxo-1,3-benzodiazol-5-yl]heptanoyl]-6-oxo-octahydropyrrolo[1,2-a][1,5]diazocin-5-yl]carbamate | 915.35 | (400 MHz, DMSO-$d_6$) δ 11.09 (s, 1H), 7.82 (dd, J = 9.2, 6.7 Hz, 1H), 7.37-7.23 (m, 5H), 7.14-6.96 (m, 3H), 6.88-6.83 (m, 1H), 6.68 (s, 1H), 6.58 (d, J = 6.9 Hz, 1H), 5.34 (dd, J = 12.7, 5.4 Hz, 1H), 4.56-4.27 (m, 6H), 4.24-4.04 (m, 1H), 3.91-3.63 (m, 4H), 3.63-3.37 (m, 2H), 3.32 (s, 3H), 3.28-3.06 (m, 1H), 2.97-2.85 (m, 2H), 2.82-2.55 (m, 6H), 2.43 (d, J = 9.7 Hz, 1H), 2.35-2.23 (m, 1H), 2.22-2.09 (m, 4H), 2.04-1.95 (m, 1H), 1.91-1.69 (m, 2H), 1.69-1.45 (m, 2H), 1.39 (s, 9H), 1.38-1.29 (m, 4H), 1.07 (d, J = 6.3, 3H) |

TABLE 47-continued

Characterization data for intermediates prepare according to the procedure above.

| Inter-me-diate | Structure | Chemical Name | MS: [(M + 1)]$^+$ | $^1$H-NMR |
|---|---|---|---|---|
| G97 | 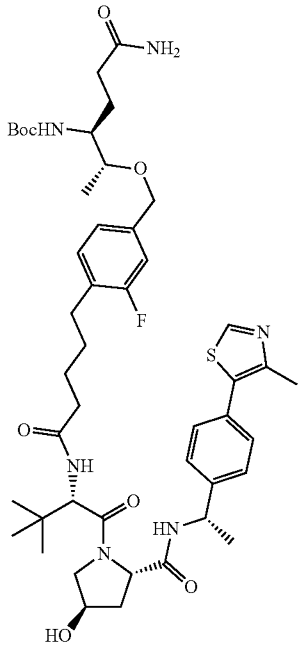 [SMILES: Cc1ncsc1-c1ccc([C@H](C)NC(=O)[C@@H]2C[C@@H](O)CN2C(=O)[C@@H](NC(=O)CCCCc2ccc(CO[C@H](C)[C@H](CCC(N)=O)NC(=O)OC(C)(C)C)cc2F)C(C)(C)C)cc1] | tert-butyl ((2R,3S)-6-amino-2-((3-fluoro-4-(5-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-5-oxopentyl)benzyl)oxy)-6-oxohexan-3-yl)carbamate | 881.40 | (400 MHz, DMSO-$d_6$) δ 8.99 (s, 1H), 8.37 (d, J = 7.8 Hz, 1H), 7.81 (d, J = 9.3 Hz, 1H), 7.47-7.35 (m, 4H), 7.26-7.16 (m, 2H), 7.08 (t, J = 10.7 Hz, 2H), 6.71-6.61 (m, 2H), 5.09 (d, J = 3.6 Hz, 1H), 4.96-4.88 (m, 1H), 4.51 (d, J = 9.2 Hz, 1H), 4.44 (d, J = 9.1 Hz, 3H), 4.28 (s, 1H), 3.60 (s, 2H), 3.48-3.39 (m, 2H), 2.58 (s, 3H), 2.46 (s, 3H), 2.33-2.26 (m, 1H), 2.18-2.10 (m, 1H), 2.04-1.99 (m, 1H), 1.89-1.71 (m, 1H), 1.52 (s, 8H), 1.41-1.36 (m, 11H), 1.06 (d, J = 6.2 Hz, 3H), 0.93 (s, 9H) |

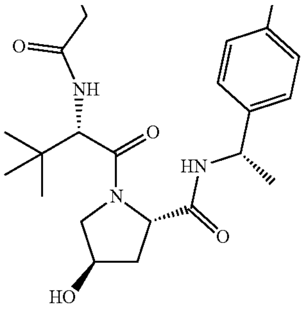

TABLE 47-continued

Characterization data for intermediates prepare according to the procedure above.

| Inter-me-diate | Structure | Chemical Name | MS: [(M + 1)]+ | $^1$H-NMR |
|---|---|---|---|---|
| G98 | 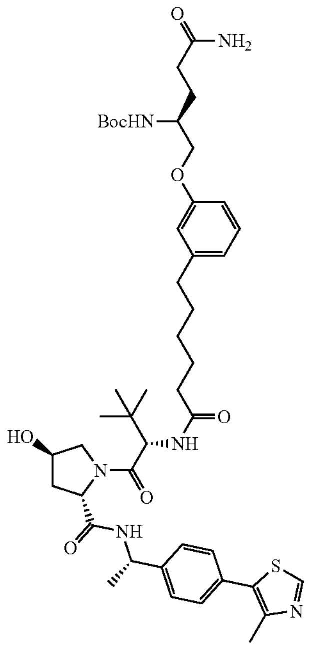 [SMILES: Cc1ncsc1-c1ccc([C@H](C)NC(=O)[C@@H]2C[C@@H](O)CN2C(=O)[C@@H](NC(=O)CCCCCc2cccc(OC[C@H](CCC(N)=O)NC(=O)OC(C)(C)C)c2)C(C)(C)C)cc1] | tert-butyl N-[(2S)-4-carbamoyl-1-[3-(5-[[(2S)-1-[(2S,4R)-4-hydroxy-2-[[(1S)-1-[4-(4-methyl-1,3-thiazol-5-yl)phenyl]ethyl] carbamoyl]pyrrolidin-1-yl]-3,3-dimethyl-1-oxobutan-2-yl]carbamoyl]pentyl) phenoxy]butan-2-yl]carbamate | 849.50 | $^1$H NMR (400 MHz, DMSO-$d_6$) δ 8.99 (s, 1H), 8.37 (d, J = 7.8 Hz, 1H), 7.79 (d, J = 9.3 Hz, 1H), 7.47-7.39 (m, 2H), 7.38 (d, J = 8.3 Hz, 2H), 7.26 (s, 1H), 7.16 (t, J = 7.9 Hz, 1H), 6.81 (d, J = 8.4 Hz, 1H), 6.78-6.69 (m, 4H), 5.10 (d, J = 3.5 Hz, 1H), 4.92 (p, J = 7.4, 6.5 Hz, 1H), 4.52 (d, J = 9.3 Hz, 1H), 4.43 (t, J = 8.1 Hz, 1H), 4.29 (s, 1H), 3.84 (qd, J = 9.6, 5.9 Hz, 2H), 3.74-3.59 (m, 2H), 3.18 (d, J = 5.3 Hz, 2H), 2.46 (s, 3H), 2.26 (m, 1H), 2.17-2.07 (m, 3H), 2.10-1.96 (m, 1H), 1.80 (m, 2H), 1.69-1.45 (m, 6H), 1.39 (d, J = 2.4 Hz, 9H), 1.37 (s, 3H), 1.32-1.22 (m, 2H), 0.93 (s, 9H) |
| G99 | 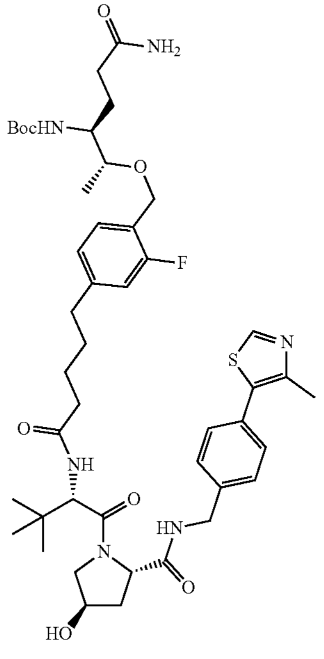 [SMILES: Cc1ncsc1-c1ccc(CNC(=O)[C@@H]2C[C@@H](O)CN2C(=O)[C@@H](NC(=O)CCCCc2ccc(CO[C@H](C)[C@H](CCC(N)=O)NC(=O)OC(C)(C)C)c(F)c2)C(C)(C)C)cc1] | tert-butyl N-[(3S,4R)-1-carbamoyl-4-[[2-fluoro-4-(4-[[(2S)-1-[(2S,4R)-4-hydroxy-2-([[4-(4-methyl-1,3-thiazol-5-yl)phenyl]methyl] carbamoyl)pyrrolidin-1-yl]-3,3-dimethyl-1-oxobutan-2-yl]carbamoyl]butyl) phenyl]methoxy]pentan-3-yl]carbamate | 867.30 | (400 MHz, DMSO-$d_6$) δ 8.99 (s, 1H), 8.55 (t, J = 6.0 Hz, 1H), 7.88 (d, J = 9.3 Hz, 1H), 7.47-7.36 (m, 5H), 7.33 (t, J = 7.8 Hz, 1H), 7.20 (s, 1H), 7.01-6.98 (m, 2H), 6.67 (s, 1H), 6.58 (d, J = 8.8 Hz, 1H), 5.12 (s, 1H), 4.61-4.39 (m, 6H), 4.35 (s, 1H), 4.22 (dd, J = 15.8, 5.3 Hz, 1H), 3.72-3.60 (m, 2H), 3.41 (t, J = 5.8 Hz, 2H), 2.57 (t, J = 7.1 Hz, 1H), 2.45 (s, 3H), 2.37-2.25 (m, 1H), 2.20-1.84 (m, 4H), 1.81-1.72 (m, 1H), 1.58-1.43 (m, 5H), 1.38 (s, 9H), 1.06 (d, J = 5.6 Hz, 3H), 0.94 (s, 9H) |

TABLE 47-continued

| Inter-me-diate | Structure | Chemical Name | MS: [(M + 1)]$^+$ | $^1$H-NMR |
|---|---|---|---|---|
| Characterization data for intermediates prepare according to the procedure above. | | | | |
| G100 | 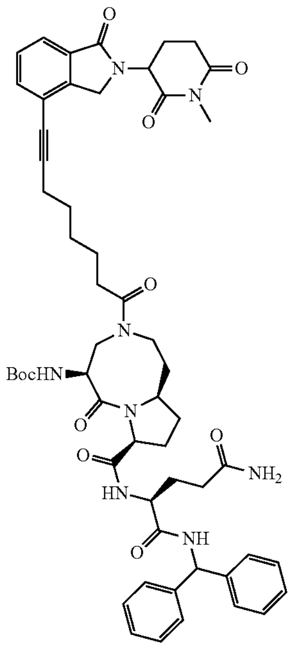 [SMILES: CN1C(=O)CCC(N2Cc3c(C#CCCCCCC(=O)N4CC[C@H]5CC[C@@H](C(=O)N[C@@H](CCC(N)=O)C(=O)NC(c6ccccc6)c6ccccc6)N5C(=O)[C@@H](NC(=O)OC(C)(C)C)C4)cccc3C2=O)C1=O] | tert-butyl N-[(5S,8S,10aR)-8-[[(1S)-3-carbamoyl-1-(diphenylmethylcarbamoyl)propyl]carbamoyl]-3-[8-[2-(1-methyl-2,6-dioxopiperidin-3-yl)-1-oxo-3H-isoindol-4-yl]oct-7-ynoyl]-6-oxo-octahydropyrrolo[1,2-a][1,5]diazocin-5-yl]carbamate | 999.00 | (400 MHz, $CDCl_3$) δ 7.81 (d, J = 7.6 Hz, 1H), 7.70 (d, J = 7.8 Hz, 1H), 7.60-7.55 (m, 1H), 7.46-7.42 (m, 1H), 7.36-7.28 (m, 6H), 7.28-7.24 (m, 5H), 6.31-6.21 (m, 1H), 5.76-5.70 (m, 1H), 5.52-4.45 (m, 1H), 5.25-5.16 (m, 1H), 4.57-4.31 (m, 2H), 4.26-4.24 (m, 1H), 4.07-3.95 (m, 3H), 3.89 (s, 3H), 3.20-2.81 (m, 3H), 258-2.52 (m, 4H), 2.50-2.40 (m, 4H), 2.23-2.18 (m, 3H), 2.09-1.95 (m, 2H), 1.85-1.61 (m, 8H), 1.52-1.49 (m, 2H), 1.45 (s, 9H) |
| G101 | 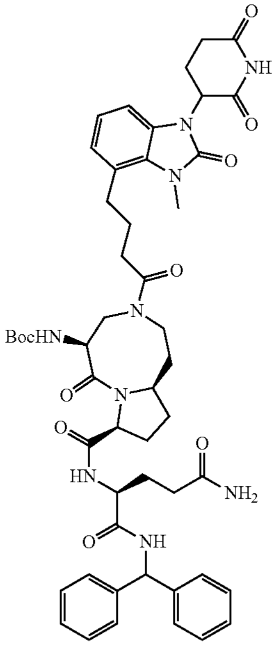 [SMILES: Cn1c(=O)n(C2CCC(=O)NC2=O)c2cccc(CCCC(=O)N3CC[C@H]4CC[C@@H](C(=O)N[C@@H](CCC(N)=O)C(=O)NC(c5ccccc5)c5ccccc5)N4C(=O)[C@@H](NC(=O)OC(C)(C)C)C3)c21] | tert-butyl N-[(5S,8S,10aR)-8-[[(1S)-3-carbamoyl-1-(diphenylmethylcarbamoyl)propyl]carbamoyl]-3-[4-[1-(2,6-dioxopiperidin-3-yl)-3-methyl-2-oxo-1,3-benzodiazol-4-yl]butanoyl]-6-oxo-octahydropyrrolo[1,2-a][1,5]diazocin-5-yl]carbamate | 948.30 | (400 MHz, DMSO-$d_6$) δ 11.11 (s, 1H), 8.74 (d, J = 8.4 Hz, 1H), 8.20 (d, J = 7.7 Hz, 1H), 7.34-7.24 (m, 11H), 6.99-6.95 (m, 2H), 6.93-6.84 (m, 1H), 6.74 (d, J = 17.2 Hz, 1H), 6.53 (d, J = 6.8 Hz, 1H), 6.09 (d, J = 8.4 Hz, 1H), 5.37 (dd, J = 12.5, 5.4 Hz, 1H), 4.52-4.25 (m, 3H), 4.24-4.09 (m, 1H), 3.80-3.64 (m, 1H), 3.58 (s, 3H), 3.29-3.22 (m, 1H), 3.13 (t, J = 12.7 Hz, 1H), 2.97-2.89 (m, 2H), 2.88-2.82 (m, 1H), 2.77-2.58 (m, 3H), 2.18-2.05 (m, 3H), 2.03-1.95 (m, 3H), 1.95-1.81 (m, 4H), 1.82-1.70 (m, 3H), 1.67-1.55 (m, 2H), 1.39 (s, 9H) |

TABLE 47-continued

| Characterization data for intermediates prepare according to the procedure above. | | | | |
|---|---|---|---|---|
| Inter-me-diate | Structure | Chemical Name | MS: [(M + 1)]+ | $^1$H-NMR |
| G102 | 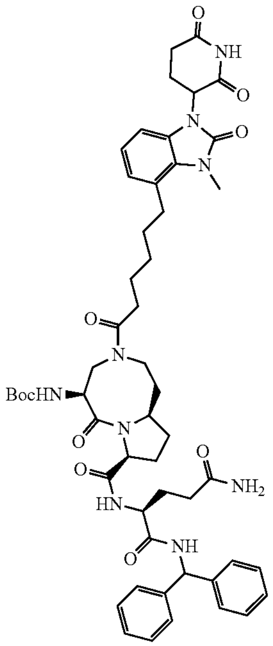 [SMILES: Cn1c(=O)n(C2CCC(=O)NC2=O)c2cccc(CCCCCC(=O)N3CC[C@H]4CC[C@@H](C(=O)N[C@@H](CCC(N)=O)C(=O)NC(c5ccccc5)c5ccccc5)N4C(=O)[C@@H](NC(=O)OC(C)(C)C)C3)c21] | tert-butyl N-[(5S,8S,10aR)-8-[[(1S)-3-carbamoyl-1-(diphenylmethylcarbamoyl)propyl]carbamoyl]-3-[6-[1-(2,6-dioxopiperidin-3-yl)-3-methyl-2-oxo-1,3-benzodiazol-4-yl]hexanoyl]-6-oxo-octahydropyrrolo[1,2-a][1,5]diazocin-5-yl]carbamate | 976.45 | (400 MHz, DMSO-$d_6$) δ 11.10 (s, 1H), 8.73 (d, J = 8.4 Hz, 1H), 8.19 (t, J = 8.2 Hz, 1H), 7.40-7.18 (m, 9.4 Hz, 11H), 6.96 (q, J = 7.9, 5.6 Hz, 2H), 6.91-6.84 (m, 1H), 6.78-6.58 (m, 1H), 6.46 (d, J = 6.7 Hz, 1H), 6.10 (d, J = 8.4 Hz, 1H), 5.38 (dd, J = 12.7, 5.3 Hz, 1H), 4.50-4.26 (m, 3H), 4.18-3.99 (m, 2H), 3.73 (d, J = 14.3 Hz, 1H), 3.56 (s, 3H), 3.29-3.17 (m, 1H), 3.16-3.08 (m, 1H), 2.89 (q, J = 6.6 Hz, 3H), 2.78-2.68 (m, 1H), 2.68-2.59 (m, 1H), 2.47 (d, J = 7.6 Hz, 2H), 2.21-2.06 (m, 3H), 2.05-1.96 (m, 3H), 1.97-1.88 (m, 1H), 1.84-1.72 (m, 2H), 1.68-1.56 (m, 5H), 1.48-1.42 (m, 1H), 1.37 (s, 9H), 1.19 (t, J = 7.2 Hz, 2H) |
| G103 | 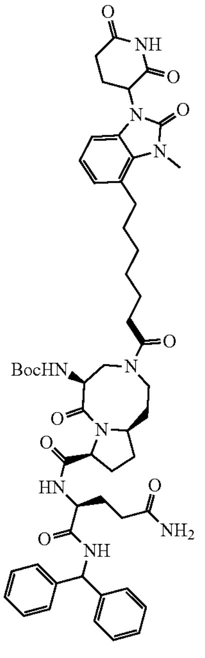 | tert-butyl N-[(5S,8S,10aR)-8-[[(1S)-3-carbamoyl-1-(diphenylmethylcarbamoyl)propyl]carbamoyl]-3-[7-[3-methyl-1-(1-methyl-2,6-dioxopiperidin-3-yl)-2-oxo-1,3-benzodiazol-5-yl]heptanoyl]-6-oxo-octahydropyrrolo[1,2-a][1,5]diazocin-5-yl]carbamate | 1004.75 | (400 MHz, $CDCl_3$) δ 7.40-7.17 (m, 10H), 6.93-6.83 (m, 2H), 6.70 (d, J = 7.2 Hz, 1H), 6.23 (t, J = 8.4 Hz, 1H), 5.73 (d, J = 6.3 Hz, 1H), 5.51 (s, 1H), 5.18 (dd, J = 12.8, 5.2 Hz, 1H), 4.61-4.02 (m, 4H), 3.89 (d, J = 13.8 Hz, 1H), 3.44 (s, 3H), 3.27 (s, 3H), 3.12-3.02 (m, 1H), 2.92-2.79 (m, 1H), 2.79-2.61 (m, 3H), 2.6-2.42 (m, 1H), 2.40-2.12 (m, 3H), 2.11-1.98 (m, 12H), 1.97-1.71 (m, 1H), 1.68-1.55 (m, 5H), 1.46 (s, 9H), 1.40-1.35 (m, 5H). |

TABLE 47-continued

| Characterization data for intermediates prepare according to the procedure above. | | | | |
|---|---|---|---|---|
| Inter-me-diate | Structure | Chemical Name | MS: [(M + 1)]$^+$ | $^1$H-NMR |
| G104 | 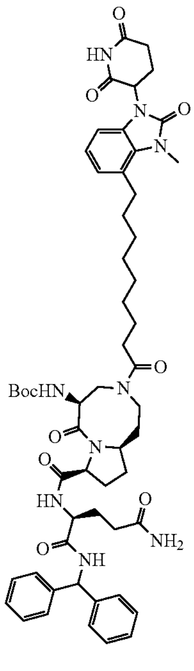 [SMILES: Cn1c(=O)n(C2CCC(=O)NC2=O)c2cccc(CCCCCCCCC(=O)N3CC[C@H]4CC[C@@H](C(=O)N[C@@H](CCC(N)=O)C(=O)NC(c5ccccc5)c5ccccc5)N4C(=O)[C@@H](NC(=O)OC(C)(C)C)C3)c21] | tert-butyl N-[(5S,8S,10aR)-8-[[(1S)-3-carbamoyl-1-(diphenylmethylcarbamoyl)propyl]carbamoyl]-3-[9-[1-(2,6-dioxopiperidin-3-yl)-3-methyl-2-oxo-1,3-benzodiazol-4-yl]nonanoyl]-6-oxo-octahydropyrrolo[1,2-a][1,5]diazocin-5-yl]carbamate | 1018.45 | (400 MHz, DMSO-$d_6$) δ 11.10 (s, 1H), 8.74 (d, J = 8.7 Hz, 1H), 8.19 (t, J = 7.9 Hz, 1H), 7.39-7.20 (m, 11H), 7.00-6.91 (m, 2H), 6.89-6.84 (m, 1H), 6.76-6.68 (m, 1H), 6.48 (d, J = 6.9 Hz, 1H), 6.10 (d, J = 8.4 Hz, 1H), 5.37 (dd, J = 12.6, 5.4 Hz, 1H), 4.48-4.23 (m, 3H), 4.19-4.06 (m, 2H), 3.71-3.62 (m, 2H), 3.55 (s, 3H), 3.14-3.06 (m, 1H), 2.96-2.83 (m, 3H), 2.78-2.58 (m, 2H), 2.48-2.42 (m, 1H), 2.22-2.06 (m, 3H), 2.03-1.97 (m, 3H), 1.95-1.89 (m, 1H), 1.85-1.67 (m, 3H), 1.63-1.57 (m, 3H), 1.56-1.48 (m, 2H), 1.42-1.28 (m, 18H) |
| G105 | 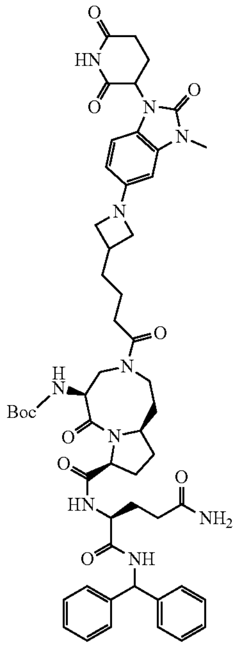 [SMILES: Cn1c(=O)n(C2CCC(=O)NC2=O)c2ccc(N3CC(CCCC(=O)N4CC[C@H]5CC[C@@H](C(=O)N[C@@H](CCC(N)=O)C(=O)NC(c6ccccc6)c6ccccc6)N5C(=O)[C@@H](NC(=O)OC(C)(C)C)C4)C3)cc21] | tert-butyl N-[(5S,8S,10aR)-8-[[(1S)-3-carbamoyl-1-(diphenylmethylcarbamoyl)propyl]carbamoyl]-3-(4-[1-[1-(2,6-dioxopiperidin-3-yl)-3-methyl-2-oxo-1,3-benzodiazol-5-yl]azetidin-3-yl]butanoyl)-6-oxo-octahydropyrrolo[1,2-a][1,5]diazocin-5-yl]carbamate | 1003.35 | (400 MHz, DMSO-$d_6$) δ 11.05 (s, 1H), 8.73 (d, J = 8.6 Hz, 1H), 8.22-8.13 (m, 1H), 7.38-7.28 (m, 6H), 7.28-7.25 (m, 3H), 7.25-7.22 (m, 1H), 7.21 (s, 1H), 6.96-6.89 (m, 1H), 6.72 (d, J = 16.2 Hz, 1H), 6.51 (d, J = 6.9 Hz, 1H), 6.28 (dd, J = 3.8, 2.1 Hz, 1H), 6.15-6.04 (m, 2H), 5.27 (dd, J = 12.8, 5.4 Hz, 1H), 4.50-4.43 (m, 1H), 4.42-4.35 (m, 1H), 4.32 (t, J = 7.0 Hz, 1H), 4.20-4.07 (m, 1H), 3.95-3.87 (m, 2H), 3.76-3.68 (m, 1H), 3.42-3.36 (m, 3H), 3.28 (s, 3H), 3.19-2.98 (m, 2H), 2.97-2.83 (m,1H), 2.74-2.57 (m, 3H), 2.49-2.41 (m, 2H), 2.14 (d, J = 5.7 Hz, 1H), 2.12 (d, J = 6.1 Hz, 1H), 2.03-1.88 (m, 4H), 1.82-1.70 (m, 3H), 1.68-1.46 (m, 6H), 1.38 (s, 9H) |

TABLE 47-continued

| Characterization data for intermediates prepare according to the procedure above. | | | | |
|---|---|---|---|---|
| Intermediate | Structure | Chemical Name | MS: [(M + 1)]+ | 1H-NMR |
| G106 | 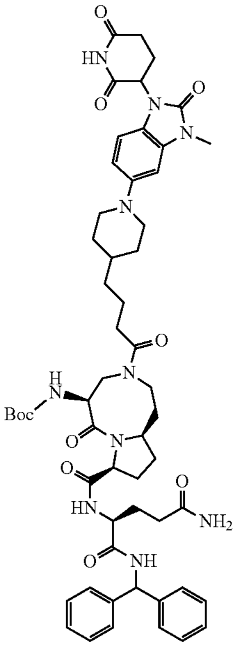 [SMILES: Cn1c(=O)n(C2CCC(=O)NC2=O)c2ccc(N3CCC(CCCC(=O)N4CC[C@H]5CC[C@@H](C(=O)N[C@@H](CCC(N)=O)C(=O)NC(c6ccccc6)c6ccccc6)N5C(=O)[C@@H](NC(=O)OC(C)(C)C)C4)CC3)cc21] | tert-butyl N-[(5S,8S,10aR)-8-[[(1S)-3-carbamoyl-1-(diphenylmethylcarbamoyl)propyl]carbamoyl]-3-(4-[1-[1-(2,6-dioxopiperidin-3-yl)-3-methyl-2-oxo-1,3-benzodiazol-5-yl]piperidin-4-yl]butanoyl)-6-oxo-octahydropyrrolo[1,2-a][1,5]diazocin-5-yl]carbamate | 1031.40 | (400 MHz, DMSO-$d_6$) δ 11.07 (s, 1H), 8.73 (d, J = 8.5 Hz, 1H), 8.19 (d, J = 7.5 Hz, 1H), 7.37-7.22 (m, 11H), 6.93 (d, J = 8.6 Hz, 1H), 6.82 (d, J = 2.3 Hz, 1H), 6.78-6.69 (m, 1H), 6.65-6.58 (m, 1H), 6.50 (d, J = 6.8 Hz, 1H), 6.10 (d, J = 8.4 Hz, 1H), 5.29 (dd, J = 12.9, 5.4 Hz, 1H), 4.50-4.23 (m, 3H), 4.17-4.08 (m, 1H), 3.72 (d, J = 14.1 Hz, 2H), 3.62-3.56 (m, 3H), 3.30 (s, 3H), 3.20-3.08 (m, 2H), 2.97-2.77 (m, 2H), 2.76-2.56 (m, 4H), 2.48-2.42 (m, 2H), 2.17-2.10 (m, 2H), 2.09-2.04 (m, 2H), 2.02-1.97 (m, 1H), 1.97-1.88 (m, 2H), 1.80-1.72 (m, 3H), 1.64-1.56 (m, 4H), 1.39 (s, 9H), 1.32-1.24 (m, 4H) |

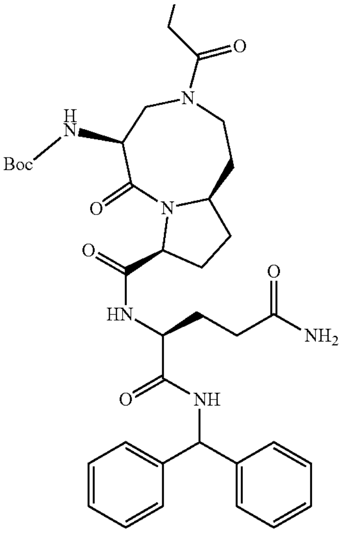

TABLE 47-continued

| Characterization data for intermediates prepare according to the procedure above. | | | | |
|---|---|---|---|---|
| Intermediate | Structure | Chemical Name | MS: [(M + 1)]$^+$ | $^1$H-NMR |
| G107 | 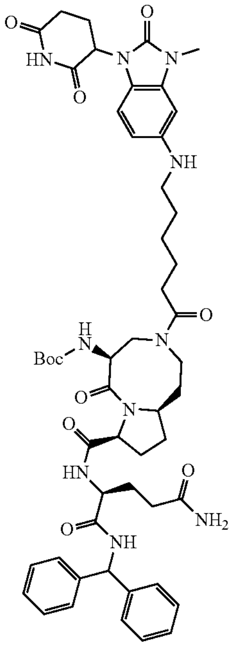 [SMILES: Cn1c(=O)n(C2CCC(=O)NC2=O)c2ccc(NCCCCCC(=O)N3CC[C@H]4CC[C@@H](C(=O)N[C@@H](CCC(N)=O)C(=O)NC(c5ccccc5)c5ccccc5)N4C(=O)[C@@H](NC(=O)OC(C)(C)C)C3)cc21] | tert-butyl N-[(5S,8S,10aR)-8-[[(1S)-3-carbamoyl-1-(diphenylmethylcarbamoyl)propyl]carbamoyl]-3-(6-[[1-(2,6-dioxopiperidin-3-yl)-3-methyl-2-oxo-1,3-benzodiazol-5-yl]amino]hexanoyl)-6-oxo-octahydropyrrolo[1,2-a][1,5]diazocin-5-yl]carbamate | 991.35 | (400 MHz, DMSO-$d_6$) δ 11.04 (s, 1H), 8.73 (d, J = 8.5 Hz, 1H), 8.19 (d, J = 6.4 Hz, 1H), 7.44-7.13 (m, 12H), 6.85-6.68 (m, 2H), 6.51 (d, J = 6.7 Hz, 1H), 6.42-6.36 (m, 1H), 6.31-6.26 (m, 1H), 6.10 (d, J = 8.4 Hz, 1H), 5.24 (dd, J = 12.7, 5.3 Hz, 1H), 4.48-4.50 (m, 3H), 4.16-4.09 (m, 1H), 3.81-3.58 (m, 2H), 3.25 (s, 3H), 2.95-2.78 (m, 3H), 2.76-2.54 (m, 3H), 2.52-2.47 (m, 3H), 2.39-2.27 (m, 1H), 2.15-2.08 (m, 3H), 2.02-1.86 (m, 4H), 1.62-1.56 (m, 7H), 1.42-1.34 (m, 11H) |
| G108 | 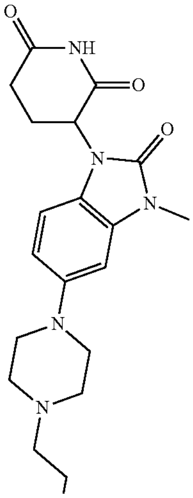 | tert-butyl N-[(5S,8S,10aR)-8-[[(1S)-3-carbamoyl-1-(diphenylmethylcarbamoyl)propyl]carbamoyl]-3-(4-[4-[1-(2,6-dioxopiperidin-3-yl)-3-methyl-2-oxo-1,3-benzodiazol-5-yl]piperazin-1-yl]butanoyl)-6-oxo-octahydropyrrolo[1,2-a][1,5]diazocin-5-yl]carbamate | 1032.55 | (400 MHz, DMSO-$d_6$) δ 11.07 (s, 1H), 8.71 (d, J = 8.5 Hz, 1H), 8.21 (d, J = 7.5 Hz, 1H), 7.18-7.38 (m, 11H), 6.95 (d, J = 8.5 Hz, 1H), 6.87-6.83 (m, 1H), 6.77 (d, J = 8.9 Hz, 1H), 6.72-6.56 (m, 2H), 6.10 (d, J = 8.5 Hz, 1H), 5.30 (dd, J = 12.9, 5.4 Hz, 1H), 4.55-4.49 (m, 1H), 4.47-4.25 (m, 3H), 4.18-4.14 (m, 1H), 3.86-3.61 (m, 3H), 3.31 (s, 3H), 3.20-3.14 (m, 4H), 2.97-2.82 (m, 2H), 2.79-2.57 (m, 6H), 2.45-2.26 (m, 2H), 2.23-2.06 (m, 4H), 2.05-1.92 (m, 4H), 1.86-1.52 (m, 6H), 1.38 (s, 9H) |

TABLE 47-continued

Characterization data for intermediates prepare according to the procedure above.

| Inter-me-diate | Structure | Chemical Name | MS: [(M + 1)]+ | 1H-NMR |
| --- | --- | --- | --- | --- |
| | 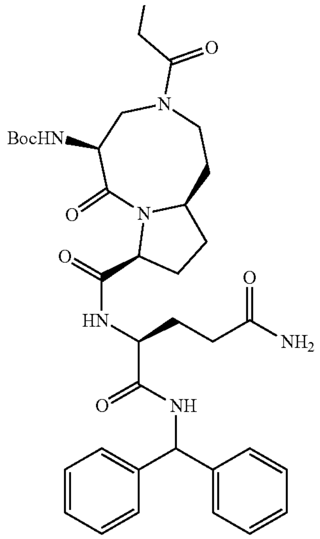 | | | |
| G109 | 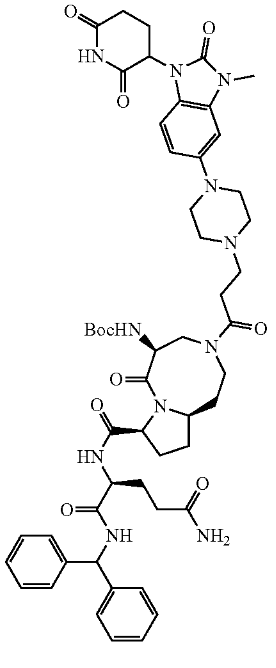 [SMILES: Cn1c(=O)n(C2CCC(=O)NC2=O)c2ccc(N3CCN(CCC(=O)N4CC[C@H]5CC[C@@H](C(=O)N[C@@H](CCC(N)=O)C(=O)NC(c6ccccc6)c6ccccc6)N5C(=O)[C@@H](NC(=O)OC(C)(C)C)C4)CC3)cc21] | tert-butyl N-[(5S,8S,10aR)-8-[[(1S)-3-carbamoyl-1-(diphenylmethylcarbamoyl)propyl]carbamoyl]-3-(3-[4-[1-(2,6-dioxopiperidin-3-yl)-3-methyl-2-oxo-1,3-benzodiazol-5-yl]piperazin-1-yl]propanoyl)-6-oxo-octahydropyrrolo[1,2-a][1,5]diazocin-5-yl]carbamate | 1018.30 | (400 MHz, DMSO-$d_6$) δ 11.08 (s, 1H), 8.64 (d, J = 8.7 Hz, 1H), 8.30-8.18 (m, 1H), 7.37-7.21 (m, 11H), 6.98 (d, J = 8.6 Hz, 1H), 6.91 (d, J = 1.9 Hz, 1H), 6.83-6.78 (m, 1H), 6.68 (d, J = 8.5 Hz, 2H), 6.10 (d, J = 8.3 Hz, 1H), 5.34-5.29 (m, 1H), 4.72-4.15 (m, 4H), 3.74-3.50 (m, 5H), 3.31 (s, 3H), 3.23-3.14 (m, 1H), 2.96-2.80 (m, 5H), 2.68-2.63 (m, 3H), 2.34 (d, J = 1.9 Hz, 1H), 2.22-2.06 (m, 6H), 2.05-1.80 (m, 4H), 1.72-1.69 (m, 1H), 1.68-1.49 (m, 4H), 1.40 (s, 9H) |

TABLE 47-continued

Characterization data for intermediates prepare according to the procedure above.

| Inter-me-diate | Structure | Chemical Name | MS: [(M + 1)]$^+$ | $^1$H-NMR |
|---|---|---|---|---|
| G110 | 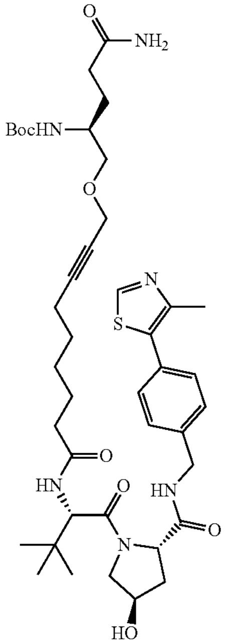 [SMILES: Cc1ncsc1-c1ccc(CNC(=O)[C@@H]2C[C@@H](O)CN2C(=O)[C@@H](NC(=O)CCCCCC#CCOC[C@H](CCC(N)=O)NC(=O)OC(C)(C)C)C(C)(C)C)cc1] | tert-butyl N-[(2S)-4-carbamoyl-1-[(8-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]oct-2-yn-1-yl)oxy]butan-2-yl]carbamate | 797.30 | (400 MHz, DMSO-$d_6$) δ 8.99 (s, 1H), 8.57 (t, J = 6.1 Hz, 1H), 7.89 (d, J = 9.3 Hz, 1H), 7.48-7.38 (m, 5H), 7.24 (s, 1H), 6.71 (s, 1H), 6.64 (d, J = 8.6 Hz, 1H), 5.13 (d, J = 3.6 Hz, 1H), 4.55 (d, J = 9.4 Hz, 1H), 4.45-4.42 (m, 2H), 4.36-4.34 (m, 1H), 4.22 (dd, J = 15.8, 5.4 Hz, 1H), 4.09 (s, 2H), 3.72-3.59 (m, 2H), 3.51-3.48 (m, 1H), 3.23-3.29 (m, 3H), 2.45 (s, 3H), 2.33-2.17 (m, 2H), 2.17-1.98 (m, 4H), 1.92-1.89 (m, 1H), 1.79-1.65 (m, 1H), 1.48-1.38 (m, 4H), 1.38 (s, 9H), 1.35-1.31 (m, 1H), 0.94 (s, 9H). |
| G111 | 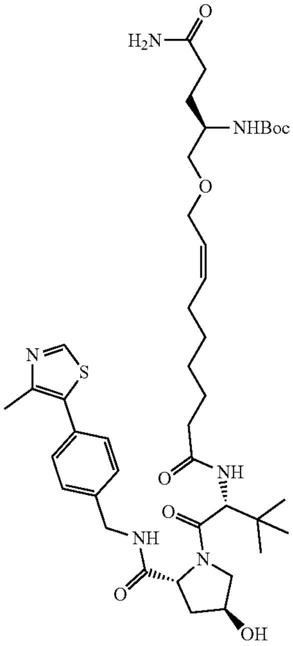 [SMILES: Cc1ncsc1-c1ccc(CNC(=O)[C@H]2C[C@H](O)CN2C(=O)[C@H](NC(=O)CCCCC/C=C\COC[C@@H](CCC(N)=O)NC(=O)OC(C)(C)C)C(C)(C)C)cc1] | tert-butyl N-[(2S)-4-carbamoyl-1-[[(2Z)-8-[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]oct-2-en-1-yl]oxy]butan-2-yl]carbamate | 799.30 | (400 MHz, DMSO-$d_6$) δ 8.99 (s, 1H), 8.56 (t, J = 6.0 Hz, 1H), 7.86 (d, J = 9.3 Hz, 1H), 7.41 (q, J = 8.4 Hz, 5H), 7.23 (s, 1H), 6.78-6.59 (m, 1H), 6.60 (d, J = 8.6 Hz, 1H), 5.54-5.41 (m, 2H), 5.20-5.09 (m, 1H), 4.55 (d, J = 9.3 Hz, 1H), 4.50-4.39 (m, 2H), 4.36 (s, 1H), 4.22 (dd, J = 15.9, 5.4 Hz, 1H), 3.96 (d, J = 5.6 Hz, 2H), 3.76-3.56 (m, 2H), 3.55-3.43 (m, 2H), 3.29-3.12 (m, 3H), 2.45 (s, 3H), 2.32-2.22 (m, 1H), 2.16-2.00 (m, 6H), 1.95-1.88 (m, 1H), 1.75-1.59 (m, 1H), 1.53-1.44 (m, 1H), 1.38 (s, 9H), 1.34-1.16 (m, 2H), 0.94 (s, 9H), 0.93-0.88 (m, 1H) |

TABLE 47-continued

Characterization data for intermediates prepare according to the procedure above.

| Inter-me-diate | Structure | Chemical Name | MS: [(M + 1)]+ | 1H-NMR |
|---|---|---|---|---|
| G112 | 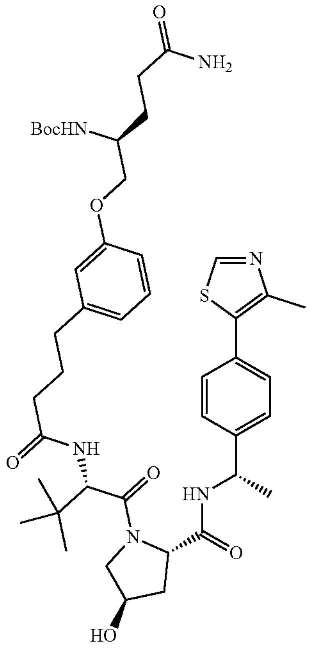 [SMILES: Cc1ncsc1-c1ccc([C@H](C)NC(=O)[C@@H]2C[C@@H](O)CN2C(=O)[C@@H](NC(=O)CCCc2cccc(OC[C@H](CCC(N)=O)NC(=O)OC(C)(C)C)c2)C(C)(C)C)cc1] | tert-butyl N-[(2S)-4-carbamoyl-1-[3-(3-[[(2S)-1-[(2S,4R)-4-hydroxy-2-[[(1S)-1-[4-(4-methyl-1,3-thiazol-5-yl)phenyl]ethyl]-carbamoyl]pyrrolidin-1-yl]-3,3-dimethyl-1-oxobutan-2-yl]carbamoyl]propyl)-phenoxy]butan-2-yl]carbamate | 821.60 | (400 MHz, DMSO-$d_6$) δ 8.99 (s, 1H), 8.37 (d, J = 7.8 Hz, 1H), 7.84 (d, J = 9.3 Hz, 1H), 7.44 (d, J = 8.3 Hz, 2H), 7.39 (d, J = 8.3 Hz, 2H), 7.29-7.24 (m, 1H), 7.22-7.14 (m, 1H), 6.81 (d, J = 8.4 Hz, 1H), 6.75 (dd, J = 7.2, 4.7 Hz, 4H), 5.10 (d, J = 3.6 Hz, 1H), 4.93 (p, J = 6.9 Hz, 1H), 4.54 (d, J = 9.3 Hz, 1H), 4.44 (t, J = 8.0 Hz, 1H), 4.34 (d, J = 4.2 Hz, 1H), 4.29 (s, 1H), 3.87-3.83 (m, 2H), 3.81-3.69 (m, 1H), 3.63 (d, J = 3.3 Hz, 2H), 2.46 (s, 3H), 2.30-2.26 (m, 1H), 2.22-2.08 (m, 2H), 2.04-2.00 (m, 1H), 1.86-1.71 (m, 3H), 1.62-1.58 (m, 1H), 1.42-1.35 (m, 14H), 1.27-1.23 (m, 1H), 0.95 (s, 9H) |
| G114 | 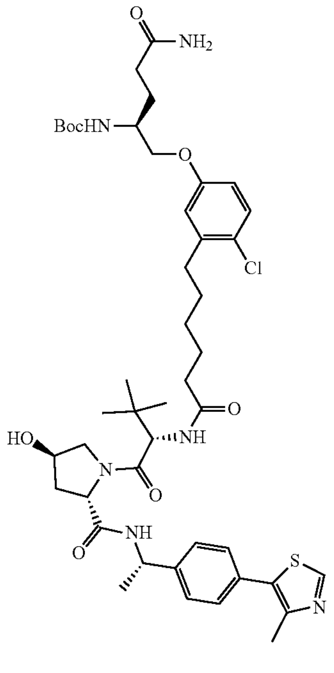 [SMILES: Cc1ncsc1-c1ccc([C@H](C)NC(=O)[C@@H]2C[C@@H](O)CN2C(=O)[C@@H](NC(=O)CCCCCc2cc(OC[C@H](CCC(N)=O)NC(=O)OC(C)(C)C)ccc2Cl)C(C)(C)C)cc1] | tert-butyl N-[(2S)-4-carbamoyl-1-[4-chloro-3-(5-[[(2S)-1-[(2S,4R)-4-hydroxy-2-[[(1S)-1-[4-(4-methyl-1,3-thiazol-5-yl)phenyl]ethyl] carbamoyl]pyrrolidin-1-yl]-3,3-dimethyl-1-oxobutan-2-yl]carbamoyl]pentyl) phenoxy]butan-2-yl]carbamate | 883.60 | (400 MHz, DMSO-$d_6$) δ 8.99 (s, 1H), 8.37 (d, J = 7.8 Hz, 1H), 7.79 (d, J = 8.1 Hz, 1H), 7.48-7.36 (m, 4H), 7.40-7.24 (m, 2H), 7.28-7.24 (m, 1H), 6.90 (d, J = 3.1 Hz, 1H), 6.86-6.71 (m, 2H), 5.12-5.08 (m, 1H), 4.92 (d, J = 7.4 Hz, 1H), 4.52 (d, J = 9.3 Hz, 1H), 4.43 (d, J = 8.0 Hz, 1H), 4.31-4.27 (m, 1H), 3.85 (d, J = 6.5 Hz, 1H), 3.73-3.69 (m, 1H), 3.63-3.59 (m, 1H), 2.62 (d, J = 7.7 Hz, 1H), 2.45 (s, 3H), 2.27 (d, J = 15.1, 7.7 Hz, 1H), 2.16-2.06 (m, 3H), 2.01 (d, J = 10.0 Hz, 1H), 1.80-1.78(m, 2H), 1.52-1.53 (m, 4H), 1.37 (s, 9H), 1.35-1.27 (m, 2H), 1.2-1.23 (m, 4H), 0.94 (s, 9H), 0.90-0.76 (m, 3H) |

TABLE 47-continued

| Characterization data for intermediates prepare according to the procedure above. | | | | |
|---|---|---|---|---|
| Intermediate | Structure | Chemical Name | MS: [(M + 1)]$^+$ | $^1$H-NMR |
| G115 | 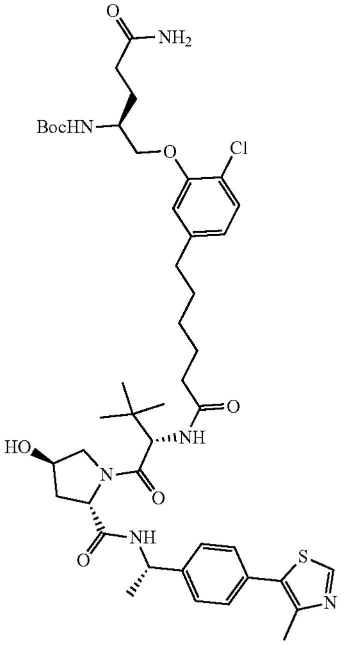 [SMILES: Cc1ncsc1-c1ccc([C@H](C)NC(=O)[C@@H]2C[C@@H](O)CN2C(=O)[C@@H](NC(=O)CCCCCc2ccc(Cl)c(OC[C@H](CCC(N)=O)NC(=O)OC(C)(C)C)c2)C(C)(C)C)cc1] | tert-butyl N-[(2S)-4-carbamoyl-1-[2-chloro-5-(5-[[(2S)-1-[(2S,4R)-4-hydroxy-2-[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenoxy]butan-2-yl]carbamate | 883.60 | (300 MHz, DMSO-$d_6$) δ 9.00 (s, 1H), 8.42-8.33 (m, 2H), 7.79 (d, J = 9.2 Hz, 1H), 7.44-7.40 (m, 4H), 7.28 (d, J = 7.9 Hz, 1H), 7.02-6.96 (m, 2H), 6.79-6.75 (m, 2H), 5.11-5.02 (m, 1H), 4.99-4.88 (m, 2H), 4.58-4.48 (m, 2H), 4.49-4.38 (m, 2H), 4.32-4.26 (m, 1H), 3.98-3.87 (m, 2H), 3.81-3.71 (m, 1H), 3.62-3.50 (m, 2H), 2.45 (s, 3H), 2.35-2.18 (m, 1H), 2.14-2.10 (m, 2H), 2.08 (s, 3H), 2.00-1.98 (m, 1H), 1.88-1.73 (m, 2H), 1.60-1.44 (m, 5H), 1.39-1.37 (m, 7H), 1.25-1.23 (m, 4H), 0.94 (s, 9H) |
| G116 | 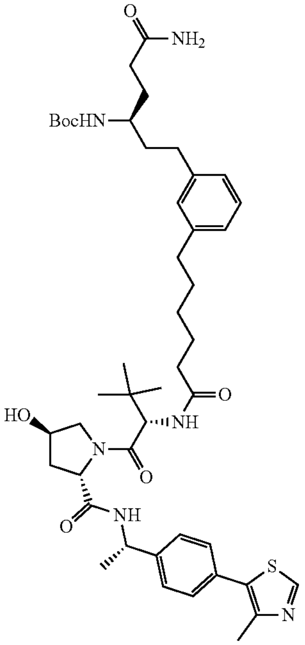 [SMILES: Cc1ncsc1-c1ccc([C@H](C)NC(=O)[C@@H]2C[C@@H](O)CN2C(=O)[C@@H](NC(=O)CCCCCc2cccc(CC[C@H](CCC(N)=O)NC(=O)OC(C)(C)C)c2)C(C)(C)C)cc1] | tert-butyl N-[(3R)-1-carbamoyl-5-[3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenyl]pentan-3-yl]carbamate | 847.70 | (300 MHz, DMSO-d6) δ 8.97 (s, 1H), 8.34 (d, J = 7.7 Hz, 1H), 7.76 (d, J = 9.2 Hz, 1H), 7.40 (q, J = 8.4 Hz, 4H), 7.27-7.09 (m, 2H), 6.97 (d, J = 7.0 Hz, 3H), 6.67 (d, J = 8.7 Hz, 2H), 5.08 (d, J = 3.5 Hz, 1H), 4.93 (q, J = 12 Hz, 1H), 4.54-4.37 (m, 2H), 4.35-4.26 (m, 1H), 3.60 (d, J = 3.6 Hz, 2H), 3.42-3.35 (m, 1H), 3.32-3.26 (m, 2H), 2.45 (s, 3H), 2.31-2.18 (m, 1H), 2.17-1.94 (m, 4H), 1.85-1.72 (m, 2H), 1.68-1.54 (m, 8H), 1.42-1.34 (m, 12H), 1.32-1.27 (m, 2H), 0.93 (s, 9H) |

TABLE 47-continued

Characterization data for intermediates prepare according to the procedure above.

| Inter-me-diate | Structure | Chemical Name | MS: [(M + 1)]+ | 1H-NMR |
|---|---|---|---|---|
| G117 | 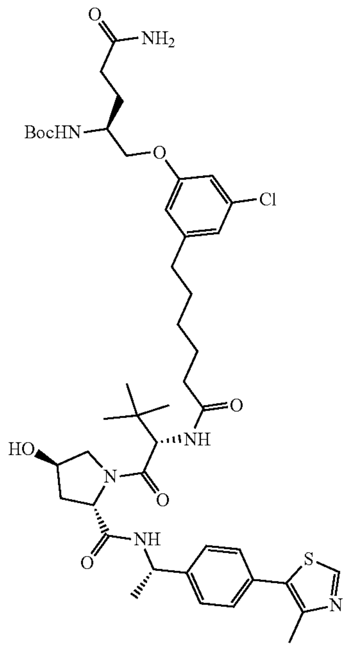 [SMILES: Cc1ncsc1-c1ccc([C@H](C)NC(=O)[C@@H]2C[C@@H](O)CN2C(=O)[C@@H](NC(=O)CCCCCc2cc(Cl)cc(OC[C@H](CCC(N)=O)NC(=O)OC(C)(C)C)c2)C(C)(C)C)cc1] | tert-butyl N-[(2S)-4-carbamoyl-1-[3-chloro-5-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenoxy]butan-2-yl]carbamate | 883.15 | (400 MHz, DMSO-$d_6$) δ 8.97 (s, 1H), 8.35 (d, J = 7.7 Hz, 1H), 7.77 (d, J = 9.2 Hz, 1H), 7.47-7.34 (m, 4H), 7.24 (s, 1H), 6.86-6.76 (m, 3H), 6.73 (d, J = 2.3 Hz, 2H), 5.08 (d, J = 3.5 Hz, 1H), 5.00-4.85 (m, 1H), 4.51 (d, J = 9.3 Hz, 1H), 4.42 (t, J = 8.0 Hz, 1H), 4.31-4.25 (m, 1H), 3.91-3.83 (m, 2H), 3.60 (d, J = 3.4 Hz, 2H), 2.45 (s, 3H), 2.30-2.20 (m, 1H), 2.17-2.07 (m, 4H), 2.03-1.92 (m, 1H), 1.86-1.72 (m, 3H), 1.60-1.46 (m, 6H), 1.38 (s, 9H), 1.25 (d, J = 9.7 Hz, 3H), 1.06 (t, J = 12.1 Hz, 2H), 0.92 (s, 9H) |
| G118 | 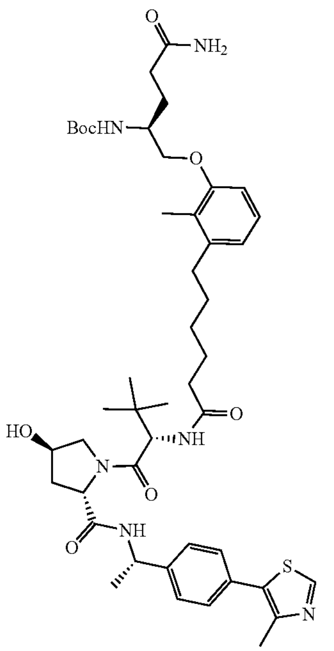 [SMILES: Cc1ncsc1-c1ccc([C@H](C)NC(=O)[C@@H]2C[C@@H](O)CN2C(=O)[C@@H](NC(=O)CCCCCc2cccc(OC[C@H](CCC(N)=O)NC(=O)OC(C)(C)C)c2C)C(C)(C)C)cc1] | tert-butyl N-[(2S)-4-carbamoyl-1-[3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)-2-methylphenoxy]butan-2-yl]carbamate | 863.45 | (400 MHz, DMSO-$d_6$) δ 8.99 (s, 1H), 8.38 (d, J = 7.8 Hz, 1H), 7.80 (d, J = 9.3 Hz, 1H), 7.44 (d, J = 8.3 Hz, 2H), 7.38 (d, J = 8.3 Hz, 2H), 7.27 (s, 1H), 7.03 (t, J = 7.9 Hz, 1H), 6.82 (d, J = 7.9 Hz, 1H), 6.73 (dd, J = 7.9, 4.2 Hz, 3H), 5.10 (d, J = 3.5 Hz, 1H), 4.96-4.88 (m, 1H), 4.52 (d, J = 9.3 Hz, 1H), 4.42 (t, J = 8.0 Hz, 1H), 4.31-4.25 (m, 1H), 3.89-3.71 (m, 3H), 3.64-3.58 (m, 2H), 2.46 (s, 3H), 2.31-2.23 (m, 1H), 2.18-2.11 (m, 3H), 2.10 (s, 3H), 2.04-1.98 (m, 1H), 1.86-1.76 (m, 2H), 1.68-1.42 (m, 3H), 1.40-1.37 (m, 12H), 1.37-1.34 (m, 2H), 1.33-1.20 (m, 2H), 0.94 (s, 9H), 0.89-0.82 (m, 2H) |

TABLE 47-continued

Characterization data for intermediates prepare according to the procedure above.

| Inter-me-diate | Structure | Chemical Name | MS: [(M + 1)]+ | $^1$H-NMR |
|---|---|---|---|---|
| G119 | 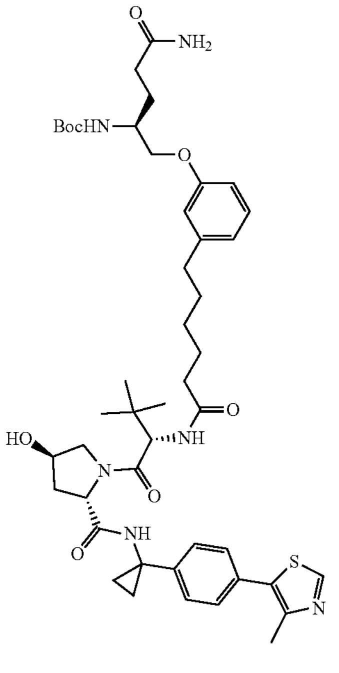 [SMILES: Cc1ncsc1-c1ccc(C2(NC(=O)[C@@H]3C[C@@H](O)CN3C(=O)[C@@H](NC(=O)CCCCCc3cccc(OC[C@H](CCC(N)=O)NC(=O)OC(C)(C)C)c3)C(C)(C)C)CC2)cc1] | tert-butyl N-[(2S)-4-carbamoyl-1-[3-(5-[[(2S)-1-[(2S,4R)-4-hydroxy-2-([1-[4-(4-methyl-1,3-thiazol-5-yl)phenyl] cyclopropyl]carbamoyl) pyrrolidin-1-yl]-3,3-dimethyl-1-oxobutan-2-yl]carbamoyl]pentyl) phenoxy]butan-2-yl]carbamate | 861.40 | (400 MHz, DMSO-$d_6$) δ 8.97 (s, 1H), 8.80 (s, 1H), 7.91 (d, J = 9.3 Hz, 1H), 7.37-7.28 (m, 4H), 7.26 (s, 1H), 7.16 (t, J = 7.9 Hz, 1H), 6.82 (d, J = 8.5 Hz, 1H), 6.79-6.69 (m, 4H), 5.13 (d, J = 3.4 Hz, 1H), 4.55 (d, J = 9.4 Hz, 1H), 4.41-4.37 (m, 2H), 3.91-3.77 (m, 2H), 3.65 (d, J = 3.3 Hz, 2H), 2.44 (s, 3H), 2.30-2.26 (m, 1H), 2.15-2.11 (m, 3H), 2.05-1.95 (m, 1H), 1.89-1.85 (m, 1H), 1.56-1.52 (m, 4H), 1.39 (s, 9H), 1.34-1.20 (m, 5H), 1.19-1.07 (m, 2H), 0.94 (s, 9H), 0.91-0.80 (m, 4H) |
| G120 | 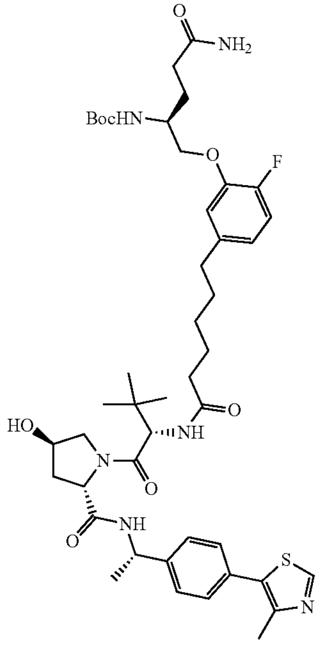 [SMILES: Cc1ncsc1-c1ccc([C@H](C)NC(=O)[C@@H]2C[C@@H](O)CN2C(=O)[C@@H](NC(=O)CCCCCc2ccc(F)c(OC[C@H](CCC(N)=O)NC(=O)OC(C)(C)C)c2)C(C)(C)C)cc1] | tert-butyl N-[(2S)-4-carbamoyl-1-[2-fluoro-5-(5-[[(2S)-1-[(2S,4R)-4-hydroxy-2-[[(1S)-1-[4-(4-methyl-1,3-thiazol-5-yl)phenyl]ethyl] carbamoyl]pyrrolidin-1-yl]-3,3-dimethyl-1-oxobutan-2-yl]carbamoyl]pentyl) phenoxy]butan-2-yl]carbamate | 867.40 | (400 MHz, DMSO-$d_6$) δ 8.99 (s, 1H), 8.38 (d, J = 7.8 Hz, 1H), 7.80 (d, J = 9.3 Hz, 1H), 7.47-7.41 (m, 2H), 7.41-7.31 (m, 2H), 7.27 (s, 1H), 7.06 (d, J = 11.5, 8.2 Hz, 1H), 6.99 (d, J = 8.3, 2.0 Hz, 1H), 6.84 (d, J = 8.5 Hz, 1H), 6.73 (d, J = 8.2, 4.4, 1.9 Hz, 2H), 5.11 (d, J = 3.6 Hz, 1H), 4.92 (d, J = 7.4 Hz, 1H), 4.54-4.50 (m, 1H), 4.44-4.40 (m, 1H), 4.31-4.27 (m, 1H), 3.94-3.90 (m, 2H), 3.73 (s, 1H), 3.63-3.59 (m, 2H), 2.46 (s, 3H), 2.28-2.24 (m, 1H), 2.16-2.12 (m, 2H), 2.07-1.96 (m, 4H), 1.82-1.78 (m, 2H), 1.57-1.44 (m, 3H), 1.37 (s, 9H), 1.36-1.20 (m, 7H), 0.93 (s, 9H) |

TABLE 47-continued

| Characterization data for intermediates prepare according to the procedure above. | | | | |
|---|---|---|---|---|
| Intermediate | Structure | Chemical Name | MS: [(M + 1)]+ | $^1$H-NMR |
| G121 | 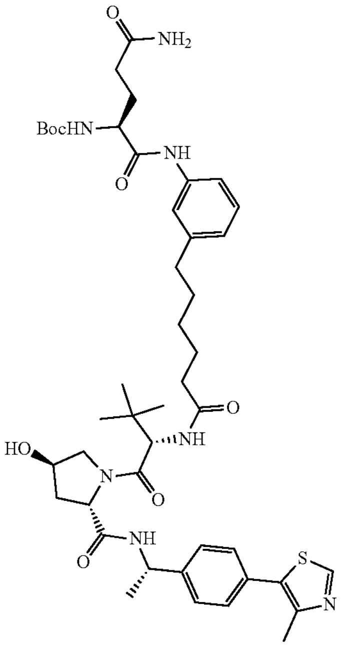 [SMILES: Cc1ncsc1-c1ccc([C@H](C)NC(=O)[C@@H]2C[C@@H](O)CN2C(=O)[C@@H](NC(=O)CCCCCc2cccc(NC(=O)[C@H](CCC(N)=O)NC(=O)OC(C)(C)C)c2)C(C)(C)C)cc1] | tert-butyl N-[(1S)-3-carbamoyl-1-[[3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenyl]carbamoyl]propyl]carbamate | 862.55 | (300 MHz, DMSO-$d_6$) δ 9.84 (s, 1H), 8.97 (s, 1H), 8.35 (d, J = 7.8 Hz, 1 H), 7.76 (d, J = 9.2 Hz, 1H), 7.45-7.36 (m, 7H), 7.27 (s, 1H), 7.24-7.13 (m, 1H), 6.98 (d, J = 7.7 Hz, 1H), 6.87 (d, J = 7.5 Hz, 1H), 6.76 (s, 1H), 5.08 (d, J = 3.5 Hz, 1H), 4.96-4.85 (m, 1H), 4.50 (d, J = 9.3 Hz, 1H), 4.42 (t, J = 8.0 Hz, 1H), 4.28 (s, 1H), 4.02 (s, 1H), 3.60 (s, 2H), 3.48-3.35 (m, 4H), 2.45 (s, 3H), 2.30-1.95 (m, 4H), 1.95-1.71 (m, 1H), 1.59-1.45 (m, 4H), 1.37 (s, 9H), 1.36-1.34 (m, 3H), 1.31-1.23 (m, 2H), 0.92 (s, 9H) |
| G122 | 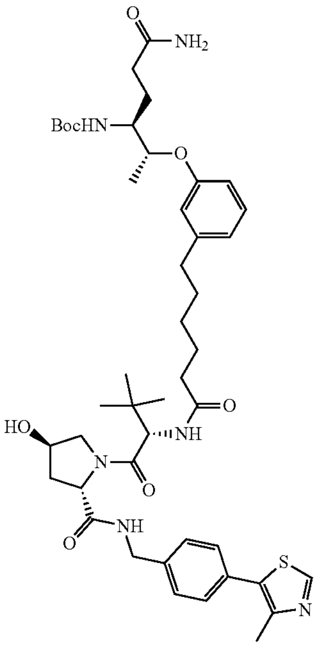 [SMILES: Cc1ncsc1-c1ccc(CNC(=O)[C@@H]2C[C@@H](O)CN2C(=O)[C@@H](NC(=O)CCCCCc2cccc(O[C@H](C)[C@H](CCC(N)=O)NC(=O)OC(C)(C)C)c2)C(C)(C)C)cc1] | tert-butyl N-[(3S,4R)-1-carbamoyl-4-[3-(5-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]pentyl)phenoxy]pentan-3-yl]carbamate | 849.60 | (300 MHz, DMSO-$d_6$) δ 9.00 (s, 1H), 8.56 (t, J = 6.0 Hz, 1H), 7.86 (d, J = 9.3 Hz, 1H), 7.48-7.37 (m, 5H), 7.25 (s, 1H), 7.21-7.10 (m, 1H), 6.76-6.68 (m, 5H), 5.13 (d, J = 3.5 Hz, 1H), 4.56 (d, J = 9.3 Hz, 1H), 4.51-4.16 (m, 5H), 3.71-3.63 (m, 2H), 3.59-3.43 (m, 1H), 2.46 (s, 3H), 2.33-2.24 (m, 1H), 2.19-1.78 (m, 6H), 1.61-1.47 (m, 4H), 1.40 (s, 9H), 1.34-1.21 (m, 4H), 1.18 (d, J = 6.1 Hz, 3H), 0.95 (s, 9H) |

TABLE 47-continued

| Characterization data for intermediates prepare according to the procedure above. | | | | |
|---|---|---|---|---|
| Intermediate | Structure | Chemical Name | MS: [(M + 1)]$^+$ | $^1$H-NMR |
| G123 | 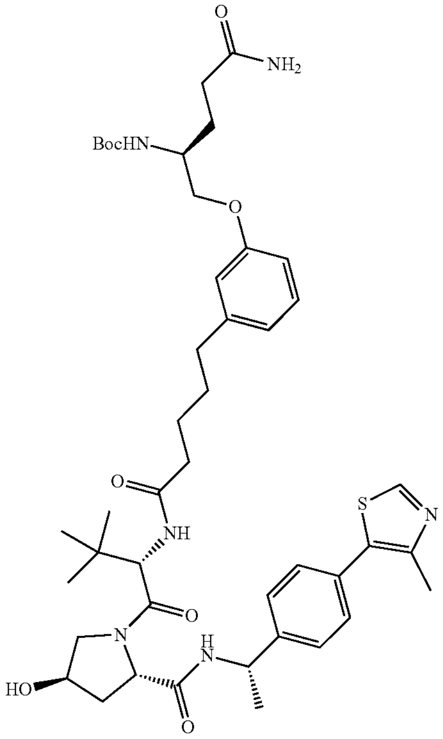 [SMILES: Cc1ncsc1-c1ccc([C@H](C)NC(=O)[C@@H]2C[C@@H](O)CN2C(=O)[C@@H](NC(=O)CCCCc2cccc(OC[C@H](CCC(N)=O)NC(=O)OC(C)(C)C)c2)C(C)(C)C)cc1] | tert-butyl N-[(2S)-4-carbamoyl-1-[3-(4-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]butyl)phenoxy]butan-2-yl]carbamate | 835.40 | (400 MHz, DMSO-$d_6$) δ 8.99 (s, 1H), 8.38 (d, J = 7.8 Hz, 1H), 7.83 (d, J = 9.3 Hz, 1H), 7.44 (d, J = 8.3 Hz, 2H), 7.38 (d, J = 8.3 Hz, 2H), 7.27 (s, 1H), 7.17 (t, J = 7.8 Hz, 1H), 6.83 (d, J = 8.4 Hz, 1H), 6.77-6.70 (m, 4H), 5.10 (d, J = 3.6 Hz, 1H), 4.94-4.90 (m, 1H), 4.52 (d, J = 9.3 Hz, 1H), 4.43 (t, J = 8.0 Hz, 1H), 4.28 (s, 1H), 3.85-3.81 (m, 2H), 3.63-3.59 (m, 2H), 2.54 (s, 2H), 2.46 (s, 3H), 2.35-2.25 (m, 1H), 2.18-2.07 (m, 2H), 2.03-1.98 (m, 1H), 1.81-1.77 (m, 2H), 1.55-1.51 (m, 7H), 1.39 (s, 9H), 1.27-1.23 (m, 2H), 1.08-1.04 (m, 1H), 0.94 (s, 9H) |

TABLE 47-continued

Characterization data for intermediates prepare according to the procedure above.

| Inter-me-diate | Structure | Chemical Name | MS: [(M + 1)]$^+$ | $^1$H-NMR |
|---|---|---|---|---|
| G124 | 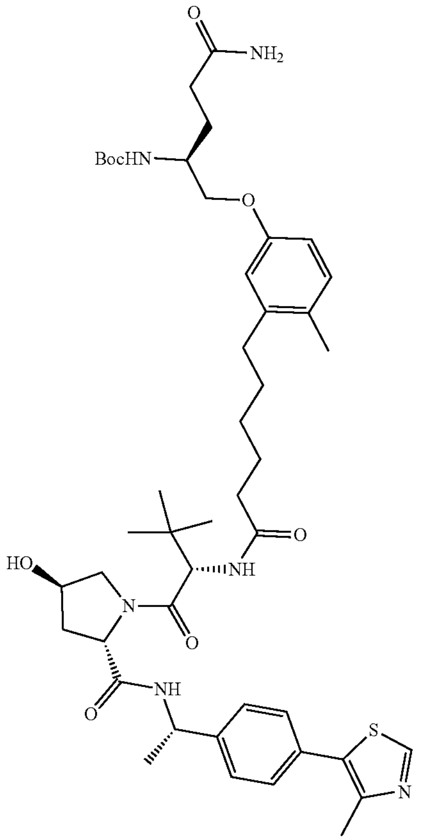 [SMILES: Cc1ccc(OC[C@H](CCC(N)=O)NC(=O)OC(C)(C)C)cc1CCCCCC(=O)N[C@H](C(=O)N1C[C@H](O)C[C@H]1C(=O)N[C@@H](C)c1ccc(-c2scnc2C)cc1)C(C)(C)C] | tert-butyl N-[(2S)-4-carbamoyl-1-[3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)-4-methylphenoxy]butan-2-yl]carbamate | 863.45 | (400 MHz, DMSO-$d_6$) δ 8.99 (s, 1H), 8.38 (d, J = 7.9 Hz, 1H), 7.81 (d, J = 9.3 Hz, 1H), 7.44 (d, J = 8.3 Hz, 2H), 7.38 (d, J = 8.3 Hz, 2H), 7.27 (s, 1H), 7.01 (d, J = 8.3 Hz, 1H), 6.81 (d, J = 8.4 Hz, 1H), 6.74 (s, 1H), 6.69 (d, J = 2.7 Hz, 1H), 6.64 (dd, J = 8.2, 2.7 Hz, 1H), 5.10-5.08 (m, 1H), 4.93-4.91 (m, 1H), 4.53-4.51 (m, 1H), 4.43-4.41 (m, 2H), 4.28-4.26 (m, 1H), 3.86-3.75 (m, 2H), 3.69-3.67 (m, 2H), 3.61-3.58 (m, 2H), 3.32-3.30 (m, 2H), 2.45 (s, 3H), 2.17-2.15 (m, 5H), 1.80-1.78 (m, 2H), 1.57-1.46 (m, 4H), 1.38-1.36 (m, 12H), 1.30-1.22 (m, 4H), 0.94 (s, 9H) |

TABLE 47-continued

Characterization data for intermediates prepare according to the procedure above.

| Intermediate | Structure | Chemical Name | MS: [(M + 1)]+ | ¹H-NMR |
|---|---|---|---|---|
| G125 | 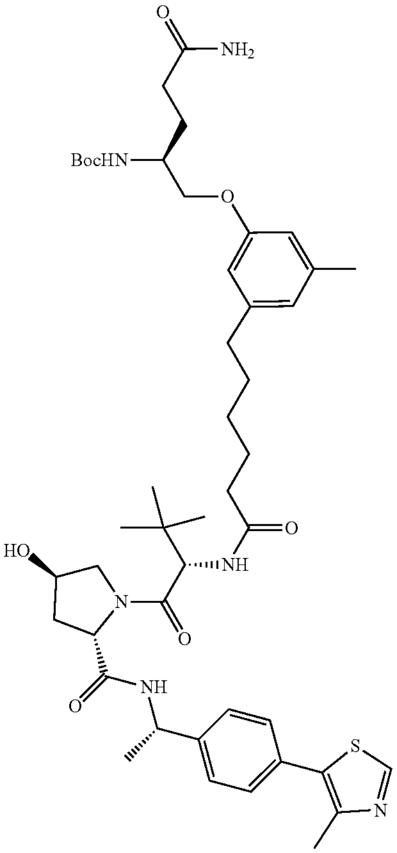 [SMILES: Cc1cc(CCCCCC(=O)N[C@H](C(=O)N2C[C@H](O)C[C@H]2C(=O)N[C@@H](C)c2ccc(-c3scnc3C)cc2)C(C)(C)C)cc(OC[C@H](CCC(N)=O)NC(=O)OC(C)(C)C)c1] | tert-butyl N-[(2S)-4-carbamoyl-1-[3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)-5-methylphenoxy]butan-2-yl]carbamate | 863.45 | (400 MHz, DMSO-$d_6$) δ 8.99 (s, 1H), 8.38 (d, J = 7.8 Hz, 1H), 7.80 (d, J = 9.3 Hz, 1H), 7.44 (d, J = 8.3 Hz, 2H), 7.38 (d, J = 8.3 Hz, 2H), 7.27 (s, 1H), 6.81 (d, J = 8.5 Hz, 1H), 6.74 (s, 1H), 6.59-6.51 (m, 3H), 5.17-5.03 (m, 1H), 4.94-4.90 (m, 1H), 4.52 (d, J = 9.3 Hz, 1H), 4.43 (t, J = 8.0 Hz, 1H), 4.28 (s, 1H), 3.83-3.79 (m, 2H), 3.74-3.67 (m, 1H), 3.61 (d, J = 3.9 Hz, 2H), 2.46 (s, 3H), 2.23 (s, 3H), 2.14-2.09 (m, 2H), 1.87-1.74 (m, 1H), 1.58-1.49 (m, 6H), 1.42-1.35 (m, 13H), 1.25-1.20 (m, 6H), 0.93 (s, 9H) |

TABLE 47-continued

| Characterization data for intermediates prepare according to the procedure above. | | | | |
|---|---|---|---|---|
| Inter-me-diate | Structure | Chemical Name | MS: [(M + 1)]+ | 1H-NMR |
| G126 | 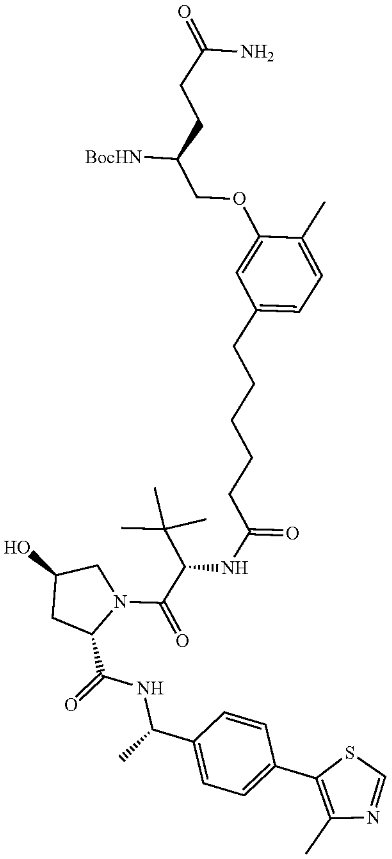 [SMILES: Cc1ccc(CCCCCC(=O)N[C@H](C(=O)N2C[C@H](O)C[C@H]2C(=O)N[C@@H](C)c2ccc(-c3scnc3C)cc2)C(C)(C)C)cc1OC[C@H](CCC(N)=O)NC(=O)OC(C)(C)C] | tert-butyl N-[(2S)-4-carbamoyl-1-[5-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)-2-methylphenoxy]butan-2-yl]carbamate | 863.40 | (400 MHz, Chloroform-d) δ 8.70 (s, 1H), 7.40-7.30 (m, 5H), 7.03 (d, J = 7.6 Hz, 1H), 6.69 (d, J = 7.5, 1.5 Hz, 1H), 6.61 (d, J = 1.6 Hz, 1H), 6.5-6.47 (m, 1H), 6.36 (d, J = 8.7 Hz, 1H), 5.75 (s, 1H), 5.32 (s, 1H), 5.10 (d, J = 14.9, 7.4 Hz, 2H), 4.72 (s, 1H), 4.58 (d, J = 8.8 Hz, 1H), 4.53 (d, J = 4.4, 2.2 Hz, 1H), 4.13-3.94 (m, 4H), 3.63 (d, J = 11.3, 3.8 Hz, 1H), 3.50 (s, 1H), 2.56-2.52 (m, 4H), 2.38-2.34 (m, 2H), 2.19-2.10 (m, 3H), 2.03-1.98 (m, 2H), 1.62-1.59 (m, 3H), 1.49 (d, J = 7.0 Hz, 3H), 1.43 (s, 9H), 1.29-1.25 (m, 3H), 1.04 (s, 9H), 0.91-0.87 (m, 4H) |

TABLE 47-continued

Characterization data for intermediates prepare according to the procedure above.

| Intermediate | Structure | Chemical Name | MS: [(M + 1)]+ | 1H-NMR |
|---|---|---|---|---|
| G127 | 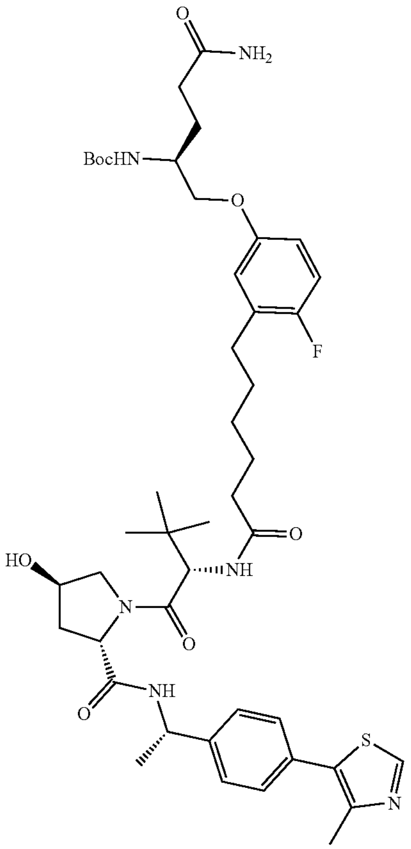 [SMILES: Cc1ncsc1-c1ccc([C@H](C)NC(=O)[C@@H]2C[C@@H](O)CN2C(=O)[C@@H](NC(=O)CCCCCc2cc(OC[C@H](CCC(N)=O)NC(=O)OC(C)(C)C)ccc2F)C(C)(C)C)cc1] | tert-butyl N-[(2S)-4-carbamoyl-1-[4-fluoro-3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenoxy]butan-2-yl]carbamate | 867.35 | (400 MHz, DMSO-$d_6$) δ 8.99 (s, 1H), 8.38 (d, J = 7.8 Hz, 1H), 7.80 (d, J = 9.3 Hz, 1H), 7.44 (d, J = 8.3 Hz, 2H), 7.38 (d, J = 8.3 Hz, 2H), 7.27 (s, 1H), 7.02 (t, J = 9.3 Hz, 1H), 6.86-6.79 (m, 2H), 6.77-6.73 (m, 2H), 4.94-4.90 (m, 1H), 4.52 (d, J = 9.4 Hz, 1H), 4.43 (t, J = 8.0 Hz, 1H), 4.31-4.27 (m, 1H), 3.84-3.80 (m, 2H), 3.70 (d, J = 10.3 Hz, 1H), 3.61 (d, J = 3.7 Hz, 2H), 2.55 (d, J = 7.6 Hz, 2H), 2.46 (s, 3H), 2.28-2.24 (m, 1H), 2.14-2.10 (m, 3H), 2.08 (s, 2H), 2.04-2.00 (m, 1H), 1.82-1.78 (m, 1H), 1.56-1.52 (m, 6H), 1.39 (s, 9H), 1.39-1.35 (m, 2H), 1.29-1.25 (m, 2H), 0.93 (s, 9H) |

TABLE 47-continued

Characterization data for intermediates prepare according to the procedure above.

| Intermediate | Structure | Chemical Name | MS: [(M + 1)]+ | 1H-NMR |
|---|---|---|---|---|
| G128 | 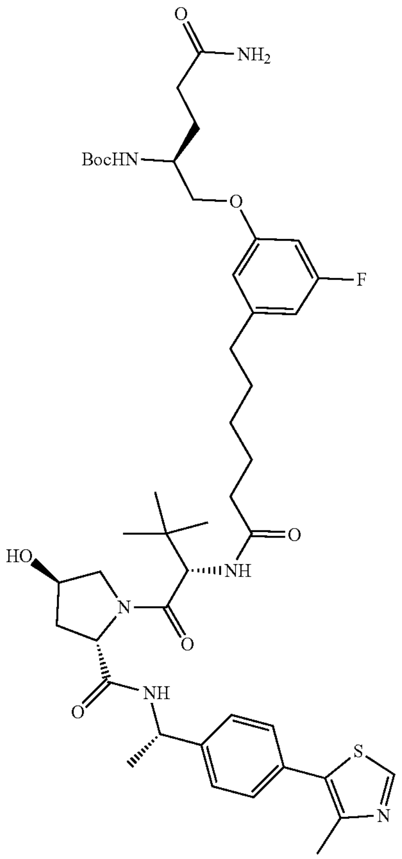 [SMILES: Cc1ncsc1-c1ccc([C@H](C)NC(=O)[C@@H]2C[C@@H](O)CN2C(=O)[C@@H](NC(=O)CCCCCc2cc(F)cc(OC[C@H](CCC(N)=O)NC(=O)OC(C)(C)C)c2)C(C)(C)C)cc1] | tert-butyl N-[(2S)-4-carbamoyl-1-[3-fluoro-5-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenoxy]butan-2-yl]carbamate | 867.40 | (400 MHz, DMSO-$d_6$) δ 8.99 (s, 1H), 8.38 (d, J = 7.8 Hz, 1H), 7.80 (d, J = 9.3 Hz, 1H), 7.49-7.31 (m, 4H), 7.27 (s, 1H), 6.84 (d, J = 8.5 Hz, 1H), 6.74 (s, 1H), 6.60 (d, J = 9.1 Hz, 3H), 5.11 (s, 1H), 4.94-4.90 (m, 1H), 4.55-4.47 (m, 1H), 4.43 (t, J = 8.0 Hz, 1H), 4.28 (s, 1H), 3.92-3.80 (m, 2H), 3.74-3.67 (m, 1H), 3.66-3.55 (m, 2H), 2.54 (s, 1H), 2.46 (s, 3H), 2.30-2.20 (m, 1H), 2.17-2.07 (m, 3H), 2.10-1.96 (m, 1H), 1.82-1.78 (m, 3H), 1.67-1.44 (m, 6H), 1.40-1.36 (m, 11H), 1.28-1.24 (m, 2H), 0.93 (s, 9H) |

TABLE 47-continued

| Characterization data for intermediates prepare according to the procedure above. | | | | |
|---|---|---|---|---|
| Inter-me-diate | Structure | Chemical Name | MS: [(M + 1)]$^+$ | $^1$H-NMR |
| G129 | 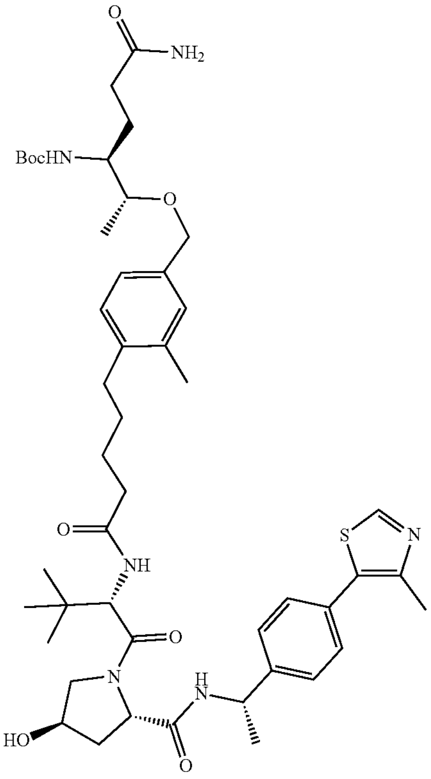 [SMILES: Cc1cc(CO[C@H](C)[C@H](CCC(N)=O)NC(=O)OC(C)(C)C)ccc1CCCCC(=O)N[C@H](C(=O)N1C[C@H](O)C[C@H]1C(=O)N[C@@H](C)c1ccc(-c2scnc2C)cc1)C(C)(C)C] | tert-butyl N-[(3S,4R)-1-carbamoyl-4-[[4-(4-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]butyl)-3-methylphenyl]methoxy]pentan-3-yl]carbamate | 877.35 | (400 MHz, DMSO-$d_6$) δ 8.99 (s, 1H), 8.38 (d, J = 7.8 Hz, 1H), 7.83 (d, J = 9.3 Hz, 1H), 7.47-7.41 (m, 2H), 7.38 (d, J = 8.3 Hz, 2H), 7.22 (s, 1H), 7.07 (d, J = 10.3 Hz, 3H), 6.69 (s, 1H), 6.60 (d, J = 9.2 Hz, 1H), 5.10 (s, 1H), 4.96-4.89 (m, 1H), 4.53 (d, J = 9.3 Hz, 1H), 4.48-4.35 (m, 3H), 4.28 (s, 1H), 3.65-3.56 (m, 2H), 3.46-3.37 (m, 3H), 2.56-2.54 (m, 1H), 2.46 (s, 3H), 2.37-2.27 (m, 1H), 2.24 (s, 3H), 2.21-1.95 (m, 4H), 1.83-1.77 (m, 2H), 1.59-1.44 (m, 6H), 1.39 (s, 9H), 1.37-1.36 (m, 2H), 1.05 (d, J = 6.0 Hz, 3H), 0.94 (s, 9H) |

TABLE 47-continued

| Characterization data for intermediates prepare according to the procedure above. | | | | |
|---|---|---|---|---|
| Intermediate | Structure | Chemical Name | MS: [(M + 1)]+ | 1H-NMR |
| G130 | 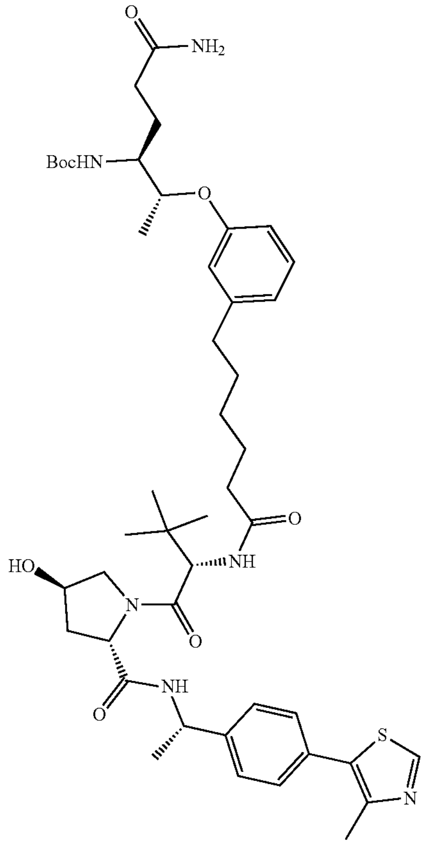 [SMILES: Cc1ncsc1-c1ccc([C@H](C)NC(=O)[C@@H]2C[C@@H](O)CN2C(=O)[C@@H](NC(=O)CCCCCc2cccc(O[C@H](C)[C@H](CCC(N)=O)NC(=O)OC(C)(C)C)c2)C(C)(C)C)cc1] | tert-butyl N-[(3S,4R)-1-carbamoyl-4-[3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenoxy]pentan-3-yl]carbamate | 863.50 | (400 MHz, DMSO-$d_6$) δ 8.99 (s, 1H), 8.38 (d, J = 7.8 Hz, 1H), 7.81 (d, J = 9.2 Hz, 1H), 7.47-7.35 (m, 4H), 7.25 (s, 1H), 7.15 (t, J = 7.7 Hz, 1H), 6.80-6.62 (m, 5H), 5.11 (d, J = 3.6 Hz, 1H), 4.96-4.88 (m, 1H), 4.52 (d, J = 9.2 Hz, 1H), 4.43 (t, J = 8.0 Hz, 1H), 4.32-4.26 (m, 2H), 3.64-3.59 (m, 2H), 3.54-3.47 (m, 1H), 2.46 (s, 3H), 2.30-2.21 (m, 1H), 2.16-1.95 (m, 7H), 1.94-1.73 (m, 3H), 1.60-1.47 (m, 5H), 1.38 (s, 9H), 1.31-1.24 (m, 3H), 1.17 (d, J = 6.1 Hz, 3H), 0.93 (s, 9H) |

TABLE 47-continued

| Characterization data for intermediates prepare according to the procedure above. | | | | |
|---|---|---|---|---|
| Intermediate | Structure | Chemical Name | MS: [(M + 1)]+ | 1H-NMR |
| G131 | 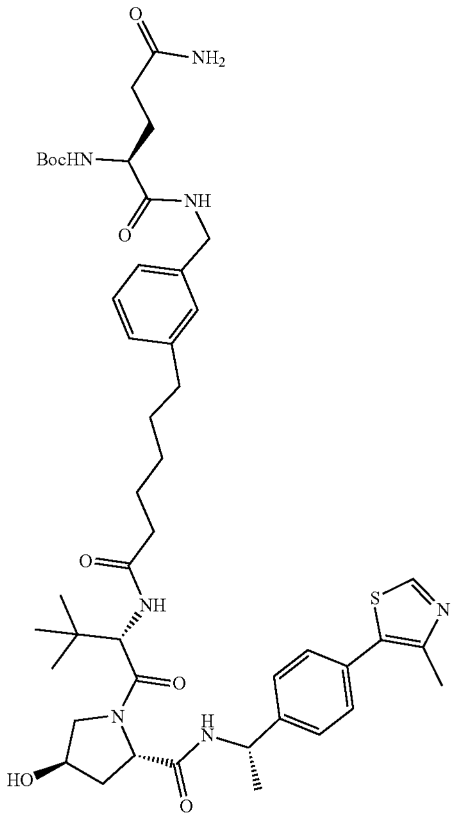 [SMILES: Cc1ncsc1-c1ccc([C@H](C)NC(=O)[C@@H]2C[C@@H](O)CN2C(=O)[C@@H](NC(=O)CCCCCc2cccc(CNC(=O)[C@H](CCC(N)=O)NC(=O)OC(C)(C)C)c2)C(C)(C)C)cc1] | tert-butyl N-[(1S)-3-carbamoyl-1-([[3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenyl]methyl]carbamoyl)propyl]carbamate | 876.70 | (400 MHz, Methanol-$d_4$) δ 8.89 (s, 1H), 7.48-7.42 (m, 4H), 7.22 (t, J = 7.5 Hz, 1H), 7.11 (dd, J = 19.7, 9.7 Hz, 3H), 5.02 (q, J = 7.0 Hz, 1H), 4.68-4.63 (m, 1H), 4.59 (t, J = 8.3 Hz, 1H), 4.48-4.43 (m, 1H), 4.36 (t, J = 15.6 Hz, 2H), 4.14-4.06 (m, 1H), 3.90 (d, J = 11.0 Hz, 1H), 3.77 (dd, J = 11.0, 3.9 Hz, 1H), 2.61 (t, J = 7.6 Hz, 2H), 2.50 (s, 3H), 2.32 (d, J = 2.1 Hz, 1H), 2.31-2.27 (m, 2H), 2.26-2.20 (m, 1H), 2.09-2.02 (m, 1H), 1.98 (ddd, J = 13.2, 9.0, 4.5 Hz, 1H), 1.93-1.85 (m, 1H), 1.69-1.61 (m, 4H), 1.59-1.48 (m, 4H), 1.46 (s, 9H), 1.37 (d, J = 7.9 Hz, 2H), 1.06-1.03 (m, 9H) |

TABLE 47-continued

| Characterization data for intermediates prepare according to the procedure above. | | | | |
|---|---|---|---|---|
| Inter-me-diate | Structure | Chemical Name | MS: [(M + 1)]$^+$ | $^1$H-NMR |
| G132 | 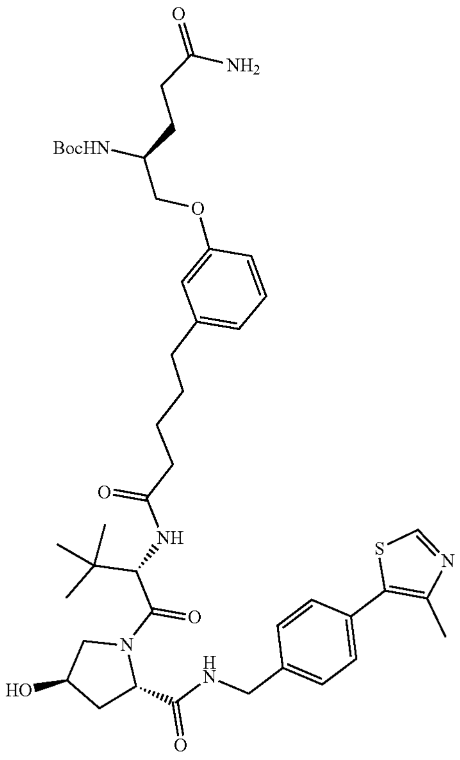 [SMILES: Cc1ncsc1-c1ccc(CNC(=O)[C@@H]2C[C@@H](O)CN2C(=O)[C@@H](NC(=O)CCCCc2cccc(OC[C@H](CCC(N)=O)NC(=O)OC(C)(C)C)c2)C(C)(C)C)cc1] | tert-butyl N-[(2S)-4-carbamoyl-1-[3-(4-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]butyl)phenoxy]butan-2-yl]carbamate | 821.30 | (400 MHz, Methanol-$d_4$) δ 8.90 (s, 1H), 7.52-7.39 (m, 4H), 7.16 (t, J = 8.0 Hz, 1H), 6.81-6.70 (m, 3H), 4.68-4.46 (m, 4H), 4.37 (d, J = 15.6 Hz, 1H), 3.99-3.76 (m, 5H), 2.60 (t, J = 6.9 Hz, 2H), 2.49 (s, 3H), 2.40-2.18 (m, 5H), 2.14-1.95 (m, 2H), 1.80 (s, 1H), 1.65 (t, J = 6.0 Hz, 4H), 1.46 (s, 9H), 1.05 (s, 9H) |

TABLE 47-continued

| Characterization data for intermediates prepare according to the procedure above. | | | | |
|---|---|---|---|---|
| Inter-me-diate | Structure | Chemical Name | MS: [(M + 1)]$^+$ | $^1$H-NMR |
| G133 | 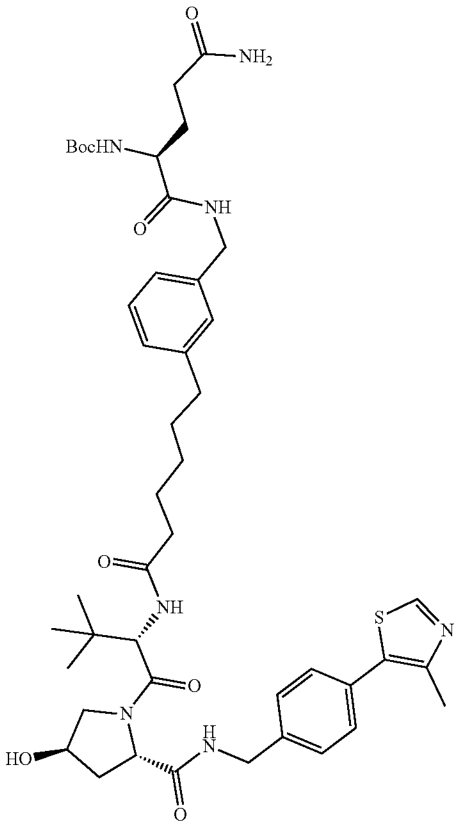 [SMILES: Cc1ncsc1-c1ccc(CNC(=O)[C@@H]2C[C@@H](O)CN2C(=O)[C@@H](NC(=O)CCCCCc2cccc(CNC(=O)[C@H](CCC(N)=O)NC(=O)OC(C)(C)C)c2)C(C)(C)C)cc1] | tert-butyl N-[(3S,4R)-1-carbamoyl-4-[[4-(4-[[(2S)-1-[(2S,4R)-4-hydroxy-2-[[4-(4-methyl-1,3-thiazol-5-yl)phenoxy]carbamoyl]pyrrolidin-1-yl]-3,3-dimethyl-1-oxobutan-2-yl]carbamoyl]butyl)phenyl]methoxy]pentan-3-yl]carbamate | 862.40 | $^1$H NMR (400 MHz, Methanol-$d_4$) δ 8.89 (s, 1H), 7.48 (d, J = 8.3 Hz, 2H), 7.43 (d, J = 8.3 Hz, 2H), 7.21 (t, J = 7.6 Hz, 1H), 7.14 (s, 1H), 7.12-7.05 (m, 2H), 4.66 (d, J = 5.8 Hz, 1H), 4.62-4.55 (m, 1H), 4.54-4.51 (m, 2H), 4.42-4.40 (m, 2H), 4.37-4.31 (m, 2H), 4.13-4.09 (m, 1H), 3.93-3.91 (m, 1H), 3.82 (dd, J = 10.9, 3.9 Hz, 1H), 2.61 (t, J = 7.6 Hz, 2H), 2.39-2.21 (m, 6H), 2.15-2.01 (m, 1H), 1.92-1.88 (m, 1H), 1.68-1.60 (m, 4H), 1.45 (s, 9H), 1.39-1.35 (m, 2H), 1.05 (s, 9H). |

TABLE 47-continued

| Characterization data for intermediates prepare according to the procedure above. | | | | |
|---|---|---|---|---|
| Inter-me-diate | Structure | Chemical Name | MS: [(M + 1)]$^+$ | $^1$H-NMR |
| G134 | 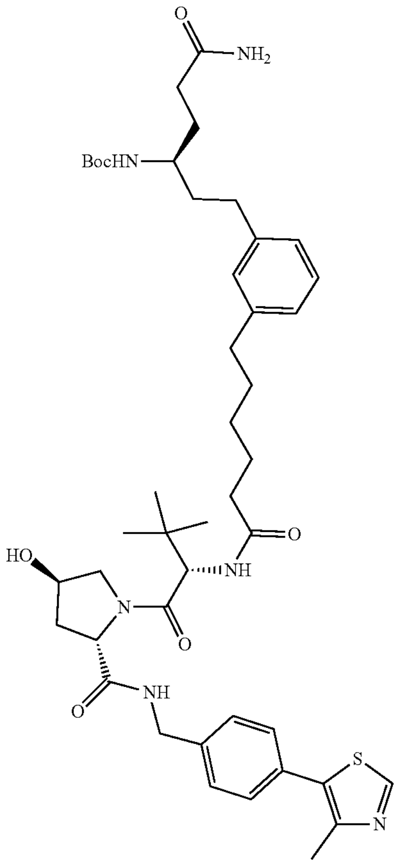 [SMILES: Cc1ncsc1-c1ccc(CNC(=O)[C@@H]2C[C@@H](O)CN2C(=O)[C@@H](NC(=O)CCCCCc2cccc(CC[C@H](CCC(N)=O)NC(=O)OC(C)(C)C)c2)C(C)(C)C)cc1] | tert-butyl N-[(3R)-1-carbamoyl-5-[3-(5-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]pentyl)phenyl]pentan-3-yl]carbamate | 833.40 | (400 MHz, DMSO-$d_6$) δ 8.99 (s, 1H), 8.56 (t, J = 6.1 Hz, 1H), 7.84 (d, J = 9.3 Hz, 1H), 7.41 (q, J = 8.4 Hz, 4H), 7.22 (s, 1H), 7.16 (t, J = 7.5 Hz, 1H), 6.98 (d, J = 7.4 Hz, 3H), 6.69 (d, J = 9.0 Hz, 2H), 5.13 (s, 1H), 4.55 (d, J = 9.4 Hz, 1H), 4.50-4.40 (m, 2H), 4.37 (s, 1H), 4.23 (dd, J = 15.9, 5.4 Hz, 1H), 3.73-3.62 (m, 2H), 2.54 (s, 2H), 2.46 (s, 3H), 2.34-2.22 (m, 1H), 2.13 (dd, J = 13.9, 6.7 Hz, 2H), 2.04 (t, J = 7.6 Hz, 3H), 1.97-1.86 (m, 1H), 1.64 (d, J = 8.0 Hz, 2H), 1.62-1.45 (m, 7H), 1.41 (s, 9H), 1.38-1.34 (m, 1H), 1.29 (q, J = 7.5 Hz, 2H), 0.94 (s, 9H) |

TABLE 47-continued

| Characterization data for intermediates prepare according to the procedure above. | | | | |
|---|---|---|---|---|
| Intermediate | Structure | Chemical Name | MS: [(M + 1)]+ | $^1$H-NMR |
| G135 | 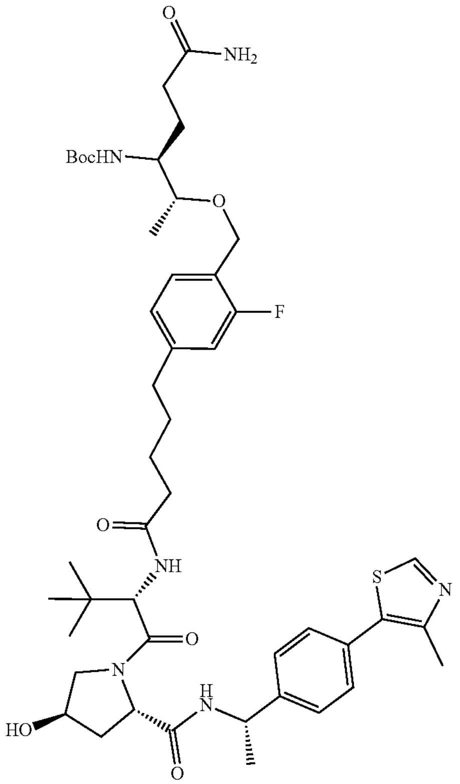 [SMILES: Cc1ncsc1-c1ccc([C@H](C)NC(=O)[C@@H]2C[C@@H](O)CN2C(=O)[C@@H](NC(=O)CCCCc2ccc(CO[C@H](C)[C@H](CCC(N)=O)NC(=O)OC(C)(C)C)c(F)c2)C(C)(C)C)cc1] | tert-butyl N-[(3S,4R)-1-carbamoyl-4-[[2-fluoro-4-(4-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]butyl)phenyl]methoxy]pentan-3-yl]carbamate | 881.55 | (400 MHz, DMSO-$d_6$) δ 8.99 (s, 1H), 8.37 (d, J = 7.8 Hz, 1H), 7.83 (d, J = 9.2 Hz, 1H), 7.47-7.36 (m, 4H), 7.34 (t, J = 8.0 Hz, 1H), 7.21 (s, 1H), 7.04-6.95 (m, 2H), 6.68 (s, 1H), 6.60 (d, J = 8.8 Hz, 1H), 5.10 (s, 1H), 4.96-4.89 (m, 1H), 4.57-4.38 (m, 5H), 4.28 (s, 1H), 3.64-3.57 (m, 2H), 3.44-3.40 (m, 1H), 2.58 (t, J = 7.2 Hz, 1H), 2.46 (s, 3H), 2.37-2.24 (m, 1H), 2.21-1.93 (m, 4H), 1.84-1.68 (m, 2H), 1.61-1.42 (m, 5H), 1.38-1.35 (m, 13H), 1.06 (d, J = 5.7 Hz, 3H), 0.94 (s, 9H) |

TABLE 47-continued

| Characterization data for intermediates prepare according to the procedure above. | | | | |
|---|---|---|---|---|
| Inter-me-diate | Structure | Chemical Name | MS: [(M + 1)]+ | 1H-NMR |
| G136 | 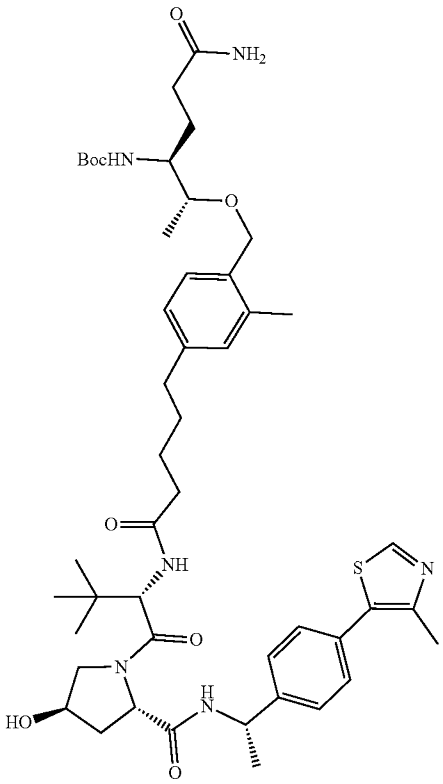 [SMILES: Cc1cc(CCCCC(=O)N[C@H](C(=O)N2C[C@H](O)C[C@H]2C(=O)N[C@@H](C)c2ccc(-c3scnc3C)cc2)C(C)(C)C)ccc1CO[C@H](C)[C@H](CCC(N)=O)NC(=O)OC(C)(C)C] | tert-butyl N-[(3S,4R)-1-carbamoyl-4-[[4-(4-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]butyl)-2-methylphenyl]methoxy]pentan-3-yl]carbamate | 877.51 | (400 MHz, Methanol-$d_4$) δ 8.89 (s, 1H), 7.48-7.41 (m, 4H), 7.21 (d, J = 7.6 Hz, 1H), 7.00 (q, J = 8.0 Hz, 2H), 5.51 (s, 2H), 5.02 (q, J = 6.9 Hz, 1H), 4.64 (s, 1H), 4.61-4.55 (m, 2H), 4.50-4.43 (m, 2H), 3.89 (d, J = 10.9 Hz, 1H), 3.76 (dd, J = 11.0, 4.0 Hz, 1H), 3.60-3.55 (m, 1H), 3.55-3.49 (m, 1H), 2.59 (d, J = 7.2 Hz, 2H), 2.50 (s, 3H), 2.34 (s, 3H), 2.30-2.17 (m, 4H), 2.01-1.93 (m, 2H), 1.65 (d, J = 1.6 Hz, 4H), 1.52 (d, J = 7.0 Hz, 3H), 1.45 (d, J = 3.7 Hz, 9H), 1.19 (d, J = 6.1 Hz, 3H), 1.06 (s, 9H) |

TABLE 47-continued

| Characterization data for intermediates prepare according to the procedure above. | | | | |
|---|---|---|---|---|
| Inter-me-diate | Structure | Chemical Name | MS: [(M + 1)]$^+$ | $^1$H-NMR |
| G137 | 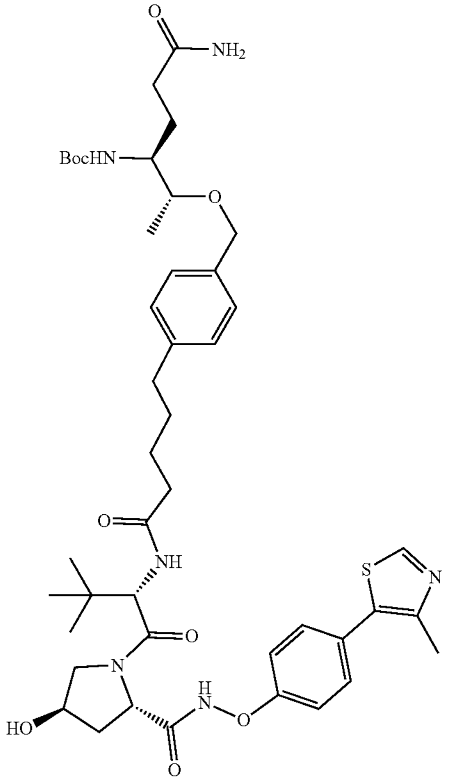 [SMILES: Cc1ncsc1-c1ccc(ONC(=O)[C@@H]2C[C@@H](O)CN2C(=O)[C@@H](NC(=O)CCCCc2ccc(CO[C@H](C)[C@H](CCC(N)=O)NC(=O)OC(C)(C)C)cc2)C(C)(C)C)cc1] | tert-butyl N-[(3S,4R)-1-carbamoyl-4-[[4-(4-[[(2S)-1-[(2S,4R)-4-hydroxy-2-[[4-(4-methyl-1,3-thiazol-5-yl)phenoxy] carbamoyl]pyrrolidin-1-yl]-3,3-dimethyl-1-oxobutan-2-yl]carbamoyl]butyl) phenyl]methoxy]pentan-3-yl]carbamate | 851.50 | (400 MHz, Methanol-$d_4$) δ 8.87 (s, 1H), 7.44-7.39 (m, 2H), 7.37-7.32 (m, 2H), 7.27 (d, J = 7.9 Hz, 2H), 7.17 (d, J = 7.8 Hz, 2H), 4.65 (s, 1H), 4.59-4.53 (m, 3H), 4.48 (d, J = 11.5 Hz, 1H), 3.95 (d, J = 10.9 Hz, 1H), 3.83 (d d, J = 11.0, 3.8 Hz, 1H), 3.61-3.55 (m, 1H), 3.52 (s, 1H), 2.64 (d, J = 7.0 Hz, 2H), 2.50-2.44 (m, 4H), 2.38-2.13 (m, 6H), 2.00-1.95 (m, 1H), 1.66 (s, 4H), 1.45 (s, 9H), 1.17 (d, J = 6.2 Hz, 3H), 1.05 (s, 9H) |
| G138 | 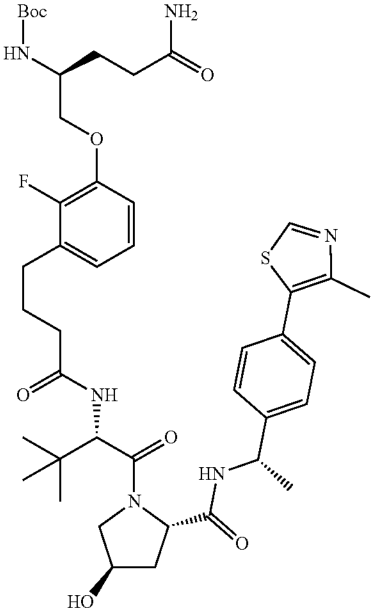 [SMILES: Cc1ncsc1-c1ccc([C@H](C)NC(=O)[C@@H]2C[C@@H](O)CN2C(=O)[C@@H](NC(=O)CCCc2cccc(OC[C@H](CCC(N)=O)NC(=O)OC(C)(C)C)c2F)C(C)(C)C)cc1] | tert-butyl N-[(2S)-4-carbamoyl-1-[2-fluoro-3-(3-[[(2S)-1-[(2S,4R)-4-hydroxy-2-[[(1S)-1-[4-(4-methyl-1,3-thiazol-5-yl)phenyl]ethyl] carbamoyl]pyrrolidin-1-yl]-3,3-dimethyl-1-oxobutan-2-yl]carbamoyl]propyl) phenoxy]butan-2-yl]carbamate | 839.40 | $^1$H NMR (400 MHz, CD3OD) δ 8.91-8.89 (m, 1H), 7.48-7.41 (m, 4H), 7.03-6.93 (m, 2H), 6.85-6.82 (m, 1H), 5.03-5.01 (m, 1H), 4.66-4.64 (m, 1H), 4.61-4.56 (m, 1H), 4.47-4.42 (m, 1H), 4.02-3.99 (m, 2H), 3.90 (d, J = 10.9 Hz, 2H), 3.79-3.76 (m, 1H), 2.71-2.67 (m, 2H), 2.50 (s, 3H), 2.34-2.32 (m, 4H), 2.24-2.18 (m, 1H), 2.06-1.89 (m, 4H), 1.85-1.81 (m, 1H), 1.53 (d, J = 7.0 Hz, 3H), 1.46 (s, 9H), 1.05 (s, 9H) |

TABLE 47-continued

| Characterization data for intermediates prepare according to the procedure above. | | | | |
|---|---|---|---|---|
| Inter-me-diate | Structure | Chemical Name | MS: [(M + 1)]$^+$ | $^1$H-NMR |
| G139 | 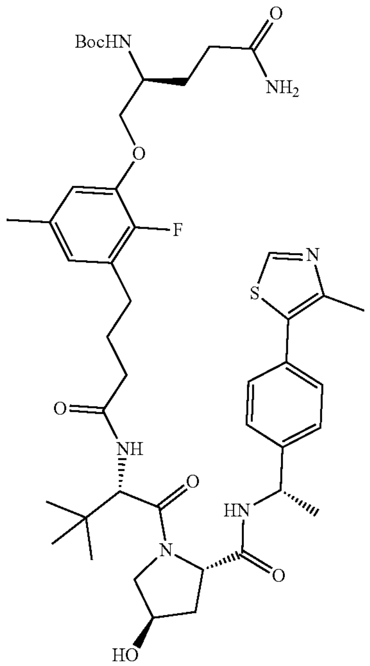 | tert-butyl N-[(2S)-4-carbamoyl-1-[2-fluoro-3-(3-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]propyl)-5-methylphenoxy]butan-2-yl]carbamate | 853.40 | $^1$H NMR (300 MHz, DMSO-d$_6$) δ 8.97 (s, 1H), 8.35 (d, J = 7.8 Hz, 1H), 7.84 (d, J = 9.2 Hz, 1H), 7.40 (q, J = 8.2 Hz, 4H), 7.25 (s, 1H), 6.83-6.76 (m, 2H), 6.72 (s, 1H), 6.59 (d, J = 6.1 Hz, 1H), 5.08 (s, 1H), 4.99-4.85 (m, 1H), 4.52 (d, J = 9.3 Hz, 1H), 4.42 (t, J = 8.0 Hz, 1H), 4.27 (s, 1H), 3.88 (d, J = 6.0 Hz, 2H), 3.78-3.66 (m, 1H), 3.64-3.56 (m, 2H), 2.45 (s, 3H), 2.28 (d, J = 6.9 Hz, 1H), 2.23 (s, 3H), 2.20-2.10 (m, 4H), 2.02-1.95 (m, 1H), 1.87-1.67 (m, 5H), 1.66-1.52 (m, 1H), 1.38 (s, 9H), 1.35 (s, 3H), 0.94 (s, 9H) |
| G140 | 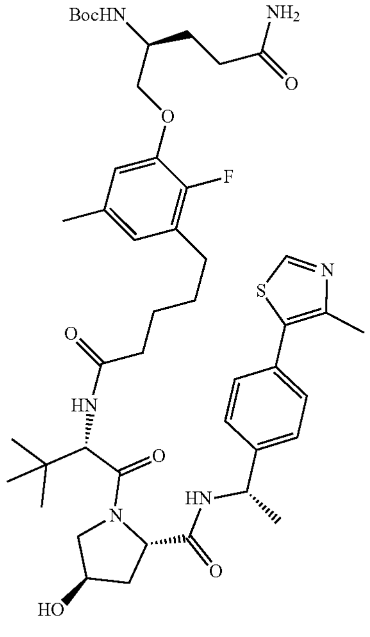 [SMILES: Cc1cc(CCCCC(=O)N[C@H](C(=O)N2C[C@H](O)C[C@H]2C(=O)N[C@@H](C)c2ccc(-c3scnc3C)cc2)C(C)(C)C)c(F)c(OC[C@H](CCC(N)=O)NC(=O)OC(C)(C)C)c1] | tert-butyl N-[(2S)-4-carbamoyl-1-[2-fluoro-3-(4-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]butyl)-5-methylphenoxy]butan-2-yl]carbamate | 867.45 | (300 MHz, DMSO-d$_6$) δ 9.00 (d, J = 1.4 Hz, 1H), 8.39 (d, J = 7.7 Hz, 1H), 7.84 (d, J = 9.3 Hz, 1H), 7.50-7.37 (m, 4H), 7.28 (s, 1H), 6.81 (dd, J = 20.1, 11.0 Hz, 3H), 6.63 (d, J = 5.9 Hz, 1H), 5.12 (s, 1H), 5.01-4.88 (m, 1H), 4.57-4.39 (m, 2H), 4.30 (s, 1H), 3.90 (d, J = 5.9 Hz, 2H), 3.79-3.69 (m, 1H), 3.65-3.58 (m, 2H), 2.47 (s, 3H), 2.25 (s, 3H), 2.19-2.12 (m, 3H), 2.09 (d, J = 1.5 Hz, 3H), 2.06-1.98 (m, 1H), 1.88-1.73 (m, 3H), 1.67-1.58 (m, 1H), 1.56-1.44 (m, 4H), 1.40 (s, 9H), 1.37 (s, 3H), 0.95 (s, 9H) |

TABLE 47-continued

| Characterization data for intermediates prepare according to the procedure above. | | | | |
|---|---|---|---|---|
| Inter-me-diate | Structure | Chemical Name | MS: [(M + 1)]$^+$ | $^1$H-NMR |
| G141 | 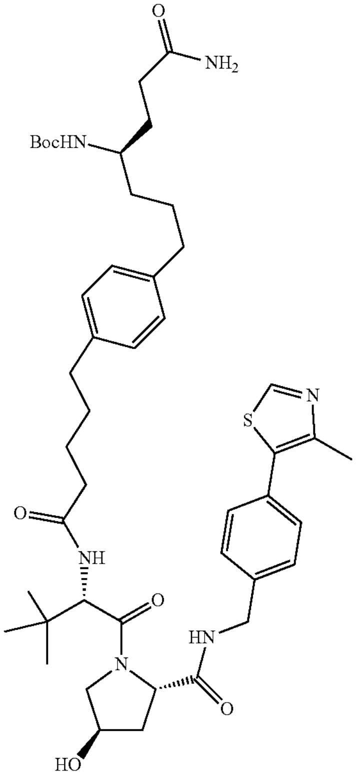 [SMILES: Cc1ncsc1-c1ccc(CNC(=O)[C@@H]2C[C@@H](O)CN2C(=O)[C@@H](NC(=O)CCCCc2ccc(CCC[C@H](CCC(N)=O)NC(=O)OC(C)(C)C)cc2)C(C)(C)C)cc1] | tert-butyl N-[(3R)-1-carbamoyl-6-[4-(4-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]butyl)phenyl]hexan-3-yl]carbamate | 847.50 | (300 MHz, DMSO-$d_6$) δ 9.00 (s, 1H), 8.39 (d, J = 7.8 Hz, 1H), 7.83 (d, J = 9.2 Hz, 1H), 7.48-7.35 (m, 4H), 7.23 (s, 1H), 7.08 (s, 4H), 6.69 (s, 1H), 6.60 (d, J = 9.2 Hz, 1H), 5.11 (d, J = 3.6 Hz, 1H), 5.01-4.87 (m, 1H), 4.59-4.39 (m, 2H), 4.30 (s, 1H), 3.62 (s, 2H), 3.46-3.38 (m, 1 H), 2.49-2.47 (m, 2H), 2.46 (s, 3H), 2.36-1.98 (m, 6H), 1.86-1.73 (m, 1H), 1.66-1.45 (m, 8H), 1.43-1.24 (m, 15H), 0.95 (s, 9H) |
| G142 | 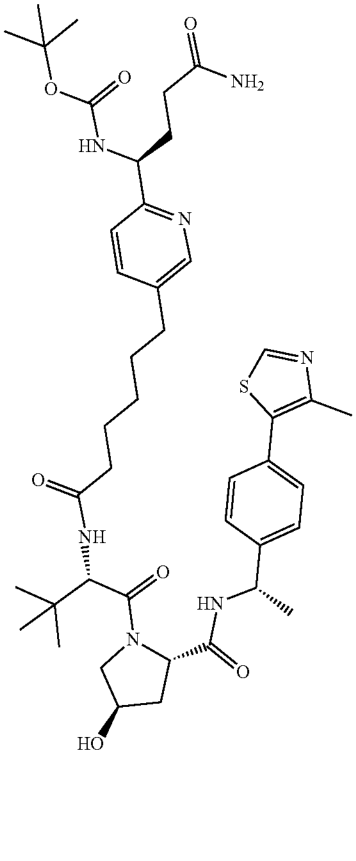 [SMILES: Cc1ncsc1-c1ccc([C@H](C)NC(=O)[C@@H]2C[C@@H](O)CN2C(=O)[C@@H](NC(=O)CCCCCc2ccc([C@H](CCC(N)=O)NC(=O)OC(C)(C)C)nc2)C(C)(C)C)cc1] | tert-butyl N-[(1S)-3-carbamoyl-1-[5-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)pyridin-2-yl]propyl]carbamate | 820.45 | (300 MHz, DMSO-$d_6$) δ 8.99 (s, 1H), 8.42-8.32 (m, 2H), 7.81-7.79 (m, 1H), 7.59-7.56 (dd, J = 8.0, 2.3 Hz, 1H), 7.48-7.41 (m, 3H), 7.41-7.32 (m, 2H), 7.28-7.23 (m, 1H), 7.21-7.19 (d, J = 8.0 Hz, 1H), 6.75 (s, 1H), 5.12-5.11 (d, J = 3.6 Hz, 1H), 4.96-4.89 (m, 1H), 4.53-4.50 (d, J = 9.3 Hz, 1H), 4.47-4.41 (s, 2H), 4.29-4.27 (m, 1H), 4.06-4.01 (m, 1H), 3.64-3.5δ (m, 2H), 2.69-2.65 (m, 2H), 2.46 (s, 3H), 2.29-2.22 (m, 1H), 2.15-2.10 (m, 1H), 2.06-1.2.02 (m, 3H), 2.00 (s, 1H), 1.93-1.74 (m, 2H), 1.68-1.61 (m, 2H), 1.56-1.48 (m, 2H), 1.38 (s, 3H), 1.37-1.35 (m, 7H), 1.27-1.19 (m, 3H), 0.93 (s, 9H) |

TABLE 47-continued

Characterization data for intermediates prepare according to the procedure above.

| Intermediate | Structure | Chemical Name | MS: [(M + 1)]+ | $^1$H-NMR |
|---|---|---|---|---|
| G143 | 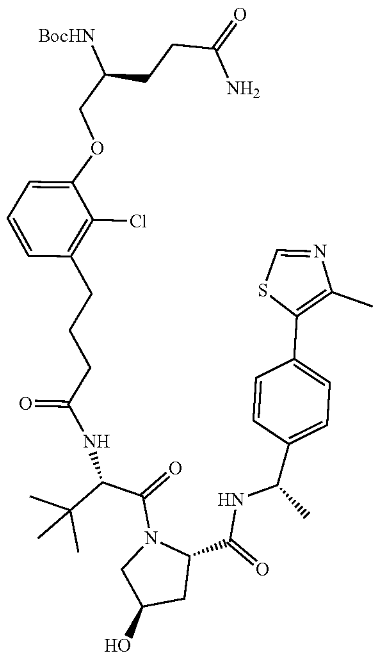 [SMILES: Cc1ncsc1-c1ccc([C@H](C)NC(=O)[C@@H]2C[C@@H](O)CN2C(=O)[C@@H](NC(=O)CCCc2cccc(OC[C@H](CCC(N)=O)NC(=O)OC(C)(C)C)c2Cl)C(C)(C)C)cc1] | tert-butyl N-[(2S)-4-carbamoyl-1-[2-chloro-3-(3-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]propyl)phenoxy]butan-2-yl]carbamate | 855.35 | (300 MHz, DMSO-$d_6$) δ 9.00 (s, 1H), 8.40 (d, J = 7.7 Hz, 1H), 7.90 (d, J = 9.2 Hz, 1H), 7.45-7.41 (m, 4H), 7.29 (s, 1H), 7.22 (t, J = 7.9 Hz, 1H), 7.00 (d, J = 8.3 Hz, 1H), 6.91 (d, J = 7.7 Hz, 1H), 6.83 (d, J = 8.3 Hz, 1H), 6.76 (s, 1H), 5.12 (s, 1H), 5.00-4.89 (m, 1H), 4.56 (d, J = 9.2 Hz, 1H), 4.45 (t, J = 8.1 Hz, 1H), 4.31 (s, 1H), 3.94 (d, J = 5.9 Hz, 2H), 3.79 (s, 1H), 3.64 (s, 2H), 2.69 (t, J = 7.7 Hz, 2H), 2.48 (s, 3H), 2.34-2.30 (m, 1H), 2.25-2.12 (m, 2H), 2.10 (s, 2H), 1.83-1.79 (m, 4H), 1.65-1.61 (m, 1H), 1.41 (s, 9H), 1.37 (d, J = 11.0 Hz, 3H), 0.97 (s, 9H) |
| G144 | 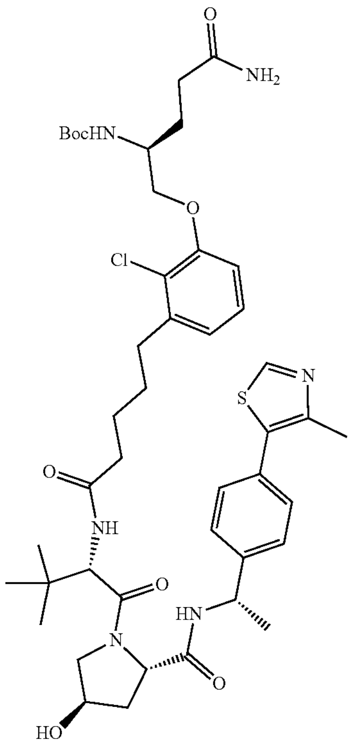 [SMILES: Cc1ncsc1-c1ccc([C@H](C)NC(=O)[C@@H]2C[C@@H](O)CN2C(=O)[C@@H](NC(=O)CCCCc2cccc(OC[C@H](CCC(N)=O)NC(=O)OC(C)(C)C)c2Cl)C(C)(C)C)cc1] | tert-butyl N-[(2S)-4-carbamoyl-1-[2-chloro-3-(3-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]propyl)phenoxy]butan-2-yl]carbamate | 869.35 | (400 MHz, DMSO-$d_6$) δ 8.99 (s, 1H), 8.39 (d, J = 7.8 Hz, 1H), 7.85 (d, J = 9.2 Hz, 1H), 7.45 (d, J = 8.3 Hz, 2H), 7.39 (d, J = 8.3 Hz, 2H), 7.30 (d, J = 15.6 Hz, 1H), 7.20 (t, J = 7.9 Hz, 1H), 6.98 (d, J = 8.2 Hz, 1H), 6.91 (dd, J = 7.6, 1.3 Hz, 1H), 6.81 (d, J = 8.5 Hz, 1H), 6.75 (s, 1H), 5.11 (d, J = 3.5 Hz, 1H), 4.99-4.87 (m, 1H), 4.53 (d, J = 9.3 Hz, 1H), 4.44 (t, J = 8.0 Hz, 1H), 4.31-4.27 (m, 1H), 3.93 (d, J = 6.1 Hz, 2H), 3.83-3.73 (m, 1H), 3.67-3.56 (m, 2H), 2.71-2.67 (m, 2H), 2.47 (s, 3H), 2.36-2.26 (m, 1H), 2.22-2.10 (m, 3H), 2.10-1.97 (m, 1H), 1.92-1.75 (m, 2H), 1.70-1.49 (m, 4H), 1.40 (s, 9H), 1.38-1.34 (m, 2H), 1.31-1.22 (m, 2H), 0.94 (s, 9H) |

TABLE 47-continued

| Characterization data for intermediates prepare according to the procedure above. | | | | |
|---|---|---|---|---|
| Intermediate | Structure | Chemical Name | MS: [(M + 1)]+ | $^1$H-NMR |
| G145 | 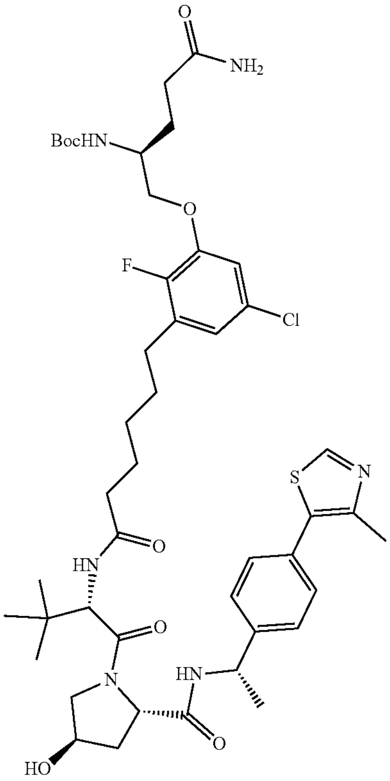 [SMILES: Cc1ncsc1-c1ccc([C@H](C)NC(=O)[C@@H]2C[C@@H](O)CN2C(=O)[C@@H](NC(=O)CCCCCc2cc(Cl)cc(OC[C@H](CCC(N)=O)NC(=O)OC(C)(C)C)c2F)C(C)(C)C)cc1] | tert-butyl N-[(2S)-4-carbamoyl-1-[5-chloro-2-fluoro-3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenoxy]butan-2-yl]carbamate | 901.35 | (400 MHz, DMSO-$d_6$) δ 8.99 (s, 1H), 8.38 (d, J = 7.8 Hz, 1H), 7.81-7.79 (m, 1H), 7.44 (d, J = 8.1 Hz, 2H), 7.38 (d, J = 8.1 Hz, 2H), 7.27 (s, 1H), 7.12-7.10 (m, 1H), 6.92-6.90 (m, 1H), 6.84 (d, J = 8.5 Hz, 1H), 6.75 (s, 1H), 5.11 (s, 1H), 4.92 (p, J = 7.3 Hz, 1H), 4.53-4.51 (m, 1H), 4.42 (t, J = 8.0 Hz, 1H), 4.29 (s, 1H), 3.97-3.93 (m, 1H), 3.75-3.73 (m, 1H), 3.61 (d, J = 4.1 Hz, 2H), 3.27-3.23 (m, 2H), 2.56 (d, J = 7.6 Hz, 1H), 2.46 (s, 3H), 2.31-2.20 (m, 1H), 2.19-2.10 (m, 2H), 2.10-2.06 (m, 2H), 2.03-2.01 (m, 1H), 1.88-1.78 (m, 2H), 1.64-1.44 (m, 5H), 1.38 (s, 9H), 1.27-1.21 (m, 4H), 0.93 (s, 9H) |
| G146 | 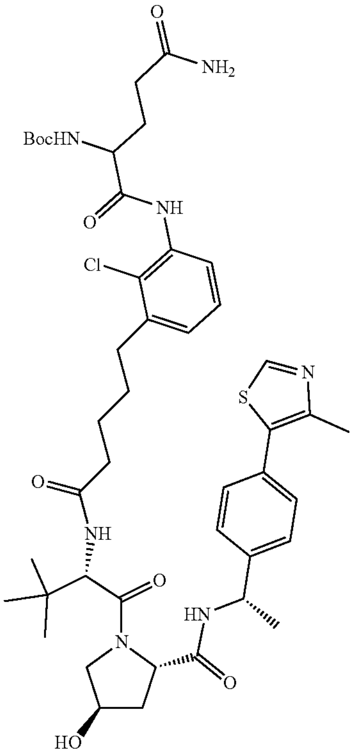 [SMILES: Cc1ncsc1-c1ccc([C@H](C)NC(=O)[C@@H]2C[C@@H](O)CN2C(=O)[C@@H](NC(=O)CCCCc2cccc(NC(=O)C(CCC(N)=O)NC(=O)OC(C)(C)C)c2Cl)C(C)(C)C)cc1] | tert-butyl N-(3-carbamoyl-1-[[2-chloro-3-(4-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]butyl)phenyl]carbamoyl]propyl)carbamate | 882.35 | (400 MHz, DMSO-$d_6$) δ 9.31 (s, 1H), 8.99 (s, 1H), 8.38 (d, J = 7.8 Hz, 1H), 7.84 (d, J = 9.3 Hz, 1H), 7.74 (d, J = 8.1 Hz, 1H), 7.68-7.53 (m, 1H), 7.44 (d, J = 8.3 Hz, 2H), 7.39 (d, J = 8.2 Hz, 2H), 7.26 (dd, J = 9.8, 6.6 Hz, 2H), 7.13 (d, J = 7.5 Hz, 1H), 6.81 (s, 1H), 5.10 (d, J = 3.6 Hz, 1H), 4.92 (p, J = 7.1 Hz, 1H), 4.53 (d, J = 9.3 Hz, 1H), 4.43 (t, J = 8.0 Hz, 1H), 4.29 (s, 1H), 4.12 (s, 1H), 3.61 (d, J = 4.2 Hz, 2H), 2.74-2.70 (m, 2H), 2.46 (s, 3H), 2.37-2.29 (m, 1H), 2.21-2.17 (m, 3H), 2.03-1.98 (m, 2H), 1.88-1.74 (m, 2H), 1.58-1.52 (m, 3H), 1.43-1.35 (m, 12H), 1.27-1.23 (m, 1H), 0.94 (s, 9H) |

TABLE 47-continued

| Characterization data for intermediates prepare according to the procedure above. | | | | |
|---|---|---|---|---|
| Intermediate | Structure | Chemical Name | MS: [(M + 1)]$^+$ | $^1$H-NMR |
| G147 | 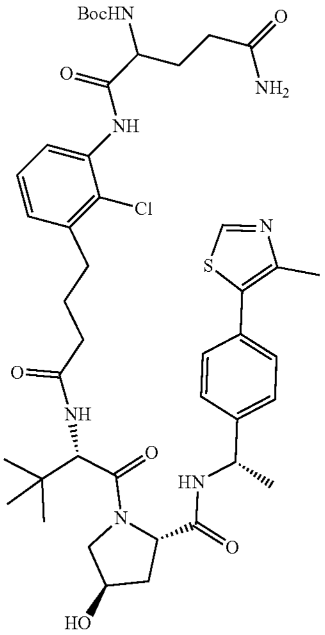 [SMILES: Cc1ncsc1-c1ccc([C@H](C)NC(=O)[C@@H]2C[C@@H](O)CN2C(=O)[C@@H](NC(=O)CCCc2cccc(NC(=O)C(CCC(N)=O)NC(=O)OC(C)(C)C)c2Cl)C(C)(C)C)cc1] | tert-butyl N-[(1S)-3-carbamoyl-1-[[2-chloro-3-(3-[[(2S)-1-[(2S,4R)-4-hydroxy-2-[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]propyl)phenyl]carbamoyl]propyl]carbamate | 868.35 | (400 MHz, DMSO-$d_6$) δ 9.32 (s, 1H), 8.99 (s, 1H), 8.38 (d, J = 7.7 Hz, 1H), 7.90 (d, J = 9.3 Hz, 1H), 7.75 (d, J = 8.1 Hz, 1H), 7.44 (d, J = 8.3 Hz, 2H), 7.38 (d, J = 8.3 Hz, 2H), 7.30 (d, J = 9.6 Hz, 2H), 7.26 (d, J = 8.1 Hz, 1H), 7.15-7.08 (m, 1H), 6.81 (s, 1H), 5.10 (s, 1H), 4.92 (p, J = 6.9 Hz, 1H), 4.55 (d, J = 9.2 Hz, 1H), 4.43 (t, J = 8.0 Hz, 1H), 4.29 (s, 1H), 4.13-4.09 (m, 1H), 3.62 (s, 2H), 2.72-2.68 (m, 2H), 2.46 (s, 3H), 2.35-2.31 (m, 1H), 2.23-2.19 (m, 2H), 2.01 (s, 1H), 1.83-1.79 (m, 4H), 1.43-1.35 (m, 12H), 1.33-1.23 (m, 2H), 0.95 (s, 9H) |
| G148 | 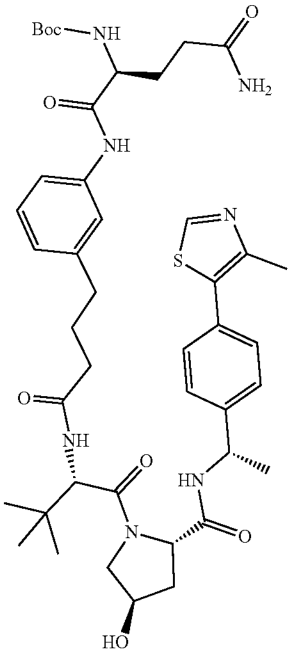 [SMILES: Cc1ncsc1-c1ccc([C@H](C)NC(=O)[C@@H]2C[C@@H](O)CN2C(=O)[C@@H](NC(=O)CCCc2cccc(NC(=O)[C@H](CCC(N)=O)NC(=O)OC(C)(C)C)c2)C(C)(C)C)cc1] | tert-butyl N-[(1S)-3-carbamoyl-1-[[3-(3-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]propyl)phenyl]carbamoyl]propyl]carbamate | 834.35 | (400 MHz, DMSO-$d_6$) δ 9.96 (s, 1H), 8.99 (s, 1H), 8.41 (d, J = 7.8 Hz, 1H), 8.26 (s, 1H), 7.87 (d, J = 9.3 Hz, 1H), 7.44 (d, J = 7.9 Hz, 4H), 7.39 (d, J = 8.3 Hz, 2H), 7.33 (d, J = 3.5 Hz, 1H), 7.21 (t, J = 7.7 Hz, 1H), 7.04 (d, J = 7.8 Hz, 1H), 6.88 (d, J = 7.7 Hz, 1H), 6.80 (s, 1H), 5.76 (s, 1H), 4.93 (p, J = 7.2 Hz, 1H), 4.54 (d, J = 9.3 Hz, 1H), 4.44 (t, J = 8.0 Hz, 1H), 4.29 (p, J = 3.2 Hz, 1H), 4.05 (q, J = 7.5 Hz, 1H), 3.63 (d, J = 3.2 Hz, 2H), 2.55 (d, J = 2.7 Hz, 1H), 2.46 (s, 3H), 2.29-2.25 (m, 1H), 2.18-2.15 (m, 3H), 2.02-1.99 (m, 1H), 1.96-1.86 (m, 1H), 1.85-1.71 (m, 4H), 1.38-1.21 (m, 12H), 0.95 (s, 9H) |

TABLE 47-continued

| Inter-me-diate | Structure | Chemical Name | MS: [(M + 1)]$^+$ | $^1$H-NMR |
|---|---|---|---|---|
| Characterization data for intermediates prepare according to the procedure above. | | | | |
| G149 | 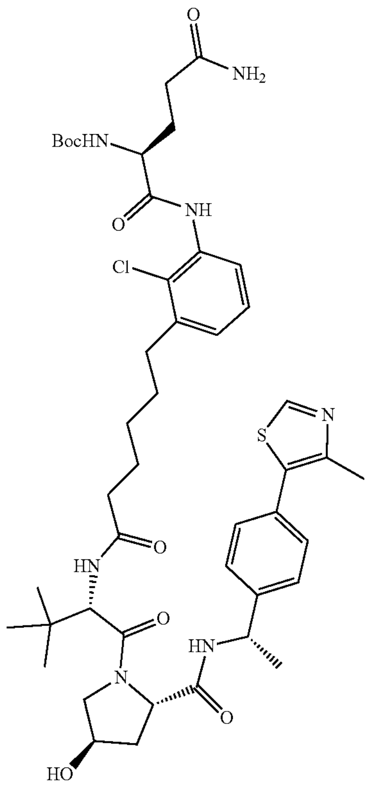 [SMILES: Cc1ncsc1-c1ccc([C@H](C)NC(=O)[C@@H]2C[C@@H](O)CN2C(=O)[C@@H](NC(=O)CCCCCc2cccc(NC(=O)[C@H](CCC(N)=O)NC(=O)OC(C)(C)C)c2Cl)C(C)(C)C)cc1] | tert-butyl N-[(1S)-3-carbamoyl-1-[[2-chloro-3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenyl]carbamoyl]propyl]carbamate | 896.45 | (300 MHz, DMSO-$d_6$) δ 9.60 (s, 1H), 9.00 (d, J = 1.2 Hz, 1H), 8.39 (d, J = 7.7 Hz, 1H), 7.78 (dd, J = 18.0, 8.8 Hz, 2H), 7.43 (q, J = 8.1 Hz, 4H), 7.32 (s, 1H), 7.15-7.01 (m, 3H), 6.82 (s, 1H), 5.12 (d, J = 3.5 Hz, 1H), 4.95 (t, J = 7.3 Hz, 1H), 4.53 (d, J = 9.2 Hz, 1H), 4.45 (t, J = 8.0 Hz, 1H), 4.36-4.24 (m, 1H), 4.20-4.15 (m, 1H), 3.63 (s, 2H), 3.36 (d, J = 1.2 Hz, 2H), 2.61 (t, J = 7.7 Hz, 2H), 2.48 (s, 3H), 2.31-2.11 (m, 3H), 2.10-1.88 (m, 1H), 1.88-1.71 (m, 2H), 1.63-1.48 (m, 2H), 1.46-1.22 (m, 14H), 0.95 (s, 9H) |
| G150 | 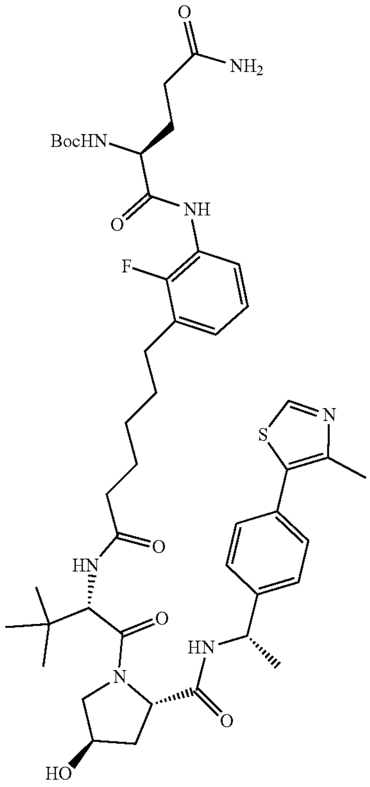 [SMILES: Cc1ncsc1-c1ccc([C@H](C)NC(=O)[C@@H]2C[C@@H](O)CN2C(=O)[C@@H](NC(=O)CCCCCc2cccc(NC(=O)[C@H](CCC(N)=O)NC(=O)OC(C)(C)C)c2F)C(C)(C)C)cc1] | tert-butyl N-[(1S)-3-carbamoyl-1-[[2-fluoro-3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenyl]carbamoyl]propyl]carbamate | 880.09 | (300 MHz, DMSO-$d_6$) δ 9.32 (s, 1H), 9.00 (d, J = 1.3 Hz, 1H), 8.39 (d, J = 7.7 Hz, 1H), 7.78 (dd, J = 18.1, 8.6 Hz, 2H), 7.49-7.36 (m, 5H), 7.32-7.25 (m, 2H), 7.14 (d, J = 7.5 Hz, 1H), 6.82 (s, 1H), 5.12 (s, 1H), 5.01-4.86 (m, 1H), 4.54 (d, J = 9.1 Hz, 1H), 4.44 (t, J = 8.0 Hz, 1H), 4.30 (s, 1H), 4.17-4.11 (m, 1H), 2.71 (t, J = 7.8 Hz, 2H), 2.48 (s, 3H), 2.34-2.12 (m, 3H), 2.07-1.96 (m, 1H), 1.86-1.77 (m, 2H), 1.62-1.50 (m, 4H), 1.46-1.20 (m, 18H), 0.95 (s, 9H) |

TABLE 47-continued

| Characterization data for intermediates prepare according to the procedure above. | | | | |
|---|---|---|---|---|
| Inter-me-diate | Structure | Chemical Name | MS: [(M + 1)]+ | $^1$H-NMR |
| G151 | 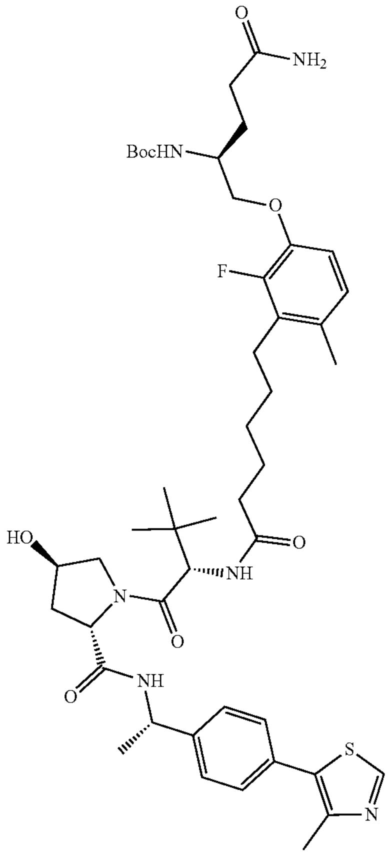 [SMILES: Cc1ccc(OC[C@H](CCC(N)=O)NC(=O)OC(C)(C)C)c(F)c1CCCCCC(=O)N[C@H](C(=O)N1C[C@H](O)C[C@H]1C(=O)N[C@@H](C)c1ccc(-c2scnc2C)cc1)C(C)(C)C] | tert-butyl N-[(2S)-4-carbamoyl-1-[2-fluoro-3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)-4-methylphenoxy]butan-2-yl]carbamate | 881.40 | (400 MHz, DMSO-$d_6$) δ 8.99 (s, 1H), 8.38 (d, J = 7.8 Hz, 1H), 7.80 (d, J = 9.3 Hz, 1H), 7.44 (d, J = 8.3 Hz, 2H), 7.45-7.31 (m, 2H), 7.27 (s, 1H), 6.92-6.85 (m, 2H), 6.82 (d, J = 8.5 Hz, 1H), 6.74 (s, 1H), 5.10 (d, J = 3.6 Hz, 1H), 4.92 (p, J = 7.3 Hz, 1H), 4.52 (d, J = 9.3 Hz, 1H), 4.43 (t, J = 8.0 Hz, 1H), 4.28 (s, 1H), 3.89-3.85 (m, 2H), 3.75-3.68 (m, 1H), 3.61 (d, J = 4.1 Hz, 2H), 2.58-2.54 (m, 2H), 2.46 (s, 3H), 2.34-2.23 (m, 1H), 2.21 (s, 3H), 2.17-2.06 (m, 3H), 2.05-1.97 (m, 2H), 1.88-1.74 (m, 2H), 1.64-1.44 (m, 5H), 1.38 (s, 9H), 1.36-1.14 (m, 4H), 0.93 (s, 9H) |

TABLE 47-continued

| Characterization data for intermediates prepare according to the procedure above. | | | | |
|---|---|---|---|---|
| Intermediate | Structure | Chemical Name | MS: [(M + 1)]+ | $^1$H-NMR |
| G152 | 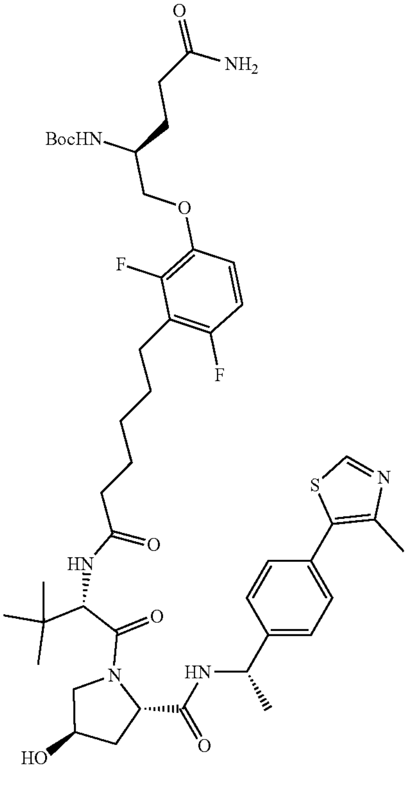 [SMILES: Cc1ncsc1-c1ccc([C@H](C)NC(=O)[C@@H]2C[C@@H](O)CN2C(=O)[C@@H](NC(=O)CCCCCc2c(F)ccc(OC[C@H](CCC(N)=O)NC(=O)OC(C)(C)C)c2F)C(C)(C)C)cc1] | tert-butyl N-[(2S)-4-carbamoyl-1-[2,4-difluoro-3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenoxy]butan-2-yl]carbamate | 885.40 | (400 MHz, DMSO-$d_6$) δ 8.99 (s, 1H), 8.38 (d, J = 7.8 Hz, 1H), 7.79 (d, J = 9.3 Hz, 1H), 7.44 (d, J = 8.3 Hz, 2H), 7.45-7.31 (m, 2H), 7.27 (s, 1H), 7.05-7.01 (m, 1H), 6.97-6.95 (m, 1H), 6.84 (d, J = 8.6 Hz, 1H), 6.74 (s, 1H), 5.10 (d, J = 3.5 Hz, 1H), 4.92 (p, J = 7.0 Hz, 1H), 4.51 (d, J = 9.3 Hz, 1H), 4.42 (t, J = 8.0 Hz, 1H), 4.28 (s, 1H), 3.90 (d, J = 6.0 Hz, 2H), 3.76-3.67 (m, 1H), 3.66-3.55 (m, 2H), 2.59 (t, J = 7.5 Hz, 2H), 2.46 (s, 3H), 2.32-2.20 (m, 1H), 2.17-2.06 (m, 3H), 2.04-1.98 (m, 1H), 1.86-1.74 (m, 2H), 1.64-1.43 (m, 5H), 1.39 (s, 9H), 1.35-1.20 (m, 4H), 1.10-1.02 (m, 1H), 0.93 (s, 9H) |
| G153 | 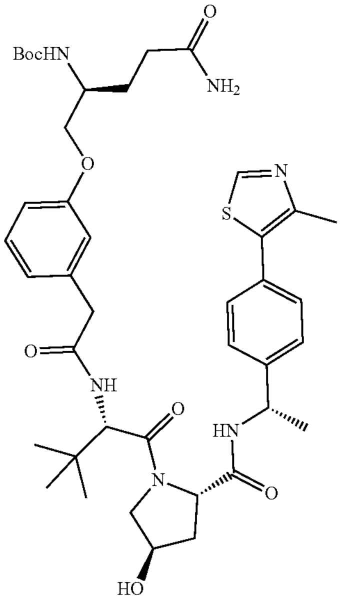 [SMILES: Cc1ncsc1-c1ccc([C@H](C)NC(=O)[C@@H]2C[C@@H](O)CN2C(=O)[C@@H](NC(=O)Cc2cccc(OC[C@H](CCC(N)=O)NC(=O)OC(C)(C)C)c2)C(C)(C)C)cc1] | tert-butyl N-[(2S)-4-carbamoyl-1-[3-([[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]methyl)phenoxy]butan-2-yl]carbamate | 793.30 | (400 MHz, DMSO-$d_6$) δ 8.99 (s, 1H), 8.40 (d, J = 7.7 Hz, 1H), 8.03 (d, J = 9.2 Hz, 1H), 7.48-7.31 (m, 4H), 7.28 (s, 1H), 7.19 (t, J = 7.9 Hz, 1H), 8.99 (s, 1H), 6.94-6.67 (m, 5H), 5.11 (d, J = 3.5 Hz, 1H), 4.99-4.87 (m, 1H), 4.52-4.39 (m, 2H), 4.30-4.24 (m, 1H), 3.90-3.67 (m, 3H), 3.66-3.54 (m, 3H), 3.40 (d, J = 13.7 Hz, 1H), 2.46 (s, 3H), 2.18-2.09 (m, 6.4 Hz, 2H), 2.03-1.99 (m, 1H), 1.83-1.70 (m, 2H), 1.68-1.54 (m, 1H), 1.42-1.38 (m, 10H), 1.38-1.36 (s, 2H), 0.92 (s, 9H) |

TABLE 47-continued

| Characterization data for intermediates prepare according to the procedure above. | | | | |
|---|---|---|---|---|
| Inter-me-diate | Structure | Chemical Name | MS: [(M + 1)]+ | $^1$H-NMR |
| G154 | 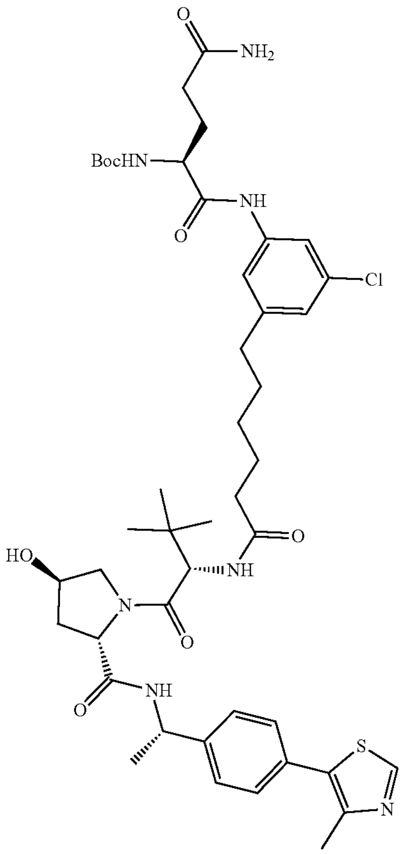 [SMILES: Cc1ncsc1-c1ccc([C@H](C)NC(=O)[C@@H]2C[C@@H](O)CN2C(=O)[C@@H](NC(=O)CCCCCc2cc(Cl)cc(NC(=O)[C@H](CCC(N)=O)NC(=O)OC(C)(C)C)c2)C(C)(C)C)cc1] | tert-butyl N-[(1S)-3-carbamoyl-1-[[3-chloro-5-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenyl]carbamoyl]propyl]carbamate | 896.45 | (300 MHz, DMSO-$d_6$) δ 10.07 (s, 1H), 8.97 (s, 1H), 8.35 (d, J = 7.8 Hz, 1H), 7.77 (d, J = 9.2 Hz, 1H), 7.64 (d, J = 2.3 Hz, 1H), 7.40 (q, J = 8.3 Hz, 4H), 7.28 (s, 2H), 7.06 (d, J = 7.5 Hz, 1H), 6.95 (t, J = 1.7 Hz, 1H), 6.77 (s, 1H), 5.09 (d, J = 3.5 Hz, 1H), 4.97-4.86 (m, 1H), 4.51 (d, J = 9.3 Hz, 1H), 4.42 (t, J = 8.0 Hz, 1H), 4.28 (s, 1H), 4.00 (d, J = 6.9 Hz, 1H), 3.60 (s, 2H), 2.53 (d, J = 7.5 Hz, 2H), 2.45 (s, 3H), 2.30-2.10 (m, 4H), 2.01-1.74 (m, 4H), 1.65-1.42 (m, 4H), 1.41-1.35 (m, 11H), 1.33-1.19 (m, 4H), 0.92 (s, 9H) |

TABLE 47-continued

| Characterization data for intermediates prepare according to the procedure above. | | | | |
|---|---|---|---|---|
| Inter-me-diate | Structure | Chemical Name | MS: [(M + 1)]$^+$ | $^1$H-NMR |
| G155 | 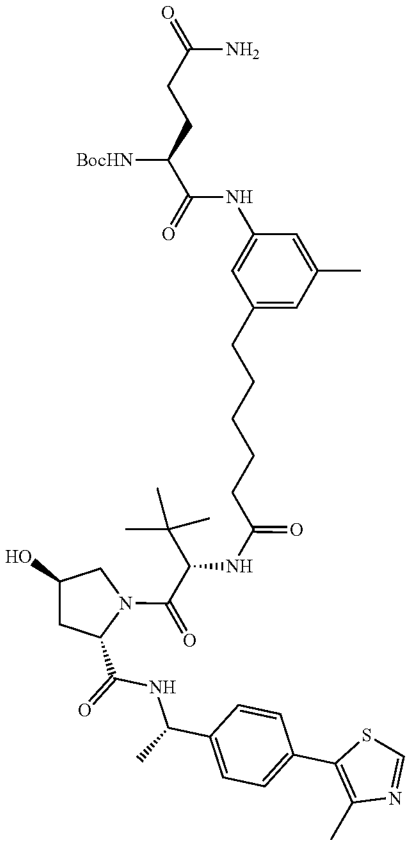 [SMILES: Cc1cc(CCCCCC(=O)N[C@H](C(=O)N2C[C@H](O)C[C@H]2C(=O)N[C@@H](C)c2ccc(-c3scnc3C)cc2)C(C)(C)C)cc(NC(=O)[C@H](CCC(N)=O)NC(=O)OC(C)(C)C)c1] | Tert-butyl N-[(1S)-3-carbamoyl-1-[[3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)-5-methylphenyl]carbamoyl]propyl] carbamate | 876.40 | (300 MHz, DMSO-$d_6$) δ 9.78 (s, 1H), 9.00 (s, 1H), 8.37 (d, J = 7.7 Hz, 1H), 7.79 (d, J = 9.2 Hz, 1H), 7.49-7.38 (m, 4H), 7.29-7.18 (m, 3H), 7.00 (d, J = 7.8 Hz, 1H), 6.79-6.72 (m, 2H), 5.10 (d, J = 3.5 Hz, 1H), 5.01-4.83 (m, 1H), 4.63-4.36 (m, 2H), 4.30 (s, 1H), 4.06-3.97 (m, 1H), 3.62 (d, J = 3.2 Hz, 2H), 3.04-2.45 (m, 6H), 2.26 (s, 3H), 2.18-2.13 (m, 6H), 1.95-1.70 (m, 2H), 1.62-1.51 (m, 4H), 1.39 (s, 9H), 1.32-1.24 (m, 4H), 0.95 (s, 9H) |

TABLE 47-continued

| Characterization data for intermediates prepare according to the procedure above. | | | | |
|---|---|---|---|---|
| Intermediate | Structure | Chemical Name | MS: [(M + 1)]+ | 1H-NMR |
| G156 | 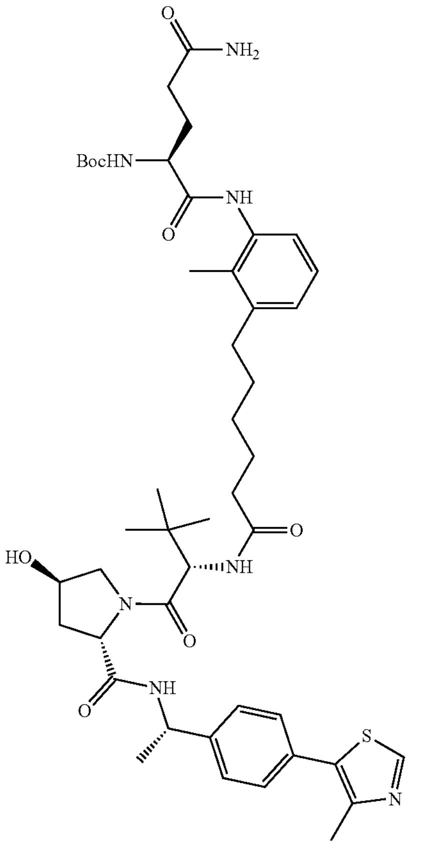 [SMILES: Cc1ncsc1-c1ccc([C@H](C)NC(=O)[C@@H]2C[C@@H](O)CN2C(=O)[C@@H](NC(=O)CCCCCc2cccc(NC(=O)[C@H](CCC(N)=O)NC(=O)OC(C)(C)C)c2C)C(C)(C)C)cc1] | tert-butyl N-[(1S)-3-carbamoyl-1-[[3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)-2-methylphenyl]carbamoyl]propyl]carbamate | 876.50 | (300 MHz, DMSO-$d_6$) δ 9.30 (s, 1H), 9.00 (s, 1H), 8.40 (d, J = 7.7 Hz, 1H), 7.82 (d, J = 9.2 Hz, 1H), 7.47-7.34 (m, 6H), 7.23-6.93 (m, 4H), 6.82 (s, 1H), 5.13 (d, J = 3.5 Hz, 1H), 4.96-4.90 (m, 1H), 4.60-4.38 (m, 2H), 4.30 (s, 1H), 4.08 (d, J = 6.8 Hz, 1H), 3.63 (d, J = 3.3 Hz, 2H), 2.60 (d, J = 7.6 Hz, 2H), 2.47 (s, 3H), 2.36-1.88 (m, 9H), 1.85-1.81 (m, 2H), 1.67-1.46 (m, 4H), 1.41 (d, J = 3.8 Hz, 11H), 1.39-1.14 (m, 2H), 0.95 (s, 9H) |
| G157 | 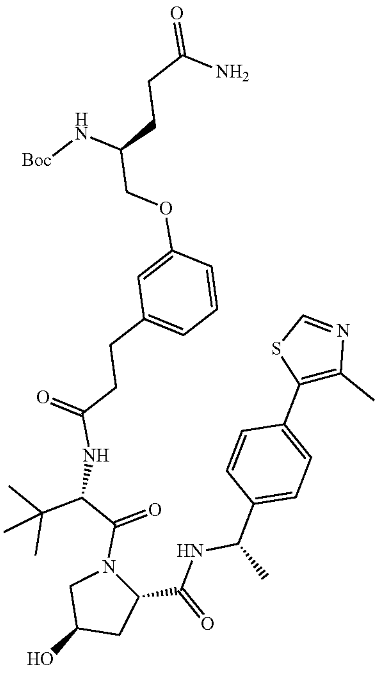 [SMILES: Cc1ncsc1-c1ccc([C@H](C)NC(=O)[C@@H]2C[C@@H](O)CN2C(=O)[C@@H](NC(=O)CCc2cccc(OC[C@H](CCC(N)=O)NC(=O)OC(C)(C)C)c2)C(C)(C)C)cc1] | tert-butyl N-[(2S)-4-carbamoyl-1-[3-(2-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]ethyl)phenoxy]butan-2-yl]carbamate | 807.3 | (400 MHz, DMSO-$d_6$) δ 8.99 (s, 1H), 8.39 (d, J = 7.8 Hz, 1H), 7.89 (d, J = 9.3 Hz, 1H), 7.44 (d, J = 8.1 Hz, 2H), 7.39 (d, J = 8.3 Hz, 2H), 7.28 (s, 1H), 7.16 (t, J = 7.8 Hz, 1H), 6.86-6.70 (m, 5H), 5.76 (s, 1H), 5.17-5.09 (m, 1H), 4.93 (p, J = 7.2 Hz, 1H), 4.53 (d, J = 9.3 Hz, 1H), 4.44 (t, J = 8.0 Hz, 1H), 4.29 (s, 1H), 3.84 (qd, J = 9.6, 5.8 Hz, 2H), 3.72 (dp, J = 9.0, 4.9 Hz, 1H), 3.62 (d, J = 3.4 Hz, 2H), 3.35-3.32 (m, 4H), 2.85-2.69 (m, 2H), 2.60-2.58 (m, 1H), 2.46 (s, 3H), 2.20-1.99 (m, 4H), 1.82-1.76 (m, 2H), 1.62-1.57 (m, 1H), 1.44 (s, 9H), 0.90 (s, 9H) |

TABLE 47-continued

Characterization data for intermediates prepare according to the procedure above.

| Inter-me-diate | Structure | Chemical Name | MS: [(M + 1)]$^+$ | $^1$H-NMR |
|---|---|---|---|---|
| G158 | 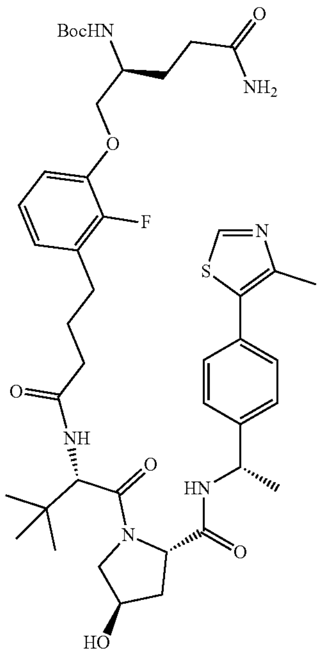 | tert-butyl N-[(2S)-4-carbamoyl-1-[2-fluoro-3-(3-[[(2S)-1-[(2S,4R)-4-hydroxy-2-[[(1S)-1-[4-(4-methyl-1,3-thiazol-5-yl)phenyl]ethyl] carbamoyl]pyrrolidin-1-yl]-3,3-dimethyl-1-oxobutan-2-yl]carbamoyl]propyl) phenoxy]butan-2-yl]carbamate | 839.40 | (300 MHz, DMSO-$d_6$) δ 9.00 (s, 1H), 8.38 (d, J = 7.8 Hz, 1H), 7.87 (d, J = 9.2 Hz, 1H), 7.42 (q, J = 8.3 Hz, 4H), 7.29 (s, 1H), 7.03-6.98 (m, 2H), 6.84-6.80 (m, 2H), 6.74 (s, 1H), 5.10 (d, J = 3.6 Hz, 1H), 4.98-4.88 (m, 1H), 4.54 (d, J = 9.3 Hz, 1H), 4.44 (t, J = 8.0 Hz, 1H), 4.29 (s, 1H), 3.93 (d, J = 6.0 Hz, 2H), 3.75-3.73 (m, 1H), 3.64-3.61 (m, 2H), 2.58 (t, J = 7.6 Hz, 2H), 2.47 (s, 3H), 2.32-2.28 (m, 1H), 2.21-2.16 (m, 2H), 2.07-1.97 (m, 1H), 1.87-1.69 (m, 5H), 1.64-1.62 (m, 1H), 1.40 (s, 9H), 0.96 (s, 9H) |
| G159 | 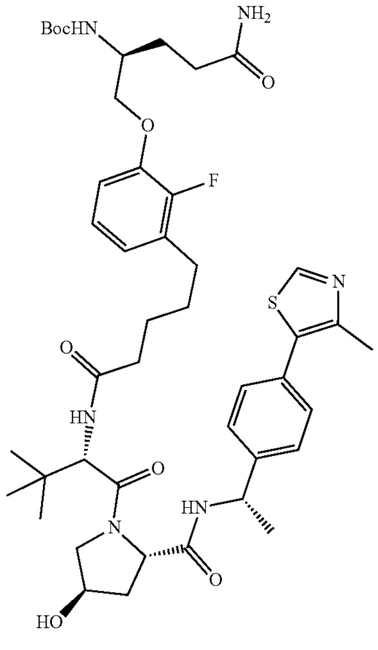 [SMILES: Cc1ncsc1-c1ccc([C@H](C)NC(=O)[C@@H]2C[C@@H](O)CN2C(=O)[C@@H](NC(=O)CCCCc2cccc(OC[C@H](CCC(N)=O)NC(=O)OC(C)(C)C)c2F)C(C)(C)C)cc1] | tert-butyl N-[(2S)-4-carbamoyl-1-[2-fluoro-3-(4-[[(2S)-1-[(2S,4R)-4-hydroxy-2-[(1S)-1-[4-(4-methyl-1,3-thiazol-5-yl)phenyl]ethyl] carbamoyl]pyrrolidin-1-yl]-3,3-dimethyl-1-oxobutan-2-yl]carbamoyl]butyl) phenoxy]butan-2-yl]carbamate | 853.35 | (400 MHz, DMSO-$d_6$) δ 9.00 (s, 1H), 8.39 (d, J = 7.8 Hz, 1H), 7.84 (d, J = 9.3 Hz, 1H), 7.45 (d, J = 8.3 Hz, 2H), 7.40 (d, J = 8.4 Hz, 2H), 7.28 (s, 1H), 7.06-6.96 (m, 2H), 6.87-6.80 (m, 2H), 6.75 (s, 1H), 5.11 (d, J = 3.5 Hz, 1H), 4.94-4.92 (m, 1H), 4.53 (d, J = 9.3 Hz, 1H), 4.44 (t, J = 8.0 Hz, 1H), 4.30-4.28 (m, 1H), 3.92 (d, J = 6.1 Hz, 2H), 3.76-3.72 (m, 1H), 3.67-3.58 (m, 2H), 2.59 (t, J = 7.0 Hz, 2H), 2.47 (s, 3H), 2.33-2.29 (m, 1H), 2.18-2.13 (m, 4H), 2.03-2.01 (m, 1H), 1.86-1.83 (m, 2H), 1.65-1.46 (m, 6H), 1.40 (s, 9H), 1.35-1.33 (m, 1H), 0.95 (s, 9H) |

TABLE 47-continued

| Characterization data for intermediates prepare according to the procedure above. | | | | |
|---|---|---|---|---|
| Inter-me-diate | Structure | Chemical Name | MS: [(M + 1)]+ | $^1$H-NMR |
| G160 | 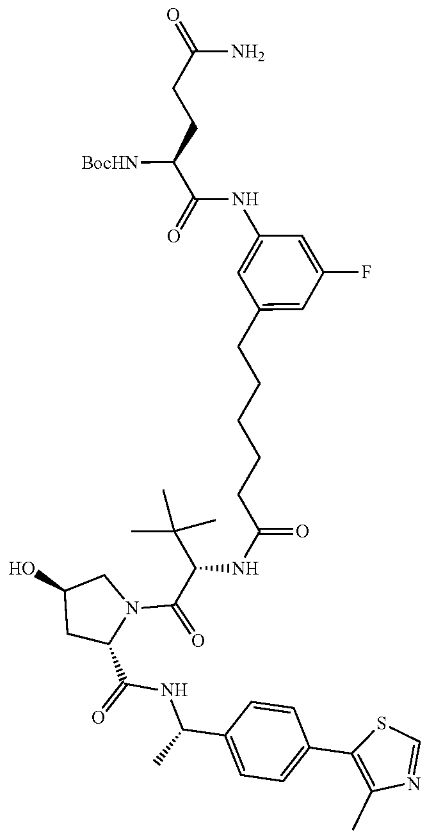 [SMILES: Cc1ncsc1-c1ccc([C@H](C)NC(=O)[C@@H]2C[C@@H](O)CN2C(=O)[C@@H](NC(=O)CCCCCc2cc(F)cc(NC(=O)[C@H](CCC(N)=O)NC(=O)OC(C)(C)C)c2)C(C)(C)C)cc1] | tert-butyl N-[(1S)-3-carbamoyl-1-[[3-fluoro-5-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenyl]carbamoyl]propyl]carbamate | 880.45 | (400 MHz, DMSO-$d_6$) δ 10.11 (s, 1H), 8.99 (s, 1H), 8.39 (d, J = 7.7 Hz, 1H), 7.80 (d, J = 9.2 Hz, 1H), 7.51-7.36 (m, 5H), 7.30 (s, 1H), 7.15 (s, 1H), 7.09 (d, J = 7.6 Hz, 1H), 6.80 (s, 1H), 6.73 (d, J = 9.5 Hz, 1H), 5.11 (s, 1H), 4.92-4.85 (m, 1H), 4.52 (d, J = 9.3 Hz, 1H), 4.42 (t, J = 8.0 Hz, 1H), 4.29 (s, 1H), 4.01 (q, J = 7.4 Hz, 1H), 3.64-3.59 (m, 2H), 3.35 (s, 2H), 2.56-2.54 (m, 2H), 2.46 (s, 3H), 2.24-2.08 (m, 2H), 2.06-1.70 (m, 4H), 1.58-1.48 (m, 4H), 1.39 (s, 9H), 1.37 (s, 2H), 1.28-1.24 (m, 3H), 0.93 (s, 9H) |

TABLE 47-continued

| Characterization data for intermediates prepare according to the procedure above. | | | | |
|---|---|---|---|---|
| Inter-me-diate | Structure | Chemical Name | MS: [(M + 1)]$^+$ | $^1$H-NMR |
| G161 | 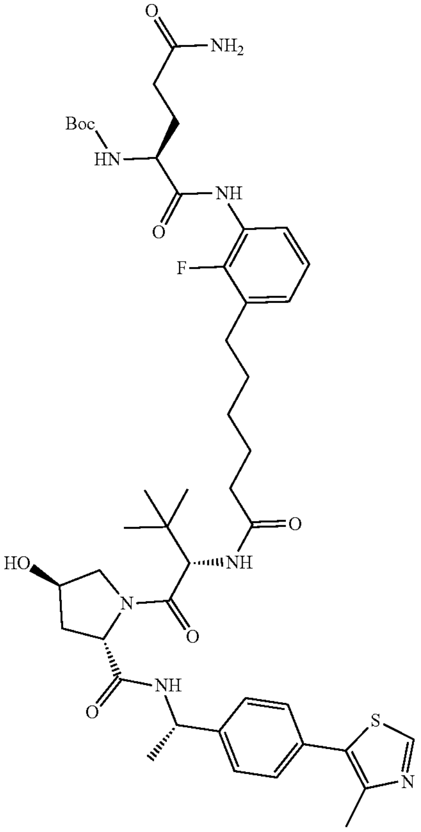 [SMILES: Cc1ncsc1-c1ccc([C@H](C)NC(=O)[C@@H]2C[C@@H](O)CN2C(=O)[C@@H](NC(=O)CCCCCc2cccc(NC(=O)[C@H](CCC(N)=O)NC(=O)OC(C)(C)C)c2F)C(C)(C)C)cc1] | tert-butyl N-(4-carbamoyl-1-[[2-fluoro-3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenyl]amino]butan-2-yl)carbamate | 866.40 | (400 MHz, DMSO-$d_6$) δ 8.99 (s, 1H), 8.37 (d, J = 7.8 Hz, 1H), 7.79 (d, J = 9.2 Hz, 1H), 7.44 (d, J = 8.3 Hz, 2H), 7.39 (d, J = 8.2 Hz, 2H), 7.24 (s, 1H), 6.85 (t, J = 7.8 Hz, 2H), 6.79 (d, J = 8.4 Hz, 1H), 6.71 (s, 1H), 6.60 (t, J = 8.2 Hz, 1H), 6.41 (t, J = 7.0 Hz, 1H), 5.22 (s, 1H), 5.10 (d, J = 3.6 Hz, 1H), 4.92 (p, J = 7.5 Hz, 1H), 4.52 (d, J = 9.3 Hz, 1H), 4.43 (t, J = 8.0 Hz, 1H), 4.28 (s, 1H), 3.64-3.56 (m, 6H), 3.12-2.99 (m, 1H), 3.06-3.02 (m, 1H), 2.46 (s, 3H), 2.32-2.20 (m, 3H), 2.17-2.07 (m, 4H), 2.09-1.97 (m, 1H), 2.03-1.99 (m, 1H), 1.85-1.73 (m, 1H), 1.57-1.53 (m, 1H), 1.54-1.50 (m, 5H), 1.39 (d, J = 13.2 Hz, 2H), 1.33-1.21 (m, 6H), 0.94 (s, 9H) |

TABLE 47-continued

| Characterization data for intermediates prepare according to the procedure above. | | | | |
|---|---|---|---|---|
| Inter-me-diate | Structure | Chemical Name | MS: [(M + 1)]$^+$ | $^1$H-NMR |
| G162 | 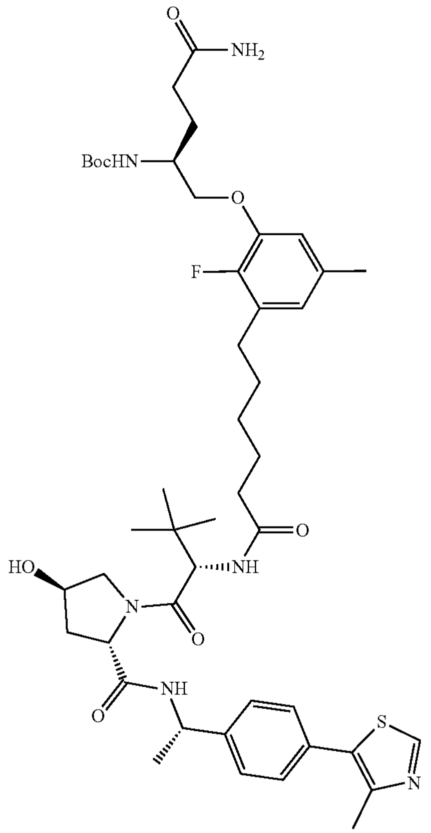 | tert-butyl N-[(2S)-4-carbamoyl-1-[2-fluoro-3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)-5-methylphenoxy]butan-2-yl]carbamate | 881.40 | (300 MHz, DMSO-$d_6$) δ 8.97 (s, 1H), 8.35 (d, J = 7.8 Hz, 1H), 7.77 (d, J = 9.2 Hz, 1H), 7.40 (q, J = 8.2 Hz, 4H), 7.25 (s, 1H), 6.79 (t, J = 7.5 Hz, 2H), 6.72 (s, 1H), 6.59 (dd, J = 6.2, 2.0 Hz, 1H), 5.08 (d, J = 3.6 Hz, 1H), 4.97-4.86 (m, 1H), 4.51 (d, J = 9.3 Hz, 1H), 4.42 (t, J = 8.0 Hz, 1H), 4.28 (s, 1H), 3.88 (d, J = 5.9 Hz, 2H), 3.78-3.66 (m, 1H), 3.64-3.57 (m, 2H), 2.45 (s, 3H), 2.33-2.24 (m, 1H), 2.22 (s, 3H), 2.17-2.08 (m, 3H), 2.06 (d, J = 0.9 Hz, 3H), 2.05-1.94 (m, 2H), 1.87-1.72 (m, 2H), 1.69-1.43 (m, 5H), 1.38 (s, 9H), 1.35 (s, 3H), 0.92 (s, 9H) |

TABLE 47-continued

Characterization data for intermediates prepare according to the procedure above.

| Intermediate | Structure | Chemical Name | MS: [(M + 1)]+ | 1H-NMR |
|---|---|---|---|---|
| G163 | 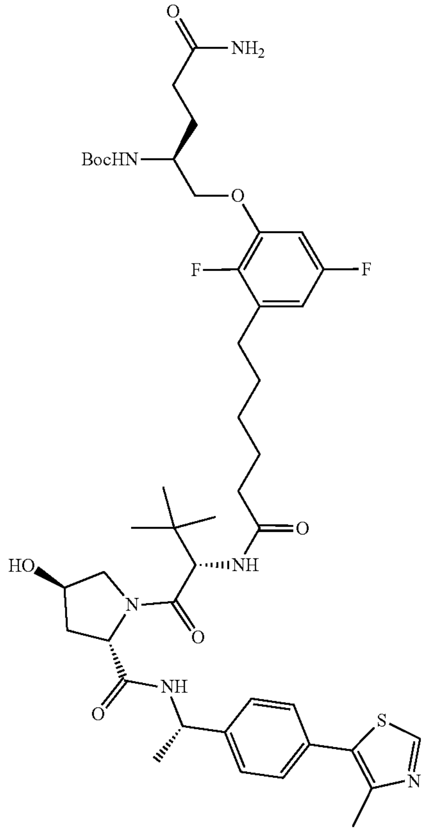 [SMILES: Cc1ncsc1-c1ccc([C@H](C)NC(=O)[C@@H]2C[C@@H](O)CN2C(=O)[C@@H](NC(=O)CCCCCc2cc(F)cc(OC[C@H](CCC(N)=O)NC(=O)OC(C)(C)C)c2F)C(C)(C)C)cc1] | tert-butyl N-[(2S)-4-carbamoyl-1-[2,5-difluoro-3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenoxy]butan-2-yl]carbamate | 885.35 | (400 MHz, CD3OD) δ 8.87 (s, 1H), 7.47-7.33 (m, 4H), 6.79-6.70 (m, 1H), 6.59-6.50 (m, 1H), 5.00 (q, J = 6.8 Hz, 1H), 4.64-4.53 (m, 2H), 4.43 (br, 1H), 3.97 (d, J = 5.4 Hz, 2H), 3.87 (d, J = 10.9 Hz, 2H), 3.74 (dd, J = 11.0, 3.9 Hz, 1H), 2.62 (t, J = 7.5 Hz, 2H), 2.47 (s, 3H), 2.39-2.12 (m, 4H), 2.04-1.90 (m, 1H), 1.85-1.73 (m, 1H), 1.70-1.54 (m, 5H), 1.50 (d, J = 7.0 Hz, 3H), 1.44 (s, 9H), 1.40-1.35 (m, 3H), 1.03 (s, 9H) |
| G164 | 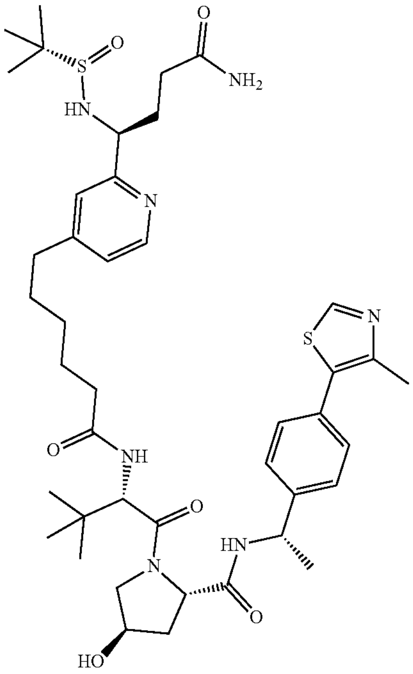 | (2S,4R)-1-[(2S)-2-(6-[2-[(1S)-3-carbamoyl-1-[(2-methylpropane-2-sulfinyl)amino]propyl]pyridin-4-yl]hexanamido)-3,3-dimethylbutanoyl]-4-hydroxy-N-[(1S)-1-[4-(4-methyl-1,3-thiazol-5-yl)phenyl]ethyl]pyrrolidine-2-carboxamide | 824.35 | (400 MHz, DMSO-$d_6$) δ 8.99 (s, 1H), 840-8.37 (t, J = 6.9 Hz, 2H), 7.81-7.79 (d, J = 9.3 Hz, 1H), 7.47-7.41 (m, 2H), 7.39-7.37 (d, J = 8.3 Hz, 2H), 7.31 (s, 1H), 7.20-7.10 (m, 2H), 6.85-6.77 (m, 1H), 5.75-5.74 (d, J = 5.5 Hz, 1H), 5.11-5.10 (d, J = 3.5 Hz, 1H), 4.96-4.89 (m, 1H), 4.53-4.50 (d, J = 9.4 Hz, 1H), 4.45-4.41 (t, J = 8.0 Hz, 1H), 4.30-4.27 (m, 1H), 4.25-4.21 (m, 1H), 3.61 (s, 1H), 2.70-2.67 (t, J = 7.5 Hz, 2H), 2.46 (s, 3H), 2.45-2.23 (m, 1H), 2.17-2.01 (m, 3H), 1.91-1.75 (m, 2H), 1.68-1.63 (m, 2H), 1.53-1.51 (m, 2H), 1.39-1.37 (d, J = 7.0 Hz, 3H), 1.31-1.23 (m, 2H), 1.20-1.16 (t, J = 7.1 Hz, 3H), 1.10 (s, 9H), 0.93 (s, 9H) |

TABLE 47-continued

| Characterization data for intermediates prepare according to the procedure above. | | | | |
|---|---|---|---|---|
| Inter-me-diate | Structure | Chemical Name | MS: [(M + 1)]$^+$ | $^1$H-NMR |
| G165 | 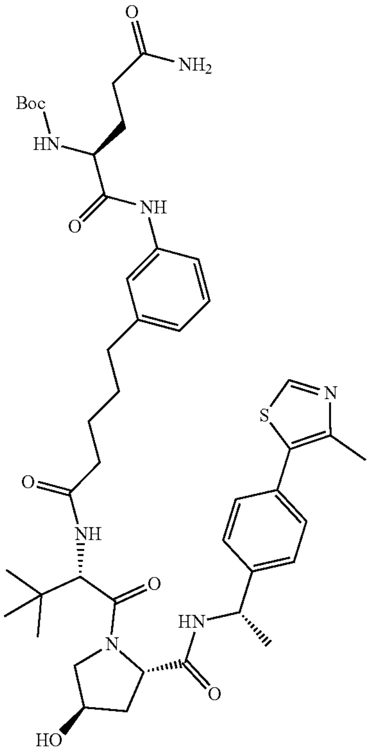 [SMILES: Cc1ncsc1-c1ccc([C@H](C)NC(=O)[C@@H]2C[C@@H](O)CN2C(=O)[C@@H](NC(=O)CCCCc2cccc(NC(=O)[C@H](CCC(N)=O)NC(=O)OC(C)(C)C)c2)C(C)(C)C)cc1] | tert-butyl N-[(1S)-3-carbamoyl-1-[[3-(4-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]butyl)phenyl]carbamoyl]propyl]carbamate | 848.65 | (300 MHz, DMSO-$d_6$) δ 9.84 (s, 1H), 8.98 (d, J = 3.6 Hz, 1H), 8.37-8.34 (m, 1H), 7.79 (d, J = 9.2 Hz, 1H), 7.43-7.36 (m, 6H), 7.29-7.17 (m, 2H), 7.05-6.69 (m, 3H), 5.08 (s, 1H), 4.96-4.87 (m, 1H), 4.51 (d, J = 9.5 Hz, 1H), 4.45-4.39 (m, 2H), 4.27 (s, 1H), 4.02 (s, 1H), 3.63-3.59 (m, 2H), 2.45 (d, J = 3.7 Hz, 3H), 2.28-2.14 (m, 4H), 2.00-1.79 (m, 5H), 1.57-1.50 (m, 4H), 1.38-1.30 (m, 12H), 0.93 (s, 9H) |
| G138 | 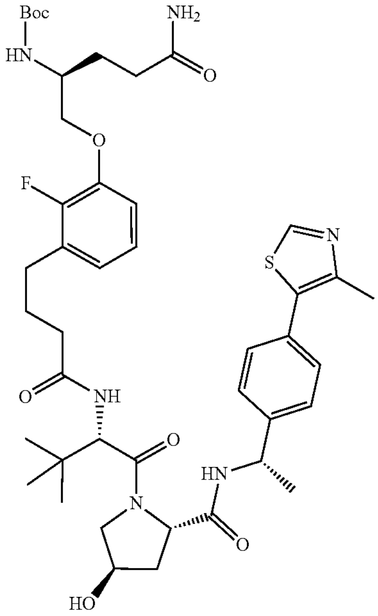 [SMILES: Cc1ncsc1-c1ccc([C@H](C)NC(=O)[C@@H]2C[C@@H](O)CN2C(=O)[C@@H](NC(=O)CCCc2cccc(OC[C@H](CCC(N)=O)NC(=O)OC(C)(C)C)c2F)C(C)(C)C)cc1] | tert-butyl N-[(2S)-4-carbamoyl-1-[2-fluoro-3-(3-[[(2S)-1-[(2S,4R)-4-hydroxy-2-[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]propyl)phenoxy]butan-2-yl]carbamate | 839.40 | (400 MHz, CD3OD) δ 8.91-8.89 (m, 1H), 7.48-7.41 (m, 4H), 7.03-6.93 (m, 2H), 6.85-6.82 (m, 1H), 5.03-5.01 (m, 1H), 4.66-4.64 (m, 1H), 4.61-4.56 (m, 1H), 4.47-4.42 (m, 1H), 4.02-3.99 (m, 2H), 3.90 (d, J = 10.9 Hz, 2H), 3.79-3.76 (m, 1H), 2.71-2.67 (m, 2H), 2.50 (s, 3H), 2.34-2.32 (m, 4H), 2.24-2.18 (m, 1H), 2.06-1.89 (m, 4H), 1.85-1.81 (m, 1H), 1.53 (d, J = 7.0 Hz, 3H), 1.46 (s, 9H), 1.05 (s, 9H) |

TABLE 47-continued

| Intermediate | Structure | Chemical Name | MS: [(M + 1)]$^+$ | $^1$H-NMR |
|---|---|---|---|---|
| Characterization data for intermediates prepare according to the procedure above. | | | | |
| G139 | 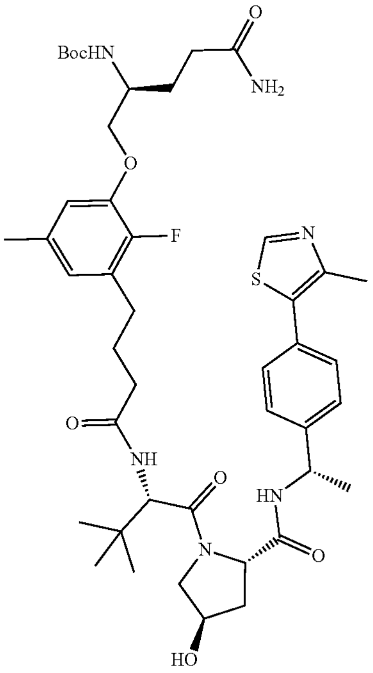 | tert-butyl N-[(2S)-4-carbamoyl-1-[2-fluoro-3-(3-[[(2S)-1-[(2S,4R)-4-hydroxy-2-[[(1S)-1-[4-(4-methyl-1,3-thiazol-5-yl)phenyl]ethyl] carbamoyl]pyrrolidin-1-yl]-3,3-dimethyl-1-oxobutan-2-yl]carbamoyl]propyl)-5-methylphenoxy] butan-2-yl]carbamate | 853.40 | (300 MHz, DMSO-$d_6$) δ 8.97 (s, 1H), 8.35 (d, J = 7.8 Hz, 1H), 7.84 (d, J = 9.2 Hz, 1H), 7.40 (q, J = 8.2 Hz, 4H), 7.25 (s, 1H), 6.83-6.76 (m, 2H), 6.72 (s, 1H), 6.59 (d, J = 6.1 Hz, 1H), 5.08 (s, 1H), 4.99-4.85 (m, 1H), 4.52 (d, J = 9.3 Hz, 1H), 4.42 (t, J = 8.0 Hz, 1H), 4.27 (s, 1H), 3.88 (d, J = 6.0 Hz, 2H), 3.78-3.66 (m, 1H), 3.64-3.56 (m, 2H), 2.45 (s, 3H), 2.28 (d, J = 6.9 Hz, 1H), 2.23 (s, 3H), 2.20-2.10 (m, 4H), 2.02-1.95 (m, 1H), 1.87-1.67 (m, 5H), 1.66-1.52 (m, 1H), 1.38 (s, 9H), 1.35 (s, 3H), 0.94 (s, 9H) |
| G140 | 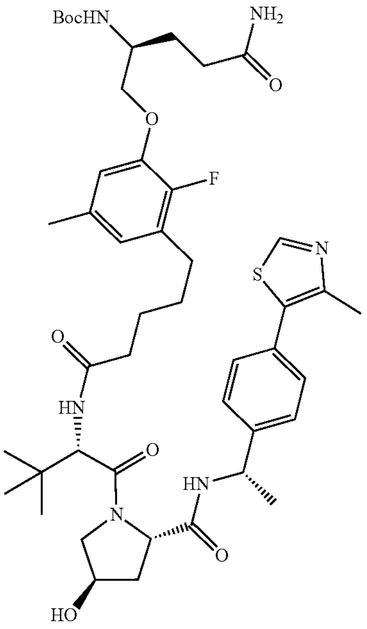 [SMILES: Cc1cc(CCCCC(=O)N[C@H](C(=O)N2C[C@H](O)C[C@H]2C(=O)N[C@@H](C)c2ccc(-c3scnc3C)cc2)C(C)(C)C)c(F)c(OC[C@H](CCC(N)=O)NC(=O)OC(C)(C)C)c1] | tert-butyl N-[(2S)-4-carbamoyl-1-[2-fluoro-3-(4-[[(2S)-1-[(2S,4R)-4-hydroxy-2-[[(1S)-1-[4-(4-methyl-1,3-thiazol-5-yl)phenyl]ethyl] carbamoyl]pyrrolidin-1-yl]-3,3-dimethyl-1-oxobutan-2-yl]carbamoyl]butyl)-5-methylphenoxy] butan-2-yl]carbamate | 867.45 | (300 MHz, DMSO-$d_6$) δ 9.00 (d, J = 1.4 Hz, 1H), 8.39 (d, J = 7.7 Hz, 1 H), 7.84 (d, J = 9.3 Hz, 1H), 7.50-7.37 (m, 4H), 7.28 (s, 1H), 6.81 (dd, J = 20.1, 11.0 Hz, 3H), 6.63 (d, J = 5.9 Hz, 1H), 5.12 (s, 1H), 5.01-4.88 (m, 1H), 4.57-4.39 (m, 2H), 4.30 (s, 1H), 3.90 (d, J = 5.9 Hz, 2H), 3.79-3.69 (m, 1H), 3.65-3.58 (m, 2H), 2.47 (s, 3H), 2.25 (s, 3H), 2.19-2.12 (m, 3H), 2.09 (d, J = 1.5 Hz, 3H), 2.06-1.98 (m, 1H), 1.88-1.73 (m, 3H), 1.67-1.58 (m, 1H), 1.56-1.44 (m, 4H), 1.40 (s, 9H), 1.37 (s, 3H), 0.95 (s, 9H) |

TABLE 47-continued

| Characterization data for intermediates prepare according to the procedure above. | | | | |
|---|---|---|---|---|
| Inter-me-diate | Structure | Chemical Name | MS: [(M + 1)]$^+$ | $^1$H-NMR |
| G141 | 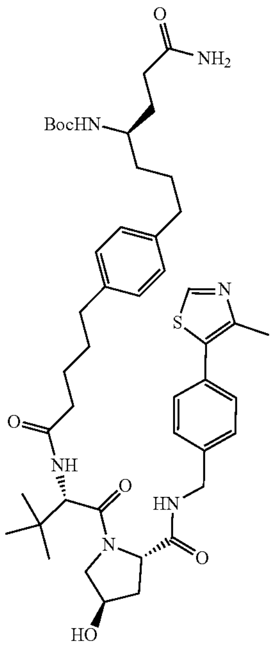 [SMILES: Cc1ncsc1-c1ccc(CNC(=O)[C@@H]2C[C@@H](O)CN2C(=O)[C@@H](NC(=O)CCCCc2ccc(CCC[C@H](CCC(N)=O)NC(=O)OC(C)(C)C)cc2)C(C)(C)C)cc1] | tert-butyl N-[(3R)-1-carbamoyl-6-[4-(4-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]butyl)phenyl]hexan-3-yl]carbamate | 847.50 | $^1$H NMR (300 MHz, DMSO-$d_6$) δ 9.00 (s, 1H), 8.39 (d, J = 7.8 Hz, 1H), 7.83 (d, J = 9.2 Hz, 1H), 7.48-7.35 (m, 4H), 7.23 (s, 1H), 7.08 (s, 4H), 6.69 (s, 1H), 6.60 (d, J = 9.2 Hz, 1H), 5.11 (d, J = 3.6 Hz, 1H), 5.01-4.87 (m, 1H), 4.59-4.39 (m, 2H), 4.30 (s, 1H), 3.62 (s, 2H), 3.46-3.38 (m, 1H), 2.49-2.47 (m, 2H), 2.46 (s, 3H), 2.36-1.98 (m, 6H), 1.86-1.73 (m, 1H), 1.66-1.45 (m, 8H), 1.43-1.24 (m, 15H), 0.95 (s, 9H) |
| G142 | 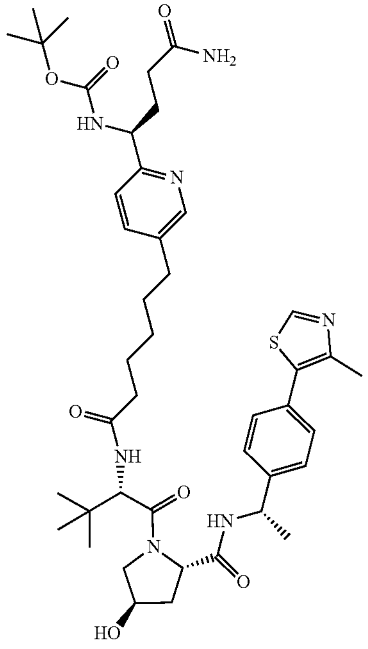 [SMILES: Cc1ncsc1-c1ccc([C@H](C)NC(=O)[C@@H]2C[C@@H](O)CN2C(=O)[C@@H](NC(=O)CCCCCc2ccc([C@H](CCC(N)=O)NC(=O)OC(C)(C)C)nc2)C(C)(C)C)cc1] | tert-butyl N-[(1S)-3-carbamoyl-1-[5-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)pyridin-2-yl]propyl]carbamate | 820.45 | (300 MHz, DMSO-$d_6$) δ 8.99 (s, 1H), 8.42-8.32 (m, 2H), 7.81-7.79 (m, 1H), 7.59-7.56 (dd, J = 8.0, 2.3 Hz, 1H), 7.48-7.41 (m, 3H), 7.41-7.32 (m, 2H), 7.28-7.23 (m, 1H), 7.21-7.19 (d, J = 8.0 Hz, 1H), 6.75 (s, 1H), 5.12-5.11 (d, J = 3.6 Hz, 1H), 4.96-4.89 (m, 1H), 4.53-4.50 (d, J = 9.3 Hz, 1H), 4.47-4.41 (s, 2H), 4.29-4.27 (m, 1H), 4.06-4.01 (m, 1H), 3.64-3.58 (m, 2H), 2.69-2.65 (m, 2H), 2.46 (s, 3H), 2.29-2.22 (m, 1H), 2.15-2.10 (m, 1H), 2.06-1.2.02 (m, 3H), 2.00 (s, 1H), 1.93-1.74 (m, 2H), 1.68-1.61 (m, 2H), 1.56-1.48 (m, 2H), 1.38 (s, 3H), 1.37-1.35 (m, 7H), 1.27-1.19 (m, 3H), 0.93 (s, 9H) |

TABLE 47-continued

| Characterization data for intermediates prepare according to the procedure above. | | | | |
|---|---|---|---|---|
| Intermediate | Structure | Chemical Name | MS: [(M + 1)]$^+$ | $^1$H-NMR |
| G143 | 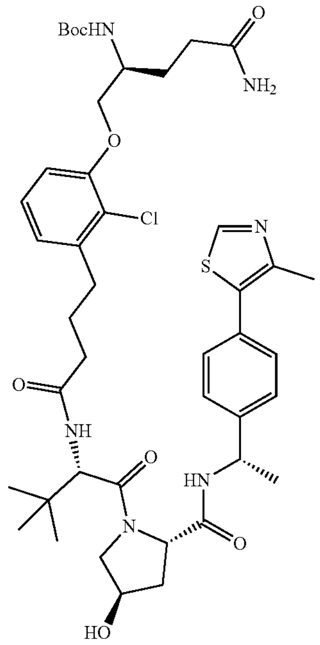 | tert-butyl N-[(2S)-4-carbamoyl-1-[2-chloro-3-(3-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]propyl)phenoxy]butan-2-yl]carbamate | 855.35 | (300 MHz, DMSO-$d_6$) δ 9.00 (s, 1H), 8.40 (d, J = 7.7 Hz, 1H), 7.90 (d, J = 9.2 Hz, 1H), 7.45-7.41 (m, 4H), 7.29 (s, 1H), 7.22 (t, J = 7.9 Hz, 1H), 7.00 (d, J = 8.3 Hz, 1H), 6.91 (d, J = 7.7 Hz, 1H), 6.83 (d, J = 8.3 Hz, 1H), 6.76 (s, 1H), 5.12 (s, 1H), 5.00-4.89 (m, 1H), 4.56 (d, J = 9.2 Hz, 1H), 4.45 (t, J = 8.1 Hz, 1H), 4.31 (s, 1H), 3.94 (d, J = 5.9 Hz, 2H), 3.79 (s, 1H), 3.64 (s, 2H), 2.69 (t, J = 7.7 Hz, 2H), 2.48 (s, 3H), 2.34-2.30 (m, 1H), 2.25-2.12 (m, 2H), 2.10 (s, 2H), 1.83-1.79 (m, 4H), 1.65-1.61 (m, 1H), 1.41 (s, 9H), 1.37 (d, J = 11.0 Hz, 3H), 0.97 (s, 9H) |
| G144 | 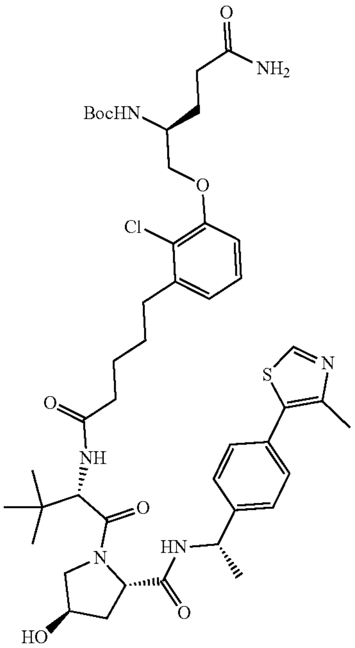 [SMILES: Cc1ncsc1-c1ccc([C@H](C)NC(=O)[C@@H]2C[C@@H](O)CN2C(=O)[C@@H](NC(=O)CCCCc2cccc(OC[C@H](CCC(N)=O)NC(=O)OC(C)(C)C)c2Cl)C(C)(C)C)cc1] | tert-butyl N-[(2S)-4-carbamoyl-1-[2-chloro-3-(3-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]propyl)phenoxy]butan-2-yl]carbamate | 869.35 | (400 MHz, DMSO-$d_6$) δ 8.99 (s, 1H), 8.39 (d, J = 7.8 Hz, 1H), 7.85 (d, J = 9.2 Hz, 1H), 7.45 (d, J = 8.3 Hz, 2H), 7.39 (d, J = 8.3 Hz, 2H), 7.30 (d, J = 15.6 Hz, 1H), 7.20 (t, J = 7.9 Hz, 1H), 6.98 (d, J = 8.2 Hz, 1H), 6.91 (dd, J = 7.6, 1.3 Hz, 1H), 6.81 (d, J = 8.5 Hz, 1H), 6.75 (s, 1H), 5.11 (d, J = 3.5 Hz, 1H), 4.99-4.87 (m, 1H), 4.53 (d, J = 9.3 Hz, 1H), 4.44 (t, J = 8.0 Hz, 1H), 4.31-4.27 (m, 1H), 3.93 (d, J = 6.1 Hz, 2H), 3.83-3.73 (m, 1H), 3.67-3.56 (m, 2H), 2.71-2.67 (m, 2H), 2.47 (s, 3H), 2.36-2.26 (m, 1H), 2.22-2.10 (m, 3H), 2.10-1.97 (m, 1H), 1.92-1.75 (m, 2H), 1.70-1.49 (m, 4H), 1.40 (s, 9H), 1.38-1.34 (m, 2H), 1.31-1.22 (m, 2H), 0.94 (s, 9H) |

TABLE 47-continued

Characterization data for intermediates prepare according to the procedure above.

| Intermediate | Structure | Chemical Name | MS: [(M + 1)]+ | $^1$H-NMR |
|---|---|---|---|---|
| G145 | 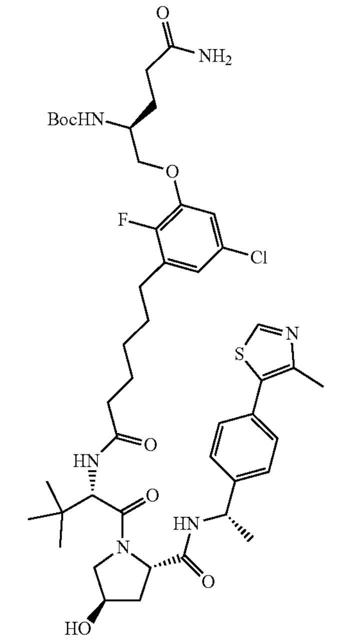 [SMILES: Cc1ncsc1-c1ccc([C@H](C)NC(=O)[C@@H]2C[C@@H](O)CN2C(=O)[C@@H](NC(=O)CCCCCc2cc(Cl)cc(OC[C@H](CCC(N)=O)NC(=O)OC(C)(C)C)c2F)C(C)(C)C)cc1] | tert-butyl N-[(2S)-4-carbamoyl-1-[5-chloro-2-fluoro-3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenoxy]butan-2-yl]carbamate | 901.35 | (400 MHz, DMSO-d$_6$) δ 8.99 (s, 1H), 8.38 (d, J = 7.8 Hz, 1H), 7.81-7.79 (m, 1H), 7.44 (d, J = 8.1 Hz, 2H), 7.38 (d, J = 8.1 Hz, 2H), 7.27 (s, 1H), 7.12-7.10 (m, 1H), 6.92-6.90 (m, 1H), 6.84 (d, J = 8.5 Hz, 1H), 6.75 (s, 1H), 5.11 (s, 1H), 4.92 (p, J = 7.3 Hz, 1H), 4.53-4.51 (m, 1H), 4.42 (t, J = 8.0 Hz, 1H), 4.29 (s, 1H), 3.97-3.93 (m, 1H), 3.75-3.73 (m, 1H), 3.61 (d, J = 4.1 Hz, 2H), 3.27-3.23 (m, 2H), 2.56 (d, J = 7.6 Hz, 1H), 2.46 (s, 3H), 2.31-2.20 (m, 1H), 2.19-2.10 (m, 2H), 2.10-2.06 (m, 2H), 2.03-2.01 (m, 1H), 1.88-1.78 (m, 2H), 1.64-1.44 (m, 5H), 1.38 (s, 9H), 1.27-1.21 (m, 4H), 0.93 (s, 9H) |
| G146 | 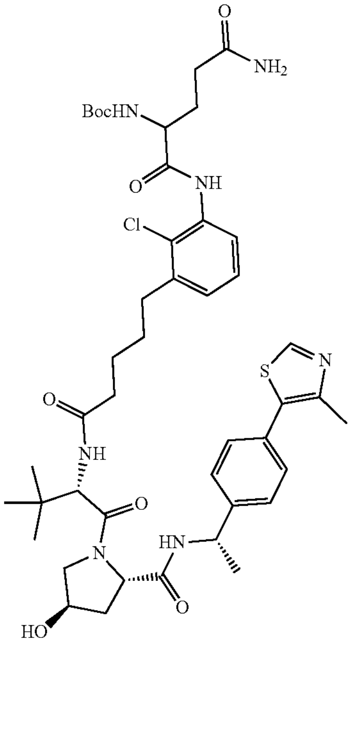 [SMILES: Cc1ncsc1-c1ccc([C@H](C)NC(=O)[C@@H]2C[C@@H](O)CN2C(=O)[C@@H](NC(=O)CCCCc2cccc(NC(=O)C(CCC(N)=O)NC(=O)OC(C)(C)C)c2Cl)C(C)(C)C)cc1] | tert-butyl N-(3-carbamoyl-1-[[2-chloro-3-(4-[[(2S)-1-[(2S,4R)-4-hydroxy-2-[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]butyl)phenyl]carbamoyl]propyl)carbamate | 882.35 | (400 MHz, DMSO-d$_6$) δ 9.31 (s, 1H), 8.99 (s, 1H), 8.38 (d, J = 7.8 Hz, 1H), 7.84 (d, J = 9.3 Hz, 1H), 7.74 (d, J = 8.1 Hz, 1H), 7.68-7.53 (m, 1H), 7.44 (d, J = 8.3 Hz, 2H), 7.39 (d, J = 8.2 Hz, 2H), 7.26 (dd, J = 9.8, 6.6 Hz, 2H), 7.13 (d, J = 7.5 Hz, 1H), 6.81 (s, 1H), 5.10 (d, J = 3.6 Hz, 1H), 4.92 (p, J = 7.1 Hz, 1H), 4.53 (d, J = 9.3 Hz, 1H), 4.43 (t, J = 8.0 Hz, 1H), 4.29 (s, 1H), 4.12 (s, 1H), 3.61 (d, J = 4.2 Hz, 2H), 2.74-2.70 (m, 2H), 2.46 (s, 3H), 2.37-2.29 (m, 1H), 2.21-2.17 (m, 3H), 2.03-1.98 (m, 2H), 1.88-1.74 (m, 2H), 1.58-1.52 (m, 3H), 1.43-1.35 (m, 12H), 1.27-1.23 (m, 1H), 0.94 (s, 9H) |

TABLE 47-continued

Characterization data for intermediates prepare according to the procedure above.

| Intermediate | Structure | Chemical Name | MS: [(M + 1)]+ | $^1$H-NMR |
|---|---|---|---|---|
| G147 | 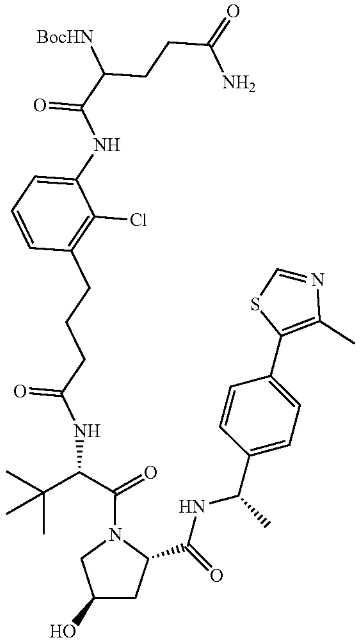 [SMILES: Cc1ncsc1-c1ccc([C@H](C)NC(=O)[C@@H]2C[C@@H](O)CN2C(=O)[C@@H](NC(=O)CCCc2cccc(NC(=O)C(CCC(N)=O)NC(=O)OC(C)(C)C)c2Cl)C(C)(C)C)cc1] | tert-butyl N-[(1S)-3-carbamoyl-1-[[2-chloro-3-(3-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]propyl)phenyl]carbamoyl]propyl]carbamate | 868.35 | (400 MHz, DMSO-$d_6$) δ 9.32 (s, 1H), 8.99 (s, 1H), 8.38 (d, J = 7.7 Hz, 1H), 7.90 (d, J = 9.3 Hz, 1H), 7.75 (d, J = 8.1 Hz, 1H), 7.44 (d, J = 8.3 Hz, 2H), 7.38 (d, J = 8.3 Hz, 2H), 7.30 (d, J = 9.6 Hz, 2H), 7.26 (d, J = 8.1 Hz, 1H), 7.15-7.08 (m, 1H), 6.81 (s, 1H), 5.10 (s, 1H), 4.92 (p, J = 6.9 Hz, 1H), 4.55 (d, J = 9.2 Hz, 1H), 4.43 (t, J = 8.0 Hz, 1H), 4.29 (s, 1H), 4.13-4.09 (m, 1H), 3.62 (s, 2H), 2.72-2.68 (m, 2H), 2.46 (s, 3H), 2.35-2.31 (m, 1H), 2.23-2.19 (m, 2H), 2.01 (s, 1H), 1.83-1.79 (m, 4H), 1.43-1.35 (m, 12H), 1.33-1.23 (m, 2H), 0.95 (s, 9H) |
| G148 | 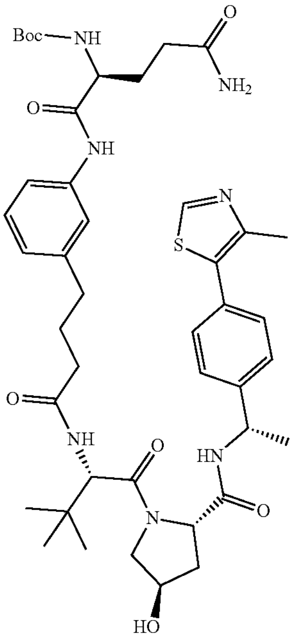 [SMILES: Cc1ncsc1-c1ccc([C@H](C)NC(=O)[C@@H]2C[C@@H](O)CN2C(=O)[C@@H](NC(=O)CCCc2cccc(NC(=O)[C@H](CCC(N)=O)NC(=O)OC(C)(C)C)c2)C(C)(C)C)cc1] | tert-butyl N-[(1S)-3-carbamoyl-1-[[3-(3-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]propyl)phenyl]carbamoyl]propyl]carbamate | 834.35 | (400 MHz, DMSO-$d_6$) δ 9.96 (s, 1H), 8.99 (s, 1H), 8.41 (d, J = 7.8 Hz, 1H), 8.26 (s, 1H), 7.87 (d, J = 9.3 Hz, 1H), 7.44 (d, J = 7.9 Hz, 4H), 7.39 (d, J = 8.3 Hz, 2H), 7.33 (d, J = 3.5 Hz, 1H), 7.21 (t, J = 7.7 Hz, 1H), 7.04 (d, J = 7.8 Hz, 1H), 6.88 (d, J = 7.7 Hz, 1H), 6.80 (s, 1H), 5.76 (s, 1H), 4.93 (p, J = 7.2 Hz, 1H), 4.54 (d, J = 9.3 Hz, 1H), 4.44 (t, J = 8.0 Hz, 1H), 4.29 (p, J = 3.2 Hz, 1H), 4.05 (q, J = 7.5 Hz, 1H), 3.63 (d, J = 3.2 Hz, 2H), 2.55 (d, J = 2.7 Hz, 1H), 2.46 (s, 3H), 2.29-2.25 (m, 1H), 2.18-2.15 (m, 3H), 2.02-1.99 (m, 1H), 1.96-1.86 (m, 1H), 1.85-1.71 (m, 4H), 1.38-1.21 (m, 12H), 0.95 (s, 9H) |

Characterization data for intermediates prepare according to the procedure above.

| Inter-me-diate | Structure | Chemical Name | MS: [(M + 1)]+ | 1H-NMR |
|---|---|---|---|---|
| G149 | 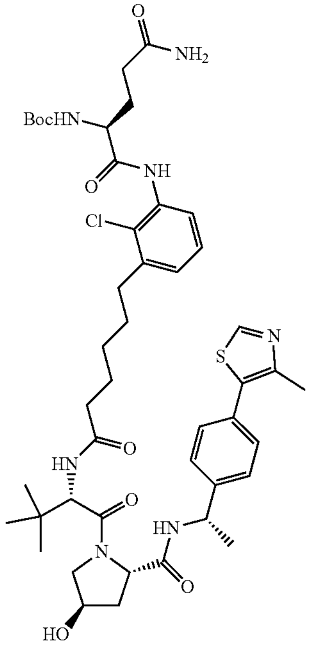 [SMILES: Cc1ncsc1-c1ccc([C@H](C)NC(=O)[C@@H]2C[C@@H](O)CN2C(=O)[C@@H](NC(=O)CCCCCc2cccc(NC(=O)[C@H](CCC(N)=O)NC(=O)OC(C)(C)C)c2Cl)C(C)(C)C)cc1] | tert-butyl N-[(1S)-3-carbamoyl-1-[[2-chloro-3-(5-[[(2S)-1-[(2S,4R)-4-hydroxy-2-[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenyl]carbamoyl]propyl]carbamate | 896.45 | (300 MHz, DMSO-$d_6$) δ 9.60 (s, 1H), 9.00 (d, J = 1.2 Hz, 1H), 8.39 (d, J = 7.7 Hz, 1H), 7.78 (dd, J = 18.0, 8.8 Hz, 2H), 7.43 (q, J = 8.1 Hz, 4H), 7.32 (s, 1H), 7.15-7.01 (m, 3H), 6.82 (s, 1H), 5.12 (d, J = 3.5 Hz, 1H), 4.95 (t, J = 7.3 Hz, 1H), 4.53 (d, J = 9.2 Hz, 1H), 4.45 (t, J = 8.0 Hz, 1H), 4.36-4.24 (m, 1H), 4.20-4.15 (m, 1H), 3.63 (s, 2H), 3.36 (d, J = 1.2 Hz, 2H), 2.61 (t, J = 7.7 Hz, 2H), 2.48 (s, 3H), 2.31-2.11 (m, 3H), 2.10-1.88 (m, 1H), 1.88-1.71 (m, 2H), 1.63-1.48 (m, 2H), 1.46-1.22 (m, 14H), 0.95 (s, 9H) |
| G150 | 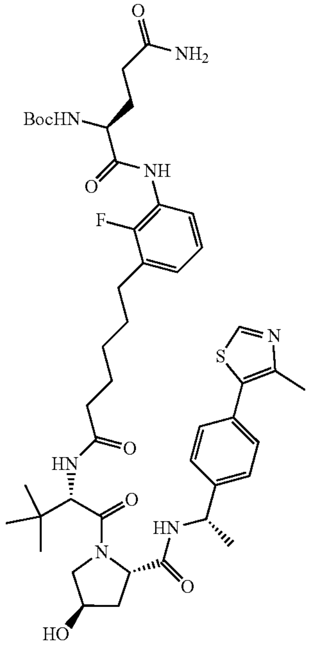 [SMILES: Cc1ncsc1-c1ccc([C@H](C)NC(=O)[C@@H]2C[C@@H](O)CN2C(=O)[C@@H](NC(=O)CCCCCc2cccc(NC(=O)[C@H](CCC(N)=O)NC(=O)OC(C)(C)C)c2F)C(C)(C)C)cc1] | tert-butyl N-[(1S)-3-carbamoyl-1-[[2-fluoro-3-(5-[[(2S)-1-[(2S,4R)-4-hydroxy-2-[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenyl]carbamoyl]propyl]carbamate | 880.09 | (300 MHz, DMSO-$d_6$) δ 9.32 (s, 1H), 9.00 (d, J = 1.3 Hz, 1H), 8.39 (d, J = 7.7 Hz, 1H), 7.78 (dd, J = 18.1, 8.6 Hz, 2H), 7.49-7.36 (m, 5H), 7.32-7.25 (m, 2H), 7.14 (d, J = 7.5 Hz, 1H), 6.82 (s, 1H), 5.12 (s, 1H), 5.01-4.86 (m, 1H), 4.54 (d, J = 9.1 Hz, 1H), 4.44 (t, J = 8.0 Hz, 1H), 4.30 (s, 1H), 4.17-4.11 (m, 1H), 2.71 (t, J = 7.8 Hz, 2H), 2.48 (s, 3H), 2.34-2.12 (m, 3H), 2.07-1.96 (m, 1H), 1.86-1.77 (m, 2H), 1.62-1.50 (m, 4H), 1.46-1.20 (m, 18H), 0.95 (s, 9H) |

TABLE 47-continued

| Characterization data for intermediates prepare according to the procedure above. | | | | |
|---|---|---|---|---|
| Intermediate | Structure | Chemical Name | MS: [(M + 1)]+ | $^1$H-NMR |
| G151 | 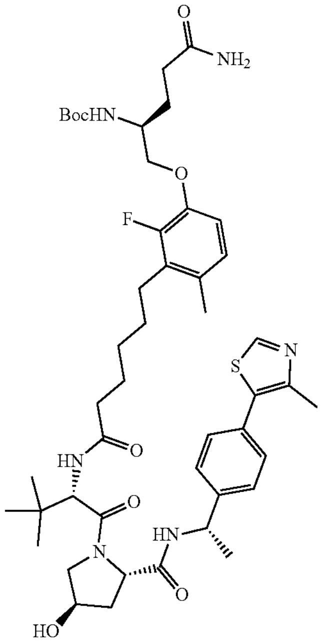 [SMILES: Cc1ccc(OC[C@H](CCC(N)=O)NC(=O)OC(C)(C)C)c(F)c1CCCCCC(=O)N[C@H](C(=O)N1C[C@H](O)C[C@H]1C(=O)N[C@@H](C)c1ccc(-c2scnc2C)cc1)C(C)(C)C] | tert-butyl N-[(2S)-4-carbamoyl-1-[2-fluoro-3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)-4-methylphenoxy]butan-2-yl]carbamate | 881.40 | (400 MHz, DMSO-$d_6$) δ 8.99 (s, 1H), 8.38 (d, J = 7.8 Hz, 1H), 7.80 (d, J = 9.3 Hz, 1H), 7.44 (d, J = 8.3 Hz, 2H), 7.45-7.31 (m, 2H), 7.27 (s, 1H), 6.92-6.85 (m, 2H), 6.82 (d, J = 8.5 Hz, 1H), 6.74 (s, 1H), 5.10 (d, J = 3.6 Hz, 1H), 4.92 (p, J = 7.3 Hz, 1H), 4.52 (d, J = 9.3 Hz, 1H), 4.43 (t, J = 8.0 Hz, 1H), 4.28 (s, 1H), 3.89-3.85 (m, 2H), 3.75-3.68 (m, 1H), 3.61 (d, J = 4.1 Hz, 2H), 2.58-2.54 (m, 2H), 2.46 (s, 3H), 2.34-2.23 (m, 1H), 2.21 (s, 3H), 2.17-2.06 (m, 3H), 2.05-1.97 (m, 2H), 1.88-1.74 (m, 2H), 1.64-1.44 (m, 5H), 1.38 (s, 9H), 1.36-1.14 (m, 4H), 0.93 (s, 9H) |
| G152 | 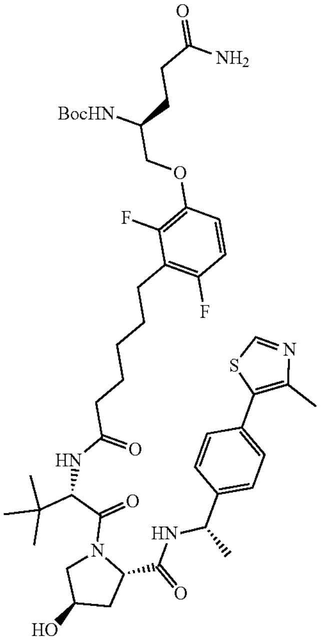 [SMILES: Cc1ncsc1-c1ccc([C@H](C)NC(=O)[C@@H]2C[C@@H](O)CN2C(=O)[C@@H](NC(=O)CCCCCc2c(F)ccc(OC[C@H](CCC(N)=O)NC(=O)OC(C)(C)C)c2F)C(C)(C)C)cc1] | tert-butyl N-[(2S)-4-carbamoyl-1-[2,4-difluoro-3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenoxy]butan-2-yl]carbamate | 885.40 | (400 MHz, DMSO-$d_6$) δ 8.99 (s, 1H), 8.38 (d, J = 7.8 Hz, 1H), 7.79 (d, J = 9.3 Hz, 1H), 7.44 (d, J = 8.3 Hz, 2H), 7.45-7.31 (m, 2H), 7.27 (s, 1H), 7.05-7.01 (m, 1H), 6.97-6.95 (m, 1H), 6.84 (d, J = 8.6 Hz, 1H), 6.74 (s, 1H), 5.10 (d, J = 3.5 Hz, 1H), 4.92 (p, J = 7.0 Hz, 1H), 4.51 (d, J = 9.3 Hz, 1H), 4.42 (t, J = 8.0 Hz, 1H), 4.28 (s, 1H), 3.90 (d, J = 6.0 Hz, 2H), 3.76-3.67 (m, 1H), 3.66-3.55 (m, 2H), 2.59 (t, J = 7.5 Hz, 2H), 2.46 (s, 3H), 2.32-2.20 (m, 1H), 2.17-2.06 (m, 3H), 2.04-1.98 (m, 1H), 1.86-1.74 (m, 2H), 1.64-1.43 (m, 5H), 1.39 (s, 9H), 1.35-1.20 (m, 4H), 1.10-1.02 (m, 1H), 0.93 (s, 9H) |

TABLE 47-continued

| Characterization data for intermediates prepare according to the procedure above. | | | | |
|---|---|---|---|---|
| Inter-me-diate | Structure | Chemical Name | MS: [(M + 1)]$^+$ | $^1$H-NMR |
| G153 | 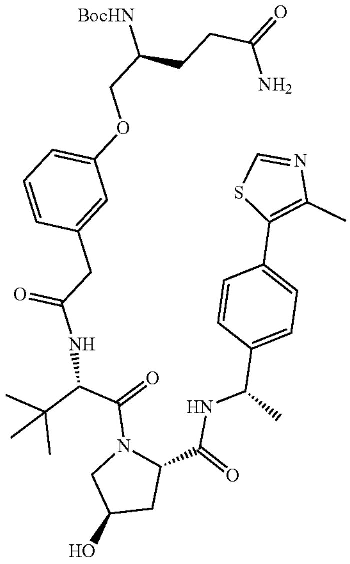 [SMILES: Cc1ncsc1-c1ccc([C@H](C)NC(=O)[C@@H]2C[C@@H](O)CN2C(=O)[C@@H](NC(=O)Cc2cccc(OC[C@H](CCC(N)=O)NC(=O)OC(C)(C)C)c2)C(C)(C)C)cc1] | tert-butyl N-[(2S)-4-carbamoyl-1-[3-([[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]methyl)phenoxy]butan-2-yl]carbamate | 793.30 | (400 MHz, DMSO-$d_6$) δ 8.99 (s, 1 H), 8.40 (d, J = 7.7 Hz, 1H), 8.03 (d, J = 9.2 Hz, 1H), 7.48-7.31 (m, 4H), 7.28 (s, 1H), 7.19 (t, J = 7.9 Hz, 1H), 8.99 (s, 1H), 6.94-6.67 (m, 5H), 5.11 (d, J = 3.5 Hz, 1H), 4.99-4.87 (m, 1H), 4.52-4.39 (m, 2H), 4.30-4.24 (m, 1H), 3.90-3.67 (m, 3H), 3.66-3.54 (m, 3H), 3.40 (d, J = 13.7 Hz, 1H), 2.46 (s, 3H), 2.18-2.09 (m, 6.4 Hz, 2H), 2.03-1.99 (m, 1H), 1.83-1.70 (m, 2H), 1.68-1.54 (m, 1H), 1.42-1.38 (m, 10H), 1.38-1.36 (s, 2H), 0.92 (s, 9H) |
| G154 | 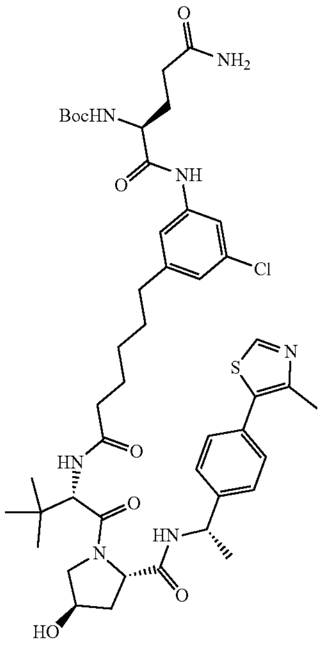 [SMILES: Cc1ncsc1-c1ccc([C@H](C)NC(=O)[C@@H]2C[C@@H](O)CN2C(=O)[C@@H](NC(=O)CCCCCc2cc(Cl)cc(NC(=O)[C@H](CCC(N)=O)NC(=O)OC(C)(C)C)c2)C(C)(C)C)cc1] | tert-butyl N-[(1S)-3-carbamoyl-1-[[3-chloro-5-(5-[[(2S)-1-[(2S,4R)-4-hydroxy-2-[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenyl]carbamoyl]propyl]carbamate | 896.45 | (300 MHz, DMSO-$d_6$) δ 10.07 (s, 1H), 8.97 (s, 1H), 8.35 (d, J = 7.8 Hz, 1H), 7.77 (d, J = 9.2 Hz, 1H), 7.64 (d, J = 2.3 Hz, 1H), 7.40 (q, J = 8.3 Hz, 4H), 7.28 (s, 2H), 7.06 (d, J = 7.5 Hz, 1H), 6.95 (t, J = 1.7 Hz, 1H), 6.77 (s, 1H), 5.09 (d, J = 3.5 Hz, 1H), 4.97-4.86 (m, 1H), 4.51 (d, J = 9.3 Hz, 1H), 4.42 (t, J = 8.0 Hz, 1H), 4.28 (s, 1H), 4.00 (d, J = 6.9 Hz, 1H), 3.60 (s, 2H), 2.53 (d, J = 7.5 Hz, 2H), 2.45 (s, 3H), 2.30-2.10 (m, 4H), 2.01-1.74 (m, 4H), 1.65-1.42 (m, 4H), 1.41-1.35 (m, 11H), 1.33-1.19 (m, 4H), 0.92 (s, 9H) |

TABLE 47-continued

| Characterization data for intermediates prepare according to the procedure above. | | | | |
|---|---|---|---|---|
| Intermediate | Structure | Chemical Name | MS: [(M + 1)]+ | ¹H-NMR |
| G155 | 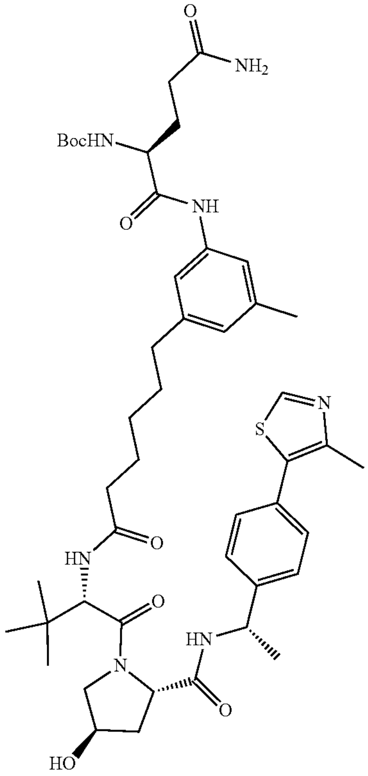 [SMILES: Cc1cc(CCCCCC(=O)N[C@H](C(=O)N2C[C@H](O)C[C@H]2C(=O)N[C@@H](C)c2ccc(-c3scnc3C)cc2)C(C)(C)C)cc(NC(=O)[C@H](CCC(N)=O)NC(=O)OC(C)(C)C)c1] | Tert-butyl N-[(1S)-3-carbamoyl-1-[[3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)-5-methylphenyl]carbamoyl]propyl]carbamate | 876.40 | (300 MHz, DMSO-$d_6$) δ 9.78 (s, 1H), 9.00 (s, 1H), 8.37 (d, J = 7.7 Hz, 1H), 7.79 (d, J = 9.2 Hz, 1H), 7.49-7.38 (m, 4H), 7.29-7.18 (m, 3H), 7.00 (d, J = 7.8 Hz, 1H), 6.79-6.72 (m, 2H), 5.10 (d, J = 3.5 Hz, 1H), 5.01-4.83 (m, 1H), 4.63-4.36 (m, 2H), 4.30 (s, 1H), 4.06-3.97 (m, 1H), 3.62 (d, J = 3.2 Hz, 2H), 3.04-2.45 (m, 6H), 2.26 (s, 3H), 2.18-2.13 (m, 6H), 1.95-1.70 (m, 2H), 1.62-1.51 (m, 4H), 1.39 (s, 9H), 1.32-1.24 (m, 4H), 0.95 (s, 9H) |
| G156 | 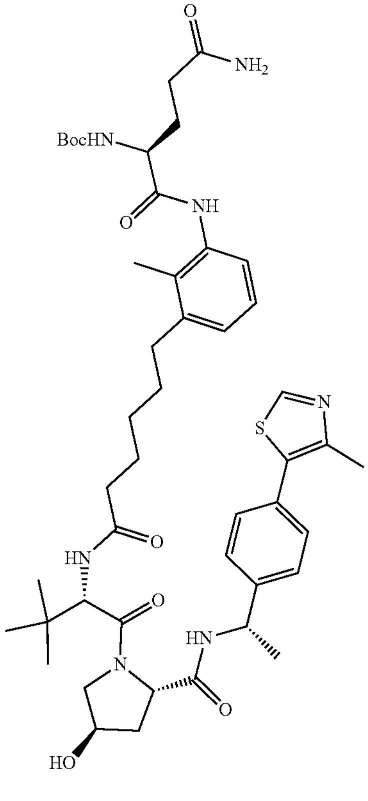 [SMILES: Cc1ncsc1-c1ccc([C@H](C)NC(=O)[C@@H]2C[C@@H](O)CN2C(=O)[C@@H](NC(=O)CCCCCc2cccc(NC(=O)[C@H](CCC(N)=O)NC(=O)OC(C)(C)C)c2C)C(C)(C)C)cc1] | tert-butyl N-[(1S)-3-carbamoyl-1-[[3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)-2-methylphenyl]carbamoyl]propyl]carbamate | 876.50 | (300 MHz, DMSO-$d_6$) δ 9.30 (s, 1H), 9.00 (s, 1H), 8.40 (d, J = 7.7 Hz, 1H), 7.82 (d, J = 9.2 Hz, 1H), 7.47-7.34 (m, 6H), 7.23-6.93 (m, 4H), 6.82 (s, 1H), 5.13 (d, J = 3.5 Hz, 1H), 4.96-4.90 (m, 1H), 4.60-4.38 (m, 2H), 4.30 (s, 1H), 4.08 (d, J = 6.8 Hz, 1H), 3.63 (d, J = 3.3 Hz, 2H), 2.60 (d, J = 7.6 Hz, 2H), 2.47 (s, 3H), 2.36-1.88 (m, 9H), 1.85-1.81 (m, 2H), 1.67-1.46 (m, 4H), 1.41 (d, J = 3.8 Hz, 11H), 1.39-1.14 (m, 2H), 0.95 (s, 9H) |

TABLE 47-continued

Characterization data for intermediates prepare according to the procedure above.

| Inter-me-diate | Structure | Chemical Name | MS: [(M + 1)]+ | $^1$H-NMR |
|---|---|---|---|---|
| G157 | 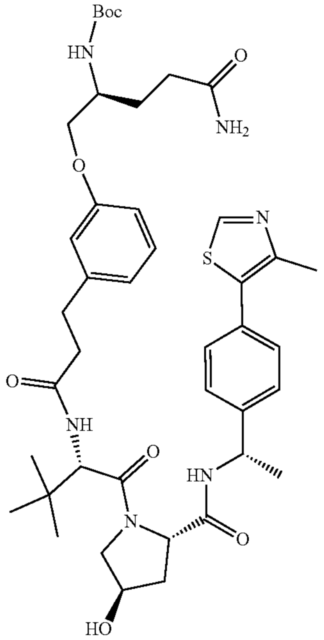 [SMILES: Cc1ncsc1-c1ccc([C@H](C)NC(=O)[C@@H]2C[C@@H](O)CN2C(=O)[C@@H](NC(=O)CCc2cccc(OC[C@H](CCC(N)=O)NC(=O)OC(C)(C)C)c2)C(C)(C)C)cc1] | tert-butyl N-[(2S)-4-carbamoyl-1-[3-(2-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]ethyl)phenoxy]butan-2-yl]carbamate | 807.3 | (400 MHz, DMSO-$d_6$) δ 8.99 (s, 1H), 8.39 (d, J = 7.8 Hz, 1H), 7.89 (d, J = 9.3 Hz, 1H), 7.44 (d, J = 8.1 Hz, 2H), 7.39 (d, J = 8.3 Hz, 2H), 7.28 (s, 1H), 7.16 (t, J = 7.8 Hz, 1H), 6.86-6.70 (m, 5H), 5.76 (s, 1H), 5.17-5.09 (m, 1H), 4.93 (p, J = 7.2 Hz, 1H), 4.53 (d, J = 9.3 Hz, 1H), 4.44 (t, J = 8.0 Hz, 1H), 4.29 (s, 1H), 3.84 (qd, J = 9.6, 5.8 Hz, 2H), 3.72 (dp, J = 9.0, 4.9 Hz, 1H), 3.62 (d, J = 3.4 Hz, 2H), 3.35-3.32 (m, 4H), 2.85-2.69 (m, 2H), 2.60-2.58 (m, 1H), 2.46 (s, 3H), 2.20-1.99 (m, 4H), 1.82-1.76 (m, 2H), 1.62-1.57 (m, 1H), 1.44 (s, 9H), 0.90 (s, 9H) |
| G158 | 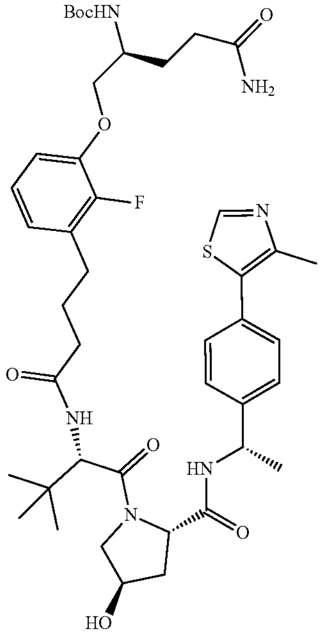 [SMILES: Cc1ncsc1-c1ccc([C@H](C)NC(=O)[C@@H]2C[C@@H](O)CN2C(=O)[C@@H](NC(=O)CCCc2cccc(OC[C@H](CCC(N)=O)NC(=O)OC(C)(C)C)c2F)C(C)(C)C)cc1] | tert-butyl N-[(2S)-4-carbamoyl-1-[2-fluoro-3-(3-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]propyl)phenoxy]butan-2-yl]carbamate | 839.40 | (300 MHz, DMSO-$d_6$) δ 9.00 (s, 1H), 8.38 (d, J = 7.8 Hz, 1H), 7.87 (d, J = 9.2 Hz, 1H), 7.42 (q, J = 8.3 Hz, 4H), 7.29 (s, 1H), 7.03-6.98 (m, 2H), 6.84-6.80 (m, 2H), 6.74 (s, 1H), 5.10 (d, J = 3.6 Hz, 1H), 4.98-4.88 (m, 1H), 4.54 (d, J = 9.3 Hz, 1H), 4.44 (t, J = 8.0 Hz, 1H), 4.29 (s, 1H), 3.93 (d, J = 6.0 Hz, 2H), 3.75-3.73 (m, 1H), 3.64-3.61 (m, 2H), 2.58 (t, J = 7.6 Hz, 2H), 2.47 (s, 3H), 2.32-2.28 (m, 1H), 2.21-2.16 (m, 2H), 2.07-1.97 (m, 1H), 1.87-1.69 (m, 5H), 1.64-1.62 (m, 1H), 1.40 (s, 9H), 0.96 (s, 9H) |

TABLE 47-continued

Characterization data for intermediates prepare according to the procedure above.

| Inter-me-diate | Structure | Chemical Name | MS: [(M + 1)]$^+$ | $^1$H-NMR |
|---|---|---|---|---|
| G159 | 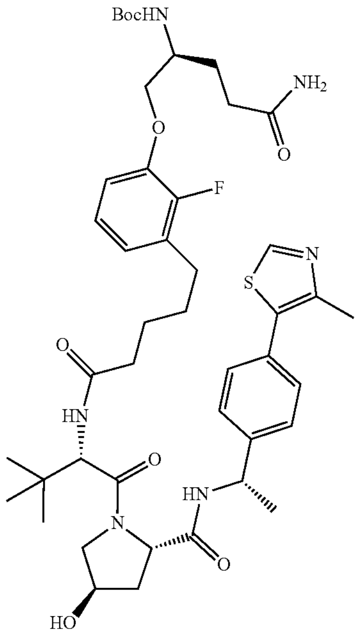 [SMILES: Cc1ncsc1-c1ccc([C@H](C)NC(=O)[C@@H]2C[C@@H](O)CN2C(=O)[C@@H](NC(=O)CCCCc2cccc(OC[C@H](CCC(N)=O)NC(=O)OC(C)(C)C)c2F)C(C)(C)C)cc1] | tert-butyl N-[(2S)-4-carbamoyl-1-[2-fluoro-3-(4-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]butyl)phenoxy]butan-2-yl]carbamate | 853.35 | (400 MHz, DMSO-$d_6$) δ 9.00 (s, 1H), 8.39 (d, J = 7.8 Hz, 1H), 7.84 (d, J = 9.3 Hz, 1H), 7.45 (d, J = 8.3 Hz, 2H), 7.40 (d, J = 8.4 Hz, 2H), 7.28 (s, 1H), 7.06-6.96 (m, 2H), 6.87-6.80 (m, 2H), 6.75 (s, 1H), 5.11 (d, J = 3.5 Hz, 1H), 4.94-4.92 (m, 1H), 4.53 (d, J = 9.3 Hz, 1H), 4.44 (t, J = 8.0 Hz, 1H), 4.30-4.28 (m, 1H), 3.92 (d, J = 6.1 Hz, 2H), 3.76-3.72 (m, 1H), 3.67-3.58 (m, 2H), 2.59 (t, J = 7.0 Hz, 2H), 2.47 (s, 3H), 2.33-2.29 (m, 1H), 2.18-2.13 (m, 4H), 2.03-2.01 (m, 1H), 1.86-1.83 (m, 2H), 1.65-1.46 (m, 6H), 1.40 (s, 9H), 1.35-1.33 (m, 1H), 0.95 (s, 9H) |
| G160 | 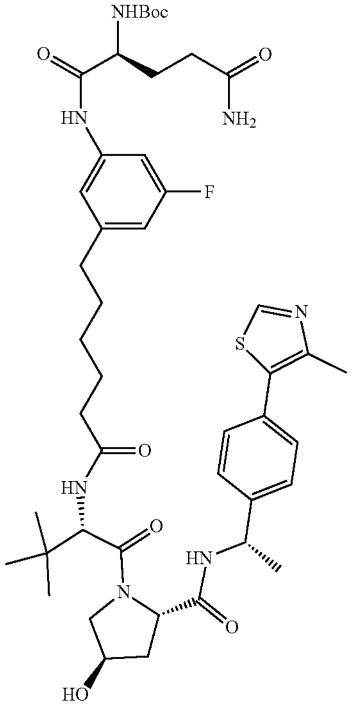 [SMILES: Cc1ncsc1-c1ccc([C@H](C)NC(=O)[C@@H]2C[C@@H](O)CN2C(=O)[C@@H](NC(=O)CCCCCc2cc(F)cc(NC(=O)[C@H](CCC(N)=O)NC(=O)OC(C)(C)C)c2)C(C)(C)C)cc1] | tert-butyl N-[(1S)-3-carbamoyl-1-[[3-fluoro-5-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenyl]carbamoyl]propyl]carbamate | 880.45 | (400 MHz, DMSO-$d_6$) δ 10.11 (s, 1H), 8.99 (s, 1H), 8.39 (d, J = 7.7 Hz, 1H), 7.80 (d, J = 9.2 Hz, 1H), 7.51-7.36 (m, 5H), 7.30 (s, 1H), 7.15 (s, 1H), 7.09 (d, J = 7.6 Hz, 1H), 6.80 (s, 1H), 6.73 (d, J = 9.5 Hz, 1H), 5.11 (s, 1H), 4.92-4.85 (m, 1H), 4.52 (d, J = 9.3 Hz, 1H), 4.42 (t, J = 8.0 Hz, 1H), 4.29 (s, 1H), 4.01 (q, J = 7.4 Hz, 1H), 3.64-3.59 (m, 2H), 3.35 (s, 2H), 2.56-2.54 (m, 2H), 2.46 (s, 3H), 2.24-2.08 (m, 2H), 2.06-1.70 (m, 4H), 1.58-1.48 (m, 4H), 1.39 (s, 9H), 1.37 (s, 2H), 1.28-1.24 (m, 3H), 0.93 (s, 9H) |

TABLE 47-continued

Characterization data for intermediates prepare according to the procedure above.

| Intermediate | Structure | Chemical Name | MS: [(M + 1)]$^+$ | $^1$H-NMR |
|---|---|---|---|---|
| G161 | 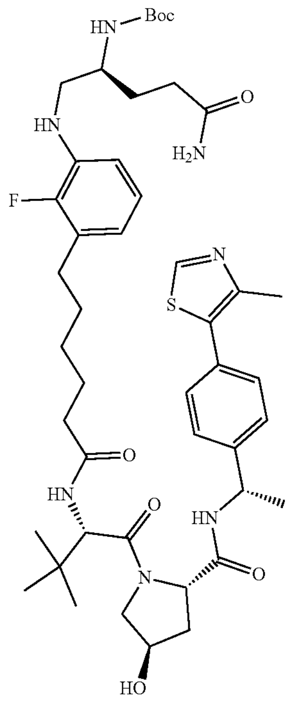 [SMILES: Cc1ncsc1-c1ccc([C@H](C)NC(=O)[C@@H]2C[C@@H](O)CN2C(=O)[C@@H](NC(=O)CCCCCc2cccc(NC[C@H](CCC(N)=O)NC(=O)OC(C)(C)C)c2F)C(C)(C)C)cc1] | tert-butyl N-(4-carbamoyl-1-[[2-fluoro-3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenyl]amino]butan-2-yl)carbamate | 866.40 | (400 MHz, DMSO-$d_6$) δ 8.99 (s, 1H), 8.37 (d, J = 7.8 Hz, 1H), 7.79 (d, J = 9.2 Hz, 1H), 7.44 (d, J = 8.3 Hz, 2H), 7.39 (d, J = 8.2 Hz, 2H), 7.24 (s, 1H), 6.85 (t, J = 7.8 Hz, 2H), 6.79 (d, J = 8.4 Hz, 1H), 6.71 (s, 1H), 6.60 (t, J = 8.2 Hz, 1H), 6.41 (t, J = 7.0 Hz, 1H), 5.22 (s, 1H), 5.10 (d, J = 3.6 Hz, 1H), 4.92 (p, J = 7.5 Hz, 1H), 4.52 (d, J = 9.3 Hz, 1H), 4.43 (t, J = 8.0 Hz, 1H), 4.28 (s, 1H), 3.64-3.56 (m, 6H), 3.12-2.99 (m, 1H), 3.06-3.02 (m, 1H), 2.46 (s, 3H), 2.32-2.20 (m, 3H), 2.17-2.07 (m, 4H), 2.09-1.97 (m, 1H), 2.03-1.99 (m, 1H), 1.85-1.73 (m, 1H), 1.57-1.53 (m, 1H), 1.54-1.50 (m, 5H), 1.39 (d, J = 13.2 Hz, 2H), 1.33-1.21 (m, 6H), 0.94 (s, 9H) |
| G162 | 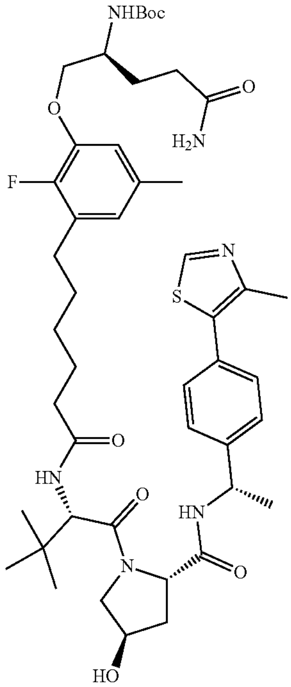 [SMILES: Cc1cc(CCCCCC(=O)N[C@H](C(=O)N2C[C@H](O)C[C@H]2C(=O)N[C@@H](C)c2ccc(-c3scnc3C)cc2)C(C)(C)C)c(F)c(OC[C@H](CCC(N)=O)NC(=O)OC(C)(C)C)c1] | tert-butyl N-[(2S)-4-carbamoyl-1-[2-fluoro-3-(5-[[(2S)-1-[(2S,4R)-4-hydroxy-2-[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)5-methylphenoxy]butan-2-yl]carbamate | 881.40 | $^1$H NMR (300 MHz, DMSO-$d_6$) δ 8.97 (s, 1H), 8.35 (d, J = 7.8 Hz, 1H), 7.77 (d, J = 9.2 Hz, 1H), 7.40 (q, J = 8.2 Hz, 4H), 7.25 (s, 1H), 6.79 (t, J = 7.5 Hz, 2H), 6.72 (s, 1H), 6.59 (d d, J = 6.2, 2.0 Hz, 1H), 5.08 (d, J = 3.6 Hz, 1H), 4.97-4.86 (m, 1H), 4.51 (d, J = 9.3 Hz, 1H), 4.42 (t, J = 8.0 Hz, 1H), 4.28 (s, 1H), 3.88 (d, J = 5.9 Hz, 2H), 3.78-3.66 (m, 1H), 3.64-3.57 (m, 2H), 2.45 (s, 3H), 2.33-2.24 (m, 1H), 2.22 (s, 3H), 2.17-2.08 (m, 3H), 2.06 (d, J = 0.9 Hz, 3H), 2.05-1.94 (m, 2H), 1.87-1.72 (m, 2H), 1.69-1.43 (m, 5H), 1.38 (s, 9H), 1.35 (s, 3H), 0.92 (s, 9H) |

TABLE 47-continued

Characterization data for intermediates prepare according to the procedure above.

| Inter-me-diate | Structure | Chemical Name | MS: [(M + 1)]$^+$ | $^1$H-NMR |
|---|---|---|---|---|
| G163 | 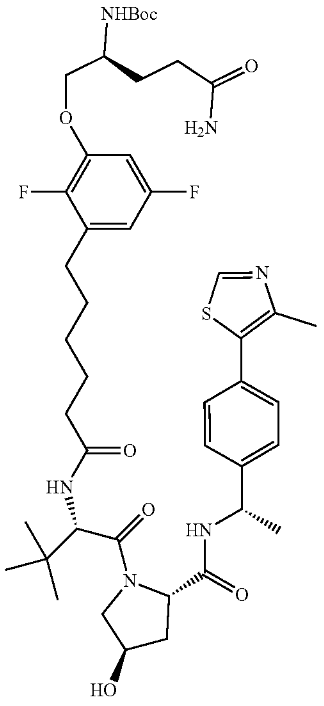 [SMILES: Cc1ncsc1-c1ccc([C@H](C)NC(=O)[C@@H]2C[C@@H](O)CN2C(=O)[C@@H](NC(=O)CCCCCc2cc(F)cc(OC[C@H](CCC(N)=O)NC(=O)OC(C)(C)C)c2F)C(C)(C)C)cc1] | tert-butyl N-[(2S)-4-carbamoyl-1-[2,5-difluoro-3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenoxy]butan-2-yl]carbamate | 885.35 | $^1$H NMR (400 MHz, CD3OD) δ 8.87 (s, 1H), 7.47-7.33 (m, 4H), 6.79-6.70 (m, 1H), 6.59-6.50 (m, 1H), 5.00 (q, J = 6.8 Hz, 1H), 4.64-4.53 (m, 2H), 4.43 (br, 1H), 3.97 (d, J = 5.4 Hz, 2H), 3.87 (d, J = 10.9 Hz, 2H), 3.74 (dd, J = 11.0, 3.9 Hz, 1H), 2.62 (t, J = 7.5 Hz, 2H), 2.47 (s, 3H), 2.39-2.12 (m, 4H), 2.04-1.90 (m, 1H), 1.85-1.73 (m, 1H), 1.70-1.54 (m, 5H), 1.50 (d, J = 7.0 Hz, 3H), 1.44 (s, 9H), 1.40-1.35 (m, 3H), 1.03 (s, 9H) |
| G164 | 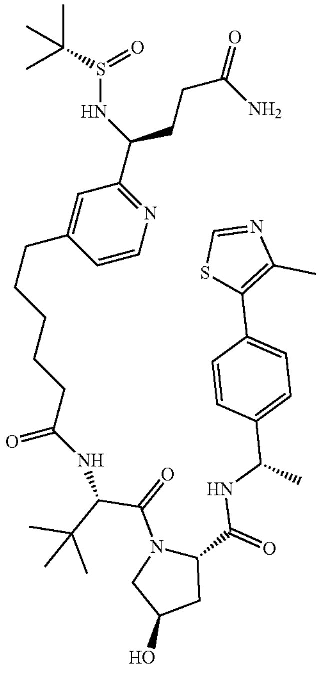 | (2S,4R)-1-[(2S)-2-(6-[2-[(1S)-3-carbamoyl-1-[(2-methylpropane-2-sulfinyl)amino]propyl]pyridin-4-yl]hexanamido)-3,3-dimethylbutanoyl]-4-hydroxy-N-[(1S)-1-[4-(4-methyl-1,3-thiazol-5-yl)phenyl]ethyl]pyrrolidine-2-carboxamide | 824.35 | (400 MHz, DMSO-d$_6$) δ 8.99 (s, 1H), 840-8.37 (t, J = 6.9 Hz, 2H), 7.81-7.79 (d, J = 9.3 Hz, 1H), 7.47-7.41 (m, 2H), 7.39-7.37 (d, J = 8.3 Hz, 2H), 7.31 (s, 1H), 7.20-7.10 (m, 2H), 6.85-6.77 (m, 1H), 5.75-5.74 (d, J = 5.5 Hz, 1H), 5.11-5.10 (d, J = 3.5 Hz, 1H), 4.96-4.89 (m, 1H), 4.53-4.50 (d, J = 9.4 Hz, 1H), 4.45-4.41 (t, J = 8.0 Hz, 1H), 4.30-4.27 (m, 1H), 4.25-4.21 (m, 1H), 3.61 (s, 1H), 2.70-2.67 (t, J = 7.5 Hz, 2H), 2.46 (s, 3H), 2.45-2.23 (m, 1H), 2.17-2.01 (m, 3H), 1.91-1.75 (m, 2H), 1.68-1.63 (m, 2H), 1.53-1.51 (m, 2H), 1.39-1.37 (d, J = 7.0 Hz, 3H), 1.31-1.23 (m, 2H), 1.20-1.16 (t, J = 7.1 Hz, 3H), 1.10 (s, 9H), 0.93 (s, 9H) |

TABLE 47-continued

| Characterization data for intermediates prepare according to the procedure above. | | | | |
|---|---|---|---|---|
| Intermediate | Structure | Chemical Name | MS: [(M + 1)]+ | $^1$H-NMR |
| G165 | 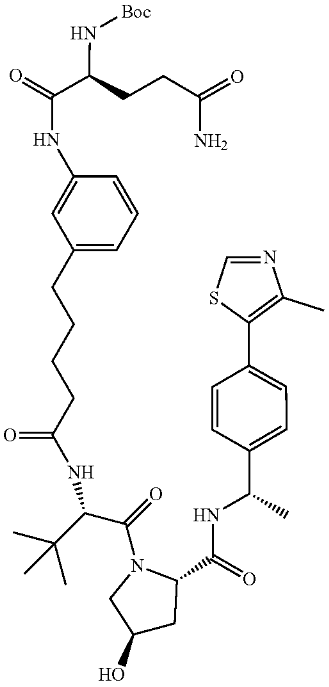 [SMILES: Cc1ncsc1-c1ccc([C@H](C)NC(=O)[C@@H]2C[C@@H](O)CN2C(=O)[C@@H](NC(=O)CCCCc2cccc(NC(=O)[C@H](CCC(N)=O)NC(=O)OC(C)(C)C)c2)C(C)(C)C)cc1] | tert-butyl N-[(1S)-3-carbamoyl-1-[[3-(4-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]butyl)phenyl]carbamoyl]propyl]carbamate | 848.65 | (300 MHz, DMSO-$d_6$) δ 9.84 (s, 1H), 8.98 (d, J = 3.6 Hz, 1H), 8.37-8.34 (m, 1H), 7.79 (d, J = 9.2 Hz, 1H), 7.43-7.36 (m, 6H), 7.29-7.17 (m, 2H), 7.05-6.69 (m, 3H), 5.08 (s, 1H), 4.96-4.87 (m, 1H), 4.51 (d, J = 9.5 Hz, 1H), 4.45-4.39 (m, 2H), 4.27 (s, 1H), 4.02 (s, 1H), 3.63-3.59 (m, 2H), 2.45 (d, J = 3.7 Hz, 3H), 2.28-2.14 (m, 4H), 2.00-1.79 (m, 5H), 1.57-1.50 (m, 4H), 1.38-1.30 (m, 12H), 0.93 (s, 9H) |
| G168 | 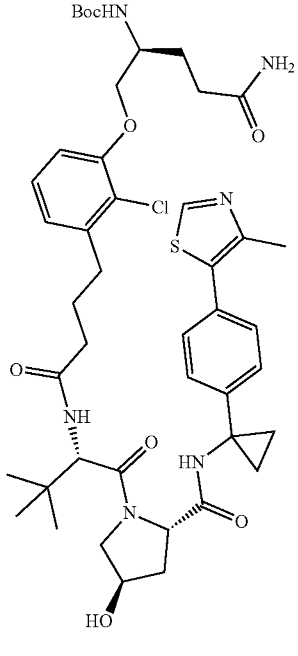 [SMILES: Cc1ncsc1-c1ccc(C2(NC(=O)[C@@H]3C[C@@H](O)CN3C(=O)[C@@H](NC(=O)CCCc3cccc(OC[C@H](CCC(N)=O)NC(=O)OC(C)(C)C)c3Cl)C(C)(C)C)CC2)cc1] | tert-butyl N-[(2S)-4-carbamoyl-1-[2-chloro-3-(3-[[(2S)-1-[(2S,4R)-4-hydroxy-2-([1-[4-(4-methyl-1,3-thiazol-5-yl)phenyl]cyclopropyl]carbamoyl)pyrrolidin-1-yl]-3,3-dimethyl-1-oxobutan-2-yl]carbamoyl]propyl)phenoxy]butan-2-yl]carbamate | 867.20 | (400 MHz, Methanol-$d_4$) δ 8.88 (d, J = 2.6 Hz, 1H), 7.43-7.32 (m, 4H), 7.22-7.16 (m, 1H), 6.99-6.91 (m, 2H), 4.67-4.51 (m, 3H), 4.04-3.91 (m, 3H), 3.85-3.80 (m, 1H), 2.84-2.76 (m, 2H), 2.52-2.45 (m, 3H), 2.45-2.33 (m, 4H), 2.26-2.18 (m, 1H), 2.10-2.02 (m, 3H), 1.98-1.81 (m, 3H), 1.50-1.42 (m, 9H), 1.40-1.28 (m, 4H), 1.07 (s, 9H) |

TABLE 47-continued

| Characterization data for intermediates prepare according to the procedure above. | | | | |
|---|---|---|---|---|
| Intermediate | Structure | Chemical Name | MS: [(M + 1)]$^+$ | $^1$H-NMR |
| G169 | 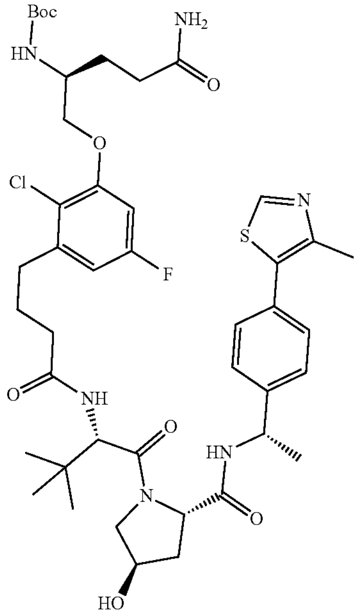 [SMILES: Cc1ncsc1-c1ccc([C@H](C)NC(=O)[C@@H]2C[C@@H](O)CN2C(=O)[C@@H](NC(=O)CCCc2cc(F)cc(OC[C@H](CCC(N)=O)NC(=O)OC(C)(C)C)c2Cl)C(C)(C)C)cc1] | tert-butyl N-[(2S)-4-carbamoyl-1-[2-chloro-5-fluoro-3-(3-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]propyl)phenoxy]butan-2-yl]carbamate | 873.30 | (300 MHz, DMSO-$d_6$) δ 9.00 (s, 1H), 8.39 (d, J = 7.8 Hz, 1H), 7.91 (d, J = 9.3 Hz, 1H), 7.42-7.78 (m, 4H), 7.28 (s, 1H), 6.98 (d, J = 10.3 Hz, 1H), 6.87-6.73 (m, 3H), 5.11 (d, J = 3.5 Hz, 1H), 4.99-4.90 (m, 1H), 4.54 (d, J = 9.3 Hz, 1H), 4.44 (t, J = 8.0 Hz, 1H), 4.30-4.28 (m, 1H), 4.01-3.91 (m, 2H), 3.79-3.75 (m, 1H), 2.68 (t, J = 7.6 Hz, 2H), 2.47 (s, 3H), 2.30-2.16 (m, 4H), 2.07-1.95 (m, 1H), 1.89-1.79 (m, 6H), 1.65-1.62 (m, 1H), 1.39 (s, 9H), 1.34-1.32 (m, 3H), 0.96 (s, 9H) |
| G170 | 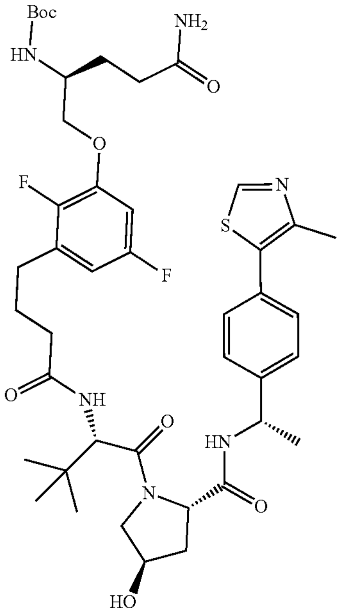 [SMILES: Cc1ncsc1-c1ccc([C@H](C)NC(=O)[C@@H]2C[C@@H](O)CN2C(=O)[C@@H](NC(=O)CCCc2cc(F)cc(OC[C@H](CCC(N)=O)NC(=O)OC(C)(C)C)c2F)C(C)(C)C)cc1] | tert-butyl N-[(2S)-4-carbamoyl-1-[2,5-difluoro-3-(3-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]propyl)phenoxy]butan-2-yl]carbamate | 857.30 | (300 MHz, DMSO-$d_6$) δ 9.00 (d, J = 1.2 Hz, 1H), 8.39 (d, J = 7.7 Hz, 1H), 7.90 (d, J = 9.3 Hz, 1H), 7.42 (q, J = 8.2 Hz, 4H), 7.29 (s, 1H), 6.98 (s, 1H), 6.87 (d, J = 8.2 Hz, 1H), 6.76 (s, 1H), 6.69 (s, 1H), 5.12-5.10 (m, 1H), 5.02-4.88 (m, 1H), 4.54 (d, J = 9.0 Hz, 1H), 4.44 (t, J = 8.0 Hz, 1H), 4.30-4.28 (m, 1H), 3.95-3.91 (m, 2H), 3.75-3.72 (m, 1H), 3.63-3.61 (m, 2H), 2.59-2.57 (m, 2H), 2.47 (s, 3H), 2.28-2.25 (m, 3H), 2.17-2.11 (m, 2H), 1.77-1.71 (m, 5H), 1.39-1.36 (m, 12H), 0.96 (s, 9H) |

TABLE 47-continued

| Characterization data for intermediates prepare according to the procedure above. | | | | |
|---|---|---|---|---|
| Inter-me-diate | Structure | Chemical Name | MS: [(M + 1)]+ | $^1$H-NMR |
| G171 | 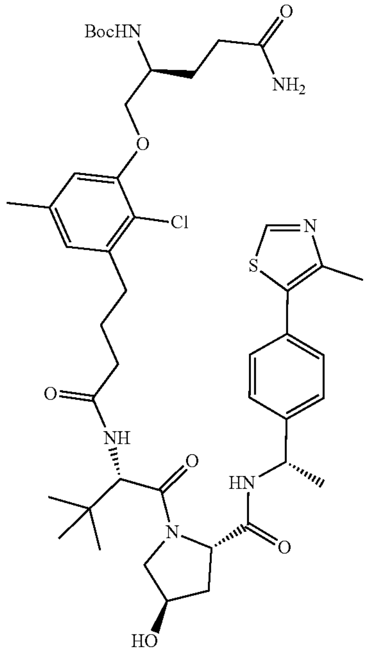 | tert-butyl N-[(2S)-4-carbamoyl-1-[2-chloro-3-(3-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]propyl)-5-methylphenoxy]butan-2-yl]carbamate | 869.35 | (300 MHz, DMSO-$d_6$) δ 9.00 (s, 1H), 8.39 (d, J = 7.8 Hz, 1H), 7.88 (d, J = 9.2 Hz, 1H), 7.42 (q, J = 8.4 Hz, 4H), 7.28 (s, 1H), 6.87-6.67 (m, 4H), 5.11 (d, J = 3.5 Hz, 1H), 4.98-4.88 (m, 1H), 4.55 (d, J = 9.3 Hz, 1H), 4.44 (t, J = 8.0 Hz, 1H), 4.29 (s, 1H), 3.91 (d, J = 6.1 Hz, 2H), 3.82-3.74 (m, 1H), 3.63 (d, J = 3.3 Hz, 2H), 2.63 (t, J = 7.6 Hz, 2H), 2.47 (s, 3H), 2.36-2.23 (m, 5H), 2.22-2.10 (m, 2H), 2.07-1.97 (m, 1H), 1.93-1.68 (m, 4 H), 1.66-1.55 (m, 1H), 1.40-1.37 (m, 12H), 0.96 (s, 9H) |

Tert-butyl N-[(3S,4R)-1-carbamoyl-4-([4-[3-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]amino)propyl]phenyl]methoxy)pentan-3-yl]carbamate (Intermediate G113)

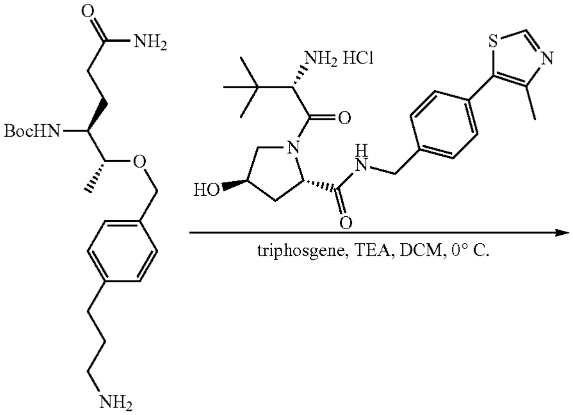

-continued

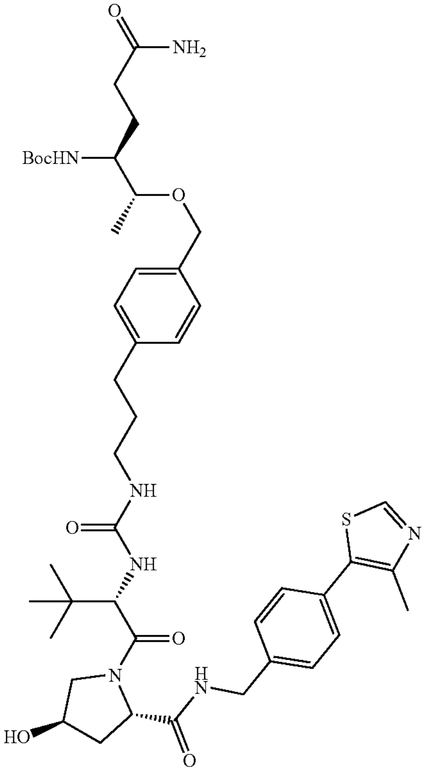

Intermediaite G113

To a stirred solution of tert-butyl N-[(3S,4R)-4-[[4-(3-aminopropyl)phenyl]methoxy]-1-carbamoylpentan-3-yl] carbamate (1.31 g, 3.329 mmol) and TEA (1.01 g, 9.987 mmol) in DCM (10.00 mL) was added triphosgene (345.74 mg, 1.165 mmol) in portions at 0° C. under nitrogen atmosphere. The resulting mixture was stirred for 2 h at 0° C. under nitrogen atmosphere. To the above mixture was added (2S,4R)-1-[(2S)-2-amino-3,3-dimethylbutanoyl]-4-hydroxy-N-[[4-(4-methyl-1,3-thiazol-5-yl)phenyl]methyl] pyrrolidine-2-carboxamide (1.44 g, 3.335 mmol) in portions at 0° C. The resulting mixture was stirred for additional 2 h at room temperature. The resulting mixture was concentrated under reduced pressure. The residue was purified by silica gel column chromatography, eluted with $CH_2Cl_2$/MeOH (12:1) to afford the title compound as a yellow solid (1.15 g, 41%): $^1$H NMR (400 MHz, $CDCl_3$) δ 8.70 (s, 1H), 7.67 (s, 1H), 7.34 (d, J=1.3 Hz, 3H), 7.21 (t, J=6.9 Hz, 4H), 7.14 (dd, J=12.2, 7.8 Hz, 4H), 6.45 (d, J=27.0 Hz, 2H), 4.90 (d, J=9.5 Hz, 2H), 4.56 (dd, J=11.6, 3.9 Hz, 2H), 4.39-4.28 (m, 3H), 3.57-3.52 (m, 5H), 2.65-2.60 (m, 4H), 2.51 (s, 3H), 2.26-2.20 (m, 2H), 2.09-1.89 (m, 2H), 1.81-1.77 (m, 2H), 1.60-1.56 (m, 2H), 1.43 (s, 9H), 1.19 (s, 3H), 0.95 (s, 9H); LC/MS (ESI, m/z): $[(M+1)]^+$=850.65.

4-[3-([2-[(tert-Butoxycarbonyl)amino]-4-carbamoylbutyl](methyl)amino)-2-fluorophenyl]butyl 4-nitrophenyl carbonate (Intermediate G166)

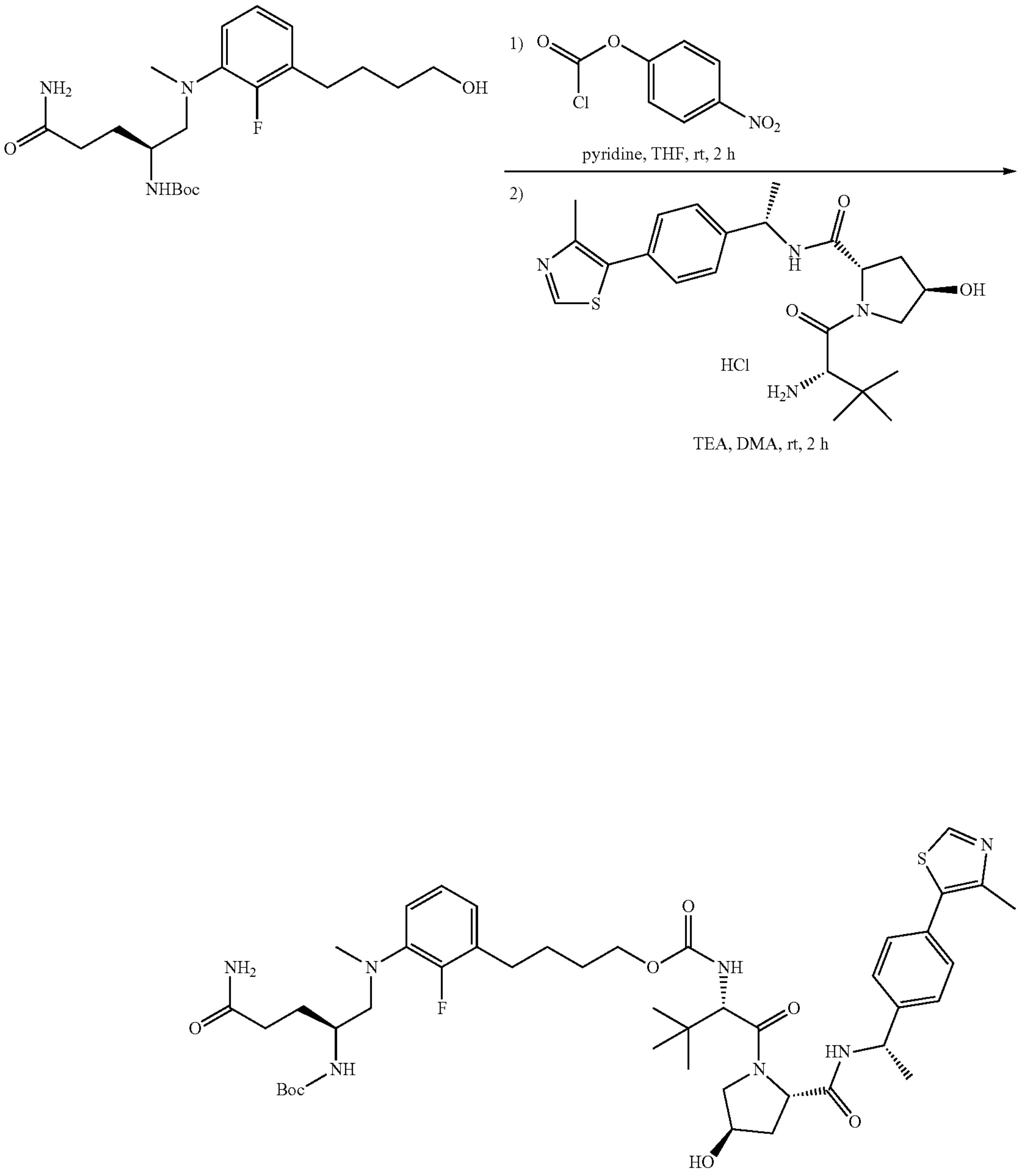

G166

4-[3-([2-[(tert-butoxycarbonyl)amino]-4-carbamoyl-butyl](methyl)amino)-2-fluorophenyl]butyl N-[(2S)-1-[(2SAR)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamate. To a stirred solution of tert-butyl N-(4-carbamoyl-1-[[2-fluoro-3-(4-hydroxybutyl)phenyl](methyl)amino]butan-2-yl)carbamate (693 mg, 1.69 mmol) and pyridine (200 mg, 2.53 mmol) in THF (10 mL) was added 4-nitrophenyl carbonochloridate (374 mg, 1.85 mmol) in THF (10 mL) dropwise at 0° C. under nitrogen atmosphere. The resulting mixture was stirred for 2 h at room temperature under nitrogen atmosphere until the active ester was fully converted. The reaction mixture was quenched with Sat.aq. $NaHCO_3$ (20 mL) and extracted with EA (20 mL). The organic layer was washed with brine (10 mL), dried over anhydrous $Na_2SO_4$ and filtered. The filtrate was concentrated under vacuum to give crude 4-[3-([2-[(tert-butoxycarbonyl)amino]-4-carbamoylbutyl](methyl)amino)-2-fluorophenyl]butyl 4-nitrophenyl carbonate intermediate. The crude intermediate was re-dissolved in THF (10 mL). Then to above solution were added (2S,4R)-1-[(2S)-2-amino-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride (972 mg, 2.02 mmol), TEA (340 mg, 3.37 mmol) and DMA (5 mL) at room temperature under nitrogen atmosphere. The resulting mixture was stirred for 2 h at room temperature under nitrogen atmosphere. The resulting mixture was concentrated under reduced pressure and the residue was purified by reverse phase flash chromatography with the following conditions: column, Spherical C18 Column, 20~40 um, 330 g; Mobile Phase A: Water (plus 10 mmol/L$NH_4HCO_3$), Mobile Phase B: ACN; Gradient: 40% to 60% B in 20 min; Detector: UV 254/220 nm. Desired fractions were collected at 53% B, concentrated under reduced pressure and lyophilized to afford title compound (852 mg, 57.36%) as a white solid; $^1$H NMR (400 MHz, DMSO-$d_6$) δ 8.99 (s, 1H), 8.39 (d, J=7.7 Hz, 1H), 7.41 (d, J=17.1 Hz, 4H), 7.22 (s, 1H), 6.94 (t, J=7.7 Hz, 2H), 6.79 (t, J=8.2 Hz, 1H), 6.73 (t, J=6.8 Hz, 1H), 6.69 (s, 1H), 6.55 (d, J=9.1 Hz, 1H), 5.11 (s, 1H), 4.95-4.87 (m, 1H), 4.44 (t, J=8.0 Hz, 1H), 4.29 (s, 1H), 4.18 (d, J=9.1 Hz, 1H), 4.01 (s, 1H), 3.95 (s, 1H), 3.62-3.58 (m, 2H), 3.08-3.02 (m, 2H), 2.79 (d, J=4.0 Hz, 3H), 2.60-2.56 (m, 3H), 2.46 (s, 3H), 2.08-1.94 (m, 4H), 1.84-1.73 (m, 2H), 1.63-1.57 (m, 4H), 1.46-1.42 (m, 1H), 1.37 (s, 9H), 1.34-1.30 (m, 2H), 0.94 (s, 9H); LC/MS (ESI, m/z): $[(M+1)]^+$=882.35

The intermediates in Table 48 were prepared according to the procedure to prepare Intermediate G166.

TABLE 48

Characterization data for intermediates prepared according to above.

| Intermediate | Structure | Chemical Name | MS: $[(M + 1)]^+$ | $^1$H-NMR |
|---|---|---|---|---|
| G167 625 | 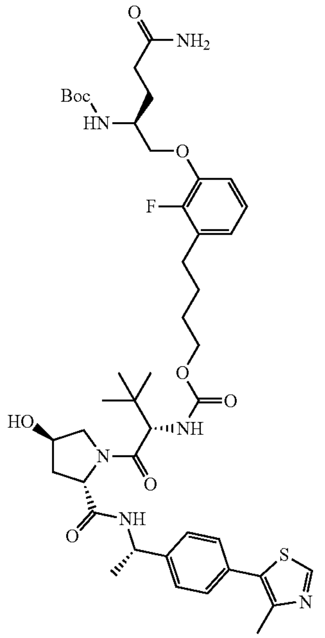 [SMILES: Cc1ncsc1-c1ccc([C@H](C)NC(=O)[C@@H]2C[C@@H](O)CN2C(=O)[C@@H](NC(=O)OCCCCc2cccc(OC[C@H](CCC(N)=O)NC(=O)OC(C)(C)C)c2F)C(C)(C)C)cc1] | 4-[3-[(2S)-2-[(tert-butoxycarbonyl)amino]-4-carbamoylbutoxy]-2-fluorophenyl]butyl N-[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamate | 869.60 | (400 MHz, DMSO-$d_6$) δ 8.99 (s, 1H), 8.39 (d, J = 7.8 Hz, 1H), 7.47-7.42 (m, 2H), 7.38 (d, J = 8.4 Hz, 2H), 7.27 (s, 1H), 7.06-6.97 (m, 2H), 6.99-6.91 (m, 1H), 6.83 (td, J = 6.6, 2.5 Hz, 2H), 6.74 (s, 1H), 5.11 (s, 1H), 4.91 (p, J = 7.0 Hz, 1H), 4.44 (t, J = 8.0 Hz, 1H), 4.29 (s, 1H), 4.17 (d, J = 9.2 Hz, 1H), 4.00 (s, 1H), 3.92 (d, J = 6.0 Hz, 3H), 3.74 (s, 1H), 3.62-3.58 (m, 2H), 2.63-2.59 (m, 1H), 2.46 (s, 3H), 2.15-2.11 (m, 2H), 2.08-1.97 (m, 1H), 1.81-1.77 (m, 2H), 1.58 (s, 5H), 1.39 (s, 9H), 1.33 (s, 2H), 1.25 (s, 2H), 0.94 (s, 9H) |

(4S,5R)-4-amino-5-([4-1[3-(2-1[3- [1-(2,6-dioxopiperidin-3-yl)-3-methyl-2-oxo-1,3-benzodiazol-5-yl] propoxy]ethoxy)propyl]phenyl]methoxy)hexanamide hydrochloride (Intermediate H)

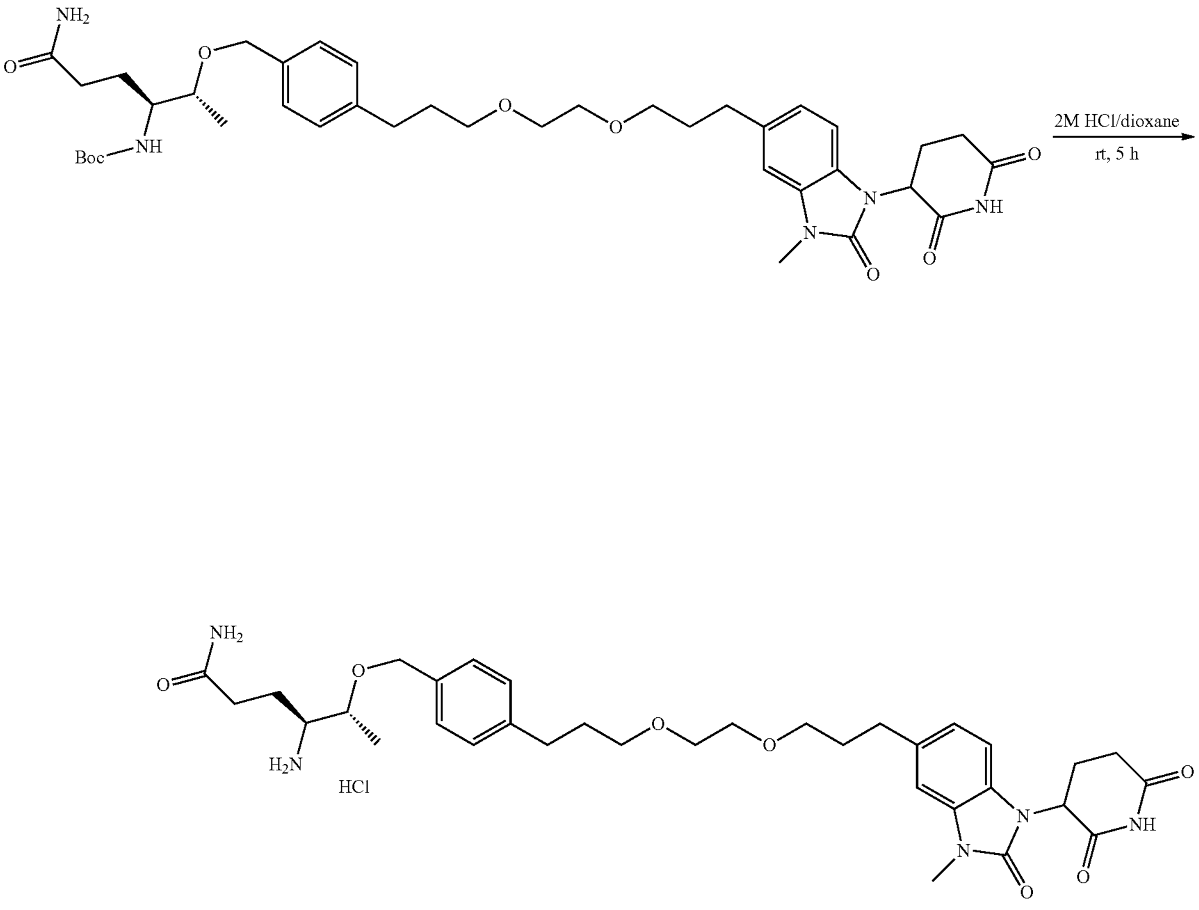

Intermediate H

To a solution of tert-butyl N-[(3S,4R)-1-carbamoyl-4-([4-[3-(2-[3-[1-(2,6-dioxopiperidin-3-yl)-3-methyl-2-oxo-1,3-benzodiazol-5-yl]propoxy]ethoxy)propyl]phenyl]methoxy) pentan-3-yl]carbamate (400 mg, 0.54 minol) in 1,4-dioxane (6.00 mL) was added HCl (4Min 1,4-dioxane, 6.00 mL) at 0° C. under nitrogen atmosphere. The resulting mixture was stirred for 5 hours at room temperature. The resulting mixture was concentrated under reduced pressure to afford the title compound as a brown solid (350 mg, 96%): $^1$H NMR (400 MHz, DMSO-$d_6$) δ 11.08 (s, 1H), 7.73-7.66 (m, 1H), 7.43 (s, 1H), 7.29 (d, J=8.0 Hz, 2H), 7.18 (d, J=7.9 Hz, 2H), 7.05-6.99 (m, 2H), 6.90-6.84 (m, 2H), 5.34 (dd, J=12.9, 5.2 Hz, 1H), 4.53 (d, J=11.8 Hz, 1H), 4.45 (d, J=11.7 Hz, 1H), 4.22 (d, J=6.5 Hz, 1H), 3.75 (dd, J=6.2, 3.4 Hz, 1H), 3.52-3.48 (m, 7H), 3.34-3.29 (m, 4H), 2.68-2.60 (m, 5H), 2.27-2.21 (m, 2H), 2.04-1.95 (m, 2H), 1.81-1.73 (m, 6H), 1.69-1.59 (m, 2H), 1.28-1.21 (m, 3H), 1.15 (d, J=6.6 Hz, 2H); MS (ESI, m/z): [(M+1)]$^+$=638.40.

The following intermediates in Table 49 were prepared according to the above procedure to prepare Intermediate H.

TABLE 49

| Characterization data for intermediates prepared according to procedure above. | | | | |
|---|---|---|---|---|
| Intermediate | Structure | Chemical Name | MS: $[(M + 1)]^+$ | $^1$H-NMR |
| H1 | 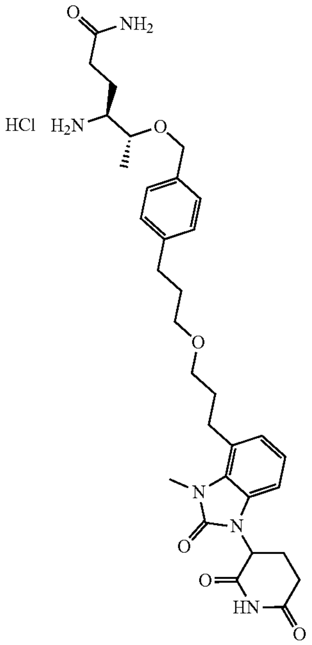 [SMILES: Cl ; C[C@@H](OCc1ccc(CCCOCCCc2cccc3c2n(C)c(=O)n3C2CCC(=O)NC2=O)cc1)[C@@H](N)CCC(N)=O] | (4S,5R)-4-amino-5-[[4-(3-[3-[1-(2,6-dioxopiperidin-3-yl)-3-methyl-2-oxo-1,3-benzodiazol-4-yl]propoxylpro-pyl)phenyl]meth-oxy]hexanamide hydrochloride | 594.4 | (400 MHz, $CD_3OD$) δ 7.32 (d, J = 8.0 Hz, 2H), 7.29-7.16 (m, 2H), 7.09-7.02 (m, 1H), 6.98 (td, J = 8.4, 7.5, 1.4 Hz, 2H), 5.34 (dd, J = 12.3, 5.4 Hz, 1H), 4.64 (d, J = 11.6 Hz, 1H), 4.56-4.44 (m, 1H), 3.89-3.75 (m, 1H), 3.77 (s, 1H), 3.70-3.66 (m, 8H), 3.61 (s, 1H), 3.52-3.46 (m, 4H), 3.38 (dt, J = 8.3, 4.3 Hz, 1H), 3.13-3.04 (m, 2H), 2.97-2.87 (m, 1H), 2.87-2.74 (m, 2H), 2.71 (t, J = 7.6 Hz, 2H), 2.44 (dt, J = 11.3, 7.2 Hz, 1H), 2.00-1.90 (m, 1H), 1.92 (s, 3H), 1.93-1.81 (m, 2H), 1.25 (d, J = 6.5 Hz, 3H). |
| H2 | 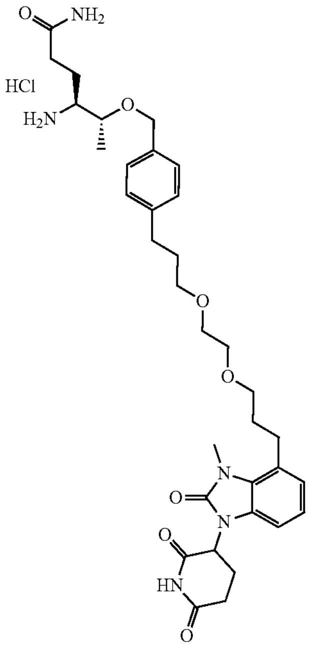 [SMILES: Cl ; C[C@@H](OCc1ccc(CCCOCCOCCCc2cccc3c2n(C)c(=O)n3C2CCC(=O)NC2=O)cc1)[C@@H](N)CCC(N)=O] | (4S,5R)-4-amino-5-[[4-[3-(2-[3-[1-(2,6-dioxopiperidin-3-yl)-3-methyl-2-oxo-1,3-benzodiazol-4-yl]propoxy] ethoxy)pro-pyl]phenyl]meth-oxy)hexanamide hydrochloride | 638.5 | (400 MHz, $CD_3OD$) δ 7.46-7.14 (m, 4H), 7.03-6.87 (m, 3H), 5.33 (s, 1H), 4.61 (d, J = 11.5 Hz, 1H), 4.48 (d, J = 11.5 Hz, 1H), 4.22 (s, 1H), 3.77 (s, 4H), 3.62 (s, 9H), 3.09 (s, 2H), 2.92 (d, J = 14.0 Hz, 2H), 2.80 (d, J = 14.8 Hz, 2H), 2.71 (s, 2H), 2.42 (s, 2H), 2.16 (s, 2H), 1.60 (s, 1H), 1.42 (s, 1H), 1.24 (d, J = 6.3 Hz, 3H). |

TABLE 49-continued

Characterization data for intermediates prepared according to procedure above.

| Intermediate | Structure | Chemical Name | MS: $[(M + 1)]^+$ | $^1$H-NMR |
|---|---|---|---|---|
| H3 | 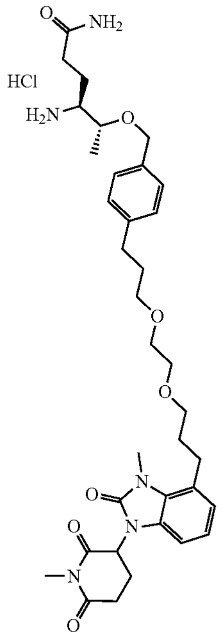 [SMILES: Cl ; C[C@@H](OCc1ccc(CCCOCCOCCCc2cccc3c2n(C)c(=O)n3C2CCC(=O)N(C)C2=O)cc1)[C@@H](N)CCC(N)=O] | (4S,5R)-4-amino-5-([4-[3-(2-[3-[3-methyl-1-(1-methyl-2,6-dioxopiperidin-3-yl)-2-oxo-1,3-benzodiazol-4-yl]propoxy] ethoxy)propyl]phenyl]methoxy)hexanamide hydrochloride | 652.5 | (400 MHz, $CD_3OD$) δ 7.30 (d, J = 8.0 Hz, 2H), 7.22 (d, J = 7.4 Hz, 2H), 7.09-6.92 (m, 3H), 5.35 (dd, J = 13.0, 5.2 Hz, 1H), 4.85 (s, 2H), 3.83-3.74 (m, 2H), 3.70-3.62 (m, 4H), 3.63 (d, J = 14.5 Hz, 4H), 3.63-3.55 (m, 2H), 3.58-3.46 (m, 2H), 3.19 (d, J = 5.5 Hz, 2H), 3.09 (t, J = 7.7 Hz, 2H), 2.94 (s, 1H), 2.75 (dt, J = 32.0, 6.6 Hz, 2H), 1.97-1.84 (m, 6H), 1.41 (d, J = 4.8 Hz, 4H), 1.33-1.20 (m, 4H). |
| H4 | 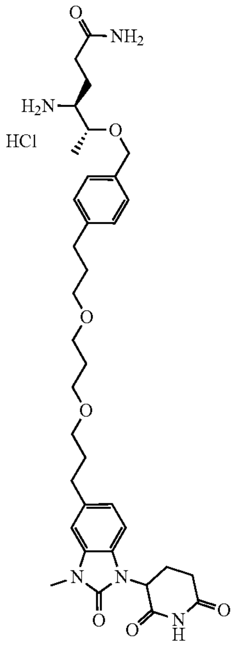 [SMILES: Cl ; C[C@@H](OCc1ccc(CCCOCCCOCCCc2ccc3c(c2)n(C)c(=O)n3C2CCC(=O)NC2=O)cc1)[C@@H](N)CCC(N)=O] | (4S,5R)-4-amino-5-([4-[3-(3-[3-[1-(2,6-dioxopiperidin-3-yl)-3-methyl-2-oxo-1,3-benzodiazol-5-yl]propoxylpropoxy)propyl]phenyl]methoxy)hexanamide hydrochloride | 652.4 | (400 MHz, $CDCl_3$) δ 8.73 (s, 1H), 7.24 (d, J = 7.8 Hz, 2H), 7.17 (d, J = 7.7 Hz, 2H), 6.94-6.86 (m, 2H), 6.73 (d, J = 8.0 Hz, 1H), 4.81-4.78 (m, 1H), 4.45-4.42 (m, 1H), 4.33 (t, J = 4.7 Hz, 2H), 4.26-4.21 (m, 1H), 3.92-3.88 (m, 4H), 3.81 (s, 5H), 3.58-3.53 (m, 4H), 3.47-3.41 (m, 3H), 2.80-2.54 (m, 7H), 1.88 (s, 5H), 1.27 (s, 3H). |

TABLE 49-continued

| Characterization data for intermediates prepared according to procedure above. | | | | |
|---|---|---|---|---|
| Intermediate | Structure | Chemical Name | MS: [(M + 1)]+ | 1H-NMR |
| H5 | 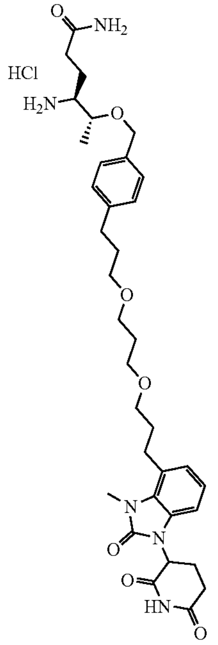 [SMILES: Cl ; C[C@@H](OCc1ccc(CCCOCCCOCCCc2cccc3c2n(C)c(=O)n3C2CCC(=O)NC2=O)cc1)[C@@H](N)CCC(N)=O] | (4S,5R)-4-amino-5-([4-[3-(3-[3-[1-(2,6-dioxopiperidin-3-yl)-3-methyl-2-oxo-1,3-benzodiazol-4-yl]propoxy]propoxy)propyl]phenyl]methoxy)hexanamide hydrochloride | 652.5 | (400 MHz, $CD_3OD$) δ 7.33-7.21 (m, 2H), 7.21 (d, J = 8.2 Hz, 2H), 7.05 (t, J = 7.8 Hz, 1H), 6.98 (t, J = 8.2 Hz, 2H), 5.34 (dd, J = 12.3, 5.4 Hz, 1H), 4.70-4.54 (m, 1H), 4.53-4.44 (m, 1H), 3.89-3.75 (m, 2H), 3.68-3.62 (m, 3H), 3.67-3.52 (m, 4H), 3.44 (t, J = 6.4 Hz, 2H), 3.33 (s, 4H), 3.07 (t, J = 7.9 Hz, 2H), 2.96-2.87 (m, 1H), 2.81 (d, J = 14.0 Hz, 2H), 2.70 (t, J = 7.7 Hz, 2H), 2.43 (dt, J = 11.6, 7.4 Hz, 1H), 1.93-1.86 (m, 8H), 1.23-1.19 (m, 3H). |
| H6 | 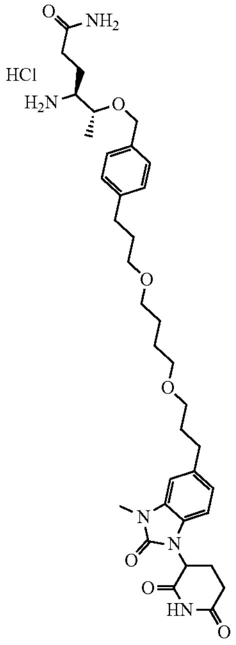 [SMILES: Cl ; C[C@@H](OCc1ccc(CCCOCCCCOCCCc2ccc3c(c2)n(C)c(=O)n3C2CCC(=O)NC2=O)cc1)[C@@H](N)CCC(N)=O] | (4S,5R)-4-amino-5-([4-[3-(4-[3-[1-(2,6-dioxopiperidin-3-yl)-3-methyl-2-oxo-1,3-benzodiazol-5-yl]propoxy]butoxy)propyl]phenyl]methoxy)hexanamide hydrochloride | 666.5 | (400 MHz, DMSO-$d_6$) δ 11.08 (s, 1H), 7.87 (d, J = 45.3 Hz, 2H), 7.31-7.27 (m, 1H), 7.20-7.16 (m, 2H), 7.07 (s, 1H), 7.02 (d, J = 14.9 Hz, 2H), 6.87 (d, J = 8.1 Hz, 1H), 5.76 (s, 1H), 5.34 (dd, J = 12.8, 5.3 Hz, 1H), 4.57-4.41 (m, 2H), 4.12 (dd, J = 11.0, 6.0 Hz, 1H), 4.07-3.99 (m, 1H), 3.87 (s, 2H), 3.78-3.72 (m, 2H), 3.40 (s, 6H), 2.70-2.55 (m, 5H), 2.27-2.17 (m, 2H), 2.08 (s, 2H), 2.01 (d, J = 8.1 Hz, 1H), 1.92 (s, 1H), 1.79 (dq, J = 15.2, 7.7 Hz, 5H), 1.60-1.50 (m, 4H), 1.36 (s, 1H), 1.24 (s, 1H), 1.16-1.07 (m, 3H). |

TABLE 49-continued

Characterization data for intermediates prepared according to procedure above.

| Intermediate | Structure | Chemical Name | MS: [(M + 1)]$^+$ | $^1$H-NMR |
|---|---|---|---|---|
| H7 | 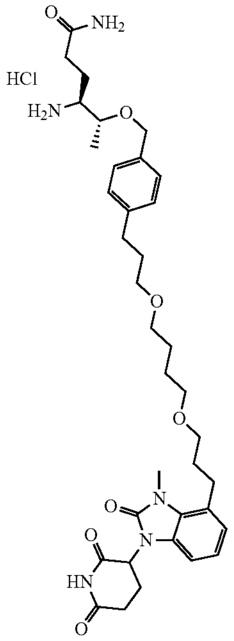 [SMILES: Cl ; C[C@@H](OCc1ccc(CCCOCCCCOCCCc2cccc3c2n(C)c(=O)n3C2CCC(=O)NC2=O)cc1)[C@@H](N)CCC(N)=O] | (4S,5R)-4-amino-5-([4-[3-(4-[3-[1-(2,6-dioxopiperidin-3-yl)-3-methyl-2-oxo-1,3-benzodiazol-4-yl]propoxy]butoxy)propyl]phenyl]methoxy)hexanamide hydrochloride | 666.4 | (400 MHz, DMSO-$d_6$) δ 11.09 (s, 1H), 8.02 (s, 2H), 7.45 (s, 1H), 7.38 (d, J = 8.1 Hz, 1H), 7.29 (d, J = 7.8 Hz, 2H), 7.26-7.09 (m, 3H), 6.97 (d, J = 5.8 Hz, 2H), 6.96-6.83 (m, 2H), 5.38 (dd, J = 12.5, 5.4 Hz, 1H), 4.52 (d, J = 11.6 Hz, 1H), 4.48-4.34 (m, 1H), 4.16-4.06 (m, 1H), 3.80-3.72 (m, 1H), 3.53-3.46 (m, 1H), 3.44 (d, J = 5.3 Hz, 1H), 3.41 (s, 5H), 3.40 (s, 4H), 3.39-3.31 (m, 2H), 3.26 (s, 1H), 2.96 (t, J = 7.9 Hz, 2H), 2.29-2.17 (m, 2H), 2.00 (dd, J = 11.8, 4.8 Hz, 2H), 1.78 (tt, J = 21.4, 8.1 Hz, 6H), 1.36 (s, 3H), 1.22-1.06 (m, 4H). |
| H8 | 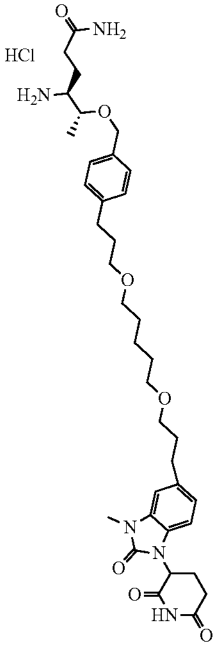 [SMILES: Cl ; C[C@@H](OCc1ccc(CCCOCCCCCOCCCc2ccc3c(c2)n(C)c(=O)n3C2CCC(=O)NC2=O)cc1)[C@@H](N)CCC(N)=O] | (4S,5R)-4-amino-5-[(4-[3-[(6-[3-[1-(2,6-dioxopiperidin-3-yl)-3-methyl-2-oxo-1,3-benzodiazol-5-yl]propoxy]hexyl)oxy]propyl]phenyl)methoxy]hexanamide hydrochloride | 680.4 | (400 MHz, $CD_3OD$) δ 7.28 (d, J = 7.8 Hz, 2H), 7.18 (d, J = 7.8 Hz, 2H), 7.02 (d, J = 8.3 Hz, 2H), 6.98 (d, J = 8.1 Hz, 1H), 5.32 (dd, J = 12.6, 5.5 Hz, 1H), 4.62 (d, J = 11.5 Hz, 1H), 4.50 (d, J = 11.5 Hz, 1H), 4.23 (d, J = 6.6 Hz, 1H), 3.84-3.73 (m, 3H), 3.68 (d, J = 1.1 Hz, 11H), 2.92 (dd, J = 18.3, 5.2 Hz, 1H), 2.79 (q, J = 9.9, 8.1 Hz, 4H), 2.68 (t, J = 7.7 Hz, 2H), 2.51-2.35 (m, 2H), 2.17 (d, J = 10.5 Hz, 1H), 1.89 (dp, J = 21.9, 6.9 Hz, 2H), 1.63 (q, J = 6.9 Hz, 5H), 1.52 (s, 2H), 1.31 (s, 1H), 1.24 (d, J = 6.4 Hz, 3H). |

TABLE 49-continued

Characterization data for intermediates prepared according to procedure above.

| Intermediate | Structure | Chemical Name | MS: $[(M+1)]^+$ | $^1$H-NMR |
|---|---|---|---|---|
| H9 | 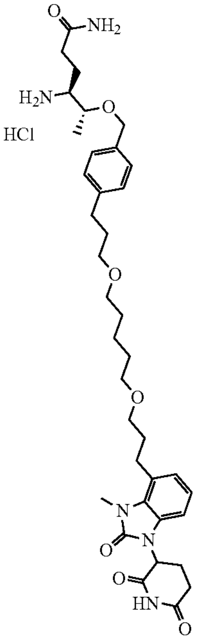 [SMILES: Cl ; C[C@@H](OCc1ccc(CCCOCCCCCOCCCc2cccc3c2n(C)c(=O)n3C2CCC(=O)NC2=O)cc1)[C@@H](N)CCC(N)=O] | (4S,5R)-4-amino-5-[(4-[3-[(5-[3-[1-(2,6-dioxopiperidin-3-yl)-3-methyl-2-oxo-1,3-benzodiazol-4-yl]propoxy]pentyl)oxy]propyl]phenyl)methoxy]hexanamide hydrochloride | 680.5 | (400 MHz, $CD_3OD$) δ 7.29 (d, J = 7.9 Hz, 2H), 7.19 (d, J = 7.9 Hz, 2H), 7.09-6.93 (m, 3H), 5.34 (dd, J = 12.2, 5.4 Hz, 1H), 4.62 (d, J = 11.5 Hz, 1H), 4.50 (d, J = 11.6 Hz, 1H), 3.77 (s, 2H), 3.62 (s, 9H), 3.48-3.42 (m, 6H), 3.12-3.03 (m, 2H), 2.85-2.77 (m, 2H), 2.69 (t, J = 7.7 Hz, 2H), 2.51-2.36 (m, 1H), 1.93 (s, 3H), 1.87 (td, J = 15.3, 14.4, 6.5 Hz, 2H), 1.64 (t, J = 7.0 Hz, 5H), 1.58-1.46 (m, 2H), 1.25 (d, J = 6.5 Hz, 3H). |
| H10 | 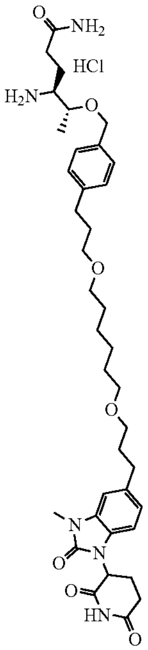 [SMILES: C[C@@H](OCc1ccc(CCCOCCCCCCOCCCc2ccc3c(c2)n(C)c(=O)n3C2CCC(=O)NC2=O)cc1)[C@@H](N)CCC(N)=O ; Cl] | (4S,5R)-4-amino-5-[(4-[3-[(6-[3-[1-(2,6-dioxopiperidin-3-yl)-3-methyl-2-oxo-1,3-benzodiazol-5-yl]propoxy]hexyl)oxy]propyl]phenyl)methoxy]hexanamide hydrochloride | 692.4 | (400 MHz, DMSO-$d_6$) δ 7.37 (s, 1H), 7.27 (d, J = 7.8 Hz, 2H), 7.24-7.13 (m, 2H), 7.05-6.98 (m, 2H), 6.90-6.81 (m, 2H), 5.34 (dd, J = 12.7, 5.3 Hz, 1H), 4.51 (d, J = 11.7 Hz, 1H), 4.47 (s, 1H), 4.43 (d, J = 11.7 Hz, 1H), 3.60 (dd, J = 6.6, 3.6 Hz, 1H), 3.51 (d, J = 4.9 Hz, 1H), 3.42-3.30 (m, 14H), 3.09-3.02 (m, 1H), 2.95 (s, 6H), 2.93-2.84 (m, 1H), 2.79 (s, 6H), 2.05-1.96 (m, 1H), 1.85-1.73 (m, 5H), 1.71 (dd, J = 10.1, 4.8 Hz, 1H), 1.64-1.50 (m, 2H), 1.54-1.46 (m, 4H). |

TABLE 49-continued

| Characterization data for intermediates prepared according to procedure above. | | | | |
|---|---|---|---|---|
| Intermediate | Structure | Chemical Name | MS: [(M + 1)]+ | $^1$H-NMR |
| H11 | 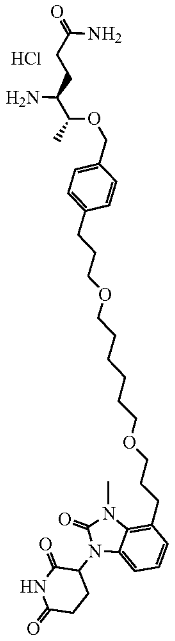 [SMILES: Cl ; C[C@@H](OCc1ccc(CCCOCCCCCCOCCCc2cccc3c2n(C)c(=O)n3C2CCC(=O)NC2=O)cc1)[C@@H](N)CCC(N)=O] | (4S,5R)-4-amino-5-[(4-[3-[(6-[3-[1-(2,6-dioxopiperidin-3-yl)-3-methyl-2-oxo-1,3-benzodiazol-4-yl]propoxy]hexyl)oxy]propyl]phenyl)methoxy]hexanamide hydrochloride | 694.6 | (400 MHz, DMSO-d$_6$) δ 11.09 (s, 1H), 8.00 (s, 2H), 7.44 (s, 1H), 7.29 (d, J = 7.7 Hz, 2H), 7.18 (s, 1H), 7.16 (s, 1H), 7.00-6.83 (m, 4H), 5.38 (dd, J = 12.5, 5.3 Hz, 1H), 4.53 (d, J = 11.6 Hz, 1H), 4.45 (d, J = 11.7 Hz, 1H), 4.25 (s, 2H), 3.80-3.73 (m, 1H), 3.43 (d, J = 5.9 Hz, 1H), 3.42-3.30 (m, 9H), 3.26 (s, 1H), 2.90 (s, 1H), 2.77-2.56 (m, 4H), 2.29-2.17 (m, 3H), 2.04-1.95 (m, 1H), 1.82 (s, 2H), 1.83-1.69 (m, 4H), 1.51 (d, J = 7.8 Hz, 5H), 1.36 (s, 4H), 1.15 (d, J = 6.3 Hz, 3H). |
| H12 | 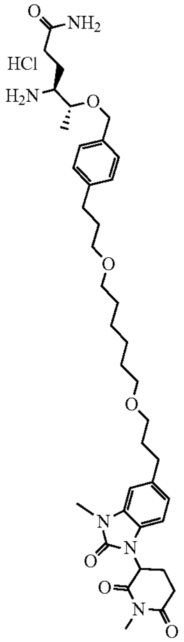 [SMILES: Cl ; C[C@@H](OCc1ccc(CCCOCCCCCCOCCCc2ccc3c(c2)n(C)c(=O)n3C2CCC(=O)N(C)C2=O)cc1)[C@@H](N)CCC(N)=O] | (4S,5R)-4-amino-5-[(4-[3-[(6-[3-[3-methyl-1-(1-methyl-2,6-dioxopiperidin-3-yl)-2-oxo-1,3-benzodiazol-5-yl]propoxy]hexyl)oxy]propyl]phenyl)methoxy]hexanamide hydrochloride | 708.6 | (400 MHz, DMSO-d$_6$) δ 7.99 (s, 2H), 7.44 (s, 1H), 7.29 (d, J = 7.8 Hz, 2H), 7.17 (d, J = 7.9 Hz, 2H), 7.06-6.98 (m, 2H), 6.94-6.82 (m, 2H), 5.41 (dd, J = 12.9, 5.3 Hz, 1H), 4.78 (s, 3H), 4.57-4.42 (m, 2H), 3.82-3.73 (m, 1H), 3.42-3.31 (m, 4H), 3.27 (s, 1H), 3.04 (s, 3H), 3.02-2.92 (m, 1H), 2.80 (s, 1H), 2.78-2.67 (m, 1H), 2.63 (dt, J = 20.4, 7.8 Hz, 4H), 2.29-2.17 (m, 2H), 2.01 (d, J = 12.7 Hz, 1H), 1.82-1.76 (m, J = 16.3, 8.0, 7.3 Hz, 6H), 1.51 (s, 5H), 1.37 (s, 4H), 1.33 (s, 4H), 1.22-1.12 (m, 3H). |

TABLE 49-continued

| Characterization data for intermediates prepared according to procedure above. | | | | |
|---|---|---|---|---|
| Intermediate | Structure | Chemical Name | MS: $[(M+1)]^+$ | $^1H$-NMR |
| H13 | 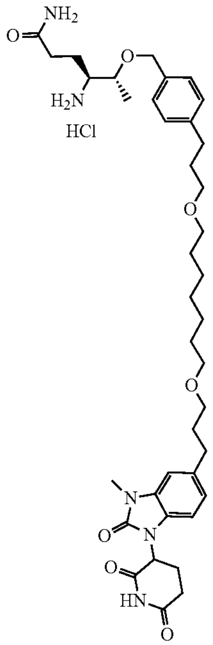 [SMILES: C[C@@H](OCc1ccc(CCCOCCCCCCCOCCCc2ccc3c(c2)n(C)c(=O)n3C2CCC(=O)NC2=O)cc1)[C@@H](N)CCC(N)=O ; Cl] | (4S,5R)-4-amino-5-[(4-[3-[(7-[3-[1-(2,6-dioxopiperidin-3-yl)-3-methyl-2-oxo-1,3-benzodiazol-5-yl]propoxy]heptyl)oxy]propyl]phenyl)methoxy]hexanamide hydrochloride | 708.6 | (400 MHz, DMSO-$d_6$) δ 11.08 (s, 1H), 7.95 (s, 2H), 7.43 (s, 1H), 7.29 (d, J = 7.8 Hz, 2H), 7.17 (d, J = 7.7 Hz, 2H), 7.05-6.97 (m, 2H), 6.93 (s, 1H), 6.86 (d, J = 8.6 Hz, 1H), 5.34 (dd, J = 12.7, 5.3 Hz, 1H), 4.53 (d, J = 11.6 Hz, 1H), 4.45 (d, J = 11.7 Hz, 1H), 3.42-3.30 (m, 8H), 3.34 (s, 8H), 2.91 (s, 1H), 2.73-2.56 (m, 6H), 2.28-2.17 (m, 2H), 2.01 (d, J = 8.2 Hz, 1H), 1.81-1.74 (m, 4H), 1.50 (s, 5H), 1.36-1.31 (m, 5H), 1.15 (d, J = 6.5 Hz, 3H). |
| H14 | 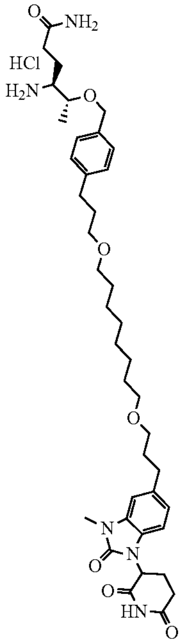 [SMILES: Cl ; C[C@@H](OCc1ccc(CCCOCCCCCCCCOCCCc2ccc3c(c2)n(C)c(=O)n3C2CCC(=O)NC2=O)cc1)[C@@H](N)CCC(N)=O] | (4S,5R)-4-amino-5-[(4-[3-[(8-[3-[1-(2,6-dioxopiperidin-3-yl)-3-methyl-2-oxo-1,3-benzodiazol-5-yl]propoxy]octyl)oxy]propyl]phenyl)methoxy]hexanamide hydrochloride | 722.7 | (400 MHz, DMSO-$d_6$) δ 7.88 (s, 1H), 7.76-7.61 (m, 5H), 7.26 (q, J = 9.7, 8.8 Hz, 1H), 7.23-7.10 (m, 1H), 7.05-6.98 (m, 1H), 6.86 (d, J = 10.2 Hz, 1H), 4.53 (d, J = 11.5 Hz, 1H), 4.23 (t, J = 6.5 Hz, 5H), 3.93 (d, J = 5.8 Hz, 1H), 3.65 (s, 1H), 3.57 (s, 1H), 3.33 (s, 3H), 2.67-2.58 (m, 2H), 2.19 (s, 1H), 1.79 (dd, J = 17.1, 9.3 Hz, 2H), 1.71-1.59 (m, 3H), 1.45-1.31 (m, 5H), 1.36 (s, 6H), 1.34-1.24 (m, 1H), 1.29 (s, 4H), 1.25 (s, 2H), 1.21-1.06 (m, 2H), 0.96-0.81 (m, 9H). |

TABLE 49-continued

| Intermediate | Structure | Chemical Name | MS: [(M + 1)]$^+$ | $^1$H-NMR |
|---|---|---|---|---|
| Characterization data for intermediates prepared according to procedure above. | | | | |
| H15 | 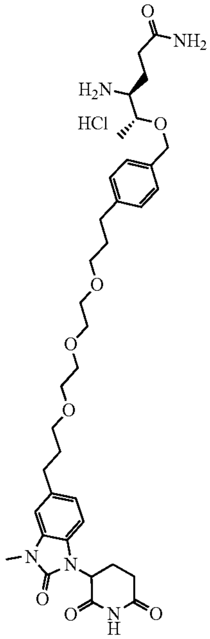 [SMILES: C[C@@H](OCc1ccc(CCCOCCOCCOCCCc2ccc3c(c2)n(C)c(=O)n3C2CCC(=O)NC2=O)cc1)[C@@H](N)CCC(N)=O ; Cl] | (4S,5R)-4-amino-5-[(4-[3-[2-(2-[3-[1-(2,6-dioxopiperidin-3-yl)-3-methyl-2-oxo-1,3-benzodiazol-5-yl]propoxy]ethoxy)ethoxy]propyl]phenyl)methoxy]hexanamide hydrochloride | 682.4 | (400 MHz, DMSO-$d_6$) δ 11.08 (s, 1H), 7.68-7.53 (m, 4H), 7.28 (d, J = 7.6 Hz, 2H), 7.17 (d, J = 7.8 Hz, 2H), 7.07-6.98 (m, 2H), 6.87 (d, J = 8.1 Hz, 1H), 5.38-5.29 (m, 1H), 4.65 (d, J = 6.5 Hz, 1H), 4.57-4.42 (m, 4H), 4.21 (d, J = 8.3 Hz, 2H), 4.14-4.07 (m, 3H), 3.94-3.82 (m, 3H), 3.82-3.72 (m, 3H), 3.14-3.04 (m, 2H), 2.63 (dt, J = 21.6, 7.8 Hz, 6H), 2.24 (t, J = 7.6 Hz, 2H), 2.00 (d, J = 15.7 Hz, 2H), 1.91 (d, J = 2.6 Hz, 2H), 1.86-1.64 (m, 7H), 1.51 (d, J = 6.6 Hz, 1H). |
| H16 | 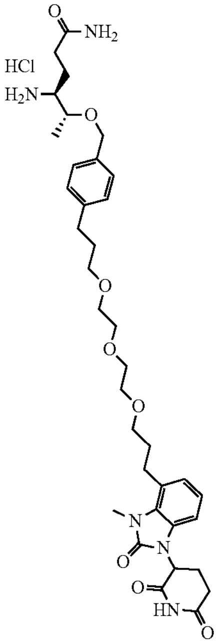 [SMILES: Cl ; C[C@@H](OCc1ccc(CCCOCCOCCOCCCc2cccc3c2n(C)c(=O)n3C2CCC(=O)NC2=O)cc1)[C@@H](N)CCC(N)=O] | (4S,5R)-4-amino-5-[(4-[3-[2-(2-[3-[1-(2,6-dioxopiperidin-3-yl)-3-methyl-2-oxo-1,3-benzodiazol-4-yl]propoxy]ethoxy)ethoxy]propyl]phenyl)methoxy]hexanamide hydrochloride | 682.5 | (400 MHz, DMSO-$d_6$) δ 11.09 (s, 1H), 7.67-7.53 (m, 1H), 7.43 (s, 1H), 7.28 (d, J = 7.9 Hz, 2H), 7.17 (d, J = 7.5 Hz, 2H), 6.99-6.91 (m, 3H), 6.91-6.84 (m, 1H), 5.37 (dd, J = 12.6, 5.4 Hz, 1H), 4.52 (d, J = 11.7 Hz, 1H), 4.45 (d, J = 11.5 Hz, 1H), 4.16-4.08 (m, 1H), 3.78-3.72 (m, 1H), 3.65 (s, 2H), 3.56 (s, 3H), 3.40 (s, 8H), 3.27 (s, 1H), 3.00-2.83 (m, 3H), 2.67-2.56 (m, 3H), 2.24 (t, J = 7.5 Hz, 2H), 2.08-1.95 (m, 2H), 1.92 (s, 1H), 1.78 (ddd, J = 22.8, 15.2, 8.0 Hz, 4H), 1.77 (s, 2H), 1.19 (d, J = 2.6 Hz, 1H), 1.12 (dd, J = 18.1, 6.6 Hz, 3H). |

TABLE 49-continued

| Characterization data for intermediates prepared according to procedure above. | | | | |
|---|---|---|---|---|
| Intermediate | Structure | Chemical Name | MS: [(M + 1)]+ | $^1$H-NMR |
| H17 | 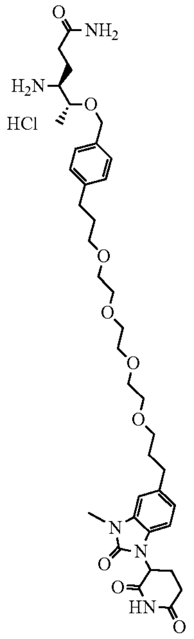 [SMILES: Cl ; C[C@@H](OCc1ccc(CCCOCCOCCOCCOCCCc2ccc3c(c2)n(C)c(=O)n3C2CCC(=O)NC2=O)cc1)[C@@H](N)CCC(N)=O] | (4S,5R)-4-amino-5-[(4-[16-[1-(2,6-dioxopiperidin-3-yl)-3-methyl-2-oxo-2,3-dihydro-1H-1,3-benzodiazol-5-yl]-4,7,10,13-tetraoxahexadecan-1-yl]phenyl)methoxy]hexanamide hydrochloride | 726.6 | (400 MHz, DMSO-$d_6$) δ 11.10 (s, 1H), 8.02 (s, 2H), 7.64 (t, J = 6.1 Hz, 1H), 7.63-7.52 (m, 1H), 7.46 (s, 1H), 7.32-7.21 (m, 2H), 7.17 (d, J = 7.9 Hz, 2H), 7.07-6.98 (m, 2H), 6.94 (s, 1H), 6.91-6.84 (m, 1H), 5.35 (dd, J = 12.7, 5.3 Hz, 1H), 4.53 (d, J = 11.7 Hz, 1H), 4.45 (d, J = 11.7 Hz, 1H), 4.09-3.98 (m, 1H), 3.76 (dt, J = 8.8, 4.3 Hz, 1H), 3.66 (s, 1H), 3.56-3.45 (m, 3H), 3.40 (s, 5H), 3.44-3.34 (m, 3H), 3.32 (s, 3H), 3.27 (s, 1H), 2.93-2.85 (m, 1H), 2.66 (tt, J = 22.6, 8.3 Hz, 6H), 2.25 (t, J = 7.5 Hz, 2H), 2.01 (d, J = 9.2 Hz, 2H), 1.80 (dd, J = 18.8, 7.8 Hz, 5H), 1.77-1.67 (m, 1H), 1.27-1.04 (m, 4H). |
| H18 | 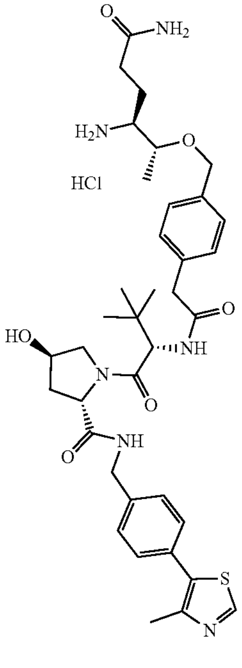 [SMILES: Cc1ncsc1-c1ccc(CNC(=O)[C@@H]2C[C@@H](O)CN2C(=O)[C@@H](NC(=O)Cc2ccc(CO[C@H](C)[C@@H](N)CCC(N)=O)cc2)C(C)(C)C)cc1 ; Cl] | (2S,4R)-1-[(2S)-2-[2-[4-([[(2R,3S)-3-amino-5-carbamoylpentan-2-yl]oxy]methyl)phenyl]acetamido]-3,3-dimethylbutanoyl]-4-hydroxy-N-[[4-(4-methyl-1,3-thiazol-5-yl)phenyl]methyl]pyrrolidine-2-carboxamide hydrochloride | 707.5 | (400 MHz, DMSO-$d_6$) δ 8.60 (s, 1H), 8.10 (d, J = 9.3 Hz, 1H), 8.06 (s, 2H), 7.47-7.37 (m, 4H), 7.31 (d, J = 8.0 Hz, 2H), 7.26 (d, J = 8.0 Hz, 2H), 6.92 (s, 1H), 6.80 (s, 1H), 4.58-4.39 (m, 4H), 4.35 (s, 1H), 4.23 (dd, J = 15.9, 5.3 Hz, 1H), 3.79-3.73 (m, 1H), 3.66 (dt, J = 14.6, 5.8 Hz, 3H), 3.49-3.37 (m, 1H), 3.26 (s, 1H), 2.46 (s, 3H), 2.24 (t, J = 7.2 Hz, 2H), 2.10-2.00 (m, 1H), 1.96-1.85 (m, 1H), 1.81-1.71 (m, 1H), 1.75 (s, 2H), 1.15 (d, J = 6.3 Hz, 3H), 0.92 (s, 9H). |

TABLE 49-continued

| Characterization data for intermediates prepared according to procedure above. | | | | |
|---|---|---|---|---|
| Intermediate | Structure | Chemical Name | MS: $[(M + 1)]^+$ | $^1$H-NMR |
| H19 | 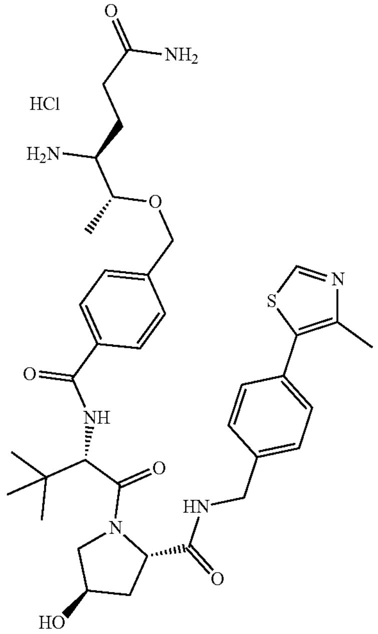 [SMILES: Cc1ncsc1-c1ccc(CNC(=O)[C@@H]2C[C@@H](O)CN2C(=O)[C@@H](NC(=O)c2ccc(CO[C@H](C)[C@@H](N)CCC(N)=O)cc2)C(C)(C)C)cc1 ; Cl] | (2S,4R)-1-[(2S)-2-[[4-([[(2R,3S)-3-amino-5-carbamoylpentan-2-yl]oxy]methyl)phenyl]formamido]-3,3-dimethylbutanoyl]-4-hydroxy-N-[[4-(4-methyl-1,3-thiazol-5-yl)phenyl]methyl]pyrrolidine-2-carboxamide hydrochloride | 693.5 | (400 MHz, $CD_3OD$) δ 9.86 (s, 1H), 7.85 (t, J = 7.5 Hz, 2H), 7.56 (dt, J = 14.6, 8.0 Hz, 6H), 4.76 (d, J = 12.3 Hz, 1H), 4.68-4.53 (m, 5H), 4.44 (d, J = 15.6 Hz, 1H), 4.01 (d, J = 10.9 Hz, 1H), 3.87 (s, 2H), 3.77 (s, 1H), 3.62 (s, 1H), 3.44 (s, 2H), 3.37 (s, 3H), 2.51-2.38 (m, 1H), 2.27 (s, 1H), 2.12 (s, 1H), 1.99-1.83 (m, 1H), 1.31-1.28 (m, 2H), 1.12 (d, J = 11.3 Hz, 9H). |
| H20 | 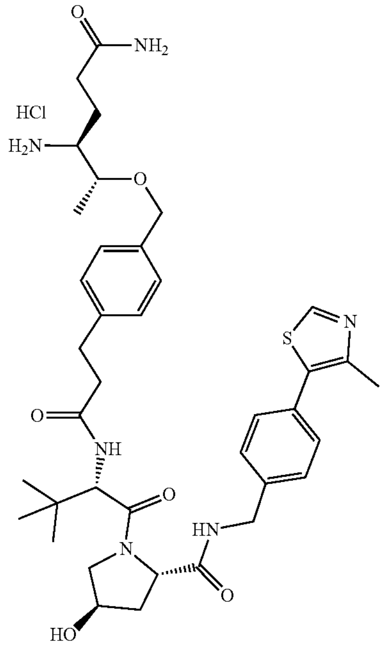 [SMILES: Cc1ncsc1-c1ccc(CNC(=O)[C@@H]2C[C@@H](O)CN2C(=O)[C@@H](NC(=O)CCc2ccc(CO[C@H](C)[C@@H](N)CCC(N)=O)cc2)C(C)(C)C)cc1 ; Cl] | (2S,4R)-1-[(2S)-2-[3-[4-([[(2R,3S)-3-amino-5-carbamoylpentan-2-yl]oxy]methyl)phenyl]propanamido]-3,3-dimethylbutanoyl]-4-hydroxy-N-[[4-(4-methyl-1,3-thiazol-5-yl)phenyl]methyl]pyrrolidine-2-carboxamide hydrochloride | 721.5 | (400 MHz, DMSO-$d_6$) δ 9.01 (s, 1H), 8.58 (t, J = 6.1 Hz, 1H), 8.07-7.98 (m, 2H), 7.94 (d, J = 9.4 Hz, 1H), 7.49-7.35 (m, 4H), 7.28 (d, J = 8.1 Hz, 2H), 7.20 (d, J = 7.8 Hz, 2H), 6.92 (s, 1H), 4.58-4.49 (m, 3H), 4.48-1.43 (m, 5H), 3.76 (dd, J = 6.5, 3.5 Hz, 1H), 3.66 (dd, J = 6.8, 3.0 Hz, 1H), 3.26 (d, J = 7.7 Hz, 1H), 2.88-2.72 (m, 2H), 2.48-2.41 (m, 4H), 2.24 (t, J = 7.5 Hz, 2H), 2.05-2.02 (m, 1H), 1.92 (td, J = 8.4, 4.2 Hz, 1H), 1.74 (p, J = 7.5, 7.0 Hz, 2H), 1.14 (d, J = 6.4 Hz, 3H), 0.91 (s, 9H). |

TABLE 49-continued

| Characterization data for intermediates prepared according to procedure above. | | | | |
|---|---|---|---|---|
| Intermediate | Structure | Chemical Name | MS: [(M + 1)]+ | ¹H-NMR |
| H21 | 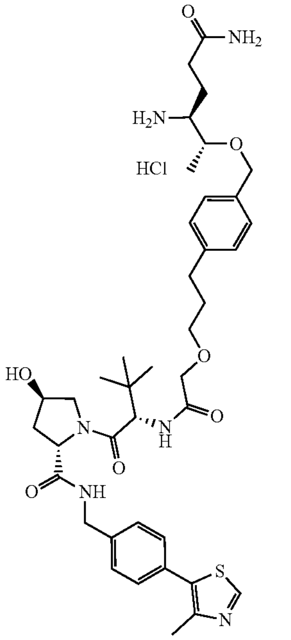 [SMILES: Cc1ncsc1-c1ccc(CNC(=O)[C@@H]2C[C@@H](O)CN2C(=O)[C@@H](NC(=O)COCCCc2ccc(CO[C@H](C)[C@@H](N)CCC(N)=O)cc2)C(C)(C)C)cc1 ; Cl] | (2S,4R)-1-[(2S)-2-(2-[3-[4-([[(2R,3S)-3-amino-5-carbamoylpentan-2-yl]oxy]methyl)phenyl]propoxy]acetamido)-3,3-dimethylbutanoyl]-4-hydroxy-N-[[4-(4-methyl-1,3-thiazol-5-yl)phenyl]methyl]pyrrolidine-2-carboxamide hydrochloride | 765.5 | (400 MHz, DMSO-$d_6$) δ 9.28 (s, 1H), 8.64 (d, J = 23.9 Hz, 1H), 8.18 (s, 2H), 7.43-7.38 (m, 6H), 7.25 (d, J = 8.0 Hz, 2H), 7.15 (d, J = 7.1 Hz, 3H), 4.54 (d, J = 9.7 Hz, 1H), 4.45 (s, 2H), 4.35 (s, 1H), 4.26 (s, 1H), 3.93 (d, J = 11.7 Hz, 2H), 3.77 (s, 2H), 3.46 (s, 3H), 3.39 (s, 1H), 3.16 (d, J = 12.4 Hz, 2H), 2.62 (d, J = 9.4 Hz, 3H), 2.43 (s, 3H), 2.24 (s, 2H), 2.06 (s, 1H), 1.82-1.76 (m, 5H), 1.12 (d, J = 6.5 Hz, 3H), 0.94 (s, 9H). |
| H22 | 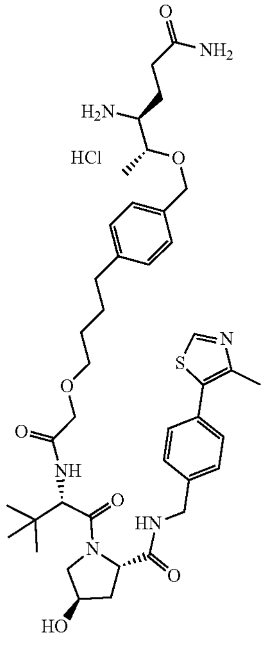 [SMILES: Cc1ncsc1-c1ccc(CNC(=O)[C@@H]2C[C@@H](O)CN2C(=O)[C@@H](NC(=O)COCCCCc2ccc(CO[C@H](C)[C@@H](N)CCC(N)=O)cc2)C(C)(C)C)cc1 ; Cl] | (2S,4R)-1-[(2S)-2-(2-[4-[4-([[(2R,3S)-3-amino-5-carbamoylpentan-2-yl]oxy]methyl)phenyl]butoxy]acetamido)-3,3-dimethylbutanoyl]-4-hydroxy-N-[[4-(4-methyl-1,3-thiazol-5-yl)phenyl]methyl]pyrrolidine-2-carboxamide hydrochloride | 779.5 | (400 MHz, DMSO-$d_6$) δ 9.04 (d, J = 24.2 Hz, 1H), 8.61 (t, J = 6.2 Hz, 1H), 8.02 (d, J = 45.4 Hz, 3H), 7.45-7.36 (m, 5H), 7.27 (d, J = 7.6 Hz, 2H), 7.17 (d, J = 7.7 Hz, 2H), 6.92 (s, 1H), 3.91 (d, J = 3.1 Hz, 2H), 3.75 (dd, J = 6.0, 3.2 Hz, 1H), 3.65 (d, J = 3.2 Hz, 2H), 3.62 (s, 1H), 3.50 (s, 3H), 3.39 (d, J = 2.7 Hz, 6H), 3.17 (d, J = 3.3 Hz, 1H), 2.60 (t, J = 7.3 Hz, 2H), 2.44 (s, 3H), 2.24 (t, J = 7.4 Hz, 2H), 2.07 (t, J = 10.4 Hz, 1H), 1.91 (td, J = 8.8, 8.3, 4.4 Hz, 1H), 1.75 (q, J = 7.9 Hz, 2H), 1.68-1.60 (m, 2H), 1.57 (d, J = 6.9 Hz, 2H), 1.14 (d, J = 6.4 Hz, 3H), 0.94 (d, J = 2.9 Hz, 9H). |

TABLE 49-continued

Characterization data for intermediates prepared according to procedure above.

| Intermediate | Structure | Chemical Name | MS: [(M + 1)]+ | 1H-NMR |
|---|---|---|---|---|
| H23 | 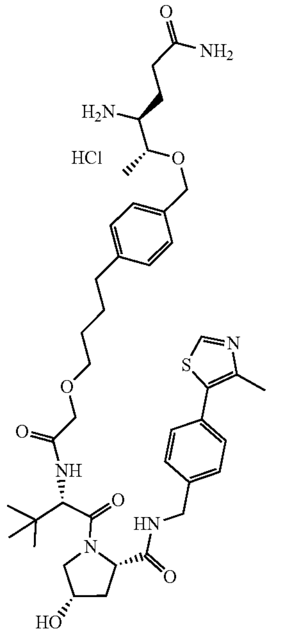 [SMILES: Cc1ncsc1-c1ccc(CNC(=O)[C@@H]2C[C@H](O)CN2C(=O)[C@@H](NC(=O)COCCCCc2ccc(CO[C@H](C)[C@@H](N)CCC(N)=O)cc2)C(C)(C)C)cc1 ; Cl] | (2S,4S)-1-[(2S)-2-(2-[4-[4-([[(2R,3S)-3-amino-5-carbamoylpentan-2-yl]oxy]methyl)phenyl]butoxy]acetamido)-3,3-dimethylbutanoyl]-4-hydroxy-N-[[4-(4-methyl-1,3-thiazol-5-yl)phenyl]methyl]pyrrolidine-2-carboxamide hydrochloride | 779.5 | (400 MHz, $CD_3OD$) δ 9.67 (s, 1H), 7.55 (d, J = 8.3 Hz, 2H), 7.51 (d, J = 8.5 Hz, 2H), 7.30 (d, J = 7.5 Hz, 2H), 7.22 (d, J = 8.0 Hz, 2H), 4.63 (d, J = 9.1 Hz, 1H), 4.58-4.39 (m, 3H), 3.96 (d, J = 4.7 Hz, 2H), 3.88-3.84 (m, 9H), 3.52-3.48 (m, 2H), 3.37 (s, 4H), 2.67 (d, J = 7.6 Hz, 2H), 2.58 (s, 3H), 2.44 (dd, J = 12.7, 6.6 Hz, 1H), 1.72 (d, J = 28.6 Hz, 3H), 1.25 (d, J = 6.4 Hz, 3H), 1.05 (s, 9H). |
| H24 | 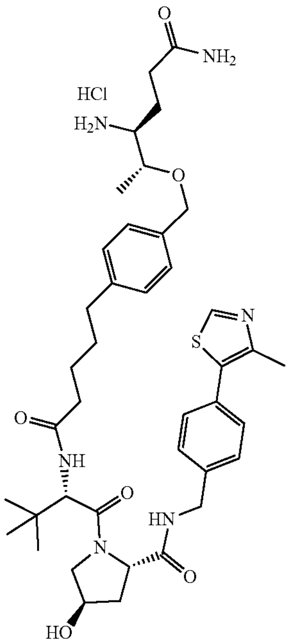 [SMILES: Cc1ncsc1-c1ccc(CNC(=O)[C@@H]2C[C@@H](O)CN2C(=O)[C@@H](NC(=O)CCCCc2ccc(CO[C@H](C)[C@@H](N)CCC(N)=O)cc2)C(C)(C)C)cc1 ; Cl] | (2S,4R)-1-((S)-2-(5-(4-((((2R,3S)-3,6-diamino-6-oxohexan-2-yl)oxy)methyl)phenyl)pentanamido)-3,3-dimethylbutanoyl)-4-hydroxy-N-(4-(4-methylthiazol-5-yl)benzyl)pyrrolidine-2-carboxamide | 749.4 | (400 MHz, DMSO-$d_6$) δ 9.06 (d, J = 2.8 Hz, 1H), 8.68 (s, 1H), 8.57 (t, J = 6.2 Hz, 1H), 8.06 (s, 4H), 7.85 (d, J = 9.3 Hz, 1H), 7.49 (d, J = 8.2 Hz, 1H), 7.46-7.36 (m, 5H), 7.29 (d, J = 7.7 Hz, 3H), 7.16 (d, J = 7.8 Hz, 4H), 6.90 (s, 1H), 4.58-4.49 (m, 2H), 4.46 (d, J = 6.5 Hz, 1H), 4.42 (dd, J = 10.8, 3.1 Hz, 1H), 4.36 (s, 1H), 4.31-4.12 (m, 1H), 3.77 (td, J = 6.6, 3.8 Hz, 1H), 3.25 (s, 1H), 3.17 (s, 1H), 2.56 (d, J = 7.2 Hz, 1H), 2.46 (d, J = 4.4 Hz, 4H), 2.25 (t, J = 7.4 Hz, 3H), 2.21-2.11 (m, 1H), 2.03 (d, J = 8.6 Hz, 1H), 1.93 (dd, J = 12.8, 8.4 Hz, 1H), 1.81-1.68 (m, 2H), 1.56-1.50 (m, 4H), 1.18-1.12 (m, 4H), 1.09 (d, J = 6.3 Hz, 1H), 0.93 (s, 2H). |

TABLE 49-continued

| Characterization data for intermediates prepared according to procedure above. | | | | |
|---|---|---|---|---|
| Intermediate | Structure | Chemical Name | MS: $[(M+1)]^+$ | $^1$H-NMR |
| H25 | 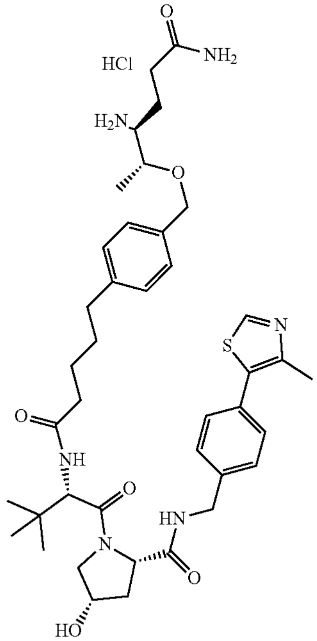 [SMILES: Cc1ncsc1-c1ccc(CNC(=O)[C@@H]2C[C@H](O)CN2C(=O)[C@@H](NC(=O)CCCCc2ccc(CO[C@H](C)[C@@H](N)CCC(N)=O)cc2)C(C)(C)C)cc1 ; Cl] | (2S,4S)-1-[(2S)-2-[5-[4-([[(2R,3S)-3-amino-5-carbamoylpentan-2-yl]oxy]methyl)phenyl]pentanamido]-3,3-dimethylbutanoyl]-4-hydroxy-N-[[4-(4-methyl-1,3-thiazol-5-yl)phenyl]methyl]pyrrolidine-2-carboxamide hydrochloride | 749.4 | (400 MHz, DMSO-$d_6$) δ 9.13-9.02 (m, 2H), 8.64 (t, J = 6.1 Hz, 1H), 7.86 (d, J = 8.8 Hz, 1H), 7.51-7.31 (m, 7H), 7.28 (t, J = 6.6 Hz, 3H), 7.23-7.12 (m, 3H), 6.90 (s, 1H), 4.56-4.45 (m, 3H), 4.44 (d, J = 4.4 Hz, 1H), 4.45-4.32 (m, 2H), 4.31-4.12 (m, 2H), 3.93 (dd, J = 10.0, 5.7 Hz, 1H), 3.81-3.72 (m, 1H), 3.47-3.36 (m, 1H), 3.40 (s, 5H), 3.26 (s, 2H), 3.17 (s, 3H), 2.56 (d, J = 7.3 Hz, 4H), 2.33-2.21 (m, 3H), 2.20-2.11 (m, 1H), 1.09 (d, J = 6.1 Hz, 1H), 0.94 (s, 9H). |
| H26 | 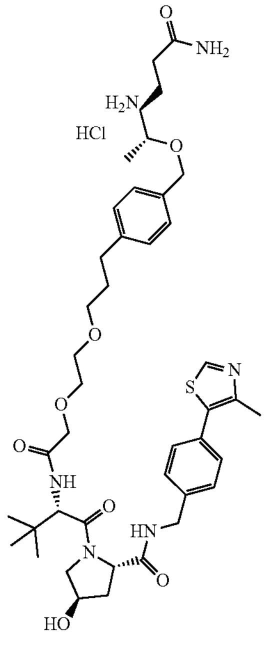 [SMILES: Cc1ncsc1-c1ccc(CNC(=O)[C@@H]2C[C@@H](O)CN2C(=O)[C@@H](NC(=O)COCCOCCCc2ccc(CO[C@H](C)[C@@H](N)CCC(N)=O)cc2)C(C)(C)C)cc1 ; Cl] | (2S,4R)-1-[(2S)-2-[2-(2-[3-[4-([[(2R,3S)-3-amino-5-carbamoylpentan-2-yl]oxy]methyl)phenyl]propoxy]ethoxy)acetamido]-3,3-dimethylbutanoyl]-4-hydroxy-N-[[4-(4-methyl-1,3-thiazol-5-yl)phenyl]methyl]pyrrolidine-2-carboxamide hydrochloride | 809.5 | (400 MHz, DMSO-$d_6$) δ 9.07 (s, 1H), 8.62 (t, J = 6.1 Hz, 1H), 8.06 (s, 2H), 7.41 (d, J = 8.6 Hz, 4H), 7.27 (d, J = 7.9 Hz, 2H), 7.15 (d, J = 7.8 Hz, 2H), 6.92 (s, 1H), 4.60-4.32 (m, 6H), 4.31-4.20 (m, 1H), 3.77 (d, J = 8.8 Hz, 1H), 3.54 (s, 8H), 3.43 (t, J = 4.4 Hz, 2H), 3.25 (s, 1H), 2.60 (t, J = 7.8 Hz, 2H), 2.44 (s, 3H), 2.25 (t, J = 7.5 Hz, 2H), 2.07 (t, J = 10.6 Hz, 1H), 1.76 (tq, J = 14.9, 6.9 Hz, 4H), 1.14 (d, J = 6.4 Hz, 3H), 0.95 (s, 9H). |

TABLE 49-continued

| Characterization data for intermediates prepared according to procedure above. | | | | |
|---|---|---|---|---|
| Intermediate | Structure | Chemical Name | MS: $[(M+1)]^+$ | $^1$H-NMR |
| H27 | 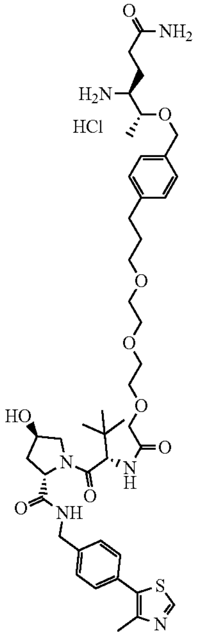 [SMILES: Cc1ncsc1-c1ccc(CNC(=O)[C@@H]2C[C@@H](O)CN2C(=O)[C@@H](NC(=O)COCCOCCOCCCc2ccc(CO[C@H](C)[C@@H](N)CCC(N)=O)cc2)C(C)(C)C)cc1 ; Cl] | (2S,4R)-1-[(2S)-2-[2-[2-(2-[3-[4-([[(2R,3S)-3-amino-5-carbamoylpentan-2-yl]oxy]methyl)phenyl]propoxy]ethoxy)ethoxy]acetamido]-3,3-dimethylbutanoyl]-4-hydroxy-N-[[4-(4-methyl-1,3-thiazol-5-yl)phenyl]methyl]pyrrolidine-2-carboxamide hydrochloride | 853.6 | (400 MHz, DMSO-$d_6$) δ 9.06 (s, 1H), 8.63 (t, J = 6.0 Hz, 1H), 8.06 (s, 3H), 7.41 (s, 5H), 7.28 (d, J = 7.3 Hz, 2H), 7.17 (t, J = 9.3 Hz, 2H), 6.92 (s, 1H), 4.60-4.50 (m, 2H), 4.48-4.41 (m, 2H), 4.41-4.33 (m, 2H), 4.25 (dd, J = 15.9, 5.7 Hz, 1H), 4.14 (d, J = 5.7 Hz, 1H), 3.98 (s, 1H), 3.81-3.73 (m, 1H), 3.65 (d, J = 3.8 Hz, 2H), 3.61 (s, 2H), 3.52-3.47 (m, 5H), 3.39-3.24 (m, 4H), 3.25 (s, 1H), 2.64-2.54 (m, 2H), 2.45 (s, 3H), 2.25 (t, J = 7.5 Hz, 3H), 1.80-1.72 (m, 5H), 1.15 (dd, J = 6.3, 2.0 Hz, 3H), 0.95 (s, 9H). |
| H28 | 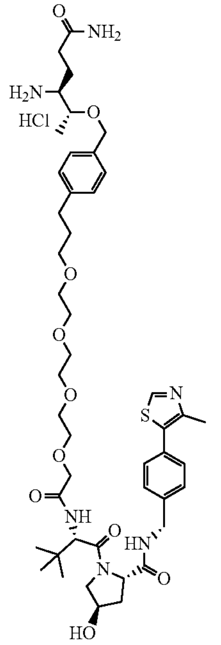 | (2S,4R)-1-[(2S)-2-[15-[4-([[(2R,3S)-3-amino-5-carbamoylpentan-2-yl]oxy]methyl)phenyl]-3,6,9,12-tetraoxapentadecanamido]-3,3-dimethylbutanoyl]-4-hydroxy-N-[[4-(4-methyl-1,3-thiazol-5-yl)phenyl]methyl]pyrrolidine-2-carboxamide hydrochloride | 897.6 | (400 MHz, DMSO-$d_6$) δ 9.01 (s, 1H), 8.61 (t, J = 6.0 Hz, 1H), 7.98 (s, 3H), 7.42 (d, J = 12.3 Hz, 6H), 7.29 (d, J = 7.9 Hz, 2H), 7.17 (d, J = 8.0 Hz, 2H), 6.93 (s, 1H), 4.61-4.49 (m, 2H), 4.49-4.34 (m, 4H), 4.25 (dd, J = 15.8, 5.7 Hz, 1H), 3.97 (s, 2H), 3.76 (s, 1H), 3.71-3.64 (m, 1H), 3.62 (s, 3H), 3.57-3.43 (m, 4H), 3.40-3.35 (m, 4H), 3.27 (s, 1H), 2.59 (t, J = 7.6 Hz, 2H), 2.45 (s, 3H), 2.24 (t, J = 7.5 Hz, 2H), 2.12-2.02 (m, 1H), 1.96-1.86 (m, 2H), 1.75 (h, J = 7.8, 7.3 Hz, 4H), 1.18-1.10 (m, 4H), 0.95 (s, 9H). |

TABLE 49-continued

Characterization data for intermediates prepared according to procedure above.

| Intermediate | Structure | Chemical Name | MS: $[(M+1)]^+$ | $^1$H-NMR |
|---|---|---|---|---|
| H29 | 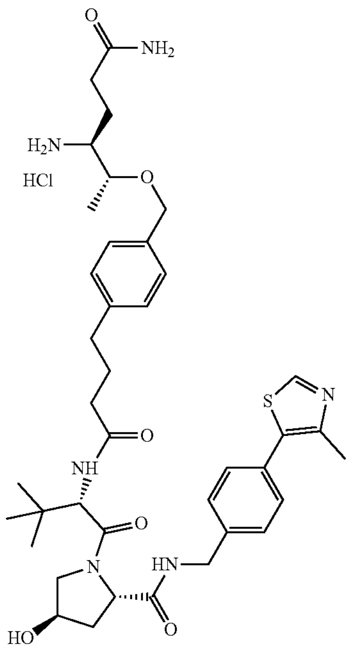 [SMILES: Cc1ncsc1-c1ccc(CNC(=O)[C@@H]2C[C@@H](O)CN2C(=O)[C@@H](NC(=O)CCCc2ccc(CO[C@H](C)[C@@H](N)CCC(N)=O)cc2)C(C)(C)C)cc1 ; Cl] | (2S,4R)-1-[(2S)-2-[4-[4-([[(2R,3S)-3-amino-5-carbamoylpentan-2-yl]oxy]methyl)phenyl]butanamido]-3,3-dimethylbutanoyl]-4-hydroxy-N-[[4-(4-methyl-1,3-thiazol-5-yl)phenyl]methyl]pyrrolidine-2-carboxamide hydrochloride | 735.4 | Used directly in next step without further purification |
| H30 | 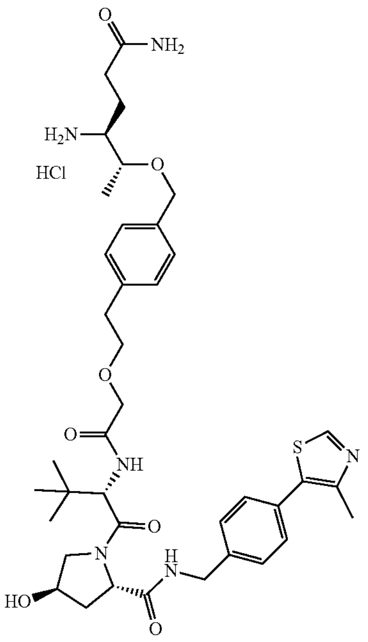 [SMILES: Cc1ncsc1-c1ccc(CNC(=O)[C@@H]2C[C@@H](O)CN2C(=O)[C@@H](NC(=O)COCCc2ccc(CO[C@H](C)[C@@H](N)CCC(N)=O)cc2)C(C)(C)C)cc1 ; Cl] | (2S,4R)-1-[(2S)-2-(2-[2-[4-([[(2R,3S)-3-amino-5-carbamoylpentan-2-yl]oxy]methyl)phenyl]ethoxy]acetamido)-3,3-dimethylbutanoyl]-4-hydroxy-N-[[4-(4-methyl-1,3-thiazol-5-yl)phenyl]methyl]pyrrolidine-2-carboxamide hydrochloride | 751.5 | (400 MHz, DMSO-$d_6$) δ 9.02 (s, 1H), 8.63 (t, J = 6.1 Hz, 1H), 7.99 (s, 3H), 7.46-7.36 (m, 4H), 7.33-7.19 (m, 4H), 6.93 (s, 1H), 4.59-4.51 (m, 1H), 4.51-4.35 (m, 3H), 4.36 (s, 1H), 4.27 (dd, J = 15.8, 5.7 Hz, 1H), 3.95 (s, 2H), 3.78-3.67 (m, 1H), 3.39 (s, 3H), 3.26 (s, 1H), 3.17 (s, 1H), 2.95 (s, 1H), 2.87 (t, J = 6.8 Hz, 2H), 2.79 (s, 1H), 2.44 (s, 3H), 2.24 (t, J = 7.5 Hz, 2H), 2.07 (t, J = 10.3 Hz, 1H), 1.99-1.85 (m, 2H), 1.79-1.70 (m, 1H), 1.15-1.12 (m, 3H), 0.93 (s, 9H). |

TABLE 49-continued

| Characterization data for intermediates prepared according to procedure above. | | | | |
|---|---|---|---|---|
| Intermediate | Structure | Chemical Name | MS: $[(M + 1)]^+$ | $^1$H-NMR |
| H31 | 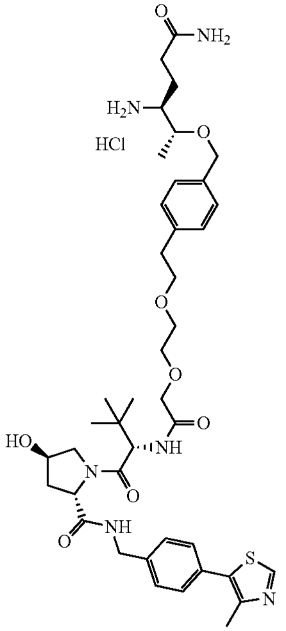 [SMILES: Cc1ncsc1-c1ccc(CNC(=O)[C@@H]2C[C@@H](O)CN2C(=O)[C@@H](NC(=O)COCCOCCc2ccc(CO[C@H](C)[C@@H](N)CCC(N)=O)cc2)C(C)(C)C)cc1 ; Cl] | (2S,4R)-1-[(2S)-2-[2-(2-[2-[4-([[(2R,3S)-3-amino-5-carbamoylpentan-2-yl]oxy]methyl)phenyl]ethoxy]ethoxy)acetamido]-3,3-dimethylbutanoyl]-4-hydroxy-N-[[4-(4-methyl-1,3-thiazol-5-yl)phenyl]methyl]pyrrolidine-2-carboxamide hydrochloride | 795.6 | (400 MHz, DMSO-$d_6$) δ 9.02 (s, 1H), 8.61 (t, J = 5.9 Hz, 1H), 8.01 (s, 3H), 7.30-7.17 (m, 3H), 6.91 (s, 1H), 4.62-4.41 (m, 5H), 4.40 (d, J = 8.9 Hz, 1H), 4.37 (s, 2H), 4.26 (dd, J = 15.9, 5.7 Hz, 2H), 3.97 (s, 3H), 3.76 (d, J = 6.0 Hz, 2H), 3.49 (d, J = 6.5 Hz, 1H), 3.40 (s, 6H), 3.27 (s, 1H), 3.18 (s, 1H), 2.85-2.82 (m, 3H), 2.43 (s, 2H), 2.25 (t, J = 7.5 Hz, 2H), 2.12-1.99 (m, 2H), 1.97-1.86 (m, 1H), 1.74 (dd, J = 14.8, 7.4 Hz, 2H), 1.15 (d, J = 6.4 Hz, 4H), 1.08 (d, J = 6.2 Hz, 1H), 0.96 (s, 9H). |
| H32 | 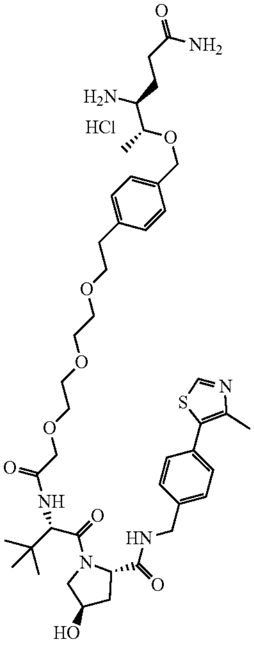 [SMILES: Cc1ncsc1-c1ccc(CNC(=O)[C@@H]2C[C@@H](O)CN2C(=O)[C@@H](NC(=O)COCCOCCOCCc2ccc(CO[C@H](C)[C@@H](N)CCC(N)=O)cc2)C(C)(C)C)cc1 ; Cl] | (2S,4R)-1-[(2S)-2-[2-[2-(2-[2-[4-([[(2R,3S)-3-amino-5-carbamoylpentan-2-yl]oxy]methyl)phenyl]ethoxy]ethoxy)ethoxy]acetamido]-3,3-dimethylbutanoyl]-4-hydroxy-N-[[4-(4-methyl-1,3-thiazol-5-yl)phenyl]methyl]pyrrolidine-2-carboxamide hydrochloride | 839.6 | (400 MHz, DMSO-$d_6$) δ 9.00 (s, 1H), 8.61 (t, J = 6.1 Hz, 1H), 7.94 (s, 3H), 7.43 (d, J = 9.1 Hz, 3H), 7.40 (s, 3H), 7.28 (d, J = 7.9 Hz, 2H), 7.20 (d, J = 7.9 Hz, 2H), 6.93 (s, 1H), 4.61-4.49 (m, 2H), 4.48-4.35 (m, 4H), 3.97 (s, 2H), 3.57 (t, J = 10.4 Hz, 10H), 3.39 (s, 2H), 3.27 (s, 1H), 2.77 (t, J = 6.9 Hz, 2H), 2.44 (s, 3H), 2.26-2.21 (m, 5H), 1.74 (p, J = 7.5 Hz, 2H), 1.18-1.12 (m, 3H), 0.95 (s, 9H). |

TABLE 49-continued

| Characterization data for intermediates prepared according to procedure above. | | | | |
|---|---|---|---|---|
| Intermediate | Structure | Chemical Name | MS: $[(M + 1)]^+$ | $^1$H-NMR |
| H33 | 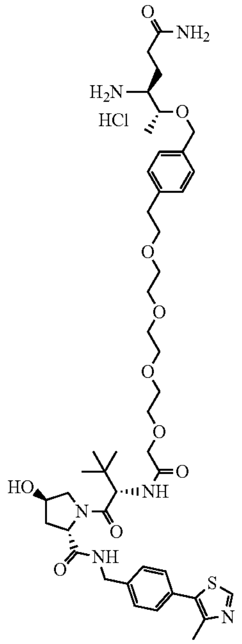 [SMILES: Cc1ncsc1-c1ccc(CNC(=O)[C@@H]2C[C@@H](O)CN2C(=O)[C@@H](NC(=O)COCCOCCOCCOCCc2ccc(CO[C@H](C)[C@@H](N)CCC(N)=O)cc2)C(C)(C)C)cc1 ; Cl] | (2S,4R)-1-[(2S)-2-[14-[4-([[(2R,3S)-3-amino-5-carbamoylpentan-2-yl]oxy]methyl)phenyl]-3,6,9,12-tetraoxatetradecanamido]-3,3-dimethylbutanoyl]-4-hydroxy-N-[[4-(4-methyl-1,3-thiazol-5-yl)phenyl]methyl]pyrrolidine-2-carboxamide hydrochloride | 883.7 | (400 MHz, DMSO-$d_6$) δ 9.08 (s, 1H), 8.65-8.48 (m, 1H), 8.11 (s, 3H), 7.41 (s, 5H), 7.29 (d, J = 7.9 Hz, 2H), 7.20 (d, J = 7.9 Hz, 2H), 6.91 (s, 1H), 4.60-4.49 (m, 2H), 4.49-4.40 (m, 2H), 4.40-4.34 (m, 2H), 4.25 (dd, J = 15.8, 5.7 Hz, 1H), 3.81-3.73 (m, 2H), 3.66 (d, J = 3.8 Hz, 1H), 3.64-3.59 (m, 3H), 3.56-3.53 (m, 3H), 3.53-3.50 (m, 3H), 3.48 (s, 4H), 3.40 (s, 2H), 3.25 (s, 1H), 2.78 (t, J = 7.0 Hz, 2H), 2.46 (s, 3H), 2.25 (t, J = 7.9 Hz, 2H), 2.07 (t, J = 10.4 Hz, 1H), 1.91 (ddd, J = 13.0, 8.7, 4.6 Hz, 1H), 1.80-1.71 (m, 2H), 1.17-1.12 (m, 3H), 0.95 (s, 9H). |
| H34 | 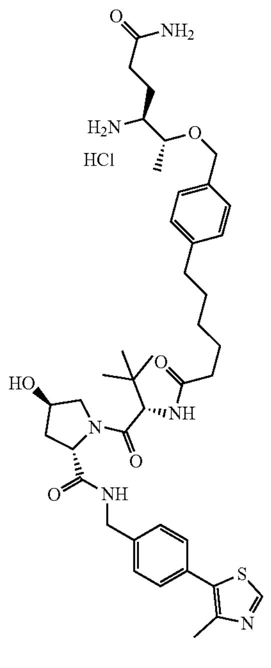 [SMILES: Cc1ncsc1-c1ccc(CNC(=O)[C@@H]2C[C@@H](O)CN2C(=O)[C@@H](NC(=O)CCCCCc2ccc(CO[C@H](C)[C@@H](N)CCC(N)=O)cc2)C(C)(C)C)cc1 ; Cl] | (2S,4R)-1-((S)-2-(6-(4-((((2R,3S)-3,6-diamino-6-oxohexan-2-yl)oxy)methyl)phenyl)hexanamido)-3,3-dimethylbutanoyl)-4-hydroxy-N-(4-(4-methylthiazol-5-yl)benzyl) pyrrolidine-2-carboxamide | 763.4 | (400 MHz, DMSO-$d_6$) δ 9.08 (d, J = 1.1 Hz, 1H), 8.58 (t, J = 6.1 Hz, 1H), 8.10 (s, 3H), 7.84 (d, J = 9.3 Hz, 1H), 7.51-7.37 (m, 5H), 7.33-7.25 (m, 2H), 7.19-7.14 (m, 2H), 6.91 (s, 1H), 4.58-4.49 (m, 2H), 4.45-4.40 (m, 3H), 4.35 (s, 1H), 4.22 (dd, J = 15.9, 5.4 Hz, 1H), 3.82-3.74 (m, 1H), 3.67-3.63 (m, 1H), 3.61 (s, 1H), 3.39 (s, 1H), 3.25 (s, 1H), 2.58-2.53 (m, 2H), 2.46 (d, J = 4.2 Hz, 3H), 2.30-2.21 (m, 3H), 2.17-2.00 (m, 2H), 1.90 (ddd, J = 12.9, 8.6, 4.6 Hz, 1H), 1.81-1.72 (m, 2H), 1.59-1.46 (m, 4H), 1.27 (q, J = 7.6 Hz, 2H), 1.15 (d, J = 6.4 Hz, 3H), 0.93 (d, J = 3.6 Hz, 9H). |

TABLE 49-continued

| Characterization data for intermediates prepared according to procedure above. | | | | |
|---|---|---|---|---|
| Intermediate | Structure | Chemical Name | MS: $[(M + 1)]^+$ | $^1$H-NMR |
| H35 | 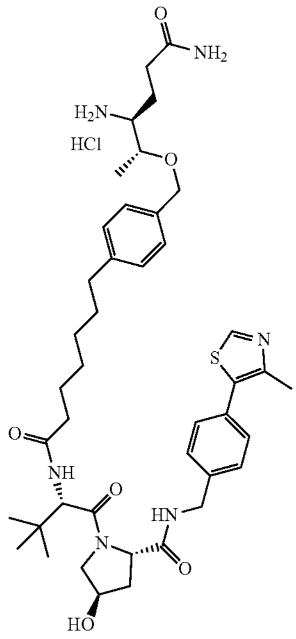 [SMILES: Cc1ncsc1-c1ccc(CNC(=O)[C@@H]2C[C@@H](O)CN2C(=O)[C@@H](NC(=O)CCCCCCc2ccc(CO[C@H](C)[C@@H](N)CCC(N)=O)cc2)C(C)(C)C)cc1 ; Cl] | (2S,4R)-1-[(2S)-2-[7-[4-([[(2R,3S)-3-amino-5-carbamoylpentan-2-yl]oxy]methyl)phenyl]heptanamido]-3,3-dimethylbutanoyl]-4-hydroxy-N-[[4-(4-methyl-1,3-thiazol-5-yl)phenyl]methyl]pyrrolidine-2-carboxamide hydrochloride | 777.7 | (400 MHz, $CD_3OD$) δ 9.90 (d, J = 15.5 Hz, 1H), 7.65-7.48 (m, 4H), 7.33-7.29 (m, 2H), 7.19 (d, J = 7.8 Hz, 2H), 4.64-4.46 (m, 10H), 2.62 (s, 4H), 2.48-2.41 (m, 4H), 2.33-2.26 (m, 3H), 2.10 (s, 2H), 1.94 (s, 2H), 1.63 (s, 4H), 1.38 (s, 4H), 1.26 (d, J = 6.4 Hz, 3H), 1.06 (s, 9H). |
| H36 | 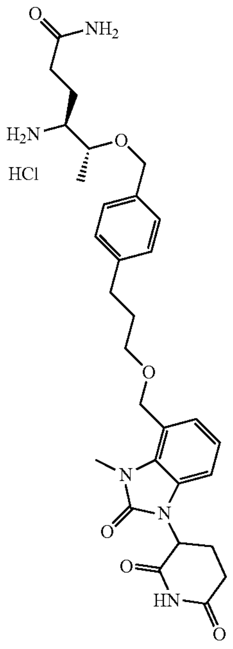 [SMILES: Cl ; C[C@@H](OCc1ccc(CCCOCc2cccc3c2n(C)c(=O)n3C2CCC(=O)NC2=O)cc1)[C@@H](N)CCC(N)=O] | (4S,5R)-4-amino-5-[[4-(3-[[1-(2,6-dioxopiperidin-3-yl)-3-methyl-2-oxo-1,3-benzodiazol-4-yl]methoxy]propyl)phenyl]methoxy]hexanamide hydrochloride | 566.4 | (400 MHz, $CD_3OD$) δ 7.27 (d, J = 7.8 Hz, 2H), 7.18-7.08 (m, 3H), 7.08 (q, J = 3.7 Hz, 2H), 5.38 (dd, J = 12.3, 5.4 Hz, 1H), 4.98 (s, 2H), 4.76 (s, 2H), 4.62 (d, J = 11.6 Hz, 1H), 4.49 (d, J = 11.6 Hz, 1H), 3.80 (qd, J = 6.4, 3.4 Hz, 1H), 3.70 (s, 3H), 3.53 (t, J = 6.2 Hz, 2H), 3.02-2.85 (m, 1H), 2.88-2.76 (m, 2H), 2.67 (t, J = 7.5 Hz, 2H), 2.52-2.33 (m, 2H), 2.24-2.14 (m, 1H), 2.01-1.78 (m, 2H), 1.59 (s, 1H), 1.25 (d, J = 6.4 Hz, 3H). |

TABLE 49-continued

| Characterization data for intermediates prepared according to procedure above. | | | | |
|---|---|---|---|---|
| Intermediate | Structure | Chemical Name | MS: [(M + 1)]$^+$ | $^1$H-NMR |
| H37 | 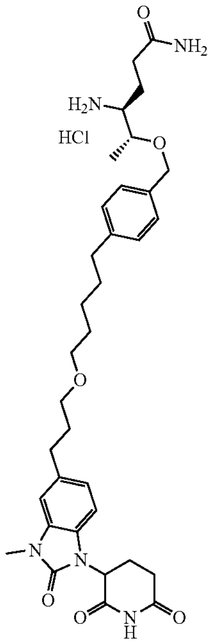 [SMILES: C[C@@H](OCc1ccc(CCCCCOCCCc2ccc3c(c2)n(C)c(=O)n3C2CCC(=O)NC2=O)cc1)[C@@H](N)CCC(N)=O ; Cl] | (4S,5R)-4-amino-5-[[4-(5-[3-[1-(2,6-dioxopiperidin-3-yl)-3-methyl-2-oxo-1,3-benzodiazol-5-yl]propoxy]pentyl)phenyl]methoxy]hexanamide hydrochloride | 622.4 | (400 MHz, DMSO-d$_6$) δ 11.08 (s, 1H), 7.92 (s, 3H), 7.42 (s, 1H), 7.28 (d, J = 7.6 Hz, 2H), 7.18 (d, J = 8.0 Hz, 2H), 7.01 (d, J = 10.0 Hz, 2H), 6.93 (s, 1H), 6.86 (d, J = 8.0 Hz, 1H), 5.34 (dd, J = 12.7, 5.2 Hz, 1H), 4.52 (d, J = 11.6 Hz, 1H), 4.45 (d, J = 11.6 Hz, 1H), 4.14-4.10 (m, 3H), 3.87 (s, 2H), 3.75 (d, J = 3.5 Hz, 1H), 3.61 (dd, J = 7.4, 3.4 Hz, 1H), 3.52-3.50 (m, 1H), 3.38-3.32 (m, 4H), 2.68-2.62 (m, 3H), 2.58 (t, J = 7.6 Hz, 2H), 2.24 (s, 1H), 2.02-1.97 (m, 1H), 1.81 (d, J = 8.6 Hz, 2H), 1.75 (d, J = 9.1 Hz, 1H), 1.54 (dt, J = 13.6, 7.7 Hz, 4H), 1.35-1.31 (m, 3H), 1.14 (d, J = 6.4 Hz, 3H). |
| H38 | 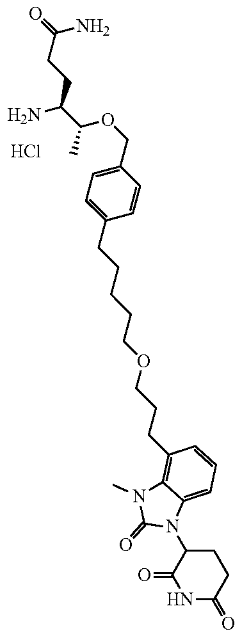 [SMILES: Cl ; C[C@@H](OCc1ccc(CCCCCOCCCc2cccc3c2n(C)c(=O)n3C2CCC(=O)NC2=O)cc1)[C@@H](N)CCC(N)=O] | (4S,5R)-4-amino-5-[[4-(5-[3-[1-(2,6-dioxopiperidin-3-yl)-3-methyl-2-oxo-1,3-benzodiazol-4-yl]propoxy]pentyl)phenyl]methoxy]hexanamide hydrochloride | 622.5 | (400 MHz, DMSO-d$_6$) δ 11.09 (s, 1H), 7.44 (s, 1H), 7.28 (d, J = 7.7 Hz, 2H), 7.18 (d, J = 8.0 Hz, 2H), 6.97 (d, J = 5.9 Hz, 2H), 6.93 (d, J = 7.0 Hz, 1H), 6.86 (dd, J = 6.5, 2.4 Hz, 1H), 5.38 (dd, J = 12.5, 5.4 Hz, 1H), 4.51 (d, J = 11.6 Hz, 1H), 4.44 (d, J = 11.7 Hz, 1H), 3.75 (dd, J = 6.5, 3.5 Hz, 1H), 3.65 (s, 1H), 3.61 (dd, J = 7.7, 4.0 Hz, 1H), 3.54 (s, 3H), 3.51 (d, J = 5.3 Hz, 2H), 3.42 (d, J = 5.9 Hz, 2H), 3.36 (d, J = 6.4 Hz, 2H), 3.26 (s, 1H), 2.92 (s, 2H), 2.74-2.62 (m, 2H), 2.60-2.53 (m, 3H), 2.23 (d, J = 7.5 Hz, 1H), 1.80-1.72 (m, 4H), 1.60-1.52 (m, 4H), 1.38-1.31 (m, 2H), 1.14 (d, J = 6.4 Hz, 3H). |

TABLE 49-continued

| Characterization data for intermediates prepared according to procedure above. | | | | |
|---|---|---|---|---|
| Intermediate | Structure | Chemical Name | MS: $[(M + 1)]^+$ | $^1$H-NMR |
| H39 | 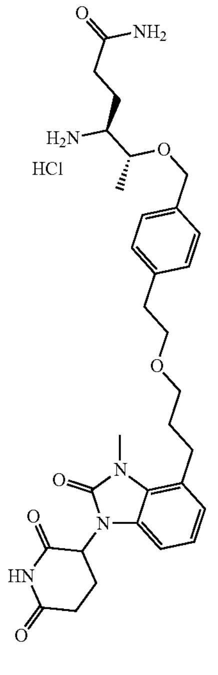 [SMILES: C[C@@H](OCc1ccc(CCOCCCc2cccc3c2n(C)c(=O)n3C2CCC(=O)NC2=O)cc1)[C@@H](N)CCC(N)=O ; Cl] | (4S,5R)-4-amino-5-[[4-(2-[3-[1-(2,6-dioxopiperidin-3-yl)-3-methyl-2-oxo-1,3-benzodiazol-4-yl]propoxy]ethyl)phenyl]methoxy]hexanamide hydrochloride | 580.3 | (400 MHz, DMSO-$d_6$) δ 11.09 (s, 1H), 7.98 (s, 2H), 7.43 (s, 1H), 7.31 (d, J = 7.8 Hz, 2H), 7.24 (d, J = 7.8 Hz, 2H), 6.99-6.90 (m, 2H), 6.81 (d, J = 7.2 Hz, 1H), 5.37 (dd, J = 12.6, 5.3 Hz, 1H), 4.63 (s, 3H), 4.54 (d, J = 11.8 Hz, 1H), 4.46 (d, J = 11.6 Hz, 1H), 3.76 (dd, J = 6.5, 3.4 Hz, 1H), 3.68-3.56 (m, 2H), 3.55-3.37 (m, 5H), 3.27 (s, 1H), 2.95-2.89 (m, 3H), 2.83 (t, J = 6.7 Hz, 2H), 2.74-2.63 (m, 1H), 2.24 (t, J = 7.4 Hz, 2H), 1.99 (d, J = 12.3 Hz, 1H), 1.83-1.74 (m, 3H), 1.73 (d, J = 7.7 Hz, 1H), 1.14 (d, J = 6.4 Hz, 3H). |
| H40 | 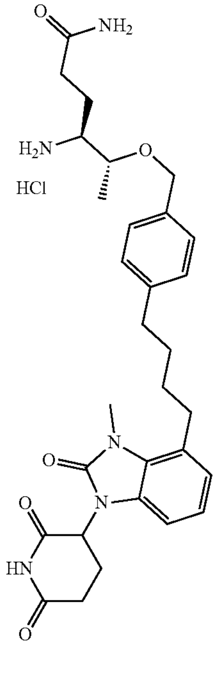 [SMILES: Cl ; C[C@@H](OCc1ccc(CCCCc2cccc3c2n(C)c(=O)n3C2CCC(=O)NC2=O)cc1)[C@@H](N)CCC(N)=O] | (4S,5R)-4-amino-5-[(4-[4-[1-(2,6-dioxopiperidin-3-yl)-3-methyl-2-oxo-1,3-benzodiazol-4-yl]butyl]phenyl)methoxy]hexanamide hydrochloride | 550.5 | (400 MHz, DMSO-$d_6$) δ 11.08 (s, 1H), 8.26-8.04 (m, 3H), 7.29 (d, J = 7.7 Hz, 2H), 7.19 (d, J = 7.8 Hz, 2H), 6.95 (h, J = 7.8, 5.8 Hz, 3H), 6.85 (dd, J = 6.9, 1.9 Hz, 1H), 5.38 (dd, J = 12.6, 5.4 Hz, 1H), 4.57-4.42 (m, 2H), 3.78 (qd, J = 6.3, 3.1 Hz, 1H), 3.51 (s, 3H), 3.25 (s, 1H), 2.98-2.86 (m, 3H), 2.71 (dd, J = 15.0, 10.6 Hz, 1H), 2.63 (q, J = 7.8, 7.2 Hz, 3H), 2.26 (t, J = 7.5 Hz, 2H), 1.99 (dd, J = 11.4, 5.6 Hz, 1H), 1.84-1.57 (m, 6H), 1.15 (d, J = 6.2 Hz, 3H). |

TABLE 49-continued

| Characterization data for intermediates prepared according to procedure above. | | | | |
|---|---|---|---|---|
| Intermediate | Structure | Chemical Name | MS: [(M + 1)]$^+$ | $^1$H-NMR |
| H41 | 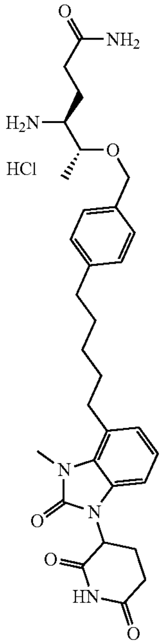 [SMILES: Cl ; C[C@@H](OCc1ccc(CCCCCc2cccc3c2n(C)c(=O)n3C2CCC(=O)NC2=O)cc1)[C@@H](N)CCC(N)=O] | (4S,5R)-4-amino-5-[(4-[5-[1-(2,6-dioxopiperidin-3-yl)-3-methyl-2-oxo-1,3-benzodiazol-4-yl]pentyl]phenyl)methoxy]hexanamide hydrochloride | 564.5 | (400 MHz, DMSO-$d_6$) δ 11.09 (s, 1H), 7.99 (s, 2H), 7.44 (s, 1H), 7.29 (d, J = 7.9 Hz, 2H), 7.18 (d, J = 7.9 Hz, 2H), 6.99-6.91 (m, 2H), 6.85 (dd, J = 6.6, 2.4 Hz, 1H), 5.37 (dd, J = 12.6, 5.3 Hz, 1H), 4.53 (d, J = 11.7 Hz, 1H), 4.46 (d, J = 11.6 Hz, 1H), 3.76 (dd, J = 6.5, 3.5 Hz, 1H), 3.48 (s, 1H), 3.40 (s, 1H), 3.27 (s, 1H), 2.92-2.86 (m, 3H), 2.72 (dd, J = 15.2, 10.8 Hz, 1H), 2.66-2.55 (m, 3H), 2.24 (t, J = 7.4 Hz, 2H), 2.03-1.96 (m, 1H), 1.74 (dq, J = 14.7, 7.1 Hz, 2H), 1.63 (s, 5H), 1.41 (s, 2H), 1.15 (d, J = 6.3 Hz, 3H). |
| H42 | 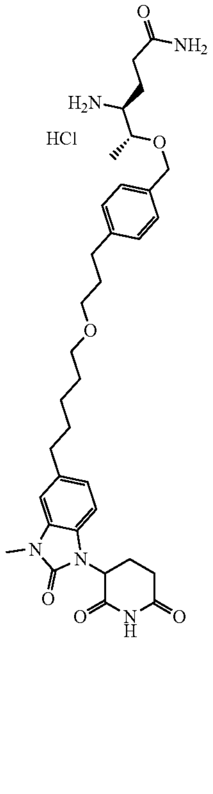 [SMILES: C[C@@H](OCc1ccc(CCCOCCCCCc2ccc3c(c2)n(C)c(=O)n3C2CCC(=O)NC2=O)cc1)[C@@H](N)CCC(N)=O ; Cl] | (4S,5R)-4-amino-5-([4-[3-([5-[1-(2,6-dioxopiperidin-3-yl)-3-methyl-2-oxo-1,3-benzodiazol-5-yl]pentyl]oxy)propyl]phenyl]methoxy)hexanamide hydrochloride | 622.4 | (400 MHz, DMSO-$d_6$) δ 11.08 (s, 1H), 7.86 (s, 3H), 7.41 (s, 1H), 7.32-7.21 (m, 3H), 7.17 (d, J = 7.9 Hz, 2H), 7.05-6.96 (m, 2H), 6.94 (s, 1H), 6.87 (d, J = 7.7 Hz, 1H), 4.54 (d, J = 11.4 Hz, 1H), 4.45 (d, J = 11.8 Hz, 1H), 3.51 (d, J = 3.3 Hz, 1H), 3.36-3.31 (m, 4H), 2.63-2.58 (m, 7H), 2.27-2.19 (m, 2H), 1.76 (s, 6H), 1.61 (s, 3H), 1.58-1.50 (m, 2H), 1.35 (s, 3H), 1.24 (s, 1H), 1.15 (d, J = 6.4 Hz, 3H). |

TABLE 49-continued

| Intermediate | Structure | Chemical Name | MS: $[(M + 1)]^+$ | $^1$H-NMR |
|---|---|---|---|---|
| | Characterization data for intermediates prepared according to procedure above. | | | |
| H43 | 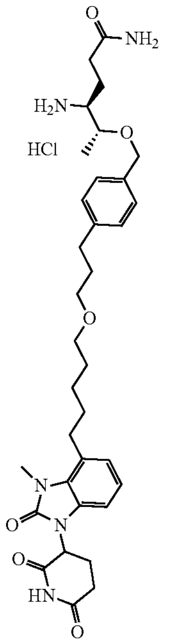 [SMILES: C[C@@H](OCc1ccc(CCCOCCCCCc2cccc3c2n(C)c(=O)n3C2CCC(=O)NC2=O)cc1)[C@@H](N)CCC(N)=O ; Cl] | (4S,5R)-4-amino-5-([4-[3-([5-[1-(2,6-dioxopiperidin-3-yl)-3-methyl-2-oxo-1,3-benzodiazol-4-yl]pentyl]oxy)propyl]phenyl]methoxy)hexanamide hydrochloride | 622.4 | (400 MHz, DMSO-$d_6$) δ 11.09 (s, 1H), 7.96 (s, 2H), 7.43 (s, 1H), 7.29 (d, J = 7.8 Hz, 2H), 7.18 (d, J = 7.8 Hz, 2H), 6.99-6.91 (m, 3H), 6.91-6.84 (m, 1H), 5.37 (dd, J = 12.5, 5.4 Hz, 1H), 4.54 (d, J = 11.7 Hz, 1H), 4.46 (d, J = 11.6 Hz, 1H), 3.76 (d, J = 7.5 Hz, 1H), 3.65 (s, 1H), 3.58 (s, 5H), 3.42-3.31 (m, 5H), 3.27 (s, 1H), 2.93-2.87 (m, 3H), 2.67-2.56 (m, 3H), 2.24 (t, J = 7.4 Hz, 2H), 1.99 (d, J = 11.9 Hz, 1H), 1.77 (s, 3H), 1.65-1.53 (m, 2H), 1.45 (d, J = 7.4 Hz, 2H), 1.24-1.11 (m, 3H), 0.11 (s, 1H). |
| H44 | 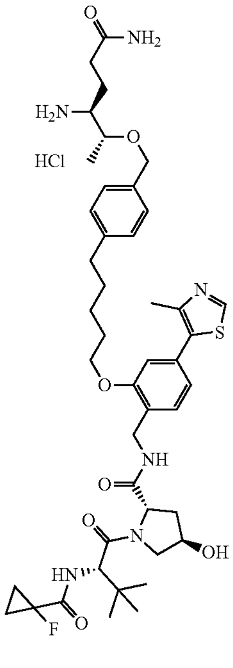 [SMILES: Cc1ncsc1-c1ccc(CNC(=O)[C@@H]2C[C@@H](O)CN2C(=O)[C@@H](NC(=O)C2(F)CC2)C(C)(C)C)c(OCCCCCc2ccc(CO[C@H](C)[C@@H](N)CCC(N)=O)cc2)c1 ; Cl] | (2S,4R)-N-[[2-([5-[4-([[(2R,3S)-3-amino-5-carbamoylpentan-2-yl]oxy]methyl)phenyl]pentyl]oxy)-4-(4-methyl-1,3-thiazol-5-yl)phenyl]methyl]-1-[(2S)-2-[(1-fluorocyclopropyl)formamido]-3,3-dimethylbutanoyl]-4-hydroxypyrrolidine-2-carboxamide hydrochloride | 837.6 | (400 MHz, DMSO-$d_6$) δ 9.02 (s, 1H), 8.52 (t, J = 5.9 Hz, 1H), 8.01 (s, 3H), 7.48-7.37 (m, 2H), 7.29 (d, J = 7.9 Hz, 3H), 7.19 (d, J = 7.9 Hz, 2H), 7.00 (s, 1H), 6.98-6.87 (m, 2H), 4.60 (d, J = 9.2 Hz, 1H), 4.57-4.50 (m, 2H), 4.45 (d, J = 11.6 Hz, 1H), 4.37 (s, 1H), 4.30-4.25 (m, 1H), 4.24-4.17 (m, 1H), 4.05 (t, J = 6.2 Hz, 2H), 3.77 (dd, J = 6.8, 3.4 Hz, 1H), 3.62 (s, 2H), 3.48 (s, 1H), 3.26 (s, 1H), 2.61 (t, J = 7.7 Hz, 2H), 2.46 (s, 3H), 2.24 (t, J = 7.5 Hz, 2H), 2.11 (t, J = 10.3 Hz, 1H), 1.93 (t, J = 6.4 Hz, 1H), 1.81-1.78 (m, 3H), 1.64 (q, J = 7.8 Hz, 2H), 1.49 (d, J = 7.5 Hz, 2H), 1.37 (dd, J = 18.4, 9.6 Hz, 2H), 1.23 (d, J = 8.0 Hz, 2H), 1.15 (d, J = 6.3 Hz, 3H), 0.97 (s, 9H). |

TABLE 49-continued

| Characterization data for intermediates prepared according to procedure above. | | | | |
|---|---|---|---|---|
| Intermediate | Structure | Chemical Name | MS: [(M + 1)]$^+$ | $^1$H-NMR |
| H45 | 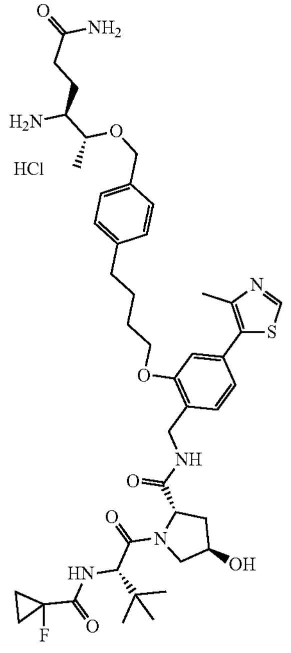 [SMILES: Cc1ncsc1-c1ccc(CNC(=O)[C@@H]2C[C@@H](O)CN2C(=O)[C@@H](NC(=O)C2(F)CC2)C(C)(C)C)c(OCCCCc2ccc(CO[C@H](C)[C@@H](N)CCC(N)=O)cc2)c1 ; Cl] | (2S,4R)-N-[(2-[4-[4-([[(2R,3S)-3-amino-5-carbamoylpentan-2-yl]oxy]meth-yl)phenyl]butoxy]-4-(4-methyl-1,3-thiazol-5-yl)phenyl)methyl]-1-[(2S)-2-[(1-fluorocyclo-propyl)formamido]-3,3-dimethylbutanoyl]-4-hydroxypyrrolidine-2-carboxamide hydrochloride | 823.6 | (400 MHz, $CD_3OD$) δ 10.06-9.88 (m, 1H), 7.62 (d, J = 7.8 Hz, 1H), 7.32 (d, J = 7.8 Hz, 2H), 7.25 (d, J = 7.9 Hz, 2H), 7.11 (d, J = 7.4 Hz, 2H), 4.69-4.61 (m, 2H), 4.56-4.48 (m, 3H), 4.14 (s, 2H), 3.92-3.75 (m, 3H), 3.68-3.66 (m, 4H), 3.62 (s, 2H), 3.38 (d, J = 9.9 Hz, 1H), 2.74 (s, 2H), 2.62 (d, J = 1.4 Hz, 3H), 2.44 (h, J = 8.5 Hz, 1H), 2.25 (t, J = 10.5 Hz, 1H), 2.18-2.07 (m, 1H), 1.89 (s, 6H), 1.42-1.29 (m, 1H), 1.26 (d, J = 6.4 Hz, 3H), 1.06 (s, 9H). |
| H46 | 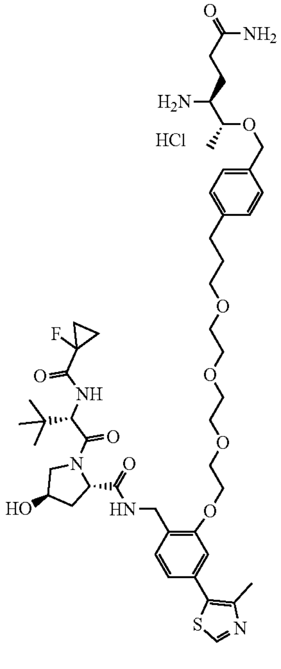 [SMILES: Cc1ncsc1-c1ccc(CNC(=O)[C@@H]2C[C@@H](O)CN2C(=O)[C@@H](NC(=O)C2(F)CC2)C(C)(C)C)c(OCCOCCOCCOCCCc2ccc(CO[C@H](C)[C@@H](N)CCC(N)=O)cc2)c1 ; Cl] | (2S,4R)-N-[(2-[2-[2-(2-[3-[4-([[(2R,3S)-3-amino-5-carbamoylpentan-2-yl]oxy]meth-yl)phenyl]pro-poxylethoxy)eth-oxy]ethoxy]-4-(4-methyl-1,3-thiazol-5-yl)phenyl)methyl]-1-[(2S)-2-[(1-fluorocyclo-propyl)formamido]-3,3-dimethylbutanoyl]-4-hydroxypyrrolidine-2-carboxamide hydrochloride | [(M/2 + 1)]$^+$ = 471.6 | (400 MHz, DMSO-$d_6$) δ 9.02 (s, 1H), 8.50 (t, J = 5.9 Hz, 1H), 8.01 (s, 3H), 7.41 (d, J = 7.8 Hz, 1H), 7.25-7.12 (m, 6H), 7.04 (d, J = 1.7 Hz, 1H), 6.97 (d, J = 7.9 Hz, 1H), 6.91 (s, 1H), 4.60 (d, J = 9.2 Hz, 1H), 4.57-4.48 (m, 2H), 4.45 (d, J = 11.7 Hz, 1H), 4.38-4.26 (m, 3H), 4.23 (d, J = 5.7 Hz, 1H), 4.19 (s, 2H), 3.80-2.77 (m, 4H), 3.70-3.60 (m, 2H), 3.54-3.51 (m, 2H), 3.49-3.43 (m, 2H), 3.37 (t, J = 6.5 Hz, 2H), 3.26 (s, 1H), 2.59 (t, J = 7.7 Hz, 2H), 2.46 (s, 3H), 2.24 (t, J = 7.5 Hz, 2H), 2.10 (t, J = 10.3 Hz, 1H), 1.99-1.86 (m, 1H), 1.76-1.70 (m, 5H), 1.43-1.31 (m, 2H), 1.26-1.19 (m, 2H), 1.14 (d, J = 6.4 Hz, 3H), 0.96 (s, 10H). |

TABLE 49-continued

Characterization data for intermediates prepared according to procedure above.

| Intermediate | Structure | Chemical Name | MS: [(M + 1)]$^+$ | $^1$H-NMR |
|---|---|---|---|---|
| H47 | 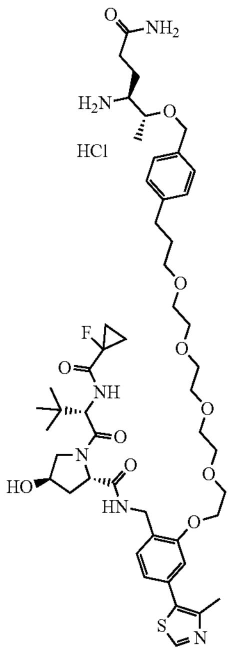 [SMILES: Cc1ncsc1-c1ccc(CNC(=O)[C@@H]2C[C@@H](O)CN2C(=O)[C@@H](NC(=O)C2(F)CC2)C(C)(C)C)c(OCCOCCOCCOCCOCCCc2ccc(CO[C@H](C)[C@@H](N)CCC(N)=O)cc2)c1 ; Cl] | (2S,4R)-N-[[2-([15-[4-([[(2R,3S)-3-amino-5-carbamoylpentan-2-yl]oxy]methyl)phenyl]-3,6,9,12-tetraoxapentadecan-1-yl]oxy)-4-(4-methyl-1,3-thiazol-5-yl)phenyl]methyl]-1-[(2S)-2-[(1-fluorocyclopropyl)formamido]-3,3-dimethylbutanoyl]-4-hydroxypyrrolidine-2-carboxamide hydrochloride | [(M/2 + 1)]$^+$ = 493.6 | (400 MHz, DMSO-d$_6$) δ 9.01 (s, 1H), 8.48 (d, J = 6.1 Hz, 1H), 7.97 (s, 3H), 7.41 (d, J = 8.0 Hz, 1H), 7.30-7.27 (m, 3H), 7.17 (d, J = 7.9 Hz, 2H), 7.04 (s, 1H), 6.97 (d, J = 8.0 Hz, 1H), 6.92 (s, 1H), 4.60 (d, J = 9.2 Hz, 1H), 4.56-4.49 (m, 2H), 4.45 (d, J = 11.7 Hz, 1H), 4.36 (s, 2H), 4.31 (d, J = 10.3 Hz, 1H), 4.31-4.21 (m, 1H), 4.19 (d, J = 5.0 Hz, 2H), 3.80-3.74 (m, 3H), 3.68-3.60 (m, 3H), 3.58-3.49 (m, 7H), 3.49-3.44 (m, 2H), 3.40-3.36 (m, 4H), 3.27 (s, 1H), 2.59 (t, J = 7.7 Hz, 2H), 2.46 (s, 3H), 2.24 (t, J = 7.4 Hz, 2H), 2.10 (t, J = 9.3 Hz, 1H), 1.98-1.87 (m, 1H), 1.77-1.72 (m, 4H), 1.37 (dd, J = 18.5, 9.2 Hz, 2H), 1.23 (d, J = 9.3 Hz, 2H), 1.15 (d, J = 6.3 Hz, 3H), 0.96 (s, 9H). |
| H48 | 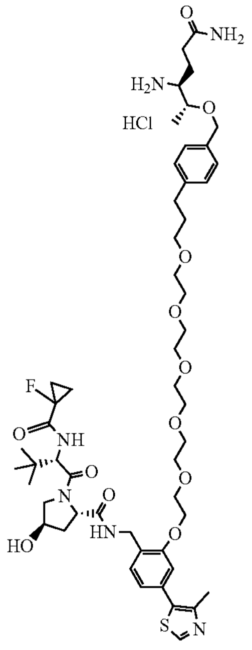 [SMILES: Cc1ncsc1-c1ccc(CNC(=O)[C@@H]2C[C@@H](O)CN2C(=O)[C@@H](NC(=O)C2(F)CC2)C(C)(C)C)c(OCCOCCOCCOCCOCCOCCCc2ccc(CO[C@H](C)[C@@H](N)CCC(N)=O)cc2)c1 ; Cl] | (2S,4R)-N-[[2-([18-[4-[[(2R,3S)-3-amino-5-carbamoylpentan-2-yl]oxy]methyl)phenyl]-3,6,9,12,15-pentaoxaoctadecan-1-yl]oxy)-4-(4-methyl-1,3-thiazol-5-yl)phenyl]methyl]-1-[(2S)-2-[(1-fluorocyclopropyl)formamido]-3,3-dimethylbutanoyl]-4-hydroxy-pyrrolidine-2-carboxamide hydrochloride | [(M/2 + 1)]$^+$ = 515.7 | (400 MHz, DMSO-d$_6$) δ 9.02 (s, 1H), 8.50 (t, J = 6.0 Hz, 1H), 8.02 (s, 3H), 7.63 (dd, J = 11.9, 7.1 Hz, 1H), 7.45-7.34 (m, 1H), 7.31-7.29 (m, 3H), 7.17 (d, J = 7.8 Hz, 2H), 7.04 (s, 1H), 6.97 (d, J = 8.2 Hz, 1H), 6.91 (s, 1H), 4.60 (d, J = 9.2 Hz, 1H), 4.56-4.49 (m, 2H), 4.45 (d, J = 11.5 Hz, 1H), 4.38-4.26 (m, 2H), 4.26-4.08 (m, 3H), 3.83-3.73 (m, 3H), 3.70-3.59 (m, 3H), 3.56-3.44 (m, 14H), 3.40-3.36 (m, 5H), 3.26 (s, 1H), 2.60 (t, J = 7.7 Hz, 2H), 2.47 (s, 3H), 2.25 (t, J = 7.5 Hz, 2H), 2.10 (t, J = 10.4 Hz, 1H), 1.99-1.88 (m, 1H), 1.80-1.73 (m, 4H), 1.43-1.30 (m, 2H), 1.26-1.19 (m, 2H), 1.15 (d, J = 6.3 Hz, 3H), 0.96 (s, 9H). |

TABLE 49-continued

Characterization data for intermediates prepared according to procedure above.

| Intermediate | Structure | Chemical Name | MS: $[(M + 1)]^+$ | $^1$H-NMR |
|---|---|---|---|---|
| H49 | 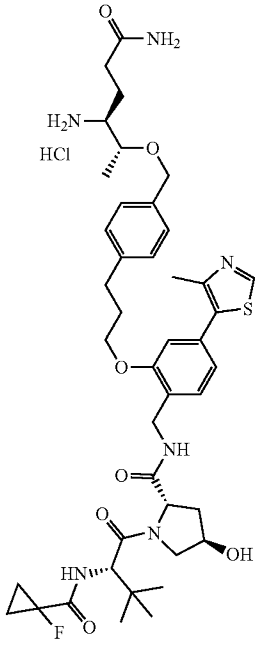 [SMILES: Cc1ncsc1-c1ccc(CNC(=O)[C@@H]2C[C@@H](O)CN2C(=O)[C@@H](NC(=O)C2(F)CC2)C(C)(C)C)c(OCCCc2ccc(CO[C@H](C)[C@@H](N)CCC(N)=O)cc2)c1 ; Cl] | (2S,4R)-N-[(2-[3-[4-([[(2R,3S)-3-amino-5-carbamoylpentan-2-yl]oxy]methyl)phenyl]propoxy]-4-(4-methyl-1,3-thiazol-5-yl)phenyl)methyl]-1-[(2S)-2-[(1-fluorocyclopropyl)formamido]-3,3-dimethylbutanoyl]-4-hydroxypyrrolidine-2-carboxamide hydrochloride | 809.6 | (400 MHz, DMSO-$d_6$) δ 9.01 (s, 1H), 7.97 (s, 3H), 7.42 (d, J = 8.1 Hz, 2H), 7.33-7.30 (m, 3H), 7.24 (d, J = 8.0 Hz, 2H), 6.97 (d, J = 7.3 Hz, 2H), 6.93 (s, 1H), 4.61 (d, J = 9.1 Hz, 1H), 4.57-4.50 (m, 2H), 4.46 (d, J = 11.7 Hz, 1H), 4.38-4.21 (m, 3H), 4.05 (s, 3H), 3.75 (s, 1H), 3.39 (s, 2H), 3.27 (s, 1H), 2.79 (t, J = 7.6 Hz, 2H), 2.45 (s, 3H), 2.24 (t, J = 7.5 Hz, 2H), 2.12-2.03 (m, 3H), 1.74 (d, J = 16.2 Hz, 1H), 1.74 (s, 1H), 1.38 (dd, J = 18.5, 9.7 Hz, 1H), 1.25-1.21 (m, 3H), 1.15 (d, J = 6.4 Hz, 3H), 0.97 (s, 9H). |
| H50 | 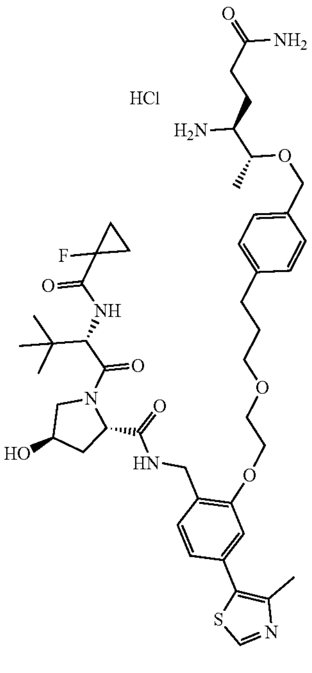 [SMILES: Cc1ncsc1-c1ccc(CNC(=O)[C@@H]2C[C@@H](O)CN2C(=O)[C@@H](NC(=O)C2(F)CC2)C(C)(C)C)c(OCCOCCCc2ccc(CO[C@H](C)[C@@H](N)CCC(N)=O)cc2)c1 ; Cl] | (2S,4R)-N-[[2-(2-[3-[4-([[(2R,3S)-3-amino-5-carbamoylpentan-2-yl]oxy]methyl)phenyl]propoxy]ethoxy)-4-(4-methyl-1,3-thiazol-5-yl)phenyl]methyl]-1-[(2S)-2-[(1-fluorocyclopropyl)formamido]-3,3-dimethylbutanoyl]-4-hydroxypyrrolidine-2-carboxamide hydrochloride | 853.5 | (400 MHz, $CDCl_3$) δ 8.71 (s, 1H), 7.36 (d, J = 7.6 Hz, 1H), 7.32 (d, J = 5.8 Hz, 1H), 7.22 (d, J = 7.8 Hz, 2H), 7.16 (d, J = 7.8 Hz, 2H), 7.07 (dd, J = 9.0, 3.4 Hz, 1H), 6.99 (dd, J = 7.7, 1.5 Hz, 1H), 6.94 (d, J = 1.6 Hz, 1H), 6.39 (s, 1H), 5.51 (s, 1H), 4.95 (d, J = 9.7 Hz, 1H), 4.67 (t, J = 7.8 Hz, 1H), 4.61-4.54 (m, 2H), 4.51 (q, J = 6.2, 5.6 Hz, 2H), 4.47-4.35 (m, 3H), 4.22 (q, J = 5.2 Hz, 2H), 3.95 (d, J = 11.0 Hz, 1H), 3.90-3.82 (m, 3H), 3.66 (dd, J = 11.1, 3.9 Hz, 2H), 3.60-3.56 (m, 3H), 2.71 (t, J = 7.5 Hz, 2H), 2.55 (s, 3H), 2.42 (dt, J = 13.0, 6.9 Hz, 1H), 2.27 (d, J = 9.5 Hz, 2H), 1.99-1.91 (m, 4H), 1.76-1.66 (m, 1H), 1.35-1.26 (m, 4H), 1.22 (d, J = 6.2 Hz, 3H), 0.96 (s, 9H). |

TABLE 49-continued

Characterization data for intermediates prepared according to procedure above.

| Intermediate | Structure | Chemical Name | MS: [(M + 1)]+ | 1H-NMR |
|---|---|---|---|---|
| H51 | 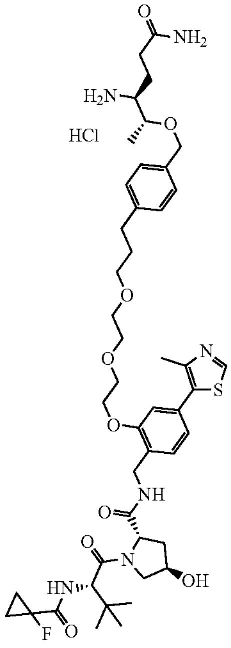 [SMILES: Cc1ncsc1-c1ccc(CNC(=O)[C@@H]2C[C@@H](O)CN2C(=O)[C@@H](NC(=O)C2(F)CC2)C(C)(C)C)c(OCCOCCOCCCc2ccc(CO[C@H](C)[C@@H](N)CCC(N)=O)cc2)c1 ; Cl] | (2S,4R)-N-([2-[2-(2-[3-[4-([[(2R,3S)-3-amino-5-carbamoylpentan-2-yl]oxy]methyl)phenyl]propoxy]ethoxy)ethoxy]-4-(4-methyl-1,3-thiazol-5-yl)phenyl]methyl)-1-[(2S)-2-[(1-fluorocyclopropyl)formamido]-3,3-dimethylbutanoyl]-4-hydroxypyrrolidine-2-carboxamide hydrochloride | 897.7 | (400 MHz, $CD_3OD$) δ 9.39 (s, 1H), 7.55 (d, J = 7.8 Hz, 1H), 7.31-7.28 (m, 3H), 7.23-7.19 (m, 3H), 7.12 (s, 1H), 7.08 (d, J = 8.2 Hz, 2H), 4.62 (s, 5H), 4.53-4.48 (m, 5H), 4.44 (s, 2H), 4.29 (s, 4H), 3.96 (d, J = 4.7 Hz, 4H), 2.71-2.68 (m, 4H), 2.56 (s, 5H), 2.48-2.43 (m, 4H), 2.22 (s, 2H), 2.08 (s, 2H), 1.93 (d, J = 5.2 Hz, 3H), 1.89-1.84 (m, 5H), 1.39-1.30 (m, 8H), 1.30-1.22 (m, 4H). |
| H52 | 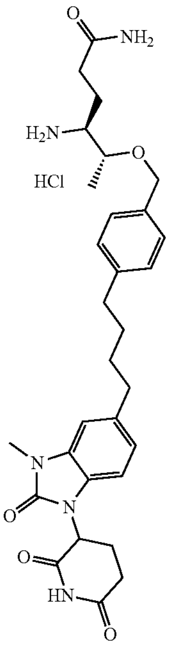 [SMILES: C[C@@H](OCc1ccc(CCCCc2ccc3c(c2)n(C)c(=O)n3C2CCC(=O)NC2=O)cc1)[C@@H](N)CCC(N)=O ; Cl] | (4S,5R)-4-amino-5-[(4-[4-[1-(2,6-dioxopiperidin-3-yl)-3-methyl-2-oxo-1,3-benzodiazol-5-yl]butyl]phenyl)methoxy]hexanamide hydrochloride | 550.2 | crude to next step without further purification |

TABLE 49-continued

| Characterization data for intermediates prepared according to procedure above. | | | | |
|---|---|---|---|---|
| Intermediate | Structure | Chemical Name | MS: [(M + 1)]+ | 1H-NMR |
| H53 | 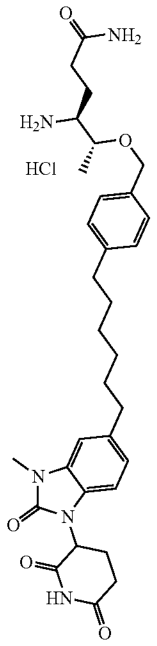 [SMILES: C[C@@H](OCc1ccc(CCCCCCc2ccc3c(c2)n(C)c(=O)n3C2CCC(=O)NC2=O)cc1)[C@@H](N)CCC(N)=O ; Cl] | (4S,5R)-4-amino-5-[(4-[6-[1-(2,6-dioxopiperidin-3-yl)-3-methyl-2-oxo-1,3-benzodiazol-5-yl]hexyl]phenyl) methoxy] hexanamide hydrochloride | 578.5 | crude to next step without further purification |
| H54 | 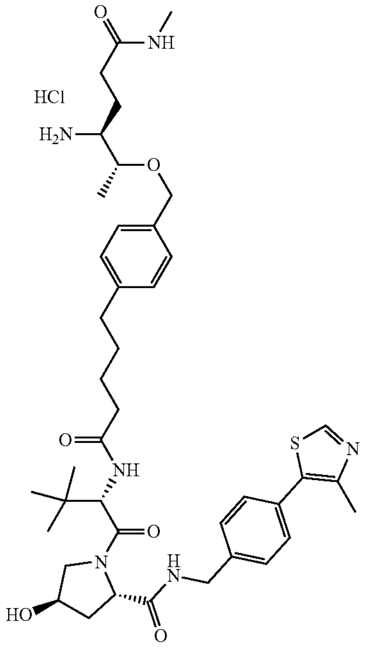 [SMILES: CNC(=O)CC[C@H](N)[C@@H](C)OCc1ccc(CCCCC(=O)N[C@H](C(=O)N2C[C@H](O)C[C@H]2C(=O)NCc2ccc(-c3scnc3C)cc2)C(C)(C)C)cc1 ; Cl] | (2S,4R)-1-[(2S)-2-[5-[4-([[(2R,3S)-3-amino-5-(methyl-carbamoyl)pentan-2-yl]oxy]meth-yl)phenyl]pentan-amido]-3,3-dimethylbutanoyl]-4-hydroxy-N-[[4-(4-methyl-1,3-thiazol-5-yl)phenyl]meth-yl]pyrrolidine-2-carboxamide hydrochloride | 763.6 | (400 MHz, DMSO-$d_6$) δ 9.11 (d, J = 2.1 Hz, 1H), 8.60 (t, J = 6.1 Hz, 1H), 8.12 (s, 3H), 7.98 (s, 1H), 7.88 (d, J = 9.4 Hz, 1H), 7.46-7.37 (m, 4H), 7.28 (d, J = 7.8 Hz, 2H), 7.15 (d, J = 7.9 Hz, 2H), 4.54 (d, J = 8.7 Hz, 2H), 4.51-4.38 (m, 3H), 4.35 (s, 1H), 4.22 (dd, J = 15.7, 5.2 Hz, 1H), 3.85-3.75 (m, 1H), 3.71-3.59 (m, 2H), 3.23 (s, 1H), 2.60-2.52 (m, 5H), 2.46 (s, 3H), 2.26 (t, J = 7.5 Hz, 2H), 2.20-2.11 (m, 1H), 2.04 (t, J = 10.1 Hz, 1H), 1.90 (ddd, J = 12.9, 8.3, 4.6 Hz, 1H), 1.75 (h, J = 6.9 Hz, 2H), 1.55-1.40 (m, 5H), 1.14 (d, J = 6.4 Hz, 3H), 0.93 (s, 9H). |

TABLE 49-continued

| Characterization data for intermediates prepared according to procedure above. | | | | |
|---|---|---|---|---|
| Intermediate | Structure | Chemical Name | MS: [(M + 1)]$^+$ | $^1$H-NMR |
| H55 | 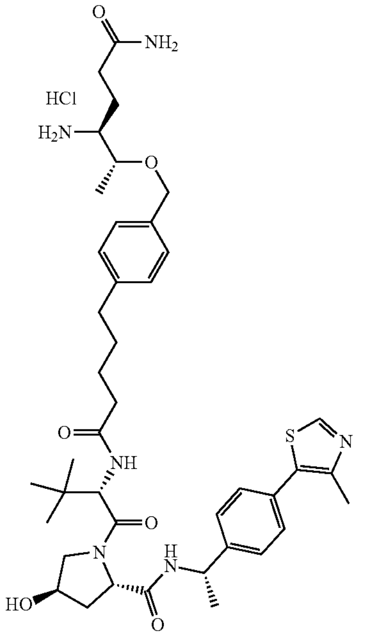 [SMILES: Cc1ncsc1-c1ccc([C@H](C)NC(=O)[C@@H]2C[C@@H](O)CN2C(=O)[C@@H](NC(=O)CCCCc2ccc(CO[C@H](C)[C@@H](N)CCC(N)=O)cc2)C(C)(C)C)cc1 ; Cl] | (2S,4R)-1-[(2S)-2-[5-[4-([[(2R,3S)-3-amino-5-carbamoylpentan-2-yl]oxy]methyl)phenyl]pentanamido]-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride | 763.3 | (400 MHz, $CD_3OD$) δ 10.10-9.93 (m, 1H), 7.62-7.51 (m, 4H), 7.31 (d, J = 7.9 Hz, 2H), 7.20 (d, J = 8.0 Hz, 2H), 5.04 (q, J = 7.0 Hz, 1H), 4.68-4.49 (m, 4H), 4.45 (s, 1H), 3.90 (d, J = 11.1 Hz, 1H), 3.87-3.79 (m, 1H), 3.76 (dd, J = 11.0, 3.9 Hz, 1H), 3.65-3.58 (m, 1H), 3.37 (q, J = 6.1, 5.2 Hz, 1H), 2.67 (d, J = 6.9 Hz, 2H), 2.63 (s, 3H), 2.53-2.17 (m, 3H), 2.01-1.79 (m, 2H), 1.73-1.61 (m, 5H), 1.53 (d, J = 7.0 Hz, 3H), 1.28-1.23 (m, 3H), 1.22-1.17 (m, 1H), 1.06 (s, 8H), 1.03 (s, 1H). |
| H56 | 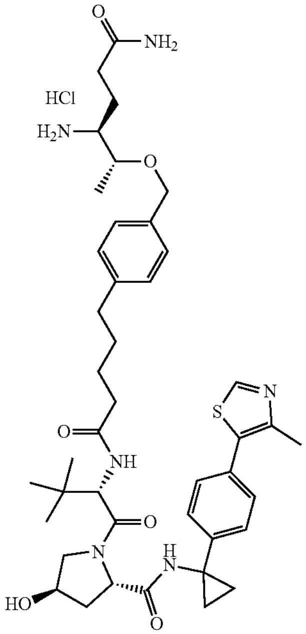 [SMILES: Cc1ncsc1-c1ccc(C2(NC(=O)[C@@H]3C[C@@H](O)CN3C(=O)[C@@H](NC(=O)CCCCc3ccc(CO[C@H](C)[C@@H](N)CCC(N)=O)cc3)C(C)(C)C)CC2)cc1 ; Cl] | (2S,4R)-1-[(2S)-2-[5-[4-([[(2R,3S)-3-amino-5-carbamoylpentan-2-yl]oxy]methyl)phenyl]pentanamido]-3,3-dimethylbutanoyl]-4-hydroxy-N-[1-[4-(4-methyl-1,3-thiazol-5-yl)phenyl]cyclopropyl]pyrrolidine-2-carboxamide hydrochloride | 775.4 | Used directly in next step without further purification |

TABLE 49-continued

| Characterization data for intermediates prepared according to procedure above. | | | | |
|---|---|---|---|---|
| Intermediate | Structure | Chemical Name | MS: [(M + 1)]$^+$ | $^1$H-NMR |
| H57 | 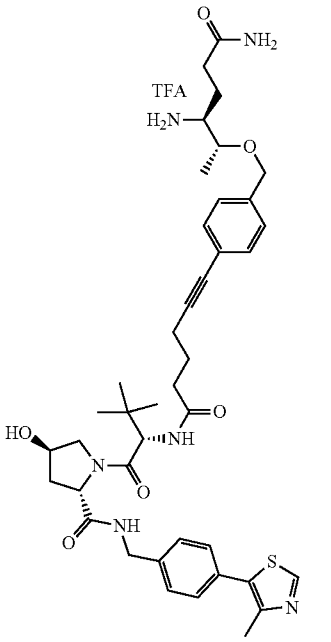 [SMILES: Cc1ncsc1-c1ccc(CNC(=O)[C@@H]2C[C@@H](O)CN2C(=O)[C@@H](NC(=O)CCCC#Cc2ccc(CO[C@H](C)[C@@H](N)CCC(N)=O)cc2)C(C)(C)C)cc1 ; "TFA"] | (2S,4R)-1-[(2S)-2-[6-[4-([[(2R,3S)-3-amino-5-carbamoylpentan-2-yl]oxy]methyl)phenyl]hex-5-ynamido]-3,3-dimethylbutanoyl]-4-hydroxy-N-[[4-(4-methyl-1,3-thiazol-5-yl)phenyl]methyl]pyrrolidine-2-carboxamide; trifluoroacetaldehyde | 759.3 | Used directly in next step without further purification |
| H58 | 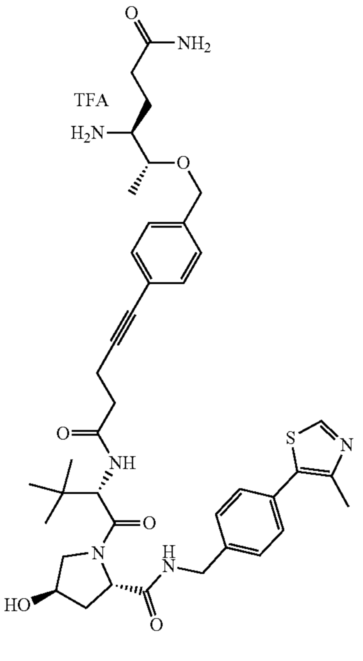 [SMILES: Cc1ncsc1-c1ccc(CNC(=O)[C@@H]2C[C@@H](O)CN2C(=O)[C@@H](NC(=O)CCC#Cc2ccc(CO[C@H](C)[C@@H](N)CCC(N)=O)cc2)C(C)(C)C)cc1 ; "TFA"] | (2S,4R)-1-[(2S)-2-[5-[4-([[(2R,3S)-3-amino-5-carbamoylpentan-2-yl]oxy]methyl)phenyl]pent-4-ynamido]-3,3-dimethylbutanoyl]-4-hydroxy-N-[[4-(4-methyl-1,3-thiazol-5-yl)phenyl]methyl]pyrrolidine-2-carboxamide; trifluoroacetaldehyde | 745.3 | Used directly in next step without further purification |

TABLE 49-continued

| Characterization data for intermediates prepared according to procedure above. | | | | |
|---|---|---|---|---|
| Intermediate | Structure | Chemical Name | MS: [(M + 1)]+ | 1H-NMR |
| H59 | 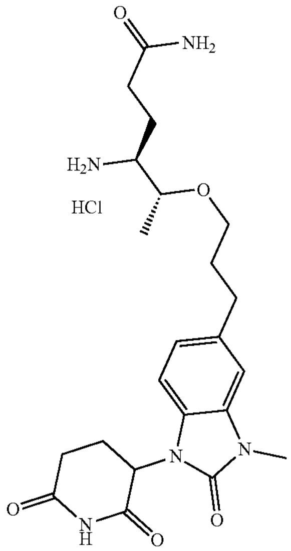 [SMILES: C[C@@H](OCCCc1ccc2c(c1)n(C)c(=O)n2C1CCC(=O)NC1=O)[C@@H](N)CCC(N)=O ; Cl] | (4S,5R)-4-amino-5-[3-[1-(2,6-dioxopiperidin-3-yl)-3-methyl-2-oxo-1,3-benzodiazol-5-yl]propoxy]hexanamide hydrochloride | 446.2 | Used directly in next step without further purification |
| H60 | 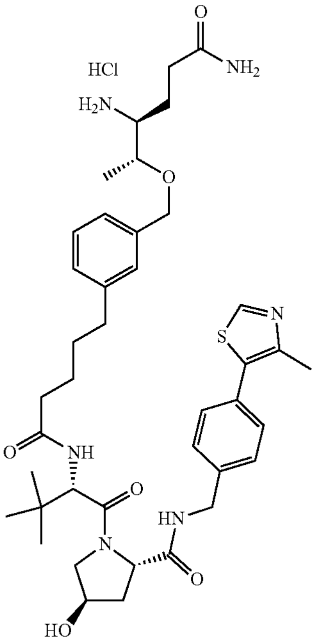 [SMILES: Cc1ncsc1-c1ccc(CNC(=O)[C@@H]2C[C@@H](O)CN2C(=O)[C@@H](NC(=O)CCCCc2cccc(CO[C@H](C)[C@@H](N)CCC(N)=O)c2)C(C)(C)C)cc1 ; Cl] | (2S,4R)-1-[(2S)-2-[5-[3-([[(2R,3S)-3-amino-5-carbamoylpentan-2-yl]oxy]methyl)phenyl]pentanamido]-3,3-dimethylbutanoyl]-4-hydroxy-N-[[4-(4-methyl-1,3-thiazol-5-yl)phenyl]methyl]pyrrolidine-2-carboxamide hydrochloride | 749.3 | (400 MHz, $CD_3OD$) δ 9.96 (s, 1H), 7.57 (m, 4H), 7.32-7.18 (m, 3H), 7.15 (d, J = 7.4 Hz, 1H), 4.70-4.47 (m, 6H), 4.43 (d, J = 15.8 Hz, 1H), 3.93 (d, J = 10.9 Hz, 1H), 3.83 (ddd, J = 10.5, 7.3, 4.2 Hz, 2H), 3.39 (dd, J = 8.3, 4.0 Hz, 1H), 2.66 (dd, J = 14.7, 7.6 Hz, 2H), 2.62 (s, 3H), 2.53-2.36 (m, 2H), 2.35-2.16 (m, 2H), 2.15-2.02 (m, 1H), 2.02-1.80 (m, 2H), 1.70-1.60 (m, 5H), 1.33-1.16 (m, 3H), 1.05 (s, 9H). |

TABLE 49-continued

Characterization data for intermediates prepared according to procedure above.

| Intermediate | Structure | Chemical Name | MS: [(M + 1)]+ | 1H-NMR |
|---|---|---|---|---|
| H61 | 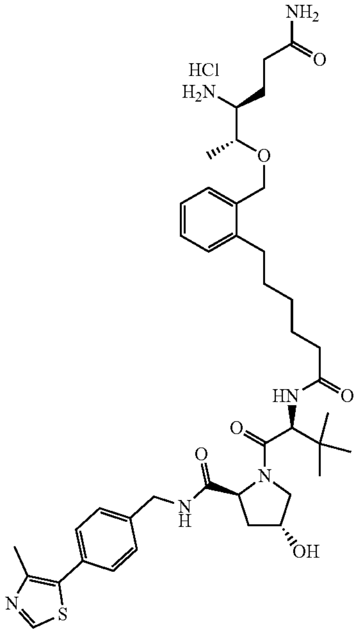 [SMILES: Cc1ncsc1-c1ccc(CNC(=O)[C@@H]2C[C@@H](O)CN2C(=O)[C@@H](NC(=O)CCCCCc2ccccc2CO[C@H](C)[C@@H](N)CCC(N)=O)C(C)(C)C)cc1 ; Cl] | (2S,4R)-1-[(2S)-2-[6-[2-([[(2R,3S)-3-amino-5-carbamoylpentan-2-yl]oxy]methyl)phenyl]hexanamido]-3,3-dimethylbutanoyl]-4-hydroxy-N-[[4-(4-methyl-1,3-thiazol-5-yl)phenyl]methyl]pyrrolidine-2-carboxamide hydrochloride | 763.6 | Used directly in next step without further purification |
| H62 | 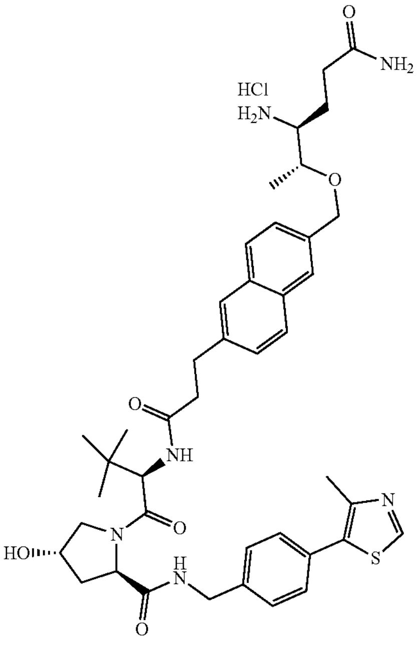 [SMILES: Cc1ncsc1-c1ccc(CNC(=O)[C@H]2C[C@H](O)CN2C(=O)[C@H](NC(=O)CCc2ccc3cc(CO[C@H](C)[C@@H](N)CCC(N)=O)ccc3c2)C(C)(C)C)cc1 ; Cl] | (2S,4R)-1-[(2S)-2-[3-[6-([[(2R,3S)-3-amino-5-carbamoylpentan-2-yl]oxy]methyl)naphthalen-2-yl]propanamido]-3,3-dimethylbutanoyl]-4-hydroxy-N-[[4-(4-methyl-1,3-thiazol-5-yl)phenyl]methyl]pyrrolidine-2-carboxamide hydrochloride | 771.3 | Used directly in next step without further purification |

TABLE 49-continued

Characterization data for intermediates prepared according to procedure above.

| Intermediate | Structure | Chemical Name | MS: [(M + 1)]$^+$ | $^1$H-NMR |
|---|---|---|---|---|
| H63 | 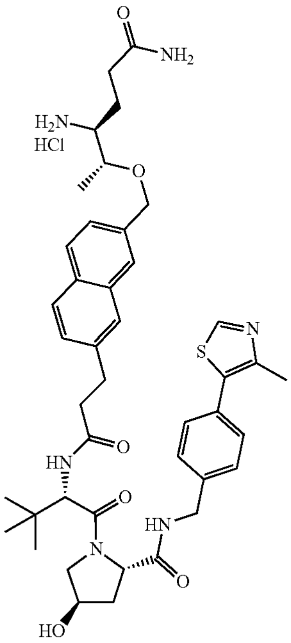 [SMILES: Cc1ncsc1-c1ccc(CNC(=O)[C@@H]2C[C@@H](O)CN2C(=O)[C@@H](NC(=O)CCc2ccc3ccc(CO[C@H](C)[C@@H](N)CCC(N)=O)cc3c2)C(C)(C)C)cc1 ; Cl] | tert-butyl N-[(3S,4R)-1-carbamoyl-4-[[7-(2-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]ethyl)naphthalen-2-yl]methoxy]pentan-3-yl]carbamate. | 771.40 | Used in the next step without further purification |
| H64 | 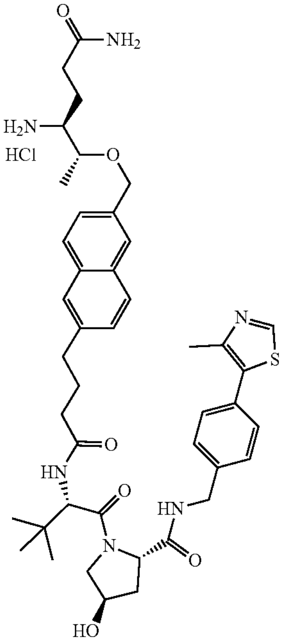 [SMILES: Cl ; Cc1ncsc1-c1ccc(CNC(=O)[C@@H]2C[C@@H](O)CN2C(=O)[C@@H](NC(=O)CCCc2ccc3cc(CO[C@H](C)[C@@H](N)CCC(N)=O)ccc3c2)C(C)(C)C)cc1] | (2S,4R)-1-[(2S)-2-[4-[6-([[(2R,3S)-3-amino-5-carbamoylpentan-2-yl]oxy]methyl)naphthalen-2-yl]butanamido]-3,3-dimethylbutanoyl]-4-hydroxy-N-[[4-(4-methyl-1,3-thiazol-5-yl)phenyl]methyl]pyrrolidine-2-carboxamide | 785.40 | (400 MHz, $CD_3OD$) δ 7.85-7.75 (m, 4H), 7.68 (s, 1H), 7.58-7.47 (m, 5H), 7.40 (dd, J = 8.5, 1.7 Hz, 1H), 4.81 (s, 1H), 4.75-4.65 (m, 2H), 4.65-4.52 (m, 2H), 4.53 (s, 1H), 4.41 (d, J = 15.7 Hz, 1H), 3.95 (d, J = 11.0 Hz, 1H), 3.92-3.79 (m, 2H), 3.45-3.39 (m, 1H), 2.83 (q, J = 8.7, 7.8 Hz, 2H), 2.57 (s, 3H), 2.53- 2.30 (m, 3H), 2.29-2.20 (m, 1H), 2.15-2.02 (m, 2H), 2.01 (s, 2H), 2.00-1.81 (m, 2H), 1.29 (d, J = 6.4 Hz, 3H), 1.07 (s, 9H) |

TABLE 49-continued

| Characterization data for intermediates prepared according to procedure above. | | | | |
|---|---|---|---|---|
| Intermediate | Structure | Chemical Name | MS: [(M + 1)]+ | $^1$H-NMR |
| H65 | 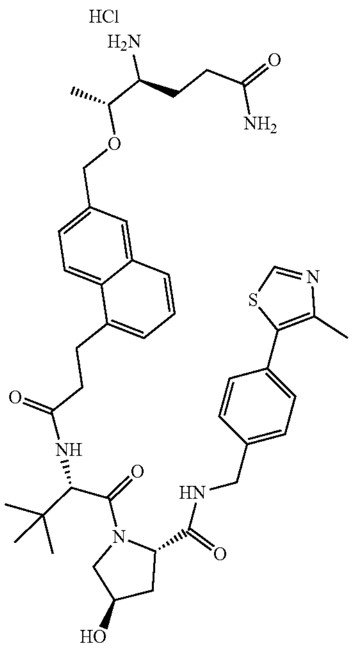 [SMILES: Cl ; Cc1ncsc1-c1ccc(CNC(=O)[C@@H]2C[C@@H](O)CN2C(=O)[C@@H](NC(=O)CCc2cccc3cc(CO[C@H](C)[C@@H](N)CCC(N)=O)ccc23)C(C)(C)C)cc1] | (2S,4R)-1-((S)-2-(3-(6-((((2R,3S)-3,6-diamino-6-oxohexan-2-yl)oxy)methyl)naphthalen-1-yl)propanamido)-3,3-dimethylbutanoyl)-4-hydroxy-N-(4-(4-methylthiazol-5-yl)benzyl)pyrrolidine-2-carboxamide hydrochloride | 771.30 | (400 MHz, DMSO-d$_6$) δ 9.09 (s, 1H), 8.61 (t, J = 6.0 Hz, 1H), 8.15 (s, 3H), 8.08-8.06 (m, 2H), 7.92 (d, J = 1.7 Hz, 1H), 7.76 (d, J = 8.0 Hz, 1H), 7.59 (dd, J = 8.8, 1.7 Hz, 1H), 7.52-7.34 (m, 6H), 6.93 (s, 1H), 5.76 (s, 1H), 4.75 (d, J = 12.2 Hz, 1H), 4.68 (d, J = 12.1 Hz, 1H), 4.59 (d, J = 9.4 Hz, 1H), 4.49-4.35 (m, 2H), 4.25-4.18 (m, 1H), 4.07-4.05 (m, 1H), 3.86 (dd, J = 6.5, 3.4 Hz, 1H), 3.69 (d, J = 4.3 Hz, 2H), 3.39 (s, 1H), 3.33-3.20 (m, 3H), 2.77-2.65 (m, 1H), 2.59-2.56 (m, 1H), 2.45 (s, 3H), 2.27 (t, J = 7.5 Hz, 2H), 2.05 (d, J = 8.3 Hz, 1H), 2.01-1.87 (m, 1H), 1.79-1.77 (m, 2H), 1.26-1.23 (m, 3H), 0.93 (s, 9H). |
| H66 | 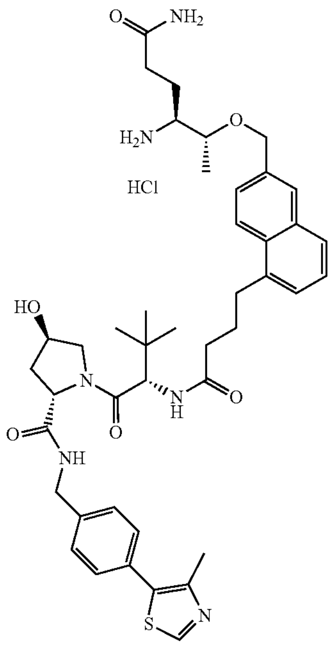 [SMILES: Cc1ncsc1-c1ccc(CNC(=O)[C@@H]2C[C@@H](O)CN2C(=O)[C@@H](NC(=O)CCCc2cccc3cc(CO[C@H](C)[C@@H](N)CCC(N)=O)ccc23)C(C)(C)C)cc1 ; Cl] | (2S,4R)-1-((S)-2-(4-(6-((((2R,3S)-3,6-diamino-6-oxohexan-2-yl)oxy)methyl)naphthalen-1-yl)butanamido)-3,3-dimethylbutanoyl)-4-hydroxy-N-(4-(4-methylthiazol-5-yl)benzyl)pyrrolidine-2-carboxamide | 785.35 | (400 MHz, DMSO-d$_6$) δ 9.06 (d, J = 1.7 Hz, 1H), 8.58 (t, J = 6.1 Hz, 1H), 8.19-8.03 (m, 4H), 7.97 (d, J = 9.3 Hz, 1H), 7.90 (s, 1H), 7.76 (d, J = 8.2 Hz, 1H), 7.57 (d, J = 8.7 Hz, 1H), 7.51-7.36 (m, 5H), 7.33 (d, J = 6.9 Hz, 1H), 6.92 (s, 1H), 4.80-4.63 (m, 2H), 4.60 (d, J = 9.4 Hz, 1H), 4.51-4.38 (m, 2H), 4.37-4.33 (m, 4H), 3.85 (d, J = 6.6 Hz, 1H), 3.69-3.65 (m, 2H), 3.40-3.36 (m, 2H), 3.33-3.30 (m, 1H), 3.05-3.01 (m, 2H), 2.45 (s, 3H), 2.30-2.25 (m, 3H), 2.05-2.03 (m, 1H), 1.97-1.74 (m, 3H), 1.20 (d, J = 6.4 Hz, 3H), 0.95 (s, 9H). |

TABLE 49-continued

| Characterization data for intermediates prepared according to procedure above. | | | | |
|---|---|---|---|---|
| Intermediate | Structure | Chemical Name | MS: $[(M+1)]^+$ | $^1$H-NMR |
| H67 | 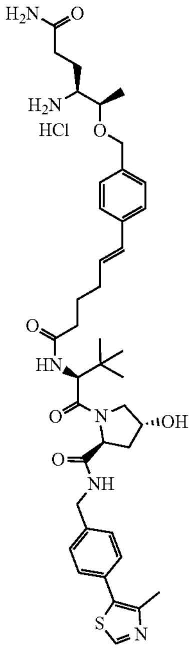 [SMILES: Cc1ncsc1-c1ccc(CNC(=O)[C@@H]2C[C@@H](O)CN2C(=O)[C@@H](NC(=O)CCC/C=C/c2ccc(CO[C@H](C)[C@@H](N)CCC(N)=O)cc2)C(C)(C)C)cc1 ; Cl] | (2S,4R)-1-[(2S)-2-[(5E)-6-[4-([[(2R,3S)-3-amino-5-carbamoylpentan-2-yl]oxy]methyl)phenyl]hex-5-enamido]-3,3-dimethylbutanoyl]-4-hydroxy-N-[[4-(4-methyl-1,3-thiazol-5-yl)phenyl]methyl]pyrrolidine-2-carboxamide | 761.30 | Used in the next step without further purification |
| H68 | 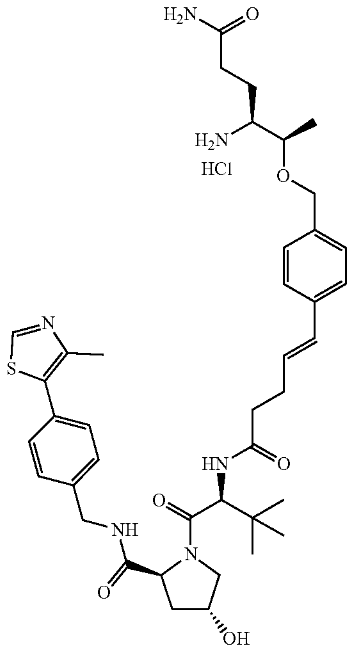 [SMILES: Cc1ncsc1-c1ccc(CNC(=O)[C@@H]2C[C@@H](O)CN2C(=O)[C@@H](NC(=O)CC/C=C/c2ccc(CO[C@H](C)[C@@H](N)CCC(N)=O)cc2)C(C)(C)C)cc1 ; Cl] | (2S,4R)-1-[(2S)-2-[(4E)-5-[4-([[(2R,3S)-3-amino-5-carbamoylpentan-2-yl]oxy]methyl)phenyl]pent-4-enamido]-3,3-dimethylbutanoyl]-4-hydroxy-N-[[4-(4-methyl-1,3-thiazol-5-yl)phenyl]methyl]pyrrolidine-2-carboxamide | 747.30 | (400 MHz, DMSO-$d_6$) δ 9.00 (s, 1H), 8.61-8.55 (m, 1H), 7.97 (d, J = 7.8 Hz, 2H), 7.87-7.84 (m, 1H), 7.46-7.37 (m, 4H), 7.36-7.30 (m, 6H), 7.20 (s, 3H), 7.07 (s, 3H), 6.93 (s, 1H), 6.42 (d, J = 15.9 Hz, 1H), 4.61-4.39 (m, 4H), 4.36 (s, 1H), 4.22 (dd, J = 15.9, 5.4 Hz, 1H), 3.73-3.60 (m, 2H), 2.45 (s, 3H), 2.34 (d, J = 2.2 Hz, 1H), 2.24 (t, J = 7.4 Hz, 1H), 2.04 (s, 1H), 1.91 (d, J = 3.6 Hz, 1H), 1.78-1.70 (m, 1H), 1.24 (s, 3H), 1.14 (d, J = 6.4 Hz, 2H), 1.11-1.01 (m, 1H), 0.93 (s, 9H) |

TABLE 49-continued

Characterization data for intermediates prepared according to procedure above.

| Intermediate | Structure | Chemical Name | MS: [(M + 1)]+ | 1H-NMR |
|---|---|---|---|---|
| H69 | 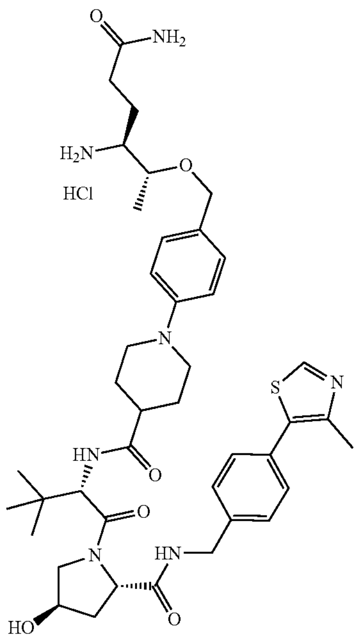 [SMILES: Cc1ncsc1-c1ccc(CNC(=O)[C@@H]2C[C@@H](O)CN2C(=O)[C@@H](NC(=O)C2CCN(c3ccc(CO[C@H](C)[C@@H](N)CCC(N)=O)cc3)CC2)C(C)(C)C)cc1 ; Cl] | 1-[4-([[(2R,3S)-3-amino-5-carbamoylpentan-2-yl]oxy]methyl)phenyl]-N-[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]piperidine-4-carboxamide hydrochloride | 776.30 | Used in the next step without further purification |
| H70 | 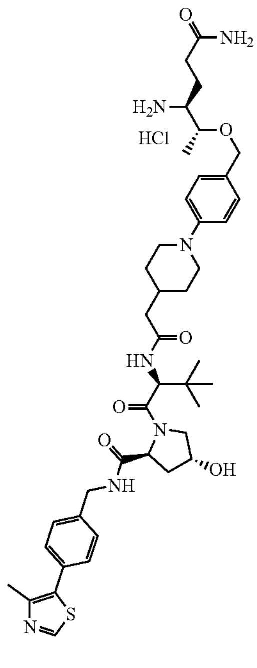 [SMILES: Cc1ncsc1-c1ccc(CNC(=O)[C@@H]2C[C@@H](O)CN2C(=O)[C@@H](NC(=O)CC2CCN(c3ccc(CO[C@H](C)[C@@H](N)CCC(N)=O)cc3)CC2)C(C)(C)C)cc1 ; Cl] | (2S,4R)-1-[(2S)-2-(2-[1-[4-([[(2R,3S)-3-amino-5-carbamoylpentan-2-2-yl]oxy]methyl)phenyl]piperidin-4-yl]acetamido)-3,3-dimethylbutanoyl]-4-hydroxy-N-[[4-(4-methyl-1,3-thiazol-5-yl)phenyl]methyl]pyrrolidine-2-carboxamide hydrochloride | 790.65 | (400 MHz, DMSO-$d_6$) δ 9.04 (s, 1H), 8.59 (t, J = 6.1 Hz, 1H), 8.24-8.02 (m, 3H), 7.93-7.87 (m, 2H), 7.57 (d, J = 8.2 Hz, 2H), 7.41 (q, J = 8.4 Hz, 4H), 4.61-4.49 (m, 2H), 4.48-4.40 (m, 1H), 4.37 (s, 16H), 4.23 (dd, J = 16.0, 5.1 Hz, 1H), 3.86-3.79 (m, 1H), 3.73-3.62 (m, 2H), 3.44-3.34 (m, 1H), 3.27 (s, 1H), 2.46 (s, 3H), 2.26-2.03 (m, 3H), 2.05 (t, J = 10.3 Hz, 1H), 1.96-1.85 (m, 1H), 1.79-1.73 (m, 1H), 1.17 (d, J = 6.4 Hz, 3H), 1.10 (t, J = 7.0 Hz, 1H), 0.96 (s, 9H) |

TABLE 49-continued

| Characterization data for intermediates prepared according to procedure above. | | | | |
|---|---|---|---|---|
| Intermediate | Structure | Chemical Name | MS: $[(M + 1)]^+$ | $^1$H-NMR |
| H71 | 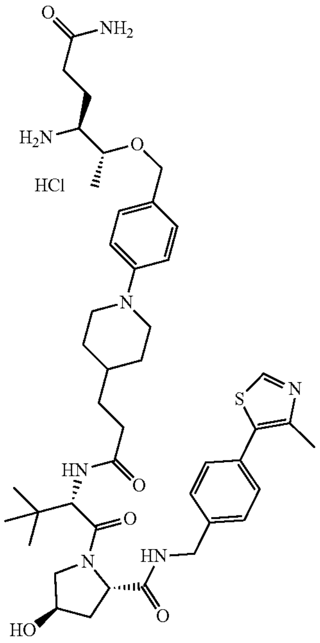 [SMILES: Cc1ncsc1-c1ccc(CNC(=O)[C@@H]2C[C@@H](O)CN2C(=O)[C@@H](NC(=O)CCC2CCN(c3ccc(CO[C@H](C)[C@@H](N)CCC(N)=O)cc3)CC2)C(C)(C)C)cc1 ; Cl] | (2S,4R)-1-((S)-2-(3-(1-(4-((((2R,3S)-3,6-diamino-6-oxohexan-2-yl)oxy)methyl)phenyl)piperidin-4-yl)propanamido)-dimethylbutanoyl)-4-hydroxy-N-(4-(4-methylthiazol-5-yl)benzyl)pyrrolidine-2-carboxamide | $[(M - 1)]^-$ = 802.55 | (400 MHz, DMSO-$d_6$) δ 9.04 (s, 1H), 8.60 (t, J = 6.1 Hz, 1H), 8.18-8.12 (m, 2H), 7.98 (d, J = 9.3 Hz, 1H), 7.86 (s, 2H), 7.57 (d, J = 8.2 Hz, 2H), 7.41 (q, J = 8.3 Hz, 5H), 6.92 (s, 1H), 4.65-4.50 (m, 3H), 4.48-4.41 (m, 2H), 4.22 (dd, J = 16.0, 5.4 Hz, 1H), 3.88-3.79 (m, 1H), 3.68 (s, 2H), 3.53-3.48 (m, 4), 3.39 (q, J = 7.0 Hz, 2H), 3.27 (s, 1H), 2.45 (s, 3H), 2.26 (t, J = 7.5 Hz, 3H), 2.09-2.03 (m, 1H), 1.96-1.87 (m, 3), 1.83-1.71 (m, 1H), 1.67-1.54 (m, 4H), 1.18 (d, J = 6.4 Hz, 3H), 1.10 (t, J = 7.0 Hz, 3H), 0.96 (s, 9H) |
| H72 | 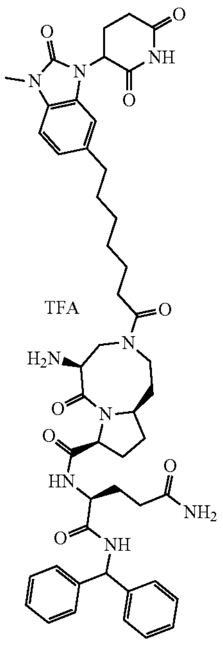 [SMILES: Cn1c(=O)n(C2CCC(=O)NC2=O)c2cc(CCCCCCC(=O)N3CC[C@H]4CC[C@@H](C(=O)N[C@@H](CCC(N)=O)C(=O)NC(c5ccccc5)c5ccccc5)N4C(=O)[C@@H](N)C3)ccc21] | (2S)-2-[[(5S,8S,10aR)-5-amino-3-[7-[3-(2,6-dioxopiperidin-3-yl)-1-methyl-2-oxo-1,3-benzodiazol-5-yl]heptanoyl]-6-oxo-octahydropyrrolo[1,2-a][1,5]diazocin-8-yl]formamido]-(diphenylmethyl)pentanediamide trifluoroacetate | 890.35 | $^1$H NMR (400 MHz, DMSO-$d_6$) δ 11.09 (s, 1H), 8.86 (d, J = 8.2 Hz, 1H), 8.29 (d, J = 5.3 Hz, 2H), 7.39-7.22 (m, 12H), 7.12-7.05 (m, 1H), 7.02-6.97 (m, 1H), 6.91 (d, J = 8.1 Hz, 1H), 6.79 (s, 1H), 6.11 (d, J = 8.4 Hz, 1H), 5.36 (dd, J = 12.8, 5.4 Hz, 1H), 4.52-4.45 (m, 2H), 4.42-4.35 (m, 1H), 4.26-4.14 (m, 2H), 3.98-3.89 (m, 1H), 3.85-3.78 (m, 1H), 3.32 (m, 3H), 3.24-3.12 (m, 1H), 2.97-2.89 (m, 1H), 2.81-2.70 (m, 1H), 2.68-2.55 (m, 3H), 2.36-2.08 (m, 4H), 2.06-1.98 (m, 5H), 1.81-1.75 (m, 1H), 1.70 (d, J = 9.8 Hz, 2H), 1.62-1.54 (m, 5H), 1.37-1.32 (m, 4H) |

TABLE 49-continued

| Characterization data for intermediates prepared according to procedure above. | | | | |
|---|---|---|---|---|
| Intermediate | Structure | Chemical Name | MS: [(M + 1)]$^+$ | $^1$H-NMR |
| H73 | 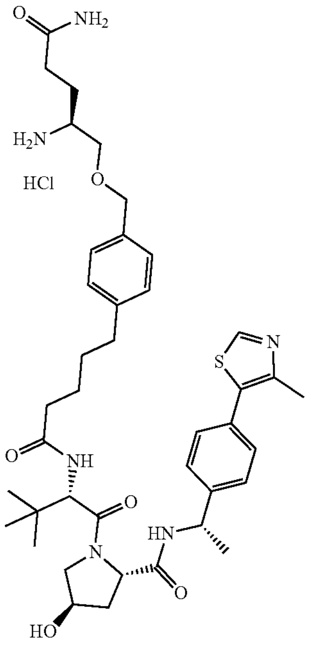 [SMILES: Cc1ncsc1-c1ccc([C@H](C)NC(=O)[C@@H]2C[C@@H](O)CN2C(=O)[C@@H](NC(=O)CCCCc2ccc(COC[C@@H](N)CCC(N)=O)cc2)C(C)(C)C)cc1 ; Cl] | (2S,4R)-1-[(2S)-2-[5-(4-[[(2S)-4-Carbamoyl-2-(chloro-amino)butoxy]meth-yl]phenyl)pentan-amido]-3,3-dimethylbutanoyl]-4-hydroxy-N-[(1S)-1-[4-(4-methyl-1,3-thiazol-5-yl)phenyl]eth-yl]pyrrolidine-2-carboxamide hydrochloride | 749.30 | (400 MHz, DMSO-$d_6$) δ 9.22 (s, 1H), 8.44 (d, J = 7.6 Hz, 1H), 8.30-8.10 (m, 3H), 7.83 (d, J = 9.1 Hz, 1H), 7.55-7.36 (m, 4H), 7.28 (d, J = 7.6 Hz, 2H), 7.17 (d, J = 7.6 Hz, 2H), 6.91 (s, 1H), 4.91 (q, J = 7.1 Hz, 1H), 4.56-4.37 (m, 4H), 4.27 (s, 1H), 3.63-3.58 (m, 6H), 2.62-2.53 (m, 2H), 2.48 (s, 3H), 2.35-1.97 (m, 3H), 1.82-1.76 (m, 2H), 1.59 (s, 7H), 1.37 (d, J = 6.9 Hz, 3H), 0.93 (s, 9H) |
| H74 | 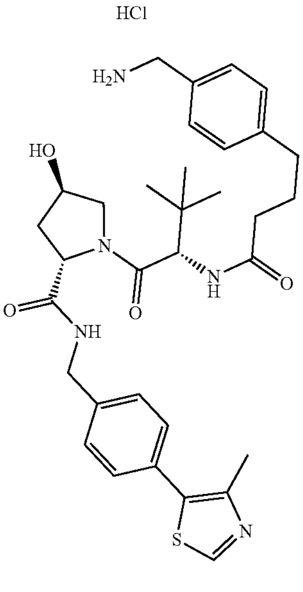 [SMILES: Cl ; Cc1ncsc1-c1ccc(CNC(=O)[C@@H]2C[C@@H](O)CN2C(=O)[C@@H](NC(=O)CCCc2ccc(CN)cc2)C(C)(C)C)cc1] | (2S,4R)-1-[(2S)-2-[4-[4-(aminometh-yl)phenyl]butan-amido]-3,3-dimethylbutanoyl]-4-hydroxy-N-[[4-(4-methyl-1,3-thiazol-5-yl)phenyl]meth-yl]pyrrolidine-2-carboxamide hydrochloride | 606.30 | (400 MHz, DMSO-$d_6$) δ 9.02 (s, 1H), 8.59 (t, J = 6.1 Hz, 1H), 8.28 (br, 2H), 7.92 (d, J = 9.3 Hz, 1H), 7.46-7.34 (m, 6H), 7.23 (d, J = 8.0 Hz, 2H), 4.56 (d, J = 9.4 Hz, 1H), 4.48-4.39 (m, 2H), 4.36 (s, 1H), 4.22 (dd, J = 15.9, 5.4 Hz, 1H), 4.02-3.97 (m, 2H), 3.69-3.65 (m, 2H), 2.59-2.55 (m, 2H), 2.45 (s, 3H), 2.36-2.24 (m, 1H), 2.18-2.15 (m, 1H), 2.06-2.02 (m, 1H), 1.92-1.89 (m, 1H), 1.79-1.76 (m, 2H), 0.95 (s, 9H) |

TABLE 49-continued

Characterization data for intermediates prepared according to procedure above.

| Intermediate | Structure | Chemical Name | MS: [(M + 1)]$^+$ | $^1$H-NMR |
| --- | --- | --- | --- | --- |
| H75 | 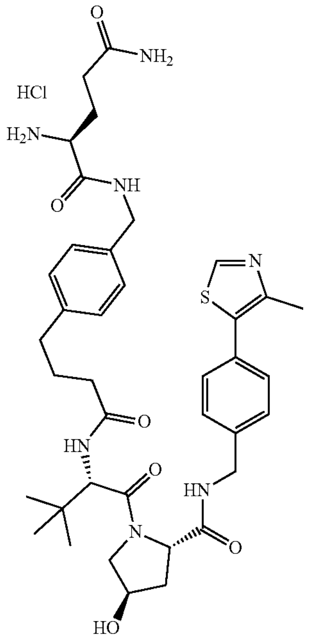 [SMILES: Cl ; Cc1ncsc1-c1ccc(CNC(=O)[C@@H]2C[C@@H](O)CN2C(=O)[C@@H](NC(=O)CCCc2ccc(CNC(=O)[C@@H](N)CCC(N)=O)cc2)C(C)(C)C)cc1] | (2S)-2-amino-N-[[4-(3-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]propyl)phenyl]methyl]pentanediamide hydrochloride | 734.30 | (400 MHz, DMSO-$d_6$) δ 9.04 (s, 1H), 8.98 (t, J = 5.7 Hz, 1H), 8.59 (t, J = 6.0 Hz, 1H), 8.33-8.29 (m, 3H), 7.92 (d, J = 9.3 Hz, 1H), 7.46-7.37 (m, 5H), 7.22 (d, J = 8.1 Hz, 2H), 7.16 (d, J = 8.1 Hz, 2H), 6.95 (s, 1H), 4.59-4.54 (m, 1H), 4.43 (t, J = 8.0 Hz, 2H), 4.36 (d, J = 4.7 Hz, 1H), 4.31 (dd, J = 9.8, 5.5 Hz, 2H), 4.26-4.22 (m, 2H), 2.45 (s, 3H), 2.31-2.24 (m, 1H), 2.20-2.12 (m, 4H), 2.09-2.01 (m, 2H), 2.00-1.87 (m, 4H), 1.86-1.75 (m, 3H), 0.95 (s, 9H) |
| H76 | 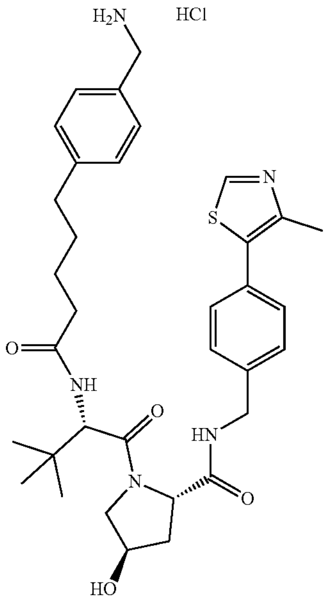 [SMILES: Cl ; Cc1ncsc1-c1ccc(CNC(=O)[C@@H]2C[C@@H](O)CN2C(=O)[C@@H](NC(=O)CCCCc2ccc(CN)cc2)C(C)(C)C)cc1] | (2S,4R)-1-[(2S)-2-[5-[4-(aminomethyl)phenyl]pentanamido]-3,3-dimethylbutanoyl]-4-hydroxy-N-[[4-(4-methyl-1,3-thiazol-5-yl)phenyl]methyl]pyrrolidine-2-carboxamide | 620.20 | (400 MHz, DMSO-$d_6$) δ 9.05 (s, 1H), 8.59 (t, J = 6.0 Hz, 1H), 8.32 (s, 2H), 7.88 (d, J = 9.3 Hz, 1H), 7.40 (dd, J = 8.9, 7.2 Hz, 6H), 7.23 (d, J = 8.1 Hz, 2H), 3.57 (m, 7H), 2.95 (s, 4H), 2.79 (m, 2H), 2.37-2.25 (m, 1H), 2.21-2.13 (m, 1H), 2.04 (m, J = 10.5 Hz, 1H), 1.96 (m, 2H), 1.60 (m, 1H), 1.58-1.38 (m, 4H), 1.24 (m, 1H), 0.94 (s, 9H) |

TABLE 49-continued

| Intermediate | Structure | Chemical Name | MS: [(M + 1)]+ | $^1$H-NMR |
|---|---|---|---|---|
| | Characterization data for intermediates prepared according to procedure above. | | | |
| H77 | 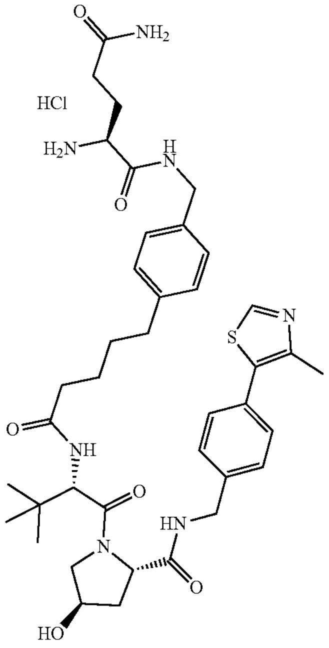 [SMILES: Cc1ncsc1-c1ccc(CNC(=O)[C@@H]2C[C@@H](O)CN2C(=O)[C@@H](NC(=O)CCCCc2ccc(CNC(=O)[C@@H](N)CCC(N)=O)cc2)C(C)(C)C)cc1 ; Cl] | (2S)-2-amino-N-[[4-(4-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]butyl)phenyl]methyl]pentanediamide hydrochloride | 748.25 | Used in the next step without further purification |
| H78 | 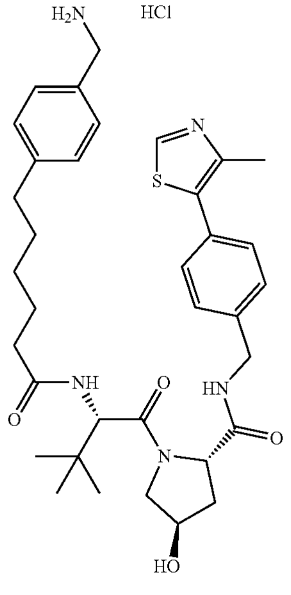 [SMILES: Cl ; Cc1ncsc1-c1ccc(CNC(=O)[C@@H]2C[C@@H](O)CN2C(=O)[C@@H](NC(=O)CCCCCc2ccc(CN)cc2)C(C)(C)C)cc1] | (2S,4R)-1-[(2S)-2-[6-[4-(aminomethyl)phenyl]hexanamido]-3,3-dimethylbutanoyl]-4-hydroxy-N-[[4-(4-methyl-1,3-thiazol-5-yl)phenyl]methyl]pyrrolidine-2-carboxamide hydrochloride | 634.30 | (400 MHz, DMSO-$d_6$) δ 9.08 (s, 1H), 8.60 (t, J = 6.0 Hz, 1H), 8.39 (s, 1H), 7.86 (d, J = 9.3 Hz, 1H), 7.48-7.36 (m, 5H), 7.26-7.18 (m, 2H), 5.07 (s, 1H), 4.59-4.52 (m, 1H), 4.48-4.40 (m, 2H), 4.38-4.34 (m, 1H), 4.22 (dd, J = 15.8, 5.2 Hz, 1H), 4.03-3.84 (m, 2H), 3.75-3.60 (m, 2H), 2.56 (t, J = 7.6 Hz, 2H), 2.46 (s, 3H), 2.26 (dt, J = 14.8, 7.5 Hz, 1H), 2.18-1.98 (m, 2H), 1.92-1.87 (m, 1H), 1.59-1.42 (m, 4H), 1.29-1.25 (m, 2H), 0.94 (s, 9H). |

TABLE 49-continued

| Characterization data for intermediates prepared according to procedure above. | | | | |
|---|---|---|---|---|
| Intermediate | Structure | Chemical Name | MS: $[(M + 1)]^+$ | $^1H$-NMR |
| H79 | 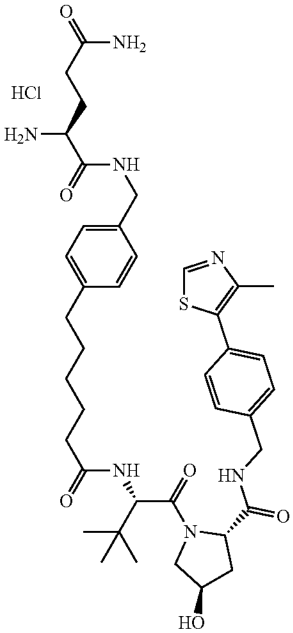 [SMILES: Cl ; Cc1ncsc1-c1ccc(CNC(=O)[C@@H]2C[C@@H](O)CN2C(=O)[C@@H](NC(=O)CCCCCc2ccc(CNC(=O)[C@@H](N)CCC(N)=O)cc2)C(C)(C)C)cc1] | (2S)-2-amino-N-[[4-(5-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]pentyl)phenyl]methyl]pentanediamide hydrochloride | 762.35 | (400 MHz, DMSO-$d_6$) δ 9.03 (s, 1H), 8.96 (m, J = 5.7 Hz, 1H), 8.59 (d, J = 6.0 Hz, 1H), 8.32-8.27 (m, 2H), 7.86-7.85 (m, 1H), 7.43-7.39 (m, 5H), 7.22-7.14 (m, 4H), 6.97-6.95 (m, 1H), 4.59-4.50 (m, 1H), 4.46-4.42 (m, 2H), 4.37-4.19 (m, 5H), 4.03-3.84 (m, 2H), 3.75-3.60 (m, 2H), 2.45 (s, 3H), 2.30-2.17 (m, 3H), 2.17-2.01 (m, 2H), 1.99-1.89 (m, 3H), 1.61-1.52 (m, 6H), 1.28-1.24 (m, 2H), 0.93 (s, 9H) |
| H80 | 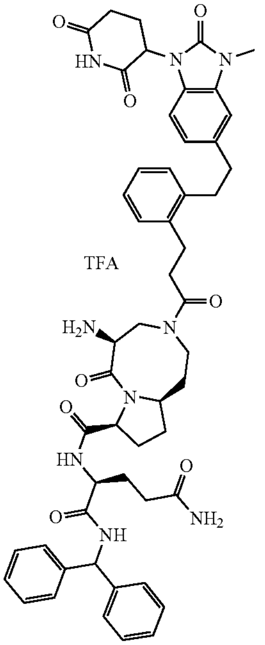 [SMILES: Cn1c(=O)n(C2CCC(=O)NC2=O)c2ccc(CCc3ccccc3CCC(=O)N3CC[C@H]4CC[C@@H](C(=O)N[C@@H](CCC(N)=O)C(=O)NC(c5ccccc5)c5ccccc5)N4C(=O)[C@@H](N)C3)cc21] | (2S)-2-[[(5S,8S,10aR)-5-amino-3-[3-(2-[2-[1-(2,6-dioxopiperidin-3-yl)-3-methyl-2-oxo-1,3-benzodiazol-5-yl]ethyl]phenyl)propanoyl]-6-oxo-octahydropyrrolo[1,2-a][1,5]diazocin-8-yl]formamido]-N-(diphenylmethyl)pentanediamide trifluoroacetates | 938.30 | (400 MHz, DMSO-$d_6$) δ 11.10 (s, 1H), 8.87-8.76 (m, 1H), 8.30-8.26 (m, 3H), 7.37-7.09 (m, 14H), 7.02 (t, J = 7.9 Hz, 1H), 6.93 (d, J = 8.1 Hz, 1H), 6.80 (d, J = 21.5 Hz, 1H), 6.15-6.04 (m, 1H), 5.34 (d, J = 13.0 Hz, 1H), 4.50-4.24 (m, 4H), 4.24-3.85 (m, 3H), 3.80 (t, J = 19.8 Hz, 2H), 3.42-3.40 (m, 1H), 3.34 (s, 3H), 3.27-3.07 (m, 1H), 2.95-2.85 (m, 6H), 2.79-2.57 (m, 5H), 2.29-1.38 (m, 11H) |

TABLE 49-continued

Characterization data for intermediates prepared according to procedure above.

| Intermediate | Structure | Chemical Name | MS: $[(M + 1)]^+$ | $^1$H-NMR |
|---|---|---|---|---|
| H81 | 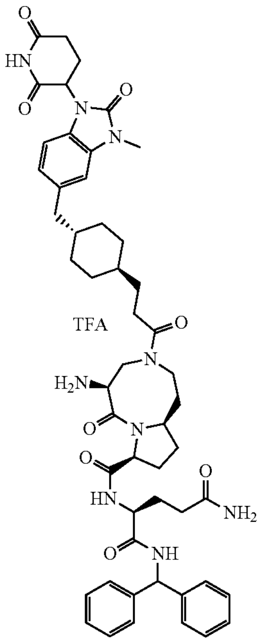 [SMILES: Cn1c(=O)n(C2CCC(=O)NC2=O)c2ccc(C[C@H]3CC[C@H](CCC(=O)N4CC[C@H]5CC[C@@H](C(=O)N[C@@H](CCC(N)=O)C(=O)NC(c6ccccc6)c6ccccc6)N5C(=O)[C@@H](N)C4)CC3)cc21] | (2S)-2-[[(5S,8S,10aR)-5-amino-6-oxo-3-[3-[(1r,4r)-4-[[1-(2,6-dioxopiperidin-3-yl)-3-methyl-2-oxo-1,3-benzodiazol-5-yl]methyl]cyclohex-yl]propanoyl]-octa-hydropyrrolo[1,2-a][1,5]diazocin-8-yl]formamido]-N-(diphenylmeth-yl)pentanediamide trifluoroacetate | 930.35 | (400 MHz, DMSO-$d_6$) δ 11.08 (s, 1H), 8.73 (d, J = 8.4 Hz, 1H), 8.18-8.16 (m, 2H), 7.39-7.18 (m, 11H), 7.02-6.96 (m, 2H), 6.81 (dd, J = 8.1, 1.7 Hz, 1H), 6.72 (d, J = 19.1 Hz, 1H), 6.47 (d, J = 6.9 Hz, 1H), 6.09 (d, J = 8.3 Hz, 1H), 5.76 (s, 2H), 5.34 (dd, J = 12.6, 5.4 Hz, 1H), 4.43-4.27 (m, 2H), 4.09-4.01 (m, 1H), 3.70-3.66 (m, 2H), 3.32-3.30 (m, 11H), 3.24-3.04 (m, 1H), 2.98-2.84 (m, 1H), 2.75-2.60 (m, 2H), 2.47-2.44 (m, 1H), 2.17-2.04 (m, 3H), 2.09-1.90 (m, 2H), 1.83-1.56 (m, 6H), 1.43-1.34 (m, 2H), 1.18 (t, J = 7.1 Hz, 1H), 0.98-0.79 (m, 4H) |
| H82 | 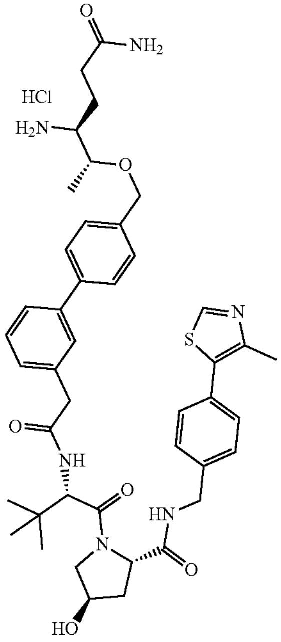 [SMILES: Cc1ncsc1-c1ccc(CNC(=O)[C@@H]2C[C@@H](O)CN2C(=O)[C@@H](NC(=O)Cc2cccc(-c3ccc(CO[C@H](C)[C@@H](N)CCC(N)=O)cc3)c2)C(C)(C)C)cc1 ; Cl] | (2S,4R)-1-[(2S)-2-[2-[4-([[(2R,3S)-3-amino-5-carbamoylpentan-2-yl]oxy]methyl)-[1,1-biphenyl]-3-yl]acetamido]-3,3-dimethylbutanoyl]-4-hydroxy-N-[[4-(4-methyl-1,3-thiazol-5-yl)phenyl]meth-yl]pyrrolidine-2-carboxamide hydrochloride | 783.30 | (400 MHz, DMSO-$d_6$) δ 9.11 (s, 1H), 8.63 (t, J = 6.0 Hz, 1H), 8.20-8.15 (m, 4H), 7.64-7.60 (m, 3H), 7.54-7.46 (m, 4H), 7.46-7.37 (m, 4H), 7.37-7.19 (m, 2H), 6.93 (s, 1H), 4.64-4.51 (m, 3H), 4.49-4.39 (m, 2H), 4.35 (s, 1H), 4.23 (dd, J = 15.8, 5.5 Hz, 1H), 3.84 (dd, J = 6.5, 3.3 Hz, 1H), 3.75 (d, J = 13.7 Hz, 1H), 3.71-3.59 (m, 2H), 3.28 (s, 1H), 2.46 (s, 3H), 2.28 (t, J = 7.5 Hz, 2H), 2.05 (t, J = 10.3 Hz, 1H), 1.94-1.87 (m, 1H), 1.84-1.72 (m, 2H), 1.24 (s, 1H), 1.19 (d, J = 6.4 Hz, 3H), 0.93 (s, 9H) |

TABLE 49-continued

Characterization data for intermediates prepared according to procedure above.

| Intermediate | Structure | Chemical Name | MS: $[(M + 1)]^+$ | $^1$H-NMR |
|---|---|---|---|---|
| H83 | 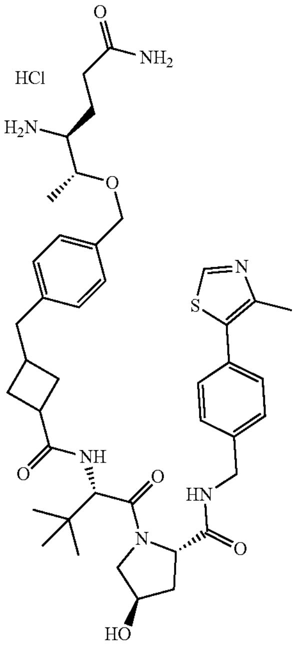 [SMILES: Cc1ncsc1-c1ccc(CNC(=O)[C@@H]2C[C@@H](O)CN2C(=O)[C@@H](NC(=O)C2CC(Cc3ccc(CO[C@H](C)[C@@H](N)CCC(N)=O)cc3)C2)C(C)(C)C)cc1 ; Cl] | (2S,4R)-1-[(2S)-3,3-dimethyl-2-[[(1r,3r)-3-[[4-([[(2R,3S)-3-amino-5-carbamoylpentan-2-yl]oxy]methyl)phenyl]methyl]cyclobutyl]formamido]butanoyl]-4-hydroxy-N-[[4-(4-methyl-1,3-thiazol-5-yl)phenyl]methyl]pyrrolidine-2-carboxamide hydrochloride | 761.35 | (400 MHz, DMSO-$d_6$) δ 9.04 (d, J = 2.0 Hz, 1H), 8.58 (t, J = 6.1 Hz, 1H), 8.03 (s, 4H), 7.69 (d, J = 9.3 Hz, 1H), 7.46-7.34 (m, 4H), 7.28 (dd, J = 7.8, 4.4 Hz, 2H), 7.14 (t, J = 7.8 Hz, 2H), 6.92 (s, 1H), 4.59-4.49 (m, 2H), 4.43 (dd, J = 14.9, 9.4 Hz, 4H), 4.22 (dd, J = 15.8, 5.4 Hz, 1H), 3.77 (d, J = 7.6 Hz, 1H), 3.66 (s, 1H), 3.26 (s, 2H), 3.05 (p, J = 8.7 Hz, 1H), 2.62 (d, J = 7.5 Hz, 2H), 2.46 (d, J = 4.7 Hz, 1H), 2.45 (s, 3H), 2.24 (t, J = 7.5 Hz, 2H), 2.07 (dd, J = 36.2, 8.7 Hz, 3H), 1.96-1.84 (m, 2H), 1.75 (tt, J = 15.1, 8.4 Hz, 3H), 1.60 (s, 3H), 1.16 (t, J = 6.2 Hz, 3H), 0.92 (s, 9H); |
| H84 | 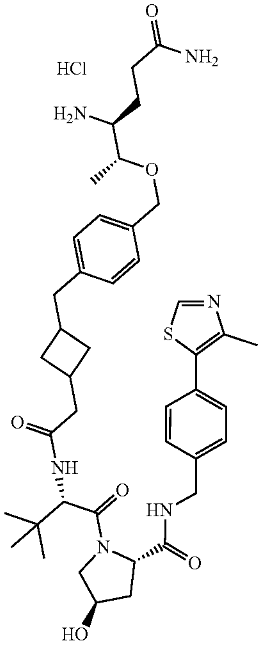 [SMILES: Cc1ncsc1-c1ccc(CNC(=O)[C@@H]2C[C@@H](O)CN2C(=O)[C@@H](NC(=O)CC2CC(Cc3ccc(CO[C@H](C)[C@@H](N)CCC(N)=O)cc3)C2)C(C)(C)C)cc1 ; Cl] | (2S,4R)-1-[(2S)-2-[2-(3-[[4-([[(2R,3S)-3-amino-5-carbamoylpentan-2-yl]oxy]methyl)phenyl]methyl]cyclobutyl)acetamido]-3,3-dimethylbutanoyl]-4-hydroxy-N-[[4-(4-methyl-1,3-thiazol-5-yl)phenyl]methyl]pyrrolidine-2-carboxamide hydrochloride | 775.35 | $^1$H NMR (400 MHz, $CD_3OD$) δ 10.07 (s, 1H), 7.58 (q, J = 8.0 Hz, 4H), 7.37-7.26 (m, 2H), 7.16 (t, J = 7.9 Hz, 2H), 4.66-4.62 (m, 1H), 4.64-4.48 (m, 7H), 4.45-4.41 (m, 1H), 3.94-3.77 (m, 3H), 3.66-3.47 (m, 1H), 3.41-3.37 (m, 1H), 2.77 (d, J = 7.8 Hz, 1H), 2.71-2.65 (m, 2H), 2.64 (s, 3H), 2.63-2.54 (m, 1H), 2.54-2.29 (m, 4H), 2.30-2.15 (m, 1H), 2.14-2.02 (m, 1H), 2.03-1.91 (m, 1H), 1.91-1.80 (m, 1H), 1.52-1.47 (m, 1H), 1.26 (s, 3H), 1.24-1.16(m, 1H), 1.04 (d, J = 2.7 Hz, 9H) |

TABLE 49-continued

| Intermediate | Structure | Chemical Name | MS: [(M + 1)]+ | $^1$H-NMR |
|---|---|---|---|---|
| Characterization data for intermediates prepared according to procedure above. | | | | |
| H85 | 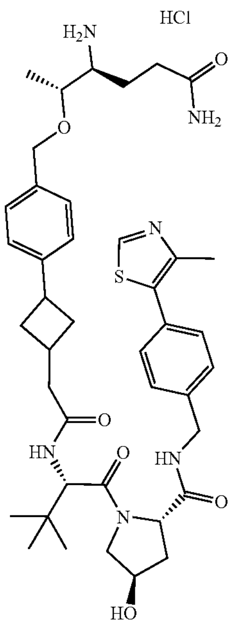 [SMILES: Cl ; Cc1ncsc1-c1ccc(CNC(=O)[C@@H]2C[C@@H](O)CN2C(=O)[C@@H](NC(=O)CC2CC(c3ccc(CO[C@H](C)[C@@H](N)CCC(N)=O)cc3)C2)C(C)(C)C)cc1] | (2S,4R)-1-[(2S)-2-(2-[3-[4-([[(2R,3S)-3-amino-5-carbamoylpentan-2-yl]oxy]methyl)phenyl]cyclobutyl]acetamido)-3,3-dimethylbutanoyl]-4-hydroxy-N-[[4-(4-methyl-1,3-thiazol-5-yl)phenyl]methyl]pyrrolidine-2-carboxamide hydrochloride | 761.35 | (400 MHz, $CD_3OD$) δ 10.01-9.95 (m, 1H), 7.63-7.51 (m, 4H), 7.37-7.20 (m, 4H), 4.69-4.65 (m, 1H), 4.66-4.49 (m, 6H), 4.43 (d, J = 15.7 Hz, 1H), 3.93 (d, J = 11.0 Hz, 1H), 3.88-3.79 (m, 2H), 3.66-3.54 (m, 1H), 3.43-3.34 (m, 2H), 2.82-2.63 (m, 1H), 2.63 (d, J = 1.0 Hz, 3H), 2.61-2.50 (m, 1H), 2.51-2.29 (m, 3H), 2.30-2.20 (m, 2H), 2.15-2.02 (m, 1H), 2.02-1.79 (m, 2H), 1.62-1.58 (m, 1H), 1.25 (s, 3H), 1.06 (s, 9H) |
| H86 | 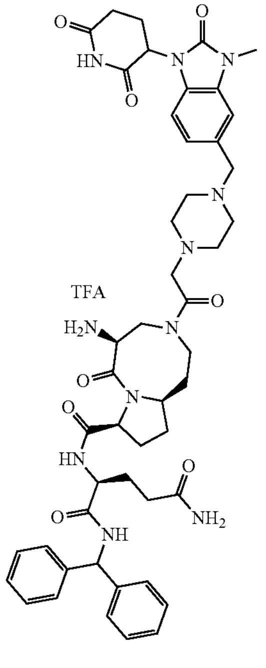 [SMILES: Cn1c(=O)n(C2CCC(=O)NC2=O)c2ccc(CN3CCN(CC(=O)N4CC[C@H]5CC[C@@H](C(=O)N[C@@H](CCC(N)=O)C(=O)NC(c6ccccc6)c6ccccc6)N5C(=O)[C@@H](N)C4)CC3)cc21] | (2S)-2-((5S,8S,10aR)-5-amino-3-(2-(4-((1-(2,6-dioxopiperidin-3-yl)-3-methyl-2-oxo-2,3-dihydro-1H-benzo[d]imidazol-5-yl)methyl)piperazin-1-yl)acetyl)-6-oxodecahydro-pyrrolo[1,2-a][1,5]diazocine-8-carboxamido)-N1-benzhydrylpentane diamide trifluoroacetate | 918.54 | (400 MHz, DMSO-$d_6$) δ 11.09 (s, 1H), 8.74 (d, J = 8.4 Hz, 1H), 8.21-8.17 (m, 1H), 7.38-7.20 (m, 15H), 7.10 (d, J = 1.4 Hz, 1H), 7.05 (d, J = 8.0 Hz, 1H), 6.97 (dd, J = 8.1, 1.4 Hz, 1H), 6.75-6.70 (m, 1H), 6.10 (d, J = 8.4 Hz, 1H), 5.36 (dd, J = 12.7, 5.5 Hz, 1H), 4.42-4.29 (m, 3H), 4.10-3.95 (m, 1H), 3.81-3.69 (m, 1H), 3.47 (s, 3H), 3.26-3.05 (m, 5H), 3.00-2.86 (m, 3H), 2.77-2.58 (m, 2H), 2.49-2.22 (m, 10H), 2.16-2.09 (m, 2H), 2.06-1.70 (m, 2H), 1.68-1.49 (m, 2H), 1.32-1.17 (m, 2H) |

TABLE 49-continued

| Characterization data for intermediates prepared according to procedure above. | | | | |
|---|---|---|---|---|
| Intermediate | Structure | Chemical Name | MS: [(M + 1)]+ | 1H-NMR |
| H87 | 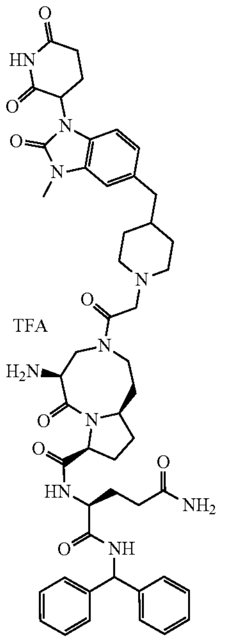 [SMILES: Cn1c(=O)n(C2CCC(=O)NC2=O)c2ccc(CC3CCN(CC(=O)N4CC[C@H]5CC[C@@H](C(=O)N[C@@H](CCC(N)=O)C(=O)NC(c6ccccc6)c6ccccc6)N5C(=O)[C@@H](N)C4)CC3)cc21] | (2S)-2-[[(5S,8S,10aR)-5-amino-3-[2-(4-[[1-(2,6-Dioxopiperidin-3-yl)-3-methyl-2-oxo-1,3-benzoazol-5-yl]methyl]piperidin-1-yl)acetyl]-6-oxo-octahydro-pyrrolo[1,2-a][1,5]diazocin-8-yl]formamido]-N-(diphenylmeth-yl)pentanediamide trifluoroacetate | 917.40 | (400 MHz, DMSO-$d_6$) δ 11.10 (s, 1H), 9.41 (s, 1H), 8.85-8.69 (m, 1H), 8.48-8.26 (m, 2H), 7.40-7.18 (m, 11H), 7.04 (h, J = 4.1, 3.5 Hz, 2H), 6.91-6.75 (m, 2H), 6.10 (d, J = 8.2 Hz, 1H), 5.36 (dd, J = 12.9, 5.4 Hz, 1H), 4.74-4.18 (m, 4H), 3.53-3.38 (m, 1H), 3.33 (s, 3H), 3.18-2.80 (m, 6H), 2.78-2.54 (m, 4H), 2.20-2.08 (m, 4H), 2.01-1.85 (m, 2H), 1.88-1.64 (m, 12H), 1.63-1.49 (m, 2H) |
| H88 | 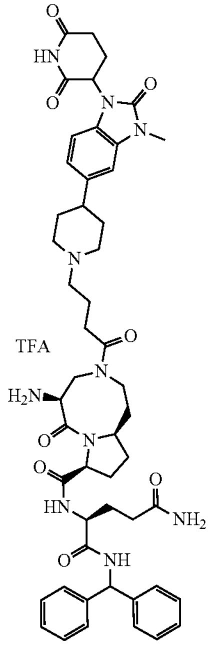 [SMILES: Cn1c(=O)n(C2CCC(=O)NC2=O)c2ccc(C3CCN(CCCC(=O)N4CC[C@H]5CC[C@@H](C(=O)N[C@@H](CCC(N)=O)C(=O)NC(c6ccccc6)c6ccccc6)N5C(=O)[C@@H](N)C4)CC3)cc21] | (2S)-2-[[(5S,8S,10aR)-3-(4-[4-[1-(2,6-dioxopiperidin-3-yl)-3-methyl-2-oxo-1,3-benzodiazol-5-yl]piperidin-1-yl]butanoyl)-6-oxo-5-(2,2,2-trifluoroacetamido)-octahydro-pyrrolo[1,2-a][1,5]diazocin-8-yl]formamido]-N-(diphenylmeth-yl)pentanediamide trifluoroacetate | 931.40 | (400 MHz, DMSO-$d_6$) δ 11.10 (s, 1H), 9.50 (s, 1H), 8.83-8.74 (m, 1H), 8.46-8.27 (m, 2H), 7.41-7.14 (m, 11H), 7.13-6.97 (m, 2H), 6.92 (dt, J = 8.2, 1.9 Hz, 1H), 6.80 (d, J = 13.5 Hz, 1H), 6.11 (d, J = 8.4 Hz, 1H), 5.37 (dd, J = 12.8, 5.4 Hz, 1H), 4.64-4.14 (m, 5H), 3.93-3.85 (m, 5H), 3.35 (s, 3H), 3.20-2.97 (m, 6H), 2.99-2.79 (m, 3H), 2.79-2.57 (m, 4H), 2.29-1.60 (m, 10H), 1.31-1.20 (m, 1H), 0.86-0.82 (m, 1H) |

TABLE 49-continued

Characterization data for intermediates prepared according to procedure above.

| Intermediate | Structure | Chemical Name | MS: [(M + 1)]+ | $^1$H-NMR |
|---|---|---|---|---|
| H89 | 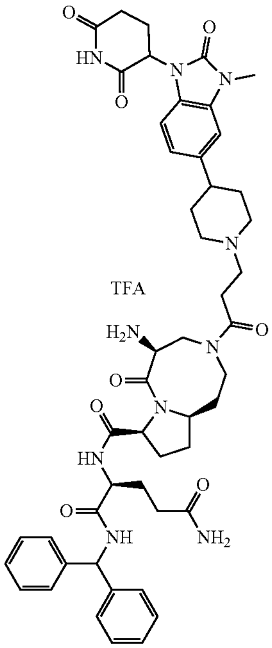 [SMILES: Cn1c(=O)n(C2CCC(=O)NC2=O)c2ccc(C3CCN(CCC(=O)N4CC[C@H]5CC[C@@H](C(=O)N[C@@H](CCC(N)=O)C(=O)NC(c6ccccc6)c6ccccc6)N5C(=O)[C@@H](N)C4)CC3)cc21] | (2S)-2-[[(5S,8S,10aR)-3-(3-[4-[1-(2,6-dioxopiperidin-3-yl)-3-methyl-2-oxo-1,3-benzodiazol-5-yl]piperidin-1-yl]propanoyl)-6-oxo-5-(2,2,2-trifluoro-acetamido)-octahydro-pyrrolo[1,2-a][1,5]diazocin-8-yl]formamido]-N-(diphenylmeth-yl)pentanediamide trifluoroacetate | 917.45 | (400 MHz, DMSO-$d_6$) δ 11.11 (s, 1H), 9.43-9.26 (m, 1H), 8.89-8.25 (m, 3H), 7.37-7.18 (m, 11H), 7.12-6.98 (m, 2H), 6.96-6.88 (m, 1H), 6.81 (d, J = 15.4 Hz, 1H), 6.11 (d, J = 8.3 Hz, 1H), 5.37 (dd, J = 12.7, 5.5 Hz, 1H), 4.68-4.30 (m, 4H), 3.69-3.59 (m, 4H), 3.48-3.37 (m, 5H), 3.35 (s, 3H), 3.15-3.06 (m, 5H), 2.97-2.77 (m, 3H), 2.78-2.57 (m, 3H), 2.30-1.87 (m, 8H), 1.87-1.79 (m, 3H) |
| H90 | 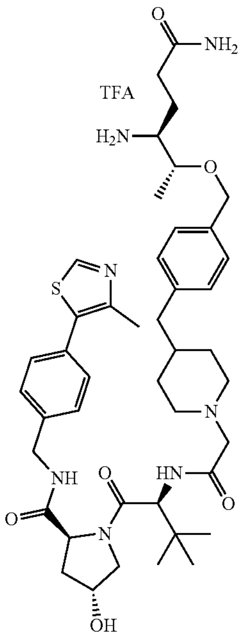 [SMILES: Cc1ncsc1-c1ccc(CNC(=O)[C@@H]2C[C@@H](O)CN2C(=O)[C@@H](NC(=O)CN2CCC(Cc3ccc(CO[C@H](C)[C@@H](N)CCC(N)=O)cc3)CC2)C(C)(C)C)cc1] | (2S,4R)-1-[(2S)-2-[2-(4-[[4-([[(2R,3S)-3-amino-5-carbamoylpentan-2-yl]oxy]meth-yl)phenyl]meth-yl]piperidin-1-yl)acetamido]-3,3-dimethylbutanoyl]-4-hydroxy-N-[[4-(4-methyl-1,3-thiazol-5-yl)phenyl]meth-yl]pyrrolidine-2-carboxamide trifluoroacetate | 804.35 | Used in the next step without further purification |

TABLE 49-continued

| Characterization data for intermediates prepared according to procedure above. | | | | |
|---|---|---|---|---|
| Intermediate | Structure | Chemical Name | MS: $[(M + 1)]^+$ | $^1$H-NMR |
| H91 | 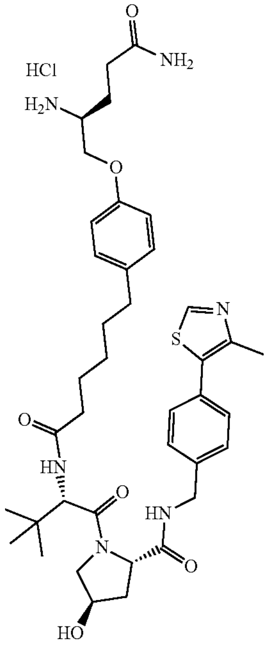 [SMILES: Cc1ncsc1-c1ccc(CNC(=O)[C@@H]2C[C@@H](O)CN2C(=O)[C@@H](NC(=O)CCCCCc2ccc(OC[C@@H](N)CCC(N)=O)cc2)C(C)(C)C)cc1 ; Cl] | (2S,4R)-1-[(2S)-2-(6-[4-[(2S)-2-Amino-4-carbamoylbutoxy]phenyl]hexanamido)-3,3-dimethylbutanoyl]-4-hydroxy-N-[[4-(4-methyl-1,3-thiazol-5-yl)phenyl]methyl]pyrrolidine-2-carboxamide hydrochloride | 735.30 | (400 MHz, DMSO-$d_6$) δ 9.03 (s, 1H), 8.58 (t, J = 6.0 Hz, 1H), 8.28-8.23 (m, 3H), 7.84 (d, J = 9.4 Hz, 1H), 7.41 (q, J = 8.4 Hz, 5H), 7.15-7.08 (m, 2H), 6.98-6.86 (m, 2H), 4.61-4.50 (m, 1H), 4.48-4.40 (m, 2H), 4.36 (s, 1H), 4.28-4.09 (m, 2H), 3.71-3.61 (m, 2H), 3.53-3.47 (m, 1H), 2.56-2.54 (m, 1H), 2.51-2.47 (m, 1H), 2.46 (s, 3H), 2.37-2.20 (m, 3H), 2.16-1.99 (m, 2H), 1.97-1.80 (m, 3H), 1.59-1.42 (m, 4H), 1.26 (q, J = 7.5 Hz, 2H), 0.94 (s, 9H) |
| H92 | 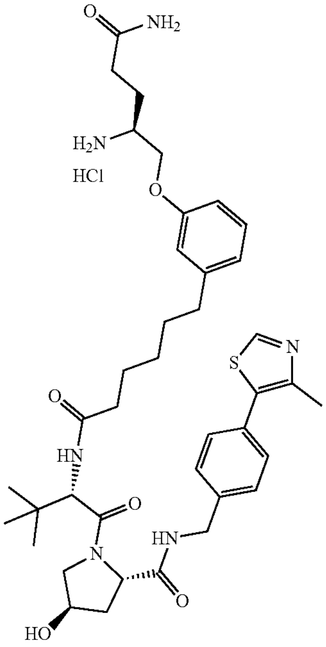 [SMILES: Cc1ncsc1-c1ccc(CNC(=O)[C@@H]2C[C@@H](O)CN2C(=O)[C@@H](NC(=O)CCCCCc2cccc(OC[C@@H](N)CCC(N)=O)c2)C(C)(C)C)cc1 ; Cl] | (2S,4R)-1-[(2S)-2-(6-[3-[(2S)-2-amino-4-carbamoylbutoxy]phenyl]hexanamido)-3,3-dimethylbutanoyl]-4-hydroxy-N-[[4-(4-methyl-1,3-thiazol-5-yl)phenyl]methyl]pyrrolidine-2-carboxamide hydrochloride | 735.34 | (400 MHz, DMSO-$d_6$) δ 9.03 (s, 1H), 8.57 (t, J = 6.1 Hz, 1H), 8.30-8.26 (m, 2H), 7.84 (d, J = 9.3 Hz, 1H), 7.41 (q, J = 8.3 Hz, 4H), 7.21 (t, J = 7.9 Hz, 1H), 6.92 (s, 1H), 6.86-6.75 (m, 3H), 4.54 (d, J = 9.3 Hz, 1H), 4.47-4.39 (m, 2H), 4.36 (s, 1H), 4.18-4.11 (m, 3H), 4.02 (dd, J = 10.5, 6.5 Hz, 1H), 3.71-3.60 (m, 2H), 3.50 (s, 1H), 3.06-3.02 (m, 2H), 2.45 (s, 3H), 2.34-2.23 (m, 3H), 2.17-1.99 (m, 2H), 1.97-1.83 (m, 3H), 1.78-1.71 (m, 2H), 1.62-1.41 (m, 5H), 1.31-1.25 (m, 2H), 0.93 (s, 9H) |

TABLE 49-continued

| Characterization data for intermediates prepared according to procedure above. | | | | |
|---|---|---|---|---|
| Intermediate | Structure | Chemical Name | MS: [(M + 1)]+ | 1H-NMR |
| H93 | 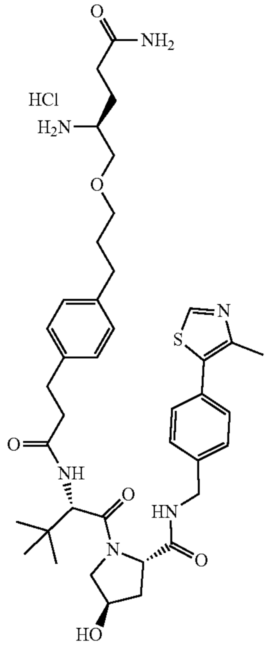 [SMILES: Cc1ncsc1-c1ccc(CNC(=O)[C@@H]2C[C@@H](O)CN2C(=O)[C@@H](NC(=O)CCc2ccc(CCCOC[C@@H](N)CCC(N)=O)cc2)C(C)(C)C)cc1 ; Cl] | (2S,4R)-1-[(2S)-2-[3-(4-[3-[(2S)-2-amino-4-carbamoylbutoxy]propyl]phenyl)propanamido]-3,3-dimethylbutanoyl]-4-hydroxy-N-[[4-(4-methyl-1,3-thiazol-5-yl)phenyl]methyl]pyrrolidine-2-carboxamide hydrochloride | 771.42 | Used in the next step without further purification |
| H94 | 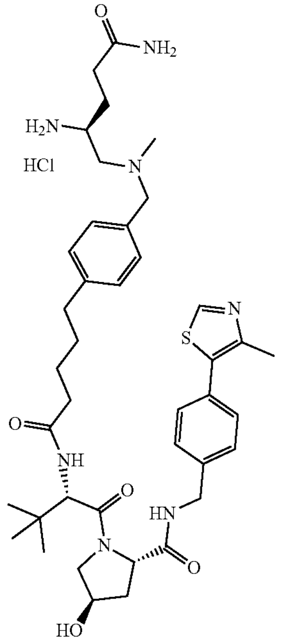 [SMILES: Cc1ncsc1-c1ccc(CNC(=O)[C@@H]2C[C@@H](O)CN2C(=O)[C@@H](NC(=O)CCCCc2ccc(CN(C)C[C@@H](N)CCC(N)=O)cc2)C(C)(C)C)cc1 ; Cl] | (2S,4R)-1-[(2S)-2-[5-[4-([[(2S)-2-amino-4-carbamoylbutyl](methyl)amino]methyl)phenyl]pentanamido]-3,3-dimethylbutanoyl]-4-hydroxy-N-[[4-(4-methyl-1,3-thiazol-5-yl)phenyl]methyl]pyrrolidine-2-carboxamide hydrochloride | 748.40 | Used in the next step without further purification |

TABLE 49-continued

Characterization data for intermediates prepared according to procedure above.

| Intermediate | Structure | Chemical Name | MS: [(M + 1)]+ | 1H-NMR |
|---|---|---|---|---|
| H95 | 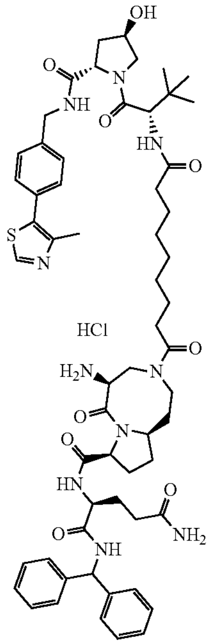 [SMILES: Cc1ncsc1-c1ccc(CNC(=O)[C@@H]2C[C@@H](O)CN2C(=O)[C@@H](NC(=O)CCCCCCCC(=O)N2CC[C@H]3CC[C@@H](C(=O)N[C@@H](CCC(N)=O)C(=O)NC(c4ccccc4)c4ccccc4)N3C(=O)[C@@H](N)C2)C(C)(C)C)cc1 ; Cl] | (2S)-2-[[(5S,8S,10aR)-5-amino-3-(8-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]octanoyl)-6-oxo-octahydropyrrolo[1,2-a][1,5]diazocin-8-yl]formamido]-N-(diphenylmethyl)pentanediamide hydrochloride | 1103.39 | (400 MHz, DMSO-$d_6$) δ 8.99 (s, 1H), 8.59-8.54 (m, 1H), 8.30 (s, 3H), 7.85 (d, J = 9.2 Hz, 1H), 7.46-7.29 (m, 10H), 7.31-7.24 (m, 6H), 6.79 (s, 1H), 6.10 (d, J = 8.4 Hz, 1H), 4.55 (d, J = 9.1 Hz, 1H), 4.48-4.40 (m, 2H), 4.20 (s, 2H), 3.60-3.55 (m, 5H), 2.71-2.63 (m, 1H), 2.47-2.43 (m, 5H), 2.36- 2.32 (m, 2H), 2.13-2.08 (m, 8H), 1.54-1.50 (m, 4H), 1.32-1.21 (m, 9H), 1.17-1.14 (m, 1H), 0.96-0.92 (m, 14H) |
| H96 | 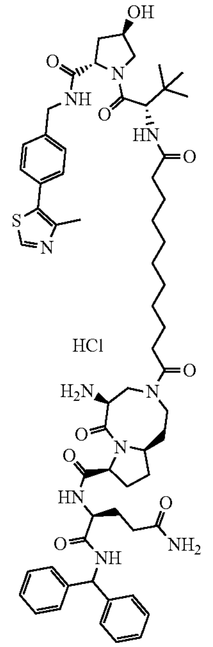 [SMILES: Cc1ncsc1-c1ccc(CNC(=O)[C@@H]2C[C@@H](O)CN2C(=O)[C@@H](NC(=O)CCCCCCCCCC(=O)N2CC[C@H]3CC[C@@H](C(=O)N[C@@H](CCC(N)=O)C(=O)NC(c4ccccc4)c4ccccc4)N3C(=O)[C@@H](N)C2)C(C)(C)C)cc1 ; Cl] | (2S)-2-[[(5S,8S,10aR)-5-amino-3-(10-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]decanoyl)-6-oxo-octahydropyrrolo[1,2-a][1,5]diazocin-8-yl]formamido]-N-(diphenylmethyl)pentanediamide hydrochloride | 1131.50 | (400 MHz, DMSO-$d_6$) δ 9.00 (s, 1H), 8.86 (t, J = 7.6 Hz, 1H), 8.33 (s, 2H), 7.85 (d, J = 9.2 Hz, 1H), 7.45-7.22 (m, 16H), 6.79 (s, 1H), 6.11 (d, J = 7.8 Hz, 1H), 4.55 (d, J = 9.2 Hz, 1H), 4.48-4.39 (m, 5H), 4.36 (s, 2H), 3.68-3.38 (m, 11H), 2.48-2.44 (m, 7H), 2.18-1.69 (m, 3H), 1.58-1.53 (m, 6H), 1.3-1.25 (m, 15H), 0.95 (s, 9H) |

TABLE 49-continued

| Characterization data for intermediates prepared according to procedure above. | | | | |
|---|---|---|---|---|
| Intermediate | Structure | Chemical Name | MS: [(M + 1)]+ | 1H-NMR |
| H97 | 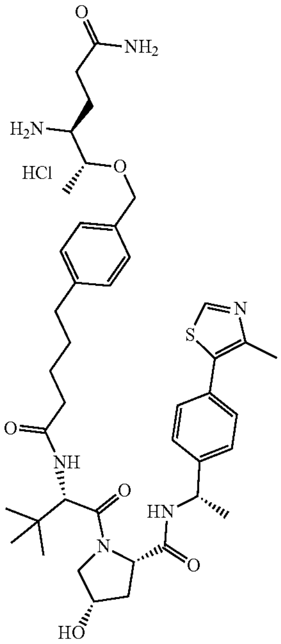 [SMILES: Cc1ncsc1-c1ccc([C@H](C)NC(=O)[C@@H]2C[C@H](O)CN2C(=O)[C@@H](NC(=O)CCCCc2ccc(CO[C@H](C)[C@@H](N)CCC(N)=O)cc2)C(C)(C)C)cc1 ; Cl] | (2S,4S)-1-[(2S)-2-[5-[4-([[(2R,3S)-3-amino-5-carbamoylpentan-2-yl]oxy]methyl)phenyl]pentanamido]-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride | 763.45 | (400 MHz, $CD_3OD$) δ 10.07 (s, 1H), 7.62-7.51 (m, 4H), 7.31 (d, J = 7.9 Hz, 2H), 7.20 (d, J = 7.9 Hz, 2H), 5.04 (q, J = 7.0 Hz, 1H), 4.64 (d, J = 11.6 Hz, 1H), 4.56-4.45 (m, 3H), 4.39 (t, J = 4.6 Hz, 1H), 4.03 (dd, J = 10.7, 5.1 Hz, 1H), 3.88-3.80 (m, 1H), 3.42-3.35 (m, 1H), 2.64 (s, 3H), 2.47-2.43 (m, 2H), 2.35-2.31 (m, 1H), 1.99-1.82 (m, 2H), 1.65 (s, 6H), 1.64-1.60 (m, 4H), 1.53 (d, J = 7.0 Hz, 3H), 1.26 (d, J = 6.4 Hz, 3H), 1.07 (s, 9H) |
| H98 | 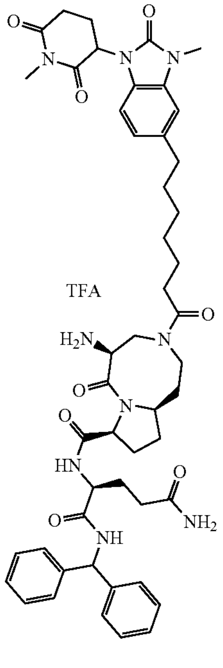 [SMILES: CN1C(=O)CCC(n2c(=O)n(C)c3cc(CCCCCCC(=O)N4CC[C@H]5CC[C@@H](C(=O)N[C@@H](CCC(N)=O)C(=O)NC(c6ccccc6)c6ccccc6)N5C(=O)[C@@H](N)C4)ccc32)C1=O ; "TFA"] | (2S)-2-[(5S,8S,10aR)-5-amino-3-[7-[3-methyl-1-(1-methyl-2,6-dioxopiperidin-3-yl)-2-oxo-1,3-benzodiazol-5-yl]heptanoyl]-6-octahydropyrrolo[1,2-a][1,5]diazocin-8-yl]formamido]-N-(diphenylmethyl)pentanediamide trifluoroacetate | 904.40 | (400 MHz, DMSO-$d_6$) δ 8.84 (t, J = 8.0 Hz, 1H), 8.38-8.23 (m, 3H), 7.77-7.10 (m, 13H), 7.05-6.97 (m, 2H), 6.85 (d, J = 8.0 Hz, 1H), 6.78 (s, 1H), 6.11 (d, J = 8.4 Hz, 1H), 5.41 (dd, J = 12.9, 5.3 Hz, 1H), 4.52-4.32 (m, 3H), 4.28-4.14 (m, 1H), 3.97 (d, J = 14.2 Hz, 1H), 3.82 (d, J = 14.2 Hz, 1H), 3.50-3.42 (m, 1H), 3.34 (s, 3H), 3.29-3.08 (m, 1H), 3.04 (s, 3H), 3.01-2.91 (m, 1H), 2.84-2.67 (m, 2H), 2.62 (t, J = 7.7 Hz, 2H), 2.48-2.10 (m, 4H), 2.06-1.98 (m, 1H), 1.98-1.85 (m, 2H), 1.85-1.65 (m, 4H), 1.65-1.44 (m, 4H), 1.43-1.19 (m, 4H). |

TABLE 49-continued

| Characterization data for intermediates prepared according to procedure above. | | | | |
|---|---|---|---|---|
| Intermediate | Structure | Chemical Name | MS: $[(M + 1)]^+$ | $^1$H-NMR |
| H99 | 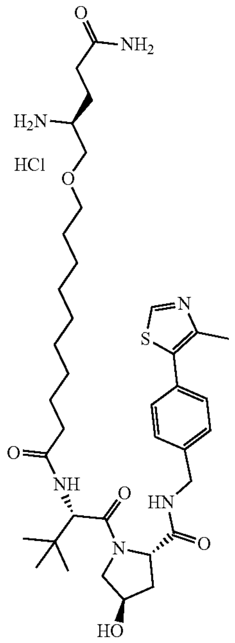 [SMILES: Cc1ncsc1-c1ccc(CNC(=O)[C@@H]2C[C@@H](O)CN2C(=O)[C@@H](NC(=O)CCCCCCCCCOC[C@@H](N)CCC(N)=O)C(C)(C)C)cc1 ; Cl] | (2S,4R)-1-[(2S)-2-[10-[(2S)-2-amino-4-carbamoylbutoxy]decanamido]-3,3-dimethylbutanoyl]-4-hydroxy-N-[[4-(4-methyl-1,3-thiazol-5-yl)phenyl]methyl]pyrrolidine-2-carboxamide hydrochloride | 715.40 | (400 MHz, DMSO-$d_6$) δ 9.08 (d, J = 4.9 Hz, 1H), 8.59 (t, J = 6.0 Hz, 1H), 8.05 (s, 2H), 7.84 (d, J = 9.3 Hz, 1H), 7.48-7.36 (m, 5H), 6.90 (s, 1H), 4.58-4.50 (m, 1H), 4.48-4.39 (m, 2H), 4.35 (s, 1H), 4.23 (dd, J = 15.8, 5.2 Hz, 1H), 3.71-3.60 (m, 2H), 3.52 (dd, J = 10.4, 4.0 Hz, 1H), 3.47-3.36 (m, 3H), 3.23 (s, 1H), 2.46 (s, 3H), 2.28-2.21 (m, 3H), 2.16-1.99 (m, 2H), 1.94-1.87 (m, 1H), 1.81-1.70 (m, 2H), 1.58-1.46 (m, 4H), 1.28-1.23 (m, 12H), 0.94 (s, 9H) |
| H100 | 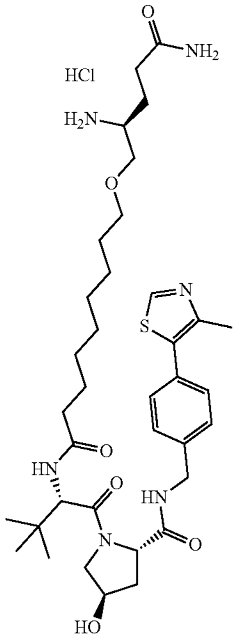 [SMILES: Cc1ncsc1-c1ccc(CNC(=O)[C@@H]2C[C@@H](O)CN2C(=O)[C@@H](NC(=O)CCCCCCCCOC[C@@H](N)CCC(N)=O)C(C)(C)C)cc1 ; Cl] | (2S,4R)-1-[(2S)-2-[9-[(2S)-2-amino-4-carbamoylbutoxy]nonanamido]-3,3-dimethylbutanoyl]-4-hydroxy-N-[[4-(4-methyl-1,3-thiazol-5-yl)phenyl]methyl]pyrrolidine-2-carboxamide hydrochloride | 701.25 | (400 MHz, DMSO-$d_6$) δ 9.26-9.03 (m, 1H), 8.61-8.57 (m, 1H), 7.84 (d, J = 9.3 Hz, 1H), 7.57-7.31 (m, 5H), 6.90 (s, 1H), 4.88-4.50 (m, 1H), 4.46-4.37 (m, 2H), 4.37-4.30 (m, 1H), 4.28-4.25 (m, 1H), 3.74-3.61 (m, 2H), 3.52 (dd, J = 10.4, 4.0 Hz, 1H), 3.46-3.32 (m, 4H), 3.23 (s, 1H), 2.46 (s, 3H), 2.27-2.24 (m, 3H), 2.17-2.01 (m, 2H), 1.91 (td, J = 8.5, 4.3 Hz, 1H), 1.78-1.75 (m, 2H), 1.52-1.47 (m, 6H), 1.28-1.22 (m 8H), 0.94 (s, 9H) |

TABLE 49-continued

Characterization data for intermediates prepared according to procedure above.

| Intermediate | Structure | Chemical Name | MS: [(M + 1)]+ | 1H-NMR |
|---|---|---|---|---|
| H101 | 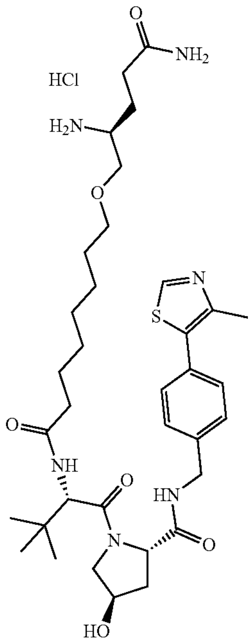 [SMILES: Cc1ncsc1-c1ccc(CNC(=O)[C@@H]2C[C@@H](O)CN2C(=O)[C@@H](NC(=O)CCCCCCCOC[C@@H](N)CCC(N)=O)C(C)(C)C)cc1 ; Cl] | (2S,4R)-1-((S)-2-(8-(((S)-2,5-diamino-5-oxopentyl)oxy)octanamido)-3,3-dimethylbutanoyl)-4-hydroxy-N-(4-(4-methylthiazol-5-yl)benzyl)pyrrolidine-2-carboxamide hydrochloride | 687.55 | (400 MHz, DMSO-$d_6$) δ 9.05 (s, 1H), 8.58 (t, J = 6.0 Hz, 1H), 8.10-7.97 (m, 2H), 7.84 (d, J = 9.3 Hz, 1H), 7.48-7.37 (m, 5H), 6.90 (s, 1H), 4.58-4.16 (m, 5H), 3.72-3.61 (m, 2H), 3.55-3.35 (m, 4H), 3.23 (s, 1H), 3.13-2.99 (m, 2H), 2.45 (s, 3H), 2.33-2.00 (m, 4H), 1.94-1.69 (m, 3H), 1.56-1.40 (m, 2H), 1.35-1.16 (m, 9H), 0.94 (s, 9H) |
| H102 | 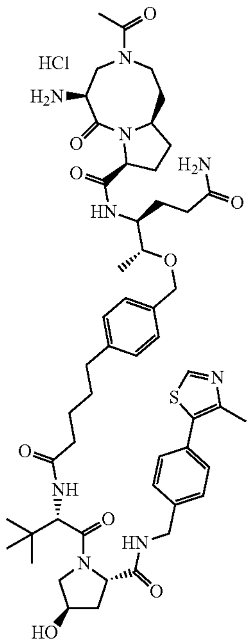 [SMILES: CC(=O)N1CC[C@H]2CC[C@@H](C(=O)N[C@@H](CCC(N)=O)[C@@H](C)OCc3ccc(CCCCC(=O)N[C@H](C(=O)N4C[C@H](O)C[C@H]4C(=O)NCc4ccc(-c5scnc5C)cc4)C(C)(C)C)cc3)N2C(=O)[C@@H](N)C1 ; Cl] | (2S,4R)-1-[(2S)-2-[5-[4-([[(2R,3S)-3-[[(5S,8S,10aR)-3-acetyl-5-amino-6-oxo-octahydropyrrolo[1,2-a][1,5]diazocin-8-yl]formamido]-5-carbamoylpentan-2-yl]oxy]methyl)phenyl]pentanamido]-3,3-dimethylbutanoyl]-4-hydroxy-N-[[4-(4-methyl-1,3-thiazol-5-yl)phenyl]methyl]pyrrolidine-2-carboxamide hydrochloride | 1000.45 | (400 MHz, DMSO-$d_6$) δ 9.07 (s, 1H), 8.59 (s, 1H), 8.50 (s, 1H), 8.37 (d, J = 17.5 Hz, 1H), 7.95 (d, J = 9.0 Hz, 1H), 7.88 (d, J = 9.3 Hz, 1H), 7.41 (q, J = 8.1 Hz, 4H), 7.22 (d, J = 7.7 Hz, 2H), 7.13 (d, J = 7.7 Hz, 3H), 6.71 (s, 1H), 4.54 (d, J = 9.3 Hz, 1H), 4.44 (d, J = 13.8 Hz, 5H), 4.35 (s, 1H), 4.21 (d, J = 15.7 Hz, 2H), 4.03 (d, J = 14.4 Hz, 1H), 3.76 (s, 2H), 3.63 (dd, J = 16.7, 6.0 Hz, 2H), 3.45-3.37 (m, 2H), 3.28-3.23 (m, 1H), 3.19-3.16 (m, 1H), 3.15-3.11 (m, 1H), 2.55 (s, 2H), 2.45 (s, 3H), 2.35-2.27 (m, 1H), 2.30-1.99 (m, 6H), 1.98-1.65 (m, 2H), 1.54-1.49 (m, 10H), 1.41-1.33 (m, 1H), 1.26-1.22 (m, 1H), 1.07 (d, J = 6.1 Hz, 3H), 0.93 (s, 9H) |

TABLE 49-continued

Characterization data for intermediates prepared according to procedure above.

| Intermediate | Structure | Chemical Name | MS: [(M + 1)]+ | 1H-NMR |
|---|---|---|---|---|
| H103 | 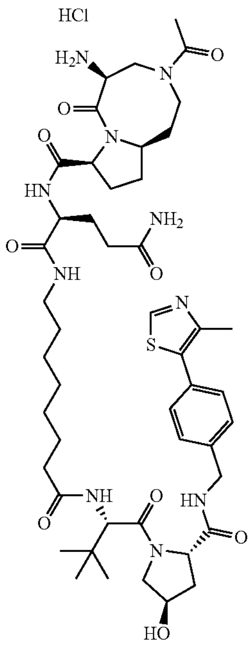 [SMILES: Cl ; CC(=O)N1CC[C@H]2CC[C@@H](C(=O)N[C@@H](CCC(N)=O)C(=O)NCCCCCCCC(=O)N[C@H](C(=O)N3C[C@H](O)C[C@H]3C(=O)NCc3ccc(-c4scnc4C)cc3)C(C)(C)C)N2C(=O)[C@@H](N)C1] | (2S)-2-[[(5S,8S,10aR)-3-acetyl-5-amino-6-oxo-octa-hydropyrrolo[1,2-a][1,5]diazocin-8-yl]formamido]-N-(7-[[(2S)-1-[(2S,4R)-4-hydroxy-2-([[4-(4-methyl-1,3-thiazol-5-yl)phenyl]meth-yl]car-bamoyl)pyrrolidin-1-yl]-3,3-dimethyl-1-oxobutan-2-yl]carbamoyl]hep-tyl)pentanediamide hydrochloride | 951.80 | (400 MHz, DMSO-$d_6$) δ 9.02 (d, J = 5.0 Hz, 1H), 8.58 (s, 1H), 8.44 (s, 1H), 8.28 (s, 2H), 7.92 (s, 1H), 7.85 (d, J = 9.3 Hz, 1H), 7.46-7.36 (m, 4H), 7.25 (s, 1H), 6.76 (s, 1H), 4.58-4.52 (m, 1H), 4.52-4.39 (m, 3H), 4.36 (s, 1H), 4.27 (s, 1H), 4.31-4.17 (m, 2H), 4.10-3.96 (m, 2H), 3.95-3.80 (m, 2H), 3.72-3.60 (m, 6H), 3.57 (s, 1H), 3.47-3.37 (m, 1H), 3.29-3.18 (m, 1H), 3.07-3.02 (m, 1H), 2.45 (s, 3H), 2.29-2.24 (m, 2H), 2.21-1.99 (m, 7H), 1.93-1.89 (m, 1H), 1.84-1.70 (m, 2H), 1.55-1.47 (m, 1H), 1.43-1.33 (m, 2H), 1.26-1.22 (m, 8H), 0.94 (s, 9H) |
| H104 | 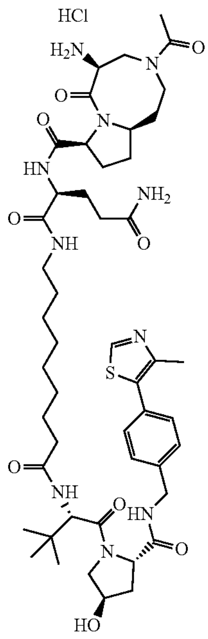 [SMILES: CC(=O)N1CC[C@H]2CC[C@@H](C(=O)N[C@@H](CCC(N)=O)C(=O)NCCCCCCCCC(=O)N[C@H](C(=O)N3C[C@H](O)C[C@H]3C(=O)NCc3ccc(-c4scnc4C)cc3)C(C)(C)C)N2C(=O)[C@@H](N)C1 ; Cl] | (2S)-2-[[(5S,8S,10aR)-3-acetyl-5-amino-6-oxo-octahydropyrrolo[1,2-a][1,5]diazocin-8-yl]formamido]-N-(8-[[(2S)-1-[(2S,4R)-4-hydroxy-2-([[4-(4-methyl-1,3-thiazol-5-yl)phenyl]methyl]car-bamoyl)pyrrolidin-1-yl]-3,3-dimethyl-1-oxobutan-2-yl]carbamoyl]oc-tyl)pentane-diamide hydrochloride | 965.80 | (400 MHz, DMSO-$d_6$) δ 9.04 (d, J = 8.6 Hz, 1H), 8.59 (s, 1H), 8.48 (s, 1H), 8.31 (d, J = 19.3 Hz, 2H), 7.93 (s, 1H), 7.89-7.82 (m, 1H), 7.46-7.36 (m, 4H), 7.26 (s, 1H), 6.77 (s, 1H), 4.58-4.52 (m, 1H), 4.48-4.44 (m, 3H), 4.35 (s, 1H), 4.31-4.13 (m, 3H), 3.81-3.73 (m, 1H), 3.73-3.57 (m, 3H), 3.53-3.37 (m, 1H), 3.29-2.96 (m, 2H), 2.46 (s, 3H), 2.28-2.24 (m, 2H), 2.21-1.99 (m, 7H), 1.92-1.89 (m, 1H), 1.83-1.80 (m, 9H), 1.80-1.65 (m, 2H), 1.60-1.42 (m, 1H), 1.41-1.34 (m, 2H), 1.26-1.10 (m, 8H), 0.94 (s, 9H) |

TABLE 49-continued

Characterization data for intermediates prepared according to procedure above.

| Intermediate | Structure | Chemical Name | MS: [(M + 1)]$^+$ | $^1$H-NMR |
|---|---|---|---|---|
| H105 | 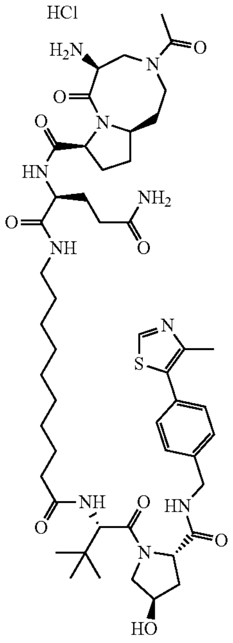 [SMILES: Cl ; CC(=O)N1CC[C@H]2CC[C@@H](C(=O)N[C@@H](CCC(N)=O)C(=O)NCCCCCCCCCC(=O)N[C@H](C(=O)N3C[C@H](O)C[C@H]3C(=O)NCc3ccc(-c4scnc4C)cc3)C(C)(C)C)N2C(=O)[C@@H](N)C1] | (2S)-2-[[(5S,8S,10aR)-3-acetyl-5-amino-6-oxo-octahydropyrrolo[1,2-a][1,5]diazocin-8-yl]formamido]-N-(9-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]nonyl)pentanediamide hydrochloride | 979.60 | (400 MHz, DMSO-$d_6$) δ 9.04 (s, 1H), 8.58 (t, J = 6.1 Hz, 1H), 8.47 (s, 1H), 8.36-8.25 (m, 2H), 7.92 (t, J = 5.5 Hz, 1H), 7.84 (d, J = 9.4 Hz, 1H), 7.46-7.36 (m, 4H), 7.31-7.19 (m, 1H), 6.76 (s, 1H), 4.55 (d, J = 9.4 Hz, 1H), 4.46 (s, 2H), 4.52-4.39 (m, 2H), 4.36 (s, 1H), 4.27-4.17 (m, 2H), 4.01 (d, J = 12.9 Hz, 1H), 3.81-3.57 (m, 5H), 3.59-3.55 (m, 5H), 3.53-3.35 (m, 1H), 3.26-3.22 (m, 1H), 3.15-2.97 (m, 2H), 2.46 (s, 3H), 2.32-2.17 (m, 2H), 2.12-2.08 (m, 6H), 1.93-1.89 (m, 1H), 1.85-1.66 (m, 2H), 1.58-1.42 (m, 2H), 1.39-1.35 (m, 3H), 1.26-1.06 (m, 10H), 0.94 (s, 9H) |
| H106 | 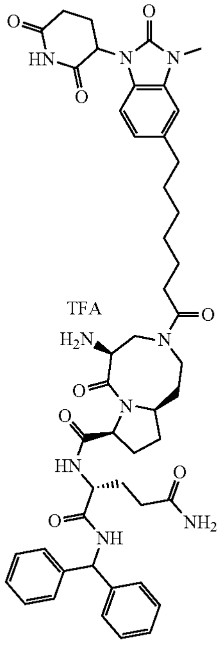 [SMILES: Cn1c(=O)n(C2CCC(=O)NC2=O)c2ccc(CCCCCCC(=O)N3CC[C@H]4CC[C@@H](C(=O)N[C@H](CCC(N)=O)C(=O)NC(c5ccccc5)c5ccccc5)N4C(=O)[C@@H](N)C3)cc21] | (2R)-2-[[(5S,8S,10aR)-5-amino-3-[7-[1-(2,6-dioxopiperidin-3-yl)-3-methyl-2-oxo-1,3-benzodiazol-5-yl]heptanoyl]-6-oxo-octahydropyrrolo[1,2-a][1,5]diazocin-8-yl]formamido]-N-(diphenylmethyl)pentanediamide trifluoroacetate | 890.55 | (400 MHz, $CD_3OD$) δ 7.39-7.31 (m, 6H), 7.27 (qd, J = 7.4, 6.4, 2.8 Hz, 4H), 7.06-6.99 (m, 2H), 6.99-6.92 (m, 1H), 6.17 (d, J = 2.5 Hz, 1H), 5.32 (dd, J = 12.5, 5.4 Hz, 1H), 4.67-4.54 (m, 1H), 4.52 (dd, J = 9.0, 4.7 Hz, 1H), 4.39 (d, J = 13.3 Hz, 1H), 4.23 (dd, J = 10.4, 2.8 Hz, 1H), 4.12 (q, J = 7.4 Hz, 1H), 4.03-3.88 (m, 1H), 3.73-3.64 (m, 1H), 3.42 (s, 3H), 3.31-3.16 (m, 1H), 3.10-2.95 (m, 1H), 2.91 (dd, J = 17.4, 4.9 Hz, 1H), 2.86-2.66 (m, 3H), 2.47 (ddd, J = 15.7, 9.2, 6.6 Hz, 1H), 2.42-2.29 (m, 3H), 2.32-2.26 (m, 1H), 2.26-2.06 (m, 4H), 1.97 (dt, J = 14.7, 7.1 Hz, 1H), 1.89-1.78 (m, 3H), 1.74-1.56 (m, 4H), 1.40 (m, 4H) |

TABLE 49-continued

Characterization data for intermediates prepared according to procedure above.

| Intermediate | Structure | Chemical Name | MS: [(M + 1)]+ | 1H-NMR |
|---|---|---|---|---|
| H107 | 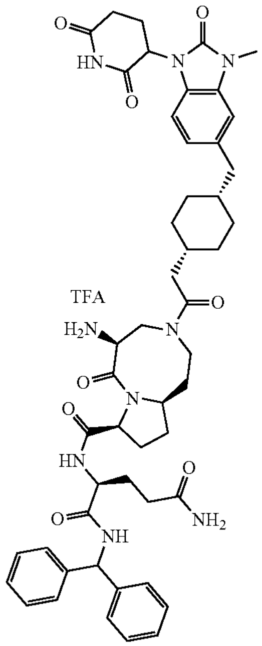 [SMILES: Cn1c(=O)n(C2CCC(=O)NC2=O)c2ccc(C[C@H]3CC[C@@H](CC(=O)N4CC[C@H]5CC[C@@H](C(=O)N[C@@H](CCC(N)=O)C(=O)NC(c6ccccc6)c6ccccc6)N5C(=O)[C@@H](N)C4)CC3)cc21] | (2S)-2-[[(5S,8S,10aR)-5-amino-6-oxo-3-[2-[(1s,4s)-4-[[1-(2,6-dioxopiperidin-3-yl)-3-methyl-2-oxo-1,3-benzodiazol-5-yl]methyl]cyclohexyl]acetyl]-octahydropyrrolo[1,2-a][1,5]diazocin-8-yl]formamido]-N-(diphenylmethyl)pentanediamide; trifluoroacetaldehyde | 916.80 | (300 MHz, DMSO-$d_6$) δ 11.10 (s, 1H), 8.86 (d, J = 8.4 Hz, 1H), 8.57-8.23 (m, 4H), 7.35-7.28 (m, 11H), 7.11-6.94 (m, 2H), 6.90-6.70 (m, 2H), 6.12 (d, J = 8.3 Hz, 1H), 5.36 (dd, J = 12.8, 5.4 Hz, 1H), 4.46-4.41 (m, 4H), 4.22-4.20 (m, 2H), 4.05-2.95 (m, 3H), 3.52-3.50 (m, 1H), 3.23-3.20 (m, 1H), 3.05-2.91 (m, 2H), 2.83-2.54 (m, 4H), 2.42-1.59 (m, 13H), 1.40 (d, J = 31.4 Hz, 10H) |
| H108 | 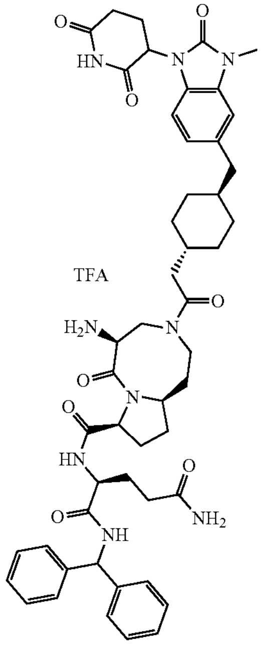 [SMILES: Cn1c(=O)n(C2CCC(=O)NC2=O)c2ccc(C[C@H]3CC[C@H](CC(=O)N4CC[C@H]5CC[C@@H](C(=O)N[C@@H](CCC(N)=O)C(=O)NC(c6ccccc6)c6ccccc6)N5C(=O)[C@@H](N)C4)CC3)cc21] | (2S)-2-[[(5S,8S,10aR)-5-amino-6-oxo-3-[2-[(1r,4r)-4-[[1-(2,6-dioxopiperidin-3-yl)-3-methyl-2-oxo-1,3-benzodiazol-5-yl]methyl]cyclohexyl]acetyl]-octahydropyrrolo[1,2-a][1,5]diazocin-8-yl]formamido]-N-(diphenylmethyl)pentanediamide trifluoroacetate | 916.80 | (300 MHz, DMSO-$d_6$) δ 11.10 (s, 1H), 8.86 (d, J = 8.4 Hz, 1H), 8.57-8.21 (m, 4H), 7.31 (tdd, J = 13.9, 6.8, 4.2 Hz, 12H), 7.07-6.94 (m, 2H), 6.90-6.71 (m, 2H), 6.12 (d, J = 8.3 Hz, 1H), 5.36 (dd, J = 12.8, 5.4 Hz, 1H), 4.45 (dq, J = 16.8, 9.2, 8.8 Hz, 4H), 4.29-3.38 (m, 4H), 3.25-2.80 (m, 1H), 2.80-2.56 (m, 4H), 2.48-1.63 (m, 14H), 1.40 (d, J = 29.0 Hz, 9H) |

TABLE 49-continued

| Characterization data for intermediates prepared according to procedure above. | | | | |
|---|---|---|---|---|
| Intermediate | Structure | Chemical Name | MS: $[(M + 1)]^+$ | $^1$H-NMR |
| H109 | 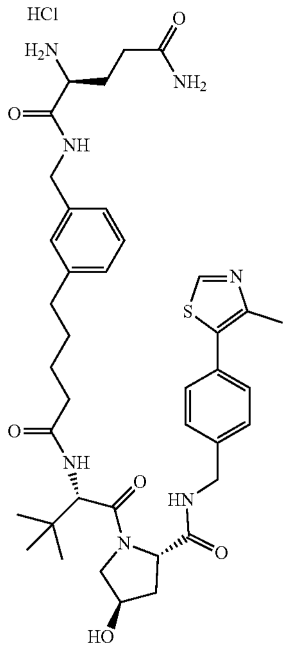 [SMILES: Cl ; Cc1ncsc1-c1ccc(CNC(=O)[C@@H]2C[C@@H](O)CN2C(=O)[C@@H](NC(=O)CCCCc2cccc(CNC(=O)[C@@H](N)CCC(N)=O)c2)C(C)(C)C)cc1] | (2S)-2-amino-N-[[3-(4-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]butyl)phenyl]methyl]pentanediamide hydrochloride | $[(M-1)]^- =$ 746.23 | (300 MHz, DMSO-$d_6$) δ 8.99 (s, 1H), 8.93 (t, J = 5.9 Hz, 1H), 8.55 (t, J = 6.0 Hz, 1H), 8.30-8.22 (m, 3H), 7.87 (d, J = 9.3 Hz, 1H), 7.44 (d, J = 8.1 Hz, 2H), 7.40 (d, J = 3.7 Hz, 3H), 7.28-7.20 (m, 1H), 7.10-7.08 (m, 4H), 6.99-6.94 (m, 1H), 4.59-4.49 (m, 1H), 4.49-4.37 (m, 2H), 4.36-4.31 (m, 2H), 4.21 (dd, J = 15.8, 5.0 Hz, 1H), 3.56-3.49 (m, 7H), 2.44 (s, 3H), 2.34-2.09 (m, 3H), 2.09-1.83 (m, 3H), 1.60-1.48 (m, 5H), 0.93 (s, 9H) |
| H110 | 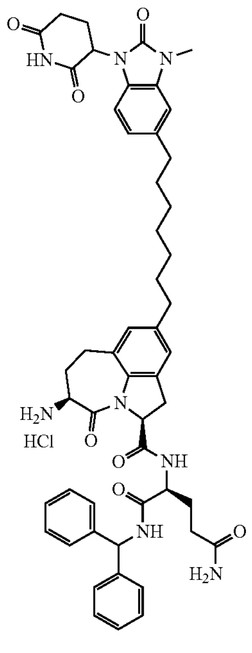 [SMILES: Cn1c(=O)n(C2CCC(=O)NC2=O)c2ccc(CCCCCCCc3cc4c5c(c3)C[C@@H](C(=O)N[C@@H](CCC(N)=O)C(=O)NC(c3ccccc3)c3ccccc3)N5C(=O)[C@@H](N)CC4)cc21 ; Cl] | (2S)-2-[[(2S,11S)-11-amino-6-[7-[1-(2,6-dioxopiperidin-3-yl)-3-methyl-2-oxo-1,3-benzodiazol-5-yl]heptyl]-12-oxo-1-azatricyclo[6.4.1.0^[4,13]]trideca-4(13),5,7-trien-2-yl]formamido]-N-(diphenylmethyl)pentanediamide hydrochloride | 895.55 | (400 MHz, DMSO-$d_6$) δ 11.08 (s, 1H), 8.87 (d, J = 8.4 Hz, 1H), 8.58-8.27 (m, 3H), 7.49-7.18 (m, 9H), 7.13-6.95 (m, 2H), 6.95-6.73 (m, 3H), 6.15-6.00 (m, 1H), 5.35 (dd, J = 12.8, 5.2 Hz, 1H), 5.15 (dd, J = 10.8, 3.1 Hz, 1H), 4.48-4.11 (m, 3H), 3.90-3.66 (m, 4H), 3.32 (s, 3H), 3.02 (d, J = 61.9 Hz, 2H), 2.87 (dd, J = 20.5, 14.4 Hz, 2H), 2.82-2.57 (m, 4H), 2.33-1.78 (m, 7H), 1.78-1.44 (m, 4H), 1.28 (d, J = 28.1 Hz, 7H) |

TABLE 49-continued

Characterization data for intermediates prepared according to procedure above.

| Intermediate | Structure | Chemical Name | MS: [(M + 1)]$^+$ | $^1$H-NMR |
|---|---|---|---|---|
| H111 | 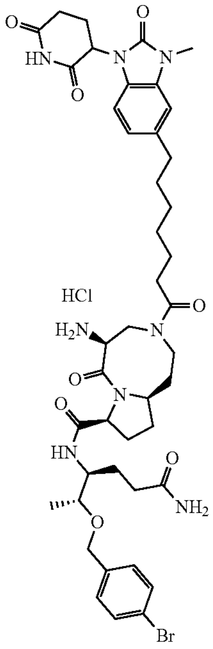 [SMILES: C[C@@H](OCc1ccc(Br)cc1)[C@H](CCC(N)=O)NC(=O)[C@@H]1CC[C@@H]2CCN(C(=O)CCCCCCc3ccc4c(c3)n(C)c(=O)n4C3CCC(=O)NC3=O)C[C@H](N)C(=O)N21 ; Cl] | (4S,5R)-4-[[(5S,8S,10aR)-5-Amino-3-[7-[1-(2,6-dioxopiperidin-3-yl)-3-methyl-2-oxo-1,3-benzodiazol-5-yl]heptanoyl]-6-oxo-octahydropyrrolo[1,2-a][1,5]diazocin-8-yl]formamido]-5-[(4-bromophenyl)meth-oxy]hexanamide hydrochloride | 893.20, 895.20 | (400 MHz, DMSO-$d_6$) δ 11.09 (s, 1H), 8.50-8.26 (m, 2H), 7.97 (dd, J = 9.5, 3.3 Hz, 1H), 7.57-7.49 (m, 2H), 7.29 (dt, J = 8.5, 2.1 Hz, 2H), 7.16 (s, 1H), 7.07-6.96 (m, 2H), 6.86 (dt, J = 8.5, 2.1 Hz, 1H), 6.68 (d, J = 25.0 Hz, 1H), 6.62-6.53 (m, 1H), 5.34 (dd, J = 12.7, 5.4 Hz, 1H), 4.56-4.28 (m, 5H), 4.21-4.04 (m, 1H), 3.87-3.46 (m, 4H), 3.41 (p, J = 6.2 Hz, 1H), 3.34 (s, 3H), 3.30-3.09 (m, 1H), 2.98-2.84 (m, 1H), 2.77-2.55 (m, 5H), 2.47-2.37 (m, 1H), 2.34-1.91 (m, 4H), 1.91-1.43 (m, 6H), 1.43-1.27 (m, 4H), 1.06 (d, J = 6.3 Hz, 3H) |
| H112 | 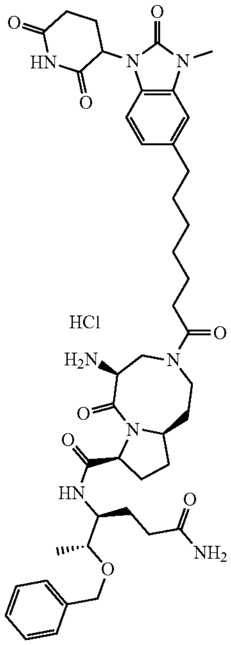 [SMILES: C[C@@H](OCc1ccccc1)[C@H](CCC(N)=O)NC(=O)[C@@H]1CC[C@@H]2CCN(C(=O)CCCCCCc3ccc4c(c3)n(C)c(=O)n4C3CCC(=O)NC3=O)C[C@H](N)C(=O)N21 ; Cl] | (4S,5R)-4-[(5S,8S,10aR)-5-Amino-3-[7-[1-(2,6-dioxopiperidin-3-yl)-3-methyl-2-oxo-1,3-benzodiazol-5-yl]heptanoyl]-6-oxo-octahydropyrrolo[1,2-a][1,5]diazocin-8-yl]formamido]-5-(benzyloxy)hexan-amide hydrochloride | 815.30 | (400 MHz, DMSO-$d_6$) δ 11.09 (s, 1H), 8.58-8.48 (m, 1H), 8.45-8.31 (m, 2H), 8.03-7.96 (m, 1H), 7.45-7.22 (m, 5H), 7.16 (s, 1H), 7.06-6.96 (m, 2H), 6.89-6.84 (m, 1H), 6.71 (s, 1H), 5.35 (dd, J = 12.7, 5.4 Hz, 1H), 4.57-4.34 (m, 3H), 4.32-4.08 (m, 5H), 3.87-3.74 (m, 2H), 3.52-3.43 (m, 2H), 3.33 (s, 3H), 3.28-3.05 (m, 2H), 2.98-2.84 (m, 1H), 2.78-2.56 (m, 4H), 2.48-2.39 (m, 1H), 2.37-1.65 (m, 6H), 1.64-1.48 (m, 6H), 1.45-1.24 (m, 4H), 1.10 (d, J = 6.3 Hz, 3H) |

TABLE 49-continued

| Intermediate | Structure | Chemical Name | MS: [(M + 1)]+ | 1H-NMR |
|---|---|---|---|---|
| | Characterization data for intermediates prepared according to procedure above. | | | |
| H113 | 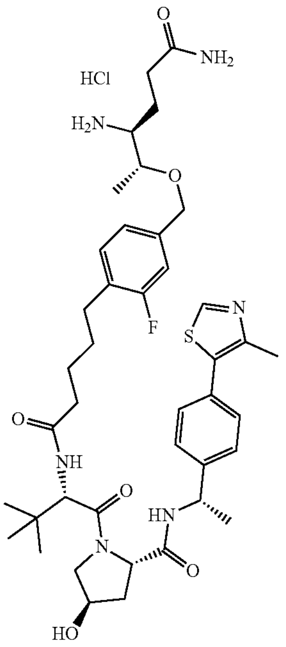 [SMILES: Cc1ncsc1-c1ccc([C@H](C)NC(=O)[C@@H]2C[C@@H](O)CN2C(=O)[C@@H](NC(=O)CCCCc2ccc(CO[C@H](C)[C@@H](N)CCC(N)=O)cc2F)C(C)(C)C)cc1 ; Cl] | (2S,4R)-1-[(2S)-2-[5-[4-([[(2R,3S)-3-amino-5-carbamoylpentan-2-yl]oxy]methyl)-2-fluorophenyl]pentan-amido]-3,3-dimethylbutanoyl]-4-hydroxy-N-[(1S)-1-[4-(4-methyl-1,3-thiazol-5-yl)phenyl]eth-yl]pyrrolidine-2-carboxamide hydrochloride | 881.40 | (400 MHz, DMSO-$d_6$) δ 9.03 (s, 1H), 8.38 (d, J = 7.8 Hz, 1H), 8.02 (s, 2H), 7.82 (d, J = 9.3 Hz, 1H), 7.47-7.36 (m, 4H), 7.23 (d, J = 13.1 Hz, 1H), 7.12 (d, J = 7.9 Hz, 1H), 6.93 (s, 1H), 4.92 (t, J = 7.1 Hz, 1H), 4.61-4.36 (m, 5H), 3.79 (s, 1H), 3.28 (s, 1H), 2.64-2.58 (m, 3H), 2.46 (s, 3H), 2.39-2.21 (m, 4H), 2.15 (s, 1H), 2.07-1.96 (m, 1H), 1.84-1.70 (m, 4H), 1.62-1.58 (m, 1H), 1.54-1.49 (m, 5H), 1.38 (d, J = 6.9 Hz, 3H), 1.16 (d, J = 6.3 Hz, 3H), 0.93 (s, 9H) |
| H114 | 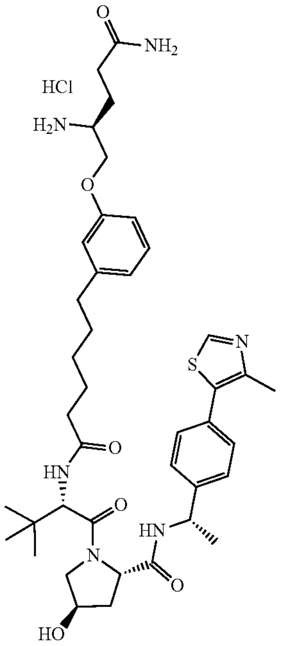 [SMILES: Cc1ncsc1-c1ccc([C@H](C)NC(=O)[C@@H]2C[C@@H](O)CN2C(=O)[C@@H](NC(=O)CCCCCc2cccc(OC[C@@H](N)CCC(N)=O)c2)C(C)(C)C)cc1 ; Cl] | (2S,4R)-1-[(2S)-2-(6-[3-[(2S)-2-amino-4-carbamoylbu-toxy]phenyl]hexan-amido)-3,3-dimethylbutanoyl]-4-hydroxy-N-[(1S)-1-[4-(4-methyl-1,3-thiazol-5-yl)phenyl]eth-yl]pyrrolidine-2-carboxamide hydrochloride | 749.45 | (400 MHz, DMSO-$d_6$) δ 9.06 (s, 1H), 8.40 (d, J = 7.8 Hz, 1H), 7.80 (d, J = 9.3 Hz, 1H), 7.45 (d, J = 8.0 Hz, 3H), 7.39 (d, J = 7.9 Hz, 2H), 7.21 (t, J = 7.6 Hz, 1H), 6.98 (d, J = 38.6 Hz, 1H), 6.82 (d, J = 7.0 Hz, 3H), 4.91 (q, J = 7.4 Hz, 1H), 4.77 (m, 4H), 4.51 (d, J = 8.9 Hz, 1H), 4.42 (t, J = 8.1 Hz, 1H), 4.30 (d, J = 17.0 Hz, 1H), 4.16 (d, J = 11.1 Hz, 1H), 4.07-3.99 (m, 1H), 3.60 (s, 2H), 3.44-2.56 (m, 2H), 2.55 (m, 1H), 2.47 (s, 3H), 2.28-2.18 (m, 3H), 2.17-1.98 (m, 2H), 1.95-1.74 (m, 2H), 1.62-1.46 (m, 3H), 1.38 (d, J = 7.0 Hz, 3H), 1.31-1.22 (m, 3H), 0.93 (s, 9H) |

TABLE 49-continued

| Characterization data for intermediates prepared according to procedure above. | | | | |
|---|---|---|---|---|
| Intermediate | Structure | Chemical Name | MS: $[(M + 1)]^+$ | $^1$H-NMR |
| H115 | 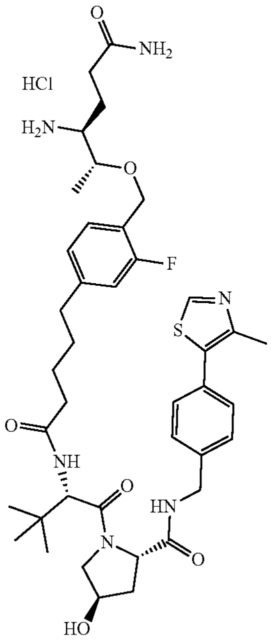 [SMILES: Cc1ncsc1-c1ccc(CNC(=O)[C@@H]2C[C@@H](O)CN2C(=O)[C@@H](NC(=O)CCCCc2ccc(CO[C@H](C)[C@@H](N)CCC(N)=O)c(F)c2)C(C)(C)C)cc1 ; Cl] | (2S,4R)-1-[(2S)-2-[5-[4-([[(2R,3S)-3-amino-5-carbamoylpentan-2-yl]oxy]methyl)-3-fluorophenyl]pentan-amido]-3,3-dimethylbutanoyl]-4-hydroxy-N-[[4-(4-methyl-1,3-thiazol-5-yl)phenyl]meth-yl]pyrrolidine-2-carboxamide hydrochloride | 767.50 | (400 MHz, DMSO-$d_6$) δ 9.08 (s, 1H), 8.58 (t, J = 6.1 Hz, 1H), 8.15-8.06 (m, 3H), 7.88 (d, J = 9.3 Hz, 1H), 7.47-7.37 (m, 6H), 7.05-6.98 (m, 3H), 6.92 (s, 1H), 4.63-4.38 (m, 6H), 4.35 (s, 1H), 4.22 (dd, J = 15.9, 5.2 Hz 1H) 3.88-3.72 (m, 1H), 3.72-3.61 (m, 1H), 3.26 (s, 1H), 2.59 (t, J = 7.2 Hz, 1H), 2.46 (s, 3H), 2.35-2.23 (m, 3H), 2.18-2.12 (m, 1H), 2.07-2.02 (m, 1H), 1.97-1.85 (m, 1H), 1.80-1.70 (m, 2H), 1.57-1.41 (m, 4H), 1.15 (d, J = 6.3 Hz, 3H), 0.94 (s, 9H) |
| H116 | 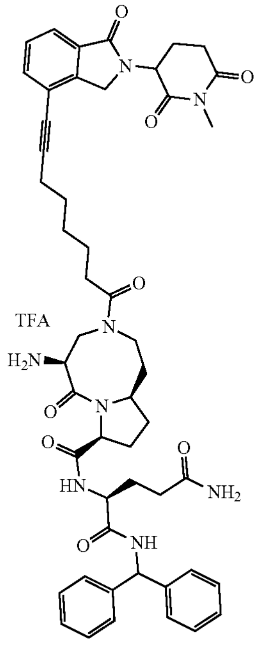 [SMILES: CN1C(=O)CCC(N2Cc3c(C#CCCCCCC(=O)N4CC[C@H]5CC[C@@H](C(=O)N[C@@H](CCC(N)=O)C(=O)NC(c6ccccc6)c6ccccc6)N5C(=O)[C@@H](N)C4)cccc3C2=O)C1=O] | (5S,8S,10aR)-8-[[(1S)-3-carbamoyl-1-(diphenylmethylcar-bamoyl)propyl]car-bamoyl]-3-[8-[2-(1-methyl-2,6-dioxopiperidin-3-yl)-1-oxo-3H-isoindol-4-yl]oct-7-ynoyl]-6-oxo-octahydropyrrolo[1,2-a][1,5]diazocin-5-aminium trifluoroacetate | 899.20 | Used in the next step without further purification |

TABLE 49-continued

| Characterization data for intermediates prepared according to procedure above. | | | | |
|---|---|---|---|---|
| Intermediate | Structure | Chemical Name | MS: $[(M + 1)]^+$ | $^1$H-NMR |
| H117 | 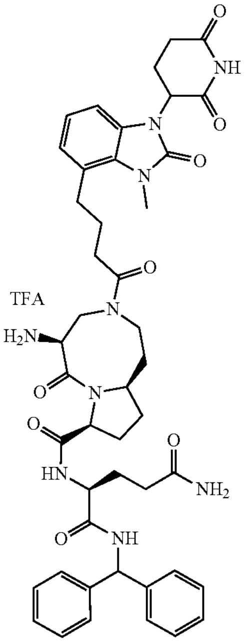 [SMILES: Cn1c(=O)n(C2CCC(=O)NC2=O)c2cccc(CCCC(=O)N3CC[C@H]4CC[C@@H](C(=O)N[C@@H](CCC(N)=O)C(=O)NC(c5ccccc5)c5ccccc5)N4C(=O)[C@@H](N)C3)c21] | (2S)-2-[[(5S,8S,10aR)-5-amino-3-[4-[1-(2,6-dioxopiperidin-3-yl)-3-methyl-2-oxo-1,3-benzodiazol-4-yl]butanoyl]-6-oxo-octahydropyrrolo[1,2-a][1,5]diazocin-8-yl]formamido]-N-(diphenylmethyl)pentanediamide trifluoroacetate | 848.30 | (400 MHz, DMSO-$d_6$) δ 11.10 (s, 1H), 8.84 (dd, J = 8.5, 7.0 Hz, 1H), 8.34-8.29 (m, 2H), 8.31 (d, J = 5.7 Hz, 1H), 7.35-7.23 (m, 11H), 6.98 (d, J = 4.6 Hz, 2H), 6.91-6.86 (m, 1H), 6.79 (s, 1H), 6.10 (d, J = 8.4 Hz, 1H), 5.37 (dd, J = 12.4, 5.4 Hz, 1H), 4.51-4.35 (m, 3H), 4.29-4.19 (m, 1H), 4.08-3.95 (m, 1H), 3.82 (d, J = 14.7 Hz, 1H), 3.59 (s, 3H), 3.33-3.13 (m, 1H), 3.01-2.83 (m, 4H), 2.77-2.53 (m, 4H), 2.25-2.03 (m, 3H), 2.02-1.95 (m, 2H), 1.95-1.85 (m, 4H), 1.83-1.63 (m, 4H) |
| H118 | 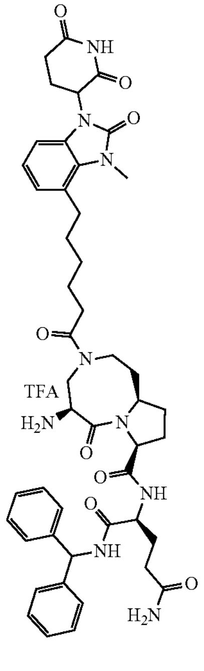 [SMILES: Cn1c(=O)n(C2CCC(=O)NC2=O)c2cccc(CCCCCC(=O)N3CC[C@H]4CC[C@@H](C(=O)N[C@@H](CCC(N)=O)C(=O)NC(c5ccccc5)c5ccccc5)N4C(=O)[C@@H](N)C3)c21] | (2S)-2-[[(5S,8S,10aR)-5-amino-3-[6-[1-(2,6-dioxopiperidin-3-yl)-3-methyl-2-oxo-1,3-benzodiazol-4-yl]hexanoyl]-6-oxo-octahydropyrrolo[1,2-a][1,5]diazocin-8-yl]formamido]-N-(diphenylmethyl)pentanediamide trifluoroacetate | 876.40 | (400 MHz, DMSO-$d_6$) δ 11.10 (s, 1H), 8.84 (t, J = 7.9 Hz, 1H), 8.36-8.28 (m, 2H), 7.38-7.27 (m, 8H), 7.26-7.18 (m, 4H), 6.97 (d, J = 4.6 Hz, 2H), 6.88 (d, J = 4.6 Hz, 1H), 6.78 (s, 1H), 6.11 (d, J = 8.2 Hz, 1H), 5.37 (dd, J = 12.6, 5.4 Hz, 1H), 4.51-4.35 (m, 4H), 4.25-4.13 (m, 1H), 4.01-3.89 (m, 1H), 3.86-3.78 (m, 1H), 3.56 (s, 3H), 3.49-3.40 (m, 1H), 3.24-3.08 (m, 2H), 3.05-2.86 (m, 4H), 2.80-2.59 (m, 4H), 2.46-2.38 (m, 2H), 2.25-1.84 (m, 4H), 1.85-1.50 (m, 6H), 1.46-1.39 (m, 2H) |

TABLE 49-continued

| Characterization data for intermediates prepared according to procedure above. | | | | |
|---|---|---|---|---|
| Intermediate | Structure | Chemical Name | MS: $[(M + 1)]^+$ | $^1$H-NMR |
| H119 | 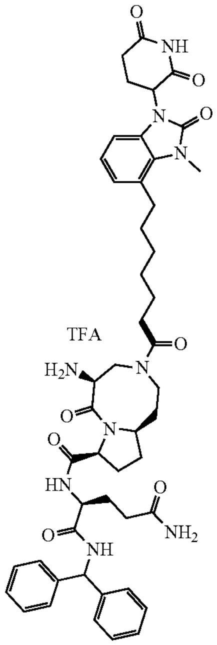 | (2S)-2-[[(5S,8S,10aR)-5-amino-3-[7-[1-(2,6-dioxopiperidin-3-yl)-3-methyl-2-oxo-1,3-benzodiazol-4-yl]heptanoyl]-6-oxo-octahydropyrrolo[1,2-a][1,5]diazocin-8-yl]formamido]-N-(diphenylmethyl)pentanediamide trifluoroacetate | 890.40 | (400 MHz, DMSO-$d_6$) δ 11.10 (s, 1H), 8.89-8.82 (m, 1H), 8.36-8.28 (m, 3H), 7.36-7.23 (m, 11H), 7.00-6.92 (m, 2H), 6.91-6.83 (m, 1H), 6.82-6.75 (m, 1H), 6.16-6.12 (m, 1H), 5.37 (dd, J = 12.5, 5.4 Hz 1H), 4.52-4.34 (m, 3H), 4.30-4.14 (m, 1H), 4.02-3.94 (m, 1H), 3.88-3.77 (m, 1H), 3.54 (s, 3H), 3.28-3.08 (m, 1H), 2.96-2.84 (m, 3H), 2.75-2.68 (m, 1H), 2.66-2.58 (m, 1H), 2.50-2.27 (m, 3H), 2.25-2.17 (m, 1H), 2.14-2.04 (m, 2H), 2.03-1.95 (m, 2H), 1.95-1.84 (m, 2H), 1.83-1.66 (m, 4H), 1.62-1.50 (m, 4H), 1.49-1.37 (m, 4H) |
| H120 | 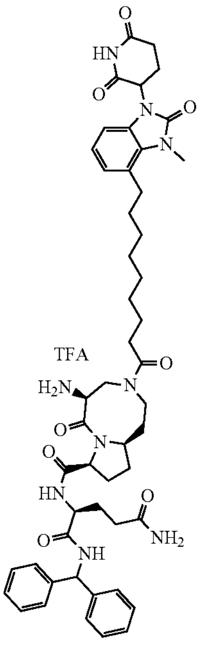 [SMILES: Cn1c(=O)n(C2CCC(=O)NC2=O)c2cccc(CCCCCCCCC(=O)N3CC[C@H]4CC[C@@H](C(=O)N[C@@H](CCC(N)=O)C(=O)NC(c5ccccc5)c5ccccc5)N4C(=O)[C@@H](N)C3)c21] | (2S)-2-[[(5S,8S,10aR)-5-amino-3-[9-[1-(2,6-dioxopiperidin-3-yl)-3-methyl-2-oxo-1,3-benzodiazol-4-yl]nonanoyl]-6-oxo-octahydropyrrolo[1,2-a][1,5]diazocin-8-yl]formamido]-N-(diphenylmethyl)pentanediamide trifluoroacetate | 918.40 | (400 MHz, DMSO-$d_6$) δ 11.10 (s, 1H), 8.85 (t, J = 8.0 Hz, 1H), 8.38-8.27 (m, 3H), 7.38-7.21 (m, 11H), 6.99-6.91 (m, 2H), 6.91-6.83 (m, 1H), 6.79 (s, 1H), 6.11 (d, J = 8.4 Hz, 1H), 5.37 (dd, J = 12.6, 5.4 Hz, 1H), 4.52-4.34 (m, 3H), 4.27-4.15 (m, 1H), 4.08-3.93 (m, 1H) 3.88-3.78 (m, 1H), 3.55 (s, 3H), 3.28-3.06 (m, 1H), 3.03-2.83 (m, 3H), 2.78-2.69 (m, 1H), 2.67-2.58 (m, 1H), 2.49-2.24 (m, 2H), 2.17-2.05 (m, 2H), 2.05-1.85 (m, 4H), 1.85-1.64 (m, 4H), 1.64-1.46 (m, 4H), 1.43-1.33 (m, 3H), 1.33-1.27 (m, 6H), 1.26-1.09 (m, 1H) |

TABLE 49-continued

Characterization data for intermediates prepared according to procedure above.

| Intermediate | Structure | Chemical Name | MS: [(M + 1)]+ | 1H-NMR |
|---|---|---|---|---|
| H121 | 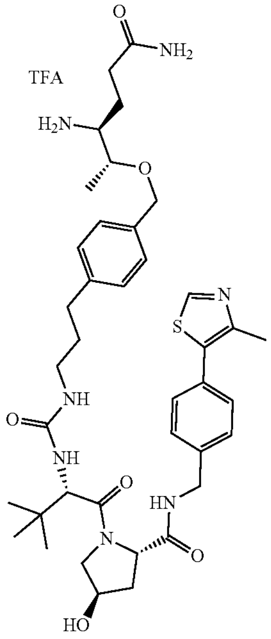 [SMILES: Cc1ncsc1-c1ccc(CNC(=O)[C@@H]2C[C@@H](O)CN2C(=O)[C@@H](NC(=O)NCCCc2ccc(CO[C@H](C)[C@@H](N)CCC(N)=O)cc2)C(C)(C)C)cc1 ; "TFA"] | (2S,4R)-1-[(2S)-2-[([3-[4-([[(2R,3S)-3-amino-5-carbamoylpentan-2-yl]oxy]methyl)phenyl]propyl]carbamoyl)amino]-3,3-dimethylbutanoyl]-4-hydroxy-N-[[4-(4-methyl-1,3-thiazol-5-yl)phenyl]methyl]pyrrolidine-2-carboxamide trifluoroacetate | 750.60 | (400 MHz, DMSO-$d_6$) δ 5 9.01 (d, J = 5.3 Hz, 1H), 7.50-7.41 (m, 4H), 7.29 (dd, J = 8.2, 1.8 Hz, 4H), 7.20-7.16 (m, 4H), 6.13 (s, 1H), 4.53 (d, J = 11.6 Hz, 2H), 4.49-4.35 (m, 5H), 3.66-3.64 (m, 1H), 3.33-3.24 (m, 2H), 2.99 (d, J = 6.9 Hz, 2H), 2.58 (d, J = 7.8 Hz, 4H), 2.48-2.44 (m, 4H), 2.24 (t, J = 7.4 Hz, 4H), 1.75 (q, J = 7.9 Hz, 2H), 1.68-1.64 (m, 4H), 1.14 (s, 3H), 0.97 (s, 9H) |
| H122 | 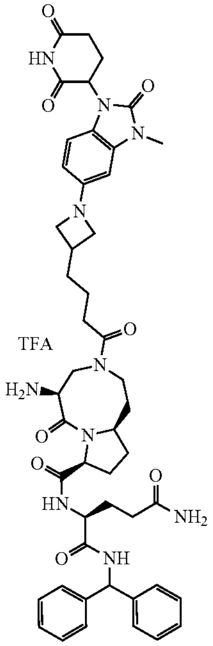 [SMILES: Cn1c(=O)n(C2CCC(=O)NC2=O)c2ccc(N3CC(CCCC(=O)N4CC[C@H]5CC[C@@H](C(=O)N[C@@H](CCC(N)=O)C(=O)NC(c6ccccc6)c6ccccc6)N5C(=O)[C@@H](N)C4)C3)cc21] | (2S)-2-[[(5S,8S,10aR)-5-amino-3-(4-[1-[1-(2,6-dioxopiperidin-3-yl)-3-methyl-2-oxo-1,3-benzodiazol-5-yl]azetidin-3-yl]butanoyl)-6-oxo-octahydropyrrolo[1,2-a][1,5]diazocin-8-yl]formamido]-N-(diphenylmethyl)pentanediamide trifluoroacetate | 903.30 | (400 MHz, DMSO-$d_6$) δ 11.10 (s, 1H), 8.84 (dd, J = 10.4, 8.5 Hz, 1H), 8.36-8.29 (m, 3H), 7.41-7.19 (m, 11H), 7.07 (d, J = 8.4 Hz, 1H), 6.85 (s, 1H), 6.80 (s, 1H), 6.57 (s, 1H), 6.10 (d, J = 8.6 Hz, 1H), 5.35 (dd, J = 12.9, 5.3 Hz, 1H), 4.52-4.31 (m, 3H), 4.28-4.19 (m, 3H), 3.96 (d, J = 14.2 Hz, 1H), 3.82-3.74 (m, 2H), 3.49 (d, J = 12.9 Hz, 1H), 3.34 (s, 3H), 3.30-3.13 (m, 1H), 3.08-3.01 (m, 1H), 2.90 (t, J = 14.9 Hz, 1H), 2.80 (t, J = 7.4 Hz, 1H), 2.73-2.58 (m, 2H), 2.48-2.30 (m, 2H), 2.25-2.09 (m, 2H), 2.04-1.97 (m, 1H), 1.96-1.86 (m, 2H), 1.85-1.62 (m, 7H), 1.59-1.37 (m, 3H) |

TABLE 49-continued

| Characterization data for intermediates prepared according to procedure above. | | | | |
|---|---|---|---|---|
| Intermediate | Structure | Chemical Name | MS: $[(M + 1)]^+$ | $^1$H-NMR |
| H123 | 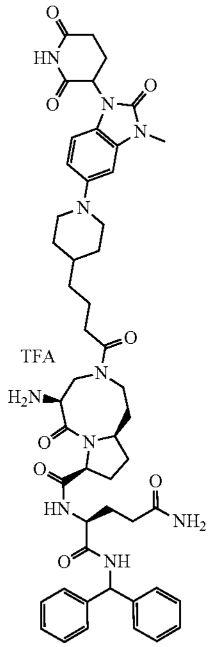 [SMILES: Cn1c(=O)n(C2CCC(=O)NC2=O)c2ccc(N3CCC(CCCC(=O)N4CC[C@H]5CC[C@@H](C(=O)N[C@@H](CCC(N)=O)C(=O)NC(c6ccccc6)c6ccccc6)N5C(=O)[C@@H](N)C4)CC3)cc21] TFA | (2S)-2-[[(5S,8S,10aR)-5-amino-3-(4-[1-[1-(2,6-dioxopiperidin-3-yl)-3-methyl-2-oxo-1,3-benzodiazol-5-yl]piperidin-4-yl]butanoyl)-6-oxo-octahydropyrrolo[1,2-a][1,5]diazocin-8-yl]formamido]-N-(diphenylmethyl)pentanediamide trifluoroacetate | 931.30 | (400 MHz, DMSO-$d_6$) δ 11.09 (s, 1H), 8.82 (t, J = 8.5 Hz, 1H), 8.40-8.24 (m, 3H), 7.38-7.29 (m, 4H), 7.28-7.19 (m, 9H), 7.07 (d, J = 8.1 Hz, 1H), 6.77 (s, 1H), 6.09 (d, J = 8.1 Hz, 1H), 5.40-5.30 (m, 1H), 4.49-4.36 (m, 3H), 4.28-4.14 (m, 1H), 4.02-3.90 (m, 2H), 3.85-3.76 (m, 1H), 3.57 (s, 3H), 3.16-3.07 (m, 2H), 3.05-2.99 (m, 2H), 2.94-2.86 (m, 2H), 2.72-2.57 (m, 2H), 2.25-2.06 (m, 2H), 2.03-1.95 (m, 1H), 1.93-1.78 (m, 5H), 1.76-1.68 (m, 4H), 1.65-1.52 (m, 4H), 1.46-1.37 (m, 1H), 1.35-1.26 (m, 2H), 1.26-1.21 (m, 1H) |
| H124 | 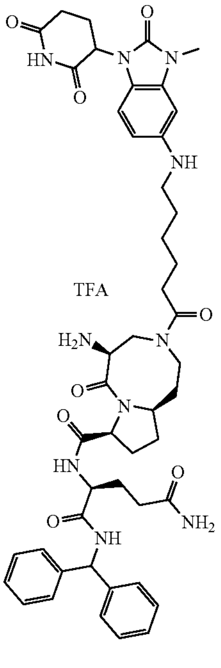 [SMILES: Cn1c(=O)n(C2CCC(=O)NC2=O)c2ccc(NCCCCCC(=O)N3CC[C@H]4CC[C@@H](C(=O)N[C@@H](CCC(N)=O)C(=O)NC(c5ccccc5)c5ccccc5)N4C(=O)[C@@H](N)C3)cc21] TFA | (2S)-2-[[(5S,8S,10aR)-5-amino-3-(6-[[1-(2,6-dioxopiperidin-3-yl)-3-methyl-2-oxo-1,3-benzodiazol-5-yl]amino]hexanoyl)-6-oxo-octahydropyrrolo[1,2-a][1,5]diazocin-8-yl]formamido]-N-(diphenylmethyl) Pentanediamide trifluoroacetate | 891.35 | (400 MHz, DMSO-$d_6$) δ 11.16 (s, 1H), 8.84 (t, J = 8.4 Hz, 1H), 8.36-8.29 (m, 4H), 7.41-7.13 (m, 14H), 6.80 (s, 1H), 6.10 (d, J = 8.4 Hz, 1H), 5.43 (dd, J = 12.7, 5.4 Hz, 1H), 4.53-4.30 (m, 4H), 4.29-3.74 (m, 3H), 3.38 (s, 3H), 3.32-3.28 (m, 2H), 3.28-3.10 (m, 2H), 2.97-2.83 (m, 2H), 2.79-2.57 (m, 2H), 2.48-2.25 (m, 2H), 2.25-1.99 (m, 4H), 1.99-1.82 (m, 4H), 1.71-1.47 (m, 4H), 1.43-1.35 (m, 2H), 1.26-1.22 (m, 1H) |

TABLE 49-continued

| Characterization data for intermediates prepared according to procedure above. | | | | |
|---|---|---|---|---|
| Intermediate | Structure | Chemical Name | MS: [(M + 1)]+ | 1H-NMR |
| H125 | 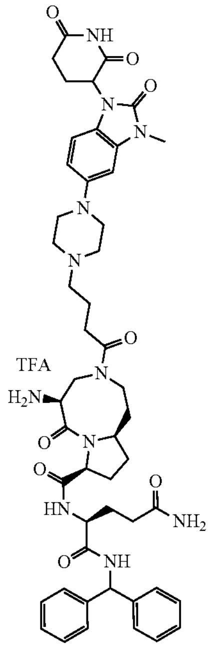 [SMILES: Cn1c(=O)n(C2CCC(=O)NC2=O)c2ccc(N3CCN(CCCC(=O)N4CC[C@H]5CC[C@@H](C(=O)N[C@@H](CCC(N)=O)C(=O)NC(c6ccccc6)c6ccccc6)N5C(=O)[C@@H](N)C4)CC3)cc21] | (2S)-2-[[(5S,8S,10aR)-5-amino-3-(4-[4-[1-(2,6-dioxopiperidin-3-yl)-3-methyl-2-oxo-1,3-benzodiazol-5-yl]piperazin-1-yl]butanoyl)-6-oxo-octahydropyrrolo[1,2-a][1,5]diazocin-8-yl]formamido]-N-(diphenylmethyl)pentanediamide trifluoroacetate | 932.75 | (400 MHz, DMSO-$d_6$) δ 11.08 (s, 1H), 8.80-8.74 (m, 1H), 8.36-8.30 (m, 3H), 7.44-7.14 (m, 11H), 7.01 (d, J = 8.6 Hz, 1H), 6.96-6.90 (m, 1H), 6.81-6.74 (m, 1H), 6.73-6.65 (m, 1H), 6.11 (dd, J = 8.3, 2.3 Hz, 1H), 5.32 (dd, J = 12.9, 5.4 Hz, 1H), 4.64-4.52 (m, 1H), 4.48-4.27 (m, 3H), 4.26-4.22 (m, 2H), 3.92-3.86 (m, 1H), 3.82-3.75 (m, 3H), 3.34 (s, 3H), 3.20-3.14 (m, 5H), 3.05-2.82 (m, 3H), 2.77-2.58 (m, 3H), 2.40-2.34 (m, 1H), 2.29-2.06 (m, 3H), 2.05-1.88 (m, 5H), 1.87-1.64 (m, 6H) |
| H126 | 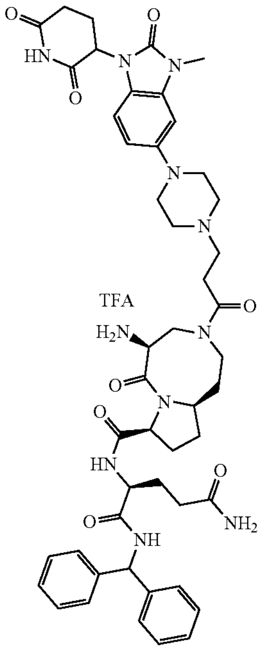 [SMILES: Cn1c(=O)n(C2CCC(=O)NC2=O)c2ccc(N3CCN(CCC(=O)N4CC[C@H]5CC[C@@H](C(=O)N[C@@H](CCC(N)=O)C(=O)NC(c6ccccc6)c6ccccc6)N5C(=O)[C@@H](N)C4)CC3)cc21] | (2S)-2-[[(5S,8S,10aR)-5-amino-3-(3-[4-[1-(2,6-dioxopiperidin-3-yl)-3-methyl-2-oxo-1,3-benzodiazol-5-yl]piperazin-1-yl]propanoyl)-6-oxo-octahydropyrrolo[1,2-a][1,5]diazocin-8-yl]formamido]-N-(diphenylmethyl)pentanediamide trifluoroacetate | 918.70 | (400 MHz, DMSO-$d_6$) δ 11.09 (s, 1H), 8.81-8.58 (m, 2H), 8.45-8.31 (m, 2H), 7.60-7.10 (m, 11H), 7.01 (dd, J = 8.7, 1.8 Hz, 1H), 6.93 (dd, J = 4.4, 2.2 Hz, 1H), 6.86-6.80 (m, 1H), 6.75-6.64 (m, 1H), 6.11 (d, J = 8.3 Hz, 1H), 5.32 (dd, J = 12.9, 5.3 Hz, 1H), 4.66-4.53 (m, 1H), 4.52-4.23 (m, 3H), 4.15-3.84 (m, 1H), 3.78 (t, J = 13.3 Hz, 2H), 3.65 (t, J = 13.0 Hz, 2H), 3.54-3.37 (m, 2H), 3.34 (s, 3H), 3.29-3.09 (m, 4H), 2.99-2.79 (m, 4H), 2.77-2.56 (m, 2H), 2.35-2.07 (m, 4H), 2.06-1.89 (m, 3H), 1.88-1.80 (m, 6H) |

TABLE 49-continued

| Characterization data for intermediates prepared according to procedure above. | | | | |
|---|---|---|---|---|
| Intermediate | Structure | Chemical Name | MS: [(M + 1)]$^+$ | $^1$H-NMR |
| H127 | 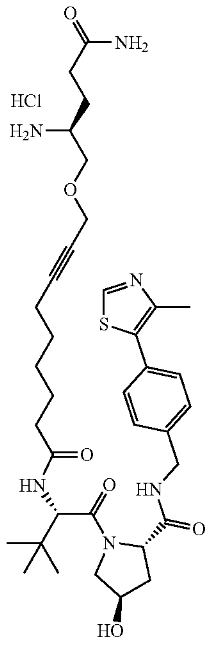 [SMILES: Cc1ncsc1-c1ccc(CNC(=O)[C@@H]2C[C@@H](O)CN2C(=O)[C@@H](NC(=O)CCCCCC#CCOC[C@@H](N)CCC(N)=O)C(C)(C)C)cc1 ; Cl] | (2S,4R)-1-[(2S)-2-[9-[(2S)-2-amino-4-carbamoylbu-toxy]non-7-ynamido]-3,3-dimethylbutanoyl]-4-hydroxy-N-[[4-(4-methyl-1,3-thiazol-5-yl)phenyl]meth-yl]pyrrolidine-2-carboxamide hydrochloride | 697.30 | (400 MHz, DMSO-$d_6$) δ 9.07 (s, 1H), 8.58 (t, J = 6.0 Hz, 1H), 8.13-8.09 (m, 2H), 7.87 (d, J = 9.3 Hz, 1H), 7.53-7.29 (m, 4H), 6.92-6.89 (m, 1H), 4.59-4.52 (m, 1H), 4.48-4.41 (m, 2H), 4.37-4.35 (m, 1H), 4.25 (d, J = 5.2 Hz, 1H), 4.22-4.16 (m, 2H), 3.73-3.63 (m, 2H), 3.62-3.56 (m, 4H), 3.52-3.49 (m, 1H), 3.29-2.25 (m, 2H), 2.46 (s, 3H), 2.32-2.01 (m, 6H), 1.93-1.89 (m, 1H), 1.78-1.72 (m, 2H), 1.51-1.43 (m, 3H), 1.40-1.26 (m, 2H), 0.94 (s, 9H). |
| H128 | 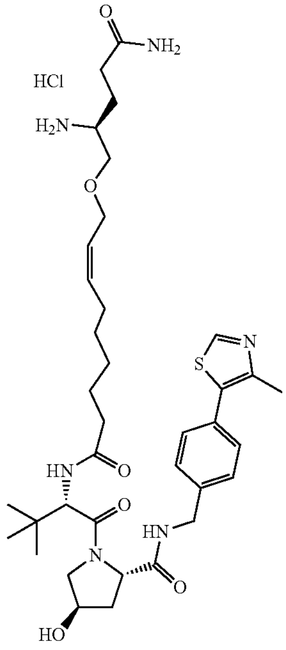 [SMILES: Cc1ncsc1-c1ccc(CNC(=O)[C@@H]2C[C@@H](O)CN2C(=O)[C@@H](NC(=O)CCCCC/C=C\COC[C@@H](N)CCC(N)=O)C(C)(C)C)cc1 ; Cl] | (2S,4R)-1-[(2S)-2-[(7Z)-9-[(2S)-2-amino-4-carbamoylbu-toxy]non-7-enamido]-3,3-dimethylbutanoyl]-4-hydroxy-N-[[4-(4-methyl-1,3-thiazol-5-yl)-phenyl]meth-yl]pyrrolidine-2-carboxamide hydrochloride | 699.25 | (400 MHz, DMSO-$d_6$) δ 9.16-9.11 (m, 1H), 8.60 (s, 1H), 8.36 (s, 1H), 8.13 (s, 2H), 7.86 (d, J = 9.3 Hz, 1H), 7.57-7.28 (m, 5H), 6.91 (s, 1H), 5.63-5.38 (m, 7H), 4.54 (d, J = 9.3 Hz, 1H), 4.47-4.38 (m, 2H), 4.35 (s, 1H), 4.23 (dd, J = 15.0, 4.8 Hz, 1H), 4.05 (d, J = 5.6 Hz, 1H), 3.71-3.60 (m, 2H), 3.57 (s, 3H), 3.56-3.52 (m, 2H), 3.48-3.33 (m, 1H), 3.24 (s, 1H), 2.47-2.45 (m, 3H), 2.30-2.20 (m, 2H), 2.18-1.96 (m, 3H), 1.94-1.87 (m, 1H), 1.83-1.67 (m, 1H), 1.56-1.44 (m, 1H), 1.34-1.22 (m, 1H), 0.94 (s, 9H) |

TABLE 49-continued

| Characterization data for intermediates prepared according to procedure above. | | | | |
|---|---|---|---|---|
| Intermediate | Structure | Chemical Name | MS: $[(M+1)]^+$ | $^1$H-NMR |
| H129 | 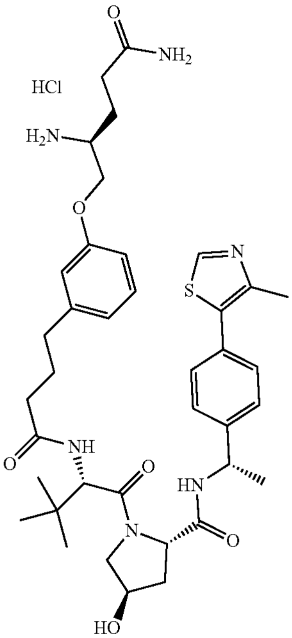 [SMILES: Cc1ncsc1-c1ccc([C@H](C)NC(=O)[C@@H]2C[C@@H](O)CN2C(=O)[C@@H](NC(=O)CCCc2cccc(OC[C@@H](N)CCC(N)=O)c2)C(C)(C)C)cc1 ; Cl] | (2S,4R)-1-[(2S)-2-(4-[3-[(2S)-2-amino-4-carbamoylbutoxy]phenyl]butanamido)-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride | 721.55 | (400 MHz, DMSO-$d_6$) δ 9.21 (s, 1H), 8.43 (s, 4H), 7.85 (d, J = 9.2 Hz, 1H), 7.46 (d, J = 8.3 Hz, 2H), 7.40 (d, J = 8.2 Hz, 2H), 7.22 (dd, J = 9.2, 7.2 Hz, 1H), 6.93 (s, 1H), 6.87-6.78 (m, 3H), 4.92 (p, J = 6.9 Hz, 1H), 4.54 (d, J = 9.3 Hz, 1H), 4.44 (t, J = 8.0 Hz, 1H), 4.28 (s, 1H), 4.18 (dd, J = 10.3, 3.6 Hz, 1H), 4.05 (dd, J = 10.4, 6.3 Hz, 1H), 3.48 (s, 1H), 2.54 (s, 2H), 2.48 (s, 3H), 2.38-2.22 (m, 2H), 2.20-2.16 (m, 1H), 2.08-1.85 (m, 2H), 1.81-1.78 (s, 3H), 1.62-1.58 (m, 5H), 1.38 (d, J = 7.0 Hz, 3H), 0.95 (s, 9H) |
| H130 | 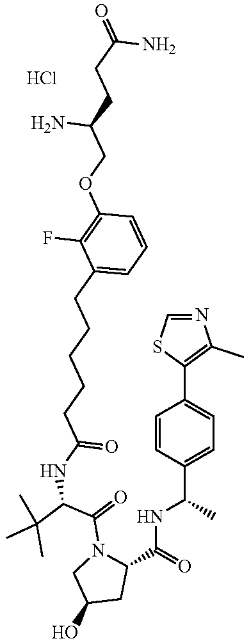 [SMILES: Cc1ncsc1-c1ccc([C@H](C)NC(=O)[C@@H]2C[C@@H](O)CN2C(=O)[C@@H](NC(=O)CCCCCc2cccc(OC[C@@H](N)CCC(N)=O)c2F)C(C)(C)C)cc1 ; Cl] | (2S,4R)-1-[(2S)-2-(6-[3-[(2S)-2-amino-4-carbamoylbutoxy]-2-fluorophenyl]hexanamido)-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride | 767.97 | (400 MHz, DMSO-$d_6$) δ 9.14 (s, 1H), 8.43 (d, J = 7.7 Hz, 3H), 7.45 (d, J = 8.3 Hz, 4H), 7.39 (d, J = 8.3 Hz, 2H), 7.07-7.03 (m, 2H), 6.94 (s, 1H), 6.91-6.87 (m, 1H), 4.94-4.90 (m, 1H), 4.51 (d, J = 9.4 Hz, 1H), 4.45-4.41 (m, 1H), 4.30-4.26 (m, 1H), 4.25-4.20 (m, 1H), 4.17-4.15 (m, 2H), 3.68-3.55 (m, 3H), 2.61-2.57 (m, 2H), 2.47 (s, 3H), 2.30-2.26 (m, 2H), 2.08 (s, 1H), 2.17-1.86 (m, 3H), 1.84-1.71 (m, 1H), 1.62-1.42 (m, 5H), 1.40-1.36 (m, 3H), 1.33-1.20 (m, 2H), 0.93 (s, 9H) |

TABLE 49-continued

| Characterization data for intermediates prepared according to procedure above. | | | | |
|---|---|---|---|---|
| Intermediate | Structure | Chemical Name | MS: $[(M + 1)]^+$ | $^1$H-NMR |
| H131 | 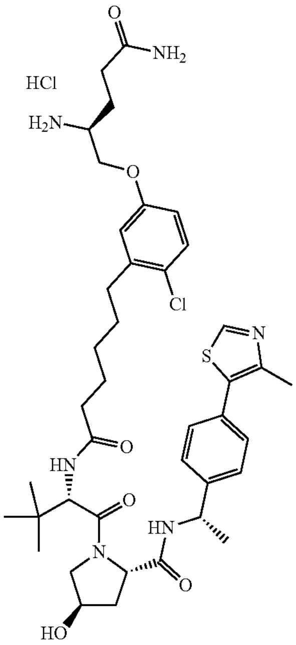 [SMILES: Cc1ncsc1-c1ccc([C@H](C)NC(=O)[C@@H]2C[C@@H](O)CN2C(=O)[C@@H](NC(=O)CCCCCc2cc(OC[C@@H](N)CCC(N)=O)ccc2Cl)C(C)(C)C)cc1 ; Cl] | (2S,4R)-1-[(2S)-2-(6-[5-[(2S)-2-amino-4-carbamoylbutoxy]-2-chlorophenyl]hexanamido)-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride | 783.55 | (400 MHz, DMSO-$d_6$) δ 9.12 (s, 1H), 8.45-8.37 (m, 5H), 7.84-7.75 (m, 1H), 7.48-7.29 (m, 5H), 6.98 (d, J = 3.0 Hz, 1H), 6.87 (d, J = 8.8, 3.0 Hz, 1H), 4.92 (d, J = 7.3 Hz, 1H), 4.52 (d, J = 9.3 Hz, 1H), 4.47-4.38 (m, 2H), 4.28 (s, 1H), 4.19 (d, J = 10.3, 3.6 Hz, 1H), 4.10-4.01 (m, 1H), 3.70-3.56 (m, 3H), 2.68-2.59 (m, 2H), 2.47 (s, 3H), 2.37-2.19 (m, 4H), 2.14-2.10 (m, 1H), 2.04-2.00 (m, 1H), 1.92-1.89 (m, 1H), 1.87-1.69 (m, 2H), 1.60 (s, 1H), 1.57-1.44 (m, 3H), 1.38 (d, J = 7.0 Hz, 3H), 1.38-1.27 (m, 1H), 1.25-1.21 (m, 1H), 0.93 (s, 9H) |
| H132 | 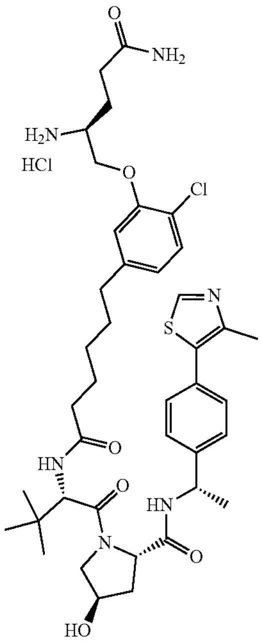 [SMILES: Cc1ncsc1-c1ccc([C@H](C)NC(=O)[C@@H]2C[C@@H](O)CN2C(=O)[C@@H](NC(=O)CCCCCc2ccc(Cl)c(OC[C@@H](N)CCC(N)=O)c2)C(C)(C)C)cc1 ; Cl] | (2S,4R)-1-[(2S)-2-(6-[3-[(2S)-2-amino-4-carbamoylbutoxy]-4-chlorophenyl]hexanamido)-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride | 783.30 | (400 MHz, DMSO-$d_6$) δ 9.02 (s, 1H), 8.39 (d, J = 7.8 Hz, 2H), 8.25 (s, 2H), 7.83-7.76 (m, 2H), 7.35-7.32 (m, 2H), 7.22 (d, J = 9.9 Hz, 1H), 7.13-7.03 (m, 2H), 6.95 (s, 1H), 6.85-6.83 (m, 1H), 4.92-4.90 (m, 2H), 4.52-4.50 (m, 2H), 4.42-4.40 (m, 3H), 4.25-4.21 (m, 2H), 4.15-4.13 (m, 1H), 3.67-3.59 (m, 3H), 3.42-3.40 (m, 1H), 2.57-2.55 (m, 2H), 2.31-2.29 (m, 1H), 2.16-2.06 (m, 2H), 2.01 (s, 3H), 1.94-1.92 (m, 2H), 1.85-1.75 (m, 4H), 1.62-1.51 (m, 2H), 1.47-1.35 (m, 1H), 1.27-1.25 (m, 2H), 1.23 (s, 9H) |

TABLE 49-continued

| Characterization data for intermediates prepared according to procedure above. | | | | |
|---|---|---|---|---|
| Intermediate | Structure | Chemical Name | MS: $[(M+1)]^+$ | $^1$H-NMR |
| H133 | 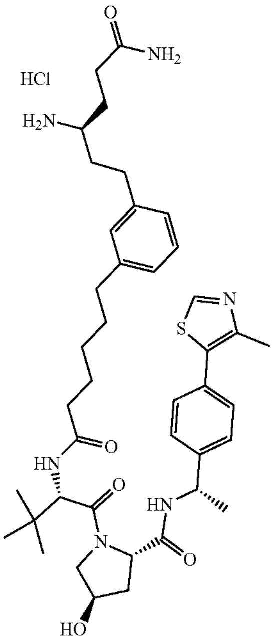 [SMILES: Cc1ncsc1-c1ccc([C@H](C)NC(=O)[C@@H]2C[C@@H](O)CN2C(=O)[C@@H](NC(=O)CCCCCc2cccc(CC[C@@H](N)CCC(N)=O)c2)C(C)(C)C)cc1 ; Cl] | (2S,4R)-1-[(2S)-2-(6-[3-[(3R)-3-amino-5-carbamoylpentyl]phenyl]hexanamido)-3,3-dimethylbutanoyl]-4-hydroxy-N-[(1S)-1-[4-(4-methyl-1,3-thiazol-5-yl)phenyl]ethylpyrrolidine-2-carboxamide hydrochloride | 747.60 | (300 MHz, DMSO-$d_6$) δ 9.09 (s, 1H), 8.38 (d, J = 7.7 Hz, 1H), 8.17 (s, 2H), 7.76 (d, J = 9.2 Hz, 1H), 7.41 (q, J = 8.4 Hz, 4H), 7.18 (t, J = 7.4 Hz, 1H), 7.11-6.96 (m, 3H), 6.89 (s, 1H), 4.90 (d, J = 7.3 Hz, 1H), 4.50 (d, J = 9.4 Hz, 1H), 4.42 (t, J = 8.0 Hz, 1H), 4.27 (s, 1H), 3.62-3.58 (m, 3H), 3.08 (s, 1H), 2.68-2.57 (m, 2H), 2.56-2.53 (m, 1H), 2.46 (s, 3H), 2.34-1.95 (m, 4H), 1.91-1.74 (m, 6H), 1.57-1.42 (m, 4H), 1.43-1.24 (m, 4H), 1.32-1.24 (m, 2H), 0.92 (s, 9H) |
| H134 | 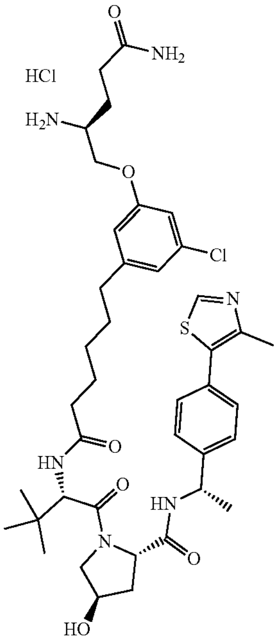 [SMILES: Cc1ncsc1-c1ccc([C@H](C)NC(=O)[C@@H]2C[C@@H](O)CN2C(=O)[C@@H](NC(=O)CCCCCc2cc(Cl)cc(OC[C@@H](N)CCC(N)=O)c2)C(C)(C)C)cc1 ; Cl] | (2S,4R)-1-[(2S)-2-(6-[3-[(2S)-2-amino-4-carbamoylbutoxy]-5-chlorophenyl]hexanamido)-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride | 783.20 | (400 MHz, DMSO-$d_6$) δ 9.20 (s, 1H), 8.42 (d, J = 6.9 Hz, 3H), 7.79 (d, J = 9.2 Hz, 1H), 7.46 (d, J = 8.3 Hz, 2H), 7.40 (d, J = 8.3 Hz, 2H), 7.12 (s, 2H), 6.90 (d, J = 1.9 Hz, 2H), 6.82 (t, J = 1.8 Hz, 1H), 4.98-4.85 (m, 1H), 4.51 (d, J = 9.3 Hz, 1H), 4.47-4.39 (m, 1H), 4.31-4.26 (m, 1H), 4.24-4.18 (m, 1H), 4.12-4.04 (m, 1H), 3.61 (d, J = 4.4 Hz, 2H), 2.48 (s, 3H), 2.38-2.20 (m, 3H), 2.18-2.07 (m, 1H), 2.03 (t, J = 10.9 Hz, 1H), 1.98-1.87 (m, 1H), 1.83-1.68 (m, 1H), 1.60 (s, 3H), 1.58-1.44 (m, 4H), 1.38 (d, J = 7.0 Hz, 3H), 1.32-1.21 (m, 3H), 1.14-1.02 (m, 1H), 0.93 (s, 9H) |

TABLE 49-continued

| Characterization data for intermediates prepared according to procedure above. | | | | |
|---|---|---|---|---|
| Intermediate | Structure | Chemical Name | MS: [(M + 1)]+ | $^1$H-NMR |
| H135 | 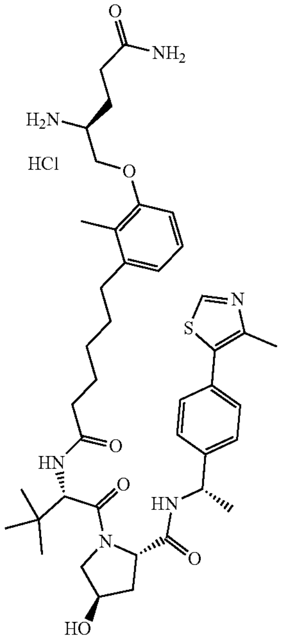 [SMILES: Cc1ncsc1-c1ccc([C@H](C)NC(=O)[C@@H]2C[C@@H](O)CN2C(=O)[C@@H](NC(=O)CCCCCc2cccc(OC[C@@H](N)CCC(N)=O)c2C)C(C)(C)C)cc1 ; Cl] | (2S,4R)-1-[(2S)-2-(6-[3-[(2S)-2-amino-4-carbamoylbutoxy]-2-methylphenyl]hexan-amido)-3,3-dimethylbutanoyl]-4-hydroxy-N-[(1S)-1-[4-(4-methyl-1,3-thiazol-5-yl)phenyl]eth-yl]pyrrolidine-2-carboxamide hydrochloride | 763.35 | (400 MHz, DMSO-$d_6$) δ 9.09 (s, 1H), 8.50-8.28 (m, 3H), 7.80 (d, J = 9.2 Hz, 1H), 7.45 (d, J = 8.3 Hz, 2H), 7.39 (d, J = 8.3 Hz, 2H), 7.07 (t, J = 7.9 Hz, 1H), 6.93 (s, 1H), 6.82-6.74 (m, 2H), 4.96-4.89 (m, 1H), 4.55-4.49 (m, 1H), 4.43 (t, J = 8.0 Hz, 1H), 4.28 (s, 1H), 4.14 (dd, J = 10.4, 3.5 Hz, 1H), 4.02 (dd, J = 10.4, 5.6 Hz, 1H), 3.64-3.58 (m, 6H), 3.53-3.49 (m, 1H), 2.57-2.53 (m, 1H), 2.47 (s, 3H), 2.35-2.23 (m, 2H), 2.17 (s, 3H), 2.14-1.87 (m, 3H), 1.84-1.71 (m, 4H), 1.57-1.44 (m, 3H), 1.38 (d, J = 7.0 Hz, 3H), 1.35-1.13 (m, 1H), 0.94 (s, 9H) |
| H136 | 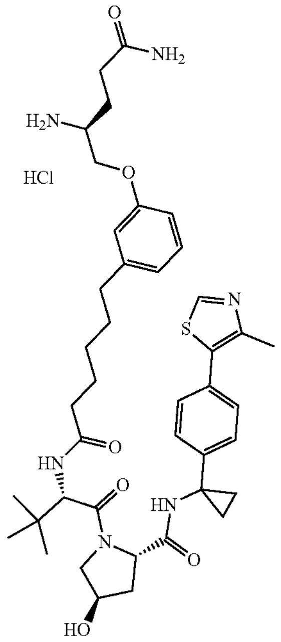 [SMILES: Cc1ncsc1-c1ccc(C2(NC(=O)[C@@H]3C[C@@H](O)CN3C(=O)[C@@H](NC(=O)CCCCCc3cccc(OC[C@@H](N)CCC(N)=O)c3)C(C)(C)C)CC2)cc1 ; Cl] | (2S,4R)-1-[(2S)-2-(6-[3-[(2S)-2-amino-4-carbamoylbu-toxy]phenyl]hexan-amido)-3,3-dimethylbutanoyl]-4-hydroxy-N-[1-[4-(4-methyl-1,3-thiazol-5-yl)phenyl]cyclopro-pyl]pyrrolidine-2-carboxamide hydrochloride | 761.55 | (400 MHz, DMSO-$d_6$) δ 9.09 (s, 1H), 8.83 (s, 1H), 8.38-8.34 (m, 2H), 7.90 (d, J = 9.3 Hz, 1H), 7.37-7.27 (m, 4H), 7.21 (t, J = 7.8 Hz, 1H), 6.92 (s, 1H), 6.86-6.77 (m, 2H), 4.55 (d, J = 9.4 Hz, 1H), 4.39 (dd, J = 17.1, 8.9 Hz, 2H), 4.17 (dd, J = 10.3, 3.6 Hz, 1H), 4.04 (dd, J = 10.4, 6.4 Hz, 1H), 3.61 (d, J = 5.8 Hz, 3H), 2.56 (d, J = 7.8 Hz, 2H), 2.45 (s, 3H), 2.39-2.22 (m, 2H), 2.14 (dt, J = 14.2, 7.2 Hz, 1H), 2.05-1.81 (m, 2H), 1.78-1.74 (m, 5H), 1.60 (s, 3H), 1.53-1.49 (m, 1H), 1.27-1.23 (m, 6H), 1.17-1.09 (m, 1H), 0.94 (s, 9H) |

TABLE 49-continued

| Characterization data for intermediates prepared according to procedure above. | | | | |
|---|---|---|---|---|
| Intermediate | Structure | Chemical Name | MS: $[(M + 1)]^+$ | $^1$H-NMR |
| H137 | 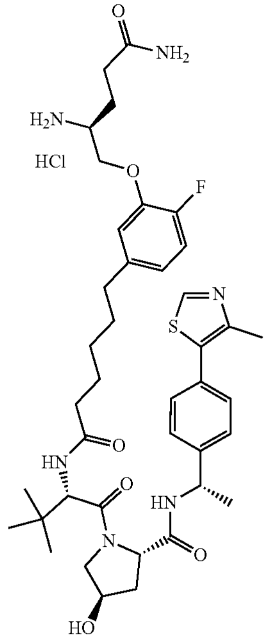 [SMILES: Cc1ncsc1-c1ccc([C@H](C)NC(=O)[C@@H]2C[C@@H](O)CN2C(=O)[C@@H](NC(=O)CCCCCc2ccc(F)c(OC[C@@H](N)CCC(N)=O)c2)C(C)(C)C)cc1 ; Cl] | (2S,4R)-1-[(2S)-2-(6-[3-[(2S)-2-amino-4-carbamoylbutoxy]-4-fluorophenyl]hexanamido)-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride | 767.35 | (400 MHz, DMSO-$d_6$) δ 6 9.08 (s, 1H), 8.41 (d, J = 7.7 Hz, 1H), 8.35-8.32 (m, 3H), 7.80 (d, J = 9.3 Hz, 1H), 7.48-7.32 (m, 5H), 7.17-7.04 (m, 2H), 6.94 (s, 1H), 4.96-4.88 (m, 2H), 4.52 (d, J = 9.1 Hz, 1H), 4.43 (d, J = 8.0 Hz, 1H), 4.31-4.20 (m, 2H), 4.15 (d, J = 8.3 Hz, 1H), 3.69-3.56 (m, 6H), 3.54-3.50 (m, 1H), 2.47 (s, 3H), 2.29-2.25 (m, 2H), 2.14-2.10 (m, 1H), 2.04-2.00 (m, 1H), 1.95-1.91 (m, 1H), 1.79-1.75 (m, 2H), 1.57-1.53 (m, 4H), 1.38 (d, J = 7.0 Hz, 3H), 1.25 (m, 1H), 0.93 (d, 9H) |
| H138 | 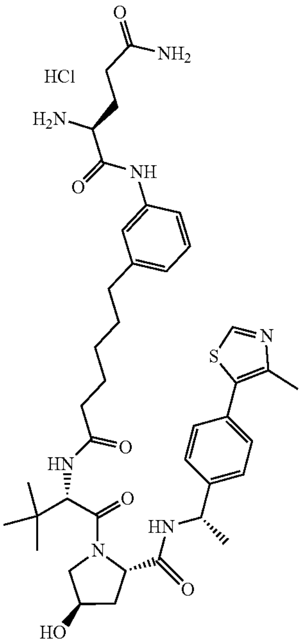 [SMILES: Cc1ncsc1-c1ccc([C@H](C)NC(=O)[C@@H]2C[C@@H](O)CN2C(=O)[C@@H](NC(=O)CCCCCc2cccc(NC(=O)[C@@H](N)CCC(N)=O)c2)C(C)(C)C)cc1 ; Cl] | (2S)-2-amino-N-[3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenyl]pentanediamide hydrochloride | 762.45 | (300 MHz, DMSO-$d_6$) δ 10.72 (s, 1H), 9.04 (s, 1H), 8.47-8.36 (m, 4H), 7.76 (d, J = 9.2 Hz, 1H), 7.49-7.36 (m, 7H), 7.24 (t, J = 7.8 Hz, 1H), 6.94 (d, J = 7.6 Hz, 2H), 4.94-4.88 (m, 1H), 4.57-4.36 (m, 2H), 4.27 (s, 1H), 4.03 (s, 1H), 2.57-2.55 (m, 1H), 2.46 (s, 3H), 2.28-2.20 (m, 3H), 2.16-1.97 (m, 4H), 1.83-1.74 (m, 1H), 1.64-1.43 (m, 6H), 1.37 (d, J = 6.7 Hz, 3H), 1.33-1.20 (m, 3H), 0.92 (s, 9H) |

TABLE 49-continued

Characterization data for intermediates prepared according to procedure above.

| Intermediate | Structure | Chemical Name | MS: $[(M + 1)]^+$ | $^1$H-NMR |
|---|---|---|---|---|
| H139 | 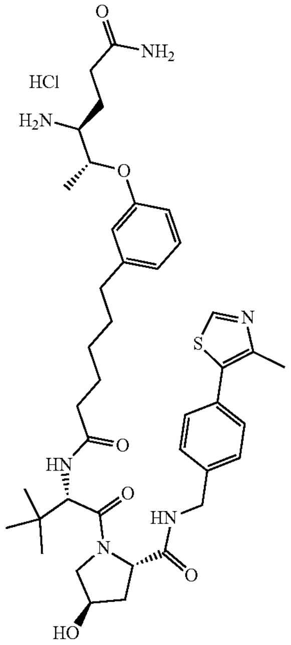 [SMILES: Cc1ncsc1-c1ccc(CNC(=O)[C@@H]2C[C@@H](O)CN2C(=O)[C@@H](NC(=O)CCCCCc2cccc(O[C@H](C)[C@@H](N)CCC(N)=O)c2)C(C)(C)C)cc1 ; Cl] | (2S,4R)-1-[(2S)-2-[6-(3-[[(2R,3S)-3-amino-5-carbamoylpentan-2-yl]oxy]phenyl)hexanamido]-3,3-dimethylbutanoyl]-4-hydroxy-N-[[4-(4-methyl-1,3-thiazol-5-yl)phenyl]methyl]pyrrolidine-2-carboxamide | 749.30 | (300 MHz, DMSO-$d_6$) δ 6 9.04 (s, 1H), 8.58 (t, J = 6.0 Hz, 1H), 8.21 (s, 3H), 7.85 (d, J = 9.3 Hz, 1H), 7.49-7.39 (m, 6H), 7.21 (t, J = 7.7 Hz, 1H), 6.96 (s, 1H), 6.89-6.78 (m, 4H), 4.55 (d, J = 9.3 Hz, 1H), 4.51-4.33 (m, 3H), 4.24 (dd, J = 15.9, 5.4 Hz, 1H), 3.73-3.63 (m, 2H), 3.40 (q, J = 7.0 Hz, 2H), 2.47 (s, 3H), 2.37-2.24 (m, 3H), 2.20-1.81 (m, 4H), 1.62-1.49 (m, 5H), 1.34-1.28 (m, 1H), 1.24 (d, J = 6.3 Hz, 3H), 1.11 (t, J = 7.0 Hz, 1H), 0.95 (s, 9H) |
| H140 | 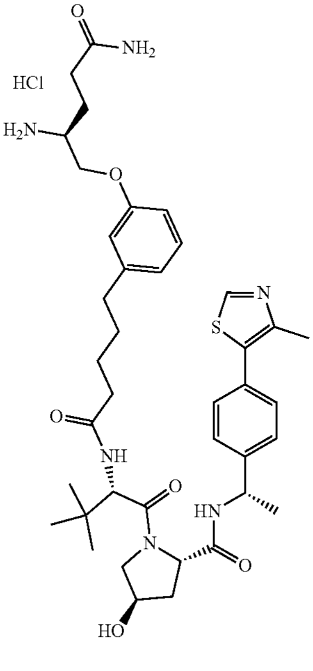 [SMILES: Cl ; Cc1ncsc1-c1ccc([C@H](C)NC(=O)[C@@H]2C[C@@H](O)CN2C(=O)[C@@H](NC(=O)CCCCc2cccc(OC[C@@H](N)CCC(N)=O)c2)C(C)(C)C)cc1] | (2S,4R)-1-[(2S)-2-(5-[3-[(2S)-2-amino-4-carbamoylbutoxy]phenyl]pentanamido)-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride | 735.35 | (400 MHz, DMSO-$d_6$) δ 9.12 (d, J = 1.5 Hz, 1H), 8.36 (s, 2H), 7.83 (d, J = 9.2 Hz, 1H), 7.49-7.37 (m, 4H), 7.22 (t, J = 7.8 Hz, 1H), 6.93 (s, 1H), 6.81 (d, J = 8.8 Hz, 3H), 4.92 (p, J = 7.1 Hz, 1H), 4.52 (d, J = 9.2 Hz, 1H), 4.43 (t, J = 8.0 Hz, 1H), 4.28 (s, 1H), 4.19-4.15 (m, 1H), 4.05-4.01 (m, 1H), 3.69-3.60 (m, 1H), 3.52-3.36 (m, 1H), 2.57-2.53 (m, 1H), 2.47 (s, 3H), 2.32-2.28 (m, 2H), 2.18-2.14 (m, 1H), 2.07-2.03 (m, 1H), 1.92-1.88 (m, 2H), 1.82-1.69 (m, 6H), 1.62-1.58 (m, 2H), 1.58-1.43 (m, 2H), 1.38 (d, J = 7.0 Hz, 3H), 1.26-1.22(m, 1H), 0.94 (s, 9H) |

TABLE 49-continued

Characterization data for intermediates prepared according to procedure above.

| Intermediate | Structure | Chemical Name | MS: $[(M + 1)]^+$ | $^1$H-NMR |
|---|---|---|---|---|
| H141 | 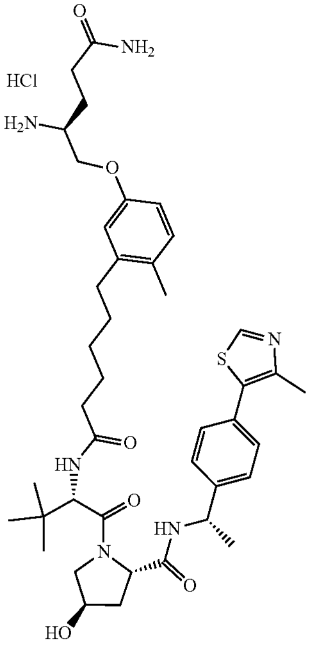 [SMILES: Cc1ccc(OC[C@@H](N)CCC(N)=O)cc1CCCCCC(=O)N[C@H](C(=O)N1C[C@H](O)C[C@H]1C(=O)N[C@@H](C)c1ccc(-c2scnc2C)cc1)C(C)(C)C ; Cl] | (2S,4R)-1-[(2S)-2-(6-[5-[(2S)-2-amino-4-carbamoylbutoxy]-2-methylphenyl]hexanamido)-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride | 763.35 | crude used next step without purification |
| H142 | 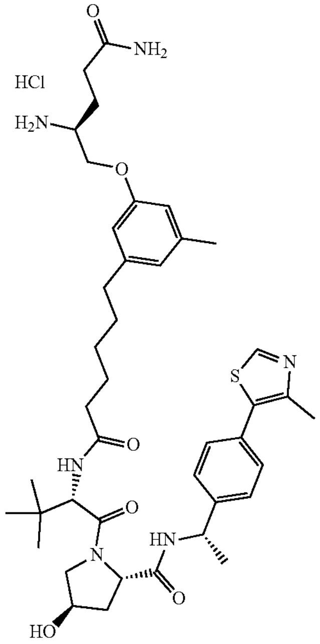 [SMILES: Cc1cc(CCCCCC(=O)N[C@H](C(=O)N2C[C@H](O)C[C@H]2C(=O)N[C@@H](C)c2ccc(-c3scnc3C)cc2)C(C)(C)C)cc(OC[C@@H](N)CCC(N)=O)c1 ; Cl] | (2S,4R)-1-[(2S)-2-(6-[3-[(2S)-2-amino-4-carbamoylbutoxy]-5-methylphenyl]hexanamido)-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride | 763.35 | crude used next step without purification |

TABLE 49-continued

| Characterization data for intermediates prepared according to procedure above. | | | | |
|---|---|---|---|---|
| Intermediate | Structure | Chemical Name | MS: [(M + 1)]+ | 1H-NMR |
| H143 | 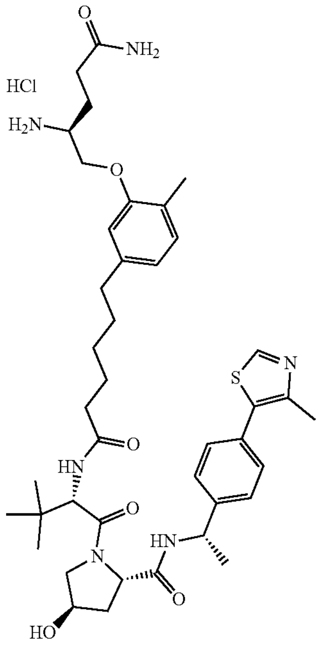 [SMILES: Cc1ccc(CCCCCC(=O)N[C@H](C(=O)N2C[C@H](O)C[C@H]2C(=O)N[C@@H](C)c2ccc(-c3scnc3C)cc2)C(C)(C)C)cc1OC[C@@H](N)CCC(N)=O ; Cl] | (2S,4R)-1-[(2S)-2-(6-[3-[(2S)-2-amino-4-carbamoylbutoxy]-4-methylphenyl]hexanamido)-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride | 763.35 | (400 MHz, Chloroform-d) δ 8.70 (s, 1H), 7.41-7.30 (m, 5H), 7.03 (d, J = 7.6 Hz, 1H), 6.69 (d, J = 7.5, 1.5 Hz, 1H), 6.61 (d, J = 1.6 Hz, 1H), 6.52-6.47 (m, 1H), 6.36 (d, J = 8.7 Hz, 1H), 5.75 (s, 1H), 5.32 (s, 1H), 5.10 (d, J = 14.9, 7.4 Hz, 2H), 4.73 (s, 1H), 4.58 (d, J = 8.8 Hz, 1H), 4.55-4.51 (m, 1H), 4.13-3.94 (m, 4H), 3.63 (d, J = 11.3, 3.8 Hz, 1H), 3.50 (s, 1H), 2.56-2.52 (m, 4H), 2.36 (d, J = 6.8, 2.2 Hz, 2H), 2.19-2.10 (m, 3H), 2.03-1.99 (m, 2H), 1.62-1.59 (m, 3H), 1.51-1.47 (m, 3H), 1.46-1.40 (m, 5H), 1.29-1.25 (m, 3H), 1.04 (s, 9H) |
| H144 | 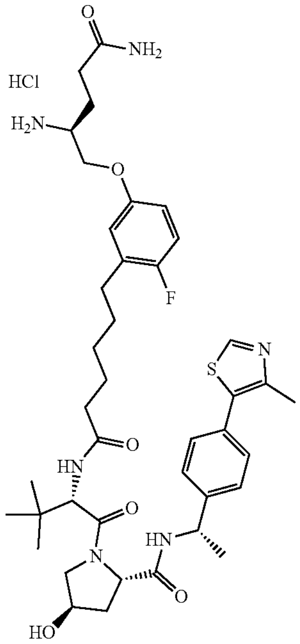 [SMILES: Cc1ncsc1-c1ccc([C@H](C)NC(=O)[C@@H]2C[C@@H](O)CN2C(=O)[C@@H](NC(=O)CCCCCc2cc(OC[C@@H](N)CCC(N)=O)ccc2F)C(C)(C)C)cc1 ; Cl] | (2S,4R)-1-[(2S)-2-(6-[5-[(2S)-2-amino-4-carbamoylbutoxy]-2-fluorophenyl]hexanamido)-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride | 767.35 | (400 MHz, DMSO-$d_6$) δ 9.29 (s, 1H), 8.46 (s, 3H), 7.80 (d, J = 9.2 Hz, 1H), 7.47 (dd, J = 8.3, 2.1 Hz, 2H), 7.44-7.33 (m, 2H), 7.06 (t, J = 9.2 Hz, 1H), 6.91 (dd, J = 6.3, 3.1 Hz, 1H), 6.84 (dd, J = 8.8, 3.8 Hz, 1H), 4.98-4.86 (m, 1H), 4.51 (d, J = 9.3 Hz, 1H), 4.43 (t, J = 8.0 Hz, 1H), 4.27 (s, 1H), 4.21-4.12 (m, 1H), 4.04 (dd, J = 10.3, 6.3 Hz, 1H), 3.45 (s, 2H), 2.55 (t, J = 7.6 Hz, 2H), 2.45 (s, 3H), 2.31-2.27 (m, 3H), 2.18-2.01 (m, 1H), 2.00-1.85 (m, 2H), 1.83-1.77 (m, 1H), 1.59 (s, 3H), 1.57-1.44 (m, 6H), 1.37 (d, J = 7.0 Hz, 3H), 1.33-1.21 (m, 2H), 0.93 (s, 9H) |

TABLE 49-continued

| Characterization data for intermediates prepared according to procedure above. | | | | |
|---|---|---|---|---|
| Intermediate | Structure | Chemical Name | MS: $[(M + 1)]^+$ | $^1$H-NMR |
| H145 | 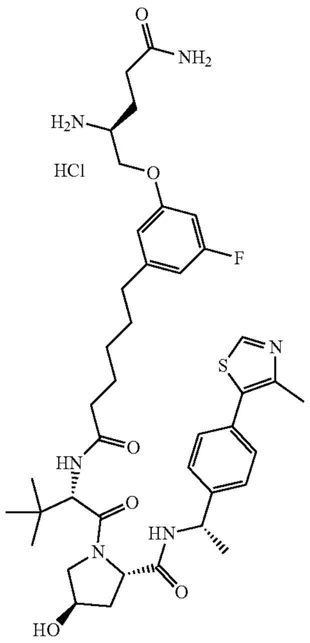 [SMILES: Cc1ncsc1-c1ccc([C@H](C)NC(=O)[C@@H]2C[C@@H](O)CN2C(=O)[C@@H](NC(=O)CCCCCc2cc(F)cc(OC[C@@H](N)CCC(N)=O)c2)C(C)(C)C)cc1 ; Cl] | (2S,4R)-1-[(2S)-2-(6-[3-[(2S)-2-amino-4-carbamoylbutoxy]-5-fluorophenyl]hexanamido)-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride | 767.30 | (400 MHz, DMSO-$d_6$) δ 9.22 (s, 1H), 8.45-8.41 (m, 3H), 7.80 (d, J = 9.3 Hz, 1H), 7.46 (d, J = 8.4 Hz, 2H), 7.40 (d, J = 8.1 Hz, 2H), 6.72-6.63 (m, 3H), 4.94-4.90 (m, 1H), 4.51 (d, J = 9.3 Hz, 1H), 4.43 (t, J = 8.0 Hz, 1H), 4.30-4.16 (m, 1H), 4.16-4.03 (m, 1H), 3.62-3.58 (m, 6H), 2.55 (d, J = 7.6 Hz, 1H), 2.48 (s, 3H), 2.31-2.27 (m, 2H), 2.18-2.01 (m, 1H), 1.94-1.90 (m, 1H), 1.82-1.70 (m, 9H), 1.61-1.57 (m, 2H), 1.38 (d, J = 7.0 Hz, 3H), 1.27-1.23 (m, 1H), 0.93 (s, 9H) |
| H146 | 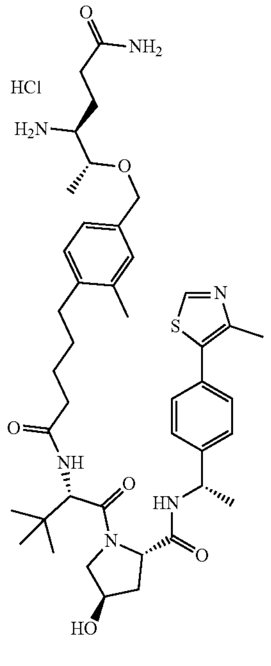 [SMILES: Cc1cc(CO[C@H](C)[C@@H](N)CCC(N)=O)ccc1CCCCC(=O)N[C@H](C(=O)N1C[C@H](O)C[C@H]1C(=O)N[C@@H](C)c1ccc(-c2scnc2C)cc1)C(C)(C)C ; Cl] | (2S,4R)-1-[(2S)-2-[5-[4-([[(2R,3S)-3-amino-5-carbamoylpentan-2-yl]oxy]methyl)-2-methylphenyl]pentanamido]-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride | 777.05 | (400 MHz, DMSO-$d_6$) δ 9.03 (s, 1H), 8.39 (d, J = 7.8 Hz, 1H), 8.03-7.98 (m, 3H), 7.82 (d, J = 9.4 Hz, 1H), 7.45 (d, J = 8.1 Hz, 3H), 7.39 (d, J = 8.3 Hz, 2H), 7.16-7.06 (m, 4H), 6.93 (s, 1H), 4.92 (t, J = 7.2 Hz, 1H), 4.54-4.36 (m, 3H), 4.28 (s, 1H), 3.79-3.70 (m, 1H), 3.64-3.60 (m, 2H), 3.27 (s, 1H), 2.57-2.54 (m, 1H), 2.46 (s, 3H), 2.36-2.29 (m, 1H), 2.26-2.23 (m, 5H), 2.20-2.10 (m, 1H), 2.05-1.99 (m, 1H), 1.85-1.67 (m, 3H), 1.57-1.46 (m, 5H), 1.38 (d, J = 7.0 Hz, 3H), 1.15 (d, J = 6.3 Hz, 3H), 0.94 (s, 9H) |

TABLE 49-continued

Characterization data for intermediates prepared according to procedure above.

| Intermediate | Structure | Chemical Name | MS: [(M + 1)]+ | 1H-NMR |
|---|---|---|---|---|
| H147 | 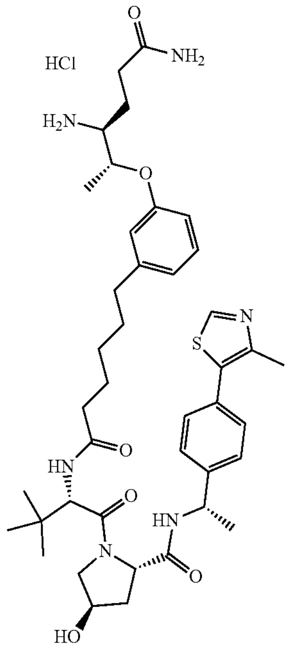 [SMILES: Cc1ncsc1-c1ccc([C@H](C)NC(=O)[C@@H]2C[C@@H](O)CN2C(=O)[C@@H](NC(=O)CCCCCc2cccc(O[C@H](C)[C@@H](N)CCC(N)=O)c2)C(C)(C)C)cc1 ; Cl] | (2S,4R)-1-((S)-2-(6-(3-(((2R,3S)-3,6-diamino-6-oxohexan-2-yl)oxy)phenyl)hexanamido)-3,3-dimethylbutanoyl)-4-hydroxy-N-((S)-1-(4-(4-methylthiazol-5-yl)phenyl)ethyl)pyrrolidine-2-carboxamide hydrochloride | 763.35 | (400 MHz, DMSO-$d_6$) δ 9.14 (s, 1H), 8.42 (d, J = 7.8 Hz, 1H), 8.35-8.30 (m, 3H), 7.80 (d, J = 9.2 Hz, 1H), 7.48-7.36 (m, 4H), 7.20 (t, J = 7.8 Hz, 1H), 6.96 (s, 1H), 6.89-6.77 (m, 3H), 4.96-4.88 (m, 1H), 4.74-4.69 (m, 1H), 4.51 (d, J = 9.3 Hz, 1H), 4.42 (t, J = 8.0 Hz, 1H), 4.28 (s, 1H), 3.64-3.58 (m, 4H), 3.42-3.30 (m, 1H), 2.47 (s, 3H), 2.39-2.17 (m, 4H), 2.17-1.97 (m, 2H), 1.97-1.69 (m, 3H), 1.64-1.42 (m, 5H), 1.38 (d, J = 7.0 Hz, 3H), 1.13-1.27 (m, 1H), 1.23 (d, J = 6.3 Hz, 3H), 0.93 (s, 9H) |
| H148 | 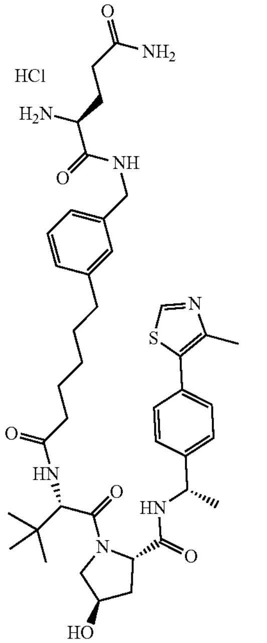 [SMILES: Cc1ncsc1-c1ccc([C@H](C)NC(=O)[C@@H]2C[C@@H](O)CN2C(=O)[C@@H](NC(=O)CCCCCc2cccc(CNC(=O)[C@@H](N)CCC(N)=O)c2)C(C)(C)C)cc1 ; Cl] | (2S)-2-amino-N-[[3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenyl]methyl]pentanediamide hydrochloride | 776.55 | crude used next step without purification |

TABLE 49-continued

Characterization data for intermediates prepared according to procedure above.

| Intermediate | Structure | Chemical Name | MS: [(M + 1)]$^+$ | $^1$H-NMR |
|---|---|---|---|---|
| H149 | 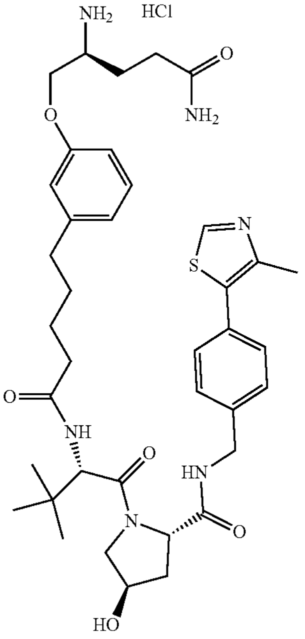 [SMILES: Cl ; Cc1ncsc1-c1ccc(CNC(=O)[C@@H]2C[C@@H](O)CN2C(=O)[C@@H](NC(=O)CCCCc2cccc(OC[C@@H](N)CCC(N)=O)c2)C(C)(C)C)cc1] | (2S,4R)-1-[(2S)-2-(5-[3-[(2S)-2-amino-4-carbamoylbutoxy]phenyl[pentanamido)-3,3-dimethylbutanoyl]-4-hydroxy-N-[[4-(4-methyl-1,3-thiazol-5-yl)phenyl]methyl]pyrrolidine-2-carboxamide hydrochloride | 721.45 | (400 MHz, DMSO-$d_6$) δ 11.97 (s, 1H), 8.99-8.94 (m, 2H), 8.87 (s, 1H), 8.56 (t, J = 6.1 Hz, 1H), 8.09 (d, J = 8.2 Hz, 1H), 7.94 (dd, J = 8.8, 1.6 Hz, 1H), 7.87 (d, J = 9.3 Hz, 1H), 7.42-7.39 (m, 3H), 7.24 (s, 1H), 7.19-7.15 (m, 1H), 7.11-7.08 (m, 1H), 6.99 (t, J = 7.5 Hz, 1H), 6.79-6.69 (m, 1H), 5.09 (dd, J = 10.7, 2.9 Hz, 1H), 4.69 (t, J = 9.4 Hz, 1H), 4.55 (d, J = 9.3 Hz, 1H), 4.48-4.39 (m, 2H), 4.35 (s, 1H), 4.22 (dd, J = 15.8, 5.4 Hz, 1H), 4.02-3.96 (m, 1H), 3.92-3.88 (m, 2H), 3.70-3.61 (m, 2H), 2.88 (d, J = 16.6 Hz, 1H), 2.45 (s, 3H), 2.35-2.33 (m, 1H), 2.32-1.96 (m, 4H), 1.96-1.61 (m, 3H), 1.57-1.47 (m, 3H), 0.94 (s, 9H) |
| H150 | 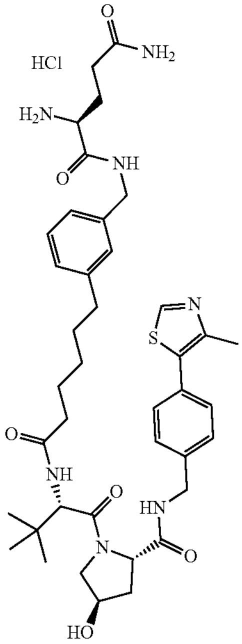 [SMILES: Cc1ncsc1-c1ccc(CNC(=O)[C@@H]2C[C@@H](O)CN2C(=O)[C@@H](NC(=O)CCCCCc2cccc(CNC(=O)[C@@H](N)CCC(N)=O)c2)C(C)(C)C)cc1 ; Cl] | (2S)-2-amino-N-[[3-(5-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]pentyl)phenyl]methyl]pentanediamide hydrochloride | 762.50 | (400 MHz, DMSO-$d_6$) δ 9.06 (s, 1H), 9.02 (t, J = 5.8 Hz, 1H), 8.58 (t, J = 6.1 Hz, 1H), 8.36 (d, J = 14.9 Hz, 2H), 7.85 (d, J = 9.3 Hz, 1H), 7.46-7.38 (m, 4H), 7.24 (t, J = 7.5 Hz, 1H), 7.14-7.07 (m, 2H), 6.95 (s, 1H) 4.54 (d J = 9.2 Hz 1H) 4.48-4.38 (m 1H), 4.33 (dd, J = 11.7, 7.1 Hz, 2H), 4.27-4.18 (m, 1H), 3.93-3.75 (m, 1H), 3.70-3.60 (m, 2H), 2.57-2.54 (m, 2H), 2.46 (s, 3H), 2.34-2.18 (m, 2H), 2.17-1.86 (m, 4H), 1.61-1.45 (m, 4H), 1.27 (dd, J = 14.4, 7.0 Hz, 2H), 0.94 (s, 9H). |

TABLE 49-continued

| Characterization data for intermediates prepared according to procedure above. | | | | |
|---|---|---|---|---|
| Intermediate | Structure | Chemical Name | MS: $[(M + 1)]^+$ | $^1$H-NMR |
| H151 | 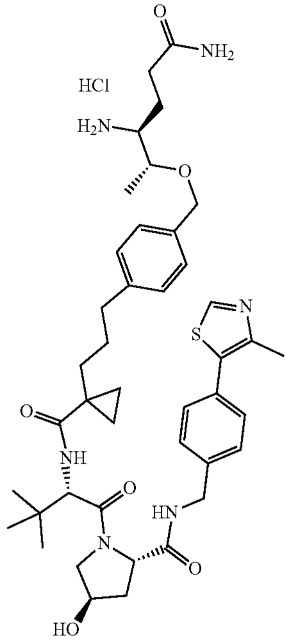 [SMILES: Cc1ncsc1-c1ccc(CNC(=O)[C@@H]2C[C@@H](O)CN2C(=O)[C@@H](NC(=O)C2(CCCc3ccc(CO[C@H](C)[C@@H](N)CCC(N)=O)cc3)CC2)C(C)(C)C)cc1 ; Cl] | (2S,4R)-1-[(2S)-2-[(1-[3-[4-([[(2R,3S)-3-amino-5-carbamoylpentan-2-yl]oxy]methyl)phenyl]propyl]cyclopropyl)formamido]-3,3-dimethylbutanoyl]-4-hydroxy-N-[[4-(4-methyl-1,3-thiazol-5-yl)phenyl]methyl]pyrrolidine-2-carboxamide hydrochloride | 775.50 | crude used next step without purification |
| H152 | 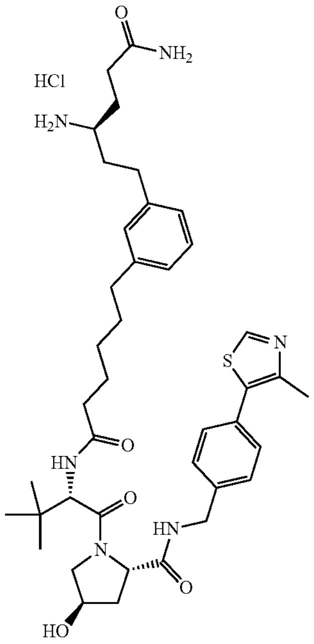 [SMILES: Cc1ncsc1-c1ccc(CNC(=O)[C@@H]2C[C@@H](O)CN2C(=O)[C@@H](NC(=O)CCCCCc2cccc(CC[C@@H](N)CCC(N)=O)c2)C(C)(C)C)cc1 ; Cl] | (2S,4R)-1-[(2S)-2-(6-[3-[(3R)-3-amino-5-carbamoylpentyl]phenyl]hexanamido)-3,3-dimethylbutanoyl]-4-hydroxy-N-[[4-(4-methyl-1,3-thiazol-5-yl)phenyl]methyl]pyrrolidine-2-carboxamide hydrochloride | 733.30 | (400 MHz, DMSO-$d_6$) δ 9.13 (s, 1H), 8.60 (t, J = 6.0 Hz, 1H), 8.22 (s, 2H), 7.85 (d, J = 9.3 Hz, 1H), 7.46-7.38 (m, 4H), 7.19 (t, J = 7.5 Hz, 1H), 7.03 (dd, J = 12.4, 5.3 Hz, 3H), 6.04-5.98 (m, 1H), 4.54 (d, J = 9.4 Hz, 1H), 4.48-4.38 (m, 2H), 4.36 (s, 1H), 4.23 (dd, J = 15.9, 5.3 Hz, 1H), 3.72-3.60 (m, 2H), 3.39 (q, J = 7.0 Hz, 1H) 3.08 (s, 1H), 2.69-2.58 (m, 2H), 2.46 (s, 3H), 2.33-2.18 (m, 3H), 2.17-2.10 (m, 1H), 2.05 (t, J = 10.4 Hz, 1H), 1.96-1.88 (m, 1H), 1.87-1.80 (m, 4H), 1.62-1.43 (m, 5H), 1.33-1.21 (m, 2H), 1.09 (t, J = 7.0 Hz, 2H), 0.93 (s, 9H) |

TABLE 49-continued

| Characterization data for intermediates prepared according to procedure above. | | | | |
|---|---|---|---|---|
| Intermediate | Structure | Chemical Name | MS: $[(M + 1)]^+$ | $^1$H-NMR |
| H153 | 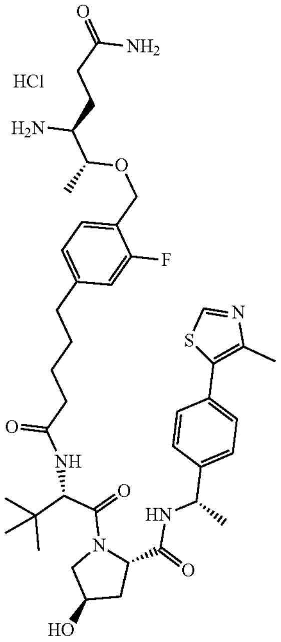 [SMILES: Cc1ncsc1-c1ccc([C@H](C)NC(=O)[C@@H]2C[C@@H](O)CN2C(=O)[C@@H](NC(=O)CCCCc2ccc(CO[C@H](C)[C@@H](N)CCC(N)=O)c(F)c2)C(C)(C)C)cc1 ; Cl] | (2S,4R)-1-[(2S)-2-[5-[4-([[(2R,3S)-3-amino-5-carbamoylpentan-2-yl]oxy]methyl)-3-fluorophenyl]pentanamido]-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride | 781.50 | (400 MHz, DMSO-$d_6$) δ 9.09 (s, 1H), 8.41 (d, J = 7.8 Hz, 1H), 8.14-8.07 (m, 3H), 7.83 (d, J = 9.3 Hz, 1H), 7.49-7.36 (m, 6H), 7.04-7.01 (m, 2H), 6.92 (s, 1H), 4.95-4.90 (m, 1H), 4.63-4.46 (m, 3H), 4.43 (t, J = 8.0 Hz, 1H), 4.28 (s, 1H), 3.84-3.79 (m, 1H), 3.66-3.59 (m, 2H), 3.26 (s, 1H), 2.59 (t, J = 7.2 Hz, 1H), 2.47 (s, 3H), 2.36-2.20 (m, 3H), 2.20-2.09 (m, 1H), 2.05-2.00 (m, 1H), 1.85-1.68 (m, 4H), 1.58-1.41 (m, 4H), 1.38 (d, J = 7.0 Hz, 3H), 1.16 (d, J = 6.3 Hz, 3H), 0.94 (s, 9H) |
| H154 | 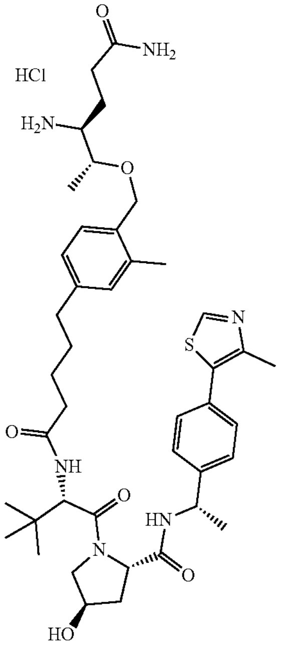 [SMILES: Cc1cc(CCCCC(=O)N[C@H](C(=O)N2C[C@H](O)C[C@H]2C(=O)N[C@@H](C)c2ccc(-c3scnc3C)cc2)C(C)(C)C)ccc1CO[C@H](C)[C@@H](N)CCC(N)=O ; Cl] | (2S,4R)-1-[(2S)-2-[5-[4-([[(2R,3S)-3-amino-5-carbamoylpentan-2-yl]oxy]methyl)-3-methylphenyl]pentanamido]-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride | 777.30 | (400 MHz, DMSO-$d_6$) δ 9.18 (s, 1H), 8.43 (d, J = 7.8 Hz, 1H), 8.14 (d, J = 10.9 Hz, 2H), 7.82 (d, J = 9.2 Hz, 1H), 7.48-7.44 (m, 3H), 7.40 (d, J = 8.3 Hz, 2H), 7.27 (d, J = 7.6 Hz, 2H), 6.99-6.97 (d, J = 10.0 Hz, 3H), 4.92 (p, J = 6.9 Hz, 1H), 4.52 (dd, J = 10.5, 5.3 Hz, 2H), 4.46-4.40 (m, 2H), 4.29-4.27 (m, 1H), 3.87-3.72 (m, 2H), 3.38 (q, J = 7.0 Hz, 1H), 3.26-3.24 (m, 1H), 2.48 (s, 3H), 2.34-2.24 (m, 4H), 2.15 (dd, J = 13.5, 6.4 Hz, 1H), 2.02 (t, J = 10.3 Hz, 1H), 1.82-1.75 (m, 3H), 1.60 (s, 3H), 1.52 (s, 3H), 1.38 (d, J = 7.0 Hz, 3H), 1.16 (d, J = 6.3 Hz, 3H), 1.09 (t, J = 7.0 Hz, 2H), 0.94 (s, 9H) |

TABLE 49-continued

Characterization data for intermediates prepared according to procedure above.

| Intermediate | Structure | Chemical Name | MS: [(M + 1)]+ | 1H-NMR |
|---|---|---|---|---|
| H155 | 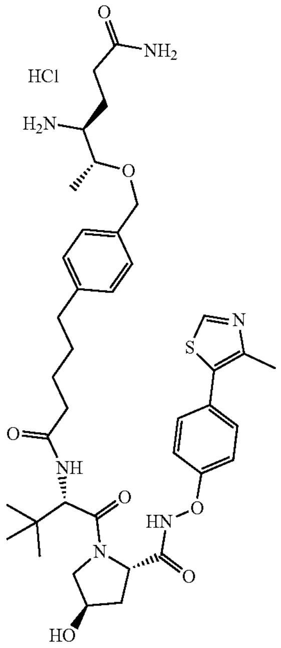 [SMILES: Cc1ncsc1-c1ccc(ONC(=O)[C@@H]2C[C@@H](O)CN2C(=O)[C@@H](NC(=O)CCCCc2ccc(CO[C@H](C)[C@@H](N)CCC(N)=O)cc2)C(C)(C)C)cc1 ; Cl] | (2S,4R)-1-[(2S)-2-[5-[4-([[(2R,3S)-3-amino-5-carbamoylpentan-2-yl]oxy]methyl)phenyl]pentanamido]-3,3-dimethylbutanoyl]-4-hydroxy-N-[4-(4-methyl-1,3-thiazol-5-yl)phenoxy]pyrrolidine-2-carboxamide hydrochloride | 751.55 | (400 MHz, Methanol-$d_4$) δ 9.90 (d, J = 8.1 Hz, 1H), 7.54 (d, J = 8.4 Hz, 2H), 7.42 (d, J = 8.5 Hz, 2H), 7.31 (d, J = 7.7 Hz, 2H), 7.21 (d, J = 7.6 Hz, 2H), 4.64 (t, J = 5.9 Hz, 2H), 4.57 (s, 1H), 4.52 (d, J = 11.6 Hz, 1H), 3.96 (d, J = 11.0 Hz, 1H), 3.83 (t, J = 6.2 Hz, 2H), 3.72-3.66 (m, 6H), 3.36-3.34 (m, 1H) 2.66 (s, 1H), 2.60 (s, 2H), 2.49-2.40 (m, 2H), 2.30 (d, J = 18.7 Hz, 2H), 1.90 (m, 2H), 1.66 (s, 3H), 1.25 (d, J = 6.3 Hz, 3H), 1.05 (s, 9H) |
| H156 | 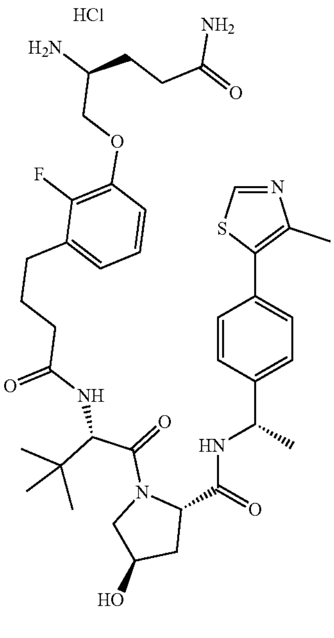 [SMILES: Cl ; Cc1ncsc1-c1ccc([C@H](C)NC(=O)[C@@H]2C[C@@H](O)CN2C(=O)[C@@H](NC(=O)CCCc2cccc(OC[C@@H](N)CCC(N)=O)c2F)C(C)(C)C)cc1] | (2S,4R)-1-[(2S)-2-(4-[3-[(2S)-2-amino-4-carbamoylbutoxy]-2-fluorophenyl]butanamido)-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride | 739.20 | (400 MHz, DMSO-$d_6$) δ 9.04-9.02 (m, 1H), 8.40 (d, J = 7.8 Hz, 1H), 8.36-8.33 (m, 1H), 8.32-8.27 (m, 2H), 7.89 (d, J = 9.2 Hz, 1H), 7.45 (d, J = 8.3 Hz, 2H), 7.39 (d, J = 8.4 Hz, 2H), 7.09-7.05 (m, 2H), 6.98-6.95 (m, 1H), 6.92-6.86 (m, 1H), 4.92-4.91 (m, 2H), 4.53 (d, J = 9.3 Hz, 1H), 4.44-4.42 (m, 1H), 4.32-4.28 (m, 1H), 4.25-4.21 (m, 1H), 4.15-4.11 (m, 1H), 3.62-3.60 (m, 2H), 2.63-2.58 (m, 2H), 2.50-2.45 (m, 3H), 2.31-2.28 (m, 4H), 2.21-2.18 (m, 1H), 2.04-2.02 (m, 1H), 1.93-1.90 (m, 2H), 1.85-1.72 (m, 4H), 1.38 (d, J = 7.0 Hz, 3H), 0.95 (s, 9H) |

TABLE 49-continued

| Characterization data for intermediates prepared according to procedure above. | | | | |
|---|---|---|---|---|
| Intermediate | Structure | Chemical Name | MS: $[(M + 1)]^+$ | $^1$H-NMR |
| H157 | 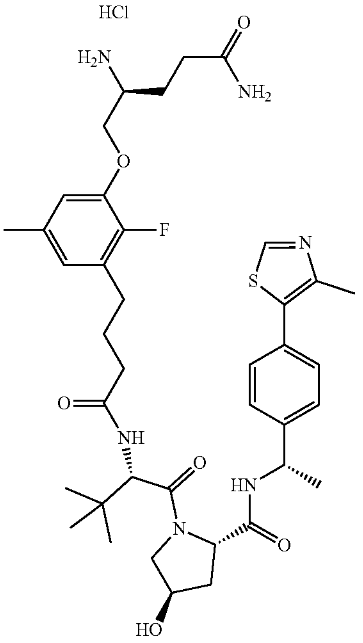 | (2S,4R)-1-[(2S)-2-(4-[3-[(2S)-2-amino-4-carbamoylbutoxy]-2-fluoro-5-methylphenyl]butanamido)-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride | 753.35 | (400 MHz, DMSO-$d_6$) δ 9.12 (s, 1H), 8.48-8.34 (m, 3H), 7.87 (d, J = 9.2 Hz, 1H), 7.48-7.37 (m, 5H), 7.00-6.84 (m, 2H), 6.67 (d, J = 5.9 Hz, 1H), 4.96-4.88 (m, 1H), 4.53 (d, J = 9.2 Hz, 1H), 4.43 (t, J = 8.0 Hz, 1H), 4.28 (s, 1H), 4.24-4.17 (m, 1H), 4.17-4.09 (m, 1H), 2.60-2.53 (m, 2H), 2.47 (s, 3H), 2.37-2.28 (m, 2H), 2.26 (s, 3H), 2.22-2.12 (m, 1H), 2.07-1.98 (m, 1H), 1.91 (q, J = 6.9 Hz, 2H), 1.81-1.72 (m, 8H), 1.38 (s, 3H), 0.95 (s, 9H) |
| H158 | 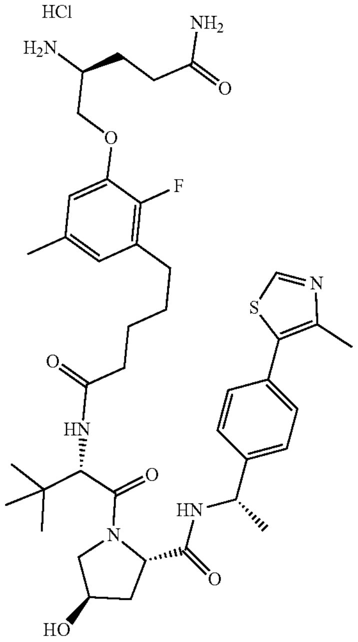 [SMILES: Cl ; Cc1cc(CCCCC(=O)N[C@H](C(=O)N2C[C@H](O)C[C@H]2C(=O)N[C@@H](C)c2ccc(-c3scnc3C)cc2)C(C)(C)C)c(F)c(OC[C@@H](N)CCC(N)=O)c1] | (2S,4R)-1-[(2S)-2-(5-[3-[(2S)-2-amino-4-carbamoylbutoxy]-2-fluoro-5-methylphenyl]pentanamido)-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride | 767.40 | (300 MHz, DMSO-$d_6$) δ 9.07 (s, 1H), 8.42-8.32 (m, 3H), 7.80 (d, J = 9.3 Hz, 1H), 7.50-7.40 (m, 3H), 7.40-7.27 (m, 2H), 6.99-6.80 (m, 2H), 6.72-6.64 (m, 1H), 4.91 (p, J = 7.2 Hz, 1H), 4.50 (d, J = 9.2 Hz, 1H), 4.41 (t, J = 8.0 Hz, 1H), 4.27 (s, 1H), 4.19 (dd, J = 10.6, 3.6 Hz, 1H), 4.10 (dd, J = 10.6, 6.1 Hz, 1H), 2.46 (s, 3H), 2.36-2.28 (m, 2H), 2.24 (s, 3H), 2.22-2.08 (m, 2H), 2.06-1.83 (m, 4H), 1.78-1.71 (m, 5H), 1.54-1.45 (m, 5H), 1.37 (s, 3H), 0.92 (s, 9H) |

TABLE 49-continued

| Characterization data for intermediates prepared according to procedure above. | | | | |
|---|---|---|---|---|
| Intermediate | Structure | Chemical Name | MS: $[(M + 1)]^+$ | $^1$H-NMR |
| H159 | 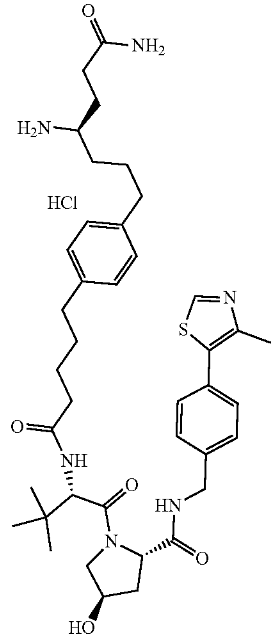 [SMILES: Cc1ncsc1-c1ccc(CNC(=O)[C@@H]2C[C@@H](O)CN2C(=O)[C@@H](NC(=O)CCCCc2ccc(CCC[C@@H](N)CCC(N)=O)cc2)C(C)(C)C)cc1 ; Cl] | (2S,4R)-1-[(2S)-2-(5-[4-[(4R)-4-amino-6-carbamoylhex-yl]phenyl]pentan-amido)-3,3-dimethylbutanoyl]-4-hydroxy-N-[(1S)-1-[4-(4-methyl-1,3-thiazol-5-yl)phenyl]eth-yl]pyrrolidine-2-carboxamide hydrochloride | 747.45 | (300 MHz, DMSO-$d_6$) δ 9.03 (s, 1H), 8.40 (d, J = 7.7 Hz, 1H), 8.02-7.78 (m, 4H), 7.53-7.31 (m, 5H), 7.12 (s, 4H), 4.99-4.88 (m, 1H), 4.55-4.38 (m, 2H), 4.30 (s, 1H), 3.18-3.01 (m, 2H), 2.50-2.37 (m, 5H), 2.35-1.97 (m, 6H), 1.90-1.69 (m, 4H), 1.69-1.45 (m, 10H), 1.39 (d, J = 6.9 Hz, 3H), 0.95 (s, 9H) |
| H160 | 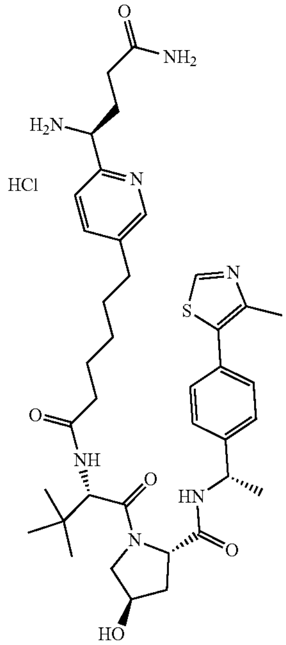 [SMILES: Cl ; Cc1ncsc1-c1ccc([C@H](C)NC(=O)[C@@H]2C[C@@H](O)CN2C(=O)[C@@H](NC(=O)CCCCCc2ccc([C@@H](N)CCC(N)=O)nc2)C(C)(C)C)cc1] | (2S,4R)-1-[(2S)-2-(6-[6-[(1S)-1-amino-3-carbamoylpro-pyl]pyridin-3-yl]hexanamido)-3,3-dimethylbutanoyl]-4-hydroxy-N-[(1S)-1-[4-(4-methyl-1,3-thiazol-5-yl)phenyl]eth-yl]pyrrolidine-2-carboxamide hydrochloride | 720.45 | (300 MHz, DMSO-$d_6$) δ 9.12 (s, 1H), 9.07 (s, 3H), 9.02-9.01 (d, J = 2.0 Hz, 1H), 8.76-8.73 (dd, J = 8.4, 2.0 Hz, 1H), 8.46-8.44 (d, J = 7.8 Hz, 1H), 8.08-8.06 (d, J = 8.4 Hz, 1H), 7.85-7.83 (d, J = 9.3 Hz, 1H), 7.50-7.44 (d, J = 8.1 Hz, 2H), 7.41-7.36 (d, J = 8.3 Hz, 2H), 6.85 (s, 1H), 4.96-4.88 (m, 1H), 4.58 (s, 1H), 4.53-4.51 (d, J = 9.4 Hz, 1H), 4.45-4.41 (t, J = 8.1 Hz, 1H), 4.29-4.27 (m, 1H), 3.61-3.60 (d, J = 3.3 Hz, 2H), 3.57 (s, 7H), 3.08-3.05 (t, J = 7.8 Hz, 2H), 2.47 (s, 3H), 2.36-2.11 (m, 2H), 2.08-1.97 (m, 2H), 1.80-1.75 (m, 3H), 1.62-1.44 (m, 2H), 1.39 (s, 1H), 1.37 (s, 1H), 0.94 (s, 9H) |

TABLE 49-continued

Characterization data for intermediates prepared according to procedure above.

| Intermediate | Structure | Chemical Name | MS: [(M + 1)]+ | 1H-NMR |
|---|---|---|---|---|
| H161 | HCl 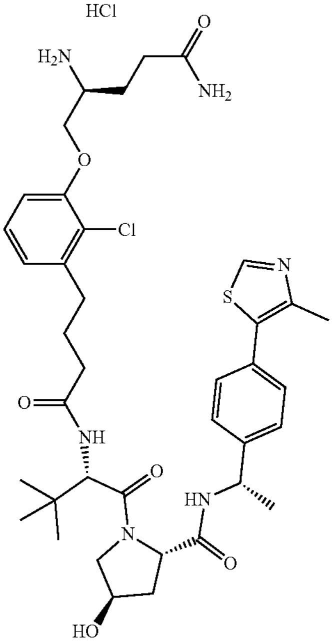 [SMILES: Cl ; Cc1ncsc1-c1ccc([C@H](C)NC(=O)[C@@H]2C[C@@H](O)CN2C(=O)[C@@H](NC(=O)CCCc2cccc(OC[C@@H](N)CCC(N)=O)c2Cl)C(C)(C)C)cc1] | (2S,4R)-1-[(2S)-2-(4-[3-[(2S)-2-amino-4-carbamoylbutoxy]-2-chlorophenyl]butanamido)-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride | 755.30 | (400 MHz, DMSO-$d_6$) δ 9.03 (s, 1H), 8.40 (d, J = 7.9 Hz, 1H), 8.27 (s, 2H), 7.89 (d, J = 9.1 Hz, 1H), 7.45 (d, J = 8.3 Hz, 2H), 7.39 (d, J = 8.2 Hz, 2H), 7.26 (t, J = 7.9 Hz, 1H), 7.06 (d, J = 8.1 Hz, 1H), 6.97 (d, J = 8.2 Hz, 1H), 4.96-4.88 (m, 1H), 4.71-4.60 (m, 1H), 4.57-4.49 (m, 1H), 4.43 (t, J = 7.9 Hz, 1H), 4.28 (s, 1H), 4.26-4.17 (m, 1H), 4.15-4.11 (m, 1H), 3.76-3.63 (m, 1H), 3.60 (d, J = 3.6 Hz, 2H), 3.53-3.45 (m, 1H), 3.46-3.37 (m, 1H), 2.71 (d, J = 7.8 Hz, 1H), 2.46 (s, 3H), 2.32-2.28 (m, 1H), 2.22-2.18 (m, 1H), 1.99-1.95 (m, 2H), 1.84-1.75 (m, 4H), 1.68-1.58 (m, 1H), 1.55-1.45 (m, 1H), 1.38 (d, J = 7.0 Hz, 3H), 1.24 (s, 1H), 0.95 (s, 9H) |
| H162 | HCl 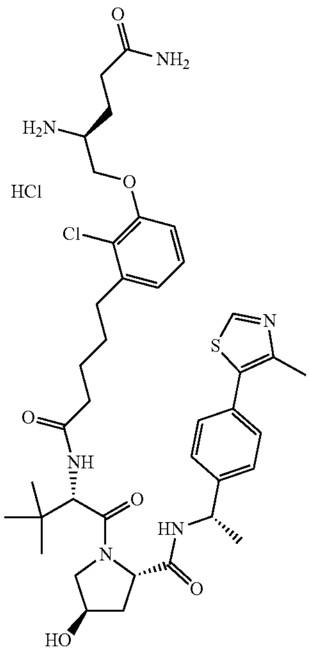 [SMILES: Cc1ncsc1-c1ccc([C@H](C)NC(=O)[C@@H]2C[C@@H](O)CN2C(=O)[C@@H](NC(=O)CCCCc2cccc(OC[C@@H](N)CCC(N)=O)c2Cl)C(C)(C)C)cc1 ; Cl] | (2S,4R)-1-[(2S)-2-(5-[3-[(2S)-2-amino-4-carbamoylbutoxy]-2-chlorophenyl]pentanamido)-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride | 769.25 | (400 MHz, DMSO-$d_6$) δ 9.06 (s, 1H), 8.41 (d, J = 7.7 Hz, 1H), 8.36 (s, 2H), 7.84 (d, J = 9.3 Hz, 1H), 7.45 (d, J = 8.3 Hz, 2H), 7.39 (d, J = 8.3 Hz, 2H), 7.25 (t, J = 7.9 Hz, 1H), 7.05 (dd, J = 8.3, 1.4 Hz, 1H), 7.02-6.96 (m, 1H), 4.93 (p, J = 7.0 Hz, 1H), 4.52 (d, J = 9.3 Hz, 1H), 4.43 (t, J = 8.0 Hz, 1H), 4.31-4.20 (m, 1H), 4.15 (dd, J = 10.5, 5.6 Hz, 1H), 3.69-3.57 (m, 3H), 2.70 (d, J = 7.1 Hz, 2H), 2.47 (s, 3H), 2.41-2.23 (m, 2H), 2.23-2.11 (m, 1H), 2.07-1.91 (m, 4H), 1.85-1.72 (m, 3H), 1.63-1.60 (m, 1H), 1.59-1.51 (m, 5H), 1.38 (d, J = 7.0 Hz, 3H), 0.94 (s, 9H) |

TABLE 49-continued

Characterization data for intermediates prepared according to procedure above.

| Intermediate | Structure | Chemical Name | MS: $[(M+1)]^+$ | $^1$H-NMR |
|---|---|---|---|---|
| H163 | 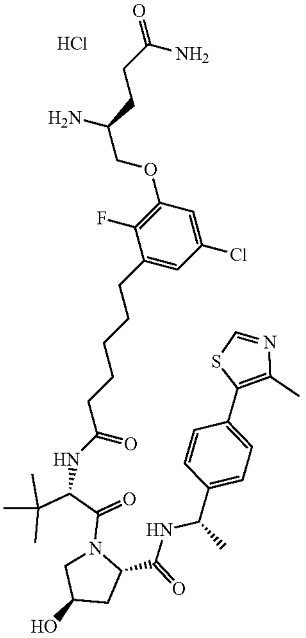 [SMILES: Cc1ncsc1-c1ccc([C@H](C)NC(=O)[C@@H]2C[C@@H](O)CN2C(=O)[C@@H](NC(=O)CCCCCc2cc(Cl)cc(OC[C@@H](N)CCC(N)=O)c2F)C(C)(C)C)cc1 ; Cl] | (2S,4R)-1-[(2S)-2-(6-[3-[(2S)-2-amino-4-carbamoylbutoxy]-5-chloro-2-fluorophenyl]hexanamido)-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride | 801.35 | used next step directly without purification |
| H164 | 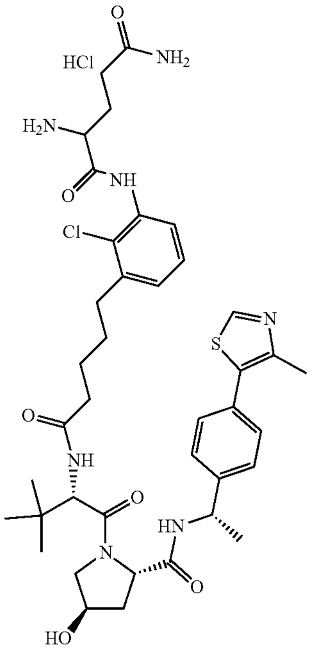 [SMILES: Cc1ncsc1-c1ccc([C@H](C)NC(=O)[C@@H]2C[C@@H](O)CN2C(=O)[C@@H](NC(=O)CCCCc2cccc(NC(=O)C(N)CCC(N)=O)c2Cl)C(C)(C)C)cc1 ; Cl] | 2-amino-N-[2-chloro-3-(4-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]butyl)phenyl]pentanediamide hydrochloride | 782.25 | (300 MHz, DMSO-$d_6$) δ 10.23 (s, 1H), 9.04 (s, 1H), 8.45 (s, 2H), 8.38 (d, J = 7.7 Hz, 1H), 7.81 (d, J = 9.2 Hz, 1H), 7.61 (dd, J = 11.4, 7.0 Hz, 1H), 7.60-7.42 (m, 2H), 7.45-7.26 (m, 2H), 7.29-7.16 (m, 1H), 6.96 (s, 1H), 4.91 (t, J = 7.2 Hz, 1H), 4.51 (d, J = 9.3 Hz, 1H), 4.42 (t, J = 8.0 Hz, 1H), 4.27 (s, 1H), 4.17 (s, 1H), 3.68-3.58 (m, 4H), 2.74-2.70 (m, 2H), 2.45 (s, 3H), 2.34-2.30 (m, 3H), 2.22-2.03 (m, 3H), 2.01-1.97 (m, 1H), 1.86-1.71 (m, 2H), 1.56-1.52 (m, 4H), 1.37 (d, J = 7.0 Hz, 3H), 0.93 (s, 9H) |

TABLE 49-continued

Characterization data for intermediates prepared according to procedure above.

| Intermediate | Structure | Chemical Name | MS: $[(M + 1)]^+$ | $^1$H-NMR |
|---|---|---|---|---|
| H165 | HCl 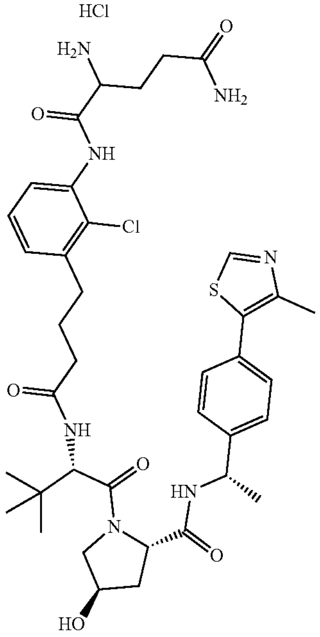 [SMILES: Cl ; Cc1ncsc1-c1ccc([C@H](C)NC(=O)[C@@H]2C[C@@H](O)CN2C(=O)[C@@H](NC(=O)CCCc2cccc(NC(=O)C(N)CCC(N)=O)c2Cl)C(C)(C)C)cc1] | (2S)-2-amino-N-[2-chloro-3-(3-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]propyl)phenyl]pentanediamide hydrochloride | 768.25 | (400 MHz, DMSO-$d_6$) δ 10.26 (s, 1H), 9.03 (s, 1H), 8.41 (d, J = 7.8 Hz, 1H), 7.91 (d, J = 9.2 Hz, 1H), 7.53 (d, J = 8.2 Hz, 2H), 7.45 (d, J = 8.2 Hz, 2H), 7.27 (s, 2H), 7.15 (s, 2H), 6.99 (s, 1H), 4.93 (p, J = 7.3 Hz, 1H), 4.54 (d, J = 9.2 Hz, 1H), 4.43 (t, J = 8.0 Hz, 1H), 4.29 (s, 1H), 4.17 (d, J = 6.5 Hz, 1H), 3.67-3.58 (m, 1H), 2.72 (t, J = 7.3 Hz, 2H), 2.47 (s, 3H), 2.33 (q, J = 7.4 Hz, 3H), 2.23-2.19 (m, 1H), 2.10-2.06 (m, 3H), 1.80-1.76 (m, 4H), 1.85-1.73 (m, 2H), 1.62-1.58 (m, 1H), 1.38 (d, J = 7.0 Hz, 3H), 0.95 (s, 9H) |
| H166 | HCl 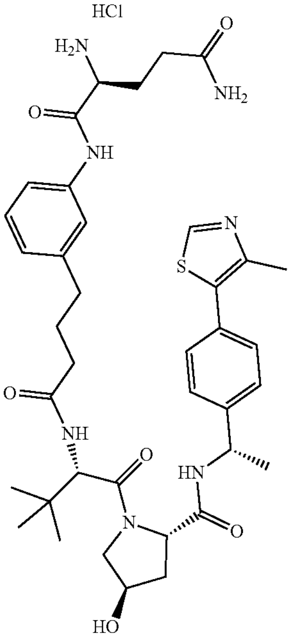 [SMILES: Cl ; Cc1ncsc1-c1ccc([C@H](C)NC(=O)[C@@H]2C[C@@H](O)CN2C(=O)[C@@H](NC(=O)CCCc2cccc(NC(=O)[C@@H](N)CCC(N)=O)c2)C(C)(C)C)cc1] | (2S)-2-amino-N-[3-(3-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]propyl)phenyl]pentanediamide hydrochloride | 734.30 | (400 MHz, DMSO-$d_6$) δ 10.88 (s, 1H), 9.03 (s, 1H), 8.49 (s, 3H), 8.15 (s, 1H), 7.87 (d, J = 9.2 Hz, 1H), 7.56-7.46 (m, 3H), 7.44 (d, J = 7.9 Hz, 2H), 7.39 (d, J = 8.2 Hz, 2H), 7.25 (t, J = 7.8 Hz, 1H), 6.94 (d, J = 7.2 Hz, 2H), 4.92 (p, J = 7.2 Hz, 1H), 4.53 (d, J = 9.2 Hz, 1H), 4.43 (t, J = 8.0 Hz, 1H), 4.28-3.61 (m, 3H), 2.54-2.51 (m, 1H), 2.46 (s, 3H), 2.34-2.14 (m, 4H), 2.12-1.98 (m, 4H), 1.79-1.75 (m, 4H), 1.38-1.33 (m, 3H), 0.95 (s, 9H) |

TABLE 49-continued

| Characterization data for intermediates prepared according to procedure above. | | | | |
|---|---|---|---|---|
| Intermediate | Structure | Chemical Name | MS: [(M + 1)]$^+$ | $^1$H-NMR |
| H167 | 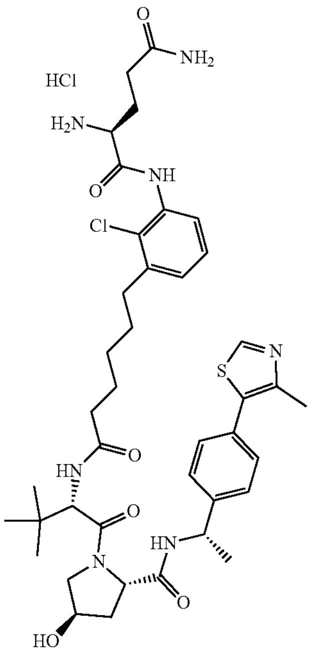 [SMILES: Cc1ncsc1-c1ccc([C@H](C)NC(=O)[C@@H]2C[C@@H](O)CN2C(=O)[C@@H](NC(=O)CCCCCc2cccc(NC(=O)[C@@H](N)CCC(N)=O)c2Cl)C(C)(C)C)cc1 ; Cl] | (2S)-2-amino-N-[2-chloro-3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenyl]pentanediamide hydrochloride | 796.35 | (300 MHz, DMSO-$d_6$) δ 10.30 (s, 1H), 9.10 (s, 1H), 8.61-8.32 (m, 5H), 7.82 (d, J = 9.1 Hz, 1H), 7.54-7.39 (m, 6H), 7.34-7.22 (m, 2H), 6.99 (s, 1H), 4.93 (t, J = 7.2 Hz, 1H), 4.53 (d, J = 9.2 Hz, 1H), 4.44 (t, J = 8.0 Hz, 1H), 4.30 (s, 1H), 4.23-4.17 (m, 2H), 3.62 (s, 2H), 2.73 (t, J = 7.8 Hz, 2H), 2.48 (s, 3H), 2.41-2.22 (m, 2H), 2.21-1.98 (m, 4H), 1.84-1.77 (m, 1H), 1.66-1.44 (m, 4H), 1.39 (d, J = 6.9 Hz, 3H), 1.36-1.19 (m, 1H), 0.95 (s, 9H) |
| H168 | 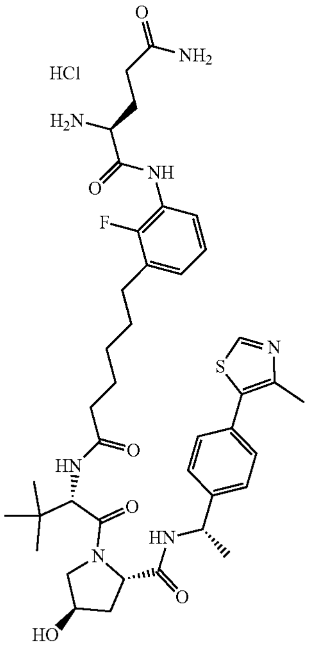 [SMILES: Cc1ncsc1-c1ccc([C@H](C)NC(=O)[C@@H]2C[C@@H](O)CN2C(=O)[C@@H](NC(=O)CCCCCc2cccc(NC(=O)[C@@H](N)CCC(N)=O)c2F)C(C)(C)C)cc1 ; Cl] | (2S)-2-amino-N-[2-fluoro-3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenyl]pentanediamide hydrochloride | 780.40 | (300 MHz, DMSO-$d_6$) δ 10.45 (s, 1H), 9.09 (s, 1H), 8.57-8.35 (m, 4H), 7.81 (d, J = 9.3 Hz, 1H), 7.73-7.68 (m, 1H), 7.55 (s, 1H), 7.43 (q, J = 8.3 Hz, 4H), 7.12 (d, J = 6.4 Hz, 2H), 6.99 (s, 1H), 4.98-4.88 (m, 1H), 4.52 (d, J = 9.3 Hz, 1H), 4.44 (t, J = 8.0 Hz, 1H), 4.29 (s, 1H), 4.17 (s, 1H), 2.62 (t, J = 7.4 Hz, 2H), 2.48 (s, 3H), 2.34-2.23 (m, 3H), 2.19-1.97 (m, 5H), 1.88-1.72 (m, 1H), 1.65-1.44 (m, 5H), 1.39 (d, J = 7.0 Hz, 3H), 1.35-1.18 (m, 2H), 0.94 (s, 9H) |

TABLE 49-continued

| Characterization data for intermediates prepared according to procedure above. | | | | |
|---|---|---|---|---|
| Intermediate | Structure | Chemical Name | MS: [(M + 1)]$^+$ | $^1$H-NMR |
| H169 | 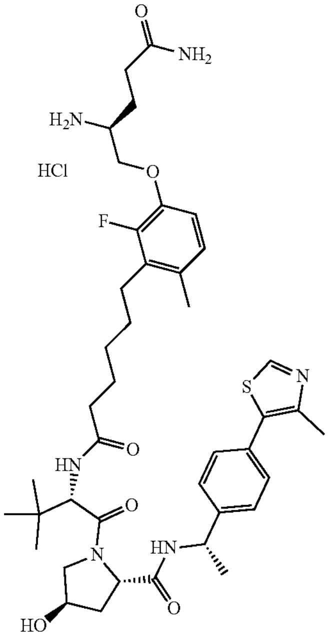 [SMILES: Cc1ccc(OC[C@@H](N)CCC(N)=O)c(F)c1CCCCCC(=O)N[C@H](C(=O)N1C[C@H](O)C[C@H]1C(=O)N[C@@H](C)c1ccc(-c2scnc2C)cc1)C(C)(C)C ; Cl] | (2S,4R)-1-[(2S)-2-(6-[3-[(2S)-2-amino-4-carbamoylbutoxy]-2-fluoro-6-methylphenyl]hexanamido)-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride | 781.35 | (400 MHz, DMSO-$d_6$) δ 9.07 (s, 1H), 8.41 (d, J = 7.8 Hz, 1H), 8.33 (s, 2H), 7.81 (d, J = 9.2 Hz, 1H), 7.48-7.42 (m, 2H), 7.42-7.32 (m, 2H), 6.94 (d, J = 6.7 Hz, 2H), 4.92 (p, J = 7.3 Hz, 1H), 4.52 (d, J = 9.3 Hz, 1H), 4.42 (t, J = 8.0 Hz, 1H), 4.28 (s, 1H), 4.18 (dd, J = 10.5, 3.6 Hz, 1H), 4.11-4.07 (m, 1H), 3.67-3.60 (m, 2H), 2.65-2.53 (m, 2H), 2.47 (s, 3H), 2.39-2.26 (m, 2H), 2.23 (s, 3H), 2.18-1.97 (m, 2H), 1.96-1.85 (m, 2H), 1.85-1.76 (m, 2H), 1.75-1.71 (m, 1H), 1.60 (s, 3H), 1.55-1.42 (m, 5H), 1.41-1.27 (m, 4H), 0.93 (s, 9H) |
| H170 | 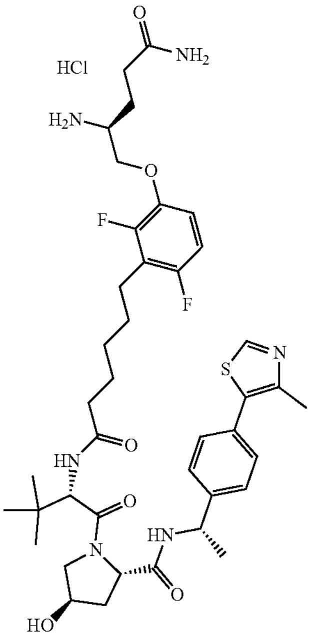 [SMILES: Cc1ncsc1-c1ccc([C@H](C)NC(=O)[C@@H]2C[C@@H](O)CN2C(=O)[C@@H](NC(=O)CCCCCc2c(F)ccc(OC[C@@H](N)CCC(N)=O)c2F)C(C)(C)C)cc1 ; Cl] | (2S,4R)-1-[(2S)-2-(6-[3-[(2S)-2-amino-4-carbamoylbutoxy]-2,6-difluorophenyl]hexanamido)-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride | 785.35 | (400 MHz, DMSO-$d_6$) δ 9.12 (s, 1H), 8.41 (s, 1H), 7.80 (d, J = 9.3 Hz, 1H), 7.48-7.37 (m, 4H), 7.37-7.31 (m, 1H), 7.13 (td, J = 9.3, 5.3 Hz, 1H), 7.01 (td, J = 9.2, 1.8 Hz, 1H), 6.94 (s, 1H), 4.92 (p, J = 7.1 Hz, 1H), 4.51 (d, J = 9.3 Hz, 1H), 4.42 (t, J = 8.0 Hz, 1H), 4.28 (s, 1H), 4.22 (dd, J = 10.4, 3.6 Hz, 1H), 4.14 (dd, J = 10.5, 6.1 Hz, 1H), 3.67-3.60 (m, 2H), 2.61 (s, 2H), 2.47 (s, 3H), 2.39-2.20 (m, 3H), 2.16-1.98 (m, 1H), 1.98-1.84 (m, 2H), 1.81-1.78 (m, 2H), 1.60 (s, 3H), 1.54-1.44 (m, 5H), 1.38 (d, J = 6.9 Hz, 3H), 1.30-1.26 (m, 2H), 0.92 (s, 9H) |

TABLE 49-continued

| Characterization data for intermediates prepared according to procedure above. | | | | |
|---|---|---|---|---|
| Intermediate | Structure | Chemical Name | MS: [(M + 1)]$^+$ | $^1$H-NMR |
| H171 | 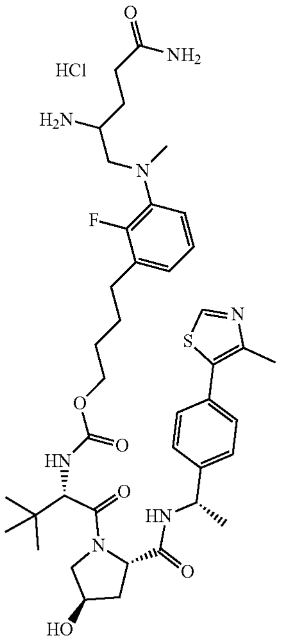 [SMILES: Cc1ncsc1-c1ccc([C@H](C)NC(=O)[C@@H]2C[C@@H](O)CN2C(=O)[C@@H](NC(=O)OCCCCc2cccc(N(C)CC(N)CCC(N)=O)c2F)C(C)(C)C)cc1 ; Cl] | 4-[3-[(2-amino-4-carbamoylbutyl)(methyl)amino]-2-fluorophenyl]butyl N-[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamate hydrochloride | 782.35 | (400 MHz, DMSO-d$_6$) δ 9.14 (s, 1H), 8.44 (d, J = 7.7 Hz, 1H), 8.15 (s, 2H), 7.50-7.33 (m, 4H), 7.06-6.94 (m, 2H), 6.95-6.84 (m, 2H), 4.91 (p, J = 7.1 Hz, 1H), 4.45 (t, J = 8.0 Hz, 1H), 4.28 (s, 1H), 4.17 (d, J = 9.1 Hz, 1H), 4.00-3.96 (m, 2H), 3.69-3.59 (m, 4H), 3.45-3.34 (m, 2H), 3.14 (d, J = 8.7 Hz, 2H), 2.76 (s, 3H), 2.63-2.59 (m, 2H), 2.48 (s, 3H), 2.31-2.27 (m, 2H), 2.05-2.01 (m, 1H), 1.91-1.71 (m, 4H), 1.60 (s, 3H), 1.38 (d, J = 7.0 Hz, 3H), 0.94 (s, 9H) |
| H172 | 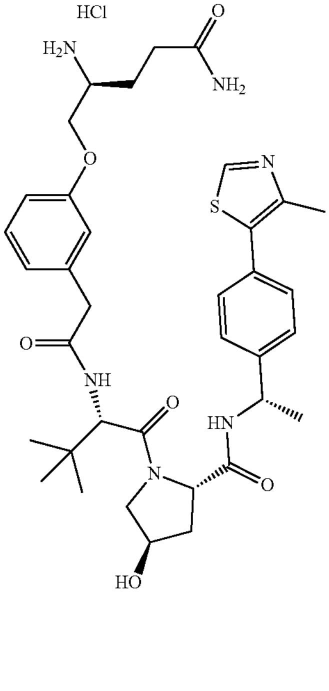 [SMILES: Cc1ncsc1-c1ccc([C@H](C)NC(=O)[C@@H]2C[C@@H](O)CN2C(=O)[C@@H](NC(=O)Cc2cccc(OC[C@@H](N)CCC(N)=O)c2)C(C)(C)C)cc1 ; Cl] | (2S,4R)-1-[(2S)-2-(2-[3-[(2S)-2-amino-4-carbamoylbutoxy]phenyl]acetamido)-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride | 693.35 | (300 MHz, DMSO-d$_6$) δ 9.19 (s, 1H), 8.45 (d, J = 10.0 Hz, 3H), 8.02 (d, J = 9.2 Hz, 1H), 7.45-7.38 (m, 4H), 7.22 (t, J = 7.8 Hz, 1H), 6.98-6.76 (m, 4H), 4.92-7.88 (m, 1H), 4.59-4.33 (m, 2H), 4.33-3.89 (m, 3H), 3.51-3.30 (m, 3H), 2.47 (s, 3H), 2.28-2.21 (m, 2H), 2.10-1.69 (m, 4H), 1.41-1.35 (m, 3H), 0.91 (s, 9H) |

TABLE 49-continued

| Characterization data for intermediates prepared according to procedure above. | | | | |
|---|---|---|---|---|
| Intermediate | Structure | Chemical Name | MS: [(M + 1)]$^+$ | $^1$H-NMR |
| H173 | 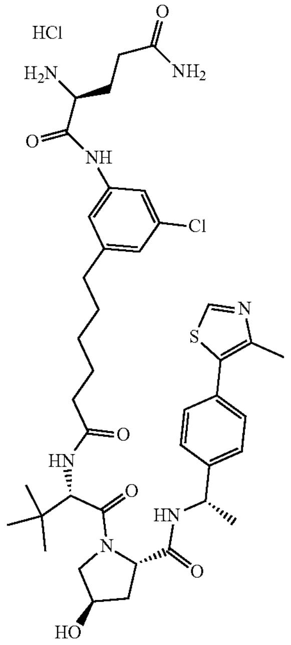 [SMILES: Cc1ncsc1-c1ccc([C@H](C)NC(=O)[C@@H]2C[C@@H](O)CN2C(=O)[C@@H](NC(=O)CCCCCc2cc(Cl)cc(NC(=O)[C@@H](N)CCC(N)=O)c2)C(C)(C)C)cc1 ; Cl] | (2S)-2-amino-N-[3-chloro-5-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenyl]pentanediamide hydrochloride | [(M − 1)]$^-$ = 794.55 | (300 MHz, DMSO-d$_6$) δ 11.05 (s, 1H), 9.04 (s, 1H), 8.44 (s, 1H), 8.40 (d, J = 7.9 Hz, 2H), 7.81 (d, J = 9.3 Hz, 1H), 7.69 (d, J = 2.0 Hz, 1H), 7.48-7.35 (m, 5H), 7.05 (d, J = 1.9 Hz, 1H), 6.96 (s, 1H), 4.95-4.80 (m, 3H) 4.53 (d, J = 9.4 Hz, 1H), 4.44 (t, J = 8.0 Hz, 1H), 4.29 (s, 1H), 4.07 (s, 1H), 3.61 (s, 2H), 2.58 (d, J = 7.4 Hz, 2H), 2.47 (s, 3H), 2.27 (t, J = 7.9 Hz, 3H), 2.18-2.01 (m, 4H), 1.82-1.73 (m, 1H), 1.60-1.44 (m, 4H), 1.39 (d, J = 6.9 Hz, 3H), 1.33-1.22 (m, 2H), 0.94 (s, 9H) |
| H174 | 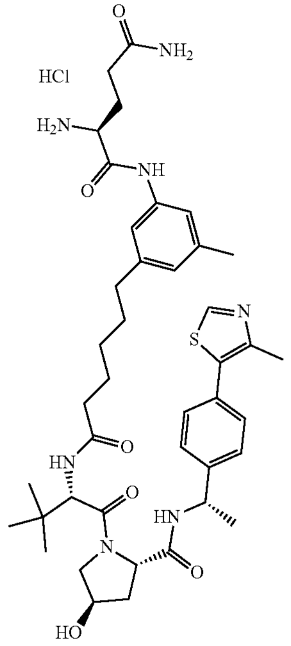 [SMILES: Cc1cc(CCCCCC(=O)N[C@H](C(=O)N2C[C@H](O)C[C@H]2C(=O)N[C@@H](C)c2ccc(-c3scnc3C)cc2)C(C)(C)C)cc(NC(=O)[C@@H](N)CCC(N)=O)c1 ; Cl] | (2S)-2-amino-N-[3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)-5-methylphenyl]pentanediamide hydrochloride | 776.35 | (300 MHz, DMSO-d$_6$) δ 9.78 (s, 1H), 9.00 (s, 1H), 8.52-8.43 (m, 3H), 7.79 (d, J = 9.2 Hz, 1H), 7.49-7.38 (m, 4H), 7.29-7.18 (m, 3H), 7.00 (d, J = 7.8 Hz, 1H), 6.79-6.72 (m, 2H), 5.10 (d, J = 3.5 Hz, 1H), 5.01-4.83 (m, 1H), 4.63-4.36 (m, 2H), 4.30 (s, 1H), 4.06-3.97 (m, 1H), 3.62 (d, J = 3.2 Hz, 2H), 3.04-2.45 (m, 6H), 2.26 (s, 3H), 2.18-2.13 (m, 6H), 1.95-1.70 (m, 2H), 1.62-1.51 (m, 4H), 1.32-1.24 (m, 4H), 0.95 (s, 9H) |

TABLE 49-continued

| Characterization data for intermediates prepared according to procedure above. | | | | |
|---|---|---|---|---|
| Intermediate | Structure | Chemical Name | MS: [(M + 1)]$^+$ | $^1$H-NMR |
| H175 | 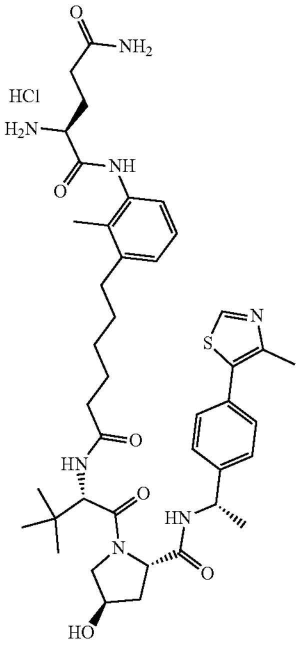 [SMILES: Cl ; Cc1ncsc1-c1ccc([C@H](C)NC(=O)[C@@H]2C[C@@H](O)CN2C(=O)[C@@H](NC(=O)CCCCCc2cccc(NC(=O)[C@@H](N)CCC(N)=O)c2C)C(C)(C)C)cc1] | (2S)-2-amino-N-[3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)-2-methylphenyl]pentanediamide hydrochloride | [(M − H)]$^-$ = 774.45 | (300 MHz, DMSO-$d_6$) δ 10.18 (s, 1H), 9.13 (d, J = 1.6 Hz, 1H), 8.49 (s, 3H), 8.40 (d, J = 7.8 Hz, 1H), 7.78 (d, J = 9.2 Hz, 1H), 7.41 (q, J = 8.3 Hz, 4H), 7.17 (dd, J = 5.5, 2.9 Hz, 1H), 7.09 (t, J = 7.6 Hz, 1H), 7.02 (d, J = 7.3 Hz, 1H), 6.77-6.64 (m, 2H), 4.95-4.90 (m, 1H), 4.51 (d, J = 9.2 Hz, 1H), 4.42 (t, J = 8.0 Hz, 1H), 4.27 (s, 1H), 4.13 (d, J = 5.8 Hz, 1H), 3.70-3.56 (m, 3H), 2.57 (t, J = 7.7 Hz, 2H), 2.46 (s, 3H), 2.31 (t, J = 7.9 Hz, 2H), 2.15-1.95 (m, 4H), 1.86-1.65 (m, 2H), 1.58-1.48 (m, 5H), 1.37 (d, J = 7.0 Hz, 3H), 1.36-1.22 (m, 1H), 1.25-1.14 (m, 1H), 1.13-1.02 (m, 1H), 0.92 (s, 9H) |
| H176 | 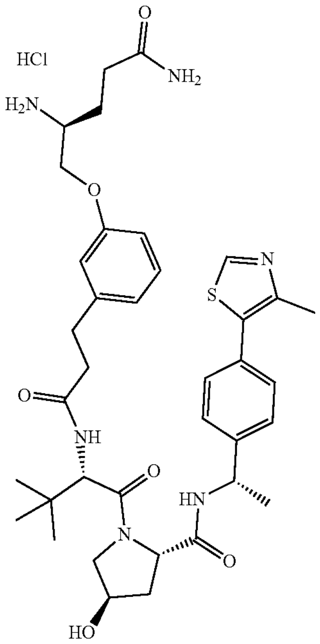 [SMILES: Cc1ncsc1-c1ccc([C@H](C)NC(=O)[C@@H]2C[C@@H](O)CN2C(=O)[C@@H](NC(=O)CCc2cccc(OC[C@@H](N)CCC(N)=O)c2)C(C)(C)C)cc1 ; Cl] | (2S,4R)-1-[(2S)-2-(3-[3-[(2S)-2-amino-4-carbamoylbutoxy]phenyl]propanamido)-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride | 707.35 | (400 MHz, DMSO-$d_6$) δ 9.17 (s, 1H), 8.49-8.35 (m, 5H), 7.90 (d, J = 9.3 Hz, 1H), 7.45 (d, J = 7.8 Hz, 2H), 7.40 (d, J = 8.1 Hz, 2H), 7.20 (t, J = 7.8 Hz, 1H), 6.91-6.76 (m, 3H), 5.76 (s, 1H), 4.92 (t, J = 7.3 Hz, 1H), 4.52 (d, J = 9.3 Hz, 1H), 4.43 (t, J = 8.0 Hz, 1H), 4.28 (s, 1H), 4.17 (dd, J = 10.4, 3.5 Hz, 1H), 4.04 (dd, J = 10.4, 6.4 Hz, 1H), 3.60-3.55 (m, 3H), 2.78 (d, J = 7.7 Hz, 3H), 2.60-2.55 (m, 1H), 2.48 (s, 3H), 2.30-2.24 (m, 1H), 2.08-1.73 (m, 5H), 1.38-1.33 (m, 3H), 0.91 (s, 9H) |

TABLE 49-continued

| Characterization data for intermediates prepared according to procedure above. | | | | |
|---|---|---|---|---|
| Intermediate | Structure | Chemical Name | MS: $[(M + 1)]^+$ | $^1$H-NMR |
| H177 | 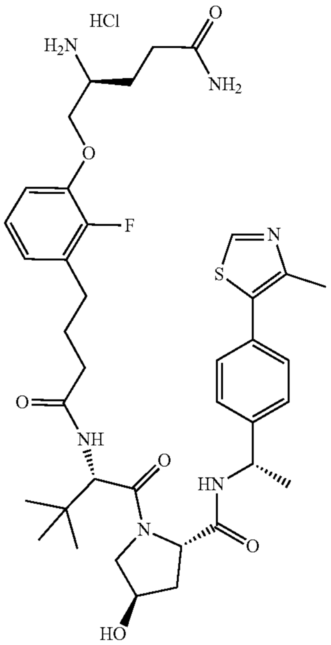 [SMILES: Cc1ncsc1-c1ccc([C@H](C)NC(=O)[C@@H]2C[C@@H](O)CN2C(=O)[C@@H](NC(=O)CCCc2cccc(OC[C@@H](N)CCC(N)=O)c2F)C(C)(C)C)cc1 ; Cl] | (2S,4R)-1-[(2S)-2-(4-[3-[(2S)-2-amino-4-carbamoylbutoxy]-2-fluorophenyl]butan-amido)-3,3-dimethylbutanoyl]-4-hydroxy-N-[(1S)-1-[4-(4-methyl-1,3-thiazol-5-yl)phenyl]eth-yl]pyrrolidine-2-carboxamide hydrochloride | 739.30 | (300 MHz, DMSO-$d_6$) δ 9.11 (s, 1H), 8.44-4.36 (m, 4H), 7.88 (d, J = 9.2 Hz, 1H), 7.44 (q, J = 8.1 Hz, 4H), 7.12-7.04 (m, 2H), 6.95-6.85 (m, 2H), 4.92 (t, J = 7.2 Hz, 1H), 4.54 (d, J = 9.2 Hz, 1H), 4.44 (t, J = 8.0 Hz, 1H), 4.34-4.12 (m, 3H), 3.65-3.62 (m, 2H), 3.53-3.49 (m, 2H), 2.61 (t, J = 7.1 Hz, 2H), 2.45 (s, 3H), 2.27-2.22 (m, 3H), 2.09-1.89 (m, 2H), 1.87-1.74 (m, 5H), 1.39 (d, J = 6.9 Hz, 3H), 0.96 (s, 9H) |
| H178 | 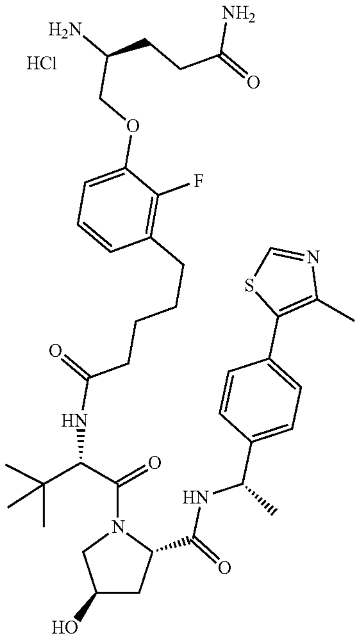 [SMILES: Cc1ncsc1-c1ccc([C@H](C)NC(=O)[C@@H]2C[C@@H](O)CN2C(=O)[C@@H](NC(=O)CCCCc2cccc(OC[C@@H](N)CCC(N)=O)c2F)C(C)(C)C)cc1 ; Cl] | (2S,4R)-1-[(2S)-2-(5-[3-[(2S)-2-amino-4-carbamoylbutoxy]-2-fluorophenyl]pentan-amido)-3,3-dimethylbutanoyl]-4-hydroxy-N-[(1S)-1-[4-(4-methyl-1,3-thiazol-5-yl)phenyl]eth-yl]pyrrolidine-2-carboxamide hydrochloride | 753.35 | (400 MHz, DMSO-$d_6$) δ 8.99 (s, 1H), 8.38 (d, J = 7.8 Hz, 1H), 7.83 (d, J = 9.3 Hz, 1H), 7.44 (d, J = 8.3 Hz, 2H), 7.39 (d, J = 8.4 Hz, 2H), 7.28 (s, 1H), 7.06-6.94 (m, 2H), 6.85-6.77 (m, 2H), 6.76-6.67 (m, 2H), 5.12-5.10 (m, 1H), 4.92 (t, J = 7.1 Hz, 1H), 4.56-4.48 (d, J = 7.3 Hz 1H), 4.43 (t, J = 8.0 Hz, 1H), 4.29-4.27 (m, 1H), 3.87-3.85 (m, 1H), 3.81-3.78 (m, 1H), 3.67-3.56 (m, 2H), 2.97-2.95 (m, 1H), 2.60 (t, J = 6.9 Hz, 2H), 2.46 (s, 3H), 2.35-2.20 (m, 2H), 2.17-2.14 (m, 2H), 2.03-1.99 (m, 1H), 1.86-1.70 (m, 2H), 1.57-1.44 (m, 5H), 1.38 (d, J = 7.0 Hz, 3H), 0.94 (s, 9H) |

TABLE 49-continued

| Characterization data for intermediates prepared according to procedure above. | | | | |
|---|---|---|---|---|
| Intermediate | Structure | Chemical Name | MS: [(M + 1)]$^+$ | $^1$H-NMR |
| H179 | 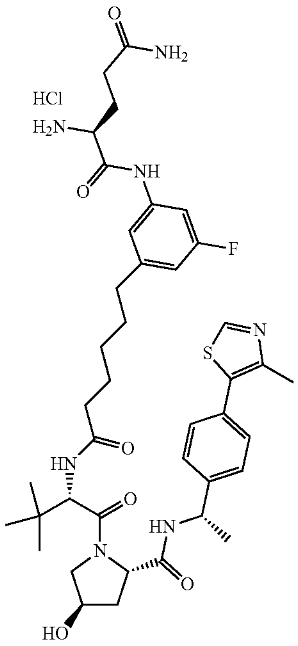 [SMILES: Cc1ncsc1-c1ccc([C@H](C)NC(=O)[C@@H]2C[C@@H](O)CN2C(=O)[C@@H](NC(=O)CCCCCc2cc(F)cc(NC(=O)[C@@H](N)CCC(N)=O)c2)C(C)(C)C)cc1 ; Cl] | (2S)-2-amino-N-[3-fluoro-5-(5-[[(2S)-1-[(2S,4R)-4-hydroxy-2-[[(1S)-1-[4-(4-methyl-1,3-thiazol-5-yl)phenyl]-ethyl]carbamoyl]pyrrolidin-1-yl]-3,3-dimethyl-1-oxobutan-2-yl]carbamoyl]pentyl)phenyl]pentanediamide hydrochloride | 780.25 | (400 MHz, DMSO-$d_6$) δ 11.25 (s, 1H), 9.19 (d, J = 5.6 Hz, 1H), 8.53 (d, J = 5.2 Hz, 3H), 8.43 (d, J = 7.8 Hz, 1H), 7.80 (d, J = 9.2 Hz, 1H), 7.53-7.43 (m, 3H), 7.40 (d, J = 8.2 Hz, 2H), 7.26 (s, 1H), 6.85-6.75 (m, 1H), 4.98-4.92 (m, 1H), 4.51 (d, J = 9.3 Hz, 1H), 4.44 (q, J = 8.0, 7.3 Hz, 1H), 4.29 (d, J = 3.9 Hz, 1H), 4.10 (d, J = 5.8 Hz, 1H), 3.60 (d, J = 4.0 Hz, 2H), 2.55 (t, J = 7.7 Hz, 3H), 2.48 (s, 3H), 2.34-2.19 (m, 3H), 2.19-1.95 (m, 4H), 1.85-1.77 (m, 1H), 1.64-1.42 (m, 5H), 1.38 (d, J = 6.9 Hz, 3H), 1.27 (q, J = 7.5 Hz, 2H), 0.93 (s, 9H) |
| H180 | 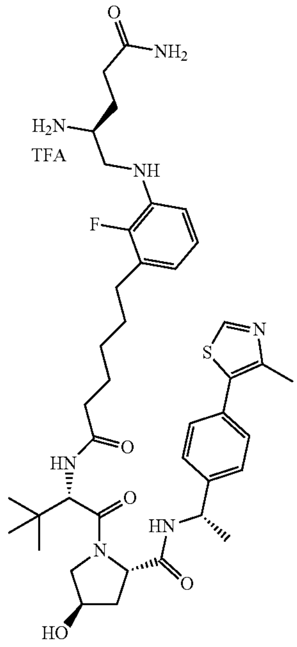 [SMILES: Cc1ncsc1-c1ccc([C@H](C)NC(=O)[C@@H]2C[C@@H](O)CN2C(=O)[C@@H](NC(=O)CCCCCc2cccc(NC[C@@H](N)CCC(N)=O)c2F)C(C)(C)C)cc1 ; "TFA"] | (2S,4R)-1-[(2S)-2-(6-[3-[(2-amino-4-carbamoylbutyl)amino]-2-fluorophenyl]hexanamido)-3,3-dimethylbutanoyl]-4-hydroxy-N-[(1S)-1-[4-(4-methyl-1,3-thiazol-5-yl)phenyl]ethyl]pyrrolidine-2-carboxamide trifluoroacetate | 766.35 | (400 MHz, DMSO-$d_6$) δ 9.01 (s, 1H), 8.37 (d, J = 7.7 Hz, 1H), 7.86 (s, 2H), 7.79 (d, J = 9.2 Hz, 1H), 7.45 (d, J = 7.8 Hz, 2H), 7.39 (d, J = 8.1 Hz, 2H), 6.97 (s, 1H), 6.90 (t, J = 7.7 Hz, 1H), 6.62 (t, J = 8.1 Hz, 1H), 6.50 (t, J = 7.0 Hz, 1H), 4.92 (t, J = 7.2 Hz, 1H) 4.52 (d, J = 9.1 Hz, 1H), 4.42 (t, J = 8.1 Hz, 1H), 4.29 (s, 1H), 3.56 (s, 2H), 3.32-3.18 (m, 3H), 2.48 (s, 3H), 2.29-2.25 (m, 3H), 2.15-2.07 (m, 1H), 2.02 (d, J = 15.4 Hz, 2H), 1.84-1.80 (m, 3H), 1.57-1.46 (m, 4H), 1.41-1.37 (m, 3H), 1.24-1.20 (m, 6H), 0.94 (s, 9H) |

TABLE 49-continued

| Characterization data for intermediates prepared according to procedure above. | | | | |
|---|---|---|---|---|
| Intermediate | Structure | Chemical Name | MS: [(M + 1)]+ | 1H-NMR |
| H181 | 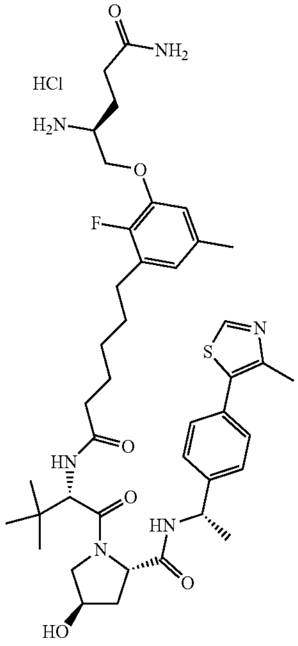 [SMILES: Cc1cc(CCCCCC(=O)N[C@H](C(=O)N2C[C@H](O)C[C@H]2C(=O)N[C@@H](C)c2ccc(-c3scnc3C)cc2)C(C)(C)C)c(F)c(OC[C@@H](N)CCC(N)=O)c1 ; Cl] | (2S,4R)-1-[(2S)-2-(6-[3-[(2S)-2-amino-4-carbamoylbutoxy]-2-fluoro-5-methylphenyl]hexan-amido)-3,3-dimethylbutanoyl]-4-hydroxy-N-[(1S)-1-[4-(4-methyl-1,3-thiazol-5-yl)phenyl]eth-yl]pyrrolidine-2-carboxamide hydrochloride | 781.35 | (300 MHz, DMSO-$d_6$) δ 9.09 (s, 1H), 8.38 (d, J = 7.1 Hz, 3H), 7.77 (d, J = 9.2 Hz, 1H), 7.41 (q, J = 8.2 Hz, 5H), 6.85 (d, J = 7.7 Hz, 2H), 6.67 (d, J = 5.9 Hz, 1H), 4.91 (t, J = 7.2 Hz, 1H), 4.50 (d, J = 9.3 Hz, 1H), 4.42 (t, J = 8.1 Hz, 1H), 4.30-4.25 (m, 1H), 4.19 (dd, J = 10.5, 3.8 Hz, 1H), 4.14-4.05 (m, 1H), 3.62-3.58 (m, 2H), 3.52-3.42 (m, 1H), 2.57-2.51 (m, 2H), 2.46 (s, 3H), 2.34-2.26 (m, 2H), 2.24 (s, 3H), 2.18-1.95 (m, 3H), 1.95-1.86 (m, 2H), 1.84-1.71 (m, 1H), 1.58-1.44 (m, 4H), 1.41-1.34 (s, 3H), 1.31-1.18 (m, 3H), 0.92(s, 9H) |
| H182 | 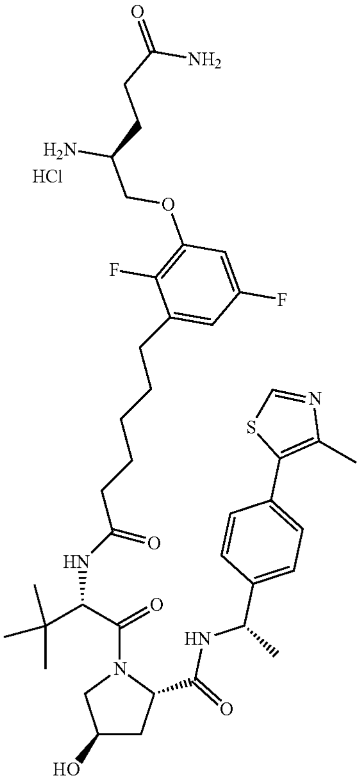 [SMILES: Cc1ncsc1-c1ccc([C@H](C)NC(=O)[C@@H]2C[C@@H](O)CN2C(=O)[C@@H](NC(=O)CCCCCc2cc(F)cc(OC[C@@H](N)CCC(N)=O)c2F)C(C)(C)C)cc1 ; Cl] | (2S,4R)-1-[(2S)-2-(6-[3-[(2S)-2-amino-4-carbamoylbutoxy]-2,5-difluorophenyl]hexan-amido)-3,3-dimethylbutanoyl]-4-hydroxy-N-[(1S)-1-[4-(4-methyl-1,3-thiazol-5-yl)phenyl]eth-yl]pyrrolidine-2-carboxamide hydrochloride | 785.40 | (300 MHz, CD3OD) δ 10.03 (s, 1H), 7.63-7.46 (m, 4H), 6.93-6.81 (m, 1H), 6.74-6.65 (m, 1H), 5.04 (q, J = 6.9 Hz, 1H), 4.66-4.53 (m, 2H), 4.45 (br, 1H), 4.30 (dd, J = 10.5, 3.5 Hz, 1H), 4.21-4.13 (m, 1H), 3.90 (d, J = 11.0 Hz, 1H), 3.76-3.69 (m, 5H), 2.72-2.65 (m, 1H), 2.63 (s, 3H), 2.52 (q, J = 7.0 Hz, 1H), 2.37-2.15 (m, 2H), 2.15-2.03 (m, 2H), 2.01-1.87 (m, 1H), 1.69-1.57 (m, 4H), 1.53 (d, J = 7.0 Hz, 3H), 1.47-1.27 (m, 2H), 1.05 (s, 9H) |

TABLE 49-continued

| Characterization data for intermediates prepared according to procedure above. | | | | |
|---|---|---|---|---|
| Intermediate | Structure | Chemical Name | MS: $[(M+1)]^+$ | $^1$H-NMR |
| H183 | 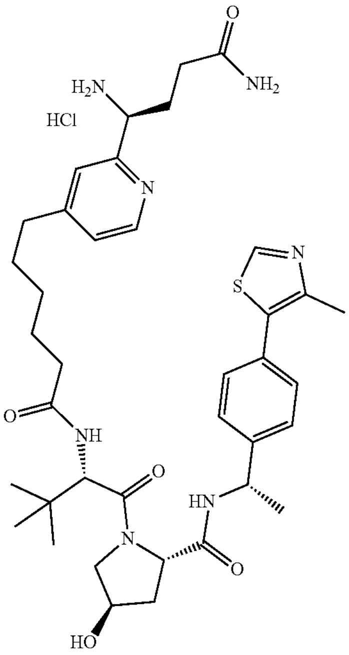 [SMILES: Cc1ncsc1-c1ccc([C@H](C)NC(=O)[C@@H]2C[C@@H](O)CN2C(=O)[C@@H](NC(=O)CCCCCc2ccnc([C@@H](N)CCC(N)=O)c2)C(C)(C)C)cc1 ; Cl] | (2S,4R)-1-[(2S)-2-(6-[2-[(1S)-1-amino-3-carbamoylpropyl]pyridin-4-yl]hexanamido)-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride | 720.30 | (300 MHz, DMSO-$d_6$) δ 9.14 (s, 3H), 9.02 (s, 1H), 8.87-8.85 (d, J = 6.0 Hz, 1H), 8.41-8.38 (d, J = 7.8 Hz, 1H), 8.13 (s, 1H), 8.03 (s, 1H), 7.81-7.78 (d, J = 9.2 Hz, 1H), 7.45-7.27 (q, J = 8.3 Hz, 4H), 6.85 (s, 1H), 4.93-4.88 (t, J = 7.2 Hz, 1H), 4.53-4.38 (m, 1H), 4.27 (s, 1H), 3.59 (s, 3H), 3.56 (s, 4H), 3.09-3.00 (m, 4H), 2.45 (s, 2H), 2.33-2.11 (m, 1H), 2.07 (s, 2H), 1.78-1.74 (m, 3H), 1.53 (s, 2H), 1.38-1.28 (d, J = 7.0 Hz, 2H), 1.23-1.16 (m, 5H), 0.93 (s, 9H) |
| H184 | 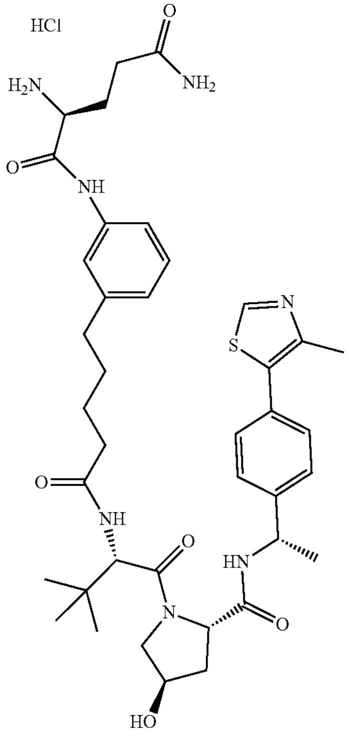 [SMILES: Cc1ncsc1-c1ccc([C@H](C)NC(=O)[C@@H]2C[C@@H](O)CN2C(=O)[C@@H](NC(=O)CCCCc2cccc(NC(=O)[C@@H](N)CCC(N)=O)c2)C(C)(C)C)cc1 ; Cl] | (2S)-2-amino-N-[3-(4-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]butyl)phenyl]pentanediamide hydrochloride | 748.40 | (300 MHz, DMSO-$d_6$) δ 10.55 (s, 1H), 9.01 (s, 1H), 8.39-8.30 (m, 5H), 7.82 (d, J = 9.1 Hz, 1H), 7.52-7.34 (m, 7H), 7.30-7.25 (m, 1H), 6.99-6.96 (m, 2H), 4.96-4.88 (m, 1H), 4.55-4.41 (m, 2H), 4.31-4.28 (m, 1H), 4.04-3.96 (m, 1H), 2.61-2.57 (m, 2H), 2.47 (s, 3H), 2.31-2.14 (m, 2H), 2.09-1.77 (m, 5H), 1.59-1.48 (m, 5H), 1.39 (d, J = 7.0 Hz, 3H), 1.27-1.25 (m, 1H), 0.95 (s, 9H) |

TABLE 49-continued

| Characterization data for intermediates prepared according to procedure above. | | | | |
|---|---|---|---|---|
| Intermediate | Structure | Chemical Name | MS: [(M + 1)]$^+$ | $^1$H-NMR |
| H185 | 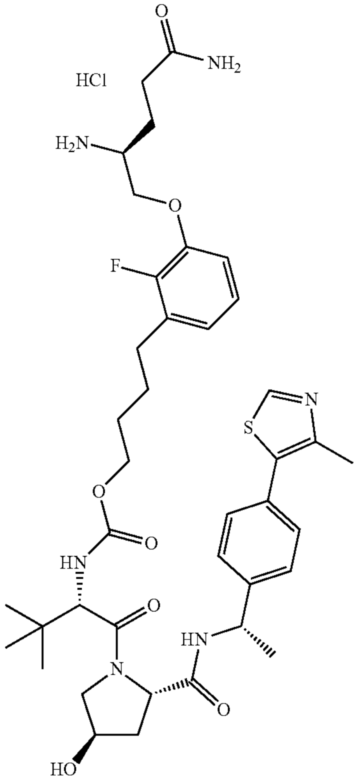 [SMILES: Cc1ncsc1-c1ccc([C@H](C)NC(=O)[C@@H]2C[C@@H](O)CN2C(=O)[C@@H](NC(=O)OCCCCc2cccc(OC[C@@H](N)CCC(N)=O)c2F)C(C)(C)C)cc1 ; Cl] | 4-[3-[(2S)-2-amino-4-carbamoylbutoxy]-2-fluorophenyl]butyl N-[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamate hydrochloride | 769.35 | (400 MHz, DMSO-$d_6$) δ 9.06 (s, 1H), 8.44 (s, 1H), 7.44 (d, J = 2.6 Hz, 3H), 7.39 (s, 1H), 7.32 (s, 2H), 7.19 (s, 2H), 7.10-7.03 (m, 1H), 6.91 (s, 1H), 4.90 (q, J = 7.2 Hz, 1H), 4.44 (t, J = 8.0 Hz, 1H), 4.31-4.10 (m, 3H), 3.97 (d, J = 11.9 Hz, 2H), 3.67-3.57 (m, 4H), 2.63 (d, J = 7.6 Hz, 2H), 2.47 (s, 3H), 2.33-2.29 (m, 2H), 2.10-1.97 (m, 1H), 1.93 (s, 2H), 1.84-1.71 (m, 6H), 1.62-1.58 (m, 2H), 1.38 (d, J = 7.0 Hz, 3H), 0.94 (s, 9H) |
| H186 | 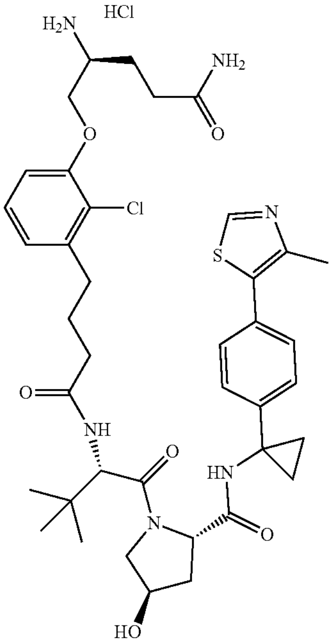 [SMILES: Cl ; Cc1ncsc1-c1ccc(C2(NC(=O)[C@@H]3C[C@@H](O)CN3C(=O)[C@@H](NC(=O)CCCc3cccc(OC[C@@H](N)CCC(N)=O)c3Cl)C(C)(C)C)CC2)cc1] | (2S,4R)-1-[(2S)-2-(4-[3-[(2S)-2-amino-4-carbamoylbutoxy]-2-chlorophenyl]butanamido)-3,3-dimethylbutanoyl]-4-hydroxy-N-[1-[4-(4-methyl-1,3-thiazol-5-yl)phenyl]cyclopropyl]pyrrolidine-2-carboxamide hydrochloride | 767.20 | (300 MHz, DMSO-$d_6$) δ 9.06 (s, 1H), 8.88-8.83 (m, 1H), 8.39-8.33 (m, 2H), 8.02 (d, J = 9.2 Hz, 1H), 7.51-7.46 (m, 1H), 7.38-7.31 (m, 3H), 7.30-7.19 (m, 2H), 7.10-7.02 (m, 1H), 7.01-6.90 (m, 2H), 4.58 (d, J = 9.3 Hz, 1H), 4.45-4.39 (m, 4H), 3.68-3.65 (m, 1H), 3.63-3.51 (m, 5H), 2.75-2.70 (m, 2H), 2.46 (s, 3H), 2.37-2.20 (m, 4H), 2.04-1.94 (m, 3H), 1.85-1.76 (m, 2H), 1.29-1.23 (m, 2H), 0.96 (s, 9H) |

TABLE 49-continued

Characterization data for intermediates prepared according to procedure above.

| Intermediate | Structure | Chemical Name | MS: [(M + 1)]$^+$ | $^1$H-NMR |
|---|---|---|---|---|
| H187 | 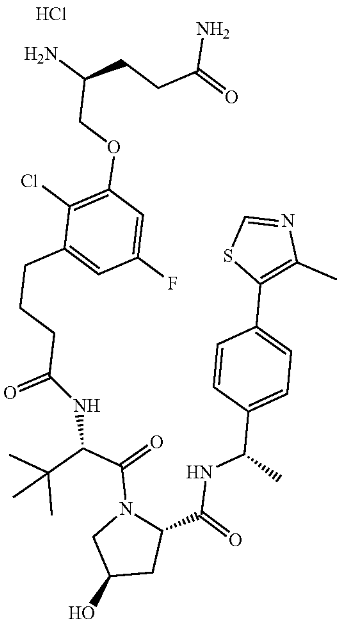 [SMILES: Cl ; Cc1ncsc1-c1ccc([C@H](C)NC(=O)[C@@H]2C[C@@H](O)CN2C(=O)[C@@H](NC(=O)CCCc2cc(F)cc(OC[C@@H](N)CCC(N)=O)c2Cl)C(C)(C)C)cc1] | (2S)-2-amino-N-[2-chloro-3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenyl]pentanediamide hydrochloride | 773.25 | (300 MHz, DMSO-$d_6$) δ 9.08 (s, 1H), 8.47-8.30 (m, 4H), 7.91 (d, J = 9.2 Hz, 1H), 7.48-7.38 (m, 4H), 7.12-7.06 (m, 1H), 7.03 (s, 1H), 6.87 (dd, J = 9.2, 2.8 Hz, 1H), 4.94-4.90 (m, 1H), 4.54 (d, J = 9.3 Hz, 1H), 4.44 (t, J = 7.9 Hz, 1H), 4.35-4.24 (m, 2H), 4.19-3.77 (m, 2H), 3.60-3.57 (m, 2H), 2.71 (t, J = 7.6 Hz, 2H), 2.48 (s, 3H), 2.34-2.30 (m, 3H), 2.19-1.98 (m, 4H), 1.87-1.71 (m, 3H), 1.39 (d, J = 7.0 Hz, 3H), 1.26-1.24 (m, 1H), 0.96 (s, 9H) |
| H188 | 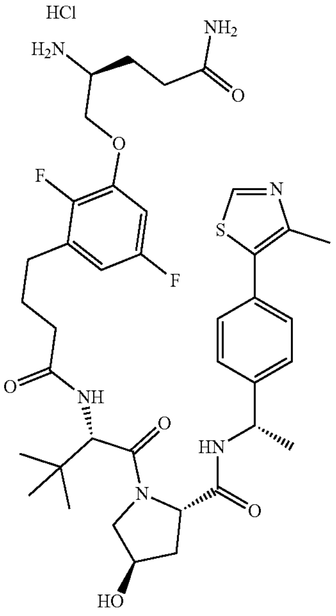 [SMILES: Cl ; Cc1ncsc1-c1ccc([C@H](C)NC(=O)[C@@H]2C[C@@H](O)CN2C(=O)[C@@H](NC(=O)CCCc2cc(F)cc(OC[C@@H](N)CCC(N)=O)c2F)C(C)(C)C)cc1] | (2S,4R)-1-[(2S)-2-(4-[3-[(2S)-2-amino-4-carbamoylbutoxy]-2,5-difluorophenyl]butanamido)-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride | 757.30 | (300 MHz, DMSO-$d_6$) δ 9.08 (s, 1H), 8.40-8.36 (m, 3H), 7.91 (d, J = 9.2 Hz, 1H), 7.52-7.41 (m, 4H), 7.42-4.38 (m, 2H), 7.07-7.01 (m, 2H), 6.77 (s, 1H), 5.13-5.10 (m, 1H), 4.93 (t, J = 7.4 Hz, 1H), 4.54 (d, J = 9.1 Hz, 1H), 4.44 (t, J = 8.1 Hz, 1H), 4.27 (d, J = 11.6 Hz, 2H), 4.20-4.18 (m, 1H), 3.64-3.60 (m, 3H), 2.61-2.54 (m, 2H), 2.49 (s, 3H), 2.31-2.29 (m, 3H), 2.26-2.10 (m, 2H), 1.98-1.95 (m, 2H), 1.79-1.72 (m, 3H), 1.39 (d, J = 7.0 Hz, 3H), 0.96 (s, 9H) |

TABLE 49-continued

Characterization data for intermediates prepared according to procedure above.

| Intermediate | Structure | Chemical Name | MS: [(M + 1)]+ | $^1$H-NMR |
|---|---|---|---|---|
| H189 | 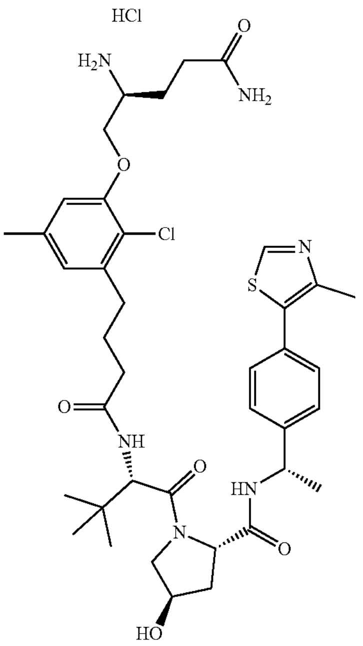 | (2S,4R)-1-[(2S)-2-(4-[3-[(2S)-2-amino-4-carbamoylbutoxy]-2-chloro-5-methylphenyl]butanamido)-3,3-dimethylbutanoyl]-4-hydroxy-N-[(1S)-1-[4-(4-methyl-1,3-thiazol-5-yl)phenyl]ethyl]pyrrolidine-2-carboxamide | 769.00 | (400 MHz, DMSO-$d_6$) δ 9.09 (d, J = 1.6 Hz, 1H), 8.46-8.32 (m, 4H), 7.89 (d, J = 9.3 Hz, 1H), 7.47-7.41 (m, 2H), 7.39 (d, J = 8.4 Hz, 2H), 6.94 (s, 1H), 6.89 (d, J = 1.9 Hz, 1H), 6.78 (d, J = 1.8 Hz, 1H), 4.95-4.88 (m, 1H), 4.53 (d, J = 9.3 Hz, 1H), 4.42 (t, J = 8.0 Hz, 1H), 4.30-4.26 (m, 1H), 4.24-4.20 (m, 1H), 4.13 (dd, J = 10.5, 5.7 Hz, 1H), 3.62-3.61 (m, 2H), 3.57 (s, 3H), 2.66-2.61 (m, 2H), 2.47 (s, 3H), 2.36-2.23 (m, 5H), 2.22-2.14 (m, 1H), 2.05-1.91 (m, 3H), 1.83-1.73 (m, 3H), 1.38 (d, J = 7.0 Hz, 3H), 0.95 (s, 9H) |

(9H-fluoren-9-yl)methyl ((3S,6S)-6-(((2R,3S)-6-amino-2-((4-(3-(2-(3-(1-(2,6-dioxopiperidin-3-yl)-3-methyl-2-oxo-2,3-dihydro-1H-benzo[d]imidazol-5-yl)propoxy)ethoxy)propyl)benzyl)oxy)-6-oxohexan-3-yl)carbamoyl)-4-oxo-1,2,3,4,6,7-hexahydroazepino[3,2,1-hi]indol-3-yl)carbamate (Intermediate I)

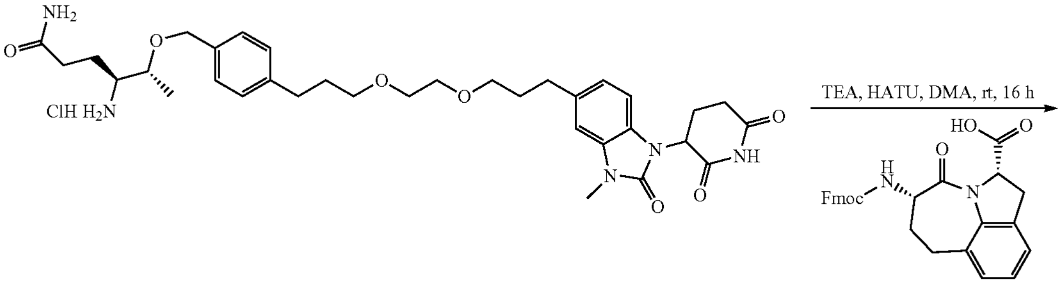

-continued

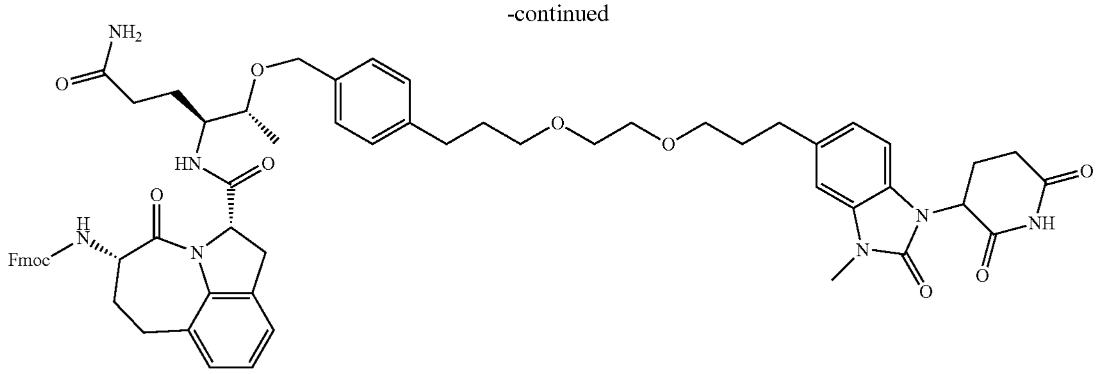

Intermediate I

To a solution of (3S,6S)-3-((((9H-fluoren-9-yl)methoxy) carbonyl)amino)-4-oxo-1,2,3,4,6,7-hexahydroazepino[3,2,1-hi]indole-6-carboxylic acid (139 mg, 0.30 mmol) in DMA (7.00 mL) were added TEA (120 mg, 1.19 mmol) and HATU (147 mg, 0.39 mmol) at 0° C. under nitrogen atmosphere. The resulting mixture was stirred for 10 min at room temperature followed by the addition of (4S,5R)-4-amino-5-([4-[3-(2-[3-[1-(2,6-dioxopiperidin-3-yl)-3-methyl-2-oxo-1,3-benzodiazol-5-yl]propoxy]ethoxy)propyl]phenyl] methoxy)hexanamide hydrochloride (200 mg, 0.30 mmol). The resulting mixture was stirred for 16 hours at room temperature under nitrogen atmosphere. Upon completion, the resulting mixture was purified by reversed phase flash chromatography with the following conditions: Column: WelFlash™ C18-I, 20~40 um, 120 g; EluentA: Water (plus 10 mmol/LAcOH); Eluent B: ACN; Gradient: 30% - 50% B in 20 min; Flow rate: 50 mL/min; Detector: UV 220/200 nm; desired fractions were collected at 46% B and concentrated under reduced pressure to afford the title compound as a white solid (200 mg, 62%): $^1$H NMR (400 MHz, DMSO-d4) δ 11.08 (s, 1H), 7.90 (d, J=7.6 Hz, 2H), 7.84 (d, J=9.0 Hz, 1H), 7.75 (q, J=7.0 Hz, 3H), 7.43 (t, J=7.4 Hz, 2H), 7.34 (t, J=7.4 Hz, 2H), 7.31-7.26 (m, 1H), 7.20-7.08 (m, 4H), 7.08-6.92 (m, 5H), 6.87 (d, J=8.0 Hz, 1H), 6.69 (s, 1H), 5.33 (dd, J=12.7, 5.4 Hz, 1H), 5.06 (d, J=10.6 Hz, 1H), 4.45 (s, 1H), 4.40 (s, 2H), 4.27 (p, J=8.3, 7.3 Hz, 3H), 4.13 (s, 1H), 3.78 (s, 1H), 3.51 (s, 3H), 3.48-3.38 (m, 4H), 3.32-3.33 (m, 9H), 3.05 (s, 2H), 2.85 (d, J=15.9 Hz, 2H), 2.56-2.73 (m, 5H), 2.2.00-2.10 (m, 1H), 1.92-1.75 (m, 5H), 1.56 (s, 1H), 1.07 (d, J=6.4 Hz, 3H); MS (ESI, m/z): [(M+1)]$^+$=1088.30.

The following intermediates in Table 50 were synthesized according to the above procedure to prepare Intermediate I.

TABLE 50

Characterization data for intermediates prepared according to above.

| Inter-mediate | Structure | Chemical Name | MS: [(M + 1)]$^+$ | $^1$H NMR |
|---|---|---|---|---|
| I1 | 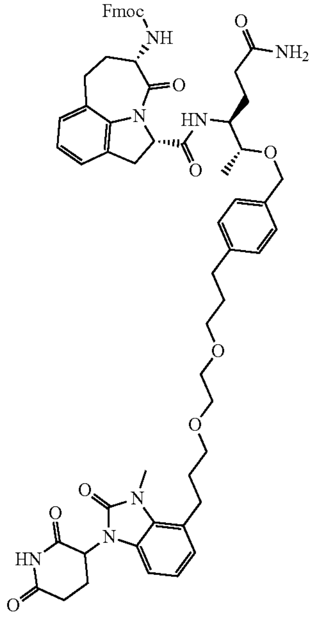 | 9H-fluoren-9-ylmethyl N-[(2S,11S)-2-[[(3S,4R)-1-carbamoyl-4-([4-[3-(2-[3-[1-(2,6-dioxopiperidin-3-yl)-3-methyl-2-oxo-1,3-benzodiazol-4-yl]propoxy]ethoxy) propyl]phenyl]methoxy) pentan-3-yl]carbamoyl]-12-oxo-1-azatricyclo[6.4.1.0^[4,13]] trideca-4(13),5,7-trien-11-yl]carbamate | 1088.6 | (400 MHz, DMSO-d$_6$) δ 11.09 (s, 1H), 7.90 (d, J = 7.6 Hz, 2H), 7.83 (d, J = 9.2 Hz, 1H), 7.75 (q, J = 8.0, 7.5 Hz, 3H), 7.43 (t, J = 7.5 Hz, 2H), 7.34 (t, J = 7.5 Hz, 2H), 7.17 (d, J = 7.7 Hz, 3H), 7.12 (d, J = 7.8 Hz, 2H), 7.05 (d, J = 7.7 Hz, 2H), 7.00-6.93 (m, 3H), 6.91-6.84 (m, 1H), 6.68 (s, 1H), 5.36 (dd, J = 12.4, 5.4 Hz, 1H), 5.06 (d, J = 10.5 Hz, 1H), 4.39 (s, 2H), 4.27 (s, 2H), 4.25 (s, 1H), 4.13 (s, 1H), 3.78 (s, 2H), 3.56 (m, 3H), 3.52 (m, 3H), 3.44 (dt, J = 27.9, 6.2 Hz, 4H), 3.32 (s, 4H), 3.07 (d, J = 15.5 Hz, 1H), 2.96 (t, J = 7.8 Hz, 2H), 2.85 (d, J = 17.2 Hz, 2H), 2.76-2.68 (m, 1H), 2.66-2.56 (m, 3H), 2.52 (s, 3H), 2.08 (s, 1H), 1.82 (m, 5H), 1.54 (s, 1H), 1.07 (d, J = 6.2 Hz, 3H). |

TABLE 50-continued

| Characterization data for intermediates prepared according to above. | | | | |
|---|---|---|---|---|
| Intermediate | Structure | Chemical Name | MS: [(M + 1)]$^+$ | $^1$H NMR |
| I2 | 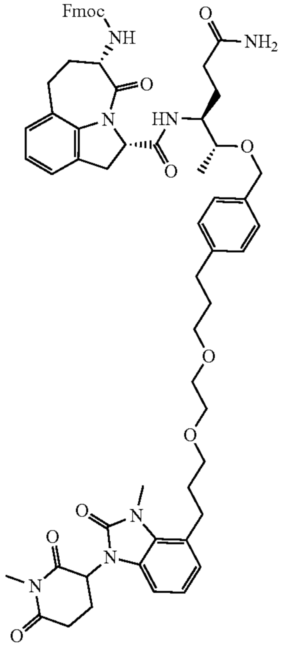 | 9H-fluoren-9-ylmethyl N-[(2S,11S)-2-[[(3S,4R)-1-carbamoyl-4-([4-[3-(2-[3-[3-methyl-1-(1-methyl-2,6-dioxopiperidin-3-yl)-2-oxo-1,3-benzodiazol-4-yl]propoxy]ethoxy)propyl]phenyl]methoxy)pentan-3-yl]carbamoyl]-12-oxo-1-azatricyclo[6.4.1.0^[4,13]]trideca-4(13),5,7-trien-11-yl]carbamate | [(M + 23)]$^+$ = 1102.8 | (400 MHz, DMSO-$d_6$) δ 7.90 (d, J = 7.5 Hz, 2H), 7.83 (d, J = 9.3 Hz, 1H), 7.74 (q, J = 8.9, 8.0 Hz, 3H), 7.43 (t, J = 7.4 Hz, 2H), 7.34 (t, J = 7.5 Hz, 2H), 7.26-7.08 (m, 4H), 7.04 (d, J = 7.4 Hz, 2H), 6.95 (d, J = 7.3 Hz, 3H), 6.94-6.84 (m, 1H), 6.68 (s, 1H), 5.76 (d, J = 1.4 Hz, 2H), 5.47-5.39 (m, 1H), 5.06 (d, J = 10.7 Hz, 1H), 4.41 (d, J = 12.5 Hz, 2H), 4.26 (d, J = 7.7 Hz, 3H), 4.13 (s, 1H), 3.78 (s, 2H), 3.56 (s, 3H), 3.52 (s, 4H), 3.49-3.36 (m, 5H), 3.32 (s, 1H), 3.03 (s, 3H), 2.96 (t, J = 7.8 Hz, 2H), 2.89-2.77 (m, 1H), 2.77-2.66 (m, 1H), 2.61 (t, J = 7.8 Hz, 2H), 2.50 (s, 2H), 2.08 (d, J = 1.5 Hz, 3H), 1.81 (m, 6 H), 1.56 (s, 1H), 1.07 (d, J = 6.2 Hz, 3H). |
| I3 | 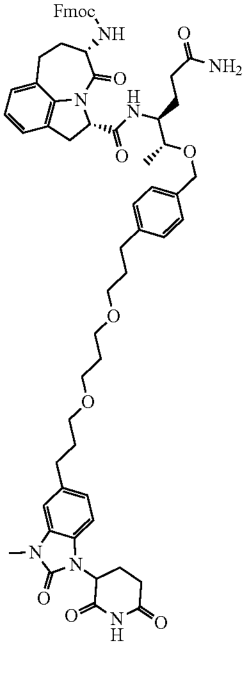 | 9H-fluoren-9-ylmethyl N-[(2S,11S)-2-[[(3S,4R)-1-carbamoyl-4-([4-[3-(3-[3-[1-(2,6-dioxopiperidin-3-yl)-3-methyl-2-oxo-1,3-benzodiazol-5-yl]propoxy]propoxy)propyl]phenyl]methoxy)pentan-3-yl]carbamoyl]-12-oxo-1-azatricyclo[6.4.1.0^[4,13]]trideca-4(13),5,7-trien-11-yl]carbamate | 1102.6 | (400 MHz, $CDCl_3$) δ 8.83 (d, J = 35.6 Hz, 1H), 7.79 (d, J = 7.7 Hz, 2H), 7.64 (s, 2H), 7.42 (t, J = 7.5 Hz, 2H), 7.33 (t, J = 7.4 Hz, 2H), 7.16 (t, J = 7.7 Hz, 2H), 7.06 (s, 3H), 6.93-6.84 (m, 2H), 6.72 (d, J = 7.9 Hz, 1H), 6.10 (d, J = 7.0 Hz, 1H), 6.00 (s, 1H), 5.20 (d, J = 19.3 Hz, 2H), 4.58 (s, 1H), 4.39 (m, 4H), 4.26 (s, 1H), 3.98 (s, 1H), 3.60 (s, 1H), 3.53 (t, J = 6.2 Hz, 3H), 3.43 (s, 3H), 3.39 (s, 2H), 3.30 (s, 2H), 3.23 (s, 1H), 3.10 (d, J = 17.8 Hz, 1H), 2.97-2.81 (m, 1H), 2.72 (dd, J = 19.5, 11.8 Hz, 5H), 2.32 (s, 1H), 2.22 (s, 1H), 2.05 (s, 1H), 1.89 (d, J = 7.0 Hz, 5H), 1.65 (s, 8H), 1.28 (s, 1H), 1.22 (s, 3H). |

TABLE 50-continued

| Characterization data for intermediates prepared according to above. | | | | |
|---|---|---|---|---|
| Inter-mediate | Structure | Chemical Name | MS: [(M + 1)]$^+$ | $^1$H NMR |
| I4 | 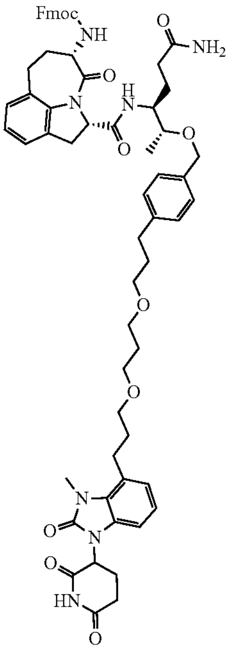 | 9H-fluoren-9-ylmethyl N-[(2S,11S)-2-[[(3S,4R)-1-carbamoyl-4-([4-[3-(3-[3-[1-(2,6-dioxopiperidin-3-yl)-3-methyl-2-oxo-1,3-benzodiazol-4-yl]propoxy]propoxy)propyl]phenyl]methoxy)pentan-3-yl]carbamoyl]-12-oxo-1-azatricyclo[6.4.1.0^[4,13]]trideca-4(13),5,7-trien-11-yl]carbamate | 1102.7 | (400 MHz, $CD_3OD$) δ 7.81 (d, J = 7.6 Hz, 2H), 7.70 (t, J = 8.4 Hz, 2H), 7.43-7.30 (m, 5H), 7.23 (d, J = 7.7 Hz, 3H), 7.13 (d, J = 7.7 Hz, 3H), 7.09-7.00 (m, 5H), 7.02-6.90 (m, 3H), 5.33 (d, J = 12.4 Hz, 1H), 5.11 (d, J = 10.8 Hz, 1H), 4.47 (d, J = 8.3 Hz, 2H), 4.44-4.35 (m, 3H), 4.32 (d, J = 9.8 Hz, 1H), 4.25 (s, 1H), 3.96 (s, 1H), 3.64 (s, 4H), 3.52 (dd, J = 12.3, 6.1 Hz, 7H), 3.41 (d, J = 14.6 Hz, 1H), 3.13 (s, 2H), 3.08-3.00 (m, 3H), 2.79 (d, J = 14.1 Hz, 3H), 2.68 (t, J = 7.7 Hz, 3H), 2.24 (s, 3H), 8, 1.87 (s, 8H), 1.66 (s, 1H), 1.18 (d, J = 6.3 Hz, 3H). |
| I5 | 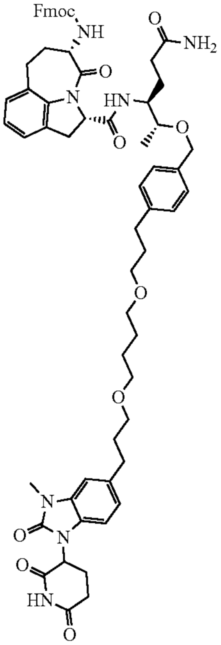 | 9H-fluoren-9-ylmethyl N-[(2S,11S)-2-[[(3S,4R)-1-carbamoyl-4-([4-[3-(4-[3-[1-(2,6-dioxopiperidin-3-yl)-3-methyl-2-oxo-1,3-benzodiazol-5-yl]propoxy]butoxy)propyl]phenyl]methoxy)pentan-3-yl]carbamoyl]-12-oxo-1-azatricyclo[6.4.1.0^[4,13]]trideca-4(13),5,7-trien-11-yl]carbamate | 1116.6 | (400 MHz, DMSO-$d_6$) δ 11.08 (s, 1H), 7.96-7.69 (m, 5H), 7.54 (s, 1H), 7.39 (dt, J = 34.1, 7.4 Hz, 4H), 7.23-6.93 (m, 10H), 6.87 (d, J = 8.1 Hz, 1H), 6.69 (s, 1H), 5.34 (dd, J = 12.5, 5.4 Hz, 1H), 5.16-4.93 (m, 1H), 4.40 (s, 2H), 4.27 (p, J = 5.9, 5.2 Hz, 2H), 4.12 (d, J = 6.8 Hz, 1H), 3.78 (s, 1H), 3.45-3.34 (m, 9H), 3.12-2.98 (m, 2H), 2.87 (dd, J = 16.6, 9.6 Hz, 3H), 2.64 (m, 9H), 2.25 (s, 1H), 2.16-1.94 (m, 5H), 1.80 (dp, J = 14.0, 6.7 Hz, 5H), 1.56 (p, J = 3.2 Hz, 5H), 1.24 (s, 1H), 1.08 (d, J = 6.2 Hz, 2H). |

TABLE 50-continued

Characterization data for intermediates prepared according to above.

| Intermediate | Structure | Chemical Name | MS: [(M + 1)]$^+$ | $^1$H NMR |
|---|---|---|---|---|
| I6 | 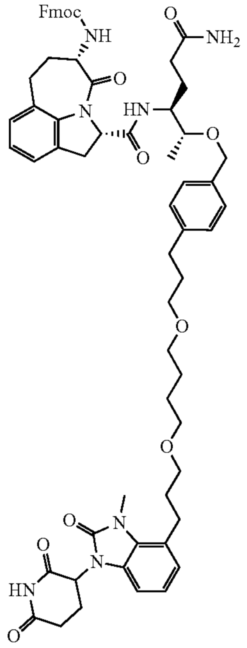 | 9H-fluoren-9-ylmethyl N-[(2S,11S)-2-[[(3S,4R)-1-carbamoyl-4-([4-[3-(4-[3-[1-(2,6-dioxopiperidin-3-yl)-3-methyl-2-oxo-1,3-benzodiazol-4-yl]propoxy]butoxy)propyl]phenyl]methoxy)pentan-3-yl]carbamoyl]-12-oxo-1-azatricyclo[6.4.1.0^[4,13]]trideca-4(13),5,7-trien-11-yl]carbamate | 1116.8 | (400 MHz, DMSO-$d_6$) δ 11.09 (s, 1H), 7.90 (d, J = 7.5 Hz, 2H), 7.84 (d, J = 9.0 Hz, 1H), 7.75 (q, J = 7.3 Hz, 3H), 7.43 (t, J = 7.4 Hz, 2H), 7.34 (t, J = 7.3 Hz, 2H), 7.17 (d, J = 7.5 Hz, 3H), 7.11 (d, J = 7.8 Hz, 2H), 7.05 (d, J = 7.7 Hz, 2H), 6.99-6.93 (m, 2H), 6.86 (t, J = 4.5 Hz, 1H), 6.69 (s, 1H), 5.36 (dd, J = 12.7, 5.4 Hz, 1H), 5.06 (d, J = 10.5 Hz, 1H), 4.40 (s, 2H), 4.27 (dd, J = 12.5, 7.0 Hz, 2H), 4.13 (s, 1H), 3.78 (s, 1H), 3.56 (s, 3H), 3.47-3.34 (m, 13 H), 3.30 (s, 1H), 2.95 (t, J = 7.9 Hz, 2H), 2.87 (s, 1H), 2.67-2.56 (m, 3H), 2.53 (s, 3 H), 2.25 (s, 1H), 2.08 (s, 2H), 1.80 (m , 5H), 1.57 (s, 5H), 1.08 (d, J = 6.2 Hz, 3H). |
| I7 | 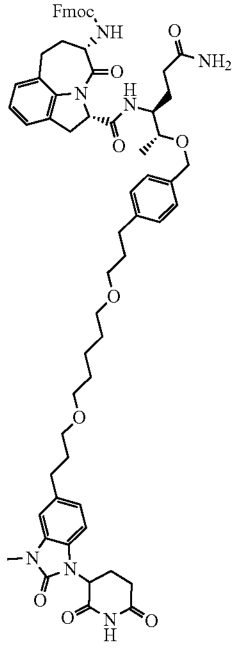 | 9H-fluoren-9-ylmethyl N-[(2S,11S)-2-[[(3S,4R)-1-carbamoyl-4-[(4-[3-[(6-[3-[1-(2,6-dioxopiperidin-3-yl)-3-methyl-2-oxo-1,3-benzodiazol-5-yl]propoxy]hexyl)oxy]propyl]phenyl)methoxy]pentan-3-yl]carbamoyl]-12-oxo-1-azatricyclo[6.4.1.0^[4,13]]trideca-4(13),5,7-trien-11-yl]carbamate | 1130.5 | (400 MHz, $CD_3OD$) δ 7.81 (d, J = 7.5 Hz, 1H), 7.70 (t, J = 8.3 Hz, 1H), 7.40 (d, J = 7.6 Hz, 1H), 7.32 (t, J = 7.5 Hz, 1H), 7.22 (d, J = 7.8 Hz, 2H), 7.15-6.91 (m, 6H), 5.30 (d, J = 7.5 Hz, 1H), 5.11 (d, J = 10.7 Hz, 1H), 4.48 (d, J = 8.7 Hz, 1H), 4.41 (dd, J = 17.8, 8.9 Hz, 1H), 4.25 (s, 1H), 3.97 (s, 1H), 3.56 (s, 1H), 3.44 (t, J = 6.5 Hz, 5H), 3.38 (s, 2H), 3.13 (s, 1H), 3.00 (d, J = 17.6 Hz, 1H), 2.94-2.85 (m, 1H), 2.81 (s, 1H), 2.75 (t, J = 7.5 Hz, 2H), 2.67 (t, J = 7.6 Hz, 1H), 2.24 (s, 2H), 2.16 (s, 2H), 1.99 (s, 1H), 1.88 (dq, J = 14.6, 7.5, 7.0 Hz, 3H), 1.62 (d, J = 8.5 Hz, 4H), 1.50 (d, J = 7.6 Hz, 2H), 1.31 (s, 1H), 1.18 (d, J = 6.3 Hz, 3H). |

TABLE 50-continued

| Inter-mediate | Structure | Chemical Name | MS: [(M + 1)]$^+$ | $^1$H NMR |
|---|---|---|---|---|
| Characterization data for intermediates prepared according to above. | | | | |
| I8 | 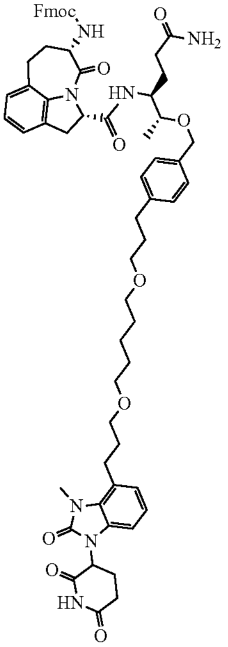 | 9H-fluoren-9-ylmethyl N-[(2S,11S)-2-[[(3S,4R)-1-carbamoyl-4-[(4-[3-[(5-[3-[1-(2,6-dioxopiperidin-3-yl)-3-methyl-2-oxo-1,3-benzodiazol-4-yl]propoxy]pentyl)oxy]propyl]phenyl)methoxy]pentan-3-yl]carbamoyl]-12-oxo-1-azatricyclo[6.4.1.0^[4,13]]trideca-4(13),5,7-trien-11-yl]carbamate | 1130.75 | (400 MHz, $CD_3OD$) δ 7.81 (d, J = 7.5 Hz, 2H), 7.72 (dt, J = 17.3, 8.1 Hz, 2H), 7.58 (s, 1H), 7.40 (t, J = 7.3 Hz, 2H), 7.32 (t, J = 7.5 Hz, 2H), 7.21 (d, J = 7.8 Hz, 2H), 7.15-6.89 (m, 9H), 5.33 (dd, J = 12.0, 5.0 Hz, 1H), 5.10 (d, J = 10.8 Hz, 1H), 4.50 (d, J = 11.6 Hz, 1H), 4.47-4.35 (m, 2H), 4.34-4.23 (m, 1H), 3.97 (d, J = 11.6 Hz, 1H), 3.64 (s, 3H), 3.55 (s, 2H), 3.52-3.40 (m, 7H), 3.40 (d, J = 11.0 Hz, 1H), 3.32 (s, 3H), 3.12 (s, 2H), 3.07-2.99 (m, 2H), 2.94-2.84 (m, 1H), 2.78 (d, J = 14.5 Hz, 2H), 2.67 (t, J = 7.7 Hz, 2H), 2.24 (d, J = 7.5 Hz, 2H), 2.18-2.03 (m, 3H), 1.88 (s, 4H), 1.85 (d, J = 6.7 Hz, 1H), 1.62 (m, 6H), 1.50 (d, J = 6.8 Hz, 1H), 1.18 (s, 3H). |
| I9 | 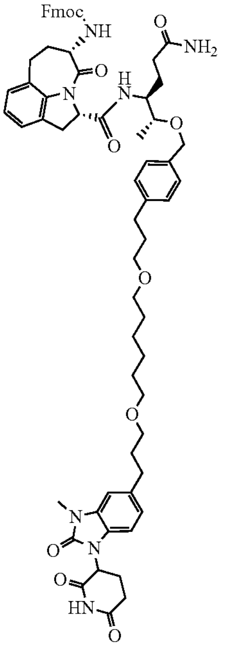 | 9H-fluoren-9-ylmethyl N-[(2S,11S)-2-[[(3S,4R)-1-carbamoyl-4-[(4-[3-[(6-[3-[1-(2,6-dioxopiperidin-3-yl)-3-methyl-2-oxo-1,3-benzodiazol-5-yl]propoxy]hexyl)oxy]propyl]phenyl)methoxy]pentan-3-yl]carbamoyl]-12-oxo-1-azatricyclo[6.4.1.0^[4,13]]trideca-4(13),5,7-trien-11-yl]carbamate | 1144.7 | (400 MHz, DMSO-$d_6$) δ 11.08 (s, 1H), 7.90 (d, J = 7.4 Hz, 2H), 7.83 (d, J = 9.2 Hz, 1H), 7.75 (q, J = 8.1, 7.6 Hz, 3H), 7.43 (t, J = 7.5 Hz, 2H), 7.34 (t, J = 7.3 Hz, 2H), 7.17 (m, 3H), 7.14-6.94 (m, 7H), 6.86 (d, J = 7.9 Hz, 1H), 6.69 (s, 1H), 5.34 (dd, J = 12.5, 5.5 Hz, 1H), 5.06 (d, J = 10.1 Hz, 1H), 4.40 (s, 2H), 4.26 (d, J = 8.0 Hz, 3H), 4.13 (s, 1H), 3.78 (s, 2H), 3.44 (s, 2H), 3.05 (s, 2H), 2.87 (s, 3H), 2.67-2.55 (m, 5H), 2.49 (m, 9H), 2.08 (s, 1H), 2.02 (s, 5H), 1.79 (dt, J = 15.7, 7.5 Hz, 6H), 1.51 (m, 6H), 1.33 (s, 1H), 1.24 (s, 1H), 1.08 (s, 3H). |

TABLE 50-continued

Characterization data for intermediates prepared according to above.

| Intermediate | Structure | Chemical Name | MS: [(M + 1)]$^+$ | $^1$H NMR |
|---|---|---|---|---|
| I10 | 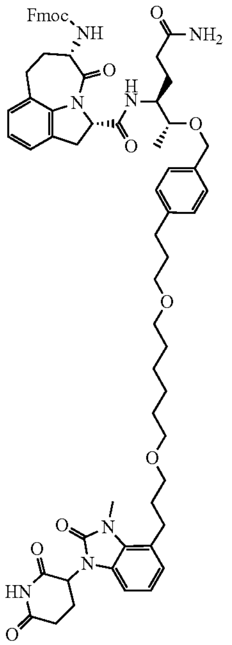 | 9H-fluoren-9-ylmethyl N-[(2S,11S)-2-[[(3S,4R)-1-carbamoyl-4-[(4-[3-[(6-[3-[1-(2,6-dioxopiperidin-3-yl)-3-methyl-2-oxo-1,3-benzodiazol-4-yl]propoxy]hexyl)oxy]propyl]phenyl)methoxy]pentan-3-yl]carbamoyl]-12-oxo-1-azatricyclo[6.4.1.0^[4,13]]trideca-4(13),5,7-trien-11-yl]carbamate | 1144.8 | (400 MHz, DMSO-$d_6$) δ 11.09 (s, 1H), 7.90 (dd, J = 7.7, 3.9 Hz, 2H), 7.84 (t, J = 7.3 Hz, 1H), 7.75 (q, J = 8.1, 7.6 Hz, 3H), 7.43 (t, J = 4.5 Hz, 2H), 7.34 (dd, J = 9.5, 5.6 Hz, 2H), 7.17 (d, J = 7.5 Hz, 3H), 7.10 (d, J = 7.8 Hz, 2H), 7.05 (d, J = 7.7 Hz, 2H), 7.00-6.91 (m, 3H), 6.86 (dd, J = 5.6, 3.3 Hz, 1H), 6.69 (s, 1H), 5.37 (dd, J = 12.5, 5.4 Hz, 1H), 5.06 (d, J = 10.6 Hz, 1H), 4.40 (s, 2H), 4.28 (dd, J = 12.7, 7.1 Hz, 2H), 4.13 (s, 1H), 3.78 (s, 1H), 3.56 (s, 3H), 3.33-3.46 (m, 8H), 2.95 (t, J = 7.9 Hz, 2H), 2.90-2.81 (m, 2H), 2.77-2.58 (m, 2H), 2.58 (d, J = 8.2 Hz, 2H), 2.51-2.52 (m, 3H), 2.12-1.94 (m, 5H), 1.69-1.85 (m, 6H), 1.52 (s, 5H), 1.50 (d, J = 5.6 Hz, 1H), 1.32-1.36 (m, 4H), 1.08 (d, J = 6.2 Hz, 3H). |
| I11 | 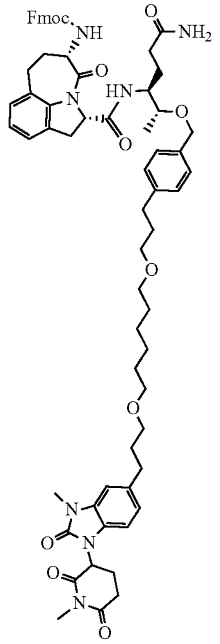 | 9H-fluoren-9-ylmethyl N-[(2S,11S)-2-[[(3S,4R)-1-carbamoyl-4-[(4-[3-[(6-[3-[3-methyl-1-(1-methyl-2,6-dioxopiperidin-3-yl)-2-oxo-1,3-benzodiazol-5-yl]propoxy]hexyl)oxy]propyl]phenyl)methoxy]pentan-3-yl]carbamoyl]-12-oxo-1-azatricyclo[6.4.1.0^[4,13]]trideca-4(13),5,7-trien-11-yl]carbamate | 1158.8 | (400 MHz, DMSO-$d_6$) δ 7.90 (d, J = 7.6 Hz, 2H), 7.83 (d, J = 9.2 Hz, 1H), 7.79-7.69 (m, 3H), 7.43 (t, J = 7.4 Hz, 2H), 7.34 (t, J = 7.4 Hz, 2H), 7.18 (s, 1H), 7.16 (s, 2H), 7.11 (d, J = 7.8 Hz, 2H), 7.05 (d, J = 7.6 Hz, 2H), 7.05-6.97 (m, 2H), 6.96 (t, J = 7.5 Hz, 1H), 6.85 (dd, J = 8.1, 1.6 Hz, 1H), 6.68 (s, 1H), 5.40 (dd, J = 13.0, 5.3 Hz, 1H), 5.06 (d, J = 10.4 Hz, 1H), 4.40 (s, 2H), 4.28 (dd, J = 12.5, 7.2 Hz, 3H), 4.13 (s, 1H), 3.78 (s, 1H), 3.48-3.41 (m, 1H), 3.35-3.39 (m, 7H), 3.32 (s, 4H), 3.09 (s, 1H), 3.04 (s, 3H), 3.02-2.91 (m, 1H), 2.86 (d, J = 16.6 Hz, 1H), 2.77 (d, J = 17.1 Hz, 1H), 2.74-2.65 (m, 1H), 2.67-2.53 (m, 4H), 2.08 (s, 3H), 2.06-1.94 (m, 1H), 1.92 (s, 1H), 1.87-1.71 (m, 6H), 1.51 (s, 6H), 1.39-1.29 (m, 4H), 1.08 (d, J = 6.2 Hz, 3H). |

TABLE 50-continued

| Characterization data for intermediates prepared according to above. | | | | |
|---|---|---|---|---|
| Intermediate | Structure | Chemical Name | MS: [(M + 1)]$^+$ | $^1$H NMR |
| I12 | 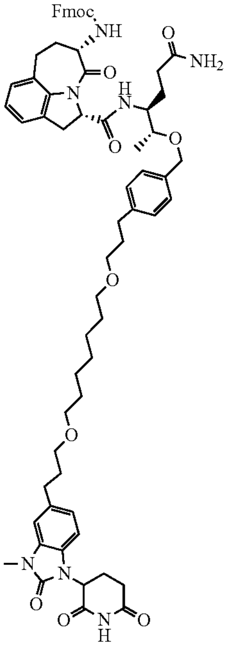 | 9H-fluoren-9-ylmethyl N-[(2S,11S)-2-[[(3S,4R)-1-carbamoyl-4-[(4-[3-[(7-[3-[1-(2,6-dioxopiperidin-3-yl)-3-methyl-2-oxo-1,3-benzodiazol-5-yl]propoxy]heptyl)oxy]propyl]phenyl)methoxy]pentan-3-yl]carbamoyl]-12-oxo-1-azatricyclo[6.4.1.0^[4,13]]trideca-4(13),5,7-trien-11-yl]carbamate | 1158.7 | (400 MHz, DMSO-$d_6$) δ 11.08 (s, 1H), 7.90 (d, J = 7.5 Hz, 2H), 7.84 (d, J = 9.2 Hz, 1H), 7.75 (q, J = 7.0 Hz, 3H), 7.43 (t, J = 7.5 Hz, 2H), 7.34 (t, J = 7.4 Hz, 2H), 7.17 (d, J = 7.5 Hz, 3H), 7.14-6.92 (m, 7H), 6.90-6.82 (m, 1H), 6.69 (s, 1H), 5.76 (s, 1H), 5.34 (dd, J = 12.6, 5.4 Hz, 1H), 5.06 (d, J = 10.5 Hz, 1H), 4.40 (s, 2H), 4.27 (s, 2H), 4.13 (s, 1H), 3.78 (s, 1H), 3.45 (d, J = 6.5 Hz, 1H), 3.35-3.34 (m, 5H), 3.06 (dt, J = 23.6, 12.4 Hz, 2H), 2.86 (dd, J = 16.4, 9.8 Hz, 2H), 2.77-2.54 (m, 7H), 2.11 (s, 0H), 2.08-1.97 (m, 10H), 1.85-1.72 (m, 6H), 1.50 (s, 1H), 1.36 (s, 3H), 1.35-1.25 (m, 6H), 1.24 (s, 1H), 1.08 (d, J = 6.2 Hz, 3H). |
| I13 | 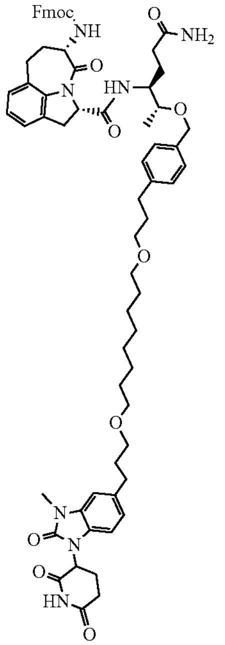 | 9H-fluoren-9-ylmethyl N-[(2S,11S)-2-[[(3S,4R)-1-carbamoyl-4-[(4-[3-[(8-[3-[1-(2,6-dioxopiperidin-3-yl)-3-methyl-2-oxo-1,3-benzodiazol-5-yl]propoxy]octyl)oxy]propyl]phenyl)methoxy]pentan-3-yl]carbamoyl]-12-oxo-1-azatricyclo[6.4.1.0^[4,13]]trideca-4(13),5,7-trien-11-yl]carbamate | 1172.5 | (400 MHz, DMSO-$d_6$) δ 11.08 (s, 1H), 7.90 (d, J = 7.5 Hz, 2H), 7.84 (d, J = 9.1 Hz, 1H), 7.75 (q, J = 6.5, 5.8 Hz, 3H), 7.43 (t, J = 7.5 Hz, 2H), 7.34 (t, J = 7.4 Hz, 2H), 7.19-7.13 (m, 3H), 7.14-6.92 (m, 7H), 6.90-6.83 (m, 1H), 6.69 (s, 1H), 5.34 (dd, J = 12.7, 5.3 Hz, 1H), 5.06 (d, J = 10.3 Hz, 1H), 4.40 (s, 2H), 4.27 (dd, J = 12.4, 7.0 Hz, 2H), 4.13 (s, 1H), 3.78 (s, 2H), 3.48-3.29 (m, 7H), 3.13-2.98 (m, 2H), 2.97-2.81 (m, 2H), 2.76-2.61 (m, 3H), 2.58 (t, J = 7.6 Hz, 3H), 2.19 (s, 1H), 2.08 (s, 1H), 2.07-2.04 (m, 4H), 2.03-1.95 (m, 1H), 1.89-1.70 (m, 6H), 1.60-1.45 (m, 5H), 1.40-1.35 (m, 3H), 1.31-1.22 (m, 8H), 1.08 (d, J = 6.2 Hz, 3H). |

TABLE 50-continued

Characterization data for intermediates prepared according to above.

| Intermediate | Structure | Chemical Name | MS: [(M + 1)]$^+$ | $^1$H NMR |
|---|---|---|---|---|
| I14 | 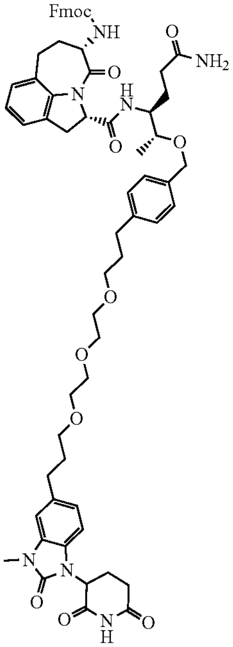 | 9H-fluoren-9-ylmethyl N-[(2S,11S)-2-[[(3S,4R)-1-carbamoyl-4-[(4-[3-[2-(2-[3-[1-(2,6-dioxopiperidin-3-yl)-3-methyl-2-oxo-1,3-benzodiazol-5-yl]propoxy]ethoxy)ethoxy]propyl]phenyl)methoxy]pentan-3-yl]carbamoyl]-12-oxo-1-azatricyclo[6.4.1.0^[4,13]]trideca-4(13),5,7-trien-11-yl]carbamate | 1132.7 | (400 MHz, DMSO-$d_6$) δ 11.08 (s, 1H), 7.90 (d, J = 7.6 Hz, 2H), 7.77-7.67 (m, 3H), 7.43 (t, J = 7.4 Hz, 2H), 7.34 (t, J = 7.5 Hz, 2H), 7.25-7.13 (m, 3H), 7.10 (d, J = 7.8 Hz, 2H), 7.07-7.00 (m, 4H), 7.00-6.92 (m, 2H), 6.86 (dd, J = 8.0, 1.6 Hz, 1H), 6.68 (s, 1H), 5.76 (s, 3H), 5.33 (dd, J = 12.7, 5.3 Hz, 1H), 5.12-5.02 (m, 1H), 4.40 (s, 2H), 4.34-4.25 (m, 3H), 4.13 (s, 1H), 3.76 (d, J = 18.5 Hz, 1H), 3.57-3.53 (m, 4H), 3.52-3.47 (m, 4H), 3.45-3.35 (m, 5H), 3.18-2.97 (m, 2H), 2.93-2.80 (m, 3H), 2.72-2.63 (m, 3H), 2.62-2.54 (m, 3H), 2.16-1.94 (m, 5H), 1.87-1.70 (m, 5H), 1.56 (s, 1H), 1.07 (d, J = 6.3 Hz, 3H). |
| I15 | 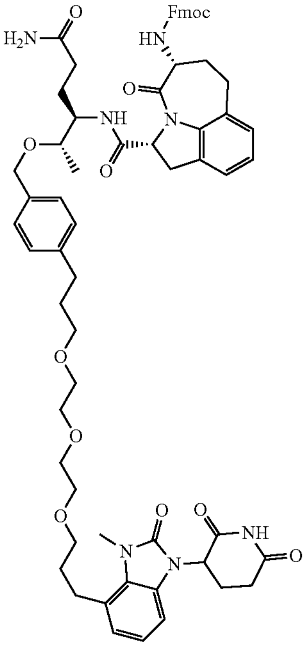 | 9H-fluoren-9-ylmethyl N-[(2S,11S)-2-[[(3S,4R)-1-carbamoyl-4-[(4-[3-[2-(2-[3-[1-(2,6-dioxopiperidin-3-yl)-3-methyl-2-oxo-1,3-benzodiazol-4-yl]propoxy]ethoxy)ethoxy]propyl]phenyl)methoxy]pentan-3-yl]carbamoyl]-12-oxo-1-azatricyclo[6.4.1.0^[4,13]]trideca-4(13),5,7-trien-11-yl]carbamate | 1132.8 | (400 MHz, DMSO-$d_6$) δ 11.09 (s, 1H), 7.98-7.67 (m, 6H), 7.54 (s, 1H), 7.44-7.30 (m, 4H), 7.19-6.91 (m, 9H), 6.86 (dd, J = 5.9, 3.1 Hz, 1H), 6.69 (s, 1H), 5.82-5.65 (m, 5H), 5.36 (dd, J = 12.5, 5.4 Hz, 1H), 5.06 (d, J = 10.5 Hz, 1H), 4.39 (s, 2H), 4.30-4.22 (m, 3H), 4.16-4.07 (m, 1H), 3.78 (s, 1H), 3.58-3.35 (m, 15H), 3.13-3.03 (m, 1H), 2.95 (t, J = 7.8 Hz, 2H), 2.85 (d, J = 17.8 Hz, 2H), 2.73-2.63 (m, 1H), 2.59 (t, J = 7.6 Hz, 2H), 2.14-1.95 (m, 4H), 1.82-1.66 (m, 5H), 1.55 (d, J = 11.8 Hz, 1H), 1.07 (d, J = 6.2 Hz, 3H). |

TABLE 50-continued

Characterization data for intermediates prepared according to above.

| Intermediate | Structure | Chemical Name | MS: [(M + 1)]+ | $^1$H NMR |
|---|---|---|---|---|
| I16 | 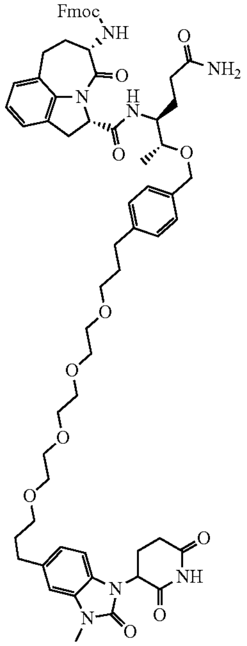 | (9H-fluoren-9-yl)methyl N-[(2S,11S)-2-[[(3S,4R)-1-carbamoyl-4-[(4-[16-[1-(2,6-dioxopiperidin-3-yl)-3-methyl-2-oxo-2,3-dihydro-1H-1,3-benzodiazol-5-yl]-4,7,10,13-tetraoxahexadecan-1-yl]phenyl)methoxy] pentan-3-yl]carbamoyl]-12-oxo-1-azatricyclo[6.4.1.0^[4,13]] trideca-4(13),5,7-trien-11-yl]carbamate | $[(M/2 + 18)]^+$ = 606.4 | (400 MHz, DMSO-$d_6$) δ 11.10 (s, 1H), 7.94-7.82 (m, 3H), 7.81-7.72 (m, 3H), 7.43 (t, J = 7.5 Hz, 2H), 7.35 (t, J = 7.4 Hz, 2H), 7.22-7.14 (m, 3H), 7.11 (d, J = 7.9 Hz, 2H), 7.08-6.93 (m, 5H), 6.87 (dd, J = 8.1, 1.6 Hz, 1H), 6.71 (s, 1H), 5.34 (dd, J = 12.7, 5.4 Hz, 1H), 5.06 (d, J = 10.2 Hz, 1H), 4.40 (s, 2H), 4.28 (dd, J = 12.3, 6.8 Hz, 2H), 4.12 (dd, J = 8.5, 3.8 Hz, 1H), 3.79 (s, 2H), 3.58-3.30 (m, 17H), 3.16-2.99 (m, 1H), 2.87 (t, J = 13.9 Hz, 2H), 2.77-2.54 (m, 6H), 2.54-2.51 (m, 7H), 2.09 (s, 1H), 2.07-1.96 (m, 1H), 1.85-1.69 (m, 6H), 1.56 (s, 1H), 1.08 (d, J = 6.2 Hz, 3H). |
| I17 | 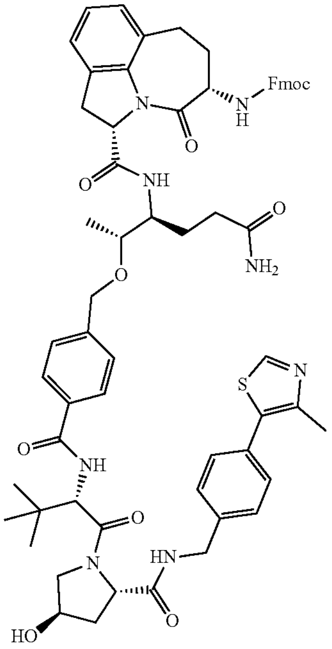 | 9H-fluoren-9-ylmethyl N-[(2S,11S)-2-[[(3S,4R)-1-carbamoyl-4-[(4-[[(2S)-1-(2S,4R)-4-hydroxy-2-([[4-(4-methyl-1,3-thiazol-5-yl)phenyl]methyl] carbamoyl)pyrrolidin-1-yl]-3,3-dimethyl-1-oxobutan-2-yl]carbamoyl]phenyl) methoxy]pentan-3-yl]carbamoyl]-12-oxo-1-azatricyclo[6.4.1.0^[4,13]] trideca-4(13),5,7-trien-11-yl]carbamate | 1143.8 | (400 MHz, DMSO-$d_6$) δ 8.97 (d, J = 11.4 Hz, 1H), 8.58 (d, J = 7.5 Hz, 1H), 7.92-7.83 (m, 4H), 7.79 (t, J = 8.3 Hz, 1H), 7.75-7.71 (m, 4H), 7.45-7.36 (m, 5H), 7.34-7.30 (m, 4H), 7.17 (s, 1H), 7.05 (d, J = 8.3 Hz, 2H), 7.00 (d, J = 14.2 Hz, 1H), 6.96 (s, 1H), 6.69 (s, 1H), 5.16 (d, J = 3.6 Hz, 1H), 5.06 (s, 1H), 4.78 (t, J = 8.5 Hz, 1H), 4.54-4.43 (m, 3H), 4.39 (s, 1H), 4.28 (s, 1H), 4.32-4.20 (m, 4H), 3.82 (s, 1H), 3.73 (d, J = 8.1 Hz, 2H), 3.32-3.26 (m, 3H), 3.18 (d, J = 5.2 Hz, 1H), 3.06 (s, 2H), 2.88-2.79 (m, 1H), 2.50-2.40 (m, 4H), 2.13-2.01 (m, 6H), 1.78 (s, 2H), 1.56 (s, 1H), 1.04 (d, J = 9.0 Hz, 9H). |

TABLE 50-continued

| Characterization data for intermediates prepared according to above. | | | | |
|---|---|---|---|---|
| Intermediate | Structure | Chemical Name | MS: [(M + 1)]$^+$ | $^1$H NMR |
| I18 | 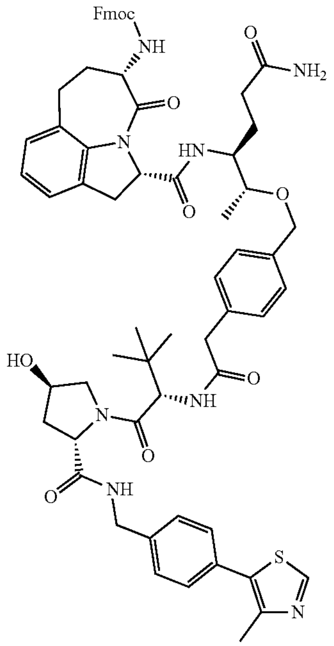 | 9H-fluoren-9-ylmethyl N-[(2S,11S)-2-[[(3S,4R)-1-carbamoyl-4-[[4-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methyl)phenyl]methoxy]pentan-3-yl]carbamoyl]-12-oxo-1-azatricyclo[6.4.1.0^[4,13]]trideca-4(13),5,7-trien-11-yl]carbamate | 1157.8 | (400 MHz, DMSO-$d_6$) δ 8.99 (s, 1H), 8.58 (t, J = 6.1 Hz, 1H), 8.10 (d, J = 9.3 Hz, 1H), 7.90 (d, J = 7.5 Hz, 2H), 7.85 (d, J = 9.2 Hz, 1H), 7.78-7.71 (m, 3H), 7.54 (s, 1H), 7.47-7.30 (m, 8H), 7.25-7.14 (m, 5H), 7.06 (d, J = 7.9 Hz, 2H), 6.97 (t, J = 7.5 Hz, 1H), 5.12 (d, J = 3.6 Hz, 1H), 5.10-5.02 (m, 1H), 4.53 (d, J = 9.4 Hz, 1H), 4.49-4.38 (m, 4H), 4.35 (s, 1H), 4.32-4.18 (m, 4H), 4.12 (d, J = 7.1 Hz, 1H), 3.78 (s, 1H), 3.71-3.59 (m, 3H), 3.45-3.37 (m, 1H), 3.32 (s, 3H), 3.08 (dd, J = 16.6, 7.4 Hz, 1H), 2.47-2.43 (m, 3H), 2.08-2.07 (m, 3H), 2.08 (s, 3H), 2.04 (s, 2H), 2.04 (d, J = 16.8 Hz, 2H), 1.96-1.85 (m, 1H), 1.07 (d, J = 6.2 Hz, 3H), 0.92 (s, 9H). |
| I19 | 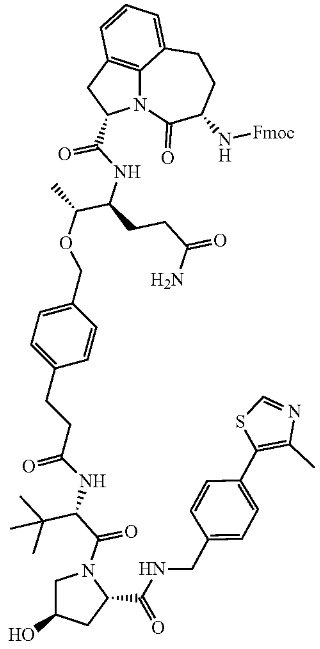 | 9H-fluoren-9-ylmethyl N-[(2S,11S)-2-[[(3S,4R)-1-carbamoyl-4-[[4-(2-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]ethyl)phenyl]methoxy]pentan-3-yl]carbamoyl]-12-oxo-1-azatricyclo[6.4.1.0^[4,13]]trideca-4(13),5,7-trien-11-yl]carbamate | 1171.8 | (400 MHz, $CDCl_3$) δ 8.71 (s, 1H), 7.79 (d, J = 7.6 Hz, 2H), 7.64 (d, J = 7.4 Hz, 2H), 7.53 (s, 1H), 7.46-7.39 (m, 2H), 7.38-7.30 (m, 5H), 7.26 (s, 1H), 7.13 (d, J = 7.4 Hz, 1H), 7.12-7.02 (m, 3H), 6.84 (d, J = 10.1 Hz, 1H), 6.22-6.07 (m, 1H), 5.92 (d, J = 46.8 Hz, 1H), 5.21-5.05 (m, 1H), 4.97 (s, 1H), 4.68 (d, J = 8.0 Hz, 1H), 4.61 (d, J = 11.8 Hz, 1H), 4.52 (d, J = 8.0 Hz, 3H), 4.43 (d, J = 7.6 Hz, 2H), 4.35 (d, J = 19.6 Hz, 2H), 4.28-4.19 (m, 1H), 4.06-3.82 (m, 2H), 3.60 (dd, J = 10.7, 4.0 Hz, 2H), 3.44-3.31 (m, 2H), 3.21 (d, J = 8.3 Hz, 1H), 3.10 (d, J = 17.3 Hz, 1H), 2.96 (t, J = 7.4 Hz, 1H), 2.88 (s, 1H), 2.62 (s, 1H), 2.60-2.50 (m, 4H), 2.43 (s, 1H), 2.29 (s, 1H), 2.12 (d, J = 12.3 Hz, 1H), 2.03 (s, 3H), 1.88-1.78 (m, 3H), 1.21 (d, J = 6.7 Hz, 3H), 0.90 (s, 9H). |

TABLE 50-continued

| Characterization data for intermediates prepared according to above. | | | | |
|---|---|---|---|---|
| Inter-mediate | Structure | Chemical Name | MS: [(M + 1)]$^+$ | $^1$H NMR |
| I20 | 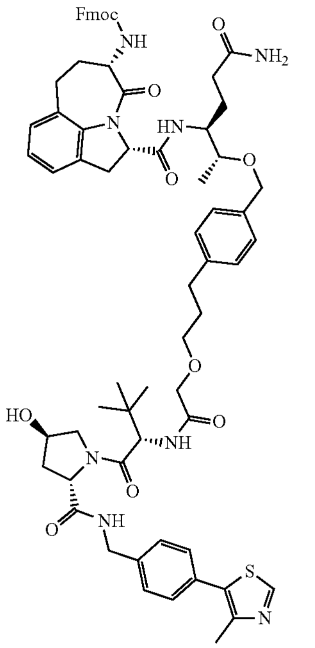 | 9H-fluoren-9-ylmethyl N-[(2S,11S)-2-[[(3S,4R)-1-carbamoyl-4-([4-[3-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methoxy)propyl]phenyl]methoxy)pentan-3-yl]carbamoyl]-12-oxo-1-azatricyclo[6.4.1.0^[4,13]]trideca-4(13),5,7-trien-11-yl]carbamate | 1215.8 | (400 MHz, DMSO-$d_6$) δ 8.97 (s, 1H), 8.61 (t, J = 6.2 Hz, 1H), 7.90 (d, J = 7.6 Hz, 2H), 7.84 (d, J = 9.1 Hz, 1H), 7.80-7.69 (m, 3H), 7.43-7.35 (m, 9H), 7.18-7.11 (m, 5H), 7.05 (d, J = 7.6 Hz, 2H), 6.97 (d, J = 7.4 Hz, 1H), 6.69 (s, 1H), 5.81-5.72 (m, 3H), 5.16 (d, J = 3.5 Hz, 1H), 5.06 (d, J = 10.7 Hz, 1H), 4.57 (d, J = 9.5 Hz, 1H), 4.46 (t, J = 8.3 Hz, 1H), 4.38 (s, 2H), 4.30-4.23 (m, 3H), 4.13 (s, 1H), 3.94 (s, 2H), 3.78 (s, 1H), 3.70-3.59 (m, 2H), 3.58 (s, 1H), 3.52-3.44 (m, 4H), 3.06 (s, 2H), 2.85 (d, J = 16.8 Hz, 1H), 2.64 (t, J = 7.8 Hz, 2H), 2.42 (s, 2H), 2.15-2.04 (m, 5H), 1.95-1.71 (m, 4H), 1.07 (d, J = 6.2 Hz, 3H), 0.95 (s, 9H). |
| I21 | 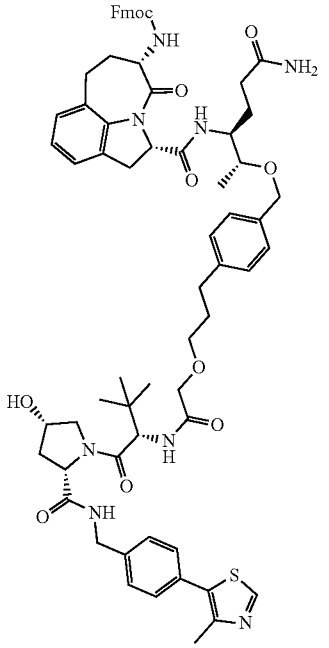 | 9H-fluoren-9-ylmethyl N-[(2S,11S)-2-[[(3S,4R)-1-carbamoyl-4-([4-[3-([[(2S)-1-[(2S,4S)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methoxy)propyl]phenyl]methoxy)pentan-3-yl]carbamoyl]-12-oxo-1-azatricyclo[6.4.1.0^[4,13]]trideca-4(13),5,7-trien-11-yl]carbamate | 1215.8 | (400 MHz, DMSO-$d_6$) δ 8.97 (s, 1H), 8.67 (t, J = 6.0 Hz, 1H), 7.90 (d, J = 7.5 Hz, 2H), 7.83 (d, J = 9.2 Hz, 1H), 7.77-7.70 (m, 3H), 7.48-7.35 (m, 7H), 7.16-7.10 (m, 6H), 7.07-7.01 (m, 3H), 7.00-6.93 (m, 1H), 5.76 (s, 1H), 5.45 (d, J = 7.3 Hz, 1H), 5.06 (d, J = 10.4 Hz, 1H), 4.54 (d, J = 9.3 Hz, 1H), 4.47-4.35 (m, 5H), 4.35-4.24 (m, 5H), 4.12 (d, J = 10.6 Hz, 1H), 3.93 (d, J = 2.2 Hz, 2H), 3.63-3.50 (m, 7H), 3.46 (dt, J = 11.9, 6.2 Hz, 3H), 2.86 (d, J = 16.6 Hz, 1H), 2.64 (t, J = 7.7 Hz, 2H), 2.43 (s, 3H), 2.12-2.07 (m, 5H), 1.08 (d, J = 6.1 Hz, 3H), 0.97 (s, 9H). |

TABLE 50-continued

| Characterization data for intermediates prepared according to above. | | | | |
|---|---|---|---|---|
| Intermediate | Structure | Chemical Name | MS: [(M + 1)]+ | 1H NMR |
| I22 | 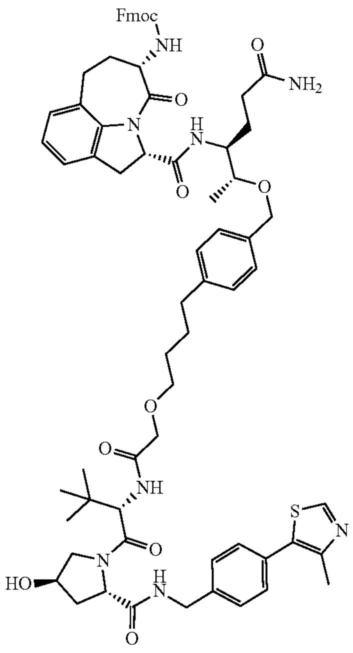 | 9H-fluoren-9-ylmethyl N-[(2S,11S)-2-[[(3S,4R)-1-carbamoyl-4-([4-[4-([[(2,S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methoxy)butyl]phenyl]methoxy)pentan-3-yl]carbamoyl]-12-oxo-1-azatricyclo[6.4.1.0^[4,13]]trideca-4(13),5,7-trien-11-yl]carbamate | 1229.2 | (400 MHz, DMSO-$d_6$) δ 8.98 (d, J = 2.4 Hz, 1H), 8.60 (s, 1H), 7.91 (d, J = 7.5 Hz, 2H), 7.83 (d, J = 9.4 Hz, 1H), 7.80-7.66 (m, 3H), 7.47-7.29 (m, 9H), 7.19-7.09 (m, 5H), 7.05 (d, J = 7.8 Hz, 2H), 6.97 (d, J = 7.0 Hz, 1H), 6.68 (s, 1H), 5.82-5.71 (m, 4H), 5.15 (s, 1H), 5.06 (d, J = 10.6 Hz, 1H), 4.57 (d, J = 9.6 Hz, 1H), 4.47 (d, J = 8.3 Hz, 1H), 4.34-4.30 (m, 3H), 4.30-4.22 (m, 3H), 4.13 (s, 1H), 3.92 (s, 1H), 3.78 (s, 1H), 3.70-3.58 (m, 2H), 3.50 (s, 4H), 3.06 (s, 1H), 2.86 (d, J = 16.8 Hz, 1H), 2.58 (d, J = 6.8 Hz, 2H), 2.47-2.42 (m, 3H), 2.15-2.00 (m, 4H), 1.90 (d, J = 10.5 Hz, 1H), 1.79 (s, 1H), 1.74-1.57 (m, 5H), 1.07 (d, J = 6.2 Hz, 3H), 0.95 (d, J = 1.9 Hz, 9H). |
| I23 | 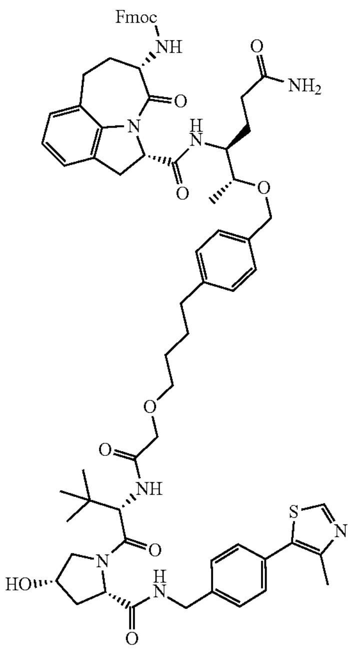 | 9H-fluoren-9-ylmethyl N-[(2S,11S)-2-[[(3S,4R)-1-carbamoyl-4-([4-[4-([[(2,S)-1-[(2S,4S)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methoxy)butyl]phenyl]methoxy)pentan-3-yl]carbamoyl]-12-oxo-1-azatricyclo[6.4.1.0^[4,13]]trideca-4(13),5,7-trien-11-yl]carbamate | 1229.7 | (400 MHz, DMSO-$d_6$) δ 8.98 (s, 1H), 8.66 (d, J = 5.9 Hz, 1H), 7.90 (d, J = 7.6 Hz, 2H), 7.83 (d, J = 9.3 Hz, 1H), 7.80-7.70 (m, 3H), 7.47-7.30 (m, 7H), 7.20-7.11 (m, 3H), 7.10 (d, J = 7.9 Hz, 2H), 7.05 (d, J = 7.6 Hz, 2H), 7.00-6.92 (m, 1H), 6.68 (s, 1H), 5.44 (d, J = 7.3 Hz, 1H), 5.06 (d, J = 10.4 Hz, 1H), 4.52 (d, J = 9.3 Hz, 1H), 4.47-4.34 (m, 4H), 4.34-4.20 (m, 5H), 4.13 (s, 1H), 3.93-3.85 (m, 2H), 3.78 (s, 1H), 3.51-3.39 (m, 4H), 3.05 (s, 2H), 2.86 (d, J = 16.9 Hz, 1H), 2.58 (t, J = 7.3 Hz, 2H), 2.50-2.49 (m, 5H), 2.43 (s, 3H), 2.08 (s, 1H), 1.75 (s, 1H), 1.62 (d, J = 8.3 Hz, 2H), 1.58-1.52 (m, 4H), 1.07 (d, J = 6.2 Hz, 3H), 0.95 (s, 9H). |

TABLE 50-continued

| Characterization data for intermediates prepared according to above. | | | | |
|---|---|---|---|---|
| Inter-mediate | Structure | Chemical Name | MS: [(M + 1)]+ | $^1$H NMR |
| I24 | 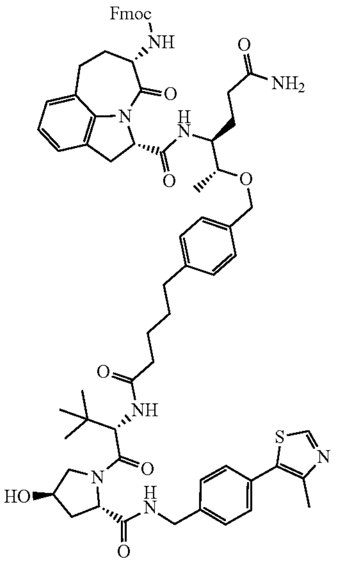 | 9H-fluoren-9-ylmethyl N-[(2S,11S)-2-[[(3S,4R)-1-carbamoyl-4-[[4-(4-[[(2S)-1-[(2S,4R)-4-hydroxy-2-([[4-(4-methyl-1,3-thiazol-5-yl)phenyl]methyl] carbamoyl)pyrrolidin-1-yl]-3,3-dimethyl-1-oxobutan-2-yl]carbamoyl]butyl) phenyl]methoxy]pentan-3-yl]carbamoyl]-12-oxo-1-azatricyclo[6.4.1.0^[4,13]] trideca-4(13),5,7-trien-11-yl]carbamate | 1200.0 | (400 MHz, $CD_3OD$) δ 8.88 (s, 1H), 8.63 (t, J = 6.1 Hz, 1H), 7.81 (d, J = 7.8 Hz, 2H), 7.69 (t, J = 8.4 Hz, 2H), 7.47 (d, J = 8.1 Hz, 2H), 7.43-7.38 (m, 4H), 7.32 (t, J = 7.5 Hz, 2H), 7.22 (d, J = 7.9 Hz, 2H), 7.12 (d, J = 7.9 Hz, 2H), 7.10-7.00 (m, 3H), 5.12 (d, J = 10.6 Hz, 1H), 4.65 (d, J = 8.9 Hz, 1H), 4.57 (t, J = 8.3 Hz, 1H), 4.49 (s, 1H), 4.46 (d, J = 11.4 Hz, 1H), 4.38 (d, J = 5.9 Hz, 1H), 4.36-4.29 (m, 2H), 4.25 (t, J = 6.9 Hz, 1H), 4.02-3.88 (m, 2 H), 3.81 (dd, J = 10.9, 3.9 Hz, 1H), 3.63 (q, J = 7.1 Hz, 1H), 3.58-3.53 (m, 1H), 3.46 (dd, J = 16.5, 11.0 Hz, 1H), 3.37 (s, 4H), 3.14 (s, 2H), 3.01 (d, J = 16.9 Hz, 1H), 2.62 (s, 2H), 2.48 (s, 3H), 2.31-2.15 (m, 6H), 2.09 (ddd, J = 13.3, 9.1, 4.6 Hz, 1H), 2.01 (s, 1H), 1.70-1.61 (m, 4H), 1.20-1.17 (m, 3H), 1.04 (s, 9H). |
| I25 | 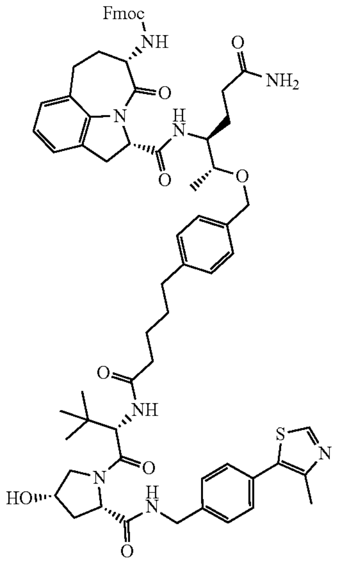 | 9H-fluoren-9-ylmethyl N-[(2S,11S)-2-[[(3S,4R)-1-carbamoyl-4-[[4-(4-[[(2S)-1-[(2S,4S)-4-hydroxy-2-([[4-(4-methyl-1,3-thiazol-5-yl)phenyl]methyl] carbamoyl)pyrrolidin-1-yl]-3,3-dimethyl-1-oxobutan-2-yl]carbamoyl]butyl) phenyl]methoxy]pentan-3-yl]carbamoyl]-12-oxo-1-azatricyclo[6.4.1.0^[4,13]] trideca-4(13),5,7-trien-11-yl]carbamate | 1199.1 | (400 MHz, DMSO-$d_6$) δ 8.99 (d, J = 2.5 Hz, 1H), 8.62 (t, J = 6.1 Hz, 1H), 7.93-7.86 (m, 2H), 7.88-7.80 (m, 1H), 7.79-7.63 (m, 3H), 7.47-7.24 (m, 9H), 7.17 (d, J = 7.7 Hz, 3H), 7.13-7.02 (m, 4H), 6.97 (t, J = 7.4 Hz, 1H), 6.68 (s, 1H), 5.43 (dd, J = 6.9, 1.7 Hz, 1H), 5.10-5.03 (m, 1H), 4.51-4.32 (m, 4H), 4.29-4.20 (m, 4H), 3.94 (dd, J = 10.2, 5.7 Hz, 1H), 3.79 (s, 1H), 3.44 (dd, J = 9.7, 5.3 Hz, 3H), 2.86 (d, J = 16.6 Hz, 1H), 2.54 (d, J = 7.5 Hz, 2H), 2.44 (d, J = 3.5 Hz, 3H), 2.31 (s, 2H), 2.50-2.49 (m, 4H), 2.09 (s, 4H), 2.08 (s, 2H), 1.75 (dt, J = 12.3, 5.9 Hz, 1H), 1.58-1.47 (m, 5H), 1.08 (d, J = 6.2 Hz, 3H), 0.96-0.89 (m, 9H). |

TABLE 50-continued

| Characterization data for intermediates prepared according to above. | | | | |
|---|---|---|---|---|
| Intermediate | Structure | Chemical Name | MS: [(M + 1)]$^+$ | $^1$H NMR |
| I26 | 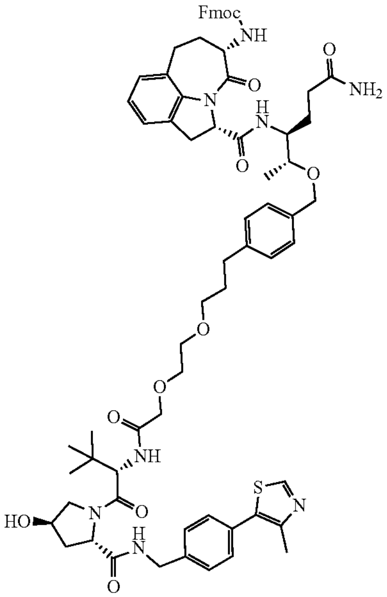 | 9H-fluoren-9-ylmethyl N-[(2S,11S)-2-[[(3S,4R)-1-carbamoyl-4-[(4-[3-[2-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methoxy)ethoxy]propyl]phenyl)methoxy]pentan-3-yl]carbamoyl]-12-oxo-1-azatricyclo[6.4.1.0^[4,13]]trideca-4(13),5,7-trien-11-yl]carbamate | 1259.7 | (400 MHz, DMSO-$d_6$) δ 8.97 (s, 1H), 8.60 (t, J = 6.1 Hz, 1H), 7.95-7.81 (m, 3H), 7.80-7.71 (m, 3H), 7.47-7.38 (m, 6H), 7.37-7.30 (m, 3H), 7.21-7.13 (m, 3H), 7.12-7.00 (m, 4H), 6.97 (d, J = 7.4 Hz, 1H), 6.70 (s, 1H), 5.22-5.03 (m, 2H), 4.58 (d, J = 9.5 Hz, 1H), 4.49-4.33 (m, 5H), 4.14 (d, J = 9.5 Hz, 1H), 3.99 (s, 2H), 3.78 (s, 1H), 3.71-3.37 (m, 11H), 3.18-2.99 (m, 2H), 2.85 (d, J = 16.3 Hz, 1H), 2.58 (t, J = 7.8 Hz, 2H), 2.43 (s, 3H), 2.16-1.97 (m, 5H), 1.97-1.86 (m, 3H), 1.79 (t, J = 7.5 Hz, 3H), 1.55 (s, 1H), 1.06 (t, J = 6.9 Hz, 3H), 0.96 (s, 9H). |
| I27 | 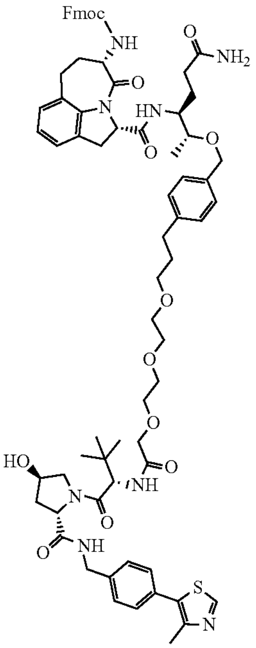 | 9H-fluoren-9-ylmethyl N-[(2S,11S)-2-[[(3S,4R)-1-carbamoyl-4-[[4-(3-[2-[2-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methoxy)ethoxy]ethoxy]propyl)phenyl]methoxy]pentan-3-yl]carbamoyl]-12-oxo-1-azatricyclo[6.4.1.0^[4,13]]trideca-4(13),5,7-trien-11-yl]carbamate | [(M/2 + 1)]$^+$ = 652.8 | (400 MHz, DMSO-$d_6$) δ 8.98 (s, 1H), 8.60 (t, J = 6.0 Hz, 1H), 7.90 (d, J = 7.6 Hz, 2H), 7.84 (d, J = 9.3 Hz, 1H), 7.81-7.71 (m, 3H), 7.46-7.38 (m, 6H), 7.35 (q, J = 7.1 Hz, 3H), 7.19-7.12 (m, 3H), 7.12-7.03 (m, 4H), 6.97 (d, J = 7.4 Hz, 1H), 6.69 (s, 1H), 5.15 (d, J = 3.5 Hz, 1H), 5.06 (d, J = 10.3 Hz, 1H), 4.57 (d, J = 9.5 Hz, 1H), 4.45 (t, J = 8.2 Hz, 1H), 4.42-4.34 (m, 5H), 4.31-4.21 (m, 4H), 4.13 (d, J = 6.5 Hz, 1H), 3.98 (s, 2H), 3.78 (s, 1H), 3.68 (dd, J = 10.7, 3.8 Hz, 1H), 3.65-3.51 (m, 7H), 3.49 (t, J = 4.8 Hz, 2H), 3.44 (t, J = 6.7 Hz, 2H), 3.39 (d, J = 5.9 Hz, 1H), 3.36 (d, J = 6.3 Hz, 1H), 3.05 (t, J = 15.6 Hz, 2H), 2.91-2.79 (m, 2H), 2.62-2.53 (m, 3H), 2.44 (s, 3 H), 2.04 (q, J = 8.3, 6.8 Hz, 2H), 1.83-1.70 (m, 3H), 1.55 (d, J = 12.1 Hz, 1H), 1.08 (d, J = 6.2 Hz, 3H), 0.95 (s, 9H). |

TABLE 50-continued

Characterization data for intermediates prepared according to above.

| Inter-mediate | Structure | Chemical Name | MS: [(M + 1)]$^+$ | $^1$H NMR |
|---|---|---|---|---|
| I28 | 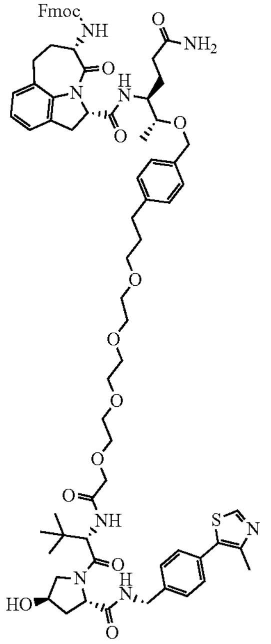 | 9H-fluoren-9-ylmethyl N-[(2S,11S)-2-[[(3S,4R)-1-carbamoyl-4-[[4-(1-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]-2,5,8,11-tetraoxatetradecan-14-yl)phenyl]methoxy]pentan-3-yl]carbamoyl]-12-oxo-1-azatricyclo[6.4.1.0^[4,13]]trideca-4(13),5,7-trien-11-yl]carbamate | [(M + 23)]$^+$ = 1370.0 | (400 MHz, DMSO-$d_6$) δ 8.98 (d, J = 3.2 Hz, 1H), 8.60 (s, 1H), 7.90 (d, J = 7.4 Hz, 2H), 7.84 (d, J = 8.8 Hz, 1H), 7.82-7.70 (m, 3H), 7.46-7.36 (m, 7H), 7.34 (t, J = 7.4 Hz, 2H), 7.22-7.15 (m, 3H), 7.14-7.02 (m, 4H), 6.97 (d, J = 7.7 Hz, 1H), 6.69 (s, 1H), 5.15 (d, J = 3.5 Hz, 1H), 5.06 (d, J = 10.5 Hz, 1H), 4.57 (d, J = 9.7 Hz, 1H), 4.49-4.35 (m, 5H), 4.30-4.24 (m, 3H), 4.11-4.05 (m, 3H), 3.97 (s, 2H), 3.78 (s, 1H), 3.68-3.44 (m, 12H), 3.40-3.28 (m, 10H), 2.62-2.55 (m, 3H), 2.50-2.42 (m, 3H), 2.11-2.04 (m, 5H), 1.91 (s, 1H), 1.08 (d, J = 6.3 Hz, 3H), 0.94 (d, J = 2.7 Hz, 9H). |
| I29 | 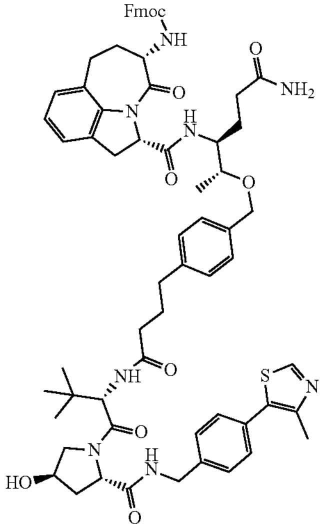 | 9H-fluoren-9-ylmethyl N-[(2S,11S)-2-[[(3S,4R)-1-carbamoyl-4-[[4-(3-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]propyl)phenyl]methoxy]pentan-3-yl]carbamoyl]-12-oxo-1-azatricyclo[6.4.1.0^[4,13]]trideca-4(13),5,7-trien-11-yl]carbamate | 1185.5 | (400 MHz, DMSO-$d_6$) δ 8.99 (s, 1H), 8.56 (t, J = 6.1 Hz, 1H), 7.90-7.73 (m, 5H), 7.74-7.68 (m, 4H), 7.46-7.30 (m, 7H), 7.22-7.14 (m, 3H), 7.13-7.02 (m, 4H), 7.01-6.93 (m, 1H), 6.70 (s, 1H), 5.76 (s, 2H), 5.12 (d, J = 3.6 Hz, 1H), 5.06 (d, J = 10.5 Hz, 1H), 4.57 (d, J = 9.2 Hz, 1H), 4.49-4.38 (m, 5H), 4.36 (s, 1H), 4.32-4.17 (m, 4H), 3.78 (s, 2H), 3.67 (s, 2H), 3.48-3.40 (m, 2H), 3.12-3.04 (m, 3H), 2.95 (s, 1H), 2.83 (d, J = 32.1 Hz, 2H), 2.60-2.51 (m, 3H), 2.09 (s, 4H), 2.02 (d, J = 8.7 Hz, 3H), 1.95 (d, J = 14.0 Hz, 1H), 1.94-1.85 (m, 1H), 1.08 (d, J = 6.2 Hz, 3H), 0.95 (s, 9H). |

TABLE 50-continued

| Characterization data for intermediates prepared according to above. | | | | |
|---|---|---|---|---|
| Inter-mediate | Structure | Chemical Name | MS: [(M + 1)]$^+$ | $^1$H NMR |
| I30 | 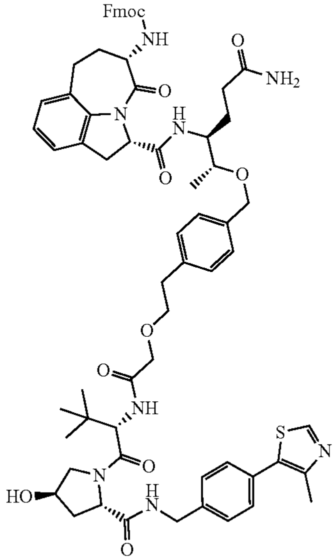 | 9H-fluoren-9-ylmethyl N-[(2S,11S)-2-[[(3S,4R)-1-carbamoyl-4-([4-[2-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methoxy)ethyl]phenyl]methoxy)pentan-3-yl]carbamoyl]-12-oxo-1-azatricyclo[6.4.1.0^[4,13]]trideca-4(13),5,7-trien-11-yl]carbamate | [(M/2 + 1)]$^+$ = 601.7 | (400 MHz, DMSO-$d_6$) δ 8.97 (s, 1H), 8.61 (t, J = 6.0 Hz, 1H), 7.90 (d, J = 7.6 Hz, 2H), 7.84 (d, J = 9.2 Hz, 1H), 7.80-7.70 (m, 3H), 7.47-7.38 (m, 5H), 7.37 (dd, J = 9.0, 2.7 Hz, 2H), 7.33 (d, J = 7.3 Hz, 1H), 7.22-7.15 (m, 3H), 7.05 (d, J = 7.8 Hz, 2H), 7.01-6.92 (m, 1H), 6.70 (s, 1H), 5.16 (d, J = 3.5 Hz, 1H), 5.06 (d, J = 10.5 Hz, 1H), 4.55 (d, J = 9.6 Hz, 1H), 4.44 (dt, J = 16.2, 8.7 Hz, 2H), 4.44-4.32 (m, 3H), 4.30-4.24 (m, 4H), 3.98-3.88 (m, 2H), 3.78 (s, 1H), 3.75-3.63 (m, 1H), 3.61 (d, J = 10.6 Hz, 1H), 3.43 (q, J = 11.8, 10.4 Hz, 2H), 3.33 (s, 1H), 3.14-3.03 (m, 1H), 3.06 (s, 1H), 2.89-2.81 (m, 3H), 2.43 (s, 3H), 2.12-2.04 (m, 3H), 1.96-1.85 (m, 1H), 1.78 (s, 1H), 1.55 (d, J = 12.3 Hz, 1H), 1.06 (d, J = 6.2 Hz, 3H), 0.93 (s, 9H). |
| I31 | 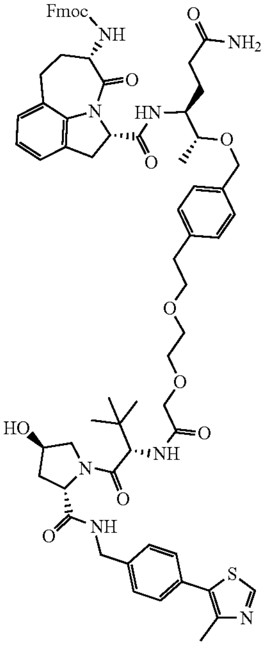 | 9H-fluoren-9-ylmethyl N-[(2S,11S)-2-[[(3S,4R)-1-carbamoyl-4-[(4-[2-[2-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methoxy)ethoxy]ethyl]phenyl)methoxy]pentan-3-yl]carbamoyl]-12-oxo-1-azatricyclo[6.4.1.0^[4,13]]trideca-4(13),5,7-trien-11-yl]carbamate | 1245.9 | (400 MHz, DMSO-$d_6$) δ 8.97 (s, 1H), 8.59 (t, J = 6.0 Hz, 1H), 7.91 (d, J = 7.6 Hz, 2H), 7.84 (d, J = 9.2 Hz, 1H), 7.80-7.69 (m, 3H), 7.47-7.31 (m, 8H), 7.24-7.11 (m, 4H), 7.06 (d, J = 7.6 Hz, 2H), 7.01-6.93 (m, 1H), 6.68 (s, 1H), 5.15 (d, J = 3.5 Hz, 1H), 5.07 (d, J = 10.5 Hz, 1H), 4.59 (d, J = 9.6 Hz, 1H), 4.47 (t, J = 8.1 Hz, 1H), 4.48-4.37 (m, 4H), 4.32-4.24 (m, 4H), 4.14 (s, 1H), 3.98 (s, 2H), 3.79 (s, 2H), 3.69 (dd, J = 10.7, 4.0 Hz, 1H), 3.66-3.54 (m, 7H), 3.14-2.99 (m, 1H), 2.88 (s, 1H), 2.82 (t, J = 7.2 Hz, 2H), 2.43 (s, 3H), 2.15-2.04 (m, 6H), 1.98-1.87 (m, 1H), 1.79 (s, 1H), 1.57 (s, 1H), 1.08 (d, J = 6.2 Hz, 3H), 0.96 (s, 9H). |

TABLE 50-continued

| Characterization data for intermediates prepared according to above. | | | | |
|---|---|---|---|---|
| Inter-mediate | Structure | Chemical Name | MS: [(M + 1)]+ | $^1$H NMR |
| I32 | 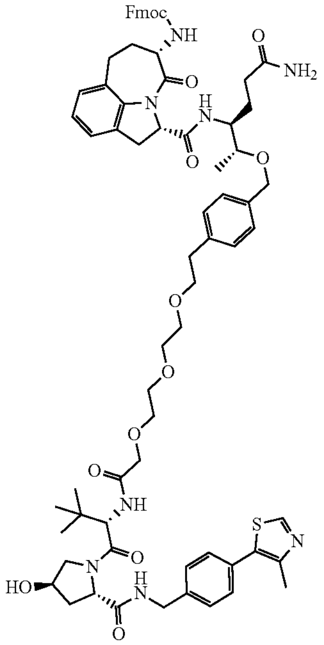 | 9H-fluoren-9-ylmethyl N-[(2S,11S)-2-[[(3S,4R)-1-carbamoyl-4-[[4-(2-[2-[2-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methoxy)ethoxy]ethoxy]ethyl)phenyl]methoxy]pentan-3-yl]carbamoyl]-12-oxo-1-azatricyclo[6.4.1.0^[4,13]]trideca-4(13),5,7-trien-11-yl]carbamate | 1289.8 | (400 MHz, $CD_3OD$) δ 8.86 (s, 1H), 7.82 (d, J = 7.7 Hz, 2H), 7.70 (t, J = 8.3 Hz, 2H), 7.59 (s, 1H), 7.49-7.37 (m, 6H), 7.33 (t, J = 7.5 Hz, 2H), 7.23 (d, J = 7.6 Hz, 2H), 7.16 (d, J = 7.9 Hz, 2H), 7.10-6.99 (m, 3H), 5.13 (d, J = 10.7 Hz, 1H), 4.71 (s, 1H), 4.63-4.46 (m, 4H), 4.45-4.22 (m, 6H), 4.10-3.97 (m, 2H), 3.89 (d, J = 11.1 Hz, 1H), 3.85-3.78 (m, 1H), 3.70-3.61 (m, 11 H), 3.58 (d, J = 17.6 Hz, 1H), 3.44 (d, J = 11.2 Hz, 1H), 3.14 (s, 1H), 3.01 (d, J = 16.6 Hz, 1H), 2.83 (t, J = 6.9 Hz, 2H), 2.47 (s, 3H), 2.30-2.20 (m, 5H), 2.07 (d, J = 16.1 Hz, 1H), 2.00 (s, 2H), 1.67 (s, 1H), 1.19 (d, J = 6.5 Hz, 3H), 1.05 (s, 9H). |
| I33 | 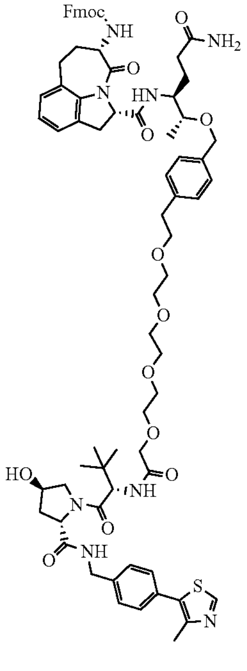 | 9H-fluoren-9-ylmethyl N-[(2S,11S)-2-[[(3S,4R)-1-carbamoyl-4-[[4-(1-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]-2,5,8,11-tetraoxatridecan-13-yl)phenyl]methoxy]pentan-3-yl]carbamoyl]-12-oxo-1-azatricyclo[6.4.1.0^[4,13]]trideca-4(13),5,7-trien-11-yl]carbamate | 1333.9 | (400 MHz, DMSO-$d_6$) δ 8.98 (s, 1H), 8.60 (t, J = 6.0 Hz, 1H), 7.90-7.82 (m, 3H), 7.80-7.73 (m, 3H), 7.47-7.36 (m, 6H), 7.35 (q, J = 7.2 Hz, 3H), 7.20-7.12 (m, 5H), 7.05 (d, J = 7.7 Hz, 2H), 7.00-6.93 (m, 1H), 6.69 (s, 1H), 5.15 (s, 1H), 5.10-5.02 (m, 1H), 4.57 (d, J = 9.6 Hz, 1H), 4.48-4.34 (m, 5H), 4.32-4.24 (m, 4H), 4.13 (q, J = 7.6, 6.1 Hz, 1H), 3.97 (s, 2H), 3.78 (s, 1H), 3.68 (dd, J = 10.7, 3.9 Hz, 1H), 3.65-3.47 (m, 16H), 3.47-3.37 (m, 3H), 3.07 (q, J = 18.5, 13.8 Hz, 2H), 2.90-2.82 (m, 1H), 2.78 (q, J = 7.0, 5.7 Hz, 2H), 2.44 (s, 3H), 2.07-2.00 (m, 2H), 1.96-1.91 (m, 1H), 1.78 (s, 1H), 1.56 (d, J = 12.0 Hz, 1H), 1.08 (d, J = 6.2 Hz, 3H), 0.95 (s, 9H). |

TABLE 50-continued

Characterization data for intermediates prepared according to above.

| Inter-mediate | Structure | Chemical Name | MS: [(M + 1)]$^+$ | $^1$H NMR |
|---|---|---|---|---|
| I44 | 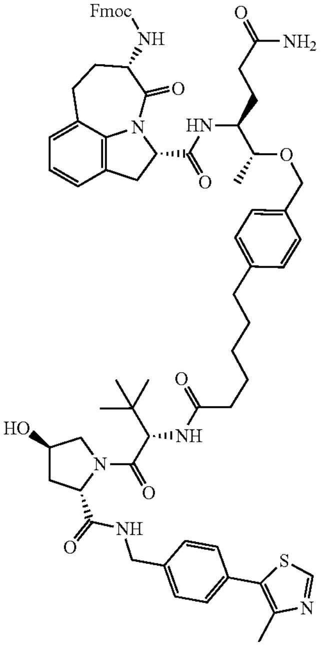 | 9H-fluoren-9-ylmethyl N-[(2S,11S)-2-[[(3S,4R)-1-carbamoyl-4-[[4-(5-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]pentyl)phenyl]methoxy]pentan-3-yl]carbamoyl]-12-oxo-1-azatricyclo[6.4.1.0^[4,13]]trideca-4(13),5,7-trien-11-yl]carbamate | 1213.2 | (400 MHz, $CDCl_3$) δ 8.71 (s, 1H), 7.79 (d, J = 7.6 Hz, 2H), 7.64 (d, J = 7.5 Hz, 2H), 7.41 (q, J = 7.4 Hz, 2H), 7.37-7.30 (m, 5H), 7.26 (d, J = 7.7 Hz, 2H), 7.13 (d, J = 7.8 Hz, 2H), 7.11-7.01 (m, 3H), 6.83 (d, J = 9.5 Hz, 1H), 6.24 (d, J = 8.6 Hz, 1H), 6.11-5.89 (m, 2H), 5.25-5.00 (m, 2H), 4.69 (t, J = 7.9 Hz, 1H), 4.66-4.46 (m, 2H), 4.46-4.19 (m, 6H), 4.10 (d, J = 11.3 Hz, 1H), 3.69-3.51 (m, 2H), 3.33 (d, J = 11.4 Hz, 1H), 3.16 (d, J = 46.2 Hz, 1H), 2.57 (t, J = 7.7 Hz, 2H), 2.53 (s, 3H), 2.28 (d, J = 13.7 Hz, 1H), 2.24-1.96 (m, 9H), 1.77 (s, 2H), 1.67-1.53 (m, 4H), 1.40-1.15 (m, 5H), 0.93 (s, 9H). |
| I45 | 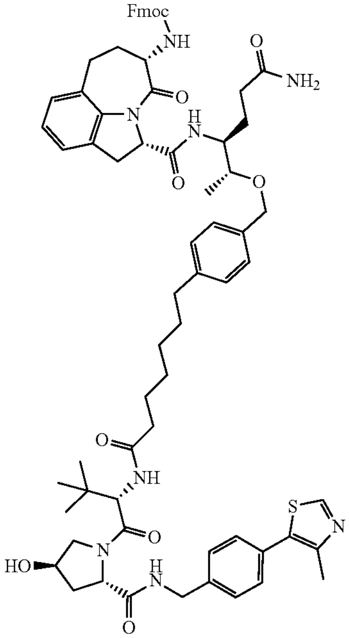 | 9H-fluoren-9-ylmethyl N-(2S,11S)-2-[[(3S,4R)-1-carbamoyl-4-[[4-(6-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]hexyl)phenyl]methoxy]pentan-3-yl]carbamoyl]-12-oxo-1-azatricyclo[6.4.1.0^[4,13]]trideca-4(13),5,7-trien-11-yl]carbamate | [(M + 2)/2]$^+$ = 614.6 | (400 MHz, $CD_3OD$) δ 8.88 (s, 1H), 7.82 (d, J = 7.5 Hz, 2H), 7.70 (t, J = 8.3 Hz, 2H), 7.47 (d, J = 8.1 Hz, 2H), 7.45-7.37 (m, 4H), 7.33 (t, J = 7.5 Hz, 2H), 7.23 (d, J = 7.8 Hz, 2H), 7.15-6.99 (m, 6H), 5.13 (d, J = 10.6 Hz, 1H), 4.67-4.40 (m, 6H), 4.30 (s, 1H), 3.92 (d, J = 11.0 Hz, 1H), 3.81 (dd, J = 10.9, 3.9 Hz, 1H), 3.63-3.40 (m, 2H), 3.07 (d, J = 61.1 Hz, 3H), 2.60 (t, J = 7.6 Hz, 2H), 2.48 (s, 3H), 2.25 (dq, J = 14.6, 8.1, 7.2 Hz, 5H), 2.14-1.95 (m, 2H), 1.62 (s, 7H), 1.34 (d, J = 18.9 Hz, 6H), 1.19 (d, J = 6.4 Hz, 4H), 1.05 (s, 9H). |

TABLE 50-continued

Characterization data for intermediates prepared according to above.

| Inter-mediate | Structure | Chemical Name | MS: [(M + 1)]+ | $^1$H NMR |
|---|---|---|---|---|
| I46 | 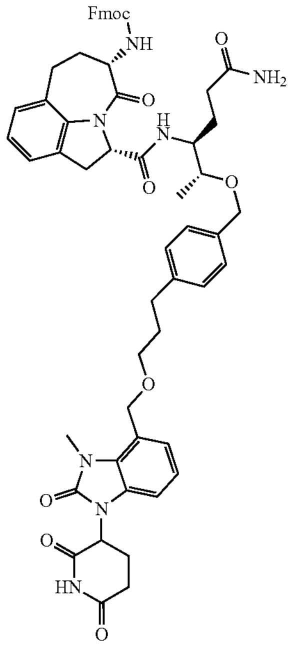 | 9H-fluoren-9-ylmethyl N-[(2S,11S)-2-[[(3S,4R)-1-carbamoyl-4-[[4-(3-[[1-(2,6-dioxopiperidin-3-yl)-3-methyl-2-oxo-1,3-benzodiazol-4-yl]methoxy]propyl) phenyl]methoxy]pentan-3-yl]carbamoyl]-12-oxo-1-azatricyclo[6.4.1.0^[4,13]] trideca-4(13),5,7-trien-11-yl]carbamate | 1016.5 | (400 MHz, DMSO-$d_6$) δ 11.10 (s, 1H), 7.90 (d, J = 7.4 Hz, 2H), 7.83 (d, J = 9.0 Hz, 1H), 7.77-7.69 (m, 3H), 7.42 (t, J = 7.4 Hz, 2H), 7.35 (d, J = 7.4 Hz, 2H), 7.17-7.13 (m, 4H), 7.09 (t, J = 9.3 Hz, 2H), 7.07-6.99 (m, 3H), 7.02-6.92 (m, 1H), 6.68 (s, 1H), 5.43-5.35 (m, 1H), 5.05 (d, J = 10.4 Hz, 1H), 4.69 (s, 2H), 4.39 (s, 2H), 4.27-4.26 (m, 3H), 4.12 (s, 1H), 3.77 (s, 2H), 3.59 (d, J = 2.8 Hz, 3H), 3.47 (t, J = 6.5 Hz, 2H), 3.42 (s, 3H), 3.05 (s, 1H), 2.86 (t, J = 14.7 Hz, 2H), 2.72 (d, J = 13.3 Hz, 1H), 2.67-2.55 (m, 2H), 2.07 (d, J = 3.2 Hz, 1H), 2.05 (s, 2H), 2.00 (s, 1H), 1.82 (s, 2H), 1.54 (s, 2H), 1.07 (d, J = 6.2 Hz, 3H). |
| I47 | 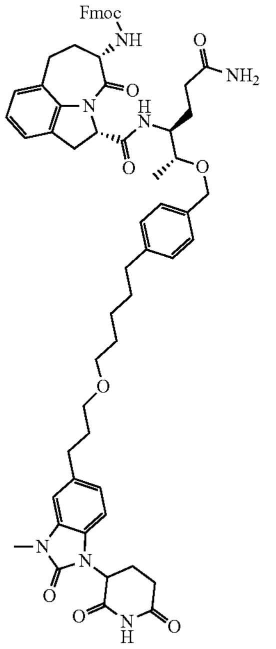 | 9H-fluoren-9-ylmethyl N-[(2S,11S)-2-[[(3S,4R)-1-carbamoyl-4-[[4-(5-[3-[1-(2,6-dioxopiperidin-3-yl)-3-methyl-2-oxo-1,3-benzodiazol-5-yl]propoxy]pentyl) phenyl]methoxy]pentan-3-yl]carbamoyl]-12-oxo-1-azatricyclo[6.4.1.0^[4,13]] trideca-4(13),5,7-trien-11-yl]carbamate | 1072.9 | (400 MHz, DMSO-$d_6$) δ 11.08 (s, 1H), 7.90 (d, J = 7.5 Hz, 2H), 7.84 (t, J = 8.3 Hz, 1H), 7.79-7.71 (m, 3H), 7.43 (t, J = 7.5 Hz, 2H), 7.35 (d, J = 7.5 Hz, 2H), 7.20-6.94 (m, 10H), 6.89-6.83 (m, 1H), 6.68 (s, 1H), 5.34 (dd, J = 12.6, 5.3 Hz, 1H), 5.06 (d, J = 10.6 Hz, 1H), 4.40 (s, 2H), 4.28-4.24 (m, 3H), 4.13 (s, 1H), 3.78 (s, 1H), 3.43 (s, 2H), 3.38-3.32 (m, 6H), 3.09 (s, 1H), 3.07-2.98 (m, 1H), 2.88 (s, 1H), 2.75-2.52 (m, 4H), 2.08 (s, 2H), 1.85-1.78 (m, 4H), 1.55 (dd, J = 14.8, 7.5 Hz, 6H), 1.41-1.31 (m, 2H), 1.07 (d, J = 6.2 Hz, 3H). |

TABLE 50-continued

Characterization data for intermediates prepared according to above.

| Inter-mediate | Structure | Chemical Name | MS: [(M + 1)]+ | $^1$H NMR |
|---|---|---|---|---|
| I48 | 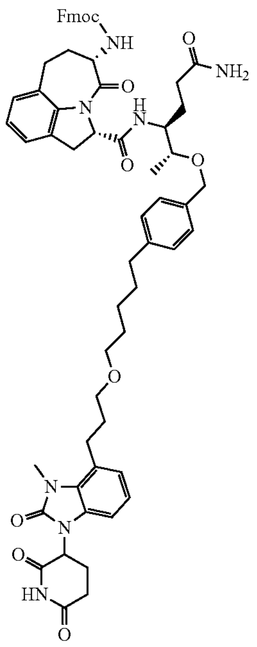 | 9H-fluoren-9-ylmethyl N-[(2S,11S)-2-[[(3S,4R)-1-carbamoyl-4-[[4-(5-[3-[1-(2,6-dioxopiperidin-3-yl)-3-methyl-2-oxo-1,3-benzodiazol-4-yl]propoxy]pentyl)phenyl]methoxy]pentan-3-yl]carbamoyl]-12-oxo-1-azatricyclo[6.4.1.0^[4,13]]trideca-4(13),5,7-trien-11-yl]carbamate | 1072.8 | (400 MHz, DMSO-$d_6$) δ 11.09 (s, 1H), 7.90 (d, J = 7.7 Hz, 2H), 7.84 (t, J = 7.6 Hz, 1H), 7.79-7.71 (m, 3H), 7.43 (t, J = 7.4 Hz, 2H), 7.34 (dd, J = 9.7, 5.2 Hz, 2H), 7.19-7.15 (m, 3H), 7.11 (d, J = 7.8 Hz, 2H), 7.05 (d, J = 7.6 Hz, 2H), 6.98-6.95 (m, 3H), 6.85 (dd, J = 5.8, 3.2 Hz, 1H), 6.69 (s, 1H), 5.37 (dd, J = 12.5, 5.4 Hz, 1H), 5.06 (d, J = 10.4 Hz, 1H), 4.39 (s, 2H), 4.27-4.26 (m, 3H), 4.13 (s, 1H), 3.78 (s, 1H), 3.45-3.28 (m, 6H), 3.32 (s, 2H), 3.06 (q, J = 17.1, 13.3 Hz, 1H), 2.94 (t, J = 7.8 Hz, 2H), 2.88 (s, 2H), 2.75-2.62 (m, 1H), 2.56 (t, J = 7.6 Hz, 2H), 2.08 (s, 2H), 1.85-1.79 (m, 4H), 1.56 (dt, J = 14.8, 7.7 Hz, 6H), 1.34 (d, J = 7.7 Hz, 2H), 1.07 (d, J = 6.2 Hz, 3H). |
| I49 | 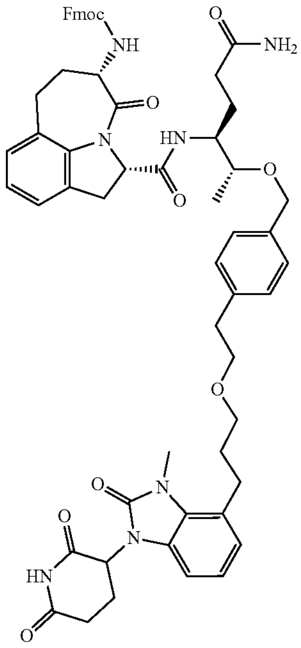 | 9H-fluoren-9-ylmethyl N-[(2S,11S)-2-[[(3S,4R)-1-carbamoyl-4-[[4-(2-[3-[1-(2,6-dioxopiperidin-3-yl)-3-methyl-2-oxo-1,3-benzodiazol-4-yl]propoxy]ethyl)phenyl]methoxy]pentan-3-yl]carbamoyl]-12-oxo-1-azatricyclo[6.4.1.0^[4,13]]trideca-4(13),5,7-trien-11-yl]carbamate | 1030.3 | (400 MHz, DMSO-$d_6$) δ 11.09 (s, 1H), 7.90 (d, J = 7.5 Hz, 2H), 7.84 (d, J = 9.2 Hz, 1H), 7.75 (q, J = 7.8, 7.4 Hz, 3H), 7.43 (t, J = 7.4 Hz, 2H), 7.34 (t, J = 7.5 Hz, 2H), 7.19-7.15 (m, 5H), 7.05 (d, J = 7.7 Hz, 2H), 7.00-6.90 (m, 3H), 6.81 (dd, J = 6.4, 2.4 Hz, 1H), 6.69 (s, 1H), 5.36 (dd, J = 12.5, 5.4 Hz, 1H), 5.06 (d, J = 11.0 Hz, 1H), 4.41 (s, 2H), 4.32-4.26 (m, 3H), 4.13 (s, 1H), 3.78 (s, 1H), 3.58 (q, J = 10.4, 8.6 Hz, 2H), 3.46 (d, J = 5.6 Hz, 1H), 3.13-3.03 (m, 2H), 3.01-2.80 (m, 6H), 2.81 (t, J = 6.9 Hz, 2H), 2.76-2.66 (m, 1H), 2.64 (s, 1H), 2.60 (s, 1H), 2.08 (s, 4H), 1.82-1.80 (m, 4H), 1.56 (s, 2H), 1.07 (d, J = 6.2 Hz, 3H). |

TABLE 50-continued

| Characterization data for intermediates prepared according to above. | | | | |
|---|---|---|---|---|
| Inter-mediate | Structure | Chemical Name | MS: [(M + 1)]$^+$ | $^1$H NMR |
| I50 | 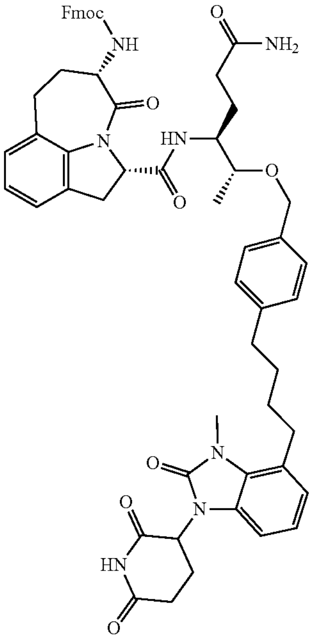 | 9H-fluoren-9-ylmethyl N-[(2S,11S)-2-[[(3S,4R)-1-carbamoyl-4-[(4-[4-[1-(2,6-dioxopiperidin-3-yl)-3-methyl-2-oxo-1,3-benzodiazol-4-yl]butyl]phenyl)methoxy]pentan-3-yl]carbamoyl]-12-oxo-1-azatricyclo[6.4.1.0^[4,13]]trideca-4(13),5,7-trien-11-yl]carbamate | 1000.7 | (400 MHz, $CDCl_3$) δ 8.53 (s, 1H), 7.78 (d, J = 7.5 Hz, 2H), 7.64 (d, J = 6.4 Hz, 2H), 7.42 (t, J = 7.4 Hz, 2H), 7.42-7.25 (m, 3H), 7.28 (s, 1H), 7.15 (t, J = 8.1 Hz, 2H), 7.10-7.00 (m, 3H), 7.00-6.88 (m, 2H), 6.85 (d, J = 7.8 Hz, 1H), 6.67 (dd, J = 7.8, 2.8 Hz, 1H), 6.06 (s, 1H), 5.29-5.05 (m, 3H), 4.62 (d, J = 11.6 Hz, 1H), 4.45-4.31 (m, 4H), 4.26 (t, J = 7.3 Hz, 1H), 3.97 (s, 1H), 3.71-3.57 (m, 2H), 3.52-3.45 (m, 3H), 3.39-3.18 (m, 3H), 3.10 (d, J = 17.5 Hz, 1H), 3.00-2.61 (m, 8H), 2.32 (d, J = 13.2 Hz, 1H), 2.25-2.16 (m, 2H), 2.10 (d, J = 9.4 Hz, 2H), 1.75 (s, 2H), 1.65 (d, J = 9.1 Hz, 2H), 1.24 (d, J = 6.3 Hz, 3H). |
| I51 | 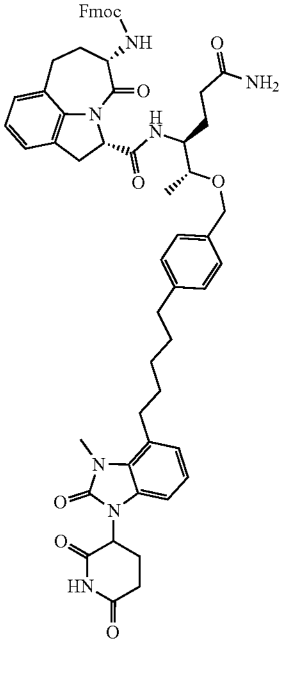 | 9H-fluoren-9-ylmethyl N-[(2S,11S)-2-[[(3S,4R)-1-carbamoyl-4-[(4-[5-[1-(2,6-dioxopiperidin-3-yl)-3-methyl-2-oxo-1,3-benzodiazol-4-yl]pentyl]phenyl)methoxy]pentan-3-yl]carbamoyl]-12-oxo-1-azatricyclo[6.4.1.0^[4,13]]trideca-4(13),5,7-trien-11-yl]carbamate | 1014.3 | (400 MHz, DMSO-$d_6$) δ 11.09 (s, 1H), 7.90 (d, J = 7.6 Hz, 2H), 7.84 (d, J = 9.3 Hz, 1H), 7.76-7.72 (m, 3H), 7.43 (t, J = 7.4 Hz, 2H), 7.34 (t, J = 7.5 Hz, 2H), 7.18-7.15 (m, 3H), 7.11 (d, J = 7.8 Hz, 2H), 7.05 (d, J = 7.7 Hz, 2H), 7.00-6.91 (m, 3H), 6.85 (dd, J = 6.0, 2.9 Hz, 1H), 6.69 (s, 1H), 5.37 (dd, J = 12.5, 5.4 Hz, 1H), 5.06 (d, J = 9.7 Hz, 1H), 4.46-4.35 (m, 2H), 4.27 (dd, J = 12.1, 7.8 Hz, 2H), 3.78 (s, 2H), 3.48-3.37 (m, 2H), 3.32 (s, 3H), 3.07 (s, 1H), 3.13-2.98 (m, 1H), 2.88 (s, 2H), 2.88 (d, J = 15.7 Hz, 1H), 2.77-2.66 (m, 1H), 2.65 (s, 1H), 2.57 (t, J = 7.7 Hz, 2H), 2.11-2.08 (m, 3H), 2.01 (s, 2H), 1.79 (s, 1H), 1.62 (s, 6H), 1.41 (t, J = 7.6 Hz, 2H), 1.08 (d, J = 6.2 Hz, 3H). |

TABLE 50-continued

Characterization data for intermediates prepared according to above.

| Intermediate | Structure | Chemical Name | MS: [(M + 1)]+ | $^1$H NMR |
|---|---|---|---|---|
| I52 | 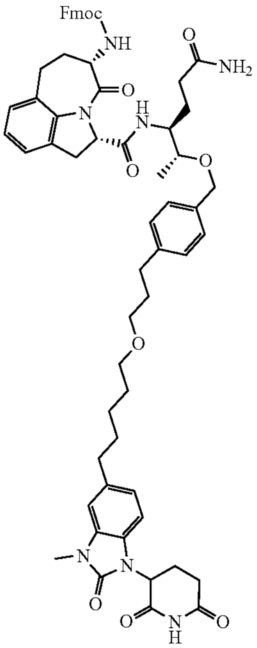 | 9H-fluoren-9-ylmethyl N-[(2S,11S)-2-[[(3S,4R)-1-carbamoyl-4-([4-[3-([5-[1-(2,6-dioxopiperidin-3-yl)-3-methyl-2-oxo-1,3-benzodiazol-5-yl]pentyl]oxy)propyl]phenyl]methoxy)pentan-3-yl]carbamoyl]-12-oxo-1-azatricyclo[6.4.1.0^[4,13]]trideca-4(13),5,7-trien-11-yl]carbamate | 1072.8 | (400 MHz, DMSO-$d_6$) δ 11.07 (s, 1H), 7.90 (d, J = 7.6 Hz, 2H), 7.83 (d, J = 9.2 Hz, 1H), 7.84-7.63 (m, 3H), 7.43 (t, J = 7.4 Hz, 2H), 7.34 (t, J = 7.4 Hz, 2H), 7.19-7.15 (m, 3H), 7.13-7.04 (m, 3H), 7.03 (d, J = 6.0 Hz, 2H), 6.98 (t, J = 8.7 Hz, 2H), 6.86 (d, J = 8.5 Hz, 1H), 6.69 (s, 1H), 5.33 (dd, J = 12.7, 5.3 Hz, 1H), 5.06 (d, J = 11.1 Hz, 1H), 4.40 (s, 2H), 4.28 (dd, J = 12.3, 6.8 Hz, 2H), 4.13 (s, 1H), 3.78 (s, 1H), 3.45 (d, J = 6.0 Hz, 2H), 3.36-3.33 (m, 3H), 3.07 (d, J = 16.2 Hz, 2H), 2.92-2.81 (m, 2H), 2.72-2.54 (m, 6H), 2.08 (s, 1H), 2.02 (s, 2H), 1.98 (d, J = 6.0 Hz, 2H), 1.76 (t, J = 7.6 Hz, 4H), 1.66-1.50 (m, 6H), 1.36 (d, J = 7.7 Hz, 2H), 1.08 (d, J = 6.2 Hz, 3H). |
| I53 | 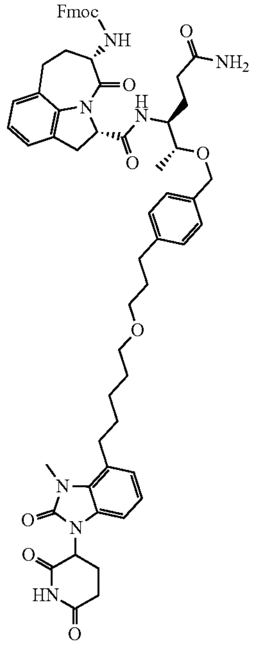 | 9H-fluoren-9-ylmethyl N-[(2S,11S)-2-[[(3S,4R)-1-carbamoyl-4-([4-[3-([5-[1-(2,6-dioxopiperidin-3-yl)-3-methyl-2-oxo-1,3-benzodiazol-4-yl]pentyl]oxy)propyl]phenyl]methoxy)pentan-3-yl]carbamoyl]-12-oxo-1-azatricyclo[6.4.1.0^[4,13]]trideca-4(13),5,7-trien-11-yl]carbamate | 1072.7 | (400 MHz, DMSO-$d_6$) δ 11.08 (s, 1H), 7.90 (d, J = 7.4 Hz, 2H), 7.83 (d, J = 9.6 Hz, 1H), 7.79-7.70 (m, 3H), 7.43 (t, J = 7.3 Hz, 1H), 7.35 (d, J = 7.3 Hz, 1H), 7.21-7.15 (m, 3H), 7.14-7.02 (m, 4H), 6.97-6.96 (m, 3H), 6.88 (s, 1H), 6.69 (s, 1H), 5.36 (d, J = 7.6 Hz, 1H), 5.06 (d, J = 9.6 Hz, 1H), 4.41 (s, 2H), 4.28-4.24 (m, 3H), 4.13 (s, 1H), 3.78 (s, 2H), 3.55 (s, 3H), 3.38-3.32 (m, 3H), 2.94-2.86 (m, 3H), 2.84 (s, 2H), 2.64 (s, 3H), 2.61-2.56 (m, 3H), 2.09-2.07 (m, 4H), 1.77 (s, 3H), 1.68-1.45 (m, 6H), 1.45 (d, J = 7.2 Hz, 2H), 1.08 (d, J = 6.2 Hz, 3H). |

TABLE 50-continued

Characterization data for intermediates prepared according to above.

| Inter-mediate | Structure | Chemical Name | MS: [(M + 1)]$^+$ | $^1$H NMR |
|---|---|---|---|---|
| I54 | 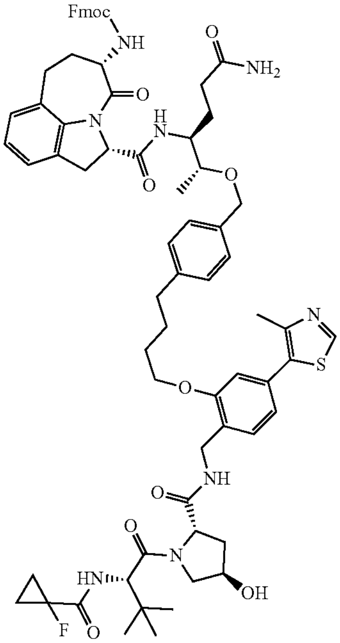 | 9H-fluoren-9-ylmethyl N-[(2S,11S)-2-[[(3S,4R)-1-carbamoyl-4-[(4-[4-[2-([[(2S,4R)-1-[(2S)-2-[(1-fluorocyclopropyl) formamido]-3,3-dimethylbutanoyl]-4-hydroxypyrrolidin-2-yl]formamido]methyl)-5-(4-methyl-1,3-thiazol-5-yl)phenoxy]butyl]phenyl) methoxy]pentan-3-yl]carbamoyl]-12-oxo-1-azatricyclo[6.4.1.0^[4,13]] trideca-4(13),5,7-trien-11-yl]carbamate | 1273.8 | (400 MHz, DMSO-$d_6$) δ 8.98 (d, J = 3.7 Hz, 1H), 8.48 (s, 1H), 7.89 (s, 2H), 7.84 (s, 1H), 7.76-7.73 (m, 3H), 7.45-7.41 (m, 3H), 7.36-7.34 (m, 5H), 7.17-7.14 (m, 7H), 7.04-6.99 (m, 4H), 6.94 (s, 2H), 6.68 (s, 1H), 5.16 (s, 1H), 5.05 (d, J = 11.1 Hz, 1H), 4.60 (d, J = 9.0 Hz, 1H), 4.52 (s, 1H), 4.40 (s, 2H), 4.35 (s, 1H), 4.28-4.27 (m, 4H), 4.17-4.05 (m, 3H), 3.78 (s, 2H), 3.62 (d, J = 10.2 Hz, 2H), 3.44-3.43 (m, 3H), 2.85 (d, J = 16.5 Hz, 1H), 2.65-2.64 (m, 3H), 2.46-2.44 (m, 4H), 2.12-2.05 (m, 4H), 1.79-1.72 (m, 3H), 1.35 (s, 1H), 1.22 (s, 1H), 1.07 (s, 3H), 0.96 (s, 9H). |
| I55 | 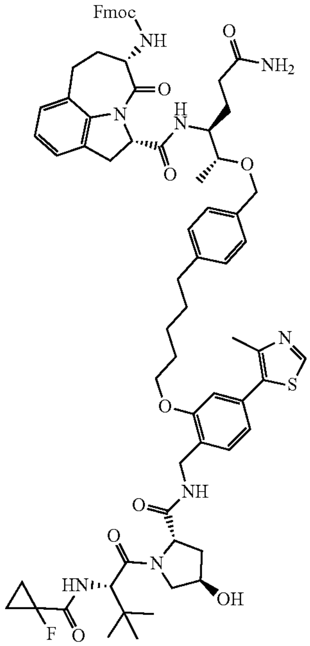 | 9H-fluoren-9-ylmethyl N-[(2S,11S)-2-[[(3S,4R)-1-carbamoyl-4-[(4-[5-[2-([[(2S,4R)-1-[(2S)-2-[(1-fluorocyclopropyl) formamido]-3,3-dimethylbutanoyl]-4-hydroxypyrrolidin-2-yl]formamido]methyl)-5-(4-methyl-1,3-thiazol-5-yl)phenoxy]pentyl] phenyl)methoxy]pentan-3-yl]carbamoyl]-12-oxo-1-azatricyclo[6.4.1.0^[4,13]] trideca-4(13),5,7-trien-11-yl]carbamate | 1287.9 | (400 MHz, DMSO-$d_6$) δ 8.98 (s, 1H), 8.49 (t, J = 6.0 Hz, 1H), 7.90 (d, J = 7.6 Hz, 2H), 7.83 (d, J = 9.2 Hz, 1H), 7.79-7.69 (m, 3H), 7.47-7.26 (m, 6H), 7.18-7.12 (m, 5H), 7.06-6.98 (m, 4H), 6.95 (d, J = 7.6 Hz, 2H), 6.68 (s, 1H), 5.17 (d, J = 3.6 Hz, 1H), 5.06 (d, J = 11.3 Hz, 1H), 4.60 (d, J = 9.2 Hz, 1H), 4.53 (t, J = 8.2 Hz, 1H), 4.43-4.28 (m, 3H), 4.30-4.19 (m, 3H), 4.13 (s, 1H), 4.05 (t, J = 6.3 Hz, 2H), 3.78 (s, 1H), 3.70-3.55 (m, 2H), 3.45 (d, J = 5.9 Hz, 1H), 3.06 (d, J = 13.1 Hz, 2H), 2.86 (d, J = 16.8 Hz, 1H), 2.59 (t, J = 7.7 Hz, 2H), 2.46 (s, 3H), 2.08 (s, 1H), 2.08-2.04 (m, 3H), 1.83-1.75 (m, 3H), 1.63 (d, J = 7.4 Hz, 2H), 1.49 (d, J = 7.6 Hz, 1H), 1.42-1.33 (m, 1H), 1.26-1.19 (m, 2H), 1.08 (d, J = 6.2 Hz, 3H), 1.01 (s, 2H), 0.96 (s, 9H). |

TABLE 50-continued

| Characterization data for intermediates prepared according to above. | | | | |
|---|---|---|---|---|
| Intermediate | Structure | Chemical Name | MS: [(M + 1)]$^+$ | $^1$H NMR |
| I56 | 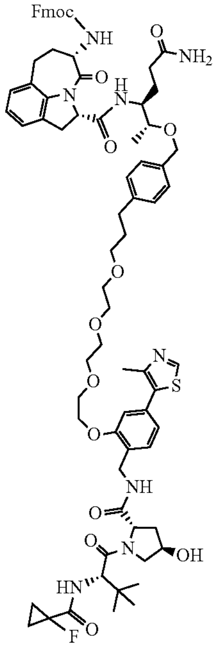 | 9H-fluoren-9-ylmethyl N-[(2S,11S)-2-[[(3S,4R)-1-carbamoyl-4-[(4-[3-[2-(2-[2-[2-([[(2S,4R)-1-[(2S)-2-[(1-fluorocyclopropyl) formamido]-3,3-dimethylbutanoyl]-4-hydroxypyrrolidin-2-yl]formamido]methyl)-5-(4-methyl-1,3-thiazol-5-yl)phenoxy]ethoxy] ethoxy)ethoxy]propyl] phenyl)methoxy]pentan-3-yl]carbamoyl]-12-oxo-1-azatricyclo[6.4.1.0^[4,13]] trideca-4(13),5,7-trien-11-yl]carbamate | [(M/2 + 1)]$^+$ = 696.9 | (400 MHz, DMSO-$d_6$) δ 8.98 (s, 1H), 8.47 (t, J = 6.0 Hz, 1H), 7.90 (d, J = 7.5 Hz, 2H), 7.83 (d, J = 9.2 Hz, 1H), 7.79-7.69 (m, 3H), 7.47-7.34 (m, 3H), 7.36-7.25 (m, 2H), 7.18-7.14 (m, 3H), 7.10 (d, J = 7.8 Hz, 2H), 7.08-7.01 (m, 4H), 6.97 (dd, J = 7.7, 1.6 Hz, 2H), 6.68 (s, 1H), 5.16 (d, J = 3.6 Hz, 1H), 5.06 (d, J = 10.5 Hz, 1H), 4.60 (d, J = 9.2 Hz, 1H), 4.52 (t, J = 8.2 Hz, 1H), 4.38 (d, J = 13.7 Hz, 4H), 4 35-4.09 (m, 7H), 3.80 (d, J = 9.4 Hz, 1H), 3.80 (s, 3H), 3.70-3.60 (m, 4H), 3.58 (d, J = 1.8 Hz, 1H), 3.59-3.50 (m, 4H), 3.48 (s, 1H), 3.49-3.40 (m, 3H), 3.37 (t, J = 6.5 Hz, 2H), 3.05 (dd, J = 18.6, 12.6 Hz, 2H), 2.86 (d, J = 16.6 Hz, 1H), 2.58 (t, J = 7.7 Hz, 2H), 2.46 (s, 3H), 2.08 (s, 3H), 1.92 (tt, J = 9.5, 4.5 Hz, 1H), 1.81-1.72 (m, 3H), 1.55 (d, J = 11.4 Hz, 1H), 1.43-1.31 (m, 1H), 1.22 (dd, J = 8.2, 3.3 Hz, 2H), 1.08 (d, J = 6.2 Hz, 3H), 0.96 (s, 9H). |
| I57 | 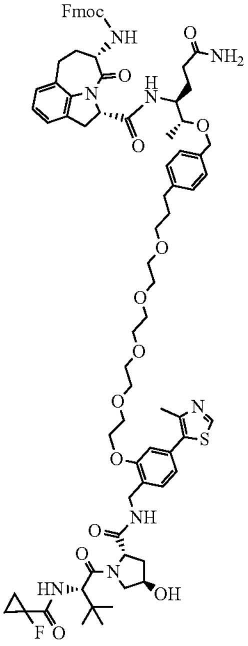 | 9H-fluoren-9-ylmethyl N-[(2S,11S)-2-[[(3S,4R)-1-carbamoyl-4-[(4-[1-[2-([[(2S,4R)-1-[(2S)-2-[(1-fluorocyclopropyl) formamido]-3,3-dimethylbutanoyl]-4-hydroxypyrrolidin-2-yl]formamido]methyl)-5-(4-methyl-1,3-thiazol-5-yl)phenoxy]-3,6,9,12-tetraoxapentadecan-15-yl]phenyl)methoxy] pentan-3-yl]carbamoyl]-12-oxo-1-azatricyclo[6.4.1.0^[4,13]] trideca-4(13),5,7-trien-11-yl]carbamate | [(M/2 + 1)]$^+$ = 718.9 | (400 MHz, DMSO-$d_6$) δ 8.98 (s, 1H), 8.47 (t, J = 6.0 Hz, 1H), 7.90 (d, J = 7.5 Hz, 2H), 7.83 (d, J = 9.3 Hz, 1H), 7.79-7.39 (m, 3H), 7.47-7.25 (m, 6H), 7.20-7.01 (m, 9H), 6.97 (dd, J = 7.7, 1.8 Hz, 2H), 6.68 (s, 1H), 5.16 (d, J = 3.6 Hz, 1H), 5.06 (d, J = 10.9 Hz, 1H), 4.60 (d, J = 9.2 Hz, 1H), 4.52 (t, J = 8.2 Hz, 1H), 4.41-4.35 (m, 3H), 4.32-4.21 (m, 4H), 4.18 (t, J = 4.7 Hz, 2H), 3.79 (d, J = 9.2 Hz, 1H), 3.79 (s, 3H), 3.69-3.52 (m, 5H), 3.55-3.44 (m, 8H), 3.36 (t, J = 6.5 Hz, 2H), 3.11-2.98 (m, 2H), 2.86 (d, J = 16.8 Hz, 1H), 2.58 (t, J = 7.7 Hz, 2H), 2.46 (s, 3H), 2.08 (s, 1H), 2.03 (s, 1H), 1.92 (d, J = 3.3 Hz, 1H), 1.79-7.71 (m, 3H), 1.56 (s, 1H), 1.45-1.35 (m, 1H), 1.23 (d, J = 8.6 Hz, 2H), 1.07 (d, J = 6.2 Hz, 3H), 1.00 (s, 2H), 0.96 (s, 9H). |

TABLE 50-continued

| Characterization data for intermediates prepared according to above. | | | | |
|---|---|---|---|---|
| Inter-mediate | Structure | Chemical Name | MS: [(M + 1)]$^+$ | $^1$H NMR |
| I58 | 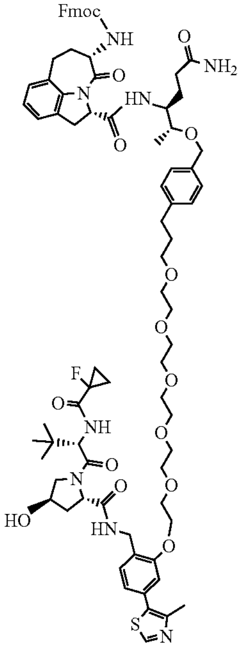 | 9H-fluoren-9-ylmethyl N-[(2S,11S)-2-[[(3S,4R)-1-carbamoyl-4-[(4-[1-[2-([[(2S,4R)-1-[(2S)-2-[(1-fluorocyclopropyl) formamido]-3,3-dimethylbutanoyl]-4-hydroxypyrrolidin-2-yl]formamido]methyl)-5-(4-methyl-1,3-thiazol-5-yl)phenoxy]-3,6,9,12,15-pentaoxaoctadecan-18-yl]phenyl)methoxy] pentan-3-yl]carbamoyl]-12-oxo-1-azatricyclo[6.4.1.0^[4,13]] trideca-4(13),5,7-trien-11-yl]carbamate | [(M/2 + 1)]$^+$ = 740.9 | (400 MHz, DMSO-$d_6$) δ 8.98 (s, 1H), 8.47 (t, J = 6.0 Hz, 1H), 7.90 (d, J = 7.6 Hz, 2H), 7.83 (d, J = 9.2 Hz, 1H), 7.81-7.68 (m, 3H), 7.47-7.20 (m, 6H), 7.17 (d, J = 8.2 Hz, 3H), 7.11 (d, J = 7.8 Hz, 2H), 7.05 (m, 4H), 6.97 (dd, J = 7.8, 1.7 Hz, 2H), 6.68 (s, 1H), 5.16 (d, J = 3.6 Hz, 1H), 5.06 (d, J = 10.5 Hz, 1H), 4.60 (d, J = 9.2 Hz, 1H), 4.52 (t, J = 8.2 Hz, 1H), 4.38 (d, J = 15.8 Hz, 3H), 4.33-4.25 (m, 2H), 4.27-4.21 (m, 1H), 4.21-4.11 (m, 2H), 3.82-3.75 (m, 3H), 3.70-3.59 (m, 3H), 3.55 (dd, J = 5.9, 3.5 Hz, 2H), 3.50-3.41 (m, 2H), 3.41-3.29 (m, 4H), 3.15-3.07 (m, 1H), 3.05 (s, 1H), 2.86 (d, J = 16.8 Hz, 1H), 2.58 (t, J = 7.7 Hz, 2H), 2.47-2.46 (m, 4H), 2.09 (m, 6H), 2.08 (s, 2H), 2.04 (t, J = 9.8 Hz, 2H), 1.93 (tt, J = 8.2, 4.6 Hz, 1H), 1.81-1.74 (m, 3H), 1.55 (d, J = 10.0 Hz, 1H), 1.43-1.31 (m, 2H), 1.22 (dd, J = 8.9, 3.1 Hz, 2H), 1.08 (d, J = 6.2 Hz, 3H), 1.01 (s, 2H), 0.96 (s, 9H). |
| I59 | 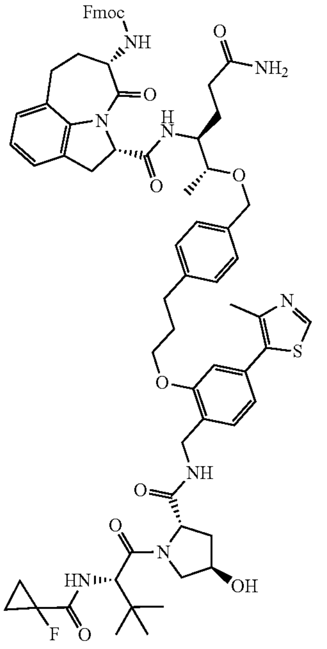 | 9H-fluoren-9-ylmethyl N-[(2S,11S)-2-[[(3S,4R)-1-carbamoyl-4-[(4-[3-[2-([[(2S,4R)-1-[(2S)-2-[(1-fluorocyclopropyl) formamido]-3,3-dimethylbutanoyl]-4-hydroxypyrrolidin-2-yl]formamido]methyl)-5-(4-methyl-1,3-thiazol-5-yl)phenoxy]propyl] phenyl)methoxy]pentan-3-yl]carbamoyl]-12-oxo-1-azatricyclo[6.4.1.0^[4,13]] trideca-4(13),5,7-trien-11-yl]carbamate | 1259.9 | (400 MHz, DMSO-$d_6$) δ 8.98 (s, 1H), 8.52 (t, J = 6.0 Hz, 1H), 7.85-7.82 (m, H), 7.78-7.52 (m, 4H), 7.44-7.40 (m, 3H), 7.38-7.29 (m, 2H), 7.29 (s, 1H), 7.19-7.17 (m, 6H), 7.06-6.89 (m, 6H), 6.69 (s, 1H), 5.17 (d, J = 3.6 Hz, 1H), 5.05 (d, J = 11.2 Hz, 1H), 4.61 (d, J = 9.2 Hz, 1H), 4.53 (t, J = 8.1 Hz, 1H), 4.41 (s, 2H), 4.36-4.23 (m, 3H), 4.13 (s, 1H), 4.05 (t, J = 6.0 Hz, 2H), 3.79 (s, 1H), 3.70-3.57 (m, 2H), 3.08 (s, 2H), 3.02 (d, J = 16.5 Hz, 1H), 2.89-2.73 (m, 4H), 2.48 (s, 1H), 2.46-2.45 (m, 3H), 2.08 (s, 2H), 1.92 (dd, J = 16.6, 7.9 Hz, 1H), 1.78 (s, 1H), 1.55 (s, 1H), 1.43-1.29 (m, 2H), 1.22 (dd, J = 8.5, 3.4 Hz, 2H), 1.08 (d, J = 6.2 Hz, 3H), 0.97 (s, 9H), 0.96 (s, 2H). |

TABLE 50-continued

Characterization data for intermediates prepared according to above.

| Inter-mediate | Structure | Chemical Name | MS: [(M + 1)]$^+$ | $^1$H NMR |
|---|---|---|---|---|
| I60 | 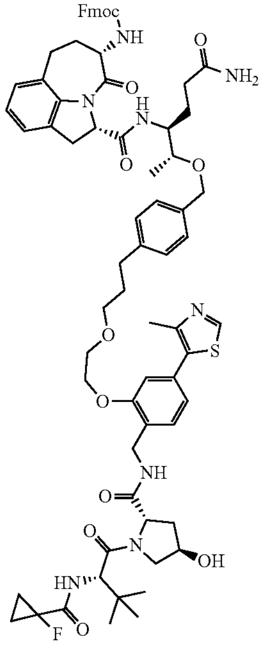 | 9H-fluoren-9-ylmethyl N-[(2S,11S)-2-[[(3S,4R)-1-carbamoyl-4-[[4-(3-[2-[2-([[(2S,4R)-1-[(2S)-2-[(1-fluorocyclopropyl) formamido]-3,3-dimethylbutanoyl]-4-hydroxypyrrolidin-2-yl]formamido]methyl)-5-(4-methyl-1,3-thiazol-5-yl)phenoxy]ethoxy] propyl)phenyl]methoxy] pentan-3-yl]carbamoyl]-12-oxo-1-1-azatricyclo[6.4.1.0^[4,13]] trideca-4(13),5,7-trien-11-yl]carbamate | 1303.8 | (400 MHz, $CDCl_3$) δ 8.76 (s, 1H), 7.78 (d, J = 7.5 Hz, 2H), 7.64 (s, 2H), 7.41 (t, J = 7.4 Hz, 2H), 7.35 (m, 4H), 7.26 (s, 1H), 7.16 (d, J = 7.7 Hz, 2H), 7.15-7.05 (m, 4H), 6.98 (d, J = 7.7 Hz, 1H), 6.91 (s, 1H), 5.95 (s, 1H), 5.20 (s, 1H), 5.03 (s, 1H), 4.68-4.55 (m, 3H), 4.51-4.38 (m, 5H), 4.35 (s, 1H), 4.30-4.14 (m, 3H), 4.04-3.90 (m, 2H), 3.82 (s, 2H), 3.68-3.53 (m, 4H), 3.36 (s, 1H), 2.69 (t, J = 7.7 Hz, 2H), 2.56 (s, 3H), 2.38-2.35 (m, 4H), 2.08-2.07 (m, 3H), 1.94 (d, J = 7.3 Hz, 3H), 1.37-1.28 (m, 3H), 1.24 (d, J = 6.2 Hz, 3H), 0.96 (s, 9H). |
| I61 | 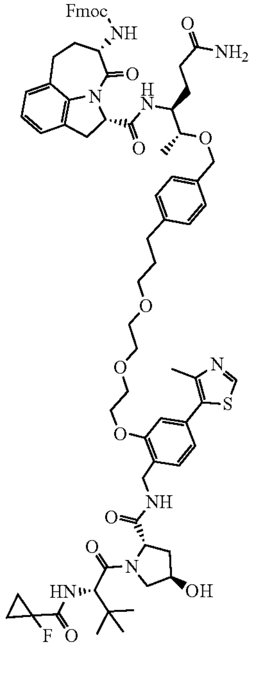 | 9H-fluoren-9-ylmethyl N-[(2S,11S)-2-[[(3S,4R)-1-carbamoyl-4-([4-[3-(2-[2-[2-([[(2S,4R)-1-[(2S)-2-[(1-fluorocyclopropyl) formamido]-3,3-dimethylbutanoyl]-4-hydroxypyrrolidin-2-yl]formamido]methyl)-5-(4-methyl-1,3-thiazol-5 yl)phenoxy]ethoxy] ethoxy)propyl]phenyl] methoxy)pentan-3-yl]carbamoyl]-12-oxo-1-azatricyclo[6.4.1.0^[4,13]] trideca-4(13),5,7-trien-11-yl]carbamate | 1348.0 | (400 MHz, DMSO-$d_6$) δ 8.98 (s, 1H), 8.49 (s, 1H), 7.91 (d, J = 7.5 Hz, 2H), 7.84 (d, J = 10.0 Hz, 1H), 7.80-7.72 (m, 2H), 7.42 (d, J = 7.8 Hz, 2H), 7.33 (dd, J = 15.9, 8.3 Hz, 2H), 7.19-7.07 (m, 5H), 7.06-7.05 (m, 3H), 6.97 (d, J = 7.7 Hz, 2H), 6.69 (s, 1H), 5.17 (s, 1H), 5.06 (d, J = 11.5 Hz, 1H), 4.60 (d, J = 9.2 Hz, 1H), 4.53 (d, J = 8.1 Hz, 1H), 4.40 (s, 2H), 4.35 (s, 1H), 4.32-4.27 (m, 3H), 4.27-4.25 (m, 6H), 4.20 (s, 2H), 3.81 (s, 3H), 3.65-3.61 (m, 3H), 3.52 (s, 1H), 3.43-3.35 (m, 2H), 3.05 (s, 1H), 2.85 (d, J = 17.1 Hz, 1H), 2.59-2.54 (m, 4H), 2.46 (s, 3H), 2.08-2.07 (m, 6H), 1.91 (s, 3H), 1.76 (s, 2H), 1.38 (s, 1H), 1.34 (s, 1H), 1.23 (d, J = 9.2 Hz, 2H), 1.08 (d, J = 6.2 Hz, 3H), 0.96 (s, 9H). |

TABLE 50-continued

Characterization data for intermediates prepared according to above.

| Inter-mediate | Structure | Chemical Name | MS: [(M + 1)]$^+$ | $^1$H NMR |
|---|---|---|---|---|
| I62 | 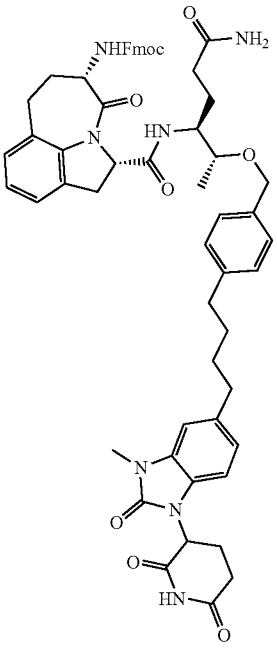 | 9H-fluoren-9-ylmethyl N-[(2S,11S)-2-[[(3S,4R)-1-carbamoyl-4-[(4-[4-[1-(2,6-dioxopiperidin-3-yl)-3-methyl-2-oxo-1,3-benzodiazol-5-yl]butyl]phenyl)methoxy]pentan-3-yl]carbamoyl]-12-oxo-1-azatricyclo[6.4.1.0^[4,13]]trideca-4(13),5,7-trien-11-yl]carbamate | 1000.6 | (400 MHz, DMSO-$d_6$) δ 11.08 (s, 1H), 7.88-7.82 (m, 3H), 7.81-7.67 (m, 3H), 7.50-7.38 (m, 3H), 7.34 (t, J = 7.4 Hz, 2H), 7.19-7.12 (m, 4H), 7.10 (d, J = 7.9 Hz, 1H), 7.08-6.89 (m, 4H), 6.89-6.81 (m, 1H), 6.76-6.42 (m, 1H), 5.38-5.33 (m, 1H), 5.12-5.05 (m, 1H), 4.40-4.38 (m, 3H), 4.26-4.21 (m, 5H), 4.16-4.07 (m, 1H), 3.79-3.70 (m, 2H), 3.49-3.37 (m, 2H), 3.31 (s, 3H), 3.16-3.06 (m, 2H), 2.97-2.76 (m, 2H), 2.76-2.54 (m, 3H), 2.15-1.99 (m, 4H), 1.76-1.71 (m, 1H), 1.65-1.50 (m, 3H), 1.26-1.21 (m, 2H), 1.03 (d, J = 6.2 Hz, 3H). |
| I63 | 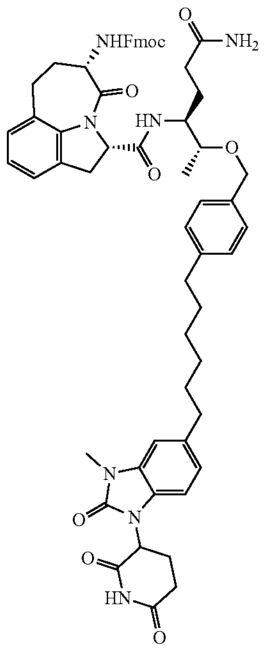 | 9H-fluoren-9-ylmethyl N-[(2S,11S)-2-[[(3S,4R)-1-carbamoyl-4-[(4-[6-[1-(2,6-dioxopiperidin-3-yl)-3-methyl-2-oxo-1,3-benzodiazol-5-yl]hexyl]phenyl)methoxy]pentan-3-yl]carbamoyl]-12-oxo-1-azatricyclo[6.4.1.0^[4,13]]trideca-4(13),5,7-trien-11-yl]carbamate | 1028.6 | (400 MHz, $CDCl_3$) δ 7.84-7.69 (m, 6H), 7.67 (d, J = 7.5 Hz, 2H), 7.48-7.33 (m, 4H), 7.32-7.27 (m, 4H), 7.22-7.09 (m, 5H), 6.89-6.81 (m, 1H), 6.37-6.26 (m, 1H), 6.11 (s, 2H), 5.40-5.34 (m, 1H), 5.33-5.31 (m, 4H), 5.26-4.98 (m, 1H), 4.93-4.54 (m, 1H), 4.53-4.31 (m, 5H), 4.27 (t, J = 7.5 Hz, 1H), 3.76-3.50 (m, 2H), 3.48 (s, 3H), 3.42 (s, 1H), 3.25-3.04 (m, 3H), 2.97-2.69 (m, 1H), 2.76-2.60 (m, 2H), 2.43-2.16 (m, 2H), 2.09 (m, 1H), 1.99-1.71 (m, 1H), 1.72-1.61 (m, 2H), 1.45-1.30 (m, 4H), 0.96 (d, J = 6.2 Hz, 3H). |

TABLE 50-continued

Characterization data for intermediates prepared according to above.

| Inter-mediate | Structure | Chemical Name | MS: [(M + 1)]+ | $^1$H NMR |
|---|---|---|---|---|
| I64 | 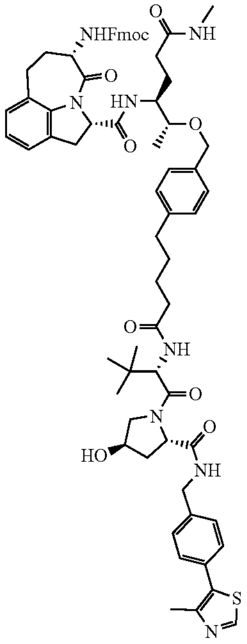 | 9H-fluoren-9-ylmethyl N-[(2S,11S)-2-[[(3S,4R)-4-[[4-(4-[[(2S)-1-(2S,4R)-4-hydroxy-2-([[4-(4-methyl-1,3-thiazol-5-yl)phenyl]methyl] carbamoyl)pyrrolidin-1-yl]-3,3-dimethyl-1-oxobutan-2-yl]carbamoyl]butyl) phenyl]methoxy]-1-(methylcarbamoyl) pentan-3-yl]carbamoyl]-12-oxo-1-azatricyclo[6.4.1.0^[4,13]] trideca-4(13),5,7-trien-11-yl]carbamate | 1213.9 | (400 MHz, DMSO-d$_6$) δ 8.99 (s, 1H), 8.57 (t, J = 6.1 Hz, 1H), 7.93-7.84 (m, 4H), 7.80-7.70 (m, 3H), 7.57 (d, J = 4.9 Hz, 1H), 7.46-7.29 (m, 8H), 7.16 (d, J = 7.9 Hz, 2H), 7.10 (d, J = 7.9 Hz, 2H), 7.05 (d, J = 7.6 Hz, 2H), 7.01-6.93 (m, 1H), 5.13 (s, 1H), 5.05-5.01 (m, 1H), 4.55 (d, J = 9.4 Hz, 1H), 4.48-4.32 (m, 4H), 4.32-4.16 (m, 3H), 4.12 (d, J = 8.9 Hz, 1H), 3.82-3.71 (m, 1H), 3.71-3.64 (m, 2H), 3.45-3.41 (m, 2H), 3.10-3.02 (m, 2H), 2.84-2.81 (m, 1H), 2.57-2.54 (m, 6H), 2.45 (s, 3H), 2.37-2.27 (m, 1H), 2.18-2.00 (m, 5H), 1.92-1.90 (m, 1H), 1.54-1.48 (m, 4H), 1.36-1.31 (m, 4H), 1.07 (d, J = 6.2 Hz, 3H), 0.94 (s, 9H). |
| I65 | 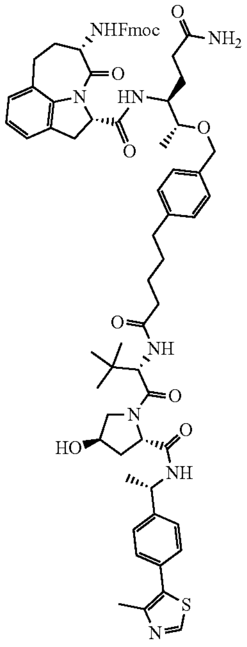 | 9H-fluoren-9-ylmethyl N-[(2S,11S)-2-[[(3S,4R)-1-carbamoyl-4-[[4-(4-[[(2S)-1-[(2S,4R)-4-hydroxy-2-[[(1S)-1-[4-(4-methyl-1,3-thiazol-5-yl)phenyl]ethyl] carbamoyl]pyrrolidin-1-yl]-3,3-dimethyl-1-oxobutan-2-yl]carbamoyl]butyl) phenyl]methoxy]pentan-3-yl]carbamoyl]-12-oxo-1-azatricyclo[6.4.1.0^[4,13]] trideca-4(13),5,7-trien-11-yl]carbamate | 1213.9 | (400 MHz, DMSO-d$_6$) δ 8.99 (s, 1H), 8.57 (t, J = 6.1 Hz, 1H), 7.93-7.84 (m, 4H), 7.8-7.70 (m, 3H), 7.57 (d, J = 4.9 Hz, 1H), 7.45-7.30 (m, 8H), 7.16 (d, J = 7.9 Hz, 2H), 7.10 (d, J = 7.9 Hz, 2H), 7.05 (d, J = 7.6 Hz, 2H), 7.00-6.93 (m, 1H), 6.88 (s, 1H), 5.13 (s, 1H), 5.05-5.01 (m, 1H), 4.55 (d, J = 9.4 Hz, 1H), 4.48-4.32 (m, 4H), 4.32-4.17 (m, 3H), 4.12 (d, J = 8.9 Hz, 1H), 3.81-3.71 (m, 1H), 3.71-3.64 (m, 2H), 3.43-3.41 (m, 2H), 3.07-3.02 (m, 2 H), 2.84-2.81 (m, 1H), 2.60-2.55-2.52 (m, 6H), 2.45 (s, 3H), 2.37-2.27 (m, 1H), 2.20-1.99 (m, 4H), 1.92-1.90 (m, 1H), 1.54-1.48 (m, 4H), 1.36-1.32 (m, 4H), 1.07 (d, J = 6.2 Hz, 3H), 0.94 (s, 9H). |

TABLE 50-continued

| Characterization data for intermediates prepared according to above. | | | | |
|---|---|---|---|---|
| Intermediate | Structure | Chemical Name | MS: [(M + 1)]+ | 1H NMR |
| I66 | 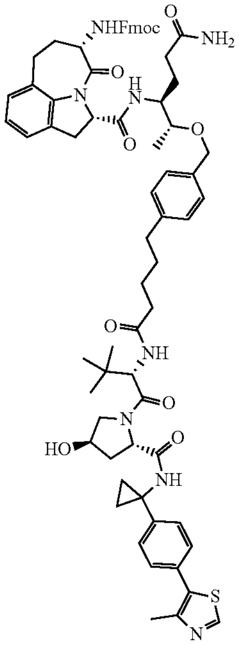 | 9H-fluoren-9-ylmethyl N-[(2S,11S)-2-[[(3S,4R)-1-carbamoyl-4-[[4-(4-[[(2S)-1-[(2S,4R)-4-hydroxy-2-([1-[4-(4-methyl-1,3-thiazol-5-yl)phenyl]cyclopropyl] carbamoyl)pyrrolidin-1-yl]-3,3-dimethyl-1-oxobutan-2-yl]carbamoyl]butyl) phenyl]methoxy]pentan-3-yl]carbamoyl]-12-oxo-1-azatricyclo[6.4.1.0^[4,13]] trideca-4(13),5,7-trien-11-yl]carbamate | 1225.2 | (400 MHz, DMSO-$d_6$) δ 8.97 (s, 1H), 8.81 (s, 1H), 7.98-7.81 (m, 4H), 7.80-7.70 (m, 3H), 7.54 (s, 1H), 7.43 (t, J = 7.4 Hz, 2H), 7.38-7.26 (m, 5H), 7.24-7.02 (m, 6H), 7.01-6.93 (m, 1H), 6.70 (s, 1H), 5.13 (d, J = 3.4 Hz, 1H), 5.10-5.02 (m, 1H), 4.56 (d, J = 9.4 Hz, 1H), 4.40 (d, J = 16.4 Hz, 1H), 4.40-4.38 (m, 3H), 4.36 (s, 1H), 4.32-4.23 (m, 2H), 4.10-4.08 (m, 2H), 3.79 (s, 1H), 3.65-3.62 (m, 2H), 3.48-3.37 (m, 2H), 3.18 (d, J = 5.2 Hz, 5H), 3.08-3.06 (m, 1H), 2.86 (d, J = 16.6 Hz, 1H), 2.55 (d, J = 7.1 Hz, 2H), 2.44 (s, 3H), 2.09-2.07 (m, 3H), 1.94-1.82 (m, 1H), 1.79 (s, 1H), 1.54-1.51 (m, 8 H), 1.29-1.15 (m, 3H), 1.08 (d, J = 6.1 Hz, 3H), 0.94 (s, 9H). |
| I67 | 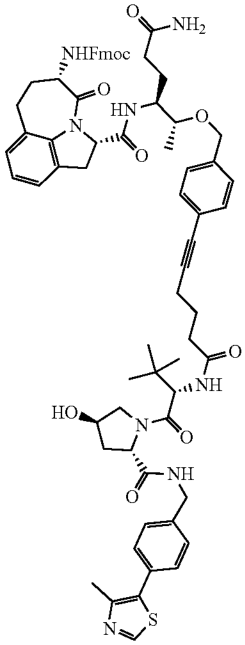 | 9H-fluoren-9-ylmethyl N-[(2S,11S)-2-[[(3S,4R)-1-carbamoyl-4-[[4-(5-[[(2S)-1-[(2S,4R)-4-hydroxy-2-([[4-(4-methyl-1,3-thiazol-5-yl)phenyl]methyl] carbamoyl)pyrrolidin-1-yl]-3,3-dimethyl-1-oxobutan-2-yl]carbamoyl]pent-1-yn-1-yl)phenyl]methoxy] pentan-3-yl]carbamoyl]-12-oxo-1-azatricyclo[6.4.1.0^[4,13]] trideca-4(13),5,7-trien-11-yl]carbamate | 1209.2 | (400 MHz, DMSO-$d_6$) δ 8.99 (s, 1H), 8.58-8.56 (m, 1H), 7.99 (d, J = 9.3 Hz, 1H), 7.91-7.89 (m, 3H), 7.77-7.75 (m, 4H), 7.40-7.33 (m, 9H), 7.25 (d, J = 8.0 Hz, 1H), 7.20-7.10 (m, 1H), 7.09-7.01 (m, 3H), 6.98-6.95 (m, 1H), 6.71 (s, 1H), 5.15 (s, 1H), 5.10-5.01 (m, 1H), 4.62-4.40 (m, 3H), 4.40-4.20 (m, 4H), 4.20-3.99 (m, 4H), 3.81-3.68 (m, 2H), 3.52-3.48 (m, 2H), 3.19 (m, 10H), 2.84 (d, J = 16.2 Hz, 1H), 2.49 (s, 3H), 2.20-1.88 (m, 4H), 1.88-1.49 (m, 3H), 1.10 (d, J = 6.1 Hz, 3H), 0.97 (s, 9H). |

TABLE 50-continued

Characterization data for intermediates prepared according to above.

| Inter-mediate | Structure | Chemical Name | MS: [(M + 1)]+ | 1H NMR |
|---|---|---|---|---|
| I68 | 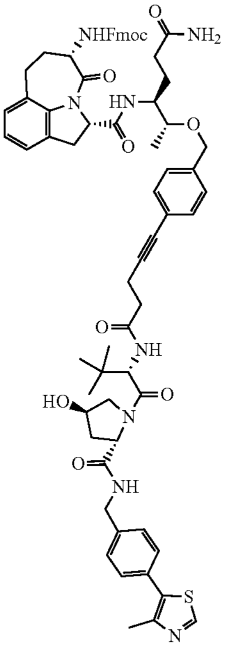 | 9H-fluoren-9-ylmethyl N-[(2S,11S)-2-[[(3S,4R)-1-carbamoyl-4-[[4-(4-[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]but-1-yn-1-yl)phenyl]methoxy]pentan-3-yl]carbamoyl]-12-oxo-1-azatricyclo[6.4.1.0^[4,13]]trideca-4(13),5,7-trien-11-yl]carbamate | 1195.2 | (400 MHz, $CD_3OD$) δ 7.81 (d, J = 7.5 Hz, 2H), 7.74-7.54 (m, 4H), 7.50-7.19 (m, 10H), 7.10-7.05 (m, 4H), 5.26-5.07 (m, 1H), 4.69-4.67 (m, 1H), 4.61-4.46 (m, 3H), 4.44-4.18 (m, 9H), 4.03-3.78 (m, 2H), 3.65-3.48 (m, 1H), 3.35-3.17 (m, 7H), 2.94 (d, J = 16.5 Hz, 1H), 2.72-2.69 (m, 1H), 2.52-2.47 (m, 2H), 2.22-2.16 (m, 5H), 2.02 (d, J = 7.6 Hz, 1H), 1.64-1.59 (m, 1H), 1.18-1.16 (m, 3H), 1.04 (s, 9H). |
| I69 | 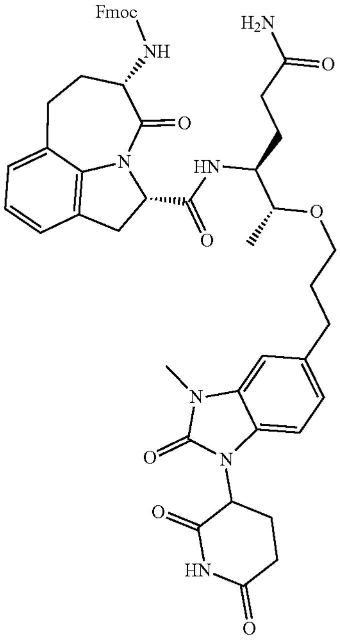 | 9H-fluoren-9-ylmethyl N-[(2S,11S)-2-[[(3S,4R)-1-carbamoyl-4-[3-[1-(2,6-dioxopiperidin-3-yl)-3-methyl-2-oxo-1,3-benzodiazol-5-yl]propoxy]pentan-3-yl]carbamoyl]-12-oxo-1-azatricyclo[6.4.1.0^[4,13]]trideca-4(13),5,7-trien-11-yl]carbamate | 896.3 | (400 MHz, $CD_3OD$) δ 7.81 (d, J = 7.5 Hz, 2H), 7.72-7.69 (m, 2H), 7.41 (t, J = 7.5 Hz, 2H), 7.32 (t, J = 7.4 Hz, 2H), 7.11-6.91 (m, 6H), 5.31-5.27 (m, 1H), 5.22-5.10 (m, 1H), 4.38-4.35 (m, 1H), 4.33-4.29 (d, J = 10.1 Hz, 2H), 4.28-4.20 (m, 1H), 3.92 (d, J = 11.9 Hz, 1H), 3.51-3.49 (m, 1H), 3.47-3.35 (m, 7H), 3.09-3.05 (m, 1H), 2.95-2.86 (m, 1H), 2.84-2.70 (m, 4H), 2.27-2.24 (m, 5H), 2.18-2.10 (m, 1H), 2.04-2.02 (m, 1H), 1.98-1.97 (m, 1H), 1.87 (t, J = 7.3 Hz, 2H), 1.15 (d, J = 6.4 Hz, 3H). |

TABLE 50-continued

| Characterization data for intermediates prepared according to above. | | | | |
|---|---|---|---|---|
| Inter-mediate | Structure | Chemical Name | MS: [(M + 1)]$^+$ | $^1$H NMR |
| I70 | 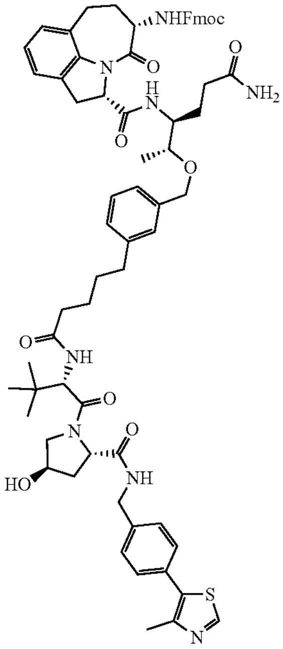 | 9H-fluoren-9-ylmethyl N-[(2S,11S)-2-[[(3S,4R)-1-carbamoyl-4-[[3-(4-[[(2S)-1-[(2S,4R)-4-hydroxy-2-([[4-(4-methyl-1,3-thiazol-5-yl)phenyl]methyl] carbamoyl)pyrrolidin-1-yl]-3,3-dimethyl-1-oxobutan-2-yl]carbamoyl]butyl) phenyl]methoxy]pentan-3-yl]carbamoyl]-12-oxo-1-azatricyclo[6.4.1.0^[4,13]] trideca-4(13),5,7-trien-11-yl]carbamate | 1199.2 | (400 MHz, $CD_3OD$) δ 8.87 (s, 1H), 7.81 (d, J = 7.6 Hz, 2H), 7.69 (t, J = 8.2 Hz, 2H), 7.46 (d, J = 8.0 Hz, 2H), 7.43-7.36 (m, 4H), 7.32-7.28 (m, 2H), 7.19 (d, J = 8.5 Hz, 2H), 7.14-6.97 (m, 5H), 5.11-5.09 (m, 1H), 4.68-4.58 (m, 1H), 4.58-4.51 (m, 5H), 4.41-4.28 (m, 3H), 4.24 (t, J = 7.0 Hz, 1H), 3.94-3.92 (m, 2H), 3.80-3.78 (m, 1H), 3.68-3.40 (m, 2H), 3.37 (s, 1H), 3.17-3.14 (m, 3H), 3.08-2.87 (m, 1H), 2.69-2.60 (m, 3H), 2.47 (s, 3H), 2.37-2.14 (m, 2H), 2.10-2.08 (m, 1H), 1.71-1.62 (m, 6H), 1.22-1.17 (m, 4H), 1.04-0.98 (m, 11H). |
| I71 | 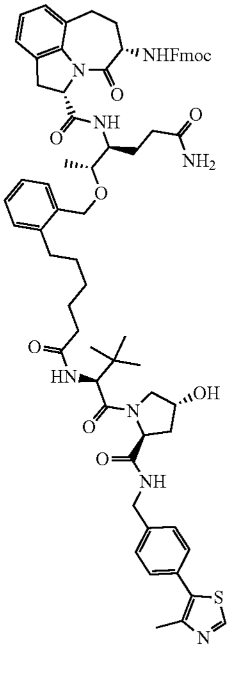 | 9H-fluoren-9-ylmethyl N-[(2S,11S)-2-[[(3S,4R)-1-carbamoyl-4-[[2-(5-[[(2S)-1-[(2S,4R)-4-hydroxy-2-([[4-(4-methyl-1,3-thiazol-5-yl)phenyl]methyl] carbamoyl)pyrrolidin-1-yl]-3,3-dimethyl-1-oxobutan-2-yl]carbamoyl]pentyl) phenyl]methoxy]pentan-3-yl]carbamoyl]-12-oxo-1-azatricyclo[6.4.1.0^[4,13]] trideca-4(13),5,7-trien-11-yl]carbamate | 1213.8 | (400 MHz, DMSO-$d_6$) δ 8.99 (s, 1H), 8.57 (t, J = 6.0 Hz, 1H), 7.89-7.82 (m, 4H), 7.75-7.71 (m, 3H), 7.47-7.29 (m, 9H), 7.25-6.92 (m, 7H), 6.72 (s, 1H), 5.18-4.95 (m, 2H), 4.58-4.32 (m, 7H), 4.32-4.07 (m, 5H), 3.85-3.64 (m, 3H), 3.55-3.38 (m, 1H), 3.19-2.98 (m, 1H), 2.85 (d, J = 16.7 Hz, 1H), 2.55-2.52 (m, 2H), 2.45 (s, 3H), 2.35-2.00 (m, 6H), 1.95-1.86 (m, 1H), 1.61-1.42 (m, 5H), 1.36 (s, 1H), 1.27-1.24 (m, 2H), 1.15-1.00 (m, 5H), 0.93 (s, 9 H). |

TABLE 50-continued

Characterization data for intermediates prepared according to above.

| Intermediate | Structure | Chemical Name | MS: [(M + 1)]+ | $^1$H NMR |
|---|---|---|---|---|
| I72 | 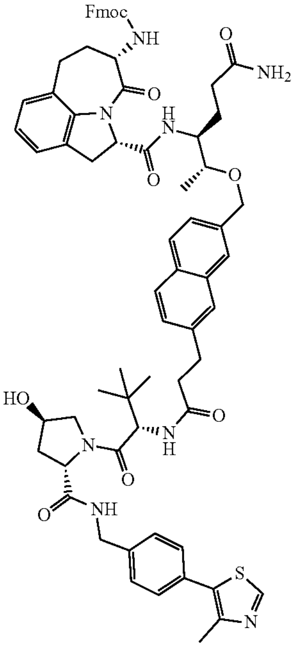 | 9H-fluoren-9-ylmethyl N-[(2S,11S)-2-[[(3S,4R)-1-carbamoyl-4-7-(2-[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]ethyl)naphthalen-2-yl]methoxy]pentan-3-yl]carbamoyl]-12-oxo-1-azatricyclo[6.4.1.0^[4,13]]trideca-4(13),5,7-trien-11-yl]carbamate | 1221.60 | (400 MHz, DMSO-$d_6$) δ 8.98 (s, 1H), 8.57 (t, J = 6.1 Hz, 1H), 8.00 (d, J = 9.3 Hz, 1H), 7.91-7.86 (m, 3H), 7.83-7.67 (m, 6H), 7.64 (s, 1H), 7.45-7.38 (m, 6H), 7.35-7.33 (m, 3H), 7.18 (s, 1H), 7.07-7.00 (m, 1H), 6.95-6.93 (m, 2H), 6.71 (s, 1H), 5.16 (d, J = 3.6 Hz, 1H), 5.09-5.01 (m, 1H), 4.62-4.58 (m, 3H), 4.44-4.41 (m, 2H), 4.36 (s, 1H), 4.31-4.17 (m, 3H), 4.12-4.09 (m, 3H), 3.82-3.79 (m, 1H), 3.69-3.67 (m, 2H), 3.52-3.41 (m, 1H), 3.19-3.15 (m, 5H), 3.13-2.93 (m, 2H), 2.84-2.67 (m, 2H), 2.44 (s, 3H), 2.10-2.00 (m, 4H), 1.92-1.90 (m, 1H), 1.83-1.78 (m, 2H), 1.60-1.56 (d, 1H), 1.11 (d, J = 6.2 Hz, 3H), 0.88 (s, 9H). |
| I73 | 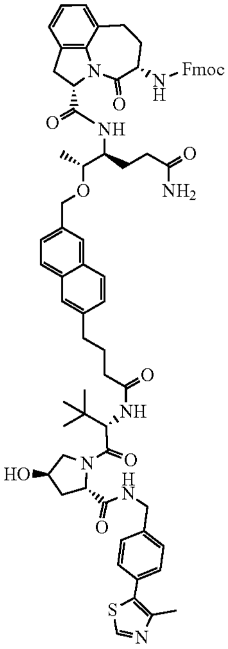 | 9H-fluoren-9-ylmethyl N-[(2S,11S)-2-[[(3S,4R)-1-carbamoyl-4-[[6-(3-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]propyl)naphthalen-2-yl]methoxy]pentan-3-yl]carbamoyl]-12-oxo-1-azatricyclo[6.4.1.0^[4,13]]trideca-4(13),5,7-trien-11-yl]carbamate | 1235.95 | Used in the next step without further purification |

TABLE 50-continued

| Characterization data for intermediates prepared according to above. | | | | |
|---|---|---|---|---|
| Inter-mediate | Structure | Chemical Name | MS: [(M + 1)]$^+$ | $^1$H NMR |
| I74 | 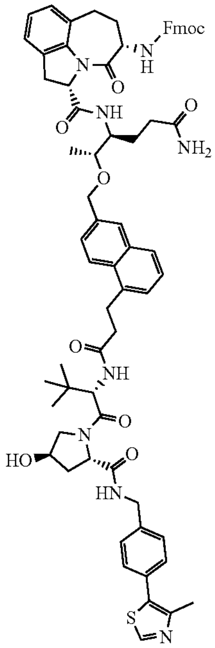 | 9H-fluoren-9-ylmethyl N-[(2S,11S)-2-[[(3S,4R)-1-carbamoyl-4-[[5-(2-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]ethyl)naphthalen-2-yl]methoxy]pentan-3-yl]carbamoyl]-12-oxo-1-azatricyclo[6.4.1.0^[4,13]]trideca-4(13),5,7-trien-11-yl]carbamate | 1221.30 | (400 MHz, DMSO-$d_6$) δ 8.99 (s, 1H), 8.58 (t, J = 6.0 Hz, 1H), 8.07 (d, J = 9.3 Hz, 1H), 7.99 (d, J = 8.7 Hz, 1H), 7.91-7.87 (m, 4H), 7.78-7.73 (m, 6H), 7.43-7.36 (m, 7H), 7.21-7.19 (m, 1H), 7.13-7.11 (d, J = 7.2 Hz, 1H), 7.09-6.93 (m, 4H), 6.74-6.72 (m, 1H), 5.18 (d, J = 3.5 Hz, 1H), 5.07-5.03 (m, 2H), 4.64-4.61 (m, 2H), 4.54-4.34 (m, 2H), 4.29-4.21 (m, 4H), 4.15-4.11 (m, 1H), 3.87-3.85 (m, 1H), 3.69-3.67 (m, 2H), 3.52-3.49 (m, 1H), 3.36-3.31 (m, 2H), 3.19-2.94 (m, 4H), 2.83-3.81 (m, 2H), 2.76-2.67 (m, 1H), 2.63-2.54 (m, 1H), 2.45 (s, 3H), 2.10-2.06 (s, 4H), 1.97-1.76 (m, 2H), 1.62-1.59 (m, 1H), 1.13 (d, J = 6.1 Hz, 3H), 0.94 (s, 9H). |
| I75 | 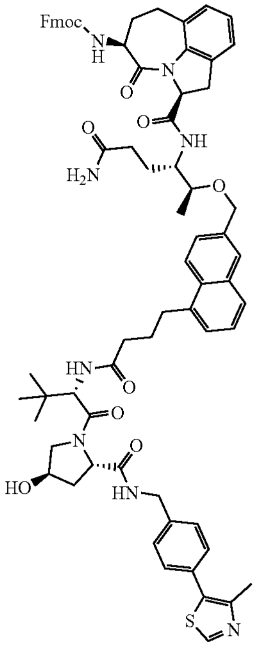 | 9H-fluoren-9-ylmethyl N-[(2S,11S)-2-[[(3S,4S)-1-carbamoyl-4-[[5-(3-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]propyl)naphthalen-2-yl]methoxy]pentan-3-yl]carbamoyl]-12-oxo-1-azatricyclo[6.4.1.0^[4,13]]trideca-4(13),5,7-trien-11-yl]carbamate | 1235.45 | (400 MHz, DMSO-$d_6$) δ 8.99 (s, 1H), 8.57 (t, J = 6.1 Hz, 1H), 7.99 (t, J = 8.1 Hz, 2H), 7.92-7.86 (m, 4H), 7.76-7.72 (m, 6H), 7.47-7.27 (m, 9H), 7.19 (s, 1H), 7.14-6.88 (m, 3H), 6.72 (s, 1H), 5.13 (d, J = 3.6 Hz, 1H), 5.06 (d, J = 10.3 Hz, 1H), 4.63-4.60 (m, 3H), 4.45-4.40 (m, 2H), 4.37-3.35 (m, 1H), 4.3-4.18 (m, 4H), 4.12-4.08 (m, 2H), 3.85-3.83 (m, 1H), 3.72-3.63 (m, 2 H), 3.52-3.50 (m, 1H), 3.45-3.36 (m, 1H), 3.14-2.96 (m, 3H), 2.79 (d, J = 17.0 Hz, 1H), 2.44 (s, 3H), 2.42-2.25 (m, 1H), 2.10-2.03 (m, 6H), 1.98-1.74 (m, 4H), 1.60-1.58 (m, 1H), 1.12 (d, J = 6.3 Hz, 3H), 0.96 (s, 9H). |

TABLE 50-continued

| Characterization data for intermediates prepared according to above. | | | | |
|---|---|---|---|---|
| Inter-mediate | Structure | Chemical Name | MS: [(M + 1)]+ | $^1$H NMR |
| I76 | 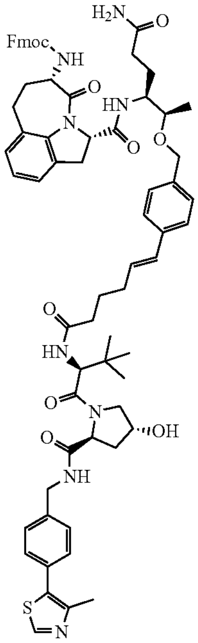 | 9H-fluoren-9-ylmethyl N-[(2S,11S)-2-[[(3S,4R)-1-carbamoyl-4-([4-[(1E)-5-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]pent-1-en-1-yl]phenyl]methoxy)pentan-3-yl]carbamoyl]-12-oxo-1-azatricyclo[6.4.1.0^[4,13]]trideca-4(13),5,7-trien-11-yl]carbamate | 1121.58 | (400 MHz, DMSO-$d_6$) δ 8.99 (s, 1H), 8.58 (s, 1H), 7.91-7.88 (m, 4H), 7.75 (t, J = 6.9 Hz, 3H), 7.46-7.35 (m, 5H), 7.35-7.29 (m, 3H), 7.22-7.18 (m, 4 H), 7.05 (d, J = 7.8 Hz, 2H), 6.99-6.97 (m, 1H), 6.71 (s, 1H), 6.42-6.27 (m, 1H), 5.77 (s, 1H), 5.15 (d, J = 3.6 Hz, 1H), 5.06-5.04 (m, 1H), 4.57 (d, J = 9.2 Hz, 1H), 4.49-4.39 (m, 4H), 4.38-4.36 (m, 1H), 4.26 (d, J = 7.5 Hz, 2H), 3.67 (s, 2H), 3.45-3.4 (m, 1H), 3.32 (s, 11H), 2.82 (d, J = 16.6 Hz, 1H), 2.45 (s, 3H), 2.33 (s, 1H), 2.17 (m, 2H), 2.07 (d, J = 14.7 Hz, 5H), 1.93-1.88 (m, 1H), 1.69-1.66 (m, 1H), 1.26-1.22 (m, 1H), 1.08 (d, J = 6.2 Hz, 3 H), 0.95 (s, 9H) |
| I77 | 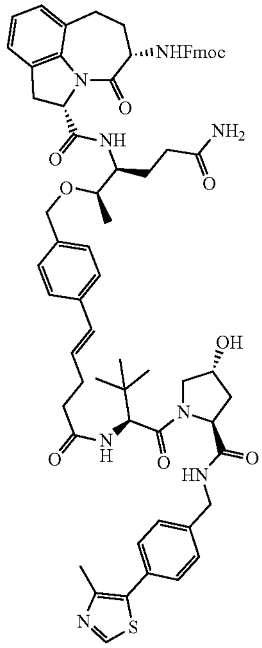 | 9H-fluoren-9-ylmethyl N-[(2S,11S)-2-[[(3S,4R)-1-carbamoyl-4-([4-[(1E)-4-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]but-1-en-1-yl]phenyl]methoxy)pentan-3-yl]carbamoyl]-12-oxo-1-azatricyclo[6.4.1.0^[4,13]]trideca-4(13),5,7-trien-11-yl]carbamate | 1197.45 | (400 MHz, $CDCl_3$) δ 8.70 (s, 1H), 8.03 (s, 1H), 7.76 (d, J = 7.6 Hz, 4H), 7.61 (d, J = 7.4 Hz, 4H), 7.40 (t, J = 7.4 Hz, 4H), 7.33-7.29 (m, 9H), 7.06-7.02 (m, 7H), 6.25-6.21 (m, 1H), 5.30 (s, 3H), 4.55-4.52 (m, 2H), 4.38 (d, J = 7.5 Hz, 4H), 4.25-4.21 (m, 2H), 4.03 (d, J = 10.9 Hz, 1H), 3.52-3.42 (m, 2H), 3.33-3.30 (m, 3H), 3.11 (d, J = 18.4 Hz, 4H), 2.96 (s, 1H), 2.89 (d, J = 0.7 Hz, 1H), 2.49 (s, 3H), 2.33-2.30 (m, 1H), 2.16 (d, J = 12.2 Hz, 2H), 2.06-2.02 (m, 2H), 1.25 (s, 2H), 1.18 (d, J = 6.4 Hz, 3H), 0.89 (s, 9H). |

TABLE 50-continued

Characterization data for intermediates prepared according to above.

| Inter-mediate | Structure | Chemical Name | MS: [(M + 1)]$^+$ | $^1$H NMR |
|---|---|---|---|---|
| I78 | 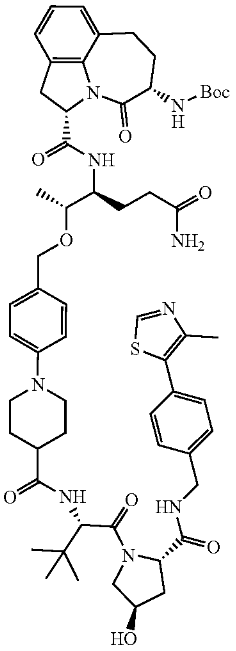 [SMILES: Cc1ncsc1-c1ccc(CNC(=O)[C@@H]2C[C@@H](O)CN2C(=O)[C@@H](NC(=O)C2CCN(c3ccc(CO[C@H](C)[C@H](CCC(N)=O)NC(=O)[C@@H]4Cc5cccc6c5N4C(=O)[C@@H](NC(=O)OC(C)(C)C)CC6)cc3)CC2)C(C)(C)C)cc1] | tert-butyl N-[(2S,11S)-2-[[(3S,4R)-1-carbamoyl-4-[[4-(4-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]piperidin-1-yl)phenyl]methoxy]pentan-3-yl]carbamoyl]-12-oxo-1-azatricyclo[6.4.1.0^[4,13]]trideca-4(13),5,7-trien-11-yl]carbamate | 1105.38 | (400 MHz, DMSO-d$_6$) δ 9.00 (d, J = 1.8 Hz, 1H), 8.64-8.55 (m, 1H), 7.88 (d, J = 9.4 Hz, 1H), 7.80 (d, J = 9.1 Hz, 1H), 7.45-7.38 (m, 5H), 7.16 (s, 1 H), 7.09 (s, 2H), 7.05 (d, J = 6.8 Hz, 2H), 6.96 (s, 1H), 6.85 (d, J = 8.5 Hz, 1H), 6.68 (s, 1H), 5.76 (s, 3H), 5.15-5.01 (m, 2H), 4.62-4.53 (m, 1H), 4.50-4.41 (m, 3H), 4.39-4.30 (m, 3H), 4.04 (s, 1H), 3.68 (dd, J = 18.0, 10.6 Hz, 5H), 2.64 (d, J = 12.1 Hz, 2H), 2.46 (s, 3H), 2.10-2.02 (m, 5H), 1.94-1.88 (m, 1H), 1.85-1.76 (m, 3H), 1.69-1.62 (m, 2H), 1.39 (s, 9H), 1.24 (s, 1H), 1.14 (d, J = 6.3 Hz, 3H), 1.10-1.04 (m, 4H), 0.96 (s, 9H). |
| I79 | 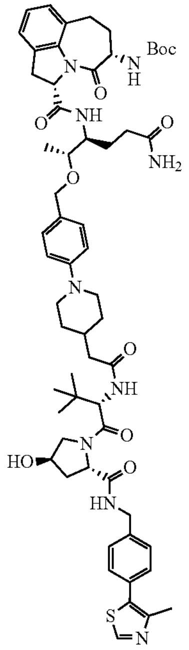 [SMILES: Cc1ncsc1-c1ccc(CNC(=O)[C@@H]2C[C@@H](O)CN2C(=O)[C@@H](NC(=O)CC2CCN(c3ccc(CO[C@H](C)[C@H](CCC(N)=O)NC(=O)[C@@H]4Cc5cccc6c5N4C(=O)[C@@H](NC(=O)OC(C)(C)C)CC6)cc3)CC2)C(C)(C)C)cc1] | tert-butyl N-[(2S,11S)-2-[[(3S,4R)-1-carbamoyl-4-([4-[4-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methyl)piperidin-1-yl]phenyl]methoxy)pentan-3-yl]carbamoyl]-12-oxo-1-azatricyclo[6.4.1.0^[4,13]]trideca-4(13),5,7-trien-11-yl]carbamate | 1118.57 | (400 MHz, CD$_3$OD) δ 8.89 (s, 1H), 7.49 (d, J = 8.3 Hz, 2H), 7.46-7.42 (m, 2H), 7.22-7.18 (m, 2H), 7.08 (t, J = 8.2 Hz, 2H), 7.01 (t, J = 7.4 Hz, 1H), 6.94-6.89 (m, 2H), 5.11 (dd, J = 10.9, 3.4 Hz, 1H), 4.70-4.65 (m, 1H), 4.60-4.56 (m, 1H), 4.53 (d, J = 7.2 Hz, 2H), 4.49-4.39 (m, 3H), 4.25 (dd, J = 8.5, 3.7 Hz, 1H), 4.00-3.92 (m, 2H), 3.83 (dd, J = 10.9, 3.9 Hz, 1H), 3.67 (d, J = 13.6 Hz, 2H), 3.55 (dd, J = 6.4, 4.5 Hz, 1H), 3.45 (dd, J = 16.7, 10.9 Hz, 1H), 3.15 (q, J = 6.7, 5.7 Hz, 2 H), 2.96 (dd, J = 16.6, 3.3 Hz, 1H), 2.76-2.63 (m, 3H), 2.49 (s, 3H), 2.30-2.25 (m, 4H), 2.21 (d, J = 6.3 Hz, 2H), 2.13-2.10 (m, 1H), 2.01-1.89 (m, 2H), 1.82 (d, J = 13.0 Hz, 2H), 1.72-1.62 (m, 1H), 1.52-1.44 (m, 12H), 1.18 (d, J = 6.4 Hz, 3H), 1.07 (s, 9H). |

TABLE 50-continued

Characterization data for intermediates prepared according to above.

| Inter-mediate | Structure | Chemical Name | MS: [(M + 1)]$^+$ | $^1$H NMR |
|---|---|---|---|---|
| I80 | 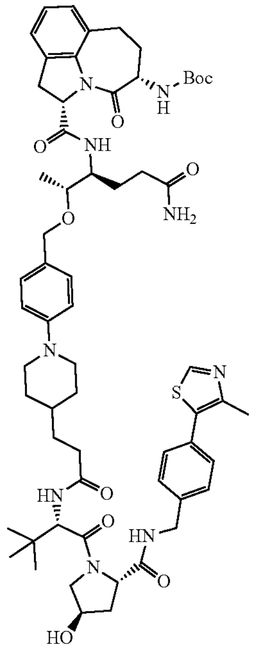 [SMILES: Cc1ncsc1-c1ccc(CNC(=O)[C@@H]2C[C@@H](O)CN2C(=O)[C@@H](NC(=O)CCC2CCN(c3ccc(CO[C@H](C)[C@H](CCC(N)=O)NC(=O)[C@@H]4Cc5cccc6c5N4C(=O)[C@@H](NC(=O)OC(C)(C)C)CC6)cc3)CC2)C(C)(C)C)cc1] | tert-butyl N-[(2S,11S)-2-[[(3S,4R)-1-carbamoyl-4-([4-[4-(2-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]ethyl)piperidin-1-yl]phenyl]methoxy)pentan-3-yl]carbamoyl]-12-oxo-1-azatricyclo[6.4.1.0^[4,13]]trideca-4(13),5,7-trien-11-yl]carbamate | 1132.90 | (400 MHz, $CD_3OD$) δ 8.89 (s, 1H), 8.37 (s, 1H), 7.92 (dd, J = 15.1, 9.2 Hz, 1H), 7.52-7.39 (m, 5H), 7.20 (d, J = 8.0 Hz, 2H), 7.08 (t, J = 8.2 Hz, 2H), 7.01 (t, J = 7.4 Hz, 1H), 6.92 (d, J = 8.0 Hz, 2H), 5.11 (dd, J = 10.9, 3.4 Hz, 1H), 4.71-4.64 (m, 1H), 4.61-4.55 (m, 2H), 4.54-4.51 (m, 1H), 4.44 (d, J = 8.9 Hz, 2H), 4.42-4.33 (m, 1H), 4.27-4.23 (m, 1H), 4.00-3.92 (m, 2H), 3.83 (dd, J = 11.0, 3.9 Hz, 1H), 3.71-3.64 (m, 3H), 3.60-3.51 (m, 1H), 3.51-3.39 (m, 1H), 3.22-3.08 (m, 2H), 2.96 (dd, J = 16.7, 3.3 Hz, 1H), 2.67 (t, J = 11.7 Hz, 2H), 2.49 (s, 3H), 2.37 (q, J = 8.0 Hz, 2H), 2.31-2.15 (m, 4H), 2.14-2.07 (m, 1H), 2.06-1.94 (m, 1H), 1.85 (d, J = 11.9 Hz, 2H), 1.73-1.57 (m, 2H), 1.48 (s, 9H), 1.44-1.29 (m, 1H), 1.18 (d, J = 6.3 Hz, 3H), 1.07 (s, 9H). |
| I81 | 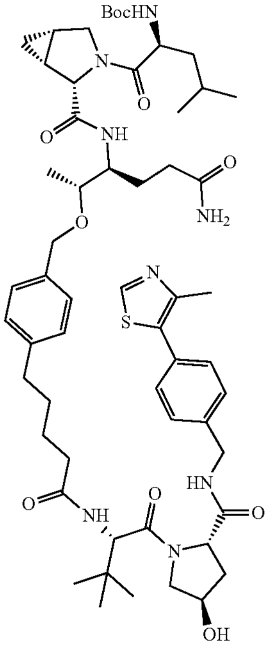 [SMILES: Cc1ncsc1-c1ccc(CNC(=O)[C@@H]2C[C@@H](O)CN2C(=O)[C@@H](NC(=O)CCCCc2ccc(CO[C@H](C)[C@H](CCC(N)=O)NC(=O)[C@@H]3[C@@H]4C[C@@H]4CN3C(=O)[C@H](CC(C)C)NC(=O)OC(C)(C)C)cc2)C(C)(C)C)cc1] | tert-butyl N-[(2S)-1-[(1R,2S,5S)-2-[[(3S,4R)-1-carbamoyl-4-[[4-(4-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]butyl)phenyl]methoxy]pentan-3-yl]carbamoyl]-3-azabicyclo[3.1.0]hexan-3-yl]-4-methyl-1-oxopentan-2-yl]carbamate | 1071.30 | (400 MHz, DMSO-$d_6$) δ 8.99 (s, 1H), 8.57 (t, J = 6.0 Hz, 1H), 7.89 (d, J = 9.3 Hz, 1H), 7.58 (d, J = 9.3 Hz, 1H), 7.41 (q, J = 8.4 Hz, 4H), 7.24 (d, J = 7.8 Hz, 2H), 7.14 (d, J = 7.8 Hz, 2 H), 7.05 (s, 1H), 6.96 (d, J = 7.7 Hz, 1H), 6.67 (s, 1H), 5.13 (d, J = 3.5 Hz, 1H), 4.55 (d, J = 9.4 Hz, 1H), 4.50-4.32 (m, 6H), 4.26-4.18 (m, 1H), 4.12-4.06 (m, 1H), 3.89-3.85 (m, 1H), 3.75-3.60 (m, 2H), 3.53 (d, J = 9.6 Hz, 1H), 3.36-3.32 (m, 3H), 2.56-2.53 (m, 1H), 2.45 (s, 3H), 2.33-2.30 (m, 1H), 2.22-1.99 (m, 4H), 1.95-1.86 (m, 2H), 1.83-1.72 (m, 2H), 1.64-1.52 (m, 7H), 1.37 (s, 9H), 1.24-1.20 (m, 1H), 1.08 (d, J = 6.2 Hz, 3H), 0.94 (s, 9H), 0.86 (d, J = 6.6 Hz, 6H), 0.72-0.69 (m, 1H), 0.61-0.53 (m, 1H). |

TABLE 50-continued

| Characterization data for intermediates prepared according to above. | | | | |
|---|---|---|---|---|
| Inter-mediate | Structure | Chemical Name | MS: [(M + 1)]$^+$ | $^1$H NMR |
| I82 | 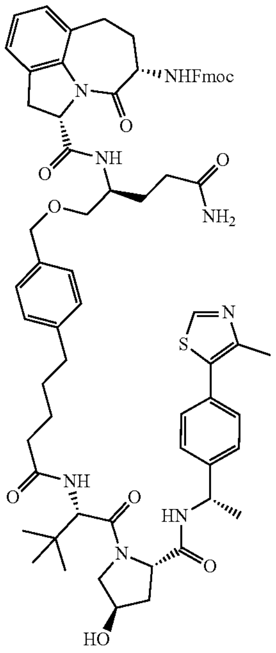 | 9H-Fluoren-9-ylmethyl N-[(2S,11S)-2-[[(2S)-4-carbamoyl-1-[[4-(4-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]butyl)phenyl]methoxy]butan-2-yl]carbamoyl]-12-oxo-1-azatricyclo[6.4.1.0^[4,13]]trideca-4(13),5,7-trien-11-yl]carbamate | 1199.45 | (400 MHz, DMSO-$d_6$) δ 8.99 (s, 1H), 8.38 (d, J = 7.8 Hz, 1H), 7.92-7.85 (m, 4H), 7.74 (q, J = 7.6, 7.2 Hz, 3H), 7.47-7.29 (m, 8H), 7.25-7.09 (m, 5H), 7.08-6.91 (m, 3H), 6.72 (s, 1H), 5.11 (d, J = 3.6 Hz, 1H), 5.02 (dd, J = 10.6, 2.9 Hz, 1H), 4.92 (p, J = 7.1 Hz, 1 H), 4.52 (d, J = 9.3 Hz, 1H), 4.42 (d, J = 6.7 Hz, 3H), 4.35-4.15 (m, 4H), 4.15-4.06 (m, 1H), 3.83 (m, 1H), 3.70-3.53 (m, 2H), 3.21-2.94 (m, 2H), 2.94-2.65 (m, 1H), 2.56 (d, J = 7.1 Hz, 1H), 2.46 (s, 3H), 2.36-2.23 (m, 1H), 2.08 (s, 12H), 1.83-1.77 (m, 1H), 1.67-1.43 (m, 4H), 1.38 (d, J = 6.9 Hz, 3H), 0.94 (s, 9H). |
| I83 | 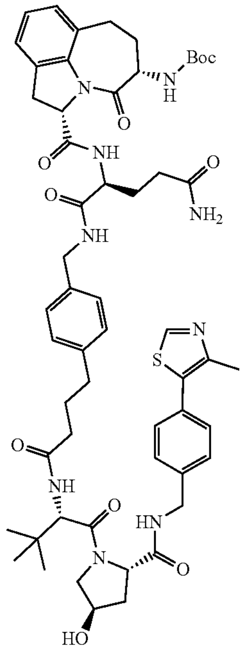 [SMILES: Cc1ncsc1-c1ccc(CNC(=O)[C@@H]2C[C@@H](O)CN2C(=O)[C@@H](NC(=O)CCCc2ccc(CNC(=O)[C@H](CCC(N)=O)NC(=O)[C@@H]3Cc4cccc5c4N3C(=O)[C@@H](NC(=O)OC(C)(C)C)CC5)cc2)C(C)(C)C)cc1] | tert-butyl N-[(2S,11S)-2-[[(1S)-3-carbamoyl-1-([[4-(3-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]propyl)phenyl]methyl]carbamoyl)propyl]carbamoyl]-12-oxo-1-azatricyclo[6.4.1.0^[4,13]]trideca-4(13),5,7-trien-11-yl]carbamate | 1062.40 | (400 MHz DMSO-$d_6$) δ 8.99 (s, 1H), 8.57 (t, J = 6.1 Hz, 1H), 8.35 (t, J = 5.9 Hz, 1H), 8.20 (d, J = 7.9 Hz, 1H), 7.91 (d, J = 9.3 Hz, 1H), 7.43 (d, J = 8.4 Hz, 2H), 7.39 (d, J = 8.4 Hz, 2H), 7.26 (s, 1H), 7.12-7.08 (m, 4H), 7.08 (d, J = 6.4 Hz, 2H), 6.98-6.96 (m, 2H), 6.76 (s, 1H), 5.16-5.08 (m, 2H), 4.56 (d, J = 9.3 Hz, 1H), 4.47-4.40 (m, 2H), 4.36-4.34 (m, 1H), 4.24-4.20 (m, 4H), 4.05 (d, J = 9.1 Hz, 1H), 3.68-3.66 (m, 2H), 3.32-3.30 (m, 2H), 3.10-30.6 (m, 2H), 3.02-2.96 (m, 2H), 2.45 (s, 3H), 2.28-2.17 (m, 2H), 2.09-2.01 (m, 6H), 1.93-1.91 (m, 1H), 1.78-1.74 (m, 3H), 1.39 (s, 9H), 0.95 (s, 9H) |

TABLE 50-continued

| Characterization data for intermediates prepared according to above. | | | | |
|---|---|---|---|---|
| Inter-mediate | Structure | Chemical Name | MS: [(M + 1)]$^+$ | $^1$H NMR |
| I84 | 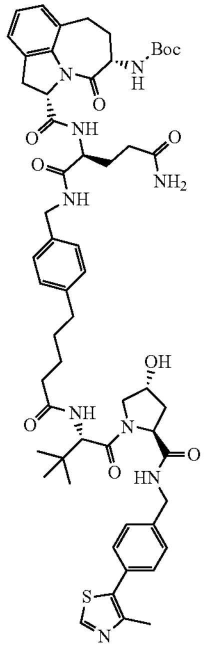 [SMILES: Cc1ncsc1-c1ccc(CNC(=O)[C@@H]2C[C@@H](O)CN2C(=O)[C@@H](NC(=O)CCCCc2ccc(CNC(=O)[C@H](CCC(N)=O)NC(=O)[C@@H]3Cc4cccc5c4N3C(=O)[C@@H](NC(=O)OC(C)(C)C)CC5)cc2)C(C)(C)C)cc1] | tert-butyl N-[(2S,11S)-2-[[(1S)-3-carbamoyl-1-([[4-(4-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]butyl)phenyl]methyl]carbamoyl)propyl]carbamoyl]-12-oxo-1-azatricyclo[6.4.1.0^[4,13]]trideca-4(13),5,7-trien-11-yl]carbamate | 1076.60 | (400 MHz, $CD_3OD$) δ 8.89 (s, 1H), 7.48 (d, J = 8.2 Hz, 2H), 7.43 (d, J = 8.2 Hz, 2H), 7.20-6.98 (m, 7H), 5.17 (dd, J = 10.9, 3.3 Hz, 1H), 4.66-4.45 (m, 5H), 4.40-4.19 (m, 4H), 3.89 (s, 1H), 3.81 (dd, J = 11.0, 3.9 Hz, 1H), 3.56-3.45 (m, 1H), 3.37 (s, 3H), 3.21-3.08 (m, 1H), 2.69-2.57 (m, 3H), 2.49 (s, 3H), 2.41-2.16 (m, 5H), 2.14-1.89 (m, 2H), 1.63 (s, 5H), 1.47 (s, 9H), 1.04 (s, 9H) |
| I85 | 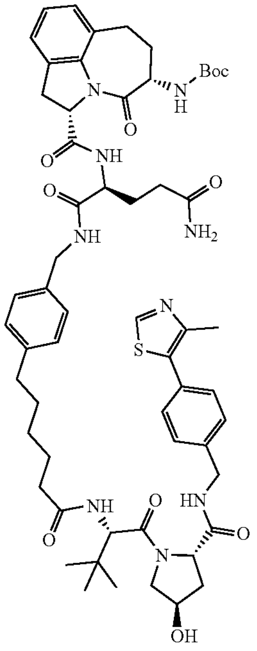 [SMILES: Cc1ncsc1-c1ccc(CNC(=O)[C@@H]2C[C@@H](O)CN2C(=O)[C@@H](NC(=O)CCCCCc2ccc(CNC(=O)[C@H](CCC(N)=O)NC(=O)[C@@H]3Cc4cccc5c4N3C(=O)[C@@H](NC(=O)OC(C)(C)C)CC5)cc2)C(C)(C)C)cc1] | tert-butyl N-[(2S,11S)-2-[[(1S)-3-carbamoyl-1-([[4-(5-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]pentyl)phenyl]methyl]carbamoyl)propyl]carbamoyl]-12-oxo-1-azatricyclo[6.4.1.0^[4,13]]trideca-4(13),5,7-trien-11-yl]carbamate | 1090.40 | (400 MHz, DMSO-$d_6$) δ 8.99 (s, 1H), 8.57 (m, J = 6.1 Hz, 1H), 8.35 (m, J = 5.8 Hz, 1H), 8.20 (d, J = 7.9 Hz, 1 H), 7.86 (d, J = 9.3 Hz, 1H), 7.44-7.37 (m, 4H), 7.26 (s, 1H), 7.13-7.03 (m, 7H), 6.97-6.95 (m, 2H), 6.76 (s, 1H), 5.15-5.08 (m, 2H), 4.54 (d, J = 9.4 Hz, 1H), 4.47-4.40 (m, 2H), 4.35 (s, 1H), 4.24-4.18 (m, 4H), 4.05-4.03 (m, 1H), 3.70-3.62 (m, 2H), 3.46-3.39 (m, 1H), 3.12-2.92 (m, 3H), 2.45 (s, 3H), 2.28-2.24 (m, 1H), 2.15-1.99 (m, 7H), 1.93-1.89 (m, 2H), 1.77-1.75 (m, 1H), 1.55-1.49 (m, 4H), 1.39 (s, 9H), 1.28-1.24 (m, 2H), 0.93 (s, 9H) |

TABLE 50-continued

| Characterization data for intermediates prepared according to above. | | | | |
|---|---|---|---|---|
| Inter-mediate | Structure | Chemical Name | MS: [(M + 1)]$^+$ | $^1$H NMR |
| I86 | 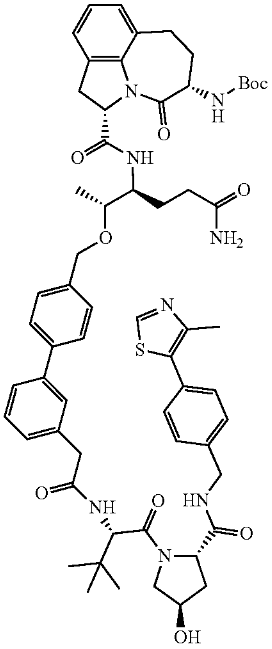 [SMILES: Cc1ncsc1-c1ccc(CNC(=O)[C@@H]2C[C@@H](O)CN2C(=O)[C@@H](NC(=O)Cc2cccc(-c3ccc(CO[C@H](C)[C@H](CCC(N)=O)NC(=O)[C@@H]4Cc5cccc6c5N4C(=O)[C@@H](NC(=O)OC(C)(C)C)CC6)cc3)c2)C(C)(C)C)cc1] | tert-butyl N-[(2S,11S)-2-[[(3S,4R)-1-carbamoyl-4-[[3'-([[(2S)-1-[(2S,4R)-4-hydroxy-2-([[4-(4-methyl-1,3-thiazol-5-yl)phenyl]methyl] carbamoyl)pyrrolidin-1-yl]-3,3-dimethyl-1-oxobutan-2-yl]carbamoyl]methyl)-[1,1'-biphenyl]-4-yl]methoxy]pentan-3-yl]carbamoyl]-12-oxo-1-azatricyclo[6.4.1.0^[4,13]] trideca-4(13),5,7-trien-11-yl]carbamate | 1111.70 | (400 MHz, DMSO-$d_6$) δ 9.00 (s, 1H), 8.59 (t, J = 6.1 Hz, 1H), 8.19 (d, J = 9.3 Hz, 1H), 7.87 (d, J = 9.3 Hz, 1H), 7.61-7.55 (m, 3H), 7.51 (d, J = 7.8 Hz, 1H), 7.49-7.37 (m, 7H), 7.28 (d, J = 7.6 Hz, 1H), 7.19 (s, 1H), 7.10 (d, J = 7.9 Hz, 1H), 7.06-7.02 (m, 2H), 6.96 (t, J = 7.4 Hz, 1H), 6.70 (s, 1H), 5.77 (s, 3H), 5.14-5.12 (m, 1H), 5.08 (dd, J = 10.7, 2.8 Hz, 1H), 4.56 (d, J = 9.3 Hz, 1H), 4.50-4.42 (m, 4H), 4.36 (s, 1H), 4.23 (dd, J = 15.9, 5.5 Hz, 1H), 4.06 (t, J = 8.5 Hz, 1H), 3.84-3.82 (m, 1H), 3.76 (d, J = 13.8 Hz, 1H), 3.70-3.62 (m, 2H), 3.57-3.46 (m, 3H), 3.10-2.99 (m, 1H), 2.87 (d, J = 16.5 Hz, 1H), 2.46 (s, 3H), 2.15-2.04 (m, 3H), 1.95-1.88 (m, 1H), 1.81-1.79 (m, 1H), 1.63-1.56 (m, 1H), 1.39 (s, 9H), 1.12 (d, J = 6.2 Hz, 3H), 0.94 (s, 9H) |
| I87 | 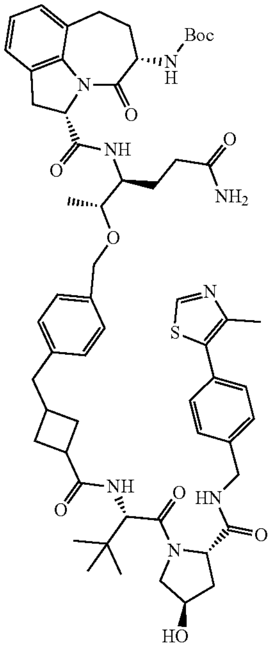 [SMILES: Cc1ncsc1-c1ccc(CNC(=O)[C@@H]2C[C@@H](O)CN2C(=O)[C@@H](NC(=O)C2CC(Cc3ccc(CO[C@H](C)[C@H](CCC(N)=O)NC(=O)[C@@H]4Cc5cccc6c5N4C(=O)[C@@H](NC(=O)OC(C)(C)C)CC6)cc3)C2)C(C)(C)C)cc1] | tert-butyl N-[(2S,11S)-2-[[(3S,4R)-1-carbamoyl-4-[(4-[[(1r,3r)-3-[[(2S)-1-[(2S,4R)-4-hydroxy-2-([[4-(4-methyl-1,3-thiazol-5-yl)phenyl]methyl] carbamoyl)pyrrolidin-1-yl]-3,3-dimethyl-1-oxobutan-2-yl]carbamoyl]cyclobutyl] methyl]phenyl)methoxy] pentan-3-yl]carbamoyl]-12-oxo-1-azatricyclo[6.4.1.0^[4,13]] trideca-4(13),5,7-trien-11-yl]carbamate | 1189.54 | (400 MHz, DMSO-$d_6$) δ 8.99 (d, J = 1.2 Hz, 1H), 8.56 (t, J = 6.0 Hz, 1H), 7.83 (d, J = 9.2 Hz, 1H), 7.68 (t, J = 8.6 Hz, 1H), 7.45-7.35 (m, 4H), 7.16 (d, J = 7.9 Hz, 3H), 7.10-7.02 (m, 5H), 7.00-6.93 (m, 1H), 6.68 (s, 1H), 5.14 (s, 1H), 5.06 (dd, J = 10.8, 2.7 Hz, 1H), 4.55 (d, J = 9.4 Hz, 1H), 4.48-4.32 (m, 5H), 4.22 (dd, J = 15.9, 5.5 Hz, 1H), 4.05 (t, J = 8.7 Hz, 1H), 3.79 (s, 1H), 3.67 (s, 2H), 3.50-3.36 (m, 2H), 3.11-2.95 (m, 2H), 2.86 (d, J = 16.6 Hz, 1H), 2.65 (dd, J = 33.6, 7.6 Hz, 2H), 2.45 (s, 3H), 2.43-2.32 (m, 1H), 2.22-1.97 (m, 3H), 1.96-1.84 (m, 2H), 1.78 (q, J = 9.5 Hz, 2H), 1.56 (dd, J = 17.1, 8.1 Hz, 1H), 1.40-1.38 (m, 11H), 1.25-1.23 (m, 1H), 1.08 (d, J = 6.3 Hz, 3H), 0.93 (s, 9H) |

TABLE 50-continued

| Characterization data for intermediates prepared according to above. | | | | |
|---|---|---|---|---|
| Intermediate | Structure | Chemical Name | MS: [(M + 1)]$^+$ | $^1H$ NMR |
| I88 | 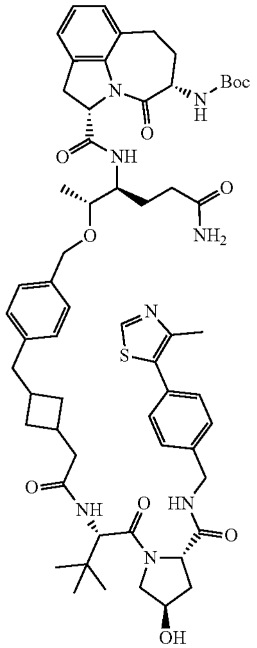 [SMILES: Cc1ncsc1-c1ccc(CNC(=O)[C@@H]2C[C@@H](O)CN2C(=O)[C@@H](NC(=O)CC2CC(Cc3ccc(CO[C@H](C)[C@H](CCC(N)=O)NC(=O)[C@@H]4Cc5cccc6c5N4C(=O)[C@@H](NC(=O)OC(C)(C)C)CC6)cc3)C2)C(C)(C)C)cc1] | tert-butyl N-[(2S,11S)-2-[[(3S,4R)-1-carbamoyl-4-[(4-[[3-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methyl)cyclobutyl]methyl]phenyl)methoxy]pentan-3-yl]carbamoyl]-12-oxo-1-azatricyclo[6.4.1.0^[4,13]]trideca-4(13),5,7-trien-11-yl]carbamate | 1103.39 | Used in the next step without further purification |
| I89 | 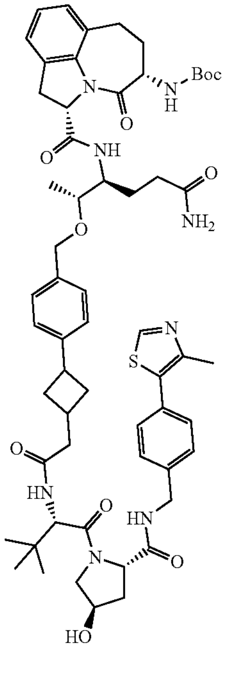 [SMILES: Cc1ncsc1-c1ccc(CNC(=O)[C@@H]2C[C@@H](O)CN2C(=O)[C@@H](NC(=O)CC2CC(c3ccc(CO[C@H](C)[C@H](CCC(N)=O)NC(=O)[C@@H]4Cc5cccc6c5N4C(=O)[C@@H](NC(=O)OC(C)(C)C)CC6)cc3)C2)C(C)(C)C)cc1] | tert-butyl N-[(2S,11S)-2-[[(3S,4R)-1-carbamoyl-4-([4-[3-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methyl)cyclobutyl]phenyl]methoxy)pentan-3-yl]carbamoyl]-12-oxo-1-azatricyclo[6.4.1.0^[4,13]]trideca-4(13),5,7-trien-11-yl]carbamate | 1089.70 | (400 MHz, $CD_3OD$) δ 8.89 (d, J = 1.3 Hz, 1H), 8.11 (s, 1H), 7.48 (dd, J = 8.4, 2.6 Hz, 2H), 7.48-7.39 (m, 2H), 7.29-7.13 (m, 4H), 7.09 (d, J = 7.3 Hz, 1H), 7.07-6.95 (m, 2H), 5.12 (dt, J = 10.5, 3.0 Hz, 1H), 4.67 (d, J = 4.3 Hz, 1H), 4.64-4.44 (m, 5H), 4.37 (dd, J = 15.5, 2.9 Hz, 1H), 4.28-4.21 (m, 1H), 4.12 (q, J = 7.1 Hz, 1H), 4.00 (d, J = 6.3 Hz, 1H), 3.92 (d, J = 10.9 Hz, 1H), 3.84-3.80 (m, 1H), 3.69-3.53 (m, 1H), 3.51-3.35 (m, 1H), 3.23-3.05 (m, 2H), 3.01-2.97 (m, 1H), 2.78-2.54 (m, 1H), 2.49 (s, 3H), 2.47-2.35 (m, 1H), 2.33-2.24 (m, 3H), 2.23-2.18 (m, 5H), 2.14-2.01 (m, 2H), 1.88-1.84 (m, 1H), 1.71-1.67 (m, 1H), 1.57 (s, 1H), 1.48 (s, 9H), 1.19 (s, 3H), 1.06 (s, 9H) |

TABLE 50-continued

| Characterization data for intermediates prepared according to above. | | | | |
|---|---|---|---|---|
| Inter-mediate | Structure | Chemical Name | MS: [(M + 1)]$^+$ | $^1$H NMR |
| I90 | 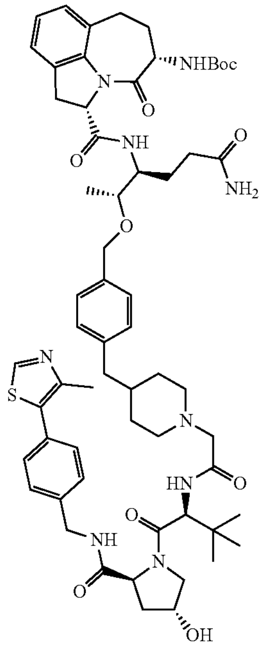 [SMILES: Cc1ncsc1-c1ccc(CNC(=O)[C@@H]2C[C@@H](O)CN2C(=O)[C@@H](NC(=O)CN2CCC(Cc3ccc(CO[C@H](C)[C@H](CCC(N)=O)NC(=O)[C@@H]4Cc5cccc6c5N4C(=O)[C@@H](NC(=O)OC(C)(C)C)CC6)cc3)CC2)C(C)(C)C)cc1] | tert-butyl N-[(2S,11S)-2-[[(3S,4R)-1-carbamoyl-4-[(4-[[1-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methyl)piperidin-4-yl]methyl]phenyl)methoxy]pentan-3-yl]carbamoyl]-12-oxo-1-azatricyclo[6.4.1.0^[4,13]]trideca-4(13),5,7-trien-11-yl]carbamate | 1132.50 | (400 MHz, DMSO-$d_6$) δ 9.75 (s, 1H), 9.02 (s, 1H), 8.76 (d, J = 8.9 Hz, 1H), 8.62 (t, J = 6.1 Hz, 1H), 8.55-8.49 (m, 2H), 8.05 (d, J = 9.2 Hz, 1H), 7.91-7.75 (m, 1H), 7.48-7.39 (m, 5H), 7.29-6.87 (m, 6H), 6.74 (s, 1H), 5.14 (dd, J = 10.9, 3.2 Hz, 1H), 4.57 (d, J = 9.1 Hz, 1H), 4.48-4.28 (m, 4H), 4.30-4.13 (m, 2H), 3.85-3.78 (m, 2H), 3.76-3.55 (m, 4H), 3.50-3.38 (m, 5H), 3.28-3.10 (m, 2H), 3.11-2.76 (m, 3H), 2.70-2.62 (m, 2H), 2.45 (s, 3H), 2.24 (d, J = 12.0 Hz, 1H), 2.15-1.83 (m, 5H), 1.85-1.64 (m, 4H), 1.58-1.49 (m, 4H), 1.24-1.19 (m, 1H), 1.11-1.02 (m, 5H), 0.98 (s, 9H). |
| I91 | 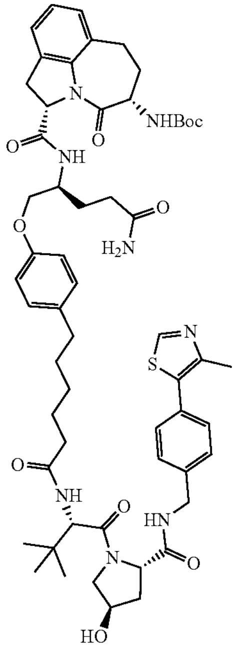 [SMILES: Cc1ncsc1-c1ccc(CNC(=O)[C@@H]2C[C@@H](O)CN2C(=O)[C@@H](NC(=O)CCCCCc2ccc(OC[C@H](CCC(N)=O)NC(=O)[C@@H]3Cc4cccc5c4N3C(=O)[C@@H](NC(=O)OC(C)(C)C)CC5)cc2)C(C)(C)C)cc1] | Tert-butyl N-[(2S,11S)-2-[[(2S)-4-carbamoyl-1-[4-(5-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]pentyl)phenoxy]butan-2-yl]carbamoyl]-12-oxo-1-azatricyclo[6.4.1.0^[4,13]]trideca-4(13),5,7-trien-11-yl]carbamate | 1063.45 | (400 MHz, DMSO-$d_6$) δ 8.99 (s, 1H), 8.56 (t, J = 6.1 Hz, 1H), 8.04 (d, J = 8.3 Hz, 1H), 7.84 (d, J = 9.3 Hz, 1H), 7.41 (q, J = 8.4 Hz, 4H), 7.25-7.22 (m, 1H), 7.13-7.02 (m, 5H), 6.95 (t, J = 7.4 Hz, 1H), 6.86-6.78 (m, 2H), 6.75-6.72 (m, 1H), 5.13 (d, J = 3.5 Hz, 1H), 5.03 (dd, J = 10.7, 2.8 Hz, 1H), 4.61-4.15 (m, 5H), 4.06-3.81 (m, 4H), 3.71-3.62 (m, 2H), 3.44-3.38 (m, 1H), 3.18-2.95 (m, 2H), 2.92-2.77 (m, 1H), 2.45 (s, 3H), 2.30-1.96 (m, 8H), 1.96-1.44 (m, 8H), 1.39 (s, 9H), 1.26 (q, J = 7.3 Hz, 2H), 0.93 (s, 9H) |

TABLE 50-continued

Characterization data for intermediates prepared according to above.

| Intermediate | Structure | Chemical Name | MS: [(M + 1)]+ | $^1$H NMR |
|---|---|---|---|---|
| I92 | 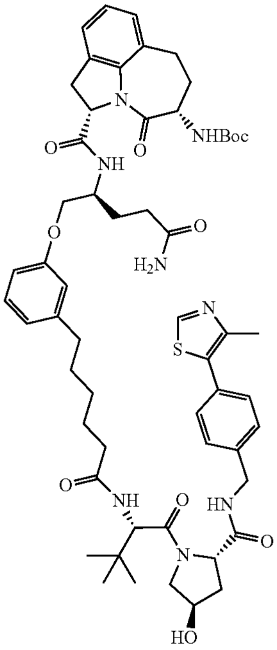 [SMILES: Cc1ncsc1-c1ccc(CNC(=O)[C@@H]2C[C@@H](O)CN2C(=O)[C@@H](NC(=O)CCCCCc2cccc(OC[C@H](CCC(N)=O)NC(=O)[C@@H]3Cc4cccc5c4N3C(=O)[C@@H](NC(=O)OC(C)(C)C)CC5)c2)C(C)(C)C)cc1] | tert-butyl N-[(2S,11S)-2-[[(2S)-4-carbamoyl-1-[3-(5-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]pentyl)phenoxy]butan-2-yl]carbamoyl]-12-oxo-1-azatricyclo[6.4.1.0^[4,13]]trideca-4(13),5,7-trien-11-yl]carbamate | 1063.74 | (400 MHz, DMSO-$d_6$) δ 8.99 (s, 1H), 8.55 (t, J = 6.1 Hz, 1H), 8.03 (d, J = 8.3 Hz, 1H), 7.84 (d, J = 9.3 Hz, 1H), 7.41 (q, J = 8.3 Hz, 4H), 7.23 (s, 1H), 7.17 (dd, J = 8.9, 7.4 Hz, 1H), 7.12-7.01 (m, 3H), 7.00-6.92 (m, 1H), 6.77-6.71 (m, 4H), 5.12 (d, J = 3.6 Hz, 1H), 5.04 (dd, J = 10.6, 2.7 Hz, 1H), 4.55 (d, J = 9.3 Hz, 1H), 4.48-4.39 (m, 2H), 4.36 (s, 1H), 4.23 (dd, J = 15.9, 5.4 Hz, 1H), 4.10-3.93 (m, 1H), 3.93-3.85 (m, 3H), 3.72-3.61 (m, 3H), 3.45-3.37 (m, 2H), 3.12-2.99 (m, 3H), 2.86 (d, J = 16.6 Hz, 1H), 2.45 (s, 3H), 2.31-2.23 (m, 1H), 2.13 (q, J = 7.6, 7.1 Hz, 2H), 2.06-2.01 (m, 4H), 1.95-1.61 (m, 1H), 1.61-1.44 (m, 4H), 1.39 (s, 9H), 1.31-1.23 (m, 3H), 0.94 (s, 9H) |
| I93 | 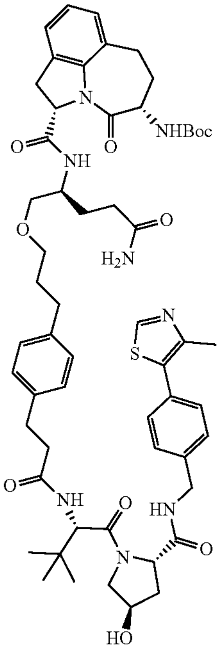 [SMILES: Cc1ncsc1-c1ccc(CNC(=O)[C@@H]2C[C@@H](O)CN2C(=O)[C@@H](NC(=O)CCc2ccc(CCCOC[C@H](CCC(N)=O)NC(=O)[C@@H]3Cc4cccc5c4N3C(=O)[C@@H](NC(=O)OC(C)(C)C)CC5)cc2)C(C)(C)C)cc1] | tert-butyl N-[(2S,11S)-2-[[(2S)-4-carbamoyl-1-[3-[4-(2-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]ethyl)phenyl]propoxy]butan-2-yl]carbamoyl]-12-oxo-1-azatricyclo[6.4.1.0^[4,13]]trideca-4(13),5,7-trien-11-yl]carbamate | 1063.33 | (400 MHz, DMSO-$d_6$) δ 8.99 (s, 1H), 8.57 (t, J = 6.1 Hz, 1H), 7.99-7.83 (m, 2H), 7.41 (q, J = 8.3 Hz, 5H), 7.24-7.21 (m, 2H), 7.16-7.00 (m, 7H), 6.97-6.92 (m, 1H), 6.71 (s, 1H), 5.15 (d, J = 3.5 Hz, 1H), 5.06-4.98 (m, 1H), 4.55 (dd, J = 9.4, 2.1 Hz, 1H), 4.50-4.40 (m, 2H) 4.36 (s, 1H), 4.28-4.17 (m, 1H), 4.06-4.02 (m, 2H), 3.82-3.77 (m, 1H), 3.70-3.65 (m, 2H), 3.51-3.34 (m, 2H), 3.33-3.25 (m, 3H), 3.16-2.94 (m, 2H), 2.94-2.71 (m, 2H), 2.71-2.55 (m, 2H), 2.45 (s, 3H), 2.43-2.31 (m, 1H), 2.16-1.96 (m, 4H), 1.94-1.87 (m, 1H), 1.78-1.70 (m, 3H), 1.66-1.48 (m, 1H), 1.39 (s, 9H), 0.89 (s, 9H) |

TABLE 50-continued

| Characterization data for intermediates prepared according to above. | | | | |
|---|---|---|---|---|
| Inter-mediate | Structure | Chemical Name | MS: [(M + 1)]$^+$ | $^1$H NMR |
| I94 | 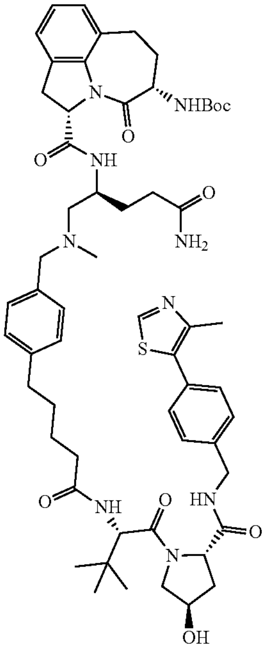 [SMILES: Cc1ncsc1-c1ccc(CNC(=O)[C@@H]2C[C@@H](O)CN2C(=O)[C@@H](NC(=O)CCCCc2ccc(CN(C)C[C@H](CCC(N)=O)NC(=O)[C@@H]3Cc4cccc5c4N3C(=O)[C@@H](NC(=O)OC(C)(C)C)CC5)cc2)C(C)(C)C)cc1] | tert-butyl N-[(2S,11S)-2-[[(2S)-4-carbamoyl-1-([[4-(4-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]butyl)phenyl]methyl](methyl)amino)butan-2-yl]carbamoyl]-12-oxo-1-azatricyclo[6.4.1.0^[4,13]]trideca-4(13),5,7-trien-11-yl]carbamate | 1076.80 | (400 MHz, $CD_3OD$) δ 8.89 (s, 1H), 7.51-7.39 (m, 5H), 7.19 (d, J = 7.9 Hz, 1H), 7.15-7.00 (m, 5H), 5.17-5.09 (m, 1H), 4.65 (d, J = 2.2 Hz, 1H), 4.62-4.47 (m, 4H), 4.36 (d, J = 15.4 Hz, 1 H), 4.30-4.16 (m, 1H), 4.07 (s, 1H), 3.91 (d, J = 11.0 Hz, 1H), 3.84-3.80 (m, 1H), 3.59-3.37 (m, 3H), 3.24-3.03 (m, 4H), 2.64-2.60 (m, 2H), 2.49 (s, 3H), 2.37-2.05 (m, 9H), 2.02-1.94 (m, 1H), 1.69-1.62 (m, 7H), 1.47 (s, 9H), 1.05 (s, 9H) |
| I95 | 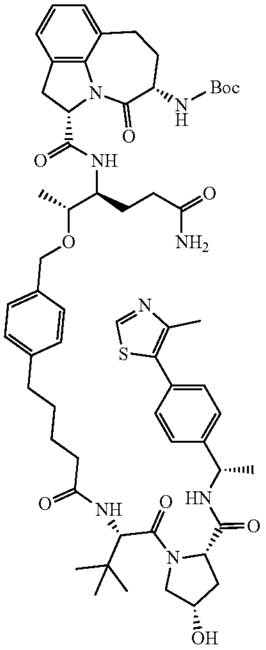 [SMILES: Cc1ncsc1-c1ccc([C@H](C)NC(=O)[C@@H]2C[C@H](O)CN2C(=O)[C@@H](NC(=O)CCCCc2ccc(CO[C@H](C)[C@H](CCC(N)=O)NC(=O)[C@@H]3Cc4cccc5c4N3C(=O)[C@@H](NC(=O)OC(C)(C)C)CC5)cc2)C(C)(C)C)cc1] | tert-butyl N-[(2S,11S)-2-[[(3S,4R)-1-carbamoyl-4-[[4-(4-[[(2S)-1-[(2S,4S)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]butyl)phenyl]methoxy]pentan-3-yl]carbamoyl]-12-oxo-1-azatricyclo[6.4.1.0^[4,13]]trideca-4(13),5,7-trien-11-yl]carbamate | 1091.60 | (400 MHz, $CD_3OD$) δ 8.89 (s, 1H), 8.35 (d, J = 7.6 Hz, 1H), 7.98 (d, J = 9.5 Hz, 1H), 7.88 (d, J = 8.2 Hz, 1H), 7.45 (s, 3H), 7.24 (d, J = 8.0 Hz, 2H), 7.14 (d, J = 8.0 Hz, 2H), 7.04 (td, J = 15.1, 14.6, 7.9 Hz, 2H), 5.13 (dd, J = 10.9, 3.4 Hz, 1H), 5.05-5.01 (m, 1H), 4.57-4.43 (m, 3H), 4.37 (t, J = 4.5 Hz, 1H), 4.25 (d, J = 8.2 Hz, 1H), 4.04-4.00 (m, 1H), 3.68 (dd, J = 10.5, 3.7 Hz, 1H), 3.62-3.53 (m, 1H), 3.47 (dd, J = 16.6, 10.9 Hz, 1H), 3.17-3.13 (m, 2H), 3.01 (dd, J = 16.5, 3.4 Hz, 1H), 2.66-2.62 (m, 2H), 2.50 (s, 3H), 2.44-2.26 (m, 2H), 2.25-2.15 (m, 2H), 2.07-2.03 (m, 7H), 1.95-1.86 (m, 1H), 1.74-1.61 (m, 5H), 1.52 (d, J = 7.0 Hz, 3H), 1.48 (s, 9H), 1.20 (d, J = 6.3 Hz, 3H), 1.05 (s, 9H) |

TABLE 50-continued

| Characterization data for intermediates prepared according to above. | | | | |
|---|---|---|---|---|
| Intermediate | Structure | Chemical Name | MS: [(M + 1)]+ | $^1H$ NMR |
| I96 | 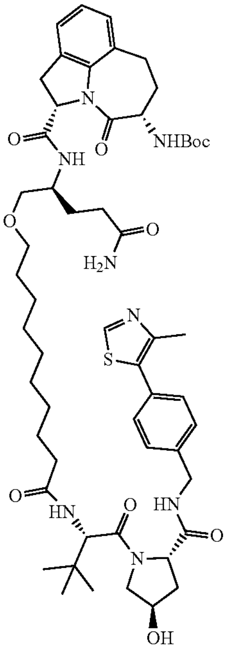 [SMILES: Cc1ncsc1-c1ccc(CNC(=O)[C@@H]2C[C@@H](O)CN2C(=O)[C@@H](NC(=O)CCCCCCCCCOC[C@H](CCC(N)=O)NC(=O)[C@@H]2Cc3cccc4c3N2C(=O)[C@@H](NC(=O)OC(C)(C)C)CC4)C(C)(C)C)cc1] | tert-butyl N-[(2S,11S)-2-[[(2S)-4-carbamoyl-1-[(9-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]nonyl)oxy]butan-2-yl]carbamoyl]-12-oxo-1-azatricyclo[6.4.1.0^[4,13]]trideca-4(13),5,7-trien-11-yl]carbamate | 1043.55 | (400 MHz, DMSO-$d_6$) δ 8.99 (s, 1H), 8.56 (t, J = 6.1 Hz, 1H), 7.83 (t, J = 8.6 Hz, 2H), 7.45-7.33 (m, 5H), 7.19 (s, 1H), 7.14-6.99 (m, 3H), 6.99-6.90 (m, 1H), 6.69 (s, 1H), 5.12 (d, J = 3.6 Hz, 1H), 5.00 (dd, J = 12.0, 4.0 Hz, 1H), 4.55 (d, J = 9.4 Hz, 1H), 4.48-4.39 (m, 2H), 4.35 (s, 1H), 4.22 (dd, J = 15.8, 5.5 Hz, 1H), 4.09-3.95 (m, 1H), 3.83-3.71 (m, 1H), 3.71-3.60 (m, 2H), 3.47-3.38 (m, 1H), 3.31-3.30 (m, 4H), 3.29-3.24 (m, 2H), 3.15-2.94 (m, 2H), 2.87 (d, J = 16.5 Hz, 1H), 2.45 (s, 3H), 2.30-2.23 (m, 1H), 2.17-1.96 (m, 5H), 1.94-1.87 (m, 1H), 1.79-1.41 (m, 2H), 1.39 (s, 9H), 1.28-1.22 (m, 14H), 0.94 (s, 9H) |
| I97 | 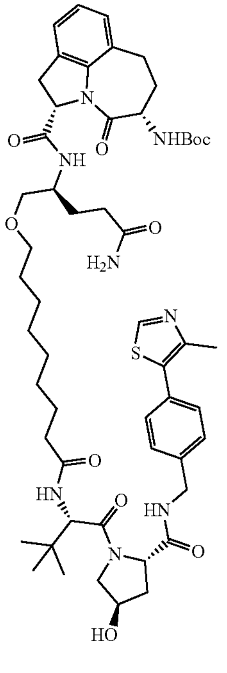 [SMILES: Cc1ncsc1-c1ccc(CNC(=O)[C@@H]2C[C@@H](O)CN2C(=O)[C@@H](NC(=O)CCCCCCCCOC[C@H](CCC(N)=O)NC(=O)[C@@H]2Cc3cccc4c3N2C(=O)[C@@H](NC(=O)OC(C)(C)C)CC4)C(C)(C)C)cc1] | tert-butyl N-[(2S,11S)-2-[[(2S)-4-carbamoyl-1-[8-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]octyl)oxy]butan-2-yl]carbamoyl]-12-oxo-1-azatricyclo[6.4.1.0^[4,13]]trideca-4(13),5,7-trien-11-yl]carbamate | 1029.60 | (400 MHz, DMSO-$d_6$) δ 8.99 (s, 1H), 8.56 (t, J = 6.1 Hz, 1H), 7.95-7.77 (m, 2H), 7.45-7.36 (m, 5H), 7.20 (s, 1H), 7.13-7.02 (m, 3H), 6.96 (d, J = 7.4 Hz, 1H), 6.74-6.65 (m, 1H), 5.14-5.12 (m, 1H), 5.01 (dd, J = 10.7, 2.7 Hz, 1H), 4.55 (d, J = 9.4 Hz, 1H), 4.49-4.40 (m, 2H), 4.36-4.32 (m, 2H), 4.22 (dd, J = 15.8, 5.4 Hz, 1H), 4.04 (t, J = 9.4 Hz, 1H), 3.79-2.75 (m, 2H), 3.70-3.62 (m, 2H), 3.51-3.41 (m, 1H), 3.30-3.24 (m, 2H), 3.15-2.96 (m, 2H), 2.92-2.79 (m, 1H), 2.45 (s, 4H), 2.28-2.24 (m, 1H), 2.15-1.95 (m, 8H), 1.92-1.89 (m, 1H), 1.76-1.64 (m, 1H), 1.59-1.42 (m, 6H), 1.39 (s, 9H), 0.94 (s, 9H). |

TABLE 50-continued

Characterization data for intermediates prepared according to above.

| Inter-mediate | Structure | Chemical Name | MS: [(M + 1)]+ | 1H NMR |
|---|---|---|---|---|
| I98 | 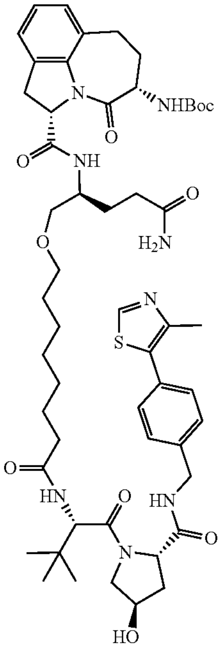 [SMILES: Cc1ncsc1-c1ccc(CNC(=O)[C@@H]2C[C@@H](O)CN2C(=O)[C@@H](NC(=O)CCCCCCCOC[C@H](CCC(N)=O)NC(=O)[C@@H]2Cc3cccc4c3N2C(=O)[C@@H](NC(=O)OC(C)(C)C)CC4)C(C)(C)C)cc1] | tert-butyl ((3S,6S)-6-(((S)-5-amino-1-((8-(((S)-1-((2S,4R)-4-hydroxy-2-((4-(4-methylthiazol-5-yl)benzyl)carbamoyl) pyrrolidin-1-yl)-3,3-dimethyl-1-oxobutan-2-yl)amino)-8-oxooctyl)oxy)-5-oxopentan-2-yl)carbamoyl)-4-oxo-1,2,3,4,6,7-hexahydroazepino[3,2,1-hi]indol-3-yl)carbamate | 1014.80 | (400 MHz, DMSO-$d_6$) δ 8.99 (s, 1H), 8.56 (t, J = 6.1 Hz, 1H), 7.88-7.82 (m, 2H), 7.48-7.35 (m, 4H), 7.22-7.17 (m, 1H), 7.09-7.01 (m, 3H), 6.96 (t, J = 7.4 Hz, 1H), 6.69 (s, 1H), 5.12 (d, J = 3.5 Hz, 1H), 5.07-5.01 (m, 1H), 4.55 (d, J = 9.4 Hz, 1H), 4.49-4.39 (m, 2H), 4.35 (s, 1H), 4.26-4.20 (m, 1H), 4.04 (t, J = 9.3 Hz, 1H), 3.80-3.74 (m, 1H), 3.65 (t, J = 8.8 Hz, 2H), 3.49-3.40 (m, 1H), 3.28-3.25 (m, 2H), 3.11-2.96 (m, 2H), 2.91-2.82 (m, 1H), 2.45 (s, 3H), 2.12-2.04 (m, 10H), 1.99-1.85 (m, 1H), 1.68 (d, J = 7.0 Hz, 1H), 1.49-1.43 (m, 3H), 1.39 (s, 9H), 1.29-1.21 (m, 7H), 0.94 (s, 9H) |
| I99 | 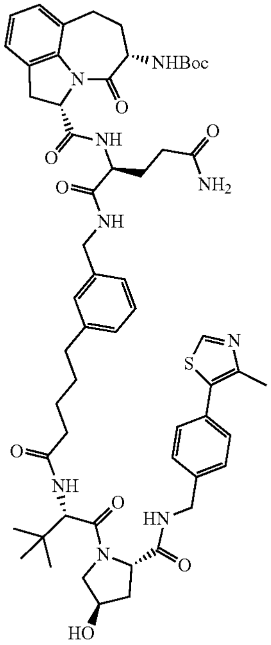 [SMILES: Cc1ncsc1-c1ccc(CNC(=O)[C@@H]2C[C@@H](O)CN2C(=O)[C@@H](NC(=O)CCCCc2cccc(CNC(=O)[C@H](CCC(N)=O)NC(=O)[C@@H]3Cc4cccc5c4N3C(=O)[C@@H](NC(=O)OC(C)(C)C)CC5)c2)C(C)(C)C)cc1] | tert-butyl N-[(2S,11S)-2-[[(1S)-3-carbamoyl-1-([[3-(4-[[(2S)-1-[(2S,4R)-4-hydroxy-2-([[4-(4-methyl-1,3-thiazol-5-yl)phenyl]methyl] carbamoyl)pyrrolidin-1-yl]-3,3-dimethyl-1-oxobutan-2-yl]carbamoyl]butyl) phenyl]methyl]carbamoyl) propyl]carbamoyl]-12-oxo-1-azatricyclo[6.4.1.0^[4,13]] trideca-4(13),5,7-trien-11-yl]carbamate | 1076.61 | (400 MHz, DMSO-$d_6$) δ 8.99 (s, 1H), 8.56 (t, J = 6.1 Hz, 1H), 8.39 (t, J = 5.9 Hz, 1H), 8.20 (d, J = 7.8 Hz, 1H), 7.90 (d, J = 9.4 Hz, 1H), 7.44-7.37 (m, 4H), 7.27 (s, 1H), 7.19 (t, J = 7.8 Hz, 1H), 7.09-7.00 (m, 6H), 6.96 (t, J = 7.7 Hz, 2H), 6.77 (s, 1H), 5.17-5.07 (m, 2H), 4.55 (d, J = 9.4 Hz, 1H), 4.47-4.39 (m, 2H), 4.35 (s, 1H), 4.27-4.18 (m, 4H), 4.10-3.99 (m, 1H), 3.73-3.61 (m, 2H), 3.41 (dd, J = 16.8, 10.9 Hz, 1H), 3.14-2.92 (m, 2H), 2.45 (s, 3H), 2.37-2.22 (m, 1H), 2.19-1.97 (m, 7H), 1.94-1.87 (m, 2H), 1.83-1.73 (m, 1H), 1.55-1.46 (m, 5H), 1.39 (s, 9H), 0.94 (s, 9H) |

TABLE 50-continued

Characterization data for intermediates prepared according to above.

| Inter-mediate | Structure | Chemical Name | MS: [(M + 1)]$^+$ | $^1$H NMR |
|---|---|---|---|---|
| I100 | 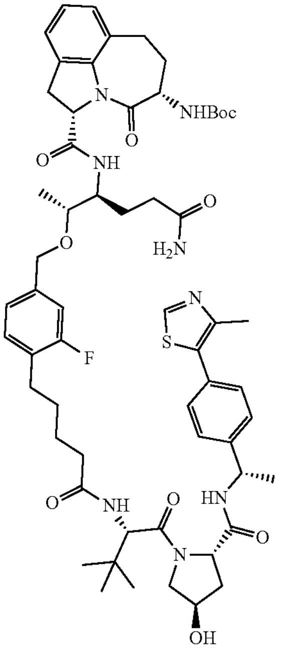 [SMILES: Cc1ncsc1-c1ccc([C@H](C)NC(=O)[C@@H]2C[C@@H](O)CN2C(=O)[C@@H](NC(=O)CCCCc2ccc(CO[C@H](C)[C@H](CCC(N)=O)NC(=O)[C@@H]3Cc4cccc5c4N3C(=O)[C@@H](NC(=O)OC(C)(C)C)CC5)cc2F)C(C)(C)C)cc1] | tert-butyl N-[(2S,11S)-2-[[(3S,4R)-1-carbamoyl-4-[[3-fluoro-4-(4-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]butyl)phenyl]methoxy]pentan-3-yl]carbamoyl]-12-oxo-1-azatricyclo[6.4.1.0^[4,13]]trideca-4(13),5,7-trien-11-yl]carbamate | 1109.75 | (400 MHz, DMSO-$d_6$) δ 8.99 (s, 1H), 8.38 (d, J = 7.7 Hz, 1H), 7.85 (dd, J = 13.7, 9.3 Hz, 2H), 7.44 (d, J = 7.9 Hz, 2H), 7.38 (d, J = 7.9 Hz, 2H), 7.23-7.15 (m, 2H), 7.12-6.99 (m, 5H), 6.95 (t, J = 7.4 Hz, 1H), 6.69 (s, 1H), 5.12-5.02 (m, 2H), 4.92 (p, J = 7.2 Hz, 1H), 4.52 (d, J = 9.3 Hz, 1H), 4.43 (q, J = 6.7, 5.4 Hz, 3H), 4.28 (s, 1H), 4.04 (t, J = 8.8 Hz, 1H), 3.78 (s, 1H), 3.62-3.59 (m, 2H), 3.48-3.44 (m, 1H), 3.07 (s, 1H), 3.02-2.98 (m, 1H), 2.86-2.82 (m, 1H), 2.60-2.56 (m, 2H), 2.46 (s, 3H), 2.33-2.29 (m, 1H), 2.19-2.07 (m, 1H), 2.05-2.01 (m, 6H), 1.84-1.74 (m, 1H), 1.57-1.50 (m, 6H), 1.40-1.36 (m, 12H), 1.09 (d, J = 6.2 Hz, 3H), 0.93 (s, 9H) |
| I101 | 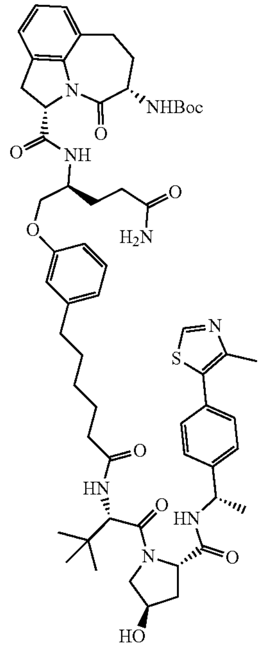 [SMILES: Cc1ncsc1-c1ccc([C@H](C)NC(=O)[C@@H]2C[C@@H](O)CN2C(=O)[C@@H](NC(=O)CCCCCc2cccc(OC[C@H](CCC(N)=O)NC(=O)[C@@H]3Cc4cccc5c4N3C(=O)[C@@H](NC(=O)OC(C)(C)C)CC5)c2)C(C)(C)C)cc1] | tert-butyl N-[(2S,11S)-2-[[(2S)-4-carbamoyl-1-[3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenoxy]butan-2-yl]carbamoyl]-12-oxo-1-azatricyclo[6.4.1.0^[4,13]]trideca-4(13),5,7-trien-11-yl]carbamate | 1077.80 | (400 MHz, DMSO-$d_6$) δ 8.99 (s, 1H), 8.38 (d, J = 7.7 Hz, 1H), 8.05 (d, J = 8.3 Hz, 1H), 7.80 (d, J = 9.3 Hz, 1H), 7.44 (d, J = 7.9 Hz, 2H), 7.38 (d, J = 7.9 Hz, 2H), 7.24 (s, 1H), 7.17 (t, J = 8.1 Hz, 1H), 7.08 (dd, J = 21.9, 8.0 Hz, 3H), 6.96 (t, J = 7.4 Hz, 1H), 6.77 (d, J = 7.4 Hz, 1H), 6.73 (s, 3H), 5.13-5.08 (m, 1H), 5.03 (d, J = 10.7 Hz, 1H), 4.93 (q, J = 7.0 Hz, 1H), 4.52 (d, J = 9.2 Hz, 1H), 4.42 (t, J = 7.8 Hz, 1H), 4.28 (s, 1H), 4.03 (d, J = 9.0 Hz, 1H), 3.97 (s, 1H), 3.89 (s, 2H), 3.61 (s, 2H), 3.41 (dd, J = 16.9, 10.2 Hz, 1H), 3.31 (s, 2H), 3.17-2.95 (m, 3H), 2.85 (d, J = 16.6 Hz, 1H), 2.46 (s, 3H), 2.26-2.21 (m, 1H), 2.20-1.93 (m, 4H), 1.90-1.46 (m, 7H), 1.39 (s, 9H), 1.37 (s, 3H), 1.31-1.22 (m, 3H), 0.93 (s, 9H) |

TABLE 50-continued

Characterization data for intermediates prepared according to above.

| Inter-mediate | Structure | Chemical Name | MS: [(M + 1)]+ | $^1H$ NMR |
|---|---|---|---|---|
| I102 | 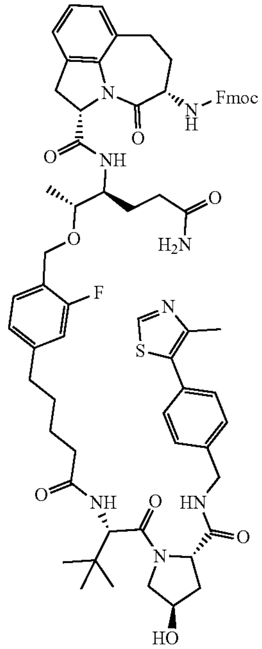 | 9H-fluoren-9-ylmethyl N-[(2S,11S)-2-[[(3S,4R)-1-carbamoyl-4-[[2-fluoro-4-(4-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]butyl)phenyl]methoxy]pentan-3-yl]carbamoyl]-12-oxo-1-azatricyclo[6.4.1.0^[4,13]]trideca-4(13),5,7-trien-11-yl]carbamate | 1217.47 | (400 MHz, DMSO-$d_6$) δ 8.98 (s, 1H), 8.55 (t, J = 6.0 Hz, 1H), 7.94-7.80 (m, 4H), 7.74 (q, J = 8.0, 7.5 Hz, 3H), 7.45-7.39 (m, 5H), 7.35 (dd, J = 14.2, 6.8 Hz, 2H), 7.24 (t, J = 7.8 Hz, 1H), 7.16 (s, 1H), 7.08-6.91 (m, 6H), 6.68 (s, 1H), 5.15-5.01 (m, 2H), 4.62-4.08 (m, 11H), 3.83-3.60 (m, 3H), 3.52-3.36 (m, 2H), 3.20-2.97 (m, 2H), 2.84 (d, J = 16.5 Hz, 1H), 2.57 (t, J = 7.1 Hz, 1H), 2.45 (s, 3H), 2.37-2.28 (m, 1H), 2.20-1.96 (m, 6H), 1.95-1.69 m, 1H), 1.57-1.49 (m, 6H), 1.08 (d, J = 6.3 Hz, 3H), 0.94 (s, 9H) |
| I103 | 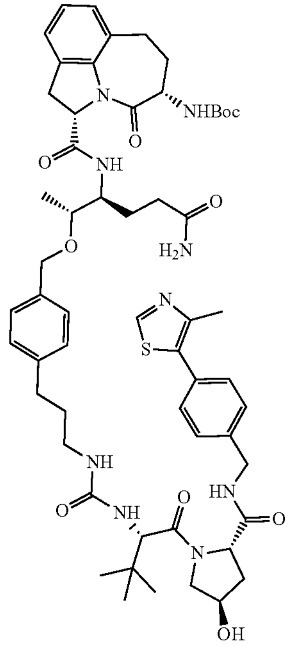 [SMILES: Cc1ncsc1-c1ccc(CNC(=O)[C@@H]2C[C@@H](O)CN2C(=O)[C@@H](NC(=O)NCCCc2ccc(CO[C@H](C)[C@H](CCC(N)=O)NC(=O)[C@@H]3Cc4cccc5c4N3C(=O)[C@@H](NC(=O)OC(C)(C)C)CC5)cc2)C(C)(C)C)cc1] | tert-butyl N-[(2S,11S)-2-[[(3S,4R)-1-carbamoyl-4-([4-[3-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]amino)propyl]phenyl]methoxy)pentan-3-yl]carbamoyl]-12-oxo-1-azatricyclo[6.4.1.0^[4,13]]trideca-4(13),5,7-trien-11-yl]carbamate | 1078.85 | (400 MHz, DMSO-$d_6$) δ 8.99 (s, 1H), 8.58 (t, J = 6.1 Hz, 1H), 7.83 (d, J = 9.2 Hz, 1H), 7.46-7.37 (m, 3H), 7.26-7.01 (m, 9H), 6.96 (dd, J = 8.3, 6.6 Hz, 1H), 6.70-6.66 (m, 1H), 6.23-6.10 (m, 2H), 5.13 (s, 1H), 5.06 (dd, J = 10.7, 2.8 Hz, 1H), 4.48-4.31 (m, 5H), 4.22 (dd, J = 15.9, 5.4 Hz, 1H), 4.04 (t, J = 8.7 Hz, 1H), 3.78 (s, 1H), 3.69-3.64 (m, 3H), 3.53-3.35 (m, 4H), 3.15-2.97 (m, 2H), 2.85 (d, J = 16.7 Hz, 1H), 2.56 (t, J = 7.4 Hz, 2H), 2.07 (d, J = 11.8 Hz, 7H), 1.93-1.89 (m, 4.6 Hz, 1H), 1.79-1.75 (m, 1H), 1.65 (t, J = 7.6 Hz, 2H), 1.57-1.53 (m, 2H), 1.39 (s, 9H), 1.08 (s, 3H), 0.93 (s, 9H) |

TABLE 50-continued

Characterization data for intermediates prepared according to above.

| Inter-mediate | Structure | Chemical Name | MS: [(M + 1)]$^+$ | $^1$H NMR |
|---|---|---|---|---|
| I104 | 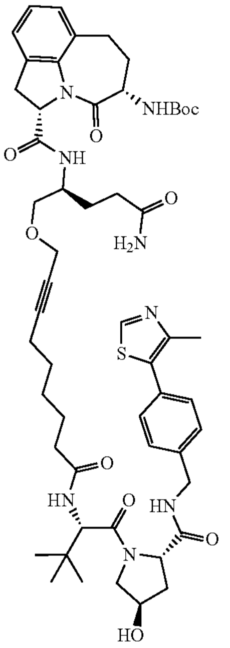 [SMILES: Cc1ncsc1-c1ccc(CNC(=O)[C@@H]2C[C@@H](O)CN2C(=O)[C@@H](NC(=O)CCCCCC#CCOC[C@H](CCC(N)=O)NC(=O)[C@@H]2Cc3cccc4c3N2C(=O)[C@@H](NC(=O)OC(C)(C)C)CC4)C(C)(C)C)cc1] | tert-butyl N-[(2S,11S)-2-[[(2S)-4-carbamoyl-1-[(8-[[(2,S)-1-[(2S,4R)-4-hydroxy-2-([[4-(4-methyl-1,3-thiazol-5-yl)phenyl]methyl] carbamoyl)pyrrolidin-1-yl]-3,3-dimethyl-1-oxobutan-2-yl]carbamoyl]oct-2-yn-1-yl)oxy]butan-2-yl]carbamoyl]-12-oxo-1-azatricyclo[6.4.1.0^[4,13]] trideca-4(13),5,7-trien-11-yl]carbamate | 1025.43 | (400 MHz, DMSO-$d_6$) δ 8.99 (s, 1H), 8.55 (t, J = 6.1 Hz, 1H), 7.87 (dd, J = 9.0, 3.8 Hz, 2H), 7.45-7.36 (m, 5H), 7.19 (s, 1H), 7.09-7.04 (m, 3H), 6.97-6.93 (m, 1H), 6.70 (s, 1H), 5.12 (d, J = 3.5 Hz, 1H), 5.02 (dd, J = 10.7, 2.7 Hz, 1H), 4.55 (d, J = 9.4 Hz, 1H), 4.48-4.40 (m, 2H), 4.38-4.34 (m, 1H), 4.23 (dd, J = 15.9, 5.4 Hz, 1H), 4.09 (d, J = 2.2 Hz, 2H), 4.03 (d, J = 8.4 Hz, 1H), 3.78-3.75 (m, 1H), 3.72-3.59 (m, 2H), 3.44-3.42 (m, 1H), 3.15-2.93 (m, 2H), 2.92-2.83 (m, 1H), 2.45 (s, 3H), 2.23-2.18 (m, 3H), 2.09-1.97 (m, 10H), 1.92-1.89 (m, 1H), 1.81-1.66 (m, 1H), 1.63-1.42 (m, 2H), 1.41-1.37 (m, 12H), 0.94 (s, 9H). |
| I105 | 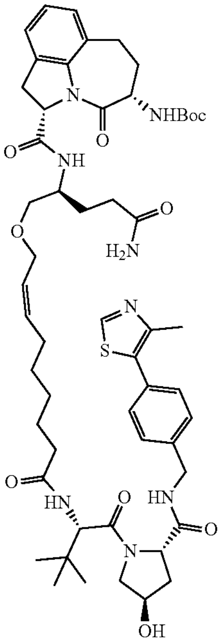 [SMILES: Cc1ncsc1-c1ccc(CNC(=O)[C@@H]2C[C@@H](O)CN2C(=O)[C@@H](NC(=O)CCCCC/C=C\COC[C@H](CCC(N)=O)NC(=O)[C@@H]2Cc3cccc4c3N2C(=O)[C@@H](NC(=O)OC(C)(C)C)CC4)C(C)(C)C)cc1] | tert-butyl N-[(2S,11S)-2-[[(2S)-4-carbamoyl-1-[[(2Z)-8-[[(2S)-1-[(2S,4R)-4-hydroxy-2-([[4-(4-methyl-1,3-thiazol-5-yl)phenyl]methyl] carbamoyl)pyrrolidin-1-yl]-3,3-dimethyl-1-oxobutan-2-yl]carbamoyl]oct-2-en-1-yl]oxy]butan-2-yl]carbamoyl]-12-oxo-1-azatricyclo[6.4.1.0^[4,13]] trideca-4(13),5,7-trien-11-yl]carbamate | [(M + Na)]$^+$ = 1049.85 | (400 MHz, DMSO-$d_6$) δ 8.99 (s, 1H), 8.57 (t, J = 6.1 Hz, 1H), 7.86 (d, J = 9.0 Hz, 2H), 7.41 (q, J = 8.3 Hz, 4H), 7.27-7.17 (m, 1H), 7.13-7.01 (m, 3H), 6.95 (t, J = 7.4 Hz, 1H), 6.72 (d, J = 15.7 Hz, 1H), 5.53-5.41 (m, 1H), 5.13 (d, J = 3.5 Hz, 1H), 5.14-5.00 (m, 1H), 4.55 (d, J = 9.4 Hz, 1H), 4.48-4.39 (m, 2H), 4.36 (s, 1H), 4.22 (dd, J = 15.8, 5.6 Hz, 1H), 4.03 (t, J = 7.7 Hz, 1H), 3.96 (d, J = 6.0 Hz, 2H), 3.78-3.70 (m, 1H), 3.71-3.60 (m, 2 H), 3.46 (s, 2H), 3.28 (d, J = 5.6 Hz, 2H), 3.09-3.01 (m, 2H), 2.91-2.82 (m, 1H), 2.45 (s, 3H), 2.27-2.24 (m, 1H), 2.12 (dd, J = 8.3, 6.2 Hz, 1H), 2.07-1.95 (m, 6H), 1.99-1.91 (m, 1H), 1.70 (d, J = 5.3 Hz, 1H), 1.57-1.44 (m, 4H), 1.39 (s, 9H), 1.30-1.21 (m, 4H), 0.94 (s, 9H) |

TABLE 50-continued

| Characterization data for intermediates prepared according to above. | | | | |
|---|---|---|---|---|
| Inter-mediate | Structure | Chemical Name | MS: [(M + 1)]$^+$ | $^1$H NMR |
| I106 | 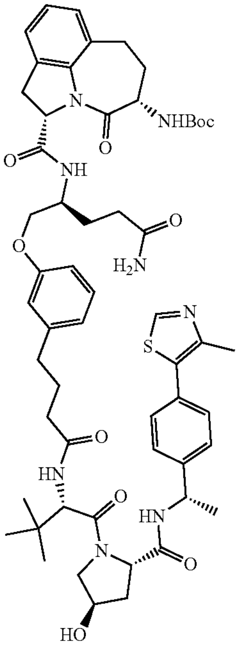 [SMILES: Cc1ncsc1-c1ccc([C@H](C)NC(=O)[C@@H]2C[C@@H](O)CN2C(=O)[C@@H](NC(=O)CCCc2cccc(OC[C@H](CCC(N)=O)NC(=O)[C@@H]3Cc4cccc5c4N3C(=O)[C@@H](NC(=O)OC(C)(C)C)CC5)c2)C(C)(C)C)cc1] | tert-butyl N-[(2S,11S)-2-[[(2S)-4-carbamoyl-1-[3-(3-[[(2S)-1-[(2S,4R)-4-hydroxy-2-[[(1S)-1-[4-(4-methyl-1,3-thiazol-5-yl)phenyl]ethyl] carbamoyl]pyrrolidin-1-yl]-3,3-dimethyl-1-oxobutan-2-yl]carbamoyl]propyl) phenoxy]butan-2-yl]carbamoyl]-12-oxo-1-azatricyclo[6.4.1.0^[4,13]] trideca-4(13),5,7-trien-11-yl]carbamate | 1049.80 | (400 MHz, DMSO-$d_6$) δ 8.99 (s, 1H), 8.37 (d, J = 7.8 Hz, 1H), 8.05 (d, J = 8.2 Hz, 1H), 7.85 (d, J = 9.2 Hz, 1H), 7.47-7.40 (m, 2H), 7.43-7.35 (m, 2H), 7.24 (s, 1H), 7.19 (t, J = 7.7 Hz, 1H), 7.13-7.02 (m, 3H), 7.00-6.91 (m, 1H), 6.80-6.71 (m, 4H), 5.10 (s, 1H), 5.04 (dd, J = 10.7, 2.8 Hz, 1H), 4.93 (p, J = 7.3 Hz, 1H), 4.55 (d, J = 9.3 Hz, 1H), 4.43 (t, J = 8.0 Hz, 1H), 4.29 (s, 1H), 4.04-4.00 (m, 1H), 3.97-3.87 (m, 2H), 3.62 (d, J = 3.3 Hz, 2H), 3.42 (dd, J = 16.7, 10.4 Hz, 1H), 3.04 (t, J = 9.3 Hz, 2H), 2.88-2.86 (m, 1H), 2.46 (s, 3H), 2.30-2.26 (m, 1H), 2.22-2.11 (m, 2H), 2.10-1.97 (m, 1H), 1.86-1.66 (m, 2H), 1.42-1.37 (m, 18H), 1.34-1.23 (m, 3H), 0.95 (s, 9H) |
| I107 | 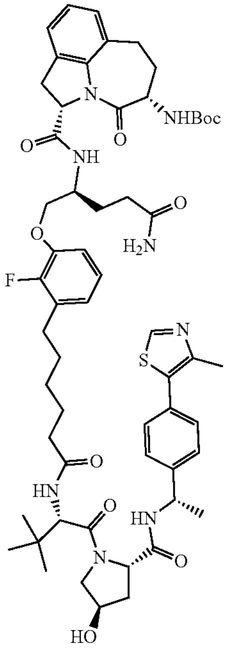 [SMILES: Cc1ncsc1-c1ccc([C@H](C)NC(=O)[C@@H]2C[C@@H](O)CN2C(=O)[C@@H](NC(=O)CCCCCc2cccc(OC[C@H](CCC(N)=O)NC(=O)[C@@H]3Cc4cccc5c4N3C(=O)[C@@H](NC(=O)OC(C)(C)C)CC5)c2F)C(C)(C)C)cc1] | tert-butyl N-[(2S,11S)-2-[[(2S)-4-carbamoyl-1-[2-fluoro-3-(5-[[(2S)-1-[(2S,4R)-4-hydroxy-2-[[(1S)-1-[4-(4-methyl-1,3-thiazol-5-yl)phenyl]ethyl] carbamoyl]pyrrolidin-1-yl]-3,3-dimethyl-1-oxobutan-2-yl]carbamoyl]pentyl) phenoxy]butan-2-yl]carbamoyl]-12-oxo-1-azatricyclo[6.4.1.0^[4,13]] trideca-4(13),5,7-trien-11-yl]carbamate | 1095.34 | (400 MHz, DMSO-$d_6$) δ 8.99 (s, 1H), 8.38 (d, J = 7.8 Hz, 1H), 8.08 (d, J = 7.5 Hz, 1H), 7.80 (d, J = 9.3 Hz, 1H), 7.47-7.41 (m, 2H), 7.41-7.30 (m, 2H), 7.24 (s, 1H), 7.10 (d, J = 8.0 Hz, 1H), 7.06-6.96 (m, 4H), 6.99-6.91 (m, 1H), 6.85-6.83 (m, 1H), 6.75 (s, 1H), 5.10 (d, J = 3.6 Hz, 1H), 5.05-5.01 (m, 1H), 4.94-4.90 (m, 1H), 4.52 (d, J = 9.3 Hz, 1H), 4.47-4.32 (m, 1H), 4.28 (s, 1H), 4.07-3.90 (m, 1H), 3.61 (s, 2H), 3.48-3.44 (m, 1H), 3.12-2.96 (m, 1H), 2.92-2.82 (m, 1H), 2.57 (t, J = 7.6 Hz, 2H), 2.46 (s, 3H), 2.26-2.22 (m, 1H), 2.16-2.12 (m, 2H), 2.03-1.97 (m, 5H), 1.87-1.83 (m, 2H), 1.81-1.77 (m, 1H), 1.74-1.66 (m, 1H), 1.56-1.52 (m, 4H), 1.59-1.44 (m, 1H), 1.40-1.36 (m, 12H), 1.34-1.21 (m, 2H), 1.08-1.05 (m, 1H), 0.93 (s, 9H) |

TABLE 50-continued

| Characterization data for intermediates prepared according to above. | | | | |
|---|---|---|---|---|
| Intermediate | Structure | Chemical Name | MS: [(M + 1)]+ | $^1$H NMR |
| I108 | 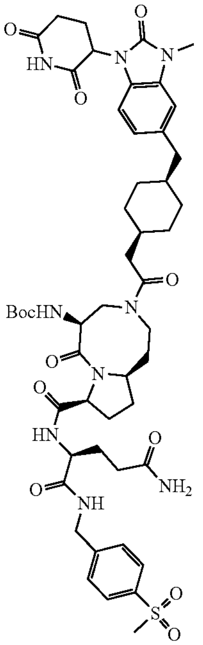 [SMILES: Cn1c(=O)n(C2CCC(=O)NC2=O)c2ccc(C[C@H]3CC[C@@H](CC(=O)N4CC[C@H]5CC[C@@H](C(=O)N[C@@H](CCC(N)=O)C(=O)NCc6ccc(S(C)(=O)=O)cc6)N5C(=O)[C@@H](NC(=O)OC(C)(C)C)C4)CC3)cc21] | tert-butyl N-[(5S,8S,10aR)-8-[[(1S)-3-carbamoyl-1-[[(4-methanesulfonylphenyl)methyl]carbamoyl]propyl]carbamoyl]-6-oxo-3-[2-[(1S,4S)-4-[[1-(2,6-dioxopiperidin-3-yl)-3-methyl-2-oxo-1,3-benzodiazol-5-yl]methyl]cyclohexyl]acetyl]-octahydropyrrolo[1,2-a][1,5]diazocin-5-yl]carbamate | 1018.75 | (300 MHz, DMSO-d$_6$) δ 11.06 (s, 1H), 8.49 (t, J = 6.0 Hz, 1H), 8.24 (d, J = 7.7 Hz, 1H), 7.96-7.74 (m, 2H), 7.50 (dd, J = 8.6, 2.9 Hz, 2H), 7.20 (s, 1H), 6.98 (dd, J = 8.7, 4.4 Hz, 2H), 6.86-6.72 (m, 2H), 6.52 (d, J = 6.9 Hz, 1H), 5.33 (dd, J = 12.7, 5.3 Hz, 1H), 4.52-4.34 (m, 3H), 4.30-3.96 (m, 2H), 3.83-3.73 (m, 2H), 3.31 (s, 3H), 3.18 (s, 3H), 3.01 (td, J = 6.7, 3.9 Hz, 3H), 2.93-2.82 (m, 2H), 2.76-2.55 (m, 4H), 2.44-2.30 (m, 2H), 2.23-2.11 (m, 2H), 2.05-1.88 (m, 4H), 1.86-1.57 (m, 5H), 1.44 (s, 9H), 1.48-1.30 (m, 8H) |
| I109 | 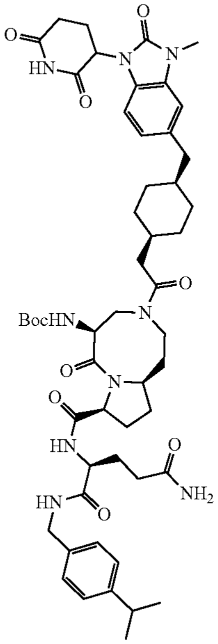 [SMILES: CC(C)c1ccc(CNC(=O)[C@H](CCC(N)=O)NC(=O)[C@@H]2CC[C@@H]3CCN(C(=O)C[C@H]4CC[C@@H](Cc5ccc6c(c5)n(C)c(=O)n6C5CCC(=O)NC5=O)CC4)C[C@H](NC(=O)OC(C)(C)C)C(=O)N32)cc1] | tert-butyl N-[(5S,8S,10aR)-8-[[(1S)-3-carbamoyl-1-[[(4-isopropylphenyl)methyl]carbamoyl]propyl]carbamoyl]-6-oxo-3-[2-[(1S,4S)-4-[[1-(2,6-dioxopiperidin-3-yl)-3-methyl-2-oxo-1,3-benzodiazol-5-yl]methyl]cyclohexyl]acetyl]-octahydropyrrolo[1,2-a][1,5]diazocin-5-yl]carbamate | 982.50 | (300 MHz, DMSO-d$_6$) δ 11.09 (s, 1H), 8.31 (t, J = 6.1 Hz, 1H), 8.20 (d, J = 8.1 Hz, 1H), 7.27-7.12 (m, 5H), 7.00 (dd, J = 8.6, 5.5 Hz, 2H), 6.93-6.68 (m, 2H), 6.52 (d, J = 6.7 Hz, 1H), 5.35 (dd, J = 12.7, 5.4 Hz, 1H), 4.55-3.96 (m, 6H), 3.88-3.68 (m, 3H), 3.35-3.32 (m, 7H), 3.23-3.08 (m, 1H), 3.01-2.80 (m, 2H), 2.80-2.55 (m, 6H), 2.47-2.27 (m, 1H), 2.27-2.10 (m, 4H), 2.09 (s, 3H), 1.86-1.58 (m, 1H), 1.58-1.24 (m, 17H), 1.18 (dd, J = 6.9, 4.1 Hz, 6H) |

TABLE 50-continued

| Characterization data for intermediates prepared according to above. | | | | |
|---|---|---|---|---|
| Intermediate | Structure | Chemical Name | MS: [(M + 1)]$^+$ | $^1$H NMR |
| I110 | 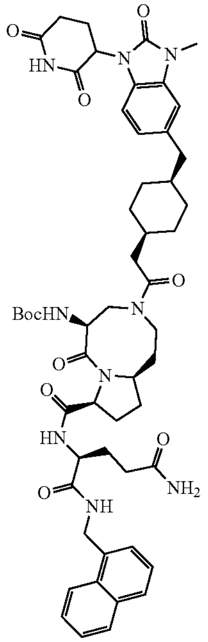 [SMILES: Cn1c(=O)n(C2CCC(=O)NC2=O)c2ccc(C[C@H]3CC[C@@H](CC(=O)N4CC[C@H]5CC[C@@H](C(=O)N[C@@H](CCC(N)=O)C(=O)NCc6cccc7ccccc67)N5C(=O)[C@@H](NC(=O)OC(C)(C)C)C4)CC3)cc21] | tert-butyl N-[(5S,8S,10aR)-8-[[(1S)-3-carbamoyl-1-[(naphthalen-1-ylmethyl)carbamoyl]propyl]carbamoyl]-6-oxo-3-[2-[(1S,4S)-4-[[1-(2,6-dioxopiperidin-3-yl)-3-methyl-2-oxo-1,3-benzodiazol-5-yl]methyl]cyclohexyl]acetyl]-octahydropyrrolo[1,2-a][1,5]diazocin-5-yl]carbamate | 990.75 | (300 MHz, DMSO-$d_6$) δ 11.06 (s, 1H), 8.38 (t, J = 5.7 Hz, 1H), 8.22 (d, J = 7.7 Hz, 1H), 8.10-7.99 (m, 1H), 7.99-7.88 (m, 1H), 7.84 (q, J = 4.0, 3.2 Hz, 1H), 7.60-7.49 (m, 2H), 7.49-7.40 (m, 2H), 7.19 (s, 1H), 7.04-6.90 (m, 2H), 6.82 (t, J = 7.6 Hz, 1H), 6.70 (d, J = 15.0 Hz, 1H), 6.48 (d, J = 6.8 Hz, 1H), 5.33 (dd, J = 12.8, 5.4 Hz, 1H), 4.74 (d, J = 5.6 Hz, 2H), 4.40 (q, J = 9.1 Hz, 2H), 4.25 (q, J = 7.5 Hz, 1H), 4.21-3.91 (m, 2H), 3.86-3.65 (m, 2H), 3.52 (d, J = 10.6 Hz, 1H), 3.31 (s, 3H), 3.22-2.80 (m, 4H), 2.76-2.54 (m, 4H), 2.47-2.21 (m, 2H), 2.21-1.85 (m, 12H), 1.85-1.54 (m, 4H), 1.44 (s, 9H), 1.35 (m, 2H) |
| I111 | 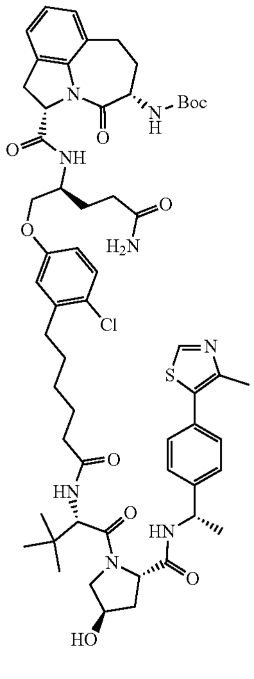 [SMILES: Cc1ncsc1-c1ccc([C@H](C)NC(=O)[C@@H]2C[C@@H](O)CN2C(=O)[C@@H](NC(=O)CCCCCc2cc(OC[C@H](CCC(N)=O)NC(=O)[C@@H]3Cc4cccc5c4N3C(=O)[C@@H](NC(=O)OC(C)(C)C)CC5)ccc2Cl)C(C)(C)C)cc1] | tert-butyl N-[(11S)-2-[[(2S)-4-carbamoyl-1-[4-chloro-3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenoxy]butan-2-yl]carbamoyl]-12-oxo-1-azatricyclo[6.4.1.0^[4,13]]trideca-4(13),5,7-trien-11-yl]carbamate | 1111.80 | (300 MHz, DMSO-$d_6$) δ 8.97 (s, 1H), 8.34 (d, J = 7.7 Hz, 1H), 8.02 (d, J = 8.0 Hz, 1H), 7.77 (d, J = 9.3 Hz, 1H), 7.41-7.39 (m, J = 8.3 Hz, 4H), 7.34-7.18 (m, 2H), 7.10-7.00 (m, 3H), 6.94 (d, J = 8.0, 6.7 Hz, 1H), 6.86 (d, J = 3.0 Hz, 1H), 6.78 (d, J = 8.8, 2.9 Hz, 1H), 6.71 (s, 1H), 5.11-4.97 (m, 2H), 4.91 (d, J = 7.2 Hz, 1H), 4.51 (d, J = 9.3 Hz, 1H), 4.42 (d, J = 8.0 Hz, 1H), 4.30-4.24 (m, 5H), 4.03 (s, 1H), 3.97-3.87 (m, 3H), 3.63--3.57 (m, 3H), 3.03-3.01 (m, 3H), 2.82 (d, J = 16.7 Hz, 1H), 2.60 (m, 2H), 2.45 (s, 3H), 2.14-2.01 (m, 1H), 1.86-1.63 (m, 2H), 1.52-1.50 (m, 3H), 1.38-1.35 (m, 11H), 1.35-1.31 (m, 3H), 1.28-1.24 (m, 3H), 0.92 (s, 9H) |

TABLE 50-continued

Characterization data for intermediates prepared according to above.

| Inter-mediate | Structure | Chemical Name | MS: [(M + 1)]+ | $^1$H NMR |
|---|---|---|---|---|
| I112 | 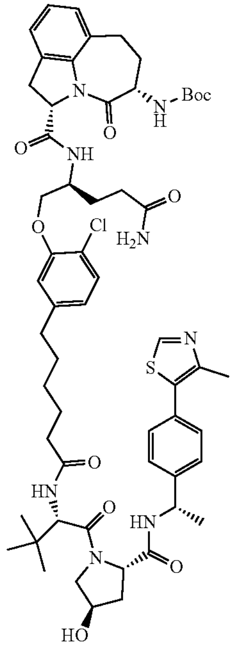 [SMILES: Cc1ncsc1-c1ccc([C@H](C)NC(=O)[C@@H]2C[C@@H](O)CN2C(=O)[C@@H](NC(=O)CCCCCc2ccc(Cl)c(OC[C@H](CCC(N)=O)NC(=O)[C@@H]3Cc4cccc5c4N3C(=O)[C@@H](NC(=O)OC(C)(C)C)CC5)c2)C(C)(C)C)cc1] | tert-butyl N-[(2S,11S)-2-[[(2S)-4-carbamoyl-1-[2-chloro-5-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenoxy]butan-2-yl]carbamoyl]-12-oxo-1-azatricyclo[6.4.1.0^[4,13]]trideca-4(13),5,7-trien-11-yl]carbamate | 1111.80 | (300 MHz, DMSO-$d_6$) δ 9.03-8.97 (m, 2H), 8.42-8.34 (m, 1H), 7.85-7.71 (m, 1H), 7.50-7.35 (m, 5H), 7.37-7.21 (m, 2H), 7.08-6.96 (m, 4H), 6.84-6.72 (m, 2H), 4.44-4.42 (m, 1H), 4.30-4.28 (m, 1H), 4.09-4.01 (m, 3H), 3.65-3.59 (m, 3H), 3.42-3.25 (m, 10H), 2.50-2.44 (m, 5H), 2.32-2.25 (m, 2H), 2.19-2.12 (m, 4H), 2.10-2.04 (m, 2H), 1.59-1.51 (m, 5H), 1.39 (s, 9H), 1.32-1.23 (m, 4H), 0.90 (s, 9H) |
| I113 | 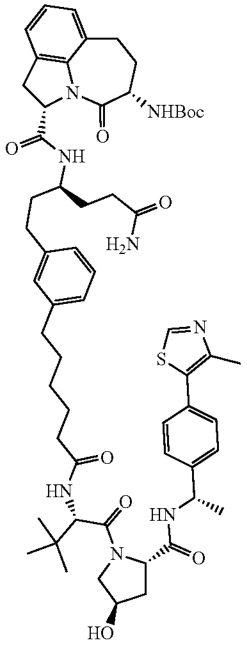 [SMILES: Cc1ncsc1-c1ccc([C@H](C)NC(=O)[C@@H]2C[C@@H](O)CN2C(=O)[C@@H](NC(=O)CCCCCc2cccc(CC[C@H](CCC(N)=O)NC(=O)[C@@H]3Cc4cccc5c4N3C(=O)[C@@H](NC(=O)OC(C)(C)C)CC5)c2)C(C)(C)C)cc1] | tert-butyl N-[(2S,11S)-2-[[(3R)-1-carbamoyl-5-[3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenyl]pentan-3-yl]carbamoyl]-12-oxo-1-azatricyclo[6.4.1.0^[4,13]]trideca-4(13),5,7-trien-11-yl]carbamate | 1075.45 | (400 MHz, DMSO-$d_6$) δ 8.99 (s, 1H), 8.37 (d, J = 7.8 Hz, 1H), 7.91-7.76 (m, 2H), 7.49-7.36 (m, 4H), 7.29-7.02 (m, 5H), 7.02-6.92 (m, 4H), 6.69 (d, J = 6.9 Hz, 1H), 5.13-4.86 (m, 3H), 4.53 (d, J = 9.3 Hz, 1H), 4.43 (t, J = 8.0 Hz, 1H), 4.33-4.24 (m, 1H), 4.10-4.01 (m, 1H), 3.68-3.56 (m, 4H), 3.55-3.41 (m, 1H), 3.12-2.93 (m, 4H), 2.46 (s, 3H), 2.32-2.20 (m, 2H), 2.16-1.98 (m, 10H), 1.84-1.75 (m, 2H), 1.75-1.44 (m, 4H), 1.42-1.35 (m, 12H), 1.33-1.19 (m, 2H), 0.94 (s, 9H) |

TABLE 50-continued

Characterization data for intermediates prepared according to above.

| Intermediate | Structure | Chemical Name | MS: [(M + 1)]+ | $^1$H NMR |
|---|---|---|---|---|
| I114 | 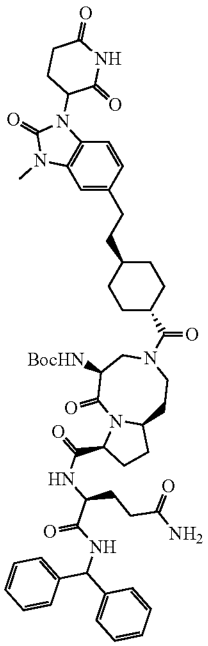 [SMILES: Cn1c(=O)n(C2CCC(=O)NC2=O)c2ccc(CC[C@H]3CC[C@H](C(=O)N4CC[C@H]5CC[C@@H](C(=O)N[C@@H](CCC(N)=O)C(=O)NC(c6ccccc6)c6ccccc6)N5C(=O)[C@@H](NC(=O)OC(C)(C)C)C4)CC3)cc21] | tert-butyl N-[(5S,8S,10aR)-8-[[(1S)-3-carbamoyl-1-(diphenylmethyl carbamoyl) propyl]carbamoyl]-6-oxo-3-[(1r,4r)-4-[2-[1-(2,6-dioxopiperidin-3-yl)-3-methyl-2-oxo-1,3-benzodiazol-5-yl]ethyl] cyclohexanecarbonyl]-octahydropyrrolo[1,2-a][1,5]diazocin-5-yl]carbamate | 1016.30 | (400 MHz, DMSO-$d_6$) δ 11.08 (s, 1H), 8.74 (d, J = 8.5 Hz, 1H), 8.22-8.12 (m, 1H), 7.38-7.29 (m, 3H), 7.29 (td, J = 7.3, 5.8, 3.5 Hz, 5H), 7.28-7.22 (m, 2H), 7.21 (s, 1H), 7.04-6.91 (m, 2H), 6.86 (d, J = 8.1 Hz, 1H), 6.74 (s, 1H), 6.10 (d, J = 8.4 Hz, 1H), 5.34 (dd, J = 12.7, 5.4 Hz, 1H), 4.47 (s, 1H), 4.43-4.29 (m, 2H), 4.08 (s, 1H), 3.78 (dt, J = 12.4, 6.2 Hz, 1H), 3.71 (s, 2H), 3.33 (s, 3H), 3.22 (s, 1H), 3.17-3.10 (m, 1H), 2.90 (s, 1H), 2.83 (s, 1H), 2.78-2.59 (m, 4H), 2.22-2.05 (m, 2H), 2.05-1.55 (m, 11H), 1.53-1.46 (m, 1H), 1.41 (s, 9H), 1.37-1.19 (m, 4H), 1.07-1.02 (m, 4H) |
| I115 | 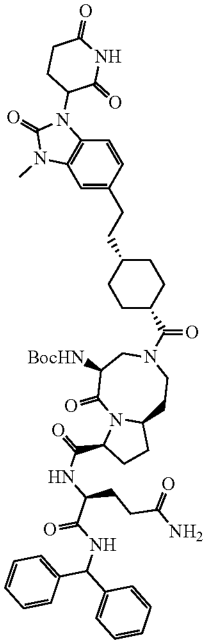 [SMILES: Cn1c(=O)n(C2CCC(=O)NC2=O)c2ccc(CC[C@H]3CC[C@@H](C(=O)N4CC[C@H]5CC[C@@H](C(=O)N[C@@H](CCC(N)=O)C(=O)NC(c6ccccc6)c6ccccc6)N5C(=O)[C@@H](NC(=O)OC(C)(C)C)C4)CC3)cc21] | tert-butyl N-[(5S,8S,10 aR)-8-[[(1S)-3-carbamoyl-1-(diphenylmethyl carbamoyl)propyl] carbamoyl]-6-oxo-3-[(1s,4s)-[4-[2-[1-(2,6-dioxopiperidin-3-yl)-3-methyl-2-oxo-1,3-benzodiazol-5-yl]ethyl]cyclohexane-carbonyl]-octahydro-pyrrolo[1,2-a][1,5] diazocin-5-yl]carbamate | 1016.30 | (400 MHz, DMSO-$d_6$) δ 11.08 (s, 1H), 8.73 (d, J = 8.5 Hz, 1H), 8.19 (d, J = 7.7 Hz, 1H), 7.38-7.22 (m, 11H), 7.20 (s, 1H), 7.07-6.97 (m, 2H), 6.88 (d, J = 8.1 Hz, 1H), 6.74 (s, 1H), 6.10 (d, J = 8.4 Hz, 1H), 5.34 (dd, J = 12.8, 5.5 Hz, 1H), 4.45 (s, 1H), 4.36 (dd, J = 19.1, 9.5 Hz, 2H), 4.09 (s, 1H), 3.72 (d, J = 14.0 Hz, 2H), 3.32 (s, 3H), 3.21 (s, 1H), 3.12 (s, 1H), 2.96-2.84 (m, 2H), 2.74-2.63 (m, 1H), 2.61 (s, 4H), 2.10 (d, J = 11.9 Hz, 4H), 2.04-1.97 (m, 1H), 1.92 (s, 2H), 1.62-1.58 (m, 14H), 1.39 (s, 9H) |

TABLE 50-continued

Characterization data for intermediates prepared according to above.

| Intermediate | Structure | Chemical Name | MS: [(M + 1)]+ | $^1$H NMR |
|---|---|---|---|---|
| I116 | 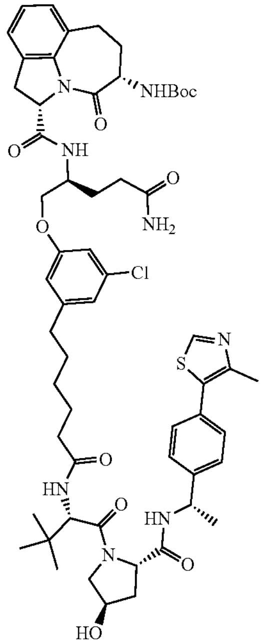 [SMILES: Cc1ncsc1-c1ccc([C@H](C)NC(=O)[C@@H]2C[C@@H](O)CN2C(=O)[C@@H](NC(=O)CCCCCc2cc(Cl)cc(OC[C@H](CCC(N)=O)NC(=O)[C@@H]3Cc4cccc5c4N3C(=O)[C@@H](NC(=O)OC(C)(C)C)CC5)c2)C(C)(C)C)cc1] | tert-butyl N-[(2S,11S)-2-[[(2S)-4-carbamoyl-1-[3-chloro-5-(5-[[(2S)-1-[(2S,4R)-4-hydroxy-2-[[(1S)-1-[4-(4-methyl-1,3-thiazol-5-yl)phenyl]ethyl] carbamoyl] pyrrolidin-1-yl]-3,3-dimethyl-1-oxobutan-2-yl]carbamoyl]pentyl) phenoxy]butan-2-yl]carbamoyl]-12-oxo-1-azatricyclo[6.4.1.0^[4,13]] trideca-4(13),5,7-trien-11-yl]carbamate | 1111.35 | (300 MHz, DMSO-$d_6$) δ 8.99 (s, 1H), 8.37 (d, J = 7.8 Hz, 1H), 8.04 (d, J = 8.0 Hz, 1H), 7.79 (d, J = 9.2 Hz, 1H), 7.47-7.36 (m, 5H), 7.27-7.20 (m, 1H), 7.05 (d, J = 7.5 Hz, 2H), 7.00-6.91 (m, 1H), 6.87-6.78 (m, 2H), 6.76-6.69 (m, 2H), 5.10 (d, J = 3.6 Hz, 1H), 5.07-4.99 (m, 1H), 4.98-4.87 (m 1H), 4.52 (d, J = 9.3 Hz, 1H), 4.43 (t, J = 8.0 Hz, 1H), 4.32-4.26 (m, 1H), 4.04 (d, J = 8.6 Hz, 1H), 3.99-3.86 (m, 3H), 3.67-3.55 (m, 2H), 3.45-3.38 (m, 1H), 3.13-3.97 (m, 2H), 2.90-2.80 (m, 1H), 2.46 (s, 3H), 2.33-2.21 (m, 1H), 2.19-1.95 (m, 7H), 1.86-1.76 (m, 2H), 1.74-1.64 (m, 1H), 1.59-1.47 (m, 4H), 1.39 (s, 9H), 1.38-1.36 (m, 2H), 1.32-1.22 (m, 4H), 0.94 (s, 9H) |
| I117 | 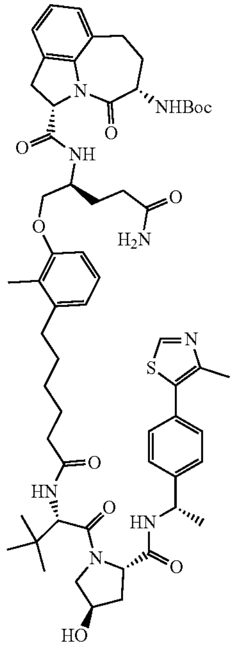 [SMILES: Cc1ncsc1-c1ccc([C@H](C)NC(=O)[C@@H]2C[C@@H](O)CN2C(=O)[C@@H](NC(=O)CCCCCc2cccc(OC[C@H](CCC(N)=O)NC(=O)[C@@H]3Cc4cccc5c4N3C(=O)[C@@H](NC(=O)OC(C)(C)C)CC5)c2C)C(C)(C)C)cc1] | tert-butyl N-[(2S,11S)-2-[[(2S)-4-carbamoyl-1-[3-(5-[[(2S)-1-[(2S,4R)-4-hydroxy-2-[[(1S)-1-[4-(4-methyl-1,3-thiazol-5-yl)phenyl]ethyl] carbamoyl] pyrrolidin-1-yl]-3,3-dimethyl-1-oxobutan-2-yl]carbamoyl]pentyl)-2-methylphenoxy]butan-2-yl]carbamoyl]-12-oxo-1-azatricyclo[6.4.1.0^[4,13]] trideca-4(13),5,7-trien-11-yl]carbamate | 1091.55 | (400 MHz, DMSO-$d_6$) δ 8.99 (s, 1H), 8.36 (d, J = 7.8 Hz, 1H), 8.05 (d, J = 8.4 Hz, 1H), 7.79 (d, J = 9.3 Hz, 1H), 7.47-7.41 (m, 2H), 7.38 (d, J = 8.4 Hz, 2H), 7.23 (s, 1H), 7.16-6.92 (m, 7H), 6.78-6.68 (m, 3H), 5.14-5.00 (m, 2H), 4.96-4.89 (m, 1H), 4.55-4.49 (m, 1H), 4.43 (t, J = 8.0 Hz, 1H), 4.28 (s, 1H), 4.07-4.00 (m, 2H), 3.92-3.83 (m, 2H), 3.64-3.59 (m, 2H), 3.13-2.97 (m, 2H), 2.86 (dd, J = 16.9, 2.8 Hz, 1H), 2.55-2.53 (m, 3H), 2.46 (s, 3H), 2.30-2.24 (m, 1H), 2.19-2.09 (m, 2H), 2.04-1.98 (m, 1H), 1.92-1.67 (m, 2H), 1.63-1.43 (m, 3H), 1.39 (s, 9H), 1.33-1.19 (m, 4H), 0.94 (s, 9H), 0.90-0.80 (m, 7H) |

TABLE 50-continued

| Characterization data for intermediates prepared according to above. | | | | |
|---|---|---|---|---|
| Inter-mediate | Structure | Chemical Name | MS: [(M + 1)]+ | $^1$H NMR |
| I118 | 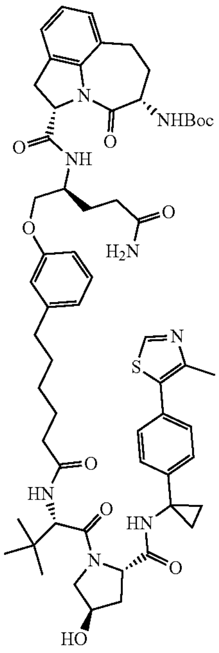 [SMILES: Cc1ncsc1-c1ccc(C2(NC(=O)[C@@H]3C[C@@H](O)CN3C(=O)[C@@H](NC(=O)CCCCCc3cccc(OC[C@H](CCC(N)=O)NC(=O)[C@@H]4Cc5cccc6c5N4C(=O)[C@@H](NC(=O)OC(C)(C)C)CC6)c3)C(C)(C)C)CC2)cc1] | tert-butyl N-[(2S,11S)-2-[[(2S)-4-carbamoyl-1-[3-(5-[[(2S)-1-[(2S,4R)-4-hydroxy-2-([1-[4-(4-methyl-1,3-thiazol-5-yl)phenyl]cyclopropyl]carbamoyl)pyrrolidin-1-yl]-3,3-dimethyl-1-oxobutan-2-yl]carbamoyl]pentyl)phenoxy]butan-2-yl]carbamoyl]-12-oxo-1-azatricyclo[6.4.1.0^[4,13]]trideca-4(13),5,7-trien-11-yl]carbamate | 1090.85 | (400 MHz, DMSO-d$_6$) δ 8.97 (s, 1H), 8.79 (s, 1H), 8.03 (d, J = 8.3 Hz, 1H), 7.90 (d, J = 9.4 Hz, 1H), 7.36-7.27 (m, 4H), 7.25-7.13 (m, 2H), 7.08-7.04 (m, 3H), 6.95 (t, J = 7.4 Hz, 1H), 6.75 (dd, J = 17.3, 7.2 Hz, 4H), 5.12 (d, J = 3.4 Hz, 1H), 5.06-5.02 (m, 1H), 4.55 (d, J = 9.3 Hz, 1H), 4.41-4.37 (m, 2H), 4.05 (s, 1H), 3.98 (s, 1H), 3.89 (t, J = 5.0 Hz, 1H), 3.65 (d, J = 3.5 Hz, 2H), 3.43-3.39 (m, 1H), 3.04 (s, 2H), 2.86 (d, J = 17.0 Hz, 1H), 2.55 (s, 1H), 2.44 (s, 3H), 2.31-2.27 (m, 1H), 2.17-2.09 (m, 2H), 2.04-2.00 (m, 1H), 1.93-1.86 (m, 1H), 1.85 (s, 1H), 1.72-1.68 (m, 1H), 1.55 (s, 3H), 1.40 (s, 9H), 1.34-1.23 (m, 5H), 1.21-1.12 (m, 1H), 0.94 (s, 9H), 0.91-0.80 (m, 6H) |
| I119 | 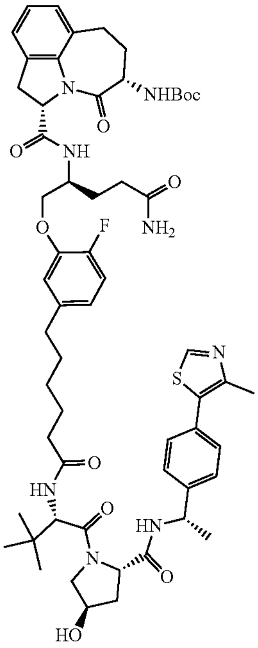 [SMILES: Cc1ncsc1-c1ccc([C@H](C)NC(=O)[C@@H]2C[C@@H](O)CN2C(=O)[C@@H](NC(=O)CCCCCc2ccc(F)c(OC[C@H](CCC(N)=O)NC(=O)[C@@H]3Cc4cccc5c4N3C(=O)[C@@H](NC(=O)OC(C)(C)C)CC5)c2)C(C)(C)C)cc1] | tert-butyl N-[(11S)-2-[[(2S)-4-carbamoyl-1-[2-fluoro-5-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenoxy]butan-2-yl]carbamoyl]-12-oxo-1-azatricyclo[6.4.1.0^[4,13]]trideca-4(13),5,7-trien-11-yl]carbamate | 1095.25 | (300 MHz, DMSO-d$_6$) δ 8.97 (s, 1H), 8.34 (d, J = 7.8 Hz, 1H), 8.06 (s, 1H), 7.76 (d, J = 9.1 Hz, 1H), 7.40-7.35 (m, 4H), 7.22 (s, 1H), 7.13-6.88 (m, 7H), 6.72 (s, 1H), 5.11-4.98 (m, 1H), 4.97-4.86 (m, 1H), 4.51 (d, J = 9.3 Hz, 1H), 4.42 (d, J = 8.0 Hz, 1H), 4.28 (s, 2H), 4.01-3.97 (m, 5H), 3.60 (s, 2H), 3.03 (s, 2H), 2.88-2.84 (m, 1H), 2.45 (s, 3H), 2.13-2.09 (m, 3H), 2.04-2.00 (m, 3H), 1.53-1.49 (m, 5H), 1.37-1.31 (m, 13H), 1.24-1.20 (m, 6H), 0.92 (s, 9H) |

TABLE 50-continued

Characterization data for intermediates prepared according to above.

| Intermediate | Structure | Chemical Name | MS: [(M + 1)]$^+$ | $^1$H NMR |
|---|---|---|---|---|
| I120 | 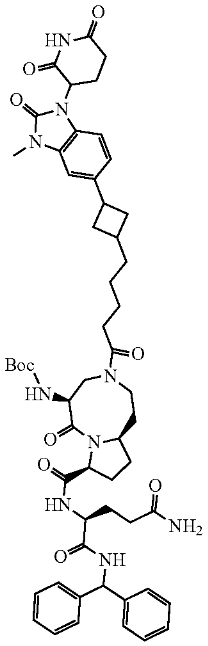 [SMILES: Cn1c(=O)n(C2CCC(=O)NC2=O)c2ccc(C3CC(CCCCC(=O)N4CC[C@H]5CC[C@@H](C(=O)N[C@@H](CCC(N)=O)C(=O)NC(c6ccccc6)c6ccccc6)N5C(=O)[C@@H](NC(=O)OC(C)(C)C)C4)C3)cc21] | tert-butyl N-[(5S,8S,10aR)-8-[[(1S)-3-carbamoyl-1-(diphenylmethyl carbamoyl) propyl]carbamoyl]-3-(5-[3-[1-(2,6-dioxopiperidin-3-yl)-3-methyl-2-oxo-1,3-benzodiazol-5-yl]cyclobutyl] pentanoyl)-6-oxo-octahydropyrrolo[1,2-a][1,5]diazocin-5-yl]carbamate | 1016.40 | (400 MHz, Chloroform-d) δ 9.34-8.49 (m, 1H), 7.82-7.77 (m, 1H), 7.42-7.32 (m, 2H), 7.25-7.19 (m, 2H), 7.00-6.66 (m, 5H), 6.41 (s, 1H), 6.21 (d, J = 7.7 Hz, 2H), 5.90-5.48 (m, 3H), 5.26-5.19 (m, 2H), 4.90-4.12 (m, 7H), 4.05-3.88 (m, 3H), 3.45 (s, 3H), 3.41-3.31 (m, 2H), 3.20-3.04 (m, 3H), 2.98-2.60 (m, 4H), 2.55-2.45 (m, 3H), 2.38-1.79 (m, 10H), 1.46 (s, 9H), 1.45-1.19 (m, 6H) |
| I121 | 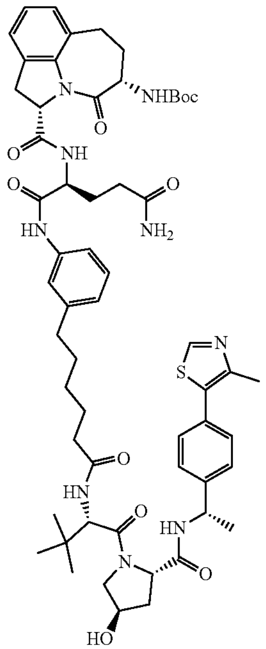 [SMILES: Cc1ncsc1-c1ccc([C@H](C)NC(=O)[C@@H]2C[C@@H](O)CN2C(=O)[C@@H](NC(=O)CCCCCc2cccc(NC(=O)[C@H](CCC(N)=O)NC(=O)[C@@H]3Cc4cccc5c4N3C(=O)[C@@H](NC(=O)OC(C)(C)C)CC5)c2)C(C)(C)C)cc1] | tert-butyl N-[(2S,11S)-2-[[(1S)-3-carbamoyl-1-[[3-(5-[[(2S)-1-[(2S,4R)-4-hydroxy-2-[[(1S)-1-[4-(4-methyl-1,3-thiazol-5-yl)phenyl]ethyl] carbamoyl] pyrrolidin-1-yl]-3,3-dimethyl-1-oxobutan-2-yl]carbamoyl]pentyl) phenyl]carbamoyl] propyl]carbamoyl]-12-oxo-1-azatricyclo[6.4.1.0^[4,13]] trideca-4(13),5,7-trien-11-yl]carbamate | 1090.45 | (300 MHz DMSO-$d_6$) δ 9.91 (s, 1H), 8.97 (s, 1H), 8.32 (dd, J = 15.7, 7.6 Hz, 2H), 7.76 (d, J = 9.3 Hz, 1H), 7.45-7.36 (m, 7H), 7.29 (s, 1H), 7.17 (t, J = 8.1 Hz, 1H), 7.13-6.98 (m, 3H), 6.98-6.82 (m, 2H), 6.76 (s, 1H), 5.18-5.02 (m, 2H), 5.01-4.83 (m, 1H), 4.51 (d, J = 9.2 Hz, 1H), 4.42 (t, J = 8.0 Hz, 1H), 4.33-4.26 (m, 2H), 4.05 (s, 1H), 3.60 (s, 2H), 3.51-3.35 (m, 1H), 3.28 (s, 2H), 3.08-2.95 (m, 3H), 2.45 (s, 3H), 2.31-1.72 (m, 9H), 1.59-1.45 (m, 3H), 1.38 (s, 11H), 1.36 (s, 2H), 1.32-1.19 (m, 2H), 0.92 (s, 9H) |

TABLE 50-continued

| Characterization data for intermediates prepared according to above. | | | | |
|---|---|---|---|---|
| Inter-mediate | Structure | Chemical Name | MS: [(M + 1)]+ | $^1$H NMR |
| I122 | 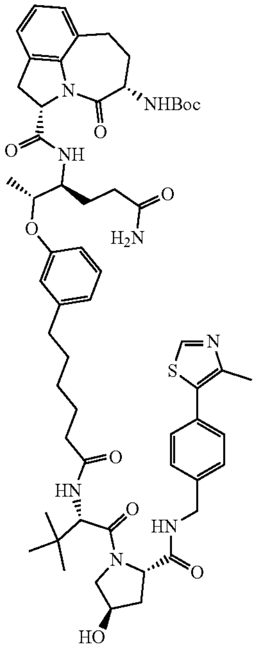 [SMILES: Cc1ncsc1-c1ccc(CNC(=O)[C@@H]2C[C@@H](O)CN2C(=O)[C@@H](NC(=O)CCCCCc2cccc(O[C@H](C)[C@H](CCC(N)=O)NC(=O)[C@@H]3Cc4cccc5c4N3C(=O)[C@@H](NC(=O)OC(C)(C)C)CC5)c2)C(C)(C)C)cc1] | tert-butyl N-[(2S,11S)-2-[[(3S,4R)-1-carbamoyl-4-[3-(5-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]pentyl)phenoxy]pentan-3-yl]carbamoyl]-12-oxo-1-azatricyclo[6.4.1.0^[4,13]]trideca-4(13),5,7-trien-11-yl]carbamate | 1077.45 | (300 MHz, DMSO-$d_6$) δ 9.00 (s, 1H), 8.57 (t, J = 6.0 Hz, 1H), 7.90 (dd, J = 25.3, 9.1 Hz, 2H), 7.49-7.34 (m, 5H), 7.25-6.89 (m, 7H), 6.81-6.63 (m, 5H), 5.14 (d, J = 3.6 Hz, 1H), 5.11-5.01 (m, 1H), 4.56 (d, J = 9.3 Hz, 1H), 4.50-4.32 (m, 4H), 4.24 (dd, J = 15.8, 5.4 Hz, 1H), 4.09-4.01 (m, 1H), 3.88-3.79 (m, 1H), 3.72-3.63 (m, 2H), 3.11-2.99 (m, 2H), 2.79 (d, J = 17.3 Hz, 1H), 2.46 (s, 3H), 2.36-2.20 (m, 1H), 2.16-1.86 (m, 9H), 1.64-1.50 (m, 3H), 1.40 (s, 9H), 1.31-1.26 (m, 3H), 1.19 (d, J = 6.1 Hz, 3H), 0.95 (s, 9H) |
| I123 | 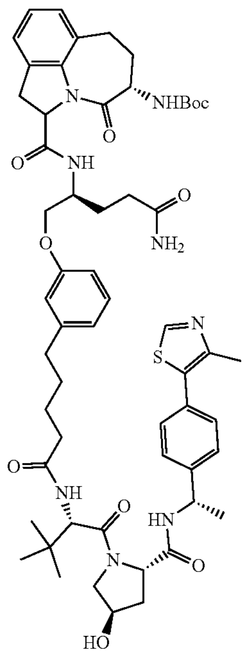 [SMILES: Cc1ncsc1-c1ccc([C@H](C)NC(=O)[C@@H]2C[C@@H](O)CN2C(=O)[C@@H](NC(=O)CCCCc2cccc(OC[C@H](CCC(N)=O)NC(=O)C3Cc4cccc5c4N3C(=O)[C@@H](NC(=O)OC(C)(C)C)CC5)c2)C(C)(C)C)cc1] | tert-butyl N-[(2S,11S)-2-[[(2S)-4-carbamoyl-1-[3-(4-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]butyl)phenoxy]butan-2-yl]carbamoyl]-12-oxo-1-azatricyclo[6.4.1.0^[4,13]]trideca-4(13),5,7-trien-11-yl]carbamate | 1063.45 | (400 MHz, DMSO-$d_6$) δ 8.99 (s, 1H), 8.38 (d, J = 7.8 Hz, 1H), 8.05 (d, J = 8.3 Hz, 1H), 7.83 (d, J = 9.3 Hz, 1H), 7.48-7.41 (m, 2H), 7.41-7.29 (m, 2H), 7.26-7.02 (m, 5H), 6.96 (dd, J = 7.9, 7.0 Hz, 1H), 6.80-6.69 (m, 4H), 5.10 (d, J = 3.5 Hz, 1H), 5.06-5.02 (m, 1H), 4.92 (p, J = 6.9 Hz, 1H), 4.52 (d, J = 9.3 Hz, 1H), 4.42 (t, J = 8.0 Hz, 1H), 4.28 (s, 1H), 4.07-3.95 (m, 1H), 3.95-3.83 (m, 2H), 3.66-3.55 (m, 2H), 3.44-3.40 (m, 1H), 3.31 (s, 3H), 3.12-2.97 (m, 1H), 2.87-2.83 (m, 1H), 2.56-2.52 (m, 2H), 2.46 (s, 3H), 2.31-2.27 (m, 1H), 2.18-1.97 (m, 4H), 1.88-1.64 (m, 3H), 1.55-1.51 (m, 4H), 1.39 (s, 9H), 1.39-1.35 (m, 1H), 1.28-1.24 (m, 3H), 0.94 (s, 9H) |

TABLE 50-continued

| Characterization data for intermediates prepared according to above. | | | | |
|---|---|---|---|---|
| Inter-mediate | Structure | Chemical Name | MS: [(M + 1)]$^+$ | $^1$H NMR |
| I124 | 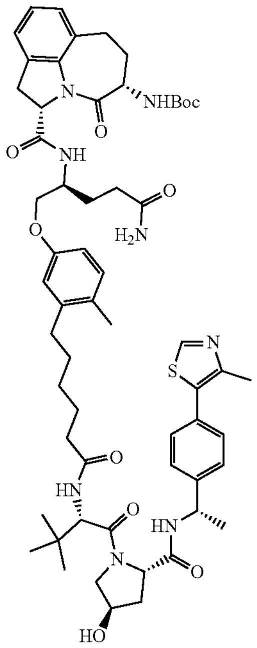 [SMILES: Cc1ccc(OC[C@H](CCC(N)=O)NC(=O)[C@@H]2Cc3cccc4c3N2C(=O)[C@@H](NC(=O)OC(C)(C)C)CC4)cc1CCCCCC(=O)N[C@H](C(=O)N1C[C@H](O)C[C@H]1C(=O)N[C@@H](C)c1ccc(-c2scnc2C)cc1)C(C)(C)C] | tert-butyl N-[(2S,11S)-2-[[(2S)-4-carbamoyl-1-[3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)-4-methylphenoxy]butan-2-yl]carbamoyl]-12-oxo-1-azatricyclo[6.4.1.0^[4,13]]trideca-4(13),5,7-trien-11-yl]carbamate | 1091.55 | (400 MHz, DMSO-$d_6$) δ 8.99 (s, 1H), 8.38 (d, J = 7.8 Hz, 1H), 8.03 (d, J = 8.4 Hz, 1H), 7.81 (d, J = 9.3 Hz, 1H), 7.44 (d, J = 8.3 Hz, 2H), 7.38 (d, J = 8.3 Hz, 2H), 7.24 (s, 1H), 7.10 (d, J = 8.0 Hz, 1H), 7.03 (dd, J = 13.9, 7.9 Hz, 3H), 6.96 (dd, J = 8.0, 6.9 Hz, 1H), 6.74 (s, 1H), 6.70-6.60 (m, 1H), 5.10-5.08 (m, 1H), 5.03-5.01 (m, 1H), 4.9-4.90 (m, 1H), 4.53-4.51 (m, 1H), 4.43-4.41 (m, 1H), 4.28 (s, 1H), 4.07-4.01 (m, 1H), 3.96-3.94 (m, 2H), 3.91-3.79 (m, 2H), 3.6-3.58 (m, 2H), 3.41-3.38 (m, 1H), 3.16-2.97 (m, 2H), 2.85-2.83 (m, 1H), 2.45 (s, 3H), 2.28-2.26 (m, 1H), 2.18-2.16 (m, 3H), 2.12-2.10 (m, 3H), 2.03-1.87 (m, 4H), 1.80-1.78 (m, 2H), 1.73-1.62 (m, 2H), 1.62-1.43 (m, 4H), 1.38 (s, 9H), 1.37-1.35 (m, 2H), 1.32-1.30 (m, 1H), 1.29-1.22 (m, 2H), 0.94 (s, 9H) |
| I125 | 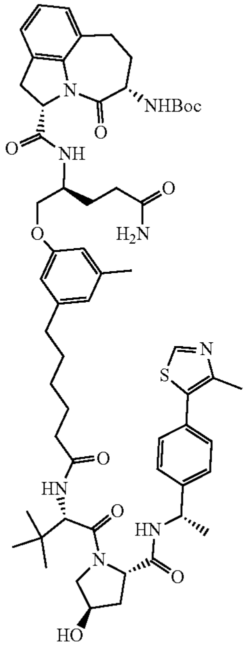 [SMILES: Cc1cc(CCCCCC(=O)N[C@H](C(=O)N2C[C@H](O)C[C@H]2C(=O)N[C@@H](C)c2ccc(-c3scnc3C)cc2)C(C)(C)C)cc(OC[C@H](CCC(N)=O)NC(=O)[C@@H]2Cc3cccc4c3N2C(=O)[C@@H](NC(=O)OC(C)(C)C)CC4)c1] | tert-butyl N-[(2S,11S)-2-[[(2S)-4-carbamoyl-1-[3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)-5-methylphenoxy]butan-2-yl]carbamoyl]-12-oxo-1-azatricyclo[6.4.1.0^[4,13]]trideca-4(13),5,7-trien-11-yl]carbamate | 1091.50 | (400 MHz, DMSO-$d_6$) δ 8.99 (s, 1H), 8.38 (d, J = 7.8 Hz, 1H), 8.03 (d, J = 8.3 Hz, 1H), 7.80 (d, J = 9.3 Hz, 1H), 7.44 (d, J = 8.3 Hz, 2H), 7.45-7.35 (m, 2H), 7.24 (s, 1H), 7.10 (d, J = 8.0 Hz, 1H), 7.05 (d, J = 7.5 Hz, 2H), 6.96 (d, J = 8.1, 6.8 Hz, 1H), 6.74 (s, 1H), 6.58 (s, 1H), 6.53 (d, J = 4.7 Hz, 2 H), 5.11 (d, J = 3.6 Hz, 1H), 5.04 (d, J = 10.7, 2.7Hz, 1H), 4.94-4.90 (m, 1H), 4.52 (d, J = 9.3 Hz, 1H), 4.43 (d, J = 8.0 Hz, 1H), 4.28 (m, 1H), 4.06-4.02 (m, 1H), 3.99-3.97 (m, 1H), 3.96-3.81 (m, 2H), 3.63-3.59 (m, 2H), 3.43-3.39 (m, 1H), 2.88-2.84 (m, 1H), 2.24 (s, 3H), 2.16-2.02 (m, 4H), 1.82-1.78 (m, 2H), 1.74-1.63 (m, 1H), 1.59-1.44 (m, 4H), 1.43-1.35 (m, 14H), 1.32-1.21 (m, 7H), 0.94 (s, 9H), 0.88-0.83 (m, 3H) |

TABLE 50-continued

Characterization data for intermediates prepared according to above.

| Intermediate | Structure | Chemical Name | MS: [(M + 1)]+ | $^1$H NMR |
|---|---|---|---|---|
| I126 | 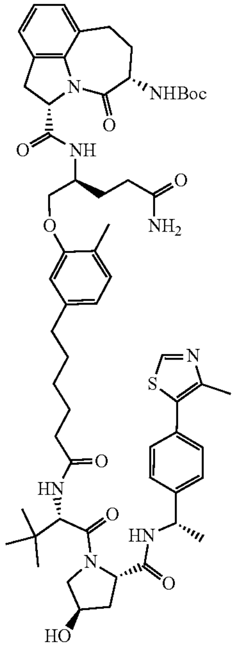 [SMILES: Cc1ccc(CCCCCC(=O)N[C@H](C(=O)N2C[C@H](O)C[C@H]2C(=O)N[C@@H](C)c2ccc(-c3scnc3C)cc2)C(C)(C)C)cc1OC[C@H](CCC(N)=O)NC(=O)[C@@H]1Cc2cccc3c2N1C(=O)[C@@H](NC(=O)OC(C)(C)C)CC3] | tert-butyl N-[(2S,11S)-2-[[(2S)-4-carbamoyl-1-[5-(5-[[(2S)-1-[(2S,4R)-4-hydroxy-2-[[(1S)-1-[4-(4-methyl-1,3-thiazol-5-yl)phenyl]ethyl] carbamoyl] pyrrolidin-1-yl]-3,3-dimethyl-1-oxobutan-2-yl]carbamoyl]pentyl)-2-methylphenoxy]butan-2-yl]carbamoyl]-12-oxo-1-azatricyclo[6.4.1.0^[4,13]] trideca-4(13),5,7-trien-11-yl]carbamate | 1091.55 | (400 MHz, DMSO-$d_6$) δ 8.99 (s, 1H), 8.36 (d, J = 7.8 Hz, 1H), 8.03 (d, J = 8.4 Hz, 1H), 7.77 (d, J = 9.3 Hz, 1H), 7.46-7.42 (m, 2H), 7.38 (d, J = 8.4 Hz, 2H), 7.23 (s, 1H), 7.11-7.02 (m, 2H), 7.02-6.99 (m, 2H), 6.98-6.92 (m, 1H), 6.75-6.70 (m, 2H), 6.65 (d, J = 7.5, 1.4 Hz, 1H), 5.12-5.01 (m, 2H), 4.92 (s, 1H), 4.52 (d, J = 9.4 Hz, 1H), 4.43 (s, 1H), 4.33-4.25 (m, 1H), 4.04-4.00 (m, 2H), 3.93-3.89 (m, 1H), 3.66-3.55 (m, 2H), 3.47-3.37 (m, 1H), 3.32-3.28 (m, 1H), 3.06-2.97 (m, 1H), 2.90-2.81 (m, 1H), 2.46 (s, 3H), 2.33-2.19 (m, 1H), 2.15-2.11 (m, 1H), 2.10-2.06 (m, 6H), 1.84-1.80 (m, 1H), 1.57-1.48 (m, 3H), 1.42-1.36 (m, 12H), 1.29-1.24 (m, 4H), 0.93 (s, 9H), 0.89-0.86 (m, 3H), 0.85-0.84 (m, 2H) |
| I127 | 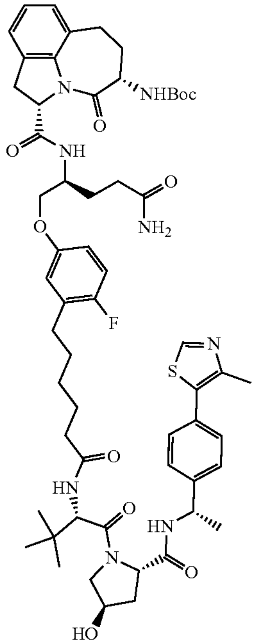 [SMILES: Cc1ncsc1-c1ccc([C@H](C)NC(=O)[C@@H]2C[C@@H](O)CN2C(=O)[C@@H](NC(=O)CCCCCc2cc(OC[C@H](CCC(N)=O)NC(=O)[C@@H]3Cc4cccc5c4N3C(=O)[C@@H](NC(=O)OC(C)(C)C)CC5)ccc2F)C(C)(C)C)cc1] | tert-butyl N-[(2S,11S)-2-[[(2S)-4-carbamoyl-1-[4-fluoro-3-(5-[[(2S)-1-[(2S,4R)-4-hydroxy-2-[[(1S)-1-[4-(4-methyl-1,3-thiazol-5-yl)phenyl]ethyl] carbamoyl] pyrrolidin-1-yl]-3,3-dimethyl-1-oxobutan-2-yl]carbamoyl]pentyl) phenoxy]butan-2-yl]carbamoyl]-12-oxo-1-azatricyclo[6.4.1.0^[4,13]] trideca-4(13),5,7-trien-11-yl]carbamate | 1095.50 | (400 MHz, DMSO-$d_6$) δ 8.99 (s, 1H), 8.38 (d, J = 7.8 Hz, 1H), 8.04 (d, J = 8.3 Hz, 1H), 7.80 (d, J = 9.3 Hz, 1H), 7.47-.41 (m, 2H), 7.41-7.30 (m, 2H), 7.24 (s, 1H), 7.13-7.03 (m, 2H), 7.07-6.99 (m, 2H), 6.99-6.92 (m, 1H), 6.80 (dd, J = 6.2, 3.1 Hz, 1H), 6.80-6.72 (m, 2H), 5.10 (d, J = 3.6 Hz, 1H), 5.05-5.02 (m, 1H), 4.94-4.90 (m, 1H), 4.52 (d, J = 9.3 Hz, 1H), 4.42 (t, J = 8.0 Hz, 1H), 4.28 (s, 1H), 4.03 (d, J = 8.5 Hz, 1H), 3.99-3.93 (m, 2H), 3.87 (t, J = 5.2 Hz, 2H), 3.60 (s, 2H), 3.44-3.40 (m, 1H), 3.06-3.02 (m, 2H), 2.87-2.83 (m, 1H), 2.56-2.52 (m, 2H), 2.46 (s, 3H), 2.30-2.20 (m, 1H), 2.17-1.96 (m, 5H), 1.81-1.77 (m, 1H), 1.71-1.67 (m, 1H), 1.57-1.44 (m, 4H), 1.38 (s, 9H), 1.31-1.23 (m, 6H), 0.93 (s, 9H) |

TABLE 50-continued

| Intermediate | Structure | Chemical Name | MS: [(M + 1)]+ | $^1$H NMR |
|---|---|---|---|---|
| Characterization data for intermediates prepared according to above. | | | | |
| I128 | 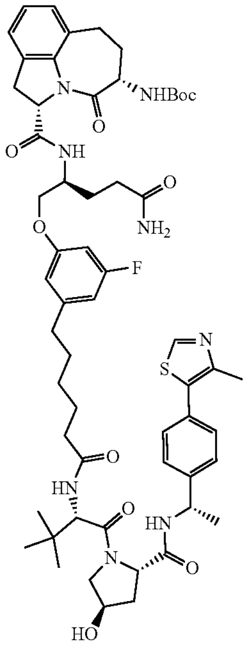 [SMILES: Cc1ncsc1-c1ccc([C@H](C)NC(=O)[C@@H]2C[C@@H](O)CN2C(=O)[C@@H](NC(=O)CCCCCc2cc(F)cc(OC[C@H](CCC(N)=O)NC(=O)[C@@H]3Cc4cccc5c4N3C(=O)[C@@H](NC(=O)OC(C)(C)C)CC5)c2)C(C)(C)C)cc1] | N-[(2S,11S)-2-[[(2S)-4-carbamoyl-1-[3-fluoro-5-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenoxy]butan-2-yl]carbamoyl]-12-oxo-1-azatricyclo[6.4.1.0^[4,13]]trideca-4(13),5,7-trien-11-yl]carbamate | 1095.45 | (400 MHz, DMSO-$d_6$) δ 8.99 (s, 1H), 8.38 (d, J = 7.8 Hz, 1H), 8.05 (d, J = 8.2 Hz, 1H), 7.80 (d, J = 9.3 Hz, 1H), 7.48-7.37 (m, 4H), 7.24 (s, 1H), 7.08 (dd, J = 21.2, 7.8 Hz, 3H), 6.96 (dd, J = 7.9, 6.9 Hz, 1H), 6.74 (s, 1H), 6.65-6.57 (m, 3H), 5.10 (d, J = 3.6 Hz, 1H), 5.05-5.01 (m, 1H), 4.94-4.90 (m, 1H), 4.52 (d, J = 9.3 Hz, 1H), 4.42 (t, J = 8.0 Hz, 1H), 4.28 (s, 1H), 4.07-3.87 (m, 2H), 3.66-3.55 (m, 2H), 3.44-3.40 (m, 1H), 3.07 (s, 2H), 3.05-2.97 (m, 1H), 2.85 (d, J = 16.5 Hz, 1H), 2.54 (s, 1H), 2.46 (s, 3H), 2.28-2.24 (m, 1H), 2.14-2.10 (m, 2H), 2.04-2.00 (m, 4H), 1.85-1.75 (m, 1H), 1.71-1.67 (m, 1H), 1.55 (s, 3H), 1.51-1.47 (m, 1H), 1.40-1.36 (m, 12H), 1.27-1.23 (m, 5H), 0.93 (s, 9H) |
| I129 | 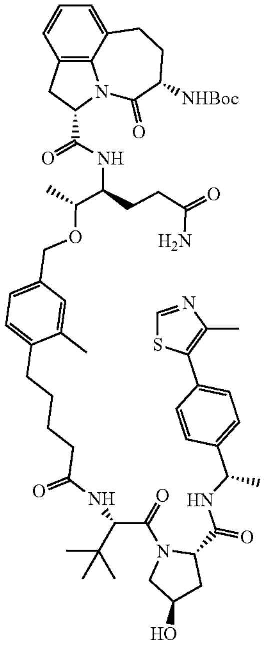 [SMILES: Cc1cc(CO[C@H](C)[C@H](CCC(N)=O)NC(=O)[C@@H]2Cc3cccc4c3N2C(=O)[C@@H](NC(=O)OC(C)(C)C)CC4)ccc1CCCCC(=O)N[C@H](C(=O)N1C[C@H](O)C[C@H]1C(=O)N[C@@H](C)c1ccc(-c2scnc2C)cc1)C(C)(C)C] | tert-butyl N-[(2S,11S)-2-[[(3S,4R)-1-carbamoyl-4-[[4-(4-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]butyl)-3-methylphenyl]methoxy]pentan-3-yl]carbamoyl]-12-oxo-1-azatricyclo[6.4.1.0^[4,13]]trideca-4(13),5,7-trien-11-yl]carbamate | 1105.65 | (300 MHz, DMSO-$d_6$) δ 8.99 (s, 1H), 8.38 (d, J = 7.7 Hz, 1H), 7.83 (d, J = 9.2 Hz, 2H), 7.41 (q, J = 8.2 Hz, 4H), 7.23-6.88 (m, 9H), 6.69 (s, 1H), 5.14-5.00 (m, 2H), 4.92 (t, J = 7.2 Hz, 1H), 4.53 (d, J = 9.3 Hz, 1H), 4.46-4.33 (m, 3H), 4.28 (s, 1H), 4.08-4.01 (m, 1H), 3.77 (s, 1H), 3.64-3.61 (m, 2H), 3.47-3.41 (m, 1H), 3.10-2.95 (m, 2H), 2.84 (d, J = 16.7 Hz, 1H), 2.46 (s, 3 H), 2.35-2.28 (m, 1H), 2.22 (s, 3H), 2.10-1.97 (m, 6H), 1.86-1.70 (m, 2H), 1.61-1.46 (m, 3H), 1.39-1.34 (m, 16H), 1.07 (d, J = 6.2 Hz, 3H), 0.94 (s, 9H) |

TABLE 50-continued

Characterization data for intermediates prepared according to above.

| Inter-mediate | Structure | Chemical Name | MS: [(M + 1)]+ | 1H NMR |
|---|---|---|---|---|
| I130 | 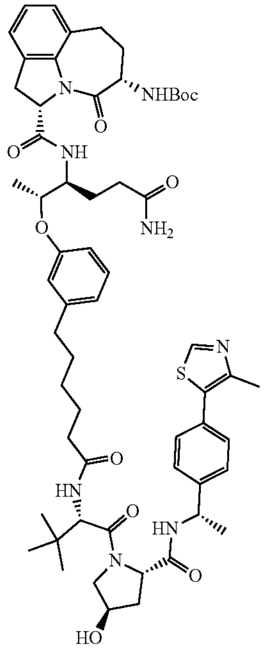 [SMILES: Cc1ncsc1-c1ccc([C@H](C)NC(=O)[C@@H]2C[C@@H](O)CN2C(=O)[C@@H](NC(=O)CCCCCc2cccc(O[C@H](C)[C@H](CCC(N)=O)NC(=O)[C@@H]3Cc4cccc5c4N3C(=O)[C@@H](NC(=O)OC(C)(C)C)CC5)c2)C(C)(C)C)cc1] | tert-butyl N-[(2S,11S)-2-[[(3S,4R)-1-carbamoyl-4-[3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenoxy]pentan-3-yl]carbamoyl]-12-oxo-1-azatricyclo[6.4.1.0^[4,13]]trideca-4(13),5,7-trien-11-yl]carbamate | 1091.85 | (400 MHz, DMSO-$d_6$) δ 8.99 (s, 1H), 8.36 (d, J = 7.8 Hz, 1H), 7.93 (d, J = 9.0 Hz, 1H), 7.79 (d, J = 9.2 Hz, 1H), 7.48-7.36 (m, 4H), 7.24-6.90 (m, 10 H), 6.78-6.63 (m, 4H), 5.15-5.04 (m, 3H), 4.96-4.89 (m, 1H), 4.52 (d, J = 9.3 Hz, 1H), 4.47-4.33 (m, 2H), 4.33-4.25 (m, 1H), 4.14-3.98 (m, 2H), 3.86-3.78 (m, 1H), 3.14-2.99 (m, 5H), 2.46 (s, 3H), 2.17-1.72 (m, 9H), 1.70-1.45 (m, 5H), 1.40 (s, 9H), 1.31-1.20 (m, 2H), 1.18 (d, J = 6.1 Hz, 3H), 0.94 (s, 9H) |
| I131 | 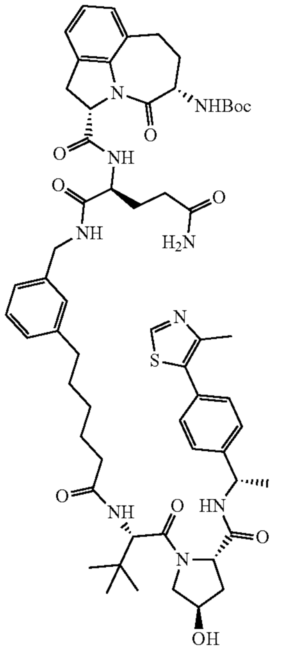 [SMILES: Cc1ncsc1-c1ccc([C@H](C)NC(=O)[C@@H]2C[C@@H](O)CN2C(=O)[C@@H](NC(=O)CCCCCc2cccc(CNC(=O)[C@H](CCC(N)=O)NC(=O)[C@@H]3Cc4cccc5c4N3C(=O)[C@@H](NC(=O)OC(C)(C)C)CC5)c2)C(C)(C)C)cc1] | tert-butyl N-[(2S,11S)-2-[[(1S)-3-carbamoyl-1-([[3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenyl]methyl]carbamoyl)propyl]carbamoyl]-12-oxo-1-azatricyclo[6.4.1.0^[4,13]]trideca-4(13),5,7-trien-11-yl]carbamate | 1104.65 | (400 MHz, Methanol-$d_4$) δ 8.89 (s, 1 H), 7.48-7.41 (m, 4H), 7.20 (t, J = 7.5 Hz, 1H), 7.15-7.06 (m, 6H), 7.04-6.99 (m, 1H),5.18 (dd, J = 10.8, 3.4 Hz, 1H), 5.02 (q, J = 6.9 Hz, 1H), 4.66-4.64 (m, 1H), 4.61-4.56 (m, 1H), 4.46-4.40 (m, 2H), 4.38 (d, J = 2.0 Hz, 2H), 4.25 (d, J = 8.6 Hz, 1H), 3.89 (d, J = 11.1 Hz, 1H), 3.76 (dd, J = 11.0, 3.9 Hz, 1H), 3.54-3.46 (m, 1H), 3.18 (t, J = 6.3 Hz, 2H), 3.10 (dd, J = 16.8, 3.4 Hz, 1H), 2.58 (t, J = 7.5 Hz, 2H), 2.50 (s, 3H), 2.32 (t, J = 7.5 Hz, 2H), 2.29-2.18 (m, 5H), 2.01-1.93 (m, 2H), 1.65-1.53 (m, 4H), 1.52 (d, J = 7.0 Hz, 3H), 1.47 (s, 9H), 1.31 (t, J = 7.7 Hz, 2H), 1.04 (s, 9H) |

TABLE 50-continued

Characterization data for intermediates prepared according to above.

| Intermediate | Structure | Chemical Name | MS: [(M + 1)]$^+$ | $^1$H NMR |
|---|---|---|---|---|
| I132 | 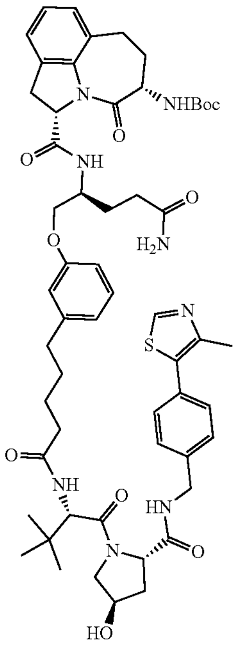 [SMILES: Cc1ncsc1-c1ccc(CNC(=O)[C@@H]2C[C@@H](O)CN2C(=O)[C@@H](NC(=O)CCCCc2cccc(OC[C@H](CCC(N)=O)NC(=O)[C@@H]3Cc4cccc5c4N3C(=O)[C@@H](NC(=O)OC(C)(C)C)CC5)c2)C(C)(C)C)cc1] | tert-butyl N-[(2S,11S)-2-[[(2S)-4-carbamoyl-1-[3-(4-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]butyl)phenoxy]butan-2-yl]carbamoyl]-12-oxo-1-azatricyclo[6.4.1.0^[4,13]]trideca-4(13),5,7-trien-11-yl]carbamate | 1049.55 | (400 MHz, DMSO-$d_6$) δ 8.99 (s, 1H), 8.57 (t, J = 6.1 Hz, 1H), 8.05 (d, J = 8.3 Hz, 1H), 7.88 (d, J = 9.3 Hz, 1H), 7.41 (q, J = 8.3 Hz, 4H), 7.24 (s, 1H), 7.17 (dd, J = 8.9, 7.5 Hz, 1H), 7.11 (d, J = 8.1 Hz, 1H), 7.07-7.03 (m, 2H), 6.99-6.92 (m, 1H), 6.79-6.69 (m, 5H), 5.13 (d, J = 3.5 Hz, 1H), 5.03 (dd, J = 10.7, 2.8 Hz, 1H), 4.55 (d, J = 9.4 Hz, 1H), 4.48-4.39 (m, 2H), 4.35 (s, 1H), 4.22 (dd, J = 15.8, 5.4 Hz, 1H), 4.07-3.93 (m, 1H), 3.92-3.85 (m, 2H), 3.69-3.64 (m, 2H), 3.45-3.38 (m, 2H), 3.15-2.96 (m, 2H), 2.85 (d, J = 16.5 Hz, 1H), 2.57-2.53 (m, 2H), 2.45 (s, 3H), 2.36-2.26 (m, 1H), 2.20-1.98 (m, 6H), 1.95-1.76 (m, 1H), 1.76-1.63 (m, 1H), 1.59-1.47 (m, 4H), 1.39 (s, 9H), 0.94 (s, 9H) |
| I133 | 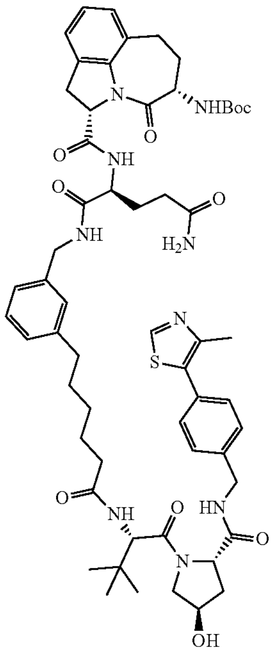 [SMILES: Cc1ncsc1-c1ccc(CNC(=O)[C@@H]2C[C@@H](O)CN2C(=O)[C@@H](NC(=O)CCCCCc2cccc(CNC(=O)[C@H](CCC(N)=O)NC(=O)[C@@H]3Cc4cccc5c4N3C(=O)[C@@H](NC(=O)OC(C)(C)C)CC5)c2)C(C)(C)C)cc1] | tert-butyl N-[(2S,11S)-2-[[(1S)-3-carbamoyl-1-([[3-(5-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]pentyl)phenyl]methyl]carbamoyl)propyl]carbamoyl]-12-oxo-1-azatricyclo[6.4.1.0^[4,13]]trideca-4(13),5,7-trien-11-yl]carbamate | 1090.65 | (400 MHz, Methanol-$d_4$) δ 8.89 (s, 1H), 7.53-7.39 (m, 5H), 7.19 (t, J = 7.6 Hz, 1H), 7.12-7.03 (m, 4H), 7.01 (t, J = 7.4 Hz, 1H), 5.17 (dd, J = 10.9, 3.4 Hz, 1H), 4.65 (s, 1H), 4.63-4.55 (m, 2H), 4.54-4.50 (m, 2H), 4.45-4.38 (m, 2H), 4.36 (d, J = 3.3 Hz, 2H), 4.25 (d, J = 8.9 Hz, 1H), 3.92 (d, J = 11.0 Hz, 1H), 3.82-3.80 (m, 1H), 3.51-.378 (m, 1H), 3.25-3.05 (m, 2H), 2.58-2.53 (m, 2H), 2.49 (s, 3H), 2.40-2.17 (m, 7H), 2.17-2.04 (m, 2H), 1.97-1.75 (m, 1H), 1.63-1.58 (m, 4H), 1.47 (s, 9H), 1.39-1.24 (m, 2H), 1.04 (s, 9H). |

TABLE 50-continued

Characterization data for intermediates prepared according to above.

| Inter-mediate | Structure | Chemical Name | MS: [(M + 1)]+ | $^1H$ NMR |
|---|---|---|---|---|
| I134 | 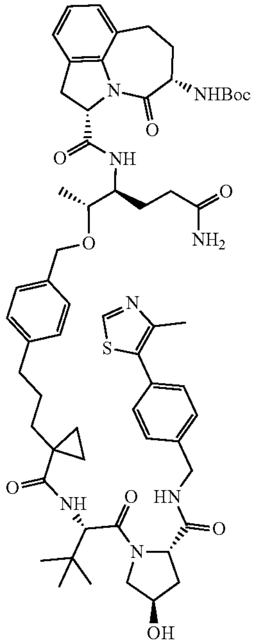 [SMILES: Cc1ncsc1-c1ccc(CNC(=O)[C@@H]2C[C@@H](O)CN2C(=O)[C@@H](NC(=O)C2(CCCc3ccc(CO[C@H](C)[C@H](CCC(N)=O)NC(=O)[C@@H]4Cc5cccc6c5N4C(=O)[C@@H](NC(=O)OC(C)(C)C)CC6)cc3)CC2)C(C)(C)C)cc1] | tert-butyl N-[(2S,11S)-2-[[(3S,4R)-1-carbamoyl-4-([4-[3-(1-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]cyclopropyl)propyl]phenyl]methoxy)pentan-3-yl]carbamoyl]-12-oxo-1-azatricyclo[6.4.1.0^[4,13]]trideca-4(13),5,7-trien-11-yl]carbamate | 1103.50 | (400 MHz, Methanol-$d_4$) δ 8.90 (s, 1H), 7.53-7.40 (m, 4H), 7.23 (d, J = 7.9 Hz, 2H), 7.16 (d, J = 8.0 Hz, 2H), 7.07 (dd, J = 12.3, 7.2 Hz, 1H), 7.05-6.99 (m, 1H), 6.94 (d, J = 9.3 Hz, 1H), 5.12 (dd, J = 10.9, 3.4 Hz, 1H), 4.72 (d, J = 9.2 Hz, 1H), 4.64-4.55 (m, 2H), 4.51 (s, 1H), 4.48 (d, J = 3.7 Hz, 2H), 4.35 (d, J = 15.5 Hz, 1H), 4.25 (d, J = 8.7 Hz, 1H), 3.99 (s, 1H), 3.87 (d, J = 11.2 Hz, 1H), 3.81 (dd, J = 11.1, 3.8 Hz, 1H), 3.59-3.52 (m, 1H), 3.50-3.41 (m, 1H), 3.13 (dd, J = 23.3, 17.8 Hz, 1H), 3.05-2.92 (m, 1H), 2.66 (t, J = 7.2 Hz, 2H), 2.48 (s, 3H), 2.33-2.16 (m, 4H), 2.09 (ddt, J = 13.8, 9.1, 4.5 Hz, 1H), 1.99 (s, 1H), 1.84-1.77 (m, 3H), 1.75-1.64 (m, 1H), 1.52-1.49 (m, 3H), 1.48 (s, 9H), 1.31 (s, 1H), 1.21-1.09 (m, 4H), 1.03 (s, 9H), 0.65 (d, J = 2.2 Hz, 2H) |
| I135 | 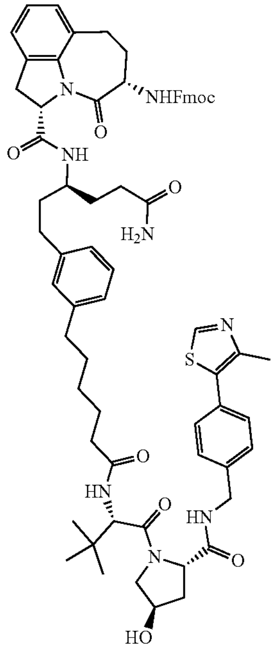 | 9H-fluoren-9-ylmethyl N-[(2S,11S)-2-[[(3R)-1-carbamoyl-5-[3-(5-[[(2S)-1-[(2S,4R)-4-hydroxy-2-([[4-(3-methylthiophen-2-yl)phenyl]methyl]carbamoyl)pyrrolidin-1-yl]-3,3-dimethyl-1-oxobutan-2-yl]carbamoyl]pentyl)phenyl]pentan-3-yl]carbamoyl]-12-oxo-1-azatricyclo[6.4.1.0^[4,13]]trideca-4(13),5,7-trien-11-yl]carbamate | 1183.45 | (400 MHz, DMSO-$d_6$) δ 8.98 (d, J = 0.9 Hz, 1H), 8.57 (t, J = 6.1 Hz, 1H), 7.93-7.86 (m, 3H), 7.84 (s, 1H), 7.75 (q, J = 9.0, 8.3 Hz, 3H), 7.45-7.38 (m, 6H), 7.37-7.28 (m, 2H), 7.22 (d, J = 18.8 Hz, 1H), 7.13 (q, J = 7.5, 7.0 Hz, 2H), 7.06 (d, J = 7.9 Hz, 1H), 6.97 (d, J = 8.0 Hz, 4H), 6.71 (s, 1H), 5.06-4.99 (m, 1H), 4.55 (d, J = 9.3 Hz, 1H), 4.48-4.40 (m, 2H), 4.36 (s, 1H), 4.31-4.09 (m, 5H), 3.70-3.62 (m, 3H), 3.55-3.44 (m, 3H), 3.17-2.86 (m, 3H), 2.57 (d, J = 25.3 Hz, 1H), 2.47 (d, J = 7.7 Hz, 2H), 2.45 (s, 3H), 2.33-2.21 (m, 1H), 2.12 (d, J = 9.5 Hz, 3H), 2.05 (d, J = 6.7 Hz, 3H), 1.97-1.85 (m, 1H), 1.64 (d, J = 17.5 Hz, 3H), 1.60-1.44 (m, 5H), 1.32-1.21 (m, 2H), 0.94 (s, 9H) |

TABLE 50-continued

Characterization data for intermediates prepared according to above.

| Intermediate | Structure | Chemical Name | MS: [(M + 1)]+ | $^1$H NMR |
|---|---|---|---|---|
| I136 | 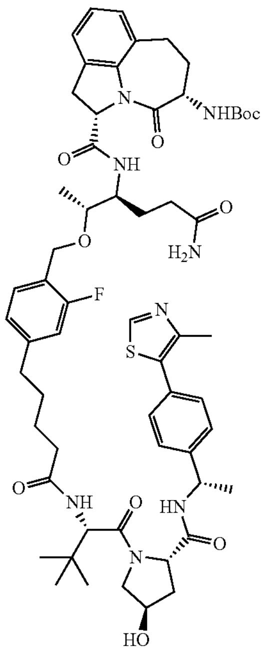 [SMILES: Cc1ncsc1-c1ccc([C@H](C)NC(=O)[C@@H]2C[C@@H](O)CN2C(=O)[C@@H](NC(=O)CCCCc2ccc(CO[C@H](C)[C@H](CCC(N)=O)NC(=O)[C@@H]3Cc4cccc5c4N3C(=O)[C@@H](NC(=O)OC(C)(C)C)CC5)c(F)c2)C(C)(C)C)cc1] | tert-butyl N-[(2S,11S)-2-[[(3S,4R)-1-carbamoyl-4-[[2-fluoro-4-(4-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]butyl)phenyl]methoxy]pentan-3-yl]carbamoyl]-12-oxo-1-azatricyclo[6.4.1.0^[4,13]]trideca-4(13),5,7-trien-11-yl]carbamate | 1109.65 | Crude used next step without further purification |
| I137 | 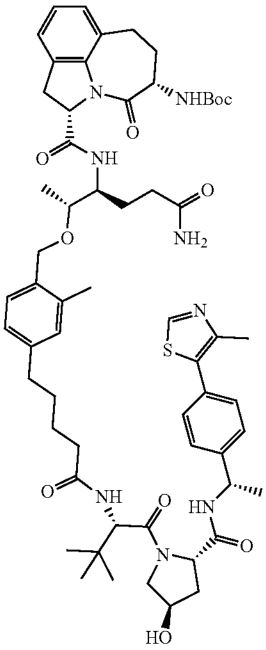 [SMILES: Cc1cc(CCCCC(=O)N[C@H](C(=O)N2C[C@H](O)C[C@H]2C(=O)N[C@@H](C)c2ccc(-c3scnc3C)cc2)C(C)(C)C)ccc1CO[C@H](C)[C@H](CCC(N)=O)NC(=O)[C@@H]1Cc2cccc3c2N1C(=O)[C@@H](NC(=O)OC(C)(C)C)CC3] | tert-butyl N-[(2S,11S)-2-[[(3S,4R)-1-carbamoyl-4-[[4-(4-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]butyl)-2-methylphenyl]methoxy]pentan-3-yl]carbamoyl]-12-oxo-1-azatricyclo[6.4.1.0^[4,13]]trideca-4(13),5,7-trien-11-yl]carbamate | 1105.45 | (400 MHz, Methanol-$d_4$) δ 8.89 (s, 1H), 7.48-7.41 (m, 4H), 7.17 (d, J = 7.6 Hz, 1H), 7.08 (t, J = 7.4 Hz, 1H), 7.05-7.01 (m, 3H), 6.95 (d, J = 8.1 Hz, 1H), 5.12 (dd, J = 10.9, 3.4 Hz, 1H), 5.02 (q, J = 7.0 Hz, 1H), 4.65-4.62 (m, 1H), 4.61-4.53 (m, 2H), 4.49-4.43 (m, 2H), 4.28-4.21 (m, 1H), 4.05-3.95 (m, 1H), 3.89 (d, J = 11.1 Hz, 1H), 3.76 (dd, J = 10.9, 4.0 Hz, 1H), 3.59 (dd, J = 6.3, 4.6 Hz, 1H), 3.47 (dd, J = 16.7, 11.0 Hz, 1H), 3.18-3.11 (m, 2H), 3.02 (dd, J = 16.6, 3.4 Hz, 1H), 2.62-2.58 (m, 2H), 2.50 (s, 3H), 2.33-2.30 (m, 4H), 2.28 (td, J = 5.3, 3.4 Hz, 3H), 2.25-2.16 (m, 3H), 2.00-1.97 (m, 2H), 1.70-1.65 (m, 4H), 1.52 (d, J = 7.0 Hz, 3H), 1.48 (s, 9H), 1.21 (d, J = 6.4 Hz, 3H), 1.05 (s, 9H) |

TABLE 50-continued

| Characterization data for intermediates prepared according to above. | | | | |
|---|---|---|---|---|
| Inter-mediate | Structure | Chemical Name | MS: [(M + 1)]+ | $^1$H NMR |
| I138 | 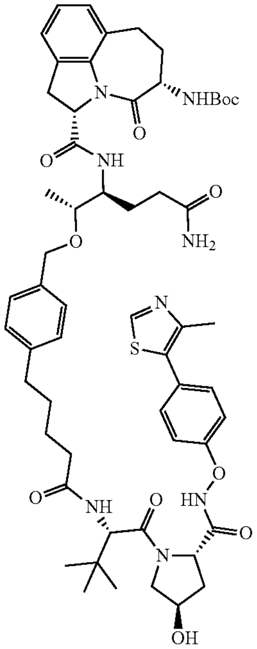 [SMILES: Cc1ncsc1-c1ccc(ONC(=O)[C@@H]2C[C@@H](O)CN2C(=O)[C@@H](NC(=O)CCCCc2ccc(CO[C@H](C)[C@H](CCC(N)=O)NC(=O)[C@@H]3Cc4cccc5c4N3C(=O)[C@@H](NC(=O)OC(C)(C)C)CC5)cc2)C(C)(C)C)cc1] | tert-butyl N-[(2S,11S)-2-[[(3S,4R)-1-carbamoyl-4-[[4-(4-[[(2S)-1-[(2S,4R)-4-hydroxy-2-[[4-(4-methyl-1,3-thiazol-5-yl)phenoxy]carbamoyl]pyrrolidin-1-yl]-3,3-dimethyl-1-oxobutan-2-yl]carbamoyl]butyl)phenyl]methoxy]pentan-3-yl]carbamoyl]-12-oxo-1-azatricyclo[6.4.1.0^[4,13]]trideca-4(13),5,7-trien-11-yl]carbamate | 1079.53 | (400 MHz, Methanol-d$_4$) δ 8.89 (s, 1H), 7.41 (d, J = 8.5 Hz, 2H), 7.34 (d, J = 8.5 Hz, 2H), 7.24 (d, J = 7.7 Hz, 2H), 7.15 (d, J = 7.8 Hz, 2H), 7.12-6.99 (m, 3H), 5.13 (dd, J = 10.9, 3.4 Hz, 1H), 4.65 (s, 1H), 4.55 (d, J = 10.2 Hz, 2H), 4.50 (d, J = 4.5 Hz, 2H), 4.25 (dd, J = 8.3, 3.5 Hz, 1H), 4.03-3.92 (m, 2H), 3.83 (dd, J = 11.0, 3.7 Hz, 1H), 3.60-3.54 (m, 1H), 3.51-3.43 (m, 1H), 3.16 (d, J = 22.1 Hz, 2H), 3.01 (dd, J = 16.6, 3.4 Hz, 1H), 2.65 (s, 2H), 2.47 (s, 3H), 2.39-2.24 (m, 5H), 2.24-2.14 (m, 3H), 2.02 (dd, J = 13.8, 7.8 Hz, 1H), 1.67 (s, 4H), 1.48 (s, 9H), 1.31 (d, J = 5.5 Hz, 1H), 1.19 (d, J = 6.3 Hz, 3H), 1.05 (s, 9H) |
| I139 | 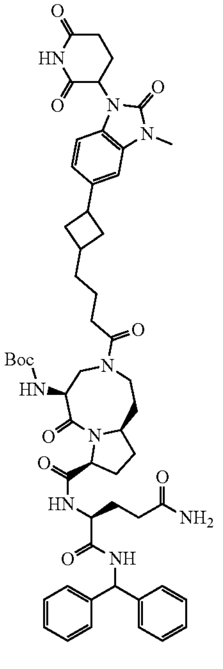 [SMILES: Cn1c(=O)n(C2CCC(=O)NC2=O)c2ccc(C3CC(CCCC(=O)N4CC[C@H]5CC[C@@H](C(=O)N[C@@H](CCC(N)=O)C(=O)NC(c6ccccc6)c6ccccc6)N5C(=O)[C@@H](NC(=O)OC(C)(C)C)C4)C3)cc21] | tert-butyl N-[(5S,8S,10aR)-8-[[(1S)-3-carbamoyl-1-(diphenylmethyl carbamoyl) propyl]carbamoyl]-3-(4-[3-[1-(2,6-dioxopiperidin-3-yl)-3-methyl-2-oxo-1,3-benzodiazol-5-yl]cyclobutyl]butanoyl)-6-oxo-octahydropyrrolo[1,2-a][1,5]diazocin-5-yl]carbamate | 1002.40 | (400 MHz, DMSO-d$_6$) δ 11.07 (s, 1H), 8.71 (d, J = 8.5 Hz, 1H), 8.18 (d, J = 7.8 Hz, 1H), 7.41-7.18 (m, 11H), 7.11-7.07 (m, 1H), 7.07-6.98 (m, 2H), 6.97-6.90 (m, 1H), 6.87 (d, J = 8.2 Hz, 1H), 6.72 (d, J = 16.8 Hz, 1H), 6.49 (d, J = 6.3 Hz, 1H), 6.10 (d, J = 8.4 Hz, 1H), 5.39-5.30 (m, 1H), 4.45-4.35 (m, 2H), 4.12-3.98 (m, 1H), 3.74-3.72 (m, 1H), 3.37-3.34 (m, 3H), 3.33-3.28 (m, 3 H), 3.17-2.99 (m, 1H), 2.97-2.85 (m, 1H), 2.78-2.58 (m, 3H), 2.46-2.43 (m, 2H), 2.39-2.18 (m, 3H), 2.17-1.87 (m, 6H), 1.85-1.42 (m, 8H), 1.42-1.33 (m, 10H). |

TABLE 50-continued

| Characterization data for intermediates prepared according to above. | | | | |
|---|---|---|---|---|
| Intermediate | Structure | Chemical Name | MS: $[(M+1)]^+$ | $^1H$ NMR |
| I140 | 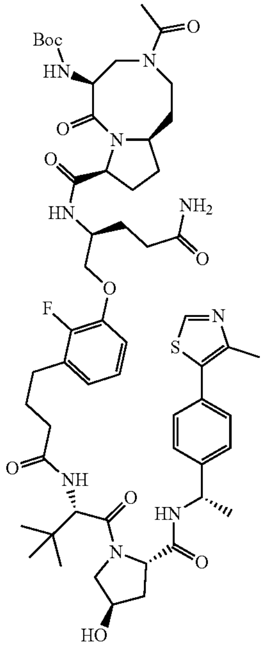 [SMILES: CC(=O)N1CC[C@H]2CC[C@@H](C(=O)N[C@@H](CCC(N)=O)COc3cccc(CCCC(=O)N[C@H](C(=O)N4C[C@H](O)C[C@H]4C(=O)N[C@@H](C)c4ccc(-c5scnc5C)cc4)C(C)(C)C)c3F)N2C(=O)[C@@H](NC(=O)OC(C)(C)C)C1] | tert-butyl N-[(5S,8S,10aR)-3-acetyl-8-[[(2S)-4-carbamoyl-1-[2-fluoro-3-(3-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]propyl)phenoxy]butan-2-yl]carbamoyl]-6-oxo-octahydropyrrolo[1,2-a][1,5]diazocin-5-yl]carbamate | 1090.55 | (400 MHz, $CD_3OD$) δ 8.92-8.89 (m, 1H), 7.46-7.44 (m, 4H), 7.04-6.92 (m, 2H), 6.86-6.81 (m, 1H), 5.03-5.01 (m, 1H), 4.67-4.64 (m, 1H), 4.61-4.55 (m, 1H), 4.46-4.39 (m, 2H), 4.28-4.24 (m, 2H), 4.07-4.05 (m, 1H), 4.01-3.95 (m, 1H), 3.90 (d, J = 10.8 Hz, 1H), 3.84-3.74 (m, 2H), 3.71-3.68 (m, 1H), 3.60-3.50 (m, 2H), 2.69-2.67 (m, 2H), 2.45-4.42 (m, 2H), 2.36-4.32 (m, 3H), 2.26-2.17 (m, 6H), 2.12-2.06 (m, 3H), 2.02-1.84 (m, 7H), 1.82-1.79 (m, 2H), 1.53 (d, J = 7.0 Hz, 3H), 1.46 (s, 9H), 1.07 (s, 9H) |
| I141 | 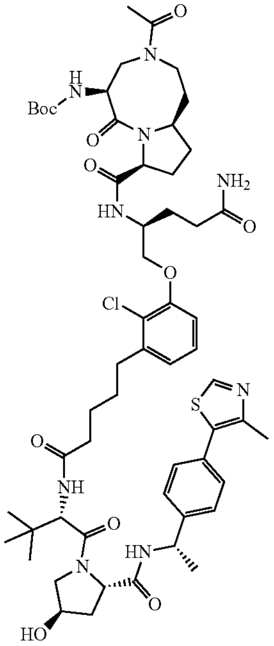 [SMILES: CC(=O)N1CC[C@H]2CC[C@@H](C(=O)N[C@@H](CCC(N)=O)COc3cccc(CCCCC(=O)N[C@H](C(=O)N4C[C@H](O)C[C@H]4C(=O)N[C@@H](C)c4ccc(-c5scnc5C)cc4)C(C)(C)C)c3Cl)N2C(=O)[C@@H](NC(=O)OC(C)(C)C)C1] | tert-butyl N-[(5S,8S,10aR)-3-acetyl-8-[[(2S)-4-carbamoyl-1-[2-chloro-3-(4-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]butyl)phenoxy]butan-2-yl]carbamoyl]-6-oxo-octahydropyrrolo[1,2-a][1,5]diazocin-5-yl]carbamate | 1120.45 | (400 MHz, DMSO-$d_6$) δ 9.00 (s, 1H), 8.39 (d, J = 7.8 Hz, 1H), 8.01 (dd, J = 8.4, 4.2 Hz, 1H), 7.84 (d, J = 9.3 Hz, 1H), 7.48-7.30 (m, 4H), 7.24-7.15 (m, 2H), 7.01-6.97 (m, 1H), 6.91 (d, J = 7.6 Hz, 1H), 6.75 (s, 1H), 6.68-6.58 (m, 1H), 5.11 (d, J = 3.5 Hz, 1H), 4.93 (p, J = 7.1 Hz, 1H), 4.56-4.37 (m, 3H), 4.37-4.27 (m, 2H), 4.20 (d, J = 23.5 Hz, 2H), 4.07 (s, 1H), 4.03-3.09 (m, 1H), 3.93-3.87 (m, 1H), 3.70-3.56 (m, 4H), 3.32 (s, 1H), 3.21-3.17 (m, 1H), 2.71-2.67 (m, 2H), 2.47 (s, 3H), 2.36-2.27 (m, 1H), 2.25-2.11 (m, 3H), 2.08 (d, J = 1.9 Hz, 3H), 2.07-1.95 (m, 2H), 1.91-1.74 (m, 2H), 1.74-1.62 (m, 2H), 1.57-1.43 (m, 4H), 1.40 (s, 9H), 1.38 (s, 3H), 1.33-1.22 (m, 2H), 1.19-1.07 (m, 1H), 0.94 (s, 9H) |

TABLE 50-continued

| Characterization data for intermediates prepared according to above. | | | | |
|---|---|---|---|---|
| Inter-mediate | Structure | Chemical Name | MS: [(M + 1)]$^+$ | $^1$H NMR |
| I142 | 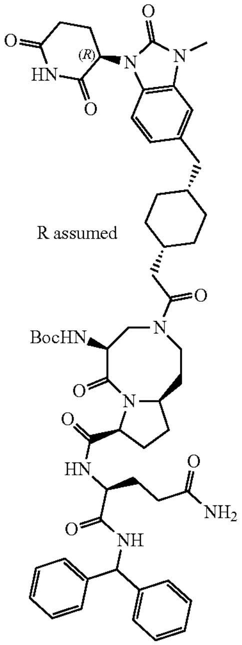 R assumed | tert-butyl N-[(5S,8S,10aR)-8-[[(1S)-3-carbamoyl-1-(diphenylmethyl carbamoyl) propyl]carbamoyl]-6-oxo-3-[2-[(1s,4s)-4-[[1-(2,6-dioxopiperidin-3-yl)-3-methyl-2-oxo-1,3-benzodiazol-5-yl]methyl]cyclohexyl] acetyl]-octahydropyrrolo[1,2-a][1,5]diazocin-5-yl]carbamate | 1016.50 | (400 MHz,DMSO-$d_6$) δ 11.09 (s, 1H), 8.74 (d, J = 8.3 Hz, 1H), 8.29-8.14 (m, 1H), 7.43-7.16 (m, 11H), 7.06-6.92 (m, 2H), 6.89-6.68 (m, 2H), 6.47 (d, J = 6.7 Hz, 1H), 6.10 (d, J = 8.4 Hz, 1H), 5.34 (dd, J = 12.7, 5.4 Hz, 1H), 4.49-4.22 (m, 3H), 4.14-3.97 (m, 6H), 3.83-3.75 (m, 1H), 3.32 (s, 3H), 3.21-3.05 (m, 1H), 2.95-2.86 (m, 1H), 2.78-2.55 (m, 5H), 2.47-2.26 (m, 1H), 2.20-2.08 (m, 5H), 2.04-1.87 (m, 1H), 1.87-1.51 (m, 4H), 1.46 (s, 9H), 1.43-1.30 (m, 8H) |
| I143 | 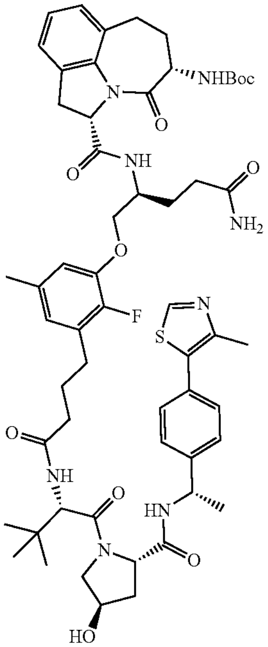 [SMILES: Cc1cc(CCCC(=O)N[C@H](C(=O)N2C[C@H](O)C[C@H]2C(=O)N[C@@H](C)c2ccc(-c3scnc3C)cc2)C(C)(C)C)c(F)c(OC[C@H](CCC(N)=O)NC(=O)[C@@H]2Cc3cccc4c3N2C(=O)[C@@H](NC(=O)OC(C)(C)C)CC4)c1] | tert-butyl N-[(2S,11S)-2-[[(2S)-4-carbamoyl-1-[2-fluoro-3-(3-[[(2S)-1-[(2S,4R)-4-hydroxy-2-[[(1S)-1-[4-(4-methyl-1,3-thiazol-5-yl)phenyl]ethyl] carbamoyl] pyrrolidin-1-yl]-3,3-dimethyl-1-oxobutan-2-yl]carbamoyl]propyl)-5-methylphenoxy]butan-2-yl]carbamoyl]-12-oxo-1-azatricyclo[6.4.1.0^[4,13]] trideca-4(13),5,7-trien-11-yl]carbamate | 1081.50 | (300 MHz, DMSO-$d_6$) δ 8.97 (s, 1H), 8.35 (d, J = 7.8 Hz, 1H), 8.05 (d, J = 7.4 Hz, 1H), 7.85 (d, J = 9.2 Hz, 1H), 7.40 (q, J = 8.4 Hz, 4H), 7.25 (s, 1H), 7.11-6.99 (m, 3H), 6.94 (dd, J = 8.4, 6.3 Hz, 1H), 6.80 (d, J = 7.7 Hz, 1H), 6.72 (s, 1H), 6.64-6.56 (m, 1H), 5.15-4.98 (m, 2H), 4.91 (t, J = 7.2 Hz, 1H), 4.53 (d, J = 9.3 Hz, 1H), 4.42 (t, J = 8.0 Hz, 1H), 4.32-4.25 (m, 1H), 4.09-3.86 (m, 4H), 3.65-3.58 (m, 2H), 3.49-3.37 (m, 2H), 3.17-2.93 (m, 3H), 2.85 (d, J = 16.6 Hz, 1H), 2.59-2.51 (m, 1H), 2.45 (s, 3H), 2.22 (s, 3H), 2.20-2.09 (m, 4H), 2.05-1.96 (m, 2H), 1.87-1.60 (m, 5H), 1.38 (s, 9H), 1.35 (s, 3H), 0.94 (s, 9H) |

TABLE 50-continued

| Characterization data for intermediates prepared according to above. | | | | |
|---|---|---|---|---|
| Inter-mediate | Structure | Chemical Name | MS: [(M + 1)]$^+$ | $^1$H NMR |
| I144 | 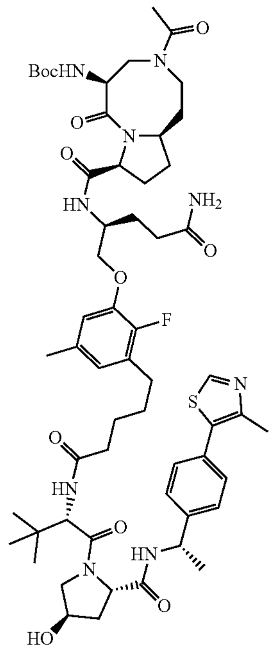 [SMILES: CC(=O)N1CC[C@H]2CC[C@@H](C(=O)N[C@@H](CCC(N)=O)COc3cc(C)cc(CCCCC(=O)N[C@H](C(=O)N4C[C@H](O)C[C@H]4C(=O)N[C@@H](C)c4ccc(-c5scnc5C)cc4)C(C)(C)C)c3F)N2C(=O)[C@@H](NC(=O)OC(C)(C)C)C1] | tert-butyl N-[(5S,8S,10aR)-3-acetyl-8-[[(2S)-4-carbamoyl-1-[2-fluoro-3-(4-[[(2S)-1-[(2S,4R)-4-hydroxy-2-[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]butyl)-5-methylphenoxy]butan-2-yl]carbamoyl]-6-oxo-octahydropyrrolo[1,2-a][1,5]diazocin-5-yl]carbamate | 1118.60 | (300 MHz, DMSO-$d_6$) δ 8.97 (s, 1H), 8.35 (d, J = 7.8 Hz, 1H), 8.04-7.93 (m, 1H), 7.80 (d, J = 9.3 Hz, 1H), 7.40 (q, J = 8.4 Hz, 4H), 7.17 (s, 1H), 6.80 (d, J = 7.8 Hz, 1H), 6.72 (s, 1H), 6.58 (dd, J = 10.9, 6.5 Hz, 2H), 5.08 (s, 1H), 4.91 (p, J = 7.2 Hz, 1H), 4.55-4.36 (m, 3H), 4.35-4.24 (m, 2H), 4.21-4.09 (m, 1H), 4.07-3.80 (m, 4H), 3.72-3.51 (m, 4H), 3.37-3.26 (m, 4H), 2.45 (s, 3H), 2.34-2.25 (m, 1H), 2.22 (s, 3H), 2.20-2.09 (m, 4H), 2.04-1.91 (m, 3H), 1.90-1.75 (m, 4H), 1.74-1.56 (m, 4H), 1.55-1.45 (m, 4H), 1.37 (s, 9H), 1.35 (s, 3H), 0.92 (s, 9H) |
| I145 | 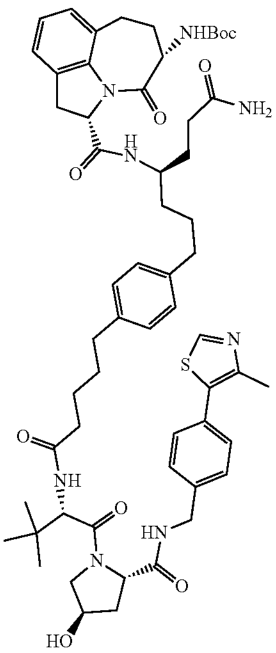 [SMILES: Cc1ncsc1-c1ccc(CNC(=O)[C@@H]2C[C@@H](O)CN2C(=O)[C@@H](NC(=O)CCCCc2ccc(CCC[C@H](CCC(N)=O)NC(=O)[C@@H]3Cc4cccc5c4N3C(=O)[C@@H](NC(=O)OC(C)(C)C)CC5)cc2)C(C)(C)C)cc1] | tert-butyl N-[(2S,11S)-2-[[(3R)-1-carbamoyl-6-[4-(4-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]butyl)phenyl]hexan-3-yl]carbamoyl]-12-oxo-1-azatricyclo[6.4.1.0^[4,13]]trideca-4(13),5,7-trien-11-yl]carbamate | 1075.60 | (400 MHz, DMSO-$d_6$) δ 9.00 (s, 1H), 8.39 (d, J = 8.0 Hz, 1H), 7.91-7.67 (m, 2H), 7.49-7.29 (m, 4H), 7.13-7.00 (m, 9H), 6.69 (s, 1H), 5.11 (d, J = 3.6 Hz, 1H), 5.03-4.81 (m, 2H), 4.58-4.35 (m, 2H), 4.28 (s, 1H), 4.03 (s, 1H), 3.73-3.56 (m, 3H), 3.53-3.37 (m, 3H), 3.15-2.78 (m, 1H), 2.46 (s, 3H), 2.36-2.25 (m, 1H), 2.20-1.91 (m, 6H), 1.86-1.72 (m, 1H), 1.67-1.29 (m, 17H), 1.39 (s, 9H), 0.94 (s, 9H) |

TABLE 50-continued

| Characterization data for intermediates prepared according to above. | | | | |
|---|---|---|---|---|
| Inter-mediate | Structure | Chemical Name | MS: [(M + 1)]+ | $^1$H NMR |
| I146 | 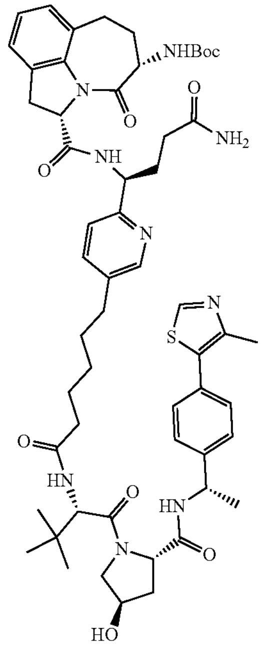 [SMILES: Cc1ncsc1-c1ccc([C@H](C)NC(=O)[C@@H]2C[C@@H](O)CN2C(=O)[C@@H](NC(=O)CCCCCc2ccc([C@H](CCC(N)=O)NC(=O)[C@@H]3Cc4cccc5c4N3C(=O)[C@@H](NC(=O)OC(C)(C)C)CC5)nc2)C(C)(C)C)cc1] | tert-butyl N-[(2S,11S)-2-[[(1S)-3-carbamoyl-1-[5-(5-[[(2S)-1-[(2S,4R)-4-hydroxy-2-[[(1S)-1-[4-(4-methyl-1,3-thiazol-5-yl)phenyl]ethyl] carbamoyl] pyrrolidin-1-yl]-3,3-dimethyl-1-oxobutan-2-yl]carbamoyl]pentyl) pyridin-2-yl]propyl]carbamoyl]-12-oxo-1-azatricyclo[6.4.1.0^[4,13]] trideca-4(13),5,7-trien-11-yl]carbamate | 1048.60 | (300 MHz, DMSO-$d_6$) δ 9.00 (s, 1H), 8.66-8.59 (d, J = 7.9 Hz, 1H), 8.42-8.33 (m, 2H), 7.81-7.79 (d, J = 9.3 Hz, 1H), 7.59-7.56 (dd, J = 8.0, 2.4 Hz, 1H), 7.46-7.44 (d, J = 8.3 Hz, 2H), 7.40-7.36 (d, J = 8.2 Hz, 2H), 7.26-7.18 (m, 2H), 7.14-7.12 (d, J = 8.0 Hz, 1H), 7.06-7.02 (t, J = 7.5 Hz, 2H), 6.95-6.91 (t, J = 7.5 Hz, 1H), 6.76 (s, 1H), 5.12-5.11 (d, J = 3.5 Hz, 1H), 5.08-5.06 (dd, J = 10.8, 2.8 Hz, 1H), 4.96-4.89 (m, 1H), 4.72-4.66 (m, 1H), 4.53-4.48 (d, J = 9.3 Hz, 1H), 4.45-4.41 (t, J = 8.0 Hz, 1H), 4.29 (s, 1H), 4.07-4.03 (m, 1H), 3.62-3.61 (d, J = 3.9 Hz, 2H), 3.48-3.41 (m, 1H), 3.11-2.99 (m, 2H), 2.77-2.69 (m, 1H), 2.71-2.65 (m, 2H), 2.47 (s, 3H), 2.29-2.22 (m, 1H), 2.18-2.03 (m, 3H), 2.06-1.98 (m, 1H), 1.98-1.85 (m, 1H), 1.83-1.77 (m, 1H), 1.66-1.61 (m, 2H), 1.55-1.47 (m, 2H), 1.40-1.38 (m, 12H), 1.32-1.25 (m, 2H), 0.94 (s, 9H) |
| I147 | 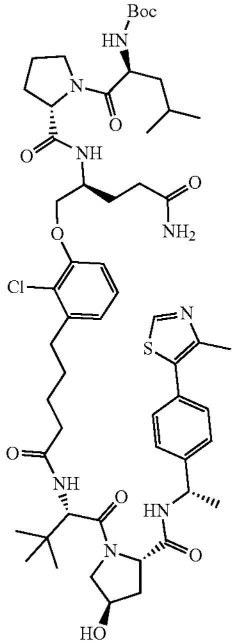 [SMILES: Cc1ncsc1-c1ccc([C@H](C)NC(=O)[C@@H]2C[C@@H](O)CN2C(=O)[C@@H](NC(=O)CCCCc2cccc(OC[C@H](CCC(N)=O)NC(=O)[C@@H]3CCCN3C(=O)[C@H](CC(C)C)NC(=O)OC(C)(C)C)c2Cl)C(C)(C)C)cc1] | tert-butyl N-[(2S)-1-[(2S)-2-[[(2S)-4-carbamoyl-1-[2-chloro-3-(4-[[(2S)-1-[(2S,4R)-4-hydroxy-2-[[(1S)-1-[4-(4-methyl-1,3-thiazol-5-yl)phenyl]ethyl] carbamoyl] pyrrolidin-1-yl]-3,3-dimethyl-1-oxobutan-2-yl]carbamoyl]butyl) phenoxy]butan-2-yl]carbamoyl]pyrrolidin-1-yl]-4-methyl-1-oxopentan-2-yl]carbamate | 1079.50 | (400 MHz, DMSO-$d_6$) δ 9.00 (s, 1H), 8.39 (d, J = 7.8 Hz, 1H), 7.84 (d, J = 8.9 Hz, 2H), 7.45 (d, J = 8.3 Hz, 2H), 7.39 (d, J = 8.2 Hz, 2H), 7.24-7.13 (m, 2H), 7.00-6.88 (m, 2H), 6.75 (s, 1H), 6.07 (s, 1H), 4.93 (p, J = 7.2 Hz, 1H), 4.53 (d, J = 9.3 Hz, 1H), 4.43 (t, J = 8.0 Hz, 1H), 4.32-4.28 (m, 2H), 4.27-4.17 (m, 1H), 4.07-3.87 (m, 3H), 3.69-3.55 (m, 3H), 3.51 (d, J = 6.3 Hz, 1H), 3.45-3.36 (m, 1H), 2.73-2.65 (m, 2H), 2.47 (s, 3H), 2.35-2.31 (m, 1H), 2.18-2.14 (m, 3H), 2.02-1.98 (m, 2H), 1.91-1.75 (m, 3H), 1.73-1.62 (m, 1H), 1.61-1.42 (m, 4H), 1.41-1.37 (m, 1H), 1.37 (s, 9H), 1.38-1.34 (m, 2H), 1.33-1.21 (m, 4H), 1.20-1.07 (m, 1H), 0.94 (s, 9H), 0.88-0.84 (m, 6H) |

TABLE 50-continued

| Characterization data for intermediates prepared according to above. | | | | |
|---|---|---|---|---|
| Inter-mediate | Structure | Chemical Name | MS: [(M + 1)]+ | $^1H$ NMR |
| I148 | 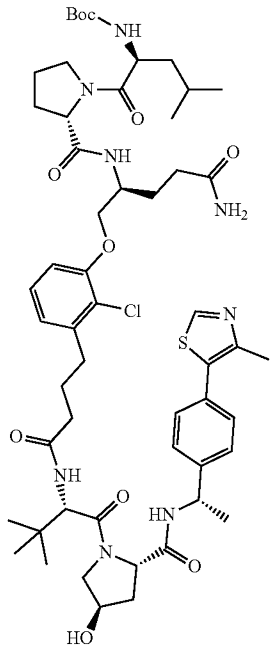 [SMILES: Cc1ncsc1-c1ccc([C@H](C)NC(=O)[C@@H]2C[C@@H](O)CN2C(=O)[C@@H](NC(=O)CCCc2cccc(OC[C@H](CCC(N)=O)NC(=O)[C@@H]3CCCN3C(=O)[C@H](CC(C)C)NC(=O)OC(C)(C)C)c2Cl)C(C)(C)C)cc1] | tert-butyl N-[(2S)-1-[(2S)-2-[[(2S)-4-carbamoyl-1-[2-chloro-3-(3-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]propyl)phenoxy]butan-2-yl]carbamoyl]pyrrolidin-1-yl]-4-methyl-1-oxopentan-2-yl]carbamate | 1065.45 | (400 MHz, DMSO-$d_6$) δ 8.99 (s, 1H), 8.39 (d, J = 7.8 Hz, 1H), 7.90 (d, J = 8.2 Hz, 1H), 7.84 (d, J = 8.2 Hz, 1H), 7.44 (d, J = 8.2 Hz, 2H), 7.38 (d, J = 8.4 Hz, 2H), 7.22-7.15 (m, 2H), 6.98 (d, J = 8.4 Hz, 1H), 6.93 (d, J = 8.2 Hz, 1H), 6.90-6.87 (d, J = 8.2 Hz, 1H), 6.72 (s, 1H), 4.94-4.90 (m, 1H), 4.54 (d, J = 9.3 Hz, 1H), 4.43 (t, J = 8.0 Hz, 1H), 4.31-4.28 (m, 2H), 4.23-4.18 (m, 1H), 4.09-4.02 (m, 1H), 3.99-3.96 (m, 1H), 3.91-3.89 (m, 1H), 3.62 (d, J = 3.3 Hz, 3H), 3.54-3.46 (m, 3H), 2.67 (t, J = 7.1 Hz, 2H), 2.46 (s, 3H), 2.33-2.29 (m, 1H), 2.24-2.12 (m, 4H), 2.02-1.97 (m, 3H), 1.92-1.86 (m, 1H), 1.81-1.76 (m, 5H), 1.68-1.64 (m, 2H), 1.38-1.34 (m, 12H), 0.95 (s, 9H), 0.88 (t, J = 6.4 Hz, 6H) |
| I149 | 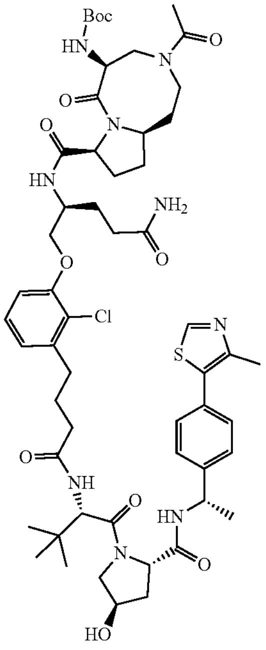 [SMILES: CC(=O)N1CC[C@H]2CC[C@@H](C(=O)N[C@@H](CCC(N)=O)COc3cccc(CCCC(=O)N[C@H](C(=O)N4C[C@H](O)C[C@H]4C(=O)N[C@@H](C)c4ccc(-c5scnc5C)cc4)C(C)(C)C)c3Cl)N2C(=O)[C@@H](NC(=O)OC(C)(C)C)C1] | tert-butyl N-[(5S,8S,10aR)-3-acetyl-8-[[(2S)-4-carbamoyl-1-[2-chloro-3-(3-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]propyl)phenoxy]butan-2-yl]carbamoyl]-6-oxo-octahydropyrrolo[1,2-a][1,5]diazocin-5-yl]carbamate | 1106.55 | (400 MHz, DMSO-$d_6$) δ 8.99 (s, 1H), 8.39 (d, J = 7.8 Hz, 1H), 8.01 (d, J = 8.2 Hz, 1H), 7.89 (d, J = 9.3 Hz, 1H), 7.44 (d, J = 8.3 Hz, 2H), 7.38 (d, J = 8.4 Hz, 2H), 7.24-7.17 (m, 2H), 6.99 (dd, J = 8.3, 3.2 Hz, 1H), 6.89 (d, J = 7.6 Hz, 1H), 6.75-6.71 (m, 1H), 6.68-6.58 (m, 1H), 6.06-6.01 (m, 2H), 4.92 (p, J = 7.2 Hz, 1H), 4.57-4.39 (m, 2H), 4.37-4.25 (m, 2H), 4.25-4.14 (m, 1H), 4.11-3.96 (m, 2H), 3.91-3.88 (m, 1H), 3.62 (d, J = 3.4 Hz, 3H), 3.48-3.13 (m, 1H), 2.67-2.65 (m, 2H), 2.46 (s, 3H), 2.31-2.29 (m, 1H), 2.18 (s, 3H), 2.08-2.05 (m, 3H), 2.03-1.96 (m, 3H), 1.79-1.77 (m, 2H), 1.73-1.43 (m, 5H), 1.38 (s, 9H), 1.25-1.22 (m, 2H), 1.18-1.01 (m, 2H), 0.95 (s, 9H), 0.85-0.82 (m, 3H) |

TABLE 50-continued

Characterization data for intermediates prepared according to above.

| Inter-mediate | Structure | Chemical Name | MS: [(M + 1)]+ | ¹H NMR |
|---|---|---|---|---|
| I150 | 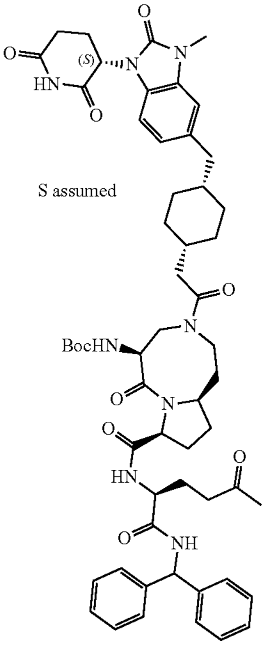 S assumed | tert-butyl N-[(5S,8S,10aR)-8-[[(1S)-3-carbamoyl-1-(diphenylmethyl carbamoyl) propyl]carbamoyl]-6-oxo-3-[2-[(1s,4s)-4-[[1-(2,6-dioxopiperidin-3-yl)-3-methyl-2-oxo-1,3-benzodiazol-5-yl]methyl]cyclohexyl] acetyl]-octahydropyrrolo[1,2-a][1,5]diazocin-5-yl]carbamate | 1016.45 | (400 MHz, DMSO-$d_6$) δ 11.09 (s, 1H), 8.76 (t, J = 8.0 Hz, 1H), 8.27-8.19 (m, 1H), 7.37-7.20 (m, 10H), 7.04-6.93 (m, 2H), 6.87-6.70 (m, 2H), 6.48 (d, J = 6.6 Hz, 1H), 6.10 (d, J = 8.4 Hz, 1H), 5.34 (dd, J = 12.7, 5.4 Hz, 1H), 4.54-4.19 (m, 3H), 4.19-3.88 (m, 1H), 3.83-3.75 (m, 2H), 3.37-3.35 (m, 5H), 3.32 (s, 3H), 3.24-3.02 (m, 1H), 2.98-2.82 (m, 1H), 2.77-2.55 (m, 4H), 2.46-2.25 (m, 1H), 2.20-2.10 (m, 2H), 2.05-1.87 (m, 4H), 1.87-1.51 (m, 6H), 1.45-1.41 (m, 13H), 1.38-1.29 (m, 3H) |
| I151 | 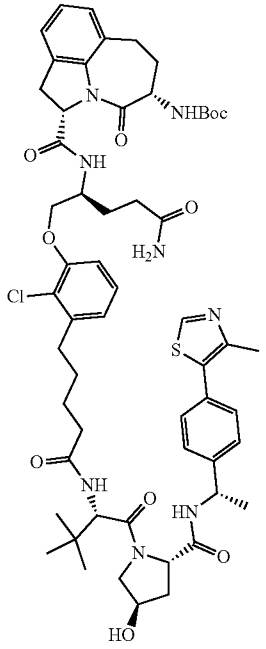 [SMILES: Cc1ncsc1-c1ccc([C@H](C)NC(=O)[C@@H]2C[C@@H](O)CN2C(=O)[C@@H](NC(=O)CCCCc2cccc(OC[C@H](CCC(N)=O)NC(=O)[C@@H]3Cc4cccc5c4N3C(=O)[C@@H](NC(=O)OC(C)(C)C)CC5)c2Cl)C(C)(C)C)cc1] | tert-butyl N-[(2S,11S)-2-[[(2S)-4-carbamoyl-1-[2-chloro-3-(4-[[(2S)-1-[(2S,4R)-4-hydroxy-2-[[(1S)-1-[4-(4-methyl-1,3-thiazol-5-yl)phenyl]ethyl] carbamoyl] pyrrolidin-1-yl]-3,3-dimethyl-1-oxobutan-2-yl]carbamoyl]butyl) phenoxy]butan-2-yl]carbamoyl]-12-oxo-1-azatricyclo[6.4.1.0^[4,13]] trideca-4(13),5,7-trien-11-yl]carbamate | 1097.45 | (300 MHz, DMSO-$d_6$) δ 8.97 (s, 1H), 8.36 (d, J = 7.8 Hz, 1H), 8.06 (d, J = 7.6 Hz, 1H), 7.82 (d, J = 9.3 Hz, 1H), 7.40 (q, J = 8.4 Hz, 4H), 7.19 (dd, J = 16.2, 8.3 Hz, 2H), 7.12-6.85 (m, 6H), 6.73 (s, 1H), 6.01 (s, 2H), 5.74 (s, 1H), 5.03 (dd, J = 10.6, 2.7 Hz, 1H), 4.90 (p, J = 7.2 Hz, 1H), 4.51 (d, J = 9.2 Hz, 1H), 4.42 (t, J = 8.0 Hz, 1H), 4.27 (s, 1H), 4.01 (s, 3H), 4.06-3.90 (m, 1H), 3.60 (d, J = 3.7 Hz, 2H), 3.42-3.38 (m, 1H), 3.05-3.01 (m, 2H), 2.95-2.91 (m, 1H), 2.70-2.66 (m, 2H), 2.45 (s, 3H), 2.33-2.29 (m, 1H), 2.20-2.08 (m, 3H), 2.03 (d, J = 6.9 Hz, 3H), 1.86-1.66 (m, 1H), 1.55-1.51 (m, 4H), 1.38-1.34 (m, 2H), 1.26-1.22 (m, 3H), 0.93 (s, 9H), 0.90-0.76 (m, 7H) |

TABLE 50-continued

| Characterization data for intermediates prepared according to above. | | | | |
|---|---|---|---|---|
| Inter-mediate | Structure | Chemical Name | MS: [(M + 1)]$^+$ | $^1$H NMR |
| I152 | 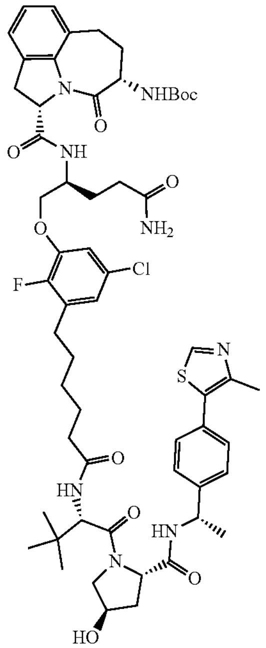 [SMILES: Cc1ncsc1-c1ccc([C@H](C)NC(=O)[C@@H]2C[C@@H](O)CN2C(=O)[C@@H](NC(=O)CCCCCc2cc(Cl)cc(OC[C@H](CCC(N)=O)NC(=O)[C@@H]3Cc4cccc5c4N3C(=O)[C@@H](NC(=O)OC(C)(C)C)CC5)c2F)C(C)(C)C)cc1] | tert-butyl N-[(2S,11S)-2-[[(2S)-4-carbamoyl-1-[5-chloro-2-fluoro-3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenoxy]butan-2-yl]carbamoyl]-12-oxo-1-azatricyclo[6.4.1.0^[4,13]]trideca-4(13),5,7-trien-11-yl]carbamate | 1129.45 | (400 MHz, DMSO-$d_6$) δ 8.99 (s, 1H), 8.38 (d, J = 7.8 Hz, 1H), 8.09 (d, J = 7.5 Hz, 1H), 7.81 (d, J = 9.3 Hz, 1H), 7.44 (d, J = 8.3 Hz, 2H), 7.38 (d, J = 8.2 Hz, 2H), 7.25 (s, 1H), 7.14-7.10 (m, 2H), 7.06-7.00 (m, 2H), 6.96 (d, J = 7.5 Hz, 1H), 6.93-6.91 (m, 1H), 6.76 (s, 1H), 5.11 (d, J = 3.5 Hz, 1H), 5.03-5.00 (m, 1H), 4.92 (t, J = 7.2 Hz, 1H), 4.52 (d, J = 9.3 Hz, 1H), 4.42 (t, J = 8.0 Hz, 1H), 4.30-4.25 (m, 1H), 4.07-3.94 (m, 4H), 3.61 (d, J = 3.8 Hz, 2H), 3.43-3.38 (m, 2H), 3.05-3.01 (m, 2H), 2.85 (d, J = 16.0 Hz, 1H), 2.57 (d, J = 7.3 Hz, 1H), 2.46 (s, 3H), 2.31-2.18 (m, 2H), 2.17-2.10 (m, 3H), 2.06-1.96 (m, 3H), 1.83-1.78 (m, 2H), 1.70-1.68 (m, 1H), 1.53-1.47 (m, 5H), 1.39 (s, 9H), 1.29-1.25 (m, 3H), 0.93 (s, 9H) |
| I153 | 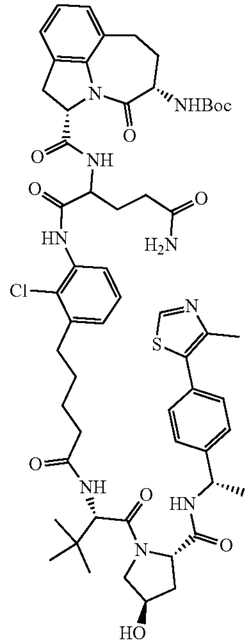 [SMILES: Cc1ncsc1-c1ccc([C@H](C)NC(=O)[C@@H]2C[C@@H](O)CN2C(=O)[C@@H](NC(=O)CCCCc2cccc(NC(=O)C(CCC(N)=O)NC(=O)[C@@H]3Cc4cccc5c4N3C(=O)[C@@H](NC(=O)OC(C)(C)C)CC5)c2Cl)C(C)(C)C)cc1] | tert-butyl ((3S,6S)-6-((5-amino-1-((2-chloro-3-(5-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-5-oxopentyl)phenyl)amino)-1,5-dioxopentan-2-yl)carbamoyl)-4-oxo-1,2,3,4,6,7-hexahydroazepino[3,2,1-hi]indol-3-yl)carbamate | 1110.40 | (400 MHz, DMSO-$d_6$) δ 9.49 (s, 1H), 8.99 (s, 1H), 8.40 (t, J = 8.4 Hz, 2H), 7.85 (dd, J = 9.3, 3.5 Hz, 1H), 7.62-7.58 (m, 1H), 7.48-7.41 (m, 2H), 7.39 (d, J = 8.3 Hz, 2H), 7.33 (d, J = 4.5 Hz, 1H), 7.25 (td, J = 7.8, 5.8 Hz, 1H), 7.16-7.12 (m, 1H), 7.14-7.00 (m, 3H), 6.99-6.95 (m, 1H), 6.82 (s, 1H), 5.14 (dt, J = 13.9, 3.5 Hz, 1H), 4.93 (p, J = 7.0 Hz, 1H), 4.53 (dd, J = 9.3, 2.0 Hz, 1H), 4.44 (q, J = 9.5, 8.0 Hz, 2H), 4.29 (s, 1H), 4.05 (t, J = 7.9 Hz, 1H), 3.62 (d, J = 4.0 Hz, 2H), 3.48-3.44 (m, 1H), 3.06-3.02 (m, 3H), 2.73-2.69 (m, 2H), 2.46 (s, 3H), 2.36-2.28 (m, 1H), 2.21-2.17 (m, 2H), 2.07-2.03 (m, 3H), 1.95-1.74 (m, 2H), 1.58-1.49 (m, 5H), 1.42-1.35 (m, 12H), 1.32-1.19 (m, 2H), 0.99-0.91 (m, 9H) |

TABLE 50-continued

| Characterization data for intermediates prepared according to above. | | | | |
|---|---|---|---|---|
| Inter-mediate | Structure | Chemical Name | MS: [(M + 1)]$^+$ | $^1$H NMR |
| I154 | 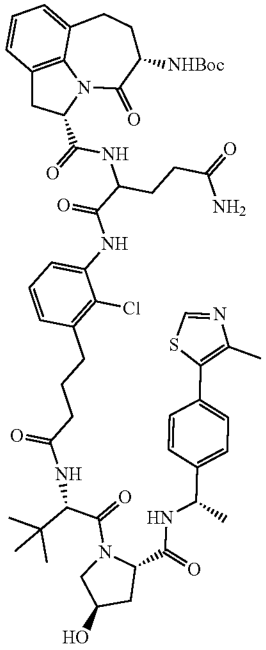 [SMILES: Cc1ncsc1-c1ccc([C@H](C)NC(=O)[C@@H]2C[C@@H](O)CN2C(=O)[C@@H](NC(=O)CCCc2cccc(NC(=O)C(CCC(N)=O)NC(=O)[C@@H]3Cc4cccc5c4N3C(=O)[C@@H](NC(=O)OC(C)(C)C)CC5)c2Cl)C(C)(C)C)cc1] | tert-butyl N-[(2S,11i)-2-[[(1S)-3-carbamoyl-1-[[2-chloro-3-(3-[[(2S)-1-[(2S,4R)-4-hydroxy-2-[[(1S)-1-[4-(4-methyl-1,3-thiazol-5-yl)phenyl]ethyl] carbamoyl] pyrrolidin-1-yl]-3,3-dimethyl-1-oxobutan-2-yl]carbamoyl]propyl) phenyl]carbamoyl] propyl] carbamoyl]-12-oxo-1-azatricyclo[6.4.1.0^[4,13]] trideca-4(13),5,7-trien-11-yl]carbamate | 1096.40 | (400 MHz, DMSO-$d_6$) δ 9.49 (s, 1H), 8.99 (s, 1H), 8.40 (t, J = 9.0 Hz, 2H), 7.90 (d, J = 9.2 Hz, 1H), 7.61 (dd, J = 23.2, 8.1 Hz, 1H), 7.44 (d, J = 8.3 Hz, 2H), 7.38 (d, J = 8.3 Hz, 2H), 7.33 (s, 1H), 7.27-7.23 (m, 1H), 7.15-7.02 (m, 4H), 6.99-6.95 (m, 1H), 6.82 (s, 1H), 5.14 (dd, J = 14.8, 6.0 Hz, 2H), 4.93 (p, J = 7.2 Hz, 1H), 4.55 (d, J = 9.6 Hz, 1H), 4.45 (s, 1H), 4.42 (d, J = 8.1 Hz, 1H), 4.31-4.26 (m, 2H), 4.04 (d, J = 8.3 Hz, 1H), 3.62 (d, J = 3.1 Hz, 2H), 3.51-3.40 (m, 1H), 3.05-3.01 (m, 3H), 2.70-2.66 (m, 2H), 2.46 (s, 3H), 2.33-2.29 (m, 1H), 2.21-2.17 (m, 3H), 2.08-2.04 (m, 2H), 2.03-1.99 (m, 1H), 1.90-1.86 (m, 1H), 1.81-1.77 (m, 2H), 1.42-1.35 (m, 12H), 1.27-1.22 (m, 1H), 0.95 (s, 9H) |
| I155 | 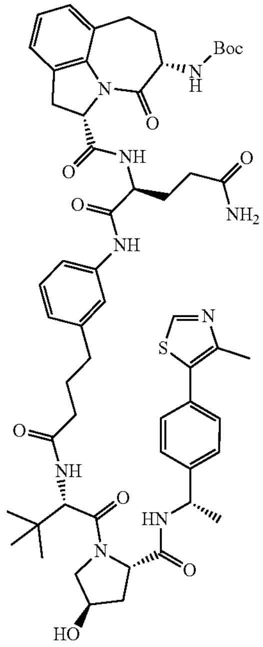 [SMILES: Cc1ncsc1-c1ccc([C@H](C)NC(=O)[C@@H]2C[C@@H](O)CN2C(=O)[C@@H](NC(=O)CCCc2cccc(NC(=O)[C@H](CCC(N)=O)NC(=O)[C@@H]3Cc4cccc5c4N3C(=O)[C@@H](NC(=O)OC(C)(C)C)CC5)c2)C(C)(C)C)cc1] | tert-butyl N-[(2S,11S)-2-[[(1S)-3-carbamoyl-1-[[3-(3-[[(2S)-1-[(2S,4R)-4-hydroxy-2-[[(1S)-1-[4-(4-methyl-1,3-thiazol-5-yl)phenyl]ethyl] carbamoyl] pyrrolidin-1-yl]-3,3-dimethyl-1-oxobutan-2-yl]carbamoyl]propyl) phenyl]carbamoyl] propyl] carbamoyl]-12-oxo-1-azatricyclo[6.4.1.0^[4,13]] trideca-4(13),5,7-trien-11-yl]carbamate | 1062.35 | (400 MHz, DMSO-$d_6$) δ 9.97 (s, 1H), 8.99 (s, 1H), 8.39 (d, J = 7.8 Hz, 1H), 8.34 (d, J = 7.3 Hz, 1H), 7.86 (d, J = 9.2 Hz, 1H), 7.41 (dt, J = 15.3, 8.3 Hz, 6H), 7.32 (s, 1H), 7.20 (t, J = 7.8 Hz, 1H), 7.14-7.08 (m, 2H), 7.03 (d, J = 7.7 Hz, 1H), 6.95 (t, J = 7.5 Hz, 1H), 6.87 (d, J = 7.6 Hz, 1H), 6.80 (s, 1H), 5.13 (dd, J = 10.6, 2.8 Hz, 1H), 4.92 (p, J = 7.1 Hz, 1H), 4.54 (d, J = 9.3 Hz, 1H), 4.43 (t, J = 8.0 Hz, 1H), 4.29 (dd, J = 7.8, 5.1 Hz, 2H), 4.05-3.78 (m, 2H), 3.62-3.45 (m, 3H), 3.03-2.95 (m, 3H), 2.54-2.51 (m, 1H), 2.46 (s, 3H), 2.32-1.97 (m, 5H), 1.96-1.70 (m, 2H), 1.65-1.42 (m, 3H), 1.35 (s, 9H), 1.05-1.01 (m, 6H), 0.95 (s, 9H) |

TABLE 50-continued

| Characterization data for intermediates prepared according to above. | | | | |
|---|---|---|---|---|
| Inter-mediate | Structure | Chemical Name | MS: [(M + 1)]+ | $^1$H NMR |
| I156 | 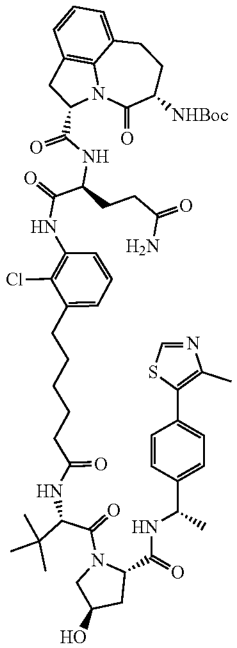 [SMILES: Cc1ncsc1-c1ccc([C@H](C)NC(=O)[C@@H]2C[C@@H](O)CN2C(=O)[C@@H](NC(=O)CCCCCc2cccc(NC(=O)[C@H](CCC(N)=O)NC(=O)[C@@H]3Cc4cccc5c4N3C(=O)[C@@H](NC(=O)OC(C)(C)C)CC5)c2Cl)C(C)(C)C)cc1] | tert-butyl N-[(2S,11S)-2-[[(1S)-3-carbamoyl-1-[[2-chloro-3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenyl]carbamoyl]propyl]carbamoyl]-12-oxo-1-azatricyclo[6.4.1.0^[4,13]]trideca-4(13),5,7-trien-11-yl]carbamate | 1124.55 | (300 MHz, DMSO-$d_6$) δ 9.48-9.45 (m, 1H), 9.00 (s, 1H), 8.40 (t, J = 8.0 Hz, 2H), 7.80 (d, J = 9.2 Hz, 1H), 7.62-7.55 (m, 1H), 7.42 (q, J = 8.3 Hz, 4H), 7.33 (s, 1H), 7.28-7.22 (m, 1H), 7.18-7.02 (m, 3H), 7.01-6.97 (m, 1H), 6.82 (s, 1H), 5.20-5.07 (m, 2H), 4.98-4.88 (m, 1H), 4.53 (d, J = 9.2 Hz, 1H), 4.44 (t, J = 8.0 Hz, 1H), 4.30 (s, 1H), 4.09-4.04 (m, 1H), 3.62 (s, 2H), 3.56-3.38 (m, 1H), 3.34 (s, 2H), 3.05-2.99 (m, 3H), 2.69 (t, J = 7.7 Hz, 2H), 2.47 (s, 3H), 2.35-1.96 (m, 10H), 1.96-1.74 (m, 1H), 1.61-1.48 (m, 3H), 1.41-1.28 (m, 14H), 0.95 (s, 9H) |
| I157 | 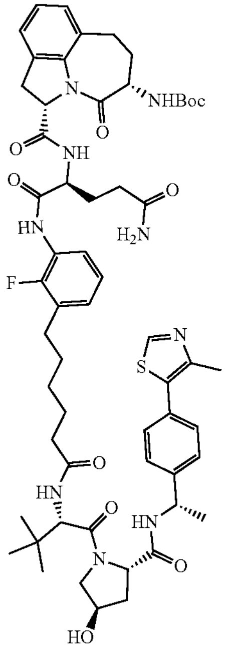 [SMILES: Cc1ncsc1-c1ccc([C@H](C)NC(=O)[C@@H]2C[C@@H](O)CN2C(=O)[C@@H](NC(=O)CCCCCc2cccc(NC(=O)[C@H](CCC(N)=O)NC(=O)[C@@H]3Cc4cccc5c4N3C(=O)[C@@H](NC(=O)OC(C)(C)C)CC5)c2F)C(C)(C)C)cc1] | tert-butyl N-[(2S,11S)-2-[[(1S)-3-carbamoyl-1-[[2-fluoro-3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenyl]carbamoyl]propyl]carbamoyl]-12-oxo-1-azatricyclo[6.4.1.0^[4,13]]trideca-4(13),5,7-trien-11-yl]carbamate | 1108.55 | (300 MHz, DMSO-$d_6$) δ 9.73 (s, 1H), 9.00 (s, 1H), 8.38 (t, J = 7.1 Hz, 2H), 7.80 (d, J = 9.1 Hz, 1H), 7.72-7.67 (m, 1H), 7.47-7.35 (m, 5H), 7.17-6.90 (m, 6H), 6.82 (s, 1H), 5.17-5.12 (m, 2H), 5.03-4.84 (m, 1H), 4.58-4.39 (m, 3H), 4.30 (s, 1H), 4.09-4.04 (m, 1H), 3.52-3.35 (m, 2H), 3.11-2.96 (m, 3H), 2.63-2.58 (m, 2H), 2.48 (s, 3H), 2.35-1.74 (m, 10H), 1.60-1.51 (m, 5H), 1.42-1.39 (m, 12H), 1.35-1.18 (m, 2H), 0.95 (s, 9H) |

TABLE 50-continued

| Characterization data for intermediates prepared according to above. | | | | |
|---|---|---|---|---|
| Inter-mediate | Structure | Chemical Name | MS: [(M + 1)]$^+$ | $^1$H NMR |
| I158 | 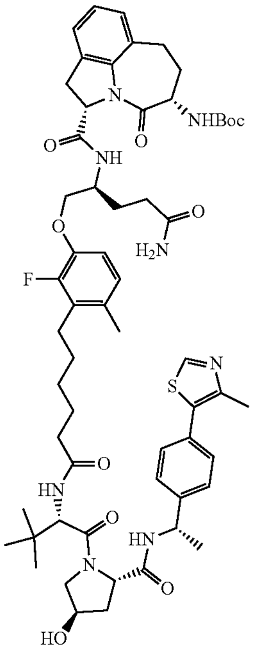 [SMILES: Cc1ccc(OC[C@H](CCC(N)=O)NC(=O)[C@@H]2Cc3cccc4c3N2C(=O)[C@@H](NC(=O)OC(C)(C)C)CC4)c(F)c1CCCCCC(=O)N[C@H](C(=O)N1C[C@H](O)C[C@H]1C(=O)N[C@@H](C)c1ccc(-c2scnc2C)cc1)C(C)(C)C] | tert-butyl N-[(2S,11S)-2-[[(2S)-4-carbamoyl-1-[2-fluoro-3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)-4-methylphenoxy]butan-2-yl]carbamoyl]-12-oxo-1-azatricyclo[6.4.1.0^[4,13]]trideca-4(13),5,7-trien-11-yl]carbamate | 1109.50 | (400 MHz, DMSO-$d_6$) δ 8.99 (s, 1H), 8.38 (d, J = 7.8 Hz, 1H), 8.07 (d, J = 7.8 Hz, 1H), 7.81 (d, J = 9.3 Hz, 1H), 7.44 (d, J = 8.2 Hz, 2H), 7.38 (d, J = 8.2 Hz, 2H), 7.27-7.22 (m, 1H), 7.10 (d, J = 8.0 Hz, 1H), 7.04 (d, J = 7.5 Hz, 2H), 6.99-6.92 (m, 1H), 6.92-6.84 (m, 2H), 6.75 (s, 1H), 5.11 (d, J = 3.5 Hz, 1H), 5.03 (dd, J = 10.8, 2.8 Hz, 1H), 4.92 (p, J = 7.2 Hz, 1H), 4.53 (d, J = 9.3 Hz, 1H), 4.43 (t, J = 8.0 Hz, 1H), 4.28 (s, 1H), 4.09-4.00 (m, 1H), 3.97-3.85 (m, 1H), 3.66-3.59 (m, 2H), 3.48-3.36 (m, 1H), 3.34 (s, 1H), 3.23-2.95 (m, 3H), 2.87 (d, J = 16.6 Hz, 1H), 2.56 (s, 2H), 2.46 (s, 3H), 2.30-2.26 (m, 1H), 2.21 (s, 3H), 2.18-1.97 (m, 4H), 1.89-1.76 (m, 1H), 1.76-1.64 (m, 1H), 1.61-1.42 (m, 3H), 1.39 (s, 9H), 1.37 (s, 3H), 1.34-1.22 (m, 5H), 1.17-1.05 (m, 1H), 0.94 (s, 9H) |
| I159 | 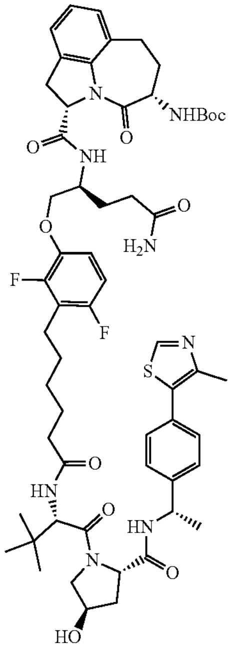 [SMILES: Cc1ncsc1-c1ccc([C@H](C)NC(=O)[C@@H]2C[C@@H](O)CN2C(=O)[C@@H](NC(=O)CCCCCc2c(F)ccc(OC[C@H](CCC(N)=O)NC(=O)[C@@H]3Cc4cccc5c4N3C(=O)[C@@H](NC(=O)OC(C)(C)C)CC5)c2F)C(C)(C)C)cc1] | tert-butyl N-[(2S,11S)-2-[[(2S)-4-carbamoyl-1-[2,4-difluoro-3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenoxy]butan-2-yl]cabamoyl]-12-oxo-1-azatricyclo[6.4.1.0^[4,13]]trideca-4(13),5,7-trien-11-yl]carbamate | 1113.45 | (400 MHz, DMSO-$d_6$) δ 8.99 (s, 1H), 8.38 (d, J = 7.8 Hz, 1H), 8.09 (d, J = 7.6 Hz, 1H), 7.80 (d, J = 9.3 Hz, 1H), 7.44 (d, J = 8.3 Hz, 2H), 7.45-7.31 (m, 2H), 7.27-7.22 (m, 1H), 7.09 (t, J = 8.3 Hz, 1H), 7.04 (d, J = 7.2 Hz, 3H), 6.97-6.93 (m, 2H), 6.75 (s, 1H), 5.10 (d, J = 3.6 Hz, 1H), 5.03 (dd, J = 10.7, 2.8 Hz, 1H), 4.98-4.86 (m, 1H), 4.52 (d, J = 9.3 Hz, 1H), 4.42 (t, J = 8.0 Hz, 1H), 4.31-4.21 (m, 1H), 4.11-3.88 (m, 3H), 3.66-3.55 (m, 2H), 3.49-3.35 (m, 1H), 3.12-2.97 (m, 1H), 2.90-2.82 (m, 1H), 2.64-2.56 (m, 2H), 2.46 (s, 3H), 2.32-2.21 (m, 1H), 2.20-1.96 (m, 6H), 1.88-1.75 (m, 1H), 1.73-1.63 (m, 1H), 1.59-1.44 (m, 2H), 1.39 (s, 9H), 1.37 (s, 3H), 1.33-1.20 (m, 6H), 1.19-1.05 (m, 1H), 0.93 (s, 9H) |

TABLE 50-continued

Characterization data for intermediates prepared according to above.

| Intermediate | Structure | Chemical Name | MS: [(M + 1)]$^+$ | $^1$H NMR |
|---|---|---|---|---|
| I160 | 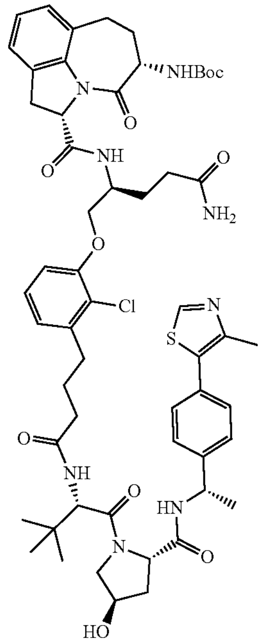 [SMILES: Cc1ncsc1-c1ccc([C@H](C)NC(=O)[C@@H]2C[C@@H](O)CN2C(=O)[C@@H](NC(=O)CCCc2cccc(OC[C@H](CCC(N)=O)NC(=O)[C@@H]3Cc4cccc5c4N3C(=O)[C@@H](NC(=O)OC(C)(C)C)CC5)c2Cl)C(C)(C)C)cc1] | tert-butyl N-[(2S,11S)-2-[[(2S)-4-carbamoyl-1-[2-chloro-3-(3-[[(2S)-1-[(2S,4R)-4-hydroxy-2-[[(1S)-1-[4-(4-methyl-1,3-thiazol-5-yl)phenyl]-ethyl] carbamoyl] pyrrolidin-1-yl]-3,3-dimethyl-1-oxobutan-2-yl]carbamoyl]propyl) phenoxy]butan-2-yl]carbamoyl]-12-oxo-1-azatricyclo[6.4.1.0^[4,13]] trideca-4(13),5,7-trien-11-yl]carbamate | 1083.45 | (300 MHz, DMSO-$d_6$) δ 8.97 (s, 1H), 8.33 (d, J = 7.8 Hz, 1H), 8.04 (d, J = 7.6 Hz, 1H), 7.85 (d, J = 9.1 Hz, 1H), 7.40 (q, J = 8.3 Hz, 3H), 7.39 (s, 1H), 7.24-7.13 (m, 2H), 6.99 (dt, J = 17.4, 7.3 Hz, 5H), 6.94-6.84 (m, 1H), 6.70 (s, 1H), 5.10-4.97 (m, 2H), 4.91 (t, J = 7.3 Hz, 1H), 4.54 (d, J = 9.3 Hz, 1H), 4.42 (t, J = 8.0 Hz, 1H), 4.28 (s, 1H), 4.09-3.89 (m, 4H), 3.60 (d, J = 9.7 Hz, 2H), 3.40 (t, J = 14.2 Hz, 2H), 3.03 (s, 3H), 2.93 (d, J = 16.9 Hz, 1H), 2.67 (t, J = 7.8 Hz, 2H), 2.45 (s, 3H), 2.32-2.10 (m, 3H), 2.07-1.95 (m, 2H), 1.90-1.67 (m, 3H), 1.53-1.42 (m, 1H), 1.37 (d, J = 6.6 Hz, 12H), 1.23 (s, 1H), 0.95 (s, 9H) |
| I161 | 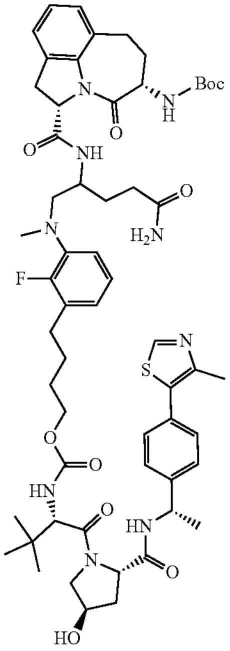 [SMILES: Cc1ncsc1-c1ccc([C@H](C)NC(=O)[C@@H]2C[C@@H](O)CN2C(=O)[C@@H](NC(=O)OCCCCc2cccc(N(C)CC(CCC(N)=O)NC(=O)[C@@H]3Cc4cccc5c4N3C(=O)[C@@H](NC(=O)OC(C)(C)C)CC5)c2F)C(C)(C)C)cc1] | 4-[3-[(2-[[(2S,11S)-11-[(tert-butoxycarbonyl)amino]-12-oxo-1-azatricyclo[6.4.1.0^[4,13]] trideca-4(13),5,7-trien-2-yl]formamido]-4-carbamoylbutyl)(methyl) amino]-2-fluorophenyl]butyl N-[(2S)-1-[(2S,4R)-4-hydroxy-2-[[(1S)-1-[4-(4-methyl-1,3-thiazol-5-yl)phenyl]ethyl] carbamoyl]pyrrolidin-1-yl]-3,3-dimethyl-1-oxobutan-2-yl]carbamate | 1110.45 | (400 MHz, DMSO-$d_6$) δ 8.99 (s, 1H), 8.39 (d, J = 7.7 Hz, 1H), 7.78 (d, J = 9.0 Hz, 1H), 7.47-7.41 (m, 3H), 7.38 (d, J = 8.2 Hz, 2H), 7.17 (s, 1H), 7.08 (s, 1H), 7.02 (d, J = 6.6 Hz, 2H), 6.95-6.91 (m, 2H), 6.77-6.73 (m, 3H), 5.11 (d, J = 3.6 Hz, 1H), 4.92 (p, J = 12.5 Hz, 2H), 4.44 (t, J = 8.0 Hz, 1H), 4.28 (s, 1H), 4.17 (d, J = 8.8 Hz, 1H), 4.02 (s, 2H), 3.97-3.93 (m, 3H), 3.60 (s, 2H), 3.17-3.00 (m, 3H), 2.73 (s, 3H), 2.59 (s, 3H), 2.59-2.55 (m, 2H), 2.46 (s, 3H), 2.06-2.02 (m, 2H), 1.81-1.77 (m, 1H), 1.64-1.60 (m, 4H), 1.41-1.37 (m, 2H), 1.41-1.37 (m, 12H), 1.29-1.25 (m, 2H), 0.94 (s, 9H) |

TABLE 50-continued

| Characterization data for intermediates prepared according to above. | | | | |
|---|---|---|---|---|
| Inter-mediate | Structure | Chemical Name | MS: [(M + 1)]+ | $^1$H NMR |
| I162 | 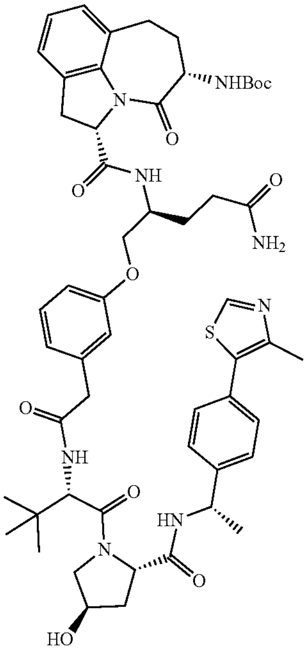 [SMILES: Cc1ncsc1-c1ccc([C@H](C)NC(=O)[C@@H]2C[C@@H](O)CN2C(=O)[C@@H](NC(=O)Cc2cccc(OC[C@H](CCC(N)=O)NC(=O)[C@@H]3Cc4cccc5c4N3C(=O)[C@@H](NC(=O)OC(C)(C)C)CC5)c2)C(C)(C)C)cc1] | tert-butyl N-[(2S,11S)-2-[[(2S)-4-carbamoyl-1-[3-([[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]methyl)phenoxy]butan-2-yl]carbamoyl]-12-oxo-1-azatricyclo[6.4.1.0^[4,13]]trideca-4(13),5,7-trien-11-yl]carbamate | [(M − H)]$^-$ = 1019.60 | (300 MHz, DMSO-$d_6$) δ 8.97 (s, 1H), 8.37 (d, J = 7.8 Hz, 1H), 8.05 (dd, J = 15.2, 8.8 Hz, 2H), 7.41-7.35 (q, J = 8.4 Hz, 4H), 7.23-6.66 (m, 10H), 5.15-4.86 (m, 3H), 4.54-4.34 (m, 2H), 4.09-3.81 (m, 4H), 3.67-3.53 (m, 3H), 3.41 (d, J = 13.6 Hz, 2H), 3.16-2.71 (m, 3H), 2.45 (s, 3H), 2.18-2.09 (m, 2H), 1.99-1.97 (m, 2H), 1.91-1.61 (m, 4H), 1.40-1.35 (m, 13H), 0.91 (s, 9H) |
| I163 | 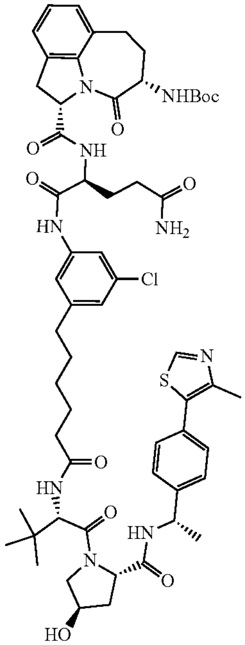 [SMILES: Cc1ncsc1-c1ccc([C@H](C)NC(=O)[C@@H]2C[C@@H](O)CN2C(=O)[C@@H](NC(=O)CCCCCc2cc(Cl)cc(NC(=O)[C@H](CCC(N)=O)NC(=O)[C@@H]3Cc4cccc5c4N3C(=O)[C@@H](NC(=O)OC(C)(C)C)CC5)c2)C(C)(C)C)cc1] | tert-butyl N-[(2S,11S)-2-[[(1S)-3-carbamoyl-1-[[3-chloro-5-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenyl]carbamoyl]propyl]carbamoyl]-12-oxo-1-azatricyclo[6.4.1.0^[4,13]]trideca-4(13),5,7-trien-11-yl]carbamate | [(M − H)]$^-$ = 1122.68 | (300 MHz, DMSO-$d_6$) δ 10.12 (d, J = 15.1 Hz, 1H), 9.00 (s, 1H), 8.38 (d, J = 7.7 Hz, 2H), 7.80 (d, J = 9.3 Hz, 1H), 7.63 (t, J = 1.9 Hz, 1H), 7.45 (d, J = 8.3 Hz, 3H), 7.39 (d, J = 8.3 Hz, 2H), 7.32 (s, 1H), 7.26 (s, 1H), 7.11 (s, 2H), 7.04 (d, J = 7.4 Hz, 1H), 7.01-6.90 (m, 2H), 6.81 (s, 1H), 5.13 (d, J = 11.6 Hz, 2H), 4.99-4.88 (m, 1H), 4.52 (d, J = 9.3 Hz, 1H), 4.43 (t, J = 8.0 Hz, 1H), 4.29 (s, 2H), 4.06 (t, J = 8.4 Hz, 1H), 3.62 (s, 2H), 3.45 (t, J = 13.6 Hz, 2H), 3.15-2.93 (m, 3H), 2.47 (s, 3H), 2.33-2.11 (m, 4H), 2.01-1.73 (m, 5H), 1.66-1.45 (m, 5H), 1.44-1.31 (m, 12H), 1.30-1.22 (m, 2H), 0.94 (s, 9H) |

TABLE 50-continued

Characterization data for intermediates prepared according to above.

| Intermediate | Structure | Chemical Name | MS: [(M + 1)]+ | $^1$H NMR |
|---|---|---|---|---|
| I164 | 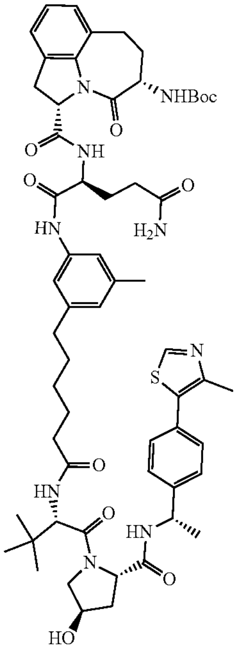 [SMILES: Cc1cc(CCCCCC(=O)N[C@H](C(=O)N2C[C@H](O)C[C@H]2C(=O)N[C@@H](C)c2ccc(-c3scnc3C)cc2)C(C)(C)C)cc(NC(=O)[C@H](CCC(N)=O)NC(=O)[C@@H]2Cc3cccc4c3N2C(=O)[C@@H](NC(=O)OC(C)(C)C)CC4)c1] | Tert-butyl N-[(2S,11S)-2-[[(1S)-3-carbamoyl-1-[[3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)-5-methylphenyl]carbamoyl]propyl]carbamoyl]-12-oxo-1-azatricyclo[6.4.1.0^[4,13]]trideca-4(13),5,7-trien-11-yl]carbamate | 1104.50 | (400 MHz, DMSO-$d_6$) δ 9.85 (s, 1H), 8.99 (s, 1H), 8.38 (d, J = 7.8 Hz, 1H), 8.31 (d, J = 7.4 Hz, 1H), 7.80 (d, J = 9.2 Hz, 1H), 7.44 (d, J = 8.1 Hz, 2H), 7.38 (d, J = 8.2 Hz, 2H), 7.36-7.30 (m, 1H), 7.26-7.21 (m, 2H), 7.10 (d, J = 7.5 Hz, 2H), 7.04 (d, J = 7.9 Hz, 1H), 6.95 (t, J = 7.4 Hz, 1H), 6.79 (s, 1H), 6.70 (s, 1H), 5.18-5.03 (m, 2H), 4.92 (p, J = 7.2 Hz, 1H), 4.52 (d, J = 9.3 Hz, 1H), 4.33-4.24 (m, 2H), 4.11-4.02 (m, 2H), 3.61 (d, J = 3.6 Hz, 2H), 3.53-3.40 (m, 2H), 3.15-2.93 (m, 3H), 2.52-2.43 (m, 5H), 2.49-2.41 (m, 2H), 2.32-2.24 (m, 2H), 2.23 (s, 3H), 2.19-1.74 (m, 6H), 1.60-1.45 (m, 4H), 1.38 (s, 9H), 1.29-1.23 (m, 4H), 0.93 (s, 9H) |
| I165 | 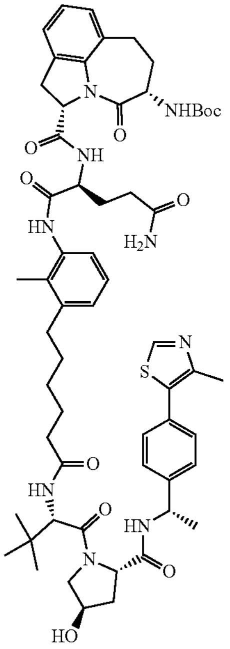 [SMILES: Cc1ncsc1-c1ccc([C@H](C)NC(=O)[C@@H]2C[C@@H](O)CN2C(=O)[C@@H](NC(=O)CCCCCc2cccc(NC(=O)[C@H](CCC(N)=O)NC(=O)[C@@H]3Cc4cccc5c4N3C(=O)[C@@H](NC(=O)OC(C)(C)C)CC5)c2C)C(C)(C)C)cc1] | tert-butyl N-[(2S,11S)-2-[[(1S)-3-carbamoyl-1-[[3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)-2-methylphenyl]carbamoyl]propyl]carbamoyl]-12-oxo-1-azatricyclo[6.4.1.0^[4,13]]trideca-4(13),5,7-trien-11-yl]carbamate | 1104.50 | (400 MHz, DMSO-$d_6$) δ 9.39 (s, 1H), 8.99 (s, 1H), 8.39 (d, J = 7.8 Hz, 1H), 8.31 (d, J = 7.5 Hz, 1H), 7.81 (d, J = 9.2 Hz, 1H), 7.44 (d, J = 8.3 Hz, 2H), 7.39 (d, J = 8.3 Hz, 2H), 7.36-7.29 (m, 1H), 7.16-7.01 (m, 5H), 7.01-6.92 (m, 2H), 6.86-6.77 (m, 1H), 5.21-5.06 (m, 2H), 4.96-4.90 (m, 1H), 4.53 (d, J = 9.3 Hz, 1H), 4.47-4.23 (m, 6H), 4.13-3.99 (m, 1H), 3.80-3.77 (m, 2H), 3.62 (d, J = 3.7 Hz, 2H), 3.53-3.39 (m, 1H), 3.38-3.26 (m, 4H), 3.17-2.94 (m, 2H), 2.56 (t, J = 7.6 Hz, 2H), 2.46 (s, 3H), 2.34-2.10 (m, 2H), 2.04-1.98 (m, 3H), 1.95-1.68 (m, 1H), 1.68-1.44 (m, 3H), 1.40 (s, 9H), 1.38 (s, 3H), 1.34-1.19 (m, 2H), 0.94 (s, 9H) |

TABLE 50-continued

| Characterization data for intermediates prepared according to above. | | | | |
|---|---|---|---|---|
| Inter-mediate | Structure | Chemical Name | MS: [(M + 1)]$^+$ | $^1$H NMR |
| I166 | 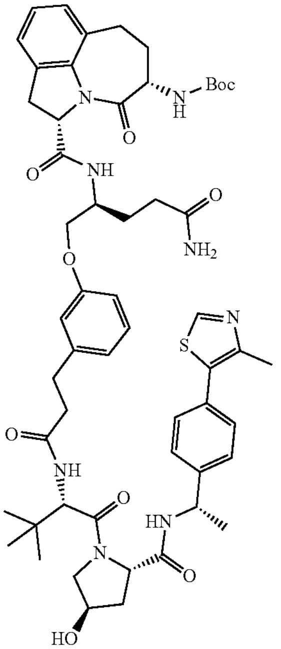 [SMILES: Cc1ncsc1-c1ccc([C@H](C)NC(=O)[C@@H]2C[C@@H](O)CN2C(=O)[C@@H](NC(=O)CCc2cccc(OC[C@H](CCC(N)=O)NC(=O)[C@@H]3Cc4cccc5c4N3C(=O)[C@@H](NC(=O)OC(C)(C)C)CC5)c2)C(C)(C)C)cc1] | tert-butyl N-[(2S,11S)-2-[[(2S)-4-carbamoyl-1-[3-(2-[[(2S)-1-[(2S,4R)-4-hydroxy-2-[[(1S)-1-[4-(4-methyl-1,3-thiazol-5-yl)phenyl]ethyl] carbamoyl] pyrrolidin-1-yl]-3,3-dimethyl-1-oxobutan-2-yl]carbamoyl]ethyl) phenoxy]butan-2-yl]carbamoyl]-12-oxo-1-azatricyclo[6.4.1.0^[4,13]] trideca-4(13),5,7-trien-11-yl]carbamate | 1035.50 | (400 MHz, DMSO-$d_6$) δ 8.99 (s, 1H), 8.39 (d, J = 7.8 Hz, 1H), 8.07 (d, J = 8.3 Hz, 1H), 7.89 (d, J = 9.3 Hz, 1H), 7.44 (d, J = 8.3 Hz, 2H), 7.39 (d, J = 8.2 Hz, 2H), 7.25 (s, 1H), 7.21-7.01 (m, 3H), 6.97 (q, J = 7.6 Hz, 2H), 6.83-6.70 (m, 3H), 5.76 (s, 4H), 5.04 (ddd, J = 10.5, 6.5, 2.6 Hz, 2H), 4.93 (p, J = 7.1 Hz, 1H), 4.54 (d, J = 9.3 Hz, 1H), 4.44 (t, J = 8.0 Hz, 1H), 4.29 (d, J = 3.9 Hz, 1H), 4.12-3.94 (m, 2H), 3.94-3.86 (m, 2H), 3.62 (d, J = 3.4 Hz, 2H), 3.46 (ddd, J = 32.8, 16.8, 11.1 Hz, 1H), 3.17-2.94 (m, 2H), 2.92-2.74 (m, 2H), 2.46 (s, 3H), 2.23-1.94 (m, 7H), 1.92-1.67 (m, 2H), 1.39 (s, 9H), 0.91 (s, 9H) |
| I167 | 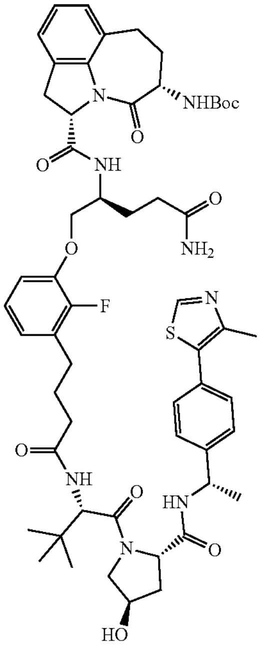 [SMILES: Cc1ncsc1-c1ccc([C@H](C)NC(=O)[C@@H]2C[C@@H](O)CN2C(=O)[C@@H](NC(=O)CCCc2cccc(OC[C@H](CCC(N)=O)NC(=O)[C@@H]3Cc4cccc5c4N3C(=O)[C@@H](NC(=O)OC(C)(C)C)CC5)c2F)C(C)(C)C)cc1] | tert-butyl N-(2S,11S)-2-[[(2S)-4-carbamoyl-1-[2-fluoro-3-(3-[[(2S)-1-[(2S,4R)-4-hydroxy-2-[[(1S)-1-[4-(4-methyl-1,3-thiazol-5-yl)phenyl]ethyl] carbamoyl] pyrrolidin-1-yl]-3,3-dimethyl-1-oxobutan-2-yl]carbamoyl]propyl) phenoxy]butan-2-yl]carbamoyl]-12-oxo-1-azatricyclo[6.4.1.0^[4,13]] trideca-4(13),5,7-trien-11-yl]carbamate | 1067.45 | (400 MHz, DMSO-$d_6$) δ 8.99 (s, 1H), 8.38 (d, J = 7.8 Hz, 1H), 8.10 (d, J = 7.5 Hz, 1H), 7.89 (d, J = 9.2 Hz, 1H), 7.44 (d, J = 8.3 Hz, 2H), 7.39 (d, J = 8.3 Hz, 2H), 7.27-7.23 (m, 1H), 7.11 (d, J = 8.0 Hz, 1H), 7.06-7.00 (m, 4H), 6.98-6.92 (m, 1H), 6.82-6.81 (m, 1H), 6.75 (s, 1H), 5.04 (d, J = 10.7 Hz, 1H), 4.92 (t, J = 7.4 Hz, 1H), 4.55 (d, J = 9.3 Hz, 1H), 4.43 (t, J = 8.0 Hz, 1H), 4.29 (s, 1H), 4.05-3.97 (m, 4H), 3.63-3.61 (m, 2H), 3.43-3.39 (m, 1H), 3.14-2.96 (m, 2H), 2.87 (d, J = 16.7 Hz, 1H), 2.58 (t, J = 7.8 Hz, 2H), 2.46 (s, 3H), 2.37-2.25 (m, 1H), 2.24-2.11 (m, 3H), 2.09-2.04 (m, 3H), 2.07-1.94 (m, 4H), 1.93-1.63 (m, 5H), 1.39 (s, 9H), 0.95 (s, 9H) |

TABLE 50-continued

| Characterization data for intermediates prepared according to above. | | | | |
|---|---|---|---|---|
| Intermediate | Structure | Chemical Name | MS: [(M + 1)]$^+$ | $^1$H NMR |
| I168 | 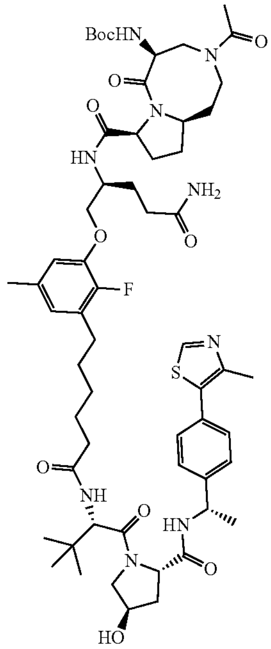 [SMILES: CC(=O)N1CC[C@H]2CC[C@@H](C(=O)N[C@@H](CCC(N)=O)COc3cc(C)cc(CCCCCC(=O)N[C@H](C(=O)N4C[C@H](O)C[C@H]4C(=O)N[C@@H](C)c4ccc(-c5scnc5C)cc4)C(C)(C)C)c3F)N2C(=O)[C@@H](NC(=O)OC(C)(C)C)C1] | tert-butyl N-[(5S,8S,10aR)-3-acetyl-8-[[(2S)-4-carbamoyl-1-[2-fluoro-3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)-5-methylphenoxy]butan-2-yl]carbamoyl]-6-oxo-octahydropyrrolo[1,2-a][1,5]diazocin-5-yl]carbamate | 1132.40 | (300 MHz, DMSO-$d_6$) δ 8.97 (s, 1H), 8.35 (d, J = 7.8 Hz, 1H), 8.01-7.93 (m, 1H), 7.82-7.74 (m, 1H), 7.43 (d, J = 8.4 Hz, 2H), 7.37 (d, J = 8.4 Hz, 2H), 7.17 (s, 1H), 6.83-6.52 (m, 4H), 5.08 (s, 1H), 4.97-4.83 (m, 1H), 4.51 (d, J = 9.3 Hz, 2H), 4.42 (t, J = 8.0 Hz, 2H), 4.35-4.11 (m, 4H), 4.09-3.78 (m, 4H), 3.74-3.51 (m, 5H), 3.48-3.10 (m, 6H), 2.45 (s, 3H), 2.22 (s, 3H), 2.18-2.12 (m, 2H), 2.02-1.96 (m, 2H), 1.89-1.77 (m, 4H), 1.75-1.60 (m, 4H), 1.57-1.43 (m, 5H), 1.38 (s, 9H), 1.35 (s, 3H), 0.92 (s, 9H) |
| I169 | 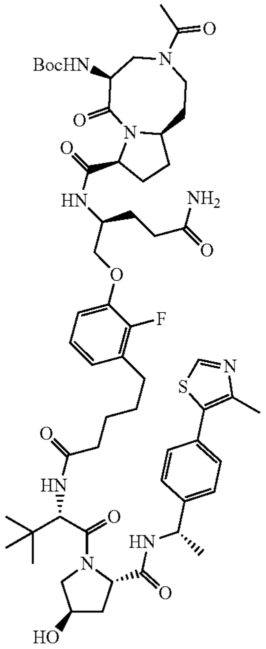 [SMILES: CC(=O)N1CC[C@H]2CC[C@@H](C(=O)N[C@@H](CCC(N)=O)COc3cccc(CCCCC(=O)N[C@H](C(=O)N4C[C@H](O)C[C@H]4C(=O)N[C@@H](C)c4ccc(-c5scnc5C)cc4)C(C)(C)C)c3F)N2C(=O)[C@@H](NC(=O)OC(C)(C)C)C1] | tert-butyl N-[(5S,8S,10aR)-3-acetyl-8-[[(2S)-4-carbamoyl-1-[2-fluoro-3-(4-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]butyl)phenoxy]butan-2-yl]carbamoyl]-6-oxo-octahydropyrrolo[1,2-a][1,5]diazocin-5-yl]carbamate | 1104.50 | (400 MHz, DMSO-$d_6$) δ 8.99 (s, 1H), 8.38 (d, J = 7.8 Hz, 1H), 8.02 (t, J = 7.5 Hz, 1H), 7.83 (d, J = 9.2 Hz, 1H), 7.44 (d, J = 8.3 Hz, 2H), 7.39 (d, J = 8.3 Hz, 2H), 7.19 (s, 1H), 7.05-6.94 (m, 2H), 6.82 (t, J = 6.5, 3.1 Hz, 1H), 6.75 (s, 1H), 6.67-6.56 (m, 1H), 5.11 (d, J = 3.5 Hz, 1H), 4.93 (t, J = 7.1 Hz, 1H), 4.52 (d, J = 9.2 Hz, 1H), 4.43 (t, J = 8.0 Hz, 1H), 4.35-4.27 (m, 2H), 4.25-4.12 (m, 2H), 4.09-4.01 (m, 1H), 4.01-3.98 (m, 1H), 3.91-3.89 (m, 1H), 3.70-3.56 (m, 4H), 3.36-3.30 (m, 2H), 3.23-3.14 (m, 1H), 2.60 (t, J = 6.7 Hz, 2H), 2.46 (s, 3H), 2.32-2.28 (m, 1H), 2.25-2.13 (m, 2H), 2.08 (d, J = 3.7 Hz, 3H), 2.06-1.92 (m, 2H), 1.85-1.78 (m, 2H), 1.70-1.66 (m, 2H), 1.53-1.49 (m, 4H), 1.42-1.37 (m, 7H), 1.38-1.36 (s, 9H), 0.94 (s, 9H) |

TABLE 50-continued

| Characterization data for intermediates prepared according to above. | | | | |
|---|---|---|---|---|
| Intermediate | Structure | Chemical Name | MS: [(M + 1)]$^+$ | $^1$H NMR |
| I170 | 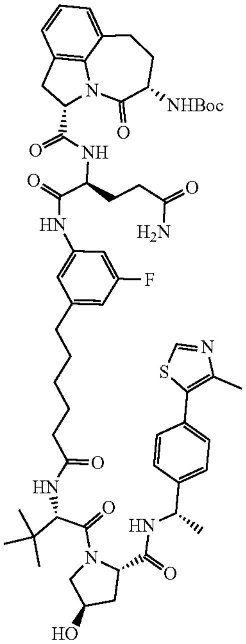 [SMILES: Cc1ncsc1-c1ccc([C@H](C)NC(=O)[C@@H]2C[C@@H](O)CN2C(=O)[C@@H](NC(=O)CCCCCc2cc(F)cc(NC(=O)[C@H](CCC(N)=O)NC(=O)[C@@H]3Cc4cccc5c4N3C(=O)[C@@H](NC(=O)OC(C)(C)C)CC5)c2)C(C)(C)C)cc1] | tert-butyl N-[(2S,11S)-2-[[(1S)-3-carbamoyl-1-[[3-fluoro-5-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenyl]carbamoyl]propyl]carbamoyl]-12-oxo-1-azatricyclo[6.4.1.0^[4,13]]trideca-4(13),5,7-trien-11-yl]carbamate | 1108.45 | (400 MHz, DMSO-$d_6$) δ 10.16 (s, 1H), 8.99 (s, 1H), 8.38 (d, J = 7.6 Hz, 2H), 7.80 (d, J = 9.3 Hz, 1H), 7.49-7.36 (m, 5H), 7.34 (d, J = 10.0 Hz, 1H), 7.16-7.07 (m, 3H), 7.04 (d, J = 7.8 Hz, 1H), 6.98-6.91 (m, 1H), 6.84-6.77 (m, 1H), 6.75-6.70 (m, 1H), 5.13-5.11 (m, 2H), 4.96-4.92 (m, 1H), 4.52 (d, J = 9.4 Hz, 1H), 4.43 (t, J = 8.1 Hz, 1H), 4.36 (d, J = 4.2 Hz, 2H), 4.28 (d, J = 5.8 Hz, 2H), 4.12-3.99 (m, 1H), 3.79-3.78 (m, 2H), 3.61 (d, J = 3.5 Hz, 2H), 3.53-3.39 (m, 1H), 3.35 (s, 5H), 3.18-2.91 (m, 2H), 2.58-2.52 (m, 3H), 2.46 (s, 3H), 2.31-2.09 (m, 2H), 2.07-1.75 (m, 2H), 1.60-1.48 (m, 4H), 1.39 (s, 9H), 1.32-1.21 (m, 2H), 0.93 (s, 9H) |
| I171 | 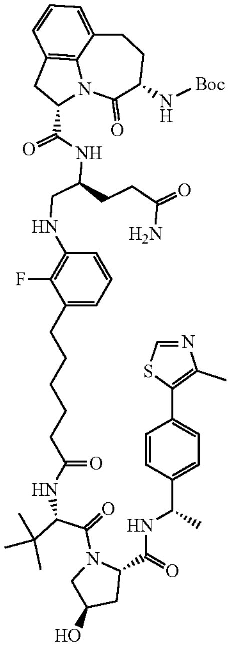 [SMILES: Cc1ncsc1-c1ccc([C@H](C)NC(=O)[C@@H]2C[C@@H](O)CN2C(=O)[C@@H](NC(=O)CCCCCc2cccc(NC[C@H](CCC(N)=O)NC(=O)[C@@H]3Cc4cccc5c4N3C(=O)[C@@H](NC(=O)OC(C)(C)C)CC5)c2F)C(C)(C)C)cc1] | tert-butyl N-[(2S,11S)-2-[(4-carbamoyl-1-[[2-fluoro-3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenyl]amino]butan-2-yl)carbamoyl]-12-oxo-1-azatricyclo[6.4.1.0^[4,13]]trideca-4(13),5,7-trien-11-yl]carbamate | 1094.50 | (400 MHz, DMSO-$d_6$) δ 8.99 (s, 1H), 8.38 (d, J = 7.8 Hz, 1H), 7.96 (t, J = 8.7 Hz, 1H), 7.80 (d, J = 9.3 Hz, 1H), 7.44 (d, J = 8.3 Hz, 2H), 7.39 (d, J = 8.2 Hz, 2H), 7.23 (d, J = 14.6 Hz, 1H), 7.10 (d, J = 7.8 Hz, 1H), 7.08-7.00 (m, 3H), 7.01-6.91 (m, 1H), 6.83 (t, J = 7.8 Hz, 1H), 6.72 (s, 1H), 6.62 (t, J = 8.4 Hz, 1H), 6.40 (t, J = 7.1 Hz, 1H), 5.28 (s, 1H), 5.10 (d, J = 3.6 Hz, 1H), 5.03-4.87 (m, 2H), 4.52 (d, J = 9.3 Hz, 1H), 4.43 (t, J = 8.0 Hz, 1H), 4.28 (s, 1H), 4.05 (s, 1H), 3.83 (s, 1H), 3.61 (s, 1H), 3.43-3.39 (m, 1H), 3.33-3.29 (m, 1H), 3.10-3.06 (m, 4H), 3.06-2.97 (m, 1H), 2.84-2.80 (m, 2H), 2.46 (s, 3H), 2.28-2.24 (m, 1H), 2.15-2.11 (m, 1H), 2.07-2.03 (m, 5H), 1.85-1.74 (m, 1H), 1.66-1.56 (m, 1H), 1.54-1.50 (m, 5H), 1.39 (s, 9H), 1.41-1.37 (m, 2H), 1.27-1.23 (m, 2H), 0.94 (s, 9H) |

TABLE 50-continued

| Characterization data for intermediates prepared according to above. | | | | |
|---|---|---|---|---|
| Inter-mediate | Structure | Chemical Name | MS: [(M + 1)]+ | $^1$H NMR |
| I172 | 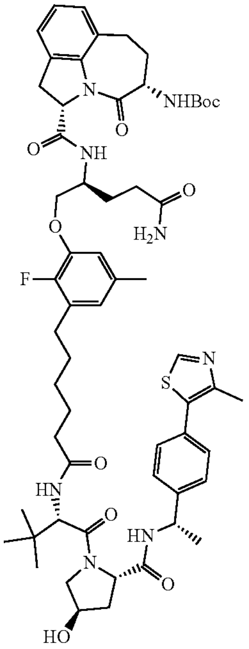 [SMILES: Cc1cc(CCCCCC(=O)N[C@H](C(=O)N2C[C@H](O)C[C@H]2C(=O)N[C@@H](C)c2ccc(-c3scnc3C)cc2)C(C)(C)C)c(F)c(OC[C@H](CCC(N)=O)NC(=O)[C@@H]2Cc3cccc4c3N2C(=O)[C@@H](NC(=O)OC(C)(C)C)CC4)c1] | tert-butyl N-[(2S,11S)-2-[[(2S)-4-carbamoyl-1-[2-fluoro-3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)-5-methylphenoxy]butan-2-yl]carbamoyl]-12-oxo-1-azatricyclo[6.4.1.0^[4,13]]trideca-4(13),5,7-trien-11-yl]carbamate | 1109.50 | (300 MHz, DMSO-$d_6$) δ 8.97 (s, 1H), 8.35 (d, J = 7.8 Hz, 1H), 8.04 (d, J = 7.4 Hz, 1H), 7.77 (d, J = 9.2 Hz, 1H), 7.40 (q, J = 8.2 Hz, 4H), 7.22 (s, 1H), 7.11-6.99 (m, 3H), 6.99-6.88 (m, 1H), 6.78 (dd, J = 7.8, 2.0 Hz, 1H), 6.72 (s, 1H), 6.65-6.56 (m, 1H), 5.12-4.98 (m, 2H), 4.97-4.85 (m, 1H), 4.51 (d, J = 9.3 Hz, 1H), 4.43 (q, J = 8.0, 6.7 Hz, 1H), 4.27 (s, 1H), 4.08-3.86 (m, 4H), 3.64-3.57 (m, 2H), 3.48-3.25 (m, 5H), 3.17-2.96 (m, 2H), 2.91-2.79 (m, 1H), 2.59-2.51 (m, 2H), 2.45 (s, 3H), 2.30-2.23 (m, 1H), 2.21 (s, 3H), 2.18-2.09 (m, 3H), 2.01-1.95 (m, 1H), 1.84-1.78 (m, 1H), 1.74-1.67 (m, 1H), 1.60-1.42 (m, 5H), 1.38 (s, 9H), 1.35 (s, 3H), 0.92 (s, 9H) |
| I173 | 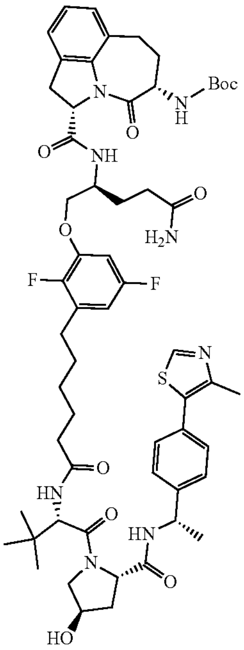 [SMILES: Cc1ncsc1-c1ccc([C@H](C)NC(=O)[C@@H]2C[C@@H](O)CN2C(=O)[C@@H](NC(=O)CCCCCc2cc(F)cc(OC[C@H](CCC(N)=O)NC(=O)[C@@H]3Cc4cccc5c4N3C(=O)[C@@H](NC(=O)OC(C)(C)C)CC5)c2F)C(C)(C)C)cc1] | tert-butyl N-[(2S,11S)-2-[[(2S)-4-carbamoyl-1-[2,5-difluoro-3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenoxy]butan-2-yl]carbamoyl]-12-oxo-1-azatricyclo[6.4.1.0^[4,13]]trideca-4(13),5,7-trien-11-yl]carbamate | 1113.55 | (400 MHz, CD3OD) δ 8.88 (s, 1H), 7.49-7.35 (m, 4H), 7.12-7.06 (m, 2H), 7.04-6.97 (m, 1H), 6.82-6.74 (m, 1H), 6.61-6.54 (m, 1H), 5.14 (dd, J = 11.0, 3.5 Hz, 1H), 5.06-4.99 (m, 1H), 4.67-4.62 (m, 1H), 4.58 (t, J = 8.2 Hz, 1H), 4.45 (br, 1H), 4.29-4.21 (m, 2H), 4.10 (dd, J = 9.9, 4.6 Hz, 1H), 4.04-3.97 (m, 1H), 3.89 (d, J = 11.1 Hz, 1H), 3.80-3.71 (m, 1H), 3.55-3.46 (m, 1H), 3.23-3.13 (m, 2H), 3.06 (dd, J = 16.5, 3.5 Hz, 1H), 2.64 (t, J = 7.5 Hz, 2H), 2.50 (s, 3H), 2.37 (t, J = 7.5 Hz, 2H), 2.33-2.16 (m, 5H), 2.11-1.80 (m, 2H), 1.71-1.55 (m, 5H), 1.52 (d, J = 7.0 Hz, 3H), 1.48 (s, 9H), 1.44-1.34 (m, 2H), 1.05 (s, 9H) |

TABLE 50-continued

Characterization data for intermediates prepared according to above.

| Inter-mediate | Structure | Chemical Name | MS: [(M + 1)]$^+$ | $^1$H NMR |
|---|---|---|---|---|
| I174 | 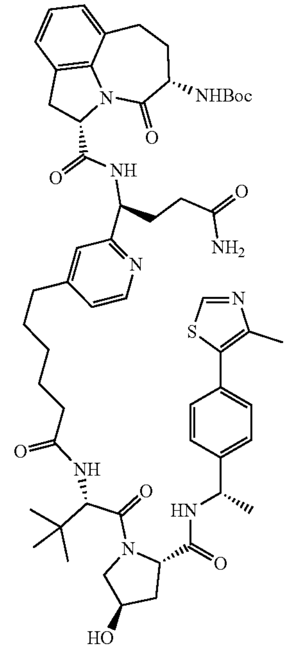 [SMILES: Cc1ncsc1-c1ccc([C@H](C)NC(=O)[C@@H]2C[C@@H](O)CN2C(=O)[C@@H](NC(=O)CCCCCc2ccnc([C@H](CCC(N)=O)NC(=O)[C@@H]3Cc4cccc5c4N3C(=O)[C@@H](NC(=O)OC(C)(C)C)CC5)c2)C(C)(C)C)cc1] | tert-butyl N-[(2S,11S)-2-[[(1S)-3-carbamoyl-1-[4-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)pyridin-2-yl]propyl]carbamoyl]-12-oxo-1-azatricyclo[6.4.1.0^[4,13]]trideca-4(13),5,7-trien-11-yl]carbamate | 1048.45 | (300 MHz, DMSO-$d_6$) δ 8.97 (s, 1H), 8.61-8.59 (d, J = 7.8 Hz, 1H), 8.38-8.34 (t, J = 6.8 Hz, 2H), 7.79-7.76 (d, J = 9.2 Hz, 1H), 7.47-7.31 (q, J = 8.4 Hz, 4H), 7.22 (s, 1H), 7.16-6.98 (m, 5H), 6.96-6.85 (m, 1H), 6.74 (s, 1H), 5.10-5.06 (m, 2H), 4.96-4.87 (p, J = 6.9 Hz, 1H), 4.68-4.61 (q, J = 7.3 Hz, 1H), 4.52-4.49 (d, J = 9.3 Hz, 1H), 4.45-4.39 (t, J = 8.0 Hz, 1H), 4.27 (s, 1H), 4.08-4.02 (d, J = 7.7 Hz, 1H), 3.61-3.60 (d, J = 3.4 Hz, 2H), 3.50-3.41 (m, 1H), 3.04-3.02 (m, 2H), 2.94 (s, 3H), 2.80-2.74 (d, J = 2.4 Hz, 1H), 2.68-2.64 (m, 2H), 2.45 (s, 3H), 2.24-2.16 (m, 1H), 2.17-2.08 (m, 2H), 2.09-2.03 (d, J = 9.5 Hz, 2H), 1.92-1.73 (m, 3H), 1.66-1.60 (m, 2H), 1.55-1.45 (m, 2H), 1.38 (s, 9H), 1.30-1.25 (m, 3H), 0.92 (s, 9H) |
| I175 | 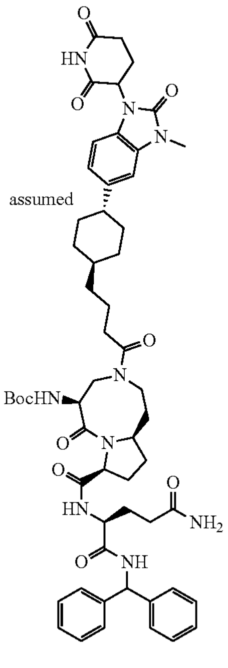 [SMILES: Cn1c(=O)n(C2CCC(=O)NC2=O)c2ccc([C@H]3CC[C@H](CCCC(=O)N4CC[C@H]5CC[C@@H](C(=O)N[C@@H](CCC(N)=O)C(=O)NC(c6ccccc6)c6ccccc6)N5C(=O)[C@@H](NC(=O)OC(C)(C)C)C4)CC3)cc21] | tert-butyl N-[(5S,8S,10aR)-8-[[(1S)-3-carbamoyl-1-(diphenylmethylcarbamoyl)propyl]carbamoyl]-6-oxo-3-[4-[(1r,4s)-4-[1-(2,6-dioxopiperidin-3-yl)-3-methyl-2-oxo-1,3-benzodiazol-5-yl]cyclohexyl]butanoyl]-octahydropyrrolo[1,2-a][1,5]diazocin-5-yl]carbamate | 1030.55 | (300 MHz, CD3OD) δ 8.73 (s, 1H), 7.33-7.26 (m, 10H), 7.08-7.06 (m 1H), 7.04-6.97 (m, 2H), 6.17-6.11 (m, 1H), 5.33-5.30 (m, 1H), 4.61 (d, J = 9.9 Hz, 1H), 4.45-4.41 (m, 2H), 4.25-4.23 (m, 1H), 3.82-3.77 (m, 2H), 3.45-3.40 (m, 3H), 2.95-2.75 (m, 3H), 2.64-2.59 (m, 3H), 2.35 (d, J = 8.3 Hz, 2H), 2.20-2.14 (m, 4H), 1.96 (d, J = 9.7 Hz, 3H), 1.78-1.61 (m, 15H), 1.58-1.50 (m, 2H), 1.45 (s, 9H) |

TABLE 50-continued

Characterization data for intermediates prepared according to above.

| Inter-mediate | Structure | Chemical Name | MS: [(M + 1)]$^+$ | $^1$H NMR |
|---|---|---|---|---|
| I176 | 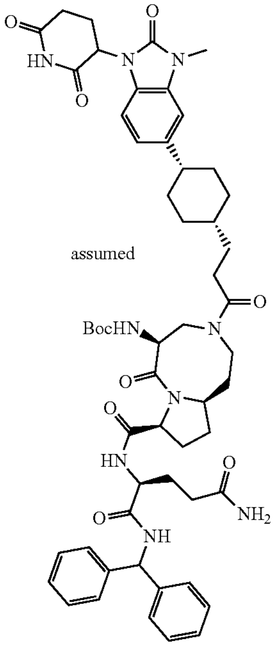 [SMILES: Cn1c(=O)n(C2CCC(=O)NC2=O)c2ccc([C@H]3CC[C@@H](CCC(=O)N4CC[C@H]5CC[C@@H](C(=O)N[C@@H](CCC(N)=O)C(=O)NC(c6ccccc6)c6ccccc6)N5C(=O)[C@@H](NC(=O)OC(C)(C)C)C4)CC3)cc21] assumed | tert-butyl N-[(5S,8S,10aR)-8-[[(1S)-3-carbamoyl-1-(diphenylmethyl carbamoyl) propyl]carbamoyl]-6-oxo-3-[3-[(1s,4s)-4-[1-(2,6-dioxopiperidin-3-yl)-3-methyl-2-oxo-1,3-benzodiazol-5-yl]cyclohexyl]propanoyl]-octahydropyrrolo[1,2-a][1,5]diazocin-5-yl]carbamate | 1016.50 | (300 MHz, DMSO-$d_6$) δ 11.09 (s, 1H), 8.73 (d, J = 8.4 Hz, 1H), 8.19 (t, J = 6.4 Hz, 1H), 7.41-7.20 (m, 10H), 7.09-6.85 (m, 3H), 6.73 (d, J = 12.2 Hz, 1H), 6.49 (d, J = 6.8 Hz, 1H), 6.11 (d, J = 8.3 Hz, 1H), 5.34 (dd, J = 12.8, 5.4 Hz, 1H), 4.53-4.24 (m, 3H), 4.15-4.11 (m, 2H), 3.74-3.71 (m, 3H), 3.27-3.06 (m, 4H), 2.89-2.58 (m, 4H), 2.15-2.13 (m, 4H), 1.88-1.62 (m, 12H), 1.69-1.45 (m, 4H), 1.40 (s, 9H), 1.07-1.05 (m, 4H) |
| I177 | 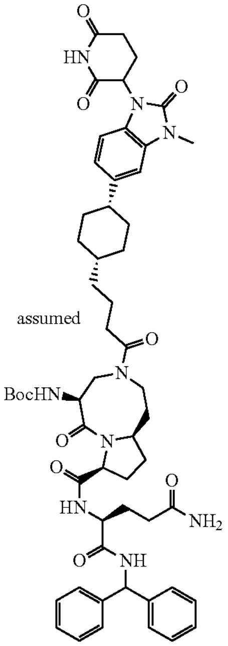 [SMILES: Cn1c(=O)n(C2CCC(=O)NC2=O)c2ccc([C@H]3CC[C@@H](CCCC(=O)N4CC[C@H]5CC[C@@H](C(=O)N[C@@H](CCC(N)=O)C(=O)NC(c6ccccc6)c6ccccc6)N5C(=O)[C@@H](NC(=O)OC(C)(C)C)C4)CC3)cc21] assumed | tert-butyl N-(5S,8S,10aR)-8-[[(1S)-3-carbamoyl-1-(diphenylmethyl carbamoyl) propyl]carbamoyl]-6-oxo-3-[4-[(1s,4r)-4-[1-(2,6-dioxopiperidin-3-yl)-3-methyl-2-oxo-1,3-benzodiazol-5-yl]cyclohexyl]butanoyl]-octahydropyrrolo[1,2-a][1,5]diazocin-5-yl]carbamate | 1030.55 | (300 MHz, CD3OD) δ 7.39-7.21 (m, 10H), 7.05-6.97 (m, 3H), 6.14 (d, J = 6.3 Hz, 1H), 5.33-5.30 (m, 1H), 4.62 (d, J = 11.9 Hz, 1H), 4.46-4.40 (m, 2H), 4.25-4.23 (m, 1H), 3.81-3.77 (m, 2H), 3.41 (m, 3H), 3.10-2.86 (m, 2H), 2.81 (d, J = 4.9 Hz, 1H), 2.78-2.76 (m, 1H), 2.55-2.51 (m, 2H), 2.39-2.36 (m, 2H), 2.28-2.10 (m, 4H), 1.99-1.90 (m, 8H), 1.78-1.74 (m, 3H), 1.57-1.53 (m, 2H), 1.46 (s, 9H), 1.45-1.05 (m, 7H) |

TABLE 50-continued

| Characterization data for intermediates prepared according to above. | | | | |
|---|---|---|---|---|
| Inter-mediate | Structure | Chemical Name | MS: [(M + 1)]+ | $^1$H NMR |
| I178 | 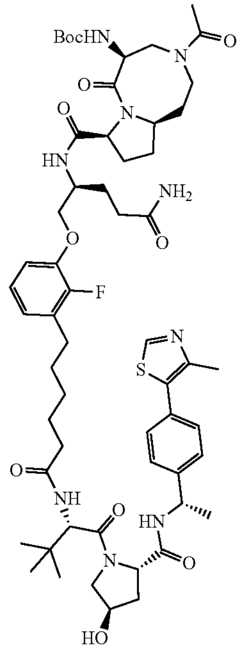 [SMILES: CC(=O)N1CC[C@H]2CC[C@@H](C(=O)N[C@@H](CCC(N)=O)COc3cccc(CCCCCC(=O)N[C@H](C(=O)N4C[C@H](O)C[C@H]4C(=O)N[C@@H](C)c4ccc(-c5scnc5C)cc4)C(C)(C)C)c3F)N2C(=O)[C@@H](NC(=O)OC(C)(C)C)C1] | tert-butyl N-[(5S,8S,10aR)-3-acetyl-8-[[(2S)-4-carbamoyl-1-[2-fluoro-3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenoxy]butan-2-yl]carbamoyl]-6-oxo-octahydropyrrolo[1,2-a][1,5]diazocin-5-yl]carbamate | 1118.55 | (400 MHz, DMSO-$d_6$) δ 8.99 (s, 1H), 8.38 (d, J = 7.8 Hz, 1H), 8.02 (t, J = 7.4 Hz, 1H), 7.80 (d, J = 9.3 Hz, 1H), 7.44 (d, J = 8.2 Hz, 2H), 7.39 (d, J = 8.2 Hz, 2H), 7.19 (s, 1H), 7.08-6.96 (m, 2H), 6.86-6.78 (m, 1H), 6.74 (s, 1H), 6.67-6.56 (m, 1H), 5.10 (d, J = 3.5 Hz, 1H), 4.92 (q, J = 7.5 Hz, 1H), 4.55-4.39 (m, 2H), 4.37-4.26 (m, 2H), 4.18 (d, J = 9.8 Hz, 1H), 4.04 (s, 1H), 3.98 (t, J = 7.2 Hz, 1H), 3.92-3.88 (m, 1H), 3.66 (d, J = 12.6 Hz, 1H), 3.61 (s, 3H), 3.52-3.35 (m, 1H), 3.24-3.13 (m, 1H), 2.58-2.54 (m, 3H), 2.46 (s, 3H), 2.32-2.18 (m, 2H), 2.17-2.05 (m, 4H), 2.03-1.97 (m, 2H), 1.92-1.76 (m, 3H), 1.74-1.65 (m, 2H), 1.52-1.48 (m, 4H), 1.39 (s, 9H), 1.37 (s, 3H), 1.37-1.23 (m, 6H), 0.93 (s, 9H) |
| I179 | 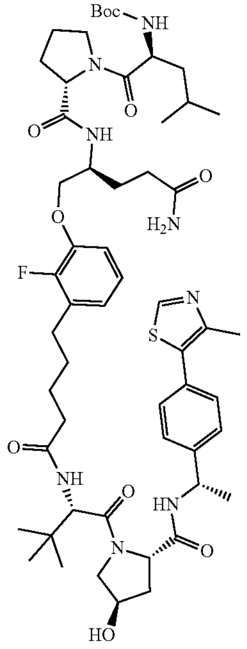 [SMILES: Cc1ncsc1-c1ccc([C@H](C)NC(=O)[C@@H]2C[C@@H](O)CN2C(=O)[C@@H](NC(=O)CCCCc2cccc(OC[C@H](CCC(N)=O)NC(=O)[C@@H]3CCCN3C(=O)[C@H](CC(C)C)NC(=O)OC(C)(C)C)c2F)C(C)(C)C)cc1] | tert-butyl N-[(2S)-1-[(2S)-2-[[(2S)-4-carbamoyl-1-[2-fluoro-3-(4-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]butyl)phenoxy]butan-2-yl]carbamoyl]pyrrolidin-1-yl]-4-methyl-1-oxopentan-2-yl]carbamate | 1063.55 | (400 MHz, DMSO-$d_6$) δ 8.99 (s, 1H), 8.37 (d, J = 7.8 Hz, 1H), 7.83 (t, J = 8.5 Hz, 2H), 7.44 (d, J = 8.0 Hz, 2H), 7.38 (d, J = 8.3 Hz, 2H), 7.16 (s, 1H), 7.06-6.88 (m, 3H), 6.82 (s, 1H), 6.73 (s, 1H), 5.10 (s, 1H), 4.92 (t, J = 7.3 Hz, 1H), 4.52 (d, J = 9.3 Hz, 1H), 4.43 (t, J = 8.0 Hz, 1H), 4.29 (s, 2H), 4.21 (s, 1H), 3.98 (d, J = 13.6 Hz, 2H), 3.94-3.90 (m, 1H), 3.66-3.55 (m, 3H), 3.53-3.49 (m, 1H), 2.59-2.56 (m, 3H), 2.46 (s, 3H), 2.34-2.26 (m, 1H), 2.16-2.12 (m, 3H), 2.03-1.98 (m, 3H), 1.92-1.72 (m, 2H), 1.71-1.63 (m, 1H), 1.57-1.43 (m, 5H), 1.37 (s, 9H), 1.33-1.23 (m, 3H), 0.93 (s, 9H), 0.91-0.82 (m, 9H) |

TABLE 50-continued

| Inter-mediate | Structure | Chemical Name | MS: [(M + 1)]+ | 1H NMR |
|---|---|---|---|---|
| Characterization data for intermediates prepared according to above. | | | | |
| I180 | 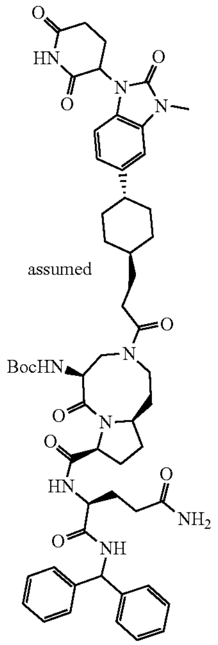 [SMILES: Cn1c(=O)n(C2CCC(=O)NC2=O)c2ccc([C@H]3CC[C@H](CCC(=O)N4CC[C@H]5CC[C@@H](C(=O)N[C@@H](CCC(N)=O)C(=O)NC(c6ccccc6)c6ccccc6)N5C(=O)[C@@H](NC(=O)OC(C)(C)C)C4)CC3)cc21] assumed | tert-butyl N-(5S,8S,10aR)-8-[[(1S)-3-carbamoyl-1-(diphenyl-methylcarbamoyl)propyl]carbamoyl]-6-oxo-3-[3-[(1r,4r)-4-[1-(2,6-dioxopiperidin-3-yl)-3-methyl-2-oxo-1,3-benzodiazol-5-yl]cyclohexyl]propanoyl]-octahydropyrrolo[1,2-a][1,5]diazocin-5-yl]carbamate | 1016.50 | (300 MHz, DMSO-$d_6$) δ 11.09 (s, 1H), 8.73 (d, J = 8.4 Hz, 1H), 8.21 (d, J = 7.3 Hz, 1H), 7.31 (q, J = 7.7, 6.8 Hz, 11H), 7.14-6.88 (m, 3H), 6.75 (s, 1H), 6.47 (d, J = 6.6 Hz, 1H), 6.11 (d, J = 8.4 Hz, 1H), 5.77 (d, J = 1.0 Hz, 1H), 5.40-5.25 (m, 1H), 4.41 (dd, J = 23.7, 14.0 Hz, 3H), 4.15-4.13 (m, 1H), 3.76 (d, J = 14.4 Hz, 1H), 2.90-2.84 (m, 4H), 2.79-2.58 (m, 5H), 2.24-1.86 (m, 11H), 1.85-1.53 (m, 13H), 1.39 (s, 9H) |
| I181 | 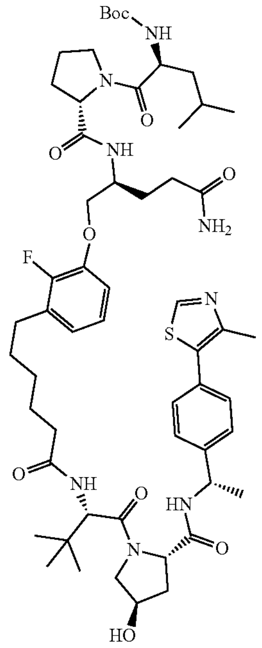 [SMILES: Cc1ncsc1-c1ccc([C@H](C)NC(=O)[C@@H]2C[C@@H](O)CN2C(=O)[C@@H](NC(=O)CCCCCc2cccc(OC[C@H](CCC(N)=O)NC(=O)[C@@H]3CCCN3C(=O)[C@H](CC(C)C)NC(=O)OC(C)(C)C)c2F)C(C)(C)C)cc1] | tert-butyl N-[(2S)-1-[(2S)-2-[[(2S)-4-carbamoyl-1-[2-fluoro-3-(5-[[(2S)-1-[(2S,4R)-4-hydroxy-2-[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenoxy]butan-2-yl]carbamoyl]pyrrolidin-1-yl]-4-methyl-1-oxopentan-2-yl]carbamate | 1077.15 | (300 MHz, CD3OD) δ 8.88 (s, 1H), 7.47-7.40 (m, 4H), 7.00-6.89 (m, 2H), 6.84-6.77 (m, 1H), 5.03-5.00 (m, 1H), 4.64-4.54 (m, 2H), 4.44-4.41 (m, 3H), 4.25-4.21 (m, 1H), 4.07-4.02 (m, 1H), 3.98-3.96 (m, 1H), 3.91-3.80 (m, 2H), 3.77-3.76 (m, 1H), 3.64-3.62 (m, 1H), 2.65-2.62 (m, 2H), 2.49 (s, 3H), 2.40-2.36 (m, 2H), 2.32-2.25 (m, 2H), 2.22-2.14 (m, 2H), 2.10-2.05 (m, 1H), 1.98-1.95 (m, 3H), 1.66-1.61 (m, 5H), 1.55-1.51 (m, 4H), 1.44 (s, 9H), 1.41-1.29 (m, 4H), 1.04 (s, 9H), 0.99-0.93 (m, 6H) |

TABLE 50-continued

Characterization data for intermediates prepared according to above.

| Inter-mediate | Structure | Chemical Name | MS: [(M + 1)]+ | $^1$H NMR |
|---|---|---|---|---|
| I182 | 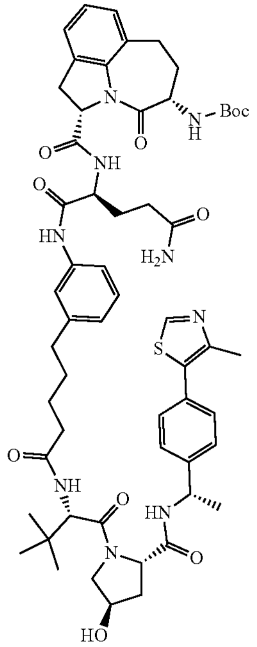 [SMILES: Cc1ncsc1-c1ccc([C@H](C)NC(=O)[C@@H]2C[C@@H](O)CN2C(=O)[C@@H](NC(=O)CCCCc2cccc(NC(=O)[C@H](CCC(N)=O)NC(=O)[C@@H]3Cc4cccc5c4N3C(=O)[C@@H](NC(=O)OC(C)(C)C)CC5)c2)C(C)(C)C)cc1] | tert-butyl N-[(2S,11S)-2-[[(1S)-3-carbamoyl-1-[[3-(4-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]butyl)phenyl]carbamoyl]propyl]carbamoyl]-12-oxo-1-azatricyclo[6.4.1.0^[4,13]]trideca-4(13),5,7-trien-11-yl]carbamate | 1076.60 | (300 MHz DMSO-$d_6$) δ 9.94 (s, 1H), 9.00 (s, 1H), 8.35 (dd, J = 16.5, 7.4 Hz, 2H), 7.81 (d, J = 9.2 Hz, 1H), 7.50-7.35 (m, 6H), 7.32 (s, 1H), 7.20 (s, 1H), 7.16-7.00 (m, 2H), 6.93 (dd, J = 25.3, 7.5 Hz, 1H), 6.79 (s, 1H), 5.16-5.10 (m, 2H), 4.96-4.91 (m, 1H), 4.53 (d, J = 9.2 Hz, 1H), 4.43 (t, J = 7.9 Hz, 1H), 4.33-4.28 (m, 2H), 4.10-4.04 (m, 1H), 3.62 (s, 2H), 3.09-2.98 (m, 3H), 2.47 (s, 3H), 2.33-2.27 (m, 1H), 2.20-1.73 (m, 10H), 1.58-1.48 (m, 6H), 1.41-1.36 (m, 14H), 0.95 (s, 9H) |
| I183 | 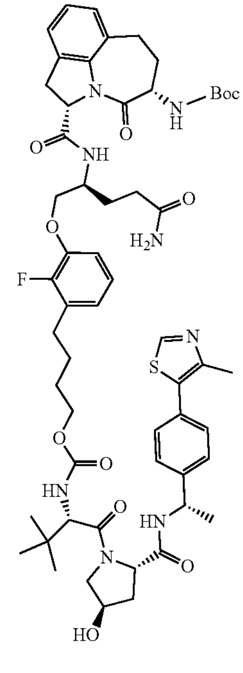 [SMILES: Cc1ncsc1-c1ccc([C@H](C)NC(=O)[C@@H]2C[C@@H](O)CN2C(=O)[C@@H](NC(=O)OCCCCc2cccc(OC[C@H](CCC(N)=O)NC(=O)[C@@H]3Cc4cccc5c4N3C(=O)[C@@H](NC(=O)OC(C)(C)C)CC5)c2F)C(C)(C)C)cc1] | 4-[3-[(2S)-2-[[(2S,11S)-11-[(tert-butoxycarbonyl)amino]-12-oxo-1-azatricyclo[6.4.1.0^[4,13]]trideca-4(13),5,7-trien-2-yl]formamido]-4-carbamoylbutoxy]-2-fluorophenyl]butyl N-[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamate | 1097.80 | (400 MHz, DMSO-$d_6$) δ 8.99 (s, 1H), 8.39 (d, J = 7.8 Hz, 1H), 8.09 (d, J = 7.4 Hz, 1H), 7.48-7.41 (m, 2H), 7.45-7.33 (m, 2H), 7.24 (s, 1H), 7.13-6.90 (m, 7H), 6.86-6.82 (m, 1H), 6.74 (s, 1H), 5.11 (s, 1H), 5.05-5.01 (m, 1H), 4.93-4.89 (m, 1H), 4.44 (t, J = 8.0 Hz, 1H), 4.28 (s, 1H), 4.17 (d, J = 9.0 Hz, 1H), 4.06-3.98 (m, 2H), 3.98-3.94 (m, 5H), 3.62-3.58 (m, 2H), 2.86 (d, J = 16.5 Hz, 1H), 2.62 (s, 3H), 2.46 (s, 3H), 2.16-2.12 (m, 2H), 2.07-1.98 (m, 3H), 1.61-1.57 (m, 5H), 1.41-1.34 (m, 12H), 1.33-1.24 (m, 1H), 1.27-1.23 (m, 2H), 0.94 (s, 9H) |

TABLE 50-continued

Characterization data for intermediates prepared according to above.

| Intermediate | Structure | Chemical Name | MS: [(M + 1)]$^+$ | $^1$H NMR |
|---|---|---|---|---|
| I188 | 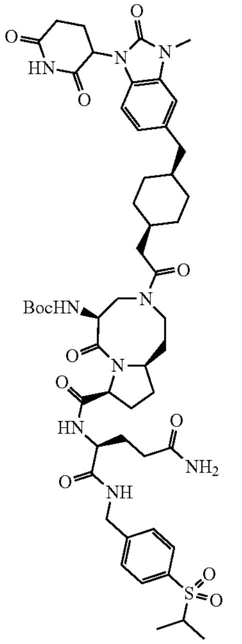 [SMILES: CC(C)S(=O)(=O)c1ccc(CNC(=O)[C@H](CCC(N)=O)NC(=O)[C@@H]2CC[C@@H]3CCN(C(=O)C[C@H]4CC[C@@H](Cc5ccc6c(c5)n(C)c(=O)n6C5CCC(=O)NC5=O)CC4)C[C@H](NC(=O)OC(C)(C)C)C(=O)N32)cc1] | tert-butyl N-[(5S,8S,10aR)-8-[[(1S)-3-carbamoyl-1-([[4-(propane-2-sulfonyl)phenyl]methyl]carbamoyl)propyl]carbamoyl]-6-oxo-3-[2-[(1s,4s)-4-[[1-(2,6-dioxopiperidin-3-yl)-3-methyl-2-oxo-1,3-benzodiazol-5-yl]methyl]cyclohexyl]acetyl]-octahydropyrrolo[1,2-a][1,5]diazocin-5-yl]carbamate | 1046.45 | (400 MHz, DMSO-$d_6$) δ 11.09 (s, 1H), 8.53 (t, J = 6.0 Hz, 1H), 8.28 (t, J = 7.4 Hz, 1H), 7.81-7.76 (m, 2H), 7.53 (t, J = 6.6 Hz, 2H), 7.24 (s, 1H), 7.03-6.94 (m, 2H), 6.87-6.69 (m, 2H), 6.54 (d, J = 6.8 Hz, 1H), 5.34 (dd, J = 12.7, 5.4 Hz, 1H), 4.47-4.35 (m, 5H), 4.25-4.20 (m, 1H), 3.84-3.72 (m, 2H), 3.43-3.36 (m, 2H), 3.32 (s, 3H), 3.25-2.99 (m, 1H), 2.95-2.86 (m, 1H), 2.77-2.55 (m, 6H), 2.45-2.25 (m, 1H), 2.23-2.10 (m, 4H), 2.04-1.92 (m, 5H), 1.87-1.53 (m, 6H), 1.45-1.32 (m, 12H), 1.16-1.13 (m, 8H) |
| I189 | 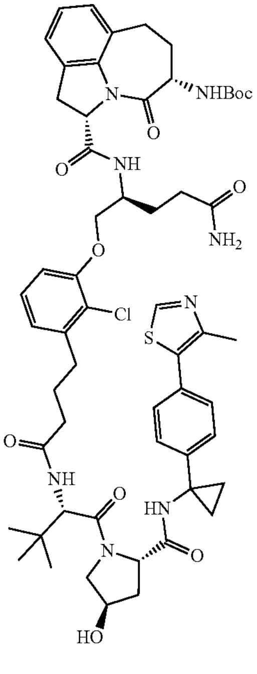 [SMILES: Cc1ncsc1-c1ccc(C2(NC(=O)[C@@H]3C[C@@H](O)CN3C(=O)[C@@H](NC(=O)CCCc3cccc(OC[C@H](CCC(N)=O)NC(=O)[C@@H]4Cc5cccc6c5N4C(=O)[C@@H](NC(=O)OC(C)(C)C)CC6)c3Cl)C(C)(C)C)CC2)cc1] | tert-butyl N-[(2S,11S)-2-[[(2S)-4-carbamoyl-1-[2-chloro-3-(3-[[(2S)-1-[(2S,4R)-4-hydroxy-2-([1-[4-(4-methyl-1,3-thiazol-5-yl)phenyl]cyclopropyl]carbamoyl)pyrrolidin-1-yl]-3,3-dimethyl-1-oxobutan-2-yl]carbamoyl]propyl)phenoxy]butan-2-yl]carbamoyl]-12-oxo-1-azatricyclo[6.4.1.0^[4,13]]trideca-4(13),5,7-trien-11-yl]carbamate | [(M − H)]$^-$ = 1093.50 | (300 MHz, DMSO-$d_6$) δ 8.98 (s, 1H), 8.86-8.79 (m, 1H), 8.16-8.00 (m, 2H), 7.37-7.28 (m, 3H), 7.25 (d, J = 7.9 Hz, 1H), 7.19 (d, J = 7.9 Hz, 1H), 7.12 (d, J = 8.1 Hz, 1H), 7.09-7.01 (m, 3H), 7.00-6.89 (m, 3H), 6.79-6.73 (m, 1H), 5.09-5.01 (m, 1H), 4.59 (d, J = 9.3 Hz, 1H), 4.45-4.38 (m, 2H), 4.08-3.94 (m, 4H), 3.69-3.64 (m, 2H), 3.13-2.90 (m, 4H), 2.76-2.68 (m, 2H), 2.45 (s, 3H), 2.38-2.31 (m, 1H), 2.26-2.12 (m, 3H), 2.09-1.97 (m, 3H), 1.94-1.72 (m, 6H), 1.40 (s, 9H), 1.27-1.14 (m, 4H), 0.96 (s, 9H) |

TABLE 50-continued

| Characterization data for intermediates prepared according to above. | | | | |
|---|---|---|---|---|
| Intermediate | Structure | Chemical Name | MS: [(M + 1)]$^+$ | $^1$H NMR |
| I190 | 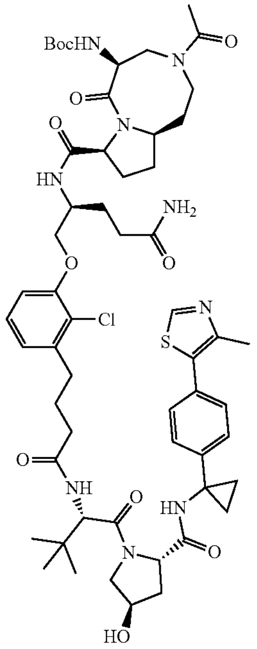 [SMILES: CC(=O)N1CC[C@H]2CC[C@@H](C(=O)N[C@@H](CCC(N)=O)COc3cccc(CCCC(=O)N[C@H](C(=O)N4C[C@H](O)C[C@H]4C(=O)NC4(c5ccc(-c6scnc6C)cc5)CC4)C(C)(C)C)c3Cl)N2C(=O)[C@@H](NC(=O)OC(C)(C)C)C1] | tert-butyl N-[(5S,8S,10aR)-3-acetyl-8-[[(2S)-4-carbamoyl-1-[2-chloro-3-(3-[[(2S)-1-[(2S,4R)-4-hydroxy-2-([1-[4-(4-methyl-1,3-thiazol-5-yl)phenyl]cyclopropyl]carbamoyl)pyrrolidin-1-yl]-3,3-dimethyl-1-oxobutan-2-yl]carbamoyl]propyl)phenoxy]butan-2-yl]carbamoyl]-6-oxo-octahydropyrrolo[1,2-a][1,5]diazocin-5-yl]carbamate | 1118.60 | (300 MHz, DMSO-$d_6$) δ 9.01 (s, 1H), 8.85-8.81 (m, 1H), 8.06-7.99 (m, 2H), 7.39-7.28 (m, 4H), 7.26-7.20 (m, 2H), 7.13-6.97 (m, 1H), 6.91 (d, J = 7.6 Hz, 1H), 6.76 (s, 1H), 6.69-6.55 (m, 1H), 4.58 (d, J = 9.2 Hz, 1H), 4.41-4.35 (m, 4H), 4.23-4.09 (m, 1H), 4.12-3.98 (m, 2H), 3.94-3.90 (m, 1H), 3.68-3.61 (m, 4H), 3.36-3.15 (m, 1H), 3.09-3.02 (m, 1H), 2.76-2.64 (m, 2H), 2.46 (s, 3H), 2.37-2.32 (m, 1H), 2.25-2.18 (m, 3H), 2.12-2.07 (m, 3H), 2.03-1.59 (m, 13H), 1.39 (s, 9H), 1.27-1.12 (m, 4H), 0.96 (s, 9H) |
| I191 | 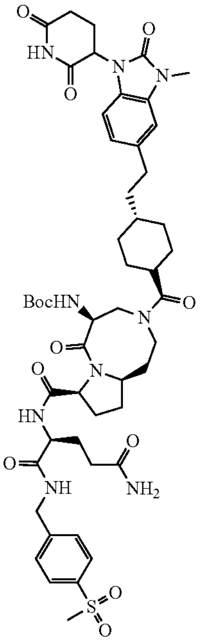 | tert-butyl N-[(5S,8S,10aR)-8-[[(1S)-3-carbamoyl-1-[[(4-methanesulfonylphenyl)methyl]carbamoyl]propyl]carbamoyl]-3-(4-[2-[1-(2,6-dioxopiperidin-3-yl)-3-methyl-2-oxo-1,3-benzodiazol-5-yl]ethyl]cyclohexane-carbonyl)-6-oxo-octahydropyrrolo[1,2-a][1,5]diazocin-5-yl]carbamate | 1018.35 | (300 MHz, DMSO-$d_6$) δ 11.10 (s, 1H), 8.53 (d, J = 6.5 Hz, 1H), 8.27 (d, J = 7.5 Hz, 1H), 7.87 (d, J = 8.3 Hz, 2H), 7.51 (d, J = 7.9 Hz, 2H), 7.23 (s, 1H), 7.01 (d, J = 8.9 Hz, 2H), 6.87 (d, J = 7.9 Hz, 1H), 6.77 (s, 1H), 6.57 (d, J = 6.9 Hz, 1H), 5.35 (dd, J = 12.8, 5.4 Hz, 1H), 4.48 (s, 1H), 4.40 (d, J = 5.2 Hz, 3H), 4.29-3.99 (m, 2H), 3.71 (d, J = 14.7 Hz, 2H), 3.20 (s, 3H), 3.00-2.72 (m, 1H), 2.70-2.58 (m, 3H), 2.14-2.10 (m, 4H), 2.09-2.05 (m, 6H), 2.04-2.01 (m, 7H), 1.84-1.79 (m, 5H), 1.66-1.61 (m, 2H), 1.49-1.47 (m, 2H), 1.40 (s, 9H), 1.19-1.15 (m, 3H) |

TABLE 50-continued

Characterization data for intermediates prepared according to above.

| Intermediate | Structure | Chemical Name | MS: [(M + 1)]$^+$ | $^1$H NMR |
|---|---|---|---|---|
| I192 | 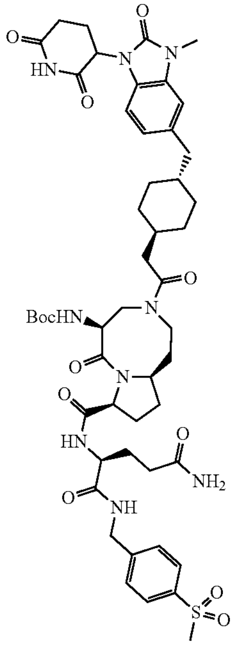 [SMILES: Cn1c(=O)n(C2CCC(=O)NC2=O)c2ccc(C[C@H]3CC[C@H](CC(=O)N4CC[C@H]5CC[C@@H](C(=O)N[C@@H](CCC(N)=O)C(=O)NCc6ccc(S(C)(=O)=O)cc6)N5C(=O)[C@@H](NC(=O)OC(C)(C)C)C4)CC3)cc21] | tert-butyl N-[(5S,8S,10aR)-8-[[(1S)-3-carbamoyl-1-[[(4-methanesulfonylphenyl)methyl]carbamoyl]propyl]carbamoyl]-6-oxo-3-[2-[(1r,4r)-4-[[1-(2,6-dioxopiperidin-3-yl)-3-methyl-2-oxo-1,3-benzodiazol-5-yl]methyl]cyclohexyl]acetyl]-octahydropyrrolo[1,2-a][1,5]diazocin-5-yl]carbamate | 1018.40 | (300 MHz, DMSO-d6) δ 11.11 (s, 1H), 8.58-8.48 (m, 1H), 8.25 (d, J = 7.6 Hz, 1H), 7.87 (dd, J = 8.2, 2.9 Hz, 2H), 7.52 (d, J = 8.0 Hz, 2H), 7.23 (s, 1H), 7.01 (d, J = 7.9 Hz, 2H), 6.83 (d, J = 8.0 Hz, 1H), 6.76 (d, J = 10.9 Hz, 1H), 6.62 (d, J = 7.1 Hz, 1H), 5.36 (dd, J = 12.7, 5.3 Hz, 1H), 4.49-4.33 (m, 4H), 4.27-4.18 (m, 1H), 4.14-4.07 (m, 1H), 3.68 (d, J = 12.7 Hz, 2H), 3.34 (s, 3H), 3.20 (s, 3H), 3.16-2.82 (m, 3H), 2.81-2.58 (m, 3H), 2.50-2.47 (m, 1H), 2.35-2.26 (m, 1H), 2.24-2.11 (m, 4H), 2.07-1.87 (m, 4H), 1.86-1.59 (m, 10H), 1.40 (s, 9H), 1.04-0.87 (m, 4H) |
| I193 | 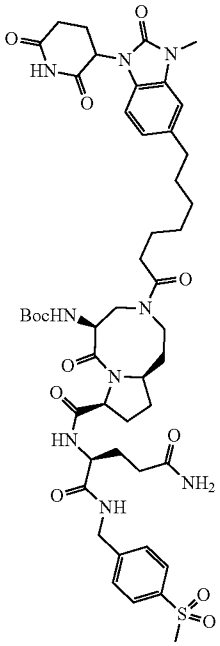 [SMILES: Cn1c(=O)n(C2CCC(=O)NC2=O)c2ccc(CCCCCCC(=O)N3CC[C@H]4CC[C@@H](C(=O)N[C@@H](CCC(N)=O)C(=O)NCc5ccc(S(C)(=O)=O)cc5)N4C(=O)[C@@H](NC(=O)OC(C)(C)C)C3)cc21] | tert-butyl N-[(5S,8S,10aR)-8-[[(1S)-3-carbamoyl-1-[[(4-methanesulfonylphenyl)methyl]carbamoyl]propyl]carbamoyl]-3-[7-[1-(2,6-dioxopiperidin-3-yl)-3-methyl-2-oxo-1,3-benzodiazol-5-yl]heptanoyl]-6-oxo-octahydropyrrolo[1,2-a][1,5]diazocin-5-yl]carbamate | 992.25 | (300 MHz, DMSO-$d_6$) δ 11.10 (s, 1H), 8.56-8.47 (m, 1H), 8.25 (d, J = 7.6 Hz, 1H), 7.87 (dd, J = 8.3, 1.6 Hz, 2H), 7.52 (d, J = 8.1 Hz, 2H), 7.23 (s, 1H), 7.05-6.98 (m, 2H), 6.87 (d, J = 7.7 Hz, 1H), 6.78 (s, 1H), 6.59 (d, J = 6.9 Hz, 1H), 5.35 (dd, J = 12.7, 5.4 Hz, 1H), 4.54-4.34 (m, 4H), 4.29-4.07 (m, 2H), 3.70 (d, J = 13.8 Hz, 2H), 3.34 (s, 3H), 3.19 (s, 3H), 3.15-3.07 (m, 1H), 2.99-2.84 (m, 1H), 2.80-2.55 (m, 4H), 2.49-2.26 (m, 2H), 2.23-2.11 (m, 3H), 2.07-1.91 (m, 3H), 1.90-1.72 (m, 4H), 1.72-1.47 (m, 6H), 1.40 (s, 9H), 1.37-1.28 (m, 4H) |

TABLE 50-continued

Characterization data for intermediates prepared according to above.

| Inter-mediate | Structure | Chemical Name | MS: [(M + 1)]+ | 1H NMR |
|---|---|---|---|---|
| I194 | 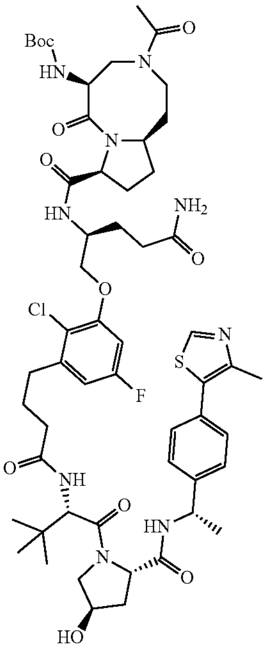 [SMILES: CC(=O)N1CC[C@H]2CC[C@@H](C(=O)N[C@@H](CCC(N)=O)COc3cc(F)cc(CCCC(=O)N[C@H](C(=O)N4C[C@H](O)C[C@H]4C(=O)N[C@@H](C)c4ccc(-c5scnc5C)cc4)C(C)(C)C)c3Cl)N2C(=O)[C@@H](NC(=O)OC(C)(C)C)C1] | tert-butyl N-[(5S,8S,10aR)-3-acetyl-8-[[(2S)-4-carbamoyl-1-[2-chloro-5-fluoro-3-(3-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]propyl)phenoxy]butan-2-yl]carbamoyl]-6-oxo-octahydropyrrolo[1,2-a][1,5]diazocin-5-yl]carbamate | 1123.90 | (300 MHz, DMSO-$d_6$) δ 9.00 (s, 1H), 8.38 (d, J = 7.7 Hz, 2H), 8.01-7.99 (m, 1H), 7.91 (d, J = 9.1 Hz, 1H), 7.48-7.36 (m, 4H), 7.20-7.00 (m, 2H), 6.78-6.59 (m, 3H), 5.11 (d, J = 3.4 Hz, 1H), 4.97-4.89 (m, 1H), 4.54-4.44 (m, 2H), 4.32-4.28 (m, 2H), 4.12-4.10 (m, 1H), 4.05-4.02 (m, 1H), 3.93-3.75 (m, 4H), 2.76-2.60 (m, 4H), 2.47 (s, 3H), 2.34-2.10 (m, 9H), 2.09-1.60 (m, 13H), 1.39 (s, 9H), 1.36 (d, J = 7.0 Hz, 3H), 0.96 (s, 9H) |
| I195 | 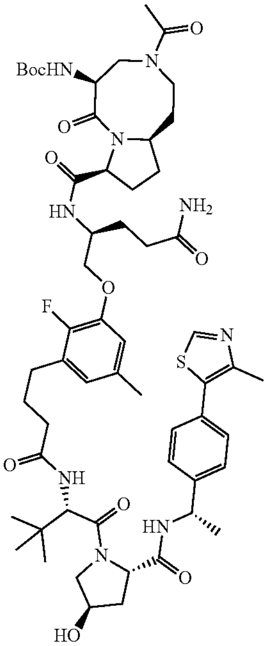 [SMILES: CC(=O)N1CC[C@H]2CC[C@@H](C(=O)N[C@@H](CCC(N)=O)COc3cc(C)cc(CCCC(=O)N[C@H](C(=O)N4C[C@H](O)C[C@H]4C(=O)N[C@@H](C)c4ccc(-c5scnc5C)cc4)C(C)(C)C)c3F)N2C(=O)[C@@H](NC(=O)OC(C)(C)C)C1] | tert-butyl N-[(5S,8S,10aR)-3-acetyl-8-[[(2S)-4-carbamoyl-1-[2-fluoro-3-(3-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]propyl)-5-methylphenoxy]butan-2-yl]carbamoyl]-6-oxo-octahydropyrrolo[1,2-a][1,5]diazocin-5-yl]carbamate | 1104.55 | (400 MHz, DMSO-$d_6$) δ 8.99 (s, 1H), 8.38 (d, J = 7.8 Hz, 1H), 8.05-7.97 (m, 1H), 7.87 (d, J = 9.2 Hz, 1H), 7.44 (d, J = 8.3 Hz, 2H), 7.44-7.35 (m, 2H), 7.19 (s, 1H), 6.82 (d, J = 7.7 Hz, 1H), 6.75 (s, 1H), 6.67-6.57 (m, 2H), 5.10 (d, J = 3.0 Hz, 1H), 4.92 (p, J = 7.4 Hz, 1H), 4.53 (d, J = 9.3 Hz, 1H), 4.49 (s, 1H), 4.43 (t, J = 8.0 Hz, 1H), 4.37-4.26 (m, 2H), 4.25-4.14 (m, 1H), 4.06-4.00 (m, 1H), 3.97 (d, J = 10.4 Hz, 1H), 3.92-3.84 (m, 1H), 3.71-3.59 (m, 4H), 3.18 (t, J = 12.6 Hz, 1H), 2.88-2.80 (m, 1H), 2.46 (s, 3H), 2.34-2.10 (m, 7H), 2.08 (d, J = 3.0 Hz, 3H), 2.00 (d, J = 8.6 Hz, 1H), 1.92-1.77 (m, 4H), 1.75-1.59 (m, 4H), 1.57-1.45 (m, 1H), 1.39 (s, 9H), 1.37 (s, 3H), 1.32-1.22 (m, 4H), 0.95 (s, 9H) |

TABLE 50-continued

| Characterization data for intermediates prepared according to above. | | | | |
|---|---|---|---|---|
| Intermediate | Structure | Chemical Name | MS: [(M + 1)]$^+$ | $^1$H NMR |
| I196 | 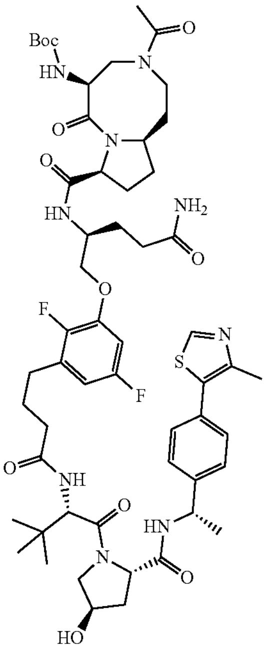 [SMILES: CC(=O)N1CC[C@H]2CC[C@@H](C(=O)N[C@@H](CCC(N)=O)COc3cc(F)cc(CCCC(=O)N[C@H](C(=O)N4C[C@H](O)C[C@H]4C(=O)N[C@@H](C)c4ccc(-c5scnc5C)cc4)C(C)(C)C)c3F)N2C(=O)[C@@H](NC(=O)OC(C)(C)C)C1] | tert-butyl N-[(5S,8S,10aR)-3-acetyl-8-[[(2S)-4-carbamoyl-1-[2,5-difluoro-3-(3-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]propyl)phenoxy]butan-2-yl]carbamoyl]-6-oxo-octahydropyrrolo[1,2-a][1,5]diazocin-5-yl]carbamate | 1108.56 | (300 MHz, DMSO-$d_6$) δ 9.00 (d, J = 1.3 Hz, 1H), 8.39 (d, J = 7.8 Hz, 1H), 8.04 (s, 1H), 7.91 (d, J = 9.0 Hz, 1H), 7.54-7.41 (m, 4H), 7.39-7.37 (m, 1H), 7.20-7.18 (m, 1H), 7.00 (s, 1H), 6.72 (d, J = 28.1 Hz, 1H), 6.09 (s, 1H), 4.94 (t, J = 7.1 Hz, 1H), 4.54 (d, J = 9.3 Hz, 1H), 4.44 (t, J = 8.0 Hz, 1H), 4.32-4.29 (m, 1H), 4.21-4.19 (m, 1H), 4.05-4.01 (m, 2H), 3.94-3.91 (m, 1H), 3.65-3.61 (m, 4H), 2.93-2.91 (m, 1H), 2.60-2.56 (m, 2H), 2.49 (s, 3H), 2.35-1.96 (m, 12H), 1.88-1.65 (m, 9H), 1.39-1.36 (m, 12H), 0.96 (s, 9H) |
| I197 | 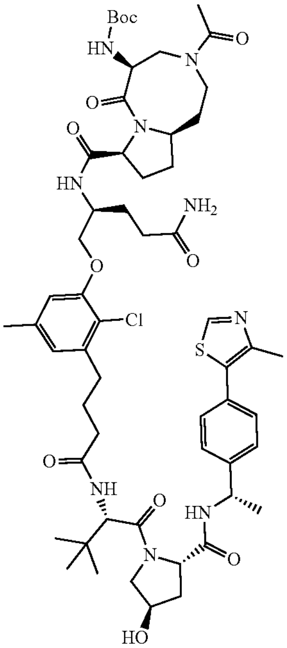 | tert-butyl ((5S,8S,10aR)-3-acetyl-8-(((S)-5-amino-1-(2-chloro-3-(4-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-4-oxobutyl)-5-methylphenoxy)-5-oxopentan-2-yl)carbamoyl)-6-oxodecahydropyrrolo[1,2-a][1,5]diazocin-5-yl)carbamate | 1120.45 | (300 MHz, DMSO-$d_6$) δ 9.00 (d, J = 1.2 Hz, 1H), 8.39 (d, J = 7.7 Hz, 1H), 8.01 (dd, J = 8.7, 3.2 Hz, 1H), 7.89 (d, J = 9.1 Hz, 1H), 7.50-7.35 (m, 4H), 7.21 (s, 1H), 6.85 (s, 1H), 6.76-6.72 (m, 2H), 6.69-6.52 (m, 1H), 5.12 (s, 1H), 4.99-4.89 (m, 1H), 4.57-4.51 (m, 1H), 4.44 (t, J = 8.1 Hz, 1H), 4.38-4.25 (m, 1H), 4.12-3.82 (m, 2H), 3.73-3.54 (m, 4H), 3.49-3.17 (m, 12H), 2.63 (t, J = 7.7 Hz, 2H), 2.47 (s, 3H), 2.34-2.16 (m, 6H), 2.10 (d, J = 1.3 Hz, 6H), 1.93-1.55 (m, 4H), 1.41-1.38 (d, J = 6.7 Hz, 12H), 0.97 (s, 9H) |

TABLE 50-continued

| Characterization data for intermediates prepared according to above. | | | | |
|---|---|---|---|---|
| Inter-mediate | Structure | Chemical Name | MS: [(M + 1)]$^+$ | $^1$H NMR |
| I198 | 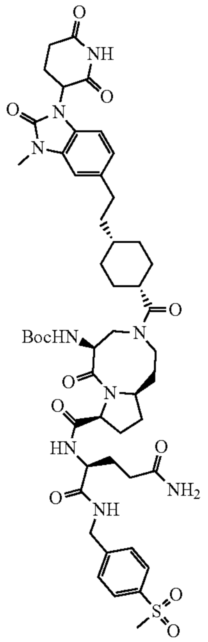 [SMILES: Cn1c(=O)n(C2CCC(=O)NC2=O)c2ccc(CC[C@H]3CC[C@@H](C(=O)N4CC[C@H]5CC[C@@H](C(=O)N[C@@H](CCC(N)=O)C(=O)NCc6ccc(S(C)(=O)=O)cc6)N5C(=O)[C@@H](NC(=O)OC(C)(C)C)C4)CC3)cc21] | tert-butyl N-[(5S,8S,10aR)-8-[[(1S)-3-carbamoyl-1-[[(4-methanesulfonylphenyl)methyl]carbamoyl]propyl]carbamoyl]-6-oxo-3-[(1s,4s)-4-[2-[1-(2,6-dioxopiperidin-3-yl)-3-methyl-2-oxo-1,3-benzodiazol-5-yl]ethyl]cyclohexane-carbonyl]-octahydropyrrolo[1,2-a][1,5]diazocin-5-yl]carbamate | 1018.45 | (300 MHz, Chloroform-d) δ 9.36 (d, J = 15.8 Hz, 1H), 7.84 (d, J = 8.0 Hz, 3H), 7.42 (d, J = 8.1 Hz, 3H), 7.01 (d, J = 8.1 Hz, 1H), 6.92-6.74 (m, 3H), 6.53 (s, 1H), 6.04-5.90 (m, 1H), 5.88-5.67 (m, 1H), 5.29-5.15 (m, 1H), 5.08-4.99 (m, 1H), 4.59-4.40 (m, 4H), 4.12-3.85 (m, 2H), 3.39 (s, 3H), 3.03 (s, 3H), 2.90-2.69 (m, 2H), 2.68-2.55 (m, 3H), 2.54-2.36 (m, 2H), 2.34-2.09 (m, 6H), 1.91-1.80 (m, 2H), 1.79-1.62 (m, 7H), 1.44 (s, 9H) |

Tert-butyl N-I(2S,11S)-2-II(1S)-3-carbamoyl-1-(diphenylmethylcarbamoyl)propyl]carbamoyl]-7-14-[1-(2,6-dioxopiperidin-3-yl)-3-methyl-2-oxo-1,3-benzodiazol-5-yl]butoxy]-12-oxo-1-azatricyclo[6.4.1.0[4,13]]trideca-4(13), 5,7-trien-11-yl]carbamate (Intermediate 1184)

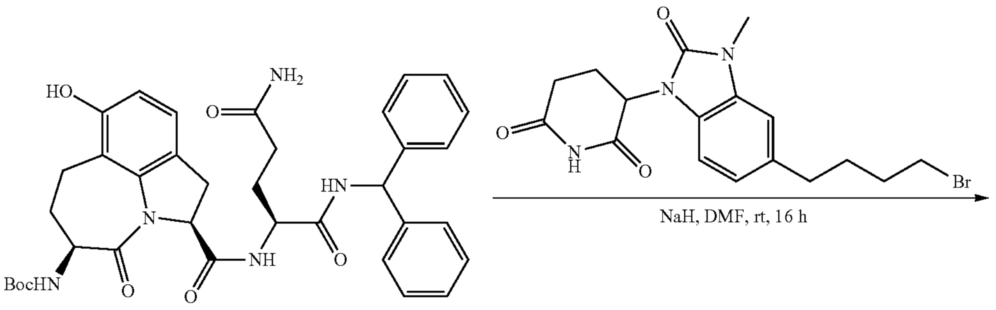

-continued

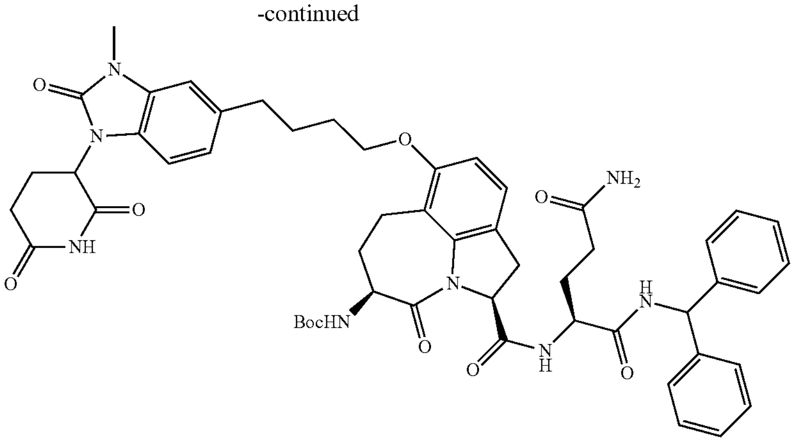

I184

Tert-butyl N-[(2S,11S)-2-[[(1S)-3-carbamoyl-1-(diphenylmethylcarbamoyl)propyl]carbamoyl]-7-[4-[1-(2,6-dioxopiperidin-3-yl)-3-methyl-2-oxo-1,3-benzodiazol-5-yl] butoxyl-12-oxo-1-azatricyclo[6.4.1.0[4,131]trideca-4(13), 5,7-trien-11-yl]carbamate. To a solution of 3-[5-(4-bromobutyl)-3-methyl-2-oxo-1,3-benzodiazol-1-yl]piperidine-2,6-dione (234 mg, 0.59 mmol) in DMF (6 mL) was added NaH (48 mg, 1.19 mmol, 60 wt % in mineral oil) at 0° C. The mixture was stirred for 15 min followed by the addition of 3-[5-(4-bromobutyl)-3-methyl-2-oxo-1,3-benzodiazol-1-yl]piperidine-2,6-dione (234 mg, 0.59 mmol) and the mixture was stirred for 16 h at ambient temperature. The reaction was quenched by the addition of sat. NH4C1 (aq.) (4 mL) at 0° C. The resulting mixture was filtered. The filtered cake was washed with DMF (3×1 mL). The filtrate was concentrated under reduced pressure. The residue was purified by reverse phase flash chromatography with the following conditions: Column: WelFlash™ C18-I, 20~40 um, 120 g; EluentA: Water (plus 10 mmol/L FA); Eluent B: ACN; Gradient: 35% - 60% B in 25 min; Flow rate: 50 mL/min; Detector: UV 220/254 nm; desired fractions were collected at 50% B and concentrated under reduced pressure to afford tert-butyl N-[(2S,11S)-2-[[(1S)-3-carbamoyl-1-(diphenylmethylcarbamoyl)propyl]carbamoyl]-7-[4-[1-(2,6-dioxopiperidin-3-yl)-3-methyl-2-oxo-1,3-benzodiazol-5-yl] butoxy]-12-oxo-1-azatricyclo[6.4.1.0[4,13]]trideca-4(13), 5,7-trien-11-yl]carbamate (90 mg, 15%) as a yellow solid: $^{1}$H NMR (300 MHz, DMSO-$d_6$) δ 11.09 (s, 1H), 8.78-8.72 (m, 1H), 8.35-8.11 (m, 1H), 7.42-7.15 (m, 11H), 7.11-6.84 (m, 5H), 6.83-6.53 (m, 2H), 6.10 (dd, J=8.5, 3.7 Hz, 1H), 5.35 (dd, J=12.5, 5.0 Hz, 1H), 5.21-4.92 (m, 1H), 4.38-4.32 (m, 1H), 4.14-4.05 (m, 3H), 3.78 (q, J=6.3 Hz, 1H), 3.22 (s, 3H), 3.06-2.58 (m, 6H), 2.20-1.87 (m, 6H), 1.82-1.74 (m, 6H), 1.39 (s, 9H); LC/MS (ESI, m/z): $[(M+1)]^+$=969.40.

The intermediates in Table 51 were prepared according to the procedure to prepare Intermediate 1184

TABLE 51

| Characterization data for intermediates prepared according to above. | | | | |
|---|---|---|---|---|
| Inter-mediate | Structure | Chemical Name | MS: $[(M + 1)]^+$ | $^1$H-NMR |
| I185 | 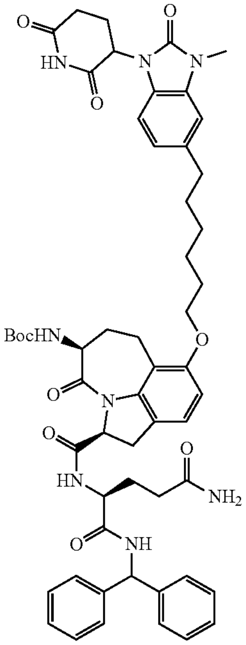 [SMILES: Cn1c(=O)n(C2CCC(=O)NC2=O)c2ccc(CCCCCCOc3ccc4c5c3CC[C@H](NC(=O)OC(C)(C)C)C(=O)N5[C@H](C(=O)N[C@@H](CCC(N)=O)C(=O)NC(c3ccccc3)c3ccccc3)C4)cc21] | Tert-butyl N-[(2S,11S)-2-[[(1S)-3-carbamoyl-1-(diphenylmethylcarbamoyl)propyl]carbamoyl]-7-([6-[1-(2,6-dioxopiperidin-3-yl)-3-methyl-2-oxo-1,3-benzodiazol-5-yl]hexyl]oxy)-12-oxo-1-azatricyclo[6.4.1.0^[4,13]]trideca-4(13),5,7-trien-11-yl]carbamate | 997.45 | (300 MHz, DMSO-$d_6$) δ 11.09 (s, 1H), 8.71 (d, J = 8.1 Hz, 1H), 8.30-8.24 (m, 2H), 7.36-7.28 (m, 11H), 7.11-6.84 (m, 4H), 6.81-6.50 (m, 2H), 6.10 (dd, J = 8.5, 3.7 Hz, 1H), 5.35 (dd, J = 12.5, 5.0 Hz, 1H), 5.21-4.92 (m, 2H), 4.38-4.32 (m, 1H), 4.14-4.05 (m, 4H), 3.78 (q, J = 6.3 Hz, 2H), 3.22 (s, 3H), 3.06-2.58 (m, 6H), 2.20-1.87 (m, 6H), 1.82-1.74 (m, 6H), 1.39 (s, 9H), 1.28-1.21 (m, 2H) |

(3R,5S)-1-[(2S)-2-(6-[3-[(2S)-2-[[(2S,11S)-11-[(tert-butoxycarbonyl)amino]-12-oxo-1-azatricyclo[6.4.1.0[4,13]]trideca-4(13), 5,7-trien-2-yl]formamido]-4-carbamoylbutoxy]-2-fluorophenyl]hexanamido)-3,3-dimethylbutanoyl]-5-[[(1S)-1-[4-(4-methyl-1,3-thiazol-5-yl)phenyl]ethyl]carbamoyl]pyrrolidin-3-ylacetate (Intermediate 1186)

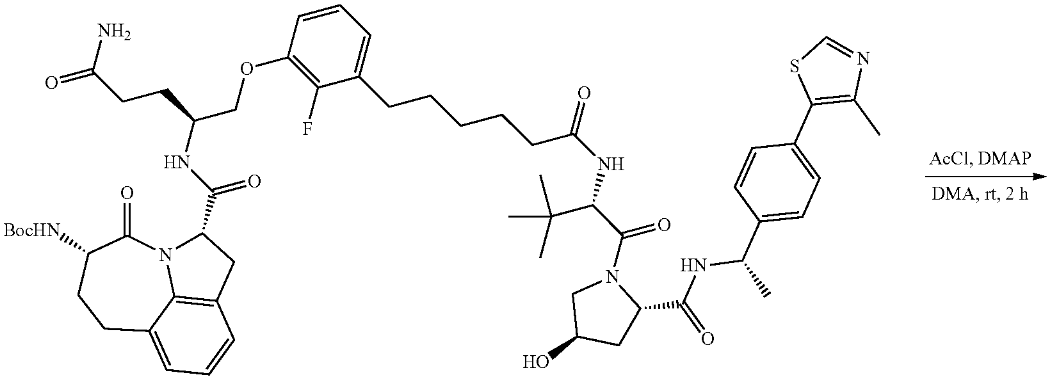

-continued

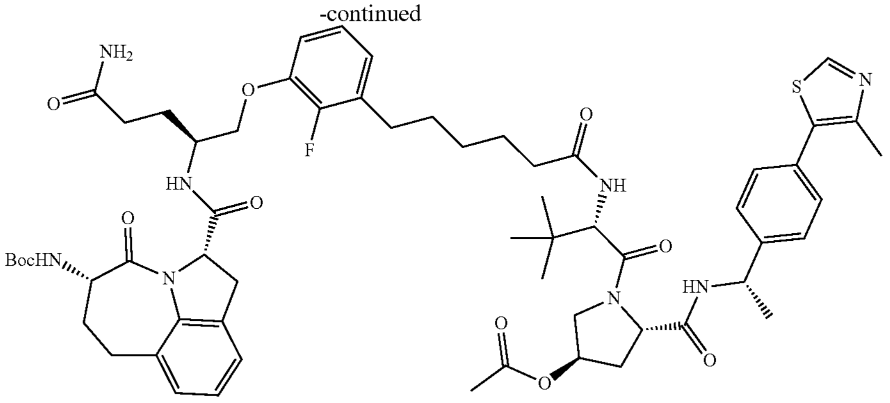

I186

(3R,5S)-1-[(2S)-2-(6-[3-[(2S)-2-[[(2S,11S)-11-[(tert-butoxycarbonyl)amino]-12-oxo-1-azatricyclo[6.4.1.0[4,13]]trideca-4(13), 5,7-trien-2-yl]formamido]-4-carbamoylbutoxy]-2-fluorophenyl]hexanamido)-3,3-dimethylbutanoyl]-5-[[(1S)-1-[4-(4-methyl-1,3-thiazol-5-yl)phenyl]ethyl]carbamoyl]pyrrolidin-3-yl acetate. To a stirred solution of tert-butyl N-[(2S,11S)-2-[[(2S)-4-carbamoyl-1-[2-fluoro-3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenoxy]butan-2-yl]carbamoyl]-12-oxo-1-azatricyclo[6.4.1.0[4,13]]trideca-4(13), 5,7-trien-11-yl]carbamate (800 mg, 0.73 mmol), TEA (185 mg, 1.83 mmol) and DMAP (8.92 mg, 0.073 mmol) in DMA (1 mL) was added acetyl chloride (287 mg, 3.65 mmol) in DMA (1 mL) dropwise at 0° C. under nitrogen atmosphere. After stirring for 2 h at room temperature, the mixture was purified by reverse phase flash chromatography with the following conditions: column, Spherical C18 Column, 20~40 um, 330 g; Mobile Phase A: Water (plus 10 mmol/$LNH_4HCO_3$), Mobile Phase B: ACN; Gradient: 30% to 50% B in 20 min; Detector: UV 254/220 nm. Desired fractions were collected at 43% B, concentrated under reduced pressure and lyophilized to afford (3R,5S)-1-[(2S)-2-(6-[3-[(2S)-2-[[(2S,11S)-11-[(tert-butoxycarbonyl)amino]-12-oxo-1-azatricyclo[6.4.1.0[4,13]]trideca-4(13), 5,7-trien-2-yl]formamido]-4-carbamoylbutoxy]-2-fluorophenyl]hexanamido)-3,3-dimethylbutanoyl]-5-[[(1S)-1-[4-(4-methyl-1,3-thiazol-5-yl)phenyl]ethyl]carbamoyl]pyrrolidin-3-ylacetate (755 mg, 91%) as a white solid: $^1H$ NMR (400 MHz, DMSO-$d_6$) δ 8.99 (s, 1H), 8.41 (d, J=7.8 Hz, 1H), 8.08 (d, J=7.4 Hz, 1H), 7.82 (d, J=8.7 Hz, 1H), 7.44 (d, J=8.0 Hz, 2H), 7.38 (d, J=8.2 Hz, 2H), 7.24 (s, 1H), 7.13-7.02 (m, 3H), 7.02-6.91 (m, 3H), 6.84-6.80 (m, 1H), 6.74 (s, 1H), 5.19 (s, 1H), 5.06-5.02 (m, 1H), 4.91 (q, J=7.1 Hz, 1H), 4.47 (t, J=8.4 Hz, 1H), 4.36 (d, J=8.7 Hz, 1H), 4.00-3.96 (m, 5H), 3.76-3.72 (m, 1H), 3.44-3.40 (m, 1H), 3.08 (s, 1H), 3.01 (d, J=17.2 Hz, 1H), 2.89-2.85 (m, 1H), 2.59-2.55 (m, 2H), 2.46 (s, 3H), 2.25-2.21 (m, 2H), 2.12 (dd, J=14.8, 7.7 Hz, 3H), 2.00 (s, 3H), 1.84 (s, 1H), 1.71 (s, 1H), 1.53-1.49 (m, 5H), 1.39 (s, 9H), 1.34-1.23 (m, 6H), 1.15-1.11 (m, 1H), 0.95 (s, 9H); LC/MS (ESI, m/z): $[(M+1)]^+$=1137.50.

Tert-butyl N-[(2S,11S)-2-[[(1S)-3-carbamoyl-1-(diphenylmethylcarbamoyl)propyl]carbamoyl]-6-[(4-[[1-(2,6-dioxopiperidin-3-yl)-3-methyl-2-oxo-1,3-benzodiazol-5-yl]methyl]cyclohexyl)methyl]-12-oxo-1-azatricyclo[6.4.1.0[4,13]]trideca-4(13), 5,7-trien-11-yl]carbamate (Intermediate 1187)

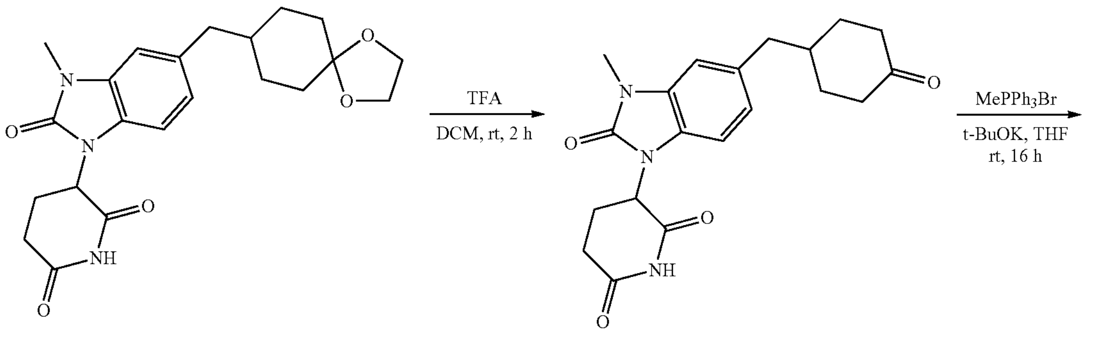

-continued

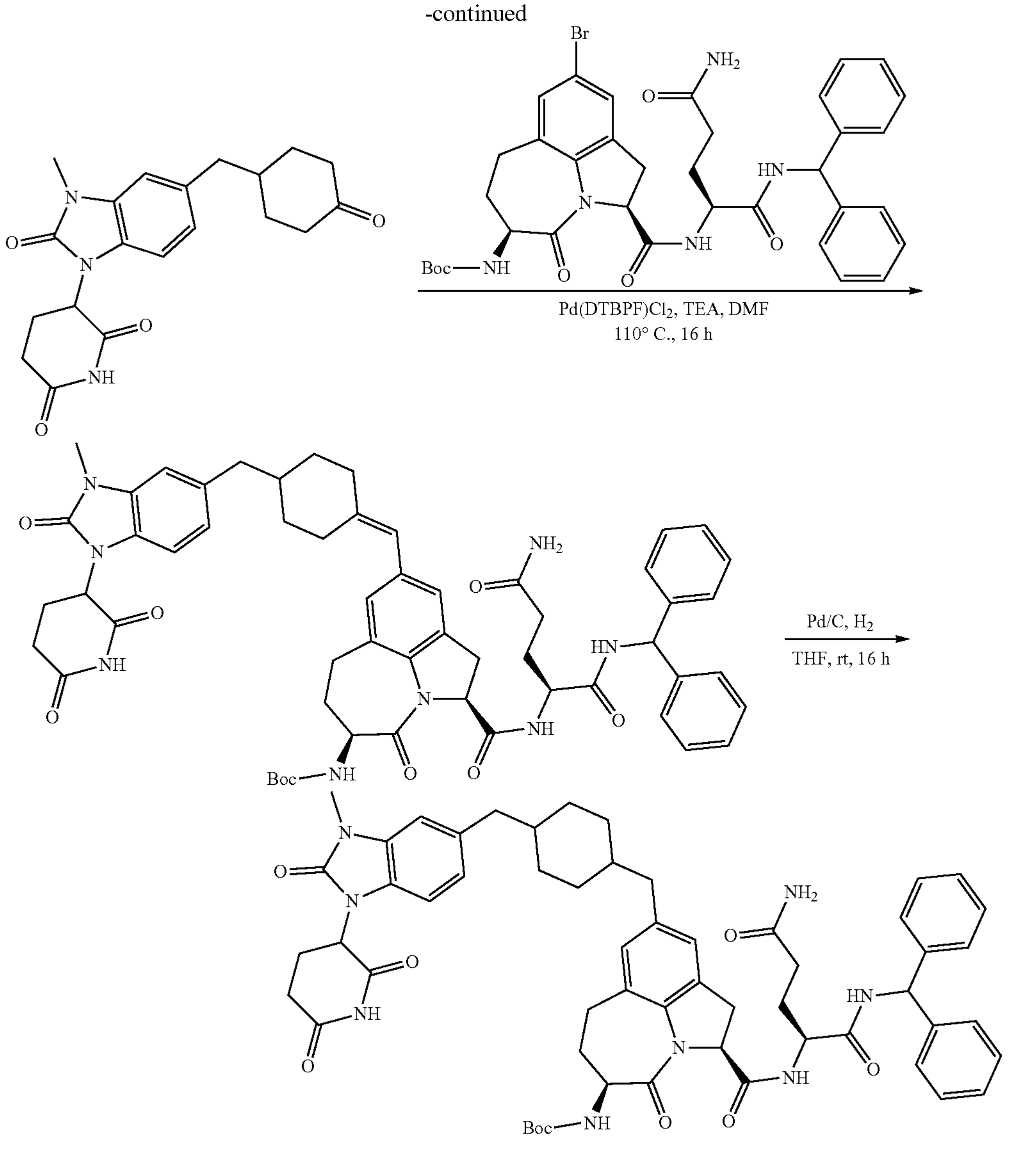

I187

Step 1: 3-[3-methyl-2-oxo-5-[(4-oxocyclohexyl)methyl]-1,3-benzodiazol-1-yl]piperidine-2,6-dione. To a stirred solution of 3-(5-[1,4-dioxaspiro[4.5]decan-8-ylmethyl]-3-methyl-2-oxo-1,3-benzodiazol-1-yl)piperidine-2,6-dione (1 g, 2.42 mmol) in DCM (40 mL) was added TFA (4 mL, 53.8 mmol). The resulting mixture was stirred for 2 h at ambient temperature under nitrogen atmosphere. The resulting mixture was concentrated under reduced pressure. The crude product was purified by reverse phase flash chromatography with the following conditions (Column: Spherical C18 Column, 20~40 um, 120 g; Mobile Phase A: Water (plus 0.1% TFA), Mobile Phase B: ACN; Flow rate: 60 mL/min; Gradient: 30% B to 50% B in 25 min; Detector: UV 254/220 nm. The fractions containing the desired product were collected at 40% B and concentrated under reduced pressure to afford 3-[3-methyl-2-oxo-5-[(4-oxocyclohexyl)methyl]-1,3-benzodiazol-1-yl]piperidine-2,6-dione (570 mg, 64%) as a white solid: $^1$H NMR (300 MHz, CD3OD) δ 7.02 (d, J=7.1 Hz, 2H), 6.93 (d, J=8.1 Hz, 1H), 5.34-5.31 (m, 1H), 4.88-4.86 (m, 2H), 3.45-3.41 (m 3H), 3.32-3.31 (m, 1H), 2.98-2.76 (m, 2H), 2.60 (d, J=6.7 Hz, 2H), 2.01-1.96 (m, 2H), 1.61 (d, J=11.0 Hz, 3H), 1.28-1.25 (m, 3H); LC/MS (ESI, m/z): $[(M+1)]^+$=370.20.

Step 2: 3-[3-methyl-5-[(4-methylidenecyclohexyl)methyl]-2-oxo-1,3-benzodiazol-1-yl]piperidine-2,6-dione. To a stirred solution of methyltriphenylphosphanium bromide (2.27 g, 6.36 mmol) in THF (10 mL) was added t-BuOK (713 mg, 6.36 mmol) in portions at 0° C. under nitrogen atmosphere and stirring for 30 min. To the above mixture was added 3-[3-methyl-2-oxo-5-[(4-oxocyclohexyl)methyl]-1,3-benzodiazol-1-yl]piperidine-2,6-dione (470 mg, 1.27 mmol) in THF (5 mL) at 0° C. The resulting mixture was stirred for additional 1 h at ambient temperature. The mixture was acidified to pH 6 with 1 N HCl. The resulting mixture was filtered, the filtered cake was washed with DCM (3×20 mL). The filtrate was concentrated under reduced pressure. The crude product was purified by reverse phase flash chromatography with the following conditions:

Column: Spherical C18 Column, 20~40 um, 120 g; Mobile Phase A: Water (plus 0.1% FA), Mobile Phase B: ACN; Flow rate: 60 mL/min; Gradient: 50% B to 80% B in 25 min Detector: UV 254/220 nm. The fractions containing the desired product were collected at 70% B and concentrated under reduced pressure to afford 3-[3-methyl-5-[(4-methylidenecyclohexyl)methyl]-2-oxo-1,3-benzodiazol-1-yl]piperidine-2,6-dione (410 mg, 88%) as a white solid: $^1$H NMR (300 MHz, CDCl3) δ 8.05 (d, J=26.4 Hz, 1H), 6.90-6.81 (m, 2H), 6.72 (d, J=8.0 Hz, 1H), 5.38-5.17 (m, 2H), 4.65-4.58 (m, 1H), 3.46-3.43 (m, 3H), 3.00-2.70 (m, 3H), 2.60-2.58 (m, 2H), 2.31-2.29 (m, 2H), 2.01-1.99 (m 2H), 1.80 (d, J=14.0 Hz, 3H), 1.28-1.26 (m, 1H), 1.12-1.10 (m 1H); LC/MS (ESI, m/z): $[(M+1)]^+$=368.25.

Step 3: tert-butyl N-[(2S,11S)-2-[[(1S)-3-carbamoyl-1-(diphenylmethylcarbamoyl)propyl]carbamoyl]-6-[(4-[[1-(2,6-dioxopiperidin-3-yl)-3-methyl-2-oxo-1,3-benzodiazol-5-yl]methyl]cyclohexylidene)methyl]-12-oxo-1-azatricyclo[6.4.1.0[4,13]]trideca-4(13), 5,7-trien-11-yl]carbamate. To a stirred solution of 3-[3-methyl-5-[(4-methylidenecyclohexyl)methyl]-2-oxo-1,3-benzodiazol-1-yl]piperidine-2,6-dione (200 mg, 0.55 mmol) and tert-butyl N-[(2S,11S)-6-bromo-2-[[(1S)-3-carbamoyl-1-(diphenylmethylcarbamoyl)propyl]carbamoyl]-12-oxo-1-azatricyclo[6.4.1.0[4,13]]trideca-4(13), 5,7-trien-11-yl]carbamate (783 mg, 1.09 mmol) in DMA (5 mL) were added Pd(DTBPF)C12 (36 mg, 0.054 mmol) and TEA (165 mg, 1.63 mmol) at ambient temperature. The resulting mixture was stirred for 16 h at 110° C. under nitrogen atmosphere. After cooling down to ambient temperature, the mixture was purified by reverse phase flash chromatography with the following conditions: Column: Spherical C18 Column, 20~40 um, 120 g; Mobile Phase A: Water (plus 0.1% HOAc), Mobile Phase B: ACN; Flow rate: 60 mL/min; Gradient: 40% B to 60% B in 20 min; Detector: UV 254/220 nm. The fractions containing the desired product were collected at 56% B and concentrated under reduced pressure to afford tert-butyl N-[(2S,11S)-2-[[(1S)-3-carbamoyl-1-(diphenylmethylcarbamoyl)propyl]carbamoyl]-6-[(4-[[1-(2,6-dioxopiperidin-3-yl)-3-methyl-2-oxo-1,3-benzodiazol-5-yl]methyl]cyclohexylidene)methyl]-12-oxo-1-azatricyclo[6.4.1.0[4,13]]trideca-4(13), 5,7-trien-11-yl]carbamate (100 mg, 19%) as a brown solid: $^1$H NMR (400 MHz, DMSO-$d_6$) δ 11.09 (s, 1H), 8.79 (d, J=8.2 Hz, 1H), 8.22-8.15 (m, 1H), 7.30-7.23 (m, 11H), 7.02-6.68 (m, 4H), 6.86-6.84 (m, 3H), 6.77-6.74 (m, 1H), 6.30-6.05 (m, 2H), 5.35-5.33 (m, 1H), 5.09 (d, J=10.2 Hz, 1H), 4.33-4.31 (m, 1H), 4.04 (d, J=6.9 Hz, 1H), 2.94-2.89 (m, 5H), 2.70-2.67 (m, 3H), 2.44-2.41 (m, 1H), 2.33-2.30 (m, 1H), 2.26-1.84 (m, 9H), 1.80-1.76 (m, 4H), 1.38 (s, 9H), 1.30-0.81 (m, 4H); LC/MS (ESI, m/z): $[(M+1)]^+$=1005.40.

Step 4: tert-butyl N-[(2S,11S)-2-[[(1S)-3-carbamoyl-1-(diphenylmethylcarbamoyl)propyl]carbamoyl]-6-[(4-[[1-(2,6-dioxopiperidin-3-yl)-3-methyl-2-oxo-1,3-benzodiazol-5-yl]methyl]cyclohexyl)methyl]-12-oxo-1-azatricyclo[6.4.1.0[4,13]]trideca-4(13), 5,7-trien-11-yl]carbamate. To a stirred solution of tert-butyl N-[(2S,11S)-2-[[(1S)-3-carbamoyl-1-(diphenylmethylcarbamoyl)propyl]carbamoyl]-6-[(4-[[1-(2,6-dioxopiperidin-3-yl)-3-methyl-2-oxo-1,3-benzodiazol-5-yl]methyl]cyclohexylidene)methyl]-12-oxo-1-azatricyclo[6.4.1.0[4,13]]trideca-4(13), 5,7-trien-11-yl]carbamate (200 mg, 0.20 mmol) in THF (8 mL) was added Pd/C (50 mg, 10% wt) at room temperature. The resulting mixture was stirred for 16 h at room temperature under hydrogen atmosphere (1.5 atm). The resulting mixture was filtered, the filtered cake was washed with MeOH (5×25 mL). The filtrate was concentrated under reduced pressure. The residue was purified by reverse phase flash chromatography with the following conditions: Column: Spherical C18 Column, 20~40 um, 120 g; Mobile Phase A: Water (plus 0.1% HOAc v/v), Mobile Phase B: ACN; Flow rate: 60 mL/min; Gradient: 30% B to 50% B in 25 min; Detector: UV 254/220 nm. The fractions containing the desired product were collected at 40% B and concentrated under reduced pressure to afford tert-butyl N-[(2S,11S)-2-[[(1S)-3-carbamoyl-1-(diphenylmethylcarbamoyl)propyl]carbamoyl]-6-[(4-[[1-(2,6-dioxopiperidin-3-yl)-3-methyl-2-oxo-1,3-benzodiazol-5-yl]methyl]cyclohexyl)methyl]-12-oxo-1-azatricyclo[6.4.1.0[4,13]]trideca-4(13), 5,7-trien-11-yl]carbamate (170 mg, 85%) as a white solid: $^1$H NMR (400 MHz, DMSO-$d_6$) δ 11.09 (s, 1H), 8.75-8.73 (m, 1H), 8.31-8.12 (m, 1H), 7.36-7.19 (m, 11H), 7.08-6.94 (m, 3H), 6.89-6.75 (m, 3H), 6.11-6.04 (m, 1H), 5.38-5.30 (m, 1H), 5.08-5.06 (m, 1H), 4.35-4.29 (m, 1H), 4.05-3.98 (m, 1H), 3.46 (d, J=1.8 Hz, 2H), 3.09-2.82 (m, 4H), 2.76-2.54 (m, 4H), 2.38-2.36 (m, 1H), 2.13-1.96 (m, 5H), 1.93-1.87 (m, 1H), 1.79-1.77 (m, 1H), 1.64 (d, J=8.6 Hz, 2H), 1.56-1.52 (m, 2H), 1.47-1.40 (m, 3H)$_{1.38}$ (s, 9H), 1.30-1.03 (m, 6H), 0.96-0.75 (m, 3H); LC/MS (ESI, m/z): $[(M+1)]^+$=1007.45.

(4S,5R)-4-[[(2S,11S)-11-amino-12-oxo-1-azatricyclo[6.4.1.0[4,13]]trideca-4(13), 5,7-trien-2-yl]formamido]-5-([4-[3-(2-[3-[1-(2,6-dioxopiperidin-3-yl)-3-methyl-2-oxo-1,3-benzodiazol-5-yl]propoxy]ethoxy)propyl]phenyl]methoxy)hexanamide acetate (Intermediate J)

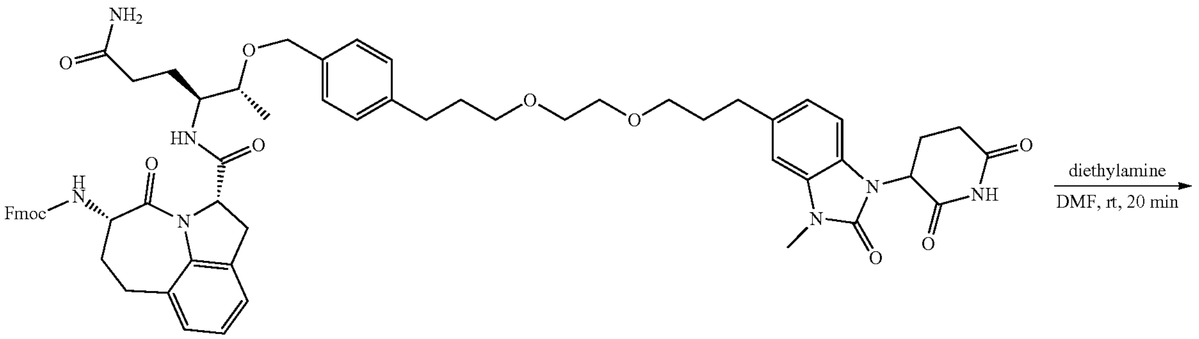

-continued

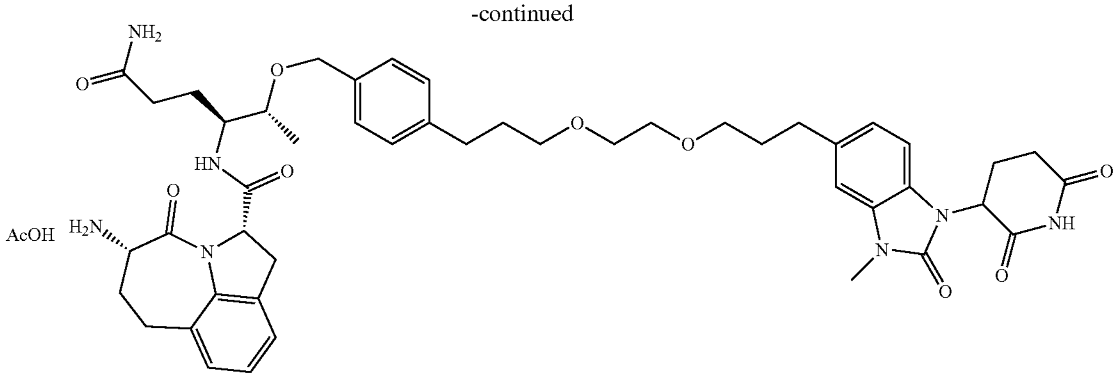

Intermediate J

A solution of 9H-fluoren-9-ylmethyl N-[(2S,11S)-2-[[(3S, 4R)-1-carbamoyl-4-([4-[3-(2-[3-[1-(2,6-dioxopiperidin-3-yl)-3-methyl-2-oxo-1,3-benzodiazol-5-yl]propoxy]ethoxy) propyl]phenyl]methoxy)pentan-3-yl]carbamoyl]-12-oxo-1-azatricyclo[6.4.1.0[4,13]]trideca-4(13), 5,7-trien-11-yl] carbamate (200 mg, 0.18 mmol) in DMF (3.50 mL) was treated with diethylamine (0.70 mL) for 20 min at room temperature under nitrogen atmosphere. The mixture was acidified to pH=5 with AcOH. The mixture was concentrated under reduced pressure. The residue was purified by reversed phase flash chromatography with the following conditions: Column: WelFlash™ C18-I, 20~40 um, 120 g; EluentA: Water (plus 10 mmol/LAcOH); Eluent B: ACN; Gradient: 15% - 35% B in 20 min; Flow rate: 50 mL/min; Detector: UV 220/200 nm; desired fractions were collected at 28% B and concentrated under reduced pressure to afford the title compound as a white solid (85 mg, 54%): $^1$H NMR (400 MHz, DMSO-d4) δ 7.80 (d, J=9.3 Hz, 1H), 7.18 (d, J=7.9 Hz, 2H), 7.15-7.09 (m, 2H), 7.06-6.97 (m, 4H), 6.96-6.84 (m, 2H), 6.67 (s, 1H), 5.33 (dd, J=12.6, 5.4 Hz, 1H), 5.05 (d, J=10.8 Hz, 1H), 4.41 (s, 2H), 3.84-3.73 (m, 1H), 3.55 (d, J=5.0 Hz, 2H), 3.51 (s, 3H), 3.46-3.35 (m, 4H), 3.06-2.95 (m, 2H), 2.92-2.80 (m, 2H), 2.73-2.57 (m, 5H), 2.47-2.37 (m, 3H), 2.12-1.93 (m, 4H), 1.90 (s, 3H), 1.89-1.70 (m, 5H), 1.62-1.47 (m, 2H), 1.08 (d, J=6.3 Hz, 3H); MS (ESI, m/z): $[(M+1)]^+$=866.50.

The following intermediates in Table 52 were synthesized according to the procedure to prepare Intermediate J.

TABLE 52

Characterization data for intermediates prepare according to above.

| Inter-mediate | Structure | Chemical Name | MS: $[(M + 1)]^+$ | $^1$H NMR |
|---|---|---|---|---|
| J1 | 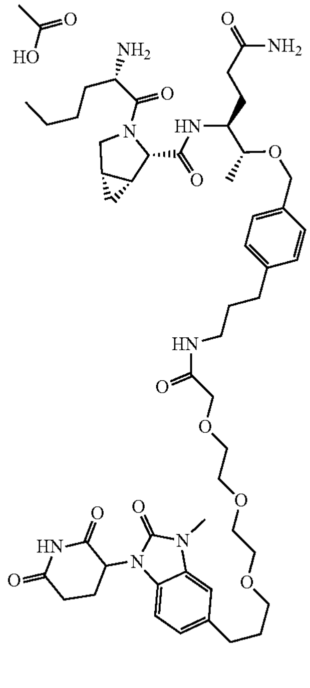 | (4S,5R)-4-[[(1R,2S,5S)-3-aminohexanoyl]-3-azabicyclo[3.1.0]hexan-2-yl]formamido]-5-[[4-(3-[2-[2-(2-[3-[1-(2,6-dioxopiperidin-3-yl)-3-methyl-2-oxo-2,3-dihydro-1H-1,3-benzodiazol-5-yl]propoxy]ethoxy)ethoxy]acetamido]propyl)phenyl]methoxy]hexanamide acetate | 961.6 | (400 MHz, DMSO-$d_6$) δ 8.07 (d, J = 9.2 Hz, 1H), 7.71 (t, J = 5.8 Hz, 1H), 7.54 (d, J = 9.2 Hz, 1H), 7.26-7.20 (m, 2H), 7.18-7.11 (m, 2H), 7.10-6.97 (m, 3H), 6.87 (dd, J = 8.2, 1.6 Hz, 1H), 6.66 (s, 1H), 5.34 (dd, J = 12.6, 5.3 Hz, 1H), 4.52-4.33 (m, 3H), 3.88 (s, 2H), 3.83 (dd, J = 9.8, 5.3 Hz, 1H), 3.75-3.65 (m, 1H), 3.60-3.49 (m, 8H), 3.53-3.37 (m, 3H), 3.40-3.34 (m, 1H), 3.32 (s, 3H), 3.11 (q, J = 6.7 Hz, 2H), 2.98-2.84 (m, 1H), 2.77-2.52 (m, 8H), 2.19-2.07 (m, 1H), 2.05-1.96 (m, 1H), 1.90 (s, 3H), 1.87-1.77 (m, 2H), 1.77-1.66 (m, 2H), 1.56-1.40 (m, 2H), 1.29-1.20 (m, 5H), 1.10 (dd, J = 12.7, 6.2 Hz, 3H), 0.89-0.81 (m, 3H), 0.70 (d, J = 4.6 Hz, 1H), 0.55 (s, 1H). |

TABLE 52-continued

| Characterization data for intermediates prepare according to above. | | | | |
|---|---|---|---|---|
| Intermediate | Structure | Chemical Name | MS: $[(M+1)]^+$ | $^1H$ NMR |
| J2 | 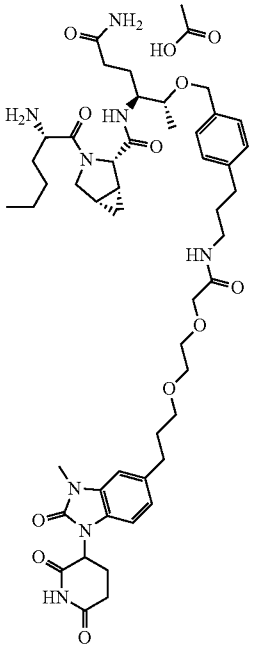 | (4S,5R)-4-[[(1R,2S,5S)-3-[(2S)-2-aminohexanoyl]-3-azabicyclo[3.1.0]hexan-2-yl]formamido]-5-[(4-[3-[2-(2-[3-[1-(2,6-dioxopiperidin-3-yl)-3-methyl-2-oxo-2,3-dihydro-1H-1,3-benzodiazol-5-yl]propoxy]ethoxy)acetamido]propyl]phenyl)methoxy]hexanamide acetate | 917.7 | (400 MHz, DMSO-$d_6$) δ 8.07 (d, J = 9.2 Hz, 1H), 7.72 (t, J = 5.9 Hz, 1H), 7.54 (d, J = 9.2 Hz, 1H), 7.23 (dd, J = 7.9, 3.8 Hz, 2H), 7.18-7.10 (m, 2H), 7.07 (s, 1H), 7.05-6.97 (m, 2H), 6.88 (dd, J = 8.1, 1.6 Hz, 1H), 6.66 (s, 1H), 5.34 (dd, J = 12.7, 5.4 Hz, 1H), 4.50-4.33 (m, 3H), 3.90 (s, 2H), 3.83 (dd, J = 9.9, 5.3 Hz, 1H), 3.70 (d, J = 9.2 Hz, 1H), 3.60 (dd, J = 6.1, 3.4 Hz, 2H), 3.58-3.51 (m, 3H), 3.49-3.30 (m, 4H), 3.12 (q, J = 6.7 2H), 2.99-2.84 (m, 2H), 2.76-2.58 (m, 4H), 2.57-2.52 (m, 4H), 2.20-1.95 (m, 3H), 1.90 (s, 3H), 1.87-1.78 (m, 2H), 1.75-1.64 (m, 2H), 1.60-1.39 (m, 1H), 1.37-1.16 (m, 6H), 1.10 (dd, J = 12.6, 6.2 Hz, 3H), 0.85 (t, J = 6.8 Hz, 3H), 0.71 (q, J = 4.4 Hz, 1H), 0.55 (d, J = 4.6 Hz, 1H). |
| J3 | 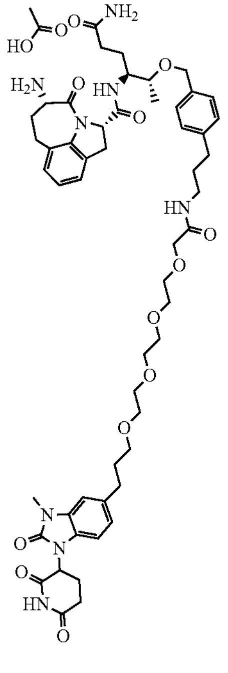 | N-[3-[4-([[(2R,3S)-3-[[(2S,11S)-11-amino-12-oxo-1-azatricyclo[6.4.1.0^[4,13]]trideca-4(13),5,7-trien-2-yl]formamido]-5-carbamoylpentan-2-yl]oxylmethyl)phenyl]propyl]-15-[1-(2,6-dioxopiperidin-3-yl)-3-methyl-2-oxo-2,3-dihydro-1H-1,3-benzodiazol-5-yl]-3,6,9,12-tetraoxapentadecanamide acetate | 1011.7 | (400 MHz, DMSO-$d_6$) δ 7.82 (d, J = 9.3 Hz, 1H), 7.72 (t, J = 6.1 Hz, 1H), 7.22-7.16 (m, 2H), 7.12 (d, J = 7.8 Hz, 2H), 7.04-6.99 (m, 3H), 6.93 (dd, J = 8.1, 6.7 Hz, 1H), 6.86 (d, J = 8.1 Hz, 1H), 6.69 (s, 1H), 5.34 (dd, J = 12.8, 5.4 Hz, 1H), 5.06 (dd, J = 11.0, 3.1 Hz, 1H), 4.47-4.35 (m, 2H), 3.87 (s, 2H), 3.83-3.72 (m, 1H), 3.57 (s, 4H), 3.53 (m, 5H), 3.50-3.45 (m, 2H), 3.43-3.32 (m, 8H), 3.15-3.09 (m, 2H), 3.07-2.98 (m, 1H), 2.90 (s, 2H), 2.86 (d, J = 3.9 Hz, 1H), 2.73-2.61 (m, 2H), 2.56 (d, J = 7.5 Hz, 1H), 2.13-1.85 (m, 10H), 1.84-1.77 (m, 2H), 1.75-1.67 (m, 2H), 1.63-1.50 (m, 1H), 1.09 (dd, J = 9.1, 6.7 Hz, 3H). |

TABLE 52-continued

| Characterization data for intermediates prepare according to above. | | | | |
|---|---|---|---|---|
| Intermediate | Structure | Chemical Name | MS: $[(M + 1)]^+$ | $^1H$ NMR |
| J4 | 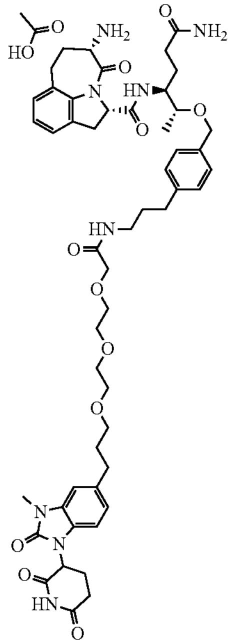 | (4S,5R)-4-[[(2S,11S)-11-amino-12-oxo-1-azatricyclo[6.4.1.0^[4,13]]trideca-4(13),5,7-trien-2-yl]formamido]-5-[[4-(3-[2-[2-(2-[3-[1-(2,6 dioxopiperidin-3-yl)-3-methyl-2-oxo-2,3-dihydro-1H-1,3-benzodiazol-5-yl]propoxy]ethoxy) ethoxy]acetamido] propyl)phenyl] methoxy] hexanamide acetate | 967.7 | (400 MHz, DMSO-$d_6$) δ 7.91-7.76 (m, 1H), 7.71 (t, J = 5.7 Hz, 1H), 7.16 (m, 3H), 7.10 (d, J = 7.9 Hz, 2H), 7.04-6.95 (m, 4H), 6.91 (dd, J = 8.2, 6.6 Hz, 1H), 6.85 (dd, J = 8.1, 1.6 Hz, 1H), 6.67 (s, 1H), 5.32 (dd, J = 12.7, 5.4 Hz, 1H), 5.04 (dd, J = 11.0, 3.2 Hz, 1H), 4.44-4.34 (m, 2H), 3.87 (s, 2H), 3.84-3.72 (m, 1H), 3.60-3.51 (m, 6H), 3.55-3.45 (m, 2H), 3.45-3.34 (m, 11H), 3.11 (q, J = 6.7 Hz, 2H), 3.06-2.97 (m, 1H), 2.90-2.78 (m, 2H), 2.75-2.57 (m, 4H), 2.56-2.50 (m, 2H), 2.10-1.94 (m, 3H), 1.93-1.86 (m, 4H), 1.85-1.63 (m, 4H), 1.61-1.49 (d, J = 9.7 Hz, 1H), 1.06 (d, J = 6.3 Hz, 3H). |
| J5 | 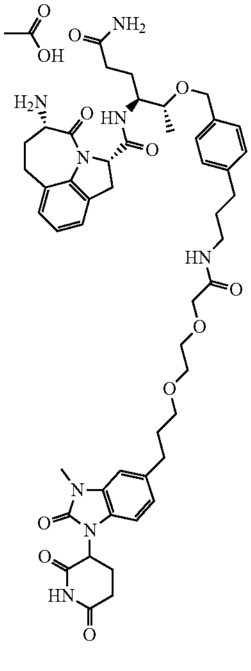 | (4S,5R)-4-[[(2S,11S)-11-amino-12-oxo-1-azatricyclo[6.4.1.0^[4,13]]trideca-4(13),5,7-trien-2-yl]formamido]-5-[(4-[3-[2-(2-[3-[1-(2,6-dioxopiperidin-3-yl)-3-methyl-2-oxo-2,3-dihydro-1H-1,3-benzodiazol-5-yl]propoxy]ethoxy) acetamido]propyl] phenyl)methoxy] hexanamide acetate | 923.5 | (400 MHz, DMSO-$d_6$) δ 7.82 (d, J = 9.2 Hz, 1H), 7.74 J = 6.0 Hz, 1H), 7.17 (d, J = 7.8 Hz, 2H), 7.11 (d, J = 7.8 Hz, 2H), 7.05-6.97 (m, 4H), 6.92 (dd, J = 8.2, 6.6 Hz, 1H), 6.86 (dd, J = 8.1, 1.5 Hz, 1H), 6.69 (s, 1H), 5.34 (dd, J = 12.8, 5.3 Hz, 1H), 5.06 (d, J = 10.8 Hz, 1H), 4.41 (s, 2H), 3.90 (s, 2H), 3.84-3.73 (m, 1H), 3.61 (dd, J = 6.0, 3.4 Hz, 2H), 3.56 (dd, J = 5.8, 3.2 Hz, 2H), 3.49-3.37 (m, 4H), 3.37-3.28 (m, 8H), 3.13 (d, J = 6.3 Hz, 2H), 3.06-2.98 (m, 2H), 2.98-2.78 (m, 2H), 2.76-2.60 (m, 4H), 2.57-2.50 (m, 2H), 2.15-1.93 (m, 2H), 1.91 (s, 3H), 1.88-1.67 (m, 4H), 1.56 (d, J = 9.6 Hz, 1H), 1.08 (d, J = 6.2 Hz, 3H). |

TABLE 52-continued

Characterization data for intermediates prepare according to above.

| Intermediate | Structure | Chemical Name | MS: $[(M+1)]^+$ | $^1H$ NMR |
|---|---|---|---|---|
| J6 | 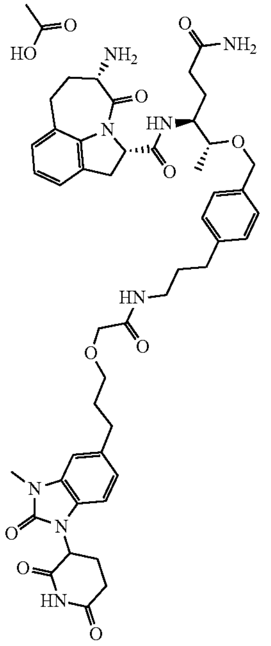 | (4S,5R)-4-[[(2S,11S)-11-amino-12-oxo-1-azatricyclo[6.4.1.0^[4,13]]trideca-4(13),5,7-trien-2-yl]formamido]-5-([4-[3-[2-[3-[1-(2,6-dioxopiperidin-3-yl)-3-methyl-2-oxo-2,3-dihydro-1H-1,3-benzodiazol-5-yl]propoxy]acetamido)propyl]phenyl]methoxy)hexanamide acetate | 879.7 | (400 MHz, DMSO-$d_6$) δ 7.82 (d, J = 9.2 Hz, 1H), 7.75 (t, J = 6.0 Hz, 1H), 7.22-7.09 (m, 5H), 7.08-6.96 (m, 4H), 6.95-6.84 (m, 2H), 6.69 (s, 1H), 5.34 (dd, J = 12.7, 5.3 Hz, 1H), 5.05 (dd, J = 11.0, 3.2 Hz, 1H), 4.46-4.37 (m, 2H), 3.84 (s, 2H), 3.82-3.71 (m, 1H), 3.50-3.32 (m, 9H), 3.13 (q, J = 6.7 Hz, 2H), 3.03 (d, J = 13.4 Hz, 2H), 2.86 (t, J = 16.2 Hz, 2H), 2.78-2.58 (m, 4H), 2.56-2.50 (m, 2H), 2.13-1.94 (m, 5H), 1.93-1.83 (m, 5H), 1.73 (q, J = 7.4 Hz, 2H), 1.61-1.45 (m, 1H), 1.08 (d, J = 6.2 Hz, 3H). |
| J7 | 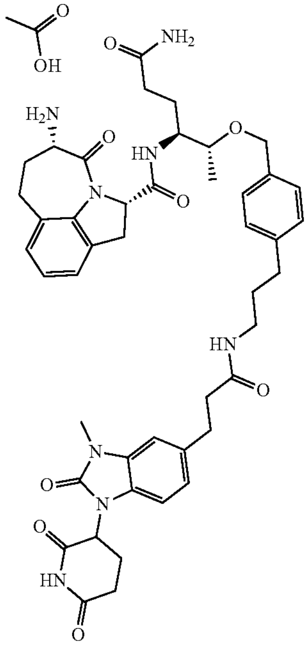 | (4S,5R)-4-[[(2S,11S)-11-amino-12-oxo-1-azatricyclo[6.4.1.0^[4,13]]trideca-4(13),5,7-trien-2-yl]formamido]-5-[[4-(3-[3[1(2,6-dioxopiperidin-3-yl)-3-methyl-2-oxo-2,3-dihydro-1H-1,3-benzodiazol-5-yl]propanamido]propyl)phenyl]methoxy]hexanamide acetate | 835.6 | (400 MHz, DMSO-$d_6$) δ 7.90-7.80 (m, 2H), 7.18 (d, J = 7.4 Hz, 2H), 7.09 (d, J = 7.8 Hz, 2H), 7.06-6.98 (m, 4H), 6.97-6.88 (m, 2H), 6.70 (s, 1H), 5.33 (dd, J = 12.7, 5.3 Hz, 1H), 5.07 (dd, J = 11.0, 3.2 Hz, 1H), 4.48-4.33 (m, 2H), 3.84-3.73 (m, 1H), 3.52-3.32 (m, 9H), 3.09-2.99 (m, 4H), 2.92-2.82 (m, 4H), 2.75-2.56 (m, 2H), 2.41 (t, J = 7.7 Hz, 2H), 2.12-1.87 (m, 7H), 1.85-1.73 (m, 1H), 1.72-1.43 (m, 3H), 1.09 (d, J = 6.2 Hz, 3H). |

TABLE 52-continued

| Characterization data for intermediates prepare according to above. | | | | |
|---|---|---|---|---|
| Intermediate | Structure | Chemical Name | MS: $[(M + 1)]^+$ | $^1H$ NMR |
| J8 | 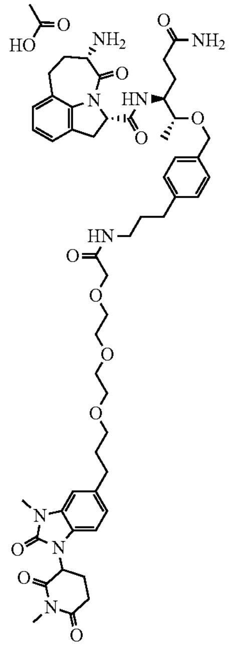 | (4S,5R)-4-[[(2S,11S)-11-amino-12-oxo-1-azatricyclo[6.4.1.0^[4,13]]trideca-4(13),5,7-trien-2-yl]formamido]-5-[4-(3-[2-[2-(2-[3-[3-methyl-1-(1-methyl-2,6-dioxopiperidin-3-yl)-2-oxo-1,3-benzodiazol-5-yl]propoxy]ethoxy)ethoxy]acetamido]propyl)phenyl]methoxy]hexanamide acetate | 981.6 | (400 MHz, DMSO-$d_6$) δ 7.80 (d, J = 9.3 Hz, 1H), 7.71 (t, J = 5.8 Hz, 1H), 7.21-7.08 (m, 5H), 7.06-6.97 (m, 4H), 6.92 (dd, J = 8.2, 6.6 Hz, 1H), 6.85 (d, J = 8.1 Hz, 1H), 6.67 (s, 1H), 5.40 (dd, J = 13.0, 5.3 Hz, 1H), 5.06 (dd, J = 11.0, 3.2 Hz, 1H), 4.46-4.35 (m, 2H), 3.88 (s, 2H), 3.83-3.70 (m, 1H), 3.62-3.53 (m, 6H), 3.53-3.34 (m, 10H), 3.32 (s, 3H), 3.12 (q, J = 6.8 Hz, 2H), 3.04 (s, 3H), 2.89-2.70 (m, 2H), 2.70-2.60 (m, 3H), 2.55-2.50 (m, 2H), 2.12-1.94 (m, 3H), 1.91 (s, 6H), 1.87-1.67 (m, 4H), 1.62-1.48 (m, 1H), 1.08 (d, J = 6.2 Hz, 3H). |
| J9 | 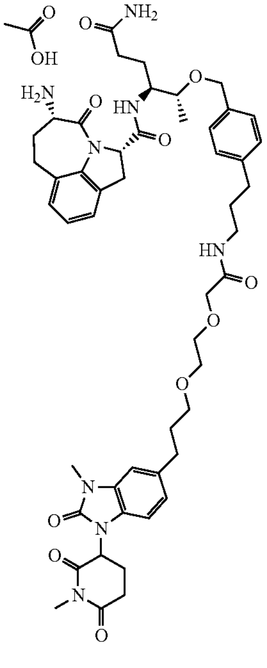 | (4S,5R)-4-[[(2S,11S)-11-amino-12-oxo-1-azatricyclo[6.4.1.0^[4,13]]trideca-4(13),5,7-trien-2-yl]formamido]-5-[(4-[3-[2-(2-[3-[3-methyl-1-(1-methyl-2,6-dioxopiperidin-3-yl)-2-oxo-1,3-benzodiazol-5-yl]propoxy]ethoxy)acetamido]propyl]phenyl)methoxy]hexanamide acetate | 937.5 | (400 MHz, DMSO-$d_6$) δ 7.80 (d, J = 9.1 Hz, 1H), 7.73 (d, J = 5.9 Hz, 1H), 7.21-7.15 (m, 3H), 7.11 (d, J = 8.0 Hz, 2H), 7.06-6.98 (m, 4H), 6.92 (dd, J = 8.2, 6.6 Hz, 1H), 6.85 (d, J = 8.0 Hz, 1H), 6.67 (s, 1H), 5.40 (dd, J = 13.0, 5.3 Hz, 1H), 5.05 (dd, J = 10.9, 3.3 Hz, 1H), 4.46-4.35 (m, 2H), 3.90 (s, 2H), 3.83-3.72 (m, 1H), 3.61 (dd, J = 6.1, 3.4 Hz, 2H), 3.58-3.53 (m, 2H), 3.47-3.39 (m, 4H), 3.38-3.28 (m, 3H), 3.13 (q, J = 6.6 Hz, 2H), 3.07-2.90 (m, 6H), 2.89-2.78 (m, 2H), 2.77-2.61 (m, 4H), 2.55-2.50 (m, 2H), 2.08-1.94 (m, 5H), 1.91 (s, 3H), 1.89-1.68 (m, 5H), 1.62-1.48 (m, 1H), 1.08 (d, J = 6.2 Hz, 3H). |

TABLE 52-continued

Characterization data for intermediates prepare according to above.

| Inter-mediate | Structure | Chemical Name | MS: $[(M + 1)]^+$ | $^1H$ NMR |
|---|---|---|---|---|
| J10 | 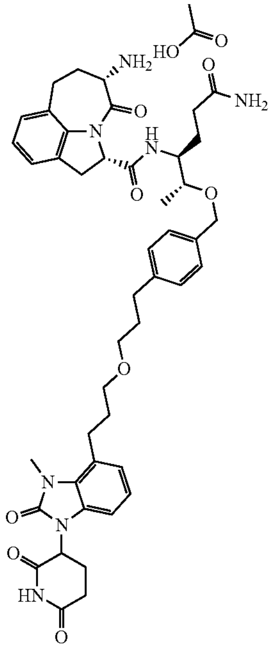 | (4S,5R)-4-[[(2S,11S)-11-amino-12-oxo-1-azatricyclo[6.4.1.0^[4,13]]trideca-4(13),5,7-trien-2-yl]formamido]-5-[[4-(3-[3-[1-(2,6-dioxopiperidin-3-yl)-3-methyl-2-oxo-1,3-benzodiazol-4-yl]propoxy]propyl)phenyl]methoxy]hexanamide acetate | 822.6 | (400 MHz, DMSO-$d_6$) δ 7.79 (d, J = 9.3 Hz, 1H), 7.19 (d, J = 7.8 Hz, 2H), 7.16-7.10 (m, 3H), 7.04-6.95 (m, 4H), 6.94-6.85 (m, 2H), 6.66 (s, 1H), 5.36 (d, J = 8.5 Hz, 1H), 5.05 (d, J = 9.1 Hz, 1H), 4.40 (d, J = 12.4 Hz, 2H), 3.83-3.70 (m, 1H), 3.57 (s, 3H), 3.46-3.35 (m, 6H), 3.02-2.93 (m, 3H), 2.93-2.80 (m, 1H), 2.67-2.58 (m, 4H), 2.55-2.50 (m, 2H), 2.07-1.93 (m, 6H), 1.90 (s, 3H), 1.87-1.73 (m, 5H), 1.61-1.48 (m, 1H), 1.08 (d, J = 6.2 Hz, 3H). |
| J11 | 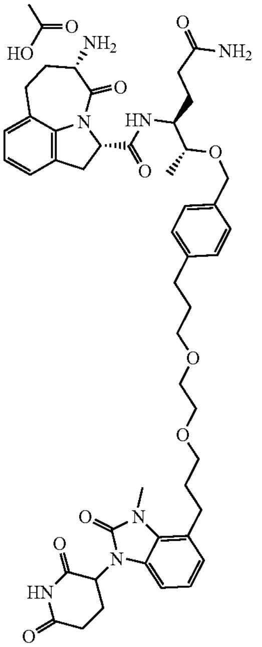 | (4S,5R)-4-[[(2S,11S)-11-amino-12-oxo-1-azatricyclo[6.4.1.0^[4,13]]trideca-4(13),5,7-trien-2-yl]formamido]-5-([4-[3-(2-[3-[1-(2,6-dioxopiperidin-3-yl)-3-methyl-2-oxo-1,3-benzodiazol-4-yl]propoxy]ethoxy)propyl]phenyl]methoxy)hexanamide acetate | 866.6 | (400 MHz, DMSO-$d_6$) δ 7.79 (d, J = 9.2 Hz, 1H), 7.22-7.10 (m, 6H), 7.01 (d, J = 7.5 Hz, 2H), 6.98-6.89 (m, 3H), 6.8 (dt, J = 5.5, 3.4 Hz, 1H), 6.67 (s, 1H), 5.36 (dd, J = 12.7, 5.4 Hz, 1H), 5.05 (d d, J = 10.9, 3.2 Hz, 1H), 4.41 (d, J = 3.3 Hz, 2H), 3.82-3.73 (m, 1H), 3.58-3.30 (m, 20H), 3.07-2.80 (m, 5H), 2.76-2.57 (m, 3H), 2.12-1.92 (d, J = 14.5 Hz, 2H), 1.89 (s, 3H), 1.86-1.73 (m, 4H), 1.61-1.49 (m, 1H), 1.08 (d, J = 6.4 Hz, 3H). |

TABLE 52-continued

Characterization data for intermediates prepare according to above.

| Intermediate | Structure | Chemical Name | MS: [(M + 1)]+ | $^1$H NMR |
|---|---|---|---|---|
| J12 | 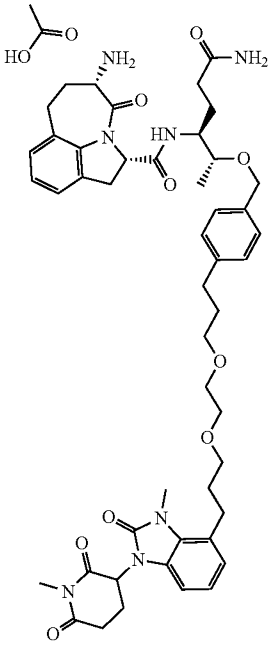 | (4S,5R)-4-[[(2S,11S)-11-amino-12-oxo-1-azatricyclo[6.4.1.0^[4,13]]trideca-4(13),5,7-trien-2-yl]formamido]-5-([4-[3-(2-[3-[3-methyl-1-(1-methyl-2,6-dioxopiperidin-3-yl)-2-oxo-1,3-benzodiazol-4-yl]propoxy]ethoxy)propyl]phenyl]methoxy)hexanamide acetate | 880.6 | (400 MHz, DMSO-$d_6$) δ 7.79 (d, J = 9.2 Hz, 1H), 7.21-7.08 (m, 3H), 7.04-6.90 (m, 4H), 6.89 (s, 1H), 6.66 (s, 1H), 5.43 (d, J = 13.0 Hz, 1H), 5.05 (d, J = 10.0 Hz, 1H), 4.44-4.35 (m, 2H), 3.84-3.69 (m, 1H), 3.56 (d, J = 3.4 Hz, 3H), 3.50-3.43 (m, 3H), 3.48-3.27 (m, 9H), 3.03 (d, J = 3.2 Hz, 3H), 3.02-2.90 (m, 2H), 2.95 (m, 4H), 2.88-2.77 (m, 2H), 2.73 (d, J = 12.6 Hz, 1H), 2.61 (s, 2H), 2.05-1.94 (m,4H), 1.89 (s, 3H), 1.86-1.68 (m, 4H), 1.61-1.46 (m, 1H), 1.07 (dd, J = 6.4, 2.9 Hz, 3H). |
| J13 | 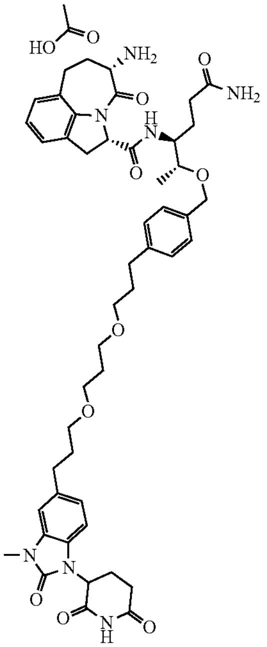 | (4S,5R)-4-[[(2S,11S)-11-Amino-12-oxo-1-azatricyclo[6.4.1.0^[4,13]]trideca-4(13),5,7-trien-2-yl]formamido]-5-([4-[3-(3-[3-[1-(2,6-dioxopiperidin-3-yl)-3-methyl-2-oxo-1,3-benzodiazol-5-yl]propoxy]propoxy)propyl]phenyl]methoxy)hexanamide acetate | 880.5 | Crude to next step without further purification |

TABLE 52-continued

| Characterization data for intermediates prepare according to above. | | | | |
|---|---|---|---|---|
| Intermediate | Structure | Chemical Name | MS: $[(M + 1)]^+$ | $^1$H NMR |
| J14 | 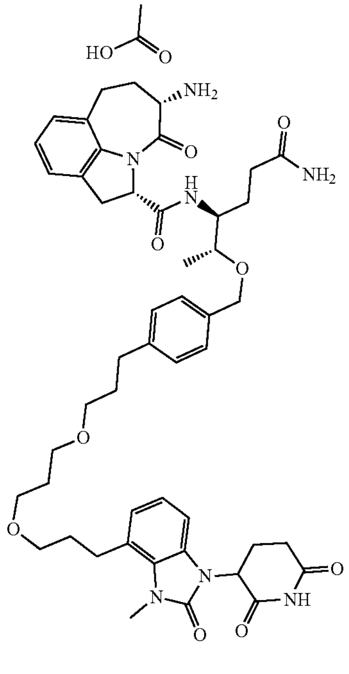 | (4S,5R)-4-[(2S,11S)-11-amino-12-oxo-1-azatricyclo[6.4.1.0^[4,13]]trideca-4(13),5,7-trien-2-yl]formamido]-5-([4-[3-(3-[3-[1(2,6-dioxopiperidin-3-yl)-3-methyl-2-oxo-1,3-benzodiazol-4-yl]propoxy]propoxy)propyl]phenyl]methoxy)hexanamide acetate | 880.6 | Crude to next step without further purification |
| J15 | 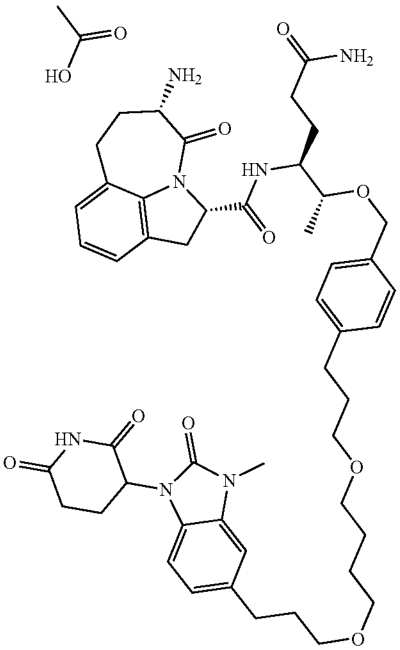 | (4S,5R)-4-[[(2S,11S)-11-Amino-12-oxo-1-azatricyclo[6.4.1.0^[4,13]]trideca-4(13),5,7-trien-2-yl]formamido]-5-([4-[3-(4-[3-[1-(2,6-dioxopiperidin-3-yl)-3-methyl-2-oxo-1,3-benzodiazol-5-yl]propoxy]butoxy)propyl]phenyl]methoxy)hexanamid acetate | 894.7 | (400 MHz, DMSO-$d_6$) δ 7.81 (d, J = 9.3 Hz, 1H), 7.21-7.09 (m, 5H), 7.05-6.97 (m, 4H), 6.97-6.89 (m, 1H), 6.87 (d, J = 8.1 Hz, 1H), 6.68 (s, 1H), 5.34 (dd, J = 12.7, 5.4 Hz, 1H), 5.06 (dd, J = 10.9, 3.2 Hz, 1H), 4.41 (s, 2H), 3.85-3.72 (m, 1H), 3.52-3.45 (m, 1H), 3.48-3.30 (m, 15H), 3.02 (t, J = 5.5 Hz, 2H), 2.96-2.80 (m, 2H), 2.76-2.57 (m, 6H), 2.55-2.50 (m, 2H), 2.08 (dd, J = 10.6, 4.9 Hz, 1H), 2.07-1.91 (m, 3H), 1.91 (s, 3H), 1.87-1.72 (m, 5H), 1.60-1.53 (m, 5H), 1.08 (d, J = 6.2 Hz, 3H). |

TABLE 52-continued

| Characterization data for intermediates prepare according to above. | | | | |
|---|---|---|---|---|
| Inter-mediate | Structure | Chemical Name | MS: [(M + 1)]+ | $^1$H NMR |
| J16 | 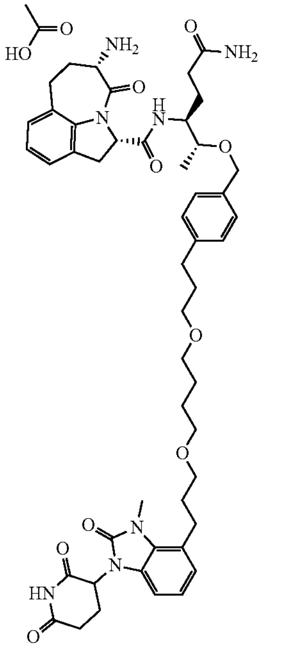 | (4S,5R)-4-[[(2S, 11S)-11-amino-12-oxo-1-azatricyclo[6.4.1.0^[4,13]]trideca-4(13),5,7-trien-2-yl]formamido]-5-([4-[3-(4-[3-[1-(2,6-dioxopiperidin-3-yl)-3-methyl-2-oxo-1,3-benzodiazol-4-yl]propoxy]butoxy) propyl]phenyl] methoxy)hexanamide acetate | 894.6 | (400 MHz, DMSO-$d_6$) δ 7.81 (d, J = 9.3 Hz, 1H), 7.22-7.09 (m, 5H), 7.01 (d, J = 7.4 Hz, 2H), 6.99 -6.88 (m, 3H), 6.86 (dd, J = 5.6, 3.3 Hz, 1H), 6.68 (s, 1H), 5.37 (dd, J = 12.5, 5.4 Hz, 1H), 5.06 (dd, J = 11.0, 3.2 Hz, 1H), 4.46-4.35 (m, 2H), 3.79 (t, J = 5.2 Hz, 1H), 3.56 (s, 3H), 3.46-3.32 (m, 13H), 3.07-2.80 (m, 6H), 2.72 (td, J = 12.8, 4.4 Hz, 1H), 2.65-2.54 (m, 3H), 2.13-1.93 (m, 3H), 1.90 (s, 3H), 1.86-1.71 (m, 5H), 1.64-1.48 (m, 5H), 1.08 (d, J = 6.3 Hz, 3H). |
| J17 | 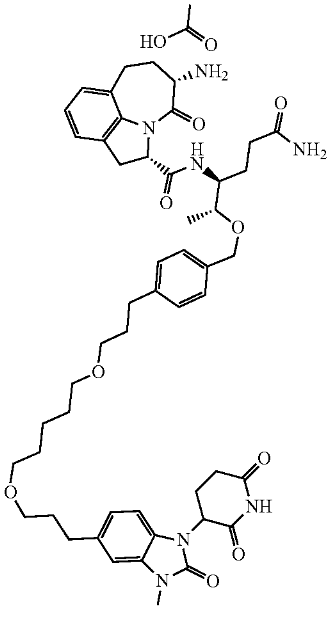 | (4S,5R)-4-[[(2S,11S)-11-amino-12-oxo-1-azatricyclo[6.4.1.0^[4,13]]trideca-4(13),5,7-trien-2-yl]formamido]-5-[(4-[3[(6-[3-[1-(2,6-dioxopiperidin-3-yl)-3-methyl-2-oxo-1,3-benzodiazol-5-yl]propoxy]hexyl) oxy]propyl]phenyl) methoxy]hexanamide acetate | 908.7 | (400 MHz, DMSO-$d_6$) δ 7.80 (d, J = 9.2 Hz, 1H), 7.22-7.15 (m, 3H), 7.11 (d, J = 7.9 Hz, 2H), 7.05-6.97 (m, 4H), 6.92 (dd, J = 8.1, 6.7 Hz, 1H), 6.86 (dd, J = 8.1, 1.6 Hz, 1H), 6.68 (s, 1H), 5.34 (dd, J = 12.7, 5.3 Hz, 1H), 5.05 (dd, J = 11.0, 3.2 Hz, 1H), 4.41 (d, J = 2.2 Hz, 2H), 3.82-3.76 (m, 1H), 3.47-3.40 (m, 2H), 3.43-3.29 (m, 13H), 3.07-2.98 (m, 2H), 2.95-2.79 (m, 2H), 2.77-2.55 (m, 7H), 2.13-1.93 (m, 3H), 1.90 (s, 3H), 1.85-1.73 (m, 5H), 1.61-1.46 (m, 5H), 1.43-1.31 (m, 2H), 1.08 (d, J = 6.3 Hz, 3H). |

TABLE 52-continued

| Characterization data for intermediates prepare according to above. | | | | |
|---|---|---|---|---|
| Intermediate | Structure | Chemical Name | MS: [(M + 1)]$^+$ | $^1$H NMR |
| J18 | 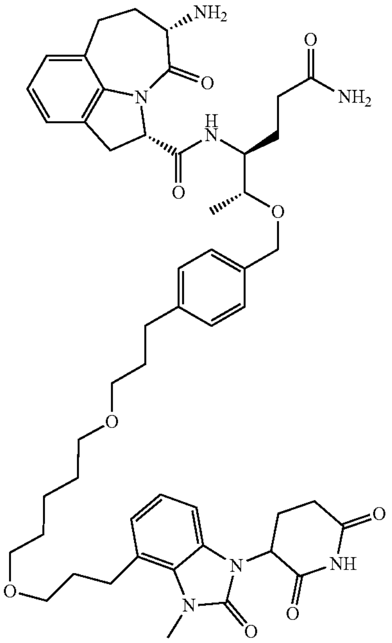 [SMILES: C[C@@H](OCc1ccc(CCCOCCCCCOCCCc2cccc3c2n(C)c(=O)n3C2CCC(=O)NC2=O)cc1)[C@H](CCC(N)=O)NC(=O)[C@@H]1Cc2cccc3c2N1C(=O)[C@@H](N)CC3] | (4S,5R)-4-[[(2S,11S)-11-amino-12-oxo-1-azatricyclo[6.4.1.0^[4,13]]trideca-4(13),5,7-trien-2-yl]formamido]-5-[(4-[3-[(5-[3-[1-(2,6-dioxopiperidin-3-yl)-3-methyl-2-oxo-1,3-benzodiazol-4-yl]propoxy] pentypoxylpropyl] phenyl) methoxylhexanamide | 908.7 | (400 MHz, $CD_3OD$) δ 7.22 (d, J = 7.6 Hz, 2H), 7.13 (d, J = 7.7 Hz, 2H), 7.10-6.99 (m, 4H), 6.99-6.91 (m, 2H), 5.38-5.27(m, 1H), 5.13 (d, J = 11.2 Hz, 1H), 4.48 (t, J = 9.1 Hz, 2H), 4.03-3.95 (m, 1H), 3.73 (d, J = 9.8 Hz, 1H), 3.69-3.62 (m, 4H), 3.61-3.54 (m, 1H), 3.53-3.40 (m, 6H), 3.40-3.26 (m, 6H), 3.16 (t, J = 6.5 Hz, 2H), 3.10-2.87 (m, 4H), 2.80 (d, J = 14.7 Hz, 2H), 2.69 (t, J = 7.7 Hz, 2H), 2.37-2.20 (m, 2H), 2.20-2.07 (m, 2H), 1.96-1.83 (m, 7H), 1.77-1.58 (m, 4H), 1.52 (d, J = 6.7 Hz, 1H), 1.20 (d, J = 6.2 Hz, 3H). |
| J19 | 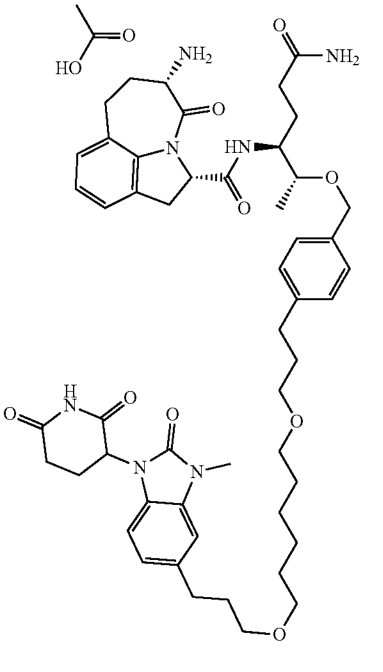 | (4S,5R)-4-[[(2S,11S)-11-amino-12-oxo-1-azatricyclo[6.4.1.0^[4,13]]trideca-4(13),5,7-trien-2-yl]formamido]-5-[(4-[3-[(6-[3-[1-(2,6-dioxopiperidin-3-yl)-3-methyl-2-oxo-1,3-benzodiazol-5-yl]propoxy]hexyl) oxy]propyl]phenyl) methoxy]hexanamide acetate | 922.4 | (400 MHz, $CD_3OD$) δ 7.24 (d, J = 7.8 Hz, 2H), 7.17-7.01 (m, 6H), 7.01 (d, J = 4.4 Hz, 1H), 7.01-6.93 (m, 1H), 5.31 (dd, J = 12.5, 5.4 Hz, 1H), 5.15 (dd, J = 10.9, 3.6 Hz, 1H), 4.56-4.44 (m, 2H), 4.01 (dt, J = 11.2, 3.7 Hz, 1H), 3.87-3.80 (m, 1H), 3.58 (p, J = 6.2 Hz, 1H), 3.51-3.38 (m, 11H), 3.36-3.29 (m, 6H), 3.18 (t, J = 6.7 Hz, 2H), 3.01 (dd, J = 16.7, 3.6 Hz, 1H), 2.95-2.86 (m, 1H), 2.84-2.72 (m, 4H), 2.68 (t, J = 7.6 Hz, 2H), 2.36-2.20 (m, 2H), 2.17 (dd, J = 11.3, 5.7 Hz, 1H), 2.01 (dd, J = 13.1, 7.2 Hz, 1H), 1.93 (s, 3H), 1.97-1.81 (m, 4H), 1.76-1.65 (m, 1H), 1.64-1.55 (m, 1H), 1.50-1.38 (m, 4H), 1.20 (d, J = 6.3 Hz, 3H). |

TABLE 52-continued

| Characterization data for intermediates prepare according to above. | | | | |
|---|---|---|---|---|
| Intermediate | Structure | Chemical Name | MS: $[(M + 1)]^+$ | $^1H$ NMR |
| J20 | 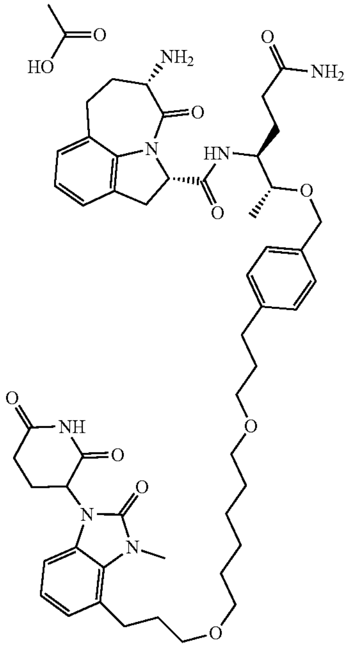 | (4S,5R)-4-[[(2S,11S)-11-amino-12-oxo-1-azatricyclo[6.4.1.0^[4,13]]trideca-yl]formamido]-5-4(13),5,7-trien-2-[(4-[3-[((6-[3-[1-(2,6-dioxopiperidin-3-yl)-3-methyl-2-oxo-1,3-benzodiazol-4-yl]propoxy]hexyl)oxy]propyl]phenyl)methoxy]hexanamide acetate | $[(M/2 + 1)]^+$ = 462.0 | (400 MHz, DMSO-$d_6$) δ 7.81 (d, J = 9.3 Hz, 1H), 7.22-7.15 (m, 3H), 7.11 (d, J = 7.9 Hz, 2H), 7.01 (d, J = 7.4 Hz, 2H), 6.99-6.88 (m, 3H), 6.86 (dd, J = 5.5, 3.4 Hz, 1H), 6.68 (s, 1H), 5.37 (dd, J = 12.5, 5.4 Hz, 1H), 5.06 (dd, J = 10.9, 3.2 Hz, 1H), 4.46-4.35 (m, 2H), 3.81-3.75 (m, 1H), 3.49-3.25 (m, 12H), 3.07-2.78 (m, 6H), 2.72 (td, J = 12.8, 4.4 Hz, 1H), 2.66-2.59 (m, 1H), 2.58 (d, J = 7.9 Hz, 2H), 2.55-2.50 (m, 2H), 2.13-2.05 (m, 1H), 2.03-1.91 (m, 2H), 1.90 (s, 3H), 1.88-1.71 (m, 6H), 1.56-1.47 (m, 6H), 1.40-1.30 (m, 4H), 1.08 (d, J = 6.2 Hz, 3H). |
| J21 | 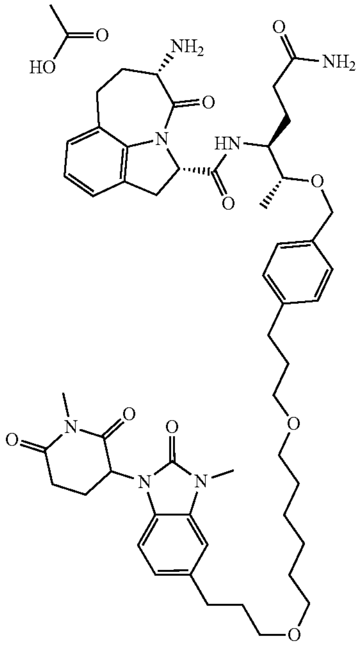 | (4S,5R)-4-[[(2S,11S)-11-amino-12-oxo-1-azatricyclo[6.4.1.0^[4,13]]trideca-4(13),5,7-trien-2-yl]formamido]-5-[(4-[3-[(6-[3-[3-methyl-1-(1-methyl-2,6-dioxopiperidin-3-yl)-2-oxo-1,3-benzodiazol-5-yl]propoxy]hexyl)oxy]propyl]phenyl)methoxy]hexanamide acetate | 936.7 | (400 MHz, DMSO-$d_6$) δ 7.79 (d, J = 9.3 Hz, 1H), 7.27-7.08 (m, 5H), 7.07-6.99 (m, 4H), 6.92 (dd, J = 8.2, 6.7 Hz, 1H), 6.85 (dd, J = 8.1, 1.6 Hz, 1H), 6.66 (s, 1H), 5.40 (dd, J = 13.0, 5.3 Hz, 1H), 5.06 (dd, J = 10.9, 3.3 Hz, 1H), 4.47-4.36 (m, 2H), 3.84-3.73 (m, 1H), 3.49-3.40 (m, 1H), 3.40-3.25 (m, 16H), 3.06-2.91 (m, 4H), 2.88-2.71 (m, 2H), 2.70-2.56 (m, 4H), 2.55-2.50 (m, 2H), 2.12-1.95 (m, 2H), 1.91 (s, 3H), 1.86-1.73 (m, 5H), 1.60-1.46 (m, 6H), 1.37-1.30 (m, 4H), 1.08 (d, J = 6.2 Hz, 3H). |

TABLE 52-continued

| Characterization data for intermediates prepare according to above. | | | | |
|---|---|---|---|---|
| Inter-mediate | Structure | Chemical Name | MS: $[(M + 1)]^+$ | $^1$H NMR |
| J22 | 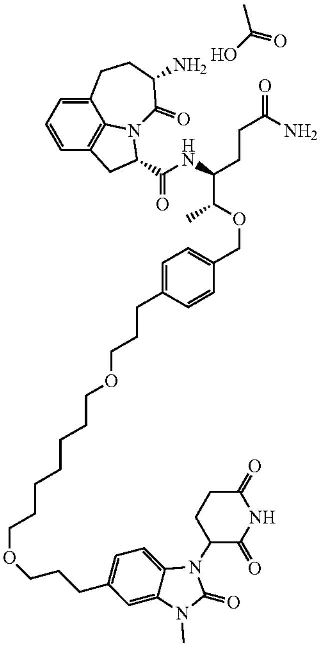 | (4S,5R)-4-[[(2S,11S)-11-amino-12-oxo-1-azatricyclo[6.4.1.0^[4,13]]trideca-4(13),5,7-trien-2-yl]formamido]-5-[(4-[3-[(7-[3-[1-(2,6-dioxopiperidin-3-yl)-3-methyl-2-oxo-1,3-benzodiazol-5-yl]propoxy] heptypoxylpropyl] phenyl) methoxylhexanamide acetate | 936.6 | (400 MHz, DMSO-$d_6$) δ 7.81 (d, J = 9.3 Hz, 1H), 7.23-7.15 (m, 3H), 7.11 (d, J = 7.8 Hz, 2H), 7.06-6.97 (m, 4H), 6.96-6.89 (m, 1H), 6.86 (d, J = 8.1 Hz, 1H), 6.68 (s, 1H), 5.34 (dd, J = 12.7, 5.3 Hz, 1H), 5.06 (dd, J = 11.0, 3.2 Hz, 1H), 4.41 (d, J = 2.1 Hz, 2H), 3.84-3.73 (m, 1H), 3.49-3.31 (m, 12H), 3.03 (q, J = 5.9, 5.2 Hz, 2H), 2.87 (td, J = 16.5, 4.0 Hz, 2H), 2.76-2.55 (m, 6H), 2.55-2.50 (m, 2H), 2.12-2.03 (m, 1H), 2.05-1.93 (m, 4H), 1.90 (s, 3H), 1.85-1.70 (m, 5H), 1.61-1.44 (m, 5H), 1.37-1.22 (m, 6H), 1.08 (d, J = 6.2 Hz, 3H). |
| J23 | 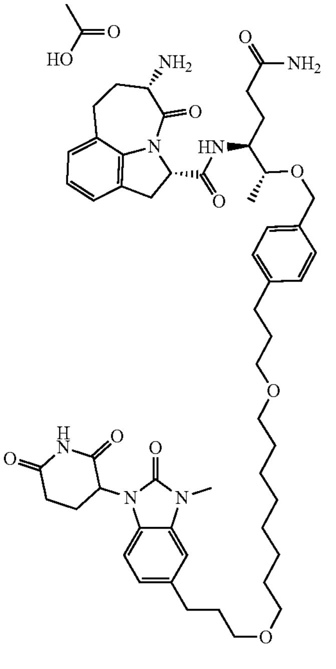 | (4S,5R)-4-[[(2S,11S)-11-amino-12-oxo-1-azatricyclo[6.4.1.0^[4,13]]trideca-4(13),5,7-trien-2-yl]formamido]-5-[(4-[3-[(8-[3-[1-(2,6-dioxopiperidin-3-yl)-3-methyl-2-oxo-1,3-benzodiazol-5-yl]propoxy]octyl) oxy]propyl]phenyl) methoxy]hexanamide acetate | 950.7 | (400 MHz, DMSO-$d_6$) δ 11.08 (s, 1H), 8.40 (d, J = 5.0 Hz, 3H), 8.01 (d, J = 9.2 Hz, 1H), 7.21-7.13 (m, 3H), 7.13-7.02 (m, 4H), 7.05-6.96 (m, 3H), 6.86 (dd, J = 8.2, 1.6 Hz, 1H), 6.74 (s, 1H), 5.34 (dd, J = 12.8, 5.3 Hz, 1H), 5.13 (dd, J = 11.0, 3.0 Hz, 1H), 4.40 (s, 2H), 4.20 (d, J = 8.1 Hz, 1H), 4.11-3.94 (m, 3H), 3.81 (s, 1H), 3.49-3.43 (m, 2H), 3.43-3.29 (m, 11H), 3.14 (d, J = 6.1 Hz, 2H), 2.87 (dd, J = 16.7, 9.7 Hz, 2H), 2.67-2.53 (m, 6H), 2.19 (d, J = 14.3 Hz, 1H), 2.15-1.96 (m, 2H), 1.85-1.69 (m, 5H), 1.67-1.43 (m, 6H), 1.29 (s, 9H), 1.09 (d, J = 6.2 Hz, 3H). |

TABLE 52-continued

| Characterization data for intermediates prepare according to above. | | | | |
|---|---|---|---|---|
| Intermediate | Structure | Chemical Name | MS: $[(M + 1)]^+$ | $^1H$ NMR |
| J24 | 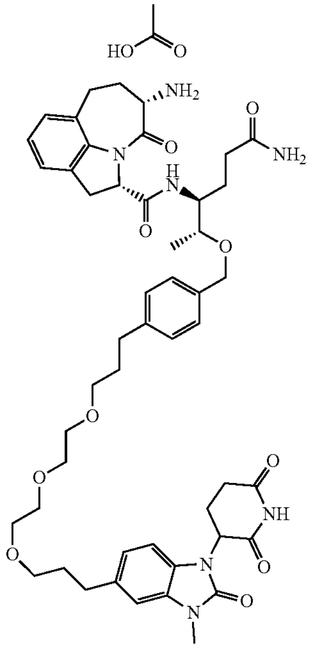 | (4S,5R)-4-[[(2S,11S)-11-amino-12-oxo-1-azatricyclo[6.4.1.0^[4,13]]trideca-4(13),5,7-trien-2-yl]formamido]-5-[(4-[3-[2-(2-[3-[1-(2,6-dioxopiperidin-3-yl)-3-methyl-2-oxo-1,3-benzodiazol-5-yl]propoxy]ethoxy)ethoxylpropyl]phenyl)methoxy]hexanamide acetate | $[(M/2 + 1)]^+$ = 456.0 | Used in the next step without further purification |
| J25 | 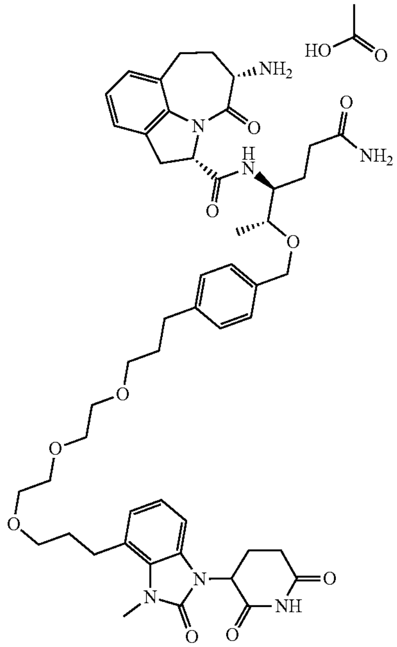 | (4S,5R)-4-[[(2S,11S)-11-Amino-12-oxo-1-azatricyclo[6.4.1.0^[4,13]]trideca-4(13),5,7-trien-2-yl]formamido]-5-[(4-[3-[2-(2-[3-[1-(2,6-dioxopiperidin-3-yl)-3-methyl-2-oxo-1,3-benzodiazol-4-yl]propoxy]ethoxy)ethoxylpropyl]phenyl)methoxy]hexanamide acetate | 910.7 | (400 MHz, DMSO-$d_6$) δ 7.80 (d, J = 9.3 Hz, 1H), 7.25-7.07 (m, 5H), 7.02 (d, J = 7.4 Hz, 2H), 6.98-6.95 (m, 2H), 6.95-6.91 (m, 1H), 6.87 (dd, J = 5.8, 3.1 Hz, 1H), 6.67 (s, 1H), 5.36 (dd, J = 12.5, 5.4 Hz, 1H), 5.06 (dd, J = 11.0, 3.2 Hz, 1H), 4.47-4.35 (m, 2H), 3.83-3.71 (m, 1H), 3.61-3.42 (m, 16H), 3.41-3.33 (m, 3H), 3.06-2.80 (m, 6H), 2.76-2.55 (m, 4H), 2.13-1.94 (m, 4H), 1.91 (s, 3H), 1.86-1.73 (m, 5H), 1.61-1.50 (m, 1H), 1.08 (d, J = 6.2 Hz, 3H). |

TABLE 52-continued

Characterization data for intermediates prepare according to above.

| Intermediate | Structure | Chemical Name | MS: $[(M + 1)]^+$ | $^1H$ NMR |
|---|---|---|---|---|
| J26 | 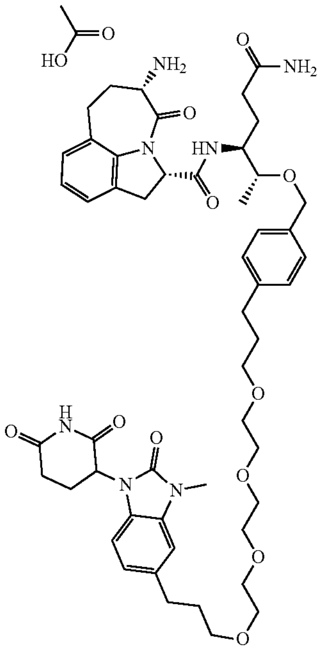 | (4S,5R)-4-[[(2S,11S)-11-amino-12-oxo-1-azatricyclo[6.4.1.0^[4,13]]trideca-4(13),5,7-trien-2-yl]formamido]-5-[(4-[16-[1-(2,6-dioxopiperidin-3-yl)-3-methyl-2-oxo-2,3-dihydro-1H-1,3-benzodiazol-5-yl]-4,7,10,13-tetraoxahexadecan-1-yl]phenyl)methoxy] hexanamide acetate | 954.7 | (400 MHz, DMSO-$d_6$) δ 7.83 (d, J = 9.3 Hz, 1H), 7.22-7.15 (m, 3H), 7.12 (d, J = 7.9 Hz, 2H), 7.07-6.97 (m, 4H), 6.93 (dd, J = 8.2, 6.7 Hz, 1H), 6.87 (dd, J = 8.1, 1.6 Hz, 1H), 6.70 (s, 1H), 5.34 (dd, J = 12.7, 5.4 Hz, 1H), 5.06 (dd, J = 10.9, 3.2 Hz, 1H), 4.41 (d, J = 2.0 Hz, 2H), 3.83-3.72 (m, 1H), 3.58-3.32 (m, 22H), 3.04 (d, J = 12.8 Hz, 2H), 2.93-2.80 (m, 2H), 2.78-2.53 (m, 6H), 2.55-2.50 (m, 2H), 2.13-1.94 (m, 3H), 1.91 (s, 3H), 1.84-1.70 (m, 5H), 1.62-1.49 (m, 1H), 1.08 (d, J = 6.2 Hz, 3H). |
| J27 | 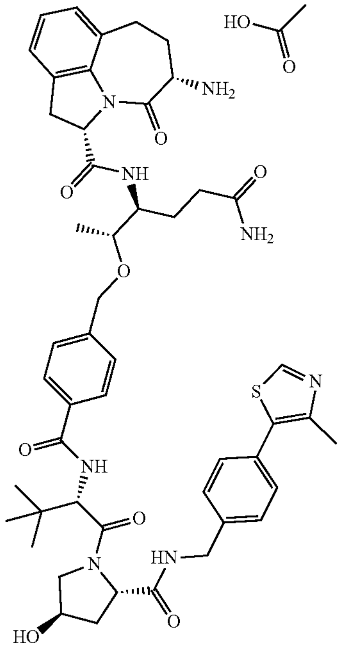 | (2S,4R)-1-[(2S)-2-[[4-([[(2R,3S)-3-[[(2S,11S)-11-amino-12-oxo-1-azatricyclo[6.4.1.0^[4,13]]trideca-4(13),5,7-trien-2-yl]formamido]-5-carbamoylpentan-2-yl]oxy]methyl) phenyl] formamido]-3,3-dimethylbutanoyl]-4-hydroxy-N-[[4-(4-methyl-1,3-thiazol-5-yl)phenyl]methyl] pyrrolidine-2-carboxamide acetate | 921.4 | (400 MHz, DMSO-$d_6$) δ 8.99 (s, 1H), 8.60 (d, J = 6.0 Hz, 1H), 7.90 (d, J = 9.1 Hz, 1H), 7.86-7.76 (m, 3H), 7.47-7.33 (m, 6H), 7.17 (s, 1H), 7.02 (d, J = 7.5 Hz, 2H), 6.96-6.88 (m, 1H), 6.68 (s, 1H), 5.16 (s, 1H), 5.10-5.02 (m, 1H), 4.78 (d, J = 9.0 Hz, 1H), 4.53 (s, 2H), 4.48 (d, J = 8.0 Hz, 1H), 4.47-4.39 (m, 1H), 4.39 (s, 1H), 4.30-4.21 (m, 1H), 3.88-3.78 (m, 1H), 3.74 (s, 2H), 3.51-3.39 (m, 2H), 3.07-2.97 (m, 2H), 2.84 (d, J = 14.9 Hz, 1H), 2.45 (s, 3H), 2.13-2.02 (m, 3H), 2.00-1.94 (m, 3H), 1.91 (s, 3H), 1.84-1.71 (m, 1H), 1.64-1.50 (m, 1H), 1.11 (d, J = 6.3 Hz, 3H), 1.05 (s, 9H). |

TABLE 52-continued

| Characterization data for intermediates prepare according to above. | | | | |
|---|---|---|---|---|
| Inter-mediate | Structure | Chemical Name | MS: [(M + 1)]+ | $^1H$ NMR |
| J28 | 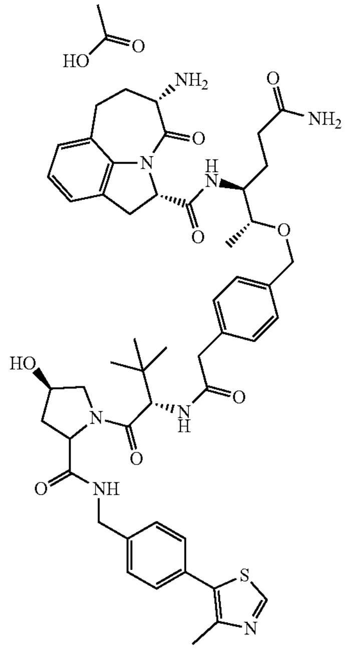 | (2S,4R)-1-[(2S)-2-[2-[4-([[(2R,3S)-3-[(2S,11S)-11-amino-12-oxo-1-azatricyclo[6.4.1.0^[4,13]]trideca-4(13),5,7-trien-2-yl]formamido]-5-carboylpentan-2-yl]oxy]methyl)phenyl]acetamido]-3,3-dimethylbutanoyl]-4-hydroxy-N-[[4-(4-methyl-1,3-thiazol-5-yl)phenyl]methyl]pyrrolidine-2-carboxamide acetate | [M/2 + 1]+ = 468.5 | (400 MHz, DMSO-$d_6$) δ 8.99 (s, 1H), 8.59 (t, J = 6.1 Hz, 1H), 8.12 (d, J = 9.3 Hz, 1H), 7.82 (d, J = 9.3 Hz, 1H), 7.47-7.34 (m, 4H), 7.28-7.14 (m, 5H), 7.02 (dd, J = 7.2, 4.6 Hz, 2H), 6.97-6.89 (m, 1H), 6.68 (s, 1H), 5.06 (dd, J = 10.9, 3.3 Hz, 1H), 4.53 (d, J = 9.3 Hz, 1H), 4.49-4.37 (m, 4H), 4.37-4.32 (m, 1H), 4.23 (dd, J = 15.9, 5.4 Hz, 1H), 3.84-3.72 (m, 1H), 3.71-3.59 (m, 4H), 3.49-3.31 (m, 6H), 3.08-2.99 (m, 2H), 2.89-2.77 (m, 1H), 2.46 (s, 3H), 2.13-1.93 (m, 3H), 1.90 (s, 3H), 1.85-1.72 (m, 1H), 1.63-1.52 (m, 1H), 1.08 (d, J = 6.2 Hz, 3H), 0.92 (s, 9H). |
| J29 | 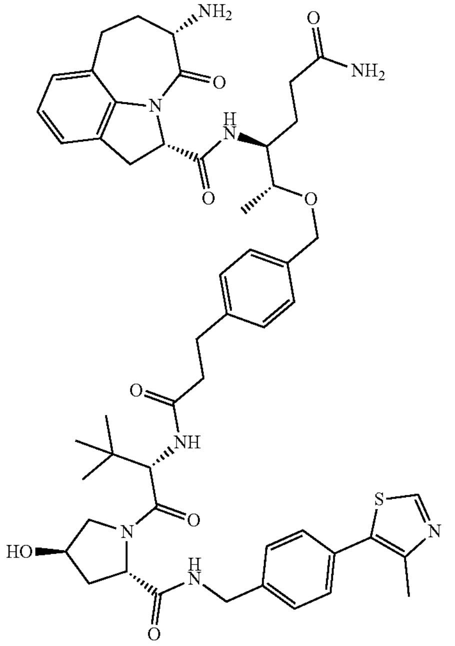 [SMILES: Cc1ncsc1-c1ccc(CNC(=O)[C@@H]2C[C@@H](O)CN2C(=O)[C@@H](NC(=O)CCc2ccc(CO[C@H](C)[C@H](CCC(N)=O)NC(=O)[C@@H]3Cc4cccc5c4N3C(=O)[C@@H](N)CC5)cc2)C(C)(C)C)cc1] | (2S,4R)-1-[(2,5)-2-[3-[4-([[(2R,3S)-3-[[(2S,11S)-11-Amino-12-oxo-1-azatricyclo[6.4.1.0^[4,13]]trideca-4(13),5,7-trien-2-yl]formamido]-5-carbamoylpentan-2-yl]oxy]methyl)phenyl]propanamido]-3,3-dimethylbutanoyl]-4-hydroxy-N-[[4-(4-methyl-1,3-thiazol-5-yl)phenyl]methyl]pyrrolidine-2-carboxamide | 949.7 | (400 MHz, $CDCl_3$) δ 8.67 (s, 1H), 7.39-7.29 (m, 5H), 7.19 (d, J = 7.8 Hz, 2H), 7.07 (d, J = 4.0 Hz, 1H),7.01 (d, J = 3.7 Hz, 2H), 6.74 (s, 1H), 5.99 (s, 1H), 5.09 (d, J = 9.8 Hz, 1H), 4.73-4.52 (m, 4H), 4.43 (d, J = 11.8 Hz, 1H), 4.26 (dd, J = 15.1, 4.4 Hz, 1H), 4.15 (d, J = 11.4 Hz, 1H), 3.97-3.89 (m, 1H), 3.68-3.61 (m, 2H), 3.52 (d, J = 10.0 Hz, 1H), 3.37 (d, J = 16.5 Hz, 1H), 3.27 (d, J = 10.3 Hz, 1H), 3.14-3.01 (m, 2H), 2.86 (dt, J = 13.4, 6.3 Hz, 2H), 2.63-2.51 (m, 3H), 2.48 (s, 3H), 2.27-1.97 (m, 5H), 1.93-1.80 (m, 2H), 1.21 (d, J = 6.4 Hz, 3H), 0.95 (s, 9H). |

TABLE 52-continued

Characterization data for intermediates prepare according to above.

| Inter-mediate | Structure | Chemical Name | MS: $[(M+1)]^+$ | $^1H$ NMR |
|---|---|---|---|---|
| J30 | 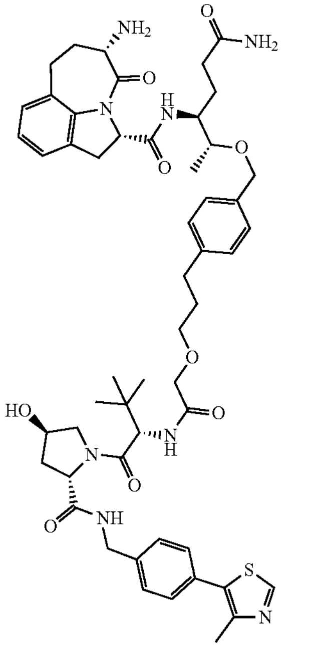 [SMILES: Cc1ncsc1-c1ccc(CNC(=O)[C@@H]2C[C@@H](O)CN2C(=O)[C@@H](NC(=O)COCCCc2ccc(CO[C@H](C)[C@H](CCC(N)=O)NC(=O)[C@@H]3Cc4cccc5c4N3C(=O)[C@@H](N)CC5)cc2)C(C)(C)C)cc1] | (2S,4R)-1-[(2S)-2-(2-[3-[4-([[(2R,3S)-3-[[(2S,11S)-11-Amino-12-oxo-1-azatricyclo[6.4.1.0^[4,13]]trideca-4(13),5,7-trien-2-yl]formamido]-5-carbamoylpentan-2-yl]oxy]methyl)phenyl]propoxy]acetamido)-3,3-dimethylbutanoyl]-4-hydroxy-N-[[4-(4-methyl-1,3-thiazol-5-yl)phenyl]methyl]pyrrolidine-2-carboxamide | 993.3 | (400 MHz, DMSO-$d_6$) δ 8.97 (d, J = 2.0 Hz, 1H), 8.59 (d, J = 6.3 Hz, 1H), 7.78 (d, J = 9.3 Hz, 1H), 7.47-7.35 (m, 5H), 7.22-7.10 (m, 5H), 7.01 (d, J = 7.5 Hz, 2H), 6.92 (t, J = 7.5 Hz, 1H), 6.66 (s, 1H), 5.16 (d, J = 3.6 Hz, 1H), 5.05 (d, J = 11.7 Hz, 1H), 4.57 (d, J = 9.4 Hz, 1H), 4.46 (t, J = 8.2 Hz, 1H), 442-4.32 (m, 4H), 4.31-4.18 (m, 1H), 3.94 (s, 2H), 3.84-3.72 (m, 1H), 3.72-3.58 (m, 2H), 3.53-3.38 (m, 4H), 3.06-2.96 (m, 2H), 2.85 (d, J = 16.6 Hz, 1H), 2.71-2.60 (m, 3H), 2.42 (s, 3H), 2.17-1.70 (m, 9H), 1.62-1.44 (m, 1H), 1.08 (d, J = 6.1 Hz, 3H), 0.95 (s, 9H). |
| J31 | 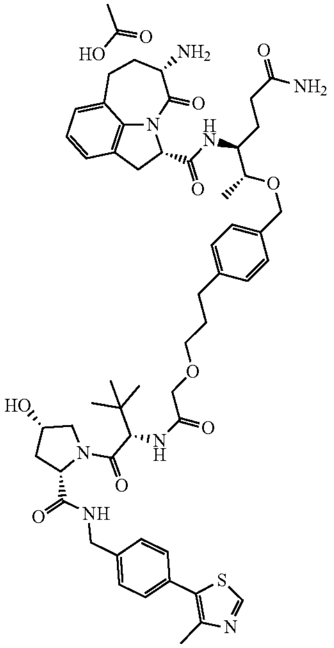 | (2S,4S)-1-[(2S)-2-(2-[3-[4-([[(2R,3S)-3-[[(2S,11S)-11-amino-12-oxo-1-azatricyclo[6.4.1.0^[4,13]]trideca-4(13),5,7-trien-2-yl]formamido]-5-carbamoylpentan-2-yl]oxy]methyl)phenyl]propoxy]acetamido)-3,3-dimethylbutanoyl]-4-hydroxy-N-[[4-(4-methyl-1,3-thiazol-5-yl)phenyl]methyl]pyrrolidine-2-carboxamide acetate | 993.7 | (400 MHz, DMSO-$d_6$) δ 8.97 (s, 1H), 8.68 (t, J = 6.0 Hz, 1H), 7.80 (d, J = 9.3 Hz, 1H), 7.44-7.34 (m, 5H), 7.23-7.07 (m, 5H), 7.01 (d, J = 7.5 Hz, 2H), 6.92 (dd, J = 8.1, 6.7 Hz, 1H), 6.67 (s, 1H), 5.05 (dd, J = 11.0, 3.2 Hz, 1H), 4.53 (d, J = 9.3 Hz, 1H), 4.47-4.35 (m, 4H), 4.33-4.18 (m, 2H), 3.93 (s, 2H), 3.91-3.84 (m, 1H), 3.85-3.70 (m, 1H), 3.60-3.30 (m, 8H), 3.02 (q, J = 5.9, 5.3 Hz, 2H), 2.85 (dd, J = 16.9, 3.2 Hz, 1H), 2.64 (t, J = 7.7 Hz, 2H), 2.42 (s, 3H), 2.40-2.29 (m, 1H), 2.11-1.94 (m, 2H), 1.89 (s, 3H), 1.87-1.70 (m, 4H), 1.64-1.46 (m, 1H), 1.07 (d, J = 6.3 Hz, 3H), 0.96 (s, 9H). |

TABLE 52-continued

Characterization data for intermediates prepare according to above.

| Inter-mediate | Structure | Chemical Name | MS: $[(M + 1)]^+$ | $^1H$ NMR |
|---|---|---|---|---|
| J32 | 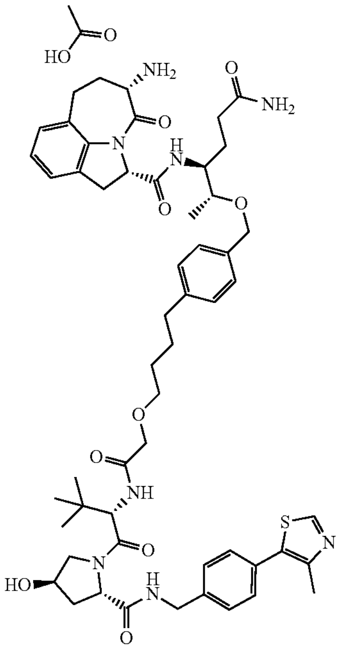 | (2S,4R)-1-[(2S)-2-(2-[4-[4-([[(2R,3S)-3-[[(2S,11S)-11-Amino-12-oxo-1-azatricyclo[6.4.1.0^[4,13]]trideca-4(13),5,7-trien-2-yl]formamido]-5-carbamoylpentan-2-yl]oxy]methyl)phenyl]butoxy]acetamido)-3,3-dimethylbutanoyl]-4-hydroxy-N-[[4-(4-methyl-1,3-thiazol-yl)phenyl]methyl]pyrrolidine-2-carboxamide acetate | 1007.7 | (400 MHz, DMSO-$d_6$) δ 8.98 (s, 1H), 8.61 (s, 1H), 7.80 (d, J = 9.4 Hz, 1H), 7.48-7.35 (m, 5H), 7.20-7.09 (m, 5H), 7.01 (d, J = 7.4 Hz, 2H), 6.95-6.88 (m, 1H), 6.68 (s, 1H), 5.05 (d, J = 9.3 Hz, 1H), 4.56 (d, J = 9.5 Hz, 1H), 4.48-4.3 (m, 5H), 4.28 (d, J = 5.7 Hz, 1H), 3.92 (s, 2H), 3.83-3.74 (m, 1H), 3.73-3.56 (m, 1H), 3.51 (d, J = 6.6 Hz, 2H), 3.47-3.39 (m, 2H), 3.38-3.30 (m, 2H), 3.08-2.97 (m, 2H), 2.84 (d, J = 16.1 Hz, 1H), 2.58 (d, J = 7.5 Hz, 2H), 2.55-2.50 (m, 2H), 2.43 (s, 3H), 2.12-2.00 (m, 2H), 2.00-1.82 (m, 6H), 1.68-1.48 (m, 5H), 1.07 (d, J = 6.1 Hz, 3H), 0.94 (s, 9H). |
| J33 | 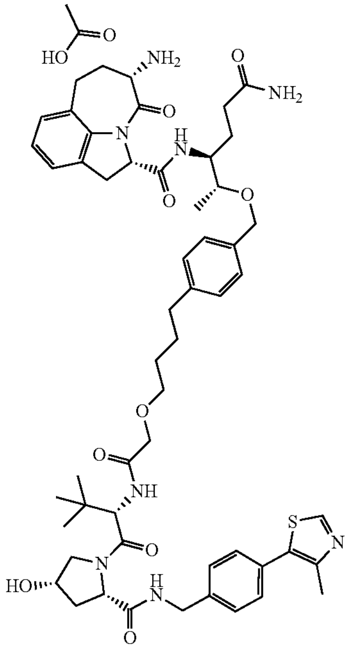 | (2S,4S)-1-[(2S)-2-(2-[4-[4-([[(2R,3S)-3-[[(2S,11S)-11-amino-12-oxo-1-azatricyclo[6.4.1.0^[4,13]]trideca-4(13),5,7-trien-2-yl]formamido]-5-carbamoylpentan-2-yl]oxy]methyl)phenyl]butoxy]acetamido)-3,3-dimethylbutanoyl]-4-hydroxy-N-[[4-(4-methyl-1,3-thiazol-5-yl)phenyl]methyl]pyrrolidine-2-carboxamide acetate | 1007.7 | (400 MHz, DMSO-$d_6$) δ 8.98 (s, 1H), 8.67 (t, J = 6.1 Hz, 1H), 7.79 (d, J = 9.3 Hz, 1H), 7.48-7.32 (m, 4H), 7.20-7.08 (m, 5H), 7.01 (d, J = 7.4 Hz, 2H), 6.92 (dd, J = 8.1, 6.7 Hz, 1H), 6.66 (s, 1H), 5.44 (s, 1H), 5.05 (dd, J = 10.9, 3.2 Hz, 1H), 4.52 (d, J = 9.3 Hz, 1H), 4.47-4.36 (m, 4H), 4.34-4.17 (m, 2H), 3.94-3.83 (m, 3H), 3.82-3.72 (m, 1H), 3.51-3.26 (m, 9H), 3.05-2.95 (m, 2H), 2.85 (dd, J = 16.8, 3.2 Hz, 1H), 2.59 (t, J = 7.4 Hz, 2H), 2.44 (s, 3H), 2.40-2.29 (m, 1H), 2.12-1.92 (m, 3H), 1.90 (s, 3H), 1.75 (dt, J = 12.3, 6.0 Hz, 1H), 1.63-1.49 (m, 4H), 1.07 (d, J = 6.2 Hz, 3H), 0.95 (s, 9H). |

TABLE 52-continued

Characterization data for intermediates prepare according to above.

| Inter-mediate | Structure | Chemical Name | MS: [(M + 1)]+ | $^1$H NMR |
|---|---|---|---|---|
| J34 | 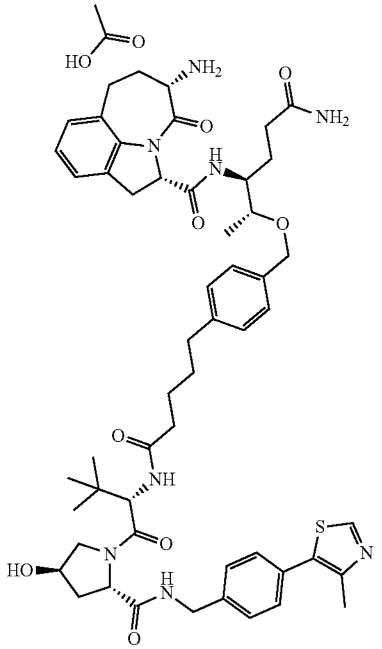 | (2S,4R)-1-[(2S)-2-[5-[4-([[(2R,3S)-3-[[(2S,11S)-11-amino-12-oxo-1-azatricyclo[6.4.1.0^[4,13]]trideca-4(13),5,7-trien-2-yl]formamido]-5-carbamoylpentan-2-yl]oxy]methyl)phenyl]pentanamido]-3,3-dimethylbutanoyl]-4-hydroxy-N-[[4-(4-methyl-1,3-thiazol-5-yl)phenyl]methyl]pyrrolidine-2-carboxamide acetate | 977.9 | (400 MHz, $CD_3OD$) δ 8.89 (s, 1H), 7.48 (d, J = 8.1 Hz, 2H), 7.43 (d, J = 8.3 Hz, 2H), 7.23 (d, J = 7.8 Hz, 2H), 7.14 (d, J = 7.9 Hz, 2H), 7.11-7.06 (m, 2H), 7.05-7.00 (m, 1H), 5.16 (dd, J = 10.9, 3.7 Hz, 1H), 4.61-4.55 (m, 1H), 4.55-4.43 (m, 3H), 4.39-4.32 (m, 1H), 4.04-3.98 (m, 1H), 3.90 (t, J = 10.6 Hz, 2H), 3.82 (dd, J = 10.9, 4.0 Hz, 1H), 3.65-3.54 (m, 1H), 3.52-3.41 (m, 1H), 3.23-3.14 (m, 2H), 3.06 (d, J = 7.3 Hz, 1H), 3.04-2.99 (m, 1H), 2.67-2.60 (m, 2H), 2.48 (s, 3H), 2.38-2.15 (m, 6H), 2.10 (ddd, J = 13.3, 9.0, 4.5 Hz, 1H), 2.00 (d, J = 8.7 Hz, 1H), 1.95 (s, 3H), 1.76-1.58 (m, 6H), 1.32 (t, J = 7.3 Hz, 1H), 1.20 (d, J = 6.4 Hz, 3H), 1.04 (s, 9H). |
| J35 | 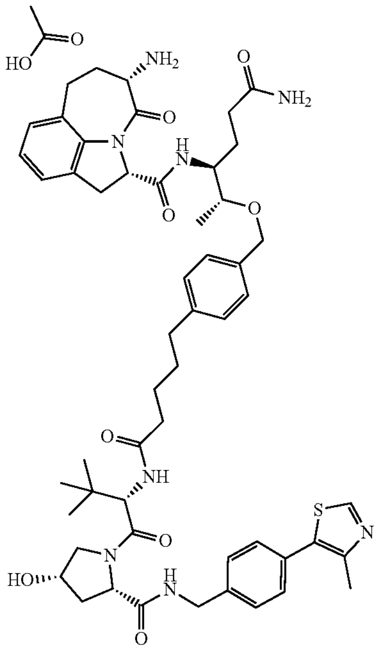 | (2S,4S)-1-[(2S)-2-[5-[4-([[(2R,3S)-3-[[(2S,11S)-11-amino-12-oxo-1-azatricyclo[6.4.1.0^[4,13]]trideca-4(13),5,7-trien-2-yl]formamido]-5-carbamoylpentan-2-yl]oxy]methyl)phenyl]pentanamido]-3,3-dimethylbutanoyl]-4-hydroxy-N-[[4-(4-methyl-1,3-thiazol-5-yl)phenyl]methyl]pyrrolidine-2-carboxamide acetate | [M/2 + 1)]+ = 489.6 | (400 MHz, DMSO-$d_6$) δ 8.99 (s, 1H), 8.62 (t, J = 6.1 Hz, 1H), 7.87 (d, J = 8.8 Hz, 1H), 7.80 (d, J = 9.3 Hz, 1H), 7.45-7.35 (m, 4H), 7.23-7.16 (m, 3H), 7.15-7.06 (m, 2H), 7.02 (d, J = 7.4 Hz, 2H), 6.93 (dd, J = 8.1, 6.8 Hz, 1H), 6.66 (s, 1H), 5.06 (dd, J = 10.9, 3.2 Hz, 1H), 4.50-4.32 (m, 5H), 4.31-4.15 (m, 2H), 3.94 (dd, J = 10.2, 5.7 Hz, 1H), 3.78 (q, J = 7.7, 5.2 Hz, 1H), 3.50-3.32 (m, 5H), 3.02 (t, J = 5.5 Hz, 2H), 2.86 (dd, J = 16.8, 3.3 Hz, 1H), 2.55 (d, J = 7.3 Hz, 2H), 2.45 (s, 3H), 2.37-2.23 (m, 2H), 2.21-1.93 (m, 3H), 1.90 (s, 3H), 1.85-1.69 (m, 2H), 1.63-1.45 (m, 6H), 1.08 (d, J = 6.2 Hz, 3H), 0.96-0.92 (m, 9H). |

TABLE 52-continued

Characterization data for intermediates prepare according to above.

| Intermediate | Structure | Chemical Name | MS: $[(M + 1)]^+$ | $^1H$ NMR |
|---|---|---|---|---|
| J36 | 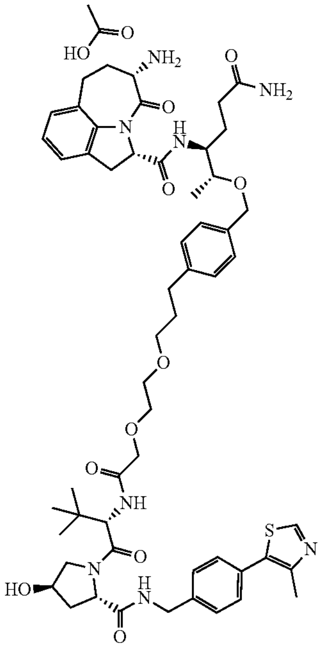 | (2S,4R)-1-[(2S)-2-[2-[2-(2-[3-[4-((2R,3S)-3-[[(2S,11S)-11-Amino-12-oxo-1-azatricyclo[6.4.1.0^[4,13]]trideca-4(13),5,7-trien-2-yl]formamido]-5-carbamoylpentan-2-yl]oxy]methyl)phen yl]propoxy]ethoxy)ethoxy]acetamido]-dimethylbutanoyl]-4-hydroxy-N-[[4-(4-methyl-1,3-thiazol-5-yl)phenyl]methyl]pyrrolidine-2-carboxamide acetate | 1037.7 | (400 MHz, DMSO-$d_6$) δ 8.98 (s, 1H), 8.59 (t, J = 6.0 Hz, 1H), 7.80 (d, J = 9.3 Hz, 1H), 7.46-7.33 (m, 5H), 7.21-7.14 (m, 3H), 7.10 (d, J = 7.8 Hz, 2H), 7.01 (d, J = 7.5 Hz, 2H), 6.96-6.88 (m, 1H), 6.67 (s, 1H), 5.05 (dd, J = 10.9, 3.2 Hz, 1H), 4.58 (d, J = 9.6 Hz, 1H), 4.48-4.33 (m, 5H), 4.25 (dd, J = 15.7, 5.6 Hz, 1H), 3.99 (s, 2H), 3.78 (s, 1H), 3.71-3.59 (m, 4H), 3.54 (t, J = 4.6 Hz, 2H), 3.48-3.28 (m, 6H), 3.03 (d, J = 12.8 Hz, 2H), 2.90-2.80 (m, 1H), 2.59 (t, J = 7.7 Hz, 2H), 2.44 (s, 3H), 2.13-2.00 (m, 3H), 1.99-1.92 (m, 2H), 1.91 (s, 3H), 1.84-1.70 (m, 3H), 1.62-1.45 (m, 1H), 1.08 (d, J = 6.2 Hz, 3H), 0.95 (s, 9H). |
| J37 | 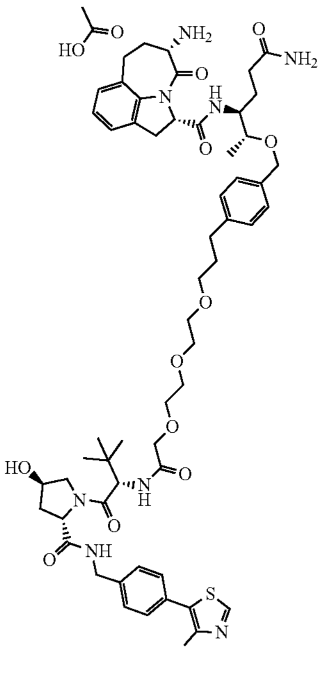 | (2S,4R)-1-[(2S)-2-[2-[2-(2-[3-[4-([[(2R,3S)-3-[[(2S,11S)-11-Amino-12-oxo-1-azatricyclo[6.4.1.0^[4,13]]trideca-4(13),5,7-trien-2-yl]formamido]-5-carbamoylpentan-2-yl]oxy]methyl)phenyl]propoxy]ethoxy)ethoxylacetamido]-dimethylbutanoyl]-4-hydroxy-N-[[4-(4-methyl-1,3-thiazol-yl)phenyl]methyl]pyrrolidine-2-carboxamide acetate | 1081.8 | (400 MHz, DMSO-$d_6$) δ 8.98 (s, 1H), 8.60 (t, J = 6.1 Hz, 1H), 7.80 (d, J = 9.3 Hz, 1H), 7.45-7.38 (m, 5H), 7.22-7.08 (m, 4H), 7.02 (d, J = 7.5 Hz, 2H), 6.96-6.90 (m, 1H), 6.67 (s, 1H), 5.06 (dd, J = 11.0, 3.2 Hz, 1H), 4.58 (d, J = 9.6 Hz, 1H), 4.48-4.33 (m, 5H), 4.30-4.20 (m, 1H), 3.98 (s, 2H), 3.85-3.73 (m, 1H), 3.70-3.56 (m, 6H), 3.50 (t, J = 4.8 Hz, 2H), 3.47-3.42 (m, 2H), 3.40-3.25 (m, 9H), 3.04 (d, J = 12.6 Hz, 2H), 2.86 (d, J = 15.1 Hz, 1H), 2.58 (t, J = 7.8 Hz, 2H), 2.45 (s, 3H), 2.12-1.90 (m, 3H), 1.87 (s, 3H), 1.82-1.70 (m, 2H), 1.63-1.50 (m, 1H), 1.09 (d, J = 6.2 Hz, 3H), 0.95 (s, 9H). |

TABLE 52-continued

Characterization data for intermediates prepare according to above.

| Inter-mediate | Structure | Chemical Name | MS: [(M + 1)]+ | $^1H$ NMR |
|---|---|---|---|---|
| J38 | 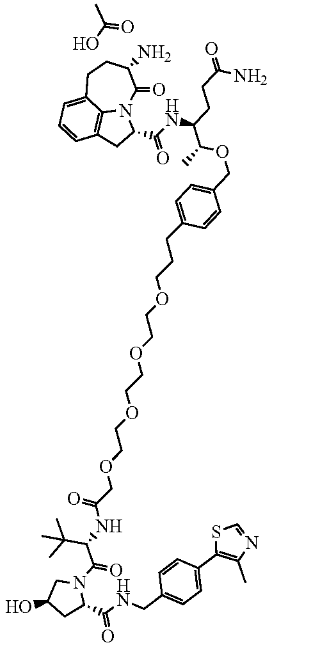 | (2S,4R)-1-[(2S)-2-[15-[4-([[(2R,3S)-3-[[(2S,11S)-11-amino-12-oxo-1-azatricyclo[6.4.1.0^[4,13]]trideca-4(13),5,7-trien-2-yl]formamido]-5-carbamoylpentan-2-yl]oxy]methyl)phenyl]-3,6,9,12-tetraoxapenta-decanamido]-3,3-dimethylbutanoyl]-4-hydroxy-N-[[4-(4-methyl-1,3-thiazol-5-yl)phenyl]methyl]pyrrolidine-2-carboxamide acetate | 1125.8 | (400 MHz, DMSO-$d_6$) δ 8.98 (d, J = 3.1 Hz, 1H), 8.60 (s, 1H), 7.85-7.77 (m, 1H), 7.46-7.35 (m, 5H), 7.21-7.14 (m, 3H), 7.11 (d, J = 7.8 Hz, 2H), 7.01 (t, J = 5.9 Hz, 2H), 6.93 (dd, J = 11.8, 7.6 Hz, 1H), 6.68 (s, 1H), 5.06 (d, J = 11.0 Hz, 1H), 4.57 (d, J = 9.4 Hz, 1H), 4.49-4.34 (m, 5H), 4.30-4.16 (m, 1H), 3.96 (d, J = 2.6 Hz, 2H), 3.78 (s, 1H), 3.64-3.43 (m, 16H), 3.40-3.30 (m, 6H), 3.11-2.96 (m, 2H), 2.85 (d, J = 16.9 Hz, 1H), 2.57 (d, J = 7.8 Hz, 2H), 2.44 (s, 3H), 2.12-1.94 (m, 4H), 1.91 (s, 3H), 1.84-1.68 (m, 2H), 1.61-1.47 (m, 1H), 1.08 (dd, J = 6.2, 2.8 Hz, 3H), 0.94 (s, 9H). |
| J39 | 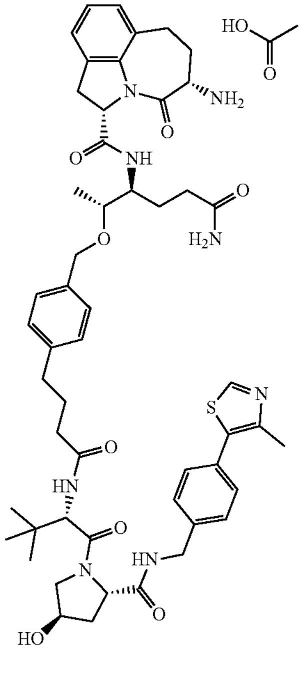 | (3S,6S)-3-Amino-N-((2R,3S)-6-amino-2-((4-(4-(((S)-1((2S,4R)-4-hydroxy-2-((4-(4-methylthiazol-5-yl)benzyl)carbamoyl)pyrrolidin-1-yl)-3,3-dimethyl-1-oxobutan-2-yl)amino)-4-oxobutyl)benzyl)oxy)-6-oxohexan-3-yl)-4-oxo-1,2,3,4,6,7-hexahydroazepino[3,2,1-hi]indole-6-carboxamide acetate | [M/2 + 1]+ = 482.5 | (400 MHz, DMSO-$d_6$) δ 8.99 (s, 1H), 8.56 (t, J = 6.0 Hz, 1H), 7.90 (d, J = 9.2 Hz, 1H), 7.80 (d, J = 9.2 Hz, 1H), 7.46-7.35 (m, 4H), 7.19 (d, J = 8.1 Hz, 1H), 7.11 (d, J = 7.9 Hz, 2H), 7.01 (d, J = 7.6 Hz, 2H), 6.97-6.89 (m, 1H), 6.68 (s, 1H), 5.13 (s, 1H), 5.05 (dd, J = 10.9, 3.3 Hz, 1H), 4.57 (d, J = 9.4 Hz, 1H), 4.49-4.30 (m, 5H), 4.22 (dd, J = 15.7, 5.4 Hz, 1H), 3.78 (s, 1H), 3.70-3.61 (m, 2H), 3.47-3.40 (m, 2H), 3.40-3.30 (m, 4H), 3.02 (s, 2H), 2.85 (d, J = 15.7 Hz, 1H), 2.68-2.57 (m, 2H), 2.45 (s, 3H), 2.28 (q, J = 7.3 Hz, 1H), 2.17 (q, J = 7.2 Hz, 1H), 2.05 (s, 2H), 2.12-1.99 (m, 1H), 1.90 (s, 3H), 1.84-1.69 (m, 2H), 1.62-1.45 (m, 1H), 1.08 (d, J = 6.2 Hz, 3H), 0.95 (s, 9H). |

TABLE 52-continued

| Characterization data for intermediates prepare according to above. | | | | |
|---|---|---|---|---|
| Intermediate | Structure | Chemical Name | MS: $[(M + 1)]^+$ | $^1H$ NMR |
| J40 | 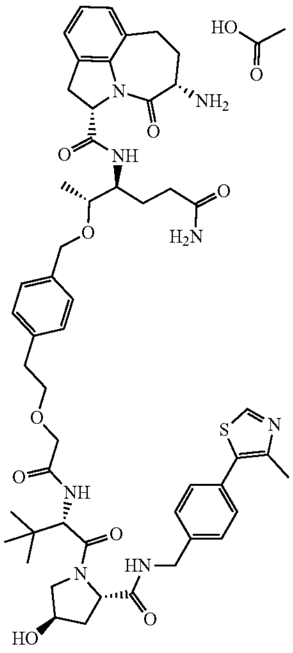 | (2S,4R)-1-[(2S)-2-(2-[2-[4-([[(2R,3S)-3-[[(2S,11S)-11-amino-12-oxo-1-azatricyclo[6.4.1.0^[4,13]]trideca-4(13),5,7-trien-2-yl]formamido]-5-carbamoylpentan-2-yl]oxy]methyl)phenyl]ethoxy]acetamido)-3,3-dimethylbutanoyl]-4-hydroxy-N-[[4-(4-methyl-1,3-thiazol-5-yl)phenyl]methyl]pyrrolidine-2-carboxamide acetate | 979.7 | (400 MHz, DMSO-$d_6$) δ 8.98 (s, 1H), 8.61 (t, J = 6.0 Hz, 1H), 7.80 (d, J = 9.2 Hz, 1H), 7.48-7.33 (m, 5H), 7.20 (s, 4H), 7.15 (s, 1H), 7.05-6.98 (m, 2H), 6.97-6.88 (m, 1H), 6.67 (s, 1H), 5.05 (dd, J = 10.8, 3.3 Hz, 1H), 4.55 (d, J = 9.6 Hz, 1H), 4.50-4.34 (m, 5H), 4.26 (dd, J = 15.9, 5.6 Hz, 1H), 3.98-3.88 (m, 2H), 3.78 (s, 1H), 3.74-3.58 (m, 4H), 3.48-3.31 (m, 4H), 3.03 (d, J = 12.7 Hz, 2H), 2.90-2.80 (m, 4H), 2.43 (s, 3H), 2.09-2.03 (m, 3H), 2.01-1.86 (m, 1H), 1.90 (s, 3H), 1.79 (s, 1H), 1.59-1.51 (m, 1H), 1.07 (d, J = 6.2 Hz, 3H), 0.93 (s, 9H). |
| J41 | 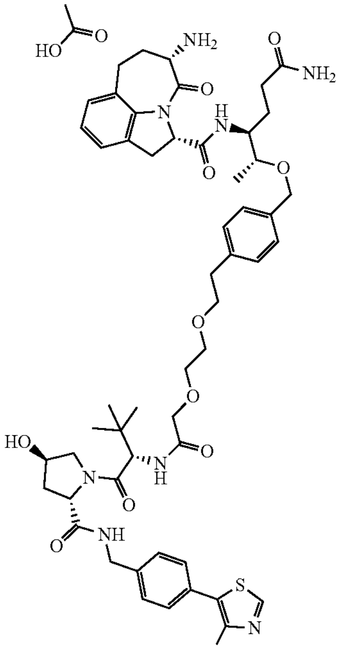 | (2S,4R)-1-[(2S)-2-([[(2R,3S)-3-[[(2S,11S)-11-amino-12-oxo-1-azatricyclo[6.4.1.0^[4,13]]trideca-4(13),5,7-trien-2-yl]formamido]-5-carbamoylpentan-2-yl]oxy]methyl)phenyl]ethoxy]ethoxy)acetamido]-3,3-dimethylbutanoyl]-4-hydroxy-N-[[4-(4-methyl-1,3-thiazol-5-yl)phenyl]methyl]pyrrolidine-2-carboxamide acetate | 1023.7 | (400 MHz, DMSO-$d_6$) δ 8.97 (s, 1H), 8.59 (t, J = 6.1 Hz, 1H), 7.80 (d, J = 9.3 Hz, 1H), 7.49-7.35 (m, 5H), 7.21-7.15 (m, 4H), 7.02 (d, J = 7.4 Hz, 2H), 6.93 (dd, J = 8.2, 6.7 Hz, 1H), 6.67 (s, 1H), 5.06 (dd, J = 10.9, 3.2 Hz, 1H), 4.59 (d, J = 9.6 Hz, 1H), 4.51-4.35 (m, 5H), 4.26 (dd, J = 15.8, 5.7 Hz, 1H), 3.98 (s, 2H), 3.85-3.78 (m, 1H), 3.73-3.54 (m, 9H), 3.50-3.41 (m, 2H), 3.37 (dd, J = 16.9, 11.1 Hz, 1H), 3.02 (s, 2H), 2.90-2.78 (m, 4H), 2.43 (s, 3H), 2.15-2.03 (m, 2H), 2.00-1.93 (m, 2H), 1.91 (s, 3H), 1.84-1.77 (m, 1H), 1.58 (dd, J = 15.0, 9.7 Hz, 1H), 1.08 (d, J = 6.2 Hz, 3H), 0.96 (s, 9H). |

TABLE 52-continued

Characterization data for intermediates prepare according to above.

| Inter-mediate | Structure | Chemical Name | MS: $[(M + 1)]^+$ | $^1H$ NMR |
| --- | --- | --- | --- | --- |
| J42 | 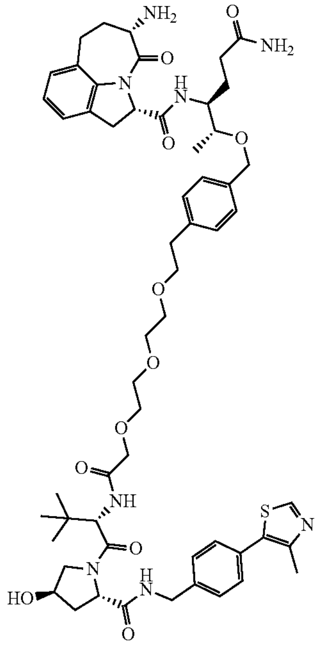 [SMILES: Cc1ncsc1-c1ccc(CNC(=O)[C@@H]2C[C@@H](O)CN2C(=O)[C@@H](NC(=O)COCCOCCOCCc2ccc(CO[C@H](C)[C@H](CCC(N)=O)NC(=O)[C@@H]3Cc4cccc5c4N3C(=O)[C@@H](N)CC5)cc2)C(C)(C)C)cc1] | (2S,4R)-1-[(2S)-2-[15-[4-([[(2R,3S)-3-[[(2S,11S)-11-amino-12-oxo-1-azatricyclo[6.4.1.0^[4,13]]trideca-4(13),5,7-trien-2-yl]formamido]-5-carbamoylpentan-2-yl]oxy]methyl) phenyl]-3,6,9,12-tetraoxapenta-decanamido]-3,3-dimethylbutanoyl]-4-hydroxy-N-[[4-(4-methyl-1,3-thiazol-5-yl)phenyl]methyl] pyrrolidine-2-carboxamide | 1067.7 | (400 MHz, DMSO-$d_6$) δ 8.98 (d, J = 3.7 Hz, 1H), 8.59 (s, 1H), 7.80 (d, J = 9.3 Hz, 1H), 7.46-7.37 (m, 5H), 7.19-7.10 (m, 5H), 7.01 (d, J = 7.3 Hz, 2H), 6.92 (t, J = 7.6 Hz, 1H), 6.67 (s, 1H), 5.05 (d, J = 11.1 Hz, 1H), 4.57 (d, J = 9.3 Hz, 1H), 4.49-4.31 (m, 6H), 4.25 (d, J = 15.5 Hz, 1H), 3.97 (s, 2H), 3.78 (s, 1H), 3.70-3.49 (m, 13H), 3.48-3.30 (m, 3H), 3.01 (s, 2H), 2.84 (d, J = 16.5 Hz, 1H), 2.76 (t, J = 7.4 Hz, 2H), 2.44 (s, 3H), 2.12-1.92 (m, 4H), 1.89 (s, 3H), 1.85-1.71 (m, 1H), 1.62-1.48 (m, 1H), 1.07 (d, J = 6.2 Hz, 3H), 0.95 (m, 9H). |
| J43 | 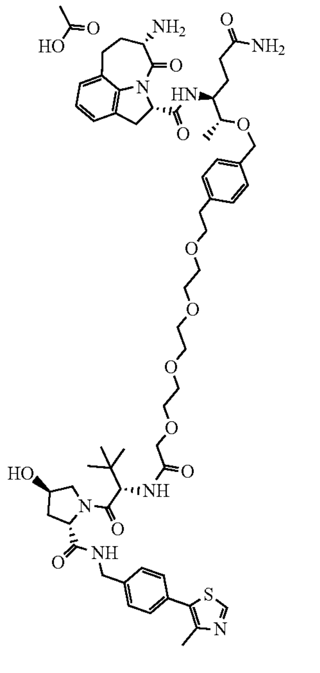 | (2S,4R)-1-[(2S)-2-[14-[4-([[(2R,3S)-3-[[(2S,11S)-11-Amino-12-oxo-1-azatricyclo[6.4.1.0^[4,13]]trideca-4(13),5,7-trien-2-yl]formamido]-5-carbamoylpentan-2-yl]oxy]methyl) phenyl]-3,6,9,12-tetraoxatetra-decanamido]-3,3-dimethylbutanoyl]-4-hydroxy-N-[[4-(4-methyl-1,3-thiazol-5-yl)phenyl]methyl] pyrrolidine-2-carboxamide acetate | 1111.7 | (400 MHz, DMSO-$d_6$) δ 8.98 (s, 1H), 8.61 (t, J = 6.0 Hz, 1H), 7.83 (d, J = 9.2 Hz, 1H), 7.46-7.38 (m, 5H), 7.18 (t, J = 6.6 Hz, 5H), 7.02 (d, J = 7.5 Hz, 2H), 6.93 (dd, J = 8.0, 6.8 Hz, 1H), 6.68 (s, 1H), 5.07 (dd, J = 10.9, 3.2 Hz, 1H), 4.58 (d, J = 9.6 Hz, 2H), 4.49-4.34 (m, 6H), 4.25 (dd, J = 15.8, 5.6 Hz, 1H), 3.97 (s, 2H), 3.84-3.75 (m, 1H), 3.68 (dd, J = 10.7, 3.9 Hz, 1H), 3.65-3.50 (m, 16H), 3.44 (dd, J = 12.4, 6.5 Hz, 2H), 3.40-3.33 (m, 1H), 3.03 (q, J = 5.9, 5.0 Hz, 2H), 2.85 (dd, J = 16.6, 3.2 Hz, 1H), 2.82-2.75 (m, 2H), 2.45 (s, 3H), 2.15-1.97 (m, 4H), 1.92 (td, J = 8.6, 4.3 Hz, 2H), 1.79 (ddd, J = 10.0, 6.7, 3.5 Hz, 1H), 1.62-1.51 (m, 1H), 1.08 (d, J = 6.3 Hz, 3H), 0.95 (s, 9H). |

TABLE 52-continued

Characterization data for intermediates prepare according to above.

| Inter-mediate | Structure | Chemical Name | MS: $[(M + 1)]^+$ | $^1H$ NMR |
|---|---|---|---|---|
| J44 | 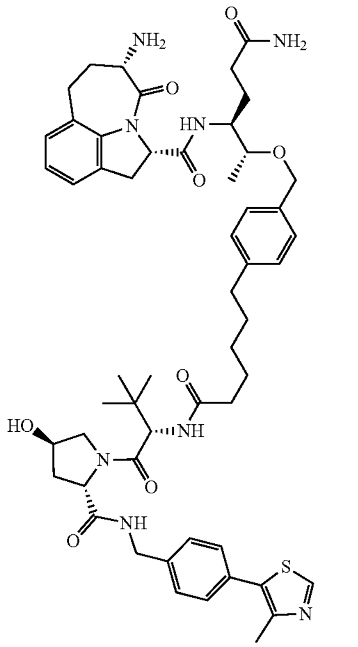 [SMILES: Cc1ncsc1-c1ccc(CNC(=O)[C@@H]2C[C@@H](O)CN2C(=O)[C@@H](NC(=O)CCCCCc2ccc(CO[C@H](C)[C@H](CCC(N)=O)NC(=O)[C@@H]3Cc4cccc5c4N3C(=O)[C@@H](N)CC5)cc2)C(C)(C)C)cc1] | (2S,4R)-1-[(2S)-2-[6-[4-([[(2R,3S)-3-[[(2S,11S)-11-Amino-12-oxo-1-azatricyclo[6.4.1.0^[4,13]]trideca-4(13),5,7-trien-2-yl]formamido]-5-carbamoylpentan-2-yl]oxy]methyl) phenyl]hexanamido]-3,3-dimethylbutanoyl]-4-hydroxy-N-[[4-(4-methyl-1,3-thiazol-5-yl)phenyl]methyl] pyrrolidine-2-carboxamide | 991.3 | (400 MHz, $CDCl_3$) δ 8.70 (s, 1H), 7.43 (t, J = 6.0 Hz, 1H), 7.40-7.33 (m, 4H), 7.27 (d, J = 7.8 Hz, 2H), 7.16 (d, J = 7.8 Hz, 2H), 7.09-6.99 (m, 4H), 6.43 (d, J = 8.8 Hz, 1H), 6.36 (s, 1H), 5.55 (s, 1H), 5.14 (dd, J = 9.8, 3.2 Hz, 1H), 4.70 (t, J = 8.0 Hz, 1H), 4.65-4.50 (m, 4H), 4.41-4.31 (m, 2H), 4.11 (d, J = 11.4 Hz, 1H), 3.93 (s, 1H), 3.66-3.54 (m, 3H), 3.38-3.21 (m, 2H), 3.05 (d, J = 6.3 Hz, 2H), 2.61 (m, 3H), 2.53 (s, 3H), 2.50-2.44 (m, 1H), 2.23-2.10 (m, 4H), 2.09-1.91 (m, 6H), 1.74 (dt, J = 18.2, 6.7 Hz, 1H), 1.66-1.56 (m, 4H), 1.31 (p, J = 7.7, 7.2 Hz, 2H), 1.22 (d, J = 6.3 Hz, 3H), 0.95 (s, 9H). |
| J45 | 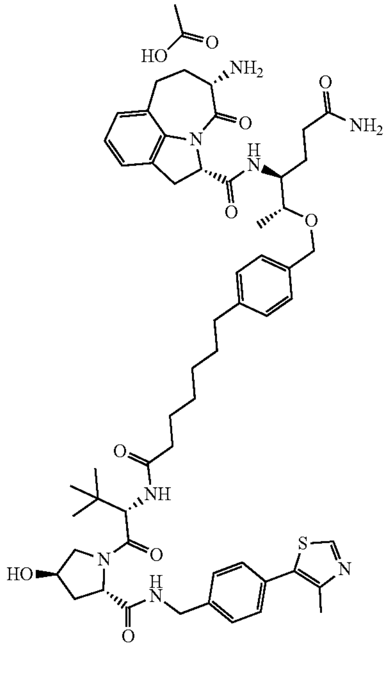 | (2S,4R)-1-[(2S)-2-[7-[4-([[(2R,3S)-3-[[(2S,11S)-11-amino-12-oxo-1-azatricyclo[6.4.1.0^[4,13]]trideca-4(13),5,7-trien-2-yl]formamido]-5-carbamoylpentan-2-yl]oxy]methyl) phenyl]heptanamido]-3,3-dimethylbutanoyl]-4-hydroxy-N-[[4-(4-methyl-1,3-thiazol-5-yl)phenyl]methyl] pyrrolidine-2-carboxamide acetate | 1005.8 | (400 MHz, $CD_3OD$) δ 8.87 (s, 1H), 7.49-7.37 (m, 4H), 7.21 (d, J = 7.9 Hz, 2H), 7.14-6.94 (m, 5H), 5.12 (dd, J = 11.0, 3.7 Hz, 1H), 4.62 (s, 1H), 4.60-4.42 (m, 7H), 4.34 (d, J = 15.4 Hz, 2H), 3.98 (d, J = 11.7 Hz, 1H), 3.89 (d, J = 11.2 Hz, 1H), 3.79 (dd, J = 11.0, 3.9 Hz, 1H), 3.67 (d, J = 9.6 Hz, 1H), 3.63-3.52 (m, 1H), 3.49-3.37 (m, 2H), 3.15 (s, 2H), 3.04-2.94 (m, 1H), 2.59 (t, J = 7.6 Hz, 2H), 2.47 (s, 3H), 2.31-1.99 (m, 5H), 1.90 (s, 3H), 1.78-1.53 (m, 5H), 1.44-1.30 (m, 4H), 1.18 (d, J = 6.3 Hz, 3H), 1.03 (s, 9H). |

TABLE 52-continued

| Characterization data for intermediates prepare according to above. | | | | |
|---|---|---|---|---|
| Inter-mediate | Structure | Chemical Name | MS: [(M + 1)]$^+$ | $^1$H NMR |
| J46 | 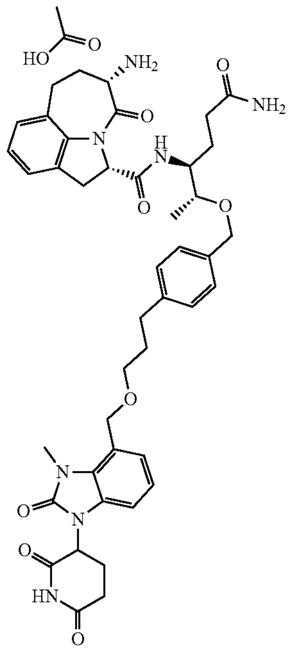 | (4S,5R)-4-[[(2S,11S)-11-amino-12-oxo-1-azatricyclo[6.4.1.0^[4,13]]trideca-4(13),5,7-trien-2-yl]formamido]-5-[[4-(3-[[1-(2,6-dioxopiperidin-3-yl)-3-methyl-2-oxo-1,3-benzodiazol-4-yl]methoxy]propyl)phenyl]methoxy]hexanamide acetate | 794.5 | (400 MHz, DMSO-d$_6$) δ 7.79 (d, J = 9.3 Hz, 1H), 7.20-7.12 (m, 3H), 7.10 (t, J = 8.2 Hz, 2H), 7.04-6.95 (m, 4H), 6.95-6.86 (m, 1H), 6.66 (s, 1H), 5.40 (dd, J = 12.9, 5.5 Hz, 1H), 5.05 (dd, J = 10.9, 3.1 Hz, 1H), 4.70 (s, 2H), 4.46-4.35 (m, 2H), 3.83-3.72 (m, 1H), 3.59 (s, 3H), 3.52-3.39 (m, 4H), 3.35-3.30 (m, 3H), 3.01 (s, 2H), 2.86 (t, J = 16.2 Hz, 2H), 2.72 (d, J = 12.7 Hz, 1H), 2.64 (d, J = 14.5 Hz, 1H), 2.59 (d, J = 8.2 Hz, 2H), 2.11-1.91 (m, 4H), 1.90 (s, 3H), 1.87-1.72 (m, 2H), 1.61-1.46 (m, 1H), 1.08 (d, J = 6.2 Hz, 3H). |
| J47 | 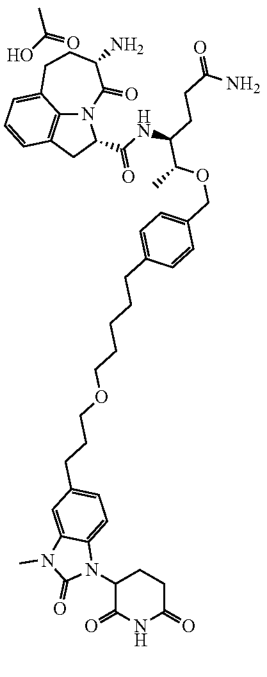 | (4S,5R)-4-[[2S,11S)-11-amino-12-oxo-1-azatricyclo[6.4.1.0^[4,13]]trideca-4(13),5,7-trien-2-yl]formamido]-5-[[4-(5-[3-[1-(2,6-dioxopiperidin-3-yl)-3-methyl-2-oxo-1,3-benzodiazol-5-yl]propoxy]pentyl)phenyl]methoxy]hexanamide acetate | 850.7 | (400 MHz, DMSO-d$_6$) δ 7.80 (d, J = 9.2 Hz, 1H), 7.21-7.09 (m, 5H), 7.05-6.97 (m, 4H), 6.92 (dd, J = 8.2, 6.6 Hz, 1H), 6.86 (dd, J = 8.1, 1.6 Hz, 1H), 6.67 (s, 1H), 5.34 (dd, J = 12.8, 5.3 Hz, 1H), 5.06 (dd, J = 10.9, 3.2 Hz, 1H),4.41 (d, J = 2.4 Hz, 2H), 3.79 (s, 1H), 3.46-3.40 (m, 2H), 3.35-3.30 (m, 7H), 3.02 (s, 2H), 2.97-2.80 (m, 2H), 2.78-2.53 (m, 8H), 2.13-1.94 (m, 4H), 1.90 (s, 3H), 1.86-1.75 (m, 3H), 1.62-1.50 (m, 5H), 1.35 (dt, J = 11.2, 6.6 Hz, 2H), 1.08 (d, J = 6.2 Hz, 3H). |

TABLE 52-continued

| Characterization data for intermediates prepare according to above. | | | | |
|---|---|---|---|---|
| Inter-mediate | Structure | Chemical Name | MS: $[(M + 1)]^+$ | $^1H$ NMR |
| J48 | 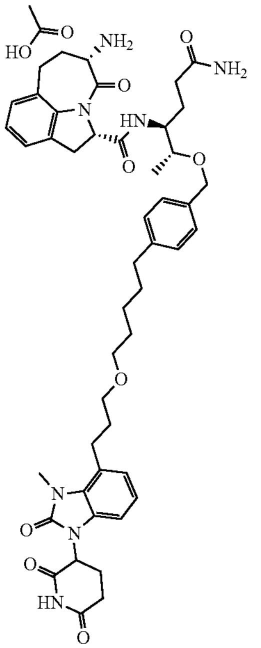 | (4S,5R)-4-[[(2S,11S)-11-amino-12-oxo-1-azatricyclo[6.4.1.0^[4,13]]trideca-4(13),5,7-trien-2-yl]formamido]-5-[[4-(5-(3-[1-(2,6-dioxopiperidin-3-yl)-3-methyl-2-oxo-1,3-benzodiazol-4-yl]propoxy]pentyl)phenyl]methoxy]hexanamide acetate | 850.6 | (400 MHz, DMSO-$d_6$) δ 7.81 (d, J = 9.3 Hz, 1H), 7.22-7.16 (m, 3H), 7.12 (d, J = 7.9 Hz, 2H), 7.01 (d, J = 7.4 Hz, 2H), 7.01-6.89 (m, 3H), 6.86 (dd, J = 5.8, 3.1 Hz, 1H), 6.68 (s, 1H), 5.37 (dd, J = 12.6, 5.4 Hz, 1H), 5.06 (dd, J = 10.9, 3.2 Hz, 1H), 4.45-4.34 (m, 2H), 3.78 (p, J = 5.4 Hz, 1H), 3.70-3.60 (m, 5H), 3.50-3.40 (m, 7H), 3.03 (q, J = 6.1, 5.2 Hz, 2H), 2.98-2.87 (m, 3H), 2.84 (dd, J = 12.3, 4.5 Hz, 1H), 2.72 (td, J = 12.9, 4.3 Hz, 1H), 2.66-2.53 (m, 3H), 2.12-2.03 (m, 1H), 1.99 (qd, J = 11.9, 10.4, 6.9 Hz, 2H), 1.89 (s, 3H), 1.87-1.73 (m, 3H), 1.65-1.50 (m, 5H), 1.35 (h, J = 7.4, 6.3 Hz, 2H), 1.08 (d, J = 6.1 Hz, 3H). |
| J49 | 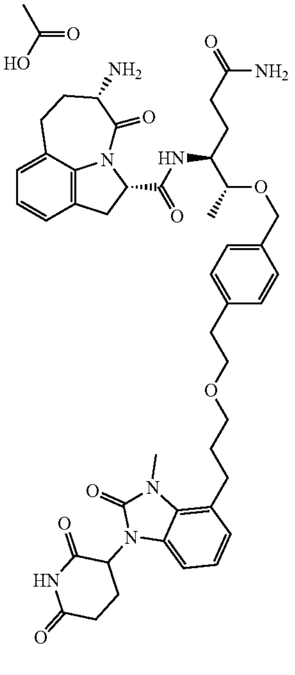 | (4S,5R)-4-[[(2S,11S)-11-amino-12-oxo-1-azatricyclo[6.4.1.0^4,13]]trideca-4(13),5,7-trien-2-yl]formamido]-5-[[4-(2-[3-[1-(2,6-dioxopiperidin-3-yl)-3-methyl-2-oxo-1,3-benzodiazol-4-yl]propoxy]ethy)phenyl]methoxy]hexanamide acetate | 809.5 | (400 MHz, DMSO-$d_6$) δ 7.80 (d, J = 9.2 Hz, 1H), 7.23-7.18 (m, 4H), 7.16 (d, J = 9.8 Hz, 1H), 7.01 (d, J = 7.5 Hz, 2H), 6.98-6.88 (m, 3H), 6.81 (dd, J = 6.5, 2.4 Hz, 1H), 6.67 (s, 1H), 5.36 (dd, J = 12.5, 5.4 Hz, 1H), 5.05 (dd, J = 10.9, 3.2 Hz, 1H), 4.48-4.37 (m, 2H), 3.78 (s, 1H), 3.60 (t, J = 6.8 Hz, 2H), 3.57-3.52 (m, 7H), 3.50-3.40 (m, 4H), 3.37 (dd, J = 16.8, 10.9 Hz, 1H), 3.03 (d, J = 13.3 Hz, 1H), 2.96-2.85 (m, 2H), 2.85-2.78 (m, 2H), 2.73-2.58 (m, 2H), 2.12-1.93 (m, 4H), 1.91 (s, 3H), 1.86-1.75 (m, 3H), 1.55 (d, J = 11.7 Hz, 1H), 1.08 (d, J = 6.2 Hz, 3H). |

TABLE 52-continued

| Characterization data for intermediates prepare according to above. | | | | |
|---|---|---|---|---|
| Intermediate | Structure | Chemical Name | MS: $[(M + 1)]^+$ | $^1H$ NMR |
| J50 | 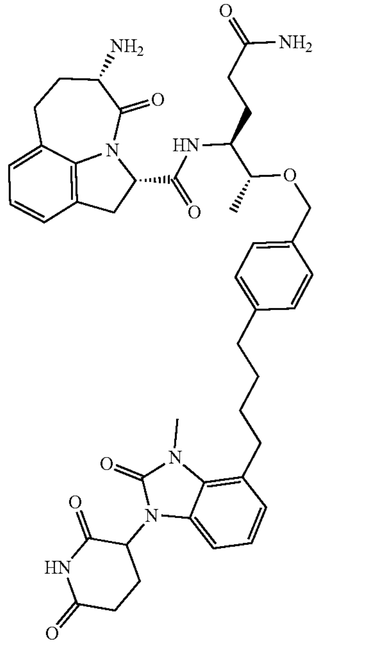 [SMILES: C[C@@H](OCc1ccc(CCCCc2cccc3c2n(C)c(=O)n3C2CCC(=O)NC2=O)cc1)[C@H](CCC(N)=O)NC(=O)[C@@H]1Cc2cccc3c2N1C(=O)[C@@H](N)CC3] | (4S,5R)-4-[[(2S,11S)-11-Amino-12-oxo-1-azatricyclo[6.4.1.0^[4,13]]trideca-4(13),5,7-trien-2-yl]formamido]-5-[(4-[4-[1-(2,6-dioxopiperidin-3-yl)-3-methyl-2-oxo-1,3-benzodiazol-4-yl]butyl]phenyl) methoxy]hexanamide | 778.4 | (400 MHz, $CDCl_3$) δ 7.34-7.27 (m, 2H), 7.16 (dd, J = 7.9, 4.9 Hz, 2H), 7.08 (d, J = 7.0 Hz, 1H), 7.05-6.94 (m, 3H), 6.92-6.86 (m, 1H), 6.73-6.66 (m, 1H), 6.49-6.34 (m, 1H), 5.52-5.35 (m, 1H), 5.19 (td, J = 10.0, 9.6, 4.3 Hz, 1H), 4.62 (d, J = 11.5 Hz, 1H), 4.41 (dd, J = 11.5, 8.4 Hz, 1H), 3.96 (d, J = 10.6 Hz, 1H), 3.67-3.57 (m, 2H), 3.53-3.48 (m, 3H), 3.37-3.26 (m, 2H), 3.08 (d, J = 8.0 Hz, 2H), 2.98-2.86 (m, 3H), 2.85-2.74 (m, 2H), 2.70 (q, J = 7.0 Hz, 2H), 2.27-1.95 (m, 7H), 1.84-1.62 (m, 4H), 1.23 (dd, J = 6.4, 2.0 Hz, 3H). |
| J51 | 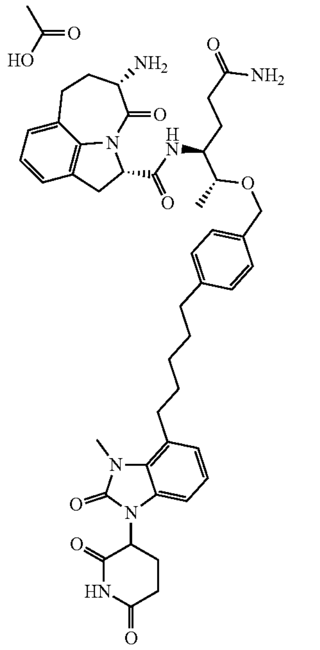 | (4S,5R)-4-[[(2S,11S)-11-amino-12-oxo-1-azatricyclo[6.4.1.0^[4,13]]trideca-4(13),5,7-trien-2-yl]formamido]-5-[(4-[5-[1-(2,6-dioxopiperidin-3-yl)-3-methyl-2-oxo-1,3-benzodiazol-4-yl]pentyl]phenyl) methoxy] hexanamide acetate | 792.7 | (400 MHz, DMSO-$d_6$) δ 7.80 (d, J = 9.3 Hz, 1H), 7.21-7.15 (m, 3H), 7.12 (d, J = 7.8 Hz, 2H), 7.02 (d, J = 7.5 Hz, 2H), 6.98-6.82 (m, 4H), 6.67 (s, 1H), 5.36 (dd, J = 12.5, 5.3 Hz, 1H), 5.06 (dd, J = 11.0, 3.2 Hz, 1H), 4.47-4.36 (m, 2H), 3.78 (s, 1H), 3.43 (dd, J = 12.7, 7.4 Hz, 2H), 3.39-3.32 (m, 6H), 3.02 (s, 2H), 2.95-2.80 (m, 4H), 2.70-2.65 (m, 1H), 2.62-2.54 (m, 2H), 2.12-1.90 (m, 4H), 1.91 (s, 3H), 1.85-1.75 (m, 1H), 1.67-1.52 (m, 5H), 1.46-1.37 (m, 2H), 1.08 (d, J = 6.2 Hz, 3H). |

TABLE 52-continued

| Characterization data for intermediates prepare according to above. | | | | |
|---|---|---|---|---|
| Intermediate | Structure | Chemical Name | MS: $[(M + 1)]^+$ | $^1H$ NMR |
| J52 | 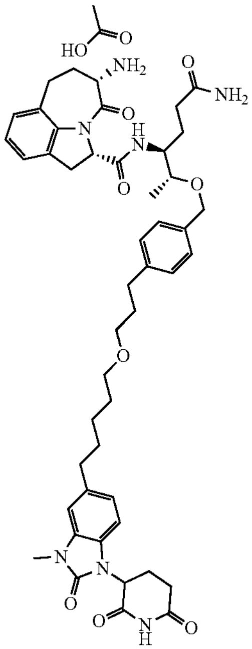 | (4S,5R)-4-[[(2S,11S)-11-amino-12-oxo-1-azatricyclo[6.4.1.0^[4,13]]trideca-4(13),5,7-trien-2-yl]formamido]-5-([4-[3-([5-[1-(2,6-dioxopiperidin-3-yl)-3-methyl-2-oxo-1,3-benzodiazol-5-yl]pentyl]oxy)propyl]phenyl]methoxy)hexanamide acetate | 850.7 | (400 MHz, DMSO-$d_6$) δ 7.79 (d, J = 9.3 Hz, 1H), 7.22-7.08 (m, 5H), 7.05-7.00 (m, 4H), 6.96-6.83 (m, 2H), 6.67 (s, 1H), 5.33 (dd, J = 12.9, 5.2 Hz, 1H), 5.09-5.01 (m, 1H), 4.41 (d, J = 2.4 Hz, 2H), 3.79 (s, 1H), 3.50-3.38 (m, 1H), 3.35-3.30 (m, 13H), 3.01 (s, 2H), 2.86 (t, J = 13.9 Hz, 2H), 2.70-2.55 (m, 4H), 2.12-1.95 (m, 3H), 1.87 (s, 3H), 1.85-1.75 (m, 3H), 1.65-1.50 (m, 5H), 1.36 (s, 2H), 1.08 (d, J = 6.2 Hz, 3H). |
| J53 | 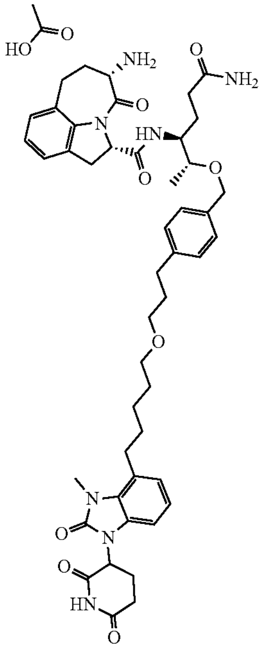 | (4S,5R)-4-[[(2S,11S)-11-amino-12-oxo-1-azatricyclo[6.4.1.0^[4,13]]trideca-4(13),5,7-trien-2-yl]formamido]-5-([4-[3-([5-[1-(2,6-dioxopiperidin-3-yl)-3-methyl-2-oxo-1,3-benzodiazol-4-yl]pentyl]oxy)propyl]phenyl]methoxy)hexanamide acetate | 850.6 | (400 MHz, DMSO-$d_6$) δ 7.79 (d, J = 9.1 Hz, 1H), 7.19 (d, J = 7.9 Hz, 2H), 7.15 (s, 1H), 7.12 (d, J = 7.8 Hz, 2H), 7.02 (d, J = 7.5 Hz, 2H), 6.99-6.88 (m, 3H), 6.87 (dd, J = 5.5, 3.4 Hz, 1H), 6.66 (s, 1H), 5.36 (dd, J = 12.6, 5.3 Hz, 1H), 5.06 (dd, J = 10.7, 3.1 Hz, 1H), 4.47-4.36 (m, 2H), 3.79 (s, 1H), 3.56 (s, 3H), 3.48-3.42 (m, 2H), 3.36-3.30 (m, 6H), 3.02 (s, 2H), 2.95-2.86 (m, 4H), 2.75-2.56 (m, 4H), 2.06-1.93 (m, 4H), 1.91 (s, 3H), 1.82-1.74 (m, 3H), 1.68-1.55 (m, 5H), 1.45 (d, J = 7.5 Hz, 2H), 1.09 (d, J = 6.2 Hz, 3H). |

TABLE 52-continued

Characterization data for intermediates prepare according to above.

| Inter-mediate | Structure | Chemical Name | MS: $[(M + 1)]^+$ | $^1H$ NMR |
|---|---|---|---|---|
| J54 | 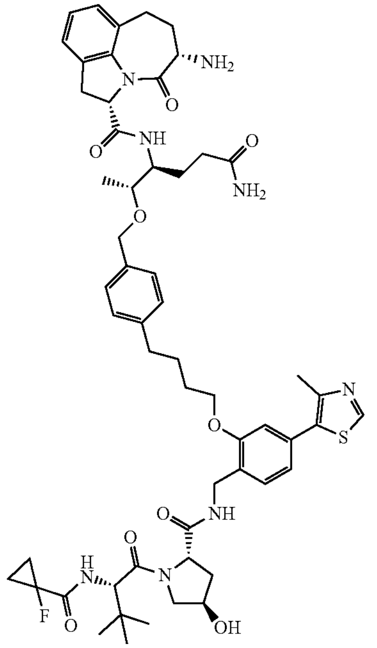 [SMILES: Cc1ncsc1-c1ccc(CNC(=O)[C@@H]2C[C@@H](O)CN2C(=O)[C@@H](NC(=O)C2(F)CC2)C(C)(C)C)c(OCCCCc2ccc(CO[C@H](C)[C@H](CCC(N)=O)NC(=O)[C@@H]3Cc4cccc5c4N3C(=O)[C@@H](N)CC5)cc2)c1] | (2S,4R)-N-[(2-[4-[4-([[(2R,3S)-3-[[(2S,11S)-11-amino-12-oxo-1-azatricyclo[6.4.1.0^[4,13]]trideca-4(13),5,7-trien-2-yl]formamido]-5-carbamoylpentan-2-yl]oxy]methyl) phenyl]butoxy]-4-(4-methyl-1,3-thiazol-yl)phenyl)methyl]-1-[(2S)-2-[(1-fluorocyclopropyl) formamido]-3,3-dimethylbutanoyl]-4-hydroxypyrrolidine-2-carboxamide | 1051.7 | Used directly in next step without further purification |
| J55 | 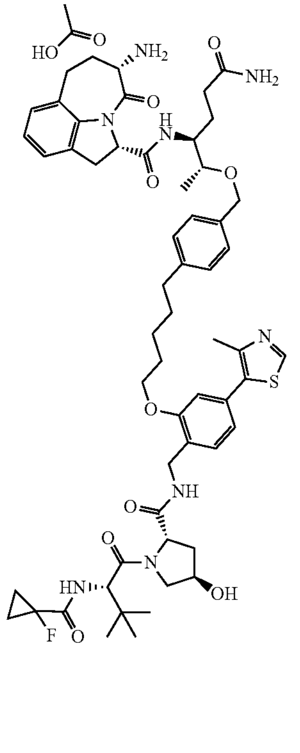 | (2S,4R)-N-[[2-([5-[4-([[(2R,3S)-3-[[(2S,11S)-11-amino-12-oxo-1-azatricyclo[6.4.1.0^[4,13]]trideca-4(13),5,7-trien-2-yl]formamido]-5-carbamoylpentan-2-yl]oxy]methyl) phenyl]pentyl] oxy)-4-(4-methyl-1,3-thiazol-yl)phenyl]methyl]-1-[(2S)-2-[(1-fluorocyclopropyl) formamido]-3,3-dimethylbutanoyl]-4-hydroxypyrrolidine-2-carboxamide acetate | $[(M + 18)]^+$ = 1083.5 | (400 MHz, DMSO-$d_6$) δ 8.98 (s, 1H), 8.49 (t, J = 6.0 Hz, 1H), 7.79 (d, J = 9.3 Hz, 1H), 7.41 (d, J = 7.8 Hz, 1H), 7.29 (dd, J = 9.2, 2.8 Hz, 1H), 7.22-7.11 (m, 5H), 7.04-6.98 (m, 3H), 6.95 (dd, J = 7.7, 1.6 Hz, 1H), 6.95-6.87 (m, 1H), 6.66 (s, 1H), 5.05 (dd, J = 10.9, 3.2 Hz, 1H), 4.61 (d, J = 9.2 Hz, 1H), 4.53 (t, J = 8.2 Hz, 1H), 4.46-4.39 (m, 2H), 4.36 (s, 1H), 4.30 (dd, J = 16.5, 6.0 Hz, 1H), 4.20 (dd, J = 16.6, 5.5 Hz, 1H), 4.05 (t, J = 6.3 Hz, 2H), 3.78-3.70 (m, 1H), 3.71-3.57 (m, 2H), 3.48-3.31 (m, 4H), 3.01 (s, 2H), 2.85 (dd, J = 16.6, 3.2 Hz, 1H), 2.60 (t, J = 7.6 Hz, 2H), 2.46 (s, 3H), 2.12-2.01 (m, 2H), 1.99-1.90 (m, 2H), 1.90 (s, 3H), 1.86-1.76 (m, 3H), 1.75-1.70 (m, 2H), 1.69-1.53 (m, 2H), 1.50 (d, J = 7.2 Hz, 2H), 1.43-1.31 (m, 2H), 1.23 (dd, J = 8.6, 3.4 Hz, 2H), 1.08 (d, J = 6.2 Hz, 3H), 0.97 (s, 9H). |

TABLE 52-continued

| Characterization data for intermediates prepare according to above. | | | | |
|---|---|---|---|---|
| Inter-mediate | Structure | Chemical Name | MS: $[(M + 1)]^+$ | $^1$H NMR |
| J56 | 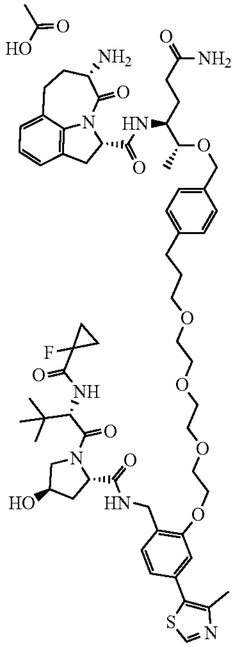 | (2S,4R)-N-[(2-[2-[2-(2-[3-[4-([[(2R,3S)-3-[[(2S,11S)-11-amino-12-oxo-1-azatricyclo[6.4.1.0^[4,13]]trideca-4(13),5,7-trien-2-yl]formamido]-5-carbamoylpentan-2-yl]oxy]methyl)phenyl]propoxy]ethoxy)ethoxylethoxyl-4-(4-methyl-1,3-thiazol-yl)phenyl)methyl]-1-[(2S)-2-[(1-fluorocyclopropyl)formamido]-3,3-dimethylbutanoyl]-4-hydroxypyrrolidine-2-carboxamide acetate | $[(M/2 + 1]^+$ = 585.7 | (400 MHz, DMSO-$d_6$) δ 8.98 (s, 1H), 8.48 (d, J = 6.2 Hz, 1H), 7.80 (d, J = 9.2 Hz, 1H), 7.41 (d, J = 7.9 Hz, 1H), 7.29 (d, J = 8.9 Hz, 1H), 7.23-7.14 (m, 3H), 7.11 (d, J = 7.9Hz, 2H), 7.06-6.99 (m, 3H), 6.99-6.93 (m, 1H), 6.92 (dd, J = 8.3, 6.6 Hz, 1H), 6.67 (s, 1H), 5.05 (dd, J = 10.9, 3.2 Hz, 1H), 4.60 (d, J = 9.1 Hz, 1H), 4.52 (t, J = 8.3 Hz, 1H), 4.41 (s, 2H), 4.36 (s, 1H), 4.30 (d, J = 6.2 Hz, 1H), 4.25-4.15 (m, 3H), 3.85-3.75 (m, 3H), 3.70-3.62 (m, 3H), 3.60-3.51 (m, 4H), 3.50-3.40 (m, 3H), 3.41-3.30 (m, 5H), 3.02 (s, 2H), 2.85 (d, J = 15.4 Hz, 1H), 2.58 (t, J = 7.7 Hz, 2H), 2.46 (s, 3H), 2.12-2.05 (m, 2H), 2.03-1.93 (m, 4H), 1.90 (s, 3H), 1.81-1.72 (m, 3H), 1.60-1.50 (m, 1H), 1.45-1.34 (m, 2H), 1.23 (d, J = 8.6 Hz, 2H), 1.08 (d, J = 6.2 Hz, 3H), 0.96 (s, 9H). |
| J57 | 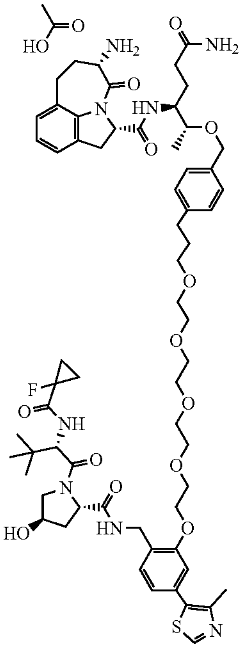 | (2S,4R)-N-[[2-([15-[4-([[(2R,3S)-3-[[(2S,11S)-11-amino-12-oxo-1-azatricyclo[6.4.1.0^[4,13]]trideca-4(13),5,7-trien-2-yl]formamido]-5-carbamoylpentan-2-yl]oxy]methyl)phenyl]-3,6,9,12-tetraoxapentadecan-1-yl]oxy)-4-(4-methyl-1,3-thiazol-5-yl)phenyl]methyl]-1-[(2S)-2-[(1-fluorocyclopropyl)formamido]-3,3-dimethylbutanoyl]-hydroxypyrrolidine-2-carboxamide acetate | 1213.9 | (400 MHz, DMSO-$d_6$) δ 8.98 (s, 1H), 7.80 (d, J = 9.2 Hz, 1H),7.41 (d, J = 7.9 Hz, 1H), 7.29 (d, J = 8.3 Hz, 1H), 7.18 (d, J = 8.0 Hz, 2H), 7.12 (d, J = 7.9 Hz, 2H), 7.06-6.88 (m, 5H), 6.67 (s, 1H), 5.17 (s, 1H), 5.09-5.02 (m, 1H), 4.60 (d, J = 9.0 Hz, 1H), 4.52 (t, J = 8.0 Hz, 1H), 4.41 (s, 2H), 4.36 (s, 1H), 4.30 (s, 1H), 4.25-4.15 (m, 3H), 3.85-3.76 (m, 3H), 3.66-3.60 (m, 3H), 3.58-3.54 (m, 2H), 3.54-3.50 (m, 6H), 3.49-3.41 (m, 4H), 3.40-3.30 (m, 8H), 3.02 (s, 2H), 2.85 (d, J = 17.0 Hz, 1H), 2.59 (t, J = 7.7 Hz, 2H), 2.46 (s, 3H), 2.08 (d, J = 10.3 Hz, 2H), 1.91 (s, 3H), 1.81-1.73 (m, 3H), 1.37 (d, J = 7.9 Hz, 2H), 1.22 (d, J = 4.5 Hz, 2H), 1.08 (d, J = 6.2 Hz, 3H), 0.96 (s, 9H). |

TABLE 52-continued

Characterization data for intermediates prepare according to above.

| Inter-mediate | Structure | Chemical Name | MS: [(M + 1)]+ | $^1$H NMR |
|---|---|---|---|---|
| J58 | 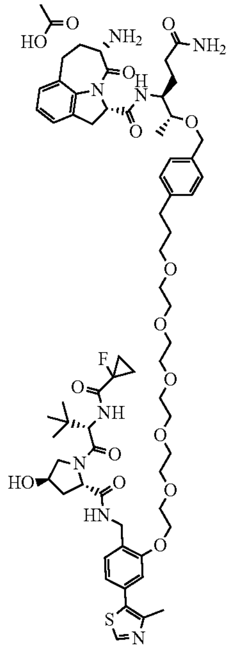 | (2S,4R)-N-[[2-([18-[4-([[(2R,3S)-3-[[(2S,11S)-11-amino-12-oxo-1-azatricyclo[6.4.1.0^[4,13]]trideca-4(13),5,7-trien-2-yl]formamido]-5-carbamoylpentan-2-yl]oxy]methyl) phenyl]-3,6,9,12,15-pentaoxaoctadecan-1-yl]oxy)-4-(4-methyl-1,3-thiazol-5-yl)phenyl]methyl]-1-[(2S)-2-[(1-fluorocyclopropyl) formamido]-3,3-dimethylbutanoyl]-hydroxypyrrolidine-2-carboxamide acetate | N/A | (400 MHz, DMSO-$d_6$) δ 8.98 (s, 1H), 8.47 (t, J = 6.0 Hz, 1H), 7.79 (d, J = 9.1 Hz, 1H), 7.41 (d, J = 7.8 Hz, 1H), 7.29 (d, J = 9.2 Hz, 1H), 7.23-7.09 (m, 5H), 7.08-6.99 (m, 3H), 6.97 (dd, J = 7.8, 1.7 Hz, 1H), 6.92 (dd, J = 8.2, 6.7 Hz, 1H), 6.66 (s, 1H), 5.05 (dd, J = 10.8, 3.2 Hz, 1H), 4.60 (d, J = 9.3 Hz, 1H), 4.52 (t, J = 8.2 Hz, 1H), 4.41 (d, J = 2.8 Hz, 2H), 4.38-4.26 (m, 2H), 4.26-4.15 (m, 3H), 3.79 (m, 3H), 3.70-3.59 (m, 3H), 3.58-3.31 (m, 22H), 3.02 (s, 2H), 2.90-2.81 (m, 1H), 2.59 (t, J = 7.7 Hz, 2H), 2.46 (s, 3H), 2.14-1.99 (m, 2H), 1.96 (m, 2H), 1.90 (s, 3H), 1.77 (m, 3H), 1.55 (d, J = 10.6 Hz, 1H), 1.43-1.31 (m, 2H), 1.26-1.19 (m, 2H), 1.08 (d, J = 6.2 Hz, 3H), 0.96 (s, 9H). |
| J59 | 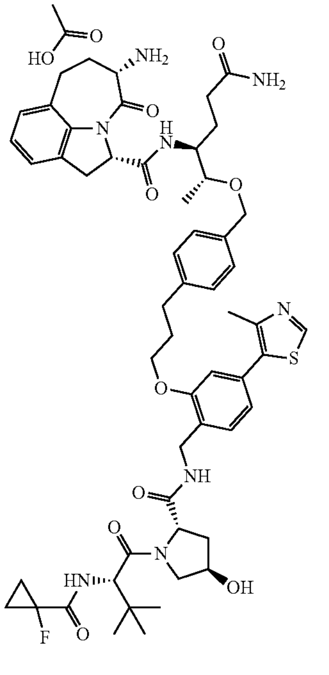 | (2S,4R)-N-[(2-[3-[4-([[(2R,3S)-3-[[(2S,11S)-11-amino-12-oxo-1-azatricyclo[6.4.1.0^[4,13]]trideca-4(13),5,7-trien-2-yl]formamido]-5-carbamoylpentan-2-yl]oxy]methyl) phenyl]propoxy]-4-(4-methyl-1,3-thiazol-5-yl)phenyl)methyl]-1-[(2S)-2-[(1-fluorocyclopropyl) formamido]-3,3-dimethylbutanoyl]-hydroxypyrrolidine-2-carboxamide acetate | 1037.3 | (400 MHz, DMSO-$d_6$) δ 8.98 (s, 1H), 8.52 (t, J = 6.0 Hz, 1H), 7.80 (d, J = 9.2 Hz, 1H), 7.43 (d, J = 7.7 Hz, 1H), 7.33-7.26 (m, 1H), 7.25-7.15 (m, 5H), 7.03-6.93 (m, 4H), 6.89 (dd, J = 8.1, 6.7 Hz, 1H), 6.67 (s, 1H), 5.16 (s, 1H), 5.05 (dd, J = 11.0, 3.2 Hz, 1H), 4.61 (d, J = 9.2 Hz, 1H), 4.53 (t, J = 8.2 Hz, 1H), 4.42 (s, 2H), 4.35-4.25 (m, 2H), 4.06 (t, J = 6.1 Hz, 2H), 3.79 (s, 1H), 3.70-3.57 (m, 2H), 3.44 (dd, J = 9.1, 3.3 Hz, 2H), 3.36-3.30 (m, 4H), 3.05-2.98 (m, 2H), 2.89-2.80 (m, 1H), 2.78 (t, J = 7.6 Hz, 2H), 2.45 (s, 3H), 2.14-1.95 (m, 5H), 1.90 (s, 3H), 1.81-1.74 (m, 1H), 1.55 (d, J = 10.7 Hz, 1H), 1.43-1.29 (m, 2H), 1.22 (dd, J = 8.2, 3.4 Hz, 2H), 1.08 (d, J = 6.2 Hz, 3H), 0.97 (s, 9H). |

TABLE 52-continued

| Characterization data for intermediates prepare according to above. | | | | |
|---|---|---|---|---|
| Inter-mediate | Structure | Chemical Name | MS: [(M + 1)]+ | $^1$H NMR |
| J60 | 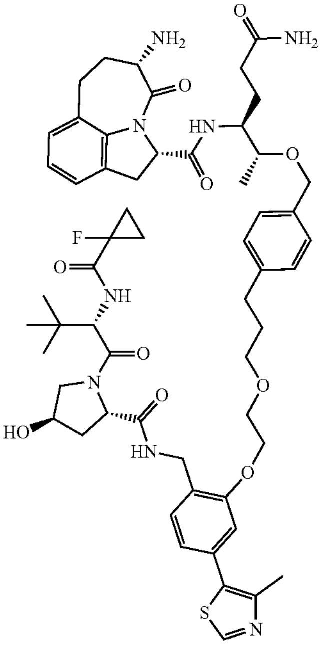 [SMILES: Cc1ncsc1-c1ccc(CNC(=O)[C@@H]2C[C@@H](O)CN2C(=O)[C@@H](NC(=O)C2(F)CC2)C(C)(C)C)c(OCCOCCCc2ccc(CO[C@H](C)[C@H](CCC(N)=O)NC(=O)[C@@H]3Cc4cccc5c4N3C(=O)[C@@H](N)CC5)cc2)c1] | (2S,4R)-N-[[2-(2-[3-[4-([[(2R,3S)-3-[[(2S,11S)-11-Amino-12-oxo-1-azatricyclo[6.4.1.0^[4,13]]trideca-4(13),5,7-trien-2-yl]formamido]-5-carbamoylpentan-2-yl]oxy]methyl)phenyl]propoxy]ethoxy)-4-(4-methyl-1,3-thiazol-5-yl)phenyl]methyl]-1-[(2S)-2-[(1-fluorocyclopropyl)formamido]-3,3-dimethylbutanoyl]-4-hydroxypyrrolidine-2-carboxamide | 1081.7 | (400 MHz, $CDCl_3$) δ 8.70 (s, 1H), 7.39 (d, J = 6.5 Hz, 1H), 7.36 (d, J = 7.7 Hz, 1H), 7.25 (d, J = 7.8 Hz, 2H), 7.17 (d, J = 7.8 Hz, 2H), 7.12-7.05 (m, 2H), 7.03-6.97 (m, 3H), 6.93 (d, J = 1.7 Hz, 1H), 6.36 (s, 1H), 5.34 (s, 1H), 5.27-5.17 (m, 1H), 4.66 (t, J = 7.9 Hz, 1H), 4.62-4.54 (m, 2H), 4.48 (s, 1H), 4.43 (m, 3H), 4.22 (dq, J = 9.2, 4.8, 3.7 Hz, 2H), 3.98 (d, J = 10.6 Hz, 1H), 3.94-3.79 (m, 3H), 3.71-3.54 (m, 5H), 3.40-3.26 (m, 2H), 3.08 (t, J = 6.9 Hz, 2H), 2.73 (m, 2H), 2.55 (s, 3H), 2.34 (ddd, J = 12.8, 7.8, 4.7 Hz, 1H), 2.14-2.02 (m, 5H), 1.96 (m, 2H), 1.81 (dd, J = 12.5, 7.1 Hz, 1H), 1.36-1.31 (m, 2H), 1.29 (d, J = 6.2 Hz, 2H), 1.24 (d, J = 6.3 Hz, 3H), 0.97 (s, 9H). |
| J61 | 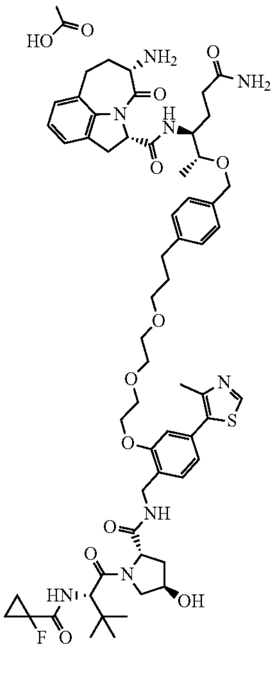 | (2S,4R)-N-([2-[2-(2-[3-[4-([[(2R,3S)-3-[[(2S,11S)-11-amino-12-oxo-1-azatricyclo[6.4.1.0^[4,13]]trideca-4(13),5,7-trien-2-yl]formamido]-5-carbamoylpentan-2-yl]oxy]methyl)phenyl]propoxy]ethoxy)ethoxy]-4-(4-methyl-1,3-thiazol-5-yl)phenyl]methyl)-1-[(2S)-2-[(1-fluorocyclopropyl)formamido]-3,3-dimethylbutanoyl]-4-hydroxypyrrolidine-2-carboxamide acetate | 1125.8 | (400 MHz, DMSO-$d_6$) 8.98 (d, J = 4.2 Hz, 1H), 8.48 (s, 1H), 7.80 (d, J = 9.4 Hz, 1H), 7.41 (d, J = 7.9 Hz, 1H), 7.29 (d, J = 9.2 Hz, 1H), 7.18 (s, 1H), 7.16 (s, 2H), 7.10 (d, J = 7 .8 Hz, 2H), 7.07-6.87 (m, 4H), 6.67 (s, 1H), 5.05 (d, J = 10.2 Hz, 1H), 4.60 (d, J = 9.0 Hz, 1H), 4.51 (t, J = 8.4 Hz, 1H), 4.42-4.38 (m, 2H), 4.32 (d, J = 15.8 Hz, 2H), 4.25-4.15 (m, 2H), 3.85-3.73 (m, 3H), 3.69-3.56 (m, 3H), 3.55-3.48 (m, 1H), 3.45-3.30 (m, 6H), 3.05-2.96 (m, 2H), 2.84 (d, J = 16.1 Hz, 1H), 2.63-2.53 (m, 3H), 2.52-2.41 (m, 5H), 2.12-2.00 (m, 3H), 2.00-1.92 (m, 2H), 1.90 (s, 3H), 1.83-1.70 (m, 3H), 1.61-1.46 (m, 1H), 1.35 (d, J = 16.1 Hz, 2H), 1.22 (d, J = 9.3 Hz, 2H), 1.07 (d, J = 6.2 Hz, 3H), 0.95 (s, 9H). |

TABLE 52-continued

| Characterization data for intermediates prepare according to above. | | | | |
|---|---|---|---|---|
| Intermediate | Structure | Chemical Name | MS: $[(M + 1)]^+$ | $^1H$ NMR |
| J62 | 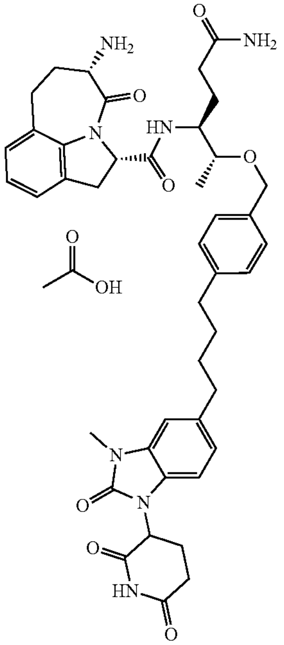 | (4S,5R)-4-[[(2S,11S)-11-amino-12-oxo-1-azatricyclo[6.4.1.0^[4,13]]trideca-4(13),5,7-trien-2-yl]formamido]-5-[(4-[4-[1-(2,6-dioxopiperidin-3-yl)-3-methyl-2-oxo-1,3-benzodiazol-5-yl]butyl]phenyl) methoxy]hexanamide; acetic acid | 778.4 | (400 MHz, DMSO-$d_6$) δ 7.80 (d, J = 9.3 Hz, 1H), 7.22-7.08 (m, 4H), 7.05-6.96 (m, 3H), 6.90-6.80 (m, 2H), 6.68 (s, 1H), 5.33 (dd, J = 13.1, 5.3 Hz, 1H), 5.12-5.01 (m, 1H), 4.41 (s, 2H), 3.79 (s, 2 H), 3.59-3.35 (m, 7H), 3.01 (s, 2H), 2.90-2.80 (m, 2H), 2.75-2.55 (m, 5H), 2.13-1.72 (m, 9H), 1.68-1.48 (m, 4H), 1.08 (d, J = 6.3 H, 3H). |
| J63 | 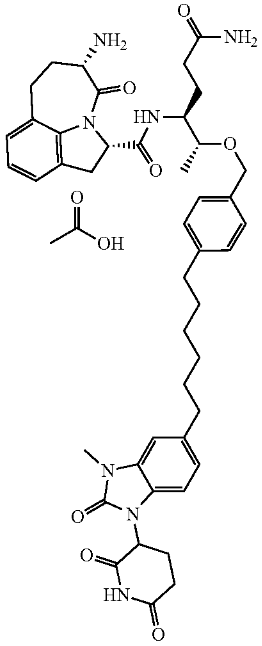 | (4S,5R)-4-[[(2S,11S)-11-amino-12-oxo-1-azatricyclo[6.4.1.0^[4,13]]trideca-4(13),5,7-trien-2-yl]formamido]-5-[(4-[6-[1-(2,6-dioxopiperidin-3-yl)-3-methyl-2-oxo-1,3-benzodiazol-5-yl]hexyl]phenyl) methoxy]hexanamide; acetic acid | 806.5 | (400 MHz, DMSO-$d_6$) δ 7.81 (d, J = 9.3 Hz, 1H), 7.21-7.07 (m, 4H), 7.04-6.97 (m, 3H), 6.94-6.82 (m, 2H), 6.68 (s, 1H), 5.33 (dd, J = 12.7, 5.3 Hz, 1H), 5.05 (dd, J = 11.0, 3.2 Hz, 1H), 4.40 (d, J = 2.3 Hz, 2H), 3.90-3.74 (m, 1H), 3.45-3.32 (m, 11H), 3.01 (dt, J = 9.8, 5.2 Hz, 2H), 2.93-2.79 (m, 2H), 2.76-2.66 (m, 1H), 2.59 (m, 3H), 2.17-1.92 (m, 4H), 1.88 (s, 3H), 1.78 (ddd, J = 10.4, 6.8, 3.4 Hz, 1H), 1.56 (q, J = 10.9 Hz, 4H), 1.41-1.25 (m, 3H), 1.07 (d, J = 6.2 Hz, 3H). |

TABLE 52-continued

Characterization data for intermediates prepare according to above.

| Intermediate | Structure | Chemical Name | MS: [(M + 1)]+ | $^1$H NMR |
|---|---|---|---|---|
| J64 | 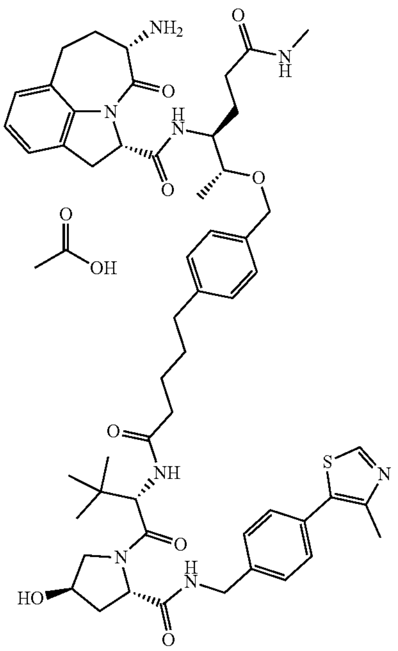 | (2S,4R)-1-[(2S)-2-[5-[4-([[(2R,3S)-3-[[(2S,11S)-11-amino-12-oxo-1-azatricyclo[6.4.1.0^[4,13]]trideca-4(13),5,7-trien-2-yl]formamido]-5-(methylcarbamoyl) pentan-2-yl]oxy]methyl) phenyl]pentanamido]-3,3-dimethylbutanoyl]-4-hydroxy-N-[[4-(4-methyl-1,3-thiazol-5-yl)phenyl]methyl] pyrrolidine-2-carboxamide; acetic acid | 991.8 | (400 MHz, DMSO-$d_6$) δ 8.99 (s, 1H), 8.57 (t, J = 6.1 Hz, 1H), 7.89 (d, J = 9.4 Hz, 1H), 7.84 (d, J = 9.3 Hz, 1H), 7.61-7.54 (m, 1H), 7.41 (q, J = 8.4 Hz, 4H), 7.18 (d, J = 8.0 Hz, 2H), 7.11 (d, J = 8.1 Hz, 2H), 7.02 (d, J = 7.5 Hz, 2H), 6.97-6.85 (m, 2H), 5.05 (dd, J = 11.0, 3.3 Hz, 1H), 4.55 (d, J = 9.4 Hz, 1H), 4.49-4.32 (m, 5H), 4.22 (dd, J = 15.8, 5.1 Hz, 1H), 3.81-3.65 (m, 2H), 3.69-3.59 (m, 4H), 3.60 (dq, J = 4.1, 1.5 Hz, 1H), 3.53-3.32 (m, 3H), 3.03 (s, 2H), 2.92-2.79 (m, 1H), 2.60-2.50 (m, 5H), 2.45 (s, 3H), 2.32 (s, 1H), 2.19 (s, 1H), 2.08-2.00 (m, 1H), 1.89 (s, 3H), 1.81-1.73 (m, 3H), 1.59-1.48 (m, 5H), 1.08 (d, J = 6.1 Hz, 3H), 0.94 (s, 9H). |
| J65 | 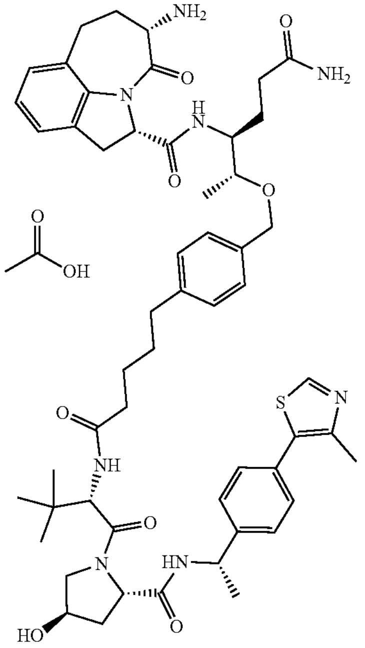 | (2S,4R)-1-[(2S)-2-[5-[4-([[(2R,3S)-3-[[(2S,11S)-11-amino-12-oxo-1-azatricyclo[6.4.1.0^[4,13]]trideca-4(13),5,7-trien-2-yl]formamido]-5-carbamoylpentan-2-yl]oxy]methyl) phenyl]pentanamido]-3,3-dimethylbutanoyl]-4-hydroxy-N-[(1S)-1-[4-(4-methyl-1,3-thiazol-5-yl)phenyl]ethyl] pyrrolidine-2-carboxamide; acetic acid | 991.4 | (400 MHz, DMSO-$d_6$) δ 8.99 (s, 1H), 8.38 (d, J = 7.8 Hz, 1H), 7.83 (dd, J = 9.3, 3.8 Hz, 2H), 7.44 (d, J = 8.3 Hz, 2H), 7.45-7.29 (m, 2H), 7.18 (d, J = 7.8 Hz, 3H), 7.11 (d, J = 7.9 Hz, 2H), 7.02 (d, J = 7.4 Hz, 2H), 6.98-6.89 (m, 1H), 6.69 (s, 1H), 5.10-5.02 (m, 1H), 4.92 (p, J = 6.9 Hz, 1H), 4.52 (d, J = 9.3 Hz, 1H), 4.47-4.39 (m, 3H), 4.28 (d, J = 4.0 Hz, 1H), 3.79 (m, 1H), 3.66-3.56 (m, 2H), 3.49-3.35 (m, 2H), 3.34-3.30 (m, 5H), 3.03 (s, 2H), 2.90-2.81 (m, 1H), 2.56 (s, 2H), 2.46 (s, 3H), 2.30 (d, J = 6.3 Hz, 1H), 2.20-1.98 (m, 3H), 1.91 (s, 3H), 1.79 (ddd, J = 13.0, 6.8, 3.4 Hz, 2H), 1.70-1.43 (m, 7H), 1.41-1.34 (m, 3H), 1.08 (d, J = 6.2 Hz, 3H), 0.94 (s, 9H). |

TABLE 52-continued

| Characterization data for intermediates prepare according to above. | | | | |
|---|---|---|---|---|
| Inter-mediate | Structure | Chemical Name | MS: [(M + 1)]+ | $^1$H NMR |
| J66 | 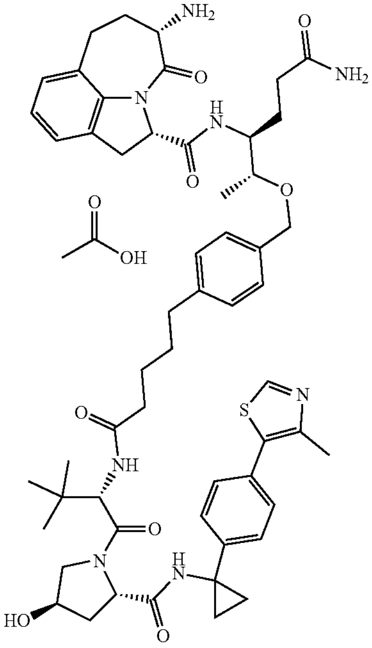 | (2S,4R)-1-[(2S)-2-[5-[4-([[(2R,3S)-3-[[(2S,11S)-11-amino-12-oxo-1-azatricyclo[6.4.1.0^[4,13]]trideca-4(13),5,7-trien-2-yl]formamido]-5-carbamoylpentan-2-yl]oxy]methyl) phenyl]pentanamido]-3,3-dimethylbutanoyl]-4-hydroxy-N-[1-[4-(4-methyl-1,3-thiazol-5-yl)phenyl]cyclopropyl] pyrrolidine-2-carboxamide; acetic acid | 1004.3 | (400 MHz, $CD_3OD$) δ 8.87 (s, 1H), 7.45-7.30 (m, 4H), 7.23 (d, J = 7.7 Hz, 2H), 7.17-7.08 (m, 3H), 7.05 (dd, J = 13.7, 6.5 Hz, 2H), 5.51 (d, J = 1.7 Hz, 1H), 5.21-5.13 (m, 1H), 4.64 (s, 1H), 4.57 (q, J = 7.9 Hz, 1H), 4.54-4.45 (m, 3H), 4.07-4.00 (m, 2H), 3.91 (d, J = 11.0 Hz, 1H), 3.80 (dd, J = 11.1, 3.8 Hz, 1H), 3.62-3.55 (m, 1H), 3.52-3.45 (m, 1H), 3.22 (t, J = 6.5 Hz, 2H), 3.08-2.99 (m, 1H), 2.64 (d, J = 6.9 Hz, 2H), 2.47 (s, 3H), 2.41-2.27 (m, 5H), 2.30-2.22 (m, 1H), 2.24-2.17 (m, 1H), 2.12-2.00 (m, 1H), 1.96 (s, 3H), 1.80-1.60 (m, 4H), 1.41-1.25 (m, 5H), 1.20 (d, J = 6.2 Hz, 3H), 1.05 (s, 9H). |
| J67 | 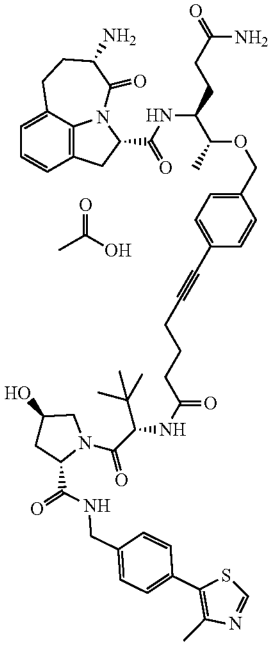 | (2S,4R)-1-[(2S)-2-[6-[4-([[(2R,3S)-3-[[(2S,11S)-11-amino-12-oxo-1-azatricyclo[6.4.1.0^[4,13]]trideca-4(13),5,7-trien-2-yl]formamido]-5-carbamoylpentan-2-yl]oxy]methyl)phenyl] hex-5-ynamido]-3,3-dimethylbutanoyl]-4-hydroxy-N-[[4-(4-methyl-1,3-thiazol-5-yl)phenyl]methyl] pyrrolidine-2-carboxamide; acetic acid | 987.3 | (400 MHz, DMSO-$d_6$) δ 8.99 (d, J = 1.8 Hz, 1H), 8.58 (t, J = 6.1 Hz, 1H), 7.98 (d, J = 9.6 Hz, 1H), 7.83 (d, J = 9.5 Hz, 1H), 7.47-7.28 (m, 7H), 7.26 (d, J = 8.0 Hz, 2H), 7.17 (s, 1H), 7.02 (d, J = 5.7 Hz, 2H), 6.93 (t, J = 7.4 Hz, 1H), 6.69 (s, 1H), 5.77 (d, J = 1.8 Hz, 1H), 5.06 (d, J = 11.2 Hz, 1H), 4.57 (d, J = 9.3 Hz, 1H), 4.46 (m, 3H), 4.44 (d, J = 7.9 Hz, 1H), 4.37 (s, 1H), 4.23 (dd, J = 15.8, 5.4 Hz, 1H), 3.80 (s, 1H), 3.68 (s, 2H), 3.37 (dd, J = 16.6, 11.0 Hz, 1H), 3.03 (s, 2H), 2.87-2.78 (m, 1H), 2.44 (d, J = 11.4 Hz, 6H), 2.31 (dd, J = 15.0, 7.5 Hz, 1H), 2.08 (s, 3H), 2.06-1.92 (m, 5H), 1.91 (s, 3H), 1.82-1.75 (m, 3H), 1.57 (s, 1H), 1.09 (d, J = 6.3 Hz, 3H), 0.96 (s, 9H). |

TABLE 52-continued

| Characterization data for intermediates prepare according to above. | | | | |
|---|---|---|---|---|
| Inter-mediate | Structure | Chemical Name | MS: $[(M + 1)]^+$ | $^1H$ NMR |
| J68 | 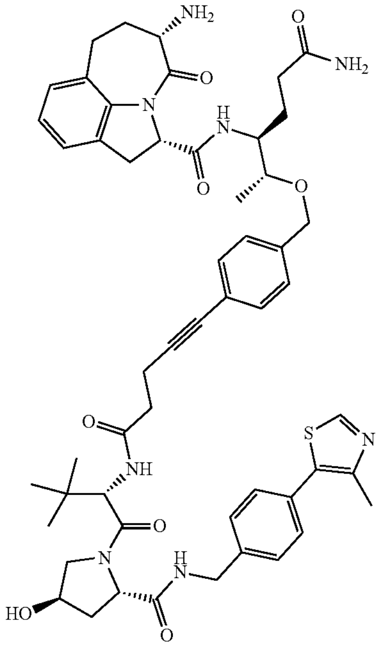 [SMILES: Cc1ncsc1-c1ccc(CNC(=O)[C@@H]2C[C@@H](O)CN2C(=O)[C@@H](NC(=O)CCC#Cc2ccc(CO[C@H](C)[C@H](CCC(N)=O)NC(=O)[C@@H]3Cc4cccc5c4N3C(=O)[C@@H](N)CC5)cc2)C(C)(C)C)cc1] | (2S,4R)-1-[(2S)-2-[5-[4-([[(2R,3S)-3-[[(2S,11S)-11-amino-12-oxo-1-azatricyclo[6.4.1.0^[4,13]]trideca-4(13),5,7-trien-2-yl]formamido]-5-carbamoylpentan-2-yl]oxy]methyl) phenyl]pent-4-ynamido]-3,3-dimethylbutanoyl]-4-hydroxy-N-[[4-(4-methyl-1,3-thiazol-5-yl)phenyl]methyl] pyrrolidine-2-carboxamide | $[M/2 + 1]^+$ = 487.5 | (400 MHz, DMSO-$d_6$) δ 9.00 (s, 1H), 8.61 (t, J = 6.0 Hz, 1H), 8.08 (d, J = 9.4 Hz, 1H), 7.91-7.83 (m, 1H), 7.45-7.21 (m, 8H), 7.10-6.94 (m, 2H), 6.75 (s, 1H), 4.60 (d, J = 9.3 Hz, 1H), 4.50-4.33 (m, 4H), 4.22 (dd, J = 15.8, 5.3 Hz, 1H), 3.84-3.62 (m, 2H), 3.45 (s, 1H), 2.88-2.33 (m, 5H), 2.46 (s, 3H), 2.20-1.50 (m, 1 4H), 1.10 (t, J = 6.5 Hz, 3H), 0.95 (s, 9H). |
| J69 | 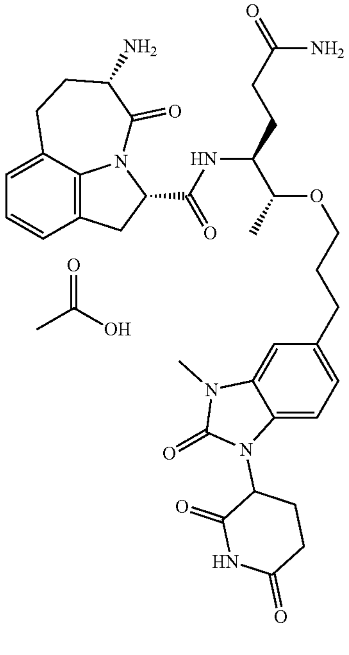 | (4S,5R)-4-[[(2S,11S)-11-amino-12-oxo-1-azatricyclo[6.4.1.0^[4,13]]trideca-4(13),5,7-trien-2-yl]formamido]-5-[3-[1-(2,6-dioxopiperidin-3-yl)-3-methyl-2-oxo-1,3-benzodiazol-5-yl]propoxy] hexanamide; acetic acid | 674.5 | (400 MHz, $CD_3OD$) δ 7.11-6.93 (m, 6H), 5.16 (d, J = 7.0 Hz, 1H), 3.96 (s, 1H), 3.55-3.38 (m, 5H), 3.19 (d, J = 7.6 Hz, 2H), 2.97-2.88 (m, 1H), 2.85-2.71 (m, 4H), 2.36-2.20 (m, 8H), 2.15-2.00 (m, 1H), 1.94 (s, 3H), 1.93-1.80 (m, 4H), 1.70 (s, 1H), 1.17 (d, J = 6.3 Hz, 3H). |

TABLE 52-continued

Characterization data for intermediates prepare according to above.

| Inter-mediate | Structure | Chemical Name | MS: $[(M + 1)]^+$ | $^1H$ NMR |
|---|---|---|---|---|
| J70 | 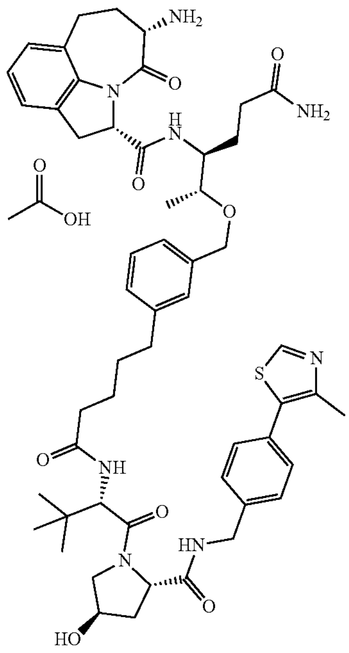 | (2S,4R)-1-[(2S)-2-[5-[3-([[(2R,3S)-3-[[(2S,11S)-11-amino-12-oxo-1-azatricyclo[6.4.1.0^[4,13]]trideca-4(13),5,7-trien-2-yl]formamido]-5-carbamoylpentan-2-yl]oxy]methyl) phenyl] pentanamido]-3,3-dimethylbutanoyl]-4-hydroxy-N-[[4-(4-methyl-1,3-thiazol-5-yl)phenyl]methyl] pyrrolidine-2-carboxamide; acetic acid | 977.4 | (400 MHz, $CD_3OD$) δ 8.90 (s, 1H), 7.48 (d, J = 8.4 Hz, 2H), 7.47-7.40 (m, 2H), 7.26-7.14 (m, 2H), 7.16-6.99 (m, 5H), 5.16 (dd, J = 11.0, 3.7 Hz, 1H), 4.65 (s, 1H), 4.62-4.46 (m, 4H), 4.37 (d, J = 15.5 Hz, 1H), 4.06-3.98 (m, 1H), 3.98-3.88 (m, 2H), 3.82 (dd, J = 11.0, 3.9 Hz, 1H), 3.63-3.53 (m, 1H), 3.48 (dd, J = 16.7, 10.8 Hz, 1H), 3.37 (s, 2H), 3.21 (s, 2H), 3.11-2.97 (m, 2H), 2.62 (s, 2H), 2.49 (s, 3H), 2.38-2.18 (m, 4H), 2.15-1.99 (m, 2H), 1.96 (s, 3H), 1.70-1.65 (m, 5H), 1.32 (t, J = 7.3 Hz, 1H), 1.21 (d, J = 6.4 Hz, 3H), 1.04 (s, 9H). |
| J71 | 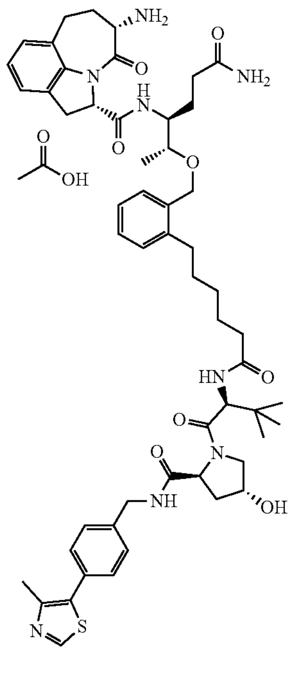 | (2S,4R)-1-[(2S)-2-[6-[2-([[(2R,3S)-3-[[(2S,11S)-11-amino-12-oxo-1-azatricyclo[6.4.1.0^[4,13]]trideca-4(13),5,7-trien-2-yl]formamido]-5-carbamoylpentan-2-yl]oxy]methyl)phenyl] hexanamido]-3,3-dimethylbutanoyl]-4-hydroxy-N-[[4-(4-methyl-1,3-thiazol-5-yl)phenyl]methyl] pyrrolidine-2-carboxamide; acetic acid | 991.3 | (400 MHz, DMSO-$d_6$) δ 8.99 (s, 1H), 8.58 (t, J = 6.1 Hz, 1H), 7.88 (d, J = 9.5 Hz, 1H), 7.82 (d, J = 9.2 Hz, 1H), 7.40 (q, J = 8.3 Hz, 4H), 7.24 (t, J = 6.4 Hz, 1H), 7.18 (dd, J = 8.6, 7.0 Hz, 2H), 7.1 7-7.07 (m, 1H), 7.01 (d, J = 7.4 Hz, 2H), 6.96-6.85 (m, 1H), 6.71 (s, 1H), 5.05 (dd, J = 11.0, 3.3 Hz, 1H), 4.58-4.50 (m, 1H), 4.50-4.42 (m, 1H), 4.45-4.37 (m, 2H), 4.35 (s, 1H), 4.22 (dd, J = 15.8, 5.4 Hz, 1H), 3.78 (s, 1H), 3.66 (s, 1H), 3.52-3.30 (m, 6H), 3.01 (s, 2H), 2.84 (d, J = 16.4 Hz, 1H), 2.56 (d, J = 7.7 Hz, 2H), 2.53 (s, 2H), 2.45 (s, 3H), 2.27 (dt, J = 14.7, 7.5 Hz, 1H), 2.15-1.90 (m, 5H), 1.89 (s, 3H), 1.56-1.46 (m, 4H), 1.38-1.22 (m, 4H), 1.08 (d, J = 6.7 Hz, 3H), 0.93 (s, 9H). |

TABLE 52-continued

Characterization data for intermediates prepare according to above.

| Inter-mediate | Structure | Chemical Name | MS: $[(M+1)]^+$ | $^1H$ NMR |
|---|---|---|---|---|
| J72 | 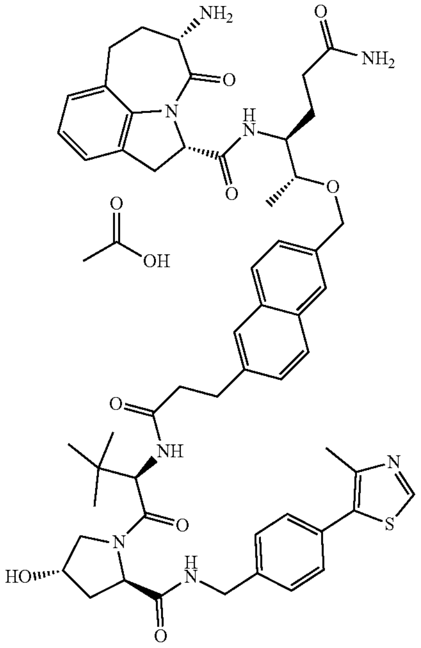 | (2R,4S)-1-[(2R)-2-[3-[6-([[(2R,3S)-3-[[(2S,11S)-11-amino-12-oxo-1-azatricyclo[6.4.1.0^[4,13]]trideca-4(13),5,7-trien-2-yl]formamido]-5-carbamoylpentan-2-yl]oxy]methyl) naphthalen-2-yl]propanamido]-3,3-dimethylbutanoyl]-4-hydroxy-N-[[4-(4-methyl-1,3-thiazol-5-yl)phenyl]methyl] pyrrolidine-2-carboxamide; acetic acid | 999.7 | (400 MHz, $CD_3OD$) δ 8.89 (s, 1H), 7.75 (m, 3H), 7.69 (s, 1H), 7.51-7.36 (m, 6H), 7.07 (d, J = 7.5 Hz, 1H), 6.98 (t, J = 7.5 Hz, 1H), 6.91 (d, J = 7.3 Hz, 1H), 5.12 (dd, J = 11.0, 3.6 Hz, 1H), 4.76-4.51 (m, 5H), 4.50 (s, 1H), 4.35 (d, J = 1 5.5 Hz, 1H), 4.03 (dd, J = 9.7, 5.5 Hz, 1H), 3.95-3.80 (m, 2H), 3.77 (dd, J = 10.9, 4.0 Hz, 1H), 3.64 (dd, J = 6.4, 4.5 Hz, 1H), 3.19 (d, J = 5.9 Hz, 2H), 3.15-3.06 (m, 2H), 3.09-2.99 (m, 1H), 2.93-2.83 (m, 1H), 2.82-2.62 (m, 2H), 2.48 (s, 3H), 2.40-2.22 (m, 3H), 2.20 (d, J = 8.8 Hz, 1H), 2.07 (ddd, J = 13.2, 8.9, 4.5 Hz, 1H), 1.95 (s, 3H), 1.36-1.24 (m, 2H), 1.80-1.70 (m, 1H), 1.22 (d, J = 6.7 Hz, 3H), 0.91 (s, 9H). |
| J82 | 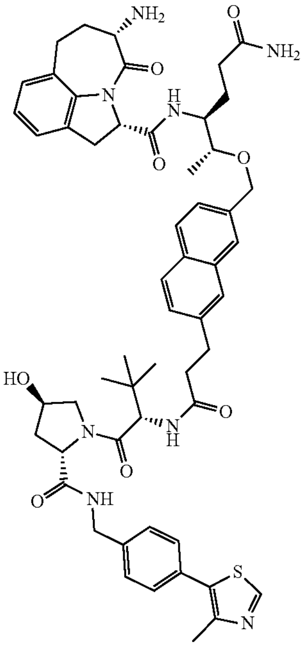 [SMILES: Cc1ncsc1-c1ccc(CNC(=O)[C@@H]2C[C@@H](O)CN2C(=O)[C@@H](NC(=O)CCc2ccc3ccc(CO[C@H](C)[C@H](CCC(N)=O)NC(=O)[C@@H]4Cc5cccc6c5N4C(=O)[C@@H](N)CC6)cc3c2)C(C)(C)C)cc1] | (2S,4R)-1-[(2S)-2-[3-[7-([[(2R,3S)-3-[[(2S,11S)-11-amino-12-oxo-1-azatricyclo[6.4.1.0^[4,13]]trideca-4(13),5,7-trien-2-yl]formamido]-5-carbamoylpentan-2-yl]oxy]methyl) naphthalen-2-yl]propanamido]-3,3-dimethylbutanoyl]-4-hydroxy-N-[[4-(4-methyl-1,3-thiazol-5-yl)phenyl]methyl] pyrrolidine-2-carboxamide | 999.50 | $^1H$ NMR (400 MHz, DMSO-$d_6$) δ 8.98 (s, 1H), 8.57 (d, J = 6.1 Hz, 1H), 8.00 (d, J = 9.3 Hz, 1H), 7.84 (d, J = 9.2 Hz, 1H), 7.80 (dd, J = 8.5, 4.4 Hz, 2H), 7.71 (s, 1H), 7.65 (s, 1H), 7.46-7.33 (m, 6H), 7.17 (s, 1H), 7.00 (d, J = 7.3 Hz, 1H), 6.97-6.86 (m, 2H), 6.69 (s, 1H), 5.05 (dd, J = 11.0, 3.3 Hz, 1H), 4.67-4.52 (m, 3H), 4.50-4.46 (m, 3H), 4.37-4.35 (m, 1H), 4.24-4.21 (m, 1H), 3.83-3.81 (m, 1H), 3.68-3.66 (m, 2H), 3.53-3.43 (m, 2H), 3.35-3.33 (m, 1H), 3.07-2.87 (m, 2H), 2.83-2.78 (m, 1H), 2.77-2.67 (m, 2H), 2.58-2.51 (m, 1H), 2.44 (s, 3H), 2.14-1.99 (m, 2H), 1.94-1.92 (m, 2H), 1.91-1.88 (m, 5H), 1.61-1.59 (m, 1H), 1.12 (d, J = 6.3 Hz, 3H), 0.88 (s, 9H) |

TABLE 52-continued

| Characterization data for intermediates prepare according to above. | | | | |
|---|---|---|---|---|
| Intermediate | Structure | Chemical Name | MS: [(M + 1)]$^+$ | $^1$H NMR |
| J83 | 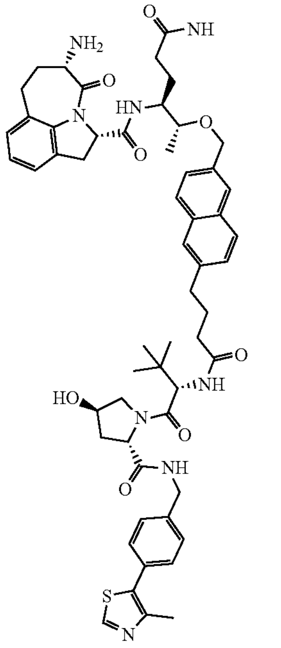 [SMILES: Cc1ncsc1-c1ccc(CNC(=O)[C@@H]2C[C@@H](O)CN2C(=O)[C@@H](NC(=O)CCCc2ccc3cc(CO[C@H](C)[C@H](CCC(N)=O)NC(=O)[C@@H]4Cc5cccc6c5N4C(=O)[C@@H](N)CC6)ccc3c2)C(C)(C)C)cc1] | (2S,4R)-1-[(2S)-2-[4-[6-([[(2R,3S)-3-[[(2S,11S)-11-amino-12-oxo-1-azatricyclo[6.4.1.0^[4,13]]trideca-4(13),5,7-trien-2-yl]formamido]-5-carbamoylpentan-2-yl]oxy]methyl) naphthalen-2-yl]butanamido]-3,3-dimethylbutanoyl]-4-hydroxy-N-[[4-(4-methyl-1,3-thiazol-5-yl)phenyl]methyl] pyrrolidine-2-carboxamide | 1013.75 | $^1$H NMR (400 MHz, $CD_3OD$) δ 8.91 (s, 1H), 7.79-7.71 (m, 3H), 7.68 (d, J = 8.7 Hz, 1H), 7.52-7.35 (m, 6H), 7.09 (d, J = 7.8 Hz, 1H), 6.99 (t, J = 7.5 Hz, 1H), 6.88 (d, J = 7.3 Hz, 1H), 5.14 (dd, J = 11.0, 3.6 Hz, 1H), 4.74-4.66 (m, 2H), 4.62-4.50 (m, 3H), 4.36 (d, J = 15.5 Hz, 1H), 4.18 (d, J = 10.8 Hz, 1H), 4.05 (d, J = 11.7 Hz, 1H), 3.95 (d, J = 10.9 Hz, 1H), 3.83 (dd, J = 11.0, 3.9 Hz, 1H), 3.64 (dd, J = 6.3, 4.5 Hz, 1H), 3.24 (d, J = 6.7 Hz, 2H), 2.90-2.78 (m, 3H), 2.48 (s, 3H), 2.43 (s, 0H), 2.41-2.31 (m, 3H), 2.29-2.20 (m, 2H), 2.04 (dd, J = 14.9, 7.6 Hz, 3H), 1.75(s, 1H), 1.25 (d, J = 6.3 Hz, 3H), 1.06 (s, 9H) |
| J84 | 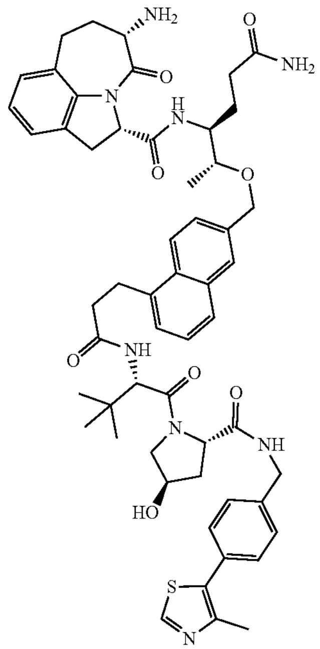 [SMILES: Cc1ncsc1-c1ccc(CNC(=O)[C@@H]2C[C@@H](O)CN2C(=O)[C@@H](NC(=O)CCc2cccc3cc(CO[C@H](C)[C@H](CCC(N)=O)NC(=O)[C@@H]4Cc5cccc6c5N4C(=O)[C@@H](N)CC6)ccc23)C(C)(C)C)cc1] | (2S,4R)-1-[(2S)-2-[3-[6-([[(2R,3S)-3-[[(2S,11S)-11-amino-12-oxo-1-azatricyclo[6.4.1.0^[4,13]]trideca-4(13),5,7-trien-2-yl]formamido]-5-carbamoylpentan-2-yl]oxy]methyl) naphthalen-1-yl]propanamido]-3,3-dimethylbutanoyl]-4-hydroxy-N-[[4-(4-methyl-1,3-thiazol-5-yl)phenyl]methyl] pyrrolidine-2-carboxamide | 999.30 | $^1$H NMR (400 MHz, DMSO-$d_6$) δ 8.99 (s, 1H), 8.58 (t, J = 6.1 Hz, 1H), 8.07 (d, J = 9.4 Hz, 1H), 8.01 (d, J = 8.8 Hz, 1H), 7.85 (d, J = 9.2 Hz, 1H), 7.81 (d, J = 1.4 Hz, 1H), 7.72 (d, J = 8.0 Hz, 1H), 7.46-7.39 (m, 7H), 7.19 (s, 1H), 7.01 (d, J = 7.1 Hz, 1H), 6.97-6.87 (m, 2H), 6.71 (s, 1H), 5.18 (s, 1H), 5.06 (d, J = 9.5 Hz, 1H), 4.66-4.55 (m, 3H), 4.50-4.34 (m, 3H), 4.23 (dd, J = 15.6, 5.1 Hz, 1H), 3.85 (s, 1H), 3.70 (s, 2H), 3.59-3.41 (m, 2H), 3.34-3.30 (m, 6H), 3.04 (d, J = 12.5 Hz, 2H), 2.82 (d, J = 17.0 Hz, 1H), 2.69 (t, J = 7.0 Hz, 1H), 2.51-2.49 (m, 2H), 2.45 (s, 3H), 2.10-2.06 (m, 2H), 2.00-1.88 (m, 2H), 1.83-1.79 (m, 1H), 1.59-1.57 (m, 1H), 1.13 (d, J = 6.3 Hz, 3H), 0.94 (s, 9H). |

TABLE 52-continued

| Intermediate | Structure | Chemical Name | MS: [(M + 1)]+ | 1H NMR |
|---|---|---|---|---|
| Characterization data for intermediates prepare according to above. | | | | |
| J85 | 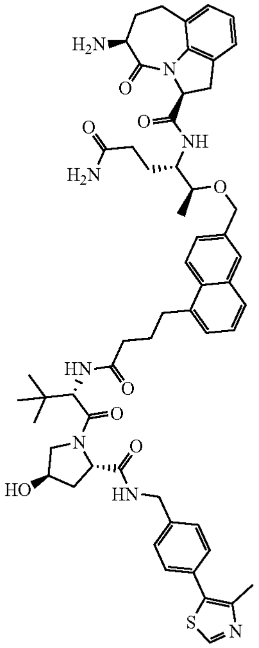 [SMILES: Cc1ncsc1-c1ccc(CNC(=O)[C@@H]2C[C@@H](O)CN2C(=O)[C@@H](NC(=O)CCCc2cccc3cc(CO[C@@H](C)[C@H](CCC(N)=O)NC(=O)[C@@H]4Cc5cccc6c5N4C(=O)[C@@H](N)CC6)ccc23)C(C)(C)C)cc1] | (2S,4R)-1-[(2S)-2-[4-[6-([[(2S,3S)-3-[[(2S,11S)-11-amino-12-oxo-1-azatricyclo[6.4.1.0^[4,13]]trideca-4(13),5,7-trien-2-yl]formamido]-5-carbamoylpentan-2-yl]oxy]methyl) naphthalen-1-yl]butanamido]-3,3-dimethylbutanoyl]-4-hydroxy-N-[[4-(4-methyl-1,3-thiazol-yl)phenyl]methyl] pyrrolidine-2-carboxamide | 1013.20 | $^1$H NMR (400 MHz, DMSO-d$_6$) δ 8.99 (s, 1H), 8.57 (t, J = 6.1 Hz, 1H), 8.00 (dd, J = 13.5, 9.1 Hz, 2H), 7.91-7.77 (m, 3H), 7.71 (d, J = 8.2 Hz, 1H), 7.52-7.29 (m, 6H), 7.18 (s, 1H), 7.01 (dd, J = 6.8, 2.3 Hz, 1H), 6.96-6.84 (m, 2H), 6.70 (s, 1H), 5.05 (dd, J = 11.0, 3.2 Hz, 1H), 4.64-4.59 (m, 3H), 4.46-4.42 (m, 2H), 4.37-4.35 (m, 1H), 4.24-4.15 (m, 1H), 3.89-3.79 (m, 2H), 3.69 (d, J = 3.2 Hz, 2H), 3.54-3.49 (m, 1H), 3.37-3.62 (m, 1H), 3.03-2.98 (m, 2H), 2.86-2.66 m, 3H), 2.45 (s, 3H), 2.42-2.24 (m, 2H), 2.18-2.00 (m, 2H), 1.92-1.88 (m, 10H), 1.62-1.60 (m, 1H), 1.20-1.03 (m, 3H), 0.96 (s, 9H). |
| J86 | 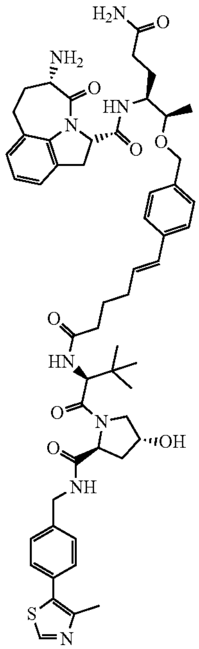 | (2S,4R)-1-[(2S)-2-[(5E)-6-[4-([[(2R,3S)-3-[[(2S,11S)-11-amino-12-oxo-1-azatricyclo[6.4.1.0^4,13]]trideca-4(13),5,7-trien-2-yl]formamido]-5-carbamoylpentan-2-yl]oxy]methyl) phenyl]hex-5-enamido]-3,3 dimethylbutanoyl]-4-hydroxy-N-[[4-(4-methyl-1,3-thiazol-5-yl)phenyl]methyl] pyrrolidine-2-carboxamide | 989.65 | $^1$H NMR (400 MHz, DMSO-d$_6$) δ 8.99 (s, 1H), 8.60 (t, J = 6.0 Hz, 1H), 8.28 (s, 1H), 7.94-7.90 (m, 2H), 7.41 (q, J = 8.2 Hz, 5H), 7.32 (d, J = 8.0 Hz, 2H), 7.21 (d, J = 8.1 Hz, 3H), 7.03 (d, J = 7.5 Hz, 2H), 6.95 (dd, J = 8.2, 6.5 Hz, 1H), 6.72 (s, 1H), 6.38 (d, J = 15.9 Hz, 1H), 6.34-6.23 (m, 1H), 5.07 (dd, J = 11.2, 3.2 Hz, 1H), 4.57 (d, J = 9.3 Hz, 1H), 4.49-4.39 (m, 4H), 4.37 (s, 1H), 4.22 (dd, J = 15.9, 5.3 Hz, 1H), 3.81-3.75 (m, 2H), 3.70-3.66 (m, 2H), 3.47-3.36 (m, 6H), 3.08-3.05 (m, 2H), 2.82 (d, J = 16.6 Hz, 1H), 2.45 (s, 3H), 2.37-2.33 (m, 1H), 2.24-2.14 (m, 3H), 2.12-1.97 (m, 3H), 1.94-1.87 (m, 1H), 1.84-1.72 (m, 1H), 1.70-1.62 (m, 1H), 1.58-1.52 (m, 1H), 1.08 (d, J = 6.2 Hz, 3H), 0.95 (s, 9H). |

TABLE 52-continued

| Characterization data for intermediates prepare according to above. | | | | |
|---|---|---|---|---|
| Intermediate | Structure | Chemical Name | MS: $[(M+1)]^+$ | $^1H$ NMR |
| J87 | 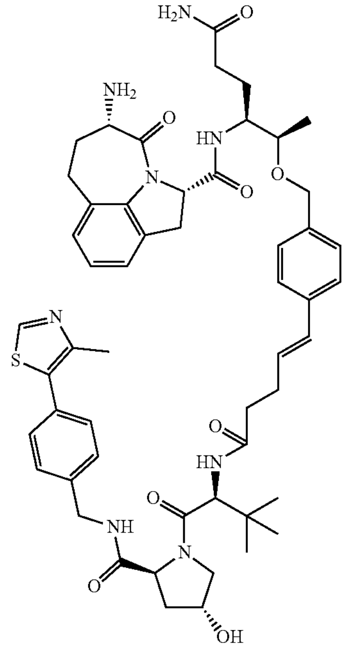 [SMILES: Cc1ncsc1-c1ccc(CNC(=O)[C@@H]2C[C@@H](O)CN2C(=O)[C@@H](NC(=O)CC/C=C/c2ccc(CO[C@H](C)[C@H](CCC(N)=O)NC(=O)[C@@H]3Cc4cccc5c4N3C(=O)[C@@H](N)CC5)cc2)C(C)(C)C)cc1] | (2S,4R)-1-[(2S)-2-[(4E)-5-[4-([[(2R,3S)-3-[[(2S,11S)-11-amino-12-oxo-1-azatricyclo[6.4.1.0^[4,13]]trideca-yl]formamido]-5-4(13),5,7-trien-2-carbamoylpentan-2-yl]oxy]methyl) phenyl]pent-4-enamido]-3,3-dimethylbutanoyl]-4-hydroxy-N-[[4-(4-methyl-1,3-thiazol-5-yl)phenyl]methyl] pyrrolidine-2-carboxamide | 975.4 | $^1H$ NMR (400 MHz, DMSO-$d_6$) δ 8.99 (s, 1H), 8.57 (t, J = 5.8 Hz, 1H), 7.97 (d, J = 9.9 Hz, 1H), 7.85-7.81 (m, 1H), 7.41 (q, J = 8.2 Hz, 4H), 7.28 (d, J = 7.9 Hz, 2H), 7.23-7.15 (m, 3H), 7.02 (d, J = 7.0 Hz, 2H), 6.94 (d, J = 7.6 Hz, 1H), 6.69 (s, 1H), 6.41 (d, J = 15.8 Hz, 1H), 6.31-6.21 (m, 1H), 5.14 (d, J = 3.5 Hz, 1H), 5.05 (d, J = 10.9 Hz, 1H), 4.58 (d, J = 9.3 Hz, 1H), 4.49-4.39 (m, 4H), 4.36 (s, 1H), 4.22 (dd, J = 16.0, 5.3 Hz, 1H), 3.79 (s, 1H), 3.69-3.66 (m, 2H), 3.46-3.42 (m, 1H), 3.05-3.01 (m, 2H), 2.83 (d, J = 16.8 Hz, 1H), 2.68 (p, J = 1.9 Hz, 2H), 2.44 (s, 3H), 2.33 (p, J = 1.9 Hz, 3H), 2.09-2.01 (m, 4H), 1.91 (s, 4H), 1.58-1.55 (m, 1H), 1.15 (s, 1H), 1.08 (d, J = 6.2 Hz, 4H), 0.93 (s, 9H) |
| J88 | 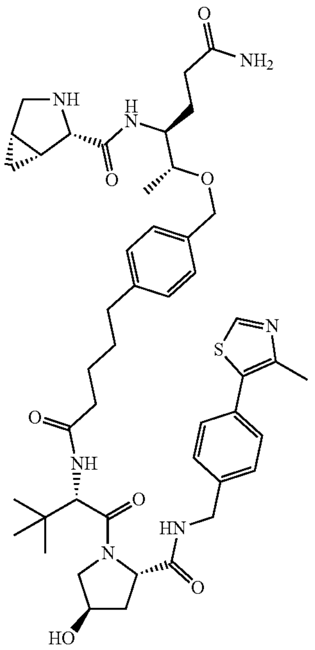 [SMILES: Cc1ncsc1-c1ccc(CNC(=O)[C@@H]2C[C@@H](O)CN2C(=O)[C@@H](NC(=O)CCCCc2ccc(CO[C@H](C)[C@H](CCC(N)=O)NC(=O)[C@H]3NC[C@H]4C[C@H]43)cc2)C(C)(C)C)cc1] | (2S,4R)-1-[(2S)-2-[5-[4-([[(2R,3S)-3-[(1R,2S,5S)-3-azabicyclo[3.1.0]hexan-2-ylformamido]-5-carbamoylpentan-2-yl]oxy]methyl) phenyl]pentanamido]-3,3-dimethylbutanoyl]-4-hydroxy-N-[[4-(4-methyl-1,3-thiazol-5-yl)phenyl]methyl] pyrrolidine-2-carboxamide | 858.35 | $^1H$ NMR (400 MHz, DMSO-$d_6$) δ 8.99 (s, 1H), 8.59 (t, J = 6.1 Hz, 1H), 7.92-7.83 (m, 2H), 7.72 (d, J = 9.3 Hz, 1H), 7.46-7.32 (m, 5H), 7.29 -7.18 (m, 2H), 7.14 (d, J = 7.8 Hz, 2H), 6.70 (s, 1H), 4.55 (d, J = 9.4 Hz, 1H), 4.51-4.38 (m, 4H), 4.36 (s, 1H), 4.22 (dd, J = 15.9, 5.3 Hz, 1H), 3.77 (d, J = 8.1 Hz, 1H), 3.66 (t, J = 8.8 Hz, 2H), 3.60-3.52 (m, 1H), 3.52-3.40 (m, 1H), 3.00-2.89 (m, 1H), 2.86-2.76 (m, 1H), 2.71 (q, J = 7.1 Hz, 4H), 2.56 (t, J = 6.8 Hz, 2H), 2.45 (s, 3 H), 2.37-2.26 (m, 1H), 2.15 (dt, J = 13.9, 6.7 Hz, 1H), 2.03 (tdd, J = 14.7, 9.4, 4.0 Hz, 2H), 1.91 (ddd, J = 13.1, 8.7, 4.6 Hz, 1H), 1.63-1.43 (m, 4H), 1.35 (td, J = 7.3, 3.8 Hz, 1H), 1.15-1.06 (m, 4H), 0.94 (s, 9H), 0.33 (q, J = 4.2 Hz, 1H), 0.25 (td, J = 7.7, 4.6 Hz, 1H) |

TABLE 52-continued

Characterization data for intermediates prepare according to above.

| Inter-mediate | Structure | Chemical Name | MS: $[(M + 1)]^+$ | $^1H$ NMR |
|---|---|---|---|---|
| J89 | 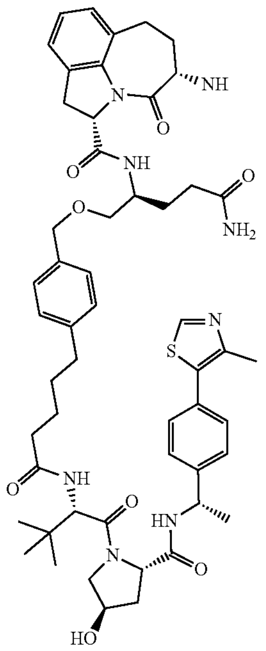 [SMILES: Cc1ncsc1-c1ccc([C@H](C)NC(=O)[C@@H]2C[C@@H](O)CN2C(=O)[C@@H](NC(=O)CCCCc2ccc(COC[C@H](CCC(N)=O)NC(=O)[C@@H]3Cc4cccc5c4N3C(=O)[C@@H](N)CC5)cc2)C(C)(C)C)cc1] | (2S,4R)-1-[(2S)-2-[5-(4-[[(2S)-2-[[(2S,11S)-11-Amino-12-oxo-1-azatricyclo[6.4.1.0^[4,13]]trideca-4(13),5,7-trien-2-yl]formamido]-4-carbamoylbutoxy]methyl]phenyl)pentanamido]-3,3-dimethylbutanoyl]-4-hydroxy-N-[(1S)-1-[4-(4-methyl-1,3-thiazol-5-yl)phenyl]ethyl]pyrrolidine-2-carboxamide | 977.35 | $^1H$ NMR (400 MHz, DMSO-$d_6$) δ 8.99 (s, 1H), 8.39 (d, J = 7.9 Hz, 1H), 7.84 (td, J = 15.3, 14.3, 8.6 Hz, 2H), 7.45-7.35 (m, 4H), 7.24-7.12 (m, 4H), 7.11-6.89 (m, 4H), 6.71 (s, 1H), 5.11 (d, J = 8.3 Hz, 1H), 5.01 (dt, J = 11.0, 3.4 Hz, 1H), 4.92 (p, J = 6.9 Hz, 1H), 4.52 (d, J = 9.3 Hz, 1H), 4.42 (t, J = 3.9 Hz, 3H), 4.31-4.25 (m, 1H), 3.86-3.77 (m, 1H), 3.6 (dd, J = 15.8, 11.7 Hz, 2H), 3.53-3.42 (m, 1H), 3.14-2.64 (m, 5H), 2.56 (d, J = 10.0 Hz, 3H), 2.46 (s, 3H), 2.37-2.21 (m, 1H), 2.21-1.85 (m, 5H), 1.79 (ddt, J = 13.2, 9.5, 4.5 Hz, 2H), 1.68-1.42 (m, 6H), 1.38 (d, J = 7.0 Hz, 3H), 1.25 (d, J = 3.0 Hz, 1H), 1.14-1.03 (m, 1H), 0.94 (s, 9H) |
| J146 | 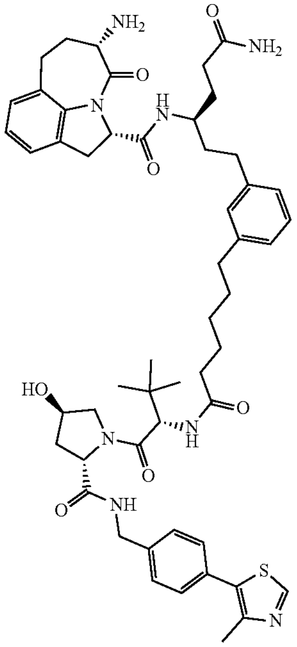 [SMILES: Cc1ncsc1-c1ccc(CNC(=O)[C@@H]2C[C@@H](O)CN2C(=O)[C@@H](NC(=O)CCCCCc2cccc(CC[C@H](CCC(N)=O)NC(=O)[C@@H]3Cc4cccc5c4N3C(=O)[C@@H](N)CC5)c2)C(C)(C)C)cc1] | (2S,4R)-1-[(2S)-2-(6-[3-[(3R)-3-[[(2S,11S)-11-amino-12-oxo-1-azatricyclo[6.4.1.0^[4,13]]trideca-4(13),5,7-trien-2-yl]formamido]-5-carbamoylpentyl]phenyl]hexanamido)-3,3-dimethylbutanoyl]-4-hydroxy-N-[[4-(4-methyl-1,3-thiazol-5-yl)phenyl]methyl]pyrrolidine-2-carboxamide | 961.40 | $^1H$ NMR (400 MHz, DMSO-$d_6$) δ 8.99 (s, 1H), 8.57 (t, J = 6.1 Hz, 1H), 7.84 (dd, J = 10.9, 9.1 Hz, 2H), 7.41 (q, J = 8.4 Hz, 4H), 7.21-7.10 (m, 2H), 7.07 (d, J = 7.1 Hz, 1H), 7.05-6.88 (m, 5H), 6.69 (s, 1H), 5.14 (s, 1H), 5.07-4.97 (m, 1H), 4.55 (d, J = 9.4 Hz, 1H), 4.49-4.39 (m, 2H), 4.36 (s, 1H), 4.22 (dd, J = 15.9, 5.4 Hz, 1H), 3.72-3.61 (m, 3H), 3.51-3.39 (m, 3H), 3.02 (d, J = 6.3 Hz, 2H), 2.91 (dd, J = 16.7, 3.5 Hz, 1H), 2.61-2.54 (m, 1H), 2.45 (s, 3H), 2.32-2.19 (m, 1H), 2.18-2.08 (m, 3H), 2.05 (d, J = 8.1 Hz, 3H), 2.00-1.86 (m, 3H), 1.75-1.59 (m, 4H), 1.58-1.41 (m, 5H), 1.27 (q, J = 7.6 Hz, 2H), 0.94 (s, 9H) |

(2S)-2- [[(5S,8S,10aR)-5-amino-3-1[6- [1-(2,6-di-oxopiperidin-3-yl)-3-methyl-2-oxo-1,3-benzodiazol-5-yl]hexanoyl]-6-oxo-octahydropyrrolo[1,2-a][1,5]diazocin-8-yl]formamido]-N-(diphenylmethyl)pentanediamide; trifluoroacetic acid (Intermediate J73)

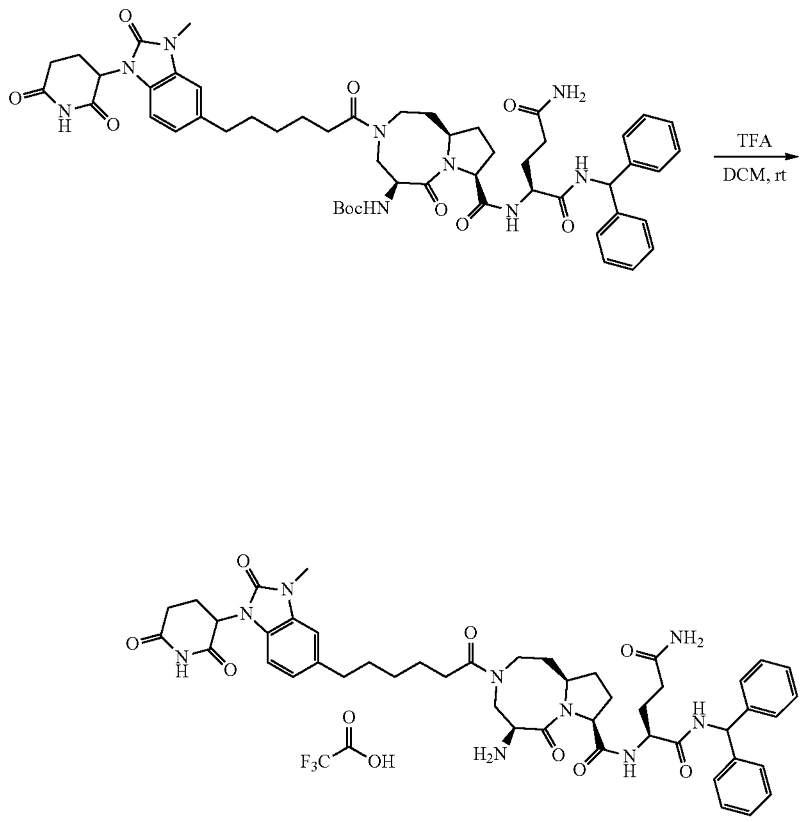

The titled compound was prepared according to Step 4 to prepare Intermediate G. 8H NMR (400 MHz, DMSO-d) 11.10 (s, 1H), 8.86 (t, J=8.4 Hz, 1H), 8.40-8.25 (i, 4H), 7.38-7.21 (, 11H), 7.07-6.97 (m, 2H), 6.87 (dt, J=8.1, 1.8 Hz, 1H), 6.79 (s, 1H), 6.10 (d, J=8.4 Hz, 1H), 5.34 (dd, J=12.8, 5.4 Hz, 1H), 4.56-4.31 (o, 4H), 4.19 (dd, J=11.3, 5.7 Hz, 1H), 3.95 (d, J=14.3 Hz, 1H), 3.81 (s, 1H), 3.50-3.35 (N, 1H), 3.33 (s, 3H), 3.25-3.08 (m, 1H), 3.05-2.81 (3, 2H), 2.77-2.56 (m, 5H), 2.46-2.26 (m, 1H), 2.25-1.44 (m, 12H), 1.45-1.18 (m, 2H); MS (ESI, m(z): $[(M-1)]^-$=874.10.

The following intermediates in Table 53 were prepared according to the procedure of Step 4 of the procedure to prepare Intermediate G.

TABLE 53

Characterization data for intermediates prepared according to above.

| Intermediate | Structure | Chemical Name | MS: [(M + 1)]+ | 1H NMR |
|---|---|---|---|---|
| J74 | 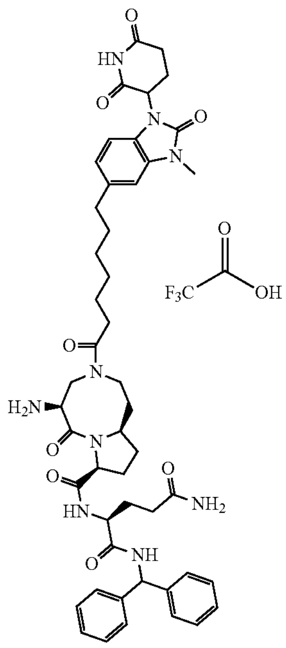 [SMILES: Cn1c(=O)n(C2CCC(=O)NC2=O)c2ccc(CCCCCCC(=O)N3CC[C@H]4CC[C@@H](C(=O)N[C@@H](CCC(N)=O)C(=O)NC(c5ccccc5)c5ccccc5)N4C(=O)[C@@H](N)C3)cc21 ; O=C(O)C(F)(F)F] | (2S)-2-[[(5S,8S,10aR)-5-amino-3-[7-[1-(2,6-dioxopiperidin-3-yl)-3-methyl-2-oxo-1,3-benzodiazol-5-yl]heptanoyl]-6-oxo-octahydropyrrolo[1,2-a][1,5]diazocin-8-yl]formamido]-N-(diphenylmethyl)-pentanediamide; trifluoroacetic acid | 890.6 | (400 MHz, DMSO-$d_6$) δ 11.09 (s, 1H), 8.85 (t, J = 8.0 Hz, 1H), 8.39-8.21 (m, 3H), 7.39-7.18 (m, 11H), 7.07-6.94 (m, 2H), 6.86 (d, J = 8.0 Hz, 1H), 6.81 (s, 1H), 6.11 (d, J = 8.4 Hz, 1H), 5.34 (dd, J = 12.8, 5.4 Hz, 1H), 4.53-4.30 (m, 4H), 4.18 (d, J = 15.3 Hz, 1H), 3.96 (d, J = 14.1 Hz, 1H), 3.81 (d, J = 14.0 Hz, 1H), 3.56-3.33 (m, 1H), 3.27 (s, 3H), 3.28-3.08 (m, 1H), 3.04-2.83 (m, 1H), 2.78-2.68 (m, 1H), 2.68-2.57 (m, 4H), 2.50-2.24 (m, 2H), 2.25-2.05 (m, 3H), 2.05-1.85 (m, 3H), 1.85-1.65 (m, 4H), 1.65-1.43 (m, 4H), 1.34 (m, 4H). |
| J75 | 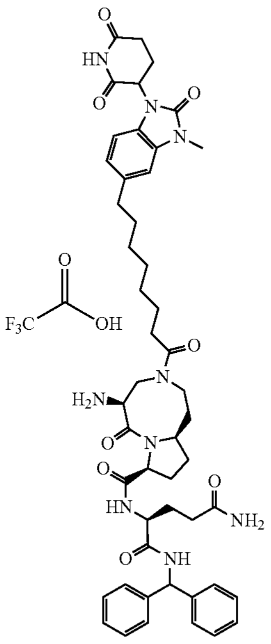 [SMILES: O=C(O)C(F)(F)F ; Cn1c(=O)n(C2CCC(=O)NC2=O)c2ccc(CCCCCCCC(=O)N3CC[C@H]4CC[C@@H](C(=O)N[C@@H](CCC(N)=O)C(=O)NC(c5ccccc5)c5ccccc5)N4C(=O)[C@@H](N)C3)cc21] | (2S)2-[[5S,8S,10aR)-5-amino-3-[8-(1-(2,6-dioxopiperidin-3-yl)-3-methyl-2-oxo-1,3-benzodiazol-5-yl]octanoyl]-6-oxo-octahydropyrrolo[1,2-a][1,5]diazocin-8-yl]formamido]-N-(diphenylmethyl)-pentanediamide; trifluoroacetic acid | 904.6 | (400 MHz, DMSO-$d_6$) δ 11.09 (s, 1H), 8.85 (t, J = 8.9 Hz, 1H), 8.31 (m, 3H), 7.40-7.29 (m, 4H), 7.26 (m, 7H), 7.05-6.97 (m, 2H), 6.86 (d, J = 8.1 Hz, 1H), 6.79 (s, 1H), 6.10 (d, J = 8.3 Hz, 1H), 5.34 (dd, J = 12.7, 5.4 Hz, 1H), 4.54-4.25 (m, 4H), 4.25-4.20 (m, 2H), 4.03-3.71 (m, 1H), 3.52-3.36 (m, 1H), 3.34 (s, 3H), 3.27-3.05 (m, 1H), 3.05-2.83 (m, 1H), 2.83-2.57 (m, 4H), 2.46-1.64 (m, 13H), 1.60-1.45 (m, 4H), 1.35-1.25 (m, 6H). |

TABLE 53-continued

Characterization data for intermediates prepared according to above.

| Intermediate | Structure | Chemical Name | MS: $[(M+1)]^+$ | $^1H$ NMR |
|---|---|---|---|---|
| J76 | 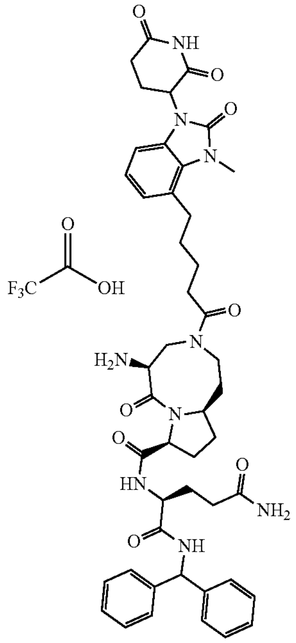 [SMILES: O=C(O)C(F)(F)F ; Cn1c(=O)n(C2CCC(=O)NC2=O)c2cccc(CCCCC(=O)N3CC[C@H]4CC[C@@H](C(=O)N[C@@H](CCC(N)=O)C(=O)NC(c5ccccc5)c5ccccc5)N4C(=O)[C@@H](N)C3)c21] | (2S)-2-[[5S,8S,10aR)-5-amino-3-[5-[1-(2,6-dioxopiperidin-3-yl)-3-methyl-2-oxo-1,3-benzodiazol-4-yl]pentanoyl]-6-oxo-octahydropyrrolo[1,2-a][1,5]diazocin-8-yl]formamido]-N-(diphenylmethyl)-pentanediamide; trifluoroacetic acid | 862.4 | (400 MHz, DMSO-$d_6$) δ 11.10 (s, 1H), 8.84 (t, J = 9.4 Hz, 1H), 8.36-5.24 (m, 4H), 7.39-7.17 (m, 11H), 7.04-6.93 (m, 2H), 6.88 (s, 1H), 6.78 (s, 1H), 6.10 (d, J = 8.1 Hz, 1H), 5.37 (dd, J = 12.6, 5.5 Hz, 1H), 4.51-4.33 (m, 4H), 4.26-4.12 (m, 1H), 3.96 (d, J = 14.1 Hz, 1H), 3.83 (d, J = 14.3 Hz, 1H), 3.58 (s, 3H), 3.51-3.38 (m, 1H), 3.27-3.06 (m, 1H), 3.03-2.82 (m, 5H), 2.79-2.51 (m, 3H), 2.50-2.31 (m, 2H), 2.25-2.05 (m, 2H), 1.96-1.59 (m, 9H). |
| J77 | 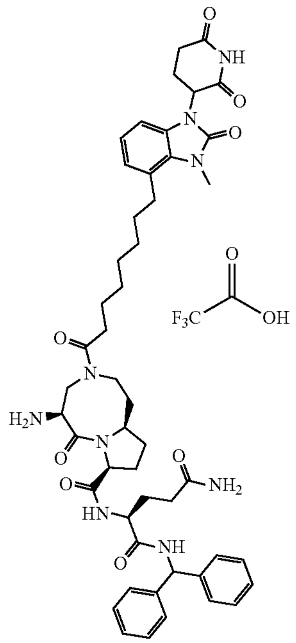 [SMILES: Cn1c(=O)n(C2CCC(=O)NC2=O)c2cccc(CCCCCCCC(=O)N3CC[C@H]4CC[C@@H](C(=O)N[C@@H](CCC(N)=O)C(=O)NC(c5ccccc5)c5ccccc5)N4C(=O)[C@@H](N)C3)c21 ; O=C(O)C(F)(F)F] | (2S)-2-[[(5S,8S,10aR)-5-amino-3-[8-[1-(2,6-dioxopiperidin-3-yl)-3-methyl-2-oxo-1,3-benzodiazol-4-yl]octanoyl]-6-oxo-octahydropyrrolo[1,2-a][1,5]diazocin-8-yl]formamido]-N-(diphenylmethyl)-pentanediamide; trifluoroacetic acid | 904.6 | (400 MHz, DMSO-$d_6$) δ 11.11 (s, 1H), 8.86 (t, J = 8.4 Hz, 1H), 8.37-8.23 (m, 4H), 7.40-7.19 (m, 11H), 7.04-6.93 (m, 2H), 6.86 (dd, J = 5.7, 3.3 Hz, 1H), 6.79 (s, 1H), 6.10 (d, J = 8.4 Hz, 1H), 5.37 (dd, J = 12.5, 5.4 Hz, 1H), 4.56-4.33 (m, 4H), 4.28-4.10 (m, 1H), 4.07-3.91 (m, 1H), 3.81 (d, J = 11.7 Hz, 1H), 3.64-3.58 (m, 1H), 3.55 (s, 3H), 3.47 (d, J = 15.4 Hz, 1H), 3.27-3.08 (m, 1H), 3.05-2.82 (m, 4H), 2.78-2.57 (m, 2H), 2.50-2.30 (m, 2H), 2.24-2.05 (m, 2H), 2.05-1.47 (m, 8H), 1.45-1.27 (m, 6H). |

TABLE 53-continued

| Characterization data for intermediates prepared according to above. | | | | |
|---|---|---|---|---|
| Intermediate | Structure | Chemical Name | MS: $[(M+1)]^+$ | $^1H$ NMR |
| J78 | 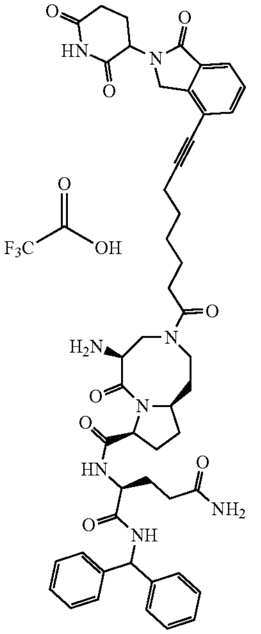 [SMILES: O=C(O)C(F)(F)F ; NC(=O)CC[C@H](NC(=O)[C@@H]1CC[C@@H]2CCN(C(=O)CCCCCC#Cc3cccc4c3CN(C3CCC(=O)NC3=O)C4=O)C[C@H](N)C(=O)N21)C(=O)NC(c1ccccc1)c1ccccc1] | (2S)-2-[[(5S,8S,10aR)-5-amino-3-[8-[2-(2,6-dioxopiperidin-3-yl)-1-oxo-3H-isoindol-4-yl]oct-7-ynoyl]-6-oxo-octahydropyrrolo[1,2-a][1,5]diazocin-8-yl]formamido]-N-(diphenylmethyl)-pentanediamide; trifluoroacetic acid | 885.6 | (400 MHz, DMSO-$d_6$) δ 11.01 (s, 1H), 8.85 (t, J = 8.7 Hz, 1H), 8.30 (m, 4H), 7.72 (dd, J = 7.5, 1.2 Hz, 1H), 7.63 (dd, J = 7.6, 1.1 Hz, 1H), 7.53 (td, J = 7.6, 1.5 Hz, 1H), 7.37-7.20 (m, 12H), 6.79 (s, 1H), 6.10 (d, J = 8.3 Hz, 1H), 5.16 (dd, J = 13.3, 5.1 Hz, 1H), 4.52-4.28 (m, 5H), 4.19 (dq, J = 16.2, 5.5, 4.8 Hz, 2H), 3.96 (d, J = 14.3 Hz, 1H), 3.82 (t, J = 14.0 Hz, 1H), 3.46 (d, J = 11.3 Hz, 1H), 3.27-3.06 (m, 1H), 3.06-2.83 (m, 2H), 2.66-2.55 (m, 2H), 2.50-2.27 (m, 2H), 2.27-1.39 (m, 16H). |
| J90 | 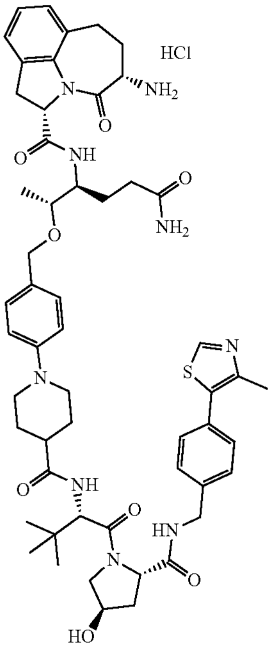 [SMILES: Cc1ncsc1-c1ccc(CNC(=O)[C@@H]2C[C@@H](O)CN2C(=O)[C@@H](NC(=O)C2CCN(c3ccc(CO[C@H](C)[C@H](CCC(N)=O)NC(=O)[C@@H]4Cc5cccc6c5N4C(=O)[C@@H](N)CC6)cc3)CC2)C(C)(C)C)cc1 ; Cl] | 1-[4-([[(2R,3S)-3-[[2S,11S)-11-amino-12-oxo-1-azatricyclo[6.4.1.0^[4,13]]trideca-4(13),5,7-trien-2-yl]formamido]-5-carbamoylpentan-2-yl]oxy]methyl)phenyl]-N-[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]piperidine-4-carboxamide hydrochloride | 1041.72 | Used in the next step without further purification |

TABLE 53-continued

| Characterization data for intermediates prepared according to above. | | | | |
|---|---|---|---|---|
| Intermediate | Structure | Chemical Name | MS: [(M + 1)]$^+$ | $^1$H NMR |
| J91 | 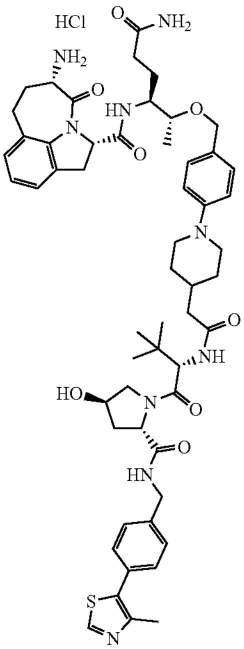 [SMILES: Cc1ncsc1-c1ccc(CNC(=O)[C@@H]2C[C@@H](O)CN2C(=O)[C@@H](NC(=O)CC2CCN(c3ccc(CO[C@H](C)[C@H](CCC(N)=O)NC(=O)[C@@H]4Cc5cccc6c5N4C(=O)[C@@H](N)CC6)cc3)CC2)C(C)(C)C)cc1 ; Cl] | (2S,4R)-1-[(2S)-2-(2-[1-[4-([[(2R,3S)-3-[[(2S,11S)-11-amino-12-oxo-1-azatricyclo[6.4.1.0^[4,13]]trideca-4(13),5,7-trien-2-yl]formamido]-5-carbamoylpentan-2-yl]oxy]methyl) phenyl]piperidin-4-yl]acetamido)-3,3-dimethylbutanoyl]-4-hydroxy-N-[[4-(4-methyl-1,3-thiazol-5-yl)phenyl]methyl] pyrrolidine-2-carboxamide hydrochloride | 1018.51 | (400 MHz, DMSO-$d_6$) δ 9.02 (s, 1H), 8.59 (t, J = 6.1 Hz, 1H), 8.48 (d, J = 16.6 Hz, 3H), 8.07 (d, J = 8.9 Hz, 1H), 7.79 (s, 1H), 7.45-7.38 (m, 6H), 7.23 (s, 1H), 7.10 (t, J = 8.2 Hz, 2H), 7.06-7.01 (m, 1H), 6.75 (s, 1H), 5.14 (dd, J = 10.9, 3.0 Hz, 1H), 4.58 (d, J = 9.3 Hz, 1H), 4.50-4.41 (m, 5H), 4.35 (d, J = 9.8 Hz, 2H), 4.25-4.19 (m, 5H) 3.84 (d, J = 4.6 Hz, 1H), 3.54-3.41 (m, 6H), 3.15 (t, J = 7.9 Hz, 2H), 2.86 (d, J = 16.2 Hz, 1H), 2.46 (s, 3H), 2.23 (d, J = 13.8 Hz, 2H), 2.23-2.03 (m, 6H), 1.97-1.71 (m, 6H), 1.61 (s, 1H), 1.11 (d, J = 6.3 Hz, 3H), 0.97 (s, 9H) |
| J92 | 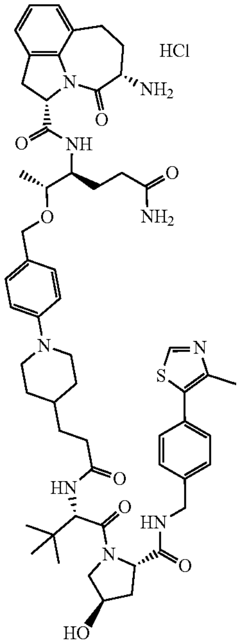 [SMILES: Cc1ncsc1-c1ccc(CNC(=O)[C@@H]2C[C@@H](O)CN2C(=O)[C@@H](NC(=O)CCC2CCN(c3ccc(CO[C@H](C)[C@H](CCC(N)=O)NC(=O)[C@@H]4Cc5cccc6c5N4C(=O)[C@@H](N)CC6)cc3)CC2)C(C)(C)C)cc1 ; Cl] | (2S,4R)-1-[(2S)-2-(3-11-[4-([[2R,3S)-3-[[(2S,11S)-11-amino-12-oxo-1-azatricyclo[6.4.1.0^[4,13]]trideca-4(13),5,7-trien-2-yl]formamido)-5-carbamoylpentan-2-yl]oxy]methyl) phenyl]piperidin-4-yl]propanamido)-3,3-dimethylbutanoyl]-4-hydroxy-N-[[4-(4-methyl-1,3-thiazol-5-yl)phenyl]methyl] pyrrolidine-2-carboxamide hydrochloride | 1032.80 | (400 MHz, DMSO-$d_6$) δ 9.02 (s, 1H), 8.60 (t, J = 6.1 Hz, 1H), 8.53-8.47 (m, 3H), 8.07 (d, J = 9.3 Hz, 1H), 7.98 (d, J = 9.3 Hz, 1H), 7.78 (s, 2H), 7.41 (q, J = 8.4 Hz, 7H), 7.16-6.96 (m, 3H), 6.75 (s, 1H), 5.14 (dd, J = 10.9, 3.1 Hz, 1H), 4.57 (d, J = 9.3 Hz, 1H), 4.53-4.40 (m, 3H), 4.39-4.31 (m, 1H), 4.30-4.17 (m, 6H), 3.90-3.77 (m, 2H), 3.72-3.66 (m, 2H), 3.54-3.42 (m, 2H), 3.17-3.13 (m, 1H), 2.86 (d, J = 16.7 Hz, 1H), 2.45 (s, 3H), 2.41-2.18 (m, 4H), 2.20-1.97 (m, 4H), 1.97-1.71 (m, 5H), 1.71-1.44 (m, 5H), 1.11 (d, J = 6.2 Hz, 3H), 0.96 (s, 9H) |

TABLE 53-continued

Characterization data for intermediates prepared according to above.

| Intermediate | Structure | Chemical Name | MS: $[(M+1)]^+$ | $^1H$ NMR |
|---|---|---|---|---|
| J93 | 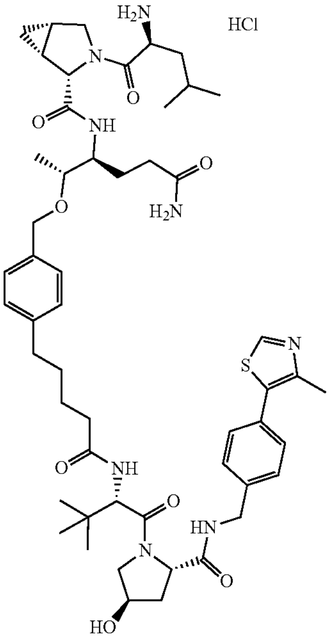 [SMILES: Cc1ncsc1-c1ccc(CNC(=O)[C@@H]2C[C@@H](O)CN2C(=O)[C@@H](NC(=O)CCCCc2ccc(CO[C@H](C)[C@H](CCC(N)=O)NC(=O)[C@@H]3[C@@H]4C[C@@H]4CN3C(=O)[C@@H](N)CC(C)C)cc2)C(C)(C)C)cc1 ; Cl] HCl | (2S,4R)-1-[(2S)-2-[5-[4-([[(2R,3S)-3-[[(1R,2S,5S)-3-[(2S)-2-amino-4-methylpentanoyl]-3-azabicyclo[3.1.0] hexan-2-yl]formamido]-5-carbamoylpentan-2-yl]oxy]methyl)-phenyl]pentanamido]-3,3-dimethylbutanoyl]-4-hydroxy-N-[[4-(4-methyl-1,3-thiazol-5-yl)phenyl]methyl] pyrrolidine-2-carboxainide hydrochloride | 971.35 | (400 MHz, DMSO-$d_6$) δ 9.05 (s, 1H), 8.59 (t, J = 6.1 Hz, 1H), 8.22-8.18 (m, 2H), 7.87-7.83 (m, 2H), 7.41 (q, J = 8.3Hz, 4H), 7.23 (d, J = 7.9 Hz, 2H), 7.14 (d, J = 7.7 Hz, 2H), 7.05 (s, 1H), 6.72 (s, 1H), 4.54 (d, J = 9.3 Hz, 1H), 4.50-4.39 (m, 4H), 4.34-4.30 (m, 4H), 3.94-3.92 (m, 2H), 3.79-3.61 (m, 2H), 3.47 (d, J = 9.9 Hz, 2H), 3.43-3.35 (m, 2H), 2.56 (t, J = 7.5 Hz, 1H), 2.45 (s, 3H), 2.39-2.25 (m, 1H), 2.12-2.05 (m, 3H), 1.96-1.73 (m, 2H), 1.55-1.50 (m, 7H), 1.18-1.05 (m, 4H), 0.93-0.87 (m, 16H), 0.68-0.65 (m, 1H), 0.63-0.56 (m, 1H). |
| J94 | 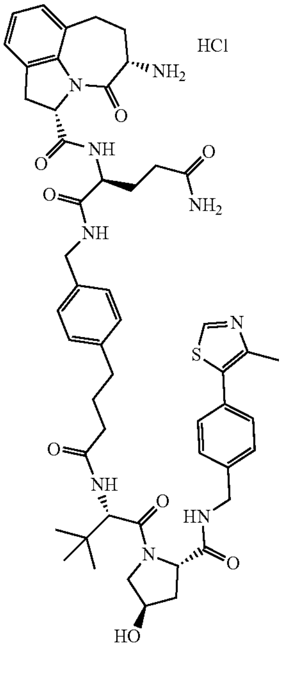 [SMILES: Cc1ncsc1-c1ccc(CNC(=O)[C@@H]2C[C@@H](O)CN2C(=O)[C@@H](NC(=O)CCCc2ccc(CNC(=O)[C@H](CCC(N)=O)NC(=O)[C@@H]3Cc4cccc5c4N3C(=O)[C@@H](N)CC5)cc2)C(C)(C)C)cc1 ; Cl] HCl | (2S)-2-[[2S,11S)-11-amino-12-oxo-1-azatricyclo[6.4.1.0^[4,13]]trideca-4(13),5,7-trien-2-yl]formamido]-N-[[4-(3-[[(2S)-1-[(2S,4R)-hydroxy-2-([[4-(4-methyl-1,3-thiazol-5-yl)phenyl]methyl] carbamoyl)pyrrolidin-1-yl]-3,3-dimethyl-1-oxobutan-2-yl]carbamoyl]propyl) phenyl]methyl] pentanediamide hydrochloride | 962.40 | (400 MHz, DMSO-$d_6$) δ 8.99 (s, 1H), 8.57 (t, J = 6.1 Hz, 1H), 8.33 (t, J = 5.9 Hz, 1H), 8.19 (d, J = 7.9 Hz, 1H), 7.92 (d, J = 9.3 Hz, 1H), 7.43-7.38 (m, 4H), 7.27 (s, 1H), 7.15-7.07 (m, 4H), 7.06-7.02 (m, 2H), 6.94 (t, J = 7.4 Hz, 1H), 6.76 (s, 1H), 5.15-5.06 (m, 2H), 4.56 (d, J = 9.4 Hz, 1H), 4.47-4.39 (m, 2H), 4.35 (s, 1H), 4.26-4.17 (m, 4H), 4.11 (q, J = 5.3 Hz, 1H), 3.67 (d, J = 3.6 Hz, 2H), 3.46 (dd, J = 9.5, 2.6 Hz, 1H), 3.33-3.29 (m, 2H), 3.17 (d, J = 5.0 Hz, 2H), 3.04 (d, J = 12.5 Hz, 2H), 2.97-2.92 (m, 1H), 2.45 (s, 3H), 2.35-2.26 (m, 1H), 2.20-2.13 (m, 1H), 2.15-2.08 (m, 2H), 2.05-1.96 (m, 2H), 1.94-1.86 (m, 3H), 1.82-1.72 (m, 3H), 0.95 (s, 9H) |

TABLE 53-continued

Characterization data for intermediates prepared according to above.

| Intermediate | Structure | Chemical Name | MS: $[(M + 1)]^+$ | $^1H$ NMR |
|---|---|---|---|---|
| J95 | 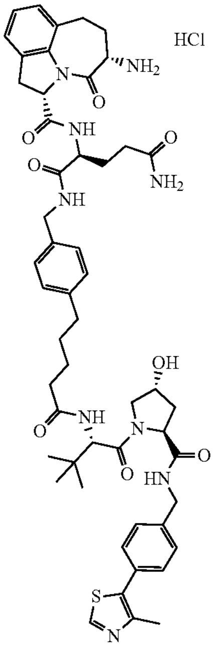 [SMILES: Cc1ncsc1-c1ccc(CNC(=O)[C@@H]2C[C@@H](O)CN2C(=O)[C@@H](NC(=O)CCCCc2ccc(CNC(=O)[C@H](CCC(N)=O)NC(=O)[C@@H]3Cc4cccc5c4N3C(=O)[C@@H](N)CC5)cc2)C(C)(C)C)cc1 ; Cl] | (2,S)-2-[[(2S,11S)-11-amino-12-oxo-1-azatricyclo[6.4.1.0^[4,13]]trideca-4(13),5,7-trien-2-yl]formamido]-N-[[4-(4-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl)butyl)phenyl]methyl]pentanediamide hydrochloride | 976.50 | (400 MHz, DMSO-$d_6$) δ 9.01 (s, 1H), 8.59 (t, J = 6.1 Hz, 1H), 8.45 (d, J = 14.8 Hz, 3H), 8.44-8.36 (m, 1H), 7.89 (d, J = 9.3 Hz, 1H), 7.41 (q, J = 8.4 Hz, 4H), 7.31 (s, 1H), 7.13-7.05 (m, 6H), 7.01 (t, J = 7.4 Hz, 1H), 6.80 (s, 1H), 5.17 (dd, J = 11.0, 3.0 Hz, 1H), 4.58-4.51 (m, 1H), 4.46-4.43 (m, 2H), 4.35 (s, 1H), 4.25-4.17 (m, 6H), 3.53-3.41 (m, 1H), 3.41-3.39 (m, 1H), 3.14 (d, J = 6.8 H,. 2H), 3.00-2.87 (m, 1H), 2.56-2.53 (m, 2H), 2.45 (s, 3H), 2.35-2.03 (m, 7H), 1.90-1.80 (m, 2H), 1.80-1 75 (m, 1H), 1.53-1.48 (m, 4H), 0.93 (s, 9H) |
| J96 | 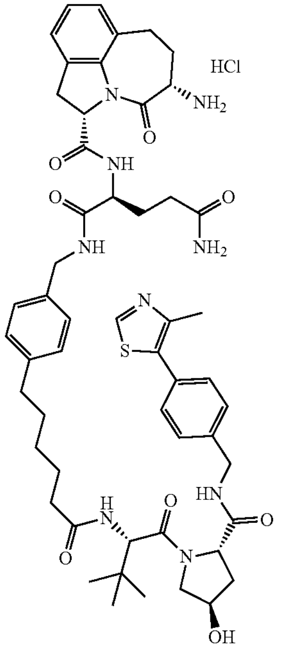 [SMILES: Cc1ncsc1-c1ccc(CNC(=O)[C@@H]2C[C@@H](O)CN2C(=O)[C@@H](NC(=O)CCCCCc2ccc(CNC(=O)[C@H](CCC(N)=O)NC(=O)[C@@H]3Cc4cccc5c4N3C(=O)[C@@H](N)CC5)cc2)C(C)(C)C)cc1 ; Cl] | (2S)-2-[[(2S,11S)-11-amino-12-oxo-1-azatricyclo[6.4.1.0^[4,13]]trideca-4(13),5,7-trien-2-yl]formamido]-N-[[4-(5-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]pentyl)phenyl]methyl]pentanediamide hydrochloride | 990.40 | (400 MHz, DMSO-$d_6$) δ 9.03 (s, 1H), 8.58 (m, J = 6.1 Hz, 1H), 8.51-8.38 (m, 4H), 7.86 (d, J = 9.3 Hz, 1H), 7.41 (m, J = 8.3 Hz, 4H), 7.31 (s, 1H), 7.13-7.06 (m, 6H), 7.01-6.99 (m, 1H), 6.80 (s, 1H), 5.17 (dd, J = 10.9, 3.0 Hz, 1H), 4.57-4.51 (m, 1H), 4.47-4.40 (m, 2H), 4.36-4.34 (m, 1H), 4.24-4.198 (m, 4H), 3.71-3.61 (m, 2H), 3.50-3.47 (m, 2H), 3.14 (d, J = 6.3 Hz, 2H), 2.96-2.94 (m, 1H), 2.45 (s, 3H), 2.36-2.00 (m, 9H), 1.91-1.89 (m, 2H), 1.84-1.75 (m, 1H), 1.53-1.48 (m, 4H), 1.29-1.22 (m, 3H), 0.93 (s, 9H) |

TABLE 53-continued

| Characterization data for intermediates prepared according to above. | | | | |
|---|---|---|---|---|
| Intermediate | Structure | Chemical Name | MS: [(M + 1)]+ | 1H NMR |
| J97 | 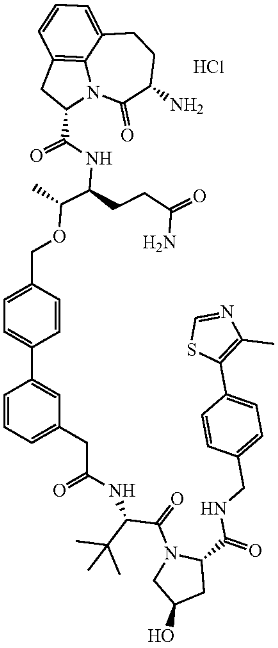 [SMILES: Cc1ncsc1-c1ccc(CNC(=O)[C@@H]2C[C@@H](O)CN2C(=O)[C@@H](NC(=O)Cc2cccc(-c3ccc(CO[C@H](C)[C@H](CCC(N)=O)NC(=O)[C@@H]4Cc5cccc6c5N4C(=O)[C@@H](N)CC6)cc3)c2)C(C)(C)C)cc1 ; Cl] | (2S,4R)-1-[(2S)-2-[2-[4-([[2R,3S)-3-[[(2S,11S)-11-amino-12-oxo-1-azatricyclo [6.4.1.0^[4,13]]trideca-4(13),5,7-trien-2-yl]formamido]-5-carbamoylpentan-2-yl]oxy]methyl)-[1,1-biphenyl]-3-yl]acetamido]-3,3-dimethylbutanoyl]-4-hydroxy-N-[[4-(4-methyl-1,3-thiazol-5-yl)phenyl]methyl] pyrrolidine-2-carboxamide hydrochloride | 1011.47 | (400 MHz, DMSO-$d_6$) δ 9.06 (s, 1H), 8.61 (t, J = 6.1 Hz, 1H), 8.51 (m, 3H), 8.19 (d, J = 9.4 Hz, 1H), 8.06 (d, J = 9.2 Hz, 1H), 7.59 (s, 1H), 7.55 (d, J = 8.0 Hz, 2H), 7.50 (d, J = 7.8 Hz, 1H), 7.46-7.37 (m, 6H), 7.35 (d, J = 8.1 Hz, 2H), 7.28 (d, J = 7.7 Hz, 1H), 7.07 (t, J = 6.3 Hz, 2H), 7.00 (t, J = 7.4 Hz, 1H), 6.76 (s, 1H), 5.15 (dd, J = 10.9, 3.1 Hz, 1H), 4.56 (d, J = 9.3 Hz, 2H), 4.50-4.46 (m, 4H), 4.43 (d, J = 7.0 Hz, 1H), 4.35 (s, 1H), 4.25 (d, J = 5.2 Hz, 1H), 4.21 (d, J = 5.4 Hz, 1H), 3.89-3.83 (m, 1H), 3.77 (d, J = 13.9 Hz, 1H), 3.68-3.63 (m, 2H), 3.14 (d, J = 6.1 Hz, 2H), 2.88 (d, J = 16.7 Hz, 1H), 2.46 (s, 3H), 2.24 (d, J = 13.1 Hz, 1H), 2.15-2.13 (m, 1H), 2.07-2.03 (m, 4H), 1.92-1.89 (m, 1H), 1.82-1.79 (m, 1H), 1.64-1.62 (m, 1H), 1.13 (d, J = 6.3 Hz, 3H), 0.94 (s, 9H) |
| J98 | 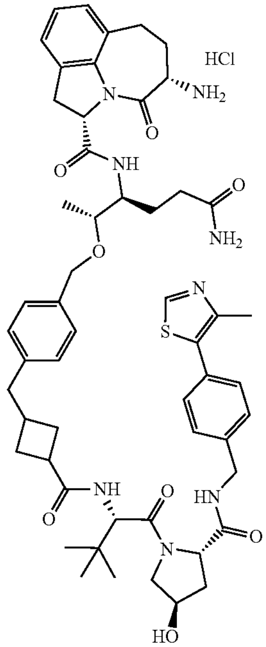 [SMILES: Cc1ncsc1-c1ccc(CNC(=O)[C@@H]2C[C@@H](O)CN2C(=O)[C@@H](NC(=O)C2CC(Cc3ccc(CO[C@H](C)[C@H](CCC(N)=O)NC(=O)[C@@H]4Cc5cccc6c5N4C(=O)[C@@H](N)CC6)cc3)C2)C(C)(C)C)cc1 ; Cl] | (2S,4R)-1-[(2S)-3,3-dimethyl-2-[[(1r,3r)-3-[[4-([[2R,3S)-3-[[(2S,11S)-11-amino-12-oxo-1-azatricyclo [6.4.1.0^[4,13]]trideca-4(13),5,7-trien-2-yl]formamido]-5-carbamoylpentan-2-yl]oxy]methyl) phenyl]methyl] cyclobutyl] formamido]butanoyl]-4-hydroxy-N-[[4-(4-methyl-1,3-thiazol-5-yl)phenyl]methyl] pyrrolidine-2-carboxamide hydrochloride | 1089.54 | (400 MHz, DMSO-$d_6$) δ 9.01 (d, J = 1.9 Hz, 1H), 8.57 (s, 1H), 8.01 (d, J = 9.3 Hz, 1H), 7.69 (d, J = 9.1 Hz, 1H), 7.46-7.35 (m, 4H), 7.19 (s, 1H), 7.14 (d, J = 7.8 Hz, 3H), 7.10-7.00 (m, 6H), 6.74 (s, 1H), 5.14 (s, 1H), 5.06 (dd, J = 10.8, 2.7 Hz, 1H), 4.55 (d, J = 9.4 Hz, 1H), 4.48-4.32 (m, 5H), 4.22 (dd, J = 15.9, 5.5 Hz, 1H), 4.05 (t, J = 8.7 Hz, 1H), 3.79 (s, 1H), 3.67 (s, 2H), 3.50-3.36 (m, 2H), 3.11-2.95 (m, 2H), 2.86 (d, J = 16.6 Hz, 1H), 2.65 (dd, J = 33.6, 7.6 Hz, 2H), 2.45 (s, 3H), 2.43-2.32 (m, 1H), 2.22-1.97 (m, 3H), 1.96-1.84 (m, 2H), 1.78 (q, J = 9.5 Hz, 2H), 1.58-1.54 (m, 1H), 1.40-1.38 (m, 2H), 1.25-1.23 (m, 1H), 1.08 (d, J = 6.3 Hz, 3H), 0.93 (s, 9H) |

TABLE 53-continued

| Characterization data for intermediates prepared according to above. | | | | |
|---|---|---|---|---|
| Intermediate | Structure | Chemical Name | MS: [(M + 1)]$^+$ | $^1$H NMR |
| J99 | 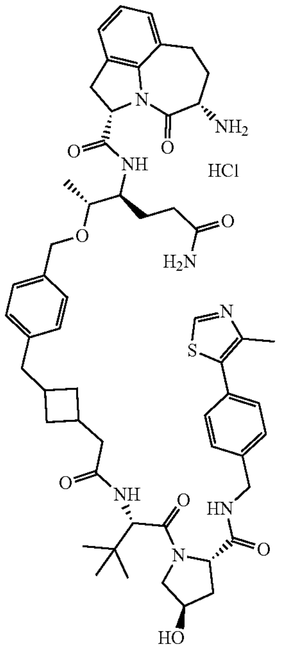 [SMILES: Cc1ncsc1-c1ccc(CNC(=O)[C@@H]2C[C@@H](O)CN2C(=O)[C@@H](NC(=O)CC2CC(Cc3ccc(CO[C@H](C)[C@H](CCC(N)=O)NC(=O)[C@@H]4Cc5cccc6c5N4C(=O)[C@@H](N)CC6)cc3)C2)C(C)(C)C)cc1 ; Cl] | (2S,4R)-1-[(2S)-2-[2-(3-[[4-([[(2R,3S)-3-[[(2S,11S)-11-amino-12-oxo-1-azatricyclo [6.4.1.0^[4,13]] trideca-4(13),5,7-trien-2-yl]formamido]-5-carbamoylpentan-2-yl]oxy]methyl)-phenyl]methyl]-cyclobutyl)acetamido]-3,3-dimethylbutanoyl]-4-hydroxy-N-[[4-(4-methyl-1,3-thiazol-5-yl)phenyl]methyl] pyrrolidine-2-carboxamide hydrochloride | 1003.35 | (400 MHz, $CD_3OD$) δ 9.96 (s, 1H), 7.62-7.51 (m, 4H), 7.25-7.18 (m, 2H), 7.13 (d, J = 7.4 Hz, 1H), 7.08 (dt, J = 11.6, 7.4 Hz, 4H), 5.20 (dd, J = 11.0, 3.5 Hz, 1H), 4.66-4.53 (m, 4H), 4.50 (s, 2H), 4.46-4.35 (m, 1H), 4.25-4.16 (m, 1H), 4.07-3.99 (m, 1H), 3.90 (d, J = 11.1 Hz, 1H), 3.85-3.73 (m, 1H), 3.68 (s, 3H), 3.66-3.55 (m, 2H), 3.55-3.46 (m, 1H), 3.27 (dd, J = 8.1, 4.7 Hz, 2H), 3.09-3.00 (m, 1H), 2.76 (d, J = 7.7 Hz, 1H), 2.66 (d, J = 7.3 Hz, 1H), 2.62 (s, 3H), 2.54-2.16 (m, 6H), 2.14-1.97 (m, 1H), 1.96-1.81 (m, 1H), 1.78-1.65 (m, 1H), 1.59-1.41 (m, 2H), 1.31 (s, 1H), 1.21 (s, 3H), 1.04 (s, 9H) |
| J100 | 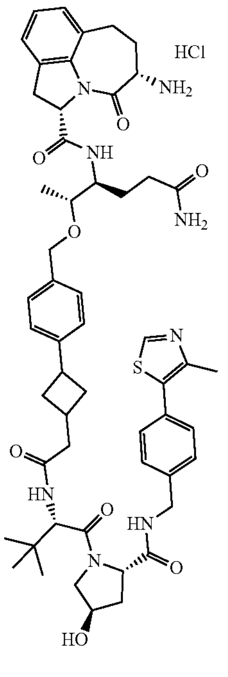 [SMILES: Cc1ncsc1-c1ccc(CNC(=O)[C@@H]2C[C@@H](O)CN2C(=O)[C@@H](NC(=O)CC2CC(c3ccc(CO[C@H](C)[C@H](CCC(N)=O)NC(=O)[C@@H]4Cc5cccc6c5N4C(=O)[C@@H](N)CC6)cc3)C2)C(C)(C)C)cc1 ; Cl] | (2S,4R)-1-[(2S,)-2-(2-[3-[4-([[2R,3S)-3-[[(2S,11S)-11-amino-12-oxo-1-azatricyclo [6.4.1.0^[4,13]] trideca-4(13),5,7-trien-2-yl]formamido]-5-carbamoylpentan-2-yl]oxy]methyl)-phenyl]cyclobutyl] acetamido)-3,3-dimethylbutanoyl]-4-hydroxy-N-[[4-(4-methyl-1,3-thiazol-5-yl)phenyl]methyl] pyrrolidine-2-carboxamide hydrochloride | 989.05 | (400 MHz, $CD_3OD$) δ 9.99 (dd, J = 5.1. 2.0 Hz, 1H), 7.63-7.51 (m, 4H), 7.29-7.02 (m, 7H), 5.20 (ddd, J = 11.1, 3.6, 1.6 Hz, 1H), 4.67 (d, J = 4.7 Hz, 1H), 4.64-4.36 (m, 6H), 4.25-4.16 (m, 1H), 4.07-3.99 (m, 1H), 3.93 (d, J = 11.0 Hz, 1H), 3.89-3.67 (m, 2H), 3.63 (d, J = 12.5 Hz, 1H), 3.60-3.46 (m, 1H), 3.42-3.33 (m, 1H), 3.30-3.23 (m, 3H), 3.08-2.97 (m, 1H), 2.74-2.62 (m, 1H), 2.62 (s, 3H), 2.61-2.50 (m, 1H), 2.49-2.20 (m, 6H), 2.15-1.97 (m, 2H), 1.88-1.84 (m, 1H), 1.79-1.67 (m, 1H), 1.59-1.55 (m, 1H), 1.21 (s, 3H), 1.06 (s, 9H) |

TABLE 53-continued

Characterization data for intermediates prepared according to above.

| Intermediate | Structure | Chemical Name | MS: $[(M + 1)]^+$ | $^1H$ NMR |
|---|---|---|---|---|
| J101 | 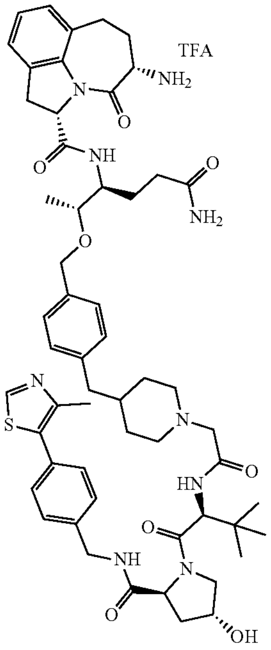 [SMILES: Cc1ncsc1-c1ccc(CNC(=O)[C@@H]2C[C@@H](O)CN2C(=O)[C@@H](NC(=O)CN2CCC(Cc3ccc(CO[C@H](C)[C@H](CCC(N)=O)NC(=O)[C@@H]4Cc5cccc6c5N4C(=O)[C@@H](N)CC6)cc3)CC2)C(C)(C)C)cc1 ; "TFA"] | (2S,4R)-1-[(2S)-2-[2-(4-[[4-([[2R,3S)-3-[[(2S,11S)-11-amino-12-oxo-1-azatricyclo [6.4.1.0^[4,13]] trideca-4(13),5,7-trien-2-yl]formamido]-5-carbamoylpentan-2-yl]oxy]methyl)-phenyl]-methyl]piperidin-1-yl)acetamido]-3,3-dimethylbutanoyl]-4-hydroxy-N-[[4-(4-methyl-1,3-thiazol-5-yl)phenyl]methyl] pyrrolidine-2-carboxamide trifluoroacetate | 1032.70 | (400 MHz, DMSO-$d_6$) δ 8.99 (s, 1H), 8.62 (t, J = 6.0 Hz, 1H), 8.33 (s, 1H), 7.78 (d, J = 9.7 Hz, 1H), 7.43 (s, 4H), 7.29-7.16 (m, 3H), 7.09 (d, J = 7.8 Hz, 2H), 6.85-6.50 (m, 2H), 4.53-4.23 (m, 8H), 3.83-3.52 (m, 5H), 3.50-3.38 (m, 6H), 3.10-2.67 (m, 5H), 2.49-2.44 (m, 4H), 2.12-1.98 (m, 4H), 1.95-1.67 (m, 3H), 1.66-1.42 (m, 5H), 1.42-1.36 (m, 3H), 1.24-1.20 (m, 3H), 1.06 (d, J = 6.0 Hz, 3H), 0.94 (s, 9H). |
| J102 | 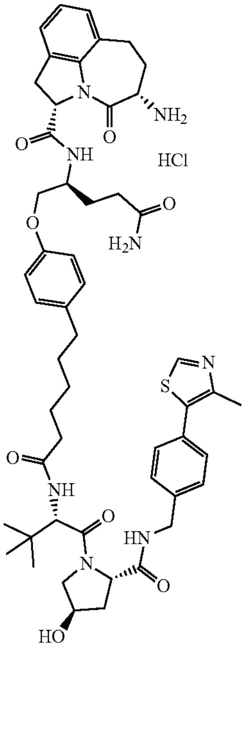 [SMILES: Cc1ncsc1-c1ccc(CNC(=O)[C@@H]2C[C@@H](O)CN2C(=O)[C@@H](NC(=O)CCCCCc2ccc(OC[C@H](CCC(N)=O)NC(=O)[C@@H]3Cc4cccc5c4N3C(=O)[C@@H](N)CC5)cc2)C(C)(C)C)cc1 ; Cl] | (2S,4R)-1-[(2S)-2-(6-[4-[(2S)-2-[[(2S,11S)-11-amino-12-oxo-1-azatricyclo [6.4.1.0^[4,13]] trideca-4(13),5,7-trien-2-yl]formamido]-4-carbamoylbutoxy] phenyl]hexanamido)-3,3-dimethylbutanoyl]-4-hydroxy-N-[[4-(4-methyl-1,3-thiazol-5-yl)phenyl]methyl] pyrrolidine-2-carboxamide hydrochloride | 963.35 | (400 MHz, DMSO-d6) δ 9.06 (s, 1H), 8.62-8.42 (m, 4H), 8.26 (d, J = 8.2 Hz, 1H), 7.85 (d, J = 9.3 Hz, 1H), 7.41 (q, J = 8.4 Hz, 4H), 7.13-6.94 (m, 6H), 6.85-6.74 (m, 2H), 5.10 (dd, J = 10.9, 3.0 Hz, 1H), 4.56-4.48 (m, 1H), 4.48-4.15 (m, 6H), 4.03-3.82 (m, 2H), 3.71-3.63 (m, 2H), 3.49-3.41 (m, 1H), 3.14 (d, J = 6.8 Hz, 2H), 2.88-2.84 (m, 1H), 2.46 (s, 3H), 2.32-1.98 (m, 6H), 1.98-1.66 (m, 4H), 1.58-1.42 (m, 6H), 1.32-1.24 (m, 4H), 0.93 (s, 9H) |

TABLE 53-continued

Characterization data for intermediates prepared according to above.

| Intermediate | Structure | Chemical Name | MS: $[(M + 1)]^+$ | $^1H$ NMR |
|---|---|---|---|---|
| J103 | 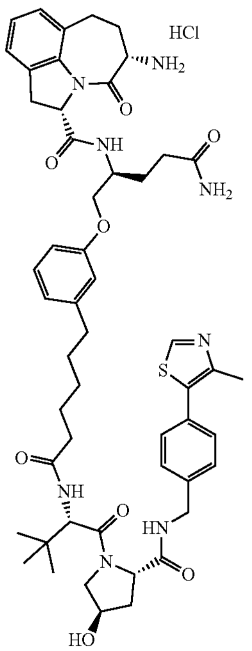 [SMILES: Cc1ncsc1-c1ccc(CNC(=O)[C@@H]2C[C@@H](O)CN2C(=O)[C@@H](NC(=O)CCCCCc2cccc(OC[C@H](CCC(N)=O)NC(=O)[C@@H]3Cc4cccc5c4N3C(=O)[C@@H](N)CC5)c2)C(C)(C)C)cc1 ; Cl] | (2S,4R)-1-[(2S)-2-(6-[3-[(2S)-2-[[(2S,11S)-11-amino-12-oxo-1-azatricyclo [6.4.1.0^[4,13]] trideca-4(13),5,7-trien-2-yl]formamido]-4-carbamoylbutoxy] phenyl]hexanamido)-3,3-dimethylbutanoyl]-4-hydroxy-N-[[4-(4-methyl-1,3-thiazol-5-yl)phenyl]methyl] pyrrolidine-2-carboxamide hydrochloride | 963.42 | (400 MHz, DMSO-$d_6$) δ 9.04 (s, 1H), 8.57 (t, J = 6.0 Hz, 1H), 8.53-8.47 (m, 2H), 8.24 (d, J = 8.1 Hz, 1H), 7.84 (d, J = 9.3 Hz, 1H), 7.45-7.36 (m, 4H), 7.17 (dd, J = 8.8, 7.6 Hz, 1H), 7.08 (d, J = 7.7 Hz, 2H), 7.04-6.96 (m, 1H), 6.78-6.72 (m, 4H), 5.10 (dd, J = 10.9, 3.0 Hz, 1H), 4.54 (d, J = 9.3 Hz, 1H), 4.48-4.39 (m, 2H), 4.35 (s, 1H), 4.30-4.24 (m, 4H), 3.99-3.86 (m, 4H), 3.72-3.60 (m, 2H), 3.49-3.35 (m, 3H), 3.17-3.13 (m, 2H), 2.86 (d, J = 16.8 Hz, 1H), 2.45 (s, 3H), 2.32-1.99 (m, 4H), 1.96-1.65 (m, 3H), 1.63-1.40 (m, 4H), 1.34-1.17 (m, 3H), 1.10 (t, J = 7.0 Hz, 2H), 0.93 (s, 9H) |
| J104 | 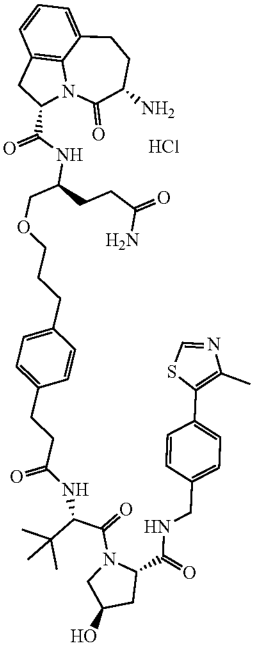 [SMILES: Cc1ncsc1-c1ccc(CNC(=O)[C@@H]2C[C@@H](O)CN2C(=O)[C@@H](NC(=O)CCc2ccc(CCCOC[C@H](CCC(N)=O)NC(=O)[C@@H]3Cc4cccc5c4N3C(=O)[C@@H](N)CC5)cc2)C(C)(C)C)cc1 ; Cl] | (2S,4R)-1-[(2S)-2-[3-(4-[3-[(2S)-2-[[(2S,11S)-11-amino-12-oxo-1-azatricyclo [6.4.1.0^[4,13]] trideca-4(13),5,7-trien-2-yl]formamido]-4-carbamoylbutoxy] propyl]phenyl) propanamido]-3,3-dimethylbutanoyl]-4-hydroxy-N-[[4-(4-methyl-1,3-thiazol-5-yl)phenyl]methyl] pyrrolidine-2-carboxamide hydrochloride | 963.21 | (400 MHz, DMSO-$d_6$) δ 9.00 (s, 1H), 8.57 (t, J = 6.0 Hz, 1H), 8.37 (s, 2H), 8.11-8.03 (m, 1H), 7.92 (d, J = 9.5 Hz, 1H), 7.41 (q, J = 8.3 Hz, 4H), 7.21 (s, 1H), 7.13 (d, J = 8.1 Hz, 2H), 7.07 (d, J = 7.8 Hz, 2H), 7.01-6.96 (m, 1H), 6.75 (s, 1H), 5.13-5.03 (m, 1H), 4.55 (d, J = 8.7 Hz, 1H), 4.48-4.38 (m, 2H), 4.36 (s, 1H), 4.25-4.20 (m, 3H), 3.80 (s, 1H), 3.66 (s, 2H), 3.62-3.54 (m, 5H), 3.41-3.30 (m, 2H), 3.15 (s, 2H), 2.93-2.74 (m, 3H), 2.57 (s, 2H), 2.45 (s, 3H), 2.18 (d, J = 12.5 Hz, 1H), 2.09 (d, J = 9.0 Hz, 4H), 1.96-1.86 (m, 1H), 1.79-1.69 (m, 2H), 1.50 (d, J = 85.9 Hz, 2H), 1.28-1.22 (m, 1H), 1.16-1.06 (m, 1H), 0.89 (s, 9H) |

TABLE 53-continued

| Intermediate | Structure | Chemical Name | MS: [(M + 1)]+ | $^1$H NMR |
|---|---|---|---|---|
| Characterization data for intermediates prepared according to above. | | | | |
| J105 | 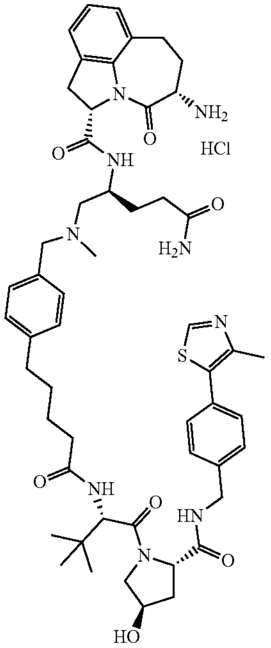 [SMILES: Cc1ncsc1-c1ccc(CNC(=O)[C@@H]2C[C@@H](O)CN2C(=O)[C@@H](NC(=O)CCCCc2ccc(CN(C)C[C@H](CCC(N)=O)NC(=O)[C@@H]3Cc4cccc5c4N3C(=O)[C@@H](N)CC5)cc2)C(C)(C)C)cc1 ; Cl] | (2S,4R)-1-[(2S)-2-[5-(4-([[(2S)-2-[[(2S,11S)-11-amino-12-oxo-1-azatricyclo [6.4.1.0^[4,13]] trideca-4(13),5,7-trien-2-yl]formamido]-4-carbamoylbutoxy]-(methyl)amino] methyl)phenyl] pentanamido]-3,3-dimethylbutanoyl]-4-hydroxy-N-[[4-(4-methyl-1,3-thiazol-5-yl)phenyl]methyl] pyrrolidine-2-carboxamide hydrochloride | 976.65 | (400 MHz, DMSO-$d_6$) δ 10.37 (d, J = 138.2 Hz, 1H), 9.01 (s, 1H), 8.64-8.40 (m, 5H), 7.88 (d, J = 9.3 Hz, 1H), 7.52 (dd, J = 12.7, 7.8 Hz, 2H), 7.41 (q, J = 8.2 Hz, 5H), 7.32-7.22 (m, 3H), 7.17-6.98 (m, 4H), 6.80 (s, 1H), 5.13-5.04 (m, 1H), 4.59-4.52 (m, 1H), 4.47-4.41 (m, 2H), 4.38-4.33 (m, 2H), 4.26-4.12 (m, 3H), 3.70-3.59 (m, 2H), 3.54-3.37 (m, 1H), 3.20-3.11 (m, 5H), 2.72-2.56 (m, 3H), 2.45 (s, 3H), 2.38-1.99 (m, 6H), 1.95-1.88 (m, 1H), 1.82-1.74 (m, 1H), 1.67-1.48 (m, 6H), 0.94 (s, 9H) |
| J106 | 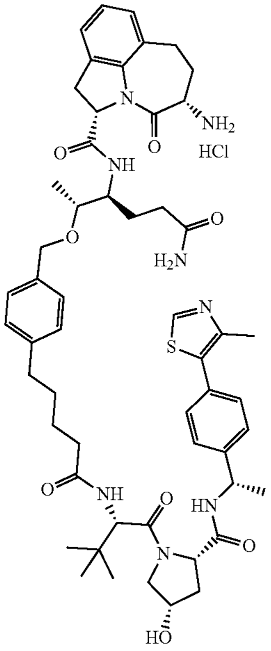 [SMILES: Cc1ncsc1-c1ccc([C@H](C)NC(=O)[C@@H]2C[C@H](O)CN2C(=O)[C@@H](NC(=O)CCCCc2ccc(CO[C@H](C)[C@H](CCC(N)=O)NC(=O)[C@@H]3Cc4cccc5c4N3C(=O)[C@@H](N)CC5)cc2)C(C)(C)C)cc1 ; Cl] | (2S,4R)-1-[(2S)-2-[5-[4-([[(2R,3S)-3-[[(2S,11S)-11-amino-12-oxo-1-azatricyclo [6.4.1.0^[4,13]] trideca-4(13),5,7-trien-2-yl]formamido]-5-carbamoylpentan-2-yl]oxy]methyl) phenyl]pentanamido]-3,3-dimethylbutanoyl]-4-hydroxy-N-[(1S)-1-[4-(4-methyl-1,3-thiazol-5-yl)phenyl]ethyl] pyrrolidine-2-carboxamide hydrochloride | 991.70 | (400 MHz, $CD_3OD$) δ 9.99 (s, 1H), 7.61-7.46 (m, 4H), 7.23 (d, J = 8.1 Hz, 2H), 7.17-7.02 (m, 5H), 5.20 (dd, J = 11.0, 3.6 Hz, 1H), 5.04 (q, J = 6.9 Hz, 1H), 4.58-4.50 (m, 3H), 4.50-4.46 (m, 1H), 4.38 (q, J = 4.6 Hz, 1H), 4.25-4.16 (m, 1H), 4.03 (dd, J = 10.5, 5.1 Hz, 2H), 3.64-3.47 (m, 2H), 3.27 (dd, J = 8.3, 4.7 Hz, 2H), 3.04 (dd, J = 16.8, 3.6 Hz, 1H), 2.63 (s, 3H), 2.47-2.21 (m, 5H), 2.05-1.95 (m, 1H), 1.90-1.86 (m, 1H), 1.70-1.64 (m, 9H), 1.62 (s, 1H), 1.53 (d, J = 7.0 Hz, 3H), 1.21 (d, J = 6.3 Hz, 3H), 1.06 (s, 9H) |

TABLE 53-continued

| Characterization data for intermediates prepared according to above. | | | | |
|---|---|---|---|---|
| Intermediate | Structure | Chemical Name | MS: $[(M + 1)]^+$ | $^1H$ NMR |
| J107 | 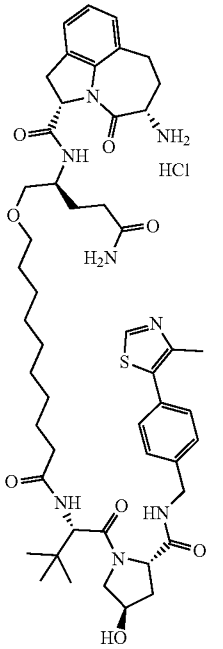 [SMILES: Cc1ncsc1-c1ccc(CNC(=O)[C@@H]2C[C@@H](O)CN2C(=O)[C@@H](NC(=O)CCCCCCCCCOC[C@H](CCC(N)=O)NC(=O)[C@@H]2Cc3cccc4c3N2C(=O)[C@@H](N)CC4)C(C)(C)C)cc1 ; Cl] | (2S,4R)-1-[(2S)-2-[10-[(2S)-2-[[2S,11S)-11-amino-12-oxo-1-azatricyclo[6.4.1.0^[4,13]]trideca-4(13),5,7-trien-2-yl]formamido]-4-carbamoylbutoxy]decanamido]-3,3-dimethylbutanoyl]-4-hydroxy-N-[[4-(4-methyl-1,3-thiazol-5-yl)phenyl]methyl]pyrrolidine-2-carboxamide hydrochloride | 943.15 | (400 MHz, DMSO-$d_6$) δ 9.08 (s, 1H), 8.64-8.42 (m, 4H), 8.05 (d, J = 8.5 Hz, 1H), 7.85 (d, J = 9.3 Hz, 1H), 7.47-7.35 (m, 5H), 7.09-7.06 (m, 2H), 7.04-6.94 (m, 1H), 5.08 (dd, J = 10.9, 3.0 Hz, 1H), 4.46-4.31 (m, 3H), 4.29-4.11 (m, 1H), 3.72-3.61 (m, 2H), 3.49-3.41 (m, 1H), 3.37-3.24 (m, 4H), 3.17-3.12 (m, 2H), 2.87 (dd, J = 17.0, 3.0 Hz, 1H), 2.46 (s, 3H), 2.31-2.23 (m, 2H), 2.17-1.97 (m, 5H), 1.94-1.87 (m, 1H), 1.77-1.67 (m, 1H), 1.55-1.39 (m, 1H), 1.28-1.20 (m, 18H), 0.94 (s, 9H) |
| J108 | 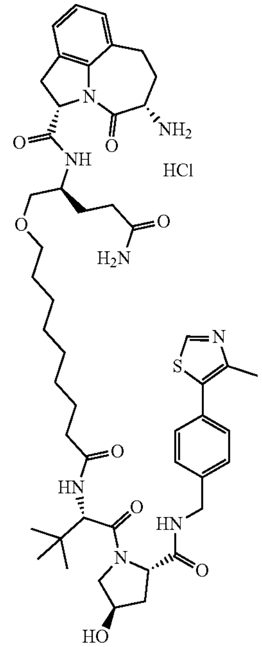 [SMILES: Cc1ncsc1-c1ccc(CNC(=O)[C@@H]2C[C@@H](O)CN2C(=O)[C@@H](NC(=O)CCCCCCCCOC[C@H](CCC(N)=O)NC(=O)[C@@H]2Cc3cccc4c3N2C(=O)[C@@H](N)CC4)C(C)(C)C)cc1 ; Cl] | (2S,4R)-1-[(2S)-2-[9-[(2S)-2-[[(2S,11S)-11-amino-12-oxo-1-azatricyclo[6.4.1.0^[4,13]]trideca-4(13),5,7-trien-2-yl]formamido-4-carbamoylbutoxy]nonanamido]-3,3-dimethylbutanoy]-4-hydroxy-N-[[4-(4-methyl-1,3-thiazol-5-yl)phenyl]methyl]pyrrolidine-2-carboxamide hydrochloride | 929.40 | (400 MHz, DMSO-$d_6$) δ 9.08 (s, 1H), 8.65-8.41 (m, 3H), 8.05 (d, J = 8.5 Hz, 1H), 7.85 (d, J = 9.2 Hz, 1H), 7.41 (q, J = 8.1 Hz, 4H), 7.04 (dt, J = 33.6, 7.4 Hz, 3H), 5.08 (dd, J = 11.1, 2.9 Hz, 1H), 4.55 (d, J = 9.1 Hz, 1H), 4.46-4.38 (m, 2H), 4.36-4.34 (m, 1H), 4.28-4.11 (m, 2H), 3.78-3.76 (m, 1H), 3.71-3.60 (m, 2H), 3.52-3.24 (m, 6H), 3.15-3.13 (m, 2H), 2.88 (d, J = 16.8 Hz, 1H), 2.46 (s, 3H), 2.28-2.24 (m, 2H), 2.13-2.08 (m, 4H), 1.91 (d, J = 6.4 Hz, 1H), 1.76-1.75 (m, 1H), 1.52-1.40 (m, 6H), 1.26-1.20 (m, 10H), 0.94 (s, 9H). |

TABLE 53-continued

Characterization data for intermediates prepared according to above.

| Intermediate | Structure | Chemical Name | MS: $[(M + 1)]^+$ | $^1$H NMR |
|---|---|---|---|---|
| J109 | 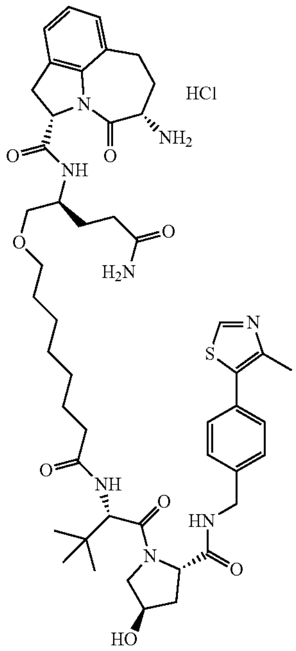 [SMILES: Cc1ncsc1-c1ccc(CNC(=O)[C@@H]2C[C@@H](O)CN2C(=O)[C@@H](NC(=O)CCCCCCCOC[C@H](CCC(N)=O)NC(=O)[C@@H]2Cc3cccc4c3N2C(=O)[C@@H](N)CC4)C(C)(C)C)cc1 ; Cl] | (3S,6S)-3-amino-N-((S)-5-amino-1-((8-(((S)-1-((2S,4R)-4-hydroxy-2-((4-(4-methylthiazol-5-yl)benzyl)carbamoyl) pyrrolidin-1-yl)-3,3-dimethyl-1-oxobutan-2-yl)amino)-8-oxooctyl)oxy)-5-oxopentan-2-yl)-4-oxo-1,2,3,4,6,7-hexahydroazepino[3,2,1-hi]indole-6-carboxamide hydrochloride | 915.50 | (400 MHz, DMSO-$d_6$) δ 9.01 (s, 1H), 8.62-8.33 (m, 3H), 8.03 (d, J = 8.4 Hz, 1H), 7.85 (d, J = 9.3 Hz, 1H), 7.41 (q, J = 8.3 Hz, 4H), 7.23 (s, 1H), 7.13-6.97 (m, 3H), 6.75(s, 1H), 5.08 (dd, J = 10.9, 3.0 Hz, 1H), 4.59-4.15 (m, 6H), 3.52-3.25 (m, 4H), 3.18-3.11 (m, 3H), 2.92-2.84 (m, 1H), 2.73-2.63 (m, 1H), 2.45 (s, 3H), 2.35-2.15 (m, 3H), 2.15-1.85 (m, 4H), 1.78-1.65 (m, 1H), 1.60-1.42 (m, 5H), 1.31-1.18 (m, 8H), 0.94 (s, 9H), 0.93-0.90 (m, 1H) |
| J110 | 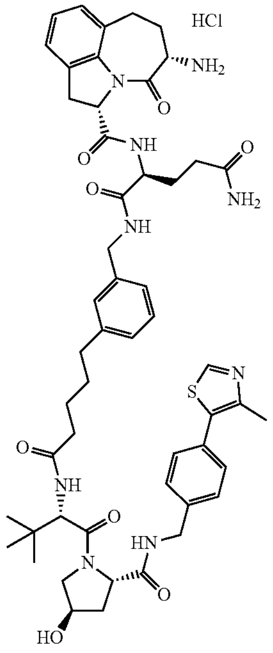 [SMILES: Cc1ncsc1-c1ccc(CNC(=O)[C@@H]2C[C@@H](O)CN2C(=O)[C@@H](NC(=O)CCCCc2cccc(CNC(=O)[C@H](CCC(N)=O)NC(=O)[C@@H]3Cc4cccc5c4N3C(=O)[C@@H](N)CC5)c2)C(C)(C)C)cc1 ; Cl] | (2S)-2-[[(2S,11S)-11-amino-12-oxo-1-azatricyclo [6.4.1.0^[4,13]] trideca-4(13),5,7-trien-2-yl]formamido]-N-[[3-(4-[[(2S)-1-[(2S,4R)-4-hydroxy-2-([[4-(4-methyl-1,3-thiazol-5-yl)phenyl]methyl] carbamoyl)pyrrolidin-1-yl]-3,3-dimethyl-1-oxobutan-2-yl]carbamoyl]butyl) phenyl]methyl]-pentanediamide hydrochloride | 976.43 | (300 MHz, DMSO-$d_6$) δ 9.02 (s, 1H), 8.60-8.35 (m, 7H), 7.86 (d, J = 9.3 Hz, 1H), 7.46-7.35 (m, 5H), 7.30 (s, 1H), 7.17 (t, J = 7.7 Hz, 1H), 7.10-6.99 (m, 8H), 6.78 (s, 1H), 5.17 (dd, J = 10.9, 3.0 Hz, 2H), 4.60-4.49 (m, 1H), 4.49-4.31 (m, 2H), 4.26-4.16 (m, 4H), 3.73-3.59 (m, 4H), 3.47-3.38 (m, 1H), 3.16-3.11 (m, 2H), 2.99-2.92 (m, 1H), 2.44 (s, 3H), 2.32-1.97 (m, 6H), 1.97-1.71 (m, 2H), 1.49 (d, J = 3.7 Hz, 4H), 0.93 (s, 9H) |

TABLE 53-continued

Characterization data for intermediates prepared according to above.

| Intermediate | Structure | Chemical Name | MS: $[(M + 1)]^+$ | $^1H$ NMR |
|---|---|---|---|---|
| J111 | 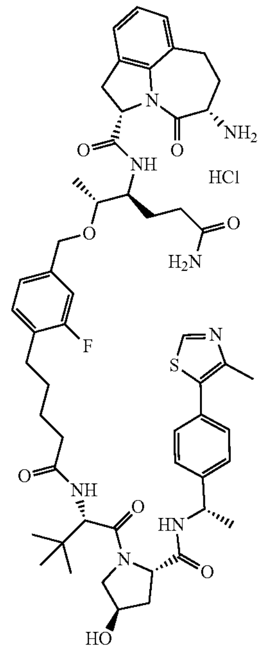 [SMILES: Cc1ncsc1-c1ccc([C@H](C)NC(=O)[C@@H]2C[C@@H](O)CN2C(=O)[C@@H](NC(=O)CCCCc2ccc(CO[C@H](C)[C@H](CCC(N)=O)NC(=O)[C@@H]3Cc4cccc5c4N3C(=O)[C@@H](N)CC5)cc2F)C(C)(C)C)cc1 ; Cl] | (2S,4R)-1-[(2S)-2-[5-[4-([[(2R,3S)-3-[[(2S,11S)-11-amino-12-oxo-1-azatricyclo [6.4.1.0^[4,13]] trideca-4(13),5,7-trien-2-yl]formamido]-5-carbamoylpentan-2-yl]oxy]methyl)-2-fluorophenyl] pentanamido]-3,3-dimethylbutanoyl]-4-hydroxy-N-[(1S)-1-(4-(4-methyl-1,3-thiazol-5-yl)phenyl]ethyl] pyrrolidine-2-carboxamide hydrochloride | 1109.45 | (400 MHz, DMSO-$d_6$) δ 9.01 (s, 1H), 8.41 (s, 3H), 8.04 (d, J = 9.4 Hz, 1H), 7.83 (d, J = 9.2 Hz, 1H), 7.44 (d, J = 7.9 Hz, 2H), 7.38 (d, J = 8.0 Hz, 2H), 7.22-7.14 (m, 2H), 7.03 (dd, J = 20.5, 7.2 Hz, 5H), 6.75 (s, 1H), 5.13 (d, J = 11.2 Hz, 1H), 4.92 (t, J = 7.1 Hz, 1H), 4.52 (d, J = 9.2 Hz, 1H), 4.43 (s, 3H), 4.28 (s, 1H), 4.24-4.16 (m, 2H), 3.51-3.39 (m, 2H), 3.15 (s, 2H), 2.85 (d, J = 16.6 Hz, 1H), 2.59 (s, 2H), 2.46 (s, 3H), 2.38-2.26 (m, 1H), 2.19-2.08 (m, 4H), 2.07-2.03 (m, 1H), 2.04-2.00 (m, 2H), 1.86-1.71 (m, 1H), 1.62-1.58 (m, 1H), 1.58-1.43 (m, 6H), 1.40-1.36 (m, 3H), 1.26-1.22 (m, 1H), 1.10 (d, J = 6.3 Hz, 3H), 0.93 (s, 9H) |
| J112 | 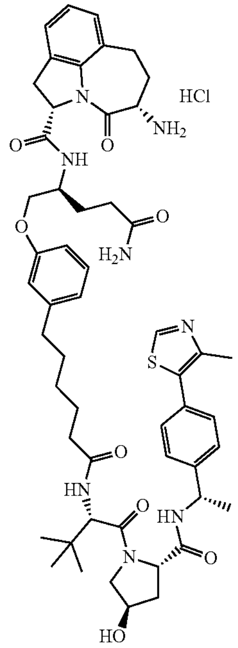 [SMILES: Cc1ncsc1-c1ccc([C@H](C)NC(=O)[C@@H]2C[C@@H](O)CN2C(=O)[C@@H](NC(=O)CCCCCc2cccc(OC[C@H](CCC(N)=O)NC(=O)[C@@H]3Cc4cccc5c4N3C(=O)[C@@H](N)CC5)c2)C(C)(C)C)cc1 ; Cl] | (2S,4R)-1-[(2S)-2-(6-[3-[(2S)-2-[[(2S,11S)-11-amino-12-oxo-1-azatricyclo [6.4.1.0^[4,13]] trideca-4(13),5,7-trien-2-yl]formamido]-4-carbamoylbutoxy] phenyl] hexanamido)-3,3-dimethylbutanoyl]-4-hydroxy-N-[(1S)-1-[4-(4-methyl-1,3-thiazol-5-yl)phenyl]ethyl] pyrrolidine-2-carboxamide hydrochloride | 977.55 | (400 MHz, $CD_3OD$) δ 10.02 (s, 1H), 7.56 (q, J = 8.2 Hz, 4H), 7.22-7.12 (m, 2H), 7.11-7.01 (m, 2H), 6.78 (m, 3H), 5.25-5.13 (m, 1H), 5.03 (q, J = 7.0 Hz, 1H), 4.65-4.55 (m, 2H), 4.44 (s, 1H), 4.30-4.16 (m, 3H), 4.08-3.96 (m, 2H), 3.89 (d, J = 10.9 Hz, 1H), 3.72-3.63 (m, 1H), 3.62 (d, J = 1.5 Hz, 1H), 3.53-3.47 (m, 1H), 3.27 (t, J = 6.6 Hz, 3H), 3.03 (d, J = 16.5 Hz, 1H), 2.63-2.56 (m, 3H), 2.49-2.15 (m, 4H), 2.05-2.01 (m, 1H), 1.97-1.89 (m, 1H), 1.62-1.57 (m, 5H), 1.53 (d, J = 7.0 Hz, 3H), 1.44-1.27 (m, 4H), 1.04 (s, 9H) |

TABLE 53-continued

Characterization data for intermediates prepared according to above.

| Intermediate | Structure | Chemical Name | MS: $[(M+1)]^+$ | $^1H$ NMR |
|---|---|---|---|---|
| J113 | 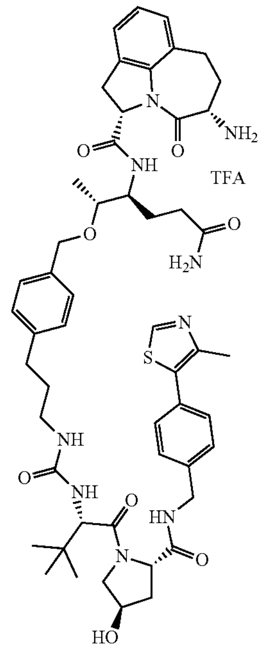 [SMILES: Cc1ncsc1-c1ccc(CNC(=O)[C@@H]2C[C@@H](O)CN2C(=O)[C@@H](NC(=O)NCCCc2ccc(CO[C@H](C)[C@H](CCC(N)=O)NC(=O)[C@@H]3Cc4cccc5c4N3C(=O)[C@@H](N)CC5)cc2)C(C)(C)C)cc1 ; "TFA"] | (2S,4R)-1-[(2S)-2-[([3-[4-([[(2R,3S)-3-[[(2S,11S)-11-amino-12-oxo-1-azatricyclo [6.4.1.0^[4,13]] trideca-4(13),5,7-trien-2-yl]formamido]-5-carbamoylpentan-2-yl]oxy]methyl) phenyl]propyl] carbamoyl) amino]-3,3-dimethylbutanoyl]-4-hydroxy-N-[[4-(4-methyl-1,3-thiazol-5-yl)phenyl]methyl] pyrrolidine-2-carboxamide trifluoroacetate | 978.70 | (400 MHz, DMSO-$d_6$) δ 9.00 (s, 1H), 8.58 (t, J = 6.1 Hz, 1H), 8.36 (s, 2H), 7.98 (s, 1H), 7.44-7.37 (m, 4H), 7.16 (d, J = 5.2 Hz, 4H), 7.12-7.07 (m, 5H), 6.14 (d, J = 9.7 Hz, 1H), 5.12 (dd, J = 11.0, 3.1 Hz, 2H), 4.41 (s, 4H), 4.36 (s, 1H), 4.27-4.19 (m, 1H), 3.86-3.82 (m, 1H), 3.48-3.44 (m, 3H), 3.15 (s, 2H), 3.00 (d, J = 8.9 Hz, 3H), 2.87 (dd, J = 17.4, 3.0 Hz, 1H), 2.55 (t, J = 7.5 Hz, 4H), 2.45 (s, 3H), 2.16-2.00 (m, 7H), 1.96-1.87 (m, 1H), 1.80-1.76 (m, 1H), 1.67-1.63 (m, 2H), 1.08 (s, 3H), 0.92 (s, 9H) |
| J114 | 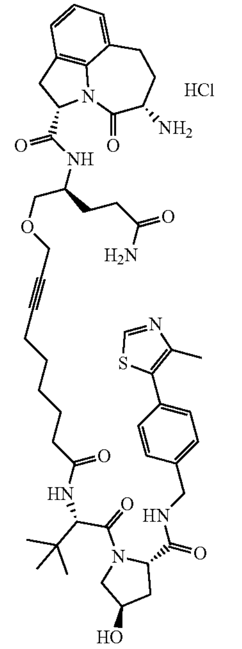 [SMILES: Cc1ncsc1-c1ccc(CNC(=O)[C@@H]2C[C@@H](O)CN2C(=O)[C@@H](NC(=O)CCCCCC#CCOC[C@H](CCC(N)=O)NC(=O)[C@@H]2Cc3cccc4c3N2C(=O)[C@@H](N)CC4)C(C)(C)C)cc1 ; Cl] | (2S,4R)-1-[(2S)-2-[9-[(2S)-2-[[(2S,11S)-11-amino-12-oxo-1-azatricyclo [6.4.1.0^[4,13]] trideca-4(13),5,7-trien-2-yl]formamido]-4-carbamoylbutoxy] non-7-ynamido]-3,3-dimethylbutanoyl]-4-hydroxy-N-[[4-(4-methyl-1,3-thiazol-5-yl)phenyl]methyl] pyrrolidine-2-carboxamide hydrochloride | 925.55 | (400 MHz, DMSO-$d_6$) δ 9.07 (s, 1H), 8.59 (t, J = 6.1 Hz, 1H), 8.54-8.50 (m, 2H), 8.18-8.06 (m, 1H), 7.88 (d, J = 9.3 Hz, 1H), 7.48-7.37 (m, 4H), 7.11-7.04 (m, 1H), 7.00 (t, J = 7.4 Hz, 1H), 6.72 (s, 1H), 5.08 (dd, J = 10.9, 3.1 Hz, 1H), 4.57-4.48 (m, 1H), 4.46-4.42 (m, 1H), 4.36-4.33 (m, 1H), 4.30-4.13 (m, 1H), 4.12-4.08 (m, 2H), 3.85-3.72 (m, 1H), 3.71-3.60 (m, 2H), 3.52-3.39 (m, 1H), 3.39-3.25 (m, 2H), 3.15-3.11 (m, 2H), 2.88 (dd, J = 17.0, 3.0 Hz, 1H), 2.46 (s, 3H), 2.36-2.01 (m, 13H), 1.92-1.87 (m, 1H), 1.76-1.72 (m, 1H), 1.67-1.56 (m, 1H), 1.47-1.43 (m, 4H), 1.38-1.30-1.26 (m, 2H), 0.94 (s, 9H) |

TABLE 53-continued

| Characterization data for intermediates prepared according to above. | | | | |
|---|---|---|---|---|
| Intermediate | Structure | Chemical Name | MS: $[(M+1)]^+$ | $^1H$ NMR |
| J115 | 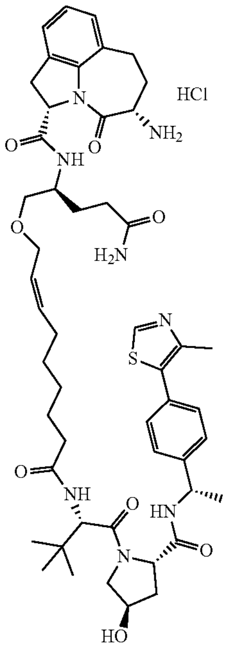 [SMILES: Cc1ncsc1-c1ccc([C@H](C)NC(=O)[C@@H]2C[C@@H](O)CN2C(=O)[C@@H](NC(=O)CCCCC/C=C\COC[C@H](CCC(N)=O)NC(=O)[C@@H]2Cc3cccc4c3N2C(=O)[C@@H](N)CC4)C(C)(C)C)cc1 ; Cl] | (2S,4R)-1-[(2S)-2-[(7Z)-9-[(2S)-2-[[(2S,11S)-11-amino-12-oxo-1-azatricyclo [6.4.1.0^[4,13]] trideca-4(13),5,7-trien-2-yl]formamido]-4-carbamoylbutoxy] non-7-enamido]-3,3-dimethylbutanoyl]-4-hydroxy-N-[[4-(4-methyl-1,3-thiazol-5-yl)phenyl]methyl] pyrrolidine-2-carboxamide hydrochloride | 927.40 | (400 MHz, DMSO-$d_6$) δ 9.11-9.03 (m, 1H), 8.58 (t, J = 6.0 Hz, 1H), 8.49 (s, 2H), 7.85 (dd, J = 9.3, 2.1 Hz, 1H), 7.40 (t, J = 7.4 Hz, 4H), 7.27 (s, 1H), 7.15-7.04 (m, 2H), 7.04-7.00 (m, 1H), 6.75 (s, 1H), 5.55-5.47 (m, 1H), 5.11-5.04 (m, 1H), 4.57-4.53 (m, 1H), 4.47-4.39 (m, 2H), 4.35 (s, 1H), 4.27-4.14 (m, 3H), 3.97 (d, J = 6.0 Hz, 1H), 3.76 (dd, J = 13.5, 5.0 Hz, 1H), 3.71-3.61 (m, 2H), 3.57 (s, 5H), 3.46-3.40 (m, 1H), 3.39 (q, J = 7.0 Hz, 1H), 3.36-3.28 (m, 1H), 3.13 (d, J = 6.3 Hz, 2H), 2.98-2.81 (m, 1H), 2.46 (s, 3H), 2.30-2.20 (m, 2H), 2.14-1.99 (m, 6H), 1.93-1.91 (m, 1H), 1.78-1.68 (m, 1H), 1.60 (s, 2H), 1.51-1.46 (m, 2H), 1.39-1.19 (m, 4H), 1.15-1.10 (m, 1H), 0.94 (s, 9H) |
| J116 | 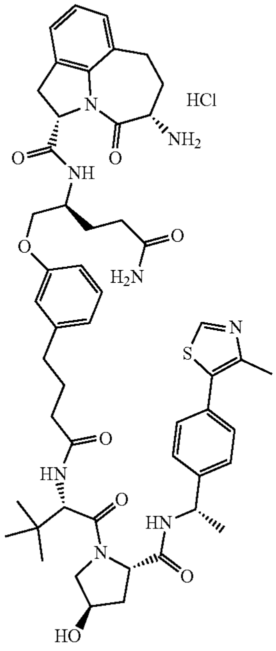 [SMILES: Cc1ncsc1-c1ccc([C@H](C)NC(=O)[C@@H]2C[C@@H](O)CN2C(=O)[C@@H](NC(=O)CCCc2cccc(OC[C@H](CCC(N)=O)NC(=O)[C@@H]3Cc4cccc5c4N3C(=O)[C@@H](N)CC5)c2)C(C)(C)C)cc1 ; Cl] | (2S,4R)-1-[(2S)-2-(4-[3-[(2S)-2-[[(2S,11S)-11-amino-12-oxo-1-azatricyclo [6.4.1.0^[4,13]] trideca-4(13),5,7-trien-2-yl]formamido]-4-carbamoylbutoxy] phenyl]butanamido)-3,3-dimethylbutanoyl]-4-hydroxy-N-[(1S)-1-[4-(4-methyl-1,3-thiazol-5-yl)phenyl]ethyl] pyrrolidine-2-carboxamide hydrochloride | 949.70 | (400 MHz, DMSO-$d_6$) δ 9.03 (s, 1H), 8.47 (s, 2H), 8.39 (d, J = 7.8 Hz, 1H), 8.25 (d, J = 8.1 Hz, 1H), 7.85 (d, J = 9.3 Hz, 1H), 7.44 (d, J = 8.2 Hz, 2H), 7.39 (d, J = 8.4 Hz, 2H), 7.27 (d, J = 15.6 Hz, 2H), 7.19 (t, J = 7.7 Hz, 1H), 7.10 (dd, J = 13.8, 6.9 Hz, 2H), 7.05-6.97 (m, 1H), 6.80-6.71 (m, 3H), 5.10 (dd, J = 10.9, 3.1 Hz, 1H), 4.96-4.88 (m, 1H), 4.54 (d, J = 9.3 Hz, 1H), 4.43 (t, J = 8.0 Hz, 1H), 4.35-4.14 (m, 4H), 3.97 (d, J = 13.8 Hz, 1H), 3.91 (s, 1H), 3.78-3.61 (m, 1H), 3.53-3.37 (m, 1H), 3.18-3.14 (m, 3H), 2.89-2.85 (m, 1H), 2.47 (s, 3H), 2.33-2.04 (m, 5H), 2.02-1.98 (m, 1H), 1.87-1.77 (m, 2H), 1.78-1.71 (m, 5H), 1.61-1.44 (m, 1H), 1.38 (d, J = 7.0 Hz, 3H), 0.95 (s, 9H) |

TABLE 53-continued

Characterization data for intermediates prepared according to above.

| Intermediate | Structure | Chemical Name | MS: $[(M + 1)]^+$ | $^1H$ NMR |
|---|---|---|---|---|
| J117 | 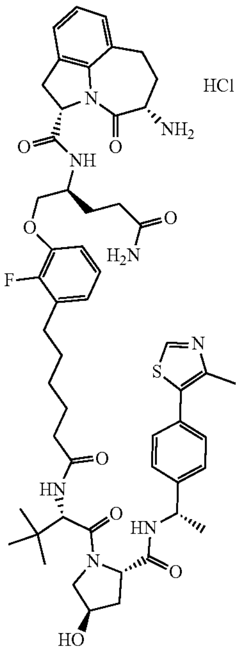 [SMILES: Cc1ncsc1-c1ccc([C@H](C)NC(=O)[C@@H]2C[C@@H](O)CN2C(=O)[C@@H](NC(=O)CCCCCc2cccc(OC[C@H](CCC(N)=O)NC(=O)[C@@H]3Cc4cccc5c4N3C(=O)[C@@H](N)CC5)c2F)C(C)(C)C)cc1 ; Cl] | (2S,4R)-1-[(2S)-2-(6-[3-[(2S)-2-[[(2S,11S)-11-amino-12-oxo-1-azatricyclo [6.4.1.0^[4,13]] trideca-4(13),5,7-trien-2-yl]formamido]-4-carbamoylbutoxy]-2-fluorophenyl] hexamido)-3,3-dimethylbutanoyl]-4-hydroxy-N-[(1S)-1-[4-(4-methyl-1,3-thiazol-5-yl)phenyl]ethyl] pyrrolidine-2-carboxamide hydrochloride | $[(M + 18)]^+$ = 995.23 | (400 MHz, DMSO-$d_6$) δ 9.01 (s, 1H), 8.46 (s, 1H), 8.44-8.35 (m, 2H), 8.27 (d, J = 7.5 Hz, 1H), 7.80 (d, J = 9.3 Hz, 1H), 7.48-7.35 (m, 3H), 7.27 (s, 1H), 7.10-6.97 (m, 6H), 6.87-6.77 (m, 2H), 5.11-5.07 (m, 1H), 4.92 (t, J = 7.1 Hz, 1H), 4.55-4.48 (m, 2H), 4.47-4.38 (m, 2H), 4.28 (s, 1H), 4.20 (d, J = 8.9 Hz, 2H), 3.73-3.59 (m, 1H), 3.53-3.37 (m, 1H), 3.14 (d, J = 5.1 Hz, 2H), 2.92-2.84 (m, 2H), 2.59-2.55 (m, 2H), 2.46 (s, 3H), 2.32-2.17 (m, 2H), 2.17-2.13 (m, 3H), 2.16-2.06 (m, 1H), 2.06-1.97 (m, 1H), 1.85-1.74 (m, 1H), 1.78-1.70 (m, 1H), 1.56-1.52 (m, 4H), 1.55-1.47 (m, 1H), 1.40-1.36 (m, 3H), 1.28 (s, 3H), 0.93 (s, 9H) |
| J118 | 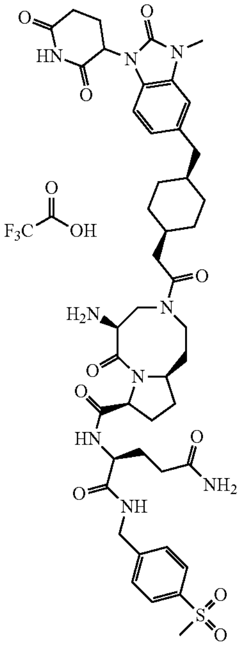 [SMILES: Cn1c(=O)n(C2CCC(=O)NC2=O)c2ccc(C[C@H]3CC[C@@H](CC(=O)N4CC[C@H]5CC[C@@H](C(=O)N[C@@H](CCC(N)=O)C(=O)NCc6ccc(S(C)(=O)=O)cc6)N5C(=O)[C@@H](N)C4)CC3)cc21 ; O=C(O)C(F)(F)F] | (2S)-2-[[(5S,8S,10aR)-5-amino-6-oxo-3-[2-[(1S,4S)-4-[[1-(2,6-dioxopiperidin-3-yl)-3-methyl-2-oxo-1,3-benzodiazol-5-yl]methyl] cyclohexyl]acetyl]-octahydropyrrolo[1,2-a][1,5]diazocin-8-yl]formamido]-N-[(4-methane-sulfonylphenyl) methyl] pentanediamide trifluoroacetate | 918.50 | (300 MHz, DMSO-$d_6$) δ 11.06 (s, 1H), 8.65-8.45 (m, 1H), 8.45-8.14 (m, 3H), 7.91-7.75 (m, 2H), 7.50 (dd, J = 8.3, 4.0 Hz, 2H), 7.22 (s, 1H), 7.08-6.92 (m, 2H), 6.92-6.71 (m, 2H), 5.33 (dd, J = 12.7, 5.4 Hz, 1H), 4.54-4.34 (m, 4H), 4.34-4.07 (m, 3H), 4.07-3.73 (m, 2H), 3.58-3.38 (m, 2H), 3.31 (s, 3H), 3.18 (s, 3H), 3.05-2.81 (m, 4H), 2.79-2.55 (m, 5H), 2.38-2.08 (m, 4H), 2.08-1.66 (m, 6H), 1.53-1.26 (m, 8H) |

TABLE 53-continued

Characterization data for intermediates prepared according to above.

| Intermediate | Structure | Chemical Name | MS: $[(M + 1)]^+$ | $^1H$ NMR |
|---|---|---|---|---|
| J119 | 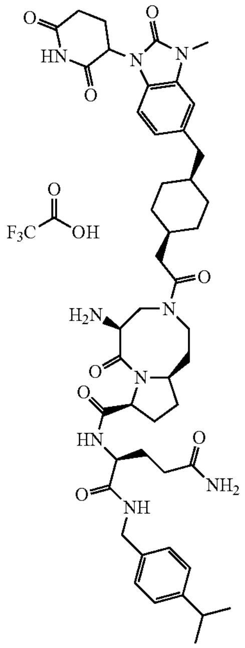 [SMILES: O=C(O)C(F)(F)F ; CC(C)c1ccc(CNC(=O)[C@H](CCC(N)=O)NC(=O)[C@@H]2CC[C@@H]3CCN(C(=O)C[C@H]4CC[C@@H](Cc5ccc6c(c5)n(C)c(=O)n6C5CCC(=O)NC5=O)CC4)C[C@H](N)C(=O)N32)cc1] | (2S)-2-[[(5S,8S,10aR)-5-amino-6-oxo-3-[2-[(1S,4S)-4-[[1-(2,6-dioxopiperidin-3-yl)-3-methyl-2-oxo-1,3-benzodiazol-5-yl]methyl]cyclohexyl]acetyl]-octahydropyrrolo[1,2-a][1,5]diazocin-8-yl]formamido]-N-[(4-isosulfonylphenyl)methyl]pentanediamide trifluoroacetate | 882.45 | (300 MHz, DMSO-$d_6$) δ 11.10 (s, 1H), 8.53-8.12 (m, 4H), 7.19 (d, J = 3.0 Hz, 5H), 7.09-6.96 (m, 2H), 6.84 (dd, J = 13.1, 6.0 Hz, 3H), 5.36 (dd, J = 12.8, 5.4 Hz, 1H), 4.60-4.11 (m, 6H), 4.11-3.71 (m, 1H), 3.56-3.44 (m, 1H), 3.34 (s, 3H), 3.283.06 (m, 1H), 3.03-2.82 (m, 2H), 2.81-2.58 (m, 4H), 2.39-1.61 (m, 15H), 1.61-1.29 (m, 9H), 1.20 (d, J = 5.8 Hz, 6H) |
| J120 | 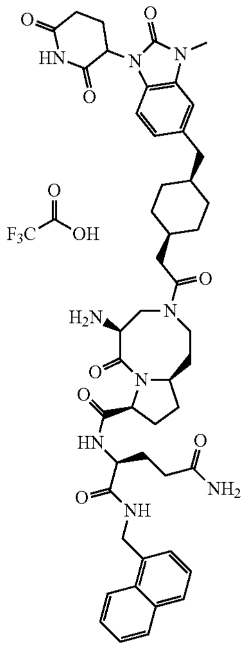 [SMILES: Cn1c(=O)n(C2CCC(=O)NC2=O)c2ccc(C[C@H]3CC[C@@H](CC(=O)N4CC[C@H]5CC[C@@H](C(=O)N[C@@H](CCC(N)=O)C(=O)NCc6cccc7ccccc67)N5C(=O)[C@@H](N)C4)CC3)cc21 ; O=C(O)C(F)(F)F] | (2S)-2-[[(5S,8S,10aR)-5-amino-6-oxo-3-[2-[(1S,4S)-4-[[1-(2,6-dioxopiperidin-3-yl)-3-methyl-2-oxo-1,3-benzodiazol-5-yl]methyl]cyclohexyl]acetyl]-octahydropyrrolo[1,2-a][1,5]diazocin-8-yl]formamido]-N-(naphthalen-1-ylmethyl)pentanediamide trifluoroacetate | 890.50 | (300 MHz, DMSO-$d_6$) δ 11.06 (s, 1H), 8.49-8.24 (m, 4H), 8.08-7.78 (m, 3H), 7.55-7.46 (m, 4H), 7.21 (s, 1H), 7.04-6.91 (m, 2H), 6.88-6.65 (m, 2H), 5.33 (dd, J = 12.7, 5.3 Hz, 1H), 5.33 (dd, J = 12.7, 5.3 Hz, 1H), 4.85-4.68 (m, 3H), 4.55-4.34 (m, 2H), 4.34-4.10 (m, 2H), 4.10-3.73 (m, 2H), 3.53-3.42 (m, 1H), 3.31 (s, 3H), 3.25-3.08 (m, 1H), 3.02-2.85 (m, 2H), 2.81-2.55 (m, 5H), 2.47-2.39 (m, 1H), 2.36-2.06 (m, 4H), 2.06-1.59 (m, 4H), 1.58-1.25 (m, 11H) |

TABLE 53-continued

Characterization data for intermediates prepared according to above.

| Intermediate | Structure | Chemical Name | MS: $[(M+1)]^+$ | $^1H$ NMR |
|---|---|---|---|---|
| J121 | 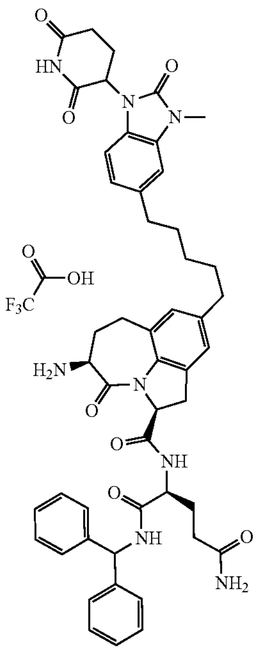 [SMILES: O=C(O)C(F)(F)F ; Cn1c(=O)n(C2CCC(=O)NC2=O)c2ccc(CCCCCc3cc4c5c(c3)C[C@@H](C(=O)N[C@@H](CCC(N)=O)C(=O)NC(c3ccccc3)c3ccccc3)N5C(=O)[C@@H](N)CC4)cc21] | (2S)-2-[[(2S,11S)-11-amino-6-[5-[1-(2,6-dioxopiperidin-3-yl)-3-methyl-2-oxo-1,3-benzodiazol-5-yl]pentyl]-12-oxo-1-azatricyclo [6.4.1.0^[4,13]] trideca-4(13),5,7-trien-2-yl]formamido]-N-(diphenylmethyl) pentanediamide trifluoroacetate | 867.75 | (300 MHz, Methanol-$d_4$) δ 7.39-7.14 (m, 10H), 7.00 (s, 2H), 6.96-6.87 (m, 3H), 6.15 (s, 1H), 5.32 (d, J = 11.8 Hz, 1H), 5.21 (d, J = 10.8 Hz, 1H), 4.49 (dd, J = 9 0, 5.0 Hz, 1H), 4.15 (d, J = 10.8 Hz, 1H), 3.40 (s, 3H), 3.21-3.16 (m, 1H), 3.13-2.75 (m, 3H), 2.69 (t, J = 7.4 Hz, 2H), 2.57 (t, J = 7.3 Hz, 2H), 2.48-2.07 (m, 4H), 2.00-1.91 (m, 1H), 1.75-1.59 (m, 4H), 1.40-1.31 (m, 6H), 0.95-0.87 (m, 1H) |
| J122 | 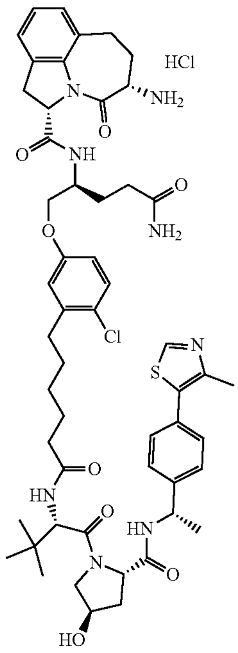 [SMILES: Cc1ncsc1-c1ccc([C@H](C)NC(=O)[C@@H]2C[C@@H](O)CN2C(=O)[C@@H](NC(=O)CCCCCc2cc(OC[C@H](CCC(N)=O)NC(=O)[C@@H]3Cc4cccc5c4N3C(=O)[C@@H](N)CC5)ccc2Cl)C(C)(C)C)cc1 ; Cl] | (2S,4R)-1-[(2S)-2-(6-[5-[(2S)-2-[[(11S)-11-amino-12-oxo-1-azatricyclo [6.4.1.0^[4,13]] trideca-4(13),5,7-trien-2-yl]fomiamido]-4-carbamoylbutoxy]-2-chlorophenyl] hexanamido)-3,3-dimethylbutanoyl]-4-hydroxy-N-[(1S)-1-[4-(4-methyl-1,3-thiazol-5-yl)phenyl]ethyl] pyrrolidine-2-carboxamide hydrochloride | 1011.70 | (300 MHz, DMSO-$d_6$) δ 9.04 (s, 1H), 8.48 (s, 3H), 8.40 (d, J = 7.8 Hz, 1H), 8.27 (d, J = 7.9 Hz, 1H), 7.81 (d, J = 8.9 Hz, 1H), 7.50-7.35 (m, 3H), 7.34-7.23 (m, 2H), 7.10 (d, J = 7.3 Hz, 3H), 7.06-6.96 (m, 1H), 6.91-6.76 (m, 2H), 5.10 (d, J = 10.9 Hz, 1H), 4.99-4.88 (m, 1H), 4.53 (d, J = 9.2 Hz, 1H), 4.20 (s, 1H), 3.97 (d, J = 8.0 Hz, 2H), 3.62-3.60 (m, 2H), 3.54-3.38 (m, 2H), 3.18-3.14 (m, 2H), 2.87-2.83 (m, 1H), 2.65-2.57 (m, 3H), 2.57-2.43 (m, 6H), 2.27-2.23 (m, 1H), 2.17-2.13 (m, 3H), 1.80-1.76 (m, 1H), 1.55-1.53 (m, 4H), 1.43-1.22 (m, 9H), 0.95 (s, 9H) |

TABLE 53-continued

Characterization data for intermediates prepared according to above.

| Intermediate | Structure | Chemical Name | MS: $[(M + 1)]^+$ | $^1H$ NMR |
|---|---|---|---|---|
| J123 | 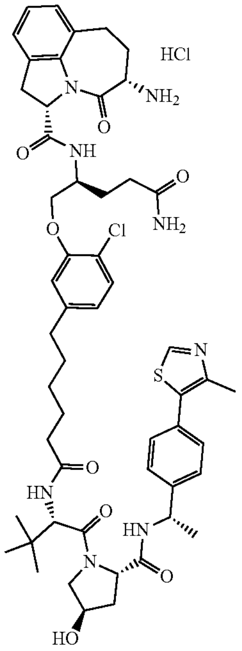 [SMILES: Cc1ncsc1-c1ccc([C@H](C)NC(=O)[C@@H]2C[C@@H](O)CN2C(=O)[C@@H](NC(=O)CCCCCc2ccc(Cl)c(OC[C@H](CCC(N)=O)NC(=O)[C@@H]3Cc4cccc5c4N3C(=O)[C@@H](N)CC5)c2)C(C)(C)C)cc1 ; Cl] | (2S,4R)-1-[(2S)-2-(6-[3-[(2S)-2-[[(2S,11S)-11-amino-12-oxo-1-azatricyclo [6.4.1.0^[4,13]] trideca-4(13),5,7-trien-2-yl]formamido]-4-carbamoylbutoxy]-4-chlorophenyl] hexanamido)-3.3-dimethylbutanoyl]-4-hydroxy-N-[(1S)-1-[4-(4-methyl-1,3-thiazol-5-yl)phenyl]ethyl] pyrrolidine-2-carboxamide | 1011.67 | (300 MHz, DMSO-$d_6$) δ 9.02 (s, 1H), 8.49-8.45 (m, 2H), 8.39 (d, J = 7.6 Hz, 1H), 7.79 (d, J = 9.3 Hz, 1H), 7.45-7.40 (m, 7H), 7.34-7.21 (m, 3H), 7.01 (d, J = 8.5 Hz, 1H), 6.79 (d, J = 7.6 Hz, 2H), 5.10 (d, J = 12.3 Hz, 1H), 4.54-4.50 (m, 1H), 4.33-4.22 (m, 3H), 4.06-4.04 (m, 2H), 3.73-3.61 (m, 3H), 3.53-3.37 (m, 1H), 3.18-3.14 (m, 2H), 3.04-2.93 (m, 1H), 2.45 (s, 3H), 2.47-2.38 (m, 3H), 2.24-2.09 (m, 2H), 1.83-1.73 (m, 4H), 1.64-1.48 (m, 6H), 1.39 (d, J = 7.1 Hz, 3H), 1.30-1.21 (m, 5H), 0.94 (s, 9H) |
| J124 | 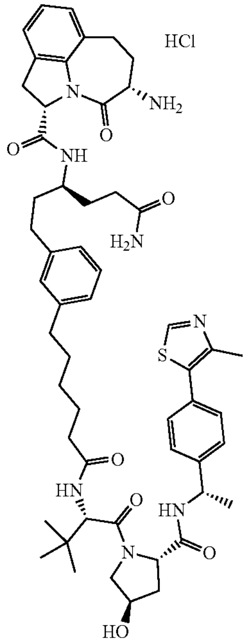 [SMILES: Cc1ncsc1-c1ccc([C@H](C)NC(=O)[C@@H]2C[C@@H](O)CN2C(=O)[C@@H](NC(=O)CCCCCc2cccc(CC[C@H](CCC(N)=O)NC(=O)[C@@H]3Cc4cccc5c4N3C(=O)[C@@H](N)CC5)c2)C(C)(C)C)cc1 ; Cl] | (2S,4R)-1-[(2S)-2-(6-[3-[(3R-3-[[(2S,11S)-11-amino-12-oxo-1-azatricyclo [6.4.1.0^[4,13]] trideca-4(13),5,7-trien-2-yl]formamido]-4-carbamoylpentyl] phenyl] hexanamido)-3,3-dimethylbutanoyl]-4-hydroxy-N-[(1S)-1-[4-(4-methyl-1,3-thiazol-5-yl)phenyl]ethyl] pyrrolidine-2-carboxamide | 975.80 | (300 MHz, DMSO-$d_6$) δ 9.07 (s, 1H), 8.58-8.43 (m, 2H), 8.38 (d, J = 7.7 Hz, 1H), 8.17-7.99 (m, 1H), 7.77 (d, J = 9.1 Hz, 1H), 7.41 (q, J = 8.4 Hz, 4H), 7.20-7.10 (m, 2H), 7.10-6.92 (m, 5H), 6.73 (s, 2H), 5.09 (dd, J = 10.9, 3.0 Hz, 1H), 4.91 (t, J = 7.2 Hz, 1H), 4.56-4.35 (m, 2H), 4.33-4.09 (m, 2H), 3.62-3.58 (m, 4H), 3.52-3.29 (m, 2H), 3.20-3.09 (m, 2H), 3.04-2.89 (m, 2H), 2.67 (m, 1H), 2.46 (s, 3H), 2.33-2.18 (m, 2H), 2.15-1.98 (m, 6H), 1.87-1.41 (m, 8H), 1.37 (d, J = 6.9 Hz, 4H), 1.33-1.17 (m, 2H), 0.93 (s, 9H) |

TABLE 53-continued

| Characterization data for intermediates prepared according to above. | | | | |
|---|---|---|---|---|
| Intermediate | Structure | Chemical Name | MS: $[(M + 1)]^+$ | $^1H$ NMR |
| J125 | 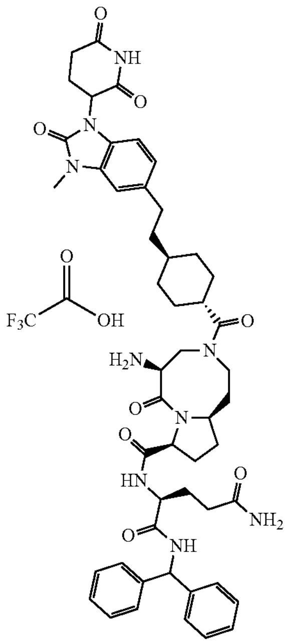 [SMILES: O=C(O)C(F)(F)F ; Cn1c(=O)n(C2CCC(=O)NC2=O)c2ccc(CC[C@H]3CC[C@H](C(=O)N4CC[C@H]5CC[C@@H](C(=O)N[C@@H](CCC(N)=O)C(=O)NC(c6ccccc6)c6ccccc6)N5C(=O)[C@@H](N)C4)CC3)cc21] | (2S)-2-[[(5S,8S,10aR)-5-amino-6-oxo-3-[(1r,4r)-4-[2-[1-(2,6-dioxopiperidin-3-yl)-3-methyl-2-oxo-1,3-benzodiazol-5-yl]ethyl]cyclohexanecarbonyl]-octahydropyrrolo[1,2-a][1,5]diazocin-8-yl]formamido]-N-(diphenylmethyl) pentanediamide trifluoroacetate | 916.45 | (400 MHz, DMSO-$d_6$) δ 11.08 (s, 1H), 8.85 (dd, J = 10.8, 8.5 Hz, 1H), 8.38-8.27 (m, 1H), 7.31-7.21 (m, 10H), 7.16 (d, J = 8.0 Hz, 2H), 7.04-6.97 (m, 2H), 6.87 (dd, 7 = 8.1, 1.6 Hz, 1H), 6.78 (s, 1H), 6.11 (d, J = 8.4 Hz, 1H), 5.34 (dd, J = 12.7, 5.4 Hz, 1H), 4.53-4.35 (m, 3H), 4.17 (s, 2H), 4.02-3.70 (m, 1H), 3.33 (s, 3H), 2.90 (td, J = 13.3, 6.8 Hz, 1H), 2.77-2.53 (m, 9H), 2.26-1.98 (m, 2H), 1.97-1.62 (m, 12H), 1.51 (q, J = 8.3 Hz, 3H), 1.28 (q, J = 10.7, 6.7 Hz, 2H), 1.17-0.98 (m, 2H) |
| J126 | 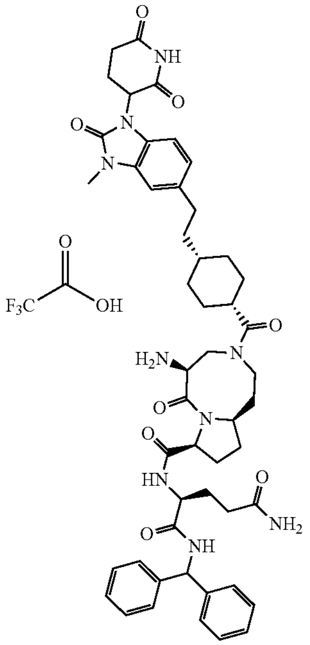 [SMILES: O=C(O)C(F)(F)F ; Cn1c(=O)n(C2CCC(=O)NC2=O)c2ccc(CC[C@H]3CC[C@@H](C(=O)N4CC[C@H]5CC[C@@H](C(=O)N[C@@H](CCC(N)=O)C(=O)NC(c6ccccc6)c6ccccc6)N5C(=O)[C@@H](N)C4)CC3)cc21] | (2S)-2-[[(5S,8S,10aR)-5-amino-6-oxo-3-[(1s,4s)-4-[2-[1-(2,6-dioxopiperidin-3-yl)-3-methyl-2-oxo-1,3-benzodiazol-5-yl]ethyl]cyclohexanecarbonyl]-octahydropyrrolo[1,2-a][1,5]diazocin-8-yl]formamido]-N-(diphenylmethyl) pentanediamide trifluoroacetate | 916.40 | (400 MHz, DMSO-$d_6$) δ 11.08 (s, 1H), 8.85 (t. J = 8.5 Hz, 1H), 8.38-8.20 (m, 1H), 7.30-7.19 (m, 10H), 7.16 (d, J = 8.0 Hz, 1H), 7.05-6.98 (m, 1H), 6.88 (d, J = 8.0 Hz, 1H), 6.78 (s, 1H), 6.11 (d, J = 8.4 Hz, 1H), 5.35 (dd, J = 12.8, 5.3 Hz, 1H), 4.52-4.37 (m, 2H), 4.52-4.37 (m, 1H), 4.01-3.72 (m, 1H), 3.50-3.38 (m, 1H), 3.34 (s, 3H), 3.19-3.05 (m, 1H), 3.03-2.85 (m, 2H), 2.78-2.55 (m, 8H), 2.37-2.28 (m, 2H), 2.23-1.84 (m, 4H), 1.83-1.37 (m, 17H) |

TABLE 53-continued

| Intermediate | Structure | Chemical Name | MS: [(M + 1)]+ | 1H NMR |
|---|---|---|---|---|
| Characterization data for intermediates prepared according to above. | | | | |
| J127 | 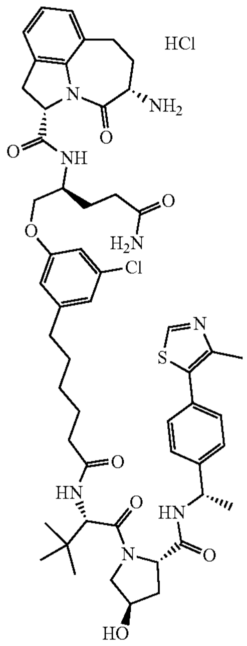 [SMILES: Cc1ncsc1-c1ccc([C@H](C)NC(=O)[C@@H]2C[C@@H](O)CN2C(=O)[C@@H](NC(=O)CCCCCc2cc(Cl)cc(OC[C@H](CCC(N)=O)NC(=O)[C@@H]3Cc4cccc5c4N3C(=O)[C@@H](N)CC5)c2)C(C)(C)C)cc1 ; Cl] | (2S,4R)-1-[(2S)-2-(6-[3-[(2S)-2-[[(2S,11S)-11-amino-12-oxo-1-azatricyclo [6.4.1.0^[4,13]] trideca-4(13),5,7-trien-2-yl]formamido]-4-carbamoylbutoxy]-5-chlorophenyl] hexanamido)-3,3-dimethylbutanoyl]-4-hydroxy-N-[(1S)-1-[4-(4-methyl-1,3-thiazol-5-yl)phenyl]ethyl] pyrrolidine-2-carboxamide | 1011.35 | (400 MHz, DMSO-$d_6$) δ 9.01 (s, 1H), 8.43 (s, 2H), 8.35 (d, J = 7.7 Hz, 1H), 8.21 (d, J = 7.7 Hz, 1H), 7.77 (d, J = 9.5 Hz, 1H), 7.47-7.32 (m, 3H), 7.25 (s, 1H), 7.07 (d, J = 7.4 Hz, 2H), 7.04-6.94 (m, 1H), 6.84 (s, 1H), 6.78 (d, J = 13.0 Hz, 2H), 6.70 (s, 1H), 5.08 (d, J = 10.1 Hz, 1H), 4.92 (d, J = 7.4 Hz, 1H), 4.51 (d, J = 9.3 Hz, 1H), 4.42 (t, J = 7.8 Hz, 1H), 4.32-4.25 (m, 1H), 4.23-4.17 (m, 1H), 3.94 (s, 3H), 3.50-3.35 (m, 2H), 3.17-3.11 (m, 2H), 2.84 (d, J = 16.1 Hz, 1H), 2.45 (s, 3H), 2.21 (d, J = 15.6 Hz, 3H), 2.15-2.04 (m, 3H), 2.03-1.96 (m, 1H), 1.89-1.70 (m, 3H), 1.61-1.44 (m, 5H), 1.37 (d, J = 7.0 Hz, 3H), 1.25 (d, J = 11.1 Hz, 5H), 0.92 (s, 9H) |
| J128 | 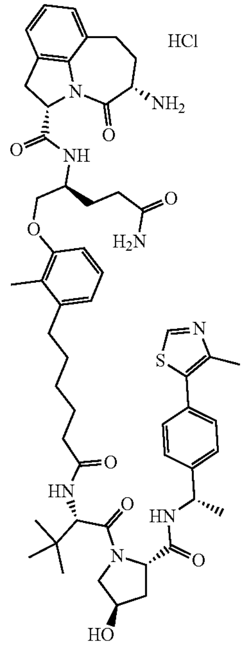 | (2S,4R)-1-[(2S)-2-(6-[3-[(2S)-2-[[(2S,11S)-11-amino-12-oxo-1-azatricyclo [6.4.1.0^[4,13]] trideca-4(13),5,7-trien-2-yl]formamido]-4-carbamoylbutoxy]-2-methylphenyl] hexanamido)-3,3-dimethylbutanoyl]-4-hydroxy-N-[(1S)-1-[4-(4-methyl-1,3-thiazol-5-yl)phenyl]ethyl] pyrrolidine-2-carboxamide | 991.35 | (400 MHz, DMSO-$d_6$) δ 9.09-9.06 (m, 1H), 8.54-8.51 (m, 3H), 8.40 (d, J = 7.6 Hz, 1H), 8.28 (d, J = 8.1 Hz, 1H), 7.81 (d, J = 9.3 Hz, 1H), 7.48-7.42 (m, 2H), 7.39 (d, J = 8.1 Hz, 2H), 7.11-6.95 (m, 4H), 6.75 (t, J = 7.5 Hz, 2H), 5.13-5.08 (m, 1H), 4.96-4.89 (m, 1H), 4.54-4.49 (m, 1H), 4.43 (t, J = 8.0 Hz, 1H), 4.28 (s, 1H), 4.25-4.11 (m, 2H), 4.05-4.01 (m, 1H), 3.94-3.83 (m, 2H), 3.67-3.59 (m, 3H), 3.44-3.39 (m, 1H), 3.17-3.14 (m, 2H), 2.85 (dd, J = 17.1, 3.1 Hz, 1H), 2.56-2.53 (s, 2H), 2.47 (s, 3H), 2.36-2.08 (m, 3H), 2.06 (s, 3H), 1.89-1.71 (m, 2H), 1.60-1.42 (m, 10H), 1.38 (d, J = 7.5 Hz, 3H), 1.35-1.29 (m, 1H), 0.94 (s, 9H) |

TABLE 53-continued

Characterization data for intermediates prepared according to above.

| Intermediate | Structure | Chemical Name | MS: $[(M + 1)]^+$ | $^1H$ NMR |
|---|---|---|---|---|
| J129 | 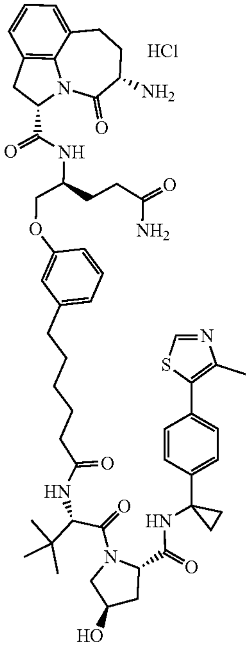 [SMILES: Cc1ncsc1-c1ccc(C2(NC(=O)[C@@H]3C[C@@H](O)CN3C(=O)[C@@H](NC(=O)CCCCCc3cccc(OC[C@H](CCC(N)=O)NC(=O)[C@@H]4Cc5cccc6c5N4C(=O)[C@@H](N)CC6)c3)C(C)(C)C)CC2)cc1 ; Cl] | (2S,4R)-1-[(2S)-2-(6-[3-[(2S)-2-amino-4-carbamoylbutoxy]phenyl]hexanamido)-3,3-dimethylbutanoyl]-4-hydroxy-N-[1-[4-(4-methyl-1,3-thiazol-5-yl)phenyl]cyclopropyl]pyrrolidine-2-carboxamide hydrochloride | 989.75 | (400 MHz, DMSO-$d_6$) δ 9.03 (s, 1H), 8.81 (s, 1H), 8.50-8.45 (m, 3H), 8.24 (d, J = 8.2 Hz, 1H), 7.90 (d, J = 9.2 Hz, 1H), 7.37-7.27 (m, 4H), 7.17 (t, J = 8.2 Hz, 1H), 7.07 (d, J = 4.4 Hz, 2H), 7.04-6.96 (m, 1H), 6.81-6.71 (m, 4H), 5.10 (dd, J = 10.9, 3.2 Hz, 1H), 4.62-4.52 (m, 1H), 4.39 (dd, J = 16.8, 8.7 Hz, 2H), 4.22-4.17 (m, 2H), 4.03-3.95 (m, 2H), 3.97-3.85 (m, 2H), 3.70-3.58 (m, 3H), 3.52-3.37 (m, 1H), 3.15 (s, 2H), 2.87 (d, J = 17.0 Hz, 1H), 2.45 (s, 3H), 2.45 (s, 2H), 2.33-2.17 (m, 2H), 2.14-2.10 (m, 3H), 2.05-1.96 (m, 1H), 1.94-1.82 (m, 1H), 1.76 (s, 1H), 1.82-1.72 (m, 2H), 1.54 (s, 2H), 1.55-1.52 (m, 1H), 1.32-1 16 (m, 4H), 1.16-1.12 (m, 1H), 0.94 (s, 9H) |
| J130 | 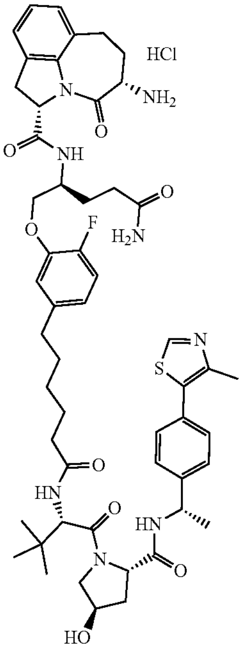 [SMILES: Cc1ncsc1-c1ccc([C@H](C)NC(=O)[C@@H]2C[C@@H](O)CN2C(=O)[C@@H](NC(=O)CCCCCc2ccc(F)c(OC[C@H](CCC(N)=O)NC(=O)[C@@H]3Cc4cccc5c4N3C(=O)[C@@H](N)CC5)c2)C(C)(C)C)cc1 ; Cl] | (2S,4R)-1-[(2S)-2-(6-[3-[(2S)-2-[[(11S)-11-amino-12-oxo-1-azatricyclo[6.4.1.0^[4,13]]trideca-4(13),5,7-trien-2-yl]formamido]-4-carbamoylbutoxy]-4-fluorophenyl]hexanamido)-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride | $[(M - 1)]^-$ = 993.15 | (400 MHz, DMSO-$d_6$) δ 9.01 (s, 1H), 8.47-8.34 (m, 3H), 8.26 (d, J = 7.5 Hz, 1H), 7.78 (d, J = 9.1 Hz, 1H), 7.44 (d, J = 8.2 Hz, 2H), 7.39 (d, J = 8.3 Hz, 2H), 7.26 (s, 1H), 7.13-7.04 (m, 3H), 7.04-6.96 (m, 2H), 6.76 (s, 2H), 5.13-5.06 (m, 1H), 4.91 (d, J = 7.1 Hz, 1H), 4.52 (d, J = 9.1 Hz, 1H), 4.45-4.41 (m, 1H), 4.29 (s, 1H), 4.20 (s, 1H), 4.04 (d, J = 8.6 Hz, 1H), 3.73-3.57 (m, 3H), 3.53-3.37 (m, 2H), 3.17-3.13 (m, 2H), 2.90-2.86 (m, 1H), 2.46 (s, 3H), 2.21-2.10 (m, 2H), 2.08 (s, 1H), 2.03-1.98 (m, 1H), 1.79 (d, J = 19.1 Hz, 3H), 1.59-1.49 (m, 4H), 1.41-1.34 (m, 4H), 1.25-1.20 (m, 7H), 0.93 (s, 9H) |

TABLE 53-continued

Characterization data for intermediates prepared according to above.

| Intermediate | Structure | Chemical Name | MS: [(M + 1)]+ | $^1$H NMR |
|---|---|---|---|---|
| J131 | 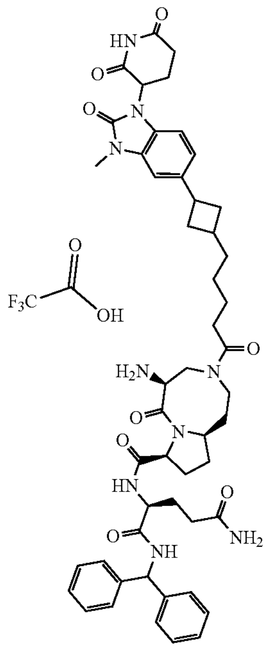 [SMILES: O=C(O)C(F)(F)F ; Cn1c(=O)n(C2CCC(=O)NC2=O)c2ccc(C3CC(CCCCC(=O)N4CC[C@H]5CC[C@@H](C(=O)N[C@@H](CCC(N)=O)C(=O)NC(c6ccccc6)c6ccccc6)N5C(=O)[C@@H](N)C4)C3)cc21] | (2S)-2-((5S,8S,10aR)-5-amino-3-(5-(3-(1-(2,6-dioxopiperidin-3-yl)-3-methyl-2-oxo-2,3-dihydro-1H-benzo[d]imidazol-5-yl)cyclobutyl) pentanoyl)-6-oxo-decahydropyrrolo[1,2-a][1,5]diazocine-8-carboxamido]-N1-benzhydryl-pentanediamide trifluoroacetate | 916.35 | (400 MHz, DMSO-$d_6$) δ 11.08 (s, 1H), 8.73 (dd, J = 8.6, 3.3 Hz, 1H), 8.26-8.08 (m, 2H), 7.36-7.24 (m, 13H), 7.12-6.96 (m, 2H), 6.90 (dd, J = 21.6, 8.1 Hz, 1H), 6.73 (d, J = 9.2 Hz, 1H), 6.10 (d, J = 8.4 Hz, 1H), 5.34 (dd, J = 12.9, 5.2 Hz, 1H), 4.43-4.28 (m, 3H), 4.19-3.40 (m, 6H), 3.34 (s, 3H), 3.28-3.10 (m, 1H), 3.05-2.79 (m, 2H), 2.75-2.61 (m, 3H), 2.48-1.47 (m, 16H), 1.45-1.40 (m, 1H), 1.34-1.23 (m, 3H) |
| J132 | 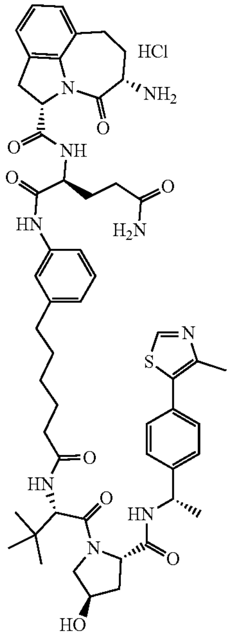 [SMILES: Cc1ncsc1-c1ccc([C@H](C)NC(=O)[C@@H]2C[C@@H](O)CN2C(=O)[C@@H](NC(=O)CCCCCc2cccc(NC(=O)[C@H](CCC(N)=O)NC(=O)[C@@H]3Cc4cccc5c4N3C(=O)[C@@H](N)CC5)c2)C(C)(C)C)cc1 ; Cl] | (2S)-2-[[(2S,11S)-11-amino-12-oxo-1-azatricyclo [6.4.1.0^[4,13]] trideca-4(13),5,7-trien-2-yl]formamido]-N-[3-(5-[[(2S)-1-[(2S,4R)-4-hydroxy-2-[[(1S)-1-[4-(4-methyl-1,3-thiazol-5-yl)phenyl]ethyl] carbamoyl] pyrrolidin-1-yl]-3,3-dimethyl-1-oxobutan-2-yl]carbamoyl]pentyl) phenyl] pentanediamide hydrochloride | 990.60 | (300 MHz, DMSO-$d_6$) δ 10.01 (s, 1H), 9.00 (s, 1H), 8.55-8.28 (m, 5H), 7.76 (d, J = 9.1 Hz, 1H), 7.45-7.36 (m, 7H), 7.23-6.91 (m, 4H), 6.87 (d, J = 7.6 Hz, 1H), 6.79 (s, 1H), 5.22-5.17 (m, 5H), 4.91 (t, J = 7.1 Hz, 1H), 4.50 (d, J = 9.3 Hz, 1H), 4.42 (t, J = 8.0 Hz, 1H), 4.36-4.10 (m, 3H), 3.59 (s, 4H), 3.52-3.37 (m, 1H), 3.16-3.11 (m, 2H), 3.03-2.96 (m, 1H), 2.45 (s, 3H), 2.31-1.69 (m, 6H), 1.59-1.45 (m, 3H), 1.37 (d, J = 7.0 Hz, 3H), 1.32-1.18 (m, 3H), 0.92 (s, 9H) |

TABLE 53-continued

| Characterization data for intermediates prepared according to above. | | | | |
|---|---|---|---|---|
| Intermediate | Structure | Chemical Name | MS: [(M + 1)]+ | 1H NMR |
| J133 | 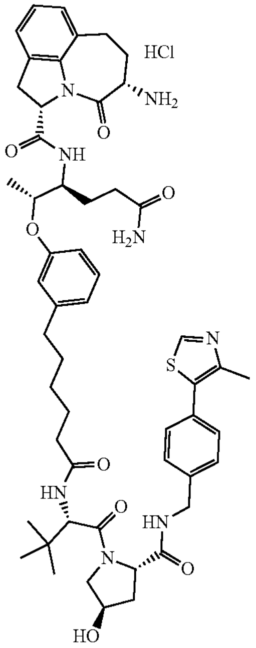 [SMILES: Cc1ncsc1-c1ccc(CNC(=O)[C@@H]2C[C@@H](O)CN2C(=O)[C@@H](NC(=O)CCCCCc2cccc(O[C@H](C)[C@H](CCC(N)=O)NC(=O)[C@@H]3Cc4cccc5c4N3C(=O)[C@@H](N)CC5)c2)C(C)(C)C)cc1 ; Cl] | (2S,4R)-1-[(2S)-2-[6-(3-[[(2R,3S)-3-[[(2S,11S)-11-amino-12-oxo-1-azatricyclo [6.4.1.0^[4,13]] trideca-4(13),5,7-trien-2-yl]formamido]-5-carbamoylpentan-2-yl]oxy]phenyl) hexanamido]-3,3-dimethylbutanoyl]-4-hydroxy-N-[[4-(4-methyl-1,3-thiazol-5-yl)phenyl]methyl] pyrrolidine-2-carboxamide | 977.55 | (400 MHz, DMSO-$d_6$) δ 9.03 (s, 1H), 8.58 (t, J = 6.1 Hz, 1H), 8.53-8.41 (m, 4H), 8.14 (d, J = 8.9 Hz, 1H), 7.85 (d, J = 9.3 Hz, 1H), 7.44-7.38 (m, 4H), 7.25 (s, 1H), 7.14 (t, J = 7.7 Hz, 1H), 7.06 (t, J = 6.6 Hz, 2H), 7.02-6.95 (m, 1H), 6.74 (d, J = 7.7 Hz, 2H), 6.69-6.66 (m, 2H), 5.12 (dd, J = 10.9, 3.0 Hz, 1H), 4.54 (d, J = 9.4 Hz, 1H), 4.48-4.32 (m, 4H), 4.27-4.12 (m, 2H), 3.83 (s, 1H), 3.74-3.60 (m, 2H), 3.39 (q, J = 7.0 Hz, 3H), 3.16-3.12 (m, 2H), 2.78 (dd, J = 17.2, 3.0 Hz, 1H), 2.45 (s, 3H), 2.34-1.98 (m, 5H), 1.98-1.81 (m, 1H), 1.73-1.43 (m, 5H), 1.32-1.22 (m, 1H), 1.19 (d, J = 4.0 Hz, 2H), 1.10 (t, J = 7.0 Hz, 4H), 0.93 (s, 9H) |
| J134 | 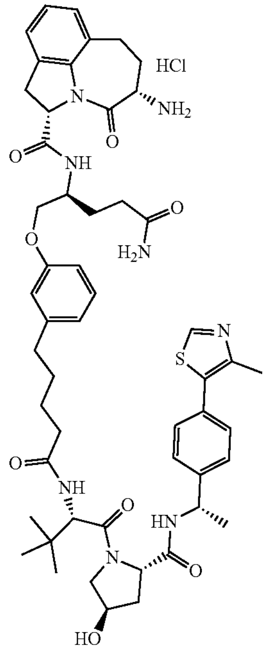 [SMILES: Cc1ncsc1-c1ccc([C@H](C)NC(=O)[C@@H]2C[C@@H](O)CN2C(=O)[C@@H](NC(=O)CCCCc2cccc(OC[C@H](CCC(N)=O)NC(=O)[C@@H]3Cc4cccc5c4N3C(=O)[C@@H](N)CC5)c2)C(C)(C)C)cc1 ; Cl] | (2S,4R)-1-[(2S)-2-(5-[3-[(2S)-2-[[(2S,11S)-11-amino-12-oxo-1-azatricyclo [6.4.1.0^[4,13]] trideca-4(13),5,7-trien-2-yl]formamido]-4-carbamoylbutoxy] phenyl] pentanamido]-3,3-dimethylbutanoyl]-4-hydroxy-N-[(1S)-1-[4-(4-methyl-1,3-thiazol-5-yl)phenyl]ethyl] pyrrolidine-2-carboxamide hydrochloride | 963.40 | (400 MHz, DMSO-$d_6$) δ 9.04 (s, 1H), 8.49 (d, J = 16.8 Hz, 3H), 8.38 (d, J = 7.8 Hz, 1H), 8.25 (d, J = 8.1 Hz, 1H), 7.82 (d, J = 9.2 Hz, 1H), 7.45 (d, J = 8.1 Hz, 2H), 7.39 (d, J = 8.2 Hz, 2H), 7.28 (s, 1H), 7.22-7.14 (m, 1H), 7.08 (d, J = 5.4 Hz, 2H), 7.05-6.96 (m, 1H), 6.77-6.73 (m, 3H), 5.12-5.08 (m, 1H), 4.91 (q, J = 7.3 Hz, 1H), 4.52 (d, J = 9.2 Hz, 1H), 4.43 (t, J = 8.0 Hz, 1H), 4.28 (s, 1H), 4.01-3.98 (m, 1H), 3.93-3.89 (m, 2H), 3.71-3.57 (m, 3H), 3.52-3.41 (m, 1H), 3.45-3.37 (m, 1H), 3.17-3.13 (m, 2H), 2.92-2.82 (m, 1H), 2.56-2.52 (m, 2H), 2.47 (s, 3H), 2.33-2.20 (m, 1H), 2.21-1.96 (m, 3H), 1.87-1.70 (m, 5H), 1.62-1.43 (m, 5H), 1.38 (d, J = 7.1 Hz, 3H), 0.94 (s, 9H) |

TABLE 53-continued

Characterization data for intermediates prepared according to above.

| Intermediate | Structure | Chemical Name | MS: $[(M + 1)]^+$ | $^1H$ NMR |
|---|---|---|---|---|
| J135 | 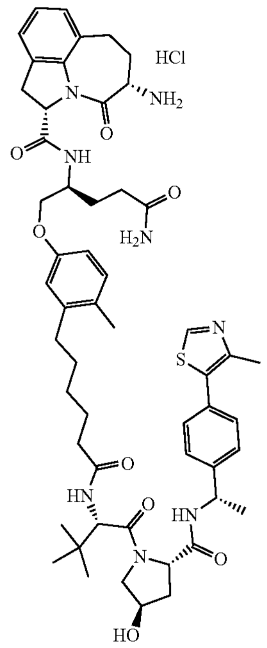 [SMILES: Cc1ccc(OC[C@H](CCC(N)=O)NC(=O)[C@@H]2Cc3cccc4c3N2C(=O)[C@@H](N)CC4)cc1CCCCCC(=O)N[C@H](C(=O)N1C[C@H](O)C[C@H]1C(=O)N[C@@H](C)c1ccc(-c2scnc2C)cc1)C(C)(C)C ; Cl] | (2S,4R)-1-[(2S)-2-(6-[5-[(2S)-2-[[(2S,11S)-11-amino-12-oxo-1-azatricyclo [6.4.1.0^[4,13]] trideca-4(13),5,7-trien-2-yl]formamido]-4-carbamoylbutoxy]-2-methylphenyl] hexanamido]-3,3-dimethylbutanoyl]-4-hydroxy-N-[(1S)-1-[4-(4-methyl-1,3-thiazol-5-yl)phenyl]ethyl] pyrrolidine-2-carboxamide hydrochloride | 991.75 | (400 MHz, DMSO-$d_6$) δ 9.10 (s, 1H), 8.59-8.55 (m, 1H), 8.52 (d, J = 5.4 Hz, 2H), 8.40 (d, J = 7.8 Hz, 1H), 8.24 (d, J = 8.3 Hz, 1H), 7.80 (d, J = 9.2 Hz, 1H), 7.49-7.32 (m, 4H), 7.30-7.28 (m, 1H), 7.11-7.05 (m, 2H), 7.05-6.96 (m, 2H), 6.77-6.75 (m, 1H), 6.70 (s, 1H), 5.10-5.08 (m, 1H), 4.92-4.90 (m, 1H), 4.56-4.48 (m, 1H), 4.43-4.41 (m, 1H), 4.28-4.26 (m, 1H), 4.21-4.14 (m, 1H), 3.87-3.85 (m, 2H), 3.70-3.58 (m, 3H), 3.50-3.36 (m, 2H), 3.14-3.12 (m, 2H), 2.86-2.84 (m, 2H), 2.45 (s, 3H), 2.28-2.26 (m, 2H), 2.21-1.97 (m, 7H), 1.87-1.66 (m, 3H), 1.62-1.43 (m, 5H), 1.48-1.46 (m, 2H), 1.35-1.32 (m, 4H), 0.94 (s, 9H) |
| J136 | 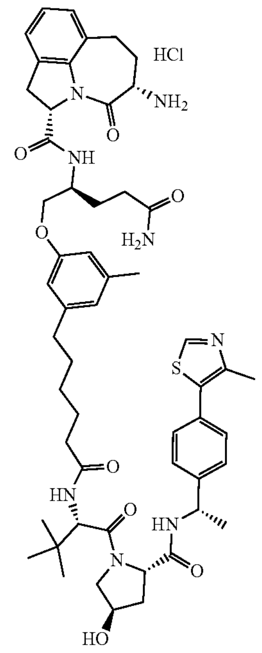 [SMILES: Cc1cc(CCCCCC(=O)N[C@H](C(=O)N2C[C@H](O)C[C@H]2C(=O)N[C@@H](C)c2ccc(-c3scnc3C)cc2)C(C)(C)C)cc(OC[C@H](CCC(N)=O)NC(=O)[C@@H]2Cc3cccc4c3N2C(=O)[C@@H](N)CC4)c1 ; Cl] | (2S,4R)-1-[(2S)-2-(6-[3-[(2S)-2-[[(2S,11S)-11-amino-12-oxo-1-azatricyclo [6.4.1.0^[4,13]] trideca-4(13),5,7-trien-2-yl]formamido]-4-carbamoylbutoxy]-5-methylphenyl] hexanamido]-3,3-dimethylbutanoyl]-4-hydroxy-N-[(1S)-1-[4-(4-methyl-1,3-thiazol-5-yl)phenyl]ethyl] pyrrolidine-2-carboxamide hydrochloride | 991.55 | (400 MHz, DMSO-$d_6$) δ 9.07 (d, J = 1H), 8.53-8.50 (m, J = 21.5 Hz, 2H), 8.39 (d, J = 7.8 Hz, 1H), 8.23 (d, J = 8.2 Hz, 1H), 7.78 (d, J = 9.3 Hz, 1H), 7.49-7.41 (m, 2H), 7.45-7.32 (m, 2H), 7.30 (s, 1H), 7.08 (d, J = 7.4 Hz, 2H), 7.00 (d, J = 8.3, 6.5 Hz, 1H), 6.77 (s, 1H), 6.59 (s, 1H), 6.53 (d, J = 6.1 Hz, 2H), 5.10 (d, J = 10.9, 3.0 Hz, 1H), 4.94-4.90 (m, 1H), 4.55-4.48 (m, 2H), 4.47-4.39 (m, 2H), 4.19 (d, J = 15.3, 10.4 Hz, 1H), 4.00-3.83 (m, 1H), 3.68-3.58 (m, 2H), 3.62-3.58 (m, 2H), 3.57-3.50 (m, 7H), 3.48-3.37 (m, 2H), 3.17-3.13 (m, 2H), 2.88-2.84 (m, 1H), 2.45 (s, 3H), 2.51-2.43 (m, 1H), 2.23 (s, 3H), 2.20-1.96 (m, 4H), 1.87-1.68 (m, 1H), 1.58-1.42 (m, 2H), 1.38 (d, J = 7.0 Hz, 3H), 1.26-1.24 (m, 2H), 0.93 (s, 9H) |

TABLE 53-continued

Characterization data for intermediates prepared according to above.

| Intermediate | Structure | Chemical Name | MS: [(M + 1)]+ | 1H NMR |
|---|---|---|---|---|
| J137 | 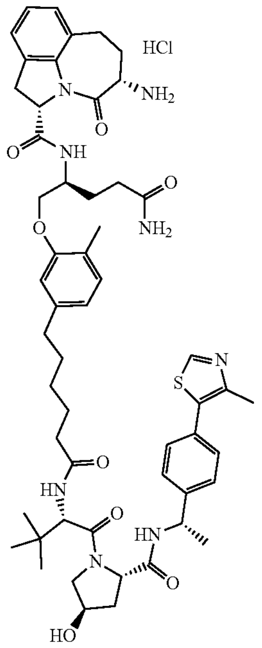 [SMILES: Cc1ccc(CCCCCC(=O)N[C@H](C(=O)N2C[C@H](O)C[C@H]2C(=O)N[C@@H](C)c2ccc(-c3scnc3C)cc2)C(C)(C)C)cc1OC[C@H](CCC(N)=O)NC(=O)[C@@H]1Cc2cccc3c2N1C(=O)[C@@H](N)CC3 ; Cl] | (2S,4R)-1-[(2S)-2-(6-[3-[(2S)-2-[[(2S,11S)-11-amino-12-oxo-1-azatricyclo [6.4.1.0^[4,13]] trideca-4(13),5,7-trien-2-yl]formamido]-4-carbamoylbutoxy]-4-methylphenyl] hexanamido]-3,3-dimethylbutanoyl]-4-hydroxy-N-[(1S)-1-[4-(4-methyl-1,3-thiazol-5-yl)phenyl]ethyl] pyrrolidine-2-carboxamide hydrochloride | 991.35 | (400 MHz, DMSO-$d_6$) δ 9.15 (d, J = 1.3 Hz, 1H), 8.56-8.50 (m, 3H), 8.42 (d, J = 7.8 Hz, 1H), 8.28 (d, J = 8.2 Hz, 1H), 7.79 (d, J = 9.3 Hz, 1H), 7.45 (d, J = 8.3 Hz, 1H), 7.42-7.32 (m, 2H), 7.06-7.02 (m, J = 6.7 Hz, 3H), 7.03-6.95 (m, 1H), 7.00 (s, 1H), 6.80 (s, 1H), 6.73 (s, 1H), 6.69-6.62 (m, 1H), 5.12 (d, J = 10.9, 3.1 Hz, 1H), 4.92 (d, J = 7.1 Hz, 1H), 4.51 (d, J = 9.4 Hz, 1H), 4.43 (d, J = 8.0 Hz, 1H), 4.28 (s, 1H), 4.21-4.13 (m, 1H), 4.02 (s, 1H), 3.98-3.84 (m, 2H), 3.69-3.56 (m, 7H), 3.49-3.36 (m, 3H), 3.17-3.13 (m, 2H), 2.87-2.83 (m, 1H), 2.48-2.46 (m, 1H), 2.45 (s, 3H), 2.32-1.98 (m, 6H), 1.86-1.69 (m, 4H), 1.62-1.45 (m, 3H), 1.38-1.34 (m, 3H), 1.30-1.21 (m, 1H), 0.93 (s, 9H) |
| J138 | 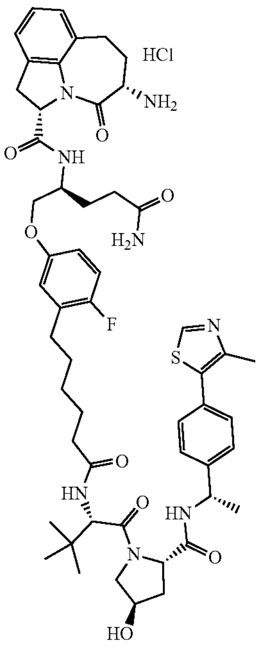 [SMILES: Cc1ncsc1-c1ccc([C@H](C)NC(=O)[C@@H]2C[C@@H](O)CN2C(=O)[C@@H](NC(=O)CCCCCc2cc(OC[C@H](CCC(N)=O)NC(=O)[C@@H]3Cc4cccc5c4N3C(=O)[C@@H](N)CC5)ccc2F)C(C)(C)C)cc1 ; Cl] | (2S,4R)-1-[(2S)-2-(6-[3-[(2S)-2-[[(2S,11S)-11-amino-12-oxo-1-azatricyclo [6.4.1.0^[4,13]] trideca-4(13),5,7-trien-2-yl]formamido]-4-carbamoylbutoxy]-2-fluorophenyl] hexanamido]-3,3-dimethylbutanoyl]-4-hydroxy-N-[(1S)-1-[4-(4-methyl-1,3-thiazol-5-yl)phenyl]ethyl] pyrrolidine-2-carboxamide hydrochloride | 995.40 | (400 MHz, DMSO-$d_6$) δ 9.08 (s, 1H), 8.54 (d, J = 17.3 Hz, 3H), 8.40 (d, J = 7.8 Hz, 1H), 8.27 (d, J = 8.2 Hz, 1H), 7.79 (d, J = 9.3 Hz, 1H), 7.49-7.32 (m, 4H), 7.30 (s, 1H), 7.08 (s, 2H), 7.04-6.96 (m, 2H), 6.84-6.71 (m, 2H), 5.12-5.08 (m, 1H), 4.93-4.89 (m, 1H), 4.52 (d, J = 9.3 Hz, 1H), 4.43 (t, J = 8.0 Hz, 1H), 4.28 (s, 1H), 4.18 (s, 1H), 4.00-3.82 (m, 2H), 3.69-3.57 (m, 6H), 3.49-3.36 (m, 1H), 3.15 (s, 2H), 2.87-2.83 (m, 1H), 2.54 (d, J = 7.4 Hz, 1H), 2.47 (s, 3H), 2.31-2.06 (m, 2H), 2.06-1.97 (m, 1H), 1.87-1.79 (m, 1H), 1.82-1.71 (m, 4H), 1.60 (s, 1H), 1.55-1.51 (m, 4H), 1.50-1.42 (m, 1H), 1.38 (d, J = 7.0 Hz, 3H), 1.30-1.26 (m, 1H), 0.93 (s, 9H) |

TABLE 53-continued

| Characterization data for intermediates prepared according to above. | | | | |
|---|---|---|---|---|
| Intermediate | Structure | Chemical Name | MS: [(M + 1)]+ | 1H NMR |
| J139 | 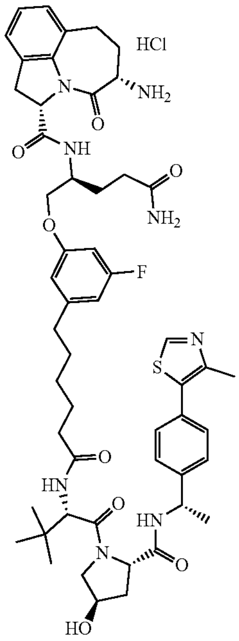 [SMILES: Cc1ncsc1-c1ccc([C@H](C)NC(=O)[C@@H]2C[C@@H](O)CN2C(=O)[C@@H](NC(=O)CCCCCc2cc(F)cc(OC[C@H](CCC(N)=O)NC(=O)[C@@H]3Cc4cccc5c4N3C(=O)[C@@H](N)CC5)c2)C(C)(C)C)cc1 ; Cl] | (2S,4R)-1-[(2S)-2-(6-[3-[(2S)-2-[[(2S,11S)-11-amino-12-oxo-1-azatricyclo [6.4.1.0^[4,13]] trideca-4(13),5,7-trien-2-yl]formamido]-4-carbamoylbutoxy]-5-fluorophenyl] hexanamido]-3,3-dimethylbutanoyl]-4-hydroxy-N-[(1S)-1-[4-(4-methyl-1,3-thiazol-5-yl)phenyl]ethyl] pyrrolidine-2-carboxamide hydrochloride | 995.40 | (400 MHz, DMSO-$d_6$) δ 9.03 (s, 1H), 8.46 (d, J = 16.0 Hz, 2H), 8.39 (d, J = 7.8 Hz, 1H), 8.25 (d, J = 7.8 Hz, 1H), 7.80 (d, J = 9.3 Hz, 1H), 7.48-7.37 (m, 3H), 7.38 (s, 1H), 7.28 (s, 1H), 7.08 (d, J = 7.6 Hz, 2H), 7.05-6.96 (m, 1H), 6.79 (s, 1H), 6.65-6.57 (m, 3H), 5.11-5.07 (m, 1H), 4.93-4.89 (m, 1H), 4.72-4.57 (m, 1H), 4.55-4.48 (m, 1H), 4.42 (t, J = 8.0 Hz, 1H), 4.28 (s, 1H), 4.20 (d, J = 9.4 Hz, 1H), 4.04-3.88 (m, 2H), 3.76-3.57 (m, 3H), 3.53-3.37 (m, 2H), 3.17-3.13 (m, 2H), 2.87-2.83 (m, 1H), 2.54 (s, 1H), 2.46 (s, 3H), 2.17-2.13 (m, 7H), 1.85-1.70 (m, 2H), 1.58-1.51 (m, 5H), 1.48-1.34 (m, 3H), 1.30-1.21 (m, 2H), 0.93 (s, 9H) |
| J140 | 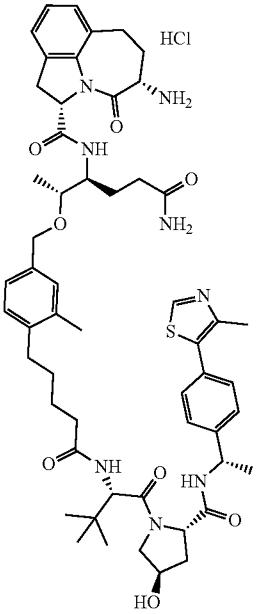 [SMILES: Cc1cc(CO[C@H](C)[C@H](CCC(N)=O)NC(=O)[C@@H]2Cc3cccc4c3N2C(=O)[C@@H](N)CC4)ccc1CCCCC(=O)N[C@H](C(=O)N1C[C@H](O)C[C@H]1C(=O)N[C@@H](C)c1ccc(-c2scnc2C)cc1)C(C)(C)C ; Cl] | (2S,4R)-1-[(2S)-2-[5-[4-([[(2R,3S)-2-[[(2S,11S)-11-amino-12-oxo-1-azatricyclo [6.4.1.0^[4,13]] trideca-4(13),5,7-trien-2-yl]formamido]-5-carbamoylpentan-2-yl]oxy]methyl)-2-methylphenyl] pentanamido]-3,3-dimethylbutanoyl]-4-hydroxy-N-[(1S)-1-[4-(4-methyl-1,3-thiazol-5-yl)phenyl]ethyl] pyrrolidine-2-carboxamide hydrochloride | 1005.60 | (400 MHz, DMSO-$d_6$) δ 9.03 (s, 1H), 8.60-8.30 (m, 4H), 8.01 (d, J = 9.2 Hz, 1H), 7.82 (d, J = 9.3 Hz, 1H), 7.47-7.35 (m, 4H), 7.26-7.11 (m, 1H), 7.11-6.95 (m, 5H), 6.74 (s, 1H), 5.13 (dd, J = 11.0, 3.1 Hz, 1H), 4.92 (t, J = 7.2 Hz, 1H), 4.54-4.52 (m, 2H), 4.43-4.41 (m, 1H), 4.37 (s, 2H), 4.28 (s, 1H), 4.22-4.16 (m, 1H), 3.86-3.74 (m, 1H), 3.64-3.60 (m, 2H), 3.52-3.35 (m, 2H), 3.17-3.13 (m, 2H), 2.90-2.84 (m, 1H), 2.57-2.54 (m, 3H), 2.46 (s, 3H), 2.38-2.27 (m, 1H), 2.24-1.96 (m, 5H), 1.83-1.75 (m, 2H), 1.64-1.43 (m, 6H), 1.38 (d, J = 7.1 Hz, 3H), 1.29-1.24 (m, 1H), 1.09 (d, J = 6.2 Hz, 3H), 0.94 (s, 9H), 0.89-0.81 (m, 1H) |

TABLE 53-continued

Characterization data for intermediates prepared according to above.

| Intermediate | Structure | Chemical Name | MS: $[(M+1)]^+$ | $^1H$ NMR |
|---|---|---|---|---|
| J141 | 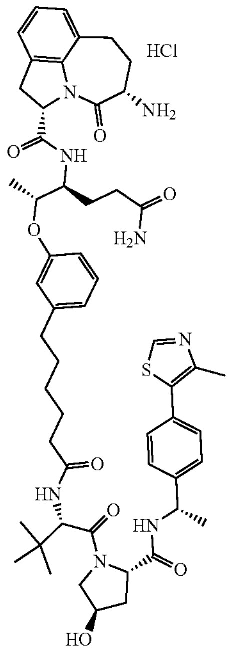 [SMILES: Cc1ncsc1-c1ccc([C@H](C)NC(=O)[C@@H]2C[C@@H](O)CN2C(=O)[C@@H](NC(=O)CCCCCc2cccc(O[C@H](C)[C@H](CCC(N)=O)NC(=O)[C@@H]3Cc4cccc5c4N3C(=O)[C@@H](N)CC5)c2)C(C)(C)C)cc1 ; Cl] | (2S,4R)-1-[(2S)-2-[6-(3-[[(2R,3S)-3-[[(2S,11S)-11-amino-12-oxo-1-azatricyclo [6.4.1.0^[4,13]] trideca-4(13),5,7-trien-2-yl]formamido]-5-carbamoylpentan-2-yl]oxy]phenyl) hexanamido]-3,3-dimethylbutanoyl]-4-hydroxy-N-[(1S)-1-[4-(4-methyl-1,3-thiazol-5-yl)phenyl]ethyl] pyrrolidine-2-carboxamide hydrochloride | 991.75 | (400 MHz, DMSO-$d_6$) δ 9.04 (s, 1H), 8.56-8.50 (m, 5H), 8.39 (d, J = 7.8 Hz, 1H), 8.16 (d, J = 8.9 Hz, 1H), 7.79 (d, J = 9.3 Hz, 1H), 7.48-7.37 (m, 6H), 7.22-6.96 (m, 7H), 6.75 (d, J = 7.6 Hz, 2H), 6.70-6.67 (m, 2H), 5.13 (dd, J = 10.9, 3.0 Hz, 1H), 4.92 (t, J = 7.2 Hz, 1H), 4.52 (d, J = 9.4 Hz, 1H), 4.47-4.37 (m, 1H), 4.28 (s, 1H), 4.18-4.16 (m, 1H), 3.86-3.82 (m, 1H), 3.16-3.12 (m, 5H), 2.78 (d, J = 16.6 Hz, 1H), 2.46 (s, 3H), 2.34-1.94 (m, 8H), 1.92-1.60 (m, 2H), 1.56-1.47 (m, 4H), 1.30-1.24 (m, 2H), 1.19 (d, J = 6.1 Hz, 3H), 0.93 (s, 9H) |
| J142 | 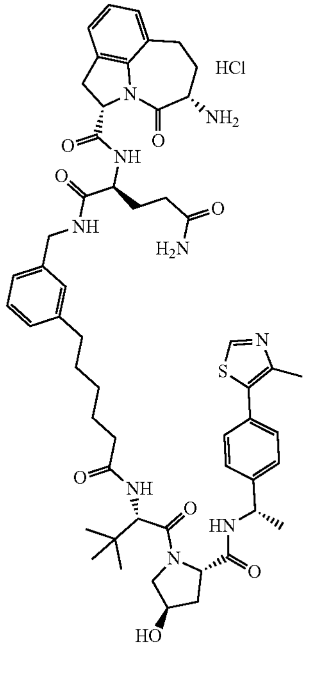 [SMILES: Cc1ncsc1-c1ccc([C@H](C)NC(=O)[C@@H]2C[C@@H](O)CN2C(=O)[C@@H](NC(=O)CCCCCc2cccc(CNC(=O)[C@H](CCC(N)=O)NC(=O)[C@@H]3Cc4cccc5c4N3C(=O)[C@@H](N)CC5)c2)C(C)(C)C)cc1 ; Cl] | (2S)-2-[[(2S,11S)-11-amino-12-oxo-1-azatricyclo [6.4.1.0^[4,13]] trideca-4(13),5,7-trien-2-yl]formamido]-N-[[3-(5-[[(2S)-1-[(2S,4R)-4-hydroxy-2-[[(1S)-1-[4-(4-methyl-1,3-(thiazol-5-yl)phenyl]ethyl] carbamoyl] pyrrolidin-1-yl]-3,3-dimethyl-1-oxobutan-2-yl]carbamoyl]pentyl) phenyl]methyl] pentanediamide hydrochloride | 1004.65 | (400 MHz, DMSO-$d_6$) δ 9.08 (s, 1H), 8.51 (d, J = 5.4 Hz, 2H), 8.44 (d, J = 6.9 Hz, 2H), 8.40 (d, J = 7.8 Hz, 1H), 7.81 (d, J = 9.3 Hz, 1H), 7.47-7.43 (m, 2H), 7.39 (d, J = 8.4 Hz, 2H), 7.18 (t, J = 7.8 Hz, 1H), 7.11-6.98 (m, 7H), 6.82-6.79 (m, 1H), 4.93 (q, J = 7.0 Hz, 1H), 4.52 (d, J = 9.3 Hz, 1H), 4.43 (t, J = 8.0 Hz, 1H), 4.31-4.14 (m, 6H), 3.48-3.36 (m, 2H), 3.13 (d, J = 6.4 Hz, 2H), 2.95 (d, J = 17.2 Hz, 1H), 2.47 (s, 3H), 2.25 (dt, J = 15.3, 7.8 Hz, 2H), 2.17-1.99 (m, 6H), 1.92 (s, 1H), 1.80 (ddd, J = 13.0, 8.6, 4.8 Hz, 2H), 1.57-1.46 (m, 5H), 1.38 (d, J = 7.0 Hz, 3H), 1.28-1.21 (m, 3H), 1.10 (t, J = 7.0 Hz, 1H), 0.93 (s, 9H) |

TABLE 53-continued

Characterization data for intermediates prepared according to above.

| Intermediate | Structure | Chemical Name | MS: $[(M + 1)]^+$ | $^1H$ NMR |
|---|---|---|---|---|
| J143 | 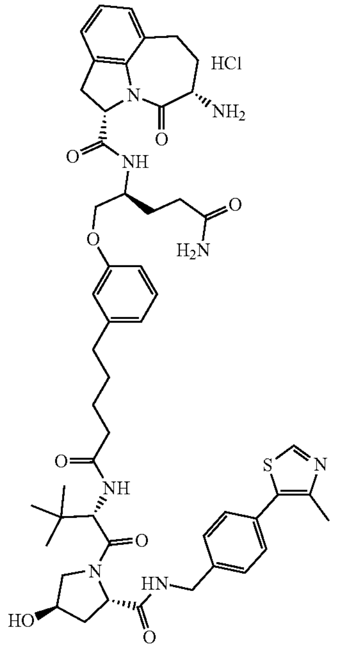 [SMILES: Cc1ncsc1-c1ccc(CNC(=O)[C@@H]2C[C@@H](O)CN2C(=O)[C@@H](NC(=O)CCCCc2cccc(OC[C@H](CCC(N)=O)NC(=O)[C@@H]3Cc4cccc5c4N3C(=O)[C@@H](N)CC5)c2)C(C)(C)C)cc1 ; Cl] | (2S,4R)-1-[(2S)-2-(5-[3-[(2S)-2-[[(2S,11S)-11-amino-12-oxo-1-azatricyclo [6.4.1.0^[4,13]] trideca-4(13),5,7-trien-2-yl]formamido]-4-carbamoylbutoxy] phenyl]pentanamido)-3,3-dimethylbutanoyl]-4-hydroxy-N-[[4-(4-methyl-1,3-thiazol-5-yl)phenyl]methyl] pyrrolidine-2-carboxamide hydrochloride | 949.55 | (300 MHz, DMSO-$d_6$) δ 9.03 (s, 1H), 8.61-8.56 (m, 1H), 8.49-8.43 (m, 3H), 8.26 (d, J = 8.0 Hz, 1H), 7.90 (d, J = 9.4 Hz, 1H), 7.46-7.35 (m, 4H), 7.29 (s, 1H), 7.22-7.12 (m, 1H), 7.12-6.93 (m, 3H), 6.85-6.68 (m, 4H), 5.09 (d, J = 10.6 Hz, 1H), 4.58-4.53 (m, 2H), 4.43-4.39 (m, 4H), 4.37-4.32 (m, 2H), 4.26-4.16 (m, 2H), 4.05-3.82 (m, 2H), 3.67-3.63 (m, 2H), 3.49-3.38 (m, 3H), 2.89-2.73 (m, 1H), 3.18-3.12 (m, 2H), 2.45 (s, 3H), 2.25-1.98 (m, 4H), 1.94-1.68 (m, 1H), 1.60-1.48 (m, 6H), 0.94 (s, 9H) |
| J144 | 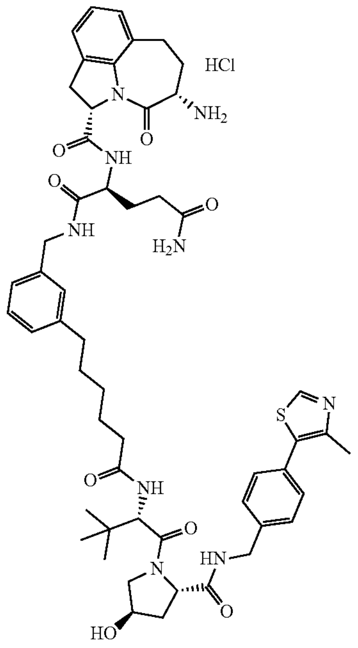 [SMILES: Cc1ncsc1-c1ccc(CNC(=O)[C@@H]2C[C@@H](O)CN2C(=O)[C@@H](NC(=O)CCCCCc2cccc(CNC(=O)[C@H](CCC(N)=O)NC(=O)[C@@H]3Cc4cccc5c4N3C(=O)[C@@H](N)CC5)c2)C(C)(C)C)cc1 ; Cl] | (2S)-2-[[(2S,11S)-11-amino-12-oxo-1-azatricyclo [6.4.1.0^[4,13]][ trideca-4(13),5,7-trien-2-yl]formamido]-N-[[3-(5-[[(2S)-1-[(2S,4R)-4-hydroxy-2-([[4-(4-methyl-1,3-thiazol-5-yl)phenyl]methyl] carbamoyl)pyrrolidin-1-yl]-3,3-dimethyl-1-oxobutan-2-yl]carbamoyl]pentyl) phenyl]methyl] pentanediamide hydrochloride | 990.60 | (400 MHz, DMSO-$d_6$) δ 9.06 (s, 1 H), 8.58 (t, J = 6.0 Hz, 1H), 8.49 (d, J = 5.3 Hz, 1H), 8.43 (d, J = 6.9 Hz, 1H), 7.86 (d, J = 9.3 Hz, 1H), 7.51-7.34 (m, 4H), 7.26-7.13 (m, 1H), 7.10-7.02 (m, 4H), 6.80 (s, 1H), 5.18 (dd, J = 10.9, 3.0 Hz, 1H), 4.61-4.51 (m, 1H), 4.49-4.39 (m, 2 H), 4.34 (d, J = 11.8 Hz, 1H), 4.22-4.20 (m, 4H), 3.73-3.59 (m, 2H), 3.49-3.41 (m, 1H), 3.40 (d, J = 1.0 Hz, 1H), 3.13 (d, J = 6.6 Hz, 1H), 3.00-2.90 (m, 1H), 2.46 (s, 3H), 2.29-2.25 (m, 2H), 2.17-1.99 (m, 4 H), 1.92-1.89 (m, 1H), 1.85-1.72 (m, 1H), 1.53-1.46 (m, 4H), 1.27-1.23 (m, 2H), 0.93 (s, 9H). |

TABLE 53-continued

| Characterization data for intermediates prepared according to above. | | | | |
|---|---|---|---|---|
| Intermediate | Structure | Chemical Name | MS: [(M + 1)]+ | $^1$H NMR |
| J145 | 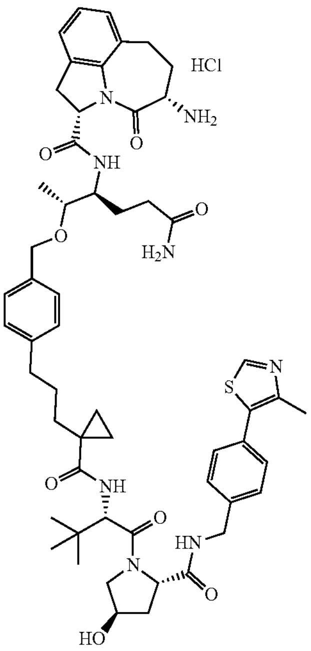 [SMILES: Cc1ncsc1-c1ccc(CNC(=O)[C@@H]2C[C@@H](O)CN2C(=O)[C@@H](NC(=O)C2(CCCc3ccc(CO[C@H](C)[C@H](CCC(N)=O)NC(=O)[C@@H]4Cc5cccc6c5N4C(=O)[C@@H](N)CC6)cc3)CC2)C(C)(C)C)cc1 ; Cl] | (2S,4R)-1-[(2S)-2-[(1-[3-[4-([[2R,3S)-3-[[(2S,11S)-11-amino-12-oxo-1-azatricyclo [6.4.1.0^[4,13]] trideca-4(13),5,7-trien-2-yl]formamido]-5-carbamoylpentan-2-yl]oxy]methyl] phenyl]propyl] cyclopropyl) formamido]-3,3-dimethylbutanoyl]-4-hydroxy-N-[[4-(4-methyl-1,3-thiazol-5-yl)phenyl]methyl] pyrrolidine-2-carboxamide hydrochloride | 1003.75 | (400 MHz, Methanol-$d_4$) δ 9.64 (d, J = 29.4 Hz, 1H), 8.11 (s, 1H), 7.61-7.47 (m, 3H), 7.22 (d, J = 7.9 Hz, 2H), 7.18-6.99 (m, 5H), 5.19 (dd, J = 10.9, 3.5 Hz, 1H), 4.71 (s, 1H), 4.69-4.58 (m, 1H), 4.58 (d, J = 3.7 Hz, 1H), 4.58-4.48 (m, 3H), 4.48-4.39 (m, 1H), 4.42-4.28 (m, 1H), 4.20 (d, J = 13.5 Hz, 1H), 4.07-3.99 (m, 1H), 3.91-3.71 (m, 2H), 3.62 (s, 2H), 3.60-3.46 (m, 1H), 3.26 (s, 3H), 3.11-2.99 (m, 1H), 2.66 (s, 2H), 2.57 (d, J = 6.4 Hz, 3H), 2.42-2.23 (m, 1H), 2.27 (s, 3H), 2.15-1.96 (m, 1H), 1.81 (s, 3H), 1.31 (s, 1H), 1.26-1.17 (m, 3H), 1.17-1.09 (m, 1H), 1.01 (d, J = 10.2 Hz, 9H), 0.96-0.85 (m, 1H), 0.65 (s, 2H) |
| J147 | 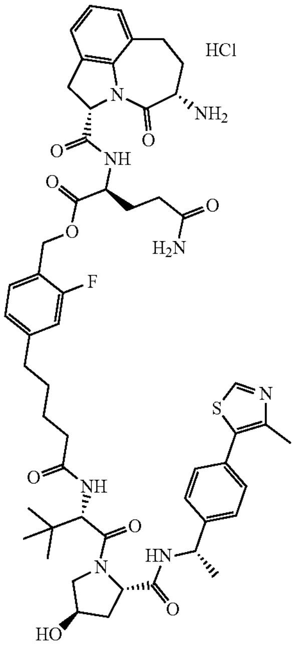 [SMILES: Cc1ncsc1-c1ccc([C@H](C)NC(=O)[C@@H]2C[C@@H](O)CN2C(=O)[C@@H](NC(=O)CCCCc2ccc(COC(=O)[C@H](CCC(N)=O)NC(=O)[C@@H]3Cc4cccc5c4N3C(=O)[C@@H](N)CC5)c(F)c2)C(C)(C)C)cc1 ; Cl] | (2S,4R)-1-[(2S)-2-[5-[4-([[(2R,3S)-3-[[(2S,11s)-11-amino-12-oxo-1-azatricyclo [6.4.1.0^[4,13]] trideca-4(13),5,7-trien-2-yl]formamido]-5-carbamoylpentan-2-yl]oxy]methyl)-3-fluorophenyl]-pentanamido]-3,3-dimethylbutanoyl]-4-hydroxy-N-[(1S)-1-[4-(4-methyl-1,3-thiazol-5-yl)phenyl]ethyl] pyrrolidine-2-carboxamide hydrochloride | 1009.55 | (400 MHz, DMSO-$d_6$) δ 9.04 (s, 1H), 8.52-8.47 (d, J = 5.3 Hz, 3H), 8.39 (d, J = 7.8 Hz, 1H), 8.03 (d, J = 9.1 Hz, 1H), 7.84 (d, J = 9.2 Hz, 1H), 7.47-7.36 (m, 4H), 7.24 (t, J = 7.9 Hz, 1H), 7.09-7.07 (m, 2H), 7.04-6.97 (m, 2H), 6.94 (d, J = 7.7 Hz, 1H), 6.73 (s, 1H), 5.12 (dd, J = 11.0, 3.1 Hz, 1H), 4.96-4.89 (m, 1H), 4.56-4.42 (m, 10H), 4.28 (s, 1H), 4.23-4.13 (m, 1H), 3.85-3.72 (m, 1H), 3.62-3.60 (m, 1H), 3.52-3.36 (m, 2H), 3.17-3.13 (m, 2H), 2.88-2.83 (m, 1H), 2.58 (t, J = 7.2 Hz, 1H), 2.47 (s, 3H), 2.38-1.95 (m, 3H), 1.83-1.74 (m, 1H), 1.64-1.41 (m, 7H), 1.38 (d, J = 7.1 Hz, 3H), 1.09 (d, J = 6.1 Hz, 3H), 0.94 (s, 9H) |

TABLE 53-continued

| Characterization data for intermediates prepared according to above. | | | | |
|---|---|---|---|---|
| Intermediate | Structure | Chemical Name | MS: $[(M+1)]^+$ | $^1H$ NMR |
| J148 | 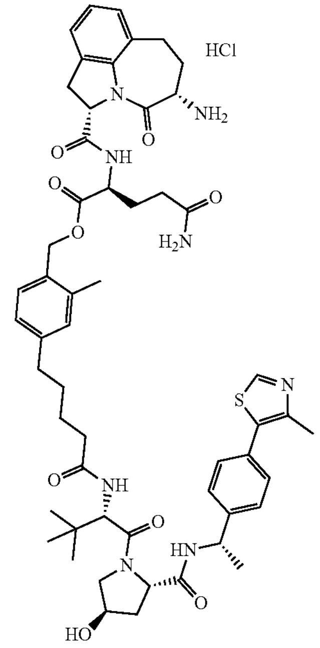 [SMILES: Cc1cc(CCCCC(=O)N[C@H](C(=O)N2C[C@H](O)C[C@H]2C(=O)N[C@@H](C)c2ccc(-c3scnc3C)cc2)C(C)(C)C)ccc1COC(=O)[C@H](CCC(N)=O)NC(=O)[C@@H]1Cc2cccc3c2N1C(=O)[C@@H](N)CC3 ; Cl] | (2S,4R)-1-[(2S)-2-[5-[4-([[(2R,3S)-3-[[(2S,11s)-11-amino-12-oxo-1-azatricyclo [6.4.1.0^[4,13]] trideca-4(13),5,7-trien-2-yl]formamido]-5-carbamoylpentan-2-yl]oxy]methyl)-3-methylphenyl] pentanamido]-3,3-dimethylbutanoyl]-4-hydroxy-N-[(1S)-1-[4-(4-methyl-1,3-thiazol-5-yl)phenyl]ethyl] pyrrolidine-2-carboxamide hydrochloride | $[(M+Na)]^+$ = 1027.80 | (400 MHz, DMSO-$d_6$) δ 9.21 (s, 1H), 8.59-8.50 (m, 3H), 8.41 (dd, J = 7.9, 2.3 Hz, 1H), 8.02 (dd, J = 24.9, 8.8 Hz, 1H), 7.82 (d, J = 9.2 Hz, 1H), 7.48-7.44 (m, 2H), 7.40 (d, J = 8.4 Hz, 2H), 7.29-7.24 (m, 1H), 7.13-7.06 (m, 3H), 7.02-6.96 (m, 2H), 6.93-6.89 (m, 1H), 6.67-6.64 (m, 4H), 5.11 (ddd, J = 22.5, 11.8, 3.1 Hz, 1H), 4.95-4.88 (m, 1H), 4.75 (s, 1H), 4.52 (d, J = 9.2 Hz, 1H), 4.46-4.40 (m, 2H), 4.38-4.33 (m, 1H), 4.29-4.27 (m, 1H), 4.16 (dd, J = 13.0, 7.9 Hz, 1H), 3.82-3.73 (m, 1H), 3.52-3.35 (m, 4H), 3.15 (d, J = 13.2 Hz, 2H), 2.94-2.79 (m, 1H), 2.48 (s, 3H), 2.35-2.26 (m, 3H), 2.22-2.11 (m, 4H), 2.08-2.00 (m, 2H), 1.81-1.77 (m, 2H), 1.61-1.59 (m, 1H), 1.56-1.48 (m, 4H), 1.38 (d, J = 7.0 Hz, 3H), 1.12-1.07 (m, 3H), 0.94 (s, 9H) |
| J149 | 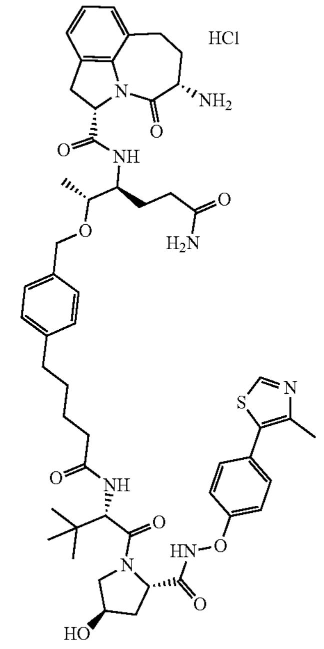 [SMILES: Cc1ncsc1-c1ccc(ONC(=O)[C@@H]2C[C@@H](O)CN2C(=O)[C@@H](NC(=O)CCCCc2ccc(CO[C@H](C)[C@H](CCC(N)=O)NC(=O)[C@@H]3Cc4cccc5c4N3C(=O)[C@@H](N)CC5)cc2)C(C)(C)C)cc1 ; Cl] | (2S,4R)-1-[(2S)-2-[5-[4-([[(2R,3S)-3-[[(2S,11s)-11-amino-12-oxo-1-azatricyclo [6.4.1.0^[4,13]] trideca-4(13),5,7-trien-2-yl]formamido]-5-carbamoylpentan-2-yl]oxy]methyl) phenyl] pentanamido]-3,3-dimethylbutanoyl]-4-hydroxy-N-[4-(4-methyl-1,3-thiazol-5-yl)phenoxy] pyrrolidine-2-carboxamide hydrochloride | 1001.55 | (400 MHz, DMSO-$d_6$) δ 9.00 (s, 1H), 8.49-8.37 (m, 2H), 7.99 (dd, J = 16.2, 9.2 Hz, 1H), 7.39-7.34 (m, 2H), 7.31-7.25 (m, 2H), 7.21-7.13 (m, 3H), 7.12-7.06 (m, 4H), 7.04-6.99 (m, 1H), 6.75 (s, 1H), 5.13 (dd, J = 11.0, 3.1 Hz, 1H), 4.57-4.54 (m, 1H), 4.39 (d, J = 6.0 Hz, 3H), 4.20 (d, J = 8.5 Hz, 1H), 3.69 (d, J = 2.5 Hz, 2H), 3.49-3.44 (m, 2H), 3.42-3.39 (m, 2H), 3.37 (d, J = 7.0 Hz, 1H), 3.18-3.13 (m, 2H), 2.90-2.83 (m, 1H), 2.52-2.55 (s, 1H) 2.43 (s, 3H), 2.17 (d, J = 6.2 Hz, 2H), 2.13-2.06 (m, 3H), 2.01-1.96 (m, 2H), 1.80-1.75 (m, 1H), 1.56-1.48 (m, 5H), 1.24 (s, 1H), 1.15-1.07 (m, 7H), 0.93 (s, 9H) |

TABLE 53-continued

Characterization data for intermediates prepared according to above.

| Intermediate | Structure | Chemical Name | MS: [(M + 1)]+ | $^1$H NMR |
|---|---|---|---|---|
| J150 | 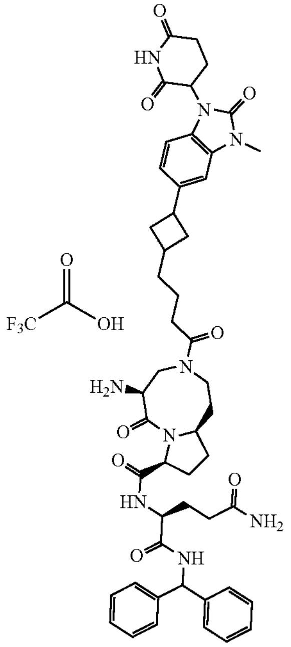 [SMILES: O=C(O)C(F)(F)F ; Cn1c(=O)n(C2CCC(=O)NC2=O)c2ccc(C3CC(CCCC(=O)N4CC[C@H]5CC[C@@H](C(=O)N[C@@H](CCC(N)=O)C(=O)NC(c6ccccc6)c6ccccc6)N5C(=O)[C@@H](N)C4)C3)cc21] | (2S)-2-[[(5S,8S,10aR)-5-amino-3-(4-[3-[1-(2,6-dioxopiperidin-3-yl)-3-methyl-2-oxo-1,3-benzodiazol-5-yl]cyclobutyl]butanoyl)-6-oxo-octahydropyrrolo[1,2-a][1,5]diazocin-8-yl]formamido]-N-(diphenylmethyl) pentanediamide trifluoroacetate | 902.35 | Used in the next step without further purification |
| J151 | 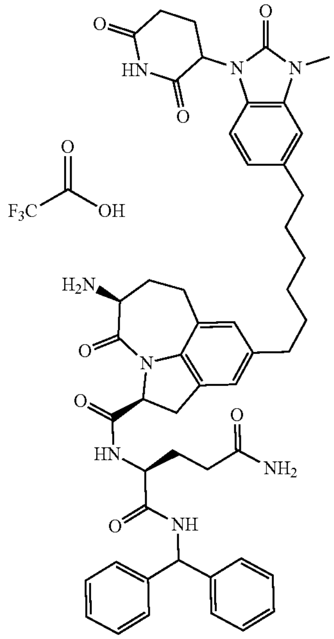 [SMILES: O=C(O)C(F)(F)F ; Cn1c(=O)n(C2CCC(=O)NC2=O)c2ccc(CCCCCCc3cc4c5c(c3)C[C@@H](C(=O)N[C@@H](CCC(N)=O)C(=O)NC(c3ccccc3)c3ccccc3)N5C(=O)[C@@H](N)CC4)cc21] | (2S)-2-[[(2S,11S)-11-amino-6-[6-[1-(2,6-dioxopiperidin-3-yl)-3-methyl-2-oxo-1,3-benzodiazol-5-yl]hexyl]-12-oxo-1-azatricyclo [6.4.1.0^[4,13]] trideca-4(13),5,7-trien-2-yl]formamido]-N-(diphenylmethyl) pentanediamide | 881.25 | (400 MHz, DMSO-d$_6$) δ 8.79 (d, J = 8.4 Hz, 1H), 8.25 (d, J = 8.0 Hz, 1H), 7.36-7.18 (m, 12H), 7.04-6.96 (m, 2H), 6.92-6.81 (m, 3H), 6.78 (s, 1H), 6.08 (d, J = 8.3 Hz, 1H), 5.34 (dd, J = 12.7, 5.4 Hz, 1H), 5.10 (dd, J = 11.0, 3.2 Hz, 1H), 4.39-4.24 (m, 1H), 3.75 (d, J = 9.7 Hz, 1H), 3.31 (s, 3H), 3.06-3.01 (m, 2H), 2.96-2.80 (m, 2H), 2.75-2.56 (m, 5H), 2.48-2.46 (m, 3H), 2.19-1.72 (m, 7H), 1.68-1.45 (m, 4H), 1.35-1.32 (m, 5H) |

TABLE 53-continued

| Characterization data for intermediates prepared according to above. | | | | |
|---|---|---|---|---|
| Intermediate | Structure | Chemical Name | MS: $[(M + 1)]^+$ | $^1H$ NMR |
| J152 | 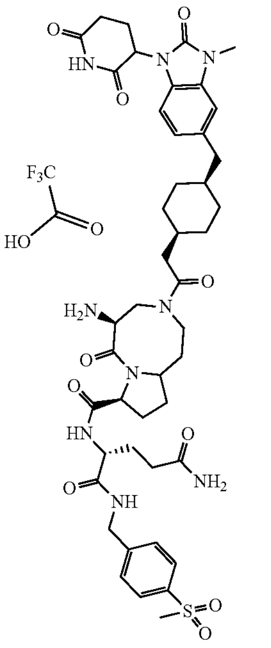 [SMILES: O=C(O)C(F)(F)F ; Cn1c(=O)n(C2CCC(=O)NC2=O)c2ccc(C[C@H]3CC[C@@H](CC(=O)N4CCC5CC[C@@H](C(=O)N[C@H](CCC(N)=O)C(=O)NCc6ccc(S(C)(=O)=O)cc6)N5C(=O)[C@@H](N)C4)CC3)cc21] | (2R)-2-[[(5S,8S,10aR)-5-amino-6-oxo-3-[2-[(1s,4s)-4-[[1-(2,6-dioxopiperidin-3-yl)-3-methyl-2-oxo-1,3-benzodiazol-5-yl)methyl]cyclohexyl]acetyl]-octahydropyrrolo[1,2-a][1,5]diazocin-8-yl]formamido]-N-[(4-methanesulfonyl-phenyl)methyl]pentanediamide trifluoroacetate | 918.30 | (400 MHz, DMSO-$d_6$) δ 11.03-10.94 (m, 1H), 8.70-8.62 (m, 1H), 8.60-8.51 (m, 1H), 8.48-8.25 (m, 1H), 8.21 (d, J = 6.6 Hz, 1H), 7.91-7.82 (m, 2H), 7.54-7.48 (m, 2H), 7.30-7.22 (, 1H), 7.06-6.95 (m, 2H), 6.88-6.71 (m, 2H), 5.34 (dd, J = 12.7, 5.4 Hz, 1H), 4.52-4.28 (m, 4H), 4.28-4.04 (m, 2H), 4.04-3.39 (m, 3H), 3.32 (s, 3H), 3.21-3.13 (m, 5H), 2.93-2.86 (m, 1H), 2.77-2.53 (m, 4H), 2.45-2.30 (m, 2H), 2.30-2.05 (m, 4H), 2.01-1.92 (m, 4H), 1.89-1.54 (m, 4H), 1.49-1.25 (m, 8H) |
| J153 | 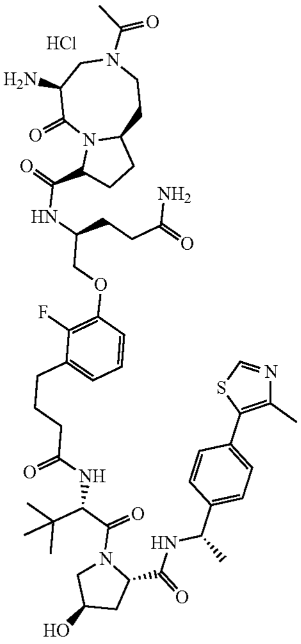 | (2S,4R)-1-[(2S)-2-(4-[3-[(2S)-2-[[(5S,8S,10aR)-3-acetyl-5-amino-6-oxo-octahydropyrrolo[1,2-a][1,5]diazocin-8-yl]formamido]-4-carbamoylbutoxy]-2-fluorophenyl]butanamido)-3,3-dimethylbutanoyl]-4-hydroxy-N-[(1S)-1-[4-4-(4-methyl-1,3-thiazol-5-yl)phenyl]ethyl]pyrrolidine-2-carboxamide hydrochloride | 990.35 | (400 MHz, DMSO-$d_6$) δ 9.05-9.03 (m, 1H), 8.50-8.46 (m, 1H), 8.40 (d, J = 7.8 Hz, 1H), 8.37-8.32 (m, 1H), 8.19 (d, J = 7.9 Hz, 1H), 7.88 (d, J = 9.3 Hz, 1H), 7.46-7.43 (m, 2H), 7.39 (d, J = 8.3 Hz, 2H), 7.26-7.24 (m, 1H), 7.04-7.00 (m, 2H), 6.85-6.75 (m, 2H), 4.93-4.91 (m, 1H), 4.53 (d, J = 9.3 Hz, 2H), 4.45-4.34 (m, 2H), 4.28-4.23 (m, 3H), 4.08-3.98 (m, 3H), 3.93-3.90 (m, 1H), 3.77 (d, J = 14.9 Hz, 1H), 3.61 (d, J = 4.3 Hz, 2H), 3.54-3.45 (m, 1H), 3.42-3.35 (m, 1H), 3.27-3 24 (m, 1H), 3 15 (d, J = 70 Hz, 1H), 2.59-2.56 (m, 2H), 2.47 (s, 3H), 2.22-2.10 (m, 7H), 2.06-1.99 (m, 1H), 1.88-1.67 (s, 9H), 1.38 (d, J = 7.0 Hz, 3H), 1.12-1.10 (m, 1H), 0.94 (s, 9H) |

TABLE 53-continued

Characterization data for intermediates prepared according to above.

| Intermediate | Structure | Chemical Name | MS: [(M + 1)]+ | 1H NMR |
|---|---|---|---|---|
| J154 | 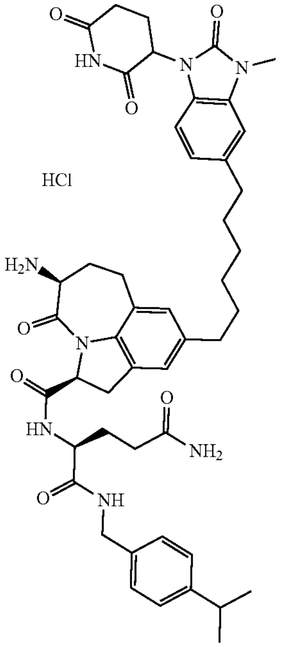 [SMILES: CC(C)c1ccc(CNC(=O)[C@H](CCC(N)=O)NC(=O)[C@@H]2Cc3cc(CCCCCCc4ccc5c(c4)n(C)c(=O)n5C4CCC(=O)NC4=O)cc4c3N2C(=O)[C@@H](N)CC4)cc1 ; Cl] | (2S)-2-[[(2S,11S)-11-amino-6-[6[1-(2,6-dioxopiperidin-3-yl)-3-methyl-2-oxo-1,3-benzodiazol-5-yl]hexyl]-12-oxo-1-azatricyclo [6.4.1.0^[4.13]]-trideca-4(13),5,7-trien-2-yl]]formamido]-N-[(4-isopropylphenyl) methyl] pentanediamide hydrochloride | 847.10 | (400 MHz, DMSO-$d_6$) δ 11.09 (s, 1H), 8.53-8.39 (m, 4H), 7.33 (s, 1H), 7.18-7.10 (m, 4H), 7.05-6.98 (m, 2H), 6.93 (s, 1H), 6.90-6.84 (m, 2H), 6.80 (s, 1H), 5.36-5.33 (m, 1H), 5.19-5.14 (m, 1H), 4.26-4.14 (m, 4H), 3.46-3.36 (m, 1H), 3.32 (s, 3H), 3.12-3.08 (m, 2H), 2.96-2.80 (m, 3H), 2.75-2.67 (m, 1H), 2.65-2.58 (m, 4H), 2.49-2.46 (m, 1H), 2.23-2.20 (m, 1H), 2.14-2.10 (m, 2H), 2.02-2.00 (m, 2H), 1.92-1.88 (m, 1H), 1.80-1.78 (m, 1H), 1.57-1.54 (m, 4H), 1.36-1.30 (m, 4H), 1.17 (d, J = 6.9 Hz, 6H) |
| J155 | 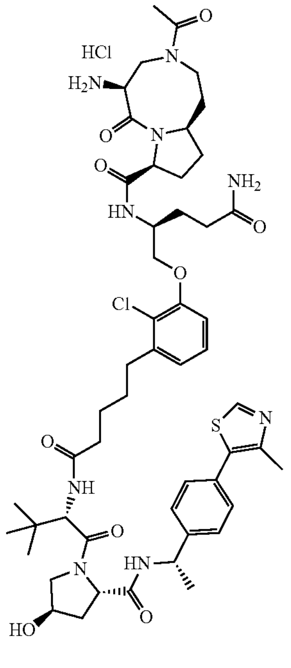 [SMILES: CC(=O)N1CC[C@H]2CC[C@@H](C(=O)N[C@@H](CCC(N)=O)COc3cccc(CCCCC(=O)N[C@H](C(=O)N4C[C@H](O)C[C@H]4C(=O)N[C@@H](C)c4ccc(-c5scnc5C)cc4)C(C)(C)C)c3Cl)N2C(=O)[C@@H](N)C1 ; Cl] | (2S,4R)-1-[(2S)-2-(5-[3-[(2S)-2-[[(5S,8S,10aR)-3-acetyl-5-amino-6-oxo-octahydropyrrolo[1,2-a][1,5]diazocin-8-yl]formamido]-4-carbamoylbutoxy]-2-chlorophenyl] pentanamido)-3,3-dimethylbutanoyl]-4-hydroxy-N-[(1S)-1-(4-(4-methyl-1,3-thiazol-5-yl)phenyl]ethyl] pyrrolidine-2-carboxamide hydrochloride | 1020.45 | (400 MHz, DMSO-$d_6$) δ 9.12 (s, 1H), 8.56 (s, 2H), 8.43 (d, J = 7.8 Hz, 1H), 8.21 (d, J = 8.2 Hz, 1H), 7.85 (d, J = 9.3 Hz, 1H), 7.49-7.43 (m, 2H), 7.40 (d, J = 8.3 Hz, 2H), 7.28 (s, 1H), 7.20 (t, J = 7.9 Hz, 1H), 6.99 (dd, J = 8.3, 1.4 Hz, 1H), 6.95-6.88 (m, 1H), 6.78 (s, 1H), 4.92 (p, J = 7.2 Hz, 1H), 4.52 (d, J = 9.3 Hz, 1H), 4.48-4.34 (m, 2H), 4.28 (s, 2H), 4.11-4.00 (m, 3H), 3.93 (d, J = 8.7 Hz, 1H), 3.78 (s, 1H), 3.71-3.57 (m, 4H), 3.53-3.36 (m, 1H), 3.31-3.15 (m, 1H), 2.71-2.67 (m, 2H), 2.48 (s, 3H), 2.40-2.26 (m, 1H), 2.19-2.15 (m, 6H), 2.11 (s, 1H), 2.08-2.00 (m, 1H), 1.98-1.85 (m, 3H), 1.85-1.66 (m, 3H), 1.61-1.43 (m, 6H), 1.38 (d, J = 7.0 Hz, 3H), 0.94 (s, 9H) |

TABLE 53-continued

| Characterization data for intermediates prepared according to above. | | | | |
|---|---|---|---|---|
| Intermediate | Structure | Chemical Name | MS: [(M + 1)]$^+$ | $^1$H NMR |
| J156 | 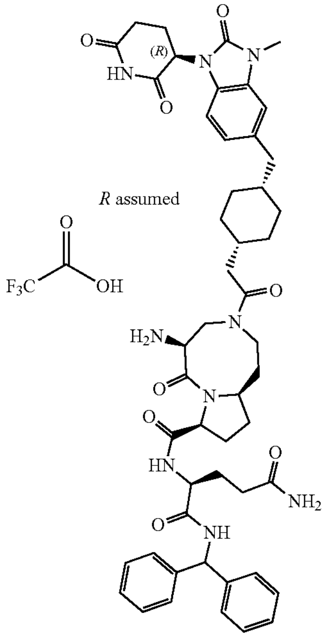 *R* assumed | (2S)-2-[[(5S,8S,10aR)-5-amino-6-oxo-3-[2-[(1s,4s)-4-[[1-(2,6-dioxopiperidin-3-yl)-3-methyl-2-oxo-1,3-benzodiazol-5-yl]methyl]cyclohexyl]acetyl]-octahydropyrrolo[1,2-a][1,5]diazocin-8-yl]formamido]-N-(diphenylmethyl)pentanediamide trifluoroacetate | 916.80 | (300 MHz, DMSO-$d_6$) δ 11.11 (s, 1H), 8.87 (d, J = 8.4 Hz, 1H), 8.55-8.18 (m, 4H), 7.38-7.25 (m, 12H), 7.10-6.92 (m, 2H), 6.90-6.71 (m, 2H), 6.12 (d, J = 8.2 Hz, 1H), 5.36 (dd, J = 12.7, 5.4 Hz, 1H), 4.57-4.33 (m, 3H), 4.23-4.17 (m, 1H), 4.13-3.74 (m, 2H), 3.40 (q, J = 7.0 Hz, 1H), 3.33 (s, 3H), 3.05-2.86 (m, 1H), 2.80-2.57 (m, 4H), 2.42-2.06 (m, 4H), 2.06-1.65 (m, 9H), 1.46-1.32 (m, 9H), 1.11 (t, J = 7.0 Hz, 1H) |
| J157 | 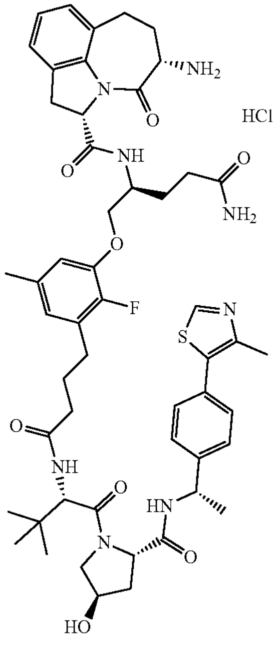 | (2S,4R)-1-[(2S)-2-(4-[3-[(2S)-2-[[(2S,11S)-11-amino-12-oxo-1-azatricyclo[6.4.1.0^[4,13]]trideca-4(13),5,7-trien-2-yl]formamido]-4-carbamoylbutoxy]-2-fluoro-5-methylphenyl]butanamido)-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride | 981.45 | (300 MHz, DMSO-$d_6$) δ 9.04 (s, 1H), 8.57-8.45 (m, 3H), 8.38 (d, J = 7.8 Hz, 1H), 8.27 (d, J = 7.2 Hz, 1H), 7.86 (d, J = 9.2 Hz, 1H), 7.47-7.35 (m, 4H), 7.09-6.94 (m, 4H), 6.81 (d, J = 7.8 Hz, 1H), 6.60 (d, J = 6.1 Hz, 1H), 5.10-5.07 (m, 2H), 4.91 (t, J = 7.2 Hz, 1H), 4.56-4.49 (m, 1H), 4.42 (t, J = 7.9 Hz, 1H), 4.30-4.25 (m, 1H), 4.22-4.12 (m, 1H), 4.04-3.87 (m, 4H), 3.62-3.59 (m, 2H), 3.51-3.34 (m, 2H), 3.18-3.09 (m, 2H), 2.91-2.80 (m, 1H), 2.45 (s, 3H), 2.32-2.25 (m, 1H), 2.22 (s, 3H), 2.19-2.08 (m, 3H), 2.07-1.94 (m, 2H), 1.87-1.63 (m, 6H), 1.37 (s, 3H), 0.94 (s, 9H) |

TABLE 53-continued

| Characterization data for intermediates prepared according to above. | | | | |
|---|---|---|---|---|
| Intermediate | Structure | Chemical Name | MS: $[(M + 1)]^+$ | $^1H$ NMR |
| J158 | 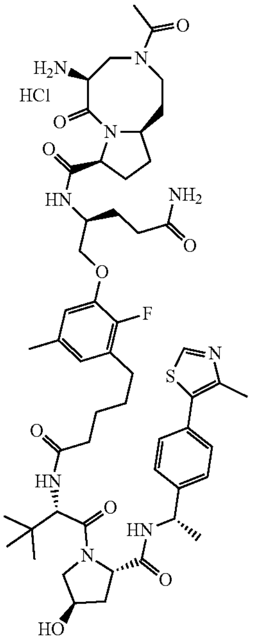 [SMILES: CC(=O)N1CC[C@H]2CC[C@@H](C(=O)N[C@@H](CCC(N)=O)COc3cc(C)cc(CCCCC(=O)N[C@H](C(=O)N4C[C@H](O)C[C@H]4C(=O)N[C@@H](C)c4ccc(-c5scnc5C)cc4)C(C)(C)C)c3F)N2C(=O)[C@@H](N)C1 ; Cl] | (2S,4R)-1-[(2S)-2-(5-[3-[(2S)-2-[[(5S,8S,10aR)-3-acetyl-5-amino-6-oxo-octahydropyrrolo[1,2-a][1,5]diazocin-8-yl]formamido]-4-carbamoylbutoxy]-2-fluoro-5-methylphenyl]pentanamido)-3,3-dimethylbutanoyl)-4-hydroxy-N-[(1S)-1-[4-(4-methyl-1,3-thiazol-5-yl)phenyl]ethyl]pyrrolidine-2-carboxamide hydrochloride | 1018.40 | $^1H$ NMR (400 MHz, DMSO-$d_6$) δ 9.32 (s, 1H), 8.69-8.55 (m, 2H), 8.50-8.39 (m, 2H), 8.26 (d, J = 8.0 Hz, 1H), 7.83 (d, J = 9.2 Hz, 1H), 7.49-7.38 (m, 5H), 6.85-6.78 (m, 1H), 6.61 (d, J = 5.8 Hz, 1H), 4.92 (p, J = 7.2 Hz, 1H), 4.54-4.35 (m, 4H), 4.32-4.17 (m, 3H), 4.10 (d, J = 13.7 Hz, 1H), 4.05-3.94 (m, 2H), 3.93-3.84 (m, 1H), 3.80-3.69 (m, 1H), 3.68-3.53 (m, 3H), 3.51-3.32 (m, 1H), 3.30-3.09 (m, 2H), 2.49 (s, 3H), 2.22 (s, 3H), 2.20-2.07 (m, 7H), 2.06-1.98 (m, 1H), 1.97-1.63 (m, 8H), 1.53-1.42 (m, 5H), 1.37 (s, 3H), 0.93 (s, 9H) |
| J159 | 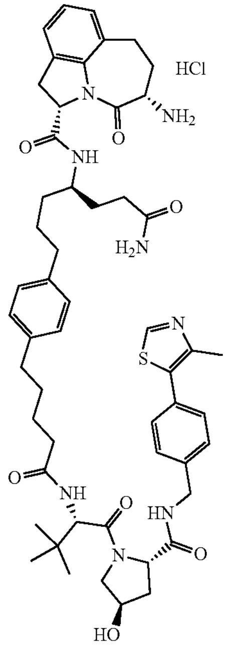 [SMILES: Cc1ncsc1-c1ccc(CNC(=O)[C@@H]2C[C@@H](O)CN2C(=O)[C@@H](NC(=O)CCCCc2ccc(CCC[C@H](CCC(N)=O)NC(=O)[C@@H]3Cc4cccc5c4N3C(=O)[C@@H](N)CC5)cc2)C(C)(C)C)cc1 ; Cl] | (2S,4R)-1-[(2S)-2-(5-[4-[(4R)-4-[[(2S,11S)-11-amino-12-oxo-1-azatricyclo[6.4.1.0^[4,13]]trideca-4(13),5,7-trien-2-yl]formamido]-6-carbamoylhexyl]phenyl]pentanamido)-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride | 975.55 | $^1H$ NMR (400 MHz, DMSO-$d_6$) δ 9.01 (s, 1H), 8.39 (d, J = 7.9 Hz, 4H), 7.91 (dd, J = 60.7, 9.1 Hz, 2H), 7.48-7.36 (m, 4H), 7.13-7.02 (m, 7H), 6.68 (s, 1H), 5.05 (d, J = 10.8 Hz, 1H), 4.96-4.89 (m, 1H), 4.52 (d, J = 9.3 Hz, 1H), 4.43 (t, J = 8.0 Hz, 1H), 4.24 (d, J = 35.5 Hz, 2H), 3.72-3.61 (m, 2H), 3.52-3.33 (m, 2H), 3.15 (s, 2H), 2.46 (s, 5H), 2.37-1.93 (m, 10H), 1.79 (s, 1H), 1.63-1.59 (m, 2H), 1.51-1.22 (m, 12H), 0.94 (s, 9H) |

TABLE 53-continued

Characterization data for intermediates prepared according to above.

| Intermediate | Structure | Chemical Name | MS: $[(M + 1)]^+$ | $^1$H NMR |
|---|---|---|---|---|
| J160 | 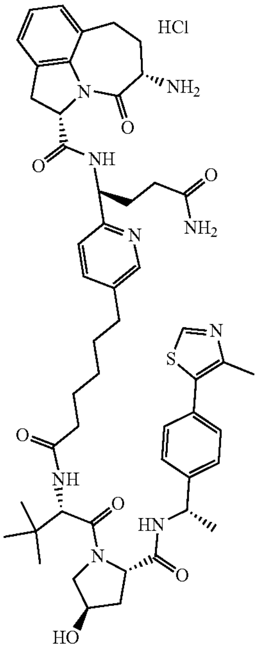 [SMILES: Cc1ncsc1-c1ccc([C@H](C)NC(=O)[C@@H]2C[C@@H](O)CN2C(=O)[C@@H](NC(=O)CCCCCc2ccc([C@@H](CCC(N)=O)NC(=O)[C@@H]3Cc4cccc5c4N3C(=O)[C@@H](N)CC5)nc2)C(C)(C)C)cc1 ; Cl] HCl | (2S,4R)-1-[(2S)-2-(6-[6-[(1S)-1-[[(2S,11S)-11-amino-12-oxo-1-azatricyclo[6.4.1.0^[4,13]]trideca-4(13),5,7-trien-2-yl]formamido]-3-carbamoylpropyl]pyridin-3-yl]hexanamido)-3,3-dimethylbutanoyl]-4-hydroxy-N-[(1S)-1-[4-(4-methyl-1,3-thiazol-5-yl)phenyl]ethyl]pyrrolidine-2-carboxamide | $[(M - H)]^-$ = 946.95 | (300 MHz, DMSO-$d_6$) δ 9.18-9.17 (d, J = 7.4 Hz, 1H), 9.05 (s, 1H), 8.72-8.71 (d, J = 2.1 Hz, 1H), 8.60-8.54 (m, 3H), 8.50-8.39 (m, 2H), 7.98-7.95 (d, J = 8.4 Hz, 1H), 7.83-7.80 (d, J = 9.3 Hz, 1H), 7.48-7.32 (m, 4H), 7.07-7.05 (m, 2H), 7.01-6.93 (m, 1H), 6.83 (s, 1H), 5.17-5.13 (dd, J = 11.0, 3.5 Hz, 1H), 4.96-4.88 (m, 2H), 4.53-4.50 (d, J = 9.3 Hz, 1H), 4.47-4.41 (m, 1H), 4.29 (s, 1H), 4.24-4.17 (m, 1H), 3.64-3.61 (d, J = 4.1 Hz, 2H), 3.52-3.45 (m, 1H), 3.14-3.12 (m, 2H), 3.03-2.99 (t, J = 7.8 Hz, 2H), 2.84-2.79 (dd, J = 17.3, 3.3 Hz, 1H), 2.47 (s, 3H), 2.31-2.24 (m, 2H), 2.20-2.12 (m, 2H), 2.08 (s, 4H), 2.06-1.94 (m, 2H), 1.84-1.67 (m, 3H), 1.58-1.47 (m, 2H), 1.39-1.37 (d, J = 7.0 Hz, 3H), 1.33-1.22 (m, 2H), 0.93 (s, 9H) |
| J161 | HCl 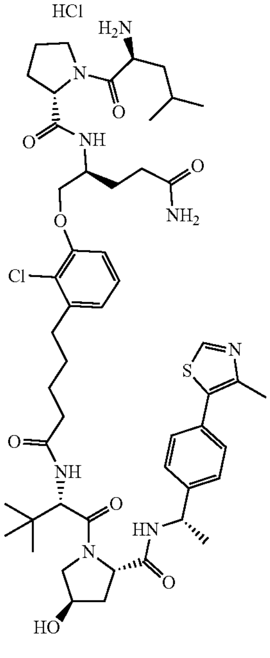 [SMILES: Cl ; Cc1ncsc1-c1ccc([C@H](C)NC(=O)[C@@H]2C[C@@H](O)CN2C(=O)[C@@H](NC(=O)CCCCc2cccc(OC[C@H](CCC(N)=O)NC(=O)[C@@H]3CCCN3C(=O)[C@@H](N)CC(C)C)c2Cl)C(C)(C)C)cc1] | (2S,4R)-1-[(2S)-2-(5-[3-[(2S)-2-[[(2S)-1-[(2S)-2-amino-4-methylpentanoyl]-pyrrolidin-2-yl]formamido]-4-carbamoylbutoxy]-2-chlorophenyl]pentanamido)-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride | 979.45 | (400 MHz, DMSO-$d_6$) δ 9.08 (s, 1H), 8.42 (d, J = 7.8 Hz, 1H), 8.25 (s, 2H), 8.06 (d, J = 8.1 Hz, 1H), 7.85 (d, J = 9.2 Hz, 1H), 7.45 (d, J = 2.3 Hz, 2H), 7.39 (d, J = 8.4 Hz, 2H), 7.22-7.18 (m, 2H), 7.06-6.95 (m, 1H), 6.91 (dd, J = 7.7. 1.3 Hz, 1H), 6.79 (s, 1H), 4.92 (p, J = 7.2 Hz, 1H), 4.52 (d, J = 9.4 Hz, 1H), 4.49-4.33 (m, 2H), 4.28 (s, 1H), 4.08 (s, 3H), 4.05-3.96 (m, 1H), 3.96-3.84 (m, 1H), 3.80-3.70 (m, 2H), 3.70-3.57 (m, 2H), 3.53-3.41 (m, 1H), 3.45-3.37 (m, 1H), 2.69 (s, 3H), 2.58-2.55 (m, 1H), 2.47 (s, 3H), 2.33-2.29 (m, 1H), 2.19-2.15 (m, 2H), 2.09-1.94 (m, 2H), 1.90-1.70 (m, 4H), 1.63-1.47 (m, 6H), 1.38 (d, J = 7.1 Hz, 3H), 0.94 (s, 15H) |

TABLE 53-continued

| Intermediate | Structure | Chemical Name | MS: [(M + 1)]+ | 1H NMR |
|---|---|---|---|---|
| Characterization data for intermediates prepared according to above. | | | | |
| J162 | HCl 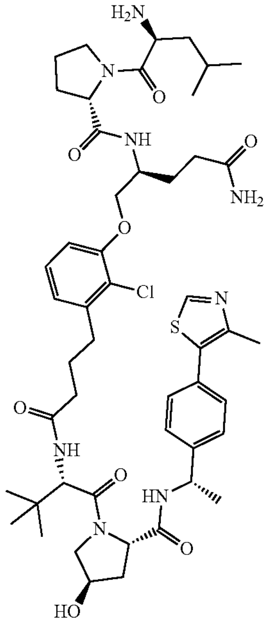 | (2S,4R)-1-[(2S)-2-(4-[3-[(2S)-2-[[(2S)-1-[(2S)-2-amino-4-methylpentanoyl] pyrrolidin-2-yl]formamido]-4-carbamoylbutoxy]-2-chlorophenyl] butanamido)-3,3-dimethylbutanoyl]-4-hydroxy-N-[(1S)-1-[4-(4-methyl-1,3-thiazol-5-yl)phenyl]ethyl] pyrrolidine-2-carboxamide hydrochloride | 965.45 | (400 MHz, DMSO-$d_6$) δ 9.09 (s, 1H), 8.42 (d, J = 7.7 Hz, 1H), 8.30-8.21 (m, 2H), 8.05 (d, J = 8.0 Hz, 1H), 7.89 (d, J = 9.3 Hz, 1H), 7.45 (d, J = 8.3 Hz, 2H), 7.39 (d, J = 8.3 Hz, 2H), 7.27-7.17 (m, 2H), 6.99 (d, J = 8.3, 1H), 6.89 (d, J = 7.6, 1H), 6.79 (s, 1H), 4.93-4.89 (m, 1H), 4.55-4.50 (m, 1H), 4.43 (t, J = 8.0 Hz, 1H), 4.38-4.34 (m, 1H), 4.29-4.27 (m, 1H), 4.08-4.04 (m, 2H), 4.04-3.97 (m, 1H), 3.94-3.91 (m, 1H), 3.76-3.72 (m, 1H), 3.62-3.59 (m, 2H), 3.46-3.39 (m, 1H), 2.67 (t, J = 7.4 Hz, 2H), 2.47 (s, 3H), 2.32-2.28 (m, 1H), 2.21-2.13 (m, 3H), 2.10-1.93 (m, 3H), 1.80-1.71 (m, 9H), 1.58-1.54 (m, 2H), 1.37 (d, J = 7.0 Hz, 3H), 0.99-0.90 (m, 15H) |
| J163 | HCl 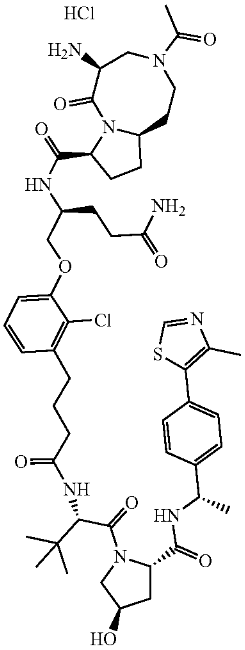 [SMILES: CC(=O)N1CC[C@H]2CC[C@@H](C(=O)N[C@@H](CCC(N)=O)COc3cccc(CCCC(=O)N[C@H](C(=O)N4C[C@H](O)C[C@H]4C(=O)N[C@@H](C)c4ccc(-c5scnc5C)cc4)C(C)(C)C)c3Cl)N2C(=O)[C@@H](N)C1 ; Cl] | (2S,4R)-1-[(2S)-2-(4-[3-[(2S)-2-[[(5S,8S,10aR)-3-acetyl-5-amino-6-oxo-octahydropyrrolo[1,2-a][1,5]diazocin-8-yl]formamido)-4-carbamoylbutoxy]-2-chlorophenyl] butanamido)-3,3-dimethylbutanoyl]-4-hydroxy-N-[(1S)-1-[4-(4-methyl-1,3-thiazol-5-yl)phenyl]ethyl] pyrrolidine-2-carboxamide hydrochloride | 1006.11 | (400 MHz, DMSO-$d_6$) δ 9.11 (d, J = 2.4 Hz, 1H), 8.59 (s, 2H), 8.43 (d, J = 8.1 Hz, 2H), 8.26-8.19 (m, 1H), 7.88 (d, J = 9.2 Hz, 1H), 7.50 (s, 2H), 7.45 (d, J = 8.3 Hz, 2H), 7.25 (s, 2H), 7.19 (d, J = 8.0 Hz, 1H), 7.03-6.97 (m, 1H), 6.89 (d, J = 7.5 Hz, 1H), 4.92 (p, J = 6.9 Hz, 1H), 4.65 (dd, J = 6.6, 2.4 Hz, 1H), 4.53 (d, J = 9.3 Hz, 1H), 4.46-4.35 (m, 2H), 4.34-4.17 (m, 3H), 4.04 (d, J = 17.0 Hz, 1H), 3.93 (d, J = 9.3 Hz, 1H), 3.87-3.64 (m, 2H), 3.60 (q, J = 3.4 Hz, 2H), 3.57-3.55 (m, 2H), 3.54-3.43 (m, 1H), 3.42-3.33 (m, 1H), 3.31-3.10 (m, 1H), 2.70-2.63 (m, 2H), 2.47 (s, 3H), 2.31-2.28 (m, 2H), 2.17-2.13 (m, 6H), 2.11-1.97 (m, 2H), 1.96-1.64 (m, 3H), 1.48-1.41 (m, 2H), 1.37-1.31 (m, 3H), 1.23-1.19 (m, 1H), 0.94 (s, 9H) |

TABLE 53-continued

| Characterization data for intermediates prepared according to above. | | | | |
|---|---|---|---|---|
| Intermediate | Structure | Chemical Name | MS: [(M + 1)]+ | 1H NMR |
| J164 | 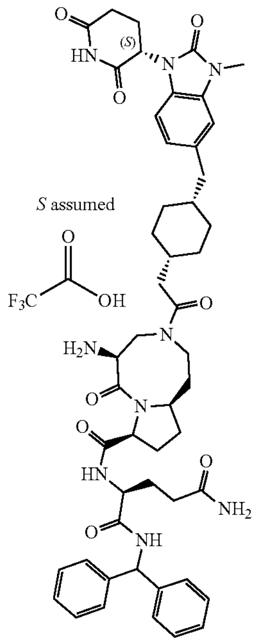 | (2S)-2-[[(5S,8S,10aR)-5-amino-6-oxo-3-[2-[(1s,4s)-4-[[1-(2,6-dioxopiperidin-3-yl)-3-methyl-2-oxo-1,3-benzodiazol-5-yl]methyl]cyclohexyl]acetyl]-octahydropyrrolo[1,2-a][1,5]diazocin-8-yl]formamido]-N-(diphenylmethyl)pentanediamide trifluoroacetate | 916.40 | (300 MHz, DMSO-$d_6$) δ 11.11 (s, 1H), 8.87 (d, J = 8.4 Hz, 1H), 8.49-8.23 (m, 4H), 7.43-7.18 (m, 12H), 7.05-6.93 (m, 2H), 6.91-6.69 (m, 2H), 6.13 (d, J = 8.2 Hz, 1H), 5.36 (dd, J = 12.7, 5.4 Hz, 1H), 4.53-4.42 (m, 3H), 4.31-4.11 (m, 1H), 4.09-3.77 (m, 1H), 3.34 (s, 3H), 3.29-2.81 (m, 3H), 2.80-2.57 (m, 4H), 2.40-1.61 (m, 13H), 1.53-1.30 (m, 9H) |
| J165 | 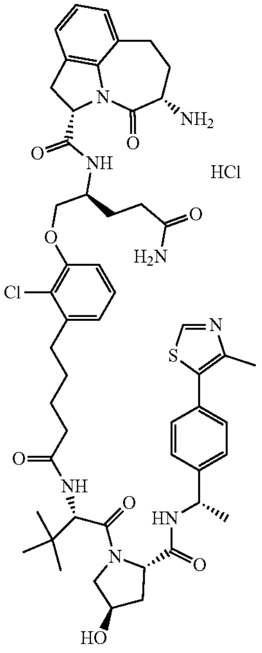 [SMILES: Cc1ncsc1-c1ccc([C@H](C)NC(=O)[C@@H]2C[C@@H](O)CN2C(=O)[C@@H](NC(=O)CCCCc2cccc(OC[C@H](CCC(N)=O)NC(=O)[C@@H]3Cc4cccc5c4N3C(=O)[C@@H](N)CC5)c2Cl)C(C)(C)C)cc1 ; Cl] | (2S,4R)-1-[(2S)-2-(5-[3-[(2S)-2-[[(2S,11S)-11-amino-12-oxo-1-azatricyclo [6.4.1.0^[4,13]] trideca-4(13),5,7-trien-2-yl]formamido]-4-carbamoylbutoxy]-2-chlorophenyl] pentanamido)-3,3-dimethylbutanoyl]-4-hydroxy-N-[(1S)-1-[4-(4-methyl-1,3-thiazol-5-yl)phenyl]ethyl] pyrrolidine-2-carboxamide hydrochloride | 997.35 | (300 MHz, DMSO-$d_6$) δ 9.19 (d, J = 4.8 Hz, 1H), 8.62 (s, 3H), 8.46 (d, J = 7.7 Hz, 1H), 8.36 (d, J = 7.0 Hz, 1H), 7.86 (d, J = 9.2 Hz, 1H), 7.60 (s, 3H), 7.26 (s, 2H), 7.20 (t, J = 7.9 Hz, 1H), 7.09-7.03 (m, 3H), 6.99 (s, 1H), 6.92 (d, J = 7.6 Hz, 1H), 5.12 (d, J = 10.5 Hz, 1H), 4.98-4.87 (m, 1H), 4.53 (d, J = 9.1 Hz, 1H), 4.45 (t, J = 8.1 Hz, 1H), 4.29 (s, 1H), 4.16 (s, 1H), 4.04 (d, J = 7.0 Hz, 2H), 4.00-3.96 (m, 1H), 3.53-3.31 (m, 2H), 3.18-3.12 (m, 3H), 2.99-2.95 (m, 1H), 2.72-2.68 (m, 3H), 2.47 (s, 3H), 2.31 (s, 2H), 2.21-2.17 (m, 1H), 2.11-1.98 (m, 2H), 1.95-1.85 (m, 1H), 1.78 (s, 3H), 1.57-1.53 (m, 5H), 1.43-1.34 (m, 3H), 0.95 (s, 9H) |

TABLE 53-continued

| Characterization data for intermediates prepared according to above. | | | | |
|---|---|---|---|---|
| Intermediate | Structure | Chemical Name | MS: [(M + 1)]+ | $^1$H NMR |
| J166 | 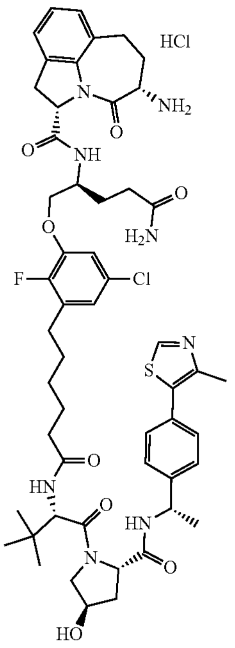 [SMILES: Cc1ncsc1-c1ccc([C@H](C)NC(=O)[C@@H]2C[C@@H](O)CN2C(=O)[C@@H](NC(=O)CCCCCc2cc(Cl)cc(OC[C@H](CCC(N)=O)NC(=O)[C@@H]3Cc4cccc5c4N3C(=O)[C@@H](N)CC5)c2F)C(C)(C)C)cc1 ; Cl] | (2S,4R)-1-[(2S)-2-(6-[3-[(2S)-2-[[(2S,11S)-11-amino-12-oxo-1-azatricyclo [6.4.1.0^[4,13]] trideca-4(13),5,7-trien-2-yl]formamido]-4-carbamoylbutoxy]-5-chloro-2-fluorophenyl] hexanamido)-3,3-dimethylbutanoyl]-4-hydroxy-N-[(1S)-1-[4-(4-methyl-1,3-thiazol-5-yl)phenyl]ethyl] pyrrolidine-2-carboxamide hydrochloride | 1029.25 | (400 MHz, DMSO-$d_6$) δ 9.03 (d, J = 5.4 Hz, 1H), 8.48 (s, 2H), 8.40 (d, J = 7.7 Hz, 1H), 8.30 (d, J = 7.3 Hz, 1H), 7.81 (d, J = 9.2 Hz, 1H), 7.44 (d, J = 8.0 Hz, 2H), 7.38 (d, J = 8.1 Hz, 2H), 7.30 (s, 1H), 7.14 (d, J = 7.2 Hz, 1H), 7.05 (d, J = 4.7 Hz, 2H), 7.01 (d, J = 7.3 Hz, 1H), 6.93 (m, 1H), 6.80 (s, 1H), 5.09 (d, J = 11.0 Hz, 1H), 4.91 (q, J = 7.3 Hz, 1H), 4.42 (t, J = 8.0 Hz, 3H), 4.30-4.26 (m, 1H), 4.20 (d, J = 7.9 Hz, 1H), 4.09-4.03 (m, 1H), 3.98-3.95 (m, 2H), 3.47-3.34 (m, 2H), 3.15-3.13 (m, 2H), 2.87 (d, J = 16.5 Hz, 1H), 2.46 (s, 3H), 2.30-2.18 (m, 3H), 2.15-2.11 (m, 3H), 2.03-1.99 (m, 1H), 1.87-1.67 (m, 4H), 1.54-1.45 (m, 5H), 1.38 (d, J = 7.2 Hz, 3H), 1.29-1.20 (m, 3H), 0.93 (s, 9H) |
| J167 | 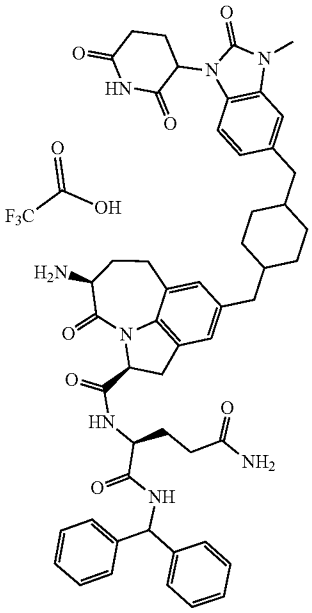 [SMILES: O=C(O)C(F)(F)F ; Cn1c(=O)n(C2CCC(=O)NC2=O)c2ccc(CC3CCC(Cc4cc5c6c(c4)C[C@@H](C(=O)N[C@@H](CCC(N)=O)C(=O)NC(c4ccccc4)c4ccccc4)N6C(=O)[C@@H](N)CC5)CC3)cc21] | (2S)-2-[[(2S,11S)-11-amino-6-[(4-[[1-(2,6-dioxopiperidin-3-yl)-3-methyl-2-oxo-1,3-benzodiazol-5-yl]methyl] cyclohexyl)methyl]-12-oxo-1-azatricyclo [6.4.1.0^[4,13]] trideca-4(13),5,7-trien-2-yl]formainido]-N-(diphenylmethyl) pentanediamide trifluoroacetate | 907.55 | (400 MHz, DMSO-$d_6$) δ 11.09 (s, 1H), 8.83 (d, J = 8.8 Hz, 1H), 8.37-8.33 (m, 3H), 7.34-7.22 (m, 11H), 7.06-6.95 (m, 2H), 6.92-6.90 (m, 1H), 4.22-4.20 (m, 1H), 3.32 (d, J = 5.2 Hz, 2H), 3.12-3.10 (m, 1H), 2.91-2.86 (m, 2H), 2.62 (d, J = 9.7 Hz, 2H), 2.37 (d, J = 7.5 Hz, 1H), 2.20-1.96 (m, 5H), 1.92-1.90 (m, 1H), 1.82-1.79 (m, 1H), 1.66-1.62 (m, 2H), 1.40 (d, J = 6.7 Hz, 3H), 1.29-1.21 (m, 5H), 1.19 (d, J = 10.8 Hz, 2H), 0.95-0.81 (m, 5H) |

TABLE 53-continued

Characterization data for intermediates prepared according to above.

| Intermediate | Structure | Chemical Name | MS: [(M + 1)]+ | 1H NMR |
|---|---|---|---|---|
| J168 | 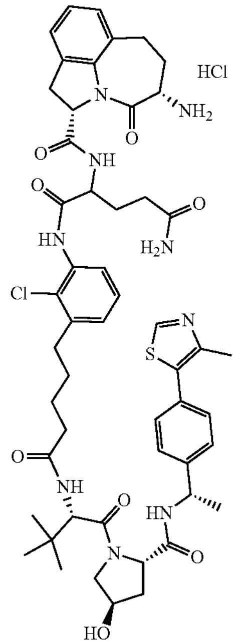 [SMILES: Cc1ncsc1-c1ccc([C@H](C)NC(=O)[C@@H]2C[C@@H](O)CN2C(=O)[C@@H](NC(=O)CCCCc2cccc(NC(=O)C(CCC(N)=O)NC(=O)[C@@H]3Cc4cccc5c4N3C(=O)[C@@H](N)CC5)c2Cl)C(C)(C)C)cc1 ; Cl] | 2-[((2S,11S)-11-amino-12-oxo-1-azatricyclo [6.4.1.0^[4,13]] trideca-4(13),5,7-trien-2-yl]formamido]-N-[2-chloro-3-(4-[[(2S)-1-[(2S,4R)-4-hydroxy-2-[[(1S)-1-[4-(4-methyl-1,3-thiazol-5-yl)phenyl]ethyl] carbamoyl] pyrrolidin-1-yl]-3,3-dimethyl-1-oxobutan-2-yl]carbamoyl]butyl) phenyl] pentanediamide hydrochloride | 1010.35 | (400 MHz, DMSO-$d_6$) δ 9.55 (d, J = 12.7 Hz, 1H), 9.06 (s, 1H), 8.60 (dd, J = 21.6, 7.7 Hz, 1H), 8.48 (d, J = 14.4 Hz, 3H), 8.41 (d, J = 7.7 Hz, 1H), 7.88-7.81 (m, 1H), 7.59 (dd, J = 24.4, 7.9 Hz, 1H), 7.48-7.32 (m, 4H), 7.25 (dd, J = 15.5, 7.3 Hz, 1H), 7.19-6.96 (m, 4H), 6.85 (s, 1H), 5.20 (s, 1H), 4.92 (t, J = 7.2 Hz, 1H), 4.52 (d, J = 9.7 Hz, 1H), 4.43 (t, J = 7.9 Hz, 2H), 4.28 (s, 1H), 4.22-4.17 (m, 2H), 3.63 (d, J = 18.5 Hz, 3H), 3.54-3.45 (m, 1H), 3.15 (s, 2H), 3.01 (d, J = 16.7 Hz, 1H), 2.73-2.69 (m, 2H), 2.47 (s, 3H), 2.29-2.25 (m, 3H), 2.20-2.16 (m, 1H), 2.05-2.01 (m, 2H), 1.92-1.88 (m, 1H), 1.85-1.73 (m, 1H), 1.56-1.52 (m, 5H), 1.38 (d, J = 7.0 Hz, 3H), 0.94 (s, 9H) |
| J169 | 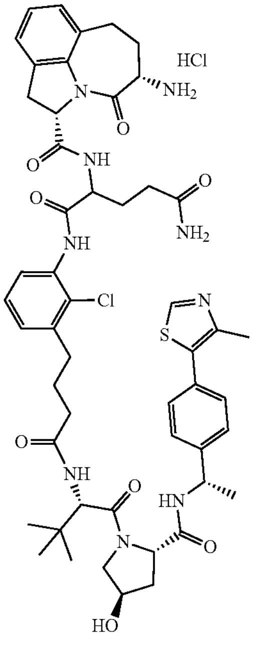 [SMILES: Cc1ncsc1-c1ccc([C@H](C)NC(=O)[C@@H]2C[C@@H](O)CN2C(=O)[C@@H](NC(=O)CCCc2cccc(NC(=O)C(CCC(N)=O)NC(=O)[C@@H]3Cc4cccc5c4N3C(=O)[C@@H](N)CC5)c2Cl)C(C)(C)C)cc1 ; Cl] | (2S)-2-[[(2S,11S)-11-amino-12-oxo-1-azatricyclo [6.4.1.0^[4,13]] trideca-4(13),5,7-trien-2-yl]formamido]-N-[2-chloro-3-(3-[[(2S)-1-[(2S,4R)-4-hydroxy-2-[[1S)-1-[4-(4-methyl-1,3-thiazol-5-yl)phenyl]ethyl] carbamoyl] pyrrolidin-1-yl]-3,3-dimethyl-1-oxobutan-2-yl]carbamoyl]propyl) phenyl] pentanediamide hydrochloride | 996.40 | (400 MHz, DMSO-$d_6$) δ 9.49 (s, 1H), 8.99 (s, 1H), 8.40 (t, J = 9.0 Hz, 2H), 7.90 (d, J = 9.2 Hz, 1H), 7.61 (dd, J = 23.2, 8.1 Hz, 1H), 7.44 (d, J = 8.3 Hz, 2H), 7.38 (d, J = 8.3 Hz, 2H), 7.33 (s, 1H), 7.27-7.23 (m, 1H), 7.15-7.02 (m, 4H), 7.02-6.92 (m, 2H), 6.82 (s, 1H), 5.14 (dd, J = 14.8, 6.0 Hz, 2H), 4.93 (p, J = 7.2 Hz, 1H), 4.55 (d, J = 9.6 Hz, 1H), 4.45 (s, 1H), 4.29 (s, 1H), 4.04 (d, J = 8.3 Hz, 1H), 3.62 (d, J = 3.1 Hz, 2H), 3.48-3.44 (m, 1H), 3.03 (s, 3H), 2.68 (d, J = 7.7 Hz, 2H), 2.46 (s, 3H), 2.33-2.29 (m, 1H), 2.21-2.17 (m, 3H), 2.08-2.04 (m, 2H), 2.03-1.99 (m, 1H), 1.90-1.86 (m, 1H), 1.81-1.77 (m, 2H), 1.39-1.35 (m, 5H), 1.27-1.22 (m, 1H), 0.95 (s, 9H) |

TABLE 53-continued

Characterization data for intermediates prepared according to above.

| Intermediate | Structure | Chemical Name | MS: [(M + 1)]+ | 1H NMR |
|---|---|---|---|---|
| J170 | 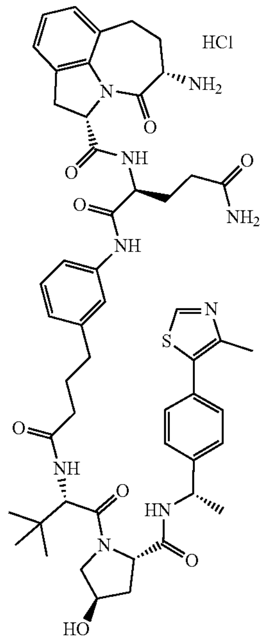 [SMILES: Cc1ncsc1-c1ccc([C@H](C)NC(=O)[C@@H]2C[C@@H](O)CN2C(=O)[C@@H](NC(=O)CCCc2cccc(NC(=O)[C@H](CCC(N)=O)NC(=O)[C@@H]3Cc4cccc5c4N3C(=O)[C@@H](N)CC5)c2)C(C)(C)C)cc1 ; Cl] | (2S)-2-[[2S,11S)-11-amino-12-oxo-1-azatricyclo [6.4.1.0^[4,13]] trideca-4(13),5,7-trien-2-yl]formamido]-N-[3-(3-[[(2S)-1-[(2S,4R)-4-hydroxy-2-[[(1S)-1-[4-(4-methyl-1,3-thiazol-5-yl)phenyl]ethyl] carbamoyl] pyrrolidin-1-yl]-3,3-dimethyl-1-oxobutan-2-yl]carbamoyl]propyl) phenyl] pentanediamide hydrochloride | 962.25 | (400 MHz, DMSO-$d_6$) δ 10.14 (s, 1H), 9.11-9.06 (m, 1H), 8.57 (d, J = 7.3 Hz, 1H), 8.52 (s, 2H), 8.42 (d, J = 7.7 Hz, 1H), 8.25 (d, J = 8.7 Hz, 0H), 7.87 (d, J = 9.2 Hz, 1H), 7.48-7.36 (m, 7H), 7.19 (t, J = 7.7 Hz, 1H), 7.13 (d, J = 7.3 Hz, 1H), 7.06 (d, J = 7.7 Hz, 1H), 6.98 (t, J = 7.4 Hz, 1H), 6.87 (q, J = 11.5, 10.9 Hz, 2H), 5.20 (dd, J = 10.9, 3.0 Hz, 1H), 4.92 (p, J = 7.0 Hz, 1H), 4.53 (d, J = 9.3 Hz, 1H), 4.43 (t, J = 8.0 Hz, 1H), 4.36-4.31 (m, 1H), 4.28 (dq, J = 6.3, 3.1 Hz, 1H), 4.25-4.14 (m, 2H), 3.91-3.77 (m, 1H), 3.76-3.65 (m, 1H), 3.62 (d, J = 1.6 Hz, 1H), 3.54-3.45 (m, 2H), 3.16-3.11 (m, 2H), 2.99-2.97 (m, 1H), 2.47 (s, 3H), 2.28-2.25 (m, 3H), 2.21-2.12 (m, 2H), 2.09-1.86 (m, 3H), 1.84-1.68 (m, 3H), 1.37-1.33 (m, 3H), 0.94 (s, 11H) |
| J171 | 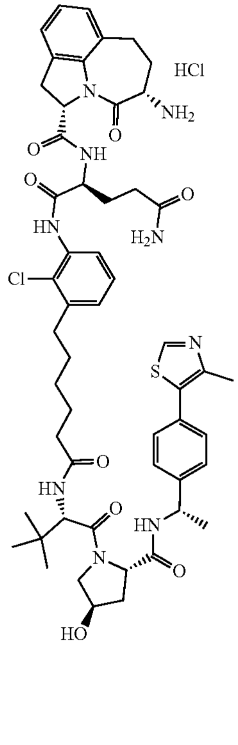 [SMILES: Cc1ncsc1-c1ccc([C@H](C)NC(=O)[C@@H]2C[C@@H](O)CN2C(=O)[C@@H](NC(=O)CCCCCc2cccc(NC(=O)[C@H](CCC(N)=O)NC(=O)[C@@H]3Cc4cccc5c4N3C(=O)[C@@H](N)CC5)c2Cl)C(C)(C)C)cc1 ; Cl] | (2S)-2-[[(2S,11S)-11-amino-12-oxo-1-azatricyclo [6.4.1.0^[4,13]] trideca-4(13),5,7-trien-2-yl]formamido]-N-[2-chloro-3-(5-[[(2S)-1-[(2S,4R)-4-hydroxy-2-[[(1S)-1-[4-(4-methyl-1,3-thiazol-5-yl)phenyl]ethyl] carbamoyl] pyrrolidin-1-yl]-3,3-dimethyl-1-oxobutan-2-yl]carbamoyl]pentyl) phenyl] pentanediamide hydrochloride | 1024.45 | (300 MHz, DMSO-$d_6$) δ 9.54 (d, J = 10.9 Hz, 1H), 9.07 (s, 1H), 8.72-8.36 (m, 5H), 7.81 (d, J = 9.2 Hz, 1H), 7.65-7.57 (m, 1H), 7.43 (q, J = 8.2 Hz, 5H), 7.31-6.95 (m, 4H), 6.86 (s, 1H), 5.23 (d, J = 10.4 Hz, 1H), 5.01-4.86 (m, 1H), 4.59-4.39 (m, 3H), 4.3-4.17 (m, 2H), 3.62 (s, 2H), 3.16 (s, 2H), 3.03 (d, J = 17.0 Hz, 1H), 2.74-2.68 (m, 2H), 2.48 (s, 3H), 2.38-1.71 (m, 10H), 1.63-1.48 (m, 6H), 1.39 (d, J = 6.9 Hz, 3H), 1.35-1.26 (m, 2H), 0.95 (s, 9H) |

TABLE 53-continued

| Characterization data for intermediates prepared according to above. | | | | |
|---|---|---|---|---|
| Intermediate | Structure | Chemical Name | MS: $[(M + 1)]^+$ | $^1H$ NMR |
| J172 | 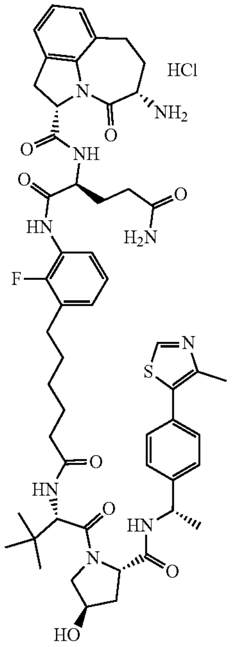 [SMILES: Cc1ncsc1-c1ccc([C@H](C)NC(=O)[C@@H]2C[C@@H](O)CN2C(=O)[C@@H](NC(=O)CCCCCc2cccc(NC(=O)[C@H](CCC(N)=O)NC(=O)[C@@H]3Cc4cccc5c4N3C(=O)[C@@H](N)CC5)c2F)C(C)(C)C)cc1 ; Cl] | (2S)-2-[[2S,11S)-11-amino-12-oxo-1-azatricyclo [6.4.1.0^[4,13]] trideca-4(13),5,7-trien-2-yl]formamido]-N-[2-fluoro-3-(5-[[(2S)-1-[(2S,4R)-4-hydroxy-2-[[(1S)-1-[4-(4-methyl-1,3-thiazol-5-yl)phenyl]ethyl] carbamoyl] pyrrolidin-1-yl]-3,3-dimethyl-1-oxobutan-2-yl]carbamoyl] pentyl)phenyl] pentanediamide hydrochloride | 1008.56 | (300 MHz, DMSO-$d_6$) δ 9.81-9.79 (m, 1H), 9.09 (s, 1H), 8.60-8.48 (m, 4H), 8.41 (d, J = 7.7 Hz, 1H), 7.79 (d, J = 9.1 Hz, 1H), 7.71-7.65 (m, 1H), 7.43 (q, J = 8.2 Hz, 4H), 7.15-6.97 (m, 5H), 6.85 (s, 1H), 5.26-5.16 (m, 1H), 4.93 (t, J = 7.2 Hz, 1H), 4.58-4.39 (m, 3H), 4.29 (s, 1H), 4.23-4.16 (m, 1H), 3.54-3.39 (m, 1H), 3.17-3.13 (m, 2H), 3.03-2.98 (m, 1H), 2.59 (t, J = 8.4 Hz, 2H), 2.48 (s, 3H), 2.35-1.70 (m, 10H), 1.61-1.47 (m, 6H), 1.39 (d, J = 7.0 Hz, 3H), 1.35-1.17 (m, 3H), 0.94 (s, 9H) |
| J173 | 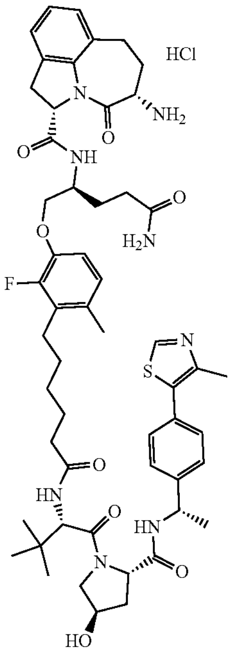 [SMILES: Cc1ccc(OC[C@H](CCC(N)=O)NC(=O)[C@@H]2Cc3cccc4c3N2C(=O)[C@@H](N)CC4)c(F)c1CCCCCC(=O)N[C@H](C(=O)N1C[C@H](O)C[C@H]1C(=O)N[C@@H](C)c1ccc(-c2scnc2C)cc1)C(C)(C)C ; Cl] | (2S,4R)-1-[(2S)-2-(6-[3-[(2S)-2-[[(2S,11S)-11-amino-12-oxo-1-azatricyclo [6.4.1.0^[4,13]] trideca-4(13),5,7-trien-2-yl]formamido]-4-carbamoylbutoxy]-2-fluoro-6-methylphenyl] hexanamido)-3,3-dimethylbutanoyl]-4-hydroxy-N-[(1S)-1-[4-(4-methyl-1,3-thiazolo-yl)phenyl]ethyl] pyrrolidine-2-carboxamide hydrochloride | 1009.45 | $^1H$ NMR (400 MHz, DMSO-$d_6$) δ 9.07 (s, 1H), 8.51 (s, 3H), 8.41 (d, J = 7.8 Hz, 1H), 8.29 (d, J = 7.6 Hz, 1H), 7.81 (d, J = 9.3 Hz, 1H), 7.48-7.28 (m, 4H), 7.08-6.96 (m, 3H), 6.87 (s, 2H), 6.79 (s, 1H), 5.10 (dd, J = 10.9, 3.1 Hz, 1H), 4.92 (p, J = 7.2 Hz, 1H), 4.52 (d, J = 9.3 Hz, 1H), 4.43 (t, J = 7.9 Hz, 1H), 4.28 (s, 1H), 4.24-4.12 (m, 1H), 4.01-3.87 (m, 2H), 3.77-3.57 (m, 3H), 3.52-3.38 (m, 2H), 3.17-3.11 (m, 3H), 2.88 (d, J = 16.9 Hz, 1H), 2.56 (s, 2H), 2.47 (s, 3H), 2.33-2.24 (m, 2H), 2.21 (s, 3H), 2.19-2.08 (m, 2H), 2.07-1.97 (m, 1H), 1.92-1.65 (m, 4H), 1.57-1.40 (m, 4H), 1.38 (d, J = 7.2 Hz, 3H), 1.35-1.22 (m, 2H), 0.93 (s, 9H) |

TABLE 53-continued

| Characterization data for intermediates prepared according to above. | | | | |
|---|---|---|---|---|
| Intermediate | Structure | Chemical Name | MS: $[(M + 1)]^+$ | $^1H$ NMR |
| J174 | 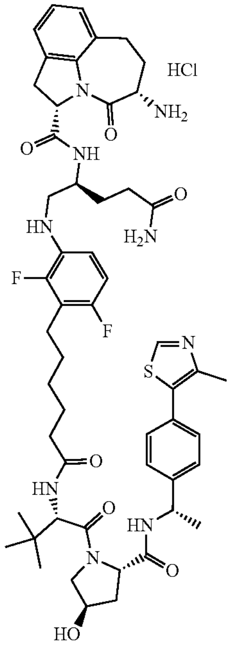 [SMILES: Cc1ncsc1-c1ccc([C@H](C)NC(=O)[C@@H]2C[C@@H](O)CN2C(=O)[C@@H](NC(=O)CCCCCc2c(F)ccc(NC[C@H](CCC(N)=O)NC(=O)[C@@H]3Cc4cccc5c4N3C(=O)[C@@H](N)CC5)c2F)C(C)(C)C)cc1 ; Cl] | (2S,4R)-1-[(2S)-2-(6-[3-[(2S)-2-[[(2S,11S)-11-amino-12-oxo-1-azatricyclo [6.4.1.0^[4,13]] trideca-4(13),5,7-trien-2-yl]formamido]-4-carbamoylbutoxy]-2,6-difluorophenyl] hexanamido)-3,3-dimethylbutanoyl]-4-hydroxy-N-[(1S)-1-[4-(4-methyl-1,3-thiazol-5-yl)phenyl]ethyl] pyrrolidine-2-carboxamide hydrochloride | 1013.40 | (400 MHz, DMSO-$d_6$) δ 9.11 (s, 1H), 8.53 (s, 3H), 8.41 (d, J = 7.7 Hz, 1H), 8.32 (d, J = 7.4 Hz, 1H), 7.80 (d, J = 9.3 Hz, 1H), 7.48-7.35 (m, 4H), 7.33 (s, 1H), 7.10-6.91 (m, 4H), 6.80 (s, 1H), 5.10 (dd, J = 10.9, 3.1 Hz, 1H), 4.91 (q, J = 7.3 Hz, 1H), 4.51 (d, J = 9.3 Hz, 1H), 4.43 (t, J = 8.0 Hz, 1H), 4.28 (s, 1H), 4.21-4.12 (m, 1H), 4.06-3.89 (m, 4H), 3.69-3.57 (m, 3H), 3.50-3.38 (m, 1H), 3.21-3.08 (m, 2H), 2.87 (d, J = 16.4 Hz, 1H), 2.58 (d, J = 8.0 Hz, 2H), 2.47 (s, 3H), 2.30-1.98 (m, 4H), 1.94-1.68 (m, 3H), 1.60 (s, 1H), 1.55-1.43 (m, 5H), 1.38 (d, J = 7.0 Hz, 3H), 1.31-1.22 (m, 2H), 0.92 (s, 9H) |
| J175 | 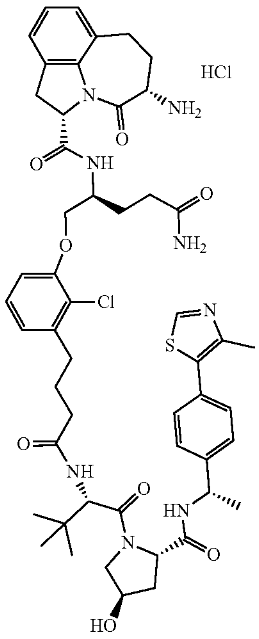 [SMILES: Cc1ncsc1-c1ccc([C@H](C)NC(=O)[C@@H]2C[C@@H](O)CN2C(=O)[C@@H](NC(=O)CCCc2cccc(OC[C@H](CCC(N)=O)NC(=O)[C@@H]3Cc4cccc5c4N3C(=O)[C@@H](N)CC5)c2Cl)C(C)(C)C)cc1 ; Cl] | (2S,4R))-1-[(2S)-2-(4-[3-[(2S)-2-[[(2S,11S)-11-amino-12-oxo-1-azatricyclo [6.4.1.0^[4,13]] trideca-4(13),5,7-trien-2-yl]formamido]-4-carbamoylbutoxy]-2-chlorophenyl] butanamido)-3,3-dimethylbutanoyl]-4-hydroxy-N-[(1S)-1-[4-(4-methyl-1,3-thiazol-5-yl)phenyl]ethyl] pyrrolidine-2-carboxamide hydrochloride | 983.50 | (400 MHz, DMSO-$d_6$) δ 9.15 (d, J = 1.5 Hz, 1H), 8.57 (s, 3H), 8.43 (d, J = 7.8 Hz, 1H), 8.32 (d, J = 7.5 Hz, 1H), 7.90 (d, J = 9.3 Hz, 1H), 7.46 (d, J = 8.0 Hz, 2H), 7.40 (d, J = 8.2 Hz, 2H), 7.20 (t, J = 7.9 Hz, 1H), 7.07 (d, J = 7.5 Hz, 2H), 7.00 (d, J = 7.8 Hz, 2H), 6.90 (d, J = 7.6 Hz, 1H), 6.85-6.71 (m, 1H), 5.11 (dd, J = 10.9, 3.1 Hz, 1H), 4.93 (p, J = 7.0 Hz, 1H), 4.55 (d, J = 9.1 Hz, 1H), 4.44 (t, J = 8.0 Hz, 1H), 4.28 (s, 1H), 4.17 (s, 1H), 4.05 (d, J = 7.5 Hz, 2H), 3.95 (s, 1H), 3.63 (d, J = 12.2 Hz, 3H), 3.49-3.37 (m, 1H), 3.16-3.12 (m, 2H), 2.98-2.94 (m, 1H), 2.71-2.67 (m, 2H), 2.48 (s, 3H), 2.39-2.24 (m, 2H), 2.24-2.12 (m, 3H), 2.10-1.98 (m, 2H), 1.93-1.85 (m, 1H), 1.83-1.68 (m, 4H), 1.38 (d, J = 7.0 Hz, 3H), 0.95 (s, 9H) |

TABLE 53-continued

Characterization data for intermediates prepared according to above.

| Intermediate | Structure | Chemical Name | MS: $[(M + 1)]^+$ | $^1$H NMR |
|---|---|---|---|---|
| J176 | 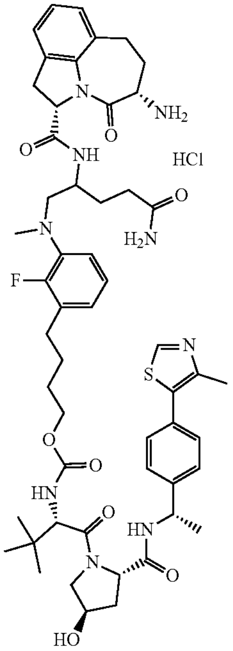 [SMILES: Cc1ncsc1-c1ccc([C@H](C)NC(=O)[C@@H]2C[C@@H](O)CN2C(=O)[C@@H](NC(=O)OCCCCc2cccc(N(C)CC(CCC(N)=O)NC(=O)[C@@H]3Cc4cccc5c4N3C(=O)[C@@H](N)CC5)c2F)C(C)(C)C)cc1 ; Cl] | 4-[3-[(2-[[(2S,11S)-11-amino-12-oxo-1-azatricyclo [6.4.1.0^[4,13]] trideca-4(13),5,7-trien-2-yl]formamido]-4-carbamoylbutyl)-(methyl)amino]-2-fluorophenyl]butyl N-[(2S)-1-[(2S,4R)-4-hydroxy-2-[[(1S)-1-[4-(4-methyl-1,3-thiazol-5-yl)phenyl]ethyl] carbamoyl] pyrrolidin-1-yl]-3,3-dimethyl-1-oxobutan-2-yl]carbamate hydrochloride | 1010.45 | (400 MHz, DMSO-$d_6$) δ 9.08 (s, 1H), 8.50 (s, 2H), 8.43 (d, J = 7.7 Hz, 1H), 8.03 (dd, J = 16.6, 8.6 Hz, 1H), 7.45 (d, J = 8.1 Hz, 2H), 7.39 (d, J = 8.2 Hz, 2H), 7.25 (s, 1H), 7.08-6.95 (m, 3H), 6.97-6.88 (m, 2H), 6.79 (s, 3H), 5.01-4.86 (m, 1H), 4.45 (t, J = 8.0 Hz, 1H), 4.28 (s, 1H), 4.17 (d, J = 9.2 Hz, 2H), 4.01 (s, 1H), 3.95 (s, 2H), 3.57 (s, 2H), 3.53-3.37 (m, 1H), 3.32-3.15 (m, 1H), 2.76 (s, 2H), 2.59-2.56 (m, 3H), 2.47 (s, 3H), 2.26-2.21 (m, 3H), 2.07-2.03 (m, 4H), 1.80-1.76 (m, 1H), 1.62-1.58 (m, 6H), 1.52-1.48 (m, 1H), 1.43-1.35 (m, 3H), 1.29-1.25 (m, 2H), 1.18-1.07 (m, 1H), 0.94 (s, 9H) |
| J177 | 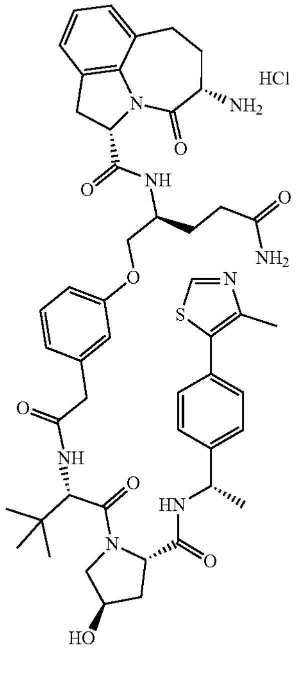 [SMILES: Cc1ncsc1-c1ccc([C@H](C)NC(=O)[C@@H]2C[C@@H](O)CN2C(=O)[C@@H](NC(=O)Cc2cccc(OC[C@H](CCC(N)=O)NC(=O)[C@@H]3Cc4cccc5c4N3C(=O)[C@@H](N)CC5)c2)C(C)(C)C)cc1 ; Cl] | (2S,4R)-1-[(2S)-2-(2-[3-[(2S)-2-[[(2S,11S)-11-amino-12-oxo-1-azatricyclo [6.4.1.0^[4,13]] trideca-4(13),5,7-trien-2-yl]formamido]-4-carbamoylbutoxy]-phenyl] acetamido)-3,3-dimethylbutanoyl]-4-hydroxy-N-[(1S)-1-[4-(4-methyl-1,3-thiazol-5-yl)phenyl]ethyl] pyrrolidine-2-carboxamide hydrochloride | $[(M - 1)]^-$ = 919.50 | (300 MHz, DMSO-$d_6$) δ 9.15 (s, 1H), 8.57-8.29 (m, 4H), 8.06 (d, J = 9.2 Hz, 1H), 7.53-7.38 (m, 4H), 7.25-6.67 (m, 8H), 5.20-4.81 (m, 2H), 4.62-4.37 (m, 2H), 4.32-3.83 (m, 5H), 3.63 (d, J = 13.8 Hz, 2H), 3.42 (dd, J = 13.6, 6.2 Hz, 2H), 3.15 (s, 2H), 2.87 (d, J = 16.8 Hz, 1H), 2.49 (s, 3H), 2.36-1.65 (m, 9H), 1.38 (d, J = 6.9 Hz, 3H), 0.93 (s, 9H) |

TABLE 53-continued

Characterization data for intermediates prepared according to above.

| Intermediate | Structure | Chemical Name | MS: $[(M + 1)]^+$ | $^1H$ NMR |
|---|---|---|---|---|
| J178 | 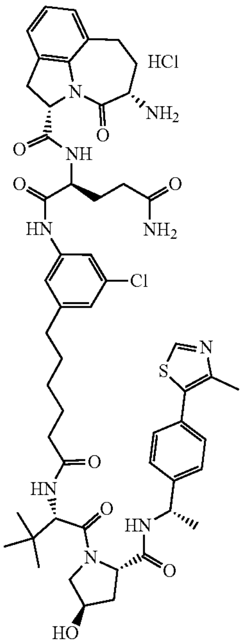 [SMILES: Cc1ncsc1-c1ccc([C@H](C)NC(=O)[C@@H]2C[C@@H](O)CN2C(=O)[C@@H](NC(=O)CCCCCc2cc(Cl)cc(NC(=O)[C@H](CCC(N)=O)NC(=O)[C@@H]3Cc4cccc5c4N3C(=O)[C@@H](N)CC5)c2)C(C)(C)C)cc1 ; Cl] | (2S)-2-[[(2S,11S)-11-amino-12-oxo-1-azatricyclo [6.4.1.0^[4,13]] trideca-4(13),5,7-trien-2-yl]formamido]-N-[3-chloro-5-(5-[[(2S)-1-[(2S,4R)-4-hydroxy-2-[[(1S)-1-[4-(4-methyl-1,3-thiazol-5-yl)phenyl]ethyl] carbamoyl] pyrrolidin-1-yl]-3,3-dimethyl-1-oxobutan-2-yl]carbamoyl] pentyl)phenyl] pentanediamide hydrochloride | $[(M - 1)]^- =$ 1022.65 | (300 MHz, DMSO-$d_6$) δ 10.44 (s, 1H), 9.12 (s, 1H), 8.63 (d, J = 6.8 Hz, 1H), 8.43 (d, J = 7.7 Hz, 1H), 7.81 (d, J = 9.2 Hz, 1H), 7.67 (s, 1H), 7.50-7.39 (m, 6H), 7.32 (s, 1H), 7.19-6.93 (m, 6H), 5.21 (d, J = 10.7 Hz, 1H), 4.99-4.88 (m, 1H), 4.52 (d, J = 9.1 Hz, 1H), 4.44 (t, J = 8.1 Hz, 1H), 4.32 (d, J = 13.3 Hz, 2H), 4.30-4.20 (s, 1H), 3.51-3.33 (m, 2H), 3.06-2.94 (m, 1H), 2.48 (s, 3H), 2.33-1.88 (m, 11H), 1.43-1.19 (m, 9H), 1.17-0.98 (m, 2H), 0.94 (s, 9H) |
| J179 | 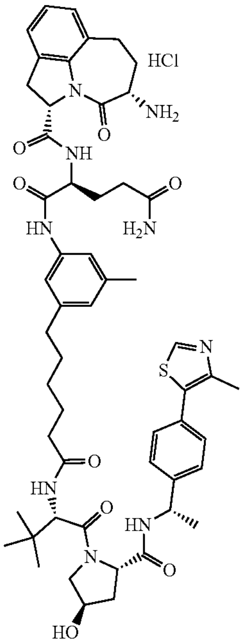 [SMILES: Cc1cc(CCCCCC(=O)N[C@H](C(=O)N2C[C@H](O)C[C@H]2C(=O)N[C@@H](C)c2ccc(-c3scnc3C)cc2)C(C)(C)C)cc(NC(=O)[C@H](CCC(N)=O)NC(=O)[C@@H]2Cc3cccc4c3N2C(=O)[C@@H](N)CC4)c1 ; Cl] | (2S)-2-[[(2S,11S)-11-amino-12-oxo-1-azatricyclo [6.4.1.0^[4,13]] trideca-4(13),5,7-trien-2-yl]formamido]-N-[3-(5-[[(2S)-1-[(2S,4R)-4-hydroxy-2-[[(1S)-1-[4-(4-methyl-1,3-thiazol-5-yl)phenyl]ethyl] carbamoyl] pyrrolidin-1-yl]-3,3-dimethyl-1-oxobutan-2-yl]carbamoyl]pentyl)-5-methylphenyl] pentanediamide hydrochioride | 1004.45 | (400 MHz, DMSO-$d_6$) δ 9.85 (s, 1H), 8.99 (s, 1H), 8.57-8.43 (m, 3H), 7.80 (d, J = 9.2 Hz, 1H), 7.44 (d, J = 8.1 Hz, 2H), 7.38 (d, J = 8.2 Hz, 2H), 7.36-7.30 (m, 1H), 7.26-7.21 (m, 2H), 7.10 (d, J = 7.5 Hz, 2H), 7.04 (d, J = 7.9 Hz, 1H), 6.95 (t, J = 7.4 Hz, 1H), 6.79 (s, 1H), 6.70 (s, 1H), 5.18-5.03 (m, 2H), 4.92 (p, J = 7.2 Hz, 1H), 4.52 (d, J = 9.3 Hz, 1H), 4.33-4.24 (m, 2H), 4.11-4.02 (m, 2H), 3.61 (d, J = 3.6 Hz, 2H), 3.53-3.40 (m, 2H), 3.15-2.93 (m, 3H), 2.52-2.43 (m, 5H), 2.49-2.41 (m, 2H), 2.32-2.24 (m, 2H), 2.23 (s, 3H), 2.19-1.74 (m, 6H), 1.60-1.45 (m, 4H), 1.29-1.23 (m, 4H), 0.93 (s, 9H) |

TABLE 53-continued

| Characterization data for intermediates prepared according to above. | | | | |
|---|---|---|---|---|
| Intermediate | Structure | Chemical Name | MS: $[(M + 1)]^+$ | $^1$H NMR |
| J180 | 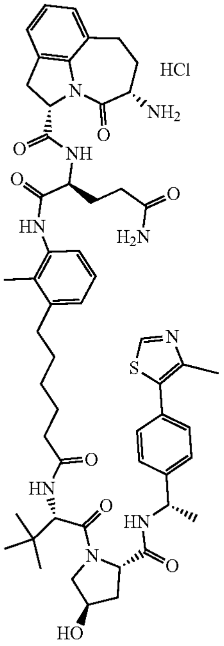 | (2S)-2-[[(2S,11S)-11-amino-12-oxo-1-azatricyclo [6.4.1.0^[4,13]] trideca-4(13),5,7-trien-2-yl]formamido]-N-[3-(5-[[(2S)-1-[(2S,4R)-4-hydroxy-2-[[(1S)-1-[4-(4-methyl-1,3-thiazol-5-yl)phenyl]ethyl] carbamoyl] pyrrolidin-1-yl]-3,3-dimethyl-1-oxobutan-2-yl]carbamoyl]pentyl)-2-methylphenyl] pentanediamide hydrochioride | $[(M - H)]^-$ = 1002.65 | (300 MHz, DMSO-$d_6$) δ 9.51 (d, J = 4.1 Hz, 1H), 9.44-9.19 (m, 1H), 8.63-8.60 (m, 5H), 8.42 (d, J = 7.8 Hz, 1H), 7.78 (d, J = 9.1 Hz, 1H), 7.42 (q, J = 8.1 Hz, 4H), 7.24-6.92 (m, 8H), 5.20 (dd, J = 10.9, 3.1 Hz, 1H), 4.96-4.90 (m, 1H), 4.56-4.35 (m, 3H), 4.27 (s, 1H), 4.16 (d, J = 8.1 Hz, 1H), 3.70-3.57 (m, 3H), 3.51-3.28 (m, 1H), 3.12 (s, 2H), 2.99 (d, J = 16.8 Hz, 1H), 2.55 (d, J = 7.9 Hz, 2H), 2.46 (s, 3H), 2.37-2.16 (m, 2H), 2.17-2.07 (m, 3H), 2.02-1.84 (m, 4H), 1.85-1.63 (m, 1H), 1.63-1.40 (m, 5H), 1.36 (d, J = 6.9 Hz, 3H), 1.27 (dd, J = 17.8, 10.3 Hz, 1H), 1.10-1.05 (m, 1H), 0.92 (s, 9H) |
| J181 | 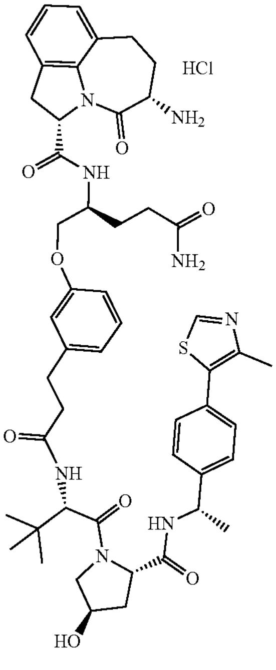 [SMILES: Cc1ncsc1-c1ccc([C@H](C)NC(=O)[C@@H]2C[C@@H](O)CN2C(=O)[C@@H](NC(=O)CCc2cccc(OC[C@H](CCC(N)=O)NC(=O)[C@@H]3Cc4cccc5c4N3C(=O)[C@@H](N)CC5)c2)C(C)(C)C)cc1 ; Cl] | (2S,4R)-1-[(2S)-2-(3-[3-[(2S)-2-[[(2S,11S)-11-amino-12-oxo-1-azatricyclo [6.4.1.0^[4,13]] trideca-4(13),5,7-trien-2-yl]formamido]-4-carbamoylbutoxy]-phenyl]propanamido)-3,3-dimethylbutanoyl]-4-hydroxy-N-[(1S)-1-[4-(4-methyl-1,3-thiazol-5-yl)phenyl]ethyl] pyrrolidine-2-carboxamide hydrochloride | 935.12 | (400 MHz, DMSO-$d_6$) δ 9.10 (s, 1H), 8.57 (s, 6H), 8.43 (d, J = 7.8 Hz, 1H), 8.30 (d, J = 8.1 Hz, 1H), 7.89 (d, J = 9.3 Hz, 1H), 7.45 (d, J = 8.2 Hz, 2H), 7.39 (d, J = 8.3 Hz, 2H), 7.17 (t, J = 7.6 Hz, 2H), 7.13-6.98 (m, 4H), 6.80 (d, J =8.1 Hz, 1H), 6.73 (d, J = 7.9 Hz, 1H), 5.10 (dt, J = 11.3, 3.6 Hz, 2H), 4.92 (p, J = 7.0 Hz, 1H), 4.53 (d, J = 9.3 Hz, 1H), 4.44 (t, J = 8.0 Hz, 1H), 4.29 (s, 1H), 4.20 (dq, J = 11.8, 6.5 Hz, 1H), 4.03 (q, J = 7.1 Hz, 1H), 3.90 (t, J = 5.7 Hz, 1H), 3.61-3.58 (m, 2H), 3.51-3.37 (m, 1H), 3.15-3.10 (m, 3H), 2.90-2.70 (m, 3H), 2.60-2.55 (m, 1H), 2.47 (s, 3H), 2.35-2.02 (m, 4H), 1.79-1.75 (m, 1H), 1.37-1.34 (m, 4H), 0.90 (s, 9H) |

TABLE 53-continued

| Characterization data for intermediates prepared according to above. | | | | |
|---|---|---|---|---|
| Intermediate | Structure | Chemical Name | MS: [(M + 1)]+ | 1H NMR |
| J182 | 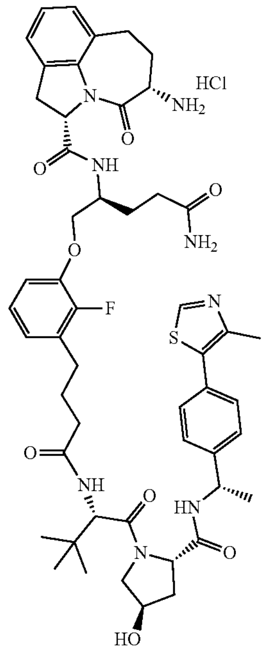 [SMILES: Cc1ncsc1-c1ccc([C@H](C)NC(=O)[C@@H]2C[C@@H](O)CN2C(=O)[C@@H](NC(=O)CCCc2cccc(OC[C@H](CCC(N)=O)NC(=O)[C@@H]3Cc4cccc5c4N3C(=O)[C@@H](N)CC5)c2F)C(C)(C)C)cc1 ; Cl] | (2S,4R)-1-[(2S)-(4-[3-[(2S)-2-[[(2S,11S)-11-amino-12-oxo-1-azatricyclo [6.4.1.0^[4,13]] trideca-4(13),5,7-trien-2-yl)formamido]-4-carbamoylbutoxy]-2-fluorophenyl] butanamido)-3,3-dimethylbutanoyl]-4-hydroxy-N-[(1S)-1-[4-(4-methyl-1,3-thiazol-5-yl)phenyl]ethyl] pyrrolidine-2-carboxamide hydrochloride | 967.35 | (400 MHz, DMSO-$d_6$) δ 9.06 (s, 1H), 8.53-8.49 (m, 2H), 8.41 (d, J = 7.8 Hz, 1H), 8.30 (d, J = 7.4 Hz, 1H), 7.89 (d, J = 9.2 Hz, 1H), 7.48-7.42 (m, 2H), 7.43-7.39 (m, 2H), 7.32-7.30 (m, 1H), 7.11-7.05 (m, 2H), 7.03-6.97 (m, 3H), 6.87-6.76 (m, 2H), 5.10 (dd, J = 11.0, 3.1 Hz, 1H), 4.91 (q, J = 7.3 Hz, 1H), 4.54 (d, J = 9.3 Hz, 1H), 4.43 (t, J = 8.0 Hz, 1H), 4.29-4.27 (m, 1H), 4.24-4.13 (m, 1H), 4.02 (m, 2H), 3.61 (t, J = 3.2 Hz, 2H), 3.46-3.36 (m, 2H), 3.16-3.13 (m, 1H), 2.90-2.83 (m, 1H), 2.59 (t, J = 8.0 Hz, 2H), 2.47 (s, 3H), 2.34-2.28 (m, 1H), 2.25-2.18 (m, 3H), 2.13-2.05 (m, 2H), 2.03-1.98 (m, 2H), 1.86-1.69 (m, 6H), 1.38 (d, J = 7.1 Hz, 3H), 0.94 (s, 9H) |
| J183 | 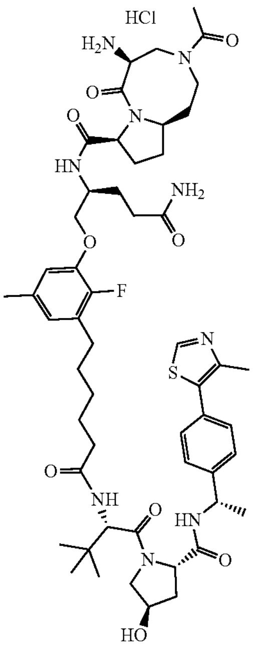 | (2S,4R)-1-[(2S)-2-(6-[3-[(2S)-2-[[(5S,8S,10aR)-3-acetyl-5-amino-6-oxo-octahydropyrrolo[1,2-a][1,5]diazocin-8-yl]formamido]-4-carbamoylbutoxy]-2-fluoro-5-methylphenyl] hexanamido)-3,3-dimethylbutanoyl]-4-hydroxy-N-[(1S)-1-[4-(4-methyl-1,3-thiazol-5-yl)phenyl]ethyl] pyrrolidine-2-carboxamide hydrochloride | 1032.45 | (300 MHz, DMSO-$d_6$) δ 9.07 (s, 1H), 8.63-8.45 (m, 3H), 8.38 (d, J = 8.0 Hz, 2H), 8.22-8.15 (m, 1H), 7.82-7.73 (m, 1H), 7.41 (q, J = 8.2 Hz, 4H), 6.80 (d, J = 7.7 Hz, 1H), 6.60 (d, J = 5.9 Hz, 1H), 4.91 (t, J = 7.2 Hz, 1H), 4.54-4.35 (m, 4H), 4.30-4.19 (m, 3H), 4.09-3.94 (m, 3H), 3.91-3.82 (m, 2H), 3.81-3.68 (m, 2H), 3.60 (s, 3 H), 3.53-3.36 (m, 2H), 3.35-3.08 (m, 3H), 2.46 (s, 3H), 2.22 (s, 3H), 1.99 (d, J = 9.9 Hz, 2H), 1.87-1.78 (m, 4H), 1.77-1.66 (m, 4H), 1.59-1.42 (m, 6H), 1.36 (s, 3H), 1.30-1.20 (m, 3H), 0.92 (s, 9H) |

TABLE 53-continued

Characterization data for intermediates prepared according to above.

| Intermediate | Structure | Chemical Name | MS: $[(M + 1)]^+$ | $^1H$ NMR |
|---|---|---|---|---|
| J184 | 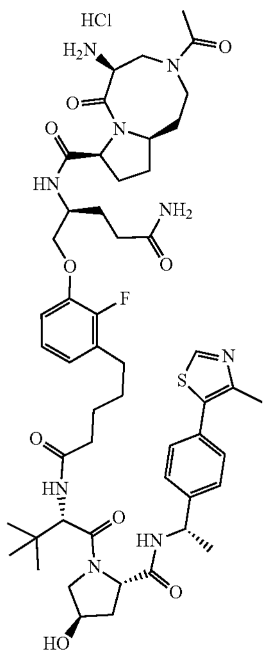 [SMILES: CC(=O)N1CC[C@H]2CC[C@@H](C(=O)N[C@@H](CCC(N)=O)COc3cccc(CCCCC(=O)N[C@H](C(=O)N4C[C@H](O)C[C@H]4C(=O)N[C@@H](C)c4ccc(-c5scnc5C)cc4)C(C)(C)C)c3F)N2C(=O)[C@@H](N)C1 ; Cl] | (2S,4R)-1-[(2S)-2-(5-[3-[(2S)-2-[[(5S,8S,10aR)-3-acetyl-5-amino-6-oxo-octahydropyrrolo[1,2-a][1,5]diazocin-8-yl)formamido]-4-carbamoylbutoxy]-2-fluorophenyl]pentanamido)-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride | 1004.40 | $^1H$ NMR (400 MHz, DMSO-$d_6$) δ 9.03 (s, 1H), 8.49-8.47 (m, 1H), 8.40 (d, J = 7.8 Hz, 1H), 8.34 (s, 1H), 8.20 (d, J = 7.9 Hz, 1H), 7.83 (d, J = 9.3 Hz, 1H), 7.45 (d, J = 8.3 Hz, 2H), 7.39 (d, J = 8 3 Hz, 2H), 7.25 (s, 1H), 7.02-7.00 (m, 2H), 6.82 (t, J = 6.4 Hz, 1H), 6.77 (s, 1H), 4.93 (t, J = 7.0 Hz, 1H), 4.50 (d, J = 12.5 Hz, 2H), 4.42-4.38 (m, 2H), 4.32-4.21 (m, 3H), 4.02 (d, J = 9.5 Hz, 2H), 3.92 (t, J = 9.8 Hz, 1H), 3.81-3.73 (m, 1H), 3.63-3.58 (m, 2H), 3.29-3.12 (m, 1H), 2.59 (t, J = 7.8 Hz, 2H), 2.47 (s, 3H), 2.35-2.28 (m, 1H), 2.22-2.15 (m, 3H), 2.12 (d, J = 9.9 Hz, 4H), 2.06-1.91 (m, 3H), 1.90-1.75 (m, 5H), 1.72-1.69 (m, 2H), 1.52-1.45 (m, 5H), 1.38 (d, J = 7.1 Hz, 3H), 0.93 (s, 9H) |
| J185 | 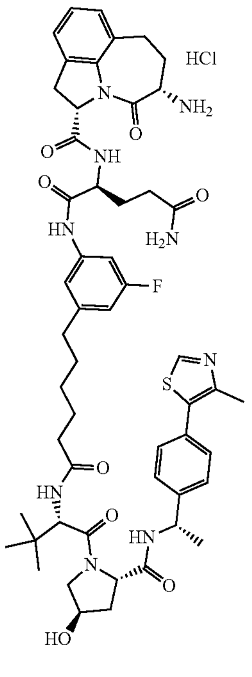 [SMILES: Cc1ncsc1-c1ccc([C@H](C)NC(=O)[C@@H]2C[C@@H](O)CN2C(=O)[C@@H](NC(=O)CCCCCc2cc(F)cc(NC(=O)[C@H](CCC(N)=O)NC(=O)[C@@H]3Cc4cccc5c4N3C(=O)[C@@H](N)CC5)c2)C(C)(C)C)cc1 ; Cl] | (2S)-2-[[(2S,11S)-11-amino-12-oxo-1-azatricyclo[6.4.1.0^[4,13]]trideca-4(13),5,7-trien-2-yl]formamido]-N-[3-fluoro-5-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenyl]-pentanediamide hydrochloride | $[(M - H)]^-$ = 1006.60 | (300 MHz, DMSO-$d_6$) δ 10.53 (d, J = 20.0 Hz, 1H), 9.41 (d, J = 10.0 Hz, 1H), 8.67 (d, J = 13.7 Hz, 5H), 8.48 (d, J = 7.7 Hz, 1H), 7.81 (d, J = 9.2 Hz, 1H), 7.52-7.39 (m, 6H), 7.23 (s, 1H), 7.18-6.91 (m, 3H), 6.77-6.65 (m, 1H), 5.23 (dd, J = 11.1, 2.9 Hz, 1H), 4.94 (t, J = 7.2 Hz, 1H), 4.59-4.40 (m, 3H), 4.43-4.24 (m, 2H), 4.18 (d, J = 9.4 Hz, 1H), 3.65 (d, J = 17.5 Hz, 2H), 3.52-3.26 (m, 2H), 3.14 (s, 2H), 3.00 (d, J = 16.9 Hz, 1H), 2.40-1.70 (m, 8H), 1.67-1.43 (m, 8H), 1.39 (d, J = 6.9 Hz, 3H), 1.33-1.18 (m, 2H), 1.18-1.00 (m, 1H), 0.94 (s, 9H) |

TABLE 53-continued

| Characterization data for intermediates prepared according to above. | | | | |
|---|---|---|---|---|
| Intermediate | Structure | Chemical Name | MS: $[(M + 1)]^+$ | $^1H$ NMR |
| J186 | 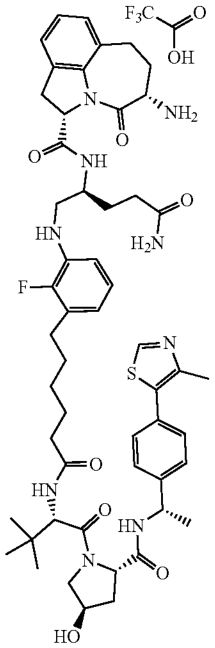 | (2S,4R)-1-[(2S)-2-(6-[3-[(2-[[(2S,11S)-11-amino-12-oxo-1-azatricyclo [6.4.1.0^[4,13]] trideca-4(13),5,7-trien-2-yl]formamido]-4-carbamoylbutyl) amino]-2-fluorophenyl] hexanamido)-3,3-dimethylbutanoyl]-4-hydroxy-N-[(1S)-1-[4-(4-methyl-1,3-thiazol-5-yl)phenyl]ethyl] pyrrolidine-2-carboxamide trifluoroacetate | 994.45 | (400 MHz, DMSO-$d_6$) δ 9.01 (s, 1H), 8.36 (s, 3H), 8.12 (d, J = 8.2 Hz, 1H), 7.79 (d, J = 9.2 Hz, 1H), 7.44 (d, J = 8.3 Hz, 2H), 7.39 (d, J = 8.3 Hz, 2H), 7.22 (s, 1H), 7.11-7.02 (m, 3H), 7.04-6.96 (m, 1H), 6.83 (t, J = 8.0 Hz, 1H), 6.77 (s, 1H), 6.63 (t, J = 8.3 Hz, 1H), 6.41 (t, J = 7.0 Hz, 1H), 5.04 (dd, J = 10.8, 3.2 Hz, 1H), 4.91 (p, J = 7.3 Hz, 1H), 4.55-4.49 (m, 2H), 4.47-4.38 (m, 2H), 4.28 (s, 1H), 3.84 (s, 1H), 3.64-3.58 (m, 3H), 3.42 (dd, J = 17.1, 11.0 Hz, 1H), 3.14-3.07 (m, 2H), 2.85-2.81 (m, 1H), 2.49-2.44 (m, 6H), 2.32-2.20 (m, 1H), 2.19-2.07 (m, 2H), 2.11-2.07 (m, 2H), 1.83-1.79 (m, 1H), 1.56-1.52 (m, 4H), 1.41-1.35 (m, 6H), 1.32-1.22 (m, 3H), 0.94 (s, 9H) |
| J187 | 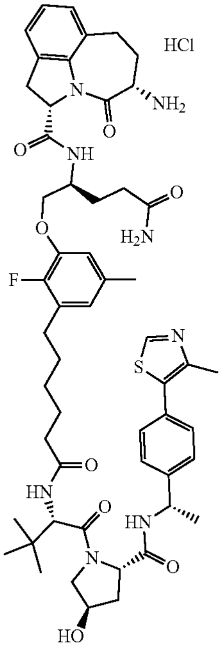 [SMILES: Cc1cc(CCCCCC(=O)N[C@H](C(=O)N2C[C@H](O)C[C@H]2C(=O)N[C@@H](C)c2ccc(-c3scnc3C)cc2)C(C)(C)C)c(F)c(OC[C@H](CCC(N)=O)NC(=O)[C@@H]2Cc3cccc4c3N2C(=O)[C@@H](N)CC4)c1 ; Cl] | (2S,4R)-1-[(2S)-2-(6-[3-[(2S)-2-[[(2S,11S)-11-amino-12-oxo-1-azatricyclo [6.4.1.0^[4,13]] trideca-4(13),5,7-trien-2-yl]formamido]-4-carbamoylbutoxy]-2-fluoro-5-methylphenyl] hexanamido)-3,3-dimethylbutanoyl]-4-hydroxy-N-[(1S)-1-[4-(4-methyl-1,3-thiazol-5-yl)phenyl]ethyl] pyrrolidine-2-carboxamide hydrochloride | 1009.50 | (300 MHz, DMSO-$d_6$) δ 9.06 (s, 1H), 8.61-8.45 (m, 3H), 8.38 (d, J = 7.8 Hz, 1H), 8.27 (d, J = 7.4 Hz, 1H), 7.78 (d, J = 9.2 Hz, 1H), 7.41 (q, J = 8.3 Hz, 4H), 7.10-6.94 (m, 3H), 6.83-6.74 (m, 2H), 6.61 (d, J = 5.9 Hz, 1H), 5.09 (dd, J = 10.9, 3.0 Hz, 1H), 4.96-4.83 (m, 1H), 4.50 (d, J = 9.3 Hz, 1H), 4.42 (t, J = 8.0 Hz, 1H), 4.30-4.23 (m, 1H), 4.21-4.11 (m, 1H), 4.03-3.89 (m, 3H), 3.61-3.58 (m, 2H), 3.56 (s, 3H), 3.49-3.34 (m, 1H), 3.18-3.07 (m, 2H), 2.86 (d, J = 16.5 Hz, 1H), 2.45 (s, 3H), 2.32-2.23 (m, 2H), 2.17-1.95 (m, 5H), 1 88-1.70 (m, 4H), 1.62-1.42 (m, 5H), 1.36 (s, 3H), 1.35-1.20 (m, 3H), 0.92 (s, 9H) |

TABLE 53-continued

Characterization data for intermediates prepared according to above.

| Intermediate | Structure | Chemical Name | MS: [(M + 1)]+ | 1H NMR |
|---|---|---|---|---|
| J188 | 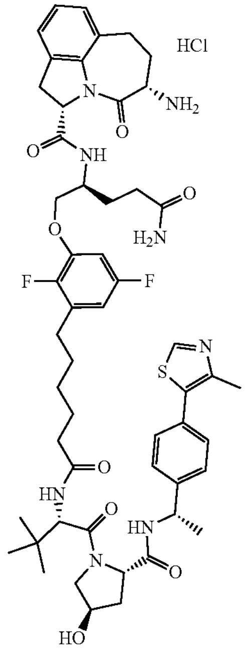 [SMILES: Cc1ncsc1-c1ccc([C@H](C)NC(=O)[C@@H]2C[C@@H](O)CN2C(=O)[C@@H](NC(=O)CCCCCc2cc(F)cc(OC[C@H](CCC(N)=O)NC(=O)[C@@H]3Cc4cccc5c4N3C(=O)[C@@H](N)CC5)c2F)C(C)(C)C)cc1 ; Cl] | (2S,4R)-1-[(2S)-2-(6-[3-[(2S)-2-[[(2S,11S)-11-amino-12-oxo-1-azatricyclo [6.4.1.0^[4,13]] trideca-4(13),5,7-trien-2-yl]formamido]-4-carbamoylbutoxy]-2,5-difluorophenyl] hexanamido)-3,3-dimethylbutanoyl]-4-hydroxy-N-[(1S)-1-[4-(4-methyl-1,3-thiazol-5-yl)phenyl]ethyl] pyrrolidine-2-carboxamide hydrochloride | 1013.35 | (400 MHz, CD3OD) δ 9.99 (s, 1H), 7.61-7.45 (m, 4H), 7.12 (d, J = 7.5 Hz, 2H), 7.10-7.01 (m, 1H), 6.83-6.75 (m, 1H), 6.64-6.55 (m, 1H), 5.20 (dd, J = 11.0, 3.5 Hz, 1H), 5.03 (q, J = 7.0 Hz, 1H), 4.65-4.55 (m, 2H), 4.44 (br, 1H), 4.30-4.09 (m, 2H), 4.07-3.98 (m, 1H), 3.90 (d, J = 11.1 Hz, 1H), 3.76 (dd, J = 11.1, 4.1 Hz, 1H), 3.64-3.49 (m, 1H), 3.27 (s, 2H), 3.10 (dd, J = 16.9, 3.6 Hz, 1H), 2.68-2.58 (m, 2H), 2.63 (s, 3H), 2.47-2.17 (m, 5H), 2.10-1.87 (m, 2H), 1.71-1.55 (m, 4H), 1.53 (d, J = 7.0 Hz, 3H), 1.43-1.27 (m, 4H), 1.05 (s, 9H), 0.92-0.87 (m, 2H) |
| J189 | 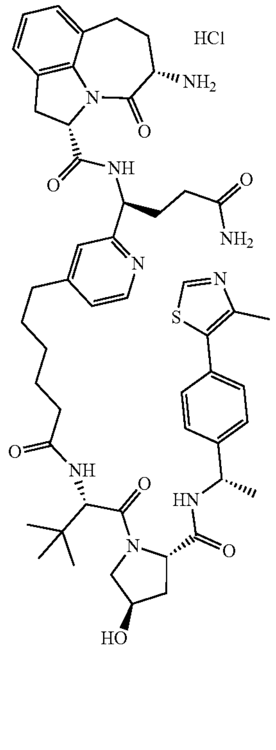 [SMILES: Cc1ncsc1-c1ccc([C@H](C)NC(=O)[C@@H]2C[C@@H](O)CN2C(=O)[C@@H](NC(=O)CCCCCc2ccnc([C@H](CCC(N)=O)NC(=O)[C@@H]3Cc4cccc5c4N3C(=O)[C@@H](N)CC5)c2)C(C)(C)C)cc1 ; Cl] | (2S,4R)-1-[(2S)-2-(6-[2-[(1S)-1-[[(2S,11S)-11-amino-12-oxo-1-azatricyclo [6.4.1.0^[4,13]] trideca-4(13),5,7-trien-2-yl]formamido]-3-carbamoylpropyl] pyridin-4-yl]hexanamido)-3,3-dimethylbutanoyl]-4-hydroxy-N-[(1S)-1-[4-(4-methyl-1,3-thiazol-5-yl)phenyl]ethyl] pyrrolidine-2-carboxamide hydrochloride | 948.40 | (300 MHz, DMSO-$d_6$) δ 9.36-9.34 (d, J = 6.9 Hz, 1H), 9.08 (s, 1H), 8.73-8.71 (d, J = 6.1 Hz, 1H), 8.62-8.55 (m, 3H), 8.42-8.40 (d, J = 7.7 Hz, 1H), 7.91-7.85 (m, 1H), 7.85-7.76 (m, 2H), 7.50-7.33 (m, 3H), 7.08-7.02 (m, 2H), 7.00-6.90 (m, 1H), 6.83 (s, 1H), 5.23-5.18 (dd, J = 11.0, 3.2 Hz, 1H), 4.93-4.83 (m, 2H), 4.52-4.45 (m, 1H), 4.44-4.42 (m, 1H), 4.27 (s, 1H), 3.54-3.29 (m, 3H), 3.11 (s, 3H), 3.03-2.98 (m, 2H), 2.96-2.81 (m, 2H), 2.78 (s, 1H), 2.54-2.41 (m, 6H), 2.31-2.14 (m, 2H), 2.05-1.90 (m, 1H), 1.95 (s, 1H), 1.85-1.65 (m, 1H), 1.53 (s, 2H), 1.38-1.23 (m, 5H), 1.10-1.06 (t, J = 7.0 Hz, 4H), 0.92 (s, 9H) |

TABLE 53-continued

| Characterization data for intermediates prepared according to above. | | | | |
|---|---|---|---|---|
| Intermediate | Structure | Chemical Name | MS: $[(M+1)]^+$ | $^1$H NMR |
| J190 | 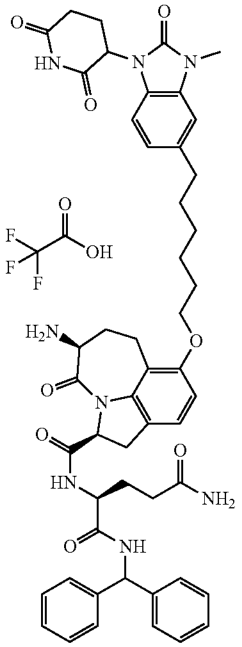 [SMILES: O=C(O)C(F)(F)F ; Cn1c(=O)n(C2CCC(=O)NC2=O)c2ccc(CCCCCCOc3ccc4c5c3CC[C@H](N)C(=O)N5[C@H](C(=O)N[C@@H](CCC(N)=O)C(=O)NC(c3ccccc3)c3ccccc3)C4)cc21] | (2S)-2-[[(2S,11S)-11-amino-7-([6-[1-(2,6-dioxopiperidin-3-yl)-3-methyl-2-oxo-1,3-benzodiazol-5-yl]hexyl]oxy)-12-oxo-1-azatricyclo [6.4.1.0^[4,13]] trideca-4(13),5,7-trien-2-yl]formamido]-N-(diphenylmethyl) pentanediamide trifluoroacetate | 897.40 | (300 MHz, DMSO-$d_6$) δ 11.10 (s, 1H), 8.81 (d, J = 8.5 Hz, 1H), 8.46-8.38 (m, 4H), 7.37-7.28 (m, 11H), 7.11-6.98 (m, 3H), 6.97-6.82-6.78 (m, 1H), 6.71-6.67 (m 1H), 6.12 (d, J = 8.3 Hz, 1H), 5.42-5.30 (m, 1H), 5.10 (dd, J = 11.2, 4.1 Hz, 1H), 4.35 (d, J = 7.0 Hz, 1H), 4.20 (d, J = 10.5 Hz, 1H), 4.04-3.90 (m, 4H), 3.34 (s, 3H), 3.27-3.19 (m, 2H), 2.99-2.57 (m, 6H), 2.30-2.08 (m, 2H), 2.08-1.87 (m, 2H), 1.74-1.67 (m, 4H), 1.57-1.34 (m, 4H), 1.28-1.22 (m, 2H) |
| J191 | 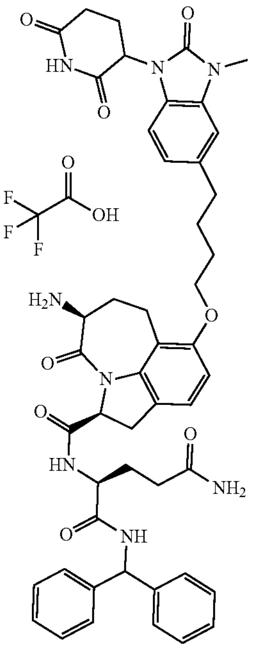 [SMILES: O=C(O)C(F)(F)F ; Cn1c(=O)n(C2CCC(=O)NC2=O)c2ccc(CCCCOc3ccc4c5c3CC[C@H](N)C(=O)N5[C@H](C(=O)N[C@@H](CCC(N)=O)C(=O)NC(c3ccccc3)c3ccccc3)C4)cc21] | (2S)-2-[[(2S,11S)-11-amino-7-[4-[1-(2,6-dioxopiperidin-3-yl)-3-methyl-2-oxo-1,3-benzodiazol-5-yl]butoxy]-12-oxo-1-azatricyclo [6.4.1.0^[4,13]] trideca-4(13),5,7-trien-2-yl]formamido]-N-(diphenylmethyl) pentanediamide trifluoroacetate | 869.35 | (300 MHz, DMSO-$d_6$) δ 11.10 (s, 1H), 8.83 (t, J = 10.4 Hz, 1H), 8.41-8.34 (m, 3H), 7.36-7.26 (m, 11H), 7.11-6.97 (m, 3H), 6.95-6.75 (m, 2H), 6.70 (d, J = 8.2 Hz, 1H), 6.18-6.02 (m, 1H), 5.36 (dd, J = 12.9. 5.1 Hz, 1H), 5.28-5.05 (m, 1H), 4.45-4.09 (m, 2H), 4.06-3.98 (m, 2H), 3.35 (s, 3H), 3.31-3.00 (m, 2H), 3.00-2.57 (m, 6H), 2.09-1.96 (m, 6H), 1.86-1 78 (m, 6H) |

TABLE 53-continued

Characterization data for intermediates prepared according to above.

| Intermediate | Structure | Chemical Name | MS: [(M + 1)]+ | 1H NMR |
|---|---|---|---|---|
| J192 | 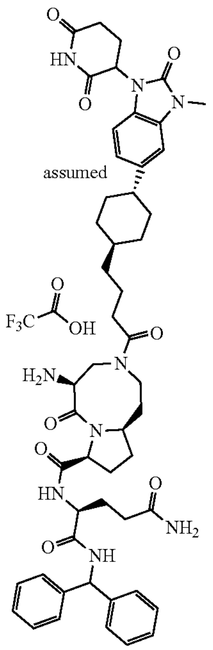 [SMILES: Cn1c(=O)n(C2CCC(=O)NC2=O)c2ccc([C@H]3CC[C@H](CCCC(=O)N4CC[C@H]5CC[C@@H](C(=O)N[C@@H](CCC(N)=O)C(=O)NC(c6ccccc6)c6ccccc6)N5C(=O)[C@@H](N)C4)CC3)cc21 ; O=C(O)C(F)(F)F] | (5S,8S,10aR)-8-[[(1S)-3-carbamoyl-1-(diphenylmethyl-carbamoyl)propyl] carbamoyl]-6-oxo-3-[4-((1r,4s)-4-[1-(2,6-dioxopiperidin-3-yl)-3-methyl-2-oxo-1,3-benzodiazol-5-yl]cyclohexyl] butanoyl]-octahydropyrrolo[1,2-a][1,5]diazocin-5-aminide trifluoroacetate | 930.65 | (400 MHz, CDCl3) δ 9.88 (s, 1H), 8.43-8.34 (m, 1H), 7.89-7.78 (m, 1H), 7.28-7.16 (m, 9H), 6.93-6.84 (m, 2H), 6.74-6.72 (m, 1H), 6.12 (d, J = 7.9 Hz, 1H), 6.01-5.98 (m, 1H) 5.17-5.14 (m, 1H), 4.44-3.93 (m, 10H), 3.20 (m, 8H), 3.01-1.87 (m, 22H), 1.77-1.71 (m, 4H), 1.41 (d, J = 8.4 Hz, 2H), 1.21 (d, J = 2.8 Hz, 1H), 1.17 (d, J = 3.1 Hz, 1H), 1.17-1.15 (m, 2H), 1.15-1.13 (m, 1H) |
| J193 | 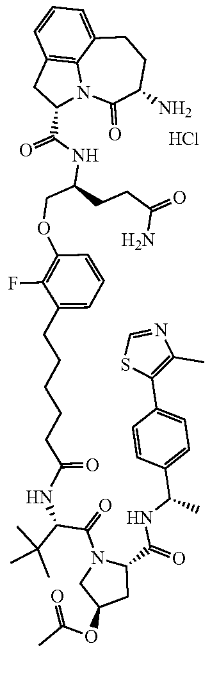 [SMILES: CC(=O)O[C@@H]1C[C@@H](C(=O)N[C@@H](C)c2ccc(-c3scnc3C)cc2)N(C(=O)[C@@H](NC(=O)CCCCCc2cccc(OC[C@H](CCC(N)=O)NC(=O)[C@@H]3Cc4cccc5c4N3C(=O)[C@@H](N)CC5)c2F)C(C)(C)C)C1 ; Cl] | (3R,5S)-1-[(2S)-2-(6-[3-[(2S)-2-[[(2S,11S)-11-amino-12-oxo-1-azatricyclo [6.4.1.0^[4,13]] trideca-4(13),5,7-trien-2-yl]formamido]-4-carbamoylbutoxy]-2-fluorophenyl] hexanamido)-3,3-dimethylbutanoyl]-5-[[(1S)-1-[4-(4-methyl-1,3-thiazol-5-yl)phenyl]ethyl] carbamoyl] pyrrolidin-3-yl acetate hydrochloride | 1037.40 | (400 MHz, DMSO-$d_6$) δ 9.08 (s, 1H), 8.58-8.43 (m, 4H), 8.31 (d, J = 7.3 Hz, 1H), 7.83 (d, J = 8.7 Hz, 1H), 7.49-7.36 (m, 4H), 7.39-7.29 (m, 1H), 7.10-7.03 (m, 2H), 7.03-6.95 (m, 3H), 6.83 (s, 1H), 5.18 (s, 1H), 5.10 (dd, J = 10.9, 3.1 Hz, 1H), 4.92 (p, J = 7.2 Hz, 1H), 4.47 (t, J = 8.3 Hz, 1H), 4.35 (d, J = 8.8 Hz, 1H), 4.24-4.14 (m, 1H), 4.02 (d, J = 7.2 Hz, 1H), 3.99-3.91 (m, 2H), 3.79-3.57 (m, 2H), 3.52-3.37 (m, 1H), 3.14 (d, J = 6.9 Hz, 2H), 2.90-2.86 (m, 1H), 2.59-2.56 (m, 3H), 2.47 (s, 3H), 2.30-2.18 (m, 3H), 2.19-2.04 (m, 1H), 1.99 (s, 3H), 1.91-1.82 (m, 1H), 1.80-1.69 (m, 2H), 1.60 (s, 1H), 1.53-1 49 (m, 5H), 1.38 (d, J = 7.0 Hz, 3H), 1.29-1.25 (m, 2H), 0.95 (s, 9H) |

TABLE 53-continued

Characterization data for intermediates prepared according to above.

| Intermediate | Structure | Chemical Name | MS: $[(M + 1)]^+$ | $^1H$ NMR |
|---|---|---|---|---|
| J194 | 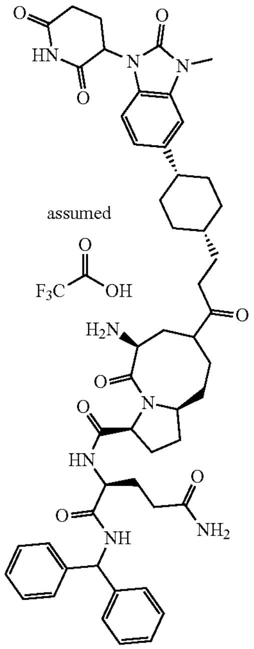 | (2S)-2-[[(5S,8S,10aR)-5-amino-6-oxo-3-[3-[(1s,4s)-4-[1-(2,6-dioxopiperidin-3-yl)-3-methyl-2-oxo-1,3-benzodiazol-5-yl]cyclohexyl]propanoyl]-octahydropyrrolo[1,2-a][1,5]diazocin-8-yl]formamido]-N-(diphenylmethyl)pentanediamide trifluoroacetate | $[(M-1)]^-$ = 914.15 | (300 MHz, DMSO-$d_6$) δ 11.09 (s, 1H), 8.85 (t, J = 7.7 Hz, 1H), 8.32 (d, J = 11.4 Hz, 3H), 7.40-7.21 (m, 10H), 7.11-6.98 (m, 2H), 6.91 (d, J = 8.3 Hz, 1H), 6.79 (s, 1H), 6.12 (d, J = 8.1 Hz, 1H), 5.77 (s, 1H), 5.35 (dd, J = 12.5, 5.2 Hz, 1H), 4.53-4.39 (m, 3H), 4.24 (s, 1H), 4.02 (d, J = 13.9 Hz, 1H), 3.84-3.49 (m, 2H), 3.30-3.16 (m, 1H), 2.96-2.91 (m, 1H), 2.76-2.58 (m, 1H), 2.16-2.11 (m, 4H), 2.07-1.66 (m, 14H), 1.58-1.41 (m, 4H), 1.35-1.32 (m, 3H), 1.25-1.21 (m, 2H), 1.10-1.05 (m, 2H) |
| J195 | 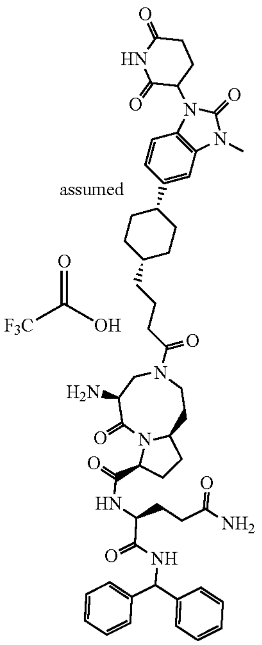 [SMILES: O=C(O)C(F)(F)F ; Cn1c(=O)n(C2CCC(=O)NC2=O)c2ccc([C@H]3CC[C@@H](CCCC(=O)N4CC[C@H]5CC[C@@H](C(=O)N[C@@H](CCC(N)=O)C(=O)NC(c6ccccc6)c6ccccc6)N5C(=O)[C@@H](N)C4)CC3)cc21] | (5S,8S,10aR)-8-[[(1S)-3-carbamoyl-1-(diphenylmethyl-carbamoyl)propyl]carbamoyl]-6-oxo-3-[4-[(1s,4r)-4-[1-(2,6-dioxopiperidin-3-yl)-3-methyl-2-oxo-1,3-benzodiazol-5-yl]cyclohexyl]butanoyl]-octahydropyrrolo[1,2-a][1,5]diazocin-5-aminide trifluoroacetate | 930.50 | (400 MHz, CDCl3) δ 11.32-11.20 (m, 10H), 11.00-10.98 (m, 1H), 10.96-10.90 (m, 2H), 10.11 (s, 1H), 9.29-9.26 (m, 1H), 8.51-8.43 (m, 2H), 8.29-8.25 (m, 1H), 8.16 (s, 1H), 7.84 (d, J = 15.9 Hz, 1H), 7.66-7.63 (m, 1H), 7.39-7.35 (m, 3H), 6.93-6.82 (m, 1H), 6.75 (d, J = 15.5 Hz, 2H), 6.55-6.52 (m, 2H), 6.39-6.32 (m, 4H), 6.15-6.04 (m, 3H), 5.92-5.87 (m, 6H), 5.68 (s, 2H), 5.52-5.49 (m, 2H), 5.32-5.28 (m, 3H), 5.16-5.12 (m, 8H) |

TABLE 53-continued

Characterization data for intermediates prepared according to above.

| Intermediate | Structure | Chemical Name | MS: $[(M + 1)]^+$ | $^1H$ NMR |
| --- | --- | --- | --- | --- |
| J196 | 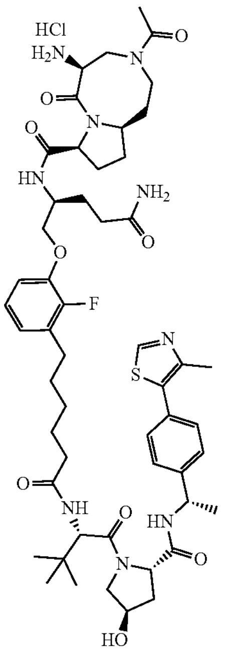 [SMILES: CC(=O)N1CC[C@H]2CC[C@@H](C(=O)N[C@@H](CCC(N)=O)COc3cccc(CCCCCC(=O)N[C@H](C(=O)N4C[C@H](O)C[C@H]4C(=O)N[C@@H](C)c4ccc(-c5scnc5C)cc4)C(C)(C)C)c3F)N2C(=O)[C@@H](N)C1 ; Cl] | (2S,4R)-1-[(2S)-2-(6-[3-[(2S)-2-[[(5S,8S,10aR)-3-acetyl-5-amino-6-oxo-octahydropyrrolo[1,2-a][1,5]diazocin-8-yl]formamido]-4-carbamoylbutoxy]-2-fluorophenyl]hexanamido)-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride | 1018.45 | (400 MHz, DMSO-$d_6$) δ 9.09 (s, 1H), 8.54 (s, 1H), 8.44-8.35 (m, 2H), 8.21 (d, J = 7.8 Hz, 1H), 7.80 (d, J = 9.3 Hz, 1H), 7.45 (d, J = 8.2 Hz, 2H), 7.39 (d, J = 8.2 Hz, 2H), 7.38-7.17 (m, 2H), 7.00 (s, 2H), 6.84-6.80 (m, 1H), 4.93-4.89 (m, 1H), 4.55-4.33 (m, 4H), 4.26 (d, J = 16.4 Hz, 3H), 4.03 (t, J = 14.0 Hz, 3H), 3.92 (t, J = 8.0 Hz, 1H), 3.77 (d, J = 14.3 Hz, 1H), 3.71-3.58 (m, 2H), 3.48-3.44 (m, 1H), 3.24-3.18 (m, 1H), 2.56 (t, J = 7.6 Hz, 3H), 2.47 (s, 3H), 2.32-2.23 (m, 1H), 2.23-2.08 (m, 6H), 2.07-1.61 (m, 6H), 1.60-1.42 (m, 7H), 1.38 (d, J = 7.0 Hz, 3H), 1.31-1.22 (m, 2H), 0.93 (s, 9H) |
| J197 | 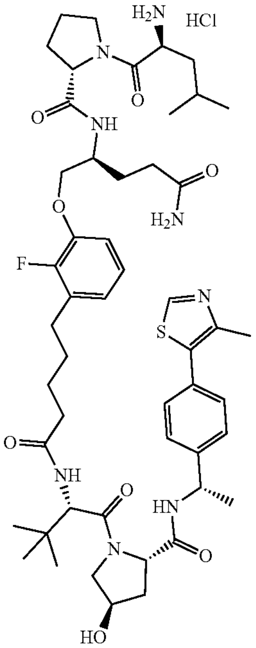 [SMILES: Cc1ncsc1-c1ccc([C@H](C)NC(=O)[C@@H]2C[C@@H](O)CN2C(=O)[C@@H](NC(=O)CCCCc2cccc(OC[C@H](CCC(N)=O)NC(=O)[C@@H]3CCCN3C(=O)[C@@H](N)CC(C)C)c2F)C(C)(C)C)cc1 ; Cl] | (2S,4R)-1-[(2S)-2-(5-[3-[(2S)-2-[[(2S)-1-[(S)-2-amino-4-methylpentanoyl]pyrrolidin-2-yl]formamido]-4-carbamoylbutoxy]-2-fluorophenyl]hexanamido)-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride | 963.45 | (400 MHz, DMSO-$d_6$) δ 9.06 (s, 1H), 8.40 (d, J = 7.8 Hz, 1H), 8.21 (s, 2H), 8.04 (d, J = 8.1 Hz, 1H), 7.82 (d, J = 9.2 Hz, 1H), 7.45 (d, J = 8.1 Hz, 2H), 7.42-7.36 (m, 2H), 7.28 (s, 1H), 7.16 (s, 1H), 7.00 (t, J = 6.7 Hz, 2H), 6.81 (d, J = 7.8 Hz, 1H), 4.92 (t, J = 7.2 Hz, 1H), 4.51 (d, J = 9.3 Hz, 1H), 4.47-4.34 (m, 1H), 4.27 (t, J = 7.0 Hz, 1H), 4.10 (s, 1H), 3.98-3.94 (m, 1H), 3.73 (s, 1H), 3.69-3.59 (m, 6H), 3.47-3.37 (m, 1H), 2.59-2.56 (m, 3H), 2.47 (s, 3H), 2.34-2.26 (m, 1H), 2.16 (s, 3H), 2.08 (s, 1H), 2.03-1.94 (m, 1H), 1.90-1.80 (m, 1H), 1.80-1.73 (m, 5H), 1.60 (s, 1H), 1.57-1.53 (m, 5H), 1.38 (d, J = 7.0 Hz, 3H), 0.94 (s, 15H) |

TABLE 53-continued

Characterization data for intermediates prepared according to above.

| Intermediate | Structure | Chemical Name | MS: $[(M + 1)]^+$ | $^1H$ NMR |
|---|---|---|---|---|
| J198 | 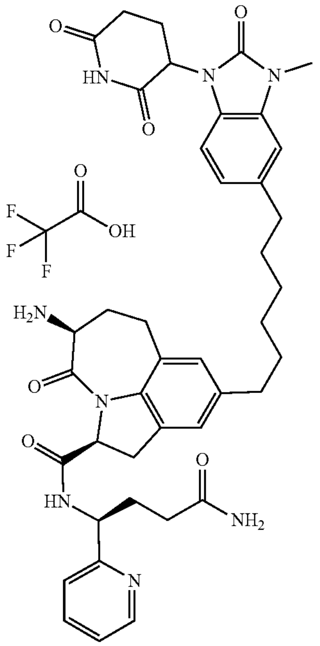 | (4S)-4-[[(2S,11S)-11-amino-6-[6-[1-(2,6-dioxopiperidin-3-yl)-3-methyl-2-oxo-1,3-benzodiazol-5-yl]hexyl]-12-oxo-1-azatricyclo [6.4.1.0^[4,13]] trideca-4(13),5,7-trien-2-yl]formamido]-4-(pyridin-2-yl)butanamide trifluoroacetate | 749.30 | (300 MHz, DMSO-$d_6$) δ 11.06 (s, 1H), 8.75-8.68 (m, 1H), 8.59-8.54 (m, 1H), 8.40-8.29 (m, 2H), 7.90-7.83 (m, 1H), 7.42-7.33 (m, 2H), 7.20 (s, 1H), 7.03-6.94 (m, 2H), 6.89 (s, 1H), 6.87-6.81 (m, 2H), 6.78-6.70 (m, 1H), 5.34-5.30 (m, 1H), 5.18-5.13 (m, 1H), 4.84-4.75 (m, 1H), 4.24-4.12 (m, 1H), 3.48-3.34 (m, 2H), 3.14-3.03 (m, 2H), 2.92-2.69 (m, 3H), 2.68-2.54 (m, 4H), 2.46-2.37 (m, 2H), 2.19-1.92 (m, 8H), 1.60-1.44 (m, 4H), 1.35-1.25 (m, 4H) |
| J199 | 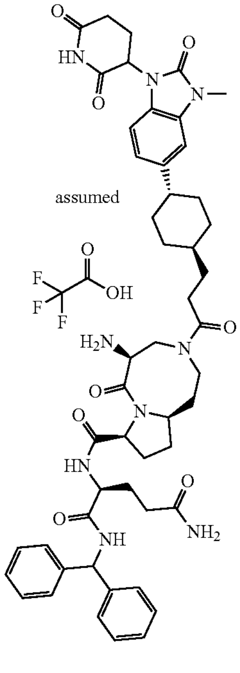 [SMILES: Cn1c(=O)n(C2CCC(=O)NC2=O)c2ccc([C@H]3CC[C@H](CCC(=O)N4CC[C@H]5CC[C@@H](C(=O)N[C@@H](CCC(N)=O)C(=O)NC(c6ccccc6)c6ccccc6)N5C(=O)[C@@H](N)C4)CC3)cc21 ; O=C(O)C(F)(F)F] | (2S)-2-[[(5S,8S,10aR)-5-amino-6-oxo-3-[3-[(1r,4r)-4-[1-(2,6-dioxopiperidin-3-yl)-3-methyl-2-oxo-1,3-benzodiazol-5-yl]cyclohexyl] propanoyl]-octahydropyrrolo[1,2-a][1,5]diazocin-8-yl]formamido]-N-(diphenylmethyl) pentanediamide trifluoroacetate | 916.40 | (300 MHz, DMSO-$d_6$) δ 11.10 (s, 1H), 8.85 (t, J = 8.0 Hz, 1H), 8.32 (d, J = 8.0 Hz, 2H), 7.41-7.19 (m, 12H), 7.09 (s, 1H), 7.02 (d, J = 8.2 Hz, 1H), 6.93 (d, J = 8.1 Hz, 1H), 6.79 (s, 1H), 6.12 (d, J = 8.1 Hz, 1H), 5.35 (dd, J = 12.8. 5.3 Hz, 1H), 4.58-4.33 (m, 4H), 4.24-4.21 (m, 1H), 4.02 (d, J = 14.3 Hz, 1H), 3.86-3.84 (m, 2H), 3.09-2.84 (m, 3H), 2.64-2.61 (m, 2H), 2.10-2.07 (m, 11H), 1.87-1.53 (m, 14H) |

TABLE 53-continued

Characterization data for intermediates prepared according to above.

| Intermediate | Structure | Chemical Name | MS: $[(M + 1)]^+$ | $^1H$ NMR |
|---|---|---|---|---|
| J200 | 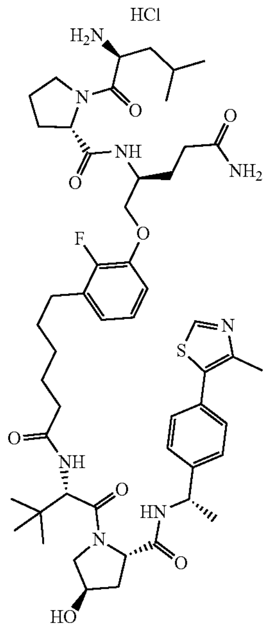 [SMILES: Cl ; Cc1ncsc1-c1ccc([C@H](C)NC(=O)[C@@H]2C[C@@H](O)CN2C(=O)[C@@H](NC(=O)CCCCCc2cccc(OC[C@H](CCC(N)=O)NC(=O)[C@@H]3CCCN3C(=O)[C@@H](N)CC(C)C)c2F)C(C)(C)C)cc1] | (2S,4R)-1-[(2S)-2-(6-[3-[(2S)-2-[[(2S)-1-[(2S)-2-amino-4-methylpentanoyl]pyrrolidin-2-yl]formamido]-4-carbamoylbutoxy]-2-fluorophenyl]hexanamido)-3,3-dimethylbutanoyl]-4-hydroxy-N-[(1S)-1-[4-(4-methyl-1,3-thiazol-5-yl)phenyl)ethyl]pyrrolidine-2-carboxamide hydrochloride | 977.45 | (400 MHz, DMSO-$d_6$) δ 9.02 (d, J = 1.8 Hz, 1H), 8.39 (d, J = 7.8 Hz, 1H), 8.17-8.15 (m, 2H), 8.02 (d, J = 8.0 Hz, 1H), 7.79 (d, J = 9.3 Hz, 1H), 7.44 (d, J = 8.2 Hz, 2H), 7.39 (d, J = 8.2 Hz, 2H), 7.00 (d, J = 6.9 Hz, 2H), 6.84-6.75 (m, 1H), 4.93-4.91 (m, 1H), 4.51 (d, J = 9.3 Hz, 1H), 4.43-4.41 (m, 2H), 4.38-4.30 (m, 4H), 4.06-3.87 (m, 4H), 3.73 (d, J = 8.9 Hz, 2H), 3.51-3.38 (m, 2H), 2.58-2.55 (m, 3H), 2.46 (s, 3H), 2.31-2.21 (m, 2H), 2.18-1.92 (m, 7H), 1.85-1.80 (m, 7H), 1.59-1.45 (m, 7H), 1.39-1.36 (m, 3H), 1.29-1.24 (m, 2H), 0.93 (s, 9H) |
| J201 | 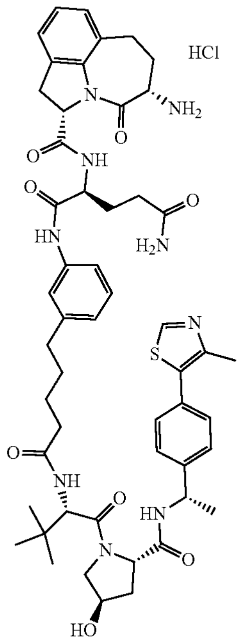 [SMILES: Cc1ncsc1-c1ccc([C@H](C)NC(=O)[C@@H]2C[C@@H](O)CN2C(=O)[C@@H](NC(=O)CCCCc2cccc(NC(=O)[C@H](CCC(N)=O)NC(=O)[C@@H]3Cc4cccc5c4N3C(=O)[C@@H](N)CC5)c2)C(C)(C)C)cc1 ; Cl] | (2S)-2-[[(2S,11S)-11-amino-12-oxo-1-azatricyclo[6.4.1.0^[4,13]]trideca-4(13),5,7-trien-2-yl]formamido]-N-(3-(4-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]butyl)phenyl]pentanediamide hydrochloride | $[(M - H)]^-$ = 974.10 | Used next step directly without purification |

TABLE 53-continued

| Characterization data for intermediates prepared according to above. | | | | |
|---|---|---|---|---|
| Intermediate | Structure | Chemical Name | MS: [(M + 1)]+ | $^1$H NMR |
| J202 | 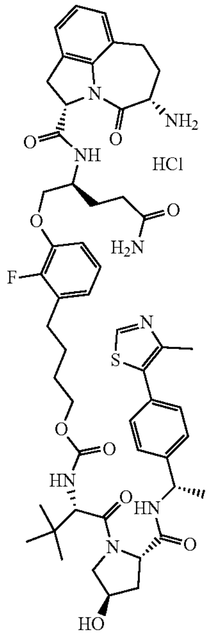 [SMILES: Cc1ncsc1-c1ccc([C@H](C)NC(=O)[C@@H]2C[C@@H](O)CN2C(=O)[C@@H](NC(=O)OCCCCc2cccc(OC[C@H](CCC(N)=O)NC(=O)[C@@H]3Cc4cccc5c4N3C(=O)[C@@H](N)CC5)c2F)C(C)(C)C)cc1 ; Cl] | 4-[3-[(2S)-2-[[(2S,11S)-11-amino-12-oxo-1-azatricyclo [6.4.1.0^[4,13]] trideca-4(13),5,7-trien-2-yl]formamido]-4-carbamoylbutoxy]-2-fluorophenyl]butyl N-[(2S)-1-[(2S,4R)-4-hydroxy-2-[[(1S)-1-[4-(4-methyl-1,3-thiazol-5-yl)phenyl]ethyl] carbamoyl] pyrrolidin-1-yl]-3,3-dimethyl-1-oxobutan-2-yl]carbamate hydrochloride | 997.75 | $^1$H NMR (400 MHz, DMSO-d$_6$) δ 9.03 (s, 1H), 8.52-8.41 (m, 2H), 8.30 (d, J = 7.2 Hz, 1H), 7.47-7.42 (m, 2H), 7.39 (d, J = 12.3 Hz, 2H), 7.29 (d, J = 10.2 Hz, 2H), 7.15 (s, 2H), 7.07 (d, J = 7.3 Hz, 2H), 7.04-6.96 (m, 2H), 6.92 (d, J = 9.1 Hz, 1H), 6.85 (q, J = 5.1, 4.3 Hz, 1H), 5.10 (dd, J = 10.9, 3.1 Hz, 1H), 4.90 (t, J = 7.2 Hz, 1H), 4.46 (dd, J = 18.7, 10.8 Hz, 2H), 4.28 (s, 1H), 4.17 (d, J = 9.2 Hz, 2H), 4.01 (s, 3H), 3.63 (dt, J = 16.4. 6.5 Hz, 1H), 3.50-3.37 (m, 1H), 3.15 (s, 2H), 2.88 (d, J = 16.4 Hz, 1H), 2.62 (s, 2H), 2.46 (s, 3H), 2.28-2.11 (m, 1H), 2.08 (s, 4H), 2.03 (s, 1H), 1.78 (dq, J = 9.8, 3.4 Hz, 2H), 1.64-1.52 (m, 6H), 1.38 (d, J = 7.1 Hz, 3H), 1.29-1.18 (m, 1H), 0.94 (s, 9H) |
| J203 | 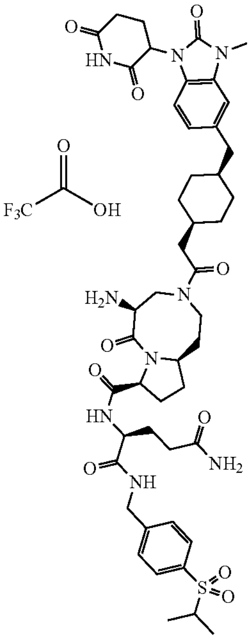 [SMILES: O=C(O)C(F)(F)F ; CC(C)S(=O)(=O)c1ccc(CNC(=O)[C@H](CCC(N)=O)NC(=O)[C@@H]2CC[C@@H]3CCN(C(=O)C[C@H]4CC[C@@H](Cc5ccc6c(c5)n(C)c(=O)n6C5CCC(=O)NC5=O)CC4)C[C@H](N)C(=O)N32)cc1] | (2S)-2-[[(5S,8S,10aR)-5-amino-6-oxo-3-[2-[(1s,4s)-4-[[1-(2,6-dioxopiperidin-3-yl)-3-methyl-2-oxo-1,3-benzodiazol-5-yl]methyl]-cyclohexyl]acetyl]-octahydropyrrolo[1,2-a][1,5]diazocin-8-yl]formamido]-N-[[4-(propane-2-sulfonyl)phenyl] methyl] pentanediamide trifluoroacetate | 946.20 | (400 MHz, DMSO-d$_6$) δ 11.10 (s, 1H), 8.63-8.48 (m, 1H), 8.24 (t, J = 7.8 Hz, 1H), 7.78 (d, J = 8.1 Hz, 2H), 7.53 (dd, J = 8.2, 6.5 Hz, 2H), 7.26 (s, 1H), 7.15-6.94 (m, 2H), 6.93-6.67 (m, 2H), 5.34 (dd, J= 12.7, 5.4 Hz, 1H), 4.46-4.35 (m, 3H), 4.27-3.88 (m, 2H), 3.80-3.58 (m, 2H), 3.50-3.38 (m, 2H), 3.32-3.18 (m, 5H), 3.01-2.84 (m, 2H), 2.76-2.68 (m, 1H), 2.65-2.59 (m, 3H), 2.38-2.25 (m, 1H), 2.18-2.12 (m, 4H), 2.07-1.52 (m, 9H), 1.52-1.19 (m, 10H), 1.14 (dd, J = 6.9, 2.8 Hz, 6H) |

TABLE 53-continued

| Characterization data for intermediates prepared according to above. | | | | |
|---|---|---|---|---|
| Intermediate | Structure | Chemical Name | MS: [(M + 1)]+ | $^1$H NMR |
| J204 | 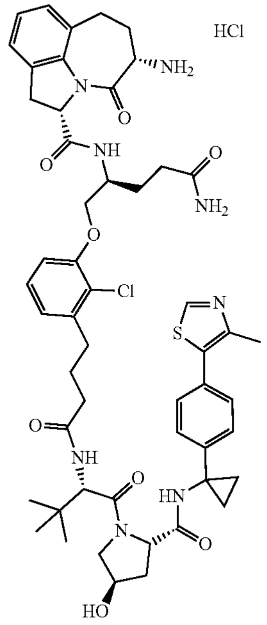 | (2S,4R)-1-[(2S)-2-(4-[3-[(2S)-2-[[(2S,11S)-11-amino-12-oxo-1-azatricyclo [6.4.1.0^[4,13]] trideca-4(13),5,7-trien-2-yl]formamido]-4-carbamoylbutoxy]-2-chlorophenyl] butanamido)-3,3-dimethylbutanoyl]-4-hydroxy-N-[1-[4-(4-methyl-1,3-thiazol-5-yl)phenyl] cyclopropyl] pyrrolidine-2-carboxamide hydrochloride | 995.45 | (300 MHz, DMSO-$d_6$) δ 9.09-9.02 (m, 1H), 8.88-8.82 (m, 1H), 8.53-8.47 (m, 2H), 8.30 (d, J = 12 Hz, 1H), 8.04 (d, J = 9.3 Hz, 1H), 7.38-7.28 (m, 5H), 7.26-7.18 (m, 1H), 7.14-7.03 (m, 2H), 7.10-7.01 (m, 2H), 6.96-6.91 (m, 1H), 6.87-6.80 (m, 1H), 5.16-5.10 (m, 1H), 4.62-4.56 (m, 1H), 4.14-4.01 (m, 4H), 3.69-3.64 (m, 2H), 3.49-3.38 (m, 1H), 3.18-3.12 (m, 2H), 3.02-2.93 (m, 1H), 2.73-2.65 (m, 2H), 2.46 (s, 3H), 2.40-2.31 (m, 1H), 2.29-1.97 (m, 8H), 1.93-1.69 (m, 6H), 1.27-1.15 (m, 4H), 0.97 (s, 9H) |
| J205 | 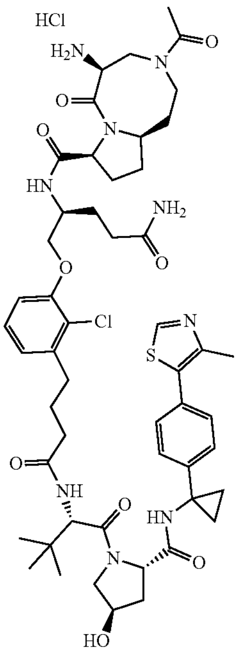 [SMILES: CC(=O)N1CC[C@H]2CC[C@@H](C(=O)N[C@@H](CCC(N)=O)COc3cccc(CCCC(=O)N[C@H](C(=O)N4C[C@H](O)C[C@H]4C(=O)NC4(c5ccc(-c6scnc6C)cc5)CC4)C(C)(C)C)c3Cl)N2C(=O)[C@@H](N)C1 ; Cl] | (2S,4R)-1-[(2S)-2-(4-[3-[(2S)-2-[[(5S,8S,10aR)-3-acetyl-5-amino-6-oxo-octahydropyrrolo[1,2-a][1,5]diazocin-8-yl]formamido]-4-carbamoylbutoxy]-2-chlorophenyl] butanamido)-3,3-dimethylbutanoyl]-4-hydroxy-N-[1-[4-(4-methyl-1,3-thiazol-5-yl)phenyl] cyclopropyl] pyrrolidine-2-carboxamide hydrochloride | 1018.50 | (300 MHz, DMSO-$d_6$) δ 9.07 (s, 1H), 8.89-8.81 (m, 1H), 8.55-8.49 (m, 1H), 8.42-8.35 (m, 1H), 8.20 (d, J = 7.8 Hz, 1H), 8.02 (d, J = 9.2 Hz, 1H), 7.37-7.28 (m, 5H), 7.27-7.20 (m, 1H), 7.05-7.00 (m, 1H), 6.95-6.89 (m, 1H), 6.78 (s, 1H), 4.58 (d, J = 9.3 Hz, 1H), 4.44-4.35 (m, 3H), 4.29-4.23 (m, 2H), 4.09-4.02 (m, 2H), 3.97-3.93 (m, 1H), 3.69-3.62 (m, 2H), 3.62-3.56 (m, 4H), 3.09-3.01 (m, 1H), 2.72-2.64 (m, 2H), 2.46 (s,3H), 2.26-2.10 (m, 8H), 2.05-1.98 (m, 2H), 1.93-1.73 (m, 10H), 1.26-1.14 (m, 4H), 0.96 (s, 9H) |

TABLE 53-continued

Characterization data for intermediates prepared according to above.

| Intermediate | Structure | Chemical Name | MS: [(M + 1)]+ | $^1$H NMR |
|---|---|---|---|---|
| J206 | 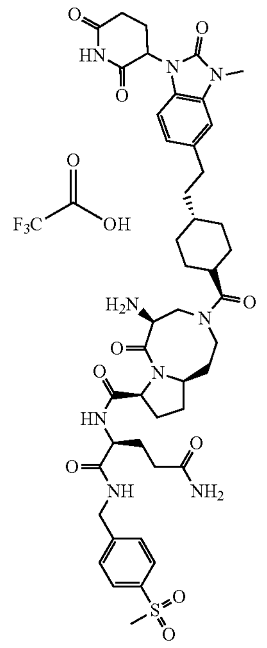 | (2S)-2-[[(5S,8S,10aR)-5-amino-6-oxo-3-[(1r,4r)-4-[2-[1-(2,6-dioxopiperidin-3-yl)-3-methyl-2-oxo-1,3-benzodiazol-5-yl]ethyl] cyclohexanecarbonyl]-octahydropyrrolo[1,2-a][1,5]diazocin-8-yl]formamido]-N-[(4-methane-sulfonylphenyl) methyl] pentanediamide trifluoroacetate | 918.35 | (300 MHz, DMSO-d$_6$) δ 11.11 (s, 1H), 8.62 (d, J = 6.2 Hz, 1H), 8.46-8.26 (m, 3H), 7.88 (d, J = 7.8 Hz, 2H), 7.56-7.48 (m, 2H), 7.26 (s, 1H), 7.02 (d, J = 9.6 Hz, 2H), 6.91-6.78 (m, 2H), 5.77 (d, J = 1.2 Hz, 1H), 5.35 (d, J = 11.9 Hz, 1H), 4.73-4.65 (m, 16H), 4.52-4.36 (m, 3H), 4.25 (dd, J = 19.0, 11.7 Hz, 1H), 3.21 (s, 3H), 2.98-2.71 (m, 2H), 2.66 (s, 3H), 2.14-2.11 (m, 1H), 2.06-1.67 (m, 8H), 1.52-1.47 (m, 2H), 1.37-1.01 (m, 4H) |
| J207 | 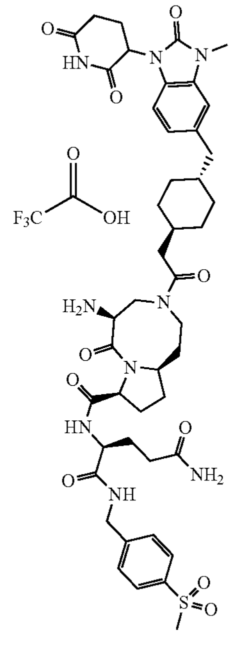 [SMILES: O=C(O)C(F)(F)F ; Cn1c(=O)n(C2CCC(=O)NC2=O)c2ccc(C[C@H]3CC[C@H](CC(=O)N4CC[C@H]5CC[C@@H](C(=O)N[C@@H](CCC(N)=O)C(=O)NCc6ccc(S(C)(=O)=O)cc6)N5C(=O)[C@@H](N)C4)CC3)cc21] | (2S)-2-((5S,8S,10aR)-5-amino-3-(2-((1r,4S)-4-((1-(2,6-dioxopiperidin-3-yl)-3-methyl-2-oxo-2,3-dihydro-1H-benzo[d]imidazol-5-yl)methyl)-cyclohexyl)acetyl)-6-oxodeca-hydropyrrolo[1,2-a][1,5]diazocine-8-carboxamido)-N-(4-(methylsulfonyl) benzyl) pentanediamide trifluoroacetate | 918.40 | (300 MHz, DMSO-d$_6$) δ 11.07 (s, 1H), 8.57 (q, J = 4.0, 2.5 Hz, 1H), 8.36 (d, J = 7.7 Hz, 1H), 8.27 (s, 2H), 7.90-7.80 (m, 2H), 7.49 (d, J = 8.3 Hz, 2H), 7.25-7.19 (m, 1H), 6.98 (d, J = 8.0 Hz, 2H), 6.87-6.74 (m, 2H), 5.33 (dd, J = 12.8, 5.3 Hz, 1H), 4.51-4.34 (m, 4H), 4.30-4.09 (m, 3H), 3.99-3.88 (m, 1H), 3.81 (d, J = 14.4 Hz, 1H), 3.31 (s, 3H), 3.18 (s, 3H), 3.14-2.81 (m, 3H), 2.77-2.55 (m, 3H), 2.38-2.07 (m, 6H), 2.04-1.62 (m, 13H), 1.04-0.86 (m, 4H) |

TABLE 53-continued

Characterization data for intermediates prepared according to above.

| Intermediate | Structure | Chemical Name | MS: $[(M + 1)]^+$ | $^1$H NMR |
|---|---|---|---|---|
| J208 | 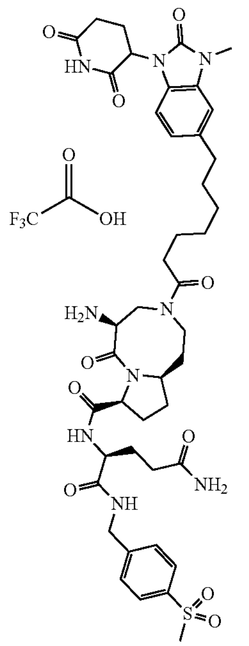 [SMILES: O=C(O)C(F)(F)F ; Cn1c(=O)n(C2CCC(=O)NC2=O)c2ccc(CCCCCCC(=O)N3CC[C@H]4CC[C@@H](C(=O)N[C@@H](CCC(N)=O)C(=O)NCc5ccc(S(C)(=O)=O)cc5)N4C(=O)[C@@H](N)C3)cc21] | (2S)-2-((5S,8S,10aR)-5-amino-3-(7-(1-(2,6-dioxopiperidin-3-yl)-3-methyl-2-oxo-2,3-dihydro-1H-benzo[d]imidazol-5-yl)heptanoyl)-6-oxodecahydro-pyrrolo[1,2-a][1,5]diazocine-8-carboxamido)-N1-(4-(methylsulfonyl)benzyl)pentanediamide trifluoroacetate | 892.40 | (400 MHz, DMSO-$d_6$) δ 11.09 (s, 1H), 8.62-8.56 (m, 1H), 8.39 (d, J = 7.7 Hz, 1H), 8.34-8.26 (m, 2H), 7.87 (d, J = 8.1 Hz, 2H), 7.50 (d, J = 7.9 Hz, 2H), 7.25 (s, 1H), 7.05-6.97 (m, 2H), 6.86 (d, J = 8.0 Hz, 1H), 6.80 (s, 1H), 5.35 (dd, J = 12 8, 5.3 Hz, 1H), 4.52-4.36 (m, 4H), 4.30-4.17 (m, 3H), 3.96 (d, J = 14.4 Hz, 1H), 3.82 (d, J = 14.3 Hz, IH), 3.33 (s, 3H), 3.19 (s, 3H), 2.97-2.85 (m, 1H), 2.76-2.67 (m, 1H)), 2.66-2.58 (m, 3H), 2.34-2.18 (m, 2H), 2.17-2.10 (m, 2H), 2.04-1.86 (m, 4H), 1.85-1.76 (m, 3H), 1.75-1.67 (m, 2H), 1.65-1.48 (m, 5H), 1.40-1.29 (m, 4H) |
| J209 | 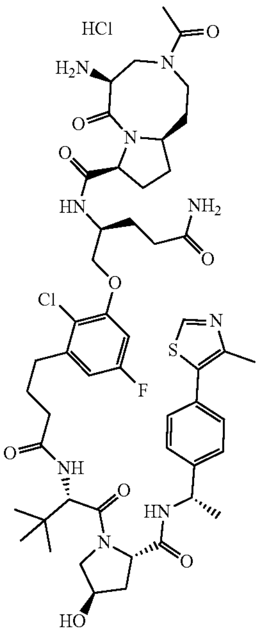 [SMILES: CC(=O)N1CC[C@H]2CC[C@@H](C(=O)N[C@@H](CCC(N)=O)COc3cc(F)cc(CCCC(=O)N[C@H](C(=O)N4C[C@H](O)C[C@H]4C(=O)N[C@@H](C)c4ccc(-c5scnc5C)cc4)C(C)(C)C)c3Cl)N2C(=O)[C@@H](N)C1 ; Cl] | (2S,4R)-1-[(2S)-2-(4-[3-[(2S)-2-[[(5S,8S,10aR-3-acetyl-5-amino-6-oxo-octahydropyrrolo[1,2-a][1,5]diazocin-8-yl]formamido]-4-carbamoylbutoxy]-2-chloro-5-fluorophenyl]butanamido)-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride | 1024.45 | (300 MHz, DMSO-$d_6$) δ 9.02 (s, 1H), 8.54-8.30 (m, 3H), 8.18 (d, J = 7.3 Hz, 1H), 7.92 (d, J = 8.9 Hz, 1H), 7.60-7.43 (m, 4H), 7.26 (s, 1H), 7.03-7.01 (m, 1H), 6.80-6.76 (m, 2H), 5.00-4.93 (m, 1H), 4.55-4.44 (m, 3H), 4.30-4.24 (m, 3H), 4.18-4.08 (m, 3H), 3.63-3.61 (m, 2H), 3.60-3.58 (m, 4H), 2.95-2.91 (m, 3H), 2.70-2.67 (m, 3H), 2.48 (s, 3H), 2.31-2.27 (m, 2H), 2.21-2.15 (m, 3H), 2.13-2.03 (m, 4H), 1.95-1.82 (m, 8H), 1.39 (d, J = 7.0 Hz, 3H), 0.96 (s, 9H) |

TABLE 53-continued

| Characterization data for intermediates prepared according to above. | | | | |
|---|---|---|---|---|
| Intermediate | Structure | Chemical Name | MS: $[(M + 1)]^+$ | $^1H$ NMR |
| J210 | 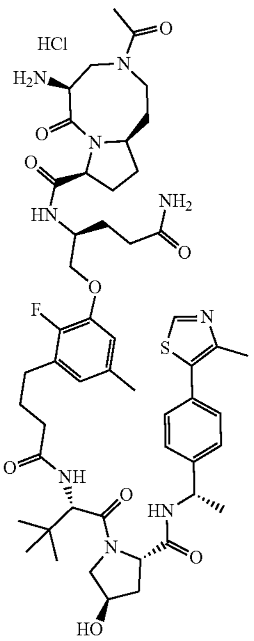 [SMILES: CC(=O)N1CC[C@H]2CC[C@@H](C(=O)N[C@@H](CCC(N)=O)COc3cc(C)cc(CCCC(=O)N[C@H](C(=O)N4C[C@H](O)C[C@H]4C(=O)N[C@@H](C)c4ccc(-c5scnc5C)cc4)C(C)(C)C)c3F)N2C(=O)[C@@H](N)C1 ; Cl] | (2S,4R)-1-[(2S)-2-(4-[3-[(2S)-2-[[(5S,8S,10aR)-3-acetyl-5-amino-6-oxo-octahydropyrrolo[1,2-a][1,5]diazocin-8-yl]formamido]-4-carbamoylbutoxy]-2-fluoro-5-methylphenyl]butanamido)-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride | 1004.45 | (400 MHz, DMSO-$d_6$) δ 9.06 (s, 1H), 8.49 (s, 1H), 8.40 (d, J = 7.7 Hz, 1H), 8.35 (s, 1H), 8 19 (d, J = 8.1 Hz, 1H), 7.87 (d, J = 9.1 Hz, 1H), 7.48-7.36 (m, 4H), 7.35-7.22 (m, 1H), 6.83 (d, J = 7.6 Hz, 1H), 6.78 (s, 1H), 6.61 (d, J = 6.1 Hz, 1H), 4.92 (t, J = 7.3 Hz, 1H), 4.53(d, J = 9.3 Hz, 1H), 4 48 (s, 1H), 4.47-4.33 (m, 2H), 4.30-4.21 (m, 3H), 4.01 (t, J = 12.1 Hz, 3H), 3.90 (d, J = 8.9 Hz, 1H), 3.77 (d, J = 14.9 Hz, 1H), 3.63 (d, J = 16.5 Hz, 3H), 3.47-3.37 (m, 1H), 3.19-3.11 (m, 1H), 2.96-2.86 (m, 1H), 2.47 (s, 3H), 2.33-2.19 (m, 6H), 2.20-2.08 (m, 6H), 2.07-1.89 (m, 1H), 1.88-1.65 (m, 8H), 1.60-1.45 (m, 1H), 1.38 (d, J = 7.0 Hz, 3H), 0.94 (s, 9H) |
| J211 | 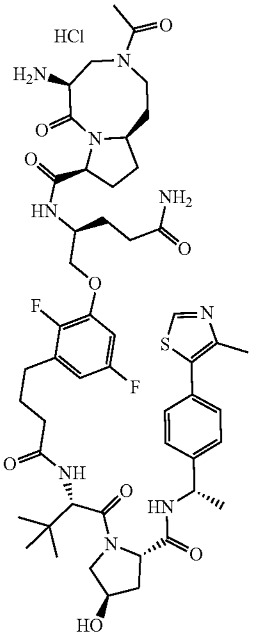 [SMILES: CC(=O)N1CC[C@H]2CC[C@@H](C(=O)N[C@@H](CCC(N)=O)COc3cc(F)cc(CCCC(=O)N[C@H](C(=O)N4C[C@H](O)C[C@H]4C(=O)N[C@@H](C)c4ccc(-c5scnc5C)cc4)C(C)(C)C)c3F)N2C(=O)[C@@H](N)C1 ; Cl] | (2S,4R)-1-[(2S)-2-(4-[3-[(2S)-2-[[(5S,8S,10aR)-3-acetyl-5-amino-6-oxo-octahydropyrrolo[1,2-a][1,5]diazocin-8-yl]formamido]-4-carbamoylbutoxy]-2,5-difluorophenyl]butanamido)-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride | 1008.15 | crude used directly without purification |

TABLE 53-continued

Characterization data for intermediates prepared according to above.

| Intermediate | Structure | Chemical Name | MS: $[(M + 1)]^+$ | $^1H$ NMR |
|---|---|---|---|---|
| J212 | HCl 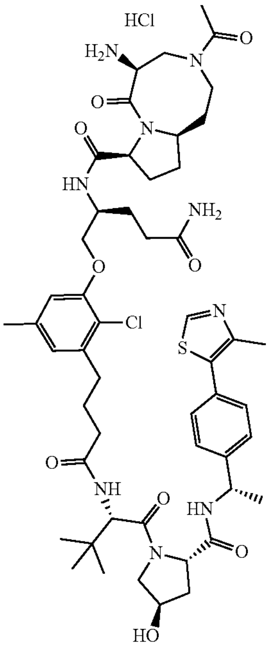 | (5S,8S,10aR)-3-acetyl-5-amino-N-((S)-5-amino-1-(2-chloro-3-(4-(((S)-1-((2S,4R)-4-hydroxy-2-(((S)-1-(4-(4-methylthiazol-5-yl)phenyl)ethyl) carbamoyl)-pyrrolidin-1-yl)-3,3-dimethyl-1-oxobutan-2-yl)amino)-4-oxobutyl)-5-methylphenoxy)-5-oxopentan-2-yl)-6-oxodecahydro-pyrrolo[1,2-a][1,5]diazocine-8-carboxamide hydrochloride | 1020.05. | (400 MHz, DMSO-$d_6$) δ 9.08 (s, 1H), 8.58-8.53 (m, 1H), 8.44-8.33 (m, 2H), 8.19 (d, J = 8.0 Hz, 1H), 7.88 (d, J = 9.3 Hz, 1H), 7.48-7.42 (d, J = 8.3 Hz, 2H), 7.39 (d, J = 8.3 Hz, 2H), 7.33-7.20 (m, 1H), 6.84 (d, J = 1.8 Hz, 1H), 6.78-6.75 (m, 1H), 6.73-6.67 (m, 1H), 4.98-4.87 (m, 1H), 4.57-4.34 (m, 3H), 4.28-4.20 (m, 3H), 4.13-3.97 (m, 3H), 3.95-3.84 (m, 1H), 3.79-3.72 (m, 1H), 3.66-3.59 (m, 2H), 3.29-3.13 (m, 2H), 2.69-2.57 (m, 2H), 2.47 (s, 3H), 2.36-2.23 (m, 5H), 2.22-2.08 (m, 6H), 2.06-1.64 (m, 12H), 1.38 (d, J = 7.0 Hz, 3H), 0.95 (s, 9H) |
| J213 | HCl 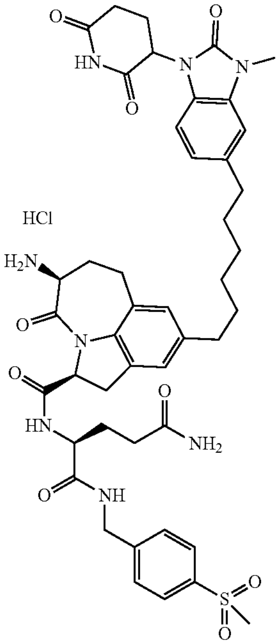 [SMILES: Cn1c(=O)n(C2CCC(=O)NC2=O)c2ccc(CCCCCCc3cc4c5c(c3)C[C@@H](C(=O)N[C@@H](CCC(N)=O)C(=O)NCc3ccc(S(C)(=O)=O)cc3)N5C(=O)[C@@H](N)CC4)cc21 ; Cl] | (2S)-2-[[(2S,11S)-11-amino-6-[6-[1-(2,6-dioxopiperidin-3-yl)-3-methyl-2-oxo-1,3-benzodiazol-5-yl]hexyl]-12-oxo-1-azatricyclo [6.4.1.0^[4,13]] trideca-4(13),5,7-trien-2-yl]formamido]-N-[(4-methanesulfonyl-phenyl)methyl] pentanediamide hydrochloride | 883.40 | (300 MHz, DMSO-$d_6$) δ 11.10 (s, 1H), 8.63 (t, J = 5.9 Hz, 1H), 8.50-8.43 (m, 3H), 7.85 (d, J = 7.2 Hz, 2H), 7.48 (d, J = 8.0 Hz, 2H), 7.34 (s, 1H), 7.05-6.94 (m, 3H), 6.90-6.80 (m, 3H), 5.41-5.31 (m, 1H), 5.20-5.12 (m, 1H), 4.38 (d, J = 5.9 Hz, 2H), 4.27-4.14 (m, 2H), 3.47-3.38 (m, 1H), 3.34 (s, 3H), 3.20 (s, 3H), 3.15-3.11 (m, 2H), 2.97-2.86 (m, 2H), 2.79-2.57 (m, 5H), 2.26-2.10 (m, 3H), 2.07-1.96 (m, 2H), 1.94-1.77 (m, 2H), 1.65-1.47 (m, 5H), 1.38-1.28 (m, 4H) |

TABLE 53-continued

| Intermediate | Structure | Chemical Name | MS: $[(M+1)]^+$ | $^1H$ NMR |
|---|---|---|---|---|
| Characterization data for intermediates prepared according to above. | | | | |
| J214 | 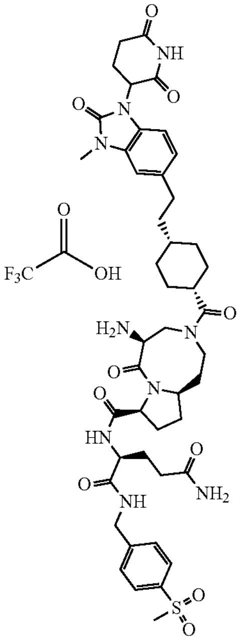 [SMILES: O=C(O)C(F)(F)F ; Cn1c(=O)n(C2CCC(=O)NC2=O)c2ccc(CC[C@H]3CC[C@@H](C(=O)N4CC[C@H]5CC[C@@H](C(=O)N[C@@H](CCC(N)=O)C(=O)NCc6ccc(S(C)(=O)=O)cc6)N5C(=O)[C@@H](N)C4)CC3)cc21] | (2S)-2-[[(5S,8S,10aR)-5-amino-6-oxo-3-[(1s,4s)-4-[2-[1-(2,6-dioxopiperidin-3-yl)-3-methyl-2-oxo-1,3-benzodiazol-5-yl]ethyl] cyclohexanecarbonyl]-octahydropyrrolo[1,2-a][1,5]diazocin-8-yl]formainido]-N-[(4-methanesulfonyl-phenyl)methyl] pentanediamide trifluoroacetate | 918.30 | (400 MHz, DMSO-$d_6$) δ 11.09 (s, 1H), 8.59 (d, J = 6.2 Hz, 1H), 8.41-8.26 (m, 3H), 7.87 (d, J = 8.1 Hz, 2H), 7.50 (dd, J = 8 4, 2.8 Hz, 2H), 7.24 (s, 1H), 7.07-6.98 (m, 2H), 6.87 (t, J = 9.3 Hz, 1H), 6.80 (s, 1H), 5.35 (dd, J = 12.6, 5.4 Hz, 1H), 4.90-4.83 (m, 1H), 4.46-4.44 (m, 1H), 4.41-4.39 (m, 1H), 4.28-4.24 (m, 1H), 4.20-4 16 (m, 1H), 3.99-3.88 (m, 1H), 3.87-3.75 (m, 1H), 3.33 (s, 3H), 3.20 (s, 3H), 2.93-2.85 (m, 1H), 2.73-2.59 (m, 5H), 2.42-2.32 (m, 1H), 2.26-2.18 (m, 2H), 2.16-2.09 (m, 2H), 2.04-1.87 (m, 4H), 1.84-1.70 (m, 6H), 1.67-1.43 (m, 10H) |

(2S)-2-1[[(5S,8S,10aR)-5-amino-3-1[6-1[1-(2,6-dioxopiperidin-3-yl)-3-methyl-2-oxo-1,3-benzodiazol-5-yl]hexanoyl]-6-oxo-octahydropyrrolo[1,2-a][1,5]diazocin-8-yl]formamido]-N-(diphenylmethyl) pentanediamide (Intermediate J79)

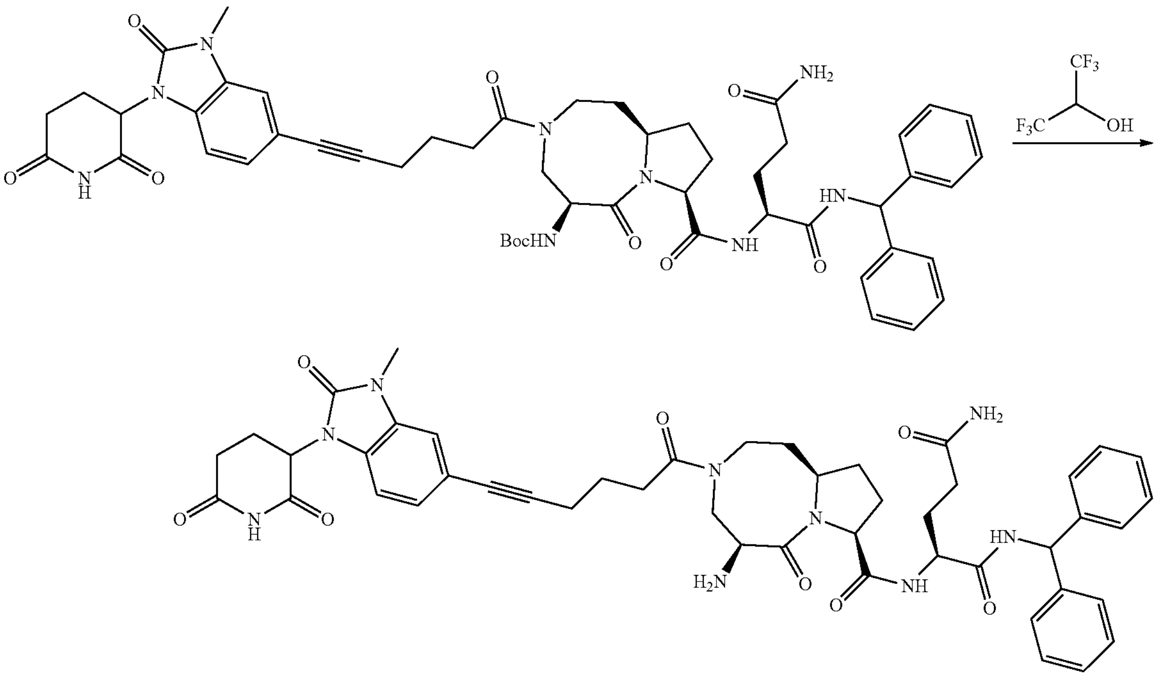

A solution of tert-butyl N-[(5S,8S,10aR)-8-[[1(1S)-3-carbamoyl-1-(diphenylmethylcarbamoyl)propyl]carbamoyl]-3-[6-[1-(2,6-dioxopiperidin-3-yl)-3-methyl-2-oxo-1,3-benzodiazol-5-yl]hex-5-ynoyl]-6-oxo-octahydropyrrolo[1,2-a][1,5]diazocin-5-yl]carbamate (300 mg, 0.31 minol) in $(CF_3)_2CHOH$ (15.0 mL) was stirred for 4 days at 65° C. under nitrogen atmosphere. The resulting mixture was cooled down to room temperature and concentrated under reduced pressure. The residue was purified by Prep-TLC ($CH_2Cl_2$:MeOH=10:1) to afford the title compound as a light yellow solid (180 mg, 640%): $^1$H NMR (400 MHz, DMSO-$d_6$) δ 11.12 (s, 1H), 8.74 (d, J=8.7 Hz, 1H), 8.15 (dd, J=16.0, 7.9 Hz, 1H), 7.36-7.19 (m, 12H), 7.14-7.07 (m, 2H), 6.75 (d, J=12.6 Hz, 1H), 6.09 (dd, J=8.5, 2.3 Hz, 1H), 5.38 (dd, J=12.8, 5.4 Hz, 1H), 4.45-4.27 (m, 5H), 4.14 (d, J=7.9 Hz, 1H), 4.00-3.72 (m, 3H), 3.72-3.43 (m, 2H), 3.32 (s, 3H), 2.94 (m, 2H), 2.79-2.55 (in, 2H), 2.49-2.41 (m, 2H), 2.20-1.89 (in, 3H), 1.89-1.54 (in, 1OH); MS (ESI, m/z): $[(M+1)]^+$=872.50.

The following intermediates in Table 54 were prepared according to the above procedure to prepare Intermediate 179.

TABLE 54

Characterization data for intermediates prepared according to above.

| Intermediate | Structure | Chemical Name | MS: $[(M + 1)]^+$ | $^1$H NMR |
|---|---|---|---|---|
| J80 | 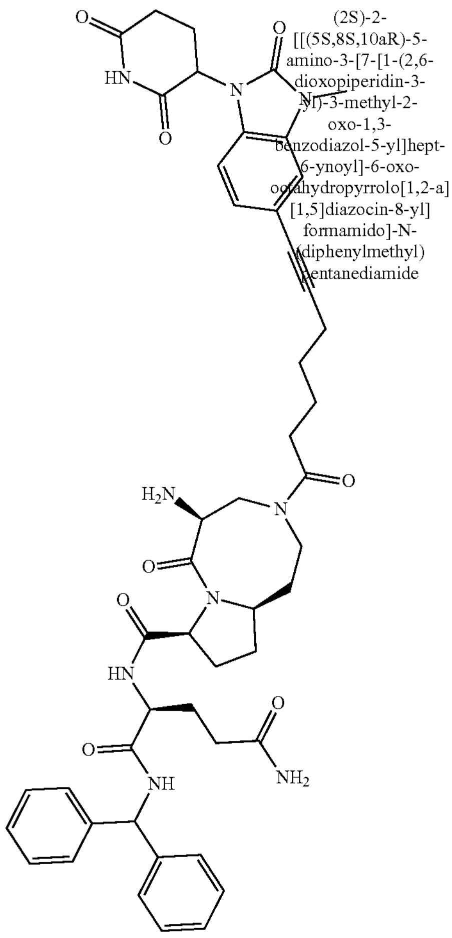 | (2S)-2-[[(5S,8S,10aR)-5-amino-3-[7-[1-(2,6-dioxopiperidin-3-yl)-3-methyl-2-oxo-1,3-benzodiazol-5-yl]hept-6-ynoyl]-6-oxo-octahydropyrrolo[1,2-a][1,5]diazocin-8-yl]formamido]-N-(diphenylmethyl)pentanediamide | 886.5 | (400 MHz, DMSO-$d_6$) δ 11.12 (s, 1H), 8.73 (dd, J = 8.5, 6.0 Hz, 1H), 8.20-8.10 (m, 1H), 7.41-7.20 (m, 12H), 7.09 (d, J = 2.2 Hz, 1H), 6.74 (d, J = 12.8 Hz, 1H), 6.10 (d, J = 8.4 Hz, 1H), 5.38 (dd, J = 12.8, 5.3 Hz, 1H), 4.47-4.27 (m, 3H), 4.12 (s, 1H), 3.85-3.77 (m, 1H), 3.77-3.55 (m, 2H), 3.52-3.38 (m, 1H), 3.32 (s, 3H), 3.27-3.15 (m, 1H), 3.05-2.80 (m, 1H), 2.80-2.57 (m, 3H), 2.48-2.26 (m, 3H), 2.23-1.40 (m, 17H). |

TABLE 54-continued

Characterization data for intermediates prepared according to above.

| Intermediate | Structure | Chemical Name | MS: [(M + 1)]$^+$ | $^1$H NMR |
|---|---|---|---|---|
| J81 | 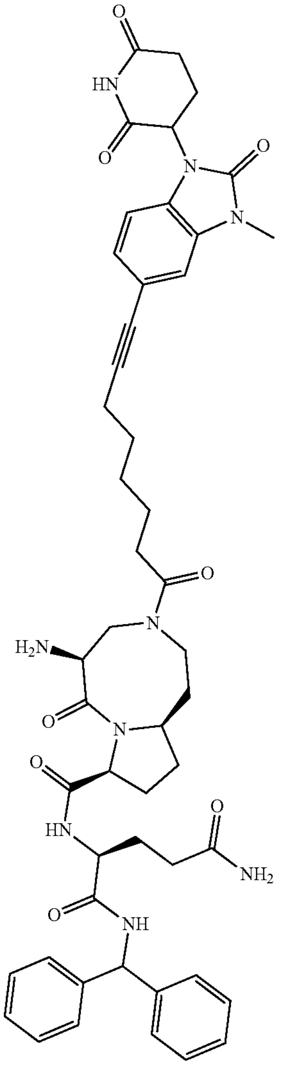 [SMILES: Cn1c(=O)n(C2CCC(=O)NC2=O)c2ccc(C#CCCCCCC(=O)N3CC[C@H]4CC[C@@H](C(=O)N[C@@H](CCC(N)=O)C(=O)NC(c5ccccc5)c5ccccc5)N4C(=O)[C@@H](N)C3)cc21] | (2S)-2-[[(5S,8S,10aR)-5-amino-3-[8-[1-(2,6-dioxopiperidin-3-yl)-3-methyl-2-oxo-1,3-benzodiazol-5-yl]oct-7-ynoyl]-6-oxo-octahydropyrrolo-[1,2-a][1,5]diazocin-8-yl]formamido]-N-(diphenylmethyl) pentanediamide | 900.3 | (400 MHz, $CDCl_3$) δ 7.78-7.55 (m, 1H), 7.50-7.15 (m, 9H), 7.15-6.86 (m, 2H), 6.82-6.58 (m, 1H), 6.19 (dd, J = 8.2, 4.5 Hz, 1H), 5.81 (s, 1H), 5.25 (m, 1H), 4.51 (s, 1H), 4.35-4.18 (m, 1H), 4.11-3.90 (m, 1H), 3.90-3.59 (m, 2H), 3.39 (s, 3H), 3.30-3.10 (m, 1H), 2.95-1.36 (m, 20H), 1.35-1.21 (m, 3H), 0.99-0.79 (m, 2H). |

Tert-butyl N-[(5S,8S,10aR)-8-[[1(S)-3-carbamoyl-1-(diphenylmethylcarbamoyl)propyl]carbamoyl]-6-oxo-octahydro-1H-pyrrolo[1,2-a][1,5]diazocin-5-yl]carbamate (Intermediate K)

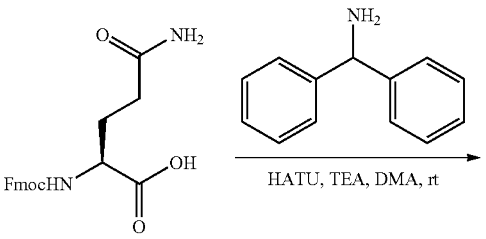

-continued

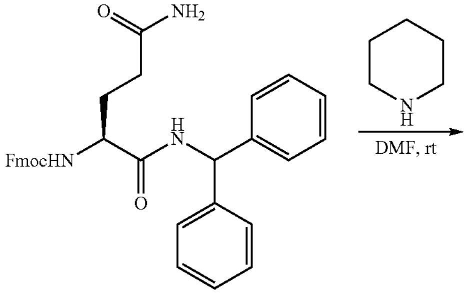

-continued

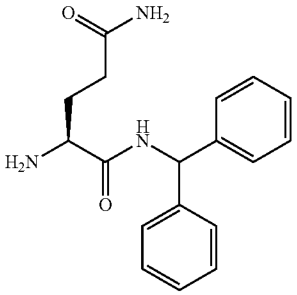

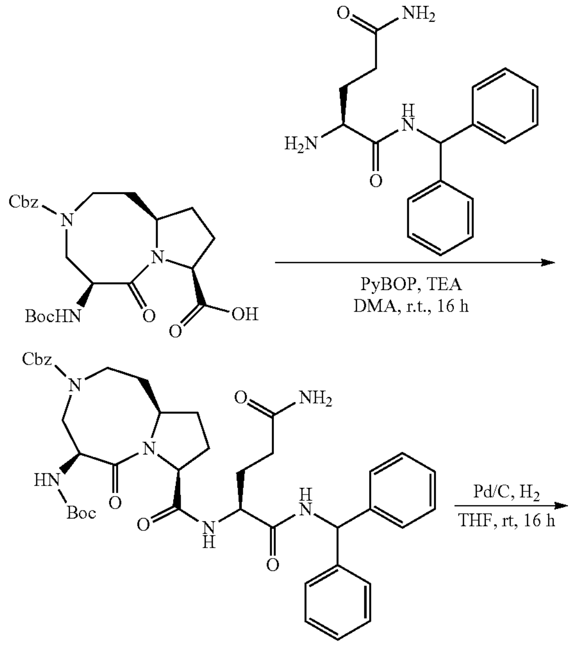

-continued

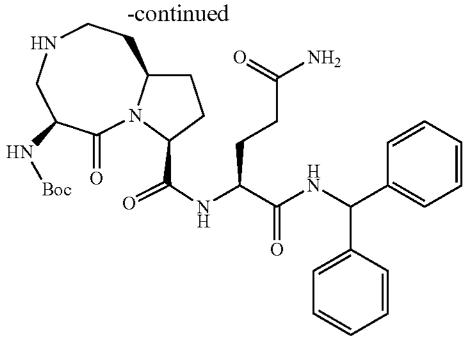

Intermediate K

Step 1: 9H-fluoren-9-ylmethyl N-L(S)-3-carbamoyl-1-(diphenylmethylcarbamoyl)propyl]carbamate. To a solution of (2S)-4-carbamoyl-2-[[(9H-fluoren-9-ylmethoxy)carbonyl]amino]butanoic acid (synthesized according to the literature WO2007/1306) (20.0 g, 54.3 mmol) and TEA (11.0 g, 110 mmol) in DMA (400 mL) were added diphenylmethanamine (10.9 g, 0.06 mmol) and HATU (24.8 g, 0.065 mmol) at 25° C. The mixture was stirred at 25° C. for 16 h. The product was precipitated by the slow addition of water (200 mL) at room temperature and was collected by filtration and washed with water (2x50.0 mL). The solids were triturated with acetone (100 mL) for 30 min. After filtration, the filtered cake was collected and washed with acetone (2x30.0 mL). The solids were dried under vacuum to afford the title compound as a white solid (38.0 g, 73%): $^1$H NMR (400 MHz, DMSO-$d_6$) δ 8.80 (d, J=8.5 Hz, 1H), 7.90 (d, J=7.5 Hz, 2H), 7.74 (dd, J=7.5, 4.8 Hz, 2H), 7.55 (d, J=8.3 Hz, 1H), 7.42 (td, J=7.5, 2.1 Hz, 2H), 7.37-7.20 (m, 12H), 6.78 (s, 1H), 6.11 (d, J=8.4 Hz, 1H), 4.33-4.08 (m, 4H), 2.30-2.03 (m, 2H), 1.91 (ddt, J=15.1, 10.3, 5.2 Hz, 1H), 1.79 (ddt, J=13.6, 9.2, 4.9 Hz, 1H); LC/MS (ESI, m/z): $[(M+1)]^+$=534.40.

The intermediates in Table 55 were prepared according to Step 1 of the procedure to prepare Intermediate K.

TABLE 55

Characterization data for intermediates prepared according to above.

| Intermediate | Structure | Chemical Name | MS: $[(M + 1)]^+$ | $^1$H-NMR |
|---|---|---|---|---|
| K-1-1 | 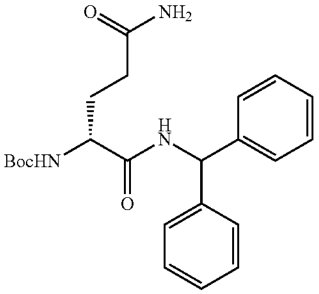 [SMILES: CC(C)(C)OC(=O)N[C@H](CCC(N)=O)C(=O)NC(c1ccccc1)c1ccccc1] | tert-butyl N-[(1R)-3-carbamoyl-1-(diphenylmethylcarbamoyl)-propyl]carbamate | 412.15 | (400 MHz, $CD_3OD$) δ 7.36-7.32 (m, 4H), 7.27 (dd, J = 8.6, 6.4 Hz, 6H), 6.17 (s, 1H), 4.16 (dd, J = 9.0, 5.1 Hz, 1H), 2.30 (t, J = 7.6 Hz, 2H), 2.08-2.04 (m, 1H), 1.89-1.86 (m, 1H), 1.46 (s, 9H) |

TABLE 55-continued

Characterization data for intermediates prepared according to above.

| Intermediate | Structure | Chemical Name | MS: $[(M + 1)]^+$ | $^1$H-NMR |
|---|---|---|---|---|
| K-1-2 | 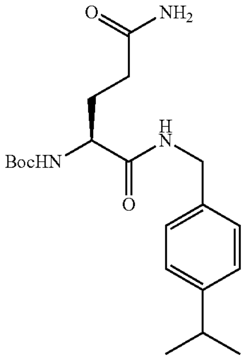 [SMILES: CC(C)c1ccc(CNC(=O)[C@H](CCC(N)=O)NC(=O)OC(C)(C)C)cc1] | tert-butyl N-[(1S)-3-carbamoyl-1-[[(4-isopropylphenyl)methyl]carbamoyl]propyl] carbamate | 378.30 | (300 MHz, DMSO-$d_6$) δ 8.45-8.16 (m, 1H), 7.32 (s, 1H), 7.19-715 (m, 4H), 6.91 (d, J = 8.0 Hz, 1H), 6.79 (s, 1H), 4.25 (t, J = 5.2 Hz, 2H), 3.97-3.78 (m, 1H), 2.86 (p, J = 6.8 Hz, 1H), 2.13 (d, J = 11.0 Hz, 2H), 1.96-1.64 (m, 2H), 1.40 (s, 9H), 1.19 (d, J = 6.7 Hz, 6H) |
| K-1-3 | 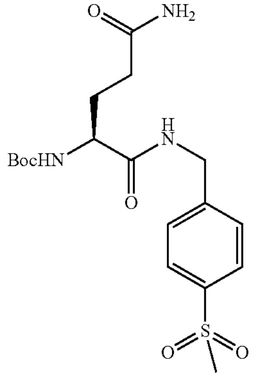 [SMILES: CC(C)(C)OC(=O)N[C@@H](CCC(N)=O)C(=O)NCc1ccc(S(C)(=O)=O)cc1] | tert-butyl N-[(1S)-3-carbamoyl-1-[[(4-methanesulfonylphenyl)-methyl]carbamoyl]propyl]-carbamate | 414.05 | (400 MHz, DMSO-$d_6$) δ 8.48 (t, J = 6.1 Hz, 1H), 7.85 (d, J = 8.1 Hz, 2H), 7.51 (d, J = 8.1 Hz, 2H), 7.28 (s, 1H), 7.02 (d, J = 7.7 Hz, 1H), 6.78 (s, 1H), 4.38 (d, J = 6.0 Hz, 2H), 3.91 (td, J = 8.5, 5.4 Hz, 1H), 3.19 (s, 3H), 2.11 (dt, J = 8.6, 6.1 Hz, 2H), 1.87 (ddt, J = 14.4, 9.3, 5.9 Hz, 1H), 1.72 (ddd, J = 15.0, 12.1, 7.5 Hz, 1H), 1.40 (s, 9H) |

Step 2: (2S)-2-Amino-N-(diphenylmethyl)pentanediamide. To a stirred solution of 9H-fluoren-9-ylmethyl N-[(1S)-3-carbamoyl-1-(diphenylmethylcarbamoyl)propyl] carbamate (4.00 g, 7.50 mmol) in DMF (10.0 mL) was added piperidine (5.00 mL) dropwise at room temperature under argon atmosphere. The resulting mixture was stirred for 1 h at room temperature. The resulting mixture was concentrated under vacuum. The residue was purified by reverse phase flash chromatography with the following conditions: Column: Spherical $C^{18}$, 20-40 um, 330 g; Mobile Phase A: water (plus 10 mmol/$LNH_4HCO_3$); Mobile Phase B: ACN; Flow rate: 80 mL/min; Gradient: 30% B - 50% B in 20 min; Detector: UV 254/220 nm. The fractions containing desired product were collected at 39% B and concentrated under reduced pressure to afford the title compound as an off-white solid (2.0 g, 86%): $^1$H NMR (400 MHz, DMSO-$d_6$) δ 8.67 (d, J=8.6 Hz, 1H), 7.39-7.21 (m, 1OH), 6.70 (s, 1H), 6.10 (d, J=7.5 Hz, 1H), 3.24 (dd, J=8.3, 5.0 Hz, 1H), 2.23-2.03 (m, 2H), 1.85 (d, J=5.4 Hz, 2H), 1.65-1.51 (m, 1H); LC/MS (ESI, m/z): $[(M+1)]^+$=312.10.

Step 3: Benzyl (5S,8S,10aR)-5-[(tert-butoxycarbonyl) amino]-8-[[(1S)-3-carbamoyl-1-(diphenylmethylcarbamoyl])propyl]carbamoyl]-6-oxo-octahydropyrrolo[1,2-a][1,5] diazocine-3-carboxylate. To a stirred solution of (5S,8S,10aR)-3-[(benzyloxy)carbonyl]-5-[(tert-butoxycarbonyl) amino]-6-oxo-octahydropyrrolo[1,2-a][1,5]diazocine-8-carboxylic acid (1.00 g, 2.17 mmol), (2S)-2-amino-N-(diphenylmethyl)pentanediamide (0.74 g, 2.38 mmol) and TEA (0.44 g, 4.33 mmol) in DMA (20.0 mL) was added PyBOP (1.69 g, 3.25 mmol) in portions at room temperature under air atmosphere. The resulting mixture was stirred for 16 h at room temperature. The reaction was quenched by the addition of water (60.0 mL). The resulting mixture was extracted with EtOAc (3×50.0 mL). The combined organic layers were washed with brine (100 mL), dried over anhydrous $Na_2SO_4$. After filtration, the filtrate was concentrated under reduced pressure to give the title compound as a yellow oil (1.50 g, crude): $^1$H NMR (400 MHz, $CDCl_3$) δ 7.41-7.13 (m, 15H), 6.19 (d, J=8.3 Hz, 1H), 5.71-5.45 (m, 2H), 5.17 (s, 2H), 4.64 (dd, J=60.9, 9.1 Hz, 2H), 4.38-4.18 (m, 1H), 3.77-3.50 (m, 2H), 3.35 (s, 1H), 2.50-2.29 (m, 2H), 2.19 (dd, J=26.1, 16.3 Hz, 3H), 2.02-1.89 (m, 3H), 1.73-1.52 (m, 2H), 1.45 (s, 9H); LC/MS (ESI, m/z): $[(M+1)]^+$=755.25.

Step 4: Tert-butyl N-[(5S,8S,10aR)-8-[[(1S)-3-carbamoyl-1-(diphenylmethylcarbamoyl)propyl]carbamoyl]-6-oxo-octahydro-1H-pyrrolo[1,2-al[1,5]diazocin-5-yl]carbamate. To a solution of benzyl (5S,8S,10aR)-5-[(tert-butoxycarbonyl)amino]-8-[[(1S)-3-carbamoyl-1-(diphenylmethylcarbamoyl)propyl]carbamoyl]-6-oxo-octahydropyrrolo[1,2-a][1,5]diazocine-3-carboxylate (10.0 g, 13.3 mmol) in THF (200 mL) was added 10% palladium on activated carbon (140 mg) under nitrogen atmosphere. The mixture was degassed for three times and was hydrogenated at room temperature for 4 h using a hydrogen balloon. The resulting mixture was filtered. The filter cake was washed with THF (3×20.0 mL). The combined filtrates was concentrated under reduced pressure. The residue was purified by reverse phase flash chromatography with the following conditions: Column: WelFlash™ C18-I, 20~40 μm, 80 g; EluentA: water (plus 10 mmol/L TEA); Eluent B:

ACN; Gradient: 35% - 55% B in 15 min; Flow rate: 50 mL/min; Detector: UV 220/254 nm; desired fractions were collected at 48% B and concentrated under reduced pressure to afford the title compound as a light yellow solid (7.0 g, 85%): $^1$H NMR (400 MHz, DMSO-d4) δ 8.91 (d, J=7.9 Hz, 1H), 8.34 (d, J=8.6 Hz, 1H), 7.40-7.18 (m, 11H), 6.78 (s, 1H), 6.09 (d, J=8.6 Hz, 1H), 5.94 (d, J=7.6 Hz, 1H), 4.70-4.58 (m, 1H), 4.36 (dt, J=19.5, 10.2 Hz, 2H), 4.30-4.17 (m, 1H), 3.13 (d, J=14.1 Hz, 1H), 3.02 (td, J=6.6, 3.9 Hz, 2H), 2.80 (dd, J=11.9, 6.2 Hz, 2H), 2.65 (t, J=12.9 Hz, 1H), 2.47-2.23 (m, 2H), 2.02 (td, J=14.2, 12.5, 6.4 Hz, 2H), 1.91-1.64 (m, 4H), 1.39 (s, 1OH); LC/MS (ESI, m/z): $[(M+1)]^+$=621.30.

The intermediates in Table 56 were prepared according to Step 4 of the procedure to prepare Intermediate K.

TABLE 56

| Characterization data for intermediates prepared according to above. | | | | |
|---|---|---|---|---|
| Intermediate | Structure | Chemical Name | MS: $[(M + 1)]^+$ | $^1$H-NMR |
| K1 | 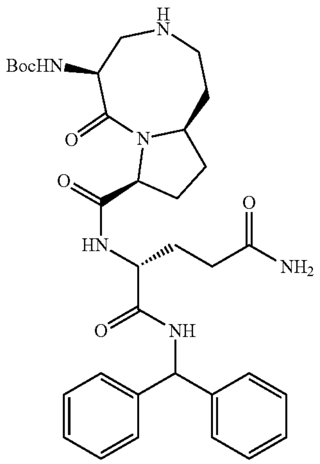 [SMILES: CC(C)(C)OC(=O)N[C@H]1CNCC[C@H]2CC[C@@H](C(=O)N[C@H](CCC(N)=O)C(=O)NC(c3ccccc3)c3ccccc3)N2C1=O] | tert-butyl N-[(5S,8S,10aR)-8-[[(1R)-3-carbamoyl-1-(diphenylmethyl-carbamoyl)propyl]-carbamoyl]-6-oxo-octahydro-1H-pyrrolo[1,2-a][1,5]diazocin-5-yl]carbamate | 621.25 | (400 MHz, DMSO-$d_6$) δ 8.94 (d, J = 8.2 Hz, 1H), 8.67 (d, J = 8.7 Hz, 1H), 7.45-7.16 (m, 11H), 6.76 (s, 1H), 6.62 (d, J = 7.4 Hz, 1H), 6.14 (dd, J = 18.3, 8.7 Hz, 1H), 4.59 (d, J = 6.0 Hz, 1H), 4.41-4.17 (m, 2H), 3.62 (d, J = 13.3 Hz, 1H), 3.30 (s, 2H), 3.07 (d, J = 15.5 Hz, 1H), 2.93-2.77 (m, 1H), 2.72 (d, J = 12.6 Hz, 1H), 2.62 (t. J = 11.8 Hz, 1H), 2.32-1.62 (m, 9H), 1.39 (s, 9H) |
| K2 | 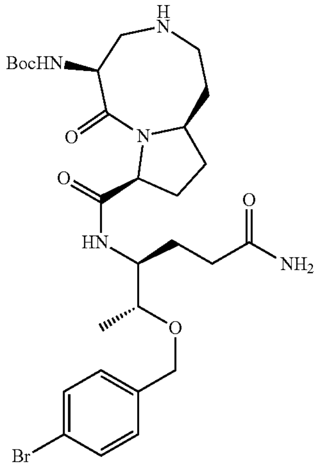 [SMILES: C[C@@H](OCc1ccc(Br)cc1)[C@H](CCC(N)=O)NC(=O)[C@@H]1CC[C@@H]2CCNC[C@H](NC(=O)OC(C)(C)C)C(=O)N21] | tert-butyl N-[(5S,8S,10aR)-8-[[(3S,4R)-4-[(4-bromophenyl)me-thoxy]-1-carbamoylpentan-3-yl]carbamoyl]-6-oxo-octahydro-1H-pyrrolo[1,2-a][1,5]diazocin-5-yl]carbamate | 624.00, 626.00 | (400 MHz, DMSO-$d_6$) δ 8.41 (d, J = 9.3 Hz, 1H), 7.58-7.49 (m, 2H), 7.35-7.27 (2, 3H), 7.16 (s, 1H), 6.84 (d, J = 7.6 Hz, 1H), 6.68 (s, 1H), 4.71-4.26 (m, 6H), 3.76-3.64 (m, 1H), 3.39 (d, J = 6.3 Hz, 1H), 3.18-3.01 (m, 1H), 2.80 (dd, J = 11.9, 6.1 Hz, 1H), 2.75-2.59 (m, 2H), 2.36-2.22 (m, 1H), 2.07-1.99 (m, 2H), 1.97-1.64 (m, 3H), 1.60-1.41 (m, 2H), 1.38 (s, 9H), 1.36-1.32 (m, 2H), 1.05 (d, J = 6.2 Hz, 3H) |

TABLE 56-continued

| Characterization data for intermediates prepared according to above. | | | | |
|---|---|---|---|---|
| Intermediate | Structure | Chemical Name | MS: $[(M + 1)]^+$ | $^1$H-NMR |
| K3 | 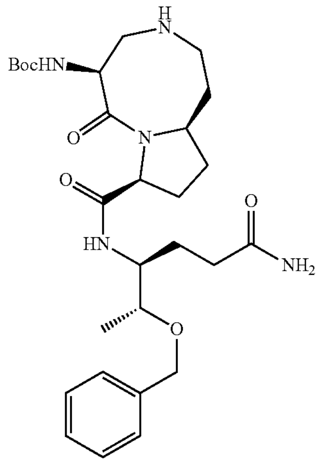 [SMILES: C[C@@H](OCc1ccccc1)[C@H](CCC(N)=O)NC(=O)[C@@H]1CC[C@@H]2CCNC[C@H](NC(=O)OC(C)(C)C)C(=O)N21] | tert-butyl N-[(5S,8S,10aR)-8-[[(3S,4R)-4-(benzyloxy)-1-carbamoylpentan-3-yl]carbamoyl]-6-oxo-octahydro-1H-pyrrolo[1,2-a][1,5]diazocin-5-yl]carbamate | 546.35 | (400 MHz, DMSO-$d_6$) δ 8.42 (d, J = 9.3 Hz, 1H), 7.39-7.23 (m, 5H), 7.18 (s, 1H), 6.84 (d, J = 7.6 Hz, 1H), 6.68 (s, 1H), 4.68-4.57 (m, 1H), 4.56-4.40 (m, 2H), 4.39-4.27 (m, 2H), 3.75-3.63 (m, 1H), 3.39 (d, J = 7.1 Hz, 2H), 3.24-3.08 (m, 2H), 2.90-2.76 (m, 1H), 2.67 (q, J = 12.2, 11.3 Hz, 2H), 2.33-2.22 (m, 1H), 2.08-1.79 (m, 4H), 1.61-1.41 (m, 2H), 1.38 (s, 9H), 1.36-1.32 (m, 2H), 1.06 (d, J = 6.2 Hz, 3H) |
| K4 | 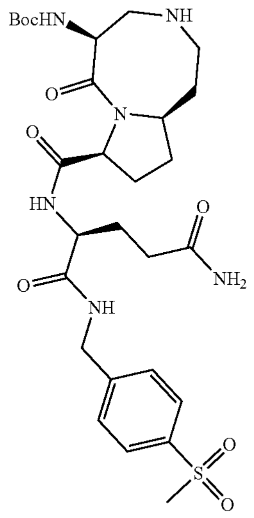 [SMILES: CC(C)(C)OC(=O)N[C@H]1CNCC[C@H]2CC[C@@H](C(=O)N[C@@H](CCC(N)=O)C(=O)NCc3ccc(S(C)(=O)=O)cc3)N2C1=O] | tert-butyl N-[(5S,8S,10aR)-8-[(3-carbamoyl-1 [[(4-methanesulfonyl-phenyl)methyl] carbamoyl]propyl) carbamoyl]-6-oxo-octahydro-1H-pyrrolo[1,2-a][1,5]diazocin-5-yl]carbamate | 623.15 | (300 MHz, CDl3) δ 9.04 (d, J = 7.6 Hz, 1H), 7.98-7.80 (m, 3H), 7.48 (d, J = 8.3 Hz, 2H), 6.51 (s, 1H), 5.66 (s, 1H), 5.18 (d, J = 8.2 Hz, 1H), 4.93-4.86 (m, 1H), 4.61-4.19 (m, 5H), 3.43-3.35 (m, 1H), 3.17-3.09 (m, 1H), 3.02 (s, 3H), 2.76-2.71 (m, 1H), 2.63-2.28 (m, 2H), 2.28-1.98 (m, 2H), 1.61-1.48 (m, 1H), 1.44 (s, 9H) |

5-[(Diethoxyphosphoryl)methyl]-1H-indole-2-carboxylic acid (Intermediate L)

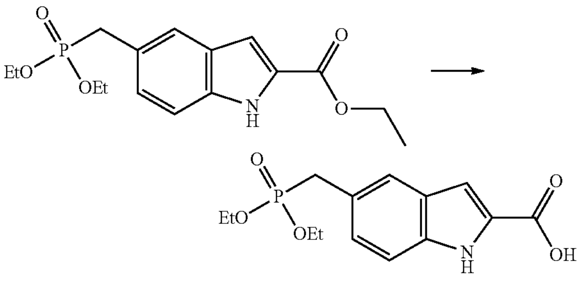

Intermediate L

To a stirred solution of ethyl 5-[(diethoxyphosphoryl) methyl]-1H-indole-2-carboxylate (synthesized according to the literature WO2010/077589) (5.00 g, 14.8 mmol) in THF (50.0 mL) was added $H_2O$ (50.0 mL) and LiOH (5.29 g, 221 mmol) in portions at room temperature. The resulting mixture was stirred for 16 h at room temperature. The mixture was acidified to pH 6 with aqueous HCl (1 M). The precipitated solids were collected by filtration and washed with water (2×10.0 mL). Then it was dried in vacuum to give the title compound as a white solid (2.20 g, 48%): $^1$H NMR (400 MHz, $CD_3OD$) δ 7.59 (ddd, J=3.4, 1.7, 0.8 Hz, 1H), 7.42 (dq, J=8.6, 1.0 Hz, 1H), 7.24 (dt, J=8.5, 1.9 Hz, 1H), 7.13 (t, J=0.8 Hz, 1H), 4.03 (dqd, J=8.1, 7.1, 2.9 Hz, 4H), 3.34 (s, 1H), 3.29 (s, 1H), 1.26 (t, J=7.1 Hz, 6H); LC/MS (ESI, m/z): $[(M+1)]^+$=312.10.

2-(4-Nitrophenoxycarbonyl)-1H-indole-5-carbonylphosphonic acid (Intermediate M)

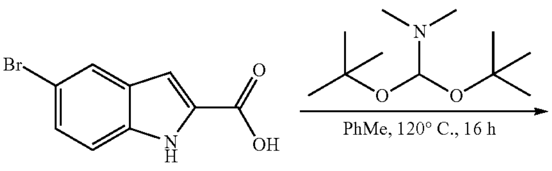

-continued

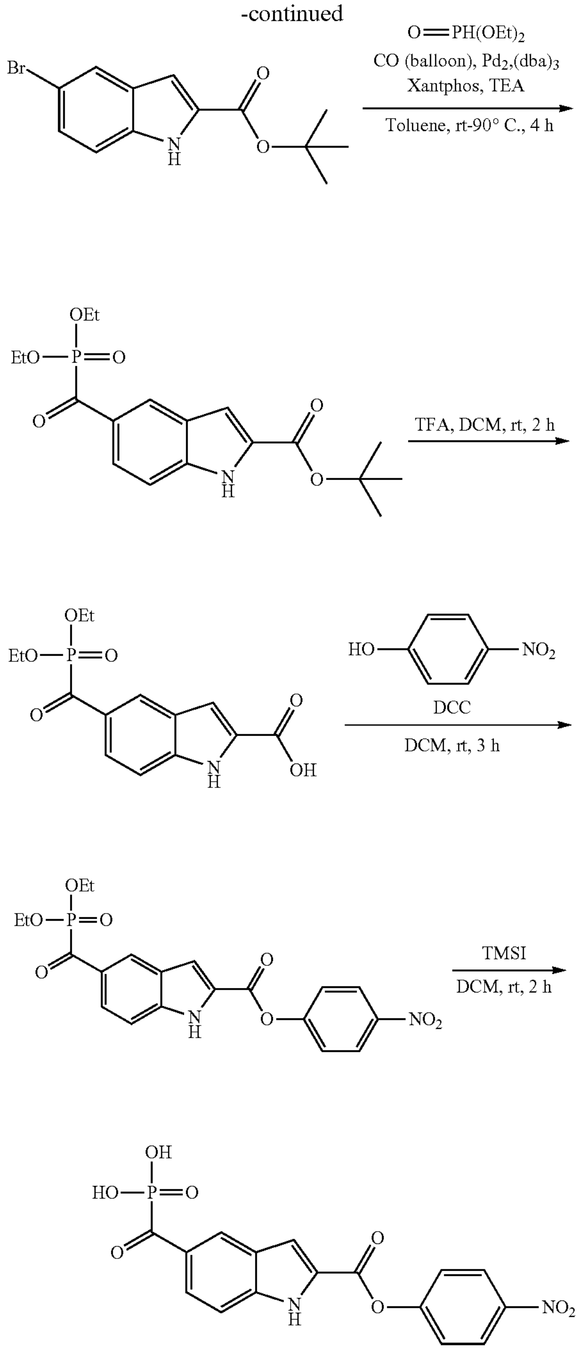

Intermediate M

Step 1: Tert-butyl 5-bromo-1H-indole-2-carboxylate. A mixture of 5-bromo-1H-indole-2-carboxylic acid (45.0 g, 188 mmol) in toluene (900 mL) was heated at 120° C. under nitrogen atmosphere. To the above mixture was added [bis(trimethyl-lambda4-oxidanyl)methyl]dimethylamine (67.2 g, 375 mmol) dropwise over 1 h at 120° C. The resulting mixture was stirred for overnight at 120° C. The resulting mixture was cooled down to room temperature and was concentrated under reduced pressure. The residue was purified by silica gel column chromatography, eluted with petroleum ether/EtOAc (10:1) to afford the title compound as a white solid (27.0 g, 49%): $^1$H NMR (400 MHz, DMSO-$d_6$) δ 11.90 (s, 1H), 7.86 (d, J=1.9 Hz, 1H), 7.42 (d, J=8.8 Hz, 1H), 7.36 (dd, J=8.8, 1.9 Hz, 1H), 7.03 (dd, J=2.2, 0.9 Hz, 1H), 1.57 (s, 9H); LC/MS (ESI, m/z): $[(M-1)]^-$=293.90, 295.90.

Step 2: Tert-butyl 5-((diethoxyphosphoryl)carbonyl)-1H-indole-2-carboxylate. To a stirred solution of tert-butyl 5-bromo-1H-indole-2-carboxylate (3.00 g, 10.2 mmol) and diethyl phosphonate (1.40 g, 10.2 mmol) in toluene (60.0 mL) were added $Pd_2(dba)_3$ $CHCl_3$ (524 mg, 0.51 mmol), XantPhos (293 mg, 0.51 mmol) and TEA (1.03 g, 10.2 mmol) in portions at room temperature under nitrogen atmosphere. The resulting mixture was stirred for 2 h at 90° C. under CO (1.5 atm.) atmosphere. The resulting mixture was cooled down to room temperature and was filtered. The filtered cake was washed with DCM (3x15.0 mL). The combined filtrates was concentrated under reduced pressure. The residue was purified by reverse phase flash with the following conditions (Column: Spherical $C^{18}$, 20~40 um, 330 g; Mobile Phase A: water (plus 0.05% FA), Mobile Phase B: ACN; Flow rate: 80 mL/min; Gradient (B%): 40%~70%, 30 min; Detector: UV 254/220 nm; Rt: 35 min.) to afford the title compound as a dark yellow oil (2.0 g, 52%): $^1$H NMR (400 MHz, DMSO-$d_6$) δ 12.28 (s, 1H), 8.76 (d, J=1.7 Hz, 1H), 7.97 (dd, J=8.9, 1.7 Hz, 1H), 7.63-7.57 (m, 1H), 7.37-7.34 (m, 1H), 4.23-4.15 (m, 4H), 1.58 (s, 9H), 1.29 (t, J=7.0 Hz, 6H); LC/MS (ESI, m/z): $[(M+1)]^+$=382.05.

Step 3: 5-((Diethoxyphosphoryl)carbonyl)-1H-indole-2-carboxylic acid. To a stirred solution of tert-butyl 5-[(diethoxyphosphoryl)carbonyl]-1H-indole-2-carboxylate (9.00 g, 23.6 mmol) in DCM (180 mL) was added TFA (90.0 mL) at room temperature under nitrogen atmosphere. The resulting mixture was stirred for 2 h at room temperature under nitrogen atmosphere. The resulting mixture was concentrated under vacuum to afford the title compound as a brown yellow solid (7.2 g, 94%): $^1$H NMR (400 MHz, DMSO-d) 8 12.36 (s, 1H), 8.78 (d, J=1.7 Hz, 1H), 7.96 (dd, J=8.9, 1.7 Hz, 1H), 7.61-7.55 (m, 1H), 7.39 (dd, J=2.1, 0.9 Hz, 1H), 4.19 (dqd, J=8.4, 7.1, 1.6 Hz, 4H), 1.29 (t, J=7.0 Hz, 6H); LC/MS (ESI, m/z): $[(M+1)]^+$=326.05.

Step 4: 4-Nitrophenyl 5-((diethoxyphosphoryl)carbonyl)-1H-indole-2-carboxylate. To a stirred mixture of 5-[(diethoxyphosphoryl)carbonyl]-1H-indole-2-carboxylic acid (500 mg, 1.54 mmol) and p-nitrophenol (321 mg, 2.31 mmol) in DCM (15.0 mL) was added DCC (476 mg, 2.31 mmol) at room temperature under nitrogen atmosphere. The resulting mixture was stirred for 3 h at room temperature under nitrogen atmosphere. The resulting mixture was concentrated under reduced pressure. The crude product was purified by reverse phase flash chromatography with the following conditions (Column: Spherical $C^{18}$, 20~40 um, 120 g; Mobile Phase A: water, Mobile Phase B: ACN; Flow rate: 45 mL/min; Gradient (B%): 40%~70%, 30 min; Detector: UV 254/220 nm; Rt: 32 min.) to afford the title compound as a yellow solid (300 mg, 440%): $^1$H NMR (400 MHz, DMSO-d) 8 12.84 (d, J=2.2 Hz, 1H), 8.88 (d, J=1.7 Hz, 1H), 8.41-8.38 (m, 2H), 8.06-8.03 (m, 1H), 7.81-7.79 (i, 1H), 7.72-7.69 (m, 2H), 7.68-7.65 (m, 1H), 4.26-4.17 (m, 4H), 1.31 (t, J=7.0 Hz, 6H); LC/MS (ESI, m/z): $[(M-1)]^-$=444.95.

The intermediates in Table 57 were prepared according to Step 4 of the procedure to prepare Intermediate M.

TABLE 57

| Characterization data for intermediates prepared according to above. | | | | |
|---|---|---|---|---|
| Intermediate | Structure | Chemical Name | MS: $[(M + 1)]^+$ | $^1H$-NMR |
| M-4-1 | 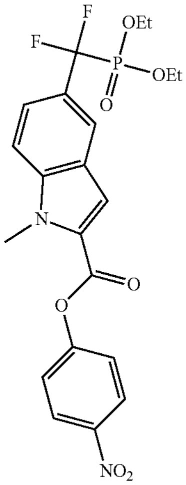 [SMILES: CCOP(=O)(OCC)C(F)(F)c1ccc2c(c1)cc(C(=O)Oc1ccc([N+](=O)[O-])cc1)n2C] | 4-nitrophenyl 5-[(diethoxyphos-phoryl) difluoromethyl]-1-methylindole-2-carboxylate | 483.1 | $^1H$ NMR (400 MHz, $CDCl_3$) δ 8.44-8.31 (m, 2H), 8.07 (d, J = 1.9 Hz, 1H), 7.70 (dt, J = 8.8, 1.4 Hz, 1H), 7.66 (d, J = 0.9 Hz, 1H), 7.53 (d, J = 8.9 Hz, 1H), 7.50-7.43 (m, 2H), 4.32-4.15 (m, 4H), 4.13 (s, 3H), 1.35 (td, J = 7.1, 0.6 Hz, 6H). |
| M-4-2 | 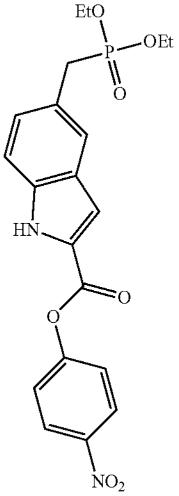 [SMILES: CCOP(=O)(Cc1ccc2[nH]c(C(=O)Oc3ccc([N+](=O)[O-])cc3)cc2c1)OCC] | 4-nitrophenyl 5-[(diethoxyphosphoryl) methyl]-1H-indole-2-carboxylate | 433.1 | $^1H$ NMR (400 MHz, DMSO-$d_6$) δ 12.22 (s, 1H), 8.44-8.31 (m, 2H), 7.71-7.64 (m, 2H), 7.63 (s, 1H), 7.48-7.41 (m, 2H), 7.27 (dt, J = 8.7, 1.8 Hz, 1H), 5.57 (d, J = 8.0 Hz, 2H), 3.94 (dqd, J = 8.8, 7.1, 1.6 Hz, 4H), 1.16 (t, J = 7.1 Hz, 6H). |
| M-4-3 | 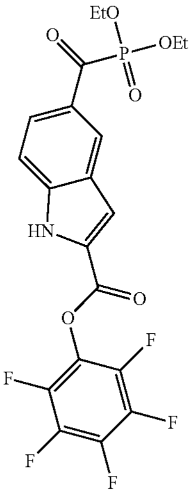 [SMILES: CCOP(=O)(OCC)C(=O)c1ccc2[nH]c(C(=O)Oc3c(F)c(F)c(F)c(F)c3F)cc2c1] | 2,3,4,5,6-pentafluorophenyl 5-[(diethoxyphos-phoryl) carbonyl]-1H-indole-2-carboxylate | $[M - 1]^- =$ 489.9 | $^1H$ NMR (400 MHz, DMSO-$d_6$) δ 13.01 (s, 1H), 8.91 (d, J = 1.6 Hz, 1H), 8.06 (dd, J = 8.8, 1.7 Hz, 1H), 7.94 (d, J = 1.5 Hz, 1H), 7.70-7.67 (m, 1H), 4.21 (dqd, J = 8.3, 7.0, 1.6 Hz, 4H), 1.30 (t, J = 7.0 Hz, 6H). |

Step 5: (2-((4-Nitrophenoxy)carbonyl)-1H-indole-5-carbonyl)phosphonic acid (Intermediate M. To a stirred solution of 4-nitrophenyl 5-[(diethoxyphosphoryl)carbonyl]-1H-indole-2-carboxylate (300 mg, 0.67 mmol) in DCM (10.0 mL) was added TMSI (404 mg, 2.02 mmol) dropwise at room temperature under nitrogen atmosphere. The resulting mixture was stirred for 2 h at room temperature under nitrogen atmosphere. The resulting mixture was concentrated under reduced pressure. The crude product was purified by reverse phase flash chromatography with the following conditions (Column: Spherical $C^{18}$, 20~40 um, 120 g; Mobile Phase A: water, Mobile Phase B: ACN; Flow rate: 45 mL/min; Gradient (B%): 15%~35%, 20 min; Detector: UV 254/220 nm; Rt: 20 min.) to afford the title compound as a yellow solid (150 mg, 570%): $^1$H NMR (400 MHz, DMSO-41) δ 12.76-12.70 (m, 1H), 8.94-8.91 (m, 1H), 8.41-8.36 (m, 2H), 8.05 (dd, J=8.8, 1.6 Hz, 1H), 7.73 (q, J=1.0 Hz, 1H), 7.72-7.67 (m, 2H), 7.62 (d, J=8.8 Hz, 1H); LC/MS (ESI, m/z): $[(M-1)]^-$=388.85.

The intermediates in Table 58 were prepared according to Step 5 of the procedure to prepare Intermediate M.

TABLE 58

| Characterization data for intermediates prepared according to above. | | | | |
|---|---|---|---|---|
| Intermediate | Structure | Chemical Name | MS: $[(M + 1)]^+$ | $^1$H-NMR |
| M1 | 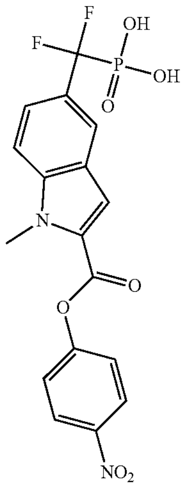 [SMILES: Cn1c(C(=O)Oc2ccc([N+](=O)[O-])cc2)cc2cc(C(F)(F)P(=O)(O)O)ccc21] | difluoro[1-methyl-2-(4-nitrophenoxycarbonyl)indol-5-yl]methylphosphonic acid | $[M - 1]^-$ = 425.05 | (400 MHz, $CDCl_3$) δ 8.35 (d, J = 9.1 Hz, 2H), 8.11 (s, 1H), 7.82 (d, J = 8.9 Hz, 1H), 7.59 (s, 1H), 7.49-7.39 (m, 3H), 4.10 (s, 3H). |
| M2 | 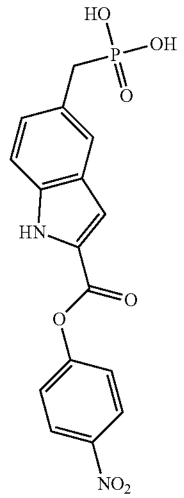 [SMILES: O=C(Oc1ccc([N+](=O)[O-])cc1)c1cc2cc(CP(=O)(O)O)ccc2[nH]1] | [2-(4-nitrophenoxycarbonyl)-1H-indol-5-yl]methylphosphonic acid | 377.05 | (400 MHz, DMSO-$d_6$) δ 12.16 (s, 1H), 8.41-8.35 (m, 2H), 7.70-7.64 (m, 2H), 7.59 (d, J = 3.0 Hz, 1H), 7.45-7.39 (m, 2H), 7.26 (d, J = 8.7 Hz, 1H), 3.04 (d, J = 21.0 Hz, 2H). |

TABLE 58-continued

| Characterization data for intermediates prepared according to above. | | | | |
|---|---|---|---|---|
| Intermediate | Structure | Chemical Name | MS: [(M + 1)]$^+$ | $^1$H-NMR |
| M3 | 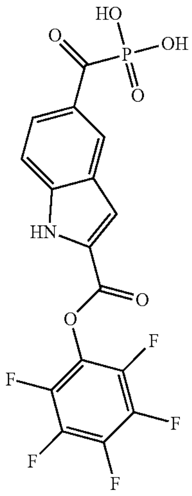 | 2-(2,3,4,5,6-pentafluorophenoxycarbonyl)-1H-indole-5-carbonylphosphonic acid | [M − 1]$^-$ = 433.80 | (400 MHz, DMSO-$d_6$) δ 12.91 (d, J = 2.2 Hz, 1H), 8.96 (d, J = 1.5 Hz, 1H), 8.08 (dd, J = 8.9, 1.6 Hz, 1H), 7.87 (d, J = 2.0 Hz, 1H), 7.67-7.61 (m, 1H). |

(2S,4R)-1-I(2S)-2-Amino-3,3-dimethylbutanoyl]-4-hydroxy-N-I(1S)-1-[4-(4-methyl-1,3-thiazol-5-yl) phenyl]ethyl]pyrrolidine-2-carboxamide hydrochloride (Intermediate N)

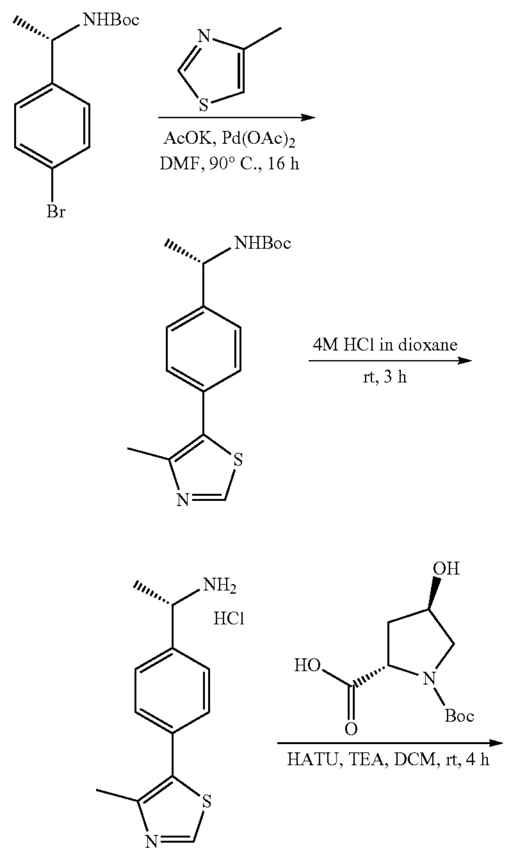

-continued

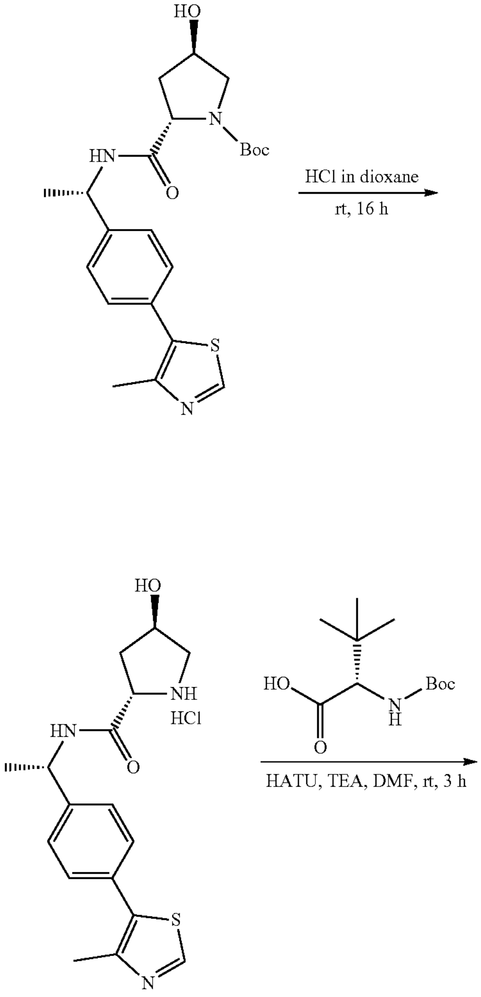

-continued

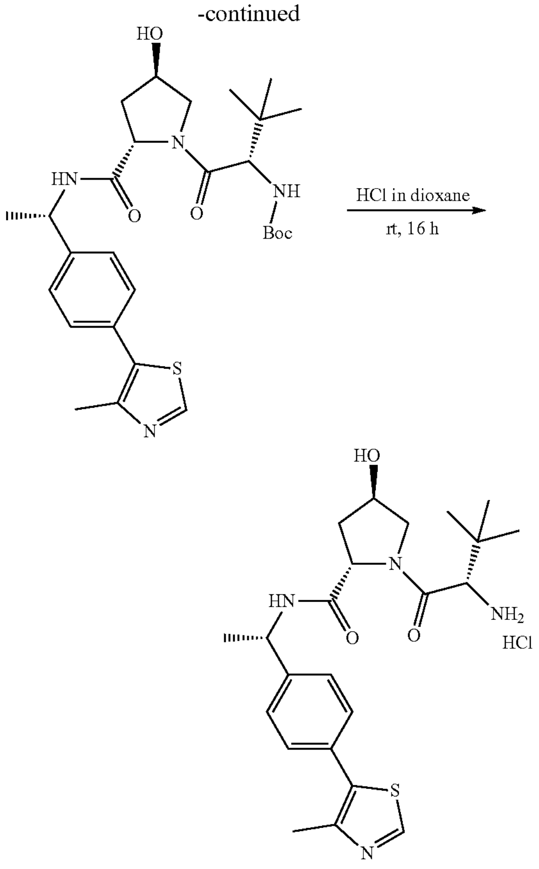

Intermediate N

Step 1: Tert-butyl N-[(1S)-1-[4-(4-methyl-1,3-thiazol-5-yl)phenyl]ethyl]carbamate. To a solution of tert-butyl N-[(1S)-1-(4-bromophenyl)ethyl]carbamate (70.0 g, 233 mmol) and 4-methylthiazole (25.5 g, 257 mmol) in DMF (500 mL) were added AcOK (45.8 g, 466 mmol) and $Pd(OAc)_2$ (5.24 g, 23.3 mmol). After being stirred for 16 h at 80° C. under nitrogen atmosphere. The reaction was cooled down to room temperature and was quenched by the addition of water (200 mL). The resulting mixture was extracted with EtOAc (3×300 mL). The combined organic layers were washed with brine (4×300 mL), dried over anhydrous $Na_2SO_4$. After filtration, the filtrate was concentrated under reduced pressure. The residue was purified by silica gel column chromatography, eluted with petroleum ether/EtOAc (10:1 to 8:1) to afford the title compound as a light yellow solid (30.0 g, 38%): $^1$H NMR (400 MHz, $CD_3OD$) δ 8.86 (s, 1H), 7.48-7.36 (m, 4H), 4.82-4.63 (m, 1H), 2.48 (s, 3H), 1.43 (s, 9H), 1.42 (d, J=6.9 Hz, 3H); LC/MS (ESI, m/z): $[(M+H)]^+$=319.15.

The intermediates in Table 59 were prepared according to Step 1 of the procedure to prepare Intermediate N.

TABLE 59

Characterization data for intermediates prepared according to above.

| Intermediate | Structure | Chemical Name | MS: $[(M + 1)]^+$ | $^1$H-NMR |
|---|---|---|---|---|
| N-1-1 | 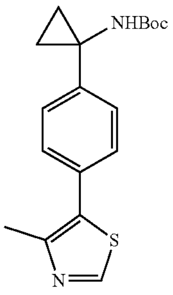 [SMILES: Cc1ncsc1-c1ccc(C2(NC(=O)OC(C)(C)C)CC2)cc1] | tert-butyl N-[1-[4-(4-methyl-1,3-thiazol-5-yl)phenyl]cyclopropyl]-carbamate | 331.20 | (400 MHz, $CDCl_3$) δ 8.69 (s, 1H), 7.45-7.34 (m, 2H), 7.27 (d, J = 8.2 Hz, 2H), 5.34 (s, 1H), 2.55 (s, 3H), 1.48 (m, 9H), 1.34-1.21 (m, 4H). |

Step 2: (1S)-1-[4-(4-methyl-1,3-thiazol-5-yl)phenyl]ethanamine hydrochloride. To a stirred solution of tert-butyl N-[(1S)-1-[4-(4-methyl-1,3-thiazol-5-yl)phenyl]ethyl]carbamate (30.0 g, 94.2 mmol) in dioxane (150 mL) was added a solution of HCl (gas) in 1,4-dioxane (4 M, 100 mL) dropwise at 25° C. under nitrogen atmosphere. The resulting mixture was stirred for 3 h at 25° C. under nitrogen atmosphere. The resulting mixture was filtered. The filter cake was washed with EtOAc (2×50.0 mL) and dried to give the title compound as a yellow solid (29.0 g, 97%): $^1$H NMR (400 MHz, $CD_3OD$) δ 10.11 (s, 1H), 7.75 (s, 4H), 4.63 (q, J=6.9 Hz, 1H), 2.67 (s, 3H), 1.73 (d, J=6.9 Hz, 3H); LC/MS (ESI, m/z): $[(M+H)]^+$=219.10.

The intermediates in Table 60 were prepared according to Step 2 of the procedure to prepare Intermediate N.

TABLE 60

Characterization data for intermediates prepared according to above.

| Intermediate | Structure | Chemical Name | MS: $[(M + 1)]^+$ | $^1$H-NMR |
|---|---|---|---|---|
| N-2-1 | 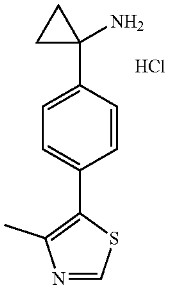 [SMILES: Cc1ncsc1-c1ccc(C2(N)CC2)cc1 ; Cl] | 1-[4-(4-methyl-1,3-thiazol-5-yl)phenyl]cyclopropan-1-amine hydrochloride | 231.15 | (400 MHz, DMSO-$d_6$) δ 9.19 (s, 1H), 9.18-9.15 (m, 3H), 7.54 (s, 4H), 2.47 (s, 3H), 1.55-1.43 (m, 2H), 1.31-1.15 (m, 2H). |

Step 3: Tert-butyl (2S,4R)-4-hydroxy-2-[[(1S)-1-[4-(4-methyl-1,3-thiazol-5-yl)phenyl]ethyl]carbamoyl]pyrrolidine-1-carboxylate. To a stirred mixture of (2S,4R)-1-(tert-butoxycarbonyl)-4-hydroxypyrrolidine-2-carboxylic acid (24.0 g, 104 mmol) and HATU (46.6 g, 123 mmol) in DMF (300 mL) were added (1S)-1-[4-(4-methyl-1,3-thiazol-5-yl)phenyl]ethanamine hydrochloride (24.0 g, 94.2 mmol) and DIEA (36.5 mL, 283 mmol) dropwise at 0° C. under nitrogen atmosphere. The resulting mixture was stirred for 4 h at 25° C. under nitrogen atmosphere. The reaction was quenched by the addition of water (200 mL) at 0° C. The resulting mixture was extracted with EtOAc (4×300 mL). The combined organic layers were washed with brine (4×300 mL), dried over anhydrous $Na_2SO_4$. After filtration, the filtrate was concentrated under reduced pressure. The residue was purified by silica gel column chromatography, eluted with petroleum ether/EtOAc (10:1 to 1:10) to give the title compound as a light yellow solid (46.0 g, 960%): $^1$H NMR (400 MHz, $CD_3OD$) δ 8.89 (s, 1H), 7.50-7.41 (m, 4H), 5.08 (td, J=7.7, 5.6 Hz, 1H), 4.44-4.27 (m, 2H), 3.57 (dt, J=11.5, 3.7 Hz, 1H), 3.50 (dt, J=11.4, 1.9 Hz, 1H), 2.50 (s,, 3H), 2.30-2.18 (m, 1H), 1.95 (ddd, J=13.1, 8.6, 4.6 Hz, 1H), 1.56-1.46 (m, 3H), 1.44s, 9H); LC/MS (ESI, m/z): $[(M+H)]^+$=432.15.

The intermediates in Table 61 were prepared according to Step 3 of the procedure to prepare Intermediate N.

TABLE 61

| Characterization data for intermediates prepared according to above. | | | | |
|---|---|---|---|---|
| Intermediate | Structure | Chemical Name | MS: $[(M+1)]^+$ | $^1H$-NMR |
| N-3-1 | 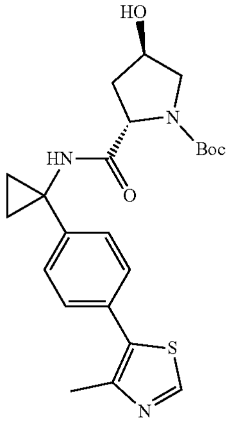 [SMILES: Cc1ncsc1-c1ccc(C2(NC(=O)[C@@H]3C[C@@H](O)CN3C(=O)OC(C)(C)C)CC2)cc1] | tert-butyl (2S,4R)-4-hydroxy-2-([1-[4-(4-methyl-1,3-thiazol-5-yl)phenyl]cyclopropyl]carbamoyl)pyrrolidine-1-carboxylate | 444.15 | (400 MHz, $CD_3OD$) δ 8.88 (s, 1H), 7.47-7.31 (m, 4H), 4.41 (tt, J = 5.8, 3.1 Hz, 1H), 4.34-4.27 (m, 1H), 3.64-3.45 (m, 2H), 2.48 (s, 3H), 2.28 (dddt, J = 17.1, 11.8, 8.0, 2.2 Hz, 1H), 2.09-1.97 (m, 1H), 1.38 (s, 9H), 1.36-1.28 (m, 4H). |
| N-3-2 | 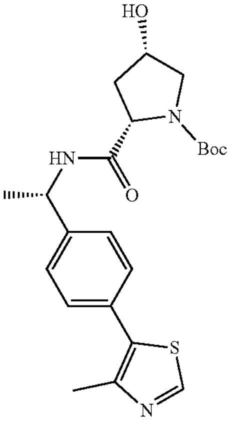 [SMILES: Cc1ncsc1-c1ccc([C@H](C)NC(=O)[C@@H]2C[C@H](O)CN2C(=O)OC(C)(C)C)cc1] | tert-butyl (2S,4S)-4-hydroxy-2-[[(1S)-1-[4-(4-methyl-1,3-thiazol-5-yl)phenyl]ethyl]carbamoyl]pyrrolidine-1-carboxylate | 432.15 | (400 MHz, $CD_3OD$) δ 8.90 (s, 1H), 7.57-7.42 (m, 4H), 5.12-5.08 (m, 1H), 4.39-4.22 (m, 2H), 3.69-3.41 (m, 2H), 2.50 (s, 3H), 2.45-2.35 (m, 1H), 1.98-1.88 (m, 1H), 1.59-1.32 (m, 12H). |

Step 4: (2S,4R')-4-hydroxy-N-[(1S)-1-[4-(4-methyl-1.3-thiazol-5-yl)phenyl]ethyl]pyrrolidine-2-carboxamide hydrochloride. To a stirred solution of tert-butyl (2S,4R)-4-hydroxy-2-[[(1S)-1-[4-(4-methyl-1,3-thiazol-5-yl)phenyl]ethyl]carbamoyl]pyrrolidine-1-carboxylate (46.0 g, 107 mmol) in dioxane (300 mL) was added a solution of HCl (gas) in 1,4-dioxane (4 M, 150 mL) dropwise at 25° C. under nitrogen atmosphere. The resulting mixture was stirred for 16 h at 25° C. under nitrogen atmosphere. The resulting mixture was filtered. The filter cake was washed with $CH_2Cl_2$ (3×50.0 mL) and dried to give the title compound as a light yellow solid (42.0 g, 96%): $^1H$ NMR (400 MHz, $CD_3OD$) δ 10.11 (s, 1H), 7.66-7.60 (d, J=8.3 Hz, 2H), 7.57 (d, J=8.3 Hz, 2H), 5.13 (q, J=7.0 Hz, 1H), 4.67-4.54 (m, 2H), 3.41 (dd, J=12. 1, 3.5 Hz, 1H), 3.37-3.29 (m, 1H), 2.65 (s, 3H), 2.56 (ddt, J=13.5, 7.5, 1.7 Hz, 1H), 1.98 (ddd, J=13.4, 10.6, 4.0 Hz, 1H), 1.56 (d, J=7.0 Hz, 3H); LC/MS (ESI, m/z): $[(M+H)]^+$=332.1.

The intermediates in Table 62 were prepared according to Step 4 of the procedure to prepare Intermediate N.

TABLE 62

Characterization data for intermediates prepared according to above.

| Inter-mediate | Structure | Chemical Name | MS: [(M + 1)]$^+$ | $^1$H-NMR |
|---|---|---|---|---|
| N-4-1 | 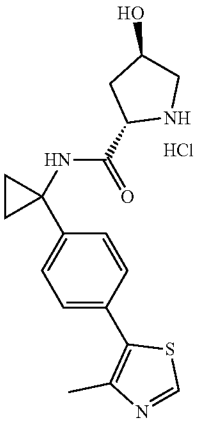 [SMILES: Cc1ncsc1-c1ccc(C2(NC(=O)[C@@H]3C[C@@H](O)CN3)CC2)cc1 ; Cl] | (2S,4R)-4-hydroxy-N-[1-[4-(4-methyl-1,3-thiazol-5-yl)phenyl]cyclopropyl]pyrrolidine-2-carboxamide hydrochloride | 344.2 | (400 MHz, $CD_3OD$) δ 9.99 (s, 1H), 7.62-7.52 (m, 2H), 7.45 (d, J = 8.5 Hz, 2H), 4.63 (t, J = 3.8 Hz, 1H), 4.55 (dd, J = 10.6, 7.5 Hz, 1H), 3.44 (dd, J = 12.1, 3.6 Hz, 1H), 3.36-3.34 (m, 1H), 2.63 (s, 3H), 2.56 (ddt, J = 13.4, 7.5, 1.7 Hz, 1H), 2.11 (ddd, J = 13.4, 10.6, 4.0 Hz, 1H), 1.42-1.36 (m, 4H). |
| N-4-2 | 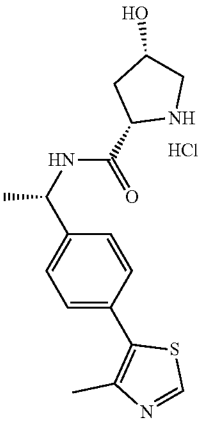 [SMILES: Cc1ncsc1-c1ccc([C@H](C)NC(=O)[C@@H]2C[C@H](O)CN2)cc1 ; Cl] | (2S,4S)-4-hydroxy-N-[(1S)-1-[4-(4-methyl-1,3-thiazol-5-yl)phenyl]ethyl]pyrrolidine-2-carboxamide hydrochloride | 332.25 | (400 MHz, $CD_3OD$) δ 10.04 (s, 1H), 7.59 (s, 4H), 5.15 (q, J = 7.0 Hz, 1H), 4.55 (ddt, J = 5.0, 3.7, 2.5 Hz, 1H), 4.46 (dd, J = 10.1, 4.7 Hz, 1H), 3.42-3.37 (m, 2H), 2.73-2.66 (m, 1H), 2.64 (s, 3H), 2.27-2.03 (m, 1H), 1.57 (d, J = 7.0 Hz, 3H). |

Step 5: Tert-butyl N-[(2S)-1-r(2S,4R)-4-hydroxy-2-[[(1S)-1-[4-(4-methyl-1.3-thiazol-5-yl)phenyl]ethyl]carbamoyl]pyrrolidin-1-yl]-3.3-dimethyl-1-oxobutan-2-yl]carbamate. To a stirred mixture of (2S)-2-[(tert-butoxycarbonyl)amino]-3,3-dimethylbutanoic acid (27.7 g, 120 minol) and TEA (45.3 mL, 448 minol) in DMF (400 mL) were added (2S,4R)-4-hydroxy-N-[(1S)-1-[4-(4-methyl-1,3-thiazol-5-yl)phenyl]ethyl]pyrrolidine-2-carboxamide hydrochloride (40.0 g, 109 minol) and HATU (53.7 g, 142 minol) in portions at 0° C. under nitrogen atmosphere. The resulting mixture was stirred for 3 h at 25° C. under nitrogen atmosphere. The reaction was quenched by the addition of water (300 mL) at 25° C. The resulting mixture was extracted with EtOAc (3×300 mL). The combined organic layers were washed with brine (3×300 mL), dried over anhydrous $Na_2SO_4$. After filtration, the filtrate was concentrated under reduced pressure. The residue was purified by trituration with EtOAc (300 mL). The precipitated solids were collected by filtration and washed with EtOAc (2×40.0 mL). This resulted in the title compound as a light yellow solid (50.0 g, 76): $^1$HNMR (400 MHz, $CD_3OD$) δ 8.90 (s, 1H), 7.50-7.36 (m, 4H), 6.40 (d, J=9.3 Hz, NH), 5.02 (p, J=7.0 Hz, 1H), 4.62 (t, J=8.3 Hz, 9H), 4.46 (s, 1H), 4.34-4.27 (, 1H), 3.87 (d, J=11.1 Hz, 1H), 3.76 (dd, J=10.9, 4.0 Hz, 1H), 2.50 (s, 3H), 2.24 (dd, J=13.2, 7.8 Hz, 1H), 2.06-1.93 (m, 1H), 1.56-1.48 (m, 3H), 1.46 (s, 9H), 1.03 (s, 9H); LC/MS (ESI, m/z): [(M+H)]$^+$=545.40.

The intermediates in Table 63 were prepared according to Step 5 of the procedure to prepare Intermediate N.

TABLE 63

Characterization data for intermediates prepared according to above.

| Intermediate | Structure | Chemical Name | MS: $[(M + 1)]^+$ | $^1$H-NMR |
|---|---|---|---|---|
| N-5-1 | 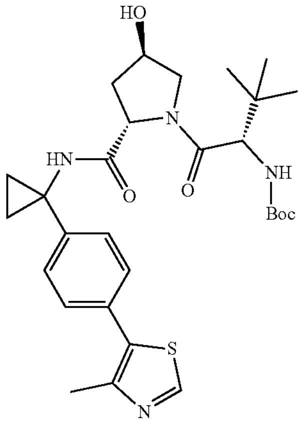 [SMILES: Cc1ncsc1-c1ccc(C2(NC(=O)[C@@H]3C[C@@H](O)CN3C(=O)[C@@H](NC(=O)OC(C)(C)C)C(C)(C)C)CC2)cc1] | tert-butyl N-[(2S)-1-[(2S,4R)-4-hydroxy-2-([1-[4-(4-methyl-1,3-thiazol-5-yl)phenyl]cyclopropyl]-carbamoyl)pyrrolidin-1-yl]-3,3-dimethyl-1-oxobutan-2-yl]carbamate | 557.25 | (400 MHz, $CD_3OD$) δ 8.87 (s, 1H), 7.45-7.33 (m, 4H), 4.61 (dd, J = 9.1, 7.5 Hz, 1H), 4.52 (s, 1H), 4.34-4.28 (m, 1H), 3.90 (d, J = 11.1 Hz, 1H), 3.80 (dd, J = 11.0, 3.9 Hz, 1H), 2.47 (s, 3H), 2.23 (ddt, J = 13.2, 7.7, 1.8 Hz, 1H), 2.07 (ddd, J = 13.3, 9.2, 4.5 Hz, 1H), 1.47 (s, 9H), 1.42-1.24 (m, 4H), 1.04 (s, 9H). |
| N-5-2 | 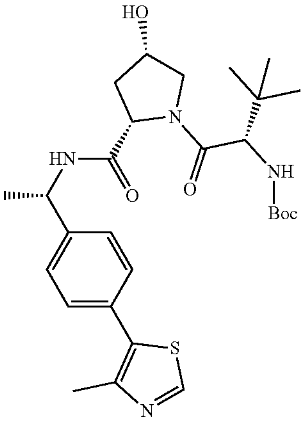 [SMILES: Cc1ncsc1-c1ccc([C@H](C)NC(=O)[C@@H]2C[C@H](O)CN2C(=O)[C@@H](NC(=O)OC(C)(C)C)C(C)(C)C)cc1] | tert-butyl N-[(2S)-1-[(2S,4S)-4-hydroxy-2-[[(1S)-1-[4-(4-methyl-1,3-thiazol-5-yl)phenyl]ethyl]car-bamoyl]pyrrolidin-1-yl]-3,3-dimethyl-1-oxobutan-2-yl]carbamate | 545.25 | (400 MHz, $CD_3OD$) δ 8.90 (s, 1H), 7.49-7.41 (m, 4H), 5.03 (qt, J = 7.1, 3.7 Hz, 1H), 4.52 (dd, J = 9.2, 4.5 Hz, 1H), 4.40 (p, J = 4.6 Hz, 1H), 4.25 (s, 1H), 4.00 (dd, J = 10.5, 5.0 Hz, 1H), 3.69 (dd, J = 10.4, 3.6 Hz, 1H), 2.50 (s, 3H), 2.48-2.39 (m, 1H), 1.92 (dt, J = 13.3, 4.4 Hz, 1H), 1.52 (d, J = 7.0 Hz, 3H), 1.46 (s, 9H), 1.04 (s, 9H). |

Step 6: (2S. 4R)-1-[(2S)-2-amino-3,3-dimethylbutanoyl]-4-hydroxy-N-[(1)-1-[4-(4-methyl 1,3-thiazol-5-yl)phenyl]ethyl]pyrrolidine-2-carboxamide hydrochloride (Intermediate N). To a stirred mixture of tert-butyl N-[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamate (49.0 g, 90.0 mmol) in MeOH (100 mL) and dioxane (400 mL) was added a solution of HCl (gas) in 1,4-dioxane (4 M, 200 mL) dropwise at 25° C. under nitrogen atmosphere. The resulting mixture was stirred for 16 h at 25° C. under nitrogen atmosphere. The resulting mixture was concentrated under reduced pressure. This resulted in the title compound as a light yellow solid (50.0 g, 98%): $^1$H NMR (400 MHz, $CD_3OD$) δ 10.10 (s, 1H), 7.66-7.57 (d, J=8.4 Hz, 2H), 7.55 (d, J=8.4 Hz, 2H), 5.03 (q, J=7.0 Hz, 1H), 4.73 (dd, J=9.5, 7.7 Hz, 1H), 4.53-4.46 (m, 1H), 4.11 (s, 1H), 3.90 (dt, J=11.3, 1.6 Hz, 1H), 3.7-3.64 (m, 1H), 3.71-3.60 (m, 1H), 2.65 (s, 3H), 2.35 (ddt, J=13.3, 7.7, 1.8 Hz, 1H), 1.94 (ddd, J=13.5, 9.5, 4.2 Hz, 1H), 1.54 (d, J=7.0 Hz, 3H), 1.16 (s, 9H); LC/MS (ESI, m/z): $[(M+H)]^+$=445.20.

The intermediates in Table 64 were prepared according to Step 6 of the procedure to prepare Intermediate N.

TABLE 64

Characterization data for intermediates prepared according to above.

| Inter-mediate | Structure | Chemical Name | MS: $[(M + 1)]^+$ | $^1$H-NMR |
|---|---|---|---|---|
| N1 | 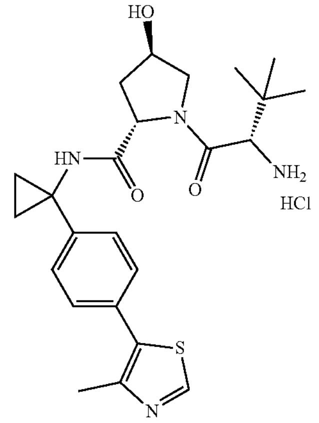 [SMILES: Cc1ncsc1-c1ccc(C2(NC(=O)[C@@H]3C[C@@H](O)CN3C(=O)[C@@H](N)C(C)(C)C)CC2)cc1 ; Cl] | (2S,4R)-1-[(2S)-2-amino-3,3-dimethylbutanoyl]-4-hydroxy-N-[1-[4-(4-methyl-1,3-thiazol-5-yl)phenyl]cyclopropyl]-pyrrolidine-2-carboxamide hydrochloride | 457.15 | (400 MHz, DMS0-$d_6$) δ 9.11 (s, 1H), 9.01 (s, 1H), 8.21 (br, 3H), 7.37-7.25 (m, 4H), 4.53 (dd, J = 9.2, 7.5 Hz, 1H), 4.38 (s, 1H), 3.90 (d, J = 5.2 Hz, 1H), 3.79 (d, J = 11.0 Hz, 1H), 2.45 (s, 3H), 2.09 (dd, J = 12.8, 7.7 Hz, 1H), 1.93-1.79 (m, 1H), 1.32-1.10 (m, 4H), 1.02 (s, 9H). |
| N2 | 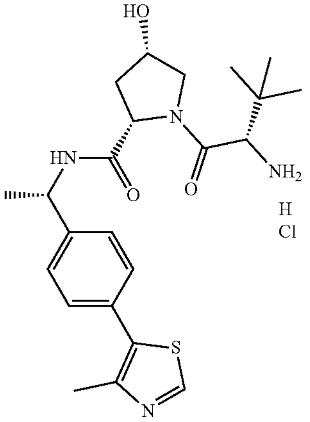 [SMILES: Cc1ncsc1-c1ccc([C@H](C)NC(=O)[C@@H]2C[C@H](O)CN2C(=O)[C@@H](N)C(C)(C)C)cc1] | (2S,4S)-1-[(2S)-2-amino-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride | 455.25 | (400 MHz, $CD_3OD$) δ 10.03 (s, 1H), 7.63-7.46 (m, 4H), 5.05 (q, J = 7.0 Hz, 1H), 4.62 (dd, J = 8.9, 5.7 Hz, 1H), 4.41 (p, J = 5.3 Hz, 1H), 4.06 (s, 1H), 3.98 (dd, J = 10.5,5.3 Hz, 1H), 3.57 (dd, J = 10.5, 4.8 Hz, 1H), 2.64 (s, 3H), 2.53 (ddd, J = 13.1, 9.1, 5.5 Hz, 1H), 1.86 (dt, J = 13.0,5.5 Hz, 1H), 1.54 (d, J = 7.0 Hz, 3H), 1.16 (s, 9H). |

(2S,4R)-1-[(2S)-2-amino-3,3-dimethylbutanoyl]-4-hydroxy-N-[4-(4-methyl-1,3-thiazol-5-yl)phenoxy] pyrrolidine-2-carboxamide hydrochloride (Intermediate N3)

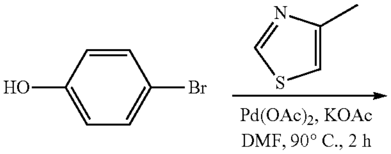

-continued

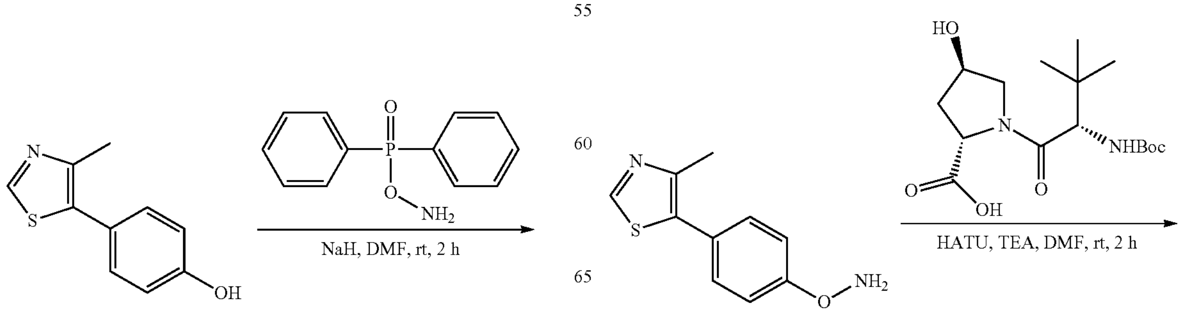

-continued

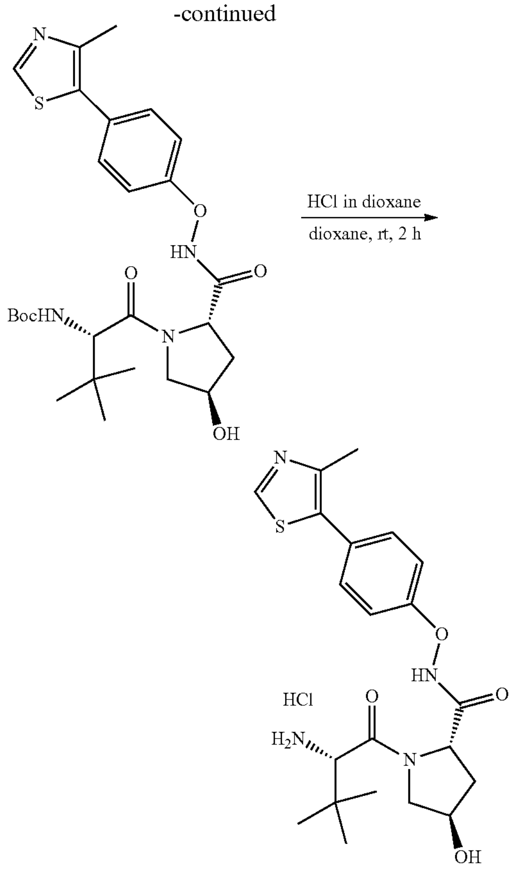

Intermedite N3

Step 1: 4-(4-Methyl-1,3-thiazol-5-yl)phenol. To a stirred mixture of 4-bromophenol (20.00 g, 115.601 mmol) and 4-methylthiazole (13.75 g, 138.679 mmol) in DMF (100.00 mL) was added KOAc (22.69 g, 231.202 mmol) and $Pd(AcO)_2$ (2.60 g, 11.581 mmol) at room temperature. The resulting mixture was stirred for 16 h at 90° C. under nitrogen atmosphere. The resulting mixture was allowed to cool down to room temperature and was filtered. The filter cake was washed with EtOAc (3×200 mL). The combined filtrate was concentrated under reduced pressure. The residue was diluted with 1 N HCl (500 mL) and extracted with EtOAc (3×300 mL). The combined organic layers were washed with brine (2×300 mL) and dried over anhydrous $Na_2SO_4$. After filtration, the filtrate was concentrated under reduced pressure. The residue was diluted with EtOAc (20 mL) and petroleum ether (5 mL). The precipitated solids were collected by filtration and washed with petroleum ether (2×20 mL). This resulted in the title compound (6 g, 27%) as a yellow solid: $^1$H NMR (400 MHz, DMSO-$d_6$). 9.74 (s, 1H), 8.91 (s, 1H), 7.33-7.26 (m, 2H), 6.89-6.83 (m, 2H), 2.42 (s, 3H); LC/MS (ESI, m/z): $[(M+1)]^+$=192.05.

Step 2: o-[4-(4-methyl-1,3-thiazol-5-yl)phenylhydroxylamine. To a stirred solution of 4-(4-methyl-1,3-thiazol-5-yl)phenol (200.00 mg, 1.046 mmol) in DMF (10.00 mL) was added NaH (62.74 mg, 1.569 mmol, 60% dispersion in mineral oil) in portions at 0° C. under nitrogen atmosphere. The resulting mixture was stirred for 30 min at 0° C. under nitrogen atmosphere. To the above mixture was added amino diphenylphosphinate (365.81 mg, 1.569 mmol) in portions over 1 min at 0° C. The resulting mixture was stirred for additional 2 h at room temperature. The reaction was quenched with water (30 mL) at 0° C. The resulting mixture was extracted with EtOAc (3×30 mL). The combined organic layers were washed with brine (2×30 mL) and dried over anhydrous $Na_2SO_4$. After filtration, the filtrate was concentrated under reduced pressure. The residue was purified by reverse phase flash with the following conditions (Column: Spherical $C^{18}$ Column, 20~40 um, 120 g; Mobile Phase A: water (0.1% TFA), Mobile Phase B: ACN; Flow rate: 60 mL/min; Gradient: 25% B to 40% B in 25 min, 254 nm. The fractions containing the desired product were collected at 32% B) to afford the title compound (166 mg, 77%) as a brown oil: $^1$H NMR (400 MHz, Methanol-$d_4$) δ 9.11-8.95 (m, 2H), 7.58-7.48 (m, 1H), 7.44 (dd, J=8.9, 2.7 Hz, 2H), 7.29-7.22 (m, 2H), 2.50 (s, 3H); LC/MS (ESI, m/z): $[(M+1)]^+$=207.15.

Step 3: Tert-butyl (2S,4R)-4-hydroxy-2-[[4-(4-methyl-1,3-thiazol-5-yl)phenoxy]carbamoyl]pyrrolidine-1-carboxylate. To a stirred solution of (2S,4R)-1-[(2S)-2-[(tert-butoxycarbonyl)amino]-3,3-dimethylbutanoyl]-4-hydroxypyrrolidine-2-carboxylic acid (1.67 g, 4.848 mmol) and HATU (1.84 g, 4.848 mmol) in DMF (15.00 mL) was added DIEA (2.51 g, 19.441 mmol) at 25° C. The resulting mixture was stirred for 15 min at 25° C. To the above mixture was added o-[4-(4-methyl-1,3-thiazol-5-yl)phenyl] hydroxylamine (1.00 g, 4.848 mmol) at 25° C. The resulting mixture was stirred for additional 2 h at 25° C. The resulting solution was purified by reverse phase flash with the following conditions (Column: Spherical $C1^8$ Column, 20~40 um, 120 g; Mobile Phase A: water (0.05% $NH4HCO_3$), Mobile Phase B: ACN; Flow rate: 60 mL/min; Gradient: 30% B to 50% B in 25 min, 254 nm. The fractions containing the desired product were collected at 40% B) to afford the title compound (1 g, 39%) as a white solid: $^1$H NMR (400 MHz, Methanol-$d_4$) δ 8.88 (s, 1H), 7.42 (d, J=8.3 Hz, 2H), 7.33 (d, J=8.4 Hz, 2H), 4.65-4.50 (m, 2H), 4.32 (s, 1H), 4.01-3.75 (m, 2H), 2.47 (s, 3H), 2.34-2.13 (m, 2H), 1.47 (s, 9H), 1.04 (s, 9H); LC/MS (ESI, m/z): $[(M+1)]^+$=533.21.

Step 4: (2S,4R)-1-[(2S)-2-amino-3,3-dimethylbutanoyl]-4-hydroxy-N-[4-(4-methyl-1,3-thiazol-5-yl)phenoxy]pyrrolidine-2-carboxamide hydrochloride. To a stirred solution of tert-butyl N-[(2S)-1-[(2S,4R)-4-hydroxy-2-[[4-(4-methyl-1,3-thiazol-5-yl)phenoxy]carbamoyl]pyrrolidin-1-yl]-3,3-dimethyl-1-oxobutan-2-yl]carbamate (4.30 g, 8.073 mmol) in dioxane (40.00 mL) was added 4 M HCl in 1,4-dioxane (20.00 mL) dropwise at 25° C. The resulting mixture was stirred for 2 h at 25° C. The resulting mixture was concentrated under reduced pressure. This resulted in the title compound (4 g, crude) as a white solid: $^1$H NMR (400 MHz, DMSO-$d_6$) δ 12.56 (s, 1H), 9.09 (s, 1H), 8.27-8.24 (m, 2H), 7.39 (d, J=8.4 Hz, 2H), 7.25 (d, J=8.4 Hz, 2H), 4.51 (t, J=8.5 Hz, 1H), 4.42 (s, 1H), 3.95-3.93 (m, 1H), 3.84 (d, J=10.9 Hz, 1H), 2.44 (s, 3H), 2.22-2.17 (m, 1H), 2.02-1.94 (m, 1H), 1.34-1.25 (m, 1H), 1.12-1.06 (m, 1H), 1.02 (s, 9H); LC/MS (ESI, m/z): $[(M+1)]^+$=433.15.

Methyl (5S,8S,10aR)-3-acetyl-5-[(tert-butoxycarbonyl)amino]-6-oxo-octahydropyrrolo[1,2-a][1,5]diazocine-8-carboxylate

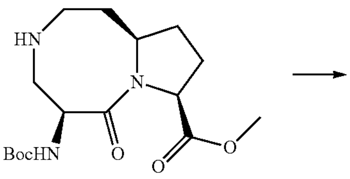

-continued

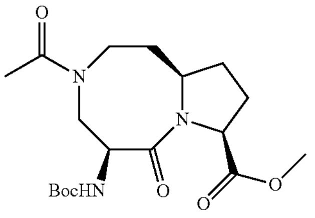

To a solution of methyl (5S,8S,10aR)-5-[(tert-butoxycarbonyl)amino]-6-oxo-octahydro-1H-pyrrolo[1,2-a][1,5]diazocine-8-carboxylate (4.44 g, 13.005 mmol) in DCM (50.00 mL) were added TEA (3.95 g, 39.015 mmol) and acetyl chloride (1.53 g, 19.507 mmol) at 0° C. and stirred at room temperature for 3 hours. The reaction was quenched by the addition of sat. $NaHCO_3$ (100 mL) and the resulting mixture was extracted with DCM (5×100 mL). The combined organic layers were concentrated under reduced pressure. The residue was purified by reverse phase flash chromatography with the following conditions: column, $C^{18}$ silica gel; mobile phase, $CH_3CN$ in water (plus 10 mmol/L $NH_4HCO_3$), 25% to 40% gradient in 15 min; Detector, UV 220/254 nm to give the title compound as a light yellow solid (4.55 g, 91%): $^1H$ NMR (400 MHz, $CDCl_3$) δ 5.84 (d, J 6.4 Hz, 1H), 4.50 (t, J 8.6 Hz, 2H), 4.17-4.13 (m, 1H), 3.97-3.83 (m, 2H), 3.77 (s, 3H), 3.42-3.28 (m, 1H), 3.21 (dd, J 14.3, 10.7 Hz, 1H), 2.42-2.33 (m, 1H), 2.30 (s, 3H), 2.24-1.97 (m, 3H), 1.90-1.72 (m, 2H), 1.44 (s, 9H). LC/MS (ESI, m/z): $[(M+1)]^+$=384.10.

Tert-butyl N-[(2S,11S)-6-bromo-2-[[(1S)-3-carbamoyl-1-(diphenylmethylcarbamoyl)propyl]carbamoyl]-12-oxo-1-azatricyclo[6.4.1.0[4,13]]trideca-4(13), 5,7-trien-11-yl]carbamate (Intermediate 0)

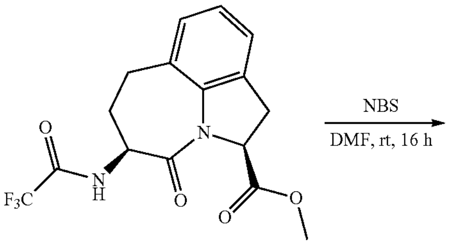

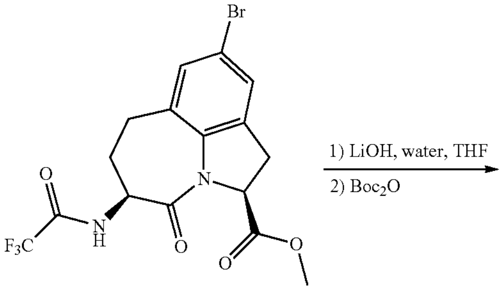

-continued

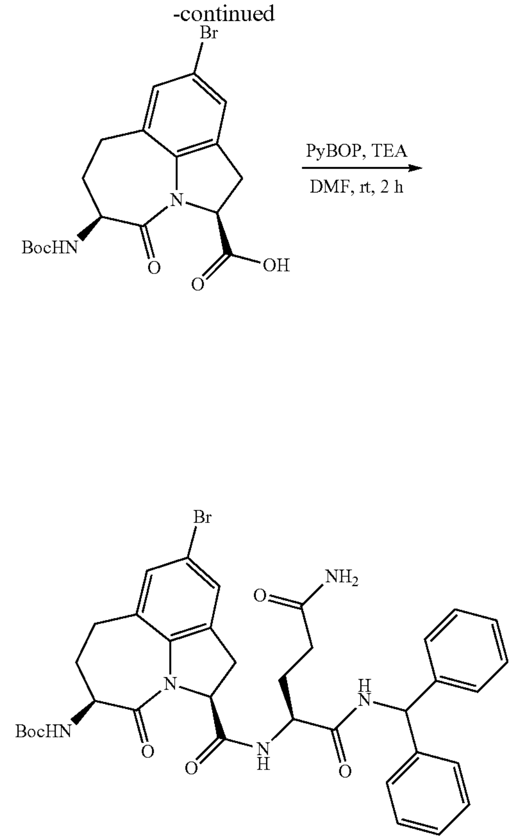

Intermediate O

Step 1. Methyl (2S,11S)-6-bromo-12-oxo-11-(2,2,2-trifluoroacetamido)-1-azatricyclo[6.4.1.0[4,13]]trideca-4(13), 5,7-triene-2-carboxylate. A solution of methyl (2S,11S)-12-oxo-11-(2,2,2-trifluoroacetamido)-1-azatricyclo[6.4.1.0[4,13]]trideca-4(13), 5,7-triene-2-carboxylate (10.00 g, 28.066 mmol) and NBS (7.49 g, 42.099 mmol) in DMF (10.00 mL) was stirred for overnight at room temperature under nitrogen atmosphere. The resulting solution was purified by reverse phase flash chromatography with the following conditions: Column: Spherical $C^{18}$, 20-40 um, 330 g; Mobile Phase A: water (plus 10 mM $NH_4HCO_3$); Mobile Phase B: ACN; Flow rate: 80 mL/min; Gradient: 5% - 5% B, 10 min, 33% B - 45% B gradient in 20 min; Detector: 254/220 nm. The fractions containing the desired product were collected at 40% B and concentrated under reduced pressure to afford the title compound as a yellow solid (7.0 g, 57%): $^1H$ NMR (400 MHz, DMSO-$d_6$) b 9.90 (d, J 7.9 Hz, 1H), 7.32 (dd, J 12.7, 2.0 Hz, 2H), 5.16 (dd, J 11.3, 2.9 Hz, 1H), 4.67-4.41 (m, 1H), 3.65 (s, 3H), 3.57-3.53 (m, 1H), 3.43-3.37 (m, 1H), 3.18-3.12 (m, 1H), 3.1-3.00 (m, 1H), 2.14-2.11 (m, 2H). LC/MS (ESI, m/z): $[(M+1)]^+$=434.95, 436.95.

Step 2. (2S,11S)-6-bromo-11-[(tert-butoxycarbonyl)aminol-12-oxo-1-azatricyclo[6.4.1.0[4,13]]trideca-4(13), 5,7-triene-2-carboxylic acid. A solution of methyl (2S,11S)-6-bromo-12-oxo-11-(2,2,2-trifluoroacetamido)-1-azatricyclo [6.4.1.0[4,13]]trideca-4(13), 5,7-triene-2-carboxylate (7.5 g, 17.234 mmol) and aqueous LiOH (2 M, 51.70 mL, 103.404 mmol) in THF (50.00 mL) was stirred for 3 h at room temperature under nitrogen atmosphere. The solution was neutralized to pH 10 with HCl (1 M). To the above solution was added $Boc_2O$ (4.06 mL, 18.585 mmol) at room temperature. The resulting mixture was stirred for additional overnight at room temperature. The resulting solution was purified by reverse phase flash chromatography with the following conditions: Column: Spherical $C^8$, 20-40 um, 330 g; Mobile Phase A: water (plus 10 mM $NH_4HCO_3$); Mobile Phase B: ACN; Flow rate: 80 mL/min; Gradient: 5% - 5% B, 10 min 33% B - 45% B gradient in 20 min; Detector: 254/220 nm. The fractions containing the desired product were collected at 4000 B and concentrated under reduced pressure to afford the title compound as a white solid (5 g, 680): $^1$H NMR (400 MHz, DMSO-$d_6$) z 7.27-7.19 (i, 2H), 6.95 (d, J 7.7 Hz, 1H), 4.76 (dd, J 10.5, 2.1 Hz, 1H), 3.99 (q, J 6.7 Hz, 1H), 3.29-3.26 (, 1H), 3.11-2.91 (i, 3H), 2.02-2.00 (m, 2H), 1.39 (s, 9H). LC/MS (ESI, m/z): $[(M+1-100)]^+$=325.05, 327.05.

The intermediates in Table 65 were prepared according to the procedure to prepare Intermediate L.

TABLE 65

Characterization data for intermediates prepared according to above.

| Inter-mediate | Structure | Chemical Name | MS: $[(M + 1)]^+$ | $^1$H-NMR |
|---|---|---|---|---|
| O-2-1 | 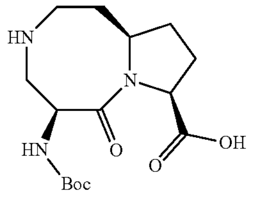 [SMILES: CC(C)(C)OC(=O)N[C@H]1CNCC[C@H]2CC[C@@H](C(=O)O)N2C1=O] | (5S,8S,10aR)-5-[(tert-butoxycarbonyl)-amino]-6-oxo-octahydro-1H-pyrrolo[1,2-a][1,5]diazocine-8-carboxylic acid | 328.15 | (400 MHz, $CD_3OD$) δ 5.11 (dd, J = 12.1, 5.8 Hz, 1H), 4.58 (td, J = 8.7, 3.8 Hz, 2H), 3.69 (dt, J = 14.4, 3.7 Hz, 1H), 3.47-3.33 (m, 2H), 3.12 (t, J = 12.3 Hz, 1H), 2.56-2.44 (m, 1H), 2.34-2.10 (m, 2H), 2.08-2.00 (m, 1H), 1.86-1.82 (m, 2H), 1.47 (s, 9H). |
| O-2-2 | 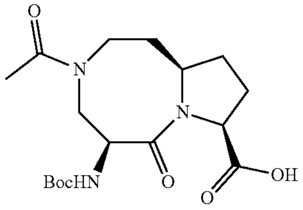 [SMILES: CC(=O)N1CC[C@H]2CC[C@@H](C(=O)O)N2C(=O)[C@@H](NC(=O)OC(C)(C)C)C1] | (5S,8S,10aR)-3-acetyl-5-[(tert-butoxycarbonyl)-amino]-6-oxo-octahydropyrrolo[1,2-a][1,5]-diazocine-8-carboxylic acid | 370.15 | (300 MHz, $CDCl_3$) δ 5.87 (d, J = 6.9 Hz, 1H), 4.67-4.65 (m, 1H), 4.54 (t, J = 8.3 Hz, 1H), 4.29-4.25 (m, 1H), 3.95-3.77 (m, 2H), 3.68-3.63 (m, 3H), 3.35 (t, J = 12.5 Hz, 1H), 2.36-2.34 (m, 2H), 2.23 (s, 3H), 2.01-1.98 (s, 1H), 1.84-1.80 (m, 1H), 1.45 (s, 9H). |
| O-2-3 | 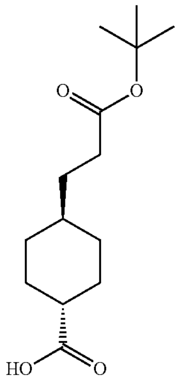 [SMILES: CC(C)(C)OC(=O)CC[C@H]1CC[C@H](C(=O)O)CC1] | (1r,4r)-4-[3-(tert-butoxy)-3-oxopropyl]cy-clohexane-1-carboxylic acid | N/A | (400 MHz, DMSO-$d_6$) δ 11.96 (s, 1H), 2.19 (t, J = 7.7 Hz, 2H), 2.14-2.07 (m, 1H), 1.89-1.86 (d, J = 12.8 Hz, 2H), 1.76-1.68 (m, 2H), 1.44-1.42 (m, 1H), 1.39 (s, 9H), 1.32-1.20 (m, 2H), 1.21-1.16 (m, 1H), 0.95-0.84 (m, 3H) |

Step 3. Tert-butyl N-(2S(11S)-6-bromo-2-[[(1S)-3-carbamoyl-1-(diphenylmethylcarbamoyl)propyl]carbamoyl]-12-oxo-11-azatricyclo [6.4.1.0[4,13]]trideca-4(13), 5,7-trien-11-yl]carbamate (Intermediate 0). The title compound was prepared according to the procedure to prepare intermediate G and 1. [H NMR (400 MHz, DMSO-$d_6$) δ 8.81 (d, J 8.4 Hz, 1H), 8.22 (d, J 7.9 Hz, 1H), 7.39-7.15 (m, 14H), 7.07 (d, J 7.9 Hz, 1H), 6.76 (s, 1H), 6.08 (d, J 8.3 Hz, 1H), 5.11 (dd, J 10.7, 2.7 Hz, 1H), 4.32 (td, J 8.4, 5.0 Hz, 1H), 4.09-3.95 (8, 1H), 3.43-3.40 (., 1H), 3.12-2.94 (5, 2H), 2.94-2.84 (m, 1H), 2.14-2.02 (, 3H), 1.91-1.87 (m, 1H), 1.83-1.71 (m, 1H), 1.39 (s, 9H). LC/MS (ESI, m/z): $[(M+1-100)]^+$=718.10, 720.10.

The intermediates in Table 66 were prepared according to the procedure to prepare Intermediate G.

TABLE 66

| Intermediate | Structure | Chemical Name | MS: $[(M + 1)]^+$ | $^1$H-NMR |
|---|---|---|---|---|
| | Characterization data for intermediates prepared according to above. | | | |
| O-3-1 | 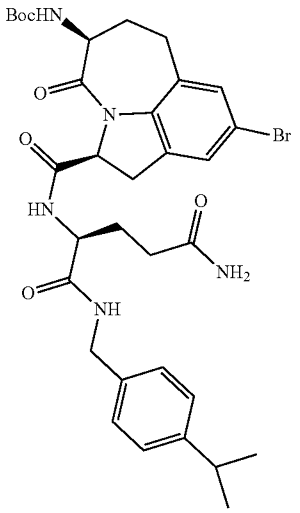 [SMILES: CC(C)c1ccc(CNC(=O)[C@H](CCC(N)=O)NC(=O)[C@@H]2Cc3cc(Br)cc4c3N2C(=O)[C@@H](NC(=O)OC(C)(C)C)CC4)cc1] | tert-butyl N-[(2S,11S)-6-bromo-2-[[(1S)-3-carbamoyl-1-[[(4-isopropylphenyl)methyl[carbamoyl]propyl]carbamoyl]-12-oxo-1-azatricyclo[6.4.1.0^[4,13]]trideca-4(13),5,7-trien-11-yl]carbamate | 684.40, 686.40 | (400 MHz, DMSO-$d_6$) δ 8.35 (t, J = 5.9 Hz, 1H), 8.26 (d, J = 7.9 Hz, 1H), 7.30-7.24 (m, 3H), 7.15-7.11 (m, 5H), 6.77 (s, 1H), 5.12-5.10 (m, 1H), 4.24-4.20 (m, 2H), 4.08-4.00 (m, 1H), 3.45-3.41 (m, 1H), 3.15-3.01 (m, 2H), 2.97-2.74 (m, 1H), 2.88-2.84 (m, 1H), 2.14-1.85 (m, 6H), 1.81-1.72 (m, 1H), 1.39 (s, 9H), 1.19 (d, J = 6.9 Hz, 6H) |
| O-3-2 | 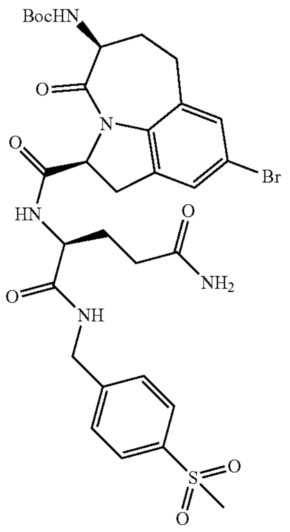 [SMILES: CC(C)(C)OC(=O)N[C@H]1CCc2cc(Br)cc3c2N(C1=O)[C@H](C(=O)N[C@@H](CCC(N)=O)C(=O)NCc1ccc(S(C)(=O)=O)cc1)C3] | tert-butyl N-[(2S,11S)-6-bromo-2-[[(1S)-3-carbamoyl-1-[[(4-methanesulfonylphenyl)methyl]carbamoyl]propyl]carbamoyl]-12-oxo-1-azatricyclo[6.4.1.0^[4,13]]trideca-4(13),5,7-trien-11-yl]carbamate | 720.15, 722.15 | (400 MHz, DMSO-$d_6$) δ 8.56 (t, J = 6.1 Hz, 1H), 8.30 (d, J = 7.7 Hz, 1H), 7.85 (d,J = 8.1Hz, 2H), 7.48 (d, J = 8.0 Hz, 2H), 7.30 (s, 1H), 7.27 (d, J = 7.8 Hz, 2H), 7.13 (d, J = 8.1 Hz, 1H), 6.79 (s, 1H), 5.12 (m, 1H), 4.44-4.32 (m, 2H), 4.21 (m, 1H), 4.09-4.02 (t, J = 9.2 Hz, 1H), 3.43 (m, 1H), 3.19 (s, 3H), 3.11-2.95 (m, 3H), 2.14-2.09 (m, 2H), 2.04-1.88 (m, 3H), 1.80 (m, 1H), 1.39 (s, 9H) |

2395

Tert-butyl 3-[(1r, 4r)-4-(hydroxymethyl)cyclohexyl]propanoate

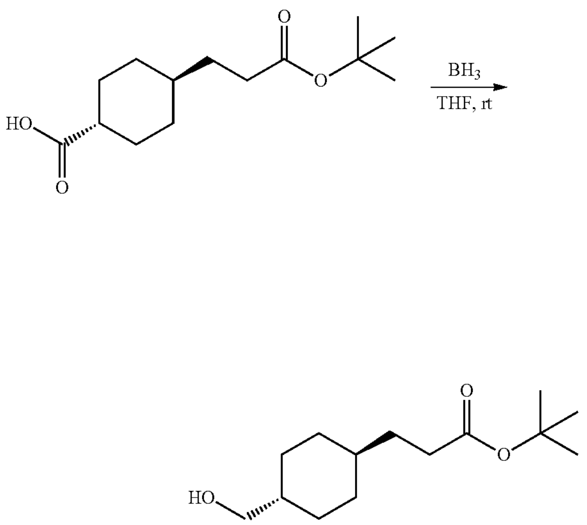

To a stirred solution of (1r, 4r)-4-[3-(tert-butoxy)-3-oxopropyl]cyclohexane-1-carboxylic acid (5.00 g, 19.505 mmol) in THF (20.00 mL) was added $BH_3$.THF (1 M in THF, 39.01 mL, 39.01 mmol) dropwise at 0° C. under air atmosphere. The resulting mixture was stirred for 16 h at room temperature. The reaction was quenched with MeOH (10 mL) and stirred for 1 h at reflux. The resulting mixture was diluted with EtOAc (150 mL). The combined organic layers were washed with brine (3x50 mL), dried over anhydrous $Na_2SO_4$. After filtration, the filtrate was concentrated under reduced pressure. The residue was purified by silica gel column chromatography, eluted with petroleum ether/EtOAc (10:1) to afford the title compound as a colorless oil (2.33 g, 49%): $^1H$ NMR (400 MHz, DMSO-$d_6$) δ 3.76 (s, 2H), 3.27-3.21 (m, 1H), 3.17 (d, J=6.3 Hz, 2H), 2.15 (t, J=7.6 Hz, 2H), 1.72-1.64 (m, 5H), 1.40-1.36 (m, 2H), 1.36 (s, 9H), 1.31-1.19 (m, 2H), 1.18-1.10 (m, 1H).

2396

Methyl (2R,3R)-2-[(tert-butoxycarbonyl)amino]-3-[(tert-butyldimethylsilyl)oxy]butanoate

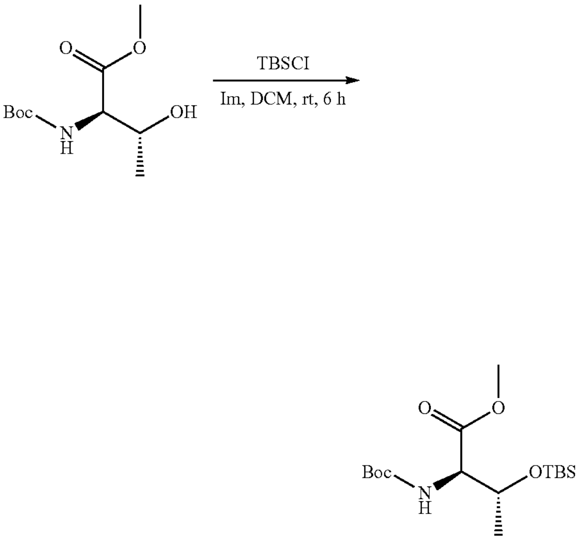

To a solution of methyl (2R,3R)-2-[(tert-butoxycarbonyl) amino]-3-hydroxybutanoate (86.0 g, 369 mmol) and imidazole (50.2 g, 738 mmol) in DCM (1.00 L) was added TBSCl (72.3 g, 480 mmol) at 25° C. and was stirred at 25° C. for 6 h. The resulting solution was diluted with $H_2O$ (1.00 L) and was extracted with EtOAc (3x1.00 L). The combined organic layers were washed with brine (3x1.00 L), dried over anhydrous $Na_2SO_4$. After filtration, the filtrate was concentrated under reduced pressure. The residue was purified by silica gel column chromatography, eluted with petroleum ether/EtOAc (100:1 to 20:1) to afford the title compound as a light yellow oil (120 g, 94%): $^1H$ NMR (400 MHz, $CDCl_3$) δ 5.34-5.26 (m, 1H), 4.26 (dd, J=8.7, 3.7 Hz, 1H), 4.13-4.06 (m, 1H), 3.76 (s, 3H), 1.61 (s, 9H), 1.25 (d, J=6.4 Hz, 3H), 0.88 (s, 9H), 0.07 (s, 6H): LC/MS (ESI, m/z): $[(M+1)]^+$=348.15.

The intermediates in Table 67 were prepared according to the above procedure.

TABLE 67

Characterization data for intermediates prepared according to above.

| Intermediate | Structure | Chemical Name | MS: $[(M + 1)]^+$ | $^1H$-NMR |
|---|---|---|---|---|
| | 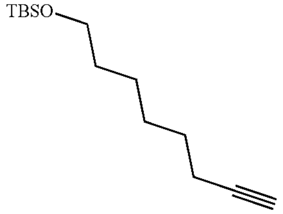 [SMILES: C#CCCCCCCO[Si](C)(C)C(C)(C)C] | Tert-butyl[(9-iodonon-7-yn-1-yl) oxy]dimethylsilane | N/A | (400 MHz, $CDCl_3$) δ 3.63 (t, J = 6.5 Hz, 2H), 2.21 (td, J = 7.1, 2.7 Hz, 2H), 1.95 (t, J = 2.7 Hz, 1H), 1.61-1.49 (m, 4H), 1.48-1.31 (m, 4H), 0.92 (s, 9H), 0.07 (s, 6H) |

Tert-butyl[(9-iodonon-7-yn-1-yl)oxy]dimethylsilane

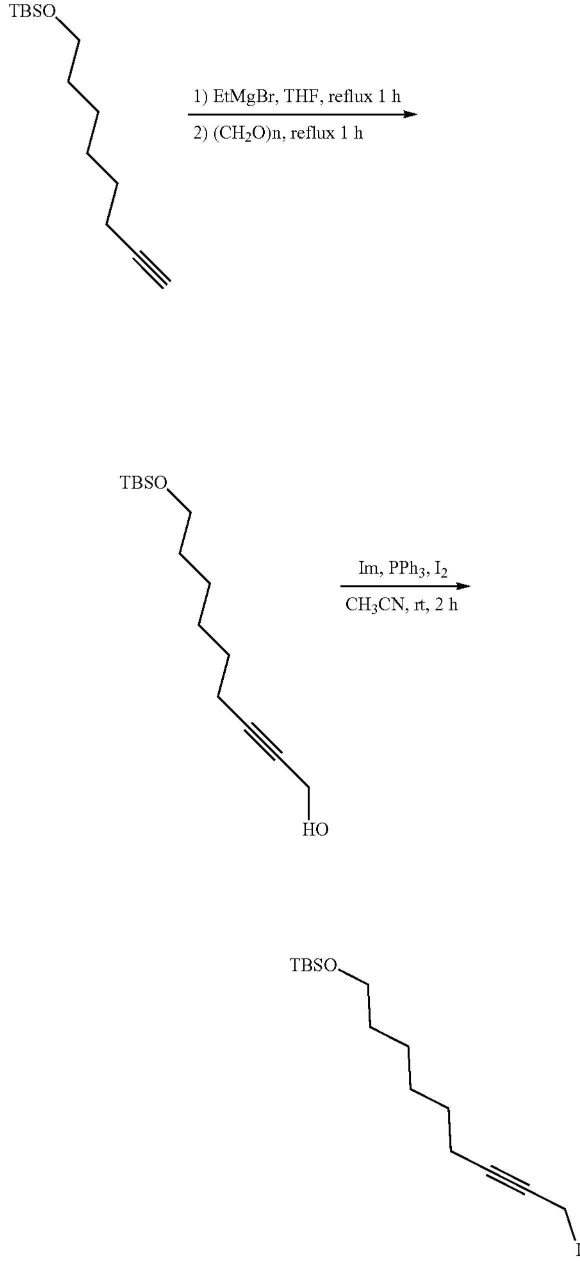

Step 1. 9-[(Tert-butyldimethylsilyl)oxy]non-2-yn-1-ol. To a solution of EtMgBr (2.8 M in THF, 20.05 mL, 56.142 mmol) in anhydrous THF (200.00 mL) was added a solution of tert-butyldimethyl(oct-7-yn-1-yloxy)silane (9 g, 37.428 mmol) in THF (20 mL) at 25° C. The solution was refluxed for 1 h and then cooled to 0° C. Paraformaldehyde (5.06 g, 56.142 mmol) was added. The mixture was refluxed for additional 1 h. Then cooled to room temperature and stirred for 12 h. The reaction was quenched with $NaHCO_3$ (50 mL). The mixture was extracted with EtOAc (3×200 mL), dried with $Na_2SO_4$ and filtered. The filtrate was concentrated in vacuum. The residue was purified by silica gel column chromatography, eluted with EtOAc in petroleum ether (0%~30%) to afford the title compound as a white solid (4.3 g, 42%): $^1H$ NMR (400 MHz, $CDCl_3$) δ 3.63 (t, J 6.5 Hz, 2H), 2.21 (td, J 7.1, 2.7 Hz, 2H), 1.95 (t, J 2.7 Hz, 1H), 1.61-1.49 (m, 4H), 1.48-1.31 (m, 4H), 0.92 (s, 9H), 0.07 (s, 6H).

Step 2. Tert-butyl[(9-iodonon-7-yn-1-yl)oxy]dimethylsilane. To a solution of imidazole (1.19 g, 17.487 mmol) and $PPh_3$ (4.59 g, 17.487 mmol) in $Et_2O$ (75.00 mL) and $CH_3CN$ (25.00 mL) was slowly added $I_2$ (4.44 g, 17.487 mmol) at 0° C. The resulting slurry was warmed to room temperature and then stirred for 20 min. The slurry was cooled to 0° C. To it was added dropwise a solution of 9-[(tert-butyldimethylsilyl)oxy]non-2-yn-1-ol (4.30 g, 15.897 mmol) in $Et_2O$ (20 mL) at 0° C. The solution was slowly warmed to room temperature and then stirred for 1 h. The reaction was diluted with hexane (100 mL). Then it was washed with aqueous $NaHCO_3$ (100 mL), brine (100 mL), dried with $Na_2SO_4$ and filtered. The filtrate was concentrated in vacuum. The residue was purified by silica gel column chromatography, eluted with 0%~5% EtOAc in petroleum ether to afford the title compound as a white solid (4 g, 66%): $^1H$ NMR (400 MHz, DMSO-d4) δ 3.89 (t, J 2.5 Hz, 2H), 3.57 (t, J 6.4 Hz, 2H), 2.22-2.17 (m, 2H), 1.52-1.23 (m, 9H), 0.86 (s, 9H), 0.03 (s, 6H).

Tert-butyl 3-(2-bromophenyl)propanoate

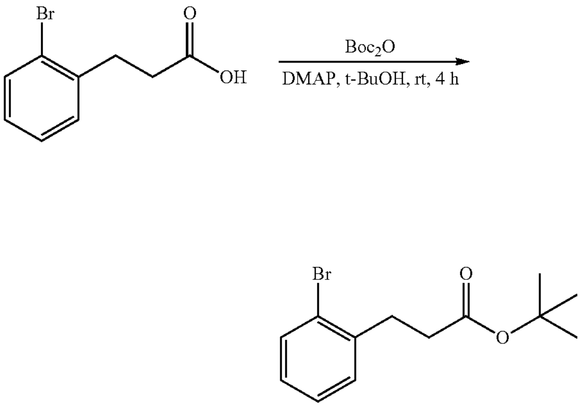

To a stirred mixture of 3-(2-bromophenyl)propanoic acid (5.00 g, 21.827 mmol) and $Boc_2O$ (9.53 g, 43.654 mmol) in t-BuOH (50.00 mL) was added DMAP (0.80 g, 6.548 mmol) at room temperature. The resulting mixture was stirred for 4 h at room temperature. The resulting mixture was concentrated under reduced pressure. The crude product was purified by reverse phase flash chromatography with the following conditions: Column: Spherical $C1^8$ Column, 20~40 um, 330 g; Mobile Phase A: water (plus 0.1 M formic acid), Mobile Phase B: ACN; Flow rate: 70 mL/min; Gradient: 80% B to 95% B in 25 min; Detector: UV 254/220 nm. The fractions containing the desired product were collected at 92% B to afford the title compound as a yellow oil (3.5 g, 56%): $^1H$ NMR (400 MHz, DMSO-d4) δ 7.62-7.57 (m, 1H), 7.35-7.31 (m, 2H), 7.18-7.16 (m, 1H), 2.93 (t, J 7.6 Hz, 2H), 2.54 (d, J 7.6 Hz, 2H), 1.38 (s, 9H).

(2S)-2-[[(5S,8S,10aR)-5-[(tert-butoxycarbonyl)amino]-6-oxo-3-[2-[(1S,4S)-4-[[1-(2,6-dioxopiperidin-3-yl)-3-methyl-2-oxo-1,3-benzodiazol-5-yl]methyl]cyclohexyl]acetyl]-octahydropyrrolo[1,2-a][1,5]diazocin-8-yl]formamido]-4-carbamoylbutanoic acid (Intermediate P)
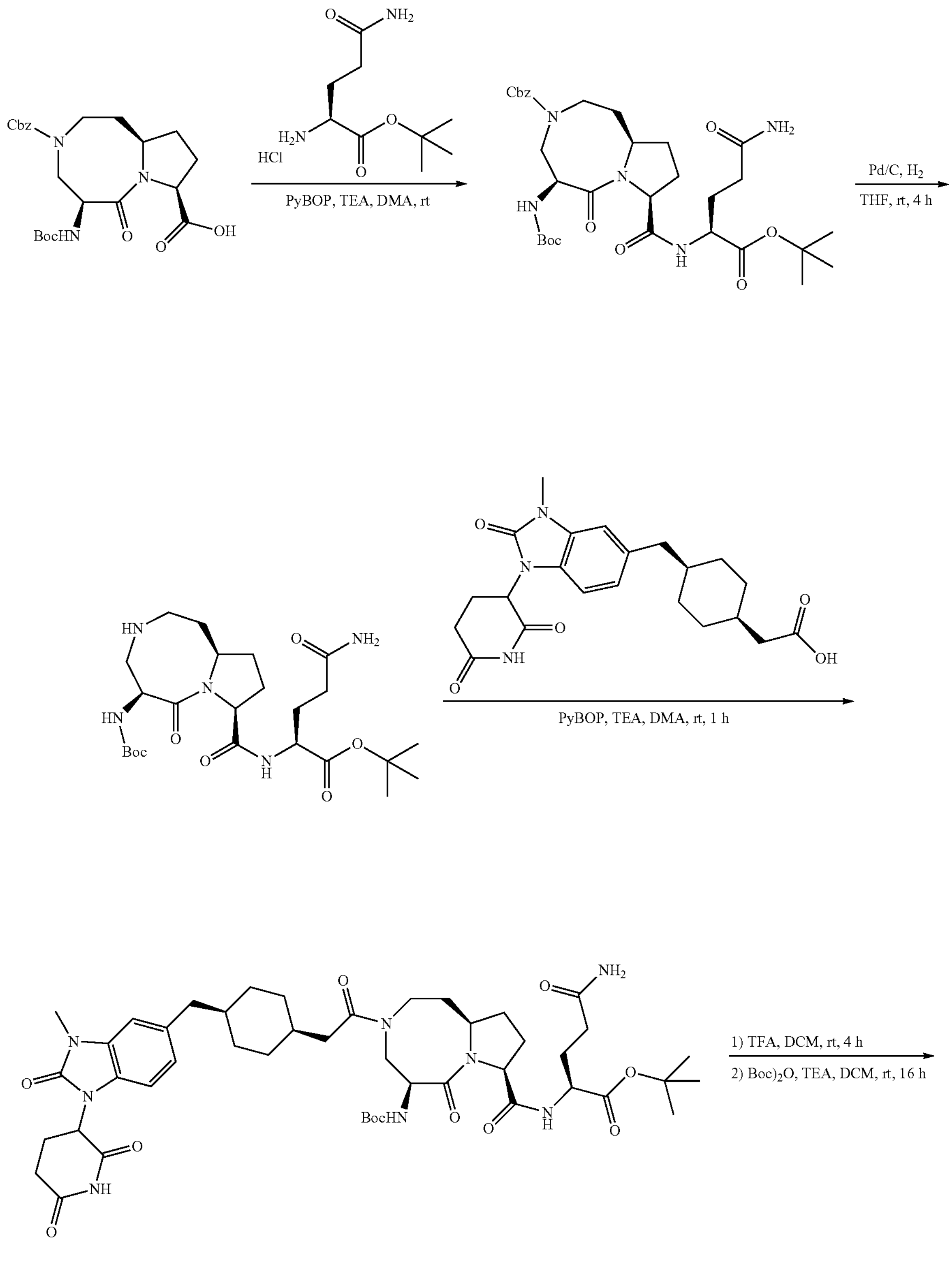

-continued

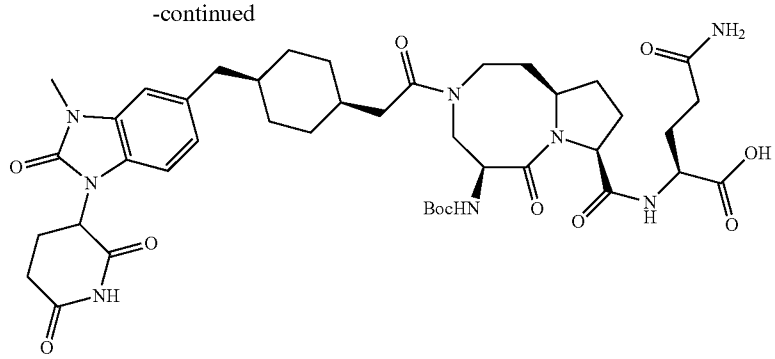

Intermediate P

Step 1: Benzyl (5S,8S,10aR)-8-[[(2S)-1-(tert-butoxy)-4-carbamoyl-1-oxobutan-2-yl]carbamoyl]-5-[tert-butoxycarbonyl)amino]-6-oxo-octahydropyrrolo[1,2-a][1,5]diazocine-3-carboxylate. To a stirred solution of (5S,8S,10aR)-3-[(benzyloxy)carbonyl]-5-[(tert-butoxycarbonyl)amino]-6-oxo-octahydropyrrolo[1,2-a][1,5]diazocine-8-carboxylic acid (4.00 g, 8.667 mmol) and glutamine t-butyl ester hydrochloride (2.28 g, 9.551 mmol) in DMA (40.00 mL) were added TEA (2.63 g, 25.991 mmol) and PyBOP (5.41 g, 10.396 mmol) at 0° C. under nitrogen atmosphere. The resulting mixture was stirred for 1 h at room temperature under nitrogen atmosphere. The resulting mixture was concentrated under reduced pressure. The residue was purified by reverse phase flash chromatography with the following conditions: Column: WelFlash™ C18-I, 20~40 µm, 330 g; Eluent A: water (plus 10 mmol/L formic acid); Eluent B: ACN; Gradient: 40% - 70% B in 30 min; Flow rate: 80 mL/min; Detector: 220 nm; desired fractions were collected at 58% B and concentrated under reduced pressure to afford the title compound (4.8 g, 81%) as a white solid: $^1H$ NMR (400 MHz, DMSO-$d_6$) δ 8.28 (d, J=7.2 Hz, 1H), 7.46-7.27 (m, 5H), 7.24-7.15 (m, 1H), 7.02-6.67 (m, 2H), 5.10 (d, J=1.7 Hz, 2H), 4.48-4.23 (m, 2H), 4.23-4.04 (m, 2H), 3.78-3.72 (m, 2H), 3.54 (t, J=14.4 Hz, 2H), 3.26-3.06 (m, 2H), 2.17 (q, J=6.2, 5.0 Hz, 3H), 2.05-1.62 (m, 4H), 1.48-1.28 (m, 20H); LC/MS (ESI, m/z): $[(M+H)]^+$=646.25.

Step 2: Tert-butyl (2S)-2-[[(5S,8S,10aR)-5-[(tert-butoxycarbonyl)amino]-6-oxo-octahydro-1H-pyrrolo[1,2-a][1,5]diazocin-8-yl]formamido]-4-carbamoylbutanoate. To a solution of benzyl (5S,8S,10aR)-8-[[(2S)-1-(tert-butoxy)-4-carbamoyl-1-oxobutan-2-yl]carbamoyl]-5-[(tert-butoxycarbonyl)amino]-6-oxo-octahydropyrrolo[1,2-a][1,5]diazocine-3-carboxylate (4.60 g, 7.123 mmol) in THF (200.00 mL) was added Pd/C (758.08 mg, 10% palladium on activated carbon) under nitrogen atmosphere. The mixture was hydrogenated at room temperature for 16 h under hydrogen atmosphere using a hydrogen balloon. After the reaction was completed, it was filtered through a Celite pad and concentrated under reduced pressure. This resulted in the title compound (3.7 g, 910%) as a white solid. The crude product was used in the next step directly without further purification: $^1H$ NMR (400 MHz, DMSO-$d_6$) δ 8.84 (d, J=7.7 Hz, 1H), 7.20 (d, J=6.4 Hz, 1H), 6.81-6.68 (m, 2H), 4.63-4.54 (m, 1H), 4.42-4.25 (m, 2H), 4.13-3.98 (m, 1H), 3.64-3.55 (m, 1H), 3.15-3.05 (m, 1H), 2.88-2.63 (m, 3H), 2.34-2.06 (m, 3H), 2.06-1.87 (m, 1H), 1.87-1.64 (m, 3H), 1.40 (s, 9H), 1.37 (s, 9H), 1.35 (d, J=8.2 Hz, 3H); LC/MS (ESI, m/z): [(M+H)]+=512.20.

Step 3: Tert-butyl (2S)-2-[[(5S,8S,10aR)-5-[(tert-butoxycarbonyl)amino]-6-oxo-3-[2-[(1S,4S)-4-[[1-(2,6-dioxopiperidin-3-yl)-3-methyl-2-oxo-1,3-benzodiazol-5-yl]methyl]cyclohexyl]acetyl]-octahydropyrrolo[1,2-ar[1,5]diazocin-8-yl]formamido]-4-carbamoylbutanoate. To a stirred solution of tert-butyl (2S)-2-[[(5S,8S,10aR)-5-[(tert-butoxycarbonyl)amino]-6-oxo-octahydro-1H-pyrrolo[1,2-a][1,5]diazocin-8-yl]formamido]-4-carbamoylbutanoate (695.00 mg, 1.358 mmol) and [(1S,4S)-4-[[1-(2,6-dioxopiperidin-3-yl)-3-methyl-2-oxo-1,3-benzodiazol-5-yl]methyl]cyclohexyl]acetic acid (561.68 mg, 1.358 mmol) in DMA (8.00 mL) were added TEA (412.38 mg, 4.075 mmol) and PyBOP (848.30 mg, 1.630 mmol) at 0° C. under nitrogen atmosphere. The resulting mixture was stirred for 1 h at room temperature under nitrogen atmosphere. The resulting mixture was concentrated under reduced pressure. The residue was purified by reverse phase flash chromatography with the following conditions: Column: WelFlash™ C18-I, 20~40 µm, 330 g; Eluent A: water (plus 10 mmol/L formic acid); Eluent B: ACN; Gradient: 35% -55% B in 20 min; Flow rate: 80 mL/min; Detector: 220/254 nm; desired fractions were collected at 50% B and concentrated under reduced pressure to afford the title compound (950 mg, 73%) as a white solid: $^1H$ NMR (300 MHz, DMSO-d4) δ 11.06 (s, 1H), 8.27 (d, J=7.7 Hz, 1H), 7.19 (d, J=7.2 Hz, 1H), 7.07-6.89 (m, 2H), 6.91-6.65 (m, 2H), 6.50 (d, J=6.8 Hz, 1H), 5.33 (dd, J=12.8, 5.4 Hz, 1H), 4.40 (q, J=8.7, 7.5 Hz, 2H), 4.20-3.86 (m, 2H), 3.77 (t, J=13.8 Hz, 2H), 3.61-3.42 (m, 1H), 3.38-3.29 (s, 3H), 3.19-3.06 (m, 1H), 2.99-2.81 (m, 2H), 2.81-2.54 (m, 6H), 2.47-2.24 (m, 2H), 2.16 (q, J=5.4, 3.0 Hz, 4H), 2.06-1.87 (m, 2H), 1.86-1.56 (m, 4H), 1.44 (s, 9H), 1.39 (s, 9H), 1.37-1.33 (m, 8H); LC/MS (ESI, m/z): $[(M+1)]^+$=907.25.

The intermediates in Table 68 were prepared according to Step 3 of the procedure to prepare Intermediate P

TABLE 68

| Characterization data for intermediates prepared according to above. | | | | |
|---|---|---|---|---|
| Intermediate | Structure | Chemical Name | MS: $[(M + 1)]^+$ | $^1$H-NMR |
| P-3-1 | 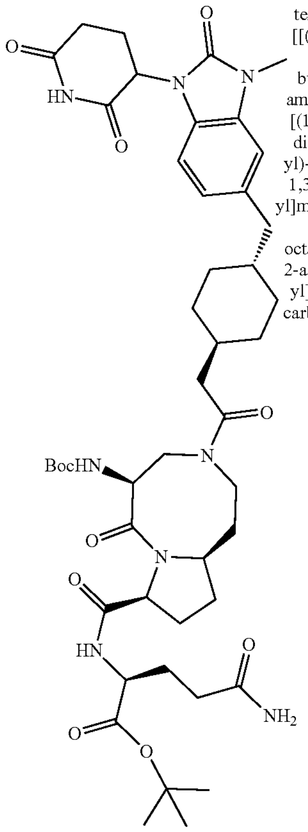 | tert-butyl (2S)-2-[[(5S,8S,10aR)-5-[tert-butoxycarbonyl)amino]-6-oxo-3-[2-[(1r,4r)-4-[[1-(2,6-dioxopiperidin-3-yl)-3-methyl-2-oxo-1,3-benzodiazol-5-yl]methyl]cyclohexyl]yl]acetyl]-octahydropyrrolo[1,2-a][1,5]diazocin-8-yl]formamido][-4-carbamoylbutanoate | 907.45 | (400 MHz, DMSO-$d_6$) δ 11.09 (s, 1H), 8.28 (t, J = 8.7 Hz, 1H), 7.21 (d, J = 6.7 Hz, 1H), 7.03-6.93 (m, 2H), 6.85-6.75 (m, 2H), 6.58 (d, J = 7.1 Hz, 1H), 5.34 (dd, J = 12.7, 5.4 Hz, 1H), 4.44-4.32 (m, 2H), 4.16-4.05 (m, 2H), 3.66 (d, J = 13.3 Hz, 1H), 3.32 (s, 3H), 3.28-3.20 (m, 1H), 3.18-3.05 (m, 1H), 2.98-2.84 (m, 1H), 2.77-2.58 (m, 2H), 2.49-2.46 (m, 1H), 2.38-2.23 (m, 2H), 2.21-2.08 (m, 4H), 2.05-1.93 (m, 3H), 1.93-1.83 (m, 2H), 1.82-1.57 (m, 10H), 1.43-1.33 (m, 18H), 1.02-0.87 (m, 4H) |

TABLE 68-continued

| Characterization data for intermediates prepared according to above. | | | | |
|---|---|---|---|---|
| Intermediate | Structure | Chemical Name | MS: $[(M + 1)]^+$ | $^1$H-NMR |
| P-3-2 | 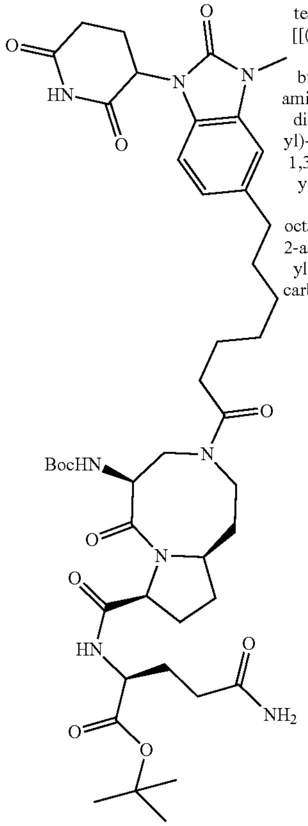 | tert-butyl (2S)-2-[[(5S,8S,10aR)-5-[(tert-butoxycarbonyl) amino]-3-[7-[1-(2,6-dioxopiperidin-3-yl)-3-methyl-2-oxo-1,3-benzodiazol-5-yl]heptanoyl]-6-oxo-octahydropyrrolo[1,2-a][1,5]diazocin-8-yl]formamido]-4-carbamoylbutanoate | 881.70 | (400 MHz, DMSO-$d_6$) δ 11.09 (s, 1H), 8.28 (t, J = 8.4 Hz, 1H), 7.21 (d,J = 14.0 Hz, 1H), 7.05-6.94 (m, 2H), 6.89-6.93 (m, 1H), 6.78 (s, 1H), 6.56 (d, J = 7.0 Hz, 1H), 5.34 (dd, J = 12.7, 5.4 Hz, 1H), 4.50-4.34 (m, 2H), 4.19-4.07 (m, 2H), 3.73-3.58 (m, 2H), 3.38-3.33 (m, 2H), 3.32 (s, 3H), 3.27-3.06 (m, 2H), 2.97-2.83 (m, 1H), 2.78-2.56 (m, 4H), 2.44-2.37 (m, 1H), 2.16 (t, J = 7.6 Hz, 3H), 1.97-1.86 (m, 2H), 1.85-1.71 (m, 3H), 1.68-1.46 (m, 6H), 1.38 (d, J = 8.2 Hz, 18H), 1.35-1.30 (m, 4H) |

Step 4: (2S)-2-[[(5S,8S,10aR)-5-[(tert-butoxycarbonyl) aminol-6-oxo-3-[2-[(1S,4S)-4-[[1-(2,6-dioxopiperidin-3-yl)-3-methyl-2-oxo-1,3-benzodiazol-5-yl]methyl]cyclohexyl]acetyl]-octahydropyrrolo[1,2-a][1,5]diazocin-8-yl] formamido]-4-carbamoylbutanoic acid. To a stirred solution of tert-butyl (2S)-2-[[(5S,8S,10aR)-5-[(tert-butoxycarbonyl) amino]-6-oxo-3-[2-[(1S,4S)-4-[[1-(2,6-dioxopiperidin-3-yl)-3-methyl-2-oxo-1,3-benzodiazol-5-yl]methyl]cyclohexyl]acetyl]-octahydropyrrolo[1,2-a][1,5]diazocin-8-yl] formamido]-4-carbamoylbutanoate (3.80 g, 4.189 mmol) in DCM (20.00 mL) was added TFA (4.00 mL, 53.852 mmol) at room temperature under nitrogen atmosphere. The resulting mixture was stirred for 4 h at room temperature under nitrogen atmosphere. The resulting mixture was concentrated under reduced pressure. The resulting mixture was diluted with DCM (10.00 mL). To the above mixture was added TEA (1.70 g, 16.800 mmol) dropwise and $Boc_2O$ (1.01 g, 4.628 mmol) at 0° C. The resulting mixture was stirred for additional 16 h at room temperature. The resulting mixture was concentrated under reduced pressure. The residue was purified by reverse phase flash chromatography with the following conditions: Column: WelFlash™ C18-I, 20~40 μm, 330 g; Eluent A: water (plus 10 mmol/L formic acid); Eluent B: ACN; Gradient: 30% - 50% B in 20 min; Flow rate: 80 mL/min; Detector: 220/254 nm; desired fractions were collected at 42% B and concentrated under reduced pressure to afford the title compound (3.0 g, 80%) as a white solid: $^1$H NMR (300 MHz, DMSO-d4) δ 12.55 (s, 1H), 11.08 (s, 1H), 8.29 (d, J=7.7 Hz, 1H), 7.22 (s, 1H), 7.01 (dd, J=8.9, 4.1 Hz, 2H), 6.93-6.68 (m, 2H), 6.53 (d, J=6.8 Hz, 1H), 5.35 (dd, J=12.6, 5.3 Hz, 1H), 4.48-4.30 (m, 3H), 4.26-3.99 (m, 2H), 3.89-3.71 (m, 2H), 3.33 (s, 3H), 3.18-3.02 (m, 1H), 2.90 (d, J=14.9 Hz, 1H), 2.81-2.56 (m, 2H), 2.42 (d, J=9.6 Hz, 1H), 2.19 (d, J=7.9 Hz, 2H), 2.02 (d, J=13.4 Hz, 2H), 1.89-1.57 (m, 2H), 1.53-1.29 (m, 12H), 1.07 (d, J=1.1 Hz, 6H), 1.05 (s, 9H); LC/MS (ESI, m/z): $[(M+H)]^+$=851.35.

The intermediates in Table 69 were prepared according to Step 3 of the procedure to prepare Intermediate P

TABLE 69

| Characterization data for intermediates prepared according to above. | | | | |
|---|---|---|---|---|
| Intermediate | Structure | Chemical Name | MS: $[(M + 1)]^+$ | $^1$H-NMR |
| P-4-1 694 | 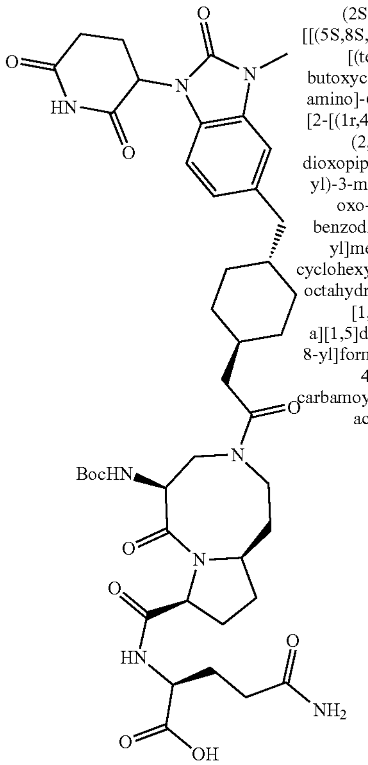 | (2S)-2-[[(5S,8S,10aR)-5-[(tert-butoxycarbonyl)amino]-6-oxo-3-[2-[(1r,4r)-4-[[1-(2,6-dioxopiperidin-3-yl)-3-methyl-2-oxo-1,3-benzodiazol-5-yl]methyl]cyclohexyl]acetyl]-octahydropyrrolo[1,2-a][1,5]diazocin-8-yl]formamido]-4-carbamoylbutanoic acid | 851.30 | (300 MHz, DMSO-$d_6$) δ 11.06 (s, 1H), 8.19 (dd, J= 15.3, 7.2 Hz, 1H), 7.22-7.14 (m, 1H), 6.98 (d, J = 8.0 Hz, 2H), 6.80 (d, J = 8.1 Hz, 1H), 6.70 (d, J = 15.2 Hz, 1H), 6.55 (d, J = 7.1 Hz, 1H), 5.32 (dd, J = 12.7, 5.3 Hz, 1H), 4.38 (q, J = 8.9 Hz, 2H), 4.18-4.01 (m, 2H), 3.66 (d, J = 13.4 Hz, 2H), 3.31 (s, 3H), 3.17 (dd, J = 25.8, 13.1 Hz, 2H), 3.04-2.80 (m, 2H), 2.77-2.57 (m, 2H), 2.47-2.43 (m, 1H), 2.39-2.23 (m, 2H), 2.21-2.09 (m, 4H), 2.04-1.87 (m, 3H), 1.86-1.54 (m, 10H), 1.37 (s, 9H), 1.01-0.84 (m, 4H) |
| P-4-2 693 | 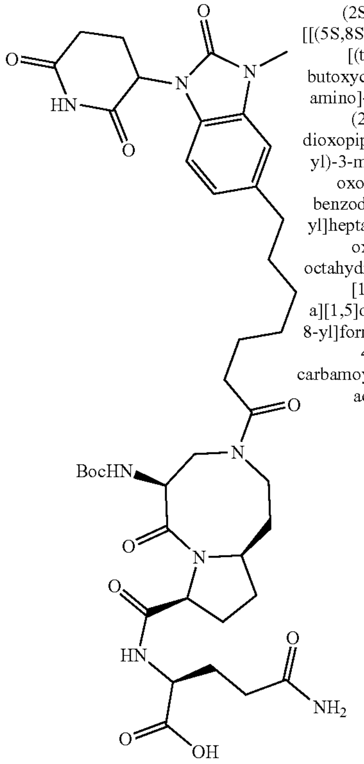 | (2S)-2-[[(5S,8S,10aR)-5-[(tert-butoxycarbonyl)amino]-3-[7-[1-(2,6-dioxopiperidin-3-yl)-3-methyl-2-oxo-1,3-benzodiazol-5-yl]heptanoyl]-6-oxo-octahydropyrrolo[1,2-a][1,5]diazocin-8-yl]formamido]-4-carbamoylbutanoic acid | 825.45 | (400 MHz, DMSO-$d_6$) δ 11.09 (s, 1H), 8.26 (t, J = 8.8 Hz, 1H), 7.20 (d, J = 15.4 Hz, 1H), 7.05-6.95 (m, 2H), 6.90-6.83 (m, 1H), 6.77 (s, 1H), 6.57 (d, J = 6.9 Hz, 1H), 5.34 (dd, J = 12.7, 5.3 Hz, 1H), 4.49-4.34 (m, 2H), 4.22-4.09 (m, 2H), 3.75-3.60 (m, 2H), 3.33 (s, 3H), 3.28-3.19 (m, 1H), 3.18-3.04 (m, 1H), 2.97-2.84 (m, 1H), 2.77-2.56 (m, 4H), 2.47-2.35 (m, 2H), 2.25-2.10 (m, 3H), 2.05-1.91 (m, 3H), 1.88-1.72 (m, 3H), 1.63-1.48 (m, 6H), 1.38 (s, 9H), 1.35-1.29 (m, 4H) |

(2S,4R)-1-I(2S)-3,3-dimethyl-2-([1-[3-(trimethylsilyl)prop-2-yn-1-yl]cyclopropyl]form amido)butanoyl]-4-hydroxy-N-[[14-(4-methyl-1,3-thiazol-5-yl)phenyl]methyl]pyrrolidine-2-carboxamide (Intermediate Q)

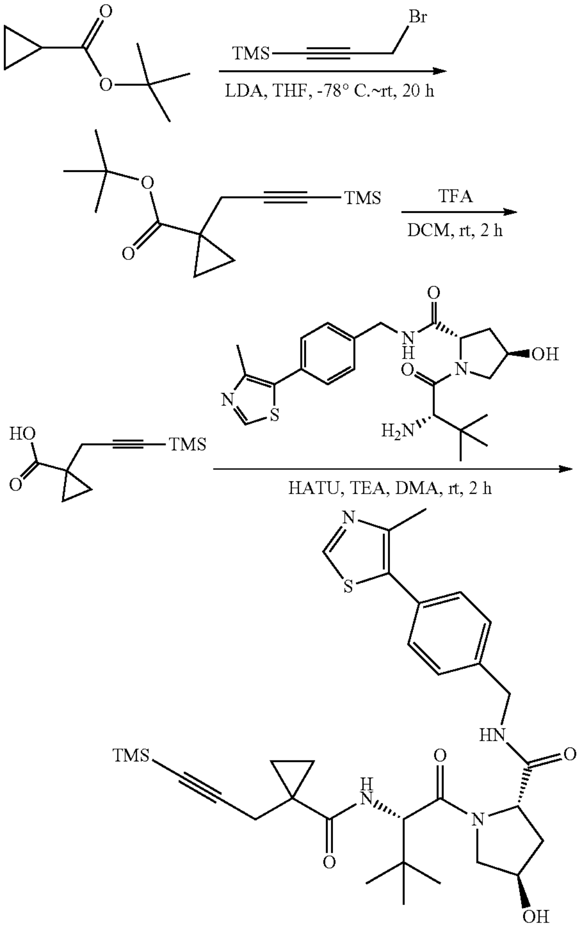

Intermediate Q

Step 1: Tert-butyl 1-[3-(trimethylsilyl)prop-2-yn-1-yl]cyclopropane-1-carboxylate. To a solution of tert-butyl cyclopropanecarboxylate(5 g, 35.162 mmol) in THF(150.00 mL) was added LDA (16.88 mL, 42.194 mmol, 2.5 M in THF) at −78° C. under nitrogen atmosphere. The solution was stirred at −78° C. for 2 h. To the above solution was added a solution of (3-bromoprop-1-yn-1-yl)trimethylsilane (8.74 g, 45.725 mmol) in THF (150.00 mL) and DMPU (60.00 mL, 498.080 mmol) dropwise at −78° C. The mixture was stirred at −78° C. for additional 2 h and then was warmed to room temperature. The reaction was stirred at 25° C. for 16 h. The reaction was quenched by water/ice (500 mL). The resulting mixture was extracted with EtOAc (3×300 mL). The combined organic layers were washed with brine (3×200 mL) and dried over anhydrous $Na_2SO_4$. After filtration, the filtrate was concentrated under reduced pressure. The residue was purified by silica gel column chromatography, eluted with petroleum ether/EtOAc (50:1 to 10:1) to afford the title compound (6 g, 68%) as a red oil: $^1$H NMR (400 MHz, $CDCl_3$) b 2.72 (s, 2H), 1.46 (s, 9H), 1.14 (q, J=3.9 Hz, 2H), 0.94 (q, J=3.9 Hz, 2H), 0.16 (s, 9H).

Step 2: 1-[3-(Trimethylsilyl)prop-2-yn-1-yl]cyclopropane-1-carboxylic acid. To a solution of tert-butyl 1-[3-(trimethylsilyl)prop-2-yn-1-yl]cyclopropane-1-carboxylate (3.00 g, 11.885 mmol) in DCM (20.00 mL) was added TFA (5.00 mL) at 25° C. The mixture was stirred at 25° C. for 2 h. The resulting mixture was concentrated under reduced pressure to afford the crude title compound (2 g), which was used to the next step without further purification: $^1$H NMR (400 MHz, $CDCl_3$) b 2.69 (s, 2H), 1.49 (q, J=4.5 Hz, 2H), 0.91 (q, J=4.8, 4.4 Hz, 2H), 0.16 (s, 9H).

Step 3: (2SAR)-1-[(2S)-3,3-dimethyl-2-([1-[3-(trimethylsilyl)prop-2-yn-1-yl]cyclopropyl]formamido)butanoyl]-4-hydroxy-N-[[4-(4-methyl-1,3-thiazol-5-yl)phenyl]methyl] pyrrolidine-2-carboxamide. To a solution of (2S,4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide (2.30 g, 5.342 mmol) and 1-[3-(trimethylsilyl) prop-2-yn-1-yl]cyclopropane-1-carboxylic acid (1.05 g, 5.342 mmol) in DMA (57.50 mL) were added HATU (2.44 g, 6.410 mmol) and TEA (2.16 g, 21.367 mmol) at 25° C. The mixture was stirred at 25° C. for 2 h. The resulting solution was purified by Prep-HPLC with the following conditions (Column: XBridge Shield RP18 OBD Column, 30×150 mm, 5 um; Mobile Phase A: water (10 mmoL/ $LNH_4HCO_3$), Mobile Phase B: ACN; Flow rate: 60 mL/min; Gradient: 20 B to 55 B in 25 min; 220 nm; RT: 23 min) to afford the title compound (650 mg, 20%) as a yellow solid: $^1$H NMR (400 MHz, $CDCl_3$) δ 8.72 (s, 1H), 7.49 (t, J=5.9 Hz, 1H), 7.40-7.30 (m, 4H), 6.97 (d, J=7.7 Hz, 1H), 4.76 (t, J=8.0 Hz, 1H), 4.57 (dd, J=14.9, 6.5 Hz, 1H), 4.48 (s, 1H), 4.40 (d, J=7.7 Hz, 1H), 4.32 (dd, J=14.8, 5.0 Hz, 1H), 4.16 (d, J=11.5 Hz, 1H), 3.54 (dd, J=11.4, 3.5 Hz, 1H), 3.19 (s, 1H), 2.66-2.53 (m, 2H), 2.51 (s, 3H), 2.37 (d, J=18.0 Hz, 1H), 2.21-2.05 (m, 1H), 1.27-1.08 (m, 3H), 0.97 (s, 9H), 0.81-0.65 (m, 1H), 0.15 (s, 9H). LC/MS (ESI, m/z): $[(M+1)]^+$=609.30.

Tert-butyl N-[(3S)-1-(3-bromophenyl)-5-carbamoylpent-1-yn-3-yl]carbamate (Intermediate R)

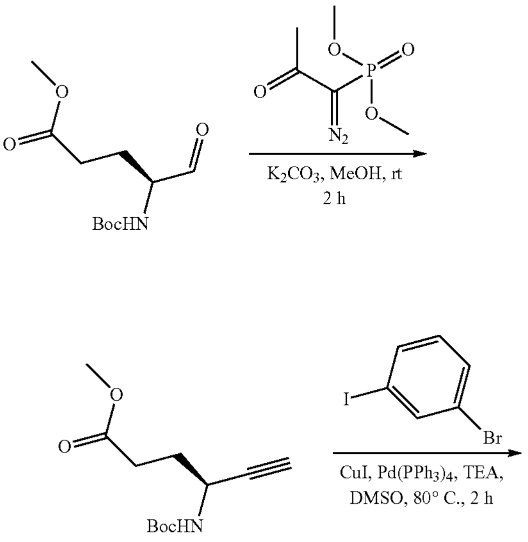

-continued

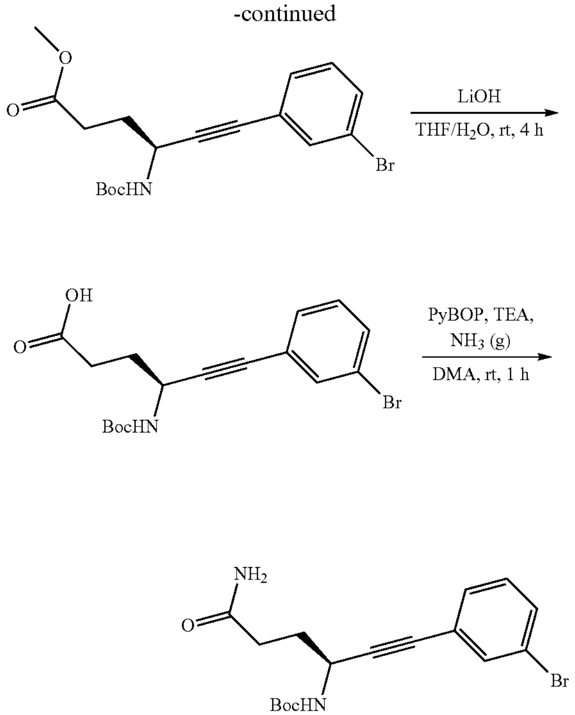

Intermediate R

Step 1: (4S)-4-[(Tert-butoxycarbonyl)amino]hex-5-ynoate. To a stirred mixture of methyl (4S)-4-[(tert-butoxycarbonyl)amino]-5-oxopentanoate (500.00 mg, 2.039 mmol) and $K_2CO_3$ (563.47 mg, 4.077 mmol) in MeOH (8.00 mL) was added seyferth-gilbert homologation (411.20 mg, 2.140 mmol) at 0° C. under air atmosphere. The resulting mixture was stirred for 2 h at room temperature under air atmosphere. The resulting mixture was filtered. The filter cake was washed with $CH_2Cl_2$ (2×5 mL). The filtrate was concentrated under reduced pressure. The residue was purified by silica gel column chromatography, eluted with 10% EtOAc in petroleum ether to afford the title compound (260 mg, 50%) as a light yellow oil: $^1H$ NMR (400 MHz, $CDCl_3$) δ 4.93-4.75 (m, 1H), 4.56-4.34 (m, 1H), 3.69 (s, 3H), 2.57-2.38 (m, 2H), 2.31 (d, J=2.3 Hz, 1H), 2.01 (qd, J=7.1, 2.2 Hz, 2H), 1.45 (s, 9H); LC/MS (ESI, m/z): $[(M+1-100)]^+$=142.10.

The intermediates in Table 70 were prepared according to the above procedure.

TABLE 70

| Characterization data for intermediates prepared according to above. | | | | |
|---|---|---|---|---|
| Intermediate | Structure | Chemical Name | MS: $[(M + 1)]^+$ | $^1H$-NMR |
| R-1-1 | 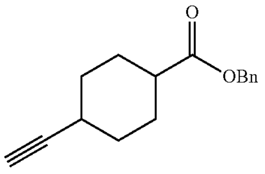 [SMILES: C#CC1CCC(C(=O)OCc2ccccc2)CC1] | benzyl 4-ethynylcyclohexane-1-carboxylate | N/A | (400 MHz, Chloroform-d) δ 7.43-7.32 (m, 5H), 5.14 (d, J = 8.6 Hz, 2H), 2.41-2.24 (m, 3H), 2.10-1.94 (m, 4H), 1.51-1.38 (m, 4H) |

Step 2: Methyl (4S)-6-(3-bromophenyl)-4-[(tert-butoxycarbonyl)amino]hex-5-ynoate. To a stirred mixture of methyl (4S)-4-[(tert-butoxycarbonyl)amino]hex-5-ynoate (1.10 g, 4.559 mmol) and 1-bromo-3-iodo-benzene (1.55 g, 5.479 mmol) in TEA (12.00 mL, 86.333 mmol) and DMSO (12.00 mL) were added CuI (86.82 mg, 0.456 mmol) and $Pd(PPh_3)_4$(526.81 mg, 0.456 mmol) at room temperature under nitrogen atmosphere. The resulting mixture was stirred for 2 h at 80° C. under nitrogen atmosphere. The mixture was allowed to cool down to room temperature and was concentrated under reduced pressure. The residue was purified by reverse phase flash chromatography with the following conditions: Column: WelFlash™ C18-I, 20~40 um, 330 g; Eluent A: water (plus 10 mmol/L formic acid); Eluent B: ACN; Gradient: 40% - 70% B in 30 min; Flow rate: 80 mL/min; Detector: 220/254 nm; desired fractions were collected at 65% B and concentrated under reduced pressure to afford the title compound (1.5 g, 79%) as a brown oil: $^1H$ NMR (400 MHz, $CDCl_3$) δ 7.57 (t, J=1.8 Hz, 1H), 7.46 (ddd, J=8.1, 2.0, 1.1 Hz, 1H), 7.35 (dt, J=7.7, 1.3 Hz, 1H), 7.19 (t, J=7.9 Hz, 1H), 4.95-4.80 (m, 1H), 4.80-4.61 (m, 1H), 3.71 (s, 3H), 2.61-2.47 (m, 2H), 2.10 (qt, J=8.4, 3.9 Hz, 2H), 1.48 (s, 9H); LC/MS (ESI, m/z): $[(M+1-100)]^+$=295.95, 297.95.

Step 3: (4S)-6-(3-Bromophenyl)-4-[(tert-butoxycarbonyl)amino]hex-5-ynoic acid. To a stirred solution of methyl (4S)-6-(3-bromophenyl)-4-[(tert-butoxycarbonyl)amino]hex-5-ynoate (1.50 g, 3.785 mmol) in dioxane (15.00 mL) was added a solution of LiOH (5.00 mL, 2 M in water) dropwise at 0° C. under nitrogen atmosphere. The resulting mixture was stirred for 4 h at room temperature under nitrogen atmosphere. The resulting mixture was concentrated under reduced pressure. The residue was diluted with water (10 mL). The mixture was acidified to pH 6 with HOAc. The precipitated solids were collected by filtration and washed with water (2×3 mL). It was dried under reduced pressure to afford the title compound (1.35 g, 89%) as a yellow solid: $^1H$ NMR (400 MHz, DMSO-d4) δ 7.61-7.55 (m, 2H), 7.55-7.46 (m, 1H), 7.43-7.37 (m, 1H), 7.33 (t, J=7.8 Hz, 1H), 4.55-4.39 (m, 1H), 2.31-2.53 (m, 2H), 1.92-1.83 (m, 2H), 1.40 (s, 9H); LC/MS (ESI, m/z): $[(M+1-100)]^+$=281.90, 283.90.

The intermediates in Table 71 were prepared according to the above procedure.

TABLE 71

Characterization data for intermediates prepared according to above.

| Inter-mediate | Structure | Chemical Name | MS: [(M + 1)] | $^1$H-NMR |
|---|---|---|---|---|
| R-3-1 | 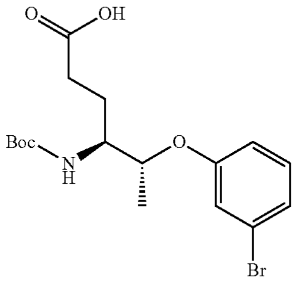 [SMILES: C[C@@H](Oc1cccc(Br)c1)[C@H](CCC(=O)O)NC(=O)OC(C)(C)C] | (4S,5R)-5-(3-bromophenoxy)-4-[(tert-butoxycarbonyl)amino]hexanoic acid | 402.05, 404.05 | (400 MHz, DMSO-$d_6$) δ 12.03 (s, 1H), 7.29-7.21 (m, 1H), 7.17-7.03 (m, 2H), 6.96-6.88 (m, 2H), 6.80 (d, J = 9.4 Hz, 1H), 4.38 (q, J = 6.0 Hz, 1H), 2.37-2.13 (m, 2H), 1.92-1.81 (m, 1H), 1.59-1.50 (m, 1H), 1.38 (s, 9H), 1.18 (d, J = 7.0 Hz, 3H) |
| R-3-2 | 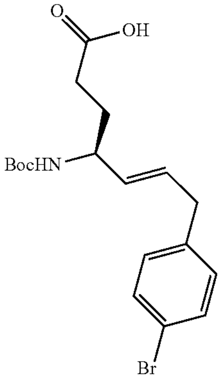 [SMILES: CC(C)(C)OC(=O)N[C@H](/C=C/Cc1ccc(Br)cc1)CCC(=O)O] | (S,E)-7-(4-bromophenyl)-4-((tert-butoxycarbonyl)amino)hept-5-enoic acid | 398.15, 400.15 | used next step directly without purification |

Step 4: Tert-butyl N-[(3S)-1-(3-bromophenyl)-5-carbamoylpent-1-yn-3-yl]carbamate. To a stirred solution of (4S)-6-(3-bromophenyl)-4-[(tert-butoxycarbonyl)amino]hex-5-ynoic acid (1.25 g, 3.270 minol) and TEA (957.56 mg, 9.463 minol) in DMA (20.00 mL) was added PyBOP (1.97 g, 3.786 minol) at room temperature under $NH_3$ (g) atmosphere. The resulting mixture was stirred for 2 h at room temperature under $NH_3$ (g) atmosphere. The resulting solution was purified by reverse phase flash chromatography with the following conditions: Column: WelFlash™ C18-I, 20~40 um, 80 g; Eluent A: water (plus 10 mmol/L formic acid); Eluent B: ACN; Gradient: 35% - 5500 B in 15 min; Flow rate: 50 mL/min; Detector: 220/254 nm; desired fractions were collected at 5000 B and concentrated under reduced pressure to afford the title compound (1.0 g, 79%) as a white solid: $^1$H NMR (400 MHz, DMSO-$d_6$) δ 7.64-7.56 (m, 2H), 7.42 (dt, J=7.8, 1.3 Hz, 2H), 7.34 (t, J=7.8 Hz, 2H), 6.80 (s, 1H), 4.47 (q, J=7.7 Hz, 1H), 2.23 (td, J=7.4, 3.8 Hz, 2H), 1.86 (q, J=7.5 Hz, 2H), 1.41 (s, 9H); LC/MS (ESI, m/z): $[(M+1-100)]^+$=280.95, 292.95.

The intermediates in Table 72 were prepared according to the above procedure.

TABLE 72

Characterization data for intermediates prepared according to above.

| Inter-mediate | Structure | Chemical Name | MS: $[(M + 1)]^+$ | $^1$H-NMR |
|---|---|---|---|---|
| R1 | 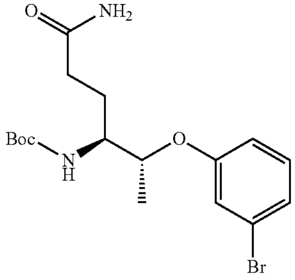 | tert-butyl N-[(3S,4R)-4-(3-bromophenoxy)-1-carbamoylpentan-3-yl]carbamate | 401.05, 403.05 | (400 MHz, DMSO-$d_6$) δ 7.29-7.19 (m, 2H), 7.13-7.06 (m, 2H), 6.95-6.88 (m, 1H), 6.82-401.05, 6.66 (m, 2H), 4.40-4.34 (m, 403.05 1H), 3.57-3.50 (m, 1H), 2.16-1.99 (m, 2H), 1.88-1.74 (m, 1H), 1.59-1.46 (m, 1H), 1.38 (s, 9H), 1.18 (d, J = 6.1 Hz, 3H) |

TABLE 72-continued

| Characterization data for intermediates prepared according to above. | | | | |
|---|---|---|---|---|
| Inter-mediate | Structure | Chemical Name | MS: $[(M + 1)]^+$ | $^1H$-NMR |
| R2 | 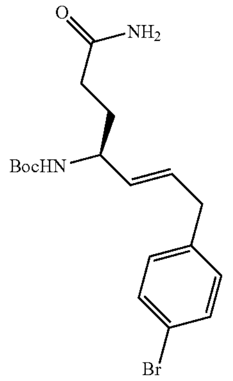 | tert-butyl N-[(3S,4E)-6-(4-bromophenyl)-1-carbamoylhex-4-en-3-yl]carbamate | 397.15, 399.15 | (400 MHz, DMSO-$d_6$) δ 7.51-7.44 (m, 2H), 7.25-7.20 (m, 1H), 7.15 (d, J = 8.4 Hz, 2H), 6.86 (d, J = 8.5 Hz, 1H), 6.71 (s, 1H), 5.64-5.53 (m, 1H), 5.40 (dd, J = 15.4, 6.6 Hz, 1H), 3.86 (s, 1H), 3.30 (d, J = 6.9 Hz, 2H), 2.03 (t, J = 7.8 Hz, 2H), 1.60 (p, J = 7.3 Hz, 2H), 1.38 (s, 9H) |

1-[4-(Propane-2-sulfonyl)phenyl]methanamine (Intermediate T)

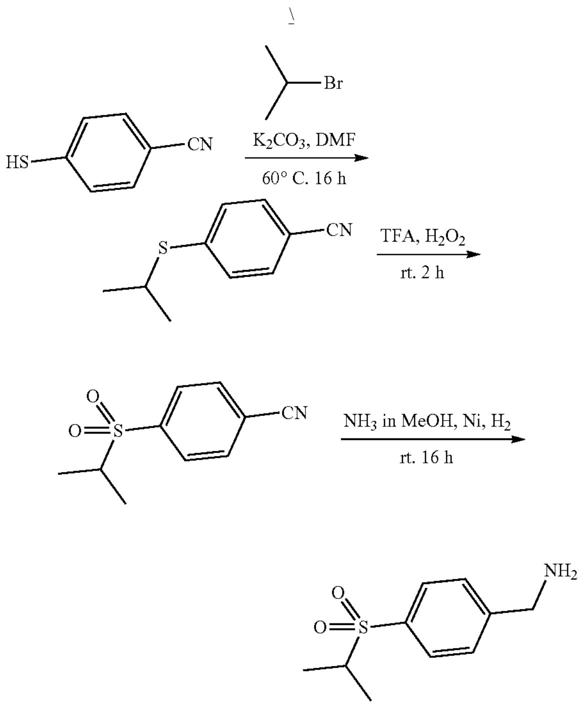

Intermediate T

Step 1: 4-(isopropylsulfanyl)benzonitrile. To a stirred mixture of 4-sulfanylbenzonitrile (10.00 g, 73.975 mmol, 1.00 equiv) and 2-bromopropane (27.30 g, 221.926 mmol, 3 equiv) in DMF (150.00 mL) was added $K_2CO_3$ (81.79 g, 591.804 mmol, 8 equiv) in portions at room temperature under air atmosphere. The resulting mixture was stirred for 16 h at 60 degrees C. under nitrogen atmosphere. The mixture was allowed to cool down to room temperature. The reaction was monitored by LCMS. The resulting mixture was extracted with EtOAc (3×100 mL). The combined organic layers were washed with brine (3×200 mL), dried over anhydrous $Na_2SO_4$. After filtration, the filtrate was concentrated under reduced pressure. The residue was purified by silica gel column chromatography, eluted with PE/EtOAc (5:1) to afford the title compound (12.7 g, 96.85%) as an orange oil; $^1H$ NMR (400 MHz, Chloroform-d) δ 7.59-7.51 (m, 2H), 7.41-7.33 (m, 2H), 3.62-3.52 (m, 1H), 1.39 (d, J=6.7 Hz, 6H); LC/MS (ESI, m/z): $[(M+H)]^+$=178.20

Step 2: 4-(propane-2-sulfonyl)benzonitrile. To a stirred mixture of 4-(isopropylsulfanyl)benzonitrile (5.00 g, 28.206 mmol, 1.00 equiv) in TFA (100.00 mL) was added $H_2$02 (30%) (100 mL) dropwise at 0 degrees C. The resulting mixture was stirred for 2 h at room temperature under air atmosphere. The reaction was monitored by LCMS. The resulting mixture was extracted with EtOAc (3×100 mL). The combined organic layers were washed with brine (200 mL), dried over anhydrous $Na_2SO_4$. After filtration, the filtrate was concentrated under reduced pressure to afford the title compound (4.8 g, 81.32%) as a white solid; $^1H$ NMR (400 MHz, Chloroform-d) δ 8.08-7.97 (m, 2H), 7.95-7.81 (m, 2H), 3.29-3.20 (m, 1H), 1.31 (d, J=6.9 Hz, 6H); LC/MS (ESI, m/z): $[(M+H)]^+$=209.95. Step 3: 1-[4-(propane-2-sulfonyl)phenyl]methanamine. To a solution of 4-(propane-2-sulfonyl)benzonitrile (4.80 g, 22.938 mmol, 1.00 equiv) in 40 mL 7 M $NH_3$ in MeOH was added Ni (5 g) under nitrogen atmosphere in a 250 mL round-bottom flask. The mixture was hydrogenated at room temperature for 16 h under hydrogen atmosphere using a hydrogen balloon, filtered through a Celite pad and concentrated under reduced pressure. The residue was purified by reverse phase Flash chromatography with the following conditions: Column: WelFlash™ C18-I, 20~40 μm, 330 g; Eluent A: Water; Eluent B: ACN; Gradient: 2% - 20% B in 25 min; Flow rate: 80 mL/min; Detector: 220/254 nm; desired fractions were collected at 12% B and concentrated under reduced pressure to afford the title compound (3.28 g, 67.04%) as a yellow oil; $^1H$ NMR (300 MHz, DMSO-$d_6$) δ 7.79 (d, J=8.6 Hz, 2H), 7.64 (d, J=8.0 Hz, 2H), 3.85 (s, 2H), 3.47-3.27 (m, 1H), 1.16 (dd, J=6.8, 1.2 Hz, 6H); LC/MS (ESI, m/z): $[(M+H)]^+$=214.15.

EXAMPLES

Example 1. Synthesis of [([4-[(1E)-1-[[(2S,11S)-2-[[(3S,4R)-1-carbamoyl-4-([4-[3-(2-[3-[1-(2,6-dioxopiperidin-3-yl)-3-methyl-2-oxo-1,3-benzodiazol-5-yl]propoxy]ethoxy)propyl]phenyl]methoxy)pentan-3-yl]carbamoyl]-12-oxo-1-azatricyclo[6.4.1.0[4,13]]trideca-4(13), 5,7-trien-11-yl]carbamoyl]prop-1-en-2-yl]phenyl]difluoromethyl([[(2,2-dimethylpropanoyl)oxy]methoxy)phosphoryl)oxy]methyl 2,2-dimethylpropanoate (I-54)

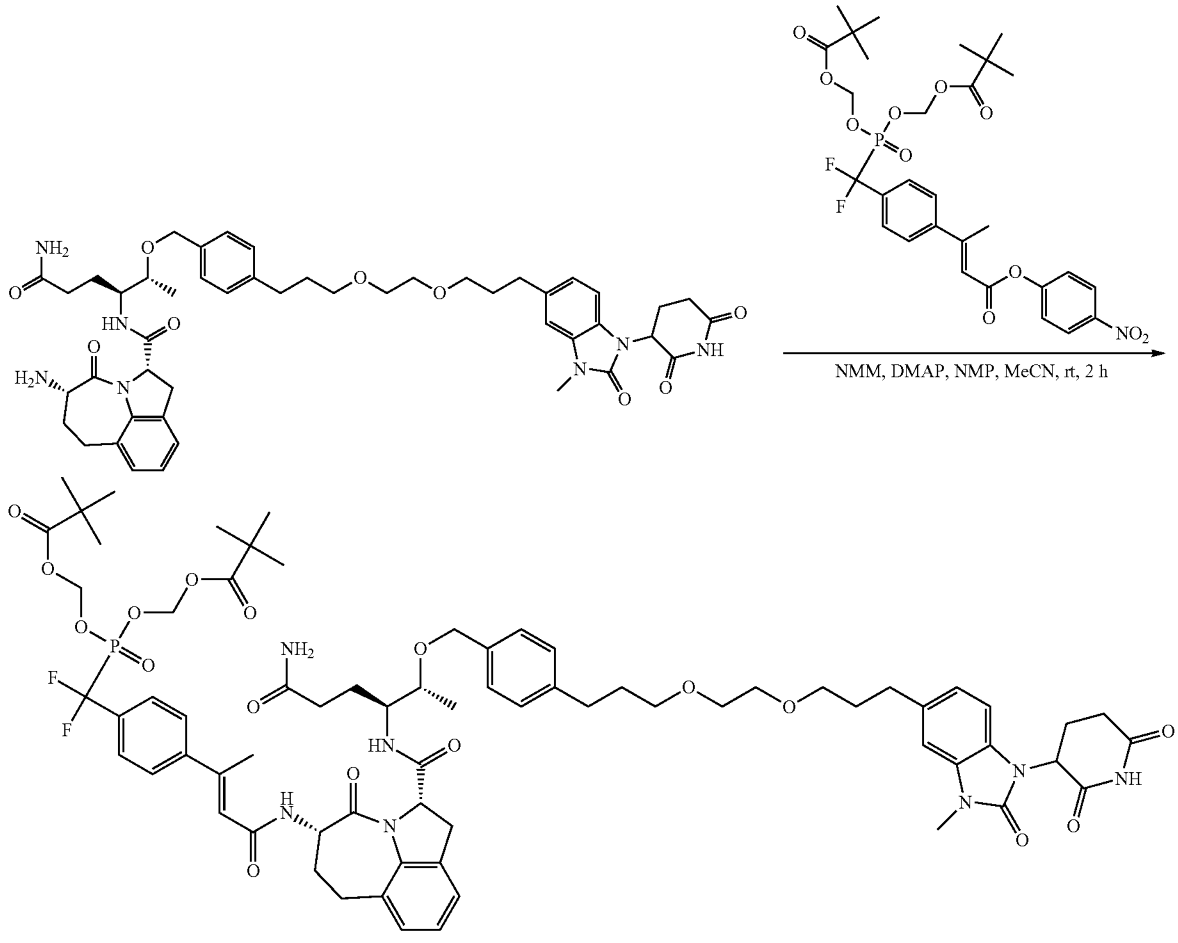

I-54

To a solution of (4S,5R)-4-[[(2S,11S)-11-amino-12-oxo-1-azatricyclo[6.4.1.0[4,13]]trideca-4(13), 5,7-trien-2-yl]formamido]-5-([4-[3-(2-[3-[1-(2,6-dioxopiperidin-3-yl)-3-methyl-2-oxo-1,3-benzodiazol-5-yl]propoxy]ethoxy)propyl]phenyl]methoxy)hexanamide acetic acid (80.0 mg, 0.086 mmol) in NMP (2.00 mL) were added NMM (26.2 mg, 0.26 mmol), DMAP (1.10 mg, 0.009 mmol) and 4-nitrophenyl (2E)-3-[4-[(bis[[(2,2-dimethylpropanoyl)oxy]methoxy]phosphoryl)difluoromethyl]phenyl]but-2-enoate (72.1 mg, 0.11 mmol) in acetonitrile (0.50 mL) at room temperature. The resulting mixture was stirred at room temperature for 2 hours. The mixture was purified by Prep-HPLC with the following conditions (Column: XBridge Shield RP18 OBD Column, 5 um, 19×150 mm; Mobile Phase A: water; Mobile Phase B: ACN; Flow rate: 25 mL/min; Gradient: 50% B to 65% B in 7 min; Detector: UV 220/254 nm. The fractions containing desired product was collected at 6.50 min and lyophilized to afford the title compound as a white solid (22.5 mg, 19%): $^1$H NMR (400 MHz, $CDCl_3$) δ 8.94 (d, J=7.8 Hz, 1H), 7.64-7.54 (m, 4H), 7.23 (d, J=6.6 Hz, 1H), 7.14-7.11 (m, 2H), 7.07 (d, J=8.5 Hz, 3H), 6.96-6.85 (m, 3H), 6.72 (d, J=7.9 Hz, 1H), 6.24-6.06 (m, 2H), 5.72-5.43 (m, 4H), 5.25-5.15 (m, 2H), 4.69-4.50 (m, 2H), 4.40 (d, J=11.6 Hz, 1H), 3.96 (s, 1H), 3.64-3.54 (m, 6H), 3.50-3.45 (m, 4H), 3.41-3.09 (m, 6H), 2.81-2.62 (m, 8H), 2.58 (s, 3H), 2.44-2.04 (m, 6H), 2.00-1.85 (m, 7H), 1.24 (s, 18H), 1.20 (s, 3H); MS (ESI, m/z): $[(M+1)]^+$=1368.75.

The following compounds in Table 73 were synthesized according to the above procedure of Example 1.

TABLE 73

| Characterization Data for Exemplary STAT3 Degraders | | | | |
|---|---|---|---|---|
| EXAMPLE | I-# | Chemical Name | MS: $[(M + 1)]^+$ | $^1H$ NMR |
| 2 | I-1 | [4-[(1E)-1-[[(2S,11S)-2-[[(3S,4R)-1-carbamoyl-4-[[4-(4-[[(2S)-1-[(2S,4R)-4-hydroxy-2-([[4-(4-methyl-1,3-thiazol-5-yl)phenyl]methyl]carbamoyl) pyrrolidin-1-yl]-3,3-dimethyl-1-oxobutan-2-yl]carbamoyl]butyl)phenyl]methoxy] pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethylphosphonic acid | 1251.7 | (400 MHz, $CD_3OD$) δ 8.88 (s, 1H), 7.72 (d, J = 8.1 Hz, 2H), 7.55 (d, J = 8.2 Hz, 2H), 7.48 (d, J = 8.3 Hz, 2H), 7.42 (d, J = 8.2 Hz, 2H), 7.23 (d, J = 7.9 Hz, 2H), 7.16-7.09 (m, 3H), 7.05 (dt, J = 14.7, 7.1 Hz, 2H), 6.37 (s, 1H), 5.15 (dd, J = 10.8, 3.4 Hz, 1H), 4.87 (s, 1H), 4.65 (d, J = 5.3 Hz, 2H), 4.59-4.55 (m, 1H), 4.54-4.42 (m, 4H), 4.36 (d, J = 15.6 Hz, 1H), 4.05-3.95 (m, 1H), 3.91 (d, J = 11.2 Hz, 1H), 3.81 (dd, J = 10.9, 4.0 Hz, 1H), 3.65-3.52 (m, 1H), 3.48 (d, J = 11.0 Hz, 1H), 3.28-3.11 (m, 2H), 3.03 (d, J = 7.3 Hz, 1H), 2.63 (s, 2H), 2.56-2.50 (m, 3H), 2.49 (s, 3H), 2.29-2.16 (m, 7H), 2.14-1.98 (m, 2H), 1.65-1.48 (m, 4H), 1.19-1.06 (m, 3H), 1.04 (s, 9H). |
| 3 | I-2 | [([4-[(1E)-1-[[(2S,11S)-2-[[(3S,4R)-1-carbamoyl-4-[[4-(4-[[(2S)-1-[(2S,4S)-4-hydroxy-2-([[4-(4-methyl-1,3-thiazol-5-yl)phenyl]methyl]carbamoyl) pyrrolidin-1-yl]-3,3-dimethyl-1-oxobutan-2-yl]carbamoyl]butyl)phenyl]methoxy] pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl([(2,2-dimethylpropanoyl)oxy]methoxy) phosphoryl)oxy]methyl 2,2-dimethylpropanoate | 1480.9 | (400 MHz, $CDCl_3$) δ 8.71 (s, 1H), 7.70-7.58 (m, 3H), 7.54 (d, J = 8.2 Hz, 2H), 7.43-7.31 (m, 4H), 7.31-7.20 (m, 3H), 7.17-7.00 (m, 5H), 6.87 (dd, J = 19.1, 7.7 Hz, 2H), 6.15-6.02 (m, 2H), 5.90 (s, 1H), 5.76 (ddd, J = 12.4, 5.0, 2.0 Hz, 2H), 5.68 (ddd, J = 12.3, 5.0, 1.8 Hz, 2H), 5.19 (dd, J = 9.7, 2.9 Hz, 1H), 5.02 (s, 1H), 4.72-4.50 (m, 5H), 4.49-4.38 (m, 2H), 4.32 (dd, J = 15.0, 5.0 Hz, 1H), 4.01-3.89 (m, 2H), 3.83 (d, J = 10.9 Hz, 1H), 3.64-3.55 (m, 1H), 3.43-3.26 (m, 3H), 3.18-3.07 (m, 1H), 2.63-2.47 (m, 8H), 2.33 (d, J = 6.4 Hz, 2H), 2.28-2.16 (m, 3H), 2.14-2.00 (m, 3H), 1.98-1.87 (m, 1H), 1.80 (dq, J = 20.5, 6.5 Hz, 1H), 1.69-1.52 (m, 4H), 1.24-1.03 (m, 21H), 0.94 (s, 9H). |
| 4 | I-3 | [([4-[(1E)-1-[[(2S,11S)-2-[[(3S,4R)-1-Carbamoyl-4-[(4-[4-[1-(2,6-dioxopiperidin-3-yl)-3-methyl-2-oxo-1,3-benzodiazol-4-yl]butyl]phenyl)methoxy]pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl([(2,2-dimethylpropanoyl)oxy]methoxy) phosphoryl)oxy]methyl 2,2-dimethylpropanoate | 1280.9 | (400 MHz, $CDCl_3$) δ 8.67 (d, J = 7.3 Hz, 1H), 7.65-7.53 (m, 4H), 7.26 (d, J = 2.5 Hz, 1H), 7.14 (d, J = 7.8 Hz, 1H), 7.11-6.91 (m, 6H), 6.87 (d, J = 7.9 Hz, 1H), 6.69 (d, J = 7.8 Hz, 1H), 6.18 (d, J = 12.3 Hz, 1H), 6.04 (d, J = 8.8 Hz, 1H), 5.72-5.60 (m, 4H), 5.25-5.10 (m, 2H), 5.03 (s, 1H), 4.62 (d, J = 11.3 Hz, 2H), 4.41 (dd, J = 11.6, 8.0 Hz, 1H), 3.96 (s, 1H), 3.59 (q, J = 6.3 Hz, 1H), 3.55-3.46 (m, 3H), 3.43-3.24 (m, 3H), 3.14 (d, J = 7.4 Hz, 1H), 2.97-2.71 (m, 5H), 2.63 (t, J = 7.0 Hz, 2H), 2.58-2.48 (m, 3H), 2.39 (d, J = 7.2 Hz, 1H), 2.23-1.94 (m, 5H), 1.86-1.58 (m, 8H), 1.24-1.04 (m, 20H). |
| 5 | I-4 | [([4-[(1E)-1-[[(2S,11S)-2-[[(3S,4R)-1-carbamoyl-4-[[4-([[(2S)-1-[(2S,4R)-4-hydroxy-2-([[4-(4-methyl-1,3-thiazol-5-yl)phenyl]methyl]carbamoyl) pyrrolidin-1-yl]-3,3-dimethyl-1-oxobutan-2-yl]carbamoyl]methyl)phenyl] methoxy]pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl([(2,2-dimethylpropanoyl)oxy]methoxy) phosphoryl)oxy]methyl 2,2-dimethylpropanoate | 1438.9 | (400 MHz, $CDCl_3$) δ 8.74 (s, 1H), 7.63 (d, J = 8.1 Hz, 2H), 7.55 (d, J = 8.2 Hz, 2H), 7.46 (s, 1H), 7.39-7.30 (m, 6H), 7.21 (d, J = 7.7 Hz, 2H), 7.14-6.92 (m, 5H), 6.23-6.13 (m, 2H), 5.92 (s, 1H), 5.77 (dt, J = 12.5, 5.2 Hz, 2H), 5.68 (ddd, J = 12.5, 5.1, 1.4 Hz, 2H), 5.18 (s, 2H), 4.72-4.58 (m, 1H), 4.58 (s, 2H), 4.58-4.46 (m, 3H), 4.44-4.30 (m, 3H), 4.00 (d, J = 11.2 Hz, 2H), 3.92 (s, 1H), 3.69-3.57 (m, 3H), 3.48 (s, 2H), 3.43 (d, J = 6.1 Hz, 1H), 3.38-3.24 (m, 3H), 3.08 (d, J = 7.7 Hz, 2H), 2.59-2.51 (m, 2H), 2.46 (ddd, J = 12.9, 8.0, 4.6 Hz, 2H), 2.36 (d, J = 13.7 Hz, 1H), 2.16-2.04 (m, 1H), 2.03 (s, 2H), 1.90 (s, 1H), 1.76 (s, 1H), 1.24 (s, 18H), 1.21-1.03 (m, 3H), 0.88 (s, 9H). |
| 6 | I-5 | [([4-[(1E)-1-[[(2S,11S)-2-[[(35,4R)-1-carbamoyl-4-[[4-(3-[[1-(2,6-dioxopiperidin-3-yl)-3-methyl-2-oxo-1,3-benzodiazol-4-yl]methoxy]propyl)phenyl]methoxy] pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl([(2,2-dimethylpropanoyl)oxy]methoxy) | 1296.9 | (400 MHz, $CDCl_3$) δ 9.53 (d, J = 8.5 Hz, 1H), 7.68-7.50 (m, 4H), 7.26-7.12 (m, 3H), 7.07 (d, J = 4.1 Hz, 1H), 7.06-6.95 (m, 3H), 6.97-6.89 (m, 3H), 6.87 (dd, J = 16.8, 8.4 Hz, 2H), 6.23 (d, J = 8.4 Hz, 1H), 5.95 (d, J = 7.2 Hz, 1H), 5.83-5.61 (m, 4H), 5.36-5.06 (m, 3H), 4.83 (dd, J = 24.2, 12.0 Hz, 1H), 4.62-4.52 (m, 3H), 4.36 (t, J = 12.2 Hz, 1H), 3.92 (t, J = 10.5 Hz, 1H), 3.75-3.64 (m, 3H), 3.60-3.48 (m, 1H), 3.48-3.17 (m, 4H), 3.17-3.02 (m, 2H), 2.97-2.70 (m, 3H), 2.68-2.53 (m, 5H), 2.37 (d, J = 13.2 Hz, 1H), 2.26-2.13 (m, 2H), |

TABLE 73-continued

Characterization Data for Exemplary STAT3 Degraders

| EXAMPLE | I-# | Chemical Name | MS: $[(M + 1)]^+$ | $^1H$ NMR |
|---|---|---|---|---|
| | | phosphoryl)oxy]methyl 2,2-dimethylpropanoate | | 2.15-2.00 (m, 2H), 2.01-1.74 (m, 3H), 1.24 (s, 18H), 1.22-1.14 (m, 4H). |
| 7 | I-6 | [([4-[(1E)-1-[[(2S,11S)-2-[[(3S,4R)-1-carbamoyl-4-[(4-[5-[1-(2,6-dioxopiperidin-3-yl)-3-methyl-2-oxo-1,3-benzodiazol-4-yl]pentyl]phenyl)methoxy]pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl([(2,2-dimethylpropanoyl)oxy]methoxy)phosphoryl)oxy]methyl 2,2-dimethylpropanoate | 1294.8 | (400 MHz, $CDCl_3$) δ 8.89 (d, J = 6.8 Hz, 1H), 7.61 (d, J = 8.1 Hz, 2H), 7.54 (dd, J = 8.4, 3.0 Hz, 2H), 7.26 (dd, J = 7.9, 4.6 Hz, 2H), 7.16-6.92 (m, 7H), 6.90-6.81 (m, 2H), 6.70 (t, J = 7.5 Hz, 1H), 6.16 (d, J = 11.5 Hz, 1H), 5.97 (s, 1H), 5.76 (dd, J = 12.5, 5.0 Hz, 2H), 5.68 (dd, J = 12.4, 5.0 Hz, 2H), 5.27-5.12 (m, 2H), 5.07 (s, 1H), 4.65-4.53 (m, 2H), 4.43 (d, J = 11.6 Hz, 1H), 3.97 (t, J = 10.5 Hz, 1H), 3.61-3.49 (m, 4H), 3.43-3.25 (m, 3H), 3.13 (d, J = 7.6 Hz, 1H), 2.98-2.67 (m, 5H), 2.63-2.48 (m, 5H), 2.37 (d, J = 13.5 Hz, 1H), 2.23-2.02 (m, 4H), 2.02-1.84 (m, 2H), 1.79 (dt, J = 13.4, 6.0 Hz, 1H), 1.63-1.51 (m, 3H), 1.41 (t, J = 6.9 Hz, 2H), 1.24-1.04 (m, 21H). |
| 8 | I-7 | [([4-[(1E)-1-[[(2S,11S)-2-[[(3S,4R)-1-carbamoyl-4-[[4-(3-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]propyl)phenyl]methoxy]pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl([(2,2-dimethylpropanoyl)oxy]methoxy)phosphoryl)oxy]methyl 2,2-dimethylpropanoate | 1465.6 | (400 MHz, $CDCl_3$) δ 9.00 (s, 1H), 7.63 (d, J = 8.2 Hz, 2H), 7.55 (d, J = 8.0 Hz, 2H), 7.38-7.23 (m, 5H), 7.16-7.00 (m, 6H), 6.92 (d, J = 9.2 Hz, 1H), 6.39 (s, 1H), 6.15 (s, 1H), 5.96 (s, 1H), 5.82-5.64 (m, 4H), 5.21 (d, J = 9.2 Hz, 2H), 4.70 (t, J = 8.0 Hz, 1H), 4.62 (d, J = 11.2 Hz, 2H), 4.59 (d, J = 5.8 Hz, 1H), 4.53 (d, J = 7.9 Hz, 2H), 4.37 (dd, J = 14.5, 6.8 Hz, 2H), 4.12 (d, J = 11.3 Hz, 1H), 3.94 (s, 2H), 3.62-3.50 (m, 3H), 3.36-3.20 (m, 4H), 3.11 (d, J = 7.3 Hz, 1H), 2.61-2.50 (m, 6H), 2.48 (s, 2H), 2.32 (s, 1H), 2.19-2.12 (m, 1H), 2.11-1.93 (m, 6H), 1.89 (s, 3H), 1.86 (d, J = 7.3 Hz, 1H), 1.25 (s, 18H), 1.24-1.05 (m, 3H), 0.96 (s, 9H). |
| 9 | I-8 | (2S,4R)-1-[(2S)-2-[5-[4-([[(2R,3S)-3-[[(25,11S)-11-amino-12-oxo-1-azatricyclo[6.4.1.0^[4,13]]trideca-4(13),5,7-trien-2-1]formamido]-5-carbamoylpentan-2-yl]oxy]methyl)phenyl]pentanamido]-3,3-dimethylbutanoyl]-4-hydroxy-N-[[4-(4-methyl-1,3-thiazol-5-yl)phenyl]methyl]pyrrolidine-2-carboxamide | 1480.3 | (400 MHz, $CD_3OD$) δ 8.95 (s, 1H), 7.99 (d, J = 9.4 Hz, 1H), 7.69 (d, J = 8.3 Hz, 2H), 7.63 (d, J = 8.2 Hz, 2H), 7.48 (d, J = 8.2 Hz, 2H),7.43 (d, J = 8.2 Hz, 2H), 7.24 (d, J = 7.9 Hz, 2H), 7.13-7.07 (m, 3H), 7.06 (dt, J = 14.7, 7.0 Hz, 2H), 6.40 (s, 1H), 5.75-5.53 (m, 4H), 5.16 (dd, J = 10.8, 3.3 Hz, 1H), 4.69-4.62 (m, 2H), 4.57 (t, J = 8.3 Hz, 2H), 4.54-4.45 (m, 3H), 4.37 (d, J = 7.6 Hz, 1H), 4.00 (s, 1H), 3.91 (d, J = 11.0 Hz, 1H), 3.81 (dd, J = 10.9, 3.8 Hz, 1H), 3.59-3.45 (m, 2H), 3.25-2.98 (m, 3H), 2.63 (s, 1H), 2.56 (d, J = 1.3 Hz, 2H), 2.49 (s, 3H), 2.33-2.20 (m, 7H), 2.13-1.99 (m, 2H), 1.65 (m, 6H), 1.23 (s, 18H), 1.20-06 (m, 3H), 1.04 (s, 9H). |
| 10 | I-9 | [([4-(1E)-1-[[(2S,11S)-2-[[(3S,4R)-1-carbamoyl-4-[[4-(2-[3-[1-(2,6-dioxopiperidin-3-yl)-3-methyl-2-oxo-1,3-benzodiazol-4-yl]propoxy]ethyl)phenyl]methoxy]pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl([(2,2-dimethylpropanoyl)oxy]methoxy)phosphoryl)oxy]methyl 2,2-dimethylpropanoate | 1310.9 | (400 MHz, $CDCl_3$) δ 8.95 (d, J = 7.6 Hz, 1H), 7.62 (d, J = 8.3 Hz, 2H), 7.59-7.51 (m, 2H), 7.28 (s, 2H), 7.20 (t, J = 7.9 Hz, 2H), 7.15-6.99 (m, 5H), 6.96 (td, J = 7.8, 3.0 Hz, 1H), 6.80 (dd, J = 14.0, 7.8 Hz, 1H), 6.69 (d, J = 7.8 Hz, 1H), 6.20 (s, 1H), 6.14 (s, 1H), 5.76 (dd, J = 12.5, 5.0 Hz, 2H), 5.68 (dd, J = 12.4, 5.0 Hz, 2H), 5.32-5.04 (m, 3H), 4.60 (d, J = 10.6 Hz, 2H), 4.40 (dd, J = 11.4, 5.0 Hz, 1H), 3.95 (s, 1H), 3.64-3.55 (m, 3H), 3.52-3.40 (m, 5H), 3.39-3.21 (m, 3H), 3.13 (d, J = 7.7 Hz, 1H), 3.02-2.66 (m, 7H), 2.58-2.49 (m, 3H), 2.39 (d, J = 13.8 Hz, 1H), 2.22-2.08 (m, 4H), 2.02-1.93 (m, 1H), 1.87 (q, J = 6.5 Hz, 2H), 1.79 (d, J = 11.8 Hz, 1H), 1.24-1.06 (m, 21H). |
| 12 | I-10 | [([4-[(1E)-1-[[(2S,11S)-2-[[(3S,4R)-1-carbamoyl-4-[[4-(3-[3-[1-(2,6-dioxopiperidin-3-yl)-3-methyl-2-oxo-1,3-benzodiazol-4-yl]propoxy]propyl)phenyl]methoxy]pentan-3-yl]carbamoyl]-12-oxo-1-azatricyclo[6.4.1.0^[4,13]]trideca-4(13),5,7-trien-11-yl]carbamoyl]prop-1-en-2- | 1324.9 | (400 MHz, $CDCl_3$) δ 7.62 (d, J = 8.2 Hz, 2H), 7.55 (d, J = 8.2 Hz, 2H), 7.28-7.22 (m, 2H), 7.15 (dd, J = 7.8, 5.7 Hz, 2H), 7.12-6.93 (m, 5H), 6.92-6.82 (m, 2H), 6.74-6.64 (m, 1H), 6.21-6.13 (m, 1H), 6.00 (d, J = 9.5 Hz, 1H), 5.76 (dd, J = 12.5, 5.0 Hz, 2H), 5.68 (dd, J = 12.4, 5.0 Hz, 2H), 5.28-5.04 (m, 3H), 4.68-4.55 (m, 2H), 4.43 (d, J = 11.6 Hz, 1H), 4.04-3.92 (m, 1H), 3.67 (d, J = 2.6 Hz, 3H), 3.63-3.55 (m, 2H), 3.51-3.27 (m, 7H), 3.12 (d, J = |

TABLE 73-continued

| Characterization Data for Exemplary STAT3 Degraders | | | | |
|---|---|---|---|---|
| EXAMPLE | I-# | Chemical Name | MS: $[(M + 1)]^+$ | $^1H$ NMR |
| | | yl]phenyl]difluoromethyl([(2,2-dimethylpropanoyl)oxy]methoxy)phosphoryl)oxy]methyl 2,2-dimethylpropanoate | | 17.6 Hz, 1H), 3.07-2.98 (m, 2H), 2.95-2.79 (m, 1H), 2.79-2.61 (m, 3H), 2.61-2.54 (m, 3H), 2.38 (d, J = 13.7 Hz, 1H), 2.27-2.00 (m, 5H), 2.01-1.73 (m, 6H), 1.27-1.03 (m, 21H). |
| 13 | I-11 | [([4-[(1E)-1-[[(2S,11S)-2-[[(3S,4R)-1-carbamoyl-4-[(4-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]phenyl)methoxy]pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl([(2,2-dimethylpropanoyl)oxy]methoxy)phosphoryl)oxy]methyl 2,2-dimethylpropanoate | 1423.9 | (400 MHz, $CDCl_3$) δ 8.77 (s, 1H), 7.73 (d, J = 7.9 Hz, 2H), 7.66-7.60 (m, 2H), 7.56 (d, J = 8.2 Hz, 2H), 7.39-7.11 (m, 6H), 7.04-6.93 (m, 4H), 6.85 (t, J = 9.5 Hz, 2H), 6.18 (s, 1H), 5.89 (s, 1H), 5.76 (dt, J = 12.4, 5.3 Hz, 2H), 5.67 (ddd, J = 12.4, 5.0, 3.4 Hz, 2H), 5.24-5.00 (m, 2H), 4.76 (d, J = 8.8 Hz, 1H), 4.72-4.50 (m, 5H), 4.50-4.31 (m, 2H), 4.10 (d, J = 11.3 Hz, 1H), 3.94 (d, J = 10.3 Hz, 1H), 3.69 (dd, J = 11.2, 3.7 Hz, 1H), 3.58 (dd, J = 6.5, 4.1 Hz, 1H), 3.45-3.20 (m, 3H), 3.16-3.01 (m, 2H), 2.63-2.41 (m, 7H), 2.42-2.28 (m, 2H), 2.18-1.94 (m, 4H), 1.94-1.67 (m, 2H), 1.24-1.04 (m, 21H), 1.02 (s, 9H). |
| 14 | I-12 | [([4-[(1E)-1-[[(2S,11S)-2-[[(3S,4R)-1-Carbamoyl-4-[[4-(2-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]ethyl)phenyl]methoxy]pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl([(2,2-dimethylpropanoyl)oxy]methoxy)phosphoryl)oxy]methyl 2,2-dimethylpropanoate | 1451.9 | (400 MHz, $CDCl_3$) δ 8.70 (s, 1H), 7.63 (d, J = 8.1 Hz, 2H), 7.54 (d, J = 8.1 Hz, 2H), 7.42-7.30 (m, 5H), 7.25 (s, 1H), 7.14-7.06 (m, 4H), 7.05 (d, J = 6.6 Hz, 1H), 6.89 (d, J = 14.1 Hz, 2H), 6.23 (d, J = 8.7 Hz, 1H), 6.09 (s, 1H), 5.88 (s, 1H), 5.76 (dt, J = 12.4, 5.3 Hz, 2H), 5.67 (dd, J = 12.4, 5.0 Hz, 2H), 5.18 (d, J = 8.3 Hz, 1H), 4.99 (s, 1H), 4.68 (t, J = 7.9 Hz, 1H), 4.60 (t, J = 10.4 Hz, 2H), 4.56-4.49 (m, 3H), 4.44-4.31 (m, 2H), 4.02 (d, J = 11.2 Hz, 1H), 3.96 (d, J = 11.2 Hz, 1H), 3.69-3.53 (m, 3H), 3.42-3.25 (m, 3H), 3.11 (d, J = 7.4 Hz, 1H), 2.89 (dt, J = 14.7, 7.4 Hz, 1H), 2.78 (dt, J = 14.1, 7.2 Hz, 1H), 2.56 (s, 3H), 2.52 (s, 3H), 2.49-2.40 (m, 2H), 2.39-2.31 (m, 1H), 2.19-1.98 (m, 5H), 1.84-1.62 (m, 3H), 1.31-1.16 (m, 21H), 0.89 (s, 9H). |
| 15 | I-13 | [([4-[(1E)-1-[[(2S,11S)-2-[[(3S,4R)-1-carbamoyl-4-([4-[2-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methoxy)ethyl]phenyl]methoxy)pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl([(2,2-dimethylpropanoyl)oxy]methoxy)phosphoryl)oxy]methyl 2,2-dimethylpropanoate | 1482.8 | (400 MHz, $CDCl_3$) δ 8.69 (s, 1H), 7.66 (t, J = 5.9 Hz, 1H), 7.64-7.57 (m, 2H), 7.53 (d, J = 8.2 Hz, 2H), 7.42-7.30 (m, 4H), 7.29 (t, J = 3.9 Hz, 2H), 7.22 (s, 2H), 7.15-6.98 (m, 4H), 6.93 (d, J = 6.1 Hz, 1H), 6.86 (d, J = 9.2 Hz, 1H), 6.10 (s, 2H), 5.76 (dt, J = 12.4, 5.1 Hz, 2H), 5.68 (dd, J = 12.5, 5.1 Hz, 2H), 5.21 (dd, J = 8.0, 4.7 Hz, 2H), 4.69 (t, J = 8.1 Hz, 1H), 4.60 (d, J = 11.3 Hz, 2H), 4.56-4.47 (m, 3H), 4.45-4.30 (m, 2H), 4.05 (d, J = 11.3 Hz, 1H), 3.90 (d, J = 15.1 Hz, 2H), 3.77 (d, J = 7.2 Hz, 1H), 3.73-3.51 (m, 4H), 3.34 (ddd, J = 15.8, 11.8, 6.2 Hz, 1H), 3.27-3.16 (m, 2H), 3.11 (d, J = 8.6 Hz, 1H), 2.86 (t, J = 6.5 Hz, 2H), 2.66-2.53 (m, 3H), 2.51 (s, 3H), 2.44-2.29 (m, 2H), 2.20-2.02 (m, 5H), 1.92 (dd, J = 7.3, 4.3 Hz, 1H), 1.80-1.66 (m, 1H), 1.24 (s, 18H), 1.19-1.06 (m, 3H), 0.97 (s, 9H). |
| 16 | I-14 | [4-[(1E)-1-[[(2S,11S)-2-[[(3S,4R)-1-carbamoyl-4-([4-[3-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methoxy)propyl]phenyl]methoxy)pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethylphosphonic acid | 1267.8 | (400 MHz, $CD_3OD$) δ 9.02 (s, 1H), 7.64-7.54 (m, 4H), 7.52-7.45 (m, 2H), 7.44-7.37 (m, 2H), 7.22 (d, J = 7.9 Hz, 2H), 7.22-7.13 (m, 2H), 7.12 (d, J = 7.3 Hz, 1H), 7.10-6.99 (m, 2H), 6.38 (d, J = 1.6 Hz, 1H), 5.16 (dd, J = 10.8, 3.3 Hz, 1H), 4.73 (s, 1H), 4.68-4.51 (m, 3H), 4.48 (d, J = 3.6 Hz, 2H), 4.35 (d, J = 15.5 Hz, 1H), 4.06-3.92 (m, 3H), 3.90 (d, J = 11.1 Hz, 2H), 3.82 (m, 4H), 3.60-3.43 (m, 5H), 3.27-3.11 (m, 1H), 2.75 (t, J = 7.6 Hz, 2H), 2.57-2.48 (m, 1H), 2.45 (s, 3H), 2.33-2.27 (m, 1H), 2.26 (s, 3H), 2.23 (s, 1H), 2.11 (ddd, J = 13.4, 9.3, 4.3 Hz, 1H), 1.95 (s, 2H), 2.02-1.89 (m, 1H), 1.72-1.61 (m, 1H), 1.19-1.10 (m, 3H), 1.06 (s, 9H). |
| 17 | 115 | [([4-[(1E)-1-[[(2S,11S)-2-[[(3S,4R)-1-carbamoyl-4-[(4-[1-[2-([[(2S,4R)-1-[(2S)-2-[(1-fluorocyclopropyl)formamido]-3,3-dimethylbutanoyl]-4- | 1760.4 | (400 MHz, $CDCl_3$) δ 8.71 (s, 1H), 7.63 (d, J = 8.1 Hz, 2H), 7.55 (d, J = 8.1 Hz, 2H), 7.35 (d, J = 7.8 Hz, 2H), 7.26 (d, J = 7.7 Hz, 2H), 7.16 (d, J = 7.8 Hz, 2H), 7.12-6.92 (m, 6H), 6.91 (d, J = 1.6 Hz, 1H), 6.81 (d, J = 9.5 Hz, |

TABLE 73-continued

| Characterization Data for Exemplary STAT3 Degraders | | | | |
|---|---|---|---|---|
| EXAMPLE | I-# | Chemical Name | MS: $[(M + 1)]^+$ | $^1H$ NMR |
| | | hydroxypyrrolidin-2-yl]formamido]methyl)-5-(4-methyl-1,3-thiazol-5-yl)phenoxy]-3,6,9,12,15-pentaoxaoctadecan-18-yl]phenyl)methoxy]pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl([(2,2-dimethylpropanoyl)oxy]methoxy)phosphoryl)oxy]methyl 2,2-dimethylpropanoate | | 1H), 6.14 (s, 1H), 5.95 (s, 1H), 5.76 (dd, J = 12.5, 5.0 Hz, 2H), 5.68 (dd, J = 12.4, 5.0 Hz, 2H), 5.18 (dd, J = 8.7, 3.9 Hz, 1H), 4.97 (s, 1H), 4.71-4.54 (m, 4H), 4.54-4.38 (m, 4H), 4.20 (ddt, J = 15.9, 10.0, 5.4 Hz, 2H), 4.06-3.84 (m, 4H), 3.83-3.71 (m, 2H), 3.69-3.66 (m, 3H), 3.65-3.58 (m, 10H), 3.57-3.51 (m, 3H), 3.49-3.26 (m, 5H), 3.13 (d, J = 7.5 Hz, 1H), 2.64 (t, J = 7.6 Hz, 2H), 2.62-2.56 (m, 3H), 2.54 (s, 3H), 2.37 (td, J = 10.6, 8.3, 4.7 Hz, 2H), 2.19-2.02 (m, 4H), 1.86-1.72 (m, 4H), 1.42-1.27 (m, 5H), 1.24-1.06 (m, 21H), 0.98 (s, 9H). |
| 18 | I-16 | [([4-[(1E)-1-[[(2S,11S)-2-[[(3S,4R)-1-carbamoyl-4-[(4-[1-[2-([[(2S,4R)-1-[(2S)-2-[(1-fluorocyclopropyl)formamido]-3,3-dimethylbutanoyl]-4-hydroxypyrrolidin-2-yl]formamido]methyl)-5-(4-methyl-1,3-thiazol-5-yl)phenoxy]-3,6,9,12-tetraoxapentadecan-15-yl]phenyl)methoxy]pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl([(2,2-dimethylpropanoyl)oxy]methoxy)phosphoryl)oxy]methyl 2,2-dimethylpropanoate | 1716.5 | (400 MHz, $CDCl_3$) δ 8.70 (s, 1H), 7.67-7.59 (m, 2H), 7.55 (d, J = 8.2 Hz, 2H), 7.35 (d, J = 7.3 Hz, 2H), 7.26 (d, J = 7.9 Hz, 2H), 7.15 (d, J = 7.8 Hz, 2H), 7.13-7.01 (m, 4H), 7.01-6.89 (m, 3H), 6.81 (d, J = 9.4 Hz, 1H), 6.13 (d, J = 1.7 Hz, 1H), 5.95 (s, 1H), 5.76 (ddd, J = 12.5, 5.0, 0.9 Hz, 2H), 5.68 (dd, J = 12.4, 5.0 Hz, 2H), 5.18 (dd, J = 8.6, 4.0 Hz, 1H), 4.96 (s, 1H), 4.67 (t, J = 7.9 Hz, 1H), 4.64-4.54 (m, 3H), 4.53-4.39 (m, 4H), 4.20 (tdd, J = 10.1, 8.0, 4.3 Hz, 2H), 4.05-3.85 (m, 4H), 3.83-3.71 (m, 2H), 3.75-3.59 (m, 9H), 3.62-3.53 (m, 3H), 3.44 (t, J = 6.4 Hz, 2H), 3.41-3.28 (m, 3H), 3.19-3.07 (m, 1H), 2.63 (t, J = 7.6 Hz, 2H), 2.62-2.55 (m, 3H), 2.54 (s, 3H), 2.37 (ddd, J = 12.8, 8.0, 4.5 Hz, 2H), 2.19-1.87 (m, 6H), 1.90-1.74 (m, 3H), 1.43-1.26 (m, 4H), 1.24-1.06 (m, 21H), 0.98 (s, 9H). |
| 19 | I-17 | [([4-[(1E)-1-[[(2S,11S)-2-[[(3S,4R)-1-carbamoyl-4-[(4-[3-[2-(2-[2-[2-([[(2S,4R)-1-[(2S)-2-[(1-fluorocyclopropyl)formamido]-3,3-dimethylbutanoyl]-4-hydroxypyrrolidin-2-yl]formamido]methyl)-5-(4-methyl-1,3-thiazol-5-yl)phenoxy]ethoxy]ethoxy)ethoxy]propyl]phenyl)methoxy]pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl([(2,2-dimethylpropanoyl)oxy]methoxy)phosphoryl)oxy]methyl 2,2-dimethylpropanoate | 1672.7 | (400 MHz, $CDCl_3$) δ 8.69 (s, 1H), 7.62 (d, J = 8.1 Hz, 2H), 7.55 (d, J = 8.2 Hz, 2H), 7.41-7.31 (m, 2H), 7.25 (d, J = 7.7 Hz, 2H), 7.15 (d, J = 7.8 Hz, 2H), 7.12-7.00 (m, 4H), 7.01-6.93 (m, 2H), 6.89 (d, J = 1.7 Hz, 1H), 6.83 (d, J = 9.4 Hz, 1H), 6.14 (s, 1H), 5.98 (s, 1H), 5.72-5.58 (m, 4H), 5.17 (dd, J = 8.2, 4.4 Hz, 1H), 5.05 (s, 1H), 4.66 (t, J = 7.9 Hz, 1H), 4.65-4.53 (m, 3H), 4.54-4.38 (m, 4H), 4.19 (tq, J = 10.5, 5.3 Hz, 2H), 3.97-3.87 (m, 4H), 3.85-3.51 (m, 10H), 3.44 (t, J = 6.4 Hz, 2H), 3.34-3.22 (m, 3H), 3.12 (d, J = 7.6 Hz, 1H), 2.70-2.48 (m, 8H), 2.44-2.26 (m, 3H), 2.13-2.02 (m, 4H), 1.99-1.72 (m, 4H), 1.52-1.39 (m, 4H), 1.24-1.05 (m, 21H), 0.97 (s, 9H). |
| 20 | I-18 | [([4-[(1E)-1-[[(2S,11S)-2-[[(3S,4R)-1-carbamoyl-4-([4-[3-(2-[2-[2-([[(2S,4R)-1-[(2S)-2-[(1-fluorocyclopropyl)formamido]-3,3-dimethylbutanoyl]-4-hydroxypyrrolidin-2-yl]formamido]methyl)-5-(4-methyl-1,3-thiazol-5-yl)phenoxy]ethoxy]ethoxy)propyl]phenyl]methoxy)pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl([(2,2-dimethylpropanoyl)oxy]methoxy)phosphoryl)oxy]methyl 2,2-dimethylpropanoate | 1629 | (400 MHz, $CDCl_3$) δ 7.62 (d, J = 8.2 Hz, 2H), 7.55 (d, J = 8.2 Hz, 2H), 7.34 (td, J = 6.8, 5.8, 2.4 Hz, 2H), 7.26 (d, J = 7.6 Hz, 2H), 7.15 (d, J = 7.8 Hz, 2H), 7.12-6.94 (m, 6H), 6.91 (d, J = 1.6 Hz, 1H), 6.85 (d, J = 9.4 Hz, 1H), 6.19-6.10 (m, 1H), 6.00 (s, 1H), 5.76 (ddd, J = 12.5, 5.0, 1.4 Hz, 2H), 5.68 (dd, J = 12.4, 5.0 Hz, 2H), 5.17 (dd, J = 8.2, 4.5 Hz, 1H), 5.08 (s, 1H), 4.73-4.54 (m, 5H), 4.55-4.38 (m, 4H), 4.30-4.10 (m, 2H), 4.04-3.88 (m, 5H), 3.83-3.55 (m, 4H), 3.46 (t, J = 6.5 Hz, 2H), 3.41-3.26 (m, 3H), 3.12 (d, J = 7.8 Hz, 1H), 2.70-2.59 (m, 2H), 2.60-2.55 (m, 3H), 2.53 (s, 3H), 2.45-2.27 (m, 3H), 2.20-1.99 (m, 5H), 2.00-1.72 (m, 4H), 1.42-1.25 (m, 4H), 1.24-1.03 (m, 21H), 0.97 (s, 9H). |
| 21 | I-19 | [([4-[(1E)-1-[[(2S,11S)-2-[[(3S,4R)-1-Carbamoyl-4-[[4-(3-[2-[2-([[(2S,4R)-1-[(2S)-2-[(1-fluorocyclopropyl)formamido]-3,3-dimethylbutanoyl]-4-hydroxypyrrolidin-2- | 1585.2 | (400 MHz, $CDCl_3$) δ 8.70 (s, 1H), 7.62 (d, J = 8.1 Hz, 2H), 7.55 (d, J = 8.1 Hz, 2H), 7.35 (t, J = 6.4 Hz, 2H), 7.24 (d, J = 7.7 Hz, 2H), 7.14 (d, J = 7.7 Hz, 2H), 7.11-7.01 (m, 5H), 6.98 (d, J = 7.7 Hz, 1H), 6.92 (s, 1H), 6.87 (d, J = 9.5 Hz, 1H), 6.16 (s, 1H), 6.03 (s, 1H), |

TABLE 73-continued

Characterization Data for Exemplary STAT3 Degraders

| EXAMPLE | I-# | Chemical Name | MS: [(M + 1)]$^+$ | $^1$H NMR |
|---|---|---|---|---|
| | | yl]formamido]methyl)-5-(4-methyl-1,3-thiazol-5-yl)phenoxy]ethoxy]propyl)phenyl]methoxy]pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl([(2,2-dimethylpropanoyl)oxy]methoxy)phosphoryl)oxy]methyl 2,2-dimethylpropanoate | | 5.76 (dd, J = 12.5, 5.0 Hz, 2H), 5.68 (dd, J = 12.4, 5.1 Hz, 2H), 5.25-5.03 (m, 2H), 4.72-4.60 (m, 4H), 4.53-4.37 (m, 4H), 4.20 (h, J = 6.4, 5.9 Hz, 2H), 4.00 (d, J = 10.4 Hz, 1H), 3.94-3.78 (m, 3H), 3.70-3.50 (m, 4H), 3.32-3.20 (m, 3H), 3.18-3.06 (m, 1H), 2.67 (t, J = 7.5 Hz, 2H), 2.55 (d, J = 12.6 Hz, 6H), 2.43-2.25 (m, 3H), 2.19-1.98 (m, 5H), 1.95-1.86 (m, 3H), 1.82 (d, J = 10.4 Hz, 1H), 1.39-1.27 (m, 3H), 1.24-1.03 (m, 21H), 0.95 (s, 9H). |
| 22 | I-20 | [([4-[(1E)-1-[[(2S,11S)-2-[[(3S,4R)-1-carbamoyl-4-[(4-[3-[2-([[(2S,4R)-1-[(2S)-2-[(1-fluorocyclopropyl)formamido]-3,3-dimethylbutanoyl]-4-hydroxypyrrolidin-2-yl]formamido]methyl)-5-(4-methyl-1,3-thiazol-5-yl)phenoxy]propyl]phenyl)methoxy]pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl([(2,2-dimethylpropanoyl)oxy]methoxy)phosphoryl)oxy]methyl 2,2-dimethylpropanoate | 1540.9 | (400 MHz, $CDCl_3$) δ 8.69 (s, 1H), 7.66-7.58 (m, 2H), 7.54 (d, J = 8.2 Hz, 2H), 7.36-7.29 (m, 2H), 7.28 (s, 1H), 7.25-7.13 (m, 3H), 7.12-6.99 (m, 5H), 6.96 (dd, J = 1.1, 1.6 Hz, 1H), 6.90-6.80 (m, 2H), 6.15 (d, J = 1.5 Hz, 1H), 5.96 (s, 1H), 5.80-5.71 (m, 2H), 5.67 (ddd, J = 12.4, 5.0, 1.6 Hz, 2H), 5.19 (dd, J = 8.8, 3.8 Hz, 1H), 5.04 (s, 1H), 4.72 (t, J = 7.7 Hz, 1H), 4.58 (dd, J = 16.1, 10.3 Hz, 3H), 4.53-4.34 (m, 4H), 4.08-3.89 (m, 4H), 3.62 (dt, J = 10.3, 5.1 Hz, 2H), 3.42-3.23 (m, 4H), 3.17-3.04 (m, 1H), 2.80 (t, J = 7.4 Hz, 2H), 2.63-2.54 (m, 3H), 2.52 (s, 3H), 2.47 (dd, J = 7.5, 5.0 Hz, 1H), 2.37 (d, J = 12.9 Hz, 1H), 2.20-1.89 (m, 8H), 1.80 (tt, J = 13.4, 6.4 Hz, 1H), 1.40-1.28 (m, 3H), 1.24-1.03 (m, 21H), 0.94 (s, 9H). |
| 23 | I-21 | [([4-[(1E)-1-[[(2S,11S)-2-[[(3S,4R)-1-carbamoyl-4-([4-[4-([[(2S)-1-[(2S,4S)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methoxy)butyl]phenyl]methoxy)pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl([(2,2-dimethylpropanoyl)oxy]methoxy)phosphoryl)oxy]methyl 2,2-dimethylpropanoate | 1508.4 | (400 MHz, $CDCl_3$) δ 8.70 (s, 1H), 7.75 (t, J = 6.2 Hz, 1H), 7.63 (d, J = 8.1 Hz, 2H), 7.54 (d, J = 8.2 Hz, 2H), 7.45-7.32 (m, 4H), 7.26 (d, J = 7.9 Hz, 2H), 7.20-7.00 (m, 6H), 6.86 (dd, J = 15.9, 7.7 Hz, 2H), 6.11 (d, J = 1.6 Hz, 1H), 5.76 (ddd, J = 12.4, 5.0, 3.2 Hz, 2H), 5.68 (ddd, J = 12.3, 5.0, 1.5 Hz, 2H), 5.21 (dd, J = 9.7, 2.8 Hz, 1H), 5.06 (s, 1H), 4.73 (d, J = 9.0 Hz, 1H), 4.68-4.53 (m, 4H), 4.48 (s, 1H), 4.44-4.29 (m, 2H), 4.03-3.81 (m, 5H), 3.59 (dt, J = 10.7, 6.1 Hz, 1H), 3.50 (t, J = 6.1 Hz, 2H), 3.44-3.26 (m, 3H), 3.13 (d, J = 17.7 Hz, 1H), 2.66-2.49 (m, 8H), 2.43-2.30 (m, 2H), 2.25-2.13 (m, 1H), 2.14-1.99 (m, 3H), 2.02-1.86 (m, 2H), 1.80 (dq, J = 13.9, 6.8 Hz, 1H), 1.73-1.56 (m, 5H), 1.24-1.01 (m, 21H), 0.96 (s, 9H). |
| 24 | 1-22 | [([4-[(1E)-1-[[(2S,11S)-2-[[(3S,4R)-1-carbamoyl-4-([4-[3-([[(2S)-1-[(2S,4S)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methoxy)propyl]phenyl]methoxy)pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl([(2,2-dimethylpropanoyl)oxy]methoxy)phosphoryl)oxy]methyl 2,2-dimethylpropanoate | [(M/2 + 1)]$^+$ = 748.9 | (400 MHz, $CDCl_3$) δ 8.79 (s, 1H), 7.74 (t, J = 5.9 Hz, 1H), 7.62 (d, J = 8.2 Hz, 2H), 7.54 (d, J = 8.2 Hz, 2H), 7.36-7.22 (m, 4H), 7.15-7.08 (m, 3H), 7.07-7.01 (m, 3H), 6.97 (d, J = 6.1 Hz, 1H), 6.87 (d, J = 9.4 Hz, 1H), 6.13 (s, 1H), 5.86 (s, 1H), 5.76 (ddd, J = 12.4, 5.0, 3.4 Hz, 2H), 5.68 (ddd, J = 12.4, 5.0, 2.1 Hz, 2H), 5.20 (dd, J = 9.9, 2.7 Hz, 1H), 5.11 (s, 1H), 4.73 (d, J = 9.0 Hz, 1H), 4.61-4.55 (m, 4H), 4.52-4.38 (m, 2H), 4.31 (dd, J = 15.0, 5.0 Hz, 1H), 4.03-3.81 (m, 6H), 3.59 (dd, J = 6.4, 4.5 Hz, 1H), 3.55-3.48 (m, 3H), 3.46-3.26 (m, 3H), 3.12 (d, J = 7.4 Hz, 1H), 2.65 (t, J = 7.7 Hz, 2H), 2.59-2.53 (m, 3H), 2.52 (s, 3H), 2.33 (d, J = 14.5 Hz, 2H), 2.24-2.04 (m, 3H), 2.01 (d, J = 7.9 Hz, 1H), 1.90-1.81 (m, 4H), 1.79 (dq, J = 13.6, 7.0 Hz, 1H), 1.24-1.02 (m, 21H), 0.97 (s, 9H). |
| 25 | I-23 | [([4-[(1E)-1-[[(2S,11S)-2-[[(3S,4R)-1-carbamoyl-4-[(4-[5-[2-([[(2S,4R)-1-[(2S)-2-[(1-fluorocyclopropyl)formamido]-3,3-dimethylbutanoyl]-4-hydroxypyrrolidin-2-yl]formamido]methyl)-5-(4-methyl-1,3-thiazol-5-yl)phenoxy]pentyl]phenyl)methoxy]pentan-3-yl]carbamoyl]-12- | 1568.9 | (400 MHz, $CDCl_3$) δ 8.70 (s, 1H), 7.62 (d, J = 8.1 Hz, 2H), 7.54 (d, J = 8.2 Hz, 2H), 7.32 (dd, J = 11.9, 6.9 Hz, 2H), 7.26 (s, 1H), 7.16 (d, J = 7.8 Hz, 2H), 7.06 (m, 4H), 6.99-6.91 (m, 2H), 6.87-6.80 (m, 2H), 6.14 (d, J = 1.6 Hz, 1H), 5.93 (s, 1H), 5.76 (ddd, J = 12.5, 5.0, 1.6 Hz, 2H), 5.68 (dd, J = 12.3, 5.0 Hz, 2H), 5.18 (dd, J = 8.7, 3.9 Hz, 1H), 5.00 (s, 1H), 4.73 (t, J = 7.7 Hz, 1H), 4.64-4.33 (m, 7H), 3.98-3.76 (m, 4H), 3.69-3.55 (m, 2H), |

TABLE 73-continued

Characterization Data for Exemplary STAT3 Degraders

| EXAMPLE | I-# | Chemical Name | MS: $[(M + 1)]^+$ | $^1H$ NMR |
|---|---|---|---|---|
| | | oxo-1-azatricyclo[6.4.1.0^[4,13]]trideca-4(13),5,7-trien-11-yl]carbamoyl]prop-1-en-2-yl]phenyl]difluoromethyl([(2,2-dimethylpropanoyl)oxy]methoxy)phosphoryl)oxy]methyl 2,2-dimethylpropanoate. | | 3.41-3.26 (m, 3H), 3.12 (d, J = 7.6 Hz, 1H), 2.62 (t, J = 7.3 Hz, 2H), 2.60-2.54 (m, 3H), 2.53-2.44 (m, 4H), 2.42-2.31 (m, 1H), 2.19-2.00 (m, 4H), 1.95 (dd, J = 8.9, 5.4 Hz, 1H), 1.85-1.76 (m, 3H), 1.70 (p, J = 7.4 Hz, 2H), 1.57-1.46 (m, 3H), 1.40-1.27 (m, 4H), 1.24-1.15 (m, 21H), 1.09 (dd, J = 15.4, 4.3 Hz, 1H), 0.96 (s, 9H). |
| 26 | I-24 | [([4-[(1E)-1-[[(2S,11S)-2-[[(3S,4R)-1-carbamoyl-4-([4-[3-(2-[3-[1-(2,6-dioxopiperidin-3-yl)-3-methyl-2-oxo-1,3-benzodiazol-4-yl]propoxy]ethoxy)propyl]phenyl]methoxy)pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl([(2,2-dimethylpropanoyl)oxy]methoxy)phosphoryl)oxy]methyl 2,2-dimethylpropanoate | 1368.8 | (400 MHz, $CDCl_3$) δ 9.14 (d, J = 7.3 Hz, 1H), 7.68-7.51 (m, 4H), 7.28-7.19 (m, 2H), 7.19-6.80 (m, 9H), 6.74-6.65 (m, 1H), 6.19 (d, J = 8.8 Hz, 1H), 6.01 (d, J = 8.0 Hz, 1H), 5.72-5.51 (m, 4H), 5.35-5.03 (m, 3H), 4.71-4.49 (m, 2H), 4.38 (dd, J = 11.8, 4.0 Hz, 1H), 3.95 (s, 1H), 3.72-3.43 (m, 12H), 3.41-3.26 (m, 1H), 3.22-2.97 (m, 4H), 2.94-2.61 (m, 5H), 2.58-2.46 (m, 3H), 2.38 (d, J = 13.4 Hz, 2H), 2.14-2.03 (m, 4H), 2.01-1.73 (m, 6H), 1.24 (s, 18H), 1.18 (s, 3H). |
| 27 | I-25 | [([4-[(1E)-1-[[(2S,11S)-2-[[(3S,4R)-1-carbamoyl-4-[(4-[3-[(6-[3-[3-methyl-1-(1-methyl-2,6-dioxopiperidin-3-yl)-2-oxo-1,3-benzodiazol-5-yl]propoxy]hexyl)oxy]propyl]phenyl)methoxy]pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl([(2,2-dimethylpropanoyl)oxy]methoxy)phosphoryl)oxy]methyl 2,2-dimethylpropanoate | 1438.2 | (400 MHz, $CDCl_3$) δ 7.63 (d, J = 8.1 Hz, 2H), 7.55 (d, J = 8.2 Hz, 2H), 7.27-7.01 (m, 6H), 6.95-6.84 (m, 3H), 6.75 (dd, J = 42.7, 8.7 Hz, 2H), 6.12 (d, J = 1.6 Hz, 1H), 5.93 (s, 1H), 5.76 (dd, J = 12.5, 5.0 Hz, 2H), 5.68 (dd, J = 12.4, 5.0 Hz, 2H), 5.18 (dt, J = 8.6, 4.6 Hz, 2H), 4.93 (s, 1H), 4.60 (d, J = 11.5 Hz, 2H), 4.43 (d, J = 11.6 Hz, 1H), 4.04-3.91 (m, 1H), 3.61 (dd, J = 6.5, 4.0 Hz, 1H), 3.46-3.32 (m, 13H), 3.25 (s, 3H), 3.18-2.97 (m, 2H), 2.90-2.59 (m, 6H), 2.57-2.45 (m, 3H), 2.42-1.74 (m, 12H), 1.68-1.54 (m, 4H), 1.41-1.27 (m, 4H), 1.24-1.03 (m, 22H). |
| 28 | I-26 | [([4-[(1E)-1-[[(2S,11S)-2-[[(3S,4R)-1-carbamoyl-4-[(4-[4-[2-([[(2S,4R)-1-[(2S)-2-[(1-fluorocyclopropyl)formamido]-3,3-dimethylbutanoyl]-4-hydroxypyrrolidin-2-yl]formamido]methyl)-5-(4-methyl-1,3-thiazol-5-yl)phenoxy]butyl]phenyl)methoxy]pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl([(2,2-dimethylpropanoyl)oxy]methoxy)phosphoryl)oxy]methyl 2,2-dimethylpropanoate | $[(M + 23)]^+$ = 1576.3 | (400 MHz, $CDCl_3$) δ 8.69 (s, 1H), 7.77-7.42 (m, 4H), 7.45-6.69 (m, 12H), 6.09 (d, J = 6.0 Hz, 2H), 5.71-5.58 (m, 4H), 5.16 (s, 2H), 4.75-4.24 (m, 8H), 3.93-3.78 (m, 4H), 3.70-3.01 (m, 7H), 2.83-2.44 (m, 8H), 2.43-2.24 (m, 3H), 2.24-2.01 (m, 4H), 2.00-1.89 (m, 3H), 1.23-1.13 (m, 28H), 0.91-0.83 (m, 10H). |
| 29 | I-27 | [([4-[(1E)-1-[[(2S,11S)-2-[[(3S,4R)-1-Carbamoyl-4-[[4-(1-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]-2,5,8,11-tetraoxatridecan-13-yl)phenyl]methoxy]pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl([(2,2-dimethylpropanoyl)oxy]methoxy)phosphoryl)oxy]methyl 2,2-dimethylpropanoate | 1614.9 | (400 MHz, $CDCl_3$) δ 8.69 (s, 1H), 7.63 (d, J = 8.2 Hz, 2H), 7.55 (d, J = 8.2 Hz, 2H), 7.45 (d, J = 6.3 Hz, 1H), 7.42-7.30 (m, 4H), 7.28-7.20 (m, 3H), 7.19 (d, J = 7.7 Hz, 2H), 7.16-7.06 (m, 3H), 7.02-6.97 (m, 1H), 6.91 (d, J = 9.4 Hz, 1H), 6.15 (s, 1H), 6.08 (s, 1H), 5.76 (dd, J = 12.5, 5.0 Hz, 2H), 5.68 (dd, J = 12.4, 5.0 Hz, 2H), 5.23-5.12 (m, 2H), 4.71 (t, J = 8.0 Hz, 1H), 4.65-4.55 (m, 2H), 4.52-4.45 (m, 3H), 4.44-4.31 (m, 2H), 4.10-4.01 (m, 1H), 3.98-3.88 (m, 3H), 3.67-3.58 (m, 15H), 3.33-3.22 (m, 3H), 3.12 (d, J = 7.1 Hz, 1H), 2.85 (t, J = 7.0 Hz, 2H), 2.57 (s, 3H), 2.55-2.46 (m, 4H), 2.37(d, J = 13.6 Hz, 1H), 2.18-2.03 (m, 4H), 1.93 (s, 1H), 1.78 (d, J = 10.6 Hz, 1H), 1.24-1.05 (m, 23H), 0.97 (s, 9H). |
| 30 | I-28 | [([4-[(1E)-1-[[(2S,11S)-2-[[(3S,4R)-1-carbamoyl-4-[[4-(6- | 1508.0 | (400 MHz, $CDCl_3$) δ 8.69 (s, 1H), 7.72-7.47 (m, 4H), 7.43-7.30 (m, 5H), 7.27 (d, J = 14.7 |

TABLE 73-continued

Characterization Data for Exemplary STAT3 Degraders

| EXAMPLE | I-# | Chemical Name | MS: $[(M + 1)]^+$ | $^1H$ NMR |
|---|---|---|---|---|
| | | [[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]hexyl)phenyl]methoxy]pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl([(2,2-dimethylpropanoyl)oxy]methoxy)phosphoryl)oxy]methyl 2,2-dimethylpropanoate | | Hz, 2H), 7.18-7.02 (m, 5H), 6.97 (d, J = 6.0 Hz, 1H), 6.87 (d, J = 9.4 Hz, 1H), 6.33-5.93 (m, 3H), 5.72-5.59 (m, 4H), 5.26-5.05 (m, 2H), 4.82-4.26 (m, 8H), 4.14-3.89 (m, 2H), 3.73-3.44 (m, 3H), 3.34 (t, J = 11.2 Hz, 3H), 3.11 (d, J = 7.4 Hz, 1H), 2.67-2.44 (m, 9H), 2.34 (s, 1H), 2.25-1.68 (m, 10H), 1.24-1.03 (m, 27H), 0.94 (s, 9H). |
| 31 | I-29 | [({4-(1E)-1-[[(2S,11S)-2-[[(3S,4R)-1-carbamoyl-4-([4-[3-([5-[1-(2,6-dioxopiperidin-3-yl)-3-methyl-2-oxo-1,3-benzodiazol-4-yl]pentyl]oxy)propyl]phenyl]methoxy)pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl([(2,2-dimethylpropanoyl)oxy]methoxy)phosphoryl)oxy]methyl 2,2-dimethylpropanoate | 1352.8 | (400 MHz, $CDCl_3$) δ 8.87 (d, J = 7.1 Hz, 1H), 7.62 (d, J = 8.3 Hz, 2H), 7.56 (d, J = 8.2 Hz, 2H), 7.26 (t, J = 7.4 Hz, 2H), 7.18-7.01 (m, 5H), 7.01-6.92 (m, 2H), 6.92-6.80 (m, 2H), 6.68 (d, J = 7.7 Hz, 1H), 6.16 (d, J = 10.4 Hz, 1H), 5.94 (s, 1H), 5.76 (dd, J = 12.5, 5.0 Hz, 2H), 5.68 (dd, J = 12.4, 5.0 Hz, 2H), 5.19-5.13 (m, 2H), 5.05 (d, J = 8.3 Hz, 1H), 4.59 (dd, J = 11.5, 8.4 Hz, 2H), 4.43 (dd, J = 11.9, 2.0 Hz, 1H), 3.98 (s, 1H), 3.70-3.54 (m, 4H), 3.33 (d, J = 6.2 Hz, 1H), 3.25 (d, J = 8.3 Hz, 1H), 3.13 (d, J = 7.5 Hz, 1H), 3.08-2.81 (m, 4H), 2.79-2.68 (m, 1H), 2.67-2.60 (m, 2H), 2.58-2.48 (m, 3H), 2.37 (s, 1H), 2.23-2.02 (m, 4H), 2.02-1.76 (m, 5H), 1.66-1.54 (m, 4H), 1.52 (q, J = 7.7 Hz, 3H), 1.34 (t, J = 7.2 Hz, 2H), 1.24 (s, 18H), 1.21-1.12 (m, 4H). |
| 32 | I-30 | [({4-[(1E)-1-[[(2S,11S)-2-[[(3S,4R)-1-carbamoyl-4-[[4-(2-[2-[2-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methoxy)ethoxy]ethoxy]ethyl)phenyl]methoxy]pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl([(2,2-dimethylpropanoyl)oxy]methoxy)phosphoryl)oxy]methyl 2,2-dimethylpropanoate | 1570.5 | (400 MHz, $CDCl_3$) δ 8.68 (s, 1H), 7.61 (d, J = 8.2 Hz, 2H), 7.55 (s, 2H), 7.49 (t, J = 5.8 Hz, 1H), 7.46-7.34 (m, 4H), 7.31-7.22 (m, 3H), 7.18 (d, J = 7.7 Hz, 2H), 7.14-7.03 (m, 4H), 6.95 (d, J = 9.4 Hz, 1H), 6.15 (s, 2H), 5.75 (ddd, J = 12.5, 5.0, 1.4 Hz, 2H), 5.67 (dd, J = 12.4, 5.0 Hz, 2H), 5.29 (s, 1H), 5.18 (dd, J = 8.8, 4.1 Hz, 1H), 4.69 (t, J = 7.8 Hz, 1H), 4.65-4.45 (m, 5H), 4.45-4.27 (m, 2H), 4.18-3.88 (m, 4H), 3.71 (d, J = 1.2 Hz, 1H), 3.67-3.51 (m, 8H), 3.41-3.23 (m, 3H), 3.10 (d, J = 7.4 Hz, 1H), 2.83 (t, J = 6.8 Hz, 2H), 2.66-2.57 (m, 3H), 2.56-2.50 (m, 3H), 2.49-2.38 (m, 1H), 2.39-2.29 (m, 1H), 2.14-2.04 (m, 4H), 1.91 (d, J = 8.2 Hz, 1H), 1.74 (q, J = 8.6, 6.5 Hz, 1H), 1.23 (s, 18H), 1.23-1.05 (m, 7H), 0.96 (s, 9H). |
| 33 | I-31 | [({4-[(1E)-1-[[(2S,11S)-2-[[(3S,4R)-1-carbamoyl-4-[(4-[2-[2-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methoxy)ethoxy]ethyl]phenyl)methoxy]pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl([(2,2-dimethylpropanoyl)oxy]methoxy)phosphoryl)oxy]methyl 2,2-dimethylpropanoate | 1526.5 | (400 MHz, $CDCl_3$) δ 8.68 (s, 1H), 7.68-7.44 (m, 5H), 7.32-7.16 (m, 6H), 7.13-6.90 (m, 5H), 6.14 (d, J = 14.2 Hz, 2H), 5.83-5.60 (m, 4H), 5.18 (d, J = 8.3 Hz, 2H), 4.79-4.27 (m, 8H), 4.11-3.49 (m, 13H), 3.43-3.03 (m, 4H), 2.88 (d, J = 7.4 Hz, 2H), 2.66-2.51 (m, 7H), 2.39-1.67 (m, 9H), 1.24-1.03 (m, 22H), 0.98 (s, 9H). |
| 34 | I-32 | [({4-[(1E)-1-[[(2S,11S)-2-[[(3S,4R)-1-carbamoyl-4-[[4-(1-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]-2,5,8,11-tetraoxatetradecan-14- | $[(M + 23)]^+$ = 1649.8 | (400 MHz, $CDCl_3$) δ 8.68 (s, 1H), 7.79-7.43 (m, 5H), 7.26-7.18 (m, 4H), 7.14 (d, J = 7.6 Hz, 2H), 7.07 (d, J = 7.2 Hz, 2H), 7.06-6.98 (m, 4H), 6.90 (d, J = 9.5 Hz, 1H), 6.13 (d, J = 11.8 Hz, 2H), 5.71-5.58 (m, 5H), 5.18 (d, J = 5.6 Hz, 2H), 4.70 (t, J = 7.9 Hz, 1H), 4.64-4.47 (m, 6H), 4.45-4.30 (m, 3H), 3.98-3.83 (m, 5H), 3.59-3.43 (m, 6H), 3.38-3.20 (m, |

TABLE 73-continued

| Characterization Data for Exemplary STAT3 Degraders | | | | |
|---|---|---|---|---|
| EXAMPLE | I-# | Chemical Name | MS: $[(M + 1)]^+$ | $^1H$ NMR |
| | | yl)phenyl]methoxy]pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl([(2,2-dimethylpropanoyl)oxy]methoxy)phosphoryl)oxy]methyl 2,2-dimethylpropanoate | | 6H), 3.11 (d, J = 7.5 Hz, 1H), 2.73-2.40 (m, 9H), 2.35 (d, J = 13.1 Hz, 2H), 2.19-1.70 (m, 12H), 1.23-1.02 (m, 21H), 0.96 (s, 9H). |
| 35 | I-33 | [([4-[(1E)-1-[[(2S,11S)-2-[[(3S,4R)-1-Carbamoyl-4-[[4-(3-[2-[2-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methoxy)ethoxy]ethoxy]propyl)phenyl]methoxy]pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl([(2,2-dimethylpropanoyl)oxy]methoxy)phosphoryl)oxy]methyl 2,2-dimethylpropanoate | 1584.9 | (400 MHz, $CDCl_3$) δ 8.77 (s, 1H), 7.67-7.54 (m, 4H), 7.37-7.23 (m, 5H), 7.18-6.88 (m, 7H), 6.10 (d, J = 40.0 Hz, 2H), 5.72-5.63 (m, 4H), 5.16 (d, J = 6.5 Hz, 2H), 4.73 (t, J = 7.8 Hz, 1H), 4.66-4.48 (m, 5H), 4.46-4.33 (m, 2H), 4.07 (t, J = 10.2 Hz, 1H), 4.02-3.92 (m, 3H), 3.71-3.56 (m, 10H), 3.47-3.31 (m, 5H), 3.13 (d, J = 7.4 Hz, 1H), 2.65 (t, J = 7.6 Hz, 2H), 2.56-2.43 (m, 7H), 2.38 (d, J = 13.5 Hz, 1H), 2.18-2.04 (m, 4H), 1.86-1.70 (m, 5H), 1.25-1.02 (m, 24H), 0.97 (s, 9H). |
| 36 | I-34 | [([4-[(1E)-1-[[(2S,11S)-2-[[(3S,4R)-1-Carbamoyl-4-([4-[4-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methoxy)butyl]phenyl]methoxy)pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl([(2,2-dimethylpropanoyl)oxy]methoxy)phosphoryl)oxy]methyl 2,2-dimethylpropanoate | 1510.9 | (400 MHz, $CDCl_3$) δ 8.70 (s, 1H), 7.63 (d, J = 8.1 Hz, 2H), 7.58-7.47 (m, 3H), 7.39-7.30 (m, 4H), 7.28 (d, J = 5.0 Hz, 2H), 7.21-7.13 (m, 3H), 7.07-6.94 (m, 3H), 6.92 (dd, J = 15.7, 7.7 Hz, 2H), 6.06 (d, J = 8.7 Hz, 2H), 5.80-5.65 (m, 4H), 5.23-5.10 (m, 2H), 4.72 (t, J = 8.0 Hz, 1H), 4.65-4.50 (m, 5H), 4.38 (dd, J = 13.8, 5.6 Hz, 2H), 4.06 (d, J = 11.2 Hz, 1H), 3.95 (s, 1H), 3.83 (q, J = 15.3 Hz, 2H), 3.69-3.54 (m, 2H), 3.47 (d, J = 8.0 Hz, 2H), 3.32-3.21 (m, 3H), 3.13 (d, J = 7.4 Hz, 1H), 2.64-2.42 (m, 10H), 2.07-1.83 (m, 6H), 1.79-1.57 (m, 5H), 1.24-1.03 (m, 21H), 0.97 (s, 9H). |
| 37 | I-35 | [([4-[(1E)-1-[[(2S,11S)-2-[[(3S,4R)-1-Carbamoyl-4-([4-[3-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methoxy)propyl]phenyl]methoxy)pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl([(2,2-dimethylpropanoyl)oxy]methoxy)phosphoryl)oxy]methyl 2,2-dimethylpropanoate | 1497 | (400 MHz, $CDCl_3$) δ 8.77 (s, 1H), 7.62 (d, J = 8.3 Hz, 2H), 7.57-7.48 (m, 3H), 7.35 (s, 4H), 7.30-7.21 (m, 4H), 7.17-7.00 (m, 6H), 6.91 (d, J = 9.5 Hz, 1H), 6.07 (d, J = 65.0 Hz, 2H), 5.80-5.63 (m, 4H), 5.33-5.10 (m, 2H), 4.72 (t, J = 8.0 Hz, 1H), 4.64-4.49 (m, 5H), 4.45-4.30 (m, 2H), 3.99-3.88 (m, 4H), 3.83 (d, J = 6.3 Hz, 1H), 3.66 (dd, J = 11.1, 3.8 Hz, 1H), 3.57 (s, 1H), 3.52-3.42 (m, 2H), 3.33 (s, 1H), 3.11 (d, J = 7.2 Hz, 1H), 2.66 (t, J = 7.6 Hz, 2H), 2.58-2.55 (m, 3H), 2.43 (s, 1H), 2.36 (d, J = 12.6 Hz, 2H), 2.20-2.10 (m, 4H), 2.02 (q, J = 7.6 Hz, 1H), 1.95-1.86 (m, 3H), 1.76 (s, 2H), 1.24-1.03 (m, 21H), 0.98 (s, 9H), 0.85 (d, J = 8.1 Hz, 1H). |
| 38 | I-36 | [([4-[(1E)-1-[[(2S,11S)-2-[[(3S,4R)-1-carbamoyl-4-([4-[3-([5-[1-(2,6-dioxopiperidin-3-yl)-3-methyl-2-oxo-1,3-benzodiazol-5-yl]pentyl]oxy)propyl]phenyl]methoxy)pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl([(2,2-dimethylpropanoyl)oxy]methoxy)phosphoryl)oxy]methyl 2,2-dimethylpropanoate | 1352.8 | (400 MHz, $CDCl_3$) δ 9.02 (d, J = 7.9 Hz, 1H), 7.58-7.43 (m, 4H), 7.25 (dd, J = 7.8, 3.5 Hz, 2H), 7.16-6.96 (m, 6H), 6.89 (d, J = 8.2 Hz, 2H), 6.85 (s, 1H), 6.73 (d, J = 7.9 Hz, 1H), 6.28-6.00 (m, 2H), 5.76 (dd, J = 12.5, 5.0 Hz, 2H), 5.68 (dd, J = 12.4, 5.0 Hz, 2H), 5.33 (s, 1H), 5.25-5.09 (m, 2H), 4.59 (dd, J = 11.5, 4.7 Hz, 2H), 4.42 (d, J = 11.6 Hz, 1H), 3.98 (s, 1H), 3.59 (s, 1H), 3.39-3.20 (m, 10H), 3.12 (d, J = 7.5 Hz, 1H), 2.95-2.77 (m, 2H), 2.76-2.62 (m, 5H), 2.58 (s, 3H), 2.38 (s, 1H), 2.14-2.02 (m, 4H), 1.95 (s, 1H), 1.85-1.73 (m, 3H), 1.62-1.50 (m, 4H), 1.43 (q, J = 8.4 Hz, 2H), 1.24 (s, 18H), 1.21-1.16 (m, 3H). |

TABLE 73-continued

| Characterization Data for Exemplary STAT3 Degraders | | | | |
|---|---|---|---|---|
| EXAMPLE | I-# | Chemical Name | MS: $[(M + 1)]^+$ | $^1H$ NMR |
| 39 | I-37 | [([4-(1E)-1-[[(2S,11S)-2-[[(3S,4R)-1-Carbamoyl-4-[(4-[3-[2-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methoxy)ethoxy]propyl]phenyl)methoxy]pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl([(2,2-dimethylpropanoyl)oxy]methoxy)phosphoryl)oxy]methyl 2,2-dimethylpropanoate | 1539.9 | (400 MHz, $CDCl_3$) δ 8.75 (s, 1H), 7.62 (d, J = 8.1 Hz, 2H), 7.54 (d, J = 8.2 Hz, 2H), 7.44 (t, J = 5.9 Hz, 1H), 7.38-7.31 (m, 4H), 7.28 (s, 2H), 7.16 (d, J = 7.7 Hz, 2H), 7.12-6.98 (m, 4H), 6.92 (d, J = 9.3 Hz, 1H), 6.15 (s, 1H), 6.04 (s, 1H), 5.76 (ddd, J = 12.5, 5.0, 2.2 Hz, 2H), 5.68 (dd, J = 12.4, 5.0 Hz, 2H), 5.20 (t, J = 6.4 Hz, 1H), 5.12 (s, 1H), 4.71 (t, J = 7.9 Hz, 1H), 4.61 (d, J = 12.4 Hz, 2H), 4.56 (d, J = 6.4 Hz, 1H), 4.54-4.46 (m, 3H), 4.41 (d, J = 11.6 Hz, 1H), 4.33 (dd, J = 15.0, 5.3 Hz, 1H), 4.10-4.02 (m, 1H), 3.97-3.86 (m, 3H), 3.69-3.55 (m, 7H), 3.46 (q, J = 6.5, 5.2 Hz, 2H), 3.38-3.28 (m, 3H), 3.12 (d, J = 7.5 Hz, 1H), 2.65 (t, J = 7.6 Hz, 2H), 2.57 (s, 3H), 2.52-2.46 (m, 4H), 2.37 (d, J = 12.8 Hz, 1H), 2.10-1.92 (m, 4H), 1.88-1.81 (m, 3H), 1.80-1.68 (m, 1H), 1.24-1.03 (m, 21H), 0.97 (s, 9H). |
| 40 | I-38 | [([4-(1E)-1-[[(2S,11S)-2-[[(3S,4R)-1-carbamoyl-4-[[4-(5-[3-[1-(2,6-dioxopiperidin-3-yl)-3-methyl-2-oxo-1,3-benzodiazol-4-yl]propoxy]pentyl)phenyl]methoxy]pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl([(2,2-dimethylpropanoyl)oxy]methoxy)phosphoryl)oxy]methyl 2,2-dimethylpropanoate | 1352.8 | (400 MHz, $CDCl_3$) δ 9.24 (d, J = 8.4 Hz, 1H), 7.62 (d, J = 8.3 Hz, 2H), 7.56 (d, J = 8.2 Hz, 2H), 7.28-7.20 (m, 3H), 7.17-7.00 (m, 6H), 6.96 (q, J = 7.8 Hz, 1H), 6.87 (q, J = 8.3, 7.4 Hz, 2H), 6.70 (d, J = 7.8 Hz, 1H), 6.25-6.17 (m, 1H), 6.17-6.03 (m, 1H), 5.76 (dd, J = 12.5, 5.1 Hz, 2H), 5.67 (dd, J = 12.4, 5.0 Hz, 2H), 5.34-5.08 (m, 3H), 4.61 (dd, J = 10.3, 5.9 Hz, 1H), 4.49 (dd, J = 17.8, 11.6 Hz, 1H), 4.36 (d, J = 11.6 Hz, 1H), 3.96 (d, J = 10.3 Hz, 1H), 3.66-3.52 (m, 4H), 3.48-3.26 (m, 6H), 3.25-3.18 (m, 1H), 3.11 (d, J = 7.5 Hz, 1H), 2.95 (td, J = 14.4, 11.6, 7.2 Hz, 2H), 2.90-2.69 (m, 3H), 2.60 (d, J = 7.0 Hz, 1H), 2.37 (d, J = 11.9 Hz, 1H), 2.23-2.02 (m, 4H), 2.01-1.71 (m, 4H), 1.61-1.46 (m, 5H), 1.38-1.27 (m, 3H), 1.24 (s, 18H), 1.21-1.12 (m, 4H). |
| 41 | I-39 | [([4-[(1E)-1-[[(2S,11S)-2-[[(3S,4R)-1-carbamoyl-4-([4-[3-(2-[3-[3-methyl-1-(l-methyl-2,6-dioxopiperidin-3-yl)-2-oxo-1,3-benzodiazol-4-yl]propoxy]ethoxy)propyl]phenyl]methoxy)pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl([(2,2-dimethylpropanoyl)oxy]methoxy)phosphoryl)oxy]methyl 2,2-dimethylpropanoate | 1382.9 | (400 MHz, $CDCl_3$) δ 7.80-7.44 (m, 4H), 7.33-6.76 (m, 10H), 6.64 (d, J = 7.7 Hz, 1H), 6.15 (s, 1H), 5.98 (s, 1H), 5.71-5.58 (m, 4H), 5.19 (dq, J = 13.9, 7.2, 6.7 Hz, 2H), 4.98 (d, J = 12.6 Hz, 1H), 4.58 (d, J = 11.0 Hz, 2H), 4.42 (d, J = 11.6 Hz, 1H), 3.96 (s, 1H), 3.78-3.41 (m, 12H), 3.43-3.17 (m, 6H), 3.17-2.91 (m, 4H), 2.92-2.51 (m, 7H), 2.47-1.68 (m, 12H), 1.27-1.03 (m, 21H). |
| 42 | I-40 | [([4-[(1E)-1-[[(2S,11S)-2-[[(3S,4R)-1-carbamoyl-4-([4-[3-(3-[3-[1-(2,6-dioxopiperidin-3-yl)-3-methyl-2-oxo-1,3-benzodiazol-4-yl]propoxy]propoxy)propyl]phenyl]methoxy)pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl([(2,2-dimethylpropanoyl)oxy]methoxy)phosphoryl)oxy]methyl 2,2-dimethylpropanoate | 1383 | (400 MHz, $CDCl_3$) δ 9.17 (d, J = 7.5 Hz, 1H), 7.72-7.50 (m, 4H), 7.28-7.19 (m, 2H), 7.19-7.10 (m, 2H), 7.10-6.82 (m, 7H), 6.74-6.67 (m, 1H), 6.19 (d, J = 9.0 Hz, 1H), 6.01 (s, 1H), 5.72-5.55 (m, 4H), 5.31-5.04 (m, 3H), 4.68-4.34 (m, 3H), 3.97 (s, 1H), 3.66 (s, 3H), 3.62-3.48 (m, 7H), 3.46-2.62 (m, 13H), 2.58 (s, 3H), 2.38 (d, J = 13.6 Hz, 1H), 2.27-2.01 (m, 4H), 1.89-1.51 (m, 8H), 1.24 (s, 18H), 1.18 (s, 3H). |
| 43 | I-41 | [([4-[(1E)-1-[[(2S,11S)-2-[[(3S,4R)-1-carbamoyl-4-([4-[3-(4-[3-[1-(2,6-dioxopiperidin-3-yl)-3-methyl-2-oxo-1,3-benzodiazol-4-yl]propoxy]butoxy)propyl]phenyl]methoxy)pentan-3-yl]carbamoyl]-12-oxo-1-azatricyclo[6.4.1.0^[4,13]]trideca- | 1396.9 | (400 MHz, $CDCl_3$) δ 8.98 (d, J = 8.9 Hz, 1H), 7.67-7.49 (m, 4H), 7.35-7.13 (m, 4H), 7.11-6.65 (m, 9H), 6.22-6.01 (m, 3H), 5.72-5.41 (m, 4H), 5.32-5.02 (m, 3H), 4.66-4.35 (m, 4H), 3.68-3.55 (m, 6H), 3.52-2.54 (m, 21H), 2.46-1.80 (m, 12H), 1.24-1.03 (m, 21H). |

TABLE 73-continued

| Characterization Data for Exemplary STAT3 Degraders | | | | |
|---|---|---|---|---|
| EXAMPLE | I-# | Chemical Name | MS: $[(M + 1)]^+$ | $^1$H NMR |
| | | 4(13),5,7-trien-11-yl]carbamoyl]prop-1-en-2-yl]phenyl]difluoromethyl([(2,2-dimethylpropanoyl)oxy]methoxy)phosphoryl)oxy]methyl 2,2-dimethylpropanoate | | |
| 44 | I-42 | [([4-[(1E)-1-[[(2S,11S)-2-[[(3S,4R)-1-Carbamoyl-4-[(4-[3-[2-(2-[3-[1-(2,6-dioxopiperidin-3-yl)-3-methyl-2-oxo-1,3-benzodiazol-4-yl]propoxy]ethoxy)ethoxy]propyl]phenyl)methoxy]pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl([(2,2-dimethylpropanoyl)oxy]methoxy)phosphoryl)oxy]methyl 2,2-dimethylpropanoate | 1412.9 | (400 MHz, $CDCl_3$) δ 9.07 (d, J = 8.1 Hz, 1H), 7.61-7.41 (m, 4H), 7.21 (d, J = 9.3 Hz, 2H), 7.16-7.00 (m, 5H), 6.92-6.84 (m, 3H), 6.70 (d, J = 7.5 Hz, 1H), 6.27-5.94 (m, 2H), 5.76 (dd, J = 12.5, 5.0 Hz, 2H), 5.68 (dd, J = 12.3, 5.0 Hz, 2H), 5.17-5.01 (m, 3H), 4.56 (d, J = 6.9 Hz, 2H), 4.39 (d, J = 10.4 Hz, 1H), 3.97 (s, 1H), 3.73-3.58 (m, 10H), 3.53-3.49 (m, 3H), 3.48 (d, J = 4.8 Hz, 2H), 3.32 (d, J = 8.4 Hz, 2H), 3.21-3.07 (m, 2H), 3.01 (d, J = 7.6 Hz, 2H), 2.95-2.72 (m, 3H), 2.65 (t, J = 7.8 Hz, 2H), 2.61-2.52 (m, 3H), 2.38 (s, 1H), 2.16-1.91 (m, 5H), 1.89-1.53 (m, 7H), 1.24-1.03 (m, 21H). |
| 45 | I-43 | [([4-[(1E)-1-[[(2S,11S)-2-[[(3S,4R)-1-carbamoyl-4-[(4-[3-[(5-[3-[1-(2,6-dioxopiperidin-3-yl)-3-methyl-2-oxo-1,3-benzodiazol-4-yl]propoxy]pentyl)oxy]propyl]phenyl)methoxy]pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl([(2,2-dimethylpropanoyl)oxy]methoxy)phosphoryl)oxy]methyl 2,2-dimethylpropanoate | 1410.9 | (400 MHz, $CDCl_3$) δ 9.10 (d, J = 10.1 Hz, 1H), 7.72-7.40 (m, 4H), 7.28-7.19 (m, 2H), 6.99-6.72 (m, 9H), 6.69 (d, J = 7.7 Hz, 1H), 6.18 (d, J = 10.2 Hz, 1H), 6.06 (s, 1H), 5.76 (dd, J = 12.5, 5.0 Hz, 2H), 5.68 (dd, J = 12.4, 5.0 Hz, 2H), 5.37-5.03 (m, 3H), 4.71-4.49 (m, 2H), 4.40 (dd, J = 11.7, 3.7 Hz, 1H), 3.97 (s, 1H), 3.67 (s, 3H), 3.63-3.51 (m, 1H), 3.52-3.25 (m, 10H), 3.24-3.07 (m, 2H), 3.06-2.70 (m, 5H), 2.65 (t, J = 7.7 Hz, 2H), 2.58 (s, 3H), 2.37 (d, J = 13.5 Hz, 1H), 2.25-2.01 (m, 5H), 1.99-1.72 (m, 6H), 1.62-1.51 (m, 3H), 1.48 (s, 2H), 1.24 (s, 18H), 1.19 (s, 3H). |
| 46 | I-44 | [([4-[(1E)-1-[[(2S,11S)-2-[[(3S,4R)-1-carbamoyl-4-[(4-[3-[(6-[3-[1-(2,6-dioxopiperidin-3-yl)-3-methyl-2-oxo-1,3-benzodiazol-4-yl]propoxy]hexyl)oxy]propyl]phenyl)methoxy]pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl([(2,2-dimethylpropanoyl)oxy]methoxy)phosphoryl)oxy]methyl 2,2-dimethylpropanoate | 1424.9 | (400 MHz, $CDCl_3$) δ 8.98 (d, J = 8.6 Hz, 1H), 7.62 (d, J = 8.1 Hz, 2H), 7.56 (d, J = 8.3 Hz, 2H), 7.25-7.17 (m, 5H), 7.15-7.12 (m, 5H), 7.11-6.93 (m, 5H), 6.93-6.79 (m, 2H), 6.69 (d, J = 7.7 Hz, 1H), 6.23-6.05 (m, 2H), 5.76 (dd, J = 12.5, 5.0 Hz, 2H), 5.68 (dd, J = 12.4, 5.0 Hz, 2H), 5.41-5.05 (m, 3H), 4.68-4.50 (m, 2H), 4.41 (d, J = 11.5 Hz, 1H), 3.97 (s, 1H), 3.67 (s, 3H), 3.58 (s, 1H), 3.44-3.35 (m, 7H), 3.30-3.18 (m, 3H), 3.11 (d, J = 7.5 Hz, 1H), 3.07-2.96 (m, 2H), 2.95-2.69 (m, 3H), 2.65 (t, J = 7.6 Hz, 2H), 2.58 (s, 3H), 2.43-2.01 (m, 6H), 1.86-1.51 (m, 5H), 1.42-1.28 (m, 4H), 1.24-1.02 (m, 20H). |
| 47 | I-45 | [([4-[(1E)-1-[[(2S,11S)-2-[[(3S,4R)-1-carbamoyl-4-[(4-[3-[(7-[3-[1-(2,6-dioxopiperidin-3-yl)-3-methyl-2-oxo-1,3-benzodiazol-5-yl]propoxy]heptyl)oxy]propyl]phenyl)methoxy]pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl([(2,2-dimethylpropanoyl)oxy]methoxy)phosphoryl)oxy]methyl 2,2-dimethylpropanoate | 1438.9 | (400 MHz, $CDCl_3$) δ 9.00 (d, J = 8.7 Hz, 1H), 7.62 (d, J = 8.1 Hz, 2H), 7.55 (d, J = 8.2 Hz, 2H), 7.26 (dd, J = 7.8, 3.9 Hz, 2H), 7.15 (dd, J = 1.1, 5.0 Hz, 2H), 7.06-6.92 (m, 4H), 6.88-6.77 (m, 3H), 6.74 (d, J = 7.3 Hz, 1H), 6.17 (d, J = 6.2 Hz, 1H), 6.10 (s, 1H), 5.76 (dd, J = 12.5, 5.0 Hz, 2H), 5.68 (dd, J = 12.3, 5.0 Hz, 2H), 5.20-5.01 (m, 3H), 4.66-4.51 (m, 3H), 4.42 (d, J = 11.6 Hz, 1H), 3.98 (s, 1H), 3.58 (s, 2H), 3.42-3.18 (m, 14H), 3.12 (d, J = 17.4 Hz, 1H), 2.97-2.79 (m, 3H), 2.74-2.68 (m, 3H), 2.65 (t, J = 7.7 Hz, 2H), 2.58 (s, 3H), 2.36 (s, 1H), 2.22 (s, 2H), 2.10 (s, 3H), 1.87-1.54 (m, 6H), 1.39-1.28 (m, 6H), 1.24-1.03 (m, 21H). |
| 48 | I-46 | [([4-[(1E)-1-[[(2S,11S)-2-[[(3S,4R)-1-Carbamoyl-4-(4-[3-(4-[3-[1-(2,6-dioxopiperidin-3-yl)-3-methyl-2-oxo-1,3-benzodiazol-5-yl]propoxy]butoxy)propyl]phenyl]methoxy)pentan-3-yl]carbamoyl]-12-oxo-1-azatricyclo[6.4.1.0^[4,13]]trideca- | 1396.8 | (400 MHz, $CDCl_3$) δ 8.87 (d, J = 6.5 Hz, 1H), 7.69-7.52 (m, 4H), 7.12-6.93 (m, 6H), 6.81-6.51 (m, 4H), 6.11 (d, J = 7.5 Hz, 2H), 5.73-5.43 (m, 4H), 5.21 (s, 3H), 4.61 (s, 2H), 4.42 (d, J = 11.6 Hz, 1H), 3.98 (s, 1H), 3.60 (s, 1H), 3.55-3.18 (m, 15H), 3.13 (d, J = 17.4 Hz, 1H), 2.97-2.55 (m, 10H), 2.45-1.75 (m, 15H), 1.25-1.04 (m, 22H). |

TABLE 73-continued

Characterization Data for Exemplary STAT3 Degraders

| EXAMPLE | I-# | Chemical Name | MS: $[(M + 1)]^+$ | $^1H$ NMR |
|---|---|---|---|---|
| | | 4(13),5,7-trien-11-yl]carbamoyl]prop-1-en-2-yl]phenyl]difluoromethyl([(2,2-dimethylpropanoyl)oxy]methoxy)phosphoryl)oxy]methyl 2,2-dimethylpropanoate | | |
| 49 | I-47 | [([4-[(1E)-1-[[(2S,11S)-2-[[(3S,4R)-1-carbamoyl-4-[(4-[3-[(5-[3-[1-(2,6-dioxopiperidin-3-yl)-3-methyl-2-oxo-1,3-benzodiazol-5-yl]propoxy]pentyl)oxy]propyl]phenyl)methoxy]pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl([(2,2-dimethylpropanoyl)oxy]methoxy)phosphoryl)oxy]methyl 2,2-dimethylpropanoate | 1411 | (400 MHz, $CDCl_3$) δ 9.30 (d, J = 8.7 Hz, 1H), 7.73-7.46 (m, 4H), 7.24 (dd, J = 7.8, 5.9 Hz, 2H), 7.18-6.99 (m, 6H), 6.93-6.83 (m, 3H), 6.73 (dd, J = 7.9, 1.9 Hz, 1H), 6.26-6.04 (m, 2H), 5.72-5.61 (m, 4H), 5.45-5.09 (m, 3H), 4.71-4.50 (m, 2H), 4.41 (d, J = 11.6 Hz, 1H), 4.11-3.89 (m, J = 5.8 Hz, 2H), 3.56 (d, J = 8.5 Hz, 1H), 3.52-3.18 (m, 14H), 3.11 (d, J = 17.5 Hz, 1H), 2.95-2.78 (m, 2H), 2.78-2.60 (m, 5H), 2.57-2.42 (m, 3H), 2.36 (d, J = 13.3 Hz, 1H), 2.24-2.03 (m, 5H), 2.00-1.71 (m, 6H), 1.63-1.50 (m, 4H), 1.48 (tt, J = 8.8, 3.8 Hz, 1H), 1.22-1.01 (m, 20H). |
| 50 | I-48 | [4-[(1E)-1-[[(2S,11S)-2-[[(3S,4R)-1-carbamoyl-4-[(4-[3-[2-(2-[3-[3-methyl-1-(1-methyl-2,6-dioxopiperidin-3-yl)-2-oxo-1,3-benzodiazol-5-yl]propoxy]ethoxy)acetamido]propyl]phenyl)methoxy]pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethylphosphonic acid | 1211.7 | (400 MHz, $D_2O$) δ 7.49-7.32 (m, 4H), 7.17-6.10 (m, 11H), 4.99-4.75 (m, 2H), 4.24-4.03 (m, 3H), 3.85 (s, 3H), 3.65-2.75 (m, 16H), 2.81-2.52 (m, 4H), 2.52-1.29 (m, 20H), 0.97 (s, 3H). |
| 51 | I-49 | ([4-[(1E)-1-[[(2S,11S)-2-[[(3S,4R)-1-carbamoyl-4-[[4-(3-[2-[2-(2-[3-[1-(2,6-dioxopiperidin-3-yl)-3-methyl-2-oxo-2,3-dihydro-1H-1,3-benzodiazol-5-yl]propoxy]ethoxy)ethoxy]acetamido]propyl)phenyl]methoxy]pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl)phosphonic acid | 1241.9 | (400 MHz, $D_2O$) δ 7.58-7.45 (m, 4H), 7.06-6.74 (m, 10H), 6.21 (s, 1H), 5.36 (s, 1H), 5.14-5.10 (m, 1H), 5.01-4.90 (m, 1H), 4.47-4.36 (m, 1H), 4.29 (s, 2H), 3.89 (s, 3H), 3.65-3.47 (m, 6H), 3.46 (s, 2H), 3.37-3.28 (m, 2H), 3.17 (s, 3H), 3.12-3.02 (m, 2H), 2.98 (s, 1H), 2.71 (s, 3H), 2.51 (s, 3H), 2.42-2.32 (m, 2H), 2.34-2.22 (m, 3H), 2.15 (s, 2H), 2.04 (s, 2H), 2.00-1.88 (m, 1H), 1.86-1.58 (m, 2H), 1.60-1.49 (m, 3H), 1.20 (s, 1H), 1.08-1.04 (m, 2H), 1.03-0.96 (m, 3H). |
| 52 | I-50 | [([4-[(1E)-1-[[(2S,11S)-2-[[(3S,4R)-1-carbamoyl-4-[[4-(5-[3-[1-(2,6-dioxopiperidin-3-yl)-3-methyl-2-oxo-1,3-benzodiazol-5-yl]propoxy]pentyl)phenyl]methoxy]pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl([(2,2-dimethylpropanoyl)oxy]methoxy)phosphoryl)oxy]methyl 2,2-dimethylpropanoate | 1353.9 | (400 MHz, $CDCl_3$) δ 9.16 (dd, J = 10.7, 5.5 Hz, 1H), 7.62 (d, J = 8.2 Hz, 2H), 7.56 (d, J = 8.3 Hz, 2H), 7.24 (d, J = 7.6 Hz, 2H), 7.14 (dd, J = 7.8, 3.2 Hz, 2H), 7.06-6.96 (m, 4H), 6.86 (d, J = 8.9 Hz, 3H), 6.75 (d, J = 7.9 Hz, 1H), 6.19 (d, J = 5.7 Hz, 1H), 6.08 (s, 1H), 5.76 (dd, J = 12.5, 5.0 Hz, 2H), 5.68 (dd, J = 12.4, 5.0 Hz, 2H), 5.23 (d, J = 11.7 Hz, 2H), 5.16 (s, 1H), 4.61 (s, 1H), 4.54 (dd, J = 11.5, 4.5 Hz, 1H), 4.37 (dd, J = 11.5, 5.2 Hz, 1H), 3.97 (s, 1H), 3.56 (s, 1H), 3.46-3.33 (m, 8H), 3.30 (s, 2H), 3.12 (d, J = 7.3 Hz, 1H), 2.85 (d, J = 8.9 Hz, 2H), 2.80-2.64 (m, 3H), 2.62-2.50 (m, 5H), 2.37 (d, J = 12.8 Hz, 1H), 2.15-2.02 (m, 6H), 1.99-1.83 (m, 3H), 1.60-1.46 (m, 4H), 1.41 (q, J = 7.6, 7.1 Hz, 2H), 1.24 (s, 18H), 1.19-1.09 (m, 3H). |
| 53 | I-51 | [([4-[(1E)-1-[[(2S,11S)-2-[[(3S,4R)-1-carbamoyl-4-[(4-[3-[(6-[3-[1-(2,6-dioxopiperidin-3-yl)-3-methyl-2-oxo-1,3-benzodiazol-5-yl]propoxy]hexyl)oxy]propyl]phenyl)methoxy]pentan-3-yl]carbamoyl]-12-oxo-1-azatricyclo[6.4.1.0^[4,13]]trideca-4(13),5,7-trien-11- | 1425 | (400 MHz, $CDCl_3$) δ 8.95 (d, J = 8.3 Hz, 1H), 7.74-7.50 (m, 4H), 7.30-7.23 (m, 2H), 7.19-6.95 (m, 6H), 6.94-6.80 (m, 3H), 6.74 (dd, J = 8.0, 1.7 Hz, 1H), 6.17 (d, J = 6.5 Hz, 1H), 5.99 (s, 1H), 5.76 (dd, J = 12.5, 5.0 Hz, 2H), 5.68 (dd, J = 12.4, 5.0 Hz, 2H), 5.29-5.07 (m, 3H), 4.60 (td, J = 11.2, 10.3, 5.0 Hz, 2H), 4.42 (d, J = 11.6 Hz, 1H), 3.98 (t, J = 10.7 Hz, 1H), 3.59 (t, J = 5.9 Hz, 1H), 3.49-3.21 (m, 14H), 3.12 (dt, J = 17.6, 4.6 Hz, 1H), |

TABLE 73-continued

| Characterization Data for Exemplary STAT3 Degraders | | | | |
|---|---|---|---|---|
| EXAMPLE | I-# | Chemical Name | MS: $[(M + 1)]^+$ | $^1$H NMR |
| | | yl]carbamoyl]prop-1-en-2-yl]phenyl]difluoromethyl([(2,2-dimethylpropanoyl)oxy]methoxy)phosphoryl)oxy]methyl 2,2-dimethylpropanoate | | 2.96-2.61 (m, 7H), 2.58 (s, 3H), 2.38 (d, J = 13.8 Hz, 1H), 2.27-2.02 (m, 5H), 1.86-1.52 (m, 8H), 1.42-1.30 (m, 5H), 1.24-1.01 (m, 21H). |
| 54 | I-52 | [([4-[(1E)-1-[[(2S,11S)-2-[[(3S,4R)-1-carbamoyl-4-[(4-[3-[(8-[3-[1-(2,6-dioxopiperidin-3-yl)-3-methyl-2-oxo-1,3-benzodiazol-5-yl]propoxy]octyl)oxy]propyl]phenyl)methoxy]pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl([(2,2-dimethylpropanoyl)oxy]methoxy)phosphoryl)oxy]methyl 2,2-dimethylpropanoate | 1452.7 | (400 MHz, $CDCl_3$) δ 8.93 (d, J = 8.6 Hz, 1H), 7.62 (d, J = 8.1 Hz, 2H), 7.55 (d, J = 8.1 Hz, 2H), 7.28-7.20 (m, 2H), 7.15 (dd, J = 7.9, 2.8 Hz, 2H), 7.07-6.93 (m, 4H), 6.88-6.78 (m, 3H), 6.74 (d, J = 7.9 Hz, 1H), 6.17 (d, J = 4.9 Hz, 1H), 6.11 (s, 1H), 5.76 (dd, J = 12.5, 5.0 Hz, 2H), 5.68 (dd, J = 12.4, 5.0 Hz, 2H), 5.23-5.03 (m, 3H), 4.66-4.52 (m, 2H), 4.42 (d, J = 11.5 Hz, 1H), 3.95 (d, J = 8.1 Hz, 1H), 3.59 (s, 1H), 3.48-3.20 (m, 14H), 3.12 (d, J = 7.2 Hz, 1H), 2.97-2.80 (m, 2H), 2.69-2.59 (m, 6H), 2.58 (s, 3H), 2.37 (d, J = 13.4 Hz, 1H), 2.21 (d, J = 12.4 Hz, 1H), 2.08-1.91 (m, 3H), 1.87-1.70 (m, 6H), 1.66-1.50 (m, 4H), 1.35-1.27 (m, 8H), 1.24-1.01 (m, 20H). |
| 55 | I-53 | [([4-[(1E)-1-[[(2S,11S)-2-[[(3S,4R)-1-carbamoyl-4-([4-[3-(3-[3-[1-(2,6-dioxopiperidin-3-yl)-3-methyl-2-oxo-1,3-benzodiazol-5-yl]propoxy]propoxy)propyl]phenyl]methoxy)pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl([(2,2-dimethylpropanoyl)oxy]methoxy)phosphoryl)oxy]methyl 2,2-dimethylpropanoate | 1382.7 | (400 MHz, $CDCl_3$) δ 9.02 (d, J = 8.9 Hz, 1H), 7.62 (d, J = 7.9 Hz, 2H), 7.56 (d, J = 8.3 Hz, 2H), 7.24 (s, 2H), 7.16-6.92 (m, 6H), 6.88-6.76 (m, 3H), 6.73 (d, J = 7.9 Hz, 1H), 6.19 (d, J = 11.9 Hz, 1H), 6.03 (s, 1H), 5.76 (dd, J = 12.5, 5.0 Hz, 2H), 5.68 (dd, J = 12.4, 5.0 Hz, 2H), 5.20-5.01 (m, 3H), 4.59 (d, J = 16.5 Hz, 2H), 4.41 (d, J = 11.5 Hz, 1H), 3.98 (s, 1H), 3.65-5.51 (m, 5H), 3.49-3.21 (m, 10H), 3.13 (d, J = 17.5 Hz, 1H), 2.86 (d, J = 8.9 Hz, 2H), 2.70-2.61 (m, 5H), 2.58 (s, 3H), 2.38 (s, 1H), 2.11 (s, 4H), 1.98-1.72 (m, 8H), 1.27-1.03 (m, 21H). |
| 56 | I-55 | [([4-[(1E)-1-[[(2S,11S)-2-[[(3S,4R)-1-carbamoyl-4-[(4-[3-[2-(2-[3-[1-(2,6-dioxopiperidin-3-yl)-3-methyl-2-oxo-1,3-benzodiazol-5-yl]propoxy]ethoxy)ethoxy]propyl]phenyl)methoxy]pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl([(2,2-dimethylpropanoyl)oxy]methoxy)phosphoryl)oxy]methyl 2,2-dimethylpropanoate | 1412.8 | (400 MHz, $CDCl_3$) δ 9.07 (d, J = 8.9 Hz, 1H), 7.62 (d, J = 8.1 Hz, 2H), 7.57 (d, J = 8.3 Hz, 2H), 7.23 (t, J = 7.9 Hz, 2H), 7.09-6.61 (m, 6H), 6.88-6.75 (m, 3H), 6.73 (d, J = 8.0 Hz, 1H), 6.20 (d, J = 14.5 Hz, 1H), 6.08 (s, 1H), 5.76 (dd, J = 12.5, 5.0 Hz, 2H), 5.68 (dd, J = 12.4, 5.0 Hz, 2H), 5.20-5.02 (m, 3H), 4.66-4.52 (m, 2H), 4.41 (d, J = 11.5 Hz, 1H), 4.06 (h, J = 6.1 Hz, 1H), 3.97 (s, 1H), 3.76-3.69 (m, 4H), 3.65-3.52 (m, 5H), 3.49-3.43 (m, 4H), 3.42-3.20 (m, 6H), 3.13 (d, J = 7.6 Hz, 1H), 2.86 (d, J = 6.9 Hz, 2H), 2.69-2.60 (m, 5H), 2.58 (s, 3H), 2.38 (s, 1H), 2.17-2.03 (m, 4H), 2.00-1.73 (m, 2H), 1.60 (s, 1H), 1.45 (d, J = 2.0 Hz, 1H), 1.28 (s, 2H), 1.24-1.02 (m, 20H). |
| 57 | 1-56 | [4-[(1E)-1-[[(2S)-1-[(1R,2S,5S)-2-[[(3S,4R)-1-carbamoyl-4-[(4-[3-[2-(2-[3-[1-(2,6-dioxopiperidin-3-yl)-3-methyl-2-oxo-1,3-benzodiazol-5-yl]propoxy]ethoxy)acetamido]propyl]phenyl)methoxy]pentan-3-yl]carbamoyl]-3-azabicyclo[3.1.0]hexan-3-yl]-1-oxohexan-2-yl]carbamoyl]prop-1-en-2-yl]phenyl]difluoromethylphosphonic acid | 1192.7 | (400 MHz, $D_2O$) δ 7.55 (d, J = 8.4 Hz, 2H), 7.47 (d, J = 8.2 Hz, 2H), 7.11 (d, J = 7.7 Hz, 2H), 6.97 (d, J = 7.8 Hz, 2H), 6.90 (s, 1H), 6.82 (s, 2H), 6.19 (s, 1H), 5.18 (d, J = 11.5 Hz, 1H), 4.35-4.03 (m, 4H), 3.90 (s, 3H), 3.84 (d, J = 11.4 Hz, 1H), 3.60-3.52 (m, 5H), 3.49-3.44 (m, 1H), 3.40 (t, J = 6.4 Hz, 2H), 3.19 (d, J = 2.4 Hz, 3H), 3.10 (t, J = 6.9 Hz, 2H), 2.84-2.67 (m, 2H), 2.57 (t, J = 7.4 Hz, 2H), 2.48 (d, J = 12.2 Hz, 1H), 2.40 (t, J = 7.7 Hz, 2H), 2.35 (s, 3H), 2.20-2.17 (m, 2H), 1.98 (s, 1H), 1.76 (t, J = 7.1 Hz, 2H), 1.70-1.61 (m, 6H), 1.56-1.42 (m, 2H), 1.31-1.13 (m, 4H), 1.03 (d, J = 6.2 Hz, 3H), 0.75 (t, J = 7.0 Hz, 3H), 0.58-0.41 (m, 2H). |
| 58 | I-57 | [4-[(1E)-1-[[(2S)-1-[(1R,2S,5S)-2-[[(3S,4R)-1-carbamoyl-4-[[4-(3-[2-[2-(2-[3-[1-(2,6-dioxopiperidin-3-yl)-3-methyl-2-oxo-1,3-benzodiazol-5-yl]propoxy]ethoxy)ethoxy]acetamido]propyl)phenyl]methoxy]pentan-3-yl]carbamoyl]-3-azabicyclo[3.1.0]hexan-3-yl]-1- | 1235.8 | (400 MHz, $CD_3OD$) δ 7.70 (d, J = 8.2 Hz, 2H), 7.53 (d, J = 8.1 Hz, 2H), 7.27 (d, J = 7.8 Hz, 2H), 7.15 (d, J = 7.7 Hz, 2H), 7.07-6.93 (m, 3H), 6.32 (s, 1H), 5.31-5.30 (m, 1H), 4.58-4.44 (m, 4H), 4.15-4.13 (m, 1H), 3.99 (s, 2H), 3.91 (d, J = 9.2 Hz, 1H), 3.77 (d, J = 9.9 Hz, 1H), 3.69-3.62 (m, 6H), 3.60-3.58 (m, 2H), 3.55-3.46 (m, 3H), 3.40 (s, 3H), 3.26-3.22 (m, 2H), 2.93-2.88 (m, 1H), 2.86- |

TABLE 73-continued

| Characterization Data for Exemplary STAT3 Degraders | | | | |
|---|---|---|---|---|
| EXAMPLE | I-# | Chemical Name | MS: $[(M + 1)]^+$ | $^1H$ NMR |
| | | oxohexan-2-yl]carbamoyl]prop-1-en-2-yl]phenyl]difluoromethylphosphonic acid | | 2.71 (m, 4H), 2.60 (t, J = 7.8 Hz, 2H), 2.52-2.49 (m, 3H), 2.34-2.23 (m, 2H), 2.15-2.11 (m, 2H), 1.96-1.84 (m, 3H), 1.79-1.73 (m, 4H), 1.71-1.54 (m, 2H), 1.43-1.35 (m, 4H), 1.20-1.15 (m, 3H), 0.96 (t, J = 7.0 Hz, 3H), 0.87 (d, J = 4.6 Hz, 1H), 0.67 (q, J = 7.8 Hz, 1H). |
| 59 | I-58 | [([4-[(1E)-1-[[(2S)-1-[(1R,2S,5S)-2-[[(3S,4R)-1-carbamoyl-4-[(4-[3-[2-(2-[3-[1-(2,6-dioxopiperidin-3-yl)-3-methyl-2-oxo-1,3-benzodiazol-5-yl]propoxy]ethoxy)acetamido]propyl]phenyl)methoxy]pentan-3-yl]carbamoyl]-3-azabicyclo[3.1.0]hexan-3-yl]-1-oxohexan-2-yl]carbamoyl]prop-1-en-2-yl]phenyl]difluoromethyl([[(2,2-dimethylpropanoyl)oxy]methoxy)phosphoryl)oxy]methyl 2,2-dimethylpropanoate | 1421.1 | (400 MHz, $CDCl_3$) δ 9.69 (d, J = 8.0 Hz, 1H), 7.60-7.55 (m, 4H), 7.15-7.10 (m, 3H), 7.03 (d, J = 7.7 Hz, 1H), 6.92-6.83 (m, 2H), 6.85-6.75 (m, 2H), 6.69-6.65 (m, 1H), 6.51-6.47 (m, 1H), 6.21 (d, J = 8.4 Hz, 1H), 5.81-5.72 (m, 2H), 5.68-5.41 (m, 2H), 5.31-5.12 (m, 1H), 4.79 (d, J = 7.2 Hz, 1H), 4.56 (t, J = 12.2 Hz, 1H), 4.30-4.27 (m, 2H), 4.11-4.02 (m, 3H), 3.98 (s, 1H), 3.78 (d, J = 10.0 Hz, 1H), 3.71 (s, 2H), 3.63 (s, 2H), 3.54-3.46 (m, 3H), 3.35-3.28 (m, 5H), 2.88 (d, J = 20.3 Hz, 2H), 2.73-2.68 (m, 3H), 2.63-2.55 (m, 4H), 2.48-2.35 (m, 2H), 2.21 (s, 1H), 2.10-1.89 (m, 7H), 1.83 (d, J = 7.3 Hz, 2H), 1.38-1.29 (m, 4H), 1.24-1.20 (m, 22H), 1.19-1.13 (m, 3H), 1.06 (d, J = 13.9 Hz, 1H), 0.91-0.86 (m, 3H), 0.67 (s, 1H). |
| 60 | I-59 | [([4-[(1E)-1-[[(2S)-1-[(1R,2S,5S)-2-[[(3S,4R)-1-carbamoyl-4-[[4-(3-[2-[2-(2-[3-[1-(2,6-dioxopiperidin-3-yl)-3-methyl-2-oxo-1,3-benzodiazol-5-yl]propoxy]ethoxy)ethoxy]acetamido]propyl)phenyl]methoxy]pentan-3-yl]carbamoyl]-3-azabicyclo[3.1.0]hexan-3-yl]-1-oxohexan-2-yl]carbamoyl]prop-1-en-2-yl]phenyl]difluoromethyl([[(2,2-dimethylpropanoyl)oxy]methoxy)phosphoryl)oxy]methyl 2,2-dimethylpropanoate | 1463.9 | (400 MHz, $CDCl_3$) δ 9.53 (d, J = 7.6 Hz, 1H), 7.60 (d, J = 8.4 Hz, 2H), 7.55 (d, J = 8.2 Hz, 2H), 7.23-7.08 (m, 4H), 7.05 (d, J = 7.7 Hz, 1H), 6.86-6.82 (m, 3H), 6.80-6.72 (m, 1H), 6.66 (d, J = 7.8 Hz, 1H), 6.32-6.30 (m, 1H), 6.18 (d, J = 7.4 Hz, 1H), 5.80-5.71 (m, 2H), 5.68-5.55 (m, 2H), 5.51 (s, 1H), 5.23 (d, J = 12.2 Hz, 1H), 4.78 (d, J = 7.1 Hz, 1H), 4.54 (d, J = 11.7 Hz, 1H), 4.32-4.29 (m, 2H), 4.13-3.91 (m, 5H), 3.78 (d, J = 9.9 Hz, 1H), 3.69 (d, J = 6.3 Hz, 6H), 3.60-3.58 (m, 2H), 3.46-3.43 (m, 2H), 3.39-3.33 (m, 4H), 3.32 (d, J = 7.1 Hz, 2H), 2.97-2.78 (m, 2H), 2.78-2.52 (m, 8H), 2.51-2.02 (m, 6H), 1.87-1.45 (m, 8H), 1.37-1.28 (m, 5H), 1.23-1.16 (m, 23H). |
| 61 | I-60 | [[([4-[(1E)-1-[[(2S,11S)-2-[[(3S,4R)-1-carbamoyl-4-[(4-[16-[1-(2,6-dioxopiperidin-3-yl)-3-methyl-2-oxo-2,3-dihydro-1H-1,3-benzodiazol-5-yl]-4,7,10,13-tetraoxahexadecan-1-yl]phenyl)methoxy]pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl)([[(2,2-dimethylpropanoyl)oxy]methoxy])phosphoryl]oxy]methyl 2,2-dimethylpropanoate | 1456.7 | (400 MHz, $CD_3OD$) δ 7.69 (d, J = 8.2 Hz, 2H), 7.62 (d, J = 8.3 Hz, 2H), 7.22 (d, J = 7.7 Hz, 2H), 7.12-7.05 (m, 3H), 7.04-6.97 (m, 4H), 6.95 (d, J = 8.4 Hz, 1H), 6.41 (d, J = 1.5 Hz, 1H), 5.81-5.66 (m, 4H), 5.31 (dd, J = 12.5, 5.4 Hz, 1H), 5.15 (dd, J = 11.0, 3.2 Hz, 1H), 4.65 (d, J = 9.8 Hz, 1H), 4.53-4.43 (m, 2H), 4.00 (s, 1H), 3.76-3.63 (m, 8H), 3.61-3.53 (m, 5H), 3.51-3.44 (m, 5H), 3.40 (s, 3H), 3.25-3.12 (m, 2H), 3.04-2.87 (m, 2H), 2.77-2.67 (m, 4H), 2.65 (t, J = 7.6 Hz, 2H), 2.55 (d, J = 1.4 Hz, 3H), 2.36-2.22 (m, 4H), 2.17-2.10 (m, 1H), 1.99 (d, J = 7.0 Hz, 1H), 1.86-1.72 (m, 4H), 1.68 (s, 1H), 1.23-1.01 (m, 21H). |
| 62 | I-61 | [[([4-[(1E)-1-[[(2S,11S)-2-[[(3S,4R)-1-carbamoyl-4-[[4-(3-[3-[1-(2,6-dioxopiperidin-3-yl)-3-methyl-2-oxo-2,3-dihydro-1H-1,3-benzodiazol-5-yl]propanamido]propyl)phenyl]methoxy]pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl)([[(2,2-dimethylpropanoyl)oxy]methoxy])phosphoryl]oxy]methyl 2,2-dimethylpropanoate | 1337.7 | (400 MHz, $CD_3OD$) δ 8.01 (d, J = 9.5 Hz, 1H), 7.69 (d, J = 8.3 Hz, 2H), 7.62 (d, J = 8.3 Hz, 2H), 7.22 (d, J = 7.8 Hz, 2H), 7.10-7.07 (m, 2H), 7.06-6.98 (m, 6H), 6.41 (d, J = 4.1 Hz, 1H), 5.75-5.34 (m, 4H), 5.29-5.22 (m, 1H), 5.18-5.16 (m, 1H), 4.66 (d, J = 9.4 Hz, 1H), 4.57-4.44 (m, 2H), 3.99 (s, 1H), 3.60-3.46 (m, 2H), 3.25-3.10 (m, 4H), 3.07-2.97 (m, 3H), 2.85 (d, J = 15.5 Hz, 1H), 2.77-2.64 (m, 2H), 2.58-2.51 (m, 6H), 2.42-2.35 (m, 2H), 2.34-2.19 (m, 4H), 1.98 (d, J = 6.5 Hz, 2H), 1.64-1.59 (m, 3H), 1.23-1.15 (m, 22H). |
| 63 | I-62 | ([4-[(1E)-1-[[(2S,11S)-2-[[(3S,4R)-1-carbamoyl-4-[[4-(3-[3-[1-(2,6-dioxopiperidin-3-yl)-3-methyl-2-oxo-2,3-dihydro-1H-1,3-benzodiazol-5-yl]propanamido]propyl)phenyl] | 1109.5 | (400 MHz, $CD_3OD$) δ 7.69 (d, J = 8.3 Hz, 2H), 7.58 (d, J = 8.0 Hz, 2H), 7.20 (d, J = 7.8 Hz, 2H), 7.14 (d, J = 7.1 Hz, 1H), 7.08-6.96 (m, 7H), 6.37 (s, 1H), 5.28-5.10 (m, 4H), 4.50 (s, 3H), 4.02 (d, J = 11.6 Hz, 1H), 3.63-3.58 (m, 1H), 3.53-3.46 (m, 1H), 3.23-3.10 |

TABLE 73-continued

Characterization Data for Exemplary STAT3 Degraders

| EXAMPLE | I-# | Chemical Name | MS: $[(M + 1)]^+$ | $^1$H NMR |
| --- | --- | --- | --- | --- |
| | | methoxy]pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl)phosphonic acid | | (m, 4H), 3.05-2.97 (m, 3H), 2.86 (d, J = 10.9 Hz, 1H), 2.76 (d, J = 17.8 Hz, 1H), 2.58-2.50 (m, 6H), 2.33-1.88 (m, 9H), 1.72-1.57 (m, 3H), 1.30-1.21 (m, 3H). |
| 64 | I-63 | ([4-[(1E)-1-[[(2S,11S)-2-[[(3S,4R)-1-carbamoyl-4-[[4-(3-[15-[1-(2,6-dioxopiperidin-3-yl)-3-methyl-2-oxo-2,3-dihydro-1H-1,3-benzodiazol-5-yl]-3,6,9,12-tetraoxapentadecanamido]propyl) phenyl]methoxy]pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl)phosphonic acid | 1285.6 | (400 MHz, $D_2O$) δ 7.62-7.41 (m, 4H), 7.04-6.67 (m, 10H), 6.21 (s, 1H), 5.09 (s, 2H), 4.24-4.03 (m, 3H), 3.85 (d, J = 7.8 Hz, 3H), 3.62-3.33 (m, 13H), 3.13-2.96 (m, 10H), 2.67-2.58 (m, 3H), 2.56-2.26 (m, 8H), 2.26-1.42 (m, HH), 0.99-0.92 (m, 3H). |
| 65 | I-64 | [[([4-[(1E)-1-[[(2S,11S)-2-[[(3S,4R)-1-carbamoyl-4-[(4-[3-[2-(2-[3-[1-(2,6-dioxopiperidin-3-yl)-3-methyl-2-oxo-2,3-dihydro-1H-1,3-benzodiazol-5-yl]propoxy]ethoxy)acetamido] propyl]phenyl)methoxy]pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl)([[(2,2-dimethylpropanoyl)oxy]methoxy]) phosphoryl]oxy]methyl 2,2-dimethylpropanoate | 1425.7 | (400 MHz, $CD_3OD$) δ 7.95 (d, J = 8.7 Hz, 1H), 7.70-7.54 (m, 4H), 7.22-7.15 (m, 2H), 7.07 (d, J = 7.6 Hz, 3H), 7.03-6.95 (m, 3H), 6.95-6.88 (m, 1H), 6.41-6.34 (m, 1H), 5.80-5.52 (m, 3H), 5.34-5.25 (m, 1H), 5.11-5.08 (m, 1H), 4.63 (d, J = 9.8 Hz, 1H), 4.52-4.40 (m, 2H), 4.02-3.87 (m, 4H), 3.68-3.63 (m, 2H), 3.62-3.60 (m, 2H), 3.59-3.36 (m, 4H), 3.35 (s, 3H), 3.30-3.08 (m, 3H), 3.01-2.83 (m, 2H), 2.83-2.67 (m, 4H), 2.58 (t, J = 7.8 Hz, 2H), 2.53-2.42 (m, 3H), 2.32-2.17 (m, 4H), 2.16-2.05 (m, 1H), 1.99-1.74 (m, 5H), 1.67 (s, 1H), 1.32-1.23 (m, 4H), 1.21 (s, 18H). |
| 66 | I-65 | ([4-[(1E)-1-[1(2S,11S)-2-[[(3S,4R)-1-carbamoyl-4-([4-[3-(2-[3-[1-(2,6-dioxopiperidin-3-yl)-3-methyl-2-oxo-2,3-dihydro-1H-1,3-benzodiazol-5-yl]propoxy]acetamido)propyl] phenyl]methoxy)pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl)phosphonic acid | 1153.7 | (400 MHz, $CD_3OD$) δ 7.69 (d, J = 8.2 Hz, 2H), 7.58 (d, J = 8.2 Hz, 2H), 7.23 (d, J = 7.8 Hz, 2H), 7.13 (d, J = 7.9 Hz, 3H), 7.09-6.96 (m, 5H), 6.37 (d, J = 1.4 Hz, 1H), 5.31 (dd, J = 12.8, 5.3 Hz, 1H), 5.14 (d, J = 10.9 Hz, 1H), 4.50 (s, 2H), 4.01 (d, J = 11.2 Hz, 1H), 3.93 (s, 2H), 3.64-3.57 (m, 1H), 3.54 (t, J = 6.4 Hz, 2H), 3.47 (d, J = 5.1 Hz, 1H), 3.39 (s, 3H), 3.27 (t, J = 7.0 Hz, 2H), 3.24-3.13 (m, 2H), 2.97 (d, J = 11.6 Hz, 2H), 2.92-2.84 (m, 1H), 2.79-2.68 (m, 3H), 2.61 (t, J = 7.7 Hz, 2H), 2.53-2.46 (m, 3H), 2.38-2.11 (m, 5H), 2.03-1.93 (m, 3H), 1.87-1.78 (m, 2H), 1.69 (s, 1H), 1.19-1.03 (m, 4H). |
| 67 | I-66 | (4-[(1E)-1-[[(2S,11S)-2-[[(3S,4R)-1-carbamoyl-4-[(4-[3-[2-(2-[3-[1-(2,6-dioxopiperidin-3-yl)-3-methyl-2-oxo-2,3-dihydro-1H-1,3-benzodiazol-5-yl]propoxy]ethoxy)acetamido] propyl]phenyl)methoxy]pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl)phosphonic acid | 1197.6 | (400 MHz, $CD_3OD$) δ 7.69 (d, J = 8.2 Hz, 2H), 7.57 (d, J = 8.1 Hz, 2H), 7.19 (dd, J = 8.1, 1.9 Hz, 2H), 7.14-7.06 (m, 3H), 7.05-6.98 (m, 4H), 6.94 (d, J = 7.9 Hz, 1H), 6.39-6.34 (m, 1H), 5.39-5.25 (m, 1H), 5.13 (dt, J = 10.9, 3.6 Hz, 1H), 4.67-4.55 (m, 2H), 4.47 (s, 2H), 4.01 (m, 3H), 3.73-3.62 (m, 4H), 3.60-3.39 (m, 4H), 3.37 (s, 3H), 3.31-3.10 (m, 4H), 3.00-2.87 (m, 2H), 2.86-2.67 (m, 4H), 2.59 (t, J = 7.8 Hz, 2H), 2.52 (d, J = 1.3 Hz, 3H), 2.37-2.09 (m, 3H), 2.04-1.85 (m, 3H), 1.81-1.77 (m, 2H), 1.74-1.61 (m, 1H), 1.29 (d, J = 9.5 Hz, 1H), 1.22-1.12 (m, 3H). |
| 68 | I-67 | [4-[(1E)-1-[[(2S,11S)-2-[[(3S,4R)-1-carbamoyl-4-[[4-(3-[2-[2-(2-[3-[3-methyl-1-(1-methyl-2,6-dioxopiperidin-3-yl)-2-oxo-1,3-benzodiazol-5-yl]propoxy]ethoxy)ethoxy]acetamido] propyl)phenyl]methoxy]pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethylphosphonic acid | 1255.7 | (400 MHz, $D_2O$) δ 7.71-7.29 (m, 4H), 7.11-6.15 (m, 11H), 4.99-4.85 (m, 2H), 4.24-4.13 (m, 3H), 3.84 (s, 3H), 3.66-3.28 (m, 9H), 3.28-2.83 (m, 12H), 2.83-2.55 (m, 4H), 2.53-1.40 (m, 19H), 0.97 (s, 3H). |

TABLE 73-continued

| Characterization Data for Exemplary STAT3 Degraders | | | | |
|---|---|---|---|---|
| EXAMPLE | I-# | Chemical Name | MS: $[(M+1)]^+$ | $^1H$ NMR |
| 69 | I-68 | [[({4-[(1E)-1-[[(2S,11S)-2-[[(3S,4R)-1-carbamoyl-4-([4-[3-(2-[3-[1-(2,6-dioxopiperidin-3-yl)-3-methyl-2-oxo-2,3-dihydro-1H-1,3-benzodiazol-5-yl]propoxy]acetamido)propyl] phenyl]methoxy)pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl)([[(2,2-dimethylpropanoyl)oxy]methoxy]) phosphoryl]oxy]methyl 2,2-dimethylpropanoate | 1381.7 | (400 MHz, $CD_3OD$) δ 7.98 (d, J = 9.5 Hz, 1H), 7.69 (d, J = 8.2 Hz, 2H), 7.62 (d, J = 8.3 Hz, 2H), 7.24 (d, J = 7.8 Hz, 2H), 7.18-7.08 (m, 3H), 7.08-6.93 (m, 5H), 6.41 (s, 1H), 5.75-5.63 (m, 4H), 5.31 (dd, J = 12.7, 5.4 Hz, 1H), 5.14 (d, J = 10.6 Hz, 1H), 4.64 (d, J = 9.7 Hz, 1H), 4.55-4.43 (m, 2H), 4.00 (s, 1H), 3.91 (s, 2H), 3.61-3.51 (m, 3H), 3.44 (d, J = 12.8 Hz, 1H), 3.38 (s, 3H), 3.27 (t, J = 7.1 Hz, 2H), 3.24-3.10 (m, 2H), 3.00 (d, J = 16.7 Hz, 1H), 2.95-2.85 (m, 1H), 2.84-2.70 (m, 4H), 2.62 (t, J = 7.7 Hz, 2H), 2.55 (d, J = 1.3 Hz, 3H), 2.26-2.19 (m, 4H), 2.17-2.07 (m, 1H), 1.98-1.84 (m, 3H), 1.82 (p, J = 7.3 Hz, 2H), 1.69 (q, J = 9.3, 5.0 Hz, 1H), 1.24-1.13 (m, 20H). |
| 70 | I-69 | [[({4-[(1E)-1-[[(2S,11S)-2-[[(3S,4R)-1-carbamoyl-4-[[4-(3-[2-[2-(2-[3-[1-(2,6-dioxopiperidin-3-yl)-3-methyl-2-oxo-2,3-dihydro-1H-1,3-benzodiazol-5-yl]propoxy]ethoxy)ethoxy]acetamido] propyl)phenyl]methoxy]pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl)([[(2,2-dimethylpropanoyl)oxy]methoxy]) phosphoryl]oxy]methyl 2,2-dimethylpropanoate | 1470.7 | (400 MHz, DMSO-$d_6$) δ 11.09 (s, 1H), 8.53 (d, J = 7.5 Hz, 1H), 7.87 (d, J = 9.3 Hz, 1H), 7.71-7.65 (m, 3H), 7.60-7.52 (m, 2H), 7.20-7.11 (m, 3H), 7.13-6.93 (m, 7H), 6.86 (d, J = 8.0 Hz, 1H), 6.70 (s, 1H), 6.53 (s, 1H), 5.77-5.65 (m, 4H), 5.33-5.28 (m, 1H), 5.13-5.05 (m, 1H), 4.48 (t, J = 8.3 Hz, 1H), 4.44-4.34 (m, 2H), 3.88 (s, 2H), 3.79 (s, 1H), 3.63-3.54 (m, 6H), 3.52-3.48 (m, 2H), 3.47-3.36 (m, 4H), 3.31 (s, 3H), 3.23-3.01 (m, 4H), 2.86-2.83 (m, 2H), 2.77-2.56 (m, 5H), 2.57-2.50 (m, 3H), 2.17-1.93 (m, 5H), 1.86-1.64 (m, 5H), 1.56 (s, 1H), 1.28-1.18 (m, 2H), 1.15 (s, 18H), 1.11 (s, 1H), 1.07 (s, 3H). |
| 71 | I-70 | [[({4-[(1E)-1-[[(2S,11S)-2-[[(3S,4R)-1-carbamoyl-4-[[4-(3-[15-[1-(2,6-dioxopiperidin-3-yl)-3-methyl-2-oxo-2,3-dihydro-1H-1,3-benzodiazol-5-yl]-3,6,9,12-tetraoxapentadecanamido]propyl) phenyl]methoxy]pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl)([[(2,2-dimethylpropanoyl)oxy]methoxy]) phosphoryl]oxy]methyl 2,2-dimethylpropanoate | 1514.7 | (400 MHz, DMSO-$d_6$) δ 11.09 (s, 1H), 8.54 (d, J = 7.5 Hz, 1H), 7.87 (d, J = 9.2 Hz, 1H), 7.71 (d, J = 8.6 Hz, 3H), 7.57 (d, J = 8.3 Hz, 2H), 7.22-6.95 (m, 10H), 6.86-6.84 (m, 1H), 6.70 (s, 1H), 6.54 (s, 1H), 5.71-5.66 (m, 4H), 5.34-5.30 (m, 1H), 5.09 (d, J = 8.9 Hz, 1H), 4.48-4.46 (m, 1H), 4.40 (s, 2H), 3.87 (s, 3H), 3.78 (d, J = 13.3 Hz, 1H), 3.58-3.50 (m, 10H), 3.49-3.41 (m, 4H), 3.39 (t, J = 6.4 Hz, 3H), 3.12-3.07 (m, 4H), 2.94-2.83 (m, 2H), 2.77-2.60 (m, 4H), 2.55-2.48 (m, 5H), 2.12-1.97 (m, 6H), 1.77-1.69 (m, 5H), 1.56 (s, 1H), 1.24 (s, 18H), 1.08 (s, 3H). |
| 72 | I-71 | [({4-[(1E)-1-[[(2S,11S)-2-[[(3S,4R)-1-Carbamoyl-4-[[4-(5-[[(2S)-1-[(2S,4R)-4-hydroxy-2-([[4-(4-methyl-1,3-thiazol-5-yl)phenyl]methyl]carbamoyl) pyrrolidin-1-yl]-3,3-dimethyl-1-oxobutan-2-yl]carbamoyl]pentyl)phenyl]methoxy] pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethyl([(2,2-dimethylpropanoyl)oxy]methoxy) phosphoryl)oxy]methyl 2,2-dimethylpropanoate | 1494.9 | (400 MHz, $CDCl_3$) δ 8.69 (s, 1H), 7.62 (d, J = 8.1 Hz, 2H), 7.54 (d, J = 8.2 Hz, 2H), 7.43-7.30 (m, 5H), 7.24 (d, J = 7.7 Hz, 2H), 7.06-6.90 (m, 6H), 6.88 (d, J = 9.4 Hz, 1H), 6.38 (d, J = 8.7 Hz, 1H), 6.09 (d, J = 7.8 Hz, 2H), 5.82-5.61 (m, 4H), 5.33-5.10 (m, 2H), 4.68 (t, J = 7.9 Hz, 1H), 4.64-4.44 (m, 5H), 4.43-4.28 (m, 2H), 4.06 (d, J = 11.2 Hz, 1H), 3.95 (s, 1H), 3.60-3.50 (m, 3H), 3.32-3.21 (m, 3H), 3.09 (d, J = 17.6 Hz, 1H), 2.63-2.27 (m, 10H), 2.21-1.68 (m, 8H), 1.56-1.40 (m, 4H), 1.23-1.04 (m, 23H), 0.93 (s, 9H). |
| 73 | I-80 | diammonium [4-[(1E)-1-[[(2S,11S)-2-[[(3S,4R)-1-carbamoyl-4-[[4-(4-[[(2S)-1-[(2S,4R)-4-hydroxy-2-([[4-(4-methyl-1,3-thiazol-5-yl)phenyl]methyl]carbamoyl) pyrrolidin-1-yl]-3,3-dimethyl-1-oxobutan-2-yl]carbamoyl]butyl)phenyl]methoxy] pentan-3-yl]carbamoyl]-12-oxo-1- | 1215.7 | (400 MHz, DMSO-$d_6$) δ 8.99 (s, 1H), 8.58 (d, J = 6.5 Hz, 1H), 8.37 (d, J = 7.2 Hz, 1H), 7.91 (t, J = 9.2 Hz, 2H), 7.42-7.35 (m, 8H), 7.21-7.15 (m, 6H), 7.11-7.05 (m, 3H), 7.06-6.90 (m, 4H), 6.75 (s, 1H), 5.48 (s, 1H), 5.25-4.99 (m, 2H), 4.63-4.14 (m, 8H), 3.91-3.74 (m, 2H), 3.66 (s, 2H), 3.10-2.95 (m, 2H), 2.89-2.76 (m, 2H), 2.54-2.51 (m, 2H), 2.42 (s, 3H), 2.32 (d, J = 15.3 Hz, 1H), 2.20-1.85 (m, 6H), 1.83-172 (s, 1H), 1.68-1.40 (m, 7H), 1.06 (m, 3H), 0.96 (s, 9H). |

TABLE 73-continued

| Characterization Data for Exemplary STAT3 Degraders | | | | |
|---|---|---|---|---|
| EXAMPLE | I-# | Chemical Name | MS: $[(M + 1)]^+$ | $^1H$ NMR |
| | | azatricyclo[6.4.1.0^[4,13]]trideca-4(13),5,7-trien-11-yl]carbamoyl]prop-1-en-2-yl]phenyl]methylphosphonate | | |
| 74 | I-82 | diammonium (2-[[(2S,11S)-2-[[(3S,4R)-1-carbamoyl-4-[[4-(4-[[(2S)-1-[(2S,4R)-4-hydroxy-2-([[4-(4-methyl-1,3-thiazol-5-yl)phenyl]methyl]carbamoyl) pyrrolidin-1-yl]-3,3-dimethyl-1-oxobutan-2-yl]carbamoyl]butyl)phenyl]methoxy] pentan-3-yl]carbamoyl]-12-oxo-1-azatricyclo[6.4.1.0^[4,13]]trideca-4(13),5,7-trien-11-yl]carbamoyl]-1H-indol-5-yl)methylphosphonate | 1214.7 | (400 MHz, $CD_3OD$) δ 8.88 (s, 1H), 8.04 (d, J = 9.4 Hz, 1H), 7.59 (d, J = 3.0 Hz, 1H), 7.51-7.35 (m, 5H), 7.28-7.20 (m, 3H), 7.16-7.07 (m, 5H), 7.06-7.01 (m, 1H), 5.18-5.14 (m, 1H), 4.81-4.76 (m, 1H), 4.64 (s, 1H), 4.61-4.55 (m, 1H), 4.53-4.46 (m, 3H), 4.36 (d, J = 15.5 Hz, 1H), 4.01-3.96 (m, 1H), 3.91 (d, J = 11.1 Hz, 1H), 3.83-3.78 (m, 1H), 3.66-3.53 (m, 1H), 3.53-3.45 (m, 1H), 3.27-3.19 (m, 2H), 3.17-3.14 (m, 1H), 3.12-2.99 (m, 2H), 2.62-2.55 (m, 2H), 2.48 (s, 3H), 2.40-2.15 (m, 7H), 2.13-2.05 (m, 2H), 1.75-1.57 (m, 5H), 1.19 (d, J = 6.3 Hz, 3H), 1.04 (s, 9H). |
| 75 | I-83 | diammonium 2-[[(2S,11S)-2-[[(3S,4R)-1-carbamoyl-4-[[4-(4-[[(2S)-1-[(2S,4R)-4-hydroxy-2-([[4-(4-methyl-1,3-thiazol-5-yl)phenyl]methyl]carbamoyl) pyrrolidin-1-yl]-3,3-dimethyl-1-oxobutan-2-yl]carbamoyl]butyl)phenyl]methoxy] pentan-3-yl]carbamoyl]-12-oxo-1-azatricyclo[6.4.1.0^[4,13]]trideca-4(13),5,7-trien-11-yl]carbamoyl]-1H-indole-5-carbonylphosphonate | 1229.3 | (400 MHz, DMSO-$d_6$) δ 11.91 (s, 1H), 8.98 (s, 1H), 8.90 (d, J = 1.5 Hz, 1H), 8.59 (t, J = 6.1 Hz, 1H), 7.98-7.86 (m, 4H), 7.47-7.34 (m, 4H), 7.25-7.13 (m, 2H), 7.12-7.04 (m, 4H), 7.00 (t, J = 7.4 Hz, 1H), 6.71 (s, 1H), 5.13-5.07 (m, 2H), 4.71-4.60 (m, 1H), 4.55 (d, J = 9.3 Hz, 1H), 4.47-4.32 (m, 4H), 4.26-4.23 (m, 2H), 3.82-3.76 (m, 1H), 3.70-3.60 (m, 2H), 3.51-3.39 (m, 2H), 3.26-3.04 (m, 2H), 2.88 (d, J = 16.6 Hz, 1H), 2.54 (d, J = 6.1 Hz, 2H), 2.44 (s, 3H), 2.37-1.94 (m, 6H), 1.92-1.87 (m, 1H), 1.77 (d, J = 6.4 Hz, 1H), 1.61-1.41 (m, 6H), 1.08-1.02 (m, 3H), 0.94 (s, 9H). |
| 76 | I-84 | 2-[[(2S,11S)-2-[[(3S,4R)-1-carbamoyl-4-[(4-[4-[1-(2,6-dioxopiperidin-3-yl)-3-methyl-2-oxo-1,3-benzodiazol-5-yl]butyl]phenyl)methoxy]pentan-3-yl]carbamoyl]-12-oxo-1-azatricyclo[6.4.1.0^[4,13]]trideca-4(13),5,7-trien-11-yl]carbamoyl]-1H-indole-5-carbonylphosphonic acid | 1029.6 | (400 MHz, DMSO-$d_6$) δ 12.13 (s, 1H), 11.09 (s, 1H), 9.00 (d, J = 8.1 Hz, 1H), 8.82 (d, J = 1.6 Hz, 1H), 7.98-7.86 (m, 2H), 7.57-7.47 (m, 2H), 7.23-7.14 (m, 3H), 7.14-7.04 (m, 4H), 7.04-6.93 (m, 3H), 6.88-6.80 (m, 1H), 6.70 (s, 1H), 5.35-5.27 (m, 1H), 5.16-5.08 (m, 1H), 4.72-4.63 (m, 1H), 4.39 (s, 2H), 3.86-3.78 (m, 2H), 3.31 (s, 3H), 3.26-2.99 (m, 2H), 2.98-2.80 (m, 2H), 2.76-2.53 (m, 7H), 2.28-2.20 (m, 2H), 2.13-1.96 (m, 3H), 1.76 (d, J = 6.0 Hz, 1H), 1.66-1.47 (m, 5H), 1.07 (d, J = 6.2 Hz, 3H). |
| 77 | I-85 | diammonium 2-[[(2S,11S)-2-[[(3S,4R)-1-carbamoyl-4-[[2-(5-[[(2S)-1-[(2S,4R)-4-hydroxy-2-([[4-(4-methyl-1,3-thiazol-5-yl)phenyl]methyl]carbamoyl) pyrrolidin-1-yl]-3,3-dimethyl-1-oxobutan-2-yl]carbamoyl]pentyl)phenyl]methoxy] pentan-3-yl]carbamoyl]-12-oxo-1-azatricyclo[6.4.1.0^[4,13]]trideca-4(13),5,7-trien-11-yl]carbamoyl]-1H-indole-5-carbonylphosphonate | 1243.8 | (400 MHz, DMSO-$d_6$) δ 11.86 (s, 1H), 9.03-8.90 (m, 2H), 8.64-8.51 (m, 1H), 7.98-7.83 (m, 3H), 7.52-7.31 (m, 6H), 7.29-6.86 (m, 9H), 6.71 (s, 1H), 5.14-5.04 (m, 2H), 4.72-4.13 (m, 9H), 3.84-3.76 (m, 1H), 3.66 (d, J = 5.4 Hz, 2H), 3.56-3.43 (m, 2H), 3.23-3.04 (m, 2H), 2.89 (d, J = 16.6 Hz, 1H), 2.70-2.64 (m, 2H), 2.45 (s, 3H), 2.35-1.96 (m, 7H), 1.93-1.70 (m, 2H), 1.62-1.42 (m, 5H), 1.33-1.21 (m, 3H), 1.14-1.05 (m, 3H), 0.93 (s, 9H). |
| 78 | I-86 | diammonium 2-[[(2S,115)-2-[[(3S,4R)-1-carbamoyl-4-[[4-(5-[[(2S)-1-[(2S,4R)-4-hydroxy-2-([[4-(4-methyl-1,3-thiazol-5-yl)phenyl]methyl]carbamoyl) pyrrolidin-1-yl]-3,3-dimethyl-1-oxobutan-2-yl]carbamoyl]pent-1-yn-1-yl)phenyl]methoxy]pentan-3-yl]carbamoyl]-12-oxo-1-azatricyclo[6.4.1.0^[4,13]]trideca-4(13),5,7-trien-11-yl]carbamoyl]-1H-indole-5-carbonylphosphonate | 1238.5 | (400 MHz, DMSO-$d_6$) δ 11.92 (s, 1H), 9.09-8.77 (m, 3H), 8.57 (d, J = 6.2 Hz, 1H), 8.01-7.86 (m, 3H), 7.46-7.35 (m, 7H), 7.35-7.21 (m, 5H), 7.18 (s, 2H), 7.08 (d, J = 4.7 Hz, 2H), 6.99 (t, J = 7.5 Hz, 1H), 6.69 (s, 1H), 5.11 (d, J = 10.6 Hz, 1H), 4.71-4.63 (m, 1H), 4.56 (d, J = 9.4 Hz, 1H), 4.48-4.39 (m, 4H), 4.37-4.34 (m, 1H), 4.27-4.20 (m, 1H), 3.85-3.63 (m, 2H), 3.49-3.41 (m, 2H), 3.30-3.07 (m, 2H), 2.84 (d, J = 16.6 Hz, 1H), 2.45-2.38 (m, 5H), 2.37-2.15 (m, 4H), 2.12-1.97 (m, 3H), 1.92 (d, J = 12.1 Hz, 1H), 1.87-1.70 (m, 3H), 1.61-1.49 (m, 1H), 1.12-1.04 (m, 3H), 0.95 (s, 9H). |
| 79 | I-87 | diammonium 2-[[(2S,11S)-2-[[(3S,4R)-1-carbamoyl-4-[[6-(2-[[(2S)-1-[(2S,4R)-4-hydroxy-2-([[4-(4-methyl-1,3-thiazol-5- | 1251.3 | (400 MHz, $CD_3OD$) δ 8.98 (t, J = 1.1 Hz, 1H), 8.89 (s, 1H), 8.13-8.01 (m, 2H), 7.80-7.68 (m, 3H), 7.62 (s, 1H), 7.55-7.38 (m, 6H), 7.38-7.28 (m, 2H), 7.11 (d, J = 7.6 Hz, 1H), |

TABLE 73-continued

| Characterization Data for Exemplary STAT3 Degraders | | | | |
|---|---|---|---|---|
| EXAMPLE | I-# | Chemical Name | MS: $[(M + 1)]^+$ | $^1H$ NMR |
| | | yl)phenyl]methyl]carbamoyl) pyrrolidin-1-yl]-3,3-dimethyl-1-oxobutan-2-yl]carbamoyl]ethyl)naphthalen-2-yl]methoxy]pentan-3-yl]carbamoyl]-12-oxo-1-azatricyclo[6.4.1.0^[4,13]]trideca-4(13),5,7-trien-11-yl]carbamoyl]-1H-indole-5-carbonylphosphonate | | 7.04-6.88 (m, 2H), 5.18-5.12 (m, 1H), 4.82-4.76 (m, 1H), 4.73-4.43 (m, 6H), 4.40-4.27 (m, 1H), 4.09-3.99 (m, 1H), 3.90 (d, J = 11.0 Hz, 1H), 3.82-3.74 (m, 1H), 3.67-3.57 (m, 1H), 3.52-3.37 (m, 1H), 3.27-3.13 (m, 2H), 3.07 (t, J = 7.9 Hz, 2H), 2.98-2.86 (m, 1H), 2.78-2.57 (m, 2H), 2.48 (s, 3H), 2.45-2.17 (m, 4H), 2.14-1.98 (m, 2H), 1.79-1.69 (m, 1H), 1.25 (d, J = 6.3 Hz, 3H), 0.93 (s, 9H). |
| 80 | I-88 | 2-[1(5S,8S,10aR)-8-[[(1S)-3-carbamoyl-1-(diphenylmethylcarbamoyl)propyl] carbamoyl]-3-[5-[1-(2,6-dioxopiperidin-3-yl)-3-methyl-2-oxo-1,3-benzodiazol-4-yl]pentanoyl]-6-oxo-octahydropyrrolo[1,2-a][1,5]diazocin-5-yl]carbamoyl]-1H-indole-5-carbonylphosphonic acid | 1113.3 | (400 MHz, DMSO-$d_6$) δ 12.13-11.98 (m, 1H), 11.10 (s, 1H), 8.85-8.70 (m, 2H), 8.40 (s, 1H), 8.28-8.16 (m, 1H), 7.95 (d, J = 8.7 Hz, 1H), 7.51 (d, J = 8.1 Hz, 1H), 7.46-7.38 (m, 1H), 7.37-7.19 (m, HH), 7.01-6.93 (m, 2H), 6.92-6.87 (m, 1H), 6.82-6.76 (m, 1H), 6.10 (t, J = 8.0 Hz, 1H), 5.42-5.31 (m, 1H), 5.03-4.86 (m, 1H), 4.46 (d, J = 8.6 Hz, 1H), 4.41-4.32 (m, 1H), 4.23-4.14 (m, 1H), 3.96 (d, J = 14.7 Hz, 1H), 3.88-3.72 (m, 2H), 3.57 (s, 3H), 3.01-2.85 (m, 3H), 2.83-2.55 (m, 3H), 2.41-2.36 (m, 2H), 2.23-2.04 (m, 3H), 2.05-1.94 (m, 4H), 1.93-1.86 (m, 2H), 1.84-1.58 (m, 7H). |
| 81 | I-89 | diammonium [4-[(1E)-1-[[(5S,8S,10aR)-8-[[(1S)-3-carbamoyl-1-(diphenylmethylcarbamoyl)propyl] carbamoyl]-3-[8-[2-(2,6-dioxopiperidin-3-yl)-1-oxo-3H-isoindol-4-yl]oct-7-ynoyl]-6-oxo-octahydropyrrolo[1,2-a][1,5]diazocin-5-yl]carbamoyl]prop-1-en-2-yl]phenyl]methylphosphonate | 1123.6 | (400 MHz, $CD_3OD$) δ 7.75 (d, J = 7.5 Hz, 1H), 7.65-7.59 (m, 1H), 7.51 (t, J = 7.7 Hz, 1H), 7.41-7.21 (m, 14H), 6.15 (d, J = 9.6 Hz, 1H), 5.55 (d, J = 5.4 Hz, 1H), 5.29-5.08 (m, 3H), 4.76-4.70 (m, 1H), 4.60-4.33 (m, 4H), 4.19-4.10 (m, 1H), 3.76 (d, J = 15.7 Hz, 2H), 3.68-3.40 (m, 4H), 3.07-3.01 (m, 1H), 2.99 (s, 1H), 2.96-2.73 (m, 2H), 2.63-2.31 (m, 7H), 2.30-2.10 (m, 3H), 2.08-1.81 (m, 4H), 1.82-1.63 (m, 5H), 1.62-1.48 (m, 2H). |
| 82 | I-90 | 2-[[(2S,11S)-2-[[(3S,4R)-1-carbamoyl-4-[[4-(4-[[(2S)-1-[(2S,4R)-4-hydroxy-2-([1-[4-(4-methyl-1,3-thiazol-5-yl)phenyl]cyclopropyl]carbamoyl) pyrrolidin-1-yl]-3,3-dimethyl-1-oxobutan-2-yl]carbamoyl]butyl)phenyl]methoxy] pentan-3-yl]carbamoyl]-12-oxo-1-azatricyclo[6.4.1.0^[4,13]]trideca-4(13),5,7-trien-11-yl]carbamoyl]-1H-indole-5-carbonylphosphonic acid | 1255.4 | (400 MHz, DMSO-$d_6$) δ 12.10 (s, 1H), 8.99 (d, J = 9.4 Hz, 2H), 8.82 (d, J = 9.0 Hz, 2H), 7.99-7.88 (m, 3H), 7.58-7.47 (m, 2H), 7.36-7.28 (m, 4H), 7.17 (d, J = 8.0 Hz, 3H), 7.14-7.08 (s, 4H), 7.02 (d, J = 7.3 Hz, 1H), 6.69 (s, 1H), 5.12 (d, J = 10.6 Hz, 2H), 4.72-4.66 (s, 1H), 4.56 (d, J = 9.1 Hz, 1H), 4.42-4.33 (m, 4H), 3.85-3.76 (m, 2H), 3.68-3.62 (m, 2H), 2.89 (d, J = 16.8 Hz, 1H), 2.68-2.58 (m, 2H), 2.44 (s, 3H), 2.37-3.30 (s, 2H), 2.29-1.94 (m, 7H), 1.88-1.68 (m, 2H), 1.61-1.44 (m, 5H), 1.28-1.18 (m, 4H), 1.16-1.05 (m, 4H), 0.94 (s, 9H). |
| 83 | I-91 | 2-[1(5S,8S,10aR)-8-[[(1S)-3-carbamoyl-1-(diphenylmethylcarbamoyl)propyl] carbamoyl]-3-[8-[1-(2,6-dioxopiperidin-3-yl)-3-methyl-2-oxo-1,3-benzodiazol-4-yl]octanoyl]-6-oxo-octahydropyrrolo[1,2-a][1,5]diazocin-5-yl]carbamoyl]-1H-indole-5-carbonylphosphonic acid | 1155.6 | (400 MHz, DMSO-$d_6$) δ 12.28-11.94 (m, 1H), 11.09 (s, 1H), 8.86-8.69 (m, 2H), 8.49-8.39 (m, 1H), 8.26-8.14 (m, 1H), 7.95 (d, J = 8.8 Hz, 1H), 7.53 (d, J = 8.8 Hz, 1H), 7.49-7.39 (m, 1H), 7.38-7.20 (m, 11H), 6.98-6.90 (m, 2H), 6.90-6.68 (m, 2H), 6.14-6.06 (m, 1H), 5.40-5.31 (m, 1H), 5.03-4.85 (m, 1H), 4.51-4.15 (m, 4H), 4.07-3.60 (m, 4H), 3.55 (s, 3H), 3.35-3.21 (m, 2H), 2.96-2.81 (m, 3H), 2.78-2.57 (m, 3H), 2.41-2.30 (m, 1H), 2.23-2.04 (m, 3H), 2.04-1.87 (m, 3H), 1.87-1.68 (m, 2H), 1.67-1.52 (m, 6H), 1.42-1.30 (m, 6H). |
| 84 | I-92 | trifluoroacetic acid; [4-[(1E)-1-[[(2S,11S)-2-[[(3S,4R)-1-carbamoyl-4-[[4-(4-[[(2S)-1-[(2S,4R)-4-hydroxy-2-([1-[4-(4-methyl-1,3-thiazol-5-yl)phenyl]cyclopropyl]carbamoyl) pyrrolidin-1-yl]-3,3-dimethyl-1-oxobutan-2-yl]carbamoyl]butyl)phenyl]methoxy] pentan-3-yl]carbamoyl]-12- | 1278.9 | (400 MHz, $CD_3OD$) δ 9.07 (d, J = 9.4 Hz, 1H), 7.64 (q, J = 8.5 Hz, 4H), 7.41 (q, J = 8.1 Hz, 4H), 7.24 (d, J = 7.7 Hz, 2H), 7.17-7.11 (m, 3H), 7.11-7.06 (m, 2H), 6.39 (s, 1H), 5.16 (d, J = 11.0 Hz, 1H), 4.65 (d, J = 16.7 Hz, 2H), 4.60-4.44 (m, 4H), 4.05-3.97 (m, 1H), 3.91 (d, J = 11.1 Hz, 1H), 3.80 (d, J = 8.4 Hz, 1H), 3.62-3.54 (m, 1H), 3.49 (d, J = 13.5 Hz, 1H), 3.17 (d, J = 15.9 Hz, 2H), 3.04 (d, J = 16.0 Hz, 1H), 2.66-2.59 (m, 2H), 2.55 (s, |

TABLE 73-continued

| Characterization Data for Exemplary STAT3 Degraders | | | | |
|---|---|---|---|---|
| EXAMPLE | I-# | Chemical Name | MS: $[(M + 1)]^+$ | $^1H$ NMR |
| | | oxo-1-azatricyclo[6.4.1.0^[4,13]]trideca-4(13),5,7-trien-11-yl]carbamoyl]prop-1-en-2-yl]phenyl]difluoromethylphosphonic acid | | 3H), 2.49 (s, 3H), 2.42-2.14 (m, 6H), 2.08-1.96 (m, 2H), 1.72-1.58 (m, 5H), 1.43-1.27 (m, 5H), 1.20 (d, J = 6.3 Hz, 3H), 1.05 (s, 9H). |
| 85 | I-93 | diammonium [4-[(1E)-1-[[(2S,11S)-2-[[(3S,4R)-1-carbamoyl-4-[[4-(4-[[(2S)-1-[(2S,4R)-4-hydroxy-2-[[(1S)-1-[4-(4-methyl-1,3-thiazol-5-yl)phenyl]ethyl]carbamoyl] pyrrolidin-1-yl]-3,3-dimethyl-1-oxobutan-2-yl]carbamoyl]butyl)phenyl]methoxy] pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethylphosphonate | 1265.8 | (400 MHz, DMSO-$d_6$) δ 8.99 (s, 1H), 8.49 (d, J = 7.5 Hz, 1H), 8.39 (d, J = 7.8 Hz, 1H), 7.85 (t, J = 10.4 Hz, 2H), 7.62-7.58 (m, 4H), 7.44 (d, J = 8.0 Hz, 2H), 7.38 (d, J = 8.0 Hz, 2H), 7.18-7.03 (m, 11H), 6.70 (s, 1H), 6.47 (s, 1H), 5.18-5.05 (m, 1H), 4.96-4.87 (m, 1H), 4.60-4.33 (m, 5H), 4.28 (d, J = 4.7 Hz, 1H), 3.83-3.75 (m, 1H), 3.63-3.57 (m, 2H), 3.47-3.42 (m, 2H), 3.22-3.00 (m, 2H), 2.87 (d, J = 16.4 Hz, 1H), 2.58-2.54 (m, 2H), 2.46 (s, 3H), 2.35-2.25 (m, 1H), 2.24-1.94 (m, 6H), 1.78 (d, J = 8.2 Hz, 2H), 1.60-1.48 (m, 5H), 1.38 (d, J = 7.0 Hz, 3H), 1.08 (d, J = 6.2 Hz, 3H), 0.94 (s, 9H). |
| 86 | I-94 | diammonium 2-[[(2S,11S)-2-[[(3S,4R)-1-carbamoyl-4-[[4-(4-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]butyl)phenyl]methoxy] pentan-3-yl]carbamoyl]-12-oxo-1-azatricyclo[6.4.1.0^[4,13]]trideca-4(13),5,7-trien-11-yl]carbamoyl]-1H-indole-5-carbonylphosphonate | 1243.6 | (400 MHz, DMSO-$d_6$) δ 11.90 (s, 1H), 9.01-8.97 (m, 3H), 8.39 (d, J = 7.8 Hz, 1H), 8.00-7.79 (m, 3H), 7.50-7.31 (m, 6H), 7.16-6.98 (m, 9H), 6.70 (s, 1H), 5.12 (d, J = 11.0 Hz, 1H), 4.92 (t, J = 7.2 Hz, 1H), 4.69 (d, J = 8.0 Hz, 1H), 4.52 (d, J = 9.2 Hz, 1H), 4.48-4.36 (m, 3H), 4.32-4.18 (m, 1H), 3.85-3.76 (m, 1H), 3.61 (s, 2H), 3.46-3.38 (m, 2H), 3.30-3.07 (m, 2H), 2.97-2.83 (m, 1H), 2.48-2.43 (m, 4H), 2.36-2.20 (m, 4H), 2.20-1.96 (m, 5H), 1.84-1.68 (m, 2H), 1.58-1.43 (m, 6H), 1.38 (d, J = 7.0 Hz, 3H), 1.08 (d, J = 6.2 Hz, 3H), 0.93 (s, 9H). |
| 87 | I-95 | diammonium 2-[[(2S,11S)-2-[[(3S,4R)-1-carbamoyl-4-[[3-(4-[[(2S)-1-[(2S,4R)-4-hydroxy-2-([[4-(4-methyl-1,3-thiazol-5-yl)phenyl]methyl]carbamoyl) pyrrolidin-1-yl]-3,3-dimethyl-1-oxobutan-2-yl]carbamoyl]butyl)phenyl]methoxy] pentan-3-yl]carbamoyl]-12-oxo-1-azatricyclo[6.4.1.0^[4,13]]trideca-4(13),5,7-trien-11-yl]carbamoyl]-1H-indole-5-carbonylphosphonate | 1228.6 | (400 MHz, DMSO-$d_6$) δ 11.89 (s, 1H), 9.10-8.85 (m, 2H), 8.65-8.50 (m, 1H), 7.98-7.85 (m, 2H), 7.76-7.66 (m, 1H), 7.46-7.32 (m, 6H), 7.22-6.94 (m, 7H), 6.72 (s, 1H), 5.16-5.06 (m, 1H), 4.74-4.63 (m, 1H), 4.55 (d, J = 9.1 Hz, 1H), 4.46-4.38 (m, 5H), 4.23 (t, J = 6.7 Hz, 2H), 3.85-3.78 (m, 1H), 3.72-3.59 (m, 2H), 3.55-3.30 (m, 2H), 3.01-2.79 (m, 2H), 2.45 (s, 3H), 2.34-1.97 (m, 5H), 1.93-1.78 (m, 2H), 1.69-1.33 (m, 7H), 1.24 (s, 3H), 1.17-1.03 (m, 9H), 1.02-0.74 (m, 3H). |
| 88 | I-96 | diammonium 2-[[(2S,11S)-2-[[(3S,4R)-1-carbamoyl-4-[[4-(4-[[(2S)-1-[(2S,4R)-4-hydroxy-2-([[4-(4-methyl-1,3-thiazol-5-yl)phenyl]methyl]carbamoyl) pyrrolidin-1-yl]-3,3-dimethyl-1-oxobutan-2-yl]carbamoyl]but-1-yn-1-yl)phenyl]methoxy]pentan-3-yl]carbamoyl]-12-oxo-1-azatricyclo[6.4.1.0^[4,13]]trideca-4(13),5,7-trien-11-yl]carbamoyl]-1H-indole-5-carbonylphosphonate | 1224.5 | (400 MHz, DMSO-$d_6$) δ 11.92 (s, 1H), 9.09-8.77 (m, 2H), 8.57 (d, J = 6.2 Hz, 1H), 8.01-7.86 (m, 1H), 7.46-7.35 (m, 5H), 7.35-7.21 (m, 5H), 7.20-6.95 (m, 2H), 6.99 (t, J = 7.5 Hz, 1H), 6.69 (s, 1H), 5.11 (d, J = 10.6 Hz, 1H), 4.71-4.63 (m, 1H), 4.56 (d, J = 9.4 Hz, 1H), 4.48-4.39 (m, 5H), 4.27-4.20 (m, 1H), 3.78-3.63 (m, 2H), 3.49-3.41 (m, 2H), 3.18-3.07 (m, 2H), 2.84 (d, J = 16.6 Hz, 1H), 2.45 (s, 3H), 2.37-2.15 (m, 2H), 2.12-1.97 (m, 4H), 1.92 (d, J = 12.1 Hz, 1H), 1.87-1.70 (m, 1H), 1.61-1.49 (m, 1H), 1.26-1.21 (m, 5H), 1.12-1.04 (m, 3H), 0.95 (s, 9H). |
| 89 | I-97 | 2-[[(5S,8S,10aR)-8-[[(1S)-3-carbamoyl-1-(diphenylmethylcarbamoyl)propyl] carbamoyl]-3-[8-[1-(2,6-dioxopiperidin-3-yl)-3-methyl-2-oxo-1,3-benzodiazol-5-yl]octanoyl]-6-oxo-octahydropyrrolo[1,2-a][1,5]diazocin-5-yl]carbamoyl]-1H-indole-5-carbonylphosphonic acid | 1156.1 | (400 MHz, DMSO-$d_6$) δ 12.13-12.01 (m, 1H), 11.09 (s, 1H), 8.87-8.67 (m, 2H), 8.44 (d, J = 6.9 Hz, 1H), 8.26-8.17 (m, 1H), 7.95 (d, J = 8.7 Hz, 1H), 7.54 (d, J = 8.8 Hz, 1H), 7.48-7.42 (m, 1H), 7.37-7.22 (m, 11H), 7.03-6.96 (m, 2H), 6.87-6.72 (m, 2H), 6.13-6.06 (m, 1H), 5.37-5.25 (m, 1H), 5.02-4.85 (m, 1H), 4.52-4.14 (m, 3H), 4.13-3.64 (m, 2H), 3.35-3.27 (m, 6H), 2.96-2.83 (m, 1H), 2.77-2.54 (m, 5H), 2.48-2.29 (m, 2H), 2.18-2.05 (m, 3H), 2.04-1.86 (m, 4H), 1.86-1.69 (m, 3H), 1.69-47 (m, 5H), 1.41-1.20 (m, 6H). |
| 90 | I-99 | 2-[[(5S,8S,10aR)-8-[[(1S)-3-carbamoyl-1-(diphenylmethylcarbamoyl)propyl] carbamoyl]-3-[7-[1-(2,6- | 1138.0 | (400 MHz, DMSO-$d_6$) δ 12.10-11.98 (m, 1H), 11.12 (s, 1H), 8.88-8.69 (m, 2H), 8.41 (d, J = 6.8 Hz, 1H), 8.28-8.15 (m, 1H), 7.96 (d, J = 8.8 Hz, 1H), 7.51 (d, J = 8.7 Hz, 1H), |

TABLE 73-continued

| EXAMPLE | I-# | Chemical Name | MS: [(M + 1)]+ | $^1$H NMR |
|---|---|---|---|---|
| | | Characterization Data for Exemplary STAT3 Degraders | | |
| | | dioxopiperidin-3-yl)-3-methyl-2-oxo-1,3-benzodiazol-5-yl]hept-6-ynoyl]-6-oxo-octahydropyrrolo[1,2-a][1,5]diazocin-5-yl]carbamoyl]-1H-indole-5-carbonylphosphonic acid | | 7.48-7.38 (m, 1H), 7.38-7.19 (m, 12H), 7.09 (s, 2H), 6.85-6.71 (m, 1H), 6.15-6.06 (m, 1H), 5.41-5.34 (m, 1H), 5.06-4.85 (m, 1H), 4.52-4.16 (m, 3H), 4.16-3.63 (m, 3H), 3.30 (s, 3H), 3.02-2.83 (m, 1H), 2.80-2.53 (m, 5H), 2.47 (d, J = 7.1 Hz, 2H), 2.21-2.08 (m, 3H), 2.06-1.96 (m, 3H), 1.95-1.86 (m, 3H), 1.84-1.56 (m, 8H). |
| 91 | I-100 | diammonium 2-[[(2S,11S)-2-[[(3S,4R)-1-carbamoyl-4-[[4-(6-[[(2S)-1-[(2S,4R)-4-hydroxy-2-([[4-(4-methyl-1,3-thiazol-5-yl)phenyl]methyl]carbamoyl) pyrrolidin-1-yl]-3,3-dimethyl-1-oxobutan-2-yl]carbamoyl]hexyl)phenyl]methoxy] pentan-3-yl]carbamoyl]-12-oxo-1-azatricyclo[6.4.1.0^[4,13]]trideca-4(13),5,7-trien-11-yl]carbamoyl]-1H-indole-5-carbonylphosphonate | 1257.7 | (400 MHz, DMSO-$d_6$) δ 11.95 (s, 1H), 9.03-8.94 (m, 2H), 8.58 (t, J = 6.0 Hz, 1H), 8.06-7.74 (m, 2H), 7.59-7.29 (m, 6H), 7.29-6.90 (m, 7H), 6.71 (s, 1H), 5.21-4.99 (m, 2H), 4.77-4.49 (m, 2H), 4.49-4.13 (m, 6H), 3.92-3.46 (m, 6H), 3.26-2.69 (m, 3H), 2.44 (s, 3H), 2.32-2.18 (m, 2H), 2.16-1.97 (m, 4H), 1.94-1.86 (m, 1H), 1.82-1.71 (s, 1H), 1.56-1.43 (m, 5H), 1.30-1.14 (m, 5H), 1.07 (d, J = 6.1 Hz, 2H), 0.94 (s, 9H). |
| 92 | I-101 | diammonium 2-[[(2S,11S)-2-[[(3S,4R)-1-carbamoyl-4-[[4-(3-[[(2S)-1-[(2S,4R)-4-hydroxy-2-([[4-(4-methyl-1,3-thiazol-5-yl)phenyl]methyl]carbamoyl) pyrrolidin-1-yl]-3,3-dimethyl-1-oxobutan-2-yl]carbamoyl]propyl)phenyl]methoxy] pentan-3-yl]carbamoyl]-12-oxo-1-azatricyclo[6.4.1.0^[4,13]]trideca-4(13),5,7-trien-11-yl]carbamoyl]-1H-indole-5-carbonylphosphonate | 1215.6 | (400 MHz, DMSO-$d_6$) δ 11.96 (s, 1H), 9.13-8.87 (m, 2H), 8.59 (t, J = 6.3 Hz, 1H), 7.99-7-87 (m, 2H), 7.67-7.33 (m, 6H), 7.33-6.89 (m, 8H), 6.71 (s, 1H), 5.20-5.10 (m, 2H), 4.72-4.52 (m, 2H), 4.52-4.31 (m, 5H), 4.27-4.17 (m, 1H), 3.80 (s, 1H), 3.68 (d, J = 3.3 Hz, 2H), 3.54-3.44 (m, 2H), 3.29-2.62 (m, 2H), 2.44 (s, 3H), 2.37-1.87 (m, 8H), 1.81-1.67 (m, 3H), 1.54 (d, J = 11.8 Hz, 1H), 1.34-1.00 (m, 6H), 0.95 (s, 9H). |
| 93 | I-102 | diammonium 2-[[(5S,8S,10aR)-8-[[(1S)-3-carbamoyl-1-(diphenylmethylcarbamoyl)propyl] carbamoyl]-3-[8-[2-(2,6-dioxopiperidin-3-yl)-1-oxo-3H-isoindol-4-yl]oct-7-ynoyl]-6-oxo-octahydropyrrolo[1,2-a][1,5]diazocin-5-yl]carbamoyl]-1-methylindole-5-carbonylphosphonate | 1150.6 | (400 MHz, DMSO-$d_6$) δ 11.00 (s, 1H), 8.88-8.74 (m, 2H), 8.39-8.03 (m, 2H), 7.76-7.42 (m, 5H), 7.34-7.16 (m, 14H), 6.83-6.68 (m, 1H), 6.14-6.04 (m, 1H), 5.17-5.08 (m, 1H), 4.97-4.77 (m, 1H), 4.56-4.13 (m, 5H), 4.03-3.85 (m, 3H), 3.82-3.68 (m, 1H), 2.93-2.80 (m, 2H), 2.72-2.55 (m, 2H), 2.47-2.28 (m, 2H), 2.21-1.36 (m, 21H). |
| 94 | I-103 | 2-[[(5S,8S,10aR)-8-[[(1S)-3-carbamoyl-1-(diphenylmethylcarbamoyl)propyl] carbamoyl]-3-[7-[1-(2,6-dioxopiperidin-3-yl)-3-methyl-2-oxo-1,3-benzodiazol-5-yl]heptanoyl]-6-oxo-octahydropyrrolo[1,2-a][1,5]diazocin-5-yl]carbamoyl]-1H-indole-5-carbonylphosphonic acid | 1141.9 | (400 MHz, DMSO-$d_6$) δ 12.35-11.96 (m, 1H), 11.09 (s, 1H), 8.85-8.75 (m, 2H), 8.43 (d, J = 6.0 Hz, 1H), 8.27-8.18 (m, 1H), 7.96 (d, J = 8.6 Hz, 1H), 7.53 (d, J = 9.0 Hz, 1H), 7.49-7.38 (m, 1H), 7.38-7.20 (m, HH), 7.05-6.95 (m, 2H), 6.90-6.70 (m, 2H), 6.14-5.07 (m, 1H), 5.40-5.28 (m, 1H), 5.02-4.83 (m, 1H), 4.49-4.34 (m, 2H), 4.32-4.16 (m, 1H) 4.06-3.90 (m, 2H), 3.86-3.75 (m, 2H), 3.65-3.35 (m, 2H), 3.30 (s, 3H), 2.96-2.88 (m, 1H), 2.77-2.54 (m, 4H), 2.49-2.32 (m, 1H), 2.20-2.08 (m, 3H), 2.05-1.85 (m, 4H), 1.85-1.71 (m, 4H), 1.69-1.53 (m, 3H), 1.45-1.28 (m, 3H). |
| 95 | I-104 | 2-[[(5S,8S,10aR)-8-[[(1S)-3-carbamoyl-1-(diphenylmethylcarbamoyl)propyl] carbamoyl]-3-[8-[1-(2,6-dioxopiperidin-3-yl)-3-methyl-2-oxo-1,3-benzodiazol-5-yl]oct-7-ynoyl]-6-oxo-octahydropyrrolo[1,2-a][1,5]diazocin-5-yl]carbamoyl]-1H-indole-5-carbonylphosphonic acid | 1151.8 | (400 MHz, DMSO-$d_6$) δ 12.13-12.02 (m, 1H), 11.11 (s, 1H), 8.85-8.72 (m, 2H), 8.45-8.40 (m, 1H), 8.26-8.15 (m, 1H), 8.03-7.84 (m, 1H), 7.57-7.37 (m, 2H), 7.37-7.20 (m, 11H), 7.08 (d, J = 6.7 Hz, 2H), 6.82-6.65 (m 1H), 6.14-6.08 (m, 1H), 5.42-5.33 (m, 1H), 5.03-4.88 (m, 1H), 4.50-4.11 (m, 3H), 4.00-3.54 (m, 3H), 3.35 (s, 3H), 2.86 (d, J = 15.9 Hz, 1H), 2.73-2.56 (m, 3H), 2.46-2.34 (m, 3H), 2.27-1.13 (m, 18H). |
| 96 | I-105 | 2-[[(5S,8S,10aR)-8-[[(1S)-3-carbamoyl-1-(diphenylmethylcarbamoyl)propyl] carbamoyl]-3-[6-[1-(2,6-dioxopiperidin-3-yl)-3-methyl-2- | 1124.0 | $^1$H NMR (400 MHz, DMSO-$d_6$) δ 12.30-11.89 (m, 1H), 11.12 (d, J = 7.5 Hz, 1H), 8.86-8.70 (m, 2H), 8.52-8.37 (m, 1H), 8.27-8.18 (m, 1H), 7.95 (d, J = 8.8 Hz, 1H), 7.53 (d, J = 8.8 Hz, 1H), 7.47-7.38 (m, 1H), 7.38-7.20 (m, |

TABLE 73-continued

| Characterization Data for Exemplary STAT3 Degraders | | | | |
|---|---|---|---|---|
| EXAMPLE | I-# | Chemical Name | MS: $[(M + 1)]^+$ | $^1H$ NMR |
| | | oxo-1,3-benzodiazol-5-yl]hex-5-ynoyl]-6-oxo-octahydropyrrolo[1,2-a][1,5]diazocin-5-yl]carbamoyl]-1H-indole-5-carbonylphosphonic acid | | 12H), 7.15-7.00 (m, 2H), 6.84-6.69 (m, 1H), 6.13-6.05 (m, 1H), 5.42-5.28 (m, 1H), 5.07-4.85 (m, 1H), 4.53-4.14 (m, 3H), 4.04-3.68 (m, 4H), 3.50-3.35 (m, 2H), 3.32 (s, 3H), 2.96-2.78 (m, 2H), 2.76-2.56 (m, 3H), 2.21-1.82 (m, 10H), 1.81-1.59 (m, 4H). |
| 97 | I-106 | diammonium 2-[[(5S,8S,10aR)-8-[[(1S)-3-carbamoyl-1-(diphenylmethylcarbamoyl)propyl]carbamoyl]-3-[8-[2-(2,6-dioxopiperidin-3-yl)-1-oxo-3H-isoindol-4-yl]oct-7-ynoyl]-6-oxo-octahydropyrrolo[1,2-a][1,5]diazocin-5-yl]carbamoyl]-1H-indole-5-carbonylphosphonate | 1123.2 | (400 MHz, $CD_3OD$) δ 7.76-7.69 (m, 1H), 7.62-7.55 (m, 2H), 7.52-7.44 (m, 1H), 7.40-7.30 (m, 6H), 7.30-7.21 (m, 5H), 7.02 (d, J = 4.1 Hz, 1H), 6.16 (d, J = 14.1 Hz, 1H), 5.27-5.00 (m, 3H), 4.58-4.39 (m, 4H), 4.39-3.90 (m, 2H), 3.89-3.66 (m, 2H), 3.64-3.45 (m, 1H), 3.20-3.04 (m, 2H), 2.94-2.61 (m, 4H), 2.58-2.48 (m, 3H), 2.39 (t, J = 7.4 Hz, 2H), 2.32-1.87 (m, 8H), 1.85-1.53 (m, 7H). |
| 98 | I-107 | 2-[[(5S,8S,10aR)-8-[[(1S)-3-carbamoyl-1-(diphenylmethylcarbamoyl)propyl]carbamoyl]-3-[6-[1-(2,6-dioxopiperidin-3-yl)-3-methyl-2-oxo-1,3-benzodiazol-5-yl]hexanoyl]-6-oxo-octahydropyrrolo[1,2-a][1,5]diazocin-5-yl]carbamoyl]-1H-indole-5-carbonylphosphonic acid | 1127.9 | (400 MHz, DMSO-$d_6$) δ 12.19-12.01 (m, 1H), 11.08 (d, J = 2.9 Hz, 1H), 8.84-8.69 (m, 2H), 8.43 (d, J = 7.1 Hz, 1H), 8.30-8.18 (m, 1H), 7.95 (d, J = 8.7 Hz, 1H), 7.53 (d, J = 8.6 Hz, 1H), 7.48-7.38 (m, 1H), 7.35-7.21 (m, 12H), 7.05-6.93 (m, 2H), 6.87 (d, J = 8.1 Hz, 1H), 6.80-6.70 (m, 1H), 6.08 (d, J = 6.0 Hz, 1H), 5.36-5.28 (m, 1H), 5.01-4.86 (m, 1H), 4.50-4.12 (m, 3H), 3.91 (d, J = 13.4 Hz, 2H), 3.84-3.68 (m, 1H), 3.38-3.34 (m, 5H), 2.89 (t, J = 13.6 Hz, 1H), 2.75-2.53 (m, 5H), 2.19-2.08 (m, 3H), 2.04-1.88 (m, 4H), 1.83-1.68 (m, 3H), 1.67-1.55 (s, 5H), 1.41-1.36 (s, 2H). |
| 99 | I-109 | diammonium difluoro([4-[(1E)-1-[[(2S,11S)-2-[[(3S,4R)-4-[[4-(4-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]butyl)phenyl]methoxy]-1-(methylcarbamoyl)pentan-3-yl]carbamoyl]-12-oxo-1-azatricyclo[6.4.1.0^[4,13]]trideca-4(13),5,7-trien-11-yl]carbamoyl]prop-1-en-2-yl]phenyl])methylphosphonate | 1265.6 | (400 MHz, $CD_3OD$) δ 8.89 (s, 1H), 8.05 (d, J = 9.5 Hz, 1H), 7.69 (d, J = 8.2 Hz, 2H), 7.58 (d, J = 8.2 Hz, 2H), 7.48 (d, J = 8.2 Hz, 2H), 7.43 (d, J = 8.2 Hz, 2H), 7.23 (d, J = 7.9 Hz, 2H), 7.13 (d, J = 8.0 Hz, 2H), 7.05 (dt, J = 14.7, 7.2 Hz, 2H), 6.38 (d, J = 1.4 Hz, 1H), 5.16-5.12 (m, 1H), 4.72-4.62 (m, 2H), 4.62-4.44 (m, 5H), 4.36 (d, J = 15.6 Hz, 1H), 4.03-3.88 (m, 2H), 3.86-3.78 (m, 1H), 3.60-3.47 (m, 1H), 3.38-3.34 (m, 2H), 3.29-3.13 (m, 3H), 3.06-2.97 (m, 1H), 2.67 (s, 3H), 2.67-2.59 (m, 2H), 2.55 (d, J = 1.4 Hz, 3H), 2.49 (s, 3H), 2.37-2.15 (m, 7H), 2.15-1.96 (m, 2H), 1.69-1.58 (m, 5H), 1.34-1.29 (m, 1H), 1.19 (d, J = 6.4 Hz, 3H), 1.04 (s, 9H). |
| 100 | I-110 | diammonium [4-[(1E)-1-[[(2S,11S)-2-[[(3S,4R)-1-carbamoyl-4-[3-[1-(2,6-dioxopiperidin-3-yl)-3-methyl-2-oxo-1,3-benzodiazol-5-yl]propoxy]pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethylphosphonate | 980.2 | (400 MHz, $CD_3OD$) δ 7.69 (d, J = 8.2 Hz, 2H), 7.55 (d, J = 8.2 Hz, 2H), 7.12-6.93 (m, 6H), 6.36 (d, J = 1.4 Hz, 1H), 5.32 (dd, J = 12.6, 5.4 Hz, 1H), 5.18 (dd, J = 10.9, 3.4 Hz, 1H), 4.70-4.56 (m, 2H), 3.93 (d, J = 11.5 Hz, 1H), 3.58-3.49 (m, 2H), 3.47-3.33 (m, 6H), 3.30-3.05 (m, 2H), 3.02-2.88 (m, 1H), 2.87-2.71 (m, 4H), 2.54 (s, 3H), 2.40-2.25 (m, 3H), 2.22-2.10 (m, 1H), 2.10-1.98 (m, 1H), 1.89 (q, J = 6.9 Hz, 2H), 1.77-1.58 (m, 1H), 1.17 (d, J = 6.3 Hz, 3H). |
| 101 | I-111 | diammonium 2-[[(5S,8S,10aR)-8-[[(1S)-3-carbamoyl-1-(diphenylmethylcarbamoyl)propyl]carbamoyl]-3-[8-[2-(2,6-dioxopiperidin-3-yl)-1-oxo-3H-isoindol-4-yl]oct-7-ynoyl]-6-oxo-octahydropyrrolo[1,2-a][1,5]diazocin-5-yl]carbamoyl]-1H-indole-5-carbonylphosphonate | 1137.0 | (400 MHz, $CD_3OD$) δ 8.97 (q, J = 2.3 Hz, 1H), 8.13-8.08 (m, 1H), 7.76-7.70 (m, 1H), 7.63-7.58 (m, 1H), 7.53-7.45 (m, 2H), 7.41-7.22 (m, HH), 6.16 (d, J = 12.5 Hz, 1H), 5.24-5.07 (m, 2H), 4.60 (d, J = 15.3 Hz, 1H), 4.55-4.42 (m, 4H), 4.38-3.90 (m, 2H), 3.74 (d, J = 10.6 Hz, 1H), 3.67-3.49 (m, 1H), 2.97-2.81 (m, 1H), 2.81-2.59 (m, 3H), 2.57-2.48 (m, 3H), 2.40 (t, J = 7.4 Hz, 2H), 2.30-2.05 (m, 4H), 2.03-1.88 (m, 3H), 1.88-1.55 (m, 8H). |
| 102 | I-112 | [4-[(1E)-1-[[(5S,8S,10aR)-8-[[(1S)-3-carbamoyl-1-(diphenylmethylcarbamoyl)propyl]carbamoyl]-3-[7-[1-(2,6-dioxopiperidin-3-yl)-3-methyl-2-oxo-1,3-benzodiazol-5-yl]heptanoyl]-6-oxo- | 1164.6 | (400 MHz, $CD_3OD$) δ 7.72-7.56 (m, 4H), 7.38-7.20 (m, 10H), 7.07-6.92 (m, 3H), 6.36 (s, 1H), 6.15 (d, J = 7.1 Hz, 1H), 5.38-5.32 (m, 1H), 5.06-4.90 (m, 1H), 4.57-4.20 (m, 3H), 4.05-3.77 (m, 2H), 3.71-3.48 (m, 1H), 3.45-3.36 (m, 4H), 2.99-2.87 (m, 1H), 2.87-2.75 (m, 2H), 2.72-2.65 (m, 2H), 2.63-2.56 (m, 1H), |

TABLE 73-continued

| Characterization Data for Exemplary STAT3 Degraders | | | | |
|---|---|---|---|---|
| EXAMPLE | I-# | Chemical Name | MS: $[(M + 1)]^+$ | $^1$H NMR |
| | | octahydropyrrolo[1,2-a][1,5]diazocin-5-yl]carbamoyl]prop-1-en-2-yl]phenyl]difluoromethylphosphonic acid | | 2.54 (s, 3H), 2.52-2.39 (m, 1H), 2.39-2.07 (m, 6H), 2.01-1.75 (m, 5H), 1.75-1.58 (m, 4H), 1.57-1.31 (m, 4H). |
| 103 | I-113 | [4-[(1E)-1-[[(5S,8S,10aR)-8-[[(1S)-3-carbamoyl-1-(diphenylmethylcarbamoyl)propyl] carbamoyl]-3-[8-[1-(2,6-dioxopiperidin-3-yl)-3-methyl-2-oxo-1,3-benzodiazol-5-yl]octanoyl]-6-oxo-octahydropyrrolo[1,2-a][1,5]diazocin-5-yl]carbamoyl]prop-1-en-2-yl]phenyl]difluoromethylphosphonic acid | 1178.7 | (400 MHz, $CD_3OD$) δ 7.68-7.55 (m, 4H), 7.39-7.22 (m, 10H), 7.06-6.92 (m, 3H), 6.39-6.32 (m, 1H), 6.15 (d, J = 10.6 Hz, 1H), 5.36-5.26 (m, 1H), 5.09-4.94 (m, 2H), 4.50-4.23 (m, 3H), 4.03-3.47 (m, 3H), 3.40 (s, 3H), 2.99-2.88 (m, 1H), 2.87-2.76 (m, 2H), 2.72-2.68 (m, 2H), 2.63-2.57 (m, 1H), 2.55-2.50 (m, 4H), 2.43-2.30 (m, 2H), 2.30-2.05 (m, 4H), 2.03-1.89 (m, 4H), 1.83-1.72 (m, 1H), 1.71-1.59 (m, 4H), 1.49-1.32 (m, 6H). |
| 104 | I-114 | [4-[(1E)-1-[[(5S,8S,10aR)-8-[[(1S)-3-carbamoyl-1-(diphenylmethylcarbamoyl)propyl] carbamoyl]-3-[6-[1-(2,6-dioxopiperidin-3-yl)-3-methyl-2-oxo-1,3-benzodiazol-5-yl]hexanoyl]-6-oxo-octahydropyrrolo[1,2-a][1,5]diazocin-5-yl]carbamoyl]prop-1-en-2-yl]phenyl]difluoromethylphosphonic acid | 1150.5 | (400 MHz, $CD_3OD$) δ 7.69-7.55 (m, 4H), 7.40-7.21 (m, 10H), 7.09-6.93 (m, 3H), 6.36 (s, 1H), 6.18-6.07 (m, 1H), 5.38-5.27 (m, 1H), 5.04-4.93 (s, 1H), 4.53-4.23 (m, 3H), 4.07-3.47 (m, 3H), 3.46-3.34 (d, J = 6.9 Hz, 3H), 3.01-2.52 (m, 8H), 2.48-2.03 (m, 9H), 2.01-1.61 (m, 9H), 1.50-1.38 (m, 2H). |
| 105 | I-115 | ((4-((E)-4-(((5S,8S,10aR)-8-(((S)-5-amino-1-(benzhydrylamino)-1,5-dioxopentan-2-yl)carbamoyl)-3-(8-(2-(2,6-dioxopiperidin-3-yl)-1-oxoisoindolin-4-yl)oct-7-ynoyl)-6-oxodecahydropyrrolo[1,2-a][1,5]diazocin-5-yl)amino)-4-oxobut-2-en-2-yl)phenyl)difluoromethyl)phosphonic acid | 1160.6 | (400 MHz, $CD_3OD$) δ 7.77-7.72 (m, 1H), 7.71-7.66 (m, 2H), 7.63-7.58 (m, 1H), 7.57-7.46 (m, 3H), 7.38-7.21 (m, 10H), 6.38-6.29 (m, 1H), 6.15 (d, J = 8.9 Hz, 1H), 5.22-5.11 (m, 1H), 5.09-4.93 (m, 1H), 4.53-4.42 (m, 4H), 4.32-4.01 (m, 1H), 3.86 (d, J = 14.5 Hz, 1H), 3.80-3.64 (m, 1H), 3.65-3.49 (m, 1H), 3.49-3.35 (m, 2H), 2.95-2.83 (m, 1H), 2.82-2.72 (m, 1H), 2.70-2.58 (m, 2H), 2.57-2.46 (m, 6H), 2.46-2.30 (m, 2H), 2.30-2.07 (m, 4H), 2.01-1.86 (s, 3H), 1.82-1.68 (m, 5H), 1.65-1.54 (m, 2H). |
| 106 | I-117 | (2-(((3S,6S)-6-(((2R,3S)-6-amino-2-((4-(6-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-6-oxohexyl)benzyl)oxy)-6-oxohexan-3-yl)carbamoyl)-4-oxo-1,2,3,4,6,7-hexahydroazepino[3,2,1-hi]indol-3-yl)carbamoyl)-1H-indole-5-carbonyl)phosphonic acid | 1242.6 | (400 MHz, DMSO-$d_6$) δ 12.02 (s, 1H), 8.90-8.86 (m, 2H), 8.56 (s, 1H), 7.85 (d, J = 9.5 Hz, 2H), 7.49-7.33 (m, 6H), 7.29-6.61 (m, 8H), 5.15-5.05 (m, 2H), 4.54-4.50 (m, 1H), 4.49-4.30 (m, 5H), 4.22 (d, J = 16.1 Hz, 1H), 3.89-3.75 (m, 3H), 3.68-3.56 (d, J = 15.6 Hz, 2H), 3.26-3.04 (m, 2H), 2.89-2.78 (m, 1H), 2.45 (s, 3H), 2.37-1.95 (m, 6H), 1.92-1.73 (m, 2H), 1.62-1.42 (m, 5H), 1.32-1.15 (m, 5H), 1.12-1.00 (m, 2H), 0.93 (s, 9H). |
| 107 | I-118 | diammonium 2-[[(2S,11S)-2-[[(3S,4R)-1-carbamoyl-4-[(4-[6-[1-(2,6-dioxopiperidin-3-yl)-3-methyl-2-oxo-1,3-benzodiazol-5-yl]hexyl]phenyl)methoxy]pentan-3-yl]carbamoyl]-12-oxo-1-azatricyclo[6.4.1.0^[4,13]]trideca-4(13),5,7-trien-11-yl]carbamoyl]-1H-indole-5-carbonylphosphonate | 1057.5 | (400 MHz, DMSO-$d_6$) δ 12.05 (s, 1H), 11.08 (s, 1H), 9.12-9.05 (m, 1H), 8.26-7.80 (m, 2H), 7.66-7.35 (m, 2H), 7.35-6.51 (m, 13H), 5.42-5.27 (m, 1H), 5.13-4.98 (m, 1H), 4.72-4.60 (m, 1H), 4.38 (s, 2H), 3.86-3.72 (m, 1H), 3.34 (s, 2H), 3.31-3.00 (m, 5H), 2.97-2.79 (m, 2H), 2.76-2.55 (m, 5H), 2.39-1.88 (m, 5H), 1.78-1.73 (m, 1H), 1.59-1.52 (m, 5H), 1.32-1.22 (m, 5H), 1.07 (d, J = 8.4 Hz, 3H). |
| 108 | I-119 | [4-[(1E)-1-[[(2S,11S)-2-[[(3S,4R)-1-carbamoyl-4-[[4-(4-[[(2S)-1-[(2S,4S)-4-hydroxy-2-([[4-(4-methyl-1,3-thiazol-5-yl)phenyl]methyl]carbamoyl) pyrrolidin-1-yl]-3,3-dimethyl-1-oxobutan-2-yl]carbamoyl]butyl)phenyl]methoxy] pentan-3-yl]carbamoyl]-12-oxo-1-azatricyclo[6.4.1.0^[4,13]]trideca- | 1251.60 | (400 MHz, $CD_3OD$) δ 8.93-8.86 (m, 1H), 7.76-7.69 (m, 2H), 7.62-7.56 (m, 2H), 7.50-7.39 (m, 4H), 7.29-7.23 (m, 2H), 7.15-7.06 (m, 2H), 7.07 (d, J = 7.0 Hz, 1H), 7.07-6.99 (m, 1H), 6.37 (d, J = 1.5 Hz, 1H), 5.16 (dd, J = 10.9, 3.4 Hz, 1H), 4.69-4.62 (m, 1H), 4.60-4.40 (m, 5H), 4.42-4.34 (m, 2H), 4.06-3.97 (m, 2H), 3.75-3.68 (m, 1H), 3.61-3.44 (m, 2H), 3.28-3.15 (m, 1H), 3.06-3.29 (m, 1H), 2.62 (s, 3H), 2.55 (d, J = 1.3 Hz, 3H), 2.49 (s, 3H), 2.45-2.13 (m, 7H), 2.03-1.94 (m, 1H), |

TABLE 73-continued

Characterization Data for Exemplary STAT3 Degraders

| EXAMPLE | I-# | Chemical Name | MS: $[(M + 1)]^+$ | $^1H$ NMR |
|---|---|---|---|---|
| | | 4(13),5,7-trien-11-yl]carbamoyl]prop-1-en-2-yl]phenyl]difluoromethylphosphonic acid | | 1.67-1.61 (m, 6H), 1.19 (d, J = 6.3 Hz, 3H), 1.04 (s, 9H) |
| 109 | I-120 | diammonium 2-[[(5S,8S,10aR)-8-[[(1S)-3-carbamoyl-1-(diphenylmethylcarbamoyl)propyl]carbamoyl]-3-[8-[2-(l-methyl-2,6-dioxopiperidin-3-yl)-1-oxo-3H-isoindol-4-yl]oct-7-ynoyl]-6-oxo-octahydropyrrolo[1,2-a][1,5]diazocin-5-yl]carbamoyl]-1H-indole-5-carbonylphosphonate | 1150.75 | (400 MHz, DMSO-$d_6$) δ 11.96-11.83 (m, 1H), 9.16-8.58 (m, 2H), 8.50-7.89 (m, 2H), 7.75-7.39 (m, 5H), 7.39-7.19 (m, 12H), 6.80-6.76 (m, 1H), 6.11-6.09 (m, 1H), 5.21-5.18 (m, 1H), 4.97-4.95 (m, 1H), 4.57-4.22 (m, 5H), 4.18-4.16 (m, 1H), 3.94-3.92 (m, 1H), 3.78-3.76 (m, 1H), 3.16-2.89 (m, 4H), 2.78-2.62 (m, 2H), 2.42-1.30 (m, 1H), 2.35-2.33 (m, 3H), 2.21-1.84 (m, 10H), 1.84-1.33 (m, 10H) |
| 110 | I-121 | diammonium 2-[[(2S,11S)-2-[[(3S,4R)-1-carbamoyl-4-[[4-(4-[[(2S)-1-[(2S,4S)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]butyl)phenyl]methoxy]pentan-3-yl]carbamoyl]-12-oxo-1-azatricyclo[6.4.1.0^[4,13]]trideca-4(13),5,7-trien-11-yl]carbamoyl]-1H-indole-5-carbonylphosphonate | 1228.55 | (400 MHz, DMSO-$d_6$) δ 11.86 (s, 1H), 9.02-8.91 (m, 2H), 8.68-8.64 (m, 1H), 7.98-7.85 (m, 3H), 7.45-7.35 (m, 6H), 7.26-6.90 (m, 9H), 6.70 (s, 1H), 5.47-5.43 (m, 1H), 5.14-5.09 (m, 1H), 4.72-4.63 (m, 1H), 4.50-4.32 (m, 6H), 4.31-4.28 (m, 1H), 4.26-4.15 (m, 2H), 3.95-3.91 (m, 1H), 3.85-3.72 (m, 1H), 3.51-3.45 (m, 4H), 3.25-3.10 (m, 1H), 2.92-2.88 (m, 1H), 2.45 (s, 3H), 2.10-1.98 (m, 4H), 1.80-1.65 (m, 3H), 1.60-1.48 (m, 6H), 1.28-1.23 (m, 3H), 1.03-1.01 (m, 3H), 0.91 (s, 9H) |
| 111 | I-122 | 2-[[(5S,8S,10aR)-8-[[(1S)-3-carbamoyl-1-(diphenylmethylcarbamoyl)propyl]carbamoyl]-3-[4-[1-(2,6-dioxopiperidin-3-yl)-3-methyl-2-oxo-1,3-benzodiazol-4-yl]butanoyl]-6-oxo-octahydropyrrolo[1,2-a][1,5]diazocin-5-yl]carbamoyl]-1H-indole-5-carbonylphosphonic acid | $[(M-1)]^- =$ 1097.15 | (400 MHz, DMSO-$d_6$) δ 12.28-11.99 (m, 1H), 11.09 (s, 1H), 8.85-8.70 (m, 2H), 8.47-8.42 (m, 1H), 8.26-8.14 (m, 1H), 7.99-7.93 (m, 1H), 7.56-7.51 (m, 1H), 7.47-7.41 (m, 1H), 7.36-7.22 (m, 11H), 7.01-6.85 (m, 3H), 6.81-6.77 (m, 1H), 6.17-6.04 (m, 1H), 5.42-5.29 (m, 1H), 5.05-4.88 (m, 1H), 4.52-4.13 (m, 4H), 4.10-3.90 (m, 2H), 3.83-3.70 (m, 2H), 3.59 (s, 3H), 3.04-2.76 (m, 5H), 2.75-2.55 (m, 3H), 2.23-2.07 (m, 3H), 2.05-1.95 (m, 3H), 1.94-1.85 (m, 3H), 1.84-1.60 (m, 4H) |
| 112 | I-123 | 2-[[(5S,8S,10aR)-8-[[(1S)-3-carbamoyl-1-(diphenylmethylcarbamoyl)propyl]carbamoyl]-3-[6-[1-(2,6-dioxopiperidin-3-yl)-3-methyl-2-oxo-1,3-benzodiazol-4-yl]hexanoyl]-6-oxo-octahydropyrrolo[1,2-a][1,5]diazocin-5-yl]carbamoyl]-1H-indole-5-carbonylphosphonic acid | $[(M-1)]^- =$ 1125.25 | (400 MHz, DMSO-$d_6$) δ 12.24-12.91 (m, 1H), 11.09 (s, 1H), 8.90-8.71 (m, 2H), 8.46-8.13 (m, 2H), 8.00-7.93 (m, 1H), 7.54-7.20 (m, 13H), 7.02-6.76 (m, 4H), 6.12-6.07 (m, 1H), 5.40-5.32 (m, 1H), 5.01-4.84 (m, 1H), 4.49-4.42 (m, 1H), 4.41-4.34 (m, 1H), 4.23-4.14 (m, 1H), 3.99-3.87 (m, 1H), 3.83-3.71 (m, 2H), 3.55 (s, 3H), 3.13-3.00 (m, 1H), 2.94-2.83 (m, 3H), 2.75-2.60 (m, 3H), 2.25-1.86 (m, 8H), 1.84-1.70 (m, 3H), 1.69-1.54 (m, 5H), 1.52-1.36 (m, 2H), 1.26-1.12 (m, 2H) |
| 113 | I-124 | 2-[[(5S,8S,10aR)-8-[[(1S)-3-carbamoyl-1-(diphenylmethylcarbamoyl)propyl]carbamoyl]-3-[7-[1-(2,6-dioxopiperidin-3-yl)-3-methyl-2-oxo-1,3-benzodiazol-4-yl]heptanoyl]-6-oxo-octahydropyrrolo[1,2-a][1,5]diazocin-5-yl]carbamoyl]-1H-indole-5-carbonylphosphonic acid | 1141.30 | (400 MHz, DMSO-$d_6$) δ 12.17-11.96 (m, 1H), 11.09 (s, 1H), 8.84-8.75 (m, 2H), 8.43 (d, J = 6.8 Hz, 1H), 8.24-8.16 (m, 1H), 7.96 (d, J = 8.7 Hz, 1H), 7.51 (d, J = 8.8 Hz, 1H), 7.46-7.41 (m, 1H), 7.40-7.20 (m, 11H), 6.99-6.89 (m, 2H), 6.89-6.82 (m, 1H), 6.79 (s, 1H), 6.12-6.08 (m, 1H), 5.36 (d, J = 8.3 Hz, 1H), 5.06-4.88 (m, 1H), 4.50-4.43 (m, 1H), 4.38 (d, J = 6.9 Hz, 1H), 4.22-4.17 (m, 1H), 4.02-3.86 (m, 1H), 3.83-3.74 (m, 2H), 3.55 (s, 3H), 3.15-3.05 (m, 2H), 2.88-2.76 (m, 4H), 2.66-2.58 (m, 3H), 2.18-2.08 (m, 3H), 2.04-1.89 (m, 4H), 1.84-1.71 (m, 2H), 1.66-1.55 (m, 6H), 1.50-1.31 (m, 4H), 1.25-1.15 (m, 1H). |
| 114 | I-125 | 2-[[(5S,8S,10aR)-8-[[(1S)-3-carbamoyl-1-(diphenylmethylcarbamoyl)propyl]carbamoyl]-3-[9-[1-(2,6-dioxopiperidin-3-yl)-3-methyl-2-oxo-1,3-benzodiazol-4-yl]nonanoyl]-6-oxo-octahydropyrrolo[1,2-a][1,5]diazocin-5-yl]carbamoyl]-1H-indole-5-carbonylphosphonic acid | 1169.35 | (400 MHz, DMSO-$d_6$) δ 12.13-12.08 (m, 1H), 11.09 (s, 1H), 8.85-8.72 (m, 2H), 8.43 (d, J = 6.6 Hz, 1H), 8.27-8.19 (m, 1H), 7.96 (d, J = 8.9 Hz, 1H), 7.62-7.16 (m, 13H), 6.96 (d, J = 6.3 Hz, 2H), 6.93-6.66 (m, 2H), 6.14-6.06 (m, 1H), 5.36-5.34 (m, 1H), 4.96-3.92 (m, 1H), 4.49-4.40 (m, 1H), 4.41-4.34 (m, 1H), 4.23-4.14 (m, 1H), 4.04-3.86 (m, 1H), 3.83-3.74 (m, 2H), 3.55 (s, 3H), 3.15-3.10 (m, 1H), 2.96-2.82 (m, 3H), 2.80-2.74 (m, 1H), 2.67-2.58 (m, 2H), 2.18-2.11 (m, 4H), 2.05-1.86 |

TABLE 73-continued

Characterization Data for Exemplary STAT3 Degraders

| EXAMPLE | I-# | Chemical Name | MS: $[(M + 1)]^+$ | $^1H$ NMR |
|---|---|---|---|---|
| | | | | (m, 4H), 1.82-1.74 (m, 3H), 1.70-1.44 (m, 6H), 1.38-1.30 (m, 7H), 1.25-1.13 (m, 2H) |
| 115 | I-126 | diammonium 2-[[(2S,11S)-2-[[(3S,4R)-1-carbamoyl-4-[[7-(2-[[(2S)-1-[(2S,4R)-4-hydroxy-2-([[4-(4-methyl-1,3-thiazol-5-yl)phenyl]methyl]carbamoyl) pyrrolidin-1-yl]-3,3-dimethyl-1-oxobutan-2-yl]carbamoyl]ethyl)naphthalen-2-yl]methoxy]pentan-3-yl]carbamoyl]-12-oxo-1-azatricyclo[6.4.1.0^[4,13]]trideca-4(13),5,7-trien-11-yl]carbamoyl]-1H-indole-5-carbonylphosphonate | 1251.85 | (400 MHz, DMSO-$d_6$) δ 11.92 (s, 1H), 9.01-8.96 (m, 2H), 8.59-5.57 (m, 1H), 8.07-7.60 (m, 6H), 7.49-7.15 (m, 8H), 7.11-6.66 (m, 4H), 5.13-5.10 (m, 1H), 4.68-4.66 (m, 1H), 4.63-4.54 (m, 2H), 4.49-4.40 (m, 2H), 4.37-4.35 (m, 1H), 4.26-4.18 (m, 1H), 3.84-3.82 (m, 1H), 3.72-3.63 (m, 2H), 3.55-3.46 (m, 6H), 3.14-3.10 (m, 3H), 3.01-2.89 (m, 2H), 2.86-2.82 (m, 2H), 2.74-2.70 (m, 1H), 2.70-2.62 (m, 1H), 2.44 (s, 3H), 2.25-2.21 (m, 2H), 2.10-2.04 (m, 2H), 1.95-1.87 (m, 1H), 1.79-1.75 (m, 1H), 1.59-1.57 (m, 1H), 1.32-1.18 (m, 2H), 1.11 (d, J = 6.2 Hz, 3H), 0.89 (m, 9H) |
| 116 | I-127 | diammonium 2-[[(2S,11S)-2-[[(3S,4R)-1-carbamoyl-4-[[6-(3-[[(2S)-1-[(2S,4R)-4-hydroxy-2-([[4-(4-methyl-1,3-thiazol-5-yl)phenyl]methyl]carbamoyl) pyrrolidin-1-yl]-3,3-dimethyl-1-oxobutan-2-yl]carbamoyl]propyl)naphthalen-2-yl]methoxy]pentan-3-yl]carbamoyl]-12-oxo-1-azatricyclo[6.4.1.0^[4,13]]trideca-4(13),5,7-trien-11-yl]carbamoyl]-1H-indole-5-carbonylphosphonate | 1264.60 | (400 MHz, DMSO-$d_6$) δ 12.01-11.80 (m, 1H), 9.09-8.91 (m, 2H), 8.58 (d, J = 6.7 Hz, 1H), 7.93-7.91 (m, 2H), 7.75 (d, J = 9.4 Hz, 2H), 7.63 (d, J = 13.5 Hz, 1H), 7.50-7.15 (m, 11H), 7.03-6.98 (m, 3H), 6.69 (d, J = 14.4 Hz, 2H), 5.38-5.29 (m, 1H), 5.12 (d, J = 14.3 Hz, 1H), 4.68-4.60 (m, 1H), 4.58 (d, J = 10.2 Hz, 2H), 4.49-4.40 (m, 1H), 4.36 (s, 1H), 4.23-4.19 (m, 1H), 3.82 (s, 1H), 3.69 (s, 1H), 3.50-3.35 (m 4H), 2.95-2.82 (m, 1H), 2.76-2.74 (m, 1H), 2.48 (s, 3H), 2.39-2.22 (m, 4H), 2.05-1.98 (m, 3H), 1.97-1.75 (m, 4H), 1.76-1.50 (m, 2H), 1.46-1.11 (m, 10H), 1.01-0.82 (m, 7H) |
| 117 | I-129 | diammonium 2-[[(2S,11S)-2-[[(3S,4R)-1-carbamoyl-4-([4-[(1E)-5-[(2S)-1-[(2S,4R)-4-hydroxy-2-([[4-(4-methyl-1,3-thiazol-5-yl)phenyl]methyl]carbamoyl) pyrrolidin-1-yl]-3,3-dimethyl-1-oxobutan-2-yl]carbamoyl]pent-1-en-1-yl]phenyl]methoxy)pentan-3-yl]carbamoyl]-12-oxo-1-azatricyclo[6.4.1.0^[4,13]]trideca-4(13),5,7-trien-11-yl]carbamoyl]-1H-indole-5-carbonylphosphonate | 1240.55 | (400 MHz, DMSO-$d_6$) δ 11.97 (s, 1H), 9.01-8.92 (m, 2H), 8.86-8.84 (m, 1H), 8.57 (t, J = 6.1 Hz, 1H), 8.01-7.84 (m, 3H), 7.54-7.35 (m, 7H), 7.35-7.23 (m, 3H), 7.22-7.19 (m, 3H), 7.11-6.97 (m, 4H), 6.69 (s, 1H), 6.45-6.18 (m, 2H), 5.13-5.09 (m, 1H), 4.70-4.65 (m, 1H), 4.57 (d, J = 9.3 Hz, 1H), 4.50-4.32 (m, 6H), 4.25-4.20 (m, 1H), 3.82-3.76 (m, 2H), 3.70-3.65 (m, 2H), 3.30-3.00 (m, 1H), 2.88-2.84 (m, 1H), 2.72-2.56 (m, 1H), 2.45 (s, 3H), 2.38-2.11 (m, 6H), 2.09-1.99 (m, 3H), 1.94-1.88 (m, 1H), 1.85-1.45 (m, 2H), 1.42-1.12 (m, 2H), 1.08 (d, J = 6.2 Hz, 3H), 0.95 (s, 9H) |
| 118 | I-130 | diammonium 2-[[(2S,11S)-2-[[(3S,4R)-1-carbamoyl-4-([4-[(1E)-4-[[(2S)-1-[(2S,4R)-4-hydroxy-2-([[4-(4-methyl-1,3-thiazol-5-yl)phenyl]methyl]carbamoyl) pyrrolidin-1-yl]-3,3-dimethyl-1-oxobutan-2-yl]carbamoyl]but-1-en-1-yl]phenyl]methoxy)pentan-3-yl]carbamoyl]-12-oxo-1-azatricyclo[6.4.1.0^[4,13]]trideca-4(13),5,7-trien-11-yl]carbamoyl]-1H-indole-5-carbonylphosphonate | 1227.50 | (400 MHz, DMSO-$d_6$) δ 11.91 (s, 1H), 8.99-8.90 (m, 3H), 8.58 (t, J = 5.9 Hz, 1H), 8.07-7.80 (m, 3H), 7.48-7.34 (m, 7H), 7.34-7.14 (m, 6H), 7.14-7.04 (m, 2H), 7.00 (t, J = 7.4 Hz, 1H), 6.70 (s, 1H), 6.41-6.36 (m, 1H), 6.32-6.15 (m, 1H), 5.13-5.10 (m, 1H), 4.70-4.65 (m, 1H), 4.57 (d, J = 9.4 Hz, 1H), 4.49-4.30 (m, 6H), 4.24-4.19 (m, 1H), 3.83-3.76 (m, 1H), 3.70-3.63 (m, 2H), 3.22-3.06 (m, 5H), 2.89-2.84 (m, 1H), 2.76-2.60 (m, 1H), 2.44 (s, 3H), 2.42-2.37 (m, 1H), 2.36-2.14 (m, 2H), 2.10-1.98 (m, 3H), 1.95-1.83 (m, 1H), 1.80-1.72 (m, 1H), 1.60-1.49 (m, 1H), 1.25-1.15 (m, 1H), 1.07 (d, J = 6.2 Hz, 3H), 0.93 (s, 9H). |
| 119 | I-133 | diammonium 2-[[(2S,11S)-2-[[(3S,4R)-1-carbamoyl-4-[[5-(3-[[(2S)-1-[(2S,4R)-4-hydroxy-2-([[4-(4-methyl-1,3-thiazol-5-yl)phenyl]methyl]carbamoyl) pyrrolidin-1-yl]-3,3-dimethyl-1-oxobutan-2-yl]carbamoyl]propyl)naphthalen-2-yl]methoxy]pentan-3-yl]carbamoyl]-12-oxo-1-azatricyclo[6.4.1.0^[4,13]]trideca-4(13),5,7-trien-11-yl]carbamoyl]-1H-indole-5-carbonylphosphonate | 1264.70 | (400 MHz, DMSO-$d_6$) δ 11.87 (s, 1H), 8.99-8.93 (m, 3H), 8.59 (t, J = 6.2 Hz, 1H), 8.00 (d, J = 8.9 Hz, 2H), 7.94 (t, J = 8.2 Hz, 2H), 7.80 (s, 1H), 7.70 (d, J = 8.1 Hz, 1H), 7.46-7.38 (m, 8H), 7.32 (d, J = 7.1 Hz, 1H), 7.21 (s, 1H), 7.11-7.09 (m, 1H), 6.98-6.96 (m, 2H), 6.72 (s, 1H), 5.14-5.10 (m, 1H), 4.73-4.53 (m, 4H), 4.50-4.40 (m, 2H), 4.37-4.35 (m, 1H), 4.26-4.20 (m, 1H), 3.88-3.82 (m, 1H), 3.72-3.67 (m, 2H), 3.57-3.50 (m, 1H), 3.21-3.13 (m, 1H), 3.04-2.98 (m, 2H), 2.86-2.82 (m, 1H), 2.45 (s, 3H), 2.43-2.37 (m, 1H), 2.37-2.17 (m, 3H), 2.16-1.97 (m, 3H), 1.97-1.72 (m, 3H), 1.66-1.45 (m, 1H), 1.30-1.23 (m, 6H), 1.13 (d, J = 6.2 Hz, 3H), 0.97 (s, 9H) |
| 120 | I-136 | diammonium 2-[[(2S,11S)-2-[[(3S,4R)-1-carbamoyl-4-[[5-(2- | 1250.55 | (400 MHz, DMSO-$d_6$) δ 11.85 (s, 1H), 8.98 (s, 1H), 8.94-8.91 (m, 2H), 8.63-8.61 (m, 1H), |

TABLE 73-continued

| Characterization Data for Exemplary STAT3 Degraders | | | | |
|---|---|---|---|---|
| EXAMPLE | I-# | Chemical Name | MS: $[(M + 1)]^+$ | $^1$H NMR |
| | | [[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]ethyl)naphthalen-2-yl]methoxy]pentan-3-yl]carbamoyl]-12-oxo-1-azatricyclo[6.4.1.0^[4,13]]trideca-4(13),5,7-trien-11-yl]carbamoyl]-1H-indole-5-carbonylphosphonate | | 8.10 (d, J = 9.4 Hz, 1H), 7.98 (d, J = 8.7 Hz, 1H), 7.93-7.90 (m, 2H), 7.80 (s, 1H), 7.70 (d, J = 7.6 Hz, 1H), 7.45-7.35 (m, HH), 7.30-7.05 (m, 2H), 7.01-6.95 (m, 2H), 6.72 (s, 1H), 5.14-5.11 (m, 1H), 4.70-4.61 (m, 4H), 4.50-4.37 (m, 3H), 4.25-4.21 (m, 1H), 3.87-3.85 (m, 1H), 3.72-3.69 (m, 2H), 3.55-3.51 (m, 2H), 3.25-3.18 (m, 2H), 2.87-2.85 (m, 1H), 2.46 (s, 3H), 2.24-2.21 (m, 1H), 2.10-2.05 (m, 2H), 1.91-1.75 (m, 2H), 1.76 (s, 3H), 1.58-1.56 (m, 1H), 1.26-1.22 (m, 3H), 1.17-1.12 (m, 4H), 0.94 (s, 9H) |
| 121 | I-137 | diammonium 2-[[(2S)-1-[(1R,2S,5S)-2-[[(3S,4R)-1-carbamoyl-4-[[4-(4-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]butyl)phenyl]methoxy]pentan-3-yl]carbamoyl]-3-azabicyclo[3.1.0]hexan-3-yl]-4-methyl-1-oxopentan-2-yl]carbamoyl]-1H-indole-5-carbonylphosphonate | 1222.95 | (400 MHz, DMSO-$d_6$) δ 11.85 (s, 1H), 8.99 (s, 1H), 8.85 (s, 1H), 8.72-8.70 (m, 1H), 8.58-8.56 (m, 1H), 7.95-7.89 (m, 1H), 7.63 (d, J = 9.2 Hz, 1H), 7.44-7.38 (m, 8H), 7.24 (d, J = 7.7 Hz, 2H), 7.14 (d, J = 7.7 Hz, 2H), 7.07 (s, 1H), 6.70 (s, 1H), 5.20-5.17 (m, 1H), 4.70-4.68 (m, 1H), 4.57-4.53 (m, 1H), 4.51-4.39 (m, 5H), 4.36-4.34 (m, 1H), 4.24-4.20 (m, 1H), 4.07-4.05 (m, 1H), 3.75-3.65 (m, 5H), 2.55-2.51 (m, 2H), 2.45 (s, 3H), 2.35-2.32 (m, 3H), 2.20-2.01 (m, 3H), 1.95-1.83 (m, 3H), 1.82-1.75 (m, 4H), 1.69-1.52 (m, 6H), 1.25-1.24 (m, 2H), 1.09 (d, J = 6.2 Hz, 3H), 0.94-0.90 (m, 12H), 0.77-0.73 (m, 1H), 0.62-0.57 (m, 1H) |
| 122 | I-138 | diammonium 2-[[(2S,11S)-2-[[(1S)-3-carbamoyl-1-([[4-(3-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]propyl)phenyl]methyl]carbamoyl)propyl]carbamoyl]-12-oxo-1-azatricyclo[6.4.1.0^[4,13]]trideca-4(13),5,7-trien-11-yl]carbamoyl]-1H-indole-5-carbonylphosphonate | 1214.60 | (400 MHz, DMSO-$d_6$) δ 11.91 (s, 1H), 8.99 (s, 1H), 8.96-8.89 (m, 1H), 8.60-8.57 (m, 1H), 8.36-8.34 (m, 1H), 8.26 (d, J = 7.8 Hz, 1H), 7.94 (dd, J = 8.6, 1.5 Hz, 2H), 7.53-7.42 (m, 6H), 7.33-7.28 (m, 3H), 7.13-7.04 (m, 6H), 7.14-7.00 (m, 1H), 6.81-6.69 (m, 1H), 5.20-5.02 (m, 2H), 4.68-4.60 (m, 1H), 4.56 (d, J = 9.3 Hz, 1H), 4.52-4.40 (m, 2H), 4.37-4.33 (m, 1H), 4.30-4.18 (m, 5H), 3.68-3.65 (m, 2H), 3.48-3.45 (m, 2H), 3.32-3.28 (m, 2H), 3.15-3.11 (m, 2H), 3.09-2.97 (m, 1H), 2.45 (s, 3H), 2.32-2.01 (m, 6H), 1.98-1.86 (m, 2H), 1.82-1.76 (m, 3H), 0.95 (s, 9H) |
| 123 | I-139 | diammonium 2-[[(2S,11S)-2-[[(1S)-3-carbamoyl-1-([[4-(4-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]butyl)phenyl]methyl]carbamoyl)propyl]carbamoyl]-12-oxo-1-azatricyclo[6.4.1.0^[4,13]]trideca-4(13),5,7-trien-11-yl]carbamoyl]-1H-indole-5-carbonylphosphonate | 1227.55 | (400 MHz, DMSO-$d_6$) δ 12.01-11.92 (m, 1H), 9.03-8.96 (m, 1H), 8.94 (d, J = 8.2 Hz, 1H), 8.92-8.86 (m, 2H), 8.63-8.58 (m, 1H), 8.01-7.90 (m, 2H), 7.51-7.42 (m, 6H), 7.31-7.24 (m, 1H), 7.13-7.08 (m, 7H), 7.04-6.93 (m, 1H), 6.82-6.74 (m, 1H), 5.15 (dd, J = 10.7, 2.9 Hz, 1H), 4.76-4.57 (m, 1H), 4.58-4.52 (m, 1H), 4.49-4.39 (m, 2H), 4.38-4.31 (m, 1H), 4.27-4.14 (m, 4H), 3.66-3.61 (m, 2H), 3.48-3.42 (m, 4H), 3.27-3.04 (m, 4H), 3.02-2.96 (m, 1H), 2.45 (s, 3H), 2.30-2.22 (m, 2H), 2.20-2.02 (m, 4H), 1.96-1.84 (m, 2H), 1.77-1.74 (m, 1H), 1.53-1.48 (m, 4H), 1.22-1.19 (m, 1H), 0.94 (s, 9H) |
| 124 | I-140 | diammonium 2-[[(2S,11S)-2-[[(1S)-3-carbamoyl-1-([[4-(5-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]pentyl)phenyl]methyl]carbamoyl)propyl]carbamoyl]-12-oxo-1-azatricyclo[6.4.1.0^[4,13]]trideca-4(13),5,7-trien-11-yl]carbamoyl]-1H-indole-5-carbonylphosphonate | $[(M-1)]^-$ = 1239.50 | (400 MHz, DMSO-$d_6$) δ 12.01-11.94 (m, 1H), 9.02-8.96 (m, 2H), 8.92-8.86 (m, 1H), 8.63-8.56 (m, 1H), 8.41-8.33 (m, 1H), 8.26 (d, J = 7.8 Hz, 1H), 8.01-7.94 (m, 1H), 7.89-7.84 (m, 1H), 7.49-7.36 (m, 6H), 7.32-7.25 (m, 1H), 7.13-7.06 (m, 6H), 7.02-6.98 (m, 1H), 6.83-6.78 (m, 1H), 5.15 (dd, J = 10.7, 2.9 Hz, 1H), 4.72-4.64 (m, 1H), 4.58-4.51 (m, 1H), 4.46-4.42 (m, 2H), 4.38-4.31 (m, 1H), 4.24-4.20 (m, 4H), 3.68-3.63 (m, 3H), 3.20-3.18 (m, 2H), 3.16-3.11 (m, 2H), 2.98-2.95 (m, 2H), 2.45 (s, 3H), 2.28-2.23 (m, 3H), 2.15-2.03 (m, 4H), 1.93-1.80 (m, 2H), 1.79-1.77 (m, 2H), 1.54-1.48 (m, 4H), 1.26-1.24 (m, 2H), 0.94 (s, 9H) |
| 125 | I-141 | diammonium 2-[[(2S,11S)-2-[[(2S)-4-carbamoyl-1-[[4-(4-[[(2S)-1-[(2S,4R)-4-hydroxy-2-[[(1S)-1-[4-(4-methyl-1,3-thiazol-5-yl)phenyl]ethyl]carbamoyl]pyrrolidin- | 1228.65 | (400 MHz, DMSO-$d_6$) δ 12.02-11.96 (m, 1H), 9.19-8.57 (m, 2H), 8.45-8.40 (m, 1H), 8.07-7.75 (m, 3H), 7.59-7.28 (m, 7H), 7.25-6.85 (m, 7H), 6.79-6.49 (m, 2H), 5.32-4.76 (m, 3H), 4.69-4.61 (m, 1H), 4.55-4.48 (m, 1H), |

TABLE 73-continued

| Characterization Data for Exemplary STAT3 Degraders | | | | |
|---|---|---|---|---|
| EXAMPLE | I-# | Chemical Name | MS: $[(M + 1)]^+$ | $^1$H NMR |
| | | 1-yl]-3,3-dimethyl-1-oxobutan-2-yl]carbamoyl]butyl)phenyl]methoxy]butan-2-yl]carbamoyl]-12-oxo-1-azatricyclo[6.4.1.0^[4,13]]trideca-4(13),5,7-trien-11-yl]carbamoyl]-1H-indole-5-carbonylphosphonate. | | 4.46-4.12 (m, 5H), 3.91-3.74 (m, 2H), 3.63-3.58 (m, 3H), 3.33-3.04 (m, 4H), 3.01-2.78 (m, 1H), 2.58-2.53 (m, 2H), 2.45 (s, 3H), 2.35-2.20 (m, 2H), 2.18-1.94 (m, 5H), 1.86-1.68 (m, 2H), 1.63-1.43 (m, 5H), 1.37 (d, J = 7.0 Hz, 3H), 0.93 (s, 9H) |
| 126 | I-142 | diammonium[3-[(1E)-1-[[(2S,11S)-2-[[(3S,4R)-1-carbamoyl-4-[[4-(4-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]butyl)phenyl]methoxy]pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethylphosphonate | 1251.65 | (400 MHz, DMSO-$d_6$) δ 9.00-8.99 (m, 1H), 8.59-8.55 (m, 2H), 7.92-7.87 (m, 2H), 7.76-7.71 (m, 1H), 7.58-7.52 (m, 2H), 7.47-7.33 (m, 6H), 7.27-7.02 (m, 5H), 6.98-6.66 (m, 1H), 6.74-6.72 (m, 1H), 6.47-6.45 (m, 1H), 5.20-4.98 (m, 2H), 4.59-4.52 (m, 1H), 4.51-4.28 (m, 6H), 4.25-4.19 (m, 1H), 3.81-3.78 (m, 2H), 3.71-3.60 (m, 3H), 3.19-2.98 (m, 2H), 2.89-2.82 (m, 1H), 2.52-2.48 (m, 4H), 2.44 (s, 3H), 2.37-2.27 (m, 2H), 2.20-1.99 (m, 8H), 1.91-1.89 (m, 1H), 1.78-1.76 (m, 2H), 1.55-1.48 (m, 6H), 1.07 (d, J = 6.1 Hz, 3H), 0.94 (s, 9H) |
| 127 | I-143 | [3-[(1E)-1-[[(8S,10aR)-8-[[(1S)-3-carbamoyl-1-(diphenylmethylcarbamoyl)propyl]carbamoyl]-3-[7-[1-(2,6-dioxopiperidin-3-yl)-3-methyl-2-oxo-1,3-benzodiazol-5-yl]heptanoyl]-6-oxo-octahydropyrrolo[1,2-a][1,5]diazocin-5-yl]carbamoyl]prop-1-en-2-yl]phenyl]difluoromethylphosphonic acid | 1164.85 | (400 MHz, DMSO-$d_6$) δ 11.15-11.04 (m, 1H), 8.82-8.72 (m, 1H), 8.52-8.00 (m, 2H), 7.71-7.56 (m, 2H), 7.56-7.49 (m, 1H), 7.44 (d, J = 6.3 Hz, 1H), 7.36-7.10 (m, 11H), 7.06-6.38 (m, 4H), 6.11-6.06 (d, J = 8.5 Hz, 1H), 5.62-5.23 (m, 2H), 4.83-4.56 (m, 1H), 4.43-4.36 (m, 2H), 4.17-4.02 (m, 1H), 3.87-3.71 (m, 2H), 3.34 (s, 3H), 3.27-2.99 (m, 1H), 2.99-2.82 (m, 2H), 2.76-2.56 (m, 5H), 2.46 (m, 2H), 2.38-2.31 (m, 1H), 2.21-2.04 (m, 4H), 2.03-1.85 (m, 4H), 1.83-1.66 (m, 3H), 1.66-1.40 (m, 6H), 1.40-1.15 (m, 5H) |
| 128 | I-144 | diammonium [3-[(1E)-1-[[(2S,11S)-2-[[(3S,4R)-1-carbamoyl-4-[[4-(4-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]butyl)phenyl]methoxy]pentan-3-yl]carbamoyl]-12-oxo-1-azatricyclo[6.4.1.0^[4,13]]trideca-4(13),5,7-trien-11-yl]carbamoyl]prop-1-en-2-yl]phenyl]difluoromethylphosphonate | 1265.70 | (400 MHz, DMSO-$d_6$) δ 8.99 (s, 1H), 8.55 (d, J = 7.7 Hz, 1H), 8.40 (d, J = 7.8 Hz, 1H), 7.88-7.84 (m, 2H), 7.73 (s, 1H), 7.57-7.53 (m, 2H), 7.45-7.37 (m, 5H), 7.21-7.16 (m, 3H), 7.13-7.05 (m, 4H), 7.01-6.96 (m, 1H), 6.75 (s, 1H), 6.46 (s, 1H), 5.10-5.08 (m, 1H), 4.94-4.92 (m, 1H), 4.53-4.45 (m, 5H), 4.30-4.26 (m, 1H), 3.86-3.84 (m, 1H), 3.62-3.58 (m, 3H), 3.32-3.30 (m, 3H), 3.20-3.10 (m, 4H), 2.92-2.89 (m, 1H), 2.56-2.49 (m, 3H), 2.46 (s, 3H), 2.32-2.28 (m, 1H), 2.17-1.98 (m, 7H), 1.81-1.78 (m, 2H), 1.62-1.42 (m, 5H), 1.38 (d, J = 7.0 Hz, 3H), 1.18 (d, J = 6.1 Hz, 3H), 0.93 (s, 9H) |
| 129 | I-150 | 2-[[(5S,8S,10aR)-8-[[(1S)-3-carbamoyl-1-(diphenylmethylcarbamoyl)propyl]carbamoyl]-3-[7-[3-methyl-1-(1-methyl-2,6-dioxopiperidin-3-yl)-2-oxo-1,3-benzodiazol-5-yl]heptanoyl]-6-oxo-octahydropyrrolo[1,2-a][1,5]diazocin-5-yl]carbamoyl]-1H-indole-5-carbonylphosphonic acid | 1155.35 | (400 MHz, DMSO-$d_6$) δ 12.19-12.01 (m, 1H), 8.82-8.75 (m, 2H), 8.41 (s, 1H), 8.29-8.13 (m, 1H), 7.98 (d, J = 8.8 Hz, 1H), 7.48 (d, J = 8.8 Hz, 1H), 7.44-7.18 (m, 14H), 7.07-6.93 (m, 2H), 6.90-6.68 (m, 2H), 6.14-6.08 (m, 1H), 5.40 (dd, J = 12.7, 5.2 Hz, 1H), 4.99-4.84 (m, 1H), 4.48-4.35 (m, 2H), 4.22-4.18 (m, 1H), 4.08-3.86 (m, 1H), 3.85-3.76 (m, 1H), 3.32 (s, 3H), 3.30-3.09 (m, 5H), 3.04 (s, 3H), 3.00-2.90 (m, 1H), 2.84-2.57 (m, 4H), 2.45-2.30 (m, 1H), 2.25-1.85 (m, 4H), 1.85-1.73 (m, 1H), 1.70-1.47 (m, 6H), 1.43-1.32 (m, 6H) |
| 130 | I-157 | 2-[[(5S,8S,10aR)-8-[[(1S)-3-carbamoyl-1-(diphenylmethylcarbamoyl)propyl]carbamoyl]-3-[2-(4-[[1-(2,6-dioxopiperidin-3-yl)-3-methyl-2-oxo-1,3-benzodiazol-5-yl]methyl]piperazin-1-yl)acetyl]-6-oxo-octahydropyrrolo[1,2-a][1,5]diazocin-5-yl]carbamoyl]-1H-indole-5-carbonylphosphonic acid | $[(M - 1)]^-$ = 1167.75 | (400 MHz, DMSO-$d_6$) δ 12.15-11.90 (m, 1H), 11.09 (s, 2H), 8.94 (s, 1H), 8.85-8.66 (m, 1H), 8.30-7.97 (m, 2H), 7.34-7.23 (m, 15H), 7.15-6.96 (m, 2H), 6.15-6.09 (m, 1H), 5.42-5.36 (m, 1H), 5.05-4.96 (m, 1H), 4.48-4.34 (m, 5H), 4.28-4.18 (m, 4H), 3.10-2.81 (m, 5H), 2.78-2.53 (m, 7H), 2.23-1.87 (m, 9H), 1.85-1.50 (m, 6H), 1.35-1.02 (m, 2H) |
| 131 | I-167 | 2-[[(5S,8S,10aR)-8-[[(1S)-3-carbamoyl-1-(diphenylmethylcarbamoyl)propyl] | 1182.40 | (400 MHz, DMSO-$d_6$) δ 12.12-11.90 (m, 1H), 11.08 (s, 1H), 8.93-8.69 (m, 2H), 8.47-8.39 (m, 1H), 8.24-8.14 (m, 1H), 8.01-7.93 (m, |

TABLE 73-continued

| Characterization Data for Exemplary STAT3 Degraders | | | | |
|---|---|---|---|---|
| EXAMPLE | I-# | Chemical Name | MS: $[(M + 1)]^+$ | $^1H$ NMR |
| | | carbamoyl]-6-oxo-3-[3-[(1r,4r)-4-[[1-(2,6-dioxopiperidin-3-yl)-3-methyl-2-oxo-1,3-benzodiazol-5-yl]methyl]cyclohexyl]propanoyl]-octahydropyrrolo[1,2-a][1,5]diazocin-5-yl]carbamoyl]-1H-indole-5-carbonylphosphonic acid | | 1H), 7.52-7.45 (m, 1H), 7.44-7.19 (m, 12H), 7.04-6.93 (m, 2H), 6.84-6.75 (m, 1H), 6.14-6.05 (m, 1H), 5.38-5.30 (m, 1H), 5.03-4.86 (m, 1H), 4.49-4.28 (m, 3H), 4.23-4.14 (m, 1H), 3.99-3.82 (m, 2H), 3.81-3.69 (m, 1H), 2.99-2.83 (m, 2H), 2.78-2.59 (m, 4H), 2.25-1.87 (m, 8H), 1.85-1.72 (m, 5H), 1.70-1.38 (m, 8H), 1.37-1.31 (m, 2H), 1.30-1.11 (m, 3H), 1.05-0.78 (m, 4H) |
| 132 | I-168 | 2-[[(5S,8S,10aR)-8-[[(1S)-3-carbamoyl-1-(diphenylmethylcarbamoyl)propyl]carbamoyl]-3-(4-[4-[1-(2,6-dioxopiperidin-3-yl)-3-methyl-2-oxo-1,3-benzodiazol-5-yl]piperazin-1-yl]butanoyl)-6-oxo-octahydropyrrolo[1,2-a][1,5]diazocin-5-yl]carbamoyl]-1H-indole-5-carbonylphosphonic acid | 1183.65 | (400 MHz, DMSO-$d_6$) δ 11.79 (s, 1H), 11.05 (s, 1H), 9.91-9.71 (m, 1H), 9.49-9.25 (m, 1H), 8.61-8.42 (m, 1H), 8.27-8.16 (m, 1H), 7.89-7.70 (m, 2H), 7.55-7.08 (m, 12H), 6.99-6.88 (m, 2H), 6.73-6.61 (m, 1H), 6.13-6.05 (m, 1H), 5.32-5.23 (m, 1H), 5.10-5.01 (m, 1H), 4.36-4.20 (m, 3H), 4.13-4.00 (m, 1H), 3.94-3.58 (m, 5H), 3.24-2.98 (m, 7H), 2.95-2.78 (m, 3H), 2.72-2.56 (m, 4H), 2.39-2.24 (m, 2H), 2.18-1.90 (m, 9H), 1.78-1.58 (m, 4H), 1.53-1.32 (m, 2H), 1.26-1.21 (m, 1H) |
| 133 | I-175 | 2-[[(5S,8S,10aR)-8-[[(1S)-3-carbamoyl-1-(diphenylmethylcarbamoyl)propyl]carbamoyl]-3-(3-[4-[1-(2,6-dioxopiperidin-3-yl)-3-methyl-2-oxo-1,3-benzodiazol-5-yl]piperazin-1-yl]propanoyl)-6-oxo-octahydropyrrolo[1,2-a][1,5]diazocin-5-yl]carbamoyl]-1H-indole-5-carbonylphosphonic acid | 1170.10 | (400 MHz, DMSO-$d_6$) δ 11.97 (s, 1H), 11.07 (s, 1H), 9.26-8.61 (m, 3H), 8.21-8.15 (m, 1H), 7.92-7.86 (m, 1H), 7.48-7.22 (m, 13H), 6.99-6.70 (m, 3H), 6.62 (s, 1H), 6.11 (d, J = 8.4 Hz, 1H), 5.33-5.28 (m, 1H), 5.11-4.91 (m, 2H), 4.44-4.32 (m, 3H), 4.00-3.67 (m, 4H), 3.30 (s, 3H), 3.16-3.03 (m, 6H), 2.95-2.86 (m, 3H), 2.80-2.56 (m, 6H), 2.27-1.84 (m, 7H), 1.74-1.66 (m, 5H). |

The following compounds in Table 74 were synthesized according to the procedure of Example 1 but using 2-(2,3,4,5,6-pentafluorophenoxycarbonyl)-1H-indole-5-carbonylphosphonic acid (Intermediate M3) instead of (2-((4-nitrophenoxy)carbonyl)-1H-indole-5-carbonyl)phosphonic acid (Intermediate M) and corresponding substrates.

TABLE 74

| Characterization Data for Exemplary STAT3 Degraders | | | | |
|---|---|---|---|---|
| 134 | I-128 | 2-[[(5S,8S,10aR)-8-[[(1S)-3-carbamoyl-1-(diphenylmethylcarbamoyl)propyl]carbamoyl]-3-(4-[1-[1-(2,6-dioxopiperidin-3-yl)-3-methyl-2-oxo-1,3-benzodiazol-5-yl]piperidin-4-yl]butanoyl)-6-oxo-octahydropyrrolo[1,2-a][1,5]diazocin-5-yl]carbamoyl]-1H-indole-5-carbonylphosphonic acid | 1182.35 | (400 MHz, DMSO-$d_6$) δ 12.18-11.98 (m, 1H), 11.09-11.1 (m, 1H), 8.85-8.74 (m, 2H), 8.48-8.42 (m, 1H), 8.29-8.11 (m, 1H), 7.96 (d, J = 8.8 Hz, 1H), 7.60-7.14 (m, 13H), 6.98-6.89 (m, 1H), 6.87-6.80 (m, 2H), 6.66-6.59 (m, 1H), 6.10 (d, J = 7.2 Hz, 1H), 5.08 (dd, J = 10.7, 2.9 Hz, 1H), 5.04-4.94 (m, 1H), 4.50-4.42 (m, 1H), 4.40-4.16 (m, 2H), 3.98-3.92 (m, 2H), 3.84-3.75 (m, 2H), 3.58-3.51 (m, 4H), 3.36 (s, 3H), 2.96-2.83 (m, 2H), 2.68-2.61 (m, 4H), 2.22-2.05 (m, 3H), 1.98-1.93 (m, 4H), 1.80-1.74 (m, 8H), 1.36-1.28 (m, 6H) |
| 135 | I-132 | 2-[[(5S,8S,10aR)-8-[[(1S)-3-carbamoyl-1-(diphenylmethylcarbamoyl)propyl]carbamoyl]-3-(6-[[1-(2,6-dioxopiperidin-3-yl)-3-methyl-2-oxo-1,3-benzodiazol-5-yl]amino]hexanoyl)-6-oxo-octahydropyrrolo[1,2-a][1,5]diazocin-5-yl]carbamoyl]-1H-indole-5-carbonylphosphonic acid | 1142.55 | (400 MHz, DMSO-$d_6$) δ 12.20-12.01 (m, 1H), 11.04 (s, 1H), 8.92-8.70 (m, 2H), 8.43 (d, J = 6.5 Hz, 1H), 8.25-8.14 (m, 1H), 7.96 (d, J = 8.8 Hz, 1H), 7.51 (d, J = 8.7 Hz, 1H), 7.47-7.18 (m, 14H), 6.87-6.60 (m,2H), 6.41 (s, 1H), 6.30 (d, J = 8.5 Hz, 1H), 6.12-6.09 (m, 1H), 5.33-5.17 (m, 1H), 4.97-4.86 (m, 1H), 4.51-4.14 (m, 3H), 3.96-3.92 (m, 1H), 3.83-3.75 (m, 1H), 3.27-3.13 (m, 3H), 3.12-2.96 (m, 3H), 2.93-2.85 (m, 2H), 2.73-2.56 (m, 2H), 2.20-2.07 (m, 3H), 2.03-1.85 (m, 4H), 1.82-1.72 (m, 4H), 1.68-1.56 (m, 6H), 1.47-1.42 (m, 2H), 1.25-1.17 (m, 1H). |
| 136 | I-134 | 2-[[(5S,8S,10aR)-8-[[(1S)-3-carbamoyl-1-(diphenylmethylcarbamoyl)propyl]carbamoyl]-3-[7-[3-(2,6-dioxopiperidin-3-yl)-1-methyl-2-oxo-1,3-benzodiazol-5-yl]heptanoyl]-6-oxo-octahydropyrrolo[1,2- | 1141.65 | (400 MHz, DMSO-$d_6$) δ 12.27-11.98 (m, 1H), 11.08 (s, 1H), 8.81-8.76 (m, 2H), 8.43 (d, J = 6.9 Hz, 1H), 8.26-8.19 (m, 1H), 7.97-7.93 (m, 1H), 7.57-7.39 (m, 2H), 7.38-7.20 (m, 11H), 7.09-6.96 (m, 2H), 6.93-6.86 (m, 1H), 6.81-6.67 (m, 1H), 6.12-6.10 (m, 1H), 5.41-5.29 (m, 1H), 5.04-4.92 (m, 1H), 4.49-4.44 (m, 1H), 4.42-4.35 (m, 2H), 4.21-4.15 (m, 1H), 3.96-3.77 (m, 4H), 3.30 (s, |

TABLE 74-continued

Characterization Data for Exemplary STAT3 Degraders

| | | | | |
|---|---|---|---|---|
| | | a][1,5]diazocin-5-yl]carbamoyl]-1H-indole-5-carbonylphosphonic acid | | 3H), 3.14-3.07 (m, 1H), 2.94-2.84 (m, 1H), 2.81-2.70 (m, 1H), 2.67-2.61 (m, 1H), 2.60-2.56 (m, 2H), 2.39-2.34 (m, 1H), 2.20-2.13 (m, 1H), 2.13-2.04 (m, 2H), 2.03-1.96 (m, 2H), 1.94-1.85 (m, 2H), 1.83-1.70 (m, 3H), 1.68-1.64 (m, 1H), 1.59-1.53 (m, 4H), 1.38-1.32 (m, 4H), 1.21-1.16 (m, 1H) |
| 137 | I-135 | 2-[[(5S,8S,10aR)-8-[[(1S)-3-carbamoyl-1-(diphenylmethylcarbamoyl)propyl]carbamoyl]-3-(4-[1-[1-(2,6-dioxopiperidin-3-yl)-3-methyl-2-oxo-1,3-benzodiazol-5-yl]azetidin-3-yl]butanoyl)-6-oxo-octahydropyrrolo[1,2-a][1,5]diazocin-5-yl]carbamoyl]-1H-indole-5-carbonylphosphonic acid | 1154.35 | (400 MHz, DMSO-$d_6$) δ 12.14 (s, 1H), 11.06 (s, 1H), 8.82-8.78 (m, 2H), 8.46 (d, J = 7.0 Hz, 1H), 8.26-8.18 (m, 1H), 7.97-7.93 (m, 1H), 7.55-7.51 (m, 1H), 7.47-7.39 (m, 1H), 7.37-7.21 (m, 12H), 6.94-6.83 (m, 1H), 6.80 (s, 1H), 6.30 (s, 1H), 6.12-6.08 (m, 2H), 5.31-5.23 (m, 1H), 5.00-4.90 (m, 1H), 4.47-4.43 (m, 1H), 4.42-4.28 (m, 2H), 4.26-4.17 (m, 1H), 3.99-3.88 (m, 4H), 3.85-3.73 (m, 3H), 3.26 (s, 3H), 2.91-2.87 (m, 1H), 2.72-2.64 (m, 3H), 2.22-2.06 (m, 4H), 2.03-1.89 (m, 4H), 1.86-1.72 (m, 4H), 1.65-1.59 (m, 6H) |
| 138 | I-145 | 2-[[(2S,11S)-2-[[(3S,4R)-1-carbamoyl-4-[[3'-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methyl)-[1,1'-biphenyl]-4-yl]methoxy]pentan-3-yl]carbamoyl]-12-oxo-1-azatricyclo[6.4.1.0^[4,13]]trideca-4(13),5,7-trien-11-yl]carbamoyl]-1H-indole-5-carbonylphosphonic acid | 1262.95 | (400 MHz, $CD_3OD$) δ 8.98 (d, J = 1.4 Hz, 1H), 8.89 (s, 1H), 8.66 (t, J J = 6.0 Hz, 1H) 8.11-8.09 (m, 1H), 8.02 (d, J J = 9.4 Hz, 1H), 7.95 (d, J = 9.1 Hz, 1H), 7.61-7.54 (m, 3H), 7.51-7.46 (m, 3H), 7.42-7.35 (m, 4H), 7.30 (d, J = 7.7 Hz, 1H), 7.11 (d, J = 3.2 Hz, 1H), 7.02-7.00 (m, 2H), 5.18-5.16 (m, 1H), 4.82-4.76 (m, 2H), 4.66 (d, J = 9.0 Hz, 1H), 4.61-4.52 (m, 5H), 4.45-4.36 (m, 1H), 4.05-4.03 (m, 1H), 3.91 (d, J = 11.0 Hz, 1H), 3.80 (dd, J = 10.9, 3.9 Hz, 1H), 3.75-3.66 (m, 2H), 3.65-3.60 (m, 1H), 3.52-3.47 (m, 1H), 3.25-3.22 (m, 1H), 3.05-2.98 (m, 1H), 2.48 (s, 3H), 2.45-2.17 (m, 5H), 2.13-1.97 (m, 2H), 1.74-1.72 (m, 1H), 1.23 (d, J = 6.4 Hz, 3H), 1.03 (s, 9H) |
| 139 | I-146 | diammonium 2-[[(2S,11S)-2-[[(3S,4R)-1-carbamoyl-4-[(4-[[(1r,3r)-3-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]cyclobutyl]methyl]phenyl)methoxy]pentan-3-yl]carbamoyl]-12-oxo-1-azatricyclo[6.4.1.0^[4,13]]trideca-4(13),5,7-trien-11-yl]carbamoyl]-1H-indole-5-carbonylphosphonate | 1240.70 | (400 MHz, $CD_3OD$) δ 9.00-8.95 (m, 1H), 8.89 (s, 1H), 8.11 (dd, J =8.8, 1.6 Hz, 1H), 8.03 (d, J = 9.3 Hz, 1H), 7.52 (d, J = 8.8 Hz, 1H), 7.51-7.45 (m, 2H), 7.45-7.38 (m, 2H), 7.38 (d, J = 0.9 Hz, 1H), 7.22 (d, J = 7.8 Hz, 2H), 7.14-7.06 (m, 4H), 5.20-5.18 (m, 1H), 4.83-4.76 (m, 1H), 4.69-4.59 (m, 1H), 4.58 (d, J = 7.1 Hz, 1H), 4.52-4.45 (m, 3H), 4.36 (d, J = 15.5 Hz, 1H), 4.01 (d, J = 11.1 Hz, 1H), 3.94 (d, J = 11.0 Hz, 1H), 3.83 (dd, J = 11.0, 3.8 Hz, 1H), 3.66-3.40 (m, 3H), 3.24 (d, J = 5.2 Hz, 2H), 3.12-2.97 (m, 2H), 2.68-2.62 (m, 2H), 2.49 (s, 3H), 2.45-2.20 (m, 7H), 2.20-1.85 (m, 5H), 1.71-1.69 (m, 1H), 1.20 (d, J = 6.3 Hz, 3H), 1.04 (s, 9H) |
| 140 | I-147 | 2-[[(5S,8S,10aR)-8-[[(1S)-3-carbamoyl-1-(diphenylmethylcarbamoyl)propyl]carbamoyl]-3-(8-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]octanoyl)-6-oxo-octahydropyrrolo[1,2-a][1,5]diazocin-5-yl]carbamoyl]-1H-indole-5-carbonylphosphonic acid | 1354.53 | (400 MHz, DMSO-$d_6$) δ 12.18-12.01 (m, 1H), 8.99 (s, 1H), 8.8.-8.76 (m, 2H), 8.58-8.56 (m, 1H), 8.42 (d, J = 6.7 Hz, 1H), 8.27-8.13 (m, 1H), 7.97 (d, J = 8.8 Hz, 1H), 7.84-7.81 (m, 1H), 7.53 (d, J = 8.7 Hz, 1H), 7.44-7.35 (m, 8H), 7.31-7.27 (m, 8H), 6.80-6.70 (m, 1H), 6.11 (dd, J = 8.5, 4.7 Hz, 1H), 5.00-4.95 (m, 2H), 4.59-4.52 (m, 1H), 4.48-4.34 (m, 5H), 4.28-4.18 (m, 2H), 3.97-3.90 (m, 1H), 3.81-3.76 (m, 1H), 3.69-3.64 (m, 4H), 3.32-3.27 (m, 4H), 2.94-2.57 (m, 1H), 2.45 (s, 3H), 2.33-2.21 (m, 1H), 2.15-2.11 (m, 5H), 2.06-1.99 (m, 2H), 1.94-1.87 (m, 2H), 1.85-1.61 (m, 1H), 1.56-1.52 (m, 1H), 1.32-1.27 (m, 11H), 0.94 (s, 9H). |
| 141 | I-148 | 2-[[(5S,8S,10aR)-8-[[(1S)-3-carbamoyl-1-(diphenylmethylcarbamoyl)propyl]carbamoyl]-3-(10-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]decanoyl)-6-oxo-octahydropyrrolo[1,2-a][1,5]diazocin-5-yl]carbamoyl]-1H-indole-5-carbonylphosphonic acid | $[(M-1)]^- =$ 1381.65 | (400 MHz, DMSO-$d_6$) δ 12.08-11.91 (m, 1H), 8.98 (s, 1H), 8.87-8.76 (m, 2H), 8.61-8.55 (m, 1H), 8.27-8.13 (m, 1H), 7.98 (d, J = 8.8 Hz, 1H), 7.84 (d, J = 9.3 Hz, 1H), 7.50-7.18 (m, 17H), 6.81-6.53 (m, 1H), 6.14-6.06 (m, 1H), 5.15-4.87 (m, 2H), 4.58-4.17 (m, 9H), 3.96-3.72 (m, 2H), 3.68-3.63 (m, 3H), 3.25-2.18 (m, 2H), 2.62-2.59 (m, 2H), 2.45 (s, 3H), 2.20-2.16 (m, 1H), 2.13-2.08 (m, 9H), 1.93-1.89 (m, 4H), 1.53-1.49 (m, 5H), 1.32-1.25 (m, 10H), 0.94 (s, 9H) |

TABLE 74-continued

| Characterization Data for Exemplary STAT3 Degraders | | | | |
|---|---|---|---|---|
| 142 | I-149 | diammonium 2-[[(2S,11S)-2-[[(3S,4R)-1-carbamoyl-4-[[4-(4-[[(2S)-1-[(2S,4S)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]butyl)phenyl]methoxy]pentan-3-yl]carbamoyl]-12-oxo-1-azatricyclo[6.4.1.0^[4,13]]trideca-4(13),5,7-trien-11-yl]carbamoyl]-1H-indole-5-carbonylphosphonate | 1243.70 | (400 MHz, DMSO-$d_6$) δ 11.98-11.90 (m, 1H), 9.04-8.87 (m, 3H), 8.34 (d, J = 7.9 Hz, 1H), 7.97 (dd, J = 8.6, 1.5 Hz, 1H), 7.89 (t, J = 8.9 Hz, 2H), 7.46-7.39 (m, 7H), 7.34-7.14 (m, 4H), 7.14-6.92 (m, 5H), 6.70 (s, 1H), 5.13 (dd, J = 10.6, 3.0 Hz, 1H), 4.96-4.91 (m, 1H), 4.71-4.66 (m, 1H), 4.49-4.29 (m, 4H), 4.22-4.17 (m, 1H), 3.94-3.89 (m, 1H), 3.84-3.78 (m, 1H), 3.53-3.42 (m, 3H), 3.41-3.37 (m, 2H), 3.30-3.04 (m, 2H), 2.93-2.88 (m, 1H), 2.47 (s, 3H), 2.35-2.24 (m, 4H), 2.20-1.94 (m, 4H), 1.86-1.72 (m, 1H), 1.69-1.63 (m, 1H), 1.57-1.45 (m, 5H), 1.39 (d, J = 6.9 Hz, 3H), 1.08 (d, J = 6.2 Hz, 3H), 0.96 (s, 9H) |
| 143 | I-151 | 2-[[(2S,11S)-2-[[(3S,4R)-1-carbamoyl-4-([4-[3-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]amino)propyl]phenyl]methoxy)pentan-3-yl]carbamoyl]-12-oxo-1-azatricyclo[6.4.1.0^[4,13]]trideca-4(13),5,7-trien-11-yl]carbamoyl]-1H-indole-5-carbonylphosphonic acid | 1229.45 | (400 MHz, DMSO-$d_6$) δ 12.06 (s, 1H), 8.99-8.97 (m, 2H), 8.84 (s, 1H), 8.58 (t, J = 6.1 Hz, 1H), 7.95 (d, J = 8.7 Hz, 1H), 7.89 (d, J = 9.0 Hz, 1H), 7.56-7.37 (m, 6H), 7.19-7.17 (m, 3H), 7.13-7.06 (m, 4H), 7.01 (t, J = 7.4 Hz, 1H), 6.69 (s, 1H), 6.24-6.13 (m, 2H), 5.16-5.09 (m, 1H), 4.71-4.66 (m, 1H), 4.49-4.33 (m, 7H), 4.27-4.20 (m, 1H), 3.82-3.79 (m, 2H), 3.69-3.64 (m, 1H), 3.53-3.50 (m, 1H), 3.49-3.42 (m, 3H), 3.25-3.17 (m, 1H), 3.18-3.10 (m, 2H), 3.07-2.90 (m, 3H), 2.57-2.55 (m, 1H), 2.45 (s, 3H), 2.26-2.22 (m, 2H), 2.10-2.00 (m, 3H), 1.96-1.85 (m, 1H), 1.83-1.72 (m, 1H), 1.67-1.52 (m, 3H), 1.08 (d, J = 6.2 Hz, 3H), 0.93 (s, 9H) |
| 144 | I-152 | 2-[[(2S,115)-2-[[(2S)-4-carbamoyl-1-[4-(5-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-y 1]carbamoyl]pentyl)phenoxy]butan-2-yl]carbamoyl]-12-oxo-1-azatricyclo[6.4.1.0^[4,13]]trideca-4(13),5,7-trien-11-yl]carbamoyl]-1H-indole-5-carbonylphosphonic acid | 1215.20 | (400 MHz, DMSO-$d_6$) δ 12.07 (s, 1H), 9.00-8.98 (m, 2H), 8.83 (s, 1H), 8.57 (t, J = 6.1 Hz, 1H), 8.11 (d, J = 8.2 Hz, 1H), 7.96 (d, J = 8.8 Hz, 1H), 7.84 (d, J = 9.3 Hz, 1H), 7.58-7.34 (m, 6H), 7.25 (s, 1H), 7.10-7.07 (m, 4H), 6.99 (t, J = 8.3 Hz, 1H), 6.81 (d, J = 8.3 Hz, 2H), 6.74 (s, 1H), 5.08 (dd, J = 10.7, 2.9 Hz, 1H), 4.71-4.67 (m, 1H), 4.54 (d, J = 9.3 Hz, 1H), 4.49-4.38 (m, 2H), 4.38-4.34 (m, 1H), 4.25-4.20 (m, 1H), 4.02-3.94 (m, 1H), 3.92-3.82 (m, 2H), 3.70-3.63 (m, 3H), 3.27-3.04 (m, 4H), 2.89-2.84 (m, 1H), 2.48-2.46 (m, 1H), 2.45 (s, 3H), 2.36-2.16 (m, 3H), 2.17-1.95 (m, 4H), 1.94-1.79 (m, 2H), 1.77-1.59 (m, 1H), 1.57-1.46 (m, 5H), 1.28-1.20 (m, 3H), 0.93 (s, 9H). |
| 145 | I-153 | 2-[[(2S,11S)-2-[[(2S)-4-carbamoyl-1-[(9-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]nonyl)oxy]butan-2-yl]carbamoyl]-12-oxo-1-azatricyclo[6.4.1.0^[4,13]]trideca-4(13),5,7-trien-11-yl]carbamoyl]-1H-indole-5-carbonylphosphonic acid | 1194.50 | (400 MHz, DMSO-$d_6$) δ 12.08 (s, 1H), 8.99-8.97 (m, 2H), 8.83 (s, 1H), 8.57 (t, J = 6.1 Hz, 1H), 8.04-7.80 (m, 3H), 7.56-7.34 (m, 7H), 7.21 (s, 1H), 7.11-7.09 (m, 2H), 7.04-6.93 (m, 1H), 6.71 (s, 1H), 5.09-5.05 (m, 1H), 4.74-4.62 (m, 1H), 4.55 (d, J = 9.4 Hz, 1H), 4.47-4.38 (m, 2H), 4.37-4.34 (m, 1H), 4.26-4.20 (m, 1H), 3.84-3.73 (m, 1H), 3.72-3.60 (m, 2H), 3.53-3.44 (m, 2H), 3.36-3.24 (m, 3H), 3.24-3.07 (m, 1H), 2.92-1.86 (m, 1H), 2.45 (s, 3H), 2.38-2.17 (m, 3H), 2.17-1.97 (m, 4H), 1.95-1.88 (m, 1H), 1.75-1.66 (m, 1H), 1.63-1.36 (m, 5H), 1.29-1.20 (m, 13H), 0.94 (s, 9H) |
| 146 | I-154 | 2-[[(2S,11S)-2-[[(2S)-4-carbamoyl-1-[(8-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]octyl)oxy]butan-2-yl]carbamoyl]-12-oxo-1-azatricyclo[6.4.1.0^[4,13]]trideca-4(13),5,7-trien-11-yl]carbamoyl]-1H-indole-5-carbonylphosphonic acid | 1180.70 | (400 MHz, DMSO-$d_6$) δ 12.08 (s, 1H), 9.00-8.96 (m, 2H), 8.83 (s, 1H), 8.57 (t, J = 6.1 Hz, 1H), 8.01-7.93 (m, 1H), 7.92-7.82 (m, 2H), 7.55-7.51 (m, 1H), 7.48 (d, J = 1.9 Hz, 1H), 7.44-7.35 (m, 4H), 7.21 (s, 1H), 7.12-7.09 (m, 2H), 7.04-6.95 (m, 1H), 6.71 (s, 1H), 5.12-5.09 (m, 1H), 5.09-5.05 (m, 1H), 4.70-4.66 (m, 1H), 4.57-4.52 (m, 1H), 4.48-4.40 (m, 2H), 4.38-4.34 (m, 1H), 4.23-4.19 (m, 1H), 3.85-3.74 (m, 1H), 3.71-3.61 (m, 2H), 3.50-3.46 (m, 1H), 3.33-3.28 (m, 3H), 3.25-3.10 (m, 2H), 2.92-2.87 (m, 1H), 2.45 (s, 3H), 2.32-2.17 (m, 3H), 2.14-1.96 (m, 4H), 1.92-1.89 (m, 1H), 1.78-1.64 (m, 1H), 1.60-1.33 (m, 6H), 1.32-1.17 (m, 10H), 0.94 (s, 9H) |
| 147 | I-155 | 2-[[(2S,11S)-2-[[(2S)-4-carbamoyl-1-[(7-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]heptyl)oxy]butan-2-yl]carbamoyl]-12-oxo-1-azatricyclo[6.4.1.0^[4,13]]trideca- | 1166.45 | (400 MHz, DMSO-$d_6$) δ 12.05 (s, 1H), 8.91-8.97 (m, 2H), 8.85 (s, 1H), 8.57 (t, J = 6.0 Hz, 1H), 8.00-7.81 (m, 3H), 7.55-7.35 (m, 6H), 7.21 (s, 1H), 7.12-7.08 (m, 2H), 7.04-6.97 (m, 1H), 6.71-6.55 (m, 1H), 5.11-4.99 (m, 1H), 4.72-4.63 (m, 1H), 4.57-4.53 (m, 1H), 4.47-4.40 (m, 2H), 4.37-4.32 (m, 1H), 4.27-4.19 (m, 1H), 3.81-3.75 (m, 2H), 3.71-3.60 (m, 2H), 3.57-3.43 (m, 2H), 3.26-3.00 (m, 2H), 2.95-2.83 (m, 1H), 2.69-2.67 (m, 1H), |

TABLE 74-continued

Characterization Data for Exemplary STAT3 Degraders

| | | | | |
|---|---|---|---|---|
| | | 4(13),5,7-trien-11-yl] carbamoyl]-1H-indole-5-carbonylphosphonic acid | | 2.45 (s, 3H), 2.35-2.17 (m, 3H), 2.16-1.97 (m, 4H), 1.94-1.87 (m, 1H), 1.78-1.62 (m, 1H), 1.61-1.31 (m, 6H), 1.28-1.22 (m, 8H), 1.09-1.02 (m, 1H), 0.96 (s, 9H) |
| 148 | I-156 | diammonium 2-[(5S,8S,10aR)-8-[[(1S)-3-carbamoyl-1-(diphenylmethylcarbamoyl)propyl] carbamoyl]-3-[3-(2-[2-[1-(2,6-dioxopiperidin-3-yl)-3-methyl-2-oxo-1,3-benzodiazol-5-yl]ethyl]phenyl)propanoyl]-6-oxo-octahydropyrrolo[1,2-a] [1,5]diazocin-5-yl]carbamoyl]-1H-indole-5-carbonylphosphonate | 1189.40 | (400 MHz, DMSO-$d_6$) δ 8.89 (s, 1H), 8.79-8.61 (m, 2H), 8.45-8.35 (m, 1H), 8.31-8.28 (m, 1H), 8.01-7.93 (m, 1H), 7.41-7.19 (m, 16H), 7.23-7.09 (m, 3H), 7.04-6.93 (m, 1H), 6.93-6.87 (m, 1H), 6.83-6.68 (m, 1H), 6.12-6.09 (m, 1H), 5.37-5.33 (m, 1H), 4.94-4.89 (m, 1H), 4.45-4.41 (m, 3H), 4.12-3.40 (m, 10H), 3.35-3.25 (m, 3H) 3.05-2.95 (m, 5H), 2.78-2.68 (m, 3H), 2.15-2.05 (m, 3H), 2.01-1.82 (m, 4H), 1.75-1.65 (m, 3H) |
| 149 | I-158 | 2-[[(5S,8S,10aR)-8-[[(1S)-3-carbamoyl-1-(diphenylmethyl-carbamoyl)propyl]carbamoyl]-3-[2-(4-[[1-(2,6-dioxopiperidin-3-yl)-3-methyl-2-oxo-1,3-benzodiazol-5-yl]methyl]piperidin-1-yl)acetyl]-6-oxo-octahydro-pyrrolo[1,2-a][1,5]diazocin-5-yl]carbamoyl]-1H-indole-5-carbonylphosphonic acid | 1168.70 | (400 MHz, DMSO-$d_6$) δ 12.38-11.81 (m, 1H), 11.10 (s, 1H), 9.33-9.28 (m, 1H), 8.95-8.55 (m, 3H), 8.30-8.26 (m, 1H), 7.96 (d, J = 8.7 Hz, 1H), 7.57-7.53 (m, 1H), 7.51-7.40 (m, 1H), 7.38-7.30 (m, 3H), 7.30-7.17 (m, 7H), 7.08-6.98 (m, 2H), 6.90-6.67 (m, 2H), 6.11-6.07 (m, 1H), 5.37-5.33 (m, 1H), 5.24-5.18 (m, 1H), 4.51-4.22 (m, 5H), 4.18-3.63 (m, 3H), 3.32 (s, 3H), 3.29-3.10 (m, 3H), 3.06-2.81 (m, 3H), 2.74-2.63 (m, 2H), 2.59-2.55 (m, 2H), 2.27-1.49 (m, 17H), 1.39-1.04 (m, 1H) |
| 150 | I-159 | 2-[[(2S,11S)-2-[[(2S)-4-carbamoyl-1-[(8-[[(2S)-1-[(2S,4R)-4-hydroxy-2-([[4-(4-methyl-1,3-thiazol-5-yl)phenyl]methyl] carbamoyl)pyrrolidin-1-yl]-3,3-dimethyl-1-oxobutan-2-yl] carbamoyl]oct-2-yn-1-yl)oxy] butan-2-yl]carbamoyl]-12-oxo-1-azatricyclo[6.4.1.0^[4,13]] trideca-4(13),5,7-trien-11-yl] carbamoyl]-1H-indole-5-carbonylphosphonic acid | 1176.65 | (400 MHz, DMSO-$d_6$) δ 12.12-11.96 (m, 1H), 9.04-8.96 (m, 1H), 8.95 (d, J = 8.0 Hz, 1H), 8.93-8.86 (m, 1H), 8.62-8.54 (m, 1H), 8.03-7.94 (m, 2H), 7.91-7.86 (m, 1H), 7.49 (d, J = 8.8 Hz, 1H), 7.46-7.37 (m, 6H), 7.22 (s, 1H), 7.13-7.09 (m, 2H), 7.03-6.97 (m, 1H), 6.76-6.68 (m, 1H), 5.08 (dd, J = 10.7, 2.9 Hz, 1H), 4.74-4.65 (m, 1H), 4.62-4.54 (m, 1H), 4.49-4.39 (m, 2H), 4.41-4.33 (m, 1H), 4.27-4.21 (m, 1H), 4.17-4.08 (m, 2H), 3.84-3.77 (m, 2H), 3.73-3.62 (m, 2H), 3.52-3.48 (m, 1H), 3.23-3.07 (m, 2H), 2.93-2.86 (m, 2H), 2.45 (s, 3H), 2.27-2.18 (m, 4H), 2.15-1.99 (m, 4H), 1.92-1.90 (m, 1H), 1.75-1.72 (m, 2H), 1.62-1.38 (m, 6H), 1.38-1.15 (m, 4H), 0.95 (s, 9H) |
| 151 | I-160 | diammonium 2-[[(2S,11S)-2-[[(3S,4R)-1-carbamoyl-4-([4-[4-(2-[(2S)-1-[(2S,4R)-4-hydroxy-2-([[4-(4-methyl-1,3-thiazol-5-yl)phenyl]methyl] carbamoyl)pyrrolidin-1-yl]-3,3-dimethyl-1-oxobutan-2-yl] carbamoyl]ethyl)piperidin-1-yl] phenyl]methoxy)pentan-3-yl] carbamoyl]-12-oxo-1-azatricyclo [6.4.1.0^[4,13]]trideca-4(13),5,7-trien-11-yl]carbamoyl]-1H-indole-5-carbonylphosphonate | 1284.05 | (400 MHz, DMSO-$d_6$) δ 11.95-11.87 (m, 1H), 8.99-8.92 (m, 2H), 8.62-8.54 (m, 1H), 8.04-7.91 (m, 2 H), 7.89-7.84 (m, 1H), 7.52-7.35 (m, 6H), 7.24-7.04 (m, 4H), 7.04-6.96 (m, 3H), 6.85-6.78 (m, 2H), 6.72-6.65 (m, 1H), 5.24-5.03 (m, 2H), 4.74-4.61 (m, 1H), 4.60-4.54 (m, 1H), 4.49-4.39 (m, 4H), 4.38-4.29 (m, 4H), 4.27-4.19 (m, 1H), 3.79-3.71 (m, 1H), 3.69-3.61 (m, 2H), 2.91-2.84 (m, 1H), 2.70-2.67 (m, 1H), 2.45 (s, 3H), 2.38-2.30 (m, 2H), 2.29-2.11 (m, 4H), 2.13-1.97 (m, 4H), 1.97-1.82 (m, 2H), 1.83-1.62 (m, 4H), 1.61-1.27 (m, 4H), 1.27-1.12 (m, 3H), 1.12-1.04 (m, 3H), 0.95 (s, 9H) |
| 152 | I-161 | diammonium 2-[[(2S,11S)-2-[[(3S,4R)-1-carbamoyl-4-[[4-(4-[(2S)-1-[(2S,4R)-4-hydroxy-2-([[4-(4-methyl-1,3-thiazol-5-yl)phenyl]methyl]carbamoyl) pyrrolidin-1-yl]-3,3-dimethyl-1-oxobutan-2-yl]carbamoyl] piperidin-1-yl)phenyl]methoxy] pentan-3-yl]carbamoyl]-12-oxo-1-azatricyclo[6.4.1.0^[4,13]] trideca-4(13),5,7-trien-11-yl]carbamoyl]-1H-indole-5-carbonylphosphonate | 1256.00 | (400 MHz, $CD_3OD$) δ 12.12-11.96 (m, 1H), 9.02-8.96 (m, 2H), 8.55-8.43 (m, 2H), 7.94-7.86 (m, 3H), 7.49-7.38 (m, 6H), 7.29-6.51 (m, 9H), 5.15-5.06 (m, 2H), 4.82-4.15 (m, 8H), 3.94-3.82 (m, 1H), 3.67 (m, 4H), 2.94-2.60 (m, 5H), 2.45 (s, 3H), 2.36-1.85 (m, 3H), 1.84-1.73 (m, 5H), 1.72-1.62 (m, 4H), 1.44-1.35 (m, 2H), 1.27-1.18 (m, 3H), 1.12-1.06 (m, 3H), 0.95 (s, 9H) |
| 153 | I-162 | diammonium 2-[[(2S,11S)-2-[[(3S,4R)-1-carbamoyl-4-([4-[4-([[(2S)-1-[(2S,4R)-4-hydroxy-2-([[4-(4-methyl-1,3-thiazol-5-yl)phenyl]methyl]carbamoyl) pyrrolidin-1-yl]-3,3-dimethyl-1-oxobutan-2-yl]carbamoyl] methyl)piperidin-1-yl]phenyl] methoxy)pentan-3-yl] carbamoyl]-12-oxo-1-azatricyclo [6.4.1.0^[4,13]]trideca-4(13),5,7-trien-11-yl]carbamoyl]-1H-indole-5-carbonylphosphonate | 1269.65 | (400 MHz, DMSO-$d_6$) δ 11.98-11.89 (m, 1H), 9.02-8.89 (m, 2H), 8.64-8.56 (m, 1H), 8.47-7.53 (m, 3H), 7.50-7.32 (m, 6H), 7.32-6.90 (m, 7H), 6.88-6.79 (m, 2H), 6.73-6.66 (m, 1H), 5.43-4.97 (m, 2H), 4.71-4.52 (m, 2H), 4.48-4.40 (m, 2H), 4.38-4.14 (m, 4H), 3.79-3.71 (m, 2H), 3.69-3.56 (m, 4H), 3.54-3.40(m, 3H), 3.22-3.09 (m, 2H) 2.91-2.87 (m, 1H), 2.71-2.54 (m, 3H), 2.45 (s, 3H), 2.32-2.25 (m, 4H), 2.18-1.88 (m, 6H), 1.83-1.76 (m, 2H), 1.73-1.43 (m, 4H), 1.41-1.15 (m, 3H), 1.09-1.01 (m, 4H), 0.96 (s, 9H) |

TABLE 74-continued

Characterization Data for Exemplary STAT3 Degraders

| | | | | |
|---|---|---|---|---|
| 154 | I-163 | diammonium 2-[[(2S,11S)-2-[(3S,4R)-1-carbamoyl-4-[(4-[[3-([[(2S)-1-[(2S,4R)-4-hydroxy-2-([[4-(4-methyl-1,3-thiazol-5-yl)phenyl]methyl]carbamoyl) pyrrolidin-1-yl]-3,3-dimethyl-1-oxobutan-2-yl]carbamoyl] methyl)cyclobutyl]methyl] phenyl)methoxy]pentan-3-yl] carbamoyl]-12-oxo-1-azatricyclo [6.4.1.0^[4,13]]trideca-4(13),5,7-trien-11-yl]carbamoyl]-1H-indole-5-carbonylphosphonate | 1255.80 | (400 MHz, DMSO-$d_6$) δ 12.12-11.98 (m, 1H), 9.03-8.96 (m, 2H), 8.85-8.79 (m, 1H), 8.56-8.47 (m, 1H), 7.98-7.92 (m, 1H), 7.91-7.87 (m, 1H), 7.86-7.82 (m, 1H), 7.53 (d, J = 8.7 Hz, 1H), 7.50-7.46 (m, 1H), 7.44-7.36 (m, 4H), 7.20-6.96 (m, 8H), 6.73-6.65 (m, 1H), 5.16-5.08 (m, 1H), 4.70-4.65 (m, 1H), 4.57-4.52 (m, 1H), 4.49-4.33 (m, 4H), 4.24-4.20 (m, 1H), 3.83-3.79 (m, 1H), 3.71-3.59 (m, 2H), 3.58-3.44 (m, 2H), 3.45-3.41 (m, 4H), 3.28-3.16 (m, 2H), 3.16-3.05 (m, 2H), 2.92-2.86 (m, 1H), 2.69-2.63 (m, 1H), 2.61-2.57 (m, 1H), 2.45 (s, 3H), 2.40-2.36 (m, 1H), 2.33-2.15 (m, 4H), 2.11-1.98 (m, 3H), 1.92-1.88 (m, 1H), 1.78-1.74 (m, 3H), 1.59-1.55 (m, 1H), 1.44-1.40 (m, 1H), 1.12-1.04 (m, 3H), 0.93 (s, 9H) |
| 155 | I-164 | 2-[[(2S,11S)-2-[[(2S)-4-carbamoyl-1-[3-(5-[[(2S)-1-[(2S,4R)-4-hydroxy-2-([[4-(4-methyl-1,3-thiazol-5-yl)phenyl]methyl] carbamoyl)pyrrolidin-1-yl]-3,3-dimethyl-1-oxobutan-2-yl] carbamoyl]pentyl)phenoxy] butan-2-yl]carbamoyl]-12-oxo-1-azatricyclo[6.4.1.0^[4,13]] trideca-4(13),5,7-trien-11-yl] carbamoyl]-1H-indole-5-carbonylphosphonic acid | [(M − 1)]$^-$ = 1212.35 | (400 MHz, DMSO-$d_6$) δ 11.86 (s, 1H), 8.99 (s, 1H), 8.96-8.88 (m, 2H), 8.61-8.55 (m, 1H), 8.12-8.05 (m, 1H), 7.98-7.92 (m, 1H), 7.89-7.82 (m, 1H), 7.45-7.35 (m, 6H), 7.29-7.22 (m, 2H), 7.20-7.13 (m, 2H), 7.12-7.06 (m, 2H), 7.05-6.95 (m, 1H), 6.79-6.69 (m, 4H), 5.13-5.03 (m, 1H), 4.72-4.65 (m, 1H), 4.58-4.52 (m, 1H), 4.48-4.39 (m, 2H), 4.38-4.32 (m, 1H), 4.26-4.19 (m, 1H), 4.03-3.96 (m, 1H), 3.91-3.87 (m, 2H), 3.70-3.60 (m, 2H), 3.47-3.41 (m, 3H), 3.16-3.08 (m, 2H), 2.92-2.84 (m, 1H), 2.45 (s, 3H), 2.35-2.22 (m, 3H), 2.16-2.01 (m, 4H), 1.95-1.78 (m, 2H),1.77-1.65 (m, 2H), 1.59-1.46 (m, 4H), 1.32-1.19 (m, 2H), 0.94 (s, 9H). |
| 156 | I-165 | 2-[[(5S,8S,10aR)-3-acetyl-8-[[(3S,4R)-1-carbamoyl-4-[[4-(4-[[(2S)-1-[(2S,4R)-4-hydroxy-2-([[4-(4-methyl-1,3-thiazol-5-yl)phenyl]methyl]carbamoyl) pyrrolidin-1-yl]-3,3-dimethyl-1-oxobutan-2-yl]carbamoyl] butyl)phenyl]methoxy]pentan-3-yl]carbamoyl]-6-oxo-octahydropyrrolo[1,2-a][1,5] diazocin-5-yl]carbamoyl]-1H-indole-5-carbonylphosphonic acid | 1252.50 | (400 MHz, DMSO-$d_6$) δ 12.24-11.96 (m, 1H), 8.99 (s, 1H), 8.87-8.79 (m, 1H), 8.61-8.46 (m, 2H), 7.99-7.94 (m, 1H), 7.92-7.76 (m, 2H), 7.53-7.48 (m, 1H), 7.47-7.35 (m, 5H), 7.26-7.20 (m, 2H), 7.20-7.11 (m, 3H), 6.79-6.55 (m, 1H), 5.19-4.95 (m, 2H), 4.61-4.51 (m, 1H), 4.48-4.38 (m, 4H), 4.37-4.30 (m, 1H), 4.30-4.18 (m, 1H), 3.93-3.83 (m, 2H), 3.80-3.75 (m, 2H), 3.70-3.64 (m, 3H), 3.48-3.43 (m, 2H), 3.43-3.39 (m, 2H), 3.37-3.29 (m, 3H), 2.59-2.53 (m, 2H), 2.45 (s, 3H), 2.36-2.26 (m, 1H), 2.23-2.09 (m, 5H), 2.08-1.97 (m, 3H), 1.95-1.71 (m, 4H), 1.69-1.62 (m, 1H), 1.59-1.38 (m, 5H), 1.13-1.02 (m, 3H), 0.94 (s, 9H) |
| 157 | I-166 | 2-[[(5S,8S,10aR)-8-[[(1S)-3-carbamoyl-1-(diphenylmethyl-carbamoyl)propyl]carbamoyl]-6-oxo-3-[2-[(1r,4r)-4-[[1-(2,6-dioxopiperidin-3-yl)-3-methyl-2-oxo-1,3-benzodiazol-5-yl] methyl]cyclohexyl]acetyl]-octahydropyrrolo[1,2-a][1,5] diazocin-5-yl]carbamoyl]-1H-indole-5-carbonylphosphonic acid | 1167.45 | (400 MHz, DMSO-$d_6$) δ 12.16-11.95 (m, 1H), 11.09 (s, 1H), 8.84-8.69 (m, 2H), 8.46-8.32 (m, 1H),8.25-8.13 (m, 1H), 7.99-7.89 (m, 2H), 7.54-7.47 (m, 1H), 7.44-7.20 (m, 11H), 7.03-6.91 (m, 2H), 6.87-6.70 (m, 2H), 6.15-6.03 (m, 1H), 5.37-5.27 (m, 1H), 4.96-4.86 (m, 1H), 4.45-4.38 (m, 2H), 3.94-3.70 (m, 5H), 3.52-3.50 (m, 1H), 3.33-3.31(m, 4H), 2.90 (s, 3H), 2.74-2.70 (m, 2H), 2.69-2.58 (m, 1H), 2.46-2.31 (m, 2H), 2.30-1.85 (m, 7H), 1.81-1.58 (m, 8H), 1.50-1.39 (m, 1H), 1.06-0.90 (m, 4H) |
| 158 | I-169 | 2-[[(5S,8S,10aR)-8-[[(1S)-3-carbamoyl-1-(diphenylmethyl-carbamoyl)propyl]carbamoyl]-3-(4-[4-[1-(2,6-dioxopiperidin-3-yl)-3-methyl-2-oxo-1,3-benzodiazol-5-yl]piperidin-1-yl] butanoyl)-6-oxo-octahydro-pyrrolo[1,2-a][1,5]diazocin-5-yl]carbamoyl]-1H-indole-5-carbonylphosphonic acid | 1183.15 | (400 MHz, DMSO-$d_6$) δ 11.88-11.82 (m, 1H), 1118-11.06 (m, 1H), 9.49-9.38 (m, 1H), 8.63-8.51 (m, 1H), 8.22 (d, J = 8.0 Hz, 1H), 7.81 (d, J = 8.9 Hz, 1H), 7.49-7.18 (m, 14H), 7.01-6.92 (m, 4H), 6.11 (d, J = 8.4 Hz, 1H), 5.28 (dd, J = 12.6, 5.2 Hz, 1H), 5.14-5.06 (m, 1H), 4.50-4.20 (m, 4H), 4.20-3.58 (m, 2H), 3.35 (s, 3H), 3.24-2.75 (m, 10H), 2.75-2.57 (m, 3H), 2.46-2.25 (m, 4H), 2.23-1.82 (m, 10H), 1.74 (m, 4H), 1.41 (m, 1H) |
| 159 | I-170 | diammonium 2-[[(2S,11S)-2-[[(2S)-4-carbamoyl-1-[3-[4-(2-[[(2S)-1-[(2S,4R)-4-hydroxy-2-([[4-(4-methyl-1,3-thiazol-5-yl)phenyl]methyl]carbamoyl) pyrrolidin-1-yl]-3,3-dimethyl-1-oxobutan-2-yl]carbamoyl] ethyl)phenyl]propoxy]butan-2-yl]carbamoyl]-12-oxo-1-azatricyclo [6.4.1.0^[4,13]]trideca-4(13),5,7-trien-11-yl]carbamoyl]-1H-indole-5-carbonylphosphonate | 1214.55 | (400 MHz, DMSO-$d_6$) δ 11.92-11.84 (m, 1H), 8.99-8.93 (m, 3H), 8.68-8.62 (m, 1H), 8.02-7.91 (m, 3H), 7.46-7.35 (m, 6H), 7.28-7.19 (m, 1H), 7.16-7.03 (m, 5H), 6.98-6.62 (m, 1H), 6.77-6.71 (m, 1H), 5.12-5.04 (m, 2H), 4.72-4.64 (m, 2H), 4.58-4.52 (m, 2H), 4.49-4.39 (m, 4H), 3.82-3.77 (m, 1H), 4.38-4.34 (m, 1H), 4.27-4.17(m, 2H), 3.86-3.74 (m, 1H), 3.69-3.64 (m, 5H), 2.81-2.72 (m, 3H), 2.45 (s, 3H), 2.44-2.42 (m, 3H), 2.07-2.02 (m, 4H), 1.94-1.87 (m, 2H), 1.96-1.85 (m, 1H), 1.82-1.76 (m, 4H), 1.61-1.56 (m, 1H), 0.89 (s, 9H) |
| 160 | I-171 | 2-[[(2S,11S)-2-[[(2S)-4-carbamoyl-1-[[(22)-8-[[(2S)-1-[(2S,4R)- | [(M − 1)]$^-$ = | (400 MHz, DMSO-$d_6$) δ 9.05-8.96 (m, 2H), 8.73-8.19 (m, 2H), 7.96-7.82 (m, 3H), 7.64-7.35 (m, |

TABLE 74-continued

| Characterization Data for Exemplary STAT3 Degraders | | | | |
|---|---|---|---|---|
| | | 4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]oct-2-en-1-yl]oxy]butan-2-yl]carbamoyl]-12-oxo-1-azatricyclo[6.4.1.0^[4,13]]trideca-4(13),5,7-trien-11-yl]carbamoyl]-1H-indole-5-carbonylphosphonic acid | 1176.70 | 8H), 7.25-7.00 (m, 3H), 6.82-6.62 (m, 1H), 5.56-5.39 (m, 4H), 4.82-4.12 (m, 8H), 4.05-3.96 (m, 2H), 3.82-3.75 (m, 2H), 3.73-3.64 (m, 3H), 3.34-3.15 (m, 6H), 2.45 (s, 3H), 2.30-1.80 (m, 12H), 1.58-1.21 (m, 4H), 0.95 (s, 9H) |
| 161 | I-172 | 2-[[(5S,8S,10aR)-3-acetyl-8-[[(1S)-3-carbamoyl-1-[(7-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]heptyl)carbamoyl]propyl]carbamoyl]-6-oxo-octahydropyrrolo[1,2-a][1,5]diazocin-5-yl]carbamoyl]-1H-indole-5-carbonylphosphonic acid | 1202.50 | (400 MHz, DMSO-$d_6$) δ 9.04-8.92 (m, 2H), 8.59-8.53 (m, 1H), 8.20-8.12 (m, 2H), 7.91-7.15 (m, 10H), 7.01-6.43 (m, 2H), 5.10-5.06 (m, 2H), 4.57-4.53 (m, 1H), 4.41-4.37 (m, 4H), 4.28-4.19 (m, 3H), 3.91-3.53 (m, 6H), 3.05-3.01 (m, 4H), 2.44 (s, 3H), 2.32-2.01 (m, 9H), 1.96-1.67 (m, 6H), 1.54-1.12 (m, 12H), 0.93 (s, 9H) |
| 162 | I-173 | 2-[[(5S,8S,10aR)-3-acetyl-8-[[(1S)-3-carbamoyl-1-[(8-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]octyl)carbamoyl]propyl]carbamoyl]-6-oxo-octahydropyrrolo[1,2-a][1,5]diazocin-5-yl]carbamoyl]-1H-indole-5-carbonylphosphonic acid | 1216.65 | (400 MHz, DMSO-$d_6$) δ 12.12-11.98 (m, 1H), 9.05-8.95 (m, 2H), 8.63-8.44 (m, 1H), 8.18-8.09 (m, 1H), 7.97 (d, J = 8.8 Hz, 1H), 7.89-7.79 (m, 2H), 7.48-7.39 (m, 6H), 7.31-7.24 (m, 2H), 6.82-6.76 (m, 1H), 5.08-4.92 (m, 2H), 4.62-4.58 (m, 1H), 4.51-4.38 (m, 3H), 4.37-4.31 (m, 1H), 4.29-4.14 (m, 3H), 3.92-3.61 (m, 6H), 3.11-2.98 (m, 3H), 2.45 (s, 3H), 2.32-2.18 (m, 4H), 2.13-2.00 (m, 6H), 1.96-1.60 (m, 7H), 1.57-1.33 (m, 5H), 1.25-1.21 (m, 8H), 0.94 (s, 9H) |
| 163 | I-174 | 2-[[(5S,8S,10aR)-8-[[(1S)-3-carbamoyl-1-(diphenylmethyl-carbamoyl)propyl]carbamoyl]-6-oxo-3-[2-[(1s,4s)-4-[[1-(2,6-dioxopiperidin-3-yl)-3-methyl-2-oxo-1,3-benzodiazol-5-yl]methyl]cyclohexyl]acetyl]-octahydropyrrolo[1,2-a][1,5]diazocin-5-yl]carbamoyl]-1H-indole-5-carbonylphosphonic acid | 1355.25 | (300 MHz, DMSO-$d_6$) δ 12.18-12.01 (m, 1H), 8.99 (s, 1H), 8.8.-8.76 (m, 2H), 8.58-8.56 (m, 1H), 8.42 (d, J = 6.7 Hz, 1H), 8.27-8.13 (m, 1H), 7.97 (d, J = 8.8 Hz, 1H), 7.84-7.81 (m, 1H), 7.53 (d, J = 8.7 Hz, 1H), 7.44-7.35 (m, 8H), 7.31-7.27 (m, 8H), 6.80-6.70 (m, 1H), 6.11 (dd, J = 8.5, 4.7 Hz, 1H), 5.00-4.95 (m, 2H), 4.59-4.52 (m, 1H), 4.48-4.34 (m, 5H), 4.28-4.18 (m, 2H), 3.97-3.90 (m, 1H), 3.81-3.76 (m, 1H), 3.69-3.64 (m, 4H), 3.32-3.27 (m, 4H), 2.94-2.57 (m, 1H), 2.45 (s, 3H), 2.33-2.21 (m, 1H), 2.15-2.11 (m, 5H), 2.06-1.99 (m, 2H), 1.94-1.87 (m, 2H), 1.85-1.61 (m, 1H), 1.56-1.52 (m, 1H), 1.32-1.27 (m, 11H), 0.94 (s, 9H) |
| 164 | I-176 | diammonium 2-[[(2S,11S)-2-[[(3S,4R)-1-carbamoyl-4-([4-[3-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methyl)cyclobutyl]phenyl]methoxy)pentan-3-yl]carbamoyl]-12-oxo-1-azatricyclo[6.4.1.0^[4,13]]trideca-4(13),5,7-trien-11-yl]carbamoyl]-1H-indole-5-carbonylphosphonate | 1240.10 | (400 MHz, DMSO-$d_6$) δ 11.91 (s, 1H), 9.02-8.84 (m, 3H), 8.64-8.53 (m, 1H), 8.08-7.84 (m, 3H), 7.45-7.37 (m, 6H), 7.34-7.05 (m, 11H), 7.02-6.98 (m, 1H), 6.70 (s, 1H), 5.14-5.10 (m, 1H), 4.68 (t, J = 7.8 Hz, 1H), 4.56 (dd, J = 9.4, 4.0 Hz, 1H), 4.47-4.36 (m, 5H), 4.25-4.20 (m, 1H), 3.85-3.77 (m, 2H), 3.70-3.63 (m, 2H), 3.46-3.43 (m, 3H), 3.21-3.07 (m, 1H), 2.94-2.85 (m, 1H), 2.74-2.54 (m, 1H), 2.46-2.44 (m, 3H), 2.42-2.33 (m, 1H), 2.28-1.99 (m, 7H), 1.96-1.67 (m, 4H), 1.60-1.50 (m, 1H), 1.09-1.07 (m, 3H), 0.96-0.94 (m, 9H). |
| 165 | I-177 | 2-[[(5S,8S,10aR)-8-[[(1S)-3-carbamoyl-1-(diphenylmethyl-carbamoyl)propyl]carbamoyl]-3-(3-[4-[1-(2,6-dioxopiperidin-3-yl)-3-methyl-2-oxo-1,3-benzodiazol-5-yl]piperidin-1-yl]propanoyl)-6-oxo-octahydro-pyrrolo[1,2-a][1,5]diazocin-5-yl]carbamoyl]-1H-indole-5-carbonylphosphonic acid | 1168.70 | (400 MHz, DMSO-$d_6$) δ 12.06-11.90 (m, 1H), 11.08 (s, 1H), 9.15-9.01 (m, 1H), 8.67 (s, 1H), 8.26-8.15 (m, 1H), 7.98-7.75 (m, 1H), 7.61-7.55 (m, 1H), 7.37-7.25 (m, 12H), 7.18-6.81 (m, 4H), 6.11 (d, J = 8.3 Hz, 1H), 5.38-5.31 (m, 1H), 5.22-5.16 (m, 1H), 4.42-4.33 (m, 4H), 4.02-3.51 (m, 6H), 3.30 (s, 3H), 3.10-2.82 (m, 7H), 2.75-2.57 (m, 2H), 2.30-1.82 (m, 12H), 1.78-1.54 (m, 6H) |
| 166 | I-178 | diammonium 2-[[(2S,11S)-2-[[(3S,4R)-1-carbamoyl-4-[(4-[[1-([(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl] | 1283.50 | (400 MHz, DMSO-$d_6$) δ 12.07-11.85 (m, 1H), 8.99-8.93 (m, 2H), 8.64-8.58 (m, 1H), 8.04-7.67 (m, 2H), 7.60-7.42 (m, 6H), 7.31-6.52 (m, 10H), 5.16-5.10 (m, 2H), 4.78-4.65 (m, 1H), 4.56-4.22 (m, 8H), 3.86-3.79 (m, 1H), 3.72-3.56 (m, 2H), 3.51-3.44 (m, 2H), 3.02-2.97 (m, 1H), 2.92-2.66 (m, 4H), 2.55 (s, 3H), 2.46-2.44 (m, 5H), 2.35- |

TABLE 74-continued

| Characterization Data for Exemplary STAT3 Degraders | | | | |
|---|---|---|---|---|
| | | methyl)piperidin-4-yl]methyl] phenyl)methoxy]pentan-3-yl] carbamoyl]-12-oxo-1-azatricyclo [6.4.1.0^[4,13]]trideca-4(13),5,7-trien-11-yl]carbamoyl]-1H-indole-5-carbonylphosphonate | | 2.14 (m, 1H), 2.16-1.85 (m, 7H), 1.81-1.73 (m, 1H), 1.61-1.45 (m, 5H), 1.25-1.19 (m, 2H), 1.10-1.06 (m, 3H), 0.94 (s, 9H) |
| 167 | I-179 | 2-[[(2S,11S)-2-[[(2S)-4-carbamoyl-1-([[4-(4-[[(2S)-1-[(2S,4R)-4-hydroxy-2-([[4-(4-methyl-1,3-thiazol-5-yl)phenyl]methyl] carbamoyl)pyrrolidin-1-yl]-3,3-dimethyl-1-oxobutan-2-yl] carbamoyl]butyl)phenyl] methyl](methyl)amino)butan-2-yl]carbamoyl]-12-oxo-1-azatricyclo[6.4.1.0^[4,13]] trideca-4(13),5,7-trien-11-yl] carbamoyl]-1H-indole-5-carbonylphosphonic acid | $[(M-1)]^-$ = 1225.45 | (400 MHz, $CD_3OD$) δ 9.02-8.98 (m, 1H), 8.91-8.86 (m, 1H), 8.10-8.04 (m, 1H), 7.53-7.38 (m, 5H), 7.35-7.25 (m, 2H), 7.18-7.13 (m, 3H), 7.09-7.03 (m, 2H), 5.22-5.05 (m, 1H), 4.74-4.44 (m, 6H), 4.41-4.21 (m, 2H), 4.20-4.02 (m, 1H), 3.96-3.77 (m, 2H), 3.65-3.47 (m, 2H), 3.28-3.09 (m, 4H), 2.82-2.53 (m, 4H), 2.48 (s, 3H), 2.39-2.19 (m, 5H), 2.14-2.05 (m, 1H), 1.98-1.68 (m, 2H), 1.62-1.56 (m, 4H), 1.55-1.42 (m, 3H), 1.42-1.27 (m, 1H), 1.05 (s, 9H) |
| 168 | I-180 | 2-[[(5S,8S,10aR)-3-acetyl-8-[[(1S)-3-carbamoyl-1-[(9-[[(2S)-1-[(2S,4R)-4-hydroxy-2-([[4-(4-methyl-1,3-thiazol-5-yl)phenyl] methyl]carbamoyl)pyrrolidin-1-yl]-3,3-dimethyl-1-oxobutan-2-yl]carbamoyl]nonyl) carbamoyl]propyl]carbamoyl]-6-oxo-octahydropyrrolo[1,2-a] [1,5]diazocin-5-yl] carbamoyl]-1H-indole-5-carbonylphosphonic acid | 1230.35 | (400 MHz, DMSO-$d_6$) δ 12.03-11.96 (m, 1H), 9.01-8.77 (m, 2H), 8.62-8.45 (m, 1H), 8.22-7.93 (m, 1H), 7.90-7.82 (m, 3H), 7.46-7.33 (m, 6H), 7.33-7.16 (m, 2H), 6.85-6.70 (m, 1H), 5.14-5.02 (m, 2H), 4.57-4.52 (m, 1H), 4.46-4.42 (m, 3H), 4.37-4.33 (m, 1H), 4.27-4.18 (m, 3H), 3.91-3.49 (m, 6H), 3.06-2.99 (m, 3H), 2.47-2.43 (m, 3H), 2.32-2.15 (m, 5H), 2.17-2.00 (m, 5H), 1.96-1.85 (m, 2H), 1.86-1.59 (m, 3H), 1.57-1.32 (m, 6H), 1.25-1.21 (m, 11H), 0.94 (s, 9H) |
| 169 | I-181 | 2-[[(5S,8S,10aR)-8-[[(1R)-3-carbamoyl-1-(diphenylmethyl-carbamoyl)propyl]carbamoyl]-3-[7-1-(2,6-dioxopiperidin-3-yl)-3-methyl-2-oxo-1,3-benzodiazol-5-yl]heptanoyl]-6-oxo-octahydropyrrolo[1,2-a][1,5] diazocin-5-yl]carbamoyl]-1H-indole-5-carbonylphosphonic acid | 1141.15 | (400 MHz, DMSO-$d_6$) δ 12.25-11.96 (m, 1H), 11.08 (s, 1H), 8.81 (s, 1H), 8.67 (d, J = 9.1 Hz, 1H), 8.61-8.57 (m, 1H), 8.46-8.42 (m, 1H), 7.97-7.93 (m, 1H), 7.87-7.83 (m, 1H), 7.54-7.44 (m, 3H), 7.43-7.27 (m, 4H), 7.30-7.16 (m, 5H), 7.20-7.09 (m, 1H), 7.06-6.98 (m, 3H), 6.90-6.81 (m, 2H), 6.76 (s, 1H), 6.25-6.76 (m, 1H), 5.36-5.30 (m, 1H), 4.89-4.62 (m, 1H), 4.52-4.14 (m, 3H), 3.96-3.91 (m, 1H), 3.85-3.81 (m, 1H), 3.37-3.28 (m, 6H), 3.15-3.00 (m, 1H), 2.96-2.84 (m, 1H), 2.73-2.55 (m, 4H), 2.24-2.19 (m, 1H), 2.16-2.03 (m, 3H), 1.97 (m, 6H), 1.80-1.45 (m, 4H), 1.37-1.33 (m, 4H) |
| 170 | I-182 | 2-[[(2S,11S)-2-[[(1S)-3-carbamoyl-1-(diphenylmethyl carbamoyl)propyl]carbamoyl]-6-[7-[1-(2,6-dioxopiperidin-3-yl)-3-methyl-2-oxo-1,3-benzodiazol-5-yl]heptyl]-12-oxo-1-azatricyclo [6.4.1.0^[4,13]]trideca-4(13),5,7-trien-11-yl]carbamoyl]-1H-indole-5-carbonylphosphonic acid | $[(M-1)]^-$ = 1144.45 | (400 MHz, DMSO-$d_6$) δ 12.08 (s, 1H), 11.08 (s, 1H), 8.94-8.90 (m, 1H), 8.87-8.70 (m, 2H), 8.23-8.19 (m, 1H), 7.95 (d, J = 8.7 Hz, 1H), 7.57-7.39 (m, 2H), 7.39-7.16 (m, HH), 7.06-6.95 (m, 2H), 6.95-6.87 (m, 3H), 6.77-6.75 (m, 1H), 6.10-6.06 (m, 1H), 5.35-5.30 (m, 1H), 5.14-5.10 (m, 1H), 4.66-4.64 (m, 1H), 4.35-4.31 (m, 1H), 3.50-3.41 (m, 2H), 3.41-3.32 (m, 3H), 3.31-3.02 (m, 3H), 2.95-2.86 (m, 3H), 2.77-2.65 (m, 2H), 2.64-2.56 (m, 3H), 2.22-2.18 (m, 2H), 2.06-2.02 (m, 3H), 1.95-1.70 (m, 2H), 1.66-1.49 (m, 4H), 1.35-1.30 (m, 6H) |
| 171 | I-183 | 2-[[(5S,8S,10aR)-8-[[3S,4R)-4-[(4-bromophenyl)methoxy]-1-carbamoylpentan-3-yl]carbamoyl]-3-[7-[1-(2,6-dioxopiperidin-3-yl)-3-methyl-2-oxo-1,3-benzodiazol-5-yl]heptanoyl]-6-oxo-octahydropyrrolo[1,2-a][1,5]diazocin-5-yl] carbamoyl]-1H-indole-5-carbonylphosphonic acid | 1144.55, 1146.55 | (400 MHz, DMSO-$d_6$) δ 12.15-11.92 (m, 1H), 11.08 (s, 1H), 8.89-8.64 (m, 2H), 8.40-7.69 (m, 2H), 7.59-7.35 (m, 4H), 7.32-6.93 (m, 5H), 6.86-6.82 (m, 1H), 6.79-6.55 (m, 1H), 5.35-5.24 (m, 1H), 5.04-4.88 (m, 1H), 4.62-4.28 (m, 4H), 4.22-4.17 (m, 1H), 3.94-3.75 (m, 4H), 3.47-3.36 (m, 3H), 3.33-3.27 (m, 3H), 2.97-2.83 (m, 1H), 2.74-2.62 (m, 2H), 2.61-2.54 (m, 3H), 2.49-2.26 (m, 1H), 2.24-1.86 (m, 5H), 1.85-1.62 (m, 4H), 1.60-1.50 (m, 5H), 1.43-1.23 (m, 4H), 1.15-0.98 (m, 4H) |
| 172 | I-184 | 2-[[(5S8S,10aR)-8-[[3S,4R)-4-(benzyloxy)-1-carbamoylpentan-3-yl]carbamoyl]-3-[7-[1-(2,6-dioxopiperidin-3-yl)-3-methyl-2-oxo-1,3-benzodiazol-5-yl]heptanoyl]-6-oxo-octahydro-pyrrolo[1,2-a][1,5 ]diazocin-5-yl]carbamoyl]-1H-indole-5-carbonylphosphonic acid | 1066.85 | (400 MHz, DMSO-$d_6$) δ 12.30-11.92 (m, 1H), 11.08 (s, 1H), 8.80 (s, 1H), 8.49 (d, J = 6.8 Hz, 1H), 8.01-7.76 (m, 2H), 7.57-7.40 (m, 2H), 7.36-7.25 (m, 5H), 7.23-7.08 (m, 1H), 7.03-6.95 (m, 2H), 6.85 (dd, J = 7.8, 6.1 Hz, 1H), 6.79-6.53 (m, 1H), 5.35-5.25 (m, 1H), 5.03-4.88 (m, 1H), 4.54-4.35 (m, 2H), 4.34-4.16 (m, 1H), 3.88 (d, J = 13.5 Hz, 1H), 3.84-3.69 (m, 2H), 3.52-3.35 (m, 4H), 3.35-3.30 (m, 1H), 3.29 (s, 3H), 2.98-2.81 (m, 1H), 2.75-2.54 (m, 5H), 2.48-2.27 (m, 1H), 2.24-2.05 (m, 3H), 2.05-1.89 (m, 3H), 1.89-1.71 (m, |

TABLE 74-continued

| Characterization Data for Exemplary STAT3 Degraders | | | | |
|---|---|---|---|---|
| | | | | 3H), 1.72-1.64 (m, 1H), 1.62-1.45 (m, 5H), 1.43-1.28 (m, 4H), 1.12-1.00 (m, 4H) |
| 173 | I-185 | diammonium 2-[[(2S,11S)-2-[[(2S)-4-carbamoyl-1-[3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenoxy]butan-2-yl]carbamoyl]-12-oxo-1-azatricyclo[6.4.1.0^[4,13]]trideca-4(13),5,7-trien-11-yl]carbamoyl]-1H-indole-5-carbonylphosphonate | 1229.90 | (400 MHz, $CD_3OD$) δ 8.97 (s, 1H), 8.86 (s, 1H), 8.09 (d, J = 8.8 Hz, 1H), 7.49 (d, J = 8.8 Hz, 1H), 7.46-7.36 (m, 4H), 7.35 (s, 1H), 7.18-7.02 (m, 4H), 6.78-6.68 (m, 3H), 5.17 (dd, J = 10.8, 3.3 Hz, 1H), 5.01-4.97 (m, 1H), 4.80-4.75 (m, 3H), 4.62-4.56 (m, 2H), 4.43 (s, 1H), 4.24-4.17 (m, 1H), 4.02-3.97 (m, 2H), 3.88 (d, J = 11.0 Hz, 1H), 3.80-3.72 (m, 2H), 3.62-3.45 (m, 2H), 3.35 (s, 1H), 3.28-3.22 (m,2H), 3.03 (d, J = 16.1 Hz, 1H), 2.58-2.52 (m, 4H), 2.10-1.85 (m, 4H), 1.58-1.56 (m, 4H), 1.50-1.45 (m, 3H), 1.31-1.26 (m, 3H), 1.03 (s, 9H) |
| 174 | I-186 | diammonium 2-[[(2S,11S)-2-[[(3S,4R)-1-carbamoyl-4-[[2-fluoro-4-(4-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]butyl)phenyl]methoxy]pentan-3-yl]carbamoyl]-12-oxo-1-azatricyclo[6.4.1.0^[4,13]]trideca-4(13),5,7-trien-11-yl]carbamoyl]-1H-indole-5-carbonylphosphonate | 1246.70 | (400 MHz, DMSO-$d_6$) δ 11.88 (s, 1H), 8.99 (s, 1H), 8.95-8.85 (m, 2H), 8.60-8.53 (m, 1H), 7.99-7.83 (m, 3H), 7.45-7.38 (m, 5H), 7.35-7.05 (m, 5H), 7.00 (dd, J = 9.2, 6.1 Hz, 2H), 6.92 (d, J = 7.8 Hz, 1H), 6.68 (s, 1H), 5.20-5.05 (m, 2H), 4.73-4.63 (m, 1H), 4.55 (d, J = 9.3 Hz, 1H), 4.53-4.30 (m, 4H), 4.25-4.20 (m, 1H), 3.78 (s, 1H), 3.71-3.60 (m, 2H), 3.50-3.41 (m, 3H), 3.20-3.04 (m, 3H), 2.94-2.82 (m, 1H), 2.68 (s, 1H), 2.45 (s, 3H), 2.37-1.83 (m, 7H), 1.76 (s, 2H), 1.56-1.47 (m, 6H), 1.27-1.12 (m, 2H), 1.15-1.05 (m, 3H), 0.94 (s, 9H) |
| 175 | I-187 | 2-[[(2S,11S)-2-[[(1S)-3-carbamoyl-1-([[3-(4-[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]butyl)phenyl]methyl]carbamoyl)propyl]carbamoyl]-12-oxo-1-azatricyclo[6.4.1.0^[4,13]]trideca-4(13),5,7-trien-11-yl]carbamoyl]-1H-indole-5-carbonylphosphonic acid | 1227.35 | (300 MHz, DMSO-$d_6$) δ 11.89 (s, 1H), 9.00 (s, 1H), 8.94-8.91 (m, 1H), 8.63-8.58 (m, 1H), 8.45-8.39 (m, 1H), 8.26 (d, J = 7.7 Hz, 1H), 7.98-7.91 (m, 2H), 7.47-7.37 (m, 5H), 7.30-6.95 (m, 3H), 7.14-7.10 (m, 1H), 7.08-6.96 (m, 6H), 6.80 (s, 1H), 5.17 (d, J = 10.5 Hz, 1H), 4.72-4.68 (m, 1H), 4.57 (d, J = 9.0 Hz, 1H), 4.51-4.32 (m, 3H), 4.29-4.21 (m, 4H), 3.67 (s, 3H), 3.53-3.47 (m, 4H), 3.25-2.94 (m, 4H), 2.46 (s, 3H), 2.32-2.23 (m, 3H), 2.19-2.04 (m, 4H), 1.94-1.87 (m, 3H), 1.59-1.45 (m, 4H), 0.95 (s, 9H) |
| 176 | I-188 | diammonium 2-[[(2S,11S)-2-[[(3S,4R)-1-carbamoyl-4-[[3-fluoro-4-(4-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]butyl)phenyl]methoxy]pentan-3-yl]carbamoyl]-12-oxo-1-azatricyclo[6.4.1,0^[4,13]]trideca-4(13),5,7-trien-11-yl]carbamoyl]-1H-indole-5-carbonylphosphonate | 1260.75 | $^1H$ NMR (300 MHz, DMSO-$d_6$) δ 11.89 (s, 1H), 9.00 (s, 1H), 8.99-8.86 (m, 2H), 8.39 (d, J = 7.7 Hz, 1H), 7.97-7.82 (m, 3H), 7.49-7.37 (m, 5H), 7.21-7.13 (m, 2H), 7.12-6.92 (m, 6H), 6.70 (s, 1H), 5.18-5.10 (m, 2H), 4.95-4.89 (m, 1H), 4.72-4.67 (m, 1H), 4.52 (d, J = 9.2 Hz, 1H), 4.43 (s, 3H), 4.28 (s, 1H), 3.82-3.78 (m, 1H), 3.60 (s, 2H), 3.48-3.44 (m, 2H), 3.25-3.05 (m, 2H), 2.88 (d, J = 16.6 Hz, 1H), 2.62-2.53 (m, 2H), 2.46 (s, 3H), 2.26-2.22 (m, 3H), 2.19-1.97 (m, 5H), 1.79-1.75 (m, 3H), 1.52-1.47 (m, 4H), 1.40-1.36 (m, 3H), 1.26-1.24 (m, 1H), 1.09 (s, 3H), 0.94 (s, 9H) |
| 177 | I-189 | diammonium 2-[[(2S,11S)-2-[[(2S)-4-carbamoyl-1-[2-fluoro-3-(4-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]butyl)phenoxy]butan-2-yl]carbamoyl]-12-oxo-1-azatricyclo[6.4.1.0^[4,13]]trideca-4(13),5,7-trien-11-yl]carbamoyl]-1H-indole-5-carbonylphosphonate | 1232.55 | (400 MHz, DMSO-$d_6$) δ 11.89 (s, 1H), 8.99 (s, 1H), 8.98-8.94 (m, 1H), 8.91 (s, 1H), 8.40 (d, J = 7.8 Hz, 1H), 8.16 (d, J = 7.4 Hz, 1H), 8.00-7.93 (m, 1H), 7.84 (d, J = 9.3 Hz, 1H), 7.47-7.37 (m, 6H), 7.28 (s, 1H), 7.11-7.07 (m, 2H), 7.01-6.97 (m, 3H), 6.84-6.08 (m, 1H), 6.78-6.74 (m, 1H), 5.09 (dd, J = 10.7, 2.9 Hz, 1H), 4.96-4.89 (m, 1H), 4.70-4.65 (m, 1H), 4.52 (d, J = 9.3 Hz, 1H), 4.48-4.42 (m, 1H), 4.30-4.26 (m, 1H), 4.02-3.92 (m, 3H), 3.63-3.59 (m, 3H), 3.49-3.43 (m, 2H), 3.21-3.19 (m, 2H), 3.14-3.09 (m, 2H), 2.89 (d, J = 16.6 Hz, 1H), 2.63-2.57 (m, 3H), 2.46 (s, 3H), 2.34-2.29 (m, 1H), 2.25-2.21 (m, 1H), 2.20-2.10 (m, 2H), 2.05-2.00 (m, 1H), 1.88-1.75 (m, 2H), 1.75-1.67 (m, 1H), 1.56-1.52 (m, 4H), 1.38 (d, J = 7.0 Hz, 3H), 0.94 (s, 9H). |
| 178 | I-190 | 2-[[(5S,8S,10aR)-8-[[(1S)-3-carbamoyl-1-(pyridin-2-yl)propyl]carbamoyl]-6-oxo-3-[2-[(1s,4s)-4-[[1-(2,6-dioxopiperidin-3-yl)-3-methyl-2-oxo-1,3-benzodiazol-5-yl]methyl]cyclohexyl]acetyl]-octahydropyrrolo[1,2-a][1,5]diazocin-5-yl]carbamoyl]-1H-indole-5-carbonylphosphonic acid | 1036.60 | (400 MHz, DMSO-$d_6$) δ 12.19 (s, 1H), 11.09 (s, 1H), 8.89-8.80 (m, 1H), 8.59-8.52 (m, 2H), 8.51-8.47 (m, 1H),7.97 (dd, J = 8.8, 1.7 Hz, 1H),7.80-7.75 (m, 1H), 7.56-7.52 (m, 1H), 7.47 (d, J = 3.8 Hz, 1H), 7.35-7.20 (m, 3H), 7.03-6.94 (m, 2H), 6.88-6.74 (m, 2H), 5.35-5.51 (m, 1H), 5.04-5.00 (m, 1H), 4.89-4.83 (m, 1H), 4.50 (t, J = 8.5 Hz, 1H), 4.21-4.17 (m, 1H), 3.94 (d, J = 14.1 Hz, 1H), 3.76 (d, J = 14.5 Hz, 1H), 3.29 (s, 2H), 2.94-2.86 (m, 1H), 2.70-2.64(m, 1H), 2.62-2.58 (m, 5H), |

TABLE 74-continued

| Characterization Data for Exemplary STAT3 Degraders | | | | |
|---|---|---|---|---|
| | | | | 2.21-2.17 (m, 1H), 2.12-2.08 (m, 2H), 2.06-1.98 (m, 10H), 1.76-1.72 (m, 3H), 1.48-1.42 (m, 8H), 1.37-1.32 (m, 2H). |
| 179 | I-191 | diammonium 2-[[(2S,11S)-2-[[(2S)-4-carbamoyl-1-[2-chloro-3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenoxy]butan-2-yl]carbamoyl]-12-oxo-1-azatricyclo[6.4.1.0^[4,13]]trideca-4(13),5,7-trien-11-yl]carbamoyl]-1H-indole-5-carbonylphosphonate | 1263.85 | (300 MHz, DMSO-$d_6$) δ 11.92 (s, 1H), 9.04-8.88 (m, 3H), 8.40 (d, J = 7.8 Hz, 1H), 8.14 (d, J = 7.3 Hz, 1H), 7.97 (d, J = 9.1 Hz, 1H), 7.82 (d, J = 9.2 Hz, 1H), 7.46-7.38 (m, 6H), 7.28 (s, 2H), 7.21-7.16 (m, 1H), 7.12-7.07 (m, 2H), 7.02-7.97 (m, 2H), 6.91 (d, J = 7.6 Hz, 1H) 6.77 (s, 1H), 5.10 (dd, J = 10.8, 2.8 Hz, 1H), 4.96-4.91 (m, 1H), 4.72-4.66 (m, 1H), 4.54 (d, J = 9.1 Hz, 1H), 4.47-4.42 (m, 1H), 4.30 (s, 1H), 4.05-3.96 (m, 3H), 3.66-3.56 (m, 2H), 3.55- 3.43 (m, 1H), 3.23-3.10 (m, 1H), 2.98 (d, J = 16.7 Hz, 1H), 2.71-2.65 (m, 2H), 2.56- 2.43 (m, 6H), 2.31-2.23 (m, 3H), 2.23-1.97 (m, 3H), 1.85-1.74 (m, 4H), 1.58-1.48 (m, 4H), 1.39 (d, J = 7.0 Hz, 3H), 1.35-1.23 (m, 2H) 0.95 (s, 9H). |
| 180 | I-192 | 2-[[(5S,8S,10aR)-8-[[(1S)-3-carbamoyl-1-(diphenylmethyl-carbamoyl)propyl]carbamoyl]-3-(4-[2-[1-(2,6-dioxopiperidin-3-yl)-3-methyl-2-oxo-1,3-benzodiazol-5-yl]ethyl]piperidine-1-carbonyl)-6-oxo-octahydro-pyrrolo[1,2-a][1,5]diazocin-5-yl]carbamoyl]-1H-indole-5-carbonylphosphonic acid | 1168.80 | (400 MHz, DMSO-$d_6$) δ 12.13 (s, 1H), 11.09 (s, 1H), 8.82-8.76 (m, 2H), 8.70-8.60 (m, 1H), 8.25 (d, J = 8.1 Hz, 1H), 7.96 (d, J = 8.7 Hz, 1H), 7.52 (d, J = 8.7 Hz, 1H), 7.43-7.39 (m, 1H), 7.38-7.20 (m, 12H), 7.06-7.01 (m, 2H), 6.89 (d, J = 8.1 Hz, 1H), 6.76 (d, J = 26.1 Hz, 1H), 6.11 (d, J = 8.4 Hz, 1H), 5.38-5.30 (m, 1H), 5.00-4.96 (m, 1H), 4.47-4.43 (m, 1H), 4.40-4.32 (m, 1H), 4.18 (s, 1H), 3.90-3.80 (m, 1H), 3.76 (s, 1H), 3.33-3.30 (m, 7H), 3.05-3.02 (m, 1H), 2.89-2.86 (m, 1H), 2.72-2.60 (m, 3H), 2.24-1.95 (m, 6H), 1.90-1.1.64 (m, 8H), 1.60-1.14 (m, 7H) |
| 181 | I-193 | 2-[[(2S,11S)-2-[[(1S)-3-carbamoyl-1-(diphenylmethyl carbamoyl)propyl]carbamoyl]-7-([5-[1-(2,6-dioxopiperidin-3-yl)-3-methyl-2-oxo-1,3-benzodiazol-5-yl]pentyl]oxy)-12-oxo-1-azatricyclo[6.4.1.0^[4,13]]trideca-4(13),5,7-trien-11-yl]carbamoyl]-1H-indole-5-carbonylphosphonic acid | 1134.65 | (300 MHz, DMSO-$d_6$) δ 12.03 (s, 1H), 8.93-8.87 (m, 1H), 8.80-8.77 (m, 1H), 8.43-8.38 (m, 1H), 8.26-8.24 (m, 1H), 7.97 (d, J = 8.7 Hz, 1H), 7.47-7.43 (m, 1H), 7.41-7.21 (m, 14H), 7.06-6.96 (m, 2H), 6.88-6.77 (m, 2H), 6.13-6.10 (m, 1H), 5.47-5.37 (m, 1H), 4.99-4.95 (m, 1H), 4.49-4.34 (m, 2H), 4.21 (s, 1H), 3.98-3.90 (m, 1H), 3.72-3.85 (m, 1H), 3.04 (s, 3H), 2.85-2.70 (m, 1H), 2.64-2.58 (m, 1H), 2.17-1.22 (m, 2H), 2.05-1.90 (m, 6H), 1.81-1.77 (m, 3H), 1.63-1.56 (m, 6H), 1.39-1.31 (m, 5H). |
| 182 | I-194 | diammonium 2-[[(2S,11S)-2-[[(2S)-4-carbamoyl-1-[3-(3-[[(2S)-1-[(2S,4R)-4-hydroxy-2-[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]propyl)phenoxy]butan-2-yl]carbamoyl]-12-oxo-1-azatricyclo[6.4.1.0^[4,13]]trideca-4(13),5,7-trien-11-yl]carbamoyl]-1H-indole-5-carbonylphosphonate | 1200.85 | (400 MHz, DMSO-$d_6$) δ 11.95-11.88 (m, 1H), 9.01-8.94 (m, 2H), 8.96-8.89 (m, 1H), 8.41 (d, J = 7.8 Hz, 1H), 8.12 (d, J = 8.1 Hz, 1H), 8.02-7.95 (m, 1H), 7.87 (d, J = 9.2 Hz, 1H), 7.47-7.38 (m, 4H), 7.38 (d, J = 8.4 Hz, 2H), 7.31-7.26 (m, 1H), 7.22-7.16 (m, 1H), 7.10 (d, J = 7.6 Hz, 2H), 7.04-6.98 (m, 1H), 6.79-6.71 (m, 4H), 5.10 (dd, J = 10.7, 2.9 Hz, 1H), 4.94-4.90 (m, 1H), 4.70-3.66 (m, 1H), 4.55 (d, J = 9.3 Hz, 1H), 4.46-4.38 (m, 1H), 4.29 (t, J = 3.7 Hz, 1H), 4.05-3.85 (m, 4H), 3.69-3.57 (m, 3H), 3.51-3.40 (m, 2H), 3.27-3.07 (m, 3H), 2.89 (d, J = 16.6 Hz, 1H), 2.65-2.61 (m, 1H), 2.46 (s, 3H), 2.34-2.08 (m, 6H), 2.08-1.98 (m, 1H), 1.90-1.67 (m, 5H), 1.38 (d, J = 7.0 Hz, 3H), 0.95 (s, 9H) |
| 183 | I-195 | 2-[[(5S,8S,10aR)-8-[[(1S)-3-carbamoyl-1-[[(4-methanesulfonylphenyl)methyl]carbamoyl]propyl]carbamoyl]-6-oxo-3-[2-[(1S,4S)-4-[[1-(2,6-dioxopiperidin-3-yl)-3-methyl-2-oxo-1,3-benzodiazol-5-yl]methyl]cyclohexyl]acetyl]-octahydro-pyrrolo[1,2-a][1,5]diazocin-5-yl]carbamoyl]-1H-indole-5-carbonylphosphonic acid | 1169.85 | (300 MHz, DMSO-$d_6$) δ 12.16-12.08 (m, 1H), 11.12-11.04 (m, 1H), 8.85-8.78 (m, 1H), 8.60-8.51 (m, 2H), 8.31-8.25 (m, 1H), 8.02-7.93 (m, 3H), 7.69-7.44 (m, 4H), 7.34-7.21 (m, 1H), 7.05-6.90 (m, 2H), 6.89-6.56 (m, 2H), 5.34 (dd, J = 12.6, 5.2 Hz, 1H), 5.02-4.89 (m, 1H), 4.64-4.35 (m, 6H), 4.35-4.14 (m, 4H), 4.14-3.73 (m, 2H), 3.36 (s, 3H), 3.20 (s, 3H), 3.01-2.84 (m, 1H), 2.76-2.63 (m, 6H), 2.31-1.62 (m, 12H), 1.57-1.30 (m, 8H) |
| 184 | I-196 | 2-[[(5S,8S,10aR)-8-[[(1S)-3-carbamoyl-1-[[(4-isopropylphenyl)methyl]carbamoyl]propyl]carbamoyl]-6-oxo-3-[2-[(1S,4S)-4-[[1-(2,6-dioxopiperidin-3-yl)-3-methyl-2-oxo-1,3-benzodiazol-5-yl]methyl] | 1133.55 | (400 MHz, DMSO-$d_6$) δ 12.12-11.95 (m, 1H), 11.14-11.06 (m, 1H), 8.86-8.81 (m, 1H), 8.59-8.13 (m, 3H), 8.03-7.93 (m, 1H), 7.61-7.42 (m, 2H), 7.31-7.22 (m, 1H), 7.21-7.10 (m, 4H), 7.07-6.93 (m, 2H), 6.90-6.69 (m, 2H), 5.34 (dd, J = 12.6, 5.5 Hz, 1H), 5.02-4.91 (m, 1H), 4.58-4.41 (m, 2H), 4.36-4.22 (m, 4H), 4.10-3.44 (m, 4H), |

TABLE 74-continued

Characterization Data for Exemplary STAT3 Degraders

| | | | | |
|---|---|---|---|---|
| | | cyclohexyl]acetyl]-octahydropyrrolo[1,2-a][1,5]diazocin-5-yl]carbamoyl]-1H-indole-5-carbonyl phosphonic acid | | 3.33 (s, 3H), 3.01-2.78 (m, 2H), 2.76-2.55 (m, 6H), 2.20-2.08 (m, 4H), 2.06-1.85 (m, 6H), 1.87-1.60 (m, 4H), 1.60-1.30 (m, 8H), 1.18 (dd, J = 7.0, 2.0 Hz, 6H) |
| 185 | I-197 | 2-[[(5S,8S,10aR)-8-[[(1S)-3-carbamoyl-1-[(naphthalen-1-yl methyl)carbamoyl]propyl]carbamoyl]-6-oxo-3-[2-[(1S,4S)-4-[[1-(2,6-dioxopiperidin-3-yl)-3-methyl-2-oxo-1,3-benzodiazol-5-yl]methyl]cyclohexyl]acetyl]-octahydropyrrolo[1,2-a][1,5]diazocin-5-yl]carbamoyl]-1H-indole-5-carbonylphosphonic acid | 1141.75 | (400 MHz, DMSO-$d_6$) δ 12.23-12.08 (m, 1H), 11.08 (d, J = 3.1 Hz, 1H), 8.81 (d, J = 3.9 Hz, 1H), 8.53-8.45 (m, 2H), 8.33-8.18 (m, 1H), 8.12-7.80 (m, 4H), 7.58-7.48 (m, 3H), 7.46-7.39 (m, 3H), 7.29-7.20 (m 1H), 7.05-6.93 (m, 2H), 6.90-6.65 (m, 2H), 5.33 (dd, J = 12.7, 5.7 Hz, 1H), 5.01-4.85 (m, 1H), 4.82-4.74 (m, 2H), 4.63-4.56 (m, 1H), 4.52-4.46 (m, 1H), 4.32-4.27 (m, 1H), 4.21-4.07 (m, 1H), 3.99-3.91 (m, 2H), 3.77-3.70 (m, 1H), 3.31 (s, 3H), 2.93-2.86 (m, 1H), 2.79-2.55 (m, 6H), 2.20-2.09 (m, 3H), 2.07-1.92 (m, 4H), 1.89-1.57 (m, 5H), 1.55-1.46 (m, 2H), 1.50-1.28 (m, 9H) |
| 186 | I-198 | 2-[[(2S,11S)-2-[[(1S)-3-carbamoyl-1-(diphenylmethyl carbamoyl)propyl]carbamoyl]-6-[5-[1-(2,6-dioxopiperidin-3-yl)-3-methyl-2-oxo-1,3-benzodiazol-5-yl]pentyl]-12-oxo-1-azatricyclo[6.4.1.0^[4,13]]trideca-4(13),5,7-trien-11-yl]carbamoyl]-1H-indole-5-carbonylphosphonic acid | 1118.55 | (400 MHz, DMSO-$d_6$) δ 12.13-11.08 (m, 1H), 11.12-11.06 (m, 1H), 8.94 (d, J = 7.9 Hz, 1H), 8.87-8.74 (m, 2H), 8.21 (d, J = 7.9 Hz, 1H), 7.95 (d, J = 8.8 Hz, 1H), 7.53 (d, J = 8.8 Hz, 1H), 7.52-7.45 (m, 1H), 7.37-7.16 (m, 11H), 7.08-6.96 (m, 2H), 6.94-6.85 (m, 3H), 6.83-6.76 (m, 1H), 6.07 (d, J = 8.3 Hz, 1H), 5.34 (dd, J = 12.7, 5.4 Hz, 1H), 5.15-5.10 (m, 1H), 4.69-4.58 (m, 1H), 4.42-4.36 (m, 1H), 3.33 (s, 3H), 3.19-3.04 (m, 2H), 2.95-2.86 (m, 2H), 2.77-2.57 (m, 5H), 2.25-2.18 (m, 2H), 2.13-1.97 (m, 3H), 1.94-1.87 (m, 2H), 1.84-1.69 (m, 2H), 1.68-1.56 (m, 6H), 1.40-1.34 (m, 2H) |
| 187 | I-199 | diammonium 2-[[(2S,11S)-2-[[(2S)-4-carbamoyl-1-[4-chloro-3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenoxy]butan-2-yl]carbamoyl]-12-oxo-1-azatricyclo[6.4.1.0^[4,13]]trideca-4(13),5,7-trien-11-yl]carbamoyl]-1H-indole-5-carbonylphosphonate | 1262.90 | (400 MHz, DMSO-$d_6$) δ 11.95-11.90 (m, 1H), 9.02-8.95 (m, 2H), 8.94-8.86 (m, 1H), 8.41 (d, J = 7.7 Hz, 1H), 8.12 (d, J = 8.1 Hz, 1H), 7.99-7.92 (m, 1H), 7.88-7.82 (m, 1H), 7.47-7.31 (m, 6H), 7.31-7.24 (m, 2H), 7.09-7.07 (m, 2H), 7.03-6.97 (m, 1H), 6.93-6.86(m, 1H), 6.83-6.74 (m, 2H), 5.13-5.05 (m, 1H), 4.97-4.89 (m, 1H), 4.71-4.65 (m, 1H), 4.32-4.25 (m, 1H), 4.02-3.84 (m, 3H), 3.62-3.58 (m, 3H), 3.51-3.39 (m, 3H), 3.24-3.07 (m, 3H), 2.88-2.84 (m, 1H), 2.62-2.58 (m, 2H), 2.45 (s, 3H), 2.27-2.21 (m, 3H), 2.18-2.08 (m, 4H), 2.07-1.97 (m, 1H), 1.85-1.75 (m, 2H), 1.74-1.66 (m, 1H), 1.57-1.44 (m, 4H), 1.38 (d, J = 7.0 Hz, 3H), 1.34-1.22 (m, 2H), 0.94 (s, 9H) |
| 188 | I-200 | 2-[[(2S,11S)-2-[[(2S)-4-carbamoyl-1-[2-chloro-5-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenoxy]butan-2-yl]carbamoyl]-12-oxo-1-azatricyclo[6.4.1.0^[4,13]]trideca-4(13),5,7-trien-11-yl]carbamoyl]-1H-indole-5-carbonylphosphonic acid | 1262.80 | (400 MHz, DMSO-$d_6$) δ 11.95-11.86 (m, 1H), 9.01-8.89 (m, 3H), 8.41 (d, J = 7.7 Hz, 1H), 8.13 (d, J = 7.5 Hz, 1H), 7.96 (d, J = 8.5 Hz, 1H), 7.80 (d, J = 9.2 Hz, 1H), 7.48-7.35 (m, 6H), 7.34-7.27 (m, 2H), 7.10-7.06 (m, 2H), 7.06-6.95 (m, 2H), 6.85-6.78 (m, 2H), 5.09-5.07 (m, 1H), 4.92-4.90 (m, 1H), 4.68-4.66 (m, 1H), 4.52-4.50 (m, 1H), 4.45-4.43 (m, 1H), 4.29-4.27 (m, 1H), 4.08-4.01 (m, 2H), 4.02-3.93 (s, 1H), 3.66-3.54 (m, 3H), 3.52-3.41 (m, 4H), 3.16-3.14 (m, 3H), 2.98-2.96 (m, 1H), 2.45 (s, 3H), 2.32-1.98 (m, 7H), 1.89-1.70 (m, 3H), 1.51-1.49 (m, 4H), 1.38 (d, J = 7.0 Hz, 3H), 1.26-1.24 (m, 2H), 0.93 (s, 9H) |
| 189 | I-201 | 2-[[(2S,11S)-2-[[(3R)-1-carbamoyl-5-[3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenyl]pentan-3-yl]carbamoyl]-12-oxo-1-azatricyclo[6.4.1.0^[4,13]]trideca-4(13),5,7-trien-11-yl]carbamoyl]-1H-indole-5-carbonylphosphonic acid | 1227.65 | $^1$H NMR (400 MHz, DMSO-$d_6$) δ 12.14-12.05 (m, 1H), 9.05-8.92 (m, 2H), 8.82-8.73 (m, 2H), 8.37 (d, J = 7.8 Hz, 1H), 8.01-7.73 (m, 3H), 7.59-7.32 (m, 7H), 7.30-7.06 (m, 4H), 7.06-6.91 (m, 6H), 6.72-6.70 (m, 1H), 5.10-5.07 (m, 1H), 4.96-4.88 (m, 1H), 4.74-4.64 (m, 1H), 4.54-4.50 (m, 1H), 4.43 (t, J = 8.0 Hz, 1H), 4.30-4.27 (m, 1H), 3.71-3.44 (m, 4H), 3.26-3.05 (m, 2H), 3.05-2.89 (m, 1H), 2.48-2.43 (m, 5H), 2.38-2.16 (m, 4H), 2.16-1.95 (m, 4H), 1.86-1.75 (m, 1H), 1.72-1.59 (m, 3H), 1.55-1.47 (m, 5H), 1.39-1.36 (m, 3H), 1.29-1.18 (m, 2H), 0.94-0.93 (m, 9H) |
| 190 | I-202 | 2-[[(5S,8S,10aR)-8-[[(1S)-3-carbamoyl-1-(diphenylmethyl-carbamoyl)propyl]carbamoyl]-6-oxo-3-[(1s,4s)-4-[2-1-(2,6-dioxopiperidin-3-yl)-3-methyl-2-oxo-1,3-benzodiazol-5-yl]ethyl]cyclohexanecarbonyl]-octahydropyrrolo[1,2-a][1,5]diazocin-5-yl]carbamoyl]-1H- | 1167.65 | (400 MHz, DMSO-$d_6$) δ 12.11-11.98 (m, 1H), 11.09 (s, 1H), 8.81-8.78 (m, 2H), 8.45-8.41 (m, 1H), 8.25-8.21 (m, 1H), 7.96 (d, J = 8.7 Hz, 1H), 7.52 (d, J = 8.7 Hz, 1H), 7.42-7.24 (m, 13H), 7.03-6.99 (m, 2H), 6.88-6.72 (m, 2H), 6.11 (d, J = 8.4 Hz, 1H), 5.38-5.30 (m, 1H), 5.01-4.79 (m, 1H), 4.46-4.35 (m, 2H), 4.29-4.10 (m, 2H), 4.02-3.91 (m, 1H), 3.79-3.69 (m, 1H), 2.94-2.83 (m, 2H), 2.74-2.60 (m, 4H), 2.57-2.54 (m, 2H), 2.24- |

TABLE 74-continued

Characterization Data for Exemplary STAT3 Degraders

| | | | | |
|---|---|---|---|---|
| | | indole-5-carbonylphosphonic acid | | 1.98 (m, 6H), 1.94-1.62 (m, 12H), 1.55-1.02 (m, 7H) |
| 191 | I-203 | 2-[[(5S,8S,10aR)-8-[[(1S)-3-carbamoyl-1-(diphenylmethyl-carbamoyl)propyl]carbamoyl]-6-oxo-3-[(1r,4r)-4-[2-[1-(2,6-dioxopiperidin-3-yl)-3-methyl-2-oxo-1,3-benzodiazol-5-yl]ethyl]cyclohexanecarbonyl]-octahydropyrrolo[1,2-a][1,5]diazocin-5-yl]carbamoyl]-1H-indole-5-carbonylphosphonic acid | 1167.60 | (400 MHz, DMSO-$d_6$) δ 12.12-11.98 (m, 1H), 11.09 (s, 1H), 8.81-8.75 (m, 2H), 8.42-8.39 (m, 1H), 8.26-8.22 (m, 1H), 7.97 (d, J = 8.7 Hz, 1H), 7.53 (d, J = 8.3 Hz, 1H), 7.46-7.19 (m, 12H), 7.06-6.97 (m, 2H), 6.89-6.87 (m, 1H), 6.78-6.72 (m, 1H), 6.11 (d, J = 8.4 Hz, 1H), 5.37-5.32 (m, 1H), 5.01-4.79 (m, 1H), 4.47-4.33 (m, 2H), 4.24-4.11 (m, 1H), 4.01-3.90 (m, 1H), 3.81-3.72 (m, 1H), 3.61-3.40 (m, 4H), 3.26-3.14 (m, 2H), 3.06-3.00 (m, 1H), 2.95-2.85 (m, 1H), 2.75-2.59 (m, 5H), 2.23-1.88 (m, 7H), 1.82-1.63 (m, 15H) |
| 192 | I-204 | 2-[[(2S,11S)-2-[[(2S)-4-carbamoyl-1-[3-chloro-5-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenoxy]butan-2-yl]carbamoyl]-12-oxo-1-azatricyclo[6.4.1.0^[4,13]]trideca-4(13),5,7-trien-11-yl]carbamoyl]-1H-indole-5-carbonylphosphonic acid | 1262.55. | (300 MHz, DMSO-$d_6$) δ 12.05 (s, 1H), 9.06-8.77 (m, 3H), 8.38 (d, J = 7.8 Hz, 1H), 8.11 (d, J = 7.7 Hz, 1H), 7.97 (d, J = 8.7 Hz, 1H), 7.80 (d, J = 9.2 Hz, 1H), 7.58-7.33 (m, 6H), 7.25 (s, 1H), 7.13-7.09 (m, 2H), 7.03-6.98 (m, 1H), 6.91-6.79 (m, 2H), 6.76-6.73 (m, 2H), 5.12-5.07 (m, 1H), 4.98-4.90 (m, 1H), 4.73-4.67 (m, 1H), 4.53 (d, J = 9.3 Hz, 1H), 4.44 (t, J = 8.0 Hz, 1H), 4.32-4.27 (m, 1H), 4.03-3.91 (m, 3H), 3.67-3.59 (m, 2H), 3.56-3.03 (m, 9H), 2.91-2.85 (m, 1H), 2.47 (s, 3H), 2.37-2.19 (m, 2H), 2.19-1.95 (m, 3H), 1.91-1.63 (m, 3H), 1.61-1.48 (m, 4H), 1.39 (d, J = 7.0 Hz, 3H), 1.34-1.16 (m, 3H), 0.94 (s, 9H) |
| 193 | I-205 | diammonium 2-[[(2S,11S)-2-[(2S)-4-carbamoyl-1-[3-(5-[[(2S)-1-[(2S,4R)-4-hydroxy-2-[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)-2-methylphenoxy]butan-2-yl]carbamoyl]-12-oxo-1-azatricyclo[6.4.1.0^[4,13]]trideca-4(13),5,7-trien-11-yl]carbamoyl]-1H-indole-5-carbonylphosphonate | 1242.65 | (300 MHz, DMSO-$d_6$) δ 11.93 (s, 1H), 9.04-8.83 (m, 3H), 8.40 (d, J = 7.8 Hz, 1H), 8.13 (d, J = 8.2 Hz, 1H), 7.98 (d, J = 8.7 Hz, 1H), 7.83 (d, J = 9.2 Hz, 1H), 7.53-7.17 (m, 11H), 7.13-6.98 (m, 4H), 6.79-6.73 (m, 3H), 5.14-5.10 (m, 1H), 4.96-4.89 (m, 1H), 4.73-4.67 (m, 1H), 4.59-4.50 (m, 1H), 4.45 (t, J = 8.0 Hz, 1H), 4.32-4.27 (m, 1H), 4.08-4.02 (m, 1H), 3.95-3.84 (m, 2H), 3.70-3.56 (m, 2H), 3.53-3.44 (m, 1H), 3.26-3.11 (m, 3H), 2.92-2.86 (m, 1H), 2.48 (s, 3H), 2.34-2.23 (m, 3H), 2.19-2.13 (m, 3H), 2.08 (s, 3H), 2.05-2.01 (m, 1H), 1.89-1.74 (m, 3H), 1.59-1.46 (m, 4H), 1.40 (d, J = 6.7 Hz, 3H), 1.34-1.26 (m, 2H), 0.95 (s, 9H) |
| 194 | I-206 | diammonium 2-[[(2S,11S)-2-[[(2S)-4-carbamoyl-1-[3-(5-[[(2S)-1-[(2S,4R)-4-hydroxy-2-([1-[4-(4-methyl-1,3-thiazol-5-yl)phenyl]cyclopropyl]carbamoyl)pyrrolidin-1-yl]-3,3-dimethyl-1-oxobutan-2-yl]carbamoyl]pentyl)phenoxy]butan-2-yl]carbamoyl]-12-oxo-1-azatricyclo[6.4.1.0^[4,13]]trideca-4(13),5,7-trien-11-yl]carbamoyl]-1H-indole-5-carbonylphosphonate | 1241.00 | (400 MHz, DMSO-$d_6$) δ 11.90 (s, 1H), 9.03-8.86 (m, 3H), 8.81 (s, 1H), 8.10 (d, J = 8.2 Hz, 1H), 8.01-7.86 (m, 2H), 7.45-7.42 (m, 2H), 7.38-7.21 (m, 6H), 7.16 (t, J = 7.7 Hz, 1H), 7.11-7.07 (m, 2H), 6.99 (t, J = 7.4 Hz, 1H), 6.82-6.67 (m, 4H), 5.11-5.08 (m, 1H), 4.71-4.66 (m, 1H), 4.55 (d, J = 9.3 Hz, 1H), 4.43-4.35 (m, 2H), 4.05-3.94 (m, 1H), 3.93-3.88 (m, 2H), 3.68-3.62 (m, 3H), 3.54-3.38 (m, 2H), 3.29-3.06 (m, 3H), 2.91-2.86 (m, 1H), 2.44 (s, 3H), 2.34-2.23 (m, 3H), 2.19-2.07 (m, 3H), 2.07-1.96 (m, 1H), 1.91-1.83 (m, 2H), 1.77-1.63 (m, 1H), 1.62-1.48 (m, 4H), 1.35-1.05 (m, 7H), 0.94 (s, 9H) |
| 195 | I-207 | diammonium 2-[[(2S,11S)-2-[[(2S)-4-carbamoyl-1-[2-fluoro-5-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenoxy]butan-2-yl]carbamoyl]-12-oxo-1-azatricyclo[6.4.1.0^[4,13]]trideca-4(13),5,7-trien-11-yl]carbamoyl]-1H-indole-5-carbonylphosphonate | $[(M-1)]^- =$ 1244.40 | (400 MHz, DMSO-$d_6$) δ 11.88 (s, 1H), 9.00-8.93 (m, 3H), 8.40 (d, J = 7.8 Hz, 1H), 8.16-8.13 (m, 1H), 7.95 (d, J = 8.9 Hz, 1H), 7.80 (d, J = 9.3 Hz, 1H), 7.67-7.58 (m, 1H), 7.46-7.34 (m, 12H), 7.27 (s, 1H), 7.16-6.93 (m, 5H), 6.77-6.74 (m, 2H), 5.15-5.04 (m, 1H), 4.96-4.89 (m, 1H), 4.70-4.66 (m, 1H),4.52 (d, J = 9.3 Hz, 1H), 4.44 (t, J = 8.1 Hz, 1H), 4.31-4.27 (m, 1H), 4.04-3.95 (m, 3H), 3.65-3.58 (m, 2H), 3.50-3.43 (m, 1H), 3.27-3.06 (m, 1H), 2.92-2.87 (m, 1H), 2.46 (s, 3H), 2.37-1.97 (m, 6H), 1.95-1.64 (m, 3H), 1.58-1.47 (m, 4H), 1.38 (d, J = 7.0 Hz, 3H), 1.29-1.23 (m, 2H), 0.93 (s, 9H) |
| 196 | I-208 | 2-[[(5S,8S,10aR)-8-[[(1S)-3-carbamoyl-1-(diphenylmethyl-carbamoyl)propyl]carbamoyl]-3-(5-[3-[1-(2,6-dioxopiperidin-3-yl)-3-methyl-2-oxo-1,3-benzodiazol-5-yl]cyclobutyl]pentanoyl)-6-oxo-octahydropyrrolo[1,2-a][1,5]diazocin-5-yl]carbamoyl]-1H-indole-5-carbonylphosphonic acid | 1167.60 | (300 MHz, DMSO-$d_6$) δ 12.13-11.95 (m, 1H), 11.08 (s, 1H), 8.93-8.70 (m, 2H), 8.46-8.42 (m, 1H), 8.30-8.18 (m, 1H), 7.98 (d, J = 8.8 Hz, 1H), 7.57-7.41 (m,2H), 7.41-7.19 (m, 11H), 7.14-6.95 (m, 2H), 6.92-6.64 (m, 2H), 6.14-6.09 (m, 1H), 5.39-5.30 (m, 1H), 5.02-4.88 (m, 1H), 4.58-4.12 (m, 4H), 4.12-3.53 (m, 4H), 3.33-3.15 (m, 4H), 2.97-2.87 (m, 1H), 2.80-2.58 (m, 3H), 2.48-2.38 (m, 2H), 2.32-1.88 (m, 10H), 1.84-1.56 (m, 8H), 1.51-1.17 (m, 4H) |
| 197 | I-209 | diammonium 2-[[(2S,11S)-2-[[(1S)-3-carbamoyl-1-[[3-(5- | 1241.60 | (300 MHz, DMSO-$d_6$) δ 12.15-11.74 (m, 1H), 9.95 (s, 1H), 9.08-8.86 (m, 3H), 8.41-8.37 (m, |

TABLE 74-continued

| Characterization Data for Exemplary STAT3 Degraders | | | |
|---|---|---|---|
| | [[(2S)-1-[(2S,4R)-4-hydroxy-2-[[(1S)-1-[4-(4-methyl-1,3-thiazol-5-yl)phenyl]ethyl]carbamoyl] pyrrolidin-1-yl]-3,3-dimethyl-1-oxobutan-2-yl]carbamoyl] pentyl)phenyl]carbamoyl] propyl]carbamoyl]-12-oxo-1-azatricyclo[6.4.1.0^[4,13]trideca-4(13),5,7-trien-11-yl] carbamoyl]-1H-indole-5-carbonylphosphonate | | 2H), 7.98-7.93 (m, 1H), 7.81 (d, J = 9.2 Hz, 1H), 7.47-7.34 (m, 8H), 7.22-7.10 (m, 4H), 7.03-6.97 (m, 1H), 6.90-6.86 (m, 1H), 6.80 (s, 1H), 5.22-5.18 (m, 1H), 4.96-4.89 (m, 1H), 4.73-4.69 (m, 1H), 4.53-4.45 (m, 2H), 4.33-4.27 (m, 2H), 3.62 (s, 3H), 3.25-3.00 (m, 5H), 2.47 (s, 3H), 2.30-2.21 (m, 4H), 2.19-2.10 (m, 3H), 2.08-1.76 (m, 5H), 1.59-1.48 (m, 4H), 1.39 (d, J = 6.9 Hz, 3H), 1.32-1.24 (m, 3H), 0.95 (s, 9H) |
| 198 I-210 | 2-[[(2S,11S)-2-[[(3S,4R)-1-carbamoyl-4-[3-(5-[[(2S)-1-[(2S,4R)-4-hydroxy-2-([[4-(4-methyl-1,3-thiazol-5-yl)phenyl] methyl]carbamoyl)pyrrolidin-1-yl]-3,3-dimethyl-1-oxobutan-2-yl]carbamoyl]pentyl)phenoxy] pentan-3-yl]carbamoyl]-1 2-oxo-1-azatricyclo[6.4.1.0^[4,13]] trideca-4(13),5,7-trien-11-yl]carbamoyl]-1H-indole-5-carbonylphosphonic acid | 1228.80 | (400 MHz, DMSO-$d_6$) δ12.04 (s, 1H), 8.99-8.96 (m, 2H), 8.84 (s, 1H), 8.59-5.55 (m, 1H), 8.05-7.96 (m, 2H), 7.86 (d, J = 9.3 Hz, 1H), 7.54-7.35 (m, 6H), 7.21 (s, 1H), 7.14-7.05 (m, 3H), 7.01-6.96 (m, 1H), 6.75-6.71 (m, 2H), 6.67-6.64 (m, 2H), 5.13-5.07 (m, 1H), 4.71-4.65 (m, 1H), 4.57-4.53 (m, 1H), 4.49-4.30 (m, 4H), 4.28-4.10 (m, 1H), 3.87-3.81 (m, 1H), 3.71-3.63 (m, 2H), 3.52-3.29 (m, 4H), 3.23-3.03 (m, 3H), 2.81-2.77 (m, 1H), 2.44 (s, 3H), 2.37-2.17 (m, 3H), 2.17-1.97 (m, 4H), 1.95-1.84 (m, 2H), 1.61-1.38 (m, 6H), 1.32-1.21 (m, 2H), 1.17 (d, J = 6.0 Hz, 3H), 0.93 (s, 9H) |
| 199 I-211 | diammonium 2-[[(2S,11S)-2-[[(2S)-4-carbamoyl-1-[3-(4-[[(2S)-1-[(2S,4R)-4-hydroxy-2-[[(1S)-1-[4-(4-methyl-1,3-thiazol-5-yl)phenyl]ethyl]carbamoyl] pyrrolidin-1-yl]-3,3-dimethyl-1-oxobutan-2-yl]carbamoyl] butyl)phenoxy]butan-2-yl] carbamoyl]-12-oxo-1-azatricyclo [6.4.1.0^[4,13]]trideca-4(13),5,7-trien-11-yl]carbamoyl]-1H-indole-5-carbonylphosphonate | $[(M-1)]^-$ = 1212.35 | (400 MHz, DMSO-$d_6$) δ 12.10-11.83 (m, 1H), 9.01-8.90 (m, 3H), 8.43-8.38 (m, 1H), 8.11 (d, J = 8.2 Hz, 1H), 7.99-7.93 (m, 1H), 7.83 (d, J = 9.2 Hz, 1H), 7.47-7.29 (m, 6H), 7.27 (s, 1H), 7.19-7.15 (m, 1H), 7.12-7.08 (m, 2H), 7.03-6.97 (m, 1H), 6.76-6.72 (m, 4H), 5.13-5.08 (m, 1H), 4.95-4.89 (m, 1H), 4.70-4.66 (t, J = 8.5 Hz, 1H), 4.55-4.51 (m, 1H), 4.47-4.43 (m, 1H), 4.31-4.26 (m, 1H), 4.01-3.97 (m, 1H), 3.92- 3.88 (m, 2H), 3.61 (s, 3H), 3.52-3.40 (m, 3H), 3.26-3.08 (m, 3H), 2.91-2.87 (m, 1H), 2.46 (s, 3H), 2.29-2.25 (m, 5H), 2.16-2.12 (m, 2H), 2.05-2.01 (m, 1H), 1.92-1.65 (m, 2H), 1.51-1.47 (m, 5H), 1.38 (d, J = 7.0 Hz, 3H), 0.94 (s, 9H) |
| 200 I-212 | 2-[[(2S,115)-2-[[(2S)-4-carbamoyl-1-[3-(5-[[(2S)-1-[(2S,4R)-4-hydroxy-2-[[(1S)-1-[4-(4-methyl-1,3-thiazol-5-yl)phenyl] ethyl]carbamoyl]pyrrolidin-1-yl]-3,3-dimethyl-1-oxobutan-2-yl]carbamoyl]pentyl)-4-methylphenoxy]butan-2-yl] carbamoyl]-12-oxo-1-azatricyclo [6.4.1.0^[4,13]]trideca-4(13),5,7-trien-11-yl]carbamoyl]-1H-indole-5-carbonylphosphonic acid | 1242.40 | (400 MHz, DMSO-$d_6$) δ 12.05 (s, 1H), 9.00-8.96 (m, 2H), 8.86-8.82 (m, 1H), 8.38 (d, J = 7.8 Hz, 1H), 8.09 (d, J = 8.2 Hz, 1H), 7.99-7.95 (m, 1H), 7.83-7.79 (m, 1H), 7.55-7.31 (m, 6H), 7.25 (s, 1H), 7.10-6.92 (m, 2H), 7.00-6.88 (m, 2H), 6.75-6.73 (m, 1H), 6.70- 6.60 (m, 2H), 5.09-4.98 (m, 1H), 4.93-4.76 (m, 1H), 4.69-4.49 (m, 1H), 4.53-4.35 (m, 1H), 4.46-4.42 (m, 1H), 4.37-4.26 (m, 2H), 3.99-3.79 (m, 2H), 3.87-3.68 (m, 3H), 3.62-3.60 (m, 2H), 3.46- 3.26 (m, 1H), 3.29-3.04 (m, 2H), 2.88-2.86 (m, 1H), 2.45 (s, 3H), 2.28-2.26 (m, 4H), 2.20-2.06 (m, 6H), 2.02-1.99 (m, 1H), 1.88-1.75 (m, 2H), 1.75-1.63 (m, 1H), 1.63-1.43 (m, 5H), 1.38 (d, J = 7.0 Hz, 3H), 1.36-1.27 (m, 2H), 0.94 (s, 9H) |
| 201 I-213 | 2-[[(2S,115)-2-[[(2S)-4-carbamoyl-1-[3-(5-[[(2S)-1-[(2S,4R)-4-hydroxy-2-[[(1S)-1-[4-(4-methyl-1,3-thiazol-5-yl)phenyl] ethyl]carbamoyl]pyrrolidin-1-yl]-3,3-dimethyl-1-oxobutan-2-yl]carbamoyl]pentyl)-5-methylphenoxy]butan-2-yl] carbamoyl]-12-oxo-1-azatricyclo [6.4.1.0^[4,13]]trideca-4(13),5,7-trien-11-yl]carbamoyl]-1H-indole-5-carbonylphosphonic acid | $[(M-1)]^-$ = 1240.35 | (300 MHz, DMSO-$d_6$) δ 12.03 (s, 1H), 8.98-8.92 (m, 2H), 8.83 (s, 1H), 8.36 (d, J = 7.8 Hz, 1H), 8.07 (d, J = 8.1 Hz, 1H), 8.00-7.91 (m, 1H), 7.78 (d, J = 9.2 Hz, 1H), 7.55-7.33 (m, 6H), 7.24 (s, 1H), 7.14-6.93 (m, 3H), 6.73 (s, 1H), 6.60-6.49 (m, 3H), 5.14-5.03 (m, 2H), 4.93-4.89 (m, 1H), 4.71-4.67 (m 1H), 4.56-4.37 (m, 3H), 4.33-4.18 (m, 1H), 4.04-3.79 (m, 5H), 3.66-3.53 (m, 2H), 3.52-3.37 (m, 2H), 3.17-3.13 (m, 2H), 2.94-2.82 (m, 1H), 2.45(s, 3H), 2.25-2.22 (m, 6), 2.15-1.94 (m, 3H), 1.86-1.66 (m, 2H), 1.49-1.47 (m, 6H), 1.37 (d, J = 6.9 Hz, 3H), 1.31-1.20 (m, 2H), 0.93 (s, 9H) |
| 202 I-214 | 2-[[(2S,11S)-2-[[(2S)-4-carbamoyl-1-[5-(5-[[(2S)-1-[(2S,4R)-4-hydroxy-2-[[(1S)-1-[4-(4-methyl-1,3-thiazol-5-yl)phenyl] ethyl]carbamoyl]pyrrolidin-1-yl]-3,3-dimethyl-1-oxobutan-2-yl]carbamoyl]pentyl)-2-methylphenoxy]butan-2-yl] carbamoyl]-12-oxo-1-azatricyclo | 1242.80 | (400 MHz, DMSO-$d_6$) δ 12.25-11.90 (m, 1H), 9.03-8.91 (m, 3H), 8.39-8.35 (m, 1H), 8.16-8.11 (m, 2H), 7.78 (d, J = 9.1 Hz, 1H), 7.59-7.35 (m, 6H), 7.28-7.24 (m, 1H), 7.06-7.01 (m, 4H), 6.70-6.66 (m, 3H), 5.13-5.08 (m, 2H), 4.95-4.89 (m, 1H), 4.70-4.66 (m, 1H), 4.54-4.50 (m, 1H), 4.45-4.41 (m, 1H), 4.30-4.26 (m, 1H), 4.05-4.01 (m, 1H), 3.91-3.88 (m, 2H), 3.61-3.59 (m, 2H), 2.88-2.84 (m, 1H), 2.46-2.42 (m, 4H), 2.26-2.00 (m, |

TABLE 74-continued

| Characterization Data for Exemplary STAT3 Degraders | | | | |
|---|---|---|---|---|
| | | [6.4.1.0^[4,13]]trideca-4(13),5,7-trien-11-yl]carbamoyl]-1H-indole-5-carbonylphosphonic acid | | 12H), 1.84-1.73 (m, 4H), 1.58-1.50 (m, 5H), 1.37 (d, J = 7.0 Hz, 3H), 1.28-1.22 (m, 4H), 0.93 (s, 9H) |
| 203 | I-215 | 2-[[(2S,11S)-2-[[(2S)-4-carbamoyl-1-[4-fluoro-3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenoxy]butan-2-yl]carbamoyl]-12-oxo-1-azatricyclo[6.4.1.0^[4,13]]trideca-4(13),5,7-trien-11-yl]carbamoyl]-1H-indole-5-carbonylphosphonic acid | 1247.10 | (400 MHz, DMSO-$d_6$) δ 11.99 (s, 1H), 9.01-8.94 (m, 2H), 8.86 (s, 1H), 8.38 (d, J = 7.8 Hz, 1H), 8.10 (d, J = 8.2 Hz, 1H), 8.00-7.93 (m, 1H), 7.80 (d, J = 9.2 Hz, 1H), 7.52-7.38 (m, 6H), 7.25 (s, 1H), 7.13-6.96 (m, 4H), 6.81 (dd, J = 6.2, 3.1 Hz, 1H), 6.78-6.70 (m, 2H), 5.13-5.06 (m, 1H), 4.95-4.88 (m, 1H), 4.72-4.68 (m, 1H), 4.52 (d, J = 9.3 Hz, 1H), 4.45-4.42 (m, 1H), 4.28 (s, 1H), 4.01-3.94 (m, 1H), 3.88 (s, 2H), 3.61 (s, 2H), 3.52-3.23 (m, 4H), 3.17-3.07 (m, 4H), 2.87 (d, J = 16.7 Hz, 1H), 2.46 (s, 3H), 2.32-2.20 (m, 3H), 2.16-2.07 (m, 3H), 2.07-1.97 (m, 1H), 1.85-1.77 (m, 2H), 1.76-1.66 (m, 1H), 1.60-1.44 (m, 4H), 1.38 (d, J = 7.2 Hz, 3H), 1.32-1.23 (m, 2H), 0.93 (s, 9H) |
| 204 | I-216 | 2-[[(2S,11S)-2-[[(2S)-4-carbamoyl-1-[3-fluoro-5-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenoxy]butan-2-yl]carbamoyl]-12-oxo-1-azatricyclo[6.4.1.0^[4,13]]trideca-4(13),5,7-trien-11-yl]carbamoyl]-1H-indole-5-carbonylphosphonic acid | 1246.40 | (400 MHz, DMSO-$d_6$) δ 12.10 (s, 1H), 9.01-8.94 (m, 2H), 8.83 (s, 1H), 8.37 (d, J = 7.8 Hz, 1H), 8.17-8.08 (m, 1H), 8.00-7.93 (m, 1H), 7.80 (d, J = 9.3 Hz, 1H), 7.54 (d, J = 8.8 Hz, 1H), 7.49 (d, J = 2.0 Hz, 1H), 7.44 (d, J = 8.2 Hz, 2H), 7.39 (d, J = 8.3 Hz, 2H), 7.25 (s, 1H), 7.13-7.08 (m, 2H), 7.02-6.98 (m, 1H), 6.75 (s, 1H), 6.65-6.57 (m, 3H), 5.11-5.08 (m, 1H), 4.94-4.90 (m, 1H), 4.75-4.66 (m, 1H), 4.53 (d, J = 9.3 Hz, 1H), 4.45-4.42 (m, 1H), 4.29 (s, 1H), 4.08-3.83 (m, 4H), 3.64-3.60 (m, 2H), 3.48-3.44 (m, 1H), 3.30-3.02 (m, 3H), 2.89-2.85 (m, 1H), 2.53 (s, 1H), 2.46 (s, 3H), 2.34-2.19 (m, 3H), 2.18-2.06 (m, 4H), 2.05-2.01 (m, 1H), 1.92-1.75 (m, 2H), 1.75-1.63 (m, 1H), 1.62-1.45 (m, 5H), 1.38 (d, J = 7.1 Hz, 3H), 1.29-1.25 (m, 2H), 0.94 (s, 9H) |
| 205 | I-217 | 2-[[(2S,11S)-2-[[(2S)-4-carbamoyl-1-[2-fluoro-3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenoxy]butan-2-yl]carbamoyl]-12-oxo-1-azatricyclo[6.4.1.0^[4,13]]trideca-4(13),5,7-trien-11-yl]carbamoyl]-1H-indole-5-carbonylphosphonic acid | $[(M + 18)]^+$ = 1246.36 | (300 MHz, DMSO-$d_6$) δ 12.01 (s, 1H), 9.04-8.82 (m, 3H), 8.35 (d, J = 7.8 Hz, 1H), 8.12 (d, J = 6.6 Hz, 1H), 8.02-7.93 (m, 1H), 7.77 (d, J = 9.2 Hz, 1H), 7.59-7.29 (m, 6H), 7.24 (s, 1H), 7.13-6.91 (m, 5H), 6.82-6.73 (m, 2H), 5.09-5.06 (m, 1H), 4.99-4.83 (m, 1H), 4.74-4.62 (m, 1H), 4.51 (d, J = 9.3 Hz, 1H), 4.43-4.41 (m, 1H), 4.29-4.26 (m, 1H), 4.04-3.89 (m, 3H), 3.64-3.35 (m, 5H), 3.18-3.13 (m, 2H), 2.94-2.82 (m, 1H), 2.59-2.50 (m, 4H), 2.45 (s, 3H), 2.13-2.09 (m, 6H), 1.86-1.65 (m, 3H), 1.58-1.42 (m, 4H), 1.38 (d, J = 6.8 Hz, 3H), 1.29-1.25 (m, 2H), 0.92 (s, 9H) |
| 206 | I-218 | diammonium 2-[[(2S,11S)-2-[[(3S,4R)-1-carbamoyl-4-[[4-(4-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]butyl)-3-methylphenyl]methoxy]pentan-3-yl]carbamoyl]-12-oxo-1-azatricyclo[6.4.1,0^[4,13]]trideca-4(13),5,7-trien-11-yl]carbamoyl]-1H-indole-5-carbonylphosphonate | 1256.25 | (400 MHz, DMSO-$d_6$) δ 11.90 (s, 1H), 8.99 (s, 1H), 8.97-8.84 (m, 2H), 8.39 (d, J = 7.8 Hz, 1H), 7.95 (dd, J = 8.8, 1.6 Hz, 1H), 7.88-7.85 (m, 2H), 7.47-7.35 (m, 6H), 7.18 (s, 1H), 7.14-6.95 (m, 6H), 6.69 (s, 1H), 5.12-5.08 (m, 1H), 4.96-4.89 (m, 1H), 4.70-4.67 (m, 1H), 4.53 (d, J = 9.3 Hz, 1H), 4.45-4.43 (m, 1H), 4.37-4.35 (m, 2H), 4.28 (s, 1H), 3.82-3.74 (m, 1H), 3.65-3.58 (m, 2H), 3.51-3.42 (m, 3H), 3.22-3.07 (m, 3H), 2.89 (d, J = 16.7 Hz, 1H), 2.46 (s, 3H), 2.35-2.32 (m, 3H), 2.32-2.11 (m, 5H), 2.10-1.95 (m, 3H), 1.83-1.75 (m, 3H), 1.60-1.44 (m, 6H), 1.38 (d, J = 7.0 Hz, 3H), 1.10 (d, J = 6.1 Hz, 3H), 0.94 (s, 9H) |
| 207 | I-219 | 2-[[(2S,11S)-2-[[(3S,4R)-1-carbamoyl-4-[3-(5-[[(2S)-1-[(2S,4R)-4-hydroxy-2-[[(1S)-1-[4-(4-methyl-l,3-thiazol-5-yl)phenyl]ethyl]carbamoyl]pyrrolidin-1-yl]-3,3-dimethyl-1-oxobutan-2-yl]carbamoyl]pentyl)phenoxy]pentan-3-yl]carbamoyl]-12-oxo-1-azatricyclo[6.4.1,0^[4,13]]trideca-4(13),5,7-trien-11-yl]carbamoyl]-1H-indole-5-carbonylphosphonic acid | 1242.45 | (400 MHz, DMSO-$d_6$) δ 12.06 (s, 1H), 9.02-8.94 (m, 2H), 8.85 (s, 1H), 8.38 (d, J = 7.8 Hz, 1H), 8.04-7.93 (m, 2H),7.81 (d, J = 9.2 Hz, 1H), 7.48-7.41 (m, 3H), 7.39-7.37 (m, 2H), 7.22 (s, 1H), 7.15-7.02 (m, 3H), 6.99-6.96 (m, 1H), 6.74 (d, J = 7.8 Hz, 2H), 6.67-6.66 (m, 2H), 5.12-5.08 (m, 2H), 4.96-4.89 (m, 1H), 4.73-4.64 (m, 1H), 4.52 (d, J = 9.3 Hz, 1H), 4.46-4.34 (m, 2H), 4.28 (s, 1H), 3.86-3.80 (m, 1H), 3.65-3.58 (m, 2H), 3.47-3.43 (m, 2H), 3.22-3.10 (m, 3H), 2.79 (d, J = 16.6 Hz, 1H), 2.68-2.65 (m, 1H), 2.46 (s, 3H), 2.29-2.21 (m, 4H), 2.16-1.97 (m, 5H), 1.94-1.73 (m, 2H), 1.71-1.41 (m, 6H), 1.38 (d, J = 7.0 Hz, 3H), 1.30-1.24 (m, 2H), 1.18 (d, J = 6.1 Hz, 3H), 0.93 (s, 9H). |
| 208 | I-220 | 2-[[(2S,11S)-2-[[(1S)-3-carbamoyl-1-([[3-(5-[[(2S)-1-[(2S,4R)-4-hydroxy-2-[[(1S)-1-[4- | 1255.55 | (400 MHz, $CD_3OD$) δ 9.00 (d, J = 14.3 Hz, 1H), 8.84 (s, 1H), 8.05 (dd, J = 15.9, 8.2 Hz, 1H), 7.54 (d, J = 8.6 Hz, 1H), 7.42-7.37 (m, 4H), 7.36-7.34 |

TABLE 74-continued

| Characterization Data for Exemplary STAT3 Degraders | | | | |
|---|---|---|---|---|
| | | (4-methyl-1,3-thiazol-5-yl) phenyl]ethyl]carbamoyl]pyrrolidin-1-yl]-3,3-dimethyl-1-oxobutan-2-yl]carbamoyl]pentyl) phenyl]methyl]carbamoyl)propyl] carbamoyl]-12-oxo-1-azatricyclo [6.4.1.0^[4,13]]trideca-4(13),5,7-trien-11-yl]carbamoyl]-1H-indole-5-carbonylphosphonic acid | | (m, 1H), 7.18-6.95 (m, 7H), 5.21-5.19 (m, 1H), 4.97 (d, J = 7.0 Hz, 1H), 4.78-4.76 (m, 1H), 4.63-4.54 (m, 2H), 4.40-4.38 (m, 2H), 4.35-4.30 (m, 2H), 3.87 (d, J J = 11.0 Hz, 1H), 3.73 (dd, J = 11.0, 3.8 Hz, 1H), 3.62-3.51 (m, 2H), 3.23-3.21 (m, 2H), 3.14-3.05 (m, 1H), 2.53-2.50 (m, 2H), 2.45 (s, 3H), 2.34-2.28 (m, 3H), 2.25-2.07 (m, 4H), 2.03-1.96 (m, 2H), 1.60-1.51 (m, 4H), 1.47 (d, J = 7.0 Hz, 3H), 1.29-1.21 (m, 2H), 1.02 (s, 9H). |
| 209 | I-221 | diammonium 2-[[(2S,11S)-2-[[(2S)-4-carbamoyl-1-[3-(4-[[(2S)-1-[(2S,4R)-4-hydroxy-2-([[4-(4-methy1-1,3-thiazol-5-yl) phenyl]methyl]carbamoyl) pyrrolidin-1-yl]-3,3-dimethyl-1-oxobutan-2-yl]carbamoyl]butyl) phenoxy]butan-2-yl] carbamoyl]-12-oxo-1-azatricyclo [6.4.1.0^[4,13]]trideca-4(13),5,7-trien-11-yl]carbamoyl]-1H-indole-5-carbonylphosphonate | 1200.75 | (400 MHz, DMSO-$d_6$) δ 11.97 (s, 1H), 8.99 (s, 1H), 8.95 (d, J = 8.1 Hz, 1H), 8.87 (s, 1H), 8.57-8.55 (m, 1H), 8.09 (d, J = 8.2 Hz, 1H), 7.94 (dd, J = 8.8, 1.6 Hz, 1H), 7.87 (d, J = 9.3 Hz, 1H), 7.48-7.38 (m, 6H), 7.24 (s, 1H), 7.17 (dd, J = 8.9, 7.3 Hz, 1H), 7.11-7.08 (m, 2H), 7.01-6.98 (m, 1H), 6.79-6.69 (m, 4H), 5.10-5.08 (m, 2H), 4.72-4.66 (m, 1H), 4.55 (d, J = 9.3 Hz, 1H), 4.47-4.39 (m, 2H), 4.35 (s, 1H), 4.22 (dd, J = 15.8, 5.4 Hz, 1H), 4.02-3.96 (m, 1H), 3.93-3.86 (m, 3H), 3.71-3.61 (m, 3H), 3.51-3.40 (m, 1H), 3.16-3.09 (m, 1H), 2.88 (d, J = 16.6 Hz, 1H), 2.69-2.67 (m, 1H), 2.45 (s, 3H), 2.35-2.33 (m, 1H), 2.31-1.99 (m, 7H), 1.96-1.62 (m, 3H), 1.60-1.47 (m, 5H), 0.94 (s, 9H). |
| 210 | I-222 | 2-[[(2S,11S)-2-[[(1S)-3-carbamoyl-1-([[3-(5-[[(2S)-1-[(2S,4R)-4-hydroxy-2-([[4-(4-methyl-1,3-thiazol-5-yl)phenyl]methyl] carbamoyl)pyrrolidin-1-yl]-3,3-dimethyl-1-oxobutan-2-yl]carbamoyl]pentyl)phenyl] methyl]carbamoyl)propyl] carbamoyl]-12-oxo-1-azatricyclo [6.4.1.0^[4,13]]trideca-4(13),5,7-trien-11-yl]carbamoyl]-1H-indole-5-carbonylphosphonic acid | 1241.55 | (400 MHz, CD3OD) δ 8.94 (s, 1H), 8.88 (s, 1H), 8.07(d, J = 8.8 Hz, 1H), 7.56 (d, J = 8.6 Hz, 1H), 7.47-7.43 (m, 2H), 7.39 (d, J = 8.2 Hz, 2H), 7.34 (s, 1H), 7.13 (d, J = 7.6 Hz, 3H), 7.09-6.98 (m, 4H), 5.21 (dd, J = 10.8, 3.5 Hz, 1H), 4.79 (d, J = 1A Hz, 1H), 4.66 (s, 1H), 4.63-4.48 (m, 3H), 4.43-4.39 (m, 1H), 4.37-4.31 (m, 3H), 3.92 (d, J = 11.1 Hz, 1H), 3.81 (dd, J = 11.1, 3.9 Hz, 1H), 3.54 (d, J = 5.5 Hz, 1H), 3.26-3.22 (m, 2H), 3.13-3.09 (m, 1H), 2.54-2.50 (m, 2H), 2.49-2.45 (m, 3H), 2.39-2.34 (m, 1H), 2.33-2.29 (m, 3H), 2.27-2.19 (m, 3H), 2.15-1.97(m, 3H), 1.60-1.55 (m, 4H), 1.33-1.23 (m, 2H), 1.04 (s, 9H) |
| 212 | I-223 | diammonium 2-[[(2S,11S)-2-[[(3S,4R)-1-carbamoyl-4-([4-[3-(1-[[(2S)-1-[(2S,4R)-4-hydroxy-2-([[4-(4-methyl-1,3-thiazol-5-yl)phenyl]methyl] carbamoyl)pyrrolidin-1-yl]-3,3-dimethyl-1-oxobutan-2-yl] carbamoyl]cyclopropyl)propyl] phenyl]methoxy)pentan-3-yl] carbamoyl]-12-oxo-1-azatricyclo [6.4.1.0^[4,13]]trideca-4(13),5,7-trien-11-yl]carbamoyl]-1H-indole-5-carbonylphosphonate | 1255.65 | (400 MHz, DMSO-$d_6$) δ 11.86 (s, 1H), 8.99-8.96 (m, 2H), 8.59 (s, 1H), 7.95-7.86 (m, 1H), 7.42-7.39 (m, 7H), 7.16-6.95 (m, 9H), 6.75-6.69 (m, 2H), 5.14-5.10 (m, 1H), 4.67 (s, 1H), 4.54 (d, J = 8.9 Hz, 1H), 4.48-4.44 (m, 1H), 4.43-4.32 (m, 3H), 4.30-4.20 (m, 1H), 3.83-3.77 (m, 1H), 3.65-3.57 (m, 2H), 3.48-3.40 (m, 3H), 3.20-3.03 (m, 2H), 2.88-2.84 (m, 1H), 2.43-2.41 (m, 4H), 2.30-2.14 (m, 2H), 2.06-2.14 (m, 3H), 1.93-1.87 (m, 1H), 1.74-1.70 (m, 4H), 1.45-1.40 (m, 3H), 1.24 (s, 1H), 1.08-1.04 (m, 3H), 0.97 (s, 9H), 0.89-0.81 (m, 4H), 0.62-0.48 (m, 2H) |
| 213 | I-224 | diammonium 2-[[(2S,11S)-2-[[(3R)-1-carbamoyl-5-[3-(5-[[(2S)-1-[(2S,4R)-4-hydroxy-2-([[4-(4-methy1-1,3-thiazol-5-yl) phenyl]methyl]carbamoyl) pyrrolidin-1-yl]-3,3-dimethyl-1-oxobutan-2-yl]carbamoyl] pentyl)phenyl]pentan-3-yl] carbamoyl]-12-oxo-1-azatricyclo [6.4.1.0^[4,13]]trideca-4(13),5,7-trien-11-yl]carbamoyl]-1H-indole-5-carbonylphosphonate | 1212.40 | (400 MHz, DMSO-$d_6$) δ 11.88 (s, 1H), 9.01-8.88 (m, 3H), 8.60-8.56 (m, 1H), 8.00-7.90 (m, 2H), 7.85 (d, J = 9.3 Hz, 1H), 7.45-7.37 (m, 6H), 7.21 (s, 1H), 7.14-7.10 (m, 3H), 7.02-6.93 (m, 4H), 6.71 (s, 1H), 5.08 (dd, J = 10.7, 2.9 Hz, 1H), 4.74-4.64 (m, 1H), 4.58-4.51 (m, 1H), 4.48-4.38 (m, 2H), 4.38-4.33 (m, 1H), 4.23 (dd, J = 15.8, 5.4 Hz, 1H), 3.69 (m, 4H), 3.58-3.43 (m, 4H), 3.23-3.07 (m, 3H), 2.95 (d, J = 16.7 Hz, 1H), 2.50-2.46 (m, 2H), 2.45 (s, 3H), 2.32-2.20 (m, 3H), 2.17-2.00 (m, 4H), 1.96-1.85 (m, 1H), 1.70-1.58 (m, 4H), 1.57-1.44 (m, 4H), 1.31-1.21 (m, 2H), 0.94 (s, 9H) |
| 215 | I-225 | diammonium 2-[[(2S,11S)-2-[[(35,4R)-1-carbamoyl-4-[[2-fluoro-4-(4-[[(2S)-1-[(2S,4R)-4-hydroxy-2-[[(1S)-1-[4-(4-methyl-1,3-thiazol-5-yl)phenyl] ethyl]carbamoyl]pyrrolidin-1-yl]-3,3-dimethyl-1-oxobutan-2-yl]carbamoyl]butyl)phenyl] methoxy]pentan-3-yl]carbamoyl]-12-oxo-1-azatricyclo [6.4.1,0^[4,13]]trideca-4(13),5,7-trien-11-yl]carbamoyl]-1H-indole-5-carbonylphosphonate | 1261.90 | (400 MHz, DMSO-$d_6$) δ 11.89 (s, 1H), 9.01-8.85 (m, 3H), 8.39 (d, J = 7.8 Hz, 1H), 7.99-7.81 (m, 3H), 7.47-7.35 (m, 6H), 7.28-7.24 (m, 1H), 7.20-6.89 (m, 6H), 6.69 (s, 1H),5.11 (dd, J = 10.7,2.9 Hz, 1H), 4.96-4.89 (m, 1H), 4.70-4.65 (m, 1H), 4.56-4.37 (m, 4H), 4.28 (s, 1H), 3.78-374 (m, 1H), 3.64-3.58 (m, 2H), 3.49-3.44 (m, 3H), 3.22-3.04 (m, 2H), 2.89 (d, J = 16.6 Hz, 1H), 2.60-2.55 (m, 2H), 2.46 (s, 3H), 2.38-1.93 (m, 6H), 1.84-1.74(m, 2H), 1.61-1.42 (m, 8H), 1.38 (d, J = 6.9 Hz, 3H), 1.08 (d, J = 6.2 Hz, 3H), 0.94 (s, 9H) |

TABLE 74-continued

Characterization Data for Exemplary STAT3 Degraders

| | | | | |
|---|---|---|---|---|
| 216 | I-226 | 2-[[(2S,11S)-2-[[(3S,4R)-1-carbamoyl-4-[[4-(4-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]butyl)-2-methylphenyl]methoxy]pentan-3-yl]carbamoyl]-12-oxo-1-azatricyclo[6.4.1.0^[4,13]]trideca-4(13),5,7-trien-11-yl]carbamoyl]-1H-indole-5-carbonylphosphonic acid | 1256.75 | (400 MHz, $CD_3OD$) δ 58.98-8.84 (m, 2H), 8.13-7.89 (m, 1H), 7.59-7.30 (m, 6H), 7.21-6.97(m, 5H), 6.93-6.90 (m, 1H), 5.18 (dd, J = 10.8, 3.3 Hz, 1H), 5.02-5.00 (m, 1H), 4.81-4.79 (m, 1H), 4.65-4.40 (m, 5H), 4.03-3.99 (m, 1H), 3.89 (d, J = 11.1 Hz, 1H), 3.76 (dd, J = 11.0, 4.0 Hz, 1H), 3.64-3.57 (m, 1H), 3.55-3.46 (m, 1H), 3.25-3.23 (m, 2H), 3.09-3.05 (m, 1H), 2.57-5.54 (m, 2H), 2.49 (d, J = 1.3 Hz, 3H), 2.45-2.16 (m, 10H), 2.06-1.92 (m,2H), 1.65 (d, J = 25.1 Hz, 5H), 1.51 (d, J = 7.0 Hz, 3H), 1.22 (d, J = 6.3 Hz, 3H), 1.05 (s, 9H) |
| 217 | I-227 | 2-[[(2S,11S)-2-[[(3S,4R)-1-carbamoyl-4-[[4-(4-[[(2S)-1-[(2S,4R)-4-hydroxy-2-[[4-(4-methyl-1,3-thiazol-5-yl)phenoxy]carbamoyl]pyrrolidin-1-yl]-3,3-dimethyl-1-oxobutan-2-yl]carbamoyl]butyl)phenyl]methoxy]pentan-3-yl]carbamoyl]-12-oxo-1-azatricyclo[6.4.1.0^[4,13]]trideca-4(13),5,7-trien-11-yl]carbamoyl]-1H-indole-5-carbonylphosphonic acid | 1230.35 | (400 MHz, $CD_3OD$) δ 8.93 (s, 1H), δ 8.86 (s, 1H), 8.08 (d, J = 9.4 Hz, 1H), 8.00 (d, J = 9.4 Hz, 1H), 7.51 (d, J = 8.8 Hz, 1H), 7.41-7.28 (m, 4H), 7.22 (d, J = 7.7 Hz, 2H), 7.15-7.03 (m, 5H), 5.19 (dd, J = 10.9, 3.3 Hz, 1H), 4.65-4.48 (m, 5H), 4.06-3.92 (m, 2H), 3.83 (dd, J = 10.8, 3.9 Hz, 1H), 3.64-3.46(m, 4H), 3.23-3.21 (m, 2H), 3.09-3.05 (m, 2H), 2.63-2.57 (m, 2H), 2.46 (s, 3H), 2.36-2.25 (m, 4H), 1.96 (s, 1H), 1.68-1.55 (m, 5H), 1.40-1.31 (m, 2H), 1.20(d, J = 6.3 Hz, 3H), 1.05 (s, 9H) |
| 218 | I-228 | 2-[[(5S,8S,10aR)-8-[[(1S)-3-carbamoyl-1-(diphenylmethyl-carbamoyl)propyl]carbamoyl]-3-(4-[3-[1-(2,6-dioxopiperidin-3-yl)-3-methyl-2-oxo-1,3-benzodiazol-5-yl]cyclobutyl]butanoyl)-6-oxo-octahydropyrrolo[1,2-a][1,5]diazocin-5-yl]carbamoyl]-1H-indole-5-carbonylphosphonic acid | 1153.65 | (400 MHz, DMSO-$d_6$) δ 12.16-11.95 (m, 1H), 11.25 (s, 1H), 8.85-8.75 (m, 2H), 8.51-8.13 (m, 2H), 7.98-7.96 (m, 1H), 7.58-7.53 (m, 2H), 7.41-7.19 (m, 11H), 7.09-7.07 (m, 1H), 6.99-6.73 (m, 4H), 6.19-5.99 (m, 1H), 5.34-5.30 (m, 1H), 5.05-4.95 (m, 1H), 4.63-4.55 (m, 2H), 4.23-4.19 (m, 1H), 4.18-4.11 (m, 1H), 4.05-3.99 (m, 1H), 3.95-3.90 (m, 1H), 3.87-3.77 (m, 2H), 3.75-3.62 (m, 2H), 3.62-3.53 (m, 1H), 2.95-2.62 (m, 4H), 2.60-2.55 (m, 2H), 2.45-2.38 (m, 2H), 2.22-1.95 (m, 8H), 1.94-1.73 (m, 3H), 1.67-1.58 (m, 4H), 1.45-1.37 (m, 2H), 1.35-1.11 (m, 1H) |
| 219 | I-229 | 2-[[(2S,11S)-2-[[(1S)-3-carbamoyl-1-(diphenylmethyl carbamoyl)propyl]carbamoyl]-6-[6-[1-(2,6-dioxopiperidin-3-yl)-3-methyl-2-oxo-1,3-benzodiazol-5-yl]hexyl]-12-oxo-1-azatricyclo[6.4.1.0^[4,13]]-trideca-4(13),5,7-trien-11-yl]carbamoyl]-1H-indole-5-carbonylphosphonic acid | 1132.20 | (400 MHz, DMSO-$d_6$) δ 12.07 (s, 1H), 11.09 (s, 1H), 8.93 (d, J = 7.8 Hz, 1H), 8.86-8.74 (m, 2H), 8.22 (d, J = 7.9 Hz, 1H), 7.95 (d, J = 8.7 Hz, 1H), 7.51 (d, J = 8.7 Hz, 1H), 7.48-7.41 (m, 1H), 7.36-7.16 (m, 13H), 7.07-6.96 (m, 2H), 6.94-6.84 (m, 3H), 6.77 (s, 1H), 6.07 (d, J = 8.3 Hz, 1H), 5.34 (dd, J = 12.7, 5.4 Hz, 1H), 5.17-5.06 (m, 1H), 4.67-4.63 (m, 1H), 4.34-4.30 (m, 1H), 3.45-3.36 (m, 3H), 3.32 (s, 3H), 3.20-3.01 (m, 1H), 2.97-2.82 (m, 2H), 2.77-2.66 (m, 2H), 2.66-2.56 (m, 3H), 2.28-2.14 (m, 2H), 2.14-1.95 (m, 2H), 1.95-1.86 (m, 1H), 1.84-1.68 (m, 1H), 1.68-1.48 (m, 4H), 1.37-1.34 (m, 5H) |
| 220 | I-230 | 2-[[(5S,8S,10aR)-8-[[(1R)-3-carbamoyl-1-[[(4-methanesulfonylphenyl)methyl]carbamoyl]propyl]carbamoyl]-6-oxo-3-[2-[(1S,4S)-4-[[1-(2,6-dioxopiperidin-3-yl)-3-methyl-2-oxo-1,3-benzodiazol-5-yl]methyl]cyclohexyl]acetyl]-octahydropyrrolo[1,2-a][1,5]diazocin-5-yl]carbamoyl]-1H-indole-5-carbonylphosphonic acid | 1169.50 | (400 MHz, DMSO-$d_6$) δ 12.03-11.96 (m, 1H), 11.21-10.76 (m, 1H), 8.87-8.82 (m, 1H), 8.67-8.31 (m, 2H), 8.28-8.24 (m, 1H), 8.03-7.94 (m, 1H), 7.82-7.74 (m 1H), 7.58-7.49 (m, 2H), 7.44-7.04 (m, 4H), 7.03-6.91 (m, 1H), 6.89-6.71 (m, 2H), 5.38-5.29 (m, 1H), 5.07-4.74 (m, 1H), 4.53-4.42 (m, 2H), 4.29-4.16 (m, 2H), 3.95-3.62 (m, 2H), 3.33 (s, 3H), 3.28-3.15 (m, 6H), 3.15-3.04 (m, 2H), 2.97-2.84 (m, 1H), 2.77-2.53 (m, 6H), 2.41-2.27 (m, 1H), 2.26-2.19 (m, 2H), 2.18-2.09 (m, 3H), 2.08-1.83 (m, 5H), 1.78-1.72 (m, 3H), 1.48-1.39 (m, 8H) |
| 221 | I-231 | diammonium 2-[[(5S,8S,10aR)-3-acetyl-8-[[(2S)-4-carbamoyl-1-[2-fluoro-3-(3-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]propyl)phenoxy]butan-2-yl]carbamoyl]-6-oxo-octahydropyrrolo[1,2-a][1,5]diazocin-5-yl]carbamoyl]-1H-indole-5-carbonylphosphonate | $[(M-1)]^- =$ 1239.95 | (400 MHz, DMSO-$d_6$) δ 9.01-8.97 (m, 1H), 8.93-8.90 (m, 1H), 8.49-8.47 (m, 1H) 8.39 (d, J = 7.8 Hz, 1H), 8.09-8.02 (m, 1H), 7.95 (d, J = 8.7 Hz, 1H), 7.88 (d, J = 9.0 Hz, 1H), 7.46-7.34 (m, 6H), 7.29-7.23 (m, 1H), 7.06-6.98 (m, 2H), 6.81-6.67 (m, 3H), 5.05-5.02 (m, 1H), 4.93-4.91 (m, 1H), 4.53 (d, J = 9.3 Hz, 1H), 4.46-4.36 (m, 2H), 4.31-5.27 (m, 2H), 4.03-3.85 (m, 4H), 3.71-3.69 (m, 2H), 3.62-3.60 (m, 2H), 3.49-3.41 (m, 3H) 2.59-2.56 (m, 3H), 2.47 (s, 3H), 2.28-2.11 (m, 8H), 2.06-2.01 (m, 2H), 1.91-1.65 (m, 9H), 1.38 (d, J = 7.0 Hz, 3H), 0.95 (s, 9H) |
| 222 | I-232 | 2-[[(2S,11S)-2-[[(1S)-3-carbamoyl-1-[[(4-isopropylphenyl)methyl]carbamoyl]propyl] | 1098.45 | (400 MHz, DMSO-$d_6$) δ 12.07 (s, 1H), 11.09 (s, 1H), 9.01-8.93 (m, 1H), 8.83 (s, 1H), 8.36-8.32 (m, 1H), 8.26 (d, J = 7.8 Hz, 1H),7.96 (d, J = 8.7 |

TABLE 74-continued

| Characterization Data for Exemplary STAT3 Degraders | | | | |
|---|---|---|---|---|
| | | carbamoyl]-6-[6-[1-(2,6-dioxopiperidin-3-yl)-3-methyl-2-oxo-1,3-benzodiazol-5-yl]hexyl]-12-oxo-1-azatricyclo[6.4.1.0^[4,13]]trideca-4(13),5,7-trien-11-yl]carbamoyl]-1H-indole-5-carbonylphosphonic acid | | Hz, 1H), 7.52 (d, J = 8.8 Hz, 1H), 7.47 (s, 1H), 7.28 (s, 1H), 7.14-7.09 (m, 4H), 7.05-6.98 (m, 2H), 6.95-6.84 (m, 3H), 6.78 (s, 1H), 5.34 (m, 1H),5.13(m, 1H),4.67(t, J = 10.4 Hz, 1H), 4.26-4.13 (m, 3H), 3.48-3.37 (m, 3H), 3.48-3.27 (m, 3H), 3.20-3.04 (m, 3H), 2.98-2.89 (m, 2H), 2.87-2.78 (m, 2H), 2.74-2.57 (m, 4H), 2.24-2.18 (m, 2H), 2.13-2.04 (m, 2H), 2.02-1.97 (m, 1H), 1.90 (m, 1H), 1.79 (m, 1H), 1.64-1.52 (m, 4H), 1.39-1.31 (m, 4H), 1.16 (d, J = 6.9 Hz, 6H) |
| 223 | I-233 | diammonium 2-[[(5S,8S,10aR)-3-acetyl-8-[[(2S)-4-carbamoyl-1-[2-chloro-3-(4-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]butyl)phenoxy]butan-2-yl]carbamoyl]-6-oxo-octahydropyrrolo[1,2-a][1,5]diazocin-5-yl]carbamoyl]-1H-indole-5-carbonylphosphonate | 1271.50 | (400 MHz, DMSO-$d_6$) δ 12.02-11.82 (m, 1H), 8.99 (s, 1H), 8.89 (s, 1H), 8.49 (d, J = 6.9 Hz, 1H), 8.39 (d, J = 7.8 Hz, 1H), 8.09-8.01 (m, 1H), 7.99-7.92 (m, 1H), 7.84 (d, J = 9.2 Hz, 1H), 7.47-7.37 (m, 5H), 7.37-7.30 (m, 1H), 7.28 (s, 1H), 7.24-7.15 (m, 1H), 7.01-6.97 (m, 1H), 6.93-6.89 (m, 1H), 6.81 (s, 1H), 5.06-5.00 (m, 1H), 4.95-4.89 (m, 1H), 4.52 (d, J = 9.3 Hz, 1H), 4.47-4.33 (m, 2H), 4.30-4.25 (m, 2H), 4.11-4.00 (m, 2H), 3.97-3.83 (m, 2H), 3.72-3.68 (m, 2H), 3.64-3.58 (m, 2H), 3.45-3.29 (m, 2H), 2.71-2.67 (m, 2H), 2.46 (s, 3H), 2.33-2.28 (m, 1H), 2.28-2.21 (m, 4H), 2.20-2.11 (m, 3H), 2.09-1.97 (m, 2H), 1.97-1.84 (m, 3H), 1.83-1.65 (m, 4H), 1.62-1.45 (m, 6H), 1.38 (d, J = 7.0 Hz, 3H), 0.94 (s, 9H) |
| 224 | I-237 | diammonium 2-[[(2S,11S)-2-[[(3R)-1-carbamoyl-6-[4-(4-[[(2S)-1-[(2S,4R)-4-hydroxy-2-[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]butyl)phenyl]hexan-3-yl]carbamoyl]-12-oxo-1-azatricyclo[6.4.1.0^[4,13]]trideca-4(13),5,7-trien-11-yl]carbamoyl]-1H-indole-5-carbonylphosphonate | 1226.55 | (300 MHz, DMSO-$d_6$) δ 11.84 (s, 1H), 9.03-8.90 (m, 3H), 8.49-8.37 (m, 1H), 8.06-7.71 (m, 3H), 7.50-7.33 (m, 6H), 7.28-6.94 (m, 8H), 6.72 (s, 1H), 5.11-5.01 (m, 1H), 4.99-4.88 (m, 1H), 4.75-4.69 (m, 1H), 4.58-4.39 (m, 2H), 4.31-1.27 (m, 1H), 3.80-3.44 (m, 4H), 3.43-3.23 (m,5H), 3.20-3.07 (m, 3H), 2.94-2.70 (m, 1H), 2.47 (s, 3H), 2.33-2.14 (m, 3H), 2.09-1.96 (m, 3H), 1.88-1.70 (m, 1H), 1.69-1.44 (m, 12H), 1.38 (d, J = 7.0 Hz, 3H), 0.95 (s, 9H) |
| 225 | I-238 | diammonium 2-[[(2S,11S)-2-[[(1S)-3-carbamoyl-1-[5-(5-[[(2S)-1-[(2S,4R)-4-hydroxy-2-[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)pyridin-2-yl]propyl]carbamoyl]-12-oxo-1-azatricyclo[6.4.1.0^[4,13]]trideca-4(13),5,7-trien-11-yl]carbamoyl]-1H-indole-5-carbonylphosphonate | 1199.50 | (300 MHz, DMSO-$d_6$) δ 12.08 (s, 1H), 9.02-8.95 (m, 1H), 8.93-8.88 (m, 1H), 8.69 (d, J = 7.7 Hz, 2H), 8.42 (d, J = 7.7 Hz, 1H), 8.38-8.33 (m, 1H), 7.97 (d, J = 8.7 Hz, 1H), 7.80 (d, J = 9.2 Hz, 1H), 7.61-7.54 (m, 1H), 7.46-7.37 (m, 6H), 7.34-7.27 (m, 1H), 7.19 (d, J = 8.0 Hz, 1H), 7.08-7.05 (m, 2H), 7.01-6.90 (m, 1H), 6.78 (s, 1H), 5.17-5.06 (m, 1H), 4.94-4.89 (m, 1H), 4.70-4.67 (m, 2H), 4.53-4.50 (d, J = 9.2 Hz, 1H), 4.46-4.43 (m, 1H), 4.30-4.28 (m, 1H), 3.61-3.60 (m, 3H), 3.52-3.43 (m, 1H), 3.16-3.10 (m, 2H), 2.81-2.61 (m, 3H), 2.46 (s, 3H), 2.32-1.17 (m, 4H), 2.16-1.98 (m, 4H), 1.96-1.72 (m, 4H), 1.68-1.44 (m, 4H), 1.39-1.36 (d, J = 7.0 Hz, 3H), 1.31-1.24 (m, 2H), 0.93 (s, 9H) |
| 226 | I-239 | diammonium 2-[[(2S)-1-[(2S)-2-[[(2S)-4-carbamoyl-1-[2-chloro-3-(4-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]butyl)phenoxy]butan-2-yl]carbamoyl]pyrrolidin-1-yl]-4-methyl-1-oxopentan-2-yl]carbamoyl]-1H-indole-5-carbonylphosphonate | 1231.40 | (400 MHz, DMSO-$d_6$) δ 11.88 (s, 1H), 8.99 (s, 1H), 8.93-8.83 (m, 1H), 8.76 (d, J = 7.9 Hz, 1H), 8.42 (d, J = 7.9 Hz, 1H), 7.99-7.93 (m, 1H), 7.92-7.83 (m, 2H), 7.48-7.30 (m, 6H), 7.25-7.16 (m, 2H), 7.03-6.95 (m, 1H), 6.95-6.89 (m, 1H), 6.83-6.78 (m, 1H), 4.96-4.88 (m, 1H), 4.87-4.83 (m, 1H), 4.55-4.50 (m, 1H), 4.48-4.40 (m, 1H), 4.37-4.30 (m, 1H), 4.30-4.26 (m, 1H), 4.09-4.05 (m, 1H), 4.00-3.89 (m, 2H), 3.88-3.79 (m, 1H), 3.66-3.55 (m, 4H), 3.50-3.30 (m, 1H), 2.71-2.67 (m, 3H), 2.46 (s, 3H), 2.33-2.29 (m, 1H), 2.24-2.11 (m, 3H), 2.07-2.03 (m, 2H), 1.95-1.78 (m, 3H), 1.77-1.66 (m, 4H), 1.56-1.52 (m, 6H), 1.38 (d, J = 7.0 Hz, 3H), 1.02-0.88 (m, 15H) |
| 227 | I-240 | 2-[[(2S)-1-[(2S)-2-[[(2S)-4-carbamoyl-1-[2-chloro-3-(3-[[(2S)-1-[(2S,4R)-4-hydroxy-2-[[(1S)-1-[4-(4-methyl-1,3-thiazo 1-5-yl)phenyl]ethyl]carbamoyl]pyrrolidin-1-yl]-3,3-dimethy 1-1-oxobutan-2-yl]carbamoyl]propyl)phenoxy]butan-2-yl]carbamoyl]pyrrolidin-1-yl]-4-methyl-1-oxopentan-2-yl]carbamoyl]-1H-indole-5-carbonylphosphonic acid | 1216.45 | (400 MHz, DMSO-$d_6$) δ 11.86-11.67 (m, 1H), 10.16-10.00 (m, 1H), 8.99 (s, 1H), 8.93-8.88 (m, 1H), 8.73 (d, J = 8.0 Hz, 1H), 8.41 (d, J = 7.7 Hz, 1H), 8.00-7.83 (m, 3H), 7.44-7.37 (m, 5H), 7.24-7.17 (m, 2H), 6.99 (d, J = 8.2 Hz, 1H), 6.89 (d, J = 7.7 Hz, 1H), 6.79 (s, 1H), 4.98-4.90 (m, 2H), 4.54 (d, J = 9.1 Hz, 1H), 4.45-4.41 (m, 1H), 4.37-4.24 (m, 2H), 4.07-4.05 (m, 1H), 3.97-3.92 (m, 2H), 3.83-3.79 (m, 1H), 3.63-3.60 (m, 2H), 3.55-3.51 (m, 1H), 3.47-3.43 (m, 2H), 3.23-3.20 (m, 2H), 2.69-2.64 (m, 4H), 2.46 (s, 3H), 2.32-2.29 (m, 1H), 2.18-2.16 (m, 2H), 2.03-2.00 (m, 2H), |

TABLE 74-continued

| Characterization Data for Exemplary STAT3 Degraders | | | | |
|---|---|---|---|---|
| | | | | 1.89-1.85 (m, 3H), 1.82-1.63 (m, 3H), 1.62-1.56 (m, 3H), 1.37 (d, J = 6.9 Hz, 3H), 0.96-0.92 (m, 15H) |
| 228 | I-241 | diammonium 2-[[(5S,8S,10aR)-3-acetyl-8-[[(2S)-4-carbamoyl-1-[2-chloro-3-(3-[[(2S)-1-[(2S,4R)-4-hydroxy-2-[[(1S)-1-[4-(4-methyl-1,3-thiazol-5-yl) phenyl]ethyl]carbamoyl] pyrrolidin-1-yl]-3,3-dimethyl-1-oxobutan-2-yl]carbamoyl] propyl)phenoxy]butan-2-yl] carbamoyl]-6-oxo-octahydropyrrolo [1,2-a][1,5]diazocin-5-yl] carbamoyl]-1H-indole-5-carbonylphosphonate | 1257.50 | (400 MHz, DMSO-$d_6$) δ 12.06-11.86 (m, 1H), 8.99 (s, 1H), 8.90-8.80 (m, 1H), 8.51 (d, J = 7.0 Hz, 1H), 8.39 (d, J = 7.8 Hz, 1H), 8.12-8.02 (m, 1H), 7.96 (dd, J = 8.7, 1.5 Hz, 1H), 7.89 (d, J = 9.1 Hz, 1H), 7.44-7.42 (m, 4H), 7.41-7.35 (m, 3H), 7.34-7.26 (m, 1H), 7.23-7.17 (m, 1H), 7.04-6.99 (m, 1H), 6.91-6.87 (m, 1H), 6.81-6.71 (m, 1H) 5.12-5.04 (m, 2H), 4.95-4.88 (m, 1H), 4.54 (d, J = 9.3 Hz, 1H), 4.47-4.33 (m, 2H), 4.28-4.25 (m, 2H), 4.13-3.81 (m, 4H), 3.70-3.65 (m, 2H), 3.62-3.59 (m, 2H), 3.41-3.25 (m, 4H), 2.68-2.61 (m, 2H), 2.46 (s, 3H), 2.29-2.25 (m, 1H), 2.23-2.10 (m, 4H), 2.08-1.97 (m, 2H), 1.88-1.85 (m, 2H), 1.78-1.69 (m, 3H), 1.38-1.32 (m, 5H), 1.27-1.22 (m, 3H), 0.95 (s, 9H) |
| 229 | I-243 | diammonium 2-[[(2S,11S)-2-[[(2S)-4-carbamoyl-1-[2-chloro-3-(4-[[(2S)-1-[(2S,4R)-4-hydroxy-2-[[(1S)-1-[4-(4-methyl-1,3-thiazol-5-yl)phenyl]ethyl] carbamoyl]pyrrolidin-1-yl]-3,3-dimethyl-1-oxobutan-2-yl] carbamoyl]butyl)phenoxy]butan-2-yl]carbamoyl]-12-oxo-1-azatricyclo[6.4.1.0^[4,13]]trideca-4(13),5,7-trien-11-yl]carbamoyl]-1H-indole-5-carbonylphosphonate | 1248.45 | (300 MHz, DMSO-$d_6$) δ 11.89 (s, 1H), 9.03-8.90 (m, 3H), 8.41 (d, J = 7.8 Hz, 1H), 8.16 (d, J = 7.5 Hz, 1H), 7.96 (dd, J = 8.7, 1.5 Hz, 1H), 7.86 (d, J = 9.2 Hz, 1H), 7.50-7.30 (m, 6H), 7.28 (s, 1H), 7.21-7.17 (m, 1H), 7.12-7.08 (m, 2H), 7.02-6.98 (m, 2H), 6.92 (dd, J = 7.7, 1.3 Hz, 1H), 6.78 (s, 1H), 5.10 (dd, J = 10.7, 2.9 Hz, 1H), 4.98-4.88 (m, 1H), 4.76-4.63 (m, 1H), 4.53 (d, J = 9.3 Hz, 1H), 4.45 (t, J = 8.0 Hz, 1H), 4.29 (s, 1H), 4.05-3.93 (m, 3H), 3.62-3.61 (m, 2H), 3.55-3.40 (m, 3H), 3.31-3.20 (m, 1H), 3.18-3.14 (m, 1H), 2.98 (d, J = 16.5 Hz, 1H), 2.73-2.68 (m, 2H), 2.47 (s, 3H), 2.39-2.11 (m, 7H), 2.12-1.97 (m, 1H), 1.93-1.70 (m, 3H), 1.58-1.54 (m, 4H), 1.39 (d, J = 7.0 Hz, 3H), 0.95 (s, 9H) |
| 230 | I-244 | 2-[[(2S,11S)-2-[[(2S)-4-carbamoyl-1-[5-chloro-2-fluoro-3-(5-[[(2S)-1-[(2S,4R)-4-hydroxy-2-[[(1S)-1-[4-(4-methyl-1,3-thiazol-5-yl)phenyl]ethyl] carbamoyl]pyrrolidin-1-yl]-3,3-dimethyl-1-oxobutan-2-yl] carbamoyl]pentyl)phenoxy]butan-2-yl]carbamoyl]-12-oxo-1-azatricyclo[6.4.1.0^[4,13]]trideca-4(13),5,7-trien-11-yl] carbamoyl]-1H-indole-5-carbonylphosphonic acid | 1280.50 | (400 MHz, DMSO-$d_6$) δ 11.88 (s, 1H), 10.27 (br, 1H), 8.99 (s, 1H), 8.98-8.95 (m, 1H), 8.93 (s, 1H), 8.52 (d, J = 2.9 Hz, 1H), 8.42 (d, J = 7.8 Hz, 1H), 8.15 (d, J = 7.1 Hz, 1H), 7.94-7.91 (m, 1H), 7.82 (d, J = 9.3 Hz, 1H), 7.46-7.36 (m, 6H), 7.27 (s, 1H), 7.14-7.11 (m, 1H), 7.10-7.08 (m, 1H), 7.07-7.05 (m, 1H), 7.00-6.98 (m, 1H), 6.93-6.91 (m, 1H), 6.77 (s, 1H), 5.12-5.07 (m, 1H), 4.94-4.90 (m, 1H), 4.73-4.65 (m, 1H), 4.52 (d, J = 9.3 Hz, 1H), 4.43 (t, J = 8.0 Hz, 1H), 4.30-4.26 (m, 1H), 3.53 (d, J = 4.6 Hz, 3H), 2.93-2.83 (m, 1H), 2.46 (s, 3H), 2.28-2.22 (m, 3H), 2.16-2.10 (m, 3H), 2.04-2.00 (m, 1H), 1.96-1.80 (m, 5H), 1.82-1.78 (m, 2H), 1.70-1.62 (m, 5H), 1.54-1.45 (m, 3H), 1.38 (d, J = 7.0 Hz, 3H), 1.28-1.22 (m, 2H), 0.93 (s, 9H) |
| 231 | I-245 | 2-[[(2S,11S)-2-[[(1S)-3-carbamoyl-1-(diphenylmethylcarbamoyl) propyl]carbamoyl]-6-[(4-[[1-(2,6-dioxopiperidin-3-yl)-3-methyl-2-oxo-1,3-benzodiazol-5-yl]methyl]cyclohexyl) methyl]-12-oxo-1-azatricyclo [6.4.1.0^[4,13]]trideca-4(13),5,7-trien-11-yl]carbamoyl]-1 H-indole-5-carbonylphosphonic acid | 1158.40 | (400 MHz, DMSO-$d_6$) δ 12.05 (s, 1H), 11.10 (s, 1H), 9.00-8.90 (m, 1H), 8.86-8.69 (m, 2H), 8.23 (d, J = 7.8 Hz, 1H), 7.97-7.94 (m, 1H), 7.54-7.44 (m, 2H), 7.41-7.10 (m, 12H), 7.04-6.96 (m, 2H), 6.93-6.69 (m, 4H), 6.07 (d, J = 8.4 Hz, 1H), 5.37-5.32 (m, 1H),5.12(d, J = 11.0 Hz, 1H), 4.66-4.63 (m, 1H), 4.32-4.29 (m, 1H), 3.32-3.30 (m, 6H), 3.17-3.11 (m, 2H), 2.94-2.88 (m, 2H), 2.74-2.58 (m, 3H), 2.39-2.36 (m, 1H), 2.29-2.11 (m, 3H), 2.12-1.97 (m, 3H), 1.91-1.89 (m, 1H), 1.78-1.76 (m, 2H), 1.66 (d, J = 8.7 Hz, 2H), 1.55-1.36 (m, 5H), 0.98-0.85 (m, 2H) |
| 232 | I-246 | diammonium 2-[[(2S,11S)-2-[(3-carbamoyl-1-[[2-chloro-3-(4-[[(2S)-1-[(2S,4R)-4-hydroxy-2-[[(1S)-1-[4-(4-methyl-1,3-thiazol-5-yl)phenyl]ethyl] carbamoyl]pyrrolidin-1-yl]-3,3-dimethyl-1-oxobutan-2-yl] carbamoyl]butyl)phenyl]carbamoyl] propyl)carbamoyl]-12-oxo-1-azatricyclo[6.4.1.0^[4,13]] trideca-4(13),5,7-trien-11-yl] carbamoyl]-1H-indole-5-carbonylphosphonate | 1262.50 | (400 MHz, DMSO-$d_6$) δ 11.89 (s, 1H), 9.48 (d, J = 4.9 Hz, 1H), 8.99 (s, 1H), 8.93 (d, J = 8.6 Hz, 1H), 8.50-8.37 (m, 2H), 7.96-7.92 (m, 1H), 7.85 (d, J = 9.3 Hz, 1H), 7.61-7.57 (m, 1H), 7.46-7.40 (m, 4H), 7.39-7.33 (m, 4H), 7.28-7.14 (m, 1H), 7.16-7.09 (m, 3H), 7.03-6.99 (m, 1H), 6.83 (s, 1H), 5.19 (d, J = 10.5 Hz, 1H), 4.95-4.89 (m, 1H), 4.69 (s, 1H), 4.52 (d, J = 9.0 Hz, 2H), 4.49-4.39 (m, 2H), 4.28 (s, 1H), 3.61 (s, 2H), 3.55-3.41 (m, 1H), 3.37 (s, 1H), 3.20-3.12 (m, 3H), 3.03 (d, J = 16.9 Hz, 1H), 2.75-2.62 (m, 3H), 2.46 (s, 3H), 2.38-2.12 (m, 4H), 2.08-1.98 (m, 2H), 1.91-1.89 (m, 1H), 1.85-1.74 (m, 1H), 1.59-1.44 (m, 5H), 1.38 (d, J = 7.0 Hz, 3H), 0.94 (s, 9H) |
| 233 | I-247 | diammonium 2-[[(2S,11S)-2-[[(1S)-3-carbamoyl-1-[[2-chloro-3-(3-[[(2S)-1-[(2S,4R)-4- | 1249.60 | (400 MHz, DMSO-$d_6$) δ 11.93 (s, 1H), 9.50 (s, 1H), 9.01-8.89 (m, 3H), 8.49 (d, J = 7.2 Hz, 1H), 8.41 (d, J = 7.8 Hz, 1H), 7.97-7.91 (m, 2H), 7.58 |

TABLE 74-continued

Characterization Data for Exemplary STAT3 Degraders

| | | | | |
|---|---|---|---|---|
| | | hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]propyl)phenyl]carbamoyl]propyl]carbamoyl]-12-oxo-1-azatricyclo[6.4.1.0^[4,13]]trideca-4(13),5,7-trien-11-yl]carbamoyl]-1H-indole-5-carbonylphosphonate | | (d, J = 7.9 Hz, 1H), 7.44-7.38 (m, 7H), 7.35-7.20 (m, 1H), 7.15-7.06 (m, 3H), 7.01-6.97 (m, 1H), 6.84 (s, 1H), 5.19 (d, J = 10.6 Hz, 1H), 4.95-4.88 (m, 1H), 4.71-4.68 (m, 1H), 4.55 (d, J = 9.3 Hz, 1H), 4.44 (t, J = 7.9 Hz, 2H), 4.29 (s, 1H), 3.66-3.57 (m, 2H), 3.54-3.50 (m, 2H), 3.21-3.17 (m, 1H), 3.14-3.10 (m, 1H),3.02 (d, J = 16.6 Hz, 1H), 2.71-2.67 (m, 2H), 2.46 (s, 3H), 2.38-2.13 (m, 7H), 2.06-2.00 (m, 2H), 1.92-1.86 (m, 1H), 1.82-1.74 (m, 4H), 1.38 (d, J = 6.9 Hz, 3H), 0.95 (s, 9H) |
| 234 | I-248 | diammonium 2-[[(2S,11S)-2-[[(1S)-3-carbamoyl-1-[[3-(3-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]propyl)phenyl]carbamoyl]propyl]carbamoyl]-12-oxo-1-azatricyclo[6.4.1.0^[4,13]]trideca-4(13),5,7-trien-11-yl]carbamoyl]-1H-indole-5-carbonylphosphonate | 1213.60 | (400 MHz, DMSO-$d_6$) δ11.85 (s, 1H), 9.96 (s, 1H), 9.01-8.90 (m, 3H), 8.39 (dd, J = 17.8, 7.5 Hz, 2H), 7.96-7.84 (m, 2H), 7.47-7.30 (m, 9H), 7.24-7.05 (m, 6H), 7.01-6.97 (m, 1H), 6.91-6.75 (m, 2H), 5.18 (dd, J = 10.6, 3.0 Hz, 1H), 4.95-4.89 (m, 1H), 4.73-4.64 (m, 1H), 4.57-4.39 (m, 2H), 4.35-4.25 (m, 2H), 3.61 (d, J = 3.2 Hz, 2H), 3.51-3.47 (m, 1H), 3.28-2.95 (m, 4H), 2.46 (s, 3H), 2.31-1.98 (m, 7H), 1.92-1.70 (m, 6H), 1.38 (d, J = 7.0 Hz, 3H), 0.94 (s, 9H) |
| 235 | I-249 | 2-[[(2S,11S)-2-[[(1S)-3-carbamoyl-1-[[2-chloro-3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenyl]carbamoyl]propyl]carbamoyl]-12-oxo-1-azatricyclo[6.4.1.0^[4,13]]trideca-4(13),5,7-trien-11-yl]carbamoyl]-1H-indole-5-carbonylphosphonic acid | 1275.45 | (300 MHz, DMSO-$d_6$) δ12.14 (s, 1H), 9.49 (s, 1H), 9.00-8.97 (m, 2H), 8.83 (d, J = 1.6 Hz, 1H), 8.47 (d, J = 7.3 Hz, 1H), 8.39 (d, J = 7.8 Hz, 1H), 7.96 (dd, J = 8.8, 1.6 Hz, 1H),7.81 (d, J =9.3 Hz, 1H), 7.61-7.52 (m, 2H), 7.50 (d, J = 2.0 Hz, 1H), 7.45-7.40 (m, 4H), 7.34 (s, 1H), 7.30-7.20 (m, 1H), 7.17-7.07 (m, 4H), 7.05-6.91 (m, 2H), 6.83 (s, 1H), 5.20 (dd, J = 10.6, 2.9 Hz, 1H), 4.98-4.88 (m, 1H), 4.77-4.65 (m, 1H), 4.53 (d, J = 9.2 Hz, 1H), 4.45-4.40 (m, 2H), 4.29 (s, 1H), 3.62 (s, 2H), 3.58-3.41 (m, 1H), 3.27-3.14 (m, 2H), 3.05 (dd, J = 17.2, 14.5 Hz, 1H), 2.72-2.68 (m, 2H), 2.47 (s, 3H), 2.35-2.10 (m, 6H), 2.03-1.96 (m, 2H), 1.89-1.74 (m, 2H), 1.60-1.47 (m, 6H), 1.39 (d, J = 7.0 Hz, 3H), 1.33-1.24 (m, 1H), 0.94 (s, 9H) |
| 236 | I-250 | 2-[[(2S,11S)-2-[[(1S)-3-carbamoyl-1-[[2-fluoro-3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenyl]carbamoyl]propyl]carbamoyl]-12-oxo-1-azatricyclo[6.4.1.0^[4,13]]trideca-4(13),5,7-trien-11-yl]carbamoyl]-1H-indole-5-carbonylphosphonic acid | 1260.65 | (300 MHz, DMSO-$d_6$) δ 12.15 (s, 1H), 9.75 (s, 1H), 9.03-8.96 (m, 2H), 8.84 (s, 1H), 8.43-8.39 (m, 2H), 7.96 (d, J = 8.7 Hz, 1H), 7.81 (d, J = 9.3 Hz, 1H), 7.72-7.69 (m, 1H), 7.57-7.47 (m, 3H), 7.45-7.36 (m, 3H), 7.15-7.09 (m, 3H), 7.07-6.98 (m, 2H), 6.83 (s, 1H), 5.19 (d, J = 10.6 Hz, 1H), 4.96-4.90 (m, 1H), 4.73-4.69 (m, 1H), 4.55-4.40 (m, 3H), 4.30 (s, 1H), 3.62 (s, 2H), 3.56-3.48 (m, 1H), 3.31-3.10 (m, 3H), 3.01 (d, J = 16.7 Hz, 1H), 2.62-2.57 (m, 3H), 2.54-2.44 (m, 3H), 2.26-2.21 (m, 4H), 2.07-1.98(m, 2H), 1.94-1.77 (m, 3H), 1.62-1.46 (m, 6H), 1.39 (d, J = 7.0 Hz, 3H), 1.33-1.24 (m, 3H), 0.94 (s, 9H) |
| 237 | I-251 | diammonium 2-[[(2S,11S)-2-[[(2S)-4-carbamoyl-1-[2-fluoro-3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)-4-methylphenoxy]butan-2-yl]carbamoyl]-12-oxo-1-azatricyclo[6.4.1.0^[4,13]]trideca-4(13),5,7-trien-11-yl]carbamoyl]-1H-indole-5-carbonylphosphonate | [(M − 1)]$^-$ = 1258.45 | (400 MHz, DMSO-$d_6$) δ 11.87 (s, 1H), 8.99 (s, 1H), 8.97-8.90 (m, 2H), 8.41 (d, J = 7.8 Hz, 1H), 8.12 (d, J = 7.6 Hz, 1H), 7.98-7.91 (m, 1H), 7.83 (d, J = 9.2 Hz, 1H), 7.47-7.35 (m, 5H), 7.26 (s, 2H), 7.13-7.04 (m, 2H), 7.01-6.97 (m, 1H), 6.86 (s, 2H), 6.76 (s, 1H), 5.13-5.05 (m, 1H), 4.93-4.89 (m, 1H), 4.71-4.66 (m, 1H), 4.52 (d, J = 9.3 Hz, 1H), 4.43 (t, J = 8.0 Hz, 1H), 4.28 (s, 1H), 3.96-3.92 (m, 3H), 3.61 (s, 2H), 3.48-3.44 (m, 1H), 3.22-3.19 (m, 1H), 3.16-3.13 (m, 1H), 2.91-2.87 (m, 1H), 2.58-2.55 (m, 4H), 2.46 (s, 3H), 2.32-2.18 (m, 6H), 2.16-2.06 (m, 3H), 2.06-1.97 (m, 1H), 1.84-1.80 (m, 2H), 1.72-1.68 (m, 1H), 1.57-1.49 (m, 1H), 1.48-1.44 (m, 4H), 1.38 (d, J = 7.0 Hz, 3H), 1.36-1.29 (m, 2H), 0.93 (s, 9H) |
| 238 | I-252 | diammonium 2-[[(2S,11S)-2-[[(2S)-4-carbamoyl-1-[2,4-difluoro-3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenoxy]butan-2-yl]carbamoyl]-12-oxo-1-azatricyclo[6.4.1.0^[4,13]] | 1265.00 | (400 MHz, DMSO-$d_6$) δ 11.90 (s, 1H), 9.04-8.88 (m, 3H), 8.41 (d, J = 7.8 Hz, 1H), 8.16 (d, J = 7.4 Hz, 1H), 7.96 (d, J = 8.7 Hz, 1H), 7.82 (d, J = 9.2 Hz, 1H), 7.51-7.35 (m, 7H), 7.28 (s, 1H), 7.13-6.89 (m, 5H), 6.77 (s, 1H), 5.09 (dd, J = 10.7, 3.0 Hz, 1H), 4.96-4.88 (m, 1H), 4.73-4.64 (m, 1H), 4.52 (d, J = 9.3 Hz, 1H), 4.43 (t, J = 8.0 Hz, 1H), 4.30-4.27 (m, 1H), 4.00-3.92 (m, 3H), 3.63-3.60 (m, 2H), 3.54-3.39 (m, 2H), 3.28-3.06 (m, 2H), 2.90-2.86 (m, 1H), 2.61-2.58 (m, 1H), 2.46 (s, |

TABLE 74-continued

Characterization Data for Exemplary STAT3 Degraders

| | | | | |
|---|---|---|---|---|
| | | trideca-4(13),5,7-trien-11-yl]carbamoyl]-1H-indole-5-carbonylphosphonate | | 3H), 2.30-2.21 (m, 3H), 2.17-2.00 (m, 5H), 1.92-1.61 (m, 3H), 1.61-1.42 (m, 5H), 1.38 (d, J = 7.0 Hz, 3H), 1.34-1.21 (m, 2H), 0.93 (s, 9H) |
| 239 | I-253 | diammonium 2-[[(2S,11S)-2-[[(2S)-4-carbamoyl-1-[2-chloro-3-(3-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]propyl)phenoxy]butan-2-yl]carbamoyl]-12-oxo-1-azatricyclo[6.4.1.0^[4,13]]trideca-4(13),5,7-trien-11-yl]carbamoyl]-1H-indole-5-carbonylphosphonate | 1234.35 | (400 MHz, DMSO-$d_6$) δ 11.90 (s, 1H), 9.05-8.84 (m, 3H), 8.40 (d, J = 7.8 Hz, 1H), 8.15 (d, J = 7.6 Hz, 1H), 7.94 (dd, J = 18.9, 9.0 Hz, 2H), 7.49-7.34 (m, 7H), 7.28 (s, 1H), 7.19 (t, J = 7.8 Hz, 1H), 7.09 (t, J = 8.1 Hz, 2H), 7.01-6.97 (m, 2H), 6.89 (d, J = 7.6 Hz, 1H), 6.77 (s, 1H), 5.13-5.06 (m, 1H), 4.97-4.87 (m, 1H), 4.68 (t, J = 9.1 Hz, 1H), 4.55 (d, J = 9.3 Hz, 1H),4.44(t, J = 8.0 Hz, 1H), 4.30-4.27 (m, 1H), 4.11-3.87 (m, 4H), 3.65-3.61 (m, 2H), 3.50-3.43 (m, 1H), 3.26-3.05 (m, 2H), 2.99-2.94 (m, 1H), 2.71-2.66 (m, 2H), 2.46 (s, 3H), 2.40-2.08 (m, 7H), 2.06-2.01 (m, 1H), 1.95-1.65 (m, 5H), 1.38 (d, J = 7.0 Hz, 3H), 0.96 (s, 9H) |
| 240 | I-254 | diammonium 2-[[(2S,11S)-2-[[4-carbamoyl-1-([2-fluoro-3-[4-([[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]oxy)butyl]phenyl](methyl)amino)butan-2-yl]carbamoyl]-12-oxo-1-azatricyclo[6.4.1,0^[4,13]]trideca-4(13),5,7-trien-11-yl]carbamoyl]-1H-indole-5-carbonylphosphonate | [(M − 1)]$^-$ = 1260.50 | (400 MHz, DMSO-$d_6$) δ 11.89 (s, 1H), 9.03-8.82 (m, 3H), 8.43 (d, J = 8.0 Hz, 1H), 7.95 (d, J = 8.6 Hz, 1H), 7.85 (d, J = 8.7 Hz, 1H), 7.51-7.29 (m, 7H), 7.26-7.20 (m, 1H), 7.16-6.84 (m, 5H), 6.84-6.64 (m, 3H), 5.00-4.85 (m, 2H), 4.65 (t, J = 7.8 Hz, 1H), 4.45 (t, J = 7.8 Hz, 1H), 4.30-4.27 (m, 1H), 4.17 (d, J = 9.2 Hz, 1H), 4.02-3.92 (m, 3H), 3.61-3.58 (m, 2H), 3.37-2.98 (m, 6H), 2.74 (s, 3H), 2.60-2.56 (m, 3H), 2.46 (s, 3H), 2.32-2.19 (m, 2H), 2.11-2.02 (m, 4H), 1.81-1.72 (m, 1H), 1.68-1.47 (m, 6H), 1.37 (d, J = 7.0 Hz, 3H), 0.94 (s, 9H) |
| 241 | I-256 | 2-[[(2S,11S)-2-[[(2S)-4-carbamoyl-1-[3-([[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]methyl)phenoxy]butan-2-yl]carbamoyl]-12-oxo-1-azatricyclo[6.4.1.0^[4,13]]trideca-4(13),5,7-trien-11-yl]carbamoyl]-1H-indole-5-carbonylphosphonic acid | 1172.45 | (300 MHz, DMSO-$d_6$) δ 12.13 (s, 1H), 9.02-9.00 (m, 2H), 8.84 (s, 1H), 8.41 (d, J = 7.8 Hz, 1H), 8.17 (d, J = 8.1 Hz, 1H), 8.06 (d, J = 9.3 Hz, 1H), 7.96 (dd, J = 8.7, 1.6 Hz, 1H), 7.60-7.36 (m, 6H), 7.27 (s, 1H), 7.20 (t, J = 7.9 Hz, 1H), 7.13-7.11 (m, 2H), 7.05-6.96 (m, 1H), 6.88-6.86 (m, 2H), 6.82-6.74 (m, 2H), 5.13-5.09 (m, 2H), 4.98-4.89 (m, 1H), 4.74-4.67 (m, 1H), 4.58-4.40 (m, 2H), 4.30-4.27 (m, 1H), 4.05-3.98 (m, 1H), 3.92-3.89 (m, 2H), 3.65-3.60 (m, 3H), 3.55-3.36 (m, 2H), 3.25-3.10 (m, 2H), 2.90-2.86 (m, 1H), 2.47 (s, 3H), 2.31-2.12 (m, 6H), 2.10-1.96 (m, 1H), 1.94-1.62 (m, 3H), 1.38 (d, J = 7.0 Hz, 3H), 0.93 (s, 9H) |
| 242 | I-257 | 2-[[(2S,11S)-2-[[(1S)-3-carbamoyl-1-[[3-chloro-5-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenyl]carbamoyl]propyl]carbamoyl]-12-oxo-1-azatricyclo[6.4.1.0^[4,13]]trideca-4(13),5,7-trien-11-yl]carbamoyl]-1H-indole-5-carbonylphosphonic acid | [(M − 1)]$^-$ = 1274.40 | (400 MHz, DMSO-$d_6$) δ 12.09 (s, 1H), 10.15 (s, 1H), 8.99-8.95 (m, 2H), 8.84 (s, 1H), 8.45 (d, J = 7.2 Hz, 1H), 8.38 (d, J = 7.8 Hz, 1H), 7.96 (d, J = 8.8 Hz, 1H), 7.80 (d, J = 9.2 Hz, 1H), 7.63 (s, 1H), 7.56-7.46 (m, 2H), 7.45-7.43 (m, 2H), 7.39-7.37 (m, 2H), 7.35-7.33 (m, 1H), 7.25 (s, 1H), 7.14 (d, J = 7.3 Hz, 1H),7.09 (d, J = 7.7 Hz, 1H), 7.02-6.92 (m, 2H), 6.81 (s, 1H), 5.19-5.11 (m, 2H), 4.96-4.88 (m, 1H), 4.73-4.65 (m, 1H), 4.52 (d, J = 9.3 Hz, 1H),4.43 (t, J = 8.1 Hz, 1H), 4.30-4.26 (m, 3H), 3.64-3.60 (m, 2H), 3.54-3.44 (m, 1H), 3.39-3.32 (m, 1H), 3.28-3.06 (m, 3H), 3.03-2.98 (m, 1H), 2.46 (s, 3H), 2.37-1.72 (m, 10H), 1.62-1.43 (m, 5H), 1.38 (d, J = 6.9 Hz, 3H), 1.28-1.22 (m, 2H), 0.93 (s, 9H) |
| 243 | I-258 | 2-[[(2S,11S)-2-[[(1S)-3-carbamoyl-1-[[3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)-5-methylphenyl]carbamoyl]propyl]carbamoyl]-12-oxo-1-azatricyclo[6.4.1.0^[4,13]]trideca-4(13),5,7-trien-11-yl]carbamoyl]-1H-indole-5-carbonylphosphonic acid | 1255.55 | (400 MHz, DMSO-$d_6$) δ 12.11 (s, 1H), 9.85 (s, 1H), 9.03-8.92 (m, 2H), 8.83 (s, 1H), 8.38-3.35 (m, 2H), 7.96 (dd, J = 8.8, 1.6 Hz, 1H), 7.79 (d, J = 9.2 Hz, 1H), 7.54 (d, J = 8.7 Hz, 1H), 7.48 (s, 1H), 7.44 (d, J = 8.2 Hz, 2H), 7.38 (d, J = 8.2 Hz, 2H), 7.32 (s, 1H), 7.24 (s, 1H), 7.18 (s, 1H), 7.14 (d, J = 7.3 Hz, 1H), 7.09 (d, J = 7.8 Hz, 1H), 7.01-6.97 (m, 1H), 6.79 (s, 1H),6.69 (s, 1H), 5.20-5.11 (m, 2H), 4.96-4.88 (m, 1H), 4.72-4.67 (m, 1H), 4.52 (d, J = 9.3 Hz, 1H), 4.43 (t, J = 8.0 Hz, 1H), 4.32-4.27 (m, 2H), 3.64-3.59 (m, 2H), 3.53-3.43 (m, 1H), 3.29-3.05 (m, 3H), 3.05-2.95 (m, 1H), 2.47-2.44 (m, 5H), 2.30-2.20 (m, 6H), 2.19-2.08 (m, 3H), 2.06-1.72 (m, 4H), 1.61-1.42 (m, 5H), 1.38 (d, J = 7.0 Hz, 3H), 1.29-1.22 (m, 2H), 0.93 (s, 9H) |
| 244 | I-259 | 6342-[[(2S,115)-2-[[(1S)-3-carbamoyl-1-[[3-(5-[[(2S)-1-[(2S,4R)-4-hydroxy-2-[[(1S)-1- | 1256.45 | (300 MHz, DMSO-$d_6$) δ 12.10 (s, 1H), 9.39 (s, 1H), 9.06-8.92 (m, 2H), 8.84 (s, 1H), 8.37 (t, J = 7.3 Hz, 2H), 7.97 (d, J = 8.8 Hz, 1H), 7.81 (d, J = |

TABLE 74-continued

Characterization Data for Exemplary STAT3 Degraders

| | | | | |
|---|---|---|---|---|
| | | [4-(4-methyl-1,3-thiazol-5-yl) phenyl]ethyl]carbamoyl] pyrrolidin-1-yl]-3,3-dimethyl-1-oxobutan-2-yl]carbamoyl]pentyl)-2-methylphenyl]carbamoyl] propyl]carbamoyl]-12-oxo-1-azatricyclo[6.4.1.0^[4,13]]trideca-4(13),5,7-trien-11-yl]carbamoyl]-1H-indole-5-carbonylphosphonic acid | | 9.3 Hz, 1H), 7.56-7.35 (m, 7H), 7.19-6.93 (m, 6H), 6.81 (s, 1H), 5.20 (d, J = 10.5 Hz, 1H), 4.98-4.89 (m, 1H), 4.74-4.67 (m, 1H), 4.54 (d, J = 9.3 Hz, 1H), 4.47-4.39 (m, 2H), 4.32-4.28 (m, 1H), 3.64-3.61 (m, 2H), 3.58-3.00 (m, 7H), 2.59-2.56 (m, 2H), 2.47 (s, 3H), 2.37-2.09 (m, 6H), 2.06 (s, 3H), 2.03-1.72 (m, 2H), 1.60-1.45 (m, 6H), 1.39 (d, J = 7.0 Hz, 3H), 1.35-1.18 (m, 2H), 0.95 (s, 9H) |
| 245 | I-260 | diammonium 2-[[(2S,11S)-2-[[(2S)-4-carbamoyl-1-[3-(2-[[(2S)-1-[(2S,4R)-4-hydroxy-2-[(1S)-1-[4-(4-methyl-1,3-thiazol-5-yl)phenyl]ethyl]carbamoyl] pyrrolidin-1-yl]-3,3-dimethyl-1-oxobutan-2-yl]carbamoyl] ethyl)phenoxy]butan-2-yl] carbamoyl]-12-oxo-1-azatricyclo [6.4.1.0^[4,13]]trideca-4(13),5,7-trien-11-yl]carbamoyl]-1H-indole-5-carbonylphosphonate | 1186.50 | (300 MHz, DMSO-$d_6$) δ 11.92 (s, 1H), 9.00-8.92 (m, 2H), 8.43 (d, J = 7.7 Hz, 1H), 8.13 (d, J = 8.0 Hz, 1H), 8.02-7.84 (m, 2H), 7.50-7.35 (m, 6H), 7.29 (s, 1H), 7.22-7.05 (m, 3H), 7.03-6.98 (m, 1H), 6.88-6.67 (m, 5H),5.11 (d, J = 10.7 Hz, 1H), 4.98-4.89 (m, 1H), 4.73-4.66 (m, 1H), 4.55 (d, J = 9.3 Hz, 1H), 4.45 (t, J = 8.0 Hz, 1H), 4.32-4.28 (m, 1H), 4.00-3.89 (m, 3H), 3.65-3.60 (m, 2H), 3.55-3.34 (m, 1H), 3.24-3.08 (m, 3H), 2.98-2.70 (m, 3H), 2.65-2.58 (m, 1H), 2.47 (s, 3H), 2.44-2.37 (m, 1H), 2.34-1.98 (m, 6H), 1.88-1.68 (m, 4H), 1.39 (d, J = 7.0 Hz, 3H), 0.92 (s, 9H) |
| 246 | I-261 | 2-[[(2S,11S)-2-[[(2S)-4-carbamoyl-1-[2-fluoro-3-(3-[[(2S)-1-[(2S,4R)-4-hydroxy-2-[[(1S)-1-[4-(4-methyl-1,3-thiazol-5-yl)phenyl]ethyl]carbamoyl] pyrrolidin-1-yl]-3,3-dimethyl-1-oxobutan-2-yl]carbamoyl] propyl)phenoxy]butan-2-yl] carbamoyl]-12-oxo-1-azatricyclo [6.4.1.0^[4,13]]trideca-4(13),5,7-trien-11-yl]carbamoyl]-1H-indole-5-carbonylphosphonic acid | 1218.40 | (300 MHz, DMSO-$d_6$) δ 12.10 (s, 1H), 9.02-8.99 (m, 2H), 8.84 (s, 1H), 8.39 (d, J = 7.8 Hz, 1H), 8.22-8.10 (m, 1H), 7.93 (dd, J = 20.5, 9.0 Hz, 2H), 7.58-7.35 (m, 6H), 7.32-7.27 (m, 1H), 7.16-6.94 (m, 5H), 6.90-6.70 (m, 2H), 5.10 (dd, J = 11.1, 2.8 Hz, 1H), 4.98-4.91 (m, 1H), 4.73-4.67 (m, 1H),4.55 (d, J = 9.2 Hz, 1H), 4.44 (t, J = 8.0 Hz, 1H), 4.32-4.28 (m, 1H), 4.05-3.95 (m, 3H), 3.66-3.61 (m, 2H), 3.57-3.01 (m, 7H), 2.92-2.87 (m, 1H), 2.62-2.57 (m, 2H), 2.47 (s, 3H), 2.37-2.00 (m, 6H), 1.94-1.61 (m, 5H), 1.39 (d, J = 7.0 Hz, 3H), 0.96 (s, 9H) |
| 247 | I-262 | 2-[[(5S,8S,10aR)-3-acetyl-8-[[(2S)-4-carbamoyl-1-[2-fluoro-3-(5-[[(2S)-1-[(2S,4R)-4-hydroxy-2-[[(1S)-1-[4-(4-methyl-1,3-thiazol-5-yl)phenyl]ethyl] carbamoyl]pyrrolidin-1-yl]-3,3-dimethyl-1-oxobutan-2-yl] carbamoyl]pentyl)-5-methylphenoxy] butan-2-yl]carbamoyl]-6-oxo-octahydropyrrolo[1,2-a] [1,5]diazocin-5-yl]carbamoyl]-1H-indole-5-carbonylphosphonic acid | 1284.55 | (400 MHz, DMSO-$d_6$) δ8.99 (s, 1H), 8.92-8.80 (m, 1H), 8.52-8.40 (m, 2H), 8.11-8.04 (m, 1H), 7.97 (dd, J = 8.7, 1.6 Hz, 1H),7.81 (d, J = 9.3 Hz, 1H), 7.49-7.34 (m, 7H), 7.34-7.23 (m, 1H), 6.84-6.80 (m, 2H), 6.62-6.60 (m, 1H), 5.05-5.01 (m, 1H), 4.96-4.89 (m, 1H), 4.52 (d, J = 9.4 Hz, 1H), 4.48-4.34 (m, 2H), 4.29-4.23 (m, 2H), 4.10-3.80 (m, 4H), 3.75-3.70 (m, 2H), 3.65-3.60 (m, 2H), 3.43-3.32 (m, 2H), 2.46 (s, 3H), 2.33-2.17 (m, 8H), 2.17-1.98 (m, 6H), 1.96-1.62 (m, 8H), 1.62-1.43 (m, 6H), 1.38 (d, J = 7.0 Hz, 3H), 1.32-1.20 (m, 2H), 0.93 (s, 9H) |
| 248 | I-263 | 2-[[(5S,8S,10aR)-3-acetyl-8-[[(2S)-4-carbamoyl-1-[2-fluoro-3-(4-[[(2S)-1-[(2S,4R)-4-hydroxy-2-[[(1S)-1-[4-(4-methyl-1,3-thiazol-5-yl)phenyl]ethyl] carbamoyl]pyrrolidin-1-yl]-3,3-dimethyl-1-oxobutan-2-yl] carbamoyl]butyl)phenoxy]butan-2-yl]carbamoyl]-6-oxo-octahydropyrrolo[1,2-a][1,5] diazocin-5-yl]carbamoyl]-1H-indole-5-carbonylphosphonic acid | 1255.45 | (300 MHz, DMSO-$d_6$) δ 12.21-12.01 (m, 1H), 9.05-8.98 (m, 1H), 8.87-8.78 (m, 1H), 8.52 (d, J = 6.9 Hz, 1H), 8.39 (d, J = 7.7 Hz, 1H), 8.09 (d, J = 8.4 Hz, 1H), 7.97 (d, J = 8.8 Hz, 1H), 7.84 (d, J = 9.2 Hz, 1H), 7.53-7.36 (m, 6H), 7.30-7.25 (m, 1H), 7.06-6.98 (m, 2H), 6.85-6.80 (m, 2H), 5.08-5.04 (m, 2H), 4.96-4.89 (m, 1H), 4.58-4.52 (m, 1H), 4.42-4.38 (m, 2H), 4.31-4.26 (m, 2H), 4.05-4.01 (m, 3H), 3.94-3.90 (m, 1H), 3.73-3.69 (m, 3H), 3.64-3.58 (m, 4H), 3.49-3.45 (m, 3H), 2.62-2.58 (m, 2H), 2.47 (s, 3H), 2.35-2.28 (m, 1H), 2.24-2.16 (m, 6H), 2.04-1.99 (m, 2H), 1.87-1.68 (m, 5H), 1.54-1.50 (m, 4H), 1.39 (d, J = 6.9 Hz, 3H), 0.95 (s, 9H) |
| 249 | I-264 | 63 2-[[(2S,11S)-2-[[(1S)-3-carbamoyl-1-[[3-fluoro-5-(5-[[(2S)-1-[(2S,4R)-4-hydroxy-2-[[(1S)-1-[4-(4-methyl-1,3-thiazol-5-yl)phenyl]ethyl]carbamoyl] pyrrolidin-1-yl]-3,3-dimethyl-1-oxobutan-2-yl]carbamoyl] pentyl)phenyl]carbamoyl] propyl]carbamoyl]-12-oxo-1-azatricyclo[6.4.1.0^[4,13]]trideca-4(13),5,7-trien-11-yl]carbamoyl]-1H-indole-5-carbonylphosphonic acid 7 | 1259.55 | (400 MHz, DMSO-$d_6$) δ 12.12-12.08 (m, 1H), 10.19-10.12 (m, 1H), 9.06-8.92 (m, 2H), 8.83 (d, J = 1.6 Hz, 1H), 8.45-8.38 (m, 2H), 7.96 (d, J = 8.8 Hz, 1H), 7.80 (d, J = 9.2 Hz, 1H), 7.53 (d, J = 8.8 Hz, 1H), 7.48 (d, J = 2.1 Hz, 1H), 7.46-7.30 (m, 6H), 7.18-7.05 (m, 3H), 7.01-6.96 (m, 1H), 6.86-6.76 (m, 1H), 6.76-6.68 (m, 1H), 5.19-5.12 (m, 2H), 4.96-4.88 (m, 1H), 4.74-4.64 (m, 1H), 4.51 (d, J = 9.3 Hz, 1H), 4.46-4.39 (m, 1H), 4.30-4.25 (m, 2H), 3.65-3.58 (m, 2H), 3.56-3.42 (m, 2H), 3.26-3.17 (m, 1H), 3.15-3.09 (m, 1H), 3.04-2.98 (m), 2.46 (s, 3H), 2.30-2.19 (m, 4H), 2.18-2.08 (m, 3H), 2.05-1.73 (m, 4H), 1.58-1.46 (m, 6H), 1.38 (d, J = 7.0 Hz, 3H), 1.29-1.20 (m, 2H), 0.93 (s, 9H) |

TABLE 74-continued

| Characterization Data for Exemplary STAT3 Degraders | | | | |
|---|---|---|---|---|
| 250 | I-265 | diammonium 2-[[(2S,11S)-2-[(4-carbamoyl-1-[[2-fluoro-3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenyl]amino]butan-2-yl)carbamoyl]-12-oxo-1-azatricyclo[6.4.1.0^[4,13]]trideca-4(13),5,7-trien-11-yl]carbamoyl]-1H-indole-5-carbonylphosphonate | 1246.55 | (400 MHz, DMSO-$d_6$) δ 12.01-11.85 (m, 1H), 9.08-8.89 (m, 3H), 8.39 (d, J = 8.9 Hz, 1H), 8.09-8.03 (m, 1H), 7.98-7.91 (m, 1H), 7.83-7.78 (m, 1H), 7.47-7.38 (m, 6H), 7.36-7.30 (m, 2H), 7.17-7.07 (m, 2H), 7.05-6.95 (m, 1H), 6.81 (d, J = 8.1 Hz, 1H), 6.79-6.73 (m, 1H), 6.67-6.60 (m, 1H), 6.42-6.36 (m, 1H), 5.36-5.22 (m, 1H), 5.14-5.02 (m, 1H), 4.96-4.88 (m, 1H), 4.72-4.68 (m, 1H), 4.54-4.41 (m, 2H), 4.30-4.25 (m, 1H), 3.87-3.81 (m, 1H), 3.64-3.59 (m, 2H), 3.51-3.20 (m, 3H), 3.19-3.07 (m, 5H), 2.92-2.88 (m, 1H), 2.76-2.72 (m, 1H), 2.45 (s, 3H), 2.13-2.06 (m, 3H), 2.04-2.00 (m, 4H), 1.80-1.76 (m, 2H), 1.52-1.47 (m, 5H), 1.38 (d, J = 7.0 Hz, 3H), 1.26-1.22 (m, 2H), 0.93 (s, 9H) |
| 251 | I-266 | 2-[[(2S,11S)-2-[[(2S)-4-carbamoyl-1-[2-fluoro-3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)-5-methylphenoxy]butan-2-yl]carbamoyl]-12-oxo-1-azatricyclo[6.4.1.0^[4,13]]trideca-4(13),5,7-trien-11-yl]carbamoyl]-1H-indole-5-carbonylphosphonic acid | 1260.55 | (400 MHz, DMSO-$d_6$) δ 11.95-11.88 (m, 1H), 9.02-8.89 (m, 3H), 8.40 (d, J = 7.7 Hz, 1H), 8.18-8.11 (m, 1H), 7.95 (d, J = 8.7 Hz, 1H), 7.81 (d, J = 9.2 Hz, 1H), 7.52-7.33 (m, 6H), 7.28-7.24 (m, 1H), 7.12-7.05 (m, 2H), 7.01-6.95 (m, 1H), 6.87-6.72 (m, 2H), 6.66-6.55 (m, 1H), 5.09 (dd, J = 10.7, 2.8 Hz, 1H), 4.95-4.89 (m, 1H), 4.72-4.65 (m, 1H), 4.55-4.49 (m, 1H), 4.46-4.39 (m, 1H), 4.31-4.24 (m, 1H), 3.98-3.85 (m, 3H), 3.66-3.58 (m, 2H), 3.49-3.41 (m, 3H), 3.30-3.26 (m, 3H), 2.91-2.85 (m, 1H), 2.46 (s, 3H), 2.32-2.22 (m, 7H), 2.17-1.98 (m, 4H), 1.90-1.64 (m,4H), 1.61-1.42 (m, 4H), 1.38 (d, J = 6.9 Hz, 3H), 1.29-1.22 (m, 2H), 0.93 (s, 9H) |
| 252 | I-267 | diammonium 2-[[(2S,11S)-2-[[(2S)-4-carbamoyl-1-[2,5-difluoro-3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenoxy]butan-2-yl]carbamoyl]-12-oxo-1-azatricyclo[6.4.1.0^[4,13]]trideca-4(13),5,7-trien-11-yl]carbamoyl]-1H-indole-5-carbonylphosphonate | 1264.50 | (400 MHz, DMSO-$d_6$) δ 11.92-11.85 (m, 1H), 8.99-8.89 (m, 3H), 8.40 (d, J = 7.8 Hz, 1H), 8.15 (d, J = 7.2 Hz, 1H), 7.94 (d, J = 8.7 Hz, 1H), 7.81 (d, J = 9.2 Hz, 1H), 7.47-7.31 (m, 6H), 7.28-7.21 (m, 1H), 7.13-7.03 (m, 2H), 7.01-6.93 (m, 2H), 6.81-6.64 (m, 2H), 5.09 (dd, J = 10.8, 2.9 Hz, 1H), 4.98-4.86 (m, 1H), 4.74-4.65 (m, 1H), 4.57-4.51 (m, 1H), 4.46-4.38 (m, 1H), 4.32-4.25 (m, 1H), 4.06-3.91 (m, 4H), 3.64-3.56 (m, 2H), 3.51-3.38 (m, 1H), 3.25-3.07 (m, 2H), 2.91-2.85 (m, 1H), 2.63-2.52 (m, 3H), 2.46 (s, 3H), 2.33-2.10 (m, 4H), 2.19-2.09 (m, 3H), 2.08-1.98 (m, 1H), 1.85-1.75 (m, 1H), 1.73-1.63 (m, 1H), 1.62-1.64 (m, 5H), 1.38 (d, J = 7.0 Hz, 3H), 1.33-1.21 (m, 2H), 0.93 (s, 9H) |
| 253 | I-268 | 2-[[(2S,17S)-2-[[(1S)-3-carbamoyl-1-[4-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)pyridin-2-yl]propyl]carbamoyl]-12-oxo-1-azatricyclo[6.4.1.0^[4,13]]trideca-4(13),5,7-trien-11-yl]carbamoyl]-1H-indole-5-carbonylphosphonic acid | 1199.50 | (300 MHz, DMSO-$d_6$) δ 11.97-11.91 (m, 1H), 9.68-9.62 (m, 1H), 9.04-8.89 (m, 3H), 8.69 (d, J = 7.7 Hz, 1H), 8.45-8.34 (m, 2H), 7.95 (d, J = 8.6 Hz, 1H), 7.84 (d, J = 9.1 Hz, 1H), 7.51-7.38 (m, 6H), 7.31-7.25 (m, 1H), 7.19-7.03 (m, 3H), 7.01-6.92 (m, 1H), 6.82-6.75 (m, 1H), 5.11 (dd, J = 10.8, 2.9 Hz, 1H), 4.99-4.87 (m, 1H), 4.72-4.66 (m, 2H), 4.58-4.39 (m, 2H), 4.33-4.26 (m, 1H), 3.75-3.45 (m, 4H), 2.87-2.61 (m, 5H), 2.47 (s, 3H), 2.31-2.19 (m, 1H), 2.14-2.01 (m, 4H), 1.99-1.75 (m, 4H), 1.72-1.59 (m, 5H), 1.58-1.52 (m, 2H), 1.39 (d, J = 6.9 Hz, 3H), 1.35-1.21 (m, 2H), 0.95 (s, 9H) |
| 254 | I-269 | 2-[[(2S,115)-2-[[(1S)-3-Carbamoyl-1-(diphenylmethylcarbamoyl)propyl]carbamoyl]-7-([6-[1-(2,6-dioxopiperidin-3-yl)-3-methyl-2-oxo-1,3-benzodiazol-5-yl]hexyl]oxy)-12-oxo-1-azatricyclo[6.4.1.0^[4,13]]trideca-4(13),5,7-trien-11-yl]carbamoyl]-1H-indole-5-carbonylphosphonic acid | 1148.40 | (400 MHz, DMSO-$d_6$) δ 12.11-12.05 (m, 1H), 11.12-11.06 (m, 1H), 8.93 (d, J = 7.6 Hz, 1H), 8.81 (s, 1H), 8.73 (d, J = 8.5 Hz, 1H), 8.32 (d, J = 7.7 Hz, 1H), 8.02-7.91 (m, 1H), 7.49 (d, J = 8.8 Hz, 1H), 7.35-7.22 (m, 12H), 7.08-6.96 (m, 3H), 6.86 (d, J = 8.1 Hz, 1H), 6.76-6.71 (m, 1H), 6.64 (d, J = 8.3 Hz, 1H), 6.08 (d, J = 8.4 Hz, 1H),5.38-5.32 (m, 1H), 5.08 (dd, J = 11.1, 4.9 Hz, 1H), 4.77-4.65 (m, 1H), 4.33-4.28 (m, 1H), 4.03-3.94 (m, 2H), 3.54-3.39 (m, 2H), 3.31 (s, 3H), 3.17-3.08 (m, 2H), 2.97-2.76 (m, 3H), 2.76-2.67 (m, 1H), 2.66-2.56 (m, 3H), 2.24-2.09 (m, 4H), 2.04-1.96 (m, 1H), 1.95-1.83 (m, 1H), 1.83-1.74 (m, 3H), 1.68-1.60 (m, 2H), 1.53-1.46 (m, 2H), 1.42-1.26 (m, 2H) |
| 255 | I-270 | 2-[[(2S,11S)-2-[[(1S)-3-carbamoyl-1-(diphenylmethyl carbamoyl)propyl]carbamoyl]-7-[4-[1-(2,6-dioxopiperidin-3-yl)-3-methyl-2-oxo-1,3-benzodiazol-5-yl]butoxy]-12-oxo-1- | 1120.40 | (300 MHz, DMSO-$d_6$) δ 12.15-12.06 (m, 1H), 11.12-11.06 (m, 1H), 8.95 (d, J = 7.7 Hz, 1H), 8.85-8.76 (m, 2H), 8.37-8.17 (m, 1H), 7.97 (d, J = 8.6 Hz, 1H), 7.61-7.43 (m, 2H), 7.41-7.19 (m, 11H), 7.11-6.98 (m, 3H), 6.93 (d, J = 7.3 Hz, 1H), 6.83-6.62 (m, 2H), 6.09 (d, J = 8.2 Hz, 1H), 5.44- |

TABLE 74-continued

Characterization Data for Exemplary STAT3 Degraders

| | | | | |
|---|---|---|---|---|
| | | azatricyclo[6.4.1.0^[4,13]]trideca-4(13),5,7-trien-11-yl]carbamoyl]-1H-indole-5-carbonylphosphonic acid | | 5.28 (m, 1H), 5.08 (dd, J = 11.1, 4.9 Hz, 1H), 4.79-4.58 (m, 1H), 4.41-4.26 (m, 1H), 4.10-3.97 (m, 3H), 3.34 (s, 3H), 3.23-3.05 (m, 1H), 3.06-2.95 (m, 2H), 2.93-2.79 (m, 2H), 2.79-2.58 (m, 4H), 2.32-1.94 (m, 6H), 1.92-1.67 (m, 6H) |
| 256 | I-271 | 2-[[(5S,8S,10aR)-8-[[(1S)-3-carbamoyl-1-(diphenylmethylcarbamoyl)propyl]carbamoyl]-6-oxo-3-[4-[(1r,4s)-4-[1-(2,6-dioxopiperidin-3-yl)-3-methyl-2-oxo-1,3-benzodiazol-5-yl]cyclohexyl]butanoyl]-octahydropyrrolo[1,2-a][1,5]diazocin-5-yl]carbamoyl]-1H-indole-5-carbonylphosphonic acid | 1181.60 | (300 MHz, DMSO-$d_6$) δ 12.17-11.98 (m, 1H), 11.12-11.06 (m, 1H), 8.85-8.71 (m, 2H), 8.46 (d, J = 6.8 Hz, 1H), 8.26-8.21 (m, 1H), 8.04-7.96 (m, 1H), 7.54 (d, J = 8.7 Hz, 1H), 7.50-7.41 (m, 1H), 7.39-7.20 (m, HH), 7.10-6.96 (m, 2H), 6.95-6.86 (m, 1H), 6.81-6.75 (m, 1H), 6.11 (dd, J = 8.5, 3.3 Hz, 1H), 5.34 (dd, J = 13.1, 5.0 Hz, 1H), 5.05-4.92 (m, 1H), 4.55-4.14 (m, 3H), 3.89 (m, 2H), 3.58-3.42(m, 3H), 3.34 (s, 3H), 2.96-2.89 (m, 2H), 2.76-2.55 (m, 6H), 2.25-1.82 (m, 5H), 1.82-1.41 (m, 18H) |
| 257 | I-272 | diammonium 2-[[(2S,11S)-2-[[(2S)-1-[3-(5-[[(2S)-1-[(2S,4R)-4-(acetyloxy)-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)-2-fluorophenoxy]-4-carbamoylbutan-2-yl]carbamoyl]-12-oxo-1-azatricyclo[6.4.1.0^[4,13]]trideca-4(13),5,7-trien-11-yl]carbamoyl]-1H-indole-5-carbonylphosphonate | 1288.55 | (400 MHz, DMSO-$d_6$) δ 11.96-11.92 (m, 1H), 8.97 (d, J = 17.8 Hz, 2H), 8.94-8.88 (m, 1H), 8.44 (d, J = 7.7 Hz, 1H), 8.16 (d, J = 7.4 Hz, 1H), 7.96 (d, J = 8.7 Hz, 1H),7.84 (d, J = 8.7 Hz, 1H), 7.47-7.41 (m, 4H), 7.38 (d, J = 8.2 Hz, 2H), 7.32-7.26 (m, 1H), 7.13-7.04 (m, 2H), 7.03-6.92 (m, 3H), 6.87-6.81 (m, 1H), 6.79-6.72(m, 1H), 5.23-5.17 (m, 1H), 5.09 (dd, J = 10.7, 3.0 Hz, 1H), 4.95-4.89 (m, 1H), 4.72-4.64 (m 1H), 4.50-4.43 (m, 1H), 4.36 (d, J = 8.7 Hz, 1H), 4.03-3.91 (m, 4H), 3.78-3.71 (m, 1H), 3.52-3.40 (m, 2H), 3.28-3.15 (m, 1H), 3.16-3.08 (m, 1H), 2.92-2.85 (m, 1H), 2.62-2.55 (m, 2H), 2.46 (s, 3H), 2.30-2.18 (m, 5H), 2.19-2.06 (m, 3H), 2.00 (s, 3H), 1.87-1.81 (m, 1H), 1.74-1.67 (m, 1H), 1.62-1.44 (m, 5H), 1.38 (d, J = 7.0 Hz, 3H), 1.32-1.24 (m, 2H), 0.95 (s, 9H) |
| 258 | I-273 | 2-[[(5S,8S,10aR)-8-[[(1S)-3-carbamoyl-1-(diphenylmethyl-carbamoyl)propyl]carbamoyl]-6-oxo-3-[3-[(1s,4s)-4-[1-(2,6-dioxopiperidin-3-yl)-3-methyl-2-oxo-1,3-benzodiazol-5-yl]cyclohexyl]propanoyl]-octahydropyrrolo[1,2-a][1,5]diazocin-5-yl]carbamoyl]-1H-indole-5-carbonylphosphonic acid | 1167.55 | (400 MHz, DMSO-$d_6$) δ 12.18-12.13 (m, 1H), 11.12-11.06 (m, 1H), 8.86-8.72 (m, 2H), 8.54-8.45 (m, 1H), 8.24-8.18 (m, 1H), 7.96 (d, J = 8.8 Hz, 1H), 7.57-7.40 (m, 2H), 7.38-7.18 (m, HH), 7.09-6.95 (m, 2H), 6.88 (d, J = 7.4 Hz, 1H), 6.78-6.69 (m, 1H),6.11 (dd, J = 8.5, 3.3 Hz, 1H), 5.37-5.29 (m, 1H), 5.08 (dd, J = 11.1, 4.9 Hz, 1H), 4.49-4.42 (m, 1H), 4.43-4.36 (m, 2H), 4.22-4.20 (m, 1H), 3.96-3.89 (m, 1H), 3.77-3.65 (m, 2H), 3.34 (s, 3H), 2.96-2.81 (m, 1H), 2.77-2.57 (m, 3H), 2.20-2.06 (m, 4H), 2.05-1.96 (m, 4H), 1.95-1.85 (m, 6H), 1.85-1.62 (m, 2H), 1.51-1.48 (m, 6H), 1.29-1.25 (m, 2H), 1.09-1.07 (m, 2H) |
| 259 | I-274 | 2-[[(5S,8S,10aR)-8-[[(1S)-3-carbamoyl-1-(diphenylmethylcarbamoyl)propyl]carbamoyl]-6-oxo-3-[4-[(1s,4r)-4-[1-(2,6-dioxopiperidin-3-yl)-3-methyl-2-oxo-1,3-benzodiazol-5-yl]cyclohexyl]butanoyl]-octahydropyrrolo[1,2-a][1,5]diazocin-5-yl]carbamoyl]-1H-indole-5-carbonylphosphonic acid | 1181.55 | (400 MHz, $CD_3OD$) δ 8.88-8.85 (m, 1H), 8.08-8.04 (m, 1H), 7.55-7.53 (m, 1H), 7.44-7.18 (m, 11H), 7.06-6.95 (m, 2H), 6.89-6.80 (m, 1H), 6.20-6.14 (m, 1H), 5.34-5.24 (m, 1H), 5.15-5.09 (m, 1H), 4.53-4.50 (m, 2H), 4.36-7.34 (m, 1H), 4.05-3.6 (m, 1H), 3.85-3.83 (m, 2H), 3.56-3.54 (m, 1H), 3.40 (s, 3H), 3.01-2.88 (m, 1H), 2.86-2.76 (m, 2H), 2.67-2.60 (m, 2H), 2.52-2.50 (m, 1H), 2.42-2.39 (m, 2H), 2.29-2.13 (m, 4H), 2.05-1.66 (m, 11H), 1.56-1.44 (m, 2H), 1.38-1.33 (m, 3H), 1.15-1.32 (m, 2H) |
| 260 | I-275 | diammonium 2-[[(5S,8S,10aR)-3-acetyl-8-[[(2S)-4-carbamoyl-1-[2-fluoro-3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenoxy]butan-2-yl]carbamoyl]-6-oxo-octahydropyrrolo[1,2-a][1,5]diazocin-5-yl]carbamoyl]-1H-indole-5-carbonylphosphonate | 1270.55 | (400 MHz, DMSO-$d_6$) δ12.09-11.79 (m, 1H), 8.99 (s, 1H), 8.92-8.78 (m, 1H), 8.52-8.38 (m, 1H), 8.12-8.02 (m, 1H), 7.99-7.93 (m, 1H), 7.80 (d, J = 9.1 Hz, 1H), 7.46-7.33 (m, 7H), 7.31-7.24 (m, 1H), 7.02-6.97 (m, 2H), 6.84-6.79 (m, 2H), 5.07-4.99 (m, 1H), 4.96-4.87 (m, 1H), 4.55-4.49 (m, 1H), 4.48-4.34 (m, 2H), 4.31-4.21 (m, 2H), 4.09-3.96 (m, 2H), 3.95-3.81 (m, 2H), 3.76-3.66 (m, 2H), 3.63-3.59 (m, 2H), 3.46-3.27 (m, 3H), 2.59-2.55 (m, 2H), 2.46 (s, 3H), 2.30-2.24 (m, 1H), 2.20 (s, 3H), 2.16-1.98 (m, 6H), 1.96-1.62 (m, 7H), 1.60-1.44 (m, 5H), 1.38 (d, J = 7.0 Hz, 3H), 1.31-1.23 (m, 2H), 0.93 (s, 9H) |
| 261 | I-276 | diammonium 2-[[(2S)-1-[(2S)-2-[[(2S)-4-carbamoyl-1-[2-fluoro-3-(4-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]butyl)phenoxy | [(M − 1)]$^-$ = 1213.05 | (400 MHz, DMSO-$d_6$) δ11.84 (s, 1H), 8.98 (s, 1H), 8.87 (s, 1H), 8.75-8.69 (m, 1H), 8.39 (d, J = 7.8 Hz, 1H), 7.97-7.93 (m, 1H), 7.90-7.86 (m, 1H), 7.84-7.80 (m, 1H), 7.47-7.29 (m, 6H), 7.20 (s, 1H), 7.04-6.95 (m, 2H), 6.86-6.75 (m, 2H), 4.94-4.79 (m, 2H), 4.51 (d, J = 9.3 Hz, 1H), 4.45-4.40 (m, 1H), 4.35-4.24 (m, 2H), 4.06-3.98 (m, 1H), 4.00-3.87 (m, 2H), 3.84-3.77 (m, 1H), 3.65- |

TABLE 74-continued

| Characterization Data for Exemplary STAT3 Degraders | | | | |
|---|---|---|---|---|
| | | ]butan-2-yl]carbamoyl]pyrrolidin-1-yl]-4-methyl-1-oxopentan-2-yl]carbamoyl]-1H-indole-5-carbonylphosphonate | | 3.57 (m, 3H), 3.47-3.34 (m, 1H), 2.62-2.55 (m, 3H), 2.45 (s, 3H), 2.33-2.25 (m, 1H), 2.19-2.11 (m, 3H), 2.07-1.97 (m, 3H), 1.93-1.74 (m, 5H), 1.72-1.62 (m, 3H), 1.61-1.44 (m, 6H), 1.37 (d, J = 7.0 Hz, 3H), 0.94-0.90 (m, 15H) |
| 267 | I-277 | 2-[[(2S,11S)-2-[[(1S)-3-carbamoyl-1-(pyridin-2-yl)propyl]carbamoyl]-6-[6-[1-(2,6-dioxopiperidin-3-yl)-3-methyl-2-oxo-1,3-benzodiazol-5-yl]hexyl]-12-oxo-1-azatricyclo[6.4.1.0^[4,13]]trideca-4(13),5,7-trien-11-yl]carbamoyl]-1H-indole-5-carbonylphosphonic acid | 1000.35 | (400 MHz, DMSO-$d_6$) δ 12.10 (s, 1H), 11.09 (s, 1H), 8.98 (d, J = 8.0 Hz, 1H), 8.83 (s, 1H), 8.58-8.46 (m, 2H), 7.99-7.93 (m, 1H), 7.80-7.71 (m, 1H), 7.57-7.46 (m, 2H), 7.35-7.29 (m, 1H), 7.27-7.19 (m, 2H), 7.06-6.98 (m, 2H), 6.95-6.83 (m, 3H), 6.72 (s, 1H), 5.38-5.30 (m, 1H), 5.19-5.13 (m, 1H), 4.85-4.74 (m, 1H), 4.72-4.62 (m, 1H), 3.48-3.41 (m, 2H), 3.32 (s, 3H), 3.23-3.06 (m, 3H), 2.96-2.79 (m, 2H), 2.76-2.58 (m, 4H), 2.49-2.45 (m, 2H), 2.30-2.13 (m, 2H), 2.07-1.85 (m, 5H), 1.66-1.49 (m, 4H), 1.38-1.27 (m, 4H) |
| 268 | I-278 | 2-[[(5S,8S,10aR)-8-[[(1S)-3-carbamoyl-1-(diphenylmethylcarbamoyl)propyl]carbamoyl]-6-oxo-3-[3-[(1r,4r)-4-[1-(2,6-dioxopiperidin-3-yl)-3-methyl-2-oxo-1,3-benzodiazol-5-yl]cyclohexyl]propanoyl]-octahydropyrrolo[1,2-a][1,5]diazocin-5-yl]carbamoyl]-1H-indole-5-carbonylphosphonic acid | 1167.55 | (400 MHz, DMSO-$d_6$) δ 12.22-12.02 (m, 1H), 11.09 (s, 1H), 8.90-8.63 (m, 3H), 8.47-8.41 (m, 1H), 8.26-8.17 (m, 1H), 7.98-7.93 (m, 1H), 7.57-7.51 (m, 1H), 7.48-7.40 (m, 1H), 7.38-7.20 (m, 10H), 7.11-7.05 (m, 1H), 7.03-6.96 (m, 1H), 6.94-6.87 (m, 1H), 6.81-6.71 (m, 1H), 6.13-6.07 (m, 1H), 5.37-5.29 (m, 1H), 5.05-4.87 (m, 1H), 4.51-4.42 (m, 1H), 4.41-4.32 (m, 1H), 4.27-4.17 (m, 1H), 4.06-3.89 (m, 1H), 3.86-3.75 (m, 1H), 3.72-3.60 (m, 1H), 3.57-3.45 (m, 1H), 3.33 (s, 3H), 2.90-2.85 (m, 1H), 2.76-2.54 (m, 5H), 2.24-1.87 (m, 8H), 1.85-1.56 (m, 16H) |
| 269 | I-279 | diammonium 2-[[(2S)-1-[(2S)-2-[[(2S)-4-carbamoyl-1-[2-fluoro-3-(5-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]pentyl)phenoxy]butan-2-yl]carbamoyl]pyrrolidin-1-yl]-4-methyl-1-oxopentan-2-yl]carbamoyl]-1H-indole-5-carbonylphosphonate | 1228.65 | (400 MHz, $CD_3OD$) δ 9.00-8.96 (m, 1H), 8.89 (s, 1H), 8.58 (d, J = 7.6 Hz, 1H), 8.18 (d, J = 8.7 Hz, 1H), 8.13-8.06 (m, 1H), 7.52-7.39 (m, 5H), 7.00-6.94 (m, 1H), 6.85-6.79 (m, 1H), 5.06-4.91 (m, 2H), 4.67-4.56 (m, 2H), 4.46-4.42 (m, 2H), 4.29-4.20 (m, 1H), 4.14-3.95 (m, 3H), 3.93-3.86 (m, 1H), 3.79-3.69 (m, 2H), 3.63-3.34 (m, 4H), 2.67-2.65 (m, 2H), 2.50 (s, 3H), 2.42-2.18 (m, 6H), 2.17-1.90 (m,4H), 1.90-1.78 (m, 3H), 1.74-1.60 (m, 4H), 1.54-1.48 (m, 3H), 1.42-1.27 (m, 2H), 1.09-0.99 (m, 13H) |
| 270 | I-280 | diammonium 2-[[(2S,11S)-2-[[(1S)-3-carbamoyl-1-[[3-(4-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]butyl)phenyl]carbamoyl]propyl]carbamoyl]-12-oxo-1-azatricyclo[6.4.1.0^[4,13]]trideca-4(13),5,7-trien-11-yl]carbamoyl]-1H-indole-5-carbonylphosphonate | 1227.60 | (300 MHz, DMSO-$d_6$) δ 11.88 (s, 1H), 9.94 (s, 1H), 9.08-8.86 (m, 3H), 8.47-8.29 (m, 2H), 7.96 (d, J = 8.7 Hz, 1H), 7.87-7.78 (m, 1H), 7.49-7.37 (m, 7H), 7.36-7.30 (m, 1H), 7.22-7.08 (m, 4H), 7.06-6.95 (m, 1H), 6.88 (d, J = 7.6 Hz, 1H), 6.79 (s, 1H), 5.25-5.12 (m, 2H), 4.97-4.86 (m, 1H), 4.73-4.67 (m, 1H), 4.57-4.40 (m, 2H), 4.36-4.27 (m, 2H), 3.65-3.50 (m, 4H), 3.08-2.97 (m, 2H), 2.47 (s, 3H), 2.36-2.22 (m, 4H), 2.21-2.10 (m, 3H), 2.06-1.77 (m, 5H), 1.58-1.47 (m, 4H), 1.39 (d, J = 6.9 Hz, 3H), 1.29-1.15 (m, 2H), 0.95 (s, 9H) |
| 271 | I-281 | diammonium 2-[[(2S,11S)-2-[[(2S)-4-carbamoyl-1-[2-fluoro-3-[4-([[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]oxy)butyl]phenoxy]butan-2-yl]carbamoyl]-12-oxo-1-azatricyclo[6.4.1.0^[4,13]]trideca-4(13),5,7-trien-11-yl]carbamoyl]-1H-indole-5-carbonylphosphonate | 1248.85 | (400 MHz, DMSO-$d_6$) δ 11.90 (s, 1H), 9.03-8.93 (m, 2H), 8.90 (s, 1H), 8.42 (d, J = 7.8 Hz, 1H), 8.18-8.12 (m, 1H), 7.96 (d, J = 8.4 Hz, 1H), 7.49-7.40 (m, 4H), 7.38 (d, J = 8.1 Hz, 2H), 7.27 (s, 1H), 7.09 (t, J = 7.7 Hz, 2H), 7.03-6.90 (m, 4H), 6.88-6.79 (m, 1H), 6.76 (s, 1H), 5.13-5.06 (m, 1H), 4.95-4.86 (m, 1H), 4.76-4.64 (m, 1H), 4.49-4.41 (m, 1H), 4.31-4.25 (m, 1H), 4.17 (d, J = 9.2 Hz, 1H), 4.05-3.93 (m, 5H), 3.62-3.57 (m, 2H), 3.50-3.43 (m, 3H), 3.22-3.09 (m, 3H), 2.94-2.84 (m, 1H), 2.65-2.58 (m, 2H), 2.46 (s, 3H), 2.32-2.19 (m, 2H), 2.18-2.09 (m, 2H), 2.07-2.00 (m, 1H), 1.88-1.66 (m, 3H), 1.65-1.50 (m, 4H), 1.37 (d, J = 7.0 Hz, 3H), 0.94 (s, 9H) |
| 272 | I-283 | diammonium 2-[(2S,11S)-2-[[(2S)-4-carbamoyl-1-[2-chloro-3-(3-[[(2S)-1-[(2S,4R)-4-hydroxy-2-([l-[4-(4-methyl-1,3-thiazol-5-yl)phenyl]cyclopropyl]carbamoyl)pyrrolidin-1-yl]-3,3-dimethyl-1-oxobutan-2-yl]carbamoyl]propyl)phenoxy]butan-2-yl]carbamoyl]-12-oxo-1-azatricyclo[6.4.1.0^[4,13]]trideca-4(13),5,7-trien-11-yl] | [(M − 1)]− = 1244.65 | (300 MHz, DMSO-$d_6$) δ 11.89 (s, 1H), 9.01-8.90 (m, 3H), 8.84 (s, 1H), 8.16 (d, J = 7.4 Hz, 1H), 8.05 (d, J = 9.3 Hz, 1H), 7.99-7.83 (m, 1H), 7.48-7.39 (m, 3H), 7.36-7.28 (m, 4H), 7.25-7.14 (m, 1H), 7.12-7.05 (m, 2H), 7.06-7.01 (m, 2H), 6.96-6.87 (m, 1H), 6.78 (s, 1H), 5.14-5.07 (m, 1H), 4.73-4.67 (m, 1H), 4.63-4.56 (m, 1H), 4.46-4.38 (m, 2H), 4.08-3.92 (m, 3H), 3.70-3.65 (m, 2H), 3.22-3.10 (m, 3H), 3.02-2.93 (m, 1H), 2.79-2.59 (m, 3H), 2.45 (s, 3H), 2.39-2.09 (m, 7H), 2.07-1.97 (m, 1H), 1.96-1.66 (m, 6H), 1.29-1.10 (m, |

TABLE 74-continued

| Characterization Data for Exemplary STAT3 Degraders | | | | |
|---|---|---|---|---|
| | | carbamoyl]-1H-indole-5-carbonylphosphonate | | 4H), 0.97 (s, 9H) |
| 273 | I-284 | diammonium 2-[[(5S,8S,10aR)-3-acetyl-8-[[(2S)-4-carbamoyl-1-[2-chloro-3-(3-[[(2S)-1-[(2S,4R)-4-hydroxy-2-([1-[4-(4-methyl-1,3-thiazol-5-yl)phenyl] cyclopropyl]carbamoyl) pyrrolidin-1-yl]-3,3-dimethyl-1-oxobutan-2-yl]carbamoyl] propyl)phenoxy]butan-2-yl] carbamoyl]-6-oxo-octahydropyrrolo [1,2-a][1,5]diazocin-5-yl] carbamoyl]-1H-indole-5-carbonylphosphonate | 1269.50 | (300 MHz, DMSO-$d_6$) δ 12.08-11.74 (m, 1H), 9.001 (s, 1H), 8.95-8.90 (m, 1H), 8.86-8.79 (m, 1H), 8.56-8.47 (m, 1H), 8.13-7.92 (m, 3H), 7.43 (d, J = 8.4 Hz, 1H), 7.37-7.29 (m, 5H), 7.26-7.18 (m, 1H), 7.07-6.97 (m, 1H), 6.95-6.88 (m, 1H), 6.82 (s, 1H), 6.71 (s, 1H), 5.07-5.01 (m, 1H), 4.64-4.52 (m, 1H), 4.44-4.21 (m, 4H), 4.14-3.99 (m, 2H), 3.98-3.83 (m, 3H), 3.77-3.64 (m, 5H), 2.76-2.62 (m, 3H), 2.45 (s, 3H), 2.40-2.28 (m, 2H), 2.27-2.08 (m, 7H), 2.07-1.85 (m, 5H), 1.85-1.63 (m, 6H), 1.26-1.16 (m, 4H), 0.96 (s, 9H) |
| 274 | I-285 | (2-(((5S,8S,10aR)-8-(((S)-5-amino-1-((4-(methylsulfonyl) benzyl)amino)-1,5-dioxopentan-2-yl)carbamoyl)-3-((1s,4S)-4-(2-(l-(2,6-dioxopiperidin-3-yl)-3-methyl-2-oxo-2,3-dihydro-1H-benzo[d]imidazol-5-yl) ethyl)cyclohexane-1-carbonyl)-6-oxodecahydropyrrolo[1, 2-a][1,5]diazocin-5-yl) carbamoyl)-1H-indole-5-carbonyl) phosphonic acid | $[(M-1)]^- =$ 1168.05 | (400 MHz, DMSO-$d_6$) δ 12.21-12.0 (m, 1H), 11.09 (s, 1H), 8.82 (s, 2H), 8.61- 8.43 (m, 2H), 8.32 (d, J = 8.1 Hz, 1H),7.97 (d, J = 8.7 Hz, 1H), 7.86 (d, J = 8.1 Hz, 2H), 7.60-7.38 (m, 4H), 7.06-6.95 (m, 2H), 6.94-6.76 (m, 2H), 5.34 (dd, J = 12.6, 5.3 Hz, 1H), 5.04-5.01 (m, 1H), 4.45 (t, J = 8.1 Hz, 1H), 4.40 (d, J = 6.0 Hz, 2H), 4.25-4.21 (m, 2H), 3.59-3.48 (m, 3H), 3.42-3.31 (m, 5H), 3.30 (s, 3H), 3.21 (s, 3H), 2.98-2.81 (m, 2H), 2.78-2.61 (m, 3H), 2.28-2.11 (m, 4H), 2.09-1.96 (m, 2H), 1.89-1.65 (m, 10H), 1.51-1.44 (m, 3H), 1.35-1.20 (m, 2H). |
| 275 | I-286 | 2-[[(5S,8S,10aR)-8-[[(1S)-3-carbamoyl-1-[[(4-methanesulfonylphenyl) methyl]carbamoyl] propyl]carbamoyl]-6-oxo-3-[2-[(1r,4r)-4-[[1-(2,6-dioxopiperidin-3-yl)-3-methyl-2-oxo-1,3-benzodiazol-5-yl]methyl] cyclohexyl]acetyl]-octahydropyrrolo [1,2-a][1,5]diazocin-5-yl]carbamoyl]-1H-indole-5-carbonylphosphonic acid; trifluoroacetic acid | 1170.35 | (300 MHz, DMSO-$d_6$) δ 12.23-12.01 (m, 1H), 11.10 (s, 1H), 8.81 (s, 1H), 8.61- 8.50 (m, 1H), 8.45 (d, J = 6.8 Hz, 1H), 8.28 (dd, J = 15.8, 7.6 Hz, 1H), 7.97 (dd, J = 9.0, 1.6 Hz, 1H), 7.87 (dd, J = 8.3, 2.9 Hz, 2H), 7.60-7.40 (m, 4H), 7.32-7.24 (m, 1H), 7.06- 6.91 (m, 2H), 6.87- 6.68 (m, 2H), 5.35 (dd, J = 12.8, 5.4 Hz, 1H), 5.01-4.84 (m, 1H), 4.51-4.35 (m, 4H), 4.31-4.11 (m, 4H), 3.96-3.86 (m, 2H), 3.82-3.78 (m, 1H), 3.33 (s, 3H), 3.20 (s, 3H), 2.77-2.63 (m, 3H), 2.31-1.95 (m, 8H), 1.93-1.60 (m, 12H), 1.53-1.46 (m, 1H), 1.09-0.87 (m, 4H) |
| 276 | I-288 | 2-[[(5S,8S,10aR)-8-[[(1S)-3-carbamoyl-1-[[(4-methanesulfonylphenyl) methyl]carbamoyl] propyl]carbamoyl]-3-[7-[1-(2,6-dioxopiperidin-3-yl)-3-methyl-2-oxo-1,3-benzodiazol-5-yl]heptanoyl]-6-oxo-octahydropyrrolo[1,2-a][1,5] diazocin-5-yl]carbamoyl]-1H-indole-5-carbonylphosphonic acid | 1143.40 | (400 MHz, DMSO-$d_6$) δ 12.21-12.01 (m, 1H), 11.09 (s, 1H), 8.87-8.79 (m, 1H), 8.59-8.53 (m, 1H), 8.48-8.40 (m, 1H), 8.29 (dd, J = 22.4, 7.6 Hz, 1H), 7.98 (d, J = 8.8 Hz, 1H), 7.86 (dd, J = 8.4, 2.4 Hz, 2H), 7.51 (m, 3H), 7.43 (d, J = 11.2 Hz, 1H), 7.27 (d, J = 17.5 Hz, 1H), 7.05-6.97 (m, 2H), 6.87-6.84 (m, 2H), 5.35 (dd, J = 12.8, 5.4 Hz, 1H), 5.01-4.94 (m, 1H), 4.48-4.37 (m, 3H), 4.29-4.20 (m, 2H), 3.96-3.73 (m, 4H), 3.65-3.50 (m, 3H), 3.31 (s, 3H), 3.21 (s, 3H), 2.95-2.85 (m, 1H), 2.77-2.57 (m, 5H), 2.22-2.09 (m, 3H), 2.03-1.77 (m, 6H), 1.71-1.51 (m, 6H), 1.43-1.28 (m, 4H) |

Example 277. Ammonium 2-[[(2S,11S)-2-[[(3S,4R)-1-carbamoyl-4-[[4-(4-[[(2S)-1-[(2S,4R)-4-hydroxy-2-[[(1S)-1-[4-(4-methyl-1,3-thiazol-5 yl)phenyl]ethyl]carbamoyl]pyrrolidin-1-yl]-3,3-dimethyl-1-oxobutan-2-yl]carbamoyl]butyl)phenyl]methoxy]pentan-3-yl]carbamoyl]-12-oxo-1-azatricyclo[6.4.1.0[4,13]]trideca-4(13), 5,7-trien-11-yl]carbamoyl]-1H-indole-5-carboxylate (I-131)

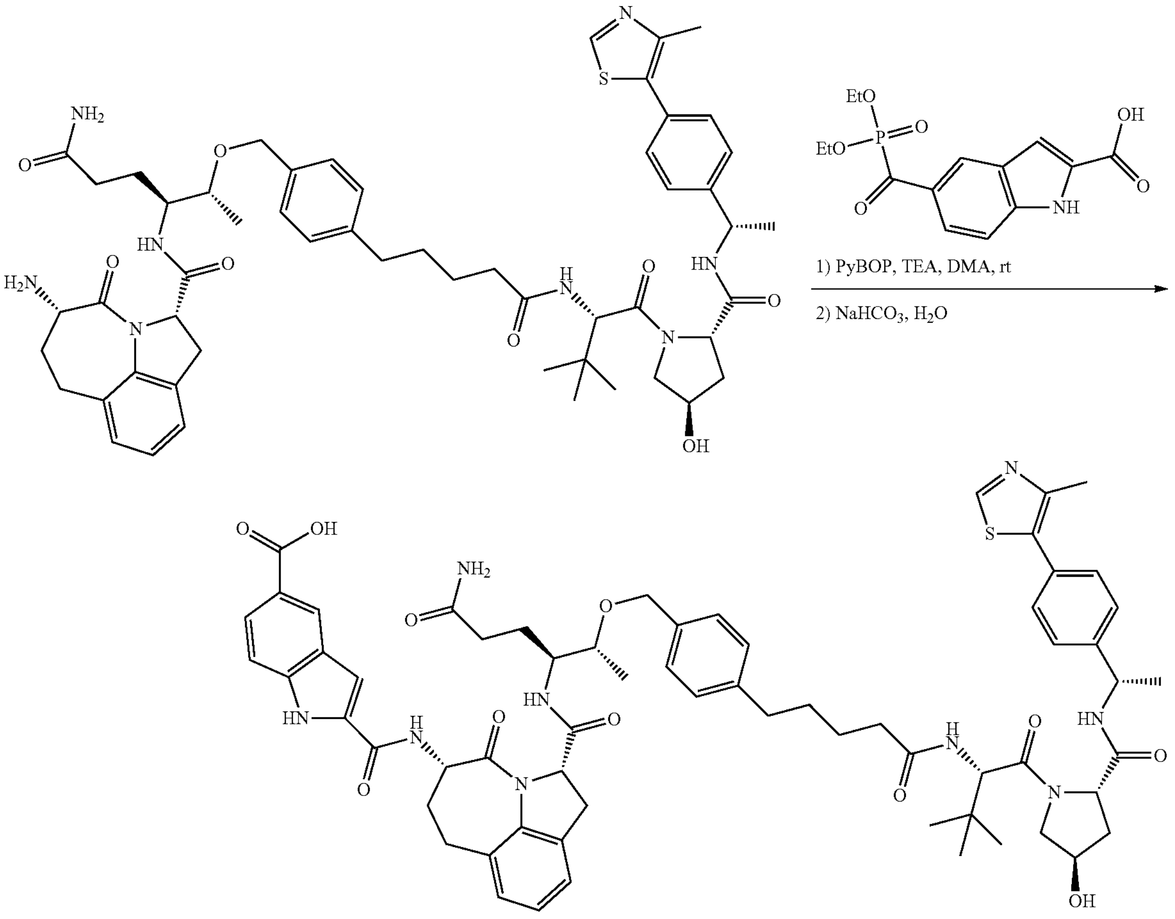

I-131

To a solution of (2S,4R)-1-[(2S)-2-[5-[4-([[(2R,3S)-3-[[(2S,11S)-11-amino-12-oxo-1-azatricyclo[6.4.1.0[4,13]]trideca-4(13), 5,7-trien-2-yl]formamido]-5-carbamoylpentan-2-yl]oxy]methyl)phenyl]pentanamido]-3,3-dimethylbutanoyl]-4-hydroxy-N-[(1S)-1-[4-(4-methyl-1,3-thiazol-5-yl)phenyl]ethyl]pyrrolidine-2-carboxamide (200.00 mg, 0.202 mmol) and 5-[(diethoxyphosphoryl)carbonyl]-1H-indole-2-carboxylic acid (78.75 mg, 0.242 mmol) in DMA (5.00 mL) were added TEA (61.25 mg, 0.605 mmol) and PyBOP (136.50 mg, 0.262 mmol) at 25° C. The solution was stirred at 25° C. for 4 h. To above resulting solution was added a solution of $NaHCO_3$ (84.75 mg, 1.009 mmol) in $H_2O$ (5.00 mL). The resulting mixture was stirred for additional 16 h at 25° C. The crude reaction solution was purified by Prep-HPLC with the following conditions: Column: XBridge Shield RP18 OBD Column, 30×150 mm, 5 um; Mobile Phase A: water (plus 10 moL/L$NH_4HCO_3$), Mobile Phase B: ACN; Flow rate: 60 mL/min; Gradient: 5 B to 35 B in 7 min; Detector: 220/254 nm; Desired fractions were collected at 6.3 min, concentrated and lyophilized to afford the title compound as a white solid (30.5 mg, 13%): $^1$H NMR (400 MHz, $CD_3OD$) δ 8.90 (s, 1H), 8.43 (s, 1H), 7.93 (d, J=8.4 Hz, 1H), 7.52 (d, J=8.3 Hz, 1H), 7.48-7.37 (m, 4H), 7.36-7.31 (m, 1H), 7.24 (d, J=7.8 Hz, 2H), 7.18-6.99 (m, 5H), 5.21-5.17 (m, 1H), 5.01 (q, J=7.1 Hz, 1H), 4.83-4.80 (m, 1H), 4.68-4.54 (m, 2H), 4.54-4.40 (m, 3H), 4.04-3.99 (m, 1H), 3.91-3.88 (m, 1H), 3.78-3.74 (m, 1H), 3.68-3.45 (m, 3H), 3.28-3.22 (m, 1H), 3.18-3.02 (m, 1H), 2.61-2.57 (m, 2H), 2.49 (s, 3H), 2.46-2.14 (m, 6H), 2.06-1.93 (m, 2H), 1.78-1.54 (m, 5H), 1.51 (d, J=7.0 Hz, 3H), 1.41-1.29 (m, 1H), 1.21 (d, J=6.3 Hz, 3H), 1.04 (s, 9H); LC/MS (ESI, m/z): $[(M+1)]^+$=1178.65.

The following compounds in Table 75 were synthesized according to the procedure to prepare I-131.

TABLE 75

| Characterization Data for Exemplary STAT3 Degraders | | | | |
|---|---|---|---|---|
| EXAMPLE | I-# | Chemical Name | MS: $[(M+1)]^+$ | $^1H$ NMR |
| 278 | I-287 | 2-[[(5S,8S,10aR)-8-[[(1S)-3-carbamoyl-1-[[(4-methanesulfonylphenyl)methyl]carbamoyl]propyl]carbamoyl]-6-oxo-3-[2-[(1s,4s)-4-[[1-(2,6-dioxopiperidin-3-yl)-3-methyl-2-oxo-1,3-benzodiazol-5-yl]methyl]cyclohexyl]acetyl]-octahydropyrrolo[1,2-a][1,5]diazocin-5-yl]carbamoyl]-1H-indole-5-carboxylic acid | $[(M-H)]^-$ = 1103.50 | (400 MHz, DMSO-$d_6$) δ 12.21-12.01 (m, 1H), 11.09 (s, 1H), 8.58 (s, 1H), 8.60-8.51 (m, 1H), 8.48-8.44 (m, 1H), 8.36-8.32 (m, 1H), 7.87 (d, J = 8.3 Hz, 2H), 7.82 (d, J = 8.4 Hz, 1H), 7.55-7.45 (m, 3H), 7.37 (d, J = 7.3 Hz, 1H), 7.27 (d, J = 16.5 Hz, 1H), 6.99-6.95 (m, 2H), 6.84-6.80 (m, 2H), 5.33 (dd, J = 12.7, 5.8 Hz, 1H), 5.03-4.98 (m, 1H), 4.46-4.40 (m, 3H), 4.30-4.23 (m, 2H), 3.99-3.75 (m, 3H), 3.33 (s, 3H), 3.29 (s, 2H), 3.19 (s, 3H), 2.93-2.89 (m, 2H), 2.86-2.59 (m, 5H), 2.16-2.05 (m, 3H), 2.04-2.70 (m, 10H), 1.55-1.35 (m, 8H) |

Example 279. (2-(((5S,8S,10aR)-8-(((S)-5-amino-1-(benzhydrylamino)-1,5-dioxopentan-2-yl)carbamoyl)-3-(2-((1S,4R)-4-((1-((R)-2,6-dioxopiperidin-3-yl)-3-methyl-2-oxo-2,3-dihydro-1H-benzo[d]imidazol-5-yl)methyl)cyclohexyl)acetyl)-6-oxodecahydropyrrolo[1,2-a][1,5]diazocin-5-yl)carbamoyl)-1H-indole-5-carbonyl)phosphonic acid (I-234)

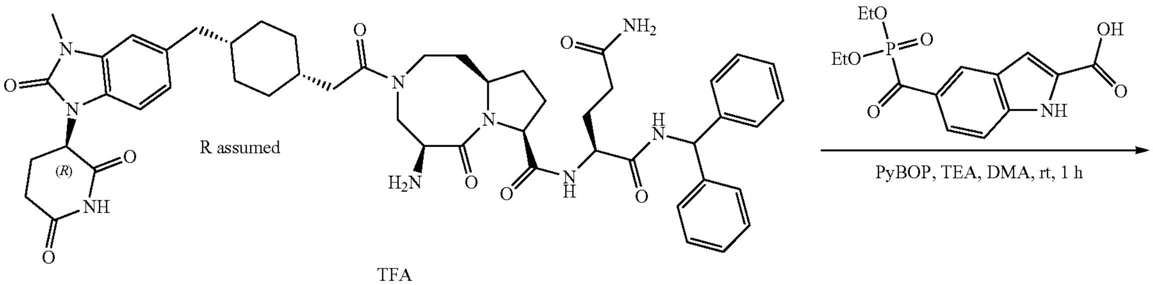

TFA

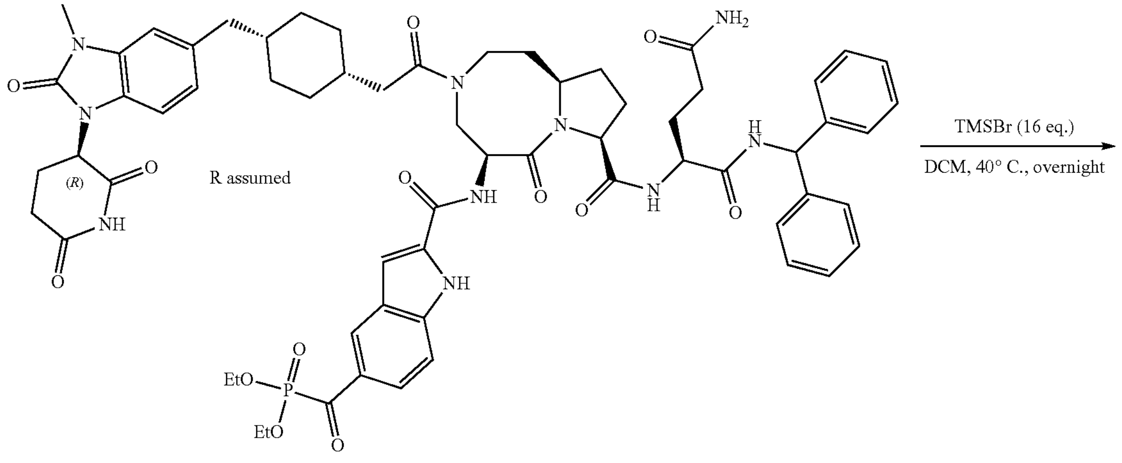

Intermediate S

-continued

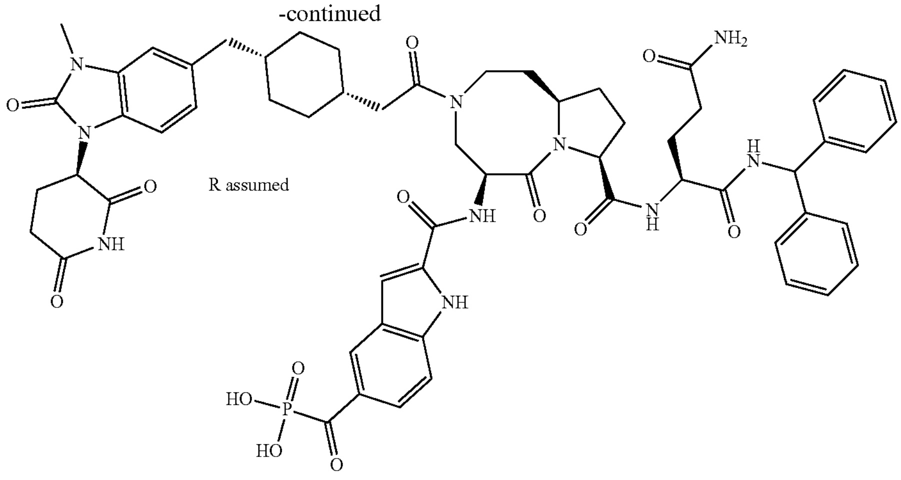

I-234

Step 1. diethyl (2-(((5S,8S,10aR)-8-(((S)-5-amino-1-(benzhydrylamino)-1,5-dioxopentan-2-yl)carbamoyl)-3-(2-((1S,4R)-4-((1-((R)-2,6-dioxopiperidin-3-yl)-3-methyl-2-oxo-2,3-dihydro-1H-benzo[d]imidazol-5-yl)methyl)cyclohexyl)acetyl)-6-oxodecahydropyrrolo[1,2-a][1,5]diazocin-5-yl)carbamoyl)-1H-indole-5-carbonyl)phosphonate. To a stirred mixture of (2S)-2-[[(5S,8S,10aR)-5-amino-6-oxo-3-[2-[(1s, 4s)-4-[[1-(2,6-dioxopiperidin-3-yl)-3-methyl-2-oxo-1,3-benzodiazol-5-yl]methyl]cyclohexyl]acetyl]-octahydropyrrolo[1,2-a][1,5]diazocin-8-yl]formamido]-N-(diphenylmethyl)pentanediamide (500 mg, 0.55 mmol) and 5-[(diethoxyphosphoryl)carbonyl]-1H-indole-2-carboxylic acid (213 mg, 0.66 mmol) in DMA (8 mL) were added PyBOP (426 mg, 0.82 mmol) and TEA (276 mg, 2.73 mmol) at room temperature. After stirring for additional 1 h, the resulting mixture was purified by reverse phase flash chromatography with the following conditions: Column: WelFlash™ C18-I, 20~40 um, 330 g; Eluent A: Water (plus 10 mmol/LFA); Eluent B: ACN; Gradient: 35% - 55% B in 25 min; Flow rate: 80 mL/min; Detector: UV 220/254 nm; Desired fractions were collected at 53% B and concentrated under reduced pressure to afford the title compound (520 mg, 78%) as a white solid: $^1H$ NMR (400 MHz, DMSO-$d_6$) δ 12.34-12.18 (m, 1H), 11.10 (s, 1H), 8.90-8.69 (m, 2H), 8.50 (d, J=6.8 Hz, 1H), 8.33-8.12 (m, 1H), 7.96 (dd, J=8.9, 1.7 Hz, 1H), 7.66-7.54 (m, 1H), 7.50 (s, 1H), 7.39-7.19 (m, 13H), 7.04-6.91 (m, 2H), 6.88-6.75 (m, 2H), 6.11 (dd, J=8.5, 3.3 Hz, 1H), 5.37-5.31 (m, 1H), 5.01-4.87 (m, 1H), 4.51-4.32 (m, 3H), 4.26-4.13 (m, 5H), 4.06-3.94 (m, 1H), 3.82-3.74 (m, 2H), 3.35 (s, 3H), 3.28 (s, 2H), 2.98-2.81 (m, 1H), 2.76-2.54 (m, 5H), 2.22-1.56 (m, 10H), 1.48-1.42 (m, 7H), 1.35-1.28 (m, 8H); LC/MS (ESI, m/z): $[(M+H)]^+$=1223.40.

The intermediates in Table 76 were prepared according to the procedure to prepare Intermediate S.

TABLE 76

| Characterization data for intermediates prepared according to above. | | | | |
|---|---|---|---|---|
| Intermediate | Structure | Chemical Name | MS: [(M + 1)]$^+$ | $^1$H-NMR |
| S1 | 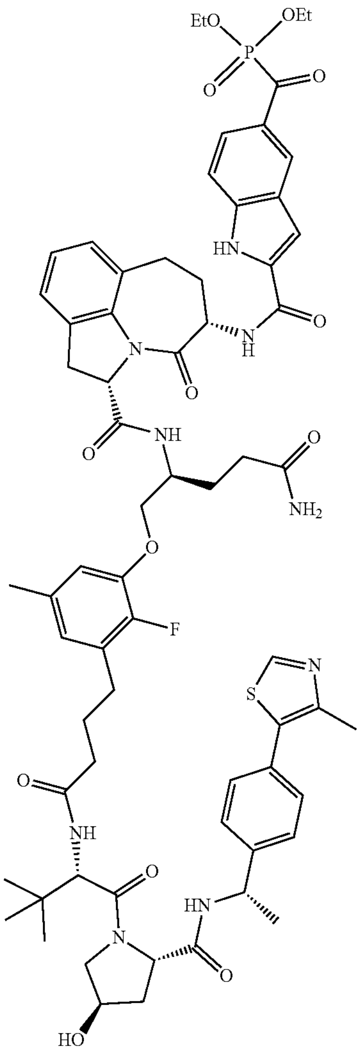 [SMILES: CCOP(=O)(OCC)C(=O)c1ccc2[nH]c(C(=O)N[C@H]3CCc4cccc5c4N(C3=O)[C@H](C(=O)N[C@@H](CCC(N)=O)COc3cc(C)cc(CCCC(=O)N[C@H](C(=O)N4C[C@H](O)C[C@H]4C(=O)N[C@@H](C)c4ccc(-c6scnc6C)cc4)C(C)(C)C)c3F)C5)cc2c1] | diethyl 2-[[(2S,11S)-2-[[(2S)-4-carbamoyl-1-[2-fluoro-3-(3-[[(2S)-1-[(2S,4R)-4-hydroxy-2-[[(1S)-1-[4-(4-methyl-1,3-thiazol-5-yl)phenyl]ethyl] carbamoyl]pyrrolidin-1-yl]-3,3-dimethyl-1-oxobutan-2-yl]carbamoyl] propyl)-5-methylphenoxy]butan-2-yl]carbamoyl]-12-oxo-1-azatricyclo[6.4.1.0^[4,13]]trideca-4(13),5,7-trien-11-yl]carbamoyl]-1H-indole-5-carbonylphosphonate | 1288.50 | (300 MHz, DMSO-$d_6$) δ 12.24 (s, 1H), 9.04-8.95 (m, 2H), 8.77-8.72 (m, 1H), 8.45-8.33 (m, 1H), 8.11 (d, J = 7.5 Hz, 1H), 7.94 (d, J = 9.1 Hz, 1H), 7.85 (d, J = 9.2 Hz, 1H), 7.58 (d, J = 8.8 Hz, 1H), 7.51 (s, 1H), 7.40 (q, J = 8.3 Hz, 4H), 7.26-7.21 (m, 1H), 7.12-7.04 (m, 2H), 7.01-6.94 (m, 1H), 6.79 (d, 1H), 6.59 (d, J = 5.9 Hz, 1H), 5.10-5.03 (m, 1H), 4.94-4.87 (m, 1H), 4.74-4.63 (m, 1H), 4.53 (d, J = 9.3 Hz, 1H), 4.41 (t, J = 8.1 Hz, 1H), 4.30-4.14 (m, 5H), 4.04-3.88 (m, 3H), 3.63-3.57 (m, 2H), 3.19-3.10 (m, 2H), 2.97-2.77 (m, 5H), 2.45 (s, 3H), 2.33-2.23 (m, 2H), 2.21 (s, 3H), 2.06-1.92 (m, 4H), 1.86-1.66 (m, 6H), 1.36 (s, 3H), 1.29 (t, J = 7.0 Hz, 6H), 0.94 (s, 9H) |

TABLE 76-continued

| Characterization data for intermediates prepared according to above. | | | | |
|---|---|---|---|---|
| Inter-mediate | Structure | Chemical Name | MS: [(M + 1)]+ | 1H-NMR |
| S2 | 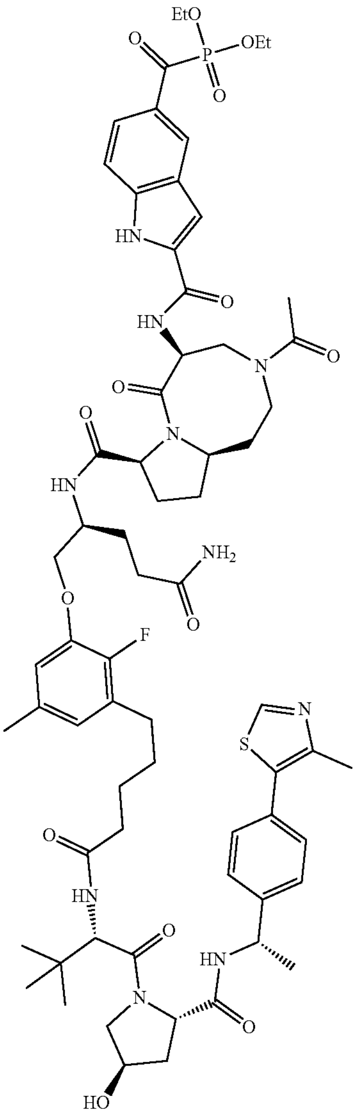 | diethyl 2-[[(5S,8S,10aR)-3-acetyl-8-[[(2S)-4-carbamoyl-1-[2-fluoro-3-(4-[[(2S)-1-[(2S,4R)-4-hydroxy-2-[[(1S)-1-[4-(4-methyl-1,3-thiazol-5-yl)phenyl]ethyl]carbamoyl]pyrrolidin-1-yl]-3,3-dimethyl-1-oxobutan-2-yl]carbamoyl]butyl)-5-methylphenoxyl]butan-2-yl]carbamoyl]-6-oxo-octahydropyrrolo[1,2-a][1,5]diazocin-5-yl]carbamoyl]-1H-indole-5-carbonylphosphonate | 1326.60 | (400 MHz, DMSO-$d_6$) δ 12.43-12.10 (m, 1H), 8.97 (s, 1H), 8.78-8.71 (m, 1H), 8.50 (d, J = 6.9 Hz, 1H), 8.35 (d, J = 7.8 Hz, 1H), 8.09-7.90 (m, 2H), 7.80 (d, J = 9.2 Hz, 1H), 7.59-7.47 (m, 2H), 7.40 (q, J = 8.3 Hz, 4H), 7.22 (d, J = 9.7 Hz, 1H), 6.86-6.75 (m, 2H), 6.68-6.57 (m, 1H), 5.08 (d, J = 3.5 Hz, 1H), 5.04-4.95 (m, 1H), 4.92 (q, J = 7.3 Hz, 1H), 4.55-4.31 (m, 4H), 4.30-4.11 (m, 6H), 4.09-3.93 (m, 2H), 3.92-3.66 (m, 4H), 3.65-3.53 (m, 2H), 2.45 (s, 3H), 2.33-2.25 (m, 1H), 2.22 (s, 3H), 2.21-2.05 (m, 7H), 2.04-1.92 (m, 3H), 1.91-1.61 (m, 7H), 1.58-1.45 (m, 4H), 1.37 (s, 3H), 1.33-1.24 (m, 7H), 0.92 (s, 9H) |

TABLE 76-continued

Characterization data for intermediates prepared according to above.

| Inter-mediate | Structure | Chemical Name | MS: [(M + 1)]$^+$ | $^1$H-NMR |
|---|---|---|---|---|
| S3 | 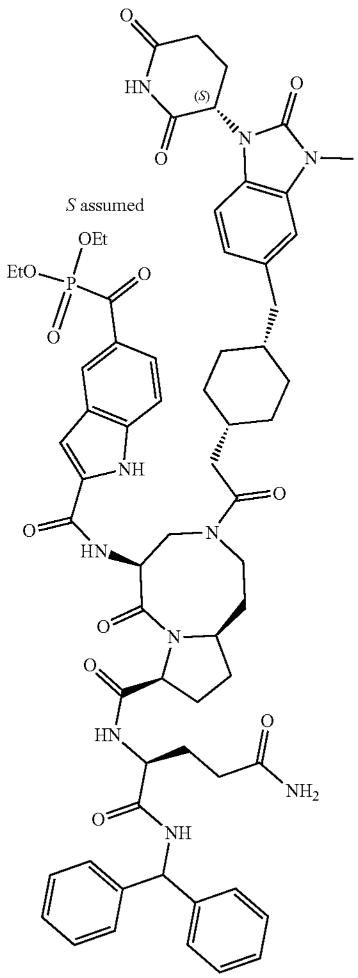 | diethyl 2-[(5S,8S,10aR)-8-[[(1S)-3-carbamoyl-1-(diphenylmethylcarbamoyl)propyl]carbamoyl]-6-oxo-3-[2-[(1s,4s)-4-[[1-(2,6-dioxopiperidin-3-yl)-3-methyl-2-oxo-1,3-benzodiazol-5-yl]methyl]cyclohexyl]acetyl]-octahydropyrrolo[1,2-a][1,5]diazocin-5-yl]carbamoyl]-1H-indole-5-carbonylphosphonate | 1223.85 | (300 MHz, DMSO-$d_6$) δ 12.35-12.18 (m, 1H), 11.09 (s, 1H), 8.90-8.69 (m, 2H), 8.51 (d, J = 6.8 Hz, 1H), 8.27-8.16 (m, 1H), 7.97 (dd, J = 8.9, 1.7 Hz, 1H), 7.63-7.56 (m, 1H), 7.52-7.50 (m, 1H), 7.42-7.14 (m, 13H), 7.07-6.91 (m, 2H), 6.91-6.66 (m, 2H), 6.12 (dd, J = 8.4, 2.2 Hz, 1H), 5.38-5.31 (m, 1H), 5.00-4.88 (m, 1H), 4.55-4.32 (m, 3H), 4.26-4.15 (m, 5H), 3.97-3.75 (m, 1H), 3.35 (s, 3H), 3.30 (s, 2H), 2.96-2.87 (m, 1H), 2.78-2.55 (m, 5H), 2.25-1.57 (m, 10H), 1.52-1.40 (m, 7H), 1.35-1.28 (m, 8H) |

TABLE 76-continued

Characterization data for intermediates prepared according to above.

| Inter-mediate | Structure | Chemical Name | MS: [(M + 1)]+ | ¹H-NMR |
|---|---|---|---|---|
| S4 | 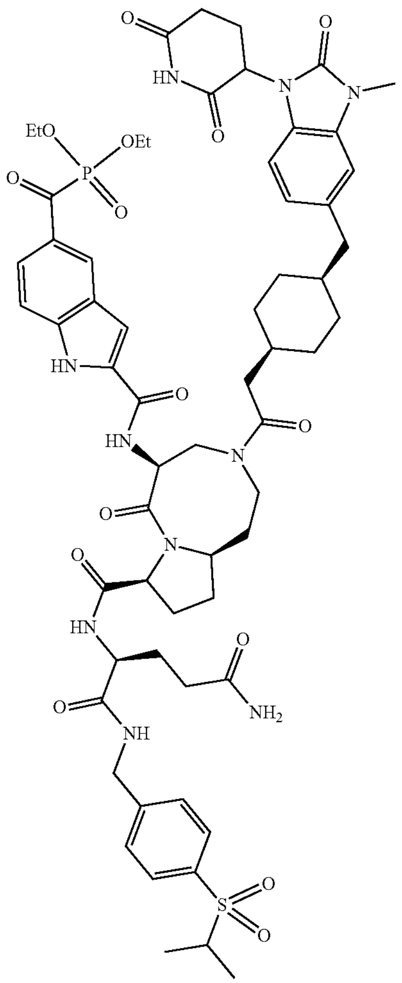 [SMILES: CCOP(=O)(OCC)C(=O)c1ccc2[nH]c(C(=O)N[C@H]3CN(C(=O)C[C@H]4CC[C@@H](Cc5ccc6c(c5)n(C)c(=O)n6C5CCC(=O)NC5=O)CC4)CC[C@H]4CC[C@@H](C(=O)N[C@@H](CCC(N)=O)C(=O)NCc5ccc(S(=O)(=O)C(C)C)cc5)N4C3=O)cc2c1] | diethyl 2-[[(5S,8S,10aR)-8-[[(1S)-3-carbamoyl-1-([[4-(propane-2-sulfonyl)phenyl]methyl]carbamoyl)propyl]carbamoyl]-6-oxo-3-[2-[(1s,4s)-4-[[1-(2,6 dioxopiperidin-3-yl)-3-methyl-2-oxo-1,3-benzodiazol-5-yl]methyl]cyclohexyl]acetyl]-octahydropyrrolo[1,2-a][1,5]diazocin-5-yl]carbamoyl]-1H-indole-5-carbonylphosphonate | 1253.60 | (400 MHz, DMSO-$d_6$) δ 12.34-12.17 (m, 1H), 11.09 (d, J = 2.5 Hz, 1H), 8.75 (dd, J = 5.1, 1.7 Hz, 1H), 8.58-8.52 (m, 2H), 8.30 (dd, J = 17.7, 7.4 Hz, 1H), 7.96 (dd, J = 8.8, 1.8 Hz, 1H), 7.79 (d, J = 8.2 Hz, 2H), 7.61 (d, J = 8.3 Hz, 1H), 7.53 (dd, J = 8.5, 2.0 Hz, 3H), 7.27 (d, J = 14.8 Hz, 1H), 7.04-6.93 (m, 2H), 6.89-6.77 (m, 2H), 5.37-5.31 (m, 1H), 4.99-4.87 (m, 1H), 4.49-4.37 (m, 3H), 4.32-4.14 (m, 6H), 4.02-3.72 (m, 2H), 3.42-3.38 (m, 2H), 3.33 (s, 2H), 3.29 (s, 2H), 2.90 (t, J = 14.8 Hz, 1H), 2.78-2.54 (m, 6H), 2.24-2.11 (m, 3H), 2.07-1.60 (m, 10H), 1.48-1.45 (m, 8H), 1.30 (t, J = 7.0, 6H), 1.14 (dd, J = 6.8, 2.1 Hz, 6H) |

TABLE 76-continued

Characterization data for intermediates prepared according to above.

| Inter-mediate | Structure | Chemical Name | MS: [(M + 1)]$^+$ | $^1$H-NMR |
|---|---|---|---|---|
| S5 | 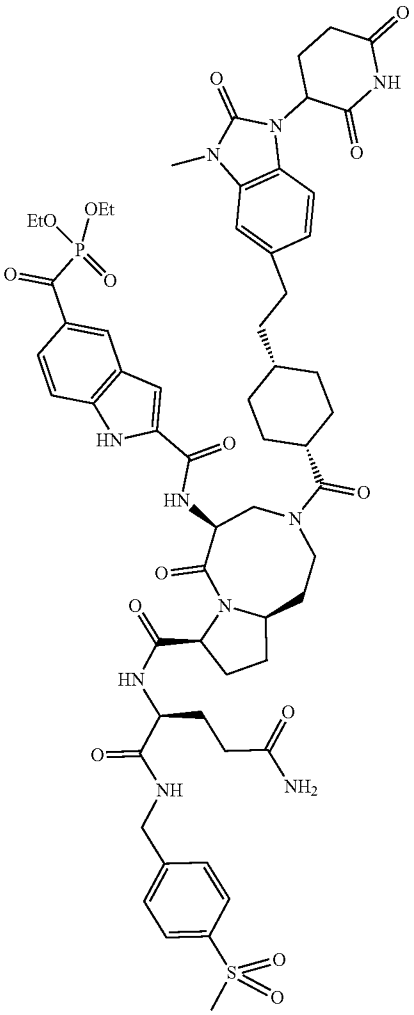 [SMILES: CCOP(=O)(OCC)C(=O)c1ccc2[nH]c(C(=O)N[C@H]3CN(C(=O)[C@H]4CC[C@@H](CCc5ccc6c(c5)n(C)c(=O)n6C5CCC(=O)NC5=O)CC4)CC[C@H]4CC[C@@H](C(=O)N[C@@H](CCC(N)=O)C(=O)NCc5ccc(S(C)(=O)=O)cc5)N4C3=O)cc2c1] | diethyl 2-[[(5S,8S,10aR)-8-[[(1S)-3-carbamoyl-1-[[(4-methanesulfonylphenyl)methyl]carbamoyl]propyl]carbamoyl]-6-oxo-3-[(1s,4s)-4-[2-[1-(2,6-dioxopiperidin-3-yl)-3-methyl-2-oxo-1,3-benzodiazol-5-yl]ethyl]cyclohexanecarbonyl]-octahydropyrrolo[1,2-a][1,5]diazocin-5-yl]carbamoyl]-1H-indole-5-carbonylphosphonate | 1225.50 | (300 MHz, DMSO-$d_6$) δ 12.31 (s, 1H), 11.08 (s, 1H), 8.87-8.71 (m, 1H), 8.57 (d, J = 5.9 Hz, 1H), 8.55-8.41 (m, 1H), 8.32 (q, J = 11.5, 10.2 Hz, 1H), 7.95 (dd, J = 8.8, 1.7 Hz, 1H), 7.86 (d, J = 8.1 Hz, 2H), 7.65-7.55 (m, 1H), 7.54-7.47 (m, 3H), 7.32-7.17 (m, 1H), 7.08-6.91 (m, 2H), 6.91-6.76 (m, 2H), 5.34 (dd,J = 12.6, 5.6 Hz, 1H), 5.04-4.91 (m, 1H), 4.89-4.75 (m, 1H), 4.43 (dd, J = 20.0, 7.0 Hz, 3H), 4.31-4.10 (m, 7H), 3.94 (d, J = 13.5 Hz, 1H), 3.87-3.71 (m, 1H), 3.46 (d, J = 2.2 Hz, 1H), 3.33 (s, 3H), 3.18 (s, 3H), 3.06-2.81 (m, 2H), 2.78-2.54 (m, 4H), 2.28-2.10 (m, 4H), 2.01-1.78 (m, 6H), 1.72-1.45 (m, 11H), 1.29 (t, J = 7.0 Hz, 6H) |

TABLE 76-continued

Characterization data for intermediates prepared according to above.

| Intermediate | Structure | Chemical Name | MS: [(M + 1)]$^+$ | $^1$H-NMR |
|---|---|---|---|---|
| S6 | 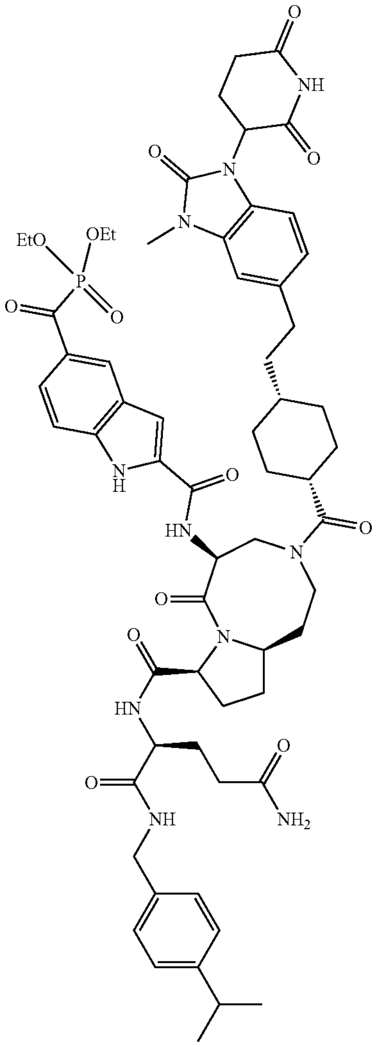 [SMILES: CCOP(=O)(OCC)C(=O)c1ccc2[nH]c(C(=O)N[C@H]3CN(C(=O)[C@H]4CC[C@@H](CCc5ccc6c(c5)n(C)c(=O)n6C5CCC(=O)NC5=O)CC4)CC[C@H]4CC[C@@H](C(=O)N[C@@H](CCC(N)=O)C(=O)NCc5ccc(C(C)C)cc5)N4C3=O)cc2c1] | diethyl (2-(((5S,8S,10aR)-8-(((5)-5-amino-1-((4-isopropylbenzyl)amino)-1,5-dioxopentan-2-yl)carbamoyl)-3-((1r,4R)-4-(2-(1-(2,6-dioxopiperidin-3-yl)-3-methyl-2-oxo-2,3-dihydro-1H-benzo[d]imidazol-5-yl)ethyl)cyclohexane-1-carbonyl)-6-oxodecahydropyrrolo[1,2-a][1,5]diazocin-5-yl)carbamoyl)-1H-indole-5-carbonyl)phosphonate | 1189.50 | (300 MHz, DMSO-$d_6$) δ 12.32-12.12 (m, 1H), 11.08 (s, 1H), 8.77-8.70 (m, 1H), 8.47-8.39 (m, 1H), 8.37-8.30 (m, 1H), 8.28-8.18 (m, 1H), 7.99-7.89 (m, 1H), 7.64-7.54 (m, 1H), 7.47 (s, 1H), 7.29-7.21 (m, 1H), 7.15 (s, 4H), 7.08-6.81 (m, 3H), 6.78 (s, 1H), 5.39-5.27 (m, 1H), 5.01-4.90 (m, 1H), 4.88-4.69 (m, 1H), 4.49-4.37 (m, 1H), 4.28-4.10 (m, 9H), 3.98-3.87 (m, 1H), 3.80-3.69 (m, 1H), 3.49-3.42 (m, 2H), 3.31 (s, 3H), 3.03-2.95 (m, 1H), 2.93-2.73 (m, 2H), 2.66-2.56 (m, 3H), 2.24-2.08 (m, 4H), 2.03-1.72 (m, 6H), 1.71-1.46 (m, 11H), 1.29 (t, J = 7.0 Hz, 6H), 1.19-1.13 (m, 6H). |

Step 2: (2-(((5S,8S,10aR)-8-(((S)-5-amino-1-(benzhydrylamino)-1,5-dioxopentan-2-yl)carbamoyl)-3-(2-((1S,4R)-4-((1-((R)-2,6-dioxopiperidin-3-yl)-3-methyl-2-oxo-2,3-dihydro-1H-benzo[d]imidazol-5-yl)methyl)cyclohexyl)acetyl)-6-oxodecahydropyrrolo[1,2-a][1,5]diazocin-5-yl)carbamoyl)-1H-indole-5-carbonyl)phosphonic acid. To a stirred solution of diethyl 2-[[(5S,8S,10aR)-8-[[(1S)-3-carbamoyl-1-(diphenylmethylcarbamoyl)propyl]carbamoyl]-6-oxo-3-[2-[(1s, 4s)-4-([1-[(3R)-2,6-dioxopiperidin-3-yl]-3-methyl-2-oxo-1,3-benzodiazol-5-yl]methyl)cyclohexyl]acetyl]-octahydropyrrolo[1,2-a][1,5]diazocin-5-yl]carbamoyl]-1H-indole-5-carbonylphosphonate (500 mg, 0.41 mmol) in DCM (10 mL) was added bromotrimethylsilane (1.0g, 6.54 mmol) dropwise at room temperature. The resulting mixture was stirred for 16 h at 40° C. under air atmosphere. The mixture was cooled down to room temperature and concentrated under reduced pressure. The residue was purified by reverse phase flash chromatography with the following conditions: Column: WelFlash™ C18-I, 20~40 um, 120 g; Eluent A: Water (plus 10 mmol/LFA); Eluent B: ACN; Gradient: 15% - 35% B in 25 min; Flow rate: 60 mL/min; Detector: UV 220/254 nm; desired fractions were collected at 36% B, concentrated under reduced pressure and lyophilized to afford the title compound (104 mg, 22%) as a white solid: $^1$H NMR (400 MHz, DMSO-$d_6$) δ 12.3-11.95 (m, 1H), 11.11-11.07 (m, 1H), 8.85-8.75 (m, 2H), 8.51-8.45 (m, 1H), 8.29-8.17 (m, 1H), 7.97 (d, J=8.8 Hz, 1H), 7.54-7.47 (m, 1H), 7.47-7.38 (m, 1H), 7.34-7.26 (m, 12H), 7.06-6.94 (m, 2H), 6.88-6.71 (m, 2H), 6.13-6.08 (m, 1H), 5.39-5.29 (m, 1H), 4.99-4.88 (m, 1H), 4.46 (t, J=8.5 Hz, 1H), 4.42-4.30 (m, 1H), 4.22-4.13 (s, 1H), 3.95 (d, J=13.7 Hz, 1H), 3.85-3.73 (m, 1H), 3.64-3.51 (m, 1H), 3.34-3.24 (m, 4H), 2.93-2.86 (m, 2H), 2.76-2.57 (m, 5H), 2.19-1.66 (m, 13H), 1.46-1.35 (m, 9H); LC/MS (ESI, m/z): $[(M+H)]^+$=1168.40.

The following compounds in Table 77 were synthesized according to the procedure to prepare I-234.

TABLE 77

Characterization Data for Exemplary STAT3 Degraders

| EXAMPLE | I-# | Chemical Name | MS: $[(M + 1)]^+$ | $^1H$ NMR |
|---|---|---|---|---|
| 280 | I-235 | diammonium 2-[[(2S,11S)-2-[[(2S)-4-carbamoyl-1-[2-fluoro-3-(3-[[(2S)-1-[(2S,4R)-4-hydroxy-2-[[(1S)-1-[4-(4-methyl-1,3-thiazol-5-yl)phenyl]ethyl] carbamoyl]pyrrolidin-1-yl]-3,3-dimethyl-1-oxobutan-2-yl] carbamoyl]propyl)-5-methyl-phenoxy]butan-2-yl]carbamoyl]-12-oxo-1-azatricyclo [6.4.1.0^[4,13]]trideca-4(13),5,7-trien-11-yl]carbamoyl]-1H-indole-5-carbonylphosphonate | 1232.45 | (400 MHz, DMSO-$d_6$) δ 11.86 (s, 1H), 8.98-8.92 (m, 2H), 8.12 (d, J = 7.9 Hz, 1H), 8.06 ( d, J = 7.8 Hz, 2H), 7.98-7.92 (m, 1H), 7.46-7.23 (m, 8H), 7.13-7.04 (m, 2H), 7.02-6.94 (m, 1H), 6.81-6.73 (m, 2H), 6.49 (d, J = 6.0 Hz, 1H), 5.08 (dd, J = 10.7, 3.0 Hz, 1H), 4.88 (p, J = 7.2 Hz, 1H), 4.72-4.64 (m, 1H), 4.41-4.29 (m, 3H), 3.98-3.78 (m, 4H), 3.56-3.42 (m, 4H), 3.22-3.08 (m, 4H), 2.91-2.85 (m, 1H), 2.47 (s, 3H), 2.30-2.21 (m, 4H), 2.18-1.99 (m, 7H), 1.97-1.86 (m, 1H), 1.87-1.79 (m, 1H), 1.73-1.56 (m, 3H), 1.38 (d, J = 7.0 Hz, 3H), 0.99 (s, 9H) |
| 281 | I-236 | diammonium 2-[[(5S,8S,10aR)-3-acetyl-8-[[(2S)-4-carbamoyl-1-[2-fluoro-3-(4-[[(2S)-1-[(2S,4R)-4-hydroxy-2-[[(1S)-1-[4-(4-methyl-1,3-thiazol-5-yl) phenyl]ethyl]carbamoyl] pyrrolidin-1-yl]-3,3-dimethyl-1-oxobutan-2-yl]carbamoyl]butyl)-5-methylphenoxy]butan-2-yl] carbamoyl]-6-oxo-octahydropyrrolo [1,2-a][1,5]diazocin-5-yl]carbamoyl]-1H-indole-5-carbonylphosphonate | 1269.60 | (400 MHz, DMSO-$d_6$) δ 12.10-11.79 (m, 1H), 8.99 (s, 1H), 8.96-8.90 (m, 1H), 8.68-8.55 (m, 1H), 8.45 (d, J = 7.0 Hz, 1H), 8.19-8.00 (m, 2H), 7.98-7.92 (m, 1H), 7.47-7.38 (m, 5H), 7.33 (s, 1H), 7.30-7.23 (m, 1H), 6.87-6.76 (m, 2H), 6.63-6.56 (m, 1H), 5.18 (s, 1H), 5.06-4.90 (m, 2H), 4.47-4.32 (m, 1H), 4.30-4.21 (m, 1H), 4.20-4.12 (m, 1H), 4.09-3.93 (m, 3H), 3.92-3.79 (m, 3H), 3.76-3.66 (m, 2H), 3.56-3.42 (m, 2H), 3.26-3.08 (m, 4H), 3.00-2.91 (m, 1H), 2.45 (s, 3H), 2.29-2.06 (m, 12H), 2.04-1.80 (m, 5H), 1.79-1.59 (m, 3H), 1.54-1.44 (m, 4H), 1.41 (d, J = 7.0, 3H), 0.94 (s, 9H) |
| 282 | I-242 | (2-(((5S,8S,10aR)-8-(((S)-5-amino-1-(benzhydrylamino)-1,5-dioxopentan-2-yl)carbamoyl)-3-(2-((1R,4R)-4-((1-((S)-2,6-dioxopiperidin-3-yl)-3-methyl-2-oxo-2,3-dihydro-1H-benzo[d]imidazol-5-yl)methyl) cyclohexyl)acetyl)-6-oxodeca-hydropyrrolo[1,2-a][1,5]diazocin-5-yl)carbamoyl)-1H-indole-5-carbonyl)phosphonic acid | 1168.40 | (400 MHz, DMSO-$d_6$) δ 12.3-11.95 (m, 1H), 11.11-11.07 (m, 1H), 8.85-8.75 (m, 2H), 8.51-8.45 (m, 1H), 8.29-8.17 (m, 1H), 7.97 ( d, J = 8.8 Hz, 1H), 7.54-7.47 (m, 1H), 7.47-7.38 (m, 1H), 7.34-7.26 (m, 12H), 7.06-6.94 (m, 2H), 6.88-6.71 (m, 2H), 6.13-6.08 (m, 1H), 5.39-5.29 (m, 1H), 4.99-4.88 (m, 1H), 4.46 (t, J = 8.5 Hz, 1H), 4.42-4.30 (m, 1H), 4.22-4.13 (s, 1H), 3.95 (d, J = 13.7 Hz, 1H), 3.85-3.73 (m, 1H), 3.64-3.51 (m, 1H), 3.34-3.24 (m, 4H), 2.93-2.86 (m, 2H), 2.76-2.57 (m, 5H), 2.19-1.66 (m, 13H), 1.46-1.35 (m, 9H) |
| 283 | I-282 | 2-[[(5S,8S,10aR)-8-[[(1S)-3-carbamoyl-1-([[4-(propane-2-sulfonyl)phenyl]methyl]carbamoyl) propyl]carbamoyl]-6-oxo-3-[2-[(1s,4s)-4-[[1-(2,6-dioxopiperidin-3-yl)-3-methyl-2-oxo-1,3-benzodiazol-5-yl] methyl]cyclohexyl]acetyl]-octa-hydropyrrolo[1,2-a][1,5]diazocin-5-yl]carbamoyl]-1H-indole-5-carbonylphosphonic acid | $[(M - H)]^-$ = 1195.60 | (300 MHz, DMSO-$d_6$) δ12.26-11.97 (m, 1H), 11.09 (s, 1H), 8.92-8.77 (m, 1H), 8.61-8.46 (m, 2H), 8.37-8.25 (m, 1H), 8.01-7.94 (m, 1H), 7.83-7.75 (m, 2H), 7.58-7.50 (m, 3H), 7.48-7.43 (m, 1H), 7.33-7.24 (m, 1H), 7.04-6.95 (m, 2H), 6.89-6.72 (m, 2H), 5.41-5.27 (m, 1H),5.08-4.84 (m, 1H), 4.53-4.37 (m, 3H), 4.33-4.14 (m, 2H), 4.03-3.75 (m, 2H), 3.42-3.33 (m, 3H), 3.30 (s, 3H), 3.00-2.84 (m, 1H), 2.77-2.58 (m, 5H), 2.32-2.11 (m, 4H), 2.09-1.96 (m, 4H), 1.94-1.57 (m, 7H), 1.56-1.22 (m, 9H), 1.15 (d, J = 6.8 Hz, 6H) |
| 284 | I-294 | (2-(((5S,8S,10aR)-8-(((S)-5-amino-1-((4-(methylsulfonyl) benzyl)amino)-1,5-dioxopentan-2-yl)carbamoyl)-3-((1r,4R)-4-(2-(l-(2,6-dioxopiperidin-3-yl)-3-methyl-2-oxo-2,3-dihydro-1H-benzo[d]imidazol-5-yl)ethyl)cyclohexane-1-carbonyl)-6-oxodecahydropyrrolo[1,2-a][1,5]diazocin-5-yl)carbamoyl)-1H-indole-5-carbonyl) phosphonic acid | $[(M - H)]^-$ = 1167.10 | (400 MHz, DMSO-$d_6$) δ 12.23-12.02 (m, 1H), 11.09 (s, 1H), 8.81 (s, 1H), 8.60-8.52 (m, 1H), 8.44 (d, J = 6.2 Hz, 1H), 8.30 (dd, J = 14.7, 7.5 Hz, 1H), 7.99-7.91 (m, 1H), 7.86 (d, J = 8.2 Hz, 2H), 7.55-7.45 (m, 4H), 7.29-7.20 (m, 1H), 7.08-6.96 (m, 2H), 6.96-6.87 (m, 1H), 6.87-6.80 (m, 1H), 5.35 (dd, J = 12.8, 5.4 Hz, 1H), 5.03-4.98 (m, 1H), 4.79-4.90 (m, 1H), 4.55-4.37 (m, 3H), 4.24-4.15 (m, 3H), 3.95 (d, J = 13.6 Hz, 1H), 3.76 (s, 1H), 3.47-3.30 (m, 4H), 3.19 (s, 3H), 3.09-3.01 (m, 1H), 2.93-2.84 (m, 1H), 2.79-2.55 (m, 4H), 2.26-2.04 (m, 4H), 2.04-1.85 (m, 4H), 1.84-1.73 (m, 5H), 1.70-1.56 (m, 10H) |
| 285 | I-295 | (2-(((5S,8S,10aR)-8-(((S)-5-amino-1-((4-isopropylbenzyl) amino)-1,5-dioxopentan-2-yl) carbamoyl)-3-((1r,4R)-4-(2-(1-(2,6-dioxopiperidin-3-yl)-3-methyl-2-oxo-2,3-dihydro-1H-benzo[d]imidazol-5-yl)ethyl) cyclohexane-1-carbonyl)-6-oxodecahydropyrrolo[1,2-a][1,5] | 1133.60 | (400 MHz, DMSO-$d_6$) δ 12.17-11.97 (m, 1H), 11.09 (s, 1H), 8.82 (s, 1H), 8.45-8.39 (m, 1H), 8.38-8.29 (m, 1H), 8.28-8.18 (m, 1H), 8.01-7.94 (m, 1H), 7.53 (d, J = 8.7 Hz, 1H), 7.48-7.41 (m, 1H), 7.29-7.20 (m, 1H), 7.17 (s, 4H), 7.08-6.98 (m, 2H), 6.95-6.85 (m, 1H), 6.79 (s, 1H), 5.39-5.30 (m, 1H), 5.05-4.93 (m, 1H), 4.91-4.75 (m, 1H), 4.49-4.40 (m, 1H), 4.28-4.16 (m, 4H), 3.98-3.91 (m, 1H), 3.84-3.71(m, 2H), 3.48-3.46 (m, |

TABLE 77-continued

| Characterization Data for Exemplary STAT3 Degraders | | | | |
|---|---|---|---|---|
| EXAMPLE | I-# | Chemical Name | MS: $[(M + 1)]^+$ | $^1H$ NMR |
| | | diazocin-5-yl)carbamoyl)-1H-indole-5-carbonyl)phosphonic acid | | 2H), 3.34 (s, 3H), 3.07-2.98 (m, 1H), 2.93-2.79 (m, 2H), 2.66-2.58 (m, 3H), 2.23-2.04 (m, 5H), 2.04-1.85 (m, 4H), 1.83-1.73 (m, 3H), 1.72-1.46 (m, 11H), 1.22-1.13 (m, 6H). |

Example 286. 4-carbamoyl-2-(3-methyl-2-oxo-5-[[(1s, 4s)-4-12-1(5S,8S,10aR)-8-[[(1S)-3-carbamoyl-1-(diphenylmethylcarbamoyl)propyl]carbamoyl]-6-oxo-5-[5-(phosphonocarbonyl)-1H-indole-2-amido]-octahydropyrrolo[1[1,2-a][1,5]diazocin-3-yl]-2-oxoethyl]cyclohexyl]methyl]-1,3-benzodiazol-1-yl)butanoic acid (1-255)

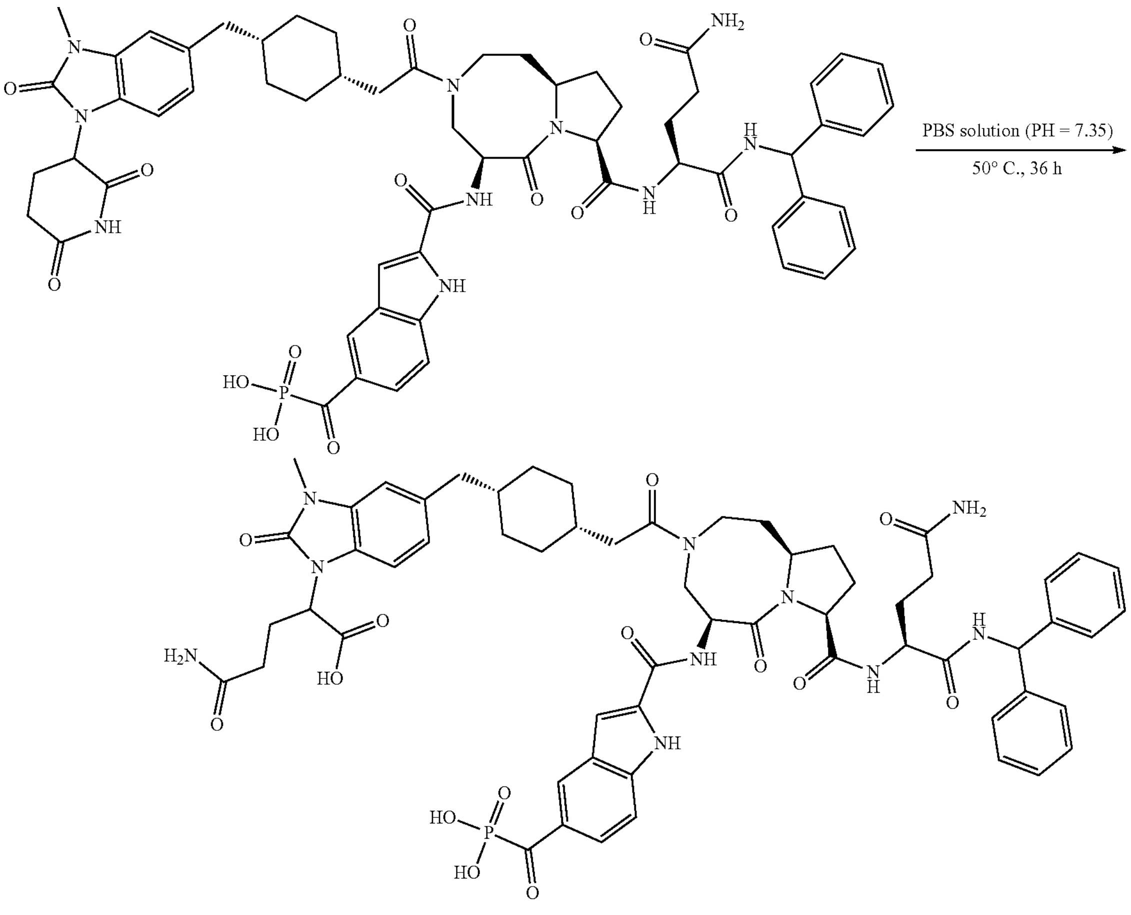

I-255

4-Carbamoyl-2-(3-methyl-2-oxo-5-[[(1s, 4s)-4-[2-[(5S, 8S10aR)-8-[[(1S)-3-carbanoyl1 (diphenylcarbamoyl)propyl]carbamoyl]-6-oxo-5-[5-(phosphonocarbonyl)-1H-indole-2-amido]-octahydropyrrolo [1,2-a][1,5]diazocin-3-yl]-2-oxoethyl]cyclohexyl]methyl-1,3-benzodiazol-11-yl) butanoic acid. A mixture of 2-[[(5S,8S,10aR)-8-[[(1S)-3-carbamoyl-1-(diphenylmethylcarbamoyl)propyl] carbamoyl]-6-oxo-3-[2-[(1s, 4s)-4-[[1-(2,6-dioxopiperidin-3-yl)-3-methyl-2-oxo-1,3-benzodiazol-5-yl]methyl]cyclohexyl]acetyl]-octahydropyrrolo [1,2-a][1,5]diazocin-5-yl] carbamoyl]-1H-indole-5-carbonylphosphonic acid (400 mg) in PBS solution (PH=7.35) was stirred for 7 days at 50° C. under air atmosphere. The resulting solution was purified by reverse phase flash chromatography with the following conditions: Column: WelFlash™ C18-I, 20~40 um, 120 g; Eluent A: Water (plus 10 mmol/LNH4HCO3); Eluent B:

ACN; Gradient: 15% - 35% B in 25 min; Flow rate: 60 mL/min; Detector: 220/254 nm; desired fractions were collected at 30% B, concentrated under reduced pressure and lyophilized to afford title compound (200 mg) as a white solid: $^1H$ NMR (400 MHz, DMSO-$d_6$) δ 11.89 (s, 1H), 8.88 (s, 1H), 8.82-8.78 (m, 1H), 8.64-8.48 (m, 1H), 8.32-8.23 (m, 1H), 7.98 (d, J=8.8 Hz, 1H), 7.56-7.40 (m, 2H), 7.40-7.17 (m, 15H), 7.01-6.62 (m, 5H), 6.11 (dd, J=8.5, 2.5 Hz, 1H), 5.06-4.61 (m, 3H), 4.47 (t, J=8.6 Hz, 1H), 4.38 (q, J=7.3 Hz, 1H), 4.29-4.17 (m, 1H), 4.05-3.97 (m, 1H), 3.81-3.65 (m, 1H), 3.40-3.21 (m, 5H), 2.63-2.56 (m, 3H), 2.44-2.31 (m, 1H), 2.27-1.88 (m, 10H), 1.88-1.55 (m, 4H), 1.51-1.33 (m, 9H); LC/MS (ESI, m/z): $[(M - H)]^-$=1183.65.

Example 287. Quantitation of STAT3 Degradation in A549 Cells by Western Blot Analysis Degradation of total cellular STAT3 protein in A549 was quantitatively measured using SDS-PAGE and Western blot analysis. A549 cells (5×105 cells/well, 2 mL) were seeded into 6-well plates and were incubated in the incubator under 5% $CO_2$ overnight to reach ~80% confluency. The next day, the culture medium was changed with 1 ml fresh media. Then, 1 mL of media containing 2X compound solution was added into the well to make the final concentration of 30 μM, 10 μM, 3 μM, 1 μM, 0.3 μM and 0 μM (DMSO). The media was thoroughly mixed and incubated for 24 hours at 37° C. under 5% $CO_2$. Then, the culture media was removed from the assay plates and the cells were washed with ice-cold PBS twice. To prepare cell lysates, 200 ul pre-chilled RIPA lysis buffer (Boston BioProducts BP-115D) with protease/phosphatase inhibitor (Roche 05892791001/Roche 04906837001) was added directly into the well to lyse the cells for 20 minutes on ice. The cell lysates were then transferred to centrifuge tubes. Insoluble part of lysates was removed by centrifuging the lysates at 13000 rpm for 20 minutes. The supernatant was then collected and mixed with 5X loading buffer (Beyotime Bio P0015) to make the final samples for SDS-PAGE analysis. The samples were heated at 100° C. for 10 minutes and cool to room temperature before centrifuging at 13000 rpm for 20 minutes. To analyze the samples by SDS-PAGE, 10 ul samples were loaded onto SDS-PAGE gel (Novex, WG1403BOX) and the SDS-PAGE gel was run for 20 minutes at 80 V, then at 120 V for 1.5 hours. The SDS-PAGE gel was then transferred to nitrocellulose membrane using the wet-transfer method at 250 mA for 1.5 hours. The membrane was then blocked with LI-COR blocking buffer (LI-COR, 927-50000) for 1 hour and was probed with primary antibody (mouse anti-STAT3 (124H6) (CST #9139S) 1:2000 or mouse anti-beta-Actin (8H10D1O) (CST #3700) 1:10000) at 4° C. overnight. The membrane was then washed three times with TBST buffer and probed with secondary antibody (anti-mouse IgG (LI-COR, 926-68070), 1:5000) for 1 hour at room temperature. The membrane was then scanned on a LI-COR Odyssey instrument and was quantified using Image Studio Version 5.2. Concentration at 50% degradation ($DC_{50}$) was calculated by fitting dose dependent degradation data using a sigmoidal equation using GraphPad Prism Version 8.0.

STAT3 protein degradation in A549 cells for compounds of the invention are presented in Table 78. The results for STAT3 $DC_{50}$ include: compounds were tested up to 30 μM and >50% degradation was seen at 30 μM or below (<30 μM); compounds were tested up to 30 μM and <50% degradation was seen at all concentrations (>30 μM); compounds were tested up to 10 μM and <50% degradation was seen at all concentrations (>10 μM).

TABLE 78

Western Blot Degradation Results.

| I-# | A549 $DC_{50}$ (μM) |
|---|---|
| I-1 | <30 |
| I-2 | >30 |
| I-3 | >30 |
| I-4 | >30 |
| I-5 | >30 |
| I-6 | >30 |
| I-7 | <30 |
| I-8 | <30 |
| I-9 | >30 |
| I-10 | >30 |
| I-11 | >30 |
| I-12 | >30 |
| I-13 | <30 |
| I-15 | >30 |
| I-16 | >30 |
| I-17 | >30 |
| I-21 | >30 |
| I-22 | >30 |
| I-23 | >30 |
| I-26 | >10 |
| I-27 | >10 |
| I-28 | <30 |
| I-29 | >10 |
| I-30 | >10 |
| I-31 | >30 |
| I-32 | >10 |
| I-33 | >10 |
| I-34 | <30 |
| I-35 | <30 |
| I-36 | >10 |
| I-37 | >10 |
| I-38 | >10 |
| I-39 | >30 |
| I-43 | >30 |
| I-44 | >30 |
| I-54 | >30 |
| I-55 | >30 |
| I-58 | >30 |
| I-59 | >30 |
| I-60 | >30 |
| I-61 | >30 |
| I-68 | >30 |
| I-69 | >30 |
| I-71 | <30 |
| I-80 | >30 |
| I-82 | >30 |
| I-83 | <30 |
| I-84 | >30 |
| I-85 | <30 |
| I-86 | <30 |
| I-87 | <30 |
| I-88 | >30 |
| I-89 | <30 |
| I-90 | <30 |
| I-91 | <30 |
| I-92 | >30 |
| I-93 | <30 |
| I-94 | <30 |
| I-95 | <30 |
| I-96 | >30 |
| I-97 | <30 |
| I-99 | <30 |
| I-100 | <30 |
| I-101 | <30 |
| I-102 | <30 |
| I-103 | <30 |
| I-104 | <30 |
| I-105 | <30 |
| I-106 | >30 |
| I-107 | <30 |
| I-109 | >30 |
| I-110 | >30 |
| I-111 | <30 |
| I-112 | <30 |
| I-113 | >30 |
| I-114 | >30 |

TABLE 78-continued

| Western Blot Degradation Results. | |
|---|---|
| I-# | A549 $DC_{50}$ (μM) |
| I-115 | <30 |
| I-117 | <30 |
| I-118 | >30 |

Example 288. HiBiT Assay Protocol

Compound preparation and Cell seeding: The transfected A549 cells were harvested from dish into cell culture medium and cell numbers counted. Cells were diluted with culture medium to the desired density and 30 μL of cell suspension (about 2000 cells/well) were added into each well of a 384-well cell culture plate as designated and transferred into 37° C. 5% $CO_2$ incubator for 24 h. Compounds were dissolved to 10 mM stock solution and 12 μL of the stock solution was transferred to a 384 LDV-plate. 3 fold, 10-point dilution was performed by transferring 4 μL compound into 8 μL DMSO using a TECAN (EVO200) liquid handler. 30 μL of diluted compound from compound source plate was transferred into the cell plate as designated by using Echo550 and transferred into 37° C. 5% $CO_2$ incubator for 24 h.

Detection: Plates were removed from incubators and equilibrated at room temperature for 15 minutes. Nano-Glo Hibit Lytic Detection reagent (Promega Cat # N3040) was thawed and equilibrated to room temperature before the experiment. 30 μL of Nano-Glo Hibit Lytic Detection reagent was added into each well to be detected. The plates were held at room temperature for 10 min followed by reading on EnSpire.

Data analysis: The remaining activity was calculated following the formula: Remaining Activity(%)=100% x (Lumsample-LumNC)/(LumPC-LumNC). Calculate the $IC_{50}$ by fitting the curve using Xlfit (v5.3.1.3), equation 201: fit=(A+((B-A)/(1+((x/C)^D))); A: Botton; B: Top; C: $IC_{50}$; and D: Slope.

STAT3 HiBiT degradation results for compounds of the invention are presented in Table 79. The letter codes for STAT3 $DC_{50}$ include: A (<0.01 μM), B (0.01-0.1 μM), C (0.1-1.0 μM), and D (>1.0 μM).

TABLE 79

| STAT3 HiBiT Degradation Results | |
|---|---|
| I-# | STAT3 HiBiT A549 degradation 24 h: Average external-Abs DC50 (μM) |
| I-119 | D |
| I-120 | D |
| I-121 | D |
| I-122 | D |
| I-123 | D |
| I-124 | D |
| I-125 | C |
| I-126 | D |
| I-127 | C |
| I-128 | C |
| I-129 | C |
| I-130 | D |
| I-131 | D |
| I-132 | C |
| I-133 | C |
| I-134 | D |

TABLE 79-continued

| STAT3 HiBiT Degradation Results | |
|---|---|
| I-# | STAT3 HiBiT A549 degradation 24 h: Average external-Abs DC50 (μM) |
| I-135 | C |
| I-136 | D |
| I-137 | B |
| I-138 | D |
| I-139 | D |
| I-140 | D |
| I-141 | B |
| I-142 | D |
| I-143 | D |
| I-144 | D |
| I-145 | D |
| I-146 | C |
| I-147 | D |
| I-148 | D |
| I-149 | D |
| I-150 | D |
| I-151 | C |
| I-152 | D |
| I-153 | D |
| I-154 | D |
| I-155 | D |
| I-156 | C |
| I-157 | C |
| I-158 | D |
| I-159 | C |
| I-160 | D |
| I-161 | D |
| I-162 | D |
| I-163 | D |
| I-164 | B |
| I-165 | C |
| I-166 | B |
| I-167 | C |
| I-168 | D |
| I-169 | C |
| I-170 | D |
| I-171 | C |
| I-172 | D |
| I-173 | D |
| I-174 | B |
| I-175 | C |
| I-176 | D |
| I-177 | C |
| I-178 | D |
| I-179 | C |
| I-180 | D |
| I-181 | D |
| I-182 | C |
| I-183 | C |
| I-184 | C |
| I-194 | B |
| I-195 | B |
| I-196 | B |
| I-197 | C |
| I-198 | C |
| I-199 | B |
| I-200 | D |
| I-202 | B |
| I-203 | B |
| I-204 | B |
| I-205 | B |
| I-206 | B |
| I-207 | C |
| I-208 | C |
| I-209 | B |
| I-210 | D |
| I-211 | B |
| I-212 | B |
| I-213 | A |
| I-214 | D |
| I-215 | B |
| I-216 | B |
| I-217 | A |

TABLE 79-continued

STAT3 HiBiT Degradation Results

| I-# | STAT3 HiBiT A549 degradation 24 h: Average external-Abs DC50 (μM) |
|---|---|
| I-218 | A |
| I-219 | C |
| I-220 | C |
| I-221 | B |
| I-222 | D |
| I-223 | C |
| I-224 | D |
| I-225 | C |
| I-226 | B |
| I-227 | C |
| I-228 | C |
| I-229 | B |
| I-230 | D |
| I-231 | B |
| I-232 | B |
| I-233 | A |
| I-234 | B |
| I-235 | D |
| I-236 | C |
| I-237 | B |
| I-238 | C |
| I-239 | A |
| I-240 | B |
| I-241 | A |
| I-243 | A |
| I-244 | A |
| I-245 | C |
| I-246 | B |
| I-247 | B |
| I-248 | B |
| I-249 | B |
| I-250 | B |
| I-251 | A |
| I-252 | A |
| I-253 | A |
| I-254 | C |
| I-255 | D |
| I-256 | D |
| I-257 | B |
| I-258 | A |
| I-259 | C |
| I-260 | D |
| I-261 | A |
| I-262 | A |
| I-263 | A |
| I-264 | B |
| I-265 | B |
| I-266 | A |
| I-267 | A |
| I-268 | C |
| I-269 | D |
| I-270 | C |
| I-271 | C |
| I-272 | A |
| I-273 | C |
| I-274 | C |
| I-275 | A |
| I-276 | A |
| I-277 | B |
| I-278 | C |
| I-279 | A |
| I-280 | B |
| I-281 | A |
| I-283 | B |
| I-284 | B |
| I-285 | B |
| I-286 | B |
| I-287 | D |
| I-288 | B |
| I-289 | A |
| I-290 | A |
| I-292 | A |
| I-293 | B |
| I-294 | A |
| I-295 | A |

Example 289. Fluorescence Polarization Assays

FIG. 1. shows that I-1 binds to both STAT3 and E3 ligase.

Example 290. AlphaLISA Assays

FIG. 2 shows that I-1 promotes the formation of the STAT3-degrader-E3 ligase ternary complex and STAT3 ubiquitination.

Example 291. Live Cell Degradation Kinetics

TABLE 80

Live Cell Degradation Materials

| Reagent | Vendor | Catalog # |
|---|---|---|
| FuGENE HD Transfection Reagent (1 mL) | Promega | E2311 |
| 384 well plate, white, flat bottom | Grenier Bio-One | 781080 |
| Endurazine (1 mL) | Promega | N2571 |

700,000 A549 HiBiT cells were seeded in 60 mm dish and rested overnight at 37° C. Cells were transfected with LgBiT vector comprising 6.5 pg plasmid DNA+19.5 μL FuGENE HD transfection reagent per 60 mm dish (scale up/down as necessary). Following 24 h post transfection, cells were trypsinized and seeded at 2,000 cells/well in 40 μL in a 384-well plate. Cells were not seeded in the 2 outermost columns/rows to avoid evaporation. Outer wells were filled with PBS. After allowing the cells to settle overnight, Endurazine 1:100 was added to the cells by first diluting 1:10 in media and further diluting 1:10 in 40 μL of cells by adding -4.4 μL of diluted Endurazine in plate #1. Cells were incubated at 37° C. for 2.5 h. Compound was added with Tecan HPd300 dispenser (final DMSO=0.1%) to both plates (10 point, 1:3 dilution; 30 μM top dose). Plate #1 luminescence was read at t=0, 30 min, 1h, 2h, 4h, 6h, 8h, 16h, 24h, 48h. Plate was returned to incubator between reads.

Figure 3:
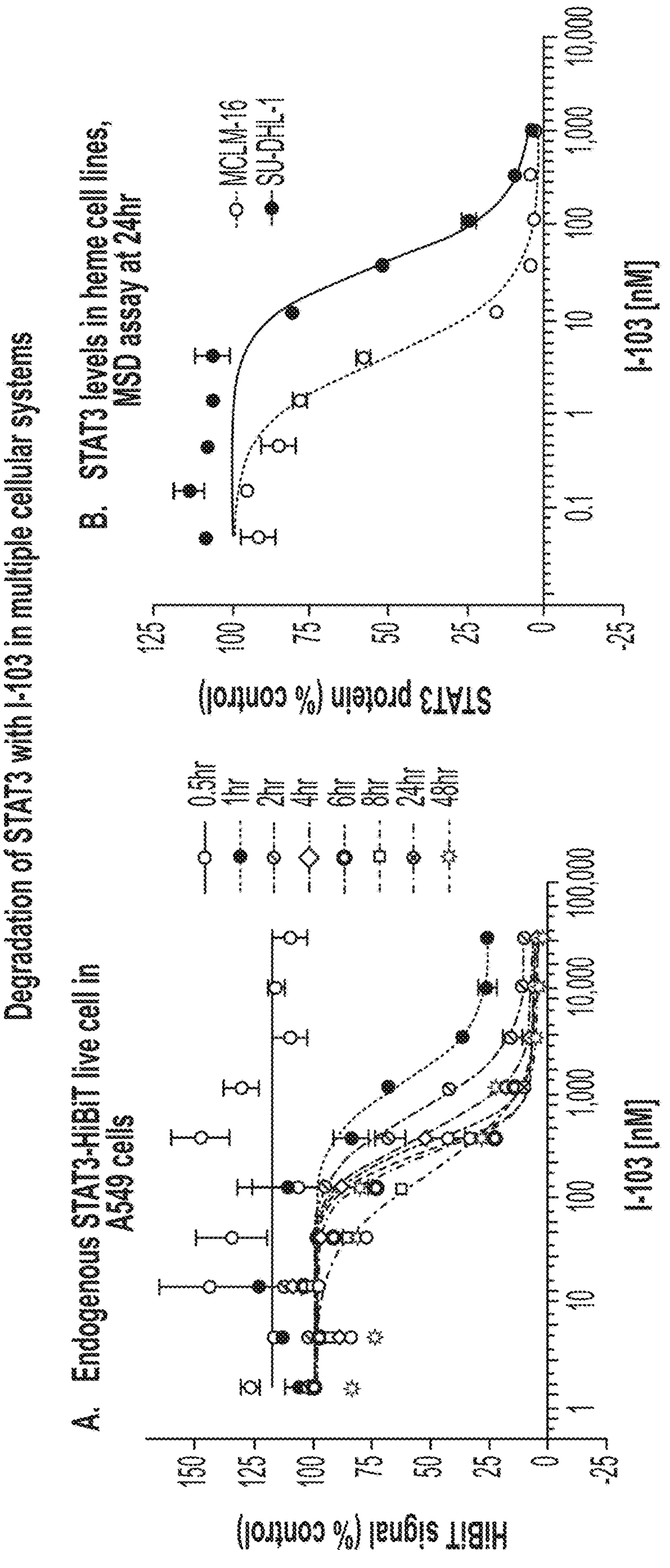
FIG. 3 includes graphical images showing the results of an endogenous STAT3-HiBiT live cell assay in A549 (A) with HiBiT signal (% control)(y-axis) over I-103 concentration (nM)(x-axis) at 0.5, 1, 2, 4, 6, 8, 24, and 48 hours and a MSD assay of STAT3 levels in heme cells lines MOLM-16 and SU-DHL-1 at 24 hours (B) with STAT3 protein (% control)(Y-axis) over I-103 concentration (nM)(x-axis).
Figure 21:
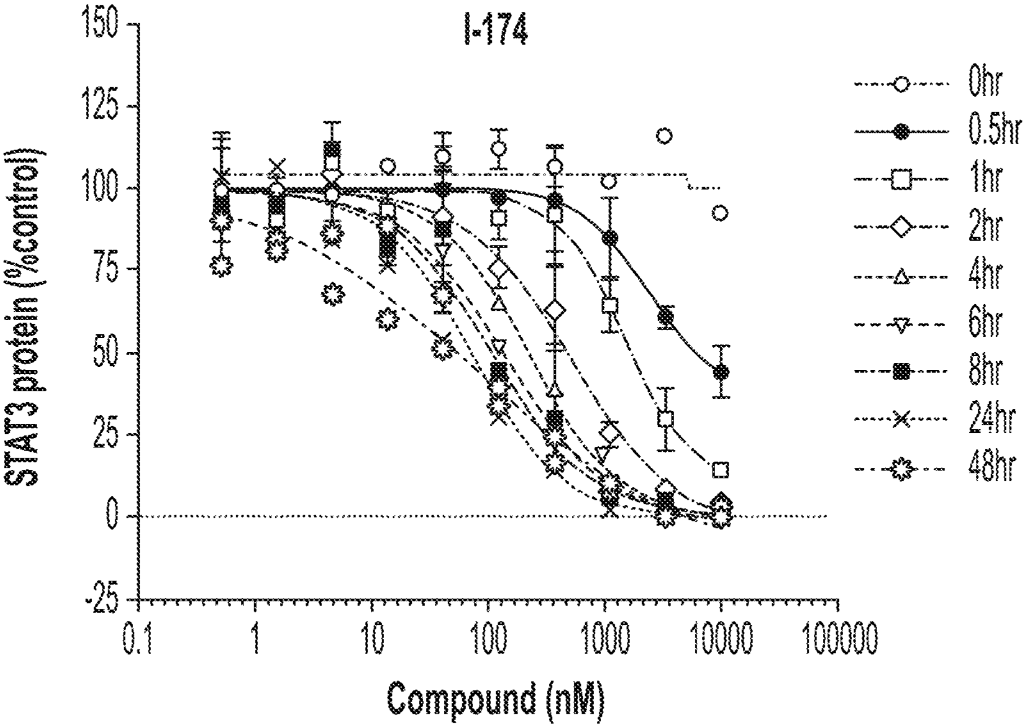
FIG. 21 depicts dose-response curves in a STAT3-HiBiT live cell assay in A549 cells using I-174 and I-94 with STAT3 protein (% control)(y-axis) over compound concentration (nM)(x-axis) at 0.5, 1, 2, 4, 6, 8, 24, and 48 hours.
Figure 21:
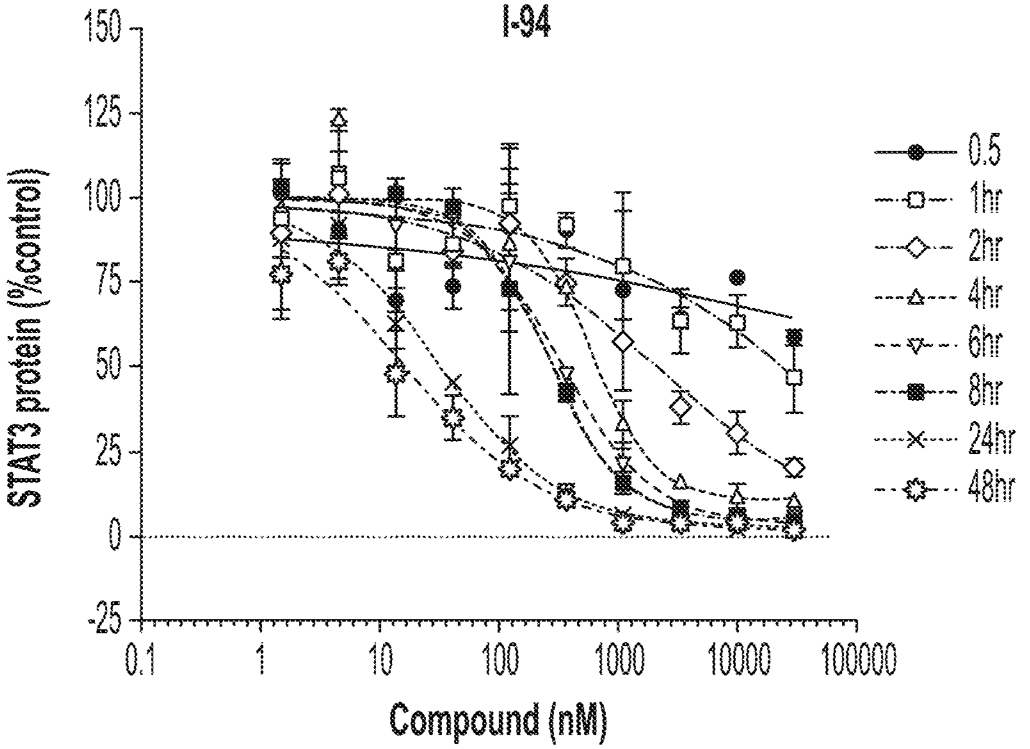

Part A of FIG. 3 shows that I-103 causes rapid and potent degradation of STAT3. FIG. 21 shows that I-174 and I-94 cause rapid and potent degradation of STAT3.

Example 292. STAT3 MSD Assay Protocol 100 nl of compounds were added into the intermediate plate with Echo (Labcyte 550) from source plate containing a 3-fold serial dilution from top concentration of 1 mM. Cells were seeded into 96-well plates (4×104 cells/well/100 ul media), mixed well, and incubated for 24 hours. The media was aspirated from the cultures and 60 μL pre-chilled PIPA lysis buffer (Boston BioProducts BP-115D) with protease/phosphatase inhibitor (Roche 05892791001/Roche 04906837001) was added into the well to lyze the cells for 20 minutes at 4° C. The MSD plate (L15XA) was coated with 2 μg/ml capture antibody (ab119352) in PBS and incubated at 4° C. overnight. The next day, the plate was washed three times with TBST (CST #9997S), 150 μL/well. MSD plates were blocked with 150 μL blocking buffer per well and shaken for 1 hr at RT and 600 rpm. The blocking buffer was 3% Blocker A (MSD, $R_{93}$BA-4) in TBST. The MSD plate was washed three times with 150 μL/well of TBST and 70 μL cell lysate was added into the well and shaken for 1 hour at RT and 600 rpm. The MSD plate was washed three times with 150 μL/well of TBST and added 25 μL/well of detection antibody (ab68153) to a final concentration of 1 μg/ml diluted in 1% blocking buffer and shaken for 1 hour at RT and 600 rpm. MSD plate was washed three times with 150 μL/well of TBST and added 25 μL/well of SULFO-TAG anti-rabbit antibody (MSD, $R_{32}$AB-1) to a final concentration of 1 μg/mL diluted in 1% blocking buffer and shaken for 1 hour at RT and 600 rpm. The MSD plate washed three times with 150 μL/well of TBST and added 150 μL/well of 2X MSD reading buffer diluted from 4X (MSD, R92TC-2) with water. Lastly the MSD instrument was read.

Figure 5:
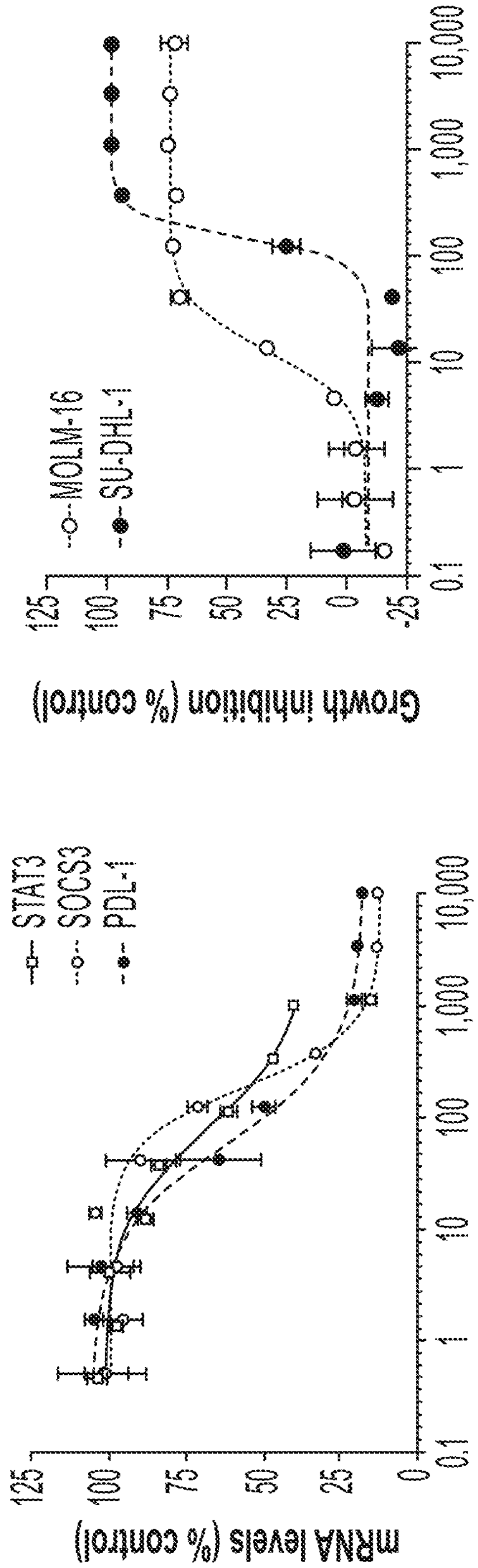
FIG. 5. Includes graphical images and tables showing the results of RT-qPCR in SU-DHL-1 cells at 24 hours (A) with mRNA levels (% control) over I-103 concentration (nM)(x-axis) for STAT3, SOCS3, and PDL-1 genes and CellTiterGlo (CTG) cell viability at 4 days (B) with growth inhibition (% control) over I-103 concentration (nM)(x-axis) for MOLM-16 and SU-DHL-1 cell lines. Also shown are the results of MSD degradation $DC_{50}$ (nM) in MOLM-16 and SU-DHL-1 cell lines at 24 hours.
Figure 6:
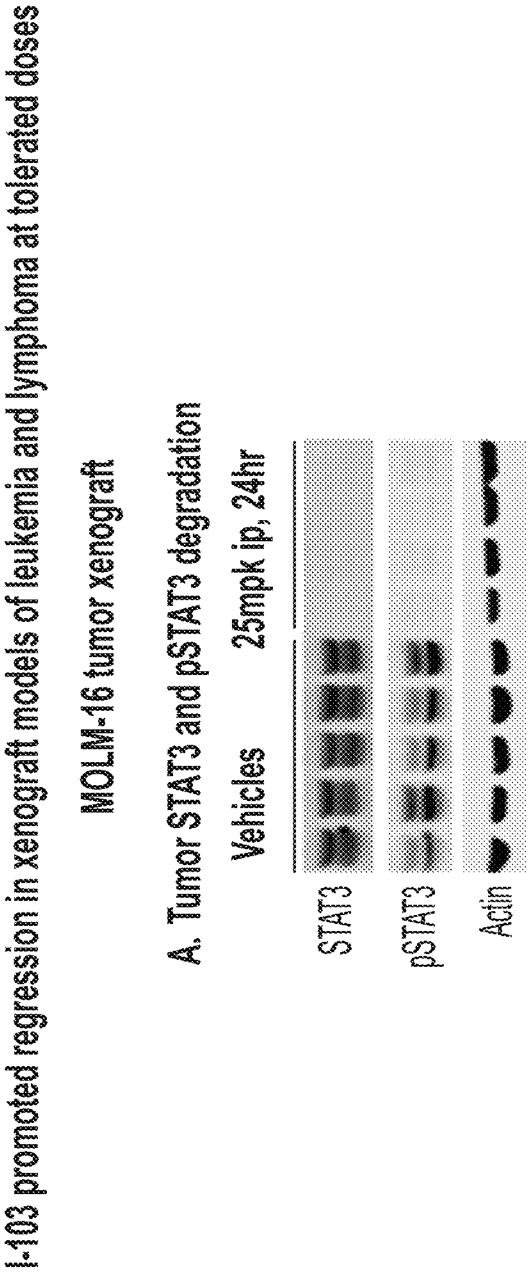
FIG. 6 includes graphical images of MOLM-16 and SU-DHL-1 tumor xenograph results using I-103 for STAT3 and pSTAST3 degradation (A), efficacy in NOD/SCID mice (B) with tumor volume median ($mm^3$) over days (post randomization) for vehicle, 25 mg/kg IP QD, and 50 and 100 mg/kg SC BIW dosing, STAT3 and pSTAT3 degradation (C) with STAT3, and pSTAT3 (relative STAT3/Actin)(left y-axis) and plasma concentration (μM)(right y-axis) for vehicle, 25 mpk QD x2 (24 hours post dose), and 50 mpk QD x 1 (48 hours post dose), efficacy in NOD/SCID mice (D) with tumor volume median ($mm^3$) over days (post randomization) for vehicle, 25 mg/kg IP (2 day on/5 day off), 50 mg/kg IP QW, 50 mg/kg IP Q2D, and 50 mg/kg IP (2 day on/5 day oft) dosing, and bodyweight changes observed in NOC/SCID mice (E) for vehicle, 50 mg/kg IP QW, 50 mg/kg IP Q2D, and 50 mg/kg IP (2 day on/5 day off) dosing.
Figure 6:
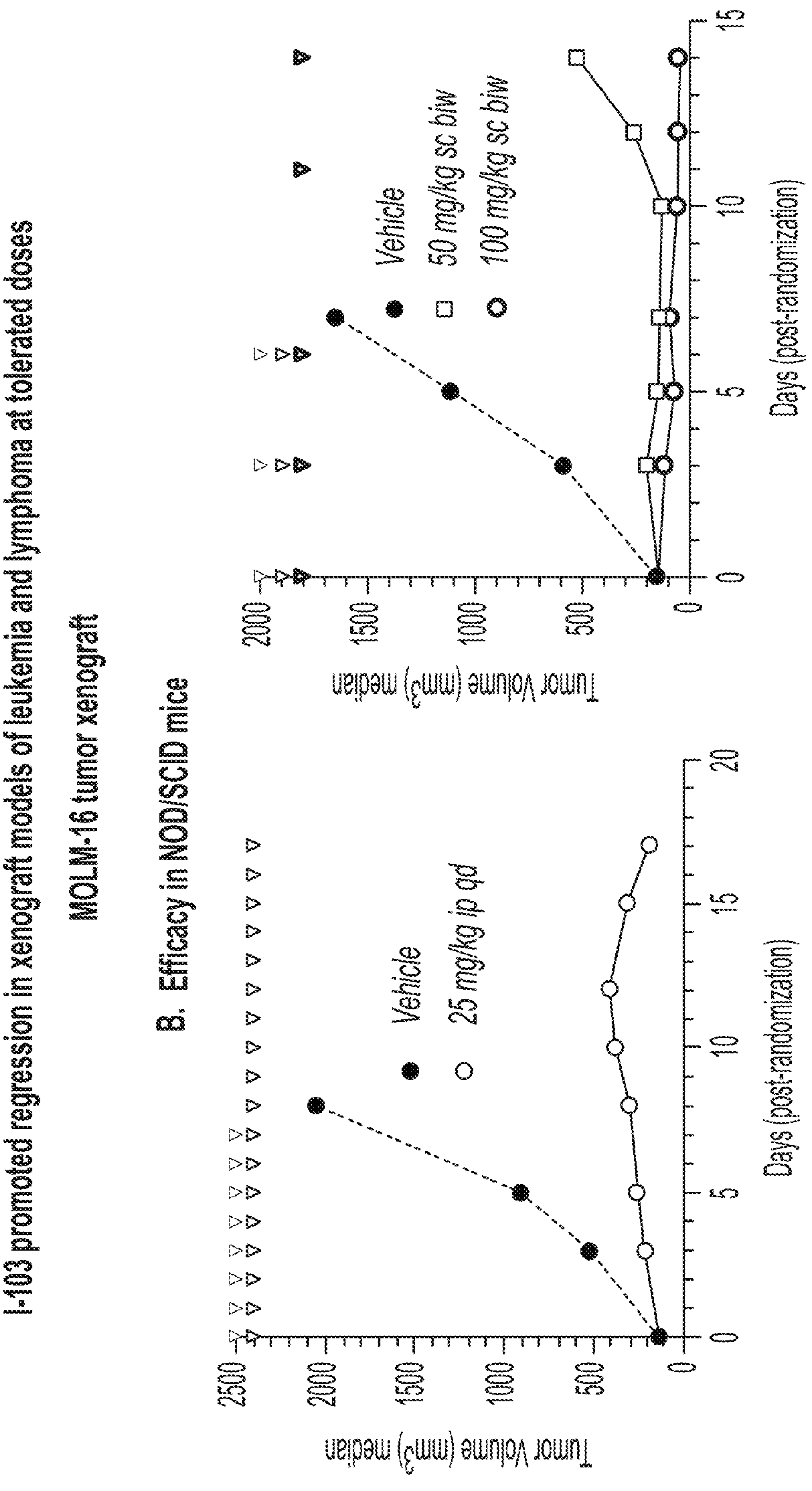
Figure 6:
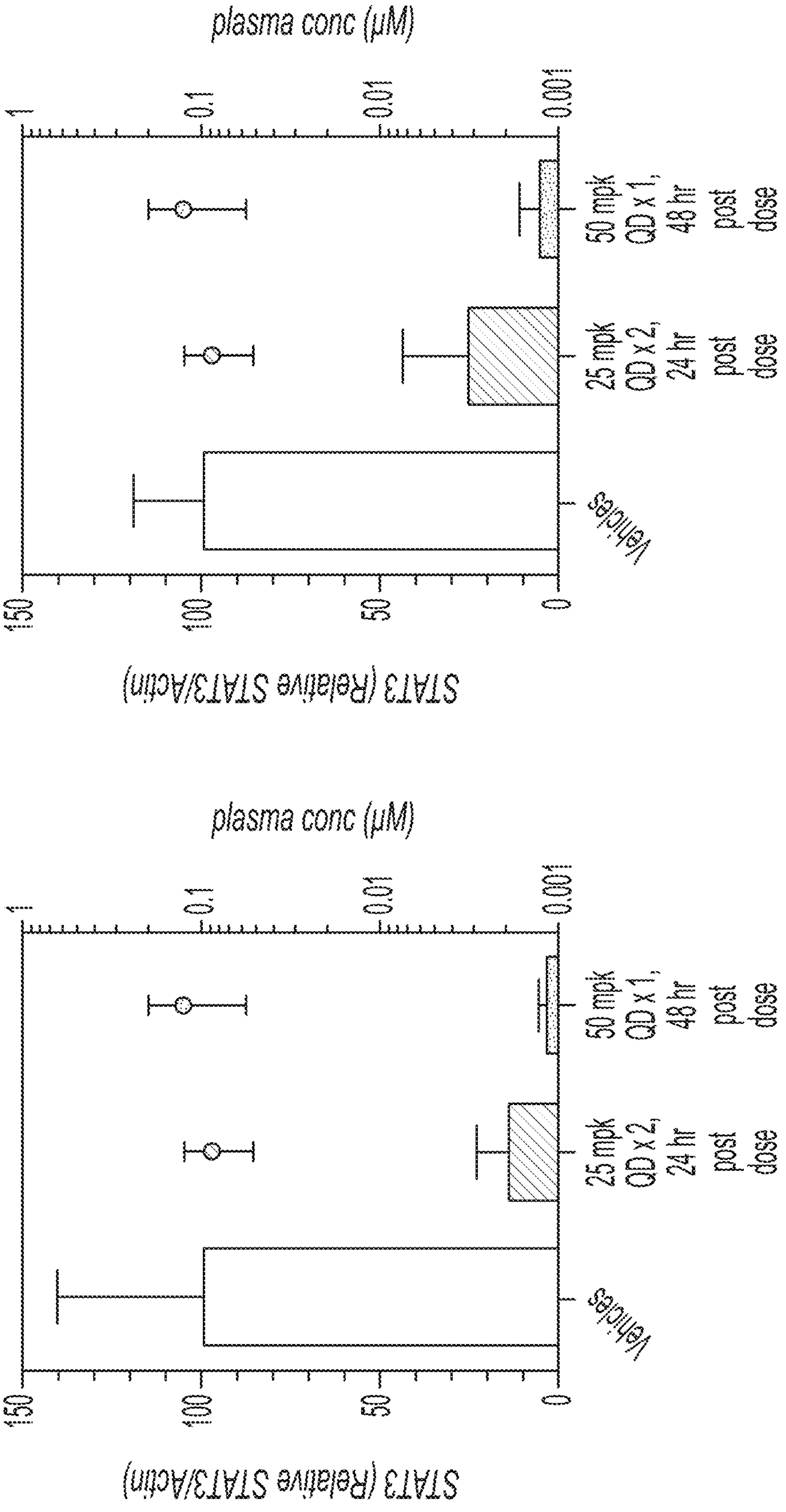
Figure 6:
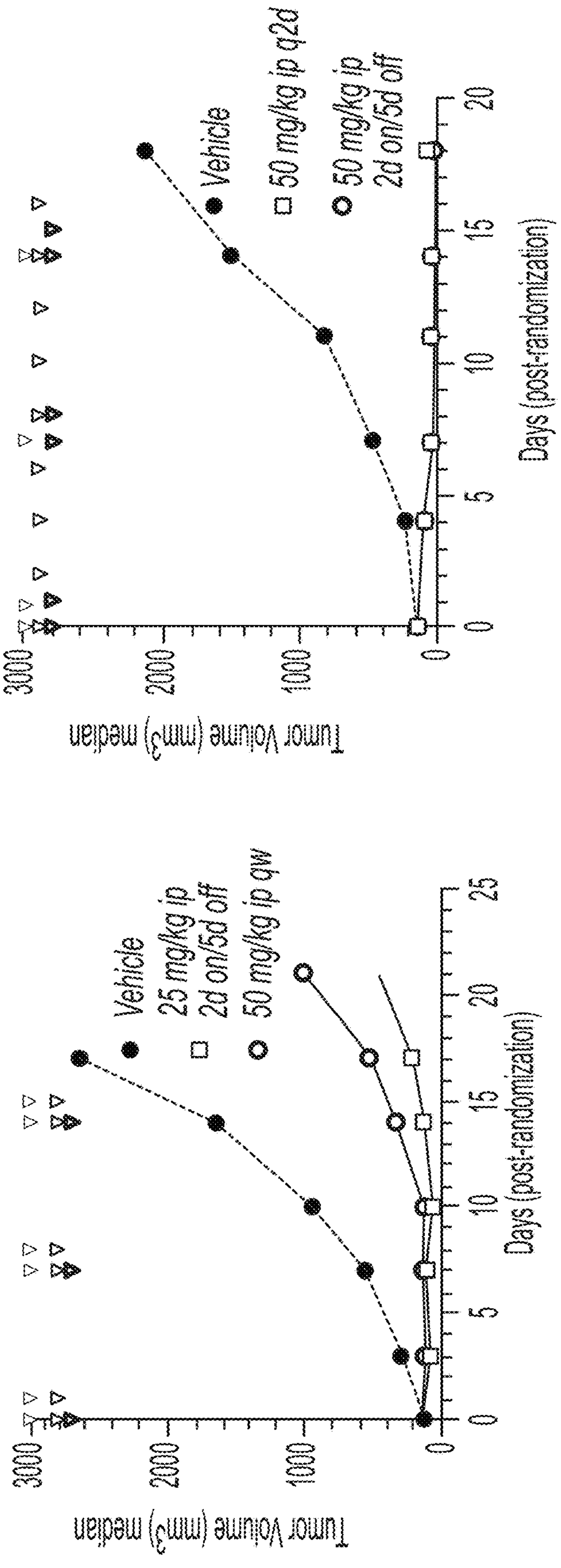
Figure 6:
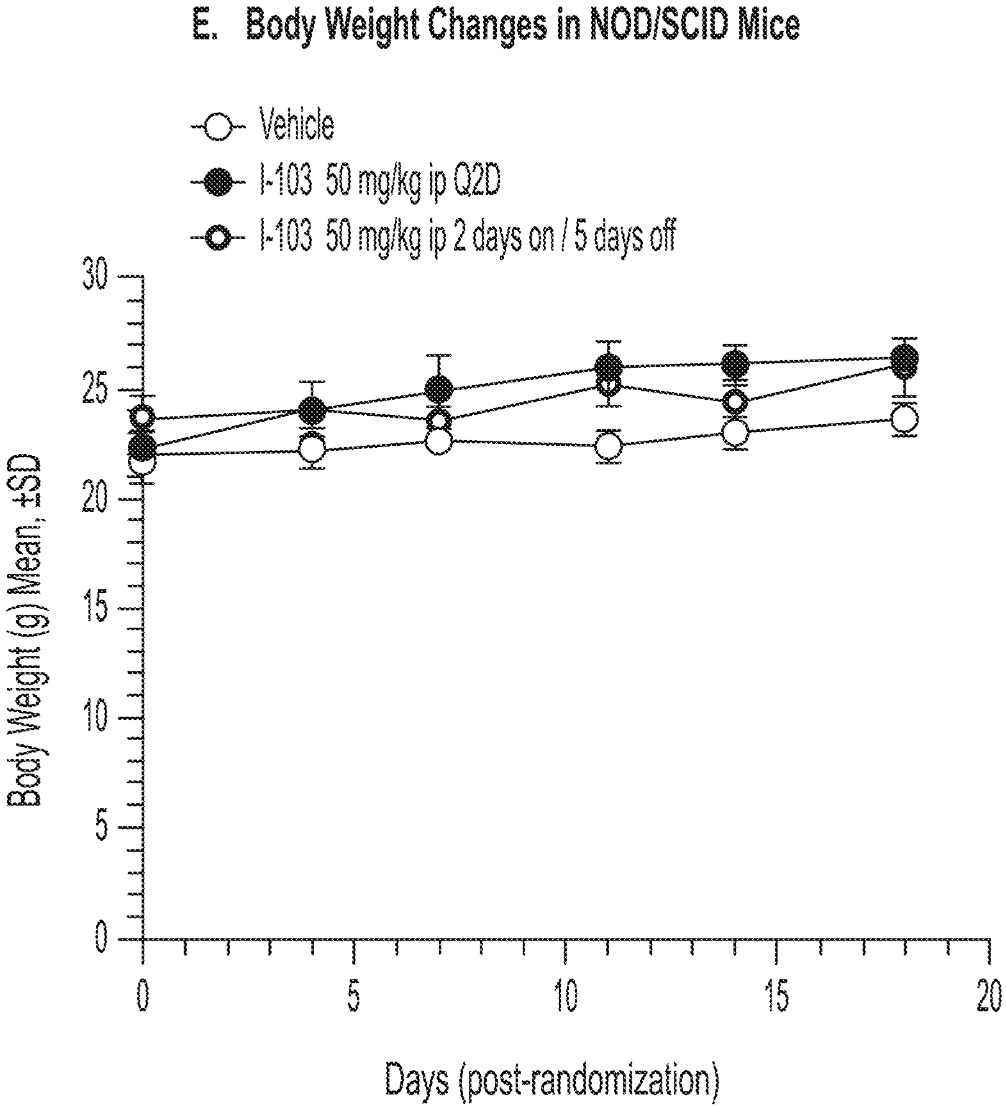
Figure 9:
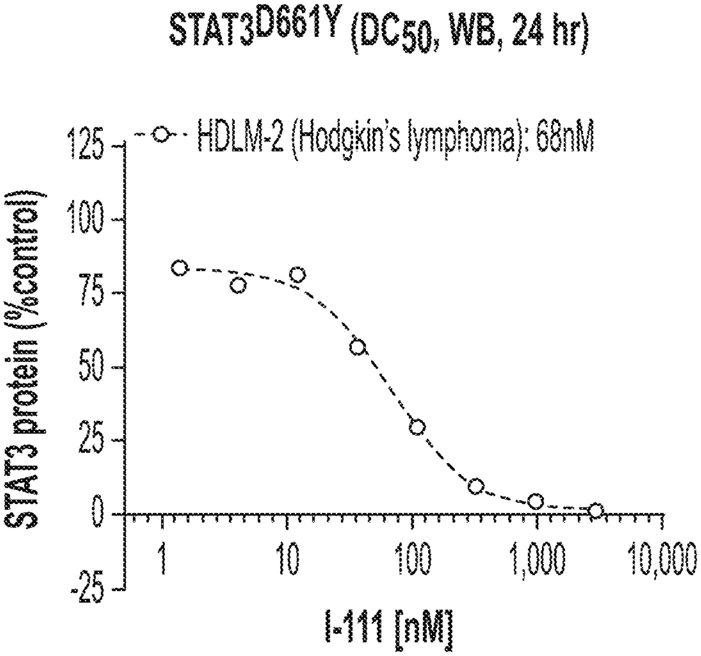
FIG. 9 depicts a dose response curve showing I-111 degrading mutant STAT3 (STAT D661Y) in HDLM-2 cell lines.
Figure 11:
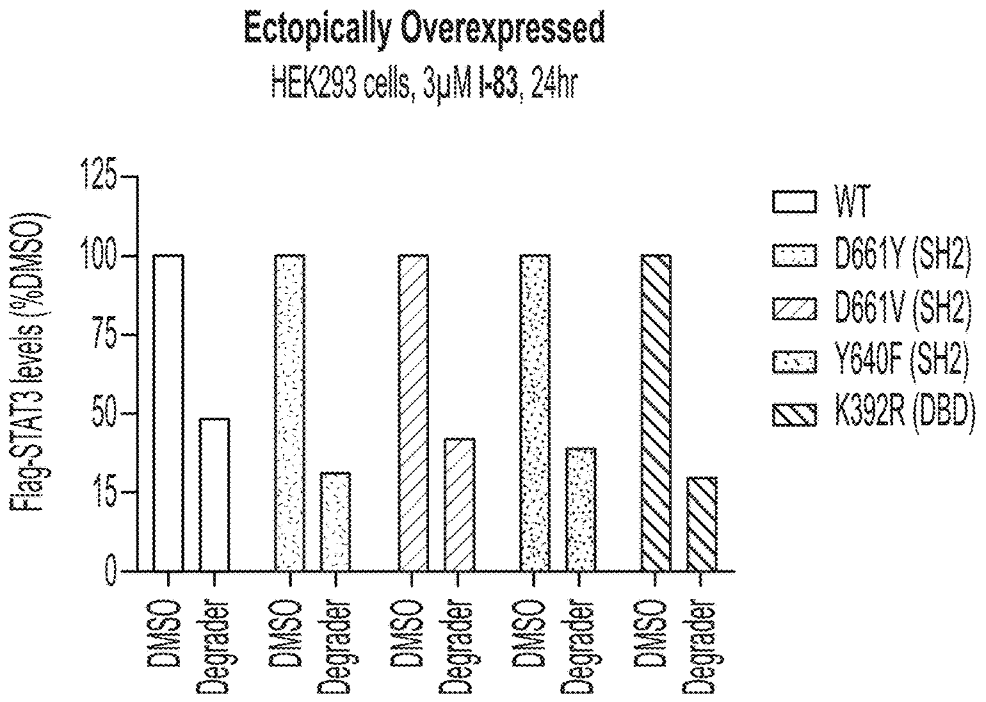
FIG. 11 depicts degradation results of the reduction of STAT3 in STAT3 mutants using I-83 (3 μM, 24 hr) in ectopically overexpressed HEK293 cells showing Flag-STAT3 levels (% DMSO)(y-axis) for WT, D661Y (SH2), D661V (SH2), Y640F (SH2), and K392R (DBD) mutants (x-axis).
Figure 12:
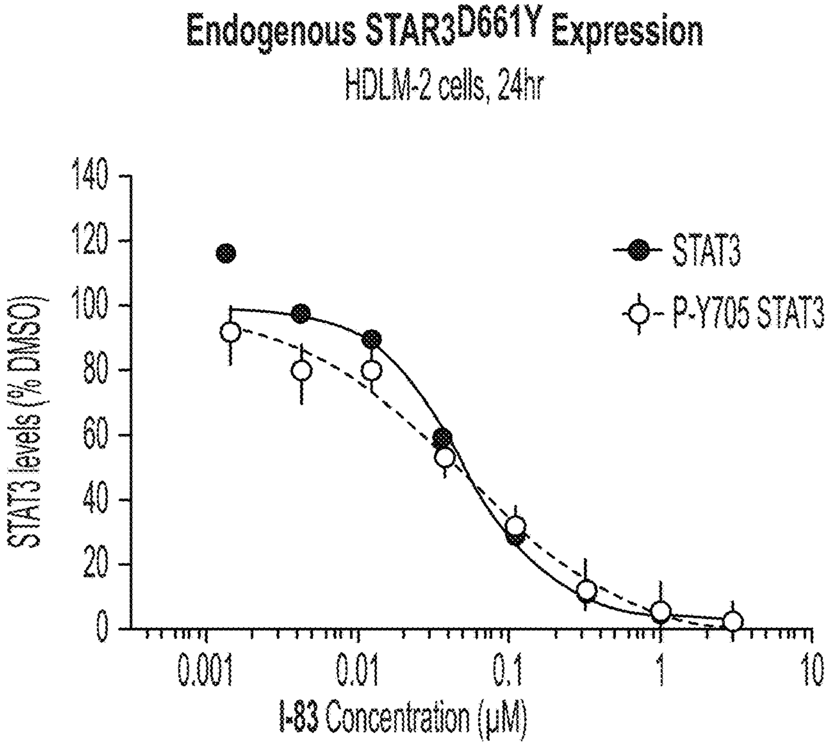
FIG. 12 depicts a dose response curve showing I-83 degrading mutant STAT3 (STAT D661Y) in HDLM-2 cell lines.
Figure 14:
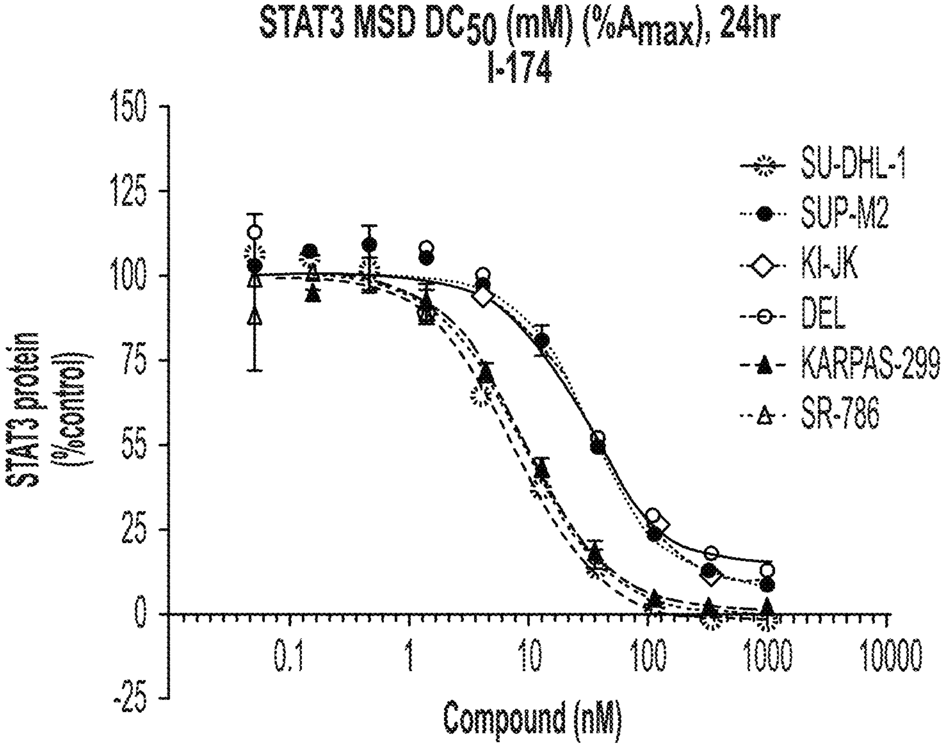
FIG. 14 depicts dose response curves and $DC_{50}$ results showing I-174 and I-94 mediated degradation in multiple ALK+ALCL cell lines.
Figure 14:
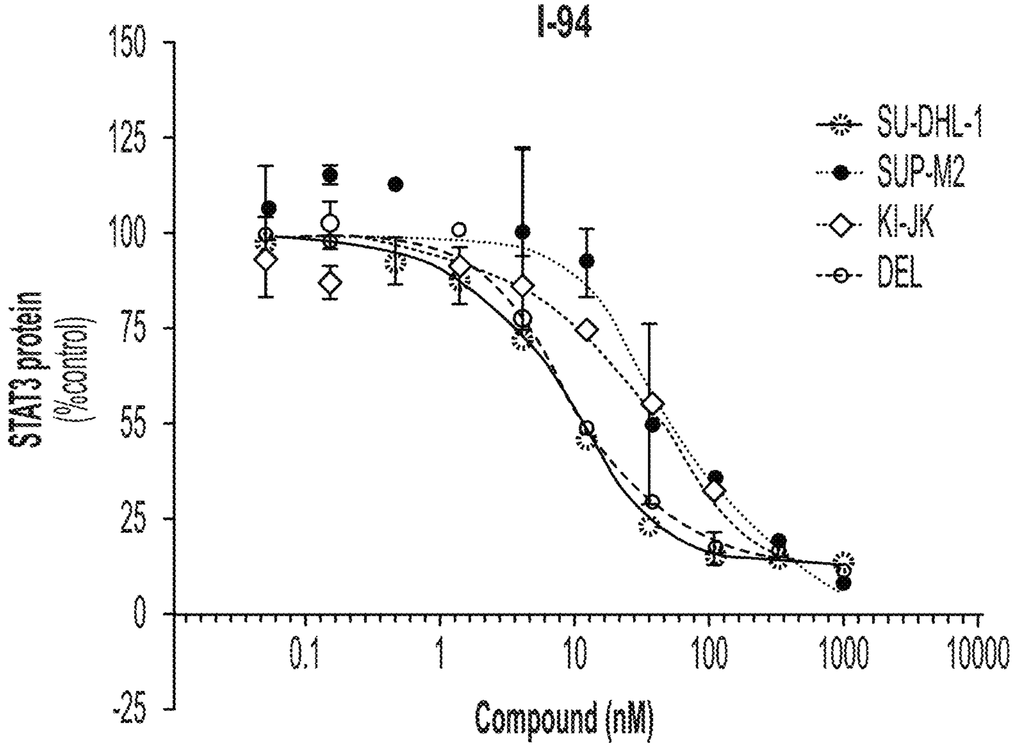

Part B of FIGS. 3 and 5 shows the MSD assay dose-response curve and $DC_{50}$ of I-103 on MOLM-16 ($DC_{50}$=4 nM) and SU-HDL-1 cells ($DC_{50}$=28 nM). FIG. 9 shows that I-111 degrades mutant STAT3 heme cell lines ($DC_{50}$=68 nM). FIG. 11 shows that I-83 degrades mutant STAT3 HEK293 cell lines. FIG. 12 shows that I-83 degrades mutant STAT3 heme cell lines. FIG. 14 shows the MSD assay dose-response curves of I-174 and I-94 in multiple ALK+ ALCL cell lines.

STAT3 MSD $DC_{50}$ results (μM, % $A_{max}$, 24 hr) in various ALK+ALCL cell lines are presented in Table 81 below.

TABLE 81

| MSD $DC_{50}$ Results in ALK+ ALCL Cell Lines | | | | | | |
|---|---|---|---|---|---|---|
| I-# | SU-DHL-1 | SUP-M2 | KI-JK | DEL | KARPAS-299 | SR-786 |
| I-94 | 0.015 (>95) | 0.062 (95) | 0.039 (95) | 0.028 (97) | 0.013 (99) | 0.009 (99) |
| I-174 | 0.015 (>95) | 0.086 (95) | 0.047 (97) | 0.016 (95) | ND | ND |

Example 293. STAT3 RT-qPCR Assay Protocol

SU-DHL-1 cells were treated with compounds for a designed time. 0.3-0.6 mL lysis buffer with 2-mercaptoehanol was added to the collected cell pellet or monolayer cells. The cells were vortexed until the cell was dispersed and the cells appear lysed. One volume of 70% ethanol was added to each volume of cell homogenate and vortex. 700 μL of the sample was transferred to the spin cartridge and centrifuged at 12000 g for 15s at RT. The flow-through was discarded and the process repeated until the entire samples had been processed. 700 ul wash buffer I was added to the spin cartridge and centrifuged at 12000 g for 15s at RT and the flow-through was discarded. 500 μL wash buffer II with ethanol was added to the spin cartridge and centrifuged at 12000 g for 15s at RT and the flow-through was discarded. The process was then repeated. The spin cartridge was centrifuged at 12000 g for 2 min to dry the membrane with bound RNA. 30-100 μL RNase-free water was added to the center of the spin cartridge and incubated for 1 min at RT. The spin cartridge was centrifuged at 12000 g for 2 min to elute the RNA from the membrane into the recovery tube and the purified RNA was stored. The concentration of the RNA was quantitated using Nano-Drop. cDNA was formed from the RNA by reverse transcription and qPCR of the cDNA with primer of the gene of interest and housekeeping gene was preformed using the volumes below:

| RNAto cDNA: | |
|---|---|
| 2× RT Buffer Mix | 10 μL |
| 20× RT Enzyme Mix | 1 μL |
| RNA | 2 μg |
| Total volume | To 20 μL |
| qPCR: | |
| 2× TaqMan ® Universal PCR Master Mix | 5 μL |
| 20× GADPH(ACTB) TaqMan probe/primer | 1 μL |
| cDNA template | 1 μL |
| Nuclease free water | 3 μL |
| Total volume | 10 μL |

Figure 15:
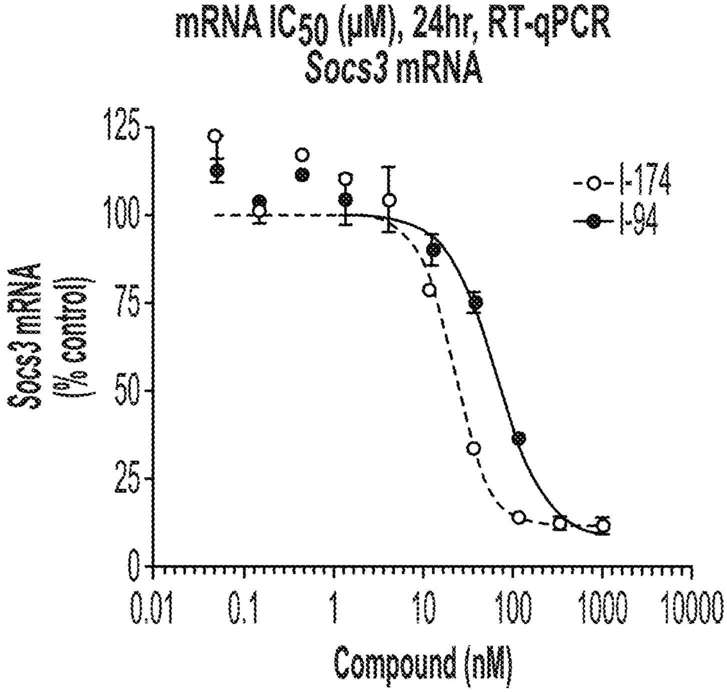
FIG. 15 depicts dose response curves and $IC_{50}$ results showing I-174 and I-94 repression of STAT3-mediated gene expression in of SOCS3 and PD-L1 in SU-DHL-1 cells.
Figure 15:
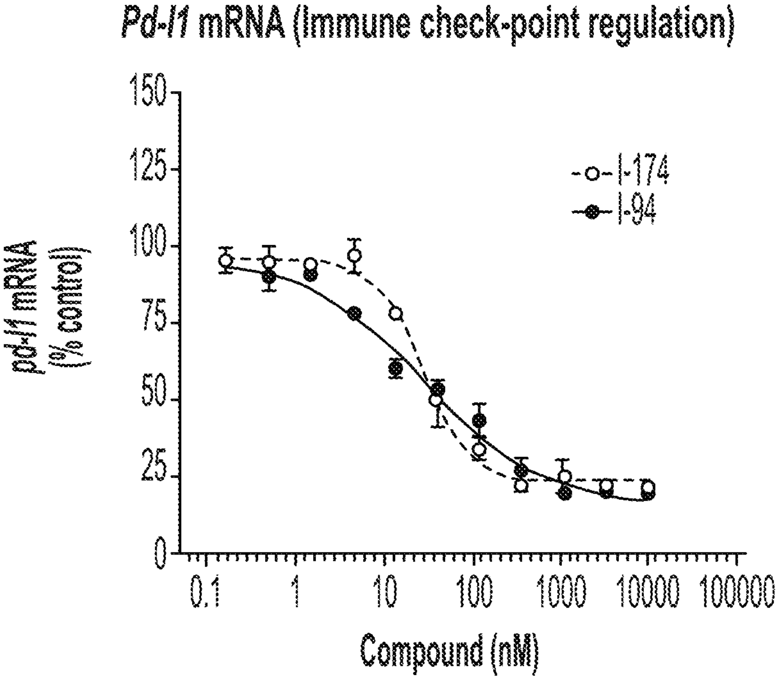

Part A of FIG. 5 shows that 1-103 downregulates STAT3-dependent gene expression of STAT3, SOCS3, and PDL-1. FIG. 15 shows that I-174 and I-94 downregulates STAT3-dependent gene expression of STAT3, SOCS3, and PDL-1.

STAT3 gene expression inhibition results are presented in Table 82 below.

TABLE 82

| STAT3 Gene Expression Inhibition Results | | |
|---|---|---|
| | mRNA (RT-qPCR) $IC_{50}$ (μM), 24 hr | |
| I-# | SOCS3 | PD-L1 |
| I-94 | 0.066 | 0.030 |
| I-174 | 0.022 | 0.029 |

Example 294. Cell Viability Protocol

Compound-mediated viability effect on MOLM-16 and SU-HDL-1 cells was quantitatively determined using the CellTiter-Glo® Luminescent Cell Viability Assay kit from Promega (Catalog number G7572) following manufacturer's recommended procedures.

Day 0: 60 nL of compounds/DMSO were stamped to the cell plate as on the recommended platemap. Compound precipitation was observed. Cells were centrifuged at 800 rpm for 5 min, suspended with culture medium, and counted with Countess (Invitrogen). The cell density was adjusted to the recommend concentration. 30 μL of cell solution (2000cells/well) was added to the assay plate according to the platemap. 30 μL of media was added to column 2 and column 23 as on the platemap. The final concentration of the compounds except for the reference compound Paclitaxel was from 10M, 3-fold dilution and 11 dose (Paclitaxel started at 500 nM). The final DMSO concentration was 0.2%. The assay plate was incubated at 37° C., 5% $CO_2$ for 4 days.

Day 4: The assay plate was equilibrated to RT for ~10 minutes. Compound precipitation was observed (96h). To determine cell viability, 30 μL of CellTiter Glo reagent was added to each well and the assay plate was centrifuged at 1000 rpm for 30 second, incubated at room temperature for 10 min, and analyzed by detecting the luminescence using a multimode plate reader (EnVision 2105, PerkinElmer). The data was then analyzed by software Prism 7.0 from GraphPad and the dose response curves were fit using a three-parameter logistic equation to calculate $EC_{50}$.

Figure 16:
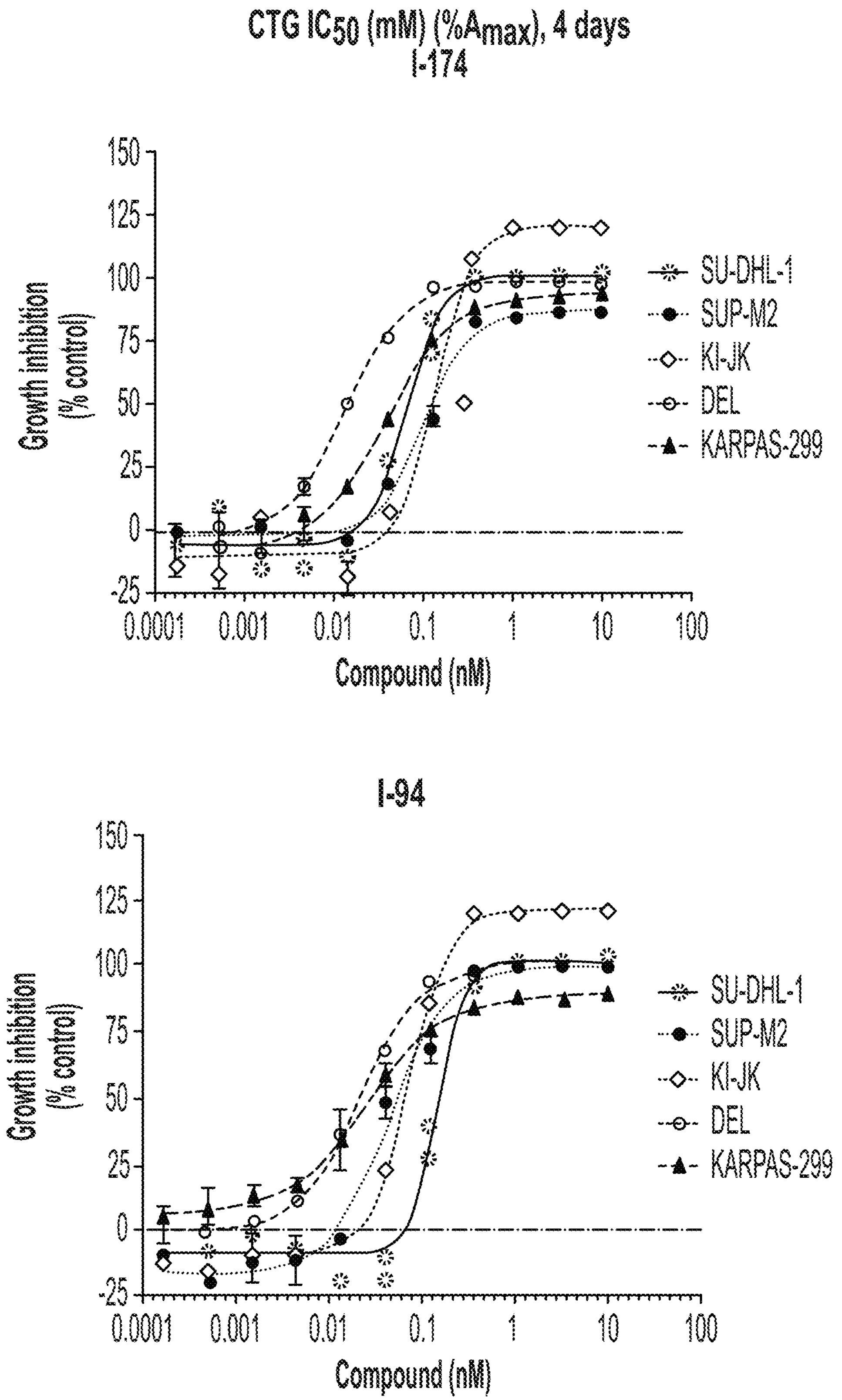
FIG. 16 depicts dose response curves showing I-174 and I-94 mediated growth inhibition in multiple ALK+ALCL cell lines.

Part B of FIG. 5 shows that I-103 inhibits MOLM-16 and SU-DHL-1 cell proliferation. FIG. 16 shows that I-174 and I-94 inhibit SU-DHL-1, SUP-M2, KI-JK, DEL, and KARPAS-299 cell proliferation.

Growth inhibition results in various cell lines is provided in Table 83 below.

TABLE 83

Cell Viability Results in Various Cell Lines

| I-# | Cell line | Tumor type | CTG, $IC_{50}$ μM (% Max inh), Day 4 |
|---|---|---|---|
| I-94 | SU-DHL-1 | ALCL (ALK+) | 0.321 (89) |
| I-94 | SUP-M2 | ALCL (ALK+) | 0.125 (>95) |
| I-94 | KI-JK | ALCL (ALK+) | 0.102 (110) |
| I-94 | DEL | ALCL (ALK+) | 0.038 (>95) |
| I-94 | KARPAS-299 | ALCL (ALK+) | 0.047 (85) |
| I-94 | SR-786 | ALCL (ALK+) | 0.25 (85) |
| I-103 | SUP-M2 | ALCL (ALK+) | 0.61 (>95) |
| I-103 | DEL | ALCL (ALK+) | 0.11 (>95) |
| I-103 | KARPAS-299 | ALCL (ALK+) | 0.14 (50-55) |
| I-103 | SR-786 | ALCL (ALK+) | 3.8 (75) |
| I-111 | A3/KAW | DLBCL | 1.9 (50-55) |
| I-174 | SU-DHL-1 | ALCL (ALK+) | 0.015 (>95) |
| I-174 | SUP-M2 | ALCL (ALK+) | 0.086 (95) |
| I-174 | KI-JK | ALCL (ALK+) | 0.047 (97) |
| I-174 | DEL | ALCL (ALK+) | 0.016 (95) |
| I-174 | KARPAS-299 | ALCL (ALK+) | 0.084 (90) |

Example 295. Protocol for the Examination of the Effect of Compounds on Cell Proliferation, Cell Cycle, Apoptosis and Cell Death in SU-DHL-1 Cells I-103 was evaluated to determine its effect on viability, cell cycle, cell proliferation, apoptosis, and STAT-3 expression. SU-DHL-1 cells were cultured until sufficient cell numbers were obtained. Timepoints were staggered in order to harvest all cells simultaneously. On day 1, cells were seeded at 12,000 cells per well in five identical 96 well-plates. Test compounds at 5 μM, 0.5 μM, and 0.05 μM and controls were added to the wells designated for the 96-hour timepoint. Test compound addition was repeated on days 2-4 for the 72, 48, and 24-hour timepoints.

At day 5. the cells were evaluated for each of the five readouts listed above. Cell viability was determined by preferentially staining dead cells with 3 μM DAPI. Cell proliferation was measured by Ki-67 expression of fixed and permeabilized cells using the Foxp3/Transcription Factor Staining Buffer Set. Cell cycle analysis was performed with the PI/RNase Staining Solution on ethanol-fixed cells. Caspase-3 and PARP internal staining was used to determine the level of apoptosis. STAT-3 expression levels were determined with as described below, fixing cells with 1.60 PFA and permeabilizing with methanol in order to stain cells with a STAT-3 antibody. All plates were analyzed by flow cytometry.

Definitions

Non-TC Non-Tissue Culture Treated

DPBS Dulbecco's Phosphate-buffered Saline

PFA Paraformaldehyde

BSA Bovine Serum Albumin

FBS Fetal Bovine Serum

PARP Poly (ADP-ribose) polymerase

PE Phycoerythrin

Table 84 shows the regaents used in the protocol.

TABLE 84

Reagents

| Reagent | Vendor | Cat. No. | Lot no. |
|---|---|---|---|
| DPBS | Hyclone | SH30028.02 | AE288871274 |
| DAPI | Biolegend | 422801 | B259697 |
| Absolute ethanol | Fisher | BP2818-500 | 174903 |
| FXCycle PI/RNase kit | ThermoFisher | F10797 | 2091866 |
| BD Stain Buffer BSA | BD | 554657 | 9092855 |
| AF647 cleaved PARP | BD | 558710 | 9070703 |
| PE Active Caspase-3 | BD | 550914 | 9073513 (fix/perm); |
| FoxP3 internal staining | eBioscience | 00-5523-00 | 2115573 |
| Ki67-APC, 100 tests | BioLegend | 350514 | B258553 |
| FBS | Peak Serum | PS-500A | 031C141 |
| 100% Methanol | Fisher | A452-4 | 190931 |
| CST Mouse anti-stat3 | CST | 9139S | 12 |
| PE Goat Anti-Mouse | Biolegend | 405307 | B288930 |
| RPMI 1640 | Gibco | A10491-01 | 2120437 |
| 96-well plate | Falcon | 351177 | 9091006 |
| 10% BSA | Miltenyi | 130-091-376 | 5170608271 |
| Rabbit α-Caspase-3 | BD | 51-68655X | 8235860 |
| PFA, 4% in PBS | Alfa Aesar | J61899 | Q15F500 |

Method:

Cell culture: SU-DHL-1 cells were cultured according to DSMZ recommendations for culture medium, passage frequency, and seeding density. Briefly, cells were seeded at $0.3\times10^6$ cells/mL and passaged every 2-3 days, not to exceed a cell density of $1.5\times10^6$/mL. SU-DHL-1 cells were cultured in RPMI 1640 medium supplemented with per FBS.

Co-culture cells and test compounds: SU-DHL-1 cells were harvested and the concentration was adjusted to 6.67×0 cells/mL. Cells were added to the wells according to the plate map below (FIG. 1). Each well received 180 p of cells for a total of 12,000 cells/well, as determined by an optimal seeding density pilot performed prior to the initiation of this experiment.

A 20 mM DMSO stock solution of I-103 was prepared. I-103 was first prepared at 1000X in DMSO and then further diluted to 10X in RPMI supplemented with 10% HI-FBS. I-103 was added at a volume of 20.L to the appropriate wells according to the plate maps. Controls were prepared as described in the table below (Table 85). Drug addition on days 2-4 followed the same protocol.

TABLE 85

| Preparation of Test Compounds and Controls | | | | |
|---|---|---|---|---|
| | | | 10X Prepared in RPMI +10% HI-FBS | |
| Final 1X Drug Conc. | 1000X Prepared in DMSO 1000x Drug Conc. | | 10X Drug Conc. | Volume needed per compound per concentration per timepoint = 200 µL |
| 5 µM | 5 mM | 3 µL 20 mM stock + 9 µl DMSO | 50 µM | 3 µL 5 mM stock + 297 µL media |
| 0.5 µM | 0.5 mM | 5 µL 5 mM stock + 45 µl DMSO | 5 µM | 5 µL 0.5 mM stock + 495 µL media |
| 0.05 µM | 0.05 mM | 5 µL 0.5 mM stock + 45 µl DMSO | 0.5 µM | 5 µL 0.01 mM stock + 495 µL media |
| Paclitaxel: | | | | |
| 25 nM | 25 µM | 2 µL 10 mM stock + 798 µl DMSO | 2.5 µM | 20 µL 1000X stock + 1.980 µL media |
| | | | DMSO: | |
| | | | 1% DMSO Ctrl stock (0.1% DMSO final cone) | 5 µL DMSO + 495 µL media |

Evaluation of cells after culture with test compounds: At the conclusion of the 96-hour incubation, each plate was evaluated for one specific endpoint readout.

Readout 1: Viability

The viability plate was removed from the incubator, centrifuged and washed with 200 µL of DPBS. Cells were centrifuged and the supernatant was decanted. The cell pellet was resuspended in 120 µL of 3 µM DAPI solution. Cells were incubated for 10 minutes at room temperature, protected from light. After the incubation, cells were centrifuged again, decanted and resuspended in 120 µL of BD stain buffer and analyzed by flow cytometry to determine cell viability.

Readout 2: Cell Cycle

The PI/RNase plate was removed from the incubator, centrifuged and washed with 200 µL of DPBS. Cells were centrifuged and the supernatant was decanted. The cell pellet was resuspended in 60 µL of DPBS. Absolute ethanol was added at 140 µL per well and mixed well to fix cells. Cells were incubated for 10 minutes at 4° C. After the incubation, cells were centrifuged and washed twice with DPBS. Cells were resuspended in 100 µL of FXCycle PI/RNase and incubated for 25 minutes at room temperature, protected from light. Cells were analyzed by flow cytometry without washing.

Readout 3: Proliferation

The Ki-67 plate was removed from the incubator, centrifuged and washed with 200 µL of DPBS. Cells were centrifuged and the supernatant was decanted. The cell pellet was resuspended in 200 µL of FoxP3 Fix/Perm Buffer. Cells were incubated for 30 minutes at room temperature, protected from light. After the incubation, cells were washed twice with 1X Perm Buffer. Following the final wash, cells were resuspended in 200 µL of BD stain buffer and stored at 4° C. until analysis by flow cytometry. At that time, cells were centrifuged and resuspended in 200 µL of 1X Perm Buffer. Again, cells were centrifuged, then resuspended in diluted Ki-67 antibody and incubated for 1 hour at room temperature, protected from light. Subsequent to the incubation with Ki-67 antibody, the volume of each well was brought to 200 µL with 1X Perm Buffer. Cells were centrifuged to remove unbound antibody. The plate was then washed with 1X Perm Buffer. After the final centrifugation, 1X Perm Buffer was decanted and cells were resuspended in 120 µL BD Stain Buffer and analyzed by flow cytometry.

Readout 4: Apoptosis

The Caspase-3/PARP plate was removed from the incubator, centrifuged and washed with 200 µL of cold DPBS. The supernatant was decanted and the cell pellet was resuspended in 100 µL of BD Cytofix/Cytoperm solution. Cells were incubated on ice for 20 minutes, protected from light. Following the incubation, cells were washed twice with BD Perm/Wash Buffer. Following the final wash, cells were resuspended in 200 µL of BD stain buffer and stored at 4° C. until analysis by flow cytometry. At that time, cells were centrifuged and washed with 200 µL of 1X BD Perm/Wash Buffer. After centrifugation, supernatant was decanted and cells were resuspended in 60 µL of diluted Caspase-3 and PARP antibody cocktail. The plate was incubated for 30 minutes at room temperature, protected from light. Following the antibody incubation, the volume of each well was brought to 200 µL with 1X BD Perm/Wash Buffer. Cells were centrifuged to remove unbound antibody. The plate was then washed with 1X BD Perm/Wash Buffer. After the final centrifugation, 1X BD Perm/Wash Buffer was decanted and cells were resuspended in 120 µL BD Stain Buffer and analyzed by flow cytometry.

Readout 5: STAT-3 Expression

The STAT-3 plate was removed from the incubator, centrifuged and resuspended in 200 µL of 1.6% PFA. Cells were incubated at room temperature for 10 minutes, protected from light. Following the incubation, cells were centrifuged and washed twice with 0.5% BSA in DPBS. Following the final wash, supernatant was decanted and the cells pellets were frozen at −80° until analysis by flow cytometry. At that time, cells were thawed at room temperature and washed with 0.5% BSA in DPBS. After centrifugation, supernatant was decanted and cells were permeabilized with 100 μL of 100% cold methanol. The plate was incubated for 10 minutes at 4° C., protected from light. Following the antibody incubation, the plate was washed three times with 0.5% BSA in DPBS. After the final centrifugation, the supernatant was decanted and cells were resuspended in 50 μL of diluted STAT-3 primary antibody and incubated at room temperature for 1 hour, protected from light. Following the primary antibody incubation, cells were washed twice with 0.5% BSA in DPBS. Cells were then stained with a PE-goat anti-mouse IgG secondary antibody for one hour at room temperature, protected from light. Following the incubation with the secondary antibody, cells were washed three times with 0.5% BSA in DPBS and then resuspended in 120 μL BD 0.5% BSA in DPBS and analyzed by flow cytometry.

Figure 7:
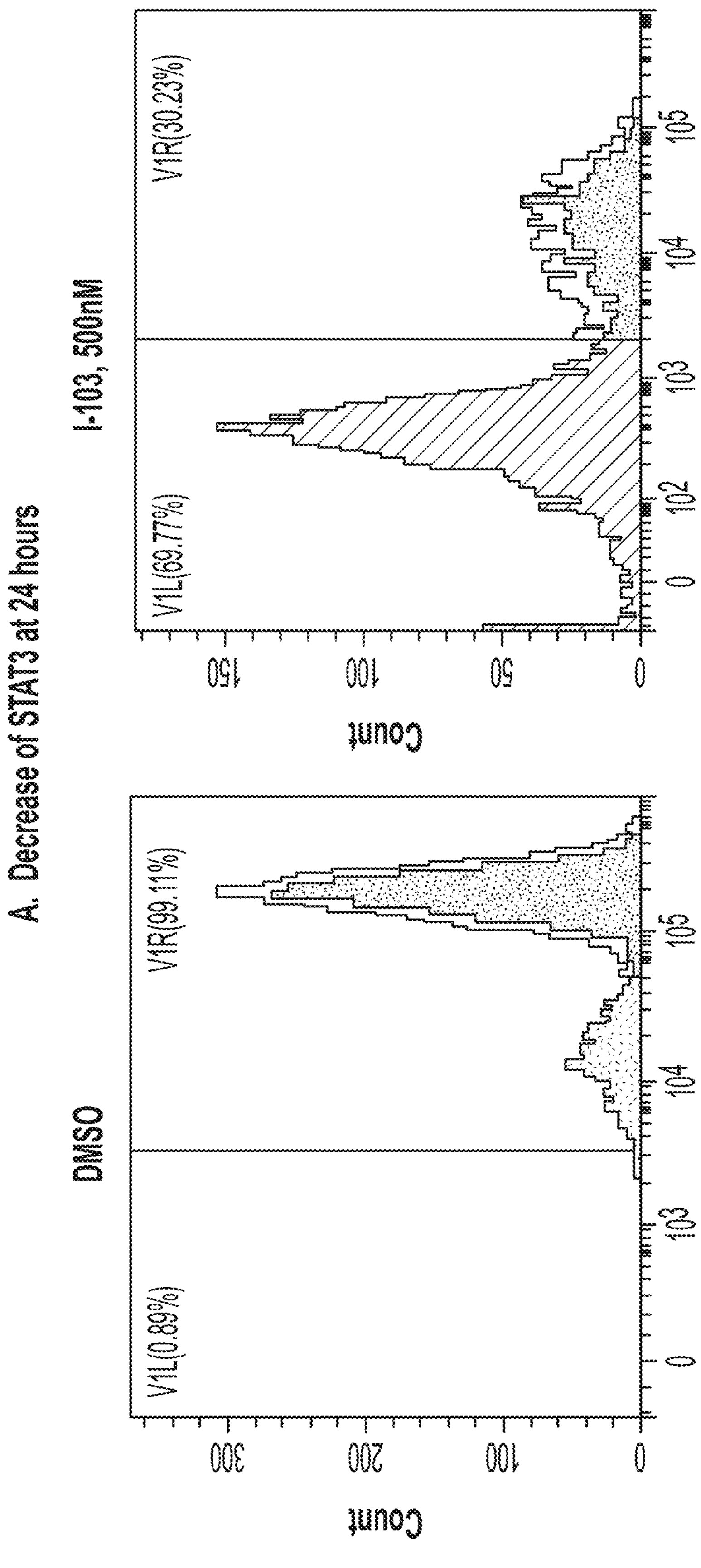
FIG. 7 depicts the decrease in STAT3 observed at 24 hours treatment with I-103 (A), the time-dependent inhibition of proliferation with I-103 (B), the increase in activated Caspase 3 at 48 hours that leads to cell death with I-103 treatment (C), and increase in subG1 cells observed with I-103 treatment (D).
Figure 7:
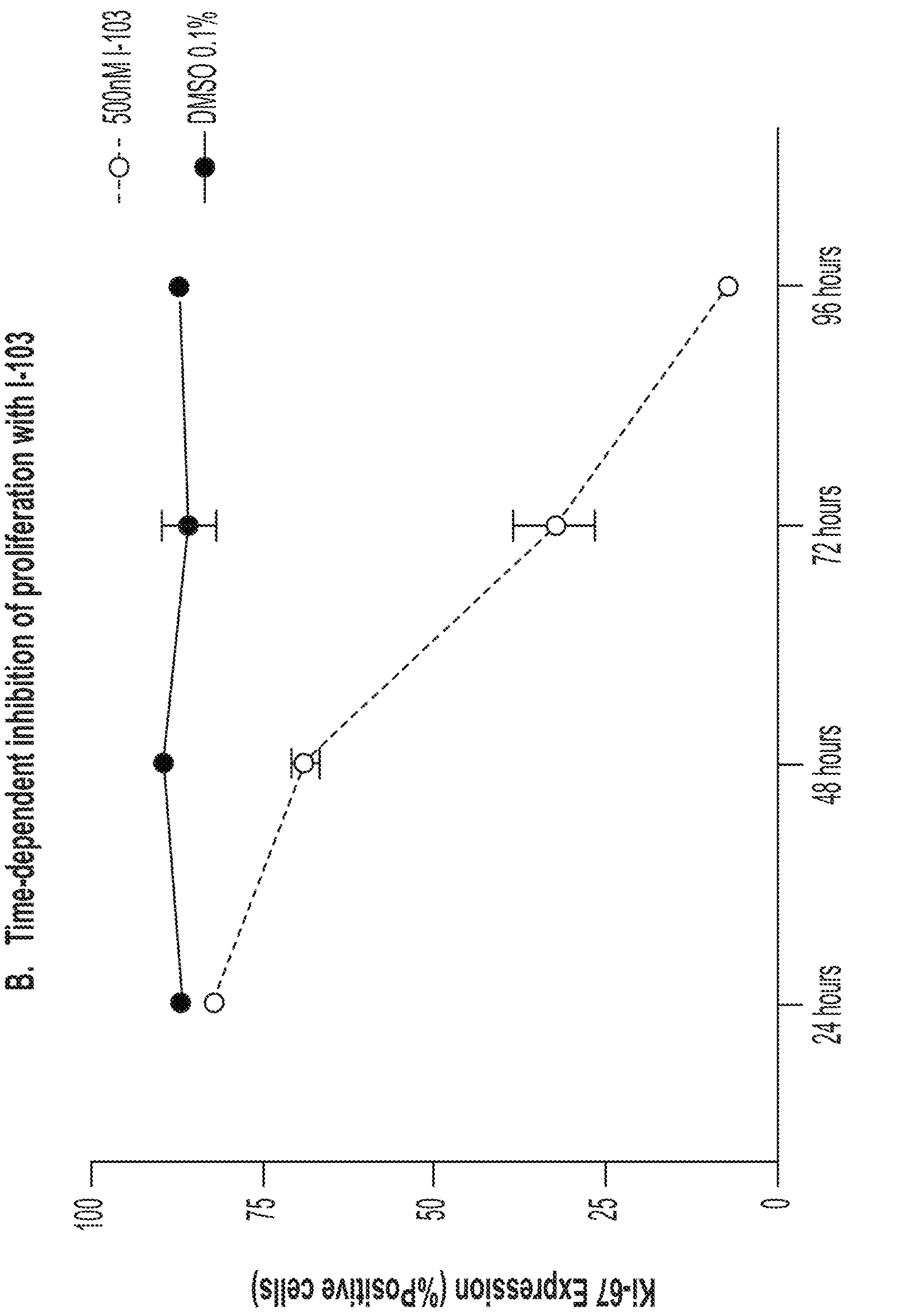
Figure 7:
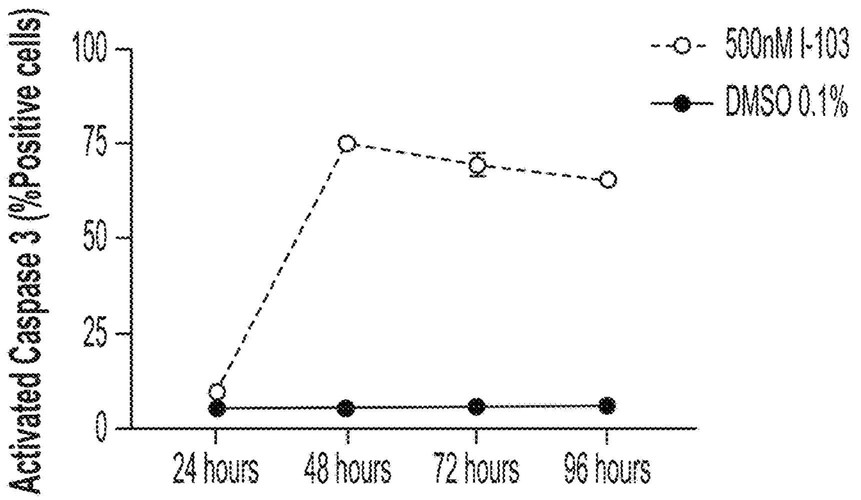
Figure 7:
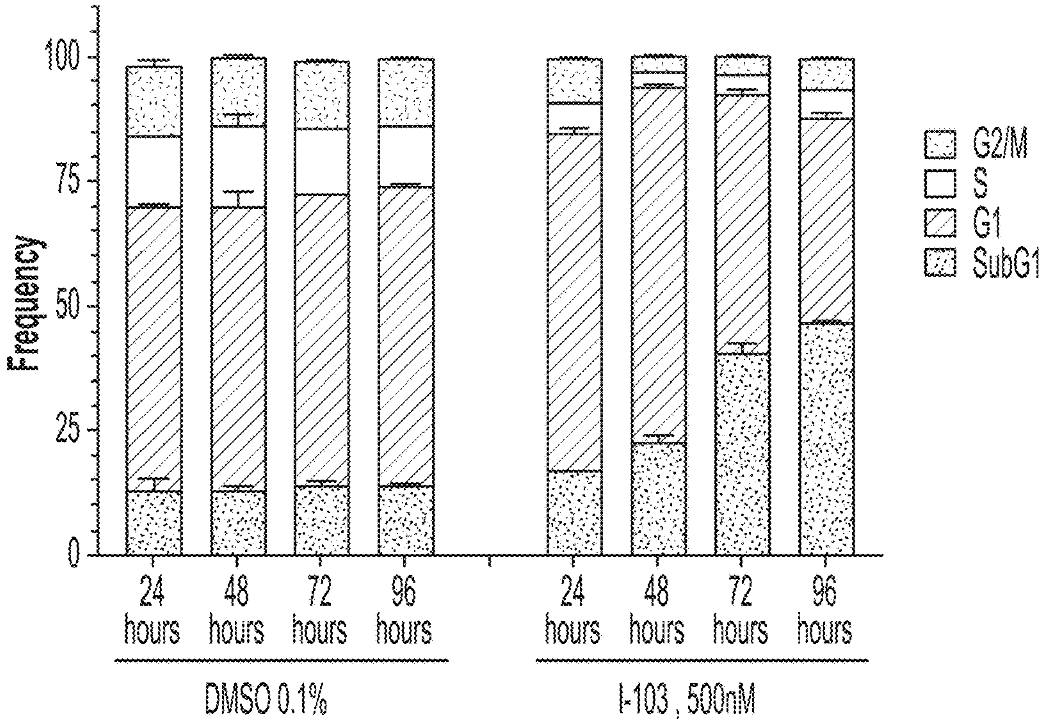

Results:

Results are depicted in FIG. 7. FIG. 7A depicts the decrease of STAT3 at 24 hours. FIG. 7B depicts the time-dependent inhibition of proliferation with I-103. I-103 treatment induces apoptosis at 48 hours that leads to cell death as depicted in FIG. 7C and FIG. 7D. FIG. 7C depicts the increase in activated Caspase 3 with treatment with I-103. FIG. 7D depicts the increase in subG1 cells (PI/RNAse analysis, FACS) seen at 48, 72, and 96 hours.

Example 296. Caspase Activity Assay

Determination of apoptosis was determined using a Caspase 3/7-Glo assay.

Method Summary

1- Prepare the Caspase-Glo® 3/7 Reagent (Promega cat #G8090)

Equilibrate the Caspase-Glo® 3/7 Buffer and lyophilized Caspase-Glo® 3/7 Substrate to room temperature before use.

Transfer the contents of the Caspase-Glo® 3/7 Buffer bottle into the amber bottle containing Caspase-Glo® 3/7 Substrate.

Mix by swirling or inverting the contents until the substrate is thoroughly dissolved to form the Caspase-Glo® 3/7 Reagent Aliquot and store at -20

2- If thawing the reagent, allow it to equilibrate to room temperature. Mix well.

3- Remove white-walled 384-well plate containing treated cells from the incubator and allow plates to equilibrate to room temperature.

4- Add Caspase-Glo® 3/7 Reagent to each well of the plate at 1:1 ratio with media. Because of the sensitivity of this assay, be careful not to touch pipet tips to the wells containing samples to avoid cross-contamination. Cover the plate with a plate sealer or lid.

5- Gently mix contents of wells using a plate shaker at 300-500 rpm for 30 seconds. Incubate at room temperature for 30-60 minutes. Note: Temperature fluctuations will affect the luminescence reading.

6—Measure the luminescence of each sample in a plate-reading luminometer as directed by the luminometer manufacturer.

Figure 8:
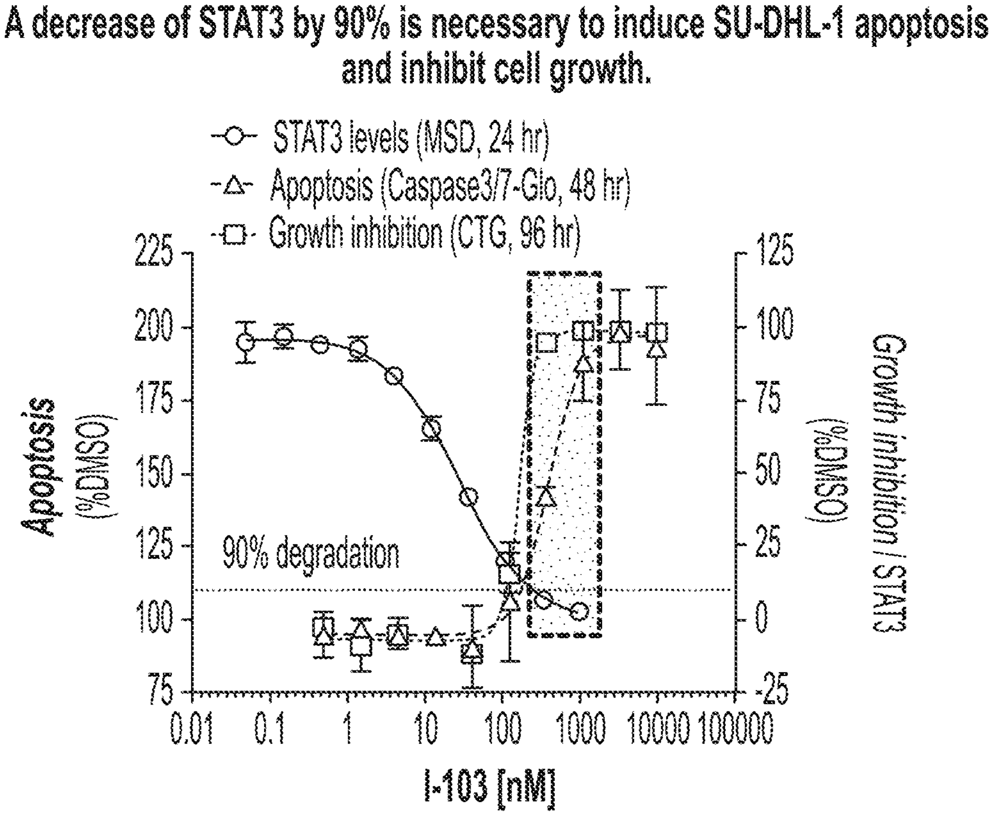
FIG. 8 depicts that a decrease of STAT3 by 90% using I-103 is necessary to induce SU-DHL-1 apoptosis and inhibit cell growth.
Figure 17:
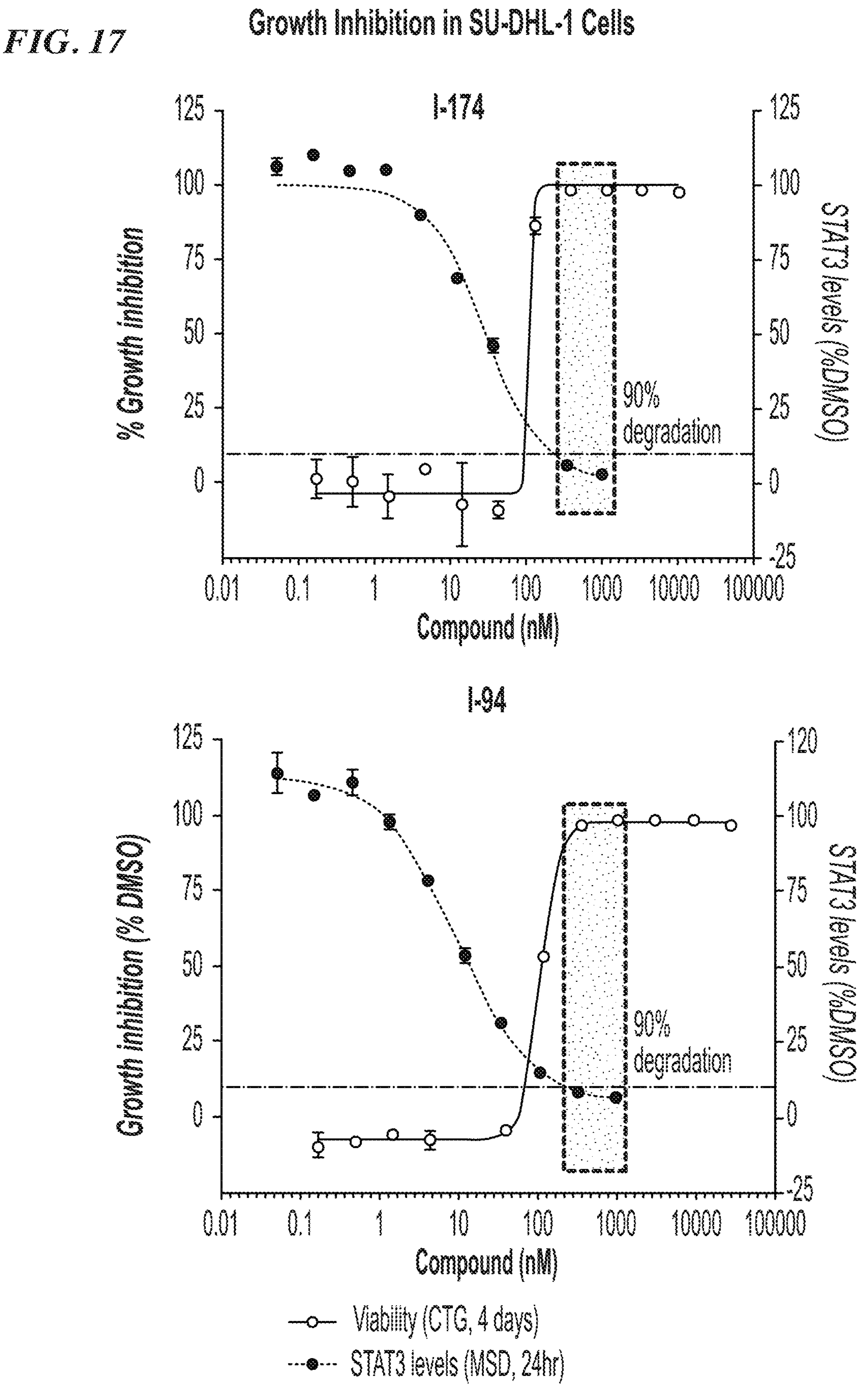
FIG. 17 depicts that a decrease of STAT3 by 90% using I-174 and I-94 is necessary to induce SU-DHL-1 apoptosis and inhibit cell growth.

STAT3 levels, Caspase activity, and growth inhibition in SU-DHL-1 cells is shown in FIG. 8 and Table 86. FIG. 17 shows that a decrease of STAT3 by 90% using I-174 and I-94 is necessary to induce SU-DHL-1 apoptosis and inhibit cell growth.

TABLE 86

SU-DHL-1 STAT3 levels, apoptosis, and growth inhibition results for I-103

| Assay | SU-DHL-1 |
|---|---|
| STAT3 levels, MSD $DC_{90}$ (μM) at 24 hr | 0.15 |
| Apoptosis, Caspase3/7-Glo $IC_{50}$ (μM) at 48 hr | 0.38 |
| Growth inhibition, CTG $IC_{50}$ (μM) at 96 hr | 0.167 |

Example 297. Wash-out study in SU-DHL-1 cells

I-103 and I-174 were tested in the wash-out protocol.

Compound Wash-Out Protocol

Day -2 and -1

Seed cell suspension in T75 flasks and treat with 0.10% DMSO and 1 uM compound for 24 and 48 hr.

Day 0

Collect cell suspension from the flasks in conical tubes after 24 and 48 hr, spin down at 1,000 rpm for 5 min.

Remove supernatant. Wash with PBS, spin down at 1,000 rpm for 5 min, repeat PBS wash one more time.

Seed the cells at 2,000 cells per well in 384-well plates for growth inhibition measurement via CellTiterGlo (CTG) and 10,000 cells per well in 96-well plates for STAT3 levels via MSD.

Measure T0 for CTG and collect pellets to measure levels of STAT3 by MSD

Day 1-4

Measure CTG every day for 4 days post wash-out.

Collect pellets and measure levels of STAT3 by MSD every day for 4 days post wash-out.

Growth Inhibition was Normalized to T0 and Graphed as % Control.

Figure 10:
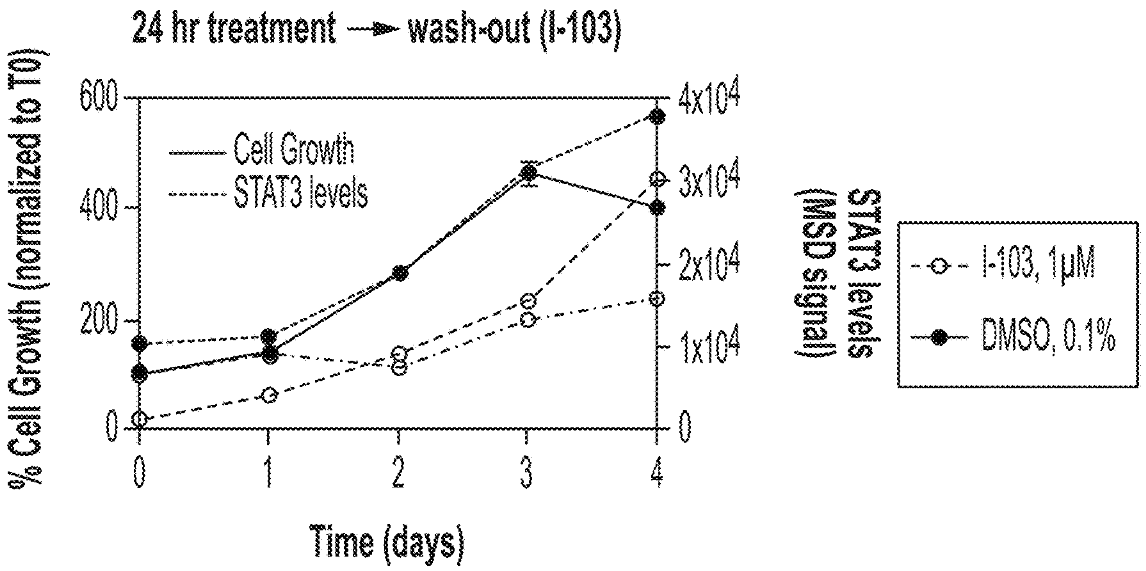
FIG. 10 depicts wash-out study results with I-103 at 24 hours (A) and 48 hours (B).
Figure 10:
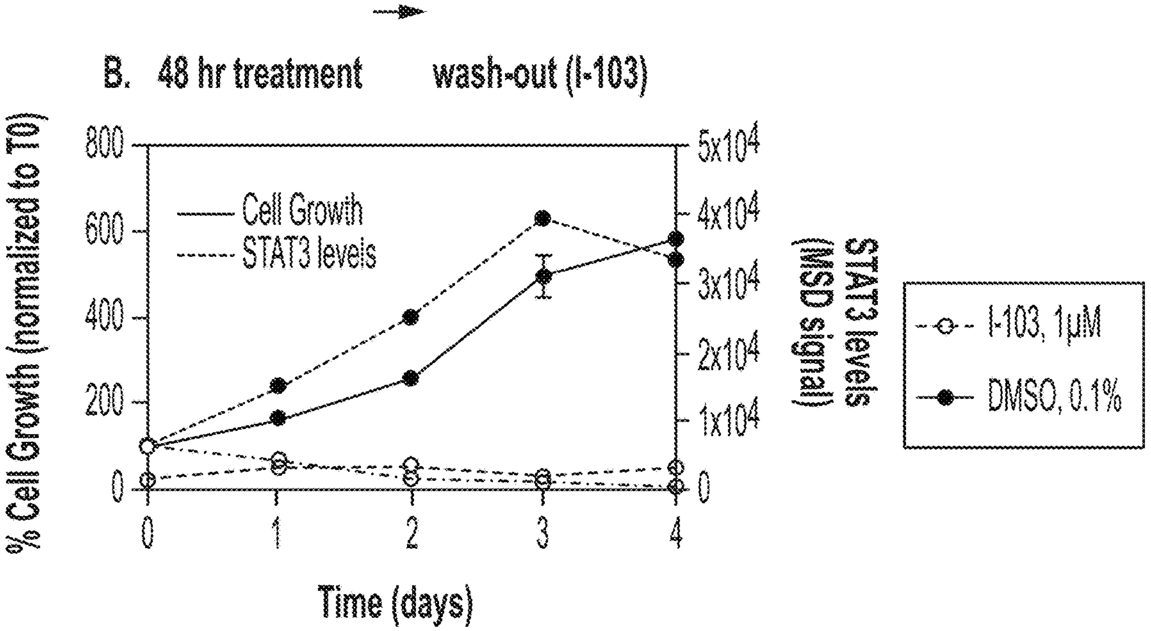
Figure 18:
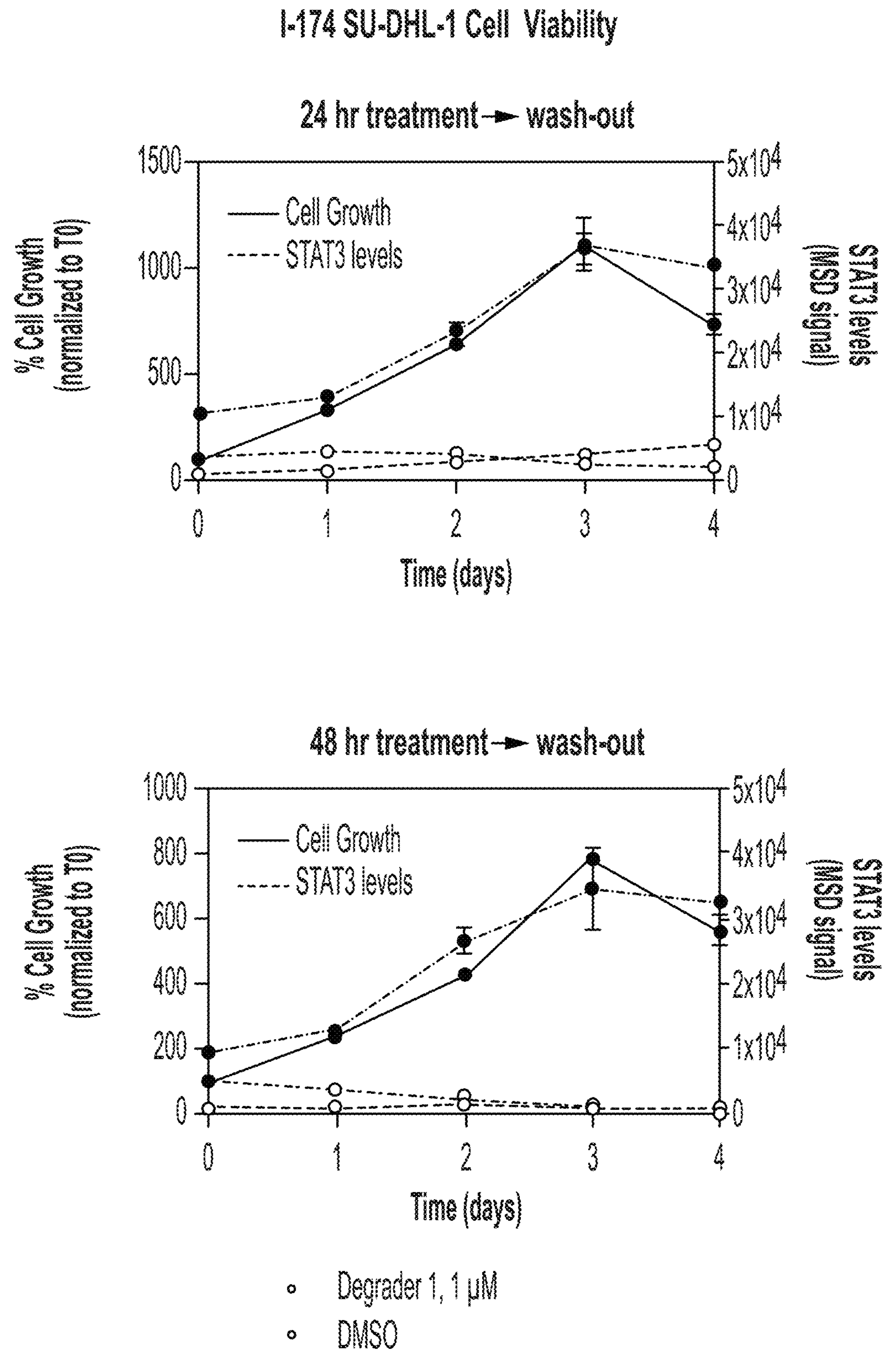
FIG. 18 depicts wash-out study results with I-174 showing strong growth inhibition and potential cell death after 4 days (24 hours wash-out) and complete growth inhibition and cell death after 4 days (48 hours wash-out) in SU-DHL-1 cells.

FIGS. 10 and 18 depict the results of the wash-out studies. FIG. 10A depicts wash-out results after a 24 hour treatment with I-103. FIG. 10B depicts wash-out results after a 48 hour treatment with I-103. FIG. 18 depicts the results with I-174 after 24 and 48 hours wash-out. Sustained degradation of STAT3 leads to profound effects on the viability of SU-DHL-1 cells.

Example 298. Deep Tandem Mass Tag Proteomics Protocol

Total protein was isolated from cells (e.g., Molm-16 and SU-DHL-1) and treated with degrader for 8 hours. Vehicle (DMSO)-treated cells were used as controls. Protein lysates, 2 biological replicates per condition, were prepared at 4C in 8M urea, 75 mM NaCl, 1 mM EDTA in 50 mM Tris HCl (pH 8), 10 mM NaF, phosphatase inhibitor cocktail 2 (1:100; Sigma, P5726) and cocktail 3 (1:100; Sigma, P0044), 2 μg/mL aprotinin (Sigma, A6103), 10 μg/mL Leupeptin (Roche, 11017101001), and 1 mM PMSF (Sigma, 78830). Lysates were spun at 20,000 rcf for 10 min and supernatant (containing extracted proteins) was transferred to a clean microcentrifuge tube. Protein concentrations were determined using the Pierce BCA assay. Protein lysates were reduced with 5 mM dithiothreitol (Thermo Scientific, 20291) for 45 min at room temperature and alkylated with 10 mM iodoacetamide (Sigma, A3221) for an additional 45 min. Protein digests were diluted 1:4 with 50 mM Tris HCl (pH 8) before digestion with LysC (Wako, 100369-826) for 2 h and with trypsin (Promega, V51 1X) overnight. Both lysis steps were performed at a 1:50 enzyme-to-protein ratio and at room temperature. Digested samples were acidified with formic acid (FA; Fluka, 56302) to a final concentration of 1% (final pH of <3), and then centrifuged at 2,000 rcf for 5 min to clear precipitated urea. Peptide lysates were desalted on C18 SepPak columns (Waters, 100 mg/lcc) and dried down using a SpeedVac Concentrator (Savant SC210A). Desalted peptides were then labeled with tandem mass tag (TMT, Thermo Fisher Scientific) reagents according to the manufacturer's instructions. TMT labeling was quenched and TMT11-plex was combined, desalted on a C18 SepPak column (Waters, 500 mg/6cc) and fractionated by high-pH reversed phase off-line chromatography into 24 fractions. Briefly, desalted TMT labelled peptides were loaded on a 4.6 mm×250 mm column RP Zorbax 300A Extend-C18 column (Agilent, 3.5 μm bead size), and separated on an Agilent 1100 Series HPLC instrument using basic reversed-phase chromatography. Ninety-six fractions were collected and subsequently concatenated as described earlier into 24 fractions. Each fraction was dried down and resuspended in 3% MeCN/0.1% FA to a peptide concentration of 1 μg/μL for LC-MS/MS analyses of the proteome. Online fractionation was performed using a nanoflow Proxeon EASY-nLC 1200 UHPLC system (Thermo Fisher Scientific) and separated peptides were analyzed on a benchtop Orbitrap Q Exactive plus mass spectrometer (Thermo Fisher Scientific). All data were analyzed using Spectrum Mill software package (Agilent Technologies). Identities interpreted for individual spectra were automatically designated as confidently assigned using the Spectrum Mill autovalidation module to use target-decoy based false discovery rate (FDR) estimates to apply score threshold at the spectral and protein levels. In total, 10,992 proteins were quantified. Downstream bioinformatic analysis was performed in Perseus software (developed by Max Planck Institute of Biochemistry, Munich, Germany).

Figure 4:
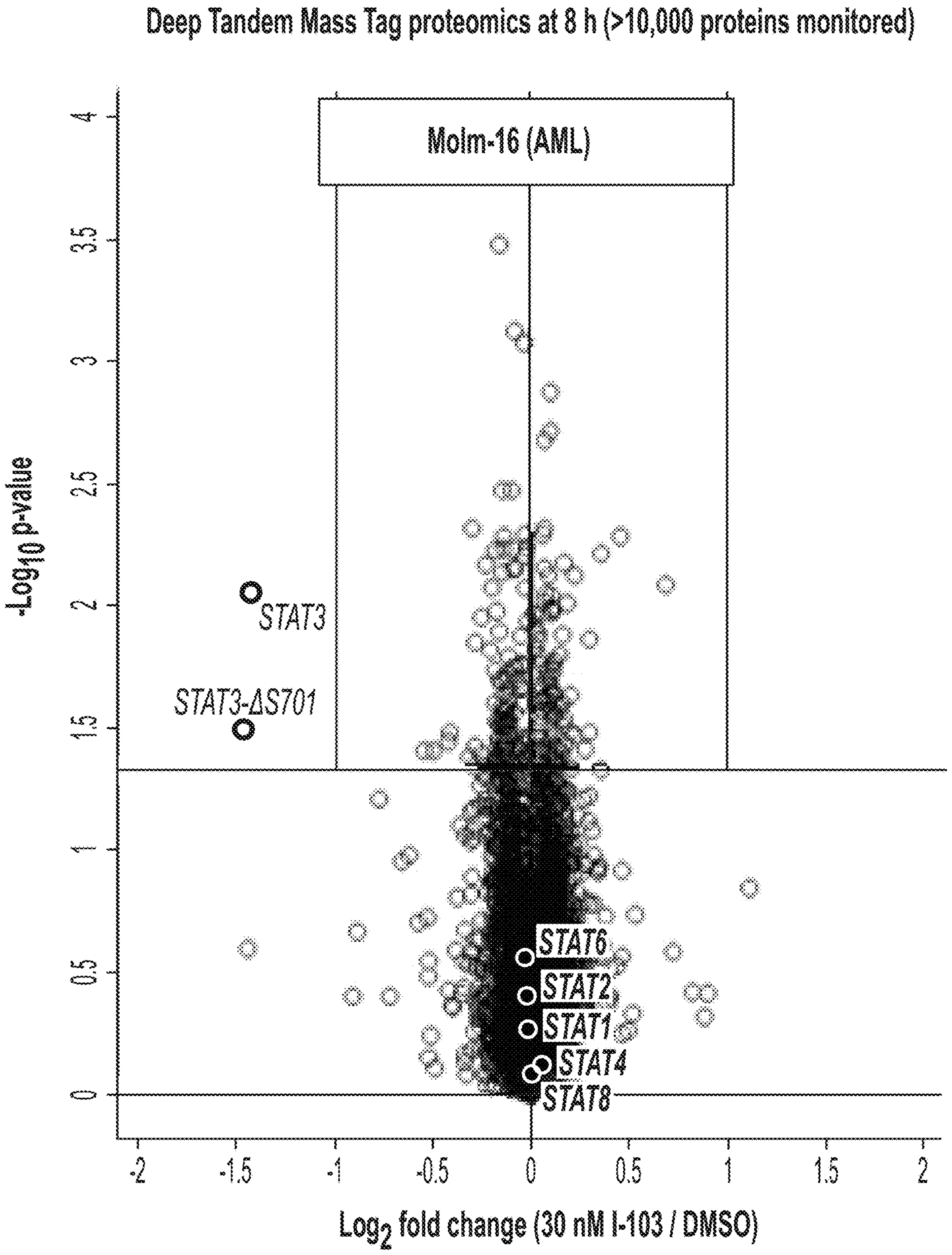
FIG. 4 includes images of deep tandem mass tag (TMT) proteomic scatterplots in MOLM-16 (AML) and SU-DHL-1 (ALCL) at 8 hours showing -Log10 p-value (y-axis) and Log2 fold change at 30 nM and 100 nM I-103 in DMSO (x-axis).
Figure 4:
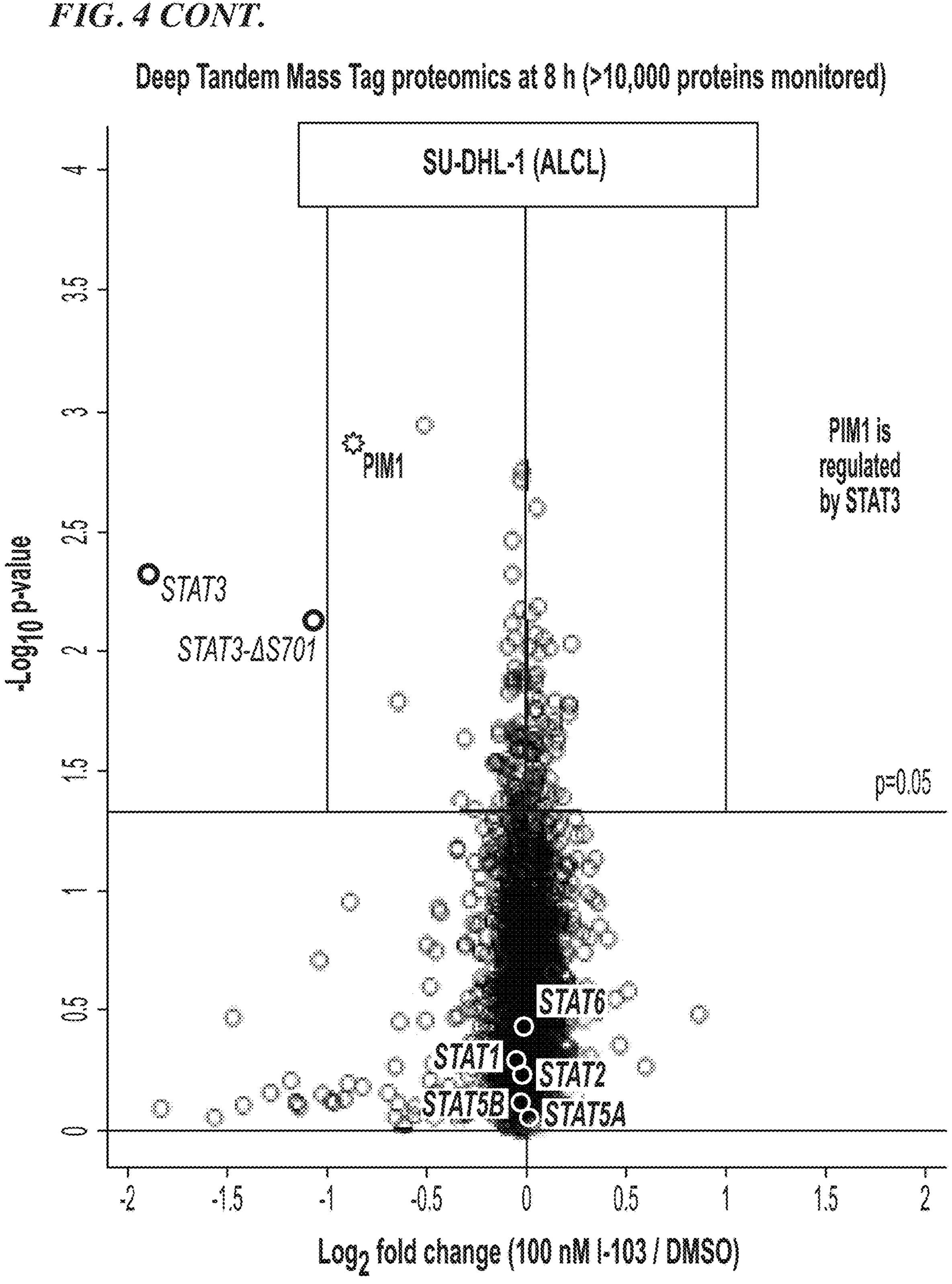
Figure 13:
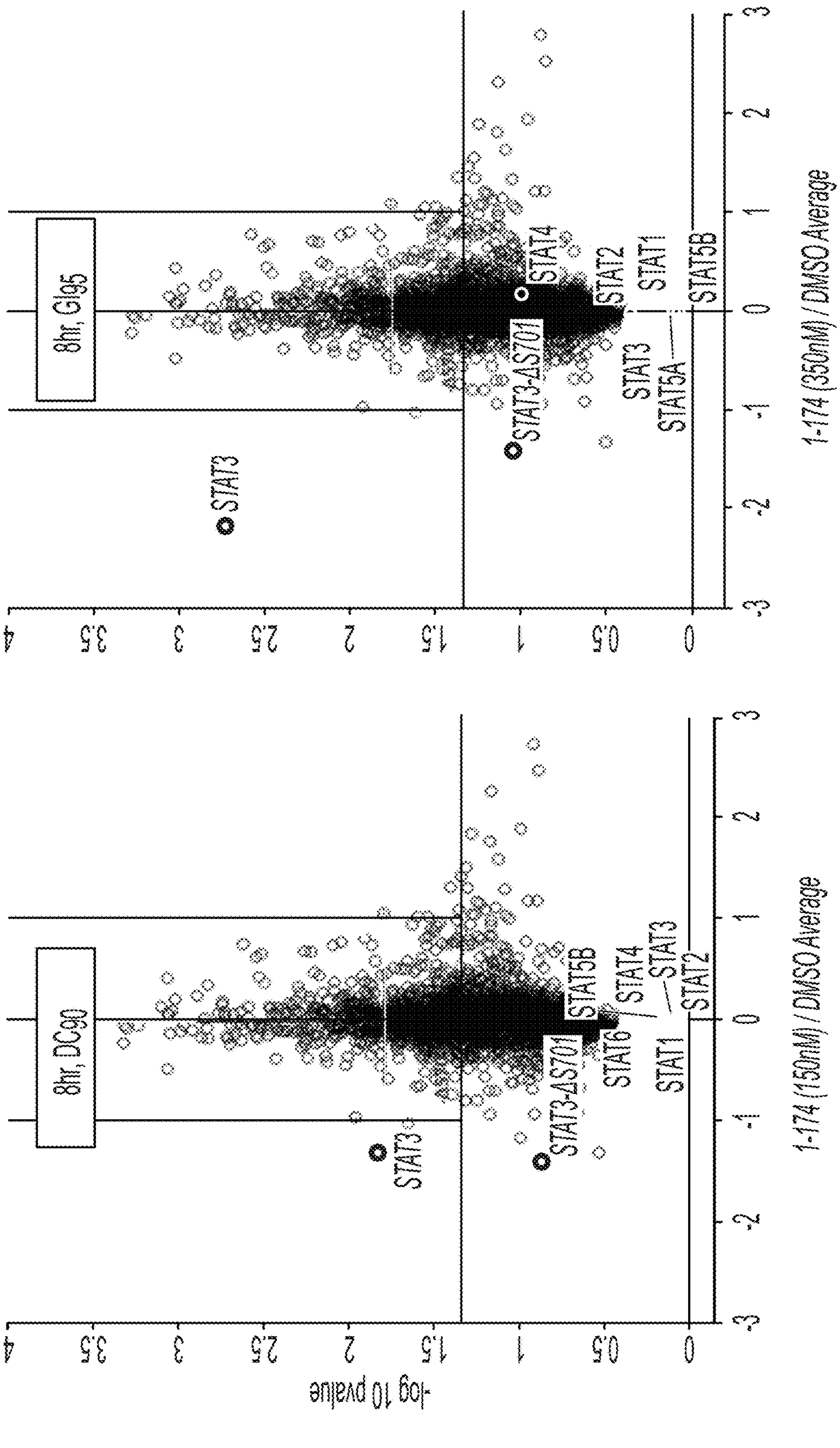
FIG. 13 includes images of deep tandem mass tag (TMT) proteomic scatterplots in SU-DHL-1 (ALCL) at 8 hours showing -Log10 p-value (y-axis) and Log2 fold change at 150 nM, 350 nM, and 3.5 pM I-174 in DMSO (x-axis).
Figure 13:
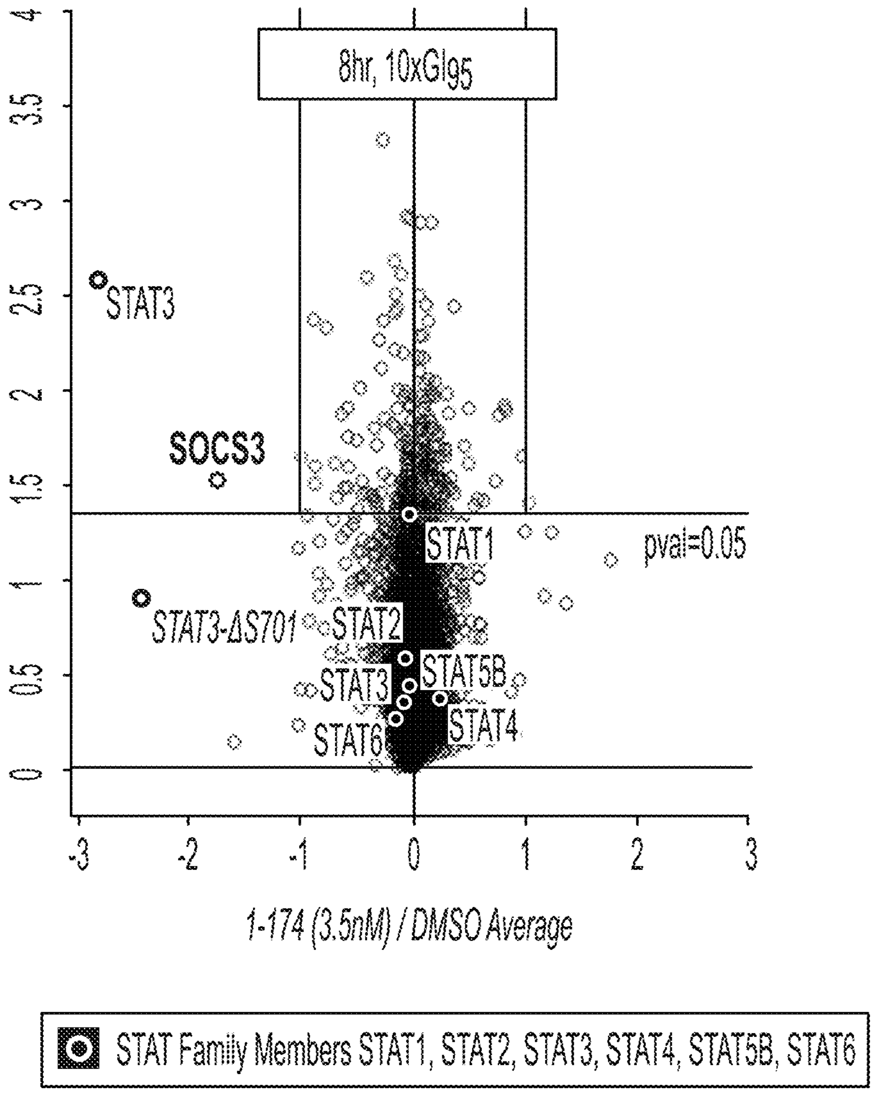

Degradation in Molm-16 and SU-DHL-1 cells was highly selective for STAT3 vs >10,000 other detected proteins (including all other STAT family members) as evaluated by deep tandem mass tag proteomics. FIGS. 4 and 13 show proteomic scatterplots for I-103 and I-174 respectively.

Example 299. Xenograph Tumor Studies

Animals: 50 6-8 week old female NOD SCID mice weighing 18 to 20 grams. 25 mice were used in each study.

Quarantine: Animals were quarantined for 7 days before study. The general health of the animals was evaluated by a veterinarian, and complete health checks were performed. Animals with abnormalities were excluded prior the study.

Housing: General procedures for animal care and housing were in accordance with the standard, Commission on Life sciences, National Research Council, Standard operating procedures (SOPs) of Pharmaron, Inc. The mice were kept in laminar flow rooms at constant temperature and humidity with 3-5 mice in each cage. Animals were housed in polycarbonate cages (300×180×150 $mm^3$) in an environmentally monitored, well-ventilated room maintained at a temperature of (22 3C) and a relative humidity of 40% 80%. Fluorescent lighting provided illumination approximately 12 hours per day. The bedding material was soft wood, which was changed once per week.

Animal ID: Each animal was assigned an identification number; the following identification method was applied. Each cage card was labeled with such information as study number, group, sex, dose, animal number, initiation date, study director and telephone number. Individual animals were identified by ear coding.

Diet: Animals had free access to irradiation sterilized dry granule food during the entire study period except for time periods specified by the protocol. Sterile drinking water in a bottle was available to all animals ad libitum during the quarantine and study periods. The bottle and the stopper with attached sipper tube was autoclaved prior to use. Samples of water from the animal facility were analyzed and results of water analysis will be retained in the facility records and were reviewed by the veterinarian, or designee, to assure that no known contaminants are present that could interfere with or affect the outcome of studies.

Method for Tumor Inoculation: Each mouse was inoculated subcutaneously with SU-DHL-1 tumor cells (1×107+Matrigel) or SUP-M2 tumor cells (5×106+Matrigel) in 0.1 ml of RPM11640 medium supplemented with 10% FBS, 100 U/ml penicillin and 100 mg/ml streptomycin for tumor development. Mice were then assigned to groups such that the mean tumor volume was the same for each treatment group and time point. The treatments were administered to the tumor-bearing mice accordingly to the study design showed in Table 87 (SU-DHL1) and Table 88 (SUP-M2). Vehicle was 25% HP—P-CD in water adjusted to pH 7.4.

TABLE 87

Groups and Treatments (SU-DUL-1)

| Group # | Animals/ Group | Drug | Dose (mg/kg) | Dose Volume (mL/kg) | Route | Regimen |
|---|---|---|---|---|---|---|
| 1 | 5 | Vehicle | — | 5 | IP | 2 days on/5 days off × 2 wks |
| 2 | 5 | I-174 | 2.5 | 5 | IP | 2 days on/5 days off × 2 wks |
| 3 | 5 | I-174 | 5 | 5 | IP | 2 days on/5 days off × 2 wks |
| 4 | 5 | I-174 | 10 | 5 | IP | 2 days on/5 days off × 2 wks |
| 5 | 5 | I-174 | 25 | 5 | IP | 2 days on/5 days off × 2 wks |

TABLE 88

Groups and Treatments (SUP-M2)

| Group # | Animals/ Group | Drug | Dose (mg/kg) | Dose Volume (mL/kg) | Route | Regimen |
|---|---|---|---|---|---|---|
| 1 | 5 | Vehicle | — | 5 | IV | 2 days on/5 days off × 2 wks |
| 2 | 5 | I-174 | 3 | 5 | IV | 2 days on/5 days off × 2 wks |
| 3 | 5 | I-174 | 10 | 5 | IV | 2 days on/5 days off × 2 wks |
| 4 | 5 | I-174 | 30 | 5 | IV | 2 days on/5 days off × 2 wks |
| 5 | 5 | I-174 | 30 | 5 | IV | QW × 2 wks |

Measurement Parameters: Study animals were monitored not only for tumor growth but also behavior such as mobility, food and water consumption (by cage side checking only), body weight (BW), eye/hair matting and any other abnormal effect. Any mortality and/or abnormal clinical signs was recorded. Sponsor was notified immediately if abnormal clinical signs, or if tolerability issues were observed. Body weights of all animals were measured and recorded twice per week. The measurement of tumor size was conducted twice weekly with a caliper and recorded. The tumor volume (mm3) was estimated using the formula: TV=a x b2/2, where "a" and "b" are long and short diameters of a tumor, respectively.

Figure 19:
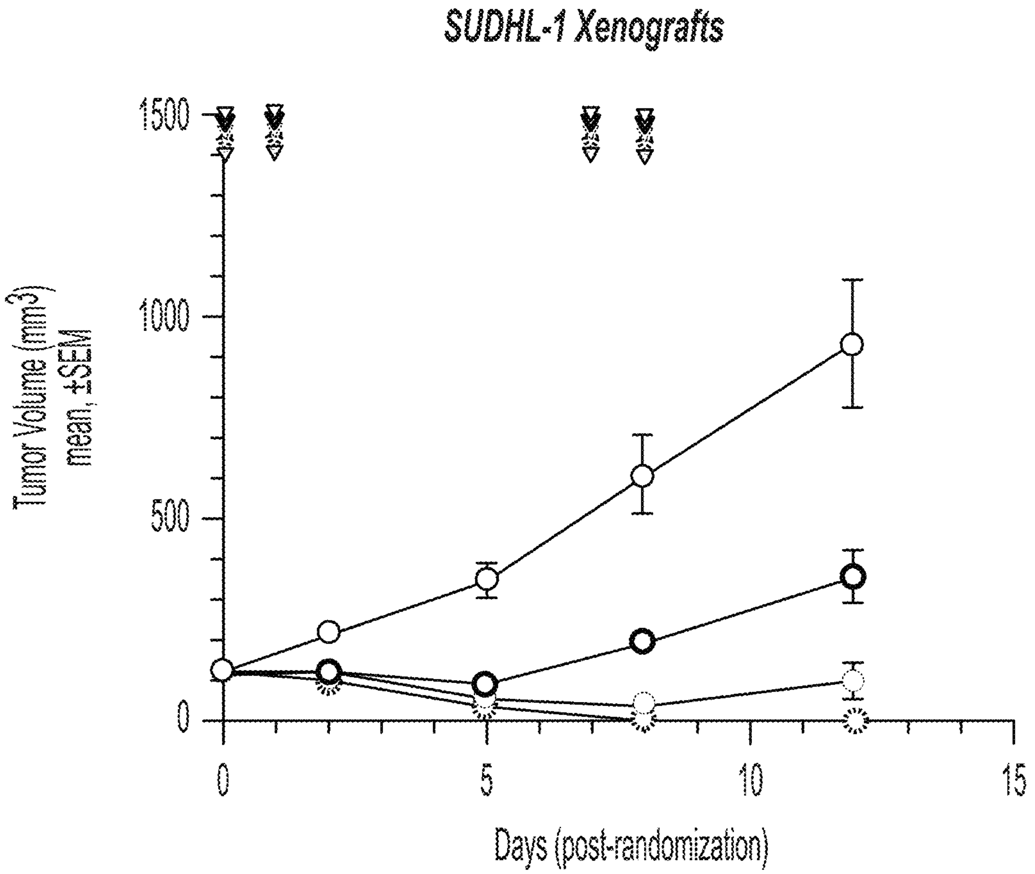
FIG. 19 depicts ALK+ALCL SU-DHL-1 mouse xenographs and $K_D$ results using I-174 for STAT3 degradation with tumor volume median ($mm^3$) over days (post randomization) for vehicle, 2.5, 5, 10 and 25 mg/kg (mpk) dosing.
Figure 20:
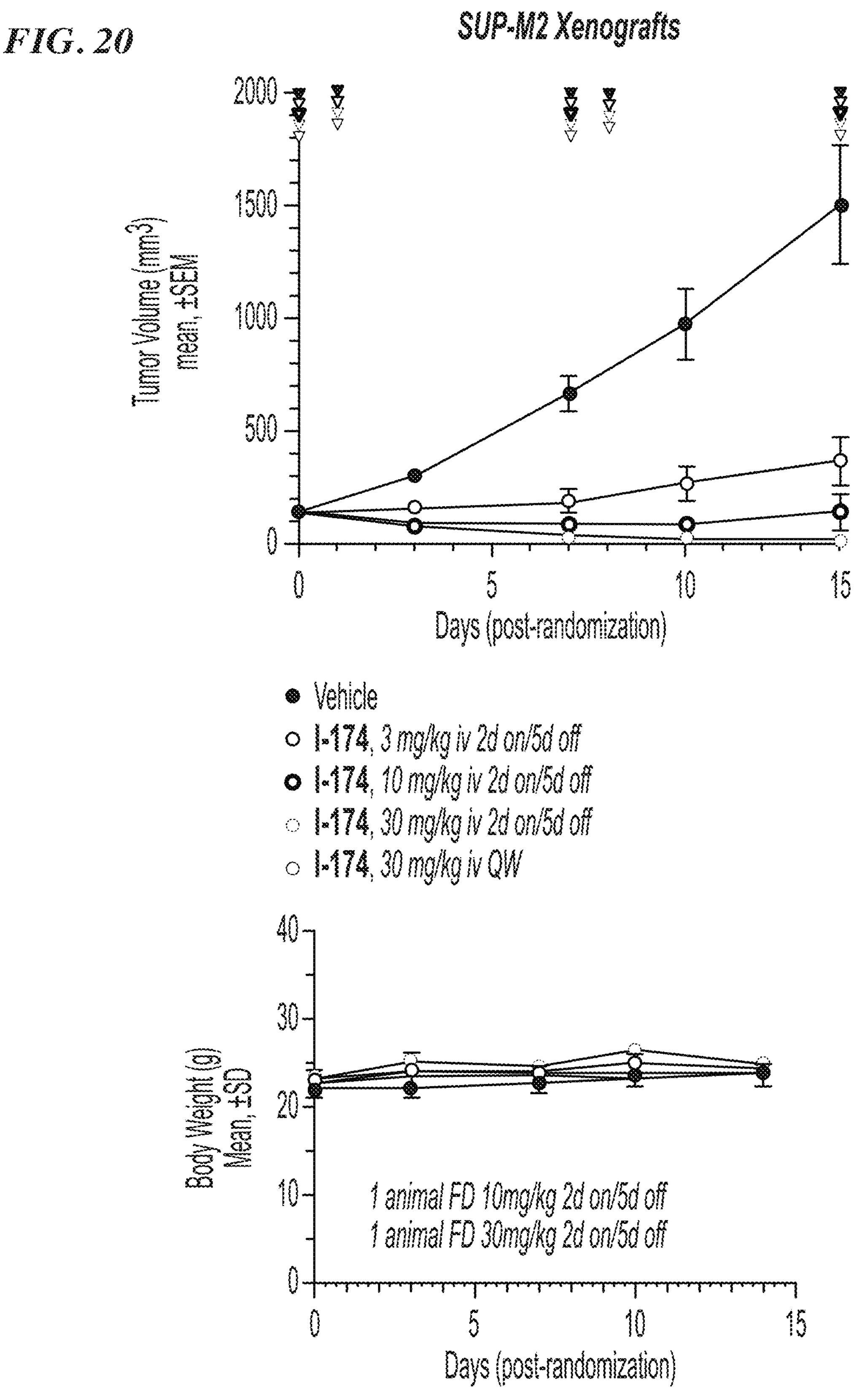
FIG. 20 includes ALK+ALCL SUP-M2 xenograph results using I-174 for STAT3 degradation with tumor volume median ($mm^3$) over days (post-randomization) for vehicle, 3 mg/kg IV 2d on/5d off, 10 mg/kg IV 2d on/5d off, 30 mg/kg IV 2d on/5d off, and 30 mg/kg IC QW dosing (upper graph) and body weight (g) over day (post-randomization) for animal FD 10 mg/kg 2d on/5d off and 30 mg/kg 2d on/5d off (lower graph).

Results: FIG. 19 shows that intermittent dosing of A-174 achieves tumor regression in ALK+ALCL xenograph model SU-DHL-1. FIG. 20 shows that intermittent dosing of 1-174 achieves tumor regression in ALK+ALCL xenograph model SUP-M2.

Results for additional compounds of the invention in SUDHL-1 xenograph tumor studies according to the above protocol are shown in Table 89. Letter codes for tumor volume include A<500 $mm^3$, B=500-1000 $mm^3$, C=>1000 $mm^3$.

TABLE 89

| 2.5-30 mg/kg and 2 days on/5 days off | | | | | |
|---|---|---|---|---|---|
| Compound | Route | 5 days | 10 days | 15 days | 20 days |
| Vehicle | IV | B | B | C | C |
| I-94 | IV | A | B | C | C |
| I-103 | IP | A | A | A | A |
| I-174 | IV | A | A | A | A |
| I-174 | IP | A | A | A | A |
| I-195 | IP | A | A | A | A |
| I-196 | IP | A | A | A | A |
| I-233 | IV | A | A | A | A |
| I-241 | IV | A | A | A | A |
| I-261 | IP | A | A | A | A |
| I-262 | IV | A | A | A | A |
| I-275 | IP | A | A | A | A |

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A compound selected from the group consisting of:

I-83

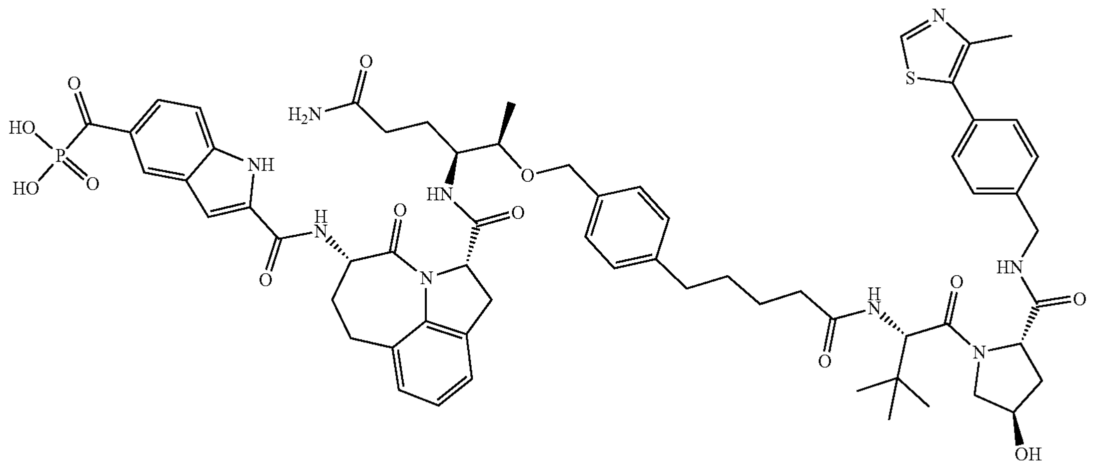

I-94

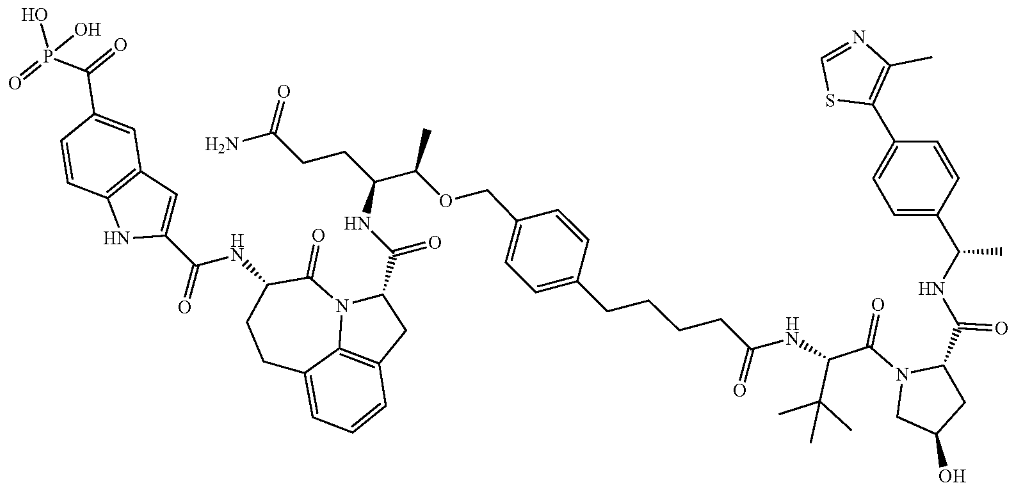

-continued
I-103
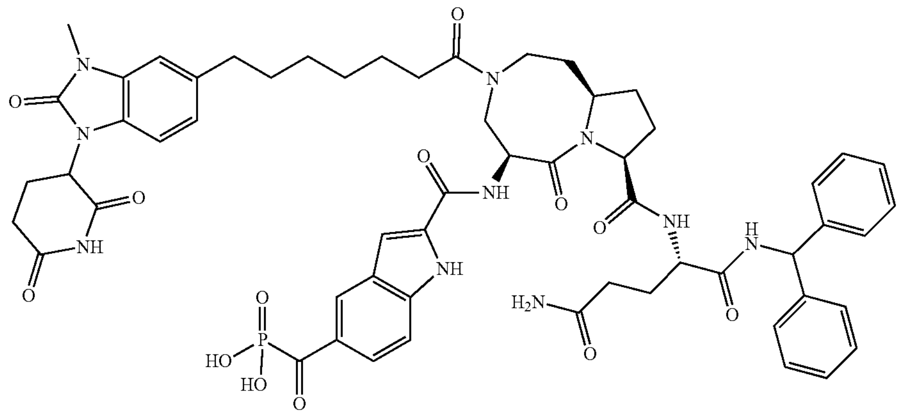
I-166
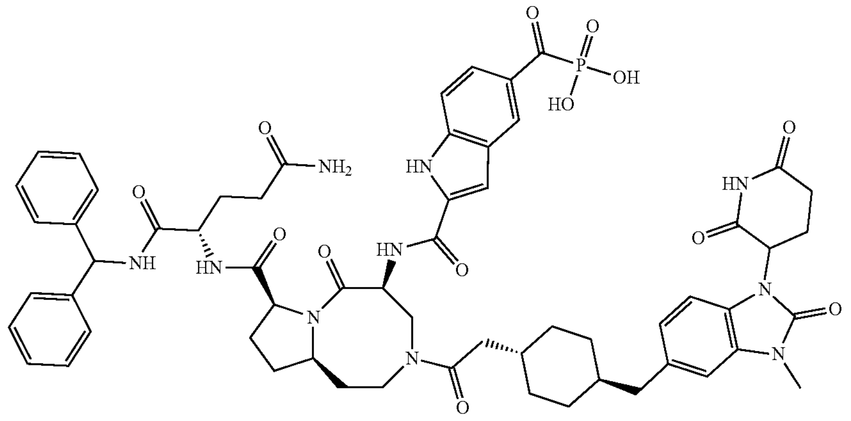
I-195
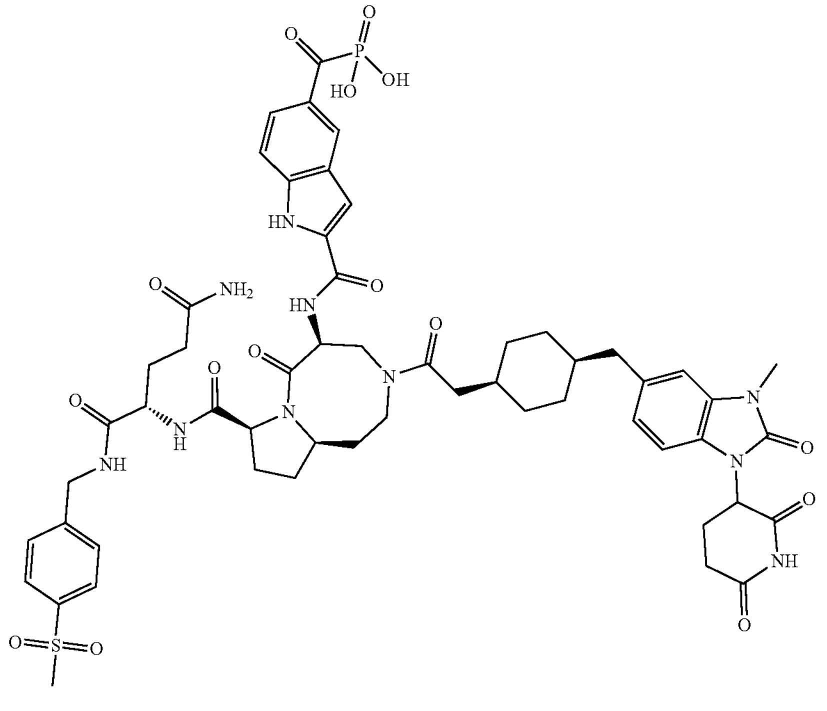

-continued
I-196
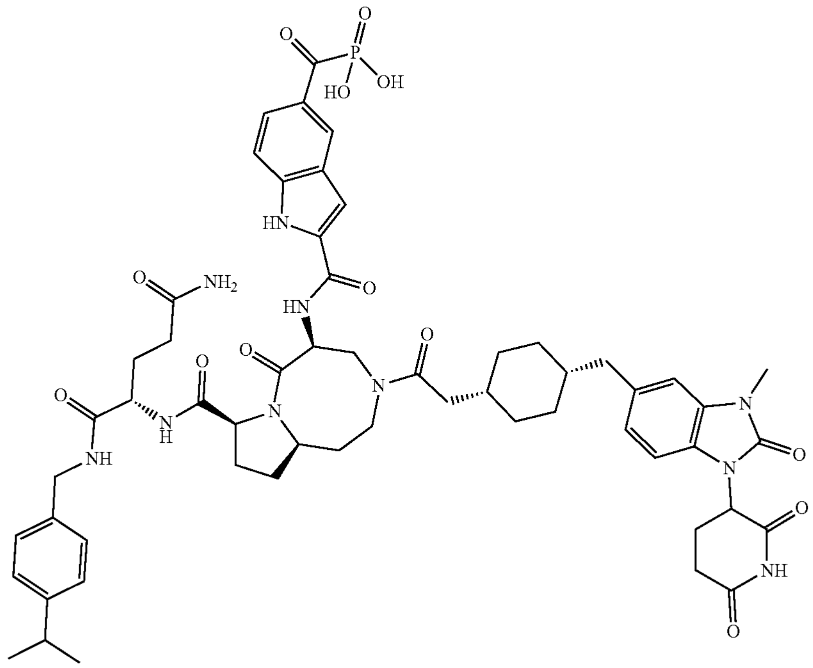
I-213
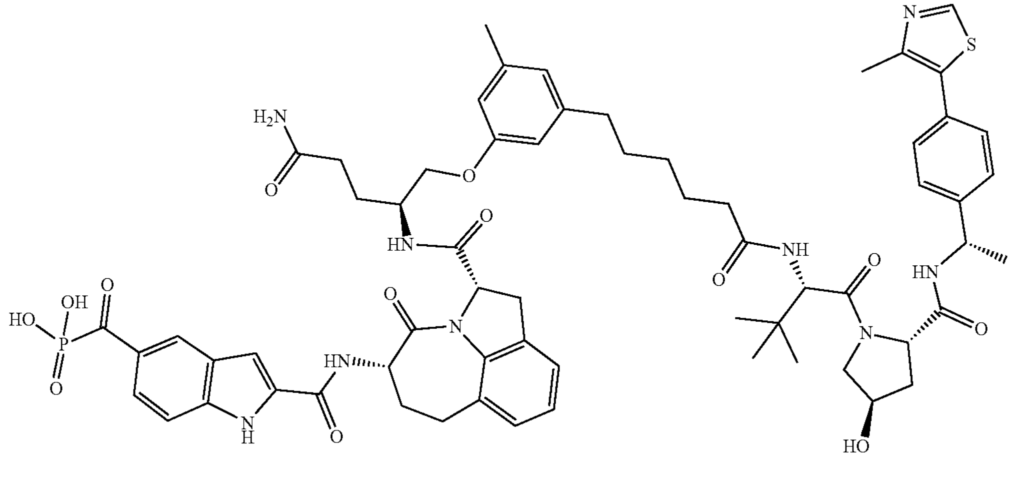
I-217
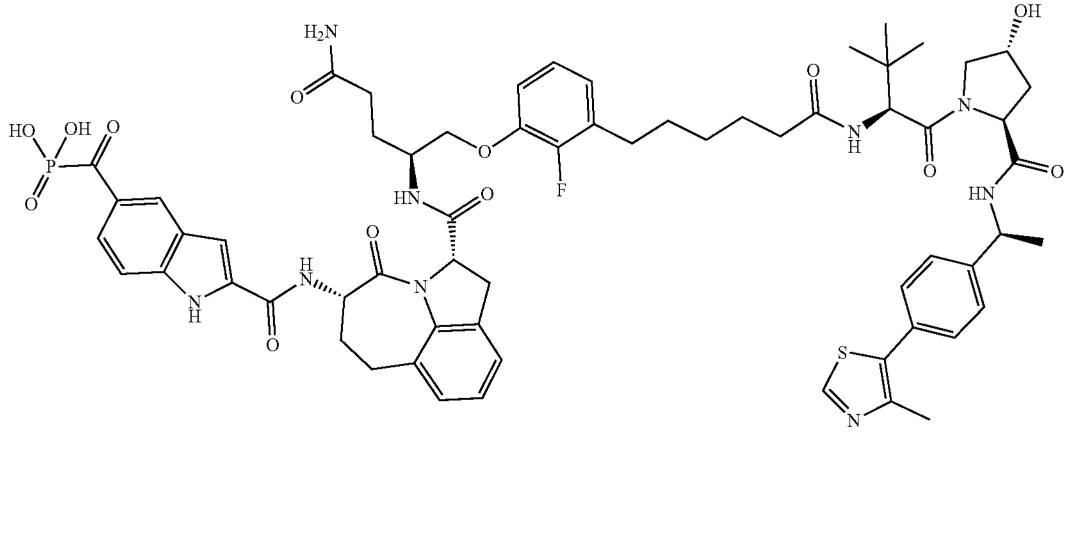

-continued
I-218
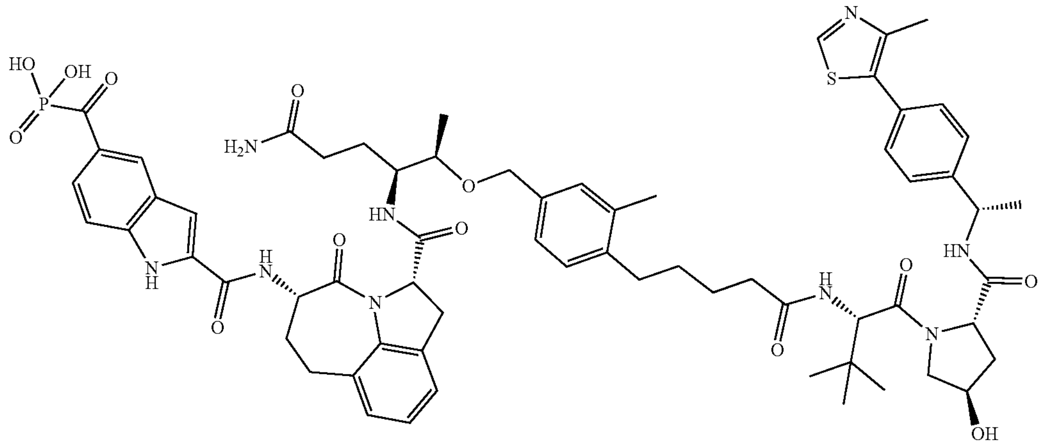
I-239
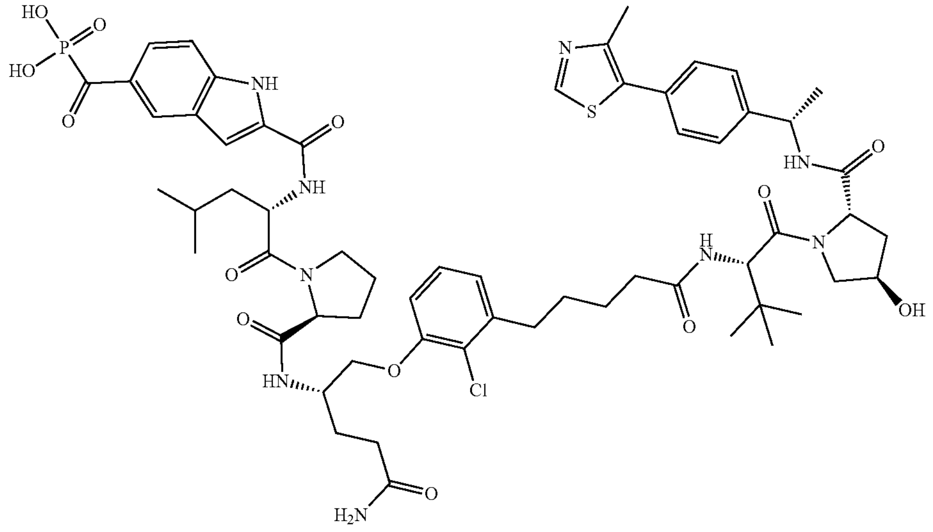
I-241
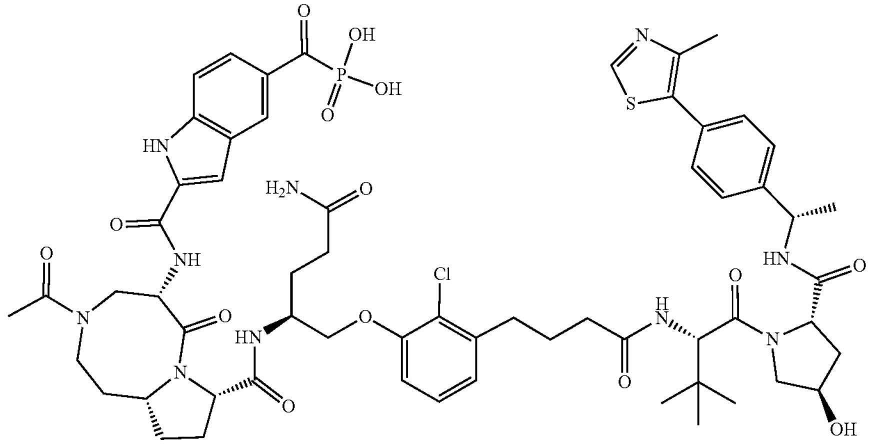

-continued
I-243
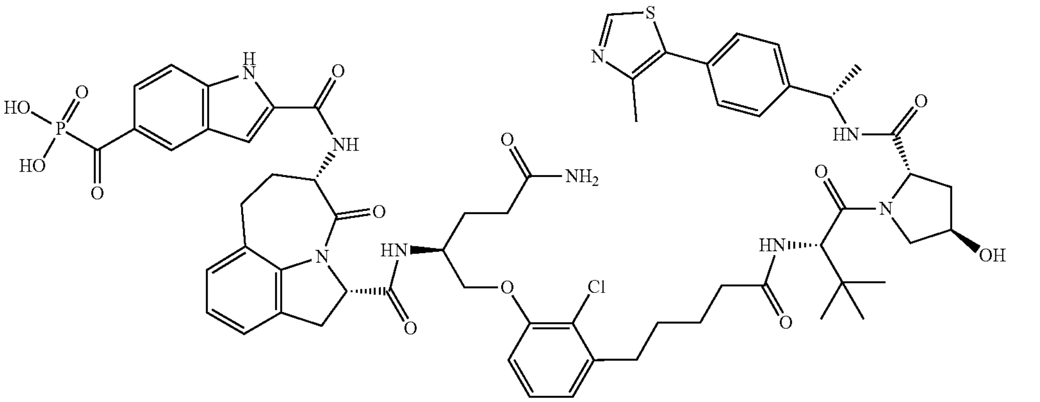
I-244
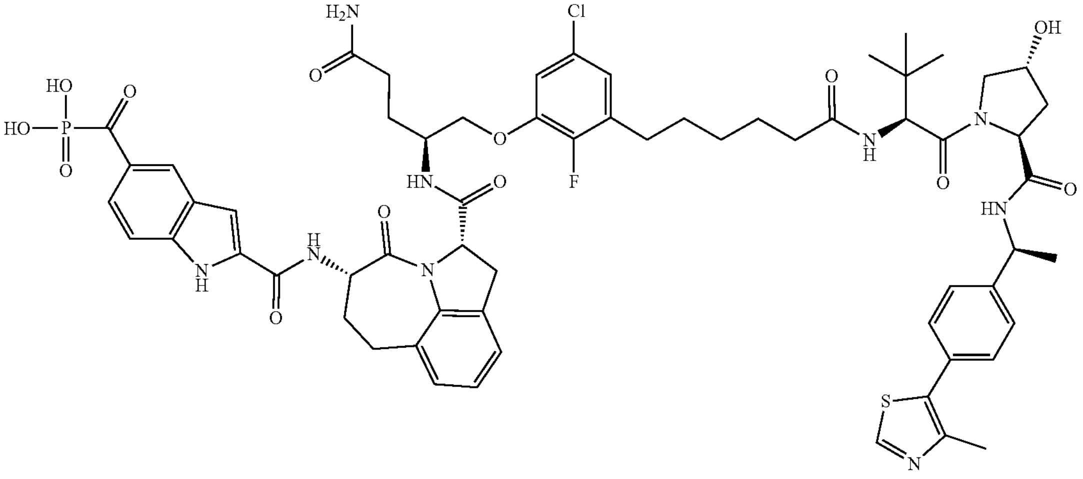
I-251
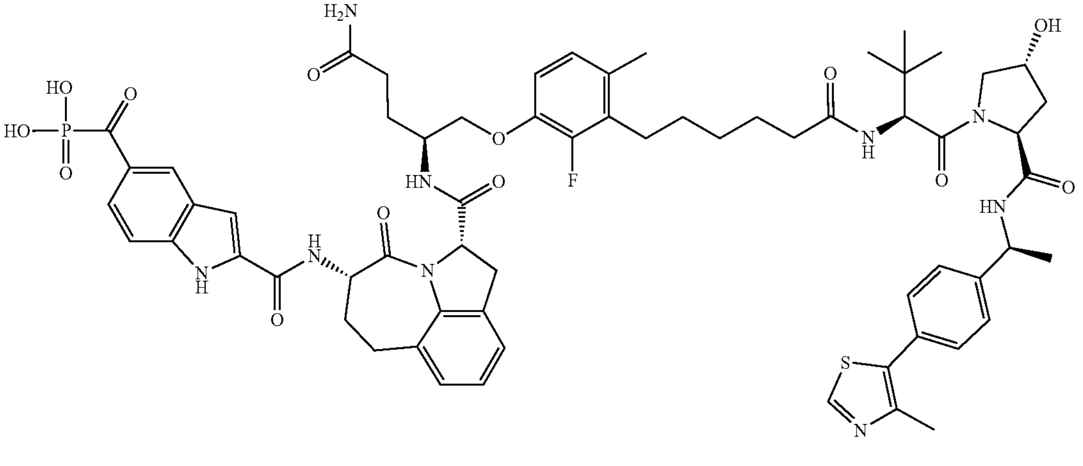

-continued
I-258
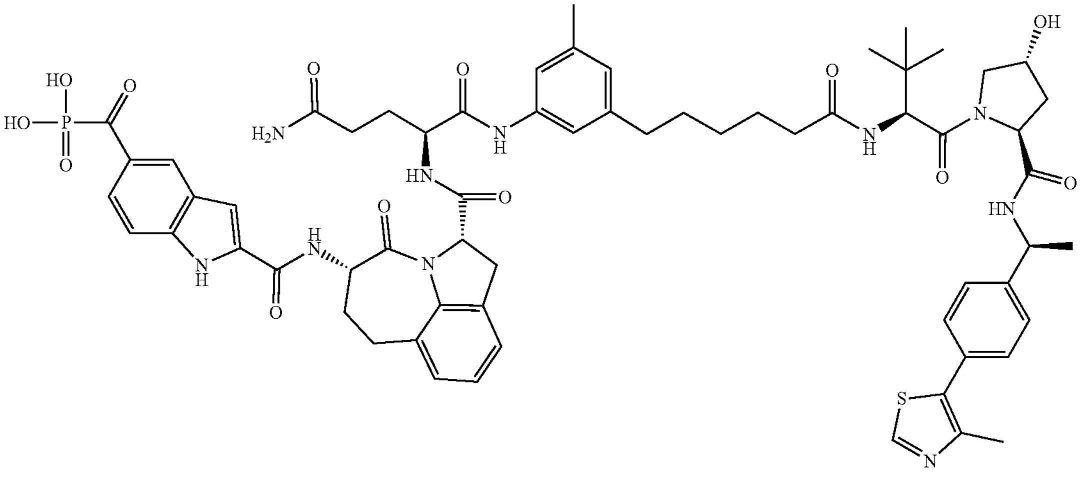
I-261
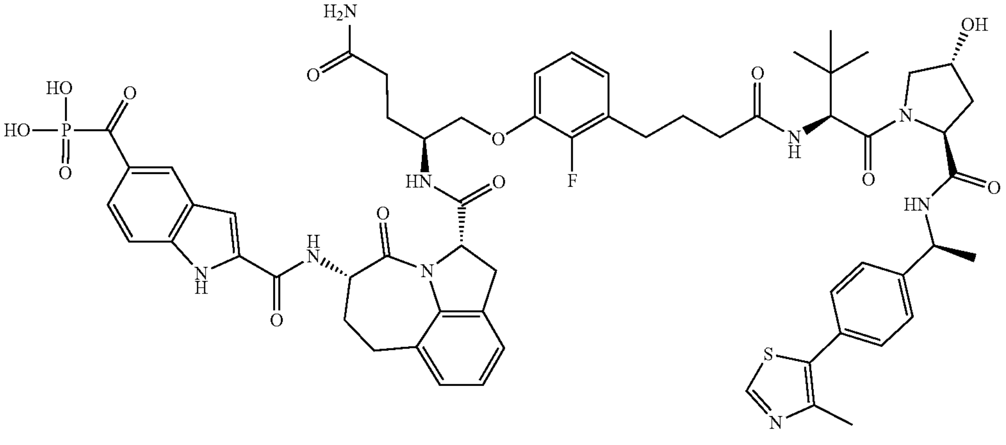
I-262
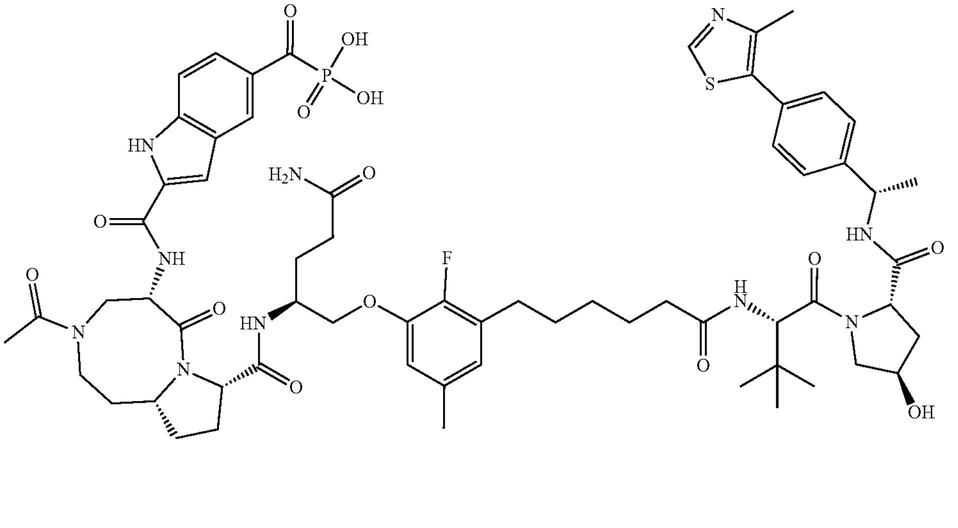

-continued
I-272
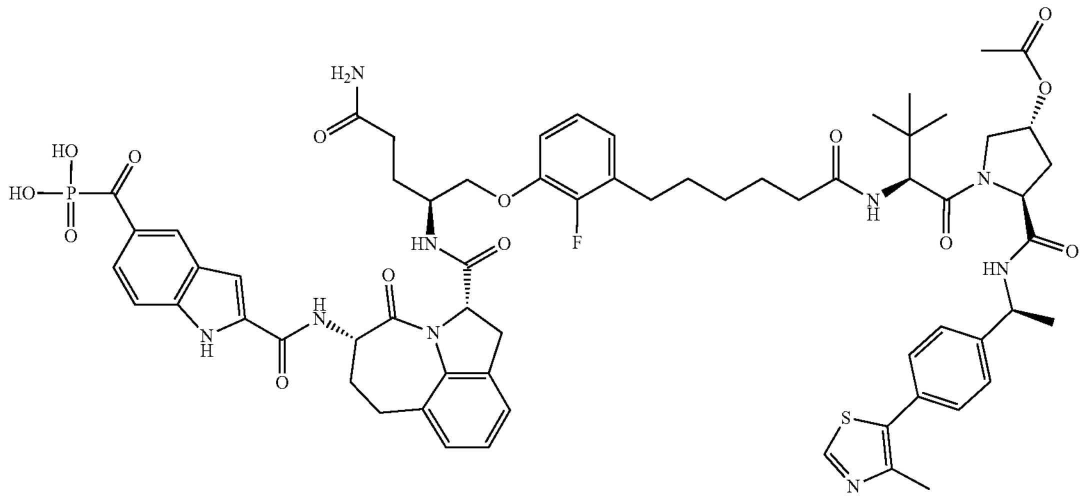
I-275
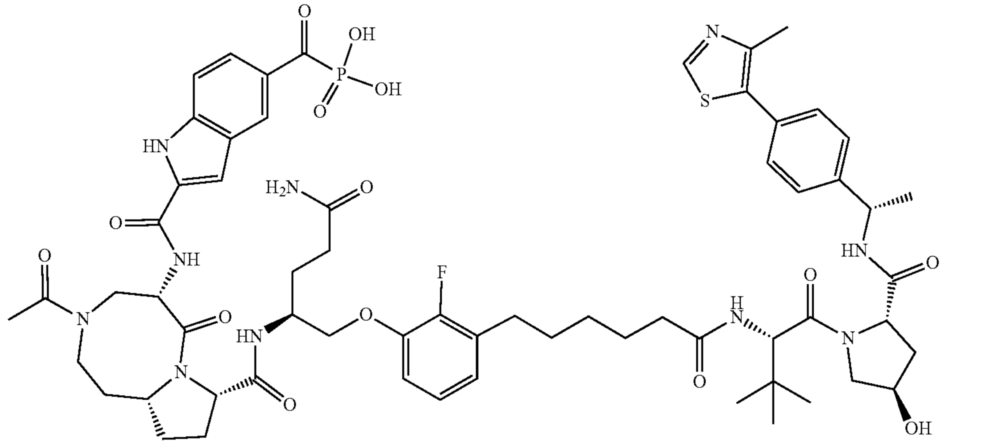
I-276
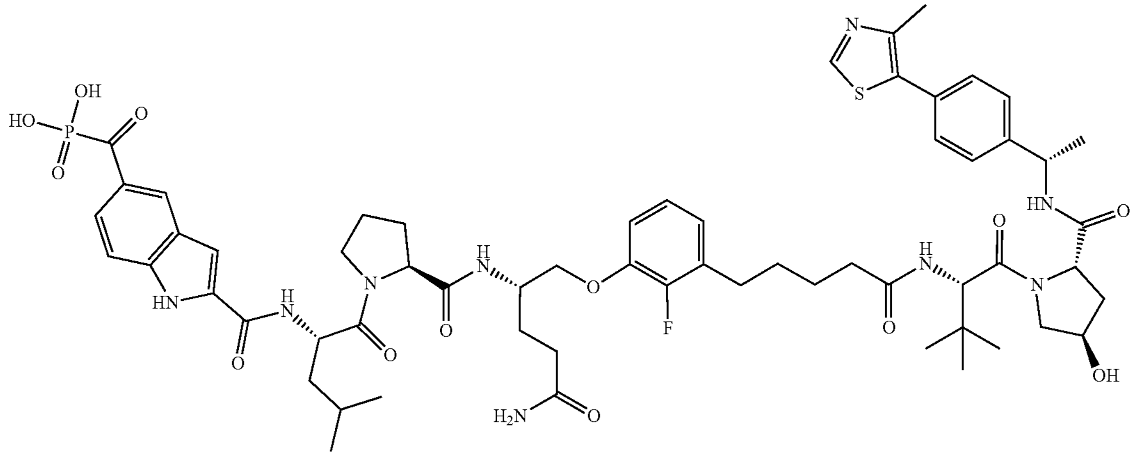

-continued
I-279
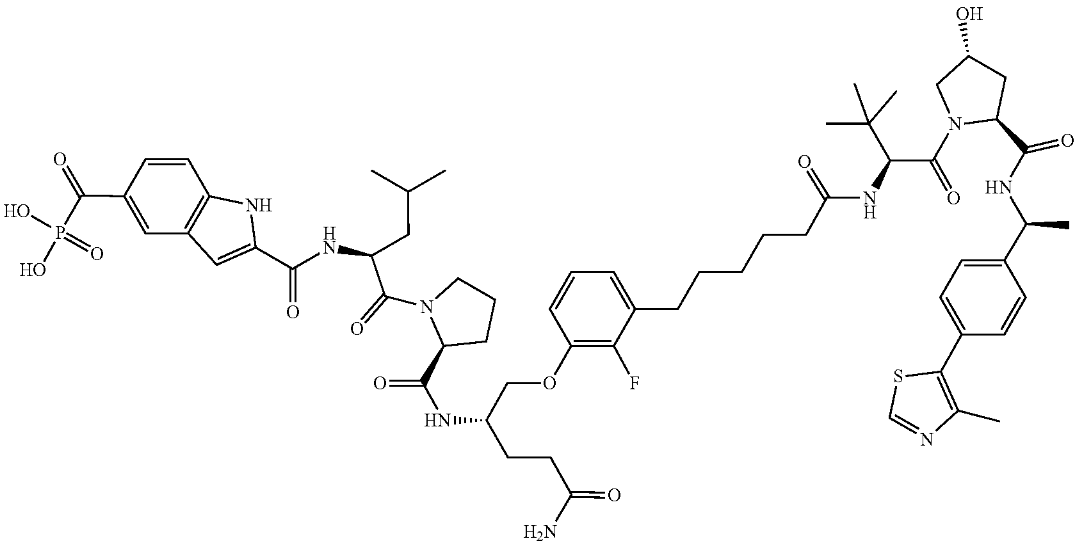
I-281
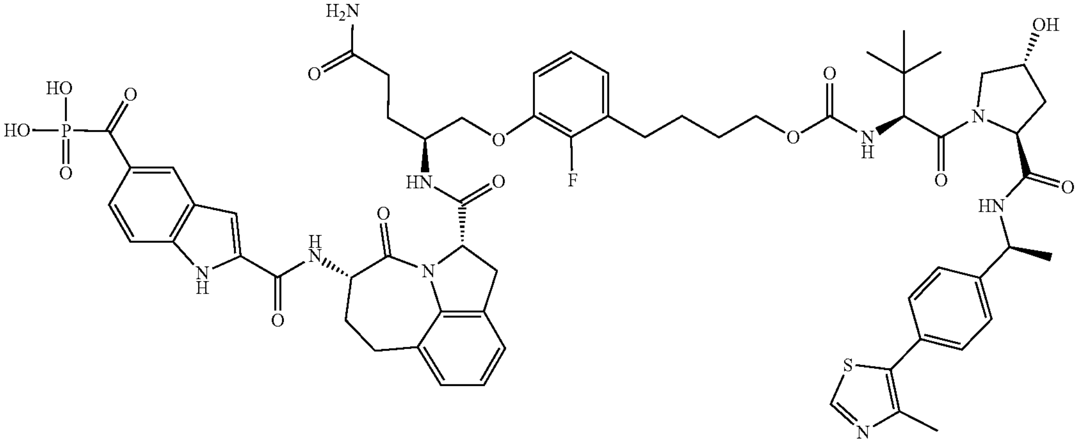
I-294
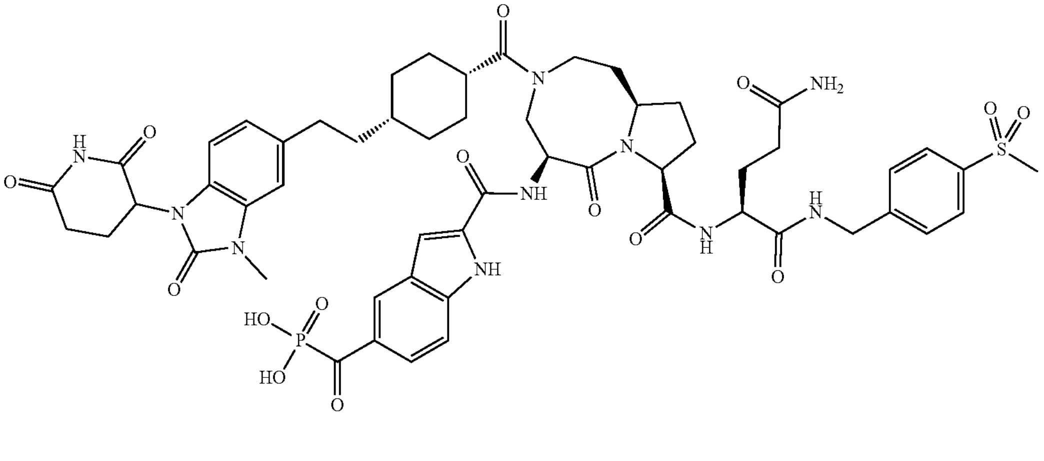

-continued
I-295
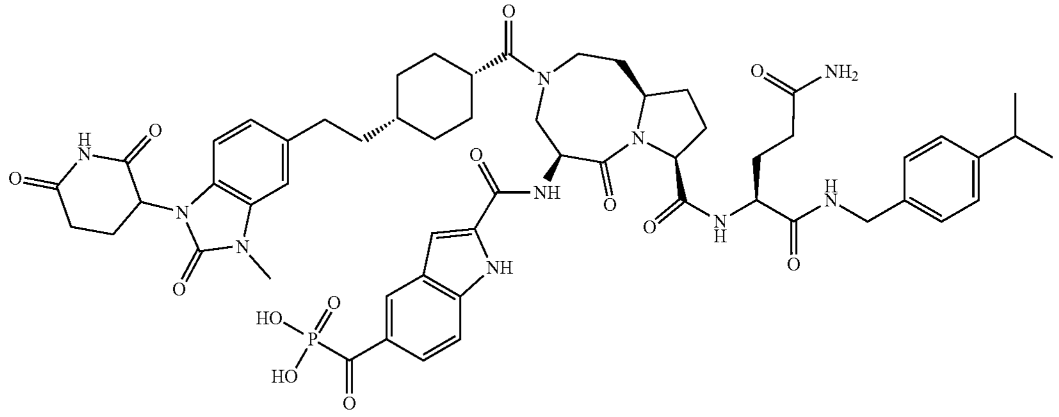
or a pharmaceutically acceptable salt thereof.
2. The compound of claim 1, wherein said compound is
I-83
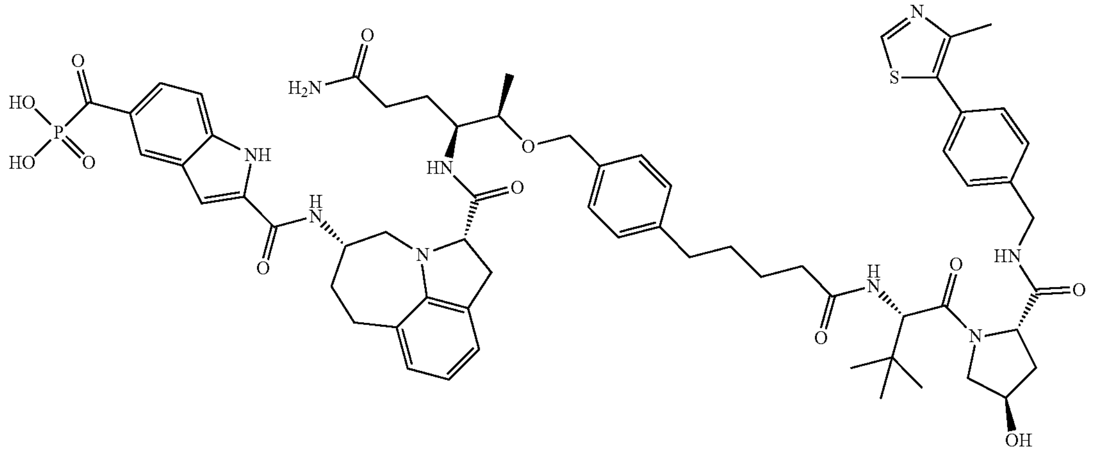
or a pharmaceutically acceptable salt thereof.
3. The compound of claim 1, wherein said compound is
I-94
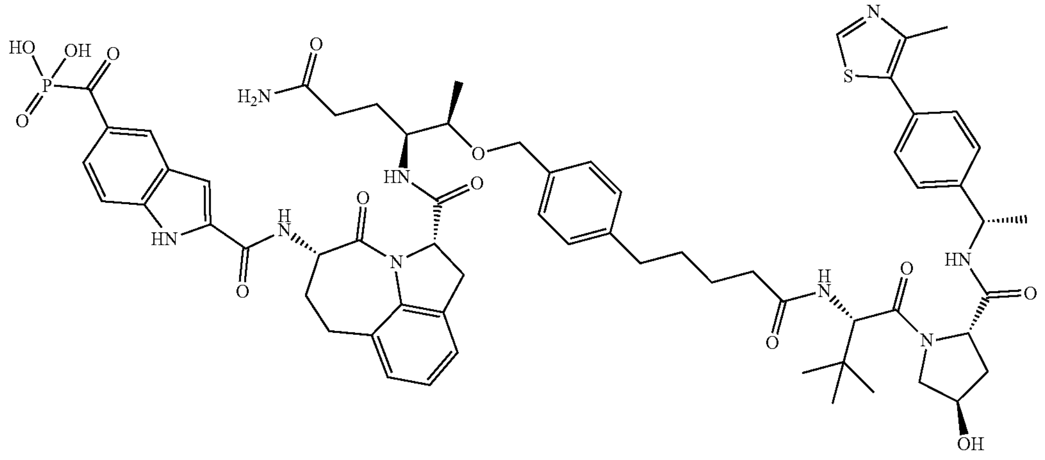
or a pharmaceutically acceptable salt thereof.

4. The compound of claim 1, wherein said compound is
I-103
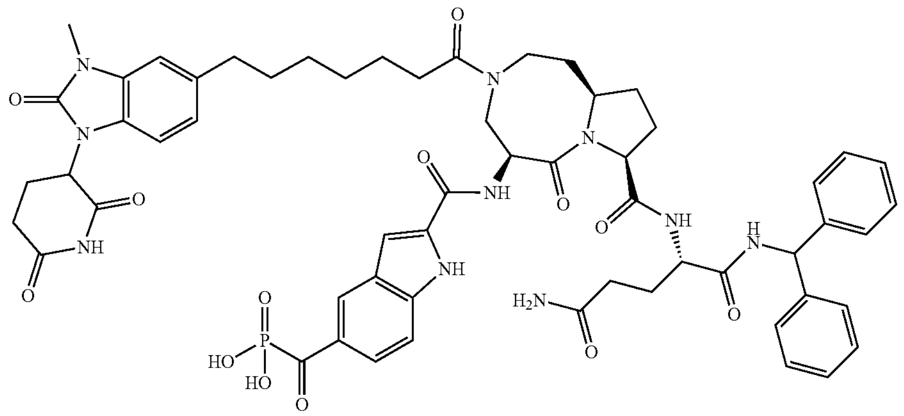
or a pharmaceutically acceptable salt thereof.
5. The compound of claim 1, wherein said compound is
I-166
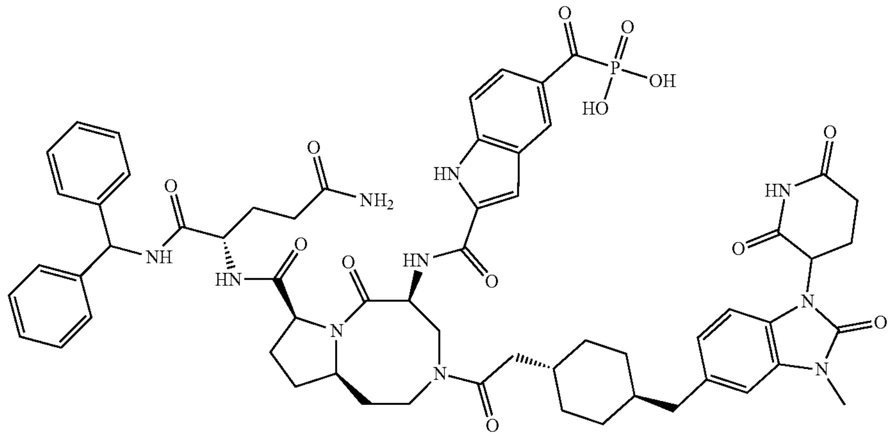
or a pharmaceutically acceptable salt thereof.

6. The compound of claim 1, wherein said compound is
I-195
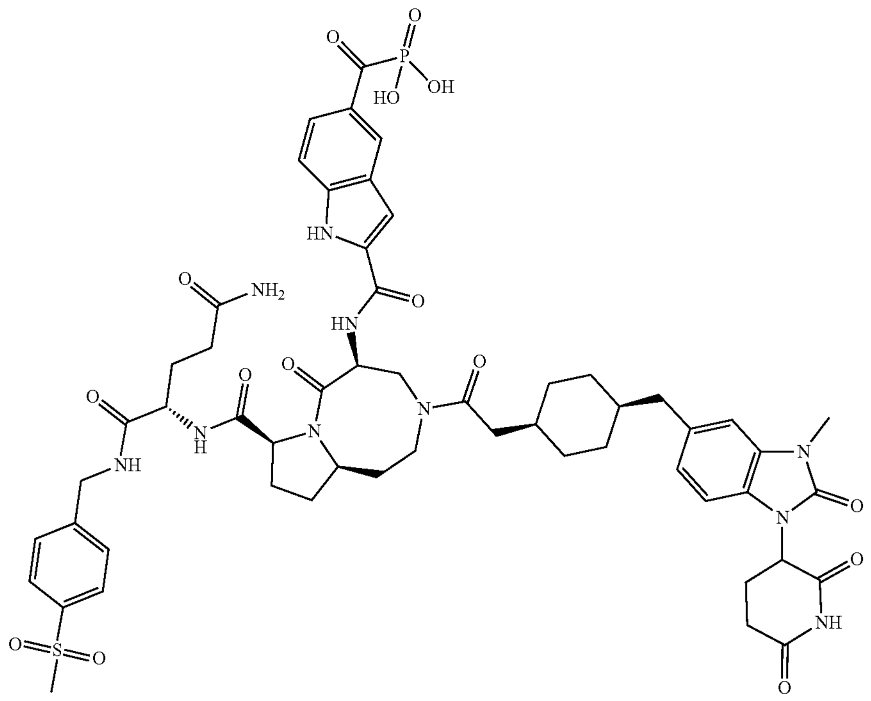
or a pharmaceutically acceptable salt thereof.
7. The compound of claim 1, wherein said compound is
I-196
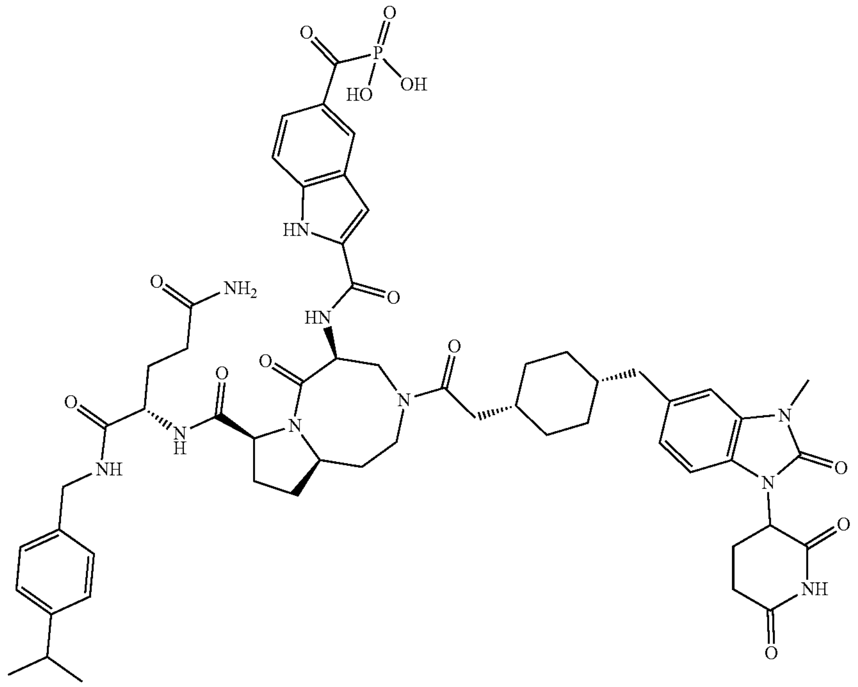
or a pharmaceutically acceptable salt thereof.

8. The compound of claim 1, wherein said compound is
I-213
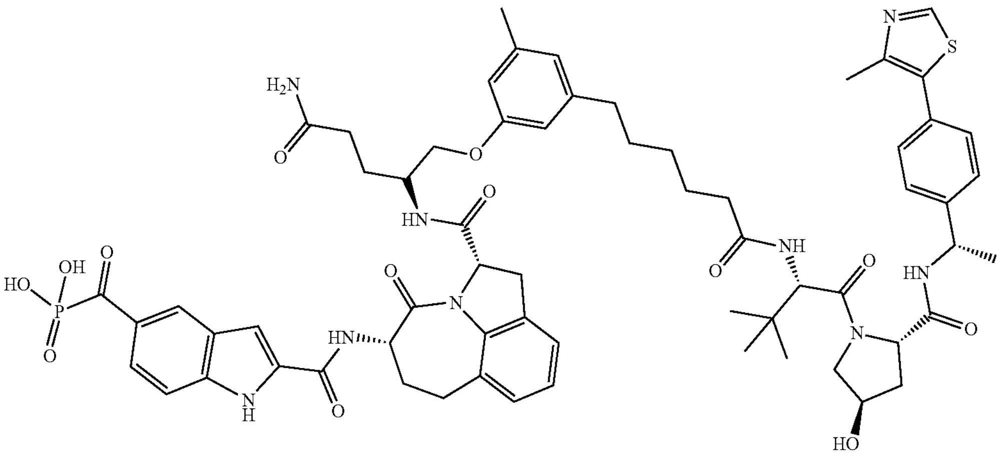
or a pharmaceutically acceptable salt thereof.
9. The compound of claim 1, wherein said compound is
I-217
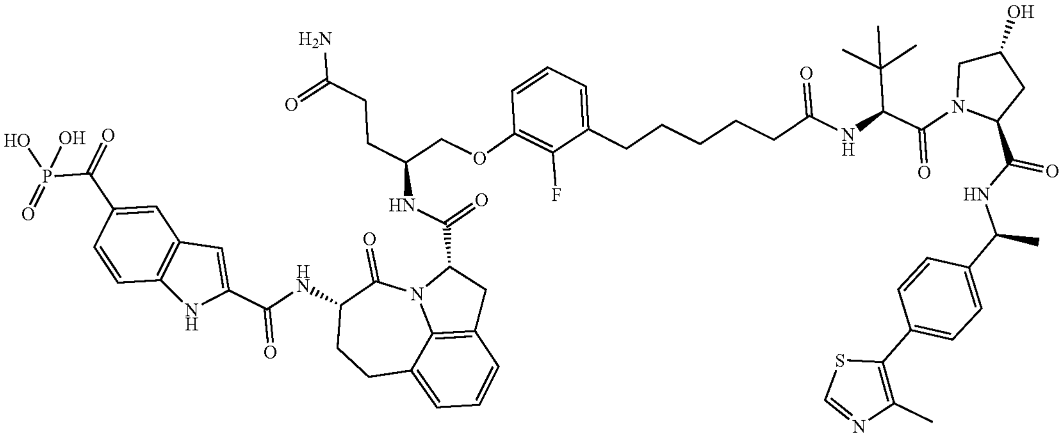
or a pharmaceutically acceptable salt thereof.

10. The compound of claim 1, wherein said compound is
I-218
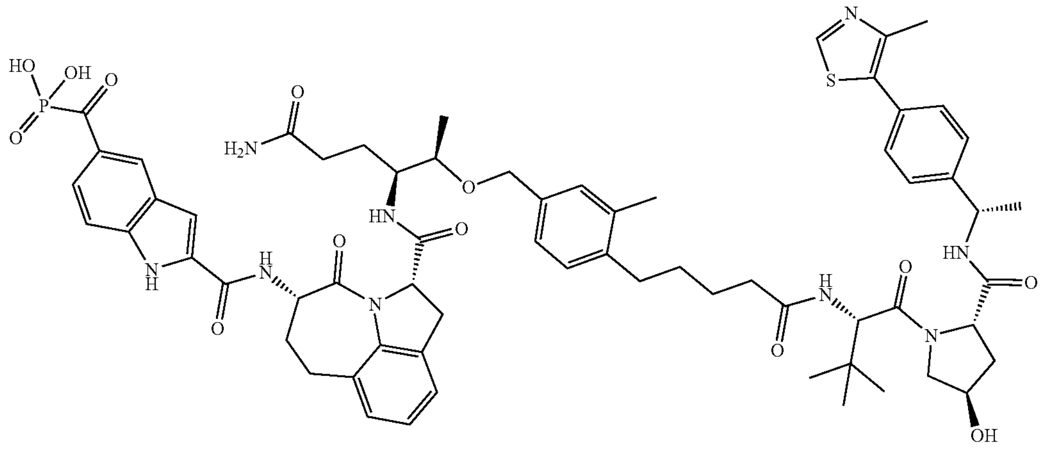
or a pharmaceutically acceptable salt thereof.
11. The compound of claim 1, wherein said compound is
I-239
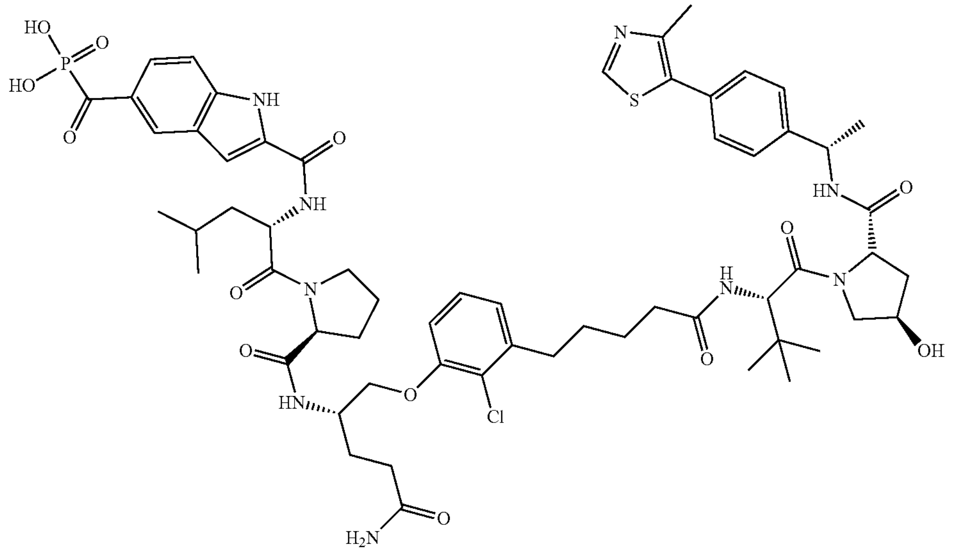
or a pharmaceutically acceptable salt thereof.

12. The compound of claim 1, wherein said compound is
I-241
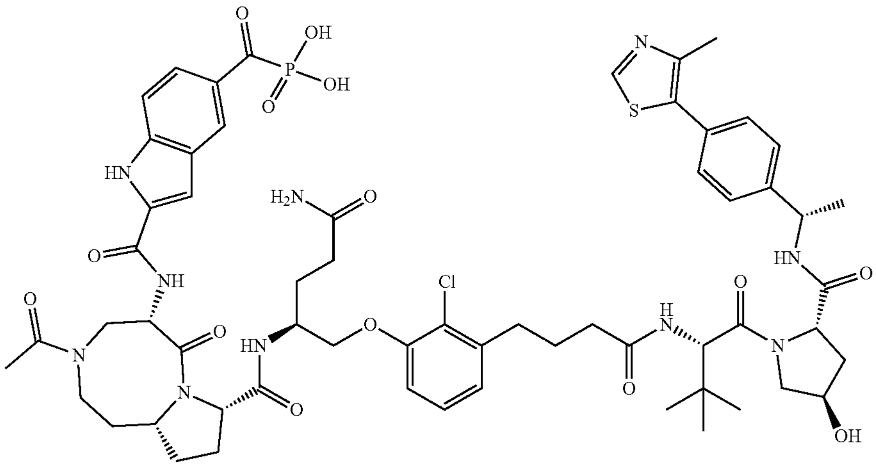
or a pharmaceutically acceptable salt thereof.
13. The compound of claim 1, wherein said compound is
I-243
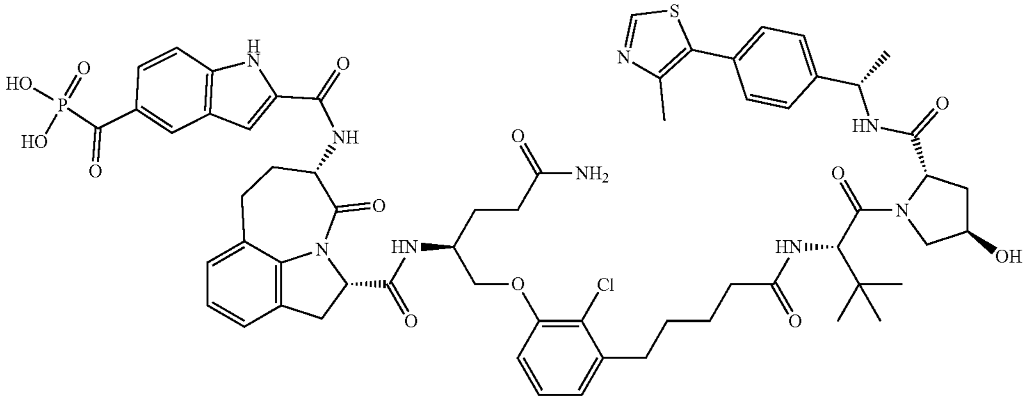
or a pharmaceutically acceptable salt thereof.
14. The compound of claim 1, wherein said compound is
I-244
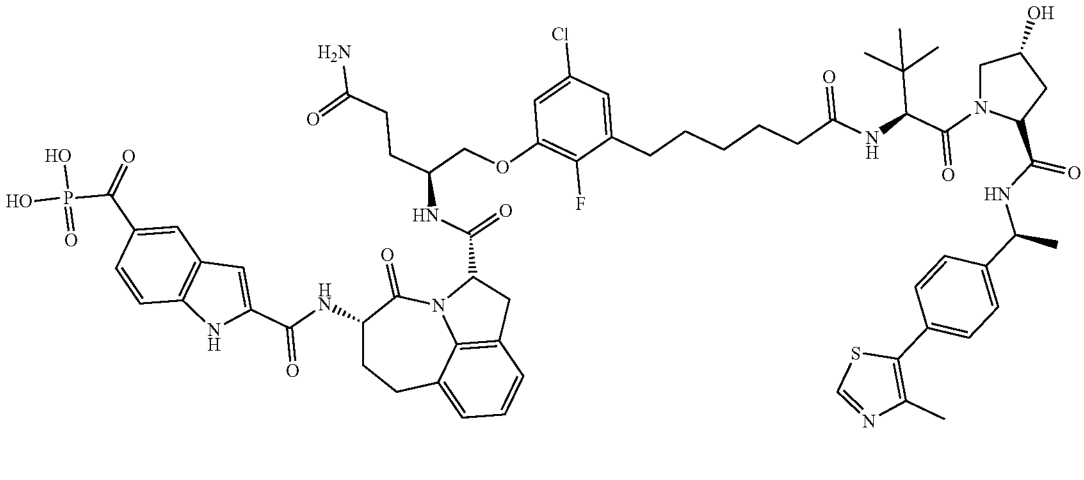
or a pharmaceutically acceptable salt thereof.

15. The compound of claim 1, wherein said compound is
I-251
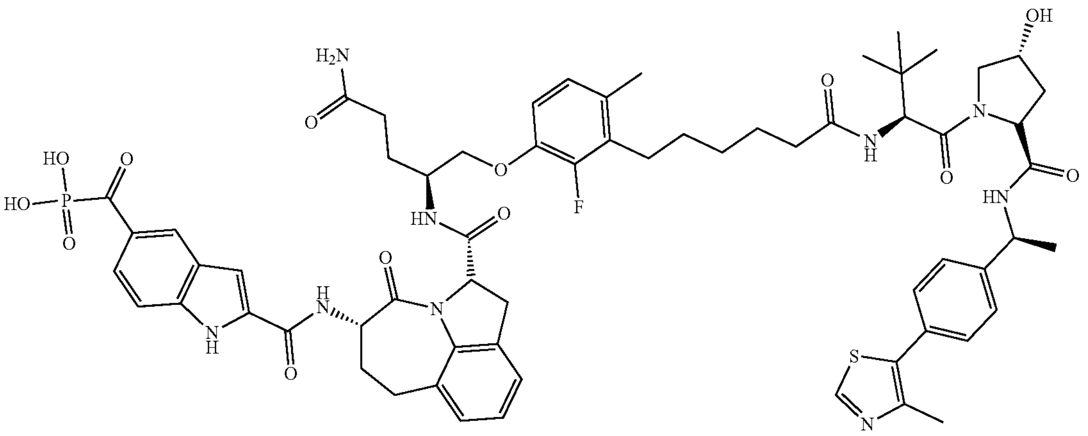
or a pharmaceutically acceptable salt thereof.
16. The compound of claim 1, wherein said compound is
I-258
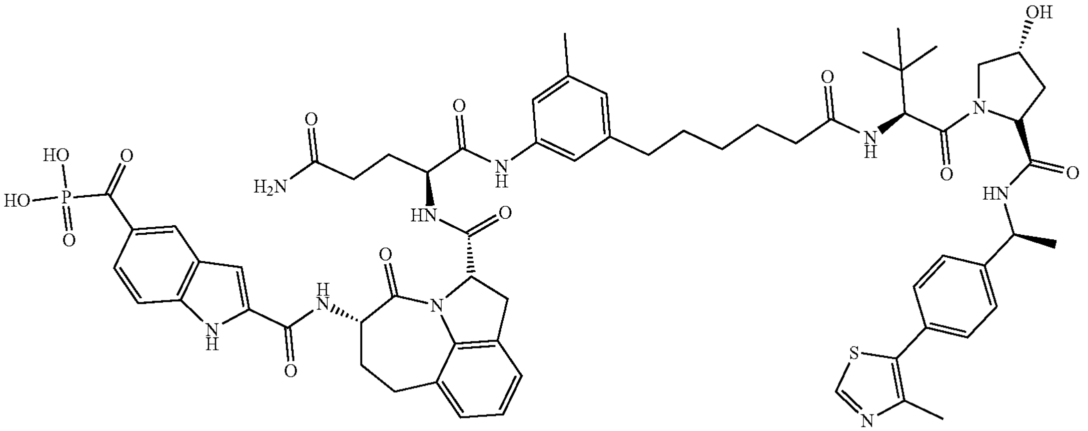
or a pharmaceutically acceptable salt thereof.
17. The compound of claim 1, wherein said compound is
I-261
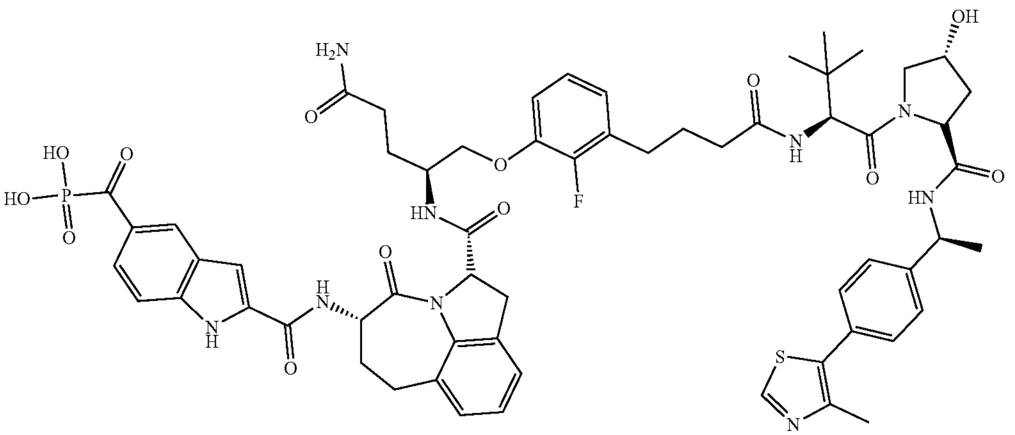
or a pharmaceutically acceptable salt thereof.

18. The compound of claim 1, wherein said compound is
I-262
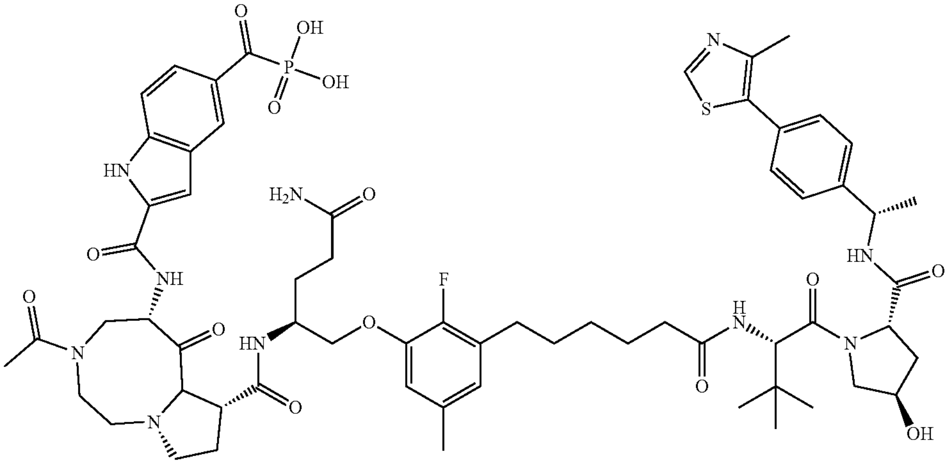
or a pharmaceutically acceptable salt thereof.
19. The compound of claim 1, wherein said compound is
I-272
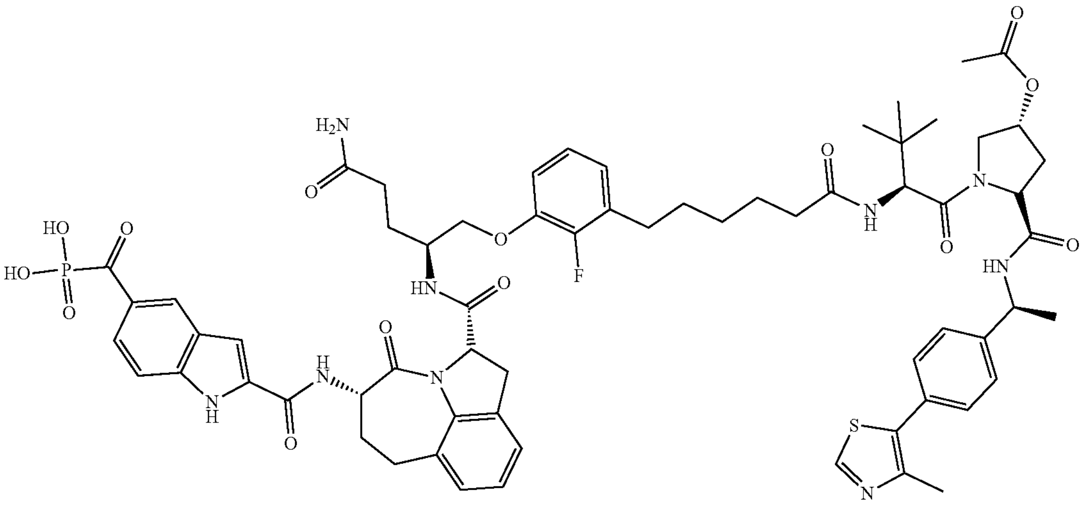
or a pharmaceutically acceptable salt thereof.

20. The compound of claim 1, wherein said compound is
I-275
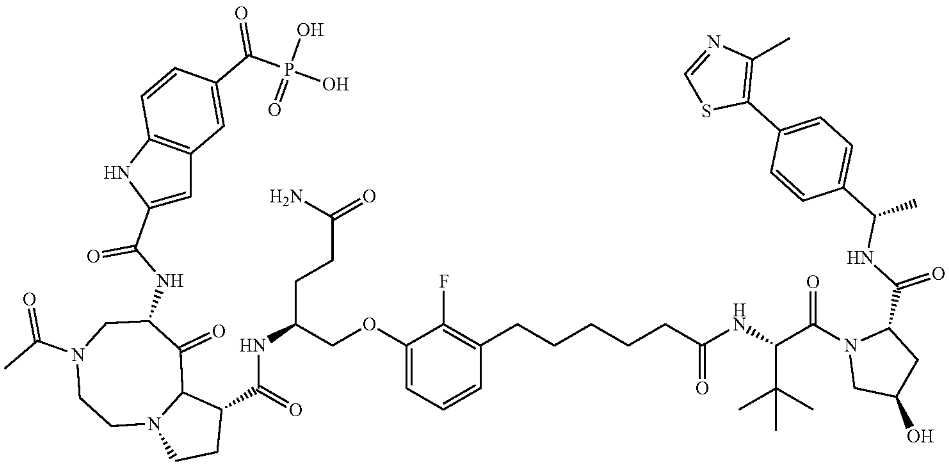
or a pharmaceutically acceptable salt thereof.
21. The compound of claim 1, wherein said compound is
I-276
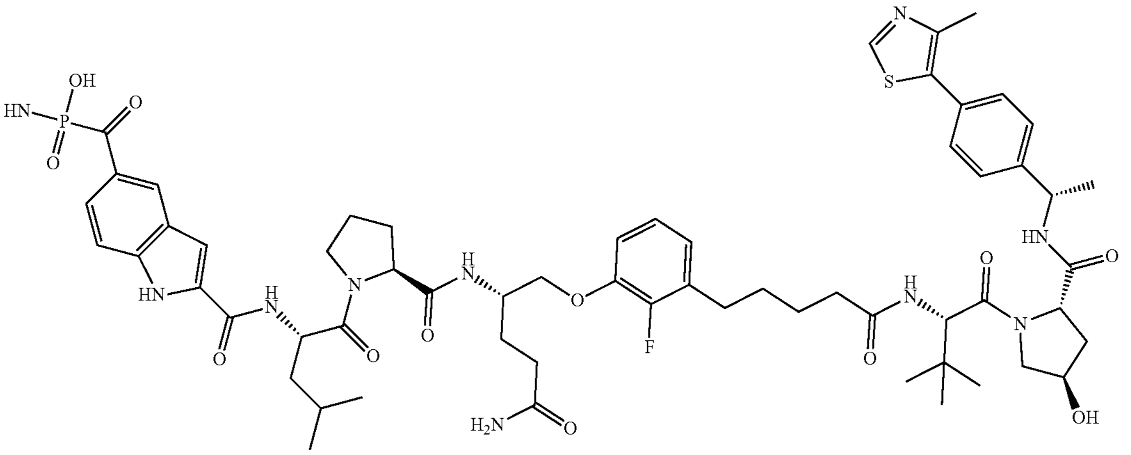
or a pharmaceutically acceptable salt thereof.

22. The compound of claim 1, wherein said compound is
I-279
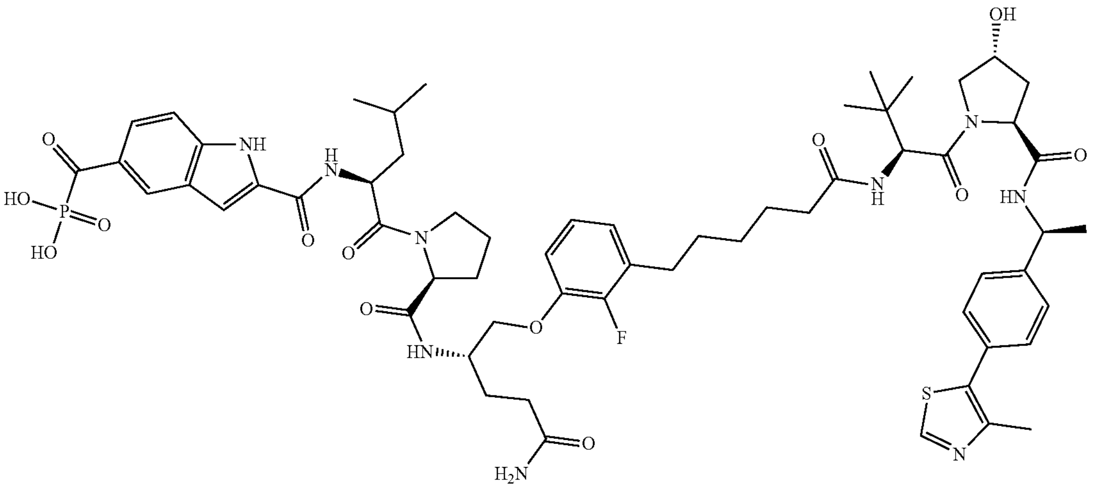
or a pharmaceutically acceptable salt thereof.
23. The compound of claim 1, wherein said compound is
I-281
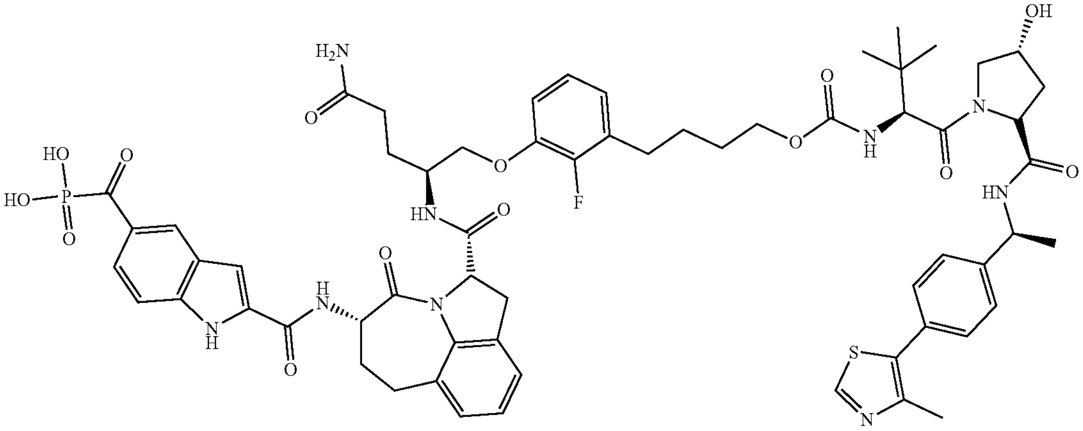
or a pharmaceutically acceptable salt thereof.
24. The compound of claim 1, wherein said compound is
I-294
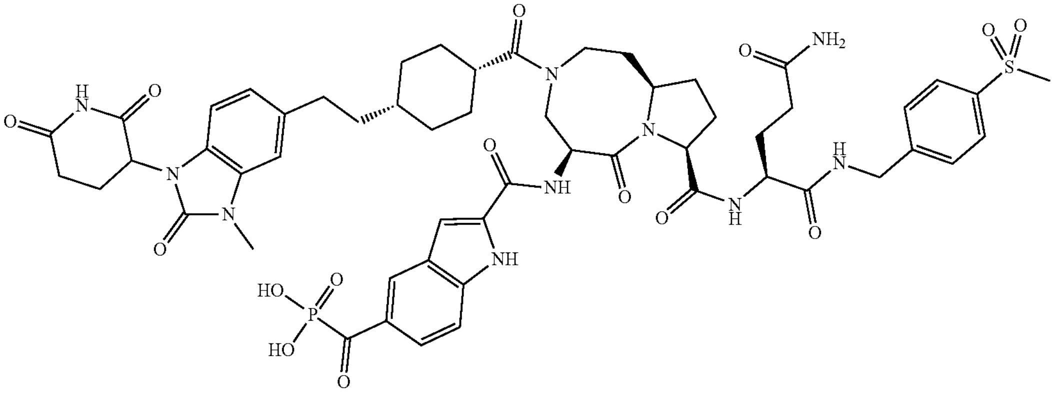
or a pharmaceutically acceptable salt thereof.

25. The compound of claim 1, wherein said compound is
I-295
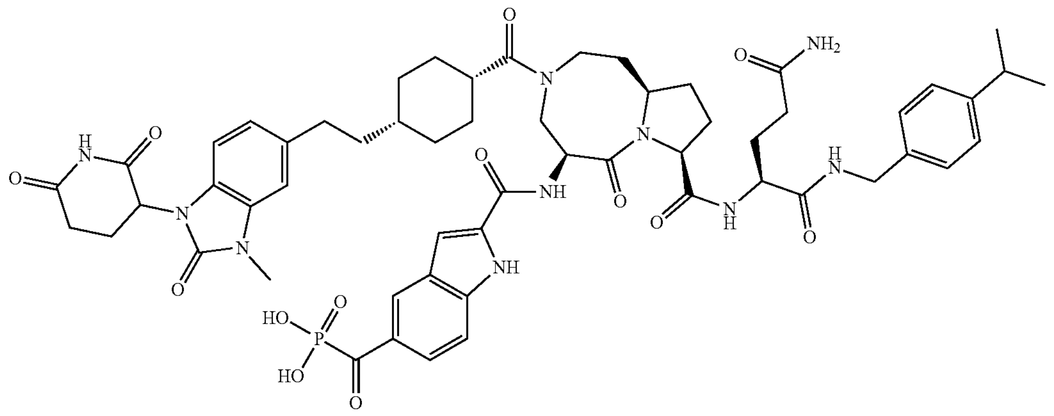
or a pharmaceutically acceptable salt thereof.
26. A pharmaceutical composition comprising a compound selected from the group consisting of:
I-83
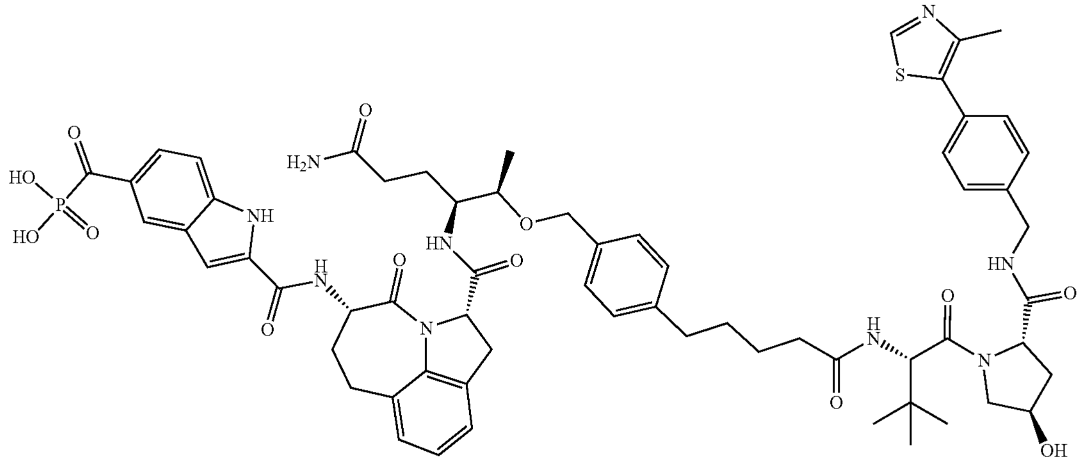
I-94
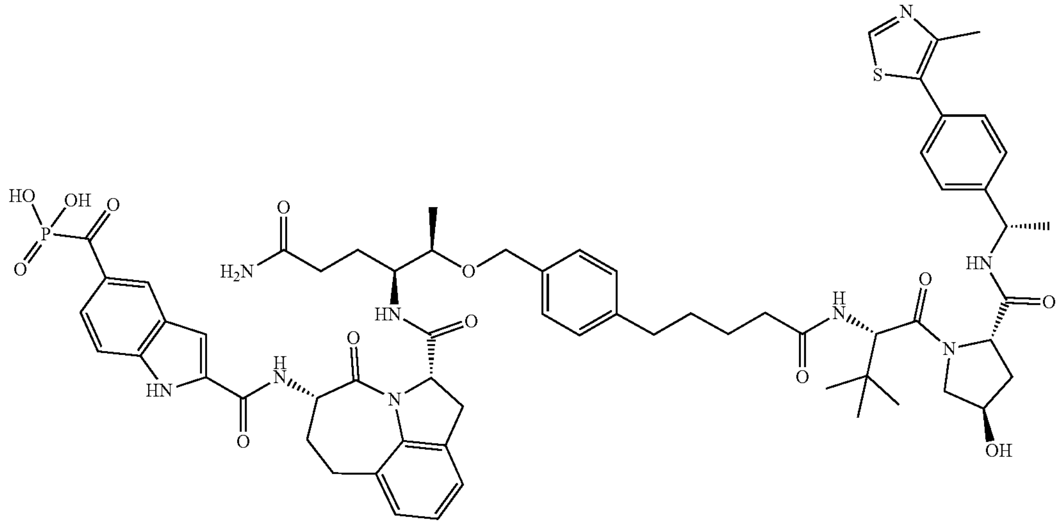

-continued
I-103
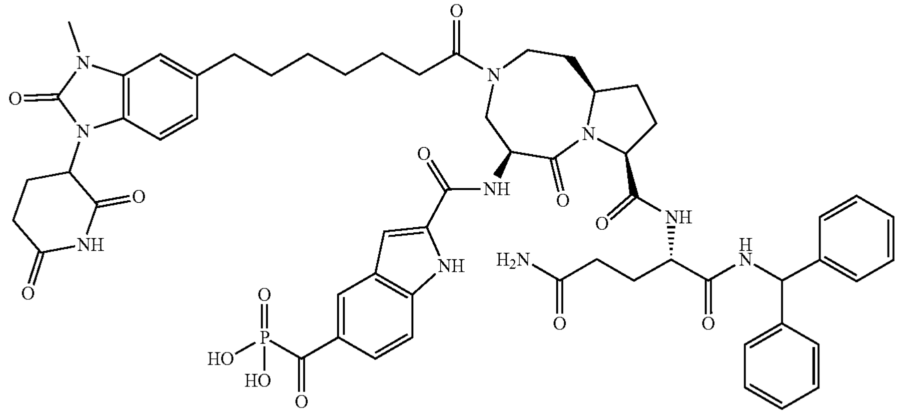
I-166
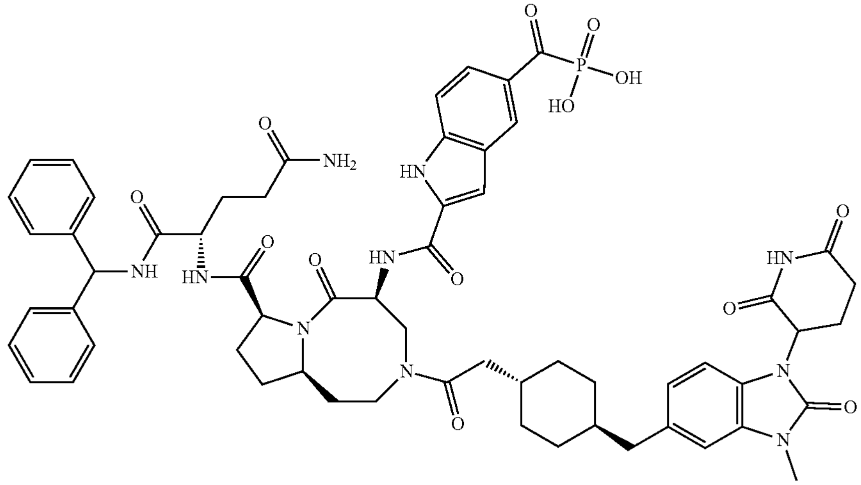
I-195
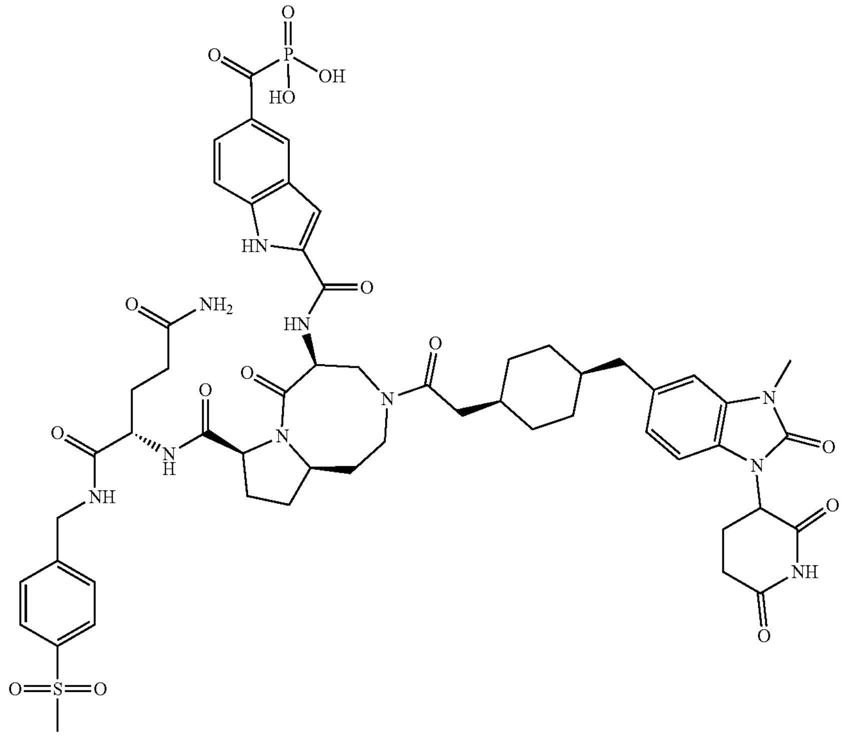

-continued
I-196
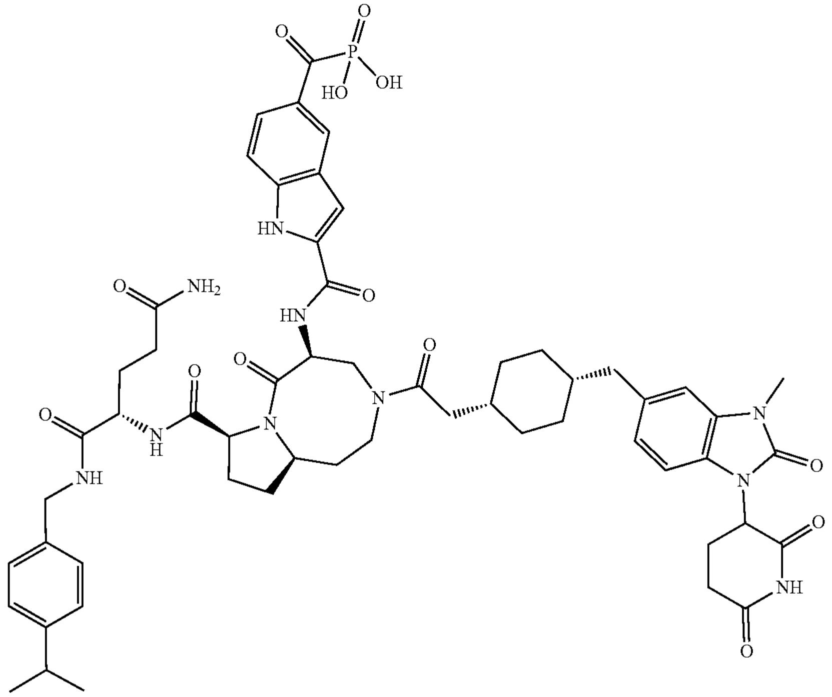
I-213
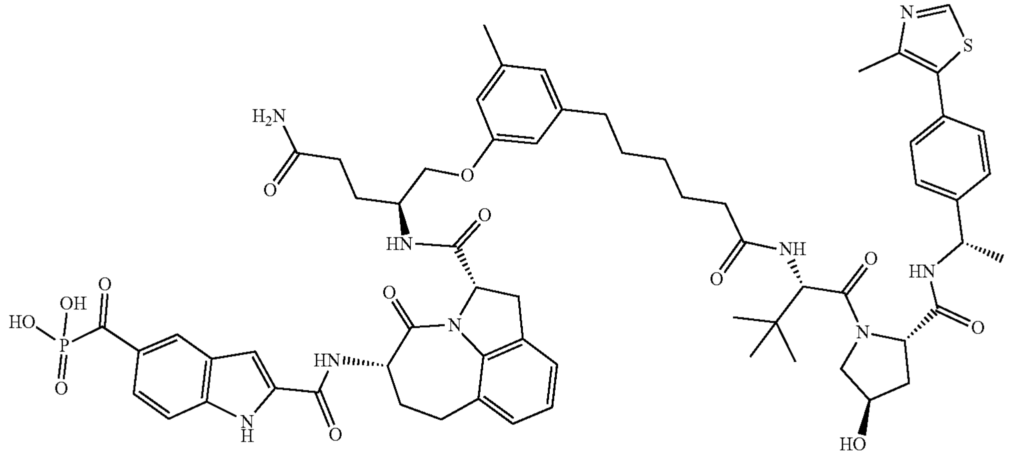
I-217
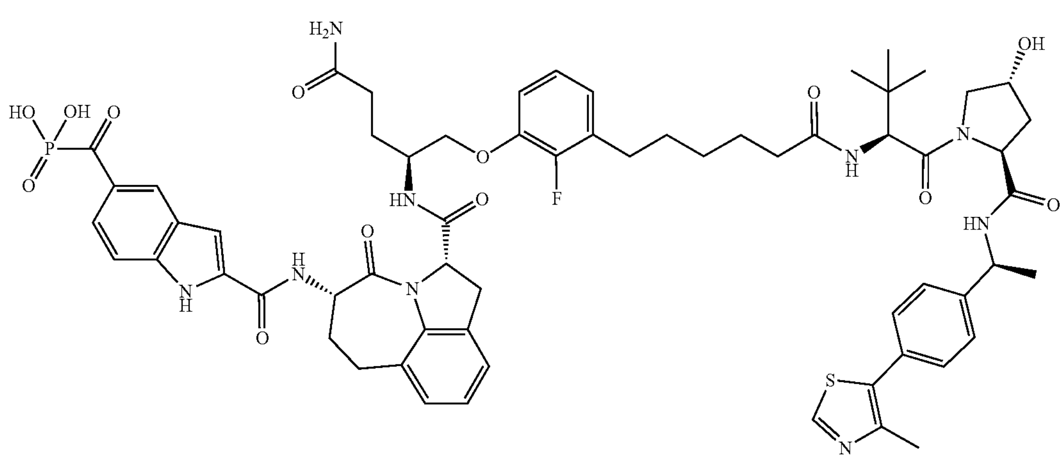

-continued
I-218
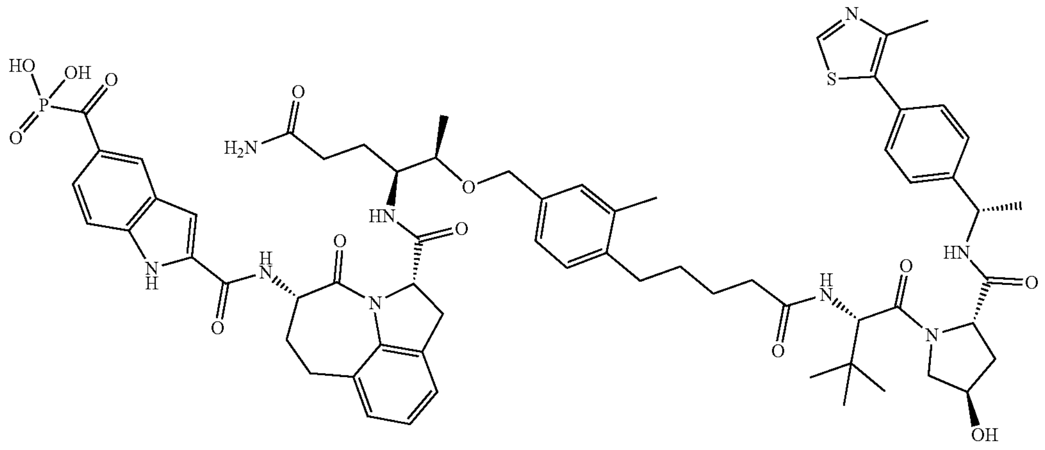
I-239
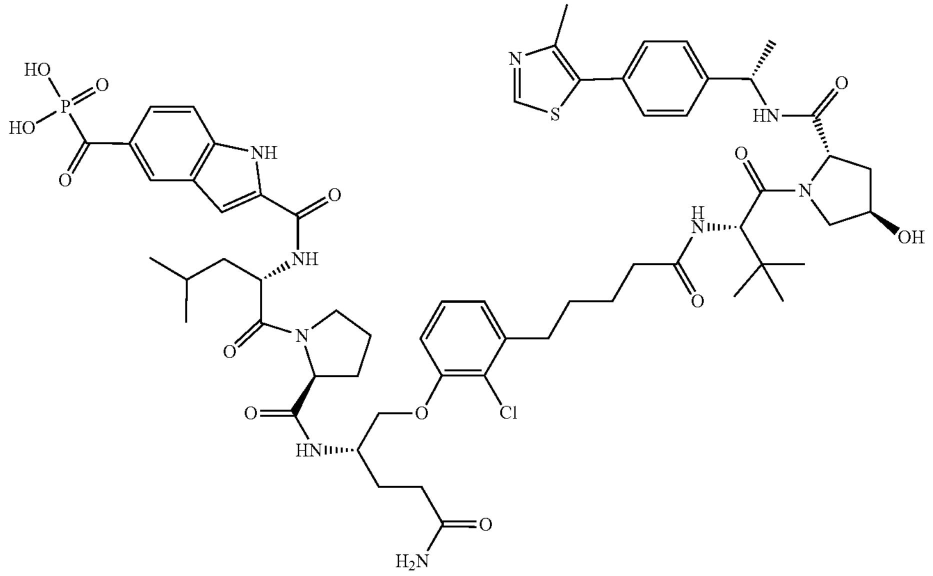
I-241
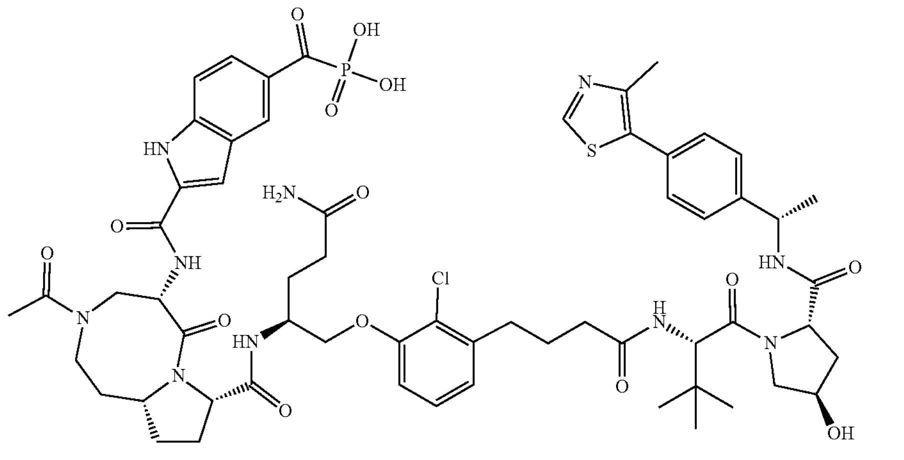

-continued
I-243
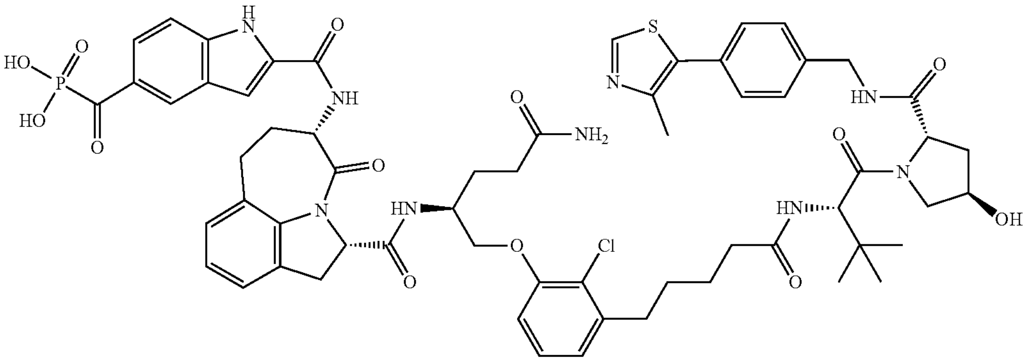
I-244
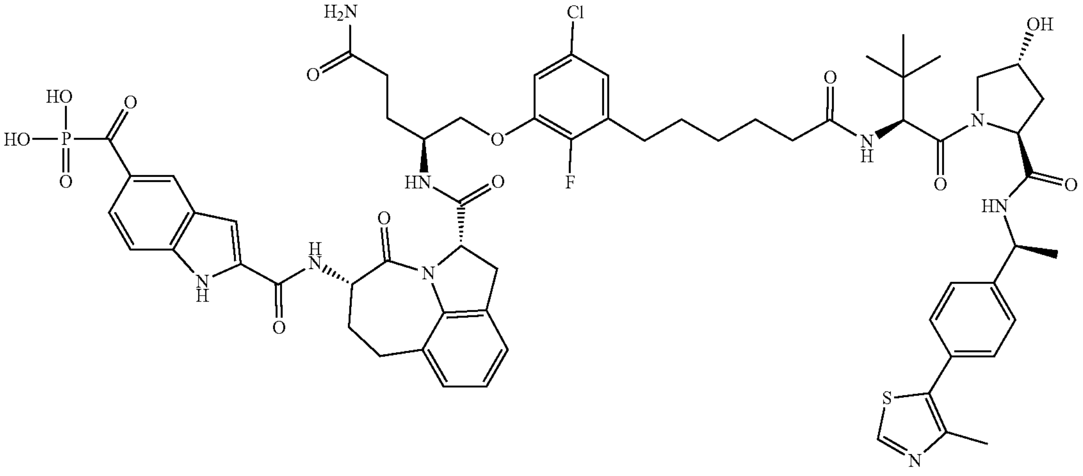
I-251
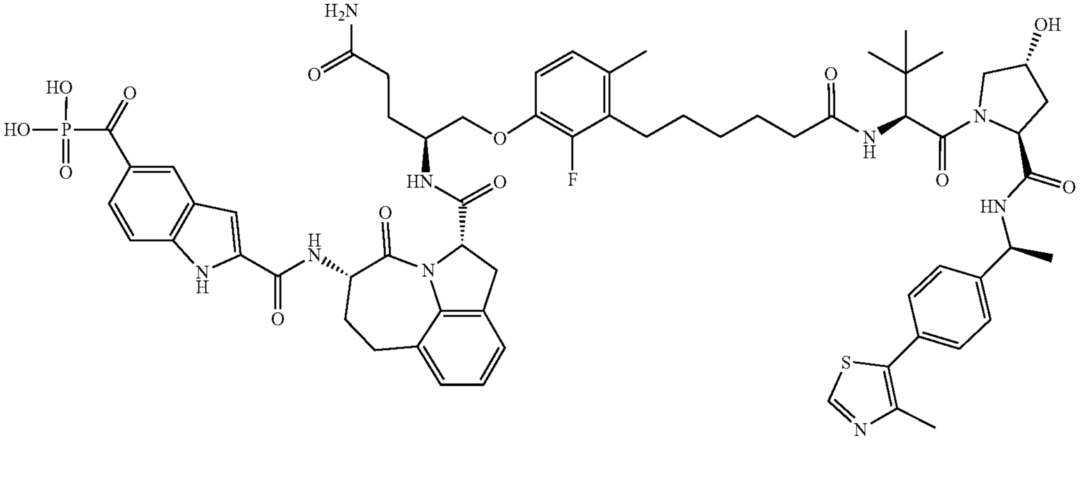

-continued
I-258
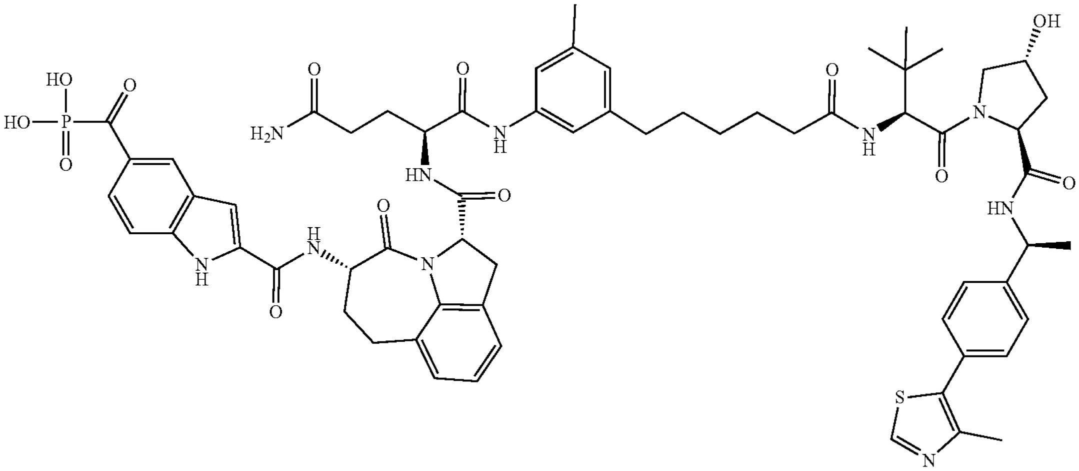
I-261
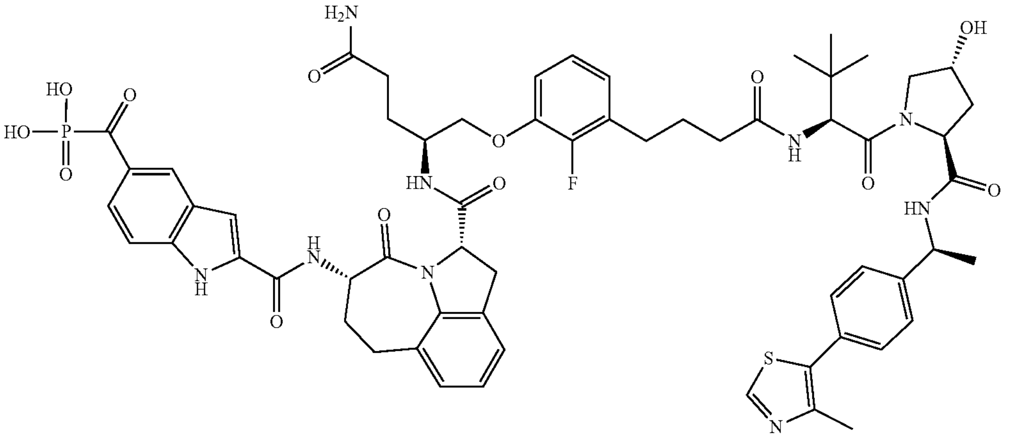
I-262
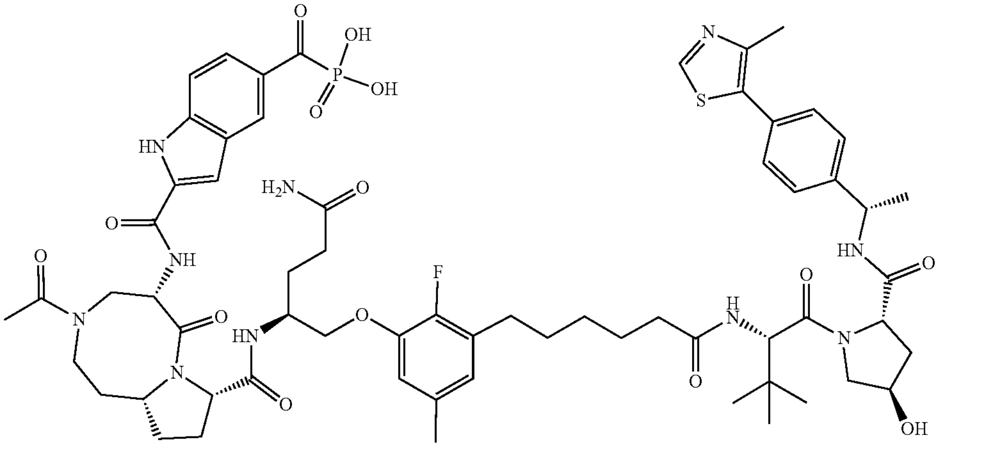

-continued
I-272
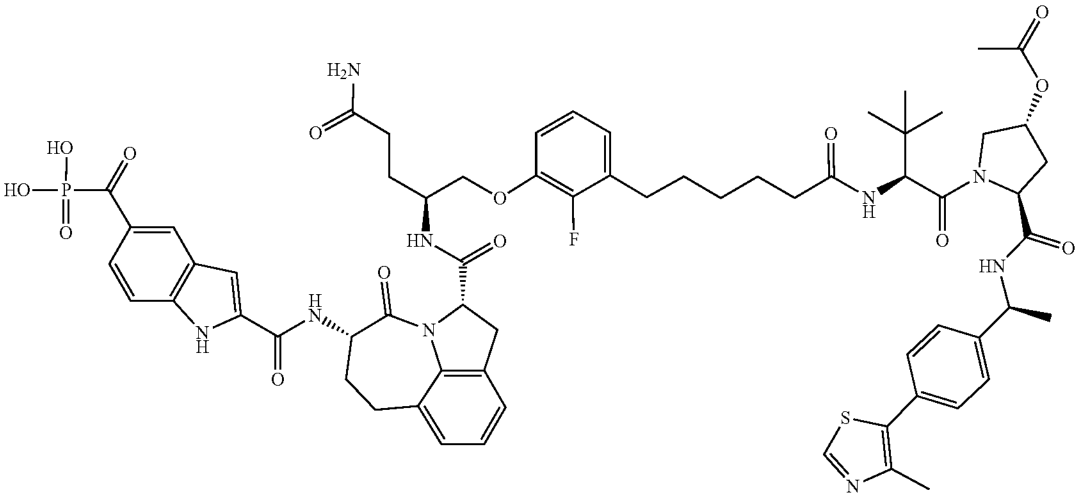
I-275
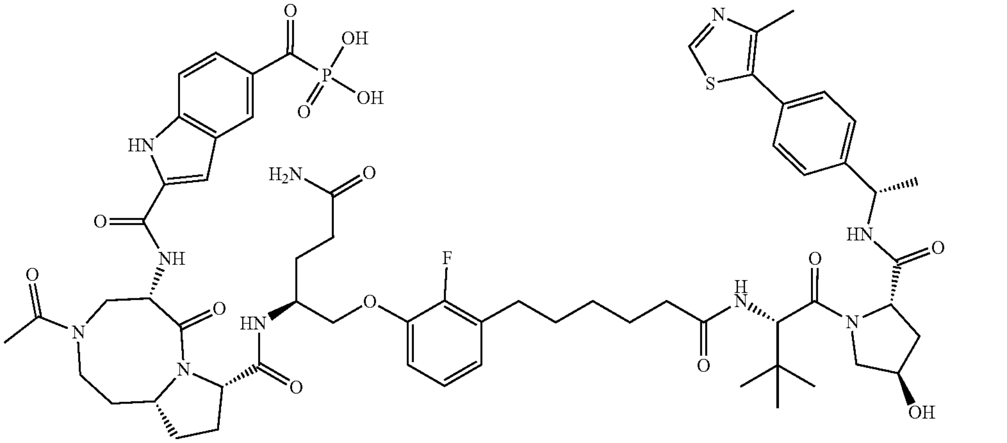
I-276
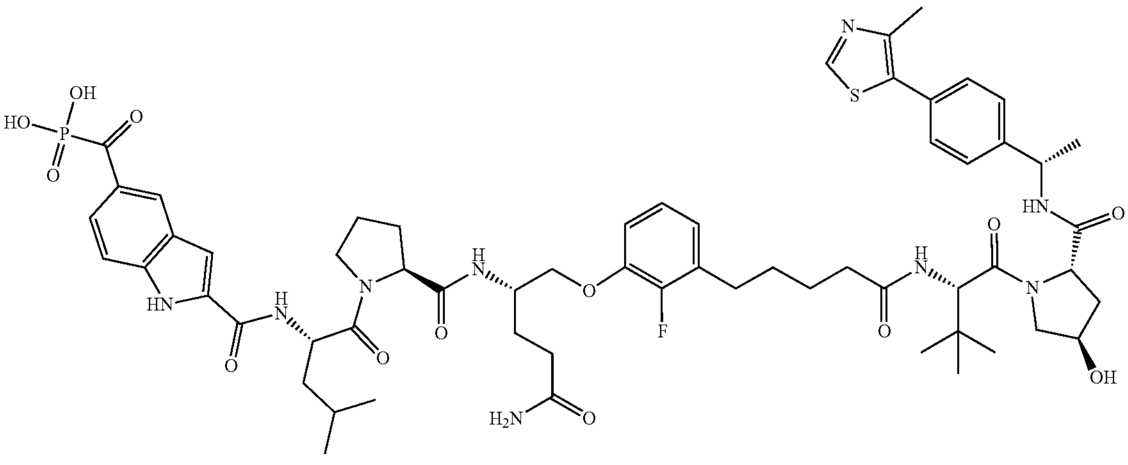

-continued
I-279
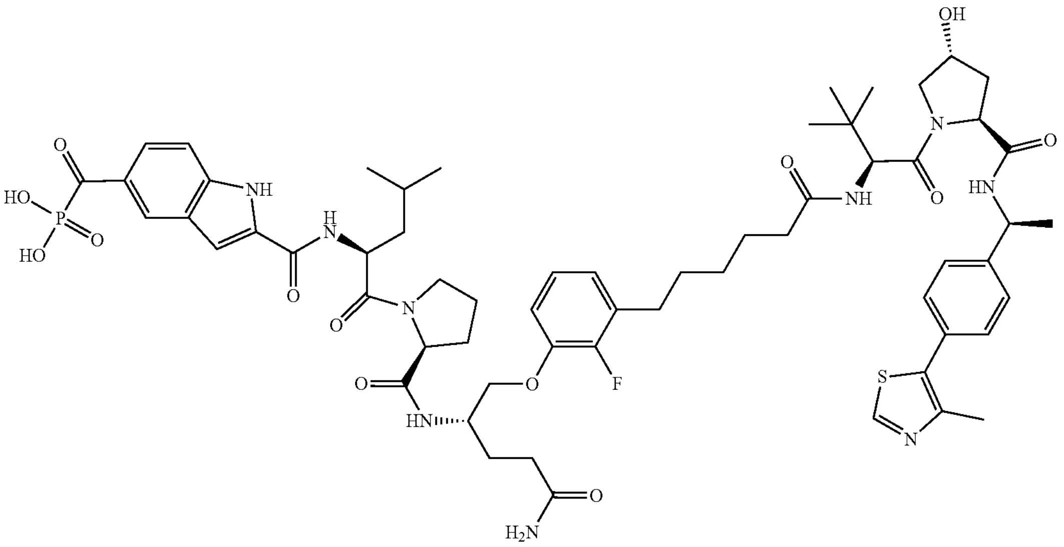
I-281
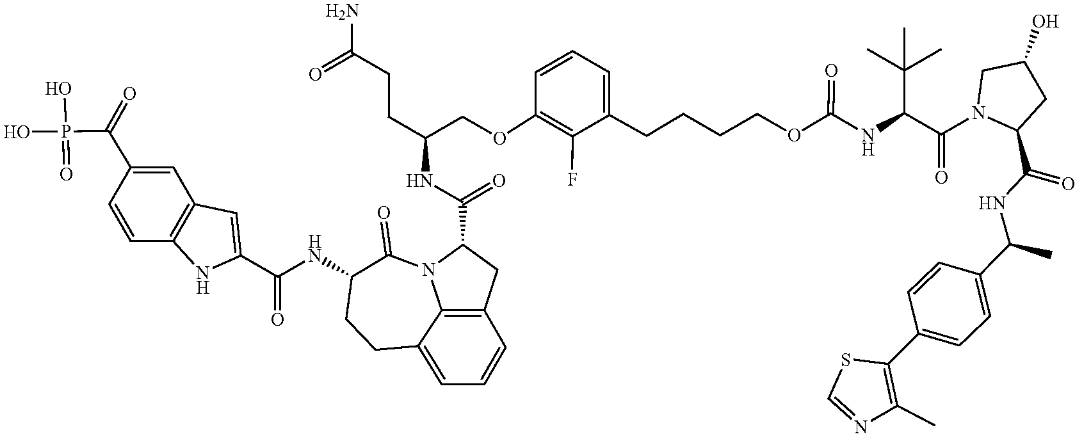
I-294
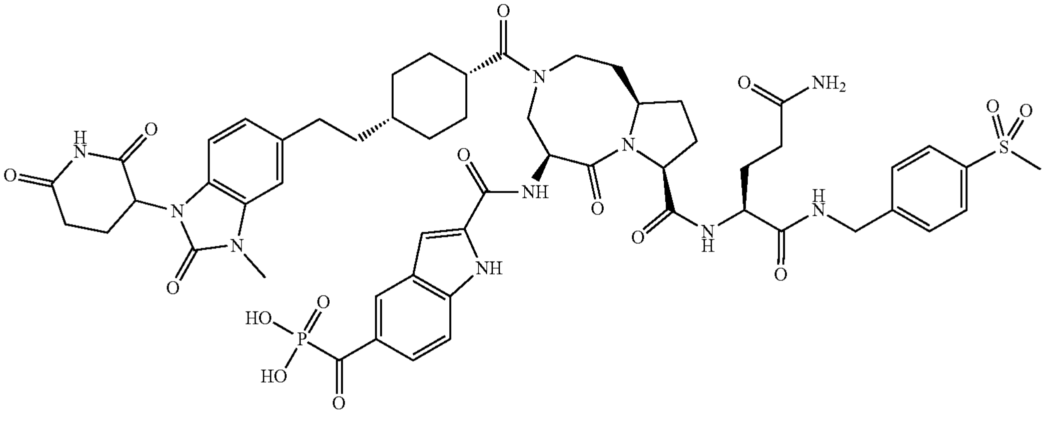
and

-continued
I-295
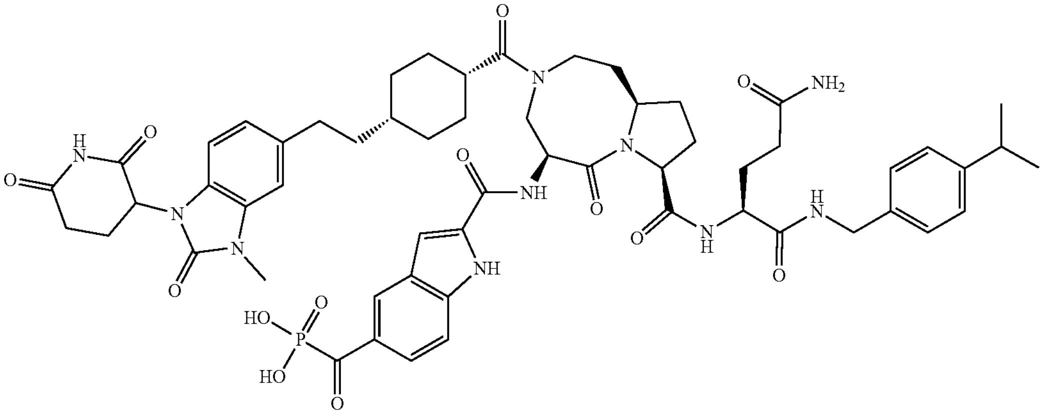
or a pharmaceutically acceptable salt thereof, and a pharmaceutically acceptable carrier, adjuvant, or vehicle.
27. The pharmaceutical composition of claim 26, wherein said compound is selected from the group consisting of:
I-83
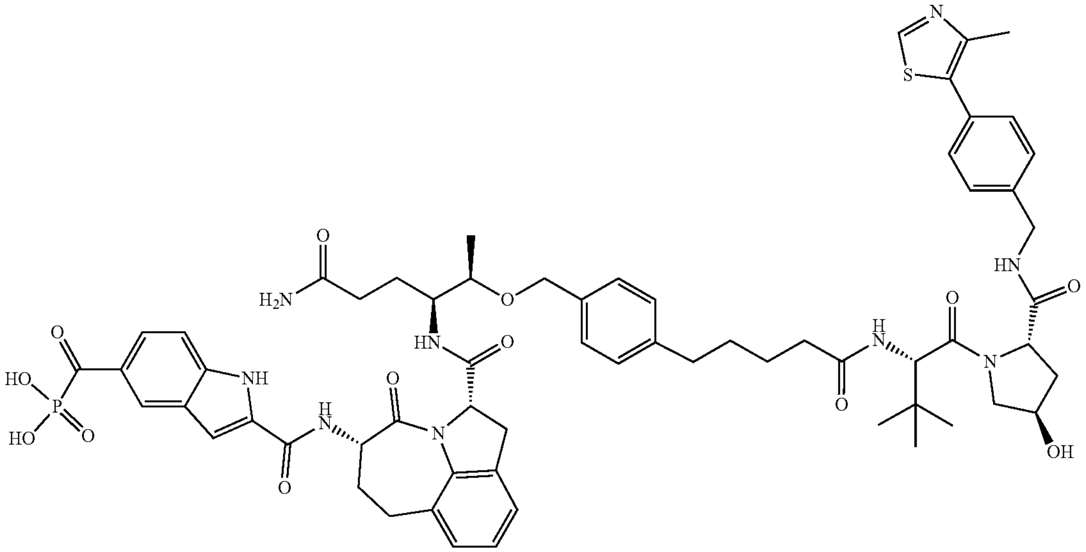
I-94
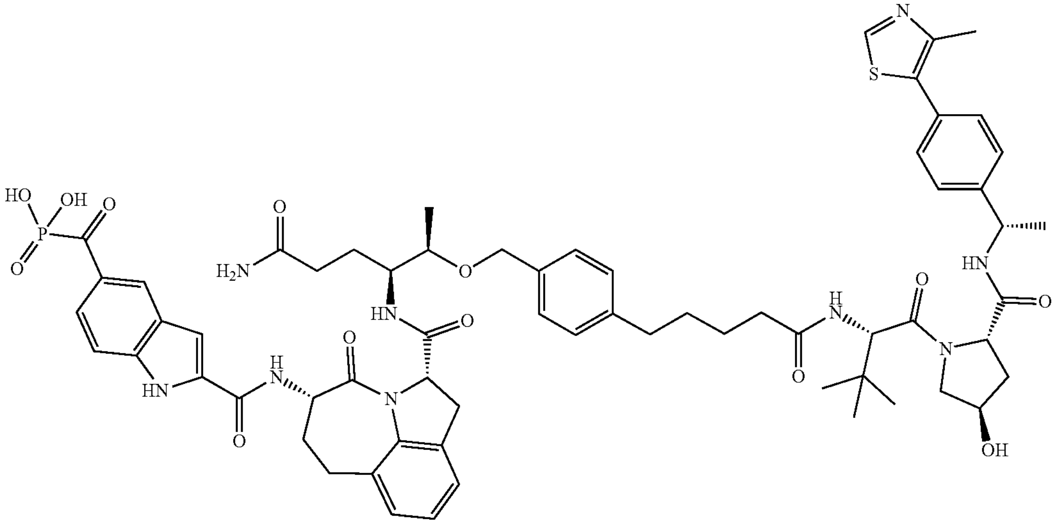

-continued
I-103
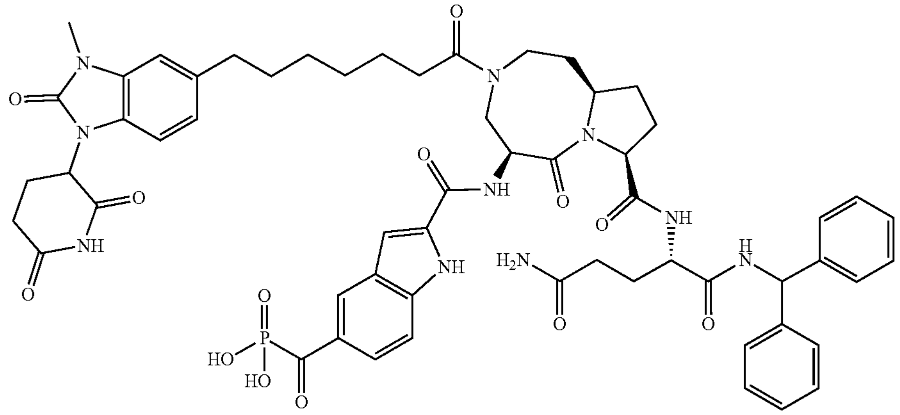
I-166
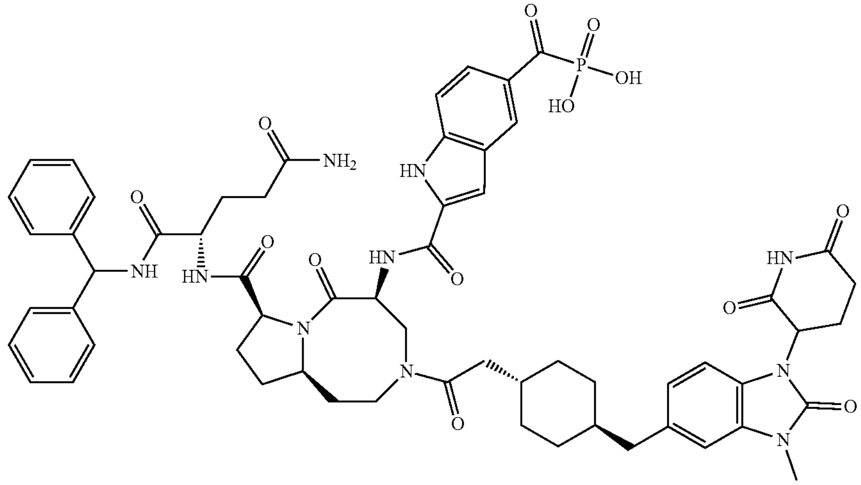
I-195
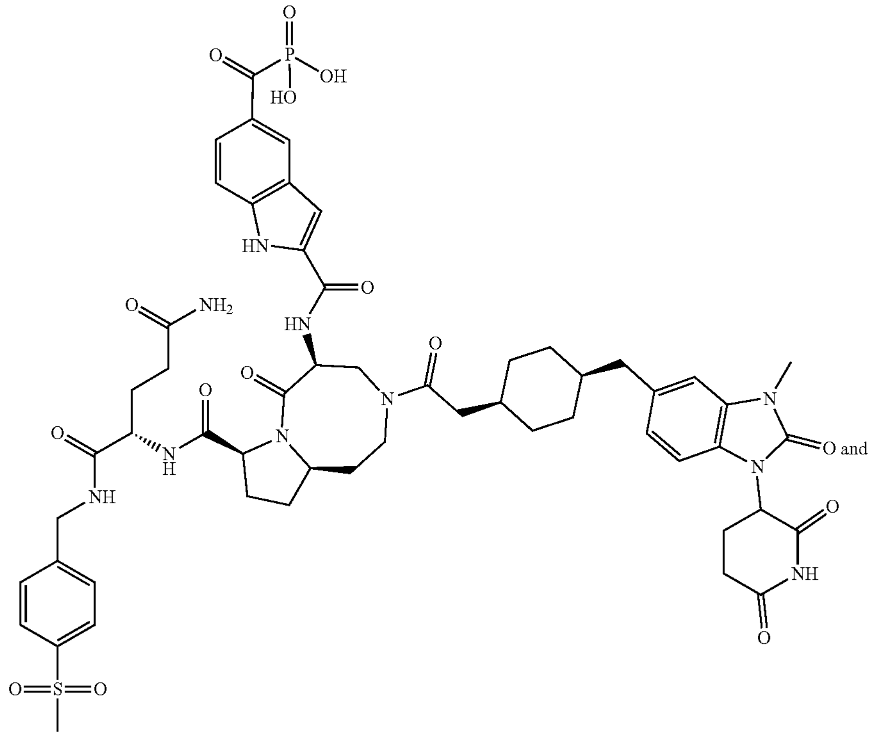 and

-continued
I-196
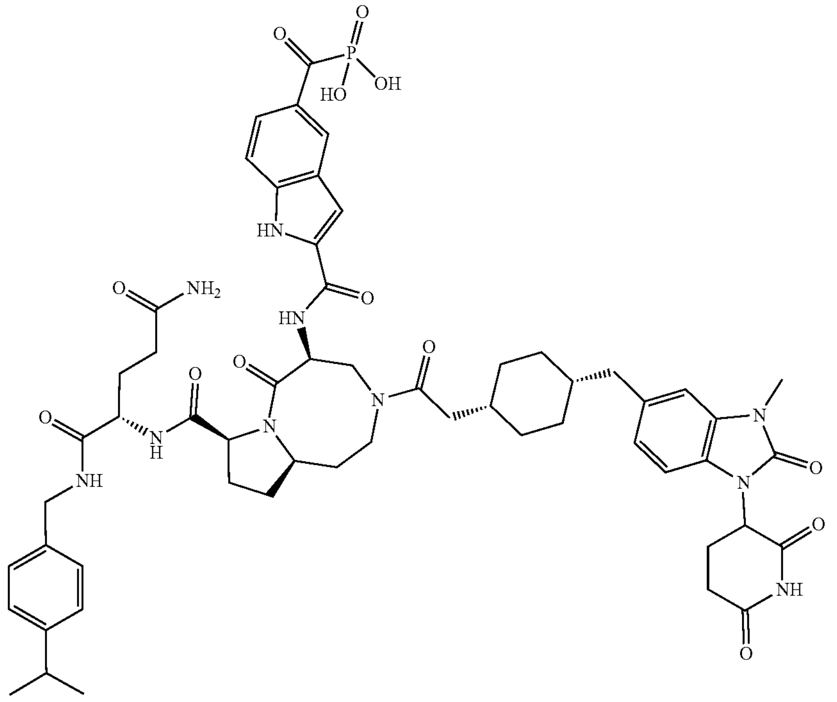
or a pharmaceutically acceptable salt thereof, and a pharmaceutically acceptable carrier, adjuvant, or vehicle.
28. The pharmaceutical composition of claim 26, wherein said compound is selected from the group consisting of:
I-213
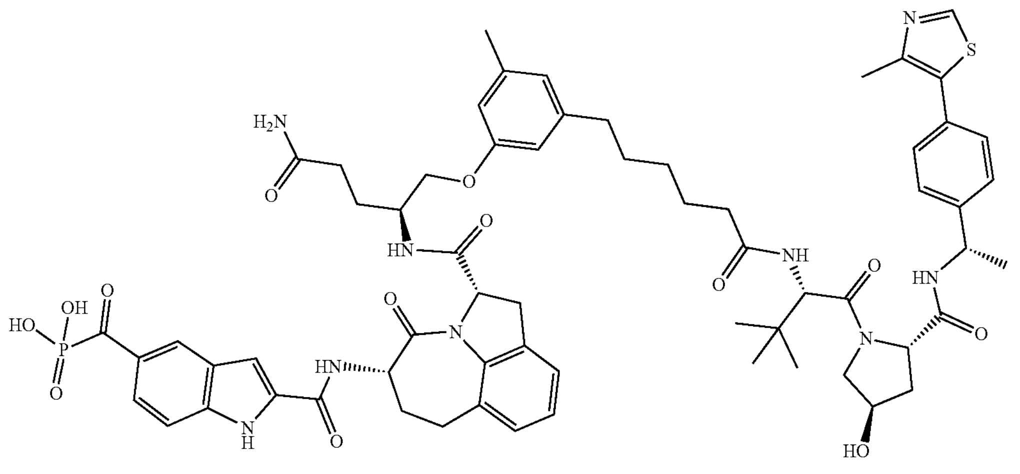

-continued
I-217
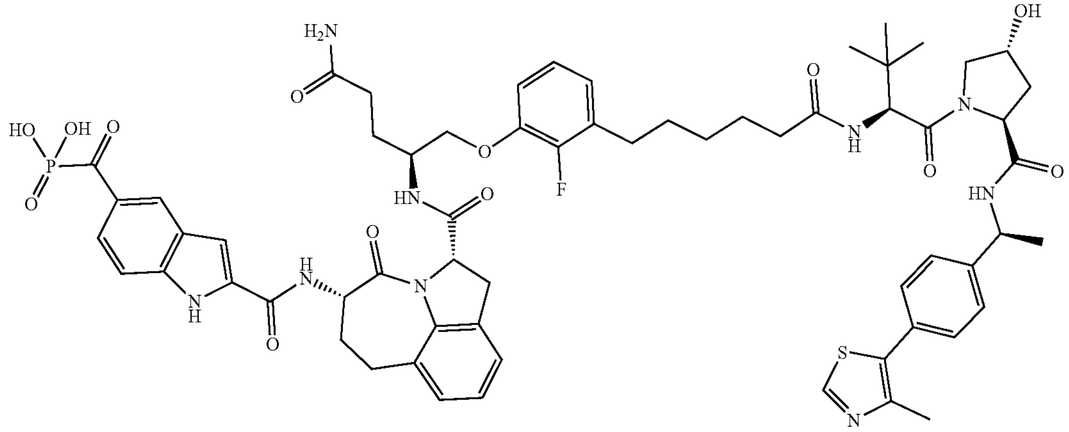
I-218
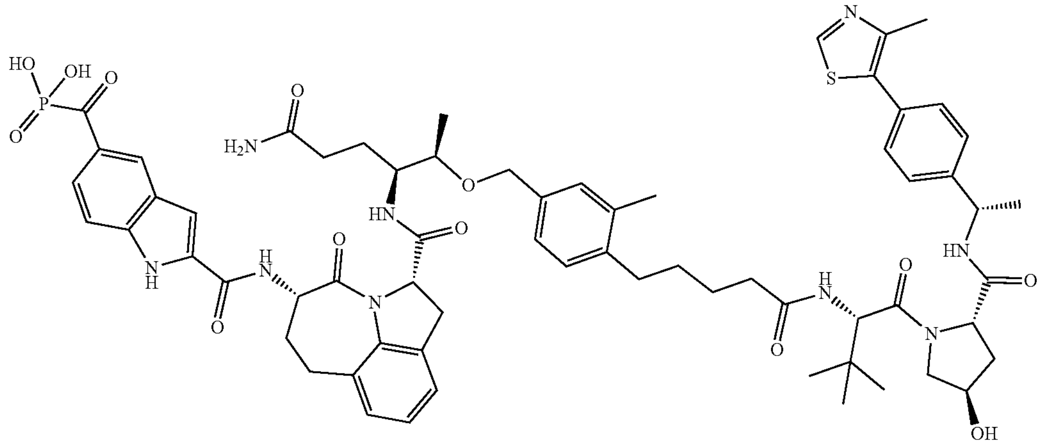
I-239
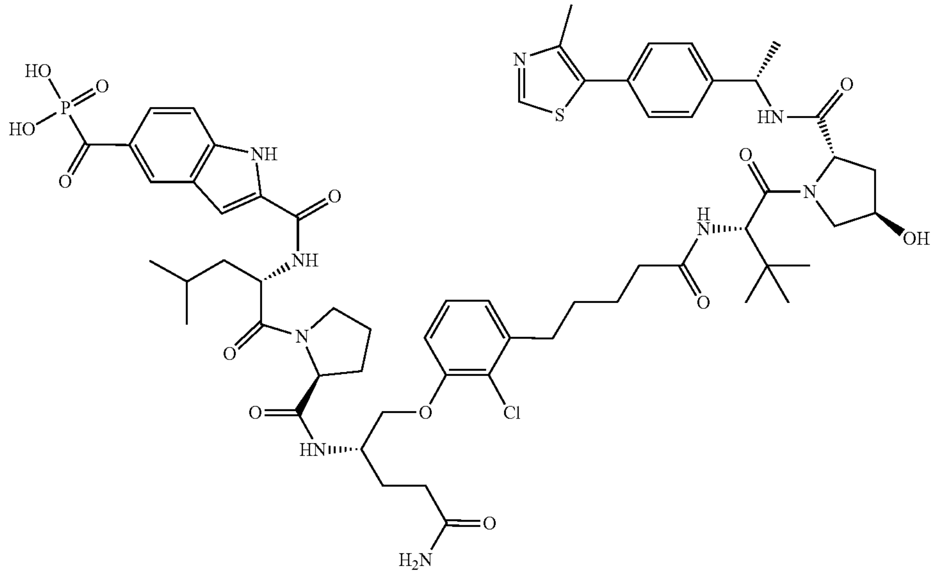

-continued
I-241
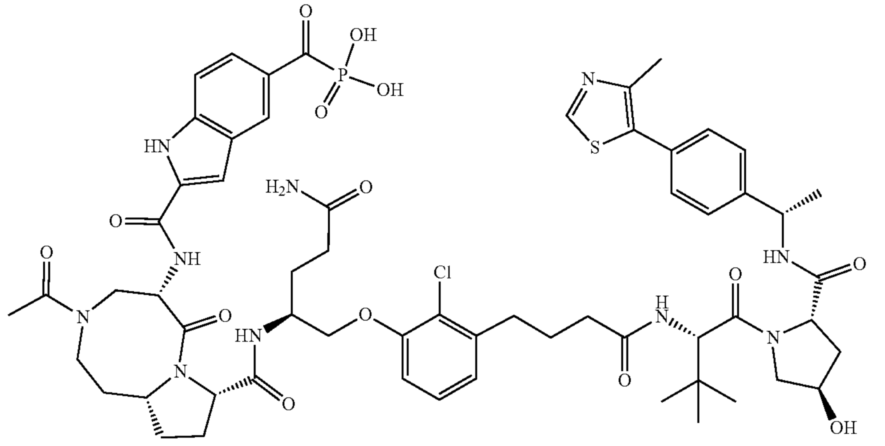
I-243
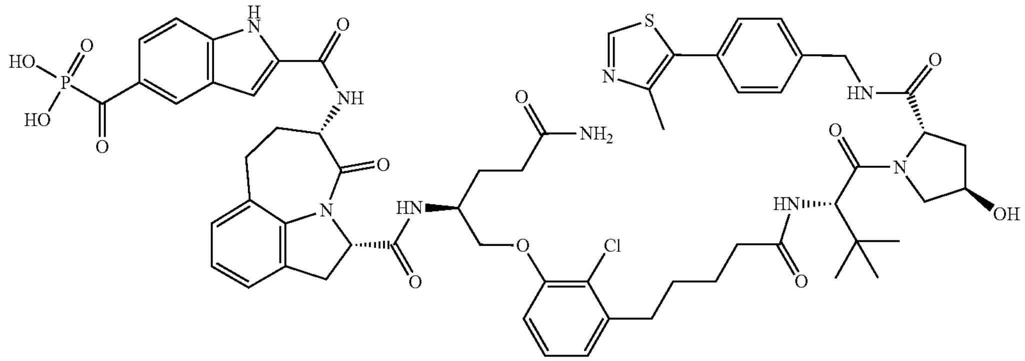
or a pharmaceutically acceptable salt thereof, and a pharmaceutically acceptable carrier, adjuvant, or vehicle.
29. The pharmaceutical composition of claim 26, wherein said compound is selected from the group consisting of:
I-244
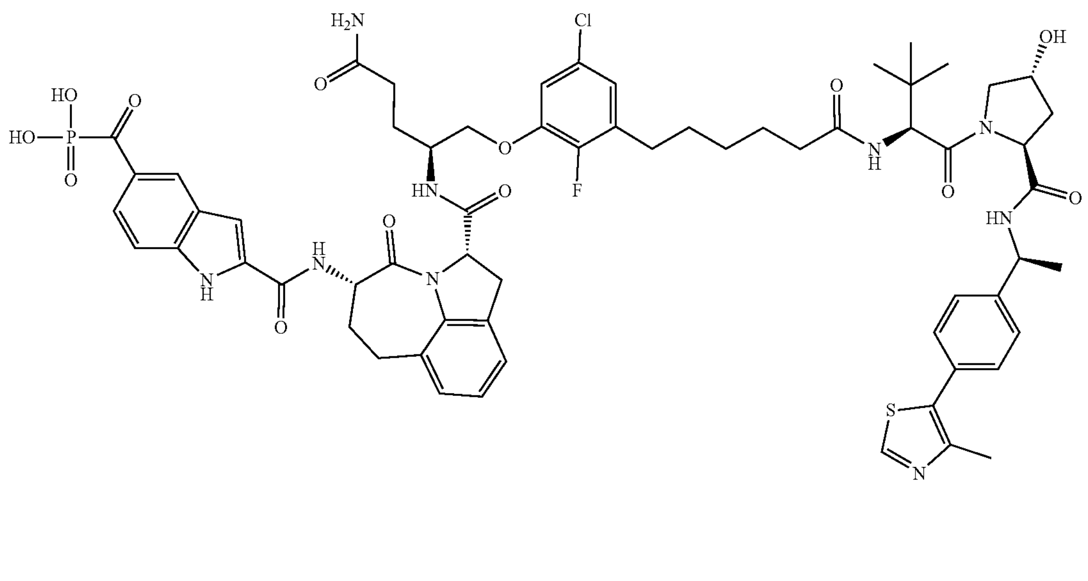

-continued
I-251
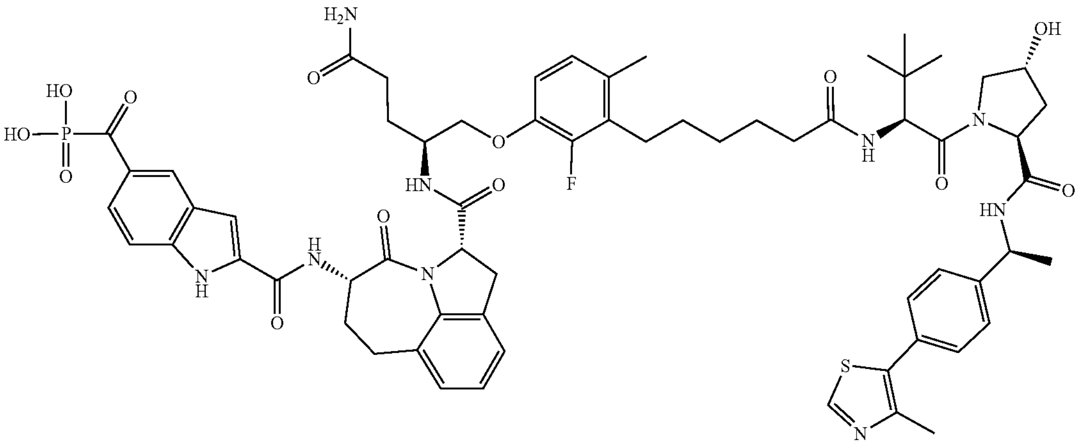
I-258
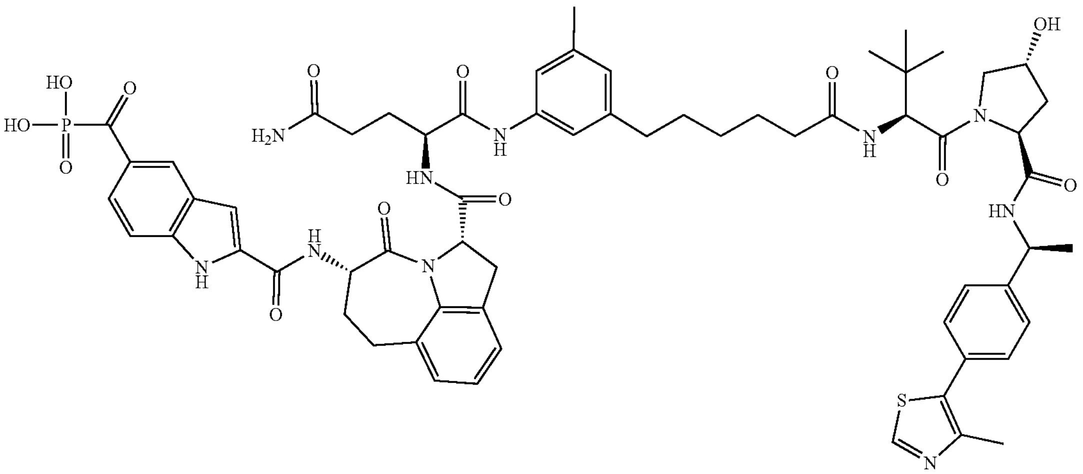
I-261
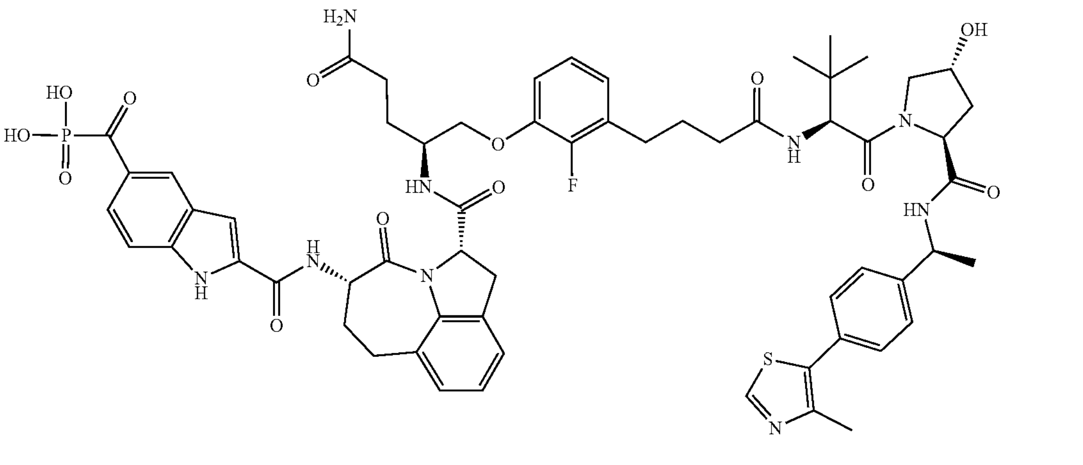

-continued
I-262
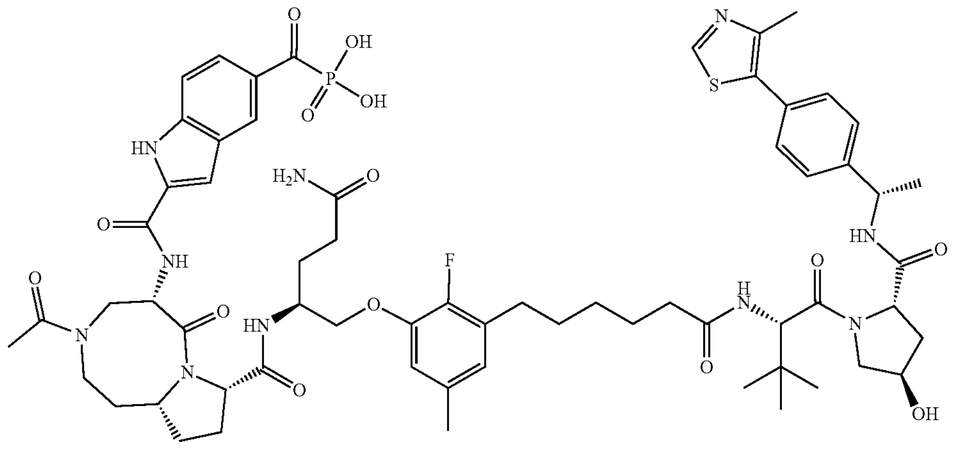
and
I-272
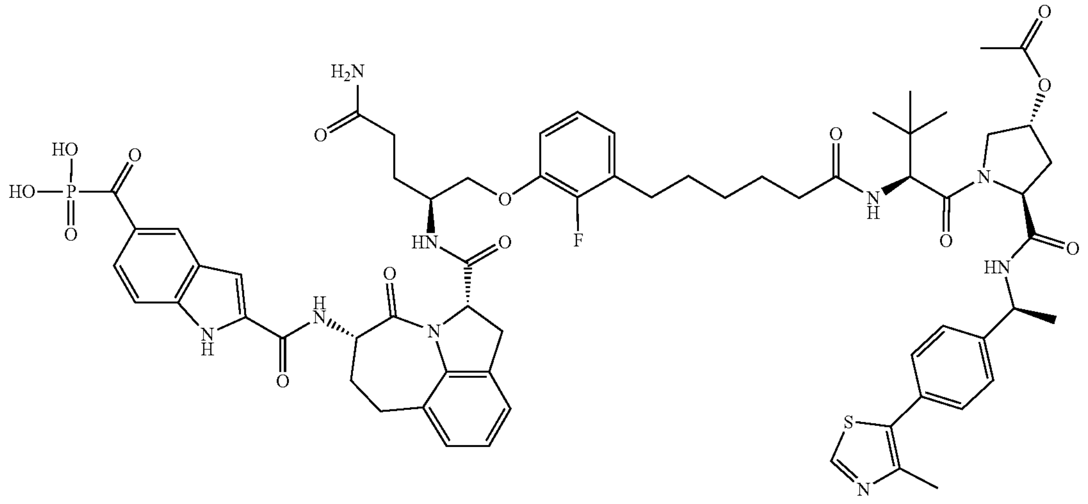
or a pharmaceutically acceptable salt thereof, and a pharmaceutically acceptable carrier, adjuvant, or vehicle.
30. The pharmaceutical composition of claim 26, wherein said compound is selected from the group consisting of
I-275
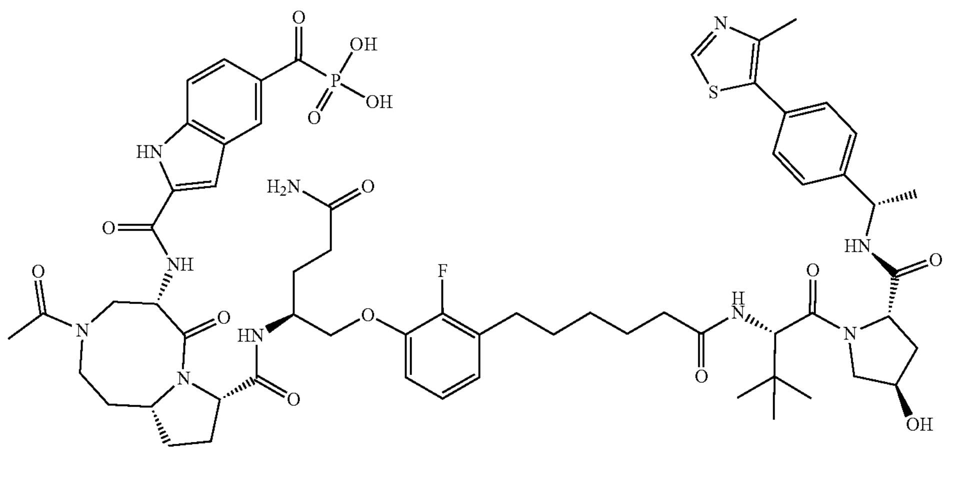

-continued
I-276
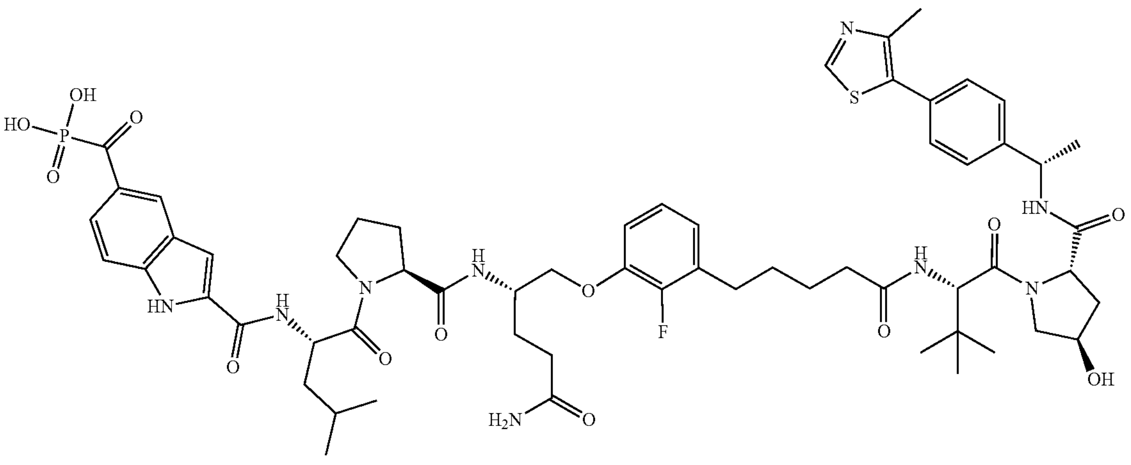
I-279
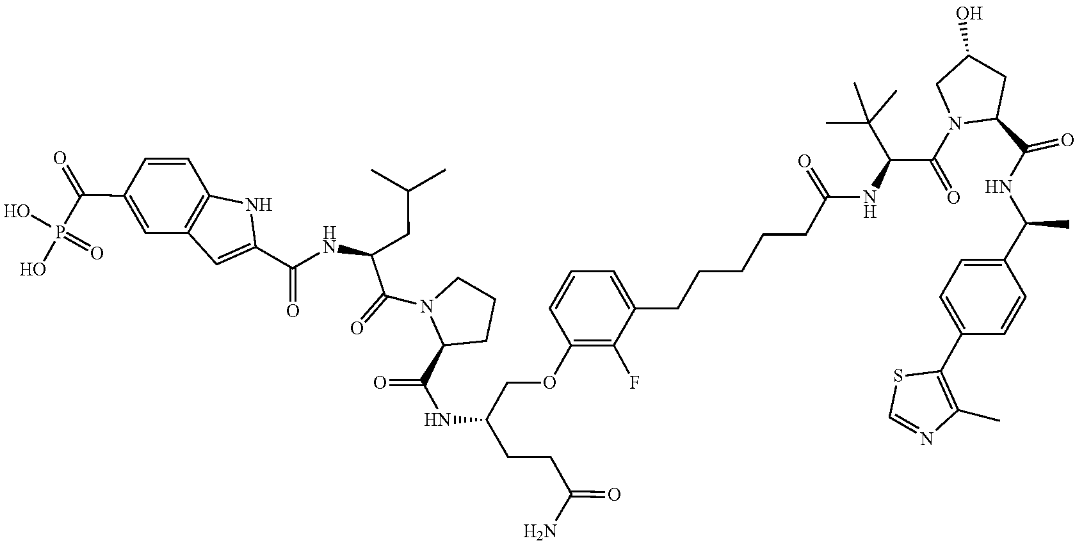
I-281
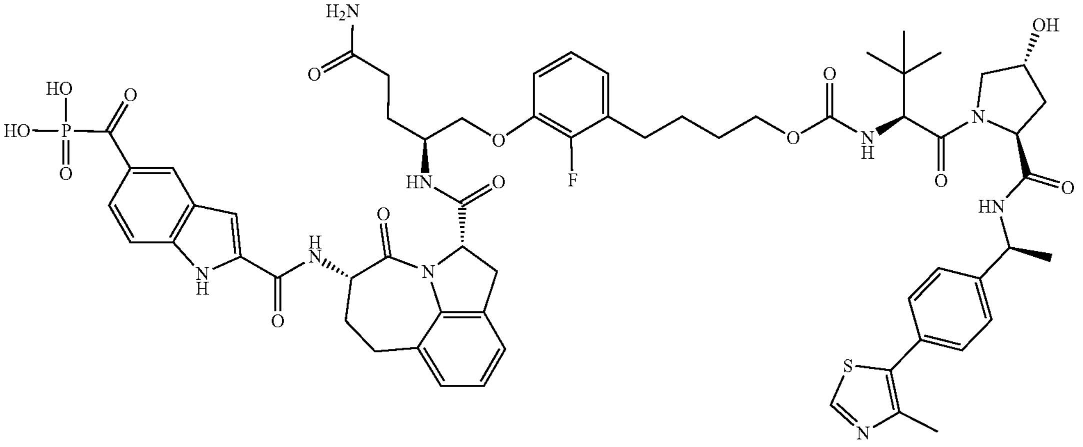

-continued
I-294
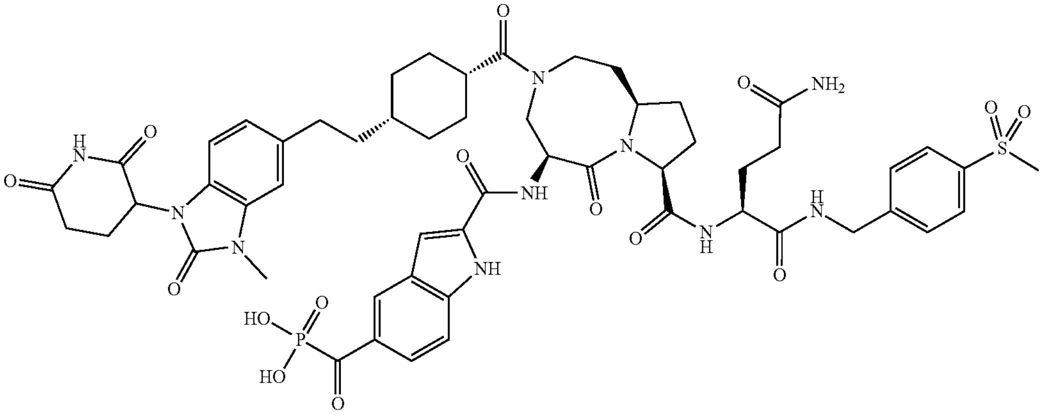
and
I-295
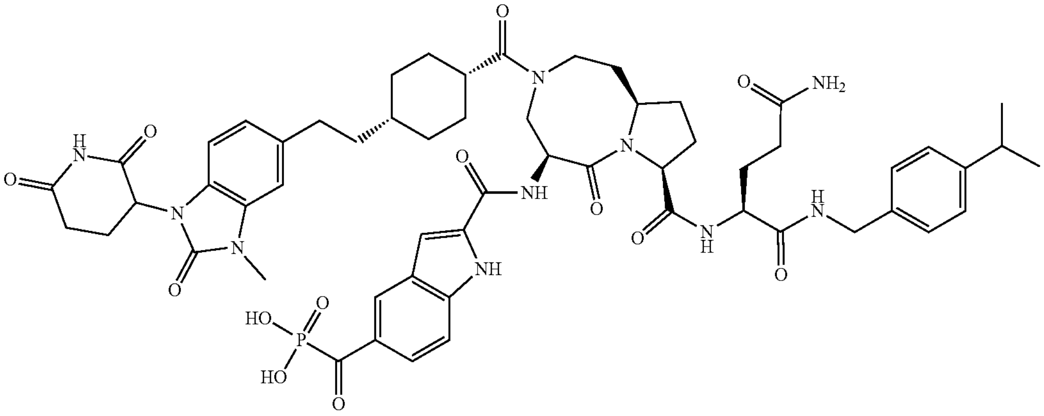
or a pharmaceutically acceptable salt thereof, and a pharmaceutically acceptable carrier, adjuvant, or vehicle.
* * * * *